US009067987B2

(12) United States Patent
Galeotti et al.

(10) Patent No.: US 9,067,987 B2

(45) **Date of Patent: *Jun. 30, 2015**

(54) NEISSERIAL ANTIGENIC PEPTIDES

(75) Inventors: Cesira Galeotti, Monteriggioni (IT); Guido Grandi, Siena (IT); Vega Masignani, Siena (IT); Marirosa Mora, Siena (IT); Mariagrazia Pizza, Siena (IT); Rino Rappuoli, Siena (IT); Guilio Ratti, Siena (IT); Vincenzo Scarlato, Siena (IT); Maria Scarselli, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/405,213

(22) Filed: Feb. 24, 2012

(65) Prior Publication Data

US 2012/0276129 A1 Nov. 1, 2012

Related U.S. Application Data

(62) Division of application No. 10/111,983, filed as application No. PCT/IB00/01661 on Oct. 30, 2000, now Pat. No. 8,734,812.

(60) Provisional application No. 60/162,616, filed on Oct. 29, 1999.

(51) Int. Cl.

| | |
|---|---|
| ***C07K 14/22*** | (2006.01) |
| ***A61K 39/095*** | (2006.01) |
| ***A61K 39/00*** | (2006.01) |
| *A61K 48/00* | (2006.01) |

(52) U.S. Cl.

CPC ................. *C07K 14/22* (2013.01); *A61K 39/00* (2013.01); *A61K 48/00* (2013.01)

(58) Field of Classification Search

None

See application file for complete search history.

(56) References Cited

U.S. PATENT DOCUMENTS

| | | | | |
|---|---|---|---|---|
| 5,965,424 | A | 10/1999 | Ambrosius | |
| 7,348,006 | B2 | 3/2008 | Contorni et al. | |
| 7,576,176 | B1 * | 8/2009 | Fraser et al. | 530/350 |
| 7,785,608 | B2 | 8/2010 | Zlotnick et al. | |
| 7,862,827 | B2 | 1/2011 | Giuliani et al. | |
| 8,101,194 | B2 | 1/2012 | Zlotnick et al. | |
| 8,226,960 | B2 | 7/2012 | Masignani et al. | |
| 8,273,360 | B2 | 9/2012 | Pizza et al. | |
| 8,293,251 | B2 | 10/2012 | Scarlato et al. | |
| 8,394,390 | B2 | 3/2013 | Galeotti et al. | |
| 8,398,988 | B2 | 3/2013 | Contorni et al. | |
| 8,398,999 | B2 | 3/2013 | Masignani et al. | |
| 8,524,251 | B2 | 9/2013 | Fraser et al. | |
| 8,563,007 | B1 | 10/2013 | Zlotnick et al. | |
| 8,574,597 | B2 | 11/2013 | Zlotnick | |
| 8,734,812 | B1 | 5/2014 | Galeotti et al. | |
| 8,840,907 | B2 | 9/2014 | Pizza | |
| 2004/0092711 | A1 | 5/2004 | Arico | |
| 2004/0110670 | A1 | 6/2004 | Arico et al. | |
| 2004/0167068 | A1 | 8/2004 | Zlotnick et al. | |
| 2005/0222385 | A1 | 10/2005 | Pizza | |
| 2006/0051840 | A1 | 3/2006 | Arico et al. | |
| 2006/0171957 | A1 | 8/2006 | Pizza | |
| 2006/0240045 | A1 | 10/2006 | Berthet et al. | |
| 2006/0251670 | A1 | 11/2006 | Comanducci et al. | |
| 2007/0026021 | A1 | 2/2007 | Fraser et al. | |
| 2007/0082014 | A1 | 4/2007 | Costantino | |
| 2007/0253984 | A1 | 11/2007 | Khandke et al. | |
| 2008/0241180 | A1 | 10/2008 | Contorni | |
| 2009/0285845 | A1 | 11/2009 | Masignani et al. | |
| 2010/0267931 | A1 | 10/2010 | Arico et al. | |
| 2012/0107339 | A1 | 5/2012 | Granoff et al. | |
| 2014/0037668 | A1 | 2/2014 | Giuliani et al. | |

FOREIGN PATENT DOCUMENTS

| | | | |
|---|---|---|---|
| EP | 0467714 | | 1/1992 |
| EP | 1645631 | A2 | 4/2006 |
| EP | 1790660 | | 5/2007 |
| EP | 2351767 | A2 | 8/2011 |
| WO | WO-93/18150 | | 9/1993 |
| WO | WO-96/12020 | A2 | 4/1996 |
| WO | WO-96/29412 | A1 | 9/1996 |

(Continued)

OTHER PUBLICATIONS

Brenda Collins. Discovery Medicine, Jul. 2011.*

1997-11-17-NM_shotgun.dbs and 1997-12-15-NM.dbs, located at <ftp://ftp.sanger.ac.uk/pub/pathogens/nm/old data/>.

Aasel et al. (1998). Abstract from the 11th International Pathogenic *Neisseria* Conference, Nice France, Nov. 1-6, 1998. pp. 37-38.

Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.

Beernink et al. (Jun. 2008). "Bactericidal antibody responses, induced by meningococcal recombinant chimeric factor H-binding protein vaccines," Infection and Immunity 76(6):2568-2575.

Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.

Bernfield L. et al. (Sep. 2002). "Identification of a novel vaccine candidate for group B *Neisseria meningitidis*," Thirteenth International Pathogenic *Neisseria* Conference, Norwegian Institute of Public Health, Oslo, Norway, pp. 116 and 124.

(Continued)

*Primary Examiner* — S. Devi

(74) *Attorney, Agent, or Firm* — Morrison & Foerster LLP

(57) ABSTRACT

This invention provides, among other things, proteins, polypeptides, and fragments thereof, derived from the bacteria *Neisseria meningitidis* B. Also provided are nucleic acids encoding for such proteins, polypeptides, and/or fragments, as well as nucleic acids complementary thereto e.g., antisense nucleic acids). Additionally, this invention provides antibodies which bind to the proteins, polypeptides, and/or fragments. This invention further provides expression vectors useful for making the proteins, polypeptides, and/or fragments, as well as host cells transformed with such vectors. This invention also provides compositions of the proteins, polypeptides, fragments, and/or nucleic acids, for use as vaccines, diagnostic reagents, immunogenic compositions, and the like. Methods of making the compositions and methods of treatment with the compositions are also provided. This invention also provides methods of detecting the proteins, polypeptides, fragments, and/or nucleic acids.

16 Claims, No Drawings

(56) References Cited

FOREIGN PATENT DOCUMENTS

| | | | |
|---|---|---|---|
| WO | WO-98/17805 | | 4/1998 |
| WO | WO-98/18810 | A1 | 5/1998 |
| WO | WO-98/49288 | A1 | 11/1998 |
| WO | WO-98/55495 | A2 | 12/1998 |
| WO | WO-99/57280 | A | 11/1999 |
| WO | WO-00/22430 | A2 | 4/2000 |
| WO | WO-00/66791 | | 11/2000 |
| WO | WO-01/31019 | | 5/2001 |
| WO | WO-01/52885 | | 7/2001 |
| WO | WO-01/64920 | A | 9/2001 |
| WO | WO-01/64922 | A2 | 9/2001 |
| WO | WO-03/009869 | A1 | 2/2003 |
| WO | WO-03/020756 | A | 3/2003 |
| WO | WO-03/063766 | | 8/2003 |
| WO | WO-2004/032958 | A1 | 4/2004 |
| WO | WO-2004/048404 | | 6/2004 |
| WO | WO-2004/065603 | A2 | 8/2004 |
| WO | WO-2004/094596 | A2 | 11/2004 |
| WO | WO-2006/024954 | A2 | 3/2006 |
| WO | WO-2006/081259 | | 8/2006 |
| WO | WO-2007/060548 | A2 | 5/2007 |
| WO | WO-2007/127665 | A2 | 11/2007 |
| WO | WO-2008/125985 | A2 | 10/2008 |
| WO | WO-2008/149238 | A2 | 12/2008 |
| WO | WO-2009/104097 | A2 | 8/2009 |
| WO | WO-2010/028859 | A1 | 3/2010 |
| WO | WO-2010/046715 | A1 | 4/2010 |

OTHER PUBLICATIONS

Boslego et al. (1991). "Gonorrhea Vaccines," Chapter 17 in Vaccines and Immunotherapy, Cryz S.J. (Ed.), Pergamon Press: New York, NY, pp. 211-223.

Cannon (1989). "Conserved Lipoproteins of Pathogenic *Neisseria* Species Bearing the H.8 Epitope: Lipid-Modified Azurin and H.8 Outer Membrane Protein," Clinical Microbiology Reviews 2(Suppl. ):S1-S4.

Cantini et al. (Mar. 2006). "Solution Structure of the Immunodominant Domain of Protective Antigen GNA 1870 of *Neisseria meningitidis*," Journal of Biological Chemistry 281(11):7220-7227.

Cruse et al. (2003). Illustrated Dictionary of Immunology, 2nd Edn.m CRC Press, pp. 46, 166, and 382.

Database accession No. NMB1994 (cf. XP2231040) (Tettelin et al.), uploaded Oct. 1, 2000.

Declaration by Dr. Julian Parkhill dated Jun. 12, 2008, submitted in opposition proceedings for EP1645631, 2 pages.

Delvig, A. A. et al. (Jul. 1997). "Vaccine-Induced IgG Antibodies to the Linear Epitope on the PorB Outer Membrane Protein Promote Opsonophagocytosis of *Neisseria meningitides* by Human Neutrophils," Clinical Immunology and Immunopathology 84(1):27-35.

Dillard, J. P. et al. (1997) "A Peptidoglcan Hydrolase Similar to Bacteriophage Endolysins Acts as an Autolysin in *Neisseria gonorrhoeae*," Molecular Microbiology 25(5):893-907.

European Search Report and Examination Report mailed Jun. 18, 2007, for European Application No. 07075161.5 filed Oct. 30, 2000, 10 pages.

Farley J. et al. (Sep. 2002). "Characterization, cloning and expression of different subfamilies of the ORF 2086 gene from *Neisseria meningitidis*," Thirteenth International Pathogenic *Neisseria* Conference, Norwegian Institute of Public Health, Oslo, Norway, p. 124.

Feavers et al. (2009). "Meningococcal protein antigens and vaccines," Vaccine 275:B42-B50.

Fleischmann et al. (1995). "Whole-Genome Random Sequencing and Assembly of *Haemophilus influenzae* Rd," Science 269:496-501.

Fletcher et al. (2004). "Vaccine Potential of the *Neisseria meningitidis* 2086 Lipoprotein," Infection and Immunity 72(4): 2088-2100.

Fontana et al. (2002). A genomic approach Abstract from the 13th International Pathogenic *Neisseria* Conference, Oslo, Norway, Sep. 1-6, 2002. p. 248.

Forster et al. (1998). "The complete nucleotide sequence of the potexvirus white clover mosaic virus," Nucleic Acid Research. 16:291-303.

Fussenegger et al. (1996). "Tetrapac (tpc), a Novel Genotype of *Neisseria Gonorrhoeae* Affecting Epithelial Cell Invasion, Natural Transformation Competence and Cell Separation," Molecular Microbiology 19:1357-1372.

Giuliani et al. (2006). "A universal vaccine for serogroup B meningococcus," PNAS 103(29):10834-10839.

Giuliani et al. (Feb. 2005). "The Region Comprising Amino Acids 100 to 255 of *Neisseria meningitidis* Lipoprotein GNA 1870 Elicits Bactericidal Antibodies," Infection and Immunity 73(2):1151-1160.

Greenspan et al. (1999). "Defining Epitopes: It's Not as Easy as It Seems," Nature Biotechnology 17:936-937.

Harlow et al. (1988). Antibodies: A Laboratory Manual. Cold Spring Harbor Laboratory: New York, p. 76.

Hou et al. (2005) "Protective antibody responses elicited by a meningococcal outer membrane vesicle vaccine with overexpressed genome-derived neisserial antigen 1870," J Infect Dis 192(4):580-90.

Jacobsson et al. (2009). "Prevalence and sequence variations of the genes encoding the five antigens included in the novel 5CVMB vaccine covering group B meningococcal disease" Vaccine 27:1579-1584.

JCVI-CMR website showing Z2491 Sanger sequence (http://cmr.jcvi.org/tigr-scripts/CMR/shared/Genomes.cgi and links). (2010).

Jiang et al., (2010) "Broad vaccine coverage predicted for a bivalent recombinant factor H binding protein based vaccine to prevent serogroup B meningococcal disease" Vaccine 28:6086-6093.

Koeberling et al. (2007). "Improved immunogenicity of a H44/76 group B outer membrane vesicle vaccine with over-expressed genome-derived Neisserial antigen 1870," Vaccine 25(10):1912-1920.

Lommatzsch et al. (1997). "Outer membrane localization of murein hydrolases: MltA, a third lipoprotein lytic transglycosylase in *Escherichia coli*," Journal of Bacteriology 179(17): 5465-5470.

Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.

Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.

Malorny et al. (1998). "Sequence Diversity, Predicted Two-Dimensional Protein Structure, and Epitope Mapping of Neisserial Opa Proteins," J. Bacteriol, 180(5):1323-1330.

Masignani V. (Mar. 17. 2003). "Vaccination against *Neisseria meningitidis* using three variants of the lipoprotein GNA1870," J. Exp. Med. 197(6):789-799.

Millan et al. (1998). "CpG DNA Can Induce Strong Th1 Humoral and Cell-Mediated Immune Responses Against Hepatitis B Surface Antigen in Young Mice," Proc. Natl. Acad. Sci. USA 95(26):15553-15558.

Morley, S. et al. (Dec. 12, 2001). "Vaccine prevention of meningococcal disease, coming soon?" Vaccine 20(5-6):666-687.

Murphy et al., (2009) "Sequence diversity of the factor H binding protein vaccine candidate in epidemiologically relevant strains of serogroup B *Neisseria meningitidis*" J Infect Dis 200:379-389.

Nassif (2000). "A Furtive Pathogen Revealed," Science 287:1767-1768.

Notice of Opposition against European Patent EP 1645631, granted on Oct. 24, 2007. Opposition filed on Jul. 23, 2008. 20 pages.

Notice of Opposition mailed Apr. 3, 2008 by GlaxoSmithKline Biologicals S.A., directed to European Patent No. EP 1534326 B1, granted Jul. 4, 2007. 21 pages.

Novartis (Oct. 9, 2008) "New Phase II data show Novartis investigational Meningitis B vaccine may also protect infants six months and older," Media Release, 4 pages.

Pajon et al., "Frequency of factor H-binding protein modular groups and susceptibility to cross-reactive bactericidal activity in invasive meningococcal isolates" Vaccine 28(2010):2122-2129.

(56) References Cited

OTHER PUBLICATIONS

Parkhill, J. et al. (Mar. 2000). "Complete DNA Sequence of a Serogroup A Strain of *Neisseria meningitides* Z2491," Nature 404:502-505.
Parkhill, "*Campylobacter jejuni* genome sequence as the Sanger Centre," Post on BIOSCI/Bionet of May 8, 1998.
Patentee's Response to Opposition mailed Jan. 19, 2009, by Novartis Vaccines and Diagnostics S.R.L., directed to European Patent No. EP 1534326 B1, granted Jul. 4, 2007. 29 pages.
Patentees' Response to Opposition against European Patent EP 1645631, granted on Oct. 24, 2007, 13 pages.
Pizza et al. (2000). "Identification of Vaccine Candidates Against Serogroup B Meningococcus by Whole-Genome Sequencing," Science 287(5459):1816-1820.
Pizza et al. (2008) "Factor H-binding protein, a unique meningococcal vaccine antigen" Vaccine 26S:I46-8.
Progress through the Sanger Institute FTP server (May 12, 2009), 15 pages.
PSORT analysis of 200 of the sequences disclosed in PCT/US99/09346 (Jan. 1, 2010), 209 pages.
PSORT analysis of Seq ID No. 4 and 6, and of 'Contig295' 300mer (May 8, 2009), 5 pages.
PSORT prediction result for Seq ID No. 2 (Mar. 30, 2010), 1 page.
Response to Communication, filed in EP Application No. 07075161. 5. Oct. 28th, 2009.
Rinaudo et al. (2009). "Vaccinology in the genome era", The Journal of Clinical Investigation, 119(9):2515-2525.
Romero et al., "Current status of meningococcal group B vaccine candidates: capsular or noncapsular?" Clin. Microbiol. Rev. 7(4):559-575, 1994.
Sanger Centre's "Projects" website as of Dec. 10, 1997 as retrievable via http://web.archive.org.
Scarselli et al. (Feb. 13, 2009). "Epitope Mapping of a Bactericidal Monoclonal Antibody against the Factor H Binding Protein of *Neisseria meningitides*," Journal of Molecular Biology 386(1):97-108.
Schneider et al. (Apr. 16, 2009) "*Neisseria meningitidis* recruits factor H using protein mimicry of host carbohydrates," Nature 458(7240):890-893.
Sequence for "Putative Lipoprotein [*Neisseria Meningitidis* Z2491]," NCBI Reference Sequence: YP_002342062.1, Mar. 30, 2000.
Serruto et al. (2009). "Genome-based approaches to develop vaccines against bacterial pathogens," Vaccine 27:3245-3250.
Sun et al. (1998). "DNA as an Adjuvant: Capacity of insect DNA and Synthetic Oligodeoxynucleotides to Augment T Cell Responses to Specific Antigen," J. Experimental Medicine 187(7):1145-1150.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Tabata. (1996). "Membrane Bound Lytic Translycosylase A MltA Synechocystis sp Strain PCC 6803," Database EMBL EB1 Acc No. Q55666.
Teerlink et al. (1987). "Antigenic and Immunogenic Properties of Cyanogen Bromide Peptides from Gonococcal Outer Membrane Protein Ib," J. Exp. Med. 166:63-76.
Telford et al. (2003). "Genomic and Proteomics in Vaccine Design", in New Bacterial Vaccines, edited by Ellis et al. Kleweur Academic/Plenum Publishers, USA. pp. 1-11.
Tettelin H et al. (Mar. 10, 2000). "Complete genome sequence of *Neisseria meningitidis* serogroup B strain MC58," Science 287(5459):789-799.
The printed output from the NCBI open reading frame finder (Oct. 20, 2008), 12 pages.
United States Office Action mailed Feb. 11, 2009, for U.S. Appl. No. 10/181,600, filed Jan. 17, 2001, 5 pages.
United States Office Action mailed on Jul. 24, 2008, for U.S. Appl. No. 10/181,600, filed Jan. 17, 2001, 23 pages.
United States Office Action mailed on Jul. 7, 2009, for U.S. Appl. No. 10/181,600, filed Jan. 17, 2001, 23 pages.
U.S. Appl. No. 60/098,685, "*Neisseria* Spp, Polypeptide, Gene Sequence and Uses Thereof," filed Sep. 1, 1998.
Welsch et al. (2004). "Protective Activity of Monclonal Antibodies to Genome-Derived Neisserial Antigen 1870, a *Neisseria meningitidis* Candidate Vaccine," The Journal of Immunology 172:5606-5615.
Welsch et al. (Oct. 30, 2006) "A novel mechanism for complement-mediated killing of encapsulated *Neisseria meningitidis* elicited by monoclonal antibodies to factor H-binding protein (genome-derived *Neisserial* antigen 1870)" Molecular Immunology 44(1-3):256.
Welsch et al. (Apr. 1, 2008). "Complement-dependent synergistic bactericidal activity of antibodies against factor H-binding protein, a sparsely distributed *meningococcal* vaccine antigen," J Infect Dis 197(7):1053-1061.
Zhu et al. (2005) "Evaluation of recombinant lipidated P2086 protein as a vaccine candidate for group B *Neisseria meningitidis* in a murine nasal challenge model," Infect Immun 73(10):6838-45.
Zollinger (1997). "New and Improved Vaccines Against Meningococcal Disease" in New Generation Vaccines, 2nd Ed., edited by Levine et al., Marcel Dekker, New York. pp. 469-488.
Aderson et al. (2010). "Effectiveness of a bivalent factor H binding protein vaccine across *Neisseria meningitidis* serogroups," 17th International Pathogenic *Neisseria* Conference 2010, p. 196.
Ala'Aldeen et al. (2010) "Human antibody response to the meningococcal factor H binding protein (LP2086) during invasive disease, colonization and carriage," Vaccine 28:7667-75.
Ambrose et al. (2006). "Characterization of LP2086 expression in *Neisseria meningitidis*," 15th International Pathogenic *Neisseria* Conference 2006, p. 103.
Anderson et al. (2008). "Functional cross-reactive antibodies are elicited by a group B *Neisseria meningitidis* bivalent recombinant lipidated LP2086 vaccine in cynomolgusmacaques," 16th International Pathogenic *Neisseria* Conference (IPNC) P100, pp. 170-171.
Anderson et al. (2009). "Epidemiology of the serogroup B *Neisseria meningitidis* (MnB) factor H binding protein and implications for vaccine development," European Society for Paediatric Infectious Disease Symposium 2009, p. 505.
Anderson et al. (2009). "Development of a factor H binding protein vaccine for borad protection against invasive *Neisseria meningitidis* serogroup B (MnB) disease," 10th European Meningococcal Disease Society Congress 2009, p. 39.
Anderson et al. (2012). "Potential impact of the bivalent rLP2086 vaccine on *Neisseria meningitidis* invasive disease and carriage isolates in two adolescent populations," European Society for Paediatric Infectious Disease Symposium 2012, p. 807.
Anderson et al. (2013) "Potential impact of the bivalent rLP2086 vaccine on *Neisseria meningitidis* carriage and invasive serogroup B disease," Hum Vacc Immunotherap 9:471-9.
Appendix I to Statement of Grounds of Appeal filed by df-mp on Sep. 28, 2012, in relation to EP1645631, 1 pages.
Appendix II to Statement of Grounds of Appeal filed by df-mp on Sep. 28, 2012, in relation to EP1645631, 2 pages.
Beernick (Jul. 2010) "Impaired immungenicity of a meningococcal factor H-binding protein vaccine engineered to eliminate factor h binding," Clin Vac Immunol 17(7):1074-1078.
Bentley et al. (2004). Identification of two immunologically distinct domains on the LP2086 outer membrane lipoprotein of *Neisseria meningitidis*, 14th International Pathogenic *Neisseria* Conference 2004, p. 144.
Bouvier et al. (1991). "A gene for a new lipoprotein in the dapA-purC interval of the *Escherichia coli* chromosome," J Bacteriol 173(17):5523-5531.
Chen, et al. (1994). "Determination of the optimal aligned spacing between the Shine-Dalgarno sequence and the translation initiation codon of *Escherichia coli* mRNAs," Nucleic Acids Res. 22(23):4953-4957.
Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1>.

(56) References Cited

OTHER PUBLICATIONS

Clinical Trial No. NCT00808028, (2008). "A study evaluating safety and immunogenicity of meningococcal B rIp2086 vaccine in adolescents," U.S. National Institutes of Health, retrieved online at <http://clinicaltrials.gov/ct2/show/NCT00808028?term=NCT00808028&rank=1>.
Cohn et al. (2010). "Potential Impact of Serogroup B Vaccines: Prevalence of candidate vaccine antigens among invasive *Neisseria meningitidis* isolates in the United States," 17th International Pathogenic *Neisseria* Conference 2010, p. 77.
Cordis, "Preparation of meningococcal antigens," posted online on Feb. 2, 2005, 2 pages.
Declaration by Dr. Ellen Murphy, Ph.D., dated Sep. 14, 2011, submitted in opposition proceedings for EP1645631, 4 pages.
Declaration by E. Richard Moxon dated Feb. 16, 2013, submitted in opposition proceedings for EP1645631, 5 pages.
Declaration by Emilio A. Emini, Ph.D., dated Nov. 2, 2011, submitted in opposition proceedings for EP1645631, 5 pages.
Declaration by Isabel Delany, dated Feb. 18, 2013, submitted in opposition proceedings for EP1645631, 5 pages.
Declaration by Prof. Paul Dunman, Ph.D., dated Sep. 25, 2012, submitted in opposition proceedings for EP1645631, 14 pages.
Declaration by Rino Rappuoli, dated Oct. 13, 2011, submitted in opposition proceedings for EP1645631, 5 pages.
Declaration by Vega Masignani dated Feb. 18, 2013, submitted in opposition proceedings for EP1645631, 4 pages.
Delgado et al. (2007). "Lipoprotein NMB0928 from *Neisseria meningitidis* serogroup B as a novel vaccine candidate," Vaccine 25:8420-8431.
Dinthilhac and Claverys (1997). "The adc locus, which affects competence for genetic transformation in *Streptococcus pneumoniae*, encodes an ABC transporter with a putative lipoprotein homologous to a family of streptococcal adhesins," Res Microbiol 148:119-131.
Dlawer et al. (2010). "Human antibody responses to the meningococcal factor H binding protein LP2086 during invasive disease," 17th International Pathogenic *Neisseria* Conference 2010, p. 130.
Facts and Submissions dated May 21, 2012, in relation to EP1645631, 30 pages.
Fraser et al. (1997). "Genomic sequence of a lyme disease spirochaete, *Borrelia burgdorferi*," Nature 390:580-586.
Fraser et al. (1998). "Complete genome sequence of *Treponema pallidum*, the syphilis spirochete," Science 281:375-388.
GenPept accession No. AAF42204, "hypothetical protein NMB1870 [*Neisseria meningitidis* MC58]," retrieved on Sep. 26, 2012, 2 pages.
Giuliani et al. (2010). "Measuring antigen-specific bactericidial responses to a multicomponent vaccine against serogroup B meningococcus," Vaccine 28:5023-5030.
Gold and Stormo (1987). "Translation Initiation", in *Escherichia* con and *Salmonella typhimurium*, Cellular and Molecular Biology, Ed. Neidhardt, pp. 1302-1307.
Gorringe et al. (2009). "16th International Pathogenic *Neisseria* Conference: recent progress towards effective meningococcal disease vaccines," Human Vaccines 5(2):53-56.
Grandi (2005). "Reverse vaccinology: a critical analysis," in Encyclopedia of Genetics, Genomics, Proteomics and Bioinformatics, pp. 1322-1326.
Granoff, DM. (2009). Relative importance of complement-mediated bactericidal and opsonic activity for protection against meningococcal disease. Vaccine 27(Supplement 2): B117-B125.
Harris et al. (2008). "Development and qualification of serum bactericidal assays for *Neisseria meningitidis* serogroup B," 16th International Pathogenic *Neisseria* Conference 2008, p. 268-269.
Harris et al. (2010). "Robustness of the Serum Bactericidal Activity (SBA) Assay for *Neisseria meningitidis* serogroup B," 17th International Pathogenic *Neisseria* Conference 2010, p. 169.
Harris et al. (2011) "Preclinical evidence for the potential of a bivalent fHBP vaccine to prevent *Neisseria meningitidis* serogroup C disease," Human Vaccines 7:1 (suppl) 1-7.
Hayashi and Wu, "Identification and characterization of lipid-modified proteins in bacteria," Chapter 10 in Lipid Modifications of Proteins: A Practical Approach, Hooper and Turner (eds.), published in 1992, 27 pages.
Hem et al. (1995). "Structure and properties of aluminum-containing adjuvants," Vaccine Design. Subunit and Adjuvant Approach, pp. 249-276.
Hodge et al. (2006). "Development of a luminex-based meningococcal rLP2086-specific human IgG assay," 15th International Pathogenic *Neisseria* Conference 2006, p. 113.
Hoiseth et al. (2008). "LP2086 and MLST distribution in epidemiologically relevant strains of serogroup B *Neisseria meningitidis*," 16th International Pathogenic *Neisseria* Conference 2008, p. 205.
Hung et al. (2011). "The *Neisseria meningitidis* macrophage infectivity potentiator protein induces cross-strain serum bactericidal sctivity and is a potential serogroup B vaccine candidate," Infect Immun 79(9):3784-3791.
Jansen et al. (2008). "Bivalent recombinant LP2086 vaccine to provide broad protection against *Neiseria meningitidis* B disease: immunological correlates of protection and how to assess coverage against invasive MnB strains," 16th International Pathogenic *Neisseria* Conference 2008, p. 80-81.
Jansen et al. (2009). "Development of a bivalent factor H binding protein vaccine to broadly protect against invasive *Neisseria meningitides* serogroup B (MnB) disease," European Society for Paediatric Infectious Disease Symposium 2009, p. 311.
Jansen et al. (2010). "Estimating effectiveness for *Neisseria meningitidis* serogroup B (MnB) vaccine candidates composed of non-serogroup specific antigens," 17th International Pathogenic *Neisseria* Conference 2010, p. 37.
Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.
Jiang et al. (2003). "Using rate of acid neutralization to characterize aluminum phosphate adjuvant," Pharma Dev Tech 8(4):349-356.
Jiang et al. (2006). "Serum IgG response induced by a bivalent recombinant LP2086 provides broad protection against serogroup B *Neisseria meningitidis*," 15th International Pathogenic *Neisseria* Conference 2006, p. 113.
Jiang et al. (2008). "Prediction of broad vaccine coverage for a bivalent rLP2086 based vaccine which elicits serum bactericidal activity against a diverse collection of serogroup B meningococci," 16th International Pathogenic *Neisseria* Conference 2008, p. 57-58.
Johnson et al. (1999). "Analysis of the human Ig isotype response to lactoferrin binding protein A from *Neisseria meningitidis*," FEMS Immun. Med. Microbial. 25(4): 349-354.
Jones et al. (2009). "Generation of human serum complement lots that perform consistently for use in *Neisseria meningitidis* serogroup B (MnB) vaccine clinical trials," European Society for Paediatric Infectious Disease Symposium 2009, p. 566.
Juncker et al. (2003). "Prediction of lipoprotein signal peptides in gram-negative bacteria," Protein Sci 12:1652-1662.
Koeberling et al. (2009). "Meningococcal outer membrane vesicle vaccines derived from mutant strains engineered to express factor H binding proteins from antigenic variant groups 1 and 2," Clin Vac Immunol, 16(2):156-162.
Liebl et al. (1997). "Properties and gene structure of the *Thermotoga maritima* alpha-amylase AmyA, a putative lipoprotein of a hyperthermophilic bacterium," J Bacteriol 179(3):941-948.
Marshall et al. (2008). "A randomized, placebo-controlled, double-blind, phase 1 trial of ascending doses of meningococcal group B rLP2086 vaccine in healthy adults," 16th International Pathogenic *Neisseria* Conference 2008, p. 271-272.
Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.
Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.

(56) References Cited

OTHER PUBLICATIONS

Marshall et al. (2013) "A phase 2 open-label safety and immunogenicity study of a meningococcal B bivalent rLP2086 vaccine in healthy adults," Vaccine 31:1569-75.
Mascioni et al. (2008). "Determination of the domain and solution structure of rLP2086, a meningococcal vaccine candidate and human factor H binding protein," 16th International Pathogenic *Neisseria* Conference 2008, p. 77-78.
Mascioni et al. (2009) "Structural basis for the immunogenic properties of the meningococcal vaccine candidate LP2086," J Biol Chem 284:8738-46.
Mascioni et al. (2010) "NMR dynamics and antibody recognition of the meningococcal lipidated outer membrane protein LP2086 in micellar solution," Biochim Biophys Acta 1798:87-93.
McNeil et al. (2009) "Detection of LP2086 on the cell surface of *Neisseria meningitidis* and its accessibility in the presence of serogroup B capsular polysaccharide," Vaccine 27:3417-21.
McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic *Neisseria* Conference 2010, p. 94.
McNeil et al. (2013) "Role of factor H binding protein in *Neisseria meningitidis* virulence and its potential as a vaccine candidate to broadly protect against meningococcal disease," Microbiol Mol Biol Rev 77:234.
Milagres et al. (1998). "Specificity of bactericidal antibody response to serogroup B meningococcal strains in Brazilian children after immunization with an outer membrane vaccine," Infection and Immun. 66(10): 4755-4781.
Munkley, et al. (1991). "Blocking of bactericidal killing of *Neisseria meningitidis* by antibodies directed against slacc 4 outer membrane proteins," Microbial Pathogenesis 11: 447-452.
Murphy et al. (2008). "Sequence diversity of vaccine candidate LP2086 in *Neisseria meningitidis* serogroup B strains causing invasive disease," 16th International Pathogenic *Neisseria* Conference 2008, p. 61.
Murphy et al. (2010). "Prevalence of Factor H Binding Protein (fHBP) Variants in *N. meningitidis* Carriage Isolates," 17th International Pathogenic *Neisseria* Conference 2010, p. 96.
Novartis (Jan. 22, 2013) "Novartis receives EU approval for Bexsero®, first vaccine to prevent the leading cause of life-threatening meningitis across Europe," Media Release, 3 pages.
Pajon et al. (2012). "Design of meningococcal factor H binding protein mutant vaccines that do not bind human complement factor H," Infect Immun 80:2667-2677.
Pettersson, et al. (2006). "Vaccine potential of the *Neisseria meningitidis* lactoferrin-binding proteins LbpA and LbpB," Vaccine 24(17):3545-3557.
Pillai et al. (2005) "Outer membrane protein (OMP) based vaccine for *Neisseria meningitidis* serogroup B," Vaccine 23(17-18):2206-2209.
Prosite, "ScanProsite Results Viewer: USERSEQ1 (280aa)," retrieved on Jun. 21, 2012, 1 page.
Pugsley (1993). "The complete general secretory pathway in gram-negative bacteria," Microbiological Rev 5(1):50-108.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Richmond et al. (2008). "A randomized, observer-blinded, active control, phase 1 trial of meningococcal serogroup B rLP2086 vaccine in healthy children and adolescents aged 8 to 14 years," 16th International Pathogenic *Neisseria* Conference 2008, p. 270-271.
Richmond et al. (2010). "Safety & immunogenicity of serogroup B *Neisseria meningitidis* (MnB) rLP2086 vaccine in adults and adolescent subjects: overview of 3 clinical trials," 17th International Pathogenic *Neisseria* Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent *Neisseria meningitidis* recombinant lipidated factor H binding protein vaccine in young adults: Results of a randomized, controlled, dose-escalation phase 1 trial," Vaccine 30(43):6163-74.
Richmond et al. (2012a) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Seeber et al. (1991). "Predicting the adsorption of proteins by aluminum-containing adjuvants," Vaccine 9(3):201-203.
Seib et al. (2010). "Influence of serogroup B meningococcal vaccine antigens on growth and survival of the mengococcus in vitro and in ex vivo and in vivo models of infection," Vaccine 28(12):2416-2427.
Sheldon et al. (2011). "Phase 1, Randomized, Open-Label, Study to Assess the Safety and Immunogenicity of Serogroup B *Neisseria Meningitidis* (Mnb) rLP2086 Vaccine in Healthy Adults," 14th Annual Conference on Vaccine Research, 2011, p. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of *Erwinia chrysanthemi* 3937," Mole Microbiol 19(3):455-466.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Sutcliffe and Russell (1995). "Lipoproteins of gram-positive bacteria," J Bacteriol 177(5):1123-1128.
Tan et al. (2010). "Advances in the development of vaccines against *Neisseria meningitidis*," NEJM 362(16):1511-1520.
TIGR website as of 1998, 8 pages.
von Heijne (1989). "The structure of signal peptides from bacterial lipoproteins," Protein Engineering 2(7):531-534.
Wang et al. (2010). "Prevalence and genetic diversity of candidate vaccine antigens among invasive *Neisseria meningitidis* isolates in the United States," 17th International Pathogenic *Neisseria* Conference 2010, p. 122.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
Wu et al. (1996). "A protein class database organized with ProSite protein groups and PIR superfamilies," J Comp Biol 3(4):547-561.
York et al. (2010). "fHBP epidemiology of invasive meningococcal B isolates from Spain and Germany: age based," 17th International Pathogenic *Neisseria* Conference 2010, p. 109.
Zhu et al. (2004). "Evaluation of the purified recombinant lipidated P2086 protein as a vaccine candidate for group B *Neisseria meningitidis* in a murine nasal challenge model," 14th International Pathogenic *Neisseria* Conference 2004, p. 199.
Zhu et al. (2006) "Intranasal immunization of mice with recombinant lipidated P2086 protein reduces nasal colonization of group B *Neisseria meningitidis*," Vaccine 24:5420-5.
Zhu et al. (2006). "Effective immunization strategy against group B *Neisseria meningitidis* using purified recombinant lipidated P2086 protein," 15th International Pathogenic *Neisseria* Conference 2006, p. 47.
Zlotnick et al. (2009). "Epidemiology of the serogroup B *Neisseria meningitidis* (MnB) factor H binding protein in strains sampled from Spain and Germany in the years 2001-2006," 10th European Meningococcal Disease Society Congress 2009, p. 81.
Zlotnick et al. (2010). "Biochemical and biophysical analysis indicates conformation plays an important role in the binding of hfH and

(56) References Cited

OTHER PUBLICATIONS antibodies to the fHBP of *N. meningitidis*," 17th International Pathogenic *Neisseria* Conference 2010, p. 38.
Adams (1996). "Should Non-Peer-Reviewed Raw DNA Sequence Data Release Be Forced on the Scientific Community?", Science, 274: 534-536.
BenMohamed et al. (2002). "Lipopeptide vaccines—yesterday, today, and tomorrow," Lancet 2(7):425-431.
Bhat et al. (1999). "Discs lost, a novel multi-PDZ domain protein, establishes and maintains epithelial polarity," Cell 96:833-845.
Biswas et al. (1995). "Characterization of IbpA, the structural gene for a lactoferrin receptor in *Neisseria gonorrhoeae*," Infection and Immunity, 63(8): 2958-2967.
Blattner et al. (1997). "The complete genome sequence of *Escherichia coli* K-12," Science 277 (5331): 1453-1474.
Cole et al. (1998). "Deciphering the biology of *Mycobacterium tuberculosis* from the complete genome sequence," Nature 394:651-653.
Database UniProt (Oct. 1, 2000), "SubName: Full=Uncharacterized protein" retrieved from EBI, accession No. Q9JXV4 Database accession No. Q9JXV4.
Decision revoking the European Patent, filed in opposition against EP1976990, dated Nov. 11, 2013, 15 pages.
Decision to refuse a patent application, filed in the Opposition against EP1645631, dated Apr. 28, 2009, 7 pages.
Declaration by Dr. Julian Parkhill, filed in the Opposition against EP1645631, dated Jul. 10, 2014, 5 pages.
Declaration by Ellen Murphy, filed in the Opposition against EP1645631, dated May 12, 2014, 3 pages.
Donnelly et al. (2010). "Qualitative and quantitative assessment of meningococcal antigens to evaluate the potential strain coverage of protein-based vaccines," Proc Natl Acad Sci U S A, 107(45):19490-5.
Elzanowski et al. (2013). "The Genetic Codes, a compilation," Retrieved from http://www.bioinformatics.org/JaMBW/2/3/TranslationTables.html.
Experimental data: expression of NspA, '287' and '741' on 3 strains of bacteria, filed in opposition against EP1534326, dated Aug. 4, 2010. 2 pages.
Gene Browser, Nature Technology Corporation, filed in the Opposition against EP1645631, dated Jun. 26, 2013, 6 pages.
Holst et al. (2014). "Variability of genes encoding surface proteins used as vaccine antigens in meningococcal endemic and epidemic strain panels from Norway," Vaccine 32:2722-2731.
Interlocutory decision in opposition proceedings, filed in the Opposition against EP1645631, dated May 21, 2012, 82 pages.
Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.
Kovacs-Simon et al. (2011). "Lipoproteins of Bacterial Pathogens," Infect Immun 79(2):548-561.
Lewis et al. (2010). "The meningococcal vaccine candidate neisserial surface protein A (NspA) binds to factor H and enhances meningococcal resistance to complement," PLoS Pathogens 6(7):e1001027.
Liechti et al. (2012). "Outer membrane biogenesis in *Escherichia coli, Neisseria meningitidis*, and *Helicobacter pylori*: paradigm deviations in *H. pylori*," Front Cell and Infect Microbiol 2:article 29.
Lindblad, (2004). "Aluminium compounds for use in vaccines," Immunol Cell Biol.,82(5):497-505.
Madico et al. (2006). "The meningococcal vaccine candidate GNA1870 binds the complement regulatory protein factor H and enhances serum resistance," J Immunol 177(1):501-510.
Meyer et al. (1984). "Pilus genes of *Neisseria gonorrheae*: Chromosomal organization and DNA sequence," Proc. Natl. Acad. Sci. USA 81: 6110-6114.
Minutes of the oral proceedings, filed in the Opposition against EP1645631, dated Feb. 11, 2014, 4 pages.
Notice of Opposition against EP 1562983, filed on Jul. 1, 2014, 23 pages.
Notice of Opposition against EP1645631, filed in the Opposition against EP1645631, dated Jul. 23, 2008, 25 pages.
Notice of Opposition filed May 24, 2012, filed in opposition against EP1976990, 19 pages.
Novartis (Jun. 9, 2011). "Novartis candidate vaccine Bexsero® shows significant potential in providing broad coverage against meningococcal serogroup B infections." Media Release, 6 pages.
Opponent's Further Submission in Preparation of the Oral Proceedings, filed in the Opposition against EP1645631, dated Nov. 3, 2011, 6 pages.
Opponent's Response to the Patentee's Submission dated Feb. 18, 2013, filed in the Opposition against EP1645631, dated Jul. 24, 2014, 34 pages.
Opponents Final Written Submission in Preparation of Oral Proceedings, filed in the Opposition against EP1645631, dated Sep. 14, 2011, 28 pages.
ORF Finder (2013). "Bacterial Code," Retrieved from http://www.ncbi.nlm.nih.gov/gorf/gorf.html, 3 pages.
Patentee's Submissions under Rule 116 EPC, filed in the Opposition against EP1645631, dated Sep. 13, 2011, 13 pages.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Sandbu et al. (2007). "Immunogenicity and safety of a combination of two serogroup B meningococcal outer membrane vesicle vaccines," Clin Vaccine Immunol, 14(9):1062-9.
Santos et al. (2002). "Serum bactericidal responses in *Rhesus macaques* immunized with novel vaccines containing recombinant proteins derived from the genome of *N. meningitidis*," 13th International Pathogenic *Neisseria* Conference 2002, p. 298.
Seib et al. (2011). "Characterization of Diverse Subvariants of the Meningococcal Factor H (fH) Binding Protein for Their Ability to Bind fH, to Mediate Serum Resistance, and to Induce Bactericidal Antibodies," Infect Immun, 79(2):970-81.
Sprengart et al. (1997). "Functional importance of RNA interactions in selection of translation initiation codons," Molecular Microbiology, 24(1): 19-28.
Submission of the Patentee of Jul. 6, 2012, filed Jun. 24, 2014, in the Opposition against EP1645631, 4 pages.
Summons to oral proceedings pursuant to Rule 115(1) EPC, filed in the Opposition against EP1645631, dated Nov. 11, 2013, 12 pages.
Supplementary Submission to the Grounds of Appeal, filed in the Opposition against EP1645631, dated Sep. 28, 2012, 2 pages.
Swaminathan (1996). "Molecular cloning of the three base restriction endonuclease R.CviJI from eukaryotic *Chlorella* virus IL-3A," Nucleic Acids Research, 24(13): 2463-2469.
TIGR Microbial Database, filed in the Opposition against EP1645631, dated Jun. 20, 2012, 14 pages.
U.S. Appl. No. 60/647,911, "GNA 1870-based vesicle vaccines for broad spectrum protection against diseases caused by *Neisseria meningitidis*," filed Jan. 27, 2005.
Vesikari et al. (2013). "Immunogenicity and safety of an investigational multicomponent, recombinant, meningococcal serogroup B vaccine (4CMenB) administered concomitantly with routine infant and child vaccinations: results of two randomized trials," Lancet 381:625-35.
Voulhoux and Tommassen (2002). "Transport of lipoproteins to the cell surface in *Neisseria meningitidis*," 13th International Pathogenic *Neisseria* Conference 2002, p. 31.
Written Submission to Oral Proceedings, filed in opposition against EP1976990, dated Jul. 24, 2013, 11 pages.
Zollinger et al. (2010). "Design and evaluation in mice of a broadly protective meningococcal group B native outer membrane vesicle vaccine," Vaccine, 28(31):5057-5067.

* cited by examiner

NEISSERIAL ANTIGENIC PEPTIDES

CROSS REFERENCE TO RELATED APPLICATIONS

This application is a Divisional of U.S. patent application Ser. No. 10/111,983, filed Feb. 26, 2003, now U.S. Pat. No. 8,734,812, which is the National Stage of International Patent Application of PCT/IB2000/001661, filed Oct. 30, 2000, which claims the benefit of U.S. Provisional Patent Application Ser. No. 60/162,616, filed Oct. 29, 1999, each of which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 223002100011SeqListing.txt, date recorded: Feb. 23, 2012, size: 19,155 KB).

TECHNICAL FIELD

This invention relates to antigenic peptide sequences from the bacteria *Neisseria meningitidis* and *Neisseria gonorrhoea.*

BACKGROUND ART

*N. meningitidis* is a non-motile, Gram-negative diplococcus that is pathogenic in humans.

Based on the organism's capsular polysaccharide, 12 serogroups of *N. meningitidis* have been identified. Group A is the pathogen most often implicated in epidemic disease in sub-Saharan Africa. Serogroups B and C are responsible for the vast majority of cases in the United States and in most developed countries. Serogroups W135 and Y are responsible for the rest of the cases in the United States and developed countries.

The meningococcal vaccine currently in use is a tetravalent polysaccharide vaccine composed of serogroups A, C, Y and W135. Meningococcus B remains a problem, however. The polysaccharide approach cannot be used because the menB capsular polysaccharide is a polymer of α(2-8)-linked N-acetyl neuraminic acid that is also present in mammalian tissue. One approach to a menB vaccine uses mixtures of outer membrane proteins (OMPs). To overcome the antigenic variability, multivalent vaccines containing up to nine different porins have been constructed [e.g., Poolman J T (1992) Development of a meningococcal vaccine. *Infect. Agents Dis.* 4:13-28]. Additional proteins to be used in outer membrane vaccines have been the opa and opc proteins, but none of these approaches have been able to overcome the antigenic variability [e.g., Ala'Aldeen & Borriello (1996)]. The meningococcal transferrin-binding proteins 1 and 2 are both surface exposed and generate bactericidal antibodies capable of killing homologous and heterologous strains. [*Vaccine* 14(1):49-53].

DISCLOSURE OF THE INVENTION

The invention provides fragments of the proteins disclosed in international patent applications WO99/57280 and WO00/22430 (the "International Applications"), wherein the fragments comprise at least one antigenic determinant.

Thus, if the length of any particular protein sequence disclosed in the International Applications is x amino acids, the present invention provides fragments of at most x−1 amino acids of that protein. The fragment may be shorter than this (e.g., x−2, x−3, x−4, . . . ), and is preferably 100 amino acids or less (e.g., 90 amino acids, 80 amino acids etc.). The fragment may be as short as 3 amino acids, but is preferably longer (e.g., up to 5, 6, 7, 8, 9, 10, 12, 15, 20, 25, 30, 35, 40, 50, 75, or 100 amino acids).

Preferred fragments comprise the meningococcal peptide sequences disclosed in Table 1, or sub-sequences thereof. The fragments may be longer than those given in Table 1 e.g., where a fragment in Table 1 runs from amino acid residue p to residue q of a protein, the invention also relates to fragments from residue (p−1), (p−2), or (p−3) to residue (q+1), (q+2), or (q+3).

The invention also provides polypeptides that are homologous (i.e., have sequence identity) to these fragments. Depending on the particular fragment, the degree of sequence identity is preferably greater than 50% (e.g., 60%, 70%, 80%, 90%, 95%, 99% or more). These homologous polypeptides include mutants and allelic variants of the fragments. Identity between the two sequences is preferably determined by the Smith-Waterman homology search algorithm as implemented in the MPSRCH program (Oxford Molecular), using an affine gap search with parameters gap open penalty=12 and gap extension penalty=1.

The invention also provides proteins comprising one or more of the above-defined fragments.

The invention is subject to the proviso that it does not include within its scope proteins limited to any of the full length protein sequences disclosed in the International Applications (i.e., the even SEQ IDs: 2-3020 of WO99/57280 and the odd SEQ IDs: 963-1045 of WO00/22430).

The proteins of the invention can, of course, be prepared by various means (e.g., recombinant expression, purification from cell culture, chemical synthesis etc.) and in various forms (e.g., native, C-terminal and/or N-terminal fusions etc.). They are preferably prepared in substantially pure form (i.e., substantially free from other Neisserial or host cell proteins). Short proteins are preferably produced using chemical peptide synthesis.

According to a further aspect, the invention provides antibodies which recognise the fragments of the invention, with the proviso that the invention does not include within its scope antibodies which recognise any of the complete protein sequences in the International Applications. The antibodies may be polyclonal or monoclonal, and may be produced by any suitable means.

The invention also provides proteins comprising peptide sequences recognised by these antibodies. These peptide sequences will, of course, include fragments of the meningococcal proteins in the International Applications, but will also include peptides that mimic the antigenic structure of the meningococcal peptides when bound to immunoglobulin.

According to a further aspect, the invention provides nucleic acid encoding the fragments and proteins of the invention, with the proviso that the invention does not include within its scope nucleic acid encoding any of the full length protein sequences in the International Applications. The nucleic acids may be as short as 10 nucleotides, but are preferably longer (e.g., up to 10, 12, 15, 18, 20, 25, 30, 35, 40, 50, 75, or 100 nucleotides).

In addition, the invention provides nucleic acid comprising sequences homologous (i.e., having sequence identity) to these sequences. The degree of sequence identity is preferably greater than 50% (e.g., 60%, 70%, 80%, 90%, 95%, 99% or more). Furthermore, the invention provides nucleic acid which can hybridise to these sequences, preferably under "high stringency" conditions (e.g., 65° C. in a 0.1×SSC, 0.5% SDS solution).

It should also be appreciated that the invention provides nucleic acid comprising sequences complementary to those described above (e.g., for antisense or probing purposes).

Nucleic acid according to the invention can, of course, be prepared in many ways (e.g., by chemical synthesis, from genomic or cDNA libraries, from the organism itself etc.) and can take various forms (e.g., single stranded, double stranded, vectors, probes etc.). In addition, the term "nucleic acid" includes DNA and RNA, and also their analogues, such as those containing modified backbones, and also peptide nucleic acids (PNA), etc.

According to a further aspect, the invention provides vectors comprising nucleotide sequences of the invention (e.g., expression vectors) and host cells transformed with such vectors.

According to a further aspect, the invention provides compositions comprising protein, antibody, and/or nucleic acid according to the invention. These compositions may be suitable as vaccines, for instance, or as diagnostic reagents, or as immunogenic compositions.

The invention also provides nucleic acid, protein, or antibody according to the invention for use as medicaments (e.g., as vaccines or as immunogenic compositions) or as diagnostic reagents. It also provides the use of nucleic acid, protein, or antibody according to the invention in the manufacture of: (i) a medicament for treating or preventing infection due to Neisserial bacteria; (ii) a diagnostic reagent for detecting the presence of Neisserial bacteria or of antibodies raised against Neisserial bacteria; and/or (iii) a reagent which can raise antibodies against Neisserial bacteria. Said Neisserial bacteria may be any species or strain (such as *N. gonorrhoeae*) but are preferably *N. meningitidis*, especially strain A or strain B.

The invention also provides a method of treating a patient, comprising administering to the patient a therapeutically effective amount of nucleic acid, protein, and/or antibody according to the invention.

According to further aspects, the invention provides various processes, for example:

A process for producing proteins of the invention is provided, comprising the step of culturing a host cell according to the invention under conditions which induce protein expression;

A process for producing protein or nucleic acid of the invention is provided, wherein the protein or nucleic acid is synthesised in part or in whole using chemical means;

A process for detecting polynucleotides of the invention is provided, comprising the steps of: (a) contacting a nucleic probe according to the invention with a biological sample under hybridizing conditions to form duplexes; and (b) detecting said duplexes; and A process for detecting proteins of the invention is provided, comprising the steps of: (a) contacting an antibody according to the invention with a biological sample under conditions suitable for the formation of an antibody-antigen complexes; and (b) detecting said complexes.

A summary of standard techniques and procedures which may be employed in order to perform the invention (e.g., to utilise the disclosed sequences for vaccination or diagnostic purposes) follows. This summary is not a limitation on the invention but, rather, gives examples which may be used, but which are not required.

General

The practice of the present invention will employ, unless otherwise indicated, conventional techniques of molecular biology, microbiology, recombinant DNA, and immunology, which are within the skill of the art. Such techniques are explained fully in the literature e.g., Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Standard abbreviations for nucleotides and amino acids are used in this specification.

All publications, patents, and patent applications cited herein are incorporated in full by reference.

DEFINITIONS

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" e.g., a composition "comprising" X may consist exclusively of X or may include something additional to X, such as X+Y.

The term "antigenic determinant" includes B-cell epitopes and T-cell epitopes.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a meningococcal sequence is heterologous to a mouse host cell. A further example would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

Expression Systems

The meningococcal nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g., structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual, 2nd ed.]*.

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell,* 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual]*.

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, INVITROGEN, Carlsbab Calif. ("MaxBac" kit). These techniques are generally known to those skilled in the art and fully described in Summers and Smith, *Texas Agricultural Experiment Station Bulletin No.* 1555 (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g., structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human γ-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plagued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, e.g., Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., Nucleic Acids Research 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology*, Malcolm B. Wilkins, ed., 1984 Pitman Publishing Limited, London, pp. 21-52. References that describe other metabolically-regulated genes: Sheen, *Plant Cell*, 2:1027-1038(1990); Maas et al., *EMBO J.* 9:3447-3452 (1990); Benkel and Hickey, *Proc. Natl. Acad. Sci.* 84:1337-1339 (1987)

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Reptr,* 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet,* 202:179-185, 1985. The genetic material may also be transferred into the plant cell by using polyethylene glycol, Krens, et al., *Nature,* 296, 72-74, 1982. Another method of introduction of nucleic acid segments is high velocity ballistic penetration by small particles with the nucleic acid either within the matrix of small beads or particles, or on the surface, Klein, et al., *Nature,* 327, 70-73, 1987 and Knudsen and Muller, 1991, *Planta,* 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA,* 79, 1859-1863, 1982.

The vector may also be introduced into the plant cells by electroporation. (Fromm et al., *Proc. Natl Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Herecallis, Nemesia, Pelargonium, Panicum, Pennisetum, Ranunculus, Senecio, Salpiglossis, Cucumis, Browaalia, Glycine, Lolium, Zea, Triticum, Sorghum,* and *Datura.*

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (e.g., structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21].

Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual]*.

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g., ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the op gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barmy et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus]*.

v. Yeast Expression

Yeast expression systems are also known to one of ordinary skill in the art. A yeast promoter is any DNA sequence capable of binding yeast RNA polymerase and initiating the downstream (3') transcription of a coding sequence (e.g., structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EP-A-0 196 056. Another example is a ubiquitin fusion protein. Such a fusion protein is made with the ubiquitin region that preferably retains a site for a processing enzyme (e.g., ubiquitin-specific processing protease) to cleave the ubiquitin from the foreign protein. Through this method, therefore, native foreign protein can be isolated (e.g., WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (e.g., see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) *Gene* 8:17-24], pCl/1 [Brake et al. (1984) *PNAS USA* 81:4642-4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [On-Weaver et al. (1983) *Methods in Enzymol.* 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct. Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g., [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; *Hansenula*]; [Das et al. (1984) *J. Bacteriol.* 158:1165; De Louvencourt et al. (1983) *J. Bacteriol.* 154: 1165; Van den Berg et al. (1990) *Bio/Technology* 8:135; *Kluyveromyces*]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75; 1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia].*

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying meningococcal proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (e.g., 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (e.g., see WO98/20734), needles, and gene guns or hyposprays. Dosage treatment may be a single dose schedule or a multiple dose schedule.

Vaccines

Vaccines according to the invention may either be prophylactic (i.e., to prevent infection) or therapeutic (i.e., to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% TWEEN™ 80, and 0.5% SPAN™ 85 (optionally containing various amounts of MTP-PE (see below), although not required) formulated into submicron particles using a microfluidizer such as Model 110Y MICROFLUIDIZER™ (Microfluidics, Newton, Mass.), (b) SAF, containing 10% Squalane, 0.4% TWEEN™ 80, 5% PLURONIC™ blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% TWEEN™ 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (e.g., the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously, intramuscularly, or transdermally/transcutaneously (e.g., WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be employed [e.g., Robinson & Torres (1997) *Seminars in Immunology* 9:271-283; Donnelly et al. (1997) *Annu Rev Immunol* 15:617-648; see later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) *Cancer Gene Therapy* 1:51-64; Kimura (1994) *Human Gene Therapy* 5:845-852; Connelly (1995) *Human Gene Therapy* 6:185-193; and Kaplitt (1994) *Nature Genetics* 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Virol.* 53:160) polytropic retroviruses e.g., MCF and MCF-MLV (see Kelly (1983) *J. Virol.* 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (e.g., HT1080 cells) or mink parent cell lines, which eliminates inactivation in human serum.

Preferred retroviruses for the construction of retroviral gene therapy vectors include Avian Leukosis Virus, Bovine Leukemia Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) *J Virol* 19:19-25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in P.O. Box 1549 Manassas, Va. 20108 USA or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci* 81:6349; and Miller (1990) *Human Gene Therapy* 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC as accession numbers ATCC VR-977 and ATCC VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in P.O. Box 1549 Manassas, Va. 20108 USA or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, Nature 339 (1989) 385 and Sabin (1973) *J. Biol. Standardization* 1:115; rhinovirus, for example ATCC VR-1110 and those described in Arnold (1990) *J Cell Biochem L*401; pox viruses such as canary pox virus or vaccinia virus, for example ATCC VR-111 and ATCC VR-2010 and those described in Fisher-Hoch (1989) *Proc Natl Acad Sci* 86:317; Flexner (1989) *Ann NY Acad Sci* 569:86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *Proc Natl Acad Sci* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *Proc Natl Acad Sci* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600:1; Bayer (1979) *Biochem Biophys Acta* 550:464; Rivnay (1987) *Meth Enzymol* 149:119; Wang (1987) *Proc Natl Acad Sci* 84:7851; Plant (1989) *Anal Biochem* 176:420.

A polynucleotide composition can comprise therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (e.g., see WO98/20734), needles, and gene guns or hyposprays. Dosage treatment may be a single dose schedule or a multiple dose schedule.

Methods for the ex vivo delivery and reimplantation of transformed cells into a subject are known in the art and described in e.g., WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta.* 1097:1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) *Proc. Natl. Acad. Sci. USA* 84:7413-7416); mRNA (Malone (1989) *Proc. Natl. Acad. Sci. USA* 86:6077-6081); and purified transcription factors (Debs (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark LIPOFECTIN™, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, e.g., Szoka (1978) *Proc. Natl. Acad. Sci. USA* 75:4194-4198; WO90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Alabaster, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See e.g., Straubinger (1983) *Meth. Immunol.* 101:512-527; Szoka (1978) *Proc. Natl. Acad. Sci. USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem.* (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C, and E, over time these lipoproteins lose A and acquire C and E apoproteins. VLDL comprises A, B, C, and E apoproteins, LDL comprises apoprotein B; and HDL comprises apoproteins A, C, and E.

The amino acid of these apoproteins are known and are described in, for example, Breslow (1985) Annu Rev. Biochem 54:699; Law (1986) Adv. Exp Med. Biol. 151:162; Chen (1986) J Biol Chem 261:12918; Kane (1980) Proc Natl Acad Sci USA 77:2465; and Utermann (1984) Hum Genet 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Techniologies, Inc., Stoughton, Mass., USA. Further description of lipoproteins can be found in Zuckermann et al. WO98/06437.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, POLYBRENE™. LIPOFECTIN™, and LIPOFECTAMINE™ are monomers that form polycationic complexes when combined with polynucleotides/polypeptides.

Immunodiagnostic Assays

Meningogoccal antigens of the invention can be used in immunoassays to detect antibody levels (or, conversely, anti-meningococcal antibodies can be used to detect antigen levels). Immunoassays based on well defined, recombinant antigens can be developed to replace invasive diagnostics methods. Antibodies to meningococcal proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 μg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 μg of yeast DNA, blotting for two hours, and hybridizing for 4-8 hours with a probe of $10^8$ cpm/μg. For a single-copy mammalian gene a conservative approach would start with 10 μg of DNA, blot overnight, and hybridize overnight in the presence of 10% dextran sulfate using a probe of greater than $10^8$ cpm/μg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10} Ci)+0.4[\%(G+C)]-0.6(\%\ \text{formamide})-600/n-1.5(\%\ \text{mismatch}).$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex, which is stable enough to be detected.

The nucleic acid probes will hybridize to the meningococcal nucleotide sequences of the invention (including both sense and antisense strands). Though many different nucleotide sequences will encode the amino acid sequence, the native meningococcal sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to the meningococcal sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional meningococcal sequence may also be helpful as a label to detect the formed duplex. For example, a non-complementary nucleotide sequence may be attached to the 5' end of the probe, with the remainder of the probe sequence being complementary to a meningococcal sequence. Alternatively, non-complementary bases or longer sequences can be interspersed into the probe, provided that the probe sequence has sufficient complementarity with the a meningococcal sequence in order to hybridize therewith and thereby form a duplex which can be detected.

The exact length and sequence of the probe will depend on the hybridization conditions, such as temperature, salt condition and the like. For example, for diagnostic applications, depending on the complexity of the analyte sequence, the nucleic acid probe typically contains at least 10-20 nucleotides, preferably 15-25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et al. [*Proc. Natl. Acad. Sci. USA* (1983) 80: 7461], or using commercially available automated oligonucleotide synthesizers.

The chemical nature of the probe can be selected according to preference. For certain applications, DNA or RNA are appropriate. For other applications, modifications may be incorporated e.g., backbone modifications, such as phosphorothioates or methylphosphonates, can be used to increase in vivo half-life, alter RNA affinity, increase nuclease resistance etc. [e.g., see Agrawal & Iyer (1995) *Curr Opin Biotechnol* 6:12-19; Agrawal (1996) *TIBTECH* 14:376-387]; analogues such as peptide nucleic acids may also be used [e.g., see Corey (1997) *TIBTECH* 15:224-229; Buchardt et al. (1993) *TIBTECH* 11:384-386].

Alternatively, the polymerase chain reaction (PCR) is another well-known means for detecting small amounts of target nucleic acids. The assay is described in: Mullis et al. [*Meth. Enzymol.* (1987) 155: 335-350]; U.S. Pat. Nos. 4,683,195 and 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired meningococcal sequence.

A thermostable polymerase creates copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the meningococcal sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

MODES FOR CARRYING OUT THE INVENTION

Preferred Fragments

The protein sequences disclosed in the International Applications have been, inter alia, subjected to computer analysis to predict antigenic peptide fragments within the full-length proteins. Three algorithms have been used in this analysis:

- AMPHI This program has been used to predict T-cell epitopes [Gao et al. (1989) *J. Immunol.* 143:3007; Roberts et al. (1996) *AIDS Res Hum Retrovir* 12:593; Quakyi et al. (1992) *Scand J Immunol* suppl. 11:9] and is available in the Protean package of DNASTAR, Inc. (1228 South Park Street, Madison, Wis. 53715 USA).
- ANTIGENIC INDEX as disclosed by Jameson & Wolf (1988) The antigenic index: a novel algorithm for predicting antigenic determinants. CABIOS, 4:181:186
- HYDROPHILICITY as disclosed by Hopp & Woods (1981) Prediction of protein antigenic determinants from amino acid sequences. PNAS, 78:3824-3828

The three algorithms often identify the same fragments. Such multiply-identified fragments are particularly preferred. The algorithms often identify overlapping fragments (e.g., for antigen "013", AMPHI identifies aa 42-46, and Antigenic Index identifies aa 39-45). The invention explicitly includes fragments resulting from a combination of these overlapping fragments (e.g., the fragment from residue 39 to residue 46, in the case of "013"). Fragments separated by a single amino acid are also often identified (e.g., for "018-2", antigenic index identifies aa 19-23 and 25-41). The invention also includes fragments spanning the two extremes of such "adjacent" fragments (e.g., 19-41 for "081-2"). The Example provides preferred antigenic fragments of the proteins disclosed in the International Applications.

Example 1

Preferred Antigenic Protein Fragments

The following amino acid sequences in Table 1 are identified by titles indicating the number assigned to the particular open reading frame (ORF), consistent with those designated in the International Applications. The titles are of the following form: [no prefix, g, or a] [#], where "no prefix" means a sequence from *N. meningitidis* serotype B, "a" means a sequence from *N. meningitidis* serotype A, and "g" means a sequence from *N. gonorrhoeae*; and "#" means the number assigned to that open reading frame (ORF). For example, "127" refers to an *N. meningitidis* B amino acid sequence, ORF number 127. The presence of a suffix "-1" or "-2" to these titles indicates an additional sequence found for that particular ORF. Thus, for example, "a12-2" refers to an *N. meningitidis* A amino acid sequence, ORF number 12, which is another sequence found for ORF 12 in addition to the originally designated ORF 12 and ORF 12-1. Each amino acid sequence is preceded by the beginning amino acid position number and followed by the ending amino acid position number.

TABLE 1

| | |
|---|---|
| 012-1 | |
| AMPHI Regions - AMPHI | |
| SEQ. ID. NO. 1 | 19-LysLeuLeuGluGlnLeuMetArgPheLeuGlnPheLeuSerGluPheLeuPheAlaLeuPheArgIle-41 |
| SEQ. ID. NO. 2 | 48-ArgAlaLeuLysPheAlaArgArg-55 |
| SEQ. ID. NO. 3 | 90-AsnPheIleArgHisThr-95 |
| SEQ. ID. NO. 4 | 133-HisAlaAlaArgThrPhe-138 |
| SEQ. ID. NO. 5 | 160-GlnGlyPheTyrGlyVal-165 |
| SEQ. ID. NO. 6 | 179-GlyPheLeuArgPheGlyArgPheLeuProThrLeuLeuGlnThrLeu-194 |
| Antigenic Index - Jameson-Wolf | |
| SEQ. ID. NO. 7 | 42-PheThrHisLysSerAsnArgAlaLeuLysPheAlaArgArgHisHis-57 |
| SEQ. ID. NO. 8 | 77-HisThrHisArgThrAspAsnArgLysArgSerGlySerAsnPhe-91 |
| SEQ. ID. NO. 9 | 93-ArgHisThrArgHis-97 |
| SEQ. ID. NO. 10 | 101-AlaAlaArgArgHisLeuIleAspGlyAspGlyGlnArgAsn-114 |
| SEQ. ID. NO. 11 | 120-ThrXxxLysLeuArgSerArgGlnThr-128 |
| SEQ. ID. NO. 12 | 137-ThrPheGlnSerGluGlnAsnLeu-144 |
| SEQ. ID. NO. 13 | 147-ArgLeuGlyAsnGlnLysHisArgArgAsnLeuMetThrGln-160 |
| SEQ. ID. NO. 14 | 173-IleGlnHisLysLysAlaGly-179 |
| Hydrophilic Regions - Hopp-Woods | |
| SEQ. ID. NO. 15 | 45-LysSerAsnArgAlaLeuLysPheAlaArgArgHisHis-57 |
| SEQ. ID. NO. 16 | 77-HisThrHisArgThrAspAsnArgLysArgSerGly-88 |
| SEQ. ID. NO. 17 | 101-AlaAlaArgArgHisLeuIleAspGlyAspGlyGlnArg-113 |
| SEQ. ID. NO. 18 | 121-XxxLysLeuArgSerArgGln-127 |
| SEQ. ID. NO. 19 | 149-GlyAsnGlnLysHisArgArgAsnLeu-157 |
| SEQ. ID. NO. 20 | 173-IleGlnHisLysLysAlaGly-179 |
| 013 | |
| AMPHI Regions - AMPHI | |
| SEQ. ID. NO. 21 | 42-AspSerTyrThrPhe-46 |
| Antigenic Index - Jameson-Wolf | |
| SEQ. ID. NO. 22 | 17-LysSerGluArgXxxSerGlyGlyAsnMetValProArgProSerProPheLeuPro-35 |
| SEQ. ID. NO. 23 | 39-ThrGlnLeuAspSerTyrThr-45 |
| SEQ. ID. NO. 24 | 58-GluAlaAlaAlaGlnLysGlnProLysThrArgAlaValGly-71 |
| SEQ. ID. NO. 25 | 91-ArgSerGlyXxxLysIle-96 |
| Hydrophilic Regions - Hopp-Woods | |
| SEQ. ID. NO. 26 | 17-LysSerGluArgXxxSerGly-23 |
| SEQ. ID. NO. 27 | 58-GluAlaAlaAlaGlnLysGlnProLysThrArgAlaValGly-71 |

TABLE 1-continued

| | |
|---|---|
| 015-2 | |
| AMPHI Regions - AMPHI | |
| SEQ. ID. NO. 28 | 33-GluLysProLeuAlaGlyPheTrpLysAlaLeuProHis-45 |
| SEQ. ID. NO. 29 | 107-MetCysCysValAlaCysIleVal-114 |
| Antigenic Index - Jameson-Wolf | |
| SEQ. ID. NO. 30 | 29-TrpLysAsnProGluLysProLeu-36 |
| SEQ. ID. NO. 31 | 90-MetArgAlaArgProArgSerThrLys-98 |
| Hydrophilic Regions - Hopp-Woods | |
| SEQ. ID. NO. 32 | 31-AsnProGluLysProLeu-36 |
| SEQ. ID. NO. 33 | 90-MetArgAlaArgProArgSerThrLys-98 |
| 018-2 | |
| AMPHI Regions - AMPHI | |
| SEQ. ID. NO. 34 | 6-IleGlnHisLeuArg-10 |
| SEQ. ID. NO. 35 | 180-HisGlyCysGlnHisIlePhe-186 |
| Antigenic Index - Jameson-Wolf | |
| SEQ. ID. NO. 36 | 1-MetValGluArgHisIleGln-7 |
| SEQ. ID. NO. 37 | 9-LeuArgAsnGlyHis-13 |
| SEQ. ID. NO. 38 | 19-ProSerGlnGlnVal-23 |
| SEQ. ID. NO. 39 | 25-GlnMetPheGlyGlyArgAlaTyrAspPheArgAlaAspLysAlaAlaGly-41 |
| SEQ. ID. NO. 40 | 67-TyrPheAlaAspAspLysPhe-73 |
| SEQ. ID. NO. 41 | 78-LeuArgGlyAsnLeuArg-83 |
| SEQ. ID. NO. 42 | 85-PheGlnThrAspLysAlaAspLeuArgThrGlyLysHisHisAlaAspGlyAlaAlaPro-104 |
| SEQ. ID. NO. 43 | 106-ThrAlaAlaAspIleArgValAlaAla-114 |
| SEQ. ID. NO. 44 | 129-GlnGlnArgGlnLeuVal-134 |
| SEQ. ID. NO. 45 | 137-IleAlaCysAspGluAspMetArgAsnThrGlyLeuHis-149 |
| SEQ. ID. NO. 46 | 151-GlnArgValGlyAsnArgTyrAla-158 |
| Hydrophilic Regions - Hopp-Woods | |
| SEQ. ID. NO. 47 | 1-MetValGluArgHisIleGln-7 |
| SEQ. ID. NO. 48 | 30-ArgAlaTyrAspPheArgAlaAspLysAlaAla-40 |
| SEQ. ID. NO. 49 | 67-TyrPheAlaAspAspLysPhe-73 |
| SEQ. ID. NO. 50 | 85-PheGlnThrAspLysAlaAspLeuArgThrGlyLysHisHisAlaAspGlyAlaAla-103 |
| SEQ. ID. NO. 51 | 106-ThrAlaAlaAspIleArgValAlaAla-114 |
| SEQ. ID. NO. 52 | 137-IleAlaCysAspGluAspMetArgAsn-145 |
| 019-2 | |
| AMPHI Regions - AMPHI | |
| SEQ. ID. NO. 53 | 33-ProAlaAspAsnIleGlu-38 |
| SEQ. ID. NO. 54 | 60-AspTyrGlyGlyTyrProSerAlaLeuAspAla-70 |
| SEQ. ID. NO. 55 | 80-AlaAlaTyrLeuGluAsnAlaGlyAsp-88 |
| SEQ. ID. NO. 56 | 90-AlaMetAlaGluAsnValArgAsnGluTrpLeuLysSer-102 |
| SEQ. ID. NO. 57 | 142-AlaAlaGluLeuValLysAsnThrGlyLysLeuProSerGlyCysThrLysLeuLeuGluGlnAlaAlaAlaSer-166 |
| SEQ. ID. NO. 58 | 173-AspAlaTrpArgArgValArg-179 |
| SEQ. ID. NO. 59 | 193-LeuAlaAlaAlaLeuGlySerProPheAspGlyGlyThrGlnGly-207 |
| SEQ. ID. NO. 60 | 215-AsnValIleGlyLysGluAlaArgLysSer-224 |
| SEQ. ID. NO. 61 | 229-AlaLeuLeuSerGluMet-234 |
| SEQ. ID. NO. 62 | 259-AsnValProAlaAlaLeuAspTyrTyrGly-268 |
| SEQ. ID. NO. 63 | 292-ArgArgTrpAspGluLeuAlaSerValIleSerHisMetProGluLysLeuGlnLys-310 |
| SEQ. ID. NO. 64 | 329-GlnGluAlaGluLysLeuTyrLysGlnAla-338 |
| SEQ. ID. NO. 65 | 367-AlaGlyLysAsnSerValArgArgMetAlaGlu-377 |
| SEQ. ID. NO. 66 | 451-ArgTyrIleSerPro-455 |
| SEQ. ID. NO. 67 | 495-GlnGlyLeuMetGlnValMet-501 |
| SEQ. ID. NO. 68 | 582-ArgAspTyrValLysLysValMet-589 |
| Antigenic Index - Jameson-Wolf | |
| SEQ. ID. NO. 69 | 22-SerSerThrAsnThr-26 |
| SEQ. ID. NO. 70 | 28-ProAlaGlyLysThrProAlaAspAsnIleGluThrAlaAspLeuSerAlaSerValProThrArgProAlaGluProGluArgLysThrLeuAlaAspTyr GlyGlyTyrProSerAla-67 |
| SEQ. ID. NO. 71 | 69-AspAlaValLysGlnLysAsnAspAla-77 |
| SEQ. ID. NO. 72 | 85-AsnAlaGlyAspSerAlaMet-91 |
| SEQ. ID. NO. 73 | 103-LeuGlyAlaArgArgGln-108 |
| SEQ. ID. NO. 74 | 115-GluTyrAlaLysLeuGluProAlaGlyArgAlaGlnGluValGluCysTyrAlaAspSerSerArgAsnAspTyrThrArgAlaAlaGluLeuValLys AsnThrGlyLysLeuProSerGlyCys-156 |
| SEQ. ID. NO. 75 | 167-GlyLeuLeuAspGlyAsnAspAlaTrpArgArgValArgGly-180 |
| SEQ. ID. NO. 76 | 182-LeuAlaGlyArgGlnThrThrAspAlaArgAsn-192 |
| SEQ. ID. NO. 77 | 199-SerProPheAspGlyGlyThrGlnGlySerArgGluTyr-211 |
| SEQ. ID. NO. 78 | 217-IleGlyLysGluAlaArgLysSerProAsnAla-227 |
| SEQ. ID. NO. 79 | 232-SerGluMetGluSerGlyLeuSerLeuGluGlnArgSer-244 |
| SEQ. ID. NO. 80 | 254-GlnSerGlnAsnLeu-258 |
| SEQ. ID. NO. 81 | 266-TyrTyrGlyLysValAlaAspArgArgGlnLeuThrAspAspGlnIle-281 |
| SEQ. ID. NO. 82 | 287-AlaAlaLeuArgAlaArgArgTrpAspGlu-296 |
| SEQ. ID. NO. 83 | 304-MetProGluLysLeuGlnLysSerProThr-313 |
| SEQ. ID. NO. 84 | 320-ArgSerArgAlaAlaThrGlyAsnThrGlnGluAlaGluLysLeuTyrLys-336 |
| SEQ. ID. NO. 85 | 339-AlaAlaThrGlyArgAsn-344 |
| SEQ. ID. NO. 86 | 350-AlaGlyGluGluLeuGlyArgLysIleAspThrArgAsnAsnValProAspAlaGlyLysAsnSerValArgArgMetAlaGluAspGlyAlaVal LysArg-383 |
| SEQ. ID. NO. 87 | 389-GlnAsnSerGlnSerAlaGlyAspAlaLysMetArgArgGlnAlaGlnAla-405 |
| SEQ. ID. NO. 88 | 409-PheAlaThrArgGlyPheAspGluAspLysLeuLeu-420 |
| SEQ. ID. NO. 89 | 438-SerAlaGluArgThrAspArgLysLeuAsnTyr-448 |
| SEQ. ID. NO. 90 | 454-SerProPheLysAspThrValIle-461 |
| SEQ. ID. NO. 91 | 464-AlaGlnAsnValAsnValAspProAla-472 |
| SEQ. ID. NO. 92 | 478-IleArgGlnGluSerArgPhe-484 |
| SEQ. ID. NO. 93 | 488-AlaGlnSerArgValGlyAla-494 |

TABLE 1-continued

| | |
|---|---|
| SEQ. ID. NO. 94 | 504-ThrAlaArgGluIleAlaGly-510 |
| SEQ. ID. NO. 95 | 520-TyrThrAlaAspGlyAsnIleArgMetGly-529 |
| SEQ. ID. NO. 96 | 535-AspThrLysArgArgLeuGlnAsnAsnGluVal-545 |
| SEQ. ID. NO. 97 | 550-GlyTyrAsnAlaGlyProGlyArgAlaArgArgTrpGlnAlaAspThrProLeuGlu-568 |
| SEQ. ID. NO. 98 | 579-SerGluThrArgAspTyrValLys-586 |
| SEQ. ID. NO. 99 | 606-LeuLysGlnArgMet-610 |
| Hydrophilic Regions - Hopp-Woods | |
| SEQ. ID. NO. 100 | 30-GlyLysThrProAlaAspAsnIleGluThrAlaAspLeu-42 |
| SEQ. ID. NO. 101 | 46-ValProThrArgProAlaGluProGluArgLysThrLeuAla-59 |
| SEQ. ID. NO. 102 | 69-AspAlaValLysGlnLysAsnAspAla-77 |
| SEQ. ID. NO. 103 | 85-AsnAlaGlyAspSerAlaMet-91 |
| SEQ. ID. NO. 104 | 103-LeuGlyAlaArgArgGln-108 |
| SEQ. ID. NO. 105 | 115-GluTyrAlaLysLeuGluProAlaGlyArgAlaGlnGluValGluCysTyrAlaAspSerSerArgAsnAspTyrThrArgAlaAlaGluLeuValLys AsnThrGlyLysLeuProSerGlyCys-156 |
| SEQ. ID. NO. 106 | 170-AspGlyAsnAspAlaTrpArgArgValArgGly-180 |
| SEQ. ID. NO. 107 | 185-ArgGlnThrThrAspAlaArgAsn-192 |
| SEQ. ID. NO. 108 | 201-PheAspGlyGlyThrGlnGlySerArgGlu-210 |
| SEQ. ID. NO. 109 | 217-IleGlyLysGluAlaArgLysSerProAsn-226 |
| SEQ. ID. NO. 110 | 232-SerGluMetGluSer-236 |
| SEQ. ID. NO. 111 | 238-LeuSerLeuGluGlnArgSer-244 |
| SEQ. ID. NO. 112 | 270-ValAlaAspArgArgGlnLeuThrAspAspGlnIle-281 |
| SEQ. ID. NO. 113 | 287-AlaAlaLeuArgAlaArgArgTrpAspGlu-296 |
| SEQ. ID. NO. 114 | 304-MetProGluLysLeuGlnLys-310 |
| SEQ. ID. NO. 115 | 320-ArgSerArgAlaAlaThr-325 |
| SEQ. ID. NO. 116 | 327-AsnThrGlnGluAlaGluLysLeuTyrLys-336 |
| SEQ. ID. NO. 117 | 350-AlaGlyGluGluLeuGlyArgLysIleAspThrArgAsnAsnValProAspAlaGlyLysAsnSerValArgArgMetAlaGluAspGlyAlaValLys Arg-383 |
| SEQ. ID. NO. 118 | 392-GlnSerAlaGlyAspAlaLysMetArgArgGlnAlaGlnAla-405 |
| SEQ. ID. NO. 119 | 411-ThrArgGlyPheAspGluAspLysLeuLeu-420 |
| SEQ. ID. NO. 120 | 438-SerAlaGluArgThrAspArgLysLeu-446 |
| SEQ. ID. NO. 121 | 478-IleArgGlnGluSerArgPhe-484 |
| SEQ. ID. NO. 122 | 504-ThrAlaArgGluIleAlaGly-510 |
| SEQ. ID. NO. 123 | 535-AspThrLysArgArgLeuGlnAsn-542 |
| SEQ. ID. NO. 124 | 554-GlyProGlyArgAlaArgArgTrpGlnAla-563 |
| SEQ. ID. NO. 125 | 579-SerGluThrArgAspTyrValLys-586 |
| SEQ. ID. NO. 126 | 606-LeuLysGlnArgMet-610 |
| 023 | |
| AMPHI Regions - AMPHI | |
| SEQ. ID. NO. 127 | 42-LysGluTyrSerAlaTrpGlnAlaPhePheSerGlnThrTrpValLysValPheThrGlnValSerPheIleAlaValPheLeuHisAlaTrpValGly-74 |
| SEQ. ID. NO. 128 | 77-AspLeuTrpMetAspTyrIleLys-84 |
| Antigenic Index - Jameson-Wolf | |
| SEQ. ID. NO. 129 | 1-MetValGluArgLysLeuThr-7 |
| SEQ. ID. NO. 130 | 40-LeuProLysGluTyrSer-45 |
| Hydrophilic Regions - Hopp-Woods | |
| SEQ. ID. NO. 131 | 1-MetValGluArgLysLeuThr-7 |
| 025-2 | |
| AMPHI Regions - AMPHI | |
| SEQ. ID. NO. 132 | 9-AlaAlaCysThrAlaValAlaAlaLeuLeuGlyGlyCysAla-22 |
| SEQ. ID. NO. 133 | 36-MetGlnAspAlaProSerSerAlaValTyrAsnAsnProTyrGlyAla-51 |
| SEQ. ID. NO. 134 | 126-AspPheArgAlaTrpAsnGlyMetThrAsp-135 |
| SEQ. ID. NO. 135 | 140-IleGlyGlnIleValLysVal-146 |
| SEQ. ID. NO. 136 | 206-AspPheArgAlaTrpAsnGlyMetThrAspAsnMet-217 |
| SEQ. ID. NO. 137 | 219-SerIleGlyGlnIleValLysVal-226 |
| SEQ. ID. NO. 138 | 248-AlaValGlnThrProValLysProAlaAla-257 |
| SEQ. ID. NO. 139 | 261-ValGlnSerAlaProGlnPro-267 |
| SEQ. ID. NO. 140 | 290-SerGlyThrArgSer-294 |
| SEQ. ID. NO. 141 | 307-LysValValAlaAspPhe-312 |
| SEQ. ID. NO. 142 | 343-GlyLeuArgGlyTyrGlyAsn-349 |
| Antigenic Index - Jameson-Wolf | |
| SEQ. ID. NO. 143 | 22-AlaThrGlnGlnPro-26 |
| SEQ. ID. NO. 144 | 33-AsnSerGlyMetGlnAspAlaProSerSer-42 |
| SEQ. ID. NO. 145 | 52-ThrProTyrSerProAlaProAlaGlyAspAlaProTyr-64 |
| SEQ. ID. NO. 146 | 108-ValArgGlyAspThr-112 |
| SEQ. ID. NO. 147 | 115-AsnIleSerLysArgTyrHisIleSerGlnAspAspPheArgAla-129 |
| SEQ. ID. NO. 148 | 131-AsnGlyMetThrAspAsnThrLeu-138 |
| SEQ. ID. NO. 149 | 144-ValLysValLysProAlaGly-150 |
| SEQ. ID. NO. 150 | 157-AlaAlaValLysSerArgProAlaVal-165 |
| SEQ. ID. NO. 151 | 170-GlnProProValGln-174 |
| SEQ. ID. NO. 152 | 188-ValArgGlyAspThr-192 |
| SEQ. ID. NO. 153 | 195-AsnIleSerLysArgTyrHisIleSerGlnAspAspPheArgAla-209 |
| SEQ. ID. NO. 154 | 211-AsnGlyMetThrAspAsnMetLeu-218 |
| SEQ. ID. NO. 155 | 224-ValLysValLysProAlaGly-230 |
| SEQ. ID. NO. 156 | 232-AlaAlaProLysThrAlaAlaValGluSerArgProAlaValPro-246 |
| SEQ. ID. NO. 157 | 252-ProValLysProAlaAlaGlnProProValGlnSerAlaProGlnPro-267 |
| SEQ. ID. NO. 158 | 270-ProAlaAlaGluAsnLysAlaValPro-278 |
| SEQ. ID. NO. 159 | 280-ProAlaProGlnSerProAlaAlaSerProSerGlyThrArgSerValGly-296 |
| SEQ. ID. NO. 160 | 302-ArgProThrGlnGlyLysValValAlaAspPheGlyGlyAsnAsnLysGlyValAsp-320 |
| SEQ. ID. NO. 161 | 333-AlaAspGlyLysVal-337 |
| SEQ. ID. NO. 162 | 342-SerGlyLeuArgGlyTyrGly-348 |
| SEQ. ID. NO. 163 | 363-TyrGlyHisAsnGln-367 |

TABLE 1-continued

| | |
|---|---|
| SEQ. ID. NO. 164 | 370-LeuValGlyGluGlyGlnGlnValLysArgGlyGlnGln-382 |
| SEQ. ID. NO. 165 | 387-GlyAsnThrAspAlaSerArgThrGlnLeu-396 |
| SEQ. ID. NO. 166 | 398-PheGluValArgGlnAsnGlyLysProValAsnProAsnSer-411 |
| Hydrophilic Regions - Hopp-Woods | |
| SEQ. ID. NO. 167 | 35-GlyMetGlnAspAlaProSer-41 |
| SEQ. ID. NO. 168 | 108-ValArgGlyAspThr-112 |
| SEQ. ID. NO. 169 | 120-TyrHisIleSerGlnAspAspPheArg-128 |
| SEQ. ID. NO. 170 | 144-ValLysValLysPro-148 |
| SEQ. ID. NO. 171 | 157-AlaAlaValLysSerArgProAlaVal-165 |
| SEQ. ID. NO. 172 | 188-ValArgGlyAspThr-192 |
| SEQ. ID. NO. 173 | 200-TyrHisIleSerGlnAspAspPheArg-208 |
| SEQ. ID. NO. 174 | 224-ValLysValLysPro-228 |
| SEQ. ID. NO. 175 | 237-AlaAlaValGluSerArgProAlaVal-245 |
| SEQ. ID. NO. 176 | 253-ValLysProAlaAla-257 |
| SEQ. ID. NO. 177 | 270-ProAlaAlaGluAsnLysAlaValPro-278 |
| SEQ. ID. NO. 178 | 290-SerGlyThrArgSer-294 |
| SEQ. ID. NO. 179 | 313-GlyGlyAsnAsnLysGlyValAsp-320 |
| SEQ. ID. NO. 180 | 333-AlaAspGlyLysVal-337 |
| SEQ. ID. NO. 181 | 373-GluGlyGlnGlnValLysArgGlyGln-381 |
| SEQ. ID. NO. 182 | 389-ThrAspAlaSerArgThr-394 |
| SEQ. ID. NO. 183 | 400-ValArgGlnAsnGlyLysProValAsn-408 |
| 031 | |
| AMPHI Regions - AMPHI | |
| SEQ. ID. NO. 184 | 11-TyrSerAlaIleArgLeuPheThrGlnAlaValIleGluPheProGlnThrAlaGluHisCysArgArgThrArgAsp-36 |
| SEQ. ID. NO. 185 | 48-ArgArgProValGln-52 |
| Antigenic Index - Jameson-Wolf | |
| SEQ. ID. NO. 186 | 1-ArgLeuLysHisGlyVal-6 |
| SEQ. ID. NO. 187 | 25-ProGlnThrAlaGluHisCysArgArgThrArgAspGlnHisGlnGluArgArgAsnArgGlnGlyPheArgArgProValGlnHisValGlyArgArg AsnGlnGlnGlnArgHisSerGlnThrCysGlyGlnSerGlyArgAsnHisAlaGlnLysGlnGlnCysAlaThrArgGln-84 |
| Hydrophilic Regions - Hopp-Woods | |
| SEQ. ID. NO. 188 | 28-AlaGluHisCysArgArgThrArgAspGlnHisGlnGluArgArgAsnArgGlnGlyPheArgArgProVal-51 |
| SEQ. ID. NO. 189 | 54-ValGlyArgArgAsnGlnGlnGlnArgHisSerGln-65 |
| SEQ. ID. NO. 190 | 69-GlnSerGlyArgAsnHisAlaGlnLysGlnGlnCysAlaThrArgGln-84 |
| 032-2 | |
| AMPHI Regions - AMPHI | |
| SEQ. ID. NO. 191 | 11-LeuArgArgProLeuArgGln-17 |
| SEQ. ID. NO. 192 | 67-ProPheAlaAspAsnValTyrPro-74 |
| SEQ. ID. NO. 193 | 94-ThrAlaAlaValHisGlnPheGluGln-102 |
| SEQ. ID. NO. 194 | 114-ValHisGlyGlnIleGlnHisProValGlnProPheLeuArg-127 |
| SEQ. ID. NO. 195 | 134-LeuGlyLeuLeuArgArgPheAspVal-142 |
| Antigenic Index - Jameson-Wolf | |
| SEQ. ID. NO. 196 | 1-MetArgArgAsnVal-5 |
| SEQ. ID. NO. 197 | 10-ValLeuArgArgProLeuArg-16 |
| SEQ. ID. NO. 198 | 28-ArgAlaValProAlaGlyLysGlnGlyPhe-37 |
| SEQ. ID. NO. 199 | 41-CysArgLeuThrGlnArgGln-47 |
| SEQ. ID. NO. 200 | 57-AlaAspGlnArgHis-61 |
| SEQ. ID. NO. 201 | 107-HisArgGlnArgVal-111 |
| SEQ. ID. NO. 202 | 138-ArgArgPheAspValGlyGlyArgVal-146 |
| SEQ. ID. NO. 203 | 160-LeuProProArgArgLysLeuAlaSerGlnArgProPheProGln-174 |
| Hydrophilic Regions - Hopp-Woods | |
| SEQ. ID. NO. 204 | 1-MetArgArgAsnVal-5 |
| SEQ. ID. NO. 205 | 10-ValLeuArgArgProLeuArg-16 |
| SEQ. ID. NO. 206 | 28-ArgAlaValProAlaGlyLys-34 |
| SEQ. ID. NO. 207 | 41-CysArgLeuThrGln-45 |
| SEQ. ID. NO. 208 | 57-AlaAspGlnArgHis-61 |
| SEQ. ID. NO. 209 | 107-HisArgGlnArgVal-111 |
| SEQ. ID. NO. 210 | 138-ArgArgPheAspValGlyGly-144 |
| SEQ. ID. NO. 211 | 161-ProProArgArgLysLeuAlaSer-168 |
| 033-2 | |
| AMPHI Regions - AMPHI | |
| SEQ. ID. NO. 212 | 6-GlnTyrGlyGlyLeuAlaGlyPheProLysArgCysGluSerGlu-20 |
| SEQ. ID. NO. 213 | 64-GlyGlnAlaPheGluAlaLeuAsnCys-72 |
| SEQ. ID. NO. 214 | 95-ValGlyAlaLeuProLysTyrLeuAlaSerAsnValValArgAspMetHisGlyLeuLeuSerThrVal-117 |
| SEQ. ID. NO. 215 | 120-GlnThrGlyLysValLeuAspLysIleProGlyAlaMetGlu-133 |
| SEQ. ID. NO. 216 | 142-IleLysThrLeuAlaGlu-147 |
| SEQ. ID. NO. 217 | 157-SerLeuPheGluAsnPhe-162 |
| SEQ. ID. NO. 218 | 168-GlyProValAspGlyHisAsnValGluAsnLeuValAspValLeuLysAspLeuArgSerArg-188 |
| SEQ. ID. NO. 219 | 207-AlaGluAsnAspPro-211 |
| SEQ. ID. NO. 220 | 213-LysTyrHisAlaValAlaAsnLeuProLysGluSerAlaAla-226 |
| SEQ. ID. NO. 221 | 242-TyrThrGlnValPheGlyLys-248 |
| SEQ. ID. NO. 222 | 280-PheProAspArgTyrPheAspVal-287 |
| SEQ. ID. NO. 223 | 307-LysProValValAlaIleTyrSer-314 |
| SEQ. ID. NO. 224 | 316-PheLeuGlnArgAlaTyrAspGlnLeu-324 |
| SEQ. ID. NO. 225 | 363-CysValProAsnMet-367 |
| SEQ. ID. NO. 226 | 390-AlaProAlaAlaValArgTyrProArgGlyThr-400 |
| SEQ. ID. NO. 227 | 406-ValSerAspGlyMetGluThrValGlu-414 |
| SEQ. ID. NO. 228 | 419-IleIleArgArgGlu-423 |
| SEQ. ID. NO. 229 | 432-PheGlySerMetValAla-437 |
| SEQ. ID. NO. 230 | 453-MetArgPheValLysProIleAspGluGlu-462 |
| SEQ. ID. NO. 231 | 469-ArgSerHisAspArgIle-474 |

TABLE 1-continued

| | |
|---|---|
| SEQ. ID. NO. 232 | 489-AlaValLeuGluValLeu-494 |
| SEQ. ID. NO. 233 | 510-AspThrValThrGlyHisGly-516 |
| SEQ. ID. NO. 234 | 518-ProLysLysLeuLeu-522 |
| Antigenic Index - Jameson-Wolf | |
| SEQ. ID. NO. 235 | 11-AlaGlyPheProLysArgCysGluSerGluTyrAspAla-23 |
| SEQ. ID. NO. 236 | 28-HisSerSerThrSerIle-33 |
| SEQ. ID. NO. 237 | 41-AlaAlaAspLysLeuLeuGlySerAspArgArgSerVal-53 |
| SEQ. ID. NO. 238 | 57-GlyAspGlyAlaMetThr-62 |
| SEQ. ID. NO. 239 | 72-CysAlaGlyAspMetAspVal-78 |
| SEQ. ID. NO. 240 | 85-AsnAspAsnGluMetSerIle-91 |
| SEQ. ID. NO. 241 | 105-AsnValValArgAspMetHisGly-112 |
| SEQ. ID. NO. 242 | 117-ValLysAlaGlnThrGlyLysValLeuAspLysIleProGly-130 |
| SEQ. ID. NO. 243 | 134-PheAlaGlnLysValGluHisLysIleLysThrLeuAlaGluGluAlaGluHisAlaLysGln-154 |
| SEQ. ID. NO. 244 | 166-TyrThrGlyProValAspGlyHisAsn-174 |
| SEQ. ID. NO. 245 | 181-ValLeuLysAspLeuArgSerArgLysGlyProGln-192 |
| SEQ. ID. NO. 246 | 198-ThrLysLysGlyAsnGlyTyrLysLeuAlaGluAsnAspProValLys-213 |
| SEQ. ID. NO. 247 | 220-LeuProLysGluSerAlaAla-226 |
| SEQ. ID. NO. 248 | 228-MetProSerGluLysGluProLysProAlaAlaLysProThrTyr-242 |
| SEQ. ID. NO. 249 | 253-ArgAlaAlaAlaAspSerArgLeu-260 |
| SEQ. ID. NO. 250 | 266-AlaMetArgGluGlySerGlyLeuValGluPheGluGlnArgPheProAspArgTyrPhe-285 |
| SEQ. ID. NO. 251 | 345-ValGlyAlaAspGlyProThrHis-352 |
| SEQ. ID. NO. 252 | 370-AlaAlaProSerAspGluAsnGluCysArg-379 |
| SEQ. ID. NO. 253 | 395-ArgTyrProArgGlyThrGlyThrGlyAlaProValSerAspGlyMetGluThrValGluIleGlyLysGlyIleIleArgArgGluGlyGluLysThr Ala-428 |
| SEQ. ID. NO. 254 | 457-LysProIleAspGluGluLeuIle-464 |
| SEQ. ID. NO. 255 | 467-LeuAlaArgSerHisAspArgIleValThrLeuGluGluAsnAlaGluGlnGlyGlyAlaGlyGly-488 |
| SEQ. ID. NO. 256 | 512-ValThrGlyHisGlyAspProLysLysLeuLeuAspAspLeuGlyLeu-527 |
| SEQ. ID. NO. 257 | 530-GluAlaValGluArgArgValArg-537 |
| SEQ. ID. NO. 258 | 540-LeuSerAspArgAspAlaAlaAsn-547 |
| Hydrophilic Regions - Hopp-Woods | |
| SEQ. ID. NO. 259 | 13-PheProLysArgCysGluSerGluTyrAsp-22 |
| SEQ. ID. NO. 260 | 41-AlaAlaAspLysLeuLeuGlySerAspArgArgSerVal-53 |
| SEQ. ID. NO. 261 | 74-GlyAspMetAspVal-78 |
| SEQ. ID. NO. 262 | 85-AsnAspAsnGluMetSerIle-91 |
| SEQ. ID. NO. 263 | 106-ValValArgAspMetHis-111 |
| SEQ. ID. NO. 264 | 123-LysValLeuAspLysIleProGly-130 |
| SEQ. ID. NO. 265 | 134-PheAlaGlnLysValGluHisLysIleLysThrLeuAlaGluGluAlaGluHisAlaLysGln-154 |
| SEQ. ID. NO. 266 | 181-ValLeuLysAspLeuArgSerArgLysGlyPro-191 |
| SEQ. ID. NO. 267 | 198-ThrLysLysGlyAsnGly-203 |
| SEQ. ID. NO. 268 | 205-LysLeuAlaGluAsnAspProValLys-213 |
| SEQ. ID. NO. 269 | 220-LeuProLysGluSerAlaAla-226 |
| SEQ. ID. NO. 270 | 228-MetProSerGluLysGluProLysProAlaAla-238 |
| SEQ. ID. NO. 271 | 253-ArgAlaAlaAlaAspSerArgLeu-260 |
| SEQ. ID. NO. 272 | 266-AlaMetArgGluGlySerGly-272 |
| SEQ. ID. NO. 273 | 274-ValGluPheGluGlnArgPheProAspArgTyrPhe-285 |
| SEQ. ID. NO. 274 | 372-ProSerAspGluAsnGluCys-378 |
| SEQ. ID. NO. 275 | 405-ProValSerAspGlyMetGluThrValGluIleGlyLysGlyIleIleArgArgGluGlyGluLysThrAla-428 |
| SEQ. ID. NO. 276 | 457-LysProIleAspGluGluLeuIle-464 |
| SEQ. ID. NO. 277 | 467-LeuAlaArgSerHisAspArgIleValThrLeuGluGluAsnAlaGluGlnGlyGly-485 |
| SEQ. ID. NO. 278 | 513-ThrGlyHisGlyAspProLysLysLeuLeuAsp-523 |
| SEQ. ID. NO. 279 | 530-GluAlaValGluArgArgValArg-537 |
| SEQ. ID. NO. 280 | 540-LeuSerAspArgAspAlaAlaAsn-547 |
| 034-2 | |
| AMPHI Regions-AMPHI | |
| SEQ. ID. NO. 281 | 35-LeuAspHisAlaAla-39 |
| SEQ. ID. NO. 282 | 52-AsnLeuGluGlnMetArgAlaIleMetGluAlaAlaAspGln-65 |
| SEQ. ID. NO. 283 | 94-AlaValGluGluPheProHisIlePro-102 |
| SEQ. ID. NO. 284 | 152-ThrValValAsnPheSer-157 |
| SEQ. ID. NO. 285 | 168-IleGlyValLeuGlyAsnLeuGluThrGly-177 |
| SEQ. ID. NO. 286 | 186-GlyAlaValGlyLysLeuSer-192 |
| SEQ. ID. NO. 287 | 226-TyrLysPheThrArgProProThrGly-234 |
| SEQ. ID. NO. 288 | 236-ValLeuArgIleAspArgIleLysGluIleHisGlnAlaLeu-249 |
| SEQ. ID. NO. 289 | 261-SerValProGlnGluTrpLeuLysValIleAsnGluTyrGlyGlyAsnIleGlyGluThrTyrGlyValProValGluGluIleValGluGlyIleLys HisGly-295 |
| SEQ. ID. NO. 290 | 314-ArgArgTyrLeuAlaGluAsn-320 |
| SEQ. ID. NO. 291 | 330-LeuSerLysThrIleGluAlaMetLys-338 |
| AntigenicIndex- Jameson-Wolf | |
| SEQ. ID. NO. 292 | 20-LeuProLysGluThrGln-25 |
| SEQ. ID. NO. 293 | 37-HisAlaAlaGluAsnSerTyrGly-44 |
| SEQ. ID. NO. 294 | 54-GluGlnMetArgAlaIleMetGluAlaAlaAspGlnValAsp-67 |
| SEQ. ID. NO. 295 | 75-SerAlaGlyAlaArgLysTyrAla-82 |
| SEQ. ID. NO. 296 | 106-HisGlnAspHisGlyAlaSerProAspValCysGlnArgSerIle-120 |
| SEQ. ID. NO. 297 | 129-MetAspGlySerLeuMetGluAspGlyLysThrProSerSerTyrGluTyr-145 |
| SEQ. ID. NO. 298 | 164-ValGluGlyGluIle-168 |
| SEQ. ID. NO. 299 | 173-AsnLeuGluThrGlyGluAlaGlyGluGluAspGlyVal-185 |
| SEQ. ID. NO. 300 | 191-LeuSerHisAspGln-195 |
| SEQ. ID. NO. 301 | 208-LysAspThrGlyVal-212 |
| SEQ. ID. NO. 302 | 221-ThrSerHisGlyAla-225 |
| SEQ. ID. NO. 303 | 227-LysPheThrArgProProThrGlyAspValLeuArgIleAspArgIleLysGluIleHis-246 |
| SEQ. ID. NO. 304 | 258-GlySerSerSerValPro-263 |

TABLE 1-continued

| | |
|---|---|
| SEQ. ID. NO. 305 | 271-AsnGluTyrGlyGlyAsnIleGlyGlu-279 |
| SEQ. ID. NO. 306 | 287-GluIleValGluGlyIleLysHisGlyValArgLysValAsnIleAspThrAspLeuArgLeuAlaSerThrGlyAlaVal-313 |
| SEQ. ID. NO. 307 | 316-TyrLeuAlaGluAsnProSerAspPheAspProArgLysTyrLeuSer-331 |
| SEQ. ID. NO. 308 | 333-ThrIleGluAlaMetLys-338 |
| SEQ. ID. NO. 309 | 350-CysGluGlyGlnAlaGlyLysIleLysProValSerLeuGluLysMetAlaSerArgTyrAlaLysGlyGluLeu-374 |
| Hydrophilic Regions - Hopp-Woods | |
| SEQ. ID. NO. 310 | 54-GluGlnMetArgAlaIleMetGluAlaAlaAspGlnValAsp-67 |
| SEQ. ID. NO. 311 | 76-AlaGlyAlaArgLysTyrAla-82 |
| SEQ. ID. NO. 312 | 108-AspHisGlyAlaSerProAspValCysGln-117 |
| SEQ. ID. NO. 313 | 132-SerLeuMetGluAspGlyLysThrProSer-141 |
| SEQ. ID. NO. 314 | 164-ValGluGlyGluIle-168 |
| SEQ. ID. NO. 315 | 175-GluThrGlyGluAlaGlyGluGluAspGlyVal-185 |
| SEQ. ID. NO. 316 | 208-LysAspThrGlyVal-212 |
| SEQ. ID. NO. 317 | 235-AspValLeuArgIleAspArgIleLysGluIleHis-246 |
| SEQ. ID. NO. 318 | 287-GluIleValGluGlyIleLysHisGlyValArgLysValAsnIleAspThrAspLeuArgLeu-307 |
| SEQ. ID. NO. 319 | 320-AsnProSerAspPheAspProArgLysTyrLeu-330 |
| SEQ. ID. NO. 320 | 333-ThrIleGluAlaMetLys-338 |
| SEQ. ID. NO. 321 | 352-GlyGlnAlaGlyLysIleLysProValSerLeuGluLysMetAlaSerArgTyrAlaLysGlyGluLeu-374 |
| 036-1 | |
| AMPHI Regions - AMPHI | |
| SEQ. ID. NO. 322 | 6-AlaValTyrSerAlaCysAlaAla-13 |
| SEQ. ID. NO. 323 | 29-GlyArgCysValAsnGlnTyr-35 |
| SEQ. ID. NO. 324 | 59-SerSerGlyArgPheCysGlnThrIleLys-68 |
| SEQ. ID. NO. 325 | 106-AlaAlaSerSerSerGlnSer-112 |
| SEQ. ID. NO. 326 | 142-AlaAsnArgArgVal-146 |
| Antigenic Index - Jameson-Wolf | |
| SEQ. ID. NO. 327 | 16-ProAlaArgThrSerSerSerArgArgCysValSerSerGlyArgCysValAsnGlnTyrSerSerArgAlaAspAla-41 |
| SEQ. ID. NO. 328 | 43-ProTrpArgArgHisSerGlyAla-50 |
| SEQ. ID. NO. 329 | 55-CysSerSerAspSerSerGlyArgPhe-63 |
| SEQ. ID. NO. 330 | 73-ProSerPheSerAlaArgLysThrCysSerAspGlyGluThrSerAlaAspSerAsnTrpArg-93 |
| SEQ. ID. NO. 331 | 96-HisAlaAspGlyLeuGlnThrAlaSerSerAlaAlaSerSerSerGlnSerAlaGlnThrAlaArgArgMetPhe-120 |
| SEQ. ID. NO. 332 | 133-SerGlyArgPheCysCysGlyArgArgAlaAsnArgArgValArgHisGlyArgGlnAspAsnArgPro-155 |
| SEQ. ID. NO. 333 | 158-ProMetArgGluSerArgArgGlnSerAla-167 |
| SEQ. ID. NO. 334 | 178-LeuProAlaArgThrArgCys-184 |
| SEQ. ID. NO. 335 | 186-CysArgLeuLysArgArgIleProProAla-195 |
| SEQ. ID. NO. 336 | 200-ProProAlaArgProAspAsnArgSerAsnGlyGlySerSerAlaTyrArgThrMetHisLysThrLeuArgProTyrGluArgPro-228 |
| Hydrophilic Regions - Hopp-Woods | |
| SEQ. ID. NO. 337 | 18-ArgThrSerSerSerArgArgCysValSerSer-28 |
| SEQ. ID. NO. 338 | 35-TyrSerSerArgAlaAsp-40 |
| SEQ. ID. NO. 339 | 45-ArgArgHisSerGly-49 |
| SEQ. ID. NO. 340 | 55-CysSerSerAspSerSerGlyArg-62 |
| SEQ. ID. NO. 341 | 75-PheSerAlaArgLysThrCysSerAspGlyGluThrSerAla-88 |
| SEQ. ID. NO. 342 | 107-AlaSerSerSerGlnSer-112 |
| SEQ. ID. NO. 343 | 114-GlnThrAlaArgArgMetPhe-120 |
| SEQ. ID. NO. 344 | 137-CysCysGlyArgArgAlaAsnArgArgValArgHisGlyArgGlnAspAsnArgPro-155 |
| SEQ. ID. NO. 345 | 160-ArgGluSerArgArgGlnSer-166 |
| SEQ. ID. NO. 346 | 178-LeuProAlaArgThrArgCys-184 |
| SEQ. ID. NO. 347 | 186-CysArgLeuLysArgArgIleProPro-194 |
| SEQ. ID. NO. 348 | 202-AlaArgProAspAsnArgSerAsnGlyGly-211 |
| SEQ. ID. NO. 349 | 217-ThrMetHisLysThrLeuArgProTyrGluArgPro-228 |
| 038 | |
| AMPHI Regions - AMPHI | |
| SEQ. ID. NO. 350 | 100-GluAlaLysAspHis-104 |
| SEQ. ID. NO. 351 | 134-GluSerIleLys-137 |
| SEQ. ID. NO. 352 | 157-GluLysGlyThrGlyGluLeuSerAlaValGlnGluValGluLys-171 |
| SEQ. ID. NO. 353 | 178-AlaProIleAlaSerLeuAsn-184 |
| SEQ. ID. NO. 354 | 195-GluPheGlyGlnPheLeuGluProValArgAlaTyrArgArgGlnTyrGlyVal-212 |
| Antigenic Index - Jameson-Wolf | |
| SEQ. ID. NO. 355 | 2-ThrAspPheArgGlnAspPhe-8 |
| SEQ. ID. NO. 356 | 22-GluPheThrThrLysAlaGlyArgArgSerPro-32 |
| SEQ. ID. NO. 357 | 38-GlyLeuPheAsnAspGlyLeu-44 |
| SEQ. ID. NO. 358 | 58-IleGluSerGlyIleArg-63 |
| SEQ. ID. NO. 359 | 85-LeuAlaGluLysGlyVal-90 |
| SEQ. ID. NO. 360 | 96-TyrAsnArgLysGluAlaLysAspHisGlyGluGlyGly-108 |
| SEQ. ID. NO. 361 | 125-ValIleSerAlaGlyThrSerValArgGluSerIleLysLeuIleGluAlaGluGlyAlaThrLeuAspArgMetGluLysGlyThrGlyGlu-162 |
| SEQ. ID. NO. 362 | 167-GlnGluValGluLysGlnTyrGlyLeu-175 |
| SEQ. ID. NO. 363 | 191-GlnAsnAsnProGluPheGlyGln-198 |
| SEQ. ID. NO. 364 | 203-ValArgAlaTyrArgArgGlnTyrGlyValGlu-213 |
| Hydrophilic Regions - Hopp-Woods | |
| SEQ. ID. NO. 365 | 2-ThrAspPheArgGlnAspPhe-8 |
| SEQ. ID. NO. 366 | 22-GluPheThrThrLysAlaGlyArgArgSer-31 |
| SEQ. ID. NO. 367 | 85-LeuAlaGluLysGlyVal-90 |
| SEQ. ID. NO. 368 | 96-TyrAsnArgLysGluAlaLysAspHisGlyGlu-106 |
| SEQ. ID. NO. 369 | 130-ThrSerValArgGluSerIleLysLeuIleGluAlaGluGlyAlaThr-145 |
| SEQ. ID. NO. 370 | 153-LeuAspArgMetGluLysGlyThrGlyGlu-162 |

TABLE 1-continued

| | |
|---|---|
| SEQ. ID. NO. 371 | 167-GlnGluValGluLysGlnTyr-173 |
| SEQ. ID. NO. 372 | 204-ArgAlaTyrArgArgGlnTyrGly-211 |
| 040-2 | |
| AMPHI Regions - AMPHI | |
| SEQ. ID. NO. 373 | 8-ValAlaHisPheArgGluAlaValProTyrIleArg-19 |
| SEQ. ID. NO. 374 | 28-AlaGlyIleAspAsp-32 |
| SEQ. ID. NO. 375 | 38-AspThrLeuAsnLysLeu-43 |
| SEQ. ID. NO. 376 | 78-ProHisTyrCysArgGlyLeuArgValThrAspGlu-89 |
| SEQ. ID. NO. 377 | 92-LeuGluGlnAlaGlnGlnPheAlaGly-100 |
| SEQ. ID. NO. 378 | 113-SerValSerGlyPheAlaArgAlaPro-121 |
| SEQ. ID. NO. 379 | 134-ArgProIleGlyValIleAspGly-141 |
| SEQ. ID. NO. 380 | 146-TyrAlaGlyValIleArg-151 |
| SEQ. ID. NO. 381 | 187-LeuGlnThrAlaAla-191 |
| SEQ. ID. NO. 382 | 207-LeuSerAspGlyIleSerArgProAspGlyThrLeuAlaGlu-220 |
| SEQ. ID. NO. 383 | 223-SerAlaGlnGluAlaGlnSerLeuAlaGluHisAla-234 |
| SEQ. ID. NO. 384 | 244-SerAlaValAlaAlaLeuGluGly-251 |
| SEQ. ID. NO. 385 | 277-IleGlyThrSerIle-281 |
| SEQ. ID. NO. 386 | 289-IleArgGlnAlaHisSerGlyAspIleProHisIleAlaAlaLeuIleArgProLeuGlu-308 |
| SEQ. ID. NO. 387 | 320-TyrLeuGluAsnHisIleSerGluPheSerIle-330 |
| SEQ. ID. NO. 388 | 338-TyrGlyCysAlaAlaLeuLysThrPheAlaGluAlaAsp-350 |
| SEQ. ID. NO. 389 | 371-ArgLeuLeuAlaHisIle-376 |
| SEQ. ID. NO. 390 | 386-SerArgLeuPheAla-390 |
| Antigenic Index - Jameson-Wolf | |
| SEQ. ID. NO. 391 | 19-ArgGlnMetArgGlyLysThrLeu-26 |
| SEQ. ID. NO. 392 | 29-GlyIleAspAspArgLeuLeuGluGlyAspThrLeuAsn-41 |
| SEQ. ID. NO. 393 | 65-HisPheLeuAspArgHisAlaAlaAlaGlnGlyArgThrProHisTyrCysArgGlyLeuArgValThrAspGluThrSerLeuGluGlnAlaGln-96 |
| SEQ. ID. NO. 394 | 101-ThrValArgSerArgPheGlu-107 |
| SEQ. ID. NO. 395 | 119-ArgAlaProSerVal-123 |
| SEQ. ID. NO. 396 | 140-AspGlyThrAspMetGluTyr-146 |
| SEQ. ID. NO. 397 | 150-IleArgLysThrAspThrAlaAla-157 |
| SEQ. ID. NO. 398 | 173-LeuGlyHisSerTyrSerGlyLysThrPhe-182 |
| SEQ. ID. NO. 399 | 208-SerAspGlyIleSerArgProAspGlyThrLeuAla-219 |
| SEQ. ID. NO. 400 | 222-LeuSerAlaGlnGluAlaGlnSerLeuAlaGluHisAlaGlyGlyGluThrArgArgLeuIle-242 |
| SEQ. ID. NO. 401 | 249-LeuGluGlyGlyVal-253 |
| SEQ. ID. NO. 402 | 261-GlyAlaAlaAspGlySerLeuLeu-268 |
| SEQ. ID. NO. 403 | 272-PheThrArgAsnGlyIleGlyThrSerIleAlaLysGluAlaPheVal-287 |
| SEQ. ID. NO. 404 | 289-IleArgGlnAlaHisSerGlyAspIle-297 |
| SEQ. ID. NO. 405 | 305-ArgProLeuGluGluGlnGly-311 |
| SEQ. ID. NO. 406 | 313-LeuLeuHisArgSerArgGluTyrLeu-321 |
| SEQ. ID. NO. 407 | 331-LeuGluHisAspGlyAsnLeuTyr-338 |
| SEQ. ID. NO. 408 | 345-ThrPheAlaGluAlaAspCysGlyGlu-353 |
| SEQ. ID. NO. 409 | 361-ProGlnAlaGlnAspGlyGlyTyrGlyGluArgLeu-372 |
| SEQ. ID. NO. 410 | 377-IleAspLysAlaArgGly-382 |
| SEQ. ID. NO. 411 | 393-ThrAsnThrGlyGlu-397 |
| SEQ. ID. NO. 412 | 402-ArgGlyPheGlnThrAlaSerGluAspGluLeuProGluThrArgArgLysAspTyrArgSerAsnGlyArgAsnSerHisIleLeu-430 |
| Hydrophilic Regions - Hopp-Woods | |
| SEQ. ID. NO. 413 | 19-ArgGlnMetArgGlyLysThr-25 |
| SEQ. ID. NO. 414 | 29-GlyIleAspAspArgLeuLeuGluGlyAspThrLeuAsn-41 |
| SEQ. ID. NO. 415 | 65-HisPheLeuAspArgHisAlaAlaAlaGlnGlyArgThr-77 |
| SEQ. ID. NO. 416 | 84-LeuArgValThrAspGluThrSerLeuGluGln-94 |
| SEQ. ID. NO. 417 | 102-ValArgSerArgPheGlu-107 |
| SEQ. ID. NO. 418 | 140-AspGlyThrAspMetGluTyr-146 |
| SEQ. ID. NO. 419 | 150-IleArgLysThrAspThrAlaAla-157 |
| SEQ. ID. NO. 420 | 210-GlyIleSerArgProAspGlyThrLeu-218 |
| SEQ. ID. NO. 421 | 222-LeuSerAlaGlnGluAlaGlnSerLeuAlaGlu-232 |
| SEQ. ID. NO. 422 | 234-AlaGlyGlyGluThrArgArgLeuIle-242 |
| SEQ. ID. NO. 423 | 291-GlnAlaHisSerGlyAsp-296 |
| SEQ. ID. NO. 424 | 305-ArgProLeuGluGluGlnGly-311 |
| SEQ. ID. NO. 425 | 315-HisArgSerArgGluTyrLeu-321 |
| SEQ. ID. NO. 426 | 345-ThrPheAlaGluAlaAspCysGlyGlu-353 |
| SEQ. ID. NO. 427 | 362-GlnAlaGlnAspGlyGlyTyrGlyGlu-370 |
| SEQ. ID. NO. 428 | 377-IleAspLysAlaArgGly-382 |
| SEQ. ID. NO. 429 | 402-ArgGlyPheGlnThrAlaSerGluAspGluLeuProGluThrArgArgLysAspTyrArgSerAsnGlyArgAsn-426 |
| 041-1 | |
| AMPHI Regions-AMPHI | |
| SEQ. ID. NO. 430 | 6-AspProTyrArgHisPheGluAsnLeuAspSerAlaGluThr-19 |
| SEQ. ID. NO. 431 | 45-AspGlyIleLeuAla-49 |
| SEQ. ID. NO. 432 | 78-LysGlyValTyrArgValCysThrAlaAla-87 |
| SEQ. ID. NO. 433 | 102-ValAlaAspPheAspGluLeuLeu-109 |
| SEQ. ID. NO. 434 | 117-GlyValSerHisLeuValGluGlnProAsn-126 |
| SEQ. ID. NO. 435 | 219-ValAsnAlaTrpArgTyrLeuAsp-226 |
| SEQ. ID. NO. 436 | 232-IleAspLeuIleGluAlaSer-238 |
| SEQ. ID. NO. 437 | 258-LeuAsnLeuProAsnAspCysAspValValGlyTyrLeu-270 |
| SEQ. ID. NO. 438 | 282-TrpAsnArgAlaAsnGln-287 |
| SEQ. ID. NO. 439 | 317-GlnAlaLeuGluSerValGluThr-324 |
| SEQ. ID. NO. 440 | 331-AlaSerLeuLeuGluAsnValGlnGlyArg-340 |
| SEQ. ID. NO. 441 | 382-AspPheThrThrProLeu-387 |
| SEQ. ID. NO. 442 | 405-GlnProGlnGlnPhe-409 |
| SEQ. ID. NO. 443 | 451-GlyPheGlyIleProGluLeuProHisTyrLeuGlySerIleGlyLys-466 |
| SEQ. ID. NO. 444 | 493-AlaAlaGlnGlyIleSerLysHisLysSerValAspAspLeuLeuAlaValValArgAspLeuSerGluArg-516 |

TABLE 1-continued

| | |
|---|---|
| SEQ. ID. NO. 445 | 519-SerSerProGluHis-523 |
| SEQ. ID. NO. 446 | 541-ValArgGluProGlnSer-546 |
| SEQ. ID. NO. 447 | 556-LeuThrAspMetIleArgTyr-562 |
| SEQ. ID. NO. 448 | 571-TrpThrAspGluTyrGlyAsnProGlnLysTyrGlu-582 |
| SEQ. ID. NO. 449 | 591-LeuSerProTyrHisAsnLeuSerAspGlyIleAspTyrProPro-605 |
| SEQ. ID. NO. 450 | 620-AlaHisAlaLeuLys-624 |
| SEQ. ID. NO. 451 | 626-TyrAlaLysLeuArg-630 |
| SEQ. ID. NO. 452 | 645-GlyHisThrGlyAsn-649 |
| SEQ. ID. NO. 453 | 651-ThrGlnArgGluSer-655 |
| AntigenicIndex- Jameson-Wolf | |
| SEQ. ID. NO. 454 | 1-MetLysSerTyrProAspProTyrArgHisPheGluAsnLeuAspSerAlaGluThrGln-20 |
| SEQ. ID. NO. 455 | 26-AlaAsnAlaGluThrArgAlaArgPheLeuGluAsnAspLysAlaArgAlaLeuSerAspGly-46 |
| SEQ. ID. NO. 456 | 51-LeuGlnAspThrArgGlnIleProPhe-59 |
| SEQ. ID. NO. 457 | 61-GlnGluHisArgAlaArg-66 |
| SEQ. ID. NO. 458 | 72-GlnAspAlaGluTyrProLysGlyVal-80 |
| SEQ. ID. NO. 459 | 89-TyrArgSerGlyTyrProGluTrp-96 |
| SEQ. ID. NO. 460 | 104-AspPheAspGluLeuLeuGlyAspAspValTyr-114 |
| SEQ. ID. NO. 461 | 123-GluGlnProAsnArg-127 |
| SEQ. ID. NO. 462 | 133-SerLysLeuGlySerAspThrAlaTyr-141 |
| SEQ. ID. NO. 463 | 145-ValAspLeuGluAlaGlyGluLeuValGlu-154 |
| SEQ. ID. NO. 464 | 161-AlaGlyLysAsnHisValSerTrpArgAspGluAsnSerVal-174 |
| SEQ. ID. NO. 465 | 178-ProAlaTrpAsnGluArgGlnLeuThrGlnSerGlyTyrProArgGluValTrpLeuValGluArgGlyLysSerPheGluGluSerLeu-207 |
| SEQ. ID. NO. 466 | 212-IleGlyGluAspGlyMet-217 |
| SEQ. ID. NO. 467 | 223-ArgTyrLeuAspProGlnGlySerProIleAspLeuIleGluAlaSerAspGlyPheTyr-242 |
| SEQ. ID. NO. 468 | 249-ValSerAlaGluGlyGluAlaLysProLeuAsnLeuProAsnAspCysAspVal-266 |
| SEQ. ID. NO. 469 | 277-ThrLeuArgLysAspTrpAsnArgAlaAsnGlnSerTyrProSer-291 |
| SEQ. ID. NO. 470 | 298-LysLeuAsnArgGlyGluLeuGly-305 |
| SEQ. ID. NO. 471 | 313-ProAspGluThrGlnAla-318 |
| SEQ. ID. NO. 472 | 320-GluSerValGluThrThrLys-326 |
| SEQ. ID. NO. 473 | 337-ValGlnGlyArgLeuLysAla-343 |
| SEQ. ID. NO. 474 | 345-ArgPheAlaAspGlyLysTrpGlnGluValGluLeuProArgLeuProSerGly-362 |
| SEQ. ID. NO. 475 | 365-GluMetThrAspGlnProTrpGlyGly-373 |
| SEQ. ID. NO. 476 | 401-ValMetArgArgGlnProGlnGlnPheAspSerAspGlyIleAsn-415 |
| SEQ. ID. NO. 477 | 422-ThrSerAlaAspGlyGluArgIle-429 |
| SEQ. ID. NO. 478 | 435-GlyLysAsnAlaAlaProAspMet-442 |
| SEQ. ID. NO. 479 | 479-AsnIleArgGlyGlyGlyGluPheGlyProArgTrpHis-491 |
| SEQ. ID. NO. 480 | 496-GlyIleSerLysHisLysSerValAspAsp-505 |
| SEQ. ID. NO. 481 | 511-ArgAspLeuSerGluArgGlyIleSerSerProGluHisIle-524 |
| SEQ. ID. NO. 482 | G528-lyGlySerAsnGly-532 |
| SEQ. ID. NO. 483 | 540-PheValArgGluProGlnSerIleGlyAla-549 |
| SEQ. ID. NO. 484 | 568-GlySerSerTrpThrAspGluTyrGlyAsnProGlnLysTyrGluValCysLysArgArgLeuGlyGluLeuSerProTyr-594 |
| SEQ. ID. NO. 485 | 596-AsnLeuSerAspGlyIleAspTyrPro-604 |
| SEQ. ID. NO. 486 | 610-ThrSerLeuSerAspAspArgValHis-618 |
| SEQ. ID. NO. 487 | 627-AlaLysLeuArgGluThrSerAla-634 |
| SEQ. ID. NO. 488 | 639-TyrSerProAspGlyGlyGlyHisThrGlyAsnGlyThrGlnArgGluSerAlaAspGluLeu-659 |
| Hydrophilic Regions - Hopp-Woods | |
| SEQ. ID. NO. 489 | 3-SerTyrProAspProTyrArgHis-10 |
| SEQ. ID. NO. 490 | 12-GluAsnLeuAspSerAlaGluThr-19 |
| SEQ. ID. NO. 491 | 26-AlaAsnAlaGluThrArgAlaArgPheLeuGluAsnAspLysAlaArgAlaLeuSer-44 |
| SEQ. ID. NO. 492 | 52-GlnAspThrArgGln-56 |
| SEQ. ID. NO. 493 | 61-GlnGluHisArgAlaArg-66 |
| SEQ. ID. NO. 494 | 72-GlnAspAlaGluTyrPro-77 |
| SEQ. ID. NO. 495 | 104-AspPheAspGluLeuLeuGly-110 |
| SEQ. ID. NO. 496 | 145-ValAspLeuGluAlaGlyGluLeuValGlu-154 |
| SEQ. ID. NO. 497 | 166-ValSerTrpArgAspGluAsnSer-173 |
| SEQ. ID. NO. 498 | 180-TrpAsnGluArgGlnLeuThr-186 |
| SEQ. ID. NO. 499 | 198-GluArgGlyLysSerPheGluGluSerLeu-207 |
| SEQ. ID. NO. 500 | 212-IleGlyGluAspGlyMet-217 |
| SEQ. ID. NO. 501 | 233-AspLeuIleGluAlaSerAsp-239 |
| SEQ. ID. NO. 502 | 249-ValSerAlaGluGlyGluAlaLysPro-257 |
| SEQ. ID. NO. 503 | 278-LeuArgLysAspTrpAsnArg-284 |
| SEQ. ID. NO. 504 | 298-LysLeuAsnArgGlyGluLeuGly-305 |
| SEQ. ID. NO. 505 | 313-ProAspGluThrGlnAla-318 |
| SEQ. ID. NO. 506 | 320-GluSerValGluThrThrLys-326 |
| SEQ. ID. NO. 507 | 337-ValGlnGlyArgLeuLysAla-343 |
| SEQ. ID. NO. 508 | 401-ValMetArgArgGlnProGlnGlnPheAspSerAspGlyIleAsn-415 |
| SEQ. ID. NO. 509 | 424-AlaAspGlyGluArg-428 |
| SEQ. ID. NO. 510 | 436-LysAsnAlaAlaProAsp-441 |
| SEQ. ID. NO. 511 | 481-ArgGlyGlyGlyGluPheGly-487 |
| SEQ. ID. NO. 512 | 496-GlyIleSerLysHisLysSerValAspAsp-505 |
| SEQ. ID. NO. 513 | 511-ArgAspLeuSerGluArgGlyIleSerSer-520 |
| SEQ. ID. NO. 514 | 540-PheValArgGluProGlnSer-546 |
| SEQ. ID. NO. 515 | 571-TrpThrAspGluTyrGlyAsn-577 |
| SEQ. ID. NO. 516 | 579-GlnLysTyrGluValCysLysArgArgLeuGlyGlu-590 |

TABLE 1-continued

| | |
|---|---|
| SEQ. ID. NO. 517 | 612-LeuSerAspAspArgValHis-618 |
| SEQ. ID. NO. 518 | 627-AlaLysLeuArgGluThrSer-633 |
| SEQ. ID. NO. 519 | 650-GlyThrGlnArgGluSerAlaAspGluLeu-659 |
| 042-1 | |
| AMPHI Regions - AMPHI | |
| SEQ. ID. NO. 520 | 17-AlaLeuSerAsnThrSerThr-23 |
| SEQ. ID. NO. 521 | 33-AlaValArgSerMetMetLysIle-40 |
| SEQ. ID. NO. 522 | 138-SerProLeuValArgIleLeuProLeuSer-147 |
| SEQ. ID. NO. 523 | 151-SerMetValValAlaPhePheAlaAsn-159 |
| Antigenic Index - Jameson-Wolf | |
| SEQ. ID. NO. 524 | 14-ArgThrSerAlaLeuSerAsnThrSerThrAlaAlaGlyProSerCys-29 |
| SEQ. ID. NO. 525 | 49-TyrSerLysGluThrGlyCysProCysProSerLeuArgLysAspSerSerThrGlyGlyArgProMetSerProCys-74 |
| SEQ. ID. NO. 526 | 77-LeuAlaAsnArgAspCysValProLysAlaAspThr-88 |
| SEQ. ID. NO. 527 | 93-ThrAspSerThrSerProArgProLeu-101 |
| SEQ. ID. NO. 528 | 122-AlaArgAlaSerLeuProLysIleArgAlaLysVal-133 |
| SEQ. ID. NO. 529 | 160-CysSerTyrAlaSerAlaProGlyPro-168 |
| Hydrophilic Regions - Hopp-Woods | |
| SEQ. ID. NO. 530 | 49-TyrSerLysGluThrGlyCys-55 |
| SEQ. ID. NO. 531 | 59-SerLeuArgLysAspSerSerThrGlyGlyArgProMet-71 |
| SEQ. ID. NO. 532 | 78-AlaAsnArgAspCysValProLysAlaAspThr-88 |
| SEQ. ID. NO. 533 | 94-AspSerThrSerProArg-99 |
| SEQ. ID. NO. 534 | 125-SerLeuProLysIleArgAlaLysVal-133 |
| 043-2 | |
| AMPHI Regions - AMPHI | |
| SEQ. ID. NO. 535 | 24-ValGluProSerArg-28 |
| SEQ. ID. NO. 536 | 36-HisGlyGlyLeuAspGlyAlaAlaGlyPheAspGluGlyGluArg-50 |
| SEQ. ID. NO. 537 | 59-AlaSerGlyAspGlyPhe-64 |
| SEQ. ID. NO. 538 | 83-AlaGlyAspPheGlyAspGlyGlnArg-91 |
| Antigenic Index - Jameson-Wolf | |
| SEQ. ID. NO. 539 | 1-MetProProAlaPro-5 |
| SEQ. ID. NO. 540 | 11-IleArgArgGlnLysSerValMetProSerGluArgPheValGluProSerArg-28 |
| SEQ. ID. NO. 541 | 35-ValHisGlyGlyLeuAspGlyAlaAlaGlyPheAspGluGlyGluArgValPhe-52 |
| SEQ. ID. NO. 542 | 56-AlaAlaGlnAlaSerGlyAspGlyPheAla-65 |
| SEQ. ID. NO. 543 | 79-GlnSerAspAlaAlaGlyAspPheGlyAspGlyGlnArgThrGlyGlu-94 |
| SEQ. ID. NO. 544 | 96-ValLeuGlnAspValGlyGly-102 |
| SEQ. ID. NO. 545 | 116-AlaGluGlyGluAlaGln-121 |
| Hydrophilic Regions - Hopp-Woods | |
| SEQ. ID. NO. 546 | 11-IleArgArgGlnLysSerValMetProSerGluArgPheValGluProSerArg-28 |
| SEQ. ID. NO. 547 | 43-AlaGlyPheAspGluGlyGluArgValPhe-52 |
| SEQ. ID. NO. 548 | 81-AspAlaAlaGlyAspPheGlyAspGlyGlnArgThrGly-93 |
| SEQ. ID. NO. 549 | 116-AlaGluGlyGluAlaGln-121 |
| 046-2 | |
| AMPHI Regions - AMPHI | |
| SEQ. ID. NO. 550 | 6-ArgProThrSerSerPro-11 |
| SEQ. ID. NO. 551 | 46-ThrSerCysSerGlyLeuMetValSer-54 |
| SEQ. ID. NO. 552 | 64-PheSerLeuPheSerSer-69 |
| SEQ. ID. NO. 553 | 113-LysSerAlaSerSer-117 |
| SEQ. ID. NO. 554 | 143-SerCysAsnAlaPheSerSer-149 |
| SEQ. ID. NO. 555 | 155-ThrSerLeuLeuGlyMetAlaAlaArgPheCysAlaThrVal-168 |
| Antigenic Index - Jameson-Wolf | |
| SEQ. ID. NO. 556 | 6-ArgProThrSerSerProProArgArgAlaCys-16 |
| SEQ. ID. NO. 557 | 20-IleArgThrArgSerSerAlaLysArgLysThrCysAsnAlaProGlyGlnSerIleArgProAlaSerCysSer-44 |
| SEQ. ID. NO. 558 | 57-ProAsnMetGluArgLeuPro-63 |
| SEQ. ID. NO. 559 | 75-SerArgTyrSerLeuGluArgThrArgAlaMetArgProGlyMetLeuAsnArgSerAlaAla-95 |
| SEQ. ID. NO. 560 | 105-SerLeuArgGluSerAlaSerSerLysSerAlaSerSerAlaProAlaArgSerAsnValLysGlyAspAlaProLeuProLysThrValTrpThrSerArg ArgLeuProVal-142 |
| SEQ. ID. NO. 561 | 169-GluProThrCysProLeuProLys-176 |
| Hydrophilic Regions - Hopp-Woods | |
| SEQ. ID. NO. 562 | 7-ProThrSerSerProProArgArgAlaCys-16 |
| SEQ. ID. NO. 563 | 20-IleArgThrArgSerSerAlaLysArgLysThrCysAsn-32 |
| SEQ. ID. NO. 564 | 36-GlnSerIleArgProAlaSer-42 |
| SEQ. ID. NO. 565 | 58-AsnMetGluArgLeuPro-63 |
| SEQ. ID. NO. 566 | 75-SerArgTyrSerLeuGluArgThrArgAlaMetArg-86 |
| SEQ. ID. NO. 567 | 105-SerLeuArgGluSerAlaSerSerLysSerAlaSer-116 |
| SEQ. ID. NO. 568 | 118-AlaProAlaArgSerAsnValLysGlyAspAlaProLeu-130 |
| 047-2 | |
| AMPHI Regions - AMPHI | |
| SEQ. ID. NO. 569 | 17-IleAlaAspIleAlaGlnAspLeuProAspGlyAla-28 |
| SEQ. ID. NO. 570 | 62-AlaGluAsnIleGlyAlaVal-68 |
| SEQ. ID. NO. 571 | 93-ArgLeuAlaLysGlnLeuGlu-99 |
| SEQ. ID. NO. 572 | 141-TyrIleAspGluIleAspValPhe-148 |
| SEQ. ID. NO. 573 | 161-SerAlaLeuLeuAla-165 |
| SEQ. ID. NO. 574 | 185-LeuLeuGluGlyAsn-189 |
| SEQ. ID. NO. 575 | 202-IleGlySerIleLeuAla-207 |
| SEQ. ID. NO. 576 | 247-SerGlyIleLysTrpProGluGlyCys-255 |
| SEQ. ID. NO. 577 | 257-IleAlaAlaValValArgAlaGlyThrGly-266 |
| SEQ. ID. NO. 578 | 293-IleLeuAsnGluLeuGluLysLeuIle-301 |
| Antigenic Index - Jameson-Wolf | |
| SEQ. ID. NO. 579 | 5-GlnAlaArgArgGlyGlyLeuLeu-12 |
| SEQ. ID. NO. 580 | 20-IleAlaGlnAspLeuProAspGlyAlaAsp-29 |

TABLE 1-continued

| | |
|---|---|
| SEQ. ID. NO. 581 | 36-TyrArgAsnAsnArgLeu-41 |
| SEQ. ID. NO. 582 | 51-IleGluGlyAspGlu-55 |
| SEQ. ID. NO. 583 | 70-ProGluLeuArgProLysGluThrSerThrArgArgIleMet-83 |
| SEQ. ID. NO. 584 | 86-GlyGlyGlyAsnIle-90 |
| SEQ. ID. NO. 585 | 96-LysGlnLeuGluHis-100 |
| SEQ. ID. NO. 586 | 106-IleIleGluCysArgProArgArgAlaGluTrpIle-117 |
| SEQ. ID. NO. 587 | 119-GluAsnLeuAspAsnThrLeu-125 |
| SEQ. ID. NO. 588 | 130-SerAlaThrAspGluThrLeuLeuAspAsnGluTyrIleAspGluIleAsp-146 |
| SEQ. ID. NO. 589 | 152-ThrAsnAspAspGluSerAsnIle-159 |
| SEQ. ID. NO. 590 | 168-LeuGlyAlaLysArgVal-173 |
| SEQ. ID. NO. 591 | 178-AsnArgSerSerTyr-182 |
| SEQ. ID. NO. 592 | 186-LeuGluGlyAsnLysIle-191 |
| SEQ. ID. NO. 593 | 208-HisIleArgArgGlyAspIleVal-215 |
| SEQ. ID. NO. 594 | 219-ProIleArgArgGlyThrAlaGluAlaIleGlu-229 |
| SEQ. ID. NO. 595 | 232-AlaHisGlyAspLysLysThrSer-239 |
| SEQ. ID. NO. 596 | 242-IleGlyArgArgIleSerGlyIleLysTrpProGluGlyCysHis-256 |
| SEQ. ID. NO. 597 | 262-ArgAlaGlyThrGlyGluThr-268 |
| SEQ. ID. NO. 598 | 277-ValIleGlnAspGlyAspHis-283 |
| SEQ. ID. NO. 599 | 288-ValSerArgArgArgIleLeuAsnGluLeuGluLys-299 |
| Hydrophilic Regions - Hopp-Woods | |
| SEQ. ID. NO. 600 | 5-GlnAlaArgArgGlyGly-10 |
| SEQ. ID. NO. 601 | 20-IleAlaGlnAspLeuProAspGlyAlaAsp-29 |
| SEQ. ID. NO. 602 | 51-IleGluGlyAspGlu-55 |
| SEQ. ID. NO. 603 | 70-ProGluLeuArgProLysGluThrSerThrArgArgIleMet-83 |
| SEQ. ID. NO. 604 | 106-IleIleGluCysArgProArgArgAlaGluTrpIle-117 |
| SEQ. ID. NO. 605 | 130-SerAlaThrAspGluThrLeuLeu-137 |
| SEQ. ID. NO. 606 | 140-GluTyrIleAspGluIleAsp-146 |
| SEQ. ID. NO. 607 | 152-ThrAsnAspAspGluSerAsnIle-159 |
| SEQ. ID. NO. 608 | 168-LeuGlyAlaLysArgVal-173 |
| SEQ. ID. NO. 609 | 186-LeuGluGlyAsnLysIle-191 |
| SEQ. ID. NO. 610 | 209-IleArgArgGlyAspIle-214 |
| SEQ. ID. NO. 611 | 219-ProIleArgArgGlyThrAlaGluAlaIleGlu-229 |
| SEQ. ID. NO. 612 | 232-AlaHisGlyAspLysLysThrSer-239 |
| SEQ. ID. NO. 613 | 242-IleGlyArgArgIleSer-247 |
| SEQ. ID. NO. 614 | 277-ValIleGlnAspGlyAsp-282 |
| SEQ. ID. NO. 615 | 289-SerArgArgArgIleLeuAsnGluLeuGluLys-299 |
| 049-2 | |
| AMPHI Regions - AMPHI | |
| SEQ. ID. NO. 616 | 15-GlnHisLeuLeuGlu-19 |
| SEQ. ID. NO. 617 | 34-AspAspAlaValAspGlyIleGlyGlnMet-43 |
| SEQ. ID. NO. 618 | 50-GlnProPheGlyGln-54 |
| SEQ. ID. NO. 619 | 61-GluHisPheAlaProValAspGlyPheArg-70 |
| SEQ. ID. NO. 620 | 79-HisGlnArgPhePheArgIle-85 |
| SEQ. ID. NO. 621 | 202-ArgGlyAlaGlyGlnArgArgValSerArgHisCys-213 |
| SEQ. ID. NO. 622 | 217-AlaArgLeuThrGlnValPheGlnThrPhePhe-227 |
| Antigenic Index - Jameson-Wolf | |
| SEQ. ID. NO. 623 | 6-PheAspTyrArgProArgLeuLeu-13 |
| SEQ. ID. NO. 624 | 21-IleGlyGluAsnArgHis-26 |
| SEQ. ID. NO. 625 | 28-LeuLeuHisArgArgSerAspAspAlaValAspGlyIleGly-41 |
| SEQ. ID. NO. 626 | 49-AspGlnProPheGly-53 |
| SEQ. ID. NO. 627 | 64-AlaProValAspGlyPheArgValGlnAspIleAspLeuAspGlyHisGlnArgPhe-82 |
| SEQ. ID. NO. 628 | 89-ValPheArgAsnArgArgLeuIle-96 |
| SEQ. ID. NO. 629 | 111-LeuSerGlyPheLys-115 |
| SEQ. ID. NO. 630 | 122-GlyIleLysProAspSerProProArgPhe-131 |
| SEQ. ID. NO. 631 | 135-PheArgAsnArgHisLeuGlnGlySerLeuArgVal-146 |
| SEQ. ID. NO. 632 | 150-PheLeuLysAspAspHisArgValGly-158 |
| SEQ. ID. NO. 633 | 182-GlnHisThrGlySer-186 |
| SEQ. ID. NO. 634 | 193-ArgHisArgArgValArgSerGlyPheArgGlyAlaGlyGlnArgArgValSerArgHisCys-213 |
| SEQ. ID. NO. 635 | 246-LysGlnThrAsnProArgProLysArgGlyLeu-256 |
| Hydrophilic Regions - Hopp-Woods | |
| SEQ. ID. NO. 636 | 21-IleGlyGluAsnArgHis-26 |
| SEQ. ID. NO. 637 | 30-HisArgArgSerAspAspAlaValAsp-38 |
| SEQ. ID. NO. 638 | 67-AspGlyPheArgValGlnAspIleAspLeuAspGlyHisGlnArg-81 |
| SEQ. ID. NO. 639 | 91-ArgAsnArgArgLeuIle-96 |
| SEQ. ID. NO. 640 | 124-LysProAspSerProProArg-130 |
| SEQ. ID. NO. 641 | 150-PheLeuLysAspAspHisArgVal-157 |
| SEQ. ID. NO. 642 | 193-ArgHisArgArgValArgSerGlyPheArgGlyAlaGlyGlnArgArgValSerArg-211 |
| SEQ. ID. NO. 643 | 246-LysGlnThrAsnProArgProLysArgGlyLeu-256 |
| 050-1 | |
| AMPHI Regions - AMPHI | |
| SEQ. ID. NO. 644 | 10-IleGlnSerIleCysAspAlaPheGlnPheIleSerTyrTyr-23 |
| SEQ. ID. NO. 645 | 25-ProLysAspTyrIleAspAlaLeuTyrLysAlaTrpGlnLys-38 |
| SEQ. ID. NO. 646 | 94-ValAsnGluGlyVal-98 |
| SEQ. ID. NO. 647 | 163-AsnProSerAspAsnIleValAspTrpValLeuLys-174 |
| SEQ. ID. NO. 648 | 177-ProThrMetGlyAla-181 |
| SEQ. ID. NO. 649 | 235-LeuGluLeuPheGluLysValAsnAla-243 |
| SEQ. ID. NO. 650 | 250-GlyLeuGlyGlyLeuThrThr-256 |
| SEQ. ID. NO. 651 | 275-AlaMetIleProAsn-279 |
| SEQ. ID. NO. 652 | 302-ArgValGluAspTrpProAspLeuThr-310 |
| SEQ. ID. NO. 653 | 315-AsnGlyLysArgValAspValAsp-322 |

TABLE 1-continued

| | |
|---|---|
| SEQ. ID. NO. 654 | 353-LysArgLeuValAspMetLeuAsnLys-361 |
| SEQ. ID. NO. 655 | 367-ValAspPheThrAsnArgLeu-373 |
| SEQ. ID. NO. 656 | 379-ProValAspProValGlyAspGlu-386 |
| SEQ. ID. NO. 657 | 396-AlaThrArgMetAspLysPheThrArgGlnMet-406 |
| SEQ. ID. NO. 658 | 410-ThrAspLeuLeuGlyMet-415 |
| SEQ. ID. NO. 659 | 422-GlyValAlaThrCysGluAlaIleAla-430 |
| SEQ. ID. NO. 660 | 452-LysSerSerLysValLeuAlaPhe-459 |
| SEQ. ID. NO. 661 | 490-AlaThrAlaProArgLysTrp-496 |
| Antigenic Index - Jameson-Wolf | |
| SEQ. ID. NO. 662 | 4-IleLysGlnGluAspPheIle-10 |
| SEQ. ID. NO. 663 | 23-TyrHisProLysAspTyrIleAspAlaLeu-32 |
| SEQ. ID. NO. 664 | 36-TrpGlnLysGluGluAsnProAlaAlaLysAspAlaMet-48 |
| SEQ. ID. NO. 665 | 55-SerArgMetCysAlaGluAsnAsnArgProIleCysGlnAspThrGly-70 |
| SEQ. ID. NO. 666 | 88-MetSerValGluGluMetValAsnGluGlyValArgArgAlaTyrThrTrpGluGlyAsnThrLeuArgAlaSerVal-113 |
| SEQ. ID. NO. 667 | 116-AspProAlaGlyLysArgGlnAsnThrLysAspAsnThr-128 |
| SEQ. ID. NO. 668 | 138-ProGlyGlyLysValGluVal-144 |
| SEQ. ID. NO. 669 | 148-AlaLysGlyGlyGlySerGluAsnLysSerLysLeu-159 |
| SEQ. ID. NO. 670 | 163-AsnProSerAspAsnIle-168 |
| SEQ. ID. NO. 671 | 192-GlyIleGlyGlyThrProGluLysAlaValLeuMetAlaLysGluSerLeu-208 |
| SEQ. ID. NO. 672 | 213-AspIleGlnGluLeuGlnGluLysAlaAlaSerGlyAlaGluLeuSerThr-229 |
| SEQ. ID. NO. 673 | 284-ArgHisValGluPheGluLeuAspGlySerGlyProValGluLeuThrProProArgValGluAspTrpProAspLeuThrTyrSerProAspAsnGly LysArgValAspValAspLysLeuThrLysGluGluValAlaSer-331 |
| SEQ. ID. NO. 674 | 345-LeuThrGlyArgAspAlaAlaHisLysArgLeuVal-356 |
| SEQ. ID. NO. 675 | 359-LeuAsnLysGlyGluGluLeuPro-366 |
| SEQ. ID. NO. 676 | 379-ProValAspProValGlyAspGluValValGlyProAlaGlyProThrThrAlaThrArgMetAspLysPheThrArgGlnMetLeuGluGlnThr Asp-411 |
| SEQ. ID. NO. 677 | 417-GlyLysSerGluArgGlyValAlaThr-425 |
| SEQ. ID. NO. 678 | 428-AlaIleAlaAspAsnLysAla-434 |
| SEQ. ID. NO. 679 | 450-AlaIleLysSerSerLys-455 |
| SEQ. ID. NO. 680 | 470-PheGluValLysAspMetPro-476 |
| SEQ. ID. NO. 681 | 481-ValAspSerLysGlyGluSerIle-488 |
| SEQ. ID. NO. 682 | 492-AlaProArgLysTrpGlnAla-498 |
| Hydrophilic Regions - Hopp-Woods | |
| SEQ. ID. NO. 683 | 4-IleLysGlnGluAspPheIle-10 |
| SEQ. ID. NO. 684 | 36-TrpGlnLysGluGluAsnProAlaAlaLysAspAlaMet-48 |
| SEQ. ID. NO. 685 | 57-MetCysAlaGluAsnAsnArgProIleCys-66 |
| SEQ. ID. NO. 686 | 88-MetSerValGluGluMetValAsnGluGlyValArgArg-100 |
| SEQ. ID. NO. 687 | 117-ProAlaGlyLysArgGlnAsnThrLysAspAsnThr-128 |
| SEQ. ID. NO. 688 | 140-GlyLysValGluVal-144 |
| SEQ. ID. NO. 689 | 148-AlaLysGlyGlyGlySerGluAsnLysSerLysLeu-159 |
| SEQ. ID. NO. 690 | 195-GlyThrProGluLysAlaValLeuMetAlaLysGluSerLeu-208 |
| SEQ. ID. NO. 691 | 213-AspIleGlnGluLeuGlnGluLysAlaAlaSer-223 |
| SEQ. ID. NO. 692 | 225-AlaGluLeuSerThr-229 |
| SEQ. ID. NO. 693 | 284-ArgHisValGluPheGluLeuAspGly-292 |
| SEQ. ID. NO. 694 | 299-ThrProProArgValGluAspTrpPro-307 |
| SEQ. ID. NO. 695 | 313-ProAspAsnGlyLysArgValAspValAspLysLeuThrLysGluGluValAlaSer-331 |
| SEQ. ID. NO. 696 | 345-LeuThrGlyArgAspAlaAlaHisLysArgLeuVal-356 |
| SEQ. ID. NO. 697 | 359-LeuAsnLysGlyGluGluLeuPro-366 |
| SEQ. ID. NO. 698 | 382-ProValGlyAspGluValVal-388 |
| SEQ. ID. NO. 699 | 397-ThrArgMetAspLysPheThrArgGlnMetLeuGluGlnThrAsp-411 |
| SEQ. ID. NO. 700 | 417-GlyLysSerGluArgGlyValAla-424 |
| SEQ. ID. NO. 701 | 428-AlaIleAlaAspAsnLysAla-434 |
| SEQ. ID. NO. 702 | 450-AlaIleLysSerSerLys-455 |
| SEQ. ID. NO. 703 | 470-PheGluValLysAspMetPro-476 |
| SEQ. ID. NO. 704 | 481-ValAspSerLysGlyGluSerIle-488 |
| SEQ. ID. NO. 705 | 492-AlaProArgLysTrpGlnAla-498 |
| 052 | |
| AMPHI Regions - AMPHI | |
| SEQ. ID. NO. 706 | 12-AlaProCysPheLysGlyCysGluProThrGlyAsp-23 |
| SEQ. ID. NO. 707 | 41-AlaLysAlaSerLysSerAlaThrSerProLysGlyLeuAspGlyValSerLys-58 |
| SEQ. ID. NO. 708 | 67-ThrAlaAlaPheHisSerPheIleSer-75 |
| SEQ. ID. NO. 709 | 84-MetProAsnLeuValThrMetLeu-91 |
| Antigenic Index - Jameson-Wolf | |
| SEQ. ID. NO. 710 | 4-ValAlaGluGluThrGluIle-10 |
| SEQ. ID. NO. 711 | 14-CysPheLysGlyCysGluProThrGlyAspSerArgLeuLeuSerThrThrLysSerAlaPro-34 |
| SEQ. ID. NO. 712 | 37-CysAlaAsnSerAlaLysAlaSerLysSerAlaThrSerProLysGlyLeuAspGlyValSerLysAsnSerSer-61 |
| SEQ. ID. NO. 713 | 75-SerValGlyAspThrArgLeuThrProMet-84 |
| SEQ. ID. NO. 714 | 97-ValValProAsnArgLeuArgLeuGluThrThrTrpSerProAlaCysArgLysValLysAsnAlaAla-119 |
| Hydrophilic Regions - Hopp-Woods | |
| SEQ. ID. NO. 715 | 4-ValAlaGluGluThrGluIle-10 |
| SEQ. ID. NO. 716 | 16-LysGlyCysGluProThrGlyAspSerArgLeu-26 |
| SEQ. ID. NO. 717 | 30-ThrLysSerAlaPro-34 |
| SEQ. ID. NO. 718 | 39-AsnSerAlaLysAlaSerLysSerAlaThrSerProLysGlyLeuAspGlyValSerLysAsnSer-60 |
| SEQ. ID. NO. 719 | 77-GlyAspThrArgLeu-81 |
| SEQ. ID. NO. 720 | 100-AsnArgLeuArgLeu-104 |
| SEQ. ID. NO. 721 | 111-AlaCysArgLysValLysAsnAlaAla-119 |
| 075 | |
| AMPHI Regions - AMPHI | |
| SEQ. ID. NO. 722 | 15-LysSerAlaAlaLysMetProThrThrIleGlnProAlaSerIleProSer-31 |
| SEQ. ID. NO. 723 | 65-AlaProTyrLeuArgGlnValLeu-72 |

TABLE 1-continued

| | |
|---|---|
| SEQ. ID. NO. 724 | 80-PheLysLysCysLeuAla-85 |
| SEQ. ID. NO. 725 | 116-AspPhePheGlnThrCysValAsnArgPhePheGluValValGluIleIleGlyIleGly-135 |
| Antigenic Index - Jameson-Wolf | |
| SEQ. ID. NO. 726 | 12-GluAsnThrLysSerAlaAlaLysMetPro-21 |
| SEQ. ID. NO. 727 | 52-AlaLysAlaArgGly-56 |
| SEQ. ID. NO. 728 | 91-PhePheArgArgProProAsnIleArgLysSerValPheGlnLysSerGluTyrAspLys-110 |
| Hydrophilic Regions - Hopp-Woods | |
| SEQ. ID. NO. 729 | 12-GluAsnThrLysSerAlaAlaLys-19 |
| SEQ. ID. NO. 730 | 52-AlaLysAlaArgGly-56 |
| SEQ. ID. NO. 731 | 91-PhePheArgArgProProAsnIleArgLysSerValPheGlnLysSerGluTyrAspLys-110 |
| 080 | |
| AMPHI Regions - AMPHI | |
| SEQ. ID. NO. 732 | 6-GluAlaMetGluArgLeuThrArg-13 |
| SEQ. ID. NO. 733 | 95-PheProAspThrValGlu-100 |
| SEQ. ID. NO. 734 | 108-ProValAlaArgTrpGlyAspHis-115 |
| SEQ. ID. NO. 735 | 144-SerAlaGluMetLeuArgArgTyrAspGluPheSerThrValLeu-158 |
| SEQ. ID. NO. 736 | 195-LysArgLeuArgLeuPheThrGluAlaTrpGlnHis-206 |
| Antigenic Index - Jameson-Wolf | |
| SEQ. ID. NO. 737 | 1-MetTrpAspAsnAlaGluAlaMetGluArgLeuThr-12 |
| SEQ. ID. NO. 738 | 33-AsnSerAsnHisLeuPro-38 |
| SEQ. ID. NO. 739 | 42-ValSerLeuLysGly-46 |
| SEQ. ID. NO. 740 | 48-LeuValTyrSerAspLysLysThrLeu-56 |
| SEQ. ID. NO. 741 | 67-AsnIleLeuArgThrAspIleAsnGlyAlaGlnGluAlaTyrArg-81 |
| SEQ. ID. NO. 742 | 90-MetValArgArgArgPheProAspThrValGlu-100 |
| SEQ. ID. NO. 743 | 103-LeuThrGluArgLysProValAlaArgTrpGly-113 |
| SEQ. ID. NO. 744 | 116-AlaLeuValAspGlyGluGlyAsnValPhe-125 |
| SEQ. ID. NO. 745 | 127-AlaArgLeuAspArgProGlyMetPro-135 |
| SEQ. ID. NO. 746 | 138-ArgGlyAlaGluGlyThrSer-144 |
| SEQ. ID. NO. 747 | 146-GluMetLeuArgArgTyrAspGlu-153 |
| SEQ. ID. NO. 748 | 163-LeuGlyIleLysGlu-167 |
| SEQ. ID. NO. 749 | 187-ArgLeuGlyArgGluAsnGluMetLysArgLeuArgLeu-199 |
| SEQ. ID. NO. 750 | 207-LeuLeuArgLysAsnLysAsnArgLeuSer-216 |
| SEQ. ID. NO. 751 | 220-MetArgTyrLysAspGlyPheSer-227 |
| SEQ. ID. NO. 752 | 230-TyrAlaSerAspGlyLeuProGluLysGluSerGluGlu-242 |
| Hydrophilic Regions - Hopp-Woods | |
| SEQ. ID. NO. 753 | 3-AspAsnAlaGluAlaMetGluArgLeuThr-12 |
| SEQ. ID. NO. 754 | 50-TyrSerAspLysLysThrLeu-56 |
| SEQ. ID. NO. 755 | 69-LeuArgThrAspIleAsnGlyAlaGlnGluAlaTyrArg-81 |
| SEQ. ID. NO. 756 | 90-MetValArgArgArgPheProAspThrVal-99 |
| SEQ. ID. NO. 757 | 103-LeuThrGluArgLysProValAlaArgTrpGly-113 |
| SEQ. ID. NO. 758 | 116-AlaLeuValAspGlyGluGlyAsnValPhe-125 |
| SEQ. ID. NO. 759 | 127-AlaArgLeuAspArgProGly-133 |
| SEQ. ID. NO. 760 | 138-ArgGlyAlaGluGlyThrSer-144 |
| SEQ. ID. NO. 761 | 146-GluMetLeuArgArgTyrAspGlu153153 |
| SEQ. ID. NO. 762 | 163-LeuGlyIleLysGlu-167 |
| SEQ. ID. NO. 763 | 187-ArgLeuGlyArgGluAsnGluMetLysArgLeuArgLeu-199 |
| SEQ. ID. NO. 764 | 208-LeuArgLysAsnLysAsnArgLeuSer-216 |
| SEQ. ID. NO. 765 | 220-MetArgTyrLysAspGlyPheSer-227 |
| SEQ. ID. NO. 766 | 234-GlyLeuProGluLysGluSerGluGlu-242 |
| 081 | |
| AMPHI Regions - AMPHI | |
| SEQ. ID. NO. 767 | 22-LysProValSerArgIleValThrAspSer-31 |
| SEQ. ID. NO. 768 | 85-LeuAlaAlaLeuGlnThrLeuAlaLysAlaTrpArgGluAsn-98 |
| SEQ. ID. NO. 769 | 116-LysGluMetLeuAlaAlaValLeuArg-124 |
| SEQ. ID. NO. 770 | 135-ThrAlaGlyAsnPhe-139 |
| SEQ. ID. NO. 771 | 165-MetAsnHisPheGlyGluLeuAlaValLeuThrXxxIleAlaLys-179 |
| SEQ. ID. NO. 772 | 185-ValAsnAsnAlaMetArg-190 |
| SEQ. ID. NO. 773 | 198-AspGlyValGlyAspIleAlaLysAla-206 |
| SEQ. ID. NO. 774 | 303-LeuAsnAspValAlaGluGlyLeuLysGlyPheSerAsnIle-316 |
| SEQ. ID. NO. 775 | 345-AlaAlaIleAspValLeuAlaArgMetPro-354 |
| SEQ. ID. NO. 776 | 360-ValMetGlyAspMetGlyGluLeuGlyGluLeuGlyGlu-372 |
| SEQ. ID. NO. 777 | 402-ValGluAlaAlaGlu-406 |
| Antigenic Index - Jameson-Wolf | |
| SEQ. ID. NO. 778 | 16-ProMetProSerGluSerLysProValSer-25 |
| SEQ. ID. NO. 779 | 27-IleValThrAspSerArgAspIleArgAlaGlyAsp-38 |
| SEQ. ID. NO. 780 | 44-AlaGlyGluArgPheAspAla-50 |
| SEQ. ID. NO. 781 | 67-ValSerArgGluAspCysAlaAla-74 |
| SEQ. ID. NO. 782 | 77-GlyAlaLeuLysValAspAspThrLeu-85 |
| SEQ. ID. NO. 783 | 94-AlaTrpArgGluAsnValAsnProPhe-102 |
| SEQ. ID. NO. 784 | 108-GlySerGlyGlyLysThrThrValLysGluMetLeu-119 |
| SEQ. ID. NO. 785 | 123-LeuArgArgArgPheGlyAspAspAlaVal-132 |
| SEQ. ID. NO. 786 | 138-AsnPheAsnAsnHisIle-143 |
| SEQ. ID. NO. 787 | 151-LysLeuAsnGluLysHisArg-157 |
| SEQ. ID. NO. 788 | 178-AlaLysProAsnAla-182 |
| SEQ. ID. NO. 789 | 194-GlyCysGlyPheAspGlyValGlyAspIleAlaLysAlaLysSerGluIle-210 |
| SEQ. ID. NO. 790 | 212-GlnGlyLeuCysSerAspGly-218 |
| SEQ. ID. NO. 791 | 223-ProGlnGluAspAlaAsn-228 |
| SEQ. ID. NO. 792 | 239-LeuAsnThrArgThrPheGlyIleAspSerGlyAspValHisAla-253 |
| SEQ. ID. NO. 793 | 269-CysGlyAspGluArgAlaAla-275 |
| SEQ. ID. NO. 794 | 280-ValProGlyArgHisAsnVal-286 |

TABLE 1-continued

| | |
|---|---|
| SEQ. ID. NO. 795 | 305-AspValAlaGluGlyLeuLys-311 |
| SEQ. ID. NO. 796 | 313-PheSerAsnIleLysGlyArgLeuAsnValLysSerGlyIleLysGly-328 |
| SEQ. ID. NO. 797 | 330-ThrLeuIleAspAspThrTyrAsnAlaAsnProAspSerMetLysAlaAla-346 |
| SEQ. ID. NO. 798 | 363-AspMetGlyGluLeuGlyGluLeuGlyGluAspGluAlaAla-376 |
| SEQ. ID. NO. 799 | 384-AlaTyrAlaArgAspGlnGlyIle-391 |
| SEQ. ID. NO. 800 | 398-GlyAspAsnSerValGluAlaAlaGluLysPheGlyAla-410 |
| SEQ. ID. NO. 801 | 425-LeuArgHisAspLeuProGluArgAlaThrVal-435 |
| SEQ. ID. NO. 802 | 437-ValLysGlySerArg-441 |
| SEQ. ID. NO. 803 | 446-GluGluValValGluAlaLeuGluAspLys-455 |
| Hydrophilic Regions - Hopp-Woods | |
| SEQ. ID. NO. 804 | 17-MetProSerGluSerLysProValSer-25 |
| SEQ. ID. NO. 805 | 27-IleValThrAspSerArgAspIleArgAla-36 |
| SEQ. ID. NO. 806 | 44-AlaGlyGluArgPheAspAla-50 |
| SEQ. ID. NO. 807 | 67-ValSerArgGluAspCysAlaAla-74 |
| SEQ. ID. NO. 808 | 77-GlyAlaLeuLysValAspAspThrLeu-85 |
| SEQ. ID. NO. 809 | 94-AlaTrpArgGluAsnVal-99 |
| SEQ. ID. NO. 810 | 109-SerGlyGlyLysThrThrValLysGluMetLeu-119 |
| SEQ. ID. NO. 811 | 123-LeuArgArgArgPheGlyAsp-129 |
| SEQ. ID. NO. 812 | 151-LysLeuAsnGluLysHisArg-157 |
| SEQ. ID. NO. 813 | 199-GlyValGlyAspIleAlaLysAlaLysSerGluIle-210 |
| SEQ. ID. NO. 814 | 223-ProGlnGluAspAlaAsn-228 |
| SEQ. ID. NO. 815 | 247-AspSerGlyAspValHisAla-253 |
| SEQ. ID. NO. 816 | 269-CysGlyAspGluArgAlaAla-275 |
| SEQ. ID. NO. 817 | 305-AspValAlaGluGlyLeuLys-311 |
| SEQ. ID. NO. 818 | 316-IleLysGlyArgLeuAsnVal-322 |
| SEQ. ID. NO. 819 | 335-ThrTyrAsnAlaAsnProAspSerMetLysAlaAla-346 |
| SEQ. ID. NO. 820 | 363-AspMetGlyGluLeuGlyGluLeuGlyGluAspGluAlaAla-376 |
| SEQ. ID. NO. 821 | 384-AlaTyrAlaArgAspGlnGlyIle-391 |
| SEQ. ID. NO. 822 | 400-AsnSerValGluAlaAlaGluLysPheGlyAla-410 |
| SEQ. ID. NO. 823 | 425-LeuArgHisAspLeuProGluArgAlaThrVal-435 |
| SEQ. ID. NO. 824 | 446-GluGluValValGluAlaLeuGluAspLys-455 |
| 084-2 | |
| AMPHI Regions - AMPHI | |
| SEQ. ID. NO. 825 | 6-ArgIleLysAsnMetAsnGlnThrLeuLysAsnThrLeuGly-19 |
| SEQ. ID. NO. 826 | 21-CysAlaLeuLeuAla-25 |
| SEQ. ID. NO. 827 | 48-AlaValGlyAlaLeuAla-53 |
| SEQ. ID. NO. 828 | 65-PheProArgValSer-69 |
| SEQ. ID. NO. 829 | 96-GlnIleValGlySerIleLeuGluSer-104 |
| SEQ. ID. NO. 830 | 111-GluPheValGlyAsnLeuProGly-118 |
| Antigenic Index - Jameson-Wolf | |
| SEQ. ID. NO. 831 | 1-MetLysGlnSerAlaArgIleLysAsnMetAsnGlnThrLeuLysAsnThr-17 |
| SEQ. ID. NO. 832 | 40-TyrGluTyrGlyTyrArgTyrSer-47 |
| SEQ. ID. NO. 833 | 102-LeuGluSerAsnProAlaGluAlaArgGluPheValGly-114 |
| SEQ. ID. NO. 834 | 139-ValSerGlyGlyGly-143 |
| Hydrophilic Regions - Hopp-Woods | |
| SEQ. ID. NO. 835 | 1-MetLysGlnSerAlaArgIleLysAsnMetAsnGlnThrLeu-14 |
| SEQ. ID. NO. 836 | 105-AsnProAlaGluAlaArgGluPheVal-113 |
| 085-2 | |
| AMPHI Regions - AMPHI | |
| SEQ. ID. NO. 837 | 41-GluArgValSerGlnIleGlyLysMetPheAspGlyLeu-53 |
| SEQ. ID. NO. 838 | 60-LeuLysAspAlaLeuAspAsnGlyPheAsp-69 |
| SEQ. ID. NO. 839 | 90-AsnGlyGlyArgValLeuGlyAspIleGluLeuLeuAlaAsp-103 |
| SEQ. ID. NO. 840 | 125-ThrSerLeuValGlyTyr-130 |
| SEQ. ID. NO. 841 | 141-IleAlaGlyAsnIleGlyThr-147 |
| SEQ. ID. NO. 842 | 174-GluAsnThrGluSerLeu-179 |
| SEQ. ID. NO. 843 | 193-HisLeuAspArgTyrAspAspLeuLeuAspTyr-203 |
| SEQ. ID. NO. 844 | 212-ArgGlyAspGlyValGln-217 |
| SEQ. ID. NO. 845 | 225-PheCysArgAlaMetLysArgAla-232 |
| SEQ. ID. NO. 846 | 275-HisAsnAlaAlaAsnValMetAlaAlaValAlaLeuCysGluAla-289 |
| SEQ. ID. NO. 847 | 300-HisValLysThrPheGlnGlyLeuProHisArgValGluLysIleGly-315 |
| SEQ. ID. NO. 848 | 336-AlaAlaIleAlaGlyLeu-341 |
| SEQ. ID. NO. 849 | 353-GlyLysGlyGlnAspPheThr-359 |
| SEQ. ID. NO. 850 | 395-AspCysAlaThrLeuGlyGluAlaValGlnThr-405 |
| SEQ. ID. NO. 851 | 424-SerPheAspMetPheLysGlyTyr-431 |
| Antigenic Index - Jameson-Wolf | |
| SEQ. ID. NO. 852 | 4-GlnAsnLysLysIleLeu-9 |
| SEQ. ID. NO. 853 | 23-TyrLeuArgLysAsnGlyAlaGluValAlaAlaTyrAspAlaGluLeuLysProGluArgValSerGlnIleGlyLysMetPheAsp-51 |
| SEQ. ID. NO. 854 | 58-GlyArgLeuLysAspAlaLeuAspAsnGlyPhe-68 |
| SEQ. ID. NO. 855 | 74-SerProGlyIleSerGluArgGlnProAspIleGluAlaPheLysGlnAsnGlyGlyArgValLeuGly-96 |
| SEQ. ID. NO. 856 | 104-IleValAsnArgArgAspAspLysValIle-113 |
| SEQ. ID. NO. 857 | 116-ThrGlySerAsnGlyLysThrThr-123 |
| SEQ. ID. NO. 858 | 153-GluTrpGlnArgGluGlyLysLysAlaAsp-162 |
| SEQ. ID. NO. 859 | 169-SerSerPheGlnLeuGluAsnThrGluSerLeuArgProThrAla-183 |
| SEQ. ID. NO. 860 | 189-IleSerGluAspHisLeuAspArgTyrAspAspLeuLeu-201 |
| SEQ. ID. NO. 861 | 204-AlaHisThrLysAlaLysIlePheArgGlyAspGlyVal-216 |
| SEQ. ID. NO. 862 | 220-AsnAlaAspAspAlaPheCysArgAlaMetLysArgAlaGlyArgGluValLys-237 |
| SEQ. ID. NO. 863 | 247-PheTrpLeuGluArgGluThrGlyArgLeuLysGlnGlyAsnGluAspLeuIleVal-265 |
| SEQ. ID. NO. 864 | 291-GlyLeuSerArgGluAlaLeu-297 |
| SEQ. ID. NO. 865 | 307-LeuProHisArgValGluLysIleGlyGluLysAsnGly-319 |
| SEQ. ID. NO. 866 | 322-PheIleAspAspSerLysGlyThrAsnVal-331 |

TABLE 1-continued

| | |
|---|---|
| SEQ. ID. NO. 867 | 351-GlyMetGlyLysGlyGlnAspPheThrProLeuArgAspAlaLeuValGlyLysAlaLys-370 |
| SEQ. ID. NO. 868 | 378-AspAlaProGlnIleArgArgAspLeuAspGlyCysGly-390 |
| SEQ. ID. NO. 869 | 431-TyrAlaHisArgSer-435 |
| Hydrophilic Regions - Hopp-Woods | |
| SEQ. ID. NO. 870 | 4-GlnAsnLysLysIleLeu-9 |
| SEQ. ID. NO. 871 | 25-ArgLysAsnGlyAlaGlu-30 |
| SEQ. ID. NO. 872 | 32-AlaAlaTyrAspAlaGluLeuLysProGluArgValSerGln-45 |
| SEQ. ID. NO. 873 | 59-ArgLeuLysAspAlaLeuAspAsnGlyPhe-68 |
| SEQ. ID. NO. 874 | 76-GlyIleSerGluArgGlnProAspIleGluAlaPheLysGlnAsnGlyGly-92 |
| SEQ. ID. NO. 875 | 104-IleValAsnArgArgAspAspLysVal-112 |
| SEQ. ID. NO. 876 | 118-SerAsnGlyLysThrThr-123 |
| SEQ. ID. NO. 877 | 153-GluTrpGlnArgGluGlyLysLysAlaAsp-162 |
| SEQ. ID. NO. 878 | 174-GluAsnThrGluSerLeuArgPro-181 |
| SEQ. ID. NO. 879 | 189-IleSerGluAspHisLeuAspArgTyrAspAspLeuLeu-201 |
| SEQ. ID. NO. 880 | 204-AlaHisThrLysAlaLysIlePheArgGlyAspGly-215 |
| SEQ. ID. NO. 881 | 220-AsnAlaAspAspAlaPheCysArgAlaMetLysArgAlaGlyArgGluValLys-237 |
| SEQ. ID. NO. 882 | 247-PheTrpLeuGluArgGluThrGlyArgLeuLysGlnGlyAsnGluAspLeuIleVal-265 |
| SEQ. ID. NO. 883 | 291-GlyLeuSerArgGluAlaLeu-297 |
| SEQ. ID. NO. 884 | 309-HisArgValGluLysIleGlyGluLysAsnGly-319 |
| SEQ. ID. NO. 885 | 324-AspAspSerLysGlyThrAsn-330 |
| SEQ. ID. NO. 886 | 353-GlyLysGlyGlnAsp-357 |
| SEQ. ID. NO. 887 | 359-ThrProLeuArgAspAlaLeuValGlyLysAlaLys-370 |
| SEQ. ID. NO. 888 | 380-ProGlnIleArgArgAspLeuAspGly-388 |
| SEQ. ID. NO. 889 | 431-TyrAlaHisArgSer-435 |
| 086-2 | |
| AMPHI Regions - AMPHI | |
| SEQ. ID. NO. 890 | 55-MetArgThrTrpArgArgLeuValPro-63 |
| SEQ. ID. NO. 891 | 83-IleAsnGlyAlaThrArg-88 |
| SEQ. ID. NO. 892 | 99-ProThrGluLeuPheLysLeuAlaVal-107 |
| SEQ. ID. NO. 893 | 120-GluValLeuArgSerMetGluSerLeuGlyTrpGlnSerIleTrpArgGlyThrAlaAsn-139 |
| SEQ. ID. NO. 894 | 155-GluMetTyrGlyArgPhe-160 |
| SEQ. ID. NO. 895 | 185-SerPheValValIle-189 |
| SEQ. ID. NO. 896 | 228-ArgValGlnArgValValAlaPheLeuAspProTrpLysAspProGln-243 |
| SEQ. ID. NO. 897 | 293-GlyPhePheGlyMetCys-298 |
| SEQ. ID. NO. 898 | 336-TrpIleGlyIleGlnSerPhe-342 |
| Antigenic Index - Jameson-Wolf | |
| SEQ. ID. NO. 899 | 20-LeuAlaSerLysGluGlyGlyAsp-27 |
| SEQ. ID. NO. 900 | 55-MetArgThrTrpArgArg-60 |
| SEQ. ID. NO. 901 | 79-AlaGlyArgGluIleAsnGlyAlaThr-87 |
| SEQ. ID. NO. 902 | 115-PheThrArgArgGluGluValLeuArgSerMetGlu-126 |
| SEQ. ID. NO. 903 | 134-TrpArgGlyThrAla-138 |
| SEQ. ID. NO. 904 | 144-AlaThrAsnProGlnAlaArgArgGluThrLeuGluMet-156 |
| SEQ. ID. NO. 905 | 225-AlaProTyrArgVal-229 |
| SEQ. ID. NO. 906 | 236-LeuAspProTrpLysAspProGlnGlyAla-245 |
| SEQ. ID. NO. 907 | 265-GlyLeuGlyAlaSerLeuSerLysArgGlyPheLeu-276 |
| SEQ. ID. NO. 908 | 313-SerIleGlyLysGlnSerArgAspLeuGly-322 |
| SEQ. ID. NO. 909 | 352-LeuProThrLysGlyLeu-357 |
| SEQ. ID. NO. 910 | 382-IleAspTyrGluAsnArgArgLysMetArgGlyTyrArgValGlu-396 |
| Hydrophilic Regions - Hopp-Woods | |
| SEQ. ID. NO. 911 | 21-AlaSerLysGluGlyGlyAsp-27 |
| SEQ. ID. NO. 912 | 79-AlaGlyArgGluIleAsnGly-85 |
| SEQ. ID. NO. 913 | 115-PheThrArgArgGluGluValLeuArgSerMetGlu-126 |
| SEQ. ID. NO. 914 | 147-ProGlnAlaArgArgGluThrLeuGluMet-156 |
| SEQ. ID. NO. 915 | 238-ProTrpLysAspProGlnGly-244 |
| SEQ. ID. NO. 916 | 270-LeuSerLysArgGlyPheLeu-276 |
| SEQ. ID. NO. 917 | 316-LysGlnSerArgAspLeu-321 |
| SEQ. ID. NO. 918 | 382-IleAspTyrGluAsnArgArgLysMetArgGlyTyrArgValGlu-396 |
| 087-2 | |
| AMPHI Regions - AMPHI | |
| SEQ. ID. NO. 919 | 23-ValAlaAspSerLeuArg-28 |
| SEQ. ID. NO. 920 | 80-GlnThrValArgGluAlaGlnArgIleIle-89 |
| SEQ. ID. NO. 921 | 99-GlyPheGlyGlyPheValThrPheProGlyGlyLeuAlaAlaLysLeuLeu-115 |
| SEQ. ID. NO. 922 | 129-GlyLeuSerAsnArgHisLeuSerArgTrpAlaLysArgValLeuTyrAlaPheProLys-148 |
| SEQ. ID. NO. 923 | 157-ValGlyAsnProValArg-162 |
| SEQ. ID. NO. 924 | 192-GlyAlaAspValLeuAsnLysThrVal-200 |
| SEQ. ID. NO. 925 | 241-ValGluPheIleThrAspMetValSerAlaTyr-251 |
| SEQ. ID. NO. 926 | 313-GluLysLeuAlaGluIleLeuGly-320 |
| SEQ. ID. NO. 927 | 330-TrpAlaGluAsnAla-334 |
| Antigenic Index - Jameson-Wolf | |
| SEQ. ID. NO. 928 | 25-AspSerLeuArgAlaArgGly-31 |
| SEQ. ID. NO. 929 | 37-LeuGlySerLysAspSerMetGluGluArgIleValProGlnTyrGlyIle-53 |
| SEQ. ID. NO. 930 | 61-LysGlyValArgGlyAsnGlyIleLysArgLysLeu-72 |
| SEQ. ID. NO. 931 | 81-ThrValArgGluAlaGlnArgIleIleArgLysHisArgVal-94 |
| SEQ. ID. NO. 932 | 130-LeuSerAsnArgHisLeuSerArgTrpAlaLys-140 |
| SEQ. ID. NO. 933 | 150-PheSerHisGluGlyGlyLeu-156 |
| SEQ. ID. NO. 934 | 159-AsnProValArgAlaAspIleSer-166 |
| SEQ. ID. NO. 935 | 171-ProAlaGluArgPheGlnGlyArgGluGlyArgLeu-182 |
| SEQ. ID. NO. 936 | 195-ValLeuAsnLysThrVal-200 |
| SEQ. ID. NO. 937 | 207-LeuProAspAsnAlaArgProGlnMetTyrHisGlnSerGlyArgGlyLysLeuGly-225 |
| SEQ. ID. NO. 938 | 229-AlaAspTyrAspAla-233 |

TABLE 1-continued

| | |
|---|---|
| SEQ. ID. NO. 939 | 235-GlyValLysAlaGluCys-240 |
| SEQ. ID. NO. 940 | 249-SerAlaTyrArgAspAlaAsp-255 |
| SEQ. ID. NO. 941 | 284-AlaValAspAspHisGlnThrAla-291 |
| SEQ. ID. NO. 942 | 309-GlnLeuThrAlaGluLysLeuAlaGlu-317 |
| SEQ. ID. NO. 943 | 321-GlyLeuAsnArgGluLysCysLeuLys-329 |
| SEQ. ID. NO. 944 | 331-AlaGluAsnAlaArgThr-336 |
| SEQ. ID. NO. 945 | 341-HisSerAlaAspAspValAlaGlu-348 |
| Hydrophilic Regions - Hopp-Woods | |
| SEQ. ID. NO. 946 | 25-AspSerLeuArgAlaArgGly-31 |
| SEQ. ID. NO. 947 | 39-SerLysAspSerMetGluGluArgIleVal-48 |
| SEQ. ID. NO. 948 | 66-AsnGlyIleLysArgLysLeu-72 |
| SEQ. ID. NO. 949 | 81-ThrValArgGluAlaGlnArgIleIleArgLysHisArgVal-94 |
| SEQ. ID. NO. 950 | 134-HisLeuSerArgTrpAlaLys-140 |
| SEQ. ID. NO. 951 | 161-ValArgAlaAspIle-165 |
| SEQ. ID. NO. 952 | 171-ProAlaGluArgPheGlnGlyArgGluGlyArgLeu-182 |
| SEQ. ID. NO. 953 | 219-SerGlyArgGlyLysLeu-224 |
| SEQ. ID. NO. 954 | 235-GlyValLysAlaGluCys-240 |
| SEQ. ID. NO. 955 | 249-SerAlaTyrArgAspAlaAsp-255 |
| SEQ. ID. NO. 956 | 284-AlaValAspAspHisGlnThrAla-291 |
| SEQ. ID. NO. 957 | 310-LeuThrAlaGluLysLeuAlaGlu-317 |
| SEQ. ID. NO. 958 | 322-LeuAsnArgGluLysCysLeuLys-329 |
| SEQ. ID. NO. 959 | 331-AlaGluAsnAlaArg-335 |
| SEQ. ID. NO. 960 | 341-HisSerAlaAspAspValAlaGlu-348 |
| 088-2 | |
| AMPHI Regions - AMPHI | |
| SEQ. ID. NO. 961 | 7-HisPheSerAsnTrpLeuThrGlyLeuAsnIlePheGlnTyrThrThr-22 |
| SEQ. ID. NO. 962 | 24-ArgAlaValMetAlaAlaLeu-30 |
| SEQ. ID. NO. 963 | 43-ThrIleArgArgLeuThrAlaLeuLysCysGlyGln-54 |
| SEQ. ID. NO. 964 | 88-LeuTrpGlyAsnTrpAlaAsn-94 |
| SEQ. ID. NO. 965 | 111-GlyPheTyrAspAspTrpArgLysValValTyr-121 |
| SEQ. ID. NO. 966 | 140-AlaIleIleAlaSerLeuAlaLeu-147 |
| SEQ. ID. NO. 967 | 175-GlyPheLeuValLeuSerTyrLeuThrIle-184 |
| SEQ. ID. NO. 968 | 187-ThrSerAsnAlaValAsnLeuThrAspGlyLeuAspGlyLeuAlaThr-202 |
| SEQ. ID. NO. 969 | 221-HisSerGlnPheAlaGlnTyrLeuGlnLeuProTyr-232 |
| SEQ. ID. NO. 970 | 245-AlaMetCysGlyAlaCysLeuGlyPhe-253 |
| Antigenic Index - Jameson-Wolf | |
| SEQ. ID. NO. 971 | 48-ThrAlaLeuLysCysGlyGlnAlaValArgThrAspGlyProGln-62 |
| SEQ. ID. NO. 972 | 66-ValLysAsnGlyThrProThrMet-73 |
| SEQ. ID. NO. 973 | 114-AspAspTrpArgLysValValTyrLysAspProAsnGlyValSerAlaLysPhe-131 |
| SEQ. ID. NO. 974 | 193-LeuThrAspGlyLeuAsp-198 |
| SEQ. ID. NO. 975 | 312-LysLysThrLysLysArgIle-318 |
| SEQ. ID. NO. 976 | 328-TyrGluGlnLysGlyTrpLysGluThrGlnVal-338 |
| Hydrophilic Regions - Hopp-Woods | |
| SEQ. ID. NO. 977 | 56-ValArgThrAspGlyProGln-62 |
| SEQ. ID. NO. 978 | 114-AspAspTrpArgLysValValTyrLysAspProAsnGlyVal-127 |
| SEQ. ID. NO. 979 | 312-LysLysThrLysLysArgIle-318 |
| SEQ. ID. NO. 980 | 331-LysGlyTrpLysGlu-335 |
| 089-2 | |
| AMPHI Regions - AMPHI | |
| SEQ. ID. NO. 981 | 40-PheSerThrArgCysGlyArgProTrpLysValLeu-51 |
| SEQ. ID. NO. 982 | 74-LeuAlaAlaLeuCysArgProCysAsnGlyMetSerCys-86 |
| SEQ. ID. NO. 983 | 118-SerArgProAlaArgPhe-123 |
| Antigenic Index - Jameson-Wolf | |
| SEQ. ID. NO. 984 | 1-MetProProLysIleThrLysSerGlyPhe-10 |
| SEQ. ID. NO. 985 | 40-PheSerThrArgCysGlyArgProTrpLys-49 |
| SEQ. ID. NO. 986 | 54-SerSerAsnAlaSerArgAspLysProMetAlaSerHisLysAla-68 |
| SEQ. ID. NO. 987 | 79-ArgProCysAsnGlyMetSerCys-86 |
| SEQ. ID. NO. 988 | 95-CysPheArgArgProValSerArgSerAsnGlnLysSerAlaSerCysSerAsnGluAsnHisPheThrSerArgProAlaArgPheIleAlaArgGlnAsn AlaSerSerAlaPheLysThrCysThrProSerProArgLysIleLeu-144 |
| Hydrophilic Regions - Hopp-Woods | |
| SEQ. ID. NO. 989 | 43-ArgCysGlyArgPro-47 |
| SEQ. ID. NO. 990 | 56-AsnAlaSerArgAspLysProMetAlaSerHisLysAla-68 |
| SEQ. ID. NO. 991 | 95-CysPheArgArgProValSerArgSerAsnGlnLysSerAlaSerCysSerAsn-112 |
| SEQ. ID. NO. 992 | 119-ArgProAlaArgPheIleAla-125 |
| SEQ. ID. NO. 993 | 137-ThrProSerProArgLysIle-143 |
| 090-1 | |
| AMPHI Regions - AMPHI | |
| SEQ. ID. NO. 994 | 10-SerGlnSerLeuLysArgPheAspLysHisPheArg-21 |
| SEQ. ID. NO. 995 | 56-SerGlnSerGlyAlaValGlyHisIle-64 |
| SEQ. ID. NO. 996 | 141-AlaAspPhePheHisAlaValArgGlnAla-150 |
| SEQ. ID. NO. 997 | 152-GluGlyPheAspValPheGluGlnCysPheAla-162 |
| SEQ. ID. NO. 998 | 164-GlnThrAspGlyLeuThrGln-170 |
| SEQ. ID. NO. 999 | 177-ValSerGlyValValGlnThrLeuGlnArg-186 |
| SEQ. ID. NO. 1000 | 226-LeuHisArgAlaAlaGluArgIleValArgIleGlnAsnLeuHisAlaVal-242 |
| SEQ. ID. NO. 1001 | 387-IleGluThrValValGlnArgIlePheGlnThrAla-398 |
| SEQ. ID. NO. 1002 | 404-ProValLysHisLeuThrAspLeuArg-412 |
| SEQ. ID. NO. 1003 | 425-AsnLeuArgAlaValPheAlaGlnValGlyAsnHisGlyAsnThrArgThrAlaGluSer-444 |
| Antigenic Index - Jameson-Wolf | |
| SEQ. ID. NO. 1004 | 9-AlaSerGlnSerLeuLysArgPheAspLysHisPheArg-21 |
| SEQ. ID. NO. 1005 | 29-HisIleLysAlaArgAlaGlyGlyAlaGluGlnHis-40 |

TABLE 1-continued

| | |
|---|---|
| SEQ. ID. NO. 1006 | 53-AsnGlyPheSerGlnSerGly-59 |
| SEQ. ID. NO. 1007 | 73-AlaAspLeuArgArgIleAspThrAsnGlnGlu-83 |
| SEQ. ID. NO. 1008 | 94-AlaGlnGlyArgGluVal-99 |
| SEQ. ID. NO. 1009 | 107-GlnAsnHisGluGluArgIleLeuGlnThrGlyAsnArgGlyGlySerArgAlaAspIleArg-127 |
| SEQ. ID. NO. 1010 | 149-GlnAlaLeuGluGly-153 |
| SEQ. ID. NO. 1011 | 161-PheAlaArgGlnThrAspGlyLeuThrGlnSerHisGlySerHisAspValSerGly-179 |
| SEQ. ID. NO. 1012 | 187-AsnValLeuArgAspAsnGln-193 |
| SEQ. ID. NO. 1013 | 214-PheGlnArgLysProPheTyr-220 |
| SEQ. ID. NO. 1014 | 228-ArgAlaAlaGluArgIleValArg-235 |
| SEQ. ID. NO. 1015 | 269-GlnHisArgArgArgSerArgThrGlnAla-278 |
| SEQ. ID. NO. 1016 | 285-GluAlaGlyLysLeuGln-290 |
| SEQ. ID. NO. 1017 | 304-ArgLeuGlnAsnArgArgAlaAspIleAlaArgAspAsnGlyIle-318 |
| SEQ. ID. NO. 1018 | 320-ProAlaLeuAspThrGluIleAlaAspGlnAlaArgTyrArgGly-334 |
| SEQ. ID. NO. 1019 | 339-AlaGlyAsnArgAsnTyr-344 |
| SEQ. ID. NO. 1020 | 353-ValArgGlnGlnPhe-357 |
| SEQ. ID. NO. 1021 | 379-AspAlaGlyThrGluSerGlnAsnIle-387 |
| SEQ. ID. NO. 1022 | 398-AlaArgValLysHisGlnProValLysHisLeuThrAspLeuArgHis-413 |
| SEQ. ID. NO. 1023 | 421-IleIleArgSerAsnLeuArg-427 |
| SEQ. ID. NO. 1024 | 434-GlyAsnHisGlyAsnThrArgThrAlaGluSerGlyAspGluAspPhePhe-450 |
| Hydrophilic Regions - Hopp-Woods | |
| SEQ. ID. NO. 1025 | 11-GlnSerLeuLysArgPheAspLysHisPheArg-21 |
| SEQ. ID. NO. 1026 | 29-HisIleLysAlaArgAlaGlyGlyAlaGluGlnHis-40 |
| SEQ. ID. NO. 1027 | 73-AlaAspLeuArgArgIleAspThrAsnGln-82 |
| SEQ. ID. NO. 1028 | 94-AlaGlnGlyArgGluVal-99 |
| SEQ. ID. NO. 1029 | 107-GlnAsnHisGluGluArgIleLeu-114 |
| SEQ. ID. NO. 1030 | 117-GlyAsnArgGlyGlySerArgAlaAspIleArg-127 |
| SEQ. ID. NO. 1031 | 163-ArgGlnThrAspGlyLeuThr-169 |
| SEQ. ID. NO. 1032 | 173-GlySerHisAspVal-177 |
| SEQ. ID. NO. 1033 | 187-AsnValLeuArgAspAsnGln-193 |
| SEQ. ID. NO. 1034 | 228-ArgAlaAlaGluArgIleValArg-235 |
| SEQ. ID. NO. 1035 | 269-GlnHisArgArgArgSerArgThrGln-277 |
| SEQ. ID. NO. 1036 | 285-GluAlaGlyLysLeuGln-290 |
| SEQ. ID. NO. 1037 | 305-LeuGlnAsnArgArgAlaAspIleAlaArgAspAsnGlyIle-318 |
| SEQ. ID. NO. 1038 | 322-LeuAspThrGluIleAlaAspGlnAlaArgTyrArg-333 |
| SEQ. ID. NO. 1039 | 380-AlaGlyThrGluSerGlnAsnIle-387 |
| SEQ. ID. NO. 1040 | 398-AlaArgValLysHisGlnPro-404 |
| SEQ. ID. NO. 1041 | 407-HisLeuThrAspLeuArgHis-413 |
| SEQ. ID. NO. 1042 | 421-IleIleArgSerAsnLeu-426 |
| SEQ. ID. NO. 1043 | 437-GlyAsnThrArgThrAlaGluSerGlyAspGluAspPhePhe-450 |
| 091-2 | |
| AMPHI Regions - AMPHI | |
| SEQ. ID. NO. 1044 | 11-ProLeuSerAspGlyIleAlaSerCys-19 |
| SEQ. ID. NO. 1045 | 21-IleThrArgLeuGlnAlaLeuVal-28 |
| SEQ. ID. NO. 1046 | 33-ValLeuValSerValLeuThrSerLeuAlaLys-43 |
| Antigenic Index - Jameson-Wolf | |
| SEQ. ID. NO. 1047 | 1-LeuSerArgArgCysProProLeuProLysProLeuSerAspGlyIleAla-17 |
| SEQ. ID. NO. 1048 | 73-LeuArgCysArgLeuProLysProSerAspArgPheAsp-85 |
| SEQ. ID. NO. 1049 | 105-LeuAspAsnProLeuArgCysArgLeuProIleProSerAspArgPheGly-121 |
| Hydrophilic Regions - Hopp-Woods | |
| SEQ. ID. NO. 1050 | 1-LeuSerArgArgCysProProLeu-8 |
| SEQ. ID. NO. 1051 | 75-CysArgLeuProLysProSerAspArgPheAsp-85 |
| SEQ. ID. NO. 1052 | 107-AsnProLeuArgCys-111 |
| SEQ. ID. NO. 1053 | 115-IleProSerAspArgPhe-120 |
| 092 | |
| AMPHI Regions - AMPHI | |
| SEQ. ID. NO. 1054 | 55-GlyMetSerGlyIleAlaGluValLeuHis-64 |
| SEQ. ID. NO. 1055 | 76-AlaArgAsnAlaAlaThrGluHisLeu-84 |
| SEQ. ID. NO. 1056 | 95-HisThrAlaGluHisValAsnGly-102 |
| SEQ. ID. NO. 1057 | 120-ValAlaAlaLeuGlu-124 |
| SEQ. ID. NO. 1058 | 137-AlaGluLeuMetArgPheArgAsp-144 |
| SEQ. ID. NO. 1059 | 209-LeuThrProIleMetSerValValThrAsnIleAsp-220 |
| SEQ. ID. NO. 1060 | 226-ThrTyrGlyHisSerValGluLysLeuHisGlnAlaPheIleAspPheIleHisArg-244 |
| SEQ. ID. NO. 1061 | 259-HisValArgAlaIleLeuProLysValSerLysProTyr-271 |
| SEQ. ID. NO. 1062 | 273-ThrTyrGlyLeuAspAspThrAla-280 |
| SEQ. ID. NO. 1063 | 321-AsnValLeuAsnAlaLeuAlaAlaIle-329 |
| SEQ. ID. NO. 1064 | 339-ValGluAlaIleGlnLysGly-345 |
| SEQ. ID. NO. 1065 | 353-GlyArgArgPheGlnLysTyrGlyAspIleLys-363 |
| SEQ. ID. NO. 1066 | 407-ArgTyrThrArgThrArgAspLeuPheGluAspPheThrLysValLeuAsnThrValAspAlaLeu-428 |
| SEQ. ID. NO. 1067 | 449-LeuAlaArgAlaIleArgValLeuGlyLysLeu-459 |
| SEQ. ID. NO. 1068 | 464-CysGluAsnValAlaAspLeuProGluMetLeuLeuAsn-476 |
| Antigenic Index - Jameson-Wolf | |
| SEQ. ID. NO. 1069 | 14-LeuTrpArgAlaAsnGlyGlnProPheLys-23 |
| SEQ. ID. NO. 1070 | 25-ThrProLeuArgIleGluAsnProProGluArgAsnIleMetMetLysAsnArgVal-43 |
| SEQ. ID. NO. 1071 | 70-ValSerGlySerAspGlnAlaArgAsnAlaAla-80 |
| SEQ. ID. NO. 1072 | 111-AlaValLysLysGluAsnProGluVal-119 |
| SEQ. ID. NO. 1073 | 140-MetArgPheArgAspGlyIle-146 |
| SEQ. ID. NO. 1074 | 150-GlyThrHisGlyLysThrThrThr-157 |
| SEQ. ID. NO. 1075 | 184-GlyThrAsnAlaArgLeuGlyLysGlyGluTyr-194 |
| SEQ. ID. NO. 1076 | 198-GluAlaAspGluSerAspAla-204 |
| SEQ. ID. NO. 1077 | 218-AsnIleAspGluAspHisMetAspThrTyrGly-228 |

TABLE 1-continued

| | |
|---|---|
| SEQ. ID. NO. 1078 | 230-SerValGluLysLeuHis-235 |
| SEQ. ID. NO. 1079 | 255-IleAspSerGluHisVal-260 |
| SEQ. ID. NO. 1080 | 263-IleLeuProLysValSerLysProTyrAla-272 |
| SEQ. ID. NO. 1081 | 275-GlyLeuAspAspThrAlaAsp-281 |
| SEQ. ID. NO. 1082 | 286-AspIleGluAsnValGlyAla-292 |
| SEQ. ID. NO. 1083 | 302-MetLysGlyHisGluGlnGlySerPhe-310 |
| SEQ. ID. NO. 1084 | 351-GlyValGlyArgArgPheGlnLysTyrGlyAspIleLysLeuProAsnGlyGly-368 |
| SEQ. ID. NO. 1085 | 374-AspAspTyrGlyHisHisPro-380 |
| SEQ. ID. NO. 1086 | 393-AlaTyrLeuGluLysArgLeu-399 |
| SEQ. ID. NO. 1087 | 404-GlnProHisArgTyrThrArgThrArgAspLeuPheGluAspPheThrLys-420 |
| SEQ. ID. NO. 1088 | 435-AlaAlaGlyGluGluProIleAlaAlaAlaAspSerArgAlaLeuAlaArg-451 |
| SEQ. ID. NO. 1089 | 466-AsnValAlaAspLeuPro-471 |
| SEQ. ID. NO. 1090 | 478-LeuGlnAspGlyAspIle-483 |
| SEQ. ID. NO. 1091 | 488-GlyAlaGlySerIleAsn-493 |
| Hydrophilic Regions - Hopp-Woods | |
| SEQ. ID. NO. 1092 | 26-ProLeuArgIleGluAsnProProGluArgAsnIleMetMetLysAsnArgVal-43 |
| SEQ. ID. NO. 1093 | 71-SerGlySerAspGlnAlaArgAsnAlaAla-80 |
| SEQ. ID. NO. 1094 | 111-AlaValLysLysGluAsnProGlu-118 |
| SEQ. ID. NO. 1095 | 140-MetArgPheArgAsp-144 |
| SEQ. ID. NO. 1096 | 152-HisGlyLysThrThr-156 |
| SEQ. ID. NO. 1097 | 187-AlaArgLeuGlyLysGlyGlu-193 |
| SEQ. ID. NO. 1098 | 198-GluAlaAspGluSerAspAla-204 |
| SEQ. ID. NO. 1099 | 218-AsnIleAspGluAspHisMetAsp-225 |
| SEQ. ID. NO. 1100 | 230-SerValGluLysLeuHis-235 |
| SEQ. ID. NO. 1101 | 256-AspSerGluHisVal-260 |
| SEQ. ID. NO. 1102 | 275-GlyLeuAspAspThrAlaAsp-281 |
| SEQ. ID. NO. 1103 | 303-LysGlyHisGluGlnGlySer-309 |
| SEQ. ID. NO. 1104 | 351-GlyValGlyArgArgPheGlnLys-358 |
| SEQ. ID. NO. 1105 | 360-GlyAspIleLysLeu-364 |
| SEQ. ID. NO. 1106 | 393-AlaTyrLeuGluLysArgLeu-399 |
| SEQ. ID. NO. 1107 | 407-ArgTyrThrArgThrArgAspLeuPheGluAspPheThrLys-420 |
| SEQ. ID. NO. 1108 | 435-AlaAlaGlyGluGluProIleAlaAlaAlaAspSerArgAlaLeuAlaArg-451 |
| SEQ. ID. NO. 1109 | 466-AsnValAlaAspLeuPro-471 |
| SEQ. ID. NO. 1110 | 479-GlnAspGlyAspIle-483 |
| 093-2 | |
| AMPHI Regions - AMPHI | |
| SEQ. ID. NO. 1111 | 26-ThrAlaIleLeuAsn-30 |
| SEQ. ID. NO. 1112 | 59-ThrAlaPheAsnIleLeuHisGly-66 |
| SEQ. ID. NO. 1113 | 159-LysSerValTyrGluGluLeuLysHisLeu-168 |
| SEQ. ID. NO. 1114 | 196-IleHisIleIleProAlaThrGluPhe-204 |
| SEQ. ID. NO. 1115 | 254-PheLeuLysAspThr-258 |
| SEQ. ID. NO. 1116 | 267-IleAsnThrLeuProGlyMetThrSer-275 |
| Antigenic Index - Jameson-Wolf | |
| SEQ. ID. NO. 1117 | 12-GlyGlyPheSerSerGluArgGluIleSerLeuAspSerGlyThr-26 |
| SEQ. ID. NO. 1118 | 32-LeuLysSerLysGlyIleAsp-38 |
| SEQ. ID. NO. 1119 | 41-AlaPheAspProLysGluThrProLeuSerGluLeuLysAlaGlnGly-56 |
| SEQ. ID. NO. 1120 | 66-GlyThrTyrGlyGluAspGlyAlaVal-74 |
| SEQ. ID. NO. 1121 | 96-GlyMetAspLysTyrArgCys-102 |
| SEQ. ID. NO. 1122 | 120-HisAspAspThrAspPheAspAlaValGluGluLysLeuGly-133 |
| SEQ. ID. NO. 1123 | 140-ProAlaAlaGluGlySerSer-146 |
| SEQ. ID. NO. 1124 | 151-LysValLysGlyLysGlyArgLeuLysSerValTyrGluGluLeuLysHisLeuGln-169 |
| SEQ. ID. NO. 1125 | 176-ArgPheIleGlyGlyGlyGluTyrSer-184 |
| SEQ. ID. NO. 1126 | 189-AsnGlyLysGlyLeuPro-194 |
| SEQ. ID. NO. 1127 | 203-GluPheTyrAspTyrGluAlaLysTyrAsnArgAspAspThrIleTyrGlnCysProSerGluAspLeuThrGluAlaGluGluSerLeuMetArg-234 |
| SEQ. ID. NO. 1128 | 245-GlyAlaGluGlyCysVal-250 |
| SEQ. ID. NO. 1129 | 253-AspPheLeuLysAspThrAspGly-260 |
| SEQ. ID. NO. 1130 | 270-LeuProGlyMetThr-274 |
| SEQ. ID. NO. 1131 | 279-ValProLysSerAlaAla-284 |
| Hydrophilic Regions - Hopp-Woods | |
| SEQ. ID. NO. 1132 | 15-SerSerGluArgGluIleSerLeu-22 |
| SEQ. ID. NO. 1133 | 32-LeuLysSerLysGlyIleAsp-38 |
| SEQ. ID. NO. 1134 | 41-AlaPheAspProLysGluThrProLeuSerGluLeuLysAla-54 |
| SEQ. ID. NO. 1135 | 68-TyrGlyGluAspGlyAlaVal-74 |
| SEQ. ID. NO. 1136 | 96-GlyMetAspLysTyrArgCys-102 |
| SEQ. ID. NO. 1137 | 120-HisAspAspThrAspPheAspAlaValGluGluLysLeuGly-133 |
| SEQ. ID. NO. 1138 | 140-ProAlaAlaGluGlySerSer-146 |
| SEQ. ID. NO. 1139 | 151-LysValLysGlyLysGlyArgLeuLysSerValTyrGluGluLeuLysHisLeuGln-169 |
| SEQ. ID. NO. 1140 | 205-TyrAspTyrGluAlaLysTyrAsnArgAspAspThrIle-217 |
| SEQ. ID. NO. 1141 | 221-ProSerGluAspLeuThrGluAlaGluGluSerLeuMetArg-234 |
| SEQ. ID. NO. 1142 | 253-AspPheLeuLysAspThrAspGly-260 |
| 094 | |
| AMPHI Regions - AMPHI | |
| SEQ. ID. NO. 1143 | 17-LeuProProIleThrLysValGlySer-25 |
| SEQ. ID. NO. 1144 | 80-PheSerPheLeuThrAlaVal-86 |

TABLE 1-continued

| | |
|---|---|
| Antigenic Index - Jameson-Wolf | |
| SEQ. ID. NO. 1145 | 3-SerProLeuProLysArgAlaLeu-10 |
| SEQ. ID. NO. 1146 | 24-GlySerSerProAlaAlaProArgMetGluAla-34 |
| SEQ. ID. NO. 1147 | 50-MetProSerArgLysArgIleAsnSerAlaAsnIleArgAlaArgGlyIleThr-67 |
| Hydrophilic Regions - Hopp-Woods | |
| SEQ. ID. NO. 1148 | 5-LeuProLysArgAlaLeu-10 |
| SEQ. ID. NO. 1149 | 28-AlaAlaProArgMetGluAla-34 |
| SEQ. ID. NO. 1150 | 51-ProSerArgLysArgIleAsn-57 |
| SEQ. ID. NO. 1151 | 60-AsnIleArgAlaArgGly-65 |
| 095-2 | |
| AMPHI Regions - AMPHI | |
| SEQ. ID. NO. 1152 | 9-CysAlaSerAsnLeuPheArgGlnCysGlnGlnArgGlyGlyAspAlaValAsp-26 |
| SEQ. ID. NO. 1153 | 38-ValLeuGlnAsnValGlnGlnHisPheGlyGlnIleGlyAsnValPheAlaVal-55 |
| SEQ. ID. NO. 1154 | 86-PheGlyGlnHisGlnArgValAsnGlyIleGluAspPheGlyLysValPheLysGlnIleAlaArg-107 |
| SEQ. ID. NO. 1155 | 132-GlyArgArgHisPheAspGlyValValSer-141 |
| SEQ. ID. NO. 1156 | 174-PheLeuAspArgPheAsnArgCysAlaAspPheGlnArgHisAlaAspGlyCysGlnCysValGlnHisVal-197 |
| SEQ. ID. NO. 1157 | 204-GlnHisAspPheLys-208 |
| SEQ. ID. NO. 1158 | 236-AspValGlyGlyIleValGlnThrValSerSerIle-247 |
| SEQ. ID. NO. 1159 | 274-ThrValAspGluIleAspLysArgLeuMetGlnPhePheAspAlaVal-289 |
| SEQ. ID. NO. 1160 | 313-GlyCysIleArgLeuValGly-319 |
| SEQ. ID. NO. 1161 | 370-AsnGlyAspAlaValThrGluAlaHisGlnLeuArgGlnHisGlnGlyAla-386 |
| SEQ. ID. NO. 1162 | 412-AspAspIleArgThrValAsnValPheGlyGlyMet-423 |
| SEQ. ID. NO. 1163 | 435-MetLeuGlySerGlyIleSerArgLeuIleArgThrGly-447 |
| SEQ. ID. NO. 1164 | 451-AlaGlnIleValGlnAspPheGlyAspAlaAlaHisAla-463 |
| Antigenic Index - Jameson-Wolf | |
| SEQ. ID. NO. 1165 | 6-SerGlyGlyCysAlaSerAsnLeu-13 |
| SEQ. ID. NO. 1166 | 16-GlnCysGlnGlnArgGlyGlyAspAlaValAspAlaSerArgAlaHisIle-32 |
| SEQ. ID. NO. 1167 | 62-GlnHisAlaAspGlyAlaGlyLysSerAlaGlyIleGlyGlyGlyAsnArgLeuPhe-80 |
| SEQ. ID. NO. 1168 | 88-GlnHisGlnArgValAsnGlyIleGluAspPheGlyLys-100 |
| SEQ. ID. NO. 1169 | 112-ValArgLeuGluGlyGluTyr-118 |
| SEQ. ID. NO. 1170 | 127-AlaCysGlyGlyLysGlyArgArgHisPheAspGly-138 |
| SEQ. ID. NO. 1171 | 144-ValHisGlnGluArgGlyProAla-151 |
| SEQ. ID. NO. 1172 | 163-AlaAlaAlaAspAlaPheLysAlaGluGlnAlaPhe-174 |
| SEQ. ID. NO. 1173 | 176-AspArgPheAsnArgCysAlaAspPheGlnArgHisAlaAspGlyCysGln-192 |
| SEQ. ID. NO. 1174 | 205-HisAspPheLysArg-209 |
| SEQ. ID. NO. 1175 | 253-GlyGlnAsnArgAlaAspVal-259 |
| SEQ. ID. NO. 1176 | 263-AsnThrGlnLysGlyPheAlaVal-270 |
| SEQ. ID. NO. 1177 | 273-HisThrValAspGluIleAspLysArgLeu-282 |
| SEQ. ID. NO. 1178 | 300-IleGlyAsnAspGlyHisAsnArgCysGlnValGlnLysGlyCys-314 |
| SEQ. ID. NO. 1179 | 339-PheAlaAlaAspAsnGluSerArgValLysSerCysArgAlaGluAspGlyGlyGlyGlnAlaGlyGlyArgGlyPheAlaValArgAlaGlyAsnGly AspAlaValThr-375 |
| SEQ. ID. NO. 1180 | 378-HisGlnLeuArgGlnHisGlnGlyAlaArgAsnAsnGlyAsn-391 |
| SEQ. ID. NO. 1181 | 394-LeuGlnArgSerAspAsnPheGly-401 |
| SEQ. ID. NO. 1182 | 405-PheAspGlyGlyArgGlyAsnAspAspIleArgThr-416 |
| SEQ. ID. NO. 1183 | 442-ArgLeuIleArgThrGlyAsnPheLys-450 |
| SEQ. ID. NO. 1184 | 461-AlaHisAlaAspAlaAlaAspThrAspLysMetAspValGlyAsn-475 |
| Hydrophilic Regions - Hopp-Woods | |
| SEQ. ID. NO. 1185 | 17-CysGlnGlnArgGlyGlyAspAlaValAspAlaSerArgAlaHisIle-32 |
| SEQ. ID. NO. 1186 | 64-AlaAspGlyAlaGlyLysSerAlaGly-72 |
| SEQ. ID. NO. 1187 | 93-AsnGlyIleGluAspPheGlyLys-100 |
| SEQ. ID. NO. 1188 | 112-ValArgLeuGluGlyGluTyr-118 |
| SEQ. ID. NO. 1189 | 128-CysGlyGlyLysGlyArgArgHisPhe-136 |
| SEQ. ID. NO. 1190 | 145-HisGlnGluArgGlyPro-150 |
| SEQ. ID. NO. 1191 | 163-AlaAlaAlaAspAlaPheLysAlaGluGlnAlaPhe-174 |
| SEQ. ID. NO. 1192 | 182-AlaAspPheGlnArgHisAlaAspGly-190 |
| SEQ. ID. NO. 1193 | 205-HisAspPheLysArg-209 |
| SEQ. ID. NO. 1194 | 273-HisThrValAspGluIleAspLysArgLeu-282 |
| SEQ. ID. NO. 1195 | 300-IleGlyAsnAspGlyHisAsnArgCysGlnVal-310 |
| SEQ. ID. NO. 1196 | 339-PheAlaAlaAspAsnGluSerArgValLysSerCysArgAlaGluAspGlyGlyGly-357 |
| SEQ. ID. NO. 1197 | 368-AlaGlyAsnGlyAspAlaValThr-375 |
| SEQ. ID. NO. 1198 | 378-HisGlnLeuArgGlnHisGlnGlyAlaArgAsnAsnGly-390 |
| SEQ. ID. NO. 1199 | 395-GlnArgSerAspAsn-399 |
| SEQ. ID. NO. 1200 | 407-GlyGlyArgGlyAsnAspAspIleArgThr-416 |
| SEQ. ID. NO. 1201 | 461-AlaHisAlaAspAlaAlaAspThrAspLysMetAspVal-473 |
| 096-2 | |
| AMPHI Regions - AMPHI | |
| SEQ. ID. NO. 1202 | 19-GlyIlePheGluGluIleAspAlaHis-27 |
| SEQ. ID. NO. 1203 | 37-AlaAlaAsnArgGln-41 |
| SEQ. ID. NO. 1204 | 61-GlyValValAlaVal-65 |
| SEQ. ID. NO. 1205 | 112-GlnPhePheValAsnAlaPheGln-119 |
| SEQ. ID. NO. 1206 | 129-AlaTyrAlaAlaAlaPheGlyArg-136 |
| SEQ. ID. NO. 1207 | 172-AsnGlnPheAlaAla-176 |
| SEQ. ID. NO. 1208 | 187-AspThrAlaAlaGlyIleGlyAsnAlaGln-196 |
| SEQ. ID. NO. 1209 | 228-GlnTrpGlyPhePhe-232 |
| Antigenic Index - Jameson-Wolf | |
| SEQ. ID. NO. 1210 | 1-MetAlaArgHisThrGlyGlnGlyVal-9 |
| SEQ. ID. NO. 1211 | 22-GluGluIleAspAla-26 |
| SEQ. ID. NO. 1212 | 30-PheArgThrAspCysLeuArgAlaAlaAsn-39 |
| SEQ. ID. NO. 1213 | 75-GlyCysGlyAsnAspValTyrAla-82 |
| SEQ. ID. NO. 1214 | 88-ValGlnAspGlyAla-92 |

TABLE 1-continued

| | |
|---|---|
| SEQ. ID. NO. 1215 | 97-AlaAlaAspLysThrPheGlyAsn-104 |
| SEQ. ID. NO. 1216 | 137-ArgPheHisLysHisArgGln-143 |
| SEQ. ID. NO. 1217 | 157-ValGlnAspGlyGluLeuGlyAsnGlyGlnSerGlnCysLeu-170 |
| SEQ. ID. NO. 1218 | 181-AlaAspGlyGlyCysGlyAspThr-188 |
| SEQ. ID. NO. 1219 | 211-ThrValLysAspValGluCysArgLeu-219 |
| Hydrophilic Regions - Hopp-Woods | |
| SEQ. ID. NO. 1220 | 1-MetAlaArgHisThrGlyGln-7 |
| SEQ. ID. NO. 1221 | 22-GluGluIleAspAla-26 |
| SEQ. ID. NO. 1222 | 33-AspCysLeuArgAlaAlaAsn-39 |
| SEQ. ID. NO. 1223 | 97-AlaAlaAspLysThrPheGly-103 |
| SEQ. ID. NO. 1224 | 137-ArgPheHisLysHisArgGln-143 |
| SEQ. ID. NO. 1225 | 158-GlnAspGlyGluLeuGlyAsn-164 |
| SEQ. ID. NO. 1226 | 183-GlyGlyCysGlyAspThr-188 |
| SEQ. ID. NO. 1227 | 211-ThrValLysAspValGluCysArgLeu-219 |
| 097-2 | |
| AMPHI Regions - AMPHI | |
| SEQ. ID. NO. 1228 | 28-AlaGlyLeuThrThrPheLeuThrMetCysTyrIleVal-40 |
| SEQ. ID. NO. 1229 | 72-MetGlyPheValGly-76 |
| SEQ. ID. NO. 1230 | 166-AlaThrLeuValGlyLeuGlyAspIleHisGlnProSerAlaLeuLeuAlaLeuPheGly-185 |
| SEQ. ID. NO. 1231 | 207-ThrIleThrValIleAlaSerLeuMetGlyLeuAsnGluPheHisGlyIleIleGlyGluValProSerIle-230 |
| SEQ. ID. NO. 1232 | 242-LeuPheThrValSer-246 |
| SEQ. ID. NO. 1233 | 260-PheAspSerThrGlyThrLeu-266 |
| SEQ. ID. NO. 1234 | 342-LeuAlaLysSerValProAlaPheAlaThr-351 |
| SEQ. ID. NO. 1235 | 362-MetLeuArgSerAlaArgAspIle-369 |
| Antigenic Index - Jameson-Wolf | |
| SEQ. ID. NO. 1236 | 1-MetAspThrSerLysGlnThrLeu-8 |
| SEQ. ID. NO. 1237 | 13-PheLysLeuLysAlaAsnGlyThrThrValArgThrGluLeu-26 |
| SEQ. ID. NO. 1238 | 125-LysValArgGluMetLeu-130 |
| SEQ. ID. NO. 1239 | 260-PheAspSerThrGly-264 |
| SEQ. ID. NO. 1240 | 277-ValAspGlyLysLeuProArgLeuLysArg-286 |
| SEQ. ID. NO. 1241 | 317-SerAlaGlyGlyArgThrGly-323 |
| SEQ. ID. NO. 1242 | 364-ArgSerAlaArgAspIleAspTrpAspAspMetThrGlu-376 |
| SEQ. ID. NO. 1243 | 410-LeuCysArgArgThrLysAspValProPro-419 |
| Hydrophilic Regions - Hopp-Woods | |
| SEQ. ID. NO. 1244 | 1-MetAspThrSerLys-5 |
| SEQ. ID. NO. 1245 | 16-LysAlaAsnGlyThrThrValArgThrGluLeu-26 |
| SEQ. ID. NO. 1246 | 125-LysValArgGluMetLeu-130 |
| SEQ. ID. NO. 1247 | 279-GlyLysLeuProArgLeuLysArg-286 |
| SEQ. ID. NO. 1248 | 318-AlaGlyGlyArgThr-322 |
| SEQ. ID. NO. 1249 | 364-ArgSerAlaArgAspIleAspTrpAspAspMetThrGlu-376 |
| SEQ. ID. NO. 1250 | 410-LeuCysArgArgThrLysAspValPro-418 |
| 098-2 | |
| AMPHI Regions - AMPHI | |
| SEQ. ID. NO. 1251 | 29-AlaGluAlaGlyAspGlnPheValGlyAsp-38 |
| SEQ. ID. NO. 1252 | 110-ValGlyAspPhePheLysLeuAlaPhe-118 |
| SEQ. ID. NO. 1253 | 120-CysGlnIleGlnAsnValValThrAlaIleAlaGlnIleValAla-134 |
| SEQ. ID. NO. 1254 | 163-LeuSerSerPheSerHisGly-169 |
| Antigenic Index - Jameson-Wolf | |
| SEQ. ID. NO. 1255 | 24-ValGlnGluAspAlaAlaGluAlaGlyAspGlnPheVal-36 |
| SEQ. ID. NO. 1256 | 68-MetGlyMetCysArg-72 |
| SEQ. ID. NO. 1257 | 78-PheAsnHisThrAspArgGlnAlaAla-86 |
| SEQ. ID. NO. 1258 | 136-ThrAlaAsnGlyThrGlnSerGlyIleThrGlyArgAsnAlaArgLysArgAsnGlyPhe-155 |
| SEQ. ID. NO. 1259 | 158-PheGluGlyArgGlyLeuSerSerPheSerHisGlyIle-170 |
| SEQ. ID. NO. 1260 | 180-ValPheArgArgProMetArgIleCys-188 |
| Hydrophilic Regions - Hopp-Woods | |
| SEQ. ID. NO. 1261 | 24-ValGlnGluAspAlaAlaGluAlaGlyAsp-33 |
| SEQ. ID. NO. 1262 | 79-AsnHisThrAspArgGlnAla-85 |
| SEQ. ID. NO. 1263 | 144-IleThrGlyArgAsnAlaArgLysArgAsnGly-154 |
| SEQ. ID. NO. 1264 | 158-PheGluGlyArgGly-162 |
| SEQ. ID. NO. 1265 | 180-ValPheArgArgProMetArg-186 |
| 099 (delete this one - mistaken sequence) | |
| AMPHI Regions - AMPHI | |
| SEQ. ID. NO. 1266 | 6-SerMetMetArgLeuProAspIle-13 |
| SEQ. ID. NO. 1267 | 47-AlaPheValGluPhePheGlyGluGly-55 |
| SEQ. ID. NO. 1268 | 102-LysLeuValGluThrTyrAlaLysThr-110 |
| SEQ. ID. NO. 1269 | 114-TrpAlaAspAlaLeuLysThrAla-121 |
| SEQ. ID. NO. 1270 | 135-ThrArgAsnMetAlaGlyProSerAsn-143 |
| SEQ. ID. NO. 1271 | 154-AlaAlaLysGlyLeuAlaLysProTyrGluGluProSerAspGly-168 |
| SEQ. ID. NO. 1272 | 178-AlaAlaIleThrSerCysThrAsnThrSerAsnProArgAsnVal-192 |
| SEQ. ID. NO. 1273 | 251-ThrCysAsnGlyMetSer-256 |
| SEQ. ID. NO. 1274 | 341-IleAspAlaValValAlaGluTyrValLysProGlnGlnPheArgAspValTyrVal-359 |
| SEQ. ID. NO. 1275 | 371-ProSerProLeuTyrAspTrpArg-378 |
| SEQ. ID. NO. 1276 | 381-SerThrTyrIleArg-385 |
| SEQ. ID. NO. 1277 | 398-ArgThrLeuArgGlyMetArgProLeu-406 |
| SEQ. ID. NO. 1278 | 443-AspPheAsnSerTyrAlaThr-449 |
| SEQ. ID. NO. 1279 | 468-PheAsnGluMetValLys-473 |
| SEQ. ID. NO. 1280 | 494-MetArgMetTrpGluAlaIleGluThrTyrMet-504 |
| SEQ. ID. NO. 1281 | 532-ArgLeuAlaGlyVal-536 |
| SEQ. ID. NO. 1282 | 539-IleValAlaGluGlyPheGluArgIleHisArgThrAsn-551 |
| SEQ. ID. NO. 1283 | 575-GlyThrGluThrTyr-579 |

TABLE 1-continued

| | |
|---|---|
| Antigenic Index - Jameson-Wolf | |
| SEQ. ID. NO. 1284 | 17-GluLeuAsnGlyLysArgGlnAlaGly-25 |
| SEQ. ID. NO. 1285 | 38-PheLeuArgLysGluArgValVal-45 |
| SEQ. ID. NO. 1286 | 53-GlyGluGlyAlaArgSer-58 |
| SEQ. ID. NO. 1287 | 60-SerIleGlyAspArgAlaThr-66 |
| SEQ. ID. NO. 1288 | 70-MetThrProGluPhe-74 |
| SEQ. ID. NO. 1289 | 83-IleAspGluGlnThr-87 |
| SEQ. ID. NO. 1290 | 94-ThrGlyArgAspAspAlaGlnValLysLeu-103 |
| SEQ. ID. NO. 1291 | 133-SerValThrArgAsnMetAlaGlyProSerAsnProHis-145 |
| SEQ. ID. NO. 1292 | 157-GlyLeuAlaLysProTyrGluGluProSerAspGlyGlnMetProAspGly-173 |
| SEQ. ID. NO. 1293 | 183-CysThrAsnThrSerAsnProArgAsnVal-192 |
| SEQ. ID. NO. 1294 | 201-AsnAlaAsnArgLeuGlyLeuLysArgLysProTrpVal-213 |
| SEQ. ID. NO. 1295 | 216-SerPheAlaProGlySerLysValAla-224 |
| SEQ. ID. NO. 1296 | 235-ProGluMetGluLysLeu-240 |
| SEQ. ID. NO. 1297 | 251-ThrCysAsnGlyMetSerGlyAlaLeuAspProLysIleGlnLysGluIleIleAspArgAspLeuTyr-273 |
| SEQ. ID. NO. 1298 | 279-SerGlyAsnArgAsnPheAspGlyArgIleHisProTyrAlaLys-293 |
| SEQ. ID. NO. 1299 | 312-IleArgPheAspIleGluAsnAspVal-320 |
| SEQ. ID. NO. 1300 | 322-GlyValAlaAspGlyLysGluIleArgLeuLysAsp-333 |
| SEQ. ID. NO. 1301 | 335-TrpProAlaAspGluGluIleAspAlaVal-344 |
| SEQ. ID. NO. 1302 | 348-TyrValLysProGlnGlnPheArgAspVal-357 |
| SEQ. ID. NO. 1303 | 363-AspThrGlyThrAlaGlnLysAlaProSerProLeuTyrAspTrpArgProMetSerThrTyrIleArgArgProProTyrTrp-390 |
| SEQ. ID. NO. 1304 | 394-LeuAlaGlyGluArgThrLeuArgGlyMetArg-404 |
| SEQ. ID. NO. 1305 | 409-LeuProAspAsnIleThrThrAspHisLeuSerProSerAsn-422 |
| SEQ. ID. NO. 1306 | 438-GlyLeuProGluGluAspPheAsnSerTyrAlaThrHisArgGlyAspHisLeuThr-456 |
| SEQ. ID. NO. 1307 | 463-AlaAsnProLysLeuPhe-468 |
| SEQ. ID. NO. 1308 | 471-MetValLysAsnGluAspGlySerValArgGlnGlySerPheAlaArgValGluProGluGlyGluThr-493 |
| SEQ. ID. NO. 1309 | 503-TyrMetAsnArgLysGlnPro-509 |
| SEQ. ID. NO. 1310 | 516-AlaAspTyrGlyGlnGlySerSerArgAspTrpAlaAlaLysGlyValArg-532 |
| SEQ. ID. NO. 1311 | 543-GlyPheGluArgIleHisArgThrAsnLeu-552 |
| SEQ. ID. NO. 1312 | 562-PheLysProAspThrAsnArgHis-569 |
| SEQ. ID. NO. 1313 | 571-LeuGlnLeuAspGlyThrGluThrTyrAspValValGlyGluArgThrProArgCysAspLeu-591 |
| SEQ. ID. NO. 1314 | 595-IleHisArgLysAsnGlyGluThrValGlu-604 |
| SEQ. ID. NO. 1315 | 612-AspThrAlaGluGlu-616 |
| Hydrophilic Regions - Hopp-Woods | |
| SEQ. ID. NO. 1316 | 18-LeuAsnGlyLysArgGlnAlaGly-25 |
| SEQ. ID. NO. 1317 | 38-PheLeuArgLysGluArgValVal-45 |
| SEQ. ID. NO. 1318 | 53-GlyGluGlyAlaArg-57 |
| SEQ. ID. NO. 1319 | 60-SerIleGlyAspArgAlaThr-66 |
| SEQ. ID. NO. 1320 | 83-IleAspGluGlnThr-87 |
| SEQ. ID. NO. 1321 | 94-ThrGlyArgAspAspAlaGlnValLysLeu-103 |
| SEQ. ID. NO. 1322 | 157-GlyLeuAlaLysProTyrGluGluProSerAspGlyGlnMetProAsp-172 |
| SEQ. ID. NO. 1323 | 205-LeuGlyLeuLysArgLysProTrpVal-213 |
| SEQ. ID. NO. 1324 | 235-ProGluMetGluLysLeu-240 |
| SEQ. ID. NO. 1325 | 259-LeuAspProLysIleGlnLysGluIleIleAspArgAspLeuTyr-273 |
| SEQ. ID. NO. 1326 | 282-ArgAsnPheAspGlyArgIle-288 |
| SEQ. ID. NO. 1327 | 312-IleArgPheAspIleGluAsnAspVal-320 |
| SEQ. ID. NO. 1328 | 324-AlaAspGlyLysGluIleArgLeuLysAsp-333 |
| SEQ. ID. NO. 1329 | 335-TrpProAlaAspGluGluIleAspAlaVal-344 |
| SEQ. ID. NO. 1330 | 366-ThrAlaGlnLysAlaPro-371 |
| SEQ. ID. NO. 1331 | 394-LeuAlaGlyGluArgThrLeuArgGlyMetArg-404 |
| SEQ. ID. NO. 1332 | 438-GlyLeuProGluGluAspPheAsn-445 |
| SEQ. ID. NO. 1333 | 450-HisArgGlyAspHis-454 |
| SEQ. ID. NO. 1334 | 471-MetValLysAsnGluAspGlySerValArg-480 |
| SEQ. ID. NO. 1335 | 485-AlaArgValGluProGluGlyGluThr-493 |
| SEQ. ID. NO. 1336 | 503-TyrMetAsnArgLysGlnPro-509 |
| SEQ. ID. NO. 1337 | 518-TyrGlyGlnGlySerSerArgAspTrpAlaAlaLysGlyValArg-532 |
| SEQ. ID. NO. 1338 | 543-GlyPheGluArgIleHisArg-549 |
| SEQ. ID. NO. 1339 | 562-PheLysProAspThrAsnArgHis-569 |
| SEQ. ID. NO. 1340 | 574-AspGlyThrGluThr-578 |
| SEQ. ID. NO. 1341 | 580-AspValValGlyGluArgThrProArgCysAsp-590 |
| SEQ. ID. NO. 1342 | 596-HisArgLysAsnGlyGluThrValGlu-604 |
| SEQ. ID. NO. 1343 | 612-AspThrAlaGluGlu-616 |
| 099-2 | |
| AMPHI Regions - AMPHI | |
| SEQ. ID. NO. 1344 | 30-ProGlySerTyrAspLysLeuPro-37 |
| SEQ. ID. NO. 1345 | 57-ProThrLeuGlnSerTrpLeuGlyGln-65 |
| SEQ. ID. NO. 1346 | 91-ThrAlaLeuValAspLeuAlaGlyLeuArgAsp-101 |
| SEQ. ID. NO. 1347 | 106-LysGlyGlyAspProAlaLysValAsn-114 |
| SEQ. ID. NO. 1348 | 138-AlaPheArgLysAsn-142 |
| SEQ. ID. NO. 1349 | 212-AspSerLeuGlyVal-216 |
| SEQ. ID. NO. 1350 | 234-AlaSerMetMetArgLeuProAspIle-242 |
| SEQ. ID. NO. 1351 | 276-AlaPheValGluPhePheGlyGluGly-284 |
| SEQ. ID. NO. 1352 | 331-LysLeuValGluThrTyrAlaLysThr-339 |
| SEQ. ID. NO. 1353 | 343-TrpAlaAspAlaLeuLysThrAla-350 |
| SEQ. ID. NO. 1354 | 364-ThrArgAsnMetAlaGlyProSerAsn-372 |
| SEQ. ID. NO. 1355 | 383-AlaAlaLysGlyLeuAlaLysProTyrGluGluProSerAspGly-397 |
| SEQ. ID. NO. 1356 | 407-AlaAlaIleThrSerCysThrAsnThrSerAsnProArgAsnVal-421 |
| SEQ. ID. NO. 1357 | 480-ThrCysAsnGlyMetSer-485 |
| SEQ. ID. NO. 1358 | 570-IleAspAlaValValAlaGluTyrValLysProGlnGlnPheArgAspValTyrVal-588 |

TABLE 1-continued

| | |
|---|---|
| SEQ. ID. NO. 1359 | 600-ProSerProLeuTyrAspTrpArg-607 |
| SEQ. ID. NO. 1360 | 610-SerThrTyrIleArg-614 |
| SEQ. ID. NO. 1361 | 627-ArgThrLeuArgGlyMetArgProLeu-635 |
| SEQ. ID. NO. 1362 | 672-AspPheAsnSerTyrAlaThr-678 |
| SEQ. ID. NO. 1363 | 697-PheAsnGluMetValLys-702 |
| SEQ. ID. NO. 1364 | 723-MetArgMetTrpGluAlaIleGluThrTyrMet-733 |
| SEQ. ID. NO. 1365 | 761-ArgLeuAlaGlyVal-765 |
| SEQ. ID. NO. 1366 | 768-IleValAlaGluGlyPheGluArgIleHisArgThrAsn-780 |
| SEQ. ID. NO. 1367 | 804-GlyThrGluThrTyr-808 |
| Antigenic Index - Jameson-Wolf | |
| SEQ. ID. NO. 1368 | 3-AlaAsnGlnArgTyrArgLysProLeuProGlyThrAspLeuGluTyrTyrAsp-20 |
| SEQ. ID. NO. 1369 | 22-ArgAlaAlaCysGluAspIleLysProGlySerTyrAspLysLeuProTyr-38 |
| SEQ. ID. NO. 1370 | 47-LeuValAsnArgAlaAspLysValAspLeuPro-57 |
| SEQ. ID. NO. 1371 | 67-IleGluGlyLysGlnGluIle-73 |
| SEQ. ID. NO. 1372 | 97-AlaGlyLeuArgAspAlaIleAlaGluLysGlyGlyAspProAlaLys-112 |
| SEQ. ID. NO. 1373 | 131-CysGlyGlyTyrAspProAspAlaPheArgLysAsnArgGluIleGluAspArgArgAsnGluAspArgPhe-154 |
| SEQ. ID. NO. 1374 | 162-ThrAlaPheGluAsn-166 |
| SEQ. ID. NO. 1375 | 181-AsnLeuGluLysMetSer-186 |
| SEQ. ID. NO. 1376 | 200-ThrCysValGlyThrAspSerHisThrProHisValAspSer-213 |
| SEQ. ID. NO. 1377 | 222-GlyGlyLeuGluAlaGluThr-228 |
| SEQ. ID. NO. 1378 | 246-GluLeuAsnGlyLysArgGlnAlaGly-254 |
| SEQ. ID. NO. 1379 | 267-PheLeuArgLysGluArgValVal-274 |
| SEQ. ID. NO. 1380 | 282-GlyGluGlyAlaArgSer-287 |
| SEQ. ID. NO. 1381 | 289-SerIleGlyAspArgAlaThr-295 |
| SEQ. ID. NO. 1382 | 299-MetThrProGluPhe-303 |
| SEQ. ID. NO. 1383 | 312-IleAspGluGlnThr-316 |
| SEQ. ID. NO. 1384 | 323-ThrGlyArgAspAspAlaGlnValLysLeu-332 |
| SEQ. ID. NO. 1385 | 362-SerValThrArgAsnMetAlaGlyProSerAsnProHis-374 |
| SEQ. ID. NO. 1386 | 386-GlyLeuAlaLysProTyrGluGluProSerAspGlyGlnMetProAspGly-402 |
| SEQ. ID. NO. 1387 | 412-CysThrAsnThrSerAsnProArgAsnVal-421 |
| SEQ. ID. NO. 1388 | 430-AsnAlaAsnArgLeuGlyLeuLysArgLysProTrpVal-442 |
| SEQ. ID. NO. 1389 | 445-SerPheAlaProGlySerLysValAla-453 |
| SEQ. ID. NO. 1390 | 464-ProGluMetGluLysLeu-469 |
| SEQ. ID. NO. 1391 | 480-ThrCysAsnGlyMetSerGlyAlaLeuAspProLysIleGlnLysGluIleIleAspArgAspLeuTyr-502 |
| SEQ. ID. NO. 1392 | 508-SerGlyAsnArgAsnPheAspGlyArgIleHisProTyrAlaLys-522 |
| SEQ. ID. NO. 1393 | 541-IleArgPheAspIleGluAsnAspVal-549 |
| SEQ. ID. NO. 1394 | 551-GlyValAlaAspGlyLysGluIleArgLeuLysAsp-562 |
| SEQ. ID. NO. 1395 | 564-TrpProAlaAspGluGluIleAspAlaVal-573 |
| SEQ. ID. NO. 1396 | 577-TyrValLysProGlnGlnPheArgAspVal-586 |
| SEQ. ID. NO. 1397 | 592-AspThrGlyThrAlaGlnLysAlaProSerProLeuTyrAspTrpArgProMetSerThrTyrIleArgArgProProTyrTrp-619 |
| SEQ. ID. NO. 1398 | 623-LeuAlaGlyGluArgThrLeuArgGlyMetArg-633 |
| SEQ. ID. NO. 1399 | 638-LeuProAspAsnIleThrThrAspHisLeuSerProSerAsn-651 |
| SEQ. ID. NO. 1400 | 667-GlyLeuProGluGluAspPheAsnSerTyrAlaThrHisArgGlyAspHisLeuThr-685 |
| SEQ. ID. NO. 1401 | 692-AlaAsnProLysLeuPhe-697 |
| SEQ. ID. NO. 1402 | 700-MetValLysAsnGluAspGlySerValArgGlnGlySerPheAlaArgValGluProGluGlyGluThr-722 |
| SEQ. ID. NO. 1403 | 732-TyrMetAsnArgLysGlnPro-738 |
| SEQ. ID. NO. 1404 | 745-AlaAspTyrGlyGlnGlySerSerArgAspTrpAlaAlaLysGlyValArg-761 |
| SEQ. ID. NO. 1405 | 772-GlyPheGluArgIleHisArgThrAsnLeu-781 |
| SEQ. ID. NO. 1406 | 791-PheLysProAspThrAsnArgHis-798 |
| SEQ. ID. NO. 1407 | 800-LeuGlnLeuAspGlyThrGluThrTyrAspValValGlyGluArgThrProArgCysAspLeu-820 |
| SEQ. ID. NO. 1408 | 824-IleHisArgLysAsnGlyGluThrValGlu-833 |
| SEQ. ID. NO. 1409 | 841-AspThrAlaGluGlu-845 |
| Hydrophilic Regions - Hopp-Woods | |
| SEQ. ID. NO. 1410 | 5-GlnArgTyrArgLysProLeuPro-12 |
| SEQ. ID. NO. 1411 | 22-ArgAlaAlaCysGluAspIleLysProGlySerTyrAsp-34 |
| SEQ. ID. NO. 1412 | 47-LeuValAsnArgAlaAspLysValAspLeu-56 |
| SEQ. ID. NO. 1413 | 67-IleGluGlyLysGlnGluIle-73 |
| SEQ. ID. NO. 1414 | 97-AlaGlyLeuArgAspAlaIleAlaGluLysGlyGlyAspProAlaLys-112 |
| SEQ. ID. NO. 1415 | 132-GlyGlyTyrAspProAspAlaPheArgLysAsnArgGluIleGluAspArgArgAsnGluAspArgPhe-154 |
| SEQ. ID. NO. 1416 | 181-AsnLeuGluLysMetSer-186 |
| SEQ. ID. NO. 1417 | 205-AspSerHisThrProHis-210 |
| SEQ. ID. NO. 1418 | 224-LeuGluAlaGluThr-228 |
| SEQ. ID. NO. 1419 | 247-LeuAsnGlyLysArgGlnAlaGly-254 |
| SEQ. ID. NO. 1420 | 267-PheLeuArgLysGluArgValVal-274 |
| SEQ. ID. NO. 1421 | 282-GlyGluGlyAlaArg-286 |
| SEQ. ID. NO. 1422 | 289-SerIleGlyAspArgAlaThr-295 |
| SEQ. ID. NO. 1423 | 312-IleAspGluGlnThr-316 |
| SEQ. ID. NO. 1424 | 323-ThrGlyArgAspAspAlaGlnValLysLeu-332 |
| SEQ. ID. NO. 1425 | 386-GlyLeuAlaLysProTyrGluGluProSerAspGlyGlnMetProAsp-401 |
| SEQ. ID. NO. 1426 | 434-LeuGlyLeuLysArgLysProTrpVal-442 |
| SEQ. ID. NO. 1427 | 464-ProGluMetGluLysLeu-469 |
| SEQ. ID. NO. 1428 | 488-LeuAspProLysIleGlnLysGluIleIleAspArgAspLeuTyr-502 |
| SEQ. ID. NO. 1429 | 511-ArgAsnPheAspGlyArgIle-517 |
| SEQ. ID. NO. 1430 | 541-IleArgPheAspIleGluAsnAspVal-549 |
| SEQ. ID. NO. 1431 | 553-AlaAspGlyLysGluIleArgLeuLysAsp-562 |
| SEQ. ID. NO. 1432 | 564-TrpProAlaAspGluGluIleAspAlaVal-573 |
| SEQ. ID. NO. 1433 | 595-ThrAlaGlnLysAlaPro-600 |
| SEQ. ID. NO. 1434 | 623-LeuAlaGlyGluArgThrLeuArgGlyMetArg-633 |
| SEQ. ID. NO. 1435 | 667-GlyLeuProGluGluAspPheAsn-674 |
| SEQ. ID. NO. 1436 | 679-HisArgGlyAspHisLeuThr-685 |

TABLE 1-continued

| | |
|---|---|
| SEQ. ID. NO. 1437 | 700-MetValLysAsnGluAspGlySerValArg-709 |
| SEQ. ID. NO. 1438 | 714-AlaArgValGluProGluGlyGluThr-722 |
| SEQ. ID. NO. 1439 | 732-TyrMetAsnArgLysGlnPro-738 |
| SEQ. ID. NO. 1440 | 747-TyrGlyGlnGlySerSerArgAspTrpAlaAlaLysGlyValArg-761 |
| SEQ. ID. NO. 1441 | 772-GlyPheGluArgIleHisArg-778 |
| SEQ. ID. NO. 1442 | 791-PheLysProAspThrAsnArgHis-798 |
| SEQ. ID. NO. 1443 | 803-AspGlyThrGluThr-807 |
| SEQ. ID. NO. 1444 | 809-AspValValGlyGluArgThrProArgCysAsp-819 |
| SEQ. ID. NO. 1445 | 824-IleHisArgLysAsnGlyGluThrValGlu-833 |
| SEQ. ID. NO. 1446 | 841-AspThrAlaGluGlu-845 |
| 102 | |
| AMPHI Regions - AMPHI | |
| SEQ. ID. NO. 1447 | 42-ValLeuLeuTyrThrTrpPheSerMetLeu-51 |
| SEQ. ID. NO. 1448 | 67-GlyAlaSerPheAspThrMetValLysAspLeuLeuGlyArgGlyTrpAsnIleIleAsnGlyIleAla-89 |
| SEQ. ID. NO. 1449 | 109-ThrAlaLysGlyLeuGlySerAlaAla-117 |
| SEQ. ID. NO. 1450 | 128-LeuValPhePheGlyIleLeuAlaPheCys-137 |
| SEQ. ID. NO. 1451 | 144-LeuValAspArgPheThrGlyValLeu-152 |
| SEQ. ID. NO. 1452 | 155-GlyMetValLeuThr-159 |
| SEQ. ID. NO. 1453 | 207-AsnValSerSerLeuLeuLysTyrPheLys-216 |
| SEQ. ID. NO. 1454 | 221-LysValAlaLysSerIle-226 |
| SEQ. ID. NO. 1455 | 265-ValLeuIleGluThrLeuSerLysPheAlaGlnThrGlyAsnMetAspLysIleLeuSerLeuPheSerTyrMetAla-290 |
| SEQ. ID. NO. 1456 | 303-PheAspTyrIleAlaAspIlePheLysTrpAsnAsp-314 |
| SEQ. ID. NO. 1457 | 341-PheValThrAlaIleGlyTyr-347 |
| SEQ. ID. NO. 1458 | 352-AlaThrValTrpThrGlyIleIlePro-360 |
| SEQ. ID. NO. 1459 | 374-GlyLysThrTyrLysVal-379 |
| Antigenic Index - Jameson-Wolf | |
| SEQ. ID. NO. 1460 | 1-MetProAsnLysThrProSer-7 |
| SEQ. ID. NO. 1461 | 64-TyrProHisGlyAla-68 |
| SEQ. ID. NO. 1462 | 77-LeuLeuGlyArgGly-81 |
| SEQ. ID. NO. 1463 | 107-AspLeuThrAlaLysGlyLeuGlySerAlaAlaGlyGly-119 |
| SEQ. ID. NO. 1464 | 169-AlaAspAlaLysProSerVal-175 |
| SEQ. ID. NO. 1465 | 179-ThrGlnAlaProAlaGlyThr-185 |
| SEQ. ID. NO. 1466 | 214-TyrPheLysGlyAspAlaProLysValAla-223 |
| SEQ. ID. NO. 1467 | 246-GlyAsnLeuProArgAsnGluPhe-253 |
| SEQ. ID. NO. 1468 | 274-AlaGlnThrGlyAsnMetAspLysIle-282 |
| SEQ. ID. NO. 1469 | 311-LysTrpAsnAspSerIleSerGlyArgThrLysThr-322 |
| SEQ. ID. NO. 1470 | 364-LeuTyrArgSerArgLysLysPheGlyAlaGlyLysThrTyrLysVal-379 |
| Hydrophilic Regions - Hopp-Woods | |
| SEQ. ID. NO. 1471 | 1-MetProAsnLysThr-5 |
| SEQ. ID. NO. 1472 | 169-AlaAspAlaLysPro-173 |
| SEQ. ID. NO. 1473 | 215-PheLysGlyAspAlaProLysValAla-223 |
| SEQ. ID. NO. 1474 | 248-LeuProArgAsnGluPhe-253 |
| SEQ. ID. NO. 1475 | 277-GlyAsnMetAspLys-281 |
| SEQ. ID. NO. 1476 | 316-IleSerGlyArgThrLysThr-322 |
| SEQ. ID. NO. 1477 | 366-ArgSerArgLysLysPheGlyAla-373 |
| 105-2 | |
| AMPHI Regions - AMPHI | |
| SEQ. ID. NO. 1478 | 11-TrpIleGlyLeuGly-15 |
| SEQ. ID. NO. 1479 | 22-ValThrArgLeuLeuAsp-27 |
| SEQ. ID. NO. 1480 | 51-LysValTyrGlyAsnThrAlaGluLeu-59 |
| SEQ. ID. NO. 1481 | 74-AlaAlaValCysAspIleLeuAsnGlyValArgAspGlyLeu-87 |
| SEQ. ID. NO. 1482 | 97-ThrIleSerProThr-101 |
| SEQ. ID. NO. 1483 | 110-ValGluAlaAlaGlyGlyGlnPheAlaGluAlaProVal-122 |
| SEQ. ID. NO. 1484 | 143-AlaValLeuAsnProLeuGlnLysIlePheSer-153 |
| SEQ. ID. NO. 1485 | 162-PheGlyAspValGlyLysGlySer-169 |
| SEQ. ID. NO. 1486 | 176-AsnSerLeuLeuGlyIlePheGlyGluAlaTyr-186 |
| SEQ. ID. NO. 1487 | 203-IleValGluAlaIleGlyXxxSerAla-211 |
| SEQ. ID. NO. 1488 | 249-LeuGluGlnAlaGlyAsnThrLeuProAlaValGlu-260 |
| SEQ. ID. NO. 1489 | 263-AlaAlaSerTyrArgLysAlaValGluAla-272 |
| Antigenic Index - Jameson-Wolf | |
| SEQ. ID. NO. 1490 | 25-LeuLeuAspGlyGlyIleGlu-31 |
| SEQ. ID. NO. 1491 | 34-ValTyrAsnArgSerProAspLysThrAlaProIleSerAlaLysGlyAlaLysValTyrGlyAsnThr-56 |
| SEQ. ID. NO. 1492 | 81-AsnGlyValArgAspGlyLeuAla-88 |
| SEQ. ID. NO. 1493 | 96-SerThrIleSerProThrGluAsnLeuAla-105 |
| SEQ. ID. NO. 1494 | 121-ProValSerGlySerValGlyProAlaThr-130 |
| SEQ. ID. NO. 1495 | 139-GlyGlySerGluAla-143 |
| SEQ. ID. NO. 1496 | 155-ValGlyLysLysThrPheHisPheGlyAspValGlyLysGlySerGly-170 |
| SEQ. ID. NO. 1497 | 196-PheGlyIleAspThrAspThrIleVal-204 |
| SEQ. ID. NO. 1498 | 211-AlaMetAspSerProMetPheGlnThrLysLysSerLeuTrpAlaAsnArgGluPheProPro-231 |
| SEQ. ID. NO. 1499 | 237-HisAlaSerLysAspLeuAsnLeuAlaValLysGluLeuGluGlnAlaGlyAsnThrLeuPro-257 |
| SEQ. ID. NO. 1500 | 264-AlaSerTyrArgLysAlaValGluAlaGlyTyrGlyGluGlnAspValSerGly-281 |
| Hydrophilic Regions - Hopp-Woods | |
| SEQ. ID. NO. 1501 | 25-LeuLeuAspGlyGlyIle-30 |
| SEQ. ID. NO. 1502 | 37-ArgSerProAspLysThrAlaProIleSerAlaLysGlyAlaLys-51 |
| SEQ. ID. NO. 1503 | 81-AsnGlyValArgAspGlyLeuAla-88 |
| SEQ. ID. NO. 1504 | 164-AspValGlyLysGlySerGly-170 |
| SEQ. ID. NO. 1505 | 196-PheGlyIleAspThrAspThrIle-203 |
| SEQ. ID. NO. 1506 | 218-GlnThrLysLysSerLeuTrpAla-225 |

TABLE 1-continued

| | |
|---|---|
| SEQ. ID. NO. 1507 | 237-HisAlaSerLysAspLeuAsnLeuAlaValLysGluLeuGluGlnAlaGly-253 |
| SEQ. ID. NO. 1508 | 265-SerTyrArgLysAlaValGlu-271 |
| SEQ. ID. NO. 1509 | 273-GlyTyrGlyGluGlnAspVal-279 |
| 109-2 | |
| AMPHI Regions - AMPHI | |
| SEQ. ID. NO. 1510 | 6-GlyThrTyrArgAspLeuHisArgProAlaSerGlu-17 |
| SEQ. ID. NO. 1511 | 53-LeuIleProAlaMetAlaGlyThrIleGly-62 |
| SEQ. ID. NO. 1512 | 69-AlaValAlaAlaAlaPhe-74 |
| SEQ. ID. NO. 1513 | 145-GlyLeuLeuMetAla-149 |
| SEQ. ID. NO. 1514 | 156-IleMetAlaLysLeuThrSer-162 |
| SEQ. ID. NO. 1515 | 177-GlyThrThrGlyGlnValLysLysLeuPheSerTrpAlaGly-190 |
| SEQ. ID. NO. 1516 | 207-ValMetTyrAlaLeuLeuGluHisTrpLysLysArgTrpLeu-220 |
| SEQ. ID. NO. 1517 | 222-ValProLeuGlyCysLeuIleAla-229 |
| SEQ. ID. NO. 1518 | 294-HisGlnValPheGlnLysIle-300 |
| SEQ. ID. NO. 1519 | 326-ValGlySerIleLeuGly-331 |
| SEQ. ID. NO. 1520 | 336-ThrSerSerTrpGlyThr-341 |
| SEQ. ID. NO. 1521 | 471-AlaValGlyMetLeuProGlyIleProProPheLeuGluHisPheLysSerLeu-488 |
| Antigenic Index - Jameson-Wolf | |
| SEQ. ID. NO. 1522 | 1-MetGluLysHisAsnGlyThrTyrArgAspLeuHisArgProAlaSer-16 |
| SEQ. ID. NO. 1523 | 18-PheAlaThrArgAspGluTyrLeuGlu-26 |
| SEQ. ID. NO. 1524 | 32-MetGlnProLysArgTrpArgProAsnLeuProPheArgAspTyrArgPheGluTrp-50 |
| SEQ. ID. NO. 1525 | 78-LeuGlyLeuProAsp-82 |
| SEQ. ID. NO. 1526 | 109-ProGlyAlaAsnLeuProGlyThrHis-117 |
| SEQ. ID. NO. 1527 | 160-LeuThrSerAsnGlyVal-165 |
| SEQ. ID. NO. 1528 | 179-ThrGlyGlnValLysLys-184 |
| SEQ. ID. NO. 1529 | 259-GluAsnSerGlyTrp-263 |
| SEQ. ID. NO. 1530 | 301-SerTyrProGluLysThrAspLysVal-309 |
| SEQ. ID. NO. 1531 | 312-AsnIleAspAspThrMetThr-318 |
| SEQ. ID. NO. 1532 | 348-IleAlaLysArgProIleProGlyGly-356 |
| SEQ. ID. NO. 1533 | 398-AlaGlyMetGluMetThrArgLysGlyLysThrThrGln-410 |
| SEQ. ID. NO. 1534 | 441-GlyCysLysGluArgSerAla-447 |
| Hydrophilic Regions - Hopp-Woods | |
| SEQ. ID. NO. 1535 | 1-MetGluLysHisAsnGlyThrTyrArgAspLeuHisArgProAlaSer-16 |
| SEQ. ID. NO. 1536 | 18-PheAlaThrArgAspGluTyrLeuGlu-26 |
| SEQ. ID. NO. 1537 | 35-LysArgTrpArgPro-39 |
| SEQ. ID. NO. 1538 | 44-ArgAspTyrArgPheGluTrp-50 |
| SEQ. ID. NO. 1539 | 180-GlyGlnValLysLys-184 |
| SEQ. ID. NO. 1540 | 301-SerTyrProGluLysThrAspLysVal-309 |
| SEQ. ID. NO. 1541 | 313-IleAspAspThrMetThr-318 |
| SEQ. ID. NO. 1542 | 348-IleAlaLysArgProIlePro-354 |
| SEQ. ID. NO. 1543 | 398-AlaGlyMetGluMetThrArgLysGlyLysThrThrGln-410 |
| SEQ. ID. NO. 1544 | 441-GlyCysLysGluArgSerAla-447 |
| 111-2 | |
| AMPHI Regions - AMPHI | |
| SEQ. ID. NO. 1545 | 6-ArgLeuProAsnPheIleArgVal-13 |
| SEQ. ID. NO. 1546 | 27-SerGluGlnThrTyrThrValLys-48 |
| SEQ. ID. NO. 1547 | 58-ProSerProAlaGluIleGlnLysArgIleAspAspAlaLeuLysGluValAsnArgGlnMetSerPheAsnGlnHisThrAlaGlyLeuArgIleSer-102 |
| SEQ. ID. NO. 1548 | 128-GlyProLeuValAsnLeuTrp-134 |
| SEQ. ID. NO. 1549 | 151-IleLysGlnAlaAlaSerTyrThrGlyAspTyrAlaSerLeu-174 |
| SEQ. ID. NO. 1550 | 183-LeuAspLeuSerSerIleAlaLys-190 |
| SEQ. ID. NO. 1551 | 198-AlaGlyGluTyrLeuValGluIleGlyGly-215 |
| SEQ. ID. NO. 1552 | 237-AsnIleValGlnLeuSerHisIle-276 |
| SEQ. ID. NO. 1553 | 314-GluThrGluAlaLeu-318 |
| Antigenic Index - Jameson-Wolf | |
| SEQ. ID. NO. 1554 | 1-MetProSerGluThrArgLeuProAsnPhe-10 |
| SEQ. ID. NO. 1555 | CysSerGluGlnThrAla-31 |
| SEQ. ID. NO. 1556 | 37-GlnGlyGluThrMetGlyTyr-45 |
| SEQ. ID. NO. 1557 | 49-TyrLeuSerAsnAsnArgAspLysLeuProSerProAlaGluIleGlnLysArgIleAspAspAlaLeuLysGluValAsnArgGlnMetSerThrTyr GlnProAspSerGluIleSerArgPheAsnGlnHisThrAlaGlyLysProLeuArgIleSerSerAspPhe-105 |
| SEQ. ID. NO. 1558 | 111-GluAlaValArgLeuAsnArg-117 |
| SEQ. ID. NO. 1559 | GlyPheGlyProAspLysSerValThrArgGluProSerProGluGlnIleLysGlnThrGly-159 |
| SEQ. ID. NO. 1560 | 163-IleIleLeuLysGlnGlyLysAspTyrAlaSerLeuSerLysThrHisProLysAla-181 |
| SEQ. ID. NO. 1561 | 187-SerPheGlyValAspLysValAlaGlyGluLeuGluLysTyrGly-205 |
| SEQ. ID. NO. 1562 | 213-IleGlyGlyGluLeuHisGlyLysGlyLysAsnAlaArgGlyGluProTrpArgIleGlyIleGluGlnProAsnIle-238 |
| SEQ. ID. NO. 1563 | 240-GlnGlyGlyAsnLeuAsnAsnArgSerLeuAlaThrSerGlyAspTyrArg-262 |
| SEQ. ID. NO. 1564 | 264-PheHisValAspLysAsnGlyLysArgLeuSerIleAsnProAsnAsnLysArgProIleSerAlaMetThrAlaAspGlyLeuSer-306 |
| SEQ. ID. NO. 1565 | 314-GluThrGluAlaLeuLysLeuAlaGluArgGluLysLeu-326 |
| SEQ. ID. NO. 1566 | 332-ValArgAspLysGlyGlyTyrArgMetSerSerGluPheGluLysLeuLeuArg-351 |
| Hydrophilic Regions - Hopp-Woods | |
| SEQ. ID. NO. 1567 | 1-MetProSerGluThrArgLeu-7 |
| SEQ. ID. NO. 1568 | 26-CysSerGluGlnThrAlaThrMet-41 |
| SEQ. ID. NO. 1569 | 51-SerAsnAsnArgAspLysLeuProSer-59 |
| SEQ. ID. NO. 1570 | 61-AlaGluIleGlnLysArgIleAspAspAlaLeuLysGluValAsnArgGlnGlnProAspSerGluIleSerArg-89 |
| SEQ. ID. NO. 1571 | 97-LysProLeuArgIleSerSer-103 |
| SEQ. ID. NO. 1572 | 111-GluAlaValArgLeuAsnArg-117 |
| SEQ. ID. NO. 1573 | 137-GlyProAspLysSerValThrArgGluProSerProGluGlnIleLysGln-153 |
| SEQ. ID. NO. 1574 | 163-IleIleLeuLysGlnGlyLysAspTyrAlaSer-173 |
| SEQ. ID. NO. 1575 | 175-SerLysThrHisPro-179 |
| SEQ. ID. NO. 1576 | 196-LysValAlaGlyGluLeuGluLysTyrGly-205 |
| SEQ. ID. NO. 1577 | 217-LeuHisGlyLysGlyLysAsnAlaArgGlyGluProTrp-229 |

TABLE 1-continued

| | |
|---|---|
| SEQ. ID. NO. 1578 | 267-AspLysAsnGlyLysArgLeuSerProAsnAsnLysArgProIle-285 |
| SEQ. ID. NO. 1579 | 299-AlaMetThrGlyLeuGluThrGluAlaLeuLysLeuAlaGluArgGluLysLeu-326 |
| SEQ. ID. NO. 1580 | 332-ValArgAspLysGlyGlyTyr-338 |
| SEQ. ID. NO. 1581 | 344-SerGluPheGluLysLeuLeuArg-351 |
| 117-1 | |
| AMPHI Regions - AMPHI | |
| SEQ. ID. NO. 1582 | 6-ProIleGlnAspThrGlnSerAla-13 |
| SEQ. ID. NO. 1583 | 15-LeuGlnGluLeuArgGluTrpPheAspSerTyrCysAlaThrPro-55 |
| SEQ. ID. NO. 1584 | 57-GlyGluProLeuProAspHisHisGluLeuAspLeuLeu-77 |
| SEQ. ID. NO. 1585 | 79-AspAlaValAlaAlaThrLeuLeuAlaAspIleGlyArgTyr-92 |
| SEQ. ID. NO. 1586 | 94-ProAspTrpLeuValSerCysAsnSerThrValAlaGluLeuValLysGlyValAspGluValGlnLysLeuThrHisPheAlaArgValAspSerLeu GlnAlaGluThrLysMetLeuLeuAlaMet-150 |
| SEQ. ID. NO. 1587 | 170-PheLeuSerAsnAlaProAspSerProGluLysAspIlePhe-191 |
| SEQ. ID. NO. 1588 | 216-LysProGluLysTyrArgArgLeuGluTyrIleGluAsnPheLeuAsnIleLeuArg-246 |
| SEQ. ID. NO. 1589 | 260-GlyArgProLysHisIleTyrSerIleTyrLys-270 |
| SEQ. ID. NO. 1590 | 282-LeuPheAspIleArg-286 |
| SEQ. ID. NO. 1591 | 290-IleLeuValAspThrValProGluCysTyrThrThrLeuGlyIleValHisSerLeuTrpGlnProIleProGlyGluPheAspAspTyrIleAla-321 |
| SEQ. ID. NO. 1592 | 327-GlyTyrLysSerLeuHisThr-333 |
| SEQ. ID. NO. 1593 | 351-AspMetHisGlnPheAsnGluPheGlyValAla-361 |
| SEQ. ID. NO. 1594 | 385-GlnLeuLeuAspTrp-389 |
| SEQ. ID. NO. 1595 | 412-AspThrHisGlyLysValHisSerSerIleGlyAspArgLeuGluAsn-465 |
| SEQ. ID. NO. 1596 | 485-TyrGluLysAlaIleGlyLysIleArgAlaTyrGlnGlnAsnAlaAsp-508 |
| SEQ. ID. NO. 1597 | 510-ValArgGluGlnLeuAlaLysLeuGlnGluLeuAlaGluGlyTyrLysLysProGluAspLeuTyrThrAsnArgAlaIleGlnLysAlaCysGly ThrLeuAsnGluProPro-571 |
| SEQ. ID. NO. 1598 | 585-LysIleLysLysGlyGlyMetThrThrLeuAlaLysCysCysLysProAlaAspAspIleIleGly-620 |
| SEQ. ID. NO. 1599 | 636-ProSerPheGlnHisLeuAlaGluHisAlaProGluLysValLeuAspAlaLeuGlnGlu-659 |
| SEQ. ID. NO. 1600 | 679-ArgAspValSerAspAla-684 |
| SEQ. ID. NO. 1601 | 714-GlnValAsnAspLeuProArgValLeuAlaSerLeuGlyAspValLysGlyValLeuSerValThrArg-736 |
| AntigenicIndex -Jameson-Wolf | |
| SEQ. ID. NO. 1602 | 5-SerProIleGlnAspThrGlnSerAlaThr-14 |
| SEQ. ID. NO. 1603 | 16-GlnGluLeuArgGluTrpPheAspSerTyrCysAlaAlaLeuProAspAsnAspLysAsnLeuHisTyrProAla-50 |
| SEQ. ID. NO. 1604 | 52-AlaAlaThrProTyrGlyGluProLeuProAspHisPhe-64 |
| SEQ. ID. NO. 1605 | 72-HisAspLeuLeuPro-78 |
| SEQ. ID. NO. 1606 | 88-AspIleGlyArgTyrValProAspTrp-96 |
| SEQ. ID. NO. 1607 | 100-ValSerGluArgCysAsnSerThrVal-108 |
| SEQ. ID. NO. 1608 | 110-GluLeuValLysGlyValAspGluValGlnLysHis-123 |
| SEQ. ID. NO. 1609 | 125-AlaArgValAspSerLeuAlaThrProGluGluArgAlaGlnGlnAlaGluThrMetArg-144 |
| SEQ. ID. NO. 1610 | 162-AlaMetArgThrArgThr-167 |
| SEQ. ID. NO. 1611 | 173-AsnAlaProAspSerProGluLysArgAlaValAlaLysGluThrLeu-188 |
| SEQ. ID. NO. 1612 | 209-AspLeuGlyPheArgHisGlnLysProGluLysTyrArgGluLeuAspGluLysArgThrGluArgLeuGluTyr-237 |
| SEQ. ID. NO. 1613 | 245-LeuArgGlyGluLeuLysLysTyrAsnValAlaGlyArgProLysHisLysMetValLysLysLysLeuSerPhe-279 |
| SEQ. ID. NO. 1614 | 283-PheArgAlaThrValProGluCysTyr-299 |
| SEQ. ID. NO. 1615 | 311-ProIleProGlyGluPheAspAspTyrIleAlaAsnProLysGlyAsnGlyTyrLysSerIleValGlyProGluAspLysGlyValGluValGlnIle ArgThr-349 |
| SEQ. ID. NO. 1616 | 356-AsnGlyTrpArgTyrLysGluGlyGlyLysGlyAspSerAlaTyrGluGlnLys-379 |
| SEQ. ID. NO. 1617 | 387-LeuAspTrpArgGluAsnMetAlaGluSerGlyLysGluAspLeuAlaAla-403 |
| SEQ. ID. NO. 1618 | 418-ThrProHisGlyLysProThrGly-429 |
| SEQ. ID. NO. 1619 | 440-HisSerSerIleGlyAspArgCysArgGlyAlaLysValGluGlyThrProLeuGluAsnGlyGlnArgValGluIleIleThrAlaLysGluGlyHisPro SerValAsnGlyTrpValLysSerAsnLysAlaIleGlyLysAla-500 |
| SEQ. ID. NO. 1620 | 502-IleArgGlnGlnAsnAlaAspThrValArgGluGluGlyArgValGlnLeuAspLysGlnLeuAla-523 |
| SEQ. ID. NO. 1621 | 525-LeuThrProLysProAsnLeuGlnGluLeuAlaGlu-536 |
| SEQ. ID. NO. 1622 | 538-LeuGlyTyrLysLysProGluAspLeuGlyGlnGlyGluIleSerAsnArgAlaIleGlnLysAlaCysGlyThrLeuAsnGluProProProVal Pro-574 |
| SEQ. ID. NO. 1623 | 582-LysGlnSerLysIleLysLysGlyGlyLysAsnGlyVal-594 |
| SEQ. ID. NO. 1624 | 596-IleAspGlyGluAspGlyLeu-602 |
| SEQ. ID. NO. 1625 | 608-LysCysCysLysProAlaProProAspAspIleIleValThrArgGluArgGlyIleSerValHisArgLysThrCysProSerPhe-638 |
| SEQ. ID. NO. 1626 | 644-HisAlaProGluLysValLeuAspGlnIleGluIleArgAlaGlnAspArgSerGlyLeuLeuArgAspValSerAspAlaLeuAlaArgHisLys Leu-690 |
| SEQ. ID. NO. 1627 | 696-GlnThrGlnSerArgAspLeuGluAlaSerMet-706 |
| SEQ. ID. NO. 1628 | 710-LeuGluValLysGlnValAsnAspLeuProArg-720 |
| SEQ. ID. NO. 1629 | 726-GlyAspValLysGly-730 |
| Hydrophilic Regions - Hopp-Woods | |
| SEQ. ID. NO. 1630 | 8-GlnAspThrGlnSer-12 |
| SEQ. ID. NO. 1631 | 16-GlnGluLeuArgGluTrpPhe-22 |
| SEQ. ID. NO. 1632 | 30-ProAspAsnAspLysAsnLeu-36 |
| SEQ. ID. NO. 1633 | 48-TyrProAlaProLeuProHisAspLeuLeuPro-78 |
| SEQ. ID. NO. 1634 | 100-ValSerGluArgCysAsnSerThrGluLeuValLysGlyValAspGluValGlnLysHis-123 |
| SEQ. ID. NO. 1635 | 125-AlaArgValAspSer-129 |
| SEQ. ID. NO. 1636 | 131-AlaThrProGluGluArgAlaGlnGlnAlaGluThrMetArg-144 |
| SEQ. ID. NO. 1637 | 162-AlaMetArgThrArgThrAlaProAspSerProGluLysArgAlaValAlaLysGluThrLeu-188 |
| SEQ. ID. NO. 1638 | 209-AspLeuGlyPheArgHisGlnLysProGluLysTyrArgGluLeuAspGluLysArgThrGluArgLeuGluTyr-237 |
| SEQ. ID. NO. 1639 | 245-LeuArgGlyGluLeuLysLysTyr-252 |
| SEQ. ID. NO. 1640 | 258-ValAlaGlyArgLysHisLysMetValLysLysLysLeuSerPhe-279 |
| SEQ. ID. NO. 1641 | 283-PheArgAlaThrValPro-296 |
| SEQ. ID. NO. 1642 | 314-GlyGluPheAspAsp-318 |
| SEQ. ID. NO. 1643 | 323-ProLysGlyAsnGly-327 |
| SEQ. ID. NO. 1644 | 337-GlyProGluAspLysGlyValGluValGlnIleArgThr-349 |
| SEQ. ID. NO. 1645 | 351-AspGlnArgTyrLysGluGlyGlyLysGlyAspSerAlaTyrGluGlnLeuAspTrpArgGluAsnMetAlaGluSerGlyLysGluAspLeu AlaAla-403 |

TABLE 1-continued

| | |
|---|---|
| SEQ. ID. NO. 1646 | 405-PheLysLeuPheIleGlyAspArgCysArgGlyAlaLysValGluGlyLeuGluAsnGlyGlnArgValGluIleIleThrAlaLysGluGly HisPro-479 |
| SEQ. ID. NO. 1647 | 489-ValLysSerAsnLysAlaIleGlyLysAla-500 |
| SEQ. ID. NO. 1648 | 502-IleGlnAsnAlaAspThrValArgGluGluGlyArgValGlnLeuAspLysGlnLeuAla-523 |
| SEQ. ID. NO. 1649 | 538-LeuGlyTyrLysLysProGluAspLeuGly-551 |
| SEQ. ID. NO. 1650 | 553-GlyGluIleSerAsn-557 |
| SEQ. ID. NO. 1651 | 582-LysGlnSerLysIleLysLysGlyGlyLysVal-594 |
| SEQ. ID. NO. 1652 | 596-IleAspGlyGluAspGlyLeu-602 |
| SEQ. ID. NO. 1653 | 608-LysCysCysLysProAlaProProAspAsp-617 |
| SEQ. ID. NO. 1654 | 623-ThrArgGluArgGlyIleSerValHisArgLysThrCysHisAlaProGluLysValLeu-650 |
| SEQ. ID. NO. 1655 | 658-GlnIleGluIleArgAlaGlnAspArgSerGlyLeuLeuArgAspValSerAspAlaLeuAlaArgHisLysLeuThrGlnSerArgAspLeuGluAla SerMet-706 |
| SEQ. ID. NO. 1656 | 710-LeuGluValLysGlnValAsnAspLeuProArg-720 |
| SEQ. ID. NO. 1657 | 726-GlyAspValLysGly-730 |
| 118-2 | |
| AMPHI Regions - AMPHI | |
| SEQ. ID. NO. 1658 | 11-ArgArgAsnIleGlyLysTrpTyrAsp-31 |
| SEQ. ID. NO. 1659 | 61-ProArgTyrIleGlyThrIleIleAspPheLeuMetValProAsn-79 |
| SEQ. ID. NO. 1660 | 102-GluArgLeuLysThrMetLeuArg-109 |
| Antigenic Index - Jameson-Wolf | |
| SEQ. ID. NO. 1661 | 8-LysAsnPheArgArgAsnIleThrCysPheGluGlyTyrAspGluAsnSerPhe-25 |
| SEQ. ID. NO. 1662 | 27-GlyLysTrpTyrAspAspGlyValTrpAspAspGluGluTyrTrpLysLeuGluAsnAspLeuIleGluValArgLysLysTyrProTyrProMetAsp Ile-60 |
| SEQ. ID. NO. 1663 | 93-AspSerValGlyIleAsnGluArgTyrGluArgLeuLysThr-106 |
| SEQ. ID. NO. 1664 | 112-PheThrGluLysAspIleValAspTyrTyrAsnLysLys-128 |
| Hydrophilic Regions - Hopp-Woods | |
| SEQ. ID. NO. 1665 | 8-LysAsnPheArgArgAsnIleThr-15 |
| SEQ. ID. NO. 1666 | 33-GlyValTrpAspAspGluGluTyrTrpLysLeuGluAsnAspLeuIleGluValArgLysLysTyrProTyrAspIle-60 |
| SEQ. ID. NO. 1667 | 95-ValGlyIleAsnGluArgTyrGluArgLeuLysThr-106 |
| SEQ. ID. NO. 1668 | 112-PheThrGluLysAspIleVal-118 |
| 120-2 | |
| AMPHI Regions - AMPHI | |
| SEQ. ID. NO. 1669 | 6-LysAsnIlePheSerAla-11 |
| SEQ. ID. NO. 1670 | 49-SerGlyAsnAlaTyrLysIleValSerThrIleLys-60 |
| SEQ. ID. NO. 1671 | 77-AsnThrLeuHisProThrTyrTyrArgAspIleArgArg-89 |
| SEQ. ID. NO. 1672 | 142-IleThrAsnGlyLysLysLeuTyrSerValGlyGlyLeuAsnLysAlaGly-158 |
| SEQ. ID. NO. 1673 | 189-ProSerLeuAsnAsnIleProAla-196 |
| Antigenic Index - Jameson-Wolf | |
| SEQ. ID. NO. 1674 | 3-LysThrPheLys-6 |
| SEQ. ID. NO. 1675 | 35-SerGlySerTyrGly-39 |
| SEQ. ID. NO. 1676 | 45-ThrPheGluArgSerGlyAsnAlaTyrLys-54 |
| SEQ. ID. NO. 1677 | 68-PheGluSerGlyGlyThrValVal-75 |
| SEQ. ID. NO. 1678 | 85-ArgAspIleArgArgGlyLysLeuTyrAlaGlu-95 |
| SEQ. ID. NO. 1679 | 97-LysPheAlaAspGlySerValThrTyrGlyLysAlaGlyGluSerLysThrGluGlnSerProLysAla-119 |
| SEQ. ID. NO. 1680 | 131-AlaAsnAspAlaLysLeuProProGlyLeuLysIleThrAsnGlyLysLysLeuTyrSer-150 |
| SEQ. ID. NO. 1681 | 153-GlyLeuAsnLysAlaGlyThrGlyLysTyrSerIleGlyGlyValGluThrGluValValLysTyrArgValArgArgGlyAspAspAlaVal-183 |
| SEQ. ID. NO. 1682 | 199-GlyTyrThrAspAspGlyLysThrTyr-207 |
| SEQ. ID. NO. 1683 | 218-GlyGlnAlaAlaLysPro-223 |
| Hydrophilic Regions - Hopp-Woods | |
| SEQ. ID. NO. 1684 | 45-ThrPheGluArgSerGlyAsn-51 |
| SEQ. ID. NO. 1685 | 85-ArgAspIleArgArgGlyLysLeuTyrAla-94 |
| SEQ. ID. NO. 1686 | 107-LysAlaGlyGluSerLysThrGluGlnSerProLysAla-119 |
| SEQ. ID. NO. 1687 | 131-AlaAsnAspAlaLysLeu-136 |
| SEQ. ID. NO. 1688 | 143-ThrAsnGlyLysLysLeuTyr-149 |
| SEQ. ID. NO. 1689 | 155-AsnLysAlaGlyThrGly-160 |
| SEQ. ID. NO. 1690 | 167-ValGluThrGluValValLysTyrArgValArgArgGlyAspAspAla-182 |
| SEQ. ID. NO. 1691 | 200-TyrThrAspAspGlyLysThrTyr-207 |
| SEQ. ID. NO. 1692 | 219-GlnAlaAlaLysPro-223 |
| 121-1 | |
| AMPHI Regions - AMPHI | |
| SEQ. ID. NO. 1693 | 42-ProGlyArgLeuArgArg-47 |
| SEQ. ID. NO. 1694 | 68-GlnGluLeuSerArgLeuTyrAlaGlnThr-77 |
| SEQ. ID. NO. 1695 | 101-ThrValArgHisAlaPro-106 |
| SEQ. ID. NO. 1696 | 148-ProAlaPheHisGlu-152 |
| SEQ. ID. NO. 1697 | 165-LeuAsnIleGlyGlyIleAlaAsnIle-173 |
| SEQ. ID. NO. 1698 | 189-ProGlyAsnMetLeuMetAspAlaTrpThr-198 |
| SEQ. ID. NO. 1699 | 216-GlyAsnIleLeuProGlnLeuLeuAspArgLeuLeu-227 |
| SEQ. ID. NO. 1700 | 237-ProLysSerThrGly-241 |
| SEQ. ID. NO. 1701 | 251-GluThrTyrLeuAsp-255 |
| SEQ. ID. NO. 1702 | 262-AspValLeuArgThrLeuSerArgPheThrAlaGlnThrValCysAspAlaValSerHis-281 |
| SEQ. ID. NO. 1703 | 303-AlaAspLeuAlaGluCysPhe-309 |
| SEQ. ID. NO. 1704 | 341-IleAsnArgIleProGlySerPro-348 |
| Antigenic Index - Jameson-Wolf | |
| SEQ. ID. NO. 1705 | 13-ThrSerMetAspGlyAlaAsp-19 |
| SEQ. ID. NO. 1706 | 23-IleArgMetAspGlyGlyLysTrpLeuGly-32 |
| SEQ. ID. NO. 1707 | 40-ProTyrProGlyArgLeuArgArgGlnLeuLeuAspLeuGlnAspThrGlyAlaAspGluLeuHisArgSerArgIleLeuSer-67 |
| SEQ. ID. NO. 1708 | 86-AsnLeuAlaProSerAspIleThrAla-94 |
| SEQ. ID. NO. 1709 | 97-CysHisGlyGlnThrValArgHisAlaProGluHisGlyTyrSer-111 |
| SEQ. ID. NO. 1710 | 119-LeuLeuAlaGluArgThrArg-125 |
| SEQ. ID. NO. 1711 | 128-ThrValGlyAspPheArgSerArgAspLeuAlaAlaGlyGlyGlnGly-143 |

TABLE 1-continued

| | |
|---|---|
| SEQ. ID. NO. 1712 | 154-LeuPheArgAspAsnArgGluThrArgAla-163 |
| SEQ. ID. NO. 1713 | 177-ProProAspAlaPro-181 |
| SEQ. ID. NO. 1714 | 184-GlyPheAspThrGlyProGlyAsn-191 |
| SEQ. ID. NO. 1715 | 205-ProTyrAspLysAsnGlyAlaLysAlaAlaGlnGlyAsn-217 |
| SEQ. ID. NO. 1716 | 235-ProHisProLysSerThrGlyArgGlu-243 |
| SEQ. ID. NO. 1717 | 253-TyrLeuAspGlyGlyGluAsnArgTyrAspValLeuArgThrLeuSerArg-269 |
| SEQ. ID. NO. 1718 | 283-AlaAlaAspAlaArgGln-288 |
| SEQ. ID. NO. 1719 | 293-GlyGlyGlyIleArgAsnProValLeu-301 |
| SEQ. ID. NO. 1720 | 321-LeuAsnLeuAspProGlnTrp-327 |
| SEQ. ID. NO. 1721 | 344-IleProGlySerProHisLysAlaThrGlyAlaSerLysProCysIle-359 |
| Hydrophilic Regions - Hopp-Woods | |
| SEQ. ID. NO. 1722 | 13-ThrSerMetAspGlyAlaAsp-19 |
| SEQ. ID. NO. 1723 | 43-GlyArgLeuArgArgGlnLeuLeuAspLeuGlnAspThrGlyAlaAspGluLeuHisArgSerArgIleLeuSer-67 |
| SEQ. ID. NO. 1724 | 101-ThrValArgHisAlaPro-106 |
| SEQ. ID. NO. 1725 | 119-LeuLeuAlaGluArgThrArg-125 |
| SEQ. ID. NO. 1726 | 131-AspPheArgSerArgAspLeuAlaAla-139 |
| SEQ. ID. NO. 1727 | 154-LeuPheArgAspAsnArgGluThrArgAla-163 |
| SEQ. ID. NO. 1728 | 206-TyrAspLysAsnGlyAlaLysAlaAlaGln-215 |
| SEQ. ID. NO. 1729 | 236-HisProLysSerThrGlyArgGlu-243 |
| SEQ. ID. NO. 1730 | 254-LeuAspGlyGlyGluAsnArgTyrAspVal-263 |
| SEQ. ID. NO. 1731 | 283-AlaAlaAspAlaArgGln-288 |
| SEQ. ID. NO. 1732 | 345-ProGlySerProHisLysAlaThrGlyAlaSer-355 |
| 122-1 | |
| AMPHI Regions - AMPHI | |
| SEQ. ID. NO. 1733 | 6-AsnIleHisLysThrPhe-11 |
| SEQ. ID. NO. 1734 | 42-ThrPheLeuArgCysLeuAsnAlaLeuGluMetProGlu-54 |
| SEQ. ID. NO. 1735 | 102-LeuGluAsnValMetGlu-107 |
| SEQ. ID. NO. 1736 | 126-LysLeuLeuGluLys-130 |
| SEQ. ID. NO. 1737 | 176-ProGluLeuValGlnAspValLeuAspThrMetLysGluLeuAla-190 |
| SEQ. ID. NO. 1738 | 227-ProGlnAspLeuPheAspHisPro-234 |
| Antigenic Index - Jameson-Wolf | |
| SEQ. ID. NO. 1739 | 5-ArgAsnIleHisLysThrPheGlyGluAsnThrIle-16 |
| SEQ. ID. NO. 1740 | 23-AspValCysLysGlyGln-28 |
| SEQ. ID. NO. 1741 | 34-GlyProSerGlySerGlyLysThrThr-42 |
| SEQ. ID. NO. 1742 | 51-GluMetProGluAspGlyGlnIleGluPheAspAsnGluArgProLeuLysIleAspPheSerLysLysProSerLysHisAspIle-79 |
| SEQ. ID. NO. 1743 | 81-AlaLeuArgArgLysSerGlyMet-88 |
| SEQ. ID. NO. 1744 | 96-PheProHisLysThrAlaLeu-102 |
| SEQ. ID. NO. 1745 | 114-GlyLysProAlaAlaGlnAlaArgGluGluAlaLeuLysLeuLeuGlu-129 |
| SEQ. ID. NO. 1746 | 131-ValGlyLeuGlyAspLysValAspLeuTyr-140 |
| SEQ. ID. NO. 1747 | 142-TyrGlnLeuSerGlyGlyGlnGlnGlnArgValGlyIle-154 |
| SEQ. ID. NO. 1748 | 168-AspGluProThrSerAlaLeuAspProGluLeuVal-179 |
| SEQ. ID. NO. 1749 | 182-ValLeuAspThrMetLysGluLeuAlaGlnGluGly-193 |
| SEQ. ID. NO. 1750 | 216-MetAspGlyGlyVal-220 |
| SEQ. ID. NO. 1751 | 222-ValGluGlnGlySerProGlnAspLeuPheAspHisProLysHisGluArgThrArgArgPheLeuSer-244 |
| SEQ. ID. NO. 1752 | 246-IleGlnSerThrLysIle-251 |
| Hydrophilic Regions - Hopp-Woods | |
| SEQ. ID. NO. 1753 | 51-GluMetProGluAspGlyGlnIleGluPheAspAsnGluArgProLeuLysIleAspPheSerLysLysProSerLysHisAsp-78 |
| SEQ. ID. NO. 1754 | 81-AlaLeuArgArgLysSerGly-87 |
| SEQ. ID. NO. 1755 | 114-GlyLysProAlaAlaGlnAlaArgGluGluAlaLeuLysLeuLeuGlu-129 |
| SEQ. ID. NO. 1756 | 131-ValGlyLeuGlyAspLysValAsp-138 |
| SEQ. ID. NO. 1757 | 168-AspGluProThrSerAlaLeuAspProGluLeuVal-179 |
| SEQ. ID. NO. 1758 | 182-ValLeuAspThrMetLysGluLeuAlaGln-191 |
| SEQ. ID. NO. 1759 | 229-AspLeuPheAspHisProLysHisGluArgThrArgArgPheLeu-243 |
| 126-1 | |
| AMPHI Regions - AMPHI | |
| SEQ. ID. NO. 1760 | 73-GlyCysGlnSerValGlnGluAla-80 |
| SEQ. ID. NO. 1761 | 112-PheGlnLeuValGluAla-117 |
| SEQ. ID. NO. 1762 | 143-LeuAspAlaGlyCysGln-148 |
| SEQ. ID. NO. 1763 | 150-LeuMetProTrpAlaAlaProIleGlyThrGlyLeuGlyAlaVal-164 |
| SEQ. ID. NO. 1764 | 213-SerGlyAspProValAsnMetAlaArgAlaPhe-223 |
| Antigenic Index - Jameson-Wolf | |
| SEQ. ID. NO. 1765 | 7-GluThrPheProSerArgLeu-13 |
| SEQ. ID. NO. 1766 | 24-GluIleLeuLysGlnSerIle-30 |
| SEQ. ID. NO. 1767 | 41-SerLeuArgArgAlaGlySerGlyGlyGluAlaHisGlyGlnGlyPhe-56 |
| SEQ. ID. NO. 1768 | 85-GlnMetAlaArgGluValPheGlu-92 |
| SEQ. ID. NO. 1769 | 99-GluLeuIleGlyAspAspAspThrLeuGln-108 |
| SEQ. ID. NO. 1770 | 121-LeuIleLysAspGlyPheLysValLeu-129 |
| SEQ. ID. NO. 1771 | 141-ArgLeuLeuAspAlaGlyCys-147 |
| SEQ. ID. NO. 1772 | 171-ValLeuArgGluArgLeuProAspThrProLeu-181 |
| SEQ. ID. NO. 1773 | 209-AlaValSerArgSerGlyAspProValAsn-218 |
| SEQ. ID. NO. 1774 | 228-GluSerGlyArgLeuAlaPhe-234 |
| SEQ. ID. NO. 1775 | 237-GlyProValGluAlaArgAspLysAlaGlnAlaSerThrProThrVal-252 |
| Hydrophilic Regions - Hopp-Woods | |
| SEQ. ID. NO. 1776 | 41-SerLeuArgArgAlaGlySerGlyGlyGluAlaHis-52 |
| SEQ. ID. NO. 1777 | 85-GlnMetAlaArgGluValPheGlu-92 |
| SEQ. ID. NO. 1778 | 100-LeuIleGlyAspAspAspThrLeuGln-108 |
| SEQ. ID. NO. 1779 | 171-ValLeuArgGluArgLeuProAsp-178 |
| SEQ. ID. NO. 1780 | 210-ValSerArgSerGlyAspPro-216 |

TABLE 1-continued

| | |
|---|---|
| SEQ. ID. NO. 1781 | 228-GluSerGlyArgLeuAlaPhe-234 |
| SEQ. ID. NO. 1782 | 237-GlyProValGluAlaArgAspLysAlaGlnAla-247 |
| 127 | |
| AMPHI Regions - AMPHI | |
| SEQ. ID. NO. 1783 | 6-MetLeuAspThrTrpLeuGlyAla-13 |
| SEQ. ID. NO. 1784 | 20-AlaValGluSerValAlaAla-26 |
| SEQ. ID. NO. 1785 | 119-ValGlyAspTyrIleGluIle-125 |
| SEQ. ID. NO. 1786 | 135-IleAsnLeuLeuAsnThrLeuMet-142 |
| SEQ. ID. NO. 1787 | 147-ProAsnProLeuValGlyGlnLeuAla-155 |
| SEQ. ID. NO. 1788 | 206-LeuGluProLeuCysAlaPro-212 |
| SEQ. ID. NO. 1789 | 214-IleProAlaIleGlnArgXxxLeuGluAsnValGln-225 |
| SEQ. ID. NO. 1790 | 250-ArgIleIleValArgPheAlaSerProVal-259 |
| SEQ. ID. NO. 1791 | 268-AlaValMetAspGluPheLeuArgVal-276 |
| Antigenic Index - Jameson-Wolf | |
| SEQ. ID. NO. 1792 | 16-IleArgAlaGluAlaValGlu-22 |
| SEQ. ID. NO. 1793 | 41-HisPheLysArgHisProAspPheGlyIleGluSerLysArgArgPheLeuVal-58 |
| SEQ. ID. NO. 1794 | 112-SerAlaThrGlnGlnTyrSerVal-119 |
| SEQ. ID. NO. 1795 | 126-AsnGlyLeuArgGlyArgValValAsp-134 |
| SEQ. ID. NO. 1796 | 169-HisProValArgArgAspAsnIleLeu-177 |
| SEQ. ID. NO. 1797 | 193-LeuAspSerAspGluAlaValCysArg-201 |
| SEQ. ID. NO. 1798 | 234-AlaAlaArgProArgValThrArgValProTyrAspAspLysAlaTyr-249 |
| SEQ. ID. NO. 1799 | 257-SerProValSerLysArgLeuGluIle-265 |
| SEQ. ID. NO. 1800 | 282-AsnHisProAlaGlySerGluThrLeu-290 |
| Hydrophilic Regions - Hopp-Woods | |
| SEQ. ID. NO. 1801 | 16-IleArgAlaGluAlaValGlu-22 |
| SEQ. ID. NO. 1802 | 42-PheLysArgHisProAspPheGlyIleGluSerLysArgArgPheLeuVal-58 |
| SEQ. ID. NO. 1803 | 126-AsnGlyLeuArgGlyArgValVal-133 |
| SEQ. ID. NO. 1804 | 170-ProValArgArgAspAsnIleLeu-177 |
| SEQ. ID. NO. 1805 | 193-LeuAspSerAspGluAlaValCysArg-201 |
| SEQ. ID. NO. 1806 | 235-AlaArgProArgValThrArgValProTyrAspAspLysAlaTyr-249 |
| SEQ. ID. NO. 1807 | 259-ValSerLysArgLeuGluIle-265 |
| SEQ. ID. NO. 1808 | 285-AlaGlySerGluThrLeu-290 |
| 128-1 | |
| AMPHIRegions- AMPHI | |
| SEQ. ID. NO. 1809 | 43-AlaGlnThrHisThrGlyTrpAlaAsnThrValGluProLeuThrGlyIleThrGluArgValGlyArgIleTrpGlyValValSerHisLeuAsnSerVal AlaAspThrProGluLeu-82 |
| SEQ. ID. NO. 1810 | 85-ValTyrAsnGluLeuMetProGluIle-93 |
| SEQ. ID. NO. 1811 | 102-GlnAspIleGluLeuTyrAsnArgPheLysThrIleLysAsnSerProGluPhe-119 |
| SEQ. ID. NO. 1812 | 166-PheSerGlnAsnValLeuAspAlaThrAsp-175 |
| SEQ. ID. NO. 1813 | 189-GlyIleProGluAspAla-194 |
| SEQ. ID. NO. 1814 | 218-HisTyrLeuAlaVal-222 |
| SEQ. ID. NO. 1815 | 245-GluLeuSerAspAspGlyLysPheAspAsnThrAlaAsnIleAspArgThrLeuAlaAsnAlaLeuGlnThrAlaLysLeuLeuGlyPheLys AsnTyrAlaGlu-279 |
| SEQ. ID. NO. 1816 | 286-MetAlaAspThrProGluGlnValLeuAsnPheLeuHisAspLeuAlaArgArgAla-304 |
| SEQ. ID. NO. 1817 | 313-AlaGluValLysAlaPheAlaArg-320 |
| SEQ. ID. NO. 1818 | 359-GlyLysValLeuAsnGlyLeuPheAlaGlnIleLysLysLeuTyrGly-374 |
| SEQ. ID. NO. 1819 | 472-LeuHisHisLeuLeuThrGlnValAspGluLeu-482 |
| SEQ. ID. NO. 1820 | 496-GluLeuProSerGlnPhe-501 |
| SEQ. ID. NO. 1821 | 565-GlyArgLeuLysAsnTrpGlnGlnValLeuAspSerVal-577 |
| SEQ. ID. NO. 1822 | 610-SerTyrAlaTrpAlaGlu-615 |
| SEQ. ID. NO. 1823 | 623-AlaAlaPheGluGluSerAspAsp-630 |
| SEQ. ID. NO. 1824 | 636-LysArgPheTrpGluIleLeuAla-644 |
| SEQ. ID. NO. 1825 | 651-AlaAlaGluSerPheLysAlaPheArg-659 |
| AntigenicIndex -Jameson-Wolf | |
| SEQ. ID. NO. 1826 | 9-LeuGlyGluGluProArgPheAspGlnIleLysThrGluAspIleLysProAlaLeu-27 |
| SEQ. ID. NO. 1827 | 32-AlaGluAlaArgGluGlnIleAla-39 |
| SEQ. ID. NO. 1828 | 43-AlaGlnThrHisThrGlyTrp-49 |
| SEQ. ID. NO. 1829 | 51-AsnThrValGluProLeuThrGlyIleThrGluArgValGlyArgIleTrp-67 |
| SEQ. ID. NO. 1830 | 75-SerValAlaAspThrProGluLeu-82 |
| SEQ. ID. NO. 1831 | 100-IleGlyGlnAspIleGluLeuTyrAsnArgPheLysThrIleLysAsnSerProGluPheAspThrLeuSerProAlaGlnLysThrLysLeuAsn HisAspLeuArgAsp-136 |
| SEQ. ID. NO. 1832 | 138-ValLeuSerGlyAlaGluLeuProProGluGlnGlnAlaGluLeuAlaLysLeuGlnThrGluGlyAlaGlnLeu-162 |
| SEQ. ID. NO. 1833 | 165-LysPheSerGlnAsnVal-170 |
| SEQ. ID. NO. 1834 | 172-AspAlaThrAspAla-176 |
| SEQ. ID. NO. 1835 | 190-IleProGluAspAla-194 |
| SEQ. ID. NO. 1836 | 202-AlaGlnSerGluSerLysThrGlyTyrLysIle-212 |
| SEQ. ID. NO. 1837 | 226-AlaAspAsnArgGluLeuArgGluGlnIle-235 |
| SEQ. ID. NO. 1838 | 240-ValThrArgAlaSerGluLeuSerAspAspGlyLysPheAspAsnThrAlaAsnIleAspArgThrLeu-262 |
| SEQ. ID. NO. 1839 | 285-LysMetAlaAspThrProGluGln-292 |
| SEQ. ID. NO. 1840 | 300-LeuAlaArgArgAlaLysProTyrAlaGluLysAspLeuAlaGlu-314 |
| SEQ. ID. NO. 1841 | 316-LysAlaPheAlaArgGluSerLeuAsn-324 |
| SEQ. ID. NO. 1842 | 335-TyrAlaSerGluLysLeuArgGluAlaLysTyrAlaPheSerGluThrGluValLysLys-354 |
| SEQ. ID. NO. 1843 | 376-GlyPheThrGluLysThrVal-382 |
| SEQ. ID. NO. 1844 | 387-LysAspValArgTyrPheGluLeuGlnGlnAsnGlyGluThrIle-401 |
| SEQ. ID. NO. 1845 | 409-TyrAlaArgGluGlyLysArgGlyGlyAla-418 |
| SEQ. ID. NO. 1846 | 420-MetAsnAspTyrLysGlyArgArgArgPheSerAspGlyThrLeu-434 |
| SEQ. ID. NO. 1847 | 447-ProProValGlyGlyArgGluAlaArgLeuSerHisAspGlu-460 |
| SEQ. ID. NO. 1848 | 478-GlnValAspGluLeuGlyVal-484 |
| SEQ. ID. NO. 1849 | 496-GluLeuProSerGln-500 |
| SEQ. ID. NO. 1850 | 516-SerAlaHisGluGluThrGlyVal-523 |

TABLE 1-continued

| | |
|---|---|
| SEQ. ID. NO. 1851 | 560-SerGluAspAspGluGlyArgLeuLysAsn-569 |
| SEQ. ID. NO. 1852 | 575-AspSerValArgLysLysValAla-582 |
| SEQ. ID. NO. 1853 | 586-ProProGluTyrAsnArg-591 |
| SEQ. ID. NO. 1854 | 605-SerAlaGlyTyrTyrSerTyr-611 |
| SEQ. ID. NO. 1855 | 625-PheGluGluSerAspAspValAlaAlaThrGlyLysArgPheTrp-639 |
| SEQ. ID. NO. 1856 | 646-GlyGlySerArgSerAlaAlaGluSerPheLysAlaPheArgGlyArgGluProSerIle-665 |
| SEQ. ID. NO. 1857 | 669-LeuArgHisSerGlyPheAspAsnAlaVal-678 |
| Hydrophilic Regions - Hopp-Woods | |
| SEQ. ID. NO. 1858 | 9-LeuGlyGluGluProArgPheAspGlnIleLysThrGluAspIleLysPro-25 |
| SEQ. ID. NO. 1859 | 32-AlaGluAlaArgGluGlnIleAla-39 |
| SEQ. ID. NO. 1860 | 59-IleThrGluArgValGly-64 |
| SEQ. ID. NO. 1861 | 77-AlaAspThrProGluLeu-82 |
| SEQ. ID. NO. 1862 | 100-IleGlyGlnAspIleGluLeu-106 |
| SEQ. ID. NO. 1863 | 111-LysThrIleLysAsnSerProGluPheAspThr-121 |
| SEQ. ID. NO. 1864 | 123-SerProAlaGlnLysThrLysLeuAsnHisAspLeuArgAsp-136 |
| SEQ. ID. NO. 1865 | 143-GluLeuProProGluGlnGlnAlaGluLeuAlaLysLeuGlnThrGluGlyAlaGlnLeu-162 |
| SEQ. ID. NO. 1866 | 190-IleProGluAspAla-194 |
| SEQ. ID. NO. 1867 | 202-AlaGlnSerGluSerLysThrGlyTyr-210 |
| SEQ. ID. NO. 1868 | 226-AlaAspAsnArgGluLeuArgGluGlnIle-235 |
| SEQ. ID. NO. 1869 | 242-ArgAlaSerGluLeuSerAspAspGlyLysPheAspAsn-254 |
| SEQ. ID. NO. 1870 | 256-AlaAsnIleAspArgThrLeu-262 |
| SEQ. ID. NO. 1871 | 285-LysMetAlaAspThrProGlu-291 |
| SEQ. ID. NO. 1872 | 300-LeuAlaArgArgAlaLysProTyrAlaGluLysAspLeuAlaGlu-314 |
| SEQ. ID. NO. 1873 | 316-LysAlaPheAlaArgGluSerLeuAsn-324 |
| SEQ. ID. NO. 1874 | 335-TyrAlaSerGluLysLeuArgGluAlaLysTyrAlaPheSerGluThrGluValLysLys-354 |
| SEQ. ID. NO. 1875 | 377-PheThrGluLysThr-381 |
| SEQ. ID. NO. 1876 | 387-LysAspValArgTyr-391 |
| SEQ. ID. NO. 1877 | 396-GlnAsnGlyGluThr-400 |
| SEQ. ID. NO. 1878 | 409-TyrAlaArgGluGlyLysArgGlyGly-417 |
| SEQ. ID. NO. 1879 | 423-TyrLysGlyArgArgArgPheSerAsp-431 |
| SEQ. ID. NO. 1880 | 449-ValGlyGlyArgGluAlaArgLeuSerHisAspGlu-460 |
| SEQ. ID. NO. 1881 | 478-GlnValAspGluLeuGly-483 |
| SEQ. ID. NO. 1882 | 516-SerAlaHisGluGluThrGly-522 |
| SEQ. ID. NO. 1883 | 560-SerGluAspAspGluGlyArgLeuLysAsn-569 |
| SEQ. ID. NO. 1884 | 575-AspSerValArgLysLysValAla-582 |
| SEQ. ID. NO. 1885 | 625-PheGluGluSerAspAspValAlaAlaThrGly-635 |
| SEQ. ID. NO. 1886 | 647-GlySerArgSerAlaAlaGluSerPheLysAlaPheArgGlyArgGluProSerIle-665 |
| 130-2 | |
| AMPHI Regions - AMPHI | |
| SEQ. ID. NO. 1887 | 16-ThrLeuValSerGlyIle-21 |
| SEQ. ID. NO. 1888 | 36-GlySerGlySerPheGly-41 |
| SEQ. ID. NO. 1889 | 56-GlnProValGlyGlnLeu-61 |
| SEQ. ID. NO. 1890 | 91-AsnValProAsnAlaPro-96 |
| SEQ. ID. NO. 1891 | 110-GlnGlyPheAspThrLeuPheGlnHisAlaLeuAsnGlyPheAsnAlaMet-126 |
| SEQ. ID. NO. 1892 | 171-ThrAlaSerAlaPro-175 |
| SEQ. ID. NO. 1893 | 204-PheGluAlaThrCysGln-209 |
| SEQ. ID. NO. 1894 | 211-CysHisGlyGlySerIleProGlyIlePro-220 |
| SEQ. ID. NO. 1895 | 234-LysGlyLysGluThr-238 |
| SEQ. ID. NO. 1896 | 245-GluGlyPheAsnAlaMet-250 |
| Antigenic Index - Jameson-Wolf | |
| SEQ. ID. NO. 1897 | 1-MetLysGlnLeuArgAspAsnLysAlaGlnGlySer-12 |
| SEQ. ID. NO. 1898 | 35-AlaGlySerGlySerPheGlyAspValAspAlaThrThrGluAlaAlaThrGlnThrArgIleGlnProValGly-59 |
| SEQ. ID. NO. 1899 | 63-MetGlyAspGlyIleProValGlyGluArgGlnGlyGlu-75 |
| SEQ. ID. NO. 1900 | 87-AlaAlaAspSerAsnValProAsnAlaProLysLeuGluHisAsnGlyAspTrpAla-105 |
| SEQ. ID. NO. 1901 | 108-IleAlaGlnGlyPhe-112 |
| SEQ. ID. NO. 1902 | 126-MetProAlaLysGlyGlyAla-132 |
| SEQ. ID. NO. 1903 | 134-AspLeuThrAspGlnGluLeuLysArg-142 |
| SEQ. ID. NO. 1904 | 148-AlaAsnLysSerGlyGlySerPheProAsnProAspGluAlaAlaProAlaAspAsnAlaAlaSerGlyThrAlaSerAlaProAlaAspSerAlaAla ProAlaGluAlaLysAlaGluAspLysGlyAlaAla-192 |
| SEQ. ID. NO. 1905 | 197-GlyValAspGlyLysLysValPheGlu-205 |
| SEQ. ID. NO. 1906 | 221-GlyIleGlyLysLysAspAspTrpAlaProArgIleLysLysGlyLysGluThrLeuHis-240 |
| SEQ. ID. NO. 1907 | 251-ProAlaLysGlyGlyAsnAlaGlyLeuSerAspAspGluValLysAla-266 |
| SEQ. ID. NO. 1908 | 274-GlnSerGlyAlaLys-278 |
| Hydrophilic Regions - Hopp-Woods | |
| SEQ. ID. NO. 1909 | 1-MetLysGlnLeuArgAspAsnLysAlaGlnGly-11 |
| SEQ. ID. NO. 1910 | 41-GlyAspValAspAlaThrThrGluAlaAlaThr-51 |
| SEQ. ID. NO. 1911 | 68-ProValGlyGluArgGlnGlyGlu-75 |
| SEQ. ID. NO. 1912 | 87-AlaAlaAspSerAsnVal-92 |
| SEQ. ID. NO. 1913 | 96-ProLysLeuGluHisAsnGly-102 |
| SEQ. ID. NO. 1914 | 127-ProAlaLysGlyGlyAla-132 |
| SEQ. ID. NO. 1915 | 134-AspLeuThrAspGlnGluLeuLysArg-142 |
| SEQ. ID. NO. 1916 | 156-ProAsnProAspGluAlaAlaProAlaAspAsnAlaAla-168 |
| SEQ. ID. NO. 1917 | 174-AlaProAlaAspSerAlaAlaProAlaGluAlaLysAlaGluAspLysGlyAlaAla-192 |
| SEQ. ID. NO. 1918 | 198-ValAspGlyLysLysValPheGlu-205 |

TABLE 1-continued

| | |
|---|---|
| SEQ. ID. NO. 1919 | 222-IleGlyLysLysAspAspTrpAlaProArgIleLysLysGlyLysGluThrLeuHis-240 |
| SEQ. ID. NO. 1920 | 251-ProAlaLysGlyGlyAsn-256 |
| SEQ. ID. NO. 1921 | 258-GlyLeuSerAspAspGluValLysAla-266 |
| 132-2 | |
| AMPHI Regions - AMPHI | |
| SEQ. ID. NO. 1922 | 13-IleIleSerAlaLeuAlaVal-19 |
| SEQ. ID. NO. 1923 | 70-AlaThrCysMetAlaMetVal-76 |
| SEQ. ID. NO. 1924 | 92-ValGlnGlnThrGlnGlnAlaProLysProValSerAsnThr-105 |
| Antigenic Index - Jameson-Wolf | |
| SEQ. ID. NO. 1925 | 26-GlnHisGlyLysGlyAlaAspAla-33 |
| SEQ. ID. NO. 1926 | 38-GlySerGlySerGlySerAla-44 |
| SEQ. ID. NO. 1927 | 81-HisThrThrLysHisGlyLeuAspPhe-89 |
| SEQ. ID. NO. 1928 | 91-AsnValGlnGlnThrGlnGlnAlaProLysProValSerAsnThrGluPro-SerAlaProValProGlnGlnGlnLys-116 |
| Hydrophilic Regions - Hopp-Woods | |
| SEQ. ID. NO. 1929 | 28-GlyLysGlyAlaAspAla-33 |
| SEQ. ID. NO. 1930 | 97-GlnAlaProLysProValSerAsnThrGluProSerAla-109 |
| 134 | |
| AMPHI Regions - AMPHI | |
| SEQ. ID. NO. 1931 | 39-IleGlnSerAlaGlyThrVal-45 |
| SEQ. ID. NO. 1932 | 47-GlyLysLysThrGly-51 |
| SEQ. ID. NO. 1933 | 58-TrpMetGluIleGluLysGlnArg-65 |
| SEQ. ID. NO. 1934 | 83-ValAsnLeuLeuAspThrProGlyHis-91 |
| SEQ. ID. NO. 1935 | 97-AspThrTyrArgValLeuThrAlaVal-105 |
| SEQ. ID. NO. 1936 | 114-AlaAlaGlyValGlu-119 |
| SEQ. ID. NO. 1937 | 123-IleLysLeuLeuAsnValCysArg-130 |
| SEQ. ID. NO. 1938 | 142-LysTyrAspArgGluVal-147 |
| SEQ. ID. NO. 1939 | 149-AspSerLeuGluLeuLeuAspGluValGluAsnIleLeuLys-162 |
| SEQ. ID. NO. 1940 | 176-LysAsnPheLysGlyValTyrHisIleLeu-185 |
| SEQ. ID. NO. 1941 | 201-HisGluPheAspIleIleLysGlyIleAspAsn-211 |
| SEQ. ID. NO. 1942 | 254-PheGlySerAlaIle-258 |
| SEQ. ID. NO. 1943 | 265-GluIleLeuAsnSerLeuIleAspTrpAlaPro-275 |
| SEQ. ID. NO. 1944 | 322-LysPheGluArgGlyMetLys-328 |
| SEQ. ID. NO. 1945 | 361-AspIleIleGlyIleProAsnHis-368 |
| SEQ. ID. NO. 1946 | 395-LeuPheArgSerValArgIleLys-402 |
| SEQ. ID. NO. 1947 | 404-ProLeuLysIleLysGln-409 |
| SEQ. ID. NO. 1948 | 411-GlnLysGlyLeuGlnGlnLeuGlyGlu-419 |
| SEQ. ID. NO. 1949 | 423-ValGlnValPheLysProMetSer-430 |
| SEQ. ID. NO. 1950 | 449-SerArgLeuAlaAsnGluTyr-455 |
| SEQ. ID. NO. 1951 | 481-AlaGluPheGluLysAlaAsn-487 |
| SEQ. ID. NO. 1952 | 515-ArgTrpProAspIle-519 |
| Antigenic Index - Jameson-Wolf | |
| SEQ. ID. NO. 1953 | 4-GluIleLeuAspGlnValArgArgArgArgThrPhe-15 |
| SEQ. ID. NO. 1954 | 19-SerHisProAspAlaGlyLysThrThrLeuThr-29 |
| SEQ. ID. NO. 1955 | 43-GlyThrValLysGlyLysLysThrGlyLysPheAlaThr-55 |
| SEQ. ID. NO. 1956 | 57-AspTrpMetGluIleGluLysGlnArgGly-66 |
| SEQ. ID. NO. 1957 | 76-PheAspTyrLysAspHisThrVal-83 |
| SEQ. ID. NO. 1958 | 85-LeuLeuAspThrProGlyHisGlnAspPheSerGluAspThrTyrArg-100 |
| SEQ. ID. NO. 1959 | 113-AspAlaAlaLysGlyValGlu-119 |
| SEQ. ID. NO. 1960 | 129-CysArgLeuArgAspThrPro-135 |
| SEQ. ID. NO. 1961 | 140-MetAsnLysTyrAspArgGluValArgAspSerLeuGluLeuLeuAspGluValGluAsn-159 |
| SEQ. ID. NO. 1962 | 173-GlyMetGlyLysAsnPheLys-179 |
| SEQ. ID. NO. 1963 | 194-AlaGlyGlyGluArgLeuProHis-201 |
| SEQ. ID. NO. 1964 | 207-LysGlyIleAspAsnProGluLeuGluGlnArgPheProLeu-220 |
| SEQ. ID. NO. 1965 | 223-GlnGlnLeuArgAspGluIleGluLeu-231 |
| SEQ. ID. NO. 1966 | 235-AlaSerAsnGluPheAsnLeu-241 |
| SEQ. ID. NO. 1967 | 275-ProAlaProLysProArgAspAlaThrValArgMetValGluProAspGluProLysPhe-294 |
| SEQ. ID. NO. 1968 | 302-GlnAlaAsnMetAspProLysHisArgAspArgIleAla-314 |
| SEQ. ID. NO. 1969 | 317-ArgValCysSerGlyLysPheGluArgGlyMetLysMetLysHisLeuArgIleAsnArgGluIleAla-339 |
| SEQ. ID. NO. 1970 | 348-SerHisAspArgGluLeuValGlu-355 |
| SEQ. ID. NO. 1971 | 365-IleProAsnHisGly-369 |
| SEQ. ID. NO. 1972 | 373-IleGlyAspSerPheSerGluGlyGluGln-382 |
| SEQ. ID. NO. 1973 | 399-ValArgIleLysAsnProLeuLysIleLysGlnLeuGlnLysGlyLeuGlnGlnLeuGlyGluGluGlyAla-422 |
| SEQ. ID. NO. 1974 | 450-ArgLeuAlaAsnGluTyrGlyVal-457 |
| SEQ. ID. NO. 1975 | 459-AlaValPheAspSer-463 |
| SEQ. ID. NO. 1976 | 473-SerCysAspAspLysLysLysLeuAlaGluPheGluLysAlaAsnAla-488 |
| SEQ. ID. NO. 1977 | 503-AlaProAsnArgValAsnLeu-509 |
| SEQ. ID. NO. 1978 | 511-LeuThrGlnGluArgTrpProAspIleVal-520 |
| SEQ. ID. NO. 1979 | 523-GluThrArgGluHisSerVal-529 |
| Hydrophilic Regions- Hopp-Woods | |
| SEQ. ID. NO. 1980 | 4-GluIleLeuAspGlnValArgArgArgArgThr-14 |
| SEQ. ID. NO. 1981 | 21-ProAspAlaGlyLys-25 |
| SEQ. ID. NO. 1982 | 43-GlyThrValLysGlyLysLysThrGlyLys-52 |
| SEQ. ID. NO. 1983 | 59-MetGluIleGluLysGlnArgGly-66 |
| SEQ. ID. NO. 1984 | 77-AspTyrLysAspHisThr-82 |
| SEQ. ID. NO. 1985 | 92-GlnAspPheSerGluAspThrTyr-99 |
| SEQ. ID. NO. 1986 | 113-AspAlaAlaLysGlyValGlu-119 |
| SEQ. ID. NO. 1987 | 129-CysArgLeuArgAspThrPro-135 |
| SEQ. ID. NO. 1988 | 142-LysTyrAspArgGluValArgAspSerLeuGluLeuLeuAspGluValGluAsn-159 |
| SEQ. ID. NO. 1989 | 194-AlaGlyGlyGluArgLeuProHis-201 |

TABLE 1-continued

| | |
|---|---|
| SEQ. ID. NO. 1990 | 207-LysGlyIleAspAsnProGluLeuGluGlnArgPheProLeu-220 |
| SEQ. ID. NO. 1991 | 223-GlnGlnLeuArgAspGluIleGluLeu-231 |
| SEQ. ID. NO. 1992 | 277-ProLysProArgAspAlaThrValArgMetValGluProAspGluProLysPhe-294 |
| SEQ. ID. NO. 1993 | 305-MetAspProLysHisArgAspArgIleAla-314 |
| SEQ. ID. NO. 1994 | 319-CysSerGlyLysPheGluArgGlyMetLysMetLysHisLeuArgIleAsnArgGluIleAla-339 |
| SEQ. ID. NO. 1995 | 348-SerHisAspArgGluLeuValGlu-355 |
| SEQ. ID. NO. 1996 | 376-SerPheSerGluGlyGluGln-382 |
| SEQ. ID. NO. 1997 | 399-ValArgIleLysAsnProLeuLysIleLysGlnLeuGlnLysGlyLeu-414 |
| SEQ. ID. NO. 1998 | 417-LeuGlyGluGluGlyAla-422 |
| SEQ. ID. NO. 1999 | 473-SerCysAspAspLysLysLysLeuAlaGluPheGluLysAlaAsnAla-488 |
| SEQ. ID. NO. 2000 | 512-ThrGlnGluArgTrpPro-517 |
| SEQ. ID. NO. 2001 | 523-GluThrArgGluHisSerVal-529 |
| 135 | |
| AMPHI Regions - AMPHI | |
| SEQ. ID. NO. 2002 | 85-GluTyrThrAlaAsnLeu-90 |
| SEQ. ID. NO. 2003 | 169-AspIleAspGlyLeuTyrThr-175 |
| SEQ. ID. NO. 2004 | 185-ValArgLeuAspLysIleGluHis-192 |
| SEQ. ID. NO. 2005 | 212-GlyMetLeuThrLysIle-217 |
| SEQ. ID. NO. 2006 | 236-LeuLysProAspAla-240 |
| SEQ. ID. NO. 2007 | 242-AlaGluAlaAlaGlu-246 |
| SEQ. ID. NO. 2008 | 284-AlaGluHisAlaLeuSer-289 |
| SEQ. ID. NO. 2009 | 300-IleAlaGlyIleGluGly-305 |
| SEQ. ID. NO. 2010 | 308-SerArgMetAspThrValThrValTyr-316 |
| SEQ. ID. NO. 2011 | 318-LysAlaThrLysGlnPro-323 |
| Antigenic Index - Jameson-Wolf | |
| SEQ. ID. NO. 2012 | 1-MetLysTyrLysArgIleVal-7 |
| SEQ. ID. NO. 2013 | 11-GlyThrSerSerIleThrHisSerAspGlySerLeuSerArgGlyLysIleGlnThr-29 |
| SEQ. ID. NO. 2014 | 60-GlyPheLysLysArgProValLysIleAlaAspLysGlnAlaSer-74 |
| SEQ. ID. NO. 2015 | 90-LeuSerSerAspGlyIle-95 |
| SEQ. ID. NO. 2016 | 105-AlaAspPheAlaAspLysArgArgTyrGlnAsnAlaGlyGly-118 |
| SEQ. ID. NO. 2017 | 124-LeuGlnArgArgAlaVal-129 |
| SEQ. ID. NO. 2018 | 132-IleAsnGluAsnAspThrValSerValGluGluLeuLysIleGlyAspAsnAspThrLeu-151 |
| SEQ. ID. NO. 2019 | 176-GlyAsnProAsnSerAsnProAspAlaValArgLeuAspLysIleGluHisIleAsn-194 |
| SEQ. ID. NO. 2020 | 202-GlyGlySerGlySerAlaAsnGlyThrGly-211 |
| SEQ. ID. NO. 2021 | 215-ThrLysIleLysAla-219 |
| SEQ. ID. NO. 2022 | 224-AlaGluSerGlyVal-228 |
| SEQ. ID. NO. 2023 | 233-CysSerSerLeuLysProAspAlaLeuAlaGluAlaAlaGluHisGlnAlaAspGly-251 |
| SEQ. ID. NO. 2024 | 257-ArgAlaLysGlyLeuArgThrGlnLysGln-266 |
| SEQ. ID. NO. 2025 | 271-TyrSerGluSerArgGlySerValTyrValAspGluGlyAlaGluHisAlaLeuSerGluGlnGlyLysSerLeuLeu-296 |
| SEQ. ID. NO. 2026 | 305-GlyHisPheSerArgMetAspThr-312 |
| SEQ. ID. NO. 2027 | 317-SerLysAlaThrLysGlnProLeuGlyLysGlyArgVal-329 |
| SEQ. ID. NO. 2028 | 335-AlaAlaGluAspLeuLeuLysSerArgLysAlaLys-346 |
| SEQ. ID. NO. 2029 | 350-IleHisArgAspAspTrpIleSer-357 |
| Hydrophilic Regions - Hopp-Woods | |
| SEQ. ID. NO. 2030 | 1-MetLysTyrLysArgIleVal-7 |
| SEQ. ID. NO. 2031 | 16-ThrHisSerAspGlySerLeuSerArgGlyLysIle-27 |
| SEQ. ID. NO. 2032 | 60-GlyPheLysLysArgProValLysIleAlaAspLysGlnAlaSer-74 |
| SEQ. ID. NO. 2033 | 105-AlaAspPheAlaAspLysArgArgTyrGlnAsn-115 |
| SEQ. ID. NO. 2034 | 124-LeuGlnArgArgAlaVal-129 |
| SEQ. ID. NO. 2035 | 133-AsnGluAsnAspThrValSerValGluGluLeuLysIleGlyAspAsnAspThrLeu-151 |
| SEQ. ID. NO. 2036 | 178-ProAsnSerAsnProAspAlaValArgLeuAspLysIleGluHisIleAsn-194 |
| SEQ. ID. NO. 2037 | 215-ThrLysIleLysAla-219 |
| SEQ. ID. NO. 2038 | 236-LeuLysProAspAlaLeuAlaGluAlaAlaGluHisGlnAlaAsp-250 |
| SEQ. ID. NO. 2039 | 257-ArgAlaLysGlyLeuArgThrGlnLys-265 |
| SEQ. ID. NO. 2040 | 272-SerGluSerArgGly-276 |
| SEQ. ID. NO. 2041 | 278-ValTyrValAspGluGlyAlaGluHisAlaLeuSerGluGlnGlyLys-293 |
| SEQ. ID. NO. 2042 | 306-HisPheSerArgMetAspThr-312 |
| SEQ. ID. NO. 2043 | 318-LysAlaThrLysGlnProLeuGlyLysGlyArgVal-329 |
| SEQ. ID. NO. 2044 | 335-AlaAlaGluAspLeuLeuLysSerArgLysAlaLys-346 |
| SEQ. ID. NO. 2045 | 351-HisArgAspAspTrp-355 |
| 136 | |
| AMPHI Regions - AMPHI | |
| SEQ. ID. NO. 2046 | 37-LeuArgPheValAspAspCysLeuPro-45 |
| SEQ. ID. NO. 2047 | 50-IleArgGlnCysIleArgGln-56 |
| SEQ. ID. NO. 2048 | 84-GlnCysHisAspGlyIleLysGlnLeuPheLysArgPheIleIleAspGlyPheLysProIleGlyArgHis-107 |
| SEQ. ID. NO. 2049 | 119-CysValLysIleAla-123 |
| SEQ. ID. NO. 2050 | 148-ArgHisCysGlnAsn-152 |
| SEQ. ID. NO. 2051 | 170-GlnHisPheGlyGlnPro-175 |
| SEQ. ID. NO. 2052 | 177-GluArgCysGlnPheVal-182 |
| SEQ. ID. NO. 2053 | 194-AsnLeuValAlaThr-198 |
| SEQ. ID. NO. 2054 | 210-GlnPheAlaGlnPro-214 |
| SEQ. ID. NO. 2055 | 216-PheGlyCysPheGlyLysPheSerGlyIleHis-226 * |
| Antigenic Index - Jameson-Wolf | |
| SEQ. ID. NO. 2056 | 1-MetGluThrAsnAla-5 |
| SEQ. ID. NO. 2057 | 38-ArgPheValAspAspCysLeu-44 |
| SEQ. ID. NO. 2058 | 48-ValAspIleArgGlnCysIle-54 |
| SEQ. ID. NO. 2059 | 69-LeuGlnThrAspSer-73 |
| SEQ. ID. NO. 2060 | 84-GlnCysHisAspGlyIleLysGlnLeuPhe-93 |
| SEQ. ID. NO. 2061 | 99-AspGlyPheLysProIleGlyArgHisAsnIle-109 |
| SEQ. ID. NO. 2062 | 139-IleArgHisArgGlyGlyCysPheHisArgHisCysGlnAsnGlnProPheAsp-156 |

TABLE 1-continued

| | |
|---|---|
| SEQ. ID. NO. 2063 | 159-ThrPheGlyGlyGlyLysLeuArg-166 |
| SEQ. ID. NO. 2064 | 171-HisPheGlyGlnProValGluArg-178 |
| SEQ. ID. NO. 2065 | 184-ProAlaGlnGlnArgArgHisLysThr-192 |
| SEQ. ID. NO. 2066 | 214-ProProPheGlyCysPheGlyLysPheSerGly-224 |
| SEQ. ID. NO. 2067 | 236-ProTyrTyrArgArgAsnAlaVal-243 |
| Hydrophilic Regions - Hopp-Woods | |
| SEQ. ID. NO. 2068 | 48-ValAspIleArgGlnCysIle-54 |
| SEQ. ID. NO. 2069 | 87-AspGlyIleLysGlnLeuPhe-93 |
| SEQ. ID. NO. 2070 | 185-AlaGlnGlnArgArgHisLysThr-192 |
| 137 | |
| AMPHI Regions - AMPHI | |
| SEQ. ID. NO. 2071 | 24-LeuSerTyrIleLeuGlyPhe-30 |
| SEQ. ID. NO. 2072 | 49-ThrLysGluSerLeu-53 |
| SEQ. ID. NO. 2073 | 55-AspPheLeuThrTrpGly-60 |
| SEQ. ID. NO. 2074 | 78-PheSerAspTyrLeuAlaHisProLeuAspIlePheLysValTrpGluGlyGly-95 |
| SEQ. ID. NO. 2075 | 120-PheLeuLysLeuMetAspThrValAlaProLeuValPro-132 |
| SEQ. ID. NO. 2076 | 139-ArgIleGlyAsnPheIle-144 |
| SEQ. ID. NO. 2077 | 149-TrpGlyArgValThrAspIleAsnAlaPhe-158 |
| SEQ. ID. NO. 2078 | 178-ProLeuTrpAlaGluTrpLeuGlnGlnTyr-187 |
| SEQ. ID. NO. 2079 | 190-LeuProArgHisProSerGlnLeu-197 |
| SEQ. ID. NO. 2080 | 232-TyrGlyIlePheArgPheIleAlaGluPheAlaArgGlnProAspAspTyrLeuGly-250 |
| Antigenic Index - Jameson-Wolf | |
| SEQ. ID. NO. 2081 | 36-LeuGlyArgArgArgIleAlaGln-43 |
| SEQ. ID. NO. 2082 | 48-PheThrLysGluSerLeuAspAsp-55 |
| SEQ. ID. NO. 2083 | 92-TrpGluGlyGlyMet-96 |
| SEQ. ID. NO. 2084 | 111-LeuPheGlyArgLysHisGly-117 |
| SEQ. ID. NO. 2085 | 136-AlaSerGlyArgIle-140 |
| SEQ. ID. NO. 2086 | 164-ProGlnAlaArgTyrGluAspAlaGluAlaAlaAla-175 |
| SEQ. ID. NO. 2087 | 191-ProArgHisProSerGlnLeu-197 |
| SEQ. ID. NO. 2088 | 214-PheSerLysLysGlnArgSerThrGlyGln-223 |
| SEQ. ID. NO. 2089 | 241-PheAlaArgGlnProAspAspTyrLeu-249 |
| SEQ. ID. NO. 2090 | 277-PheGlyMetLysLysGlnHis-283 |
| Hydrophilic Regions - Hopp-Woods | |
| SEQ. ID. NO. 2091 | 37-GlyArgArgArgIleAla-42 |
| SEQ. ID. NO. 2092 | 48-PheThrLysGluSerLeuAsp-54 |
| SEQ. ID. NO. 2093 | 112-PheGlyArgLysHisGly-117 |
| SEQ. ID. NO. 2094 | 166-AlaArgTyrGluAspAlaGluAlaAlaAla-175 |
| SEQ. ID. NO. 2095 | 216-LysLysGlnArgSerThrGly-222 |
| SEQ. ID. NO. 2096 | 241-PheAlaArgGlnProAspAspTyr-248 |
| SEQ. ID. NO. 2097 | 278-GlyMetLysLysGlnHis-283 |
| 138 | |
| AMPHI Regions - AMPHI | |
| SEQ. ID. NO. 2098 | 21-ProTyrIleArgArgPheSerGlySer-29 |
| SEQ. ID. NO. 2099 | 74-AsnAlaMetLeuGluLysVal-80 |
| SEQ. ID. NO. 2100 | 85-GluPheValGlnGlyMet-90 |
| SEQ. ID. NO. 2101 | 109-ValAsnLysGluIleValSerMetIleAsnThrTyrGly-121 |
| SEQ. ID. NO. 2102 | 152-IleGlyGlnValGlyThrValGluSerIle-161 |
| SEQ. ID. NO. 2103 | 163-ThrGlyLeuValLysGlyLeu-169 |
| SEQ. ID. NO. 2104 | 199-GlyLysLeuAlaGluGluLeu-205 |
| SEQ. ID. NO. 2105 | 213-MetThrAsnIleAlaGlyValMetAspLysThrGlyAsnLeuLeuThrLysLeuThr-231 |
| SEQ. ID. NO. 2106 | 234-ArgIleAspGluLeuIle-239 |
| SEQ. ID. NO. 2107 | 247-GlyMetLeuProLysIleAlaSerAlaValGluAlaAlaValAsn-261 |
| SEQ. ID. NO. 2108 | 276-AlaLeuLeuLeuGluIlePheThrAspAla-285 |
| Antigenic Index - Jameson-Wolf | |
| SEQ. ID. NO. 2109 | 1-MetGluSerGluAsnIle-6 |
| SEQ. ID. NO. 2110 | 9-AlaAlaAspLysAlaArgIleLeu-16 |
| SEQ. ID. NO. 2111 | 23-IleArgArgPheSerGlySer-29 |
| SEQ. ID. NO. 2112 | 35-TyrGlyGlyAsnAlaMetThr-41 |
| SEQ. ID. NO. 2113 | 43-ProAlaLeuLysGluGlyPheAla-50 |
| SEQ. ID. NO. 2114 | 68-GlyGlyGlyProGln-72 |
| SEQ. ID. NO. 2115 | 76-MetLeuGluLysValGlyLysLysGlyGluPhe-86 |
| SEQ. ID. NO. 2116 | 91-ArgValThrAspLysGluAlaMetAsp-99 |
| SEQ. ID. NO. 2117 | 109-ValAsnLysGluIle-113 |
| SEQ. ID. NO. 2118 | 128-SerGlyArgAspAspHisPheIleLysAlaLysLysLeuLeuIleAspThrProGluGlnAsnGlyValAspIleGlyGln-154 |
| SEQ. ID. NO. 2119 | 159-GluSerIleAspThrGlyLeu-165 |
| SEQ. ID. NO. 2120 | 169-LeuIleGluArgGlyCysIle-175 |
| SEQ. ID. NO. 2121 | 182-GlyValGlyGluLysGlyGluAla-189 |
| SEQ. ID. NO. 2122 | 200-LysLeuAlaGluGluLeuAsnAlaGluLys-209 |
| SEQ. ID. NO. 2123 | 219-ValMetAspLysThrGlyAsnLeuLeuThrLysLeuThrProLysArgIleAspGluLeuIleAla-240 |
| SEQ. ID. NO. 2124 | 259-AlaValAsnGlyValLys-264 |
| SEQ. ID. NO. 2125 | 269-IleAspGlyArgLeuProAsnAla-276 |
| SEQ. ID. NO. 2126 | 292-LeuGlyGlyGlyGluAspAla-298 |
| Hydrophilic Regions - Hopp-Woods | |
| SEQ. ID. NO. 2127 | 1-MetGluSerGluAsn-5 |
| SEQ. ID. NO. 2128 | 9-AlaAlaAspLysAlaArgIleLeu-16 |
| SEQ. ID. NO. 2129 | 43-ProAlaLeuLysGluGlyPheAla-50 |
| SEQ. ID. NO. 2130 | 76-MetLeuGluLysValGlyLysLysGlyGluPhe-86 |
| SEQ. ID. NO. 2131 | 91-ArgValThrAspLysGluAlaMetAsp-99 |
| SEQ. ID. NO. 2132 | 109-ValAsnLysGluIle-113 |
| SEQ. ID. NO. 2133 | 128-SerGlyArgAspAspHisPheIleLysAlaLysLysLeuLeuIleAspThrProGluGlnAsnGlyValAsp-151 |

TABLE 1-continued

| | |
|---|---|
| SEQ. ID. NO. 2134 | 183-ValGlyGluLysGlyGluAla-189 |
| SEQ. ID. NO. 2135 | 200-LysLeuAlaGluGluLeuAsnAlaGluLys-209 |
| SEQ. ID. NO. 2136 | 219-ValMetAspLysThrGly-224 |
| SEQ. ID. NO. 2137 | 230-LeuThrProLysArgIleAspGluLeuIleAla-240 |
| SEQ. ID. NO. 2138 | 269-IleAspGlyArgLeu-273 |
| SEQ. ID. NO. 2139 | 294-GlyGlyGluAspAla-298 |
| 140-2 | |
| AMPHI Regions - AMPHI | |
| SEQ. ID. NO. 2140 | 23-ThrThrLeuSerAlaCysLeuGly-30 |
| SEQ. ID. NO. 2141 | 105-AspPheProAsnProAsnAspAlaTyrLysAsnLeuIle-117 |
| SEQ. ID. NO. 2142 | 139-ThrGlyGluSerValGlySerIleSerPhePro-149 |
| SEQ. ID. NO. 2143 | 201-AspIleArgHisValLysGluIleGlyHisIleAspLeuValSer-215 |
| SEQ. ID. NO. 2144 | 253-AlaAlaIleArgAsnAlaTrpValLysLeuGly-263 |
| SEQ. ID. NO. 2145 | 266-GlyValArgIleVal-270 |
| SEQ. ID. NO. 2146 | 282-ThrAlaAspLeuPheGlnIle-288 |
| SEQ. ID. NO. 2147 | 311-GlyIleArgLeuMetGlnGlnSerAsp-319 |
| SEQ. ID. NO. 2148 | 370-AspArgSerGlyGluLysPheLysArgGluMetTyr-381 |
| SEQ. ID. NO. 2149 | 415-ThrArgThrAsnPro-419 |
| SEQ. ID. NO. 2150 | 458-ThrAlaGlnAspIle-462 |
| SEQ. ID. NO. 2151 | 476-LeuAspAlaGlyLysAlaMetAsnGlyPro-485 |
| SEQ. ID. NO. 2152 | 608-TyrThrArgLeuGlyLysLeuLeuLys-616 |
| SEQ. ID. NO. 2153 | 673-SerLeuAspSerValGluLysThrAlaGly-682 |
| SEQ. ID. NO. 2154 | 696-AsnAlaAlaArgThrAlaSer-702 |
| SEQ. ID. NO. 2155 | 736-SerAlaThrProGluThrValGluThrAlaAla-746 |
| SEQ. ID. NO. 2156 | 763-ArgAlaAlaAlaAlaValGlnHisAlaAsnAlaAlaAspGlyValArgIlePheAsnSerLeuAlaAlaThr-786 |
| SEQ. ID. NO. 2157 | 803-LeuLysAlaValSerAspGlyLeuAsp-811 |
| SEQ. ID. NO. 2158 | 817-LeuArgValIleAlaGln-822 |
| SEQ. ID. NO. 2159 | 882-SerLeuPheAlaGly-886 |
| SEQ. ID. NO. 2160 | 894-IleGlyTyrLeuLysGlyLeuPheSerTyr-903 |
| SEQ. ID. NO. 2161 | 918-GluHisAlaGluGlySer-923 |
| SEQ. ID. NO. 2162 | 931-LeuGlyAlaLeuGly-935 |
| SEQ. ID. NO. 2163 | 980-GlyThrLeuValGlyLeu-985 |
| SEQ. ID. NO. 2164 | 1019-GlyGlyPheThrGlyAlaThr-1025 |
| SEQ. ID. NO. 2165 | 1040-ArgLeuValAlaGlyLeu-1045 |
| SEQ. ID. NO. 2166 | 1053-AsnGlyTrpAsnGlyLeuAlaArg-1060 |
| Antigenic Index -Jameson-Wolf | |
| SEQ. ID. NO. 2167 | 1-MetArgThrThrPro-5 |
| SEQ. ID. NO. 2168 | 7-PheProThrLysThrPheLysProThr-15 |
| SEQ. ID. NO. 2169 | 30-GlyGlyGlyGlyGlyGlyThrSerAlaProAspPheAsnAlaGlyGlyThrGlyIleGlySerAsnSerArgAlaThrThrAlaLys-58 |
| SEQ. ID. NO. 2170 | 67-IleLysAsnGluMetCysLysAspArgSerMet-77 |
| SEQ. ID. NO. 2171 | 79-CysAlaGlyArgAspAspValAlaValThrAspArgAspAlaLysIleAsnAlaProProProAsnLeuHisThrGlyAspPheProAsnProAsnAsp AlaTyrLysAsn-115 |
| SEQ. ID. NO. 2172 | 127-TyrThrGlyArgGlyValGlu-133 |
| SEQ. ID. NO. 2173 | 138-AspThrGlyGluSerValGlySerIleSerPhe-148 |
| SEQ. ID. NO. 2174 | 151-LeuTyrGlyArgLysGluHisGlyTyrAsnGluAsnTyrLysAsn-165 |
| SEQ. ID. NO. 2175 | 170-MetArgLysGluAlaProGluAspGlyGlyGlyLysAspIleGluAlaSerPheAspAspGluAlaValIleGluThrGluAlaLysProThrAspIle ArgHisValLysGluIleGlyHis-210 |
| SEQ. ID. NO. 2176 | 220-GlyArgSerValAspGlyArgProAlaGlyGlyIleAlaProAspAla-235 |
| SEQ. ID. NO. 2177 | 241-AsnThrAsnAspGluThrLysAsnGluMet-250 |
| SEQ. ID. NO. 2178 | 262-LeuGlyGluArgGlyValArg-268 |
| SEQ. ID. NO. 2179 | 272-AsnSerPheGlyThrThrSerArgAlaGlyThrAlaAsp-284 |
| SEQ. ID. NO. 2180 | 288-IleAlaAsnSerGluGluGlnTyrArg-296 |
| SEQ. ID. NO. 2181 | 301-AspTyrSerGlyGlyAspLysThrAspGluGlyIleArg-313 |
| SEQ. ID. NO. 2182 | 315-MetGlnGlnSerAspTyrGlyAsn-322 |
| SEQ. ID. NO. 2183 | 327-IleArgAsnLysAsnMet-332 |
| SEQ. ID. NO. 2184 | 337-SerThrGlyAsnAspAlaGlnAlaGlnProAsnThr-348 |
| SEQ. ID. NO. 2185 | 355-TyrGluLysAspAlaGlnLys-361 |
| SEQ. ID. NO. 2186 | 368-GlyValAspArgSerGlyGluLysPheLysArgGluMetTyrGlyGluProGlyThrGluProLeuGluTyrGlySerAsnHis-395 |
| SEQ. ID. NO. 2187 | 412-ValArgPheThrArgThrAsnPro-419 |
| SEQ. ID. NO. 2188 | 446-MetSerAsnAspAsnLeuArgThr-453 |
| SEQ. ID. NO. 2189 | 467-ValAspSerLysPheGly-472 |
| SEQ. ID. NO. 2190 | 477-AspAlaGlyLysAlaMetAsnGlyProAla-486 |
| SEQ. ID. NO. 2191 | 492-AspPheThrAlaAspThrLysGlyThrSer-501 |
| SEQ. ID. NO. 2192 | 506-SerPheArgAsnAspIleSerGlyThr-514 |
| SEQ. ID. NO. 2193 | 516-GlyLeuIleLysLysGlyGlySerGln-524 |
| SEQ. ID. NO. 2194 | 529-GlyAsnAsnThrTyrThrGlyLysThrIleIleGluGlyGlySer-543 |
| SEQ. ID. NO. 2195 | 548-GlyAsnAsnLysSerAspMetArgValGluThrLysGly-560 |
| SEQ. ID. NO. 2196 | 568-AlaSerGlyGlySerLeuAsnSerAspGly-577 |
| SEQ. ID. NO. 2197 | 582-AlaAspThrAspGlnSerGlyAlaAsnGlu-591 |
| SEQ. ID. NO. 2198 | 593-ValHisIleLysGlySerLeuGlnLeuAspGlyLysGlyThrLeu-607 |
| SEQ. ID. NO. 2199 | 615-LeuLysValAspGly-619 |
| SEQ. ID. NO. 2200 | 629-MetSerAlaArgGlyLysGlyAlaGly-637 |
| SEQ. ID. NO. 2201 | 640-AsnSerThrGlyArgArgValPro-647 |
| SEQ. ID. NO. 2202 | 653-LysIleGlyGlnAspTyr-658 |
| SEQ. ID. NO. 2203 | 663-AsnIleGluThrAspGlyGlyLeu-670 |
| SEQ. ID. NO. 2204 | 675-AspSerValGluLysThrAlaGlySerGluGlyAspThrLeu-688 |
| SEQ. ID. NO. 2205 | 691-TyrValArgArgGlyAsnAlaAlaArgThrAlaSer-702 |
| SEQ. ID. NO. 2206 | 714-HisAlaValGluGlnGlyGlySerAsnLeuGlu-724 |
| SEQ. ID. NO. 2207 | 730-LeuAspAlaSerGluSerSerAlaThrProGluThrValGlu-743 |
| SEQ. ID. NO. 2208 | 745-AlaAlaAlaAspArgThrAspMetProGlyIleArgProTyrGly-759 |

TABLE 1-continued

| | |
|---|---|
| SEQ. ID. NO. 2209 | 772-AsnAlaAlaAspGly-776 |
| SEQ. ID. NO. 2210 | 788-TyrAlaAspSerThrAlaAla-794 |
| SEQ. ID. NO. 2211 | 797-AspMetGlnGlyArgArgLeuLysAlaValSerAspGlyLeuAspHisAsnGlyThrGlyLeu-817 |
| SEQ. ID. NO. 2212 | 823-ThrGlnGlnAspGlyGlyThrTrpGluGlnGlyGlyValGluGlyLysMetArgGlySerThrGln-844 |
| SEQ. ID. NO. 2213 | 849-AlaAlaLysThrGlyGluAsnThrThr-857 |
| SEQ. ID. NO. 2214 | 863-GlyMetGlyArgSerThrTrpSerGluAsnSerAlaAsnAlaLysThrAspSerIle-881 |
| SEQ. ID. NO. 2215 | 887-IleArgHisAspAlaGlyAsp-893 |
| SEQ. ID. NO. 2216 | 902-SerTyrGlyArgTyrLysAsnSerIleSerArgSerThrGlyAlaAspGluHisAlaGluGlySerValAsn-925 |
| SEQ. ID. NO. 2217 | 943-AlaThrGlyAspLeuThrValGluGlyGlyLeuArg-954 |
| SEQ. ID. NO. 2218 | 961-AspAlaPheAlaGluLysGlySerAlaLeuGlyTrpSerGlyAsnSerLeuThrGluGlyThr-981 |
| SEQ. ID. NO. 2219 | 990-LeuSerGlnProLeuSerAspLys-997 |
| SEQ. ID. NO. 2220 | 1005-GlyValGluArgAspLeuAsnGlyArgAspTyrThrVal-1017 |
| SEQ. ID. NO. 2221 | 1027-AlaThrGlyLysThrGlyAlaArgAsnMetProHisThr-1039 |
| SEQ. ID. NO. 2222 | 1049-ValGluPheGlyAsnGlyTrp-1055 |
| SEQ. ID. NO. 2223 | 1062-SerTyrAlaGlySerLysGlnTyrGlyAsnHisSerGlyArgValGlyVal-1078 |
| Hydrophilic Regions- Hopp-Woods | |
| SEQ. ID. NO. 2224 | 50-SerAsnSerArgAlaThrThrAlaLys-58 |
| SEQ. ID. NO. 2225 | 67-IleLysAsnGluMetCysLysAspArgSerMet-77 |
| SEQ. ID. NO. 2226 | 80-AlaGlyArgAspAspValAlaValThrAspArgAspAlaLysIleAsnAla-96 |
| SEQ. ID. NO. 2227 | 106-PheProAsnProAsnAspAlaTyr-113 |
| SEQ. ID. NO. 2228 | 138-AspThrGlyGluSerValGly-144 |
| SEQ. ID. NO. 2229 | 152-TyrGlyArgLysGluHisGlyTyr-159 |
| SEQ. ID. NO. 2230 | 170-MetArgLysGluAlaProGluAspGlyGlyGlyLysAspIleGluAlaSerPheAspAspGluAlaValIleGluThrGluAlaLysProThrAsp IleArgHisValLysGluIleGlyHis-210 |
| SEQ. ID. NO. 2231 | 221-ArgSerValAspGlyArgProAlaGly-229 |
| SEQ. ID. NO. 2232 | 242-ThrAsnAspGluThrLysAsnGluMet-250 |
| SEQ. ID. NO. 2233 | 262-LeuGlyGluArgGlyValArg-268 |
| SEQ. ID. NO. 2234 | 278-SerArgAlaGlyThr-282 |
| SEQ. ID. NO. 2235 | 290-AsnSerGluGluGlnTyrArg-296 |
| SEQ. ID. NO. 2236 | 303-SerGlyGlyAspLysThrAspGluGlyIleArg-313 |
| SEQ. ID. NO. 2237 | 327-IleArgAsnLysAsn-331 |
| SEQ. ID. NO. 2238 | 339-GlyAsnAspAlaGlnAla-344 |
| SEQ. ID. NO. 2239 | 355-TyrGluLysAspAlaGlnLys-361 |
| SEQ. ID. NO. 2240 | 368-GlyValAspArgSerGlyGluLysPheLysArgGluMetTyrGly-382 |
| SEQ. ID. NO. 2241 | 384-ProGlyThrGluProLeuGlu-390 |
| SEQ. ID. NO. 2242 | 412-ValArgPheThrArg-416 |
| SEQ. ID. NO. 2243 | 477-AspAlaGlyLysAlaMetAsn-483 |
| SEQ. ID. NO. 2244 | 493-PheThrAlaAspThrLysGlyThrSer-501 |
| SEQ. ID. NO. 2245 | 509-AsnAspIleSerGly-513 |
| SEQ. ID. NO. 2246 | 517-LeuIleLysLysGlyGlySer-523 |
| SEQ. ID. NO. 2247 | 550-AsnLysSerAspMetArgValGluThrLysGly-560 |
| SEQ. ID. NO. 2248 | 583-AspThrAspGlnSerGlyAlaAsnGlu-591 |
| SEQ. ID. NO. 2249 | 601-LeuAspGlyLysGly-605 |
| SEQ. ID. NO. 2250 | 615-LeuLysValAspGly-619 |
| SEQ. ID. NO. 2251 | 631-AlaArgGlyLysGly-635 |
| SEQ. ID. NO. 2252 | 642-ThrGlyArgArgValPro-647 |
| SEQ. ID. NO. 2253 | 664-IleGluThrAspGly-668 |
| SEQ. ID. NO. 2254 | 675-AspSerValGluLysThrAlaGlySerGluGlyAspThr-687 |
| SEQ. ID. NO. 2255 | 692-ValArgArgGlyAsnAlaAlaArgThrAlaSer-702 |
| SEQ. ID. NO. 2256 | 714-HisAlaValGluGlnGlyGlySerAsnLeu-723 |
| SEQ. ID. NO. 2257 | 730-LeuAspAlaSerGluSerSerAlaThrProGluThrValGlu-743 |
| SEQ. ID. NO. 2258 | 745-AlaAlaAlaAspArgThrAspMetProGly-754 |
| SEQ. ID. NO. 2259 | 772-AsnAlaAlaAspGly-776 |
| SEQ. ID. NO. 2260 | 797-AspMetGlnGlyArgArgLeuLysAlaValSerAspGlyLeuAspHisAsnGlyThr-815 |
| SEQ. ID. NO. 2261 | 833-GlyGlyValGluGlyLysMetArgGlySerThr-843 |
| SEQ. ID. NO. 2262 | 851-LysThrGlyGluAsnThrThr-857 |
| SEQ. ID. NO. 2263 | 872-AsnSerAlaAsnAlaLysThrAspSer-880 |
| SEQ. ID. NO. 2264 | 887-IleArgHisAspAlaGlyAsp-893 |
| SEQ. ID. NO. 2265 | 905-ArgTyrLysAsnSerIleSerArgSerThrGlyAlaAspGluHisAlaGluGlySerVal-924 |
| SEQ. ID. NO. 2266 | 961-AspAlaPheAlaGluLysGlySer-968 |
| SEQ. ID. NO. 2267 | 992-GlnProLeuSerAspLys-997 |
| SEQ. ID. NO. 2268 | 1005-GlyValGluArgAspLeuAsnGlyArgAspTyrThr-1016 |
| SEQ. ID. NO. 2269 | 1027-AlaThrGlyLysThrGlyAlaArgAsnMetPro-1037 |
| 141 | |
| AMPHIRegions- AMPHI | |
| SEQ. ID. NO. 2270 | 11-GlnSerSerThrMetArgProIleGlyGluIle-21 |
| SEQ. ID. NO. 2271 | 44-ProAlaGluAlaPheLysLeuPro-51 |
| SEQ. ID. NO. 2272 | 80-AlaAspAlaLeuArgHisIle-86 |
| SEQ. ID. NO. 2273 | 131-PheHisAlaIleGlyAla-136 |
| SEQ. ID. NO. 2274 | 139-AsnLeuLeuAlaAlaMetLeuAspAsn-147 |
| SEQ. ID. NO. 2275 | 174-GlnLeuArgAsnIleIleAspGlyMetGlyLysProValAspGlyValMetArgPro-192 |
| SEQ. ID. NO. 2276 | 212-AspIleSerAspLeuLysGluArgLeuGlyIleLeuVal-225 |
| SEQ. ID. NO. 2277 | 245-MetAlaAlaLeuLeuLysAspAlaIleLysProAsnLeu-257 |
| SEQ. ID. NO. 2278 | 259-GlnThrIleGluGlyThrPro-265 |
| SEQ. ID. NO. 2279 | 272-ProPheAlaAsnIleAlaHisGlyCysAsnSerValThrAlaThrArgLeuAlaLysHisLeuAlaAspTyrAla-296 |
| SEQ. ID. NO. 2280 | 330-AlaThrValArgAla-334 |
| SEQ. ID. NO. 2281 | 351-LeuAspAlaLeuGluLysGlyLeuProAsnLeuLeuLysHisIleSerAsnLeuLysAsnValPheGly-373 |
| SEQ. ID. NO. 2282 | 406-SerLeuThrGluValTrpGlyLys-413 |

TABLE 1-continued

| | |
|---|---|
| SEQ. ID. NO. 2283 | 420-AspLeuAlaArgLysValValAsnAlaIleGluSerGln-432 |
| SEQ. ID. NO. 2284 | 473-IleAlaSerLeuGluLys-478 |
| SEQ. ID. NO. 2285 | 525-ValAlaLeuCysGlyAsnMetMetLysMetProGlyLeuProLysValProAlaAla-543 |
| Antigenic Index - Jameson-Wolf | |
| SEQ. ID. NO. 2286 | 3-PheLysThrAspAlaGluIleAlaGlnSerSerThrMetArgProIleGly-19 |
| SEQ. ID. NO. 2287 | 27-LeuAsnAlaAspAsnIleGluProTyrGly-36 |
| SEQ. ID. NO. 2288 | 38-TyrLysAlaLysIleAsnProAlaGluAlaPheLysLeuProGlnLysGlnGlyArg-56 |
| SEQ. ID. NO. 2289 | 64-AsnProThrProAlaGlyGluGlyLysThrThr-74 |
| SEQ. ID. NO. 2290 | 81-AspAlaLeuArgHisIleGlyLysAspAla-90 |
| SEQ. ID. NO. 2291 | 94-LeuArgGluProSerLeuGlyPro-101 |
| SEQ. ID. NO. 2292 | 105-ValLysGlyGlyAlaAlaGlyGlyGly-113 |
| SEQ. ID. NO. 2293 | 151-GlnGlyAsnGluLeuAsnIleAspProLysArgValLeuTrp-164 |
| SEQ. ID. NO. 2294 | 166-ArgValValAspMetAsnAspArgGlnLeuArgAsnIleIleAspGlyMetGlyLysProValAspGlyValMetArgProAspGlyPheAspIle-197 |
| SEQ. ID. NO. 2295 | 211-LysAspIleSerAspLeuLysGluArgLeuGly-221 |
| SEQ. ID. NO. 2296 | 227-TyrAlaLysAspGlySerProValTyr-235 |
| SEQ. ID. NO. 2297 | 237-LysAspLeuLysAlaAsnGly-243 |
| SEQ. ID. NO. 2298 | 251-AspAlaIleLysProAsnLeu-257 |
| SEQ. ID. NO. 2299 | 287-ArgLeuAlaLysHisLeuAla-293 |
| SEQ. ID. NO. 2300 | 306-LeuGlyAlaGluLysPheCysAspIleLysCysArgLeuAlaGlyLeuLysProAspAla-325 |
| SEQ. ID. NO. 2301 | 335-LeuLysTyrAsnGlyGlyValGluArgAlaAsnLeuGlyGluGluAsnLeuAspAlaLeuGluLysGlyLeuProAsnLeu-361 |
| SEQ. ID. NO. 2302 | 383-PheValSerAspAlaAspAlaGluLeuAlaMetIleGluLysAlaCysAla-399 |
| SEQ. ID. NO. 2303 | 411-TrpGlyLysGlyGlyAlaGlyGlyAlaAspLeuAlaArgLysValValAsn-427 |
| SEQ. ID. NO. 2304 | 429-IleGluSerGlnThrAsnAsnPheGly-437 |
| SEQ. ID. NO. 2305 | 444-LeuGlyIleLysAspLysIleArgAlaIleAla-454 |
| SEQ. ID. NO. 2306 | 458-TyrGlyAlaGluAspValAspPheSerAla-467 |
| SEQ. ID. NO. 2307 | 474-AlaSerLeuGluLysLeuGlyLeuAspLysMetPro-485 |
| SEQ. ID. NO. 2308 | 494-SerLeuSerAspAsnAlaLys-500 |
| SEQ. ID. NO. 2309 | 503-GlyCysProGluAspPheArgIle-510 |
| SEQ. ID. NO. 2310 | 534-MetProGlyLeuPro-538 |
| SEQ. ID. NO. 2311 | 541-ProAlaAlaGluLysIleAspValAspAlaGluGly-552 |
| Hydrophilic Regions- Hopp-Woods | |
| SEQ. ID. NO. 2312 | 3-PheLysThrAspAlaGluIleAlaGln-11 |
| SEQ. ID. NO. 2313 | 38-TyrLysAlaLysIleAsnPro-44 |
| SEQ. ID. NO. 2314 | 46-GluAlaPheLysLeuProGlnLysGlnGlyArg-56 |
| SEQ. ID. NO. 2315 | 67-ProAlaGlyGluGlyLysThr-73 |
| SEQ. ID. NO. 2316 | 81-AspAlaLeuArgHisIleGlyLysAspAla-90 |
| SEQ. ID. NO. 2317 | 94-LeuArgGluProSer-98 |
| SEQ. ID. NO. 2318 | 155-LeuAsnIleAspProLysArgValLeuTrp-164 |
| SEQ. ID. NO. 2319 | 166-ArgValValAspMetAsnAspArgGlnLeuArgAsnIleIle-179 |
| SEQ. ID. NO. 2320 | 181-GlyMetGlyLysProValAspGlyValMetArgProAspGlyPhe-195 |
| SEQ. ID. NO. 2321 | 211-LysAspIleSerAspLeuLysGluArgLeuGly-221 |
| SEQ. ID. NO. 2322 | 228-AlaLysAspGlySer-232 |
| SEQ. ID. NO. 2323 | 237-LysAspLeuLysAla-241 |
| SEQ. ID. NO. 2324 | 287-ArgLeuAlaLysHisLeuAla-293 |
| SEQ. ID. NO. 2325 | 306-LeuGlyAlaGluLysPheCysAspIleLysCysArgLeuAlaGlyLeuLysProAspAla-325 |
| SEQ. ID. NO. 2326 | 339-GlyGlyValGluArgAlaAsnLeuGlyGluGluAsnLeuAspAlaLeuGluLysGlyLeu-358 |
| SEQ. ID. NO. 2327 | 383-PheValSerAspAlaAspAlaGluLeuAlaMetIleGluLysAlaCysAla-399 |
| SEQ. ID. NO. 2328 | 420-AspLeuAlaArgLysValValAsn-427 |
| SEQ. ID. NO. 2329 | 444-LeuGlyIleLysAspLysIleArgAlaIleAla-454 |
| SEQ. ID. NO. 2330 | 458-TyrGlyAlaGluAspValAspPheSerAla-467 |
| SEQ. ID. NO. 2331 | 474-AlaSerLeuGluLysLeuGlyLeuAspLysMetPro-485 |
| SEQ. ID. NO. 2332 | 503-GlyCysProGluAspPheArgIle-510 |
| SEQ. ID. NO. 2333 | 541-ProAlaAlaGluLysIleAspValAspAlaGluGly-552 |
| 142-2 | |
| AMPHI Regions - AMPHI | |
| SEQ. ID. NO. 2334 | 26-ArgPheAlaAlaMetProAspValValGlyLys-36 |
| SEQ. ID. NO. 2335 | 44-GlyGlnProGlyLysMetPhe-50 |
| SEQ. ID. NO. 2336 | 100-AlaValThrProCysArg-105 |
| SEQ. ID. NO. 2337 | 107-ValCysArgAspAspMet-112 |
| SEQ. ID. NO. 2338 | 130-PheLeuGlnIleArgHisPheSerProLeu-139 |
| SEQ. ID. NO. 2339 | 174-LeuArgValGlnArgIleLeuAspPheGlyLysPheCysGlnGlnVal-189 |
| SEQ. ID. NO. 2340 | 202-LeuAspSerValValAlaPheValHisPhePheAlaAspPheLeuIle-217 |
| SEQ. ID. NO. 2341 | 239-AlaAspAsnGlnThrArgPhePheLysAlaGly-249 |
| SEQ. ID. NO. 2342 | 259-AsnAlaArgLeuIleArgGlnIleLeuLys-268 |
| Antigenic Index - Jameson-Wolf | |
| SEQ. ID. NO. 2343 | 31-ProAspValValGly-35 |
| SEQ. ID. NO. 2344 | 38-LeuPheGlyArgGlnAlaGlyGlnProGlyLysMet-49 |
| SEQ. ID. NO. 2345 | 59-GlnArgIleAspAlaGluAlaAlaValPheArgGlnAspArgAsnAspSerArgThrProValAspAlaGlnHisHisGlyArgArgLeuValGly AsnArgArgAspArgArgHisCysAsnAla-100 |
| SEQ. ID. NO. 2346 | 102-ThrProCysArgThrValCysArgAspAspMetAsnAlaCysArgAlaArgCysHisArgIleThrGluArgSerLeu-127 |
| SEQ. ID. NO. 2347 | 147-AlaAlaHisLysAlaSerPro-153 |
| SEQ. ID. NO. 2348 | 155-CysSerSerPheAspSerLysSerArgArgSerAspValSerAlaArgTyr-171 |
| SEQ. ID. NO. 2349 | 180-LeuAspPheGlyLysPheCys-186 |
| SEQ. ID. NO. 2350 | 225-GlnLeuGlnLysAsnThrSer-231 |
| SEQ. ID. NO. 2351 | 237-PheGlnAlaAspAsnGlnThrArgPhePheLysAlaGlyGlnAspThrGlyGlnAlaGlyAlaGlnAsn-259 |
| SEQ. ID. NO. 2352 | 267-LeuLysValGlnArgAlaValPheArgGlnLysThrAspAsnProPro-282 |
| SEQ. ID. NO. 2353 | 291-IleGlnAsnArgProGluLeuGlyHisGlnGly-301 |
| SEQ. ID. NO. 2354 | 307-GlnThrAspIleAspArgArgMetPhe-315 |

TABLE 1-continued

Hydrophilic Regions - Hopp-Woods
SEQ. ID. NO. 2355 42-GlnAlaGlyGlnPro-46
SEQ. ID. NO. 2356 59-GlnArgIleAspAlaGluAlaAlaValPheArgGlnAspArgAsnAspSerArgThrProValAspAlaGlnHisHisGlyArgArgLeuValGly AsnArgArgAspArgArgHisCys-98
SEQ. ID. NO. 2357 106-ThrValCysArgAspAspMetAsnAlaCysArgAlaArgCysHisArgIleThrGluArgSerLeu-127
SEQ. ID. NO. 2358 147-AlaAlaHisLysAlaSerPro-153
SEQ. ID. NO. 2359 158-PheAspSerLysSerArgArgSerAspValSerAla-169
SEQ. ID. NO. 2360 237-PheGlnAlaAspAsnGlnThrArgPhePheLysAlaGlyGlnAspThrGlyGln-254
SEQ. ID. NO. 2361 267-LeuLysValGlnArgAlaValPheArgGlnLysThrAspAsn-280
SEQ. ID. NO. 2362 291-IleGlnAsnArgProGluLeuGly-298
SEQ. ID. NO. 2363 309-AspIleAspArgArgMetPhe-315
144-2
AMPHI Regions - AMPHI
SEQ. ID. NO. 2364 36-LeuGlyGlyIleValGlnGluPhe-43
SEQ. ID. NO. 2365 45-ValLeuAlaAspGlyValArg-51
SEQ. ID. NO. 2366 71-IleAsnLysGlnIleGlyArgValAlaGlyArg-81
SEQ. ID. NO. 2367 136-SerAlaAspGlyTyr-140
SEQ. ID. NO. 2368 212-SerAspAspLeuGluValPheAspPheSerArgProLys-224 *
SEQ. ID. NO. 2369 234-ArgArgGluThrGlyArgAlaGlyPhe-242
SEQ. ID. NO. 2370 244-AlaTyrArgValProSerAspIleGlyArgProAlaAla-257
SEQ. ID. NO. 2371 283-ProGlnAspPheAlaArg-288
SEQ. ID. NO. 2372 295-AspAlaLeuAlaThr-299
SEQ. ID. NO. 2373 306-AspSerLeuAsnTrpProGluPheGlyAsn-315
Antigenic Index - Jameson-Wolf
SEQ. ID. NO. 2374 1-MetSerAspThrProAlaThrArgAspPheGlyLeuIleAspGlyArgAla-17
SEQ. ID. NO. 2375 23-LeuSerAsnArgArgGlyThrArg-30
SEQ. ID. NO. 2376 48-AspGlyValArgGlu-52
SEQ. ID. NO. 2377 58-PheAspAspAlaAlaSerTyrAlaAspAsnProPheGlnIleAsn-72
SEQ. ID. NO. 2378 78-ValAlaGlyArgIleArgGlyAlaAla-86
SEQ. ID. NO. 2379 88-AspIleAsnGlyArgThrTyrArgValGluAlaAsnGluGlyArgAsnAlaLeuHisGlyGlySerHis-110
SEQ. ID. NO. 2380 121-AlaAlaAspGlyArgSerValValLeu-129
SEQ. ID. NO. 2381 131-SerArgLeuGlnGlnSerAlaAspGlyTyrProAsnAspLeuAspLeuAspIleSerTyrArgLeuAspGluAspAspArgLeuThrVal-160
SEQ. ID. NO. 2382 199-MetProAlaAspAlaGluLysLeuPro-207
SEQ. ID. NO. 2383 210-ThrValSerAspAspLeuGluValPheAspPheSerArgProLysProLeuAsp-227
SEQ. ID. NO. 2384 232-AlaLeuArgArgGluThrGlyArgAlaGlyPheAspAspAlaTyrArgValProSerAspIleGlyArgPro-255
SEQ. ID. NO. 2385 261-AlaGlyArgArgArgArgIleSerIleTyrSerAspArgAsnGly-275
SEQ. ID. NO. 2386 282-AlaProGlnAspPheAlaArgHisAspAlaGlyVal-293
SEQ. ID. NO. 2387 300-GluAlaGlnThrLeuProAspSerLeuAsnTrpProGlu-312
SEQ. ID. NO. 2388 314-GlyAsnIleArgLeuAsnLysGlyAspThrArgGluAlaThr-327
Hydrophilic Regions - Hopp-Woods
SEQ. ID. NO. 2389 1-MetSerAspThrProAlaThrArgAsp-9
SEQ. ID. NO. 2390 24-SerAsnArgArgGlyThrArg-30
SEQ. ID. NO. 2391 48-AspGlyValArgGlu-52
SEQ. ID. NO. 2392 58-PheAspAspAlaAlaSer-63
SEQ. ID. NO. 2393 78-ValAlaGlyArgIleArgGlyAlaAla-86
SEQ. ID. NO. 2394 89-IleAsnGlyArgThrTyrArgValGluAlaAsnGluGlyArgAsnAlaLeu-105
SEQ. ID. NO. 2395 121-AlaAlaAspGlyArgSerValValLeu-129
SEQ. ID. NO. 2396 131-SerArgLeuGlnGlnSerAlaAspGlyTyrProAsnAspLeuAspLeu-146
SEQ. ID. NO. 2397 150-TyrArgLeuAspGluAspAspArgLeuThrVal-160
SEQ. ID. NO. 2398 199-MetProAlaAspAlaGluLysLeuPro-207
SEQ. ID. NO. 2399 210-ThrValSerAspAspLeuGluVal-217
SEQ. ID. NO. 2400 221-SerArgProLysProLeuAsp-227
SEQ. ID. NO. 2401 232-AlaLeuArgArgGluThrGlyArgAlaGlyPheAspAspAlaTyrArgValProSerAspIleGlyArg-254
SEQ. ID. NO. 2402 261-AlaGlyArgArgArgArgIleSerIleTyrSerAspArgAsnGly-275
SEQ. ID. NO. 2403 285-AspPheAlaArgHisAspAlaGlyVal-293
SEQ. ID. NO. 2404 317-ArgLeuAsnLysGlyAspThrArgGluAlaThr-327
146
AMPHI Regions - AMPHI
SEQ. ID. NO. 2405 19-LysGlnTyrGlyLeuLeuAspPheMetProCys-29
SEQ. ID. NO. 2406 24-ProLeuAspAsnPheProThrVal-41
SEQ. ID. NO. 2407 69-ValAlaAsnLeuArgArg-74
SEQ. ID. NO. 2408 95-LeuArgAlaCysAlaValIleValAlaLysTyrValGlyValPheGlnLys-111
SEQ. ID. NO. 2409 140-AlaArgArgValArg-144
SEQ. ID. NO. 2410 158-ArgHisGlnArgGlyPheAlaArg-165
SEQ. ID. NO. 2411 191-ProIleValSerGlnTrpThrPro-198
Antigenic Index - Jameson-Wolf
SEQ. ID. NO. 2412 6-LeuArgSerArgGlnValValIleAspHisAspLysValLysGln-20
SEQ. ID. NO. 2413 30-LeuArgGlnProProLeuAspAsn-37
SEQ. ID. NO. 2414 41-ValArgProAlaSerValGluAlaArgGlyLysTyrValGluArgArgArgGlnAspLysAspAlaAspGlyPheGlyGlnArg-68
SEQ. ID. NO. 2415 70-AlaAsnLeuArgArgAlaLeu-76
SEQ. ID. NO. 2416 86-AlaCysArgArgGlnArgIleHisThr-94
SEQ. ID. NO. 2417 112-SerPheLeuArgAspLysArgLeuLys-120
SEQ. ID. NO. 2418 138-ArgArgAlaArgArgValArgHisGlyAsnAlaGln-149
SEQ. ID. NO. 2419 155-GlnGlnProArgHisGlnArgGlyPheAla-164
SEQ. ID. NO. 2420 166-AlaGlySerGlyArgAsnAspLysAspValAlaPheSerIle-179
Hydrophilic Regions - Hopp-Woods
SEQ. ID. NO. 2421 6-LeuArgSerArgGlnValValIleAspHisAspLysValLysGln-20
SEQ. ID. NO. 2422 44-AlaSerValGluAlaArgGlyLysTyrValGluArgArgArgGlnAspLysAspAlaAspGlyPheGly-66
SEQ. ID. NO. 2423 70-AlaAsnLeuArgArgAlaLeu-76
SEQ. ID. NO. 2424 86-AlaCysArgArgGlnArgIleHisThr-94

TABLE 1-continued

| | |
|---|---|
| SEQ. ID. NO. 2425 | 113-PheLeuArgAspLysArgLeuLys-120 |
| SEQ. ID. NO. 2426 | 138-ArgArgAlaArgArgValArgHisGlyAsn-147 |
| SEQ. ID. NO. 2427 | 156-GlnProArgHisGlnArgGlyPheAla-164 |
| SEQ. ID. NO. 2428 | 167-GlySerGlyArgAsnAspLysAspValAla-176 |
| 148 | |
| AMPHI Regions - AMPHI | |
| SEQ. ID. NO. 2429 | 25-AlaAspLysIleArgLysIleGluAsnTrpPro-35 |
| SEQ. ID. NO. 2430 | 49-GlnSerAlaGluTyrPheArgLeuLeuValAspLeu-60 |
| SEQ. ID. NO. 2431 | 150-AlaGlyLeuGluLeuIleArgLysLeuGlyGlyGluIle-162 |
| SEQ. ID. NO. 2432 | 165-AlaAlaAlaIleLeuGluPheThrAspLeuGlnGlyGlyLysAsnIleArg-181 |
| Antigenic Index - Jameson-Wolf | |
| SEQ. ID. NO. 2433 | 4-LysThrSerAsnLeu-8 |
| SEQ. ID. NO. 2434 | 24-LeuAlaAspLysIleArgLysIleGluAsnTrpProGlnLysGly-38 |
| SEQ. ID. NO. 2435 | 66-MetAspGlnLysIleAspIle-72 |
| SEQ. ID. NO. 2436 | 76-LeuAspAlaArgGly-80 |
| SEQ. ID. NO. 2437 | 97-ProIleArgLysLysGlyLysLeuPro-105 |
| SEQ. ID. NO. 2438 | 117-TyrGlyGluAlaAlaVal-122 |
| SEQ. ID. NO. 2439 | 124-IleHisThrAspAlaValLysLeuGlySer-133 |
| SEQ. ID. NO. 2440 | 153-GluLeuIleArgLysLeuGlyGlyGluIleValGlu-164 |
| SEQ. ID. NO. 2441 | 172-ThrAspLeuGlnGlyGlyLysAsnIleArgAlaSerGlyAlaPro-186 |
| SEQ. ID. NO. 2442 | 192-GlnAsnGluGlyCysMetLysGly-199 |
| Hydrophilic Regions - Hopp-Woods | |
| SEQ. ID. NO. 2443 | 24-LeuAlaAspLysIleArgLysIleGluAsnTrpPro-35 |
| SEQ. ID. NO. 2444 | 66-MetAspGlnLysIleAspIle-72 |
| SEQ. ID. NO. 2445 | 97-ProIleArgLysLysGlyLysLeuPro-105 |
| SEQ. ID. NO. 2446 | 117-TyrGlyGluAlaAlaVal-122 |
| SEQ. ID. NO. 2447 | 124-IleHisThrAspAlaValLysLeuGlySer-133 |
| SEQ. ID. NO. 2448 | 153-GluLeuIleArgLysLeuGlyGlyGluIleValGlu-164 |
| SEQ. ID. NO. 2449 | 178-LysAsnIleArgAlaSerGly-184 |
| SEQ. ID. NO. 2450 | 195-GlyCysMetLysGly-199 |
| 149-2 | |
| AMPHI Regions - AMPHI | |
| SEQ. ID. NO. 2451 | 78-AsnLeuGlyAspAlaLeuAspGlyValProGlyIle-89 |
| SEQ. ID. NO. 2452 | 107-ThrGlyArgArgIleLysValLeuAsnHisHisGlyGluThrGlyAspMet-123 |
| SEQ. ID. NO. 2453 | 141-GlnValGluIleLeuArgGlyProValThr-150 |
| SEQ. ID. NO. 2454 | 158-ValAlaGlyLeuValAsp-163 |
| SEQ. ID. NO. 2455 | 170-ProGluLysMetProGluAsnGlyVal-178 |
| SEQ. ID. NO. 2456 | 190-AsnLeuGluLysLeu-194 |
| SEQ. ID. NO. 2457 | 226-TyrArgAsnLeuLysArgLeuProAspSerHis-236 |
| SEQ. ID. NO. 2458 | 351-PheProGlyPheGlu-355 |
| SEQ. ID. NO. 2459 | 372-AlaGlyAspAlaValGluAsnPhePheAsnAsn-382 |
| SEQ. ID. NO. 2460 | 395-ProIleGlyArgLeuLys-400 |
| SEQ. ID. NO. 2461 | 415-LeuSerAlaIleSerGluAlaVal-422 |
| SEQ. ID. NO. 2462 | 571-ArgPheGlyAsnTyrIleTyrAlaGln-579 |
| SEQ. ID. NO. 2463 | 582-AsnAspGlyArgGlyProLysSerIleGluAsp-592 |
| SEQ. ID. NO. 2464 | 633-ArgGlyArgLeuLysAsnLeuProSer-641 |
| Antigenic Index - Jameson-Wolf | |
| SEQ. ID. NO. 2465 | 1-MetArgArgGluAlaLysMetAla-8 |
| SEQ. ID. NO. 2466 | 31-HisGluThrGluGlnSerValAspLeuGluThr-41 |
| SEQ. ID. NO. 2467 | 46-GlyLysSerArgProArgAlaThrSerGly-55 |
| SEQ. ID. NO. 2468 | 61-ThrAlaSerAspLysIleIleSerGlyAspThrLeuArgGlnLysAla-76 |
| SEQ. ID. NO. 2469 | 103-IleArgGlyGlnThrGlyArgArgIleLysVal-113 |
| SEQ. ID. NO. 2470 | 115-AsnHisHisGlyGluThrGlyAspMetAlaAspPheSerProAspHis-130 |
| SEQ. ID. NO. 2471 | 143-GluIleLeuArgGlyPro-148 |
| SEQ. ID. NO. 2472 | 163-AspValAlaAspGlyLysIleProGluLysMetProGluAsnGlyValSerGlyGluLeuGlyLeu-184 |
| SEQ. ID. NO. 2473 | 186-LeuSerSerGlyAsnLeuGluLysLeuThrSerGlyGly-198 |
| SEQ. ID. NO. 2474 | 213-GlyLeuTyrArgLysSerGlyAspTyrAlaValProArgTyrArgAsnLeuLysArgLeuProAspSerHisAlaAspSerGlnThrGly-242 |
| SEQ. ID. NO. 2475 | 250-GlyGluLysGlyPhe-254 |
| SEQ. ID. NO. 2476 | 258-AlaTyrSerAspArgArgAspGlnTyrGly-267 |
| SEQ. ID. NO. 2477 | 269-ProAlaHisSerHisGluTyrAspAspCysHisAla-280 |
| SEQ. ID. NO. 2478 | 287-SerLeuIleAsnLysArgTyrLeu-294 |
| SEQ. ID. NO. 2479 | 301-LeuThrGluGluAspIleAspTyrAspAsnProGlyLeu-313 |
| SEQ. ID. NO. 2480 | 316-GlyPheHisAspAspAspAsnAlaHis-324 |
| SEQ. ID. NO. 2481 | 326-HisThrHisSerGlyArgProTrpIleAspLeuArgAsnLysArgTyrGluLeuArgAlaGluTrpLysGlnProPheProGly-353 |
| SEQ. ID. NO. 2482 | 360-HisLeuAsnArgAsnAspTyrArgHisAspGluLysAlaGlyAspAlaVal-376 |
| SEQ. ID. NO. 2483 | 380-PheAsnAsnGlnThrGlnAsnAlaArgIleGluLeuArgHisGlnProIleGlyArgLeuLysGlySerTrp-403 |
| SEQ. ID. NO. 2484 | 408-LeuGlnGlnLysSerSerAla-414 |
| SEQ. ID. NO. 2485 | 428-LeuAspAsnLysVal-432 |
| SEQ. ID. NO. 2486 | 443-AlaAsnTrpAspAsnPheThrLeuGluGlyGlyValArgValGluLysGlnLysAlaSerIleGlnTyrAspLysAlaLeuIleAspArgGluAsnTyr TyrAsnHisProLeuProAsp-482 |
| SEQ. ID. NO. 2487 | 484-GlyAlaHisArgGlnThrAla-490 |
| SEQ. ID. NO. 2488 | 512-SerHisGlnGluArgLeuProSerThrGlnGluLeuTyrAlaHisGly-527 |
| SEQ. ID. NO. 2489 | 537-ValGlyAsnLysHisLeuAsnLysGluArgSerAsnAsnIle-550 |
| SEQ. ID. NO. 2490 | 556-TyrGluGlyAspArgTrpGln-562 |
| SEQ. ID. NO. 2491 | 568-TyrArgAsnArgPheGlyAsn-574 |
| SEQ. ID. NO. 2492 | 580-ThrLeuAsnAspGlyArgGlyProLysSerIleGluAspAspSerGluMetLysLeu-598 |
| SEQ. ID. NO. 2493 | 600-ArgTyrAsnGlnSerGlyAlaAspPheTyrGlyAlaGluGly-613 |
| SEQ. ID. NO. 2494 | 615-IleTyrPheLysProThrProArgTyrArgIle-625 |
| SEQ. ID. NO. 2495 | 627-ValSerGlyAspTyrValArgGlyArgLeuLysAsnLeuProSerLeuProGlyArgGluAspAlaTyrGlyAsnArgPro-653 |
| SEQ. ID. NO. 2496 | 655-IleAlaGlnAspAspGlnAsnAlaProArgValProAla-667 |

TABLE 1-continued

| | |
|---|---|
| SEQ. ID. NO. 2497 | 677-SerLeuThrAspArgIleAspAla-684 |
| SEQ. ID. NO. 2498 | 695-AsnLysLeuAlaArgTyrGluThrArgThrProGlyHis-707 |
| SEQ. ID. NO. 2499 | 713-GlyAlaAsnTyrArgArgAsnThrArgTyrGlyGluTrp-725 |
| SEQ. ID. NO. 2500 | 731-AlaAspAsnLeuLeu-735 |
| SEQ. ID. NO. 2501 | 745-PheLeuSerAspThrProGlnMetGlyArgSerPheThrGlyGlyVal-760 |
| Hydrophilic Regions- Hopp-Woods | |
| SEQ. ID. NO. 2502 | 1-MetArgArgGluAlaLysMetAla-8 |
| SEQ. ID. NO. 2503 | 31-HisGluThrGluGlnSerValAspLeuGluThr-41 |
| SEQ. ID. NO. 2504 | 46-GlyLysSerArgProArgAlaThr-53 |
| SEQ. ID. NO. 2505 | 61-ThrAlaSerAspLysIleIleSer-68 |
| SEQ. ID. NO. 2506 | 70-AspThrLeuArgGlnLysAla-76 |
| SEQ. ID. NO. 2507 | 106-GlnThrGlyArgArgIleLysVal-113 |
| SEQ. ID. NO. 2508 | 118-GlyGluThrGlyAspMetAlaAspPheSerPro-128 |
| SEQ. ID. NO. 2509 | 163-AspValAlaAspGlyLysIleProGluLysMetProGluAsnGlyValSer-179 |
| SEQ. ID. NO. 2510 | 187-SerSerGlyAsnLeuGluLysLeuThr-195 |
| SEQ. ID. NO. 2511 | 213-GlyLeuTyrArgLysSerGlyAsp-220 |
| SEQ. ID. NO. 2512 | 225-ArgTyrArgAsnLeuLysArgLeuProAspSerHisAlaAspSerGlnThr-241 |
| SEQ. ID. NO. 2513 | 259-TyrSerAspArgArgAspGlnTyr-266 |
| SEQ. ID. NO. 2514 | 273-HisGluTyrAspAspCysHisAla-280 |
| SEQ. ID. NO. 2515 | 301-LeuThrGluGluAspIleAspTyrAspAsn-310 |
| SEQ. ID. NO. 2516 | 317-PheHisAspAspAspAsnAlaHis-324 |
| SEQ. ID. NO. 2517 | 336-LeuArgAsnLysArgTyrGluLeuArgAlaGluTrp-347 |
| SEQ. ID. NO. 2518 | 360-HisLeuAsnArgAsnAspTyrArgHisAspGluLysAlaGlyAspAlaVal-376 |
| SEQ. ID. NO. 2519 | 384-ThrGlnAsnAlaArgIleGluLeuArgHis-393 |
| SEQ. ID. NO. 2520 | 397-GlyArgLeuLysGly-401 |
| SEQ. ID. NO. 2521 | 452-GlyGlyValArgValGluLysGlnLysAla-461 |
| SEQ. ID. NO. 2522 | 468-AlaLeuIleAspArgGluAsnTyr-475 |
| SEQ. ID. NO. 2523 | 484-GlyAlaHisArgGlnThrAla-490 |
| SEQ. ID. NO. 2524 | 512-SerHisGlnGluArgLeuProSer-519 |
| SEQ. ID. NO. 2525 | 541-HisLeuAsnLysGluArgSerAsnAsn-549 |
| SEQ. ID. NO. 2526 | 556-TyrGluGlyAspArgTrp-561 |
| SEQ. ID. NO. 2527 | 581-LeuAsnAspGlyArgGlyProLysSerIleGluAspAspSerGluMetLysLeu-598 |
| SEQ. ID. NO. 2528 | 609-TyrGlyAlaGluGly-613 |
| SEQ. ID. NO. 2529 | 619-ProThrProArgTyrArgIle-625 |
| SEQ. ID. NO. 2530 | 630-AspTyrValArgGlyArgLeuLysAsn-638 |
| SEQ. ID. NO. 2531 | 643-ProGlyArgGluAspAlaTyrGly-650 |
| SEQ. ID. NO. 2532 | 655-IleAlaGlnAspAspGlnAsnAlaProArgValProAla-667 |
| SEQ. ID. NO. 2533 | 677-SerLeuThrAspArgIleAspAla-684 |
| SEQ. ID. NO. 2534 | 696-LysLeuAlaArgTyrGluThrArgThrProGly-706 |
| SEQ. ID. NO. 2535 | 715-AsnTyrArgArgAsnThrArgTyrGly-723 |
| 150-2 | |
| AMPHIRegions- AMPHI | |
| SEQ. ID. NO. 2536 | 20-IleThrGlnLeuLeuSerGlyLeuAsp-28 |
| SEQ. ID. NO. 2537 | 80-ValAlaAspLysAlaAlaAspSerLeuGlu-89 |
| SEQ. ID. NO. 2538 | 138-AsnGlyLysLysAlaProLysLeu-145 |
| SEQ. ID. NO. 2539 | 159-SerTyrProAsnPheCysGlnAlaGlyLysAspPheAspArgArgPheGlu-175 |
| SEQ. ID. NO. 2540 | 198-AlaTrpThrAspAsnIleAla-204 |
| SEQ. ID. NO. 2541 | 223-ThrProProAlaGlyLeuGln-229 |
| SEQ. ID. NO. 2542 | 293-ArgGluIleLeuAspLeuLeu-299 |
| SEQ. ID. NO. 2543 | 316-ValAlaArgAlaLeuSer-321 |
| SEQ. ID. NO. 2544 | 333-PheValLysGlyTyrAlaAlaPheAlaHisTyrGluGluLeuAspLysIleIle-350 |
| SEQ. ID. NO. 2545 | 365-IleValAspValLeuHisArgPheProAlaSerLeu-376 |
| SEQ. ID. NO. 2546 | 379-GluGlnPheIleArgLeuLeuArgProLeuAla-389 |
| SEQ. ID. NO. 2547 | 468-GlyValAlaProPheArg-473 |
| SEQ. ID. NO. 2548 | 505-ThrGluTrpGlnGlnPheAlaLys-512 |
| SEQ. ID. NO. 2549 | 537-IleArgGluGlnAla-541 |
| SEQ. ID. NO. 2550 | 560-AlaAlaLysMetAlaLysAspValGluAlaAlaLeuLeuAspValIle-575 |
| SEQ. ID. NO. 2551 | 588-GluTyrLeuAspMetLeuArgGluGlu-596 |
| Antigenic Index - Jameson-Wolf | |
| SEQ. ID. NO. 2552 | 1-MetSerGluHisAspMetGlnAsnThrAsnProPro-12 |
| SEQ. ID. NO. 2553 | 16-LeuProProGluIle-20 |
| SEQ. ID. NO. 2554 | 42-LysAlaGlyAsnGlyAlaSerAlaGlyLeu-51 |
| SEQ. ID. NO. 2555 | 72-SerGlnThrGlyAsnAlaLysSerValAlaAspLysAlaAlaAspSerLeuGlu-89 |
| SEQ. ID. NO. 2556 | 96-SerArgAlaGluLeuLysAspTyrLysAlaLysAsnIleAlaGlyGluArgArgLeu-114 |
| SEQ. ID. NO. 2557 | 118-ThrSerThrGlnGlyGluGlyGluProProLysGluAlaValVal-132 |
| SEQ. ID. NO. 2558 | 137-LeuAsnGlyLysLysAlaProLysLeuAspLys-147 |
| SEQ. ID. NO. 2559 | 154-GlyLeuGlyAspSerSerTyrProAsnPheCysGlnAlaGlyLysAspPheAspArgArgPheGluGluLeuGlyAlaLysArgLeuLeuGluArg ValAspAlaAspLeuAspPhe-192 |
| SEQ. ID. NO. 2560 | 207-LeuLysGluGluAlaAlaLysAsnArgAlaThrProAlaProGlnThrThrProProAlaGlyLeuGlnThrAlaProAspGlyArgTyrCysLys-238 |
| SEQ. ID. NO. 2561 | 250-GlnLysIleThrAlaArgGlnSerAspLysAspValArgHisIleGluIleAspLeuSerGlySerAspLeu-273 |
| SEQ. ID. NO. 2562 | 276-LeuProGlyAspAla-280 |
| SEQ. ID. NO. 2563 | 285-PheAspAsnAspProAlaLeuVal-292 |
| SEQ. ID. NO. 2564 | 302-AspProAlaThrGluIleGlnAlaGlyGlyLysMetMetPro-315 |
| SEQ. ID. NO. 2565 | 324-PheGluLeuThrGlnAsnThrProAlaPhe-333 |
| SEQ. ID. NO. 2566 | 344-GluGluLeuAspLysIleIleAla-351 |
| SEQ. ID. NO. 2567 | 397-SerAlaGlnAlaGluValGlyAspGluValHis-407 |
| SEQ. ID. NO. 2568 | 415-PheGluHisGluGlyArgAlaArgThrGlyGlyAlaSerGlyPheLeu-430 |
| SEQ. ID. NO. 2569 | 432-AspArgLeuGluGluAspGlyThrVal-440 |
| SEQ. ID. NO. 2570 | 443-PheValGluArgAsnAspGlyPheArgLeuProGluAspSerArgLysPro-459 |
| SEQ. ID. NO. 2571 | 464-GlySerGlyThrGly-468 |

TABLE 1-continued

| | |
|---|---|
| SEQ. ID. NO. 2572 | 478-GlnArgAlaAlaGluAsnAlaGluGlyLysAsn-488 |
| SEQ. ID. NO. 2573 | 509-GlnPheAlaLysAspGlyPheLeuHisArgTyrAspPheAlaTrpSerArgAspGlnGluGluLysIleTyrVal-533 |
| SEQ. ID. NO. 2574 | 535-AspLysIleArgGluGlnAlaGlu-542 |
| SEQ. ID. NO. 2575 | 559-AspAlaAlaLysMetAlaLysAspValGlu-568 |
| SEQ. ID. NO. 2576 | 579-GlyHisLeuAspGluGluGlyAlaGluGluTyrLeuAspMetLeuArgGluGluLysArgTyrGlnArgAspValTyr |
| Hydrophilic Regions- Hopp-Woods | |
| SEQ. ID. NO. 2577 | 1-MetSerGluHisAspMetGlnAsn-8 |
| SEQ. ID. NO. 2578 | 75-GlyAsnAlaLysSerValAlaAspLysAlaAlaAspSerLeuGlu-89 |
| SEQ. ID. NO. 2579 | 96-SerArgAlaGluLeuLysAspTyrLysAlaLysAsnIleAlaGlyGluArgArgLeu-114 |
| SEQ. ID. NO. 2580 | 120-ThrGlnGlyGluGlyGluProProLysGluAlaValVal-132 |
| SEQ. ID. NO. 2581 | 137-LeuAsnGlyLysLysAlaProLysLeuAspLys-147 |
| SEQ. ID. NO. 2582 | 166-AlaGlyLysAspPheAspArgArgPheGluGluLeuGlyAlaLysArgLeuLeuGluArgValAspAlaAspLeuAspPhe-192 |
| SEQ. ID. NO. 2583 | 207-LeuLysGluGluAlaAlaLysAsnArgAlaThrPro-218 |
| SEQ. ID. NO. 2584 | 230-ThrAlaProAspGlyArgTyrCysLys-238 |
| SEQ. ID. NO. 2585 | 251-LysIleThrAlaArgGlnSerAspLysAspValArgHisIleGluIleAspLeuSerGly-270 |
| SEQ. ID. NO. 2586 | 288-AspProAlaLeuVal-292 |
| SEQ. ID. NO. 2587 | 344-GluGluLeuAspLysIleIleAla-351 |
| SEQ. ID. NO. 2588 | 398-AlaGlnAlaGluValGlyAspGluValHis-407 |
| SEQ. ID. NO. 2589 | 415-PheGluHisGluGlyArgAlaArgThrGlyGly-425 |
| SEQ. ID. NO. 2590 | 432-AspArgLeuGluGluAspGlyThrVal-440 |
| SEQ. ID. NO. 2591 | 443-PheValGluArgAsnAspGlyPheArgLeuProGluAspSerArgLysPro-459 |
| SEQ. ID. NO. 2592 | 479-ArgAlaAlaGluAsnAlaGluGlyLys-487 |
| SEQ. ID. NO. 2593 | 523-TrpSerArgAspGlnGluGluLysIleTyrVal-533 |
| SEQ. ID. NO. 2594 | 535-AspLysIleArgGluGlnAlaGlu-542 |
| SEQ. ID. NO. 2595 | 559-AspAlaAlaLysMetAlaLysAspValGlu-568 |
| SEQ. ID. NO. 2596 | 580-HisLeuAspGluGluGlyAlaGluGluTyrLeuAspMetLeuArgGluGluLysArgTyrGlnArgAspValTyr-604 |
| 151 | |
| AMPHI Regions - AMPHI | |
| SEQ. ID. NO. 2597 | 6-AsnIleAlaIleIleAla-11 |
| SEQ. ID. NO. 2598 | 22-AspGlnLeuLeuArg-26 |
| SEQ. ID. NO. 2599 | 72-ValAspThrProGlyHis-77 |
| SEQ. ID. NO. 2600 | 81-GlyGlyGluValGluArgValLeuGlyMetValAspCysVal-94 |
| SEQ. ID. NO. 2601 | 128-LysIleAspLysPro-132 |
| SEQ. ID. NO. 2602 | 144-PheGluLeuPheAspAsnLeuGlyAlaThr-153 |
| SEQ. ID. NO. 2603 | 165-SerGlyLeuSerGlyPheAlaLysLeuGluGluThrAspGluSerAsn-180 |
| SEQ. ID. NO. 2604 | 184-ProLeuPheAspThrIleLeuLysTyrThr-193 |
| SEQ. ID. NO. 2605 | 248-GlyArgIleAsnGlnLeuLeuGlyPheLysGlyLeuGluArgVal-262 |
| SEQ. ID. NO. 2606 | 273-ValIleIleSerGlyIleGlu-279 |
| SEQ. ID. NO. 2607 | 330-IleArgAspArgLeuGlnLysGluLeu-338 |
| SEQ. ID. NO. 2608 | 348-AspThrAlaAspAla-352 |
| SEQ. ID. NO. 2609 | 396-CysGluProTyrGluAsnLeuThrValAsp-405 |
| SEQ. ID. NO. 2610 | 457-LeuThrArgGlyValGly-462 |
| SEQ. ID. NO. 2611 | 464-MetSerHisValPheAsp-469 |
| SEQ. ID. NO. 2612 | 537-LysGlyLysLysLeuThrAsnIle-544 |
| SEQ. ID. NO. 2613 | 551-GluAlaValArgLeuThrThr-557 |
| Antigenic Index - Jameson-Wolf | |
| SEQ. ID. NO. 2614 | 1-MetLysGlnIleArg-5 |
| SEQ. ID. NO. 2615 | 13-ValAspHisGlyLysThrThrLeu-20 |
| SEQ. ID. NO. 2616 | 24-LeuLeuArgGlnSerGlyThrPheArgAlaAsnGlnGlnValAspGluArgValMetAspSerAsnAspLeuGluLysGluArgGlyIle-53 |
| SEQ. ID. NO. 2617 | 59-AsnThrAlaIleAspTyrGluGlyTyr-67 |
| SEQ. ID. NO. 2618 | 72-ValAspThrProGlyHisAlaAspPheGlyGlyGluValGluArg-86 |
| SEQ. ID. NO. 2619 | 99-AspAlaGlnGluGlyProMetProGlnThrArgPheValThr-112 |
| SEQ. ID. NO. 2620 | 128-LysIleAspLysProSerAlaArgProSerTrp-138 |
| SEQ. ID. NO. 2621 | 151-GlyAlaThrAspGluGlnLeuAsp-158 |
| SEQ. ID. NO. 2622 | 171-AlaLysLeuGluGluThrAspGluSerAsnAspMetArgProLeu-185 |
| SEQ. ID. NO. 2623 | 193-ThrProAlaProSerGlySerAlaAspGluThrLeu-204 |
| SEQ. ID. NO. 2624 | 211-LeuAspTyrAspAsnTyrThrGly-218 |
| SEQ. ID. NO. 2625 | 226-LeuAsnGlyArgIleLysProGlyGln-234 |
| SEQ. ID. NO. 2626 | 240-AsnHisAspGlnGlnIleAla-246 |
| SEQ. ID. NO. 2627 | 257-LysGlyLeuGluArgValProLeuGluGluAlaGluAlaGlyAsp-271 |
| SEQ. ID. NO. 2628 | 277-GlyIleGluAspIleGly-282 |
| SEQ. ID. NO. 2629 | 287-IleThrAspLysAspAsnProLysGlyLeuPro-297 |
| SEQ. ID. NO. 2630 | 300-SerValAspGluProThrLeu-306 |
| SEQ. ID. NO. 2631 | 314-ThrSerProLeuAlaGlyThrGluGlyLysPheValThrSerArgGlnIleArgAspArgLeuGlnLysGluLeuLeu-339 |
| SEQ. ID. NO. 2632 | 344-LeuArgValGluAspThrAlaAspAlaAspValPheArgValSerGlyArgGlyGluLeu-363 |
| SEQ. ID. NO. 2633 | 371-AsnMetArgArgGluGlyTyr-377 |
| SEQ. ID. NO. 2634 | 381-ValGlyLysProArgValValTyrArgAspIleAspGlyGlnLysCysGluProTyrGluAsnLeuThrValAspValProAspAspAsnGln GlyAlaValMetGluGluLeuGlyArgArgArgGlyGluLeuThrAsnMetGluSerAspGlyAsnGlyArgThrArgLeuGluTyr-440 |
| SEQ. ID. NO. 2635 | 467-ValPheAspAspTyrAlaProValLysProAspMetProGlyArgHisAsnGly-484 |
| SEQ. ID. NO. 2636 | 489-GlnGluGlnGlyGlu-493 |
| SEQ. ID. NO. 2637 | 501-AsnLeuGluAspArgGlyArgMetPheValSerProAsnAspLysIleTyr-517 |
| SEQ. ID. NO. 2638 | 524-IleHisSerArgAspAsnAspLeu-531 |
| SEQ. ID. NO. 2639 | 535-ProLeuLysGlyLysLysLeuThrAsnIleArgAlaSerGlyThrAspGluAlaValArg-554 |
| SEQ. ID. NO. 2640 | 569-PheIleAspAspAspGluLeuValGlu-577 |
| SEQ. ID. NO. 2641 | 579-ThrProGlnSerIleArgLeuArgLysArgTyrLeuSerGluLeuGluArgArgArgHisPheLysLysLeuAsp-603 |
| Hydrophilic Regions- Hopp-Woods | |
| SEQ. ID. NO. 2642 | 1-MetLysGlnIleArg-5 |
| SEQ. ID. NO. 2643 | 29-GlyThrPheArgAla-33 |
| SEQ. ID. NO. 2644 | 35-GlnGlnValAspGluArgValMetAspSerAsnAspLeuGluLysGluArgGlyIle-53 |
| SEQ. ID. NO. 2645 | 80-PheGlyGlyGluValGluArg-86 |

TABLE 1-continued

| | |
|---|---|
| SEQ. ID. NO. 2646 | 99-AspAlaGlnGluGlyProMetPro-106 |
| SEQ. ID. NO. 2647 | 128-LysIleAspLysProSerAla-134 |
| SEQ. ID. NO. 2648 | 151-GlyAlaThrAspGluGlnLeuAsp-158 |
| SEQ. ID. NO. 2649 | 171-AlaLysLeuGluGluThrAspGluSerAsnAspMetArgProLeu-185 |
| SEQ. ID. NO. 2650 | 198-GlySerAlaAspGluThrLeu-204 |
| SEQ. ID. NO. 2651 | 226-LeuAsnGlyArgIleLysPro-232 |
| SEQ. ID. NO. 2652 | 241-HisAspGlnGlnIleAla-246 |
| SEQ. ID. NO. 2653 | 258-GlyLeuGluArgValProLeuGluGluAlaGluAlaGlyAsp-271 |
| SEQ. ID. NO. 2654 | 277-GlyIleGluAspIleGly-282 |
| SEQ. ID. NO. 2655 | 287-IleThrAspLysAspAsnProLysGly-295 |
| SEQ. ID. NO. 2656 | 300-SerValAspGluProThrLeu-306 |
| SEQ. ID. NO. 2657 | 318-AlaGlyThrGluGlyLysPheValThr-326 |
| SEQ. ID. NO. 2658 | 328-ArgGlnIleArgAspArgLeuGlnLysGluLeuLeu-339 |
| SEQ. ID. NO. 2659 | 344-LeuArgValGluAspThrAlaAspAlaAspValPheArgValSerGlyArgGlyGluLeu-363 |
| SEQ. ID. NO. 2660 | 371-AsnMetArgArgGluGlyTyr-377 |
| SEQ. ID. NO. 2661 | 381-ValGlyLysProArgValValTyrArgAspIleAspGlyGlnLysCysGluProTyrGlu-400 |
| SEQ. ID. NO. 2662 | 405-AspValProAspAspAsnGlnGlyAlaValMetGluGluLeuGlyArgArgArgGlyGluLeuThrAsnMetGluSerAspGlyAsnGlyArgThr ArgLeu-438 |
| SEQ. ID. NO. 2663 | 472-AlaProValLysProAspMetProGlyArgHis-482 |
| SEQ. ID. NO. 2664 | 489-GlnGluGlnGlyGlu-493 |
| SEQ. ID. NO. 2665 | 502-LeuGluAspArgGlyArgMet-508 |
| SEQ. ID. NO. 2666 | 512-ProAsnAspLysIleTyr-517 |
| SEQ. ID. NO. 2667 | 525-HisSerArgAspAsnAspLeu-531 |
| SEQ. ID. NO. 2668 | 536-LeuLysGlyLysLysLeuThrAsn-543 |
| SEQ. ID. NO. 2669 | 545-ArgAlaSerGlyThrAspGluAlaValArg-554 |
| SEQ. ID. NO. 2670 | 569-PheIleAspAspAspGluLeuValGlu-577 |
| SEQ. ID. NO. 2671 | 583-IleArgLeuArgLysArgTyrLeuSerGluLeuGluArgArgArgHisPheLysLysLeuAsp-603 |
| 152 | |
| AMPHI Regions - AMPHI | |
| SEQ. ID. NO. 2672 | 10-LeuProThrArgLeuPhe-15 |
| SEQ. ID. NO. 2673 | 66-ArgPheSerArgPheValGlnGlyTrpAlaGlyIleArgGlyTyrLeuLysAsnGlyIleProGluHisIleGlnProGlyHisAsnProLeu-96 |
| SEQ. ID. NO. 2674 | 103-AlaLeuLeuAlaAla-107 |
| SEQ. ID. NO. 2675 | 130-LeuAsnHisLeuValSerGluHisThrGlySerLeu-141 |
| SEQ. ID. NO. 2676 | 150-PheLysLeuLeuAlaValPheSerAlaIleHisIleAlaAlaValAlaAlaTyr-167 |
| Antigenic Index - Jameson-Wolf | |
| SEQ. ID. NO. 2677 | 1-MetLysAsnLysThrLysVal-7 |
| SEQ. ID. NO. 2678 | 29-SerAlaLysAlaGlyGlyAsp-35 |
| SEQ. ID. NO. 2679 | 61-GlySerAspThrAlaArgPheSerArg-69 |
| SEQ. ID. NO. 2680 | 79-GlyTyrLeuLysAsnGlyIleProGluHisIleGlnProGlyHisAsnProLeu-96 |
| SEQ. ID. NO. 2681 | 118-AlaAlaAspGluAsnThrPheSerThrAsnGlyTyr-129 |
| SEQ. ID. NO. 2682 | 137-HisThrGlySerLeuMetArg-143 |
| SEQ. ID. NO. 2683 | 169-ValPheLysLysLysAsnLeu-175 |
| SEQ. ID. NO. 2684 | 186-IleGluGlyLysThrSerIle-192 |
| Hydrophilic Regions - Hopp-Woods | |
| SEQ. ID. NO. 2685 | 1-MetLysAsnLysThrLysVal-7 |
| SEQ. ID. NO. 2686 | 63-AspThrAlaArgPhe-67 |
| SEQ. ID. NO. 2687 | 118-AlaAlaAspGluAsnThrPhe-124 |
| SEQ. ID. NO. 2688 | 169-ValPheLysLysLysAsnLeu-175 |
| SEQ. ID. NO. 2689 | 186-IleGluGlyLysThrSerIle-192 |
| 153 | |
| AMPHI Regions - AMPHI | |
| SEQ. ID. NO. 2690 | 17-AlaAlaSerValLeuSerLeuProGluMetMetArgLeuMetValPhe-32 |
| SEQ. ID. NO. 2691 | 96-ThrLeuValAlaTyrIleLysLeuSerSerValAlaGlu-108 |
| SEQ. ID. NO. 2692 | 130-ValSerValProGlnHisTrp-136 |
| SEQ. ID. NO. 2693 | 222-ValAsnThrIleLeuAsnGlyIleAlaTyr-231 |
| SEQ. ID. NO. 2694 | 274-AlaLysLysLeuSerHisLeuTyrArgIleThrGluAlaValGlyArgTrpSerMetIleAspIlePheValIle-298 |
| Antigenic Index - Jameson-Wolf | |
| SEQ. ID. NO. 2695 | 65-IleArgLysGlnAla-69 |
| SEQ. ID. NO. 2696 | 81-ValArgLeuArgGln-85 |
| SEQ. ID. NO. 2697 | 107-AlaGluValArgPhe-111 |
| SEQ. ID. NO. 2698 | 143-ArgLeuThrGlyAspAsnAlaValGlnThrAlaSerGluGlyLysThrCysCysSer-161 |
| SEQ. ID. NO. 2699 | 165-TyrPheArgAspSerAlaGluSerProCysGly-175 |
| SEQ. ID. NO. 2700 | 180-GluLeuTyrArgArgArgProLysSerLeuSer-190 |
| SEQ. ID. NO. 2701 | 215-SerAsnProAlaAlaThr-220 |
| SEQ. ID. NO. 2702 | 234-AspGluGlyAspArgLeu-239 |
| SEQ. ID. NO. 2703 | 272-ThrGlyAlaLysLysLeu-277 |
| SEQ. ID. NO. 2704 | 339-LeuLeuTrpAspLysArgAlaSerAspGlyIleAla-350 |
| SEQ. ID. NO. 2705 | 352-AsnGluThrGluLysHisAsp-358 |
| Hydrophilic Regions - Hopp-Woods | |
| SEQ. ID. NO. 2706 | 81-ValArgLeuArgGln-85 |
| SEQ. ID. NO. 2707 | 107-AlaGluValArgPhe-111 |
| SEQ. ID. NO. 2708 | 152-ThrAlaSerGluGlyLysThrCysCys-160 |
| SEQ. ID. NO. 2709 | 168-AspSerAlaGluSerPro-173 |
| SEQ. ID. NO. 2710 | 180-GluLeuTyrArgArgArgProLysSerLeuSer-190 |
| SEQ. ID. NO. 2711 | 234-AspGluGlyAspArgLeu-239 |
| SEQ. ID. NO. 2712 | 273-GlyAlaLysLysLeu-277 |

TABLE 1-continued

SEQ. ID. NO. 2713 339-LeuLeuTrpAspLysArgAlaSerAsp-347
SEQ. ID. NO. 2714 352-AsnGluThrGluLysHisAsp
154
AMPHI Regions - AMPHI
SEQ. ID. NO. 2715 122-GlyValThrGlyLeuGlyThrLeuLeu-130
SEQ. ID. NO. 2716 152-GlnAspIleProProValThr-158
SEQ. ID. NO. 2717 262-ThrLysAsnSerLysAsnValLysSer-270
SEQ. ID. NO. 2718 298-PheLysGlnSerVal-302
SEQ. ID. NO. 2719 360-SerLysGluHisTrpLysGlnGlnPheGlnThrAlaLeuAsnLysGlyLeuThrAla-378
SEQ. ID. NO. 2720 389-SerLysMetIleGluLeuAsnAsp-396
SEQ. ID. NO. 2721 429-LysLeuAlaAspLeuLeuAspLysPheAspLysLeuPro-441
SEQ. ID. NO. 2722 446-ValAlaGluLeuAsnGly-451
SEQ. ID. NO. 2723 467-LeuSerSerIleAspLysLeuValGlyLysProGlnThrGlnAsnIleProAsnGluLeuAsnGlnThrLeuLysGluLeuArgThrThr-496
SEQ. ID. NO. 2724 506-IleTyrGlyAspValGlnAsnThrLeuGlnSerLeuAspLysThrLeuLysAspValGlnProValIleAsnThrLeuLysGluLys-534
Antigenic Index - Jameson-Wolf
SEQ. ID. NO. 2725 1-MetThrAspAsnSerProProProAsnGlyHisAlaGlnAlaArgValArgLysAsnAsnThr-21
SEQ. ID. NO. 2726 43-LysGluIleArgAsnArgGlyProVal-51
SEQ. ID. NO. 2727 57-AspSerAlaGluGlyIleGluValAsnAsnThr-67
SEQ. ID. NO. 2728 75-AspValGlyArgValThrArgIleLysLeuArgAspAspGlnLysGlyValGlu-92
SEQ. ID. NO. 2729 100-AspValSerGlyLeuIleArgSerAspThrGln-110
SEQ. ID. NO. 2730 114-ValLysProArgIleAspGlnSerGly-122
SEQ. ID. NO. 2731 138-ThrProGlyLysSerAspGluAlaLysAspValPheGln-150
SEQ. ID. NO. 2732 169-LeuIleGlyLysAsnAspArgIleLeuAsn-178
SEQ. ID. NO. 2733 196-AlaHisPheAspProSerAspGlnSer-204
SEQ. ID. NO. 2734 212-GlnSerProAsnAspLysLeuIle-219
SEQ. ID. NO. 2735 228-GluSerGlyIleAsnIleGluThrThrGlySerGlyIleLysLeuAsnSer-244
SEQ. ID. NO. 2736 256-SerPheAspSerProLysThrLysAsnSerLysAsnValLysSerGluAspSer-273
SEQ. ID. NO. 2737 275-ThrLeuTyrAspSerArgSerGluValAlaAsnLeuProAspAspArgSerLeu-292
SEQ. ID. NO. 2738 300-GlnSerValArgGlyLeu-305
SEQ. ID. NO. 2739 311-ValGluTyrLysGlyLeuAsn-317
SEQ. ID. NO. 2740 325-ProTyrPheAspArgAsnAspSer-332
SEQ. ID. NO. 2741 345-IleArgIleGluProSerArgLeuGluIleAsnAlaAspGluGlnSerLysGluHisTrpLysGlnGlnPhe-368
SEQ. ID. NO. 2742 371-AlaLeuAsnLysGlyLeu-376
SEQ. ID. NO. 2743 386-LeuThrGlySerLysMetIleGluLeuAsnAspGlnProSerAlaSerProLysLeuArgPro-406
SEQ. ID. NO. 2744 419-GlnGlyGlyGlyLeuAspAspLeuGlnValLysLeu-430
SEQ. ID. NO. 2745 432-AspLeuLeuAspLysPheAspLysLeuProLeuAspLysThrValAla-447
SEQ. ID. NO. 2746 450-AsnGlySerLeuAlaGluLeuLysSerThrLeuLysSerAlaAsn-464
SEQ. ID. NO. 2747 469-SerIleAspLysLeuValGlyLysProGlnThrGlnAsnIleProAsnGluLeuAsnGlnThrLeuLysGluLeuArgThrThr-496
SEQ. ID. NO. 2748 500-ValSerProGlnSer-504
SEQ. ID. NO. 2749 516-SerLeuAspLysThrLeuLysAspValGln-525
SEQ. ID. NO. 2750 530-ThrLeuLysGluLysProAsn-536
SEQ. ID. NO. 2751 541-AsnSerSerSerLysAspProIleProLysGlySerArg-553
Hydrophilic Regions- Hopp-Woods
SEQ. ID. NO. 2752 1-MetThrAspAsnSerProProPro-8
SEQ. ID. NO. 2753 12-AlaGlnAlaArgValArgLysAsnAsn-20
SEQ. ID. NO. 2754 43-LysGluIleArgAsnArgGly-49
SEQ. ID. NO. 2755 57-AspSerAlaGluGlyIleGlu-63
SEQ. ID. NO. 2756 75-AspValGlyArgValThrArgIleLysLeuArgAspAspGlnLysGlyValGlu-92
SEQ. ID. NO. 2757 105-IleArgSerAspThr-109
SEQ. ID. NO. 2758 116-ProArgIleAspGln-120
SEQ. ID. NO. 2759 140-GlyLysSerAspGluAlaLysAspValPheGln-150
SEQ. ID. NO. 2760 171-GlyLysAsnAspArgIleLeu-177
SEQ. ID. NO. 2761 196-AlaHisPheAspProSerAspGln-203
SEQ. ID. NO. 2762 214-ProAsnAspLysLeuIle-219
SEQ. ID. NO. 2763 258-AspSerProLysThrLysAsnSerLysAsnValLysSerGluAspSer-273
SEQ. ID. NO. 2764 278-AspSerArgSerGluVal-283
SEQ. ID. NO. 2765 285-AsnLeuProAspAspArgSer-291
SEQ. ID. NO. 2766 311-ValGluTyrLysGly-315
SEQ. ID. NO. 2767 328-AspArgAsnAspSer-332
SEQ. ID. NO. 2768 345-IleArgIleGluProSerArgLeuGluIleAsnAlaAspGluGlnSerLysGluHisTrpLys-365
SEQ. ID. NO. 2769 390-LysMetIleGluLeuAsnAspGlnProSerAlaSerProLysLeuArgPro-406
SEQ. ID. NO. 2770 421-GlyGlyLeuAspAspLeuGlnValLysLeu-430
SEQ. ID. NO. 2771 432-AspLeuLeuAspLysPheAspLysLeuProLeuAspLysThrValAla-447
SEQ. ID. NO. 2772 454-AlaGluLeuLysSerThrLeuLysSerAlaAsn-464
SEQ. ID. NO. 2773 469-SerIleAspLysLeuValGly-475
SEQ. ID. NO. 2774 482-IleProAsnGluLeu-486
SEQ. ID. NO. 2775 498-GlnThrLeuLysGluLeuArgThr-495
SEQ. ID. NO. 2776 516-SerLeuAspLysThrLeuLysAspValGln-525
SEQ. ID. NO. 2777 530-ThrLeuLysGluLysProAsn-536
SEQ. ID. NO. 2778 543-SerSerLysAspProIleProLysGlySerArg-553
155
AMPHI Regions - AMPHI
SEQ. ID. NO. 2779 28-LysLeuGlyPheGlu-32
SEQ. ID. NO. 2780 42-AlaAlaSerLeuAsp-46
SEQ. ID. NO. 2781 105-LeuArgAlaLysLysVal-110
SEQ. ID. NO. 2782 118-ValProArgIleSerArgAlaGlnAlaLeuAspAlaLeuSerSerMetAlaAsnIleSerGlyTyrArgAlaValIleGluAlaAlaAsnAlaPheGly ArgPhePheThrGly-155
SEQ. ID. NO. 2783 175-ValAlaGlyLeuAlaAlaIleGlyThrAlaAsnSerLeuGlyAlaValValArgAlaPhe-194
SEQ. ID. NO. 2784 201-AlaGluGlnIleGluSerMetGlyGly-209
SEQ. ID. NO. 2785 225-AspGlyTyrAlaLysValMet-231

TABLE 1-continued

| | |
|---|---|
| SEQ. ID. NO. 2786 | 262-LysProAlaProLysLeuIleThrLysGluMetValGluSerMetLys-277 |
| SEQ. ID. NO. 2787 | 295-LeuThrArgProGlyGlu-300 |
| SEQ. ID. NO. 2788 | 308-ValLysIleIleGlyTyrThrAspMetAlaAsnArgLeuAlaGlyGln-323 |
| SEQ. ID. NO. 2789 | 330-ThrAsnLeuValAsnLeuThrLysLeuLeuSer-340 |
| SEQ. ID. NO. 2790 | 404-LysLeuAlaProAlaVal-409 |
| SEQ. ID. NO. 2791 | 428-AsnHisPheIleVal-432 |
| SEQ. ID. NO. 2792 | 451-LeuHisThrProLeuMetSerValThrAsnAlaIleSerGlyIleIle-466 |
| SEQ. ID. NO. 2793 | 469-GlyAlaLeuLeuGln-473 |
| SEQ. ID. NO. 2794 | 478-AsnGlyPheValSerLeuLeuSerPheValAla-488 |
| SEQ. ID. NO. 2795 | 494-IleAsnIlePheGlyGly-499 |
| Antigenic Index - Jameson-Wolf | |
| SEQ. ID. NO. 2796 | 4-GlyIleProArgGluSerLeuSerGlyGluThrArgVal-16 |
| SEQ. ID. NO. 2797 | 44-SerLeuAspAspAlaAla-49 |
| SEQ. ID. NO. 2798 | 72-ValAsnAlaProSerGluGlnGluLeu-80 |
| SEQ. ID. NO. 2799 | 94-TrpProArgGlnAsnGluAlaLeu-101 |
| SEQ. ID. NO. 2800 | 105-LeuArgAlaLysLysValAsn-111 |
| SEQ. ID. NO. 2801 | 117-MetValProArgIleSerArg-123 |
| SEQ. ID. NO. 2802 | 159-AlaAlaGlyLysValProProAla-166 |
| SEQ. ID. NO. 2803 | 194-PheAspThrArgLeuGluValAlaGluGlnIleGluSerMetGlyGlyLys-210 |
| SEQ. ID. NO. 2804 | 215-AspPheProGlnGluSerGlyGlySerGlyAspGlyTyrAlaLysValMetSer-232 |
| SEQ. ID. NO. 2805 | 242-LeuPheAlaGluGlnAlaLysGluValAsp-251 |
| SEQ. ID. NO. 2806 | 259-IleProGlyLysProAlaProLysLeuIleThr-269 |
| SEQ. ID. NO. 2807 | 271-GluMetValGluSerMetLysSerGlySer-280 |
| SEQ. ID. NO. 2808 | 289-ThrGlyGlyAsnCysGluLeuThrArgProGlyGluLeuSerVal-303 |
| SEQ. ID. NO. 2809 | 320-LeuAlaGlyGlnSerSer-325 |
| SEQ. ID. NO. 2810 | 338-LeuLeuSerProAsnLysAspGlyGluIle-347 |
| SEQ. ID. NO. 2811 | 349-LeuAspPheGluAspValIle-355 |
| SEQ. ID. NO. 2812 | 361-ValThrHisAspGlyGluIleThrPhePro-370 |
| SEQ. ID. NO. 2813 | 378-AlaGlnProGlnGlnThrProSerGluLysAlaValProAlaAlaLysProGluProLysPro-398 |
| Hydrophilic Regions - Hopp-Woods | |
| SEQ. ID. NO. 2814 | 4-GlyIleProArgGluSerLeuSerGlyGluThrArgVal-16 |
| SEQ. ID. NO. 2815 | 44-SerLeuAspAspAlaAla-49 |
| SEQ. ID. NO. 2816 | 74-AlaProSerGluGlnGluLeu-80 |
| SEQ. ID. NO. 2817 | 96-ArgGlnAsnGluAlaLeu-101 |
| SEQ. ID. NO. 2818 | 105-LeuArgAlaLysLysValAsn-111 |
| SEQ. ID. NO. 2819 | 117-MetValProArgIleSerArg-123 |
| SEQ. ID. NO. 2820 | 194-PheAspThrArgLeuGluValAlaGluGlnIleGluSerMetGly-208 |
| SEQ. ID. NO. 2821 | 215-AspPheProGlnGluSerGlyGlySerGlyAspGlyTyrAla-228 |
| SEQ. ID. NO. 2822 | 242-LeuPheAlaGluGlnAlaLysGluValAsp-251 |
| SEQ. ID. NO. 2823 | 260-ProGlyLysProAlaPro-265 |
| SEQ. ID. NO. 2824 | 271-GluMetValGluSerMetLysSer-278 |
| SEQ. ID. NO. 2825 | 291-GlyAsnCysGluLeuThrArgProGlyGlu-300 |
| SEQ. ID. NO. 2826 | 340-SerProAsnLysAspGlyGluIle-347 |
| SEQ. ID. NO. 2827 | 349-LeuAspPheGluAspValIle-355 |
| SEQ. ID. NO. 2828 | 363-HisAspGlyGluIle-367 |
| SEQ. ID. NO. 2829 | 382-GlnThrProSerGluLysAlaValProAlaAlaLysProGluProLysPro-398 |
| 156 | |
| AMPHI Regions - AMPHI | |
| SEQ. ID. NO. 2830 | 56-AsnGlyPheGluAlaPheAlaProPhe-64 |
| Antigenic Index - Jameson-Wolf | |
| SEQ. ID. NO. 2831 | 21-TyrAlaLysLysAlaGlyGlyPheArgPheLysAspAsnHisAsnProArgGly-38 |
| SEQ. ID. NO. 2832 | 44-GlnGlyAlaAlaAla-48 |
| SEQ. ID. NO. 2833 | 51-HisAlaAlaGlnGlnAsnGlyPheGlu-59 |
| SEQ. ID. NO. 2834 | 73-AlaThrGlyAsnAlaAla-78 |
| SEQ. ID. NO. 2835 | 103-AspLysAlaAlaMet-107 |
| Hydrophilic Regions - Hopp-Woods | |
| SEQ. ID. NO. 2836 | 21-TyrAlaLysLysAlaGlyGlyPheArgPheLysAspAsnHisAsnPro-36 |
| SEQ. ID. NO. 2837 | 103-AspLysAlaAlaMet-107 |
| 157 | |
| AMPHI Regions - AMPHI | |
| SEQ. ID. NO. 2838 | 21-GlyArgAspValArgAlaAla-27 |
| SEQ. ID. NO. 2839 | 32-IleAsnHisLeuLeuLysArg-38 |
| SEQ. ID. NO. 2840 | 61-PheValArgAlaAlaGln-66 |
| SEQ. ID. NO. 2841 | 167-GlnLeuValAspArg-171 |
| SEQ. ID. NO. 2842 | 176-AlaHisAspArgSerLeuAspGlyPhe-184 |
| Antigenic Index - Jameson-Wolf | |
| SEQ. ID. NO. 2843 | 1-MetArgAsnGluGluLysArgAlaLeuArgArgGluLeuArgGlyArgArgSerGlnMetGlyArgAspValArgAla-26 |
| SEQ. ID. NO. 2844 | 38-ArgTyrIleLysLysGlyArgLysIle-46 |
| SEQ. ID. NO. 2845 | 51-ProMetGlyLysGluLeuArgLeuAspGlyPheVal-62 |
| SEQ. ID. NO. 2846 | 64-AlaAlaGlnLysArgGlyAla-70 |
| SEQ. ID. NO. 2847 | 77-IleGluProArgSerArgArgMetTrp-85 |
| SEQ. ID. NO. 2848 | 89-TyrProAlaAspGlyValLysGlnGluArgLysArgGlyArgAlaLysLeuHis-106 |
| SEQ. ID. NO. 2849 | 111-AlaGlyArgLysLysArgValHisAsp-119 |
| SEQ. ID. NO. 2850 | 129-GlyMetAspArgLeuGlyTyr-135 |
| SEQ. ID. NO. 2851 | 151-MetLysTyrArgLeuGlnAla-157 |
| SEQ. ID. NO. 2852 | 172-LeuProValGluAlaHisAspArgSerLeuAspGlyPheVal-185 |
| Hydrophilic Regions - Hopp-Woods | |
| SEQ. ID. NO. 2853 | 1-MetArgAsnGluGluLysArgAlaLeuArgArgGluLeuArgGlyArgArgSerGlnMetGlyArgAspValArgAla-26 |
| SEQ. ID. NO. 2854 | 38-ArgTyrIleLysLysGlyArgLysIle-46 |
| SEQ. ID. NO. 2855 | 54-LysGluLeuArgLeu-58 |

TABLE 1-continued

| | |
|---|---|
| SEQ. ID. NO. 2856 | 64-AlaAlaGlnLysArgGlyAla-70 |
| SEQ. ID. NO. 2857 | 77-IleGluProArgSerArgArg-83 |
| SEQ. ID. NO. 2858 | 92-AspGlyValLysGlnGluArgLysArgGlyArgAlaLysLeu-105 |
| SEQ. ID. NO. 2859 | 111-AlaGlyArgLysLysArgValHisAsp-119 |
| SEQ. ID. NO. 2860 | 131-AspArgLeuGlyTyr-135 |
| SEQ. ID. NO. 2861 | 151-MetLysTyrArgLeuGlnAla-157 |
| SEQ. ID. NO. 2862 | 172-LeuProValGluAlaHisAspArgSerLeuAsp-182 |
| 158 | |
| AMPHI Regions - AMPHI | |
| SEQ. ID. NO. 2863 | 20-PheSerArgAlaAlaGluGlnLeu-27 |
| SEQ. ID. NO. 2864 | 33-AlaValSerArgIleValLysArgLeuGlu-42 |
| SEQ. ID. NO. 2865 | 46-GlyValAsnLeuLeuAsnArgThr-53 |
| SEQ. ID. NO. 2866 | 63-GlyAlaGlnTyrPheArgArgAlaGlnArgIleLeuGlnGlu-76 |
| SEQ. ID. NO. 2867 | 85-LeuAlaValHisGluIleProGln-92 |
| SEQ. ID. NO. 2868 | 166-ValIleAlaSerPro-170 |
| SEQ. ID. NO. 2869 | 178-ThrProGlnSerThrGluGluLeu-185 |
| SEQ. ID. NO. 2870 | 188-HisGlnCysLeuGlyPheThrGluProGlySerLeuAsnThrTrpAlaVal-204 |
| Antigenic Index - Jameson-Wolf | |
| SEQ. ID. NO. 2871 | 1-MetLysThrAsnSerGluGluLeu-8 |
| SEQ. ID. NO. 2872 | 16-GluSerGlySerPheSerArgAlaAlaGlu-25 |
| SEQ. ID. NO. 2873 | 36-ArgIleValLysArgLeuGluGluLysLeuGly-46 |
| SEQ. ID. NO. 2874 | 49-LeuLeuAsnArgThrThrArgGlnLeuSerLeuThrGluGluGlyAlaGlnTyrPheArgArgAlaGlnArgIleLeuGln-75 |
| SEQ. ID. NO. 2875 | 78-AlaAlaAlaGluThrGluMet-84 |
| SEQ. ID. NO. 2876 | 114-LysPheAsnGluArgTyrProHisIleArg-123 |
| SEQ. ID. NO. 2877 | 136-IleGluArgLysValAspIle-142 |
| SEQ. ID. NO. 2878 | 144-LeuArgAlaGlyGluLeuAspAspSerGlyLeuArgAla-156 |
| SEQ. ID. NO. 2879 | 158-HisLeuPheAspSerArgPheArgVal-166 |
| SEQ. ID. NO. 2880 | 168-AlaSerProGluTyrLeuAlaLysHisGlyThrProGlnSerThrGluGluLeuAla-186 |
| SEQ. ID. NO. 2881 | 192-GlyPheThrGluProGlySerLeuAsn-200 |
| SEQ. ID. NO. 2882 | 207-AlaGlnGlyAsnProTyrLysIle-214 |
| SEQ. ID. NO. 2883 | 216-ProHisPheThrAlaSerSerGlyGluIleLeu-226 |
| SEQ. ID. NO. 2884 | 229-LeuCysLeuSerGlyCys-234 |
| SEQ. ID. NO. 2885 | 243-LeuValAspAsnAspIleAlaGluGlyLysLeu-253 |
| SEQ. ID. NO. 2886 | 259-GluGlnThrSerAspLysThrHisProPhe-268 |
| SEQ. ID. NO. 2887 | 273-TyrSerAspLysAlaValAsnLeu-280 |
| SEQ. ID. NO. 2888 | 292-GluLeuGlyAsnAsnLeuCysGly-299 |
| Hydrophilic Regions - Hopp-Woods | |
| SEQ. ID. NO. 2889 | 1-MetLysThrAsnSerGluGluLeu-8 |
| SEQ. ID. NO. 2890 | 19-SerPheSerArgAlaAlaGlu-25 |
| SEQ. ID. NO. 2891 | 36-ArgIleValLysArgLeuGluGluLysLeuGly-46 |
| SEQ. ID. NO. 2892 | 58-SerLeuThrGluGluGlyAlaGlnTyrPheArgArgAlaGlnArgIleLeuGln-75 |
| SEQ. ID. NO. 2893 | 78-AlaAlaAlaGluThrGluMet-84 |
| SEQ. ID. NO. 2894 | 114-LysPheAsnGluArgTyrPro-120 |
| SEQ. ID. NO. 2895 | 136-IleGluArgLysValAspIle-142 |
| SEQ. ID. NO. 2896 | 144-LeuArgAlaGlyGluLeuAspAspSerGlyLeuArgAla-156 |
| SEQ. ID. NO. 2897 | 162-SerArgPheArgVal-166 |
| SEQ. ID. NO. 2898 | 180-GlnSerThrGluGluLeuAla-186 |
| SEQ. ID. NO. 2899 | 246-AsnAspIleAlaGluGlyLysLeu-253 |
| SEQ. ID. NO. 2900 | 260-GlnThrSerAspLysThrHis-266 |
| SEQ. ID. NO. 2901 | 276-LysAlaValAsnLeu-280 |
| 160 | |
| AMPHI Regions - AMPHI | |
| SEQ. ID. NO. 2902 | 6-LysLeuValAspPheAlaGlnLeuThrGly-15 |
| SEQ. ID. NO. 2903 | 72-GlyLeuGlyHisVal-76 |
| SEQ. ID. NO. 2904 | 121-AlaAspLeuMetAsnGlyLeuProGluThr-130 |
| SEQ. ID. NO. 2905 | 157-GlyThrValSerMetValAsnAlaLeuSerSer-167 |
| SEQ. ID. NO. 2906 | 186-LeuSerGlyValLeuLysGlyTrpGlnAspLysArg-197 |
| SEQ. ID. NO. 2907 | 200-HisLeuIleGlnLysValIleAspLysProGlu-210 |
| SEQ. ID. NO. 2908 | 218-MetValAlaAlaAlaAsn-223 |
| SEQ. ID. NO. 2909 | 229-LeuMetArgArgPhe-233 |
| SEQ. ID. NO. 2910 | 242-HisAlaPheValAsnHisIleArg-249 |
| SEQ. ID. NO. 2911 | 279-PheGlyLysAlaPheLys-284 |
| Antigenic Index - Jameson-Wolf | |
| SEQ. ID. NO. 2912 | 2-AspIleLeuAspLysLeuVal-8 |
| SEQ. ID. NO. 2913 | 28-SerValArgHisGluThrLeuGlnArgGluGlyLeu-39 |
| SEQ. ID. NO. 2914 | 51-CysIleAspGlyGluThrSerProArgProValSerThrGlyAsp-65 |
| SEQ. ID. NO. 2915 | 77-LeuSerHisAspGlyLysCysGlyGluSerLeuGlnProAspMetArgGlnHisGly-95 |
| SEQ. ID. NO. 2916 | 101-GlnCysGlyAsnGlyGlnAspMet-108 |
| SEQ. ID. NO. 2917 | 115-PheArgTyrAspThrHisAla-121 |
| SEQ. ID. NO. 2918 | 123-LeuMetAsnGlyLeu-127 |
| SEQ. ID. NO. 2919 | 149-LeuGluSerLysLysProLeu-155 |
| SEQ. ID. NO. 2920 | 178-LeuGluGlnAspLysAspValGluLeu-186 |
| SEQ. ID. NO. 2921 | 192-GlyTrpGlnAspLysArgLeuGly-199 |
| SEQ. ID. NO. 2922 | 205-ValIleAspLysProGluAspGluTrpAsnValAspLysMetVal-219 |
| SEQ. ID. NO. 2923 | 228-GlnLeuMetArgArgPheLysSerArgValGlyLeuSerProHis-242 |
| SEQ. ID. NO. 2924 | 255-LeuLeuLeuLysLysAsnProAspSerVal-264 |
| SEQ. ID. NO. 2925 | 274-GlnSerGluThrHisPhe-279 |

TABLE 1-continued

| | |
|---|---|
| SEQ. ID. NO. 2926 | 281-LysAlaPheLysArg-285 |
| SEQ. ID. NO. 2927 | 290-SerProGlyGlnTyrArgLysGluGlyGlyGlnLys-301 |
| Hydrophilic Regions - Hopp-Woods | |
| SEQ. ID. NO. 2928 | 2-AspIleLeuAspLysLeuVal-8 |
| SEQ. ID. NO. 2929 | 29-ValArgHisGluThrLeuGlnArgGluGlyLeu-39 |
| SEQ. ID. NO. 2930 | 53-AspGlyGluThrSerProArgProValSer-62 |
| SEQ. ID. NO. 2931 | 79-HisAspGlyLysCysGlyGluSerLeuGlnProAspMetArgGln-93 |
| SEQ. ID. NO. 2932 | 101-GlnCysGlyAsnGlyGlnAsp-107 |
| SEQ. ID. NO. 2933 | 149-LeuGluSerLysLysProLeu-155 |
| SEQ. ID. NO. 2934 | 178-LeuGluGlnAspLysAspValGluLeu-186 |
| SEQ. ID. NO. 2935 | 193-TrpGlnAspLysArgLeuGly-199 |
| SEQ. ID. NO. 2936 | 205-ValIleAspLysProGluAspGluTrpAsnVal-215 |
| SEQ. ID. NO. 2937 | 228-GlnLeuMetArgArgPheLysSerArgValGly-238 |
| SEQ. ID. NO. 2938 | 255-LeuLeuLeuLysLysAsnProAspSer-263 |
| SEQ. ID. NO. 2939 | 281-LysAlaPheLysArg-285 |
| SEQ. ID. NO. 2940 | 293-GlnTyrArgLysGluGlyGlyGlnLys-301 |
| 163 | |
| AMPHI Regions - AMPHI | |
| SEQ. ID. NO. 2941 | 60-SerSerLeuGlyAsnIle-65 |
| SEQ. ID. NO. 2942 | 67-LeuGlyArgAspGluAsp-72 |
| SEQ. ID. NO. 2943 | 76-PheGlyPheLeuSerTrpLeuAlaMetLeuPhe-86 |
| SEQ. ID. NO. 2944 | 100-AlaGluProLeuMetHisTyrPheSerAspIleThrAla-112 |
| SEQ. ID. NO. 2945 | 170-IleSerGlyArgPheGlyAspAlaIleAspIleMetAlaLeuLeuAlaThrPhePheGlyIleIleThrThr-193 |
| SEQ. ID. NO. 2946 | 227-MetSerLeuAlaValValSerAlaIleSerGlyValGlyLysGlyValLysValLeuSer-246 |
| SEQ. ID. NO. 2947 | 272-AlaPheGlyAspAsnIleGlyAsnTyrLeuGlyAsnLeuValArg-286 |
| SEQ. ID. NO. 2948 | 313-TrpCysSerTrpAlaProPheValGlyLeuPheIleAla-325 |
| SEQ. ID. NO. 2949 | 346-LeuPheGlyValLeuTrpPhe-352 |
| SEQ. ID. NO. 2950 | 367-AlaGlyGlyMetLeuGluLysMetThrSerSer-377 |
| SEQ. ID. NO. 2951 | 380-ThrLeuLeuPheLysPhePheAsnTyrLeuProLeuProGluLeuThrSerIleValSerLeuLeu-401 |
| SEQ. ID. NO. 2952 | 438-TrpGlyValLeuMetSerAla-444 |
| SEQ. ID. NO. 2953 | 454-GlyLeuGlyAsnLeuGlnSerMetThrLeu-463 |
| SEQ. ID. NO. 2954 | 520-GluGlnAspIleLeuLysPheLeuLysGlnThrAlaSerPro-533 |
| SEQ. ID. NO. 2955 | 535-MetHisGluLeuGlnArgGluLeu-542 |
| SEQ. ID. NO. 2956 | 574-AspPheMetTyrGlyIle-579 |
| SEQ. ID. NO. 2957 | 583-GlyGlnAspValSerAspGlnLeu-590 |
| SEQ. ID. NO. 2958 | 630-AlaAspIleLeuLysAsnTyr-636 |
| Antigenic Index - Jameson-Wolf | |
| SEQ. ID. NO. 2959 | 29-AspArgAlaLysGlu-33 |
| SEQ. ID. NO. 2960 | 65-IleArgLeuGlyArgAspGluAspValPro-74 |
| SEQ. ID. NO. 2961 | 111-ThrAlaGlyThrProGluHisArgGlnGln-120 |
| SEQ. ID. NO. 2962 | 166-LeuLysGluLysIleSerGlyArgPheGlyAspAlaIleAsp-179 |
| SEQ. ID. NO. 2963 | 200-GlnLeuGlyAlaGlyLeu-205 |
| SEQ. ID. NO. 2964 | 237-GlyValGlyLysGlyValLysVal-244 |
| SEQ. ID. NO. 2965 | 293-AlaTyrGluArgGluHisLysProTrpPhe-302 |
| SEQ. ID. NO. 2966 | 326-ArgIleSerLysGlyArgThrIleArg-334 |
| SEQ. ID. NO. 2967 | 370-MetLeuGluLysMetThrSerSerProGlu-379 |
| SEQ. ID. NO. 2968 | 409-ThrSerAlaAspSerGlyIle-415 |
| SEQ. ID. NO. 2969 | 421-IleThrSerArgAspLysGlyLeuSerAlaProArgTrp-433 |
| SEQ. ID. NO. 2970 | 451-ArgSerGlyGlyLeuGlyAsn-457 |
| SEQ. ID. NO. 2971 | 484-LeuSerAlaAspLysLysTyrPheGluThrArgValAsnProThrSer-499 |
| SEQ. ID. NO. 2972 | 503-ThrGlyGlyLysTrpLysGluArgLeu-511 |
| SEQ. ID. NO. 2973 | 516-SerGlnThrGlnGluGlnAspIle-523 |
| SEQ. ID. NO. 2974 | 527-LeuLysGlnThrAlaSer-532 |
| SEQ. ID. NO. 2975 | 537-GluLeuGlnArgGluLeuSerGluGluTyrGlyLeu-548 |
| SEQ. ID. NO. 2976 | 550-ValArgValAspLysMetPheHisArgAspGluProAla-562 |
| SEQ. ID. NO. 2977 | 566-ValIleArgLysGluThrMetArg-573 |
| SEQ. ID. NO. 2978 | 581-SerValGlyGlnAspValSerAspGlnLeuIleAsnAspGlyLysLeuProHisIleArgHisGlnThrThrTyrLysProTyr-608 |
| SEQ. ID. NO. 2979 | 612-PheAspGlyArgValGlyTyr-618 |
| SEQ. ID. NO. 2980 | 622-TyrMetAsnLysAspGluLeuIle-629 |
| SEQ. ID. NO. 2981 | 632-IleLeuLysAsnTyrGlu-637 |
| SEQ. ID. NO. 2982 | 654-GluGlnValGluLeuAlaGlu-660 |
| Hydrophilic Regions - Hopp-Woods | |
| SEQ. ID. NO. 2983 | 29-AspArgAlaLysGlu-33 |
| SEQ. ID. NO. 2984 | 66-ArgLeuGlyArgAspGluAspValPro-74 |
| SEQ. ID. NO. 2985 | 114-ThrProGluHisArgGlnGln-120 |
| SEQ. ID. NO. 2986 | 166-LeuLysGluLysIleSerGlyArgPheGlyAsp-176 |
| SEQ. ID. NO. 2987 | 238-ValGlyLysGlyValLysVal-244 |
| SEQ. ID. NO. 2988 | 293-AlaTyrGluArgGluHisLysPro-300 |
| SEQ. ID. NO. 2989 | 327-IleSerLysGlyArgThrIleArg-334 |
| SEQ. ID. NO. 2990 | 370-MetLeuGluLysMetThrSerSerPro-378 |
| SEQ. ID. NO. 2991 | 422-ThrSerArgAspLysGlyLeuSer-429 |
| SEQ. ID. NO. 2992 | 484-LeuSerAlaAspLysLysTyrPheGlu-492 |
| SEQ. ID. NO. 2993 | 506-LysTrpLysGluArgLeu-511 |
| SEQ. ID. NO. 2994 | 517-GlnThrGlnGluGlnAspIle-523 |
| SEQ. ID. NO. 2995 | 537-GluLeuGlnArgGluLeuSerGluGluTyrGlyLeu-548 |
| SEQ. ID. NO. 2996 | 550-ValArgValAspLysMetPheHisArgAspGluProAla-562 |
| SEQ. ID. NO. 2997 | 566-ValIleArgLysGluThrMetArg-573 |
| SEQ. ID. NO. 2998 | 581-SerValGlyGlnAspValSerAsp-588 |

TABLE 1-continued

| | |
|---|---|
| SEQ. ID. NO. 2999 | 590-LeuIleAsnAspGlyLysLeuProHis-598 |
| SEQ. ID. NO. 3000 | 622-TyrMetAsnLysAspGluLeuIle-629 |
| SEQ. ID. NO. 3001 | 654-GluGlnValGluLeuAlaGlu-660 |
| 164 | |
| AMPHI Regions - AMPHI | |
| SEQ. ID. NO. 3002 | 6-AlaAsnPheTyrGluMetLeuAlaAlaAla-15 |
| SEQ. ID. NO. 3003 | 33-AlaTyrArgAlaLeuLysGlnGlu-40 |
| SEQ. ID. NO. 3004 | 75-AlaIleSerAlaIleGlyAlaVal-82 |
| SEQ. ID. NO. 3005 | 97-TyrIleLeuAsnAspCys-102 |
| SEQ. ID. NO. 3006 | 113-LeuSerLysGluLeuAlaGlyLeuLysAla-122 |
| SEQ. ID. NO. 3007 | 148-PheGluAspValArgArgPheProGlu-156 |
| SEQ. ID. NO. 3008 | 160-LeuGlyArgGlnProArgIleAsnAspLeuAlaHis-171 |
| SEQ. ID. NO. 3009 | 189-TyrAlaAsnLeuPheAlaAsnLeuAsnGlyIleGluArgIlePheLys-204 |
| SEQ. ID. NO. 3010 | 264-ValProAlaIleTyrThr-269 |
| SEQ. ID. NO. 3011 | 282-TrpPheAsnArgIle-286 |
| SEQ. ID. NO. 3012 | 311-AlaLysLeuLeuGluGlyTyrGlyLeuSer-320 |
| SEQ. ID. NO. 3013 | 362-GluValGlyGluLeuIle-367 |
| SEQ. ID. NO. 3014 | 374-MetArgGlyTyrLeuAsn-379 |
| SEQ. ID. NO. 3015 | 387-ThrIleValAsnGlyTrpLeuLys-394 |
| SEQ. ID. NO. 3016 | 424-ValTyrProArgGluIleGluGluGlu-432 |
| SEQ. ID. NO. 3017 | 459-PheValGlnLeuLysGluGlyMet-466 |
| SEQ. ID. NO. 3018 | 472-GluIleArgArgHisLeuArgThrVal-480 |
| SEQ. ID. NO. 3019 | 484-PheLysIleProLysGln-489 |
| SEQ. ID. NO. 3020 | 499-AsnAlaThrGlyLysValLeuLysArgValLeuLysGluGlnPheAspGlyAsn-516 |
| AntigenicIndex -Jameson-Wolf | |
| SEQ. ID. NO. 3021 | 1-MetAsnArgThrTyr-5 |
| SEQ. ID. NO. 3022 | 15-AlaCysArgLysAsnGlyAsnGly-22 |
| SEQ. ID. NO. 3023 | 26-PheAspGlyLysGluLysThrAlaTyrArgAlaLeuLysGlnGluAlaGluAla-43 |
| SEQ. ID. NO. 3024 | 63-ValSerAsnSerThrGlu-68 |
| SEQ. ID. NO. 3025 | 88-ThrPheLeuLysAsnSerGlu-94 |
| SEQ. ID. NO. 3026 | 100-AsnAspCysLysAla-104 |
| SEQ. ID. NO. 3027 | 112-GlyLeuSerLysGluLeuAlaGly-119 |
| SEQ. ID. NO. 3028 | 121-LysAlaGlnThrProValGlu-127 |
| SEQ. ID. NO. 3029 | 130-IleTrpThrAspLysSerArgProThrGlyGluThrAlaGluGlyAspAlaPhePheGluAspValArgArgPheProGluLysProAspLeuGlyArg GlnProArgIleAsnAsp-168 |
| SEQ. ID. NO. 3030 | 176-SerGlyThrThrGlyHisProLysGlyAla-185 |
| SEQ. ID. NO. 3031 | 196-LeuAsnGlyIleGluArgIlePheLysIleSerLysArgAspArgPhe-211 |
| SEQ. ID. NO. 3032 | 253-ThrLeuLeuLysArg-257 |
| SEQ. ID. NO. 3033 | 290-IleSerGlyGlyAlaProLeuAla-297 |
| SEQ. ID. NO. 3034 | 304-PheLysAlaLysPheProArg-310 |
| SEQ. ID. NO. 3035 | 317-TyrGlyLeuSerGluAlaSer-323 |
| SEQ. ID. NO. 3036 | 330-ThrProGluArgGlnLysAlaArgSer-338 |
| SEQ. ID. NO. 3037 | 343-LeuProGlyLeuGluAlaLysAlaValAspGluGluLeuValGluValProArgGlyGluValGly-364 |
| SEQ. ID. NO. 3038 | 367-IleValArgGlyGlySerValMet-374 |
| SEQ. ID. NO. 3039 | 382-AlaAlaThrAspGluThrIle-388 |
| SEQ. ID. NO. 3040 | 393-LeuLysThrGlyAsp-397 |
| SEQ. ID. NO. 3041 | 400-ThrIleAspGluAspGly-405 |
| SEQ. ID. NO. 3042 | 410-ValAspArgLysLysAspLeuIleIleSerLysGlyGlnAsnValTyrProArgGluIleGluGluGluIleTyrLys-435 |
| SEQ. ID. NO. 3043 | 446-GlyValLysAspArgTyrAlaAspGluGluIle-456 |
| SEQ. ID. NO. 3044 | 462-LeuLysGluGlyMetAspLeuGlyGluAsnGluIleArgArgHisLeuArg-478 |
| SEQ. ID. NO. 3045 | 490-IleHisPheLysAspGlyLeuProArgAsnAlaThrGlyLysValLeuLysArgValLeuLysGluGlnPheAspGlyAsnLys-517 |
| Hydrophilic Regions - Hopp-Woods | |
| SEQ. ID. NO. 3046 | 15-AlaCysArgLysAsnGlyAsn-21 |
| SEQ. ID. NO. 3047 | 26-PheAspGlyLysGluLysThrAlaTyrArgAlaLeuLysGlnGluAlaGluAla-43 |
| SEQ. ID. NO. 3048 | 112-GlyLeuSerLysGluLeuAlaGly-119 |
| SEQ. ID. NO. 3049 | 133-AspLysSerArgProThrGlyGluThrAlaGluGlyAspAlaPhePheGluAspValArgArgPheProGluLysProAspLeuGlyArgGlnPro ArgIleAsnAsp-168 |
| SEQ. ID. NO. 3050 | 198-GlyIleGluArgIlePheLysIleSerLysArgAspArgPhe-211 |
| SEQ. ID. NO. 3051 | 253-ThrLeuLeuLysArg-257 |
| SEQ. ID. NO. 3052 | 304-PheLysAlaLysPheProArg-310 |
| SEQ. ID. NO. 3053 | 330-ThrProGluArgGlnLysAlaArgSer-338 |
| SEQ. ID. NO. 3054 | 346-LeuGluAlaLysAlaValAspGluGluLeuValGluValProArgGlyGluValGly-364 |
| SEQ. ID. NO. 3055 | 382-AlaAlaThrAspGluThrIle-388 |
| SEQ. ID. NO. 3056 | 400-ThrIleAspGluAspGly-405 |
| SEQ. ID. NO. 3057 | 410-ValAspArgLysLysAspLeuIleIle-418 |
| SEQ. ID. NO. 3058 | 425-TyrProArgGluIleGluGluGluIleTyrLys-435 |
| SEQ. ID. NO. 3059 | 446-GlyValLysAspArgTyrAlaAspGluGluIle-456 |
| SEQ. ID. NO. 3060 | 462-LeuLysGluGlyMetAspLeuGlyGluAsnGluIleArgArgHisLeuArg-478 |
| SEQ. ID. NO. 3061 | 494-AspGlyLeuProArgAsnAlaThr-501 |
| SEQ. ID. NO. 3062 | 503-LysValLeuLysArgValLeuLysGluGlnPheAspGlyAsnLys-517 |
| 165-1 | |
| AMPHI Regions - AMPHI | |
| SEQ. ID. NO. 3063 | 17-AlaThrLeuGlyValLeuLeuLysGluLeu-26 |
| SEQ. ID. NO. 3064 | 33-ThrLeuIleGluArgLeuGluAsp-40 |
| SEQ. ID. NO. 3065 | 72-IleIleAspProAlaArgAlaLeuAsnIleAla-82 |
| SEQ. ID. NO. 3066 | 90-GlnPheTrpAlaThr-94 |
| SEQ. ID. NO. 3067 | 108-AsnAlaValProHis-112 |
| SEQ. ID. NO. 3068 | 125-LeuGlnLysArgTyrAspAlaPheLysThrGlnLysLeuPheGluAsnMet-141 |
| SEQ. ID. NO. 3069 | 182-ArgLeuThrArgGlnMetValLysTyrLeuGlnGly-193 |
| SEQ. ID. NO. 3070 | 198-ThrGluPheAsnArgHisValGluAspIleLysArgGlu-210 |

TABLE 1-continued

| | |
|---|---|
| SEQ. ID. NO. 3071 | 348-GlyTrpAlaAsnMetPro-353 |
| SEQ. ID. NO. 3072 | 364-LysThrLysGluGlu-368 |
| SEQ. ID. NO. 3073 | 371-AlaSerLeuLeuGluTyrTyr-377 |
| SEQ. ID. NO. 3074 | 453-TrpGluAspArgLeuLysGluLeu-460 |
| Antigenic Index - Jameson-Wolf | |
| SEQ. ID. NO. 3075 | 1-MetAlaGluAlaThrAsp-6 |
| SEQ. ID. NO. 3076 | 24-LysGluLeuGluProSerTrp-30 |
| SEQ. ID. NO. 3077 | 36-GluArgLeuGluAspValAlaLeuGluSerSerAsnAlaTrpAsnAsnAlaGlyThrGly-55 |
| SEQ. ID. NO. 3078 | 97-AlaGluGlyLysLeuGluAspAsnSer-105 |
| SEQ. ID. NO. 3079 | 117-MetAsnGluAspHisCysSerTyrLeuGlnLysArgTyrAspAlaPheLysThrGlnLysLeuPheGlu-139 |
| SEQ. ID. NO. 3080 | 141-MetGluPheSerThrAspArgAsnLysIleSerAsp-152 |
| SEQ. ID. NO. 3081 | 157-MetMetArgGlyArgAspGluAsnGlnPro-166 |
| SEQ. ID. NO. 3082 | 169-AlaAsnTyrSerAlaGluGlyThrAspValAspPheGlyArgLeuThrArgGlnMet-187 |
| SEQ. ID. NO. 3083 | 191-LeuGlnGlyLysGlyValLysThrGluPheAsnArgHisValGluAspIleLysArgGluSerAspGly-213 |
| SEQ. ID. NO. 3084 | 319-ThrAlaAspThrArgAsnProAspGlyGlnLeu-229 |
| SEQ. ID. NO. 3085 | 249-GlnLysSerGlyIleProGluGlyLysGlyTyrGly-260 |
| SEQ. ID. NO. 3086 | 269-PheArgAsnSerAsnProGluThrAlaGluGlnHisAsn-281 |
| SEQ. ID. NO. 3087 | 300-LeuAspThrArgAsnValAspGlyLysArgHisLeu-311 |
| SEQ. ID. NO. 3088 | 322-AsnPheLeuLysGlnGlySerLeuMet-330 |
| SEQ. ID. NO. 3089 | 361-GluLeuArgLysThrLysGluGluArgPhe-370 |
| SEQ. ID. NO. 3090 | 377-TyrProGluAlaAsnProAspAspTrpGlu-386 |
| SEQ. ID. NO. 3091 | 395-GlnIleIleLysLysAspSerGluLysGlyGly-405 |
| SEQ. ID. NO. 3092 | 415-AlaHisAlaAspGlySer-420 |
| SEQ. ID. NO. 3093 | 428-SerProGlyAlaSerThr-433 |
| SEQ. ID. NO. 3094 | 446-PheProGluArgAlaProSerTrpGluAspArgLeuLysGluLeuValProGlyTyr-464 |
| SEQ. ID. NO. 3095 | 467-LysLeuAsnGluAsnProGluArgAlaAspGlu-477 |
| Hydrophilic Regions- Hopp-Woods | |
| SEQ. ID. NO. 3096 | 1-MetAlaGluAlaThrAsp-6 |
| SEQ. ID. NO. 3097 | 24-LysGluLeuGluPro-28 |
| SEQ. ID. NO. 3098 | 36-GluArgLeuGluAspValAlaLeuGluSer-45 |
| SEQ. ID. NO. 3099 | 97-AlaGluGlyLysLeuGluAspAsnSer-105 |
| SEQ. ID. NO. 3100 | 117-MetAsnGluAspHisCys-122 |
| SEQ. ID. NO. 3101 | 125-LeuGlnLysArgTyrAspAlaPheLysThr-134 |
| SEQ. ID. NO. 3102 | 141-MetGluPheSerThrAspArgAsnLysIleSerAsp-152 |
| SEQ. ID. NO. 3103 | 158-MetArgGlyArgAspGluAsnGlnPro-166 |
| SEQ. ID. NO. 3104 | 172-SerAlaGluGlyThrAspValAspPhe-180 |
| SEQ. ID. NO. 3105 | 182-ArgLeuThrArgGlnMet-187 |
| SEQ. ID. NO. 3106 | 194-LysGlyValLysThrGluPheAsnArgHisValGluAspIleLysArgGluSerAspGly-213 |
| SEQ. ID. NO. 3107 | 219-ThrAlaAspThrArgAsnProAspGly-227 |
| SEQ. ID. NO. 3108 | 252-GlyIleProGluGlyLysGly-258 |
| SEQ. ID. NO. 3109 | 272-SerAsnProGluThrAlaGluGlnHisAsn-281 |
| SEQ. ID. NO. 3110 | 300-LeuAspThrArgAsnValAspGlyLysArg-309 |
| SEQ. ID. NO. 3111 | 361-GluLeuArgLysThrLysGluGluArgPhe-370 |
| SEQ. ID. NO. 3112 | 380-AlaAsnProAspAspTrpGlu-386 |
| SEQ. ID. NO. 3113 | 395-GlnIleIleLysLysAspSerGluLysGlyGly-405 |
| SEQ. ID. NO. 3114 | 446-PheProGluArgAlaProSerTrpGluAspArgLeuLysGluLeuVal-461 |
| SEQ. ID. NO. 3115 | 467-LysLeuAsnGluAsnProGluArgAlaAspGlu-477 |
| Hydrophilic Regions- Hopp-Woods | |
| SEQ. ID. NO. 3116 | 1-MetAlaGluAlaThrAsp-6 |
| SEQ. ID. NO. 3117 | 24-LysGluLeuGluPro-28 |
| SEQ. ID. NO. 3118 | 36-GluArgLeuGluAspValAlaLeuGluSer-45 |
| SEQ. ID. NO. 3119 | 97-AlaGluGlyLysLeuGluAspAsnSer-105 |
| SEQ. ID. NO. 3120 | 117-MetAsnGluAspHisCys-122 |
| SEQ. ID. NO. 3121 | 125-LeuGlnLysArgTyrAspAlaPheLysThr-134 |
| SEQ. ID. NO. 3122 | 141-MetGluPheSerThrAspArgAsnLysIleSerAsp-152 |
| SEQ. ID. NO. 3123 | 158-MetArgGlyArgAspGluAsnGlnPro-166 |
| SEQ. ID. NO. 3124 | 172-SerAlaGluGlyThrAspValAspPhe-180 |
| SEQ. ID. NO. 3125 | 182-ArgLeuThrArgGlnMet-187 |
| SEQ. ID. NO. 3126 | 194-LysGlyValLysThrGluPheAsnArgHisValGluAspIleLysArgGluSerAspGly-213 |
| SEQ. ID. NO. 3127 | 219-ThrAlaAspThrArgAsnProAspGly-227 |
| SEQ. ID. NO. 3128 | 252-GlyIleProGluGlyLysGly-258 |
| SEQ. ID. NO. 3129 | 272-SerAsnProGluThrAlaGluGlnHisAsn-281 |
| SEQ. ID. NO. 3130 | 300-LeuAspThrArgAsnValAspGlyLysArg-309 |
| SEQ. ID. NO. 3131 | 361-GluLeuArgLysThrLysGluGluArgPhe-370 |
| SEQ. ID. NO. 3132 | 380-AlaAsnProAspAspTrpGlu-386 |
| SEQ. ID. NO. 3133 | 395-GlnIleIleLysLysAspSerGluLysGlyGly-405 |
| SEQ. ID. NO. 3134 | 446-PheProGluArgAlaProSerTrpGluAspArgLeuLysGluLeuVal-461 |
| SEQ. ID. NO. 3135 | 467-LysLeuAsnGluAsnProGluArgAlaAspGlu-477 |
| 204-2 | |
| AMPHI Regions - AMPHI | |
| SEQ. ID. NO. 3136 | 43-GlnAlaPheAsnArgIleThrAspLeuPhePhe-53 |
| SEQ. ID. NO. 3137 | 62-AlaLeuSerGlnIle-66 |
| SEQ. ID. NO. 3138 | 70-AsnArgArgIleValAspIlePheAspPheGluAsn-81 |
| SEQ. ID. NO. 3139 | 83-PheArgArgAlaLeuTyrArgValLeuArgLeuPheArgArgIlePheGly-99 |
| Antigenic Index - Jameson-Wolf | |
| SEQ. ID. NO. 3140 | 34-AspGlnSerAspAsnIleLeu-40 |
| SEQ. ID. NO. 3141 | 44-AlaPheAsnArgIle-48 |
| SEQ. ID. NO. 3142 | 66-IleGlnThrGlyAsnArgArgIleValAsp-75 |
| SEQ. ID. NO. 3143 | 77-PheAspPheGluAsnArgPheArgArgAlaLeu-87 |
| SEQ. ID. NO. 3144 | 101-AlaAlaGlyGlyLysGlnGlnAla-108 |

TABLE 1-continued

| | |
|---|---|
| SEQ. ID. NO. 3145 | 112-TyrGlyLysArgCysPhe-117 |
| SEQ. ID. NO. 3146 | 126-SerLysCysArgLeuLysArgGlyArgArgArgPheGlyArgHisArgValHisPheAsnGlyArgMetProThrAlaSerArgThrLeuSer AsnAsnSerArgAlaSerLeu-163 |
| SEQ. ID. NO. 3147 | 169-ProAlaCysLysIle-173 |
| SEQ. ID. NO. 3148 | 177-CysGluGlySerAla-181 |
| Hydrophilic Regions - Hopp-Woods | |
| SEQ. ID. NO. 3149 | 68-ThrGlyAsnArgArgIleValAsp-75 |
| SEQ. ID. NO. 3150 | 77-PheAspPheGluAsnArgPheArgArgAlaLeu-87 |
| SEQ. ID. NO. 3151 | 104-GlyLysGlnGlnAla-108 |
| SEQ. ID. NO. 3152 | 112-TyrGlyLysArgCysPhe-117 |
| SEQ. ID. NO. 3153 | 126-SerLysCysArgLeuLysArgGlyArgArgArgPheGlyArgHisArgVal-142 |
| SEQ. ID. NO. 3154 | 148-MetProThrAlaSerArgThrLeuSerAsnAsnSerArgAlaSerLeu-163 |
| 205-1 (same as orf108, so delete this one) | |
| AMPHI Regions - AMPHI | |
| SEQ. ID. NO. 3155 | 21-SerGluAsnThrAlaGluGlnProGlnAsnAlaValGlnSerAlaProLys-37 |
| SEQ. ID. NO. 3156 | 79-GluGlnAsnValIleArgLeuIleGlyLysHisProGlyAspLeu-93 |
| SEQ. ID. NO. 3157 | 119-HisThrLeuPheAlaLysLeuValGlyAsnIleAlaGluAspGlyGlyLys-135 |
| Antigenic Index - Jameson-Wolf | |
| SEQ. ID. NO. 3158 | 18-CysGlyLysSerGluAsnThrAlaGluGlnProGlnAsnAlaValGlnSerAlaProLysProValPhe-40 |
| SEQ. ID. NO. 3159 | 55-LeuGlyGlnSerSerGluGlyLysThrAsnAspGlyLysLysGlnIle-70 |
| SEQ. ID. NO. 3160 | 73-ProIleLysGlyLeuProGluGlnAsnVal-82 |
| SEQ. ID. NO. 3161 | 86-IleGlyLysHisProGlyAspLeuGluAlaValSerGlyLysCysMetGluThrAspAspLysAspSerProAlaGlyTrpAlaGlu-114 |
| SEQ. ID. NO. 3162 | 129-IleAlaGluAspGlyGlyLysLeuThr-137 |
| SEQ. ID. NO. 3163 | 149-TyrGlnAlaGlyLysSerGlyTyr-156 |
| SEQ. ID. NO. 3164 | 168-IleAspSerGluGly-172 |
| SEQ. ID. NO. 3165 | 175-TyrPheArgArgArgHisTyr-181 |
| Hydrophilic Regions - Hopp-Woods | |
| SEQ. ID. NO. 3166 | 19-GlyLysSerGluAsnThrAlaGluGlnProGln-29 |
| SEQ. ID. NO. 3167 | 56-GlyGlnSerSerGluGlyLysThrAsnAspGlyLysLysGlnIle-70 |
| SEQ. ID. NO. 3168 | 89-HisProGlyAspLeuGluAlaValSer-97 |
| SEQ. ID. NO. 3169 | 99-LysCysMetGluThrAspAspLysAspSerPro-109 |
| SEQ. ID. NO. 3170 | 129-IleAlaGluAspGlyGlyLysLeu-136 |
| SEQ. ID. NO. 3171 | 150-GlnAlaGlyLysSerGly-155 |
| SEQ. ID. NO. 3172 | 168-IleAspSerGluGly-172 |
| SEQ. ID. NO. 3173 | 176-PheArgArgArgHisTyr-181 |
| 206-2 | |
| AMPHI Regions - AMPHI | |
| SEQ. ID. NO. 3174 | 32-ProLysGlnThrValArgGlnIleGlnAlaVal-42 |
| SEQ. ID. NO. 3175 | 44-IleSerHisIleAspArgThrGlnGly-52 |
| SEQ. ID. NO. 3176 | 81-CysSerGlyMetIleGln-86 |
| SEQ. ID. NO. 3177 | 99-ArgThrAlaArgAspMet-104 |
| SEQ. ID. NO. 3178 | 150-SerGlyLysThrIleLysThrGlu-157 |
| Antigenic Index - Jameson-Wolf | |
| SEQ. ID. NO. 3179 | 2-PheProProAspLysThrLeu-8 |
| SEQ. ID. NO. 3180 | 21-GlyThrThrSerGlyLysHisArgGlnProLysProLysGlnThrValArg-37 |
| SEQ. ID. NO. 3181 | 45-SerHisIleAspArgThrGlnGlySerGln-54 |
| SEQ. ID. NO. 3182 | 66-ThrProTyrLysTrpGlyGlySerSerThr-75 |
| SEQ. ID. NO. 3183 | 96-LysLeuProArgThrAlaArgAspMetAlaAlaAlaSerArgLysIleProAspSerArgLeuLysAlaGly-119 |
| SEQ. ID. NO. 3184 | 126-ThrGlyGlyAlaHisArgTyrSer-133 |
| SEQ. ID. NO. 3185 | 148-ProSerSerGlyLysThrIleLysThrGluLysLeuSer-160 |
| Hydrophilic Regions - Hopp-Woods | |
| SEQ. ID. NO. 3186 | 23-ThrSerGlyLysHisArgGlnProLysProLysGlnThrVal-36 |
| SEQ. ID. NO. 3187 | 45-SerHisIleAspArgThrGlnGlySerGln-54 |
| SEQ. ID. NO. 3188 | 96-LysLeuProArgThrAlaArgAspMetAlaAlaAlaSerArgLysIleProAspSerArgLeuLysAlaGly-119 |
| SEQ. ID. NO. 3189 | 149-SerSerGlyLysThrIleLysThrGluLysLeuSer-160 |
| 211-2 | |
| AMPHI Regions - AMPHI | |
| SEQ. ID. NO. 3190 | 18-ValGlyAsnGlyValAspGluPheGlyArgGlyAla-29 |
| SEQ. ID. NO. 3191 | 57-GlnPheGluArgAla-61 |
| SEQ. ID. NO. 3192 | 98-IleGluGlyPheAspLysIleAsnProAla-107 |
| Antigenic Index - Jameson-Wolf | |
| SEQ. ID. NO. 3193 | 8-AsnGlnLeuGlyGlyArgAsnGlyThrAlaValGlyAsnGlyValAspGluPheGlyArgGlyAlaAspAsnGlnValGluPheLeuGlu-37 |
| SEQ. ID. NO. 3194 | 44-GlyAlaSerGlyArgAlaAla-50 |
| SEQ. ID. NO. 3195 | 73-GlyGluAspAspValVal-78 |
| SEQ. ID. NO. 3196 | 100-GlyPheAspLysIleAsnProAlaVal-108 |
| Hydrophilic Regions - Hopp-Woods | |
| SEQ. ID. NO. 3197 | 10-LeuGlyGlyArgAsnGlyThr-16 |
| SEQ. ID. NO. 3198 | 21-GlyValAspGluPheGlyArgGlyAlaAspAsnGlnValGluPheLeuGlu-37 |
| SEQ. ID. NO. 3199 | 73-GlyGluAspAspValVal-78 |
| SEQ. ID. NO. 3200 | 100-GlyPheAspLysIleAsn-105 |
| 212-2 | |
| AMPHI Regions - AMPHI | |
| SEQ. ID. NO. 3201 | 6-TrpAspGlyIleProAspIleArgThr-14 |
| SEQ. ID. NO. 3202 | 40-PheGlnThrAlaGlnAsp-45 |
| SEQ. ID. NO. 3203 | 64-LeuGlnPheAspSerIleAsnLeuIleGluHisIle-75 |
| SEQ. ID. NO. 3204 | 91-HisLeuHisGluHis-95 |
| SEQ. ID. NO. 3205 | 199-ArgLeuLeuGlyHis-203 |
| SEQ. ID. NO. 3206 | 238-HisAsnHisLeuTyrArgSerIleThrSerAlaGluAlaGluLysIle-253 |
| SEQ. ID. NO. 3207 | 397-TrpAsnGluAlaGluGluAla-403 |
| SEQ. ID. NO. 3208 | 439-AspSerProAspHis-443 |

TABLE 1-continued

| | |
|---|---|
| SEQ. ID. NO. 3209 | 445-ProLeuValGlyAlaLeuGlyAspIleAlaAlaMet-456 |
| SEQ. ID. NO. 3210 | 487-HisGlyThrArgGlyLeu-492 |
| SEQ. ID. NO. 3211 | 501-AlaIleAlaAlaGlnIleLeuGlyLeuPro-510 |
| Antigenic Index - Jameson-Wolf | |
| SEQ. ID. NO. 3212 | 8-GlyIleProAspIleArgThrLeuAspGlnAlaIleArgLysHisAlaProProLeuAsn-27 |
| SEQ. ID. NO. 3213 | 33-ProAspAsnGlnIleProAspPheGlnThrAlaGlnAspAlaSerAspAlaGluCysArgLeuLysHisArgLeuAspGln-59 |
| SEQ. ID. NO. 3214 | 85-ProProSerArgThr-89 |
| SEQ. ID. NO. 3215 | 105-AlaIleProGlnThrGluSerLysProAspLysProTrp-117 |
| SEQ. ID. NO. 3216 | 120-LeuProGlnThrSerGluArgGlnLysProGluHis-131 |
| SEQ. ID. NO. 3217 | 158-LeuGluAlaArgLysAlaAlaGln-165 |
| SEQ. ID. NO. 3218 | 168-SerGlyAsnArgGlnGly-173 |
| SEQ. ID. NO. 3219 | 178-LysIleSerProHisAspThrGluGlnThrGlu-188 |
| SEQ. ID. NO. 3220 | 193-GlyTyrGlyTyrThrLys-198 |
| SEQ. ID. NO. 3221 | 205-LeuProGluSerGluThrTrpGlyGlyAsnGly-215 |
| SEQ. ID. NO. 3222 | 220-AsnTyrSerArgThrGluGlnGlnArgAsnHisGluLeuGlyLeu-234 |
| SEQ. ID. NO. 3223 | 246-ThrSerAlaGluAlaGluLysIleAla-254 |
| SEQ. ID. NO. 3224 | 260-ValProTyrAspHisProSerCys-267 |
| SEQ. ID. NO. 3225 | 294-LeuHisGluAspThrProLeu-300 |
| SEQ. ID. NO. 3226 | 302-AspIleSerHisAspGlyGluLysTrpIle-311 |
| SEQ. ID. NO. 3227 | 328-ThrGlyAlaAsnSerProTyrLeuPro-336 |
| SEQ. ID. NO. 3228 | 346-ArgGlnIleArgGlyGlnThrGlyLeuThrProSerThrProPheSerGluGlnLeuArg-365 |
| SEQ. ID. NO. 3229 | 376-ProSerTrpHisGly-380 |
| SEQ. ID. NO. 3230 | 391-AsnSerSerHisThrGlyTrpAsnGluAlaGluGluAlaSerAsnArgGlnAla-408 |
| SEQ. ID. NO. 3231 | 424-AsnProAsnProGlnLysHisGlnGly-432 |
| SEQ. ID. NO. 3232 | 436-IleArgCysAspSerProAspHisLeuPro-445 |
| SEQ. ID. NO. 3233 | 464-AlaLeuAspLysAsnTyrArgIleAspThrProCys-475 |
| SEQ. ID. NO. 3234 | 487-HisGlyThrArgGlyLeuAla-493 |
| SEQ. ID. NO. 3235 | 511-HisProPheSerGlnArgLeuArgHisAlaLeuHisProAsnArgThrIle-527 |
| SEQ. ID. NO. 3236 | 531-IleValArgArgLysAspLeuThrPro-539 |
| Hydrophilic Regions - Hopp-Woods | |
| SEQ. ID. NO. 3237 | 10-ProAspIleArgThrLeuAspGlnAlaIleArgLysHisAlaPro-24 |
| SEQ. ID. NO. 3238 | 44-GlnAspAlaSerAspAlaGluCysArgLeuLysHisArgLeuAspGln-59 |
| SEQ. ID. NO. 3239 | 105-AlaIleProGlnThrGluSerLysProAspLys-115 |
| SEQ. ID. NO. 3240 | 122-GlnThrSerGluArgGlnLysProGluHis-131 |
| SEQ. ID. NO. 3241 | 158-LeuGluAlaArgLysAlaAlaGln-165 |
| SEQ. ID. NO. 3242 | 180-SerProHisAspThrGluGlnThrGlu-188 |
| SEQ. ID. NO. 3243 | 206-ProGluSerGluThr-210 |
| SEQ. ID. NO. 3244 | 222-SerArgThrGluGlnGlnArgAsnHisGlu-231 |
| SEQ. ID. NO. 3245 | 246-ThrSerAlaGluAlaGluLysIleAla-254 |
| SEQ. ID. NO. 3246 | 294-LeuHisGluAspThrProLeu-300 |
| SEQ. ID. NO. 3247 | 303-IleSerHisAspGlyGluLysTrpIle-311 |
| SEQ. ID. NO. 3248 | 346-ArgGlnIleArgGly-350 |
| SEQ. ID. NO. 3249 | 398-AsnGluAlaGluGluAlaSerAsnArgGlnAla-408 |
| SEQ. ID. NO. 3250 | 426-AsnProGlnLysHisGlnGly-432 |
| SEQ. ID. NO. 3251 | 436-IleArgCysAspSerProAsp-442 |
| SEQ. ID. NO. 3252 | 467-LysAsnTyrArgIleAspThr-473 |
| SEQ. ID. NO. 3253 | 515-GlnArgLeuArgHis-519 |
| SEQ. ID. NO. 3254 | 531-IleValArgArgLysAspLeuThrPro-539 |
| 214-1 | |
| AMPHI Regions - AMPHI | |
| SEQ. ID. NO. 3255 | 6-CysLysLeuPheValLeuIle-12 |
| SEQ. ID. NO. 3256 | 69-ValThrArgGlyGlyLysGlyGlyGluSerVal-79 |
| SEQ. ID. NO. 3257 | 88-PheSerGlnThrLeuAsp-93 |
| SEQ. ID. NO. 3258 | 122-LysValGlnArgGlyGlyAspVal-129 |
| SEQ. ID. NO. 3259 | 150-ThrLysSerGlyAlaLysSerAlaSerLys-159 |
| Antigenic Index - Jameson-Wolf | |
| SEQ. ID. NO. 3260 | 23-LeuGlnSerAspSerArgGlnProIle-31 |
| SEQ. ID. NO. 3261 | 33-IleGluAlaAspGlnGlySerLeuAspGlnAlaAsnGlnSerThrThrPheSerGlyAsn-52 |
| SEQ. ID. NO. 3262 | 71-ArgGlyGlyLysGlyGlyGluSerValArgAlaGluGlySerProValArgPheSerGlnThrLeuAspGlyGlyLysGlyThrValArgGlyGlnAla AsnAsn-105 |
| SEQ. ID. NO. 3263 | 119-GlyAsnAlaLysValGlnArgGlyGlyAspValAlaGlu-131 |
| SEQ. ID. NO. 3264 | 137-TyrAsnThrLysThrGluVal-143 |
| SEQ. ID. NO. 3265 | 148-GlySerThrLysSerGlyAlaLysSerAlaSerLysSerGlyArgValSerVal-165 |
| SEQ. ID. NO. 3266 | 168-GlnProSerSerThrGlnLysSerGlu-176 |
| Hydrophilic Regions - Hopp-Woods | |
| SEQ. ID. NO. 3267 | 25-SerAspSerArgGlnProIle-31 |
| SEQ. ID. NO. 3268 | 33-IleGluAlaAspGlnGlySerLeuAspGlnAlaAsn-44 |
| SEQ. ID. NO. 3269 | 71-ArgGlyGlyLysGlyGlyGluSerValArgAlaGluGlySerPro-85 |
| SEQ. ID. NO. 3270 | 92-LeuAspGlyGlyLysGlyThrValArgGlyGlnAla-103 |
| SEQ. ID. NO. 3271 | 121-AlaLysValGlnArgGlyGlyAspValAlaGlu-131 |
| SEQ. ID. NO. 3272 | 148-GlySerThrLysSerGlyAlaLysSerAlaSerLysSerGlyArg-162 |
| SEQ. ID. NO. 3273 | 171-SerThrGlnLysSerGlu-176 |
| 215-2 | |
| AMPHI Regions - AMPHI | |
| SEQ. ID. NO. 3274 | 21-SerLeuSerAlaTrpLeuGlyArgIle-29 |
| SEQ. ID. NO. 3275 | 67-SerAlaLysGlyAlaLysGlnPheProGlu-76 |
| Antigenic Index - Jameson-Wolf | |
| SEQ. ID. NO. 3276 | 3-ValArgTrpArgTyrGly-8 |
| SEQ. ID. NO. 3277 | 28-ArgIleSerGluValGluIleGluGluValArgLeuAsnProAspGluProGlnTyrThrMetAspGlyLeuAspGlyArgArgPheAspGluGlnGly TyrLeuLys-63 |

TABLE 1-continued

| | |
|---|---|
| SEQ. ID. NO. 3278 | 65-HisLeuSerAlaLysGlyAlaLysGlnPheProGluSerSerAspIleHisPheAspSerProHisLeu-87 |
| SEQ. ID. NO. 3279 | 99-ValGlySerAspGluAlaValTyrHisThrGluAsnLysGlnValLeuPhe-115 |
| SEQ. ID. NO. 3280 | 123-LysThrAlaAspGlyLysArgGlnAlaGlyLysValGluAlaGluLysLeuHisValAspThrGluSerGlnTyrAlaGlnThrAspThrProVal-154 |
| SEQ. ID. NO. 3281 | 160-AlaSerHisGlyGlnAlaGlyGlyMetThrTyrAspHisLysThrGly-175 |
| SEQ. ID. NO. 3282 | 179-PheSerSerLysValLys-184 |
| SEQ. ID. NO. 3283 | 187-IleTyrAspThrLysAspMet-193 |
| Hydrophilic Regions - Hopp-Woods | |
| SEQ. ID. NO. 3284 | 29-IleSerGluValGluIleGluGluValArgLeuAsnProAspGluProGlnTyr-46 |
| SEQ. ID. NO. 3285 | 49-AspGlyLeuAspGlyArgArgPheAspGlu-58 |
| SEQ. ID. NO. 3286 | 65-HisLeuSerAlaLysGlyAlaLysGlnPheProGluSerSerAspIleHisPhe-82 |
| SEQ. ID. NO. 3287 | 99-ValGlySerAspGluAlaValTyr-106 |
| SEQ. ID. NO. 3288 | 108-ThrGluAsnLysGlnValLeu-114 |
| SEQ. ID. NO. 3289 | 123-LysThrAlaAspGlyLysArgGlnAlaGlyLysValGluAlaGluLysLeuHisValAspThrGluSerGlnTyrAla-148 |
| SEQ. ID. NO. 3290 | 170-TyrAspHisLysThr-174 |
| SEQ. ID. NO. 3291 | 187-IleTyrAspThrLysAspMet-193 |
| 216-2 | |
| AMPHI Regions - AMPHI | |
| SEQ. ID. NO. 3292 | 6-LysTyrLeuAspTrpAlaArg-12 |
| SEQ. ID. NO. 3293 | 19-AlaGluGlyLeuArgGluIleAlaAlaGluLeu-29 |
| SEQ. ID. NO. 3294 | 60-ArgLysMetAlaAla-64 |
| SEQ. ID. NO. 3295 | 165-LeuGlyAspAlaLeuAlaVal-171 |
| SEQ. ID. NO. 3296 | 201-ValAlaAspIleMetHis-206 |
| SEQ. ID. NO. 3297 | 216-LeuGlyThrProLeuLysGlu-222 |
| SEQ. ID. NO. 3298 | 242-GlyArgLeuLysGlyVal-247 |
| SEQ. ID. NO. 3299 | 251-GlyAspLeuArgArgLeuPheGlnGluCysAspAsnPheThrGlyLeuSerIle-268 |
| SEQ. ID. NO. 3300 | 272-MetHisThrHisProLysThrIleSerAla-281 |
| SEQ. ID. NO. 3301 | 290-LysValMetGlnAlaAsn-295 |
| Antigenic Index - Jameson-Wolf | |
| SEQ. ID. NO. 3302 | 1-MetAlaGluAsnGlyLysTyr-7 |
| SEQ. ID. NO. 3303 | 14-ValLeuHisAlaGluAlaGluGlyLeuArgGluIleAlaAlaGluLeuAspLysAsnPhe-33 |
| SEQ. ID. NO. 3304 | 43-CysLysGlyArgVal-47 |
| SEQ. ID. NO. 3305 | 51-GlyMetGlyLysSerGlyHisIleGlyArgLysMetAla-63 |
| SEQ. ID. NO. 3306 | 80-GluAlaAlaHisGlyAspLeu-86 |
| SEQ. ID. NO. 3307 | 90-ValAspAsnAspVal-94 |
| SEQ. ID. NO. 3308 | 99-SerAsnSerGlyGluSerAspGluIle-107 |
| SEQ. ID. NO. 3309 | 113-AlaLeuLysArgLysAspIle-119 |
| SEQ. ID. NO. 3310 | 125-ThrAlaArgProAspSerThrMetAlaArgHisAlaAsp-137 |
| SEQ. ID. NO. 3311 | 144-ValSerLysGluAlaCysPro-150 |
| SEQ. ID. NO. 3312 | 177-ArgAlaPheThrProAspAspPheAla-185 |
| SEQ. ID. NO. 3313 | 188-HisProAlaGlySerLeuGlyLys-195 |
| SEQ. ID. NO. 3314 | 203-AspIleMetHisLysGlyGlyGlyLeuProAla-213 |
| SEQ. ID. NO. 3315 | 216-LeuGlyThrProLeuLysGluAlaIle-224 |
| SEQ. ID. NO. 3316 | 227-MetSerGluLysGlyLeu-232 |
| SEQ. ID. NO. 3317 | 237-ValThrAspGlyGlnGlyArgLeuLysGly-246 |
| SEQ. ID. NO. 3318 | 248-PheThrAspGlyAspLeuArgArgLeuPheGlnGluCysAspAsnPheThr-264 |
| SEQ. ID. NO. 3319 | 275-HisProLysThrIleSerAlaGluArgLeuAlaThrGluAlaLeuLys-290 |
| SEQ. ID. NO. 3320 | 303-ThrAspAlaAspGly-307 |
| Hydrophilic Regions - Hopp-Woods | |
| SEQ. ID. NO. 3321 | 1-MetAlaGluAsnGlyLys-6 |
| SEQ. ID. NO. 3322 | 14-ValLeuHisAlaGluAlaGluGlyLeuArgGluIleAlaAlaGluLeuAspLys-31 |
| SEQ. ID. NO. 3323 | 43-CysLysGlyArgVal-47 |
| SEQ. ID. NO. 3324 | 56-GlyHisIleGlyArgLysMetAla-63 |
| SEQ. ID. NO. 3325 | 100-AsnSerGlyGluSerAspGluIle-107 |
| SEQ. ID. NO. 3326 | 113-AlaLeuLysArgLysAspIle-119 |
| SEQ. ID. NO. 3327 | 126-AlaArgProAspSerThrMetAlaArgHisAlaAsp-137 |
| SEQ. ID. NO. 3328 | 144-ValSerLysGluAlaCys-149 |
| SEQ. ID. NO. 3329 | 177-ArgAlaPheThrProAspAspPheAla-185 |
| SEQ. ID. NO. 3330 | 218-ThrProLeuLysGluAlaIle-224 |
| SEQ. ID. NO. 3331 | 227-MetSerGluLysGlyLeu-232 |
| SEQ. ID. NO. 3332 | 239-AspGlyGlnGlyArgLeuLys-245 |
| SEQ. ID. NO. 3333 | 251-GlyAspLeuArgArgLeuPheGlnGluCysAspAsn-262 |
| SEQ. ID. NO. 3334 | 277-LysThrIleSerAlaGluArgLeuAlaThrGluAlaLeuLys-290 |
| SEQ. ID. NO. 3335 | 303-ThrAspAlaAspGly-307 |
| 218-2 | |
| AMPHI Regions - AMPHI | |
| SEQ. ID. NO. 3336 | 37-LeuLeuAlaValThr-41 |
| SEQ. ID. NO. 3337 | 121-AlaLysValValSerThrMet-127 |
| SEQ. ID. NO. 3338 | 136-ThrMetAspGluIleHisSer-142 |
| SEQ. ID. NO. 3339 | 190-AlaArgSerTrpTrpArgAsnLeuHisGlyThrPheGlyThrTrpValSerLeuIleLeu-209 |
| SEQ. ID. NO. 3340 | 223-TrpGlyGlyLysPheValGlnAlaTrpSerGlnPhePro-235 |
| SEQ. ID. NO. 3341 | 288-AspGluProMetThrLeuGluThrValAspArgPheAlaArgGlu-302 |
| SEQ. ID. NO. 3342 | 359-TyrAsnProPheGlyLysPheMet-366 |
| SEQ. ID. NO. 3343 | 377-LeuGlyTrpTrpSerValLeuAlaAsn-385 |
| Antigenic Index - Jameson-Wolf | |
| SEQ. ID. NO. 3344 | 3-ThrGlnIleLysThrGluAlaAspAsnGlnSerAsnArgArgTyrLeu-18 |
| SEQ. ID. NO. 3345 | 51-IleThrGlyLysGluGlyGluArgIleHis-60 |
| SEQ. ID. NO. 3346 | 74-AlaGluAlaAlaArgSerAlaValAsnProGluThrSerSer-87 |
| SEQ. ID. NO. 3347 | 94-ProArgAlaAspAspMet-99 |
| SEQ. ID. NO. 3348 | 105-ValAsnAsnGluGlyLysAla-111 |
| SEQ. ID. NO. 3349 | 125-SerThrMetProArgAsnGlnGlyTrp-133 |

TABLE 1-continued

| | |
|---|---|
| SEQ. ID. NO. 3350 | 174-ValLysArgArgGlyIleLysAla-181 |
| SEQ. ID. NO. 3351 | 183-LeuLeuProSerLysGlyArgAlaArgSerTrpTrp-194 |
| SEQ. ID. NO. 3352 | 196-AsnLeuHisGlyThrPheGly-202 |
| SEQ. ID. NO. 3353 | 235-ProAlaGlyLysTrpGlyValGluProAsnProVal-246 |
| SEQ. ID. NO. 3354 | 255-ValLeuAsnAspGlyLysValLysGlu-263 |
| SEQ. ID. NO. 3355 | 279-ThrValGlyLysAspGlyIleAsnProAspGluProMetThr-292 |
| SEQ. ID. NO. 3356 | 294-GluThrValAspArgPheAlaArg-301 |
| SEQ. ID. NO. 3357 | 303-IleGlyPheLysGlyArgTyrGlnLeuAsnLeuProLysGlyGluAspGly-319 |
| SEQ. ID. NO. 3358 | 323-LeuSerGlnAspSerMetSerTyr-330 |
| SEQ. ID. NO. 3359 | 336-PheAlaAspArgThrValHis-342 |
| SEQ. ID. NO. 3360 | 344-AspGlnTyrSerGlyLysIleLeuAla-352 |
| SEQ. ID. NO. 3361 | 354-IleArgPheAspAspTyrAsnProPhe-362 |
| SEQ. ID. NO. 3362 | 404-TrpLysArgArgProThrGlyAla-411 |
| SEQ. ID. NO. 3363 | 417-ProAlaGlnLysValLysLeu-423 |
| Hydrophilic Regions - Hopp-Woods | |
| SEQ. ID. NO. 3364 | 3-ThrGlnIleLysThrGluAlaAspAsnGlnSerAsnArgArgTyr-17 |
| SEQ. ID. NO. 3365 | 52-ThrGlyLysGluGlyGluArgIleHis-60 |
| SEQ. ID. NO. 3366 | 74-AlaGluAlaAlaArgSerAlaValAsnProGluThrSerSer-87 |
| SEQ. ID. NO. 3367 | 94-ProArgAlaAspAspMet-99 |
| SEQ. ID. NO. 3368 | 105-ValAsnAsnGluGlyLysAla-111 |
| SEQ. ID. NO. 3369 | 175-LysArgArgGlyIleLys-180 |
| SEQ. ID. NO. 3370 | 186-SerLysGlyArgAla-190 |
| SEQ. ID. NO. 3371 | 255-ValLeuAsnAspGlyLysValLysGlu-263 |
| SEQ. ID. NO. 3372 | 279-ThrValGlyLysAspGlyIleAsnProAspGluProMetThr-292 |
| SEQ. ID. NO. 3373 | 294-GluThrValAspArgPheAlaArg-301 |
| SEQ. ID. NO. 3374 | 314-ProLysGlyGluAspGly-319 |
| SEQ. ID. NO. 3375 | 325GlnAspSerMetSer-329 |
| SEQ. ID. NO. 3376 | 336-PheAlaAspArgThrValHis-342 |
| SEQ. ID. NO. 3377 | 354-IleArgPheAspAsp-358 |
| SEQ. ID. NO. 3378 | 405-LysArgArgProThrGly-410 |
| 219-2 (included in 218, so delete this one) | |
| AMPHI Regions - AMPHI | |
| SEQ. ID. NO. 3379 | 37-LeuLeuAlaValThr-41 |
| SEQ. ID. NO. 3380 | 121-AlaLysValValSerThrMet-127 |
| SEQ. ID. NO. 3381 | 136-ThrMetAspGluIleHisSer-142 |
| SEQ. ID. NO. 3382 | 190-AlaArgSerTrpTrpArgAsnLeuHisGlyThrPheGlyThrTrpValSerLeuIleLeu-209 |
| SEQ. ID. NO. 3383 | 223-TrpGlyGlyLysPheValGlnAlaTrpSerGlnPhePro-235 |
| SEQ. ID. NO. 3384 | 288-AspGluProMetThrLeuGluThrValAspArgPheAlaArgGlu-302 |
| SEQ. ID. NO. 3385 | 359-TyrAsnProPheGlyLysPheMet-366 |
| SEQ. ID. NO. 3386 | 377-LeuGlyTrpTrpSerValLeuAlaAsn-385 |
| Antigenic Index - Jameson-Wolf | |
| SEQ. ID. NO. 3387 | 3-ThrGlnIleLysThrGluAlaAspAsnGlnSerAsnArgArgTyrLeu-18 |
| SEQ. ID. NO. 3388 | 51-IleThrGlyLysGluGlyGluArgIleHis-60 |
| SEQ. ID. NO. 3389 | 74-AlaGluAlaAlaArgSerAlaValAsnProGluThrSerSer-87 |
| SEQ. ID. NO. 3390 | 94-ProArgAlaAspAspMet-99 |
| SEQ. ID. NO. 3391 | 105-ValAsnAsnGluGlyLysAla-111 |
| SEQ. ID. NO. 3392 | 125-SerThrMetProArgAsnGlnGlyTrp-133 |
| SEQ. ID. NO. 3393 | 174-ValLysArgArgGlyIleLysAla-181 |
| SEQ. ID. NO. 3394 | 183-LeuLeuProSerLysGlyArgAlaArgSerTrpTrp-194 |
| SEQ. ID. NO. 3395 | 196-AsnLeuHisGlyThrPheGly-202 |
| SEQ. ID. NO. 3396 | 235-ProAlaGlyLysTrpGlyValGluProAsnProVal-246 |
| SEQ. ID. NO. 3397 | 255-ValLeuAsnAspGlyLysValLysGlu-263 |
| SEQ. ID. NO. 3398 | 279-ThrValGlyLysAspGlyIleAsnProAspGluProMetThr-292 |
| SEQ. ID. NO. 3399 | 294-GluThrValAspArgPheAlaArg-301 |
| SEQ. ID. NO. 3400 | 303-IleGlyPheLysGlyArgTyrGlnLeuAsnLeuProLysGlyGluAspGly-319 |
| SEQ. ID. NO. 3401 | 323-LeuSerGlnAspSerMetSerTyr-330 |
| SEQ. ID. NO. 3402 | 336-PheAlaAspArgThrValHis-342 |
| SEQ. ID. NO. 3403 | 344-AspGlnTyrSerGlyLysIleLeuAla-352 |
| SEQ. ID. NO. 3404 | 354-IleArgPheAspAspTyrAsnProPhe-362 |
| SEQ. ID. NO. 3405 | 404-TrpLysArgArgProThrGlyAla-411 |
| SEQ. ID. NO. 3406 | 417-ProAlaGlnLysValLysLeu-423 |
| Hydrophilic Regions - Hopp-Woods | |
| SEQ. ID. NO. 3407 | 3-ThrGlnIleLysThrGluAlaAspAsnGlnSerAsnArgArgTyr-17 |
| SEQ. ID. NO. 3408 | 52-ThrGlyLysGluGlyGluArgIleHis-60 |
| SEQ. ID. NO. 3409 | 74-AlaGluAlaAlaArgSerAlaValAsnProGluThrSerSer-87 |
| SEQ. ID. NO. 3410 | 94ProArgAlaAspAspMet-99 |
| SEQ. ID. NO. 3411 | 105-ValAsnAsnGluGlyLysAla-111 |
| SEQ. ID. NO. 3412 | 175-LysArgArgGlyIleLys-180 |
| SEQ. ID. NO. 3413 | 186-SerLysGlyArgAla-190 |
| SEQ. ID. NO. 3414 | 255-ValLeuAsnAspGlyLysValLysGlu-263 |
| SEQ. ID. NO. 3415 | 279-ThrValGlyLysAspGlyIleAsnProAspGluProMetThr-292 |
| SEQ. ID. NO. 3416 | 294-GluThrValAspArgPheAlaArg-301 |
| SEQ. ID. NO. 3417 | 314-ProLysGlyGluAspGly-319 |
| SEQ. ID. NO. 3418 | 325-GlnAspSerMetSer-329 |

TABLE 1-continued

| | |
|---|---|
| SEQ. ID. NO. 3419 | 336-PheAlaAspArgThrValHis-342 |
| SEQ. ID. NO. 3420 | 354-IleArgPheAspAsp-358 |
| SEQ. ID. NO. 3421 | 405-LysArgArgProThrGly-410 |
| 225-1 | |
| AMPHI Regions - AMPHI | |
| SEQ. ID. NO. 3422 | 23-LeuAlaAspGluLeuThrAsn-29 |
| SEQ. ID. NO. 3423 | 37-IleLeuArgGlnPhe-41 |
| SEQ. ID. NO. 3424 | 126-AsnAlaMetGlyLeu-130 |
| SEQ. ID. NO. 3425 | 151-PheMetGlnHisIlePheLys-157 |
| SEQ. ID. NO. 3426 | 217-ThrGlyLysAsnIle-221 |
| Antigenic Index - Jameson-Wolf | |
| SEQ. ID. NO. 3427 | 22-AlaLeuAlaAspGluLeuThr-28 |
| SEQ. ID. NO. 3428 | 32-SerSerArgGluGlnIleLeu-38 |
| SEQ. ID. NO. 3429 | 41-PheAlaGluAspGluGlnProVal-48 |
| SEQ. ID. NO. 3430 | 52-AsnArgAlaProAlaArgArgAlaGlyAsnAlaAspGluLeuIle-66 |
| SEQ. ID. NO. 3431 | 71-GlyLeuAsnGluGlnProVal-77 |
| SEQ. ID. NO. 3432 | 81-AsnArgValProAlaArgArgAlaGlyAsnAlaAspGluLeuIle-95 |
| SEQ. ID. NO. 3433 | 100-GlyLeuAsnGluGlnProVal-106 |
| SEQ. ID. NO. 3434 | 108-ProValAsnArgAlaProAlaArgArgAlaGlyAsnAlaAspGluLeuIle-124 |
| SEQ. ID. NO. 3435 | 144-ThrGlyPheAspCysSerGly-150 |
| SEQ. ID. NO. 3436 | 164-LeuProArgThrSerAlaGluGlnAlaArgMet-174 |
| SEQ. ID. NO. 3437 | 176-ThrProValAlaArgSerGluLeuGlnProGlyAsp-187 |
| SEQ. ID. NO. 3438 | 194-LeuGlyGlySerArgIle-199 |
| SEQ. ID. NO. 3439 | 213-HisAlaProArgThrGlyLysAsnIleGlu-222 |
| SEQ. ID. NO. 3440 | 225-SerLeuSerHisLysTyrTrpSerGlyLys-234 |
| SEQ. ID. NO. 3441 | 239-ArgArgValLysLysAsnAspProSerArgPhe-249 |
| Hydrophilic Regions - Hopp-Woods | |
| SEQ. ID. NO. 3442 | 22-AlaLeuAlaAspGluLeuThr-28 |
| SEQ. ID. NO. 3443 | 32-SerSerArgGluGlnIleLeu-38 |
| SEQ. ID. NO. 3444 | 41-PheAlaGluAspGluGlnPro-47 |
| SEQ. ID. NO. 3445 | 53-ArgAlaProAlaArgArgAlaGlyAsnAlaAspGluLeuIle-66 |
| SEQ. ID. NO. 3446 | 83-ValProAlaArgArgAlaGlyAsnAlaAspGluLeuIle-95 |
| SEQ. ID. NO. 3447 | 111-ArgAlaProAlaArgArgAlaGlyAsnAlaAspGluLeuIle-124 |
| SEQ. ID. NO. 3448 | 166-ArgThrSerAlaGluGlnAlaArgMet-174 |
| SEQ. ID. NO. 3449 | 178-ValAlaArgSerGluLeuGlnPro-185 |
| SEQ. ID. NO. 3450 | 216-ArgThrGlyLysAsnIleGlu-222 |
| SEQ. ID. NO. 3451 | 239-ArgArgValLysLysAsnAspProSerArg-248 |
| 226 | |
| AMPHI Regions - AMPHI | |
| SEQ. ID. NO. 3452 | 44-LeuIleAlaTyrLeuLys-49 |
| SEQ. ID. NO. 3453 | 61-AlaAlaGlnPheIleAspPheTrpLeu-69 |
| SEQ. ID. NO. 3454 | 98-GlnLeuAlaGlySerValThrGlyIleValThr-108 |
| SEQ. ID. NO. 3455 | 141-ArgSerIleGlyGlyIleProAlaIleThr-150 |
| SEQ. ID. NO. 3456 | 157-AlaGlyLeuValGlyGlnIleAlaGlyTyrLys-167 |
| SEQ. ID. NO. 3457 | 197-GluArgSerArgArg-201 |
| Antigenic Index - Jameson-Wolf | |
| SEQ. ID. NO. 3458 | 3-GluIleLeuArgGlnProSer-9 |
| SEQ. ID. NO. 3459 | 25-ValArgThrArgThrGlyAsnIle-32 |
| SEQ. ID. NO. 3460 | 81-TyrGlnAsnArgArgLysIle-87 |
| SEQ. ID. NO. 3461 | 117-GlyAlaGluArgGluVal-122 |
| SEQ. ID. NO. 3462 | 128-SerLysSerValThrAsn-133 |
| SEQ. ID. NO. 3463 | 139-IleThrArgSerIleGlyGly-145 |
| SEQ. ID. NO. 3464 | 167-LysMetLeuLysAsnThrVal-173 |
| SEQ. ID. NO. 3465 | 195-SerLeuGluArgSerArgArgMetAla-203 |
| Hydrophilic Regions - Hopp-Woods | |
| SEQ. ID. NO. 3466 | 25-ValArgThrArgThr-29 |
| SEQ. ID. NO. 3467 | 82-GlnAsnArgArgLysIle-87 |
| SEQ. ID. NO. 3468 | 117-GlyAlaGluArgGluVal-122 |
| SEQ. ID. NO. 3469 | 195-SerLeuGluArgSerArgArgMetAla-203 |
| 227-2 | |
| AMPHI Regions - AMPHI | |
| SEQ. ID. NO. 3470 | 36-GlyValLeuPheAlaLeuLeuGlnAla-44 |
| SEQ. ID. NO. 3471 | 52-LeuGlnGlnLeuThrAspAlaLeu-59 |
| SEQ. ID. NO. 3472 | 74-ValIleSerTyrLeuAspLeuIleAlaAspAspTrpPheSer-87 |
| 228 | |
| AMPHI Regions - AMPHI | |
| SEQ. ID. NO. 3473 | 24-GluValLysGluAlaValGlnAlaValGlu-33 |
| SEQ. ID. NO. 3474 | 40-AlaAlaSerAlaAlaGluSerAlaAlaSerAlaValGluGluAlaLysAspGlnValLysAspAla-61 |
| SEQ. ID. NO. 3475 | 78-GluAlaValThrGluAlaAlaLysAspThrLeuAsnLysAlaAlaAspAlaThrGlnGluAlaAlaAspLysMetLysAspAlaAla-106 |
| Antigenic Index - Jameson-Wolf | |
| SEQ. ID. NO. 3476 | 18-SerGlnGluAlaLysGlnGluValLysGluAlaValGln-30 |
| SEQ. ID. NO. 3477 | 32-ValGluSerAspValLysAspThrAlaAlaSerAlaAlaGluSerAlaAlaSerAlaValGluGluAlaLysAspGlnValLysAspAlaAlaAlaAsp AlaLysAlaSerAlaGluGluAlaValThrGluAlaLysGluAlaValThrGluAlaAlaLysAspThrLeuAsnLysAlaAlaAspAlaThrGlnGluAla AlaAspLysMetLysAspAlaAlaLys-107 |

TABLE 1-continued

Hydrophilic Regions - Hopp-Woods
SEQ. ID. NO. 3478 18-SerGlnGluAlaLysGlnGluValLysGluAlaValGln-30
SEQ. ID. NO. 3479 32-ValGluSerAspValLysAspThrAlaAlaSerAlaAlaGluSerAlaAlaSerAlaValGluGluAlaLysAspGlnValLysAspAlaAlaAlaAsp AlaLysAlaSerAlaGluGluAlaValThrGluAlaLysGluAlaValThrGluAlaAlaLysAspThrLeuAsnLysAlaAlaAspAlaThrGlnGluAla AlaAspLysMetLysAspAlaAlaLys-107
230-1
AMPHI Regions - AMPHI
SEQ. ID. NO. 3480 6-GluLysTyrArgThr-10
SEQ. ID. NO. 3481 49-AspHisSerIleAsnAsn-54
SEQ. ID. NO. 3482 56-IleGlnAsnGluGln-60
SEQ. ID. NO. 3483 73-GlnSerLeuLeuGln-77
SEQ. ID. NO. 3484 81-LeuLysGlnGlyAlaLys-86
SEQ. ID. NO. 3485 96-GlnIleLysGlnIleIle-101
SEQ. ID. NO. 3486 133-PheValGluGluIleArgAspGlnPhe-141
SEQ. ID. NO. 3487 144-GlnAsnLeuValAsnLeuVal-150
SEQ. ID. NO. 3488 161-AlaGluGlnLeuIleArgLeuThrGlnValAsnArgThrIleArg-175
SEQ. ID. NO. 3489 184-PheIleAlaGlnVal-188
SEQ. ID. NO. 3490 194-AspLeuGlnLysPheTyrAsn-200
SEQ. ID. NO. 3491 234-GluValLysAsnAlaPheGluGluArgValAlaArgLeu-246
SEQ. ID. NO. 3492 272-ValAlaAspPheAsnLys-277
SEQ. ID. NO. 3493 284-AspAspAlaPheAsnHisProSerSerLeuAlaGluAla-296
SEQ. ID. NO. 3494 319-SerGlyMetProGluAsnLeuIleAsnAlaVal-329
SEQ. ID. NO. 3495 398-LeuAsnGlyGlyLys-402
SEQ. ID. NO. 3496 426-GluAlaTyrAlaGluLeu-431
SEQ. ID. NO. 3497 444-ValArgLeuIleGlyLeuProAlaPro-452
SEQ. ID. NO. 3498 456-GluValGlnAlaValThrProProAspAspIleAla-467
SEQ. ID. NO. 3499 488-LeuLeuIleArgTyrPheAsn-494
AntigenicIndex -Jameson-Wolf
SEQ. ID. NO. 3500 4-SerIleGluLysTyrArgThrProAla-12
SEQ. ID. NO. 3501 32-SerHisProGlyAlaAsp-37
SEQ. ID. NO. 3502 42-ValGlyAspGluLysIleSerAspHisSerIle-52
SEQ. ID. NO. 3503 56-IleGlnAsnGluGlnAlaAspGlyGlyGlyProSerArgAspAlaVal-71
SEQ. ID. NO. 3504 80-TyrLeuLysGlnGlyAla-85
SEQ. ID. NO. 3505 92-ValSerSerGluGlnIleLys-98
SEQ. ID. NO. 3506 101-IleValAspAspProAsnPheHisAspAlaAsnGlyLysPheAsp-115
SEQ. ID. NO. 3507 122-TyrLeuSerGlnArgHisMetSerGluAspGlnPheValGluGluIleArgAsp-139
SEQ. ID. NO. 3508 169-GlnValAsnArgThrIleArgSerHisThrPheAsnProAspGluPhe-184
SEQ. ID. NO. 3509 189-LysValSerGluAlaAspLeu-195
SEQ. ID. NO. 3510 199-TyrAsnAlaAsnLysLysAspTyrLeu-207
SEQ. ID. NO. 3511 223-AspPheAlaAspLysGlnThrValSerGluThrGluValLysAsnAlaPheGluGluArgValAlaArg-245
SEQ. ID. NO. 3512 247-ProAlaAsnGluAlaLysProSerPheGluGlnGluLysAlaAlaValGluAsnGluLeuLysMetLysLysAlaValAlaAspPheAsnLysAla LysGluLysLeuGlyAspAspAlaPheAsnHisProSerSerLeuAlaGluAlaAlaLysAsnSerGlyLeuLysValGluThrGlnGluThrTrpLeu SerArgGlnAspAlaGlnMetSerGlyMetProGluAsn-324
SEQ. ID. NO. 3513 330-PheSerAspAspValLeuLysLysLysHisAsnSerGlu-342
SEQ. ID. NO. 3514 355-ArgAlaLysGluValArgGluGluLysThrLeuPro-366
SEQ. ID. NO. 3515 368-AlaGluAlaLysAspAlaValArg-375
SEQ. ID. NO. 3516 377-AlaTyrIleArgThrGluAlaAlaLysLeuAlaGluAsnLysAlaLysAspValLeu-395
SEQ. ID. NO. 3517 399-AsnGlyGlyLysAlaValAsp-405
SEQ. ID. NO. 3518 417-GlnGlnAlaArgGlnSerMetProProGluAlaTyr-428
SEQ. ID. NO. 3519 432-LeuLysAlaLysProAlaAsnGlyLysProAla-442
SEQ. ID. NO. 3520 459-AlaValThrProProAspAspIleAla-467
SEQ. ID. NO. 3521 476-AlaLeuAlaGlnGlnGlnSerAlaAsnThrPhe-486
SEQ. ID. NO. 3522 493-PheAsnGlyLysIleLysGlnThrLysGlyAlaGlnSerValAspAsnGlyAspGlyGln-512
Hydrophilic Regions - Hopp-Woods
SEQ. ID. NO. 3523 6-GluLysTyrArgThr-10
SEQ. ID. NO. 3524 42-ValGlyAspGluLysIleSerAsp-49
SEQ. ID. NO. 3525 56-IleGlnAsnGluGlnAlaAspGlyGlyGlyProSerArgAspAlaVal-71
SEQ. ID. NO. 3526 92-ValSerSerGluGlnIleLys-98
SEQ. ID. NO. 3527 101-IleValAspAspProAsnPhe-107
SEQ. ID. NO. 3528 110-AlaAsnGlyLysPheAsp-115
SEQ. ID. NO. 3529 126-ArgHisMetSerGluAspGlnPheValGluGluIleArgAsp-139
SEQ. ID. NO. 3530 189-LysValSerGluAlaAspLeu-195
SEQ. ID. NO. 3531 200-AsnAlaAsnLysLysAspTyrLeu-207
SEQ. ID. NO. 3532 223-AspPheAlaAspLysGlnThrValSerGluThrGluValLysAsnAlaPheGluGluArgValAlaArg-245
SEQ. ID. NO. 3533 247-ProAlaAsnGluAlaLysProSerPheGluGlnGluLysAlaAlaValGluAsnGluLeuLysMetLysLysAlaValAlaAspPheAsnLysAlaLys GluLysLeuGlyAspAspAlaPhe-287
SEQ. ID. NO. 3534 292-SerLeuAlaGluAlaAlaLysAsnSerGlyLeuLysValGluThrGlnGlu-308
SEQ. ID. NO. 3535 310-TrpLeuSerArgGlnAspAlaGlnMet-318
SEQ. ID. NO. 3536 333-AspValLeuLysLysLysHisAsnSer-341
SEQ. ID. NO. 3537 355-ArgAlaLysGluValArgGluGluLysThrLeuPro-366
SEQ. ID. NO. 3538 368-AlaGluAlaLysAspAlaValArg-375
SEQ. ID. NO. 3539 377-AlaTyrIleArgThrGluAlaAlaLysLeuAlaGluAsnLysAlaLysAspValLeu-395
SEQ. ID. NO. 3540 417-GlnGlnAlaArgGlnSerMetPro-424
SEQ. ID. NO. 3541 432-LeuLysAlaLysProAlaAsnGly-439
SEQ. ID. NO. 3542 461-ThrProProAspAspIleAla-467
SEQ. ID. NO. 3543 496-LysIleLysGlnThrLysGlyAlaGlnSerValAspAsnGlyAspGlyGln-512
231-1
AMPHI Regions - AMPHI
SEQ. ID. NO. 3544 7-IleAsnArgProTyrGlnLysProAlaGluLeu-17
SEQ. ID. NO. 3545 98-ArgIlePheSerPheProGln-104

TABLE 1-continued

| | |
|---|---|
| SEQ. ID. NO. 3546 | 209-AlaValAspAsnValLysGlyValAlaVal-218 |
| SEQ. ID. NO. 3547 | 228-AlaValAlaGlyPheArgArgCysSerAlaAla-238 |
| SEQ. ID. NO. 3548 | 263-LeuAlaAlaValProArgIleThrGln-271 |
| SEQ. ID. NO. 3549 | 281-LysProPheHisAspPhePheAsnLeu-289 |
| Antigenic Index - Jameson-Wolf | |
| SEQ. ID. NO. 3550 | 1-MetSerLysArgLysSerIleAsnArgProTyrGlnLysProAlaGlu-16 |
| SEQ. ID. NO. 3551 | 18-ProProLeuGlnAsnAsnProProPheTyrArgLysAsnArgArgLeuAsn-34 |
| SEQ. ID. NO. 3552 | 39-AlaAspGlyGlyCysAlaSerProGlnLysCysArgAlaArgGlyPheGln-55 |
| SEQ. ID. NO. 3553 | 90-SerAlaValArgProArgArgLeuArg-98 |
| SEQ. ID. NO. 3554 | 135-MetProArgArgProVal-140 |
| SEQ. ID. NO. 3555 | 150-PheAlaAspArgAsnLeuArg-156 |
| SEQ. ID. NO. 3556 | 174-AlaPheArgArgArgAlaGlnVal-181 |
| SEQ. ID. NO. 3557 | 183-AlaArgThrArgAla-187 |
| SEQ. ID. NO. 3558 | 194-ArgArgValAspIleArgHisProAspPhe-203 |
| SEQ. ID. NO. 3559 | 211-AspAsnValLysGly-215 |
| SEQ. ID. NO. 3560 | 231-GlyPheArgArgCysSerAlaAlaGlyGlyArgValGlyThr-244 |
| SEQ. ID. NO. 3561 | 246-ValProCysArgAlaGluTyrValGluTyrGlyAsnArgArgProHisArgLeuAlaAla-265 |
| SEQ. ID. NO. 3562 | 269-IleThrGlnArgThrGlnLysArgGlnGlyAspGlyLysProPhe-283 |
| SEQ. ID. NO. 3563 | 294-MetProMetProSerGluHis |
| Hydrophilic Regions - Hopp-Woods | |
| SEQ. ID. NO. 3564 | 1-MetSerLysArgLysSerIleAsn-8 |
| SEQ. ID. NO. 3565 | 10-ProTyrGlnLysProAlaGlu-16 |
| SEQ. ID. NO. 3566 | 26-PheTyrArgLysAsnArgArg-32 |
| SEQ. ID. NO. 3567 | 45-SerProGlnLysCysArgAlaArgGly-53 |
| SEQ. ID. NO. 3568 | 92-ValArgProArgArgLeuArg-98 |
| SEQ. ID. NO. 3569 | 136-ProArgArgProVal-140 |
| SEQ. ID. NO. 3570 | 150-PheAlaAspArgAsnLeuArg-156 |
| SEQ. ID. NO. 3571 | 174-AlaPheArgArgArgAlaGlnVal-181 |
| SEQ. ID. NO. 3572 | 183-AlaArgThrArgAla-187 |
| SEQ. ID. NO. 3573 | 194-ArgArgValAspIleArgHis-200 |
| SEQ. ID. NO. 3574 | 231-GlyPheArgArgCysSerAlaAlaGlyGlyArgValGlyThr-244 |
| SEQ. ID. NO. 3575 | 246-ValProCysArgAlaGluTyr-252 |
| SEQ. ID. NO. 3576 | 254-GluTyrGlyAsnArgArgProHisArg-262 |
| SEQ. ID. NO. 3577 | 269-IleThrGlnArgThrGlnLysArgGlnGlyAspGlyLysProPhe-283 |
| 232-2 | |
| AMPHI Regions - AMPHI | |
| SEQ. ID. NO. 3578 | 23-GlnPheLeuGlyAlaPheAsnAspAsnVal-32 |
| SEQ. ID. NO. 3579 | 55-GlyGlnMetLeuAsn-59 |
| SEQ. ID. NO. 3580 | 74-SerLeuSerGlyGlnLeuGlyAsnLysPheAspLysAlaValLeuAlaArgTrpValLysValLeuGluMetIleIleMet-100 |
| SEQ. ID. NO. 3581 | 127-ThrLeuPheGlyProLeuLysTyr-134 |
| SEQ. ID. NO. 3582 | 160-AlaIleLeuPheGly-164 |
| SEQ. ID. NO. 3583 | 167-LeuGlyThrAlaValAlaGlyValProProTyrIleValGlyIleLeuVal-183 |
| SEQ. ID. NO. 3584 | 214-ValArgGlyThrLysSerLeuLeuArgGlu-223 |
| SEQ. ID. NO. 3585 | 251-LeuProThrPheThrGln-256 |
| SEQ. ID. NO. 3586 | 319-ArgPheGluGlyLeuAsn-324 |
| SEQ. ID. NO. 3587 | 340-AlaValMetThrLeuIleGlyPhePheGlyGlyPhePheSerValProLeuTyrThrTrpLeu-360 |
| Antigenic Index - Jameson-Wolf | |
| SEQ. ID. NO. 3588 | 1-MetTyrAlaLysLysGlyGlyLeuGlyLeuValLysSerArgArgPhe-16 |
| SEQ. ID. NO. 3589 | 75-LeuSerGlyGlnLeuGlyAsnLysPheAspLys-85 |
| SEQ. ID. NO. 3590 | 139-AspTyrLeuAspAspLysGluLeuMetMet-148 |
| SEQ. ID. NO. 3591 | 200-ValProAlaLysAlaAlaAspThrGlnIle-209 |
| SEQ. ID. NO. 3592 | 215-ArgGlyThrLysSerLeuLeuArgGluThrValArgHisLysPro-229 |
| SEQ. ID. NO. 3593 | 258-HisLeuGlyGlyAsnAspAsnVal-265 |
| SEQ. ID. NO. 3594 | 286-LysPheSerArgGluArgLeu-292 |
| SEQ. ID. NO. 3595 | 316-HisGlyHisArgPheGluGly-322 |
| SEQ. ID. NO. 3596 | 363-AlaSerSerGluThrPheArgAlaArgAla-372 |
| SEQ. ID. NO. 3597 | 420-IleLysArgGluArgArgPheLeu-427 |
| SEQ. ID. NO. 3598 | 431-AlaIleArgLysLysPro-436 |
| Hydrophilic Regions - Hopp-Woods | |
| SEQ. ID. NO. 3599 | 2-TyrAlaLysLysGlyGly-7 |
| SEQ. ID. NO. 3600 | 11-ValLysSerArgArgPhe-16 |
| SEQ. ID. NO. 3601 | 81-AsnLysPheAspLys-85 |
| SEQ. ID. NO. 3602 | 140-TyrLeuAspAspLysGluLeuMet-147 |
| SEQ. ID. NO. 3603 | 201-ProAlaLysAlaAlaAspThrGlnIle-209 |
| SEQ. ID. NO. 3604 | 215-ArgGlyThrLysSerLeuLeuArgGluThrValArgHis-227 |
| SEQ. ID. NO. 3605 | 286-LysPheSerArgGluArgLeu-292 |
| SEQ. ID. NO. 3606 | 318-HisArgPheGluGly-322 |
| SEQ. ID. NO. 3607 | 366-GluThrPheArgAlaArgAla-372 |
| SEQ. ID. NO. 3608 | 420-IleLysArgGluArgArgPheLeu-427 |
| SEQ. ID. NO. 3609 | 431-AlaIleArgLysLysPro-436 |
| 233-2 | |
| AMPHI Regions - AMPHI | |
| SEQ. ID. NO. 3610 | 61-PheAlaAspLysValGlnThr-67 |
| SEQ. ID. NO. 3611 | 71-GlnValArgValTrpLysAsn-77 |
| SEQ. ID. NO. 3612 | 88-AsnGlyValAlaLysLeuLeuGluThr-96 |

TABLE 1-continued

| | |
|---|---|
| SEQ. ID. NO. 3613 | 119-AlaLeuThrArgLeuIleGluGlnAlaGlyAsnAla-130 |
| SEQ. ID. NO. 3614 | 138-IleProIleAlaAspThrLeuLysCysAlaAspGlyGlyAsn-151 |
| SEQ. ID. NO. 3615 | 180-AlaAlaGluAsnLeuAspGlyIleThrAsp-189 |
| Antigenic Index - Jameson-Wolf | |
| SEQ. ID. NO. 3616 | 1-MetLysArgLysAsnIle-6 |
| SEQ. ID. NO. 3617 | 16-AlaArgPheGlyAlaAspLysProLysGlnTyrValGluIleGlySerLysThrValLeu-35 |
| SEQ. ID. NO. 3618 | 43-GluArgHisGluAlaValAsp-49 |
| SEQ. ID. NO. 3619 | 56-SerProGluAspThrPheAlaAspLysValGln-66 |
| SEQ. ID. NO. 3620 | 75-TrpLysAsnGlyGlyGlnThrArgAlaGluThrValArgAsnGlyVal-90 |
| SEQ. ID. NO. 3621 | 100-AlaGluThrAspAsn-104 |
| SEQ. ID. NO. 3622 | 109-AspAlaAlaArgCys-113 |
| SEQ. ID. NO. 3623 | 115-LeuProSerGluAlaLeu-120 |
| SEQ. ID. NO. 3624 | 123-LeuIleGluGlnAlaGlyAsnAlaAlaGluGlyGly-134 |
| SEQ. ID. NO. 3625 | 142-AspThrLeuLysCysAlaAspGlyGlyAsnIle-152 |
| SEQ. ID. NO. 3626 | 155-ThrValGluArgThrSerLeu-161 |
| SEQ. ID. NO. 3627 | 182-GluAsnLeuAspGlyIleThrAspGluAlaSerAlaValGluLysLeuGlyVal-199 |
| SEQ. ID. NO. 3628 | 206-GlyAspValArgAsnLeuLysLeuThrGlnProGlnAspAlaTyr-220 |
| Hydrophilic Regions - Hopp-Woods | |
| SEQ. ID. NO. 3629 | 1-MetLysArgLysAsnIle-6 |
| SEQ. ID. NO. 3630 | 18-PheGlyAlaAspLysProLysGlnTyrVal-27 |
| SEQ. ID. NO. 3631 | 43-GluArgHisGluAlaValAsp-49 |
| SEQ. ID. NO. 3632 | 56-SerProGluAspThrPheAlaAspLysValGln-66 |
| SEQ. ID. NO. 3633 | 79-GlyGlnThrArgAlaGluThrValArg-87 |
| SEQ. ID. NO. 3634 | 100-AlaGluThrAspAsn-104 |
| SEQ. ID. NO. 3635 | 127-AlaGlyAsnAlaAlaGlu-132 |
| SEQ. ID. NO. 3636 | 142-AspThrLeuLysCysAlaAsp-148 |
| SEQ. ID. NO. 3637 | 182-GluAsnLeuAspGlyIleThrAspGluAlaSerAlaValGluLysLeuGlyVal-199 |
| SEQ. ID. NO. 3638 | 206-GlyAspValArgAsnLeuLys-212 |
| 234-2 | |
| AMPHI Regions - AMPHI | |
| SEQ. ID. NO. 3639 | 26-ArgSerLeuGluValGluLysValAlaSer-35 |
| SEQ. ID. NO. 3640 | 68-AspArgLeuGlySerGln-73 |
| SEQ. ID. NO. 3641 | 83-GlnGlnThrAsnArgPheAsnValLeuAsnArgThrAsn-95 |
| SEQ. ID. NO. 3642 | 121-GlyAspValThrGluPhe-126 |
| SEQ. ID. NO. 3643 | 206-AlaValAsnSerLeuValGlnAlaValAsp-215 |
| Antigenic Index - Jameson-Wolf | |
| SEQ. ID. NO. 3644 | 21-AlaThrGluSerSerArgSerLeuGluValGluLysValAlaSer-35 |
| SEQ. ID. NO. 3645 | 51-ThrPheAspAsnArgSerSerPhe-58 |
| SEQ. ID. NO. 3646 | 62-IlePheSerAspGlyGluAspArgLeuGlySerGlnAla-74 |
| SEQ. ID. NO. 3647 | 83-GlnGlnThrAsnArgPheAsnValLeuAsnArgThrAsn-95 |
| SEQ. ID. NO. 3648 | 99-LeuLysGlnGluSerGlyIleSerGlyLysAlaHisAsnLeuLysGlyAlaAspTyr-117 |
| SEQ. ID. NO. 3649 | 121-GlyAspValThrGluPheGlyArgArgAspValGlyAsp-133 |
| SEQ. ID. NO. 3650 | 140-LeuGlyArgGlyLysSerGlnIle-147 |
| SEQ. ID. NO. 3651 | 160-AsnThrSerGluIle-164 |
| SEQ. ID. NO. 3652 | 169-GlnGlyAlaGlyGlu-173 |
| SEQ. ID. NO. 3653 | 175-AlaLeuSerAsnArgGluIle-181 |
| SEQ. ID. NO. 3654 | 185-GlyGlyThrSerGlyTyrAspAlaThrLeuAsnGlyLysValLeu-199 |
| SEQ. ID. NO. 3655 | 214-ValAspAsnGlyAlaTrpGlnProAsnArg-223 |
| Hydrophilic Regions - Hopp-Woods | |
| SEQ. ID. NO. 3656 | 21-AlaThrGluSerSerArgSerLeuGluValGluLysValAla-34 |
| SEQ. ID. NO. 3657 | 52-PheAspAsnArgSerSerPhe-58 |
| SEQ. ID. NO. 3658 | 62-IlePheSerAspGlyGluAspArgLeuGlySerGlnAla-74 |
| SEQ. ID. NO. 3659 | 99-LeuLysGlnGluSerGlyIleSerGlyLysAlaHisAsn-111 |
| SEQ. ID. NO. 3660 | 122-AspValThrGluPheGlyArgArgAspValGlyAsp-133 |
| SEQ. ID. NO. 3661 | 141-GlyArgGlyLysSer-145 |
| SEQ. ID. NO. 3662 | 176-LeuSerAsnArgGluIle-181 |
| 235 | |
| AMPHI Regions - AMPHI | |
| SEQ. ID. NO. 3663 | 8-LeuAlaAlaValLeuAlaLeu-14 |
| SEQ. ID. NO. 3664 | 18-GlnValGlnLysAlaProAsp-24 |
| SEQ. ID. NO. 3665 | 86-LeuThrAsnAlaAlaAspIle-92 |
| SEQ. ID. NO. 3666 | 95-ValArgProGluLysLeuHisGlnIlePhe-104 |
| SEQ. ID. NO. 3667 | 120-SerTyrGlnIleLeuAspSerValThrThr-129 |
| SEQ. ID. NO. 3668 | 165-GlyAlaLeuValSerAlaValValAsnGlnIleAlaAsnSerLeuThr-180 |
| SEQ. ID. NO. 3669 | 187-SerLysThrAlaAlaTyrAsnLeuLeuSerProTyr-198 |
| Antigenic Index - Jameson-Wolf | |
| SEQ. ID. NO. 3670 | 20-GlnLysAlaProAspPheAspTyrThrSerPheLysGluSerLysProAla-36 |
| SEQ. ID. NO. 3671 | 43-ProLeuAsnGluSerProAspValAsnGlyThr-53 |
| SEQ. ID. NO. 3672 | 62-AlaProLeuSerGlu-66 |
| SEQ. ID. NO. 3673 | 79-GluThrPheLysGlnAsnGlyLeuThrAsn-88 |
| SEQ. ID. NO. 3674 | 93-HisAlaValArgProGluLysLeu-100 |
| SEQ. ID. NO. 3675 | 131-SerAlaLysAlaArgLeuValAspSerArgAsnGlyLysGluLeuTrpSerGlySerAlaSerIleArgGluGlySerAsnAsnSerAsnSer-161 |
| SEQ. ID. NO. 3676 | 178-SerLeuThrAspArgGlyTyrGlnValSerLysThrAla-190 |
| SEQ. ID. NO. 3677 | 202-GlyIleLeuLysGlyProArgPheValGluGluGlnProLys-215 |
| Hydrophilic Regions - Hopp-Woods | |
| SEQ. ID. NO. 3678 | 20-GlnLysAlaProAspPheAsp-26 |
| SEQ. ID. NO. 3679 | 29-SerPheLysGluSerLysPro-35 |
| SEQ. ID. NO. 3680 | 44-LeuAsnGluSerProAspVal-50 |
| SEQ. ID. NO. 3681 | 93-HisAlaValArgProGluLysLeu-100 |
| SEQ. ID. NO. 3682 | 131-SerAlaLysAlaArgLeuValAspSerArgAsnGlyLysGluLeuTrp-146 |

TABLE 1-continued

| | |
|---|---|
| SEQ. ID. NO. 3683 | 150-AlaSerIleArgGluGlySerAsnAsnSer-159 |
| SEQ. ID. NO. 3684 | 179-LeuThrAspArgGlyTyrGln-185 |
| SEQ. ID. NO. 3685 | 207-ProArgPheValGluGluGlnProLys-215 |
| 236-2 | |
| AMPHI Regions - AMPHI | |
| SEQ. ID. NO. 3686 | 11-LeuCysThrAlaPheAlaAsp-17 |
| SEQ. ID. NO. 3687 | 107-PheAlaGlyPheAlaAspCysArgProPhe-116 |
| SEQ. ID. NO. 3688 | 146-AspAspValProArgPhePheAlaGlyGlu-155 |
| SEQ. ID. NO. 3689 | 178-AlaAlaCysMetAlaValCysPheGly-186 |
| SEQ. ID. NO. 3690 | 214-LysValGluGlyIleThrArgIle-221 |
| SEQ. ID. NO. 3691 | 245-IleArgLeuLeuHisGlyIlePheAsnArgIleLysValAla-258 |
| SEQ. ID. NO. 3692 | 288-PheAlaAlaValIle-292 |
| SEQ. ID. NO. 3693 | 311-LeuArgCysAsnAspValAlaAspGlyPheArgHisPhe-323 |
| Antigenic Index - Jameson-Wolf | |
| SEQ. ID. NO. 3694 | 42-GlyPheSerGlyAsnGlyLysPhe-49 |
| SEQ. ID. NO. 3695 | 58-ArgHisGlnGlnSerLysAlaGln-65 |
| SEQ. ID. NO. 3696 | 77-PhePheArgArgGlyAsnPheGlyPheGlyLeuGlnGlyArgThrAspGlyPhe-94 |
| SEQ. ID. NO. 3697 | 98-GlnArgLeuAspGlyGlyGlyTyr-105 |
| SEQ. ID. NO. 3698 | 109-GlyPheAlaAspCysArgProPhe-116 |
| SEQ. ID. NO. 3699 | 126-ValAspGlyArgGluLeuValProSerMetGluGluAspAla-139 |
| SEQ. ID. NO. 3700 | 145-AlaAspAspValPro-149 |
| SEQ. ID. NO. 3701 | 155-GluAlaGlnAsnArgCysAsnGlnGluAsnGlnThrAla-167 |
| SEQ. ID. NO. 3702 | 195-ValGluValGluArgThrGlnValPheArgAlaGluArgAsnAsnValPhe-211 |
| SEQ. ID. NO. 3703 | 213-GlyLysValGluGlyIleThr-219 |
| SEQ. ID. NO. 3704 | 261-GlyLysGlnLysAlaGlnGly-267 |
| SEQ. ID. NO. 3705 | 292-IleGlyArgCysArgProGlnAlaGln-300 |
| SEQ. ID. NO. 3706 | 312-ArgCysAsnAspValAlaAspGly-319 |
| SEQ. ID. NO. 3707 | 328-ValAspAsnGluThrMet-333 |
| Hydrophilic Regions - Hopp-Woods | |
| SEQ. ID. NO. 3708 | 89-GlyArgThrAspGly-93 |
| SEQ. ID. NO. 3709 | 98-GlnArgLeuAspGlyGlyGly-104 |
| SEQ. ID. NO. 3710 | 127-AspGlyArgGluLeuValProSerMetGluGluAspAla-139 |
| SEQ. ID. NO. 3711 | 145-AlaAspAspValPro-149 |
| SEQ. ID. NO. 3712 | 156-AlaGlnAsnArgCysAsnGlnGluAsnGlnThr-166 |
| SEQ. ID. NO. 3713 | 195-ValGluValGluArgThrGlnValPheArgAlaGluArgAsnAsn-209 |
| SEQ. ID. NO. 3714 | 215-ValGluGlyIleThr-219 |
| SEQ. ID. NO. 3715 | 261-GlyLysGlnLysAlaGlnGly-267 |
| SEQ. ID. NO. 3716 | 293-GlyArgCysArgProGlnAlaGln-300 |
| SEQ. ID. NO. 3717 | 312-ArgCysAsnAspValAlaAspGly-319 |
| SEQ. ID. NO. 3718 | 328-ValAspAsnGluThrMet-333 |
| 238 | |
| AMPHI Regions - AMPHI | |
| SEQ. ID. NO. 3719 | 103-ValHisSerProPhe-107 |
| SEQ. ID. NO. 3720 | 112-SerLysSerThrSerAspPheSerGlyGlyVal-122 |
| SEQ. ID. NO. 3721 | 129-TyrGlnLeuHisArgThrGlySer-136 |
| SEQ. ID. NO. 3722 | 141-GluAspGlyTyrAspGlyProGlnGlySer-150 |
| SEQ. ID. NO. 3723 | 158-AlaArgAspIleTyrSerTyrTyrVal-166 |
| SEQ. ID. NO. 3724 | 224-AspAspValArgGlyIleValGlnGlyAlaValAsnPro-236 |
| SEQ. ID. NO. 3725 | 246-IleGlyAlaIleThrAspSerAlaValSerProValThrAspThrAlaAlaGlnGlnThrLeuGlnGlyIleAsnAspLeuGlyLysLeu-275 |
| SEQ. ID. NO. 3726 | 298-IleAsnSerAlaLysGlnTrpAlaAspAla-307 |
| SEQ. ID. NO. 3727 | 342-AspTrpValLysAsn-346 |
| SEQ. ID. NO. 3728 | 351-LysProAlaAlaArgHisMetGlnThrLeu-360 |
| SEQ. ID. NO. 3729 | 367-GlyAsnLysProIleLysSerLeuProAsn-376 |
| SEQ. ID. NO. 3730 | 398-PheAspSerValHisLysThrLeuThr-406 |
| SEQ. ID. NO. 3731 | 465-GlyLysGlnAlaLysAspTyrLeu-472 |
| Antigenic Index - Jameson-Wolf | |
| SEQ. ID. NO. 3732 | 25-HisAlaAsnGlyLeuAspAlaArgLeuArgAspAspMetGlnAlaLysHisTyrGluProGlyGlyLys-47 |
| SEQ. ID. NO. 3733 | 53-AsnAlaArgGlySerValLysLysArgValTyr-63 |
| SEQ. ID. NO. 3734 | 80-ThrHisGluArgThrGlyPheGluGly-88 |
| SEQ. ID. NO. 3735 | 96-PheSerGlyHisGlyHisGluValHisSerProPheAspHisHisAspSerLysSerThrSerAspPheSerGlyGlyValAspGlyGly-125 |
| SEQ. ID. NO. 3736 | 131-LeuHisArgThrGlySerGluIleHisProGluAspGlyTyrAspGlyProGlnGlySerAspTyrProProProGlyGlyAlaArgAsp-160 |
| SEQ. ID. NO. 3737 | 166-ValLysGlyThrSerThrLysThrLysThr-175 |
| SEQ. ID. NO. 3738 | 182-ProPheSerAspArgTrpLeuLysGluAsnAlaGlyAla-194 |
| SEQ. ID. NO. 3739 | 200-SerArgAlaAspGluAlaGly-206 |
| SEQ. ID. NO. 3740 | 210-TrpGluSerAspProAsnLysAsnTrp-218 |
| SEQ. ID. NO. 3741 | 221-AsnArgMetAspAspValArgGlyIle-229 |
| SEQ. ID. NO. 3742 | 268-GlyIleAsnAspLeuGlyLysLeuSerProGluAlaGln-280 |
| SEQ. ID. NO. 3743 | 292-PheAlaValLysAspGlyIleAsnSerAlaLysGlnTrpAla-305 |
| SEQ. ID. NO. 3744 | 307-AlaHisProAsnIle-311 |
| SEQ. ID. NO. 3745 | 329-TrpArgGlyLysLysValGluLeuAsnProThrLysTrpAspTrpValLysAsnThrGlyTyrLysLysProAlaAlaArg-355 |
| SEQ. ID. NO. 3746 | 360-LeuAspGlyGluMetAlaGlyGlyAsnLysProIleLysSerLeuProAsnSerAlaAlaGluLysArgLysGlnAsnPheGluLysPheAsnSer AsnTrpSer-394 |
| SEQ. ID. NO. 3747 | 396-AlaSerPheAspSerValHisLysThrLeuThrProAsnAla-409 |
| SEQ. ID. NO. 3748 | 413-LeuSerProAspLysValLysThrArgTyrThrSerLeuAspGlyLysIleThrIleIleLysAspAsnGluAsnAsnTyr-439 |
| SEQ. ID. NO. 3749 | 441-ArgIleHisAspAsnSerArgLysGlnTyrLeuAspSerAsnGlyAsnAlaValLysThrGlyAsnLeuGlnGlyLysGlnAlaLysAspTyrLeu Gln-473 |
| SEQ. ID. NO. 3750 | 476-ThrHisIleArgAsnLeuAspLys-483 |
| Hydrophilic Regions - Hopp-Woods | |
| SEQ. ID. NO. 3751 | 29-LeuAspAlaArgLeuArgAspAspMetGlnAlaLysHisTyrGluProGlyGly-46 |
| SEQ. ID. NO. 3752 | 54-AlaArgGlySerValLysLysArgValTyr-63 |

TABLE 1-continued

| | |
|---|---|
| SEQ. ID. NO. 3753 | 80-ThrHisGluArgThrGlyPhe-86 |
| SEQ. ID. NO. 3754 | 108-AspHisHisAspSerLysSerThrSerAspPhe-118 |
| SEQ. ID. NO. 3755 | 133-ArgThrGlySerGluIleHisProGluAspGlyTyrAspGlyProGlnGlySerAspTyrProPro-154 |
| SEQ. ID. NO. 3756 | 156-GlyGlyAlaArgAsp-160 |
| SEQ. ID. NO. 3757 | 169-ThrSerThrLysThrLysThr-175 |
| SEQ. ID. NO. 3758 | 186-ArgTrpLeuLysGluAsnAlaGly-193 |
| SEQ. ID. NO. 3759 | 200-SerArgAlaAspGluAlaGly-206 |
| SEQ. ID. NO. 3760 | 222-ArgMetAspAspValArgGly-228 |
| SEQ. ID. NO. 3761 | 271-AspLeuGlyLysLeuSerPro-277 |
| SEQ. ID. NO. 3762 | 296-AspGlyIleAsnSer-300 |
| SEQ. ID. NO. 3763 | 329-TrpArgGlyLysLysValGluLeuAsnProThr-339 |
| SEQ. ID. NO. 3764 | 347-ThrGlyTyrLysLysProAlaAlaArg-355 |
| SEQ. ID. NO. 3765 | 360-LeuAspGlyGluMetAlaGlyGlyAsnLysProIleLys-372 |
| SEQ. ID. NO. 3766 | 377-SerAlaAlaGluLysArgLysGlnAsnPheGluLysPheAsn-390 |
| SEQ. ID. NO. 3767 | 414-SerProAspLysValLysThrArgTyrThrSerLeuAspGlyLysIleThrIleIleLysAspAsnGluAsnAsn-438 |
| SEQ. ID. NO. 3768 | 443-HisAspAsnSerArgLysGlnTyrLeu-451 |
| SEQ. ID. NO. 3769 | 454-AsnGlyAsnAlaValLys-459 |
| SEQ. ID. NO. 3770 | 462-AsnLeuGlnGlyLysGlnAlaLysAspTyrLeu-472 |
| SEQ. ID. NO. 3771 | 479-ArgAsnLeuAspLys-483 |
| 239-2 | |
| AMPHI Regions - AMPHI | |
| SEQ. ID. NO. 3772 | 49-PheArgLeuIleGlnSerCys-55 |
| SEQ. ID. NO. 3773 | 72-AsnAlaHisArgLysGln-77 |
| SEQ. ID. NO. 3774 | 123-ProGlyPheAsnAlaLeuProThrIlePhe-132 |
| SEQ. ID. NO. 3775 | 165-SerSerAsnGluTrp-169 |
| SEQ. ID. NO. 3776 | 221-PheCysAlaThrIleCysAlaSerLeuArg-230 |
| Antigenic Index - Jameson-Wolf | |
| SEQ. ID. NO. 3777 | 6-GlyIleAlaArgAsnArgArgMetGlu-14 |
| SEQ. ID. NO. 3778 | 19-CysArgArgProAspArgPheValValArgGlnThrArgLeuLeu-33 |
| SEQ. ID. NO. 3779 | 53-GlnSerCysGluIleGluPro-59 |
| SEQ. ID. NO. 3780 | 66-HisAsnGlyLysSerGlyAsnAlaHisArgLysGlnGlnLysGluIle-81 |
| SEQ. ID. NO. 3781 | 100-ProAlaValArgSerAlaThrArgLysThrAla-110 |
| SEQ. ID. NO. 3782 | 132-PheArgGlySerSerGlyLysSerAlaSer-141 |
| SEQ. ID. NO. 3783 | 144-AlaAlaGlnArgGlyArgGlyAlaCys-152 |
| SEQ. ID. NO. 3784 | 164-ArgSerSerAsnGluTrpLys-170 |
| SEQ. ID. NO. 3785 | 173-ThrAlaLysArgProProSerPheArgArgHisMetThrCysGlyAsnThrAlaProThrSerSerSerSerArgLeuIleLysMet-201 |
| SEQ. ID. NO. 3786 | 209-ValAlaGlySerCysProArgSerArgValArgThr-220 |
| SEQ. ID. NO. 3787 | 245-ArgAlaIleArgArgLeuAsnArgSerSerPro-255 |
| Hydrophilic Regions - Hopp-Woods | |
| SEQ. ID. NO. 3788 | 6-GlyIleAlaArgAsnArgArgMetGlu-14 |
| SEQ. ID. NO. 3789 | 20-ArgArgProAspArgPheValValArgGlnThrArg-31 |
| SEQ. ID. NO. 3790 | 67-AsnGlyLysSerGlyAsnAlaHisArgLysGlnGlnLysGluIle-81 |
| SEQ. ID. NO. 3791 | 102-ValArgSerAlaThrArgLysThrAla-110 |
| SEQ. ID. NO. 3792 | 135-SerSerGlyLysSerAlaSer-141 |
| SEQ. ID. NO. 3793 | 146-GlnArgGlyArgGlyAlaCys-152 |
| SEQ. ID. NO. 3794 | 165-SerSerAsnGluTrpLys-170 |
| SEQ. ID. NO. 3795 | 173-ThrAlaLysArgProProSerPheArgArgHisMet-184 |
| SEQ. ID. NO. 3796 | 193-SerSerSerSerArgLeuIleLysMet-201 |
| SEQ. ID. NO. 3797 | 211-GlySerCysProArgSerArgValArgThr-220 |
| SEQ. ID. NO. 3798 | 245-ArgAlaIleArgArgLeuAsnArgSerSerPro-255 |
| 240-2 | |
| AMPHI Regions - AMPHI | |
| SEQ. ID. NO. 3799 | 19-AlaAspValGlyArgPheLeuHis-26 |
| SEQ. ID. NO. 3800 | 63-IleGlnCysLeuArgAsnHis-69 |
| SEQ. ID. NO. 3801 | 87-AlaProLeuPheAlaValCysPro-94 |
| SEQ. ID. NO. 3802 | 107-GlnGlyGluAspPheProArgAlaGlyIleGlnAsnHis-119 |
| SEQ. ID. NO. 3803 | 154-ValPheArgGlyPheIleAlaArgGlyValGlnAlaValHisAsn-168 |
| SEQ. ID. NO. 3804 | 188-PheLysArgLysPheGln-193 |
| Antigenic Index - Jameson-Wolf | |
| SEQ. ID. NO. 3805 | 9-GlyThrGluThrArgArgGlnPheAla-17 |
| SEQ. ID. NO. 3806 | 39-IleAlaHisGlyArgArgSerAspPheIleArg-49 |
| SEQ. ID. NO. 3807 | 67-ArgAsnHisLysArgPheAspCysArgThrGlyPheAsp-79 |
| SEQ. ID. NO. 3808 | 101-ValGlyGlyArgIleGlyGlnGlyGluAspPheProArgAlaGlyIleGlnAsnHisHisArgSerGly-123 |
| SEQ. ID. NO. 3809 | 139-GlnGlyLeuAsnProLeuIleGluGlyLysAspAspVal-151 |
| SEQ. ID. NO. 3810 | 173-ValProGlnAsnAspPheArg-179 |
| SEQ. ID. NO. 3811 | 187-ValPheLysArgLysPhe-192 |
| SEQ. ID. NO. 3812 | 201-AsnIleGlyLysSerAspAspValCysLys-210 |
| Hydrophilic Regions - Hopp-Woods | |
| SEQ. ID. NO. 3813 | 10-ThrGluThrArgArgGlnPheAla-17 |
| SEQ. ID. NO. 3814 | 41-HisGlyArgArgSerAspPheIleArg-49 |
| SEQ. ID. NO. 3815 | 67-ArgAsnHisLysArgPheAspCys-74 |
| SEQ. ID. NO. 3816 | 105-IleGlyGlnGlyGluAspPheProArg-113 |
| SEQ. ID. NO. 3817 | 145-IleGluGlyLysAspAspVal-151 |
| SEQ. ID. NO. 3818 | 187-ValPheLysArgLysPhe-192 |
| SEQ. ID. NO. 3819 | 203-GlyLysSerAspAspValCysLys-210 |
| 241-1 | |
| AMPHI Regions - AMPHI | |
| SEQ. ID. NO. 3820 | 6-ThrArgAlaAlaAsnProPro-12 |
| SEQ. ID. NO. 3821 | 35-ThrArgThrProArgGluProAlaSer-43 |
| SEQ. ID. NO. 3822 | 109-PheLeuIleGlyCysIleAla-115 |

TABLE 1-continued

| | |
|---|---|
| SEQ. ID. NO. 3823 | 126-PheHisAlaCysGlnArgMetValAlaVal-135 |
| SEQ. ID. NO. 3824 | 194-ArgHisIleAspArgIleAlaGlyIleLeuThrValGln-206 |
| SEQ. ID. NO. 3825 | 229-PheValGlnLysLeuIleValGlyIleIleHis-239 |
| Antigenic Index - Jameson-Wolf | |
| SEQ. ID. NO. 3826 | 1-MetProThrArgProThrArgAlaAlaAsnProProThrProProThr-16 |
| SEQ. ID. NO. 3827 | 23-CysProArgProProTyrArgProProSerValGlnThrArgThrProArgGluProAlaSerSerThrCysAlaAlaLysSerAlaAsnArgArgGluAsn SerHisAsnAlaGlnPro-62 |
| SEQ. ID. NO. 3828 | 68-ProSerAsnLysMetProSerGluThrGluGlnThrLeuPheArgArgHisGlnIleProProSerCysArgGlnSer-93 |
| SEQ. ID. NO. 3829 | 122-LeuLysAlaAspPhe-126 |
| SEQ. ID. NO. 3830 | 147-ThrIleAspAspAsnIleAla-153 |
| SEQ. ID. NO. 3831 | 166-PheAspPheAsnArgGluHisAlaArgIlePheAspThrAspGlnLeu-181 |
| SEQ. ID. NO. 3832 | 188-ArgIleValGlyArgGlnArgHisIleAspArgIleAla-200 |
| SEQ. ID. NO. 3833 | 209-PheHisGlnArgGluAsnAla-215 |
| SEQ. ID. NO. 3834 | 244-ArgAsnHisGlyIle-248 |
| SEQ. ID. NO. 3835 | 250-HisAspSerHisIleCysProPheArgAsnSerArgLeuIle-263 |
| Hydrophilic Regions - Hopp-Woods | |
| SEQ. ID. NO. 3836 | 1-MetProThrArgProThrArgAlaAlaAsn-10 |
| SEQ. ID. NO. 3837 | 32-SerValGlnThrArgThrProArgGluProAlaSer-43 |
| SEQ. ID. NO. 3838 | 46-CysAlaAlaLysSerAlaAsnArgArgGluAsnSerHis-58 |
| SEQ. ID. NO. 3839 | 70-AsnLysMetProSerGluThrGluGlnThrLeuPheArg-82 |
| SEQ. ID. NO. 3840 | 122-LeuLysAlaAspPhe-126 |
| SEQ. ID. NO. 3841 | 166-PheAspPheAsnArgGluHisAlaArgIlePheAsp-177 |
| SEQ. ID. NO. 3842 | 188-ArgIleValGlyArgGlnArgHisIleAspArgIleAla-200 |
| SEQ. ID. NO. 3843 | 209-PheHisGlnArgGluAsnAla-215 |
| 242 | |
| AMPHI Regions - AMPHI | |
| SEQ. ID. NO. 3844 | 23-SerGluValValThrGlnPheValAspPheValGlu-34 |
| SEQ. ID. NO. 3845 | 42-AlaGlyPheCysHisIleLeuGlnAsn-50 |
| SEQ. ID. NO. 3846 | 100-AlaAspGlnAlaGln-104 |
| SEQ. ID. NO. 3847 | 122-AsnProPhePheAspPhePheGlnAlaValVal-132 |
| SEQ. ID. NO. 3848 | 137-HisGlnSerGlyPheGlyAspValPhe-145 |
| SEQ. ID. NO. 3849 | 156-LeuGluGlnSerVal-160 |
| SEQ. ID. NO. 3850 | 177-PheGluLeuPheGln-181 |
| SEQ. ID. NO. 3851 | 191-PheGlyHisThrArgLeuPheAspIleCys-200 |
| SEQ. ID. NO. 3852 | 262-HisProPheAlaAspPheGlyAsnPheGlnAsnLeuLeuAlaLeu-276 |
| Antigenic Index - Jameson-Wolf | |
| SEQ. ID. NO. 3853 | 13-HisPheGluGlnArgAlaGlyGlyIleAla-22 |
| SEQ. ID. NO. 3854 | 33-ValGluGlnGluGln-37 |
| SEQ. ID. NO. 3855 | 52-ThrGlyHisArgAlaAspIle-58 |
| SEQ. ID. NO. 3856 | 75-SerHisAlaAspIlePheProProArgCysPheGlyAspGlyPheAlaGlnArgGlyPheAlaHisAlaArgArgAlaAspGlnAlaGlnAsnArgAla-107 |
| SEQ. ID. NO. 3857 | 137-HisGlnSerGlyPhe-141 |
| SEQ. ID. NO. 3858 | 154-ArgGlnLeuGluGlnSerVal-160 |
| SEQ. ID. NO. 3859 | 164-AlaTyrAspGlyGlyPheArgArgHisArgTrpHis-175 |
| SEQ. ID. NO. 3860 | 283-MetArgCysAspArgIleGly-289 |
| Hydrophilic Regions - Hopp-Woods | |
| SEQ. ID. NO. 3861 | 13-HisPheGluGlnArgAlaGlyGlyIle-21 |
| SEQ. ID. NO. 3862 | 33-ValGluGlnGluGln-37 |
| SEQ. ID. NO. 3863 | 52-ThrGlyHisArgAlaAspIle-58 |
| SEQ. ID. NO. 3864 | 95-AlaHisAlaArgArgAlaAspGlnAlaGlnAsnArgAla-107 |
| SEQ. ID. NO. 3865 | 154-ArgGlnLeuGluGlnSerVal-160 |
| SEQ. ID. NO. 3866 | 167-GlyGlyPheArgArgHisArg-173 |
| SEQ. ID. NO. 3867 | 283-MetArgCysAspArgIleGly-289 |
| 243 | |
| AMPHI Regions - AMPHI | |
| SEQ. ID. NO. 3868 | 35-IleThrArgLeuAlaArgLysAlaValGlnArgLeuThr-47 |
| SEQ. ID. NO. 3869 | 50-HisIleGlnXxxPhePheThrGlu-57 |
| SEQ. ID. NO. 3870 | 80-AspSerSerArgIleThrSerThrIle-88 |
| Antigenic Index - Jameson-Wolf | |
| SEQ. ID. NO. 3871 | 29-LeuProSerAsnAlaPro-34 |
| SEQ. ID. NO. 3872 | 37-ArgLeuAlaArgLysAlaValGln-44 |
| SEQ. ID. NO. 3873 | 58-SerHisThrGlyAlaAsnArgSerSerSerSerCysLysPro-71 |
| SEQ. ID. NO. 3874 | 77-SerAlaSerAspSerSerArgIle-84 |
| SEQ. ID. NO. 3875 | 102-SerThrThrGlyAlaValThrLysSer-110 |
| Hydrophilic Regions - Hopp-Woods | |
| SEQ. ID. NO. 3876 | 37-ArgLeuAlaArgLysAlaValGln-44 |
| SEQ. ID. NO. 3877 | 59-HisThrGlyAlaAsnArgSerSerSerSerCysLys-70 |
| SEQ. ID. NO. 3878 | 78-AlaSerAspSerSerArgIle-84 |
| 244-2 | |
| AMPHI Regions - AMPHI | |
| SEQ. ID. NO. 3879 | 22-LysCysPheLeuGlnLeuValGln-29 |
| SEQ. ID. NO. 3880 | 31-HisLeuHisAlaHis-35 |
| SEQ. ID. NO. 3881 | 109-IleSerArgLeuCysGlySerLeuPhe-117 |
| SEQ. ID. NO. 3882 | 126-CysLeuAspGlyPheHisArgLeuHis-134 |
| SEQ. ID. NO. 3883 | 137-AsnArgPhePheThr-141 |
| SEQ. ID. NO. 3884 | 165-TyrProArgLysIleArgThrPheSerArgAsnPheLysGlnLys-179 |
| Antigenic Index - Jameson-Wolf | |
| SEQ. ID. NO. 3885 | 1-MetAspIleArgIle-5 |
| SEQ. ID. NO. 3886 | 11-PheArgValAspPheLeuAsp-17 |
| SEQ. ID. NO. 3887 | 45-IleGlnLysArgHis-49 |
| SEQ. ID. NO. 3888 | 54-LeuAspArgGlnHisPheHisGlyLysLeuLeuSerGlyGluLeuValArg-70 |

TABLE 1-continued

| | |
|---|---|
| SEQ. ID. NO. 3889 | 99-GlnLeuGlyAsnProArgLeu-105 |
| SEQ. ID. NO. 3890 | 154-LeuLysThrAsnTrpLysSerLysSerSerTyrTyrProArgLysIleArgThrPheSerArgAsnPheLysGlnLysGlnArgIleSerAsnSerPheSerAsnProLeuProLysLys-193 |
| Hydrophilic Regions - Hopp-Woods | |
| SEQ. ID. NO. 3891 | 1-MetAspIleArgIle-5 |
| SEQ. ID. NO. 3892 | 11-PheArgValAspPheLeuAsp-17 |
| SEQ. ID. NO. 3893 | 156-ThrAsnTrpLysSerLysSer-162 |
| SEQ. ID. NO. 3894 | 167-ArgLysIleArgThrPheSerArgAsnPheLysGlnLysGlnArgIle-182 |
| 246-2 | |
| AMPHI Regions - AMPHI | |
| SEQ. ID. NO. 3895 | 39-AlaValAsnIleAlaGlnCysPheThr-47 |
| SEQ. ID. NO. 3896 | 67-GluGlnPheAlaAsnLeuPhePhe-74 |
| SEQ. ID. NO. 3897 | 83-AspMetGlyArgPhe-87 |
| SEQ. ID. NO. 3898 | 132-PheGlyCysAspAspValValAspAsnLeuAlaGlyPheGlyArg-146 |
| SEQ. ID. NO. 3899 | 156-GlnLeuSerGlnValPhePheGlnLeuLeuGln-166 |
| Antigenic Index - Jameson-Wolf | |
| SEQ. ID. NO. 3900 | 1-MetHisGlyArgTyrGlyGlyThrGln-9 |
| SEQ. ID. NO. 3901 | 18-GlnThrGlnArgThrCysPheSerAsnGlyLysValTyr-30 |
| SEQ. ID. NO. 3902 | 34-ThrAspIleGlySer-38 |
| SEQ. ID. NO. 3903 | 59-GlnArgArgThrGluValLeu-65 |
| SEQ. ID. NO. 3904 | 78-AspSerArgHisHisAspMetGlyArg-86 |
| SEQ. ID. NO. 3905 | 92-LeuAspAspGluLeuAla-97 |
| SEQ. ID. NO. 3906 | 133-GlyCysAspAspValValAspAsn-140 |
| SEQ. ID. NO. 3907 | 143-GlyPheGlyArgGlyPhe-148 |
| Hydrophilic Regions - Hopp-Woods | |
| SEQ. ID. NO. 3908 | 59-GlnArgArgThrGluValLeu-65 |
| SEQ. ID. NO. 3909 | 78-AspSerArgHisHisAspMet-84 |
| SEQ. ID. NO. 3910 | 92-LeuAspAspGluLeuAla-97 |
| 247-1 | |
| AMPHI Regions - AMPHI | |
| SEQ. ID. NO. 3911 | 12-SerTyrAspGlyMetLysGlyPheThrIleIle-22 |
| SEQ. ID. NO. 3912 | 25-LeuValAlaGlyLeuLeuSerMetIleValLeu-35 |
| SEQ. ID. NO. 3913 | 48-LeuAsnAspAlaAlaAsn-53 |
| SEQ. ID. NO. 3914 | 81-CysPheAsnMetSerGlu-86 |
| SEQ. ID. NO. 3915 | 123-AsnTyrGlnAsnPhePheGln-129 |
| SEQ. ID. NO. 3916 | 150-ThrValValSerSerCysAlaAlaIleSerLysProGlyLysGlnIleProThrLeu-168 |
| SEQ. ID. NO. 3917 | 256-LysTyrThrAspLysPheAspSerAla-264 |
| Antigenic Index - Jameson-Wolf | |
| SEQ. ID. NO. 3918 | 1-MetArgArgLysMetLeuAsnValProLysGlySerTyrAspGlyMetLys-17 |
| SEQ. ID. NO. 3919 | 42-TyrPheThrSerArgLysLeuAsnAspAlaAlaAsnGluArgLeuAlaAla-58 |
| SEQ. ID. NO. 3920 | 60-GlnAspLeuArgAsn-64 |
| SEQ. ID. NO. 3921 | 71-ArgAspAlaArgMetAlaGlyGlyPhe-79 |
| SEQ. ID. NO. 3922 | 83-AsnMetSerGluHisProAlaThrAspValIleProAspThrThrGlnGlnAsnSerProPheSerLeuLysArgAsnGlyIleAspLys-112 |
| SEQ. ID. NO. 3923 | 117-AlaGluSerSerAsnIleAsnTyrGln-125 |
| SEQ. ID. NO. 3924 | 140-IleAspAspValAsnAlaSerThr-147 |
| SEQ. ID. NO. 3925 | 157-AlaIleSerLysProGlyLysGlnIleProThrLeuGluAspAlaLysLysGluLeuLysIleProAspGlnAspLysGluGlnAsnGlyAsnIleAlaArgGlnArgHis-193 |
| SEQ. ID. NO. 3926 | 202-ArgIleAlaAspGluGluGlyLeu-209 |
| SEQ. ID. NO. 3927 | 212-PheGlnLeuAspAspLysGlyLysTrpGlyAsn-222 |
| SEQ. ID. NO. 3928 | 228-LysLysValArgHisMetLys-234 |
| SEQ. ID. NO. 3929 | 242-GlyCysProGluAspAspAspAlaGlyLysGluGluThrPheLysTyrThrAspLysPheAspSerAlaGln-265 |
| SEQ. ID. NO. 3930 | 279-SerGlyThrAspThrLysIleAlaAlaSerSerAspAsnHis-292 |
| SEQ. ID. NO. 3931 | 300-AlaThrIleArgGlyGlyAsnValCysAlaAsnArgThrLeu-313 |
| Hydrophilic Regions - Hopp-Woods | |
| SEQ. ID. NO. 3932 | 1-MetArgArgLysMetLeuAsn-7 |
| SEQ. ID. NO. 3933 | 11-GlySerTyrAspGly-15 |
| SEQ. ID. NO. 3934 | 46-ArgLysLeuAsnAspAlaAlaAsnGluArgLeuAlaAla-58 |
| SEQ. ID. NO. 3935 | 60-GlnAspLeuArgAsn-64 |
| SEQ. ID. NO. 3936 | 71-ArgAspAlaArgMet-75 |
| SEQ. ID. NO. 3937 | 104-SerLeuLysArgAsnGlyIleAspLys-112 |
| SEQ. ID. NO. 3938 | 140-IleAspAspValAsnAla-145 |
| SEQ. ID. NO. 3939 | 159-SerLysProGlyLysGln-164 |
| SEQ. ID. NO. 3940 | 166-ProThrLeuGluAspAlaLysLysGluLeuLysIleProAspGlnAspLysGluGlnAsnGlyAsnIleAlaArgGlnArgHis-193 |
| SEQ. ID. NO. 3941 | 202-ArgIleAlaAspGluGluGlyLeu-209 |
| SEQ. ID. NO. 3942 | 213-GlnLeuAspAspLysGlyLysTrpGly-221 |
| SEQ. ID. NO. 3943 | 228-LysLysValArgHisMetLys-234 |
| SEQ. ID. NO. 3944 | 243-CysProGluAspAspAspAlaGlyLysGluGluThrPheLysTyrThrAspLysPheAspSerAlaGln-265 |
| SEQ. ID. NO. 3945 | 280-GlyThrAspThrLysIleAlaAlaSerSerAsp-290 |
| 248-2 | |
| Hydrophilic Regions - Hopp-Woods | |
| SEQ. ID. NO. 3946 | 1-MetArgArgLysMetLeuAsn-7 |
| SEQ. ID. NO. 3947 | 11-GlySerTyrAspGly-15 |
| SEQ. ID. NO. 3948 | 46-ArgLysLeuAsnAspAlaAlaAsnGluArgLeuAlaAla-58 |
| SEQ. ID. NO. 3949 | 60-GlnAspLeuArgAsn-64 |
| SEQ. ID. NO. 3950 | 71-ArgAspAlaArgMet-75 |
| SEQ. ID. NO. 3951 | 104-SerLeuLysArgAsnGlyIleAspLys-112 |
| SEQ. ID. NO. 3952 | 140-IleAspAspValAsnAla-145 |
| SEQ. ID. NO. 3953 | 159-SerLysProGlyLysGln-164 |
| SEQ. ID. NO. 3954 | 166-ProThrLeuGluAspAlaLysLysGluLeuLysIleProAspGlnAspLysGluGlnAsnGlyAsnIleAlaArgGlnArgHis-193 |
| SEQ. ID. NO. 3955 | 202-ArgIleAlaAspGluGluGlyLeu-209 |

TABLE 1-continued

| | |
|---|---|
| SEQ. ID. NO. 3956 | 213-GlnLeuAspAspLysGlyLysTrpGly-221 |
| SEQ. ID. NO. 3957 | 228-LysLysValArgHisMetLys-234 |
| SEQ. ID. NO. 3958 | 243-CysProGluAspAspAspAlaGlyLysGluGluThrPheLysTyrThrAspLysPheAspSerAlaGln-265 |
| SEQ. ID. NO. 3959 | 280-GlyThrAspThrLysIleAlaAlaSerSerAsp-290 |
| Antigenic Index - Jameson-Wolf | |
| SEQ. ID. NO. 3960 | 1-MetArgLysGlnAsnThrLeuThr-8 |
| SEQ. ID. NO. 3961 | 11-ProThrSerAspGlyGlnArgGly-18 |
| SEQ. ID. NO. 3962 | 40-GlnSerTyrAsnThrGluGlnArgIleSerAlaAsnGluSerAspArgLysLeuAla-58 |
| SEQ. ID. NO. 3963 | 64-AlaAlaLeuArgGluGlyGluLeuGln-72 |
| SEQ. ID. NO. 3964 | 76-LeuGluTyrAspThrAspSerLysValThrPheSerGluAsnCysGlyLysGlyLeu-94 |
| SEQ. ID. NO. 3965 | 99-AsnValArgThrAsnAsnAspAsnGluGluAlaPhe-110 |
| SEQ. ID. NO. 3966 | 116-GlnGlyLysProThrValGluAlaValLysArgSerCysProAlaAsnSerThrAspLeuCysIleAspLysLysGlyMetGluTyrLysLysGlyThrArgSerValSerLysMetProArgTyr-157 |
| SEQ. ID. NO. 3967 | 162-LeuGlyValLysAsnGlyGluAsnValTyr-171 |
| SEQ. ID. NO. 3968 | 177-AlaTrpGlyLysAsnAlaAsnThr-184 |
| SEQ. ID. NO. 3969 | 192-ValSerAsnAsnAspGlu-197 |
| Hydrophilic Regions - Hopp-Woods | |
| SEQ. ID. NO. 3970 | 1-MetArgLysGlnAsnThr-6 |
| SEQ. ID. NO. 3971 | 11-ProThrSerAspGlyGlnArg-17 |
| SEQ. ID. NO. 3972 | 42-TyrAsnThrGluGlnArgIleSerAlaAsnGluSerAspArgLysLeuAla-58 |
| SEQ. ID. NO. 3973 | 64-AlaAlaLeuArgGluGlyGluLeuGln-72 |
| SEQ. ID. NO. 3974 | 76-LeuGluTyrAspThrAspSerLysValThrPhe-86 |
| SEQ. ID. NO. 3975 | 101-ArgThrAsnAsnAspAsnGluGluAlaPhe-110 |
| SEQ. ID. NO. 3976 | 119-ProThrValGluAlaValLysArgSerCysPro-129 |
| SEQ. ID. NO. 3977 | 135-LeuCysIleAspLysLysGlyMetGluTyrLysLysGlyThrArgSerValSerLysMetPro-155 |
| SEQ. ID. NO. 3978 | 165-LysAsnGlyGluAsnValTyr-171 |
| SEQ. ID. NO. 3979 | 193-SerAsnAsnAspGlu-197 |
| 249-1 | |
| AMPHI Regions - AMPHI | |
| SEQ. ID. NO. 3980 | 6-CysPheArgLeuLys-10 |
| SEQ. ID. NO. 3981 | 17-AlaLeuIleGluValLeuVal-23 |
| SEQ. ID. NO. 3982 | 42-ThrValAlaSerValArgGluAla-49 |
| SEQ. ID. NO. 3983 | 53-ThrIleValSerGlnIleThrGlnAsnLeuMetGluGlyMet-66 |
| Antigenic Index - Jameson-Wolf | |
| SEQ. ID. NO. 3984 | 1-MetLysAsnAsnAspCysPheArgLeuLysAspSerGlnSerGlyMetAla-17 |
| SEQ. ID. NO. 3985 | 44-AlaSerValArgGluAlaGluThr-51 |
| SEQ. ID. NO. 3986 | 70-ProThrIleAspSerAspSerAsnLysLysAsnTyr-81 |
| SEQ. ID. NO. 3987 | 93-ValAspGlyAspPheAla-98 |
| SEQ. ID. NO. 3988 | 101-AlaMetLysThrLysGlyGlnLeuAla-109 |
| SEQ. ID. NO. 3989 | 134-ValCysLysAspSerSerGlyAsnAlaProThrLeuSer-146 |
| SEQ. ID. NO. 3990 | 148-AsnAlaPheSerSerAsnCysAspAsnLysAlaAsnGlyAspThrLeu-163 |
| SEQ. ID. NO. 3991 | 171-AspSerAlaGlyAspSerAspIleSerArgThrAsnLeuGluValSerGlyAspAsn-189 |
| SEQ. ID. NO. 3992 | 196-AlaArgValGlyGlyArgGlu-202 |
| Hydrophilic Regions - Hopp-Woods | |
| SEQ. ID. NO. 3993 | 1-MetLysAsnAsnAspCysPheArgLeuLysAspSerGlnSer-14 |
| SEQ. ID. NO. 3994 | 44-AlaSerValArgGluAlaGluThr-51 |
| SEQ. ID. NO. 3995 | 72-IleAspSerAspSerAsnLysLysAsn-80 |
| SEQ. ID. NO. 3996 | 101-AlaMetLysThrLysGlyGlnLeuAla-109 |
| SEQ. ID. NO. 3997 | 134-ValCysLysAspSerSerGly-140 |
| SEQ. ID. NO. 3998 | 153-AsnCysAspAsnLysAlaAsnGly-160 |
| SEQ. ID. NO. 3999 | 172-SerAlaGlyAspSerAspIleSerArgThrAsnLeu-183 |
| SEQ. ID. NO. 4000 | 198-ValGlyGlyArgGlu-202 |
| 250-2 | |
| AMPHI Regions - AMPHI | |
| SEQ. ID. NO. 4001 | 34-PheAlaGlyGlySerGlu-39 |
| SEQ. ID. NO. 4002 | 41-AlaThrValAsnLeuTrpAlaGluPro-49 |
| SEQ. ID. NO. 4003 | 123-LeuThrLysThrSerThrAlaLeuPro-131 |
| Antigenic Index - Jameson-Wolf | |
| SEQ. ID. NO. 4004 | 14-MetGlnGlyGlyGlnLysGlyMetSer-22 |
| SEQ. ID. NO. 4005 | 35-AlaGlyGlySerGlu-39 |
| SEQ. ID. NO. 4006 | 80-IleProLeuLysLysAlaVal-86 |
| SEQ. ID. NO. 4007 | 103-GluIleGlnLysArgLysAlaAla-110 |
| SEQ. ID. NO. 4008 | 119-PheTyrSerGlyLeuThrLysThrSerThrAlaLeuProArgLeuSerSerLysLysThrIle-139 |
| Hydrophilic Regions - Hopp-Woods | |
| SEQ. ID. NO. 4009 | 80-IleProLeuLysLysAlaVal-86 |
| SEQ. ID. NO. 4010 | 103-GluIleGlnLysArgLysAlaAla-110 |
| SEQ. ID. NO. 4011 | 133-LeuSerSerLysLysThrIle-139 |
| 251 | |
| AMPHI Regions - AMPHI | |
| SEQ. ID. NO. 4012 | 59-AlaTyrGlyAspProIleGlyAlaGlyPhe-68 |
| SEQ. ID. NO. 4013 | 114-GlnValValAlaAspPheGlyGlyIleGluGlyPhe-125 |
| SEQ. ID. NO. 4014 | 160-ArgThrValGlyArgThrValArgLeuLeuLysMetIle-172 |
| SEQ. ID. NO. 4015 | 215-AlaArgThrValPheArgAlaHis-222 |
| SEQ. ID. NO. 4016 | 260-LeuGlyGlnGluCysArg-265 |
| SEQ. ID. NO. 4017 | 267-ArgHisIleAlaArgValGluSerLeuLeuArgValPheGluTyrAlaAlaAsp-284 |
| Antigenic Index - Jameson-Wolf | |
| SEQ. ID. NO. 4018 | 10-AlaArgAlaAspIleArgProProAlaGlnThrAspIleValProAsnCys-26 |
| SEQ. ID. NO. 4019 | 34-AspAlaAlaArgArgAlaValArg-41 |
| SEQ. ID. NO. 4020 | 49-AlaAspLeuProArgAsnAspIleSerProAlaTyrGlyAspProIleGlyAlaGly-67 |
| SEQ. ID. NO. 4021 | 80-LeuArgGlyArgValArgArgIleGly-88 |

TABLE 1-continued

SEQ. ID. NO. 4022 101-GluIleArgAlaLysAlaValLysProGluIle-111
SEQ. ID. NO. 4023 149-ArgLeuValGlyThr-153
SEQ. ID. NO. 4024 161-ThrValGlyArgThrValArg-167
SEQ. ID. NO. 4025 179-ProValValArgGluAlaGlyIle-186
SEQ. ID. NO. 4026 212-ValLysHisAlaArgThrValPhe-219
SEQ. ID. NO. 4027 244-ValThrGlyGlnArgThrArg-250
SEQ. ID. NO. 4028 256-IleLysAsnArgLeuGlyGlnGluCysArgAsnArgHisIleAlaArgValGluSer-274
SEQ. ID. NO. 4029 290-LeuLysThrLysThrArgAlaGluGlnProArgProAlaPhe-303
Hydrophilic Regions - Hopp-Woods
SEQ. ID. NO. 4030 10-AlaArgAlaAspIleArgProProAlaGln-19
SEQ. ID. NO. 4031 34-AspAlaAlaArgArgAlaValArg-41
SEQ. ID. NO. 4032 50-AspLeuProArgAsnAspIle-56
SEQ. ID. NO. 4033 82-GlyArgValArgArgIleGly-88
SEQ. ID. NO. 4034 101-GluIleArgAlaLysAlaValLysProGluIle-111
SEQ. ID. NO. 4035 161-ThrValGlyArgThrValArg-167
SEQ. ID. NO. 4036 179-ProValValArgGluAlaGlyIle-186
SEQ. ID. NO. 4037 212-ValLysHisAlaArgThrValPhe-219
SEQ. ID. NO. 4038 258-AsnArgLeuGlyGlnGluCysArgAsnArgHisIleAlaArgValGluSer-274
SEQ. ID. NO. 4039 292-ThrLysThrArgAlaGluGlnProArg-300
254-2
AMPHI Regions - AMPHI
SEQ. ID. NO. 4040 6-ArgPheAsnThrTyrSerHis-12
SEQ. ID. NO. 4041 32-GlyHisGlyAspGlyTyrArg-38
SEQ. ID. NO. 4042 66-LysLeuLysSerIleLeuLys-72
SEQ. ID. NO. 4043 142-ValLeuAlaValMetLysSerLeuThrAlaSerLeuPro-154
Antigenic Index - Jameson-Wolf
SEQ. ID. NO. 4044 2-TyrThrGlyGluArgPheAsnThrTyrSer-11
SEQ. ID. NO. 4045 32-GlyHisGlyAspGlyTyrArg-38
SEQ. ID. NO. 4046 65-GlyLysLeuLysSerIleLeuLysLysThrAspHis-76
SEQ. ID. NO. 4047 94-SerLeuArgAsnGlyProGly-100
SEQ. ID. NO. 4048 120-ThrIleGlyArgLysSerGluLysArgLeu-129
SEQ. ID. NO. 4049 177-AsnAspGluLysIleArgHisGlyHisGly-186
Hydrophilic Regions - Hopp-Woods
SEQ. ID. NO. 4050 65-GlyLysLeuLysSerIleLeuLysLysThrAspHis-76
SEQ. ID. NO. 4051 120-ThrIleGlyArgLysSerGluLysArgLeu-129
SEQ. ID. NO. 4052 177-AsnAspGluLysIleArgHis-183
255
AMPHI Regions - AMPHI
SEQ. ID. NO. 4053 23-ValLysThrCysAlaAspPheHisAlaPheAspGlyValAspAlaHisHisArg-40
SEQ. ID. NO. 4054 71-GlyIleGlnGlyPheAlaHis-77
SEQ. ID. NO. 4055 139-AlaGlyGlyGlyPhe-143
Antigenic Index - Jameson-Wolf
SEQ. ID. NO. 4056 33-AspGlyValAspAlaHisHisArgValGlyAspPheGly-45
SEQ. ID. NO. 4057 48-AlaValLysAsnArgPheAlaGlnAlaAspArgAspIleGlyCys-62
SEQ. ID. NO. 4058 66-GlnLeuArgAlaAspGlyIleGln-73
SEQ. ID. NO. 4059 91-ValGlyGlyLysLysArgIleLeu-98
SEQ. ID. NO. 4060 115-GlyAsnValGlyGlyAspPheArgAla-123
SEQ. ID. NO. 4061 130-PhePheGlyAsnGlySerGlySerAsnAlaGlyGly-141
SEQ. ID. NO. 4062 143-PheThrGlyGlyAla-147
SEQ. ID. NO. 4063 169-GlyAlaGluAlaGlyGly-174
Hydrophilic Regions - Hopp-Woods
SEQ. ID. NO. 4064 33-AspGlyValAspAlaHisHisArgValGlyAspPheGly-45
SEQ. ID. NO. 4065 48-AlaValLysAsnArgPheAlaGlnAlaAspArgAspIleGly-61
SEQ. ID. NO. 4066 66-GlnLeuArgAlaAspGly-71
SEQ. ID. NO. 4067 92-GlyGlyLysLysArgIleLeu-98
SEQ. ID. NO. 4068 119-GlyAspPheArgAla-123
SEQ. ID. NO. 4069 135-SerGlySerAsnAla-139
SEQ. ID. NO. 4070 169-GlyAlaGluAlaGlyGly-174
256-1
AMPHI Regions - AMPHI
SEQ. ID. NO. 4071 90-GlyValValValHisPheArgSerCysGlyGlyIleAlaAsn-103
SEQ. ID. NO. 4072 127-ArgTyrArgGluIleTyrAlaVal-134
SEQ. ID. NO. 4073 141-AsnAlaLeuAlaLysTyrLeuGlyGluGln-150
SEQ. ID. NO. 4074 173-ArgArgPheAspSerGlyIleThrArgLeuLeu-183
SEQ. ID. NO. 4075 197-LysSerLeuGlnGlyPheGlnThrAla-205
SEQ. ID. NO. 4076 207-AlaAlaGlyCysLysThrLeuGlyGluPheAspAspArgPheThrAlaProLeuHisGly-226
SEQ. ID. NO. 4077 233-TyrTyrArgGlnThrSerCysLysProLeuLeuLysHisValAla-247
SEQ. ID. NO. 4078 267-ProArgAlaAspGluValSer-273
Antigenic Index - Jameson-Wolf
SEQ. ID. NO. 4079 4-ThrProProAspThrProPhe-10
SEQ. ID. NO. 4080 12-LeuArgAsnGlyAsnAlaAspThrIleAla-21
SEQ. ID. NO. 4081 24-PheLeuGlnArgProAlaProAlaTyrArgArgGluLeuLeuProAspSerThrGlyLysThrLysVal-46
SEQ. ID. NO. 4082 49-AspPheSerAspGlyIleSerProAspAla-58
SEQ. ID. NO. 4083 67-LeuGluGlySerSerArgSerHisTyr-75
SEQ. ID. NO. 4084 82-AlaValArgAspArgGlyTrpHis-89
SEQ. ID. NO. 4085 112-GlyAspThrAlaGlu-116
SEQ. ID. NO. 4086 147-LeuGlyGluGlnGlyLysLysAlaLeu-155
SEQ. ID. NO. 4087 166-ValAspAlaGluAlaAlaGlyArgArgPheAspSerGlyIleThr-180
SEQ. ID. NO. 4088 192-LeuIleProLysAlaLysSerLeuGln-200
SEQ. ID. NO. 4089 212-ThrLeuGlyGluPheAspAspArgPheThr-221

TABLE 1-continued

SEQ. ID. NO. 4090 227-PheAlaAspArgHisAspTyrTyrArgGlnThrSerCysLysProLeuLeu-243
SEQ. ID. NO. 4091 259-ProPheLeuProProGluAlaLeuProArgAlaAspGluValSerGlu-274
SEQ. ID. NO. 4092 291-SerSerThrGlyGlyArgLeu-297
SEQ. ID. NO. 4093 311-AspSerPheArgThrAsnArgArg-318
Hydrophilic Regions - Hopp-Woods
SEQ. ID. NO. 4094 30-ProAlaTyrArgArgGluLeuLeuPro-38
SEQ. ID. NO. 4095 40-SerThrGlyLysThrLysVal-46
SEQ. ID. NO. 4096 68-GluGlySerSerArgSer-73
SEQ. ID. NO. 4097 83-ValArgAspArgGlyTrp-88
SEQ. ID. NO. 4098 147-LeuGlyGluGlnGlyLysLysAlaLeu-155
SEQ. ID. NO. 4099 166-ValAspAlaGluAlaAlaGlyArgArgPheAspSerGlyIle-179
SEQ. ID. NO. 4100 192-LeuIleProLysAlaLysSer-198
SEQ. ID. NO. 4101 212-ThrLeuGlyGluPheAspAspArgPheThr-221
SEQ. ID. NO. 4102 227-PheAlaAspArgHisAspTyrTyrArg-235
SEQ. ID. NO. 4103 265-AlaLeuProArgAlaAspGluValSerGlu-274
SEQ. ID. NO. 4104 313-PheArgThrAsnArgArg-318
257-2
AMPHI Regions - AMPHI
SEQ. ID. NO. 4105 24-SerPheLeuProAsn-28
SEQ. ID. NO. 4106 73-AspLeuValAsnLysValLeuAlaGluValAlaArgLeuGluLysIleValGlnProLeu-92
Antigenic Index - Jameson-Wolf
SEQ. ID. NO. 4107 1-MetGlyArgHisPheGlyArgArgArgPhe-10
SEQ. ID. NO. 4108 31-AlaAlaAspAspGluLysArgAsnGlyAspGluLysArgAsnGluAsn-46
SEQ. ID. NO. 4109 56-GlySerGlyAlaGlu-60
SEQ. ID. NO. 4110 65-GlyValAspAspArgArgAlaAlaAspLeuVal-75
SEQ. ID. NO. 4111 83-AlaArgLeuGluLysIleVal-89
Hydrophilic Regions - Hopp-Woods
SEQ. ID. NO. 4112 4-HisPheGlyArgArgArgPhe-10
SEQ. ID. NO. 4113 31-AlaAlaAspAspGluLysArgAsnGlyAspGluLysArgAsnGlu-45
SEQ. ID. NO. 4114 65-GlyValAspAspArgArgAlaAlaAspLeuVal-75
SEQ. ID. NO. 4115 83-AlaArgLeuGluLysIleVal-89
259-1
AMPHI Regions - AMPHI
SEQ. ID. NO. 4116 154-TyrGlyArgValPheAlaAspIlePheGluLeuSer-165
SEQ. ID. NO. 4117 172-AlaPheLysGlyMetLeuLysLeuThrAlaGluTyrLysAsnIlePheGlyAspAlaCysArg-192
SEQ. ID. NO. 4118 203-AsnGlnAlaLeuGlnGluIleSerLysThrSerGlu-214
Antigenic Index - Jameson-Wolf
SEQ. ID. NO. 4119 34-LysAlaTyrThrGluGluLeuProPro-42
SEQ. ID. NO. 4120 61-SerAlaArgSerLysAlaLysAlaGluLysPheTyrArgGluLysMetIleGln-78
SEQ. ID. NO. 4121 93-LeuGluHisLysPro-97
SEQ. ID. NO. 4122 105-LysAsnHisGlyLysGlyMetAlaGluGlnValArgPheLysAla-119
SEQ. ID. NO. 4123 121-ValLeuProAspAspGluAspAlaArgThrIleAla-132
SEQ. ID. NO. 4124 144-GlyThrAspAlaValAlaSerGlyGluThrTyrGlyArgVal-157
SEQ. ID. NO. 4125 168-LeuGluGlyArgAlaPhe-173
SEQ. ID. NO. 4126 189-AspAlaCysArgSerGluThrAlaLeu-197
SEQ. ID. NO. 4127 208-GluIleSerLysThrSerGluLysSerLysArg-218
Hydrophilic Regions - Hopp-Woods
SEQ. ID. NO. 4128 35-AlaTyrThrGluGluLeuPro-41
SEQ. ID. NO. 4129 62-AlaArgSerLysAlaLysAlaGluLysPheTyrArgGluLysMetIleGln-78
SEQ. ID. NO. 4130 93-LeuGluHisLysPro-97
SEQ. ID. NO. 4131 106-AsnHisGlyLysGlyMetAlaGluGlnValArgPheLysAla-119
SEQ. ID. NO. 4132 121-ValLeuProAspAspGluAspAlaArgThrIleAla-132
SEQ. ID. NO. 4133 168-LeuGluGlyArgAlaPhe-173
SEQ. ID. NO. 4134 189-AspAlaCysArgSerGluThrAlaLeu-197
SEQ. ID. NO. 4135 208-GluIleSerLysThrSerGluLysSerLysArg-218
260-2
AMPHI Regions - AMPHI
SEQ. ID. NO. 4136 12-ProPheSerSerLeuPheArgAlaLeuPhe-21
SEQ. ID. NO. 4137 53-PheIleAspSerValGlyGlnValAlaAlaArgLeuPheGlnAlaPhe-68
SEQ. ID. NO. 4138 158-GlnValGlyIleValAspLeuIlePro-166
SEQ. ID. NO. 4139 175-LeuProArgAlaValGln-180
Antigenic Index - Jameson-Wolf
SEQ. ID. NO. 4140 20-LeuPheGluAspArgValGlyIle-27
SEQ. ID. NO. 4141 30-GlyAlaHisAspAlaAlaGlu-36
SEQ. ID. NO. 4142 38-AspPheLeuProGluGluPheThrArg-46
SEQ. ID. NO. 4143 80-ProAlaPheArgAlaArgGluGlnAlaArgArgGlySerGly-93
SEQ. ID. NO. 4144 97-GlyAsnAspLeuArgMetProHisLysAspAlaValGluValAspIleAspGlyGlyAsnThrVal-118
SEQ. ID. NO. 4145 126-ThrHisPheAspAspGlyAspAla-133
SEQ. ID. NO. 4146 139-AlaGluAlaArgPhe-143
SEQ. ID. NO. 4147 184-ArgAsnAlaProGlnGly-189
SEQ. ID. NO. 4148 196-ValAlaPheArgArgValArgAla-203
Hydrophilic Regions - Hopp-Woods
SEQ. ID. NO. 4149 20-LeuPheGluAspArgValGlyIle-27
SEQ. ID. NO. 4150 30-GlyAlaHisAspAlaAlaGlu-36
SEQ. ID. NO. 4151 82-PheArgAlaArgGluGlnAlaArgArgGlySer-92
SEQ. ID. NO. 4152 98-AsnAspLeuArgMetProHisLysAspAlaValGluValAspIleAspGly-114
SEQ. ID. NO. 4153 127-HisPheAspAspGlyAspAla-133

TABLE 1-continued

| | |
|---|---|
| SEQ. ID. NO. 4154 | 139-AlaGluAlaArgPhe-143 |
| SEQ. ID. NO. 4155 | 196-ValAlaPheArgArgValArgAla-203 |
| 261 | |
| AMPHI Regions - AMPHI | |
| SEQ. ID. NO. 4156 | 22-GlnIlePheArgGln-26 |
| SEQ. ID. NO. 4157 | 32-AspThrAlaArgAlaPheAlaAlaAla-40 |
| SEQ. ID. NO. 4158 | 50-GlyLeuLeuAlaAspIle-55 |
| SEQ. ID. NO. 4159 | 94-ArgPheAspLysHis-98 |
| SEQ. ID. NO. 4160 | 137-AlaValTyrLysGlyIleArgAsnAlaValPhe-147 |
| SEQ. ID. NO. 4161 | 158-GlnGlyIleValArgAsnLeu-164 |
| SEQ. ID. NO. 4162 | 203-AspValPheAlaProVal-208 |
| SEQ. ID. NO. 4163 | 212-CysLeuAsnGlnAlaGlyGly-218 |
| Antigenic Index - Jameson-Wolf | |
| SEQ. ID. NO. 4164 | 40-AlaAlaAspAspAlaVal-45 |
| SEQ. ID. NO. 4165 | 62-ValArgGlnArgProArgLeuArgLeu-70 |
| SEQ. ID. NO. 4166 | 74-HisGlnArgArgValAspLeu-80 |
| SEQ. ID. NO. 4167 | 86-ArgGlnIleLysGlyAsnValHisArgPheAspLysHisVal-99 |
| SEQ. ID. NO. 4168 | 111-AlaHisAlaArgAspAspValProTyr-119 |
| SEQ. ID. NO. 4169 | 126-AsnArgGlyIleGluGlnGluLysArgVal-135 |
| SEQ. ID. NO. 4170 | 149-SerPheAspGlyGlyGly-154 |
| SEQ. ID. NO. 4171 | 181-ArgAsnProAlaGly-185 |
| SEQ. ID. NO. 4172 | 197-LeuGluSerAsnGlyLeuAsp-203 |
| SEQ. ID. NO. 4173 | 214-AsnGlnAlaGlyGlyArgIleLeuThrAlaArgLysAspAspGlnGlyLeu-230 |
| Hydrophilic Regions - Hopp-Woods | |
| SEQ. ID. NO. 4174 | 40-AlaAlaAspAspAlaVal-45 |
| SEQ. ID. NO. 4175 | 62-ValArgGlnArgProArgLeuArgLeu-70 |
| SEQ. ID. NO. 4176 | 74-HisGlnArgArgValAspLeu-80 |
| SEQ. ID. NO. 4177 | 91-AsnValHisArgPheAspLysHisVal-99 |
| SEQ. ID. NO. 4178 | 112-HisAlaArgAspAspValPro-118 |
| SEQ. ID. NO. 4179 | 127-ArgGlyIleGluGlnGluLysArgVal-135 |
| SEQ. ID. NO. 4180 | 221-LeuThrAlaArgLysAspAspGlnGly-229 |
| 263-2 | |
| AMPHI Regions - AMPHI | |
| SEQ. ID. NO. 4181 | 32-AsnLeuIleGlyValLeuSerAsnAla-40 |
| SEQ. ID. NO. 4182 | 42-GluAlaLeuAlaPheTyrGlnGluValGlyLysLeuAsnAlaAlaAsnSerLeuThr-60 |
| SEQ. ID. NO. 4183 | 86-LysLeuAlaThrLeuLysLys-92 |
| SEQ. ID. NO. 4184 | 100-LysAlaAlaArgAlaLeuAlaAlaGlyGlu-109 |
| SEQ. ID. NO. 4185 | 115-LeuGlyAlaLeuAlaAlaPheThrGln-123 |
| SEQ. ID. NO. 4186 | 135-GluGluLeuLysAlaPhePheAspAla-143 |
| SEQ. ID. NO. 4187 | 157-ValAlaLeuAlaThrLeuCysAsnTyrValAsnAsnLeuGly-170 |
| Antigenic Index - Jameson-Wolf | |
| SEQ. ID. NO. 4188 | 10-GluThrAlaProGluAlaAlaLysAlaArgValGluAla-22 |
| SEQ. ID. NO. 4189 | 37-LeuSerAsnAlaPro-41 |
| SEQ. ID. NO. 4190 | 72-AlaArgThrAsnGlnCysGly-78 |
| SEQ. ID. NO. 4191 | 97-GlnSerValLysAlaAlaArg-103 |
| SEQ. ID. NO. 4192 | 108-GlyGluPheAspAspAlaLysLeu-115 |
| SEQ. ID. NO. 4193 | 126-MetAlaLysLysGlyAlaValSerAspGluGluLeuLysAla-139 |
| SEQ. ID. NO. 4194 | 170-GlyGlnThrGluIleAsnProGluLeu-178 |
| Hydrophilic Regions - Hopp-Woods | |
| SEQ. ID. NO. 4195 | 11-ThrAlaProGluAlaAlaLysAlaArgValGluAla-22 |
| SEQ. ID. NO. 4196 | 97-GlnSerValLysAlaAlaArg-103 |
| SEQ. ID. NO. 4197 | 108-GlyGluPheAspAspAlaLysLeu-115 |
| SEQ. ID. NO. 4198 | 126-MetAlaLysLysGlyAlaValSerAspGluGluLeuLysAla-139 |
| 264 | |
| AMPHI Regions - AMPHI | |
| SEQ. ID. NO. 4199 | 55-ValAlaGluPheThrGlnThrGly-62 |
| SEQ. ID. NO. 4200 | 96-IleProSerTyrValArgValThrAsnThrLys-106 |
| SEQ. ID. NO. 4201 | 124-AsnArgIleIleAspValSer-130 |
| SEQ. ID. NO. 4202 | 183-LeuAsnGlnAlaAla-187 |
| Antigenic Index - Jameson-Wolf | |
| SEQ. ID. NO. 4203 | 27-AlaValValLysAlaGluLysLeuHisAlaSerAlaAsnArgSerTyrLysValAlaGlyLysArgTyrThrProLysAsnGlnVal-55 |
| SEQ. ID. NO. 4204 | 57-GluPheThrGlnThrGlyAsnAlaSerTrp-66 |
| SEQ. ID. NO. 4205 | 68-GlyGlyArgPheHisGlyArgLysThrSerGlyGlyGluArgTyrAsp-83 |
| SEQ. ID. NO. 4206 | 103-ThrAsnThrLysAsnGlyLysSerVal-111 |
| SEQ. ID. NO. 4207 | 114-ArgValAsnAspArgGlyProPheHisGlyAsnArgIleIleAspValSerLysAlaAlaAla-134 |
| SEQ. ID. NO. 4208 | 153-ValProGlyGlnSerAlaProValAlaGluAsnLysAspIlePheIle-168 |
| SEQ. ID. NO. 4209 | 170-LeuLysSerPheGlyThrGluHisGluAla-179 |
| SEQ. ID. NO. 4210 | 200-SerValGluLysArgArgTyrGluTyr-208 |
| SEQ. ID. NO. 4211 | 213-GlyProPheThrSerGlnGluArgAlaAlaGluAlaGluAlaGlnAla-228 |
| Hydrophilic Regions - Hopp-Woods | |
| SEQ. ID. NO. 4212 | 27-AlaValValLysAlaGluLysLeuHisAlaSerAlaAsnArgSerTyrLysValAlaGlyLysArgTyrThrPro-51 |
| SEQ. ID. NO. 4213 | 71-PheHisGlyArgLysThrSerGlyGlyGluArgTyrAsp-83 |
| SEQ. ID. NO. 4214 | 103-ThrAsnThrLysAsnGlyLys-109 |
| SEQ. ID. NO. 4215 | 115-ValAsnAspArgGlyProPheHis-122 |
| SEQ. ID. NO. 4216 | 125-ArgIleIleAspValSerLysAlaAlaAla-134 |
| SEQ. ID. NO. 4217 | 159-ProValAlaGluAsnLysAspIlePheIle-168 |

TABLE 1-continued

| | |
|---|---|
| SEQ. ID. NO. 4218 | 171-LysSerPheGlyThrGluHisGluAla-179 |
| SEQ. ID. NO. 4219 | 200-SerValGluLysArgArgTyrGluTyr-208 |
| SEQ. ID. NO. 4220 | 216-ThrSerGlnGluArgAlaAlaGluAlaGluAlaGlnAla-228 |
| 266-2 | |
| Antigenic Index - Jameson-Wolf | |
| SEQ. ID. NO. 4221 | 30-AlaLeuLysArgLysHisPhe-36 |
| SEQ. ID. NO. 4222 | 57-LeuGluSerArgAlaGlySerValHisAspGlnGlyTrpGlu-70 |
| SEQ. ID. NO. 4223 | 93-TrpHisThrArgAsnArgGlu-99 |
| Hydrophilic Regions - Hopp-Woods | |
| SEQ. ID. NO. 4224 | 30-AlaLeuLysArgLysHisPhe-36 |
| SEQ. ID. NO. 4225 | 59-SerArgAlaGlySerValHis-65 |
| 268-1 | |
| AMPHI Regions - AMPHI | |
| SEQ. ID. NO. 4226 | 6-AspGlyLeuHisLysPheLysHisIleCysSerAlaAla-18 |
| SEQ. ID. NO. 4227 | 22-IleLysGluProLeuAspLysVal-29 |
| SEQ. ID. NO. 4228 | 52-GlnGluAlaAlaArgValSerGluTrp-60 |
| SEQ. ID. NO. 4229 | 70-GluPheGluGlnPheTrpLysGlyLeuProGlnThrValGlnAsn-84 |
| SEQ. ID. NO. 4230 | 89-SerGlnLysThrTrpLysSerGlyMetAspLys-99 |
| SEQ. ID. NO. 4231 | 110-LysThrProAsnGlyIleLys-116 |
| Antigenic Index - Jameson-Wolf | |
| SEQ. ID. NO. 4232 | 1-ValGlnSerArgTyrAspGly-7 |
| SEQ. ID. NO. 4233 | 21-LeuIleLysGluProLeuAspLysValLysGlnArgAsnGluGluLeuGluAlaAlaGluGluAlaAlaAla-44 |
| SEQ. ID. NO. 4234 | 47-AlaLeuGlyArgGluGlnGluAlaAlaArgValSerGluTrpGluGluArgTyrLysLeuSerArgSerGluPhe-71 |
| SEQ. ID. NO. 4235 | 82-ValGlnAsnLysLeuGlnAlaSerGlnLysThrTrpLysSerGlyMetAspLysIleCysAlaAsnAsnAlaLysAlaGluGlyLysThrProAsnGlyIle LysPhe-117 |
| SEQ. ID. NO. 4236 | 119-GluLeuAlaCysLysThrAlaLysThrGluAlaArgLeuGluGluLeuHisAsnArgLysLysAlaLeuIleAspGluMetAlaArgGluAlaAspLys LysGluLeuSerLysArgLeu-158 |
| Hydrophilic Regions - Hopp-Woods | |
| SEQ. ID. NO. 4237 | 3-SerArgTyrAspGly-7 |
| SEQ. ID. NO. 4238 | 21-LeuIleLysGluProLeuAspLysValLysGlnArgAsnGluGluLeuGluAlaAlaGluGluAlaAlaAla-44 |
| SEQ. ID. NO. 4239 | 47-AlaLeuGlyArgGluGlnGluAlaAlaArgValSerGluTrpGluGluArgTyrLysLeuSerArgSerGluPhe-71 |
| SEQ. ID. NO. 4240 | 91-LysThrTrpLysSerGlyMetAspLysIleCys-101 |
| SEQ. ID. NO. 4241 | 104-AsnAlaLysAlaGluGlyLysThrProAsn-113 |
| SEQ. ID. NO. 4242 | 119-GluLeuAlaCysLysThrAlaLysThrGluAlaArgLeuGluGluLeuHisAsnArgLysLysAlaLeuIleAspGluMetAlaArgGluAlaAspLys LysGluLeuSerLysArgLeu-158 |
| 269-2 | |
| AMPHI Regions - AMPHI | |
| SEQ. ID. NO. 4243 | 39-AlaSerValProAla-43 |
| SEQ. ID. NO. 4244 | 54-TrpAspPheIleGlnAsnThr-60 |
| SEQ. ID. NO. 4245 | 73-PheLysThrArgAlaLeuGlyArgPheSerSerPro-84 |
| Antigenic Index - Jameson-Wolf | |
| SEQ. ID. NO. 4246 | 30-ArgSerAlaLeuSerCysLysProCysAlaSerValProAlaSerSer-45 |
| SEQ. ID. NO. 4247 | 60-ThrAlaSerProLysValSer-66 |
| SEQ. ID. NO. 4248 | 73-PheLysThrArgAlaLeuGlyArgPheSerSer-83 |
| SEQ. ID. NO. 4249 | 90-LeuSerGluArgGlyValLysLysProLeu-99 |
| SEQ. ID. NO. 4250 | 107-GlnValAspThrSerAla-112 |
| SEQ. ID. NO. 4251 | 117-SerLeuArgSerSer-121 |
| Hydrophilic Regions - Hopp-Woods | |
| SEQ. ID. NO. 4252 | 61-AlaSerProLysVal-65 |
| SEQ. ID. NO. 4253 | 73-PheLysThrArgAlaLeuGly-79 |
| SEQ. ID. NO. 4254 | 90-LeuSerGluArgGlyValLysLysProLeu-99 |
| 270-2 | |
| AMPHI Regions - AMPHI | |
| SEQ. ID. NO. 4255 | 41-AspLeuThrGluGlyCys-46 |
| SEQ. ID. NO. 4256 | 49-ProAspGlySerArg-53 |
| SEQ. ID. NO. 4257 | 100-GlnProSerGlyThrTrp-105 |
| Antigenic Index - Jameson-Wolf | |
| SEQ. ID. NO. 4258 | 1-MetAsnLysAsnArgLysLeu-7 |
| SEQ. ID. NO. 4259 | 41-AspLeuThrGluGlyCysThrLeuProAspGlySerArgValArgAlaAlaAlaValSerThrLysLysProPhe-65 |
| SEQ. ID. NO. 4260 | 71-HisAlaProAlaGlyThrGlu-77 |
| SEQ. ID. NO. 4261 | 86-LysAsnMetAspMetGlyPhe-92 |
| SEQ. ID. NO. 4262 | 95-TyrMetPheGluArgGlnProSerGlyThr-104 |
| SEQ. ID. NO. 4263 | 116-ValGluGlyArgArgAspPheThrAla-124 |
| SEQ. ID. NO. 4264 | 128-IleGlySerArgThrPhe-133 |
| Hydrophilic Regions - Hopp-Woods | |
| SEQ. ID. NO. 4265 | 1-MetAsnLysAsnArgLysLeu-7 |
| SEQ. ID. NO. 4266 | 49-ProAspGlySerArgValArgAla-56 |
| SEQ. ID. NO. 4267 | 60-SerThrLysLysProPhe-65 |
| SEQ. ID. NO. 4268 | 73-ProAlaGlyThrGlu-77 |
| SEQ. ID. NO. 4269 | 96-MetPheGluArgGlnPro-101 |
| SEQ. ID. NO. 4270 | 116-ValGluGlyArgArgAspPheThrAla-124 |
| 271-2 | |
| AMPHI Regions - AMPHI | |
| SEQ. ID. NO. 4271 | 6-MetAlaArgIleTrp-10 |
| SEQ. ID. NO. 4272 | 20-SerProCysProAla-24 |
| SEQ. ID. NO. 4273 | 29-ProLysSerProAla-33 |
| Antigenic Index - Jameson-Wolf | |
| SEQ. ID. NO. 4274 | 2-PheSerSerArgMetAlaArg-8 |
| SEQ. ID. NO. 4275 | 25-LeuThrThrLysProLysSerProAlaLys-34 |
| SEQ. ID. NO. 4276 | 41-ArgSerAsnCysLeu-45 |

TABLE 1-continued

| | |
|---|---|
| SEQ. ID. NO. 4277 | 61-SerSerThrThrGlyAlaProThrSerArg-70 |
| SEQ. ID. NO. 4278 | 78-SerAlaSerIleAsnLysAspThrArgMetProAlaSerVal-91 |
| SEQ. ID. NO. 4279 | 102-CysCysAlaAsnThrSerLysProProSer-111 |
| Hydrophilic Regions - Hopp-Woods | |
| SEQ. ID. NO. 4280 | 27-ThrLysProLysSerProAlaLys-34 |
| SEQ. ID. NO. 4281 | 80-SerIleAsnLysAspThrArgMet-87 |
| SEQ. ID. NO. 4282 | 105-AsnThrSerLysProPro-110 |
| 272-2 | |
| AMPHI Regions - AMPHI | |
| SEQ. ID. NO. 4283 | 44-IleThrArgIleThrAspGlu-50 |
| SEQ. ID. NO. 4284 | 70-AlaGluGluPheSerSerThrAsn-77 |
| SEQ. ID. NO. 4285 | 106-PheArgThrIleThrSer-111 |
| SEQ. ID. NO. 4286 | 165-IleIleThrIleGluAspProIleGlu-173 |
| SEQ. ID. NO. 4287 | 194-AsnTrpMetAlaAlaLeuLysAsnThrLeuArgGlnAla-206 |
| SEQ. ID. NO. 4288 | 244-AsnGlnAlaLeuAspArgIleIleAsn-252 |
| SEQ. ID. NO. 4289 | 307-GlyAsnIleHisGluIleLysGluValMetLys-317 |
| SEQ. ID. NO. 4290 | 328-AspGlnHisLeuTyrGln-333 |
| SEQ. ID. NO. 4291 | 345-AlaLeuLysAsnAlaAspSer-351 |
| Antigenic Index - Jameson-Wolf | |
| SEQ. ID. NO. 4292 | 2-PheThrAspGluAsnMetThrAlaLysGluGluLeu-13 |
| SEQ. ID. NO. 4293 | 20-MetAsnGlnAsnLysGlySerAsp-27 |
| SEQ. ID. NO. 4294 | 38-MetLysLeuAspGlyLysIleThrArgIleThrAspGluProLeuThrAlaGluLysCysMet-58 |
| SEQ. ID. NO. 4295 | 68-LysGlnAlaGluGluPheSerSerThrAsnGlu-78 |
| SEQ. ID. NO. 4296 | 85-LeuProAspThrSerArgPheArgVal-93 |
| SEQ. ID. NO. 4297 | 109-IleThrSerLysIleProLysPheGluSerLeuAsn-120 |
| SEQ. ID. NO. 4298 | 128-ValAlaLeuLysLysArgGly-134 |
| SEQ. ID. NO. 4299 | 142-ThrGlySerGlyLysSerThrSerLeu-150 |
| SEQ. ID. NO. 4300 | 154-IleAspTyrArgAsnGluAsnSerPheGly-163 |
| SEQ. ID. NO. 4301 | 168-IleGluAspProIle-172 |
| SEQ. ID. NO. 4302 | 176-HisGluHisLysAsnCys-181 |
| SEQ. ID. NO. 4303 | 184-ThrGlnArgGluValGlyValAspThrGluAsn-194 |
| SEQ. ID. NO. 4304 | 199-LeuLysAsnThrLeuArgGlnAlaProAsp-208 |
| SEQ. ID. NO. 4305 | 214-GluIleArgAspArgGluThrMet-221 |
| SEQ. ID. NO. 4306 | 241-AsnSerThrAsnGlnAlaLeuAspArg-249 |
| SEQ. ID. NO. 4307 | 254-PheProGluGluArgArgGluGlnLeuLeu-263 |
| SEQ. ID. NO. 4308 | 278-LeuValProArgAspGlyGlyLysGlyArgValAlaAla-290 |
| SEQ. ID. NO. 4309 | 310-HisGluIleLysGluValMetLysLysSerThr-320 |
| SEQ. ID. NO. 4310 | 334-LeuTyrGluLysGlyAspIleSerLeu-342 |
| SEQ. ID. NO. 4311 | 344-GluAlaLeuLysAsnAlaAspSerAlaHisAspLeu-355 |
| SEQ. ID. NO. 4312 | 361-LeuArgSerArgArgAlaGlnSerSerSerProAspLeuGluLeu-375 |
| Hydrophilic Regions - Hopp-Woods | |
| SEQ. ID. NO. 4313 | 2-PheThrAspGluAsnMetThrAlaLysGluGluLeu-13 |
| SEQ. ID. NO. 4314 | 20-MetAsnGlnAsnLysGlySerAsp-27 |
| SEQ. ID. NO. 4315 | 38-MetLysLeuAspGlyLysIleThrArgIleThrAspGluProLeuThrAlaGluLysCysMet-58 |
| SEQ. ID. NO. 4316 | 68-LysGlnAlaGluGluPheSerSer-75 |
| SEQ. ID. NO. 4317 | 87-AspThrSerArgPheArgVal-93 |
| SEQ. ID. NO. 4318 | 112-LysIleProLysPheGluSer-118 |
| SEQ. ID. NO. 4319 | 128-ValAlaLeuLysLysArgGly-134 |
| SEQ. ID. NO. 4320 | 143-GlySerGlyLysSerThrSer-149 |
| SEQ. ID. NO. 4321 | 155-AspTyrArgAsnGluAsnSer-161 |
| SEQ. ID. NO. 4322 | 168-IleGluAspProIle-172 |
| SEQ. ID. NO. 4323 | 176-HisGluHisLysAsn-180 |
| SEQ. ID. NO. 4324 | 184-ThrGlnArgGluValGlyValAspThr-192 |
| SEQ. ID. NO. 4325 | 201-AsnThrLeuArgGlnAlaPro-207 |
| SEQ. ID. NO. 4326 | 214-GluIleArgAspArgGluThrMet-221 |
| SEQ. ID. NO. 4327 | 245-GlnAlaLeuAspArg-249 |
| SEQ. ID. NO. 4328 | 255-ProGluGluArgArgGluGlnLeuLeu-263 |
| SEQ. ID. NO. 4329 | 278-LeuValProArgAspGlyGlyLysGlyArgValAlaAla-290 |
| SEQ. ID. NO. 4330 | 310-HisGluIleLysGluValMetLysLysSerThr-320 |
| SEQ. ID. NO. 4331 | 336-GluLysGlyAspIleSerLeu-342 |
| SEQ. ID. NO. 4332 | 344-GluAlaLeuLysAsnAlaAspSerAlaHisAspLeu-355 |
| SEQ. ID. NO. 4333 | 361-LeuArgSerArgArgAlaGlnSerSerSerProAspLeuGluLeu |
| 274 | |
| AMPHI Regions - AMPHI | |
| SEQ. ID. NO. 4334 | 31-TyrLysAspGlyLys-35 |
| SEQ. ID. NO. 4335 | 111-GluAlaValPheLysThrLeuSerPro-119 |
| Antigenic Index - Jameson-Wolf | |
| SEQ. ID. NO. 4336 | 25-LeuValThrAspAspTyrTyrLysAspGlyLysHisIleAsp-38 |
| SEQ. ID. NO. 4337 | 40-GlnLeuHisArgAspGluGluAlaValArgArgHisIle-52 |
| SEQ. ID. NO. 4338 | 60-ProAspMetAsnAla-64 |
| SEQ. ID. NO. 4339 | 71-GlyGluPheAspGlyLysGlnPro-78 |
| SEQ. ID. NO. 4340 | 85-HisProThrArgLysAlaAspAspGlnThrVal-95 |
| SEQ. ID. NO. 4341 | 99-ProValGlySerAlaGlnAsnGlyArgAlaGluTyr-110 |
| SEQ. ID. NO. 4342 | 117-LeuSerProThrAsnHis-122 |
| SEQ. ID. NO. 4343 | 126-ArgValGluAspAlaAlaGly-132 |
| SEQ. ID. NO. 4344 | 136-ValGluAsnLysTrpIleThrSerGlnGlyAsnAlaValAspLeuThrProMetAspLysLeuPheAsnAsnThrGluSerLys-163 |
| Hydrophilic Regions - Hopp-Woods | |
| SEQ. ID. NO. 4345 | 29-AspTyrTyrLysAspGlyLysHisIleAsp-38 |
| SEQ. ID. NO. 4346 | 40-GlnLeuHisArgAspGluGluAlaValArgArgHisIle-52 |
| SEQ. ID. NO. 4347 | 72-GluPheAspGlyLysGln-77 |

TABLE 1-continued

SEQ. ID. NO. 4348 86-ProThrArgLysAlaAspAspGlnThrVal-95
SEQ. ID. NO. 4349 104-GlnAsnGlyArgAlaGluTyr-110
SEQ. ID. NO. 4350 126-ArgValGluAspAlaAlaGly-132
SEQ. ID. NO. 4351 151-ThrProMetAspLysLeuPheAsn-158
276
AMPHI Regions - AMPHI
SEQ. ID. NO. 4352 9-MetMetArgSerAlaProSerMetValValArgArgTrpAlaThrMetMet-25
SEQ. ID. NO. 4353 60-SerPheLysMetAlaArg-65
SEQ. ID. NO. 4354 80-ProPheAspProMetGlyTrp-86
SEQ. ID. NO. 4355 115-GlyArgLeuTyrArgThrPheSerAsn-123
SEQ. ID. NO. 4356 164-ThrLysArgGlySerArgLeu-170
SEQ. ID. NO. 4357 207-SerThrSerThrLeuArgLysLeuMetArgProSerThr-219
Antigenic Index - Jameson-Wolf
SEQ. ID. NO. 4358 10-MetArgSerAlaProSerMetVal-17
SEQ. ID. NO. 4359 29-PheSerIleArgArgSerSerAlaCysTrpThrArgArgSerAspSerLeuSer-46
SEQ. ID. NO. 4360 52-SerSerAsnAsnAsnIle-57
SEQ. ID. NO. 4361 67-MetAlaThrArgCysArgCysProProAspLysLeuLeuPro-80
SEQ. ID. NO. 4362 82-AspProMetGlyTrpCysSerProSerGlyGluLeuSer-94
SEQ. ID. NO. 4363 104-ArgAlaAsnArgThrSerAlaSerProAlaSerGlyArgLeuTyr-118
SEQ. ID. NO. 4364 121-PheSerAsnArgValSerSerAsnArgAsnThrSerTrpGluThrArgAlaAsnTrpAlaArgArgGlnSerSerLeu-146
SEQ. ID. NO. 4365 158-LeuProAlaAspGlySerThrLysArgGlySerArgLeuThrThr-172
SEQ. ID. NO. 4366 176-ProLeuProGluArgProThrArgAlaThrArgSerProCysLeu-190
SEQ. ID. NO. 4367 194-LeuLysLeuSerArg-198
SEQ. ID. NO. 4368 200-LeuMetProSerGluArgTyrSerThrSerThrLeuArgLysLeuMetArgProSerThrArgCysGlyAla-223
SEQ. ID. NO. 4369 229-CysSerGlyGlyValSerArgAsnAlaHisThrProSerAlaAlaArgAsn-245
Hydrophilic Regions - Hopp-Woods
SEQ. ID. NO. 4370 29-PheSerIleArgArgSerSer-35
SEQ. ID. NO. 4371 38-TrpThrArgArgSerAspSerLeu-45
SEQ. ID. NO. 4372 67-MetAlaThrArgCysArgCysProProAspLys-77
SEQ. ID. NO. 4373 90-SerGlyGluLeuSer-94
SEQ. ID. NO. 4374 104-ArgAlaAsnArgThrSerAla-110
SEQ. ID. NO. 4375 124-ArgValSerSerAsnArgAsnThrSerTrpGluThr-135
SEQ. ID. NO. 4376 137-AlaAsnTrpAlaArgArgGlnSerSer-145
SEQ. ID. NO. 4377 161-AspGlySerThrLysArgGlySerArg-169
SEQ. ID. NO. 4378 176-ProLeuProGluArgProThrArgAlaThrArg-186
SEQ. ID. NO. 4379 194-LeuLysLeuSerArg-198
SEQ. ID. NO. 4380 200-LeuMetProSerGluArgTyrSer-207
SEQ. ID. NO. 4381 210-ThrLeuArgLysLeuMetArgProSerThrArgCys-221
SEQ. ID. NO. 4382 232-GlyValSerArgAsnAlaHis-238
277
AMPHI Regions - AMPHI
SEQ. ID. NO. 4383 39-GlyIleAlaValPheGluValValGlyGlyLeuLeuAspPheValLeu-54
SEQ. ID. NO. 4384 70-CysProAsnGluValValAspValPheTyrThr-80
SEQ. ID. NO. 4385 87-AlaPheAspAlaValGlyAspPheAlaGluTyrGlyArgAlaValAspAlaAlaAspLeuLeuGluIleGlyLysLeuGlyTyrPheHis-116
SEQ. ID. NO. 4386 180-AlaValGlyValValAlaValAla-187
Antigenic Index - Jameson-Wolf
SEQ. ID. NO. 4387 2-ProArgPheGluAspLysLeuValGlyArgGlnGlyGluGlyGlyVal-17
SEQ. ID. NO. 4388 60-ValGlyAspGlyValAlaVal-66
SEQ. ID. NO. 4389 68-ArgPheCysProAsnGluVal-74
SEQ. ID. NO. 4390 95-AlaGluTyrGlyArgAlaValAspAla-103
SEQ. ID. NO. 4391 118-ValGluProAspPheProAlaGlnThrProArgAlaGluGlyGly-132
SEQ. ID. NO. 4392 138-PheAspLysAlaAspValVal-144
SEQ. ID. NO. 4393 156-ValGluIleGluVal-160
SEQ. ID. NO. 4394 164-GlyGlySerGlyLeuGluGlyAspLeu-172
SEQ. ID. NO. 4395 196-LeuAspValGlyGlyLysProArgLeuGlyAla-206
SEQ. ID. NO. 4396 208-CysAlaGlnAlaGlyGlyGly-214
SEQ. ID. NO. 4397 219-GlyThrAspPheHis-223
SEQ. ID. NO. 4398 226-GlyLeuAspAspGlyAla-231
SEQ. ID. NO. 4399 239-LeuGlnPheGluAspAspLeuLeuGluGlyLysHisGlyLeu-252
Hydrophilic Regions - Hopp-Woods
SEQ. ID. NO. 4400 2-ProArgPheGluAspLysLeuValGlyArgGlnGlyGlu-14
SEQ. ID. NO. 4401 95-AlaGluTyrGlyArgAlaValAspAla-103
SEQ. ID. NO. 4402 118-ValGluProAspPhe-122
SEQ. ID. NO. 4403 126-ThrProArgAlaGluGly-131
SEQ. ID. NO. 4404 138-PheAspLysAlaAspValVal-144
SEQ. ID. NO. 4405 156-ValGluIleGluVal-160
SEQ. ID. NO. 4406 167-GlyLeuGluGlyAspLeu-172
SEQ. ID. NO. 4407 198-ValGlyGlyLysProArgLeuGlyAla-206
SEQ. ID. NO. 4408 226-GlyLeuAspAspGlyAla-231
SEQ. ID. NO. 4409 239-LeuGlnPheGluAspAspLeuLeuGluGlyLysHisGlyLeu-252
278
AMPHI Regions - AMPHI
SEQ. ID. NO. 4410 7-GlyAlaIlePheSerIleGly-13
SEQ. ID. NO. 4411 20-IleGlyProLeuProSerIleGlyArg-28
SEQ. ID. NO. 4412 42-ThrGlyThrSerLys-46
SEQ. ID. NO. 4413 101-ArgThrIleProSerValThrGluIle-109
SEQ. ID. NO. 4414 123-PheSerIleLeuAlaLeuIleLysSerLeuIleSer-134

TABLE 1-continued

| | |
|---|---|
| SEQ. ID. NO. 4415 | 157-LeuTyrArgGlnIleGlnAsnLeuIleThrHisPheAsnPheTyrAlaAla-173 |
| SEQ. ID. NO. 4416 | 189-GluThrLeuIleGlnHisLeuHisGlnLeuAlaAsp-200 |
| Antigenic Index - Jameson-Wolf | |
| SEQ. ID. NO. 4417 | 25-SerIleGlyArgProAsnAlaSerThrThrArgProThrSerSerArgProThrGlyThrSerLysIleArgPro-49 |
| SEQ. ID. NO. 4418 | 63-SerProAsnThrThrAlaProThrGluSerArgSerArgPheIleAla-78 |
| SEQ. ID. NO. 4419 | 80-ProLysValLeuProGlyAsnSerSerIle-89 |
| SEQ. ID. NO. 4420 | 93-IleAlaSerAspLysProTrpMetArg-101 |
| SEQ. ID. NO. 4421 | 117-SerAlaPheThrAspArgPheSer-124 |
| SEQ. ID. NO. 4422 | 146-ArgHisSerArgValGlnGlyThr-153 |
| SEQ. ID. NO. 4423 | 178-PheAspPheAspArgAspPhe-184 |
| SEQ. ID. NO. 4424 | 209-ThrValAsnAspGlyArgPheAspMetValGlu-219 |
| Hydrophilic Regions - Hopp-Woods | |
| SEQ. ID. NO. 4425 | 27-GlyArgProAsnAlaSerThrThrArgProThrSerSerArgProThrGlyThrSerLysIleArgPro-49 |
| SEQ. ID. NO. 4426 | 68-AlaProThrGluSerArgSerArgPheIleAla-78 |
| SEQ. ID. NO. 4427 | 93-IleAlaSerAspLysProTrp-99 |
| SEQ. ID. NO. 4428 | 146-ArgHisSerArgValGln-151 |
| SEQ. ID. NO. 4429 | 178-PheAspPheAspArgAspPhe-184 |
| SEQ. ID. NO. 4430 | 211-AsnAspGlyArgPheAspMetValGlu-219 |
| 279 | |
| AMPHI Regions - AMPHI | |
| SEQ. ID. NO. 4431 | 6-GlyCysLeuIleSerThr-11 |
| SEQ. ID. NO. 4432 | 13-PheArgAlaSerAla-17 |
| SEQ. ID. NO. 4433 | 47-AlaAlaAlaMetAlaArgProThrAla-55 |
| Antigenic Index - Jameson-Wolf | |
| SEQ. ID. NO. 4434 | 28-GlnTrpGluGlyThrAspThrGlySerGlyArgAlaArgLeuAla-42 |
| SEQ. ID. NO. 4435 | 64-CysProGlyGluLeuLysLeuThr-71 |
| SEQ. ID. NO. 4436 | 88-CysSerSerSerLysProArgIle-95 |
| SEQ. ID. NO. 4437 | 101-ThrProCysGlyThrAlaAspCysIleSerSerAlaArgArgArgThrSerLeu-118 |
| Hydrophilic Regions - Hopp-Woods | |
| SEQ. ID. NO. 4438 | 29-TrpGluGlyThrAspThrGlySerGlyArgAlaArgLeuAla-42 |
| SEQ. ID. NO. 4439 | 66-GlyGluLeuLysLeu-70 |
| SEQ. ID. NO. 4440 | 89-SerSerSerLysProArgIle-95 |
| SEQ. ID. NO. 4441 | 110-SerSerAlaArgArgArgThrSerLeu-118 |
| 280 | |
| AMPHI Regions - AMPHI | |
| SEQ. ID. NO. 4442 | 27-SerPheSerIleLeuGlyAspValAlaLys-36 |
| SEQ. ID. NO. 4443 | 64-AspIleLysLysIleArgSerAla-71 |
| SEQ. ID. NO. 4444 | 85-AspValGlnArgAlaValLys-91 |
| SEQ. ID. NO. 4445 | 97-TyrThrGluAlaThrLysGlyIleGlnProLeuLys-108 |
| SEQ. ID. NO. 4446 | 146-AlaTyrAlaGlnAsnValAlaLysAlaLeuIleLys-157 |
| SEQ. ID. NO. 4447 | 233-ValAlaAlaIleIleArgGlnIleLys-241 |
| SEQ. ID. NO. 4448 | 243-GluGlyIleLysAlaValPheThrGlu-251 |
| SEQ. ID. NO. 4449 | 254-LysAspThrArgMetValAspArgIleAlaLysGluThr-266 |
| SEQ. ID. NO. 4450 | 274-LeuTyrSerAspAlaLeuGlyAsnAlaProAlaAspThrTyrIle-288 |
| Antigenic Index - Jameson-Wolf | |
| SEQ. ID. NO. 4451 | 38-IleGlyGlyGluArgValSer-44 |
| SEQ. ID. NO. 4452 | 51-AlaAsnGlnAspThrHis-56 |
| SEQ. ID. NO. 4453 | 61-ThrSerGlyAspIleLysLysIleArgSerAlaLys-72 |
| SEQ. ID. NO. 4454 | 82-GluAlaAlaAspValGlnArgAlaValLysGlnSerLysValSerTyrThrGluAlaThrLysGlyIleGln-105 |
| SEQ. ID. NO. 4455 | 107-LeuLysAlaGluGluGluGlyGlyHisHisHisAspHisAspHisAspHisGluGlyHisHisHisAspHisGlyGluTyrAspProHisValTrpAsnAspPro-141 |
| SEQ. ID. NO. 4456 | 155-LeuIleLysAlaAspProGluGlyLysValTyrTyr-166 |
| SEQ. ID. NO. 4457 | 176-GlnLeuLysLysLeuHisSerAspAla-184 |
| SEQ. ID. NO. 4458 | 192-ProAlaAlaLysArgLysValLeuThr-200 |
| SEQ. ID. NO. 4459 | 208-MetGlyLysArgTyrHis-213 |
| SEQ. ID. NO. 4460 | 218-AlaProGlnGlyValSerSerGluAlaGluProSerAlaLysGln-232 |
| SEQ. ID. NO. 4461 | 238-ArgGlnIleLysArgGluGlyIle-245 |
| SEQ. ID. NO. 4462 | 251-GluAsnIleLysAspThrArgMetValAspArgIleAlaLysGluThrGlyVal-268 |
| SEQ. ID. NO. 4463 | 270-ValSerGlyLysLeuTyrSer-276 |
| SEQ. ID. NO. 4464 | 282-AlaProAlaAspThr-286 |
| SEQ. ID. NO. 4465 | 291-TyrArgHisAsnIle-295 |
| Hydrophilic Regions - Hopp-Woods | |
| SEQ. ID. NO. 4466 | 38-IleGlyGlyGluArgValSer-44 |
| SEQ. ID. NO. 4467 | 63-GlyAspIleLysLysIleArgSerAlaLys-72 |
| SEQ. ID. NO. 4468 | 82-GluAlaAlaAspValGlnArgAlaValLysGlnSerLys-94 |
| SEQ. ID. NO. 4469 | 99-GluAlaThrLysGly-103 |
| SEQ. ID. NO. 4470 | 107-LeuLysAlaGluGluGluGlyGlyHisHisHisAspHisAspHisAspHisGluGlyHisHisHisAspHisGlyGluTyrAsp-134 |
| SEQ. ID. NO. 4471 | 155-LeuIleLysAlaAspProGluGly-162 |
| SEQ. ID. NO. 4472 | 176-GlnLeuLysLysLeuHisSerAspAla-184 |
| SEQ. ID. NO. 4473 | 192-ProAlaAlaLysArgLysValLeuThr-200 |
| SEQ. ID. NO. 4474 | 222-ValSerSerGluAlaGluProSerAlaLysGln-232 |
| SEQ. ID. NO. 4475 | 238-ArgGlnIleLysArgGluGlyIle-245 |
| SEQ. ID. NO. 4476 | 251-GluAsnIleLysAspThrArgMetValAspArgIleAlaLysGluThrGlyVal-268 |
| 281-2 | |
| AMPHI Regions - AMPHI | |
| SEQ. ID. NO. 4477 | 62-AlaAlaGlyMetLeuMetAlaLeuLeuAlaGlyLeuValSerArgPhe-77 |
| SEQ. ID. NO. 4478 | 126-LeuGlnLeuIleAlaAlaValSerSerLeuThr-136 |
| SEQ. ID. NO. 4479 | 179-LeuValSerGlyPheGlnAlaLeuGlyThrLeuMetSerVal-192 |
| SEQ. ID. NO. 4480 | 205-TrpAlaLysHisMet-209 |
| SEQ. ID. NO. 4481 | 216-SerValLeuThrAlaLeuLeuCysGly-224 |

TABLE 1-continued

| | |
|---|---|
| Antigenic Index - Jameson-Wolf | |
| SEQ. ID. NO. 4482 | 25-ArgArgMetSerLeu-29 |
| SEQ. ID. NO. 4483 | 78-ThrThrLeuLysGluAspAlaAsn-85 |
| SEQ. ID. NO. 4484 | 102-SerLysAsnGlySerSerVal-108 |
| SEQ. ID. NO. 4485 | 159-SerValGlyGlyLysGlyGly-165 |
| SEQ. ID. NO. 4486 | 236-IleProSerGlyPro-240 |
| SEQ. ID. NO. 4487 | 256-LeuGlyLysGluGlyGlyIle-262 |
| SEQ. ID. NO. 4488 | 270-HisArgHisHisThrThr-275 |
| Hydrophilic Regions - Hopp-Woods | |
| SEQ. ID. NO. 4489 | 25-ArgArgMetSerLeu-29 |
| SEQ. ID. NO. 4490 | 78-ThrThrLeuLysGluAspAlaAsn-85 |
| SEQ. ID. NO. 4491 | 103-LysAsnGlySerSer-107 |
| SEQ. ID. NO. 4492 | 256-LeuGlyLysGluGlyGlyIle-262 |
| SEQ. ID. NO. 4493 | 270-HisArgHisHisThr-274 |
| 282 | |
| AMPHI Regions - AMPHI | |
| SEQ. ID. NO. 4494 | 10-LeuIleValAlaPheLeuValLeuIleAsnProPheSerAlaLeu-24 |
| SEQ. ID. NO. 4495 | 50-ValPheAlaValIleAlaValPheAlaLeuIleGlyGlyThrLeu-64 |
| SEQ. ID. NO. 4496 | 112-ArgProAlaArgAsn-116 |
| SEQ. ID. NO. 4497 | 176-ValSerArgLeuLeu-180 |
| SEQ. ID. NO. 4498 | 186-ThrIleLeuAsnArgIleMetGlyMet-194 |
| Antigenic Index - Jameson-Wolf | |
| SEQ. ID. NO. 4499 | 31-ThrAsnGlyHisSerThrLysGluArgArgLysValAlaArg-44 |
| SEQ. ID. NO. 4500 | 92-AsnGlyAsnAspAsnProAlaLysGlnAsnLeuGlyAlaGlnProGluThrGlyGlnAlaArgProAlaArgAsnAlaGly-118 |
| Hydrophilic Regions - Hopp-Woods | |
| SEQ. ID. NO. 4501 | 34-HisSerThrLysGluArgArgLysValAlaArg-44 |
| SEQ. ID. NO. 4502 | 92-AsnGlyAsnAspAsnProAlaLysGlnAsnLeu-102 |
| SEQ. ID. NO. 4503 | 104-AlaGlnProGluThrGlyGlnAlaArgProAlaArgAsn-116 |
| 283 | |
| AMPHI Regions - AMPHI | |
| SEQ. ID. NO. 4504 | 11-ThrLeuAlaSerPheLeuPro-17 |
| SEQ. ID. NO. 4505 | 32-GlyGlyAsnSerTyrSerAspValProLysGlnLeuHis-44 |
| SEQ. ID. NO. 4506 | 67-AlaAspAlaGlyLysArgThr-73 |
| Antigenic Index - Jameson-Wolf | |
| SEQ. ID. NO. 4507 | 28-TrpLysAspGlyGlyGlyAsnSerTyrSerAspValProLysGlnLeuHisProAspGlnSerGln-49 |
| SEQ. ID. NO. 4508 | 53-LeuArgThrArgGlnThrLysProAlaValLysProAlaGlnAlaAspAlaGlyLysArgThrAspGlyAlaAlaGlnGluAsnAsnProAspThrAla GluLysAsnArgGlnLeuGluGluGluLysLysArgIleAlaGluThrGluArgGlnAsnLysGluGluAsnCysArgIleSerLysMetAsnLeu-117 |
| SEQ. ID. NO. 4509 | 121-GlyAsnSerAsnAlaLysAsnLysAspAspLeuIleArgLysTyrAsnAsnAlaValAsnLysTyrCysArg-144 |
| Hydrophilic Regions - Hopp-Woods | |
| SEQ. ID. NO. 4510 | 35-SerTyrSerAspValProLys-41 |
| SEQ. ID. NO. 4511 | 43-LeuHisProAspGlnSerGln-49 |
| SEQ. ID. NO. 4512 | 53-LeuArgThrArgGlnThrLysProAlaValLysProAlaGlnAlaAspAlaGlyLysArgThrAspGlyAlaAlaGlnGluAsnAsnProAspThrAla GluLysAsnArgGlnLeuGluGluGluLysLysArgIleAlaGluThrGluArgGlnAsnLysGluGluAsnCysArgIleSerLysMetAsnLeu-117 |
| SEQ. ID. NO. 4513 | 123-SerAsnAlaLysAsnLysAspAspLeuIleArgLysTyrAsn-136 |
| 284 | |
| AMPHI Regions - AMPHI | |
| SEQ. ID. NO. 4514 | 43-GluAlaPheAlaGlyPhePheGluThrVal-52 |
| SEQ. ID. NO. 4515 | 61-ThrPheAlaAlaArgPhe-66 |
| SEQ. ID. NO. 4516 | 125-ValAspPheAspValPhe-130 |
| SEQ. ID. NO. 4517 | 154-ValValPheArgLeuPheArgGlnValValValAsp-165 |
| SEQ. ID. NO. 4518 | 174-AspThrAlaCysGlyAsnIleGlyGly-182 |
| SEQ. ID. NO. 4519 | 186-PheAlaAlaAlaPheThrGlnIleHisGln-195 |
| SEQ. ID. NO. 4520 | 216-PheValGlnPheIleArgAsnAspPheGlyHisGly-227 |
| SEQ. ID. NO. 4521 | 277-PheArgValPheGlyGlnPheAlaArgGlnPheAla-288 |
| SEQ. ID. NO. 4522 | 307-CysPheHisAspGlyPheAspValValAspLys-317 |
| SEQ. ID. NO. 4523 | 342-LeuHisGlnValHisGlnThrAla-349 |
| SEQ. ID. NO. 4524 | 352-GlyAspAsnGlnIleAspArgPheAlaGln-361 |
| SEQ. ID. NO. 4525 | 372-AlaAspAspAlaAspGlyAla-378 |
| SEQ. ID. NO. 4526 | 405-GlnSerThrArgAlaPheAlaArgPhePheAlaAlaPheGlyGlnPheLeuGlnSer-423 |
| Antigenic Index - Jameson-Wolf | |
| SEQ. ID. NO. 4527 | 1-MetProSerGluThrArgAsnArgPhe-9 |
| SEQ. ID. NO. 4528 | 109-PheAspGlyGlnPhe-113 |
| SEQ. ID. NO. 4529 | 132-HisPheGlyLysArgAsnArgAsnThrArgAla-142 |
| SEQ. ID. NO. 4530 | 147-GlyAlaProAspAlaVal-152 |
| SEQ. ID. NO. 4531 | 166-AsnValGlyAsnGlyArgTyrValAspThrAlaCysGlyAsnIleGlyGlyAsnGlnAsnPhe-186 |
| SEQ. ID. NO. 4532 | 220-IleArgAsnAspPheGlyHisGlyPheGlyGlyArgGluAsnHisAla-235 |
| SEQ. ID. NO. 4533 | 273-AspPheAspAspPheArg-278 |
| SEQ. ID. NO. 4534 | 286-GlnPheAlaAspArgAlaValProSerGlyGlyGluGlnGlnSer-300 |
| SEQ. ID. NO. 4535 | 303-ValAlaArgArgCysPheHisAspGlyPheAspValValAspLysAlaHis-319 |
| SEQ. ID. NO. 4536 | 347-GlnThrAlaArgArgGlyAspAsnGlnIleAspArgPheAlaGlnGlyThrGlyLeuValAlaGluArgArgAlaAlaAspAspAlaAspGlyAla Glu-379 |
| SEQ. ID. NO. 4537 | 398-PheAlaGlyArgGlyGlnHisGlnSerThrArgAla-409 |
| Hydrophilic Regions - Hopp-Woods | |
| SEQ. ID. NO. 4538 | 1-MetProSerGluThrArgAsnArgPhe-9 |
| SEQ. ID. NO. 4539 | 134-GlyLysArgAsnArgAsnThrArgAla-142 |
| SEQ. ID. NO. 4540 | 229-GlyGlyArgGluAsnHisAla-235 |
| SEQ. ID. NO. 4541 | 286-GlnPheAlaAspArgAlaValProSerGlyGlyGluGlnGln-299 |
| SEQ. ID. NO. 4542 | 313-AspValValAspLysAlaHis-319 |

TABLE 1-continued

| SEQ. ID. NO. 4543 | 347-GlnThrAlaArgArgGlyAspAsnGlnIleAspArgPheAla-360 |
| SEQ. ID. NO. 4544 | 366-ValAlaGluArgArgAlaAlaAspAspAlaAspGlyAlaGlu-379 |
| SEQ. ID. NO. 4545 | 402-GlyGlnHisGlnSer-406 |

285-1
AMPHI Regions - AMPHI

| SEQ. ID. NO. 4546 | 15-ValCysPheLeuGly-19 |
| SEQ. ID. NO. 4547 | 34-GlnIleProSerTrp-38 |
| SEQ. ID. NO. 4548 | 50-GlyThrLeuLeuAspGlyPheAsp-57 |
| SEQ. ID. NO. 4549 | 116-SerLeuProAspSerIleAspLeuPro-124 |
| SEQ. ID. NO. 4550 | 208-HisSerThrAlaArg-212 |
| SEQ. ID. NO. 4551 | 240-HisProPheAlaGluSerLeuAspLysThrLeuGluGluValLeu-254 |
| SEQ. ID. NO. 4552 | 266-ValProSerLeuPro-270 |
| SEQ. ID. NO. 4553 | 280-AlaIleProSerPheSerAsp-286 |
| SEQ. ID. NO. 4554 | 313-GlnValLeuGlyGly-317 |
| SEQ. ID. NO. 4555 | 592-IleGlyLysAlaAlaAspIle-598 |
| SEQ. ID. NO. 4556 | 609-ProAspThrSerArg-613 |
| SEQ. ID. NO. 4557 | 671-GlyIleAsnArgGluLeuThrArgTrp-679 |
| SEQ. ID. NO. 4558 | 747-IleAlaGluLeuHisAsnPhePheLysProProPhe-758 |
| SEQ. ID. NO. 4559 | 776-AlaArgGlyTyrLeu-780 |
| SEQ. ID. NO. 4560 | 836-PheGlyGlyAsnMetAlaAsn-842 |
| SEQ. ID. NO. 4561 | 848-ArgIleThrAlaSerLeu-853 |
| SEQ. ID. NO. 4562 | 855-AspLeuGlyAlaLeu-859 |
| SEQ. ID. NO. 4563 | 868-GlnAsnIleThrGlySerLeuAsnAlaAla-877 |
| SEQ. ID. NO. 4564 | 955-GlySerIleAlaAsp-959 |
| SEQ. ID. NO. 4565 | 1008-ThrAlaGluLeu-1012 |
| SEQ. ID. NO. 4566 | 1061-ValThrGlyMetIleLys-1066 |
| SEQ. ID. NO. 4567 | 1135-SerGlyGlySerValArgGlyValGlyThrValArg-1146 |
| SEQ. ID. NO. 4568 | 1165-ThrValSerPheValGlyProLeuAsn-1173 |
| SEQ. ID. NO. 4569 | 1190-AlaGlyValGluIleLeuGlySerLeuAsn-1199 |
| SEQ. ID. NO. 4570 | 1244-LeuAlaGlyGlnIle-1248 |
| SEQ. ID. NO. 4571 | 1305-ValLysLeuIleTyrArgLeuThrArgAlaIleGlnAlaValAlaArgIleGlySer-1323 |

AntigenicIndex -Jameson-Wolf

| SEQ. ID. NO. 4572 | 43-IleSerSerGlnAsnLeuLysGlyThrLeuLeuAspGlyPheAspGlyAspAsnTrpSerIleGluThrGluGlyAlaAspLeuLysIleSerArg-74 |
| SEQ. ID. NO. 4573 | 80-LysProSerGluLeuMetArgArgSerLeuHis-90 |
| SEQ. ID. NO. 4574 | 104-LysProThrProProLysGluGluArgProProLeuSerLeuProAspSerIleAsp-122 |
| SEQ. ID. NO. 4575 | 130-AspArgPheGluThrGlyLysIleSerMetGlyLysAlaPheAspLysGlnThrValTyr-149 |
| SEQ. ID. NO. 4576 | 151-GluArgLeuAspAlaSerTyrArgTyrAspArgLysGlyHisArgLeuAspLeuLysAlaAlaAspThrProTrpSerSerSerSerGlyAlaAla-182 |
| SEQ. ID. NO. 4577 | 185-GlyLeuLysLysProPheAla-191 |
| SEQ. ID. NO. 4578 | 198-ThrLysGlyGlyLeuGluGlyLysThrIle-207 |
| SEQ. ID. NO. 4579 | 209-SerThrAlaArgLeuSerGlySerLeuLysAspValArgAla-222 |
| SEQ. ID. NO. 4580 | 224-LeuAlaIleAspGlyGlyAsnIleArgLeuSerGlyLysSer-237 |
| SEQ. ID. NO. 4581 | 244-GluSerLeuAspLysThrLeuGlu-251 |
| SEQ. ID. NO. 4582 | 268-SerLeuProAspAla-272 |
| SEQ. ID. NO. 4583 | 292-GlySerLeuAspLeuGluAsnThrLys-300 |
| SEQ. ID. NO. 4584 | 302-GlyPheAlaAspArgAsnGlyIleProVal-311 |
| SEQ. ID. NO. 4585 | 320-IleArgGlnAspGlyThrVal-326 |
| SEQ. ID. NO. 4586 | 337-GlyArgGlyGlyIleArgLeuSerGlyLysIleAspThrGluLysAspIleLeu-354 |
| SEQ. ID. NO. 4587 | 362-SerValGlyAlaGluAspValLeu-369 |
| SEQ. ID. NO. 4588 | 372-AlaPheLysGlyArgLeuAspGlySerIle-381 |
| SEQ. ID. NO. 4589 | 387-ThrAlaSerProLysIle-392 |
| SEQ. ID. NO. 4590 | 400-ThrAlaArgThrAspGlySerLeu-407 |
| SEQ. ID. NO. 4591 | 411-SerAspProAlaAsnGlyGlnArgLysLeuVal-421 |
| SEQ. ID. NO. 4592 | 430-GlyGlnGlySerLeuThr-435 |
| SEQ. ID. NO. 4593 | 442-LeuPheLysAspArgLeuLeuLysLeuAspIleArgSerArgAlaPheAspProSerArgIleAspProGlnLeu-466 |
| SEQ. ID. NO. 4594 | 480-GluLeuAlaLysGluLysPheThrGlyLys-489 |
| SEQ. ID. NO. 4595 | 508-IleValTyrGluSerArgHisLeuProArgAlaAlaVal-520 |
| SEQ. ID. NO. 4596 | 522-LeuArgLeuGlyArgAsnIleIleLysThrAspGlyGlyPheGlyLysLysGlyAspArgLeuAsn-543 |
| SEQ. ID. NO. 4597 | 548-AlaProAspLeuSerArgPheGly-555 |
| SEQ. ID. NO. 4598 | 563-AsnValArgGlyHisLeuSerGlyAspLeuAspGlyGlyIleArgThrPheGluThrAspLeuSerGlyAlaAla-587 |
| SEQ. ID. NO. 4599 | 594-LysAlaAlaAspIleArgSer-600 |
| SEQ. ID. NO. 4600 | 605-LeuLysGlySerProAspThrSerArgProIleArgAlaAspIleLysGlySerArgLeuSerLeuSerGlyGly-629 |
| SEQ. ID. NO. 4601 | 634-AspThrAlaAspLeuMetLeuAspGlyThrGlyVal-645 |
| SEQ. ID. NO. 4602 | 647-HisArgIleArgThr-651 |
| SEQ. ID. NO. 4603 | 656-ThrLeuAspGlyLysProPheLysPheAspLeuAspAlaSerGlyGlyIleAsnArgGluLeuThrArgTrpLysGlySerIle-683 |
| SEQ. ID. NO. 4604 | 696-LeuGlnAsnArgMetThrLeu-702 |
| SEQ. ID. NO. 4605 | 704-AlaGlyAlaGluArgValAla-710 |
| SEQ. ID. NO. 4606 | 729-SerTrpAspLysLysThrGlyIleSerAlaLysGlyGlyAla-742 |
| SEQ. ID. NO. 4607 | 764-LeuAsnGlyAspTrp-768 |
| SEQ. ID. NO. 4608 | 772-TyrGlyArgAsnAlaArgGly-778 |
| SEQ. ID. NO. 4609 | 782-IleSerArgGlnSerGlyAspAlaValLeu-791 |
| SEQ. ID. NO. 4610 | 803-SerLeuLysThrArgPheGlnAsnAspArgIleGly-814 |
| SEQ. ID. NO. 4611 | 817-LeuAspGlyGlyAlaArgPheGlyArgIleAsnAla-828 |
| SEQ. ID. NO. 4612 | 844-ProLeuGlyGlyArgIleThr-850 |
| SEQ. ID. NO. 4613 | 882-GlyArgValGlySerProSerVal-889 |
| SEQ. ID. NO. 4614 | 893-ValAsnGlySerSerAsnTyrGlyLysIleAsnGly-904 |
| SEQ. ID. NO. 4615 | 908-ValGlyGlnSerArgSerPheAspThrAlaProLeuGlyGlyArgLeuAsn-924 |
| SEQ. ID. NO. 4616 | 941-GlnThrValLysGlySerLeu-947 |
| SEQ. ID. NO. 4617 | 956-SerIleAlaAspProHisLeuGlyGly-964 |
| SEQ. ID. NO. 4618 | 966-IleAsnGlyAspLysLeuTyrTyrArgAsnGlnThr-977 |
| SEQ. ID. NO. 4619 | 982-LeuAspAsnGlySerLeuArg-988 |

TABLE 1-continued

| | |
|---|---|
| SEQ. ID. NO. 4620 | 991-IleAlaGlyArgLysTrpVal-997 |
| SEQ. ID. NO. 4621 | 1001LeuLysPheArgHisGluGlyThrAlaGluLeuSerGly-1013 |
| SEQ. ID. NO. 4622 | 1015-ValGlyMetGluAsnSerGlyProAspValAspIle-1026 |
| SEQ. ID. NO. 4623 | 1031-AspLysTyrArgIleLeuSerArgProAsnArgArgLeuThr-1044 |
| SEQ. ID. NO. 4624 | 1047-GlyAsnThrArgLeuArgTyrSerProGlnLysGlyIle-1059 |
| SEQ. ID. NO. 4625 | 1065-IleLysThrAspGlnGlyLeuPheGlySerGlnLysSerSerMetProSerValGlyAspAspVal-1086 |
| SEQ. ID. NO. 4626 | 1091-GluValLysLysGluAlaAla-1097 |
| SEQ. ID. NO. 4627 | 1109-AspLeuAsnAspGlyIleArg-1115 |
| SEQ. ID. NO. 4628 | 1134-GlnSerGlyGlySerValArgGlyValGly-1143 |
| SEQ. ID. NO. 4629 | 1146-ArgValIleLysGlyArgTyrLysAlaTyrGlyGlnAspLeuAspIle |
| SEQ. ID. NO. 4630 | ThrLysGlyThr-1165 |
| SEQ. ID. NO. 4631 | 1171-ProLeuAsnAspProAsnLeuAsnIleArgAlaGluArgArgLeuSerProValGly-1189 |
| SEQ. ID. NO. 4632 | 1197-SerLeuAsnSerProArgIle-1203 |
| SEQ. ID. NO. 4633 | 1207-AlaAsnGluProMetSerGluLysAspLysLeu-1217 |
| SEQ. ID. NO. 4634 | 1225-AlaGlySerGlySerSerGlyAspAsnAlaAla-1235 |
| SEQ. ID. NO. 4635 | 1246-GlyGlnIleAsnAspArgIleGlyLeu-1254 |
| SEQ. ID. NO. 4636 | 1256-AspAspLeuGlyPheThrSerLysArgSerArgAsnAlaGlnThrGlyGluLeuAsnProAlaGlu-1277 |
| SEQ. ID. NO. 4637 | 1283-GlyLysGlnLeuThrGlyLys-1289 |
| SEQ. ID. NO. 4638 | 1299-SerSerAlaGluGlnSerVal-1305 |
| SEQ. ID. NO. 4639 | 1321-IleGlySerArgSerSerGlyGlyGluLeu-1330 |
| SEQ. ID. NO. 4640 | 1335-ArgPheAspArgPheSerGlySerAspLysLysAspSerAlaGlyAsnGlyLysGlyLys-1354 |
| Hydrophilic Regions- Hopp-Woods | |
| SEQ. ID. NO. 4641 | 56-PheAspGlyAspAsnTrpSerIleGluThrGluGlyAlaAspLeuLysIleSerArg-74 |
| SEQ. ID. NO. 4642 | 83-GluLeuMetArgArgSerLeuHis-90 |
| SEQ. ID. NO. 4643 | 105-ProThrProProLysGluGluArgProPro-114 |
| SEQ. ID. NO. 4644 | 130-AspArgPheGluThrGlyLys-136 |
| SEQ. ID. NO. 4645 | 141-LysAlaPheAspLys-145 |
| SEQ. ID. NO. 4646 | 151-GluArgLeuAspAla-155 |
| SEQ. ID. NO. 4647 | 157-TyrArgTyrAspArgLysGlyHisArgLeuAspLeuLysAlaAlaAsp-172 |
| SEQ. ID. NO. 4648 | 200-GlyGlyLeuGluGlyLysThrIle-207 |
| SEQ. ID. NO. 4649 | 215-GlySerLeuLysAspValArgAla-222 |
| SEQ. ID. NO. 4650 | 244-GluSerLeuAspLysThrLeuGlu-251 |
| SEQ. ID. NO. 4651 | 292-GlySerLeuAspLeuGluAsnThrLys-300 |
| SEQ. ID. NO. 4652 | 302-GlyPheAlaAspArgAsnGlyIlePro-310 |
| SEQ. ID. NO. 4653 | 320-IleArgGlnAspGly-324 |
| SEQ. ID. NO. 4654 | 343-LeuSerGlyLysIleAspThrGluLysAspIleLeu-354 |
| SEQ. ID. NO. 4655 | 364-GlyAlaGluAspValLeu-369 |
| SEQ. ID. NO. 4656 | 373-PheLysGlyArgLeuAspGly-379 |
| SEQ. ID. NO. 4657 | 401-AlaArgThrAspGly-405 |
| SEQ. ID. NO. 4658 | 412-AspProAlaAsnGlyGlnArgLysLeuVal-421 |
| SEQ. ID. NO. 4659 | 442-LeuPheLysAspArgLeuLeuLysLeuAspIleArgSerArgAlaPheAspProSerArgIleAspPro-464 |
| SEQ. ID. NO. 4660 | 480-GluLeuAlaLysGluLysPheThrGly-488 |
| SEQ. ID. NO. 4661 | 508-IleValTyrGluSerArgHisLeuPro-516 |
| SEQ. ID. NO. 4662 | 522-LeuArgLeuGlyArgAsnIleIleLysThrAspGlyGlyPheGlyLysLysGlyAspArgLeuAsn-543 |
| SEQ. ID. NO. 4663 | 570-GlyAspLeuAspGlyGlyIleArgThrPheGluThrAspLeuSerGlyAlaAla-587 |
| SEQ. ID. NO. 4664 | 594-LysAlaAlaAspIleArgSer-600 |
| SEQ. ID. NO. 4665 | 607-GlySerProAspThrSerArgProIleArgAlaAspIleLysGlySerArgLeuSerLeu-626 |
| SEQ. ID. NO. 4666 | 634-AspThrAlaAspLeuMetLeu-640 |
| SEQ. ID. NO. 4667 | 647-HisArgIleArgThr-651 |
| SEQ. ID. NO. 4668 | 657-LeuAspGlyLysProPheLysPheAspLeuAspAla-668 |
| SEQ. ID. NO. 4669 | 670-GlyGlyIleAsnArgGluLeuThrArgTrpLysGly-681 |
| SEQ. ID. NO. 4670 | 704-AlaGlyAlaGluArgValAla-710 |
| SEQ. ID. NO. 4671 | 729-SerTrpAspLysLysThrGlyIleSerAlaLysGlyGlyAla-742 |
| SEQ. ID. NO. 4672 | 783-SerArgGlnSerGly-787 |
| SEQ. ID. NO. 4673 | 806-ThrArgPheGlnAsnAspArgIle-813 |
| SEQ. ID. NO. 4674 | 819-GlyGlyAlaArgPheGlyArgIleAsnAla-828 |
| SEQ. ID. NO. 4675 | 1001-LeuLysPheArgHisGluGlyThrAlaGluLeu-1011 |
| SEQ. ID. NO. 4676 | 1015-ValGlyMetGluAsnSerGlyProAspValAspIle-1026 |
| SEQ. ID. NO. 4677 | 1031-AspLysTyrArgIleLeuSerArgProAsnArgArgLeuThr-1044 |
| SEQ. ID. NO. 4678 | 1049-ThrArgLeuArgTyrSerPro-1055 |
| SEQ. ID. NO. 4679 | 1065-IleLysThrAspGln-1069 |
| SEQ. ID. NO. 4680 | 1075-GlnLysSerSerMet-1079 |
| SEQ. ID. NO. 4681 | 1081-SerValGlyAspAsp-1085 |
| SEQ. ID. NO. 4682 | 1091-GluValLysLysGluAlaAla-1097 |
| SEQ. ID. NO. 4683 | 1109-AspLeuAsnAspGlyIleArg-1115 |
| SEQ. ID. NO. 4684 | 1146-ArgValIleLysGlyArgTyrLysAlaTyrGlyGlnAspLeuAspIleThrLys-1163 |
| SEQ. ID. NO. 4685 | 1179-IleArgAlaGluArgArgLeuSer-1186 |
| SEQ. ID. NO. 4686 | 1209-GluProMetSerGluLysAspLysLeu-1217 |
| SEQ. ID. NO. 4687 | 1225-AlaGlySerGlySerSerGlyAspAsnAlaAla-1235 |
| SEQ. ID. NO. 4688 | 1248-IleAsnAspArgIleGlyLeu-1254 |
| SEQ. ID. NO. 4689 | 1259-GlyPheThrSerLysArgSerArgAsnAlaGlnThrGlyGluLeuAsnPro-1275 |
| SEQ. ID. NO. 4690 | 1300-SerAlaGluGlnSerVal-1305 |
| SEQ. ID. NO. 4691 | 1321-IleGlySerArgSerSerGlyGly-1328 |
| SEQ. ID. NO. 4692 | 1335-ArgPheAspArgPheSerGlySerAspLysLysAspSerAlaGlyAsnGlyLysGlyLys-1354 |
| 286 | |
| AMPHI Regions - AMPHI | |
| SEQ. ID. NO. 4693 | 69-GluIleLysAspMetVal-74 |
| SEQ. ID. NO. 4694 | 102-ProAspAsnValLysThr-107 |
| SEQ. ID. NO. 4695 | 145-ValAlaIleLeuGlyAsp-150 |
| SEQ. ID. NO. 4696 | 157-LeuAlaGluTyrTyrArgAsnAlaLeuGluAsnTrpGlnGlnProValGlySer-174 |

TABLE 1-continued

| | |
|---|---|
| SEQ. ID. NO. 4697 | 198-ProLeuAlaLysLeuGlyAsnThr-205 |
| SEQ. ID. NO. 4698 | 238-ThrGlnArgTyrProGluGlnIleValSerGlyLeuAlaArgPhe-252 |
| SEQ. ID. NO. 4699 | 326-AspTyrTyrAsnLeuPheAsnLys-333 |
| SEQ. ID. NO. 4700 | 354-IleSerGlnProArg-358 |
| SEQ. ID. NO. 4701 | 375-ThrThrGlnAsnLeu-379 |
| SEQ. ID. NO. 4702 | 428-ThrAlaSerTrpLysArgGlnLeuLeu-436 |
| SEQ. ID. NO. 4703 | 455-ThrLeuGlyThrPheLeu-460 |
| SEQ. ID. NO. 4704 | 513-GlyAlaSerSerVal-517 |
| SEQ. ID. NO. 4705 | 555-LeuSerGlyAlaValPheHisAspMetGlyAspAlaAlaAlaAsn-569 |
| SEQ. ID. NO. 4706 | 584-ArgTrpPheSerProLeu-589 |
| Antigenic Index - Jameson-Wolf | |
| SEQ. ID. NO. 4707 | 1-MetHisAspThrArgThrMetMet-8 |
| SEQ. ID. NO. 4708 | 30-AlaAspLeuSerGluAsnLysAla-37 |
| SEQ. ID. NO. 4709 | 43-PheLysAsnLysSerProAspThrGluSerValLysLeuLysProLysPheProVal-61 |
| SEQ. ID. NO. 4710 | 64-AspThrGlnAspSerGluIleLysAspMetValGluGluHisLeu-78 |
| SEQ. ID. NO. 4711 | 83-GlnGlnGlnGluGluValLeuAspLysGluGlnThr-94 |
| SEQ. ID. NO. 4712 | 97-LeuAlaGluGluAlaProAspAsnValLysThrMetLeuArgSerLysGlyTyrPheSerSerLysValSerLeuThrGluLysAspGlyAla-127 |
| SEQ. ID. NO. 4713 | 133-ThrProGlyProArgThrLysIle-140 |
| SEQ. ID. NO. 4714 | 151-IleLeuSerAspGlyAsnLeuAlaGluTyrTyrArgAsnAlaLeuGluAsnTrpGln-169 |
| SEQ. ID. NO. 4715 | 172-ValGlySerAspPheAspGlnAspSerTrpGluAsnSerLysThrSerVal-188 |
| SEQ. ID. NO. 4716 | 192-ValThrArgLysAlaTyrPro-198 |
| SEQ. ID. NO. 4717 | 208-AlaValAsnProAspThrAlaThr-215 |
| SEQ. ID. NO. 4718 | 223-AspSerGlyArgProIleAla-229 |
| SEQ. ID. NO. 4719 | 234-GluIleThrGlyThrGlnArgTyrProGluGlnIle-245 |
| SEQ. ID. NO. 4720 | 252-PheGlnProGlyMetProTyrAspLeu-260 |
| SEQ. ID. NO. 4721 | 270-LeuGluGlnAsnGlyHisTyrSerGly-278 |
| SEQ. ID. NO. 4722 | 283-AlaAspPheAspArgLeuGlnGlyAspArgValProVal-295 |
| SEQ. ID. NO. 4723 | 298-SerValThrGluValLysArgHisLysLeuGluThrGlyIleArgLeuAspSerGluTyrGlyLeuGlyGly-321 |
| SEQ. ID. NO. 4724 | 342-AspMetAspLysTyrGluThr-348 |
| SEQ. ID. NO. 4725 | 355-SerGlnProArgAsnTyrArgGlyAsnTyrTrp-365 |
| SEQ. ID. NO. 4726 | 368-AsnValSerTyrAsnArgSerThrThrGlnAsnLeuGluLysArgAlaPheSerGlyGly-387 |
| SEQ. ID. NO. 4727 | 390-TyrValArgAspArgAlaGlyIleAspAlaArgLeuGly-402 |
| SEQ. ID. NO. 4728 | 405-PheLeuAlaGluGlyArgLysIleProGlySerAla-416 |
| SEQ. ID. NO. 4729 | 430-SerTrpLysArgGlnLeu-435 |
| SEQ. ID. NO. 4730 | 441-HisProGluAsnGlyHisTyrLeuAspGlyLysIle-452 |
| SEQ. ID. NO. 4731 | 468-ThrSerAlaArgAlaGly-473 |
| SEQ. ID. NO. 4732 | 476-PheThrProGluAsnLysLysLeu-483 |
| SEQ. ID. NO. 4733 | 496-ValAlaArgAspAsnAlaAspValProSer-505 |
| SEQ. ID. NO. 4734 | 509-PheArgSerGlyGlyAlaSerSerValArgGlyTyrGluLeuAspSer-524 |
| SEQ. ID. NO. 4735 | 534-ValLeuProGluArgAlaLeu-540 |
| SEQ. ID. NO. 4736 | 562-AspMetGlyAspAla-566 |
| SEQ. ID. NO. 4737 | 568-AlaAsnPheLysArgMetLysLeuLysHisGlySerGlyLeu-581 |
| SEQ. ID. NO. 4738 | 598-TyrGlyHisSerAspLysLysIleArg-606 |
| Hydrophilic Regions - Hopp-Woods | |
| SEQ. ID. NO. 4739 | 1-MetHisAspThrArgThrMetMet-8 |
| SEQ. ID. NO. 4740 | 30-AlaAspLeuSerGluAsnLysAla-37 |
| SEQ. ID. NO. 4741 | 44-LysAsnLysSerProAspThrGluSerValLysLeuLysProLysPhe-59 |
| SEQ. ID. NO. 4742 | 64-AspThrGlnAspSerGluIleLysAspMetValGluGluHisLeu-78 |
| SEQ. ID. NO. 4743 | 84-GlnGlnGluGluValLeuAspLysGluGlnThr-94 |
| SEQ. ID. NO. 4744 | 97-LeuAlaGluGluAlaProAspAsnValLysThrMetLeuArgSer-111 |
| SEQ. ID. NO. 4745 | 119-ValSerLeuThrGluLysAspGlyAla-127 |
| SEQ. ID. NO. 4746 | 134-ProGlyProArgThrLysIle-140 |
| SEQ. ID. NO. 4747 | 174-SerAspPheAspGlnAspSerTrpGluAsnSerLysThr-186 |
| SEQ. ID. NO. 4748 | 192-ValThrArgLysAlaTyrPro-198 |
| SEQ. ID. NO. 4749 | 209-ValAsnProAspThrAlaThr-215 |
| SEQ. ID. NO. 4750 | 239-GlnArgTyrProGlu-243 |
| SEQ. ID. NO. 4751 | 283-AlaAspPheAspArgLeuGlnGlyAspArgValProVal-295 |
| SEQ. ID. NO. 4752 | 298-SerValThrGluValLysArgHisLysLeuGluThrGlyIleArgLeuAspSerGluTyr-317 |
| SEQ. ID. NO. 4753 | 342-AspMetAspLysTyrGluThr-348 |
| SEQ. ID. NO. 4754 | 373-ArgSerThrThrGlnAsnLeuGluLysArgAlaPhe-384 |
| SEQ. ID. NO. 4755 | 391-ValArgAspArgAla395GlyIleAspAlaArgLeuGly-402 |
| SEQ. ID. NO. 4756 | 405-PheLeuAlaGluGlyArgLysIlePro-413 |
| SEQ. ID. NO. 4757 | 478-ProGluAsnLysLysLeu-483 |
| SEQ. ID. NO. 4758 | 496-ValAlaArgAspAsnAlaAspVal-503 |
| SEQ. ID. NO. 4759 | 518-ArgGlyTyrGluLeuAspSer-524 |
| SEQ. ID. NO. 4760 | 534-ValLeuProGluArgAlaLeu-540 |
| SEQ. ID. NO. 4761 | 562-AspMetGlyAspAla-566 |
| SEQ. ID. NO. 4762 | 568-AlaAsnPheLysArgMetLysLeuLysHis-577 |
| SEQ. ID. NO. 4763 | 600-HisSerAspLysLysIleArg-606 |
| 287 | |
| AMPHI Regions - AMPHI | |
| SEQ. ID. NO. 4764 | 29-LysSerAlaAspThrLeuSerLysProAlaAla-39 |
| SEQ. ID. NO. 4765 | 68-GlySerGlnAspMet-72 |
| SEQ. ID. NO. 4766 | 131-AlaThrAspAlaGlyGluSerSerGlnProAlaAsnGlnProAspMetAlaAsnAlaAlaAspGlyMet-153 |
| SEQ. ID. NO. 4767 | 164-AsnAlaGlyAsnThrAlaAlaGlnGlyAlaAsnGlnAlaGly-177 |
| SEQ. ID. NO. 4768 | 246-PheGluLysLeuSerAspAlaAspLysIleSerAsnTyrLys-259 |
| SEQ. ID. NO. 4769 | 291-ProThrSerPheAlaArgPheArgArgSerAlaArg-302 |
| SEQ. ID. NO. 4770 | 410-LysSerValAspGlyIleIleAspSer-418 |
| SEQ. ID. NO. 4771 | 437-GlyPheLysGlyThrTrpThr-443 |
| SEQ. ID. NO. 4772 | 450-ValSerGlyLysPheTyr-455 |

TABLE 1-continued

| | |
|---|---|
| Antigenic Index - Jameson-Wolf | |
| SEQ. ID. NO. 4773 | 18-CysGlyGlyGlyGlyGlyGlySerProAspValLysSerAlaAspThrLeuSerLysProAla-38 |
| SEQ. ID. NO. 4774 | 42-ValSerGluLysGluThrGluAlaLysGluAspAlaProGlnAlaGlySerGlnGlyGlnGlyAlaProSerAlaGlnGlySerGlnAspMet-72 |
| SEQ. ID. NO. 4775 | 74-AlaValSerGluGluAsnThrGlyAsnGlyGlyAlaValThrAlaAspAsnProLysAsnGluAspGluValAlaGlnAsnAspMetProGlnAsnAla AlaGlyThrAspSerSerThrProAsnHisThrProAspProAsnMet-122 |
| SEQ. ID. NO. 4776 | 126-AsnMetGluAsnGlnAlaThrAspAlaGlyGluSerSerGlnProAlaAsnGlnProAspMetAlaAsnAlaAlaAspGlyMetGlnGlyAspAspPro SerAlaGlyGlyGlnAsnAlaGlyAsnThrAlaAlaGlnGlyAlaAsnGlnAlaGlyAsnAsnGlnAlaAlaGlySerSerAspProIleProAlaSerAsnPro AlaProAlaAsnGlyGlySer AsnPheGlyArgValAspLeuAlaAsn-209 |
| SEQ. ID. NO. 4777 | 214-AspGlyProSerGlnAsn-219 |
| SEQ. ID. NO. 4778 | 223-ThrHisCysLysGlyAspSerCysSerGlyAsnAsnPheLeuAspGluGluValGlnLeuLysSerGluPheGluLysLeuSerAspAlaAspLysIle SerAsnTyrLysLysAspGlyLysAsnAspLysPhe-267 |
| SEQ. ID. NO. 4779 | 287-TyrLysProLysProThrSerPheAlaArgPheArgArgSerAlaArgSerArgArgSerLeuProAla-309 |
| SEQ. ID. NO. 4780 | 321-ThrLeuIleValAspGlyGluAla-328 |
| SEQ. ID. NO. 4781 | 340-AlaProGluGlyAsnTyrArgTyrLeu-348 |
| SEQ. ID. NO. 4782 | 351-GlyAlaGluLysLeuProGlyGlySerTyr-360 |
| SEQ. ID. NO. 4783 | 364-ValGlnGlyGluProAlaLysGlyGluMet-373 |
| SEQ. ID. NO. 4784 | 388-HisThrGluAsnGlyArgProTyrProThrArgGlyArgPheAlaAla-403 |
| SEQ. ID. NO. 4785 | 405-ValAspPheGlySerLysSerValAspGlyIleIleAspSerGlyAspAspLeuHisMetGlyThrGlnLysPheLysAlaAlaIleAspGlyAsnGlyPhe LysGlyThrTrpThrGluAsnGlySerGlyAspValSerGly-452 |
| SEQ. ID. NO. 4786 | 454-PheTyrGlyProAlaGlyGluGluValAlaGlyLysTyrSerTyrArgProThrAspAlaGluLysGlyGlyPhe-478 |
| SEQ. ID. NO. 4787 | 482-AlaGlyLysLysGluGlnAsp-488 |
| Hydrophilic Regions - Hopp-Woods | |
| SEQ. ID. NO. 4788 | 22-GlyGlyGlySerProAspValLysSerAlaAspThrLeuSerLysProAla-38 |
| SEQ. ID. NO. 4789 | 42-ValSerGluLysGluThrGluAlaLysGluAspAlaProGln-55 |
| SEQ. ID. NO. 4790 | 57-GlySerGlnGlyGlnGly-62 |
| SEQ. ID. NO. 4791 | 67-GlnGlySerGlnAsp-71 |
| SEQ. ID. NO. 4792 | 74-AlaValSerGluGluAsnThrGly-81 |
| SEQ. ID. NO. 4793 | 86-ValThrAlaAspAsnProLysAsnGluAspGluValAlaGlnAsnAspMetProGln-104 |
| SEQ. ID. NO. 4794 | 107-AlaGlyThrAspSerSerThr-113 |
| SEQ. ID. NO. 4795 | 127-MetGluAsnGlnAlaThrAspAlaGlyGluSerSerGlnProAlaAsnGlnProAspMetAlaAsnAlaAlaAspGlyMetGlnGlyAspAspProSer AlaGly-161 |
| SEQ. ID. NO. 4796 | 182-AlaGlySerSerAspProIlePro-189 |
| SEQ. ID. NO. 4797 | 225-CysLysGlyAspSerCysSer-231 |
| SEQ. ID. NO. 4798 | 235-PheLeuAspGluGluValGlnLeuLysSerGluPheGluLysLeuSerAspAlaAspLysIleSerAsnTyrLysLysAspGlyLysAsnAspLysPhe-267 |
| SEQ. ID. NO. 4799 | 295-AlaArgPheArgArgSerAlaArgSerArgArgSerLeuPro-308 |
| SEQ. ID. NO. 4800 | 322-LeuIleValAspGlyGluAla-328 |
| SEQ. ID. NO. 4801 | 351-GlyAlaGluLysLeuPro-356 |
| SEQ. ID. NO. 4802 | 364-ValGlnGlyGluProAlaLysGlyGluMet-373 |
| SEQ. ID. NO. 4803 | 390-GluAsnGlyArgProTyrProThrArgGlyArgPheAlaAla-403 |
| SEQ. ID. NO. 4804 | 405-ValAspPheGlySerLysSerValAspGlyIleIleAspSerGlyAspAspLeuHis-423 |
| SEQ. ID. NO. 4805 | 427-GlnLysPheLysAlaAlaIleAsp-434 |
| SEQ. ID. NO. 4806 | 446-GlySerGlyAspValSerGly-452 |
| SEQ. ID. NO. 4807 | 458-AlaGlyGluGluValAlaGly-464 |
| SEQ. ID. NO. 4808 | 466-TyrSerTyrArgProThrAspAlaGluLysGlyGly-477 |
| SEQ. ID. NO. 4809 | 482-AlaGlyLysLysGluGlnAsp-488 |
| 288 | |
| AMPHI Regions - AMPHI | |
| SEQ. ID. NO. 4810 | 7-ValSerArgValLeu-11 |
| SEQ. ID. NO. 4811 | 54-IleValThrLysCysAla-59 |
| SEQ. ID. NO. 4812 | 61-ArgProTyrArgThrPheSerProLeuProVal-71 |
| SEQ. ID. NO. 4813 | 97-HisSerThrLeuArg-101 |
| SEQ. ID. NO. 4814 | 150-AlaLeuPheGlnAlaGlyPheAsp-157 |
| Antigenic Index - Jameson-Wolf | |
| SEQ. ID. NO. 4815 | 2-HisThrGlyGlnAla-6 |
| SEQ. ID. NO. 4816 | 28-AsnLeuProGluArgSerAlaGlySer-36 |
| SEQ. ID. NO. 4817 | 58-CysAlaValArgProTyrArgThrPheSerPro-68 |
| SEQ. ID. NO. 4818 | 72-LeuProLysGlnProSerAla-78 |
| SEQ. ID. NO. 4819 | 89-LeuProArgProAlaValAsnArgHisSerThrLeuArgSerProAspPheProProArgMet-109 |
| SEQ. ID. NO. 4820 | 113-IleArgGlyAspCysLeuPro-119 |
| SEQ. ID. NO. 4821 | 126-IleIleThrArgAsnThrLysMetProSerGluThrValGlnValSerAspGlyIleGlnProLys-147 |
| SEQ. ID. NO. 4822 | 155-GlyPheAspGluAlaVal-160 |
| Hydrophilic Regions - Hopp-Woods | |
| SEQ. ID. NO. 4823 | 28-AsnLeuProGluArgSerAla-34 |
| SEQ. ID. NO. 4824 | 58-CysAlaValArgPro-62 |
| SEQ. ID. NO. 4825 | 98-SerThrLeuArgSerProAspPheProPro-107 |
| SEQ. ID. NO. 4826 | 113-IleArgGlyAspCys-117 |
| SEQ. ID. NO. 4827 | 126-IleIleThrArgAsnThrLysMetProSerGluThrValGlnVal-140 |
| SEQ. ID. NO. 4828 | 155-GlyPheAspGluAlaVal-160 |
| 292 | |
| AMPHI Regions - AMPHI | |
| SEQ. ID. NO. 4829 | 7-LysIleLeuThrProPheThrValLeuProLeu-17 |
| SEQ. ID. NO. 4830 | 40-GlyLysSerValAla-44 |
| SEQ. ID. NO. 4831 | 62-ValLeuSerValSerGlu-67 |
| SEQ. ID. NO. 4832 | 69-ProValLysGlyIleTyrGlu-75 |
| SEQ. ID. NO. 4833 | 110-GluArgAlaAlaAspLeu-115 |
| SEQ. ID. NO. 4834 | 124-ProLeuAspLysAlaIleLysGluValArgGly-134 |
| SEQ. ID. NO. 4835 | 150-PheCysLysArgLeuGluHisGluPheGluLysMetThrAspValThr-165 |
| SEQ. ID. NO. 4836 | 195-LysAlaTrpThrAspTrpMetArg-202 |
| SEQ. ID. NO. 4837 | 212-IleCysAspAsnProVal-217 |

TABLE 1-continued

| | |
|---|---|
| Antigenic Index - Jameson-Wolf | |
| SEQ. ID. NO. 4838 | 1-MetLysThrLysLeu-5 |
| SEQ. ID. NO. 4839 | 23-ThrProValSerAsnAlaAsnAlaGluProAlaValLysAlaGluSerAlaGlyLysSerVal-43 |
| SEQ. ID. NO. 4840 | 47-LeuLysAlaArgLeuGluLysThrTyrSerAlaGlnAspLeuLys-61 |
| SEQ. ID. NO. 4841 | 66-SerGluThrProValLysGlyIle-73 |
| SEQ. ID. NO. 4842 | 85-TyrThrAspAlaGluGlyGlyTyr-92 |
| SEQ. ID. NO. 4843 | 99-IleAsnIleAspThrArgLysAsnLeuThrGluGluArgAlaAlaAspLeuAsnLys-117 |
| SEQ. ID. NO. 4844 | 124-ProLeuAspLysAlaIleLysGluValArgGlyAsnGlyLysLeuLysVal-140 |
| SEQ. ID. NO. 4845 | 142-ValPheSerAspProAspCysProPhe-150 |
| SEQ. ID. NO. 4846 | 152-LysArgLeuGluHisGluPheGluLysMetThrAsp-163 |
| SEQ. ID. NO. 4847 | 177-HisProAspAlaAlaArgLysAla-184 |
| SEQ. ID. NO. 4848 | 189-CysGlnProAspArgAlaLysAla-196 |
| SEQ. ID. NO. 4849 | 200-TrpMetArgLysGlyLysPheProVal-208 |
| SEQ. ID. NO. 4850 | 210-GlySerIleCysAspAsnProValAlaGluThrThrSerLeuGlyGlu-225 |
| SEQ. ID. NO. 4851 | 237-PheProAsnGlyArgSerGlnSerGlyTyrSerPro-248 |
| SEQ. ID. NO. 4852 | 250-ProGlnLeuGluGluIleIleArgLysAsnGln-260 |
| Hydrophilic Regions - Hopp-Woods | |
| SEQ. ID. NO. 4853 | 1-MetLysThrLysLeu-5 |
| SEQ. ID. NO. 4854 | 28-AlaAsnAlaGluProAlaValLysAlaGluSerAlaGlyLysSerVal-43 |
| SEQ. ID. NO. 4855 | 47-LeuLysAlaArgLeuGluLysThrTyrSer-56 |
| SEQ. ID. NO. 4856 | 99-IleAsnIleAspThrArgLysAsnLeuThrGluGluArgAlaAlaAspLeuAsnLys-117 |
| SEQ. ID. NO. 4857 | 124-ProLeuAspLysAlaIleLysGluValArgGlyAsnGlyLysLeuLys-139 |
| SEQ. ID. NO. 4858 | 144-SerAspProAspCysProPhe-150 |
| SEQ. ID. NO. 4859 | 152-LysArgLeuGluHisGluPheGluLysMetThrAsp-163 |
| SEQ. ID. NO. 4860 | 179-AspAlaAlaArgLysAla-184 |
| SEQ. ID. NO. 4861 | 190-GlnProAspArgAlaLysAla-196 |
| SEQ. ID. NO. 4862 | 200-TrpMetArgLysGlyLysPhe-206 |
| SEQ. ID. NO. 4863 | 240-GlyArgSerGlnSer-244 |
| SEQ. ID. NO. 4864 | 250-ProGlnLeuGluGluIleIleArgLysAsnGln-260 |
| 294 | |
| AMPHI Regions - AMPHI | |
| SEQ. ID. NO. 4865 | 27-ArgPheProAlaAlaPheArgArgTyrSerAla-37 |
| SEQ. ID. NO. 4866 | 45-LysProAlaAspThr-49 |
| SEQ. ID. NO. 4867 | 51-TrpHisArgValArgArgPheLysSerAsnArgArgMetArgGlyGlyLysProLeuLysLysProTyrArg-74 |
| SEQ. ID. NO. 4868 | 84-ArgAlaTrpThrAlaLeuSerHisAsnIleAlaGluArgAlaArgGluSerProArgArgCysGlyLysArgTyrAlaAspIleGlyGly-113 |
| SEQ. ID. NO. 4869 | 132-TyrAlaValAlaHisIleValHisLeu-140 |
| SEQ. ID. NO. 4870 | 165-ValSerArgGluAlaArgArgGluVal-173 |
| SEQ. ID. NO. 4871 | 176-AlaMetSerTyrArg-180 |
| SEQ. ID. NO. 4872 | 206-SerIleLeuGlyGluProPheAlaThrSerPheGly-217 |
| SEQ. ID. NO. 4873 | 227-AlaPheSerValLeuAlaHisPhe-234 |
| SEQ. ID. NO. 4874 | 247-ThrValGlyTrpSerLysTyrIleHisAlaVal-257 |
| Antigenic Index - Jameson-Wolf | |
| SEQ. ID. NO. 4875 | 20-ValValArgThrSerSerAsnArgPhe-28 |
| SEQ. ID. NO. 4876 | 32-PheArgArgTyrSerAlaPhe-38 |
| SEQ. ID. NO. 4877 | 43-PheProLysProAlaAspThrProTrpHisArgValArgArgPheLysSerAsnArgArgMetArgGlyGlyLysProLeuLysLysProTyrArgProArg GlyGlyGlyCysArgCysArgArgAla-85 |
| SEQ. ID. NO. 4878 | 93-IleAlaGluArgAlaArgGluSerProArgArgCysGlyLysArgTyrAlaAspIleGlyGlyAspSerAspThrIleArgIleArgValPheArgLeuGluHis ArgMet-129 |
| SEQ. ID. NO. 4879 | 161-HisThrGlyArgValSerArgGluAlaArgArgGluValGluLysAlaMetSer-178 |
| SEQ. ID. NO. 4880 | 240-LysMetAlaArgSer-244 |
| Hydrophilic Regions - Hopp-Woods | |
| SEQ. ID. NO. 4881 | 20-ValValArgThrSerSerAsnArg-27 |
| SEQ. ID. NO. 4882 | 50-ProTrpHisArgValArgArgPheLysSerAsnArgArgMetArgGlyGlyLysProLeuLysLysProTyrArgProArgGlyGlyGlyCysArgCysArg ArgAla-85 |
| SEQ. ID. NO. 4883 | 93-IleAlaGluArgAlaArgGluSerProArgArgCysGlyLysArgTyrAlaAspIleGlyGlyAspSerAspThrIleArg-119 |
| SEQ. ID. NO. 4884 | 121-ArgValPheArgLeuGluHisArgMet-129 |
| SEQ. ID. NO. 4885 | 164-ArgValSerArgGluAlaArgArgGluValGluLysAlaMetSer-178 |
| 295 | |
| AMPHI Regions - AMPHI | |
| SEQ. ID. NO. 4886 | 79-PheArgGlnProArgArgIle-85 |
| SEQ. ID. NO. 4887 | 111-ValGlnArgPhePheArgGlnPro-118 |
| SEQ. ID. NO. 4888 | 163-ValIleArgLysIleAlaAlaLeu-170 |
| SEQ. ID. NO. 4889 | 189-HisGlnGlnArgArgIleGlyLysThr-197 |
| SEQ. ID. NO. 4890 | 240-IleCysArgGlyThrSerGly-246 |
| SEQ. ID. NO. 4891 | 263-TyrIleIleLysProLeuGluHis-270 |
| Antigenic Index - Jameson-Wolf | |
| SEQ. ID. NO. 4892 | 4-MetAlaArgHisAspAspGlnGlnArg-12 |
| SEQ. ID. NO. 4893 | 18-LeuProArgArgGlnGln-23 |
| SEQ. ID. NO. 4894 | 36-AlaAlaAlaHisGlyAsnArgProAlaSerAspAlaPhePheLysLeuProArgGlnArgPheHisLeu-58 |
| SEQ. ID. NO. 4895 | 73-HisGlyCysArgAlaGlnPheArgGlnProArgArgIleArgLeu-87 |
| SEQ. ID. NO. 4896 | 89-LeuArgGlnThrProArgGlnArgSerGlyGlyArgThrAspGlnAlaAla-105 |
| SEQ. ID. NO. 4897 | 115-PheArgGlnProArgIleArgGlnLysGlnArgHisThrArgAlaProAla-131 |
| SEQ. ID. NO. 4898 | 136-ValGlyProAspPheGly-141 |
| SEQ. ID. NO. 4899 | 144-GlnAsnAlaGluHisArgAla-150 |
| SEQ. ID. NO. 4900 | 171-ArgIleGlyLysGlnAsnLeuArgGlyPheProProArgArgGlyHisLeuArgHisGlnGlnArgArgIleGlyLysThrProProGlnLeuAla-202 |
| SEQ. ID. NO. 4901 | 207-GlyGlyThrArgPheSerAspArgAsnGlyValTyrProAsnArgAlaGlyAsnGlyIleArgIleArgLeu-230 |
| SEQ. ID. NO. 4902 | 239-ProIleCysArgGlyThrSerGly-246 |
| SEQ. ID. NO. 4903 | 253-ProTyrProTyrArgArgLysGlnProGlnTyr-263 |
| SEQ. ID. NO. 4904 | 273-IleSerCysLysThrAsnAla-279 |
| SEQ. ID. NO. 4905 | 287-PheArgGlnArgAsnGlnIleSer-294 |

TABLE 1-continued

| | |
|---|---|
| Hydrophilic Regions - Hopp-Woods | |
| SEQ. ID. NO. 4906 | 5-AlaArgHisAspAspGlnGlnArg-12 |
| SEQ. ID. NO. 4907 | 18-LeuProArgArgGlnGln-23 |
| SEQ. ID. NO. 4908 | 36-AlaAlaAlaHisGlyAsnArgProAlaSer-45 |
| SEQ. ID. NO. 4909 | 77-AlaGlnPheArgGlnProArgArgIleArgLeu-87 |
| SEQ. ID. NO. 4910 | 91-GlnThrProArgGlnArgSerGlyGlyArgThrAspGlnAlaAla-105 |
| SEQ. ID. NO. 4911 | 118-ProArgIleArgGlnLysGlnArgHisThrArg-128 |
| SEQ. ID. NO. 4912 | 146-AlaGluHisArgAla-150 |
| SEQ. ID. NO. 4913 | 171-ArgIleGlyLysGlnAsnLeu-177 |
| SEQ. ID. NO. 4914 | 180-PheProProArgArgGlyHisLeuArgHisGlnGlnArgArgIleGlyLysThrProPro-199 |
| SEQ. ID. NO. 4915 | 210-ArgPheSerAspArgAsnGly-216 |
| SEQ. ID. NO. 4916 | 226-IleArgIleArgLeu-230 |
| SEQ. ID. NO. 4917 | 239-ProIleCysArgGlyThr-244 |
| SEQ. ID. NO. 4918 | 255-ProTyrArgArgLysGlnPro-261 |
| SEQ. ID. NO. 4919 | 287-PheArgGlnArgAsnGlnIle-293 |
| 297 | |
| AMPHI Regions - AMPHI | |
| SEQ. ID. NO. 4920 | 35-ArgThrGluArgVal-39 |
| SEQ. ID. NO. 4921 | 69-GlnProGlyAspSerLeuAlaAspValLeuAla-79 |
| SEQ. ID. NO. 4922 | 86-AspGluIleAlaArgIleThrGluLysTyr-95 |
| SEQ. ID. NO. 4923 | 157-LeuProThrLeuArg-161 |
| SEQ. ID. NO. 4924 | 199-LeuLysGluGlyAspAla-204 |
| SEQ. ID. NO. 4925 | 272-LeuValTyrThrArgIleSerSer-279 |
| SEQ. ID. NO. 4926 | 333-HisAlaAsnGlyValGluThrLeuTyrAlaHisLeuSerAlaPheSer-348 |
| Antigenic Index - Jameson-Wolf | |
| SEQ. ID. NO. 4927 | 8-AlaLysHisArgLysTyrAla-14 |
| SEQ. ID. NO. 4928 | 32-SerThrGluArgThrGluArgValArgProGlnArgValGluGlnAsnLeuProProLeuSerTrpGlyGlySerGly-57 |
| SEQ. ID. NO. 4929 | 67-AlaValGlnProGlyAspSerLeuAla-75 |
| SEQ. ID. NO. 4930 | 78-LeuAlaArgSerGlyMetAlaArgAspGluIleAlaArgIleThrGluLysTyrGlyGlyGluAlaAspLeuArgHisLeuArgAlaAspGlnSerVal-110 |
| SEQ. ID. NO. 4931 | 115-GlyGlyAspGlyGlyAlaArgGluVal-123 |
| SEQ. ID. NO. 4932 | 127-ThrAspGluAspGlyGluArgAsnLeuValAlaLeuGluLysLysGlyGlyIleTrpArgArgSerAlaSerGluAlaAspMetLysVal-156 |
| SEQ. ID. NO. 4933 | 167-ThrSerAlaArgGlySerLeuAlaArgAlaGluValProValGluIleArgGluSerLeuSer-187 |
| SEQ. ID. NO. 4934 | 194-PheSerLeuAspGlyLeuLysGluGlyAspAlaVal-205 |
| SEQ. ID. NO. 4935 | 228-GluValValLysGlyGlyThrArgHis-236 |
| SEQ. ID. NO. 4936 | 240-TyrTyrArgSerAspLysGluGlyGlyGlyGlyGlyAsnTyrTyrAspGluAspGlyLysValLeuGlnGluLysGlyGlyPheAsn-268 |
| SEQ. ID. NO. 4937 | 276-ArgIleSerSerProPheGlyTyr-283 |
| SEQ. ID. NO. 4938 | 295-HisThrGlyIleAspTyrAla-301 |
| SEQ. ID. NO. 4939 | 303-ProGlnGlyThrProValArgAlaSerAlaAspGly-314 |
| SEQ. ID. NO. 4940 | 318-PheLysGlyArgLysGlyGlyTyrGly-326 |
| SEQ. ID. NO. 4941 | 333-HisAlaAsnGlyValGlu-338 |
| SEQ. ID. NO. 4942 | 350-AlaGluGlyAsnValArgGlyGlyGlu-358 |
| SEQ. ID. NO. 4943 | 365-SerThrGlyArgSerThrGlyProHisLeu-374 |
| SEQ. ID. NO. 4944 | 376-TyrGluAlaArgIleAsnGlyGlnProValAsn-386 |
| SEQ. ID. NO. 4945 | 393-ProThrProGluLeuThrGlnAlaAspLysAlaAla-404 |
| SEQ. ID. NO. 4946 | 408-GlnLysGlnLysAlaAspAlaLeu-415 |
| SEQ. ID. NO. 4947 | 426-ValSerGlnSerAsp-430 |
| Hydrophilic Regions - Hopp-Woods | |
| SEQ. ID. NO. 4948 | 8-AlaLysHisArgLysTyrAla-14 |
| SEQ. ID. NO. 4949 | 32-SerThrGluArgThrGluArgValArgProGlnArgValGluGlnAsn-47 |
| SEQ. ID. NO. 4950 | 68-ValGlnProGlyAspSerLeuAla-75 |
| SEQ. ID. NO. 4951 | 82-GlyMetAlaArgAspGluIleAlaArgIleThrGluLysTyrGlyGlyGluAlaAspLeuArgHisLeuArgAlaAspGln-108 |
| SEQ. ID. NO. 4952 | 117-AspGlyGlyAlaArgGlu-122 |
| SEQ. ID. NO. 4953 | 127-ThrAspGluAspGlyGluArgAsnLeuValAlaLeuGluLysLysGlyGlyIleTrpArgArgSerAlaSerGluAlaAspMetLysVal-156 |
| SEQ. ID. NO. 4954 | 167-ThrSerAlaArgGlySerLeuAlaArgAlaGluValProValGluIleArgGluSerLeu-186 |
| SEQ. ID. NO. 4955 | 194-PheSerLeuAspGlyLeuLysGluGlyAspAlaVal-205 |
| SEQ. ID. NO. 4956 | 228-GluValValLysGlyGlyThrArg-235 |
| SEQ. ID. NO. 4957 | 242-ArgSerAspLysGluGlyGlyGly-249 |
| SEQ. ID. NO. 4958 | 253-TyrTyrAspGluAspGlyLysValLeuGlnGluLysGlyGlyPhe-267 |
| SEQ. ID. NO. 4959 | 306-ThrProValArgAlaSerAla-312 |
| SEQ. ID. NO. 4960 | 319-LysGlyArgLysGlyGlyTyr-325 |
| SEQ. ID. NO. 4961 | 350-AlaGluGlyAsnValArgGlyGlyGlu-358 |
| SEQ. ID. NO. 4962 | 366-ThrGlyArgSerThrGly-371 |
| SEQ. ID. NO. 4963 | 378-AlaArgIleAsnGly-382 |
| SEQ. ID. NO. 4964 | 396-GluLeuThrGlnAlaAspLysAlaAla-404 |
| SEQ. ID. NO. 4965 | 408-GlnLysGlnLysAlaAspAlaLeu-415 |
| 298 | |
| AMPHI Regions - AMPHI | |
| SEQ. ID. NO. 4966 | 6-SerLeuPheSerSerIle-11 |
| SEQ. ID. NO. 4967 | 13-MetSerAlaLeuIleAla-18 |
| SEQ. ID. NO. 4968 | 26-IleAsnAlaTyrTrpGlnGln-32 |
| SEQ. ID. NO. 4969 | 42-ProLeuAlaAlaTyr-46 |
| SEQ. ID. NO. 4970 | 62-LeuSerAspGlyIleLysAlaPhe-69 |
| SEQ. ID. NO. 4971 | 82-GlySerAlaAspMetProSerGlu-89 |
| SEQ. ID. NO. 4972 | 126-LeuMetGlnGlyValAla-131 |
| SEQ. ID. NO. 4973 | 134-ValGlnLysSerLeuLys-139 |
| SEQ. ID. NO. 4974 | 157-SerTyrProSerPhePheAspTrpProLysThrIleGluGluThrLeuGlnLysHisProGluIleSer-179 |
| SEQ. ID. NO. 4975 | 188-AsnAspProTrpAspPhe-193 |

TABLE 1-continued

| | |
|---|---|
| SEQ. ID. NO. 4976 | 208-AlaGlnGluTyrLeuLysArgValAspArgIleLeuGlu-220 |
| SEQ. ID. NO. 4977 | 245-GlnMetArgTyrLeuAspLysLeuLeuSerGluHisLeu-257 |
| SEQ. ID. NO. 4978 | 276-ArgTyrThrAspSer-280 |
| SEQ. ID. NO. 4979 | 308-AlaLysIleMetGluLys-313 |
| Antigenic Index - Jameson-Wolf | |
| SEQ. ID. NO. 4980 | 22-SerGlnAsnProIleAsnAlaTyr-29 |
| SEQ. ID. NO. 4981 | 34-TyrHisArgAsnSerProLeuGluPro-42 |
| SEQ. ID. NO. 4982 | 47-GlyTrpTrpArgSerGlyAlaAlaLeuGlnGlu-57 |
| SEQ. ID. NO. 4983 | 70-LeuSerGlyGluThrProProThrAlaGlnAspGlyGlySerAlaAspMetProSerGluAlaAlaAla-92 |
| SEQ. ID. NO. 4984 | 94-GluAlaValProGlnThrGlyGluThrGluTrpLysGlnAspThrGluAlaAlaAlaValArgSerGlyAspLysValPhe-120 |
| SEQ. ID. NO. 4985 | 136-LysSerLeuLysGlnGlnTyrGlyIleGluSerValAsnLeuSerLysGlnSerThrGly-155 |
| SEQ. ID. NO. 4986 | 162-PheAspTrpProLysThrIleGluGluThrLeuGlnLysHisProGlu-177 |
| SEQ. ID. NO. 4987 | 186-GlyProAsnAspProTrpAspPheProVal-195 |
| SEQ. ID. NO. 4988 | 203-AlaSerAspGluTrpAla-208 |
| SEQ. ID. NO. 4989 | 211-TyrLeuLysArgValAspArgIleLeuGlu-220 |
| SEQ. ID. NO. 4990 | 236-TyrMetLysLysAlaLysLeuAspGlyGlnMetArgTyrLeuAsp-250 |
| SEQ. ID. NO. 4991 | 252-LeuLeuSerGluHisLeuLysGly-259 |
| SEQ. ID. NO. 4992 | 270-LeuSerGlyGlyLysAspArgTyrThrAspSerValAsnValAsnGlyLysProValArgTyrArgSerLysAspGlyIle-296 |
| SEQ. ID. NO. 4993 | 318-ProSerThrGlnProSerSerThrGlnPro-327 |
| Hydrophilic Regions - Hopp-Woods | |
| SEQ. ID. NO. 4994 | 73-GluThrProProThrAlaGlnAspGlyGlySerAlaAspMetProSerGluAlaAlaAla-92 |
| SEQ. ID. NO. 4995 | 94-GluAlaValProGlnThrGlyGluThrGluTrpLysGlnAspThrGluAlaAlaAlaValArgSerGlyAsp-117 |
| SEQ. ID. NO. 4996 | 148-AsnLeuSerLysGlnSerThr-154 |
| SEQ. ID. NO. 4997 | 166-LysThrIleGluGluThrLeuGlnLysHisProGlu-177 |
| SEQ. ID. NO. 4998 | 211-TyrLeuLysArgValAspArgIleLeuGlu-220 |
| SEQ. ID. NO. 4999 | 236-TyrMetLysLysAlaLysLeuAspGlyGlnMetArgTyrLeuAsp-250 |
| SEQ. ID. NO. 5000 | 252-LeuLeuSerGluHisLeuLysGly-259 |
| SEQ. ID. NO. 5001 | 271-SerGlyGlyLysAspArgTyrThrAsp-279 |
| SEQ. ID. NO. 5002 | 281-ValAsnValAsnGlyLysProValArgTyrArgSerLysAspGlyIle-296 |
| SEQ. ID. NO. 5003 | 319-SerThrGlnProSerSerThrGlnPro-327 |
| 299 | |
| AMPHI Regions - AMPHI | |
| SEQ. ID. NO. 5004 | 54-AlaSerProTrpMetLysLysLeuGlnSerValAlaGlnGlySer-68 |
| SEQ. ID. NO. 5005 | 71-ThrPheArgIleLeuGlnIleGly-78 |
| SEQ. ID. NO. 5006 | 85-AspPhePheThrAspSerLeuArgLysArgLeuGlnLysThrTrpGly-100 |
| SEQ. ID. NO. 5007 | 238-GlnLeuThrGlnTrpSerLysTrp-245 |
| SEQ. ID. NO. 5008 | 247-AlaAspArgMetAsnAspLeuAlaGlnThr-256 |
| SEQ. ID. NO. 5009 | 281-GluGlnLysTrpLeuAspThrValArgGlnIleArgAspSerLeu-295 |
| SEQ. ID. NO. 5010 | 307-GluSerLeuLysAsnThrLeu-313 |
| SEQ. ID. NO. 5011 | 322-ArgLeuThrGluValGlnGlnMetGlnArgArgValAlaArgGln-336 |
| SEQ. ID. NO. 5012 | 344-TrpGlnAsnAlaMetGly-349 |
| SEQ. ID. NO. 5013 | 374-GlyTyrArgArgAlaAlaGluMetLeuAlaAspSerLeuGluGluLeuValArgSerAlaAlaIleArg-396 |
| Antigenic Index - Jameson-Wolf | |
| SEQ. ID. NO. 5014 | 1-MetAsnProLysHis-5 |
| SEQ. ID. NO. 5015 | 35-ProSerAlaProTyrThrAspThrAsnGlyLeu-45 |
| SEQ. ID. NO. 5016 | 48-AspTyrGlyAsnAlaSerAlaSerProTrpMetLysLysLeuGln-62 |
| SEQ. ID. NO. 5017 | 65-AlaGlnGlySerGlyGluThr-71 |
| SEQ. ID. NO. 5018 | 78-GlyAspSerHisThrAlaGlyAspPhePheThrAspSerLeuArgLysArgLeuGlnLysThrTrpGlyAspGlyGly-103 |
| SEQ. ID. NO. 5019 | 110-AlaAsnValLysGlyGlnArg-116 |
| SEQ. ID. NO. 5020 | 121-ArgHisAsnGlyAsnTrpGlnSerLeuThrSerArgAsnAsnThrGlyAspPheProLeu-140 |
| SEQ. ID. NO. 5021 | 157-AlaSerAspGlyIleAlaSerLysGlnArgVal-167 |
| SEQ. ID. NO. 5022 | 184-GlyAsnThrValSerAlaAsnGlyGlyGly-193 |
| SEQ. ID. NO. 5023 | 221-GluAsnProAlaGlyGly-226 |
| SEQ. ID. NO. 5024 | 241-GlnTrpSerLysTrpArgAlaAspArgMetAsnAspLeuAlaGlnThrGlyAla-258 |
| SEQ. ID. NO. 5025 | 266-GlyThrAsnGluAlaPheAsnAsnAsnIleAspIleAlaAspThrGluGlnLysTrp-284 |
| SEQ. ID. NO. 5026 | 286-AspThrValArgGlnIleArgAspSerLeuPro-296 |
| SEQ. ID. NO. 5027 | 305-AlaProGluSerLeuLysAsnThr-312 |
| SEQ. ID. NO. 5028 | 319-ArgProValArgLeuThrGluValGlnGlnMetGlnArgArgValAlaArgGlnGlyGlnThr-339 |
| SEQ. ID. NO. 5029 | 361-GlyTrpAlaAlaLysAspGlyVal-368 |
| SEQ. ID. NO. 5030 | 370-PheSerAlaLysGlyTyrArgArgAlaAlaGluMetLeuAlaAspSerLeuGluGluLeuValArg-391 |
| SEQ. ID. NO. 5031 | 393-AlaAlaIleArgGln-397 |
| Hydrophilic Regions - Hopp-Woods | |
| SEQ. ID. NO. 5032 | 67-GlySerGlyGluThr-71 |
| SEQ. ID. NO. 5033 | 90-SerLeuArgLysArgLeuGlnLysThrTrpGly-100 |
| SEQ. ID. NO. 5034 | 112-ValLysGlyGlnArg-116 |
| SEQ. ID. NO. 5035 | 130-ThrSerArgAsnAsnThrGly-136 |
| SEQ. ID. NO. 5036 | 159-AspGlyIleAlaSerLysGlnArgVal-167 |
| SEQ. ID. NO. 5037 | 245-TrpArgAlaAspArgMetAsnAsp-252 |
| SEQ. ID. NO. 5038 | 276-AspIleAlaAspThrGluGlnLysTrp-284 |
| SEQ. ID. NO. 5039 | 288-ValArgGlnIleArgAspSerLeuPro-296 |
| SEQ. ID. NO. 5040 | 319-ArgProValArgLeuThrGlu-325 |
| SEQ. ID. NO. 5041 | 327-GlnGlnMetGlnArgArgValAlaArgGlnGly-337 |
| SEQ. ID. NO. 5042 | 363-AlaAlaLysAspGlyVal-368 |
| SEQ. ID. NO. 5043 | 373-LysGlyTyrArgArgAlaAlaGluMetLeuAlaAspSerLeuGluGluLeuValArg-391 |
| SEQ. ID. NO. 5044 | 393-AlaAlaIleArgGln-397 |
| 302-2 | |
| AMPHI Regions - AMPHI | |
| SEQ. ID. NO. 5045 | 20-AspGlyArgPheLeuArgThrValGluTrpLeuGlyAsnMetLeuProHisPro-37 |
| SEQ. ID. NO. 5046 | 85-LeuAsnAlaAspGlyPheIleLysIleLeuThrHisThrValLysAsnPheThrGlyPheAlaProLeuGlyThrValLeuValSerLeu-114 |
| SEQ. ID. NO. 5047 | 127-SerAlaLeuMetArg-131 |

TABLE 1-continued

| | |
|---|---|
| SEQ. ID. NO. 5048 | 176-GlyArgHisProLeuAlaGlyLeuAlaAlaAlaPheAlaGlyValSerGly-192 |
| SEQ. ID. NO. 5049 | 201-GlyThrIleAspProLeuLeuAlaGlyIleThrGlnGlnAla-214 |
| SEQ. ID. NO. 5050 | 239-ValIleAlaLeuIleGly-244 |
| SEQ. ID. NO. 5051 | 271-ArgHisSerAsnGluIle-276 |
| SEQ. ID. NO. 5052 | 294-LeuSerAlaLeuLeuAlaTrp-300 |
| SEQ. ID. NO. 5053 | 308-IleLeuArgHisProGluThrGly-315 |
| SEQ. ID. NO. 5054 | 341-TyrGlyArgValThrArgSerLeuArgGlyGluGlnGluValValAsnAlaMetAlaGluSerMetSer-363 |
| SEQ. ID. NO. 5055 | 378-PheValAlaPhePheAsnTrpThrAsnIleGlyGlnTyrIle-391 |
| SEQ. ID. NO. 5056 | 448-AlaProGluValIleGlnAlaAlaTyrArgIleGlyAspSerValThrAsnIleIleThrProMetMetSerTyrPheGlyLeuIleMetAla-478 |
| SEQ. ID. NO. 5057 | 505-IleAlaTrpIleAlaLeuPheCysIle-513 |
| Antigenic Index - Jameson-Wolf | |
| SEQ. ID. NO. 5058 | 8-LysGluLysGlnMetSerGlnThrAspThrGlnArgAspGlyArgPhe-23 |
| SEQ. ID. NO. 5059 | 61-SerValProAspProArgProValGlyAlaLysGlyArgAlaAspAspGlyLeu-78 |
| SEQ. ID. NO. 5060 | 119-IleAlaGluLysSerGly-124 |
| SEQ. ID. NO. 5061 | 134-LeuThrLysSerProArgLysLeuThr-142 |
| SEQ. ID. NO. 5062 | 152-LeuSerAsnThrAlaSerGlu-158 |
| SEQ. ID. NO. 5063 | 175-LeuGlyArgHisProLeu-180 |
| SEQ. ID. NO. 5064 | 250-LysIleValGluProGlnLeuGlyProTyrGlnSerAspLeuSerGlnGluGluLysAspIleArgHisSerAsnGluIleThrProLeuGluTyrLys-282 |
| SEQ. ID. NO. 5065 | 304-ProAlaAspGlyIleLeuArgHisProGluThrGlyLeuValSer-318 |
| SEQ. ID. NO. 5066 | 343-ArgValThrArgSerLeuArgGlyGluGlnGluVal-354 |
| SEQ. ID. NO. 5067 | 402-ValGlyLeuGlyGly-406 |
| SEQ. ID. NO. 5068 | 482-LysTyrLysLysAspAlaGlyVal-489 |
| Hydrophilic Regions - Hopp-Woods | |
| SEQ. ID. NO. 5069 | 8-LysGluLysGlnMetSerGlnThrAspThrGlnArgAspGlyArgPhe-23 |
| SEQ. ID. NO. 5070 | 63-ProAspProArgProValGlyAlaLysGlyArgAlaAspAsp-76 |
| SEQ. ID. NO. 5071 | 119-IleAlaGluLysSerGly-124 |
| SEQ. ID. NO. 5072 | 136-LysSerProArgLysLeu-141 |
| SEQ. ID. NO. 5073 | 263-LeuSerGlnGluGluLysAspIleArgHisSerAsnGlu-275 |
| SEQ. ID. NO. 5074 | 307-GlyIleLeuArgHisProGlu-313 |
| SEQ. ID. NO. 5075 | 343-ArgValThrArgSerLeuArgGlyGluGlnGluVal-354 |
| SEQ. ID. NO. 5076 | 482-LysTyrLysLysAspAlaGly-488 |
| 305-2 | |
| AMPHI Regions - AMPHI | |
| SEQ. ID. NO. 5077 | 10-LeuMetMetGlyLeuValGluGlyPheThrGluPheLeuPro-23 |
| SEQ. ID. NO. 5078 | 33-PheGlyAsnLeuIleGly-38 |
| SEQ. ID. NO. 5079 | 66-PheSerAsnValLeuHis-71 |
| SEQ. ID. NO. 5080 | 93-AlaAlaValMetGly-97 |
| SEQ. ID. NO. 5081 | 99-LeuPheGlyLysGlnIleLysGluTyrLeuPhe-109 |
| SEQ. ID. NO. 5082 | 141-AspValAspAlaLeuArgProIleAspAla-150 |
| SEQ. ID. NO. 5083 | 155-ValAlaGlnValPheAla-160 |
| SEQ. ID. NO. 5084 | 202-AlaTyrAspValLeuLysHisTyrArgPhePheThrLeuHis-215 |
| SEQ. ID. NO. 5085 | 222-IleGlyPheIleAlaAlaPheValSer-230 |
| SEQ. ID. NO. 5086 | 235-ValLysAlaLeuLeuArg-240 |
| Antigenic Index - Jameson-Wolf | |
| SEQ. ID. NO. 5087 | 41-SerAsnHisLysValPhe-469 |
| SEQ. ID. NO. 5088 | 61-GluTyrArgGlnArgPheSerAsn-68 |
| SEQ. ID. NO. 5089 | 72-GlyLeuGlyLysAspArgLysAlaAsn-80 |
| SEQ. ID. NO. 5090 | 128-ValGluLysArgGlnSerArgAlaGluProLysIleAlaAsp-141 |
| SEQ. ID. NO. 5091 | 143-AspAlaLeuArgProIleAsp-149 |
| SEQ. ID. NO. 5092 | 163-ProGlyThrSerArgSerGlySer-170 |
| SEQ. ID. NO. 5093 | 180-IleGluArgLysThrAlaThr-186 |
| SEQ. ID. NO. 5094 | 241-PheValSerLysLysAsnTyr-247 |
| Hydrophilic Regions - Hopp-Woods | |
| SEQ. ID. NO. 5095 | 62-TyrArgGlnArgPhe-66 |
| SEQ. ID. NO. 5096 | 73-LeuGlyLysAspArgLysAlaAsn-80 |
| SEQ. ID. NO. 5097 | 128-ValGluLysArgGlnSerArgAlaGluProLysIleAlaAsp-141 |
| SEQ. ID. NO. 5098 | 143-AspAlaLeuArgProIleAsp-149 |
| SEQ. ID. NO. 5099 | 165-ThrSerArgSerGlySer-170 |
| SEQ. ID. NO. 5100 | 180-IleGluArgLysThrAlaThr-186 |
| SEQ. ID. NO. 5101 | 242-ValSerLysLysAsn-246 |
| 308-1 | |
| AMPHI Regions - AMPHI | |
| SEQ. ID. NO. 5102 | 6-PheTyrArgIleLeuGlyValAla-13 |
| SEQ. ID. NO. 5103 | 15-AsnLeuTyrProArgLeu-20 |
| SEQ. ID. NO. 5104 | 27-ThrIleIleAlaGlyLeu-32 |
| SEQ. ID. NO. 5105 | 64-AlaLeuGluLeuLeuArgAlaGln-71 |
| SEQ. ID. NO. 5106 | 83-AlaGluMetAlaArgAlaSerGlu-90 |
| SEQ. ID. NO. 5107 | 101-LeuAlaAspPheValHisProIleGlyAsnIleGlyAlaCys-114 |
| SEQ. ID. NO. 5108 | 131-SerMetArgThrLeuAlaSerValAlaHisGlyPheGlyAsp-144 |
| SEQ. ID. NO. 5109 | 172-LeuAlaHisLeuAspAsnMetLysArgValThrGlu-183 |
| Antigenic Index - Jameson-Wolf | |
| SEQ. ID. NO. 5110 | 16-LeuTyrProArgLeuSerAspPheCys-24 |
| SEQ. ID. NO. 5111 | 39-TrpGluArgArgMetMetVal-45 |
| SEQ. ID. NO. 5112 | 68-LeuArgAlaGlnAspValGluThr-75 |
| SEQ. ID. NO. 5113 | 80-SerLysGlyAlaGluMetAlaArgAlaSerGluThrAlaTyrAlaArgAspGluVal-98 |
| SEQ. ID. NO. 5114 | 118-GlyThrPheLysThrAspGlyMet-125 |
| SEQ. ID. NO. 5115 | 141-GlyPheGlyAspAsnLeuLeu-147 |
| SEQ. ID. NO. 5116 | 149-ArgAlaAlaAspValValLeuLysGluArgArgArgLeu-161 |
| SEQ. ID. NO. 5117 | 166-ArgGluThrProLeu-170 |
| SEQ. ID. NO. 5118 | 176-AspAsnMetLysArgValThrGluMetGly-185 |

TABLE 1-continued

| | |
|---|---|
| SEQ. ID. NO. 5119 | 195-MetTyrArgLysProGlnThrAlaAspAspIleVal-206 |
| SEQ. ID. NO. 5120 | 219-IleAspThrProAspSerAlaGlu-226 |
| Hydrophilic Regions - Hopp-Woods | |
| SEQ. ID. NO. 5121 | 39-TrpGluArgArgMetMetVal-45 |
| SEQ. ID. NO. 5122 | 68-LeuArgAlaGlnAspValGluThr-75 |
| SEQ. ID. NO. 5123 | 81-LysGlyAlaGluMetAlaArgAlaSerGlu-90 |
| SEQ. ID. NO. 5124 | 92-AlaTyrAlaArgAspGluVal-98 |
| SEQ. ID. NO. 5125 | 120-PheLysThrAspGly-124 |
| SEQ. ID. NO. 5126 | 149-ArgAlaAlaAspValValLeuLysGluArgArgArgLeu-161 |
| SEQ. ID. NO. 5127 | 176-AspAsnMetLysArgValThrGlu-183 |
| SEQ. ID. NO. 5128 | 195-MetTyrArgLysProGlnThrAlaAspAspIleVal-206 |
| SEQ. ID. NO. 5129 | 220-AspThrProAspSerAlaGlu-226 |
| 311-1 | |
| AMPHI Regions - AMPHI | |
| SEQ. ID. NO. 5130 | 7-SerHisTrpArgValLeuAlaGluLeuAlaAspGlyLeuProGlnHisValSerGlnLeuAlaArgMetAlaAsp-31 |
| SEQ. ID. NO. 5131 | 37-LeuAsnGlyPheTrpGlnGlnMetProAlaHisIleArgGlyLeuLeuArg-53 |
| SEQ. ID. NO. 5132 | 55-HisAspGlyTyrTrpArgLeuValArgProLeuAlaValPheAspAlaGluGlyLeuArgGluLeuGly-77 |
| SEQ. ID. NO. 5133 | 124-ArgGlnGlyArgLysTrpSerHisArgLeu-133 |
| SEQ. ID. NO. 5134 | 165-ArgAlaLeuSerArg-169 |
| SEQ. ID. NO. 5135 | 219-ValGluAsnAlaAlaSerValGlnSerLeuPheGln-230 |
| SEQ. ID. NO. 5136 | 291-PheGluGlyThrValLysGlyValAspGlyGlnGlyVal-303 |
| SEQ. ID. NO. 5137 | 362-ThrValGlySerAlaProTyrArgAspLeuSerProLeu-374 |
| SEQ. ID. NO. 5138 | 391-CysAlaValCysGlyGluPheLysLys-399 |
| SEQ. ID. NO. 5139 | 426-TyrArgHisProGluGluHisGlySerAspArgTrpPheAsnAlaLeuGlySer-443 |
| SEQ. ID. NO. 5140 | 493-AsnLeuAsnArgHisAla-498 |
| SEQ. ID. NO. 5141 | 511-AlaValAlaSerGlyMetMetAspAlaValCys-521 |
| SEQ. ID. NO. 5142 | 550-AlaAlaLysValAlaGluAlaLeuProPro-559 |
| SEQ. ID. NO. 5143 | 576-TyrGlyLeuLeuAsnMet-581 |
| Antigenic Index - Jameson-Wolf | |
| SEQ. ID. NO. 5144 | 28-ArgMetAlaAspMetLysProGlnGln-36 |
| SEQ. ID. NO. 5145 | 50-GlyLeuLeuArgGlnHisAspGlyTyr-58 |
| SEQ. ID. NO. 5146 | 71-GluGlyLeuArgGluLeuGlyGluArgSerGlyPhe-82 |
| SEQ. ID. NO. 5147 | 86-LeuLysHisGluCysAlaSerSerAsnAspGluIleLeuGlu-99 |
| SEQ. ID. NO. 5148 | 102-ArgIleAlaProAspLysAlaHisLys-110 |
| SEQ. ID. NO. 5149 | 116-HisLeuGlnSerLysGlyArgGlyArgGlnGlyArgLysTrpSerHisArgLeuGlyGlu-135 |
| SEQ. ID. NO. 5150 | 145-PheAspArgProGlnTyrGluLeuGlySer-154 |
| SEQ. ID. NO. 5151 | 162-AlaCysArgArgAlaLeuSer-168 |
| SEQ. ID. NO. 5152 | 182-LeuValValGlyArgAspLysLeuGly-190 |
| SEQ. ID. NO. 5153 | 196-ThrValArgThrGlyGlyLysThrVal-204 |
| SEQ. ID. NO. 5154 | 215-LeuProLysGluValGluAsn-221 |
| SEQ. ID. NO. 5155 | 231-ThrAlaSerArgArgGlyAsnAlaAsp-239 |
| SEQ. ID. NO. 5156 | 258-TyrAlaArgAspGlyPheAla-264 |
| SEQ. ID. NO. 5157 | 272-AlaAlaAsnArgAspHisGlyLys-279 |
| SEQ. ID. NO. 5158 | 284-LeuArgAspGlyGluThrValPhe-291 |
| SEQ. ID. NO. 5159 | 293-GlyThrValLysGlyValAspGlyGlnGly-302 |
| SEQ. ID. NO. 5160 | 307-GluThrAlaGluGlyLysGlnThrValValSerGlyGluIleSerLeuArgSerAspAspArgProValSerValProLysArgArgAspSerGluArg-339 |
| SEQ. ID. NO. 5161 | 344-AspGlyGlyAsnSerArgLeu-350 |
| SEQ. ID. NO. 5162 | 364-GlySerAlaProTyrArgAspLeuSerProLeuGly-375 |
| SEQ. ID. NO. 5163 | 378-TrpAlaGluLysAlaAspGlyAsnValArgIle-388 |
| SEQ. ID. NO. 5164 | 385-GlyGluPheLysLysAlaGlnValGln-403 |
| SEQ. ID. NO. 5165 | 405-GlnLeuAlaArgLysIleGlu-411 |
| SEQ. ID. NO. 5166 | 424-AsnHisTyrArgHisProGluGluHisGlySerAspArgTrp-437 |
| SEQ. ID. NO. 5167 | 440-AlaLeuGlySerArgArgPheSerArgAsnAla-450 |
| SEQ. ID. NO. 5168 | 464-AlaLeuThrAspAspGlyHisTyrLeuGly-473 |
| SEQ. ID. NO. 5169 | 483-MetLysGluSerLeuAla-488 |
| SEQ. ID. NO. 5170 | 492-AlaAsnLeuAsnArgHisAlaGlyLysArgTyrPro-503 |
| SEQ. ID. NO. 5171 | 529-GlyArgLeuLysGluLysThrGlyAlaGlyLysProVal-541 |
| SEQ. ID. NO. 5172 | 547-GlyGlyGlyAlaAlaLysValAlaGlu-555 |
| SEQ. ID. NO. 5173 | 565-AsnThrValArgValAlaAsp-571 |
| SEQ. ID. NO. 5174 | 584-AlaGluGlyArgGluTyrGluHis-591 |
| Hydrophilic Regions - Hopp-Woods | |
| SEQ. ID. NO. 5175 | 28-ArgMetAlaAspMetLysProGlnGln-36 |
| SEQ. ID. NO. 5176 | 50-GlyLeuLeuArgGlnHis-55 |
| SEQ. ID. NO. 5177 | 71-GluGlyLeuArgGluLeuGlyGluArgSerGlyPhe-82 |
| SEQ. ID. NO. 5178 | 86-LeuLysHisGluCysAlaSerSerAsnAspGluIleLeuGlu-99 |
| SEQ. ID. NO. 5179 | 102-ArgIleAlaProAspLysAlaHisLys-110 |
| SEQ. ID. NO. 5180 | 118-GlnSerLysGlyArgGlyArgGlnGlyArgLysTrpSerHisArgLeuGlyGlu-135 |
| SEQ. ID. NO. 5181 | 162-AlaCysArgArgAlaLeuSer-168 |
| SEQ. ID. NO. 5182 | 183-ValValGlyArgAspLysLeuGly-190 |
| SEQ. ID. NO. 5183 | 196-ThrValArgThrGlyGlyLys-202 |
| SEQ. ID. NO. 5184 | 217-LysGluValGluAsn-221 |
| SEQ. ID. NO. 5185 | 232-AlaSerArgArgGlyAsnAlaAsp-239 |
| SEQ. ID. NO. 5186 | 259-AlaArgAspGlyPhe-263 |
| SEQ. ID. NO. 5187 | 272-AlaAlaAsnArgAspHisGlyLys-279 |
| SEQ. ID. NO. 5188 | 285-ArgAspGlyGluThrValPhe-291 |
| SEQ. ID. NO. 5189 | 293-GlyThrValLysGlyValAspGly-300 |
| SEQ. ID. NO. 5190 | 307-GluThrAlaGluGlyLysGlnThrValVal-316 |
| SEQ. ID. NO. 5191 | 320-IleSerLeuArgSerAspAspArgProValSerValProLysArgArgAspSerGluArg-339 |
| SEQ. ID. NO. 5192 | 346-GlyAsnSerArgLeu-350 |
| SEQ. ID. NO. 5193 | 367-ProTyrArgAspLeuSer-372 |

TABLE 1-continued

| | |
|---|---|
| SEQ. ID. NO. 5194 | 378-TrpAlaGluLysAlaAspGlyAsnVal-386 |
| SEQ. ID. NO. 5195 | 395-GlyGluPheLysLysAlaGlnVal-402 |
| SEQ. ID. NO. 5196 | 405-GlnLeuAlaArgLysIleGlu-411 |
| SEQ. ID. NO. 5197 | 424-AsnHisTyrArgHisProGluGluHisGlySer-434 |
| SEQ. ID. NO. 5198 | 442-GlySerArgArgPheSerArg-448 |
| SEQ. ID. NO. 5199 | 464-AlaLeuThrAspAspGlyHis-470 |
| SEQ. ID. NO. 5200 | 483-MetLysGluSerLeuAla-488 |
| SEQ. ID. NO. 5201 | 493-AsnLeuAsnArgHisAlaGlyLysArgTyrPro-503 |
| SEQ. ID. NO. 5202 | 529-GlyArgLeuLysGluLysThrGlyAlaGlyLysProVal-541 |
| SEQ. ID. NO. 5203 | 549-GlyAlaAlaLysValAlaGlu-555 |
| SEQ. ID. NO. 5204 | 565-AsnThrValArgValAlaAsp-571 |
| SEQ. ID. NO. 5205 | 584-AlaGluGlyArgGluTyrGluHis-591 |
| 312-2 | |
| AMPHI Regions - AMPHI | |
| SEQ. ID. NO. 5206 | 6-GlyGluIleLeuGluThrValLysMetValAla-16 |
| SEQ. ID. NO. 5207 | 33-AspCysIleSerSer-37 |
| SEQ. ID. NO. 5208 | 44-GlnAsnIleTyrAsnLysIleThrThrValGlyLys-55 |
| SEQ. ID. NO. 5209 | 82-IleAlaGlnIleAlaAlaAlaThr-89 |
| SEQ. ID. NO. 5210 | 95-ValSerValAlaGlnThrLeuAspLysAlaAlaLys-106 |
| SEQ. ID. NO. 5211 | 109-GlyValSerPheIleGlyGlyPheSerAlaLeuValGln-121 |
| SEQ. ID. NO. 5212 | 133-ArgSerIleProGluAlaMetLysThr-141 |
| SEQ. ID. NO. 5213 | 167-GlyGluThrValLysArgThrAla-174 |
| SEQ. ID. NO. 5214 | 182-GlyCysAlaLysIleValValPheCys-190 |
| SEQ. ID. NO. 5215 | 230-SerAspAlaThrThrLeuThrGluValAlaGluValValLysLys-244 |
| SEQ. ID. NO. 5216 | 249-IleThrArgValGlyGluLeuIleGlyArgGluAlaSerLys-262 |
| SEQ. ID. NO. 5217 | 281-ValGlyAspSerValAlaArgIleLeuGluGluMetGly-293 |
| SEQ. ID. NO. 5218 | 309-LeuAsnAspAlaVal-313- |
| SEQ. ID. NO. 5219 | 322-SerAlaValGlyGlyLeuSerGly-329 |
| SEQ. ID. NO. 5220 | 349-LeuThrLeuAspLysLeuGluAlaMetThrAla-359 |
| SEQ. ID. NO. 5221 | 374-ThrProAlaHisThrIleSerGlyIleIle-383 |
| SEQ. ID. NO. 5222 | 409-ValGlyAspSerValGluPheGlyGlyLeuLeuGly-420 |
| Antigenic Index - Jameson-Wolf | |
| SEQ. ID. NO. 5223 | 4-GlnSerGlyGluIleLeuGlu-10 |
| SEQ. ID. NO. 5224 | 13-LysMetValAlaAspGlnAsnPheAspVal-22 |
| SEQ. ID. NO. 5225 | 35-IleSerSerAspIle-39 |
| SEQ. ID. NO. 5226 | 52-ThrValGlyLysAspLeuValThr-59 |
| SEQ. ID. NO. 5227 | 89-ThrHisAlaAspSer-93 |
| SEQ. ID. NO. 5228 | 100-ThrLeuAspLysAlaAlaLys-106 |
| SEQ. ID. NO. 5229 | 121-GlnLysGlyMetSerProSerAspGluValLeu-131 |
| SEQ. ID. NO. 5230 | 134-SerIleProGluAlaMetLysThrThrAsp-143 |
| SEQ. ID. NO. 5231 | 152-GlySerThrArgAla-156 |
| SEQ. ID. NO. 5232 | 161-AspAlaValLysLeuAlaGlyGluThrValLysArgThrAlaGluIleThrProGluGlyPheGly-182 |
| SEQ. ID. NO. 5233 | 192-AlaValGluAspAsnProPhe-198 |
| SEQ. ID. NO. 5234 | 204-HisGlySerGlyGluAlaAspAla-211 |
| SEQ. ID. NO. 5235 | 225-AlaAlaLeuGluAsnSerAspAla-232 |
| SEQ. ID. NO. 5236 | 237-GluValAlaGluValValLys-243 |
| SEQ. ID. NO. 5237 | 251-ArgValGlyGluLeuIleGlyArgGluAlaSerLys-262 |
| SEQ. ID. NO. 5238 | 280-AlaValGlyAspSerValAlaArgIleLeuGlu-290 |
| SEQ. ID. NO. 5239 | 311-AspAlaValLysLysGlyGlyMet-318 |
| SEQ. ID. NO. 5240 | 334-ValSerGluAspGluGlyMet-340 |
| SEQ. ID. NO. 5241 | 352-AspLysLeuGluAla-356 |
| SEQ. ID. NO. 5242 | 370-ValProGlyAspThrProAla-376 |
| SEQ. ID. NO. 5243 | 383-IleAlaAspGluAlaAla-388 |
| SEQ. ID. NO. 5244 | 392-IleAsnSerLysThrThrAla-398 |
| SEQ. ID. NO. 5245 | 405-ThrGlyLysThrValGlyAspSerValGlu-414 |
| SEQ. ID. NO. 5246 | 426-ProValLysGluGlySerCys-432 |
| SEQ. ID. NO. 5247 | 435-PheValAsnArgGlyGlyArgIle-442 |
| SEQ. ID. NO. 5248 | 447-GlnSerMetLysAsn-451 |
| Hydrophilic Regions - Hopp-Woods | |
| SEQ. ID. NO. 5249 | 18-GlnAsnPheAspVal-22 |
| SEQ. ID. NO. 5250 | 52-ThrValGlyLysAspLeuValThr-59 |
| SEQ. ID. NO. 5251 | 100-ThrLeuAspLysAlaAlaLys-106 |
| SEQ. ID. NO. 5252 | 123-GlyMetSerProSerAspGluValLeu-131 |
| SEQ. ID. NO. 5253 | 134-SerIleProGluAlaMetLysThrThrAsp-143 |
| SEQ. ID. NO. 5254 | 161-AspAlaValLysLeuAlaGlyGluThrValLysArgThrAlaGluIleThrPro-178 |
| SEQ. ID. NO. 5255 | 192-AlaValGluAspAsnPro-197 |
| SEQ. ID. NO. 5256 | 207-GlyGluAlaAspAla-211 |
| SEQ. ID. NO. 5257 | 225-AlaAlaLeuGluAsnSerAspAla-232 |
| SEQ. ID. NO. 5258 | 237-GluValAlaGluValValLys-243 |
| SEQ. ID. NO. 5259 | 251-ArgValGlyGluLeuIleGlyArgGluAlaSerLys-262 |
| SEQ. ID. NO. 5260 | 284-SerValAlaArgIleLeuGlu-290 |
| SEQ. ID. NO. 5261 | 311-AspAlaValLysLysGlyGlyMet-318 |
| SEQ. ID. NO. 5262 | 334-ValSerGluAspGluGlyMet-340 |
| SEQ. ID. NO. 5263 | 352-AspLysLeuGluAla-356 |
| SEQ. ID. NO. 5264 | 383-IleAlaAspGluAlaAla-388 |
| SEQ. ID. NO. 5265 | 408-ThrValGlyAspSerValGlu-414 |
| SEQ. ID. NO. 5266 | 426-ProValLysGluGlySerCys-432 |

TABLE 1-continued

| | |
|---|---|
| SEQ. ID. NO. 5267 | 438-ArgGlyGlyArgIle-442 |
| SEQ. ID. NO. 5268 | 447-GlnSerMetLysAsn-451 |
| 313-2 | |
| AMPHI Regions - AMPHI | |
| SEQ. ID. NO. 5269 | 27-GlyMetAspAspProArgThrTyrGlySerGly-37 |
| SEQ. ID. NO. 5270 | 41-AlaThrAsnValLeu-45 |
| SEQ. ID. NO. 5271 | 60-AspAlaAlaLysGly-64 |
| SEQ. ID. NO. 5272 | 66-ValAlaValLeuLeuAlaArgValLeuGlnGluPro-77 |
| SEQ. ID. NO. 5273 | 88-ValAlaLeuAlaAlaLeuValGlyHisMetTrpPro-99 |
| SEQ. ID. NO. 5274 | 143-SerLeuAlaAlaLeuThrAlaThrIleAlaAlaProVal-155 |
| Antigenic Index - Jameson-Wolf | |
| SEQ. ID. NO. 5275 | 26-TyrGlyMetAspAspProArgThrTyrGlySerGlyAsnProGlyAla-41 |
| SEQ. ID. NO. 5276 | 46-ArgSerGlyLysLysLysAlaAla-53 |
| SEQ. ID. NO. 5277 | 73-ValLeuGlnGluProLeuGlyLeuSerAspSerAla-84 |
| SEQ. ID. NO. 5278 | 104-PheLysGlyGlyLysGlyVal-110 |
| SEQ. ID. NO. 5279 | 181-HisLysSerAsnIle-185 |
| SEQ. ID. NO. 5280 | 189-LeuGluGlyArgGluSerLysIleGlyGlySerArg-200 |
| Hydrophilic Regions - Hopp-Woods | |
| SEQ. ID. NO. 5281 | 26-TyrGlyMetAspAspProArgThrTyrGly-35 |
| SEQ. ID. NO. 5282 | 46-ArgSerGlyLysLysLysAlaAla-53 |
| SEQ. ID. NO. 5283 | 105-LysGlyGlyLysGlyVal-110 |
| SEQ. ID. NO. 5284 | 181-HisLysSerAsnIle-185 |
| SEQ. ID. NO. 5285 | 189-LeuGluGlyArgGluSerLysIleGlyGlySerArg-200 |
| 401 | |
| AMPHI Regions - AMPHI | |
| SEQ. ID. NO. 5286 | 46-ValLysProTyrAsnAlaLeu-52 |
| SEQ. ID. NO. 5287 | 65-CysTyrAsnCysHisSerGlnMetIleArgProPheArg-77 |
| SEQ. ID. NO. 5288 | 112-ValGlyGlyArgTyrSerAspGluTrpHisArgIle-123 |
| SEQ. ID. NO. 5289 | 157-MetLysAlaLeuArgLysValGlyThr-165 |
| SEQ. ID. NO. 5290 | 172-IleAlaLysAlaProGluAlaLeu-179 |
| Antigenic Index - Jameson-Wolf | |
| SEQ. ID. NO. 5291 | 5-GlnLeuAlaGluGluLysIle-11 |
| SEQ. ID. NO. 5292 | 38-AlaAlaThrGlnProAlaProGlyValLysProTyrAsn-50 |
| SEQ. ID. NO. 5293 | 55-AlaGlyArgAspIleTyrIleArgGluGlyCysTyrAsnCysHis-69 |
| SEQ. ID. NO. 5294 | 74-ArgProPheArgAlaGluThrGluArgTyrGlyHis-85 |
| SEQ. ID. NO. 5295 | 90-GlyGluSerValTyr-94 |
| SEQ. ID. NO. 5296 | 98-PheGlnTrpGlySerLysArgThrGlyProAspLeuAlaArgValGlyGlyArgTyrSerAspGluTrpHis-121 |
| SEQ. ID. NO. 5297 | 125-LeuLeuAsnProArgAspValValProGluSerAsnMetPro-138 |
| SEQ. ID. NO. 5298 | 146-AsnLysValAspValAspAla-152 |
| SEQ. ID. NO. 5299 | 158-LysAlaLeuArgLysValGlyThrProTyrSerAspGluGluIleAlaLysAlaProGlu-177 |
| SEQ. ID. NO. 5300 | 179-LeuAlaAsnLysSerGluLeuAspAla-187 |
| Hydrophilic Regions - Hopp-Woods | |
| SEQ. ID. NO. 5301 | 5-GlnLeuAlaGluGluLysIle-11 |
| SEQ. ID. NO. 5302 | 76-PheArgAlaGluThrGluArgTyrGly-84 |
| SEQ. ID. NO. 5303 | 101-GlySerLysArgThrGlyProAspLeuAlaArgValGlyGlyArgTyrSerAspGluTrpHis-121 |
| SEQ. ID. NO. 5304 | 127-AsnProArgAspValValPro-133 |
| SEQ. ID. NO. 5305 | 146-AsnLysValAspValAspAla-152 |
| SEQ. ID. NO. 5306 | 158-LysAlaLeuArgLysValGly-164 |
| SEQ. ID. NO. 5307 | 167-TyrSerAspGluGluIleAlaLysAlaProGlu-177 |
| SEQ. ID. NO. 5308 | 179-LeuAlaAsnLysSerGluLeuAspAla-187 |
| 402-2 | |
| AMPHI Regions - AMPHI | |
| SEQ. ID. NO. 5309 | 18-PheLeuSerGlyLeu-22 |
| SEQ. ID. NO. 5310 | 85-AlaGlyIleAlaAspPhe-90 |
| SEQ. ID. NO. 5311 | 100-ThrGlyPheSerGlyPheValHis-107 |
| SEQ. ID. NO. 5312 | 117-AlaValValArgGlyLeu-122 |
| SEQ. ID. NO. 5313 | 136-LysSerGlyArgGln-140 |
| SEQ. ID. NO. 5314 | 146-PheAlaAsnValAlaGly-151 |
| SEQ. ID. NO. 5315 | 218-ValPheGlnAsnIleAlaAspArgProAspArgLeuIle-230 |
| SEQ. ID. NO. 5316 | 261-AspValPheAsnSerValAsnGlyIleGlu-270 |
| SEQ. ID. NO. 5317 | 279-LysSerGlyIleArg-283 |
| SEQ. ID. NO. 5318 | 294-SerTrpAlaArgValLeuSerAlaIleProGluMetGln-306 |
| SEQ. ID. NO. 5319 | 344-ArgLysTrpLeuArgArgHisPro-351 |
| SEQ. ID. NO. 5320 | 376-AlaGluPheLeuLysGlnValGlnSerHisLeu-386 |
| SEQ. ID. NO. 5321 | 398-HisSerProHisAlaPheAlaThrAlaValHisSerIlePro-411 |
| SEQ. ID. NO. 5322 | 437-GlnArgLeuSerArgLeu-442 |
| SEQ. ID. NO. 5323 | 460-AlaAlaGlnLysVal-464 |
| Antigenic Index - Jameson-Wolf | |
| SEQ. ID. NO. 5324 | 4-ValAsnThrLysProAsnThrSer-11 |
| SEQ. ID. NO. 5325 | 66-ArgIleCysArgSerArgPheValAsp-74 |
| SEQ. ID. NO. 5326 | 130-ValGlyThrAspGlyAsnLysSerGlyArgGlnValSer-142 |
| SEQ. ID. NO. 5327 | 222-IleAlaAspArgProAspArgLeuIleGluAsnLysHisGly-235 |
| SEQ. ID. NO. 5328 | 240-TyrHisArgAspGlyAspLysValVal-248 |
| SEQ. ID. NO. 5329 | 264-AsnSerValAsnGlyIleGluArg-271 |
| SEQ. ID. NO. 5330 | 277-SerLeuLysSerGlyIleArgArg-284 |
| SEQ. ID. NO. 5331 | 321-IleAlaAspGluProGln-326 |
| SEQ. ID. NO. 5332 | 331-LeuGlnAspLysArgValGluIleValLeuAspAspGlyArgLysTrpLeuArgArgHisProAspGluLysPheAsp-356 |
| SEQ. ID. NO. 5333 | 385-HisLeuThrProAspGly-390 |
| SEQ. ID. NO. 5334 | 429-PheProAsnLysGluLeuLeuLysGlnArgLeuSer-440 |
| SEQ. ID. NO. 5335 | 444-TrpProGluSerGlyArgHisValPheAspSerSerThrVal-457 |

| | |
|---|---|
| SEQ. ID. NO. 5336 | 472-MetThrGluProSerAlaGly-478 |
| SEQ. ID. NO. 5337 | 481-ValIleThrAspAspAsnMet-487 |
| SEQ. ID. NO. 5338 | 489-ValGluTyrLysTyrGlyArgGlyIle-497 |
| Hydrophilic Regions - Hopp-Woods | |
| SEQ. ID. NO. 5339 | 131-GlyThrAspGlyAsnLysSerGlyArgGlnVal-141 |
| SEQ. ID. NO. 5340 | 222-IleAlaAspArgProAspArgLeuIleGluAsnLysHis-234 |
| SEQ. ID. NO. 5341 | 241-HisArgAspGlyAspLysValVal-248 |
| SEQ. ID. NO. 5342 | 278-LeuLysSerGlyIleArg-283 |
| SEQ. ID. NO. 5343 | 321-IleAlaAspGluProGln-326 |
| SEQ. ID. NO. 5344 | 331-LeuGlnAspLysArgValGluIleValLeuAspAspGlyArgLysTrpLeuArgArgHisProAspGluLysPheAsp-356 |
| SEQ. ID. NO. 5345 | 430-ProAsnLysGluLeuLeuLysGlnArgLeuSer-440 |
| SEQ. ID. NO. 5346 | 446-GluSerGlyArgHisValPhe-452 |
| SEQ. ID. NO. 5347 | 473-ThrGluProSerAlaGly-478 |
| SEQ. ID. NO. 5348 | 481-ValIleThrAspAspAsnMet-487 |
| 501-2 | |
| AMPHI Regions - AMPHI | |
| SEQ. ID. NO. 5349 | 63-ValGluValLeuGlnGluLeuPheArgGlnTyrArgValAlaArgGlnLeu-79 |
| SEQ. ID. NO. 5350 | 88-ValPheAlaAlaPheGlnAlaVal-95 |
| SEQ. ID. NO. 5351 | 97-PheGlnGlyPheAspAsnGlyPhe-104 |
| SEQ. ID. NO. 5352 | 126-AlaAspAlaPheGlnGly-131 |
| SEQ. ID. NO. 5353 | 139-ValPheGluValValGlyAspIleThrArgArgThrThrGluAla-153 |
| SEQ. ID. NO. 5354 | 183-AspGlyPheThrArgIleAsnArgCysGlyGlnCys-194 |
| SEQ. ID. NO. 5355 | 196-HisAlaPheGlyAspPheIleAsp-203 |
| Antigenic Index - Jameson-Wolf | |
| SEQ. ID. NO. 5356 | 6-LeuThrAlaAspAla-10 |
| SEQ. ID. NO. 5357 | 17-AlaAlaGlyGlyAspGlyLysValGlnHisHisPheAspGlyArgValAlaPhe-34 |
| SEQ. ID. NO. 5358 | 46-ValGluThrGluGlyGln-51 |
| SEQ. ID. NO. 5359 | 56-ValArgAlaAspGlyGluAlaValGluVal-65 |
| SEQ. ID. NO. 5360 | 100-PheAspAsnGlyPhe-104 |
| SEQ. ID. NO. 5361 | 108-GlnSerAlaAspGluArgAsnHisAspPheAsnValGlyGln-121 |
| SEQ. ID. NO. 5362 | 144-GlyAspIleThrArgArgThrThrGluAlaGlnHis-155 |
| SEQ. ID. NO. 5363 | 179-GlyHisThrAspAspGlyPheThrArgIleAsnArgCysGlyGlnCysArgHisAlaPhe-198 |
| SEQ. ID. NO. 5364 | 202-IleAspValGluValAspArgGlyArgValThrGlyAspThrAlaGlyAsnPhe-219 |
| Hydrophilic Regions - Hopp-Woods | |
| SEQ. ID. NO. 5365 | 6-LeuThrAlaAspAla-10 |
| SEQ. ID. NO. 5366 | 19-GlyGlyAspGlyLysVal-24 |
| SEQ. ID. NO. 5367 | 46-ValGluThrGluGlyGln-51 |
| SEQ. ID. NO. 5368 | 56-ValArgAlaAspGlyGluAlaValGluVal-65 |
| SEQ. ID. NO. 5369 | 108-GlnSerAlaAspGluArgAsnHisAsp-116 |
| SEQ. ID. NO. 5370 | 144-GlyAspIleThrArgArgThrThrGluAlaGlnHis-155 |
| SEQ. ID. NO. 5371 | 179-GlyHisThrAspAspGlyPheThrArgIleAsnArg-190 |
| SEQ. ID. NO. 5372 | 202-IleAspValGluValAspArgGlyArgValThrGlyAspThr-215 |
| 502-1 | |
| AMPHI Regions - AMPHI | |
| SEQ. ID. NO. 5373 | 6-AsnLeuPheGlnPheLeuAlaValCys-14 |
| SEQ. ID. NO. 5374 | 26-GlyAlaValAspAlaLeuLysGlnPheAsnAsnAspAlaAspGlyIleSerGlySerPheThrGln-47 |
| SEQ. ID. NO. 5375 | 98-GlnValThrLysSerSerGlnAsp-105 |
| Antigenic Index - Jameson-Wolf | |
| SEQ. ID. NO. 5376 | 32-LysGlnPheAsnAsnAspAlaAspGlyIleSerGlySer-44 |
| SEQ. ID. NO. 5377 | 48-ThrValGlnSerLysLysLysThrGlnThrAlaHisGlyThr-61 |
| SEQ. ID. NO. 5378 | 73-GluTyrThrLysProTyrArg-79 |
| SEQ. ID. NO. 5379 | 98-GlnValThrLysSerSerGlnAspGlnAlaIleGlyGlySerPro-112 |
| SEQ. ID. NO. 5380 | 116-LeuSerAsnLysThrAlaLeuGluSerSerTyrThrLeuLysGluAspGlySerSerAsnGly-136 |
| SEQ. ID. NO. 5381 | 142-AlaThrProLysArgAsnAsnAlaGly-150 |
| SEQ. ID. NO. 5382 | 158-PheLysGlyGlyAsn-162 |
| SEQ. ID. NO. 5383 | 167-GlnLeuLysAspSerPheGlyAsnGlnThr-176 |
| SEQ. ID. NO. 5384 | 184-AsnThrAsnProGlnLeuSerArgGlyAlaPhe-194 |
| SEQ. ID. NO. 5385 | 196-PheThrProProLysGlyValAspVal-204 |
| Hydrophilic Regions - Hopp-Woods | |
| SEQ. ID. NO. 5386 | 34-PheAsnAsnAspAlaAspGlyIle-41 |
| SEQ. ID. NO. 5387 | 49-ValGlnSerLysLysLysThrGlnThr-57 |
| SEQ. ID. NO. 5388 | ThrLysSerSerGlnAspGlnAlaIle-108 |
| SEQ. ID. NO. 5389 | 126-TyrThrLeuLysGluAspGlySerSerAsn-135 |
| SEQ. ID. NO. 5390 | 143-ThrProLysArgAsnAsnAla-149 |
| SEQ. ID. NO. 5391 | 167-GlnLeuLysAspSerPheGly-173 |
| 503-1 | |
| AMPHI Regions - AMPHI | |
| SEQ. ID. NO. 5392 | 96-SerSerThrSerAsnPheAlaSerAlaAlaGluMetArgSerLeu-110 |
| Antigenic Index - Jameson-Wolf | |
| SEQ. ID. NO. 5393 | 4-SerLeuTyrArgGluAlaAsnThrTrpCys-13 |
| SEQ. ID. NO. 5394 | 32-ProAlaAsnAspAlaSerGlyArgSerSerAlaValAlaGluGluArgThrAlaThrGluMetSerAlaProProAla-57 |
| SEQ. ID. NO. 5395 | 69-SerAlaSerSerCysSerGlyLysGlyValSer-79 |
| SEQ. ID. NO. 5396 | 87-LeuProThrArgAlaSerSerAlaThrSerSerThrSerAsn-100 |
| SEQ. ID. NO. 5397 | 105-AlaGluMetArgSerLeuArg-111 |
| SEQ. ID. NO. 5398 | 113-LeuCysAlaArgAsnAlaArg-119 |
| Hydrophilic Regions - Hopp-Woods | |
| SEQ. ID. NO. 5399 | 4-SerLeuTyrArgGlu-8 |
| SEQ. ID. NO. 5400 | 32-ProAlaAsnAspAlaSerGlyArgSerSerAlaValAlaGluGluArgThrAlaThrGluMetSerAla-54 |

TABLE 1-continued

| | |
|---|---|
| SEQ. ID. NO. 5401 | 73-CysSerGlyLysGlyValSer-79 |
| SEQ. ID. NO. 5402 | 89-ThrArgAlaSerSer-93 |
| SEQ. ID. NO. 5403 | 105-AlaGluMetArgSerLeuArg-111 |

505-2
AMPHI Regions - AMPHI

| | |
|---|---|
| SEQ. ID. NO. 5404 | 20-LeuThrAlaLeuLeuLysCysLeuSerLeuLeuProLeuSerCysLeu-35 |
| SEQ. ID. NO. 5405 | 37-ThrLeuGlyAsnArg-41 |
| SEQ. ID. NO. 5406 | 89-ProAlaPhePheArgLysProGluAspIleGluThrMetPheLysAlaValHisGlyTrpGluHisValGlnGlnAlaLeuAsp-116 |
| SEQ. ID. NO. 5407 | 148-AlaMetTyrLysProProLysIleLysAlaIleAspLysIleMetGlnAlaGly-165 |
| SEQ. ID. NO. 5408 | 178-IleGlnGlyValLysGlnIleIleLysAlaLeuArg-189 |
| SEQ. ID. NO. 5409 | 210-GlyValTrpValAspPhePheGlyLysPro-219 |

Antigenic Index - Jameson-Wolf

| | |
|---|---|
| SEQ. ID. NO. 5410 | 39-GlyAsnArgLeuGly-43 |
| SEQ. ID. NO. 5411 | 50-LeuLysGluAspArgAlaArgIle-57 |
| SEQ. ID. NO. 5412 | 64-AlaGlyLeuAsnProAspProLysThrValLys-74 |
| SEQ. ID. NO. 5413 | 79-GluThrAlaLysGlyGlyLeu-85 |
| SEQ. ID. NO. 5414 | 92-PheArgLysProGluAspIleGluThr-100 |
| SEQ. ID. NO. 5415 | 114-AlaLeuAspLysHisGlu-119 |
| SEQ. ID. NO. 5416 | 131-TyrAspLeuGlyGlyArgTyrIleSer-139 |
| SEQ. ID. NO. 5417 | 150-TyrLysProProLysIleLysAlaIleAspLysIleMetGln-163 |
| SEQ. ID. NO. 5418 | 165-GlyArgValArgGlyLysGlyLysThrAlaProThrSer-177 |
| SEQ. ID. NO. 5419 | 183-GlnIleIleLysAlaLeuArgSerGlyGluAlaThr-194 |
| SEQ. ID. NO. 5420 | 199-AspHisValProSerProGlnGluGlyGlyGluGlyVal-211 |
| SEQ. ID. NO. 5421 | 243-GluArgLeuProGlyGlyGlnGly-250 |
| SEQ. ID. NO. 5422 | 258-ValGlnGlyGluLeuAsnGlyAspLysAlaHisAsp-269 |
| SEQ. ID. NO. 5423 | 293-AsnArgTyrLysMetPro-298 |

Hydrophilic Regions - Hopp-Woods

| | |
|---|---|
| SEQ. ID. NO. 5424 | 50-LeuLysGluAspArgAlaArgIle-57 |
| SEQ. ID. NO. 5425 | 65-GlyLeuAsnProAspProLysThrVal-73 |
| SEQ. ID. NO. 5426 | 79-GluThrAlaLysGlyGlyLeu-85 |
| SEQ. ID. NO. 5427 | 92-PheArgLysProGluAspIleGluThr-100 |
| SEQ. ID. NO. 5428 | 114-AlaLeuAspLysHisGlu-119 |
| SEQ. ID. NO. 5429 | 151-LysProProLysIleLysAlaIleAspLysIleMetGln-163 |
| SEQ. ID. NO. 5430 | 165-GlyArgValArgGlyLysGlyLysThrAlaPro-175 |
| SEQ. ID. NO. 5431 | 183-GlnIleIleLysAlaLeuArgSerGlyGlu-192 |
| SEQ. ID. NO. 5432 | 201-ValProSerProGlnGluGlyGlyGlu-209 |
| SEQ. ID. NO. 5433 | 258-ValGlnGlyGluLeuAsnGlyAspLysAlaHisAsp-269 |

506-2
AMPHI Regions - AMPHI

| | |
|---|---|
| SEQ. ID. NO. 5434 | 6-GluValGlyArgValAlaHisCysGlyGlyGlyVal-17 |
| SEQ. ID. NO. 5435 | 25-ArgValValHisGlnValGluGlnGlyAlaArg-35 |
| SEQ. ID. NO. 5436 | 56-PheGlnArgArgPhe-60 |
| SEQ. ID. NO. 5437 | 99-AlaThrArgThrIleAspGlyAsnLeuAlaGluValTyrAlaGlnThr-114 |
| SEQ. ID. NO. 5438 | 138-GlyAsnGluValAlaArgCys-144 |
| SEQ. ID. NO. 5439 | 180-GlnValLysArgMetIleArgTyrPhePheArgVal-191 |

Antigenic Index - Jameson-Wolf

| | |
|---|---|
| SEQ. ID. NO. 5440 | 13-CysGlyGlyGlyValAla-18 |
| SEQ. ID. NO. 5441 | 31-GluGlnGlyAlaArgLeu-36 |
| SEQ. ID. NO. 5442 | 54-ValAspPheGlnArgArgPheGlyGluVal-63 |
| SEQ. ID. NO. 5443 | 98-ArgAlaThrArgThrIleAspGlyAsnLeu-107 |
| SEQ. ID. NO. 5444 | 134-GlyAlaAspThrGlyAsnGluValAlaArgCysGluGly-146 |
| SEQ. ID. NO. 5445 | 176-ProAsnPheGlyGlnValLysArgMetIle-185 |
| SEQ. ID. NO. 5446 | 195-HisAspLeuAspVal-199 |
| SEQ. ID. NO. 5447 | 201-ArgProPheArgLys-205 |

Hydrophilic Regions - Hopp-Woods

| | |
|---|---|
| SEQ. ID. NO. 5448 | 31-GluGlnGlyAlaArgLeu-36 |
| SEQ. ID. NO. 5449 | 54-ValAspPheGlnArgArgPheGlyGlu-62 |
| SEQ. ID. NO. 5450 | 98-ArgAlaThrArgThrIleAsp-104 |
| SEQ. ID. NO. 5451 | 136-AspThrGlyAsnGluValAlaArgCysGluGly-146 |
| SEQ. ID. NO. 5452 | 180-GlnValLysArgMetIle-185 |
| SEQ. ID. NO. 5453 | 195-HisAspLeuAspVal-199 |
| SEQ. ID. NO. 5454 | 201-ArgProPheArgLys-205 |

513
AMPHI Regions - AMPHI

| | |
|---|---|
| SEQ. ID. NO. 5455 | 6-AsnAlaAlaAlaAlaAla-11 |
| SEQ. ID. NO. 5456 | 19-GlnGlyMetIleGlnMetLeuGlyValPheValAsp-30 |
| SEQ. ID. NO. 5457 | 48-ProTyrGlyAspLeu-52 |
| SEQ. ID. NO. 5458 | 63-ValSerGlnValGlyGlnTrp-69 |
| SEQ. ID. NO. 5459 | 107-ThrAlaValPheArgMet-112 |
| SEQ. ID. NO. 5460 | 119-TyrPheGlyAlaValAla-124 |
| SEQ. ID. NO. 5461 | 139-IleMetAlaTrpIleAsnLeuValAlaIleLeuLeuLeuSer-152 |

Antigenic Index - Jameson-Wolf

| | |
|---|---|
| SEQ. ID. NO. 5462 | 2-GlySerAlaProAsnAla-7 |
| SEQ. ID. NO. 5463 | 11-AlaGluValLysHisProVal-17 |
| SEQ. ID. NO. 5464 | 47-GlnProTyrGlyAspLeuSerGly-54 |
| SEQ. ID. NO. 5465 | 91-AlaTyrAlaGluSerAsnVal-97 |
| SEQ. ID. NO. 5466 | 160-ArgAspTyrThrAlaLysLeuLysMetGlyLysAspProGluPheLysLeuSerGluHisProGlyLeuLysArgArgIleLysSerAspValTrp-191 |

TABLE 1-continued

| | |
|---|---|
| Hydrophilic Regions - Hopp-Woods | |
| SEQ. ID. NO. 5467 | 11-AlaGluValLysHis-15 |
| SEQ. ID. NO. 5468 | 166-LeuLysMetGlyLysAspProGluPheLysLeuSerGlu-178 |
| SEQ. ID. NO. 5469 | 180-ProGlyLeuLysArgArgIleLysSer-188 |
| 515-1 | |
| AMPHI Regions - AMPHI | |
| SEQ. ID. NO. 5470 | 8-ArgAlaAlaGlyValAlaArgGlyLeuHisThrGluPheAlaArgAlaVal-24 |
| SEQ. ID. NO. 5471 | 59-AspValArgPhePheAlaGlnValGluGluIleGlyGlnAspPhePheAlaAspAla-77 |
| SEQ. ID. NO. 5472 | 90-AlaGlyGluCysAlaAspGluValSerAspLysThr-101 |
| SEQ. ID. NO. 5473 | 122-GluSerAlaGlnSerAlaAlaGlyGlyGlyLeuThrAspGlyPheGly-137 |
| SEQ. ID. NO. 5474 | 176-CysGlyLysThrValGlyVal-182 |
| SEQ. ID. NO. 5475 | 198-GlyValPheAspAla-202 |
| SEQ. ID. NO. 5476 | 251-PheGlyGlyValAla-255 |
| SEQ. ID. NO. 5477 | 259-AspGlyGlyPheAspGlyValLeuGlnGlyPhePheGlyGluVal-273 |
| Antigenic Index - Jameson-Wolf | |
| SEQ. ID. NO. 5478 | 24-ValThrAlaGluGluIleAlaPhe-31 |
| SEQ. ID. NO. 5479 | 38-HisGluAlaArgCysGlyGlyAsn-45 |
| SEQ. ID. NO. 5480 | 51-IleAlaAlaAlaGluArgAlaGlyAsp-59 |
| SEQ. ID. NO. 5481 | 67-GluGluIleGlyGln-71 |
| SEQ. ID. NO. 5482 | 77-AlaValAspGlnGluThr-82 |
| SEQ. ID. NO. 5483 | 84-LeuAlaValGluArgAlaAlaGlyGluCysAlaAspGluValSerAspLysThrAlaArgAsnGlyGlyIleGluGluAspGlyValAlaAlaCysArgAsp AlaAlaAlaAlaGluSerAlaGln-125 |
| SEQ. ID. NO. 5484 | 128-AlaGlyGlyGlyLeuThrAspGly-135 |
| SEQ. ID. NO. 5485 | 160-GlyGlyAsnAspAlaAlaGlyAsn-167 |
| SEQ. ID. NO. 5486 | 192-LeuHisArgArgAla-196 |
| SEQ. ID. NO. 5487 | 217-AlaAspGlyGlyPheArg-222 |
| SEQ. ID. NO. 5488 | 239-HisGlnThrGlyIleGlyLysSerGly-247 |
| SEQ. ID. NO. 5489 | 256-GlyAspValAspGlyGlyPheAspGly-264 |
| SEQ. ID. NO. 5490 | 273-ValGlySerThrGlyAla-278 |
| SEQ. ID. NO. 5491 | 284-AspValAsnGlyAsnValGln-290 |
| Hydrophilic Regions - Hopp-Woods | |
| SEQ. ID. NO. 5492 | 24-ValThrAlaGluGluIleAlaPhe-31 |
| SEQ. ID. NO. 5493 | 38-HisGluAlaArgCysGly-43 |
| SEQ. ID. NO. 5494 | 51-IleAlaAlaAlaGluArgAlaGlyAsp-59 |
| SEQ. ID. NO. 5495 | 77-AlaValAspGlnGluThr-82 |
| SEQ. ID. NO. 5496 | 84-LeuAlaValGluArgAlaAlaGlyGluCysAlaAspGluValSerAspLysThrAlaArgAsnGlyGlyIleGluGluAspGlyValAlaAlaCysArgAsp AlaAlaAlaAlaGluSerAlaGln-125 |
| SEQ. ID. NO. 5497 | 162-AsnAspAlaAlaGly-166 |
| SEQ. ID. NO. 5498 | 192-LeuHisArgArgAla-196 |
| SEQ. ID. NO. 5499 | 242-GlyIleGlyLysSerGly-247 |
| SEQ. ID. NO. 5500 | 256-GlyAspValAspGlyGlyPhe-262 |
| 519-1 | |
| AMPHI Regions - AMPHI | |
| SEQ. ID. NO. 5501 | 15-GlyPheLysSerPhe-19 |
| SEQ. ID. NO. 5502 | 29-ValValGluArgLeuGlyArgPheHisArgAlaLeuThrAlaGly-43 |
| SEQ. ID. NO. 5503 | 105-MetAlaIleThrGlnLeuAlaGlnThrThrLeuArgSerVal-118 |
| SEQ. ID. NO. 5504 | 141-AlaLeuAspGluAlaAla-146 |
| SEQ. ID. NO. 5505 | 166-GluIleLeuArgSerMetGlnAla-173 |
| SEQ. ID. NO. 5506 | 192-LysIleGluGlnIle-196 |
| SEQ. ID. NO. 5507 | 221-SerAsnAlaGluLysIleAlaArgIleAsn-230 |
| SEQ. ID. NO. 5508 | 249-AlaIleArgGlnIleAlaAlaAla-256 |
| SEQ. ID. NO. 5509 | 273-GlnTyrValAlaAlaPheAsnAsnLeuAlaLys-283 |
| SEQ. ID. NO. 5510 | 292-AlaAsnValAlaAspIleGlySerLeuIleSerAlaGlyMetLysIleIleAspSerSerLysThrAla-314 |
| Antigenic Index - Jameson-Wolf | |
| SEQ. ID. NO. 5511 | 31-GluArgLeuGlyArgPheHisArg-38 |
| SEQ. ID. NO. 5512 | 58-HisSerLeuLysGluIleProLeuAspValProSerGln-70 |
| SEQ. ID. NO. 5513 | 72-CysIleThrArgAspAsnThrGlnLeuThrVal-82 |
| SEQ. ID. NO. 5514 | 91-ThrAspProLysLeuAlaSer-97 |
| SEQ. ID. NO. 5515 | 122-MetGluLeuAspLysThrPheGluGluArgAspGluIleAsn-135 |
| SEQ. ID. NO. 5516 | 141-AlaLeuAspGluAlaAlaGly-147 |
| SEQ. ID. NO. 5517 | 154-LeuArgTyrGluIleLysAspLeuValPro-163 |
| SEQ. ID. NO. 5518 | 175-IleThrAlaGluArgGluLysArgAlaArgIleAlaGluSerGluGlyArgLysIleGluGln-195 |
| SEQ. ID. NO. 5519 | 197-AsnLeuAlaSerGlyGlnArgGluAlaGluIleGlnGlnSerGluGlyGluAlaGlnAla-216 |
| SEQ. ID. NO. 5520 | 219-AsnAlaSerAsnAlaGluLysIleAlaArgIleAsnArgAlaLysGlyGluAlaGluSerLeuArgLeu-241 |
| SEQ. ID. NO. 5521 | 245-AlaAsnAlaGluAlaIleArg-251 |
| SEQ. ID. NO. 5522 | 258-GlnThrGlnGlyGlyAlaAspAlaValAsn-267 |
| SEQ. ID. NO. 5523 | 281-LeuAlaLysGluSerAsnThr-287 |
| SEQ. ID. NO. 5524 | 303-AlaGlyMetLysIleIleAspSerSerLysThrAlaLys-315 |
| Hydrophilic Regions - Hopp-Woods | |
| SEQ. ID. NO. 5525 | 31-GluArgLeuGlyArgPheHisArg-38 |
| SEQ. ID. NO. 5526 | 58-HisSerLeuLysGluIleProLeu-65 |
| SEQ. ID. NO. 5527 | 73-IleThrArgAspAsnThr-78 |
| SEQ. ID. NO. 5528 | 91-ThrAspProLysLeu-95 |
| SEQ. ID. NO. 5529 | 122-MetGluLeuAspLysThrPheGluGluArgAspGluIleAsn-135 |
| SEQ. ID. NO. 5530 | 141-AlaLeuAspGluAlaAla-146 |
| SEQ. ID. NO. 5531 | 154-LeuArgTyrGluIleLysAspLeuValPro-163 |
| SEQ. ID. NO. 5532 | 175-IleThrAlaGluArgGluLysArgAlaArgIleAlaGluSerGluGlyArgLysIleGluGln-195 |
| SEQ. ID. NO. 5533 | 200-SerGlyGlnArgGluAlaGluIleGlnGlnSerGluGlyGluAlaGlnAla-216 |
| SEQ. ID. NO. 5534 | 221-SerAsnAlaGluLysIleAlaArgIleAsnArgAlaLysGlyGluAlaGluSerLeuArgLeu-241 |
| SEQ. ID. NO. 5535 | 245-AlaAsnAlaGluAlaIleArg-251 |

TABLE 1-continued

| | |
|---|---|
| SEQ. ID. NO. 5536 | 281-LeuAlaLysGluSerAsn-286 |
| SEQ. ID. NO. 5537 | 306-LysIleIleAspSerSerLysThrAlaLys-315 |

520-1
AMPHI Regions - AMPHI

| | |
|---|---|
| SEQ. ID. NO. 5538 | 104-LeuThrLysAlaAlaAspGlyGlnValCysArgAlaPheSerSerLeu-119 |

Antigenic Index - Jameson-Wolf

| | |
|---|---|
| SEQ. ID. NO. 5539 | 20-LysProSerArgArgAlaLeu-26 |
| SEQ. ID. NO. 5540 | 47-AlaSerGlyLysIleSerLeuPro-54 |
| SEQ. ID. NO. 5541 | 84-ProProAsnAsnSerThrThrThrSerThrSerSerArgAlaThrSerSerAsnGlySerLeuThrLysAlaAlaAspGlyGlnVal-112 |
| SEQ. ID. NO. 5542 | 117-SerSerLeuLysSerHisThrAlaGluIleArgIleSerArgProLysArgArgGluIleSerSerAlaLeuSerArgAsnThrAlaAla-146 |
| SEQ. ID. NO. 5543 | 150-ProThrValProLysProLysArgProMet-159 |
| SEQ. ID. NO. 5544 | 166-SerProCysLysProThrGluMet-173 |

Hydrophilic Regions - Hopp-Woods

| | |
|---|---|
| SEQ. ID. NO. 5545 | 20-LysProSerArgArgAlaLeu-26 |
| SEQ. ID. NO. 5546 | 93-ThrSerSerArgAlaThrSerSer-100 |
| SEQ. ID. NO. 5547 | 103-SerLeuThrLysAlaAlaAsp-109 |
| SEQ. ID. NO. 5548 | 120-LysSerHisThrAlaGluIleArgIleSerArgProLysArgArgGluIleSer-137 |
| SEQ. ID. NO. 5549 | 140-LeuSerArgAsnThrAla-145 |
| SEQ. ID. NO. 5550 | 151-ThrValProLysProLysArgProMet-159 |
| SEQ. ID. NO. 5551 | 168-CysLysProThrGluMet-173 |

521-2
AMPHI Regions - AMPHI

| | |
|---|---|
| SEQ. ID. NO. 5552 | 39-ThrLysProSerLysSerCys-45 |
| SEQ. ID. NO. 5553 | 50-LeuProProIleGly-54 |
| SEQ. ID. NO. 5554 | 65-GlnThrProGluProValSerSerProSer-74 |
| SEQ. ID. NO. 5555 | 76-GlyGlyGlnValVal-80 |
| SEQ. ID. NO. 5556 | 86-ValLysThrValSerLysProAlaLys-94 |
| SEQ. ID. NO. 5557 | 133-GlnAlaArgLeuAlaLysGlyGlyAsn-141 |

Antigenic Index - Jameson-Wolf

| | |
|---|---|
| SEQ. ID. NO. 5558 | 36-ValTyrThrThrLysProSerLysSerCysHisSerThrAspLeuProProIleGlyAsnTyrSerSerGluArgTyrIleProProGlnThrProGluProValSer SerProSerAsnGlyGlyGlnValValLysTyrLysAlaProValLysThrValSerLysProAlaLysSerAsnThrProProProGlnGlnAlaProSerAsnAsn SerArgArgSerIleLeuGluThrGluLeuSerAsnGluArgLysAlaLeuValGluAlaGlnLysMetLeuSer-132 |
| SEQ. ID. NO. 5559 | 135-ArgLeuAlaLysGlyGlyAsnIleAsn-143 |
| SEQ. ID. NO. 5560 | 152-SerAsnValLeuAspArgGlnGlnAsn-160 |
| SEQ. ID. NO. 5561 | 164-LeuGlnArgGluLeuGlyArg-170 |

Hydrophilic Regions - Hopp-Woods

| | |
|---|---|
| SEQ. ID. NO. 5562 | 40-LysProSerLysSerCysHis-46 |
| SEQ. ID. NO. 5563 | 57-SerSerGluArgTyrIle-62 |
| SEQ. ID. NO. 5564 | 65-GlnThrProGluProValSer-71 |
| SEQ. ID. NO. 5565 | 80-ValLysTyrLysAlaProVal-86 |
| SEQ. ID. NO. 5566 | 88-ThrValSerLysProAlaLysSerAsnThrProPro-99 |
| SEQ. ID. NO. 5567 | 102-GlnAlaProSerAsnAsnSerArgArgSerIleLeuGluThrGluLeuSerAsnGluArgLysAlaLeuValGluAlaGlnLysMetLeuSer-132 |
| SEQ. ID. NO. 5568 | 154-ValLeuAspArgGlnGlnAsn-160 |
| SEQ. ID. NO. 5569 | 164-LeuGlnArgGluLeuGlyArg-170 |

522
AMPHI Regions - AMPHI

| | |
|---|---|
| SEQ. ID. NO. 5570 | 32-TrpValIleLeuAlaLeuLeuAlaLeuThrAlaLeuSer-45 |
| SEQ. ID. NO. 5571 | 57-LysIleValGluSerCysValLys-64 |
| SEQ. ID. NO. 5572 | 96-MetTrpGluGlnProLeuAspArgLeuSerGluLysGlnIleArgSerPheGlyLysLeuGlyAlaGlnGluGlnLeuAspLeuLeuGlyGlyAla-127 |

Antigenic Index - Jameson-Wolf

| | |
|---|---|
| SEQ. ID. NO. 5573 | 1-MetThrGluProLysHisGluMetLeuThrLysGluGlnValAlaAlaArgLysLysAlaLysAlaLysIleArgThr-26 |
| SEQ. ID. NO. 5574 | 48-AlaMetSerLysProGlnAlaLysGlnLysIleValGluSerCysValLys-64 |
| SEQ. ID. NO. 5575 | 71-LysTrpGlnAsnAspLeuArgAlaArgGlyLeuAspSerAsnAsnThrArgLeuAla-89 |
| SEQ. ID. NO. 5576 | 99-GlnProLeuAspArgLeuSerGluLysGlnIleArgSerPheGlyLysLeuGlyAla-117 |
| SEQ. ID. NO. 5577 | 128-AsnAlaPheGluAlaArgAspLysGlnCysValAlaAspLeuLysSerGlu-144 |

Hydrophilic Regions - Hopp-Woods

| | |
|---|---|
| SEQ. ID. NO. 5578 | 1-MetThrGluProLysHisGluMetLeuThrLysGluGlnValAlaAlaArgLysLysAlaLysAlaLysIleArgThr-26 |
| SEQ. ID. NO. 5579 | 48-AlaMetSerLysProGlnAlaLysGlnLysIleValGluSerCysVal-63 |
| SEQ. ID. NO. 5580 | 71-LysTrpGlnAsnAspLeuArgAlaArgGlyLeuAspSerAsnAsnThr-86 |
| SEQ. ID. NO. 5581 | 100-ProLeuAspArgLeuSerGluLysGlnIleArgSerPheGly-113 |
| SEQ. ID. NO. 5582 | 130-PheGluAlaArgAspLysGlnCysValAlaAspLeuLysSerGlu-144 |

525-1
AMPHI Regions - AMPHI

| | |
|---|---|
| SEQ. ID. NO. 5583 | 59-GluPheAlaGluPheValAsnSerHisProGln-69 |
| SEQ. ID. NO. 5584 | 86-LysHisTrpMetLysAsnGly-92 |
| SEQ. ID. NO. 5585 | 125-ArgLeuProThrIleAspGluTrpGluPhe-134 |
| SEQ. ID. NO. 5586 | 154-ThrIleLeuAspTrpTyr-159 |
| SEQ. ID. NO. 5587 | 164-ArgLysGlyLeuHisAspValGly-171 |
| SEQ. ID. NO. 5588 | 178-TrpGlyValTyrAsp-182 |
| SEQ. ID. NO. 5589 | 188-TrpGluTrpThrGlu-192 |

Antigenic Index - Jameson-Wolf

| | |
|---|---|
| SEQ. ID. NO. 5590 | 24-ValGlnIleGluGlyGlySerTyrArgProLeuTyrLeuLysLysAspThrGlyLeuIleLys-44 |
| SEQ. ID. NO. 5591 | 46-LysProPheLysLeuAspLysTyrProValThr-56 |
| SEQ. ID. NO. 5592 | 67-HisProGlnTrpGlnLysGlyArgIleGlySerLysGlnAlaGlu-81 |
| SEQ. ID. NO. 5593 | 88-TrpMetLysAsnGlySerArgSerTyrAlaProLysAlaGlyGluLeuLysGlnPro-106 |
| SEQ. ID. NO. 5594 | 122-GlnGlyLysArgLeuProThrIleAspGluTrpGlu-133 |
| SEQ. ID. NO. 5595 | 140-AlaThrGlnLysAsnGlySerAsnGluProGlyTyrAsnArgThr-154 |
| SEQ. ID. NO. 5596 | 159-TyrAlaAspGlyGlyArgLysGlyLeuHisAspValGlyLysGlyArgProAsnTyr-177 |

TABLE 1-continued

| | |
|---|---|
| SEQ. ID. NO. 5597 | 190-TrpThrGluAspPheAsnSerSerLeuLeuSerSerGlyAsnAla-204 |
| SEQ. ID. NO. 5598 | 213-AlaSerIleGlySerSerAspSerSerAsnTyr-223 |
| SEQ. ID. NO. 5599 | 234-SerLeuGlnSerLysTyr-239 |
| Hydrophilic Regions - Hopp-Woods | |
| SEQ. ID. NO. 5600 | 35-TyrLeuLysLysAspThrGlyLeuIleLys-44 |
| SEQ. ID. NO. 5601 | 46-LysProPheLysLeuAspLysTyrPro-54 |
| SEQ. ID. NO. 5602 | 71-GlnLysGlyArgIleGlySerLysGlnAlaGlu-81 |
| SEQ. ID. NO. 5603 | 91-AsnGlySerArgSerTyrAlaProLysAlaGlyGluLeuLysGln-105 |
| SEQ. ID. NO. 5604 | 122-GlnGlyLysArgLeuProThr-128 |
| SEQ. ID. NO. 5605 | 140-AlaThrGlnLysAsnGlySerAsnGluProGlyTyr-151 |
| SEQ. ID. NO. 5606 | 162-GlyGlyArgLysGlyLeuHisAspValGlyLysGlyArgPro-175 |
| SEQ. ID. NO. 5607 | 216-GlySerSerAspSerSerAsn-222 |
| 527-2 | |
| AMPHI Regions - AMPHI | |
| SEQ. ID. NO. 5608 | 7-PhePheGlnProValGln-12 |
| SEQ. ID. NO. 5609 | 28-SerAspAlaAlaGluLeuValGluLeuPheAlaLeuPhePro-41 |
| SEQ. ID. NO. 5610 | 73-GlyLysGlyIleGluArgGlnValAspAsnIleAlaAspValTyrGlyPhe-89 |
| Antigenic Index - Jameson-Wolf | |
| SEQ. ID. NO. 5611 | 26-GlyGlySerAspAlaAlaGlu-32 |
| SEQ. ID. NO. 5612 | 52-GlnLysProArgLeuGlyCys-58 |
| SEQ. ID. NO. 5613 | 71-PheIleGlyLysGlyIleGluArgGlnValAspAsnIleAla-84 |
| SEQ. ID. NO. 5614 | 107-LeuLeuArgLysGlyThrGlyLeuGluLysThrCysArgProLysProPheValGlnProHisGlyGlyArg-130 |
| Hydrophilic Regions - Hopp-Woods | |
| SEQ. ID. NO. 5615 | 27-GlySerAspAlaAlaGlu-32 |
| SEQ. ID. NO. 5616 | 52-GlnLysProArgLeuGlyCys-58 |
| SEQ. ID. NO. 5617 | 75-GlyIleGluArgGlnValAspAsnIleAla-84 |
| SEQ. ID. NO. 5618 | 107-LeuLeuArgLysGlyThrGlyLeuGluLysThrCysArgProLysPro-122 |
| 528-1 | |
| AMPHI Regions - AMPHI | |
| SEQ. ID. NO. 5619 | 7-LysTyrThrAlaMetAlaAlaLeuLeuAlaPhe-17 |
| SEQ. ID. NO. 5620 | 23-ArgLeuAlaGlyTrpTyrGluCysSerSerLeuThrGlyTrpCysLysProArgLysProAlaAlaIle-45 |
| SEQ. ID. NO. 5621 | 69-AsnArgSerValArg-73 |
| SEQ. ID. NO. 5622 | 86-TyrArgLysIleGlyLysPhe-92 |
| SEQ. ID. NO. 5623 | 106-ProLeuIleGluThrPheLys-112 |
| Antigenic Index - Jameson-Wolf | |
| SEQ. ID. NO. 5624 | 1-MetGluIleArgAla-5 |
| SEQ. ID. NO. 5625 | 29-GluCysSerSerLeuThrGlyTrpCysLysProArgLysProAlaAla-44 |
| SEQ. ID. NO. 5626 | 49-AspIleGlyGlyGluSerProProSerLeuGlyAspTyrGluIleProLeuSerAspGlyAsnArgSerValArgAlaAsnGluTyrGluSerAlaGlnGln Ser-83 |
| SEQ. ID. NO. 5627 | 88-LysIleGlyLysPheGluAlaCysGlyLeuAspTrpArgThrArgAspGlyLysProLeu-107 |
| SEQ. ID. NO. 5628 | 110-ThrPheLysGlnGlyGlyPheAspCysLeuGluLysGlnGlyLeuArgArgAsnGlyLeuSerGluArgValArgTrp-135 |
| Hydrophilic Regions - Hopp-Woods | |
| SEQ. ID. NO. 5629 | 1-MetGluIleArgAla-5 |
| SEQ. ID. NO. 5630 | 37-CysLysProArgLysProAlaAla-44 |
| SEQ. ID. NO. 5631 | 51-GlyGlyGluSerProProSer-57 |
| SEQ. ID. NO. 5632 | 59-GlyAspTyrGluIleProLeu-65 |
| SEQ. ID. NO. 5633 | 67-AspGlyAsnArgSerValArgAlaAsnGluTyrGluSerAlaGln-81 |
| SEQ. ID. NO. 5634 | 88-LysIleGlyLysPheGluAlaCys-95 |
| SEQ. ID. NO. 5635 | 99-TrpArgThrArgAspGlyLysProLeu-107 |
| SEQ. ID. NO. 5636 | 117-AspCysLeuGluLysGlnGlyLeuArgArgAsnGlyLeuSerGluArgValArgTrp-135 |
| 529 | |
| AMPHI Regions - AMPHI | |
| SEQ. ID. NO. 5637 | 11-LeuAlaLeuIleGlyLeuAlaAlaCysSer-20 |
| SEQ. ID. NO. 5638 | 35-SerHisArgLeuIle-39 |
| SEQ. ID. NO. 5639 | 49-AsnProAspGlnGlyAsnLeuTyrArgLeuProAla-60 |
| SEQ. ID. NO. 5640 | 79-GlnGlnProAlaAspAlaGluValLeuLysSerValLysGlyValArg-94 |
| SEQ. ID. NO. 5641 | 152-GlnAspSerLeuArgArgLeuPheAsp-160 |
| SEQ. ID. NO. 5642 | 196-AlaMetLysGluVal-200 |
| SEQ. ID. NO. 5643 | 223-AlaPheLeuThrArgPheMetGlnTyrLeu-232 |
| SEQ. ID. NO. 5644 | 252-AlaAsnGluMetAla-256 |
| SEQ. ID. NO. 5645 | 270-GlyArgAsnTrpArgArgThrVal-277 |
| Antigenic Index - Jameson-Wolf | |
| SEQ. ID. NO. 5646 | 19-CysSerGlySerLysThrGluGlnProLysLeuAspTyrGlnSerArgSerHisArgLeuIleLys-40 |
| SEQ. ID. NO. 5647 | 42-GluValProProAspLeuAsnAsnProAspGlnGlyAsnLeuTyr-56 |
| SEQ. ID. NO. 5648 | 60-AlaGlySerGlyAlaValArgAlaSerAspLeuGluLysArgArgThrProAlaVal-78 |
| SEQ. ID. NO. 5649 | 80-GlnProAlaAspAlaGluValLeuLysSerValLysGlyValArgLeuGluArgAspGlySerGln-101 |
| SEQ. ID. NO. 5650 | 105-ValValAspGlyLysSerProAlaGlu-113 |
| SEQ. ID. NO. 5651 | 123-GlnGluAsnGlyPheAspIleLysSerGluGluProAla-135 |
| SEQ. ID. NO. 5652 | 139-MetGluThrGluTrpAlaGluAsnArgAlaLysIleProGlnAspSerLeuArgArgLeuPheAsp-160 |
| SEQ. ID. NO. 5653 | 169-SerThrGlyGluArgAspLysPheIleValArgIleGluGlnGlyLysAsnGlyValSer-188 |
| SEQ. ID. NO. 5654 | 195-LysAlaMetLysGluValTyrGlyGlyLysAspLysAspThrThr-209 |
| SEQ. ID. NO. 5655 | 212-GlnProSerProSerAspProAsnLeu-220 |
| SEQ. ID. NO. 5656 | 233-GlyValAspGlyGlnGlnAlaGluAsnAlaSerAlaLysLysProThrLeu-249 |
| SEQ. ID. NO. 5657 | 253-AsnGluMetAlaArgIleGluGlyLysSer-262 |
| SEQ. ID. NO. 5658 | 268-AspTyrGlyArgAsnTrpArgArgThrVal-277 |
| SEQ. ID. NO. 5659 | 289-GlyGlnAsnThrGluArgHisAla-296 |
| SEQ. ID. NO. 5660 | 300-GlnLysAlaProAsnGluSerAsnAlaValThrGluGlnLysProGlyLeu-316 |
| SEQ. ID. NO. 5661 | 320-LeuLeuGlyLysGlyLysAlaGluLysProAlaGluGlnProGlu-334 |
| SEQ. ID. NO. 5662 | 342-ValAlaAsnGlySerArg-347 |

TABLE 1-continued

| | |
|---|---|
| SEQ. ID. NO. 5663 | 350-LeuLeuAsnLysAspGlySerAlaTyrAlaGlyLysAspAlaSer-364 |
| SEQ. ID. NO. 5664 | 370-LeuHisSerGluLeuArg-375 |
| Hydrophilic Regions - Hopp-Woods | |
| SEQ. ID. NO. 5665 | 20-SerGlySerLysThrGluGlnProLysLeuAspTyrGlnSerArgSerHisArgLeuIleLys-40 |
| SEQ. ID. NO. 5666 | 42-GluValProProAspLeuAsnAsnProAspGln-52 |
| SEQ. ID. NO. 5667 | 63-GlyAlaValArgAlaSerAspLeuGluLysArgArgThrProAla-77 |
| SEQ. ID. NO. 5668 | 80-GlnProAlaAspAlaGluValLeuLysSerValLysGlyValArgLeuGluArgAspGlySerGln-101 |
| SEQ. ID. NO. 5669 | 107-AspGlyLysSerProAla-112 |
| SEQ. ID. NO. 5670 | 125-AsnGlyPheAspIleLysSerGluGluProAla-135 |
| SEQ. ID. NO. 5671 | 139-MetGluThrGluTrpAlaGluAsnArgAlaLysIleProGlnAspSerLeuArgArgLeuPheAsp-160 |
| SEQ. ID. NO. 5672 | 170-ThrGlyGluArgAspLysPheIleVal-178 |
| SEQ. ID. NO. 5673 | 180-IleGluGlnGlyLysAsnGlyVal-187 |
| SEQ. ID. NO. 5674 | 195-LysAlaMetLysGluValTyrGlyGlyLysAspLysAspThrThr-209 |
| SEQ. ID. NO. 5675 | 214-SerProSerAspProAsnLeu-220 |
| SEQ. ID. NO. 5676 | 235-AspGlyGlnGlnAlaGluAsnAlaSerAlaLysLysProThr-248 |
| SEQ. ID. NO. 5677 | 253-AsnGluMetAlaArgIleGluGlyLysSer-262 |
| SEQ. ID. NO. 5678 | 269-TyrGlyArgAsnTrpArg-274 |
| SEQ. ID. NO. 5679 | 291-AsnThrGluArgHis-295 |
| SEQ. ID. NO. 5680 | 302-AlaProAsnGluSerAsnAlaValThrGluGlnLysProGlyLeu-316 |
| SEQ. ID. NO. 5681 | 320-LeuLeuGlyLysGlyLysAlaGluLysProAlaGluGlnProGlu-334 |
| SEQ. ID. NO. 5682 | 352-AsnLysAspGlySer-356 |
| SEQ. ID. NO. 5683 | 359-AlaGlyLysAspAlaSer-364 |
| SEQ. ID. NO. 5684 | 370-LeuHisSerGluLeuArg-375 |
| 531 | |
| AMPHI Regions - AMPHI | |
| SEQ. ID. NO. 5685 | 59-SerLeuAlaGlyIleLeuAlaAspTyrValAlaGlyIleTrpGlyThr-74 |
| SEQ. ID. NO. 5686 | 90-GlySerIleIleGlyIlePhePheSerLeuProGlyLeuIleLeuGly-105 |
| SEQ. ID. NO. 5687 | 108-IleGlyAlaAlaAlaGly-113 |
| SEQ. ID. NO. 5688 | 132-LeuLeuGlyLeuValVal-137 |
| Antigenic Index - Jameson-Wolf | |
| SEQ. ID. NO. 5689 | 74-ThrLysTyrThrGlyAlaGlyLysLeuAlaVal-84 |
| SEQ. ID. NO. 5690 | 114-GluLeuIleGluArgArgAsnMet-121 |
| Hydrophilic Regions - Hopp-Woods | |
| SEQ. ID. NO. 5691 | 114-GluLeuIleGluArgArgAsnMet-121 |
| 532 | |
| AMPHI Regions - AMPHI | |
| SEQ. ID. NO. 5692 | 6-GlyLysGlyAlaAsp-10 |
| SEQ. ID. NO. 5693 | 27-AlaLeuLeuSerAlaValThrHisLeuLeuAlaIlePheValProMetIleThr-44 |
| SEQ. ID. NO. 5694 | 76-TyrLeuGlnValAsnArgPheGlyPro-84 |
| SEQ. ID. NO. 5695 | 122-SerThrLeuLeuGly-126 |
| SEQ. ID. NO. 5696 | 147-LysValIleThrProThrVal-153 |
| SEQ. ID. NO. 5697 | 184-ThrPheGlySerMetGluAsnLeuGly-192 |
| SEQ. ID. NO. 5698 | 206-CysMetLysAsnPro-210 |
| SEQ. ID. NO. 5699 | 224-GlyTyrIleValAlaLeu-229 |
| SEQ. ID. NO. 5700 | 236-PheSerAlaLeuGlnAsnLeuPro-243 |
| SEQ. ID. NO. 5701 | 271-LeuSerValPheGluAlaValGlyAspLeuThrAla-282 |
| SEQ. ID. NO. 5702 | 297-ThrLysArgLeuArgGlyGlyVal-304 |
| SEQ. ID. NO. 5703 | 307-AspGlyLeuValSerValIleAlaThrAlaLeuGly-318 |
| SEQ. ID. NO. 5704 | 338-AlaSerArgHisValGlyLysTyr-345 |
| SEQ. ID. NO. 5705 | 361-ArgAlaPheThrThrIleProSerProVal-370 |
| Antigenic Index - Jameson-Wolf | |
| SEQ. ID. NO. 5706 | 1-MetSerGlyGlnLeuGlyLysGlyAlaAspAlaPro-12 |
| SEQ. ID. NO. 5707 | 18-LeuGluAspArgProProPheGlyAsn-26 |
| SEQ. ID. NO. 5708 | 80-AsnArgPheGlyPro-84 |
| SEQ. ID. NO. 5709 | 108-AlaGlyMetLysGluGlyGlyLeuThrLysAspAlaMet-120 |
| SEQ. ID. NO. 5710 | 177-PheGlyAlaLysAlaAspGlyThrPheGlySer-187 |
| SEQ. ID. NO. 5711 | 207-MetLysAsnProLeuLeuArg-213 |
| SEQ. ID. NO. 5712 | 286-ValSerAspGlnProIleGluGlyGluGluTyrThrLysArgLeuArgGlyGlyValLeu-305 |
| SEQ. ID. NO. 5713 | 391-ValSerHisGlyIleArgArgArgGluAlaVal-401 |
| SEQ. ID. NO. 5714 | 445-LeuProGluAspLysThrGluAlaAlaValLysPheAspThrAspHisLeuGluHis-463 |
| Hydrophilic Regions - Hopp-Woods | |
| SEQ. ID. NO. 5715 | 4-GlnLeuGlyLysGlyAlaAspAlaPro-12 |
| SEQ. ID. NO. 5716 | 18-LeuGluAspArgProProPhe-24 |
| SEQ. ID. NO. 5717 | 109-GlyMetLysGluGlyGlyLeuThrLysAspAlaMet-120 |
| SEQ. ID. NO. 5718 | 179-AlaLysAlaAspGly-183 |
| SEQ. ID. NO. 5719 | 289-GlnProIleGluGlyGluGluTyrThrLysArgLeuArgGly-302 |
| SEQ. ID. NO. 5720 | 394-GlyIleArgArgArgGluAlaVal-401 |
| SEQ. ID. NO. 5721 | 445-LeuProGluAspLysThrGluAlaAlaValLysPheAspThrAspHisLeuGluHis-463 |
| 537-2 | |
| AMPHI Regions - AMPHI | |
| SEQ. ID. NO. 5722 | 38-GlnIleArgAspGlyGlyAspAlaLeuHisTyrLeuAsnArgIle-52 |
| SEQ. ID. NO. 5723 | 86-HisGlyGluHisHis-90 |
| SEQ. ID. NO. 5724 | 109-GlyTyrLeuTyrAsnGlyValHisGlu-117 |
| SEQ. ID. NO. 5725 | 138-ArgGlnValAspGlyLeuMetSerAlaIleTyr-148 |
| SEQ. ID. NO. 5726 | 182-ArgPheGluArgHisCys-187 |
| SEQ. ID. NO. 5727 | 194-ProGluAlaGlyArgLysTyrTyrArgAsnAla-204 |
| SEQ. ID. NO. 5728 | 281-ArgProValArgValLeuThrAlaGly-289 |
| SEQ. ID. NO. 5729 | 315-TyrThrAlaValPheAspTyrValArgAsnGlyArgArgAla-328 |

TABLE 1-continued

| | |
|---|---|
| Antigenic Index - Jameson-Wolf | |
| SEQ. ID. NO. 5730 | 21-ThrGlnAsnGlnSerLeuProAlaGly-29 |
| SEQ. ID. NO. 5731 | 32-ValTyrProSerAlaProGlnIleArgAspGlyGlyAspAla-45 |
| SEQ. ID. NO. 5732 | 69-AsnSerAlaArgArgHisAlaSer-76 |
| SEQ. ID. NO. 5733 | 80-LeuAsnProGluAspGlyHisGlyGluHisHisProAspAsnProHis-95 |
| SEQ. ID. NO. 5734 | 99-GlnLysLeuThrGluArgThrArgLeu-107 |
| SEQ. ID. NO. 5735 | 115-ValHisGluAsnIleSerThrGluGluGluAlaAlaGluSerSerAspSerAspIleArgThrGlnGlnArgGlnValAspGlyLeu-143 |
| SEQ. ID. NO. 5736 | 152-SerLeuLeuAspArgHisThrAspGluAlaGly-162 |
| SEQ. ID. NO. 5737 | 165-PheValArgGluAsnGlyLysThr-172 |
| SEQ. ID. NO. 5738 | 178-GlnGlyAsnGlyArgPheGluArgHisCysAlaGlnGlyArgAsnGlnProGluAlaGlyArgLysTyrTyrArgAsnAlaCysHisAsnGly-208 |
| SEQ. ID. NO. 5739 | 212-TyrThrAspGluAlaMetPro-218 |
| SEQ. ID. NO. 5740 | 237-PheHisGlyGluArgProAspProValProGluTyrGluIleThrGlyAsnProAlaSer-256 |
| SEQ. ID. NO. 5741 | 258-AspPheSerGluAlaAlaGly-264 |
| SEQ. ID. NO. 5742 | 266-IleThrMetLysSer-270 |
| SEQ. ID. NO. 5743 | 274-TyrGlnGlyLysAsnGluIleArgPro-282 |
| SEQ. ID. NO. 5744 | 287-ThrAlaGlyAsnAspProAsnGlyArgLeuThr-297 |
| SEQ. ID. NO. 5745 | 320-AspTyrValArgAsnGlyArgArgAlaGlnAla-330 |
| SEQ. ID. NO. 5746 | 334-PheArgThrArgLysProAspTyrProTyr-343 |
| SEQ. ID. NO. 5747 | 345-GluValAsnGlyGlyGluThrLeuAlaValArgLysGlyGluLys-359 |
| SEQ. ID. NO. 5748 | 364-TrpArgGlyArgTrpCysLeu-370 |
| SEQ. ID. NO. 5749 | 376-TyrThrTyrArgGlnArgProGlySerArgLeuSerIleGlyArgHisGluAlaGlyGly-395 |
| SEQ. ID. NO. 5750 | 401-AspGlyMetAlaGlySer-406 |
| SEQ. ID. NO. 5751 | 408-IleThrLeuAlaProGluGlyGluThrGluArgGly-419 |
| Hydrophilic Regions - Hopp-Woods | |
| SEQ. ID. NO. 5752 | 37-ProGlnIleArgAspGlyGlyAsp-44 |
| SEQ. ID. NO. 5753 | 69-AsnSerAlaArgArgHisAla-75 |
| SEQ. ID. NO. 5754 | 81-AsnProGluAspGlyHisGlyGluHisHisProAsp-92 |
| SEQ. ID. NO. 5755 | 100-LysLeuThrGluArgThrArgLeu-107 |
| SEQ. ID. NO. 5756 | 119-IleSerThrGluGluGluAlaAlaGluSerSerAspSerAspIleArgThrGlnGlnArgGlnValAsp-141 |
| SEQ. ID. NO. 5757 | 152-SerLeuLeuAspArgHisThrAspGluAlaGly-162 |
| SEQ. ID. NO. 5758 | 165-PheValArgGluAsnGlyLys-171 |
| SEQ. ID. NO. 5759 | 179-GlyAsnGlyArgPheGluArgHisCysAlaGlnGlyArgAsnGlnProGluAlaGlyArgLysTyrTyrArg-202 |
| SEQ. ID. NO. 5760 | 238-HisGlyGluArgProAspProValProGlu-247 |
| SEQ. ID. NO. 5761 | 258-AspPheSerGluAlaAlaGly-264 |
| SEQ. ID. NO. 5762 | 266-IleThrMetLysSer-270 |
| SEQ. ID. NO. 5763 | 275-GlnGlyLysAsnGluIleArgPro-282 |
| SEQ. ID. NO. 5764 | 289-GlyAsnAspProAsnGlyArg-295 |
| SEQ. ID. NO. 5765 | 323-ArgAsnGlyArgArgAlaGlnAla-330 |
| SEQ. ID. NO. 5766 | 334PheArgThrArgLysProAsp-340 |
| SEQ. ID. NO. 5767 | 352-LeuAlaValArgLysGlyGluLys-359 |
| SEQ. ID. NO. 5768 | 377-ThrTyrArgGlnArgProGlySer-384 |
| SEQ. ID. NO. 5769 | 387-SerIleGlyArgHisGluAla-393 |
| SEQ. ID. NO. 5770 | 412-ProGluGlyGluThrGluArgGly-419 |
| 538-2 | |
| AMPHI Regions - AMPHI | |
| SEQ. ID. NO. 5771 | 42-ThrAlaLeuAlaGluAlaValGluLeuValLysAlaAlaGly-55 |
| SEQ. ID. NO. 5772 | 79-LysAlaAlaGluLeuSerGluAlaValAla-88 |
| SEQ. ID. NO. 5773 | 145-GlnLeuSerHisLeuAlaGlyArgLeuIleArgGlyTyrGlyHisLeuGln-161 |
| SEQ. ID. NO. 5774 | 188-IleAsnAlaLeuLysLysGlnLeuAla-196 |
| SEQ. ID. NO. 5775 | 211-SerGlyThrIleLysThrPheAlaLeuValGlyTyrThrAsn-224 |
| SEQ. ID. NO. 5776 | 231-PheAsnArgLeuThrLys-236 |
| SEQ. ID. NO. 5777 | 271-GlyPheValSerAspLeuProHisLysLeuIleSerAlaPheSerAlaThrLeuGlu-289 |
| SEQ. ID. NO. 5778 | 307-AsnSerGlyGlnGlnIleGluAspValGluAsnValLeuGlnGluIleHis-323 |
| SEQ. ID. NO. 5779 | 365-GluAsnThrGlyIleAspAlaLeuArgGluAlaIleAlaGluSerCysAla-381 |
| Antigenic Index - Jameson-Wolf | |
| SEQ. ID. NO. 5780 | 1-MetThrGlyArgThrGlyGlyAsnGlySerThrGlnAlaGlnProGluArg-17 |
| SEQ. ID. NO. 5781 | 24-MetLeuAspLysAspGlyThrGlySerSerAlaAlaArg-36 |
| SEQ. ID. NO. 5782 | 48-ValGluLeuValLys-52 |
| SEQ. ID. NO. 5783 | 54-AlaGlyGlyAspSerValArgValGluThrAlaLysArgAspArgProHisThr-71 |
| SEQ. ID. NO. 5784 | 77-ThrGlyLysAlaAlaGluLeuSerGlu-85 |
| SEQ. ID. NO. 5785 | 100-GluLeuThrProThrGlnGluArgAsnLeuGluLysGluLeuLysCysArgValLeuAsp-119 |
| SEQ. ID. NO. 5786 | 129-AlaArgArgAlaArgThrGlnGluGlyArgLeuGlnVal-141 |
| SEQ. ID. NO. 5787 | 161-GlnSerGlnArgGlyGlyIleGlyMetLysGlyProGlyGluThrLysLeuGluThrAspArgArgLeuIle-184 |
| SEQ. ID. NO. 5788 | 189-AsnAlaLeuLysLysGlnLeuAlaAsnLeuLysLysGlnArgAlaLeuArgArgLysSerArgGluSerGlyThrIleLysThr-216 |
| SEQ. ID. NO. 5789 | 224-AsnValGlyLysSerSerLeu-230 |
| SEQ. ID. NO. 5790 | 233-ArgLeuThrLysSerGlyIleTyrAla-241 |
| SEQ. ID. NO. 5791 | 257-TyrIleSerProGluCys-262 |
| SEQ. ID. NO. 5792 | 287-ThrLeuGluGluThrAlaGln-293 |
| SEQ. ID. NO. 5793 | 304-AlaAlaProAsnSerGlyGlnGlnIleGluAspValGluAsnValLeu-319 |
| SEQ. ID. NO. 5794 | 323-HisAlaGlyAspIlePro-328 |
| SEQ. ID. NO. 5795 | 333-TyrAsnLysThrAspLeuLeuProSerGluGluGlnAsnThrGlyIle-348 |
| SEQ. ID. NO. 5796 | 365-GluAsnThrGlyIleAspAlaLeuArgGluAlaIleAla-377 |
| SEQ. ID. NO. 5797 | 380-CysAlaAlaAlaProAsnThrAspGluThrGluMetPro-392 |
| Hydrophilic Regions - Hopp-Woods | |
| SEQ. ID. NO. 5798 | 1-MetThrGlyArgThrGlyGly-7 |
| SEQ. ID. NO. 5799 | 13-AlaGlnProGluArg-17 |
| SEQ. ID. NO. 5800 | 25-LeuAspLysAspGlyThrGly-31 |
| SEQ. ID. NO. 5801 | 48-ValGluLeuValLys-52 |
| SEQ. ID. NO. 5802 | 54-AlaGlyGlyAspSerValArgValGluThrAlaLysArgAspArgProHis-70 |
| SEQ. ID. NO. 5803 | 78-GlyLysAlaAlaGluLeuSerGlu-85 |

TABLE 1-continued

| | |
|---|---|
| SEQ. ID. NO. 5804 | 101-LeuThrProThrGlnGluArgAsnLeuGluLysGluLeuLysCysArgValLeuAsp-119 |
| SEQ. ID. NO. 5805 | 129-AlaArgArgAlaArgThrGlnGluGlyArgLeuGlnVal-141 |
| SEQ. ID. NO. 5806 | 161-GlnSerGlnArgGlyGlyIle-167 |
| SEQ. ID. NO. 5807 | 171-GlyProGlyGluThrLysLeuGluThrAspArgArgLeuIle-184 |
| SEQ. ID. NO. 5808 | 189-AsnAlaLeuLysLysGlnLeuAlaAsnLeuLysLysGlnArgAlaLeuArgArgLysSerArgGluSerGlyThr-213 |
| SEQ. ID. NO. 5809 | 287-ThrLeuGluGluThrAlaGln-293 |
| SEQ. ID. NO. 5810 | 310-GlnGlnIleGluAspValGluAsnValLeu-319 |
| SEQ. ID. NO. 5811 | 337-AspLeuLeuProSerGluGluGlnAsn-345 |
| SEQ. ID. NO. 5812 | 370-AspAlaLeuArgGluAlaIleAla-377 |
| SEQ. ID. NO. 5813 | 384-ProAsnThrAspGluThrGluMetPro-392 |
| 539-2 | |
| AMPHI Regions - AMPHI | |
| SEQ. ID. NO. 5814 | 18-ArgGlnArgGluHisHisArgLeu-25 |
| SEQ. ID. NO. 5815 | 44-LeuValGlyGlyPheAspPheLeuArgValIleGlyCysGlyGlyValAlaTyrLeuProAspPheGlnGln-67 |
| Antigenic Index - Jameson-Wolf | |
| SEQ. ID. NO. 5816 | 1-MetGluAspLeuGlnGluIleGly-8 |
| SEQ. ID. NO. 5817 | 15-LysValGlyArgGlnArgGluHisHisArgLeuHisHisProGlnProGlyAsnGlyGluAlaAspAsp-37 |
| SEQ. ID. NO. 5818 | 63-ProAspPheGlnGlnAsnValGlyLysAlaAsp-73 |
| SEQ. ID. NO. 5819 | 77-ValProAspAspAlaAlaAla-83 |
| SEQ. ID. NO. 5820 | 88-IleGluValAspAlaAspAspAlaValCys-97 |
| SEQ. ID. NO. 5821 | 102-LeuPheAspGlnProAspAlaGlyGlyAlaGlyAspAlaAlaGluHis-117 |
| Hydrophilic Regions - Hopp-Woods | |
| SEQ. ID. NO. 5822 | 1-MetGluAspLeuGlnGluIleGly-8 |
| SEQ. ID. NO. 5823 | 15-LysValGlyArgGlnArgGluHisHisArg-24 |
| SEQ. ID. NO. 5824 | 31-GlyAsnGlyGluAlaAspAsp-37 |
| SEQ. ID. NO. 5825 | 69-ValGlyLysAlaAsp-73 |
| SEQ. ID. NO. 5826 | 78-ProAspAspAlaAlaAla-83 |
| SEQ. ID. NO. 5827 | 88-IleGluValAspAlaAspAspAlaValCys-97 |
| SEQ. ID. NO. 5828 | 102-LeuPheAspGlnProAspAlaGlyGlyAlaGlyAspAlaAlaGluHis-117 |
| 542-2 | |
| AMPHI Regions - AMPHI | |
| SEQ. ID. NO. 5829 | 6-ArgIleArgArgCysSerVal-12 |
| Antigenic Index - Jameson-Wolf | |
| SEQ. ID. NO. 5830 | 1-MetProLysTrpSerArgIleArgArgCysSerVal-12 |
| SEQ. ID. NO. 5831 | 37-ValArgLeuLysSerSerAspGlyIleAlaSer-47 |
| SEQ. ID. NO. 5832 | 56-GlyProMetProSerGluThrValSerHisLysSerAspSerSerArgAsnThrSerAlaSerArgArgAsnValSerProLysCysProPhe-86 |
| SEQ. ID. NO. 5833 | 90-PheArgGlnAspAlaAlaLysProArgArgPheGlyGlyLys-103 |
| SEQ. ID. NO. 5834 | 107-LeuThrGlySerArg-111 |
| Hydrophilic Regions - Hopp-Woods | |
| SEQ. ID. NO. 5835 | 5-SerArgIleArgArgCysSer-11 |
| SEQ. ID. NO. 5836 | 37-ValArgLeuLysSerSerAspGlyIleAla-46 |
| SEQ. ID. NO. 5837 | 58-MetProSerGluThrValSerHisLysSerAspSerSerArgAsnThrSerAlaSerArgArgAsnValSerPro-82 |
| SEQ. ID. NO. 5838 | 90-PheArgGlnAspAlaAlaLysProArgArgPheGlyGly-102 |
| 544-2 | |
| AMPHI Regions - AMPHI | |
| SEQ. ID. NO. 5839 | 11-AlaLeuIleGlyIleLeu-16 |
| SEQ. ID. NO. 5840 | 55-PheTrpPheProSerCysProGlyCysValSerGluMetProLysIleIleLysThrAla-74 |
| SEQ. ID. NO. 5841 | 85-LeuAlaValAlaGlnProIleAspProIleGluSerValArgGlnTyrVal-101 |
| SEQ. ID. NO. 5842 | 116-LysAlaValGlyGlnAlaPhe-122 |
| Antigenic Index - Jameson-Wolf | |
| SEQ. ID. NO. 5843 | 1-MetLysLysIleLeu-5 |
| SEQ. ID. NO. 5844 | 22-IleProAspSerLysThrAlaPro-29 |
| SEQ. ID. NO. 5845 | 35-AspLeuHisGlyLysThrValSerAsnAlaAspLeuGlnGly-48 |
| SEQ. ID. NO. 5846 | 59-SerCysProGlyCys-63 |
| SEQ. ID. NO. 5847 | 66-GluMetProLysIleIleLysThrAlaAsnAspTyrLysAsnLysAsnPhe-82 |
| SEQ. ID. NO. 5848 | 90-ProIleAspProIleGluSerValArgGlnTyrValLysAspTyrGly-105 |
| SEQ. ID. NO. 5849 | 113-AspAlaAspLysAlaVal-118 |
| SEQ. ID. NO. 5850 | 133-IleGlyLysLysGlyGluIleLeu-140 |
| SEQ. ID. NO. 5851 | 144-ValGlyGluProAspPheGlyLysLeuTyrGlnGluIleAspThrAlaTrpArgAsnSerAspAlaVal-166 |
| Hydrophilic Regions - Hopp-Woods | |
| SEQ. ID. NO. 5852 | 1-MetLysLysIleLeu-5 |
| SEQ. ID. NO. 5853 | 23-ProAspSerLysThr-27 |
| SEQ. ID. NO. 5854 | 66-GluMetProLysIleIleLysThrAlaAsnAspTyrLysAsnLysAsn-81 |
| SEQ. ID. NO. 5855 | 92-AspProIleGluSerValArgGlnTyrValLys-102 |
| SEQ. ID. NO. 5856 | 113-AspAlaAspLysAlaVal-118 |
| SEQ. ID. NO. 5857 | 133-IleGlyLysLysGlyGluIle-139 |
| SEQ. ID. NO. 5858 | 156-IleAspThrAlaTrpArgAsnSerAspAlaVal-166 |
| 547-2 | |
| AMPHI Regions - AMPHI | |
| SEQ. ID. NO. 5859 | 7-PheAsnLysThrValAlaSerPheAlaGlnIleValGluThrPheAspVal-23 |
| SEQ. ID. NO. 5860 | 62-AsnArgSerPheLys-66 |
| SEQ. ID. NO. 5861 | 105-LeuHisIlePheThrAsnIle-111 |
| SEQ. ID. NO. 5862 | 121-GluLeuLeuThrIleLeuValLys-128 |
| Antigenic Index - Jameson-Wolf | |
| SEQ. ID. NO. 5863 | 3-ValAspAsnGlyPheAsnLysThrVal-11 |
| SEQ. ID. NO. 5864 | 35-GlnMetLysGlnArgCysGly-41 |
| SEQ. ID. NO. 5865 | 53-PheProArgCysGlyPheGluIleProAsnArgSerPheLysGlu-67 |
| SEQ. ID. NO. 5866 | 76-LeuSerGluArgPheArgThrAsnAlaGluValGluMet-88 |
| SEQ. ID. NO. 5867 | 129-AsnLeuSerProAsnGlyLysLysArgPhe-138 |

TABLE 1-continued

| | |
|---|---|
| Hydrophilic Regions - Hopp-Woods | |
| SEQ. ID. NO. 5868 | 36-MetLysGlnArgCys-40 |
| SEQ. ID. NO. 5869 | 60-IleProAsnArgSerPheLysGlu-67 |
| SEQ. ID. NO. 5870 | 76-LeuSerGluArgPheArgThrAsnAlaGluValGluMet-88 |
| SEQ. ID. NO. 5871 | 130-LeuSerProAsnGlyLysLysArgPhe-138 |
| 548-2 (from 23) | |
| AMPHI Regions - AMPHI | |
| SEQ. ID. NO. 5872 | 14-ValLeuAlaAlaLeuAlaAlaCysLys-22 |
| SEQ. ID. NO. 5873 | 39-SerAlaAlaGluAsnAlaAlaLysPro-47 |
| SEQ. ID. NO. 5874 | 89-PheThrHisCysProAspValCysProThr-98 |
| SEQ. ID. NO. 5875 | 103-TyrSerAspThrLeuLysGlnLeuGlyGlyGln-113 |
| SEQ. ID. NO. 5876 | 132-GluIleIleGlyLysTyrAlaLys-139 |
| Antigenic Index - Jameson-Wolf | |
| SEQ. ID. NO. 5877 | 21-CysLysProGlnAspAsnSerAlaAla-29 |
| SEQ. ID. NO. 5878 | 39-SerAlaAlaGluAsnAlaAlaLysProGlnThrArgGlyThrAspMetArgLysGluAspIleGlyGlyAspPheThrLeuThrAspGlyGluGlyLysPro PheAsn-74 |
| SEQ. ID. NO. 5879 | 76-SerAspLeuLysGly-80 |
| SEQ. ID. NO. 5880 | 91-HisCysProAspValCysPro-97 |
| SEQ. ID. NO. 5881 | 104-SerAspThrLeuLysGlnLeuGlyGlyGlnAlaLysAspValLys-118 |
| SEQ. ID. NO. 5882 | 124-IleAspProGluArgAspThrProGluIleIleGlyLysTyrAlaLysGlnPheAsnProAspPhe-145 |
| SEQ. ID. NO. 5883 | 150-AlaThrGlyGlyGln-154 |
| SEQ. ID. NO. 5884 | 169-LysValAsnGlnLysAspAspSerGluAsnTyrLeu-180 |
| SEQ. ID. NO. 5885 | 189-LeuIleAspLysAsnGlyGlu-195 |
| SEQ. ID. NO. 5886 | 200-SerProTyrGlySerGluProGluThrIleAlaAlaAspVal-213 |
| Hydrophilic Regions - Hopp-Woods | |
| SEQ. ID. NO. 5887 | 22-LysProGlnAspAsnSerAla-28 |
| SEQ. ID. NO. 5888 | 39-SerAlaAlaGluAsnAlaAlaLysProGlnThrArgGlyThrAspMetArgLysGluAspIleGlyGly-61 |
| SEQ. ID. NO. 5889 | 64-ThrLeuThrAspGlyGluGlyLysPro-72 |
| SEQ. ID. NO. 5890 | 76-SerAspLeuLysGly-80 |
| SEQ. ID. NO. 5891 | 111-GlyGlyGlnAlaLysAspValLys-118 |
| SEQ. ID. NO. 5892 | 124-IleAspProGluArgAspThrProGluIleIle-134 |
| SEQ. ID. NO. 5893 | 169-LysValAsnGlnLysAspAspSerGluAsnTyrLeu-180 |
| SEQ. ID. NO. 5894 | 191-AspLysAsnGlyGlu-195 |
| SEQ. ID. NO. 5895 | 203-GlySerGluProGluThrIleAlaAlaAspVal-213 |
| 548-2 (from earlier--to be deleted) | |
| AMPHI Regions - AMPHI | |
| SEQ. ID. NO. 5896 | 14-ValLeuAlaAlaLeuAlaAlaCysLys-22 |
| SEQ. ID. NO. 5897 | 39-SerAlaAlaGluAsnAlaAlaLysPro-47 |
| SEQ. ID. NO. 5898 | 89-PheThrHisCysProAspValCysProThr-98 |
| SEQ. ID. NO. 5899 | 103-TyrSerAspThrLeuLysGlnLeuGlyGlyGln-113 |
| SEQ. ID. NO. 5900 | 132-GluIleIleGlyLysTyrAlaLys-139 |
| Antigenic Index - Jameson-Wolf | |
| SEQ. ID. NO. 5901 | 21-CysLysProGlnAspAsnSerAlaAla-29 |
| SEQ. ID. NO. 5902 | 39-SerAlaAlaGluAsnAlaAlaLysProGlnThrArgGlyThrAspMetArgLysGluAspIleGlyGlyAspPheThrLeuThrAspGlyGluGlyLysPro PheAsn-74 |
| SEQ. ID. NO. 5903 | 76-SerAspLeuLysGly-80 |
| SEQ. ID. NO. 5904 | 91-HisCysProAspValCysPro-97 |
| SEQ. ID. NO. 5905 | 104-SerAspThrLeuLysGlnLeuGlyGlyGlnAlaLysAspValLys-118 |
| SEQ. ID. NO. 5906 | 124-IleAspProGluArgAspThrProGluIleIleGlyLysTyrAlaLysGlnPheAsnProAspPhe-145 |
| SEQ. ID. NO. 5907 | 150-AlaThrGlyGlyGln-154 |
| SEQ. ID. NO. 5908 | 169-LysValAsnGlnLysAspAspSerGluAsnTyrLeu-180 |
| SEQ. ID. NO. 5909 | 189-LeuIleAspLysAsnGlyGlu-195 |
| SEQ. ID. NO. 5910 | 200-SerProTyrGlySerGluProGluThrIleAlaAlaAspVal-213 |
| Hydrophilic Regions - Hopp-Woods | |
| SEQ. ID. NO. 5911 | 22-LysProGlnAspAsnSerAla-28 |
| SEQ. ID. NO. 5912 | 39-SerAlaAlaGluAsnAlaAlaLysProGlnThrArgGlyThrAspMetArgLysGluAspIleGlyGly-61 |
| SEQ. ID. NO. 5913 | 64-ThrLeuThrAspGlyGluGlyLysPro-72 |
| SEQ. ID. NO. 5914 | 76-SerAspLeuLysGly-80 |
| SEQ. ID. NO. 5915 | 111-GlyGlyGlnAlaLysAspValLys-118 |
| SEQ. ID. NO. 5916 | 124-IleAspProGluArgAspThrProGluIleIle-134 |
| SEQ. ID. NO. 5917 | 169-LysValAsnGlnLysAspAspSerGluAsnTyrLeu-180 |
| SEQ. ID. NO. 5918 | 191-AspLysAsnGlyGlu-195 |
| SEQ. ID. NO. 5919 | 203-GlySerGluProGluThrIleAlaAlaAspVal-213 |
| 552-1 | |
| AMPHI Regions - AMPHI | |
| SEQ. ID. NO. 5920 | 18-CysThrAsnAlaPheAlaAlaPro-25 |
| SEQ. ID. NO. 5921 | 29-AlaSerLeuAlaArgTrpLeuAspThr-37 |
| SEQ. ID. NO. 5922 | 41-AspArgAspIleGluLysAsnMetIleGluGlyPheAsnAlaGlyPheLysProTyrAlaAspLysAlaLeuAlaGluMet-67 |
| SEQ. ID. NO. 5923 | 75-AlaAlaGluAlaPheAsnArgTyrArgGluAsnVal-86 |
| SEQ. ID. NO. 5924 | 89-AspLeuIleThrProGluValLys-96 |
| SEQ. ID. NO. 5925 | 116-IleAspGlyMetIleAla-121 |
| SEQ. ID. NO. 5926 | 139-IleLysLysSerMetSerGluIle-146 |
| SEQ. ID. NO. 5927 | 154-SerGlyLysIleAlaGlnHisHisLeuProGluPheThrGluGluLeuArgArg-171 |
| Antigenic Index - Jameson-Wolf | |
| SEQ. ID. NO. 5928 | 25-ProProSerAspAlaSerLeu-31 |
| SEQ. ID. NO. 5929 | 35-LeuAspThrGlnAsnPheAspArgAspIleGluLysAsnMetIle-49 |
| SEQ. ID. NO. 5930 | 58-ProTyrAlaAspLysAlaLeuAlaGluMetProGluAlaLysLysAspGlnAlaAla-76 |
| SEQ. ID. NO. 5931 | 78-AlaPheAsnArgTyrArgGluAsnValLeu-87 |
| SEQ. ID. NO. 5932 | 90-LeuIleThrProGluValLysGlnAlaVal-99 |
| SEQ. ID. NO. 5933 | 105-LysAsnAlaArgGluIleTyrThrGlnGluGluIleAspGly-118 |

TABLE 1-continued

SEQ. ID. NO. 5934 131-ValValAlaLysAsnProArgLeuIleLysLysSerMetSer-144
SEQ. ID. NO. 5935 153-LeuSerGlyLysIle-157
SEQ. ID. NO. 5936 164-GluPheThrGluGluLeuArgArg-171
SEQ. ID. NO. 5937 173-IleCysGlyGlyLysAsnProAspAlaGlyCysLysGlnAlaGlyGlnValGlyLysArgHisGlnLys-195
Hydrophilic Regions - Hopp-Woods
SEQ. ID. NO. 5938 26-ProSerAspAlaSerLeu-31
SEQ. ID. NO. 5939 38-GlnAsnPheAspArgAspIleGluLysAsnMetIle-49
SEQ. ID. NO. 5940 58-ProTyrAlaAspLysAlaLeuAlaGluMetProGluAlaLysLysAspGlnAlaAla-76
SEQ. ID. NO. 5941 78-AlaPheAsnArgTyrArgGluAsnValLeu-87
SEQ. ID. NO. 5942 90-LeuIleThrProGluValLysGlnAlaVal-99
SEQ. ID. NO. 5943 105-LysAsnAlaArgGluIleTyrThr-112
SEQ. ID. NO. 5944 114-GluGluIleAspGly-118
SEQ. ID. NO. 5945 131-ValValAlaLysAsnProArgLeuIleLysLysSerMetSer-144
SEQ. ID. NO. 5946 164-GluPheThrGluGluLeuArgArg-171
SEQ. ID. NO. 5947 176-GlyLysAsnProAspAlaGlyCysLysGlnAlaGlyGlnValGlyLysArgHisGlnLys-195
553-2
AMPHI Regions - AMPHI
SEQ. ID. NO. 5948 31-LeuThrSerIleLeuSerTyrTyrGly-39
SEQ. ID. NO. 5949 59-AsnLeuAlaAspIleMetArgPheGlyAsn-68
SEQ. ID. NO. 5950 83-GluLeuSerAsnLeu-87
Antigenic Index - Jameson-Wolf
SEQ. ID. NO. 5951 10-GlyPheAsnLysLysLeuPro-16
SEQ. ID. NO. 5952 42-ThrAspLeuArgThrLeuArgGlnLysTyr-51
SEQ. ID. NO. 5953 56-LysGlyAlaAsnLeu-60
SEQ. ID. NO. 5954 65-ArgPheGlyAsnGluMetAsnLeuThrProArgAlaLeuArgLeuGluLeu
AspGluLeuSerAsn-86
SEQ. ID. NO. 5955 105-SerIleSerLysAspSerIle-111
SEQ. ID. NO. 5956 116-ProAlaValGlyMetArgLysIleLysMetAspGluValSerGlnLys-131
SEQ. ID. NO. 5957 143-ThrHisPheGluGluLysLysGluThrLysLysIleLys-155
SEQ. ID. NO. 5958 160-LeuArgGlyGlyGlnAla-165
Hydrophilic Regions - Hopp-Woods
SEQ. ID. NO. 5959 42-ThrAspLeuArgThrLeuArgGln-49
SEQ. ID. NO. 5960 75-ArgAlaLeuArgLeuGluLeuAspGluLeuSer-85
SEQ. ID. NO. 5961 106-IleSerLysAspSer-110
SEQ. ID. NO. 5962 118-ValGlyMetArgLysIleLysMetAspGluValSerGln-130
SEQ. ID. NO. 5963 144-HisPheGluGluLysLysGluThrLysLysIleLys-155
554
AMPHI Regions - AMPHI
SEQ. ID. NO. 5964 35-AlaProThrPheGlnThrProGluThrLeu-44
SEQ. ID. NO. 5965 71-AlaAlaLeuThrGlnLeuMet-77
SEQ. ID. NO. 5966 110-ArgMetPheValArgProGlyAspThrVal-119
SEQ. ID. NO. 5967 124-LeuLeuLysGlyMet-128
SEQ. ID. NO. 5968 148-SerIleGluAsnPheValGlnGlnMetAsnLysGlu-159
SEQ. ID. NO. 5969 193-GluAlaLeuMetArgAspPheProGluTyrTyrProLeuPheSer-207
SEQ. ID. NO. 5970 296-ThrValAlaGlnIle-300
SEQ. ID. NO. 5971 331-GluGlnIleLeuGluThrIleGlnProIleProAla-342
Antigenic Index - Jameson-Wolf
SEQ. ID. NO. 5972 24-SerProAlaProAsnArgProThrVal-32
SEQ. ID. NO. 5973 37-ThrPheGlnThrProGluThr-43
SEQ. ID. NO. 5974 53-LeuGlnSerLysGln-57
SEQ. ID. NO. 5975 61-AlaLysAsnIleAsnThrProValGlu-69
SEQ. ID. NO. 5976 84-LysAsnMetLysSerGlyAsnIleGlnSerGluGluAsnLeuLysIleProGlu-101
SEQ. ID. NO. 5977 104-TrpAlaSerGluGlySerArgMetPheValArgProGlyAspThrValSerThrAspLysLeuLeu-125
SEQ. ID. NO. 5978 143-ArgLeuGlyAsnGlySerIleGluAsnPhe-152
SEQ. ID. NO. 5979 156-MetAsnLysGluAlaArgArgLeuGlyMetLysAsnThrValPheLysAsnProThrGlyLeuSerArgGluGlyGlnValSerThrAlaLysAsp-187
SEQ. ID. NO. 5980 194-AlaLeuMetArgAspPheProGluTyrTyr-203
SEQ. ID. NO. 5981 214-LysAsnIleGluGlnAsnAsnArgAsnIleLeu-224
SEQ. ID. NO. 5982 226-TyrArgAspAsnAsnValAsnGlyLeuLysAlaGlyHisThrGluSerGlyGlyTyrAsn-245
SEQ. ID. NO. 5983 250-TyrSerGlyAsnGlyArgHis-256
SEQ. ID. NO. 5984 262-LeuGlySerGluSerAlaGluThrArgAlaSerAspAsnSerLys-276
SEQ. ID. NO. 5985 285-PheAspThrProLysIleTyrProLysGlyLysThr-296
SEQ. ID. NO. 5986 302-IleSerGlyGlySerLysLysThrValArg-311
SEQ. ID. NO. 5987 323-ProHisLysGluAlaLysMetAlaGluGlnIleLeu-334
SEQ. ID. NO. 5988 342-AlaProValLysLysGlyGlnIleLeuGlyLysIleLysIleArgGlnAsnGlyTyr-360
SEQ. ID. NO. 5989 362-IleAlaGluLysGluIleValAla-369
SEQ. ID. NO. 5990 371-GluAsnValLysLysArgSerArgTrpGlnArg-381
Hydrophilic Regions - Hopp-Woods
SEQ. ID. NO. 5991 26-AlaProAsnArgProThr-31
SEQ. ID. NO. 5992 85-AsnMetLysSerGlyAsnIleGlnSerGluGluAsnLeuLysIleProGlu-101
SEQ. ID. NO. 5993 107-GluGlySerArgMetPheValArgProGlyAspThrValSerThrAspLysLeuLeu-125
SEQ. ID. NO. 5994 156-MetAsnLysGluAlaArgArgLeuGlyMet-165
SEQ. ID. NO. 5995 174-ThrGlyLeuSerArgGluGlyGlnValSerThrAlaLysAsp-187
SEQ. ID. NO. 5996 214-LysAsnIleGluGlnAsnAsnArg-221
SEQ. ID. NO. 5997 227-ArgAspAsnAsnValAsn-232
SEQ. ID. NO. 5998 237-GlyHisThrGluSerGly-242
SEQ. ID. NO. 5999 264-SerGluSerAlaGluThrArgAlaSerAspAsnSerLys-276
SEQ. ID. NO. 6000 289-LysIleTyrProLysGlyLysThr-296
SEQ. ID. NO. 6001 304-GlyGlySerLysLysThrValArg-311
SEQ. ID. NO. 6002 323-ProHisLysGluAlaLysMetAlaGluGlnIleLeu-334
SEQ. ID. NO. 6003 343-ProValLysLysGlyGlnIle-349

| | |
|---|---|
| SEQ. ID. NO. 6004 | 353-IleLysIleArgGln-357 |
| SEQ. ID. NO. 6005 | 362-IleAlaGluLysGluIleValAla-369 |
| SEQ. ID. NO. 6006 | 371-GluAsnValLysLysArgSerArgTrp-379 |
| 556 | |
| AMPHI Regions - AMPHI | |
| SEQ. ID. NO. 6007 | 61-IleGluArgLeuLys-65 |
| Antigenic Index - Jameson-Wolf | |
| SEQ. ID. NO. 6008 | 1-MetAspAsnLysThrLysLeuArgLeu-9 |
| SEQ. ID. NO. 6009 | 52-ThrSerArgArgGlnGlnArgGlnPheIleGluArgLeuLysLysPheAspIleAspProGluLysGlyArgIleAsnGluAlaAsnLeuArgArgMetTyr HisSerGlyGlyGlnHisGlnLysAspAla-95 |
| SEQ. ID. NO. 6010 | 102-SerGlnLysCysSerValAspGluAlaHisAlaMetPheLysLysArgProThrArgGlnGluIleAsn-124 |
| SEQ. ID. NO. 6011 | 127-AlaAlaLysGlnSerArgGlyGlnLysArgProHisArg-139 |
| Hydrophilic Regions - Hopp-Woods | |
| SEQ. ID. NO. 6012 | 1-MetAspAsnLysThrLysLeuArgLeu-9 |
| SEQ. ID. NO. 6013 | 53-SerArgArgGlnGlnArgGlnPheIleGluArgLeuLysLysPheAspIleAspProGluLysGlyArgIleAsnGluAlaAsnLeuArgArgMetTyr-85 |
| SEQ. ID. NO. 6014 | 90-GlnHisGlnLysAspAla-95 |
| SEQ. ID. NO. 6015 | 105-CysSerValAspGluAlaHisAlaMetPheLysLysArgProThrArgGlnGluIleAsn-124 |
| SEQ. ID. NO. 6016 | 127-AlaAlaLysGlnSerArgGlyGlnLysArgProHisArg-139 |
| 557 | |
| AMPHI Regions - AMPHI | |
| SEQ. ID. NO. 6017 | 22-GlyAlaAspGlyIle-26 |
| SEQ. ID. NO. 6018 | 55-SerGlyArgValAspAspAlaAla-62 |
| Antigenic Index - Jameson-Wolf | |
| SEQ. ID. NO. 6019 | 20-LeuLysGlyAlaAspGlyIleSerProProLeuThrTyrArgSerTrpHisIleGluGlyGlyGlnAlaLeuArg-44 |
| SEQ. ID. NO. 6020 | 54-AlaSerGlyArgValAspAspAlaAlaGly-63 |
| SEQ. ID. NO. 6021 | 68-LeuArgIleAspSerValSerGlnAsnLysGluThrTyrThr-81 |
| SEQ. ID. NO. 6022 | 100-GlnValLeuLysArgGlyGluProValGlyLysProMet-112 |
| SEQ. ID. NO. 6023 | 123-AlaAspAsnGluIleLeuGlyLysGlnGluGluGluAla-135 |
| SEQ. ID. NO. 6024 | 141-MetArgGlnAspAlaAlaGluGlnIleValArg-151 |
| Hydrophilic Regions - Hopp-Woods | |
| SEQ. ID. NO. 6025 | 21-LysGlyAlaAspGlyIle-26 |
| SEQ. ID. NO. 6026 | 56-GlyArgValAspAspAlaAlaGly-63 |
| SEQ. ID. NO. 6027 | 68-LeuArgIleAspSerValSerGlnAsnLysGluThrTyrThr-81 |
| SEQ. ID. NO. 6028 | 100-GlnValLeuLysArgGlyGluProValGly-109 |
| SEQ. ID. NO. 6029 | 126-GluIleLeuGlyLysGlnGluGluGluAla-135 |
| SEQ. ID. NO. 6030 | 141-MetArgGlnAspAlaAlaGluGlnIleValArg-151 |
| 560 | |
| AMPHI Regions - AMPHI | |
| SEQ. ID. NO. 6031 | 30-PheArgAspGlyAlaHisLysMetAlaArgValTrpValGly-43 |
| SEQ. ID. NO. 6032 | 167-ArgMetAlaLysMetPhe-172 |
| SEQ. ID. NO. 6033 | 192-PheLeuLysTyrProGlyGlu-198 |
| SEQ. ID. NO. 6034 | 216-GluLeuMetGluLysCysGluHisLeuIleGlu-226 |
| Antigenic Index - Jameson-Wolf | |
| SEQ. ID. NO. 6035 | 29-ProPheArgAspGlyAlaHisLysMet-37 |
| SEQ. ID. NO. 6036 | 61-GlyAlaGluAsnIleProAspArgProAla-70 |
| SEQ. ID. NO. 6037 | 76-HisGlnSerGlyTrpGlu-81 |
| SEQ. ID. NO. 6038 | 95-ValAlaLysArgGluLeuPhe-101 |
| SEQ. ID. NO. 6039 | 116-IleGlyIleAspArgAsnAsnArgArgGluAlaAsnGluGlnLeuIle-131 |
| SEQ. ID. NO. 6040 | 134-GlyLeuValArgLysAsnGluGlyTyr-142 |
| SEQ. ID. NO. 6041 | 148-ProGluGlyThrArgLeuAlaProGlyLysArgGlyLysTyrLysLeuGlyGly-165 |
| SEQ. ID. NO. 6042 | 182-AsnSerGlyGluPheTrpProLysAsnSerPheLeuLysTyrProGlyGluIle-199 |
| SEQ. ID. NO. 6043 | 209-HisAlaSerGlySerGluAlaGluLeuMetGluLysCysGluHisLeuIle-225 |
| SEQ. ID. NO. 6044 | 242-MetProSerGluThrAla-247 |
| Hydrophilic Regions - Hopp-Woods | |
| SEQ. ID. NO. 6045 | 29-ProPheArgAspGlyAlaHisLysMet-37 |
| SEQ. ID. NO. 6046 | 64-AsnIleProAspArgProAla-70 |
| SEQ. ID. NO. 6047 | 95-ValAlaLysArgGluLeuPhe-101 |
| SEQ. ID. NO. 6048 | 116-IleGlyIleAspArgAsnAsnArgArgGluAlaAsnGluGlnLeuIle-131 |
| SEQ. ID. NO. 6049 | 134-GlyLeuValArgLysAsnGlu-140 |
| SEQ. ID. NO. 6050 | 149-GluGlyThrArgLeuAlaProGlyLysArgGlyLysTyrLysLeuGlyGly-165 |
| SEQ. ID. NO. 6051 | 211-SerGlySerGluAlaGluLeuMetGluLysCysGluHisLeuIle-225 |
| SEQ. ID. NO. 6052 | 242-MetProSerGluThrAla-247 |
| 561 | |
| AMPHI Regions - AMPHI | |
| SEQ. ID. NO. 6053 | 22-GlyLeuTrpValGlyLeuAlaAla-29 |
| SEQ. ID. NO. 6054 | 46-AlaSerValIleGluGluAlaGlyAsn-54 |
| SEQ. ID. NO. 6055 | 79-ValAlaGluPheGluLysSerLeuLysArgIleAlaGln-91 |
| SEQ. ID. NO. 6056 | 128-SerTyrArgArgProThrGlnVal-135 |
| SEQ. ID. NO. 6057 | 172-MetThrLeuValSerSer-177 |
| SEQ. ID. NO. 6058 | 188-ValIleArgProLeuGlnAlaLeuArgGluGlyAlaGluArgIleGlyArgArgCysPheAspIle-209 |
| SEQ. ID. NO. 6059 | 219-PheLysGlnValGlyArgCysPheAsnGlnMet-229 |
| SEQ. ID. NO. 6060 | 238-AspAspLeuGluGlyGlnValAlaGluGlnThrArgSerLeuGluLysGln-254 |
| SEQ. ID. NO. 6061 | 265-ThrArgAspLeuHisGlnSer-271 |
| SEQ. ID. NO. 6062 | 275-GlnGlnAlaAlaGluHisPhe-281 |
| SEQ. ID. NO. 6063 | 283-AsnArgIleLeuPro-287 |
| SEQ. ID. NO. 6064 | 317-AlaSerAspLeuGlyLysTyrHisGlu-325 |
| SEQ. ID. NO. 6065 | 339-ArgLeuLeuLeuSerPheProAsnGly-347 |
| SEQ. ID. NO. 6066 | 358-LeuGlnThrLeuGlyArgGlnLeuGly-366 |
| SEQ. ID. NO. 6067 | 392-GlnGlyLeuHisAspSerIleAlaGlnAlaLeuThr-403 |
| SEQ. ID. NO. 6068 | 434-GlyValGlnGluCysTyrGluAspValArgGluLeu-445 |

TABLE 1-continued

| | |
|---|---|
| SEQ. ID. NO. 6069 | 456-LysGluPheProGluAlaValAlaAspLeuPheAlaArgPhe-469 |
| SEQ. ID. NO. 6070 | 504-LeuSerAsnIleArgLysHisAlaArg-512 |
| SEQ. ID. NO. 6071 | 540-ThrGluLysIleGlyGluProThr-547 |
| AntigenicIndex -Jameson-Wolf | |
| SEQ. ID. NO. 6072 | 6-ArgPheSerAspGlyIleSer-12 |
| SEQ. ID. NO. 6073 | 48-ValIleGluGluAlaGlyAsn-54 |
| SEQ. ID. NO. 6074 | 66-AlaGlyGluGlySerProArgAlaGlnIleAspAsnGlnValAlaGluPheGluLysSerLeuLysArgIleAlaGlnSerAspAlaIleHisPro-97 |
| SEQ. ID. NO. 6075 | 99-IleProSerAspThrProLeu-105 |
| SEQ. ID. NO. 6076 | 124-ProProLeuGlnSerTyrArgArgProThrGlnValAspLeu-137 |
| SEQ. ID. NO. 6077 | 152-GluAsnAlaAsnGluLysAsnThr-159 |
| SEQ. ID. NO. 6078 | 193-GlnAlaLeuArgGluGlyAlaGluArgIleGlyArgArgCysPheAsp-208 |
| SEQ. ID. NO. 6079 | 210-ProValProGluGlyGlyThrProGluPheLysGlnValGlyArgCysPheAsnGlnMetGlyGlyArgLeuLysIleLeuTyrAspAspLeuGluGly GlnValAlaGluGlnThrArgSerLeuGluLysGlnAsnGlnAsnLeu-258 |
| SEQ. ID. NO. 6080 | 263-GlnThrThrArgAspLeuHisGlnSerTyrIle-273 |
| SEQ. ID. NO. 6081 | 289-ValGlyAlaAspSerGlyArgValCysLeuAspGlyGlySerAsp-303 |
| SEQ. ID. NO. 6082 | 310-HisAlaAspCysGlyThrAlaAlaSerAspLeuGlyLysTyrHisGlu-325 |
| SEQ. ID. NO. 6083 | 332-TyrGlnAsnGluThrLeuGly-338 |
| SEQ. ID. NO. 6084 | 344-PheProAsnGlyIleSerLeuAspGluAspAspArgIleLeu-357 |
| SEQ. ID. NO. 6085 | 360-ThrLeuGlyArgGlnLeu-365 |
| SEQ. ID. NO. 6086 | 371-GlyAlaLysGlnGluGluGluLysArgLeu-380 |
| SEQ. ID. NO. 6087 | 384-LeuGlnGluArgAsnLeu-389 |
| SEQ. ID. NO. 6088 | 394-LeuHisAspSerIle-398 |
| SEQ. ID. NO. 6089 | 415-AlaPheAlaGluAsnLysArgGluGluAlaAlaGlu-426 |
| SEQ. ID. NO. 6090 | 434-GlyValGlnGluCysTyrGluAspValArgGlu-444 |
| SEQ. ID. NO. 6091 | 450-ArgThrLysIleSerAsnLysGluPheProGluAlaVal-462 |
| SEQ. ID. NO. 6092 | 480-AlaTrpGluAsnGlySer-485 |
| SEQ. ID. NO. 6093 | 488-ProProGlnGluAla-492 |
| SEQ. ID. NO. 6094 | 503-SerLeuSerAsnIleArgLysHisAlaArg-512 |
| SEQ. ID. NO. 6095 | 519-ThrLeuSerGluHisGlyGlyArgPhe-527 |
| SEQ. ID. NO. 6096 | 531-IleGlnAspAsnGlyGlnGlyPheAspThrGluLysIleGlyGluProThrGlySerHis-550 |
| SEQ. ID. NO. 6097 | 556-MetGlnGluArgAlaLysArgIle-563 |
| SEQ. ID. NO. 6098 | 568-GluIleArgSerGlnAlaGlnGlnGlyThrThr-578 |
| SEQ. ID. NO. 6099 | 584-AlaSerGluGluSerLeuLys-590 |
| Hydrophilic Regions - Hopp-Woods | |
| SEQ. ID. NO. 6100 | 48-ValIleGluGluAlaGlyAsn-54 |
| SEQ. ID. NO. 6101 | 68-GluGlySerProArgAlaGlnIle-75 |
| SEQ. ID. NO. 6102 | 78-GlnValAlaGluPheGluLysSerLeuLysArgIleAlaGln-91 |
| SEQ. ID. NO. 6103 | 128-SerTyrArgArgProThrGln-134 |
| SEQ. ID. NO. 6104 | 152-GluAsnAlaAsnGluLys-157 |
| SEQ. ID. NO. 6105 | 193-GlnAlaLeuArgGluGlyAlaGluArgIleGlyArgArgCysPhe-207 |
| SEQ. ID. NO. 6106 | 213-GluGlyGlyThrProGluPheLysGlnValGly-223 |
| SEQ. ID. NO. 6107 | 235-IleLeuTyrAspAspLeuGluGlyGlnValAlaGluGlnThrArgSerLeuGluLysGlnAsnGln-256 |
| SEQ. ID. NO. 6108 | 264-ThrThrArgAspLeuHis-269 |
| SEQ. ID. NO. 6109 | 290-GlyAlaAspSerGlyArgValCysLeu-298 |
| SEQ. ID. NO. 6110 | 312-AspCysGlyThrAlaAlaSerAspLeuGlyLysTyrHisGlu-325 |
| SEQ. ID. NO. 6111 | 349-SerLeuAspGluAspAspArgIleLeu-357 |
| SEQ. ID. NO. 6112 | 371-GlyAlaLysGlnGluGluGluLysArgLeu-380 |
| SEQ. ID. NO. 6113 | 384-LeuGlnGluArgAsnLeu-389 |
| SEQ. ID. NO. 6114 | 415-AlaPheAlaGluAsnLysArgGluGluAlaAlaGlu-426 |
| SEQ. ID. NO. 6115 | 437-GluCysTyrGluAspValArgGlu-444 |
| SEQ. ID. NO. 6116 | 451-ThrLysIleSerAsnLysGluPheProGluAlaVal-462 |
| SEQ. ID. NO. 6117 | 503-SerLeuSerAsnIleArgLysHisAlaArg-512 |
| SEQ. ID. NO. 6118 | 533-AspAsnGlyGlnGlyPheAspThrGluLysIleGlyGluProThrGly-548 |
| SEQ. ID. NO. 6119 | 556-MetGlnGluArgAlaLysArgIle-563 |
| SEQ. ID. NO. 6120 | 568-GluIleArgSerGlnAlaGln-574 |
| SEQ. ID. NO. 6121 | 584-AlaSerGluGluSerLeuLys-590 |
| 562 | |
| AMPHI Regions - AMPHI | |
| SEQ. ID. NO. 6122 | 48-TrpSerLeuValSerAlaTrpMetValValIle-58 |
| SEQ. ID. NO. 6123 | 84-LeuGluThrThrValMetSerAlaValArgThrLeu-95 |
| SEQ. ID. NO. 6124 | 97-PheThrProTyrThrThrValAlaSerThrSer-107 |
| SEQ. ID. NO. 6125 | 116-ThrPhePheAlaProLeuSerArgTrp-124 |
| SEQ. ID. NO. 6126 | 133-AsnAlaProValHisSerMetThrLysSerThrProSerSerPheHis-148 |
| SEQ. ID. NO. 6127 | 184-ValSerAsnLeuValArgTrpAlaLeu-192 |
| Antigenic Index - Jameson-Wolf | |
| SEQ. ID. NO. 6128 | 9-PheAsnSerGlySerThrLysProThr-17 |
| SEQ. ID. NO. 6129 | 32-ProLeuArgAlaArgArgArgSerLeuTrpArg-42 |
| SEQ. ID. NO. 6130 | 72-AlaThrGlyGluArgGlnLeuVal-79 |
| SEQ. ID. NO. 6131 | 105-SerThrSerSerProProGlyAlaGluMet-114 |
| SEQ. ID. NO. 6132 | 139-MetThrLysSerThrProSerSerPheHisGlySerSerAla-152 |
| SEQ. ID. NO. 6133 | 154-LeuArgValGluLysLysGlyIleLeuSerProLeuThr-166 |
| SEQ. ID. NO. 6134 | 168-ArgLeuProProSerTrpAspThrSerAlaSerLysArgProCysThr-183 |
| Hydrophilic Regions - Hopp-Woods | |
| SEQ. ID. NO. 6135 | 33-LeuArgAlaArgArgArgSerLeuTrp-41 |
| SEQ. ID. NO. 6136 | 72-AlaThrGlyGluArgGlnLeuVal-79 |
| SEQ. ID. NO. 6137 | 110-ProGlyAlaGluMet-114 |
| SEQ. ID. NO. 6138 | 140-ThrLysSerThrPro-144 |

TABLE 1-continued

| | |
|---|---|
| SEQ. ID. NO. 6139 | 154-LeuArgValGluLysLysGlyIle-161 |
| SEQ. ID. NO. 6140 | 176-SerAlaSerLysArgProCysThr-183 |
| 563 | |
| AMPHI Regions - AMPHI | |
| SEQ. ID. NO. 6141 | 24-ThrLysArgGluGlyLys-29 |
| SEQ. ID. NO. 6142 | 120-AsnGlnTyrAlaGlnPhe-125 |
| SEQ. ID. NO. 6143 | 164-ValAsnGlnIleAsnSerSerHisSerSer-173 |
| SEQ. ID. NO. 6144 | 246-AspPheThrArgIleLeuSerTyrHisSer-255 |
| SEQ. ID. NO. 6145 | 290-AlaAlaAsnThrSerAsnAsnThrAla-298 |
| SEQ. ID. NO. 6146 | 313-LysLeuGlyGlyMetTyr-318 |
| SEQ. ID. NO. 6147 | 366-LysAspThrAspAsn-370 |
| SEQ. ID. NO. 6148 | 443-AsnAsnGlnGlyLysLeu-448 |
| SEQ. ID. NO. 6149 | 483-SerSerAsnGlnThrGlyAsn-489 |
| SEQ. ID. NO. 6150 | 516-SerAsnIleThrAlaProThr-522 |
| SEQ. ID. NO. 6151 | 529-ArgThrHisGlyAlaLeuAsp-535 |
| SEQ. ID. NO. 6152 | 551-GlnGlnGlyLeuAsnAsnAlaGlyGlnIle-560 |
| SEQ. ID. NO. 6153 | 611-LeuAspAsnAlaHisGlyLysLeuLeuSerAla-621 |
| SEQ. ID. NO. 6154 | 736-LeuAspAsnAlaAlaGlnGly-742 |
| SEQ. ID. NO. 6155 | 775-GlnMetAsnAsnIleGlyThr-781 |
| SEQ. ID. NO. 6156 | 848-ThrGlyLysAlaGlnArgIleHisAsnAlaGlyAlaThrIleGlu-862 |
| SEQ. ID. NO. 6157 | 874-LeuHisAsnThrAsnGlu-879 |
| SEQ. ID. NO. 6158 | 896-TyrGluAlaPheGlyArg-901 |
| SEQ. ID. NO. 6159 | 922-SerAspHisLeuArgThrProAspGlyAlaAlaHisGluAsnTrp-936 |
| SEQ. ID. NO. 6160 | 953-ThrAlaProAlaLys-957 |
| SEQ. ID. NO. 6161 | 1011-LeuHisSerTyrTrpArg-1016 |
| SEQ. ID. NO. 6162 | 1036-GluGluIleThrArg-1040 |
| SEQ. ID. NO. 6163 | 1131-LeuHisLysArgLeuGlyAspGlyTyr-1139 |
| SEQ. ID. NO. 6164 | 1147-GluGlnIleAlaGluLeuThrGlyHisArgArgLeuAspGlyTyrGlnAsn-1163 |
| SEQ. ID. NO. 6165 | 1169-LysAlaLeuMetAsp-1173 |
| SEQ. ID. NO. 6166 | 1194-GlnValAlaGlnLeu-1198 |
| SEQ. ID. NO. 6167 | 1272-ThrLeuAspAsnIleGlyGly-1278 |
| SEQ. ID. NO. 6168 | 1289-AlaThrGlnAspIleAsnAsnIleGlyGlyMetLeu-1300 |
| SEQ. ID. NO. 6169 | 1376-GlnAlaGlyArgAspIle-1381 |
| SEQ. ID. NO. 6170 | 1403-IleArgGlySerThrAsnGluValGlySerSer-1413 |
| SEQ. ID. NO. 6171 | 1461-ValAspAspAlaSerLysHisThrGlyArg-1470 |
| SEQ. ID. NO. 6172 | 1485-SerHisHisGluThr-1489 |
| SEQ. ID. NO. 6173 | 1524-GlnAlaGlyAsnHisVal-1529 |
| SEQ. ID. NO. 6174 | 1539-GlnSerGluThrTyrHisGln-1545 |
| SEQ. ID. NO. 6175 | 1594-LysHisTyrGluGlnIleGlySerThrVal-1603 |
| SEQ. ID. NO. 6176 | 1646-ProValThrAspLeuAla-1651 |
| SEQ. ID. NO. 6177 | 1685-TyrGlnThrGlyLysSerAlaGlnAsnLeuAlaAsnGlyThrThrAsn-1700 |
| SEQ. ID. NO. 6178 | 1777-GluGlnSerAsnThrGluArgGlyGln-1785 |
| SEQ. ID. NO. 6179 | 1811-GlyGlyAsnValGlyLysGlyTyrGly-1819 |
| SEQ. ID. NO. 6180 | 1964-LysAsnHisSerGlnTyr-1969 |
| SEQ. ID. NO. 6181 | 1987-LeuGlyGlnGlyAlaGlnAsnLysProGln-1996 |
| SEQ. ID. NO. 6182 | 2064-ThrAspThrAlaGluArgHisSerGlySerLeuLysAsnThrPheAsn-2079 |
| SEQ. ID. NO. 6183 | 2093-ValSerGlnAspPheSerLysAsnValGln-2102 |
| SEQ. ID. NO. 6184 | 2161-IleLeuAsnMetLeuAlaSerGlyLeuAla-2170 |
| SEQ. ID. NO. 6185 | 2193-GlyGlnHisPheLysAspLeuAlaGly-2201 |
| SEQ. ID. NO. 6186 | 2223-LeuGlyAlaAlaValAla-2228 |
| SEQ. ID. NO. 6187 | 2275-AlaIleThrAsnValLeuGlyThrAlaThrGly-2285 |
| SEQ. ID. NO. 6188 | 2289-GlyAsnSerAlaThrAspAlaAla-2296 |
| SEQ. ID. NO. 6189 | 2332-HisLysAspProGly-2336 |
| SEQ. ID. NO. 6190 | 2379-IleThrArgGluPheGlyLysAspIleAla-2388 |
| SEQ. ID. NO. 6191 | 2393-AsnSerHisGluSer-2397 |
| SEQ. ID. NO. 6192 | 2414-AlaAspGluMetIleAspGlnLeuAsnAsnGluIle-2425 |
| AntigenicIndex -Jameson-Wolf | |
| SEQ. ID. NO. 6193 | 1-MetAsnLysThrLeu-5 |
| SEQ. ID. NO. 6194 | 9-IlePheAsnArgLysArgGlyAlaVal-17 |
| SEQ. ID. NO. 6195 | 22-GluThrThrLysArgGluGlyLysSerCysAlaAspSerAspSerGlySerAlaHis-40 |
| SEQ. ID. NO. 6196 | 83-IleIleAlaAspLysAlaAlaProLysThrGlnGln-94 |
| SEQ. ID. NO. 6197 | 127-ValGlyAsnArgGlyAlaIleLeuAsnAsnSerArgSerAsnThrGlnThr-143 |
| SEQ. ID. NO. 6198 | 152-AsnProTrpLeuAla-156 |
| SEQ. ID. NO. 6199 | 158-GlyGluAlaArgVal-162 |
| SEQ. ID. NO. 6200 | 167-IleAsnSerSerHisSerSerGlnMetAsnGly-177 |
| SEQ. ID. NO. 6201 | 179-IleGluValGlyGlyArgArgAlaGluVal-188 |
| SEQ. ID. NO. 6202 | 205-AsnAlaSerArgAlaThrLeu-211 |
| SEQ. ID. NO. 6203 | 213-ThrGlyGlnProGlnTyrGlnAlaGlyAspLeuSerGlyPheLysIleArgGlnGlyAsn-232 |
| SEQ. ID. NO. 6204 | 239-GlyLeuAspAlaArgAspThrAspPhe-247 |
| SEQ. ID. NO. 6205 | 252-SerTyrHisSerLysIleAspAla-259 |
| SEQ. ID. NO. 6206 | 264-GlnAspValArgVal-268 |
| SEQ. ID. NO. 6207 | 292-AsnThrSerAsnAsnThrAlaAsnAsnGlyThr-302 |
| SEQ. ID. NO. 6208 | 310-AspThrGlyLysLeuGlyGly-316 |
| SEQ. ID. NO. 6209 | 331-AlaGlyIleArgAsnGlnGlyGlnLeu-339 |
| SEQ. ID. NO. 6210 | 349-AspAlaAsnGlyArgLeuValAsn-356 |
| SEQ. ID. NO. 6211 | 364-AsnAlaLysAspThrAspAsnThrAlaGluHisLysValAsnIleArgSerGlnGlyValGluAsnSerGlyThrAlaValSerGlnGlnGlyThrGlnIle His-398 |
| SEQ. ID. NO. 6212 | 400-GlnSerIleGlnAsnThr-405 |
| SEQ. ID. NO. 6213 | 418-AsnSerGlySerLeuLysAsnGluThrSerGlyThrIleGluAlaAlaArgLeuAlaIleAspThrAspThrLeuAsnAsnGlnGlyLysLeuSerGlnThr GlySerGlnLysLeuHisIle-458 |

TABLE 1-continued

| | |
|---|---|
| SEQ. ID. NO. 6214 | 460-AlaGlnGlyLysMetAspAsnArgGlyArgMetGlyLeuGlnAspThrAlaProThrAlaSerAsnGlySerSerAsnGlnThrGlyAsnSerTyr-491 |
| SEQ. ID. NO. 6215 | 497-SerSerThrThrThrProThrThr-504 |
| SEQ. ID. NO. 6216 | 522-ThrPheAlaAspGlyThrIleArgThrHisGlyAlaLeuAspAsnSerGlySer-539 |
| SEQ. ID. NO. 6217 | 542-AlaAsnGlyGlnThrAspValSerAla-550 |
| SEQ. ID. NO. 6218 | 552-GlnGlyLeuAsnAsnAlaGlyGln-559 |
| SEQ. ID. NO. 6219 | 566-AsnAlaLysGlySerAla-571 |
| SEQ. ID. NO. 6220 | 573-AspAsnHisAsnGly-577 |
| SEQ. ID. NO. 6221 | 589-GlySerLeuAsnAsnGlnAsnGlyAsnIleThrThrArgGlnGlnLeuGluIleGluThrAspGlnLeuAspAsnAlaHisGly-616 |
| SEQ. ID. NO. 6222 | 631-SerLeuAsnAsnGlnAsnGlyGluIleAlaThrAsn-642 |
| SEQ. ID. NO. 6223 | 646-IleIleHisAspGlyGlnGlnSer-653 |
| SEQ. ID. NO. 6224 | 659-AsnThrAsnGlyThrIleGlnSerGlyArgAspValAlaIle-672 |
| SEQ. ID. NO. 6225 | 675-LysSerLeuSerAsnAsnGly-681 |
| SEQ. ID. NO. 6226 | 685-AlaAspAsnLysLeuAspIleAlaLeu-693 |
| SEQ. ID. NO. 6227 | 695-AspAspPheTyrValGlu-700 |
| SEQ. ID. NO. 6228 | 702-AsnIleValAlaGlyAsnGluLeu-709 |
| SEQ. ID. NO. 6229 | 711-LeuSerThrArgGlySerLeuLysAsnSerHisThr-722 |
| SEQ. ID. NO. 6230 | 725-AlaGlyLysArgIleArgIleLysAlaAsnAsnLeuAspAsnAlaAlaGlnGlyAsnIleGlnSerGlyGlyThrThrAspIleGlyThrGlnHisAsnLeu ThrAsnArgGlyLeuIleAspGlyGlnGlnThrLysIleGln-772 |
| SEQ. ID. NO. 6231 | 793-AlaThrArgLeuAspAsnGlnAspGluAsnGlyThrGly-805 |
| SEQ. ID. NO. 6232 | 809-AlaAlaArgGluAsnLeuAsn-815 |
| SEQ. ID. NO. 6233 | 821-LeuAsnAsnArgGluAsnSerLeu-828 |
| SEQ. ID. NO. 6234 | 839-GlyAlaLeuAspThrAsnGlyGlnAlaThrGlyLysAlaGlnArgIleHisAsnAlaGlyAla-859 |
| SEQ. ID. NO. 6235 | 863-AlaAlaGlyLysMetArgLeuGlyValGluLysLeuHisAsnThrAsnGluHisLeuLys-882 |
| SEQ. ID. NO. 6236 | 887-GluThrGlyArgGluHisIleVal-894 |
| SEQ. ID. NO. 6237 | 903-GluLeuLeuArgGluGlyThrGlnHis-911 |
| SEQ. ID. NO. 6238 | 917-ValTyrAsnAspGluSerAspHisLeuArgThrProAspGlyAlaAlaHis-933 |
| SEQ. ID. NO. 6239 | 937-HisLysTyrAspTyrGluLysValThrGlnLysThrGlnVal-950 |
| SEQ. ID. NO. 6240 | 960-SerGlyAsnAspLeuThrIleAspGlyLysGluValPheAsnThrAspSer-976 |
| SEQ. ID. NO. 6241 | 987-GlnThrGluLysAspGlyLeuHisAsnGluGlnThrPheGlyGluLysLysValPheSerGluAsnGlyLysLeuHisSerTyrTrpArgGluLysHisLys GlyArgAspSerThrGlyHisSerGluGlnAsnTyrThrLeuProGluGluIleThrArgAsn-1041 |
| SEQ. ID. NO. 6242 | 1050-GluSerHisArgLysAlaLeu-1056 |
| SEQ. ID. NO. 6243 | 1059-HisAlaProSerGlnGlyThrGluLeuProGlnSerAsnGlyIle-1073 |
| SEQ. ID. NO. 6244 | 1100-TyrLeuValGluThrAspProArgPheAlaAsn-1110 |
| SEQ. ID. NO. 6245 | 1124-LeuLysLeuAspProAsnAsnLeuHisLysArgLeuGlyAspGlyTyrTyrGluGlnArgLeuIleAsn-1146 |
| SEQ. ID. NO. 6246 | 1153-ThrGlyHisArgArgLeuAspGlyTyrGlnAsnAspGluGlnPheLysAlaLeuMetAspAsnGlyAlaThrAlaAlArgSerMetAsn-1183 |
| SEQ. ID. NO. 6247 | 1208-LysGluValLysLeuProAspGlyGlyThr-1217 |
| SEQ. ID. NO. 6248 | 1228-ArgValLysAsnGlyAspIleAspGlyLysGly-1238 |
| SEQ. ID. NO. 6249 | 1252-GlySerLeuLysAsSerGlyThrIleAlaGlyArgAsnAla-1265 |
| SEQ. ID. NO. 6250 | 1269-AsnThrAspThrLeuAspAsnIleGlyGly-1278 |
| SEQ. ID. NO. 6251 | 1280-IleHisAlaGlnLysSerAla-1286 |
| SEQ. ID. NO. 6252 | 1310-AlaGlyAsnAsnIleAsnSerGlnSerThrThrAlaSerSerGlnAsnThrGlnGlySerSerThrTyrLeu-1333 |
| SEQ. ID. NO. 6253 | 1342-ThrGlyLysGluLysGlyVal-1348 |
| SEQ. ID. NO. 6254 | 1353-AlaGlyLysAspIleAsnIle-1359 |
| SEQ. ID. NO. 6255 | 1364-IleSerAsnGlnSerGluGlnGlyGlnThrArgLeuGlnAlaGlyArgAspIleAsnLeuAspThrValGlnThrSerLysHisGln-1392 |
| SEQ. ID. NO. 6256 | 1396-PheAspAlaAspAsnHisValIleArgGlySerThrAsnGluValGlySerSerIleGlnThrLysGlyAspVal-1420 |
| SEQ. ID. NO. 6257 | 1425-GlyAsnAsnLeuAsnAlaLysAlaAlaGluValSerSerAlaAsnGly-1440 |
| SEQ. ID. NO. 6258 | 1446-AlaLysAsnAspIle-1450 |
| SEQ. ID. NO. 6259 | 1459-ThrHisValAspAspAlaSerLysHisThrGlyArgSerGlyGlyGlyAsnLysLeuValIle-1479 |
| SEQ. ID. NO. 6260 | 1481-AspLysAlaGlnSerHisHisGluThrAlaGlnSerSerThrPheGluGlyLysGln-1499 |
| SEQ. ID. NO. 6261 | 1503-GlnAlaGlyAsnAspAlaAsn-1509 |
| SEQ. ID. NO. 6262 | 1515-ValIleSerAspAsnGlyThrGlnIleGlnAla-1525 |
| SEQ. ID. NO. 6263 | 1532-GlyThrThrGlnThrGlnSerGlnSerGluThrTyrHisGlnThrGlnLysSerGlyLeu-1551 |
| SEQ. ID. NO. 6264 | 1561-GlySerLysThrAsnThrGlnGluAsnGlnSerGlnSerAsnGluHisThrGlySerThrValGlySerLeuLysGlyAspThrThrIle-1590 |
| SEQ. ID. NO. 6265 | 1592-AlaGlyLysHisTyrGluGlnIle-1599 |
| SEQ. ID. NO. 6266 | 1603-ValSerSerProGluGlyAsnAsn-1610 |
| SEQ. ID. NO. 6267 | 1621-AlaAlaHisAsnLysLeuAsnSerAsnThrThrGlnThrTyrGluGlnLysGlyLeu-1639 |
| SEQ. ID. NO. 6268 | 1659-GlnSerSerLysGlnValGlyGlnSerLysAsnAspArgValAsn-1673 |
| SEQ. ID. NO. 6269 | 1684-AlaTyrGlnThrGlyLysSerAlaGln-1692 |
| SEQ. ID. NO. 6270 | 1694LeuAlaAsnGlyThrThrAsnAlaLys-1702 |
| SEQ. ID. NO. 6271 | 1710-TyrGlyGluGlnGlnAsnArgGlnThrThrGln-1720 |
| SEQ. ID. NO. 6272 | 1729-SerGlnIleGlnAlaGlyGlyLysThrThr-1738 |
| SEQ. ID. NO. 6273 | 1744-AlaAlaGluGlnSerAsn-1749 |
| SEQ. ID. NO. 6274 | 1754-GlySerAspValAlaGlyLys-1760 |
| SEQ. ID. NO. 6275 | 1767-AlaAspAsnAspIleThr-1772 |
| SEQ. ID. NO. 6276 | 1774-GlnSerAlaGluGlnSerAsnThrGluArgGlyGlnAsnLysSerAlaGlyTrpAsn-1792 |
| SEQ. ID. NO. 6277 | 1812-GlyAsnValGlyLysGlyTyrGlyAsnGlyAspSerIleThrHisArgHIsSerHisIleGlyAspLysGlySer-1836 |
| SEQ. ID. NO. 6278 | 1841-GlnSerGlyGlyAspThrThrIleLys-1849 |
| SEQ. ID. NO. 6279 | 1851-AlaGlnValArgGlyLysGlyValGlnValAsnAlaLysAsn-1864 |
| SEQ. ID. NO. 6280 | 1869-SerValGlnAspArgGlu1874ThrTyrGlnSerLysGlnGlnAsnAla-1883 |
| SEQ. ID. NO. 6281 | 1895-AlaGlyGlyAspTyrSerGlnSerLysIleArgAlaAspHis-1908 |
| SEQ. ID. NO. 6282 | 1912-ThrGluGlnSerGlyIleTyrAlaGlyGluAspGlyTyrGln-1925 |
| SEQ. ID. NO. 6283 | 1929-GlyAsnHisThrAspLeuLysGlyGlyIle-1938 |
| SEQ. ID. NO. 6284 | 1942-ThrGlnSerAlaGluAspLysGlyLyAsnArgPheGln-1954 |
| SEQ. ID. NO. 6285 | 1959-ThrHisSerAspIleLysAsnHisSerGlnTyrLysGlyGluSerPheGly-1975 |
| SEQ. ID. NO. 6286 | 1982-IleSerGlyLysThrLeuGlyGlnGlyAlaGlnAsnLysProGlnAsnLysHis-1999 |
| SEQ. ID. NO. 6287 | 2003-ValAlaAspLysAsnSerAlaSer Ser-2011 |
| SEQ. ID. NO. 6288 | 2014-GlyTyrGlySerAspSerAspSerGlnSerSerIleThrLysSerGlyIleAsnThrArgAsn-2034 |
| SEQ. ID. NO. 6289 | 2036-GlnIleThrAspGluAlaAlaGln-2043 |
| SEQ. ID. NO. 6290 | 2045-ArgLeuThrGlyLysThrAlaAlaGlnThrLyAlaAspIleAspThrAsnValThrThrAspThrAlaGluArgHisSerGlySerLeuLysAsnThrPhe AsnLysGluAlaValGlnSerGluLeuAspLeuGlnArgThrValSerGlnAspPheSerLysAsnValGlnGlnAlaAsnThrGluIle-2108 |

TABLE 1-continued

| | |
|---|---|
| SEQ. ID. NO. 6291 | 2110-GlnHisLeuAspLysLeuLysAlaAspLysGluAlaAlaGluThrAlaAla-2126 |
| SEQ. ID. NO. 6292 | 2131-AlaAsnGlyAspMetGluThrAlaLysArgLysAlaHisGluAlaGlnAspAlaAlaAlaLysAlaAspAsnTrpGlnGln-2157 |
| SEQ. ID. NO. 6293 | 2172-ProThrGlnSerGly-2176 |
| SEQ. ID. NO. 6294 | 2195-HisPheLysAspLeuAlaGlyGlnAsnAlaAsnGlyLysLeuThrAlaSerGlnGluThr-2214 |
| SEQ. ID. NO. 6295 | 2231-GlyAspAsnAsnAla-2235 |
| SEQ. ID. NO. 6296 | 2241-SerAlaGlyGlySerGluAla-2247 |
| SEQ. ID. NO. 6297 | 2256-LeuTyrGlyLysGluLysGlySerAspLeuThrAlaGluGluLysGluThrVal-2273 |
| SEQ. ID. NO. 6298 | 2288-ValGlyAsnSerAlaThrAspAlaAlaGlnGlySerLeuAsnAla-2302 |
| SEQ. ID. NO. 6299 | 2304-SerAlaValGluAsnAsnAspThrValGluGlnVal-2315 |
| SEQ. ID. NO. 6300 | 2319-LeuArgHisProArg-2323 |
| SEQ. ID. NO. 6301 | 2331-ValHisLysAspProGlySerThrLeuGluProAsnIle-2343 |
| SEQ. ID. NO. 6302 | 2355-PheProAsnSerGluPheGlyGlyGluGlyGlyVal-2366 |
| SEQ. ID. NO. 6303 | 2379-IleThrArgGluPheGlyLysAspIleAlaVal-2389 |
| SEQ. ID. NO. 6304 | 2391-ValGlyAsnSerHisGluSerGlyGluLysIleAsnTyrSerIleArgArgAsnLeuSerLeuAspLysAlaAspGluMetIleAsp-2419 |
| SEQ. ID. NO. 6305 | 2421-LeuAsnAsnGluIleGlyArgGluIleAla-2430 |
| SEQ. ID. NO. 6306 | 2432-AsnThrAsnArgLeuAsnThrLysGluLeu-2441 |
| SEQ. ID. NO. 6307 | 2447-GluThrTyrLysAsnAsnGlyPhe-2454 |
| SEQ. ID. NO. 6308 | 2456-GlnAlaGluArgAsnSerAsnGlyAsnTyrAspValValArgLysArgLeuSerGluLysAspTyrGlnAsnThrSerAsn-2482 |
| SEQ. ID. NO. 6309 | 2496-IleGlnGlnArgArgLysGlnIleArg-2504 |
| SEQ. ID. NO. 6310 | 2510-ArgGlnTrpArgArg-2514 |
| Hydrophilic Regions - Hopp-Woods | |
| SEQ. ID. NO. 6311 | 10-PheAsnArgLysArgGlyAla-16 |
| SEQ. ID. NO. 6312 | 22-GluThrThrLysArgGluGlyLysSerCysAlaAspSerAspSerGlySerAlaHis-40 |
| SEQ. ID. NO. 6313 | 83-IleIleAlaAspLysAlaAlaProLysThrGlnGln-94 |
| SEQ. ID. NO. 6314 | 136-AsnSerArgSerAsnThr-141 |
| SEQ. ID. NO. 6315 | 158-GlyGluAlaArgVal-162 |
| SEQ. ID. NO. 6316 | 181-ValGlyGlyArgArgAlaGluVal-188 |
| SEQ. ID. NO. 6317 | 224-SerGlyPheLysIleArgGln-230 |
| SEQ. ID. NO. 6318 | 240-LeuAspAlaArgAspThrAspPhe-247 |
| SEQ. ID. NO. 6319 | 331-AlaGlyIleArgAsn-335 |
| SEQ. ID. NO. 6320 | 364-AsnAlaLysAspThrAspAsnThrAlaGluHisLysValAsnIleArgSerGlnGlyValGluAsnSerGly-387 |
| SEQ. ID. NO. 6321 | 420-GlySerLeuLysAsnGluThrSerGlyThrIleGluAlaAlaArgLeuAlaIleAspThrAspThrLeuAsnAsn-444 |
| SEQ. ID. NO. 6322 | 446-GlyLysLeuSerGln-450 |
| SEQ. ID. NO. 6323 | 460-AlaGlnGlyLysMetAspAsnArgGlyArgMetGlyLeu-472 |
| SEQ. ID. NO. 6324 | 481-AsnGlySerSerAsnGlnThr-487 |
| SEQ. ID. NO. 6325 | 534-LeuAspAsnSerGly-538 |
| SEQ. ID. NO. 6326 | 544-GlyGlnThrAspValSerAla-550 |
| SEQ. ID. NO. 6327 | 602-GlnGlnLeuGluIleGluThrAspGlnLeuAspAsnAlaHis-615 |
| SEQ. ID. NO. 6328 | 635-GlnAsnGlyGluIleAlaThr-641 |
| SEQ. ID. NO. 6329 | 665-GlnSerGlyArgAspValAlaIle-672 |
| SEQ. ID. NO. 6330 | 685-AlaAspAsnLysLeuAspIleAlaLeu-693 |
| SEQ. ID. NO. 6331 | 715-GlySerLeuLysAsn-719 |
| SEQ. ID. NO. 6332 | 725-AlaGlyLysArgIleArgIleLysAlaAsnAsnLeuAspAsnAlaAla-740 |
| SEQ. ID. NO. 6333 | 767-GlnGlnThrLysIleGln-772 |
| SEQ. ID. NO. 6334 | 794-ThrArgLeuAspAsnGlnAspGluAsnGlyThr-804 |
| SEQ. ID. NO. 6335 | 809-AlaAlaArgGluAsnLeu-814 |
| SEQ. ID. NO. 6336 | 822-AsnAsnArgGluAsnSer-827 |
| SEQ. ID. NO. 6337 | 841-LeuAspThrAsnGly-845 |
| SEQ. ID. NO. 6338 | 847-AlaThrGlyLysAlaGlnArgIleHis-855 |
| SEQ. ID. NO. 6339 | 863-AlaAlaGlyLysMetArgLeuGlyValGluLysLeuHisAsnThrAsnGluHisLeuLys-882 |
| SEQ. ID. NO. 6340 | 887-GluThrGlyArgGluHisIleVal-894 |
| SEQ. ID. NO. 6341 | 903-GluLeuLeuArgGluGlyThrGlnHis-911 |
| SEQ. ID. NO. 6342 | 919-AsnAspGluSerAspHisLeuArgThrProAspGlyAlaAla-932 |
| SEQ. ID. NO. 6343 | 939-TyrAspTyrGluLysValThrGln-946 |
| SEQ. ID. NO. 6344 | 964-LeuThrIleAspGlyLysGluValPheAsn-973 |
| SEQ. ID. NO. 6345 | 987-GlnThrGluLysAspGlyLeuHisAsn-995 |
| SEQ. ID. NO. 6346 | 998-ThrPheGlyGluLysLysValPheSerGluAsnGlyLys-1010 |
| SEQ. ID. NO. 6347 | 1015-TrpArgGluLysHisLysGlyArgAspSerThrGlyHisSerGluGln-1030 |
| SEQ. ID. NO. 6348 | 1036-GluGluIleThrArg-1040 |
| SEQ. ID. NO. 6349 | 1050-GluSerHisArgLysAlaLeu-1056 |
| SEQ. ID. NO. 6350 | 1063-GlnGlyThrGluLeuProGln-1069 |
| SEQ. ID. NO. 6351 | 1104-ThrAspProArgPheAlaAsn-1110 |
| SEQ. ID. NO. 6352 | 1124-LeuLysLeuAspPro-1128 |
| SEQ. ID. NO. 6353 | 1130-AsnLeuHisLysArgLeuGly-1136 |
| SEQ. ID. NO. 6354 | 1153-ThrGlyHisArgArgLeuAspGlyTyrGlnAsnAspGluGluGlnPheLysAlaLeuMet-1172 |
| SEQ. ID. NO. 6355 | 1175-GlyAlaThrAlaAlaArg-1180 |
| SEQ. ID. NO. 6356 | 1208-LysGluValLysLeuProAspGlyGlyThr-1217 |
| SEQ. ID. NO. 6357 | 1229-ValLysAsnGlyAspIleAspGlyLysGly-1238 |
| SEQ. ID. NO. 6358 | 1252-GlySerLeuLysAsn-1256 |
| SEQ. ID. NO. 6359 | 1280-IleHisAlaGlnLysSerAla-1286 |
| SEQ. ID. NO. 6360 | 1324-GlnAsnThrGlnGly-1328 |
| SEQ. ID. NO. 6361 | 1343-GlyLysGluLysGlyVal-1348 |
| SEQ. ID. NO. 6362 | 1353-AlaGlyLysAspIleAsn-1358 |
| SEQ. ID. NO. 6363 | 1366-AsnGlnSerGluGlnGlyGlnThrArgLeuGlnAlaGlyArgAspIleAsnLeu-1383 |
| SEQ. ID. NO. 6364 | 1387-GlnThrSerLysHisGln-1392 |
| SEQ. ID. NO. 6365 | 1396-PheAspAlaAspAsnHisVal-1402 |
| SEQ. ID. NO. 6366 | 1406-SerThrAsnGluValGlySer-1412 |
| SEQ. ID. NO. 6367 | 1414-IleGlnThrLysGlyAspVal-1420 |
| SEQ. ID. NO. 6368 | 1428-LeuAsnAlaLysAlaAlaGluValSerSer-1437 |
| SEQ. ID. NO. 6369 | 1446-AlaLysAsnAspIle-1450 |

TABLE 1-continued

| | |
|---|---|
| SEQ. ID. NO. 6370 | 1460-HisValAspAspAlaSerLysHisThrGlyArgSerGlyGlyGly-1474 |
| SEQ. ID. NO. 6371 | 1481-AspLysAlaGlnSerHisHisGluThrAlaGln-1491 |
| SEQ. ID. NO. 6372 | 1493-SerThrPheGluGlyLysGln-1499 |
| SEQ. ID. NO. 6373 | 1537-GlnSerGlnSerGluThr-1542 |
| SEQ. ID. NO. 6374 | 1562-SerLysThrAsnThrGlnGluAsnGlnSerGlnSerAsnGluHisThrGly-1578 |
| SEQ. ID. NO. 6375 | 1584-LeuLysGlyAspThr-1588 |
| SEQ. ID. NO. 6376 | 1604-SerSerProGluGlyAsn-1609 |
| SEQ. ID. NO. 6377 | 1621AlaAlaHisAsnLysLeuAsnSer-1628 |
| SEQ. ID. NO. 6378 | 1634-TyrGluGlnLysGly-1638 |
| SEQ. ID. NO. 6379 | 1659-GlnSerSerLysGlnValGlyGlnSerLysAsnAspArgValAsn-1673 |
| SEQ. ID. NO. 6380 | 1686-GlnThrGlyLysSerAlaGln-1692 |
| SEQ. ID. NO. 6381 | 1712-GluGlnGlnAsnArgGlnThrThr-1719 |
| SEQ. ID. NO. 6382 | 1744-AlaAlaGluGlnSerAsn-1749 |
| SEQ. ID. NO. 6383 | 1756-AspValAlaGlyLys-1760 |
| SEQ. ID. NO. 6384 | 1767-AlaAspAsnAspIle-1771 |
| SEQ. ID. NO. 6385 | 1775-SerAlaGluGlnSerAsnThrGluArgGlyGlnAsnLys-1787 |
| SEQ. ID. NO. 6386 | 1822-AspSerIleThrHis-1826 |
| SEQ. ID. NO. 6387 | 1830-HisIleGlyAspLysGlySer-1836 |
| SEQ. ID. NO. 6388 | 1843-GlyGlyAspThrThrIleLys-1849 |
| SEQ. ID. NO. 6389 | 1851-AlaGlnValArgGlyLysGlyVal-1858 |
| SEQ. ID. NO. 6390 | 1869-SerValGlnAspArgGluThrTyrGlnSerLysGlnGlnAsnAla-1883 |
| SEQ. ID. NO. 6391 | 1897-GlyAspTyrSerGlnSerLysIleArgAlaAspHis-1908 |
| SEQ. ID. NO. 6392 | 1919-AlaGlyGluAspGlyTyrGln-1925 |
| SEQ. ID. NO. 6393 | 1932-ThrAspLeuLysGly-1936 |
| SEQ. ID. NO. 6394 | 1943-GlnSerAlaGluAspLysGlyLysAsnArgPhe-1953 |
| SEQ. ID. NO. 6395 | 1961-SerAspIleLysAsn-1965 |
| SEQ. ID. NO. 6396 | 1967-SerGlnTyrLysGlyGluSer-1973 |
| SEQ. ID. NO. 6397 | 1991-AlaGlnAsnLysProGlnAsnLysHis-1999 |
| SEQ. ID. NO. 6398 | 2003-ValAlaAspLysAsnSerAla-2009 |
| SEQ. ID. NO. 6399 | 2017-SerAspSerAspSerGlnSerSerIleThr-2026 |
| SEQ. ID. NO. 6400 | 2036-GlnIleThrAspGluAlaAlaGln-2043 |
| SEQ. ID. NO. 6401 | 2050-ThrAlaAlaGlnThrLysAlaAspIleAspThr-2060 |
| SEQ. ID. NO. 6402 | 2065-AspThrAlaGluArgHisSerGlySerLeu-2074 |
| SEQ. ID. NO. 6403 | 2077-ThrPheAsnLysGluAlaValGlnSerGluLeuAspLeuGlnArg-2091 |
| SEQ. ID. NO. 6404 | 2104-AlaAsnThrGluIle-2108 |
| SEQ. ID. NO. 6405 | 2110-GlnHisLeuAspLysLeuLysAlaAspLysGluAlaAlaGluThrAlaAla-2126 |
| SEQ. ID. NO. 6406 | 2133-GlyAspMetGluThrAlaLysArgLysAlaHisGluAlaGlnAspAlaAlaAlaLysAlaAspAsn-2154 |
| SEQ. ID. NO. 6407 | 2195-HisPheLysAspLeuAlaGly-2201 |
| SEQ. ID. NO. 6408 | 2208-LeuThrAlaSerGlnGluThr-2214 |
| SEQ. ID. NO. 6409 | 2243-GlyGlySerGluAla-2247 |
| SEQ. ID. NO. 6410 | 2257-TyrGlyLysGluLysGlySerAspLeuThrAlaGluGluLysGluThrVal-2273 |
| SEQ. ID. NO. 6411 | 2291-SerAlaThrAspAlaAlaGln-2297 |
| SEQ. ID. NO. 6412 | 2304-SerAlaValGluAsnAsnAspThrValGluGlnVal-2315 |
| SEQ. ID. NO. 6413 | 2319-LeuArgHisProArg-2323 |
| SEQ. ID. NO. 6414 | 2331-ValHisLysAspProGlySerThrLeu-2339 |
| SEQ. ID. NO. 6415 | 2379-IleThrArgGluPheGlyLys-2385 |
| SEQ. ID. NO. 6416 | 2393-AsnSerHisGluSerGlyGluLysIleAsnTyrSerIleArgArgAsnLeuSerLeuAspLysAlaAspGluMetIleAsp-2419 |
| SEQ. ID. NO. 6417 | 2424-GluIleGlyArgGluIleAla-2430 |
| SEQ. ID. NO. 6418 | 2435-ArgLeuAsnThrLysGluLeu-2441 |
| SEQ. ID. NO. 6419 | 2456-GlnAlaGluArgAsnSerAsnGly-2463 |
| SEQ. ID. NO. 6420 | 2466-AspValValArgLysArgLeuSerGluLysAspTyrGlnAsn-2479 |
| SEQ. ID. NO. 6421 | 2496-IleGlnGlnArgArgLysGlnIleArg-2504 |
| SEQ. ID. NO. 6422 | 2510-ArgGlnTrpArgArg-2514 |
| 564-2 | |
| AMPHIRegions- AMPHI | |
| SEQ. ID. NO. 6423 | 6-TyrLysValValPhe-10 |
| SEQ. ID. NO. 6424 | 25-LysArgGluGlyLysAsnThr-31 |
| SEQ. ID. NO. 6425 | 40-LeuProAsnAspIleAlaGlyPheAlaGlyPheIleHisSerIleSer-55 |
| SEQ. ID. NO. 6426 | 118-AsnGlnTyrAlaGlnPhe-123 |
| SEQ. ID. NO. 6427 | 162-ValAsnGlnIleAsnSerSerHisSerSerGlnLeuAsn-174 |
| SEQ. ID. NO. 6428 | 244-AspTyrThrArgIleLeuSerTyrHisSer-253 |
| SEQ. ID. NO. 6429 | 288-AlaAlaAsnThrSerAsnAsnThrAla-296 |
| SEQ. ID. NO. 6430 | 311-LysLeuGlyGlyMetTyr-316 |
| SEQ. ID. NO. 6431 | 322-LeuIleSerThrValGluGln-328 |
| SEQ. ID. NO. 6432 | 390-SerGlnThrLeuAsp-394 |
| SEQ. ID. NO. 6433 | 407-ValArgAsnLeuGlyArgLeuLysAsnGlnAsn-417 |
| SEQ. ID. NO. 6434 | 433-LeuAspAsnThrGlyAsnIleThrGlnThrGly-443 |
| SEQ. ID. NO. 6435 | 449-LeuValSerAlaGlyLysPheAspAsnSer-458 |
| SEQ. ID. NO. 6436 | 478-IleProGlnIleProSerThr-484 |
| SEQ. ID. NO. 6437 | 518-IleGlnThrThrGlyAlaPheAspAsnAlaGlySerIleAsnAla-532 |
| SEQ. ID. NO. 6438 | 561-SerPheAsnAsnThrValLys-567 |
| SEQ. ID. NO. 6439 | 600-LeuHisAsnAlaGly-604 |
| SEQ. ID. NO. 6440 | 638-GlyLeuHisAsnAlaGly-643 |
| SEQ. ID. NO. 6441 | 658-LeuArgAsnThrGlyLysVal-664 |
| SEQ. ID. NO. 6442 | 736-LeuTyrAsnGlnHisGly-741 |
| SEQ. ID. NO. 6443 | 765-AspGlyThrIleGlnSerAla-771 |
| SEQ. ID. NO. 6444 | 841-AspAsnGlnValThrGlyLys-847 |
| SEQ. ID. NO. 6445 | 871-AspGlyLeuThrHisIleGlyAlaGly-879 |
| SEQ. ID. NO. 6446 | 882-LeuThrAsnThrGlyThrGlyLysIleTyr-891 |
| SEQ. ID. NO. 6447 | 958-AlaGlyMetAlaAspThrPheVal-965 |

TABLE 1-continued

| | |
|---|---|
| SEQ. ID. NO. 6448 | 980-SerValArgAsnMetGlnAsnIleAsnAsnHis-990 |
| SEQ. ID. NO. 6449 | 1000-AlaGluLysGlnVal-1004 |
| SEQ. ID. NO. 6450 | 1125-ThrGlnTrpAspSerValThrLys-1132 |
| SEQ. ID. NO. 6451 | 1185-IleLysLeuIleAspGlyValSerThr-1193 |
| SEQ. ID. NO. 6452 | 1263-HisLysArgLeuGlyAspGlyTyr-1270 |
| SEQ. ID. NO. 6453 | 1278-GluGlnIleHisGlnLeuThrGlyTyrArgArgLeuAspGlyTyr-1292 |
| SEQ. ID. NO. 6454 | 1299-PheLysAlaLeuMetAspAsn-1305 |
| SEQ. ID. NO. 6455 | 1325-GlnValAlaArgLeu-1329 |
| SEQ. ID. NO. 6456 | 1461-ThrAlaIleAspArgMetAlaGlyIleAsnValValGlySerHisThrGluGlnValAspAsnArg-1482 |
| SEQ. ID. NO. 6457 | 1504-SerAsnGlnValLysAspGlyThrThr-1512 |
| SEQ. ID. NO. 6458 | 1515-ThrAlaGlyAsnAsn-1519 |
| SEQ. ID. NO. 6459 | 1542-ArgHisValArgGlnSerThrGluVal-1550 |
| SEQ. ID. NO. 6460 | 1596-ArgGlnIleThrGluLeu-1601 |
| SEQ. ID. NO. 6461 | 1720-IleIleGlySerLeuAsn-1725 |
| SEQ. ID. NO. 6462 | 1791-AlaGlnAsnPheIleGlnAlaAlaGlnAsnValGlyLysSer-1804 |
| SEQ. ID. NO. 6463 | 1822-TyrGlnAlaThrGlnGlnMet-1828 |
| SEQ. ID. NO. 6464 | 1870-GluAlaAlaAlaSerGln-1875 |
| SEQ. ID. NO. 6465 | 1925-GlySerGluGlnSer-1929 |
| SEQ. ID. NO. 6466 | 1955-GlyGlyAsnIleGlyLysGlyLys-1962 |
| SEQ. ID. NO. 6467 | 2106-AspIleGlnAsnHisSer-2111 |
| SEQ. ID. NO. 6468 | 2138-GlnGlyArgProThrAspArgIleSerProAla-2148 |
| SEQ. ID. NO. 6469 | 2177-AlaGlyGlnLeuAlaArgThrGlyArgThrAlaLys-2188 |
| SEQ. ID. NO. 6470 | 2204-AspGlnHisSerGlyHisLeuLysAsnSerPhe-2214 |
| SEQ. ID. NO. 6471 | 2228-GluValThrLysGluPheGlyArgAsnAlaAla-2238 |
| SEQ. ID. NO. 6472 | 2243-AlaValAlaAspLysLeuGlyAsnThrGlnSerTyrGluArgTyrGln-2258 |
| SEQ. ID. NO. 6473 | 2297-ArgTyrAspThrTrpLysGlu-2303 |
| SEQ. ID. NO. 6474 | 2308-ArgSerIleLeuHisGlyAlaAlaGly-2316 |
| SEQ. ID. NO. 6475 | 2320-ThrGlySerLeuGlyGlyIleLeuAla-2328 |
| SEQ. ID. NO. 6476 | 2336-AlaProTyrLeuAspLysAlaAlaGluAsnLeuGlyPro-2348 |
| SEQ. ID. NO. 6477 | 2352-AlaAlaValAsnAlaLeuGly-2358 |
| SEQ. ID. NO. 6478 | 2395-LysTyrAlaGluAlaLeuLysArg-2402 |
| SEQ. ID. NO. 6479 | 2404-ValGluLysArgGluGly-2409 |
| SEQ. ID. NO. 6480 | 2424-GlnIleLeuArgTrpValAspLysGlySerGlnAspGly-2436 |
| SEQ. ID. NO. 6481 | 2470-GlnThrTyrAsnAspProLysLeuPheGluGluTyr-2481 |
| SEQ. ID. NO. 6482 | 2520-GluGlyLeuThrSerLeuVal-2526 |
| SEQ. ID. NO. 6483 | 2537-LeuAlaGlyIleArgAsnLeuLysAsnIle-2546 |
| SEQ. ID. NO. 6484 | 2571-ValAlaLysGlyAspArg-2576 |
| SEQ. ID. NO. 6485 | 2620-LysProGlnArgGln-2624 |
| SEQ. ID. NO. 6486 | 2647-AspValCysThrGluCys-2652 |
| SEQ. ID. NO. 6487 | 2669-ProGluIleGluArg-2673 |
| AntigenicIndex -Jameson-Wolf | |
| SEQ. ID. NO. 6488 | 10-PheAsnLysHisArgAsnCysMet-17 |
| SEQ. ID. NO. 6489 | 22-GluAsnAlaLysArgGluGlyLysAsnThrAlaAsp-33 |
| SEQ. ID. NO. 6490 | 82-ValAlaAspLysSerAlaProAlaGlnGlnGln-92 |
| SEQ. ID. NO. 6491 | 125-ValGlyAsnArgGlyAlaIleLeuAsnAsnSerArgSerAsnThrGlnThr-141 |
| SEQ. ID. NO. 6492 | 150-AsnProTrpLeuAla-154 |
| SEQ. ID. NO. 6493 | 156-GlyGluAlaArgVal-160 |
| SEQ. ID. NO. 6494 | 165-IleAsnSerSerHisSerSerGlnLeuAsnGly-175 |
| SEQ. ID. NO. 6495 | 177-IleGluValGlyGlyArgArgAlaGluVal-186 |
| SEQ. ID. NO. 6496 | 203-AsnAlaSerArgAlaThrLeu-209 |
| SEQ. ID. NO. 6497 | 214-ProGlnTyrGlnAlaGlyAspLeuSerGlyPheLysIleArgGlnGlyAsn-230 |
| SEQ. ID. NO. 6498 | 237-GlyLeuAspAlaArgAspThrAspTyrThrArg-247 |
| SEQ. ID. NO. 6499 | 250-SerTyrHisSerLysIleAspAla-257 |
| SEQ. ID. NO. 6500 | 262-GlnAspValArgVal-266 |
| SEQ. ID. NO. 6501 | 269-GlyGlnAsnAspValAlaAlaThrGlyAspAlaHisSerPro-282 |
| SEQ. ID. NO. 6502 | 290-AsnThrSerAsnAsnThrAlaAsnAsnGlyThr-300 |
| SEQ. ID. NO. 6503 | 308-AspThrGlyLysLeuGlyGly-314 |
| SEQ. ID. NO. 6504 | 327-GluGlnAlaGlyIleArgAsnGlnGlyGln-336 |
| SEQ. ID. NO. 6505 | 347-AsnAlaGluGlyLysLeuValAsn-354 |
| SEQ. ID. NO. 6506 | 361-ThrGlyGluAsnHis-365 |
| SEQ. ID. NO. 6507 | 373-AsnValHisAsnSerGlyThrValAlaSerGlnAspAspAlaAsnIleHis-389 |
| SEQ. ID. NO. 6508 | 391-GlnThrLeuAspAsnSerGlyThrVal-399 |
| SEQ. ID. NO. 6509 | 401-SerSerGlyArgLeuThrVal-407 |
| SEQ. ID. NO. 6510 | 409-AsnLeuGlyArgLeuLysAsnGlnAsnAsnGly-419 |
| SEQ. ID. NO. 6511 | 424-AlaArgLeuAspMetSerThrGlyGlyLeuAspAsnThrGlyAsnIleThrGlnThrGlySerGln-445 |
| SEQ. ID. NO. 6512 | 453-GlyLysPheAspAsnSerGlyLysIleGlyValSerAspValProGlnThrGlyLeuAsnProAsnProSerVal-477 |
| SEQ. ID. NO. 6513 | 486-ThrGlySerGlySer-490 |
| SEQ. ID. NO. 6514 | 493-ValSerValSerLysProGlySerAsnAsnProValSerProThrAlaProAlaLysAsnTyrAla-514 |
| SEQ. ID. NO. 6515 | 525-AspAsnAlaGlySerIleAsnAlaGlyGlyGlnIleAsp-537 |
| SEQ. ID. NO. 6516 | 542-AsnGlyLeuGlyAsnSerGlySer-549 |
| SEQ. ID. NO. 6517 | 553-AlaLysLeuArgValSerGlyAspSerPheAsnAsnThrValLysGlyLysLeuGlnAla-572 |
| SEQ. ID. NO. 6518 | 580-GlnThrAlaLysAsnSerGlyHis-587 |
| SEQ. ID. NO. 6519 | 591-GlnThrGlyLysIleAspAsnArgGluLeuHisAsnAlaGlyGlu-605 |
| SEQ. ID. NO. 6520 | 615-HisSerGlyArgLeuSerAsnAspLysLysGlyAsnIle-627 |
| SEQ. ID. NO. 6521 | 647-AlaAspSerGlyThrValThrThrLysAsnAsnLeuArgAsnThrGlyLysValSerValAlaArgLeuAsnThrGluGlyGlnThrLeuAspAsnThr ArgGlyArgIleGluAlaGluThrValAsn-689 |
| SEQ. ID. NO. 6522 | 694-GlnLeuThrAsnGlnSerGlyHis-701 |
| SEQ. ID. NO. 6523 | 710-IleAsnSerArgAsnValAspAsnGlnAsnGlyLysLeuLeuSer-724 |
| SEQ. ID. NO. 6524 | 732-ValSerAspGlyLeuTyrAsnGlnHisGly-741 |
| SEQ. ID. NO. 6525 | 750-SerIleHisAspLysAsnGlnAsnThr-758 |

TABLE 1-continued

| | |
|---|---|
| SEQ. ID. NO. 6526 | 761-LeuAsnAsnAlaAspGlyThrIle-768 |
| SEQ. ID. NO. 6527 | 780-SerLeuAlaAsnAsnGlyThr-786 |
| SEQ. ID. NO. 6528 | 789-AlaGlyAsnLysLeuAsp-794 |
| SEQ. ID. NO. 6529 | 797-LeuThrAspAspPheValValGluArgAspLeuThrAlaGlyLys-811 |
| SEQ. ID. NO. 6530 | 817-IleLysGlyArgLeuLysAsnThrHisThr-826 |
| SEQ. ID. NO. 6531 | 836-AsnAlaGlyAsnIleAspAsnGlnVal-844 |
| SEQ. ID. NO. 6532 | 849-IleGlyGlyGluGlnThrAspIleThrSerGluGlnHisValAspAsnArgGlyLeuIleAsnSerAspGly-872 |
| SEQ. ID. NO. 6533 | 881-ThrLeuThrAsnThrGlyThrGlyLysIleTyr-891 |
| SEQ. ID. NO. 6534 | 903-LeuAsnArgGluGluThrThrGluGlySerThrLysAla-915 |
| SEQ. ID. NO. 6535 | 919-AlaAlaArgLysArgLeuAspIleGlyAlaLysGluIleHisAsnGlnGluGly-936 |
| SEQ. ID. NO. 6536 | 939-LeuSerSerGluGly-943 |
| SEQ. ID. NO. 6537 | 948-GlyAsnArgLeuAspGluGlnHisHis-956 |
| SEQ. ID. NO. 6538 | 985-GlnAsnIleAsnAsnHisPheLysThrGluThrTyrLeuAlaLysAlaGluLysGlnValArgAsp-1006 |
| SEQ. ID. NO. 6539 | 1017-GlnAlaGlyLysAspGlyLeuPheAspAsnSerGlnGlyGlnLysAspGlnThrThr-1035 |
| SEQ. ID. NO. 6540 | 1039-HisLeuLysAsnGlySerArgIleGluAla-1048 |
| SEQ. ID. NO. 6541 | 1060-ThrTyrLysGluArgIleIleGluAsnArgProAlaHis-1072 |
| SEQ. ID. NO. 6542 | 1076-GlyGlyAspLeuThrAlaSerGlyGlnAsnTrpLeuAsnLysAspSerArgIle-1093 |
| SEQ. ID. NO. 6543 | 1098-ArgIleIleThrAspAspLeuAsnGlnLysGluIleThrAsnGlnSerThrThrGlyLysGlyArgThrAspAlaVal-1123 |
| SEQ. ID. NO. 6544 | 1126-GlnTrpAspSerValThrLysLysGlyTrpTyrSerGlyArgLysArgGlnArgArgThrGluArgAsnIiisThrProTyrHisAsp-1154 |
| SEQ. ID. NO. 6545 | 1160-HisAspPheAspThrProVal-1166 |
| SEQ. ID. NO. 6546 | 1172-AsnAlaAlaSerProSerPhe-1178 |
| SEQ. ID. NO. 6547 | 1196-ValAsnGlyGlnArgIleHisThr-1203 |
| SEQ. ID. NO. 6548 | 1223-ThrThrHisProAspAsnLysGlyTrp-1231 |
| SEQ. ID. NO. 6549 | 1234-GluThrAspProGlnPheAlaAspTyrArgArgTrpLeuGlySerAspTyr-1250 |
| SEQ. ID. NO. 6550 | 1258-AspThrAsnHisLeuHisLysArgLeuGlyAspGlyTyrTyrGluGlnLysLeuValAsn-1277 |
| SEQ. ID. NO. 6551 | 1285-GlyTyrArgArgLeuAspGlyTyrArgSerAspGluGluGlnPheLysAlaLeuMetAspAsnGly-1306 |
| SEQ. ID. NO. 6552 | 1343-LeuSerAspGlySerThrGln-1349 |
| SEQ. ID. NO. 6553 | 1359-LeuAlaArgLysGlyAspLeuAsnThrSerGlyGly-1370 |
| SEQ. ID. NO. 6554 | 1382-GlnAsnGlyAsnLeuThrAsn-1388 |
| SEQ. ID. NO. 6555 | 1403-ArgAsnIleAsnSerAsnGlyAsnIleGln-1412 |
| SEQ. ID. NO. 6556 | 1416-IleGlyLeuLysAlaGluLysSerIleAsnIleAspGlyGlyGlnValGln-1432 |
| SEQ. ID. NO. 6557 | 1445-AsnLeuAsnGlyThrThrGlnThrSerGlyAsnGluArgAsnGlyAsnThrAlaIleAspArgMetAla-1467 |
| SEQ. ID. NO. 6558 | 1473-GlySerHisThrGluGlnValAspAsnArgThrSerAspGly-1486 |
| SEQ. ID. NO. 6559 | 1491-HisAlaSerAsnAspIle-1496 |
| SEQ. ID. NO. 6560 | 1503-ValSerAsnGlnValLysAspGlyThrThr-1512 |
| SEQ. ID. NO. 6561 | 1525-IleArgThrGluHisArgGluAlaTyrGlyThrLeuAspAspGluAsnHisArgHisValArgGlnSerThrGluValGlySerSerIleArgThrGlnAsn Gly-1559 |
| SEQ. ID. NO. 6562 | 1564-AlaGlyAsnAspLeuLysIleArgGlnGlyGluLeuGluAlaGluGluGlyLysThr-1582 |
| SEQ. ID. NO. 6563 | 1586-AlaGlyArgAspValThrIleSerGluGlyArgGlnIleThrGluLeuAspThrSerValSerGlyLysSerLysGlyIleLeuSerSerThrLysThrHis AspArgTyrArgPheSerHisAspGluAlaVal-1630 |
| SEQ. ID. NO. 6564 | 1633-AsnIleGlyGlyGlyLysMet-1639 |
| SEQ. ID. NO. 6565 | 1644-GlyGlnAspIleAsnValArgGlySerAsnLeuIleSerAspLysGlyIleVal-1661 |
| SEQ. ID. NO. 6566 | 1664-AlaGlyHisAspIleAspIleSerThrAlaHisAsnArgTyrThrGlyAsnGluTyrHisGluSerLysLysSerGlyVal-1690 |
| SEQ. ID. NO. 6567 | 1699-ThrIleGlyAsnArgLysThrThrAspAspThrAspArgThrAsnIle-1714 |
| SEQ. ID. NO. 6568 | 1723-SerLeuAsnGlyAspThr-1728 |
| SEQ. ID. NO. 6569 | 1732-AlaGlyAsnArgTyrArgGlnThrGlySerThrValSerSerProGluGlyArgAsnThrValThr-1753 |
| SEQ. ID. NO. 6570 | 1761-PheAlaAsnAsnArgTyrAlaThrAspTyrAlaHisThrGlnGluGlnLysGly-1778 |
| SEQ. ID. NO. 6571 | 1799-GlnAsnValGlyLysSerLysAsnLysArgValAsn-1810 |
| SEQ. ID. NO. 6572 | 1832-AlaProSerSerSerAlaGlyGlnGlyGlnAsnAsnAsnGlnSerProSerIle-1849 |
| SEQ. ID. NO. 6573 | 1854-ThrTyrGlyGluGlnLysSerArgAsnGluGlnLysArgHisTyrThr-1869 |
| SEQ. ID. NO. 6574 | 1878-GlyLysGlyGlnThr-1882 |
| SEQ. ID. NO. 6575 | 1886-AlaThrGlySerGlyGluGlnSerAsnIleAsn-1896 |
| SEQ. ID. NO. 6576 | 1898-ThrGlySerAspVal-1902 |
| SEQ. ID. NO. 6577 | 1919-GlnSerAlaLysGlnAspGlySerGluGlnSerLysAsnLysSerSerGlyTrpAsnAla-1938 |
| SEQ. ID. NO. 6578 | 1954-AlaGlyGlyAsnIleGlyLysGlyLysGluGlnGlyGlySerThrThrHisArgHisThrHisValGlySerThrThrGlyLysThrThrIleArgSerGly GlyAspThrThrLeu-1992 |
| SEQ. ID. NO. 6579 | 1999-GlyLysGlyIleGlnAlaAspThrArgAsnLeuHis-2010 |
| SEQ. ID. NO. 6580 | 2013-SerValGlnAspThrGluThrTyrGlnSerLysGlnGlnAsnGlyAsn-2028 |
| SEQ. ID. NO. 6581 | 2038-SerAlaSerGlySerTyrArgGlnSerLysValLysAlaAspHis-2052 |
| SEQ. ID. NO. 6582 | 2062-TyrAlaGlyGluAspGlyTyrGlnIleLysValArgAspAsnThrAspLeuLysGly-2080 |
| SEQ. ID. NO. 6583 | 2086-SerGlnSerAlaGluAspLysGlyLysAsnLeuPhe-2097 |
| SEQ. ID. NO. 6584 | 2105-SerAspIleGlnAsnHisSerArgTyrGluGlyArgSerPheGly-2119 |
| SEQ. ID. NO. 6585 | 2126-LeuAsnGlyGlyTrpAspGlyThrValThrAspLysGlnGlyArgProThrAspArgIleSerPro-2147 |
| SEQ. ID. NO. 6586 | 2151-TyrGlySerAspGlyAspSerLysAsnSerThrThrArgSerGlyValAsnThrHis-2169 |
| SEQ. ID. NO. 6587 | 2173-IleThrAspGluAlaGlyGlnLeuAlaArgThrGlyArgThrAlaLysGluThrGluAlaArgIle-2194 |
| SEQ. ID. NO. 6588 | 2197-GlyIleAspThrGluThrAlaAspGlnHisSerGlyHisLeuLysAsnSerPheAspLysAspAlaValAlaLysGluIleAsnLeuGlnArgGluVal ThrLysGluPheGlyArgAsnAlaAla-2238 |
| SEQ. ID. NO. 6589 | 2244-ValAlaAspLysLeuGlyAsnThrGlnSerTyrGluArgTyrGlnGluAlaArgThrLeuLeu-2264 |
| SEQ. ID. NO. 6590 | 2266-AlaGluLeuGlnAsnThrAspSerGluAlaGluLysAlaAlaPhe-2280 |
| SEQ. ID. NO. 6591 | 2292-AlaGluAsnGlnSerArgTyrAspThrTrpLysGluGlyGlyIleGlyArgSerIle-2310 |
| SEQ. ID. NO. 6592 | 2338-TyrLeuAspLysAlaAlaGluAsnLeuGlyProAlaGly-2350 |
| SEQ. ID. NO. 6593 | 2378-ValAspTrpAsnAsnArgGlnLeuHisProLysGluMetAlaLeu-239 |
| SEQ. ID. NO. 6594 | 2394-AspLysTyrAlaGluAlaLeuLysArgGluValGluLysArgGluGlyArgLysIleSerSerGlnGluAlaAlaMetArgIleArgArgGlnIle-2425 |
| SEQ. ID. NO. 6595 | 2428-TrpValAspLysGlySerGlnAspGlyTyrThrAspGlnSerVal-244 |
| SEQ. ID. NO. 6596 | 2448-MetLysGlyGluAspLysAlaLeu-2455 |
| SEQ. ID. NO. 6597 | 2460-AspTyrArgAspTyrGlyAlaArgAsnProGlnThrTyrAsnAspProLysLeuPheGluGluTyrArgArgGlnAspLysProGluTyrArgAsn- 2491 |
| SEQ. ID. NO. 6598 | 2496-HisSerGlyThrLysAspThrLysIleArgGlnGlyGluArgLysAsnGluGluPhe-2514 |
| SEQ. ID. NO. 6599 | 2527-AsnProAsnProArgIleLysVal-2534 |
| SEQ. ID. NO. 6600 | 2541-ArgAsnLeuLysAsnIleLysProThrValThrGlySerAspPro-255 |

TABLE 1-continued

| | |
|---|---|
| SEQ. ID. NO. 6601 | 2569-GlyAsnValAlaLysGlyAspArgIleProAspThrAlaLeuAlaSerLysGlyIleLysHisLysAsnArgLysAspGlnLeuGluLysAsnLysLysSerGlyGluAspPheGluMet-2608 |
| SEQ. ID. NO. 6602 | 2610-IleTyrGlnLysLysValLysGlnGlyPheLysProGlnArgGlnIleThrValLysThrLysSerGlyValLysThrArgLeuAspIleIleSerLysGluGlyGlyLeuAspValCysThrGluCysLysAla-2654 |
| SEQ. ID. NO. 6603 | 2659-ProLeuThrLysAsnGlnLysLysAlaPheProGluIleGluArgThrGlyAla-2676 |
| SEQ. ID. NO. 6604 | 2680-GlyLysGlyLysProGlyTyrProLysGlyThrLysIleGluProThrLysValIleIleGluArgLysArg-2703 |
| Hydrophilic Regions- Hopp-Woods | |
| SEQ. ID. NO. 6605 | 10-PheAsnLysHisArgAsn-15 |
| SEQ. ID. NO. 6606 | 22-GluAsnAlaLysArgGluGlyLysAsnThrAlaAsp-33 |
| SEQ. ID. NO. 6607 | 82-ValAlaAspLysSerAlaPro-88 |
| SEQ. ID. NO. 6608 | 134-AsnSerArgSerAsnThr-139 |
| SEQ. ID. NO. 6609 | 156-GlyGluAlaArgVal-160 |
| SEQ. ID. NO. 6610 | 179-ValGlyGlyArgArgAlaGluVal-186 |
| SEQ. ID. NO. 6611 | 222-SerGlyPheLysIleArgGln-228 |
| SEQ. ID. NO. 6612 | 238-LeuAspAlaArgAspThrAspTyr-245 |
| SEQ. ID. NO. 6613 | 271-AsnAspValAlaAla-275 |
| SEQ. ID. NO. 6614 | 329-AlaGlyIleArgAsn-333 |
| SEQ. ID. NO. 6615 | 348-AlaGluGlyLysLeu-352 |
| SEQ. ID. NO. 6616 | 361-ThrGlyGluAsnHis-365 |
| SEQ. ID. NO. 6617 | 381-AlaSerGlnAspAspAlaAsnIle-388 |
| SEQ. ID. NO. 6618 | 409-AsnLeuGlyArgLeuLysAsnGlnAsn-417 |
| SEQ. ID. NO. 6619 | 424-AlaArgLeuAspMet-428 |
| SEQ. ID. NO. 6620 | 453-GlyLysPheAspAsnSerGlyLysIleGlyVal-463 |
| SEQ. ID. NO. 6621 | 494-SerValSerLysProGlySer-500 |
| SEQ. ID. NO. 6622 | 553-AlaLysLeuArgValSerGly-559 |
| SEQ. ID. NO. 6623 | 566-ValLysGlyLysLeuGlnAla-572 |
| SEQ. ID. NO. 6624 | 580-GlnThrAlaLysAsnSer-585 |
| SEQ. ID. NO. 6625 | 593-GlyLysIleAspAsnArgGluLeuHisAsn-602 |
| SEQ. ID. NO. 6626 | 618-ArgLeuSerAsnAspLysLysGlyAsnIle-627 |
| SEQ. ID. NO. 6627 | 650-GlyThrValThrThr-654 |
| SEQ. ID. NO. 6628 | 656-AsnAsnLeuArgAsnThrGlyLys-663 |
| SEQ. ID. NO. 6629 | 669-LeuAsnThrGluGlyGlnThrLeuAspAsnThrArgGlyArgIleGluAlaGluThr-687 |
| SEQ. ID. NO. 6630 | 713-ArgAsnValAspAsnGlnAsn-719 |
| SEQ. ID. NO. 6631 | 750-SerIleHisAspLysAsnGlnAsn-757 |
| SEQ. ID. NO. 6632 | 763-AsnAlaAspGlyThrIle-768 |
| SEQ. ID. NO. 6633 | 801-PheValValGluArgAspLeuThrAla-809 |
| SEQ. ID. NO. 6634 | 817-IleLysGlyArgLeuLysAsn-823 |
| SEQ. ID. NO. 6635 | 852-GluGlnThrAspIleThrSer-858 |
| SEQ. ID. NO. 6636 | 860-GlnHisValAspAsnArgGlyLeuIle-868 |
| SEQ. ID. NO. 6637 | 903-LeuAsnArgGluGluThrThrGluGlySerThrLysAla-915 |
| SEQ. ID. NO. 6638 | 919-AlaAlaArgLysArgLeuAspIleGlyAlaLysGluIleHisAsnGlnGlu-935 |
| SEQ. ID. NO. 6639 | 949-AsnArgLeuAspGluGlnHisHis-956 |
| SEQ. ID. NO. 6640 | 995-ThrTyrLeuAlaLysAlaGluLysGlnValArgAsp-1006 |
| SEQ. ID. NO. 6641 | 1018-AlaGlyLysAspGlyLeuPhe-1024 |
| SEQ. ID. NO. 6642 | 1027-SerGlnGlyGlnLysAspGlnThr-1034 |
| SEQ. ID. NO. 6643 | 1042-AsnGlySerArgIleGluAla-1048 |
| SEQ. ID. NO. 6644 | 1060-ThrTyrLysGluArgIleIleGluAsnArgPro-1070 |
| SEQ. ID. NO. 6645 | 1087-LeuAsnLysAspSerArgIle-1093 |
| SEQ. ID. NO. 6646 | 1099-IleIleThrAspAspLeuAsnGlnLysGluIleThrAsn-1111 |
| SEQ. ID. NO. 6647 | 1114-ThrThrGlyLysGlyArgThrAspAlaVal-1123 |
| SEQ. ID. NO. 6648 | 1134-GlyTrpTyrSerGlyArgLysArgGlnArgArgThrGluArgAsnHis-1149 |
| SEQ. ID. NO. 6649 | 1235-ThrAspProGlnPheAlaAspTyrArgArg-1244 |
| SEQ. ID. NO. 6650 | 1261-HisLeuHisLysArgLeuGly-1267 |
| SEQ. ID. NO. 6651 | 1287-ArgArgLeuAspGlyTyrArgSerAspGluGluGlnPheLysAlaLeuMet-1303 |
| SEQ. ID. NO. 6652 | 1360-AlaArgLysGlyAspLeuAsnThr-1367 |
| SEQ. ID. NO. 6653 | 1416-IleGlyLeuLysAlaGluLysSerIleAsn-1425 |
| SEQ. ID. NO. 6654 | 1453-SerGlyAsnGluArgAsnGlyAsnThrAlaIleAspArgMetAla-1467 |
| SEQ. ID. NO. 6655 | 1475-HisThrGluGlnValAspAsnArgThrSerAsp-1485 |
| SEQ. ID. NO. 6656 | 1505-AsnGlnValLysAspGlyThrThr-1512 |
| SEQ. ID. NO. 6657 | 1525-IleArgThrGluHisArgGluAlaTyrGlyThrLeuAspAspGluAsnHisArgHisValArgGlnSerThrGluVal-1550 |
| SEQ. ID. NO. 6658 | 1554-IleArgThrGlnAsn-1558 |
| SEQ. ID. NO. 6659 | 1564-AlaGlyAsnAspLeuLysIleArgGlnGlyGluLeuGluAlaGluGluGlyLysThr-1582 |
| SEQ. ID. NO. 6660 | 1586-AlaGlyArgAspValThrIleSerGluGlyArgGlnIleThrGluLeuAspThr-1603 |
| SEQ. ID. NO. 6661 | 1605-ValSerGlyLysSerLysGlyIle-1612 |
| SEQ. ID. NO. 6662 | 1616-ThrLysThrHisAspArgTyrArgPheSerHisAspGluAlaVal-1630 |
| SEQ. ID. NO. 6663 | 1647-IleAsnValArgGly-1651 |
| SEQ. ID. NO. 6664 | 1653-AsnLeuIleSerAspLysGlyIleVal-1661 |
| SEQ. ID. NO. 6665 | 1664-AlaGlyHisAspIleAspIle-1670 |
| SEQ. ID. NO. 6666 | 1681-GluTyrHisGluSerLysLysSerGlyVal-1690 |
| SEQ. ID. NO. 6667 | 1701-GlyAsnArgLysThrThrAspAspThrAspArgThrAsn-1713 |
| SEQ. ID. NO. 6668 | 1734-AsnArgTyrArgGlnThrGly-1740 |
| SEQ. ID. NO. 6669 | 1744-SerSerProGluGlyArgAsnThrValThr-1753 |
| SEQ. ID. NO. 6670 | 1774-GlnGluGlnLysGly-1778 |
| SEQ. ID. NO. 6671 | 1800-AsnValGlyLysSerLysAsnLysArgValAsn-1810 |
| SEQ. ID. NO. 6672 | 1836-SerAlaGlyGlnGlyGlnAsnAsnAsnGln-1845 |
| SEQ. ID. NO. 6673 | 1856-GlyGluGlnLysSerArgAsnGluGlnLysArgHisTyrThr-1869 |
| SEQ. ID. NO. 6674 | 1888-GlySerGlyGluGlnSerAsn-1894 |
| SEQ. ID. NO. 6675 | 1919-GlnSerAlaLysGlnAspGlySerGluGlnSerLysAsnLysSerSer-1934 |
| SEQ. ID. NO. 6676 | 1957-AsnIleGlyLysGlyLysGluGlnGlyGly-1966 |
| SEQ. ID. NO. 6677 | 1982-ThrThrIleArgSerGlyGlyAspThrThrLeu-1992 |

| | |
|---|---|
| SEQ. ID. NO. 6678 | 2002-IleGlnAlaAspThrArgAsnLeuHis-2010 |
| SEQ. ID. NO. 6679 | 2013-SerValGlnAspThrGluThrTyrGlnSerLysGlnGlnAsn-2026 |
| SEQ. ID. NO. 6680 | 2041-GlySerTyrArgGlnSerLysValLysAlaAspHis-2052 |
| SEQ. ID. NO. 6681 | 2063-AlaGlyGluAspGlyTyrGlnIleLysValArgAspAsnThrAspLeuLysGly-2080 |
| SEQ. ID. NO. 6682 | 2087-GlnSerAlaGluAspLysGlyLysAsn-2095 |
| SEQ. ID. NO. 6683 | 2111-SerArgTyrGluGlyArgSer-2117 |
| SEQ. ID. NO. 6684 | 2133-ThrValThrAspLysGlnGlyArgProThrAspArgIleSerPro-2147 |
| SEQ. ID. NO. 6685 | 2152-GlySerAspGlyAspSerLysAsnSerThrThrArgSerGlyVal-2166 |
| SEQ. ID. NO. 6686 | 2173-IleThrAspGluAlaGlyGln-2179 |
| SEQ. ID. NO. 6687 | 2181-AlaArgThrGlyArgThrAlaLysGluThrGluAlaArgIle-2194 |
| SEQ. ID. NO. 6688 | 2198-IleAspThrGluThrAlaAspGlnHisSerGlyHisLeu-2210 |
| SEQ. ID. NO. 6689 | 2212-AsnSerPheAspLysAspAlaValAlaLysGluIleAsnLeuGlnArgGluValThrLysGluPheGlyArg-2235 |
| SEQ. ID. NO. 6690 | 2244-ValAlaAspLysLeuGlyAsn-2250 |
| SEQ. ID. NO. 6691 | 2252-GlnSerTyrGluArgTyrGlnGluAlaArgThrLeuLeu-2264 |
| SEQ. ID. NO. 6692 | 2266-AlaGluLeuGlnAsnThrAspSerGluAlaGluLysAlaAlaPhe-2280 |
| SEQ. ID. NO. 6693 | 2294-AsnGlnSerArgTyrAspThrTrpLysGluGlyGlyIle-2306 |
| SEQ. ID. NO. 6694 | 2338-TyrLeuAspLysAlaAlaGluAsnLeuGlyProAlaGly-2350 |
| SEQ. ID. NO. 6695 | 2384-GlnLeuHisProLysGluMetAlaLeu-2392 |
| SEQ. ID. NO. 6696 | 2394-AspLysTyrAlaGluAlaLeuLysArgGluValGluLysArgGluGlyArgLysIleSerSerGlnGluAlaAlaMetArgIleArgArgGlnIle-2425 |
| SEQ. ID. NO. 6697 | 2428-TrpValAspLysGlySerGlnAspGlyTyrThr-2438 |
| SEQ. ID. NO. 6698 | 2448-MetLysGlyGluAspLysAlaLeu-2455 |
| SEQ. ID. NO. 6699 | 2460-AspTyrArgAspTyrGlyAlaArgAsnProGlnThrTyrAsnAsp-2474 |
| SEQ. ID. NO. 6700 | 2476-LysLeuPheGluGluTyrArgArgGlnAspLysProGluTyrArg-2490 |
| SEQ. ID. NO. 6701 | 2498-GlyThrLysAspThrLysIleArgGlnGlyGluArgLysAsnGluGluPhe-2514 |
| SEQ. ID. NO. 6702 | 2528-ProAsnProArgIleLys-2533 |
| SEQ. ID. NO. 6703 | 2541-ArgAsnLeuLysAsnIleLys-2547 |
| SEQ. ID. NO. 6704 | 2570-AsnValAlaLysGlyAspArgIleProAsp-2579 |
| SEQ. ID. NO. 6705 | 2585-LysGlyIleLysHisLysAsnArgLysAspGlnLeuGluLysAsnLysLysSerGlyGluAspPheGluMet-2608 |
| SEQ. ID. NO. 6706 | 2610-IleTyrGlnLysLysValLysGlnGlyPheLysProGlnArg-2623 |
| SEQ. ID. NO. 6707 | 2625-IleThrValLysThrLysSerGlyValLysThrArgLeuAspIleIleSerLysGluGlyGlyLeu-2646 |
| SEQ. ID. NO. 6708 | 2648-ValCysThrGluCysLysAla-2654 |
| SEQ. ID. NO. 6709 | 2660-LeuThrLysAsnGlnLysLysAlaPheProGluIleGluArgThrGly-2675 |
| SEQ. ID. NO. 6710 | 2680-GlyLysGlyLysProGlyTyrProLysGlyThrLysIleGluProThrLysValIleIleGluArgLysArg-2703 |
| 565 | |
| AMPHI Regions - AMPHI | |
| SEQ. ID. NO. 6711 | 50-AlaThrCysThrArgAlaMetSerLysSer-59 |
| SEQ. ID. NO. 6712 | 66-SerSerTrpAlaArg-70 |
| SEQ. ID. NO. 6713 | 84-IleSerThrTrpSerAspLeu-90 |
| SEQ. ID. NO. 6714 | 103-AspPheMetSerGlnLeuAspLeuThr-111 |
| SEQ. ID. NO. 6715 | 140-SerHisSerGlyGluThrIleSerSerCysProAlaMetAlaSerIleThrLysProAsn-159 |
| SEQ. ID. NO. 6716 | 184-AlaAsnThrThrSerAlaPhe-190 |
| Antigenic Index - Jameson-Wolf | |
| SEQ. ID. NO. 6717 | 1-MetAspSerThrLeuSerLysThrCys-9 |
| SEQ. ID. NO. 6718 | 23-PheAlaArgProArgProAlaAlaSerAsnThrSerLeu-35 |
| SEQ. ID. NO. 6719 | 37-PheAlaSerProAsnAspThrGlySer-45 |
| SEQ. ID. NO. 6720 | 55-AlaMetSerLysSerSerAlaLysTyrGly-64 |
| SEQ. ID. NO. 6721 | 67-SerTrpAlaArgThrArgProThrValCysProProLeuProLysProThrIle-84 |
| SEQ. ID. NO. 6722 | 99-CysArgSerSerAspPheMetSer-106 |
| SEQ. ID. NO. 6723 | 109-AspLeuThrLysArgProThrSerAlaSerLeuProProLysArgLysGlyAlaIle-127 |
| SEQ. ID. NO. 6724 | 129-IleAspSerArgThrAlaAla-135 |
| SEQ. ID. NO. 6725 | 140-SerHisSerGlyGluThrIleSerSer-148 |
| SEQ. ID. NO. 6726 | 154-SerIleThrLysProAsnSerProProCysAlaArgTyr-166 |
| SEQ. ID. NO. 6727 | 170-LeuArgLeuSerProThrGlu-176 |
| SEQ. ID. NO. 6728 | 194-SerIleAlaAsnSerIleAsnThrCysArgGlnProPro-206 |
| Hydrophilic Regions - Hopp-Woods | |
| SEQ. ID. NO. 6729 | 24-AlaArgProArgProAlaAla-30 |
| SEQ. ID. NO. 6730 | 39-SerProAsnAspThrGlySer-45 |
| SEQ. ID. NO. 6731 | 55-AlaMetSerLysSerSerAla-61 |
| SEQ. ID. NO. 6732 | 69-AlaArgThrArgPro-73 |
| SEQ. ID. NO. 6733 | 100-ArgSerSerAspPhe-104 |
| SEQ. ID. NO. 6734 | 109-AspLeuThrLysArgProThrSer-116 |
| SEQ. ID. NO. 6735 | 119-LeuProProLysArgLysGlyAlaIle-127 |
| SEQ. ID. NO. 6736 | 129-IleAspSerArgThr-133 |
| SEQ. ID. NO. 6737 | 141-HisSerGlyGluThrIleSer-147 |
| SEQ. ID. NO. 6738 | 156-ThrLysProAsnSer-160 |
| 566 | |
| Hydrophilic Regions - Hopp-Woods | |
| SEQ. ID. NO. 6739 | 29-ProPheArgAspGlyAlaHisLysMet-37 |
| SEQ. ID. NO. 6740 | 64-AsnIleProAspArgProAla-70 |
| SEQ. ID. NO. 6741 | 95-ValAlaLysArgGluLeuPhe-101 |
| SEQ. ID. NO. 6742 | 116-IleGlyIleAspArgAsnAsnArgArgGluAlaAsnGluGlnLeuIle-131 |
| SEQ. ID. NO. 6743 | 134-GlyLeuValArgLysAsnGlu-140 |
| SEQ. ID. NO. 6744 | 149-GluGlyThrArgLeuAlaProGlyLysArgGlyLysTyrLysLeuGlyGly-165 |
| SEQ. ID. NO. 6745 | 211-SerGlySerGluAlaGluLeuMetGluLysCysGluHisLeuIle-225 |
| SEQ. ID. NO. 6746 | 242-MetProSerGluThrAla-247 |
| Antigenic Index - Jameson-Wolf | |
| SEQ. ID. NO. 6747 | 32-PheAlaValAspProAsnCysGlyAlaAspGlyThrGlyGlyLysGlyHisAla-49 |
| SEQ. ID. NO. 6748 | 61-AlaValGlyGlyGluGluGlyGlyValValAlaAspAspValAlaCysAlaAspGlyGlyLysAlaAspGlyArgArgIleAlaArg-89 |
| SEQ. ID. NO. 6749 | 105-SerAlaGluArgAlaGlyAspAspPheAla-114 |

TABLE 1-continued

Hydrophilic Regions - Hopp-Woods
SEQ. ID. NO. 6750 36-ProAsnCysGlyAlaAspGlyThrGlyGlyLysGlyHisAla-49
SEQ. ID. NO. 6751 63-GlyGlyGluGluGlyGlyValValAlaAspAspValAlaCys-76
SEQ. ID. NO. 6752 78-AspGlyGlyLysAlaAspGlyArgArgIleAlaArg-89
SEQ. ID. NO. 6753 105-SerAlaGluArgAlaGlyAspAspPheAla-114
567
AMPHI Regions - AMPHI
SEQ. ID. NO. 6754 60-GlyValTyrGlnVal-64
SEQ. ID. NO. 6755 98-GluLeuValGlnGluIleAlaArgGluVal-107
SEQ. ID. NO. 6756 112-AlaLeuLysAlaVal-116
SEQ. ID. NO. 6757 154-TyrAlaLeuGluGlyIleSerAspLeuIleAlaThrValArgLysIleArgGln-171
SEQ. ID. NO. 6758 180-ThrGlyIleValArg-184
SEQ. ID. NO. 6759 195-AlaGluValSerGluGlnLeuArgSerHisPheGlyAspLeuLeu-209
Antigenic Index - Jameson-Wolf
SEQ. ID. NO. 6760 10-AsnGlnLysGlyGlyValGlyLysThrThrThr-20
SEQ. ID. NO. 6761 28-LeuAlaSerArgGlyLysArg-34
SEQ. ID. NO. 6762 38-ValAspLeuAspProGlnGlyAsnAlaThrThrGlySerGlyIleAspLysAlaGlyLeuGlnSerGly-60
SEQ. ID. NO. 6763 67-GlyAspAlaAspValGln-72
SEQ. ID. NO. 6764 75-AlaValArgSerLysGluGlyGly-82
SEQ. ID. NO. 6765 95-AlaGluIleGluLeu-99
SEQ. ID. NO. 6766 101-GlnGluIleAlaArgGluValArgLeuLysAsnAlaLeuLysAlaValGluGluAspTyrAsp-121
SEQ. ID. NO. 6767 127-CysProProSerLeu-131
SEQ. ID. NO. 6768 164-AlaThrValArgLysIleArgGlnAlaValAsnProAspLeuAspIle-179
SEQ. ID. NO. 6769 185-ThrMetTyrAspSerArgSerArgLeuValAlaGluValSerGluGlnLeuArgSerHisPheGlyAspLeu-208
SEQ. ID. NO. 6770 214-IleProArgAsnIleArgLeuAlaGluAlaProSerHisGly-227
SEQ. ID. NO. 6771 235-AlaGlnAlaLysGlyThrLys-241
SEQ. ID. NO. 6772 248-AspGluLeuAlaAlaArgValSerGlyLys-257
Hydrophilic Regions - Hopp-Woods
SEQ. ID. NO. 6773 10-AsnGlnLysGlyGlyValGlyLys-17
SEQ. ID. NO. 6774 28-LeuAlaSerArgGlyLysArg-34
SEQ. ID. NO. 6775 40-LeuAspProGlnGly-44
SEQ. ID. NO. 6776 50-SerGlyIleAspLysAlaGlyLeu-57
SEQ. ID. NO. 6777 67-GlyAspAlaAspValGln-72
SEQ. ID. NO. 6778 75-AlaValArgSerLysGluGlyGly-82
SEQ. ID. NO. 6779 95-AlaGluIleGluLeu-99
SEQ. ID. NO. 6780 101-GlnGluIleAlaArgGluValArgLeuLysAsnAlaLeuLysAlaValGluGluAspTyrAsp-121
SEQ. ID. NO. 6781 164-AlaThrValArgLysIleArgGln-171
SEQ. ID. NO. 6782 175-ProAspLeuAspIle-179
SEQ. ID. NO. 6783 186-MetTyrAspSerArgSerArgLeuValAlaGluValSerGluGlnLeuArg-202
SEQ. ID. NO. 6784 216-ArgAsnIleArgLeuAlaGluAlaProSer-225
SEQ. ID. NO. 6785 235-AlaGlnAlaLysGlyThrLys-241
SEQ. ID. NO. 6786 248-AspGluLeuAlaAla-252
568
AMPHI Regions - AMPHI
SEQ. ID. NO. 6787 32-AsnIlePheArgArgIle-37
SEQ. ID. NO. 6788 49-LysAlaCysLysAsn-53
SEQ. ID. NO. 6789 71-GluLysAlaAsnThrValArgTyr-78
SEQ. ID. NO. 6790 82-SerLeuAlaGlnCysPheThr-88
SEQ. ID. NO. 6791 112-ArgProLeuProSerIleIleThrAla-120
SEQ. ID. NO. 6792 169-GluPheValGlyPheGlyAsnValPheValGlyGlnPheLeuAsnArgPhePhe-186
SEQ. ID. NO. 6793 200-GluGluPhePheAspValValVal-207
SEQ. ID. NO. 6794 228-PheAsnGlnValPheAlaAlaPheLeu-236
SEQ. ID. NO. 6795 241-HisArgHisAlaAspGlnValAlaAspSerCysArgValGlnSerGln-256
Antigenic Index - Jameson-Wolf
SEQ. ID. NO. 6796 14-SerAlaSerSerMetProCysArgIleCysArgLeuLysArgSerArgLeuProAsnIlePhe-34
SEQ. ID. NO. 6797 39-PheSerCysArgArgArgThrCysPheCysLysAlaCysLysAsnSerProIleArgAsnGluThrSerSerSerGlyArgArgGlnPheSerValGluLys AlaAsnThr-75
SEQ. ID. NO. 6798 91-SerAsnAlaSerLysProArgLeu-98
SEQ. ID. NO. 6799 100-ProIleMetArgGlyArgLysArgPhePheAla-110
SEQ. ID. NO. 6800 141-PheArgGlySerAlaPheLysCysArgLeuAsnAlaGluProCysArg-156
SEQ. ID. NO. 6801 213-ValAlaAspArgAspAlaAla-219
SEQ. ID. NO. 6802 237-GlyGlnHisGlyHisArgHisAlaAspGlnValAlaAspSerCysArgValGlnSerGln-256
Hydrophilic Regions - Hopp-Woods
SEQ. ID. NO. 6803 21-ArgIleCysArgLeuLysArgSerArgLeu-30
SEQ. ID. NO. 6804 41-CysArgArgArgThrCysPhe-47
SEQ. ID. NO. 6805 49-LysAlaCysLysAsnSerProIleArgAsnGluThrSerSerSerGlyArgArgGlnPheSerValGluLysAlaAsnThr-75
SEQ. ID. NO. 6806 93-AlaSerLysProArgLeu-98
SEQ. ID. NO. 6807 102-MetArgGlyArgLysArgPhePheAla-110
SEQ. ID. NO. 6808 144-SerAlaPheLysCysArgLeuAsnAlaGluProCysArg-156
SEQ. ID. NO. 6809 213-ValAlaAspArgAspAlaAla-219
SEQ. ID. NO. 6810 239HisGlyHisArgHisAlaAspGlnValAlaAspSerCysArgVal-253
569
AMPHI Regions - AMPHI
SEQ. ID. NO. 6811 29-AlaAlaPheCysGlyLeuIleAlaLeuIleAlaLeuTrpGluTyrAlaArgMetGlyGlyLeuCysLys-51
SEQ. ID. NO. 6812 86-PheTrpLeuAlaValMetPro-92
SEQ. ID. NO. 6813 166-SerProGlyLysSerTrpGluGlyAlaIle-175
SEQ. ID. NO. 6814 203-ThrValLeuIleGlyLeu-208
SEQ. ID. NO. 6815 210-LeuThrValValSerValCysGlyAspLeuLeuGluSerTrpLeuLys-225
SEQ. ID. NO. 6816 229-GlyIleLysAspSerSer-234

TABLE 1-continued

Antigenic Index - Jameson-Wolf
SEQ. ID. NO. 6817 50-CysLysIleLysThrAsnHis-56
SEQ. ID. NO. 6818 98-LysTrpArgLeuAsnGlyGlyTrp-105
SEQ. ID. NO. 6819 124-SerLeuArgProHisProAspAspAlaLeu-133
SEQ. ID. NO. 6820 154-LysAlaPheGlyLysHisLysIle-161
SEQ. ID. NO. 6821 165-IleSerProGlyLysSerTrpGlu-172
SEQ. ID. NO. 6822 227-AlaAlaGlyIleLysAspSerSerLysLeuLeuProGlyHis-240
SEQ. ID. NO. 6823 242-GlyValPheAspArgThrAspSer-249
Hydrophilic Regions - Hopp-Woods
SEQ. ID. NO. 6824 50-CysLysIleLysThr-54
SEQ. ID. NO. 6825 127-ProHisProAspAspAlaLeu-133
SEQ. ID. NO. 6826 155-AlaPheGlyLysHisLysIle-161
SEQ. ID. NO. 6827 227-AlaAlaGlyIleLysAspSerSerLys-235
SEQ. ID. NO. 6828 243-ValPheAspArgThrAspSer-249
570
AMPHI Regions - AMPHI
SEQ. ID. NO. 6829 6-ArgAlaPheAlaAlaAlaLeuIleGlyLeu-15
SEQ. ID. NO. 6830 22-HisAlaAspThrPheGlnLysIleGlyPheIleAsn-33
SEQ. ID. NO. 6831 43-GlnAlaArgLysIleGlnLysThrLeuAspSer-53
SEQ. ID. NO. 6832 60-AspGluLeuGlnLysLeuGln-66
SEQ. ID. NO. 6833 81-LeuArgAsnAlaLysLys-86
SEQ. ID. NO. 6834 91-GluLysTrpArgGlyLeuValAla-98
SEQ. ID. NO. 6835 122-LeuGlnGlnAsnAlaAsnArgValIleValLysIle-133
Antigenic Index - Jameson-Wolf
SEQ. ID. NO. 6836 33-AsnThrGluArgIleTyrLeuGluSerLysGlnAlaArgLysIleGlnLysThrLeuAspSerGluPheSerAlaArgGlnAspGluLeuGlnLysLeuGln ArgGluGlyLeuAspLeuGluArgGlnLeuAlaGluGlyLysLeuArgAsnAlaLysLysAlaGlnAlaGluGluLysTrpArg-94
SEQ. ID. NO. 6837 100-PheArgLysLysGlnAlaGlnPheGluGluAspTyrAsnLeuArgArgAsnGluGluPheAla-120
SEQ. ID. NO. 6838 123-GlnGlnAsnAlaAsnArgVal-129
SEQ. ID. NO. 6839 133-IleAlaLysGlnGluGlyTyrAspVal-141
SEQ. ID. NO. 6840 152-GlnTyrAspValThrAspSerValIleLysGluMetAsnAlaArg-166
Hydrophilic Regions - Hopp-Woods
SEQ. ID. NO. 6841 37-IleTyrLeuGluSerLysGlnAlaArgLysIleGlnLysThrLeuAspSerGluPheSerAlaArgGlnAspGluLeuGlnLysLeuGlnArgGluGlyLeu AspLeuGluArgGlnLeuAlaGluGlyLysLeuArgAsnAlaLysLysAlaGlnAlaGluGluLysTrpArg-94
SEQ. ID. NO. 6842 100-PheArgLysLysGlnAlaGlnPheGluGluAspTyrAsnLeuArgArgAsnGluGluPheAla-120
SEQ. ID. NO. 6843 133-IleAlaLysGlnGluGlyTyr-139
SEQ. ID. NO. 6844 154-AspValThrAspSerValIleLysGluMetAsnAlaArg-166
571
AMPHI Regions - AMPHI
SEQ. ID. NO. 6845 6-AlaValAsnValLeu-10
SEQ. ID. NO. 6846 40-AspGlyAlaArgValPheArgAlaGly-48
SEQ. ID. NO. 6847 63-AlaAlaValAlaAspPhePheAlaVal-71
SEQ. ID. NO. 6848 94-ValGluValPheLysGlu-99
Antigenic Index - Jameson-Wolf
SEQ. ID. NO. 6849 13-AlaAlaGlyArgGlyThr-18
SEQ. ID. NO. 6850 35-LysGlnAlaGlnAlaAspGlyAlaArgValPheArgAlaGlyHisArgGluGluGlnLeuGlyGlyAspVal-58
SEQ. ID. NO. 6851 76-PheArgThrGluArgAlaAla-82
SEQ. ID. NO. 6852 96-ValPheLysGluGlyAspPhe-102
SEQ. ID. NO. 6853 110-ArgAsnAlaAspPheAlaAlaGluHisGlnArGluGlyPheAlaGlnGlyGluGluProGlyLeu-131
SEQ. ID. NO. 6854 142-AlaAlaArgGlnGlyAspPheGlyVal-150
SEQ. ID. NO. 6855 155-ValAlaAlaArgArgPro-160
Hydrophilic Regions - Hopp-Woods
SEQ. ID. NO. 6856 13-AlaAlaGlyArgGly-17
SEQ. ID. NO. 6857 35-LysGlnAlaGlnAlaAspGlyAlaArgValPheArgAlaGlyHisArgGluGluGlnLeuGly-55
SEQ. ID. NO. 6858 76-PheArgThrGluArgAlaAla-82
SEQ. ID. NO. 6859 96-ValPheLysGluGlyAspPhe-102
SEQ. ID. NO. 6860 110-ArgAsnAlaAspPheAlaAlaGluHisGlnArgGluGlyPheAlaGlnGlyGluGluProGly-130
SEQ. ID. NO. 6861 155-ValAlaAlaArgArgPro-160
572-2
AMPHI Regions - AMPHI
SEQ. ID. NO. 6862 20-LeuAspValValSerArgHisProGluLysPheArgVal-32
SEQ. ID. NO. 6863 39-LysGlnValGluLysLeuAlaAlaGlnCys-48
SEQ. ID. NO. 6864 85-GlnAlaLeuValAspValAlaSerAlaAspGlu-95
SEQ. ID. NO. 6865 101-CysAlaIleValGlyAlaValGlyLeuProSerAlaLeuAla-114
SEQ. ID. NO. 6866 160-GlnValLeuProArgAspTyrAlaGlyArg-169
SEQ. ID. NO. 6867 192-LeuAsnThrPheAspArgIleThrProAlaGlnAlaValLys-205
SEQ. ID. NO. 6868 225-LysGlyLeuGluLeu-229
SEQ. ID. NO. 6869 253-IleHisSerMetValArg-258
SEQ. ID. NO. 6870 282-GlyLeuProGluArgIleAspSerGly-290
SEQ. ID. NO. 6871 299-LeuSerAlaLeuThr-303
SEQ. ID. NO. 6872 340-ValAlaAlaPheLeu-344
SEQ. ID. NO. 6873 350-PheThrAspIleAlaLysThrValAlaHisCysLeuAlaGlnAspPheSerAspGlyIleGlyAspIleGlyGly-374
Antigenic Index - Jameson-Wolf
SEQ. ID. NO. 6874 11-SerThrGlySerIleGlyGluSerThrLeu-20
SEQ. ID. NO. 6875 22-ValValSerArgHisProGluLysPheArg-31
SEQ. ID. NO. 6876 39-LysGlnValGluLysLeuAla-45
SEQ. ID. NO. 6877 59-AlaAspAlaGluHisAlaAlaArgLeu-67
SEQ. ID. NO. 6878 69-AlaLeuLeuLysArgAspGlyThrAla-77
SEQ. ID. NO. 6879 91-AlaSerAlaAspGluValSer-97
SEQ. ID. NO. 6880 117-GlnLysGlyLysThr-121
SEQ. ID. NO. 6881 125-AlaAsnLysGluThrLeu-130

TABLE 1-continued

| | |
|---|---|
| SEQ. ID. NO. 6882 | 140-ThrAlaArgAlaAsnGly-145 |
| SEQ. ID. NO. 6883 | 150-ProValAspSerGluHis-155 |
| SEQ. ID. NO. 6884 | 162-LeuProArgAspTyrAlaGlyArgLeuAsnGluHisGly-174 |
| SEQ. ID. NO. 6885 | 193-AsnThrPheAspArgIleThrProAlaGlnAlaValLysHisProAsnTrpArgMetGlyArgLysIleSerValAspSer-219 |
| SEQ. ID. NO. 6886 | 224-AsnLysGlyLeuGluLeu-229 |
| SEQ. ID. NO. 6887 | 237-AsnCysProProAspLysLeuGluVal-245 |
| SEQ. ID. NO. 6888 | 257-ValArgTyrArgAspGlySerVal-264 |
| SEQ. ID. NO. 6889 | 269-GlyAsnProAspMetArgThr-275 |
| SEQ. ID. NO. 6890 | 283-LeuProGluArgIleAspSerGlyValGlyAspLeuAspPhe-296 |
| SEQ. ID. NO. 6891 | 303-ThrPheGlnLysProAspPheAspArg-311 |
| SEQ. ID. NO. 6892 | 363-GlnAspPheSerAspGlyIleGlyAspIleGly-373 |
| SEQ. ID. NO. 6893 | 378-GlnAspAlaArgThrArgAlaGlnAla-386 |
| Hydrophilic Regions - Hopp-Woods | |
| SEQ. ID. NO. 6894 | 22-ValValSerArgHisProGluLysPheArg-31 |
| SEQ. ID. NO. 6895 | 39-LysGlnValGluLysLeuAla-45 |
| SEQ. ID. NO. 6896 | 59-AlaAspAlaGluHisAlaAlaArgLeu-67 |
| SEQ. ID. NO. 6897 | 69-AlaLeuLeuLysArgAspGlyThrAla-77 |
| SEQ. ID. NO. 6898 | 91-AlaSerAlaAspGluValSer-97 |
| SEQ. ID. NO. 6899 | 126-AsnLysGluThrLeu-130 |
| SEQ. ID. NO. 6900 | 140-ThrAlaArgAlaAsnGly-145 |
| SEQ. ID. NO. 6901 | 151-ValAspSerGluHis-155 |
| SEQ. ID. NO. 6902 | 165-AspTyrAlaGlyArgLeuAsnGlu-172 |
| SEQ. ID. NO. 6903 | 196-AspArgIleThrPro-200 |
| SEQ. ID. NO. 6904 | 210-ArgMetGlyArgLysIleSerVal-217 |
| SEQ. ID. NO. 6905 | 225-LysGlyLeuGluLeu-229 |
| SEQ. ID. NO. 6906 | 239-ProProAspLysLeuGlu-244 |
| SEQ. ID. NO. 6907 | 257-ValArgTyrArgAspGlySer-263 |
| SEQ. ID. NO. 6908 | 269-GlyAsnProAspMetArgThr-275 |
| SEQ. ID. NO. 6909 | 283-LeuProGluArgIleAspSerGlyValGlyAspLeuAspPhe-296 |
| SEQ. ID. NO. 6910 | 305-GlnLysProAspPheAspArg-311 |
| SEQ. ID. NO. 6911 | 364-AspPheSerAspGlyIleGly-370 |
| SEQ. ID. NO. 6912 | 378-GlnAspAlaArgThrArgAlaGlnAla-386 |
| 574 | |
| AMPHI Regions - AMPHI | |
| SEQ. ID. NO. 6913 | 6-ProAsnSerLeuLysLys-11 |
| SEQ. ID. NO. 6914 | 47-LeuLysGlnAlaLysSerIleProSerGlyPheTyrLysSerLeuAspAlaLeuValAspArgAsnSerGlyArgAlaAlaArgGluLeuAlaGluValValAsp-81 |
| SEQ. ID. NO. 6915 | 94-GlyLysLeuTyrArgGln-99 |
| SEQ. ID. NO. 6916 | 113-MetLeuAspSerProAspThr-119 |
| SEQ. ID. NO. 6917 | 175-GluLysAlaValGluThrAlaArgLeu-183 |
| SEQ. ID. NO. 6918 | 218-AsnValGlyLysAlaLeuGluAlaAsnLysLysCys-229 |
| SEQ. ID. NO. 6919 | 246-PheProAlaAlaValGluAlaTyrAlaAlaIleGlu-257 |
| SEQ. ID. NO. 6920 | 266-MetValGlyGluLysLeuTyrGluAlaTyrAla-276 |
| SEQ. ID. NO. 6921 | 281-ProGluGluGlyLeuAsnArgLeuThrGlyTyrMetGlnThrPheProGluLeuAspLeu-300 |
| SEQ. ID. NO. 6922 | 332-AsnGlyValTyrArg-336 |
| SEQ. ID. NO. 6923 | 357-ArgSerValIleGlyArgGlnLeuGlnArgSer-367 |
| Antigenic Index - Jameson-Wolf | |
| SEQ. ID. NO. 6924 | 1-MetArgProAsnLeuProAsnSerLeuLysLysAlaAspMetAspAsn-16 |
| SEQ. ID. NO. 6925 | 45-ThrValLeuLysGlnAlaLysSerIleProSerGlyPheTyrLysSerLeuAspAlaLeuValAspArgAsnSerGlyArgAlaAlaArgGluLeuAlaGluValValAspGlyArgProGlnSerTyrAsp-88 |
| SEQ. ID. NO. 6926 | 96-LeuTyrArgGlnArgGlyGluAsnAspLysAlaIleAsnIleHisArgThrMetLeuAspSerProAspThrValGlyGluLysArgAlaArgVal-127 |
| SEQ. ID. NO. 6927 | 135-TyrGlnSerAlaGlyLeuValAspArgAlaGlu-145 |
| SEQ. ID. NO. 6928 | 151-LeuGlnAspGlyLysMetAlaArgGluAlaArgGln-162 |
| SEQ. ID. NO. 6929 | 168-TyrGlnGlnAspArgAspTrpGluLysAlaValGluThr-180 |
| SEQ. ID. NO. 6930 | 182-ArgLeuLeuSerHisAspAspGlnThrTyr-191 |
| SEQ. ID. NO. 6931 | 221-LysAlaLeuGluAlaAsnLysLysCysThrArg-231 |
| SEQ. ID. NO. 6932 | 238-AspIleGluHisArgGlnGlyAsn-245 |
| SEQ. ID. NO. 6933 | 277-AlaGlnGlyLysProGluGluGlyLeuAsnArgLeuThrGlyTyr-291 |
| SEQ. ID. NO. 6934 | 312-LysCysGluLysGluAlaAla-318 |
| SEQ. ID. NO. 6935 | 323-GluLeuValArgArgLysProAspLeuAsnGly-333 |
| SEQ. ID. NO. 6936 | 341-LysLeuSerAspMetAsnProAlaTrpLysAlaAspAlaAspMetMetArg-357 |
| SEQ. ID. NO. 6937 | 368-ValMetTyrArgCysArgAsnCysHisPheLys-378 |
| SEQ. ID. NO. 6938 | 386-CysProAlaCysAsnLysTrpGlnThrPheThrProAsnLysIleGluVal-402 |
| Hydrophilic Regions - Hopp-Woods | |
| SEQ. ID. NO. 6939 | 1-MetArgProAsnLeu-5 |
| SEQ. ID. NO. 6940 | 7-AsnSerLeuLysLysAlaAspMetAspAsn-16 |
| SEQ. ID. NO. 6941 | 45-ThrValLeuLysGlnAlaLysSerIle-53 |
| SEQ. ID. NO. 6942 | 62-AspAlaLeuValAspArgAsnSerGlyArgAlaAlaArgGluLeuAlaGluValValAspGlyArgProGlnSer-86 |
| SEQ. ID. NO. 6943 | 96-LeuTyrArgGlnArgGlyGluAsnAspLysAlaIleAsn-108 |
| SEQ. ID. NO. 6944 | 112-ThrMetLeuAspSerProAspThrValGlyGluLysArgAlaArgVal-127 |
| SEQ. ID. NO. 6945 | 140-LeuValAspArgAlaGlu-145 |
| SEQ. ID. NO. 6946 | 152-GlnAspGlyLysMetAlaArgGluAlaArgGln-162 |
| SEQ. ID. NO. 6947 | 169-GlnGlnAspArgAspTrpGluLysAlaValGluThr-180 |
| SEQ. ID. NO. 6948 | 184-LeuSerHisAspAspGlnThrTyr-191 |
| SEQ. ID. NO. 6949 | 221-LysAlaLeuGluAlaAsnLysLysCysThrArg-231 |
| SEQ. ID. NO. 6950 | 238-AspIleGluHisArgGlnGlyAsn-245 |
| SEQ. ID. NO. 6951 | 279-GlyLysProGluGluGlyLeuAsn-286 |
| SEQ. ID. NO. 6952 | 312-LysCysGluLysGluAlaAla-318 |
| SEQ. ID. NO. 6953 | 323-GluLeuValArgArgLysProAspLeu-331 |
| SEQ. ID. NO. 6954 | 349-TrpLysAlaAspAlaAspMetMetArg-357 |

TABLE 1-continued

SEQ. ID. NO. 6955 368-ValMetTyrArgCysArgAsnCysHis-376
SEQ. ID. NO. 6956 398-AsnLysIleGluVal-402
575
AMPHI Regions - AMPHI
SEQ. ID. NO. 6957 8-PheArgLysProAlaSer-13
SEQ. ID. NO. 6958 20-PheAlaGluAlaVal-24
SEQ. ID. NO. 6959 42-SerThrValSerGlyLeuPheSerAla-50
SEQ. ID. NO. 6960 114-LeuSerLysSerLysSer-119
SEQ. ID. NO. 6961 139-SerSerAspSerPro-143
SEQ. ID. NO. 6962 150-PheThrSerPhePheGly-155
SEQ. ID. NO. 6963 163-ValSerThrSerAlaLysValIleSerMetPro-173
SEQ. ID. NO. 6964 217-SerLysValTyrGluProProAsnArgProSerAsn-228
SEQ. ID. NO. 6965 237-AlaGluThrCysSerThr-242
SEQ. ID. NO. 6966 287-AlaGlyPheSerAlaPheAlaSerGlyAla-296
SEQ. ID. NO. 6967 298-ThrPheAlaSerGlyPheSerThrGly-306
SEQ. ID. NO. 6968 308-SerThrValAlaCys-312
SEQ. ID. NO. 6969 315-GlySerAspGlyMetAspAlaValSerAlaLeu-325
Antigenic Index - Jameson-Wolf
SEQ. ID. NO. 6970 2-ValSerGlyGluGluAlaPheArgLysProAlaSerProGluGlyGluAlaGlyPhe-20
SEQ. ID. NO. 6971 34-GlyArgLeuSerGluLysSerValSer-42
SEQ. ID. NO. 6972 54-ThrAspSerGlySerGlyVal-60
SEQ. ID. NO. 6973 96-SerSerSerCysValSerAlaProAspLysMetProPhe-108
SEQ. ID. NO. 6974 113-ArgLeuSerLysSerLysSerMetArgLeuGluGly-124
SEQ. ID. NO. 6975 134-PheAlaAspAsnSerSerSerAspSerProSerLysAlaSerVal-148
SEQ. ID. NO. 6976 155-GlyAlaGlySerGly-159
SEQ. ID. NO. 6977 173-ProSerSerAlaAlaSerSerArgSerGlySerSerSerGlyThrAspSerSerValArgArgAlaArgLeuAspTrpAlaArgArgLysSerSerSerArgAla Ile-208
SEQ. ID. NO. 6978 211-AlaProProProAlaSer-216
SEQ. ID. NO. 6979 218-LysValTyrGluProProAsnArgProSerAsnSer-229
SEQ. ID. NO. 6980 232-SerValSerSerSerAlaGluThrCysSerThrGlySerGluThr-246
SEQ. ID. NO. 6981 265-GlyAlaAspSerAlaAlaVal-271
SEQ. ID. NO. 6982 280-GlyThrGlySerGlyArgThrAla-287
SEQ. ID. NO. 6983 303-PheSerThrGlyPhe-307
SEQ. ID. NO. 6984 313-LeuAspGlySerAspGlyMetAsp-320
Hydrophilic Regions - Hopp-Woods
SEQ. ID. NO. 6985 2-ValSerGlyGluGluAlaPheArgLysProAlaSerProGluGlyGluAlaGlyPhe-20
SEQ. ID. NO. 6986 34-GlyArgLeuSerGluLysSerValSer-42
SEQ. ID. NO. 6987 101-SerAlaProAspLysMetPro-107
SEQ. ID. NO. 6988 113-ArgLeuSerLysSerLysSerMetArgLeuGluGly-124
SEQ. ID. NO. 6989 137-AsnSerSerSerAspSerProSerLysAla-146
SEQ. ID. NO. 6990 176-AlaAlaSerSerArgSerGlySerSerSerGlyThrAspSerSerValArgArgAlaArgLeuAspTrpAlaArgArgLysSerSerSerArgAlaIle-208
SEQ. ID. NO. 6991 218-LysValTyrGluProProAsnArgProSerAsn-228
SEQ. ID. NO. 6992 235-SerSerAlaGluThrCysSerThrGlySerGluThr-246
SEQ. ID. NO. 6993 314-AspGlySerAspGlyMetAsp-320
576-1
AMPHI Regions - AMPHI
SEQ. ID. NO. 6994 31-AlaSerGluProAlaAlaAla-37
SEQ. ID. NO. 6995 46-SerIleGlySerThr-50
SEQ. ID. NO. 6996 63-GlyArgSerLeuLysGlnMetLys-70
SEQ. ID. NO. 6997 82-ThrGluAlaMetGln-86
SEQ. ID. NO. 6998 102-GlnGluValMetMetLysPheLeuGlnGluGlnGlnAlaLysAlaValGluLysHis-120
SEQ. ID. NO. 6999 140-AlaLysAspGlyValLysThrThr-147
SEQ. ID. NO. 7000 199-SerGlnValIleProGlyTrpThrGluGlyVal-209
Antigenic Index - Jameson-Wolf
SEQ. ID. NO. 7001 20-AlaCysGlyLysLysGluAlaAlaPro-28
SEQ. ID. NO. 7002 30-SerAlaSerGluProAlaAla-36
SEQ. ID. NO. 7003 38-SerSerAlaGlnGlyAspThrSerSerIleGly-48
SEQ. ID. NO. 7004 61-AspIleGlyArgSerLeuLysGlnMetLysGluGlnGlyAlaGluIleAspLeu-78
SEQ. ID. NO. 7005 89-TyrAspGlyLysGluIleLysMetThrGluGluGlnAlaGln-102
SEQ. ID. NO. 7006 109-LeuGlnGluGlnGlnAlaLysAlaValGluLysHisLysAlaAspAlaLysAlaAsnLysGluLysGlyGluAlaPheLeuLysGluAsnAlaAlaLys AspGlyValLysThrThrAlaSerGlyLeu-151
SEQ. ID. NO. 7007 154-LysIleThrLysGlnGlyGluGlyLysGlnProThrLysAspAspIleVal-170
SEQ. ID. NO. 7008 173-GluTyrGluGlyArgLeuIleAsp-180
SEQ. ID. NO. 7009 183-ValPheAspSerSerLysAlaAsnGlyGly-192
SEQ. ID. NO. 7010 210-GlnLeuLeuLysGluGlyGlyGlu-217
SEQ. ID. NO. 7011 224-SerAsnLeuAlaTyrArgGluGlnGlyAlaGlyAspLysIleGlyProAsnAla-241
SEQ. ID. NO. 7012 253-GlyAlaProGluAsnAlaProAlaLysGlnProAla-264
SEQ. ID. NO. 7013 266-ValAspIleLysLysValAsn-272
Hydrophilic Regions - Hopp-Woods
SEQ. ID. NO. 7014 21-CysGlyLysLysGluAlaAlaPro-28
SEQ. ID. NO. 7015 30-SerAlaSerGluProAlaAla-36
SEQ. ID. NO. 7016 40-AlaGlnGlyAspThrSerSer-46
SEQ. ID. NO. 7017 61-AspIleGlyArgSerLeuLysGlnMetLysGluGlnGlyAlaGluIleAspLeu-78
SEQ. ID. NO. 7018 89-TyrAspGlyLysGluIleLysMetThrGluGluGlnAlaGln-102
SEQ. ID. NO. 7019 112-GlnGlnAlaLysAlaValGluLysHisLysAlaAspAlaLysAlaAsnLysGluLysGlyGluAlaPheLeuLysGluAsnAlaAlaLysAspGlyVal LysThrThrAla-148
SEQ. ID. NO. 7020 155-IleThrLysGlnGlyGluGlyLysGlnProThrLysAspAspIleVal-170
SEQ. ID. NO. 7021 173-GluTyrGluGlyArgLeuIleAsp-180
SEQ. ID. NO. 7022 185-AspSerSerLysAlaAsnGly-191
SEQ. ID. NO. 7023 210-GlnLeuLeuLysGluGlyGlyGlu-217

TABLE 1-continued

SEQ. ID. NO. 7024 227-AlaTyrArgGluGlnGlyAlaGlyAspLysIleGlyPro-239
SEQ. ID. NO. 7025 253-GlyAlaProGluAsnAlaProAlaLysGlnProAla-264
SEQ. ID. NO. 7026 266-ValAspIleLysLysValAsn-272
577
AMPHI Regions - AMPHI
SEQ. ID. NO. 7027 8-GlyLysIleValGlyAsn-13
SEQ. ID. NO. 7028 24-AlaAlaSerTyrProLysProCysLysSerPheLysLeuAla-37
SEQ. ID. NO. 7029 62-ThrValIleLysIleIle-67
SEQ. ID. NO. 7030 104-AlaPheValValGlyIleIlePheGlyMetPheAlaLeuPheGlyArg-119
SEQ. ID. NO. 7031 144-GluLeuThrAlaProProAlaGln-151
Antigenic Index - Jameson-Wolf
SEQ. ID. NO. 7032 1-MetGluArgAsnGlyVal-6
SEQ. ID. NO. 7033 14-ArgIleLeuArgMetSerSerGluHisAla-23
SEQ. ID. NO. 7034 26-SerTyrProLysProCysLysSerPheLys-35
SEQ. ID. NO. 7035 88-LeuProGlyGlnLysPheAspLeu-95
SEQ. ID. NO. 7036 121-LeuSerLeuArgGlyGluAsnGlyArgLeuArgAlaGluValLysLysAsnAlaArgLeuThrGlyLysGluLeuThrAlaProProAlaGlnAsnAla
 ProGluSerThrLysGlnPro-160
Hydrophilic Regions - Hopp-Woods
SEQ. ID. NO. 7037 1-MetGluArgAsnGlyVal-6
SEQ. ID. NO. 7038 14-ArgIleLeuArgMetSerSerGluHisAla-23
SEQ. ID. NO. 7039 29-LysProCysLysSerPheLys-35
SEQ. ID. NO. 7040 121-LeuSerLeuArgGlyGluAsnGlyArgLeuArgAlaGluValLysLysAsnAlaArgLeuThrGlyLysGluLeuThr-146
SEQ. ID. NO. 7041 152-AsnAlaProGluSerThrLysGlnPro-160
578
AMPHI Regions - AMPHI
SEQ. ID. NO. 7042 10-PheAlaAspPhePheLysAspPheAlaProGlnPheGlyGlyPheGlnAsn-26
SEQ. ID. NO. 7043 34-AspPhePheAlaAlaPheLeuGlyGlyLeuGluGlyAsnMetGlyAsnThrAla-51
SEQ. ID. NO. 7044 71-AsnAlaAspAlaAlaArgPhe-77
Antigenic Index - Jameson-Wolf
SEQ. ID. NO. 7045 2-GlyLysLeuAspIle-6
SEQ. ID. NO. 7046 13-PhePheLysAspPheAlaProGlnPheGlyGly-23
SEQ. ID. NO. 7047 43-LeuGluGlyAsnMetGlyAsnThrAla-51
SEQ. ID. NO. 7048 73-AspAlaAlaArgPheAlaGlu-79
SEQ. ID. NO. 7049 90-GlnAsnIleGlnThrGlyAsnAspPheArgLeuGlnArgGlyGlyValGly-106
Hydrophilic Regions - Hopp-Woods
SEQ. ID. NO. 7050 2-GlyLysLeuAspIle-6
SEQ. ID. NO. 7051 73-AspAlaAlaArgPheAlaGlu-79
SEQ. ID. NO. 7052 96-AsnAspPheArgLeuGlnArg-102
579-1
AMPHI Regions - AMPHI
SEQ. ID. NO. 7053 6-PheAspPheLeuHisLeuIleSerValSerGlyTrpGluHisLeuAlaGlu-22
SEQ. ID. NO. 7054 49-ValAlaValMetArg-53
SEQ. ID. NO. 7055 66-IleSerPheLeuCysAsn-71
SEQ. ID. NO. 7056 115-LeuSerAsnPheAla-119
SEQ. ID. NO. 7057 129-ProPheLysValGlyAspPheIleArgValGlyGlyPheGluGlyTyrValArgGluIleLys-149
SEQ. ID. NO. 7058 258-GlnValValGluAsnLeuArg-264
Antigenic Index - Jameson-Wolf
SEQ. ID. NO. 7059 110-SerLeuLysAspGlnLeuSer-116
SEQ. ID. NO. 7060 128-ArgProPheLysVal-132
SEQ. ID. NO. 7061 136-IleArgValGlyGlyPheGluGlyTyrValArgGluIleLysMet-150
SEQ. ID. NO. 7062 154-SerLeuArgThrThrAspAsnGluGluValValLeu-165
SEQ. ID. NO. 7063 175-IleValAsnArgSerThrLeu-181
SEQ. ID. NO. 7064 198-LeuLysValAlaLysGluAlaValLeu-206
SEQ. ID. NO. 7065 216-ValGlnAsnGluGluArgGlnAla-223
SEQ. ID. NO. 7066 231-GlyAspAsnAlaIle-235
SEQ. ID. NO. 7067 244-AsnGluAlaAspArgTrpThrLeu-251
SEQ. ID. NO. 7068 253-CysAspLeuAsnGluGlnValValGluAsnLeuArgLysValAsn-267
SEQ. ID. NO. 7069 271-ProPheProGlnArgAspIleHis-278
Hydrophilic Regions - Hopp-Woods
SEQ. ID. NO. 7070 110-SerLeuLysAspGlnLeu-115
SEQ. ID. NO. 7071 144-TyrValArgGluIleLysMet-150
SEQ. ID. NO. 7072 155-LeuArgThrThrAspAsnGluGluValVal-164
SEQ. ID. NO. 7073 198-LeuLysValAlaLysGluAlaValLeu-206
SEQ. ID. NO. 7074 216-ValGlnAsnGluGluArgGlnAla-223
SEQ. ID. NO. 7075 244-AsnGluAlaAspArgTrp-249
SEQ. ID. NO. 7076 254-AspLeuAsnGluGlnValValGluAsnLeuArgLysValAsn-267
SEQ. ID. NO. 7077 273-ProGlnArgAspIleHis-278
580
AMPHI Regions - AMPHI
SEQ. ID. NO. 7078 47-ProValSerAlaSerLys-52
SEQ. ID. NO. 7079 54-SerLeuValLysProLeuSerGlnProLeuAla-64
Antigenic Index - Jameson-Wolf
SEQ. ID. NO. 7080 1-MetAspSerProLysValGlyCysGly-9
SEQ. ID. NO. 7081 35-ProPheGlyProThrMetPro-41
SEQ. ID. NO. 7082 48-ValSerAlaSerLys-52
SEQ. ID. NO. 7083 66-AlaArgProGluAlaAlaHis-72
SEQ. ID. NO. 7084 81-ArgProGluAlaLeuAlaAspSerSerValSerProThrHisAlaThrSerGlyGluVal-100
Hydrophilic Regions - Hopp-Woods
SEQ. ID. NO. 7085 1-MetAspSerProLysVal-6
SEQ. ID. NO. 7086 66-AlaArgProGluAlaAlaHis-72

| | |
|---|---|
| SEQ. ID. NO. 7087 | 81-ArgProGluAlaLeuAla-86 |
| SEQ. ID. NO. 7088 | 96-ThrSerGlyGluVal-100 |
| 581 | |
| AMPHI Regions - AMPHI | |
| SEQ. ID. NO. 7089 | 43-SerHisPheIleSerLeu-48 |
| SEQ. ID. NO. 7090 | 56-ArgGluCysPheValGlyPhe-62 |
| SEQ. ID. NO. 7091 | 76-AlaThrAlaPheGlyArgIleAsnGln-84 |
| SEQ. ID. NO. 7092 | 91-ValHisGlyPheLeuThrThrPheAlaGlyArgIleAlaAsnProAlaHisCysGlnSerGlnThr-112 |
| Antigenic Index - Jameson-Wolf | |
| SEQ. ID. NO. 7093 | 8-GlyGlnThrGlyIleGluGlnAsnThrPheCysArgArgGlyPheThrArgValAsnMetGlyGlyAsnThrAspVal-33 |
| SEQ. ID. NO. 7094 | 35-ValGlnAlaAspArgGlyLeuThrSer-43 |
| SEQ. ID. NO. 7095 | 49-SerLysLeuGluThrGluValArgGluCysPhe-59 |
| SEQ. ID. NO. 7096 | 100-GlyArgIleAlaAsnProAlaHisCysGlnSerGlnThrAla-113 |
| Hydrophilic Regions - Hopp-Woods | |
| SEQ. ID. NO. 7097 | 35-ValGlnAlaAspArgGlyLeu-41 |
| SEQ. ID. NO. 7098 | 49-SerLysLeuGluThrGluValArgGlu-57 |
| 582 | |
| AMPHI Regions - AMPHI | |
| SEQ. ID. NO. 7099 | 27-ThrAspAsnValThrArgLeuAla-34 |
| SEQ. ID. NO. 7100 | 65-ValArgSerSerLeu-69 |
| SEQ. ID. NO. 7101 | 91-GlyGluThrAlaAspIleTyrThrProLeuSer-101 |
| SEQ. ID. NO. 7102 | 139-GlySerProThrArg-143 |
| SEQ. ID. NO. 7103 | 169-IleAlaGluAspLeuPhe-174 |
| SEQ. ID. NO. 7104 | 246-SerArgSerTrpAsnArgIleTyrAlaMet-255 |
| SEQ. ID. NO. 7105 | 263-LeuThrValIleProArgValTrpValArgAlaPheAspGlnSer-277 |
| SEQ. ID. NO. 7106 | 286-IleAlaAspTyrMetGlyTyr-292 |
| SEQ. ID. NO. 7107 | 334-LeuLysGlyValValArgGlyPheHisGlyTyrGlyGlu-346 |
| Antigenic Index - Jameson-Wolf | |
| SEQ. ID. NO. 7108 | 26-LeuThrAspAsnValThr-31 |
| SEQ. ID. NO. 7109 | 34-AlaCysTyrAspArg-38 |
| SEQ. ID. NO. 7110 | 44-LeuProSerSerAlaGlyGlnGluGlyGlnGluSerLysAla-57 |
| SEQ. ID. NO. 7111 | 63-GluThrValArgSerSerLeuAspLysGlyGluAla-74 |
| SEQ. ID. NO. 7112 | 77-ValValGluLysGlyGlyAspAlaLeuProAlaAspSerAlaGlyGluThrAlaAsp-95 |
| SEQ. ID. NO. 7113 | 105-AspLeuAspLysAsnAspLeuArgGly-113 |
| SEQ. ID. NO. 7114 | 115-LeuGlyValArgGluHisAsnProMetTyr-124 |
| SEQ. ID. NO. 7115 | 131-AsnAsnSerProAsnTyrAlaProGlySerProThrArgGlyThrThrValGlnGluLysPheGlyGlnGlnLysArgAlaGluThrLysLeu-161 |
| SEQ. ID. NO. 7116 | 165-PheLysSerLysIleAlaGluAspLeuPheLysThrArgAla-178 |
| SEQ. ID. NO. 7117 | 183-GlyTyrThrGlnArgSerAspTrpGlnIleTyrAsnGlnGlyArgLysSerAlaProPheArgAsnThrAspTyrLysPro-209 |
| SEQ. ID. NO. 7118 | 216-ProValLysAlaAspLeuProPheGlyGlyArgLeuArgMet-229 |
| SEQ. ID. NO. 7119 | 237-GlnSerAsnGlyGlnSerArgProGluSerArgSerTrpAsn-250 |
| SEQ. ID. NO. 7120 | 273-AlaPheAspGlnSerGlyAspLysAsnAspAsnProAspIleAlaAsp-288 |
| SEQ. ID. NO. 7121 | 291-GlyTyrGlyAspValLysLeuGlnTyrArgLeuAsnAspArgGlnAsnVal-307 |
| SEQ. ID. NO. 7122 | 312-ArgTyrAsnProLysThrGlyTyr-319 |
| SEQ. ID. NO. 7123 | 330-IleLysGlyLysLeuLysGlyValVal-338 |
| SEQ. ID. NO. 7124 | 342-HisGlyTyrGlyGluSerLeuIleAspTyrAsnHisLysGlnAsnGly-357 |
| SEQ. ID. NO. 7125 | 365-AsnAspLeuAspGlyIle-370 |
| Hydrophilic Regions - Hopp-Woods | |
| SEQ. ID. NO. 7126 | 48-AlaGlyGlnGluGlyGlnGluSerLysAla-57 |
| SEQ. ID. NO. 7127 | 63-GluThrValArgSerSerLeuAspLysGlyGluAla-74 |
| SEQ. ID. NO. 7128 | 79-GluLysGlyGlyAspAlaLeuProAlaAspSerAlaGlyGluThrAlaAsp-95 |
| SEQ. ID. NO. 7129 | 105-AspLeuAspLysAsnAspLeuArgGly-113 |
| SEQ. ID. NO. 7130 | 115-LeuGlyValArgGluHisAsn-121 |
| SEQ. ID. NO. 7131 | 140-SerProThrArgGlyThrThrValGlnGluLysPheGlyGlnGlnLysArgAlaGluThrLysLeu-161 |
| SEQ. ID. NO. 7132 | 165-PheLysSerLysIleAlaGluAspLeuPheLysThrArgAla-178 |
| SEQ. ID. NO. 7133 | 195-GlnGlyArgLysSerAlaProPheArgAsnThrAspTyrLysPro-209 |
| SEQ. ID. NO. 7134 | 225-GlyArgLeuArgMet-229 |
| SEQ. ID. NO. 7135 | 239-AsnGlyGlnSerArgProGluSerArgSerTrp-249 |
| SEQ. ID. NO. 7136 | 274-PheAspGlnSerGlyAspLysAsnAspAsnProAspIleAlaAsp-288 |
| SEQ. ID. NO. 7137 | 293-GlyAspValLysLeu-297 |
| SEQ. ID. NO. 7138 | 299-TyrArgLeuAsnAspArgGlnAsn-306 |
| SEQ. ID. NO. 7139 | 332-GlyLysLeuLysGlyValVal-338 |
| SEQ. ID. NO. 7140 | 352-AsnHisLysGlnAsn-356 |
| 583 | |
| AMPHI Regions - AMPHI | |
| SEQ. ID. NO. 7141 | 11-HisLeuAlaPheCysAlaPheCysGlyIle-20 |
| SEQ. ID. NO. 7142 | 28-ArgLeuHisAsnArgMetTyrAsnAlaAlaAlaAlaArg-40 |
| SEQ. ID. NO. 7143 | 58-ValThrAspAlaGln-62 |
| SEQ. ID. NO. 7144 | 66-SerLysAsnGlyAspLysGlnIle-73 |
| SEQ. ID. NO. 7145 | 75-AspThrHisProGlnPro-80 |
| SEQ. ID. NO. 7146 | 117-GlyTyrAlaGlyTyrCysAspGln-124 |
| SEQ. ID. NO. 7147 | 140-AspAsnGlyGlyAsnHisThrAsp-147 |
| SEQ. ID. NO. 7148 | 162-GlyTyrGlyGlnCysGlnAsnGlnGlyAla-171 |
| Antigenic Index - Jameson-Wolf | |
| SEQ. ID. NO. 7149 | 24-ThrAlaGlyAsnArgLeuHisAsnArgMetTyr-34 |
| SEQ. ID. NO. 7150 | 41-GlyIleGlyArgGlyAsnGlySerGlnGlnGlnPheGlyLysSerGluThrValThrAspAlaGlnArgPheSerSerLysAsnGlyAspLysGlnIleSer AspThrHisProGlnProCysPheGluGlnThrAlaArgAsnHisAsnCysAspGlyAsnGlnProAsnGlnArgIleGlyGluArgThrGlnArgIleAlaHis ArgArgAlaArgPhe-114 |

TABLE 1-continued

| | |
|---|---|
| SEQ. ID. NO. 7151 | 117-GlyTyrAlaGlyTyCysAspGlnProAspGlyAsnAsnArgGlnArgAlaGlnArgHisGlyLeuAlaAspAsnGlyGlyAsnHisThrAspLysHisGlyGlnGlnArgProSerLeuArgLeuAspProValGlyTyrGlyGlnCysGlnAsnGlnGlyAlaGlnTyrCysGlyAsnGlyGluGlyTyrArgPhe-182 |
| SEQ. ID. NO. 7152 | 190-AspLeuArgLysLysAspArgProGluLysSerGluLys-202 |
| Hydrophilic Regions - Hopp-Woods | |
| SEQ. ID. NO. 7153 | 27-AsnArgLeuHisAsn-31 |
| SEQ. ID. NO. 7154 | 41-GlyIleGlyArgGlyAsnGlySer-48 |
| SEQ. ID. NO. 7155 | 51-GlnPheGlyLysSerGluThrValThrAspAlaGlnArgPheSerSerLysAsnGlyAspLysGlnIleSerAspThrHisPro-78 |
| SEQ. ID. NO. 7156 | 84-GlnThrAlaArgAsnHisAsnCysAspGlyAsnGlnProAsnGlnArgIleGlyGluArgThrGlnArgIleAlaHisArgArgAlaArgPhe-114 |
| SEQ. ID. NO. 7157 | 123-AspGlnProAspGlyAsnAsnArgGlnArgAlaGlnArg-135 |
| SEQ. ID. NO. 7158 | 137-GlyLeuAlaAspAsnGlyGlyAsnHisThrAspLysHisGlyGlnGlnArgProSerLeuArgLeuAspPro-160 |
| SEQ. ID. NO. 7159 | 178-GluGlyTyrArgPhe-182 |
| SEQ. ID. NO. 7160 | 190-AspLeuArgLysLysAspArgProGluLysSerGluLys-202 |
| 584-2 | |
| AMPHI Regions - AMPHI | |
| SEQ. ID. NO. 7161 | 28-GluPheSerGluSerAlaGly-34 |
| SEQ. ID. NO. 7162 | 60-AlaGluPheValLysLysPheAsnLysPheIleArgLys-72 |
| SEQ. ID. NO. 7163 | 115-AspPheAspGluLeuAsnArgPheIleAlaAspIle-126 |
| SEQ. ID. NO. 7164 | 148-IleAspGlnValSerLysAsp-154 |
| SEQ. ID. NO. 7165 | 166-LeuAlaGlyValLeuGly-171 |
| SEQ. ID. NO. 7166 | 186-GlySerHisIleAla-190 |
| SEQ. ID. NO. 7167 | 196-GlnAlaLysMetLeuArgAlaMet-203 |
| Antigenic Index - Jameson-Wolf | |
| SEQ. ID. NO. 7168 | 37-ValAlaGlnAspThrMetSer-43 |
| SEQ. ID. NO. 7169 | 50-AlaGluGlyArgAspLysAsnAlaVal-58 |
| SEQ. ID. NO. 7170 | 61-GluPheValLysLysPheAsnLysPheIleArgLysSerLysAsnGlySerPheLysThrGluLeuValSerArgSerAlaMetProArgTyrGlnTyrThrAsnGlyArgArgIleGlnThrGlyTrpGluGluArgAlaGluPheLysValGluGlyArgAspPheAspGluLeuAsn-120 |
| SEQ. ID. NO. 7171 | 138-HisValSerArgGluArgArgAsnGluValIleAspGlnValSerLysAspAlaValLeu-157 |
| SEQ. ID. NO. 7172 | 159-PheLysAlaArgAlaGluLysLeuAla-167 |
| SEQ. ID. NO. 7173 | 189-IleAlaGlyGlyGly-193 |
| SEQ. ID. NO. 7174 | 210-AsnMetGluGlyAlaAspSerAlaAlaProGlyValGluGluIleSer-225 |
| Hydrophilic Regions - Hopp-Woods | |
| SEQ. ID. NO. 7175 | 50-AlaGluGlyArgAspLysAsnAlaVal-58 |
| SEQ. ID. NO. 7176 | 61-GluPheValLysLysPheAsnLysPheIleArgLysSerLysAsnGlySerPheLysThrGluLeuValSer-84 |
| SEQ. ID. NO. 7177 | 95-AsnGlyArgArgIleGlnThrGlyTrpGluGluArgAlaGluPheLysValGluGlyArgAspPheAspGluLeuAsn-120 |
| SEQ. ID. NO. 7178 | 138-HisValSerArgGluArgArgAsnGluValIleAspGlnValSerLysAspAlaValLeu-157 |
| SEQ. ID. NO. 7179 | 159-PheLysAlaArgAlaGluLysLeuAla-167 |
| SEQ. ID. NO. 7180 | 210-AsnMetGluGlyAlaAspSerAlaAlaProGlyValGluGluIleSer-225 |
| 585 | |
| AMPHI Regions - AMPHI | |
| SEQ. ID. NO. 7181 | 6-ArgIlePheAlaThrPheCysAlaValIleValCys-17 |
| SEQ. ID. NO. 7182 | 46-ThrThrLeuMetGlySerIleIleSer-54 |
| SEQ. ID. NO. 7183 | 65-ArgGluIleLeuThrGluTrpLysAsp-73 |
| SEQ. ID. NO. 7184 | 93-AsnArgTyrIleAsp-97 |
| SEQ. ID. NO. 7185 | 133-LysAspTrpAspLysLeuGlnAlaArgArg-142 |
| SEQ. ID. NO. 7186 | 153-ProLeuAlaProIleTrp-158 |
| SEQ. ID. NO. 7187 | 178-LeuAlaGlyAsnIleAlaLysProIleArgIleLeuGlyAsnGlyMetAspArgValAla-197 |
| SEQ. ID. NO. 7188 | 223-PheAspLysMetValGluLysLeuGluLysLeuVal-234 |
| SEQ. ID. NO. 7189 | 247-GluMetArgSerPro-251 |
| SEQ. ID. NO. 7190 | 255-MetGlnAlaIleValGlyLeuIle-262 |
| SEQ. ID. NO. 7191 | 273-LeuLysArgLeuGluGly-278 |
| SEQ. ID. NO. 7192 | 353-LeuTyrArgAlaPheAspAsnValIleArgAsnAlaValAsn-366 |
| SEQ. ID. NO. 7193 | 430-IleIleGluGlnHisCysGlyLysIleIleAlaGlu-441 |
| Antigenic Index - Jameson-Wolf | |
| SEQ. ID. NO. 7194 | 36-AsnGlnPheAsnGlnArgArgThrIleGlu-45 |
| SEQ. ID. NO. 7195 | 56-PheArgAlaArgGlyAspAlaGlyAlaArgGluIleLeuThrGluTrpLysAspSerProValSer-77 |
| SEQ. ID. NO. 7196 | 84-GlnGlyAspGluLysLysAspIleLeu-92 |
| SEQ. ID. NO. 7197 | 99-TyrThrIleGluArgAlaArgLeu-106 |
| SEQ. ID. NO. 7198 | 120-GluTyrAspArgPheGlyGlu-126 |
| SEQ. ID. NO. 7199 | 133-LysAspTrpAspLysLeuGlnAlaArgArgLeuProSerPro-146 |
| SEQ. ID. NO. 7200 | 189-LeuGlyAsnGlyMetAspArgValAlaAsnGlyGluLeuGluThrArgIle-205 |
| SEQ. ID. NO. 7201 | 207-GlnGlnValAspAspArgAspAspGluLeuSer-217 |
| SEQ. ID. NO. 7202 | 225-LysMetValGluLysLeuGluLysLeuValAlaLysGluArgHisLeu-240 |
| SEQ. ID. NO. 7203 | 246-HisGluMetArgSerProLeuAla-253 |
| SEQ. ID. NO. 7204 | 264-AlaGlnProGlnLysGlnGluGlnTyrLeuLysArgLeuGluGlyGluLeuThrArgMetAspThrLeuAla-287 |
| SEQ. ID. NO. 7205 | 294-SerArgLeuGluThrSerAsnMetAlaLeuGluLysGluSerLeuLys-309 |
| SEQ. ID. NO. 7206 | 317-LeuValGluAspAsnGlnSerIleAlaGlnLysAsnGlyGln-330 |
| SEQ. ID. NO. 7207 | 335-SerAlaAspGlyLysIleProGluAsnThr-344 |
| SEQ. ID. NO. 7208 | 367-TyrSerProGluGlySerThr-373 |
| SEQ. ID. NO. 7209 | 377-AsnIleGlyGlnAspHisLysHis-384 |
| SEQ. ID. NO. 7210 | 388-AspValThrAspAsnGlyProGlyValAspGluMetGln-400 |
| SEQ. ID. NO. 7211 | 409-TyrArgAlaAspSerSerAlaAsnLysProGlyThrGly-421 |
| SEQ. ID. NO. 7212 | 432-GluGlnHisCysGlyLysIleIleAlaGluAsnIleLysProAsnGlyLeuArg-449 |
| SEQ. ID. NO. 7213 | 453-IleLeuProLysLysLysThrGlySerLysThrGluLysSerAlaAsn-468 |
| Hydrophilic Regions- Hopp-Woods | |
| SEQ. ID. NO. 7214 | 37-GlnPheAsnGlnArgArgThrIleGlu-45 |
| SEQ. ID. NO. 7215 | 56-PheArgAlaArgGlyAspAlaGlyAlaArgGluIleLeuThrGluTrpLysAspSerProVal-76 |
| SEQ. ID. NO. 7216 | 84-GlnGlyAspGluLysLysAspIleLeu-92 |
| SEQ. ID. NO. 7217 | 100-ThrIleGluArgAlaArgLeu-106 |
| SEQ. ID. NO. 7218 | 120-GluTyrAspArgPheGlyGlu-126 |
| SEQ. ID. NO. 7219 | 133-LysAspTrpAspLysLeuGlnAlaArgArgLeuPro-144 |

TABLE 1-continued

| | |
|---|---|
| SEQ. ID. NO. 7220 | 192-GlyMetAspArgValAlaAsnGlyGluLeuGluThrArgIle-205 |
| SEQ. ID. NO. 7221 | 207-GlnGlnValAspAspArgAspAspGluLeuSer-217 |
| SEQ. ID. NO. 7222 | 225-LysMetValGluLysLeuGluLysLeuValAlaLysGluArgHisLeu-240 |
| SEQ. ID. NO. 7223 | 246-HisGluMetArgSerProLeu-252 |
| SEQ. ID. NO. 7224 | 265-GlnProGlnLysGlnGluGlnTyrLeuLysArgLeuGluGlyGluLeuThrArgMetAspThrLeuAla-287 |
| SEQ. ID. NO. 7225 | 294-SerArgLeuGluThr-298 |
| SEQ. ID. NO. 7226 | 302-AlaLeuGluLysGluSerLeuLys-309 |
| SEQ. ID. NO. 7227 | 317-LeuValGluAspAsnGlnSerIleAlaGlnLysAsnGlyGln-330 |
| SEQ. ID. NO. 7228 | 336-AlaAspGlyLysIleProGlu-342 |
| SEQ. ID. NO. 7229 | 389-ValThrAspAsnGlyProGlyValAspGluMetGln-400 |
| SEQ. ID. NO. 7230 | 410-ArgAlaAspSerSerAlaAsnLysProGlyThr-420 |
| SEQ. ID. NO. 7231 | 438-IleIleAlaGluAsnIleLys-444 |
| SEQ. ID. NO. 7232 | 454-LeuProLysLysLysThrGlySerLysThrGluLysSerAlaAsn-468 |
| 586 | |
| AMPHI Regions - AMPHI | |
| SEQ. ID. NO. 7233 | 12-AspAsnPheLysTyrPheTrpLysThr-20 |
| SEQ. ID. NO. 7234 | 30-IleLeuAlaAlaLeuGly-35 |
| SEQ. ID. NO. 7235 | 56-ValLeuAlaAsnIleValGluLysAlaGlnSerLys-67 |
| SEQ. ID. NO. 7236 | 80-LeuGlnGlnSerTyrProHisSerIleSer-89 |
| SEQ. ID. NO. 7237 | 177-SerGlnGluAlaLeuLysAsnTyrGlyGlnAlaLeuGluLysMetProGlnAspSerValGlyArg-198 |
| Antigenic Index - Jameson-Wolf | |
| SEQ. ID. NO. 7238 | 4-HisLeuGluGluGlnGlnGluLeuAspAsn-13 |
| SEQ. ID. NO. 7239 | 42-TyrGlnAsnArgLysValSerGlnAsnGlnGluAla-53 |
| SEQ. ID. NO. 7240 | 60-IleValGluLysAlaGlnSerLysAlaProGlnSerGluIleAsnAlaGluLeuThrLysLeuGlnGln-82 |
| SEQ. ID. NO. 7241 | 100-ThrGluPheAspAlaGlnArgTyrAspValAlaGluGly-112 |
| SEQ. ID. NO. 7242 | 118-LeuSerAsnGlnLysAspSerLeu-125 |
| SEQ. ID. NO. 7243 | 140-GlnGlnLysLysTyrAspAla-146 |
| SEQ. ID. NO. 7244 | 153-ThrProValGluAlaAspPhe-159 |
| SEQ. ID. NO. 7245 | 164-MetGluThrLysGlyAspVal-170 |
| SEQ. ID. NO. 7246 | 173-AlaGlnGlyLysSerGlnGluAlaLeuLysAsnTyrGlyGlnAlaLeuGluLysMetProGlnAspSerValGlyArgGluLeuVal-201 |
| SEQ. ID. NO. 7247 | 204-LysLeuAspSerLeuLys-209 |
| Hydrophilic Regions - Hopp-Woods | |
| SEQ. ID. NO. 7248 | 4-HisLeuGluGluGlnGlnGluLeuAspAsn-13 |
| SEQ. ID. NO. 7249 | 43-GlnAsnArgLysValSerGlnAsnGlnGluAla-53 |
| SEQ. ID. NO. 7250 | 60-IleValGluLysAlaGlnSerLysAlaProGlnSerGluIleAsnAlaGluLeuThrLys-79 |
| SEQ. ID. NO. 7251 | 100-ThrGluPheAspAlaGlnArgTyrAspValAlaGluGly-112 |
| SEQ. ID. NO. 7252 | 120-AsnGlnLysAspSerLeu-125 |
| SEQ. ID. NO. 7253 | 140-GlnGlnLysLysTyrAspAla-146 |
| SEQ. ID. NO. 7254 | 153-ThrProValGluAlaAspPhe-159 |
| SEQ. ID. NO. 7255 | 164-MetGluThrLysGlyAspVal-170 |
| SEQ. ID. NO. 7256 | 174-GlnGlyLysSerGlnGluAlaLeuLys-182 |
| SEQ. ID. NO. 7257 | 187-AlaLeuGluLysMetProGlnAspSerValGlyArgGluLeuVal-201 |
| SEQ. ID. NO. 7258 | 204-LysLeuAspSerLeuLys-209 |
| 587 | |
| AMPHI Regions - AMPHI | |
| SEQ. ID. NO. 7259 | 6-LeuProAlaLeuProAlaIleLeuProLeuSerThr-17 |
| SEQ. ID. NO. 7260 | 190-AsnGlySerLysThrLeuSer-196 |
| Antigenic Index - Jameson-Wolf | |
| SEQ. ID. NO. 7261 | 27-AspIleMetThrAspLysGlyLysTrpLysLeuGluThr-39 |
| SEQ. ID. NO. 7262 | 44-LeuAsnSerGluAsnAsnArgAlaGluLeu-53 |
| SEQ. ID. NO. 7263 | 72-GluIleGlnGluAsnGlySerAsnThrAsp-81 |
| SEQ. ID. NO. 7264 | 95-GlyAsnThrAspIleTyrGlySerGlySer-104 |
| SEQ. ID. NO. 7265 | 108-HisGluGluArgLysLeuAspGlyAsnSerLysThrArgAsnLysArgMetSerAsp-126 |
| SEQ. ID. NO. 7266 | 135-PheLeuLysAspAspLysAsnProAla-143 |
| SEQ. ID. NO. 7267 | 151-ThrValTyrGluLysSerArgAsnLysAlaSerSerGlyLysSer-165 |
| SEQ. ID. NO. 7268 | 187-TyrArgIleAsnGlySerLysThrLeuSerAspGlyIleArgTyrLysSerGlyAsnTyr-206 |
| SEQ. ID. NO. 7269 | 217-AlaAsnAspArgIleSerLeuThrGlyGly-226 |
| SEQ. ID. NO. 7270 | 231-GlyArgGlnProAspArgThrAspGlyLysArgGluSerSerArgAsnThrSerThr-249 |
| SEQ. ID. NO. 7271 | 273-ValSerGlyGlnSerSerSerGluLeuLysPhe-283 |
| Hydrophilic Regions - Hopp-Woods | |
| SEQ. ID. NO. 7272 | 27-AspIleMetThrAspLysGlyLysTrpLysLeu-37 |
| SEQ. ID. NO. 7273 | 47-GluAsnAsnArgAlaGluLeu-53 |
| SEQ. ID. NO. 7274 | 72-GluIleGlnGluAsnGlySerAsnThr-80 |
| SEQ. ID. NO. 7275 | 108-HisGluGluArgLysLeuAspGlyAsnSerLysThrArgAsnLysArgMetSerAsp-126 |
| SEQ. ID. NO. 7276 | 135-PheLeuLysAspAspLysAsnPro-142 |
| SEQ. ID. NO. 7277 | 151-ThrValTyrGluLysSerArgAsnLysAlaSerSerGly-163 |
| SEQ. ID. NO. 7278 | 193-LysThrLeuSerAspGlyIleArgTyrLysSer-203 |
| SEQ. ID. NO. 7279 | 217-AlaAsnAspArgIleSer-222 |
| SEQ. ID. NO. 7280 | 232-ArgGlnProAspArgThrAspGlyLysArgGluSerSerArgAsnThr-247 |
| SEQ. ID. NO. 7281 | 277-SerSerSerGluLeuLysPhe-283 |
| 588 | |
| AMPHI Regions - AMPHI | |
| SEQ. ID. NO. 7282 | 52-GlnAspGlyArgAsnTyrThrGlySerPhe-61 |
| SEQ. ID. NO. 7283 | 99-GlyThrPheLysLys-103 |
| Antigenic Index - Jameson-Wolf | |
| SEQ. ID. NO. 7284 | 25-SerTyrGlnGluProGlyCysThrTyrAspGlyAsnValGlyLysAspGlyLysProAlaGlyLysGlyThrTrpArgCysGlnAspGlyArgAsnTyrThr GlySerPheLysAsnGlyLysPheAspGlyGlnGly-70 |
| SEQ. ID. NO. 7285 | 80-IlePheIleGluProPheAsnSerAspSerThrLysPheArg-93 |
| SEQ. ID. NO. 7286 | 100-ThrPheLysLysGlyLeuAlaHisGlyArgPheThrValSerGlnAsnGlyGluThr-118 |
| SEQ. ID. NO. 7287 | 124-CysGluAsnGlyMetIleLysGluValLysLeuProLysAsnLys-138 |

TABLE 1-continued

| | |
|---|---|
| Hydrophilic Regions - Hopp-Woods | |
| SEQ. ID. NO. 7288 | 36-AsnValGlyLysAspGlyLysProAlaGly-45 |
| SEQ. ID. NO. 7289 | 47-GlyThrTrpArgCysGlnAspGlyArgAsnTyr-57 |
| SEQ. ID. NO. 7290 | 61-PheLysAsnGlyLysPheAspGly-68 |
| SEQ. ID. NO. 7291 | 85-PheAsnSerAspSerThrLysPheArg-93 |
| SEQ. ID. NO. 7292 | 100-ThrPheLysLysGlyLeuAla-106 |
| SEQ. ID. NO. 7293 | 124-CysGluAsnGlyMetIleLysGluValLysLeuProLysAsnLys-138 |
| 589 | |
| AMPHI Regions - AMPHI | |
| SEQ. ID. NO. 7294 | 18-AlaSerArgIleGluLysValLeu-25 |
| SEQ. ID. NO. 7295 | 54-ValAlaAspIlAlaLysIleIleGluLys-63 |
| SEQ. ID. NO. 7296 | 125-SerValValGlnLeuTrpLeuAla-132 |
| SEQ. ID. NO. 7297 | 150-MetAspValLeuValThrIle-156 |
| SEQ. ID. NO. 7298 | 193-PheValSerLeuGlyLysPheLeuGluHisArg-203 |
| SEQ. ID. NO. 7299 | 225-ValGlnArgAsnGlyGlu-230 |
| SEQ. ID. NO. 7300 | 240-GlnIleGlyAspLeuIleArg-246 |
| SEQ. ID. NO. 7301 | 307-GlnThrGlnLeuGlyAspMetMetAsnAlaLeuSerGluAlaGln-321 |
| SEQ. ID. NO. 7302 | 325-AlaProIleAlaArgValAlaAspLys-333 |
| SEQ. ID. NO. 7303 | 391-MetGlyLysAlaVal-395 |
| SEQ. ID. NO. 7304 | 466-IleValSerAlaAlaGln-471 |
| SEQ. ID. NO. 7305 | 477-IleProAlaAlaGln-481 |
| SEQ. ID. NO. 7306 | 497-GlyValGlyLeuValLys-502 |
| SEQ. ID. NO. 7307 | 511-LeuAlaLeuProLysPheLeuAspGlyValTrpAspIleAlaSerIle-526 |
| SEQ. ID. NO. 7308 | 539-PheAlaLeuAlaAspAlaLeuLys-546 |
| SEQ. ID. NO. 7309 | 548-AspThrAlaGluAlaIleGlyArgLeu-556 |
| SEQ. ID. NO. 7310 | 598-GluValGlnLysLeuLysAlaAla-605 |
| SEQ. ID. NO. 7311 | 612-ValGlyAspGlyIleAsnAspAlaPro-620 |
| SEQ. ID. NO. 7312 | 635-AlaAspValAlaGluHisThr-641 |
| SEQ. ID. NO. 7313 | 648-GlnHisSerValAsnGlnLeuAlaAsp-656 |
| SEQ. ID. NO. 7314 | 675-AlaPhePheTyrAsnIleLeu-681 |
| AntigenicIndex -Jameson-Wolf | |
| SEQ. ID. NO. 7315 | 1-MetGlnGlnLysIleArgPheGlnIle-9 |
| SEQ. ID. NO. 7316 | 17-CysAlaSerArgIleGluLysValLeuAsnLysLysAspPheValGluSer-33 |
| SEQ. ID. NO. 7317 | 39-AlaSerGluGluAlaGlnValValPheAspAspSerLysThrSerVal-54 |
| SEQ. ID. NO. 7318 | 59-LysIleIleGluLysThrGlyTyrGlyAlaLysGluLysThrGluAspThrLeuProGlnProGluAlaGluHis-83 |
| SEQ. ID. NO. 7319 | 109-GlyArgHisAspTrp-113 |
| SEQ. ID. NO. 7320 | 143-IleLysGlyGlyLeu-147 |
| SEQ. ID. NO. 7321 | 200-LeuGluHisArgThrLysLysSerSerLeuAsn-210 |
| SEQ. ID. NO. 7322 | 223-ValAsnValGlnArgAsnGlyGluTrpLysGlnLeuProIleAspGln-238 |
| SEQ. ID. NO. 7323 | 248-AsnHisGlyGluArgIleAlaAla-255 |
| SEQ. ID. NO. 7324 | 257-GlyIleIleGluSerGlySerGlyTrpAlaAspGluSerHisLeuThrGlyGluSerAsnProGluGluLysLysAlaGlyGly-284 |
| SEQ. ID. NO. 7325 | 293-ThrGluGlySerVal-297 |
| SEQ. ID. NO. 7326 | 318-SerGluAlaGlnGlySerLysAlaProIle-327 |
| SEQ. ID. NO. 7327 | 329-ArgValAlaAspLysAlaAla-335 |
| SEQ. ID. NO. 7328 | 356-IleLysGlyAspTrp-360 |
| SEQ. ID. NO. 7329 | 391-MetGlyLysAlaValLys-396 |
| SEQ. ID. NO. 7330 | 404-AlaAlaAlaMetGluGluAlaAlaHis-412 |
| SEQ. ID. NO. 7331 | 417-ValLeuAspLysThrGlyThrLeuThrGluGlySerProGln-430 |
| SEQ. ID. NO. 7332 | 438-ProAspSerGlyPheAspGluAspAlaLeu-447 |
| SEQ. ID. NO. 7333 | 454-ValGluGlnAsnAla-458 |
| SEQ. ID. NO. 7334 | 493-AlaGluValGluGly-497 |
| SEQ. ID. NO. 7335 | 502-LysAlaGlyLysAlaGluPheAla-509 |
| SEQ. ID. NO. 7336 | 530-SerValAspAsnLysProIleGly-537 |
| SEQ. ID. NO. 7337 | 543-AspAlaLeuLysAlaAspThrAlaGluAlaIleGlyArgLeuLysLysHisAsnIle-561 |
| SEQ. ID. NO. 7338 | 567-SerGlyAspAsnGlnGlyThrValGluTyrValAla-578 |
| SEQ. ID. NO. 7339 | 588-GlyAsnMetSerProArgAspLysAlaAlaGluValGlnLysLeuLysAlaAlaGly-606 |
| SEQ. ID. NO. 7340 | 612-ValGlyAspGlyIleAsnAspAla-619 |
| SEQ. ID. NO. 7341 | 631-MetLysGlyGlyAlaAspValAlaGlu-639 |
| SEQ. ID. NO. 7342 | 710-AsnAlaLeuArgLeuLysArgValLysIleAsp-720 |
| Hydrophilic Regions - Hopp-Woods | |
| SEQ. ID. NO. 7343 | 1-MetGlnGlnLysIleArgPheGlnIle-9 |
| SEQ. ID. NO. 7344 | 19-SerArgIleGluLysValLeuAsnLysLysAspPheValGlu-32 |
| SEQ. ID. NO. 7345 | 39-AlaSerGluGluAlaGlnValValPheAspAspSerLysThrSerVal-54 |
| SEQ. ID. NO. 7346 | 64-ThrGlyTyrGlyAlaLysGluLysThrGluAspThrLeuProGlnProGluAlaGluHis-83 |
| SEQ. ID. NO. 7347 | 200-LeuGluHisArgThrLysLysSerSerLeu-209 |
| SEQ. ID. NO. 7348 | 224-AsnValGlnArgAsnGlyGluTrpLys-232 |
| SEQ. ID. NO. 7349 | 248-AsnHisGlyGluArgIleAlaAla-255 |
| SEQ. ID. NO. 7350 | 257-GlyIleIleGluSer-261 |
| SEQ. ID. NO. 7351 | 265-TrpAlaAspGluSerHisLeuThrGlyGluSerAsnProGluGluLysLysAlaGlyGly-284 |
| SEQ. ID. NO. 7352 | 318-SerGluAlaGlnGlySerLysAlaProIle-327 |
| SEQ. ID. NO. 7353 | 329-ArgValAlaAspLysAlaAla-335 |
| SEQ. ID. NO. 7354 | 404-AlaAlaAlaMetGluGluAlaAlaHis-412 |
| SEQ. ID. NO. 7355 | 417-ValLeuAspLysThrGlyThrLeuThrGluGlySerPro-429 |
| SEQ. ID. NO. 7356 | 440-SerGlyPheAspGluAspAlaLeu-447 |
| SEQ. ID. NO. 7357 | 454-ValGluGlnAsnAla-458 |
| SEQ. ID. NO. 7358 | 493-AlaGluValGluGly-497 |
| SEQ. ID. NO. 7359 | 502-LysAlaGlyLysAlaGluPheAla-509 |
| SEQ. ID. NO. 7360 | 531-ValAspAsnLysPro-535 |
| SEQ. ID. NO. 7361 | 543-AspAlaLeuLysAlaAspThrAlaGluAlaIleGlyArgLeuLysLysHisAsnIle-561 |
| SEQ. ID. NO. 7362 | 568-GlyAspAsnGlnGly-572 |

TABLE 1-continued

| | |
|---|---|
| SEQ. ID. NO. 7363 | 591-SerProArgAspLysAlaAlaGluValGlnLysLeuLysAlaAlaGly-606 |
| SEQ. ID. NO. 7364 | 633-GlyGlyAlaAspValAlaGlu-639 |
| SEQ. ID. NO. 7365 | 712-LeuArgLeuLysArgValLysIleAsp-720 |
| 590-1 | |
| AMPHI Regions - AMPHI | |
| SEQ. ID. NO. 7366 | 77-TyrLeuProAspAsnLeuLysThrValLeuGluGlnProValThrLeuValAsnHisIleThrHis-98 |
| SEQ. ID. NO. 7367 | 100-ProPheAlaGlyGlyPhe-105 |
| SEQ. ID. NO. 7368 | 123-LysValLeuGluArgPhePheGly-130 |
| SEQ. ID. NO. 7369 | 132-GlnValProAlaSerLeu-137 |
| SEQ. ID. NO. 7370 | 177-TyrGlnLysGlyPheLysSerTyrArgAsnGly-187 |
| SEQ. ID. NO. 7371 | 214-ThrSerAspGlyIleAsnProLeu-221 |
| SEQ. ID. NO. 7372 | 248-AsnGluLeuValAsnLeuVal-254 |
| SEQ. ID. NO. 7373 | 331-LysArgLysPheAla-335 |
| SEQ. ID. NO. 7374 | 420-LysMetLeuGluAsp-424 |
| SEQ. ID. NO. 7375 | 450-AspIleAsnGluThrLeuArgLeuMet-458 |
| SEQ. ID. NO. 7376 | 460-AspSerThrValGln-464 |
| Antigenic Index - Jameson-Wolf | |
| SEQ. ID. NO. 7377 | 1-MetLysLysProLeu-5 |
| SEQ. ID. NO. 7378 | 26-LysAlaGluGluSerLeuThrGlnGlnGlnLysIleLeuGln-39 |
| SEQ. ID. NO. 7379 | 47-GluSerHisGlnTyrGluArgGlyTrp-55 |
| SEQ. ID. NO. 7380 | 62-ThrValIleArgLeuLysProGluLeu-70 |
| SEQ. ID. NO. 7381 | 72-AsnAsnAlaArgLysTyrLeuProAspAsnLeuLysThrValLeu-86 |
| SEQ. ID. NO. 7382 | 113-ThrGluPheLysTyrAlaProGluThrGluLysValLeuGlu-126 |
| SEQ. ID. NO. 7383 | 128-PhePheGlyLysGlnValPro-134 |
| SEQ. ID. NO. 7384 | 144-AsnGlySerGlyLysMetGluVal-151 |
| SEQ. ID. NO. 7385 | 157-AspTyrGluGluLeuSerGly-163 |
| SEQ. ID. NO. 7386 | 175-ThrValTyrGlnLysGlyPheLysSerTyrArgAsnGlyTyrAspAlaPro-191 |
| SEQ. ID. NO. 7387 | 196-LysLeuAlaAspLysGlyAspAlaAlaPheGlu-206 |
| SEQ. ID. NO. 7388 | 208-ValHisPheAspSerGluThrSerAspGlyIleAsn-219 |
| SEQ. ID. NO. 7389 | 233-PheSerLeuGluTrpLysGluGlyValAspTyr-243 |
| SEQ. ID. NO. 7390 | 264-AsnProAsnGlySerIleAlaProSerLysIleGluValGly-277 |
| SEQ. ID. NO. 7391 | 281-PheSerThrLysThrGlyGluSerGlyAla-290 |
| SEQ. ID. NO. 7392 | 292-IleAsnSerGluGlyGlnPheArgPheAspThr-302 |
| SEQ. ID. NO. 7393 | 304-ValTyrGlyAspGluLysTyrGlyPro-312 |
| SEQ. ID. NO. 7394 | 330-LeuLysArgLysPheAla-335 |
| SEQ. ID. NO. 7395 | 338-SerAlaLysLysMetThrGluGluGlnIleArgAsnAspLeu-351 |
| SEQ. ID. NO. 7396 | 355-ValLysGlyGluAlaSerGlyLeuPheThrAsnAsnProValLeuAsp-370 |
| SEQ. ID. NO. 7397 | 378-LeuProSerGlyLysIleAspValGlyGly-387 |
| SEQ. ID. NO. 7398 | 389-IleMetPheLysAspMetLysLysGluAspLeuAsnGln-401 |
| SEQ. ID. NO. 7399 | 406-LeuLysLysThrGluAlaAspIleArgMet-415 |
| SEQ. ID. NO. 7400 | 437-AsnAlaGluAspGluAlaGluGlyArgAlaSerLeuAspAspIleAsnGluThrLeu-455 |
| SEQ. ID. NO. 7401 | 466-MetAlaArgGluLysTyr-471 |
| SEQ. ID. NO. 7402 | 475-AsnGlyAspGlnIleAsp-480 |
| SEQ. ID. NO. 7403 | 485-LeuLysAsnAsnGlnLeuLysLeuAsnGlyLysThrLeuGlnAsnGluProGluProAspPheAspGluGlyGlyMetValSerGluProGlnGln-516 |
| Hydrophilic Regions- Hopp-Woods | |
| SEQ. ID. NO. 7404 | 1-MetLysLysProLeu-5 |
| SEQ. ID. NO. 7405 | 26-LysAlaGluGluSerLeuThrGln-33 |
| SEQ. ID. NO. 7406 | 62-ThrValIleArgLeuLysProGluLeu-70 |
| SEQ. ID. NO. 7407 | 72-AsnAsnAlaArgLysTyrLeuProAspAsnLeuLysThrValLeu-86 |
| SEQ. ID. NO. 7408 | 113-ThrGluPheLysTyrAlaProGluThrGluLysValLeuGlu-126 |
| SEQ. ID. NO. 7409 | 147-GlyLysMetGluVal-151 |
| SEQ. ID. NO. 7410 | 157-AspTyrGluGluLeuSerGly-163 |
| SEQ. ID. NO. 7411 | 180-GlyPheLysSerTyrArgAsnGlyTyr-188 |
| SEQ. ID. NO. 7412 | 196-LysLeuAlaAspLysGlyAspAlaAlaPheGlu-206 |
| SEQ. ID. NO. 7413 | 208-ValHisPheAspSerGluThrSerAspGly-217 |
| SEQ. ID. NO. 7414 | 233-PheSerLeuGluTrpLysGluGlyValAspTyr-243 |
| SEQ. ID. NO. 7415 | 272-SerLysIleGluValGly-277 |
| SEQ. ID. NO. 7416 | 306-GlyAspGluLysTyrGlyPro-312 |
| SEQ. ID. NO. 7417 | 330-LeuLysArgLysPheAla-335 |
| SEQ. ID. NO. 7418 | 338-SerAlaLysLysMetThrGluGluGlnIleArgAsnAspLeu-351 |
| SEQ. ID. NO. 7419 | 355-ValLysGlyGluAla-359 |
| SEQ. ID. NO. 7420 | 381-GlyLysIleAspValGlyGly-387 |
| SEQ. ID. NO. 7421 | 389-IleMetPheLysAspMetLysLysGluAspLeuAsn-400 |
| SEQ. ID. NO. 7422 | 406-LeuLysLysThrGluAlaAspIleArgMet-415 |
| SEQ. ID. NO. 7423 | 437-AsnAlaGluAspGluAlaGluGlyArgAlaSerLeuAspAspIleAsnGluThrLeu-455 |
| SEQ. ID. NO. 7424 | 466-MetAlaArgGluLysTyr-471 |
| SEQ. ID. NO. 7425 | 486-LysAsnAsnGlnLeuLysLeuAsnGly-494 |
| SEQ. ID. NO. 7426 | 496-ThrLeuGlnAsnGluProGluProAspPheAspGluGlyGlyMetValSerGluProGlnGln-516 |
| 591 | |
| AMPHI Regions - AMPHI | |
| SEQ. ID. NO. 7427 | 6-AlaPheIlePheAla-10 |
| SEQ. ID. NO. 7428 | 17-LeuHisGluPheGlyHisTyrIleValAla-26 |
| SEQ. ID. NO. 7429 | 61-LeuGlyGlyTyrValLysMetValAsp-69 |
| SEQ. ID. NO. 7430 | 143-GlyAspLysIleGlnSerValAsnGlyThrProValAlaAspTrp-157 |
| SEQ. ID. NO. 7431 | 181-SerGlyAlaGlnThrValArgThrIleAspAlaAlaGlyThrProGluAlaGlyLysIleAlaLys-202 |
| SEQ. ID. NO. 7432 | 218-AlaGlyGlyValGluLys-223 |
| SEQ. ID. NO. 7433 | 234-ProGlyAspArgLeu-238 |
| SEQ. ID. NO. 7434 | 245-ProIleAlaSerTrpGlnGluTrpAlaAsnLeuThrArg-257 |
| SEQ. ID. NO. 7435 | 270-ArgAlaGlyGlnThr-274 |
| SEQ. ID. NO. 7436 | 304-AlaTrpAspAlaGlnIleArg-310 |

TABLE 1-continued

| | |
|---|---|
| SEQ. ID. NO. 7437 | 313-TyrArgProSerValValArgAlaPheGly-322 |
| SEQ. ID. NO. 7438 | 324-GlyTrpGluLysThrValSerHis-331 |
| SEQ. ID. NO. 7439 | 335-ThrLeuLysPhePheGlyLysLeuIle-343 |
| SEQ. ID. NO. 7440 | 351-HisIleSerGlyProLeuThrIleAla-359 |
| SEQ. ID. NO. 7441 | 373-TyrLeuGluPheLeuAlaLeu-379 |
| Antigenic Index - Jameson-Wolf | |
| SEQ. ID. NO. 7442 | 44-PhePheThrArgLysArgGlyAspThrGlu-53 |
| SEQ. ID. NO. 7443 | 68-ValAspThrArgGluGlyGluValSerGluAlaAspLeu-80 |
| SEQ. ID. NO. 7444 | 84-PheAspLysGlnHisProAlaLysArg-92 |
| SEQ. ID. NO. 7445 | 129-ValGluProAspThrIleAla-135 |
| SEQ. ID. NO. 7446 | 139-GlyPheGlnSerGlyAspLysIleGlnSer-148 |
| SEQ. ID. NO. 7447 | 157-TrpGlySerAlaGln-161 |
| SEQ. ID. NO. 7448 | 187-ArgThrIleAspAlaAlaGlyThrProGluAlaGlyLysIleLysAsnGlnGly-205 |
| SEQ. ID. NO. 7449 | 219-GlyGlyValGluLysGlySerProAlaGluLysAlaGlyLeuLysProGlyAspArgLeuThrAlaAlaAspGlyLysProIle-246 |
| SEQ. ID. NO. 7450 | 254-AsnLeuThrArgGlnSerProGlyLysLysIle-264 |
| SEQ. ID. NO. 7451 | 267-AsnTyrGluArgAlaGlyGlnThrHis-275 |
| SEQ. ID. NO. 7452 | 277-AlaAspIleArgProAspThrValGluGlnSerAspHis-289 |
| SEQ. ID. NO. 7453 | 295-ValGlyLeuArgProGlnProAspArgAlaTrp-305 |
| SEQ. ID. NO. 7454 | 307-AlaGlnIleArgArgSerTyrArgProSerVal-317 |
| SEQ. ID. NO. 7455 | 327-LysThrValSerHisSer-332 |
| SEQ. ID. NO. 7456 | 343-IleSerGlyAsnAla-347 |
| SEQ. ID. NO. 7457 | 362-AlaGlyGlnSerAla-366 |
| SEQ. ID. NO. 7458 | 408-IleArgGlyLysProLeuGlyGluArgValGln-418 |
| Hydrophilic Regions - Hopp-Woods | |
| SEQ. ID. NO. 7459 | 44-PhePheThrArgLysArgGlyAspThr-52 |
| SEQ. ID. NO. 7460 | 68-ValAspThrArgGluGlyGluValSerGluAlaAspLeu-80 |
| SEQ. ID. NO. 7461 | 84-PheAspLysGlnHisProAlaLysArg-92 |
| SEQ. ID. NO. 7462 | 129-ValGluProAspThrIleAla-135 |
| SEQ. ID. NO. 7463 | 139-GlyPheGlnSerGlyAspLysIleGlnSer-148 |
| SEQ. ID. NO. 7464 | 193-GlyThrProGluAlaGlyLysIleAlaLys-202 |
| SEQ. ID. NO. 7465 | 220-GlyValGluLysGlySerProAlaGluLysAlaGlyLeuLysProGlyAspArgLeuThrAlaAlaAspGlyLysPro-245 |
| SEQ. ID. NO. 7466 | 256-ThrArgGlnSerProGlyLysLysIle-264 |
| SEQ. ID. NO. 7467 | 268-TyrGluArgAlaGlyGln-273 |
| SEQ. ID. NO. 7468 | 277-AlaAspIleArgProAspThrValGluGlnSerAsp-288 |
| SEQ. ID. NO. 7469 | 299-ProGlnProAspArgAlaTrp-305 |
| SEQ. ID. NO. 7470 | 308-GlnIleArgArgSerTyrArg-314 |
| SEQ. ID. NO. 7471 | 362-AlaGlyGlnSerAla-366 |
| SEQ. ID. NO. 7472 | 411-LysProLeuGlyGluArgValGln-418 |
| 592 | |
| AMPHI Regions - AMPHI | |
| SEQ. ID. NO. 7473 | 6-PheGlyGlnIlePheSer-11 |
| SEQ. ID. NO. 7474 | 21-GlyGlyLeuLeuGlyGlyLeuIle-28 |
| SEQ. ID. NO. 7475 | 50-AlaProAsnAlaAlaAlaAlaAla-57 |
| SEQ. ID. NO. 7476 | 65-GlnGlyMetIleGlnMetLeuGlyValPheValAsp-76 |
| SEQ. ID. NO. 7477 | 94-ProTyrGlyAspLeu-98 |
| SEQ. ID. NO. 7478 | 109-ValSerGlnValGlyGlnTrp-115 |
| SEQ. ID. NO. 7479 | 153-ThrAlaValPheArgMet-158 |
| SEQ. ID. NO. 7480 | 165-TyrPheGlyAlaValAla-170 |
| SEQ. ID. NO. 7481 | 185-IleMetAlaTrpIleAsnLeuValAlaIleLeuLeuLeuSer-198 |
| Antigenic Index - Jameson-Wolf | |
| SEQ. ID. NO. 7482 | 35-GlyIleLysArgGlyLeuTyrSerAsnGluAlaGlyMetGlySerAlaProAsnAla-53 |
| SEQ. ID. NO. 7483 | 57-AlaGluValLysHisProVal-63 |
| SEQ. ID. NO. 7484 | 93-GlnProTyrGlyAspLeuSerGly-100 |
| SEQ. ID. NO. 7485 | 137-AlaTyrAlaGluSerAsnVal-143 |
| SEQ. ID. NO. 7486 | 206-ArgAspTyrThrAlaLysLeuLysMetGlyLysAspProGluPheLysLeuSerGluHisProGlyLeuLysArgArgIleLysSerAspValTrp-237 |
| Hydrophilic Regions - Hopp-Woods | |
| SEQ. ID. NO. 7487 | 35-GlyIleLysArgGlyLeuTyr-41 |
| SEQ. ID. NO. 7488 | 57-AlaGluValLysHis-61 |
| SEQ. ID. NO. 7489 | 212-LeuLysMetGlyLysAspProGluPheLysLeuSerGlu-224 |
| SEQ. ID. NO. 7490 | 226-ProGlyLeuLysArgArgIleLysSer-234 |
| 593 | |
| AMPHI Regions - AMPHI | |
| SEQ. ID. NO. 7491 | 6-GlyLeuCysLysArgPheGlyAsnLysThr-15 |
| SEQ. ID. NO. 7492 | 41-SerThrLeuLeuAsnIleIleAlaGlyIle-50 |
| SEQ. ID. NO. 7493 | 87-HisMetSerAlaLeuGlu-92 |
| SEQ. ID. NO. 7494 | 125-AlaHisArgLysProGluLysLeuSerGlyGlyGlu-136 |
| SEQ. ID. NO. 7495 | 159-PheSerSerLeuAsp-163 |
| SEQ. ID. NO. 7496 | 165-HisLeuArgGlyThrLeuArg-171 |
| SEQ. ID. NO. 7497 | 216-ProGluThrLeuValLysThrProSerCysValGlnValAlaArgLeuMetGlyLeu-234 |
| Antigenic Index - Jameson-Wolf | |
| SEQ. ID. NO. 7498 | 6-GlyLeuCysLysArgPheGlyAsnLysThrValAla-17 |
| SEQ. ID. NO. 7499 | 24-ValGlyArgGlyLysIle-29 |
| SEQ. ID. NO. 7500 | 33-LeuGlyArgSerGlyCysGlyLysSerThr-42 |
| SEQ. ID. NO. 7501 | 50-IleValArgProAspGlyGlyGlu-57 |
| SEQ. ID. NO. 7502 | 61-AsnGlyGluAsnIleThrArgMetProProGluLysArgArgIle-75 |
| SEQ. ID. NO. 7503 | 99-LysMetGlnLysMetProLysAlaGluAlaGluArgLeuAla-112 |
| SEQ. ID. NO. 7504 | 119-ValGlyLeuGluAsnGluAlaHisArgLysProGluLysLeuSerGlyGlyGluLysGlnArgLeuAlaLeu-142 |
| SEQ. ID. NO. 7505 | 157-GluSerPheSerSerLeu-162 |
| SEQ. ID. NO. 7506 | 168-GlyThrLeuArgArgMetThrAlaGluArgIleArgAsnGlyGlyIle-183 |
| SEQ. ID. NO. 7507 | 190-HisSerProGluGluAlaCysThrThrAlaAspGluIleAlaVal-204 |

TABLE 1-continued

SEQ. ID. NO. 7508 206-HisLysGlyArgIle-210
SEQ. ID. NO. 7509 214-GlyThrProGluThrLeuValLysThrProSer-224
SEQ. ID. NO. 7510 233-GlyLeuProAsnThrAspAspAsnArgHisIle-243
SEQ. ID. NO. 7511 248-ValArgPheAspGlnAspGlyMetGluCysArgValLeuSer-261
SEQ. ID. NO. 7512 263-ThrCysLeuProGluSer-268
SEQ. ID. NO. 7513 291-GlyAlaValSerGlyLysAspThrVal-299
SEQ. ID. NO. 7514 302-HisIleGluGluArgGluIleValArgPheArg-312
Hydrophilic Regions - Hopp-Woods
SEQ. ID. NO. 7515 6-GlyLeuCysLysArgPheGlyAsn-13
SEQ. ID. NO. 7516 25-GlyArgGlyLysIle-29
SEQ. ID. NO. 7517 36-SerGlyCysGlyLys-40
SEQ. ID. NO. 7518 51-ValArgProAspGlyGly-56
SEQ. ID. NO. 7519 68-MetProProGluLysArgArgIle-75
SEQ. ID. NO. 7520 99-LysMetGlnLysMetProLysAlaGluAlaGluArgLeuAla-112
SEQ. ID. NO. 7521 119-ValGlyLeuGluAsnGluAlaHisArgLysProGluLysLeuSerGlyGlyGluLysGlnArgLeuAlaLeu-142
SEQ. ID. NO. 7522 168-GlyThrLeuArgArgMetThrAlaGluArgIleArgAsn-180
SEQ. ID. NO. 7523 191-SerProGluGluAlaCysThrThrAlaAspGluIleAlaVal-204
SEQ. ID. NO. 7524 206-HisLysGlyArgIle-210
SEQ. ID. NO. 7525 236-AsnThrAspAspAsnArgHisIle-243
SEQ. ID. NO. 7526 248-ValArgPheAspGlnAspGlyMetGluCysArgValLeuSer-261
SEQ. ID. NO. 7527 293-ValSerGlyLysAspThrVal-299
SEQ. ID. NO. 7528 302-HisIleGluGluArgGluIleValArgPheArg-312
594
AMPHI Regions - AMPHI
SEQ. ID. NO. 7529 21-SerIleLeuArgLeu-25
SEQ. ID. NO. 7530 108-AlaGlyArgGluCysGlnGluThrAlaAlaAla-118
SEQ. ID. NO. 7531 138-AlaIleLysArgCysAsn-143
Antigenic Index - Jameson-Wolf
SEQ. ID. NO. 7532 1-MetGlyAlaAspThrAspGlyAspLysAspValArgLeuAsnArgThr-16
SEQ. ID. NO. 7533 51-ValGluHisProAsnArgPhe-57
SEQ. ID. NO. 7534 75-HisLeuAspGlySerThrGlyGly-82
SEQ. ID. NO. 7535 86-PheArgArgGluLysThrGlyHisLysArgArgCysHisThrGlnCys-101
SEQ. ID. NO. 7536 103-HisSerAlaArgAlaAlaGlyArgGluCysGlnGluThr-115
SEQ. ID. NO. 7537 137-ArgAlaIleLysArgCysAsn-143
Hydrophilic Regions - Hopp-Woods
SEQ. ID. NO. 7538 1-MetGlyAlaAspThrAspGlyAspLysAspValArgLeuAsnArg-15
SEQ. ID. NO. 7539 86-PheArgArgGluLysThrGlyHisLysArgArgCysHis-98
SEQ. ID. NO. 7540 105-AlaArgAlaAlaGlyArgGluCysGlnGluThr-115
SEQ. ID. NO. 7541 137-ArgAlaIleLysArgCysAsn-143
595
AMPHI Regions - AMPHI
SEQ. ID. NO. 7542 20-CysGlnProProGluAla-25
SEQ. ID. NO. 7543 140-AlaAspLeuGluLysLeuSerGlnProLeuAla-150
SEQ. ID. NO. 7544 157-GlnGlyGluValLysGluLeuVal-164
SEQ. ID. NO. 7545 169-ThrPheThrGluAlaValLysAlaGlyAspIleGluLysAla-182
SEQ. ID. NO. 7546 196-IleGluProIleAlaGluLeuPheSerGluLeuAspPro-208
SEQ. ID. NO. 7547 224-AlaGlyPheThrGlyPheHisArg-231
SEQ. ID. NO. 7548 243-SerGlyValLysGluIleAlaAlaLysLeuMetThrAspValGluAlaLeuGlnLysGluIleAsp-264
SEQ. ID. NO. 7549 274-ValGlyGlyAlaSerGluLeuIleGluGluValAlaGly-286
SEQ. ID. NO. 7550 309-AspGlySerLysLysIleValAspLeuPheArgProLeu-321
SEQ. ID. NO. 7551 337-PheLysGlnValAsnGluIleLeuAlaLys-346
SEQ. ID. NO. 7552 351-AspGlyPheGluThrTyrAspLysLeuGlyGlu-361
SEQ. ID. NO. 7553 366-AlaLeuGlnAlaSerIleAsnAlaLeuAlaGluAspLeuAlaGlnLeuArgGlyIleLeuGlyLeu-387
Antigenic Index - Jameson-Wolf
SEQ. ID. NO. 7554 1-MetArgLysPheAsn-5
SEQ. ID. NO. 7555 21-GlnProProGluAlaGluLysAlaAlaPro-30
SEQ. ID. NO. 7556 32-AlaSerGlyGluAlaGlnThrAlaAsnGluGlyGlySer-44
SEQ. ID. NO. 7557 50-AsnAspAsnAlaCysGluProMetGlu-58
SEQ. ID. NO. 7558 70-IleLysAsnAsnSerGlyArgLysLeuGluTrpGluIle-82
SEQ. ID. NO. 7559 87-MetValValAspGluArgGluAsnIleAla-96
SEQ. ID. NO. 7560 98-GlyLeuSerAspLysMetThr-104
SEQ. ID. NO. 7561 108-LeuProGlyGluTyrGluMet-114
SEQ. ID. NO. 7562 120-ThrAsnProArgGlyLysLeuValValThrAspSerGlyPheLysAspThrAlaAsnGluAlaAspLeuGluLysLeuSer-146
SEQ. ID. NO. 7563 158-GlyGluValLysGluLeuValAlaLysThrLysThrPheThrGluAlaValLysAlaGlyAspIleGluLysAlaLysSerLeuPheAla-187
SEQ. ID. NO. 7564 189-ThrArgValHisTyrGluArgIleGluProIle-199
SEQ. ID. NO. 7565 204-SerGluLeuAspProValIleAspAlaArgGluAspAspPheLysAspGlyAlaLysAspAlaGly-225
SEQ. ID. NO. 7566 238-ValGluLysAspValSerGlyValLysGluIleAlaAla-250
SEQ. ID. NO. 7567 252-LeuMetThrAspValGluAlaLeuGlnLysGluIleAsp-264
SEQ. ID. NO. 7568 269-ProProGlyLysValValGlyGlyAla-277
SEQ. ID. NO. 7569 279-GluLeuIleGluGluValAlaGlySerLysIleSerGlyGluGluAspArgTyrSerHisThrAspLeuSerAspPheGlnAlaAsnValAspGlySerLys LysIleValAsp-316
SEQ. ID. NO. 7570 322-IleGluAlaLysAsnLysAlaLeuLeuGluLysThrAspThrAsnPheLysGlnValAsn-341
SEQ. ID. NO. 7571 345-AlaLysTyrArgThrLysAspGlyPheGluThrTyrAspLysLeuGlyGluAlaAspArgLysAlaLeu-367
SEQ. ID. NO. 7572 374-LeuAlaGluAspLeuAlaGln-380
Hydrophilic Regions - Hopp-Woods
SEQ. ID. NO. 7573 1-MetArgLysPheAsn-5
SEQ. ID. NO. 7574 21-GlnProProGluAlaGluLysAlaAlaPro-30
SEQ. ID. NO. 7575 32-AlaSerGlyGluAlaGlnThrAlaAsnGluGlyGlySer-44
SEQ. ID. NO. 7576 52-AsnAlaCysGluProMetGlu-58
SEQ. ID. NO. 7577 72-AsnAsnSerGlyArgLysLeuGluTrpGluIle-82

TABLE 1-continued

| | |
|---|---|
| SEQ. ID. NO. 7578 | 87-MetValValAspGluArgGluAsnIle-95 |
| SEQ. ID. NO. 7579 | 99-LeuSerAspLysMetThr-104 |
| SEQ. ID. NO. 7580 | 110-GlyGluTyrGluMet-114 |
| SEQ. ID. NO. 7581 | 122-ProArgGlyLysLeuValVal-128 |
| SEQ. ID. NO. 7582 | 131-SerGlyPheLysAspThrAlaAsnGluAlaAspLeuGluLysLeuSer-146 |
| SEQ. ID. NO. 7583 | 158-GlyGluValLysGluLeuValAlaLysThrLysThrPheThrGluAlaValLysAlaGlyAspIleGluLysAlaLysSerLeuPheAla-187 |
| SEQ. ID. NO. 7584 | 189-ThrArgValHisTyrGluArgIleGluProIle-199 |
| SEQ. ID. NO. 7585 | 204-SerGluLeuAspProValIleAspAlaArgGluAspAspPheLysAspGlyAlaLysAspAlaGly-225 |
| SEQ. ID. NO. 7586 | 238-ValGluLysAspValSerGlyValLysGluIleAlaAla-250 |
| SEQ. ID. NO. 7587 | 252-LeuMetThrAspValGluAlaLeuGlnLysGluIleAsp-264 |
| SEQ. ID. NO. 7588 | 279-GluLeuIleGluGluValAlaGly-286 |
| SEQ. ID. NO. 7589 | 288-LysIleSerGlyGluGluAspArgTyrSerHis-298 |
| SEQ. ID. NO. 7590 | 308-ValAspGlySerLysLysIleValAsp-316 |
| SEQ. ID. NO. 7591 | 322-IleGluAlaLysAsnLysAlaLeuLeuGluLysThrAspThrAsnPhe-337 |
| SEQ. ID. NO. 7592 | 347-TyrArgThrLysAspGlyPheGluThrTyrAspLysLeuGlyGluAlaAspArgLysAlaLeu-367 |
| SEQ. ID. NO. 7593 | 374-LeuAlaGluAspLeuAlaGln-380 |
| 596 | |
| AMPHI Regions - AMPHI | |
| SEQ. ID. NO. 7594 | 9-MetLeuArgValSerLysValVal-16 |
| SEQ. ID. NO. 7595 | 50-LeuArgIleMetAlaGlyValAspLys-58 |
| SEQ. ID. NO. 7596 | 87-ValArgGluGluValGluSerGlyLeuGlyGluValAlaAlaAlaGlnLysArgLeuGluGluValTyrAlaGluTyr-112 |
| SEQ. ID. NO. 7597 | 192-ProThrAsnHisLeuAsp-197 |
| SEQ. ID. NO. 7598 | 202-GluTrpLeuGluGlnPheLeuValArgPheProGly-213 |
| SEQ. ID. NO. 7599 | 295-AlaArgPheGluGluMetSerAsnTyr-303 |
| SEQ. ID. NO. 7600 | 322-LeuGlyAsnGluValIleGluPheValAsnValSerLysSerPhe-336 |
| SEQ. ID. NO. 7601 | 366-SerThrLeuPheLysMet-371 |
| SEQ. ID. NO. 7602 | 409-AspAsnIleAlaGlu-413 |
| SEQ. ID. NO. 7603 | 440-AspGlnSerLysIleAlaGlyGlnLeuSerGlyGlyGlu-452 |
| SEQ. ID. NO. 7604 | 483-LeuArgAlaLeuGluAspAlaLeuLeuGluPheAla-494 |
| Antigenic Index - Jameson-Wolf | |
| SEQ. ID. NO. 7605 | 16-ValProProGlnLysThrIleIleLysAspIleSer-27 |
| SEQ. ID. NO. 7606 | 41-LeuAsnGlyAlaGlyLysSerThrVal-49 |
| SEQ. ID. NO. 7607 | 54-AlaGlyValAspLysGluPheGluGlyGluAla-64 |
| SEQ. ID. NO. 7608 | 75-LeuProGlnGluProGluLeuAspProGluLysThrValArgGluGluValGluSerGlyLeu-95 |
| SEQ. ID. NO. 7609 | 99-AlaAlaAlaGlnLysArgLeuGluGluValTyr-109 |
| SEQ. ID. NO. 7610 | 112-TyrAlaAsnProAspAlaAspPheAspAlaLeuAlaGluGluGlnGlyArgLeuGlu-130 |
| SEQ. ID. NO. 7611 | 136-GlySerSerThrGlyGlyGlyAlaGluHisGluLeuGluIleAlaAlaAspAlaLeuArg-155 |
| SEQ. ID. NO. 7612 | 157-ProGluTrpAspAlaLysIleAspAsnLeuSerGlyGlyGluLysArgArgValAla-175 |
| SEQ. ID. NO. 7613 | 181-LeuSerLysProAspMet-186 |
| SEQ. ID. NO. 7614 | 190-AspGluProThrAsnHisLeuAspAlaGluSer-200 |
| SEQ. ID. NO. 7615 | 219-ThrHisAspArgTyrPhe-224 |
| SEQ. ID. NO. 7616 | 233-LeuGluLeuAspArgGlyHisGlyIle-241 |
| SEQ. ID. NO. 7617 | 243-TrpLysGlyAsnTyrSerSer-249 |
| SEQ. ID. NO. 7618 | 251-LeuGluGlnLysGluLysArgLeuGluAsnGluAlaLysSerGluAlaAlaArgValLysAlaMetLysGlnGluLeuGluTrp-278 |
| SEQ. ID. NO. 7619 | 280-ArgGlnAsnAlaLysGlyArgGlnAlaLysSerLysAlaArgLeuAlaArgPheGluGluMetSerAsnTyrGluTyrGlnLysArgAsnGluThrGln Glu-313 |
| SEQ. ID. NO. 7620 | 319-AlaGluArgLeuGlyAsnGluVal-326 |
| SEQ. ID. NO. 7621 | 333-SerLysSerPheGlyAsp-338 |
| SEQ. ID. NO. 7622 | 360-ProAsnGlyAlaGlyLysSerThrLeu-368 |
| SEQ. ID. NO. 7623 | 372-IleSerGlyLysGluGlnProAspSerGlyGluValLysIle-385 |
| SEQ. ID. NO. 7624 | 395-AspGlnSerArgGluGlyLeuGlnAsnAspLysThrVal-407 |
| SEQ. ID. NO. 7625 | 411-IleAlaGluGlyArgAspIleLeu-418 |
| SEQ. ID. NO. 7626 | 425-IleProAlaArgGlnTyrLeuGlyArgPheAsnPheLysGlySerAspGlnSerLysIleAla-445 |
| SEQ. ID. NO. 7627 | 447-GlnLeuSerGlyGlyGluArgGlyArgLeuHisLeu-458 |
| SEQ. ID. NO. 7628 | 471-LeuAspGluProSerAsnAspLeuAspValGluThr-482 |
| SEQ. ID. NO. 7629 | 501-SerHisAspArgTrpPhe-506 |
| SEQ. ID. NO. 7630 | 516-AlaCysGluGlyAspSerLysTrp-523 |
| SEQ. ID. NO. 7631 | 527-AspGlyAsnTyrGlnGluTyrGluAlaAspLysLysArgArgLeuGlyGluGluGlyAlaLysProLysArgIleLysTyrLysProValThrArg-558 |
| Hydrophilic Regions- Hopp-Woods | |
| SEQ. ID. NO. 7632 | 54-AlaGlyValAspLysGluPheGluGlyGluAla-64 |
| SEQ. ID. NO. 7633 | 77-GlnGluProGluLeuAspProGluLysThrValArgGluGluValGluSerGlyLeu-95 |
| SEQ. ID. NO. 7634 | 99-AlaAlaAlaGlnLysArgLeuGluGluValTyr-109 |
| SEQ. ID. NO. 7635 | 113-AlaAsnProAspAlaAspPheAspAlaLeuAlaGluGluGlnGlyArgLeuGlu-130 |
| SEQ. ID. NO. 7636 | 141-GlyGlyAlaGluHisGluLeuGluIleAlaAlaAspAlaLeuArg-155 |
| SEQ. ID. NO. 7637 | 157-ProGluTrpAspAlaLysIleAspAsn-165 |
| SEQ. ID. NO. 7638 | 167-SerGlyGlyGluLysArgArgValAla-175 |
| SEQ. ID. NO. 7639 | 181-LeuSerLysProAsp-185 |
| SEQ. ID. NO. 7640 | 190-AspGluProThrAsn-194 |
| SEQ. ID. NO. 7641 | 196-LeuAspAlaGluSer-200 |
| SEQ. ID. NO. 7642 | 233-LeuGluLeuAspArgGlyHis-239 |
| SEQ. ID. NO. 7643 | 251-LeuGluGlnLysGluLysArgLeuGluAsnGluAlaLysSerGluAlaAlaArgValLysAlaMetLysGlnGluLeuGluTrp-278 |
| SEQ. ID. NO. 7644 | 280-ArgGlnAsnAlaLysGlyArgGlnAlaLysSerLysAlaArgLeuAlaArgPheGluGluMetSerAsn-302 |
| SEQ. ID. NO. 7645 | 304-GluTyrGlnLysArgAsnGluThrGln-312 |
| SEQ. ID. NO. 7646 | 319-AlaGluArgLeuGlyAsnGluVal-326 |
| SEQ. ID. NO. 7647 | 372-IleSerGlyLysGluGlnProAspSerGlyGluValLysIle-385 |
| SEQ. ID. NO. 7648 | 395-AspGlnSerArgGluGlyLeuGlnAsnAspLysThrVal-407 |
| SEQ. ID. NO. 7649 | 411-IleAlaGluGlyArgAspIleLeu-418 |
| SEQ. ID. NO. 7650 | 435-AsnPheLysGlySerAspGlnSerLysIle-444 |
| SEQ. ID. NO. 7651 | 449-SerGlyGlyGluArgGlyArgLeuHisLeu-458 |
| SEQ. ID. NO. 7652 | 472-AspGluProSerAsnAspLeuAspValGluThr-482 |

TABLE 1-continued

| | |
|---|---|
| SEQ. ID. NO. 7653 | 517-CysGluGlyAspSer-521 |
| SEQ. ID. NO. 7654 | 529-AsnTyrGlnGluTyrGluAlaAspLysLysArgArgLeuGlyGluGluGlyAlaLysProLysArgIleLysTyr-553 |
| 597-2 | |
| AMPHI Regions - AMPHI | |
| SEQ. ID. NO. 7655 | 30-AlaGluValLysLys-34 |
| SEQ. ID. NO. 7656 | 66-LysGluAlaAlaLysGluGlyLysGluSerLysLysThrAlaLys-80 |
| SEQ. ID. NO. 7657 | 93-GlnSerAlaArgLysGlyArgGluGly-101 |
| SEQ. ID. NO. 7658 | 112-AlaHisGlyLysPro-116 |
| SEQ. ID. NO. 7659 | 141-GlnGlyAsnProArgLysGlyGlyLys-149 |
| SEQ. ID. NO. 7660 | 163-SerAspLysAsnGlyLysAlaValLysGlnAspLysLysTyrArgGluGluLysAsn-181 |
| SEQ. ID. NO. 7661 | 217-ValSerAsnSerLeuLysGlnLeuGlnGlu-226 |
| SEQ. ID. NO. 7662 | 252-TrpAspLysPheGlnLysLeu-258 |
| SEQ. ID. NO. 7663 | 275-GlnIleSerArgPheValSerGly-282 |
| SEQ. ID. NO. 7664 | 308-LeuArgTyrThrArgTyrValAsnAla-316 |
| SEQ. ID. NO. 7665 | 318-AsnArgGluValValLysAspLeuGluLysGlnGln-329 |
| SEQ. ID. NO. 7666 | 339-IleAsnAsnGluLeuAlaArgLeuLysLys-348 |
| SEQ. ID. NO. 7667 | 351-AlaAsnValGlnSerLeu-356 |
| SEQ. ID. NO. 7668 | 364-AspAlaAlaGluGlnThrGlu-370 |
| SEQ. ID. NO. 7669 | 376-AlaLysIleAlaLysAspAlaArg-383 |
| SEQ. ID. NO. 7670 | 396-AsnLysLeuLeuSer-400 |
| SEQ. ID. NO. 7671 | 460-ProSerValMetGlyIleGlySerAlaAspGlyPheSerArgMetGlnGlyArgLeuLysLysProValAspGlyValProThrGly-488 |
| SEQ. ID. NO. 7672 | 509-ProAlaThrValGluSerIleAla-516 |
| SEQ. ID. NO. 7673 | 521-SerTyrAlaAspGluLeuAspGlyTyrGlyLys-531 |
| SEQ. ID. NO. 7674 | 543-SerIleTyrAlaGlyLeu-548 |
| Antigenic Index - Jameson-Wolf | |
| SEQ. ID. NO. 7675 | 23-AspAlaAlaHisAsnArgSerAlaGluValLysLysGlnThrLysAsnLysLysGluGlnProGluAlaAlaGluGlyLysLysGluLysGlyLysAsnGly AlaValLysAspLysLysThrGlyGlyLysGluAlaAlaLysGluGlyLysGluSerLysLysThrAlaLysAsnArgLysGluAlaGluLysGluAlaThrSer ArgGlnSerAlaArgLysGlyArgGluGlyAspLysLysSerLysAlaGluHisLysLysAlaHisGlyLysProValSerGlySerLysGluLysAsnAlaLys ThrGlnProGluAsnLysGlnGlyLysLysGluAlaLysGlyGlnGlyAsnProArgLysGlyGlyLysAlaGluLysAspThrValSerAlaAsnLysLysVal ArgSerAspLysAsnGlyLysAlaValLysGlnAspLysLysTyrArgGluGluLysAsnAlaLysThrAspSerAspGluLeuLysAla-191 |
| SEQ. ID. NO. 7676 | 196-AlaThrAsnAspValGluAsnLysLysAlaLeuLeuLysGlnSerGluGly-212 |
| SEQ. ID. NO. 7677 | 219-AsnSerLeuLysGlnLeuGlnGluGluArgIleArgGlnGluArgIleArgGlnAlaArgGlyAsnLeu-241 |
| SEQ. ID. NO. 7678 | 243-SerValAsnArgLysGlnArgGluAlaTrpAspLysPheGlnLysLeuAsnThrGluLeuAsnArgLeuLysThrGluValAlaAla-271 |
| SEQ. ID. NO. 7679 | 281-SerGlyAsnTyrLysAsnSerGlnProAsn-290 |
| SEQ. ID. NO. 7680 | 298-AsnAlaGluProGlyGlnLysAsnArgPhe-307 |
| SEQ. ID. NO. 7681 | 314-ValAsnAlaSerAsnArgGluValValLysAspLeuGluLysGlnGlnLys-330 |
| SEQ. ID. NO. 7682 | 335-GlnGluGlnLysIleAsnAsnGluLeuAlaArgLeuLysLysIleGln-350 |
| SEQ. ID. NO. 7683 | 356-LeuLeuLysLysGlnGlyValThrAspAlaAlaGluGlnThrGluSerArgArgGlnAsnAlaLysIleAlaLysAspAlaArgLysLeuLeuGluGlnLys GlyAsnGluGlnGlnLeu-395 |
| SEQ. ID. NO. 7684 | 398-LeuLeuSerAsnLeuGluLysLysLysAlaGluHisArgIleGlnAspAlaGluAlaLysArgLysLeuAlaGluAlaArgLeuAlaAlaAlaGluLysAla ArgLysGluAlaAlaGlnGlnLysAlaGluAlaArgArgAlaGluMetSerAsnLeuThrAlaGluAspArgAsnIleGlnAlaProSer-461 |
| SEQ. ID. NO. 7685 | 466-GlySerAlaAspGlyPheSerArgMetGlnGlyArgLeuLysLysProValAspGlyValProThr-487 |
| SEQ. ID. NO. 7686 | 491-GlyGlnAsnArgSerGlyGlyAspIle-499 |
| SEQ. ID. NO. 7687 | 521-SerTyrAlaAspGluLeuAspGlyTyrGly-530 |
| SEQ. ID. NO. 7688 | 536-AspHisGlyGluAsnTyr-541 |
| SEQ. ID. NO. 7689 | 561-AlaGlySerLysIleGlySerSerGlySerLeuProAspGlyGluGluGlyLeu-578 |
| SEQ. ID. NO. 7690 | 588-ValLeuAsnProSerSerTrp-594 |
| Hydrophilic Regions- Hopp-Woods | |
| SEQ. ID. NO. 7691 | 23-AspAlaAlaHisAsnArgSerAlaGluValLysLysGlnThrLysAsnLysLysGluGlnProGluAlaAlaGluGlyLysLysGluLysGlyLysAsnGly AlaValLysAspLysLysThrGlyGlyLysGluAlaAlaLysGluGlyLysGluSerLysLysThrAlaLysAsnArgLysGluAlaGluLysGluAlaThrSer ArgGlnSerAlaArgLysGlyArgGluGlyAspLysLysSerLysAlaGluHisLysLysAlaHisGlyLysProValSerGlySerLysGluLysAsnAlaLys ThrGlnProGluAsnLysGlnGlyLysLysGluAlaLysGlyGlnGlyAsnProArgLysGlyGlyLysAlaGluLysAspThrValSerAlaAsnLysLysVal ArgSerAspLysAsnGlyLysAlaValLysGlnAspLysLysTyrArgGluGluLysAsnAlaLysThrAspSerAspGluLeuLysAla-191 |
| SEQ. ID. NO. 7692 | 198-AsnAspValGluAsnLysLysAlaLeuLeuLysGlnSerGlu-211 |
| SEQ. ID. NO. 7693 | 220-SerLeuLysGlnLeuGlnGluGluArgIleArgGlnGluArgIleArgGlnAlaArgGlyAsn-240 |
| SEQ. ID. NO. 7694 | 244-ValAsnArgLysGlnArgGluAlaTrpAspLysPheGlnLysLeuAsnThrGluLeuAsnArgLeuLysThrGluValAlaAla-271 |
| SEQ. ID. NO. 7695 | 284-TyrLysAsnSerGln-288 |
| SEQ. ID. NO. 7696 | 298-AsnAlaGluProGlyGlnLysAsnArgPhe-307 |
| SEQ. ID. NO. 7697 | 317-SerAsnArgGluValValLysAspLeuGluLysGlnGlnLys-330 |
| SEQ. ID. NO. 7698 | 335-GlnGluGlnLysIleAsnAsnGluLeuAlaArgLeuLysLysIleGln-350 |
| SEQ. ID. NO. 7699 | 356-LeuLeuLysLysGlnGlyValThrAspAlaAlaGluGlnThrGluSerArgArgGlnAsnAlaLysIleAlaLysAspAlaArgLysLeuLeuGluGln LysGlyAsnGluGlnGlnLeu-395 |
| SEQ. ID. NO. 7700 | 400-SerAsnLeuGluLysLysLysAlaGluHisArgIleGlnAspAlaGluAlaLysArgLysLeuAlaGluAlaArgLeuAlaAlaAlaGluLysAlaArgLys GluAlaAlaGlnGlnLysAlaGluAlaArgArgAlaGluMet-447 |
| SEQ. ID. NO. 7701 | 451-ThrAlaGluAspArgAsnIleGln-458 |
| SEQ. ID. NO. 7702 | 474-MetGlnGlyArgLeuLysLysProValAsp-483 |
| SEQ. ID. NO. 7703 | 493-AsnArgSerGlyGlyAspIle-499 |
| SEQ. ID. NO. 7704 | 522-TyrAlaAspGluLeuAspGlyTyrGly-530 |
| SEQ. ID. NO. 7705 | 563-SerLysIleGlySer-567 |
| SEQ. ID. NO. 7706 | 570-SerLeuProAspGlyGluGluGlyLeu-578 |
| 601-2 | |
| AMPHI Regions - AMPHI | |
| SEQ. ID. NO. 7707 | 29-AlaAlaArgGluAla-33 |
| SEQ. ID. NO. 7708 | 43-ArgValLeuGlySerPro-48 |
| SEQ. ID. NO. 7709 | 50-ProTyrGlyLysGlnIleAspGlyLeuGlyAsnAlaSerSerSer-64 |
| SEQ. ID. NO. 7710 | 94-PheValAspTrpSerGly-99 |
| SEQ. ID. NO. 7711 | 101-CysGlyAsnLeuThrAlaAla-107 |
| SEQ. ID. NO. 7712 | 134-TrpGlnLysAsnIleGlyLysThrIle-142 |
| SEQ. ID. NO. 7713 | 191-LeuValAspGluIleAspValProAsnIleGlyArg-202 |
| SEQ. ID. NO. 7714 | 210-AlaGlyIleProThrValPhe-216 |

TABLE 1-continued

| | |
|---|---|
| SEQ. ID. NO. 7715 | 226-GlyLysGluLeuGlnAspAspIleAsnAsnAspAlaAlaAlaLeuGluLysPheGluLysIleArgAlaTyrGlyAlaLeu-252 |
| SEQ. ID. NO. 7716 | 254-MetGlyLeuIleSerAspValSerGluAlaAla-264 |
| SEQ. ID. NO. 7717 | 284-SerSerGlyLysThrValAsn-290 |
| SEQ. ID. NO. 7718 | 321-AlaAlaAlaValProGlyThrLeuValAsnLeuAlaAla-333 |
| SEQ. ID. NO. 7719 | 353-GlyAlaAlaAlaGlu-357 |
| Antigenic Index - Jameson-Wolf | |
| SEQ. ID. NO. 7720 | 11-TyrArgGlyGlyThrSerLysGlyValPhePheLysArgSerAspLeuProGluAlaAlaArgGluAlaGlySerAlaArgAspLysIleLeu-41 |
| SEQ. ID. NO. 7721 | 46-GlySerProAspProTyrGlyLysGlnIleAspGlyLeuGlyAsnAlaSerSerSerThrSerLys-67 |
| SEQ. ID. NO. 7722 | 69-ValIleLeuAspLysSerGluArgAlaAspHisAspValAspTyr-83 |
| SEQ. ID. NO. 7723 | 89-SerIleAspLysProPhe-94 |
| SEQ. ID. NO. 7724 | 96-AspTrpSerGlyAsnCysGly-102 |
| SEQ. ID. NO. 7725 | 116-GlyLeuValAspLysGlyLysIleProSerAspGly-127 |
| SEQ. ID. NO. 7726 | 134-TrpGlnLysAsnIleGlyLysThrIle-142 |
| SEQ. ID. NO. 7727 | 155-GluThrGlyAspPheGluLeu-161 |
| SEQ. ID. NO. 7728 | 177-AspProAlaAspGlyGluGlySerMet-185 |
| SEQ. ID. NO. 7729 | 187-ProThrGlyAsnLeuValAspGluIleAspValProAsnIleGlyArgLeuLys-204 |
| SEQ. ID. NO. 7730 | 223-GlyTyrThrGlyLysGluLeuGlnAspAspIleAsnAsnAspAlaAlaAlaLeuGluLysPheGluLysIleArgAla-248 |
| SEQ. ID. NO. 7731 | 259-AspValSerGluAlaAlaAlaArgAlaHisThrPro-270 |
| SEQ. ID. NO. 7732 | 281-TyrThrAlaSerSerGlyLysThrValAsn-290 |
| SEQ. ID. NO. 7733 | 333-AlaGlyGlyGlyThrArgLysGluValArgPheGlyHisProSerGlyThrLeuArg-351 |
| SEQ. ID. NO. 7734 | 356-AlaGluCysGlnAspGlyGln-362 |
| SEQ. ID. NO. 7735 | 369-ValMetSerArgSerAlaArgValMet-377 |
| SEQ. ID. NO. 7736 | 382-ValArgValProGluAspCysPhe-389 |
| Hydrophilic Regions - Hopp-Woods | |
| SEQ. ID. NO. 7737 | 22-LysArgSerAspLeuProGluAlaAlaArgGluAlaGlySerAlaArgAspLysIleLeu-41 |
| SEQ. ID. NO. 7738 | 49-AspProTyrGlyLysGlnIleAsp-56 |
| SEQ. ID. NO. 7739 | 62-SerSerSerThrSer-66 |
| SEQ. ID. NO. 7740 | 69-ValIleLeuAspLysSerGluArgAlaAspHisAspVal-81 |
| SEQ. ID. NO. 7741 | 89-SerIleAspLysProPhe-94 |
| SEQ. ID. NO. 7742 | 116-GlyLeuValAspLysGlyLysIleProSer-125 |
| SEQ. ID. NO. 7743 | 157-GlyAspPheGluLeu-161 |
| SEQ. ID. NO. 7744 | 177-AspProAlaAspGlyGluGly-183 |
| SEQ. ID. NO. 7745 | 191-LeuValAspGluIleAspVal-197 |
| SEQ. ID. NO. 7746 | 224-TyrThrGlyLysGluLeuGlnAspAspIleAsnAsnAspAlaAlaAlaLeuGluLysPheGluLysIleArgAla-248 |
| SEQ. ID. NO. 7747 | 259-AspValSerGluAlaAlaAlaArgAlaHisThr-269 |
| SEQ. ID. NO. 7748 | 283-AlaSerSerGlyLysThrValAsn-290 |
| SEQ. ID. NO. 7749 | 335-GlyGlyThrArgLysGluValArgPhe-343 |
| SEQ. ID. NO. 7750 | 356-AlaGluCysGlnAsp-360 |
| SEQ. ID. NO. 7751 | 372-ArgSerAlaArgValMet-377 |
| SEQ. ID. NO. 7752 | 384-ValProGluAspCysPhe-389 |
| 602-2 | |
| AMPHI Regions - AMPHI | |
| SEQ. ID. NO. 7753 | 21-ValAsnArgHisGlyGln-26 |
| SEQ. ID. NO. 7754 | 30-GlyGlyLeuAspAlaPheCys-36 |
| SEQ. ID. NO. 7755 | 54-ArgGlnIleAlaGlnIle-59 |
| SEQ. ID. NO. 7756 | 61-AlaGlyLeuHisValCysAsnSerVal-69 |
| SEQ. ID. NO. 7757 | 78-HisValIleValGluMetCysAlaTrpTyrGly-88 |
| Antigenic Index - Jameson-Wolf | |
| SEQ. ID. NO. 7758 | 5-GlnCysAspLysThrArgHisMetArgPro-14 |
| SEQ. ID. NO. 7759 | 19-ArgGlnValAsnArgHisGlyGlnThrGlyAsnGlyGlyLeuAspAla-34 |
| SEQ. ID. NO. 7760 | 36-CysSerLeuGlnGlyAsnArgLysAlaGlnValPheAspThrAspLeuIleAspArgGlnIle-56 |
| SEQ. ID. NO. 7761 | 90-SerAlaGlyGluTyr-94 |
| SEQ. ID. NO. 7762 | 99-GlnMetArgAspTyrIle-104 |
| Hydrophilic Regions - Hopp-Woods | |
| SEQ. ID. NO. 7763 | 5-GlnCysAspLysThrArgHisMetArg-13 |
| SEQ. ID. NO. 7764 | 20-GlnValAsnArgHisGlyGln-26 |
| SEQ. ID. NO. 7765 | 39-GlnGlyAsnArgLysAlaGlnValPhe-47 |
| SEQ. ID. NO. 7766 | 50-AspLeuIleAspArgGlnIle-56 |
| 603-2 | |
| AMPHI Regions - AMPHI | |
| SEQ. ID. NO. 7767 | 69-MetLeuLeuAsnGluLeuGluLys-76 |
| SEQ. ID. NO. 7768 | 107-ValMetAspGluLeuAsnAlaCysIlePro-116 |
| SEQ. ID. NO. 7769 | 121-HisAsnProAlaAsnIleSerGlyIleLeuAla-131 |
| SEQ. ID. NO. 7770 | 135-HisPheProGlyLeuProAsnValGly-143 |
| SEQ. ID. NO. 7771 | 148-SerPheHisGlnThrMetPro-154 |
| SEQ. ID. NO. 7772 | 161-AlaValProArgGluLeu-166 |
| SEQ. ID. NO. 7773 | 188-GluAlaAlaArgIleLeuGlyLysProLeuGluAspIleArgMetIleIleAlaHis-206 |
| SEQ. ID. NO. 7774 | 209-AsnGlyAlaSerIleThrAlaIleLysAsnGlyLysSerVal-222 |
| SEQ. ID. NO. 7775 | 229-ThrProIleGluGly-233 |
| SEQ. ID. NO. 7776 | 248-TyrSerTyrLeuThrSer-253 |
| SEQ. ID. NO. 7777 | 273-LeuGlyIleSerGlu-277 |
| SEQ. ID. NO. 7778 | 279-SerAsnAspCysArg-283 |
| SEQ. ID. NO. 7779 | 306-ArgLeuAlaLysTyrIleAlaSerMet-314 |
| SEQ. ID. NO. 7780 | 342-ValSerTyrLeuAsp-346 |
| Antigenic Index - Jameson-Wolf | |
| SEQ. ID. NO. 7781 | 12-GlySerSerSerLeuLysGlyAlaValIleAspArgLysSerGlySer-27 |
| SEQ. ID. NO. 7782 | 33-LeuGlyGluArgLeuThrThrProGluAla-42 |
| SEQ. ID. NO. 7783 | 45-ThrPheAsnLysAspGlyAsnLysArgGlnValProLeuSerGlyArgAsnCysHis-63 |
| SEQ. ID. NO. 7784 | 73-GluLeuGluLysHisGlyLeuHisAspArgIleLysAlaIleGly-87 |
| SEQ. ID. NO. 7785 | 91-AlaHisGlyGlyGluLysTyrSerGlu-99 |

TABLE 1-continued

| | |
|---|---|
| SEQ. ID. NO. 7786 | 106-AlaValMetAspGluLeuAsn-112 |
| SEQ. ID. NO. 7787 | 152-ThrMetProGluArgAlaTyr-158 |
| SEQ. ID. NO. 7788 | 164-ArgGluLeuArgLysLysTyrAlaPheArgArgTyrGlyPheHisGlyThrSerMetArg-183 |
| SEQ. ID. NO. 7789 | 188-GluAlaAlaArgIleLeuGlyLysProLeuGluAspIleArg-201 |
| SEQ. ID. NO. 7790 | 207-LeuGlyAsnGlyAla-211 |
| SEQ. ID. NO. 7791 | 214-ThrAlaIleLysAsnGlyLysSerValAspThrSerMetGly-227 |
| SEQ. ID. NO. 7792 | 238-ThrArgCysGlyAspIleAspProGlyVal-247 |
| SEQ. ID. NO. 7793 | 260-AlaGlnValAspGluMetLeuAsnLysLysSerGly-271 |
| SEQ. ID. NO. 7794 | 276-SerGluLeuSerAsnAspCysArgThrLeuGluIleAlaAlaAspGluGlyHisGluGlyAlaArgLeu-298 |
| SEQ. ID. NO. 7795 | 329-GlyIleGlyGluAsnSerArgAsnIleArgAlaLysThr-341 |
| SEQ. ID. NO. 7796 | 352-IleAspThrLysAlaAsnMetGluLysArgTyrGlyAsnSerGlyIle-367 |
| SEQ. ID. NO. 7797 | 369-SerProThrAspSerSerPro-375 |
| SEQ. ID. NO. 7798 | 381-ProThrAsnGluGluLeu-386 |
| Hydrophilic Regions - Hopp-Woods | |
| SEQ. ID. NO. 7799 | 19-AlaValIleAspArgLysSerGly-26 |
| SEQ. ID. NO. 7800 | 33-LeuGlyGluArgLeuThrThr-39 |
| SEQ. ID. NO. 7801 | 46-PheAsnLysAspGlyAsnLysArgGlnValProLeuSerGlyArgAsnCysHis-63 |
| SEQ. ID. NO. 7802 | 73-GluLeuGluLysHisGlyLeuHisAspArgIleLysAlaIleGly-87 |
| SEQ. ID. NO. 7803 | 92-HisGlyGlyGluLysTyrSerGlu-99 |
| SEQ. ID. NO. 7804 | 106-AlaValMetAspGluLeuAsn-112 |
| SEQ. ID. NO. 7805 | 153-MetProGluArgAlaTyr-158 |
| SEQ. ID. NO. 7806 | 164-ArgGluLeuArgLysLysTyrAlaPhe-172 |
| SEQ. ID. NO. 7807 | 188-GluAlaAlaArgIleLeuGlyLysProLeuGluAspIleArg-201 |
| SEQ. ID. NO. 7808 | 217-LysAsnGlyLysSerValAspThr-224 |
| SEQ. ID. NO. 7809 | 239-ArgCysGlyAspIleAspPro-245 |
| SEQ. ID. NO. 7810 | 260-AlaGlnValAspGluMetLeuAsnLysLysSerGly-271 |
| SEQ. ID. NO. 7811 | 277-GluLeuSerAsnAspCysArgThrLeuGluIleAlaAlaAspGluGlyHisGluGlyAlaArgLeu-298 |
| SEQ. ID. NO. 7812 | 330-IleGlyGluAsnSerArgAsnIleArgAlaLysThr-341 |
| SEQ. ID. NO. 7813 | 352-IleAspThrLysAlaAsnMetGluLysArgTyrGly-363 |
| SEQ. ID. NO. 7814 | 382-ThrAsnGluGluLeu-386 |
| 604-2 | |
| AMPHI Regions - AMPHI | |
| SEQ. ID. NO. 7815 | 36-HisArgValValGlnPheAla-42 |
| SEQ. ID. NO. 7816 | 3-ValGlyGlyValHisGlyPheAlaThr-61 |
| SEQ. ID. NO. 7817 | 95-ArgThrValSerAlaAspPheLeuGluPhePhe-105 |
| SEQ. ID. NO. 7818 | 113-AspValValLeuGlnLeuPheAlaCysValAlaGlnValGlyGlyIleGlnGluAsn-131 |
| SEQ. ID. NO. 7819 | 148-ArgHisIleAsnPheIleAspGlnIleAlaGlyTrpGlu-160 |
| SEQ. ID. NO. 7820 | 166-ValGlyTrpIleLysLysPheAsp-173 |
| SEQ. ID. NO. 7821 | 191-PheGlnAsnCysAlaValLeuHisArg-199 |
| Antigenic Index - Jameson-Wolf | |
| SEQ. ID. NO. 7822 | 11-AlaAlaCysGlyLysValAspGlnArgThrGlyTyrGlyGlyGlyGlyArgAsnGlyAsnArgGlyGlyThrHis-35 |
| SEQ. ID. NO. 7823 | 67-GlyGlyGlyArgAspGluGlyAspPheArgArgValArgAlaSerGlySerPhe-84 |
| SEQ. ID. NO. 7824 | 106-GlnSerArgGlyIle-110 |
| SEQ. ID. NO. 7825 | 127-GlyIleGlnGluAsnGlyArgAsnAlaArgValAspGluArgGlyPheGln-143 |
| SEQ. ID. NO. 7826 | 175-TyrPheGlyCysArgGluArgTyrAlaVal-184 |
| SEQ. ID. NO. 7827 | 201-MetGlyAsnAsnGly-205 |
| SEQ. ID. NO. 7828 | 211-LeuProAspPheAspArgAlaAspAlaVal-220 |
| Hydrophilic Regions - Hopp-Woods | |
| SEQ. ID. NO. 7829 | 14-GlyLysValAspGlnArgThrGlyTyr-22 |
| SEQ. ID. NO. 7830 | 24-GlyGlyGlyArgAsnGlyAsnArgGlyGlyThrHis-35 |
| SEQ. ID. NO. 7831 | 68-GlyGlyArgAspGluGlyAspPheArgArgValArgAla-80 |
| SEQ. ID. NO. 7832 | 127-GlyIleGlnGluAsnGlyArgAsnAlaArgValAspGluArgGlyPhe-142 |
| SEQ. ID. NO. 7833 | 178-CysArgGluArgTyrAlaVal-184 |
| SEQ. ID. NO. 7834 | 213-AspPheAspArgAlaAspAlaVal-220 |
| 605 | |
| AMPHI Regions - AMPHI | |
| SEQ. ID. NO. 7835 | 13-ArgGlnIleTrpLysIleAlaAsp-20 |
| SEQ. ID. NO. 7836 | 38-ThrLeuPheTyrArgPheIleSerGluAsnPheThrAspTyrMetGln-53 |
| SEQ. ID. NO. 7837 | 107-LysLeuLysGluIlePheThrAlaIle-115 |
| SEQ. ID. NO. 7838 | 128-IleLysGlyLeuPheAspAspPheAsp-136 |
| SEQ. ID. NO. 7839 | 141-ArgLeuGlySerThr-145 |
| SEQ. ID. NO. 7840 | 155-AlaValLeuLysGlyValAlaGluLeu-163 |
| SEQ. ID. NO. 7841 | 173-IleAspLeuPheGlyAspAlaTyrGluTyrLeuIleSerAsn-186 |
| SEQ. ID. NO. 7842 | 188-AlaAlaAsnAlaGlyLys-193 |
| SEQ. ID. NO. 7843 | 204-ValSerLysLeuIleAlaArg-210 |
| SEQ. ID. NO. 7844 | 217-GluLysValAsnLysIleTyrAspPro-225 |
| SEQ. ID. NO. 7845 | 240-PheAspGluHisIle-244 |
| SEQ. ID. NO. 7846 | 291-AspSerLysProPheAspAlaIleValSerAsn-301 |
| SEQ. ID. NO. 7847 | 341-HisAlaLeuAsnTyr-345 |
| SEQ. ID. NO. 7848 | 355-ValSerPheProGly-359 |
| SEQ. ID. NO. 7849 | 433-GluHisIleAlaGluIleValLysLeuPheAla-443 |
| SEQ. ID. NO. 7850 | 452-AlaGlnAsnAlaAlaGlnGlnThr-459 |
| SEQ. ID. NO. 7851 | 478-ThrArgGluIleIleAspIle-484 |
| SEQ. ID. NO. 7852 | 489-AlaGluIleGlyGluThrValAlaLysIleGluArgLeuArgArgGluIleAspGluValIleAlaGluIleGlu-513 |
| Antigenic Index - Jameson-Wolf | |
| SEQ. ID. NO. 7853 | 5-MetGlnGlnArgAlaGlnLeu-11 |
| SEQ. ID. NO. 7854 | 18-IleAlaAspGluValArgGlyAlaValAspGlyTrpAsp-30 |
| SEQ. ID. NO. 7855 | 44-IleSerGluAsnPheThrAspTyrMetGlnAlaGlyAspSerSerIleAsp-60 |
| SEQ. ID. NO. 7856 | 63-AlaMetProAspSer-67 |
| SEQ. ID. NO. 7857 | 71-ProGluIleLysAspAspAlaValLysVal-80 |

TABLE 1-continued

| | |
|---|---|
| SEQ. ID. NO. 7858 | 98-AlaHisGlnAsnGluGluLeuAsnThrLysLeuLysGlu-110 |
| SEQ. ID. NO. 7859 | 116-GluSerSerAlaSerGlyTyrProSerGluGlnAspIleLysGlyLeuPheAspAspPheAspThrThrSerSerArgLeu-142 |
| SEQ. ID. NO. 7860 | 146-ValAlaAspLysAsnLysArgLeu-153 |
| SEQ. ID. NO. 7861 | 190-AsnAlaGlyLysSerGlyGlyGluPhePheThr-200 |
| SEQ. ID. NO. 7862 | 215-GlyGlnGluLysValAsnLysIleTyrAspProAlaCysGlySerGlySer-231 |
| SEQ. ID. NO. 7863 | 235-GlnAlaLysLysGlnPheAsp-241 |
| SEQ. ID. NO. 7864 | 253-GluIleAsnHisThrThrTyrAsn-260 |
| SEQ. ID. NO. 7865 | 280-LeuGlyAspThrLeuThrAsnProLysLeuLysAspSerLysProPheAsp-296 |
| SEQ. ID. NO. 7866 | 309-IleGlySerAspAspProThrLeuIleAsnAspAspArgPheAlaPro-324 |
| SEQ. ID. NO. 7867 | 330-ProLysSerLysAlaAsp-335 |
| SEQ. ID. NO. 7868 | 345-TyrLeuSerGlyArgGlyArgAlaAla-353 |
| SEQ. ID. NO. 7869 | 362-TyrArgGlyGlyAlaGluGlnLysIleArg-371 |
| SEQ. ID. NO. 7870 | 403-LeuSerLysHisLysAspAsnThrAsp-411 |
| SEQ. ID. NO. 7871 | 419-GlyPhePheLysLysGluThrAsnAsnAsnValLeuIle-431 |
| SEQ. ID. NO. 7872 | 442-PheAlaAspLysAlaAspVal-448 |
| SEQ. ID. NO. 7873 | 458-GlnThrValLysAspAsnGlyTyr-465 |
| SEQ. ID. NO. 7874 | 473-ValGluAlaGluAspThrArgGluIleIleAsp-483 |
| SEQ. ID. NO. 7875 | 490-GluIleGlyGluThrValAlaLysIleGluArgLeuArgArgGluIleAspGluValIleAla-510 |
| Hydrophilic Regions- Hopp-Woods | |
| SEQ. ID. NO. 7876 | 5-MetGlnGlnArgAlaGlnLeu-11 |
| SEQ. ID. NO. 7877 | 18-IleAlaAspGluValArgGlyAlaValAsp-27 |
| SEQ. ID. NO. 7878 | 55-GlyAspSerSerIle-59 |
| SEQ. ID. NO. 7879 | 71-ProGluIleLysAspAspAlaValLysVal-80 |
| SEQ. ID. NO. 7880 | 98-AlaHisGlnAsnGluGluLeuAsnThrLysLeuLysGlu-110 |
| SEQ. ID. NO. 7881 | 122-TyrProSerGluGlnAspIleLysGlyLeuPheAspAspPheAspThrThrSerSerArgLeu-142 |
| SEQ. ID. NO. 7882 | 146-ValAlaAspLysAsnLysArgLeu-153 |
| SEQ. ID. NO. 7883 | 191-AlaGlyLysSerGlyGly-196 |
| SEQ. ID. NO. 7884 | 215-GlyGlnGluLysValAsnLysIleTyrAsp-224 |
| SEQ. ID. NO. 7885 | 235-GlnAlaLysLysGlnPheAsp-241 |
| SEQ. ID. NO. 7886 | 287-ProLysLeuLysAspSerLysProPhe-295 |
| SEQ. ID. NO. 7887 | 310-GlySerAspAspProThrLeuIleAsnAspAspArgPheAla-323 |
| SEQ. ID. NO. 7888 | 330-ProLysSerLysAlaAsp-335 |
| SEQ. ID. NO. 7889 | 348-GlyArgGlyArgAla-352 |
| SEQ. ID. NO. 7890 | 364-GlyGlyAlaGluGlnLysIleArg-371 |
| SEQ. ID. NO. 7891 | 404-SerLysHisLysAspAsnThrAsp-411 |
| SEQ. ID. NO. 7892 | 419-GlyPhePheLysLysGluThrAsn-426 |
| SEQ. ID. NO. 7893 | 442-PheAlaAspLysAlaAspVal-448 |
| SEQ. ID. NO. 7894 | 458-GlnThrValLysAspAsnGly-464 |
| SEQ. ID. NO. 7895 | 473-ValGluAlaGluAspThrArgGluIleIleAsp-483 |
| SEQ. ID. NO. 7896 | 490-GluIleGlyGluThrValAlaLysIleGluArgLeuArgArgGluIleAspGluValIleAla-510 |
| 606 | |
| AMPHI Regions - AMPHI | |
| SEQ. ID. NO. 7897 | 72-LeuLeuAspHisMetThrArgAspGlu-80 |
| SEQ. ID. NO. 7898 | 90-AlaHisValGlyAsnGlyAsp-96 |
| SEQ. ID. NO. 7899 | 100-LeuThrLeuIleGlnGlyValValAsnThrPhe-110 |
| SEQ. ID. NO. 7900 | 116-ArgIleIleAlaAsn-120 |
| SEQ. ID. NO. 7901 | 139-SerMetValPheGlnIleLeuPheGlyPheLeuAlaSerLeuIleVal-154 |
| SEQ. ID. NO. 7902 | 171-LysLeuValGlyAlaProLysMetIleSerAlaLeuGlnArg-184 |
| SEQ. ID. NO. 7903 | 191-AspLeuProGluGluMetAsnAla-198 |
| Antigenic Index - Jameson-Wolf | |
| SEQ. ID. NO. 7904 | 13-GluValIleAspThrProArgThrGluGluGluAla-24 |
| SEQ. ID. NO. 7905 | 31-GluAlaGlnAlaArgGlnTrpAsnLeuLysThrProGlu-43 |
| SEQ. ID. NO. 7906 | 48-HisSerProGluProAsnAla-54 |
| SEQ. ID. NO. 7907 | 57-ThrGlyAlaSerArgAsnSerSer-64 |
| SEQ. ID. NO. 7908 | 75-HisMetThrArgAspGluValGluAla-83 |
| SEQ. ID. NO. 7909 | 92-ValGlyAsnGlyAsp-96 |
| SEQ. ID. NO. 7910 | 122-IleAlaArgAsnAsnAspGlySerGlnSerGlnGlyThr-134 |
| SEQ. ID. NO. 7911 | 159-ArgGlnArgGluTyrArgAlaAspAlaGlyAla-169 |
| SEQ. ID. NO. 7912 | 182-LeuGlnArgLeuLysGlyAsnProValAspLeuProGluGluMetAsn-197 |
| SEQ. ID. NO. 7913 | 203-GlyAspThrArgAspSerLeuLeuSerThrHisProSerLeuAspAsnArgIleAlaArgLeuLysSer-225 |
| Hydrophilic Regions - Hopp-Woods | |
| SEQ. ID. NO. 7914 | 13-GluValIleAspThrProArgThrGluGluGluAla-24 |
| SEQ. ID. NO. 7915 | 59-AlaSerArgAsnSer-63 |
| SEQ. ID. NO. 7916 | 75-HisMetThrArgAspGluValGluAla-83 |
| SEQ. ID. NO. 7917 | 124-ArgAsnAsnAspGlySerGlnSer-131 |
| SEQ. ID. NO. 7918 | 159-ArgGlnArgGluTyrArgAlaAspAlaGlyAla-169 |
| SEQ. ID. NO. 7919 | 183-GlnArgLeuLysGlyAsnPro-189 |
| SEQ. ID. NO. 7920 | 191-AspLeuProGluGluMetAsn-197 |
| SEQ. ID. NO. 7921 | 203-GlyAspThrArgAspSerLeu-209 |
| SEQ. ID. NO. 7922 | 214-ProSerLeuAspAsnArgIleAlaArgLeuLysSer-225 |
| 607 | |
| AMPHI Regions - AMPHI | |
| SEQ. ID. NO. 7923 | 18-ArgLeuLeuThrThrLeuAlaLeu-25 |
| SEQ. ID. NO. 7924 | 70-PheMetGlyIleMetAlaAlaLeuAsnProMetIleAlaGln-83 |
| SEQ. ID. NO. 7925 | 90-ThrAspGluValGlyGluThr-96 |
| SEQ. ID. NO. 7926 | 104-GlyLeuPheLeuGlyValPheGlyMetValLeuMetTrpAlaAlaIleThrProPheArgAsnTrpLeuThrLeuSerAspTyrValGluGlyThrMet-136 |
| SEQ. ID. NO. 7927 | 151-MetValHisArgAlaLeuHisAlaTyrThrSerSer-162 |
| SEQ. ID. NO. 7928 | 226-PhePheArgProPheGly-231 |
| SEQ. ID. NO. 7929 | 244-PheLysGlnIleTrpLysIleGlyAla-252 |

TABLE 1-continued

| | |
|---|---|
| SEQ. ID. NO. 7930 | 320-AlaArgTyrIleSerGlyVal-326 |
| SEQ. ID. NO. 7931 | 337-IleThrValLeuSerLeuVal-343 |
| SEQ. ID. NO. 7932 | 373-PheGlnProAlaAspPheThrGlnCysIleAlaSerTyrAla-386 |
| SEQ. ID. NO. 7933 | 424-TyrGlyPheTrpThrAlaLeuIleAla-432 |
| Antigenic Index - Jameson-Wolf | |
| SEQ. ID. NO. 7934 | 15-LysGluValArgLeu-19 |
| SEQ. ID. NO. 7935 | 47-GlyAlaGlyLysGluAspLeuAla-54 |
| SEQ. ID. NO. 7936 | 86-GlyAlaGlyLysThrAspGluValGlyGluThrGlyArgGlnGlyIle-101 |
| SEQ. ID. NO. 7937 | 121-ProPheArgAsnTrp-125 |
| SEQ. ID. NO. 7938 | 128-LeuSerAspTyrValGluGlyThr-135 |
| SEQ. ID. NO. 7939 | 160-ThrSerSerLeuAsnArgProArgLeu-168 |
| SEQ. ID. NO. 7940 | 234-AlaLysPheGlyLysProAspTrp-241 |
| SEQ. ID. NO. 7941 | 311-SerLeuGlyArgArgGluPheSerArgAlaArgTyrIleSer-324 |
| SEQ. ID. NO. 7942 | 353-TyrAsnAsnAspPro-357 |
| SEQ. ID. NO. 7943 | 388-ArgGlyTyrLysValThrLys-394 |
| SEQ. ID. NO. 7944 | 447-LeuCysSerArgGluMetValArgSerHisLysAlaVal-459 |
| Hydrophilic Regions - Hopp-Woods | |
| SEQ. ID. NO. 7945 | 15-LysGluValArgLeu-19 |
| SEQ. ID. NO. 7946 | 47-GlyAlaGlyLysGluAspLeuAla-54 |
| SEQ. ID. NO. 7947 | 88-GlyLysThrAspGluValGlyGluThrGlyArg-98 |
| SEQ. ID. NO. 7948 | 163-LeuAsnArgProArg-167 |
| SEQ. ID. NO. 7949 | 312-LeuGlyArgArgGluPheSerArg-319 |
| SEQ. ID. NO. 7950 | 390-TyrLysValThrLys-394 |
| SEQ. ID. NO. 7951 | 447-LeuCysSerArgGluMetValArgSerHisLysAlaVal-459 |
| 608 | |
| AMPHI Regions - AMPHI | |
| SEQ. ID. NO. 7952 | 66-AlaValGlnLysIleLeuGln-72 |
| SEQ. ID. NO. 7953 | 93-ValLeuSerLeuLeu-97 |
| SEQ. ID. NO. 7954 | 103-ArgAlaSerAspGluLeuAlaArgIlePheGlyThrGln-115 |
| SEQ. ID. NO. 7955 | 124-AspIleGlyHisGlyIleLysGlnIleGlyArgAsnIleAlaGluGlnIleGlyGlyPheSerArgGluSerGluSer-149 |
| SEQ. ID. NO. 7956 | 154-AsnGluAlaLeuAlaAspCysLeuAspGluIleSerArgLeuArgAspGlyValGluArgLeuAsnGluArgLeuAspArgLeu-181 |
| Antigenic Index - Jameson-Wolf | |
| SEQ. ID. NO. 7957 | 13-LeuGlnSerProAspSerArgSerGluLeu-22 |
| SEQ. ID. NO. 7958 | 39-LeuAlaGlyArgIleThrGluAspGlyLeuLeuSerAlaGlyAsnGlyPheAlaAspThrGluIleThrPheArgAsnSerAla-66 |
| SEQ. ID. NO. 7959 | 71-LeuGlnGlyGlyGluProGlyAlaGlyAspIleGlyLeuGluGly-85 |
| SEQ. ID. NO. 7960 | 98-GlySerLeuArgSerArgAlaSerAspGluLeuAla-109 |
| SEQ. ID. NO. 7961 | 114-ThrGlnAlaAspIleGlySerArgAlaAlaAsp-124 |
| SEQ. ID. NO. 7962 | 131-GlnIleGlyArgAsnIleAla-137 |
| SEQ. ID. NO. 7963 | 140-IleGlyGlyPheSerArgGluSerGluSerAlaAsnIleGlyAsnGluAlaLeuAlaAspCysLeuAspGluIleSerArgLeuArgAspGlyValGlu ArgLeuAsnGluArgLeuAspArgLeuGluArgAspIleTrp-186 |
| Hydrophilic Regions - Hopp-Woods | |
| SEQ. ID. NO. 7964 | 15-SerProAspSerArgSerGluLeu-22 |
| SEQ. ID. NO. 7965 | 39-LeuAlaGlyArgIleThrGluAspGlyLeu-48 |
| SEQ. ID. NO. 7966 | 56-AlaAspThrGluIleThrPhe-62 |
| SEQ. ID. NO. 7967 | 74-GlyGluProGlyAlaGly-79 |
| SEQ. ID. NO. 7968 | 81-IleGlyLeuGluGly-85 |
| SEQ. ID. NO. 7969 | 100-LeuArgSerArgAlaSerAspGluLeuAla-109 |
| SEQ. ID. NO. 7970 | 116-AlaAspIleGlySerArgAlaAlaAsp-124 |
| SEQ. ID. NO. 7971 | 143-PheSerArgGluSerGluSerAlaAsnIleGly-153 |
| SEQ. ID. NO. 7972 | 156-AlaLeuAlaAspCysLeuAspGluIleSerArgLeuArgAspGlyValGluArgLeuAsnGluArgLeuAspArgLeuGluArgAspIleTrp-186 |
| 609 | |
| AMPHI Regions - AMPHI | |
| SEQ. ID. NO. 7973 | 15-ThrLeuAspAlaPheVal-20 |
| SEQ. ID. NO. 7974 | 30-HisHisIlePheHisGluPheArgValPheValGlyPhePhe-43 |
| SEQ. ID. NO. 7975 | 52-PheGluGlnAlaValGlu-57 |
| SEQ. ID. NO. 7976 | 67-IleAspAspPheLeu-71 |
| SEQ. ID. NO. 7977 | 114-ValAlaValCysProVal-119 |
| Antigenic Index - Jameson-Wolf | |
| SEQ. ID. NO. 7978 | 10-AlaLeuAspAspGluThrLeu-16 |
| SEQ. ID. NO. 7979 | 20-ValGlyAsnGlnArgSerSerAspIleAla-29 |
| SEQ. ID. NO. 7980 | 69-AspPheLeuAspThrAspPheGlyIle-77 |
| SEQ. ID. NO. 7981 | 79-SerGlnAlaAspGlyAsnValArg-86 |
| SEQ. ID. NO. 7982 | 99-GlyThrArgAlaLysArgGlyTyrGlyAsnHisAspLeu-111 |
| SEQ. ID. NO. 7983 | 122-PheAlaArgGluThrAspIle-128 |
| Hydrophilic Regions - Hopp-Woods | |
| SEQ. ID. NO. 7984 | 10-AlaLeuAspAspGluThrLeu-16 |
| SEQ. ID. NO. 7985 | 23-GlnArgSerSerAspIle-28 |
| SEQ. ID. NO. 7986 | 79-SerGlnAlaAspGlyAsnVal-85 |
| SEQ. ID. NO. 7987 | 100-ThrArgAlaLysArgGlyTyrGly-107 |
| SEQ. ID. NO. 7988 | 122-PheAlaArgGluThrAspIle-128 |
| 610 | |
| AMPHI Regions - AMPHI | |
| SEQ. ID. NO. 7989 | 6-MetGlnPheProTyrArg-11 |
| SEQ. ID. NO. 7990 | 18-MetArgArgMetArgArg-23 |
| SEQ. ID. NO. 7991 | 98-GluArgAlaGlnGluAlaTyr-104 |
| SEQ. ID. NO. 7992 | 111-ProSerThrValArgAlaLeuArgGluArg-120 |
| SEQ. ID. NO. 7993 | 187-IleArgGluAlaLeuGlu-192 |

TABLE 1-continued

| | |
|---|---|
| SEQ. ID. NO. 7994 | 208-TyrAlaSerAlaPheTyrGlyProPheArgAsp-218 |
| SEQ. ID. NO. 7995 | 223-SerGlyAsnLeuGlyLysAlaAsp-230 |
| SEQ. ID. NO. 7996 | 268-LeuAspValValArgArgValLysAspGlu-277 |
| SEQ. ID. NO. 7997 | 296-AlaAlaIleAlaAsn-300 |
| Antigenic Index - Jameson-Wolf | |
| SEQ. ID. NO. 7998 | 11-ArgAsnValProAlaSerArgMetArgArgMetArgArgAspAspPheSerArgArgLeuMetArgGluHisThrLeuThrAlaAspAsp-40 |
| SEQ. ID. NO. 7999 | 50-GlySerAlaArgGluGluAspValProSerMetProGlyValLysArgGlnSerLeuAsp-69 |
| SEQ. ID. NO. 8000 | 75-AlaGluGluAlaValLys-80 |
| SEQ. ID. NO. 8001 | 94-AlaAsnLysThrGluArgAlaGlnGluAlaTyrAsnProGluGlyLeuVal-110 |
| SEQ. ID. NO. 8002 | 115-ArgAlaLeuArgGluArgPhePro-122 |
| SEQ. ID. NO. 8003 | 139-GlyGlnAspGlyLeuThrAspGluAsnGlyTyrValMetAsnAspGluThrVal-156 |
| SEQ. ID. NO. 8004 | 175-AlaProSerAspMetMetAspGlyArgIleGlyAlaIleArgGluAlaLeuGluAspAlaGlyHis-196 |
| SEQ. ID. NO. 8005 | 215-ProPheArgAspAlaValGlySerSerGlyAsnLeuGlyLysAlaAspLysLysThrTyrGlnMetAspProAlaAsnThrAspGluAlaLeuHis-246 |
| SEQ. ID. NO. 8006 | 250-LeuAspIleGlnGluGlyAlaAsp-257 |
| SEQ. ID. NO. 8007 | 270-ValValArgArgValLysAspGluPheGlyVal-280 |
| SEQ. ID. NO. 8008 | 301-GlyTrpLeuAspGlyGlyLysValVal-309 |
| SEQ. ID. NO. 8009 | 317-LysArgAlaGlyAlaAspGly-323 |
| SEQ. ID. NO. 8010 | 331-GluAlaAlaLysMetLeuLysArg-338 |
| Hydrophilic Regions - Hopp-Woods | |
| SEQ. ID. NO. 8011 | 14-ProAlaSerArgMetArgArgMetArgArgAspAspPheSerArgArgLeuMetArgGluHisThrLeuThrAla-38 |
| SEQ. ID. NO. 8012 | 50-GlySerAlaArgGluGluAspValProSer-59 |
| SEQ. ID. NO. 8013 | 61-ProGlyValLysArgGlnSerLeuAsp-69 |
| SEQ. ID. NO. 8014 | 75-AlaGluGluAlaValLys-80 |
| SEQ. ID. NO. 8015 | 95-AsnLysThrGluArgAlaGlnGluAlaTyrAsn-105 |
| SEQ. ID. NO. 8016 | 115-ArgAlaLeuArgGluArgPhePro-122 |
| SEQ. ID. NO. 8017 | 141-AspGlyLeuThrAspGluAsnGly-148 |
| SEQ. ID. NO. 8018 | 151-MetAsnAspGluThrVal-156 |
| SEQ. ID. NO. 8019 | 178-AspMetMetAspGlyArgIleGlyAlaIleArgGluAlaLeuGluAspAlaGly-195 |
| SEQ. ID. NO. 8020 | 216-PheArgAspAlaValGly-221 |
| SEQ. ID. NO. 8021 | 225-AsnLeuGlyLysAlaAspLysLysThrTyrGln-235 |
| SEQ. ID. NO. 8022 | 238-ProAlaAsnThrAspGluAlaLeuHis-246 |
| SEQ. ID. NO. 8023 | 250-LeuAspIleGlnGluGlyAlaAsp-257 |
| SEQ. ID. NO. 8024 | 270-ValValArgArgValLysAspGluPheGly-279 |
| SEQ. ID. NO. 8025 | 317-LysArgAlaGlyAla-321 |
| SEQ. ID. NO. 8026 | 331-GluAlaAlaLysMetLeuLysArg-338 |
| 611 | |
| AMPHI Regions - AMPHI | |
| SEQ. ID. NO. 8027 | 15-CysArgLeuPheGlyLysLeuSerLeu-23 |
| SEQ. ID. NO. 8028 | 26-ArgLeuLeuLeuGlyLeu-31 |
| SEQ. ID. NO. 8029 | 48-ArgSerValArgArgValIle-54 |
| SEQ. ID. NO. 8030 | 63-GlnValValAlaVal-67 |
| SEQ. ID. NO. 8031 | 104-ValPheIleGluAspPheVal-110 |
| SEQ. ID. NO. 8032 | 130-GlyPheLeuGlyAsnValLeuArgThr-138 |
| Antigenic Index - Jameson-Wolf | |
| SEQ. ID. NO. 8033 | 1-MetProSerGluAsnGlyMetGlyLysArgGlnLeuAla-13 |
| SEQ. ID. NO. 8034 | 32-CysArgSerGlyValCysArgGlyArgCys-41 |
| SEQ. ID. NO. 8035 | 45-PheProSerArgSerValArgArgValIlePheArgArgValArgIle-60 |
| SEQ. ID. NO. 8036 | 119-AsnProAlaAspPheArgVal-125 |
| SEQ. ID. NO. 8037 | 142-AlaSerGlnGluAsp-146 |
| Hydrophilic Regions - Hopp-Woods | |
| SEQ. ID. NO. 8038 | 1-MetProSerGluAsnGlyMetGlyLysArgGlnLeuAla-13 |
| SEQ. ID. NO. 8039 | 35-GlyValCysArgGlyArgCys-41 |
| SEQ. ID. NO. 8040 | 53-ValIlePheArgArgValArgIle-60 |
| SEQ. ID. NO. 8041 | 121-AlaAspPheArgVal-125 |
| SEQ. ID. NO. 8042 | 142-AlaSerGlnGluAsp-146 |
| 612-2 | |
| AMPHI Regions - AMPHI | |
| SEQ. ID. NO. 8043 | 6-AsnIleAlaLysLysLeuAlaGlyValAsp-15 |
| SEQ. ID. NO. 8044 | 57-LysAlaValGluLysCysAlaGluAsnValLeu-67 |
| SEQ. ID. NO. 8045 | 81-GlyAsnPheProAsn-85 |
| Antigenic Index - Jameson-Wolf | |
| SEQ. ID. NO. 8046 | 7-IleAlaLysLysLeuAlaGlyValAsp-15 |
| SEQ. ID. NO. 8047 | 27-AspPheGlyArgAspAspAlaValArgHisSerGlyVal-39 |
| SEQ. ID. NO. 8048 | 57-LysAlaValGluLysCysAlaGlu-64 |
| SEQ. ID. NO. 8049 | 97-GlyHisHisArgAsnProTyrLysSer-105 |
| Hydrophilic Regions - Hopp-Woods | |
| SEQ. ID. NO. 8050 | 7-IleAlaLysLysLeuAlaGlyValAsp-15 |
| SEQ. ID. NO. 8051 | 28-PheGlyArgAspAspAlaValArg-35 |
| SEQ. ID. NO. 8052 | 57-LysAlaValGluLysCysAlaGlu-64 |
| SEQ. ID. NO. 8053 | 101-AsnProTyrLysSer-105 |
| 613-2 | |
| AMPHI Regions - AMPHI | |
| SEQ. ID. NO. 8054 | 7-SerArgArgSerLeu-11 |
| SEQ. ID. NO. 8055 | 95-MetProArgMetArgSer-100 |
| SEQ. ID. NO. 8056 | 103-SerProMetSerProAla-108 |
| SEQ. ID. NO. 8057 | 115-ArgIlePheCysThrAlaLeuLeuArgLys-124 |
| SEQ. ID. NO. 8058 | 140-SerSerValMetArgProAla-146 |
| SEQ. ID. NO. 8059 | 168-LeuSerGlyLeuCysArgIle-174 |

TABLE 1-continued

| | |
|---|---|
| Antigenic Index - Jameson-Wolf | |
| SEQ. ID. NO. 8060 | 1-MetSerArgSerSerArgSerArgArgSerLeuArgArgSerThrProSerArg-18 |
| SEQ. ID. NO. 8061 | 23-SerSerArgGlnSerAlaArgAla-30 |
| SEQ. ID. NO. 8062 | 35-PheAlaAspSerAspSerArgGluAsnProProIleCysSer-48 |
| SEQ. ID. NO. 8063 | 73-ProLysIleArgAlaAsnSerSerAspAlaArgGluArgArgLeuProSerArgAspSerThrAla-94 |
| SEQ. ID. NO. 8064 | 96-ProArgMetArgSerProSerSerProMetSerProAlaProGlySerProProTrp-114 |
| SEQ. ID. NO. 8065 | 130-AlaLysProPheProAlaGluSerLysProSerSerValMetArgProAlaSer-147 |
| SEQ. ID. NO. 8066 | 162-AlaAlaSerSerGluArgLeuSerGlyLeuCysArgIleArgArg-176 |
| SEQ. ID. NO. 8067 | 178-MetMetGlyArgArgAlaAspIlePheSerAspArgGlyGlyGlu-192 |
| SEQ. ID. NO. 8068 | 205-LeuSerArgTyrArgLysArgTyrGly-213 |
| Hydrophilic Regions - Hopp-Woods | |
| SEQ. ID. NO. 8069 | 1-MetSerArgSerSerArgSerArgArgSerLeuArgArgSerThrProSer-17 |
| SEQ. ID. NO. 8070 | 24-SerArgGlnSerAlaArgAla-30 |
| SEQ. ID. NO. 8071 | 36-AlaAspSerAspSerArgGluAsnProPro-45 |
| SEQ. ID. NO. 8072 | 73-ProLysIleArgAlaAsnSerSerAspAlaArgGluArgArgLeuProSerArgAspSerThrAla-94 |
| SEQ. ID. NO. 8073 | 96-ProArgMetArgSerProSer-102 |
| SEQ. ID. NO. 8074 | 133-PheProAlaGluSerLysProSerSerValMetArg-144 |
| SEQ. ID. NO. 8075 | 162-AlaAlaSerSerGluArgLeuSerGly-170 |
| SEQ. ID. NO. 8076 | 172-CysArgIleArgArg-176 |
| SEQ. ID. NO. 8077 | 178-MetMetGlyArgArgAlaAspIlePheSerAspArgGlyGlyGlu-192 |
| SEQ. ID. NO. 8078 | 206-SerArgTyrArgLysArgTyrGly-213 |
| 614-2 | |
| AMPHI Regions - AMPHI | |
| SEQ. ID. NO. 8079 | 20-SerGlnPheIleGlnGlnVal-26 |
| SEQ. ID. NO. 8080 | 65-AsnLeuIleLysThrLeuLeuAsp-72 |
| SEQ. ID. NO. 8081 | 90-AlaLeuPheTyrSerLeuLeuProValLeu-99 |
| SEQ. ID. NO. 8082 | 144-ValAlaGlyCysAspGluAlaLysGluGluValGlnGluIleValAspTyrLeuLysAlaProAsnArgTyrGlnSerLeu-170 |
| SEQ. ID. NO. 8083 | 210-AspPheValGluMetPheVal-216 |
| SEQ. ID. NO. 8084 | 222-ArgValArgAspMetPheGluGln-229 |
| SEQ. ID. NO. 8085 | 242-GluIleAspAlaValGlyArg-248 |
| SEQ. ID. NO. 8086 | 295-ProAlaLeuGlnArgProGlyArgPheAsp-304 |
| SEQ. ID. NO. 8087 | 333-SerValAspLeuLeuSerLeuAla-340 |
| SEQ. ID. NO. 8088 | 349-AlaAspLeuAlaAsnLeuValAsn-356 |
| SEQ. ID. NO. 8089 | 478-SerAsnAspPheGluArgAlaThrGlnMet-487 |
| SEQ. ID. NO. 8090 | 526-SerGluLysThrGln-530 |
| SEQ. ID. NO. 8091 | 536-GluIleArgArgIleLeuAsp-542 |
| SEQ. ID. NO. 8092 | 561-ThrMetCysLysAlaLeuMetGluTrpGluThr-571 |
| SEQ. ID. NO. 8093 | 591-AspTyrSerHisAsn-595 |
| SEQ. ID. NO. 8094 | 619-ProAlaProAlaAspThr-624 |
| Antigenic Index - Jameson-Wolf | |
| SEQ. ID. NO. 8095 | 7-LeuAspGlyLysLysGluAspAsnGlyGlnIleGlu-18 |
| SEQ. ID. NO. 8096 | 26-ValAsnAsnGlyGluValSerGly-33 |
| SEQ. ID. NO. 8097 | 45-LeuIleLysGlyGluArgThrAspLysSerThrPhe-56 |
| SEQ. ID. NO. 8098 | 60-AlaProLeuAspAspAsnLeuIle-67 |
| SEQ. ID. NO. 8099 | 70-LeuLeuAspLysAsnValArgValLysValThrProGluGluLysProSerAla-87 |
| SEQ. ID. NO. 8100 | 111-MetGlnThrGlyGlyGlyGlyLysGlyGly-120 |
| SEQ. ID. NO. 8101 | 123-SerPheGlyLysSerArgAlaArgLeuLeuAspLysAspAlaAsnLys-138 |
| SEQ. ID. NO. 8102 | 145-AlaGlyCysAspGluAlaLysGluGluValGlnGlu-156 |
| SEQ. ID. NO. 8103 | 161-LeuLysAlaProAsnArgTyrGlnSerLeuGlyGlyArgValProArgGly-177 |
| SEQ. ID. NO. 8104 | 182-GlySerProGlyThrGlyLysThrLeuLeu-191 |
| SEQ. ID. NO. 8105 | 207-SerGlySerAspPhe-211 |
| SEQ. ID. NO. 8106 | 219-GlyAlaSerArgValArgAspMetPheGluGlnAlaLysLysAsnAla-234 |
| SEQ. ID. NO. 8107 | 241-AspGluIleAspAlaValGlyArgGlnArgGlyAlaGlyLeuGlyGlyGlyAsnAspGluArgGluGlnThrLeu-265 |
| SEQ. ID. NO. 8108 | 272-MetAspGlyPheGluSerAsnGln-279 |
| SEQ. ID. NO. 8109 | 287-ThrAsnArgProAspValLeuAspProAlaLeuGlnArgProGlyArgPheAspArg-305 |
| SEQ. ID. NO. 8110 | 311-LeuProAspIleArgGlyArgGluGlnIle-320 |
| SEQ. ID. NO. 8111 | 323-ValHisSerLysLysValProLeuAspGluSerValAsp-335 |
| SEQ. ID. NO. 8112 | 341-ArgGlyThrProGlyPheSerGly-348 |
| SEQ. ID. NO. 8113 | 362-AlaGlyArgArgAsnLysValLysValAspGlnSerAspPheGluAspAlaLysAspLysIleTyrMetGlyProGluArgArgSerMetValMet HisGluAspGluLysArgAlaThrAla-402 |
| SEQ. ID. NO. 8114 | 425-ThrIleMetProArgGlyArgAla-432 |
| SEQ. ID. NO. 8115 | 438-GlnLeuProGluArgAspArgIleSerMetTyrLysAspGlnMet-452 |
| SEQ. ID. NO. 8116 | 460-PheGlyGlyArgIleAlaGlu-466 |
| SEQ. ID. NO. 8117 | 474-SerThrGlyAlaSerAsnAspPheGluArgAlaThrGlnMetAlaArgGluMetValThr-493 |
| SEQ. ID. NO. 8118 | 495-TyrGlyMetSerAspLysMetGly-502 |
| SEQ. ID. NO. 8119 | 507-AlaGluAsnGluGlyGluValPheLeu-515 |
| SEQ. ID. NO. 8120 | 518-SerValThrArgSerGlnAsnIleSerGluLysThrGlnGlnAspIleAspAlaGluIleArgArgIleLeuAspGluGlnTyr-545 |
| SEQ. ID. NO. 8121 | 551-IleLeuAspGluAsnArgAspLysMetGluThrMetCys-563 |
| SEQ. ID. NO. 8122 | 570-GluThrIleAspArgAspGlnVal-577 |
| SEQ. ID. NO. 8123 | 581-MetAlaGlyLysGlnProSerProProLysAspTyrSerHisAsnLeuArgGluAsnAlaAspAlaAlaGluAspAsnAlaProHisAlaProThr ArgGluGluThrGluAlaProAlaProAlaAspThrAlaSerThrGluSerGluGlnGlnProGluAsnLysAla-637 |
| Hydrophilic Regions - Hopp-Woods | |
| SEQ. ID. NO. 8124 | 7-LeuAspGlyLysLysGluAspAsnGlyGln-16 |
| SEQ. ID. NO. 8125 | 27-AsnAsnGlyGluValSer-32 |
| SEQ. ID. NO. 8126 | 46-IleLysGlyGluArgThrAspLysSerThr-55 |
| SEQ. ID. NO. 8127 | 61-ProLeuAspAspAsnLeuIle-67 |
| SEQ. ID. NO. 8128 | 70-LeuLeuAspLysAsnValArgValLysValThrProGluGluLysProSerAla-87 |
| SEQ. ID. NO. 8129 | 115-GlyGlyGlyLysGlyGly-120 |
| SEQ. ID. NO. 8130 | 125-GlyLysSerArgAlaArgLeuLeuAspLysAspAlaAsnLys-138 |
| SEQ. ID. NO. 8131 | 145-AlaGlyCysAspGluAlaLysGluGluValGlnGlu-156 |

TABLE 1-continued

| | |
|---|---|
| SEQ. ID. NO. 8132 | 162-LysAlaProAsnArg-166 |
| SEQ. ID. NO. 8133 | 171-GlyGlyArgValProArg-176 |
| SEQ. ID. NO. 8134 | 221-SerArgValArgAspMetPheGluGlnAlaLysLysAsnAla-234 |
| SEQ. ID. NO. 8135 | 241-AspGluIleAspAlaValGlyArgGlnArgGlyAlaGly-253 |
| SEQ. ID. NO. 8136 | 256-GlyGlyAsnAspGluArgGluGlnThr-264 |
| SEQ. ID. NO. 8137 | 273-AspGlyPheGluSer-277 |
| SEQ. ID. NO. 8138 | 287-ThrAsnArgProAspValLeuAsp-294 |
| SEQ. ID. NO. 8139 | 296-AlaLeuGlnArgProGlyArgPheAspArg-305 |
| SEQ. ID. NO. 8140 | 312-ProAspIleArgGlyArgGluGlnIle-320 |
| SEQ. ID. NO. 8141 | 324-HisSerLysLysValProLeuAspGluSerValAsp-335 |
| SEQ. ID. NO. 8142 | 362-AlaGlyArgArgAsnLysValLysValAspGlnSerAspPheGluAspAlaLysAspLysIleTyrMetGlyProGluArgArgSerMetValMet HisGluAspGluLysArgAlaThrAla-402 |
| SEQ. ID. NO. 8143 | 428-ProArgGlyArgAla-432 |
| SEQ. ID. NO. 8144 | 439-LeuProGluArgAspArgIleSerMetTyrLys-449 |
| SEQ. ID. NO. 8145 | 477-AlaSerAsnAspPheGluArgAlaThrGlnMetAlaArgGluMetValThr-493 |
| SEQ. ID. NO. 8146 | 496-GlyMetSerAspLysMetGly-502 |
| SEQ. ID. NO. 8147 | 507-AlaGluAsnGluGlyGluValPheLeu-515 |
| SEQ. ID. NO. 8148 | 518-SerValThrArgSerGlnAsnIleSerGluLysThrGlnGlnAspIleAspAlaGluIleArgArgIleLeuAspGluGlnTyr-545 |
| SEQ. ID. NO. 8149 | 551-IleLeuAspGluAsnArgAspLysMetGluThrMetCys-563 |
| SEQ. ID. NO. 8150 | 570-GluThrIleAspArgAspGlnVal-577 |
| SEQ. ID. NO. 8151 | 584-LysGlnProSerProProLysAspTyrSerHisAsnLeuArgGluAsnAlaAspAlaAlaGluAspAsnAlaPro-608 |
| SEQ. ID. NO. 8152 | 610-AlaProThrArgGluGluThrGluAlaProAlaProAlaAspThrAlaSerThrGluSerGluGlnGlnProGluAsnLysAla-637 |
| 616-2 | |
| AMPHI Regions - AMPHI | |
| SEQ. ID. NO. 8153 | 6-LysMetValValGlyLeu-11 |
| SEQ. ID. NO. 8154 | 13-AsnProGlyLysGluTyrGlu-19 |
| SEQ. ID. NO. 8155 | 48-PheGlyGluValAlaArgAla-54 |
| SEQ. ID. NO. 8156 | 77-ValAlaAlaLeuAlaGlnPheTyrLys-85 |
| SEQ. ID. NO. 8157 | 115-GlyHisAsnGlyLeuLysAspIle-122 |
| SEQ. ID. NO. 8158 | 159-HisArgArgGlnIleAspAspAlaValAlaLysSerLeuGlnAlaIleProAspIleLeuAlaGlyLysTrpGluGluAlaThrArgPheLeuHis Ser-191 |
| Antigenic Index - Jameson-Wolf | |
| SEQ. ID. NO. 8159 | 11-LeuGlyAsnProGlyLysGluTyrGluGlnThrArgHisAsnAlaGlyPhe-27 |
| SEQ. ID. NO. 8160 | 39-AlaSerPheLysGluGluLysLysPhePhe-48 |
| SEQ. ID. NO. 8161 | 55-AlaLeuProAspGly-59 |
| SEQ. ID. NO. 8162 | 70-MetAsnArgSerGlyGlnAla-76 |
| SEQ. ID. NO. 8163 | 86-IleLysProGluGlu |
| SEQ. ID. NO. 8164 | 96-AspGluLeuAspIleProCysGlyArgIleLysPhe-107 |
| SEQ. ID. NO. 8165 | 109-LeuGlyGlyGlyAsnGlyGlyHisAsnGlyLeuLysAspIleGlnAla-124 |
| SEQ. ID. NO. 8166 | 127-GlyThrAlaAspTyrTyrArg-133 |
| SEQ. ID. NO. 8167 | 138-IleGlyHisProGlyAspArgAsnLeu-146 |
| SEQ. ID. NO. 8168 | 152-LeuAsnLysProSerThrGluHisArgArgGlnIleAspAspAlaValAla-168 |
| SEQ. ID. NO. 8169 | 181-LysTrpGluGluAlaThrArg-187 |
| Hydrophilic Regions - Hopp-Woods | |
| SEQ. ID. NO. 8170 | 13-AsnProGlyLysGluTyrGluGlnThrArgHis-23 |
| SEQ. ID. NO. 8171 | 39-AlaSerPheLysGluGluLysLysPhePhe-48 |
| SEQ. ID. NO. 8172 | 86-IleLysProGluGlu-90 |
| SEQ. ID. NO. 8173 | 96-AspGluLeuAspIleProCysGlyArgIleLysPhe-107 |
| SEQ. ID. NO. 8174 | 117-AsnGlyLeuLysAspIleGlnAla-124 |
| SEQ. ID. NO. 8175 | 140-HisProGlyAspArgAsnLeu-146 |
| SEQ. ID. NO. 8176 | 155-ProSerThrGluHisArgArgGlnIleAspAspAlaValAla-168 |
| SEQ. ID. NO. 8177 | 181-LysTrpGluGluAlaThrArg-187 |
| 619 | |
| AMPHI Regions - AMPHI | |
| SEQ. ID. NO. 8178 | 50-LysLeuAlaAlaLeuLeu-55 |
| SEQ. ID. NO. 8179 | 66-GlnLeuPheGlnThrLeuThrAsn-73 |
| SEQ. ID. NO. 8180 | 134-GlnGlyGlyArgAspLeu-139 |
| SEQ. ID. NO. 8181 | 146-GlyValIlePheGlyIleLeuPheArgSerLeuSerSerLeuLeuSerArg-162 |
| SEQ. ID. NO. 8182 | 165-AspProGluGluPhe-169 |
| SEQ. ID. NO. 8183 | 175-AsnMetPheAlaGlyPheAsnThrValHisSer-185 |
| SEQ. ID. NO. 8184 | 246-AlaValValGlyProValSerPhePheGlyLeuLeuAlaAlaSerLeuAlaAsnHisPheSer-266 |
| SEQ. ID. NO. 8185 | 294-GluHisLeuLeuGly-298 |
| SEQ. ID. NO. 8186 | 303-LeuSerValValValGluPhe-309 |
| Antigenic Index - Jameson-Wolf | |
| SEQ. ID. NO. 8187 | 1-MetProSerGluLysAsnIle-7 |
| SEQ. ID. NO. 8188 | 11-AlaGlySerSerArgPro-16 |
| SEQ. ID. NO. 8189 | 35-AsnValLysGlyAspTrpAsp-41 |
| SEQ. ID. NO. 8190 | 132-IleLysGlnGlyGlyArgAspLeuSer-140 |
| SEQ. ID. NO. 8191 | 163-MetIleAspProGluGluPheThr-170 |
| SEQ. ID. NO. 8192 | 203-TrpArgGluArgTyrArgLeuAsp-210 |
| SEQ. ID. NO. 8193 | 215-GlyArgAspGlnAlaVal-220 |
| SEQ. ID. NO. 8194 | 265-PheSerProSerValLysHisSerVal-273 |
| Hydrophilic Regions - Hopp-Woods | |
| SEQ. ID. NO. 8195 | 1-MetProSerGluLysAsnIle-7 |
| SEQ. ID. NO. 8196 | 134-GlnGlyGlyArgAspLeuSer-140 |
| SEQ. ID. NO. 8197 | 163-MetIleAspProGluGluPheThr-170 |
| SEQ. ID. NO. 8198 | 203-TrpArgGluArgTyrArgLeu-209 |

TABLE 1-continued

| | |
|---|---|
| SEQ. ID. NO. 8199 | 215-GlyArgAspGlnAla-219 |
| SEQ. ID. NO. 8200 | 269-ValLysHisSerVal-273 |
| 620 | |
| AMPHI Regions - AMPHI | |
| SEQ. ID. NO. 8201 | 9-ValAlaValSerAlaLeuSerAlaCysArgGlnAla-20 |
| SEQ. ID. NO. 8202 | 31-IleSerAspArgSerVal-36 |
| SEQ. ID. NO. 8203 | 67-SerThrIleLysGlnMetPheGlyTyrThrLysLeuProGluGluProLysGlyIleArgValIleTyrValThrAspMetGlyAsnValThrAspTrp Thr-100 |
| SEQ. ID. NO. 8204 | 139-GlnAlaGluLysPhe-143 |
| Antigenic Index - Jameson-Wolf | |
| SEQ. ID. NO. 8205 | 15-SerAlaCysArgGlnAlaGluGluGlyProProProLeuProArgGlnIleSerAspArgSerValGlyHis-38 |
| SEQ. ID. NO. 8206 | 43-AsnLeuThrGluHisAsnGlyProLysAla-52 |
| SEQ. ID. NO. 8207 | 57-AsnGlyLysProAspGlnProVal-64 |
| SEQ. ID. NO. 8208 | 75-TyrThrLysLeuProGluGluProLysGlyIle-85 |
| SEQ. ID. NO. 8209 | 97-ThrAspTrpThrAsnProAsnAlaAspThrGluTrpMetAspAlaLysLys-113 |
| SEQ. ID. NO. 8210 | 125-GlyMetGlyAlaGluAspAlaLeuProPheGlyAsnLysGluGlnAlaGluLysPheAlaLysAspLysGlyGlyLysValValGlyPheAspAsp MetProAspThrTyr-161 |
| Hydrophilic Regions - Hopp-Woods | |
| SEQ. ID. NO. 8211 | 18-ArgGlnAlaGluGluGlyProProProLeu-27 |
| SEQ. ID. NO. 8212 | 30-GlnIleSerAspArgSerVal-36 |
| SEQ. ID. NO. 8213 | 46-GluHisAsnGlyProLys-51 |
| SEQ. ID. NO. 8214 | 58-GlyLysProAspGln-62 |
| SEQ. ID. NO. 8215 | 77-LysLeuProGluGluProLysGlyIle-85 |
| SEQ. ID. NO. 8216 | 103-AsnAlaAspThrGluTrpMetAspAlaLysLys-113 |
| SEQ. ID. NO. 8217 | 127-GlyAlaGluAspAlaLeu-132 |
| SEQ. ID. NO. 8218 | 135-GlyAsnLysGluGlnAlaGluLysPheAlaLysAspLysGlyGlyLys-150 |
| SEQ. ID. NO. 8219 | 155-AspAspMetProAsp-159 |
| 622 | |
| AMPHI Regions - AMPHI | |
| SEQ. ID. NO. 8220 | 28-LeuProLysAlaValArgAsnLeuAlaArg-37 |
| SEQ. ID. NO. 8221 | 62-GluGluIleIleArgTrpLeuAlaAsp-70 |
| SEQ. ID. NO. 8222 | 112-IleLeuGlyGlnIleLysAspAlaValArgValAlaGln-124 |
| SEQ. ID. NO. 8223 | 131-LysLysLeuAsnAlaLeuPheGlnLys-139 |
| SEQ. ID. NO. 8224 | 142-SerValAlaLysGluVal-147 |
| SEQ. ID. NO. 8225 | 169-GluGlnIlePheProAspIleGlyAsp-177 |
| SEQ. ID. NO. 8226 | 187-GluMetIleGluLeuValAla-193 |
| SEQ. ID. NO. 8227 | 214-AlaGlnGluLeuCysAspLys-220 |
| SEQ. ID. NO. 8228 | 232-AspLeuProAlaIleLeuHis-238 |
| SEQ. ID. NO. 8229 | 288-AspLeuAsnAspAla-292 |
| SEQ. ID. NO. 8230 | 297-ValAspAspMetValAsnIleValGlnSerGly-307 |
| SEQ. ID. NO. 8231 | 324-GluLysValAlaGluPheValArgGlnGln-333 |
| SEQ. ID. NO. 8232 | 345-LeuArgAspGluGlyGluLys-351 |
| SEQ. ID. NO. 8233 | 354-LysGlnValLeuGluAsnAlaMetLysGlnLeuAlaLys-366 |
| SEQ. ID. NO. 8234 | 372-GluValLeuGluArgLeuSerValGlnLeuThr-382 |
| SEQ. ID. NO. 8235 | 384-LysLeuLeuHisSerProThrGlnThrLeuAsnLysAlaGlyGlu-398 |
| Antigenic Index - Jameson-Wolf | |
| SEQ. ID. NO. 8236 | 16-SerIleArgGluLysLeuAla-22 |
| SEQ. ID. NO. 8237 | 30-LysAlaValArgAsnLeuAlaArgSerAsnAlaAla-41 |
| SEQ. ID. NO. 8238 | 49-ThrCysAsnArgThrGlu-54 |
| SEQ. ID. NO. 8239 | 57-CysValGlyAspSerGluGluIleIle-65 |
| SEQ. ID. NO. 8240 | 75-ProIleGluGluIleArgPro-81 |
| SEQ. ID. NO. 8241 | 87-AspMetGlnGluThrValArgHis-94 |
| SEQ. ID. NO. 8242 | 115-GlnIleLysAspAlaValArgValAlaGlnGluGlnGluSerMetGlyLysLysLeu-133 |
| SEQ. ID. NO. 8243 | 142-SerValAlaLysGluValArgThrAspThrAlaValGlyGluAsnSerVal-158 |
| SEQ. ID. NO. 8244 | 174-AspIleGlyAspLeuAsn-179 |
| SEQ. ID. NO. 8245 | 199-LysSerProArgLeu-203 |
| SEQ. ID. NO. 8246 | 210-ThrLeuAlaArgAlaGlnGluLeuCysAspLysLeuGlyValAsnAlaGlu-226 |
| SEQ. ID. NO. 8247 | 257-GlyMetValGluArgAlaLeuLysGlnArgGlnSer-268 |
| SEQ. ID. NO. 8248 | 277-AlaValProArgAspIleGluAlaGluValGlyAspLeuAsnAsp-291 |
| SEQ. ID. NO. 8249 | 305-GlnSerGlyLysGluAlaArgGlnLysAlaAlaAlaAla-317 |
| SEQ. ID. NO. 8250 | 321-LeuValSerGluLysValAlaGluPheValArgGlnGlnGlnGlyArgGlnSerVal-339 |
| SEQ. ID. NO. 8251 | 343-LysAlaLeuArgAspGluGlyGluLysAlaArgLysGlnValLeu-357 |
| SEQ. ID. NO. 8252 | 368-AlaThrAlaGluGluValLeuGlu-375 |
| SEQ. ID. NO. 8253 | 381-LeuThrAsnLysLeuLeuHisSerProThrGlnThrLeuAsnLysAlaGlyGluGluAspLysAspLeuVal-404 |
| Hydrophilic Regions - Hopp-Woods | |
| SEQ. ID. NO. 8254 | 16-SerIleArgGluLysLeuAla-22 |
| SEQ. ID. NO. 8255 | 30-LysAlaValArgAsnLeuAlaArgSerAsnAlaAla-41 |
| SEQ. ID. NO. 8256 | 59-GlyAspSerGluGluIleIle-65 |
| SEQ. ID. NO. 8257 | 75-ProIleGluGluIleArg-80 |
| SEQ. ID. NO. 8258 | 87-AspMetGlnGluThrValArgHis-94 |
| SEQ. ID. NO. 8259 | 115-GlnIleLysAspAlaValArgValAlaGlnGluGlnGluSerMetGlyLysLysLeu-133 |
| SEQ. ID. NO. 8260 | 142-SerValAlaLysGluValArgThrAspThrAlaValGlyGluAsnSerVal-158 |
| SEQ. ID. NO. 8261 | 210-ThrLeuAlaArgAlaGlnGluLeuCysAsp-219 |
| SEQ. ID. NO. 8262 | 257-GlyMetValGluArgAlaLeuLysGlnArgGlnSer-268 |
| SEQ. ID. NO. 8263 | 277-AlaValProArgAspIleGluAlaGluValGlyAspLeuAsn-290 |
| SEQ. ID. NO. 8264 | 305-GlnSerGlyLysGluAlaArgGlnLysAlaAlaAlaAla-317 |
| SEQ. ID. NO. 8265 | 321-LeuValSerGluLysValAlaGluPheValArg-331 |
| SEQ. ID. NO. 8266 | 333-GlnGlnGlyArgGlnSer-338 |

TABLE 1-continued

| | |
|---|---|
| SEQ. ID. NO. 8267 | 343-LysAlaLeuArgAspGluGlyGluLysAlaArgLysGlnValLeu-357 |
| SEQ. ID. NO. 8268 | 368-AlaThrAlaGluGluValLeuGlu-375 |
| SEQ. ID. NO. 8269 | 392-ThrLeuAsnLysAlaGlyGluGluAspLysAspLeuVal-404 |
| 624 | |
| AMPHI Regions - AMPHI | |
| SEQ. ID. NO. 8270 | 14-LeuLeuLeuGlyIleIleGlyIlePheLeuPro-24 |
| SEQ. ID. NO. 8271 | 45-ArgPheTyrArgTrpLeuHisArg-52 |
| SEQ. ID. NO. 8272 | 58-ProMetValHisAsn-62 |
| SEQ. ID. NO. 8273 | 92-PheProGlnArgTrpTrpValGlyAla-100 |
| SEQ. ID. NO. 8274 | 102-SerSerValPheCysSerLeuValAlaIle-111 |
| Antigenic Index - Jameson-Wolf | |
| SEQ. ID. NO. 8275 | 41-LysAlaSerProArgPheTyr-47 |
| SEQ. ID. NO. 8276 | 50-LeuHisArgHisArgTyrPheGlyPro-58 |
| SEQ. ID. NO. 8277 | 63-TrpGluGlnAsnGlyAlaValProArgLysAlaLys-74 |
| SEQ. ID. NO. 8278 | 115-ArgArgProGluSer-119 |
| Hydrophilic Regions - Hopp-Woods | |
| SEQ. ID. NO. 8279 | 67-GlyAlaValProArgLysAlaLys-74 |
| SEQ. ID. NO. 8280 | 115-ArgArgProGluSer-119 |
| 625 | |
| AMPHI Regions - AMPHI | |
| SEQ. ID. NO. 8281 | 25-SerGlyArgIleIleSerIleAlaAla-33 |
| SEQ. ID. NO. 8282 | 64-LysMetProProGluMetValTyrArgAla-73 |
| Antigenic Index - Jameson-Wolf | |
| SEQ. ID. NO. 8283 | 5-ArgLysMetLysLysMetThrMetCysThrArgArgVal-17 |
| SEQ. ID. NO. 8284 | 57-ProPheLysSerProGlnThrLysMetProPro-67 |
| SEQ. ID. NO. 8285 | 73-AlaSerSerSerArgMetLysGly-80 |
| SEQ. ID. NO. 8286 | 96-AspAlaProLysThrLysLeuAsnGlyMetArgLysSerAsnValGln-111 |
| Hydrophilic Regions - Hopp-Woods | |
| SEQ. ID. NO. 8287 | 5-ArgLysMetLysLysMetThrMetCysThrArgArgVal-17 |
| SEQ. ID. NO. 8288 | 60-SerProGlnThrLysMetProPro-67 |
| SEQ. ID. NO. 8289 | 74-SerSerSerArgMetLysGly-80 |
| SEQ. ID. NO. 8290 | 96-AspAlaProLysThrLysLeuAsnGlyMetArgLysSerAsnValGln-111 |
| 627-2 | |
| AMPHI Regions - AMPHI | |
| SEQ. ID. NO. 8291 | 52-TrpHisHisHisTyrGlyLysIleThrAlaPheTrpThrLeuLeuPheLeu-68 |
| SEQ. ID. NO. 8292 | 83-ThrValAlaHisAlaLeu-88 |
| SEQ. ID. NO. 8293 | 128-ValGlyThrAlaLeuAlaSerIleMetGly-137 |
| SEQ. ID. NO. 8294 | 173-IleGlyGlyGlyLeuThrPro-179 |
| SEQ. ID. NO. 8295 | 189-PheLeuLysGlyValAsp-194 |
| SEQ. ID. NO. 8296 | 245-AlaIlePheGlyLysTrp-250 |
| SEQ. ID. NO. 8297 | 258-ValValGlyAlaVal-262 |
| SEQ. ID. NO. 8298 | 284-LeuGlnAsnLeuVal-288 |
| SEQ. ID. NO. 8299 | 319-IleAlaGluValGlyLysLeuPheLeuGlyIlePheIleThrIlePheProValLeuSerIleLeuLysAlaGlyGluAlaGlyAlaLeuGlyGlyVal ValSerLeuValHisAspThrAlaGlyHisProIle-363 |
| SEQ. ID. NO. 8300 | 372-GlyIleLeuSerAlaPheLeuAspAsnAla-381 |
| SEQ. ID. NO. 8301 | 404-PheHisSerLeuLeuAlaValSer-411 |
| SEQ. ID. NO. 8302 | 416-PheMetGlyAlaLeuThrTyrIleGlyAsnAlaProAsnPheMetValLys-432 |
| SEQ. ID. NO. 8303 | 444-ThrPhePheGlyTyr-448 |
| Antigenic Index - Jameson-Wolf | |
| SEQ. ID. NO. 8304 | 20-AspLeuAspGlyAlaAsn-25 |
| SEQ. ID. NO. 8305 | 114-AspLeuAsnGlyThrProLysLeu-121 |
| SEQ. ID. NO. 8306 | 149-LeuLeuLysAlaAsnGlnAsnArgThrArgArgVal-160 |
| SEQ. ID. NO. 8307 | 172-AsnIleGlyGlyGly-176 |
| SEQ. ID. NO. 8308 | 178-ThrProLeuGlyAspProPro-184 |
| SEQ. ID. NO. 8309 | 223-ArgPhePheLysGlnGluSerIleAlaGlnAspThrProAlaGlnGlnGluLysProGluLys-243 |
| SEQ. ID. NO. 8310 | 266-GlyLeuTrpLysProGluHisProGlyPhe-275 |
| SEQ. ID. NO. 8311 | 304-ThrProLysGlnValArgAlaGlyAsnGluPheAsnPhe-316 |
| SEQ. ID. NO. 8312 | 357-AspThrAlaGlyHis-361 |
| SEQ. ID. NO. 8313 | 391-AlaGlyGlyAspAla-395 |
| SEQ. ID. NO. 8314 | 433-AlaIleAlaGluGlnArgGlyValPro-441 |
| Hydrophilic Regions - Hopp-Woods | |
| SEQ. ID. NO. 8315 | 153-AsnGlnAsnArgThrArgArgVal-160 |
| SEQ. ID. NO. 8316 | 228-GluSerIleAlaGln-232 |
| SEQ. ID. NO. 8317 | 234-ThrProAlaGlnGlnGluLysProGluLys-243 |
| SEQ. ID. NO. 8318 | 268-TrpLysProGluHisProGly-274 |
| SEQ. ID. NO. 8319 | 306-LysGlnValArgAlaGlyAsn-312 |
| SEQ. ID. NO. 8320 | 433-AlaIleAlaGluGlnArgGlyVal-440 |
| 628 | |
| AMPHI Regions - AMPHI | |
| SEQ. ID. NO. 8321 | 10-CysGlyProProAsnSerCysValSerMetLeuAlaAlaPheSerAspGlyThrSerAlaProAlaAla-32 |
| SEQ. ID. NO. 8322 | 34-GlnThrTrpIleLeuArgSer-40 |
| Antigenic Index - Jameson-Wolf | |
| SEQ. ID. NO. 8323 | 6-LysProAlaGlyCysGlyProProAsnSer-15 |
| SEQ. ID. NO. 8324 | 23-PheSerAspGlyThrSerAla-29 |
| SEQ. ID. NO. 8325 | 40-SerValLysArgLeuAsnThrAsnArgProArgLeuLysSerSerAla-55 |
| SEQ. ID. NO. 8326 | 77-MetAlaAsnGlySerAlaSerThr-84 |
| SEQ. ID. NO. 8327 | 91-GlyArgValArgSerAlaValHisLysProAspTrpIleArgLeuArgArgThrSerSerProLeuLys-113 |

Hydrophilic Regions - Hopp-Woods
SEQ. ID. NO. 8328 40-SerValLysArgLeuAsnThrAsnArgProArgLeuLysSerSerAla-55
SEQ. ID. NO. 8329 91-GlyArgValArgSerAlaValHisLys-99
SEQ. ID. NO. 8330 101-AspTrpIleArgLeuArgArgThrSerSer-110
629
AMPHI Regions - AMPHI
SEQ. ID. NO. 8331 32-ArgTrpSerAspValPheSer-38
SEQ. ID. NO. 8332 48-IleSerArgLeuProArgThrPhe-55
SEQ. ID. NO. 8333 116-ValAlaAlaLeuIleGlyMetLeu-123
SEQ. ID. NO. 8334 146-IlePheGlyGlyValIleGluAlaValAlaThr-156
SEQ. ID. NO. 8335 167-MetLeuGlyValTrpGlnGlnGlyAsp-175
SEQ. ID. NO. 8336 206-IleLeuGlyLeuGlyGlu-211
SEQ. ID. NO. 8337 252-ValValProAsnIleIleSerArgLeuMetGlyAspArgLeuArgGlnSer-268
SEQ. ID. NO. 8338 285-IleIleGlyArgVal-289
SEQ. ID. NO. 8339 300-ThrValPheGlyValLeu-305
Antigenic Index - Jameson-Wolf
SEQ. ID. NO. 8340 38-SerLeuSerAspSerGln-43
SEQ. ID. NO. 8341 50-ArgLeuProArgThr-54
SEQ. ID. NO. 8342 77-AsnArgPheValGluProSerMetValGlyAlaSerGln-89
SEQ. ID. NO. 8343 130-ArgArgLeuProProThrAla-136
SEQ. ID. NO. 8344 260-LeuMetGlyAspArgLeuArgGlnSer-268
Hydrophilic Regions - Hopp-Woods
SEQ. ID. NO. 8345 260-LeuMetGlyAspArgLeuArgGln-267
630-2
AMPHI Regions - AMPHI
SEQ. ID. NO. 8346 6-PheLeuGluLysIleGluPro-12
SEQ. ID. NO. 8347 23-TrpTyrAlaLeuTyrGlu-28
SEQ. ID. NO. 8348 64-LeuPheProAlaMetPheTyrGlyMetTyrAsn-74
SEQ. ID. NO. 8349 87-LeuLeuGlnGlnAsnIleAlaAsnAspTrpHisTyrAlaPhe-100
SEQ. ID. NO. 8350 137-GlyPheTrpGluValLeuPheAla-144
SEQ. ID. NO. 8351 190-PheGlyGlyThrGlyLysAsnPhe-197
SEQ. ID. NO. 8352 224-AlaValAspGlyTyrSerGlyAlaThrAlaLeuAlaGlnTrp-237
SEQ. ID. NO. 8353 242-AlaAspGlyLeuLysAsnAlaVal-249
SEQ. ID. NO. 8354 258-AspAlaPheIleGlyLysLeuProGlySerIleGlyGluValSer-272
SEQ. ID. NO. 8355 285-PheAlaArgIleAlaSerTrpArgIleIleAlaGlyValMet-298
SEQ. ID. NO. 8356 302-IleAlaMetSerSerLeuPheAsnPhe-310
SEQ. ID. NO. 8357 344-ValSerAlaSerPheThrAsnValGlyLysTrpTrpTyrGlyAlaLeuIleGlyValMetCysValLeuIleArgVal-369
SEQ. ID. NO. 8358 382-IleLeuPheAlaAsnLeuPheAlaProIlePheAspTyrPhe-395
Antigenic Index - Jameson-Wolf
SEQ. ID. NO. 8359 6-PheLeuGluLysIleGlu-11
SEQ. ID. NO. 8360 16-ProGlyGlyLysHisGluLys-22
SEQ. ID. NO. 8361 37-SerGlyAlaValThrArgLysAlaAlaHisValArgAspAlaLeuAspSerLysArgMet-56
SEQ. ID. NO. 8362 107-AsnMetSerSerGluAlaGlyValSerAspLysMet-118
SEQ. ID. NO. 8363 146-ValArgLysHisGluIleAsnGlu-153
SEQ. ID. NO. 8364 189-ValPheGlyGlyThrGlyLysAsnPheMet-198
SEQ. ID. NO. 8365 212-TyrProAlaAsnLeuSerGlyAspAla-220
SEQ. ID. NO. 8366 241-GlyAlaAspGlyLeuLys-246
SEQ. ID. NO. 8367 264-LeuProGlySerIleGly-269
SEQ. ID. NO. 8368 312-GlySerAspThrAsnAla-317
SEQ. ID. NO. 8369 400-AsnIleLysArgArgLysAlaArgSerAsnGly-410
Hydrophilic Regions - Hopp-Woods
SEQ. ID. NO. 8370 6-PheLeuGluLysIleGlu-11
SEQ. ID. NO. 8371 18-GlyLysHisGluLys-22
SEQ. ID. NO. 8372 39-AlaValThrArgLysAlaAlaHisValArgAspAlaLeuAspSerLysArgMet-56
SEQ. ID. NO. 8373 108-MetSerSerGluAlaGlyValSerAsp-116
SEQ. ID. NO. 8374 146-ValArgLysHisGluIleAsn-152
SEQ. ID. NO. 8375 400-AsnIleLysArgArgLysAlaArgSerAsnGly-410
638
AMPHI Regions - AMPHI
SEQ. ID. NO. 8376 30-IleValAspIleValGluHis-36
SEQ. ID. NO. 8377 46-AspIleValGluTyrPheGluProLeuGlyLys-56
SEQ. ID. NO. 8378 108-ProPheGlyAsnValValAlaAspAspLeuArgThrGly-120
SEQ. ID. NO. 8379 148-ArgIleGlyArgThrMet-153
SEQ. ID. NO. 8380 198-GluArgTyrValArgArgValTyrGlyTyrGlyThrPro-210
SEQ. ID. NO. 8381 212-ProValAlaPheAspGlyCysGlyThrValGlyArg-223
SEQ. ID. NO. 8382 242-SerGlnPheGluArgIleAlaArgProGly-251
Antigenic Index - Jameson-Wolf
SEQ. ID. NO. 8383 43-AlaAspGlyAspIle-47
SEQ. ID. NO. 8384 53-ProLeuGlyLysHisGln-58
SEQ. ID. NO. 8385 81-ValAspGlyGluThrGlnIle-87
SEQ. ID. NO. 8386 99-AlaGlyIleGlyLysAsnAlaVal-106
SEQ. ID. NO. 8387 113-ValAlaAspAspLeuArgThrGlyCysValProAsnGly-125
SEQ. ID. NO. 8388 135-GlnSerArgValAlaAsp-140
SEQ. ID. NO. 8389 156-TyrAlaAspArgIleIle-161
SEQ. ID. NO. 8390 168-AsnGlnGlyAlaArgGlySerPhe-175
SEQ. ID. NO. 8391 178-IleAsnThrGlyIleHis-183
SEQ. ID. NO. 8392 188-HisThrGlyThrGlyAsnGlyGlnValAlaGluArgTyrValArg-202
SEQ. ID. NO. 8393 205-TyrGlyTyrGlyThr-209
SEQ. ID. NO. 8394 216-AspGlyCysGlyThrValGlyArgProPheAsnArgAsnArgPheVal-231
SEQ. ID. NO. 8395 240-AlaGlySerGlnPheGluArgIleAlaArgProGlyAlaGlyLysCysGly-256

TABLE 1-continued

| | |
|---|---|
| Hydrophilic Regions - Hopp-Woods | |
| SEQ. ID. NO. 8396 | 43-AlaAspGlyAspIle-47 |
| SEQ. ID. NO. 8397 | 81-ValAspGlyGluThrGlnIle-87 |
| SEQ. ID. NO. 8398 | 113-ValAlaAspAspLeuArgThr-119 |
| SEQ. ID. NO. 8399 | 136-SerArgValAlaAsp-140 |
| SEQ. ID. NO. 8400 | 195-GlnValAlaGluArgTyrValArg-202 |
| SEQ. ID. NO. 8401 | 243-GlnPheGluArgIleAlaArgProGlyAlaGly-253 |
| 639-1 | |
| AMPHI Regions - AMPHI | |
| SEQ. ID. NO. 8402 | 95-TyrLysAsnAsnArg-99 |
| SEQ. ID. NO. 8403 | 137-LeuLysValPheAspAsnIle-143 |
| SEQ. ID. NO. 8404 | 157-ValAsnTyrSerAspIleHisAspAsnIleIleAsnLysAla-170 |
| SEQ. ID. NO. 8405 | 181-TyrAspLysLeuPheAlaAsnHisPheGlu-190 |
| SEQ. ID. NO. 8406 | 269-AlaProValSerArg-273 |
| SEQ. ID. NO. 8407 | 290-GlnPheProAlaValLeuProGly-297 |
| SEQ. ID. NO. 8408 | 322-AspGluLeuLeuLysGluValGlu-329 |
| Antigenic Index - Jameson-Wolf | |
| SEQ. ID. NO. 8409 | 13-GluGluThrAlaPro-17 |
| SEQ. ID. NO. 8410 | 23-HisAsnAsnIleLeuAspAsnSer30 |
| SEQ. ID. NO. 8411 | 41-AlaMetValArgGluAsnLysIleValGly-50 |
| SEQ. ID. NO. 8412 | 52-AlaThrLeuArgValAsnGluArgGlyAsnGly-62 |
| SEQ. ID. NO. 8413 | 75-GlyAsnAspIleSerLysGlyArgAspGlyIlePheSerAsnThrSerThrHisAsnThrTyrLysAsnAsnArgPheSerAsp-102 |
| SEQ. ID. NO. 8414 | 111-TyrThrAsnAspSerGluIleSerGly-119 |
| SEQ. ID. NO. 8415 | 121-IleSerValGlyAsnAsn-126 |
| SEQ. ID. NO. 8416 | 135-GluArgLeuLysVal-139 |
| SEQ. ID. NO. 8417 | 145-ValGlySerArgAspGlnGlyIle-152 |
| SEQ. ID. NO. 8418 | 160-SerAspIleHisAspAsnIleIleAsnLysAlaGlyLys-172 |
| SEQ. ID. NO. 8419 | 203-GluGlyThrSerLeuHisAspAsnSerPheIleAsnAsnGluSerGlnValLysTyrVal-222 |
| SEQ. ID. NO. 8420 | 228-AspTrpSerGluGlyGlyHisGlyAsnTyrTrpSerAspAsnSerAla-243 |
| SEQ. ID. NO. 8421 | 246-LeuAsnGlyAspGlyPheGlyAspSerAlaTyrArgProAsnGlyIleIle-262 |
| SEQ. ID. NO. 8422 | 297-GlyGlyValValAspSerLysProLeuMetLysProTyrAlaProLysIleGlnThr-315 |
| SEQ. ID. NO. 8423 | 318-GlnAlaMetLysAspGluLeuLeuLysGluValGluThrArgGlnSerGluTrpGlyArgAlaGluAsnGlySerLeuAsn-344 |
| Hydrophilic Regions - Hopp-Woods | |
| SEQ. ID. NO. 8424 | 41-AlaMetValArgGluAsnLysIleValGly-50 |
| SEQ. ID. NO. 8425 | 52-AlaThrLeuArgValAsnGluArgGlyAsn-61 |
| SEQ. ID. NO. 8426 | 77-AspIleSerLysGlyArgAspGlyIle-85 |
| SEQ. ID. NO. 8427 | 95-TyrLysAsnAsnArgPheSerAsp-102 |
| SEQ. ID. NO. 8428 | 113-AsnAspSerGluIleSerGly-119 |
| SEQ. ID. NO. 8429 | 135-GluArgLeuLysVal-139 |
| SEQ. ID. NO. 8430 | 146-GlySerArgAspGlnGly-151 |
| SEQ. ID. NO. 8431 | 299-ValValAspSerLysProLeuMet-306 |
| SEQ. ID. NO. 8432 | 318-GlnAlaMetLysAspGluLeuLeuLysGluValGluThrArgGlnSerGluTrpGlyArgAlaGluAsnGlySer-342 |
| 640-2 | |
| AMPHI Regions - AMPHI | |
| SEQ. ID. NO. 8433 | 6-SerIleLeuLysSerIleGlyIle-13 |
| SEQ. ID. NO. 8434 | 22-SerIleLysArgMetSer-27 |
| SEQ. ID. NO. 8435 | 47-LeuProAlaTyrAlaGluArgLeuProAspPheLeuAlaLysIleGlnPro-63 |
| SEQ. ID. NO. 8436 | 72-ArgTyrGlyLysPro-76 |
| SEQ. ID. NO. 8437 | 127-AlaLysLeuValAspHisHis-133 |
| SEQ. ID. NO. 8438 | 141-IleProHisLeuProAlaProGlyArgAlaIle-151 |
| SEQ. ID. NO. 8439 | 153-SerAsnTrpLeuProAla-158 |
| Antigenic Index - Jameson-Wolf | |
| SEQ. ID. NO. 8440 | 24-LysArgMetSerAlaPheArgAlaArgIle-33 |
| SEQ. ID. NO. 8441 | 50-TyrAlaGluArgLeuProAspPhe-57 |
| SEQ. ID. NO. 8442 | 59-AlaLysIleGlnProSerGluIlePheProGlyAlaAspArgTyrGlyLysProGluGlyLysProMetVal-82 |
| SEQ. ID. NO. 8443 | 84-ArgValTyrLysGlyAspGluGlnLeu-92 |
| SEQ. ID. NO. 8444 | 101-AlaValAsnThrArgGlyTyrSerSerLysProIleAsp-113 |
| SEQ. ID. NO. 8445 | 128-LysLeuValAspHisHisGlu-134 |
| SEQ. ID. NO. 8446 | 144-LeuProAlaProGlyArgAlaIleArg-152 |
| SEQ. ID. NO. 8447 | 168-AsnArgLeuArgLeuLysGlyLeuPro-176 |
| SEQ. ID. NO. 8448 | 178-ValProGlnProSerLysAlaThrGly-186 |
| Hydrophilic Regions - Hopp-Woods | |
| SEQ. ID. NO. 8449 | 24-LysArgMetSerAlaPheArgAlaArgIle-33 |
| SEQ. ID. NO. 8450 | 50-TyrAlaGluArgLeuPro-55 |
| SEQ. ID. NO. 8451 | 68-ProGlyAlaAspArgTyrGlyLysProGluGlyLysProMetVal-82 |
| SEQ. ID. NO. 8452 | 85-ValTyrLysGlyAspGluGlnLeu-92 |
| SEQ. ID. NO. 8453 | 128-LysLeuValAspHisHisGlu-134 |
| SEQ. ID. NO. 8454 | 146-AlaProGlyArgAlaIleArg-152 |
| SEQ. ID. NO. 8455 | 168-AsnArgLeuArgLeuLysGly-174 |
| SEQ. ID. NO. 8456 | 180-GlnProSerLysAlaThrGly-186 |
| 642-2 | |
| AMPHI Regions - AMPHI | |
| SEQ. ID. NO. 8457 | 157-IleLysHisIleValArgAlaPhe-164 |
| SEQ. ID. NO. 8458 | 179-GlyValSerAlaPheLysThrLeuArgThrGlnGluPheLeuGlnHisLeuArgGlyGlyVal-199 |
| SEQ. ID. NO. 8459 | 202-PheArgGlyGluGly-206 |
| SEQ. ID. NO. 8460 | 208-AspAspValArgLeu-212 |
| SEQ. ID. NO. 8461 | 228-AspValAlaValLysAsnLeuGlyAsnLeuMetAlaAlaProAsp-242 |
| SEQ. ID. NO. 8462 | 259-PheGlnIlePheLysAspValPheHisAsnAlaValArgHisAlaAspGlnLeuGln-277 |
| SEQ. ID. NO. 8463 | 311-ValAspGlyValThrAspGlyAla-318 |
| SEQ. ID. NO. 8464 | 337-GlnValAspAspPheGlyGluPheAlaValPhe-347 |

TABLE 1-continued

| | |
|---|---|
| SEQ. ID. NO. 8465 | 366-PheArgGlyValAsp-370 |
| SEQ. ID. NO. 8466 | 409-HisLeuGlnThrLeuArgAspLeuArgPheIleAlaGluLeuLeuGlnTrpLeuGlnHisGlnArgAlaPheAspAlaGlyThr-436 |
| SEQ. ID. NO. 8467 | 445-ProArgAsnProGlnAsp-450 |
| Antigenic Index - Jameson-Wolf | |
| SEQ. ID. NO. 8468 | 1-MetArgHisProProGlnSerAlaAlaLeu-10 |
| SEQ. ID. NO. 8469 | 17-LeuLeuHisArgProLysSerValCysArgArgArgLysCysArgLeuLysAla-34 |
| SEQ. ID. NO. 8470 | 36-ProLeuSerAspGlyIleAlaCys-43 |
| SEQ. ID. NO. 8471 | 63-ValGlnGlnGluGlyCysGly-69 |
| SEQ. ID. NO. 8472 | 75-LeuTyrGluAspLysGluSerGlyAspAspPheAlaAspLysAspPheLeuGln-92 |
| SEQ. ID. NO. 8473 | 104-GluAlaAlaAspValPheArg-110 |
| SEQ. ID. NO. 8474 | 115-AlaGlyAspGlyGlyLysAlaGly-122 |
| SEQ. ID. NO. 8475 | 144-PheGlyGlyGlyAlaAspLysLeu-151 |
| SEQ. ID. NO. 8476 | 164-PheLysAsnArgGluGlyAlaAspValAspSerAspIleAlaGly-178 |
| SEQ. ID. NO. 8477 | 184-LysThrLeuArgThrGlnGlu1-190 |
| SEQ. ID. NO. 8478 | 202-PheArgGlyGluGlyPheAspAspValArgLeu-212 |
| SEQ. ID. NO. 8479 | 217-GlyAspGlyGlyAsnArgArgAsnGlyMetAla-227 |
| SEQ. ID. NO. 8480 | 249-AspGluPheAspVal-253 |
| SEQ. ID. NO. 8481 | 271-ArgHisAlaAspGlnLeuGlnAlaAlaAlaAspLysAspValLeuGluArgAlaGlnThrGly-291 |
| SEQ. ID. NO. 8482 | 300-HisGlyGlyCysArg-304 |
| SEQ. ID. NO. 8483 | 306-PheGlyIleAspAlaValAspGlyValThrAspGly-317 |
| SEQ. ID. NO. 8484 | 331-CysPheGlyAspGluGlnGlnValAspAspPheGly-342 |
| SEQ. ID. NO. 8485 | 350-PheGlyGlyAsnGluGluGluValAlaLeu-359 |
| SEQ. ID. NO. 8486 | 369-ValAspValAsnGly-373 |
| SEQ. ID. NO. 8487 | 387-CysAsnArgArgAlaGlyGlyPhe-394 |
| SEQ. ID. NO. 8488 | 396-PheGlyAsnThrGln-400 |
| SEQ. ID. NO. 8489 | 411-GlnThrLeuArgAspLeuArgPhe-418 |
| SEQ. ID. NO. 8490 | 430-ArgAlaPheAspAlaGlyThrGlnArgAsnGly-440 |
| SEQ. ID. NO. 8491 | 443-ValMetProArgAsnProGlnAspPheLeuAsp-453 |
| SEQ. ID. NO. 8492 | 468-GluGlyGlnGlnGlnThrArg-474 |
| Hydrophilic Regions - Hopp-Woods | |
| SEQ. ID. NO. 8493 | 1-MetArgHisProPro-5 |
| SEQ. ID. NO. 8494 | 17-LeuLeuHisArgProLysSerValCysArgArgArgLysCysArgLeuLysAla-34 |
| SEQ. ID. NO. 8495 | 75-LeuTyrGluAspLysGluSerGlyAspAspPheAlaAspLysAspPheLeu-91 |
| SEQ. ID. NO. 8496 | 104-GluAlaAlaAspValPheArg-110 |
| SEQ. ID. NO. 8497 | 117-AspGlyGlyLysAla-121 |
| SEQ. ID. NO. 8498 | 147-GlyAlaAspLysLeu-151 |
| SEQ. ID. NO. 8499 | 164-PheLysAsnArgGluGlyAlaAspValAspSerAspIle-176 |
| SEQ. ID. NO. 8500 | 184-LysThrLeuArgThr-188 |
| SEQ. ID. NO. 8501 | 205-GluGlyPheAspAspValArgLeu-212 |
| SEQ. ID. NO. 8502 | 217-GlyAspGlyGlyAsnArgArgAsnGlyMet-226 |
| SEQ. ID. NO. 8503 | 249-AspGluPheAspVal-253 |
| SEQ. ID. NO. 8504 | 271-ArgHisAlaAspGlnLeuGlnAlaAlaAlaAspLysAspValLeuGluArgAlaGlnThr-290 |
| SEQ. ID. NO. 8505 | 310-AlaValAspGlyValThrAspGly-317 |
| SEQ. ID. NO. 8506 | 331-CysPheGlyAspGluGlnGlnValAspAspPheGly-342 |
| SEQ. ID. NO. 8507 | 352-GlyAsnGluGluGluValAlaLeu-359 |
| SEQ. ID. NO. 8508 | 387-CysAsnArgArgAlaGly-392 |
| SEQ. ID. NO. 8509 | 412-ThrLeuArgAspLeuArgPhe-418 |
| SEQ. ID. NO. 8510 | 435-GlyThrGlnArgAsnGly-440 |
| SEQ. ID. NO. 8511 | 446-ArgAsnProGlnAsp-450 |
| SEQ. ID. NO. 8512 | 468-GluGlyGlnGlnGln-472 |
| 644-2 | |
| AMPHI Regions - AMPHI | |
| SEQ. ID. NO. 8513 | 13-MetAspThrAlaAlaPheLeuLysHisIleGluSerAlaPheArgArgIlePheSerAspGlyIleAspLeuMetArgTyrLeu-40 |
| SEQ. ID. NO. 8514 | 69-GlnPheGluIleGlnGluValLeuArgIleAlaGly-80 |
| SEQ. ID. NO. 8515 | 99-GlnProLeuGlnGluPheGlyAsp-106 |
| SEQ. ID. NO. 8516 | 139-ArgGluMetGlnSerTyrTyrGluTyrIleAspGly-150 |
| SEQ. ID. NO. 8517 | 160-TyrTrpGlnGlyAsn-164 |
| SEQ. ID. NO. 8518 | 182-LeuAlaLysValIleAspLeuLeu-189 |
| SEQ. ID. NO. 8519 | 234-AlaGlyLeuArgAlaPheGlnAsn-241 |
| SEQ. ID. NO. 8520 | 253-MetThrHisGlyIleMetGluTyrIleLeuGluAsnLeuGluArgTyrValArgAsn-271 |
| SEQ. ID. NO. 8521 | 291-GluIleLeuTyrArgTyrValCysHis-299 |
| SEQ. ID. NO. 8522 | 301-ValSerProValAlaProValAlaHis-309 |
| SEQ. ID. NO. 8523 | 314-AlaAsnIleValLysThrLeuAla-321 |
| SEQ. ID. NO. 8524 | 330-GlnMetLeuGlnLys-334 |
| SEQ. ID. NO. 8525 | 357-PheThrIlePheGluGlyProAsn-364 |
| SEQ. ID. NO. 8526 | 366-MetLeuTyrAlaGluIleTyrAspGlnPheValArgAla-378 |
| SEQ. ID. NO. 8527 | 397-AspArgLeuGlnThr-401 |
| SEQ. ID. NO. 8528 | 414-LeuProGluAspIleArgSerPhe-421 |
| SEQ. ID. NO. 8529 | 439-GlyLysIleIleAlaArgLeu-445 |
| Antigenic Index - Jameson-Wolf | |
| SEQ. ID. NO. 8530 | 3-HisThrGluProSerAlaGlnProSerThrMetAsp-14 |
| SEQ. ID. NO. 8531 | 22-IleGluSerAlaPhe-26 |
| SEQ. ID. NO. 8532 | 29-IlePheSerAspGlyIleAsp-35 |
| SEQ. ID. NO. 8533 | 40-LeuProGluAspLysTrpLeu-46 |
| SEQ. ID. NO. 8534 | 57-PheLeuAspLysLysTyrGlyGlyArgLysGlySerGlnPheGluIle-72 |
| SEQ. ID. NO. 8535 | 103-GluPheGlyAspGluAlaGlnVal-110 |
| SEQ. ID. NO. 8536 | 118-PheLysGlyGluGlyGlyGlyLeuGly-126 |
| SEQ. ID. NO. 8537 | 128-ThrGluProGluThrSerGly-134 |
| SEQ. ID. NO. 8538 | 136-AlaIleAlaArgGluMetGlnSer-143 |
| SEQ. ID. NO. 8539 | 145-TyrGluTyrIleAspGlyGlnThr-152 |

TABLE 1-continued

| | |
|---|---|
| SEQ. ID. NO. 8540 | 160-TyrTrpGlnGlyAsnSerGlnSerAspPhe-169 |
| SEQ. ID. NO. 8541 | 174-AlaLysGluArgLysAsnGlyLysLeuAlaLys-184 |
| SEQ. ID. NO. 8542 | 193-LysThrTyrIleArg-197 |
| SEQ. ID. NO. 8543 | 199-GluThrLeuAlaSerGluGlyLeuArg-207 |
| SEQ. ID. NO. 8544 | 212-AlaValAsnArgIleAspAlaGluMet-220 |
| SEQ. ID. NO. 8545 | 228-LeuSerGlnSerAspAlaAlaGly-235 |
| SEQ. ID. NO. 8546 | 264-AsnLeuGluArgTyrValArgAsnAspIleLysPheValAspTyrGluArgArgGluIleArgArgArgHisGlnVal-289 |
| SEQ. ID. NO. 8547 | 339-LysGlyPheGluArgGlyHisThrAlaGlyAsn-349 |
| SEQ. ID. NO. 8548 | 361-GluGlyProAsnAspMetLeu-367 |
| SEQ. ID. NO. 8549 | 378-AlaThrAlaGluGluLysGluAlaGlyMetLysLeuAspLysAsnGlnThrLeuLeuAspArgLeuGlnThrAspAlaArgPhe-405 |
| SEQ. ID. NO. 8550 | 407-AlaValAlaArgAspTyrThrLeuProGluAspIleArgSerPheLeu-422 |
| SEQ. ID. NO. 8551 | 451-AlaLysHisGluAspThrAla-457 |
| SEQ. ID. NO. 8552 | 463-AspIleArgLysAspIleLeuAspCysArgTyrCysGly-475 |
| Hydrophilic Regions - Hopp-Woods | |
| SEQ. ID. NO. 8553 | 22-IleGluSerAlaPhe-26 |
| SEQ. ID. NO. 8554 | 29-IlePheSerAspGlyIleAsp-35 |
| SEQ. ID. NO. 8555 | 40-LeuProGluAspLysTrpLeu-46 |
| SEQ. ID. NO. 8556 | 58-LeuAspLysLysTyrGlyGlyArgLysGlySerGln-69 |
| SEQ. ID. NO. 8557 | 103-GluPheGlyAspGluAlaGlnVal-110 |
| SEQ. ID. NO. 8558 | 118-PheLysGlyGluGlyGly-123 |
| SEQ. ID. NO. 8559 | 128-ThrGluProGluThrSerGly-134 |
| SEQ. ID. NO. 8560 | 136-AlaIleAlaArgGluMetGlnSer-143 |
| SEQ. ID. NO. 8561 | 174-AlaLysGluArgLysAsnGlyLysLeuAlaLys-184 |
| SEQ. ID. NO. 8562 | 212-AlaValAsnArgIleAspAlaGluMet-220 |
| SEQ. ID. NO. 8563 | 229-SerGlnSerAspAlaAlaGly-235 |
| SEQ. ID. NO. 8564 | 264-AsnLeuGluArgTyrValArgAsnAspIleLysPheValAspTyrGluArgArgGluIleArgArgArgHisGlnVal-289 |
| SEQ. ID. NO. 8565 | 339-LysGlyPheGluArgGlyHisThr-346 |
| SEQ. ID. NO. 8566 | 378-AlaThrAlaGluGluLysGluAlaGlyMetLysLeuAspLysAsnGlnThrLeuLeuAspArgLeuGlnThrAspAlaArgPhe-405 |
| SEQ. ID. NO. 8567 | 416-GluAspIleArgSerPheLeu-422 |
| SEQ. ID. NO. 8568 | 451-AlaLysHisGluAspThrAla-457 |
| SEQ. ID. NO. 8569 | 463-AspIleArgLysAspIleLeuAsp-470 |
| 645-2 | |
| AMPHI Regions - AMPHI | |
| SEQ. ID. NO. 8570 | 21-AsnThrLeuAsnArgCysCysLys-28 |
| SEQ. ID. NO. 8571 | 87-ArgThrLeuProSerLeuLysGlyLeuThrLys-97 |
| Antigenic Index - Jameson-Wolf | |
| SEQ. ID. NO. 8572 | 17-ValGluGlnSerAsnThrLeuAsnArgCysCysLysLysSerArgMetThrCysSerSerSerArgSerArgSerCysProCys-44 |
| SEQ. ID. NO. 8573 | 47-ProMetArgAlaSerGlySerArgValSerSerArgSerArgIle-61 |
| SEQ. ID. NO. 8574 | 68-SerLeuCysArgLysAsnThrCysProProArgLeuSerSerArgAsnThrAlaSerArgThrLeuProSerLeu-92 |
| SEQ. ID. NO. 8575 | 99-LeuThrAlaArgArgArgLeuGly-106 |
| SEQ. ID. NO. 8576 | 110-IleSerGluLysSerArgSerProSerAsn-119 |
| SEQ. ID. NO. 8577 | 137-ThrLeuAlaArgArgArgLeuSerCysSer-146 |
| Hydrophilic Regions - Hopp-Woods | |
| SEQ. ID. NO. 8578 | 19-GlnSerAsnThrLeu-23 |
| SEQ. ID. NO. 8579 | 25-ArgCysCysLysLysSerArgMetThrCysSerSerSerArgSerArgSerCysPro-43 |
| SEQ. ID. NO. 8580 | 48-MetArgAlaSerGlySerArgValSerSerArgSerArgIle-61 |
| SEQ. ID. NO. 8581 | 69-LeuCysArgLysAsnThrCys-75 |
| SEQ. ID. NO. 8582 | 77-ProArgLeuSerSerArgAsnThrAlaSerArgThr-88 |
| SEQ. ID. NO. 8583 | 99-LeuThrAlaArgArgArgLeuGly-106 |
| SEQ. ID. NO. 8584 | 110-IleSerGluLysSerArgSerProSer-118 |
| SEQ. ID. NO. 8585 | 137-ThrLeuAlaArgArgArgLeuSer-144 |
| 647 | |
| AMPHI Regions - AMPHI | |
| SEQ. ID. NO. 8586 | 38-GlyLysValCysArgCysPheGluGlnVal-47 |
| SEQ. ID. NO. 8587 | 69-ThrValPheArgGlnIleIleSerIleVal-78 |
| Antigenic Index - Jameson-Wolf | |
| SEQ. ID. NO. 8588 | 26-GlyLeuValLysGluArgAlaArg-33 |
| SEQ. ID. NO. 8589 | 39-LysValCysArgCysPhe-44 |
| SEQ. ID. NO. 8590 | 54-GlyThrValGlyGlnThrGluArgGlyThr-63 |
| SEQ. ID. NO. 8591 | 81-AlaAspAlaGluArgThrAlaAlaHisSerArgGlyThrArgGly-95 |
| Hydrophilic Regions - Hopp-Woods | |
| SEQ. ID. NO. 8592 | 26-GlyLeuValLysGluArgAlaArg-33 |
| SEQ. ID. NO. 8593 | 56-ValGlyGlnThrGluArgGlyThr-63 |
| SEQ. ID. NO. 8594 | 81-AlaAspAlaGluArgThrAlaAlaHisSerArgGlyThrArgGly-95 |
| 648 | |
| AMPHI Regions - AMPHI | |
| SEQ. ID. NO. 8595 | 7-ArgIleGluArgAlaValArg-13 |
| SEQ. ID. NO. 8596 | 15-AlaValIleAspValLeuAsnValAsp-23 |
| SEQ. ID. NO. 8597 | 44-AlaLeuAlaAspIleArgValLeu-51 |
| SEQ. ID. NO. 8598 | 94-AlaValAspLeuHisAlaValIleLysLeuThrAspThr-106 |
| SEQ. ID. NO. 8599 | 127-GlnGlyValGluGlnGly-132 |
| SEQ. ID. NO. 8600 | 147-ArgArgLeuLysHisPheLysGluGlyAsnAlaAlaGlyMetProArgPhe-163 |
| SEQ. ID. NO. 8601 | 182-AlaArgThrLeuGlyAsnValPheHis-190 |
| SEQ. ID. NO. 8602 | 194-GlySerGlyIleAspGlyIleGlnThrIleValAlaPheAsnGlnHisThr-210 |
| Antigenic Index - Jameson-Wolf | |
| SEQ. ID. NO. 8603 | 1-MetAsnArgArgAspAlaArgIleGluArgAlaValArg-13 |
| SEQ. ID. NO. 8604 | 23-AspAlaProGlySerGlyThrLeuLeuHisGlnArgGlyLysGlnValGlySerArgAsnAspAlaLeuAla-46 |
| SEQ. ID. NO. 8605 | 65-GlyLysLysArgPheValGlnSerArgAsnLeuValGlyArgLysGlnArgAsn-82 |
| SEQ. ID. NO. 8606 | 125-MetProGlnGlyValGluGlnGlyCysArgAla-135 |
| SEQ. ID. NO. 8607 | 143-ThrGlyPheAspArgArgLeuLysHisPheLysGluGlyAsnAla-157 |

TABLE 1-continued

SEQ. ID. NO. 8608 172-ThrAlaAspThrSerGlyIleAspAlaAspAlaArgThr-184
SEQ. ID. NO. 8609 191-AsnArgAlaGlySerGlyIleAspGly-199
Hydrophilic Regions - Hopp-Woods
SEQ. ID. NO. 8610 1-MetAsnArgArgAspAlaArgIleGluArgAlaValArg-13
SEQ. ID. NO. 8611 33-GlnArgGlyLysGlnValGlySerArgAsnAspAlaLeuAla-46
SEQ. ID. NO. 8612 65-GlyLysLysArgPheValGln-71
SEQ. ID. NO. 8613 74-AsnLeuValGlyArgLysGlnArgAsn-82
SEQ. ID. NO. 8614 127-GlnGlyValGluGlnGlyCysArgAla-135
SEQ. ID. NO. 8615 143-ThrGlyPheAspArgArgLeuLysHisPheLysGluGlyAsnAla-157
SEQ. ID. NO. 8616 173-AlaAspThrSerGlyIleAspAlaAspAlaArgThr-184
649-2
AMPHI Regions - AMPHI
SEQ. ID. NO. 8617 8-AlaIleLeuLeuSerAlaIleLeuGlyLeuVal-18
SEQ. ID. NO. 8618 32-ArgAspThrLysHisIleArgLysAlaAsn-41
SEQ. ID. NO. 8619 62-SerGlnGlyAsnVal-66
SEQ. ID. NO. 8620 68-GluLeuArgGluAsnLys-73
SEQ. ID. NO. 8621 76-ArgLysAlaPheArgSerLeuPro-83
Antigenic Index - Jameson-Wolf
SEQ. ID. NO. 8622 1-MetSerValLysLys-5
SEQ. ID. NO. 8623 25-GlyThrSerGluProAlaHisArgAspThrLysHisIleArgLysAlaAsnLys-42
SEQ. ID. NO. 8624 45-LeuHisProGluCysArgLysTyrLeuGluArgArgAlaAla-58
SEQ. ID. NO. 8625 61-ArgSerGlnGlyAsnValGlnGluLeuArgGluAsnLysLysAlaArgLysAlaPheArg-80
SEQ. ID. NO. 8626 85-AlaGluGlnLysIleGlnCys-91
SEQ. ID. NO. 8627 97-AlaPheAspAspPheAspGlyGlySerPheArgArg-108
Hydrophilic Regions - Hopp-Woods
SEQ. ID. NO. 8628 1-MetSerValLysLys-5
SEQ. ID. NO. 8629 25-GlyThrSerGluProAlaHisArgAspThrLysHisIleArgLysAlaAsnLys-42
SEQ. ID. NO. 8630 47-ProGluCysArgLysTyrLeuGluArgArgAlaAla-58
SEQ. ID. NO. 8631 64-GlyAsnValGlnGluLeuArgGluAsnLysLysAlaArgLysAlaPheArg-80
SEQ. ID. NO. 8632 85-AlaGluGlnLysIleGlnCys-91
SEQ. ID. NO. 8633 97-AlaPheAspAspPheAspGlyGlySerPheArgArg-108
650-2
AMPHI Regions - AMPHI
SEQ. ID. NO. 8634 15-SerValCysProGly-19
SEQ. ID. NO. 8635 57-LeuTrpGlyGluLeuArgGln-63
SEQ. ID. NO. 8636 72-ProGluLeuValArgArgHisGlu-79
SEQ. ID. NO. 8637 89-PheAsnArgValIleAsn-94
SEQ. ID. NO. 8638 137-SerGlyLeuTrpGln-141
SEQ. ID. NO. 8639 173-AsnTyrLeuGlnTyrLeuTyrGlyLeuPheGlyAspTrpPro-186
SEQ. ID. NO. 8640 198-AsnValGlyArgAlaIleAsnArgAlaArg-207
SEQ. ID. NO. 8641 218-LeuArgMetProAsnGluThr-224
SEQ. ID. NO. 8642 269-GluAlaIleAlaArgLeuAlaGlyIleThrGlnSer-280
SEQ. ID. NO. 8643 314-SerAsnTyrLeuAsnAlaAlaProAsp-322
SEQ. ID. NO. 8644 341-IleSerThrAlaThrGlyMet-347
SEQ. ID. NO. 8645 349-IleAlaAspIleLysArgLeuAsnAsnLeu-358
SEQ. ID. NO. 8646 376-LysThrLeuGlnThrAlaSerGlu-383
SEQ. ID. NO. 8647 484-AlaAspGluLeuMetGln-489
SEQ. ID. NO. 8648 496-LeuArgArgGlnAlaGlu-501
SEQ. ID. NO. 8649 503-ThrIleSerAlaValIleGlyThrProAspThrValAlaGlu-516
SEQ. ID. NO. 8650 556-AlaSerIleHisArgValVal-562
SEQ. ID. NO. 8651 621-AspThrPheLysSerIle-626
SEQ. ID. NO. 8652 636-AspIleArgArgLeu-640
Antigenic Index - Jameson-Wolf
SEQ. ID. NO. 8653 1-MetSerLysLeuLys-5
SEQ. ID. NO. 8654 24-GlnAsnThrSerSerHis-29
SEQ. ID. NO. 8655 38-LeuAsnSerSerIleLeuAspLeuProProThrLysGlnTyrPhe-52
SEQ. ID. NO. 8656 59-GlyGluLeuArgGlnGlyPheArgMetGlyGluValAsnProGluLeuValArgArgHisGluSerLysPhe-82
SEQ. ID. NO. 8657 92-ValIleAsnArgSerArgProTyr-99
SEQ. ID. NO. 8658 105-AsnGluValLysLysArgAsnMetProAla-114
SEQ. ID. NO. 8659 128-ThrLysAlaLysSerHisValGlyAlaSerGly-138
SEQ. ID. NO. 8660 145-AlaThrGlyArgHisTyrGlyLeuGluLysThrProValTyrAspGlyArgHisAspVal-164
SEQ. ID. NO. 8661 192-TyrAsnTrpGlyGluGlyAsnValGlyArgAlaIleAsnArgAlaArgAlaGlnGlyLeuGluProThrTyrGluAsnLeuArgMetProAsnGlu ThrArgAsnTyrVal-228
SEQ. ID. NO. 8662 247-AsnIleSerAspIleAspAsnLysProTyr-256
SEQ. ID. NO. 8663 259-AlaValGluProAspArgProLeuAspAsnGluAlaIleAla-272
SEQ. ID. NO. 8664 296-ProLysSerLysArgLysLeu-302
SEQ. ID. NO. 8665 318-AsnAlaAlaProAspSer-323
SEQ. ID. NO. 8666 332-ProAlaAlaLysThrSerLeuSerAspIleSerThr-343
SEQ. ID. NO. 8667 350-AlaAspIleLysArgLeuAsnAsnLeuAsnGly-360
SEQ. ID. NO. 8668 370-LeuValAlaLysAsnGlyLysThrLeuGlnThrAlaSer-382
SEQ. ID. NO. 8669 388-IleAspIleAspAsnThrProAspThrTyrArgSerAsnMetProAla-403
SEQ. ID. NO. 8670 411-AlaArgIleArgPro-415
SEQ. ID. NO. 8671 428-LeuProGlnLysThrValArgThrGluProAspProLeuValArgIleAlaGlu-445
SEQ. ID. NO. 8672 454-GlnProGlnThrGluLysGlnThrAlaMetProSerGluThrGln-468
SEQ. ID. NO. 8673 477-ProGlnAsnAspMetGlnAlaAlaAspGluLeu-487
SEQ. ID. NO. 8674 491-ValAlaArgAsnAsnLeuArgArgGlnAlaGluGluThrIle-504
SEQ. ID. NO. 8675 509-GlyThrProAspThrValAlaGluHisLysIleSerAlaSerProGln-524

TABLE 1-continued

| | |
|---|---|
| SEQ. ID. NO. 8676 | 527-AlaAlaAlaAspGlyLysArgArgValArgLeuGluThrArgValAlaLy sAlaAlaAspGlyGluAlaGluIle-551 |
| SEQ. ID. NO. 8677 | 560-ArgValValGluGlyAspThr-566 |
| SEQ. ID. NO. 8678 | 583-ValAlaAsnAsnIleLysGlyAsnThrIleGlnLysGlyGlnValLeuArg-599 |
| SEQ. ID. NO. 8679 | 606-AlaGlnThrArgIleGluLysValSerTyrThrAlaArgLysGlyAspThrPheLys-624 |
| SEQ. ID. NO. 8680 | 634-IleAspAspIleArgArgLeuAsnProAsnLeu-644 |
| SEQ. ID. NO. 8681 | 647-IleAsnProGlyGlnArgValLysLeu-655 |
| Hydrophilic Regions - Hopp-Woods | |
| SEQ. ID. NO. 8682 | 1-MetSerLysLeuLys-5 |
| SEQ. ID. NO. 8683 | 61-LeuArgGlnGlyPheArgMetGlyGluValAsnProGluLeuValArgArgHisGluSerLysPhe-82 |
| SEQ. ID. NO. 8684 | 92-ValIleAsnArgSerArgPro-98 |
| SEQ. ID. NO. 8685 | 105-AsnGluValLysLysArgAsnMetProAla-114 |
| SEQ. ID. NO. 8686 | 128-ThrLysAlaLysSerHisVal-134 |
| SEQ. ID. NO. 8687 | 150-TyrGlyLeuGluLys-154 |
| SEQ. ID. NO. 8688 | 156-ProValTyrAspGlyArgHisAspVal-164 |
| SEQ. ID. NO. 8689 | 202-AlaIleAsnArgAlaArgAlaGlnGlyLeu-211 |
| SEQ. ID. NO. 8690 | 213-ProThrTyrGluAsnLeuArgMetProAsnGluThrArgAsnTyrVal-228 |
| SEQ. ID. NO. 8691 | 249-SerAspIleAspAsn-253 |
| SEQ. ID. NO. 8692 | 260-ValGluProAspArgProLeuAspAsnGluAlaIleAla-272 |
| SEQ. ID. NO. 8693 | 296-ProLysSerLysArgLysLeu-302 |
| SEQ. ID. NO. 8694 | 334-AlaLysThrSerLeu-338 |
| SEQ. ID. NO. 8695 | 350-AlaAspIleLysArgLeuAsn-356 |
| SEQ. ID. NO. 8696 | 373-LysAsnGlyLysThrLeuGlnThrAlaSer-382 |
| SEQ. ID. NO. 8697 | 389-AspIleAspAsnThrProAspThrTyrArg-398 |
| SEQ. ID. NO. 8698 | 411-AlaArgIleArgPro-415 |
| SEQ. ID. NO. 8699 | 431-LysThrValArgThrGluProAspProLeuValArgIleAlaGlu-445 |
| SEQ. ID. NO. 8700 | 455-ProGlnThrGluLysGlnThrAlaMetProSerGluThrGln-468 |
| SEQ. ID. NO. 8701 | 479-AsnAspMetGlnAlaAlaAspGluLeu-487 |
| SEQ. ID. NO. 8702 | 494-AsnAsnLeuArgArgGlnAlaGluGluThrIle-504 |
| SEQ. ID. NO. 8703 | 512-AspThrValAlaGluHisLysIleSerAla-521 |
| SEQ. ID. NO. 8704 | 527-AlaAlaAlaAspGlyLysArgArgValArgLeuGluThrArgValAlaLysAlaAlaAspGlyGluAlaGluIle-551 |
| SEQ. ID. NO. 8705 | 560-ArgValValGluGly-564 |
| SEQ. ID. NO. 8706 | 608-ThrArgIleGluLysValSerTyrThrAlaArgLysGlyAspThrPheLys-624 |
| SEQ. ID. NO. 8707 | 634-IleAspAspIleArgArgLeuAsn-641 |
| SEQ. ID. NO. 8708 | 649-ProGlyGlnArgValLysLeu-655 |
| 652-1 | |
| AMPHI Regions - AMPHI | |
| SEQ. ID. NO. 8709 | 6-AspIlePheAlaArg-10 |
| SEQ. ID. NO. 8710 | 52-ArgAspGlyAspLys-56 |
| SEQ. ID. NO. 8711 | 62-LysGlyValLeuLysAlaValGluHisValAsnAsnGlnIleAlaGlnAla-78 |
| SEQ. ID. NO. 8712 | 130-LeuTyrArgTyrLeuGlyGlyAlaGlyPro-139 |
| SEQ. ID. NO. 8713 | 149-ValIleAsnGlyGly-153 |
| SEQ. ID. NO. 8714 | 173-LysSerPheArgGluAlaLeuArgCys-181 |
| SEQ. ID. NO. 8715 | 184-GluIlePheHisAlaLeuLysLys-191 |
| SEQ. ID. NO. 8716 | 266-AlaGluPheAlaGluTyrLeuGluGlyLeuValAsn-277 |
| SEQ. ID. NO. 8717 | 323-AlaGluGlyIleGluLysGlyVal-330 |
| SEQ. ID. NO. 8718 | 338-ValAsnGlnIleGlyThrLeuSerGluThrLeuLysAlaValAspLeuAlaLys-355 |
| SEQ. ID. NO. 8719 | 377-AspLeuAlaValAla-381 |
| SEQ. ID. NO. 8720 | 391-SerLeuSerArgSerAspArgMetAlaLysTyrAsnGlnLeuLeuArgIleGluGlu-409 |
| SEQ. ID. NO. 8721 | 411-LeuAlaGluAlaAlaAspTyr-417 |
| Antigenic Index - Jameson-Wolf | |
| SEQ. ID. NO. 8722 | 11-GluIleLeuAspSerArgGlyAsnProThrValGlu-22 |
| SEQ. ID. NO. 8723 | 36-AlaValProSerGlyAlaSerThrGlyGlnLysGluAlaLeuGluLeuArgAspGlyAspLysSerArgTyrSerGlyLysGlyValLeuLysAlaVal GluHisValAsn-72 |
| SEQ. ID. NO. 8724 | 83-AspAlaAsnGluGlnSerTyr-89 |
| SEQ. ID. NO. 8725 | 97-LeuAspGlyThrGluAsnLysGlyAsnLeuGly-107 |
| SEQ. ID. NO. 8726 | 121-AlaAlaAlaGluAspSerGlyLeuPro-129 |
| SEQ. ID. NO. 8727 | 135-GlyGlyAlaGlyProMet-140 |
| SEQ. ID. NO. 8728 | 151-AsnGlyGlyGluHisAlaAsnAsnSer-159 |
| SEQ. ID. NO. 8729 | 173-LysSerPheArgGluAlaLeuArgCysGlyAla-183 |
| SEQ. ID. NO. 8730 | 190-LysLysLeuCysAspSerLysGlyPheProThrThrValGlyAspGluGlyGlyPhe-208 |
| SEQ. ID. NO. 8731 | 211-AsnLeuAsnSerHisLysGluAlaLeu-219 |
| SEQ. ID. NO. 8732 | 243-CysAlaSerSerGluPheTyrLysAspGlyLysTyrHisLeuGluAlaGluGlyArgSerTyrThrAsn-265 |
| SEQ. ID. NO. 8733 | 283-SerIleGluAspGlyMetAspGluAsnAspTrpGluGly-295 |
| SEQ. ID. NO. 8734 | 299-LeuThrGluLysLeuGlyGlyArgValGlnLeuValGlyAspAspLeu-314 |
| SEQ. ID. NO. 8735 | 318-AsnProLysIleLeuAlaGluGlyIleGluLysGlyVal-330 |
| SEQ. ID. NO. 8736 | 352-AspLeuAlaLysArgAsnArgTyrAla-360 |
| SEQ. ID. NO. 8737 | 363-MetSerHisArgSerGlyGluThrGluAspSerThrIle-375 |
| SEQ. ID. NO. 8738 | 388-LysThrGlySerLeuSerArgSerAspArgMetAlaLys-400 |
| SEQ. ID. NO. 8739 | 405-LeuArgIleGluGluGluLeuAlaGluAlaAlaAspTyrProSerLys-420 |
| Hydrophilic Regions - Hopp-Woods | |
| SEQ. ID. NO. 8740 | 11-GluIleLeuAspSerArgGlyAsnProThrValGlu-22 |
| SEQ. ID. NO. 8741 | 43-ThrGlyGlnLysGluAlaLeuGluLeuArgAspGlyAspLysSerArgTyrSerGly-61 |
| SEQ. ID. NO. 8742 | 63-GlyValLeuLysAlaValGlu-69 |
| SEQ. ID. NO. 8743 | 97-LeuAspGlyThrGluAsnLysGlyAsnLeu-106 |
| SEQ. ID. NO. 8744 | 121-AlaAlaAlaGluAspSerGly-127 |
| SEQ. ID. NO. 8745 | 153-GlyGluHisAlaAsn-157 |
| SEQ. ID. NO. 8746 | 173-LysSerPheArgGluAlaLeuArgCysGlyAla-183 |
| SEQ. ID. NO. 8747 | 190-LysLysLeuCysAspSerLysGly-197 |
| SEQ. ID. NO. 8748 | 202-ValGlyAspGluGlyGlyPhe-208 |

TABLE 1-continued

| | |
|---|---|
| SEQ. ID. NO. 8749 | 213-AsnSerHisLysGluAlaLeu-219 |
| SEQ. ID. NO. 8750 | 247-GluPheTyrLysAspGlyLysTyrHisLeuGluAlaGluGlyArgSerTyrThr-264 |
| SEQ. ID. NO. 8751 | 283-SerIleGluAspGlyMetAspGluAsnAspTrpGluGly-295 |
| SEQ. ID. NO. 8752 | 299-LeuThrGluLysLeuGlyGly-305 |
| SEQ. ID. NO. 8753 | 321-IleLeuAlaGluGlyIleGluLysGlyVal-330 |
| SEQ. ID. NO. 8754 | 352-AspLeuAlaLysArgAsnArgTyr-359 |
| SEQ. ID. NO. 8755 | 364-SerHisArgSerGlyGluThrGluAspSerThrIle-375 |
| SEQ. ID. NO. 8756 | 391-SerLeuSerArgSerAspArgMetAlaLys-400 |
| SEQ. ID. NO. 8757 | 405-LeuArgIleGluGluGluLeuAlaGluAlaAlaAspTyrProSer-419 |
| 653 | |
| AMPHI Regions - AMPHI | |
| SEQ. ID. NO. 8758 | 6-MetArgMetProGluValThrLysGlyPheSerGlySer-18 |
| SEQ. ID. NO. 8759 | 60-ThrMetArgLysProArgLeuThr-67 |
| SEQ. ID. NO. 8760 | 75-AlaLeuIlePheThrCysPheAla-82 |
| SEQ. ID. NO. 8761 | 96-ThrAlaLeuAlaAlaIleThrCysIle-104 |
| SEQ. ID. NO. 8762 | 111-LeuGlyLysMetGluGluPheAsn-118 |
| Antigenic Index - Jameson-Wolf | |
| SEQ. ID. NO. 8763 | 4-GluProMetArgMetProGluValThrLysGlyPheSerGlySer-18 |
| SEQ. ID. NO. 8764 | 45-GlyCysArgSerThrArgLysThr-52 |
| SEQ. ID. NO. 8765 | 56-ValArgProGluThrMetArgLysProArgLeuThrAsnSerSerAla-71 |
| SEQ. ID. NO. 8766 | 86-AsnSerGlyCysAsnAla-91 |
| SEQ. ID. NO. 8767 | 103-CysIleSerGlyProProCysArgLeuGlyLysMetGluGlu-116 |
| SEQ. ID. NO. 8768 | 125-SerArgHisLysIleThrProProArgGlyProArgArgVal-138 |
| SEQ. ID. NO. 8769 | 145-ThrLysSerGlnAsnGlyThrGly-152 |
| SEQ. ID. NO. 8770 | 154-GlyTyrSerProProAlaThrArgProAla-163 |
| Hydrophilic Regions - Hopp-Woods | |
| SEQ. ID. NO. 8771 | 4-GluProMetArgMetProGluValThrLys-13 |
| SEQ. ID. NO. 8772 | 47-ArgSerThrArgLysThr-52 |
| SEQ. ID. NO. 8773 | 57-ArgProGluThrMetArgLysProArgLeuThrAsn-68 |
| SEQ. ID. NO. 8774 | 107-ProProCysArgLeuGlyLysMetGluGlu-116 |
| SEQ. ID. NO. 8775 | 126-ArgHisLysIleThrProProArgGlyProArg-136 |
| SEQ. ID. NO. 8776 | 158-ProAlaThrArgProAla-163 |
| 656 | |
| AMPHI Regions - AMPHI | |
| SEQ. ID. NO. 8777 | 14-MetAlaArgThrLeuGlyAlaProGlu-22 |
| SEQ. ID. NO. 8778 | 42-ArgArgProSerThr-46 |
| SEQ. ID. NO. 8779 | 92-LeuAlaSerLeuAsnLysSerCys-99 |
| SEQ. ID. NO. 8780 | 117-MetGlyArgThrIleThr-122 |
| Antigenic Index - Jameson-Wolf | |
| SEQ. ID. NO. 8781 | 6-GlySerThrSerSer-10 |
| SEQ. ID. NO. 8782 | 19-GlyAlaProGluSerValProAlaGlyLysValAlaAla-31 |
| SEQ. ID. NO. 8783 | 40-SerPheArgArgProSerThrLeuGlu-48 |
| SEQ. ID. NO. 8784 | 74-ArgProThrSerLeuArgProLysSerIleAsn-84 |
| SEQ. ID. NO. 8785 | 94-SerLeuAsnLysSerCysSerLeuAlaArgSerSerAlaGlyValLeuProArgArgArgValProAla-116 |
| SEQ. ID. NO. 8786 | 122-ThrSerLeuArgSerArgArgThrArgIleSerGlyGluGluProThrMetTrpLysSerProLysSer-144 |
| Hydrophilic Regions - Hopp-Woods | |
| SEQ. ID. NO. 8787 | 40-SerPheArgArgProSerThr-46 |
| SEQ. ID. NO. 8788 | 76-ThrSerLeuArgProLysSerIle-83 |
| SEQ. ID. NO. 8789 | 99-CysSerLeuAlaArgSerSer-105 |
| SEQ. ID. NO. 8790 | 109-LeuProArgArgArgValProAla-116 |
| SEQ. ID. NO. 8791 | 124-LeuArgSerArgArgThrArgIleSerGlyGluGluProThrMet-138 |
| SEQ. ID. NO. 8792 | 140-LysSerProLysSer-144 |
| 657 | |
| AMPHI Regions - AMPHI | |
| SEQ. ID. NO. 8793 | 9-ProAlaMetLeuGly-13 |
| SEQ. ID. NO. 8794 | 20-LeuGlyArgMetPheThr-25 |
| SEQ. ID. NO. 8795 | 62-AlaAlaLeuAspGluLeuAlaLysCysAlaAla-72 |
| SEQ. ID. NO. 8796 | 85-MetArgPheLeuAlaLys-90 |
| SEQ. ID. NO. 8797 | 132-AspIleThrGluAlaSer-137 |
| SEQ. ID. NO. 8798 | 139-GlnPheLeuProGlyIleLeuLysThr-147 |
| SEQ. ID. NO. 8799 | 161-LysThrLeuAspGluLeuLysAlaAla-169 |
| SEQ. ID. NO. 8800 | 178-CysValLeuGluLysMetValAspLeu-186 |
| SEQ. ID. NO. 8801 | 203-GlnThrPheAspProAlaGluAsnIle-211 |
| SEQ. ID. NO. 8802 | 232-GlnGlnAlaArgGlnMetAlaGlnArgLeuAlaAspGluLeuAspTyrValGlyValLeu-251 |
| SEQ. ID. NO. 8803 | 314-AsnIleLeuGlyAsp-318 |
| Antigenic Index - Jameson-Wolf | |
| SEQ. ID. NO. 8804 | 16-GlyGlyGlyGlnLeuGly-21 |
| SEQ. ID. NO. 8805 | 37-ValLeuAspProAspProAspAlaProAla-46 |
| SEQ. ID. NO. 8806 | 62-AlaAlaLeuAspGluLeuAlaLys-69 |
| SEQ. ID. NO. 8807 | 75-ThrGluPheGluAsnValAsnAlaAspAla-84 |
| SEQ. ID. NO. 8808 | 91-HisThrAsnValSerProSerGlyAsp-99 |
| SEQ. ID. NO. 8809 | 106-AsnArgIleGlnGluLysAlaTrpIle-114 |
| SEQ. ID. NO. 8810 | 128-CysLysAlaGluAspIleThrGluAla-136 |
| SEQ. ID. NO. 8811 | 150-LeuGlyTyrAspGlyLysGlyGlnIleArgValLysThrLeuAspGluLeuLysAlaAlaPhe-170 |
| SEQ. ID. NO. 8812 | 182-LysMetValAspLeuArgSerGluIle-190 |
| SEQ. ID. NO. 8813 | 197-LeuAsnAsnAspAsnValGlnThrPheAspProAlaGluAsnIleHisGluAsnGly-215 |
| SEQ. ID. NO. 8814 | 230-ValGlnGlnGlnAlaArgGlnMetAla-238 |
| SEQ. ID. NO. 8815 | 240-ArgLeuAlaAspGluLeuAsp-246 |
| SEQ. ID. NO. 8816 | 269-IleAlaProArgProHisAsnSerGlyHisHis-279 |
| SEQ. ID. NO. 8817 | 288-GlnPheGlnGlnGln-292 |

TABLE 1-continued

| | |
|---|---|
| SEQ. ID. NO. 8818 | 300-ProProAlaAspThrLysLeuLeuSer-308 |
| SEQ. ID. NO. 8819 | 319-ValTrpGlnGluAspGlyGlyGluProAspTrp-329 |
| SEQ. ID. NO. 8820 | 333-GlnSerHisProAsnAla-338 |
| SEQ. ID. NO. 8821 | 344-GlyLysLysThrAlaHisLysGlyArgLysMetGly-355 |
| SEQ. ID. NO. 8822 | 361-ThrThrAspSerAspThrAlaPheGlnGluAlaLysLysLeuHis-375 |
| Hydrophilic Regions - Hopp-Woods | |
| SEQ. ID. NO. 8823 | 37-ValLeuAspProAspProAspAlaProAla-46 |
| SEQ. ID. NO. 8824 | 62-AlaAlaLeuAspGluLeuAlaLys-69 |
| SEQ. ID. NO. 8825 | 75-ThrGluPheGluAsnValAsn-81 |
| SEQ. ID. NO. 8826 | 128-CysLysAlaGluAspIleThrGluAla-136 |
| SEQ. ID. NO. 8827 | 152-TyrAspGlyLysGlyGlnIleArgValLysThrLeuAspGluLeuLysAlaAlaPhe-170 |
| SEQ. ID. NO. 8828 | 182-LysMetValAspLeuArgSerGluIle-190 |
| SEQ. ID. NO. 8829 | 197-LeuAsnAsnAspAsn-201 |
| SEQ. ID. NO. 8830 | 206-AspProAlaGluAsnIleHis-212 |
| SEQ. ID. NO. 8831 | 230-ValGlnGlnGlnAlaArgGlnMetAla-238 |
| SEQ. ID. NO. 8832 | 240-ArgLeuAlaAspGluLeuAsp-246 |
| SEQ. ID. NO. 8833 | 269-IleAlaProArgProHisAsn-275 |
| SEQ. ID. NO. 8834 | 301-ProAlaAspThrLysLeu-306 |
| SEQ. ID. NO. 8835 | 320-TrpGlnGluAspGlyGlyGluProAsp-328 |
| SEQ. ID. NO. 8836 | 344-GlyLysLysThrAlaHisLysGlyArgLysMetGly-355 |
| SEQ. ID. NO. 8837 | 362-ThrAspSerAspThrAlaPheGlnGluAlaLysLysLeuHis-375 |
| 658 | |
| AMPHI Regions - AMPHI | |
| SEQ. ID. NO. 8838 | 28-ArgGlnTyrAlaAspIleIleGlnPheValArgGlnAlaLeuArgHisLeuProArgLeuLeuLeu-49 |
| SEQ. ID. NO. 8839 | 68-ValAspValPheGlyArgValGluSer-76 |
| SEQ. ID. NO. 8840 | 92-ThrAlaGlnIleHisHisPhePheGlnAsnAlaIleHisAla-105 |
| SEQ. ID. NO. 8841 | 139-GlnLysLeuArgAlaCysPheSerAspValPheSer-150 |
| Antigenic Index - Jameson-Wolf | |
| SEQ. ID. NO. 8842 | 6-ValArgAlaArgGlyAspPheValAspAspGlnPheMetArgValThrAspAsnLysHisPhe-26 |
| SEQ. ID. NO. 8843 | 40-AlaLeuArgHisLeuPro-45 |
| SEQ. ID. NO. 8844 | 53-ThrGlnSerArgGlyAspAspGlyIleSerGlnAspAlaVal-66 |
| SEQ. ID. NO. 8845 | 72-GlyArgValGluSer-76 |
| SEQ. ID. NO. 8846 | 107-ValPheGlyLysArgGlyPheGlu-114 |
| SEQ. ID. NO. 8847 | 130-GlnArgSerArgPheGlnAspAlaGlyGlnLysLeuArgAlaCysPhe-145 |
| SEQ. ID. NO. 8848 | 155-LeuIleArgArgGlyLeuGlnSerArgPhe-164 |
| SEQ. ID. NO. 8849 | 177-AsnArgHisThrIleAlaAlaArgGlyAsnIle-187 |
| SEQ. ID. NO. 8850 | 193-LysAlaHisArgIleGly-198 |
| SEQ. ID. NO. 8851 | 202-PheLysPheSerGlyHisArgArgAla-210 |
| SEQ. ID. NO. 8852 | 219-LeuValValLysArgArgAlaGln-226 |
| SEQ. ID. NO. 8853 | 230-GlyLysPheCysCysArgArgValArgIleGlyValGluAsn-243 |
| SEQ. ID. NO. 8854 | 250-GlyPheGlyGlyAsnGlyLysHisSerAla-259 |
| Hydrophilic Regions - Hopp-Woods | |
| SEQ. ID. NO. 8855 | 6-ValArgAlaArgGlyAspPheValAsp-14 |
| SEQ. ID. NO. 8856 | 16-GlnPheMetArgValThrAspAsnLysHisPhe-26 |
| SEQ. ID. NO. 8857 | 53-ThrGlnSerArgGlyAspAspGlyIleSer-62 |
| SEQ. ID. NO. 8858 | 72-GlyArgValGluSer-76 |
| SEQ. ID. NO. 8859 | 130-GlnArgSerArgPheGlnAspAlaGlyGlnLysLeuArgAlaCysPhe-145 |
| SEQ. ID. NO. 8860 | 155-LeuIleArgArgGlyLeuGln-161 |
| SEQ. ID. NO. 8861 | 193-LysAlaHisArgIleGly-198 |
| SEQ. ID. NO. 8862 | 205-SerGlyHisArgArgAla-210 |
| SEQ. ID. NO. 8863 | 220-ValValLysArgArgAlaGln-226 |
| SEQ. ID. NO. 8864 | 233-CysCysArgArgValArgIleGlyVal-241 |
| SEQ. ID. NO. 8865 | 253-GlyAsnGlyLysHisSerAla-259 |
| 661-2 | |
| AMPHI Regions - AMPHI | |
| SEQ. ID. NO. 8866 | 19-GlyIleThrAspLysProPheArgArgLeuCysArgAspPheGlyAlaGly-35 |
| SEQ. ID. NO. 8867 | 37-AlaValCysGluMetLeu-42 |
| SEQ. ID. NO. 8868 | 75-AspProGlnGlnMetAlaAspAlaAla-83 |
| SEQ. ID. NO. 8869 | 122-AlaAlaIleLeuGluAlaValValArg-130 |
| SEQ. ID. NO. 8870 | 152-ProValIleAlaLysIleAlaGlu-159 |
| SEQ. ID. NO. 8871 | 256-AlaAlaAlaIleLeuAsnHisIleArgAlaIleHisAlaPheTyrGly-271 |
| SEQ. ID. NO. 8872 | 297-ArgArgGluIleAsnArgLeuAspSer-305 |
| SEQ. ID. NO. 8873 | 310-TyrAspMetLeuAlaGlyTyrLeuGluArgLeuAlaGluLys-323 |
| Antigenic Index - Jameson-Wolf | |
| SEQ. ID. NO. 8874 | 20-IleThrAspLysProPheArgArgLeuCysArgAspPheGlyAlaGly-35 |
| SEQ. ID. NO. 8875 | 42-LeuThrSerAspProThrLeuArgAsnThrArgLysThrLeuHisArgSerAspPheAlaAspGluGlyGly-65 |
| SEQ. ID. NO. 8876 | 72-AlaGlySerAspProGlnGlnMetAlaAspAlaAlaArg-84 |
| SEQ. ID. NO. 8877 | 97-AsnMetGlyCysProAlaLysLysValCys-106 |
| SEQ. ID. NO. 8878 | 143-GlyTrpHisAspAspHisGlnAsnLeu-151 |
| SEQ. ID. NO. 8879 | 157-IleAlaGluAspCysGly-162 |
| SEQ. ID. NO. 8880 | 169-HisGlyArgThrArgThrGlnMetTyrLysGlyGluAlaArgTyr-183 |
| SEQ. ID. NO. 8881 | 187-AlaGluThrLysCysArgLeu-193 |
| SEQ. ID. NO. 8882 | 200-AsnGlyAspIleThrSerProGlnLysAla-209 |
| SEQ. ID. NO. 8883 | 222-MetIleGlyArgGlyAlaGlnGlyArgProTrpPhe-233 |
| SEQ. ID. NO. 8884 | 236-AspLeuLysHisTyrAla-241 |
| SEQ. ID. NO. 8885 | 270-TyrGlyAspThrAlaGly-275 |
| SEQ. ID. NO. 8886 | 277-ArgIleAlaArgLysHis-282 |
| SEQ. ID. NO. 8887 | 288-AspGluMetProAspGlyGluGlnThrArgArgGluIleAsnArgLeuAspSerAla-306 |
| SEQ. ID. NO. 8888 | 319-ArgLeuAlaGluLysThrAspSerTrp-327 |
| SEQ. ID. NO. 8889 | 330-AlaTyrArgProAsnAla-335 |

TABLE 1-continued

| | |
|---|---|
| Hydrophilic Regions - Hopp-Woods | |
| SEQ. ID. NO. 8890 | 20-IleThrAspLysProPheArgArgLeuCysArgAspPhe-32 |
| SEQ. ID. NO. 8891 | 46-ProThrLeuArgAsnThrArgLysThrLeuHisArgSerAspPheAlaAspGluGlyGly-65 |
| SEQ. ID. NO. 8892 | 73-GlySerAspProGlnGlnMetAlaAspAlaAlaArg-84 |
| SEQ. ID. NO. 8893 | 100-CysProAlaLysLysValCys-106 |
| SEQ. ID. NO. 8894 | 157-IleAlaGluAspCysGly-162 |
| SEQ. ID. NO. 8895 | 170-GlyArgThrArgThrGlnMetTyrLysGlyGluAlaArgTyr-183 |
| SEQ. ID. NO. 8896 | 187-AlaGluThrLysCysArgLeu-193 |
| SEQ. ID. NO. 8897 | 203-IleThrSerProGlnLysAla-209 |
| SEQ. ID. NO. 8898 | 236-AspLeuLysHisTyrAla-241 |
| SEQ. ID. NO. 8899 | 277-ArgIleAlaArgLys-281 |
| SEQ. ID. NO. 8900 | 289-GluMetProAspGlyGluGlnThrArgArgGluIleAsnArgLeuAspSerAla-306 |
| SEQ. ID. NO. 8901 | 319-ArgLeuAlaGluLysThrAspSer-326 |
| 663 | |
| AMPHI Regions - AMPHI | |
| SEQ. ID. NO. 8902 | 19-ProPheAlaLeuLeuHisLysIleAlaAspLeuThrGlyLeuLeuAlaTyr-35 |
| SEQ. ID. NO. 8903 | 47-IleAsnLeuAlaLysCysPheSerGluTrp-56 |
| SEQ. ID. NO. 8904 | 66-LysGlnHisPheLysHisMetAlaLysLeu-75 |
| SEQ. ID. NO. 8905 | 87-AlaGlyArgLeuLysSerLeuValArg-95 |
| SEQ. ID. NO. 8906 | 168-GluGlyLeuArgAlaLeuValLysGlnPheArgLys-179 |
| SEQ. ID. NO. 8907 | 209-ThrIleThrGlyLeuSerArgIleAlaAlaLeuAlaAsn-221 |
| SEQ. ID. NO. 8908 | 243-ProAlaTrpLysSer-247 |
| SEQ. ID. NO. 8909 | 258-GlnArgMetAsnArgPheIleGluAspArgValArgGluHis-271 |
| Antigenic Index - Jameson-Wolf | |
| SEQ. ID. NO. 8910 | 38-ValLysProArgArgArgIleGlyGlu-46 |
| SEQ. ID. NO. 8911 | 56-TrpSerGluGluLysArgLysThrValLeu-65 |
| SEQ. ID. NO. 8912 | 87-AlaGlyArgLeuLysSer-92 |
| SEQ. ID. NO. 8913 | 94-ValArgTyrArgAsnLysHisTyrLeuAsp-103 |
| SEQ. ID. NO. 8914 | 105-AlaLeuAlaAlaGlyGluLys-111 |
| SEQ. ID. NO. 8915 | 139-TyrSerHisGlnLysAsnLysIleLeuAsp-148 |
| SEQ. ID. NO. 8916 | 150-GlnIleLeuLysGlyArgAsnArgTyr-158 |
| SEQ. ID. NO. 8917 | 166-ArgThrGluGlyLeuArgAlaLeu-173 |
| SEQ. ID. NO. 8918 | 175-LysGlnPheArgLysSerSerAla-182 |
| SEQ. ID. NO. 8919 | 188-ProAspGlnAspPheGlyArgAsnAspSerVal-198 |
| SEQ. ID. NO. 8920 | 229-ProValArgGluAlaAspAsnThr-236 |
| SEQ. ID. NO. 8921 | 243-ProAlaTrpLysSerPheProGlyGluAspAlaLysAlaAspAlaGlnArgMetAsnArgPheIleGluAspArgValArgGluHisProGlu-273 |
| SEQ. ID. NO. 8922 | 280-LysArgPheLysThrArgProGluGlySerProAspPheTyr-293 |
| Hydrophilic Regions - Hopp-Woods | |
| SEQ. ID. NO. 8923 | 39-LysProArgArgArgIleGlyGlu-46 |
| SEQ. ID. NO. 8924 | 56-TrpSerGluGluLysArgLysThrValLeu-65 |
| SEQ. ID. NO. 8925 | 88-GlyArgLeuLysSer-92 |
| SEQ. ID. NO. 8926 | 94-ValArgTyrArgAsn-98 |
| SEQ. ID. NO. 8927 | 105-AlaLeuAlaAlaGlyGluLys-111 |
| SEQ. ID. NO. 8928 | 142-GlnLysAsnLysIleLeuAsp-148 |
| SEQ. ID. NO. 8929 | 150-GlnIleLeuLysGlyArgAsnArgTyr-158 |
| SEQ. ID. NO. 8930 | 166-ArgThrGluGlyLeuArgAlaLeu-173 |
| SEQ. ID. NO. 8931 | 176-GlnPheArgLysSerSer-181 |
| SEQ. ID. NO. 8932 | 190-GlnAspPheGlyArgAsnAspSerVal-198 |
| SEQ. ID. NO. 8933 | 229-ProValArgGluAlaAspAsn-235 |
| SEQ. ID. NO. 8934 | 248-PheProGlyGluAspAlaLysAlaAspAlaGlnArgMetAsnArgPheIleGluAspArgValArgGluHisProGlu-273 |
| SEQ. ID. NO. 8935 | 280-LysArgPheLysThrArgProGluGlySerPro-290 |
| 664-2 | |
| AMPHI Regions - AMPHI | |
| SEQ. ID. NO. 8936 | 47-AlaAspValPheAspAlaAlaHisGlyAlaAlaGly-58 |
| SEQ. ID. NO. 8937 | 90-ProValValGluIle-94 |
| SEQ. ID. NO. 8938 | 158-PheHisArgValPheGlnArgPhe-165 |
| SEQ. ID. NO. 8939 | 201-AlaArgAspGlnSerLysGlnIleAlaArgPheGlyLysArg-214 |
| Antigenic Index - Jameson-Wolf | |
| SEQ. ID. NO. 8940 | 27-GlyAlaHisArgMetGlyGlyArgAlaCysVal-37 |
| SEQ. ID. NO. 8941 | 73-PheLeuGlnArgLysLeuGluPro-80 |
| SEQ. ID. NO. 8942 | 108-IleGlyGlyGlyAlaAlaValGlyLysAspGluLeuGlyValLysAspValGln-125 |
| SEQ. ID. NO. 8943 | 137-AlaHisGlyAspAspHisGluAsn-144 |
| SEQ. ID. NO. 8944 | 165-PheHisGlyLysAlaAspLeuGly-172 |
| SEQ. ID. NO. 8945 | 177-GlyGlyValLysLeuAspPhe-183 |
| SEQ. ID. NO. 8946 | 199-GlnIleAlaArgAspGlnSerLysGlnIleAlaArgPheGlyLysArgValPhe-216 |
| Hydrophilic Regions - Hopp-Woods | |
| SEQ. ID. NO. 8947 | 28-AlaHisArgMetGlyGly-33 |
| SEQ. ID. NO. 8948 | 74-LeuGlnArgLysLeuGluPro-80 |
| SEQ. ID. NO. 8949 | 113-AlaValGlyLysAspGluLeuGlyValLysAspValGln-125 |
| SEQ. ID. NO. 8950 | 137-AlaHisGlyAspAspHisGluAsn-144 |
| SEQ. ID. NO. 8951 | 165-PheHisGlyLysAlaAspLeuGly-172 |
| SEQ. ID. NO. 8952 | 177-GlyGlyValLysLeuAspPhe-183 |
| SEQ. ID. NO. 8953 | 199-GlnIleAlaArgAspGlnSerLysGlnIleAlaArgPheGlyLys-213 |
| 665-1 | |
| Hydrophilic Regions - Hopp-Woods | |
| SEQ. ID. NO. 8954 | 39-LysProArgArgArgIleGlyGlu-46 |
| SEQ. ID. NO. 8955 | 56-TrpSerGluGluLysArgLysThrValLeu-65 |
| SEQ. ID. NO. 8956 | 88-GlyArgLeuLysSer-92 |
| SEQ. ID. NO. 8957 | 94-ValArgTyrArgAsn-98 |
| SEQ. ID. NO. 8958 | 105-AlaLeuAlaAlaGlyGluLys-111 |

TABLE 1-continued

| | |
|---|---|
| SEQ. ID. NO. 8959 | 142-GlnLysAsnLysIleLeuAsp-148 |
| SEQ. ID. NO. 8960 | 150-GlnIleLeuLysGlyArgAsnArgTyr-158 |
| SEQ. ID. NO. 8961 | 166-ArgThrGluGlyLeuArgAlaLeu-173 |
| SEQ. ID. NO. 8962 | 176-GlnPheArgLysSerSer-181 |
| SEQ. ID. NO. 8963 | 190-GlnAspPheGlyArgAsnAspSerVal-198 |
| SEQ. ID. NO. 8964 | 229-ProValArgGluAlaAspAsn-235 |
| SEQ. ID. NO. 8965 | 248-PheProGlyGluAspAlaLysAlaAspAlaGlnArgMetAsnArgPheIleGluAspArgValArgGluHisProGlu-273 |
| SEQ. ID. NO. 8966 | 280-LysArgPheLysThrArgProGluGlySerPro-290 |
| Antigenic Index - Jameson-Wolf | |
| SEQ. ID. NO. 8967 | 8-LeuLysAspTyrGlnThrProAlaTyr-16 |
| SEQ. ID. NO. 8968 | 26-AspIleAsnGluPro-30 |
| SEQ. ID. NO. 8969 | 32-ThrValValLysSerArgLeuThrValGluProGlnArgValGlyGlu-47 |
| SEQ. ID. NO. 8970 | 49-LeuValLeuAspGlySerAla-55 |
| SEQ. ID. NO. 8971 | 80-GlyValProSerGluArgPheThrVal-88 |
| SEQ. ID. NO. 8972 | 90-ValGluThrGluIleLeuProAlaGluAsnLysSerLeu-102 |
| SEQ. ID. NO. 8973 | 115-GlnCysGluProGluGlyPheArgLys-123 |
| SEQ. ID. NO. 8974 | 128-IleAspArgProAspValMetSer-135 |
| SEQ. ID. NO. 8975 | 142-ValAlaAspLysLysArgTyrPro-149 |
| SEQ. ID. NO. 8976 | 153-SerAsnGlyAsnLysIleAspGlyGlyGluPheSerAspGlyArgHisTrpValLysTrpGluAspProPheSerLysProSer-180 |
| SEQ. ID. NO. 8977 | 191-AlaValThrGluAspTyr-196 |
| SEQ. ID. NO. 8978 | 200-MetSerGlyArgAsnValLysIle-207 |
| SEQ. ID. NO. 8979 | 211-ThrThrGluAlaAspLysProLysVal-219 |
| SEQ. ID. NO. 8980 | 230-MetLysTrpAspGluThrArgPhe-237 |
| SEQ. ID. NO. 8981 | 255-AsnMetGlyAlaMetGluAsnLysGlyLeu-264 |
| SEQ. ID. NO. 8982 | 275-AspSerArgThrAlaThrAspThrAspPheGluGlyIleGlu-288 |
| SEQ. ID. NO. 8983 | 295-TyrPheHisAsnTrpThrGlyAsnArgValThrCysArgAspTrp-309 |
| SEQ. ID. NO. 8984 | 313-SerLeuLysGluGly-317 |
| SEQ. ID. NO. 8985 | 322-ArgAspGlnGluPheSerGlyAspArgAlaSerArgAlaValArgArgIleGluAsn-340 |
| SEQ. ID. NO. 8986 | 347-HisGlnPheProGluAspAlaGlyProThrAlaHisProValArgProAlaSerTyrGluGluMetAsn-369 |
| SEQ. ID. NO. 8987 | 376-ValTyrGluLysGlyAlaGluVal-383 |
| SEQ. ID. NO. 8988 | 394-GluGlyPheGlnLysGlyMet-400 |
| SEQ. ID. NO. 8989 | 404-PheGlnArgHisAspGlyGlnAlaValThrCysAspAspPheArgAlaAlaMet-421 |
| SEQ. ID. NO. 8990 | 437-SerGlnAlaGlyThrPro-442 |
| SEQ. ID. NO. 8991 | 444-LeuGluAlaGluGlyArgLeuLysAsnAsnIle-454 |
| SEQ. ID. NO. 8992 | 459-ValLysGlnThrValProProThrProAspMetThrAspLysGlnPro-474 |
| SEQ. ID. NO. 8993 | 483-LeuLeuAsnArgAsnGlyGluAlaVal-491 |
| SEQ. ID. NO. 8994 | 494-AspTyrGlnGlyLysArgAlaThrGlu-502 |
| SEQ. ID. NO. 8995 | 537-LeuAsnTyrProTyrSerAspAspAspLeu-546 |
| SEQ. ID. NO. 8996 | 552-HisAspSerAspAla-556 |
| SEQ. ID. NO. 8997 | 578-LeuSerAspGlyValGluLeuProLysHisGluLysLeu-590 |
| SEQ. ID. NO. 8998 | 594-ValGluLysValIleSerAspAspLeuLeu-603 |
| SEQ. ID. NO. 8999 | 614-ValProSerGluAlaGluLeuTrpAspGlyAlaGluAsnIleAspProLeuArg-631 |
| SEQ. ID. NO. 9000 | 633-HisGlnAlaArgGluAlaLeu-639 |
| SEQ. ID. NO. 9001 | 652-HisGluLeuAsnArgGlnAlaAlaLysGlnGluAsnGlnSerTyrGluTyrSerProGluAlaAlaGly-674 |
| SEQ. ID. NO. 9002 | 677-ThrLeuArgAsnValCys-682 |
| SEQ. ID. NO. 9003 | 689-AlaAspProAlaHis-693 |
| SEQ. ID. NO. 9004 | 696-ThrValAlaGluLysTyrGlyGlu-703 |
| SEQ. ID. NO. 9005 | 719-AsnGlyAsnGluSerAspThrArgAsnArgLeu-729 |
| SEQ. ID. NO. 9006 | 733-PheAlaAspLysPheSerAspAspAlaLeuVal-743 |
| SEQ. ID. NO. 9007 | 752-GlySerSerArgArgSerAspThrLeuGlnGlnVal-763 |
| SEQ. ID. NO. 9008 | 768-GlnHisProLysPheSerLeuGluAsnProAsnLysAlaArgSer-782 |
| SEQ. ID. NO. 9009 | 785-GlySerPheSerArgAsnValPro-792 |
| SEQ. ID. NO. 9010 | 795-HisAlaGluAspGlySerGlyTyrArgPheIleAla-806 |
| SEQ. ID. NO. 9011 | 808-LysValIleGluIleAspArgPheAsnProGlnVal-819 |
| SEQ. ID. NO. 9012 | 831-AsnLysLeuGluProHisArgLysAsnLeuVal-841 |
| SEQ. ID. NO. 9013 | 844-AlaLeuGlnArgIleArgAlaGlnGluGlyLeuSerLysAspValGlyGluIleVal-862 |
| Hydrophilic Regions - Hopp-Woods | |
| SEQ. ID. NO. 9014 | 32-ThrValValLysSerArgLeuThrValGluProGlnArgValGlyGlu-47 |
| SEQ. ID. NO. 9015 | 82-ProSerGluArgPheThrVal-88 |
| SEQ. ID. NO. 9016 | 90-ValGluThrGluIleLeuProAlaGluAsnLysSer-101 |
| SEQ. ID. NO. 9017 | 116-CysGluProGluGlyPheArg-122 |
| SEQ. ID. NO. 9018 | 129-AspArgProAspValMetSer-135 |
| SEQ. ID. NO. 9019 | 142-ValAlaAspLysLysArgTyr-148 |
| SEQ. ID. NO. 9020 | 154-AsnGlyAsnLysIleAspGlyGlyGluPheSerAsp-165 |
| SEQ. ID. NO. 9021 | 170-ValLysTrpGluAspProPheSer-177 |
| SEQ. ID. NO. 9022 | 201-SerGlyArgAsnValLys-206 |
| SEQ. ID. NO. 9023 | 213-GluAlaAspLysProLysVal-219 |
| SEQ. ID. NO. 9024 | 230-MetLysTrpAspGluThrArgPhe-237 |
| SEQ. ID. NO. 9025 | 258-AlaMetGluAsnLysGly-263 |
| SEQ. ID. NO. 9026 | 275-AspSerArgThrAlaThrAspThrAspPheGluGlyIleGlu-288 |
| SEQ. ID. NO. 9027 | 313-SerLeuLysGluGly-317 |
| SEQ. ID. NO. 9028 | 322-ArgAspGlnGluPheSerGlyAspArgAlaSerArgAlaValArgArgIleGluAsn-340 |
| SEQ. ID. NO. 9029 | 348-GlnPheProGluAspAlaGlyPro-355 |
| SEQ. ID. NO. 9030 | 363-AlaSerTyrGluGluMetAsn-369 |
| SEQ. ID. NO. 9031 | 376-ValTyrGluLysGlyAlaGluVal-383 |
| SEQ. ID. NO. 9032 | 394-GluGlyPheGlnLysGlyMet-400 |
| SEQ. ID. NO. 9033 | 406-ArgHisAspGlyGln-410 |
| SEQ. ID. NO. 9034 | 413-ThrCysAspAspPheArgAlaAlaMet-421 |
| SEQ. ID. NO. 9035 | 444-LeuGluAlaGluGlyArgLeuLysAsnAsnIle-454 |
| SEQ. ID. NO. 9036 | 467-ProAspMetThrAspLysGlnPro-474 |

TABLE 1-continued

| | |
|---|---|
| SEQ. ID. NO. 9037 | 495-TyrGlnGlyLysArgAlaThrGlu-502 |
| SEQ. ID. NO. 9038 | 541-TyrSerAspAspAspLeu-546 |
| SEQ. ID. NO. 9039 | 552-HisAspSerAspAla-556 |
| SEQ. ID. NO. 9040 | 580-AspGlyValGluLeuProLysHisGluLysLeu-590 |
| SEQ. ID. NO. 9041 | 594-ValGluLysValIleSer-599 |
| SEQ. ID. NO. 9042 | 616-SerGluAlaGluLeu-620 |
| SEQ. ID. NO. 9043 | 622-AspGlyAlaGluAsnIleAspPro-629 |
| SEQ. ID. NO. 9044 | 633-HisGlnAlaArgGluAlaLeu-639 |
| SEQ. ID. NO. 9045 | 652-HisGluLeuAsnArgGlnAlaAlaLysGlnGluAsnGlnSer-665 |
| SEQ. ID. NO. 9046 | 689-AlaAspProAlaHis-693 |
| SEQ. ID. NO. 9047 | 696-ThrValAlaGluLysTyrGlyGlu-703 |
| SEQ. ID. NO. 9048 | 719-AsnGlyAsnGluSerAspThrArgAsnArgLeu-729 |
| SEQ. ID. NO. 9049 | 733-PheAlaAspLysPheSerAsp-739 |
| SEQ. ID. NO. 9050 | 753-SerSerArgArgSerAspThr-759 |
| SEQ. ID. NO. 9051 | 776-AsnProAsnLysAlaArgSer-782 |
| SEQ. ID. NO. 9052 | 795-HisAlaGluAspGlySerGly-801 |
| SEQ. ID. NO. 9053 | 808-LysValIleGluIleAspArgPheAsn-816 |
| SEQ. ID. NO. 9054 | 831-AsnLysLeuGluProHisArgLysAsnLeuVal-841 |
| SEQ. ID. NO. 9055 | 844-AlaLeuGlnArgIleArgAlaGlnGluGlyLeuSerLysAspValGlyGluIleVal-862 |
| 666-2 | |
| AMPHI Regions - AMPHI | |
| SEQ. ID. NO. 9056 | 89-GlyTyrAspIleLeuLysGlnGlyGlySer-98 |
| SEQ. ID. NO. 9057 | 162-LeuLysPheMetGluAla-167 |
| SEQ. ID. NO. 9058 | 177-ProAlaIleProLysLeuMetGluThrIleHisGln-188 |
| SEQ. ID. NO. 9059 | 193-LeuProTrpGlyLysLeuPheAspThrProIleArg-204 |
| SEQ. ID. NO. 9060 | 227-LeuAlaArgTyrProLys-232 |
| SEQ. ID. NO. 9061 | 249-LeuLeuLysAsnLeuGluPheAlaAspSerValGlnAlaLeu-262 |
| SEQ. ID. NO. 9062 | 265-GlnGlyAlaLysAlaLeuHisThr-272 |
| SEQ. ID. NO. 9063 | 274-LysTyrAlaGlnAsnIleValSerValVal-283 |
| SEQ. ID. NO. 9064 | 295-LeuGlnAspLeuSerAspTyrGln-302 |
| SEQ. ID. NO. 9065 | 313-TyrArgIleTyrGluValCysGlyMetGly-322 |
| SEQ. ID. NO. 9066 | 332-GlyGlnIleLeuGlyIleLeuAsnGluPheSer-342 |
| SEQ. ID. NO. 9067 | 353-LeuArgLeuLeuGlyAsp-358 |
| SEQ. ID. NO. 9068 | 411-AspPheIleHisGluTrp-416 |
| SEQ. ID. NO. 9069 | 424-LeuProSerThrSerHis-429 |
| SEQ. ID. NO. 9070 | 433-ValAspLysAlaGlyAsn-438 |
| SEQ. ID. NO. 9071 | 441-SerMetThrThrSerIleGluAsnAlaPheGlySer-452 |
| SEQ. ID. NO. 9072 | 511-ProGlyGlySerArgIleIleGlyTyrValAlaLys-522 |
| SEQ. ID. NO. 9073 | 537-AlaIleSerAlaProAsnLeuLeuAsnArgPheGly-548 |
| SEQ. ID. NO. 9074 | 562-GlnGlnAlaLeuAsnAsp-567 |
| SEQ. ID. NO. 9075 | 590-ArgLeuValGlyGly-594 |
| Antigenic Index - Jameson-Wolf | |
| SEQ. ID. NO. 9076 | 5-AsnHisGlnSerAsnSerGlyGluGlyValLeu-15 |
| SEQ. ID. NO. 9077 | 40-AsnGlnGlyLysValAsnThr-46 |
| SEQ. ID. NO. 9078 | 54-AlaAspAlaHisThrProGluHisAlaThr-63 |
| SEQ. ID. NO. 9079 | 65-LeuThrGluGlnLysGln-70 |
| SEQ. ID. NO. 9080 | 92-IleLeuLysGlnGlyGlySerAlaAla-100 |
| SEQ. ID. NO. 9081 | 114-GluProGlnSerSerGlyLeuGlyGly-122 |
| SEQ. ID. NO. 9082 | 130-AspAsnThrAlaLysThr-135 |
| SEQ. ID. NO. 9083 | 137-ThrThrPheAspGlyArgGluThrAlaPro-146 |
| SEQ. ID. NO. 9084 | 154-PheLeuAspLysAspGlyGlnPro-161 |
| SEQ. ID. NO. 9085 | 169-ValGlyGlyArgSerValGly-175 |
| SEQ. ID. NO. 9086 | 197-LysLeuPheAspThrProIleArgLeuAlaLysGlnGlyPhe-210 |
| SEQ. ID. NO. 9087 | 212-ValSerProArgLeu-216 |
| SEQ. ID. NO. 9088 | 221-GluGlnAsnGlnGlnHis-226 |
| SEQ. ID. NO. 9089 | 228-AlaArgTyrProLysThrAlaAla-235 |
| SEQ. ID. NO. 9090 | 271-HisThrGlyLysTyr-275 |
| SEQ. ID. NO. 9091 | 284-GlnAsnAlaLysAspAsnProGlyGln-292 |
| SEQ. ID. NO. 9092 | 296-GlnAspLeuSerAspTyrGlnValValGluArgProProValCys-310 |
| SEQ. ID. NO. 9093 | 320-GlyMetGlyAlaProSerSerGlyGly-328 |
| SEQ. ID. NO. 9094 | 340-GluPheSerProAsnGlnValGlyTyrAspAlaGluGlyLeuArgLeuLeuGlyAspAlaSerArg-361 |
| SEQ. ID. NO. 9095 | 363-AlaPheAlaAspArgAspValTyrLeuGlyAspProAspPheVal-377 |
| SEQ. ID. NO. 9096 | 384-LeuIleSerLysAspTyrLeuLysHisArgSerGlnLeuLeuGluGlnSerAspLysAlaLeu-404 |
| SEQ. ID. NO. 9097 | 431-SerIleValAspLysAlaGly-437 |
| SEQ. ID. NO. 9098 | 445-SerIleGluAsnAlaPhe-450 |
| SEQ. ID. NO. 9099 | 472-ProIleLysGlnGlyLysGlnValAlaAsnArgValGluProGlyLysArgProArgSerSerMet-493 |
| SEQ. ID. NO. 9100 | 500-LysAlaGlyLysProTyrMet-506 |
| SEQ. ID. NO. 9101 | 510-SerProGlyGlySerArgIle-516 |
| SEQ. ID. NO. 9102 | 548-GlySerTyrGluLeuGluThrGlyThr-556 |
| SEQ. ID. NO. 9103 | 566-AsnAspLeuGlyTyrLysThrAspValArgGluLeuAsnSerGlyVal-581 |
| SEQ. ID. NO. 9104 | 587-GluProSerArgLeuValGlyGlyAlaAspProArgArgGluGlyArgValMetGlyAsp-606 |
| Hydrophilic Regions - Hopp-Woods | |
| SEQ. ID. NO. 9105 | 8-SerAsnSerGlyGlu-12 |
| SEQ. ID. NO. 9106 | 40-AsnGlnGlyLysValAsnThr-46 |
| SEQ. ID. NO. 9107 | 55-AspAlaHisThrProGluHis-61 |
| SEQ. ID. NO. 9108 | 65-LeuThrGluGlnLysGln-70 |
| SEQ. ID. NO. 9109 | 96-GlyGlySerAlaAla-100 |
| SEQ. ID. NO. 9110 | 139-PheAspGlyArgGluThrAlaPro-146 |
| SEQ. ID. NO. 9111 | 154-PheLeuAspLysAspGlyGlnPro-161 |
| SEQ. ID. NO. 9112 | 203-IleArgLeuAlaLysGlnGlyPhe-210 |

| | |
|---|---|
| SEQ. ID. NO. 9113 | 284-GlnAsnAlaLysAspAsnProGly-291 |
| SEQ. ID. NO. 9114 | 302-GlnValValGluArgProPro-308 |
| SEQ. ID. NO. 9115 | 348-TyrAspAlaGluGlyLeuArgLeuLeuGlyAspAlaSerArg-361 |
| SEQ. ID. NO. 9116 | 363-AlaPheAlaAspArgAspValTyrLeuGly-372 |
| SEQ. ID. NO. 9117 | 388-AspTyrLeuLysHisArgSerGlnLeuLeuGluGlnSerAspLysAlaLeu-404 |
| SEQ. ID. NO. 9118 | 432-IleValAspLysAlaGly-437 |
| SEQ. ID. NO. 9119 | 472-ProIleLysGlnGlyLysGlnValAlaAsnArgValGluProGlyLysArgProArgSerSerMet-493 |
| SEQ. ID. NO. 9120 | 572-ThrAspValArgGluLeuAsnSer-579 |
| SEQ. ID. NO. 9121 | 595-AlaAspProArgArgGluGlyArgValMetGlyAsp-606 |
| 667-2 | |
| AMPHI Regions - AMPHI | |
| SEQ. ID. NO. 9122 | 6-GlyLeuCysGlyGlnValIlePro-13 |
| SEQ. ID. NO. 9123 | 48-IleIleAlaAspPheLeuGlnProAlaArg-57 |
| SEQ. ID. NO. 9124 | 59-GluCysLeuProAsnLeuAlaAla-66 |
| SEQ. ID. NO. 9125 | 74-LysThrAlaGlnPhe-78 |
| SEQ. ID. NO. 9126 | 115-IleAlaAlaValAlaGluIle-121 |
| SEQ. ID. NO. 9127 | 153-ThrAspGlnLeuArgArgMetPhePheAsnGlnPheGluLysPheSerAsnAspHis-171 |
| SEQ. ID. NO. 9128 | 202-LysMetMetLeuHisLys-207 |
| SEQ. ID. NO. 9129 | 234-ValGlnCysSerAspThr-239 |
| Antigenic Index - Jameson-Wolf | |
| SEQ. ID. NO. 9130 | 27-ProAlaAlaAspGlnThrGluThrGln-35 |
| SEQ. ID. NO. 9131 | 56-AlaArgMetGluCysLeuPro-62 |
| SEQ. ID. NO. 9132 | 71-LeuAlaArgLysThrAlaGln-77 |
| SEQ. ID. NO. 9133 | 89-ArgLeuValLysArgGluGlnIle-96 |
| SEQ. ID. NO. 9134 | 152-ProThrAspGlnLeuArg-157 |
| SEQ. ID. NO. 9135 | 165-GluLysPheSerAsn-169 |
| SEQ. ID. NO. 9136 | 190-ProThrHisAlaAlaArgAsnArgHisAsnLeu-200 |
| SEQ. ID. NO. 9137 | 226-ValGlyGlnArgGlyArgGlnLeu-233 |
| SEQ. ID. NO. 9138 | 248-IleGluSerGlnAsnArgGlyHisAspSer-257 |
| Hydrophilic Regions - Hopp-Woods | |
| SEQ. ID. NO. 9139 | 27-ProAlaAlaAspGlnThrGluThrGln-35 |
| SEQ. ID. NO. 9140 | 56-AlaArgMetGluCys-60 |
| SEQ. ID. NO. 9141 | 71-LeuAlaArgLysThrAlaGln-77 |
| SEQ. ID. NO. 9142 | 89-ArgLeuValLysArgGluGlnIle-96 |
| SEQ. ID. NO. 9143 | 165-GluLysPheSerAsn-169 |
| SEQ. ID. NO. 9144 | 192-HisAlaAlaArgOAsnArgHisAsnLeu-200 |
| SEQ. ID. NO. 9145 | 228-GlnArgGlyArgGln-232 |
| SEQ. ID. NO. 9146 | 250-SerGlnAsnArgGlyHisAsp-256 |
| 669-2 | |
| AMPHI Regions - AMPHI | |
| SEQ. ID. NO. 9147 | 24-PheLeuGlyIleLysArgPhePheArgGlnPro-34 |
| SEQ. ID. NO. 9148 | 60-LysLeuHisArgAlaPhe-65 |
| SEQ. ID. NO. 9149 | 95-GlnIlePheArgHisValGlnSer-102 |
| SEQ. ID. NO. 9150 | 119-ThrArgGlnAlaPhe-123 |
| Antigenic Index - Jameson-Wolf | |
| SEQ. ID. NO. 9151 | 5-ArgLeuGlnAsnGlyArgThrGlyArgAsnProProPheValGlnLysArgLeuAsp-23 |
| SEQ. ID. NO. 9152 | 29-ArgPhePheArgGlnProLeuGluMetArgArgIleIleLysLysHisGlnProIleAsnAla-49 |
| SEQ. ID. NO. 9153 | 69-GlyArgLysArgProHisHisHisAspSerSerLeuArgArgGlnHisGlyIleGluGlyMetGlyPhe-91 |
| SEQ. ID. NO. 9154 | 99-HisValGlnSerSerAsnArgGlnAsnGlyArgGlnProVal-112 |
| SEQ. ID. NO. 9155 | 114-AlaProAsnArgGlnThrArgGlnAlaPhe-123 |
| SEQ. ID. NO. 9156 | 137-ProThrSerAsnGlyTyrCys-143 |
| SEQ. ID. NO. 9157 | 149-SerThrHisArgThrThrHisLysAlaProProTyr-160 |
| Hydrophilic Regions - Hopp-Woods | |
| SEQ. ID. NO. 9158 | 7-GlnAsnGlyArgThrGlyArgAsn-14 |
| SEQ. ID. NO. 9159 | 18-ValGlnLysArgLeuAsp-23 |
| SEQ. ID. NO. 9160 | 34-ProLeuGluMetArgArgIleIleLysLysHisGlnPro-46 |
| SEQ. ID. NO. 9161 | 69-GlyArgLysArgProHisHisHisAspSerSerLeuArgArgGlnHisGly-85 |
| SEQ. ID. NO. 9162 | 101-GlnSerSerAsnArgGlnAsnGlyArg-109 |
| SEQ. ID. NO. 9163 | 116-AsnArgGlnThrArgGlnAlaPhe-123 |
| SEQ. ID. NO. 9164 | 151-HisArgThrThrHisLys-156 |
| 670-2 | |
| AMPHI Regions - AMPHI | |
| SEQ. ID. NO. 9165 | 10-ArgSerCysPheGly-14 |
| SEQ. ID. NO. 9166 | 16-ValLysAsnAlaSerGlyValSer-23 |
| SEQ. ID. NO. 9167 | 34-IleThrArgSerAla-38 |
| SEQ. ID. NO. 9168 | 77-ValGlySerSerAsnAsnIle-83 |
| Antigenic Index - Jameson-Wolf | |
| SEQ. ID. NO. 9169 | 4-CysArgAsnCysLeuAlaArgSerCys-12 |
| SEQ. ID. NO. 9170 | 18-AsnAlaSerGlyValSerSerSerArgIleCysProLeuSer-31 |
| SEQ. ID. NO. 9171 | 33-LysIleThrArgSerAlaThrSerArgAlaAsnProIle-45 |
| SEQ. ID. NO. 9172 | 65-AsnThrSerProThrIleSerGlySerSerAlaGluValGlySerSerAsnAsnIleThrArgGlySerIleAlaLysProArgAlaIleAla-95 |
| SEQ. ID. NO. 9173 | 98-CysCysTrpProProGluSerTrpGluGlyLysAla-109 |
| SEQ. ID. NO. 9174 | 114-AlaSerProThrArgSerLysSerSer-122 |
| SEQ. ID. NO. 9175 | 128-AlaCysSerAlaPhe-132 |
| Hydrophilic Regions - Hopp-Woods | |
| SEQ. ID. NO. 9176 | 33-LysIleThrArgSerAlaThrSerArgAlaAsn-43 |
| SEQ. ID. NO. 9177 | 73-SerSerAlaGluValGlySer-79 |

| | |
|---|---|
| SEQ. ID. NO. 9178 | 87-SerIleAlaLysProArgAlaIleAla-95 |
| SEQ. ID. NO. 9179 | 116-ProThrArgSerLysSer-121 |
| 671 | |
| AMPHI Regions - AMPHI | |
| SEQ. ID. NO. 9180 | 11-PheAsnAlaProAsn-15 |
| SEQ. ID. NO. 9181 | 72-LysGluAlaAlaLysSerLeu-78 |
| SEQ. ID. NO. 9182 | 96-ThrProArgIleAla-100 |
| SEQ. ID. NO. 9183 | 119-ArgLeuPheIleArgTyr-124 |
| Antigenic Index - Jameson-Wolf | |
| SEQ. ID. NO. 9184 | 9-ThrProPheAsnAlaProAsnThrProProLysMetArgLeuAlaLysProLysProThrAlaGlu-30 |
| SEQ. ID. NO. 9185 | 45-GlnAlaMetThrAsnArgGluMetAsnAspArgAlaAsnAlaAsnArgArgGlyTrpAsnGluAlaLysAlaArgSerAlaLysGluAlaAlaLysSer LeuAlaLysLysLysGluThrThr-85 |
| SEQ. ID. NO. 9186 | 98-ArgIleAlaAspSerThrMet-104 |
| SEQ. ID. NO. 9187 | 110-AlaGluThrArgArgSerAlaMet-117 |
| SEQ. ID. NO. 9188 | 125-LeuThrGlyAspThr-129 |
| Hydrophilic Regions - Hopp-Woods | |
| SEQ. ID. NO. 9189 | 16-ThrProProLysMetArgLeuAlaLysProLysProThrAla-29 |
| SEQ. ID. NO. 9190 | 47-MetThrAsnArgGluMetAsnAspArgAlaAsnAlaAsnArgArgGlyTrpAsnGluAlaLysAlaArgSerAlaLysGluAlaAlaLysSerLeuAla LysLysLysGluThrThr-85 |
| SEQ. ID. NO. 9191 | 110-AlaGluThrArgArgSerAlaMet-117 |
| 672 | |
| AMPHI Regions - AMPHI | |
| SEQ. ID. NO. 9192 | 38-ArgAlaValAspIleAlaArgAlaLysLys-47 |
| SEQ. ID. NO. 9193 | 50-AlaAlaLeuProProPheValSerValVal-59 |
| SEQ. ID. NO. 9194 | 67-AlaGlnAsnIleArgArgIleLeuAlaGluValPro-78 |
| SEQ. ID. NO. 9195 | 91-AlaPheCysArgGlnPheHisArgProTyr-100 |
| SEQ. ID. NO. 9196 | 105-ArgValGlnThrAlaSerAspIle-112 |
| SEQ. ID. NO. 9197 | 115-AlaAlaThrArgPheProAsp-121 |
| SEQ. ID. NO. 9198 | 131-HisProSerGluTyrGlyGlyThr-138 |
| SEQ. ID. NO. 9199 | 163-ProGluAsnValGlyGluAlaValArgIleThrGlyAlaGluSer-177 |
| Antigenic Index - Jameson-Wolf | |
| SEQ. ID. NO. 9200 | 1-MetArgLysIleArgThrLysIle-8 |
| SEQ. ID. NO. 9201 | 13-ThrProGluAspAlaAlaAla-19 |
| SEQ. ID. NO. 9202 | 35-GlySerSerArgAlaValAspIleAlaArgAlaLysLysIleThr-49 |
| SEQ. ID. NO. 9203 | 65-GluSerAlaGlnAsnIleArgArgIleLeuAla-75 |
| SEQ. ID. NO. 9204 | 84-PheHisGlyAspGluAspAspAlaPhe-92 |
| SEQ. ID. NO. 9205 | 110-SerAspIleArgAsnAlaAlaThrArgPheProAspAla-122 |
| SEQ. ID. NO. 9206 | 130-TyrHisProSerGluTyrGlyGlyThrGlyAsnArgPheAsp-143 |
| SEQ. ID. NO. 9207 | 148-AlaGluTyrSerGlyLysPro-154 |
| SEQ. ID. NO. 9208 | 160-GlyLeuThrProGluAsnValGlyGluAlaValArg-171 |
| SEQ. ID. NO. 9209 | 176-GluSerValAspValSerGlyGlyValGluAlaSerLysGlyLysLysAspAlaAlaLys-195 |
| SEQ. ID. NO. 9210 | 202-ThrAlaAsnArgLeuSerArg-208 |
| Hydrophilic Regions - Hopp-Woods | |
| SEQ. ID. NO. 9211 | 1-MetArgLysIleArgThrLysIle-8 |
| SEQ. ID. NO. 9212 | 13-ThrProGluAspAlaAlaAla-19 |
| SEQ. ID. NO. 9213 | 36-SerSerArgAlaValAspIleAlaArgAlaLysLysIleThr-49 |
| SEQ. ID. NO. 9214 | 66-SerAlaGlnAsnIleArgArgIleLeuAla-75 |
| SEQ. ID. NO. 9215 | 85-HisGlyAspGluAspAspAlaPhe-92 |
| SEQ. ID. NO. 9216 | 110-SerAspIleArgAsnAlaAla-116 |
| SEQ. ID. NO. 9217 | 134-GluTyrGlyGlyThrGlyAsn-140 |
| SEQ. ID. NO. 9218 | 165-AsnValGlyGluAlaValArg-171 |
| SEQ. ID. NO. 9219 | 176-GluSerValAspVal-180 |
| SEQ. ID. NO. 9220 | 184-ValGluAlaSerLysGlyLysLysAspAlaAlaLys-195 |
| SEQ. ID. NO. 9221 | 204-AsnArgLeuSerArg-208 |
| 673 | |
| AMPHI Regions - AMPHI | |
| SEQ. ID. NO. 9222 | 84-LeuAsnAspArgLeuAsnGlnAsnValThrGluAlaLeuGlyGlyValAspVal-101 |
| SEQ. ID. NO. 9223 | 110-ArgPheThrAspAla-114 |
| SEQ. ID. NO. 9224 | 117-ValValLeuLysGlnLeuProLys-124 |
| SEQ. ID. NO. 9225 | 172-ArgIleAlaAsnLeuLeuGluLeuIleLysProTyrLeu-184 |
| SEQ. ID. NO. 9226 | 212-LysLeuPheArgTyrLeuGlyGluGlu-220 |
| SEQ. ID. NO. 9227 | 261-GlyGluArgLeuLysLysIleSerThr-269 |
| SEQ. ID. NO. 9228 | 275-MetGluLysLeuPhe-279 |
| SEQ. ID. NO. 9229 | 285-LeuLysValTrpValLysValLys-292 |
| Antigenic Index - Jameson-Wolf | |
| SEQ. ID. NO. 9230 | 7-LeuAlaGlyGluArgAlaAlaGlyGlyTyrArg-17 |
| SEQ. ID. NO. 9231 | 24-ValGlyArgProAsnValGlyLysSerThr-33 |
| SEQ. ID. NO. 9232 | 44-SerIleThrSerLysLysAlaGlnThrThrArgAsnArgValThr-58 |
| SEQ. ID. NO. 9233 | 61-TyrThrAspAspThrAla-66 |
| SEQ. ID. NO. 9234 | 73-ThrProGlyPheGlnThrAspHisArgAsnAlaLeuAsnAspArgLeuAsnGlnAsnValThrGlu-94 |
| SEQ. ID. NO. 9235 | 110-ArgPheThrAspAlaAspArgValVal-118 |
| SEQ. ID. NO. 9236 | 121-GlnLeuProLysHisThr-126 |
| SEQ. ID. NO. 9237 | 134-LysIleAspLysAspLysAlaLysAspArgTyrAla-145 |
| SEQ. ID. NO. 9238 | 153-ValArgAlaGluPhe-157 |
| SEQ. ID. NO. 9239 | 180-IleLysProTyrLeuProGluSerVal-188 |
| SEQ. ID. NO. 9240 | 190-MetTyrProGluAspMetValThrAspLysSerAlaArg-202 |
| SEQ. ID. NO. 9241 | 208-IleValArgGluLysLeuPhe-214 |
| SEQ. ID. NO. 9242 | 217-LeuGlyGluGluLeuPro-222 |
| SEQ. ID. NO. 9243 | 227-ValGluValGluGlnPheGluGluGluAspGlyLeuAsn-239 |
| SEQ. ID. NO. 9244 | 247-ValAspLysGluSerGlnLys-253 |

TABLE 1-continued

| | |
|---|---|
| SEQ. ID. NO. 9245 | 258-GlyLysGlyGlyGluArgLeuLysLysIleSerThrGluAlaArgLeuAspMetGluLysLeuPheAsp-280 |
| SEQ. ID. NO. 9246 | 291-ValLysSerGlyTrpAlaAspAspIleArgPheLeuArg-303 |
| Hydrophilic Regions - Hopp-Woods | |
| SEQ. ID. NO. 9247 | 7-LeuAlaGlyGluArgAlaAlaGly-14 |
| SEQ. ID. NO. 9248 | 45-IleThrSerLysLysAlaGlnThrThrArgAsnArgVal-57 |
| SEQ. ID. NO. 9249 | 61-TyrThrAspAspThrAla-66 |
| SEQ. ID. NO. 9250 | 78-ThrAspHisArgAsnAlaLeuAsnAspArgLeuAsn-89 |
| SEQ. ID. NO. 9251 | 110-ArgPheThrAspAlaAspArgValVal-118 |
| SEQ. ID. NO. 9252 | 134-LysIleAspLysAspLysAlaLysAspArgTyrAla-145 |
| SEQ. ID. NO. 9253 | 153-ValArgAlaGluPhe-157 |
| SEQ. ID. NO. 9254 | 194-AspMetValThrAspLysSerAlaArg-202 |
| SEQ. ID. NO. 9255 | 208-IleValArgGluLysLeuPhe-214 |
| SEQ. ID. NO. 9256 | 217-LeuGlyGluGluLeuPro-222 |
| SEQ. ID. NO. 9257 | 227-ValGluValGluGlnPheGluGluGluAspGlyLeuAsn-239 |
| SEQ. ID. NO. 9258 | 247-ValAspLysGluSerGlnLys-253 |
| SEQ. ID. NO. 9259 | 259-LysGlyGlyGluArgLeuLysLysIleSerThrGluAlaArgLeuAspMetGluLysLeuPheAsp-280 |
| SEQ. ID. NO. 9260 | 293-SerGlyTrpAlaAspAspIleArgPheLeuArg-303 |
| 674 | |
| AMPHI Regions - AMPHI | |
| SEQ. ID. NO. 9261 | 16-ValTyrGlnSerLeuIle-21 |
| SEQ. ID. NO. 9262 | 24-ThrAlaAlaProGluIleAlaLysAsnIleArgGluMetSerAspPheAlaLysAlaAspGluGluLeu-46 |
| SEQ. ID. NO. 9263 | 58-AlaAlaGluTyrIleArgGlnIleArgPro-67 |
| SEQ. ID. NO. 9264 | 86-ThrAlaCysHisGluLeuSerAlaMetProGluThr-97 |
| SEQ. ID. NO. 9265 | 107-IleGluValThrLysThrPheGlyGlyThrAspGlyHisLysPheValAsnGlyIleLeuAspLysLeuAla-130 |
| Antigenic Index - Jameson-Wolf | |
| SEQ. ID. NO. 9266 | 1-MetLysThrAlaArgArgArgSerArgGluLeuAla-12 |
| SEQ. ID. NO. 9267 | 28-GluIleAlaLysAsnIleArgGluMetSerAspPheAlaLysAlaAspGluGluLeuPhe-47 |
| SEQ. ID. NO. 9268 | 54-ThrGlnThrAsnAla-58 |
| SEQ. ID. NO. 9269 | 63-ArgGlnIleArgProLeuLeuAspArgAspGluLysAspLeuAsnProIleGluArg-81 |
| SEQ. ID. NO. 9270 | 93-AlaMetProGluThrProTyr-99 |
| SEQ. ID. NO. 9271 | 105-GluAlaIleGluValThrLysThrPheGlyGlyThrAspGlyHisLysPhe-121 |
| SEQ. ID. NO. 9272 | 129-LeuAlaAlaGlnIleArgProAspGluProLysArgArg-141 |
| Hydrophilic Regions - Hopp-Woods | |
| SEQ. ID. NO. 9273 | 1-MetLysThrAlaArgArgArgSerArgGluLeuAla-12 |
| SEQ. ID. NO. 9274 | 28-GluIleAlaLysAsnIleArgGluMetSerAspPheAlaLysAlaAspGluGluLeuPhe-47 |
| SEQ. ID. NO. 9275 | 63-ArgGlnIleArgProLeuLeuAspArgAspGluLysAspLeuAsnProIleGluArg-81 |
| SEQ. ID. NO. 9276 | 105-GluAlaIleGluVal-109 |
| SEQ. ID. NO. 9277 | 133-IleArgProAspGluProLysArgArg-141 |
| 675 | |
| AMPHI Regions - AMPHI | |
| SEQ. ID. NO. 9278 | 21-ArgPheThrAsnGluIleGlySerGluMetLeuLysValCysCysArgThrLeuGlnGluLeuGly-42 |
| SEQ. ID. NO. 9279 | 74-AlaLeuIleAlaIle-78 |
| SEQ. ID. NO. 9280 | 123-GlnAlaIleGluArgIleGluGluLysAlaSerAsp-134 |
| SEQ. ID. NO. 9281 | 141-GluCysAlaAsnLeuValAsnLeuLeuLeuGlu-151 |
| Antigenic Index - Jameson-Wolf | |
| SEQ. ID. NO. 9282 | 6-ProAsnLeuAspGlyLysHisLeuArg-14 |
| SEQ. ID. NO. 9283 | 26-IleGlySerGluMetLeu-31 |
| SEQ. ID. NO. 9284 | 42-GlyValAlaAspGluAsnIle-48 |
| SEQ. ID. NO. 9285 | 68-SerSerGluLysPheAsp-73 |
| SEQ. ID. NO. 9286 | 82-IleArgGlyGluThrTyr-87 |
| SEQ. ID. NO. 9287 | 92-ValSerAsnGluSerGlyAlaGlyVal-100 |
| SEQ. ID. NO. 9288 | 118-ThrGluAsnAspAlaGlnAlaIleGluArgIleGluGluLysAlaSerAspAlaAlaLysValAlaVal-140 |
| SEQ. ID. NO. 9289 | 152-GluGlnPheGluAspGluGlu-158 |
| Hydrophilic Regions - Hopp-Woods | |
| SEQ. ID. NO. 9290 | 8-LeuAspGlyLysHisLeuArg-14 |
| SEQ. ID. NO. 9291 | 26-IleGlySerGluMetLeu-31 |
| SEQ. ID. NO. 9292 | 42-GlyValAlaAspGluAsnIle-48 |
| SEQ. ID. NO. 9293 | 68-SerSerGluLysPheAsp-73 |
| SEQ. ID. NO. 9294 | 82-IleArgGlyGluThrTyr-87 |
| SEQ. ID. NO. 9295 | 92-ValSerAsnGluSerGlyAlaGly-99 |
| SEQ. ID. NO. 9296 | 118-ThrGluAsnAspAlaGlnAlaIleGluArgIleGluGluLysAlaSerAspAlaAlaLysValAlaVal-140 |
| SEQ. ID. NO. 9297 | 152-GluGlnPheGluAspGluGlu-158 |
| 677 | |
| AMPHI Regions - AMPHI | |
| SEQ. ID. NO. 9298 | 20-AlaArgPheCysArgPheArgArg-27 |
| SEQ. ID. NO. 9299 | 45-LeuThrProPheArgArgValGlnAsnHisPheValAlaPheAlaArgPheAsnGln-63 |
| SEQ. ID. NO. 9300 | 79-IleAspPheIleAspAlaAsp-85 |
| SEQ. ID. NO. 9301 | 87-PheAspGlyLeuLeuAlaPro-93 |
| SEQ. ID. NO. 9302 | 105-LysHisLeuValGlyArgPhe-111 |
| SEQ. ID. NO. 9303 | 155-CysArgProValAspAspLeuAspAspPheGlyAlaPhePheValAspGlnLeuIleLysLeuValPheGlnCys-179 |
| Antigenic Index - Jameson-Wolf | |
| SEQ. ID. NO. 9304 | 23-CysArgPheArgArgHisSerArgSerValAsp-33 |
| SEQ. ID. NO. 9305 | 35-AspValPheAspArgLysAspPheAsn-43 |
| SEQ. ID. NO. 9306 | 47-ProPheArgArgValGln-52 |
| SEQ. ID. NO. 9307 | 61-PheAsnGlnThrThrSerGlnArgArgAsnProArgAsnPheVal-75 |
| SEQ. ID. NO. 9308 | 82-IleAspAlaAspAspPheAspGly-89 |
| SEQ. ID. NO. 9309 | 97-GlnGlnSerAspArgArgAlaGluLysHisLeu-107 |
| SEQ. ID. NO. 9310 | 115-GlyIleAspAspAspGlySerLeu-122 |
| SEQ. ID. NO. 9311 | 125-PheGlyGlnGluThrAspAlaAlaVal-133 |

TABLE 1-continued

SEQ. ID. NO. 9312 156-ArgProValAspAspLeuAspAspPheGly-165
SEQ. ID. NO. 9313 181-ProSerGlyGlyArgAsn-186
Hydrophilic Regions - Hopp-Woods
SEQ. ID. NO. 9314 23-CysArgPheArgArgHisSerArgSerValAsp-33
SEQ. ID. NO. 9315 35-AspValPheAspArgLysAspPhe-42
SEQ. ID. NO. 9316 65-ThrSerGlnArgArgAsnProArg-72
SEQ. ID. NO. 9317 82-IleAspAlaAspAspPheAsp-88
SEQ. ID. NO. 9318 97-GlnGlnSerAspArgArgAlaGluLysHisLeu-107
SEQ. ID. NO. 9319 115-GlyIleAspAspAspGlySer-121
SEQ. ID. NO. 9320 126-GlyGlnGluThrAspAlaAlaVal-133
SEQ. ID. NO. 9321 156-ArgProValAspAspLeuAspAsp-163
678
AMPHI Regions - AMPHI
SEQ. ID. NO. 9322 10-LeuValSerAlaValIle-15
SEQ. ID. NO. 9323 24-MetArgGlyValIle-28
SEQ. ID. NO. 9324 80-IleGlnLysMetLeuArgSerLeuLeuThrSerAla-91
SEQ. ID. NO. 9325 102-ArgIleLeuGlyGlyValPheGlyAlaLeu-111
SEQ. ID. NO. 9326 130-ProAspThrGluGlu-134
Antigenic Index - Jameson-Wolf
SEQ. ID. NO. 9327 125-SerLysThrAspLeuProAspThrGluGluTrpArgGlnSerTyrThr-140
SEQ. ID. NO. 9328 154-HisSerGlyGlyThrAlaGluThrProGluAspAsp-165
Hydrophilic Regions - Hopp-Woods
SEQ. ID. NO. 9329 125-SerLysThrAspLeuProAspThrGluGluTrpArgGln-137
SEQ. ID. NO. 9330 157-GlyThrAlaGluThrProGluAspAsp-165
681-2
AMPHI Regions - AMPHI
SEQ. ID. NO. 9331 12-PheSerGluGluAlaLysPheIleSerAlaMet-22
SEQ. ID. NO. 9332 120-CysLeuArgValGlyArgAlaValArgArg-129
Antigenic Index - Jameson-Wolf
SEQ. ID. NO. 9333 9-AlaSerAsnPheSerGluGluAlaLysPhe-18
SEQ. ID. NO. 9334 39-AlaThrProAsnSerTrpArgValArgGlnGln-49
SEQ. ID. NO. 9335 59-LeuValLysArgAlaCys-64
SEQ. ID. NO. 9336 67-ProMetArgArgCysLeuProSerArgLeu-76
SEQ. ID. NO. 9337 90-GlyPheGlyMetProSerGluGly-97
SEQ. ID. NO. 9338 102-AlaAlaSerArgArgArgPheGlyMetCysArgLeuArgGlnAlaProMetArgCysLeuArgValGlyArgAlaValArgArgPheGln-131
SEQ. ID. NO. 9339 134-PheTrpArgCysArgArgGly-140
Hydrophilic Regions - Hopp-Woods
SEQ. ID. NO. 9340 11-AsnPheSerGluGluAlaLysPhe-18
SEQ. ID. NO. 9341 44-TrpArgValArgGln-48
SEQ. ID. NO. 9342 59-LeuValLysArgAlaCys-64
SEQ. ID. NO. 9343 67-ProMetArgArgCysLeuPro-73
SEQ. ID. NO. 9344 102-AlaAlaSerArgArgArgPheGly-109
SEQ. ID. NO. 9345 112-ArgLeuArgGlnAlaPro-117
SEQ. ID. NO. 9346 119-ArgCysLeuArgValGlyArgAlaValArgArg-129
682-2
AMPHI Regions - AMPHI
SEQ. ID. NO. 9347 33-ArgLeuArgLysCysGlyArgIleLeuSerGlyIleCysGluProPhe-48
SEQ. ID. NO. 9348 99-CysArgLeuPheCysAspGly-105
Antigenic Index - Jameson-Wolf
SEQ. ID. NO. 9349 9-SerTyrGlyLysTrpArgLysAsnTrpAspIle-19
SEQ. ID. NO. 9350 30-SerSerThrArgLeuArgLysCysGlyArg-39
SEQ. ID. NO. 9351 69-ArgThrLeuArgLeuArgGlySerArgThrArg-79
SEQ. ID. NO. 9352 84-GlyProPheTrpPheCysHisArgProArgGlnSerHisGly-97
SEQ. ID. NO. 9353 102-PheCysAspGlySerMetAspGlnThrArgAspArgArgCysArgSer-117
SEQ. ID. NO. 9354 121-LeuHisSerAspArgTyrArgHisSerAsnLeuTrp-132
Hydrophilic Regions - Hopp-Woods
SEQ. ID. NO. 9355 12-LysTrpArgLysAsnTrpAsp-18
SEQ. ID. NO. 9356 32-ThrArgLeuArgLysCysGlyArg-39
SEQ. ID. NO. 9357 69-ArgThrLeuArgLeuArgGlySerArgThr-78
SEQ. ID. NO. 9358 91-ArgProArgGlnSerHisGly-97
SEQ. ID. NO. 9359 105-GlySerMetAspGlnThrArgAspArgArgCysArgSer-117
SEQ. ID. NO. 9360 122-HisSerAspArgTyrArgHis-128
683
AMPHI Regions - AMPHI
SEQ. ID. NO. 9361 26-ThrProAspLysSerAlaArgTrpGluAsnIleGlyThrIleSerAsn-41
SEQ. ID. NO. 9362 75-ArgPheAlaAsnThrPro-80
SEQ. ID. NO. 9363 101-SerSerLeuGlnLeuPhe-106
SEQ. ID. NO. 9364 124-ArgProMetSerIleLeuSerGly-131
Antigenic Index - Jameson-Wolf
SEQ. ID. NO. 9365 24-CysSerThrProAspLysSerAlaArgTrpGluAsn-35
SEQ. ID. NO. 9366 37-GlyThrIleSerAsnGly-42
SEQ. ID. NO. 9367 48-IleAsnLysAspSerValArgLysAsnGlyAsn-58
SEQ. ID. NO. 9368 63-GlnAspLysLysValValThrAsnLeuLysGlnGluArgPheAlaAsnThrProAlaTyr-82
SEQ. ID. NO. 9369 93-CysAsnAsnLysThrTyrArgLeu-100
SEQ. ID. NO. 9370 106-PheAspThrLysAsnThrGluIleSerThrGlnAsnTyrThrAlaSerSerLeuArgPro-125
SEQ. ID. NO. 9371 131-GlyThrLeuThrGluLysGlnTyrGlu-139
SEQ. ID. NO. 9372 141-ValCysGlyLysLysLeu-146
Hydrophilic Regions - Hopp-Woods
SEQ. ID. NO. 9373 25-SerThrProAspLysSerAlaArgTrpGluAsn-35
SEQ. ID. NO. 9374 48-IleAsnLysAspSerValArgLysAsnGly-57

TABLE 1-continued

SEQ. ID. NO. 9375 63-GlnAspLysLysValValThr-69
SEQ. ID. NO. 9376 71-LeuLysGlnGluArgPheAla-77
SEQ. ID. NO. 9377 107-AspThrLysAsnThrGluIleSer-114
SEQ. ID. NO. 9378 133-LeuThrGluLysGlnTyrGlu-139
SEQ. ID. NO. 9379 141-ValCysGlyLysLysLeu-146
684
AMPHI Regions - AMPHI
SEQ. ID. NO. 9380 13-AlaAlaCysGlyThrValGln-19
SEQ. ID. NO. 9381 47-LeuAlaGluProLeu-51
SEQ. ID. NO. 9382 73-TrpAlaAspThrLeuAspAspMetLeuGluAlaAlaLeuSerAsnAlaPheAsnArgLeuAspSerThr-95
SEQ. ID. NO. 9383 110-TrpThrValTyrIleAspAlaPheGlnGlySerTyr-121
SEQ. ID. NO. 9384 154-AlaMetThrAlaAlaLeuGluGlnGlyLeuLysGlnAlaAlaGlnGlnMetVal-171
Antigenic Index - Jameson-Wolf
SEQ. ID. NO. 9385 26-LeuProAspSerArgTyrIleArgProAlaThrGlnGlyGlyGluThrAlaValGluValArgLeuAlaGluProLeuLysArgGlyGlyLeu-56
SEQ. ID. NO. 9386 60-ThrAspProTyrArgLeuAsnThrAlaGln-69
SEQ. ID. NO. 9387 76-ThrLeuAspAspMetLeuGlu-82
SEQ. ID. NO. 9388 90-AsnArgLeuAspSerThrArg-96
SEQ. ID. NO. 9389 101-AlaSerArgSerGlySerThrGluLys-109
SEQ. ID. NO. 9390 117-PheGlnGlySerTyrThrGlyLysThrLeu-126
SEQ. ID. NO. 9391 133-LeuProAspGlyThrAsnArgProPheHisIleGluThrGluGlnGlnGlyAspGlyTyrAla-153
SEQ. ID. NO. 9392 161-GlnGlyLeuLysGlnAlaAla-167
Hydrophilic Regions - Hopp-Woods
SEQ. ID. NO. 9393 27-ProAspSerArgTyrIleArg-33
SEQ. ID. NO. 9394 35-AlaThrGlnGlyGlyGluThrAlaValGluValArgLeuAlaGluProLeuLysArgGlyGly-55
SEQ. ID. NO. 9395 76-ThrLeuAspAspMetLeuGlu-82
SEQ. ID. NO. 9396 90-AsnArgLeuAspSer-94
SEQ. ID. NO. 9397 102-SerArgSerGlySerThrGluLys-109
SEQ. ID. NO. 9398 141-PheHisIleGluThrGluGlnGlnGlyAsp-150
SEQ. ID. NO. 9399 161-GlnGlyLeuLysGlnAlaAla-167
685
AMPHI Regions - AMPHI
SEQ. ID. NO. 9400 7-AsnPheAlaPheCysGlyValVal-14
SEQ. ID. NO. 9401 44-CysAlaValLeuLeu-48
SEQ. ID. NO. 9402 94-TrpAlaAlaLeuAspThrLeuThrGluLeu-103
SEQ. ID. NO. 9403 137-TyrGluAlaLeuHisArgTyr-143
SEQ. ID. NO. 9404 154-GlyAlaGluAlaTyrGluGlnLeuAlaLysAsn-164
SEQ. ID. NO. 9405 182-GluLysGlnMetGluThrLeuAlaArgIlePheGlyLysGlu-195
SEQ. ID. NO. 9406 206-AspAlaLeuPheAla-210
SEQ. ID. NO. 9407 296-AlaValGluValLeuAspAsnAlaLeuVal-305
SEQ. ID. NO. 9408 336-AlaAlaGluGlnLeuLysAlaAla-343
Antigenic Index - Jameson-Wolf
SEQ. ID. NO. 9409 20-LeuAsnAsnLysHisSerTyrSerTyrAlaLysGluProHisThrValLysProArgPhe-39
SEQ. ID. NO. 9410 52-SerProGluProAlaAlaGluLysThrValSer-62
SEQ. ID. NO. 9411 74-ProThrAlaArgGlyAspAlaValValProLysAsnProGluArgValAla-90
SEQ. ID. NO. 9412 122-AlaPheAspLysAlaAla-127
SEQ. ID. NO. 9413 133-PheGluProAspTyrGluAlaLeuHisArgTyrAsn-144
SEQ. ID. NO. 9414 151-GlyGlyProGlyAlaGluAlaTyrGluGlnLeuAlaLysAsnAlaThr-166
SEQ. ID. NO. 9415 170-LeuThrValAspAsnGlyAsnIleArgThrSerGlyGluLysGlnMetGluThrLeu-188
SEQ. ID. NO. 9416 192-PheGlyLysGluAlaArgAlaAlaGluLeuLysAlaGlnIle-205
SEQ. ID. NO. 9417 211-GlnThrArgGluAlaAlaLysGlyLysGlyArgGlyLeu-223
SEQ. ID. NO. 9418 227-ValThrGlyAsnLysValSerAlaPheGlyThrGlnSerArgLeu-241
SEQ. ID. NO. 9419 247-GlyAspIleGlyLeuProProValAspGluSerLeuArgAsnGluGlyHisGlyGln-265
SEQ. ID. NO. 9420 271-TyrIleLysGluLysAsnProAspTrpIle-280
SEQ. ID. NO. 9421 285-ArgThrAlaAlaIleGlyGlnGluGlyProAla-295
SEQ. ID. NO. 9422 307-GlyThrAsnAlaTrpLysArgLysGln-315
SEQ. ID. NO. 9423 338-GluGlnLeuLysAlaAlaPheLysLysAlaGluPro-349
SEQ. ID. NO. 9424 351-AlaAlaGlyLysLys-355
Hydrophilic Regions - Hopp-Woods
SEQ. ID. NO. 9425 28-TyrAlaLysGluProHisThrValLys-36
SEQ. ID. NO. 9426 52-SerProGluProAlaAlaGluLysThrValSer-62
SEQ. ID. NO. 9427 75-ThrAlaArgGlyAspAlaValVal-82
SEQ. ID. NO. 9428 84-LysAsnProGluArgValAla-90
SEQ. ID. NO. 9429 122-AlaPheAspLysAlaAla-127
SEQ. ID. NO. 9430 135-ProAspTyrGluAla-139
SEQ. ID. NO. 9431 156-GluAlaTyrGluGlnLeuAlaLys-163
SEQ. ID. NO. 9432 175-GlyAsnIleArgThrSerGlyGluLysGlnMetGluThrLeu-188
SEQ. ID. NO. 9433 192-PheGlyLysGluAlaArgAlaAlaGluLeuLysAlaGlnIle-205
SEQ. ID. NO. 9434 211-GlnThrArgGluAlaAlaLysGlyLysGlyArgGly-222
SEQ. ID. NO. 9435 253-ProValAspGluSerLeuArgAsnGluGlyHisGly-264
SEQ. ID. NO. 9436 271-TyrIleLysGluLysAsnPro-277
SEQ. ID. NO. 9437 290-GlyGlnGluGlyProAla-295
SEQ. ID. NO. 9438 309-AsnAlaTrpLysArgLysGln-315
SEQ. ID. NO. 9439 338-GluGlnLeuLysAlaAlaPheLysLysAlaGluPro-349
SEQ. ID. NO. 9440 351-AlaAlaGlyLysLys-355
686-2
AMPHI Regions - AMPHI
SEQ. ID. NO. 9441 7-ValLeuGlyGlyIleAlaAlaLeu-14
SEQ. ID. NO. 9442 39-GlySerLeuIleGluArgIleAsnAsn-47
SEQ. ID. NO. 9443 146-SerAsnIleLysSerIleAlaAspIleLysGlyValLysThrAlaGlnSerLeuThrSerAsnTyr-167
SEQ. ID. NO. 9444 179-ValAlaValAspGlyLeuAlaGlnSerLeu-188

TABLE 1-continued

| | |
|---|---|
| SEQ. ID. NO. 9445 | 204-LeuAlaValLeuAspTyrLeuLysLysAsnPro-214 |
| SEQ. ID. NO. 9446 | 241-AspGluAlaValAlaLysPheSerThrAlaIle-251 |
| SEQ. ID. NO. 9447 | 255-LysAlaAspGlyThrLeuLysLysLeuGlyGluGlnPhe-267 |
| Antigenic Index - Jameson-Wolf | |
| SEQ. ID. NO. 9448 | 20-GlyGlySerGluGlyGlySerGlyAlaSerSerAlaProAlaGlnSerAlaVal-37 |
| SEQ. ID. NO. 9449 | 40-SerLeuIleGluArgIleAsnAsnLysGlyThrVal-51 |
| SEQ. ID. NO. 9450 | 54-GlyThrGluGlyThr-58 |
| SEQ. ID. NO. 9451 | 64-TyrHisAspLysAspGlyLysLeuThrGlyTyrAspValGluValThrArgAlaValAlaGluLysLeuGlyVal-88 |
| SEQ. ID. NO. 9452 | 90-ValGluPheLysGluThrGlnTrp-97 |
| SEQ. ID. NO. 9453 | 118-LeuThrSerProGluArgGlnAlaThrPheAspLysSerAspProTyrSerTrp-135 |
| SEQ. ID. NO. 9454 | 143-ArgAsnAspSerAsnIleLysSerIleAlaAspIleLysGlyValLysThrAlaGln-161 |
| SEQ. ID. NO. 9455 | 163-LeuThrSerAsnTyrGlyGluLysAlaLysAlaAlaGly-175 |
| SEQ. ID. NO. 9456 | 191-IleGluGlnLysArgAlaAspAlaThrLeuAsnAspGluLeuAla-205 |
| SEQ. ID. NO. 9457 | 209-TyrLeuLysLysAsnProAsnAlaGly-217 |
| SEQ. ID. NO. 9458 | 225-ProAlaAspGluLysValGlySer-232 |
| SEQ. ID. NO. 9459 | 235-IleValAsnLysGlyAsnAspGluAlaValAla-245 |
| SEQ. ID. NO. 9460 | 252-AsnGluLeuLysAlaAspGlyThrLeuLysLysLeuGly-264 |
| SEQ. ID. NO. 9461 | 267-PhePheGlyLysAspIleSerValGln-275 |
| Hydrophilic Regions - Hopp-Woods | |
| SEQ. ID. NO. 9462 | 20-GlyGlySerGluGlyGlySerGly-27 |
| SEQ. ID. NO. 9463 | 41-LeuIleGluArgIleAsnAsn-47 |
| SEQ. ID. NO. 9464 | 64-TyrHisAspLysAspGlyLysLeuThrGlyTyrAspValGluValThrArgAlaValAlaGluLysLeuGlyVal-88 |
| SEQ. ID. NO. 9465 | 90-ValGluPheLysGluThrGlnTrp-97 |
| SEQ. ID. NO. 9466 | 120-SerProGluArgGlnAlaThrPheAspLysSerAspPro-132 |
| SEQ. ID. NO. 9467 | 143-ArgAsnAspSerAsnIle-148 |
| SEQ. ID. NO. 9468 | 150-SerIleAlaAspIleLysGlyValLysThr-159 |
| SEQ. ID. NO. 9469 | 167-TyrGlyGluLysAlaLysAlaAlaGly-175 |
| SEQ. ID. NO. 9470 | 191-IleGluGlnLysArgAlaAspAlaThrLeuAsnAspGluLeuAla-205 |
| SEQ. ID. NO. 9471 | 209-TyrLeuLysLysAsnProAsnAla-216 |
| SEQ. ID. NO. 9472 | 225-ProAlaAspGluLysValGly-231 |
| SEQ. ID. NO. 9473 | 238-LysGlyAsnAspGluAlaValAla-245 |
| SEQ. ID. NO. 9474 | 252-AsnGluLeuLysAlaAspGlyThrLeuLysLysLeuGly-264 |
| 687 | |
| AMPHI Regions - AMPHI | |
| SEQ. ID. NO. 9475 | 11-AlaAlaLeuPheAlaLeu-16 |
| SEQ. ID. NO. 9476 | 64-LysValGluValLeuGluPhePheGlyTyrPheCysPro-76 |
| SEQ. ID. NO. 9477 | 78-CysAlaHisLeuGluProValLeuSerLysHisAlaLysSerPhe-92 |
| SEQ. ID. NO. 9478 | 112-LeuAlaArgLeuAlaAlaAla-118 |
| SEQ. ID. NO. 9479 | 148-ProGluValLeuLysLysTrpLeu-155 |
| SEQ. ID. NO. 9480 | 176-GlnAlaArgAlaAspLysMetGlnGluLeuThrGluThrPhe-189 |
| Antigenic Index - Jameson-Wolf | |
| SEQ. ID. NO. 9481 | 1-MetLysSerArgHis-5 |
| SEQ. ID. NO. 9482 | 19-CysAspSerLysValGlnThrSerValProAlaAspSerAlaPro-33 |
| SEQ. ID. NO. 9483 | 43-GlyLeuValGluGlyGlnAsnTyr-50 |
| SEQ. ID. NO. 9484 | 56-ProIleProGlnGlnGlnAlaGlyLysValGluVal-67 |
| SEQ. ID. NO. 9485 | 87-LysHisAlaLysSerPheLysAspAspMetTyrLeu-98 |
| SEQ. ID. NO. 9486 | 122-AlaAlaAlaAspSerLysAspValAlaAsn-131 |
| SEQ. ID. NO. 9487 | 141-GlnLysIleLysLeuGlnAsnProGluValLeuLys-152 |
| SEQ. ID. NO. 9488 | 159-ThrAlaPheAspGlyLysLysVal-166 |
| SEQ. ID. NO. 9489 | 171-GluSerProGluSerGlnAlaArgAlaAspLysMetGlnGluLeuThrGlu-187 |
| SEQ. ID. NO. 9490 | 189-PheGlnIleAspGlyThrPro-195 |
| SEQ. ID. NO. 9491 | 199-ValGlyGlyLysTyrLysValGluPheAlaAsp-209 |
| SEQ. ID. NO. 9492 | 211-GluSerGlyMetAsnThr-216 |
| SEQ. ID. NO. 9493 | 220-LeuAlaAspLysValArgGluGluGlnLysAlaAlaGln-232 |
| Hydrophilic Regions - Hopp-Woods | |
| SEQ. ID. NO. 9494 | 1-MetLysSerArgHis-5 |
| SEQ. ID. NO. 9495 | 19-CysAspSerLysValGlnThr-25 |
| SEQ. ID. NO. 9496 | 27-ValProAlaAspSerAlaPro-33 |
| SEQ. ID. NO. 9497 | 61-GlnAlaGlyLysValGluVal-67 |
| SEQ. ID. NO. 9498 | 87-LysHisAlaLysSerPheLysAspAspMetTyrLeu-98 |
| SEQ. ID. NO. 9499 | 122-AlaAlaAlaAspSerLysAspValAla-130 |
| SEQ. ID. NO. 9500 | 141-GlnLysIleLysLeuGlnAsn-147 |
| SEQ. ID. NO. 9501 | 159-ThrAlaPheAspGlyLysLysVal-166 |
| SEQ. ID. NO. 9502 | 171-GluSerProGluSerGlnAlaArgAlaAspLysMetGlnGluLeuThrGlu-187 |
| SEQ. ID. NO. 9503 | 201-GlyLysTyrLysValGluPheAlaAsp-209 |
| SEQ. ID. NO. 9504 | 220-LeuAlaAspLysValArgGluGluGlnLysAlaAlaGln-232 |
| 688 | |
| AMPHI Regions - AMPHI | |
| SEQ. ID. NO. 9505 | 23-LeuSerAlaLeuLeuGlyLeu-29 |
| SEQ. ID. NO. 9506 | 121-AspValLeuGlnAsnAlaAlaGluAlaLeuLysAsp-132 |
| Antigenic Index - Jameson-Wolf | |
| SEQ. ID. NO. 9507 | 4-TyrProSerArgPheAlaGln-10 |
| SEQ. ID. NO. 9508 | 13-IleSerValAsnLys-17 |
| SEQ. ID. NO. 9509 | 33-SerAlaGluArgValSer-38 |
| SEQ. ID. NO. 9510 | 47-IleIleGlnGlyAsnGluLeuGluProArgAla-57 |
| SEQ. ID. NO. 9511 | 62-ArgProGlyMetThrLysAspGln-69 |
| SEQ. ID. NO. 9512 | 82-AlaPheHisThrAspArgTrpAspTyr-90 |
| SEQ. ID. NO. 9513 | 92-PheAsnThrSerArgAsnGlyIleIleLysGluArgSerAsnLeu-106 |
| SEQ. ID. NO. 9514 | 116-ValArgThrGluGlyAspVal-122 |
| SEQ. ID. NO. 9515 | 126-AlaAlaGluAlaLeuLysAspArgGlnAsnThrAspLysPro-139 |

TABLE 1-continued

Hydrophilic Regions - Hopp-Woods
SEQ. ID. NO. 9516    33-SerAlaGluArgValSer-38
SEQ. ID. NO. 9517    51-AsnGluLeuGluProArgAla-57
SEQ. ID. NO. 9518    64-GlyMetThrLysAspGln-69
SEQ. ID. NO. 9519    98-GlyIleIleLysGluArgSerAsn-105
SEQ. ID. NO. 9520    116-ValArgThrGluGlyAspVal-122
SEQ. ID. NO. 9521    126-AlaAlaGluAlaLeuLysAspArgGlnAsnThrAspLysPro-139
689
AMPHI Regions - AMPHI
SEQ. ID. NO. 9522    55-TyrProGluMetSerGluLysLeuMet-63
SEQ. ID. NO. 9523    65-ValLeuMetAlaMetLeuValThrLeu-73
SEQ. ID. NO. 9524    82-LeuProAlaIleProGluMetAlaGln-90
SEQ. ID. NO. 9525    111-AlaPheGlyGlnValValGlyGly-118
SEQ. ID. NO. 9526    123-IleLysGlyArgLys-127
SEQ. ID. NO. 9527    154-LeuAsnLeuArgValValGlnAlaPheGlyAlaGly-165
SEQ. ID. NO. 9528    188-PheAlaLeuIleGlyIleIleLeu-195
SEQ. ID. NO. 9529    203-ProMetValGlyAlaLeuLeuGlnGlyLeuGlyGlyTrpGlnAlaIlePheVal-220
SEQ. ID. NO. 9530    230-LeuGlyLeuValGlnTyrPhe-236
SEQ. ID. NO. 9531    245-LysIleGlyArgAspVal-250
SEQ. ID. NO. 9532    257-ArgPheLysArgValLeu-262
SEQ. ID. NO. 9533    277-SerPheGlySerMetPheAla-283
SEQ. ID. NO. 9534    293-GlnGlnLeuTyrArgVal-298
SEQ. ID. NO. 9535    344-AlaAlaAsnLeuSerGlnLeuAlaAlaValLeuPhe-355
SEQ. ID. NO. 9536    400-ValLeuGlyValPheGlnSerLeuIleGly-409
Antigenic Index - Jameson-Wolf
SEQ. ID. NO. 9537    36-PheArgArgArgAlaVal-41
SEQ. ID. NO. 9538    45-IleGlyArgGluPheMetProSer-52
SEQ. ID. NO. 9539    57-GluMetSerGluLysLeu-62
SEQ. ID. NO. 9540    95-AspValHisArgIleGluGln-101
SEQ. ID. NO. 9541    119-SerValSerAspIleLysGlyArgLysProVal-129
SEQ. ID. NO. 9542    174-MetValArgAspTyrTyrSerGlyArgLysAlaAla-185
SEQ. ID. NO. 9543    238-ProLysProAlaValGlyGlyLysIleGlyArgAspValPhe-251
SEQ. ID. NO. 9544    257-ArgPheLysArgValLeuLysThrArgAla-266
SEQ. ID. NO. 9545    325-LeuLysThrGlyValHis-330
SEQ. ID. NO. 9546    390-PheLysGluGluGlyGlySer-396
SEQ. ID. NO. 9547    448-ArgAlaTrpLysGluAsnGlyGlnSerGluTyrLeu-459
Hydrophilic Regions - Hopp-Woods
SEQ. ID. NO. 9548    36-PheArgArgArgAlaVal-41
SEQ. ID. NO. 9549    45-IleGlyArgGluPheMet-50
SEQ. ID. NO. 9550    57-GluMetSerGluLysLeu-62
SEQ. ID. NO. 9551    95-AspValHisArgIleGluGln-101
SEQ. ID. NO. 9552    119-SerValSerAspIleLysGlyArgLysProVal-129
SEQ. ID. NO. 9553    178-TyrTyrSerGlyArgLysAlaAla-185
SEQ. ID. NO. 9554    245-LysIleGlyArgAspVal-250
SEQ. ID. NO. 9555    257-ArgPheLysArgValLeuLysThrArgAla-266
SEQ. ID. NO. 9556    390-PheLysGluGluGlyGlySer-396
SEQ. ID. NO. 9557    448-ArgAlaTrpLysGluAsnGlyGln-455
690
AMPHI Regions - AMPHI
SEQ. ID. NO. 9558    38-SerSerAlaSerSerAla-43
SEQ. ID. NO. 9559    54-SerAlaProAspAsnValLysGlnAla-62
SEQ. ID. NO. 9560    68-SerAsnCysThrSerLeuHisProAlaThrGlyIleAspAspLeuMetGlnGlnIleAlaGluHisIle-90
SEQ. ID. NO. 9561    113-GlyTyrAspAsnIleGlnArgLeu-120
SEQ. ID. NO. 9562    148-ArgThrIleSerArgGlnAlaGlnAsnAla-157
SEQ. ID. NO. 9563    186-ProLysArgThrArgTyrPhe-192
SEQ. ID. NO. 9564    210-GlyAsnPheGlnTyrIleSerGlnLeuProGlyTyrLeuLys-223
Antigenic Index - Jameson-Wolf
SEQ. ID. NO. 9565    1-MetLysAsnLysThrSer-6
SEQ. ID. NO. 9566    20-CysSerProSerLysAspAspLysThrLysGluValGlyAla-33
SEQ. ID. NO. 9567    37-SerSerSerAlaSerSerAlaProSerGlnThrAspLeuGlnProThrAlaSerAlaProAspAsnValLysGlnAlaGluSerAlaProProSerAsnCys-70
SEQ. ID. NO. 9568    76-AlaThrGlyIleAspAspLeuMet-83
SEQ. ID. NO. 9569    88-GluHisIleAspSerAspCys-94
SEQ. ID. NO. 9570    101-HisGluLeuGluThrArgPheGlyLeuProAspGlyGlyTyrAspAsnIleGln-118
SEQ. ID. NO. 9571    123-ProAspIleArgProGluAspProAspTyrHisGln-134
SEQ. ID. NO. 9572    141-GluAspLeuArgTyrGlyLysArgThrIleSerArgGlnAlaGln-155
SEQ. ID. NO. 9573    159-MetGluGlnGluArgArgLeuArgGlu-167
SEQ. ID. NO. 9574    175-GlySerGlnGluThrArgGlyGlnGlyGluGluProLysArgThrArgTyr-191
SEQ. ID. NO. 9575    196-AlaThrProAlaTyrSerSerArgHisAsnAsnGlyLeuGlyGly-210
SEQ. ID. NO. 9576    225-HisGlyGluMetLeuGluAsnGlnSerLeu-234
SEQ. ID. NO. 9577    236-ArgLeuSerAsnArgGluArgAsnProAspLysProPheLeu-249
SEQ. ID. NO. 9578    252-HisPheAspGluAsnGlyLysIleThr-260
SEQ. ID. NO. 9579    264-ValTyrGluLysAsnIle-269
SEQ. ID. NO. 9580    272-AsnProAsnThrGlyArgIle-278
Hydrophilic Regions - Hopp-Woods
SEQ. ID. NO. 9581    1-MetLysAsnLysThr-5
SEQ. ID. NO. 9582    21-SerProSerLysAspAspLysThrLysGluValGlyAla-33
SEQ. ID. NO. 9583    39-SerAlaSerSerAlaProSerGlnThrAspLeuGlnPro-51
SEQ. ID. NO. 9584    54-SerAlaProAspAsnValLysGlnAlaGluSerAlaPro-66
SEQ. ID. NO. 9585    78-GlyIleAspAspLeuMet-83

TABLE 1-continued

| | |
|---|---|
| SEQ. ID. NO. 9586 | 88-GluHisIleAspSer-92 |
| SEQ. ID. NO. 9587 | 101-HisGluLeuGluThr-105 |
| SEQ. ID. NO. 9588 | 125-IleArgProGluAspProAspTyrHis-133 |
| SEQ. ID. NO. 9589 | 141-GluAspLeuArgTyrGlyLysArgThrIleSerArgGlnAlaGln-155 |
| SEQ. ID. NO. 9590 | 159-MetGluGlnGluArgArgLeuArgGlu-167 |
| SEQ. ID. NO. 9591 | 175-GlySerGlnGluThrArgGlyGlnGlyGluGluProLysArgThrArgTyr-191 |
| SEQ. ID. NO. 9592 | 200-TyrSerSerArgHisAsnAsn-206 |
| SEQ. ID. NO. 9593 | 225-HisGlyGluMetLeuGlu-230 |
| SEQ. ID. NO. 9594 | 237-LeuSerAsnArgGluArgAsnProAspLysProPhe-248 |
| SEQ. ID. NO. 9595 | 252-HisPheAspGluAsnGlyLysIleThr-260 |
| SEQ. ID. NO. 9596 | 274-AsnThrGlyArgIle-278 |
| 691 | |
| AMPHI Regions - AMPHI | |
| SEQ. ID. NO. 9597 | 11-LysProAlaAlaSer-15 |
| SEQ. ID. NO. 9598 | 55-HisAsnGluLeuArgLysIleArgThrAla-64 |
| SEQ. ID. NO. 9599 | 108-ArgTyrLeuSerGly-112 |
| Antigenic Index - Jameson-Wolf | |
| SEQ. ID. NO. 9600 | 7-CysArgPheAlaLys-11 |
| SEQ. ID. NO. 9601 | 35-ProProAsnAspPheGlnProAsnCysAspIleArgArgLeuGlyLeuThrGlnSerGlnHisAsnGluLeuArgLysIleArgThr-63 |
| SEQ. ID. NO. 9602 | 67-MetAlaGlyAspArgAlaArgLeuLysValMetHis-78 |
| SEQ. ID. NO. 9603 | 80-GluHisSerArgArgArgSerVal-87 |
| SEQ. ID. NO. 9604 | 91-IleSerSerAspValPheAsnArgAsnGluAlaArgAspTyrValGluSerArgTyrLeuSerGlyMetAspPheAlaValAspGluLeuGluIle-122 |
| SEQ. ID. NO. 9605 | 131-ThrProGlnGlnGlnGln-136 |
| SEQ. ID. NO. 9606 | 140-SerSerCysLeuLys-144 |
| Hydrophilic Regions - Hopp-Woods | |
| SEQ. ID. NO. 9607 | 43-CysAspIleArgArgLeuGly-49 |
| SEQ. ID. NO. 9608 | 54-GlnHisAsnGluLeuArgLysIleArgThr-63 |
| SEQ. ID. NO. 9609 | 67-MetAlaGlyAspArgAlaArgLeuLysValMetHis-78 |
| SEQ. ID. NO. 9610 | 80-GluHisSerArgArgArgSerVal-87 |
| SEQ. ID. NO. 9611 | 95-ValPheAsnArgAsnGluAlaArgAspTyrValGlu-106 |
| SEQ. ID. NO. 9612 | 115-PheAlaValAspGluLeuGluIle-122 |
| 692 | |
| AMPHI Regions - AMPHI | |
| SEQ. ID. NO. 9613 | 6-CysArgCysSerGluSerIleArgArgIleArgArgAsn-18 |
| SEQ. ID. NO. 9614 | 77-LeuGlyTyrValPheLysProLeuAlaValPheVal-88 |
| SEQ. ID. NO. 9615 | 106-GlnGlyPheGlyGlnLeuHis-112 |
| SEQ. ID. NO. 9616 | 132-ThrArgGlnLeuArgGlyPheLys-139 |
| SEQ. ID. NO. 9617 | 143-PheAspValPheGlnValLeuGly-150 |
| SEQ. ID. NO. 9618 | 170-GlnPheValGluHisHis-175 |
| SEQ. ID. NO. 9619 | 177-AspAlaGlyGluValGlyArgValValGlyArgGlyTyrGlyAlaAlaValPheAspPhePheGlnArgPheGlnLeu-202 |
| SEQ. ID. NO. 9620 | 205-ValGlnSerGlnArgArgGlyArgHisLeuGluAspPheGlyAsp-219 |
| SEQ. ID. NO. 9621 | 253-IleValGlyLysLeuAspGlnPheAspGlyVal-263 |
| SEQ. ID. NO. 9622 | 275-PheAspHisIleAlaGluValAlaAsp-283 |
| Antigenic Index - Jameson-Wolf | |
| SEQ. ID. NO. 9623 | 6-CysArgCysSerGluSerIleArgArgIleArgArgAsnGlyArgGluTrpArgIleLysGlyGlnLysCysArgLeuAsnThrAspThrValGln-37 |
| SEQ. ID. NO. 9624 | 89-GlyGlyPheAspGlyArgProValAspIleGlyLysAlaArgPheLeu-104 |
| SEQ. ID. NO. 9625 | 120-AlaValAspAspGlyLysIle-126 |
| SEQ. ID. NO. 9626 | 131-AlaThrArgGlnLeuArgGlyPheLysLeuAspAspPheAsp-144 |
| SEQ. ID. NO. 9627 | 150-GlyAspValArgPheGlyCysGlyGlnArgIleAspAla-162 |
| SEQ. ID. NO. 9628 | 174-HisHisGlnAspAlaGlyGluValGlyArgValValGlyArgGlyTyr-189 |
| SEQ. ID. NO. 9629 | 204-ArgValGlnSerGlnArgArgGlyArgHisLeuGluAspPheGlyAsp-219 |
| SEQ. ID. NO. 9630 | 236-GluAspValAspVal-240 |
| SEQ. ID. NO. 9631 | 255-GlyLysLeuAspGlnPheAspGly-262 |
| SEQ. ID. NO. 9632 | 279-AlaGluValAlaAspGlyArgAlaGluAspAspPhePhePhe-292 |
| SEQ. ID. NO. 9633 | 295-AlaValValGlyGlyGlyArgSerGlyCysGlyGlyArg-307 |
| SEQ. ID. NO. 9634 | 313-AlaAlaGlyGlyGluAspGluArgGluCysGlyGlyGlyLysGlyPheGluGlu-330 |
| Hydrophilic Regions - Hopp-Woods | |
| SEQ. ID. NO. 9635 | 7-ArgCysSerGluSerIleArgArgIleArgArgAsnGlyArgGluTrpArgIleLysGlyGlnLysCysArgLeuAsnThr-33 |
| SEQ. ID. NO. 9636 | 91-PheAspGlyArgProValAspIleGlyLys-100 |
| SEQ. ID. NO. 9637 | 120-AlaValAspAspGlyLysIle-126 |
| SEQ. ID. NO. 9638 | 131-AlaThrArgGlnLeuArgGlyPheLysLeuAspAspPheAsp-144 |
| SEQ. ID. NO. 9639 | 174-HisHisGlnAspAlaGlyGluValGlyArgValValGly-186 |
| SEQ. ID. NO. 9640 | 206-GlnSerGlnArgArgGlyArgHisLeuGluAspPheGlyAsp-219 |
| SEQ. ID. NO. 9641 | 236-GluAspValAspVal-240 |
| SEQ. ID. NO. 9642 | 256-LysLeuAspGlnPheAsp-261 |
| SEQ. ID. NO. 9643 | 279-AlaGluValAlaAspGlyArgAlaGluAspAspPhePhePhe-292 |
| SEQ. ID. NO. 9644 | 299-GlyGlyArgSerGlyCysGlyGly-306 |
| SEQ. ID. NO. 9645 | 315-GlyGlyGluAspGluArgGluCysGlyGly-324 |
| SEQ. ID. NO. 9646 | 326-LysGlyPheGluGlu-330 |
| 694 | |
| AMPHI Regions - AMPHI | |
| SEQ. ID. NO. 9647 | 82-ArgGlyArgAlaCysArg-87 |
| SEQ. ID. NO. 9648 | 116-CysArgHisPheAlaGln-121 |
| SEQ. ID. NO. 9649 | 123-ValAlaValGlyArgIleGly-129 |
| SEQ. ID. NO. 9650 | 140-PheCysGlnLeuPheAsp-145 |
| SEQ. ID. NO. 9651 | 156-AspIlePheLeuVal-160 |
| SEQ. ID. NO. 9652 | 162-IleAlaAspIleGlyGlu-167 |
| SEQ. ID. NO. 9653 | 184-ArgGlyLeuAlaAspIleGlyGluPheValGlyValSerAsp-197 |
| SEQ. ID. NO. 9654 | 251-HisGlnArgAlaSerArgIleLys-258 |
| SEQ. ID. NO. 9655 | 283-ArgAlaArgArgHisPheArgGlnValPheAsn-293 |

TABLE 1-continued

| | |
|---|---|
| SEQ. ID. NO. 9656 | 311-AspPheValAlaHisIle-316 |
| SEQ. ID. NO. 9657 | 340-AlaAlaArgIleGly-344 |
| Antigenic Index - Jameson-Wolf | |
| SEQ. ID. NO. 9658 | 3-SerAlaSerGlyThrArgGlnLysCysArgLeuLysProVal-16 |
| SEQ. ID. NO. 9659 | 23-ProLysHisSerThrProAlaSer-30 |
| SEQ. ID. NO. 9660 | 47-GlyGlnAspGluHisAsnAla-53 |
| SEQ. ID. NO. 9661 | 66-ProProSerAlaTyrGly-71 |
| SEQ. ID. NO. 9662 | 79-HisPheGlyArgGlyArgAlaCysArgTyr-88 |
| SEQ. ID. NO. 9663 | 110-ArgIleAspSerAlaArgCysArgHis-118 |
| SEQ. ID. NO. 9664 | 127-ArgIleGlyArgThrAspHisAsnHisAsp-136 |
| SEQ. ID. NO. 9665 | 144-PheAspGlyGlyLeuProValGlyArgArgIleAla-155 |
| SEQ. ID. NO. 9666 | 163-AlaAspIleGlyGluThrArgValGlnArgGlyAspAspValPhe-177 |
| SEQ. ID. NO. 9667 | 180-IleAspArgGluArgGlyLeuAlaAsp-188 |
| SEQ. ID. NO. 9668 | 202-HisIleSerAspArgPheAspGlnLysHisPheAlaArgArgLysLeuProHisArgSerPheAspLeu-224 |
| SEQ. ID. NO. 9669 | 228-LeuMetProAspHisAspAspPheThr-236 |
| SEQ. ID. NO. 9670 | 250-ArgHisGlnArgAlaSerArgIleLysHisAlaGluThrAlaLeu-264 |
| SEQ. ID. NO. 9671 | 268-LeuProHisArgLeuArgTyrAla-275 |
| SEQ. ID. NO. 9672 | 280-AsnGlnCysArgAlaArgArgHisPhe-288 |
| SEQ. ID. NO. 9673 | 291-ValPheAsnLysHisArgThr-297 |
| SEQ. ID. NO. 9674 | 316-IleAsnArgArgAlaGluLeu-322 |
| SEQ. ID. NO. 9675 | 326-ThrPheAspAsnThrAspCysPro-333 |
| SEQ. ID. NO. 9676 | 336-ThrSerAlaGluAlaAlaArgIleGlyLysAspAspGlyPhe-349 |
| SEQ. ID. NO. 9677 | 370-TyrGlyGlyArgCysCysProThrProProThrProHisArgArgArg-385 |
| Hydrophilic Regions - Hopp-Woods | |
| SEQ. ID. NO. 9678 | 5-SerGlyThrArgGlnLysCysArgLeuLysPro-15 |
| SEQ. ID. NO. 9679 | 47-GlyGlnAspGluHisAsnAla-53 |
| SEQ. ID. NO. 9680 | 81-GlyArgGlyArgAlaCysArg-87 |
| SEQ. ID. NO. 9681 | 110-ArgIleAspSerAlaArgCysArgHis-118 |
| SEQ. ID. NO. 9682 | 127-ArgIleGlyArgThrAspHisAsnHis-135 |
| SEQ. ID. NO. 9683 | 150-ValGlyArgArgIleAla-155 |
| SEQ. ID. NO. 9684 | 163-AlaAspIleGlyGluThrArgValGlnArgGlyAspAsp-175 |
| SEQ. ID. NO. 9685 | 180-IleAspArgGluArgGlyLeuAlaAsp-188 |
| SEQ. ID. NO. 9686 | 202-HisIleSerAspArgPheAspGlnLysHisPheAlaArgArgLysLeuProHisArgSerPheAspLeu-224 |
| SEQ. ID. NO. 9687 | 230-ProAspHisAspAsp-234 |
| SEQ. ID. NO. 9688 | 250-ArgHisGlnArgAlaSerArgIleLysHisAlaGluThrAlaLeu-264 |
| SEQ. ID. NO. 9689 | 280-AsnGlnCysArgAlaArgArgHisPhe-288 |
| SEQ. ID. NO. 9690 | 292-PheAsnLysHisArg-296 |
| SEQ. ID. NO. 9691 | 316-IleAsnArgArgAlaGluLeu-322 |
| SEQ. ID. NO. 9692 | 327-PheAspAsnThrAsp-331 |
| SEQ. ID. NO. 9693 | 338-AlaGluAlaAlaArgIleGlyLysAspAspGly-348 |
| SEQ. ID. NO. 9694 | 380-ThrProHisArgArgArg-385 |
| 695 | |
| AMPHI Regions - AMPHI | |
| SEQ. ID. NO. 9695 | 36-HisProGlnArgPheGlnSerLysProAlaGluArgProAlaHisArgPro-52 |
| SEQ. ID. NO. 9696 | 129-ValArgLeuSerAsnGluValGlu-136 |
| SEQ. ID. NO. 9697 | 144-AlaLeuGluHisAlaLysThrHisSer-152 |
| SEQ. ID. NO. 9698 | 156-AlaTyrValGlnLysLeuAsp-162 |
| SEQ. ID. NO. 9699 | 183-ValGluThrAlaGlnAsnLeuTyrAsnGlnAlaLeuLysHisTyrLysSerGly-200 |
| SEQ. ID. NO. 9700 | 205-AlaAlaSerLeuLeuLysGlyAla-212 |
| SEQ. ID. NO. 9701 | 238-CysGluSerValIleGluIle-244 |
| SEQ. ID. NO. 9702 | 248-TyrAlaAsnArgPheLysAspSer-255 |
| SEQ. ID. NO. 9703 | 278-AlaArgAlaThrTrpArgSerLeuIleGlnThrTyrProGly-291 |
| Antigenic Index - Jameson-Wolf | |
| SEQ. ID. NO. 9704 | 1-LeuProGlnThrArgProSerArgArgHisHisArgHisArgGlnTyrPheAlaGluArgLysGlyAspAlaArgSerGlyPhe-28 |
| SEQ. ID. NO. 9705 | 31-AlaAlaGlnArgArgHisProGlnArgPheGlnSerLysProAlaGluArgProAlaHisArgProHisHisProAlaArgArgArgArgLeuAsp ProAlaSerGluLysIleMetLys-70 |
| SEQ. ID. NO. 9706 | 83-SerAlaSerCysAlaSer-88 |
| SEQ. ID. NO. 9707 | 93-ProAlaGlySerGlnThrGluMetSerThrArgGluAsnAlaSerAspGlyIleProTyr-112 |
| SEQ. ID. NO. 9708 | 117-LeuGlnAspArgLeuAspTyrLeuGlu-125 |
| SEQ. ID. NO. 9709 | 127-LysIleValArgLeuSerAsnGluValGluThrLeuAsnGlyLysValLysAlaLeuGluHisAlaLysThrHisSerSerGlyArgAlaTyrVal GlnLysLeuAspAspArgLysLeuLysGlu-168 |
| SEQ. ID. NO. 9710 | 170-TyrLeuAsnThrGluGlyGlySerAla-178 |
| SEQ. ID. NO. 9711 | 193-AlaLeuLysHisTyrLysSerGlyLysPhe-202 |
| SEQ. ID. NO. 9712 | 209-LeuLysGlyAlaAspGlyGlyAspGlyGlySerIleAlaGln-222 |
| SEQ. ID. NO. 9713 | 230-GlnSerArgAlaArgMetGlyAsnCys-238 |
| SEQ. ID. NO. 9714 | 244-IleGlyGlyArgTyrAlaAsnArgPheLysAspSerProThrAlaPro-259 |
| SEQ. ID. NO. 9715 | 266-GlyGluCysGlnTyr-270 |
| SEQ. ID. NO. 9716 | 272-LeuGlnGlnLysAspIleAla-278 |
| SEQ. ID. NO. 9717 | 289-TyrProGlySerProAlaAlaLysArgAlaAlaAlaAlaValArgLysArg-305 |
| Hydrophilic Regions - Hopp-Woods | |
| SEQ. ID. NO. 9718 | 2-ProGlnThrArgProSerArgArgHisHisArgHisArgGlnTyrPheAlaGluArgLysGlyAspAlaArgSerGlyPhe-28 |
| SEQ. ID. NO. 9719 | 31-AlaAlaGlnArgArgHisProGlnArgPheGlnSerLysProAlaGluArgProAlaHisArgProHisHisProAlaArgArgArgArgLeuAsp ProAlaSerGluLysIleMetLys-70 |
| SEQ. ID. NO. 9720 | 96-SerGlnThrGluMetSerThrArgGluAsnAlaSerAsp-108 |
| SEQ. ID. NO. 9721 | 117-LeuGlnAspArgLeuAspTyrLeuGlu-125 |
| SEQ. ID. NO. 9722 | 127-LysIleValArgLeuSerAsnGluValGluThrLeuAsnGlyLysValLysAlaLeuGluHisAlaLysThrHisSerSerGly-154 |
| SEQ. ID. NO. 9723 | 157-TyrValGlnLysLeuAspAspArgLysLeuLysGlu-168 |
| SEQ. ID. NO. 9724 | 195-LysHisTyrLysSerGlyLysPhe-202 |
| SEQ. ID. NO. 9725 | 210-LysGlyAlaAspGlyGlyAspGlyGlySerIleAlaGln-222 |
| SEQ. ID. NO. 9726 | 231-SerArgAlaArgMetGlyAsn-237 |

TABLE 1-continued

| | |
|---|---|
| SEQ. ID. NO. 9727 | 248-TyrAlaAsnArgPheLysAspSerProThrAlaPro-259 |
| SEQ. ID. NO. 9728 | 266-GlyGluCysGlnTyr-270 |
| SEQ. ID. NO. 9729 | 272-LeuGlnGlnLysAspIleAla-278 |
| SEQ. ID. NO. 9730 | 293-ProAlaAlaLysArgAlaAlaAlaAlaValArgLysArg-305 |
| 696 | |
| AMPHI Regions - AMPHI | |
| SEQ. ID. NO. 9731 | 18-PheGlyGlyIlePheHisPheValCysArgPheLeuSerArgValGlySerPheValGlnSerIlePheSerCysPheSer-44 |
| SEQ. ID. NO. 9732 | 65-IlePheAspLeuValPhe-70 |
| SEQ. ID. NO. 9733 | 94-GlyLeuAsnArgPheLeuAsnLeuLeuPheGlyPheLeuArg-107 |
| Antigenic Index - Jameson-Wolf | |
| SEQ. ID. NO. 9734 | 12-CysGlnGlyAsnLysLeu-17 |
| SEQ. ID. NO. 9735 | 73-PheAspGlyArgSerGlyArgLeuGlyGlyArgSerArgSer-86 |
| SEQ. ID. NO. 9736 | 108-ThrSerCysGlnGlySerArgHisHisCysGlyAsnGln-120 |
| Hydrophilic Regions - Hopp-Woods | |
| SEQ. ID. NO. 9737 | 73-PheAspGlyArgSerGlyArgLeuGlyGlyArgSerArgSer-86 |
| SEQ. ID. NO. 9738 | 109-SerCysGlnGlySerArgHisHisCys-117 |
| 700 | |
| AMPHI Regions - AMPHI | |
| SEQ. ID. NO. 9739 | 6-ThrLeuLeuSerValLeuIleProMetPheAlaGlyPhePheIleArgValProLys-24 |
| SEQ. ID. NO. 9740 | 27-LeuProAlaLeuAspLysValLeuSerValLeu-37 |
| SEQ. ID. NO. 9741 | 51-ArgValGluAspLeuGlySerArg-58 |
| SEQ. ID. NO. 9742 | 80-AlaLeuAlaValLeuGlyLysLeu-87 |
| SEQ. ID. NO. 9743 | 119-PheGlyLysLeuMetArgAsp-125 |
| SEQ. ID. NO. 9744 | 191-SerTrpThrLysGlyLeu-196 |
| SEQ. ID. NO. 9745 | 204-TrpTyrSerLeuSerGlyLeuVal-211 |
| SEQ. ID. NO. 9746 | 216-TyrGlyAlaValTrp-220 |
| SEQ. ID. NO. 9747 | 228-AspLeuAlaArgGluLeu-233 |
| SEQ. ID. NO. 9748 | 268-GlyAlaGlyGlyLeu-272 |
| Antigenic Index - Jameson-Wolf | |
| SEQ. ID. NO. 9749 | 21-ArgValProLysProTyrLeu-27 |
| SEQ. ID. NO. 9750 | 50-SerArgValGluAspLeuGlySerArgLeuAspAspMetAla-63 |
| SEQ. ID. NO. 9751 | 90-TrpArgIleLysGlyLysGlyLysGlyVal-99 |
| SEQ. ID. NO. 9752 | 128MetProSerGluSerAlaGlyMetTyr-136 |
| SEQ. ID. NO. 9753 | 149-LeuLysSerSerGlyValSerLeu-156 |
| SEQ. ID. NO. 9754 | 160-LeuValAsnArgArgGlyIleArgLeu-168 |
| SEQ. ID. NO. 9755 | 185-AlaSerThrAspGlyValSer-191 |
| SEQ. ID. NO. 9756 | 245-ArgPheProAspAla-249 |
| SEQ. ID. NO. 9757 | 268-GlyAlaGlyGlyLeu-272 |
| Hydrophilic Regions - Hopp-Woods | |
| SEQ. ID. NO. 9758 | 50-SerArgValGluAspLeuGlySerArgLeuAspAspMetAla-63 |
| SEQ. ID. NO. 9759 | 92-IleLysGlyLysGlyLysGlyVal-99 |
| SEQ. ID. NO. 9760 | 149-LeuLysSerSerGlyValSer-155 |
| SEQ. ID. NO. 9761 | 160-LeuValAsnArgArgGlyIleArg-167 |
| 701 | |
| AMPHI Regions - AMPHI | |
| SEQ. ID. NO. 9762 | 6-PheHisValAlaGly-10 |
| SEQ. ID. NO. 9763 | 30-CysLeuAspThrSer-34 |
| SEQ. ID. NO. 9764 | 45-ProAsnSerPheAlaSerPheLysArgPheSerSerIle-57 |
| SEQ. ID. NO. 9765 | 79-GlyProAlaProAlaMet-84 |
| Antigenic Index - Jameson-Wolf | |
| SEQ. ID. NO. 9766 | 17-AlaGlnSerThrProSerSerProThrMet-26 |
| SEQ. ID. NO. 9767 | 29-ThrCysLeuAspThrSerProGluAlaGly-38 |
| SEQ. ID. NO. 9768 | 52-LysArgPheSerSerIleSer-58 |
| SEQ. ID. NO. 9769 | 72-AsnArgAlaAspIleProThrGlyProAla-81 |
| SEQ. ID. NO. 9770 | 104-GlyLysAlaSerLeuAsnAsnArgAla-112 |
| SEQ. ID. NO. 9771 | 119-SerGlySerGlyThrArgLeu-125 |
| Hydrophilic Regions - Hopp-Woods | |
| SEQ. ID. NO. 9772 | 72-AsnArgAlaAspIleProThr-78 |
| 702 | |
| AMPHI Regions - AMPHI | |
| SEQ. ID. NO. 9773 | 51-CysSerGlyLeuValThrVal-57 |
| SEQ. ID. NO. 9774 | 118-LysIleSerArgGly-122 |
| Antigenic Index - Jameson-Wolf | |
| SEQ. ID. NO. 9775 | 1-MetProCysSerLysAlaSer-7 |
| SEQ. ID. NO. 9776 | 28-LeuAlaArgAspSerCysSerProGlyLeu-37 |
| SEQ. ID. NO. 9777 | 41-ThrAlaProAlaSerSer-46 |
| SEQ. ID. NO. 9778 | 68-LeuAlaIleArgArgMetAlaSerArgProThrGlyValArgArgValIleSer-85 |
| SEQ. ID. NO. 9779 | 88-GlyMetProProSerThrArgAlaTrpAspLysSerMetAla-101 |
| SEQ. ID. NO. 9780 | 118-LysIleSerArgGlyValSer-124 |
| SEQ. ID. NO. 9781 | 139-ArgTrpAspArgLeu-143 |
| Hydrophilic Regions - Hopp-Woods | |
| SEQ. ID. NO. 9782 | 29-AlaArgAspSerCysSer-34 |
| SEQ. ID. NO. 9783 | 69-AlaIleArgArgMetAlaSerArgProThrGlyValArgArgValIleSer-85 |
| SEQ. ID. NO. 9784 | 94-ArgAlaTrpAspLys-98 |
| SEQ. ID. NO. 9785 | 139-ArgTrpAspArgLeu-143 |
| 703 | |
| AMPHI Regions - AMPHI | |
| SEQ. ID. NO. 9786 | 21-GlnThrLeuAlaThrValAsnGly-28 |
| SEQ. ID. NO. 9787 | 64-GluValValAsnThrValValAlaGlnGlu-73 |
| SEQ. ID. NO. 9788 | 79-LeuAspArgSerAlaGlu-84 |

TABLE 1-continued

| | |
|---|---|
| SEQ. ID. NO. 9789 | 140-AlaAlaTyrAspAsnIleSerGlyPheTyrLysGly-151 |
| SEQ. ID. NO. 9790 | 181-PheAspAlaValLeu-185 |
| SEQ. ID. NO. 9791 | 204-ValProLeuLysAspLeuGluGlnGlyValProProLeuTyrGlnAlaIleLysAspLeuLysLys-225 |
| SEQ. ID. NO. 9792 | 252-ValProSerPheAsp-256 |
| SEQ. ID. NO. 9793 | 270-ArgIleAspArgAlaValGlyAlaLeu-278 |
| Antigenic Index - Jameson-Wolf | |
| SEQ. ID. NO. 9794 | 1-MetLysAlaLysIle-5 |
| SEQ. ID. NO. 9795 | 26-ValAsnGlyGlnLysIleAspSerSerVal-35 |
| SEQ. ID. NO. 9796 | 43-PheArgAlaGluAsnSerArgAlaGluAspThrProGlnLeuArg-57 |
| SEQ. ID. NO. 9797 | 72-GlnGluValLysArgLeuLysLeuAspArgSerAlaGluPheLysAsnAlaLeuAlaLysLeuArgAlaGluAlaLysLysSerGlyAspAspLysLys ProSerPheLysThr-109 |
| SEQ. ID. NO. 9798 | 129-LysThrGlnProValSerGluGlnGluValLysAlaAlaTyr-142 |
| SEQ. ID. NO. 9799 | 144-AsnIleSerGlyPheTyrLysGlyThrGlnGluValGlnLeu-157 |
| SEQ. ID. NO. 9800 | 160-IleLeuThrAspLysGluGluAsnAlaLysLysAlaValAlaAspLeuLysAlaLysLysGlyPhe-181 |
| SEQ. ID. NO. 9801 | 188-TyrSerLeuAsnAspArgThrLysGlnThrGlyAlaProValGly-202 |
| SEQ. ID. NO. 9802 | 207-LysAspLeuGluGlnGlyValProPro-215 |
| SEQ. ID. NO. 9803 | 221-LysAspLeuLysLysGlyGluPheThrAlaThrProLeuLysAsnGlyAspPhe-238 |
| SEQ. ID. NO. 9804 | 243-TyrValAsnAspSerArgGluValLysValProSerPheAspGluMetLysGly-260 |
| SEQ. ID. NO. 9805 | 266-LeuGlnAlaGluArgIleAspArgAlaVal-275 |
| SEQ. ID. NO. 9806 | 282-AlaAsnIleLysProAlaLys-288 |
| Hydrophilic Regions - Hopp-Woods | |
| SEQ. ID. NO. 9807 | 1-MetLysAlaLysIle-5 |
| SEQ. ID. NO. 9808 | 29-GlnLysIleAspSerSerVal-35 |
| SEQ. ID. NO. 9809 | 43-PheArgAlaGluAsnSerArgAlaGluAspThrProGlnLeuArg-57 |
| SEQ. ID. NO. 9810 | 72-GlnGluValLysArgLeuLysLeuAspArgSerAlaGluPheLysAsnAlaLeuAlaLysLeuArgAlaGluAlaLysLysSerGlyAspAspLys LysProSerPhe-107 |
| SEQ. ID. NO. 9811 | 131-GlnProValSerGluGlnGluValLysAlaAlaTyr-142 |
| SEQ. ID. NO. 9812 | 160-IleLeuThrAspLysGluGluAsnAlaLysLysAlaValAlaAspLeuLysAlaLysLysGlyPhe-181 |
| SEQ. ID. NO. 9813 | 189-SerLeuAsnAspArgThrLysGlnThrGly-198 |
| SEQ. ID. NO. 9814 | 207-LysAspLeuGluGln-211 |
| SEQ. ID. NO. 9815 | 221-LysAspLeuLysLysGlyGluPhe-228 |
| SEQ. ID. NO. 9816 | 245-AsnAspSerArgGluValLysValProSerPheAspGluMetLysGly-260 |
| SEQ. ID. NO. 9817 | 266-LeuGlnAlaGluArgIleAspArgAlaVal-275 |
| SEQ. ID. NO. 9818 | 282-AlaAsnIleLysProAlaLys-288 |
| 704 | |
| AMPHI Regions - AMPHI | |
| SEQ. ID. NO. 9819 | 33-GlyCysGlnAlaValAlaGlnSerIleIleAspAlaGlyLeuGly-47 |
| SEQ. ID. NO. 9820 | 65-GlnGluIleLeuAspGlnIleArgLeuTyrAspLeuProGluValGlnSerAspPheValGluThrHis-87 |
| SEQ. ID. NO. 9821 | 184-LeuGlyMetMetGln-188 |
| SEQ. ID. NO. 9822 | 208-LeuGlnIleLeuHisTrpGlyGlyPheLeuMetValLeuPro-221 |
| SEQ. ID. NO. 9823 | 232-GlnGlyAlaLeuArgAspLeuLys-239 |
| SEQ. ID. NO. 9824 | 252-AlaIleIleMetThrPheIleAlaGlyValTyrSer-263 |
| SEQ. ID. NO. 9825 | 289-PheMetGluHisIleAlaArg-295 |
| SEQ. ID. NO. 9826 | 298-AlaGlyAspAlaAlaGluArgLeuValLysLeuIleProAlaPheCysHisHisMetProAspTyrProAspThrGlnGluThr-325 |
| SEQ. ID. NO. 9827 | 400-GlyGlyThrArgLeuSerHisIleValArgLeuLeuAspArgAlaLeuAla-416 |
| SEQ. ID. NO. 9828 | 423-GluLeuAlaGluGlnTyr-428 |
| SEQ. ID. NO. 9829 | 499-AlaIleGluThrLeuAlaGln-505 |
| SEQ. ID. NO. 9830 | 527-IleSerLeuLeuArg-531 |
| SEQ. ID. NO. 9831 | 576-LeuAsnArgIleGlyGluGlyValGly-584 |
| SEQ. ID. NO. 9832 | 639-LeuLysAspSerAlaAlaGluAlaValArgGlnLeuAla-651 |
| SEQ. ID. NO. 9833 | 670-GluThrAlaArgAlaLeuGlyVal-677 |
| SEQ. ID. NO. 9834 | 691-GluTyrValLysAlaLeuGlnLysGlu-699 |
| SEQ. ID. NO. 9835 | 744-AspLeuArgThrValAlaHisLeuLeuAsp-753 |
| SEQ. ID. NO. 9836 | 780-AlaValLeuGlyTyrValGlnProTrpIleAlaAla-791 |
| SEQ. ID. NO. 9837 | 799-LeuAlaValLeuGly-803 |
| SEQ. ID. NO. 9838 | 805-AlaLeuArgLeuHisLysArg-811 |
| Antigenic Index - Jameson-Wolf | |
| SEQ. ID. NO. 9839 | 1-MetLysLysThrCys-5 |
| SEQ. ID. NO. 9840 | 8-CysGlyLeuAspValProGlu-14 |
| SEQ. ID. NO. 9841 | 21-ArgTyrGluAsnGluAspArgGluThrCysCys-31 |
| SEQ. ID. NO. 9842 | 46-LeuGlySerTyrTyrLysGlnArgThrAlaAspAlaGlnLysThrGluLeuProProGlnGluIleLeuAsp-69 |
| SEQ. ID. NO. 9843 | 77-ProGluValGlnSerAspPheValGluThrHisGlyGlyThrArgGluAla-93 |
| SEQ. ID. NO. 9844 | 112-GlnLeuLeuArgThrAspGlyIleVal-120 |
| SEQ. ID. NO. 9845 | 124-LeuAsnTyrSerThrHisArgCys-131 |
| SEQ. ID. NO. 9846 | 133-ValValTrpAspAspGlyLysIleArgLeu-142 |
| SEQ. ID. NO. 9847 | 158-ProTyrAspAlaGlnLysIleGluAlaAlaAsnGlnLysGluArgLysGlnTyr-175 |
| SEQ. ID. NO. 9848 | 199-TyrGlyGlyAspIleGluProAspPhe-207 |
| SEQ. ID. NO. 9849 | 234-AlaLeuArgAspLeuLysAsnArgArgValGlyMetAspThrProIle-249 |
| SEQ. ID. NO. 9850 | 293-IleAlaArgArgLysAlaGlyAspAlaAlaGluArgLeuVal-306 |
| SEQ. ID. NO. 9851 | 316-MetProAspTyrProAspThrGlnGluThrCysGlu-327 |
| SEQ. ID. NO. 9852 | 329-AlaValValLysLeuLysAlaGlyAsp-337 |
| SEQ. ID. NO. 9853 | 342-LysProGlyGluThrIleProValAspGlyThrVal-353 |
| SEQ. ID. NO. 9854 | 356-GlySerSerAlaValAsnGluSerMetLeuThrGlyGluSer-369 |
| SEQ. ID. NO. 9855 | 374-LysMetProSerGluLysValThrAla-382 |
| SEQ. ID. NO. 9856 | 393-IleArgThrAspArgThrGlyGlyGlyThrArg-403 |
| SEQ. ID. NO. 9857 | 414-AlaLeuAlaGlnLysProArgThrAlaGluLeuAlaGlu-426 |
| SEQ. ID. NO. 9858 | 486-ThrLeuAlaArgGluGlyIle-492 |
| SEQ. ID. NO. 9859 | 495-GlyGlyLysGlnAlaIle-500 |
| SEQ. ID. NO. 9860 | 510-IlePheAspLysThrGlyThrLeuThrGlnGlyLysProAlaValArgArg-526 |
| SEQ. ID. NO. 9861 | 528-SerLeuLeuArgGlyThrAspGluAlaPhe-537 |

TABLE 1-continued

| | |
|---|---|
| SEQ. ID. NO. 9862 | 545-LeuGluGlnGlnSerGluHisProLeu-553 |
| SEQ. ID. NO. 9863 | 560-CysArgIleSerAspGlySerValPro-568 |
| SEQ. ID. NO. 9864 | 570-IleAlaIleLysGlnArgLeuAsnArgIleGlyGluGlyVal-583 |
| SEQ. ID. NO. 9865 | 589-ValAsnGlyGluThrGln-594 |
| SEQ. ID. NO. 9866 | 605-AlaGluIleSerGlyLysGluProGlnThrGluGlyGlyGlySer-619 |
| SEQ. ID. NO. 9867 | 637-AspProLeuLysAspSerAlaAlaGluAlaValArg-648 |
| SEQ. ID. NO. 9868 | 650-LeuAlaGlyLysAsnLeu-655 |
| SEQ. ID. NO. 9869 | 659-IleLeuSerGlyAspArgGluThrAlaVal-668 |
| SEQ. ID. NO. 9870 | 684-AlaMetProGluAspLysLeuGluTyr-692 |
| SEQ. ID. NO. 9871 | 694-LysAlaLeuGlnLysGluGlyLysLys-702 |
| SEQ. ID. NO. 9872 | 707-GlyAspGlyIleAsnAspAla-713 |
| SEQ. ID. NO. 9873 | 725-AlaAlaGlyGlyThrAspIleAlaArgAspGlyAlaAsp-737 |
| SEQ. ID. NO. 9874 | 743-GluAspLeuArgThr-747 |
| SEQ. ID. NO. 9875 | 753-AspGlnAlaArgArgThrArgHisIleIle-762 |
| SEQ. ID. NO. 9876 | 807-ArgLeuHisLysArgGlyLysMetGlnSerGluLysMetProSerGluGln-823 |
| Hydrophilic Regions - Hopp-Woods | |
| SEQ. ID. NO. 9877 | 1-MetLysLysThrCys-5 |
| SEQ. ID. NO. 9878 | 21-ArgTyrGluAsnGluAspArgGluThrCys-30 |
| SEQ. ID. NO. 9879 | 50-TyrLysGlnArgThrAlaAspAlaGlnLysThrGluLeuProPro-64 |
| SEQ. ID. NO. 9880 | 77-ProGluValGlnSerAspPheValGlu-85 |
| SEQ. ID. NO. 9881 | 87-HisGlyGlyThrArgGluAla-93 |
| SEQ. ID. NO. 9882 | 112-GlnLeuLeuArgThrAspGlyIleVal-120 |
| SEQ. ID. NO. 9883 | 133-ValValTrpAspAspGlyLysIleArgLeu-142 |
| SEQ. ID. NO. 9884 | 160-AspAlaGlnLysIleGluAlaAlaAsnGlnLysGluArgLysGlnTyr-175 |
| SEQ. ID. NO. 9885 | 201-GlyAspIleGluProAspPhe-207 |
| SEQ. ID. NO. 9886 | 234-AlaLeuArgAspLeuLysAsnArgArgValGlyMet-245 |
| SEQ. ID. NO. 9887 | 293-IleAlaArgArgLysAlaGlyAspAlaAlaGluArgLeuVal-306 |
| SEQ. ID. NO. 9888 | 318-AspTyrProAspThrGlnGluThrCysGlu-327 |
| SEQ. ID. NO. 9889 | 329-AlaValValLysLeuLysAlaGlyAsp-337 |
| SEQ. ID. NO. 9890 | 374-LysMetProSerGluLysValThr-381 |
| SEQ. ID. NO. 9891 | 393-IleArgThrAspArgThrGlyGlyGlyThrArg-403 |
| SEQ. ID. NO. 9892 | 414-AlaLeuAlaGlnLysProArgThrAlaGluLeuAlaGlu-426 |
| SEQ. ID. NO. 9893 | 486-ThrLeuAlaArgGluGlyIle-492 |
| SEQ. ID. NO. 9894 | 518-ThrGlnGlyLysProAlaValArgArg-526 |
| SEQ. ID. NO. 9895 | 531-ArgGlyThrAspGlu-535 |
| SEQ. ID. NO. 9896 | 545-LeuGluGlnGlnSerGluHisProLeu-553 |
| SEQ. ID. NO. 9897 | 561-ArgIleSerAspGlySerVal-567 |
| SEQ. ID. NO. 9898 | 570-IleAlaIleLysGlnArgLeuAsnArgIleGlyGlu-581 |
| SEQ. ID. NO. 9899 | 607-IleSerGlyLysGluProGlnThrGluGlyGlyGly-618 |
| SEQ. ID. NO. 9900 | 638-ProLeuLysAspSerAlaAlaGluAlaValArg-648 |
| SEQ. ID. NO. 9901 | 661-SerGlyAspArgGluThrAlaVal-668 |
| SEQ. ID. NO. 9902 | 684-AlaMetProGluAspLysLeuGluTyr-692 |
| SEQ. ID. NO. 9903 | 694-LysAlaLeuGlnLysGluGlyLysLys-702 |
| SEQ. ID. NO. 9904 | 730-AspIleAlaArgAspGlyAlaAsp-737 |
| SEQ. ID. NO. 9905 | 743-GluAspLeuArgThr-747 |
| SEQ. ID. NO. 9906 | 753-AspGlnAlaArgArgThrArgHisIleIle-762 |
| SEQ. ID. NO. 9907 | 807-ArgLeuHisLysArgGlyLysMetGlnSerGluLysMetProSerGluGln-823 |
| 705 | |
| AMPHI Regions - AMPHI | |
| SEQ. ID. NO. 9908 | 67-LysIleLeuLeuLysLeu-72 |
| SEQ. ID. NO. 9909 | 104-AspProIleProAla-108 |
| SEQ. ID. NO. 9910 | 147-TyrMetGlnThrPheArgArgIleValAlaProGln-158 |
| SEQ. ID. NO. 9911 | 169-AsnGluPheIleGlyLeuPheLysAsn-177 |
| SEQ. ID. NO. 9912 | 183-ValValThrValThrGluLeuPheArgValAlaGln-194 |
| SEQ. ID. NO. 9913 | 196-ThrAlaAsnArgThr-200 |
| Antigenic Index - Jameson-Wolf | |
| SEQ. ID. NO. 9914 | 13-ThrGluThrArgAlaAspMet-19 |
| SEQ. ID. NO. 9915 | 132-ValProLysGlyGlnTrpGlu-138 |
| SEQ. ID. NO. 9916 | 165-ProProLeuSerAsnGlu-170 |
| SEQ. ID. NO. 9917 | 193-AlaGlnGluThrAlaAsnArgThrTyrAsp-202 |
| SEQ. ID. NO. 9918 | 226-AlaArgLeuGluLysArgPheAspArgTyrValAla-237 |
| Hydrophilic Regions - Hopp-Woods | |
| SEQ. ID. NO. 9919 | 13-ThrGluThrArgAlaAspMet-19 |
| SEQ. ID. NO. 9920 | 193-AlaGlnGluThrAlaAsnArgThr-200 |
| SEQ. ID. NO. 9921 | 226-AlaArgLeuGluLysArgPheAspArgTyrValAla-237 |
| 706 | |
| AMPHI Regions - AMPHI | |
| SEQ. ID. NO. 9922 | 9-LeuValSerArgTrpLeuAsnSerTyr-17 |
| SEQ. ID. NO. 9923 | 24-ArgLeuIleHisAlaValArg-30 |
| SEQ. ID. NO. 9924 | 70-IleTyrSerLysAlaValGluArgMetLeuGlyThrValIleGly-84 |
| SEQ. ID. NO. 9925 | 111-ThrAlaSerAlaLeuAlaGlyTrpAlaAla-120 |
| SEQ. ID. NO. 9926 | 153-ArgAlaMetAsnValLeu-158 |
| SEQ. ID. NO. 9927 | 183-LeuAlaAspAsnLeuAlaAspCysSerLysMetIleAlaGluIleSerAsnGlyArg-201 |
| SEQ. ID. NO. 9928 | 204-ThrArgGluArgLeuGluGluAsn-211 |
| SEQ. ID. NO. 9929 | 243-MetGluAlaMetGlnHisAlaHisArgLysIleVal-254 |
| SEQ. ID. NO. 9930 | 318-AlaLeuAlaGluHisLeuHis-324 |
| Antigenic Index - Jameson-Wolf | |
| SEQ. ID. NO. 9931 | 1-MetAsnThrSerGlnArgAsnArgLeu-9 |
| SEQ. ID. NO. 9932 | 11-SerArgTrpLeuAsnSerTyrGluArgTyrArgTyrArgArg-24 |
| SEQ. ID. NO. 9933 | 73-LysAlaValGluArgMetLeu-79 |

TABLE 1-continued

| | |
|---|---|
| SEQ. ID. NO. 9934 | 97-HisTyrPheHisGlyAsnLeu-103 |
| SEQ. ID. NO. 9935 | 122-GlyLysAsnGlyTyrVal-127 |
| SEQ. ID. NO. 9936 | 140-GlyAspAsnGlySerGluTrpLeuAsp-148 |
| SEQ. ID. NO. 9937 | 186-AsnLeuAlaAspCysSerLysMetIleAlaGluIleSerAsnGlyArgArgMetThrArgGluArgLeuGluGluAsnMetAlaLysMetArgGln IleAsn-219 |
| SEQ. ID. NO. 9938 | 221-ArgMetValLysSerArgSerHisLeuAlaAlaThrSerGlyGluSerArgIleSer-239 |
| SEQ. ID. NO. 9939 | 249-AlaHisArgLysIleValAsn-255 |
| SEQ. ID. NO. 9940 | 266-LysLeuGlnSerProLysLeuAsnGlySerGluIleArgLeuLeuAsp-281 |
| SEQ. ID. NO. 9941 | 300-GlyArgHisAlaArgArgIleArgIleAspThrAlaIleAsnProGluLeuGluAlaLeuAla-320 |
| SEQ. ID. NO. 9942 | 334-SerThrAsnMetArgGlnGluIle-341 |
| SEQ. ID. NO. 9943 | 349-GlnArgThrArgArgLysTrpLeuAspAlaHisGluArgGlnHisLeu-364 |
| SEQ. ID. NO. 9944 | 367-SerLeuLeuGluThrArgGluHisGly-375 |
| Hydrophilic Regions - Hopp-Woods | |
| SEQ. ID. NO. 9945 | 3-ThrSerGlnArgAsnArgLeu-9 |
| SEQ. ID. NO. 9946 | 17-TyrGluArgTyrArgTyrArgArg-24 |
| SEQ. ID. NO. 9947 | 73-LysAlaValGluArgMetLeu-79 |
| SEQ. ID. NO. 9948 | 142-AsnGlySerGluTrpLeu-147 |
| SEQ. ID. NO. 9949 | 186-AsnLeuAlaAspCysSerLysMetIleAla-195 |
| SEQ. ID. NO. 9950 | 198-SerAsnGlyArgArgMetThrArgGluArgLeuGluGluAsnMetAlaLysMetArgGlnIleAsn-219 |
| SEQ. ID. NO. 9951 | 221-ArgMetValLysSerArgSerHis-228 |
| SEQ. ID. NO. 9952 | 232-ThrSerGlyGluSerArgIle-238 |
| SEQ. ID. NO. 9953 | 249-AlaHisArgLysIleValAsn-255 |
| SEQ. ID. NO. 9954 | 266-LysLeuGlnSerProLysLeuAsnGlySerGluIleArgLeuLeuAsp-281 |
| SEQ. ID. NO. 9955 | 301-ArgHisAlaArgArgIleArgIle-308 |
| SEQ. ID. NO. 9956 | 314-ProGluLeuGluAlaLeuAla-320 |
| SEQ. ID. NO. 9957 | 336-AsnMetArgGlnGluIle-341 |
| SEQ. ID. NO. 9958 | 349-GlnArgThrArgArgLysTrpLeuAspAlaHisGluArgGlnHisLeu-364 |
| SEQ. ID. NO. 9959 | 367-SerLeuLeuGluThrArgGluHisGly-375 |
| 707 | |
| AMPHI Regions - AMPHI | |
| SEQ. ID. NO. 9960 | 9-LeuIleArgSerMetGlnArgGln-16 |
| SEQ. ID. NO. 9961 | 88-AsnLeuSerArgLeuGlnLysAla-95 |
| SEQ. ID. NO. 9962 | 170-GluGlnGlyLeuGluAsnLeuArgArgLeuProSerVal-182 |
| SEQ. ID. NO. 9963 | 219-GlyGlyLysThrThrGlyLysTyr-226 |
| SEQ. ID. NO. 9964 | 241-SerAspLeuPheTyr-245 |
| SEQ. ID. NO. 9965 | 294-ArgTyrHisGluAlaThrGlu-300 |
| SEQ. ID. NO. 9966 | 339-ThrArgGlnThrTyrLysTyrIleAspAsp-348 |
| SEQ. ID. NO. 9967 | 539-HisLysProLysGlyPheGlnThrThrAsnThr-549 |
| Antigenic Index - Jameson-Wolf | |
| SEQ. ID. NO. 9968 | 3-IleIleAsnAspAlaGluLeuIleArgSerMetGlnArgGlnGlnHisIleAsp-20 |
| SEQ. ID. NO. 9969 | 27-AlaAsnValArgPheGluGlnProLeuGluLysAsnAsnTyrValLeuSerGluAspGluThrProCysThrArg-51 |
| SEQ. ID. NO. 9970 | 56-SerLeuAspAspLysThrValArg-63 |
| SEQ. ID. NO. 9971 | 85-GlySerAsnAsnLeuSerArgLeuGlnLysAlaAla-96 |
| SEQ. ID. NO. 9972 | 114-ProGlnAsnMetAspSerGlyIleLeu-122 |
| SEQ. ID. NO. 9973 | 125-ArgValSerAlaGlyGluIleGlyAspIleArgTyrGluGluLysArgAspGlyLysSerAlaGluGlySerIle-149 |
| SEQ. ID. NO. 9974 | 157-ProLeuTyrArgAsnLysIleLeuAsn-165 |
| SEQ. ID. NO. 9975 | 167-ArgAspValGluGlnGlyLeuGluAsnLeuArgArgLeuProSerValLysThrAspIle-186 |
| SEQ. ID. NO. 9976 | 189-IleProSerGluGluGluGlyLysSerAspLeu-199 |
| SEQ. ID. NO. 9977 | 202-LysTrpGlnGlnAsnLysProIleArg-210 |
| SEQ. ID. NO. 9978 | 213-IleGlyIleAspAspAlaGlyGlyLysThrThrGlyLysTyrGlnGly-228 |
| SEQ. ID. NO. 9979 | 235-AspAsnProLeuGly-239 |
| SEQ. ID. NO. 9980 | 248-TyrGlyArgGlyLeuAlaHisLysThrAspLeuThrAspAlaThrGlyThrGluThrGluSerGlySerArgSerTyr-273 |
| SEQ. ID. NO. 9981 | 288-PheAsnHisAsnGlyHisArgTyrHisGluAlaThrGluGlyTyrSerValAsnTyrAspTyrAsnGlyLysGlnTyrGln-314 |
| SEQ. ID. NO. 9982 | 322-MetLeuTrpArgAsnArgLeuHisLysThrSerVal-333 |
| SEQ. ID. NO. 9983 | 341-GlnThrTyrLysTyrIleAspAspAlaGluIleGluValGlnArgArgArgSerAlaGlyTrpGluAlaGluLeuArgHis-367 |
| SEQ. ID. NO. 9984 | 374-TrpGlnLeuAspGlyLysLeuSerTyrLysArgGlyThrGlyMetArgGlnSerMetProAlaProGluGluAsnGlyGlyAspIleLeuPro GlyThrSerArgMetLysIle-411 |
| SEQ. ID. NO. 9985 | 438-GlnTrpAsnLysThrPro-443 |
| SEQ. ID. NO. 9986 | 446-AlaGlnAspLysLeuSerIleGlySerArgTyrThrValArgGlyPheAspGlyGluGlnSerLeuPheGlyGluArgGlyPheTyrTrpGlnAsn Thr-478 |
| SEQ. ID. NO. 9987 | 493-AlaAspTyrGlyArgValSerGlyGluSerAla-503 |
| SEQ. ID. NO. 9988 | 506-ValSerGlyLysGln-510 |
| SEQ. ID. NO. 9989 | 518-PheArgGlyGlyHisLysValGly-525 |
| SEQ. ID. NO. 9990 | 536-LysProLeuHisLysProLysGlyPheGln-545 |
| Hydrophilic Regions - Hopp-Woods | |
| SEQ. ID. NO. 9991 | 3-IleIleAsnAspAlaGluLeuIleArgSerMetGlnArgGlnGlnHisIleAsp-20 |
| SEQ. ID. NO. 9992 | 27-AlaAsnValArgPheGluGlnProLeuGluLysAsnAsn-39 |
| SEQ. ID. NO. 9993 | 42-LeuSerGluAspGluThrProCys-49 |
| SEQ. ID. NO. 9994 | 56-SerLeuAspAspLysThrValArg-63 |
| SEQ. ID. NO. 9995 | 88-AsnLeuSerArgLeuGlnLysAlaAla-96 |
| SEQ. ID. NO. 9996 | 130-GluIleGlyAspIleArgTyrGluGluLysArgAspGlyLysSerAlaGluGlySer-148 |
| SEQ. ID. NO. 9997 | 167-ArgAspValGluGlnGlyLeuGluAsnLeuArgArgLeuProSerValLysThrAspIle-186 |
| SEQ. ID. NO. 9998 | 190-ProSerGluGluGluGlyLysSerAspLeu-199 |
| SEQ. ID. NO. 9999 | 213-IleGlyIleAspAspAlaGlyGlyLysThrThrGlyLysTyr-226 |
| SEQ. ID. NO. 10000 | 252-LeuAlaHisLysThrAspLeuThrAsp-260 |
| SEQ. ID. NO. 10001 | 262-ThrGlyThrGluThrGluSerGlySerArgSer-272 |
| SEQ. ID. NO. 10002 | 294-ArgTyrHisGluAlaThrGlu-300 |
| SEQ. ID. NO. 10003 | 345-TyrIleAspAspAlaGluIleGluValGlnArgArgArgSerAlaGlyTrp-361 |
| SEQ. ID. NO. 10004 | 363-AlaGluLeuArgHis-367 |
| SEQ. ID. NO. 10005 | 378-GlyLysLeuSerTyrLysArgGlyThrGlyMetArgGlnSerMetProAlaProGluGluAsnGlyGly-400 |

TABLE 1-continued

| | |
|---|---|
| SEQ. ID. NO. 10006 | 407-SerArgMetLysIle-411 |
| SEQ. ID. NO. 10007 | 446-AlaGlnAspLysLeuSerIle-452 |
| SEQ. ID. NO. 10008 | 460-GlyPheAspGlyGluGln-465 |
| SEQ. ID. NO. 10009 | 494-AspTyrGlyArgValSerGlyGluSer-502 |
| SEQ. ID. NO. 10010 | 537-ProLeuHisLysProLysGly-543 |
| 708 | |
| AMPHI Regions - AMPHI | |
| SEQ. ID. NO. 10011 | 26-ProSerArgAlaGluLysAlaAsnGlnValSerAsnIle-38 |
| SEQ. ID. NO. 10012 | 56-ThrAlaSerIleGluAspAlaLeuLysSerAspPro-67 |
| SEQ. ID. NO. 10013 | 79-IleTyrGlnTyrLeuLys-84 |
| SEQ. ID. NO. 10014 | 89-AlaGlnGluSerPhe-93 |
| SEQ. ID. NO. 10015 | 119-AsnArgProAlaGluSerMetAla-126 |
| SEQ. ID. NO. 10016 | 128-PheAspLysAlaLeu-132 |
| SEQ. ID. NO. 10017 | 142-IleAlaAsnLeuAsnLys-147 |
| SEQ. ID. NO. 10018 | 176-ProAlaPheLysGluLeuAlaArg-183 |
| SEQ. ID. NO. 10019 | 221-LysAlaLeuGlyAsnAlaGln-227 |
| Antigenic Index - Jameson-Wolf | |
| SEQ. ID. NO. 10020 | 2-ProPheLysProSerLysArgIleSer-10 |
| SEQ. ID. NO. 10021 | 19-AlaCysSerThrSerTyrArgProSerArgAlaGluLysAlaAsnGln-34 |
| SEQ. ID. NO. 10022 | 46-TyrMetArgGlyGlnAspTyrArgGlnAlaThrAlaSerIleGluAspAlaLeuLysSerAspProLysAsnGlu-70 |
| SEQ. ID. NO. 10023 | 84-LysValAsnAspLysAlaGlnGluSerPheArg-94 |
| SEQ. ID. NO. 10024 | 97-LeuSerIleLysProAspSerAlaGluIleAsnAsnAsnTyrGlyTrp-112 |
| SEQ. ID. NO. 10025 | 115-CysGlyArgLeuAsnArgProAlaGlu-123 |
| SEQ. ID. NO. 10026 | 131-AlaLeuAlaAspProThrTyrProThr-139 |
| SEQ. ID. NO. 10027 | 145-LeuAsnLysGlyIleCysSerAlaLysGlnGlyGln-156 |
| SEQ. ID. NO. 10028 | 176-ProAlaPheLysGluLeuAlaArgThrLysMet-186 |
| SEQ. ID. NO. 10029 | 191-LeuGlyAspAlaAspTyrTyrPheLysLysTyrGlnSerArgValGluValLeuGlnAlaAspAspLeu-213 |
| SEQ. ID. NO. 10030 | 240-PheProTyrSerGluGluLeuGln-247 |
| Hydrophilic Regions - Hopp-Woods | |
| SEQ. ID. NO. 10031 | 4-LysProSerLysArgIle-9 |
| SEQ. ID. NO. 10032 | 24-TyrArgProSerArgAlaGluLysAlaAsnGln-34 |
| SEQ. ID. NO. 10033 | 46-TyrMetArgGlyGlnAspTyrArgGln-54 |
| SEQ. ID. NO. 10034 | 56-ThrAlaSerIleGluAspAlaLeuLysSerAspProLysAsnGlu-70 |
| SEQ. ID. NO. 10035 | 84-LysValAsnAspLysAlaGlnGluSerPheArg-94 |
| SEQ. ID. NO. 10036 | 99-IleLysProAspSerAlaGluIle-106 |
| SEQ. ID. NO. 10037 | 117-ArgLeuAsnArgProAlaGlu-123 |
| SEQ. ID. NO. 10038 | 149-IleCysSerAlaLysGlnGly-155 |
| SEQ. ID. NO. 10039 | 177-AlaPheLysGluLeuAlaArgThrLysMet-186 |
| SEQ. ID. NO. 10040 | 201-TyrGlnSerArgValGluValLeuGlnAlaAspAspLeu-213 |
| 709 | |
| AMPHI Regions - AMPHI | |
| SEQ. ID. NO. 10041 | 6-SerLeuLeuAspMetProArgGlyGlu-14 |
| SEQ. ID. NO. 10042 | 18-ValValValAlaLeuIleAlaAlaMetGly-27 |
| SEQ. ID. NO. 10043 | 37-ProHisMetSerIleIleAlaAlaIleValValLeu-48 |
| SEQ. ID. NO. 10044 | 54-AlaArgGlyLeuLysTyrAsn-60 |
| SEQ. ID. NO. 10045 | 64-GlnGlyMetIleGlyAlaLeuAsnGlnGly-73 |
| SEQ. ID. NO. 10046 | 115-SerSerPheAlaLeuCysSerVal-122 |
| SEQ. ID. NO. 10047 | 130-SerLeuThrThrCysAla-135 |
| SEQ. ID. NO. 10048 | 171-ProLeuSerAspThr-175 |
| SEQ. ID. NO. 10049 | 185-IleAspLeuPheGluHisIleLysAsnMetMetTyrThrThr-198 |
| SEQ. ID. NO. 10050 | 221-LeuAsnSerValGluSerPheArg-228 |
| SEQ. ID. NO. 10051 | 253-LeuMetArgIleAsnAla-258 |
| SEQ. ID. NO. 10052 | 261-AlaMetLeuPheThr-265 |
| SEQ. ID. NO. 10053 | 278-ThrProAspLeuArgGlnLeuGlyAlaTrpPhe-288 |
| SEQ. ID. NO. 10054 | 298-AlaPheLysAspValValLysLeuIleSerArgGlyGly-310 |
| SEQ. ID. NO. 10055 | 334-LeuGlyValIleProSerLeuLeuGluAlaIleArgThrPheLeuThr-349 |
| SEQ. ID. NO. 10056 | 382-ThrPheLysProVal-386 |
| SEQ. ID. NO. 10057 | 395-ArgAsnLeuSerArgThrLeuGluAspAlaGlyThrValIleAsnProLeuValProTrpSerValCysGlyValPheIleSerHis-423 |
| Antigenic Index - Jameson-Wolf | |
| SEQ. ID. NO. 10058 | 8-LeuAspMetProArgGlyGluAla-15 |
| SEQ. ID. NO. 10059 | 55-ArgGlyLeuLysTyrAsnAspMetGln-63 |
| SEQ. ID. NO. 10060 | 165-PheGlyAspLysMetSerProLeuSerAspThrThrGly-177 |
| SEQ. ID. NO. 10061 | 222-AsnSerValGluSerPheArgSerGlnLeuGlu-232 |
| SEQ. ID. NO. 10062 | 277-SerThrProAspLeuArgGln-283 |
| SEQ. ID. NO. 10063 | 290-GlyGlyTyrLysLeuGluGlyGluAlaPheLysAspValVal-303 |
| SEQ. ID. NO. 10064 | 306-IleSerArgGlyGlyLeuGlu-312 |
| SEQ. ID. NO. 10065 | 378-LeuSerGlyGluThrPheLysProValTyrAspLysLeuGlyLeuHisSerArgAsnLeuSerArgThrLeuGluAspAlaGlyThr-406 |
| Hydrophilic Regions - Hopp-Woods | |
| SEQ. ID. NO. 10066 | 8-LeuAspMetProArgGlyGluAla-15 |
| SEQ. ID. NO. 10067 | 57-LeuLysTyrAsnAspMetGln-63 |
| SEQ. ID. NO. 10068 | 168-LysMetSerProLeuSerAsp-174 |
| SEQ. ID. NO. 10069 | 225-GluSerPheArgSerGlnLeuGlu-232 |
| SEQ. ID. NO. 10070 | 279-ProAspLeuArgGln-283 |
| SEQ. ID. NO. 10071 | 293-LysLeuGluGlyGluAlaPheLysAspValVal-303 |
| SEQ. ID. NO. 10072 | 396-AsnLeuSerArgThrLeuGluAspAlaGly-405 |
| 710 | |
| AMPHI Regions - AMPHI | |
| SEQ. ID. NO. 10073 | 6-LysIleArgLeuMetArgGluLeuAsnLysTrpSerGln-18 |
| SEQ. ID. NO. 10074 | 31-GlyTyrAlaLysIleGlu-36 |

TABLE 1-continued

SEQ. ID. NO. 10075 45-ProArgLeuGluGlnLeuAlaGlnIlePheLysIleAspMetTrpAspLeuLeuLys-63
SEQ. ID. NO. 10076 104-CysLysGluMetLeuGlu-109
Antigenic Index - Jameson-Wolf
SEQ. ID. NO. 10077 1-MetGluThrHisGluLysIleArgLeuMetArgGluLeuAsnLysTrpSerGlnGluAspMetAlaGluLysLeuAla-26
SEQ. ID. NO. 10078 33-AlaLysIleGluArgGlyGluThrGlnLeuAsnIleProArgLeuGluGln-49
SEQ. ID. NO. 10079 62-LeuLysSerGlyGlyGlyGly-68
SEQ. ID. NO. 10080 73-IleAsnGluGlyAspSerGlyGlyAsp-81
SEQ. ID. NO. 10081 86-AlaSerGlyAspValSerMet-92
SEQ. ID. NO. 10082 95-GluPheLeuLysMetGluLeuLysHisCysLysGluMetLeuGluGlnLysAspLysGluIleGluLeuLeuArgLysLeuThrGlu-123
Hydrophilic Regions - Hopp-Woods
SEQ. ID. NO. 10083 1-MetGluThrHisGluLysIleArgLeuMetArgGluLeuAsnLysTrpSerGlnGluAspMetAlaGluLysLeuAla-26
SEQ. ID. NO. 10084 33-AlaLysIleGluArgGlyGluThr-40
SEQ. ID. NO. 10085 45-ProArgLeuGluGln-49
SEQ. ID. NO. 10086 74-AsnGluGlyAspSerGlyGly-80
SEQ. ID. NO. 10087 95-GluPheLeuLysMetGluLeuLysHisCysLysGluMetLeuGluGlnLysAspLysGluIleGluLeuLeuArgLysLeuThrGlu-123
711
AMPHI Regions - AMPHI
SEQ. ID. NO. 10088 28-AlaGluSerTyrArgAsnLeuThrAlaSerGluIleAlaLysValTyrThrIleAlaArgMetThrAspLeuAspMetLeuAsnAspIleLys-58
SEQ. ID. NO. 10089 67-SerGlyGlnSerPheAspAspTrpArgLysGlyIleLeu-79
SEQ. ID. NO. 10090 95-GlyLysAspIleIleAspProAlaThrGlyGluValPheGlySerProArgArgLeuGluThrIleTyrArgThrAsnMet-121
SEQ. ID. NO. 10091 128-GlyGlnTyrGlnGlyTyrMet-134
SEQ. ID. NO. 10092 158-SerAlaIleAspGly-162
SEQ. ID. NO. 10093 195-ValGluArgGlnGly-199
SEQ. ID. NO. 10094 203-GlyGlnSerThrAlaAspAsnLeuValGluThrHis-214
SEQ. ID. NO. 10095 258-LysTyrAspArgAlaLeuAlaHisGlnPheAla-268
SEQ. ID. NO. 10096 281-PheLysGlnLeuGluLysGluPheTyr-289
SEQ. ID. NO. 10097 329-GlnGluLeuAlaGlyMetThr-335
SEQ. ID. NO. 10098 352-SerArgGluGlyGlnAsnPhe-358
SEQ. ID. NO. 10099 360-AspSerTyrTyrAlaPheLeuProAspMetLeuGlnAsnProGlu-374
SEQ. ID. NO. 10100 395-TrpAlaValLeuLysTyrIleLysGluValAspGluIle-407
SEQ. ID. NO. 10101 413-ArgIleSerAsnAspLysGluIleAlaLys-422
Antigenic Index - Jameson-Wolf
SEQ. ID. NO. 10102 11-SerLeuProProLysLysAlaIleGlu-19
SEQ. ID. NO. 10103 21-LeuGluSerLysLysValThrAlaGluSerTyrArgAsnLeuThr-35
SEQ. ID. NO. 10104 55-AsnAspIleLysThrSerMet-61
SEQ. ID. NO. 10105 63-GluSerAlaLysSerGlyGlnSerPheAspAspTrpArgLysGlyIle-78
SEQ. ID. NO. 10106 82-LeuSerAsnLysGlyTrpLeuHisProAsnGlyHisAsnGlyLysAspIleIleAspProAlaThrGlyGluValPheGlySerProArgArgLeu GluThrIleTyrArgThrAsnMet-121
SEQ. ID. NO. 10107 126-AsnAlaGlyGlnTyrGlnGly-132
SEQ. ID. NO. 10108 135-AlaAsnIleAspAlaArgProTyrTrp-143
SEQ. ID. NO. 10109 147-AlaValGlyAspSerArgThrArgProAlaHisSerAla-159
SEQ. ID. NO. 10110 165-TyrArgTyrAspAspProPheTrp-172
SEQ. ID. NO. 10111 177-ProProAsnGlyTyrAsnCysArgCysSer-186
SEQ. ID. NO. 10112 190-LeuSerGluArgAspValGluArgGlnGlyArgIleValGlyGlnSerThrAlaAspAsnLeuValGlu-212
SEQ. ID. NO. 10113 215-LysIleTyrAsnLysLysGlyAspThr-223
SEQ. ID. NO. 10114 229-TyrLysAlaProAspGlySerLeuTyrThrThrAspArgGlyPheAspTyrAsnAlaGlyArgMetAsnTyrArgProAspLeuAspLysTyr AspArgAlaLeu-263
SEQ. ID. NO. 10115 268-AlaLysAlaGluMetGlyGlyAlaAspPheLysThrSerPheLysGlnLeuGluLysGluPheTyrGluValLysGlnArgLeuAspIleAspGly LysProAspLysGluGlnLysIleLysIleArgAsnAlaLeu-313
SEQ. ID. NO. 10116 324-LeuSerLysGluThrGlnGlu-330
SEQ. ID. NO. 10117 342-SerAspAspThrLeuValLysGlnValAspSerArgGluGlyGlnAsnPheAspAspSerTyrTyr-363
SEQ. ID. NO. 10118 370-LeuGlnAsnProGluHisValIleArgAspAsnArgGlu-382
SEQ. ID. NO. 10119 387-AlaArgTyrLysGlySer-392
SEQ. ID. NO. 10120 400-TyrIleLysGluValAspGlu-406
SEQ. ID. NO. 10121 411-SerTyrArgIleSerAsnAspLysGluIleAla-421
SEQ. ID. NO. 10122 424-MetAlaLysLysLysValLeuLys-431
Hydrophilic Regions - Hopp-Woods
SEQ. ID. NO. 10123 13-ProProLysLysAlaIleGlu-19
SEQ. ID. NO. 10124 21-LeuGluSerLysLysValThrAlaGluSerTyrArg-32
SEQ. ID. NO. 10125 55-AsnAspIleLysThrSerMet-61
SEQ. ID. NO. 10126 63-GluSerAlaLysSerGlyGlnSerPheAspAspTrpArgLys-76
SEQ. ID. NO. 10127 93-HisAsnGlyLysAspIleIleAsp-100
SEQ. ID. NO. 10128 108-GlySerProArgArgLeuGluThr-115
SEQ. ID. NO. 10129 147-AlaValGlyAspSerArgThrArgProAlaHisSerAla-159
SEQ. ID. NO. 10130 190-LeuSerGluArgAspValGluArgGlnGlyArgIleVal-202
SEQ. ID. NO. 10131 215-LysIleTyrAsnLysLysGlyAspThr-223
SEQ. ID. NO. 10132 238-ThrThrAspArgGlyPheAsp-244
SEQ. ID. NO. 10133 250-MetAsnTyrArgProAspLeuAspLysTyrAspArgAlaLeu-263
SEQ. ID. NO. 10134 268-AlaLysAlaGluMetGlyGlyAlaAspPheLysThrSerPheLysGlnLeuGluLysGluPheTyrGluValLysGlnArgLeuAspIleAsp GlyLysProAspLysGluGlnLysIleLysIleArgAsnAlaLeu-313
SEQ. ID. NO. 10135 324-LeuSerLysGluThrGlnGlu-330
SEQ. ID. NO. 10136 344-AspThrLeuValLysGlnValAspSerArgGluGlyGlnAsnPheAsp-359
SEQ. ID. NO. 10137 375-HisValIleArgAspAsnArgGlu-382
SEQ. ID. NO. 10138 400-TyrIleLysGluValAspGlu-406
SEQ. ID. NO. 10139 414-IleSerAsnAspLysGluIleAla-421
SEQ. ID. NO. 10140 424-MetAlaLysLysLysValLeuLys-431
712
AMPHI Regions - AMPHI
SEQ. ID. NO. 10141 12-GlySerIleArgVal-16
SEQ. ID. NO. 10142 29-ValGlnGlyLeuProGlnAsnPro-36

TABLE 1-continued

| | |
|---|---|
| SEQ. ID. NO. 10143 | 55-GluProValGlnLeuPhe-60 |
| SEQ. ID. NO. 10144 | 72-GlySerLeuAlaHisLeuMet-78 |
| SEQ. ID. NO. 10145 | 131-SerThrAlaValAsn-135 |
| SEQ. ID. NO. 10146 | 142-ThrValAlaAspArgLeuLys-148 |
| SEQ. ID. NO. 10147 | 210-ThrAlaLeuSerLysValAla-216 |
| SEQ. ID. NO. 10148 | 231-AlaAsnAlaLysAlaLeuSerAsnHisIleThrAsnValSerAsnAlaIle-247 |
| SEQ. ID. NO. 10149 | 306-ProAlaLysProLeuAsnThrLeuGlu-314 |
| SEQ. ID. NO. 10150 | 329-PheAlaGluCysAsnAsnAlaLeuTyrAsnGlyLeuThrProLeu-343 |
| SEQ. ID. NO. 10151 | 352-IleMetArgAlaValSerThrTyrThrLysSerAlaAsnAsn-365 |
| SEQ. ID. NO. 10152 | 374-IleThrThrIleArgThrLeuAspTyrValArgArgSerVal-387 |
| SEQ. ID. NO. 10153 | 411-GluIleLeuAspValLeuIle-417 |
| SEQ. ID. NO. 10154 | 421-GlnAlaGluIleIleGluAsn-427 |
| SEQ. ID. NO. 10155 | 441-GlnAsnAspProAsn-445 |
| SEQ. ID. NO. 10156 | 454-AspValValAsnGlyLeu-459 |
| Antigenic Index - Jameson-Wolf | |
| SEQ. ID. NO. 10157 | 6-AspPheAspThrIleProGlySerIleArgValProGlyGln-19 |
| SEQ. ID. NO. 10158 | 23-PheAsnThrArgAsnAlaVal-29 |
| SEQ. ID. NO. 10159 | 32-LeuProGlnAsnProGlnLys-38 |
| SEQ. ID. NO. 10160 | 61-SerAspAlaGluAlaAlaAsp-67 |
| SEQ. ID. NO. 10161 | 125-IleGlyGlyLysGlnVal-130 |
| SEQ. ID. NO. 10162 | 134-ValAsnThrGlyGluThrAla-140 |
| SEQ. ID. NO. 10163 | 143-ValAlaAspArgLeuLysThr-149 |
| SEQ. ID. NO. 10164 | 171-AlaLysHisLysGlyGluIleGlyAsnGluSerGlyLeu-183 |
| SEQ. ID. NO. 10165 | 201-GlyGlyAlaLysAsnAlaAsp-207 |
| SEQ. ID. NO. 10166 | 215-ValAlaGlyLysHis-219 |
| SEQ. ID. NO. 10167 | 225-SerProPheSerAspAspAlaAsnAlaLysAlaLeuSer-237 |
| SEQ. ID. NO. 10168 | 243-ValSerAsnAlaIleGluGlnArgGlyCys-252 |
| SEQ. ID. NO. 10169 | 268-AlaThrGlyGluIleAsnAspGlyArgMet-277 |
| SEQ. ID. NO. 10170 | 284-GlyAlaValGluProAsnGly-290 |
| SEQ. ID. NO. 10171 | 302-PheGluGluAspProAlaLysProLeuAsn-311 |
| SEQ. ID. NO. 10172 | 313-LeuGluIleLysGly-317 |
| SEQ. ID. NO. 10173 | 320-ValThrProAspAlaGln-325 |
| SEQ. ID. NO. 10174 | 332-CysAsnAsnAlaLeuTyrAsnGly-339 |
| SEQ. ID. NO. 10175 | 358-ThrTyrThrLysSerAlaAsnAsnThrAspAspProAlaLeu-371 |
| SEQ. ID. NO. 10176 | 381-AspTyrValArgArgSerValLysGluArgIleAlaLeuArgPheProArgAspLysLeuSerAspArgLeuLeuProLysValLysSerGluIle-412 |
| SEQ. ID. NO. 10177 | 419-LeuAspGlnAlaGluIleIleGluAsnAlaGluAlaAsnLysGlyLysLeuValVal-437 |
| SEQ. ID. NO. 10178 | 440-AlaGlnAsnAspProAsnArgValAsnAla-449 |
| Hydrophilic Regions - Hopp-Woods | |
| SEQ. ID. NO. 10179 | 61-SerAspAlaGluAlaAlaAsp-67 |
| SEQ. ID. NO. 10180 | 135-AsnThrGlyGluThr-139 |
| SEQ. ID. NO. 10181 | 143-ValAlaAspArgLeuLysThr-149 |
| SEQ. ID. NO. 10182 | 171-AlaLysHisLysGlyGluIleGlyAsn-179 |
| SEQ. ID. NO. 10183 | 203-AlaLysAsnAlaAsp-207 |
| SEQ. ID. NO. 10184 | 227-PheSerAspAspAlaAsnAlaLysAlaLeu-236 |
| SEQ. ID. NO. 10185 | 247-IleGluGlnArgGly-251 |
| SEQ. ID. NO. 10186 | 270-GlyGluIleAsnAspGlyArgMet-277 |
| SEQ. ID. NO. 10187 | 302-PheGluGluAspProAlaLysPro-309 |
| SEQ. ID. NO. 10188 | 313-LeuGluIleLysGly-317 |
| SEQ. ID. NO. 10189 | 362-SerAlaAsnAsnThrAspAspProAlaLeu-371 |
| SEQ. ID. NO. 10190 | 381-AspTyrValArgArgSerValLysGluArgIleAla-392 |
| SEQ. ID. NO. 10191 | 395-PheProArgAspLysLeuSerAspArgLeuLeuProLysValLysSerGluIle-412 |
| SEQ. ID. NO. 10192 | 419-LeuAspGlnAlaGluIleIleGluAsnAlaGluAlaAsnLysGlyLysLeuValVal-437 |
| SEQ. ID. NO. 10193 | 440-AlaGlnAsnAspProAsnArg-446 |
| 713 | |
| AMPHI Regions - AMPHI | |
| SEQ. ID. NO. 10194 | 18-GluHisArgHisTrpGlu-23 |
| SEQ. ID. NO. 10195 | 115-AspAlaAlaLysLysLeuAlaAlaProTrpProGlnIle-127 |
| SEQ. ID. NO. 10196 | 150-ThrValTrpGlnAlaLeuThrHisIleAlaAsnSerVal-162 |
| SEQ. ID. NO. 10197 | 257-AspAsnLeuAlaAlaLeuGln-263 |
| SEQ. ID. NO. 10198 | 265-GlnAlaLysLysGln-269 |
| Antigenic Index - Jameson-Wolf | |
| SEQ. ID. NO. 10199 | 1-MetGlnAsnAsnSerTyrGly-7 |
| SEQ. ID. NO. 10200 | 13-ArgValGlyGlyLysGluHisArgHisTrpGluArgTyrAspIleAspSerAspPhe-31 |
| SEQ. ID. NO. 10201 | 44-ArgLeuGlyProGluAlaAlaIleProAspLeuSerGlyGluSerCysGluValValIle-63 |
| SEQ. ID. NO. 10202 | 74-GlySerGlnArgHisGlyLysSerLysGlySerArgGluLeuSerLeuSerGlyArgAspLeu-94 |
| SEQ. ID. NO. 10203 | 106-LeuAsnValLysGly-110 |
| SEQ. ID. NO. 10204 | 115-AspAlaAlaLysLysLeu-120 |
| SEQ. ID. NO. 10205 | 131-ValLeuLysAlaGluAsnAsnProAlaLeuGlyLysIleAspIleGluProGlyGlu-149 |
| SEQ. ID. NO. 10206 | 167-TrpLeuGluProAspGlyThrLeu-174 |
| SEQ. ID. NO. 10207 | 177-GlyGlyAlaAspTyrSerSerProPro-185 |
| SEQ. ID. NO. 10208 | 192-SerArgThrAspSerArgCysAsnIleGluArgMetAspIleGluTrpAspThrAspAsnArgPheSerGlu-215 |
| SEQ. ID. NO. 10209 | 222-SerHisGlyArgSerGlyAspSerAlaLysHisAspLeu-234 |
| SEQ. ID. NO. 10210 | 237-ValTyrLysAspProThrMetThrLeuHisArgProLysThrValVal-252 |
| SEQ. ID. NO. 10211 | 254-SerAspAlaAspAsn-258 |
| SEQ. ID. NO. 10212 | 263-GlnLysGlnAlaLysLysGlnLeuAla-271 |
| SEQ. ID. NO. 10213 | 284-ValGlyGlyHisLysThrArgAspGly-292 |

TABLE 1-continued

SEQ. ID. NO. 10214 303-ValIleAspAspGluHisGlyIle-310
SEQ. ID. NO. 10215 321-PheMetLeuSerArgMetAspGlyThrGlnThrGluLeuArgLeuLysGluAspGlyIleTrpThrProAspAlaTyrProLysLysAlaGlu AlaAlaArgLysArgLysGlyLysArgLysGlyValSerHisLysGlyLysLysGlyGlyLysLysGlnAlaGlu-376
Hydrophilic Regions - Hopp-Woods
SEQ. ID. NO. 10216 14-ValGlyGlyLysGluHisArgHisTrpGluArgTyrAspIleAspSer-29
SEQ. ID. NO. 10217 54-LeuSerGlyGluSerCysGluValValIle-63
SEQ. ID. NO. 10218 76-GlnArgHisGlyLysSerLysGlySerArgGluLeuSerLeuSerGlyArgAspLeu-94
SEQ. ID. NO. 10219 115-AspAlaAlaLysLysLeu-120
SEQ. ID. NO. 10220 131-ValLeuLysAlaGluAsnAsnProAla-139
SEQ. ID. NO. 10221 141-GlyLysIleAspIleGluProGlyGlu-149
SEQ. ID. NO. 10222 168-LeuGluProAspGly-172
SEQ. ID. NO. 10223 193-ArgThrAspSerArgCysAsnIleGluArgMetAspIleGluTrpAspThrAspAsnArgPheSer-214
SEQ. ID. NO. 10224 222-SerHisGlyArgSerGlyAspSerAlaLysHisAspLeu-234
SEQ. ID. NO. 10225 246-HisArgProLysThr-250
SEQ. ID. NO. 10226 254-SerAspAlaAspAsn-258
SEQ. ID. NO. 10227 263-GlnLysGlnAlaLysLysGlnLeuAla-271
SEQ. ID. NO. 10228 286-GlyHisLysThrArgAsp-291
SEQ. ID. NO. 10229 303-ValIleAspAspGluHisGlyIle-310
SEQ. ID. NO. 10230 325-ArgMetAspGlyThrGlnThrGluLeuArgLeuLysGluAspGlyIleTrp-341
SEQ. ID. NO. 10231 345-AlaTyrProLysLysAlaGluAlaAlaArgLysArgLysGlyLysArgLysGlyValSerHisLysGlyLysLysGlyGlyLysLysGlnAlaGlu-376
714
AMPHI Regions - AMPHI
SEQ. ID. NO. 10232 6-IleLeuArgGlyLeuLeuPro-12
SEQ. ID. NO. 10233 34-LeuAspAlaValAlaGluSerAlaGlnSerValAla-45
SEQ. ID. NO. 10234 54-GlyGlnMetLeuAlaAspTrpGluArgValLeuGlyLeu-66
SEQ. ID. NO. 10235 79-AlaValMetAlaLysLeuAsnGluThrGly-88
SEQ. ID. NO. 10236 98-LeuAlaGluAlaAla-102
SEQ. ID. NO. 10237 110-GluProGlnProPhe-114
SEQ. ID. NO. 10238 116-AlaGlyValAsnArgAlaGlyAspArgLeu-125
SEQ. ID. NO. 10239 155-AlaGlyAspArgLeuThrAspTyrSerAspAlaValIleGluSerLeuPheAsnArgLeuLys-175
Antigenic Index - Jameson-Wolf
SEQ. ID. NO. 10240 15-SerTyrAlaArgAsnAlaProArgValArgAlaGlnAlaGluIleAspGlyAlaAla-33
SEQ. ID. NO. 10241 36-AlaValAlaGluSerAlaGlnSerVal-44
SEQ. ID. NO. 10242 46-AspAlaValAspProArgSerAla-53
SEQ. ID. NO. 10243 64-LeuGlyLeuAspGlyThrGlyLysAsnArgGlnHisArg-76
SEQ. ID. NO. 10244 83-LysLeuAsnGluThrGlyGlyLeu-90
SEQ. ID. NO. 10245 107-GlnIleAspGluProGlnProPheArgAlaGlyValAsnArgAlaGlyAspArgLeuAlaPro-127
SEQ. ID. NO. 10246 138-ValArgGlyGlyAsnAsnArgIleThrArgPheArgAlaGlyIle-152
SEQ. ID. NO. 10247 154-AlaAlaGlyAspArgLeuThrAspTyrSerAspAlaValIle-167
SEQ. ID. NO. 10248 170-LeuPheAsnArgLeuLysPro-176
Hydrophilic Regions - Hopp-Woods
SEQ. ID. NO. 10249 18-ArgAsnAlaProArgValArgAlaGlnAlaGluIleAspGlyAlaAla-33
SEQ. ID. NO. 10250 36-AlaValAlaGluSerAlaGlnSerVal-44
SEQ. ID. NO. 10251 46-AspAlaValAspProArgSerAla-53
SEQ. ID. NO. 10252 68-GlyThrGlyLysAsnArgGlnHisArg-76
SEQ. ID. NO. 10253 107-GlnIleAspGluProGlnProPhe-114
SEQ. ID. NO. 10254 117-GlyValAsnArgAlaGlyAspArgLeuAlaPro-127
SEQ. ID. NO. 10255 139-ArgGlyGlyAsnAsnArgIleThrArgPheArgAla-150
SEQ. ID. NO. 10256 154-AlaAlaGlyAspArgLeuThrAspTyrSerAspAlaValIle-167
SEQ. ID. NO. 10257 170-LeuPheAsnArgLeuLysPro-176
715
AMPHI Regions - AMPHI
SEQ. ID. NO. 10258 15-GlnIleGluArgLeuGlyAsnGlyIle-23
SEQ. ID. NO. 10259 31-ArgArgLeuSerGluThrMetHis-38
SEQ. ID. NO. 10260 64-LeuSerAspSerGlyArgLeuLysAspSerPheSer-75
SEQ. ID. NO. 10261 94-IleHisAsnPheGlyGly-99
Antigenic Index - Jameson-Wolf
SEQ. ID. NO. 10262 15-GlnIleGluArgLeuGlyAsnGlyIleGluAsnArgTyrLeuLeu-29
SEQ. ID. NO. 10263 47-TyrAlaGlyArgProLysTrpValGlyLeuLysTyrArgAspGlyLysProLeuSerAspSerGlyArgLeuLysAspSerPheSerThrLeuSer AspAsnAspThrAla-83
SEQ. ID. NO. 10264 98-GlyGlyMetAlaGlyArgAsnArgLysValArgIleProGlnArgGluPhe-114
SEQ. ID. NO. 10265 118-ThrAspAspAspLysGlnAlaLeuMetAspAspValGlnAsp-131
Hydrophilic Regions - Hopp-Woods
SEQ. ID. NO. 10266 15-GlnIleGluArgLeuGlyAsn-21
SEQ. ID. NO. 10267 57-LysTyrArgAspGlyLysProLeuSerAspSerGlyArgLeuLysAspSerPhe-74
SEQ. ID. NO. 10268 78-SerAspAsnAspThr-82
SEQ. ID. NO. 10269 101-AlaGlyArgAsnArgLysValArgIleProGlnArgGlu-113
SEQ. ID. NO. 10270 118-ThrAspAspAspLysGlnAlaLeuMetAspAspValGlnAsp-131
716
AMPHI Regions - AMPHI
SEQ. ID. NO. 10271 33-GlyValHisLysSerAlaHisGly-40
SEQ. ID. NO. 10272 71-AlaThrValLysLysThrHisLysHisThrLysAla-82
Antigenic Index - Jameson-Wolf
SEQ. ID. NO. 10273 1-MetAsnLysAsnIle-5
SEQ. ID. NO. 10274 23-AlaAlaAsnLysProAlaSerAsnAlaThrGlyValHisLysSerAlaHisGlySerCysGlyAlaSerLysSerAlaGluGlySerCysGlyAlaAlaGly SerLysAlaGlyGluGlyLysCysGlyGluGlyLysCysGlyAlaThrValLysLysThrHisLysHisThrLysAlaSerLysAlaLysAlaLysSerAlaGlu GlyLysCysGlyGluGlyLysCysGlySerLys-102
Hydrophilic Regions - Hopp-Woods
SEQ. ID. NO. 10275 23-AlaAlaAsnLysProAlaSer-29
SEQ. ID. NO. 10276 33-GlyValHisLysSerAlaHis-39

TABLE 1-continued

| | |
|---|---|
| SEQ. ID. NO. 10277 | 43-GlyAlaSerLysSerAlaGluGlySerCys-52 |
| SEQ. ID. NO. 10278 | 55-AlaGlySerLysAlaGlyGluGlyLysCysGlyGluGlyLysCys-69 |
| SEQ. ID. NO. 10279 | 71-AlaThrValLysLysThrHisLysHisThrLysAlaSerLysAlaLysAlaLysSerAlaGluGlyLysCysGlyGluGlyLysCysGlySerLys-102 |
| 717 | |
| AMPHI Regions - AMPHI | |
| SEQ. ID. NO. 10280 | 175-AlaValTyrAlaLeuAlaAsn-181 |
| SEQ. ID. NO. 10281 | 209-LeuHisArgGlyLeu-213 |
| SEQ. ID. NO. 10282 | 223-SerIleAlaTyrTrp-227 |
| SEQ. ID. NO. 10283 | 241-AlaGlyLeuGluGlnLeuGly-247 |
| SEQ. ID. NO. 10284 | 263-GlnSerIlePheSerThrValTrpThrProTyrIlePheArgAlaIleGluGlu-280 |
| SEQ. ID. NO. 10285 | 305-ThrGlyIlePheSerProLeuAlaSer-313 |
| SEQ. ID. NO. 10286 | 347-LeuAsnValValArgLysThr-353 |
| SEQ. ID. NO. 10287 | 358-LeuAlaThrLeuGlyAlaLeuAla-365 |
| SEQ. ID. NO. 10288 | 401-SerSerCysArgLeuTrpGlnProLeuLysArgLeu-412 |
| SEQ. ID. NO. 10289 | 430-CysPheGlyThrPro-434 |
| SEQ. ID. NO. 10290 | 442-GlyValTrpAlaAlaTyrLeuAlaGly-450 |
| SEQ. ID. NO. 10291 | 457-LysAspLeuHisLysLeuPheHisTyr-465 |
| Antigenic Index - Jameson-Wolf | |
| SEQ. ID. NO. 10292 | 1-MetAspThrLysGlu-5 |
| SEQ. ID. NO. 10293 | 32-ProAlaAspAspIleGlyArg-38 |
| SEQ. ID. NO. 10294 | 66-TyrAlaThrAlaAspLysAspThrLeu-74 |
| SEQ. ID. NO. 10295 | 95-SerArgProSerLeuProSerGluIle-103 |
| SEQ. ID. NO. 10296 | 135-MetGluGlyArgAla-139 |
| SEQ. ID. NO. 10297 | 192-AsnArgCysArgLeuLysAlaValArg-200 |
| SEQ. ID. NO. 10298 | 231-SerAlaAspArgLeuPheLeu-237 |
| SEQ. ID. NO. 10299 | 277-AlaIleGluGluAsnAlaProProAlaArgLeu-287 |
| SEQ. ID. NO. 10300 | 289-AlaThrAlaGluSer-293 |
| SEQ. ID. NO. 10301 | 317-ProGluAsnTyrAla-321 |
| SEQ. ID. NO. 10302 | 349-ValValArgLysThrArgProIleAla-357 |
| SEQ. ID. NO. 10303 | 376-ProSerGlyGlyAlaArgGly-382 |
| SEQ. ID. NO. 10304 | 397-PheLysThrGluSerSerCysArgLeu-405 |
| SEQ. ID. NO. 10305 | 453-LeuArgHisArgLysAspLeuHis-460 |
| Hydrophilic Regions - Hopp-Woods | |
| SEQ. ID. NO. 10306 | 1-MetAspThrLysGlu-5 |
| SEQ. ID. NO. 10307 | 66-TyrAlaThrAlaAspLysAspThrLeu-74 |
| SEQ. ID. NO. 10308 | 135-MetGluGlyArgAla-139 |
| SEQ. ID. NO. 10309 | 192-AsnArgCysArgLeuLysAlaValArg-200 |
| SEQ. ID. NO. 10310 | 277-AlaIleGluGluAsnAlaProProAlaArgLeu-287 |
| SEQ. ID. NO. 10311 | 289-AlaThrAlaGluSer-293 |
| SEQ. ID. NO. 10312 | 349-ValValArgLysThrArgPro-355 |
| SEQ. ID. NO. 10313 | 378-GlyGlyAlaArgGly-382 |
| SEQ. ID. NO. 10314 | 398-LysThrGluSerSerCys-403 |
| SEQ. ID. NO. 10315 | 453-LeuArgHisArgLysAspLeuHis-460 |
| 718-1 | |
| AMPHI Regions - AMPHI | |
| SEQ. ID. NO. 10316 | 28-IleThrAlaThrGlyArgValIleAlaGluHisProSerAsnPheIleThrProGln-46 |
| SEQ. ID. NO. 10317 | 49-ArgAlaLeuPheGlu-53 |
| SEQ. ID. NO. 10318 | 110-AspGlnAlaTyrGluMetMetAspSerLeuProThr-121 |
| SEQ. ID. NO. 10319 | 124-AspLeuIleMetAspLeuMetAspAlaValGlyHisGly-136 |
| SEQ. ID. NO. 10320 | 160-ProGlnSerTrpPheLys-165 |
| SEQ. ID. NO. 10321 | 198-ArgSerValGlnGln-202 |
| SEQ. ID. NO. 10322 | 210-ThrLeuSerTrpLeuTyrMetPhe-217 |
| SEQ. ID. NO. 10323 | 219-HisTyrAlaValHisAspPheAlaGluPheLeuGluLeu-231 |
| SEQ. ID. NO. 10324 | 255-ArgAlaValAlaGluIle-260 |
| SEQ. ID. NO. 10325 | 280-AlaAsnGlyThrThr-284 |
| SEQ. ID. NO. 10326 | 320-ThrAsnAlaLeuGlyAsnIleHisAsnGluValArg-331 |
| SEQ. ID. NO. 10327 | 341-GlnValAlaGlnThrIleThrSerGlnIleIleGlyProPhe-354 |
| SEQ. ID. NO. 10328 | 363-AspProAsnArgVal-367 |
| SEQ. ID. NO. 10329 | 376-GluProLysAspIleAlaValPheAlaAspAlaIleProLysLeuValAsp-392 |
| SEQ. ID. NO. 10330 | 395-ValGlnIleProGlu-399 |
| SEQ. ID. NO. 10331 | 420-ArgGlnValProAspAsnPro-426 |
| SEQ. ID. NO. 10332 | 448-HisGlnGluIleLeuAspGlyAlaLeuAspAsp-458 |
| SEQ. ID. NO. 10333 | 469-LeuAsnProMetValArgGlnAlaValAlaAlaLeuAsnAlaCysAsnSerTyrGlu-487 |
| Antigenic Index - Jameson-Wolf | |
| SEQ. ID. NO. 10334 | 4-IleMetAlaLysLysAsnAsnLysThrLysIleGlnLysProGluAlaAlaLeu-21 |
| SEQ. ID. NO. 10335 | 30-AlaThrGlyArgValIleAla-36 |
| SEQ. ID. NO. 10336 | 38-HisProSerAsnPhe-42 |
| SEQ. ID. NO. 10337 | 44-ThrProGlnLysMetArgAlaLeuPheGluAspAlaGluSerGlyAspIleArgAlaGlnHis-64 |
| SEQ. ID. NO. 10338 | 68-AlaAspIleGluGluArgAspSerAspIle-77 |
| SEQ. ID. NO. 10339 | 81-MetGlyThrArgLysArgAla-87 |
| SEQ. ID. NO. 10340 | 95-ValAlaProProArgAsnAlaThrProGluGluGluLysLeuSerAspGlnAlaTyrGluMet-115 |
| SEQ. ID. NO. 10341 | 119-LeuProThrLeuGlu-123 |
| SEQ. ID. NO. 10342 | 148-AspGlyLeuTyrLeuProArgAsnPheIleHisArgProGlnSerTrpPheLysTrpAspLysAspAsnGlyLeu-172 |
| SEQ. ID. NO. 10343 | 174-LeuArgThrArgGluAsnProGluGlyGluAla-184 |
| SEQ. ID. NO. 10344 | 193-HisThrGlnLysSerArgSerValGlnGlnAlaArgAsnGlyLeuPhe-208 |
| SEQ. ID. NO. 10345 | 237-ArgIleGlyLysTyrGlyAlaGlyAlaThrLysGluGluLysAsnThrLeu-253 |
| SEQ. ID. NO. 10346 | 268-MetProGluGlyMetGluIleGluLeu-276 |
| SEQ. ID. NO. 10347 | 280-AlaAsnGlyThrThrAlaThr-286 |
| SEQ. ID. NO. 10348 | 295-AspTrpCysGluLysSerAlaAla-302 |
| SEQ. ID. NO. 10349 | 310-LeuThrSerGlyAlaAspGlyLysSerSerThrAsnAlaLeuGly-324 |

TABLE 1-continued

| | |
|---|---|
| SEQ. ID. NO. 10350 | 328-AsnGluValArgArgAspLeuLeuValSerAspAlaLysGlnVal-342 |
| SEQ. ID. NO. 10351 | 359-TyrProHisAlaAspProAsnArgValProLysPheGluPheAspThrArgGluProLysAspIle-380 |
| SEQ. ID. NO. 10352 | 397-IleProGluSerTrpValArgAspLysLeuVal-407 |
| SEQ. ID. NO. 10353 | 410-AspValGlnGluGlyGluAlaValLeu-418 |
| SEQ. ID. NO. 10354 | 420-ArgGlnValProAspAsnProValAsnArg-429 |
| SEQ. ID. NO. 10355 | 440-ValProSerLysAlaThrGlyArgHisGlnGluIleLeuAspGlyAlaLeuAsp-457 |
| SEQ. ID. NO. 10356 | 459-AlaLeuValGluProAspPheAsnSerGlnLeu-469 |
| SEQ. ID. NO. 10357 | 484-AsnSerTyrGluGluAlaAspAla-491 |
| SEQ. ID. NO. 10358 | 499-AsnLeuAspAsnAlaLysLeuArgThr-507 |
| SEQ. ID. NO. 10359 | 519-LeuGlyGlnAspHisAlaArgAla-526 |
| Hydrophilic Regions - Hopp-Woods | |
| SEQ. ID. NO. 10360 | 4-IleMetAlaLysLysAsnAsnLysThrLysIleGlnLysProGluAlaAlaLeu-21 |
| SEQ. ID. NO. 10361 | 46-GlnLysMetArgAlaLeuPheGluAspAlaGluSerGlyAspIleArgAlaGlnHis-64 |
| SEQ. ID. NO. 10362 | 68-AlaAspIleGluGluArgAspSerAspIle-77 |
| SEQ. ID. NO. 10363 | 81-MetGlyThrArgLysArgAla-87 |
| SEQ. ID. NO. 10364 | 96-AlaProProArgAsnAlaThrProGluGluGluLysLeuSerAspGlnAlaTyrGluMet-115 |
| SEQ. ID. NO. 10365 | 165-LysTrpAspLysAspAsnGlyLeu-172 |
| SEQ. ID. NO. 10366 | 174-LeuArgThrArgGluAsnProGluGlyGluAla-184 |
| SEQ. ID. NO. 10367 | 195-GlnLysSerArgSerValGlnGlnAlaArg-204 |
| SEQ. ID. NO. 10368 | 245-AlaThrLysGluGluLysAsnThrLeu-253 |
| SEQ. ID. NO. 10369 | 270-GluGlyMetGluIleGluLeu-276 |
| SEQ. ID. NO. 10370 | 295-AspTrpCysGluLysSerAlaAla-302 |
| SEQ. ID. NO. 10371 | 312-SerGlyAlaAspGlyLysSerSerThr-320 |
| SEQ. ID. NO. 10372 | 328-AsnGluValArgArgAspLeuLeuValSerAspAlaLysGlnVal-342 |
| SEQ. ID. NO. 10373 | 363-AspProAsnArgValProLysPheGluPheAspThrArgGluProLysAsp-379 |
| SEQ. ID. NO. 10374 | 401-TrpValArgAspLysLeuVal-407 |
| SEQ. ID. NO. 10375 | 410-AspValGlnGluGlyGluAlaValLeu-418 |
| SEQ. ID. NO. 10376 | 421-GlnValProAspAsnProValAsn-428 |
| SEQ. ID. NO. 10377 | 440-ValProSerLysAlaThrGlyArgHisGlnGluIleLeuAspGlyAlaLeuAsp-457 |
| SEQ. ID. NO. 10378 | 485-SerTyrGluGluAlaAspAla-491 |
| SEQ. ID. NO. 10379 | 501-AspAsnAlaLysLeu-505 |
| SEQ. ID. NO. 10380 | 522-AspHisAlaArgAla-526 |
| 719 | |
| AMPHI Regions - AMPHI | |
| SEQ. ID. NO. 10381 | 21-ArgLeuLeuAlaAspThrGlnArgGlnLeuAspArgThrAla-34 |
| SEQ. ID. NO. 10382 | 68-AlaPheAsnArgLeuAlaArgSerGlyLys-77 |
| SEQ. ID. NO. 10383 | 79-SerGlnAsnAspLeu-83 |
| SEQ. ID. NO. 10384 | 104-GlyThrGlyPheAlaAspLysMetGlyLysIleGlyArgPheGlyAla-119 |
| SEQ. ID. NO. 10385 | 143-AspGluAsnIleAsnArgValSerArg-151 |
| SEQ. ID. NO. 10386 | 191-AlaLeuAspLeuIleSerGlyMetMet-199 |
| SEQ. ID. NO. 10387 | 229-ThrAlaLysLeuIleLysThrLeuLysAsp-238 |
| SEQ. ID. NO. 10388 | 254-LeuGlnSerGlyLeu-258 |
| SEQ. ID. NO. 10389 | 266-AspMetValArgGluLeuProSerLeuLeuSer-276 |
| SEQ. ID. NO. 10390 | 280-GlnAlaGlyMetAsnGlyValGlyGlyLeuAspTyrLeuLeuSerLeuLeu-296 |
| SEQ. ID. NO. 10391 | 308-GluAlaAlaThrAsnValGlnAsnLeuLeuSerLys-319 |
| SEQ. ID. NO. 10392 | 324-AspThrIleGlyArgLeuLysLysMetAlaAsnProAsnAspProLysLysGlyValAspTrpIleGlySer-347 |
| SEQ. ID. NO. 10393 | 360-GlnValLeuSerArgLeuAlaAsp-367 |
| SEQ. ID. NO. 10394 | 404-GlnLeuLeuProAspLeu-409 |
| SEQ. ID. NO. 10395 | 418-AlaThrAspMetThrGlnIleArgGluTyrMetAlaSerLeu-431 |
| SEQ. ID. NO. 10396 | 467-GluSerLeuThrGlyThr-472 |
| SEQ. ID. NO. 10397 | 477-GluThrSerPheLysLysLeuAlaAlaGlu-486 |
| SEQ. ID. NO. 10398 | 497-LeuThrThrAlaAla-501 |
| SEQ. ID. NO. 10399 | 519-GlyPheLeuLysAspValGly-525 |
| SEQ. ID. NO. 10400 | 557-AlaGlySerGlyLeu-561 |
| SEQ. ID. NO. 10401 | 588-LeuProLysGlyLeuArgGlyThr-595 |
| SEQ. ID. NO. 10402 | 597-ThrThrProGluMetIleAsnArgLeuLys-606 |
| SEQ. ID. NO. 10403 | 626-ProGlnTyrLeuAlaAlaPro-632 |
| SEQ. ID. NO. 10404 | 635-GlnProThrAspLysMetLeuSerProLeuPhe-645 |
| SEQ. ID. NO. 10405 | 676-ThrGlyLeuAlaGlnValGlnSerAlaMetAla-686 |
| SEQ. ID. NO. 10406 | 707-AsnGluValSerArg-711 |
| Antigenic Index - Jameson-Wolf | |
| SEQ. ID. NO. 10407 | 1-MetAlaAsnGlyAsnMet-6 |
| SEQ. ID. NO. 10408 | 14-AlaArgAspAspGlyAlaArgArgLeuLeuAlaAspThrGlnArgGlnLeuAspArgThrAlaLysSerArgAlaGlnLeuGluArgGlnSerHisThrTyr-47 |
| SEQ. ID. NO. 10409 | 51-GlyIleArgSerGluLysGlnIleGlnArg-60 |
| SEQ. ID. NO. 10410 | 71-ArgLeuAlaArgSerGlyLysAlaSerGlnAsnAspLeuAlaArg-85 |
| SEQ. ID. NO. 10411 | 90-ThrArgAsnArgIleArgGluLeuAsnAlaGluLeuLysGlnGlyThrGlyPheAlaAspLysMetGlyLysIleGlyArgPheGly-118 |
| SEQ. ID. NO. 10412 | 134-ProAlaMetAspAsnArgLysGlnLeuAspGluAsnIleAsnArgValSerArg-151 |
| SEQ. ID. NO. 10413 | 153-AlaPheIleGluAspAsnSerLysSerAla-162 |
| SEQ. ID. NO. 10414 | 168-GluGlyAlaGlnGlnIleLysAspLeuAla-177 |
| SEQ. ID. NO. 10415 | 180-LeuValGluLysAsnGlyGlyThrHisAspLysAlaLeuAsp-193 |
| SEQ. ID. NO. 10416 | 207-GlnThrLysAsnGluAla-212 |
| SEQ. ID. NO. 10417 | 222-SerGluGlySerGlyGluAspThrAlaLysLeu-232 |
| SEQ. ID. NO. 10418 | 234-LysThrLeuLysAspGlyGlyMetSerGlyLysAspLeuGlnLeu-248 |
| SEQ. ID. NO. 10419 | 256-SerGlyLeuAspGlyThrPheGluValArgAspMetValArgGluLeuProSer-273 |
| SEQ. ID. NO. 10420 | 299-AlaAlaAsnLysSerGlySerProAlaGluAla-309 |
| SEQ. ID. NO. 10421 | 318-SerLysThrLeuSerProAspThrIleGlyArgLeuLysLysMetAlaAsnProAsnAspProLysLysGlyValAspTrp-344 |
| SEQ. ID. NO. 10422 | 349-ValGlnGlyLysGlnAsnGlyGluAsn-357 |
| SEQ. ID. NO. 10423 | 369-MetLeuValLysAspLysGlnTyrGlnAspTyrLysLysArgAlaAlaAlaGlyAspLysThrAlaAlaGluGln-393 |
| SEQ. ID. NO. 10424 | 422-ThrGlnIleArgGluTyrMet-428 |

TABLE 1-continued

| | |
|---|---|
| SEQ. ID. NO. 10425 | 437-AspAsnGlyLysIleAlaLysAsnAsnGluAlaArgMet-449 |
| SEQ. ID. NO. 10426 | 454-AlaGlnGlnGluGlnGlnGluSer-461 |
| SEQ. ID. NO. 10427 | 463-AlaMetLeuArgGluSerLeu-469 |
| SEQ. ID. NO. 10428 | 474-ValAspMetGluThrSerPheLysLysLeuAlaAla-485 |
| SEQ. ID. NO. 10429 | 511-ThrAlaGlyGlyGlyLysGlyAlaGlyPhe-520 |
| SEQ. ID. NO. 10430 | 522-LysAspValGlySerLysAla-528 |
| SEQ. ID. NO. 10431 | 532-GlyLysAlaSerAlaGlyGly-538 |
| SEQ. ID. NO. 10432 | 545-AlaAlaGlyGlyLys-549 |
| SEQ. ID. NO. 10433 | 554-GlyLysSerAlaGlySerGlyLeuMetAsnAsnProAlaLeuValLysArgAlaGly-572 |
| SEQ. ID. NO. 10434 | 580-SerGluSerLeuGlyAspGlyThrLeuProLysGlyLeuArgGlyThrLysThrThrPro-599 |
| SEQ. ID. NO. 10435 | 601-MetIleAsnArgLeuLysAsnAsnGlyIleArgPheGluProAlaProLysArgGluGlnAlaArgGlyGlyValPro-626 |
| SEQ. ID. NO. 10436 | 631-AlaProSerAlaGlnProThrAspLysMetLeuSerPro-643 |
| SEQ. ID. NO. 10437 | 687-SerAlaSerGlnThrIleAsnThrAsnValSerLeuAsnIleAspGlyArgValIleAla-706 |
| SEQ. ID. NO. 10438 | 708-GluValSerArgTyrGln-713 |
| SEQ. ID. NO. 10439 | 718-GlyArgGlyAlaGlyGln-723 |
| Hydrophilic Regions - Hopp-Woods | |
| SEQ. ID. NO. 10440 | 14-AlaArgAspAspGlyAlaArgArgLeuLeuAlaAspThrGlnArgGlnLeuAspArgThrAlaLysSerArgAlaGlnLeuGluArgGlnSer-44 |
| SEQ. ID. NO. 10441 | 52-IleArgSerGluLysGlnIleGlnArg-60 |
| SEQ. ID. NO. 10442 | 71-ArgLeuAlaArgSerGlyLysAlaSerGlnAsnAspLeuAlaArg-85 |
| SEQ. ID. NO. 10443 | 90-ThrArgAsnArgIleArgGluLeuAsnAlaGluLeuLysGln-103 |
| SEQ. ID. NO. 10444 | 107-PheAlaAspLysMetGlyLysIleGlyArg-116 |
| SEQ. ID. NO. 10445 | 134-ProAlaMetAspAsnArgLysGlnLeuAspGluAsnIleAsnArgValSerArg-151 |
| SEQ. ID. NO. 10446 | 153-AlaPheIleGluAspAsnSerLys-160 |
| SEQ. ID. NO. 10447 | 168-GluGlyAlaGlnGlnIleLysAspLeuAla-177 |
| SEQ. ID. NO. 10448 | 180-LeuValGluLysAsnGlyGlyThrHisAspLysAlaLeuAsp-193 |
| SEQ. ID. NO. 10449 | 207-GlnThrLysAsnGluAla-212 |
| SEQ. ID. NO. 10450 | 222-SerGluGlySerGlyGluAspThrAlaLysLeu-232 |
| SEQ. ID. NO. 10451 | 234-LysThrLeuLysAspGlyGlyMetSerGlyLysAspLeuGlnLeu-248 |
| SEQ. ID. NO. 10452 | 262-PheGluValArgAspMetValArgGluLeuPro-272 |
| SEQ. ID. NO. 10453 | 299-AlaAlaAsnLysSerGlySerProAlaGluAla-309 |
| SEQ. ID. NO. 10454 | 325-ThrIleGlyArgLeuLysLysMetAlaAsnProAsnAspProLysLysGlyVal-342 |
| SEQ. ID. NO. 10455 | 349-ValGlnGlyLysGlnAsnGlyGluAsn-357 |
| SEQ. ID. NO. 10456 | 369-MetLeuValLysAspLysGlnTyrGlnAspTyrLysLysArgAlaAlaAlaGlyAspLysThrAlaAlaGluGln-393 |
| SEQ. ID. NO. 10457 | 422-ThrGlnIleArgGluTyrMet-428 |
| SEQ. ID. NO. 10458 | 437-AspAsnGlyLysIleAlaLysAsnAsnGluAlaArgMet-449 |
| SEQ. ID. NO. 10459 | 454-AlaGlnGlnGluGlnGlnGluSer-461 |
| SEQ. ID. NO. 10460 | 463-AlaMetLeuArgGluSerLeu-469 |
| SEQ. ID. NO. 10461 | 474-ValAspMetGluThrSerPheLysLysLeuAlaAla-485 |
| SEQ. ID. NO. 10462 | 522-LysAspValGlySer-526 |
| SEQ. ID. NO. 10463 | 567-LeuValLysArgAlaGly-572 |
| SEQ. ID. NO. 10464 | 590-LysGlyLeuArgGlyThrLysThrThrPro-599 |
| SEQ. ID. NO. 10465 | 601-MetIleAsnArgLeuLysAsnAsnGlyIleArgPheGluProAlaProLysArgGluGlnAlaArgGlyGly-624 |
| SEQ. ID. NO. 10466 | 635-GlnProThrAspLysMetLeu-641 |
| SEQ. ID. NO. 10467 | 700-IleAspGlyArgValIleAla-706 |
| 720 | |
| AMPHI Regions - AMPHI | |
| SEQ. ID. NO. 10468 | 6-ThrLeuLeuGlnAspAlaSer-12 |
| SEQ. ID. NO. 10469 | 24-AspGluSerAsnGlyLysAlaLeuAlaGluHisAlaArgProPhe-38 |
| SEQ. ID. NO. 10470 | 65-TyrAlaGlyArgLeuLysLysLeuLeuAspAlaLeuGluGlnPro-79 |
| SEQ. ID. NO. 10471 | 87-ProValTrpGlyArgMetHisAsnMetIleAlaAla-98 |
| SEQ. ID. NO. 10472 | 142-IleAlaAsnIleAspThrTyrArg-149 |
| SEQ. ID. NO. 10473 | 166-ValSerAlaLeuTrpGlySerAlaLeuGly-175 |
| SEQ. ID. NO. 10474 | 184-PheGlyAlaValArgArgLeuPheAspLeuAspLysIleAla-197 |
| SEQ. ID. NO. 10475 | 212-GlySerAlaLysLeuPheAlaAspIleSerVal-222 |
| SEQ. ID. NO. 10476 | 268-LeuThrGlyArgPheSerAspGlyLeuGlnAsnArgLeuAsnArgLeu-283 |
| SEQ. ID. NO. 10477 | 293-GlnAlaValArgLeuLeuSerThrSer-301 |
| SEQ. ID. NO. 10478 | 320-AlaProAspLeuIleGluValAsn-327 |
| SEQ. ID. NO. 10479 | 340-AlaLeuArgAlaValGlnThrAla-347 |
| SEQ. ID. NO. 10480 | 365-GlnThrAlaGluSerLeu-370 |
| SEQ. ID. NO. 10481 | 376-ArgLeuAsnAlaLeuValAla-382 |
| SEQ. ID. NO. 10482 | 400-GlyThrIleHisGlnIleAlaHisGluPheTyrGlyAspIleAlaArgAlaAlaGluLeuVal-420 |
| Antigenic Index - Jameson-Wolf | |
| SEQ. ID. NO. 10483 | 8-LeuGlnAspAlaSerTyrLysGlyValGlyPhe-18 |
| SEQ. ID. NO. 10484 | 21-GluValValAspGluSerAsnGlyLysAlaLeuAlaGluHisAlaArg-36 |
| SEQ. ID. NO. 10485 | 42-IleAspLeuGluAspMetGlyMetThrGlyArg-52 |
| SEQ. ID. NO. 10486 | 62-GlyLysGlyTyrAlaGlyArgLeuLysLysLeuLeuAspAlaLeuGluGlnProGlyGlyGly-82 |
| SEQ. ID. NO. 10487 | 101-SerTyrArgHisGluAlaAspTyr-108 |
| SEQ. ID. NO. 10488 | 117-ThrPheArgGluAlaAlaGluAlaGln-125 |
| SEQ. ID. NO. 10489 | 146-AspThrTyrArgGluAlaAla-152 |
| SEQ. ID. NO. 10490 | 189-ArgLeuPheAspLeuAspLys-195 |
| SEQ. ID. NO. 10491 | 197-AlaPheProAspArgGlyGlyTyrSer-205 |
| SEQ. ID. NO. 10492 | 209-PheLysAsnGlySer-213 |
| SEQ. ID. NO. 10493 | 226-ThrGlyIleArgArgGluAlaGlyLeu-234 |
| SEQ. ID. NO. 10494 | 244-TrpSerProArgGlnArgPheAspGly-252 |
| SEQ. ID. NO. 10495 | 256-ValAlaAspArgAlaAlaAlaIleProAspAsn-266 |
| SEQ. ID. NO. 10496 | 270-GlyArgPheSerAspGlyLeuGlnAsnArgLeuAsnArgLeuThrAlaLysGlnVal-288 |
| SEQ. ID. NO. 10497 | 313-AlaHisGlyGluGluMetThrAla-320 |
| SEQ. ID. NO. 10498 | 322-AspLeuIleGluValAsnArgAlaMetArgArgArgMetGlnAla-336 |
| SEQ. ID. NO. 10499 | 348-AlaAlaGluSerGlyGlyLeuThrAla-356 |
| SEQ. ID. NO. 10500 | 365-GlnThrAlaGluSerLeuArgAlaAlaAla-374 |

TABLE 1-continued

| | |
|---|---|
| SEQ. ID. NO. 10501 | 386-AsnGlnLysProProLeu-391 |
| SEQ. ID. NO. 10502 | 395-GlnAlaProIleAspGlyThr-401 |
| SEQ. ID. NO. 10503 | 413-IleAlaArgAlaAlaGlu-418 |
| SEQ. ID. NO. 10504 | 431-PheIleLysArgGlyThrLeuValAsnSerTyrAlaLys-443 |
| Hydrophilic Regions - Hopp-Woods | |
| SEQ. ID. NO. 10505 | 21-GluValValAspGluSerAsnGlyLysAlaLeuAlaGluHisAlaArg-36 |
| SEQ. ID. NO. 10506 | 42-IleAspLeuGluAspMetGlyMetThr-50 |
| SEQ. ID. NO. 10507 | 65-TyrAlaGlyArgLeuLysLysLeuLeuAspAlaLeuGluGlnProGly-80 |
| SEQ. ID. NO. 10508 | 104-HisGluAlaAspTyr-108 |
| SEQ. ID. NO. 10509 | 117-ThrPheArgGluAlaAlaGluAlaGln-125 |
| SEQ. ID. NO. 10510 | 146-AspThrTyrArgGluAlaAla-152 |
| SEQ. ID. NO. 10511 | 189-ArgLeuPheAspLeuAspLys-195 |
| SEQ. ID. NO. 10512 | 197-AlaPheProAspArgGlyGly-203 |
| SEQ. ID. NO. 10513 | 226-ThrGlyIleArgArgGluAlaGlyLeu-234 |
| SEQ. ID. NO. 10514 | 246-ProArgGlnArgPheAspGly-252 |
| SEQ. ID. NO. 10515 | 256-ValAlaAspArgAlaAlaAla-262 |
| SEQ. ID. NO. 10516 | 276-LeuGlnAsnArgLeuAsnArgLeuThrAla-285 |
| SEQ. ID. NO. 10517 | 313-AlaHisGlyGluGluMetThrAla-320 |
| SEQ. ID. NO. 10518 | 322-AspLeuIleGluValAsnArgAlaMetArgArgArgMetGlnAla-336 |
| SEQ. ID. NO. 10519 | 348-AlaAlaGluSerGlyGly-353 |
| SEQ. ID. NO. 10520 | 368-GluSerLeuArgAlaAlaAla-374 |
| SEQ. ID. NO. 10521 | 413-IleAlaArgAlaAlaGlu-418 |
| 721 | |
| AMPHI Regions - AMPHI | |
| SEQ. ID. NO. 10522 | 87-AlaGlyTrpMetArgTrpLeuGlu-94 |
| SEQ. ID. NO. 10523 | 120-ArgTyrIleSerAlaVal-125 |
| SEQ. ID. NO. 10524 | 135-SerLysIlePheHisAlaAlaLeuThrAsnPheProAlaLeuAspGlyMetAspGluValLeuAla-156 |
| SEQ. ID. NO. 10525 | 170-AsnProMetLysGluLeuLeuGlnGlnLeuPheAspLeuPro-183 |
| SEQ. ID. NO. 10526 | 210-AspValPheAlaGln-214 |
| SEQ. ID. NO. 10527 | 236-LysTyrAlaProIleSerValValGlnGluLeuGln-247 |
| SEQ. ID. NO. 10528 | 282-TrpAlaLysGlyValLeuLysGlnProGlyGly-292 |
| SEQ. ID. NO. 10529 | 294-AlaPheLeuThrGlyPheIleGlu-301 |
| Antigenic Index - Jameson-Wolf | |
| SEQ. ID. NO. 10530 | 1-MetSerLysAsnAlaGln-6 |
| SEQ. ID. NO. 10531 | 16-GluValGlnProLysAspGlyArgIle-24 |
| SEQ. ID. NO. 10532 | 27-LeuProTyrGlyGlu-31 |
| SEQ. ID. NO. 10533 | 33-ArgAlaValAspGlyArgProThrAspValProAla-44 |
| SEQ. ID. NO. 10534 | 48-ThrGluGluAsnGlyHisAsp-54 |
| SEQ. ID. NO. 10535 | 58-LeuAlaAsnSerSerArgAsnGlnLeu-66 |
| SEQ. ID. NO. 10536 | 74-ThrLeuTyrLysGluLysAsnGlyGlnProAlaPro-85 |
| SEQ. ID. NO. 10537 | 94-GluPheThrProLysGlyMetPheAla-102 |
| SEQ. ID. NO. 10538 | 105-GluTrpThrAspLysAlaAla-111 |
| SEQ. ID. NO. 10539 | 115-AlaAlaLysGluTyrArg-120 |
| SEQ. ID. NO. 10540 | 126-PheSerTyrAspThrLysGlyTyrVal-134 |
| SEQ. ID. NO. 10541 | 149-AspGlyMetAspGluValLeu-155 |
| SEQ. ID. NO. 10542 | 161-GlnIleLeuLysProGluThrGluGlnAsnProMetLysGluLeuLeu-176 |
| SEQ. ID. NO. 10543 | 183-ProAspAlaGlyGluGluGluLeuLysAla-192 |
| SEQ. ID. NO. 10544 | 198-ValGluAlaLysProLysAspValAlaLeu-207 |
| SEQ. ID. NO. 10545 | 215-LeuAlaGluLysAspSerArgIle-222 |
| SEQ. ID. NO. 10546 | 228-GlnThrAlaLysProAspLeuThrLysTyrAla-238 |
| SEQ. ID. NO. 10547 | 255-AlaLysGlnGluAlaAspLysGlyAsnGlu-264 |
| SEQ. ID. NO. 10548 | 277-ProAlaGlnLysGluTrpAla-283 |
| SEQ. ID. NO. 10549 | 286-ValLeuLysGlnProGlyGly-292 |
| SEQ. ID. NO. 10550 | 311-GlySerGlnThrGlyGlyLysAlaProAspGluArgValAla-324 |
| SEQ. ID. NO. 10551 | 327-ThrAlaGluGluAlaAlaAla-333 |
| SEQ. ID. NO. 10552 | 338-GlyMetSerGlyGluGluPheValLysIleLysGluSerGluGlyLys-353 |
| Hydrophilic Regions - Hopp-Woods | |
| SEQ. ID. NO. 10553 | 1-MetSerLysAsnAlaGln-6 |
| SEQ. ID. NO. 10554 | 17-ValGlnProLysAspGlyArgIle-24 |
| SEQ. ID. NO. 10555 | 33-ArgAlaValAspGlyArgProThrAsp-41 |
| SEQ. ID. NO. 10556 | 49-GluGluAsnGlyHis-53 |
| SEQ. ID. NO. 10557 | 74-ThrLeuTyrLysGluLysAsnGlyGln-82 |
| SEQ. ID. NO. 10558 | 105-GluTrpThrAspLysAlaAla-111 |
| SEQ. ID. NO. 10559 | 115-AlaAlaLysGluTyrArg-120 |
| SEQ. ID. NO. 10560 | 149-AspGlyMetAspGluValLeu-155 |
| SEQ. ID. NO. 10561 | 163-LeuLysProGluThrGluGlnAsnProMetLysGluLeuLeu-176 |
| SEQ. ID. NO. 10562 | 183-ProAspAlaGlyGluGluGluLeuLysAla-192 |
| SEQ. ID. NO. 10563 | 198-ValGluAlaLysProLysAspValAlaLeu-207 |
| SEQ. ID. NO. 10564 | 215-LeuAlaGluLysAspSerArgIle-222 |
| SEQ. ID. NO. 10565 | 229-ThrAlaLysProAspLeuThrLys-236 |
| SEQ. ID. NO. 10566 | 255-AlaLysGlnGluAlaAspLysGlyAsnGlu-264 |
| SEQ. ID. NO. 10567 | 277-ProAlaGlnLysGluTrpAla-283 |
| SEQ. ID. NO. 10568 | 314-ThrGlyGlyLysAlaProAspGluArgValAla-324 |
| SEQ. ID. NO. 10569 | 327-ThrAlaGluGluAlaAlaAla-333 |
| SEQ. ID. NO. 10570 | 340-SerGlyGluGluPheValLysIleLysGluSerGluGlyLys-353 |
| 723 | |
| AMPHI Regions - AMPHI | |
| SEQ. ID. NO. 10571 | 57-ThrGlnGlnValGluHisValAspPheValAlaValAla-69 |
| SEQ. ID. NO. 10572 | 87-AsnValAlaAlaLys-91 |
| SEQ. ID. NO. 10573 | 123-CysAspLeuAlaVal-127 |

TABLE 1-continued

| | |
|---|---|
| SEQ. ID. NO. 10574 | 135-ValGlyGluLeuGlnAspPhe-141 |
| SEQ. ID. NO. 10575 | 208-SerIleThrSerArg-212 |
| SEQ. ID. NO. 10576 | 245-LysAlaValValSerIle-250 |
| Antigenic Index - Jameson-Wolf | |
| SEQ. ID. NO. 10577 | 1-MetArgProLysProArgPheArgArgSerVal-11 |
| SEQ. ID. NO. 10578 | 55-HisSerThrGlnGln-59 |
| SEQ. ID. NO. 10579 | 76-HisAlaLeuSerArgArgGlnThrVal-84 |
| SEQ. ID. NO. 10580 | 92-AlaHisGlnAspGlyArgGlnIleLeuLysArgSerSerGluProProGlnIleArgValAspPheGlySerGlyValHisGlnArgGlyLeuCys-123 |
| SEQ. ID. NO. 10581 | 142-GlnLeuThrGluThrArgAsnHisIleLeuAsnArgArgValCysHis-157 |
| SEQ. ID. NO. 10582 | 164-CysSerIleGlySer-168 |
| SEQ. ID. NO. 10583 | 177-SerProThrSerAlaArgPheThrSerArgGlnProProSerAsnSerArgProProArgGlnAsnSerLeuPro-201 |
| SEQ. ID. NO. 10584 | 213-LeuSerAlaLysAlaSerAla-219 |
| SEQ. ID. NO. 10585 | 229-SerAlaSerSerAlaAspSer-235 |
| SEQ. ID. NO. 10586 | 260-SerAlaCysThrAlaSerAsn-266 |
| SEQ. ID. NO. 10587 | 269-LeuMetSerSerAsnAspGlyAlaAla-277 |
| SEQ. ID. NO. 10588 | 294-CysPheArgArgArgArgIleArgIle-302 |
| Hydrophilic Regions - Hopp-Woods | |
| SEQ. ID. NO. 10589 | 1-MetArgProLysProArgPheArgArgSerVal-11 |
| SEQ. ID. NO. 10590 | 77-AlaLeuSerArgArgGlnThrVal-84 |
| SEQ. ID. NO. 10591 | 92-AlaHisGlnAspGlyArgGlnIleLeuLysArgSerSerGluProProGlnIleArgValAspPhe-113 |
| SEQ. ID. NO. 10592 | 142-GlnLeuThrGluThrArgAsn-148 |
| SEQ. ID. NO. 10593 | 150-IleLeuAsnArgArgValCys-156 |
| SEQ. ID. NO. 10594 | 183-PheThrSerArgGlnProProSerAsnSerArgProProArgGlnAsnSer-199 |
| SEQ. ID. NO. 10595 | 213-LeuSerAlaLysAlaSerAla-219 |
| SEQ. ID. NO. 10596 | 271-SerSerAsnAspGlyAlaAla-277 |
| SEQ. ID. NO. 10597 | 294-CysPheArgArgArgArgIleArgIle-302 |
| 724 | |
| AMPHI Regions - AMPHI | |
| SEQ. ID. NO. 10598 | 6-LeuAlaLysLysThr-10 |
| SEQ. ID. NO. 10599 | 12-GlnThrAlaLysAsnIleGlyGluThrLeuArg-22 |
| SEQ. ID. NO. 10600 | 40-ArgValGlnLeuSer-44 |
| SEQ. ID. NO. 10601 | 47-AlaAspGluThrLeuGlnAspLeuGluHisLeuGlnGlu-59 |
| Antigenic Index - Jameson-Wolf | |
| SEQ. ID. NO. 10602 | 5-LysLeuAlaLysLysThrAlaGlnThrAlaLysAsnIleGlyGluThrLeuArgAlaAlaPheArgGlyLysIle-29 |
| SEQ. ID. NO. 10603 | 34-SerSerGluProIleGlnArgValGlnLeuSerGlyLeuAlaAspGluThrLeuGlnAspLeuGluHis-56 |
| SEQ. ID. NO. 10604 | 60-TyrGlyPheAlaSerHisProProAspGlySerGluAla-72 |
| SEQ. ID. NO. 10605 | 77-LeuGlyGlyAsnThrSer-82 |
| SEQ. ID. NO. 10606 | 90-GlnHisGlySerTyrArgIleLysAsnLeuLysProGlyGluThr-104 |
| SEQ. ID. NO. 10607 | 108-AsnHisGluGlyAlaLysIleValIleLysGlnGlyLysIleIleGluAlaAspCysAspVal-128 |
| SEQ. ID. NO. 10608 | 130-ArgValAsnCysLysGlnTyrGlu-137 |
| SEQ. ID. NO. 10609 | 142-ThrAspAlaLysPhe-146 |
| SEQ. ID. NO. 10610 | 162-GlnIleAsnGlyAsnGly-167 |
| SEQ. ID. NO. 10611 | 170-AlaValGluGlyGlyAspGlyAlaThrPheSerGlyAspValAsnGlnThrGlyGlySerPheAsnThrAspGlyAspValValAla-198 |
| SEQ. ID. NO. 10612 | 205-GlnHisProHisThrAspSerIleGlyGlyLysThrLeuProAlaGluProAla-222 |
| Hydrophilic Regions - Hopp-Woods | |
| SEQ. ID. NO. 10613 | 5-LysLeuAlaLysLysThrAlaGlnThrAlaLysAsnIleGlyGluThrLeuArgAlaAlaPheArgGly-27 |
| SEQ. ID. NO. 10614 | 46-LeuAlaAspGluThrLeuGlnAspLeuGluHis-56 |
| SEQ. ID. NO. 10615 | 66-ProProAspGlySerGlu-71 |
| SEQ. ID. NO. 10616 | 94-TyrArgIleLysAsnLeuLysProGlyGlu-103 |
| SEQ. ID. NO. 10617 | 110-GluGlyAlaLysIleValIleLysGlnGlyLysIleIleGluAlaAspCysAspVal-128 |
| SEQ. ID. NO. 10618 | 132-AsnCysLysGlnTyrGlu-137 |
| SEQ. ID. NO. 10619 | 142-ThrAspAlaLysPhe-146 |
| SEQ. ID. NO. 10620 | 190PheAsnThrAspGlyAspVal-196 |
| SEQ. ID. NO. 10621 | 205-GlnHisProHisThrAspSerIleGly-213 |
| 725 | |
| AMPHI Regions - AMPHI | |
| SEQ. ID. NO. 10622 | 11-GluAlaAspAspLeuAlaGlyGlnIleHisThrLeuProAlaValTrp-26 |
| SEQ. ID. NO. 10623 | 41-GlyValCysGlyArgTyrGlnAsp-48 |
| SEQ. ID. NO. 10624 | 81-AspLeuIleArgAlaValArgArgLeuLeuAsp-91 |
| SEQ. ID. NO. 10625 | 104-ValProLysAlaValArgAlaIle-111 |
| SEQ. ID. NO. 10626 | 144-ProGluArgThrAspAsnProAsp-151 |
| SEQ. ID. NO. 10627 | 155-HisIlePheThrLysTyrGlnGlyThrLeuSerGluProTrpProAspPheGlu-172 |
| SEQ. ID. NO. 10628 | 180-AspProGlnSerAla-184 |
| Antigenic Index - Jameson-Wolf | |
| SEQ. ID. NO. 10629 | 3-ArgThrValLysSerTyrAsnGlyGluAlaAspAspLeuAla-16 |
| SEQ. ID. NO. 10630 | 29-TyrGlyGlySerLysValGluProAlaSerThrGlyGlyValCysGlyArgTyrGlnAspThrAla-50 |
| SEQ. ID. NO. 10631 | 59-ArgAsnLeuArgAsnGluGlnAlaGlnArgGlnGlyGlyIleAspSerArgGluIleGlySerAsnAspLeuIleArgAlaValArgArgLeuLeuAsp GlyGlnArgLeuGlyPheAlaAspSerArgGlyLeuValProLysAlaValArg-109 |
| SEQ. ID. NO. 10632 | 134-AsnThrCysGlyLeuGluAsnAspArgTyrProGluArgThrAspAsnProAspAspProAsn-154 |
| SEQ. ID. NO. 10633 | 160-TyrGlnGlyThrLeuSerGluProTrpProAspPheGluGlyLeuAspGlyLysIleTyrAspProGlnSerAlaAspGluIlePro-188 |
| SEQ. ID. NO. 10634 | 192-ThrLeuLysAspLysGln-197 |
| Hydrophilic Regions - Hopp-Woods | |
| SEQ. ID. NO. 10635 | 8-TyrAsnGlyGluAlaAspAspLeuAla-16 |
| SEQ. ID. NO. 10636 | 32-SerLysValGluProAlaSer-38 |
| SEQ. ID. NO. 10637 | 45-ArgTyrGlnAspThrAla-50 |
| SEQ. ID. NO. 10638 | 59-ArgAsnLeuArgAsnGluGlnAlaGlnArgGlnGlyGlyIleAspSerArgGluIleGlySer-79 |
| SEQ. ID. NO. 10639 | 81-AspLeuIleArgAlaValArgArgLeuLeuAspGlyGlnArg-94 |
| SEQ. ID. NO. 10640 | 96-GlyPheAlaAspSerArgGlyLeuVal-104 |
| SEQ. ID. NO. 10641 | 137-GlyLeuGluAsnAspArgTyrProGluArgThrAspAsnProAspAspProAsn-154 |
| SEQ. ID. NO. 10642 | 172-GluGlyLeuAspGlyLysIleTyrAsp-180 |

TABLE 1-continued

| | |
|---|---|
| SEQ. ID. NO. 10643 | 182-GlnSerAlaAspGluIlePro-188 |
| SEQ. ID. NO. 10644 | 192-ThrLeuLysAspLysGln-197 |
| 726 | |
| AMPHI Regions - AMPHI | |
| SEQ. ID. NO. 10645 | 12-AspThrLeuGlyGlyIleProGlu-19 |
| SEQ. ID. NO. 10646 | 55-ProArgProSerAspTyrHisGlu-62 |
| SEQ. ID. NO. 10647 | 74-AlaAlaAlaAlaArg-78 |
| SEQ. ID. NO. 10648 | 110-IleAspSerPheTyrArg-115 |
| SEQ. ID. NO. 10649 | 122-AlaArgGlnAlaAsp-126 |
| SEQ. ID. NO. 10650 | 137-IleAlaAlaAlaArg-141 |
| SEQ. ID. NO. 10651 | 180-IleGluThrAlaProGlyLeuAspAlaLeuGluLysGluIleGlu-194 |
| Antigenic Index - Jameson-Wolf | |
| SEQ. ID. NO. 10652 | 5-PheLysAsnGlyPheTyrAspAspThrLeuGlyGlyIleProGluGly-20 |
| SEQ. ID. NO. 10653 | 24-ValArgAlaGluGluTyr-29 |
| SEQ. ID. NO. 10654 | 37-AlaGlnGlyGlyGlnIleAlaAlaAspSerAspGlyArgProValLeuThrProProArgProSerAspTyrHisGluTrpAspGlyLysLysTrpLys IleSerLys-72 |
| SEQ. ID. NO. 10655 | 78-ArgPheAlaLysGlnLysThr-84 |
| SEQ. ID. NO. 10656 | 90-LeuAlaGluLysAlaAspGluLeuLysAsnSer-100 |
| SEQ. ID. NO. 10657 | 106-ProGlnValGluIleAspSerPheTyrArgGlnGluLysGluAlaLeuAlaArgGlnAlaAspAsnAsnAlaProThr-131 |
| SEQ. ID. NO. 10658 | 151-LysValIleGluLysSerAlaArg-158 |
| SEQ. ID. NO. 10659 | 167-IleGlyLysArgGlnGlnLeuGluAspLysLeuAsnThr-179 |
| SEQ. ID. NO. 10660 | 181-GluThrAlaProGlyLeuAspAlaLeuGluLysGluIleGluGlu-195 |
| Hydrophilic Regions - Hopp-Woods | |
| SEQ. ID. NO. 10661 | 24-ValArgAlaGluGluTyr-29 |
| SEQ. ID. NO. 10662 | 42-IleAlaAlaAspSerAspGlyArgPro-50 |
| SEQ. ID. NO. 10663 | 55-ProArgProSerAspTyrHisGluTrpAspGlyLysLysTrpLysIleSerLys-72 |
| SEQ. ID. NO. 10664 | 78-ArgPheAlaLysGlnLysThr-84 |
| SEQ. ID. NO. 10665 | 90-LeuAlaGluLysAlaAspGluLeuLysAsn-99 |
| SEQ. ID. NO. 10666 | 114-TyrArgGlnGluLysGluAlaLeuAlaArgGlnAlaAspAsnAsnAla-129 |
| SEQ. ID. NO. 10667 | 151-LysValIleGluLysSerAlaArg-158 |
| SEQ. ID. NO. 10668 | 167-IleGlyLysArgGlnGlnLeuGluAspLysLeuAsnThr-179 |
| SEQ. ID. NO. 10669 | 187-AspAlaLeuGluLysGluIleGluGlu-195 |
| 727 | |
| AMPHI Regions - AMPHI | |
| SEQ. ID. NO. 10670 | 6-LeuLeuAlaAsnAsn-10 |
| SEQ. ID. NO. 10671 | 12-GlnProIleAlaIleIleAla-18 |
| Antigenic Index - Jameson-Wolf | |
| SEQ. ID. NO. 10672 | 28-HisHisGlnGlyTyrLysSerAlaPheAlaLysGln-39 |
| SEQ. ID. NO. 10673 | 41-AlaValIleAspLysMetGluArgAspLysAlaGln-52 |
| SEQ. ID. NO. 10674 | 60-AsnTyrAlaArgGluLeuGluLeuAlaArgAlaGluAlaLysLysTyrGluValLysAla-79 |
| SEQ. ID. NO. 10675 | 86-LeuAlaLysLysGlnAlaGluValSerArgLeuLysThrGluArgAspLeuCysLys-104 |
| SEQ. ID. NO. 10676 | 106-ProPheProProAspSerArgAsnProAsnThrGlyPhe-118 |
| SEQ. ID. NO. 10677 | 122-SerProGlnIleProProAsnPhe-129 |
| Hydrophilic Regions - Hopp-Woods | |
| SEQ. ID. NO. 10678 | 41-AlaValIleAspLysMetGluArgAspLysAlaGln-52 |
| SEQ. ID. NO. 10679 | 60-AsnTyrAlaArgGluLeuGluLeuAlaArgAlaGluAlaLysLysTyrGluValLysAla-79 |
| SEQ. ID. NO. 10680 | 86-LeuAlaLysLysGlnAlaGluValSerArgLeuLysThrGluArgAspLeuCys-103 |
| SEQ. ID. NO. 10681 | 109-ProAspSerArgAsnProAsnThr-116 |
| 728 | |
| AMPHI Regions - AMPHI | |
| SEQ. ID. NO. 10682 | 11-SerPhePheAlaLeuValPheAla-18 |
| SEQ. ID. NO. 10683 | 39-AlaThrGluValProLysAsnPro-46 |
| SEQ. ID. NO. 10684 | 48-AlaPheValAlaLysLeuAlaArgLeuPheArgAsnAla-60 |
| SEQ. ID. NO. 10685 | 76-AsnLeuAlaGlyThrValAspAsp-83 |
| SEQ. ID. NO. 10686 | 198-GluAspValTyrGluHisCysLeuGlyCysTyrGlnMet-210 |
| SEQ. ID. NO. 10687 | 218-TyrArgAspValAlaAsnAspGlu-225 |
| SEQ. ID. NO. 10688 | 235-SerAsnArgIleAlaSer-240 |
| SEQ. ID. NO. 10689 | 249-GlnAsnMetArgGluLeuMetProArg-257 |
| SEQ. ID. NO. 10690 | 355-GluLysGluValArgArgTyrAlaGluAlaAlaAlaArg-367 |
| Antigenic Index - Jameson-Wolf | |
| SEQ. ID. NO. 10691 | 29-IleAsnProArgTrp-33 |
| SEQ. ID. NO. 10692 | 35-LeuSerAspThrAlaThrGluValProLysAsnProAsn-47 |
| SEQ. ID. NO. 10693 | 57-PheArgAsnAlaAspArgAla-63 |
| SEQ. ID. NO. 10694 | 69-GluSerIleArgThrGluGluAsnLeuAlaGlyThrValAspAspGlyProLeuGlnSerGluLysAspTyr-92 |
| SEQ. ID. NO. 10695 | 98-ArgLeuSerArgLeuLysGluLysAlaLys-107 |
| SEQ. ID. NO. 10696 | 112-ThrGluGlnGluHisGlyLys-118 |
| SEQ. ID. NO. 10697 | 125-HisIleGlyGluGlyGly-130 |
| SEQ. ID. NO. 10698 | 136-LeuSerGlnArgSerProGluAlaPheVal-145 |
| SEQ. ID. NO. 10699 | 149-TyrLeuTyrArgAsnAspArgProPheSer-158 |
| SEQ. ID. NO. 10700 | 166-ValHisGlyGluAsnTyrGluThrThrGlyGluTyrArgVal-179 |
| SEQ. ID. NO. 10701 | 182-GlnProAspGlySerVal-187 |
| SEQ. ID. NO. 10702 | 190-AlaAlaGlyArgGlyLysIleGlyGluAspValTyr-201 |
| SEQ. ID. NO. 10703 | 217-LysTyrArgAspValAlaAsnAspGluGlnLysValTrpAspPheArgLysGluSerAsnArgIleAlaSerAspSerArgAsnSerValPheTyrGln AsnMetArgGluLeuMetProArgGlyMetLysAlaAsnSer-263 |
| SEQ. ID. NO. 10704 | 267-GlyTyrAspAlaAspGlyLeuProGlnLys-276 |
| SEQ. ID. NO. 10705 | 280-SerPheAspAsnGlyLysLysArgGlnSerPheGluTyrTyrLeuLysAsnGlyAsn-298 |
| SEQ. ID. NO. 10706 | 309-LeuLysAlaAspGlyValThr-315 |
| SEQ. ID. NO. 10707 | 329-LeuAspGlyGlyArgIleValArgGluGluLysGlnGlyAspArgLeuProAspPhe-347 |
| SEQ. ID. NO. 10708 | 352-GluAsnLeuGluLysGluValArgArgTyrAlaGluAlaAlaAlaArgArgSerGlyGlyArgArgAspLeuSerHis-377 |

TABLE 1-continued

| | |
|---|---|
| Hydrophilic Regions - Hopp-Woods | |
| SEQ. ID. NO. 10709 | 38-ThrAlaThrGluValProLysAsnPro-46 |
| SEQ. ID. NO. 10710 | 57-PheArgAsnAlaAspArgAla-63 |
| SEQ. ID. NO. 10711 | 69-GluSerIleArgThrGluGluAsnLeu-77 |
| SEQ. ID. NO. 10712 | 80-ThrValAspAspGlyProLeuGlnSerGluLysAspTyr-92 |
| SEQ. ID. NO. 10713 | 98-ArgLeuSerArgLeuLysGluLysAlaLys-107 |
| SEQ. ID. NO. 10714 | 112-ThrGluGlnGluHisGlyLys-118 |
| SEQ. ID. NO. 10715 | 136-LeuSerGlnArgSerProGlu-142 |
| SEQ. ID. NO. 10716 | 151-TyrArgAsnAspArgProPhe-157 |
| SEQ. ID. NO. 10717 | 169-GluAsnTyrGluThrThrGlyGluTyr-177 |
| SEQ. ID. NO. 10718 | 190-AlaAlaGlyArgGlyLysIleGlyGluAspValTyr-201 |
| SEQ. ID. NO. 10719 | 217-LysTyrArgAspValAlaAsnAspGluGlnLysValTrpAspPheArgLysGluSerAsnArgIleAlaSerAspSerArgAsn-244 |
| SEQ. ID. NO. 10720 | 250-AsnMetArgGluLeuMetProArgGlyMetLys-260 |
| SEQ. ID. NO. 10721 | 268-TyrAspAlaAspGlyLeuPro-274 |
| SEQ. ID. NO. 10722 | 282-AspAsnGlyLysLysArgGlnSer-289 |
| SEQ. ID. NO. 10723 | 309-LeuLysAlaAspGlyValThr-315 |
| SEQ. ID. NO. 10724 | 331-GlyGlyArgIleValArgGluGluLysGlnGlyAspArgLeuPro-345 |
| SEQ. ID. NO. 10725 | 352-GluAsnLeuGluLysGluValArgArgTyrAlaGluAlaAlaAlaArgArgSerGlyGlyArgArgAspLeuSerHis-377 |
| 729 | |
| AMPHI Regions - AMPHI | |
| SEQ. ID. NO. 10726 | 21-CysThrMetIleProGlnTyr-27 |
| SEQ. ID. NO. 10727 | 33-GluValAlaGluThrPheLysAsnAspThr-42 |
| SEQ. ID. NO. 10728 | 55-HisAspTyrPheAla-59 |
| SEQ. ID. NO. 10729 | 61-ProArgLeuGlnLysLeuIleAspIle-69 |
| SEQ. ID. NO. 10730 | 149-GlnGlyTyrPheAla-153 |
| SEQ. ID. NO. 10731 | 164-SerLeuIleAlaThrValAlaLys-171 |
| SEQ. ID. NO. 10732 | 242-LeuAlaThrLeuIleAsn-247 |
| SEQ. ID. NO. 10733 | 268-LysLeuProAlaGlyLeu-273 |
| SEQ. ID. NO. 10734 | 322-LeuGlyGlyLeuPheLysSerGly-329 |
| SEQ. ID. NO. 10735 | 371-ValGlnSerAlaPheGlnAspValAlaAsnAla-381 |
| SEQ. ID. NO. 10736 | 388-LeuAspLysAlaTyrAspAlaLeuSerLysGlnSerArg-400 |
| SEQ. ID. NO. 10737 | 419-GlyAlaLeuAspLeuLeuAspAla-426 |
| SEQ. ID. NO. 10738 | 442-LeuThrArgAlaGluAsnLeuAlaAspLeuTyrLysAlaLeuGlyGlyGlyLeuLys-460 |
| Antigenic Index - Jameson-Wolf | |
| SEQ. ID. NO. 10739 | 25-ProGlnTyrGluGlnProLysValGluVal-34 |
| SEQ. ID. NO. 10740 | 36-GluThrPheLysAsnAspThrAlaAspSerGlyIleArgAlaValAsp-51 |
| SEQ. ID. NO. 10741 | 53-GlyTrpHisAspTyrPheAlaAspProArgLeuGlnLys-65 |
| SEQ. ID. NO. 10742 | 70-AlaLeuGluArgAsnThrSerLeuArgThr-79 |
| SEQ. ID. NO. 10743 | 85-GluIleTyrArgLysGlnTyrMetIleGluArgAsnAsnLeuLeuPro-100 |
| SEQ. ID. NO. 10744 | 105-AsnAlaAsnAspSerArgGlnGlySerLeuSerGlyGlyAsnValSerSerSerTyrLysVal-125 |
| SEQ. ID. NO. 10745 | 138-GlyArgValArgSerSerSerGluAlaAla-147 |
| SEQ. ID. NO. 10746 | 155-ThrAlaAsnArgAspAlaAla-161 |
| SEQ. ID. NO. 10747 | 173-TyrPheAsnGluArgTyrAlaGluGluAlaMet-183 |
| SEQ. ID. NO. 10748 | 188-ArgValLeuLysThrArgGluGluThrTyrLysLeuSerGluLeuArgTyr-204 |
| SEQ. ID. NO. 10749 | 215-ArgGlnGlnGluAlaLeuIleGluSerAlaLysAlaAspTyr-228 |
| SEQ. ID. NO. 10750 | 232-AlaArgSerArgGluGlnAlaArgAsn-240 |
| SEQ. ID. NO. 10751 | 248-GlnProIleProGluAspLeuProAla-256 |
| SEQ. ID. NO. 10752 | 277-ValLeuLeuAspArgProAspIleArgAlaAlaGluHisAlaLeuLysGlnAlaAsnAla-296 |
| SEQ. ID. NO. 10753 | 315-ValGlyThrGlySerAlaGluLeu-322 |
| SEQ. ID. NO. 10754 | 325-LeuPheLysSerGlyThr-330 |
| SEQ. ID. NO. 10755 | 347-GlyThrAsnLysAlaAsnLeuAspValAlaLysLeuArgGlnGln-361 |
| SEQ. ID. NO. 10756 | 383-AlaAlaArgGluGlnLeuAspLysAlaTyrAspAlaLeuSerLysGlnSerArgAlaSerLysGluAlaLeuArg-407 |
| SEQ. ID. NO. 10757 | 411-LeuArgTyrLysHisGlyValSer-418 |
| SEQ. ID. NO. 10758 | 424-LeuAspAlaGluArgSerSerTyrAla-432 |
| SEQ. ID. NO. 10759 | 442-LeuThrArgAlaGluAsnLeu-448 |
| SEQ. ID. NO. 10760 | 455-LeuGlyGlyGlyLeuLysArgAspThrGlnThrAspLys-467 |
| Hydrophilic Regions - Hopp-Woods | |
| SEQ. ID. NO. 10761 | 28-GluGlnProLysValGluVal-34 |
| SEQ. ID. NO. 10762 | 36-GluThrPheLysAsnAspThrAlaAspSerGlyIleArgAlaVal-50 |
| SEQ. ID. NO. 10763 | 61-ProArgLeuGlnLys-65 |
| SEQ. ID. NO. 10764 | 70-AlaLeuGluArgAsnThrSerLeu-77 |
| SEQ. ID. NO. 10765 | 91-TyrMetIleGluArgAsnAsn-97 |
| SEQ. ID. NO. 10766 | 105-AsnAlaAsnAspSerArgGlnGlySer-113 |
| SEQ. ID. NO. 10767 | 138-GlyArgValArgSerSerSerGluAlaAla-147 |
| SEQ. ID. NO. 10768 | 156-AlaAsnArgAspAlaAla-161 |
| SEQ. ID. NO. 10769 | 177-ArgTyrAlaGluGluAlaMet-183 |
| SEQ. ID. NO. 10770 | 188-ArgValLeuLysThrArgGluGluThrTyrLysLeuSerGluLeuArgTyr-204 |
| SEQ. ID. NO. 10771 | 215-ArgGlnGlnGluAlaLeuIleGluSerAlaLysAlaAspTyr-228 |
| SEQ. ID. NO. 10772 | 232-AlaArgSerArgGluGlnAlaArgAsn-240 |
| SEQ. ID. NO. 10773 | 250-IleProGluAspLeuPro-255 |
| SEQ. ID. NO. 10774 | 277-ValLeuLeuAspArgProAspIleArgAlaAlaGluHisAlaLeuLysGlnAlaAsn-295 |
| SEQ. ID. NO. 10775 | 350-LysAlaAsnLeuAspValAlaLysLeuArgGln-360 |
| SEQ. ID. NO. 10776 | 383-AlaAlaArgGluGlnLeuAspLysAlaTyrAspAlaLeuSerLysGlnSerArgAlaSerLysGluAlaLeuArg-407 |
| SEQ. ID. NO. 10777 | 424-LeuAspAlaGluArgSerSerTyrAla-432 |
| SEQ. ID. NO. 10778 | 442-LeuThrArgAlaGluAsnLeu-448 |
| SEQ. ID. NO. 10779 | 458-GlyLeuLysArgAspThrGlnThrAspLys-467 |
| 730 | |
| AMPHI Regions - AMPHI | |
| SEQ. ID. NO. 10780 | 6-ArgLeuThrAsnLeuLeuAlaAlaCys-14 |
| SEQ. ID. NO. 10781 | 26-LeuAlaAlaAspLeu-30 |

TABLE 1-continued

| | |
|---|---|
| SEQ. ID. NO. 10782 | 67-LysIleAsnValIleGlnAspTyrThrHisGln-77 |
| SEQ. ID. NO. 10783 | 111-AsnHisAlaAlaAsp-115 |
| SEQ. ID. NO. 10784 | 141-HisProAlaAspAlaTyrAspGlyProLysGlyGlyAsnTyrProLysProThr-158 |
| SEQ. ID. NO. 10785 | 187-GlnArgIleSerAspAsnTyrSerAsnLeuGlySerAsnPheSerAspArgAlaAspGlu-206 |
| SEQ. ID. NO. 10786 | 214-HisAsnAlaLysLeu-218 |
| SEQ. ID. NO. 10787 | 220-ArgTrpGlyAsnSerMetGluPheIleAsnGlyValAla-232 |
| SEQ. ID. NO. 10788 | 234-GlyAlaLeuAsnProPheIleSer-241 |
| SEQ. ID. NO. 10789 | 262-AlaAlaMetArgAsnIleAla-268 |
| SEQ. ID. NO. 10790 | 277-AlaValIleGlyGlyLeuGlySerValAlaGlyPheGluLysAsnThrArgGluAlaValAspArgTrpIleGlnGlu-302 |
| SEQ. ID. NO. 10791 | 305-AsnAlaAlaGluThrValGluAlaValPheAsnValAlaAlaAlaAlaLysValAlaLysLeuAlaLysAlaAlaLysPro-331 |
| SEQ. ID. NO. 10792 | 338-GlyAspPheAlaAspSerTyr-344 |
| SEQ. ID. NO. 10793 | 387-AsnGlyArgGluIleAspAlaVal-394 |
| SEQ. ID. NO. 10794 | 405-ThrIleSerAlaIleAspLysProLys-413 |
| Antigenic Index - Jameson-Wolf | |
| SEQ. ID. NO. 10795 | 2-LysProLeuArgArgLeuThr-8 |
| SEQ. ID. NO. 10796 | 35-PheIleThrAspAsnAlaGlnArgGlnHisTyrGluProGlyGlyLys-50 |
| SEQ. ID. NO. 10797 | 55-GlyAspProArgGlySerValSerAspArgThrGlyLysIleAsnVal-70 |
| SEQ. ID. NO. 10798 | 97-ArgPheSerGlyHisGlyHisGluGluHisAlaProPheAsp-110 |
| SEQ. ID. NO. 10799 | 112-HisAlaAlaAspSerAlaSerGluGluLysGlyAsnValAspGluGlyPhe-128 |
| SEQ. ID. NO. 10800 | 134-AsnTrpGluGlyHisGluHisHisProAlaAspAlaTyrAspGlyProLysGlyGlyAsnTyrProLysProThrGlyAlaArgAspGluTyrThr-165 |
| SEQ. ID. NO. 10801 | 167-HisValAsnGlyThrAlaArgSerIleLysLeuAsnProThrAspThrArgSerIleArgGlnArgIleSerAspAsnTyrSerAsn-195 |
| SEQ. ID. NO. 10802 | 197-GlySerAsnPheSerAspArgAlaAspGluAlaAsnArgLysMetPheGluHisAsnAlaLysLeuAspArgTrpGlyAsnSer-224 |
| SEQ. ID. NO. 10803 | 257-TyrAlaIleAspLysAlaAlaMet-264 |
| SEQ. ID. NO. 10804 | 271-ProAlaGluGlyLys-275 |
| SEQ. ID. NO. 10805 | 287-GlyPheGluLysAsnThrArgGluAlaValAsp-297 |
| SEQ. ID. NO. 10806 | 299-TrpIleGlnGluAsnProAsnAlaAlaGluThrVal-310 |
| SEQ. ID. NO. 10807 | 321-LysValAlaLysLeuAlaLysAlaAlaLysProGlyLysAlaAlaValSerGlyAspPheAlaAspSerTyrLysLysLysLeuAlaLeuSerAspSerAlaArgGln-356 |
| SEQ. ID. NO. 10808 | 359-GlnAsnAlaLysTyrArgGluAlaLeu-367 |
| SEQ. ID. NO. 10809 | 373-AspLeuIleArgArgLysThrAspGlySerSerLysPheIleAsnGlyArgGluIleAspAlaValThrAsnAsp-397 |
| SEQ. ID. NO. 10810 | 400-IleGlnAlaLysArgThrIleSerAlaIleAspLysProLysAsnPheLeuAsnGlnLysAsnArgLysGlnIleLysAlaThrIle-428 |
| SEQ. ID. NO. 10811 | 430-AlaAlaAsnGlnGlnGlyLysArgAlaGluPhe-440 |
| SEQ. ID. NO. 10812 | 452-SerTyrIleGluSerLysGlyGlyIleValLysThrGlyLeuGlyAsp-467 |
| Hydrophilic Regions - Hopp-Woods | |
| SEQ. ID. NO. 10813 | 2-LysProLeuArgArgLeuThr-8 |
| SEQ. ID. NO. 10814 | 39-AsnAlaGlnArgGlnHisTyrGluProGlyGly-49 |
| SEQ. ID. NO. 10815 | 55-GlyAspProArgGlySerValSerAspArgThrGlyLys-67 |
| SEQ. ID. NO. 10816 | 102-GlyHisGluGluHisAlaPro-108 |
| SEQ. ID. NO. 10817 | 112-HisAlaAlaAspSerAlaSerGluGluLysGlyAsnValAspGluGly-127 |
| SEQ. ID. NO. 10818 | 135-TrpGluGlyHisGluHisHisPro-142 |
| SEQ. ID. NO. 10819 | 144-AspAlaTyrAspGlyProLysGlyGlyAsnTyrProLys-156 |
| SEQ. ID. NO. 10820 | 158-ThrGlyAlaArgAspGluTyr-164 |
| SEQ. ID. NO. 10821 | 170-GlyThrAlaArgSerIleLys-176 |
| SEQ. ID. NO. 10822 | 178-AsnProThrAspThrArgSerIleArgGlnArgIleSerAsp-191 |
| SEQ. ID. NO. 10823 | 200-PheSerAspArgAlaAspGluAlaAsnArgLysMetPheGluHisAsnAlaLysLeuAspArgTrpGlyAsn-223 |
| SEQ. ID. NO. 10824 | 257-TyrAlaIleAspLysAlaAlaMet-264 |
| SEQ. ID. NO. 10825 | 271-ProAlaGluGlyLys-275 |
| SEQ. ID. NO. 10826 | 287-GlyPheGluLysAsnThrArgGluAlaValAsp-297 |
| SEQ. ID. NO. 10827 | 303-AsnProAsnAlaAlaGluThrVal-310 |
| SEQ. ID. NO. 10828 | 321-LysValAlaLysLeuAlaLysAlaAlaLysProGlyLysAlaAlaVal-336 |
| SEQ. ID. NO. 10829 | 339-AspPheAlaAspSerTyrLysLysLysLeuAlaLeu-350 |
| SEQ. ID. NO. 10830 | 361-AlaLysTyrArgGluAlaLeu-367 |
| SEQ. ID. NO. 10831 | 373-AspLeuIleArgArgLysThrAspGlySerSer-383 |
| SEQ. ID. NO. 10832 | 386-IleAsnGlyArgGluIleAspAlaValThr-395 |
| SEQ. ID. NO. 10833 | 400-IleGlnAlaLysArgThrIleSerAlaIleAspLysProLysAsn-414 |
| SEQ. ID. NO. 10834 | 418-GlnLysAsnArgLysGlnIleLysAlaThrIle-428 |
| SEQ. ID. NO. 10835 | 430-AlaAlaAsnGlnGlnGlyLysArgAlaGluPhe-440 |
| SEQ. ID. NO. 10836 | 452-SerTyrIleGluSerLysGlyGlyIle-460 |
| 731 | |
| AMPHI Regions - AMPHI | |
| SEQ. ID. NO. 10837 | 17-AlaCysAlaValPro-21 |
| Antigenic Index - Jameson-Wolf | |
| SEQ. ID. NO. 10838 | 22-GluAlaTyrAspAspGlyGlyArgGlyHis-31 |
| SEQ. ID. NO. 10839 | 34-ProValGlnAsnGlnAlaGlyThrAspAspPheArg-45 |
| SEQ. ID. NO. 10840 | 48-SerCysGluAsnGlyLeu-53 |
| SEQ. ID. NO. 10841 | 55-ValArgValArgHisLeuAspSerGlyLysValAlaLeuArgLeuAspGlyArgArgAlaValLeuSerSerAspValAlaAlaSerGlyGluArgTyrThrAla-89 |
| SEQ. ID. NO. 10842 | 98-ThrGluTrpHisGlnLysGlyGlyGluAla-107 |
| SEQ. ID. NO. 10843 | 113-AspAlaTyrGlyAsnSerValGluThrSerCysArgAlaArg-126 |
| Hydrophilic Regions - Hopp-Woods | |
| SEQ. ID. NO. 10844 | 22-GluAlaTyrAspAspGlyGlyArgGlyHis-31 |
| SEQ. ID. NO. 10845 | 39-AlaGlyThrAspAspPheArg-45 |
| SEQ. ID. NO. 10846 | 55-ValArgValArgHisLeuAspSerGlyLysValAlaLeuArgLeuAspGlyArgArgAlaValLeu-76 |
| SEQ. ID. NO. 10847 | 80-ValAlaAlaSerGlyGluArgTyrThrAla-89 |
| SEQ. ID. NO. 10848 | 100-TrpHisGlnLysGlyGlyGlu-106 |
| SEQ. ID. NO. 10849 | 119-ValGluThrSerCysArgAlaArg-126 |
| 732 | |
| AMPHI Regions - AMPHI | |
| SEQ. ID. NO. 10850 | 14-LeuGlyAlaIleSer-18 |
| SEQ. ID. NO. 10851 | 43-ValGlnSerIleArgThrMetAlaGluValTyrGly-54 |

TABLE 1-continued

| | |
|---|---|
| SEQ. ID. NO. 10852 | 66-AspAlaAspLeuPheGluGlyAlaMetLysGlyMetVal-78 |
| SEQ. ID. NO. 10853 | 95-GluIleLysGluSerThrSerGly-102 |
| SEQ. ID. NO. 10854 | 115-AspGlyPheValLysValValSerProIleGluAsp-126 |
| SEQ. ID. NO. 10855 | 155-GluAlaValLysLysMet-160 |
| SEQ. ID. NO. 10856 | 183-ValAsnLeuThrArg-187 |
| SEQ. ID. NO. 10857 | 214-GluArgThrValGluSerValAsnThrAlaAlaLys-225 |
| SEQ. ID. NO. 10858 | 283-LysAlaIleProGluAsp-288 |
| SEQ. ID. NO. 10859 | 297-SerLeuAlaGlyIleProAlaGluLeu-305 |
| SEQ. ID. NO. 10860 | 322-SerGluIleValAlaGly-327 |
| SEQ. ID. NO. 10861 | 400-LeuValGlyHisIleGlyAsn-406 |
| SEQ. ID. NO. 10862 | 446-ArgArgIleProAsnProAlaLysAsp-454 |
| SEQ. ID. NO. 10863 | 459-LysAlaLeuAspLeuValLysSerProGluGlnTrpGlnLysSerLeu-474 |
| Antigenic Index - Jameson-Wolf | |
| SEQ. ID. NO. 10864 | 30-AlaAlaGluLysAspArgArgAspAsnGluVal-40 |
| SEQ. ID. NO. 10865 | 59-AsnTyrTyrGlnAspLysProAspAlaAspLeuPhe-70 |
| SEQ. ID. NO. 10866 | 82-AspProHisSerGluTyrMetAspLysLysGlyTyrAlaGluIleLysGluSerThrSerGlyGluPheGlyGly-106 |
| SEQ. ID. NO. 10867 | 111-IleGlyGlnGluAspGlyPhe-117 |
| SEQ. ID. NO. 10868 | 122-SerProIleGluAspThrProAlaGluArgAlaGlyValLysSerGlyAspPhe-139 |
| SEQ. ID. NO. 10869 | 144-AspAsnValSerThrArgGlyMetThr-152 |
| SEQ. ID. NO. 10870 | 155-GluAlaValLysLysMetArgGlyLysProGlyThrLysIle-168 |
| SEQ. ID. NO. 10871 | 172-LeuSerArgLysAsnAlaAspLysProIle-181 |
| SEQ. ID. NO. 10872 | 199-LeuIleGluProAspTyrGlyTyr-206 |
| SEQ. ID. NO. 10873 | 211-GlnPheGlnGluArgThrValGlu-218 |
| SEQ. ID. NO. 10874 | 221-AsnThrAlaAlaLysGluLeuValLysGluAsnLysGlyLysProLeuLys-237 |
| SEQ. ID. NO. 10875 | 242-AspLeuArgAspAspProGlyGlyLeu-250 |
| SEQ. ID. NO. 10876 | 269-ValSerThrLysGlyArgAspGlyLysAspArgMetVal-281 |
| SEQ. ID. NO. 10877 | 284-AlaIleProGluAspTyr-289 |
| SEQ. ID. NO. 10878 | 292-GlyMetGlyGlyAspSer-297 |
| SEQ. ID. NO. 10879 | 303-AlaGluLeuLysThr-307 |
| SEQ. ID. NO. 10880 | 316-SerGlySerAlaSerAla-321 |
| SEQ. ID. NO. 10881 | 330-GlnAspHisLysArgAlaVal-336 |
| SEQ. ID. NO. 10882 | 340-ThrGlnSerPheGlyLysGlySerVal-348 |
| SEQ. ID. NO. 10883 | 354-LeuSerAsnGlySer-358 |
| SEQ. ID. NO. 10884 | 368-TyrThrProAsnAspArgSerIleGln-376 |
| SEQ. ID. NO. 10885 | 384-ValGluValLysAspLysGluArgIlePheGluSerArgGluAlaAspLeu-400 |
| SEQ. ID. NO. 10886 | 405-GlyAsnProLeuGlyGlyGluAspValAsnGly-415 |
| SEQ. ID. NO. 10887 | 421-ProLeuGluLysAspAlaAspLysProAlaValLysGluLysGlyLysLysLysLysAspGluAspLeuSerSerArgArgIleProAsnProAlaLys AspAspGlnLeuArgLysAlaLeuAspLeuValLysSerProGluGlnTrpGlnLys-472 |
| SEQ. ID. NO. 10888 | 477-AlaAlaLysLysProValSerAsnLysAspLysLysAspLysLysAspLysLys-494 |
| Hydrophilic Regions - Hopp-Woods | |
| SEQ. ID. NO. 10889 | 30-AlaAlaGluLysAspArgArgAspAsnGluVal-40 |
| SEQ. ID. NO. 10890 | 60-TyrTyrGlnAspLysProAspAlaAspLeuPhe-70 |
| SEQ. ID. NO. 10891 | 82-AspProHisSerGluTyrMetAspLysLysGlyTyrAlaGluIleLysGluSerThrSerGlyGlu-103 |
| SEQ. ID. NO. 10892 | 111-IleGlyGlnGluAspGlyPhe-117 |
| SEQ. ID. NO. 10893 | 122-SerProIleGluAspThrProAlaGluArgAlaGlyValLysSerGlyAspPhe-139 |
| SEQ. ID. NO. 10894 | 144-AspAsnValSerThr-148 |
| SEQ. ID. NO. 10895 | 155-GluAlaValLysLysMetArgGlyLysProGlyThr-166 |
| SEQ. ID. NO. 10896 | 172-LeuSerArgLysAsnAlaAspLysProIle-181 |
| SEQ. ID. NO. 10897 | 211-GlnPheGlnGluArgThrValGlu-218 |
| SEQ. ID. NO. 10898 | 221-AsnThrAlaAlaLysGluLeuValLysGluAsnLysGlyLysProLeuLys-237 |
| SEQ. ID. NO. 10899 | 242-AspLeuArgAspAspProGly-248 |
| SEQ. ID. NO. 10900 | 271-ThrLysGlyArgAspGlyLysAspArgMetVal-281 |
| SEQ. ID. NO. 10901 | 303-AlaGluLeuLysThr-307 |
| SEQ. ID. NO. 10902 | 330-GlnAspHisLysArgAlaVal-336 |
| SEQ. ID. NO. 10903 | 370-ProAsnAspArgSerIleGln-376 |
| SEQ. ID. NO. 10904 | 384-ValGluValLysAspLysGluArgIlePheGluSerArgGluAlaAspLeu-400 |
| SEQ. ID. NO. 10905 | 408-LeuGlyGlyGluAspValAsnGly-415 |
| SEQ. ID. NO. 10906 | 421-ProLeuGluLysAspAlaAspLysProAlaValLysGluLysGlyLysLysLysLysAspGluAspLeuSerSerArgArgIleProAsnProAlaLys AspAspGlnLeuArgLysAlaLeuAspLeuValLysSerProGluGlnTrpGln-471 |
| SEQ. ID. NO. 10907 | 477-AlaAlaLysLysProValSerAsnLysAspLysLysAspLysLysAspLysLys-494 |
| 733 | |
| AMPHI Regions - AMPHI | |
| SEQ. ID. NO. 10908 | 6-ThrLeuSerArgLeuSer-11 |
| SEQ. ID. NO. 10909 | 33-TyrGlyGlyTyrProAspThrValTyrGluGly-43 |
| SEQ. ID. NO. 10910 | 53-LysGlnThrGluLysMetGluLysTyrPheVal-63 |
| SEQ. ID. NO. 10911 | 92-GlyAlaPheArgGlnPheGluGlu-99 |
| Antigenic Index - Jameson-Wolf | |
| SEQ. ID. NO. 10912 | 2-MetAsnProLysThrLeuSer-8 |
| SEQ. ID. NO. 10913 | 22-CysGlyGlyAsnGlyGlnLysSer-29 |
| SEQ. ID. NO. 10914 | 33-TyrGlyGlyTyrProAspThrValTyrGluGlyLeuLysAsnAspAspThrSerLeuGlyLysGlnThrGluLysMetGluLysTyrPhe-62 |
| SEQ. ID. NO. 10915 | 65-AlaGlyAsnLysLysMetAsnAlaAlaProGlyAla-76 |
| SEQ. ID. NO. 10916 | 84-LeuSerArgSerGlyAspLysGluGlyAlaPheArgGlnPheGluGluGluLysArgLeuPheProGlu-106 |
| SEQ. ID. NO. 10917 | 115-MetLysThrGlyLysGlyGlyLysArg-123 |
| Hydrophilic Regions - Hopp-Woods | |
| SEQ. ID. NO. 10918 | 40-ValTyrGluGlyLeuLysAsnAspAspThrSerLeuGlyLysGlnThrGluLysMetGluLysTyrPhe-62 |
| SEQ. ID. NO. 10919 | 65-AlaGlyAsnLysLysMetAsnAla-72 |

| | |
|---|---|
| SEQ. ID. NO. 10920 | 86-ArgSerGlyAspLysGluGlyAlaPheArgGlnPheGluGluGluLysArgLeuPhePro-105 |
| SEQ. ID. NO. 10921 | 115-MetLysThrGlyLysGlyGlyLysArg-123 |
| 734-2 | |
| AMPHI Regions - AMPHI | |
| SEQ. ID. NO. 10922 | 19-ArgAlaAlaAspThrTyr-24 |
| SEQ. ID. NO. 10923 | 26-TyrLeuAlaValTrpGlnAsnProGlnAsnAlaAsp-37 |
| SEQ. ID. NO. 10924 | 53-GluAlaPheSerGluLeuGluAlaPheCysLys-63 |
| SEQ. ID. NO. 10925 | 77-ThrGlyCysArgSerValValSer-84 |
| SEQ. ID. NO. 10926 | 92-LeuAlaTyrProLysAlaLeuGlyAlaLeuArg-102 |
| SEQ. ID. NO. 10927 | 113-ArgPheThrSerVal-117 |
| SEQ. ID. NO. 10928 | 121-AlaLeuAsnGlnCysIleLys-127 |
| Antigenic Index - Jameson-Wolf | |
| SEQ. ID. NO. 10929 | 18-AlaArgAlaAlaAsp-22 |
| SEQ. ID. NO. 10930 | 31-GlnAsnProGlnAsnAlaAspAspValLeuGln-41 |
| SEQ. ID. NO. 10931 | 43-LysThrThrLysGluAspSerThrLysSerGluAlaPheSerGlu-57 |
| SEQ. ID. NO. 10932 | 59-GluAlaPheCysLysGlyGlnAspThr-67 |
| SEQ. ID. NO. 10933 | 71-IleAlaGluAspGluProThrGlyCysArgSer-81 |
| SEQ. ID. NO. 10934 | 101-LeuArgValAspAsn-105 |
| SEQ. ID. NO. 10935 | 111-SerProArgPheThrSer-116 |
| SEQ. ID. NO. 10936 | 125-CysIleLysLysTyrGlyVal-131 |
| SEQ. ID. NO. 10937 | 145-SerSerTyrTyrGly-149 |
| Hydrophilic Regions - Hopp-Woods | |
| SEQ. ID. NO. 10938 | 18-AlaArgAlaAlaAsp-22 |
| SEQ. ID. NO. 10939 | 34-GlnAsnAlaAspAspValLeuGln-41 |
| SEQ. ID. NO. 10940 | 43-LysThrThrLysGluAspSerThrLysSerGluAlaPheSerGlu-57 |
| SEQ. ID. NO. 10941 | 59-GluAlaPheCysLysGlyGlnAspThr-67 |
| SEQ. ID. NO. 10942 | 71-IleAlaGluAspGluProThrGlyCys-79 |
| SEQ. ID. NO. 10943 | 101-LeuArgValAspAsn-105 |
| 735 | |
| AMPHI Regions - AMPHI | |
| SEQ. ID. NO. 10944 | 6-LeuLeuAlaAsnAsn-10 |
| SEQ. ID. NO. 10945 | 12-GlnProIleAlaIleIleAla-18 |
| SEQ. ID. NO. 10946 | 118-GlyCysIleAspGlyPheGly-124 |
| Antigenic Index - Jameson-Wolf | |
| SEQ. ID. NO. 10947 | 28-HisHisGlnGlyTyrLysSerAlaPheAlaLysGln-39 |
| SEQ. ID. NO. 10948 | 41-AlaValIleAspLysMetGluArgAspLysAlaGln-52 |
| SEQ. ID. NO. 10949 | 60-AsnTyrAlaArgGluLeuGluLeuAlaArgAlaGluAlaLysLysTyrGluValLysAla-79 |
| SEQ. ID. NO. 10950 | 86-LeuAlaLysLysGlnAlaGluValSerArgLeuLysThrGluAsnLysLysGluIleGluAsn-106 |
| SEQ. ID. NO. 10951 | 108-LeuThrGlnAspArgLysAsnAlaSerGlyGlyCysIleAspGlyPheGlySerHisGly-127 |
| SEQ. ID. NO. 10952 | 134-AlaLeuGlyTyrGlyAsn-139 |
| Hydrophilic Regions - Hopp-Woods | |
| SEQ. ID. NO. 10953 | 41-AlaValIleAspLysMetGluArgAspLysAlaGln-52 |
| SEQ. ID. NO. 10954 | 60-AsnTyrAlaArgGluLeuGluLeuAlaArgAlaGluAlaLysLysTyrGluValLysAla-79 |
| SEQ. ID. NO. 10955 | 86-LeuAlaLysLysGlnAlaGluValSerArgLeuLysThrGluAsnLysLysGluIleGluAsn-106 |
| SEQ. ID. NO. 10956 | 108-LeuThrGlnAspArgLysAsnAlaSer-116 |
| 736 | |
| AMPHI Regions - AMPHI | |
| SEQ. ID. NO. 10957 | 13-GlyLeuIleGlnSerLeuGlySer-20 |
| SEQ. ID. NO. 10958 | 50-GlyValLeuSerVal-54 |
| SEQ. ID. NO. 10959 | 61-GlyLeuPheValGly-65 |
| SEQ. ID. NO. 10960 | 70-LeuGlnGlyTyrThrGlnLeuSerLysPheLysSerAlaAspIle-84 |
| SEQ. ID. NO. 10961 | 93-LeuLeuArgGluLeuGlyProVal-100 |
| SEQ. ID. NO. 10962 | 120-LeuMetLysThrThrGluGlnLeuGluAlaMetAsnValMet-133 |
| SEQ. ID. NO. 10963 | 135-ValAsnProValAlaArgValVal-142 |
| SEQ. ID. NO. 10964 | 144-ProArgPheTrpAlaGlyValPheSerMetPro-154 |
| SEQ. ID. NO. 10965 | 156-LeuAlaSerIlePheAsnValAlaGlyIlePheGlyAla-168 |
| SEQ. ID. NO. 10966 | 196-AspValIleAsnGlyLeu-201 |
| SEQ. ID. NO. 10967 | 230-LeuArgAlaSerThrArgThr-236 |
| Antigenic Index - Jameson-Wolf | |
| SEQ. ID. NO. 10968 | 37-ValArgProArgLeuSerVal-43 |
| SEQ. ID. NO. 10969 | 77-SerLysPheLysSer-81 |
| SEQ. ID. NO. 10970 | 93-LeuLeuArgGluLeuGly-98 |
| SEQ. ID. NO. 10971 | 109-SerAlaGlyGlyAlaMetThrSer-116 |
| SEQ. ID. NO. 10972 | 122-LysThrThrGluGlnLeuGlu-128 |
| SEQ. ID. NO. 10973 | 186-GlnMetGlnAsnAsn-190 |
| SEQ. ID. NO. 10974 | 224-ProThrSerGluGlyIleLeuArgAlaSerThr-234 |
| Hydrophilic Regions - Hopp-Woods | |
| SEQ. ID. NO. 10975 | 39-ProArgLeuSerVal-43 |
| SEQ. ID. NO. 10976 | 77-SerLysPheLysSer-81 |
| SEQ. ID. NO. 10977 | 93-LeuLeuArgGluLeuGly-98 |
| SEQ. ID. NO. 10978 | 122-LysThrThrGluGlnLeuGlu-128 |
| 737 | |
| AMPHI Regions - AMPHI | |
| SEQ. ID. NO. 10979 | 56-AlaAlaLeuAlaArgValGlyGly-63 |
| Antigenic Index - Jameson-Wolf | |
| SEQ. ID. NO. 10980 | 24-AlaHisHisAspGlyHisGlyAspAspAspHisGlyHis-36 |
| SEQ. ID. NO. 10981 | 38-AlaHisGlnHisAsnLysGlnAspLysIleIleSer-49 |
| SEQ. ID. NO. 10982 | 51-AlaGlnAlaGluLysAlaAlaLeu-58 |
| SEQ. ID. NO. 10983 | 60-ArgValGlyGlyLysIleThrAspIleAspLeuGluHisAspAsnGlyArgProHisTyrAspValGluIleValLysAsnGlyGlnGluTyr-90 |
| SEQ. ID. NO. 10984 | 94-ValAspAlaArgThrGlyArgValIleSerSerArgArgAspAsp-108 |

TABLE 1-continued

Hydrophilic Regions - Hopp-Woods
SEQ. ID. NO. 10985   27-AspGlyHisGlyAspAspAspHisGlyHis-36
SEQ. ID. NO. 10986   40-GlnHisAsnLysGlnAspLysIleIleSer-49
SEQ. ID. NO. 10987   51-AlaGlnAlaGluLysAlaAlaLeu-58
SEQ. ID. NO. 10988   61-ValGlyGlyLysIleThrAspIleAspLeuGluHisAspAsnGlyArgProHisTyr-79
SEQ. ID. NO. 10989   82-GluIleValLysAsnGlyGlnGluTyr-90
SEQ. ID. NO. 10990   94-ValAspAlaArgThrGlyArg-100
SEQ. ID. NO. 10991   102-IleSerSerArgArgAspAsp-108
738
AMPHI Regions - AMPHI
SEQ. ID. NO. 10992   91-LeuMetAsnLeuIleTyrProGlyMetAsnAsp-101
SEQ. ID. NO. 10993   139-IleGlySerLeuLeuGlnSerCysIle-147
SEQ. ID. NO. 10994   228-ThrTyrIleAlaAlaIleAlaLeuIle-236
SEQ. ID. NO. 10995   271-ThrIleLeuGluThrPheThrGlyIle-279
SEQ. ID. NO. 10996   285-ValGluArgValAlaAsnGlyGlyPheThrAspLeuProArgGlnIleGluTrpAsn-303
SEQ. ID. NO. 10997   305-AlaLeuAlaAlaPheGlnSer-311
SEQ. ID. NO. 10998   316-GlyHisGlyTrpAsnSerPheAla-323
SEQ. ID. NO. 10999   338-AspAsnLeuLeuSerAsnLeuPheThr-346
SEQ. ID. NO. 11000   371-LeuLeuThrGlyIleAlaGlyLeuLeuLysArg-381
SEQ. ID. NO. 11001   398-MetCysHisSerMetLeu-403
SEQ. ID. NO. 11002   461-ArgLeuValAsnAlaPheSerPro-468
SEQ. ID. NO. 11003   472-AspSerAlaLysThrLeuAsnArgLys-480
SEQ. ID. NO. 11004   482-AsnGluLeuArgTyrIleSer-488
SEQ. ID. NO. 11005   507-LeuProGluTyrProGluThr-513
SEQ. ID. NO. 11006   549-AlaLysGlnTrpMetArgAlaThr-556
SEQ. ID. NO. 11007   567-TyrAlaAspGluIleArgLysLeuProVal-576
SEQ. ID. NO. 11008   579-ProLeuLeuProGluLeuLeuLysAspCysLysAlaPheAlaAlaAlaPro-595
Antigenic Index - Jameson-Wolf
SEQ. ID. NO. 11009   37-LysLeuLysProSerProAspPheTyr-45
SEQ. ID. NO. 11010   62-AlaGlyLysLysLeuPheAsp-68
SEQ. ID. NO. 11011   124-PheGlyGlnGluArgIle-129
SEQ. ID. NO. 11012   154-GlyTrpGluAspThrProLeu-160
SEQ. ID. NO. 11013   177-GlyGlnArgAsnAsnLeuGly-183
SEQ. ID. NO. 11014   196-LeuAsnGlyGlnArgLysIlePro-203
SEQ. ID. NO. 11015   242-PheArgSerAspLysSerAsnArgArgThrMet-252
SEQ. ID. NO. 11016   283-ThrAlaValGluArgValAlaAsnGlyGlyPheThrAspLeuProArgGlnIleGluTrp-302
SEQ. ID. NO. 11017   316-GlyHisGlyTrpAsnSerPheAla-323
SEQ. ID. NO. 11018   378-LeuLeuLysArgProLeuThr-384
SEQ. ID. NO. 11019   424-ProAlaGluAlaSerAspGlyIleAlaPheLysLysAlaAla-437
SEQ. ID. NO. 11020   468-ProAlaThrAspAspSerAlaLysThrLeuAsnArgLysIleAsnGlu-483
SEQ. ID. NO. 11021   508-ProGluTyrProGluThrGlnThrTrpAlaGlu-518
SEQ. ID. NO. 11022   520-AlaThrLeuLysSerLeuLysTyrArgProHisSerAla-532
SEQ. ID. NO. 11023   542-ArgGlnGlyLysValAlaGluAlaLysGlnTrpMet-553
SEQ. ID. NO. 11024   555-AlaThrGlnSerTyr-559
SEQ. ID. NO. 11025   566-ArgTyrAlaAspGluIleArgLys-573
SEQ. ID. NO. 11026   584-LeuLeuLysAspCysLysAla-590
SEQ. ID. NO. 11027   595-ProGlyHisProGluAlaLysProCysLys-604
Hydrophilic Regions - Hopp-Woods
SEQ. ID. NO. 11028   38-LeuLysProSerPro-42
SEQ. ID. NO. 11029   62-AlaGlyLysLysLeuPheAsp-68
SEQ. ID. NO. 11030   125-GlyGlnGluArgIle-129
SEQ. ID. NO. 11031   198-GlyGlnArgLysIlePro-203
SEQ. ID. NO. 11032   243-ArgSerAspLysSerAsnArgArgThrMet-252
SEQ. ID. NO. 11033   283-ThrAlaValGluArgValAla-289
SEQ. ID. NO. 11034   378-LeuLeuLysArgProLeuThr-384
SEQ. ID. NO. 11035   425-AlaGluAlaSerAsp-429
SEQ. ID. NO. 11036   431-IleAlaPheLysLysAlaAla-437
SEQ. ID. NO. 11037   469-AlaThrAspAspSerAlaLysThrLeuAsnArgLysIleAsnGlu-483
SEQ. ID. NO. 11038   525-LeuLysTyrArgPro-529
SEQ. ID. NO. 11039   542-ArgGlnGlyLysValAlaGluAlaLysGlnTrpMet-553
SEQ. ID. NO. 11040   566-ArgTyrAlaAspGluIleArgLys-573
SEQ. ID. NO. 11041   584-LeuLeuLysAspCysLysAla-590
SEQ. ID. NO. 11042   596-GlyHisProGluAlaLysProCysLys-604
739-2
AMPHI Regions - AMPHI
SEQ. ID. NO. 11043   6-AsnLysProPheArgLeu-11
SEQ. ID. NO. 11044   53-HisThrAspSerPro-57
SEQ. ID. NO. 11045   88-GlnProAspGlyThrAsp-93
SEQ. ID. NO. 11046   120-ThrAspArgGlnProAspAspAlaGlyThr-129
SEQ. ID. NO. 11047   131-AlaGluAsnThrLeu-135
Antigenic Index - Jameson-Wolf
SEQ. ID. NO. 11048   1-MetAlaLysLysProAsnLysProPheArgLeuThrPro-13
SEQ. ID. NO. 11049   39-PheAsnProAsnGlyAspLysThrLeuGlnAlaGluProGlnHisThrAspSerProArgGluThrGluPhe-62
SEQ. ID. NO. 11050   64-LeuProAsnGlyValValGlyGlnAspAlaAlaGlnProGluHisHisHis-80
SEQ. ID. NO. 11051   82-AlaSerSerGluProAlaGlnProAspGlyThrAspGluSerGlySerGlyLeuProSerProAlaAlaProLysLysAsnArgValLysProGlnProAla
                     AspThrAlaGlnThrAspArgGlnProAspAspAlaGlyThrGlnAlaGluAsnThrLeuLysGluThrProValLeuProThrAsnValProArgProGlu TABLE 1-continued

| | |
|---|---|
| | ProArgLysGluThrProGluLysGlnAlaGlnProLysGluThrProLysGluAsnHisThrLysProAspThrProLysAsnThrProProLysProHis LysGluIleLeu-187 |
| Hydrophilic Regions - Hopp-Woods | |
| SEQ. ID. NO. 11052 | 1-MetAlaLysLysProAsnLysProPheArgLeu-11 |
| SEQ. ID. NO. 11053 | 41-ProAsnGlyAspLysThrLeuGlnAlaGluProGlnHisThrAspSerProArgGluThrGlu-61 |
| SEQ. ID. NO. 11054 | 72-AspAlaAlaGlnProGluHisHisHis-80 |
| SEQ. ID. NO. 11055 | 82-AlaSerSerGluProAlaGlnProAspGlyThrAspGluSerGlySer-97 |
| SEQ. ID. NO. 11056 | 103-AlaAlaProLysLysAsnArgValLysProGlnProAlaAspThrAlaGlnThrAspArgGlnProAspAspAlaGlyThrGlnAlaGluAsnThrLeu LysGluThrPro-139 |
| SEQ. ID. NO. 11057 | 145-ValProArgProGluProArgLysGluThrProGluLysGlnAlaGlnProLysGluThrProLysGluAsnHisThrLysProAspThrProLysAsn ThrProProLysProHisLysGluIleLeu-187 |
| 740 | |
| AMPHI Regions - AMPHI | |
| SEQ. ID. NO. 11058 | 6-LeuValArgTrpLeuAlaVal-12 |
| SEQ. ID. NO. 11059 | 28-ProGluAspLysLeuGlnHisLeuIleAsnGlyIle-39 |
| Antigenic Index - Jameson-Wolf | |
| SEQ. ID. NO. 11060 | 26-AsnProProGluAspLysLeuGln-33 |
| SEQ. ID. NO. 11061 | 57-IleLysHisHisLeuLysGlnGluPheAspLeuLysArgGlnThr-71 |
| Hydrophilic Regions - Hopp-Woods | |
| SEQ. ID. NO. 11062 | 27-ProProGluAspLysLeuGln-33 |
| SEQ. ID. NO. 11063 | 57-IleLysHisHisLeuLysGlnGluPheAspLeuLysArgGlnThr-71 |
| 741 | |
| AMPHI Regions - AMPHI | |
| SEQ. ID. NO. 11064 | 32-GlyAlaGlyLeuAlaAspAlaLeuThrAla-41 |
| SEQ. ID. NO. 11065 | 93-SerArgPheAspPheIleArgGlnIleGlu-102 |
| SEQ. ID. NO. 11066 | 158-ThrSerPheAspLysLeuProGluGlyGlyArg-168 |
| SEQ. ID. NO. 11067 | 256-SerAlaGluValLysThrValAsnGlyIleArgHisIleGlyLeuAlaAlaLys-273 |
| Antigenic Index - Jameson-Wolf | |
| SEQ. ID. NO. 11068 | 21-SerSerGlyGlyGly-25 |
| SEQ. ID. NO. 11069 | 43-LeuAspHisLysAspLysGlyLeu-50 |
| SEQ. ID. NO. 11070 | 56-AspGlnSerValArgLysAsnGluLysLeuLysLeu-67 |
| SEQ. ID. NO. 11071 | 71-GlyAlaGluLysThrTyrGlyAsnGlyAspSerLeuAsnThrGlyLysLeuLysAsnAspLysValSerArgPheAspPhe-97 |
| SEQ. ID. NO. 11072 | 101-IleGluValAspGlyGlnLeu-107 |
| SEQ. ID. NO. 11073 | 117-ValTyrLysGlnSerHisSerAla-124 |
| SEQ. ID. NO. 11074 | 129-GlnThrGluGlnIleGlnAspSerGluHisSerGlyLysMetValAlaLysArgGlnPheArgIleGlyAspIleAlaGlyGluHisThrSerPheAspLys LeuProGluGlyGlyArgAlaThrTyrArg-172 |
| SEQ. ID. NO. 11075 | 174-ThrAlaPheGlySerAspAspAlaGlyGly-183 |
| SEQ. ID. NO. 11076 | 191-PheAlaAlaLysGlnGlyAsnGlyLysIleGluHisLeuLysSerProGluLeuAsnVal-210 |
| SEQ. ID. NO. 11077 | 213-AlaAlaAlaAspIleLysProAspGlyLysArgHisAla-225 |
| SEQ. ID. NO. 11078 | 234-AsnGlnAlaGluLysGlySerTyrSer-242 |
| SEQ. ID. NO. 11079 | 247-GlyGlyLysAlaGlnGluValAlaGly-255 |
| SEQ. ID. NO. 11080 | 257-AlaGluValLysThrValAsnGly-264 |
| Hydrophilic Regions - Hopp-Woods | |
| SEQ. ID. NO. 11081 | 43-LeuAspHisLysAspLysGlyLeu-50 |
| SEQ. ID. NO. 11082 | 57-GlnSerValArgLysAsnGluLysLeuLysLeu-67 |
| SEQ. ID. NO. 11083 | 71-GlyAlaGluLysThrTyrGlyAsn-78 |
| SEQ. ID. NO. 11084 | 85-GlyLysLeuLysAsnAspLysValSerArg-94 |
| SEQ. ID. NO. 11085 | 101-IleGluValAspGly-105 |
| SEQ. ID. NO. 11086 | 132-GlnIleGlnAspSerGluHisSerGly-140 |
| SEQ. ID. NO. 11087 | 142-MetValAlaLysArgGlnPheArgIle-150 |
| SEQ. ID. NO. 11088 | 152-AspIleAlaGlyGlu-156 |
| SEQ. ID. NO. 11089 | 158-ThrSerPheAspLysLeuProGluGlyGlyArgAlaThrTyr-171 |
| SEQ. ID. NO. 11090 | 177-GlySerAspAspAlaGlyGly-183 |
| SEQ. ID. NO. 11091 | 195-GlnGlyAsnGlyLysIleGluHisLeuLysSerProGluLeuAsnVal-210 |
| SEQ. ID. NO. 11092 | 213-AlaAlaAlaAspIleLysProAspGlyLysArgHisAla-225 |
| SEQ. ID. NO. 11093 | 235-GlnAlaGluLysGlySer-240 |
| SEQ. ID. NO. 11094 | 249-LysAlaGlnGluValAlaGly-255 |
| SEQ. ID. NO. 11095 | 257-AlaGluValLysThr-261 |
| 742 | |
| AMPHI Regions - AMPHI | |
| SEQ. ID. NO. 11096 | 26-ArgGluValProAsp-30 |
| SEQ. ID. NO. 11097 | 53-AsnArgProLeuGln-57 |
| SEQ. ID. NO. 11098 | 66-GluAspTrpSerArgLeu-71 |
| SEQ. ID. NO. 11099 | 77-AsnLeuPheSerGlyPheLysHisValPheAsp-87 |
| SEQ. ID. NO. 11100 | 143-LysAlaLeuGluLysLeuLysAla-150 |
| SEQ. ID. NO. 11101 | 153-AspGluThrAlaLysGluTyrArg-160 |
| SEQ. ID. NO. 11102 | 234-AsnAlaAlaGlnArgPheProAsnSerLeuTyrAsp-245 |
| SEQ. ID. NO. 11103 | 326-ValTyrAlaGlySerCysGlnGlu-333 |
| SEQ. ID. NO. 11104 | 340-SerSerProLeuVal-344 |
| SEQ. ID. NO. 11105 | 369-ArgAsnAlaLysLysIle-374 |
| SEQ. ID. NO. 11106 | 422-ThrProAlaPheThrGlyPheSerGlyThrValProValTrpLysThrValLys-439 |
| SEQ. ID. NO. 11107 | 448-LeuTyrAsnTyrAlaLysTyrLeuAsnThrAsn-458 |
| SEQ. ID. NO. 11108 | 475-LeuHisLeuLeuGlyGlyLeuHisTyr-483 |
| SEQ. ID. NO. 11109 | 505-PheGlnThrAlaSerSer-510 |
| SEQ. ID. NO. 11110 | 543-IleTyrGlySerTyrThrLysIlePheLysGlnGlnAspAsn-556 |
| SEQ. ID. NO. 11111 | 616-GlySerPheGlnThrValAlaLysProIleGlyLysValValSerArg-631 |
| SEQ. ID. NO. 11112 | 643-GluAspTrpLysValPheAlaGly-650 |
| SEQ. ID. NO. 11113 | 657-ArgTyrLysAsnAla-661 |
| SEQ. ID. NO. 11114 | 670-AlaLysAsnSerSer-674 |
| SEQ. ID. NO. 11115 | 677-ProTyrAsnPheSerAsnPheThrProValHisIle-688 |

TABLE 1-continued

| | |
|---|---|
| SEQ. ID. NO. 11116 | 714-ThrSerSerLeuTyrAsnIle-720 |
| SEQ. ID. NO. 11117 | 725-TyrGlyLeuIleAspGlyPheValArgTyr-734 |
| SEQ. ID. NO. 11118 | 736-LeuGlyLysHisAlaLysLeu-742 |
| SEQ. ID. NO. 11119 | 759-TyrAsnArgThrArgGlyAlaAsnAsnPheTyrGlyGluPro-772 |
| Antigenic Index - Jameson-Wolf | |
| SEQ. ID. NO. 11120 | 6-AlaGluAlaAspAlaGlyAsp-12 |
| SEQ. ID. NO. 11121 | 21-MetTyrGlnLysSerArgGluValProAspPheSerGly-33 |
| SEQ. ID. NO. 11122 | 37-ProCysGluAsnGlnLysThrAlaProPheSerSerThrProAlaCysAsnArgProLeuGlnLeuProArgAsnThrTyrLeuGlyGluAspTrpSer ArgLeuSerAlaAspLysTyrAsn-77 |
| SEQ. ID. NO. 11123 | 86-PheAspAsnGlyTrp-90 |
| SEQ. ID. NO. 11124 | 97-SerTyrThrLysAsnGluSerAspAlaLysVal-107 |
| SEQ. ID. NO. 11125 | 120-LeuSerGlyGluAspAla-125 |
| SEQ. ID. NO. 11126 | 130-ThrGluLysAsnGluValIleProPheGluProLysAspLysAlaLeuGluLysLeuLysAlaTyrArgAspGluThrAlaLysGluTyrArgGluArg LysAspAspPheValLysAsnArgPheAspAsnThrAla-175 |
| SEQ. ID. NO. 11127 | 177-GluGlnTyrArgSerArgArgAlaAlaGluArgLysAlaGlyPheAspLysCysMetSerAspProPheAla-200 |
| SEQ. ID. NO. 11128 | 205-CysGlnGlySerTrpGlyAspProGlyValAspAlaAspLysAlaGluPheValAsp-223 |
| SEQ. ID. NO. 11129 | 235-AlaAlaGlnArgPheProAsnSerLeuTyrAspSerSerPheAsnArgLysAlaThrAlaAsnArgArgTyrSerTyrMetPro-262 |
| SEQ. ID. NO. 11130 | 264-ArgHisThrLysAspAspArgGlnTrp-272 |
| SEQ. ID. NO. 11131 | 286-GlyArgGluHisAsp-290 |
| SEQ. ID. NO. 11132 | 295-TyrAlaTyrGlyAspGluLysIleArgSerGluTyr-306 |
| SEQ. ID. NO. 11133 | 308-GluIleTyrGluArgArgTyrArgValArgProAsnThrGlyAla-322 |
| SEQ. ID. NO. 11134 | 328-AlaGlySerCysGlnGluGluProAspGlyAspLeuSer-340 |
| SEQ. ID. NO. 11135 | 345-ArgGlyHisLysGluProAspTrpGlnAlaTyrAspGluLysGlyAsnArgThrValTyrAlaGluGluCysArgAsnAlaLysLysIleLysThrGlu ProLysLeuAspAlaGluGlyLysGln-386 |
| SEQ. ID. NO. 11136 | 389-TyrTyrAspGluTyrSerGlySerArgThr-398 |
| SEQ. ID. NO. 11137 | 405-TyrGluLeuAspGluLysGlyAsnLysIleGlnGluThrAsnProAspGlyThrPro-423 |
| SEQ. ID. NO. 11138 | 439-LysValAlaAspAspHisVal-445 |
| SEQ. ID. NO. 11139 | 454-TyrLeuAsnThrAsnLysThrHis-461 |
| SEQ. ID. NO. 11140 | 485-ArgTyrGluThrSerGlnThrLysAspMetProValArgTyrGlyGlnProAlaSerAspPheGlnThr-507 |
| SEQ. ID. NO. 11141 | 509-SerSerIleArgAlaAspGlnAspHisTyrThr-519 |
| SEQ. ID. NO. 11142 | 521-LysMetGlnGlyHisLysLeuThrPro-529 |
| SEQ. ID. NO. 11143 | 545-GlySerTyrThrLys-549 |
| SEQ. ID. NO. 11144 | 551-PheLysGlnGlnAspAsnValAspValSerAla-561 |
| SEQ. ID. NO. 11145 | 584-GlyArgLeuAsnAla-588 |
| SEQ. ID. NO. 11146 | 595-LeuGluGlnLysAsnArgThrValVal-603 |
| SEQ. ID. NO. 11147 | 610-GlyAlaGlyGlyLysGlnGlySer-617 |
| SEQ. ID. NO. 11148 | 628-ValValSerArgGlyAlaGluPheGluLeuSerGlyGluLeuAsnGluAspTrpLys-646 |
| SEQ. ID. NO. 11149 | 652-ThrTyrAsnLysSerArgTyrLysAsnAlaAlaGluValAsnAlaGluArgLeuAlaLysAsnSerSerAlaAspProTyrAsnPheSerAsn-682 |
| SEQ. ID. NO. 11150 | 708-ValSerAlaGlnSerGlyThrSerSerLeuTyrAsnIleArgGlnGlyGly-724 |
| SEQ. ID. NO. 11151 | 735-GluLeuGlyLysHisAlaLys-741 |
| SEQ. ID. NO. 11152 | 746-GlyThrAsnLeuAsnGlyArgThrTyrPheGluAsnAsnTyrAsnArgThrArgGlyAlaAsnAsnPheTyrGlyGluProArgThrValSerMet-777 |
| Hydrophilic Regions - Hopp-Woods | |
| SEQ. ID. NO. 11153 | 6-AlaGluAlaAspAlaGlyAsp-12 |
| SEQ. ID. NO. 11154 | 23-GlnLysSerArgGluValProAsp-30 |
| SEQ. ID. NO. 11155 | 67-AspTrpSerArgLeuSerAlaAspLys-75 |
| SEQ. ID. NO. 11156 | 97-SerTyrThrLysAsnGluSerAspAlaLysVal-107 |
| SEQ. ID. NO. 11157 | 120-LeuSerGlyGluAspAla-125 |
| SEQ. ID. NO. 11158 | 130-ThrGluLysAsnGluValIleProPheGluProLysAspLysAlaLeuGluLysLeuLysAlaTyrArgAspGluThrAlaLysGluTyrArgGluArg LysAspAspPheValLysAsnArgPheAspAsnThrAla-175 |
| SEQ. ID. NO. 11159 | 177-GluGlnTyrArgSerArgArgAlaAlaGluArgLysAlaGlyPheAspLysCysMetSer-196 |
| SEQ. ID. NO. 11160 | 212-ProGlyValAspAlaAspLysAlaGluPheValAsp-223 |
| SEQ. ID. NO. 11161 | 247-SerPheAsnArgLysAlaThrAlaAsnArgArgTyrSer-259 |
| SEQ. ID. NO. 11162 | 264-ArgHisThrLysAspAspArgGlnTrp-272 |
| SEQ. ID. NO. 11163 | 286-GlyArgGluHisAsp-290 |
| SEQ. ID. NO. 11164 | 297-TyrGlyAspGluLysIleArgSerGluTyr-306 |
| SEQ. ID. NO. 11165 | 308-GluIleTyrGluArgArgTyrArgValArgProAsnThr-320 |
| SEQ. ID. NO. 11166 | 331-CysGlnGluGluProAspGlyAspLeu-339 |
| SEQ. ID. NO. 11167 | 345-ArgGlyHisLysGluProAsp-351 |
| SEQ. ID. NO. 11168 | 354-AlaTyrAspGluLysGlyAsnArg-361 |
| SEQ. ID. NO. 11169 | 363-ValTyrAlaGluGluCysArgAsnAlaLysLysIleLysThrGluProLysLeuAspAlaGluGlyLysGln-386 |
| SEQ. ID. NO. 11170 | 393-TyrSerGlySerArg-397 |
| SEQ. ID. NO. 11171 | 405-TyrGluLeuAspGluLysGlyAsnLysIleGlnGluThrAsnProAspGly-421 |
| SEQ. ID. NO. 11172 | 439-LysValAlaAspAspHisVal-445 |
| SEQ. ID. NO. 11173 | 485-ArgTyrGluThrSerGlnThrLysAspMetProVal-496 |
| SEQ. ID. NO. 11174 | 500-GlnProAlaSerAsp-504 |
| SEQ. ID. NO. 11175 | 509-SerSerIleArgAlaAspGlnAspHisTyrThr-519 |
| SEQ. ID. NO. 11176 | 551-PheLysGlnGlnAspAsnValAspValSerAla-561 |
| SEQ. ID. NO. 11177 | 597-GlnLysAsnArgThrValVal-603 |
| SEQ. ID. NO. 11178 | 611-AlaGlyGlyLysGlnGlySer-617 |
| SEQ. ID. NO. 11179 | 628-ValValSerArgGlyAlaGluPheGluLeuSerGlyGluLeuAsnGluAspTrpLys-646 |
| SEQ. ID. NO. 11180 | 654-AsnLysSerArgTyrLysAsnAlaAlaGluValAsnAlaGluArgLeuAlaLysAsnSerSerAlaAsp-676 |
| SEQ. ID. NO. 11181 | 735-GluLeuGlyLysHisAlaLys-741 |
| SEQ. ID. NO. 11182 | 758-AsnTyrAsnArgThrArgGly-764 |
| SEQ. ID. NO. 11183 | 770-GlyGluProArgThrValSerMet-777 |
| 743 | |
| AMPHI Regions - AMPHI | |
| SEQ. ID. NO. 11184 | 19-TyrGlyGlySerPhe-23 |
| SEQ. ID. NO. 11185 | 58-SerTyrThrIleAsp-62 |
| SEQ. ID. NO. 11186 | 64-MetSerThrAlaThrGly-69 |

TABLE 1-continued

| | |
|---|---|
| SEQ. ID. NO. 11187 | 96-ThrLeuGluGluAlaMetLysAsnThrThrGlyValAsnValValArgAsp-112 |
| SEQ. ID. NO. 11188 | 158-ValTyrAspHisIleGluValValArgGlyAlaThrGly-170 |
| Antigenic Index - Jameson-Wolf | |
| SEQ. ID. NO. 11189 | 1-MetAsnGlnAsnHis-5 |
| SEQ. ID. NO. 11190 | 30-ValSerAspGlyAsnThrVal-36 |
| SEQ. ID. NO. 11191 | 41-ValAsnValArgGlySer-46 |
| SEQ. ID. NO. 11192 | 51-GlyLysThrGluLysThrArgSerTyrThrIleAspArgMetSerThr-66 |
| SEQ. ID. NO. 11193 | 72-IleAlaGlyLysAspThrProGlnSer-80 |
| SEQ. ID. NO. 11194 | 85-ThrArgSerArgLeuAspAspLysAlaValHisThrLeuGluGluAlaMetLysAsnThrThrGly-106 |
| SEQ. ID. NO. 11195 | 109-ValValArgAspSerGlyLeuGlnThrArgPheLeuSerArgGlyPhe-124 |
| SEQ. ID. NO. 11196 | 128-GlnIleGlyGluAspGlyMet-134 |
| SEQ. ID. NO. 11197 | 140-GlyArgSerGlyTyrThrAlaLysIleAspValSerProSerThrAsp-155 |
| SEQ. ID. NO. 11198 | 163-GluValValArgGlyAlaThrGlyLeuThrGlnSerAsnSerGluProGlyGly-180 |
| Hydrophilic Regions - Hopp-Woods | |
| SEQ. ID. NO. 11199 | 51-GlyLysThrGluLysThrArgSerTyrThrIleAspArgMetSerThr-66 |
| SEQ. ID. NO. 11200 | 72-IleAlaGlyLysAspThrProGln-79 |
| SEQ. ID. NO. 11201 | 85-ThrArgSerArgLeuAspAspLysAlaValHisThrLeuGluGluAlaMetLysAsn-103 |
| SEQ. ID. NO. 11202 | 109-ValValArgAspSerGlyLeu-115 |
| SEQ. ID. NO. 11203 | 128-GlnIleGlyGluAspGlyMet-134 |
| SEQ. ID. NO. 11204 | 174-SerAsnSerGluProGlyGly-180 |
| 744 | |
| AMPHI Regions - AMPHI | |
| SEQ. ID. NO. 11205 | 36-LeuAspGluLeuCys-40 |
| SEQ. ID. NO. 11206 | 65-AsnPheTyrLysAsnIleHisAlaThrThrLysPheValArgGluThrAspTyrSerLysPheIleGlnLeuLysLysAlaArgHisLeuThrValSer AspPheThrSerIleTrpLysValIleLeuTyr-108 |
| SEQ. ID. NO. 11207 | 124-SerSerIlePheAsnLysPheLysAlaLeuAspGluAlaIleAsnGluTyrTyrTyr-142 |
| SEQ. ID. NO. 11208 | 165-MetIlePheGlyLysPheValLysLeuGly-174 |
| SEQ. ID. NO. 11209 | 197-ArgLysPheLysAspAla-202 |
| SEQ. ID. NO. 11210 | 228-PheAspGluTyrHisGluCysValLysGlyLeuAlaAsn-240 |
| SEQ. ID. NO. 11211 | 270-IlePheAspSerLeu-274 |
| SEQ. ID. NO. 11212 | 299-TyrArgSerSerLysIlePheGlyValPheAspHisLeuLeuArgThr-314 |
| SEQ. ID. NO. 11213 | 322-LeuGluLysGlyAsnSer-327 |
| SEQ. ID. NO. 11214 | 338-AsnLeuHisAspGluTyrLysAsnLeuThrSerPheIleSerPhe-352 |
| SEQ. ID. NO. 11215 | 361-ArgAspIleLeuGlnMetLeu-367 |
| SEQ. ID. NO. 11216 | 416-TyrGlnAsnPheLeuLysPhePheGluPhe-425 |
| SEQ. ID. NO. 11217 | 434-TyrSerAspPheLeuLysAlaPheGluArgLeuLysLysHis-447 |
| SEQ. ID. NO. 11218 | 454-GluIleProLysPheMetSerThrAlaAsnGlu-464 |
| SEQ. ID. NO. 11219 | 473-AsnValIleAlaTyrLeu-478 |
| SEQ. ID. NO. 11220 | 515-SerGlyLeuSerLysAlaLeuAspValGly-524 |
| Antigenic Index - Jameson-Wolf | |
| SEQ. ID. NO. 11221 | 15-AlaAsnTyrArgArgArgGluAsnLysAspLeuPhe-26 |
| SEQ. ID. NO. 11222 | 33-GlyGluTyrLeuAspGluLeuCysGluProAsnIle-44 |
| SEQ. ID. NO. 11223 | 48-IleGlyGluLysGlyThrGlyLysThr-56 |
| SEQ. ID. NO. 11224 | 64-AsnAsnPheTyrLys-68 |
| SEQ. ID. NO. 11225 | 75-LysPheValArgGluThrAspTyr-82 |
| SEQ. ID. NO. 11226 | 89-LysLysAlaArgHis-93 |
| SEQ. ID. NO. 11227 | 113-AsnGlnIleLysCysLysGluAsnGlyIle-122 |
| SEQ. ID. NO. 11228 | 131-LysAlaLeuAspGluAlaIleAsn-138 |
| SEQ. ID. NO. 11229 | 140-TyrTyrTyrGlyAlaPheAspProGluIle-149 |
| SEQ. ID. NO. 11230 | 157-GluAsnSerLysGluAlaAla-163 |
| SEQ. ID. NO. 11231 | 171-ValLysLeuGlyGluGluGluSerGln-179 |
| SEQ. ID. NO. 11232 | 184-ThrGluSerLysPhe-188 |
| SEQ. ID. NO. 11233 | 194-PheIleGluArgLysPheLysAspAlaLeuSer-204 |
| SEQ. ID. NO. 11234 | 206-LeuLysLeuLysAspAsn-211 |
| SEQ. ID. NO. 11235 | 217-AspGlyIleAspIleArgProSerGlnIleProPhe-228 |
| SEQ. ID. NO. 11236 | 230-GluTyrHisGluCysValLys-236 |
| SEQ. ID. NO. 11237 | 251-ProSerIleLysAspSerLysGlyArgMet-260 |
| SEQ. ID. NO. 11238 | 267-ArgProAspIlePheAspSerLeuGlyLeuGlnAsnGlnAsnThrLysLeuGlnAspAsnSerVal-288 |
| SEQ. ID. NO. 11239 | 291-AspTrpArgThrAspTyrLysSerTyrArgSerSerLysIle-304 |
| SEQ. ID. NO. 11240 | 312-LeuArgThrGlnGlnGluLysGlnAspSerLeuGluLysGlyAsnSerTrpAspTyrTyrPheProTrpAsnAlaProAsnLeuHisAspGluTyrLys AsnLeu-346 |
| SEQ. ID. NO. 11241 | 353-LeuArgLysSerTyrTyrArgProArgAspIle-363 |
| SEQ. ID. NO. 11242 | 371-GlnLysAsnLysLysSerLysGluAspTyrValVal-382 |
| SEQ. ID. NO. 11243 | 384-GluAspPheAspAsnThrSerPheGlnArgGluTyrSer-396 |
| SEQ. ID. NO. 11244 | 412-SerGlnSerAspTyrGlnAsn-418 |
| SEQ. ID. NO. 11245 | 427-AsnGlyLysAspArgPheLysTyrSerAspPhe-437 |
| SEQ. ID. NO. 11246 | 439-LysAlaPheGluArgLeuLysLysHisLeuGln-449 |
| SEQ. ID. NO. 11247 | 454-GluIleProLysPhe-458 |
| SEQ. ID. NO. 11248 | 478-LeuAspAsnProGluAspGluThrLysPro-487 |
| SEQ. ID. NO. 11249 | 493-PheLysAspArgAsnTyrAlaAsnIleSerProLysIleLysThrGluThr-509 |
| SEQ. ID. NO. 11250 | 518-SerLysAlaLeuAsp-522 |
| SEQ. ID. NO. 11251 | 524-GlyThrProPheLysAsnLysGln-531 |
| Hydrophilic Regions - Hopp-Woods | |
| SEQ. ID. NO. 11252 | 15-AlaAsnTyrArgArgArgGluAsnLysAspLeuPhe-26 |
| SEQ. ID. NO. 11253 | 34-GluTyrLeuAspGluLeuCysGlu-41 |
| SEQ. ID. NO. 11254 | 50-GluLysGlyThrGly-54 |
| SEQ. ID. NO. 11255 | 75-LysPheValArgGluThrAspTyr-82 |
| SEQ. ID. NO. 11256 | 89-LysLysAlaArgHis-93 |
| SEQ. ID. NO. 11257 | 115-IleLysCysLysGluAsnGlyIle-122 |
| SEQ. ID. NO. 11258 | 131-LysAlaLeuAspGluAlaIle-137 |

TABLE 1-continued

| | |
|---|---|
| SEQ. ID. NO. 11259 | 157-GluAsnSerLysGluAlaAla-163 |
| SEQ. ID. NO. 11260 | 171-ValLysLeuGlyGluGluGluSerGln-179 |
| SEQ. ID. NO. 11261 | 184-ThrGluSerLysPhe-188 |
| SEQ. ID. NO. 11262 | 194-PheIleGluArgLysPheLysAspAlaLeuSer-204 |
| SEQ. ID. NO. 11263 | 206-LeuLysLeuLysAspAsn-211 |
| SEQ. ID. NO. 11264 | 219-IleAspIleArgPro-223 |
| SEQ. ID. NO. 11265 | 230-GluTyrHisGluCysValLys-236 |
| SEQ. ID. NO. 11266 | 251-ProSerIleLysAspSerLysGlyArgMet-260 |
| SEQ. ID. NO. 11267 | 279-GlnAsnThrLysLeuGlnAsp-285 |
| SEQ. ID. NO. 11268 | 292-TrpArgThrAspTyrLysSerTyrArgSer-301 |
| SEQ. ID. NO. 11269 | 314-ThrGlnGlnGluLysGlnAspSerLeuGluLysGlyAsnSer-327 |
| SEQ. ID. NO. 11270 | 338-AsnLeuHisAspGluTyrLysAsn-345 |
| SEQ. ID. NO. 11271 | 356-SerTyrTyrArgProArgAspIle-363 |
| SEQ. ID. NO. 11272 | 371-GlnLysAsnLysLysSerLysGluAspTyrValVal-382 |
| SEQ. ID. NO. 11273 | 384-GluAspPheAspAsn-388 |
| SEQ. ID. NO. 11274 | 427-AsnGlyLysAspArgPheLysTyr-434 |
| SEQ. ID. NO. 11275 | 439-LysAlaPheGluArgLeuLysLysHisLeuGln-449 |
| SEQ. ID. NO. 11276 | 479-AspAsnProGluAspGluThrLysPro-487 |
| SEQ. ID. NO. 11277 | 493-PheLysAspArgAsnTyr-498 |
| SEQ. ID. NO. 11278 | 503-ProLysIleLysThrGluThr-509 |
| SEQ. ID. NO. 11279 | 527-PheLysAsnLysGln-531 |
| 745 | |
| AMPHI Regions - AMPHI | |
| SEQ. ID. NO. 11280 | 9-SerValThrAlaValIle-14 |
| SEQ. ID. NO. 11281 | 33-AspValIleLeuAsnAsp-38 |
| SEQ. ID. NO. 11282 | 116-CysThrAsnPheIleLysLeuTrpAsnAlaValSer-127 |
| SEQ. ID. NO. 11283 | 145-GluLeuGluIleLeuVal-150 |
| Antigenic Index - Jameson-Wolf | |
| SEQ. ID. NO. 11284 | 21-IleAsnLysLysThrSerLysGlnLysAlaThr-31 |
| SEQ. ID. NO. 11285 | 37-AsnAspTyrGlnAsp-41 |
| SEQ. ID. NO. 11286 | 43-GlnPheValGluAlaAspAsnHisIleSerProTyrIle-55 |
| SEQ. ID. NO. 11287 | 58-ThrAlaValAspAspAsnAsnAlaArg-66 |
| SEQ. ID. NO. 11288 | 73-TyrGlnAsnLysGlyGlyGlnTrpGluLysGluArgGlyHis-86 |
| SEQ. ID. NO. 11289 | 102-AsnSerGlyValLeuAspGluAspLeuPheLys-112 |
| SEQ. ID. NO. 11290 | 132-LysIleArgGluGluGluArgLysAspThrIlePheArgGluLeuGlu-147 |
| SEQ. ID. NO. 11291 | 156-AsnProLeuLysAlaSerAspLeu-163 |
| Hydrophilic Regions - Hopp-Woods | |
| SEQ. ID. NO. 11292 | 23-LysLysThrSerLysGlnLysAlaThr-31 |
| SEQ. ID. NO. 11293 | 43-GlnPheValGluAlaAspAsnHis-50 |
| SEQ. ID. NO. 11294 | 58-ThrAlaValAspAspAsnAsnAlaArg-66 |
| SEQ. ID. NO. 11295 | 76-LysGlyGlyGlnTrpGluLysGluArgGlyHis-86 |
| SEQ. ID. NO. 11296 | 105-ValLeuAspGluAspLeuPheLys-112 |
| SEQ. ID. NO. 11297 | 132-LysIleArgGluGluGluArgLysAspThrIlePheArgGluLeuGlu-147 |
| SEQ. ID. NO. 11298 | 156-AsnProLeuLysAlaSerAspLeu-163 |
| 746 | |
| AMPHI Regions - AMPHI | |
| SEQ. ID. NO. 11299 | 10-LeuSerGlyTyrGluGlnLeuLys-17 |
| SEQ. ID. NO. 11300 | 42-LeuSerSerGlyProAlaGluGlnThrAla-51 |
| SEQ. ID. NO. 11301 | 72-SerAlaAlaAspLysProGlnAsp-79 |
| SEQ. ID. NO. 11302 | 94-SerGluProGluAsn-98 |
| SEQ. ID. NO. 11303 | 118-LeuGluAlaSerGluLysLeuGlnGlnAlaGluThrAlaLysThrAlaPro-134 |
| SEQ. ID. NO. 11304 | 153-AspThrValAlaValGlu-158 |
| SEQ. ID. NO. 11305 | 160-ProLysArgThrAlaGluThr-166 |
| SEQ. ID. NO. 11306 | 170-LysAlaGluArgThr-174 |
| SEQ. ID. NO. 11307 | 184-ThrLysThrAlaGluLysValAlaAspLysProLys-195 |
| SEQ. ID. NO. 11308 | 210-SerAlaValLysGluAlaLysLysAlaAspLysAlaGluSer-223 |
| SEQ. ID. NO. 11309 | 238-GluThrAlaGlnLysThrAspLysAlaAspLysThrLysThrAlaGluLys-254 |
| SEQ. ID. NO. 11310 | 287-SerThrIleThrGluIleMetThr-294 |
| SEQ. ID. NO. 11311 | 307-TyrLysAsnAlaArgAspAlaGluArgAspLeu-317 |
| Antigenic Index - Jameson-Wolf | |
| SEQ. ID. NO. 11312 | 1-MetSerGluAsnLysGlnAsnGluValLeuSerGlyTyrGluGlnLeuLysArgArgAsnArgArgArgLeuValThr-26 |
| SEQ. ID. NO. 11313 | 43-SerSerGlyProAlaGluGlnThrAlaGlyGluThrSerGlyValGluAsnLysAlaAlaGly-63 |
| SEQ. ID. NO. 11314 | 68-ProAlaLeuLysSerAlaAlaAspLysProGlnAspLeuAlaGlyGluAspLysProSerAlaAlaAspSerGluIleSerGluProGluAsnVal-99 |
| SEQ. ID. NO. 11315 | 108-GluArgLeuGluAspSerAsnIleLysGlyLeuGluAlaSerGluLysLeuGlnGlnAlaGluThrAlaLysThrAlaProLysGlnAlaLysGln ArgAlaAlaGluLysValProAlaThrAlaAspSerThrAspThrValAlaValGluLysProLysArgThrAlaGluThrLysProGlnLysAlaGluArg ThrAlaLysAlaLysProLysAlaLysGluThrLysThrAlaGluLysValAlaAspLysProLysThrAlaAlaGluLysThrLysProAspThrAla LysSerAspSerAlaValLysGluAlaLysLysAlaAspLysAlaGluSerLysLysThrAlaGluLysAspArgSerAspGlyLysLysHisGluThr AlaGlnLysThrAspLysAlaAspLysThrLysThrAlaGluLysGluLysSerGlyLysLysAlaAla-262 |
| SEQ. ID. NO. 11316 | 266-GlyTyrAlaGluLysGluArgAlaLeuSerLeuGlnArgLysMetLysAlaAlaGlyIle-285 |
| SEQ. ID. NO. 11317 | 292-IleMetThrAspAsnGlyLysValTyrArgValLysSerSerAsnTyrLysAsnAlaArgAspAlaGluArgAspLeuAsnLysLeuArgVal-322 |
| Hydrophilic Regions - Hopp-Woods | |
| SEQ. ID. NO. 11318 | 1-MetSerGluAsnLysGlnAsnGluVal-9 |
| SEQ. ID. NO. 11319 | 14-GluGlnLeuLysArgArgAsnArgArgArgLeuVal-25 |
| SEQ. ID. NO. 11320 | 45-GlyProAlaGluGlnThrAlaGlyGluThrSerGlyValGluAsnLysAlaAlaGly-63 |
| SEQ. ID. NO. 11321 | 68-ProAlaLeuLysSerAlaAlaAspLysProGlnAspLeuAlaGlyGluAspLysProSerAlaAlaAspSerGluIleSerGluProGluAsnVal-99 |
| SEQ. ID. NO. 11322 | 108-GluArgLeuGluAspSerAsnIleLysGlyLeuGluAlaSerGluLysLeuGlnGlnAlaGluThrAlaLysThrAlaProLysGlnAlaLysGlnArg AlaAlaGluLysValProAlaThrAlaAspSerThrAsp-153 |

TABLE 1-continued

| | |
|---|---|
| SEQ. ID. NO. 11323 | 155-ValAlaValGluLysProLysArgThrAlaGluThrLysProGlnLysAlaGluArgThrAlaLysAlaLysProLysAlaLysGluThrLysThrAla GluLysValAlaAspLysProLysThrAlaAlaGluLysThrLysProAspThrAlaLysSerAspSerAlaValLysGluAlaLysLysAlaAspLysAla GluSerLysLysThrAlaGluLysAspArgSerAspGlyLysLysHisGluThrAlaGlnLysThrAspLysAlaAspLysThrLysThrAlaGluLys GluLysSerGlyLysLysAlaAla-262 |
| SEQ. ID. NO. 11324 | 267-TyrAlaGluLysGluArgAlaLeuSerLeuGlnArgLysMetLysAlaAlaGlyIle-285 |
| SEQ. ID. NO. 11325 | 292-IleMetThrAspAsnGlyLysValTyrArgValLysSerSerAsnTyrLysAsnAlaArgAspAlaGluArgAspLeuAsnLysLeuArgVal-322 |
| 747 | |
| AMPHI Regions - AMPHI | |
| SEQ. ID. NO. 11326 | 24-AlaSerArgAspValSerLysSerAlaLysGlyTrp-35 |
| Antigenic Index - Jameson-Wolf | |
| SEQ. ID. NO. 11327 | 8-TyrAlaAspLeuArgGlyLysThrLysVal-17 |
| SEQ. ID. NO. 11328 | 23-GlyAlaSerArgAspValSerLysSerAlaLysGlyTrp-35 |
| SEQ. ID. NO. 11329 | 42-AsnValGlyLysGlnLeuThrAspSerValGlyLeuGluPheAspProTyrTyrArgHisLysThrIleTyrLysProArgGluIleValLeuAspGly AspLysThrLysMetGlyArgSerLysSerAsnGluTyrGly-88 |
| SEQ. ID. NO. 11330 | 97-SerGlnLeuLysSerLys-102 |
| Hydrophilic Regions - Hopp-Woods | |
| SEQ. ID. NO. 11331 | 8-TyrAlaAspLeuArgGlyLysThrLysVal-17 |
| SEQ. ID. NO. 11332 | 23-GlyAlaSerArgAspValSerLysSerAlaLys-33 |
| SEQ. ID. NO. 11333 | 63-ThrIleTyrLysProArgGluIleValLeuAspGlyAspLysThrLysMetGlyArgSerLysSerAsnGluTyr-87 |
| 748 | |
| AMPHI Regions - AMPHI | |
| SEQ. ID. NO. 11334 | 22-GlyAlaValGlyAlaIleGlyGly-29 |
| SEQ. ID. NO. 11335 | 37-GlyGluThrAlaGluArgThrAlaGluSerGlnHis-48 |
| SEQ. ID. NO. 11336 | 82-SerAlaLysGlnLeuGluAsnLeuPheArgThrLeu-93 |
| SEQ. ID. NO. 11337 | 155-LeuGlnGluMetArgAspPheSerAsnAspLysLeuGlnLysSerTrp-170 |
| SEQ. ID. NO. 11338 | 188-GlnAlaAlaLeuArgAspIleIleLysHisThrValGln-200 |
| SEQ. ID. NO. 11339 | 250-GlyValAlaAlaAsnSer-255 |
| SEQ. ID. NO. 11340 | 257-AspGluProGluTrp-261 |
| SEQ. ID. NO. 11341 | 268-GlnAlaValArgLeuIleArgHisPheValGluPheTrpAspArg-282 |
| SEQ. ID. NO. 11342 | 310-GlnProAspPheAlaLysAspProGlu-318 |
| SEQ. ID. NO. 11343 | 334-ArgAspProGluPheLeu-339 |
| SEQ. ID. NO. 11344 | 390-LeuGluGluTyrIleSerProPhe-397 |
| Antigenic Index - Jameson-Wolf | |
| SEQ. ID. NO. 11345 | 1-MetSerLysLysGlnProAlaGlnProThrArgArgThrLeuPhe-15 |
| SEQ. ID. NO. 11346 | 30-TyrLeuGlyGlyLysLysGlnGlyGluThrAlaGluArgThrAlaGluSerGlnHisSerProGlnAla-52 |
| SEQ. ID. NO. 11347 | 80-AlaGlnSerAlaLysGlnLeuGluAsn-88 |
| SEQ. ID. NO. 11348 | 101-ThrGlnGlyGlyGluTyrGlnAspGlyAspAspLysLeuProProAlaGlySerGly-119 |
| SEQ. ID. NO. 11349 | 125-PheAsnProAspGlyLeuThr-131 |
| SEQ. ID. NO. 11350 | 139-SerLeuPheAspGlyArgPheGlyLeuLysAspLysLysProIleHis-154 |
| SEQ. ID. NO. 11351 | 156-GlnGluMetArgAspPheSerAsnAspLysLeuGlnLysSerTrpCysAspGlyAspLeuSer-176 |
| SEQ. ID. NO. 11352 | 183-ThrProGluThrCys-187 |
| SEQ. ID. NO. 11353 | 208-IleAspGlyTrpGlnProLysSerGluProGlyAlaMetAla-221 |
| SEQ. ID. NO. 11354 | 226-LeuGlyPheArgAspGlyThrGlyAsnProLysValSerAspProLysThrAlaAspGlu-245 |
| SEQ. ID. NO. 11355 | 255-SerLeuAspGluProGluTrpAlaLysAsnGlySerTyrGlnAla-269 |
| SEQ. ID. NO. 11356 | 279-PheTrpAspArgThrProLeuGlnGluGlnThrAspIlePheGlyArgArgLysTyrSerGlyAlaProMetAspGlyLysLysGluAlaAspGlnPro AspPheAlaLysAspProGluGlyAspIleThrProLysAspSerHisIleArgLeuAlaAsnProArgAspProGluPheLeuLysLysHisArgLeuPhe Arg-346 |
| SEQ. ID. NO. 11357 | 348-AlaTyrSerTyrSerArgGlyLeuAlaSerSerGlyGlnLeu-361 |
| SEQ. ID. NO. 11358 | 385-LeuAsnGlyGluProLeuGluGluTyr-393 |
| SEQ. ID. NO. 11359 | 406-ProGlyValGluLysGlyGlyPhe-413 |
| Hydrophilic Regions - Hopp-Woods | |
| SEQ. ID. NO. 11360 | 1-MetSerLysLysGlnProAlaGlnProThrArgArgThrLeuPhe-15 |
| SEQ. ID. NO. 11361 | 32-GlyGlyLysLysGlnGlyGluThrAlaGluArgThrAlaGluSerGlnHisSer-49 |
| SEQ. ID. NO. 11362 | 80-AlaGlnSerAlaLysGlnLeuGluAsn-88 |
| SEQ. ID. NO. 11363 | 104-GlyGluTyrGlnAspGlyAspAspLysLeuProPro-115 |
| SEQ. ID. NO. 11364 | 145-PheGlyLeuLysAspLysLysProIleHis-154 |
| SEQ. ID. NO. 11365 | 156-GlnGluMetArgAspPheSerAsnAspLysLeuGlnLysSerTrpCysAspGlyAspLeu-175 |
| SEQ. ID. NO. 11366 | 211-TrpGlnProLysSerGluProGlyAlaMetAla-221 |
| SEQ. ID. NO. 11367 | 229-ArgAspGlyThrGlyAsnProLysValSerAspProLysThrAlaAsp-244 |
| SEQ. ID. NO. 11368 | 255-SerLeuAspGluProGluTrpAlaLys-263 |
| SEQ. ID. NO. 11369 | 283-ThrProLeuGlnGluGlnThrAspIlePheGlyArgArgLysTyrSer-298 |
| SEQ. ID. NO. 11370 | 301-ProMetAspGlyLysLysGluAlaAspGlnProAspPheAlaLysAspProGluGlyAspIleThrProLysAspSerHisIle-328 |
| SEQ. ID. NO. 11371 | 331-AlaAsnProArgAspProGluPheLeuLysLysHisArgLeuPheArg-346 |
| SEQ. ID. NO. 11372 | 388-GluProLeuGluGluTyr-393 |
| SEQ. ID. NO. 11373 | 407-GlyValGluLysGlyGly-412 |
| 749 | |
| AMPHI Regions - AMPHI | |
| SEQ. ID. NO. 11374 | 20-CysGlnProProGluAla-25 |
| SEQ. ID. NO. 11375 | 140-AlaAspLeuGluLysLeuSerGlnProLeuAla-150 |
| SEQ. ID. NO. 11376 | 157-GlnGlyGluValLysGluLeuVal-164 |
| SEQ. ID. NO. 11377 | 169-ThrPheThrGluAlaValLysAlaGlyAspIleGluLysAla-182 |
| SEQ. ID. NO. 11378 | 196-IleGluProIleAlaGluLeuPheSerGluLeuAspPro-208 |
| SEQ. ID. NO. 11379 | 224-AlaGlyPheThrGlyPheHisArg-231 |
| SEQ. ID. NO. 11380 | 243-SerGlyValLysGluIleAlaAlaLysLeuMetThrAspValGluAlaLeuGlnLysGluIleAsp-264 |
| SEQ. ID. NO. 11381 | 274-ValGlyGlyAlaSerGluLeuIleGluGluValAlaGly-286 |
| SEQ. ID. NO. 11382 | 309-AspGlySerLysLysIleValAspLeuPheArgProLeu-321 |
| SEQ. ID. NO. 11383 | 337-PheLysGlnValAsnGluIleLeuAlaLys-346 |

TABLE 1-continued

| | |
|---|---|
| SEQ. ID. NO. 11384 | 351-AspGlyPheGluThrTyrAspLysLeuGlyGlu-361 |
| SEQ. ID. NO. 11385 | 366-AlaLeuGlnAlaSerIleAsnAlaLeuAlaGluAspLeuAlaGlnLeuArgGlyIleLeuGlyLeu-387 |
| Antigenic Index - Jameson-Wolf | |
| SEQ. ID. NO. 11386 | 1-MetArgLysPheAsn-5 |
| SEQ. ID. NO. 11387 | 21-GlnProProGluAlaGluLysAlaAlaPro-30 |
| SEQ. ID. NO. 11388 | 32-AlaSerGlyGluAlaGlnThrAlaAsnGluGlyGlySer-44 |
| SEQ. ID. NO. 11389 | 50-AsnAspAsnAlaCysGluProMetGlu-58 |
| SEQ. ID. NO. 11390 | 70-IleLysAsnAsnSerGlyArgLysLeuGluTrpGluIle-82 |
| SEQ. ID. NO. 11391 | 87-MetValValAspGluArgGluAsnIleAla-96 |
| SEQ. ID. NO. 11392 | 98-GlyLeuSerAspLysMetThr-104 |
| SEQ. ID. NO. 11393 | 108-LeuProGlyGluTyrGluMet-114 |
| SEQ. ID. NO. 11394 | 120-ThrAsnProArgGlyLysLeuValValThrAspSerGlyPheLysAspThrAlaAsnGluAlaAspLeuGluLysLeuSer-146 |
| SEQ. ID. NO. 11395 | 158-GlyGluValLysGluLeuValAlaLysThrLysThrPheThrGluAlaValLysAlaGlyAspIleGluLysAlaLysSerLeuPheAla-187 |
| SEQ. ID. NO. 11396 | 189-ThrArgValHisTyrGluArgIleGluProIle-199 |
| SEQ. ID. NO. 11397 | 204-SerGluLeuAspProValIleAspAlaArgGluAspAspPheLysAspGlyAlaLysAspAlaGly-225 |
| SEQ. ID. NO. 11398 | 238-ValGluLysAspValSerGlyValLysGluIleAlaAla-250 |
| SEQ. ID. NO. 11399 | 252-LeuMetThrAspValGluAlaLeuGlnLysGluIleAsp-264 |
| SEQ. ID. NO. 11400 | 269-ProProGlyLysValValGlyGlyAla-277 |
| SEQ. ID. NO. 11401 | 279-GluLeuIleGluGluValAlaGlySerLysIleSerGlyGluGluAspArgTyrSerHisThrAspLeuSerAspPheGlnAlaAsnValAspGly SerLysLysIleValAsp-316 |
| SEQ. ID. NO. 11402 | 322-IleGluAlaLysAsnLysAlaLeuLeuGluLysThrAspThrAsnPheLysGlnValAsn-341 |
| SEQ. ID. NO. 11403 | 345-AlaLysTyrArgThrLysAspGlyPheGluThrTyrAspLysLeuGlyGluAlaAspArgLysAlaLeu-367 |
| SEQ. ID. NO. 11404 | 374-LeuAlaGluAspLeuAlaGln-380 |
| Hydrophilic Regions - Hopp-Woods | |
| SEQ. ID. NO. 11405 | 1-MetArgLysPheAsn-5 |
| SEQ. ID. NO. 11406 | 21-GlnProProGluAlaGluLysAlaAlaPro-30 |
| SEQ. ID. NO. 11407 | 32-AlaSerGlyGluAlaGlnThrAlaAsnGluGlyGlySer-44 |
| SEQ. ID. NO. 11408 | 52-AsnAlaCysGluProMetGlu-58 |
| SEQ. ID. NO. 11409 | 72-AsnAsnSerGlyArgLysLeuGluTrpGluIle-82 |
| SEQ. ID. NO. 11410 | 87-MetValValAspGluArgGluAsnIle-95 |
| SEQ. ID. NO. 11411 | 99-LeuSerAspLysMetThr-104 |
| SEQ. ID. NO. 11412 | 110-GlyGluTyrGluMet-114 |
| SEQ. ID. NO. 11413 | 122-ProArgGlyLysLeuValVal-128 |
| SEQ. ID. NO. 11414 | 131-SerGlyPheLysAspThrAlaAsnGluAlaAspLeuGluLysLeuSer-146 |
| SEQ. ID. NO. 11415 | 158-GlyGluValLysGluLeuValAlaLysThrLysThrPheThrGluAlaValLysAlaGlyAspIleGluLysAlaLysSerLeuPheAla-187 |
| SEQ. ID. NO. 11416 | 189-ThrArgValHisTyrGluArgIleGluProIle-199 |
| SEQ. ID. NO. 11417 | 204-SerGluLeuAspProValIleAspAlaArgGluAspAspPheLysAspGlyAlaLysAspAlaGly-225 |
| SEQ. ID. NO. 11418 | 238-ValGluLysAspValSerGlyValLysGluIleAlaAla-250 |
| SEQ. ID. NO. 11419 | 252-LeuMetThrAspValGluAlaLeuGlnLysGluIleAsp-264 |
| SEQ. ID. NO. 11420 | 279-GluLeuIleGluGluValAlaGly-286 |
| SEQ. ID. NO. 11421 | 288-LysIleSerGlyGluGluAspArgTyrSerHis-298 |
| SEQ. ID. NO. 11422 | 308-ValAspGlySerLysLysIleValAsp-316 |
| SEQ. ID. NO. 11423 | 322-IleGluAlaLysAsnLysAlaLeuLeuGluLysThrAspThrAsnPhe-337 |
| SEQ. ID. NO. 11424 | 347-TyrArgThrLysAspGlyPheGluThrTyrAspLysLeuGlyGluAlaAspArgLysAlaLeu-367 |
| SEQ. ID. NO. 11425 | 374-LeuAlaGluAspLeuAlaGln-380 |
| 750 | |
| AMPHI Regions - AMPHI | |
| SEQ. ID. NO. 11426 | 1-ValLysProArgPheTyrTrpAlaAlaCysAlaValLeuLeuThrAlaCysSerProGluProAlaAlaGluLysThrValSerAlaAlaSerAlaSerAla AlaThrLeuThrValProThrAlaArgGlyAspAlaValValProLysAsnProGluArgValAlaValTyrAspTrpAlaAlaLeuAspThrLeuThr GluLeuGlyValAsnValGlyAlaThrThrAlaProValArgValAspTyrLeuGlnProAlaPheAspLysAlaAlaThrValGlyThrLeuPheGluPro AspTyrGluAlaLeuHisArgTyrAsnProGlnLeuValIleThrGlyGlyProGlyAlaGluAlaTyrGluGlnLeuAlaLysAsnAlaThrThrIleAspLeu ThrValAspAsnGlyAsnIleArgThrSerGlyGluLysGlnMetGluThrLeuAlaArgIlePheGlyLysGluAlaArgAlaAlaGluLeuLysAlaGln IleAspAlaLeuPheAlaGlnThrArgGluAlaAlaLysGlyLysGlyArgGlyLeuValLeuSerValThrGlyAsnLysValSerAlaPheGlyThrGln SerArgLeuAlaSerTrpIleHisGlyAspIleGlyLeuProProValAspGluSerLeuArgAsnGluGlyHisGlyGlnProValSerPheGluTyrIleLys GluLysAsnProAspTrpIlePheIleIleAspArgThrAlaAlaIleGlyGlnGluGlyProAlaAlaValGluValLeuAspAsnAlaLeuValArgGly ThrAsnAlaTrpLysArgLysGlnIleIleValMetProAlaAlaAsnTyrIleValAlaGlyGlyAlaArgGlnLeuIleGlnAlaAlaGluGlnLeuLys AlaAlaPheLysLysAlaGluProValAlaAlaGlyLysLys-321 |

Antigenic Index - Jameson-Wolf
(SEQ. ID. NO. 11426)
1-ValLysProArgPheTyrTrpAlaAlaCysAlaValLeuLeuThrAlaCysSerProGluProAlaAlaGluLysThrValSerAlaAlaSerAlaSerAlaAlaThrLeuThrValProThr AlaArgGlyAspAlaValValProLysAsnProGluArgValAlaValTyrAspTrpAlaAlaLeuAspThrLeuThrGluLeuGlyValAsnValGlyAlaThrThrAlaProValArgValAsp TyrLeuGlnProAlaPheAspLysAlaAlaThrValGlyThrLeuPheGluProAspTyrGluAlaLeuHisArgTyrAsnProGlnLeuValIleThrGlyGlyProGlyAlaGluAlaTyr GluGlnLeuAlaLysAsnAlaThrThrIleAspLeuThrValAspAsnGlyAsnIleArgThrSerGlyGluLysGlnMetGluThrLeuAlaArgIlePheGlyLysGluAlaArgAlaAlaGlu LeuLysAlaGlnIleAspAlaLeuPheAlaGlnThrArgGluAlaAlaLysGlyLysGlyArgGlyLeuValLeuSerValThrGlyAsnLysValSerAlaPheGlyThrGlnSerArgLeuA laSerTrpIleHisGlyAspIleGlyLeuProProValAspGluSerLeuArgAsnGluGlyHisGlyGlnProValSerPheGluTyrIleLysGluLysAsnProAspTrpIlePheIleIleAsp ArgThrAlaAlaIleGlyGlnGluGlyProAlaAlaValGluValLeuAspAsnAlaLeuValArgGlyThrAsnAlaTrpLysArgLysGlnIleIleValMetProAlaAlaAsnTyrIle ValAlaGlyGlyAlaArgGlnLeuIleGlnAlaAlaGluGlnLeuLysAlaAlaPheLysLysAlaGluProValAlaAlaGlyLysLys-321

Hydrophilic Regions - Hopp-Woods
(SEQ. ID. NO. 11426)
1-ValLysProArgPheTyrTrpAlaAlaCysAlaValLeuLeuThrAlaCysSerProGluProAlaAlaGluLysThrValSerAlaAlaSerAlaSerAlaAlaThrLeuThrValProThrAla ArgGlyAspAlaValValProLysAsnProGluArgValAlaValTyrAspTrpAlaAlaLeuAspThrLeuThrGluLeuGlyValAsnValGlyAlaThrThrAlaProValArgValAspTyr LeuGlnProAlaPheAspLysAlaAlaThrValGlyThrLeuPheGluProAspTyrGluAlaLeuHisArgTyrAsnProGlnLeuValIleThrGlyGlyProGlyAlaGluAlaTyr GluGlnLeuAlaLysAsnAlaThrThrIleAspLeuThrValAspAsnGlyAsnIleArgThrSerGlyGluLysGlnMetGluThrLeuAlaArgIlePheGlyLysGluAlaArg AlaAlaGluLeuLysAlaGlnIleAspAlaLeuPheAlaGlnThrArgGluAlaAlaLysGlyLysGlyArgGlyLeuValLeuSerValThrGlyAsnLysValSerAlaPheGly ThrGlnSerArgLeuAlaSerTrpIleHisGlyAspIleGlyLeuProProValAspGluSerLeuArgAsnGluGlyHisGlyGlnProValSerPheGluTyrIleLysGluLysAsn TABLE 1-continued ProAspTrpIlePheIleIleAspArgThrAlaAlaIleGlyGlnGluGlyProAlaAlaValGluValLeuAspAsnAlaLeuValArgGlyThrAsnAlaTrpLysArgLysGln
IleIleValMetProAlaAlaAsnTyrIleValAlaGlyGlyAlaArgGlnLeuIleGlnAlaAlaGluGlnLeuLysAlaAlaPheLysLysAlaGluProValAlaAlaGlyLysLys-321
751
AMPHI Regions - AMPHI

| | |
|---|---|
| SEQ. ID. NO. 11427 | 11-AlaAspArgAlaValArgSerAlaThr-19 |
| SEQ. ID. NO. 11428 | 59-IleGlnAspThrAsn-63 |
| SEQ. ID. NO. 11429 | 82-LeuSerAsnAlaAla-86 |
| SEQ. ID. NO. 11430 | 139-LeuAsnAsnLysValPheGlnGlyTyr-147 |
| SEQ. ID. NO. 11431 | 156-LeuAsnGlnAspIleTyrArgGluValGlnLysMetGly-168 |
| SEQ. ID. NO. 11432 | 215-AsnValGlnAsnAspTyrAlaAspValLeu-224 |
| SEQ. ID. NO. 11433 | 281-SerTyrPheAlaGluValProLysAlaGlyThrLysGluPheAspAspTyrValLysIleTrpGlyGlu-303 |

Antigenic Index - Jameson-Wolf

| | |
|---|---|
| SEQ. ID. NO. 11434 | 9-ThrGlnAlaAspArgAlaValArg-16 |
| SEQ. ID. NO. 11435 | 18-AlaThrAlaProLys-22 |
| SEQ. ID. NO. 11436 | 29-LysIleIleAspGluLysThrGlyLysValSerPheAspThrArgGlnIle-45 |
| SEQ. ID. NO. 11437 | 50-AspLeuSerLysGluGluLeuAlaSerIleGlnAspThrAsnGlyLysVal-66 |
| SEQ. ID. NO. 11438 | 72-ProGlyIlePheAsnAsnArgGluAspSerLeuSerAsnAlaAlaLysGlnAsnArgAsnSerThrAsnGlySer-96 |
| SEQ. ID. NO. 11439 | 104-ProProThrGlyLysTyrLysSerAspSerAsnAsnLysIleLys-118 |
| SEQ. ID. NO. 11440 | 137-AspGlnLeuAsnAsnLys-142 |
| SEQ. ID. NO. 11441 | 147-TyrLeuProLysThrAsnSerGluLysLeuAsnGlnAspIleTyrArgGluValGlnLysMetGlyAsnGlyTrpSerValAspThrSerAsnHisSer ArgGlyGlyIle-183 |
| SEQ. ID. NO. 11442 | 190-LysAspTrpValAsnAsnGlnLysGlnAsnGly-200 |
| SEQ. ID. NO. 11443 | 203-ProIleArgLysAlaArgPhe-209 |
| SEQ. ID. NO. 11444 | 214-ThrAsnValGlnAsnAspTyrAlaAspValLeuGlnLysAsnGlyTyr-229 |
| SEQ. ID. NO. 11445 | 233-GlyAlaAspGlyLysThrTyrAsnSerGlySer-243 |
| SEQ. ID. NO. 11446 | 247-ValHisAspLysAspPheValGlyAsnLys-256 |
| SEQ. ID. NO. 11447 | 263-GlyThrAsnAspThrThrGlnGlyThrCysLysGlyLeuCys-276 |
| SEQ. ID. NO. 11448 | 286-ValProLysAlaGlyThrLysGluPheAspAspTyrVal-298 |
| SEQ. ID. NO. 11449 | 304-ValGluTyrAspAlaGlnGlyLysProIleAsnLysSerLysProIleLeuValGluProAsnLysThrLysAspAsnGluLysTyrGluLysGlu AlaPhe-337 |

Hydrophilic Regions - Hopp-Woods

| | |
|---|---|
| SEQ. ID. NO. 11450 | 10-GlnAlaAspArgAlaValArg-16 |
| SEQ. ID. NO. 11451 | 18-AlaThrAlaProLys-22 |
| SEQ. ID. NO. 11452 | 29-LysIleIleAspGluLysThrGlyLysValSerPheAspThr-42 |
| SEQ. ID. NO. 11453 | 50-AspLeuSerLysGluGluLeuAlaSer-58 |
| SEQ. ID. NO. 11454 | 60-GlnAspThrAsnGly-64 |
| SEQ. ID. NO. 11455 | 76-AsnAsnArgGluAspSerLeuSerAsnAlaAlaLysGlnAsnArgAsnSerThrAsn-94 |
| SEQ. ID. NO. 11456 | 105-ProThrGlyLysTyrLysSerAspSerAsnAsnLysIleLys-118 |
| SEQ. ID. NO. 11457 | 151-ThrAsnSerGluLysLeuAsnGlnAspIleTyrArgGluValGlnLysMet-167 |
| SEQ. ID. NO. 11458 | 175-ThrSerAsnHisSerArgGlyGlyIle-183 |
| SEQ. ID. NO. 11459 | 196-GlnLysGlnAsnGly-200 |
| SEQ. ID. NO. 11460 | 203-ProIleArgLysAlaArgPhe-209 |
| SEQ. ID. NO. 11461 | 219-AspTyrAlaAspValLeuGln-225 |
| SEQ. ID. NO. 11462 | 234-AlaAspGlyLysThrTyrAsn-240 |
| SEQ. ID. NO. 11463 | 247-ValHisAspLysAspPheVal-253 |
| SEQ. ID. NO. 11464 | 265-AsnAspThrThrGlnGlyThrCys-272 |
| SEQ. ID. NO. 11465 | 286-ValProLysAlaGlyThrLysGluPheAspAspTyrVal-298 |
| SEQ. ID. NO. 11466 | 304-ValGluTyrAspAlaGlnGlyLysProIleAsnLysSerLysProIleLeu-320 |
| SEQ. ID. NO. 11467 | 322-GluProAsnLysThrLysAspAsnGluLysTyrGluLysGluAlaPhe-337 |

752-2
AMPHI Regions - AMPHI

| | |
|---|---|
| SEQ. ID. NO. 11468 | 6-GluArgMetThrGlnIleAlaLysLeuLeuAsnSerSer-18 |
| SEQ. ID. NO. 11469 | 29-PheLeuThrGluIleLysAspTyrSerGluPhe-39 |
| SEQ. ID. NO. 11470 | 51-TrpAspLysPheArgArgIle-57 |
| SEQ. ID. NO. 11471 | 69-ValLysGluSerArgLysLysIleGlnLysProIleAsp-81 |
| SEQ. ID. NO. 11472 | 105-LysSerCysGlySerSerIleGly-112 |
| SEQ. ID. NO. 11473 | 114-SerSerLeuGlyGlyPheGly-120 |
| SEQ. ID. NO. 11474 | 145-GlyAlaAlaThrThrArgLysValAlaLysAspMetLeuLysSerGln-160 |
| SEQ. ID. NO. 11475 | 194-IleLeuAspLeuHisArgIleAlaThrSer-203 |
| SEQ. ID. NO. 11476 | 233-GlnProProProHisGly-238 |
| SEQ. ID. NO. 11477 | 240-ValHisThrLeuMetGluGluVal-247 |
| SEQ. ID. NO. 11478 | 254-ThrTyrAspGlyValGluAsnProPheIleHisProValValGlnAlaIle-270 |
| SEQ. ID. NO. 11479 | 272-LeuHisPheLeuIleGlyTyrIleHisPro-281 |
| SEQ. ID. NO. 11480 | 309-IleSerIleSerArgLeuLeuLysAsnAlaProAlaGlnTyr-322 |
| SEQ. ID. NO. 11481 | 347-IleLysArgAlaValAlaAspLeuGluHis-356 |
| SEQ. ID. NO. 11482 | 371-AlaIleAlaGlnTyrThrGluLysIleGlyLysLeu-382 |
| SEQ. ID. NO. 11483 | 390-LeuGlnLysAlaValGluGluSerGly-398 |
| SEQ. ID. NO. 11484 | 422-SerLysLeuGlyGluTyrArgPhe-429 |
| SEQ. ID. NO. 11485 | 435-SerGlyAsnAlaLeuGluTyrValAlaPro-444 |

Antigenic Index - Jameson-Wolf

| | |
|---|---|
| SEQ. ID. NO. 11486 | 4-LeuThrGluArgMetThrGln-10 |
| SEQ. ID. NO. 11487 | 15-LeuAsnSerSerAlaAsnAsnProAspIleAspIleProAspPheLeuThrGluIleLysAspTyrSerGlu-38 |
| SEQ. ID. NO. 11488 | 40-SerValThrAspGluAsnGlyThr-47 |
| SEQ. ID. NO. 11489 | 52-AspLysPheArgArgIleHisThrGluAspThrArgMetLysTrpArgAlaValLysGluSerArgLysLysIleGlnLysProIleAsp-81 |
| SEQ. ID. NO. 11490 | 92-IleProAspSerLeuGln-97 |
| SEQ. ID. NO. 11491 | 102-LeuIleAspLysSerCysGlySerSerIleGly-112 |
| SEQ. ID. NO. 11492 | 117-GlyGlyPheGlyArgSerGluGlnAsnArgPheLeu-128 |
| SEQ. ID. NO. 11493 | 147-AlaThrThrArgLysValAlaLysAspMetLeuLysSerGlnArgLysProLysThrLysAspGluIle-169 |
| SEQ. ID. NO. 11494 | 179-LysLysAlaValGluLeuLysAsnThr-187 |
| SEQ. ID. NO. 11495 | 204-AsnAlaIleGluAsnLysAlaGluProGlyGlnPheArgGlnAspAspGluIlePhe-222 |

TABLE 1-continued

| | |
|---|---|
| SEQ. ID. NO. 11496 | 226-IleAsnGlyAsnSerLeuTyrGlnProProProHisGly-238 |
| SEQ. ID. NO. 11497 | 253-AsnThrTyrAspGlyValGluAsnProPhe-262 |
| SEQ. ID. NO. 11498 | 280-HisProPheGlyAspGlyAsnGlyArgThrAlaArg-291 |
| SEQ. ID. NO. 11499 | 313-ArgLeuLeuLysAsnAlaPro-319 |
| SEQ. ID. NO. 11500 | 330-GluThrAspAspLeuAsp-335 |
| SEQ. ID. NO. 11501 | 342-TyrGlnCysAspIleIleLys-348 |
| SEQ. ID. NO. 11502 | 358-IleSerAspLysGlnLysHisGlnGlnGluPheLysAla-370 |
| SEQ. ID. NO. 11503 | 375-TyrThrGluLysIleGlyLysLeuAsnGlnArgGln-386 |
| SEQ. ID. NO. 11504 | 392-LysAlaValGluGluSerGlyLys-399 |
| SEQ. ID. NO. 11505 | 415-AsnThrAlaArgSerAspLeuSerLysLeuGlyGluTyrArgPhe-429 |
| SEQ. ID. NO. 11506 | 433-PheLysSerGlyAsnAlaLeu-439 |
| SEQ. ID. NO. 11507 | 445-GlnAspLeuLeuGluArgLeuGluLysLys-454 |
| Hydrophilic Regions - Hopp-Woods | |
| SEQ. ID. NO. 11508 | 4-LeuThrGluArgMetThrGln-10 |
| SEQ. ID. NO. 11509 | 19-AlaAsnAsnProAspIleAspIle-26 |
| SEQ. ID. NO. 11510 | 31-ThrGluIleLysAspTyrSerGlu-38 |
| SEQ. ID. NO. 11511 | 40-SerValThrAspGluAsnGly-46 |
| SEQ. ID. NO. 11512 | 52-AspLysPheArgArgIleHisThrGluAspThrArgMetLysTrpArgAlaValLysGluSerArgLysLysIleGlnLysProIle-80 |
| SEQ. ID. NO. 11513 | 102-LeuIleAspLysSerCysGly-108 |
| SEQ. ID. NO. 11514 | 120-GlyArgSerGluGlnAsnArgPheLeu-128 |
| SEQ. ID. NO. 11515 | 147-AlaThrThrArgLysValAlaLysAspMetLeuLysSerGlnArgLysProLysThrLysAspGluIle-169 |
| SEQ. ID. NO. 11516 | 179-LysLysAlaValGluLeuLysAsn-186 |
| SEQ. ID. NO. 11517 | 204-AsnAlaIleGluAsnLysAlaGluProGlyGlnPheArgGlnAspAspGluIlePhe-222 |
| SEQ. ID. NO. 11518 | 283-GlyAspGlyAsnGlyArgThrAlaArg-291 |
| SEQ. ID. NO. 11519 | 330-GluThrAspAspLeuAsp-335 |
| SEQ. ID. NO. 11520 | 358-IleSerAspLysGlnLysHisGlnGlnGluPheLysAla-370 |
| SEQ. ID. NO. 11521 | 375-TyrThrGluLysIleGlyLysLeuAsnGlnArgGln-386 |
| SEQ. ID. NO. 11522 | 392-LysAlaValGluGluSerGlyLys-399 |
| SEQ. ID. NO. 11523 | 416-ThrAlaArgSerAspLeuSerLysLeuGlyGlu-426 |
| SEQ. ID. NO. 11524 | 446-AspLeuLeuGluArgLeuGluLysLys-454 |
| 753 | |
| AMPHI Regions - AMPHI | |
| SEQ. ID. NO. 11525 | 44-IleValGluMetMetThrTyrIleLeu-52 |
| SEQ. ID. NO. 11526 | 75-TrpAlaTyrPheAspGluValAlaGln-83 |
| SEQ. ID. NO. 11527 | 109-GlnTrpPheAlaProLeu-114 |
| SEQ. ID. NO. 11528 | 121-ArgSerAlaValArgGlnLeu-127 |
| SEQ. ID. NO. 11529 | 129-ProSerThrThrValArgAla-135 |
| Antigenic Index - Jameson-Wolf | |
| SEQ. ID. NO. 11530 | 13-LysLeuTyrProAsnGluGlnTrpAsnGluSerGluAla-25 |
| SEQ. ID. NO. 11531 | 34-TyrGlnSerProThrHisArgGln-41 |
| SEQ. ID. NO. 11532 | 55-LeuLysAsnGlyGln-59 |
| SEQ. ID. NO. 11533 | 64-CysLysGlyThrGlnProIleGly-71 |
| SEQ. ID. NO. 11534 | 85-HisTyrLeuGluSerAspArgHisLeuArgAspAsnSerAspTrpAsnCysGlyAspAsnIle-105 |
| SEQ. ID. NO. 11535 | 112-AlaProLeuGlyHisSerHisGlnMetArgSerAlaVal-124 |
| SEQ. ID. NO. 11536 | 136-LeuTyrHisLysGlySerAspLysGlyLeuArg-146 |
| Hydrophilic Regions - Hopp-Woods | |
| SEQ. ID. NO. 11537 | 19-GlnTrpAsnGluSerGluAla-25 |
| SEQ. ID. NO. 11538 | 87-LeuGluSerAspArgHisLeuArgAspAsnSerAsp-98 |
| SEQ. ID. NO. 11539 | 139-LysGlySerAspLysGlyLeuArg-146 |
| 754 | |
| AMPHI Regions - AMPHI | |
| SEQ. ID. NO. 11540 | 29-ArgIleGlyThrLeuGluLysGlyAlaMet-38 |
| SEQ. ID. NO. 11541 | 67-MetProHisIlePheAlaGlnTyrPheProGluGlyPheLeuAsp-81 |
| SEQ. ID. NO. 11542 | 108-ArgGluThrLeuGlyArg-113 |
| SEQ. ID. NO. 11543 | 121-ProLeuPheAsnGluTrpIleAspGlyLeuGlu-131 |
| SEQ. ID. NO. 11544 | 152-PheGlnGlnTyrMetAlaGluIle-159 |
| SEQ. ID. NO. 11545 | 161-HisHisGlyArgPheValSerValSer-169 |
| SEQ. ID. NO. 11546 | 181-ArgArgAsnThrLys-185 |
| SEQ. ID. NO. 11547 | 189-SerTyrIleAlaLysGly-194 |
| SEQ. ID. NO. 11548 | 249-MetGluAspPheThrSerLeuArgGln-257 |
| SEQ. ID. NO. 11549 | 269-AlaAlaIleAlaGlnIleIleArgGlnIleSerGlyArgProAsp-283 |
| SEQ. ID. NO. 11550 | 288-HisPhePheAsnGlnLeuAlaAla-295 |
| SEQ. ID. NO. 11551 | 324-ValTyrAspValLeuAspThr-330 |
| SEQ. ID. NO. 11552 | 336-GlyThrGlnGlyIlePheAspAlaTyrAsp-345 |
| SEQ. ID. NO. 11553 | 399-TyrSerAspValLeu-403 |
| Antigenic Index - Jameson-Wolf | |
| SEQ. ID. NO. 11554 | 8-ValSerGlyAsnArgMetArgLysProArg-17 |
| SEQ. ID. NO. 11555 | 25-AlaAsnAspGluArgIleGlyThrLeuGluLysGlyAla-37 |
| SEQ. ID. NO. 11556 | 43-TyrAspAsnProAsnSerSerLeu-50 |
| SEQ. ID. NO. 11557 | 54-HisTyrGlnAspArgSerLysVal-61 |
| SEQ. ID. NO. 11558 | 75-PheProGluGlyPheLeu-80 |
| SEQ. ID. NO. 11559 | 93-AlaProPheGluAspAsnGluMetLeu-101 |
| SEQ. ID. NO. 11560 | 114-IleHisValArgCysAsnAspProLeuPhe-123 |
| SEQ. ID. NO. 11561 | 130-LeuGluMetLysAsnProArgIleLeuThrGluArgAspLeuLeu-144 |
| SEQ. ID. NO. 11562 | 163-GlyArgPheValSer-167 |
| SEQ. ID. NO. 11563 | 170-GlyIleGlnGlnLysMetSerLeuAspAlaIleArgArgAsnThrLysGlnThrAla-188 |
| SEQ. ID. NO. 11564 | 194-GlyPheAspAlaSerGluTyrProCys-202 |
| SEQ. ID. NO. 11565 | 224-ThrSerLeuSerGluAspSerSer-231 |
| SEQ. ID. NO. 11566 | 236-ArgArgPheAspValSerGluGlnGlyTyr-245 |
| SEQ. ID. NO. 11567 | 250-GluAspPheThrSer-254 |

TABLE 1-continued

| | |
|---|---|
| SEQ. ID. NO. 11568 | 256-ArgGlnTyrSerValGluAspLysTyrLysGlySerTyr-268 |
| SEQ. ID. NO. 11569 | 278-IleSerGlyArgProAspGluAspLeu-286 |
| SEQ. ID. NO. 11570 | 299-LeuLysAsnGlyAspAlaHisLeu-306 |
| SEQ. ID. NO. 11571 | 315-AspGluTyrAspVal-319 |
| SEQ. ID. NO. 11572 | 343-AlaTyrAspAspThrLeu-348 |
| SEQ. ID. NO. 11573 | 352-LeuThrAsnHisGlyLysLysThrTyrProSerLysAsnThr-365 |
| SEQ. ID. NO. 11574 | 369-PheAlaGluLysTyrCysAspLeuGlyArgGluAspAlaSerPhe-383 |
| SEQ. ID. NO. 11575 | 389-ValGlnAlaLysGluGlnVal-395 |
| SEQ. ID. NO. 11576 | 399-TyrSerAspValLeuArgGluAsnGluTrpLeu-409 |
| SEQ. ID. NO. 11577 | 415-PheIleProAspGluAsnGluGluGlyLeu-424 |
| Hydrophilic Regions - Hopp-Woods | |
| SEQ. ID. NO. 11578 | 10-GlyAsnArgMetArgLysProArg-17 |
| SEQ. ID. NO. 11579 | 25-AlaAsnAspGluArgIleGlyThrLeuGluLysGlyAla-37 |
| SEQ. ID. NO. 11580 | 55-TyrGlnAspArgSerLysVal-61 |
| SEQ. ID. NO. 11581 | 93-AlaProPheGluAspAsnGluMetLeu-101 |
| SEQ. ID. NO. 11582 | 114-IleHisValArgCysAsnAsp-120 |
| SEQ. ID. NO. 11583 | 130-LeuGluMetLysAsnProArgIleLeuThrGluArgAspLeuLeu-144 |
| SEQ. ID. NO. 11584 | 175-MetSerLeuAspAlaIleArgArgAsnThrLysGln-186 |
| SEQ. ID. NO. 11585 | 194-GlyPheAspAlaSerGlu-199 |
| SEQ. ID. NO. 11586 | 225-SerLeuSerGluAspSerSer-231 |
| SEQ. ID. NO. 11587 | 236-ArgArgPheAspValSerGlu-242 |
| SEQ. ID. NO. 11588 | 250-GluAspPheThrSer-254 |
| SEQ. ID. NO. 11589 | 258-TyrSerValGluAspLysTyrLysGly-266 |
| SEQ. ID. NO. 11590 | 278-IleSerGlyArgProAspGluAspLeu-286 |
| SEQ. ID. NO. 11591 | 300-LysAsnGlyAspAlaHisLeu-306 |
| SEQ. ID. NO. 11592 | 315-AspGluTyrAspVal-319 |
| SEQ. ID. NO. 11593 | 354-AsnHisGlyLysLysThrTyrProSer-362 |
| SEQ. ID. NO. 11594 | 369-PheAlaGluLysTyrCysAspLeuGlyArgGluAspAlaSerPhe-383 |
| SEQ. ID. NO. 11595 | 389-ValGlnAlaLysGluGlnVal-395 |
| SEQ. ID. NO. 11596 | 401-AspValLeuArgGluAsnGluTrpLeu-409 |
| SEQ. ID. NO. 11597 | 417-ProAspGluAsnGluGluGlyLeu-424 |
| 755 | |
| AMPHI Regions - AMPHI | |
| SEQ. ID. NO. 11598 | 22-AsnAsnTyrThrAsnAlaTyrSerAspIleLysThrIle-34 |
| SEQ. ID. NO. 11599 | 38-HisGlyPheGluAsnIleGlnGly-45 |
| SEQ. ID. NO. 11600 | 75-SerCysIleSerAsnIleLysPhe-82 |
| SEQ. ID. NO. 11601 | 124-GluGlnIleAsnGlnValLeu-130 |
| Antigenic Index - Jameson-Wolf | |
| SEQ. ID. NO. 11602 | 10-MetAspThrAsnCysLeuLysAspAsnTyrHisGlyAsnAsnTyrThrAsnAlaTyrSerAsp-30 |
| SEQ. ID. NO. 11603 | 42-AsnIleGlnGlySer-46 |
| SEQ. ID. NO. 11604 | 48-TyrLeuGlyArgGluGlyIleSerGluAlaHis-58 |
| SEQ. ID. NO. 11605 | 83-TyrArgLeuGluSerAspLeu-89 |
| SEQ. ID. NO. 11606 | 108-ArgValGluGlnLeuArg-113 |
| SEQ. ID. NO. 11607 | 120-GlyLeuSerAspGluGlnIle-126 |
| SEQ. ID. NO. 11608 | 129-ValLeuGluLysGlnLysPheGluLeuGluSerProAsnLeuLys-143 |
| Hydrophilic Regions - Hopp-Woods | |
| SEQ. ID. NO. 11609 | 10-MetAspThrAsnCysLeuLysAspAsnTyrHis-20 |
| SEQ. ID. NO. 11610 | 49-LeuGlyArgGluGlyIleSerGluAlaHis-58 |
| SEQ. ID. NO. 11611 | 83-TyrArgLeuGluSerAspLeu-89 |
| SEQ. ID. NO. 11612 | 108-ArgValGluGlnLeuArg-113 |
| SEQ. ID. NO. 11613 | 120-GlyLeuSerAspGluGlnIle-126 |
| SEQ. ID. NO. 11614 | 129-ValLeuGluLysGlnLysPheGluLeuGluSerProAsnLeu-142 |
| 756 | |
| AMPHI Regions - AMPHI | |
| SEQ. ID. NO. 11615 | 6-AlaGlnThrLeuValGluIleGlnAspSerLeuTyrArgValValSerThrVal-23 |
| SEQ. ID. NO. 11616 | 29-AsnLeuLysArgLeuThr-34 |
| SEQ. ID. NO. 11617 | 57-AspPheLysGluThrLeuValArgPheGlyArgAspMetLeuGlnAspMetPro-74 |
| SEQ. ID. NO. 11618 | 98-TyrLeuGluTyrLeuLysGlnValAlaSer-107 |
| SEQ. ID. NO. 11619 | 113-GluArgLeuTyrAsnAlaValAspArgLeuAlaGluSerGlnGluArg-128 |
| SEQ. ID. NO. 11620 | 130-ThrSerAlaIleLeu-134 |
| SEQ. ID. NO. 11621 | 136-GlyAlaArgGlyAlaAspPhe-142 |
| Antigenic Index - Jameson-Wolf | |
| SEQ. ID. NO. 11622 | 11-GluIleGlnAspSerLeuTyr-17 |
| SEQ. ID. NO. 11623 | 24-GlnTyrGlyAspAspAsnLeuLysArgLeuThrAlaAspLysArgLysGlnTyr-41 |
| SEQ. ID. NO. 11624 | 45-PheLysIleSerGluGlySerThrArgValGluSerAspPheLysGluThrLeu-62 |
| SEQ. ID. NO. 11625 | 65-PheGlyArgAspMetLeuGlnAspMetProProLysIleArgSer-79 |
| SEQ. ID. NO. 11626 | 105-ValAlaSerGluGlyTyrGlnThrGluArgLeuTyrAsnAlaValAspArgLeuAlaGluSerGlnGluArgIleThr-130 |
| SEQ. ID. NO. 11627 | 135-LysGlyAlaArgGlyAlaAsp-141 |
| SEQ. ID. NO. 11628 | 44-GlnIleGlyArgArgSerTyrSerArgGluAspIleSerGluAlaAsnArgArgAlaGluArgValProTyr-167 |
| SEQ. ID. NO. 11629 | 171-LeuValSerAspGlyAsn-176 |
| SEQ. ID. NO. 11630 | 182-SerAspIleGlyAsp-186 |
| Hydrophilic Regions - Hopp-Woods | |
| SEQ. ID. NO. 11631 | 11-GluIleGlnAspSerLeu-16 |
| SEQ. ID. NO. 11632 | 25-TyrGlyAspAspAsnLeuLysArgLeuThrAlaAspLysArgLysGlnTyr-41 |
| SEQ. ID. NO. 11633 | 45-PheLysIleSerGluGlySerThrArgValGluSerAspPheLysGluThrLeu-62 |
| SEQ. ID. NO. 11634 | 65-PheGlyArgAspMetLeuGln-71 |
| SEQ. ID. NO. 11635 | 73-MetProProLysIleArgSer-79 |

TABLE 1-continued

SEQ. ID. NO. 11636 114-ArgLeuTyrAsnAlaValAspArgLeuAlaGluSerGlnGluArgIleThr-130
SEQ. ID. NO. 11637 135-LysGlyAlaArgGlyAlaAsp-141
SEQ. ID. NO. 11638 144-GlnIleGlyArgArgSerTyrSerArgGluAspIleSerGluAlaAsnArgArgAlaGluArgValProTyr-167
757
AMPHI Regions - AMPHI
SEQ. ID. NO. 11639 47-AspTyrGlnSerAlaAlaAsnLys-54
SEQ. ID. NO. 11640 79-AsnLeuLeuHisAspPheSerAspGlyLeu-88
SEQ. ID. NO. 11641 97-LysAlaAspLysIleThr-102
SEQ. ID. NO. 11642 115-GlnLysAlaGluLysLeuSerLysAlaAla-124
SEQ. ID. NO. 11643 140-ArgAspThrGlyAsp-144
SEQ. ID. NO. 11644 154-AsnAlaGlnLysGluProThrArgGluTrpAla-164
Antigenic Index - Jameson-Wolf
SEQ. ID. NO. 11645 16-AlaCysGlySerGlnSerGluGluGlnProAlaSerAlaGlnProGlnGluGlnAlaGlnSerGluLeuLysThrMetPro-42
SEQ. ID. NO. 11646 46-ThrAspTyrGlnSerAlaAlaAsnLysGlyLeuAsnAspGlnLysThrGlyLeuThrLeu-65
SEQ. ID. NO. 11647 73-AspAsnAlaGluGlyLysAsnLeuLeuHisAspPheSerAspGlyLeu-88
SEQ. ID. NO. 11648 93-ValAspThrAspLysAlaAspLysIleThrAla-103
SEQ. ID. NO. 11649 108-TrpAsnThrAspAlaMetProGlnLysAlaGluLysLeuSerLys-122
SEQ. ID. NO. 11650 132-AlaProGluAspArgThrMetLeuArgAspThrGlyAspGlnIleGluMetAlaIleAspSerHisAsnAlaGlnLysGluProThrArgGluTrpAlaArgGlyGlyIle-168
Hydrophilic Regions - Hopp-Woods
SEQ. ID. NO. 11651 19-SerGlnSerGluGluGlnProAla-26
SEQ. ID. NO. 11652 29-GlnProGlnGluGlnAlaGlnSerGluLeuLysThr-40
SEQ. ID. NO. 11653 50-SerAlaAlaAsnLysGlyLeuAsnAspGlnLysThr-61
SEQ. ID. NO. 11654 73-AspAsnAlaGluGlyLysAsnLeu-80
SEQ. ID. NO. 11655 93-ValAspThrAspLysAlaAspLysIleThrAla-103
SEQ. ID. NO. 11656 112-AlaMetProGlnLysAlaGluLysLeuSerLys-122
SEQ. ID. NO. 11657 132-AlaProGluAspArgThrMetLeuArgAspThrGlyAspGlnIleGluMetAlaIle-150
SEQ. ID. NO. 11658 152-SerHisAsnAlaGlnLysGluProThrArgGluTrpAlaArg-165
758
AMPHI Regions - AMPHI
SEQ. ID. NO. 11659 15-AlaThrLeuAlaAspGluLeuGlnTyrVal-24
SEQ. ID. NO. 11660 53-AlaGluValAlaAla-57
SEQ. ID. NO. 11661 60-GlnThrValIleSerGluIleValArgArgHisThr-71
SEQ. ID. NO. 11662 87-ProTyrLeuGlyGlyLeuProGluAlaLeuHisThr-98
SEQ. ID. NO. 11663 125-PheAlaSerProGlyGlyTrpGlnIleIleGly-135
Antigenic Index - Jameson-Wolf
SEQ. ID. NO. 11664 9-ArgPheAspThrAspLeu-14
SEQ. ID. NO. 11665 32-AspHisGlnGlyLysLeuVal-38
SEQ. ID. NO. 11666 44-TyrGlyGlyGluTyrGlyProAspLeuAlaGlu-54
SEQ. ID. NO. 11667 66-IleValArgArgHisThrAla-72
SEQ. ID. NO. 11668 96-LeuHisThrProArgArgAlaValProArgThrSerValPro-109
SEQ. ID. NO. 11669 115-IleGlyGlySerGln-119
SEQ. ID. NO. 11670 145-AspLeuAsnProPro-149
SEQ. ID. NO. 11671 154-AlaGlyAspGlnValArgPheValAlaGluArgIleGluPro-167
Hydrophilic Regions - Hopp-Woods
SEQ. ID. NO. 11672 10-PheAspThrAspLeu-14
SEQ. ID. NO. 11673 32-AspHisGlnGlyLysLeuVal-38
SEQ. ID. NO. 11674 48-TyrGlyProAspLeuAlaGlu-54
SEQ. ID. NO. 11675 66-IleValArgArgHisThr-71
SEQ. ID. NO. 11676 97-HisThrProArgArgAlaValPro-104
SEQ. ID. NO. 11677 156-AspGlnValArgPheValAlaGluArgIleGluPro-167
759
AMPHI Regions - AMPHI
SEQ. ID. NO. 11678 8-ProPheCysSerValLeuSerThrLeuGlyLeu-18
SEQ. ID. NO. 11679 35-TyrGlnTyrPheArgAspPheAlaGlu-43
SEQ. ID. NO. 11680 63-LysIleLeuGlyArgValLeuAsnGlyIlePro-73
SEQ. ID. NO. 11681 94-TyrValAsnSerVal-98
SEQ. ID. NO. 11682 140-ArgLeuAsnLysLeuValThrGluIle-148
SEQ. ID. NO. 11683 185-ThrGlnGlnValArgLysAlaAsp-192
SEQ. ID. NO. 11684 207-GlyGlyThrProLeu-211
SEQ. ID. NO. 11685 261-LeuSerThrTyrAlaGlyPheAspAsnPhePheAsnLys-273
SEQ. ID. NO. 11686 282-IleArgSerThrIle-286
SEQ. ID. NO. 11687 313-ThrLeuGlnGlyLeu-317
SEQ. ID. NO. 11688 408-LysGlyAspArgLeuSerLysLeuGlyAla-417
SEQ. ID. NO. 11689 446-AlaSerAspGlySerLysGlnAla-453
SEQ. ID. NO. 11690 548-ValTyrGluTyrIle-552
SEQ. ID. NO. 11691 597-GluGlnValAlaGlnAlaGlu-603
SEQ. ID. NO. 11692 764-LysThrProGluCysTyrArgSerTyrHisSer-774
SEQ. ID. NO. 11693 788-GluAsnTyrArgAlaLeu-793
SEQ. ID. NO. 11694 820-SerIleArgAlaGlyLys-825
SEQ. ID. NO. 11695 878-ThrLeuAspGlyPheGlyThrPheArgPheLeuThrGlyIle-891
SEQ. ID. NO. 11696 921-ProGlnThrThrGlu-925
SEQ. ID. NO. 11697 948-TyrAlaAspLeuGlyAlaTyr-954
SEQ. ID. NO. 11698 967-LeuTyrAsnProLeuLys-972
SEQ. ID. NO. 11699 992-TyrAsnGlnLeuGlnAlaThrAspIleSerArgGlnValGln-1005
SEQ. ID. NO. 11700 1013-GlnAlaLeuGlnAlaTrpGlnAsnSerGln-1022
SEQ. ID. NO. 11701 1040-LysGlnThrAspProLeuThrGlyIleLeuThr-1050
SEQ. ID. NO. 11702 1062-SerAlaAspIleCysArgGlnValAlaLysAlaAlaAspThr-1075
SEQ. ID. NO. 11703 1084-GluLeuAspThrTyr-1088
SEQ. ID. NO. 11704 1102-AlaArgGlnGlyGlyAspAlaGlnAlaValGluThrAlaArgHisAlaTyrLeuAsnAlaLeuAsnArgLeuSerArgGlnIleHisSerLeu-1132

TABLE 1-continued

| | |
|---|---|
| SEQ. ID. NO. 11705 | 1139-IleArgMetProAsnLeuAlaGluLeuIleSerArgSerAlaAsnThrAla-1155 |
| SEQ. ID. NO. 11706 | 1168-GlnAlaGlyArgArgIleAspArgHisLeuThrAspPro-1180 |
| SEQ. ID. NO. 11707 | 1199-GlyThrHisArgProTyrGlnGlnThrThrAsn-1209 |
| SEQ. ID. NO. 11708 | 1234-ThrAsnAsnArgPheAspGlu-1240 |
| SEQ. ID. NO. 11709 | 1328-GluIleAsnSerProAlaGlnIle-1335 |
| SEQ. ID. NO. 11710 | 1346-AspLysThrValGlu-1350 |
| SEQ. ID. NO. 11711 | 1385-GlnAlaAlaHisGlyThrLeu-1391 |
| Antigenic Index - Jameson-Wolf | |
| SEQ. ID. NO. 11712 | 29-ValArgAsnAspValAspTyrGlnTyr-37 |
| SEQ. ID. NO. 11713 | 40-AspPheAlaGluAsnLysGlyAla-47 |
| SEQ. ID. NO. 11714 | 56-SerIleGlnAspLysGlnGlyLysIleLeu-65 |
| SEQ. ID. NO. 11715 | 73-ProMetProAspPheArgValSerAsnArgGlnThrAla-85 |
| SEQ. ID. NO. 11716 | 110-GlyAsnAspThrGlnAsnProGluGluGlnAlaTyr-121 |
| SEQ. ID. NO. 11717 | 125-LeuValSerArgAsnProHisProAspTyrAspTyrHisLeuProArgLeuAsnLysLeuValThr-146 |
| SEQ. ID. NO. 11718 | 148-IleSerProThrAla-152 |
| SEQ. ID. NO. 11719 | 160-GlyAsnGlyGlnProLysAla-166 |
| SEQ. ID. NO. 11720 | 168-AlaTyrLeuAspThrAspArgPhePro-176 |
| SEQ. ID. NO. 11721 | 181-LeuGlySerGlyThrGlnGlnValArgLysAlaAspGlyThrArgThrArgThrAlaPro-200 |
| SEQ. ID. NO. 11722 | 206-ThrGlyGlyThrProLeuLys-212 |
| SEQ. ID. NO. 11723 | 226-SerLeuThrAspGlnProLeuAsn-233 |
| SEQ. ID. NO. 11724 | 238-AlaGlyAspSerGlySerPro-244 |
| SEQ. ID. NO. 11725 | 249-AspLysHisGluAsnArg-254 |
| SEQ. ID. NO. 11726 | 285-ThrIleArgGlnTyrGluThrArgLeuAspVal-295 |
| SEQ. ID. NO. 11727 | 303-IleTrpArgAspAsnGlyAsnGlyAsnSerThr-313 |
| SEQ. ID. NO. 11728 | 316-GlyLeuAsnGluArgIleThr-322 |
| SEQ. ID. NO. 11729 | 327-AsnProSerLeuAlaProGlnAsnAspSerArgHisMetProSerGluAspAlaGlyLys-346 |
| SEQ. ID. NO. 11730 | 350-LeuSerSerArgPheAspAsnLysThr-358 |
| SEQ. ID. NO. 11731 | 364-AsnIleAsnGlnGlyAla-369 |
| SEQ. ID. NO. 11732 | 382-GlyLysAsnHisThr-386 |
| SEQ. ID. NO. 11733 | 394-ValAlaAspGlyLysArgValPhe-401 |
| SEQ. ID. NO. 11734 | 404-ValSerAsnProLysGlyAspArgLeuSerLysLeuGlyAla-417 |
| SEQ. ID. NO. 11735 | 424-GlyGlnGlyIleAsnGlnGlyAspIleSerIleGlyGluGlyThr-438 |
| SEQ. ID. NO. 11736 | 444-LysAlaAlaSerAspGlySerLysGlnAla-453 |
| SEQ. ID. NO. 11737 | 459-IleThrSerGlyArgGlyThr-465 |
| SEQ. ID. NO. 11738 | 469-AlaAspSerGlnGlnIleLysProGluAsn-478 |
| SEQ. ID. NO. 11739 | 483-PheArgGlyGlyArgLeuAspLeuAsnGlyAsnAsnLeu-495 |
| SEQ. ID. NO. 11740 | 501-ArgHisAlaAspGlyGlyAla-507 |
| SEQ. ID. NO. 11741 | 512-HisAsnProAspGlnAlaAla-518 |
| SEQ. ID. NO. 11742 | 528-LeuSerProGluHisValGlu-534 |
| SEQ. ID. NO. 11743 | 538-TrpGlyAsnArgProGlnGlyAsn-545 |
| SEQ. ID. NO. 11744 | 553-AsnProHisArgAsnArgArgThrAsp-561 |
| SEQ. ID. NO. 11745 | 566-LysProGlyGlyAsnProArgGlu-573 |
| SEQ. ID. NO. 11746 | 577-LeuAsnMetLysAsnSerThrSer-584 |
| SEQ. ID. NO. 11747 | 589-GlyAsnAsnArgGlnGlnAlaAlaGluGlnValAlaGlnAlaGluAsnAlaArgProAspLeu-609 |
| SEQ. ID. NO. 11748 | 614-GlyTyrLeuGlyGluAsnAlaGlnThrGlyLysAlaAlaProSerTyrSerLysThrAsnGluAlaAlaIleGluLysThrArgHis-642 |
| SEQ. ID. NO. 11749 | 650-GlyArgProGluTyrArgTyrAsnGly-658 |
| SEQ. ID. NO. 11750 | 664-TyrArgProLysArgThrAspSer-671 |
| SEQ. ID. NO. 11751 | 677-GlyGlyMetAsnLeuAsnGly-683 |
| SEQ. ID. NO. 11752 | 694-ValSerGlyArgProValProHisAlaTyrAspHisGlnAlaLysArgGluProValLeuGluAsnGluTrpThrAspGlySerPheLysAla-724 |
| SEQ. ID. NO. 11753 | 726-ArgPheThrLeuArgAsnHisAla-733 |
| SEQ. ID. NO. 11754 | 736-ThrAlaGlyArgAsnThrAlaHisLeuAspGlyAspIleThr-749 |
| SEQ. ID. NO. 11755 | 761-ThrGlnGlyLysThrProGluCysTyrArgSerTyrHisSerGlySerThrHis-778 |
| SEQ. ID. NO. 11756 | 785-LeuLysAlaGluAsnTyrArg-791 |
| SEQ. ID. NO. 11757 | 796-ThrGlnValArgGlyAspIleThrLeuAsnAspArgSerGluLeuArgLeuGlyLys-814 |
| SEQ. ID. NO. 11758 | 820-SerIleArgAlaGlyLysAspThrAlaValArgMetGluAlaAspSerAsnTrpThr-838 |
| SEQ. ID. NO. 11759 | 840-SerGlnSerSerHisThrGly-846 |
| SEQ. ID. NO. 11760 | 859-ProAspPheAlaAsnAsnThrHisAsnAsnArgPheAsn-871 |
| SEQ. ID. NO. 11761 | 877-GlyThrLeuAspGly-881 |
| SEQ. ID. NO. 11762 | 891-IleValArgLysGlnAsnAlaProProLeuLysLeuGluGlyAspSerArgGlyAla-909 |
| SEQ. ID. NO. 11763 | 914-ValLysAsnThrGlyGlnGluProGlnThrThrGluSer-926 |
| SEQ. ID. NO. 11764 | 932-LeuAsnProLysHisSerHisGln-939 |
| SEQ. ID. NO. 11765 | 957-IleLeuArgLysAsnAsnAsnGlyTyr-965 |
| SEQ. ID. NO. 11766 | 969-AsnProLeuLysGluAlaGluLeuGlnIleGluAlaThrArgAlaGluHisGluArgAsnGlnGlnAla-991 |
| SEQ. ID. NO. 11767 | 999-AspIleSerArgGlnValGlnHisAspSerAspAlaThrArgGlnAla-1014 |
| SEQ. ID. NO. 11768 | 1018-TrpGlnAsnSerGlnThrGluLeuAlaArgIleAspSerGln-1031 |
| SEQ. ID. NO. 11769 | 1039-LeuLysGlnThrAspProLeuThr-1046 |
| SEQ. ID. NO. 11770 | 1064-AspIleCysArgGlnValAlaLysAlaAlaAspThrAsnAsp-1077 |
| SEQ. ID. NO. 11771 | 1083-ThrGluLeuAspThrTyrIleGluArgValGluMetAlaGluSerGluLeuAspLysAlaArgGlnGlyGlyAspAlaGlnAla-1110 |
| SEQ. ID. NO. 11772 | 1123-AsnArgLeuSerArg-1127 |
| SEQ. ID. NO. 11773 | 1147-LeuIleSerArgSerAlaAsnThrAlaValSerGlu-1158 |
| SEQ. ID. NO. 11774 | 1160-AlaAlaTyrAsnThrGlyArgGlnGlnAlaGlyArgArgIleAspArgHisLeuThrAspProGlnGlnGlnAsn-1184 |
| SEQ. ID. NO. 11775 | 1188-GluThrGlyThrGlnGlnThrAspTyrHisSerGlyThrHisArgProTyrGlnGlnThrThrAsn-1209 |
| SEQ. ID. NO. 11776 | 1219-IleThrAspArgLeuSer-1224 |
| SEQ. ID. NO. 11777 | 1229-LeuThrAspGluArgThrAsnAsnArgPheAspGluGlyValSerAlaArgAsnArgSerAsnGly-1250 |
| SEQ. ID. NO. 11778 | 1255-ValLysGlyGluAsnGlyAla-1261 |
| SEQ. ID. NO. 11779 | 1269-GlyTyrSerAsnSerArgThrArgPheThrAspTyrAspGlyAlaAlaValArg-1286 |
| SEQ. ID. NO. 11780 | 1288-HisAlaTrpAspAlaGlyIleAsnThrGlyIleLysIleAspThrGlyIle-1304 |
| SEQ. ID. NO. 11781 | 1313-ArgIleAsnArgSerAsnGlyAsnArgTyrVal-1323 |
| SEQ. ID. NO. 11782 | 1326-GlyAlaGluIleAsnSerProAlaGlnIleGln-1336 |
| SEQ. ID. NO. 11783 | 1343-IleArgLeuAspLysThrValGlu-1350 |

TABLE 1-continued

| | |
|---|---|
| SEQ. ID. NO. 11784 | 1360-PheSerSerAspTyrTyrHisThrArgGlnAsnSerGlySerAla-1374 |
| SEQ. ID. NO. 11785 | 1376-SerValAsnAspArgThrLeu-1382 |
| SEQ. ID. NO. 11786 | 1398-AlaGlyTyrLysGlyTrpAsn-1404 |
| SEQ. ID. NO. 11787 | 1411-TyrGlyLysAspSerAsnThrAlaArgHisLysGlnAlaGly-1424 |
| Hydrophilic Regions - Hopp-Woods | |
| SEQ. ID. NO. 11788 | 29-ValArgAsnAspValAsp-34 |
| SEQ. ID. NO. 11789 | 40-AspPheAlaGluAsnLysGly-46 |
| SEQ. ID. NO. 11790 | 56-SerIleGlnAspLysGlnGlyLysIleLeu-65 |
| SEQ. ID. NO. 11791 | 75-ProAspPheArgValSerAsnArgGlnThr-84 |
| SEQ. ID. NO. 11792 | 111-AsnAspThrGlnAsnProGluGluGlnAlaTyr-121 |
| SEQ. ID. NO. 11793 | 129-AsnProHisProAspTyr-134 |
| SEQ. ID. NO. 11794 | 140-ArgLeuAsnLysLeuValThr-146 |
| SEQ. ID. NO. 11795 | 162-GlyGlnProLysAla-166 |
| SEQ. ID. NO. 11796 | 170-LeuAspThrAspArg-174 |
| SEQ. ID. NO. 11797 | 186-GlnGlnValArgLysAlaAspGlyThrArgThrArgThr-198 |
| SEQ. ID. NO. 11798 | 249-AspLysHisGluAsn-253 |
| SEQ. ID. NO. 11799 | 285-ThrIleArgGlnTyrGluThrArgLeuAspVal-295 |
| SEQ. ID. NO. 11800 | 306-AspAsnGlyAsnGly-310 |
| SEQ. ID. NO. 11801 | 317-LeuAsnGluArgIleThr-322 |
| SEQ. ID. NO. 11802 | 332-ProGlnAsnAspSerArgHisMetProSerGluAspAlaGlyLys-346 |
| SEQ. ID. NO. 11803 | 352-SerArgPheAspAsnLysThr-358 |
| SEQ. ID. NO. 11804 | 395-AlaAspGlyLysArg-399 |
| SEQ. ID. NO. 11805 | 406-AsnProLysGlyAspArgLeuSerLys-414 |
| SEQ. ID. NO. 11806 | 444-LysAlaAlaSerAspGlySerLysGlnAla-453 |
| SEQ. ID. NO. 11807 | 472-GlnGlnIleLysProGlu-477 |
| SEQ. ID. NO. 11808 | 484-ArgGlyGlyArgLeuAspLeuAsnGly-492 |
| SEQ. ID. NO. 11809 | 501-ArgHisAlaAspGlyGly-506 |
| SEQ. ID. NO. 11810 | 555-HisArgAsnArgArgThrAsp-561 |
| SEQ. ID. NO. 11811 | 568-GlyGlyAsnProArgGlu-573 |
| SEQ. ID. NO. 11812 | 591-AsnArgGlnGlnAlaAlaGluGlnValAlaGlnAlaGluAsnAlaArgProAsp-608 |
| SEQ. ID. NO. 11813 | 619-AsnAlaGlnThrGlyLysAlaAlaProSerTyrSerLysThrAsnGluAlaAlaIleGluLysThrArgHis-642 |
| SEQ. ID. NO. 11814 | 652-ProGluTyrArgTyr-656 |
| SEQ. ID. NO. 11815 | 664-TyrArgProLysArgThrAspSer-671 |
| SEQ. ID. NO. 11816 | 705-HisGlnAlaLysArgGluProValLeu-713 |
| SEQ. ID. NO. 11817 | 736-ThrAlaGlyArgAsn-740 |
| SEQ. ID. NO. 11818 | 744-LeuAspGlyAspIleThr-749 |
| SEQ. ID. NO. 11819 | 764-LysThrProGluCysTyrArg-770 |
| SEQ. ID. NO. 11820 | 785-LeuLysAlaGluAsnTyrArg-791 |
| SEQ. ID. NO. 11821 | 797-GlnValArgGlyAspIleThrLeuAsnAspArgSerGluLeuArgLeuGlyLys-814 |
| SEQ. ID. NO. 11822 | 822-ArgAlaGlyLysAspThrAlaValArgMetGluAlaAspSer-835 |
| SEQ. ID. NO. 11823 | 891-IleValArgLysGlnAsnAlaPro-898 |
| SEQ. ID. NO. 11824 | 900-LeuLysLeuGluGlyAspSerArgGly-908 |
| SEQ. ID. NO. 11825 | 916-AsnThrGlyGlnGluProGlnThrThrGlu-925 |
| SEQ. ID. NO. 11826 | 934-ProLysHisSerHis-938 |
| SEQ. ID. NO. 11827 | 957-IleLeuArgLysAsnAsnAsn-963 |
| SEQ. ID. NO. 11828 | 970-ProLeuLysGluAlaGluLeuGlnIleGluAlaThrArgAlaGluHisGluArgAsnGlnGln-990 |
| SEQ. ID. NO. 11829 | 1004-ValGlnHisAspSerAspAlaThrArgGlnAla-1014 |
| SEQ. ID. NO. 11830 | 1021-SerGlnThrGluLeuAlaArgIleAspSer-1030 |
| SEQ. ID. NO. 11831 | 1039-LeuLysGlnThrAspPro-1044 |
| SEQ. ID. NO. 11832 | 1064-AspIleCysArgGlnValAlaLysAlaAlaAspThrAsnAsp-1077 |
| SEQ. ID. NO. 11833 | 1087-ThrTyrIleGluArgValGluMetAlaGluSerGluLeuAspLysAlaArgGlnGlyGlyAspAlaGlnAla-1110 |
| SEQ. ID. NO. 11834 | 1164-ThrGlyArgGlnGlnAlaGlyArgArgIleAspArgHisLeuThrAspProGlnGln-1182 |
| SEQ. ID. NO. 11835 | 1200-ThrHisArgProTyrGln-1205 |
| SEQ. ID. NO. 11836 | 1219-IleThrAspArgLeuSer-1224 |
| SEQ. ID. NO. 11837 | 1229-LeuThrAspGluArgThrAsnAsnArgPheAspGluGlyValSerAlaArgAsnArgSerAsnGly-1250 |
| SEQ. ID. NO. 11838 | 1272-AsnSerArgThrArgPheThrAspTyrAspGlyAlaAlaValArg-1286 |
| SEQ. ID. NO. 11839 | 1298-IleLysIleAspThr-1302 |
| SEQ. ID. NO. 11840 | 1313-ArgIleAsnArgSerAsnGly-1319 |
| SEQ. ID. NO. 11841 | 1326-GlyAlaGluIleAsnSer-1331 |
| SEQ. ID. NO. 11842 | 1343-IleArgLeuAspLysThrValGlu-1350 |
| SEQ. ID. NO. 11843 | 1376-SerValAsnAspArgThrLeu-1382 |
| SEQ. ID. NO. 11844 | 1411-TyrGlyLysAspSerAsnThrAlaArgHisLysGlnAlaGly-1424 |
| 760 | |
| AMPHI Regions - AMPHI | |
| SEQ. ID. NO. 11845 | 16-ThrValLeuAlaAlaLeuSerSer-23 |
| SEQ. ID. NO. 11846 | 29-GlnThrGluGlyLeu-33 |
| SEQ. ID. NO. 11847 | 40-GlyGlnArgSerTyr-44 |
| SEQ. ID. NO. 11848 | 58-PheAlaAlaThrValGlyThrLys-65 |
| SEQ. ID. NO. 11849 | 67-ProAlaSerLeuArgGluIleProGlnSerVal-77 |
| SEQ. ID. NO. 11850 | 88-ArgAsnValAspThrPheAspGlnLeuAlaArg-98 |
| SEQ. ID. NO. 11851 | 131-ProAlaGlnMetGlnSerIleAsnGlyThrLeuProAsnLeuPheAlaPheAspArgValGluValMetArgGlyProSerGlyLeuPheAspSerSerGly GluMetGlyGlyIleValAsnLeuValArgLysArgProThrLysAlaPheGlnGlyHisAlaAlaAla-187 |
| SEQ. ID. NO. 11852 | 190-GlyThrHisLysGln-194 |
| SEQ. ID. NO. 11853 | 277-SerLeuProGlnHis-281 |
| SEQ. ID. NO. 11854 | 296-HisAspValPheAlaAspLeuLysHis-304 |
| SEQ. ID. NO. 11855 | 334-LeuAsnAsnThrGlyGlnAla-340 |
| SEQ. ID. NO. 11856 | 381-ArgLeuArgSerThr |
| SEQ. ID. NO. 11857 | 385AsnGluGlnGlyArgSerThr-392 |
| SEQ. ID. NO. 11858 | 398-AlaLeuAspGlyPheArgAlaLeuPro-406 |
| SEQ. ID. NO. 11859 | 419-LysGlyPheAsnHisSer-424 |

TABLE 1-continued

| | |
|---|---|
| SEQ. ID. NO. 11860 | 438-LysThrValPheArgProLeuGluGlyLeuSerLeuIleAlaGly-452 |
| SEQ. ID. NO. 11861 | 465-GlyLysThrLeuHisLysAlaSerLys-473 |
| SEQ. ID. NO. 11862 | 515-ProArgGluGlyAsnGln-520 |
| SEQ. ID. NO. 11863 | 565-GlyLysArgValMetGluGlyValGlu-573 |
| SEQ. ID. NO. 11864 | 617-AlaAsnLeuTrpThrThrTyr-623 |
| SEQ. ID. NO. 11865 | 635-ValAsnAlaMetSerGlyIleThrSerSer-644 |
| SEQ. ID. NO. 11866 | 650-GlyGlyTyrAlaThrPheAspAlaMetAlaAla-660 |
| Antigenic Index - Jameson-Wolf | |
| SEQ. ID. NO. 11867 | 29-GlnThrGluGlyLeuGlu-34 |
| SEQ. ID. NO. 11868 | 37-HisIleLysGlyGlnArgSerTyrAsn-45 |
| SEQ. ID. NO. 11869 | 48-AlaThrGluLysAsnGlyAspTyrSerSer-57 |
| SEQ. ID. NO. 11870 | 68-AlaSerLeuArgGluIleProGln-75 |
| SEQ. ID. NO. 11871 | 83-GlnGlnValLysAspArgAsnValAspThrPheAspGlnLeuAlaArgLysThrProGlyLeuArgValLeuSerAsnAspAspGlyArgSer-113 |
| SEQ. ID. NO. 11872 | 118-ArgGlyTyrGluTyrSerGluTyrAsnIleAspGlyLeu-130 |
| SEQ. ID. NO. 11873 | 148-AspArgValGluValMetArgGlyProSerGlyLeuPheAspSerSerGlyGluMetGlyGly-168 |
| SEQ. ID. NO. 11874 | 173-ValArgLysArgProThrLysAlaPhe-181 |
| SEQ. ID. NO. 11875 | 190-GlyThrHisLysGlnTyrLysAlaGluAlaAspValSerGlySerLeuAsnSerAspGlySerValArgGlyArgVal-215 |
| SEQ. ID. NO. 11876 | 221-GlyAlaSerProArgProAlaGluLysAsnAsnArgArgGluThr-235 |
| SEQ. ID. NO. 11877 | 242-TrpAspIleAsnProAspThrValLeu-250 |
| SEQ. ID. NO. 11878 | 257-GlnGlnArgArgLeuAlaProTyrAsn-265 |
| SEQ. ID. NO. 11879 | 268-ProAlaAspAlaAsnAsnLysLeuProSerLeu-278 |
| SEQ. ID. NO. 11880 | 306-PheGlyAsnGlyGlyTyrGly-312 |
| SEQ. ID. NO. 11881 | 314-ValGlyMetArgTyrSerAspArgLysAlaAspSerAsnTyr-327 |
| SEQ. ID. NO. 11882 | 330-AlaGlySerLysLeuAsnAsnThrGlyGlnAlaAsp-341 |
| SEQ. ID. NO. 11883 | 346-GlyThrAspIleLysGlnLysAlaPheAlaValAspAlaSerTyrSerArgProPhe-364 |
| SEQ. ID. NO. 11884 | 378-AspTyrAsnArgLeuArgSerThrAsnGluGlnGlyArgSerThrLeuSerLysSerValAla-398 |
| SEQ. ID. NO. 11885 | 413-AsnAlaArgAlaGlyAsnLysGlyPheAsn-422 |
| SEQ. ID. NO. 11886 | 424-SerValThrGluGluAsnLeuAspGluThrGlyLeu-435 |
| SEQ. ID. NO. 11887 | 451-AlaGlyGlyArgValGlyHisHisLysIleGluSerGlyAspGlyLysThrLeuHisLysAlaSerLysThrLysPhe-476 |
| SEQ. ID. NO. 11888 | 485-AspIleAspGlySerAsnSerLeu-492 |
| SEQ. ID. NO. 11889 | 501-ThrProGlnThrSerIleGlyThrAspGlyLysLeuLeuLysProArgGluGlyAsnGln-520 |
| SEQ. ID. NO. 11890 | 524-GlyTyrLysGlySerTyrMetAspAspArgLeuAsnThr-536 |
| SEQ. ID. NO. 11891 | 542-ArgMetLysAspLysAsnAla-548 |
| SEQ. ID. NO. 11892 | 551-ProLeuAspSerAsnAsnLysLysThrArgTyr-561 |
| SEQ. ID. NO. 11893 | 563-AlaLeuGlyLIGluThrGluIle-576 |
| SEQ. ID. NO. 11894 | 596-GlnIleLysThrAlaSerAsnSerArgAspGluGlyIle-608 |
| SEQ. ID. NO. 11895 | 614-LysHisSerAlaAsnLeu-619 |
| SEQ. ID. NO. 11896 | 663-PheThrProLysLeuLysLeu-669 |
| SEQ. ID. NO. 11897 | 671-IleAsnAlaAspAsnIlePhe-677 |
| SEQ. ID. NO. 11898 | 685-ValGlySerGluSerThrPheAsnIleProGlySerGluArgSerLeu-700 |
| Hydrophilic Regions - Hopp-Woods | |
| SEQ. ID. NO. 11899 | 39-LysGlyGlnArgSer-43 |
| SEQ. ID. NO. 11900 | 48-AlaThrGluLysAsnGlyAsp-54 |
| SEQ. ID. NO. 11901 | 68-AlaSerLeuArgGluIleProGln-75 |
| SEQ. ID. NO. 11902 | 84-GlnValLysAspArgAsnValAspThr-92 |
| SEQ. ID. NO. 11903 | 94-AspGlnLeuAlaArgLysThrProGly-102 |
| SEQ. ID. NO. 11904 | 106-LeuSerAsnAspAspGlyArgSer-113 |
| SEQ. ID. NO. 11905 | 148-AspArgValGluValMetArgGlyPro-156 |
| SEQ. ID. NO. 11906 | 162-SerSerGlyGluMet-166 |
| SEQ. ID. NO. 11907 | 173-ValArgLysArgProThrLys-179 |
| SEQ. ID. NO. 11908 | 193-LysGlnTyrLysAlaGluAlaAspVal-201 |
| SEQ. ID. NO. 11909 | 205-LeuAsnSerAspGlySerValArgGlyArgVal-215 |
| SEQ. ID. NO. 11910 | 222-AlaSerProArgProAlaGluLysAsnAsnArgArgGluThr-235 |
| SEQ. ID. NO. 11911 | 242-TrpAspIleAsnPro-246 |
| SEQ. ID. NO. 11912 | 257-GlnGlnArgArgLeuAla-262 |
| SEQ. ID. NO. 11913 | 268-ProAlaAspAlaAsnAsnLysLeu-275 |
| SEQ. ID. NO. 11914 | 314-ValGlyMetArgTyrSerAspArgLysAlaAspSer-325 |
| SEQ. ID. NO. 11915 | 247-ThrAspIleLysGlnLysAlaPheAla-355 |
| SEQ. ID. NO. 11916 | 378-AspTyrAsnArgLeuArgSerThrAsnGluGlnGlyArgSerThrLeuSer-394 |
| SEQ. ID. NO. 11917 | 414-AlaArgAlaGlyAsnLysGlyPhe-421 |
| SEQ. ID. NO. 11918 | 425-ValThrGluGluAsnLeuAspGlu-432 |
| SEQ. ID. NO. 11919 | 454-ArgValGlyHisHisLysIleGluSerGlyAspGlyLysThrLeuHisLysAlaSerLysThrLysPhe-476 |
| SEQ. ID. NO. 11920 | 506-IleGlyThrAspGlyLysLeuLeuLysProArgGluGlyAsnGln-520 |
| SEQ. ID. NO. 11921 | 528-SerTyrMetAspAspArgLeuAsnThr-536 |
| SEQ. ID. NO. 11922 | 542-ArgMetLysAspLysAsnAla-548 |
| SEQ. ID. NO. 11923 | 551-ProLeuAspSerAsnAsnLysLysThrArgTyr-561 |
| SEQ. ID. NO. 11924 | 563-AlaLeuGlyLysArgValMetGluGlyValGluThrGluIle-576 |
| SEQ. ID. NO. 11925 | 597-IleLysThrAlaSerAsnSerArgAspGluGly-607 |
| SEQ. ID. NO. 11926 | 695-GlySerGluArgSerLeu-700 |
| 761 | |
| AMPHI Regions - AMPHI | |
| SEQ. ID. NO. 11927 | 51-LysGlyTyrIleAsn-55 |
| SEQ. ID. NO. 11928 | 70-GluThrProGlnThrIleAspThrLeuAsnIle-80 |
| SEQ. ID. NO. 11929 | 89-AsnAspLeuSerSerIleLeuGlu-96 |
| SEQ. ID. NO. 11930 | 125-TyrArgAspGlyValArg-130 |
| SEQ. ID. NO. 11931 | 137-ArgSerThrAlaAsn-141 |
| SEQ. ID. NO. 11932 | 143-GluArgValGluIleLeuLysGlyProSer-152 |
| SEQ. ID. NO. 11933 | 164-ValIleAsnMetValSerLysTyrAlaAsnPheLysGlnSerArgAsnIleGlyAlaValTyrGlySerTrpAla-188 |
| SEQ. ID. NO. 11934 | 249-TyrAspAsnValGluArgThrProAspArgSerProThrLysSerVal-264 |
| SEQ. ID. NO. 11935 | 316-AspPheAspHisPheTyrAla-322 |

TABLE 1-continued

| | |
|---|---|
| SEQ. ID. NO. 11936 | 388-IleAsnProTyrAspArg-393 |
| SEQ. ID. NO. 11937 | 452-SerSerArgGlnTyr-456 |
| SEQ. ID. NO. 11938 | 475-HisThrLeuTyrAlaSerTyrAsnLysGlyPhe-485 |
| SEQ. ID. NO. 11939 | 511-TyrThrArgGlnTyrGlu-516 |
| SEQ. ID. NO. 11940 | 526-AspArgLeuSerThrThr-531 |
| SEQ. ID. NO. 11941 | 568-LeuSerAlaIleGlyGlnIleIle-575 |
| SEQ. ID. NO. 11942 | 608-AsnThrSerAsnVal-612 |
| SEQ. ID. NO. 11943 | 651-LeuProGlyPheAlaArgValAspAlaMet-660 |
| Antigenic Index - Jameson-Wolf | |
| SEQ. ID. NO. 11944 | 23-AlaAspThrGlnAspAsnGlyGluHis-31 |
| SEQ. ID. NO. 11945 | 43-GlyGlnSerAspThrSerValLeu-50 |
| SEQ. ID. NO. 11946 | 54-IleAsnTyrAspGluAlaAlaValThrArgAsnGlyGlnLeuIleLysGluThrProGlnThrIle-75 |
| SEQ. ID. NO. 11947 | 79-AsnIleGlnLysAsnLysAsnTyrGlyThrAsnAsp-90 |
| SEQ. ID. NO. 11948 | 97-GlyAsnAlaGlyIle-101 |
| SEQ. ID. NO. 11949 | 103-AlaAlaTyrAspMetArgGlyGluSerIlePhe-113 |
| SEQ. ID. NO. 11950 | 117-PheGlnAlaAspAlaSerAspIleTyrArgAspGlyValArgGluSerGlyGlnValArgArgSerThrAlaAsnIleGluArgValGluIleLeuLys GlyProSerSer-153 |
| SEQ. ID. NO. 11951 | 157-GlyArgThrAsnGlyGlyGly-163 |
| SEQ. ID. NO. 11952 | 172-AlaAsnPheLysGlnSerArgAsnIleGly-181 |
| SEQ. ID. NO. 11953 | 187-TrpAlaAsnArgSerLeuAsnMetAspIle-196 |
| SEQ. ID. NO. 11954 | 198-GluValLeuAsnLysAsnValAlaIle-206 |
| SEQ. ID. NO. 11955 | 208-LeuThrGlyGluValGlyArgAlaAsnSerPheArgSerGlyIleAspSerLysAsnVal-227 |
| SEQ. ID. NO. 11956 | 235-ValLysLeuAspAsnGlyLeuLysTrpThrGlyGlnTyrThrTyrAspAsnValGluArgThrProAspArgSerProThrLysSerValTyrAsp ArgPheGlyLeuProTyr-272 |
| SEQ. ID. NO. 11957 | 276-PheAlaHisArgAsnAspPheValLysAspLysLeuGln-288 |
| SEQ. ID. NO. 11958 | 290-TrpArgSerAspLeuGluTyrAlaPheAsnAspLysTrpArgAlaGlnTrp-306 |
| SEQ. ID. NO. 11959 | 312-ThrAlaAlaGlnAspPhe-317 |
| SEQ. ID. NO. 11960 | 322-AlaGlySerGluAsnGlyAsnLeuIleLysArgAsnTyrAlaTrpGlnGlnThrAspAsnLysThrLeuSer-345 |
| SEQ. ID. NO. 11961 | 366-GlyMetAspTyrSerArgGluHisArgAsnProThrLeu-378 |
| SEQ. ID. NO. 11962 | 389-AsnProTyrAspArgAlaSerTrpProAlaSerGlyArgLeuGlnPro-404 |
| SEQ. ID. NO. 11963 | 407-ThrGlnAsnArgHisLysAlaAspSer-415 |
| SEQ. ID. NO. 11964 | 425-SerAlaThrProAspLeuLysPheValLeuGlyGlyArgTyrAspLysTyrThrPheAsnSerGluAsnLysLeuThrGlySerSerArgGlnTyr SerGlyHisSerPheSerProAsn-464 |
| SEQ. ID. NO. 11965 | 481-TyrAsnLysGlyPheAlaProTyrGlyGlyArgGlyGly-493 |
| SEQ. ID. NO. 11966 | 506-AsnAlaAspProGluTyrThrArgGlnTyrGluThrGlyValLysSerSerTrpLeuAspAspArgLeuSerThr-530 |
| SEQ. ID. NO. 11967 | 539-ArgPheAsnIleArgTyrArgProAspProLysAsnAsnPro-552 |
| SEQ. ID. NO. 11968 | 557-ValSerGlyLysHisArgSerArgGlyValGlu-567 |
| SEQ. ID. NO. 11969 | 575-IleProLysLysLeuTyrLeu-581 |
| SEQ. ID. NO. 11970 | 591-LysValValGluAspLysGluAsnProAspArgValGly-603 |
| SEQ. ID. NO. 11971 | 607-AsnAsnThrSerAsnVal-612 |
| SEQ. ID. NO. 11972 | 619-ArgTyrThrProThrGluAsnLeuTyr-627 |
| SEQ. ID. NO. 11973 | 634-GlyThrGlyLysArgTyrGlyTyrAsnSerArgAsnLysGluValThrThr-650 |
| SEQ. ID. NO. 11974 | 663-TrpAsnHisLysAsn-667 |
| SEQ. ID. NO. 11975 | 678-LeuAsnGlnLysTyrTrpArgSerAspSerMetProGlyAsnProArgGlyTyrThrAla-697 |
| Hydrophilic Regions - Hopp-Woods | |
| SEQ. ID. NO. 11976 | 24-AspThrGlnAspAsnGlyGlu-30 |
| SEQ. ID. NO. 11977 | 43-GlyGlnSerAspThrSerVal-49 |
| SEQ. ID. NO. 11978 | 57-AspGluAlaAlaValThrArg-63 |
| SEQ. ID. NO. 11979 | 66-GlnLeuIleLysGluThrProGlnThr-74 |
| SEQ. ID. NO. 11980 | 81-GlnLysAsnLysAsnTyrGly-87 |
| SEQ. ID. NO. 11981 | 105-TyrAspMetArgGlyGluSerIlePhe-113 |
| SEQ. ID. NO. 11982 | 117-PheGlnAlaAspAlaSerAspIleTyrArgAspGlyValArgGluSerGlyGlnValArgArgSerThrAlaAsnIleGluArgValGluIleLeu LysGlyProSer-152 |
| SEQ. ID. NO. 11983 | 175-LysGlnSerArgAsn-179 |
| SEQ. ID. NO. 11984 | 208-LeuThrGlyGluValGlyArg-214 |
| SEQ. ID. NO. 11985 | 220-SerGlyIleAspSerLysAsn-226 |
| SEQ. ID. NO. 11986 | 235-ValLysLeuAspAsn-239 |
| SEQ. ID. NO. 11987 | 251-AsnValGluArgThrProAspArgSerProThr-261 |
| SEQ. ID. NO. 11988 | 278-HisArgAsnAspPheValLysAspLysLeuGln-288 |
| SEQ. ID. NO. 11989 | 312-ThrAlaAlaGlnAspPhe-317 |
| SEQ. ID. NO. 11990 | 324-SerGluAsnGlyAsnLeuIleLys-331 |
| SEQ. ID. NO. 11991 | 339-ThrAspAsnLysThrLeu-344 |
| SEQ. ID. NO. 11992 | 368-AspTyrSerArgGluHisArgAsnPro-376 |
| SEQ. ID. NO. 11993 | 390-ProTyrAspArgAlaSer-395 |
| SEQ. ID. NO. 11994 | 409-AsnArgHisLysAlaAspSer-415 |
| SEQ. ID. NO. 11995 | 436-GlyArgTyrAspLys-440 |
| SEQ. ID. NO. 11996 | 445-SerGluAsnLysLeuThrGlySerSerArgGlnTyrSer-457 |
| SEQ. ID. NO. 11997 | 507-AlaAspProGluTyrThrArgGlnTyrGluThrGlyVal-519 |
| SEQ. ID. NO. 11998 | 523-TrpLeuAspAspArgLeuSer-529 |
| SEQ. ID. NO. 11999 | 544-TyrArgProAspProLysAsn-550 |
| SEQ. ID. NO. 12000 | 559-GlyLysHisArgSerArgGlyValGlu-567 |
| SEQ. ID. NO. 12001 | 591-LysValValGluAspLysGluAsnProAspArgValGly-603 |
| SEQ. ID. NO. 12002 | 634-GlyThrGlyLysArgTyrGlyTyr-641 |
| SEQ. ID. NO. 12003 | 643-SerArgAsnLysGluValThr-649 |
| SEQ. ID. NO. 12004 | 686-AspSerMetProGlyAsnProArgGlyTyrThr-696 |
| 762 | |
| AMPHI Regions - AMPHI | |
| SEQ. ID. NO. 12005 | 1-MetLysTrpLeuLeuAsnMetIleMetArgProIleLysPheSerMetValAsnThrLeuLeuPheIleValIleCysSerSerPhePheAspLeuLeu ValGlnLeuCysThrIleLeuPheHisSerGlnLysIleTyrPheIleThrLeuPheLeuLeuPheIlePheAsnPheValThrLysSerIleTyrMetAlaIle IleTyrProIleLeuTyrPhePheThrIleLysLysTyrTyrProTyrSerArgLysValIleIleLeuLeuSerLeuAlaLeuSerIleTyrPheSerPheMet |

AspPheTyrPhePheSerIleTyrSerAspAsnLeuSerTyrGluThrGluProLeuHisLeuTyrIleProIleIleIleAsnPhePheSerLeuLeuVal SerAsnPheIleLeuSerPheIleAsnLys-147

Antigenic Index - Jameson-Wolf
(SEQ. ID. NO. 12005)
1-MetLysTrpLeuLeuAsnMetIleMetArgProIleLysPheSerMetValAsnThrLeuLeuPheIleValIleCysSerSerPhePheAspLeuLeuValGlnLeuCysThrIleLeuPhe HisSerGlnLysIleTyrPheIleThrLeuPheLeuLeuPheIlePheAsnPheValThrLysSerIleTyrMetAlaIleIleTyrProIleLeuTyrPhePheThrIleLysLysTyrTyrProTyr SerArgLysValIleIleLeuLeuSerLeuAlaLeuSerIleTyrPheSerPheMetAspPheTyrPhePheSerIleTyrSerAspAsnLeuSerTyrGluThrGluProLeuHisLeuTyrIle ProIleIleIleAsnPhePheSerLeuLeuValSerAsnPheIleLeuSerPheIleAsnLys-147

Hydrophilic Regions - Hopp-Woods
(SEQ. ID. NO. 12005)
1-MetLysTrpLeuLeuAsnMetIleMetArgProIleLysPheSerMetValAsnThrLeuLeuPheIleValIleCysSerSerPhePheAspLeuLeuValGlnLeuCysThrIleLeuPhe HisSerGlnLysIleTyrPheIleThrLeuPheLeuLeuPheIlePheAsnPheValThrLysSerIleTyrMetAlaIleIleTyrProIleLeuTyrPhePheThrIleLysLysTyrTyrProTyrSer ArgLysValIleIleLeuLeuSerLeuAlaLeuSerIleTyrPheSerPheMetAspPheTyrPhePheSerIleTyrSerAspAsnLeuSerTyrGluThrGluProLeuHisLeuTyrIleProIleIle IleAsnPhePheSerLeuLeuValSerAsnPheIleLeuSerPheIleAsnLys-147

763

AMPHI Regions - AMPHI
SEQ. ID. NO. 12006 1-MetThrLeuLeuAsnLeuMetIleMetGlnAspTyrGlyIleSerValCysLeuThrLeuThrProTyrLeuGlnHisGluLeuPheSerAlaMetLys SerTyrPheSerLysTyrIleLeuProValSerLeuPheThrLeuProLeuSerLeuSerProSerValSerAlaPheThrLeuProGluAlaTrpArgAlaAlaGln GlnHisSerAlaAspPheGlnAlaSerHisTyrGlnArgAspAlaValArgAlaArgGlnGlnGlnAlaLysAlaAlaPheLeuProHisValSerAlaAsnAla SerTyrGlnArgGlnProProSerIleSerSerThrArgGluThrGlnGlyTrpSerValGlnValGlyGlnThrLeuPheAspAlaAlaLysPheAlaGlnTyrArg GlnSerArgPheAspThrGlnAlaAlaGluGlnArgPheAspAlaAlaArgGluGluLeuLeuLeuLysValAlaGluSerTyrPheAsnValLeuLeuSer ArgAspThrValAlaAlaHisAlaAlaGluLysGluAlaTyrAlaGlnGlnValArgGlnAlaGlnAlaLeuPheAsnLysGlyAlaAlaThrAlaLeuAsp IleHisGluAlaLysAlaGlyTyrAspAsnAlaLeuAlaGlnGluIleAlaValLeuAlaGluLysGlnThrTyrGluAsnGlnLeuAsnAspTyrThrAsp LeuAspSerLysGlnIleGluAlaIleAspThrAlaAsnLeuLeuAlaArgTyrLeuProLysLeuGluArgTyrSerLeuAspGluTrpGlnArgIleAla LeuSerAsnAsnHisGluTyrArgMetGlnGlnLeuAlaLeuGlnSerSerGlyGlnAlaLeuArgAlaAlaGlnAsnSerArgTyrProThrValSerAlaHis ValGlyTyrGlnAsnAsnLeuTyrThrSerSerAlaGlnAsnAsnAspTyrHisTyrArgGlyLysGlyMetSerValGlyValGlnLeuAsnLeuProLeu TyrThrGlyGlyGluLeuSerGlyLysIleHisGluAlaGluAlaGlnTyrGlyAlaAlaGluAlaGlnLeuThrAlaThrGluArgHisIleLysLeuAlaVal ArgGlnAlaTyrThrGluSerGlyAlaAlaArgTyrGlnIleMetAlaGlnGluArgValLeuGluSerSerArgLeuLysLeuLysSerThrGluThrGly GlnGlnTyrGlyIleArgAsnArgLeuGluValIleArgAlaArgGlnGluValAlaGlnAlaGluGlnLysLeuAlaGlnAlaArgTyrLysPheMetLeuAla TyrLeuArgLeuValLysGluSerGlyLeuGlyLeuGluThrValPheAlaGlu-467

Antigenic Index - Jameson-Wolf
(SEQ. NO. ID. 12006)
1-MetThrLeuLeuAsnLeuMetIleMetGlnAspTyrGlyIleSerValCysLeuThrLeuThrProTyrLeuGlnHisGluLeuPheSerAlaMetLysSerTyrPheSerLysTyrIleLeu ProValSerLeuPheThrLeuProLeuSerLeuSerProSerValSerAlaPheThrLeuProGluAlaTrpArgAlaAlaGlnGlnHisSerAlaAspPheGlnAlaSerHisTyrGlnArgAsp AlaValArgAlaArgGlnGlnGlnAlaLysAlaAlaPheLeuProHisValSerAlaAsnAlaSerTyrGlnArgGlnProProSerIleSerSerThrArgGluThrGlnGlyTrpSerValGln ValGlyGlnThrLeuPheAspAlaAlaLysPheAlaGlnTyrArgGlnSerArgPheAspThrGlnAlaAlaGluGlnArgPheAspAlaAlaArgGluGluLeuLeuLeuLysValAlaGluSer TyrPheAsnValLeuLeuSerArgAspThrValAlaAlaHisAlaAlaGluLysGluAlaTyrAlaGlnGlnValArgGlnAlaGlnAlaLeuPheAsnLysGlyAlaAlaThrAlaLeuAspIle HisGluAlaLysAlaGlyTyrAspAsnAlaLeuAlaGlnGluIleAlaValLeuAlaGluLysGlnThrTyrGluAsnGlnLeuAsnAspTyrThrAspLeuAspSerLysGlnIleGluAlaIle AspThrAlaAsnLeuLeuAlaArgTyrLeuProLysLeuGluArgTyrSerLeuAspGluTrpGlnArgIleAlaLeuSerAsnAsnHisGluTyrArgMetGlnGlnLeuAlaLeuGlnSerSer GlyGlnAlaLeuArgAlaAlaGlnAsnSerArgTyrProThrValSerAlaHisValGlyTyrGlnAsnAsnLeuTyrThrSerSerAlaGlnAsnAsnAspTyrHisTyrArgGlyLysGlyMet SerValGlyValGlnLeuAsnLeuProLeuTyrThrGlyGlyGluLeuSerGlyLysIleHisGluAlaGluAlaGlnTyrGlyAlaAlaGluAlaGlnLeuThrAlaThrGluArgHisIleLysLeu AlaValArgGlnAlaTyrThrGluSerGlyAlaAlaArgTyrGlnIleMetAlaGlnGluArgValLeuGluSerSerArgLeuLysLeuLysSerThrGluThrGlyGlnGlnTyrGlyIleArg AsnArgLeuGluValIleArgAlaArgGlnGluValAlaGlnAlaGluGlnLysLeuAlaGlnAlaArgTyrLysPheMetLeuAlaTyrLeuArgLeuValLysGluSerGlyLeu GlyLeuGluThrValPheAlaGlu-467

Hydrophilic Regions - Hopp-Woods
(SEQ. NO. ID. 12006)
1-MetThrLeuLeuAsnLeuMetIleMetGlnAspTyrGlyIleSerValCysLeuThrLeuThrProTyrLeuGlnHisGluLeuPheSerAlaMetLysSerTyrPheSerLysTyrIleLeuPro ValSerLeuPheThrLeuProLeuSerLeuSerProSerValSerAlaPheThrLeuProGluAlaTrpArgAlaAlaGlnGlnHisSerAlaAspPheGlnAlaSerHisTyrGlnArgAspAla ValArgAlaArgGlnGlnGlnAlaLysAlaAlaPheLeuProHisValSerAlaAsnAlaSerTyrGlnArgGlnProProSerIleSerSerThrArgGluThrGlnGlyTrpSerValGlnVal GlyGlnThrLeuPheAspAlaAlaLysPheAlaGlnTyrArgGlnSerArgPheAspThrGlnAlaAlaGluGlnArgPheAspAlaAlaArgGluGluLeuLeuLeuLysValAlaGlu SerTyrPheAsnValLeuLeuSerArgAspThrValAlaAlaHisAlaAlaGluLysGluAlaTyrAlaGlnGlnValArgGlnAlaGlnAlaLeuPheAsnLysGlyAlaAlaThrAlaLeuAsp IleHisGluAlaLysAlaGlyTyrAspAsnAlaLeuAlaGlnGluIleAlaValLeuAlaGluLysGlnThrTyrGluAsnGlnLeuAsnAspTyrThrAspLeuAspSerLysGlnIleGluAla IleAspThrAlaAsnLeuLeuAlaArgTyrLeuProLysLeuGluArgTyrSerLeuAspGluTrpGlnArgIleAlaLeuSerAsnAsnHisGluTyrArgMetGlnGlnLeuAlaLeuGln SerSerGlyGlnAlaLeuArgAlaAlaGlnAsnSerArgTyrProThrValSerAlaHisValGlyTyrGlnAsnAsnLeuTyrThrSerSerAlaGlnAsnAsnAspTyrHisTyrArgGly LysGlyMetSerValGlyValGlnLeuAsnLeuProLeuTyrThrGlyGlyGluLeuSerGlyLysIleHisGluAlaGluAlaGlnTyrGlyAlaAlaGluAlaGlnLeuThrAlaThrGluArg HisIleLysLeuAlaValArgGlnAlaTyrThrGluSerGlyAlaAlaArgTyrGlnIleMetAlaGlnGluArgValLeuGluSerSerArgLeuLysLeuLysSerThrGluThrGlyGlnGlnTyr GlyIleArgAsnArgLeuGluValIleArgAlaArgGlnGluValAlaGlnAlaGluGlnLysLeuAlaGlnAlaArgTyrLysPheMetLeuAlaTyrLeuArgLeuValLysGluSerGlyLeu GlyLeuGluThrValPheAlaGlu-467

764

AMPHI Regions - AMPHI
SEQ. ID. NO. 12007 1-MetPhePheSerAlaLeuLysSerPheLeuSerArgTyrIleThrValTrpArgAsnValTrpAlaValArgAspGlnLeuLysProProLysArgThrAla GluGluGlnAlaPheLeuProAlaHisLeuGluLeuThrAspThrProValSerAlaAlaProLysTrpAlaAlaArgPheIleMetAlaPheAlaLeuLeuAla LeuLeuTrpSerTrpPheGlyLysIleAspIleValAlaAlaAlaSerGlyLysThrValSerGlyGlyArgSerLysThrIleGlnProLeuGluThrAlaValVal LysAlaValHisValArgAspGlyGlnHisValLysGlnGlyGluThrLeuAlaGluLeuGluAlaValGlyThrAspSerAspValValGlnSerGluGlnAla LeuGlnAlaAlaGlnLeuSerLysLeuArgTyrGluAlaValLeuAlaAlaLeuGluSerArgThrValProHisIleAspMetAlaGlnAlaArgSerLeuGly LeuSerAspAlaAspValGlnSerAlaGlnValLeuAlaGlnHisGlnTyrGlnAlaTrpAlaAlaGlnAspAlaGlnLeuGlnSerAlaLeuArgGlyHisGln AlaGluLeuGlnSerAlaLysAlaGlnGluGlnLysLeuValSerValGlyAlaIleGluGlnGlnLysThrAlaAspTyrArgArgLeuArgAlaAspAsnPhe IleSerGluHisAlaPheLeuGluGlnGlnSerLysSerValSerAsnTrpAsnAspLeuGluSerThrArgGlyGlnMetArgGlnIleGlnAlaAlaIleAlaGln AlaGluGlnAsnArgValLeuAsnThrGlnAsnLeuLysArgAspThrLeuAspAlaLeuArgGlnAlaAsnGluGlnIleAspGlnTyrArgGlyGlnThr AspLysAlaLysGlnArgGlnGlnLeuMetThrIleGlnSerProAlaAspGlyThrValGlnGluLeuAlaThrTyrThrValGlyGlyValValGlnAlaAla GlnLysMetMetValIleAlaProAspAspAspLysMetAspValGluValLeuValLeuAsnLysAspIleGlyPheValGluGlnGlyGlnAspAlaValVal LysIleGluSerPheProTyrThrArgTyrGlyTyrLeuThrGlyLysValLysSerValSerHisAspAlaValSerHisGluGlnLeuGlyLeuValTyrThrAla ValValSerLeuAspLysHisThrLeuAsnIleAspGlyLysAlaValAsnLeuThrAlaGlyMetAsnValThrAlaGluIleLysThrGlyLysArgArgVal LeuAspTyrLeuLeuSerProLeuGlnThrLysLeuAspGluSerPheArgGluArg-475

Antigenic Index - Jameson-Wolf
(SEQ. ID. NO. 12007)
1-MetPhePheSerAlaLeuLysSerPheLeuSerArgTyrIleThrValTrpArgAsnValTrpAlaValArgAspGlnLeuLysProProLysArgThrAlaGluGluGlnAlaPheLeuProAla HisLeuGluLeuThrAspThrProValSerAlaAlaProLysTrpAlaAlaArgPheIleMetAlaPheAlaLeuLeuAlaLeuLeuTrpSerTrpPheGlyLysIleAspIleValAlaAlaAlaSer GlyLysThrValSerGlyGlyArgSerLysThrIleGlnProLeuGluThrAlaValValLysAlaValHisValArgAspGlyGlnHisValLysGlnGlyGluThrLeuAlaGluLeuGluAla ValGlyThrAspSerAspValValGlnSerGluGlnAlaLeuGlnAlaAlaGlnLeuSerLysLeuArgTyrGluAlaValLeuAlaAlaLeuGluSerArgThrValProHisIleAspMetAla TABLE 1-continued GlnAlaArgSerLeuGlyLeuSerAspAlaAspValGlnSerAlaGlnValLeuAlaGlnHisGlnTyrGlnAlaTrpAlaAlaGlnAspAlaGlnLeuGlnSerAlaLeuArgGlyHisGlnAla
GluLeuGlnSerAlaLysAlaGlnGluGlnLysLeuValSerValGlyAlaIleGluGlnGlnLysThrAlaAspTyrArgArgLeuArgAlaAspAsnPheIleSerGluHisAlaPheLeuGluGln
GlnSerLysSerValSerAsnTrpAsnAspLeuGluSerThrArgGlyGlnMetArgGlnIleGlnAlaAlaIleAlaGlnAlaGluGlnAsnArgValLeuAsnThrGlnAsnLeuLysArgAsp
ThrLeuAspAlaLeuArgGlnAlaAsnGluGlnIleAspGlnTyrArgGlyGlnThrAspLysAlaLysGlnArgGlnGlnLeuMetThrIleGlnSerProAlaAspGlyThrValGlnGluLeu
AlaThrTyrThrValGlyGlyValValGlnAlaAlaGlnLysMetMetValIleAlaProAspAspAspLysMetAspValGluValLeuValLeuAsnLysAspIleGlyPheValGluGlnGly
GlnAspAlaValValLysIleGluSerPheProTyrThrArgTyrGlyTyrLeuThrGlyLysValLysSerValSerHisAspAlaValSerHisGluGlnLeuGlyLeuValTyrThrAlaValVal
SerLeuAspLysHisThrLeuAsnIleAspGlyLysAlaValAsnLeuThrAlaGlyMetAsnValThrAlaGluIleLysThrGlyLysArgArgValLeuAspTyrLeuLeuSerProLeuGln
ThrLysLeuAspGluSerPheArgGluArg-475
Hydrophilic Regions - Hopp-Woods
(SEQ. ID. NO. 12007)
1-MetPhePheSerAlaLeuLysSerPheLeuSerArgTyrIleThrValTrpArgAsnValTrpAlaValArgAspGlnLeuLysProProLysArgThrAlaGluGluGlnAlaPheLeuProAla
HisLeuGluLeuThrAspThrProValSerAlaAlaProLysTrpAlaAlaArgPheIleMetAlaPheAlaLeuLeuAlaLeuLeuTrpSerTrpPheGlyLysIleAspIleValAlaAlaAlaSer
GlyLysThrValSerGlyGlyArgSerLysThrIleGlnProLeuGluThrAlaValValLysAlaValHisValArgAspGlyGlnHisValLysGlnGlyGluThrLeuAlaGluLeuGluAlaVal
GlyThrAspSerAspValValGlnSerGluGlnAlaLeuGlnAlaAlaGlnLeuSerLysLeuArgTyrGluAlaValLeuAlaAlaLeuGluSerArgThrValProHisIleAspMetAlaGlnAla
ArgSerLeuGlyLeuSerAspAlaAspValGlnSerAlaGlnValLeuAlaGlnHisGlnTyrGlnAlaTrpAlaAlaGlnAspAlaGlnLeuGlnSerAlaLeuArgGlyHisGlnAlaGluLeu
GlnSerAlaLysAlaGlnGluGlnLysLeuValSerValGlyAlaIleGluGlnGlnLysThrAlaAspTyrArgArgLeuArgAlaAspAsnPheIleSerGluHisAlaPheLeuGluGlnGlnSer
LysSerValSerAsnTrpAsnAspLeuGluSerThrArgGlyGlnMetArgGlnIleGlnAlaAlaIleAlaGlnAlaGluGlnAsnArgValLeuAsnThrGlnAsnLeuLysArgAspThrLeu
AspAlaLeuArgGlnAlaAsnGluGlnIleAspGlnTyrArgGlyGlnThrAspLysAlaLysGlnArgGlnGlnLeuMetThrIleGlnSerProAlaAspGlyThrValGlnGluLeuAlaThr
TyrThrValGlyGlyValValGlnAlaAlaGlnLysMetMetValIleAlaProAspAspAspLysMetAspValGluValLeuValLeuAsnLysAspIleGlyPheValGluGlnGlyGlnAsp
AlaValValLysIleGluSerPheProTyrThrArgTyrGlyTyrLeuThrGlyLysValLysSerValSerHisAspAlaValSerHisGluGlnLeuGlyLeuValTyrThrAlaValValSerLeu
AspLysHisThrLeuAsnIleAspGlyLysAlaValAsnLeuThrAlaGlyMetAsnValThrAlaGluIleLysThrGlyLysArgArgValLeuAspTyrLeuLeuSerProLeuGlnThrLys
LeuAspGluSerPheArgGluArg-475
765
AMPHI Regions - AMPHI

| | |
|---|---|
| SEQ. ID. NO. 12008 | 36-SerAlaIleSerSerPheCys-42 |
| SEQ. ID. NO. 12009 | 45-LysIleIleHisThrTyr-50 |
| SEQ. ID. NO. 12010 | 59-ValIleGlyIleIleAsnGly-65 |
| SEQ. ID. NO. 12011 | 105-ArgPheLeuAsnArgGly-110 |
| SEQ. ID. NO. 12012 | 147-PheGlyLeuCysTyrPro-152 |

Antigenic Index - Jameson-Wolf

| | |
|---|---|
| SEQ. ID. NO. 12013 | 10-GlyAsnPheLysLysIleAlaThr-17 |
| SEQ. ID. NO. 12014 | 19-GlnGlyLeuAspArgLysTyr-25 |
| SEQ. ID. NO. 12015 | 76-ValLysAsnLysGlnLysPheLeu-83 |
| SEQ. ID. NO. 12016 | 106-PheLeuAsnArgGlyMetLys-112 |
| SEQ. ID. NO. 12017 | 132-LeuAsnGluGluGlyGlyTrpMet-139 |
| SEQ. ID. NO. 12018 | 160-LeuSerArgAspTyrLysHisIle-167 |

Hydrophilic Regions - Hopp-Woods

| | |
|---|---|
| SEQ. ID. NO. 12019 | 11-AsnPheLysLysIleAlaThr-17 |
| SEQ. ID. NO. 12020 | 19-GlnGlyLeuAspArgLys-24 |
| SEQ. ID. NO. 12021 | 76-ValLysAsnLysGlnLysPheLeu-83 |
| SEQ. ID. NO. 12022 | 133-AsnGluGluGlyGly-137 |
| SEQ. ID. NO. 12023 | 162-ArgAspTyrLysHis-166 |

767
AMPHI Regions - AMPHI

| | |
|---|---|
| SEQ. ID. NO. 12024 | 1-MetLysLeuLysHisLeuLeuProLeuLeuLeuSerAlaValLeuSerAlaGlnAlaTyrAlaLeuThrGluGlyGluAspTyrLeuValLeuAspLysPro IleProGlnGluGlnSerGlyLysIleGluValLeuGluPhePheGlyTyrPheCysValHisCysHisHisPheAspProLeuLeuLeuLysLeuGlyLysAla LeuProSerAspAlaTyrLeuArgThrGluHisValValTrpGlnProGluMetLeuGlyLeuAlaArgMetAlaAlaAlaValAsnLeuSerGlyLeuLysTyr GlnAlaAsnProAlaValPheLysAlaValTyrGluGlnLysIleArgLeuGluAsnArgSerValAlaGlyLysTrpAlaLeuSerGlnLysGlyPheAspGly LysLysLeuMetArgAlaTyrAspSerProGluAlaAlaAlaAlaAlaLeuLysMetGlnLysLeuThrGluGlnTyrArgIleAspSerThrProThrValIle ValGlyGlyLysTyrArgValIlePheAsnAsnGlyPheAspGlyGlyValHisThrIleLysGluLeuValAlaLysValArgGluGluArgLysArgGlnThr ProAlaValGlnLys-214 |

Antigenic Index - Jameson-Wolf
(SEQ. ID. NO. 12024)
1-MetLysLeuLysHisLeuLeuProLeuLeuLeuSerAlaValLeuSerAlaGlnAlaTyrAlaLeuThrGluGlyGluAspTyrLeuValLeuAspLysProIleProGlnGluGlnSerGlyLys
IleGluValLeuGluPhePheGlyTyrPheCysValHisCysHisHisPheAspProLeuLeuLeuLysLeuGlyLysAlaLeuProSerAspAlaTyrLeuArgThrGluHisValValTrpGlnPro
GluMetLeuGlyLeuAlaArgMetAlaAlaAlaValAsnLeuSerGlyLeuLysTyrGlnAlaAsnProAlaValPheLysAlaValTyrGluGlnLysIleArgLeuGluAsnArgSerValAla
GlyLysTrpAlaLeuSerGlnLysGlyPheAspGlyLysLysLeuMetArgAlaTyrAspSerProGluAlaAlaAlaAlaAlaLeuLysMetGlnLysLeuThrGluGlnTyrArgIleAspSer
ThrProThrValIleValGlyGlyLysTyrArgValIlePheAsnAsnGlyPheAspGlyGlyValHisThrIleLysGluLeuValAlaLysValArgGluGluArgLysArgGlnThrProAlaVal
GlnLys-214
Hydrophilic Regions - Hopp-Woods
(SEQ. ID. NO. 12024)
1-MetLysLeuLysHisLeuLeuProLeuLeuLeuSerAlaValLeuSerAlaGlnAlaTyrAlaLeuThrGluGlyGluAspTyrLeuValLeuAspLysProIleProGlnGluGlnSerGlyLys
IleGluValLeuGluPhePheGlyTyrPheCysValHisCysHisHisPheAspProLeuLeuLeuLysLeuGlyLysAlaLeuProSerAspAlaTyrLeuArgThrGluHisValValTrpGlnPro
GluMetLeuGlyLeuAlaArgMetAlaAlaAlaValAsnLeuSerGlyLeuLysTyrGlnAlaAsnProAlaValPheLysAlaValTyrGluGlnLysIleArgLeuGluAsnArgSerValAla
GlyLysTrpAlaLeuSerGlnLysGlyPheAspGlyLysLysLeuMetArgAlaTyrAspSerProGluAlaAlaAlaAlaAlaLeuLysMetGlnLysLeuThrGluGlnTyrArgIleAspSer
ThrProThrValIleValGlyGlyLysTyrArgValIlePheAsnAsnGlyPheAspGlyGlyValHisThrIleLysGluLeuValAlaLysValArgGluGluArgLysArgGlnThrProAlaVal
GlnLys-214
768
AMPHI Regions - AMPHI

| | |
|---|---|
| SEQ. ID. NO. 12025 | 23-ProGlnLysProValSerAlaAlaGlnThr-32 |
| SEQ. ID. NO. 12026 | 60-ProValAspGlnIleValArgArgIleHisGluAlaAla-72 |
| SEQ. ID. NO. 12027 | 93-LeuGlnGluLeuLysLysAlaGlyTyrThrAsnValAlaAsnHisGly-108 |

Antigenic Index - Jameson-Wolf

| | |
|---|---|
| SEQ. ID. NO. 12028 | 21-AlaAlaProGlnLysProValSer-28 |
| SEQ. ID. NO. 12029 | 42-ValArgSerGluGlnGluPheSerGluGlyHis-52 |
| SEQ. ID. NO. 12030 | 63-GlnIleValArgArgIleHisGluAlaAlaProAspLysAspThrPro-78 |
| SEQ. ID. NO. 12031 | 82-TyrCysArgSerGlyArgArgAlaGluAlaAlaLeuGlnGluLeuLysLysAlaGlyTyr-101 |
| SEQ. ID. NO. 12032 | 106-AsnHisGlyGlyTyrGluAspLeuLeuLysLysGlyMetLys-119 |

TABLE 1-continued

Hydrophilic Regions - Hopp-Woods
SEQ. ID. NO. 12033 22-AlaProGlnLysProValSer-28
SEQ. ID. NO. 12034 42-ValArgSerGluGlnGluPheSerGlu-50
SEQ. ID. NO. 12035 63-GlnIleValArgArgIleHisGluAlaAlaProAspLysAspThrPro-78
SEQ. ID. NO. 12036 84-ArgSerGlyArgArgAlaGluAlaAlaLeuGlnGluLeuLysLysAlaGly-100
SEQ. ID. NO. 12037 109-GlyTyrGluAspLeuLeuLysLysGlyMetLys-119
769
AMPHI Regions - AMPHI
SEQ. ID. NO. 12038 1-LeuIleMetValIlePheTyrPheCysGlyLysThrPheMetProAlaArgAsnArgTrpMetLeuLeuLeuProLeuLeuAlaSerAlaAlaTyrAlaGlu GluThrProArgGluProAspLeuArgSerArgProGluPheArgLeuHisGluAlaGluValLysProIleAspArgGluLysValProGlyGlnValArgGlu LysGlyLysValLeuGlnIleAspGlyGluThrLeuLeuLysAsnProGluLeuLeuSerArgAlaMetTyrSerAlaValValSerAsnAsnIleAlaGlyIle ArgValIleLeuProIleTyrLeuGlnGlnAlaGlnGlnAspLysMetLeuAlaLeuTyrAlaGlnGlyIleLeuAlaGlnAlaAspGlyArgValLysGluAlaIle SerHisTyrArgGluLeuIleAlaAlaGlnProAspAlaProAlaValArgMetArgLeuAlaAlaAlaLeuPheGluAsnArgGlnAsnGluAlaAlaAlaAsp GlnPheAspArgLeuLysAlaGluAsnLeuProProGlnLeuMetGluGlnValGluLeuTyrArgLysAlaLeuArgGluArgAspAlaTrpLysValAsn GlyGlyPheSerValThrArgGluHisAsnIleAsnGlnAlaProLysArgGlnGlnTyrGlyLysTrpThrPheProLysGlnValAspGlyThrAlaValAsn TyrArgLeuGlyAlaGluLysLysTrpSerLeuLysAsnGlyTrpTyrThrThrAlaGlyGlyAspValSerGlyArgValTyrProGlyAsnLysLysPheAsn AspMetThrAlaGlyValSerGlyGlyIleGlyPheAlaAspArgArgLysAspAlaGlyLeuAlaValPheHisGluArgArgThrTyrGlyAsnAspAlaTyr SerTyrThrAsnGlyAlaArgLeuTyrPheAsnArgTrpGlnThrProLysTrpGlnThrLeuSerSerAlaGluTrpGlyArgLeuLysAsnThrArgArgAla ArgSerAspAsnThrHisLeuGlnIleSerAsnSerLeuValPheTyrArgAsnAlaArgGlnTyrTrpMetGlyGlyLeuAspPheTyrArgGluArgAsnPro AlaAspArgGlyAspAsnPheAsnArgTyrGlyLeuArgPheAlaTrpGlyGlnGluTrpGlyGlySerGlyLeuSerSerLeuLeuArgLeuGlyAlaAla LysArgHisTyrGluLysProGlyPhePheSerGlyPheLysGlyGluArgArgArgAspLysGluLeuAsnThrSerLeuSerLeuTrpHisArgAlaLeuHis PheLysGlyIleThrProArgLeuThrLeuSerHisArgGluThrArgSerAsnAspValPheAsnGluTyrGluLysAsnArgAlaPheValGluPheAsnLys ThrPhe-490
Antigenic Index - Jameson-Wolf
(SEQ. ID. NO. 12038)
1-LeuIleMetValIlePheTyrPheCysGlyLysThrPheMetProAlaArgAsnArgTrpMetLeuLeuLeuProLeuLeuAlaSerAlaAlaTyrAlaGluGluThrProArgGluProAspLeu ArgSerArgProGluPheArgLeuHisGluAlaGluValLysProIleAspArgGluLysValProGlyGlnValArgGluLysGlyLysValLeuGlnIleAspGlyGluThrLeuLeuLysAsnPro GluLeuLeuSerArgAlaMetTyrSerAlaValValSerAsnAsnIleAlaGlyIleArgValIleLeuProIleTyrLeuGlnGlnAlaGlnGlnAspLysMetLeuAlaLeuTyrAlaGlnGlyIleLeu AlaGlnAlaAspGlyArgValLysGluAlaIleSerHisTyrArgGluLeuIleAlaAlaGlnProAspAlaProAlaValArgMetArgLeuAlaAlaAlaLeuPheGluAsnArgGlnAsnGluAla AlaAlaAspGlnPheAspArgLeuLysAlaGluAsnLeuProProGlnLeuMetGluGlnValGluLeuTyrArgLysAlaLeuArgGluArgAspAlaTrpLysValAsnGlyGlyPheSerVal ThrArgGluHisAsnIleAsnGlnAlaProLysArgGlnGlnTyrGlyLysTrpThrPheProLysGlnValAspGlyThrAlaValAsnTyrArgLeuGlyAlaGluLysLysTrpSerLeuLys AsnGlyTrpTyrThrThrAlaGlyGlyAspValSerGlyArgValTyrProGlyAsnLysLysPheAsnAspMetThrAlaGlyValSerGlyGlyIleGlyPheAlaAspArgArgLysAspAla GlyLeuAlaValPheHisGluArgArgThrTyrGlyAsnAspAlaTyrSerTyrThrAsnGlyAlaArgLeuTyrPheAsnArgTrpGlnThrProLysTrpGlnThrLeuSerSerAlaGluTrp GlyArgLeuLysAsnThrArgArgAlaArgSerAspAsnThrHisLeuGlnIleSerAsnSerLeuValPheTyrArgAsnAlaArgGlnTyrTrpMetGlyGlyLeuAspPheTyrArgGluArg AsnProAlaAspArgGlyAspAsnPheAsnArgTyrGlyLeuArgPheAlaTrpGlyGlnGluTrpGlyGlySerGlyLeuSerSerLeuLeuArgLeuGlyAlaAlaLysArgHisTyrGluLys ProGlyPhePheSerGlyPheLysGlyGluArgArgArgAspLysGluLeuAsnThrSerLeuSerLeuTrpHisArgAlaLeuHisPheLysGlyIleThrProArgLeuThrLeuSerHisArg GluThrArgSerAsnAspValPheAsnGluTyrGluLysAsnArgAlaPheValGluPheAsnLysThrPhe-490
Hydrophilic Regions - Hopp-Woods
(SEQ. ID. NO. 12038)
1-LeuIleMetValIlePheTyrPheCysGlyLysThrPheMetProAlaArgAsnArgTrpMetLeuLeuLeuProLeuLeuAlaSerAlaAlaTyrAlaGluGluThrProArgGluProAspLeu ArgSerArgProGluPheArgLeuHisGluAlaGluValLysProIleAspArgGluLysValProGlyGlnValArgGluLysGlyLysValLeuGlnIleAspGlyGluThrLeuLeuLysAsnPro GluLeuLeuSerArgAlaMetTyrSerAlaValValSerAsnAsnIleAlaGlyIleArgValIleLeuProIleTyrLeuGlnGlnAlaGlnGlnAspLysMetLeuAlaLeuTyrAlaGlnGlyIleLeu AlaGlnAlaAspGlyArgValLysGluAlaIleSerHisTyrArgGluLeuIleAlaAlaGlnProAspAlaProAlaValArgMetArgLeuAlaAlaAlaLeuPheGluAsnArgGlnAsnGluAla AlaAlaAspGlnPheAspArgLeuLysAlaGluAsnLeuProProGlnLeuMetGluGlnValGluLeuTyrArgLysAlaLeuArgGluArgAspAlaTrpLysValAsnGlyGlyPheSerVal ThrArgGluHisAsnIleAsnGlnAlaProLysArgGlnGlnTyrGlyLysTrpThrPheProLysGlnValAspGlyThrAlaValAsnTyrArgLeuGlyAlaGluLysLysTrpSerLeuLys AsnGlyTrpTyrThrThrAlaGlyGlyAspValSerGlyArgValTyrProGlyAsnLysLysPheAsnAspMetThrAlaGlyValSerGlyGlyIleGlyPheAlaAspArgArgLysAspAla GlyLeuAlaValPheHisGluArgArgThrTyrGlyAsnAspAlaTyrSerTyrThrAsnGlyAlaArgLeuTyrPheAsnArgTrpGlnThrProLysTrpGlnThrLeuSerSerAlaGluTrp GlyArgLeuLysAsnThrArgArgAlaArgSerAspAsnThrHisLeuGlnIleSerAsnSerLeuValPheTyrArgAsnAlaArgGlnTyrTrpMetGlyGlyLeuAspPheTyrArgGluArg AsnProAlaAspArgGlyAspAsnPheAsnArgTyrGlyLeuArgPheAlaTrpGlyGlnGluTrpGlyGlySerGlyLeuSerSerLeuLeuArgLeuGlyAlaAlaLysArgHisTyrGluLys ProGlyPhePheSerGlyPheLysGlyGluArgArgArgAspLysGluLeuAsnThrSerLeuSerLeuTrpHisArgAlaLeuHisPheLysGlyIleThrProArgLeuThrLeuSerHisArg GluThrArgSerAsnAspValPheAsnGluTyrGluLysAsnArgAlaPheValGluPheAsnLysThrPhe-490
770
AMPHI Regions - AMPHI
SEQ. ID. NO. 12039 1-MetAsnArgLeuLeuLeuLeuSerAlaAlaValLeuLeuThrAlaCysGlySerGlyGluThrAspLysIleGlyArgAlaSerThrValPheAsnIleLeu GlyLysAsnAspArgIleGluValGluGlyPheAspAspProAspValGlnGlyValAlaCysTyrIleSerTyrAlaLysLysGlyGlyLeuLysGluMetVal AsnLeuGluGluAspAlaSerAspAlaSerValSerCysValGlnThrAlaSerSerIleSerPheAspGluThrAlaValArgLysProLysGluValPheLysHis GlyAlaSerPheAlaPheLysSerArgGlnIleValArgTyrTyrAspProLysArgLysThrPheAlaTyrLeuValTyrSerAspLysIleIleGlnGlySerPro LysAsnSerLeuSerAlaValSerCysPheGlyGlyGlyIleProGlnThrAspGlyValGlnAlaAspThrSerGlyAsnLeuLeuAlaGlyAlaCysMetIle SerAsnProIleGluAsnLeuAspLysArg-186
Antigenic Index - Jameson-Wolf
(SEQ. ID. NO. 12039)
1-MetAsnArgLeuLeuLeuLeuSerAlaAlaValLeuLeuThrAlaCysGlySerGlyGluThrAspLysIleGlyArgAlaSerThrValPheAsnIleLeuGlyLysAsnAspArgIleGluVal GluGlyPheAspAspProAspValGlnGlyValAlaCysTyrIleSerTyrAlaLysLysGlyGlyLeuLysGluMetValAsnLeuGluGluAspAlaSerAspAlaSerValSerCysValGlnThr AlaSerSerIleSerPheAspGluThrAlaValArgLysProLysGluValPheLysHisGlyAlaSerPheAlaPheLysSerArgGlnIleValArgTyrTyrAspProLysArgLysThrPheAlaTyr LeuValTyrSerAspLysIleIleGlnGlySerProLysAsnSerLeuSerAlaValSerCysPheGlyGlyGlyIleProGlnThrAspGlyValGlnAlaAspThrSerGlyAsnLeuLeuAlaGly AlaCysMetIleSerAsnProIleGluAsnLeuAspLysArg-186
Hydrophilic Regions - Hopp-Woods
(SEQ. ID. NO. 12039)
1-MetAsnArgLeuLeuLeuLeuSerAlaAlaValLeuLeuThrAlaCysGlySerGlyGluThrAspLysIleGlyArgAlaSerThrValPheAsnIleLeuGlyLysAsnAspArgIleGluVal GluGlyPheAspAspProAspValGlnGlyValAlaCysTyrIleSerTyrAlaLysLysGlyGlyLeuLysGluMetValAsnLeuGluGluAspAlaSerAspAlaSerValSerCysValGlnThr AlaSerSerIleSerPheAspGluThrAlaValArgLysProLysGluValPheLysHisGlyAlaSerPheAlaPheLysSerArgGlnIleValArgTyrTyrAspProLysArgLysThrPheAlaTyr LeuValTyrSerAspLysIleIleGlnGlySerProLysAsnSerLeuSerAlaValSerCysPheGlyGlyGlyIleProGlnThrAspGlyValGlnAlaAspThrSerGlyAsnLeuLeuAlaGly AlaCysMetIleSerAsnProIleGluAsnLeuAspLysArg-186
771
AMPHI Regions - AMPHI
SEQ. ID. NO. 12040 1-MetAspLeuLeuSerValPheHisLysTyrArgLeuLysTyrAlaValAlaValLeuThrIleLeuLeuLeuAlaAlaValGlyLeuHisAlaSerValTyrArg ThrPheThrProGluAsnIleArgSerArgLeuGlnGlnSerIleAlaHisThrHisArgLysIleSerPheAspAlaAspIleGlnArgArgLeuLeuProArgPro ThrValIleLeuLysAsnLeuThrIleThrGluProGlyGlyAspGlnThrAlaValSerValGlnGluThrLysIleGlyLeuSerTrpLysAsnLeuTrpSerAsp GlnIleGlnIleGluLysTrpValValSerSerAlaGluLeuAlaLeuThrArgAspGlyLysGlyValTrpAsnIleGlnAspLeuIleAspSerGlnLysArgGln AlaSerValAsnArgIleIleValGluAsnSerThrValArgLeuAsnPheLeuGlnGluGlnLeuIleLeuLysGluIleAsnLeuAsnLeuGlnSerProAspSer TABLE 1-continued SerGlyGlnProPheGluSerSerGlyIleLeuValTrpGlyLysLeuSerValProTrpLysSerArgGlyLeuPheLeuSerAsnGlyIleGlyProProGluIle
SerProPheHisPheGluAlaSerThrSerLeuAspGlyHisGlyIleThrIleSerThrThrGlySerProSerValArgPheAsnAlaGlyGlyAlaAspAlaAla
GlyLeuGlyLeuArgAlaAspThrSerPheArgAsnLeuHisLeuThrAlaGlnIleProAlaLeuAlaLeuArgAsnAsnSerIleLysIleGluThrValAsn
GlyAlaPheThrAlaGlyGlyGluTyrAlaArgTrpAspGlySerPheLysLeuAspLysAlaAsnLeuHisSerGlyIleAlaAsnIleGlyAsnAlaGluIle
SerGlySerPheLysThrProArgHisGlnThrAsnPheSerLeuAsnSerProLeuValTrpThrGluAsnLysGlyLeuAspAlaProArgLeuTyrValSer
ThrLeuGlnAspThrValAsnArgLeuProGlnProArgPheIleSerArgLeuAspGlySerLeuSerValProAsnLeuGlnAsnTrpAsnAlaGluLeuAsn
GlyThrPheAspArgGlnThrValAlaAlaLysPheArgTyrThrHisGluAspAlaProHisLeuGluAlaAlaValAlaLeuGlnLysLeuAsnLeuThrPro
TyrLeuAspAspValArgGlnGlnAsnGlyLysIlePheProAspThrLeuAlaLysLeuSerGlyAspIleGluAlaHisLeuLysIleGlyLysValGlnLeu
ProGlyLeuGlnLeuAspAspMetGluThrTyrLeuHisAlaAspLysGlyHisIleAlaLeuSerArgPheLysSerGlyLeuTyrGlyGlyHisThrGluGly
GlyIleSerIleAlaAsnThrArgProAlaThrTyrArgLeuGlnGlnAsnAlaSerAsnIleGlnIleGlnProLeuLeuGlnAspLeuPheGlyPheHisSerPhe
SerGlyAsnGlyAspAlaValIleAspLeuThrAlaGlyGlyGluThrArgLysGluLeuIleArgSerLeuGlnGlySerLeuSerLeuAsnIleSerAsnGly
AlaTrpHisGlyIleAspMetAspAsnIleLeuLysAsnGlyIleSerGlyLysThrAlaAspAsnAlaAlaProSerThrProPheHisArgPheThrLeuAsn
SerGluIleSerAspGlyIleSerArgHisIleAspThrGluLeuPheSerAspSerLeuTyrValThrSerAsnGlyTyrThrAsnLeuAspThrGlnGluLeuSer
GluAspValLeuIleArgAsnAlaValHisProLysAsnLysProIleProLeuLysIleThrGlyThrValAspLysProSerIleThrValAspTyrGlyArgLeu
ThrGlyGlyIleAsnSerArgLysGluLysGlnLysIleLeuGluAspThrLeuLeuGluGlnTrpGlnTrpLeuLysProLysGluProAla-705

Antigenic Index - Jameson-Wolf
(SEQ. ID. NO. 12040)
1-MetAspLeuLeuSerValPheHisLysTyrArgLeuLysTyrAlaValAlaValLeuThrIleLeuLeuLeuAlaAlaValGlyLeuHisAlaSerValTyrArgThrPheThrProGluAsnIle
ArgSerArgLeuGlnGlnSerIleAlaHisThrHisArgLysIleSerPheAspAlaAspIleGlnArgArgLeuLeuProArgProThrValIleLeuLysAsnLeuThrIleThrGluProGlyGly
AspGlnThrAlaValSerValGlnGluThrLysIleGlyLeuSerTrpLysAsnLeuTrpSerAspGlnIleGlnIleGluLysTrpValValSerSerAlaGluLeuAlaLeuThrArgAspGlyLys
GlyValTrpAsnIleGlnAspLeuIleAspSerGlnLysArgGlnAlaSerValAsnArgIleIleValGluAsnSerThrValArgLeuAsnPheLeuGlnGluGlnLeuIleLeuLysGluIleAsn
LeuAsnLeuGlnSerProAspSerSerGlyGlnProPheGluSerSerGlyIleLeuValTrpGlyLysLeuSerValProTrpLysSerArgGlyLeuPheLeuSerAsnGlyIleGlyProProGluIle
SerProPheHisPheGluAlaSerThrSerLeuAspGlyHisGlyIleThrIleSerThrThrGlySerProSerValArgPheAsnAlaGlyGlyAlaAspAlaAlaGlyLeuGlyLeuArgAlaAsp
ThrSerPheArgAsnLeuHisLeuThrAlaGlnIleProAlaLeuAlaLeuArgAsnAsnSerIleLysIleGluThrValAsnGlyAlaPheThrAlaGlyGlyGluTyrAlaArgTrpAspGlySer
PheLysLeuAspLysAlaAsnLeuHisSerGlyIleAlaAsnIleGlyAsnAlaGlyIleSerGlySerPheLysThrProArgHisGlnThrAsnPheSerLeuAsnSerProLeuValTrpThrGlu
AsnLysGlyLeuAspAlaProArgLeuTyrValSerThrLeuGlnAspThrValAsnArgLeuProGlnProArgPheIleSerArgLeuAspGlySerLeuSerValProAsnLeuGlnAsnTrp
AsnAlaGluLeuAsnGlyThrPheAspArgGlnThrValAlaAlaLysPheArgTyrThrHisGluAspAlaProHisLeuGluAlaAlaValAlaLeuGlnLysLeuAsnLeuThrProTyrLeu
AspAspValArgGlnGlnAsnGlyLysIlePheProAspThrLeuAlaLysLeuSerGlyAspIleGluAlaHisLeuLysIleGlyLysValGlnLeuProGlyLeuGlnLeuAspAspMetGlu
ThrTyrLeuHisAlaAspLysGlyHisIleAlaLeuSerArgPheLysSerGlyLeuTyrGlyGlyHisThrGluGlyGlyIleSerIleAlaAsnThrArgProAlaThrTyrArgLeuGlnGlnAsn
AlaSerAsnIleGlnIleGlnProLeuLeuGlnAspLeuPheGlyPheHisSerPheSerGlyAsnGlyAspAlaValIleAspLeuThrAlaGlyGlyGluThrArgLysGluLeuIleArgSerLeu
GlnGlySerLeuSerLeuAsnIleSerAsnGlyAlaTrpHisGlyIleAspMetAspAsnIleLeuLysAsnGlyIleSerGlyLysThrAlaAspAsnAlaAlaProSerThrProPheHisArgPhe
ThrLeuAsnSerGluIleSerAspGlyIleSerArgHisIleAspThrGluLeuPheSerAspSerLeuTyrValThrSerAsnGlyTyrThrAsnLeuAspThrGlnGluLeuSerGluAspValLeu
IleArgAsnAlaValHisProLysAsnLysProIleProLeuLysIleThrGlyThrValAspLysProSerIleThrValAspTyrGlyArgLeuThrGlyGlyIleAsnSerArgLysGluLysGln
LysIleLeuGluAspThrLeuLeuGluGlnTrpGlnTrpLeuLysProLysGluProAla-705

Hydrophilic Regions - Hopp-Woods
(SEQ. ID. NO. 12040)
1-MetAspLeuLeuSerValPheHisLysTyrArgLeuLysTyrAlaValAlaValLeuThrIleLeuLeuLeuAlaAlaValGlyLeuHisAlaSerValTyrArgThrPheThrProGluAsnIle
ArgSerArgLeuGlnGlnSerIleAlaHisThrHisArgLysIleSerPheAspAlaAspIleGlnArgArgLeuLeuProArgProThrValIleLeuLysAsnLeuThrIleThrGluProGlyGly
AspGlnThrAlaValSerValGlnGluThrLysIleGlyLeuSerTrpLysAsnLeuTrpSerAspGlnIleGlnIleGluLysTrpValValSerSerAlaGluLeuAlaLeuThrArgAspGlyLys
GlyValTrpAsnIleGlnAspLeuIleAspSerGlnLysArgGlnAlaSerValAsnArgIleIleValGluAsnSerThrValArgLeuAsnPheLeuGlnGluGlnLeuIleLeuLysGluIleAsn
LeuAsnLeuGlnSerProAspSerSerGlyGlnProPheGluSerSerGlyIleLeuValTrpGlyLysLeuSerValProTrpLysSerArgGlyLeuPheLeuSerAsnGlyIleGlyProProGlu
IleSerProPheHisPheGluAlaSerThrSerLeuAspGlyHisGlyIleThrIleSerThrThrGlySerProSerValArgPheAsnAlaGlyGlyAlaAspAlaAlaGlyLeuGlyLeuArgAla
AspThrSerPheArgAsnLeuHisLeuThrAlaGlnIleProAlaLeuAlaLeuArgAsnAsnSerIleLysIleGluThrValAsnGlyAlaPheThrAlaGlyGlyGluTyrAlaArgTrpAspGly
SerPheLysLeuAspLysAlaAsnLeuHisSerGlyIleAlaAsnIleGlyAsnAlaGluIleSerGlySerPheLysThrProArgHisGlnThrAsnPheSerLeuAsnSerProLeuValTrpThr
GluAsnLysGlyLeuAspAlaProArgLeuTyrValSerThrLeuGlnAspThrValAsnArgLeuProGlnProArgPheIleSerArgLeuAspGlySerLeuSerValProAsnLeuGlnAsn
TrpAsnAlaGluLeuAsnGlyThrPheAspArgGlnThrValAlaAlaLysPheArgTyrThrHisGluAspAlaProHisLeuGluAlaAlaValAlaLeuGlnLysLeuAsnLeuThrProTyr
LeuAspAspValArgGlnGlnAsnGlyLysIlePheProAspThrLeuAlaLysLeuSerGlyAspIleGluAlaHisLeuLysIleGlyLysValGlnLeuProGlyLeuGlnLeuAspAspMet
GluThrTyrLeuHisAlaAspLysGlyHisIleAlaLeuSerArgPheLysSerGlyLeuTyrGlyGlyHisThrGluGlyGlyIleSerIleAlaAsnThrArgProAlaThrTyrArgLeuGlnGln
AsnAlaSerAsnIleGlnIleGlnProLeuLeuGlnAspLeuPheGlyPheHisSerPheSerGlyAsnGlyAspAlaValIleAspLeuThrAlaGlyGlyGluThrArgLysGluLeuIleArgSer
LeuGlnGlySerLeuSerLeuAsnIleSerAsnGlyAlaTrpHisGlyIleAspMetAspAsnIleLeuLysAsnGlyIleSerGlyLysThrAlaAspAsnAlaAlaProSerThrProPheHisArg
PheThrLeuAsnSerGluIleSerAspGlyIleSerArgHisIleAspThrGluLeuPheSerAspSerLeuTyrValThrSerAsnGlyTyrThrAsnLeuAspThrGlnGluLeuSerGluAspVal
LeuIleArgAsnAlaValHisProLysAsnLysProIleProLeuLysIleThrGlyThrValAspLysProSerIleThrValAspTyrGlyArgLeuThrGlyGlyIleAsnSerArgLysGluLys
GlnLysIleLeuGluAspThrLeuLeuGluGlnTrpGlnTrpLeuLysProLysGluProAla-705

772

AMPHI Regions - AMPHI

SEQ. ID. NO. 12041 1-MetPheGlyAlaValLeuArgIleAspAlaAspCysLeuGlnIleIleValAlaCysLysLeuPheGlnIleValAlaTyrGlyPheAlaAlaLeuValGluGly
GluPheHisGluPheGlyLysMetLeuGluIleValArgLeuAlaAspAlaValPheHisArgAsnHisThrAspAspGlyGlyIleHisPheArgArgArgVal
GluArgPheGlyArgTyrValAsnGlnHisPheHisIleGluLysIleLeuGlnHisHisAlaGlnAlaAlaValValValAlaPheArgArgGlyAsnHisThr
LeuAspHisPhePheLeuGlnHisLysValHisIleAspAspIleValArgHisLeuArgGlnLeuGluGlnLysArgCysGlyAsnValValArgGluValAla
AspAspPheLeuPheAlaCysAspAlaValGluIleLysLeuGlnTyrIleAlaPheValAsnHisGlnPheIleArgLysArgGlnArgPheGlnThrAlaTyr
AspValAlaValAspPheAspAsnValGlnAlaValGlnLeuPheArgGlnArgPheGlyAsnArgArgGlnThrArgAlaAspPheAsnHisAspIleIleArg
LeuArgAlaHisGlyValAspAsnIleAlaAspAsnProArgValLeuGlnLysIleLeuProGluThrLeuAlaGlyPheValPhePheHisArgValSerPhe
SerValGluThrProProPheArgAlaValGluSerAspSerIleTrpGluGlyArgAsnSerPheGlnIleArgMetAlaHisArgAlaValLeuTyrValSerSer
CysValLeuLysHisLysCysValTyrSerIleArgLeuMetSerAlaLeu-298

Antigenic Index - Jameson-Wolf
(SEQ. ID. NO. 12041)
1-MetPheGlyAlaValLeuArgIleAspAlaAspCysLeuGlnIleIleValAlaCysLysLeuPheGlnIleValAlaTyrGlyPheAlaAlaLeuValGluGlyGluPheHisGluPheGlyLysMet
LeuGluIleValArgLeuAlaAspAlaValPheHisArgAsnHisThrAspAspGlyGlyIleHisPheArgArgArgValGluArgPheGlyArgTyrValAsnGlnHisPheHisIleGluLysIle
LeuGlnHisHisAlaGlnAlaAlaValValValAlaPheArgArgGlyAsnHisThrLeuAspHisPhePheLeuGlnHisLysValHisIleAspAspIleValArgHisLeuArgGlnLeuGluGln
LysArgCysGlyAsnValValArgGluValAlaAspAspPheLeuPheAlaCysAspAlaValGluIleLysLeuGlnTyrIleAlaPheValAsnHisGlnPheIleArgLysArgGlnArgPheGln
ThrAlaTyrAspValAlaValAspPheAspAsnValGlnAlaValGlnLeuPheArgGlnArgPheGlyAsnArgArgGlnThrArgAlaAspPheAsnHisAspIleIleArgLeuArgAlaHis
GlyValAspAsnIleAlaAspAsnProArgValLeuGlnLysIleLeuProGluThrLeuAlaGlyPheValPhePheHisArgValSerPheSerValGluThrProProPheArgAlaValGluSer
AspSerIleTrpGluGlyArgAsnSerPheGlnIleArgMetAlaHisArgAlaValLeuTyrValSerSerCysValLeuLysHisLysCysValTyrSerIleArgLeuMetSerAlaLeu-298

Hydrophilic Regions - Hopp-Woods
(SEQ. ID. NO. 12041)
1-MetPheGlyAlaValLeuArgIleAspAlaAspCysLeuGlnIleIleValAlaCysLysLeuPheGlnIleValAlaTyrGlyPheAlaAlaLeuValGluGlyGluPheHisGluPheGlyLysMet
LeuGluIleValArgLeuAlaAspAlaValPheHisArgAsnHisThrAspAspGlyGlyIleHisPheArgArgArgValGluArgPheGlyArgTyrValAsnGlnHisPheHisIleGluLysIle
LeuGlnHisHisAlaGlnAlaAlaValValValAlaPheArgArgGlyAsnHisThrLeuAspHisPhePheLeuGlnHisLysValHisIleAspAspIleValArgHisLeuArgGlnLeuGluGln
LysArgCysGlyAsnValValArgGluValAlaAspAspPheLeuPheAlaCysAspAlaValGluIleLysLeuGlnTyrIleAlaPheValAsnHisGlnPheIleArgLysArgGlnArgPheGln
ThrAlaTyrAspValAlaValAspPheAspAsnValGlnAlaValGlnLeuPheArgGlnArgPheGlyAsnArgArgGlnThrArgAlaAspPheAsnHisAspIleIleArgLeuArgAlaHis TABLE 1-continued GlyValAspAsnIleAlaAspAsnProArgValLeuGlnLysIleLeuProGluThrLeuAlaGlyPheValPhePheHisArgValSerPheSerValGluThrProProPheArgAlaValGluSer AspSerIleTrpGluGlyArgAsnSerPheGlnIleArgMetAlaHisArgAlaValLeuTyrValSerSerCysValLeuLysHisLysCysValTyrSerIleArgLeuMetSerAlaLeu-298

773

AMPHI Regions - AMPHI

SEQ. ID. NO. 12042 1-MetGlyLeuGlyAlaThrThrPheValGlySerGlyAlaIleGlyGlyGlyLeuCysSerThrGlyIleGlyCysAlaAlaGlyGlyLeuIleAlaThrAlaGly MetThrGlyGlyTyrThrGlnAlaSerGluGlySerArgGlnLeuPheGlyThrTyrGlnSerAspPheGlyLysLysValValLeuSerLeuGlyThrProIle GluTyrGluSerProLeuValSerAspAlaLysAsnLeuAlaValTrpGlyLeuGluThrLeuIleThrArgLysLeuGlyAsnLeuAlaThrGlyValLysThr SerLeuThrProLysThrAlaAspValGlnArgAsnIleLeuSerGlnSerGluValGlyIleLysTrpGlyLysGlyIleGluGlyGlnGlyMetProTrpGluAsp TyrValGlyLysGlyLeuSerAlaAsnAlaArgLeuProLysAsnPheLysThrPheAspTyrPheAspArgGlyThrGlyThrAlaIleSerAlaLysThrLeu AspThrGlnThrThrAlaArgLeuSerLysProGluGlnLeuTyrSerThrMetLysGlyTyrIleAspLysThrAlaAsnPheLysSerTyrGluLeuSerGlu ValProLeuArgAlaAspMetIleLysGlnArgGluIleHisLeuAlaIleProAlaGlnThrAsnLysGluGlnArgLeuGlnLeuGlnArgValValGluTyr GlyLysSerGlnAsnIleThrValLysIleThrGluIleGlu-260

Antigenic Index - Jameson-Wolf (SEQ. ID. NO. 12042)

1-MetGlyLeuGlyAlaThrThrPheValGlySerGlyAlaIleGlyGlyGlyLeuCysSerThrGlyIleGlyCysAlaAlaGlyGlyLeuIleAlaThrAlaGlyMetThrGlyGlyTyrThrGln AlaSerGluGlySerArgGlnLeuPheGlyThrTyrGlnSerAspPheGlyLysLysValValLeuSerLeuGlyThrProIleGluTyrGluSerProLeuValSerAspAlaLysAsnLeuAlaVal TrpGlyLeuGluThrLeuIleThrArgLysLeuGlyAsnLeuAlaThrGlyValLysThrSerLeuThrProLysThrAlaAspValGlnArgAsnIleLeuSerGlnSerGluValGlyIleLysTrp GlyLysGlyIleGluGlyGlnGlyMetProTrpGluAspTyrValGlyLysGlyLeuSerAlaAsnAlaArgLeuProLysAsnPheLysThrPheAspTyrPheAspArgGlyThrGlyThrAlaIle SerAlaLysThrLeuAspThrGlnThrThrAlaArgLeuSerLysProGluGlnLeuTyrSerThrMetLysGlyTyrIleAspLysThrAlaAsnPheLysSerTyrGluLeuSerGluValProLeu ArgAlaAspMetIleLysGlnArgGluIleHisLeuAlaIleProAlaGlnThrAsnLysGluGlnArgLeuGlnLeuGlnArgValValGluTyrGlyLysSerGlnAsnIleThrValLysIleThr GluIleGlu-260

Hydrophilic Regions - Hopp-Woods (SEQ. ID. NO. 12042)

1-MetGlyLeuGlyAlaThrThrPheValGlySerGlyAlaIleGlyGlyGlyLeuCysSerThrGlyIleGlyCysAlaAlaGlyGlyLeuIleAlaThrAlaGlyMetThrGlyGlyTyrThrGln AlaSerGluGlySerArgGlnLeuPheGlyThrTyrGlnSerAspPheGlyLysLysValValLeuSerLeuGlyThrProIleGluTyrGluSerProLeuValSerAspAlaLysAsnLeuAla ValTrpGlyLeuGluThrLeuIleThrArgLysLeuGlyAsnLeuAlaThrGlyValLysThrSerLeuThrProLysThrAlaAspValGlnArgAsnIleLeuSerGlnSerGluValGlyIleLys TrpGlyLysGlyIleGluGlyGlnGlyMetProTrpGluAspTyrValGlyLysGlyLeuSerAlaAsnAlaArgLeuProLysAsnPheLysThrPheAspTyrPheAspArgGlyThrGlyThr AlaIleSerAlaLysThrLeuAspThrGlnThrThrAlaArgLeuSerLysProGluGlnLeuTyrSerThrMetLysGlyTyrIleAspLysThrAlaAsnPheLysSerTyrGluLeuSerGluVal ProLeuArgAlaAspMetIleLysGlnArgGluIleHisLeuAlaIleProAlaGlnThrAsnLysGluGlnArgLeuGlnLeuGlnArgValValGluTyrGlyLysSerGlnAsnIleThrValLysIle ThrGluIleGlu-260

774

AMPHI Regions - AMPHI

SEQ. ID. NO. 12043 1-MetLysIleLysLeuProLeuPheIleIleTrpLeuSerValSerAlaSerCysAlaSerValSerProValProAlaGlySerGlnThrGluMetSerThrArg GluAsnAlaSerAspGlyIleProTyrProValProThrLeuGlnAspArgLeuAspTyrLeuGluGlyLysIleValArgLeuSerAsnGluValGluThrLeu AsnGlyLysValLysAlaLeuGluHisAlaLysThrHisSerSerGlyArgAlaTyrValGlnLysLeuAspAspArgLysLeuLysGluHisTyrLeuAsn ThrGluGlyGlySerAlaSerAlaHisThrValGluThrAlaGlnAsnLeuTyrAsnGlnAlaLeuLysHisTyrLysSerGlyLysPheSerAlaAlaAlaSer LeuLeuLysGlyAlaAspGlyGlyAspGlyGlySerIleAlaGlnArgSerMetTyrLeuLeuLeuGlnSerArgAlaArgMetGlyAsnCysGluSerValIle GluIleGlyGlyArgTyrAlaAsnArgPheLysAspSerProThrAlaProGluAlaMetPheLysIleGlyGluCysGlnTyrArgLeuGlnGlnLysAspIle AlaArgAlaThrTrpArgSerLeuIleGlnThrTyrProGlySerProAlaAlaLysArgAlaAlaAlaAlaValArgLysArg-237

Antigenic Index - Jameson-Wolf (SEQ. ID. NO. 12043)

1-MetLysIleLysLeuProLeuPheIleIleTrpLeuSerValSerAlaSerCysAlaSerValSerProValProAlaGlySerGlnThrGluMetSerThrArgGluAsnAlaSerAspGlyIleProTyr ProValProThrLeuGlnAspArgLeuAspTyrLeuGluGlyLysIleValArgLeuSerAsnGluValGluThrLeuAsnGlyLysValLysAlaLeuGluHisAlaLysThrHisSerSerGlyArg AlaTyrValGlnLysLeuAspAspArgLysLeuLysGluHisTyrLeuAsnThrGluGlyGlySerAlaSerAlaHisThrValGluThrAlaGlnAsnLeuTyrAsnGlnAlaLeuLysHisTyr LysSerGlyLysPheSerAlaAlaAlaSerLeuLeuLysGlyAlaAspGlyGlyAspGlyGlySerIleAlaGlnArgSerMetTyrLeuLeuLeuGlnSerArgAlaArgMetGlyAsnCysGlu SerValIleGluIleGlyGlyArgTyrAlaAsnArgPheLysAspSerProThrAlaProGluAlaMetPheLysIleGlyGluCysGlnTyrArgLeuGlnGlnLysAspIleAlaArgAlaThrTrp ArgSerLeuIleGlnThrTyrProGlySerProAlaAlaLysArgAlaAlaAlaAlaValArgLysArg-237

Hydrophilic Regions - Hopp-Woods (SEQ. ID. NO. 12043)

1-MetLysIleLysLeuProLeuPheIleIleTrpLeuSerValSerAlaSerCysAlaSerValSerProValProAlaGlySerGlnThrGluMetSerThrArgGluAsnAlaSerAspGlyIleProTyr ProValProThrLeuGlnAspArgLeuAspTyrLeuGluGlyLysIleValArgLeuSerAsnGluValGluThrLeuAsnGlyLysValLysAlaLeuGluHisAlaLysThrHisSerSerGlyArg AlaTyrValGlnLysLeuAspAspArgLysLeuLysGluHisTyrLeuAsnThrGluGlyGlySerAlaSerAlaHisThrValGluThrAlaGlnAsnLeuTyrAsnGlnAlaLeuLysHisTyr LysSerGlyLysPheSerAlaAlaAlaSerLeuLeuLysGlyAlaAspGlyGlyAspGlyGlySerIleAlaGlnArgSerMetTyrLeuLeuLeuGlnSerArgAlaArgMetGlyAsnCysGlu SerValIleGluIleGlyGlyArgTyrAlaAsnArgPheLysAspSerProThrAlaProGluAlaMetPheLysIleGlyGluCysGlnTyrArgLeuGlnGlnLysAspIleAlaArgAlaThrTrp ArgSerLeuIleGlnThrTyrProGlySerProAlaAlaLysArgAlaAlaAlaAlaValArgLysArg-237

790

AMPHI Regions - AMPHI

SEQ. ID. NO. 12044 10-GluAlaAlaAlaGluVal-15
SEQ. ID. NO. 12045 44-GlyAsnGlnThrCysSerArgTyrSerAsn-53
SEQ. ID. NO. 12046 89-LysGlnAlaValThr-93
SEQ. ID. NO. 12047 103-ThrGlnAlaTyrAsnGluMetThrLysSerVal-113
SEQ. ID. NO. 12048 166-PheAlaArgThrGlyLysLeu-172
SEQ. ID. NO. 12049 174-GlySerPheAspLeuPheAlaSerVal-182
SEQ. ID. NO. 12050 253-ProSerGluAlaPheAspLeuProGluGlySerThr-264
SEQ. ID. NO. 12051 320-PheLeuArgPheTrpGlnAlaThrArgGlyIle-330

Antigenic Index - Jameson-Wolf

SEQ. ID. NO. 12052 1-MetAlaArgArgSerLysThrPheGluGluAlaAlaAlaGluValGluGluArgPheGlyHisArgGlyIleLys-25
SEQ. ID. NO. 12053 30-GluGlyThrAlaLysProCysVal-37
SEQ. ID. NO. 12054 39-AsnCysProLysHisGlyAsnGlnThrCysSerArgTyrSer-52
SEQ. ID. NO. 12055 57-GlySerSerTrpGlyCysProSerCysGlyAsnGluGlnAlaAla-71
SEQ. ID. NO. 12056 77-ThrLeuArgLysAsnHisIle-83
SEQ. ID. NO. 12057 95-MetThrLysGlnGluArgIleThr-102
SEQ. ID. NO. 12058 123-AspValGlnGlyAspThrThrIle-130
SEQ. ID. NO. 12059 134-HisThrHisThrHisAsnHisSerAspAlaAspGlyLysAlaLeuSer-149
SEQ. ID. NO. 12060 152-LeuThrProArgProLeuLeuSerAspArgGlnAla-163
SEQ. ID. NO. 12061 167-AlaArgThrGlyLysLeuThrGly-174
SEQ. ID. NO. 12062 194-MetProAspThrSerMet-199
SEQ. ID. NO. 12063 201-ProValIleGluLysGlyAsp-207
SEQ. ID. NO. 12064 213-ProArgMetCysProAlaAspGluAspIleAla-223
SEQ. ID. NO. 12065 226-GluLeuSerAspLysArgLeuVal-233

TABLE 1-continued

| | |
|---|---|
| SEQ. ID. NO. 12066 | 248-TyrGlnThrGlyArgProSerGluAlaPheAspLeuProGluGlySerThr-264 |
| SEQ. ID. NO. 12067 | 270-LeuGluSerLysAsnGlyLeuCysProProHisArgGlnGluGlyVal-285 |
| SEQ. ID. NO. 12068 | 301-SerAlaSerLysThrSerCysThrArgProThrAlaAlaArgLysSerAla-317 |
| SEQ. ID. NO. 12069 | 326-AlaThrArgGlyIleProLysThrArgSerTrpArgAsnProAsnAsnAla-342 |
| Hydrophilic Regions - Hopp-Woods | |
| SEQ. ID. NO. 12070 | 1-MetAlaArgArgSerLysThrPheGluGluAlaAlaAlaGluValGluGluArgPheGlyHisArgGlyIleLys-25 |
| SEQ. ID. NO. 12071 | 65-CysGlyAsnGluGlnAlaAla-71 |
| SEQ. ID. NO. 12072 | 77-ThrLeuArgLysAsnHisIle-83 |
| SEQ. ID. NO. 12073 | 96-ThrLysGlnGluArgIleThr-102 |
| SEQ. ID. NO. 12074 | 139-AsnHisSerAspAlaAspGlyLysAlaLeuSer-149 |
| SEQ. ID. NO. 12075 | 157-LeuLeuSerAspArgGlnAla-163 |
| SEQ. ID. NO. 12076 | 168-ArgThrGlyLysLeu-172 |
| SEQ. ID. NO. 12077 | 202-ValIleGluLysGlyAsp-207 |
| SEQ. ID. NO. 12078 | 213-ProArgMetCysProAlaAspGluAspIleAla-223 |
| SEQ. ID. NO. 12079 | 226-GluLeuSerAspLysArgLeuVal-233 |
| SEQ. ID. NO. 12080 | 251-GlyArgProSerGluAlaPheAspLeuProGlu-261 |
| SEQ. ID. NO. 12081 | 270-LeuGluSerLysAsnGlyLeu-276 |
| SEQ. ID. NO. 12082 | 280-HisArgGlnGluGlyVal-285 |
| SEQ. ID. NO. 12083 | 303-SerLysThrSerCysThrArgProThrAlaAlaArgLysSerAla-317 |
| SEQ. ID. NO. 12084 | 328-ArgGlyIleProLysThrArgSerTrpArgAsn-338 |
| 900-2 | |
| AMPHI Regions - AMPHI | |
| SEQ. ID. NO. 12085 | 9-ValValAlaPheAlaArgPhe-15 |
| SEQ. ID. NO. 12086 | 36-ValGlyLysHisPheArgLysPheHisArgPheArgArgArgGlyGlu-51 |
| SEQ. ID. NO. 12087 | 53-PheValAspPheLysGlnTrpAlaPheValGlyLeuPheArgLeuAlaArgLeuPheHisIleGlyAspAspPheValAspArgPheLeuGlyPhePhe-85 |
| SEQ. ID. NO. 12088 | 121-GlyGluGluPheProGluAlaValValGluAlaAlaGlyAspValAlaArgHisPheAspValLeuAspLeuVal-145 |
| SEQ. ID. NO. 12089 | 161-SerHisGlnAsnArgIle-166 |
| SEQ. ID. NO. 12090 | 198-HisGlnThrLeuGlySerAspAlaGly-206 |
| SEQ. ID. NO. 12091 | 210-ValGlnPheHisHisPheGly-216 |
| SEQ. ID. NO. 12092 | 233-GlyLysProSerGlyGlyAsnGlyLeuGlyGlyLeuValAsnHisLeuArgLeuValAla-252 |
| SEQ. ID. NO. 12093 | 268-IleGluValLeuArgArgAlaAspGlyGly-277 |
| SEQ. ID. NO. 12094 | 279-AspGlyAlaAspValValAlaGlnMet-287 |
| Antigenic Index - Jameson-Wolf | |
| SEQ. ID. NO. 12095 | 1-LeuArgArgValGlyGlyGln-7 |
| SEQ. ID. NO. 12096 | 19-GlyValAspPheArgArgGlnLysPhePheGlyPheThrProArgGlnAlaVal-36 |
| SEQ. ID. NO. 12097 | 38-LysHisPheArgLysPheHisArgPheArgArgArgGlyGluGly-52 |
| SEQ. ID. NO. 12098 | 74-GlyAspAspPheValAspArg-80 |
| SEQ. ID. NO. 12099 | 88-PheProLysArgAsnGlyValAla-95 |
| SEQ. ID. NO. 12100 | 103-SerValGlnThrAspGlnGluPhe-110 |
| SEQ. ID. NO. 12101 | 118-PheGlyGlnGlyGluGluPheProGlu-126 |
| SEQ. ID. NO. 12102 | 131-AlaAlaGlyAspValAlaArg-137 |
| SEQ. ID. NO. 12103 | 145-ValAlaProAspGly-149 |
| SEQ. ID. NO. 12104 | 157-GlnAsnIleGlySerHisGlnAsnArgIleThrGluGlnThrHisPhe-172 |
| SEQ. ID. NO. 12105 | 201-LeuGlySerAspAlaGlyGlnAsnProVal-210 |
| SEQ. ID. NO. 12106 | 230-GluSerAlaGlyLysProSerGlyGlyAsnGly-240 |
| SEQ. ID. NO. 12107 | 252-AlaPheAspAspThrValValIleGlyGluGluGluGluGlyPheGly-267 |
| SEQ. ID. NO. 12108 | 270-ValLeuArgArgAlaAspGlyGlyAlaAspGlyAlaAsp-282 |
| SEQ. ID. NO. 12109 | 285-AlaGlnMetArgAspAlaGlyGlyGlyTyrAlaGly-296 |
| SEQ. ID. NO. 12110 | 311-MetProSerGluArgGluLysAspValProIle-321 |
| SEQ. ID. NO. 12111 | 323-ProAspLeuProProThrSerSerArgGlnGlnThr-334 |
| Hydrophilic Regions - Hopp-Woods | |
| SEQ. ID. NO. 12112 | 1-LeuArgArgValGly-5 |
| SEQ. ID. NO. 12113 | 20-ValAspPheArgArgGlnLys-26 |
| SEQ. ID. NO. 12114 | 38-LysHisPheArgLysPheHisArgPheArgArgArgGlyGluGly-52 |
| SEQ. ID. NO. 12115 | 89-ProLysArgAsnGly-93 |
| SEQ. ID. NO. 12116 | 105-GlnThrAspGlnGluPhe-110 |
| SEQ. ID. NO. 12117 | 120-GlnGlyGluGluPhePro-125 |
| SEQ. ID. NO. 12118 | 131-AlaAlaGlyAspValAlaArg-137 |
| SEQ. ID. NO. 12119 | 162-HisGlnAsnArgIleThrGlu-168 |
| SEQ. ID. NO. 12120 | 201-LeuGlySerAspAlaGlyGln-207 |
| SEQ. ID. NO. 12121 | 231-SerAlaGlyLysProSerGly-237 |
| SEQ. ID. NO. 12122 | 257-ValValIleGlyGluGluGluGluGlyPheGly-267 |
| SEQ. ID. NO. 12123 | 270-ValLeuArgArgAlaAspGlyGlyAlaAspGlyAlaAsp-282 |
| SEQ. ID. NO. 12124 | 285-AlaGlnMetArgAspAlaGly-291 |
| SEQ. ID. NO. 12125 | 311-MetProSerGluArgGluLysAspValProIle-321 |
| SEQ. ID. NO. 12126 | 326-ProProThrSerSerArgGlnGln-333 |
| 901-2 | |
| AMPHI Regions - AMPHI | |
| SEQ. ID. NO. 12127 | 20-GlyLeuPheThrValLeuGly-26 |
| SEQ. ID. NO. 12128 | 55-ValSerLeuThrGluIlePheSerLysSer-64 |
| SEQ. ID. NO. 12129 | 66-GluAlaPheAlaGluIleTyrAsp-73 |
| SEQ. ID. NO. 12130 | 84-AlaPheLeuAlaGlyMetGlyGlyIleAlaLeuIle-95 |
| SEQ. ID. NO. 12131 | 97-ArgLeuValProAsnProHisGluThrLeuAsp-107 |
| SEQ. ID. NO. 12132 | 124-ValGlyMetMetAlaAlaPhe-130 |
| SEQ. ID. NO. 12133 | 136-AsnPheProGluGlyLeuAlaThrPhePheAlaThrLeuGlu-149 |
| SEQ. ID. NO. 12134 | 164-HisAsnIleProGluGlyIleSer-171 |

TABLE 1-continued

SEQ. ID. NO. 12135 190-CysLeuLeuSerGlyLeuAlaGluProLeuGlyAlaAla-202
SEQ. ID. NO. 12136 217-PheGlySerValPheGlyValIleAlaGlyValMet-228
SEQ. ID. NO. 12137 143-TyrSerAspGlyHisGlu-248
Antigenic Index - Jameson-Wolf
SEQ. ID. NO. 12138 1-MetProAspPheSerMet-6
SEQ. ID. NO. 12139 33-SerLysThrProAsnProArgVal-40
SEQ. ID. NO. 12140 61-PheSerLysSerSerGluAlaPhe-68
SEQ. ID. NO. 12141 71-IleTyrAspLysAspHisAla-77
SEQ. ID. NO. 12142 98-LeuValProAsnProHisGluThrLeuAspAlaGlnAspProSerPheGlnGluSerLysArgArgHisIleAla-122
SEQ. ID. NO. 12143 136-AsnPheProGluGly-140
SEQ. ID. NO. 12144 179-AlaThrArgSerArgLysLysThr-186
SEQ. ID. NO. 12145 193-SerGlyLeuAlaGluProLeuGly-200
SEQ. ID. NO. 12146 235-GluLeuLeuProAlaAlaLysArgTyrSerAspGlyHisGluThr-249
Hydrophilic Regions - Hopp-Woods
SEQ. ID. NO. 12147 61-PheSerLysSerSerGluAlaPhe-68
SEQ. ID. NO. 12148 71-IleTyrAspLysAspHisAla-77
SEQ. ID. NO. 12149 102-ProHisGluThrLeuAspAlaGlnAspProSerPheGlnGluSerLysArgArgHisIleAla-122
SEQ. ID. NO. 12150 180-ThrArgSerArgLysLysThr-186
SEQ. ID. NO. 12151 235-GluLeuLeuProAlaAlaLysArgTyrSerAspGlyHisGlu-248
902
AMPHI Regions - AMPHI
SEQ. ID. NO. 12152 1-LeuHisPheGlnArgIleIleLysCysSerGluGlyIleTrpAlaValGlyAlaArgProThrValGlyPhePheGlyLysSerPheLysIleThrCysLysHisVal ValLeuArgArgArgThrValGlnAlaValAspPheThrThrCysLeuPheAlaValGlyHisPheValAspValProAlaTyrValPheAlaCysAspAlaHis ThrGlyGlyValAlaValLysArgValTyrGlyAlaAspValValGlnAsnSerGlyGlyAlaPheCysGlnThrGlnGlyArgArgGlnAsnThrValPheGly IleMetPheGlnIleAlaGluGluProArgProAlaLeuArgAlaAlaProTyrHisAsnAlaValGlyGlyGlyLeuPheGluAspGlyLeuGlyPheLeuArg ArgSerAsnValAlaValAspProAspArgAspValGlnThrAlaPheGlyPheGlyAspGluPheValThrArgPheAlaPheValHisLeuArgThrArgAla SerValAspGlyLysGlyGlyAspAlaAlaIlePheGlyAspPheGlyAspAspGlyGlnValLeuMetValValValProThrGlnThrGlyPheGluGlyAsn GlyTyrAlaCysArgThrAspAspGlyPheGlnAsnGlyGlyAsnGlnArgLeuValLeuHisGlnArgAlaThrGlyLeuAspIleAlaAspPhePheSer GlyThrAlaHisValAspValAspLysLeuArgProLysAlaAspValValThrArgGlyIleArgHisLeuLeuArgIleAlaSerGlyAsnLeuHisGlyAsn AsnAlaAlaPheIleGlyLysIleAlaAlaValGlnGlyPheSerSerIleSerGluArgArgValAlaGlyGlnHisPheAlaHisArgProThrCysAlaLysIle SerAlaLysSerAlaGluArgPheValGlyAsnAlaArgHisArgArgLysCysAspGlyValValAspLysIleAlaAlaAspValHisAsnGlySerAlaPhe GlnLysSerThrProLeuTyrIlePhe-360
Antigenic Index - Jameson-Wolf
(SEQ. ID. NO. 12153)
1-LeuHisPheGlnArgIleIleLysCysSerGluGlyIleTrpAlaValGlyAlaArgProThrValGlyPhePheGlyLysSerPheLysIleThrCysLysHisValValLeuArgArgArgThrVal GlnAlaValAspPheThrThrCysLeuPheAlaValGlyHisPheValAspValProAlaTyrValPheAlaCysAspAlaHisThrGlyGlyValAlaValLysArgValTyrGlyAlaAspValVal GlnAsnSerGlyGlyAlaPheCysGlnThrGlnGlyArgArgGlnAsnThrValPheGlyIleMetPheGlnIleAlaGluGluProArgProAlaLeuArgAlaAlaProTyrHisAsnAlaValGly GlyGlyLeuPheGluAspGlyLeuGlyPheLeuArgArgSerAsnValAlaValAspProAspArgAspValGlnThrAlaPheGlyPheGlyAspGluPheValThrArgPheAlaPheValHis LeuArgThrArgAlaSerValAspGlyLysGlyGlyAspAlaAlaIlePheGlyAspPheGlyAspAspGlyGlnValLeuMetValValValProThrGlnThrGlyPheGluGlyAsnGlyTyr AlaCysArgThrAspAspGlyPheGlnAsnGlyGlyAsnGlnArgLeuValLeuHisGlnArgAlaThrGlyLeuAspIleAlaAspPhePheSerGlyThrAlaHisValAspValAspLysLeu ArgProLysAlaAspValValThrArgGlyIleArgHisLeuLeuArgIleAlaSerGlyAsnLeuHisGlyAsnAsnAlaAlaPheIleGlyLysIleAlaAlaValGlnGlyPheSerSerIleSerGlu ArgArgValAlaGlyGlnHisPheAlaHisArgProThrCysAlaLysIleSerAlaLysSerAlaGluArgPheValGlyAsnAlaArgHisArgArgLysCysAspGlyValValAspLysIleAla AlaAspValHisAsnGlySerAlaPheGlnLysSerThrProLeuTyrIlePhe-360
Hydrophilic Regions - Hopp-Woods
(SEQ. ID. NO. 12153)
1-LeuHisPheGlnArgIleIleLysCysSerGluGlyIleTrpAlaValGlyAlaArgProThrValGlyPhePheGlyLysSerPheLysIleThrCysLysHisValValLeuArgArgArgThrVal GlnAlaValAspPheThrThrCysLeuPheAlaValGlyHisPheValAspValProAlaTyrValPheAlaCysAspAlaHisThrGlyGlyValAlaValLysArgValTyrGlyAlaAspValVal GlnAsnSerGlyGlyAlaPheCysGlnThrGlnGlyArgArgGlnAsnThrValPheGlyIleMetPheGlnIleAlaGluGluProArgProAlaLeuArgAlaAlaProTyrHisAsnAlaValGly GlyGlyLeuPheGluAspGlyLeuGlyPheLeuArgArgSerAsnValAlaValAspProAspArgAspValGlnThrAlaPheGlyPheGlyAspGluPheValThrArgPheAlaPheValHis LeuArgThrArgAlaSerValAspGlyLysGlyGlyAspAlaAlaIlePheGlyAspPheGlyAspAspGlyGlnValLeuMetValValValProThrGlnThrGlyPheGluGlyAsnGlyTyr AlaCysArgThrAspAspGlyPheGlnAsnGlyGlyAsnGlnArgLeuValLeuHisGlnArgAlaThrGlyLeuAspIleAlaAspPhePheSerGlyThrAlaHisValAspValAspLysLeu ArgProLysAlaAspValValThrArgGlyIleArgHisLeuLeuArgIleAlaSerGlyAsnLeuHisGlyAsnAsnAlaAlaPheIleGlyLysIleAlaAlaValGlnGlyPheSerSerIleSerGlu ArgArgValAlaGlyGlnHisPheAlaHisArgProThrCysAlaLysIleSerAlaLysSerAlaGluArgPheValGlyAsnAlaArgHisArgArgLysCysAspGlyValValAspLysIleAla AlaAspValHisAsnGlySerAlaPheGlnLysSerThrProLeuTyrIlePhe-360
903-2
AMPHI Regions - AMPHI
SEQ. ID. NO. 12153 29-GluLeuIleArgSerMetGlnArgGln-37
SEQ. ID. NO. 12154 109-AsnLeuSerArgLeuGlnLysAla-116
SEQ. ID. NO. 12155 191-GluGlnGlyLeuGluAsnLeuArgArgLeuProSerVal-203
SEQ. ID. NO. 12156 240-GlyGlyLysThrThrGlyLysTyr-247
SEQ. ID. NO. 12157 262-SerAspLeuPheTyr-266
SEQ. ID. NO. 12158 315-ArgTyrHisGluAlaThrGlu-321
SEQ. ID. NO. 12159 360-ThrArgGlnThrTyrLysTyrIleAspAsp-369
SEQ. ID. NO. 12160 560-HisLysProLysGlyPheGlnThrThrAsnThr-570
Antigenic Index - Jameson-Wolf
SEQ. ID. NO. 12161 21-LeuAlaAlaAspGluAsnAspAlaGluLeuIleArgSerMetGlnArgGlnGlnHisIleAsp-41
SEQ. ID. NO. 12162 48-AlaAsnValArgPheGluGlnProLeuGluLysAsnAsnTyrValLeuSerGluAspGluThrProCysThrArg-72
SEQ. ID. NO. 12163 77-SerLeuAspAspLysThrValArg-84
SEQ. ID. NO. 12164 106-GlySerAsnAsnLeuSerArgLeuGlnLysAlaAla-117
SEQ. ID. NO. 12165 135-ProGlnAsnMetAspSerGlyIleLeu-143
SEQ. ID. NO. 12166 146-ArgValSerAlaGlyGluIleGlyAspIleArgTyrGluGluLysArgAspGlyLysSerAlaGluGlySerIle-170
SEQ. ID. NO. 12167 178-ProLeuTyrArgAsnLysIleLeuAsn-186
SEQ. ID. NO. 12168 188-ArgAspValGluGlnGlyLeuGluAsnLeuArgArgLeuProSerValLysThrAspIle-207
SEQ. ID. NO. 12169 210-IleProSerGluGluGluGlyLysSerAspLeu-220
SEQ. ID. NO. 12170 223-LysTrpGlnGlnAsnLysProIleArg-231
SEQ. ID. NO. 12171 234-IleGlyIleAspAspAlaGlyGlyLysThrThrGlyLysTyrGlnGly-249
SEQ. ID. NO. 12172 256-AspAsnProLeuGly-260
SEQ. ID. NO. 12173 269-TyrGlyArgGlyLeuAlaHisLysThrAspLeuThrAspAlaThrGlyThrGluThrGluSerGlySerArgSerTyr-294
SEQ. ID. NO. 12174 309-PheAsnHisAsnGlyHisArgTyrHisGluAlaThrGluGlyTyrSerValAsnTyrAspTyrAsnGlyLysGlnTyrGln-335
SEQ. ID. NO. 12175 343-MetLeuTrpArgAsnArgLeuHisLysThrSerVal-354

| | |
|---|---|
| SEQ. ID. NO. 12176 | 362-GlnThrTyrLysTyrIleAspAspAlaGluIleGluValGlnArgArgArgSerAlaGlyTrpGluAlaGluLeuArgHis-388 |
| SEQ. ID. NO. 12177 | 395-TrpGlnLeuAspGlyLysLeuSerTyrLysArgGlyThrGlyMetArgGlnSerMetProAlaProGluGluAsnGlyGlyAspIleLeuProGlyThrSerArgMetLysIle-432 |
| SEQ. ID. NO. 12178 | 459-GlnTrpAsnLysThrPro-464 |
| SEQ. ID. NO. 12179 | 467-AlaGlnAspLysLeuSerIleGlySerArgTyrThrValArgGlyPheAspGlyGluGlnSerLeuPheGlyGluArgGlyPheTyrTrpGlnAsnThr-499 |
| SEQ. ID. NO. 12180 | 514-AlaAspTyrGlyArgValSerGlyGluSerAla-524 |
| SEQ. ID. NO. 12181 | 527-ValSerGlyLysGln-531 |
| SEQ. ID. NO. 12182 | 539-PheArgGlyGlyHisLysValGly-546 |
| SEQ. ID. NO. 12183 | 557-LysProLeuHisLysProLysGlyPheGln-566 |
| Hydrophilic Regions - Hopp-Woods | |
| SEQ. ID. NO. 12184 | 21-LeuAlaAlaAspGluAsnAspAlaGluLeuIleArgSerMetGlnArgGlnGlnHisIleAsp-41 |
| SEQ. ID. NO. 12185 | 48-AlaAsnValArgPheGluGlnProLeuGluLysAsnAsn-60 |
| SEQ. ID. NO. 12186 | 63-LeuSerGluAspGluThrProCys-70 |
| SEQ. ID. NO. 12187 | 77-SerLeuAspAspLysThrValArg-84 |
| SEQ. ID. NO. 12188 | 109-AsnLeuSerArgLeuGlnLysAlaAla-117 |
| SEQ. ID. NO. 12189 | 151-GluIleGlyAspIleArgTyrGluGluLysArgAspGlyLysSerAlaGluGlySer-169 |
| SEQ. ID. NO. 12190 | 188-ArgAspValGluGlnGlyLeuGluAsnLeuArgArgLeuProSerValLysThrAspIle-207 |
| SEQ. ID. NO. 12191 | 211-ProSerGluGluGluGlyLysSerAspLeu-220 |
| SEQ. ID. NO. 12192 | 234-IleGlyIleAspAspAlaGlyGlyLysThrThrGlyLysTyr-247 |
| SEQ. ID. NO. 12193 | 273-LeuAlaHisLysThrAspLeuThrAsp-281 |
| SEQ. ID. NO. 12194 | 283-ThrGlyThrGluThrGluSerGlySerArgSer-293 |
| SEQ. ID. NO. 12195 | 315-ArgTyrHisGluAlaThrGlu-321 |
| SEQ. ID. NO. 12196 | 366-TyrIleAspAspAlaGluIleGluValGlnArgArgArgSerAlaGlyTrp-382 |
| SEQ. ID. NO. 12197 | 384-AlaGluLeuArgHis-388 |
| SEQ. ID. NO. 12198 | 399-GlyLysLeuSerTyrLysArgGlyThrGlyMetArgGlnSerMetProAlaProGluGluAsnGlyGly-421 |
| SEQ. ID. NO. 12199 | 428-SerArgMetLysIle-432 |
| SEQ. ID. NO. 12200 | 467-AlaGlnAspLysLeuSerIle-473 |
| SEQ. ID. NO. 12201 | 481-GlyPheAspGlyGluGln-486 |
| SEQ. ID. NO. 12202 | 515-AspTyrGlyArgValSerGlyGluSer-523 |
| SEQ. ID. NO. 12203 | 558-ProLeuHisLysProLysGly-564 |
| 904-2 | |
| AMPHI Regions - AMPHI | |
| SEQ. ID. NO. 12204 | 23-AspPhePheAsnProPheGlnIleCysPheGlyValPheGlyGlnCysAla-39 |
| SEQ. ID. NO. 12205 | 55-PheValAsnArgLeuAlaGlyPheHisArgIleGly-66 |
| SEQ. ID. NO. 12206 | 89-PheAsnAlaValHisTyrIleGluPhe-97 |
| SEQ. ID. NO. 12207 | 131-GluPheValSerAlaPheCysGlnThrTyr-140 |
| SEQ. ID. NO. 12208 | 164-AlaGlnAsnIleIleGlnHisLeuArgThrTyrAlaArgAlaCysArgSerCysAlaArgGln-184 |
| SEQ. ID. NO. 12209 | 193-IleSerAlaValValAspVal-199 |
| SEQ. ID. NO. 12210 | 202-ArgThrLeuArgAlaPhe-207 |
| SEQ. ID. NO. 12211 | 250-GlyIleValGlnMetLeu-255 |
| SEQ. ID. NO. 12212 | 267-GlnPhePheThrGlnPhePheArgMetGlnGlnIleGlyGlyAlaAsn-282 |
| SEQ. ID. NO. 12213 | 308-ArgCysPheAlaGlyLeuValGlu-315 |
| SEQ. ID. NO. 12214 | 332-ThrAlaPheAspValPheHisAlaCys-340 |
| SEQ. ID. NO. 12215 | 364-ValGlnThrPheMetGlnAspAla-371 |
| SEQ. ID. NO. 12216 | 390-ArgIleValAlaAlaLeu-395 |
| SEQ. ID. NO. 12217 | 402-GlyPhePheArgGlnProValAsn-409 |
| SEQ. ID. NO. 12218 | 418-ProLeuCysAlaAspTyrTyrAsnIlePheSerHis-429 |
| Antigenic Index - Jameson-Wolf | |
| SEQ. ID. NO. 12219 | 11-GlyAlaGlyGlyAspAspGlyAspArgArgAlaAlaAsp-23 |
| SEQ. ID. NO. 12220 | 66-GlyThrAlaArgGlnAspVal-72 |
| SEQ. ID. NO. 12221 | 84-AlaAspIleAspGly-88 |
| SEQ. ID. NO. 12222 | 98-SerAsnThrHisThrGlyAsn-104 |
| SEQ. ID. NO. 12223 | 106-ValAspLeuAspGly-110 |
| SEQ. ID. NO. 12224 | 114-GlyGlyGlyIleLys-118 |
| SEQ. ID. NO. 12225 | 126-SerGlyTyrArgThrGluPhe-132 |
| SEQ. ID. NO. 12226 | 147-PheGlyArgGluArgAlaArgThrAspAlaArgGlyIleGlyPheAspAspAlaGln-165 |
| SEQ. ID. NO. 12227 | 173-ThrTyrAlaArgAlaCysArgSerCysAlaArgGlnThrValGlyArgGlyAsnGluGlyIle-193 |
| SEQ. ID. NO. 12228 | 199-ValGlnGlnArgThrLeuArgAlaPheLys-208 |
| SEQ. ID. NO. 12229 | 224-HisValGlyAsnHisArgArgAsnAlaArgArgAspPhePheAspAsnArgHisHis-242 |
| SEQ. ID. NO. 12230 | 261-IleGlyLysAspGlyIle-266 |
| SEQ. ID. NO. 12231 | 279-GlyGlyAlaAsnGly-283 |
| SEQ. ID. NO. 12232 | 293-ArgAlaAspAlaAlaAlaGlyArgAla-301 |
| SEQ. ID. NO. 12233 | 314-ValGluArgAspValValArgGlnAspGlnArgAlaGlyArgArgAspPheGlnThr-332 |
| SEQ. ID. NO. 12234 | 351-GlyPheGlyGlyAspAspAsnAlaArgThrAspGluAlaVal-364 |
| SEQ. ID. NO. 12235 | 370-AspAlaAlaArgAsnGlnAlaGlnAsnGly-379 |
| SEQ. ID. NO. 12236 | 384-AspAsnGlnGlyMet-388 |
| SEQ. ID. NO. 12237 | 407-ProValAsnAspPhe-411 |
| Hydrophilic Regions - Hopp-Woods | |
| SEQ. ID. NO. 12238 | 12-AlaGlyGlyAspAspGlyAspArgArgAlaAlaAsp-23 |
| SEQ. ID. NO. 12239 | 66-GlyThrAlaArgGlnAspVal-72 |
| SEQ. ID. NO. 12240 | 84-AlaAspIleAspGly-88 |
| SEQ. ID. NO. 12241 | 147-PheGlyArgGluArgAlaArgThrAspAlaArgGlyIleGlyPheAspAspAlaGln-165 |
| SEQ. ID. NO. 12242 | 173-ThrTyrAlaArgAlaCysArgSerCysAlaArg-183 |
| SEQ. ID. NO. 12243 | 185-ThrValGlyArgGlyAsnGluGly-192 |
| SEQ. ID. NO. 12244 | 199-ValGlnGlnArgThrLeuArgAlaPheLys-208 |
| SEQ. ID. NO. 12245 | 226-GlyAsnHisArgArgAsnAlaArgArgAspPhePheAspAsnArgHisHis-242 |
| SEQ. ID. NO. 12246 | 261-IleGlyLysAspGly-265 |
| SEQ. ID. NO. 12247 | 293-ArgAlaAspAlaAlaAlaGlyArgAla-301 |
| SEQ. ID. NO. 12248 | 314-ValGluArgAspValValArgGlnAspGlnArgAlaGlyArgArgAspPheGlnThr-332 |

TABLE 1-continued

SEQ. ID. NO. 12249 352-PheGlyGlyAspAspAsnAlaArgThrAspGluAlaVal-364
SEQ. ID. NO. 12250 370-AspAlaAlaArgAsnGlnAla-376
907-2
AMPHI Regions - AMPHI
SEQ. ID. NO. 12251 42-AspAspValAlaSerValMetArgSer-50
SEQ. ID. NO. 12252 66-LysGluGlyGluArgTrpLeuSerAlaMetSer-76
SEQ. ID. NO. 12253 78-ArgLeuAlaArgPheVal-83
SEQ. ID. NO. 12254 129-GlyAlaArgGlyLeu-133
SEQ. ID. NO. 12255 142-AsnTyrIleGlyLysProAlaHis-149
SEQ. ID. NO. 12256 165-LeuArgHisTyrArgAsnLeuGluLysGlyAsn-175
SEQ. ID. NO. 12257 177-ValArgAlaLeuAlaArgPheAsnGly-185
Antigenic Index - Jameson-Wolf
SEQ. ID. NO. 12258 1-MetArgLysProThrAspThrLeuPro-9
SEQ. ID. NO. 12259 12-LeuGlnArgArgArgLeuLeu-18
SEQ. ID. NO. 12260 33-GlyAlaGlnArgGluGluThrLeuAlaAspAspValAlaSer-46
SEQ. ID. NO. 12261 51-SerValGlySerValAsnProProArgLeuValPheAspAsnProLysGluGlyGluArgTrp-71
SEQ. ID. NO. 12262 83-ValProGluGluGluGluArgArgArgLeu-92
SEQ. ID. NO. 12263 97-GlnTyrGluSerSerArgAlaGlyLeu-105
SEQ. ID. NO. 12264 115-GluValGluSerAlaPhe-120
SEQ. ID. NO. 12265 142-AsnTyrIleGlyLysProAlaHisAsn-150
SEQ. ID. NO. 12266 155-ArgThrAsnLeuArgTyrGly-161
SEQ. ID. NO. 12267 168-TyrArgAsnLeuGluLysGlyAsnIle-176
SEQ. ID. NO. 12268 184-AsnGlySerLeuGlySerAsnLysTyrProAsnAla-195
SEQ. ID. NO. 12269 200-TrpArgAsnArgTrpGlnTrp-206
Hydrophilic Regions - Hopp-Woods
SEQ. ID. NO. 12270 1-MetArgLysProThrAsp-6
SEQ. ID. NO. 12271 12-LeuGlnArgArgArgLeuLeu-18
SEQ. ID. NO. 12272 33-GlyAlaGlnArgGluGluThrLeuAlaAspAspValAlaSer-46
SEQ. ID. NO. 12273 60-LeuValPheAspAsnProLysGluGlyGluArgTrp-71
SEQ. ID. NO. 12274 83-ValProGluGluGluGluArgArgArgLeu-92
SEQ. ID. NO. 12275 99-GluSerSerArgAlaGlyLeu-105
SEQ. ID. NO. 12276 115-GluValGluSerAlaPhe-120
SEQ. ID. NO. 12277 169-ArgAsnLeuGluLysGlyAsnIle-176
908-2
AMPHI Regions - AMPHI
SEQ. ID. NO. 12278 9-TyrLysGlnAsnLys-13
SEQ. ID. NO. 12279 26-ThrAlaAlaGluLeu-30
SEQ. ID. NO. 12280 127-ThrAspCysTyrArgSerTyrAspValLeuAspValArgGluPheSerHisPheSer-145
Antigenic Index - Jameson-Wolf
SEQ. ID. NO. 12281 1-MetArgLysSerArgLeuSerArgTyrLysGlnAsnLysLeu-14
SEQ. ID. NO. 12282 51-GlnAsnSerProHis-55
SEQ. ID. NO. 12283 59-PheAspGlyGluValGluAlaAspGluSerTyrPheGlyGlyGlnArgLysGlyLysArgGlyArgGlyAlaAlaGly-84
SEQ. ID. NO. 12284 91-LeuLeuLysArgAsnGlyLysVal-98
SEQ. ID. NO. 12285 115-IleArgGluGlnValLysProAspSerIleVal-125
SEQ. ID. NO. 12286 127-ThrAspCysTyrArgSerTyrAsp-134
SEQ. ID. NO. 12287 136-LeuAspValArgGlu-140
SEQ. ID. NO. 12288 161-ArgThrThrLysProTyr-166
Hydrophilic Regions - Hopp-Woods
SEQ. ID. NO. 12289 1-MetArgLysSerArgLeuSerArgTyrLysGlnAsnLysLeu-14
SEQ. ID. NO. 12290 59-PheAspGlyGluValGluAlaAspGluSerTyr-69
SEQ. ID. NO. 12291 72-GlyGlnArgLysGlyLysArgGlyArgGlyAlaAlaGly-84
SEQ. ID. NO. 12292 92-LeuLysArgAsnGlyLys-97
SEQ. ID. NO. 12293 115-IleArgGluGlnValLysProAspSer-123
SEQ. ID. NO. 12294 136-LeuAspValArgGlu-140
909
AMPHI Regions - AMPHI
SEQ. ID. NO. 12295 71-GlyAsnAsnAlaAspGlu-76
Antigenic Index - Jameson-Wolf
SEQ. ID. NO. 12296 22-ThrTyrGlnAspGlyAsnGlyLysThrAlaValArgGlnLysTyrProAlaGly-39
SEQ. ID. NO. 12297 45-GlnAspGlySerTyrSerLysAsnMetAsnTyrAsnGlnTyrArgProGluArgHisAla-64
SEQ. ID. NO. 12298 68-AsnGlnThrGlyAsnAsnAlaAspGluGluHisArgGlnHisTrpGlnLysProLysPheGlnAsnArg-90
Hydrophilic Regions - Hopp-Woods
SEQ. ID. NO. 12299 23-TyrGlnAspGlyAsnGlyLysThrAlaValArgGlnLysTyr-36
SEQ. ID. NO. 12300 58-TyrArgProGluArgHisAla-64
SEQ. ID. NO. 12301 72-AsnAsnAlaAspGluGluHisArgGlnHisTrpGln-83
SEQ. ID. NO. 12302 85-ProLysPheGlnAsnArg-90
910
AMPHI Regions - AMPHI
SEQ. ID. NO. 12303 10-ValSerLeuSerAlaAla-15
SEQ. ID. NO. 12304 22-SerAlaGluArgGlnIle-27
SEQ. ID. NO. 12305 39-LysAlaValLysMetLeuGlu-45
SEQ. ID. NO. 12306 58-AspHisTrpGlyLysPro-63
SEQ. ID. NO. 12307 69-AlaTyrLysAspGlyArg-74
Antigenic Index - Jameson-Wolf
SEQ. ID. NO. 12308 19-AlaGlyAspSerAlaGluArgGlnIleTyrGlyAspProHisPheGluGlnAsnArgThrLysAlaValLysMetLeuGluGlnArgGlyTyrGln-50
SEQ. ID. NO. 12309 53-AspValAspAlaAspAspHisTrpGlyLysProValLeuGlu-66
SEQ. ID. NO. 12310 68-GluAlaTyrLysAspGlyArgGluTyrAsp-77
SEQ. ID. NO. 12311 83-ProAspLeuLysIleIleLysGluGlnLeuAspArg-94

TABLE 1-continued

| | |
|---|---|
| Hydrophilic Regions - Hopp-Woods | |
| SEQ. ID. NO. 12312 | 21-AspSerAlaGluArgGlnIleTyr-28 |
| SEQ. ID. NO. 12313 | 31-ProHisPheGluGlnAsnArgThrLysAlaValLysMetLeuGluGlnArgGly-48 |
| SEQ. ID. NO. 12314 | 53-AspValAspAlaAspAspHisTrpGly-61 |
| SEQ. ID. NO. 12315 | 68-GluAlaTyrLysAspGlyArgGluTyrAsp-77 |
| SEQ. ID. NO. 12316 | 86-LysIleIleLysGluGlnLeuAspArg-94 |
| 911 | |
| AMPHI Regions - AMPHI | |
| SEQ. ID. NO. 12317 | 6-LeuGluPheTrpValGlyLeuPhe-13 |
| SEQ. ID. NO. 12318 | 43-ValTyrAlaAspPheGlyAspIleGly-51 |
| SEQ. ID. NO. 12319 | 97-ValSerAlaGlnIle-101 |
| SEQ. ID. NO. 12320 | 118-GlyAspThrGluAsnLeuAla-124 |
| SEQ. ID. NO. 12321 | 140-AsnLeuIleGlyLysPheMetThrSerPhe-149 |
| Antigenic Index - Jameson-Wolf | |
| SEQ. ID. NO. 12322 | 1-MetLysLysAsnIle-5 |
| SEQ. ID. NO. 12323 | 35-GlyGlySerAspLysThrTyr-41 |
| SEQ. ID. NO. 12324 | 48-GlyAspIleGlyGlyLeuLysValAsnAlaProValLys-60 |
| SEQ. ID. NO. 12325 | 74-LeuAspProLysSerTyrGlnAlaArgValArgLeuAspLeuAspGlyLysTyrGlnPheSerSerAspVal-97 |
| SEQ. ID. NO. 12326 | 103-ThrSerGlyLeuLeuGly-108 |
| SEQ. ID. NO. 12327 | 115-GlnGlnGlyGlyAspThrGluAsn-122 |
| SEQ. ID. NO. 12328 | 149-PheAlaGluLysAsnAlaAspGlyGlyAsnAlaGluLysAlaAlaGlu-164 |
| Hydrophilic Regions - Hopp-Woods | |
| SEQ. ID. NO. 12329 | 1-MetLysLysAsnIle-5 |
| SEQ. ID. NO. 12330 | 36-GlySerAspLysThr-40 |
| SEQ. ID. NO. 12331 | 74-LeuAspProLysSerTyrGlnAlaArgValArgLeuAspLeuAspGly-89 |
| SEQ. ID. NO. 12332 | 116-GlnGlyGlyAspThrGluAsn-122 |
| SEQ. ID. NO. 12333 | 149-PheAlaGluLysAsnAlaAspGlyGlyAsnAlaGluLysAlaAlaGlu-164 |
| 912 | |
| AMPHI Regions - AMPHI | |
| SEQ. ID. NO. 12334 | 24-ProAlaAspAlaValSerGlnIle-31 |
| SEQ. ID. NO. 12335 | 62-PheAspPheGlnArgMetThrAlaLeuAlaValGlyAsnProTrpArgThrAlaSerAspAlaGlnLys-84 |
| SEQ. ID. NO. 12336 | 89-LysGluPheGlnThrLeu-94 |
| SEQ. ID. NO. 12337 | 169-TyrArgAsnGlnPheGlyGluIleIleLysAlaLys-180 |
| Antigenic Index - Jameson-Wolf | |
| SEQ. ID. NO. 12338 | 1-MetLysLysSerSer-5 |
| SEQ. ID. NO. 12339 | 29-SerGlnIleArgGlnAsnAlaThrGln-37 |
| SEQ. ID. NO. 12340 | 42-LeuLysAsnGlyAspAlaAsnThrAlaArgGlnLysAlaGluAla-56 |
| SEQ. ID. NO. 12341 | 74-AsnProTrpArgThrAlaSerAspAlaGlnLysGlnAlaLeuAlaLysGluPhe-91 |
| SEQ. ID. NO. 12342 | 104-LeuLysLeuLysAsnAlaAsnValAsnValLysAspAsnProIleValAsnLysGlyGlyLysGluIleIleVal-128 |
| SEQ. ID. NO. 12343 | 130-AlaGluValGlyValProGlyGlnLysProValAsn-141 |
| SEQ. ID. NO. 12344 | 146-ThrTyrGlnSerGlyGlyLysTyrArgThr-155 |
| SEQ. ID. NO. 12345 | 169-TyrArgAsnGlnPhe-173 |
| SEQ. ID. NO. 12346 | 177-IleLysAlaLysGlyValAspGlyLeuIleAla-187 |
| SEQ. ID. NO. 12347 | 189-LeuLysAlaLysAsnGlyGlyLys-196 |
| Hydrophilic Regions - Hopp-Woods | |
| SEQ. ID. NO. 12348 | 1-MetLysLysSerSer-5 |
| SEQ. ID. NO. 12349 | 31-IleArgGlnAsnAla-35 |
| SEQ. ID. NO. 12350 | 43-LysAsnGlyAspAlaAsnThrAlaArgGlnLysAlaGluAla-56 |
| SEQ. ID. NO. 12351 | 78-ThrAlaSerAspAlaGlnLysGlnAlaLeuAlaLysGluPhe-91 |
| SEQ. ID. NO. 12352 | 104-LeuLysLeuLysAsn-108 |
| SEQ. ID. NO. 12353 | 110-AsnValAsnValLysAspAsnProIleVal-119 |
| SEQ. ID. NO. 12354 | 121-LysGlyGlyLysGluIleIleVal-128 |
| SEQ. ID. NO. 12355 | 134-ValProGlyGlnLysProValAsn-141 |
| SEQ. ID. NO. 12356 | 177-IleLysAlaLysGlyValAsp-183 |
| SEQ. ID. NO. 12357 | 189-LeuLysAlaLysAsnGlyGlyLys-196 |
| 913 | |
| AMPHI Regions - AMPHI | |
| SEQ. ID. NO. 12358 | 22-GluThrArgProAlaAspProTyrGluGlyTyrAsnArg-34 |
| SEQ. ID. NO. 12359 | 53-ArgGlyTyrArgLysValAlaProLys-61 |
| SEQ. ID. NO. 12360 | 66-GlyValSerAsnPhePheAsnAsnLeuCysAspValValSer-79 |
| SEQ. ID. NO. 12361 | 107-LeuGlyGlyLeuIleAspIleAlaGlyAla-116 |
| SEQ. ID. NO. 12362 | 151-ValArgAspAlaLeuGlyThrGlyIleThrSerValTyrSer-164 |
| SEQ. ID. NO. 12363 | 193-AspLeuThrAspSerLeuAspGluAlaAla-202 |
| SEQ. ID. NO. 12364 | 238-LeuValGluSerAla-242 |
| SEQ. ID. NO. 12365 | 257-SerGluThrGlnAla-261 |
| Antigenic Index - Jameson-Wolf | |
| SEQ. ID. NO. 12366 | 21-AlaGluThrArgProAlaAspProTyrGluGlyTyrAsn-33 |
| SEQ. ID. NO. 12367 | 39-PheAsnAspGlnAlaAspArgTyr-46 |
| SEQ. ID. NO. 12368 | 51-AlaAlaArgGlyTyrArgLysValAlaProLysProValArgAla-65 |
| SEQ. ID. NO. 12369 | 81-GlySerAsnIleLeu-85 |
| SEQ. ID. NO. 12370 | 87-LeuAspIleLysArgAlaSerGluAspLeuVal-97 |
| SEQ. ID. NO. 12371 | 117-GlyGlyIleProAspAsnLysAsnThrLeuGlyAsp-128 |
| SEQ. ID. NO. 12372 | 132-SerTrpGlyTrpLysAsnSerAsn-139 |
| SEQ. ID. NO. 12373 | 149-SerThrValArgAspAlaLeu-155 |
| SEQ. ID. NO. 12374 | 163-TyrSerProLysAsnIle-168 |
| SEQ. ID. NO. 12375 | 172-ThrProValGlyArgTrpGly-178 |

SEQ. ID. NO. 12376 185-ValSerThrArgGluGlyLeuLeuAspLeuThrAspSerLeuAspGluAlaAlaIleAspLysTyrSerTyrThrArgAspLeuTyrMet-214
SEQ. ID. NO. 12377 216-ValArgAlaArgGlnThrGlyAlaThrProAlaGluGlyThrGluAspAsnIleAspIleAspGluLeuValGluSerAlaGluThrGlyAlaAla-247
SEQ. ID. NO. 12378 250-AlaValGlnGluAspSerValSerGluThrGlnAlaGluAlaAlaGlyGluAlaGluThrGlnProGlyThrGlnPro-275
Hydrophilic Regions - Hopp-Woods
SEQ. ID. NO. 12379 21-AlaGluThrArgProAlaAspProTyrGluGlyTyrAsn-33
SEQ. ID. NO. 12380 40-AsnAspGlnAlaAsp-44
SEQ. ID. NO. 12381 53-ArgGlyTyrArgLysValAlaProLysProValArg-64
SEQ. ID. NO. 12382 87-LeuAspIleLysArgAlaSerGluAspLeuVal-97
SEQ. ID. NO. 12383 118-GlyIleProAspAsnLysAsnThrLeu-126
SEQ. ID. NO. 12384 150-ThrValArgAspAlaLeu-155
SEQ. ID. NO. 12385 186-SerThrArgGluGlyLeuLeuAspLeuThrAspSerLeuAspGluAlaAlaIleAsp-204
SEQ. ID. NO. 12386 216-ValArgAlaArgGlnThrGly-222
SEQ. ID. NO. 12387 224-ThrProAlaGluGlyThrGluAspAsnIleAspIleAspGluLeuValGluSerAlaGluThrGlyAlaAla-247
SEQ. ID. NO. 12388 250-AlaValGlnGluAspSerValSerGluThrGlnAlaGluAlaAlaGlyGluAlaGluThrGlnPro-271
914-2
AMPHI Regions - AMPHI
SEQ. ID. NO. 12389 6-LeuGlyIleLeuThrAlaCysAlaAlaMet-15
SEQ. ID. NO. 12390 17-AlaPheAlaAspArgIleGlyAspLeu-25
SEQ. ID. NO. 12391 65-PheGlnLysThrPheGlu-70
SEQ. ID. NO. 12392 81-GlnLysValArgGlnAlaCys-87
Antigenic Index - Jameson-Wolf
SEQ. ID. NO. 12393 18-PheAlaAspArgIleGlyAspLeuGluAlaArgLeuAlaGlnLeuGluHisArgValAlaValLeuGluSerGlyGlyAsnThrValLys-47
SEQ. ID. NO. 12394 50-LeuPheGlySerAsnSer-55
SEQ. ID. NO. 12395 64-ProPheGlnLysThrPheGluAlaSerAspArgAsnGluGlyValAlaArgGlnLysValArgGlnAlaCysAsnArgGluThrSerAla-93
SEQ. ID. NO. 12396 95-PheCysGluAspGluAlaIleArgCysArgLysPheAsp-107
Hydrophilic Regions - Hopp-Woods
SEQ. ID. NO. 12397 18-PheAlaAspArgIleGlyAspLeuGluAlaArgLeuAlaGlnLeuGluHisArgValAlaVal-38
SEQ. ID. NO. 12398 67-LysThrPheGluAlaSerAspArgAsnGluGlyValAlaArgGlnLysValArgGlnAlaCysAsnArgGluThrSer-92
SEQ. ID. NO. 12399 95-PheCysGluAspGluAlaIleArgCysArgLysPheAsp-107
915-2
AMPHI Regions - AMPHI
SEQ. ID. NO. 12400 9-ValAlaValSerAlaLeuSerAlaCysArgGlnAla-20
SEQ. ID. NO. 12401 31-IleSerAspArgSerVal-36
SEQ. ID. NO. 12402 67-SerThrIleLysGlnMetPheGlyTyrThrLysLeuProGluGluProLysGlyIleArgValIleTyrValThrAspMetGlyAsnValThrAspTrp Thr-100
SEQ. ID. NO. 12403 139-GlnAlaGluLysPhe-143
Antigenic Index - Jameson-Wolf
SEQ. ID. NO. 12404 15-SerAlaCysArgGlnAlaGluGluGlyProProProLeuProArgGlnIleSerAspArgSerValGlyHis-38
SEQ. ID. NO. 12405 43-AsnLeuThrGluHisAsnGlyProLysAla-52
SEQ. ID. NO. 12406 57-AsnGlyLysProAspGlnProVal-64
SEQ. ID. NO. 12407 75-TyrThrLysLeuProGluGluProLysGlyIle-85
SEQ. ID. NO. 12408 97-ThrAspTrpThrAsnProAsnAlaAspThrGluTrpMetAspAlaLysLys-113
SEQ. ID. NO. 12409 125-GlyMetGlyAlaGluAspAlaLeuProPheGlyAsnLysGluGlnAlaGluLysPheAlaLysAspLysGlyGlyLysValValGlyPheAspAspMet ProAspThrTyr-161
Hydrophilic Regions - Hopp-Woods
SEQ. ID. NO. 12410 18-ArgGlnAlaGluGluGlyProProProLeu-27
SEQ. ID. NO. 12411 30-GlnIleSerAspArgSerVal-36
SEQ. ID. NO. 12412 46-GluHisAsnGlyProLys-51
SEQ. ID. NO. 12413 58-GlyLysProAspGln-62
SEQ. ID. NO. 12414 77-LysLeuProGluGluProLysGlyIle-85
SEQ. ID. NO. 12415 103-AsnAlaAspThrGluTrpMetAspAlaLysLys-113
SEQ. ID. NO. 12416 127-GlyAlaGluAspAlaLeu-132
SEQ. ID. NO. 12417 135-GlyAsnLysGluGlnAlaGluLysPheAlaLysAspLysGlyGlyLys-150
SEQ. ID. NO. 12418 155-AspAspMetProAsp-159
917
AMPHI Regions - AMPHI
SEQ. ID. NO. 12419 6-ProLeuAlaValLeuThrAlaLeuLeuLeu-15
SEQ. ID. NO. 12420 35-GlnAsnValLeuLysIleTyrAsnTrpSerGluTyrValAspProGluThrValAlaAsp-54
SEQ. ID. NO. 12421 99-IleLysAlaGlyAlaTyrGlnLysIleAspLysSerLeu-111
SEQ. ID. NO. 12422 124-ArgLeuMetAspGlyValAspPro-131
SEQ. ID. NO. 12423 152-ArgValLysLysAlaLeu-157
SEQ. ID. NO. 12424 188-AspSerAlaAlaGlu-192
SEQ. ID. NO. 12425 206-AsnSerSerAsnThrGluAspIleArgGluAlaThr-217
SEQ. ID. NO. 12426 292-AlaLysAsnValAlaAsnAlaHisLysTyrIleAsnAspPheLeuAsp-307
SEQ. ID. NO. 12427 325-LysProAlaArgGluLeuMetGluAsp-333
Antigenic Index - Jameson-Wolf
SEQ. ID. NO. 12428 18-CysGlyGlySerAspLysProProAlaGluLysProAlaProAlaGluAsnGlnAsnVal-37
SEQ. ID. NO. 12429 44-SerGluTyrValAspProGluThrValAlaAspPheGluLysLysAsnGlyIleLysValThr-64
SEQ. ID. NO. 12430 68-TyrAspSerAspGluThrLeuGluSerLysValLeuThrGlyLysSerGlyTyrAsp-86
SEQ. ID. NO. 12431 102-GlyAlaTyrGlnLysIleAspLysSerLeuIleProAsnTyrLysHisLeuAsnProGluMetMetArgLeuMetAspGlyValAspProGlyHisGlu Tyr-135
SEQ. ID. NO. 12432 149-AsnThrGluArgValLysLysAlaLeuGlyThrAspLysLeuProAspAsnGln-166
SEQ. ID. NO. 12433 171-PheAspProGluTyrThrSerLysLeuLysGlnCysGly-183
SEQ. ID. NO. 12434 201-LeuGlyLysAsnProAsnSerSerAsnThrGluAspIleArgGluAlaThrAlaLeuLeuLysLysAsnArgProAsnIleLysArgPheThrSerSerGly PheIle-236
SEQ. ID. NO. 12435 238-AspLeuAlaArgGlyAspThr-244
SEQ. ID. NO. 12436 255-AsnIleAlaLysArgArgAlaGluGluAlaGlyGlyLysGluLysIleArgValMetMetProLysGluGlyValGly-280
SEQ. ID. NO. 12437 287-ValIleProLysAspAlaLysAsnValAlaAsn-297
SEQ. ID. NO. 12438 305-PheLeuAspProGluValSerAlaLysAsnGlyAsn-316

TABLE 1-continued

SEQ. ID. NO. 12439 320-TyrAlaProSerSerLysProAlaArgGluLeuMetGluAspGluPheLysAsnAspAsnThrIlePheProThrGluGluAspLeuLysAsn-350
SEQ. ID. NO. 12440 368-GlnTrpGlnAspValLysAlaGlyLys-376
Hydrophilic Regions - Hopp-Woods
SEQ. ID. NO. 12441 19-GlyGlySerAspLysProProAlaGluLysProAlaProAlaGluAsn-34
SEQ. ID. NO. 12442 47-ValAspProGluThrValAlaAspPheGluLysLysAsnGlyIle-61
SEQ. ID. NO. 12443 68-TyrAspSerAspGluThrLeuGluSerLysValLeuThr-80
SEQ. ID. NO. 12444 105-GlnLysIleAspLysSerLeu-111
SEQ. ID. NO. 12445 121-GluMetMetArgLeuMetAspGlyValAspProGlyHis-133
SEQ. ID. NO. 12446 149-AsnThrGluArgValLysLysAlaLeuGlyThrAspLysLeuProAspAsnGln-166
SEQ. ID. NO. 12447 174-GluTyrThrSerLysLeuLysGln-181
SEQ. ID. NO. 12448 204-AsnProAsnSerSerAsnThrGluAspIleArgGluAlaThrAlaLeuLeuLysLysAsnArgProAsnIleLysArgPheThr-231
SEQ. ID. NO. 12449 238-AspLeuAlaArgGlyAspThr-244
SEQ. ID. NO. 12450 255-AsnIleAlaLysArgArgAlaGluGluAlaGlyGlyLysGluLysIleArgValMetMetProLysGluGly-278
SEQ. ID. NO. 12451 290-LysAspAlaLysAsnValAlaAsn-297
SEQ. ID. NO. 12452 305-PheLeuAspProGluValSerAlaLysAsn-314
SEQ. ID. NO. 12453 322-ProSerSerLysProAlaArgGluLeuMetGluAspGluPheLysAsnAspAsn-339
SEQ. ID. NO. 12454 343-ProThrGluGluAspLeuLysAsn-350
SEQ. ID. NO. 12455 370-GlnAspValLysAlaGlyLys-376
919
AMPHI Regions - AMPHI
SEQ. ID. NO. 12456 12-GlyIleAlaAlaAlaIleLeu-18
SEQ. ID. NO. 12457 24-LysSerIleGlnThrPheProGln-31
SEQ. ID. NO. 12458 37-IleAsnGlyProAspArgProValGlyIleProAsp-48
SEQ. ID. NO. 12459 76-AspPheAlaLysSerLeuGln-82
SEQ. ID. NO. 12460 98-GlnAspValCysAlaGlnAlaPheGlnThrProVal-109
SEQ. ID. NO. 12461 119-GluArgTyrPheThr-123
SEQ. ID. NO. 12462 133-LeuAlaGlyThrValThrGlyTyrTyrGlu-142
SEQ. ID. NO. 12463 161-GlyIleProAspAspPheIleSerValPro-170
SEQ. ID. NO. 12464 176-ArgSerGlyLysAlaLeuValArgIleArgGln-186
SEQ. ID. NO. 12465 191-SerGlyThrIleAspAsnThrGlyGlyThr-200
SEQ. ID. NO. 12466 307-MetGlnGlyIleLysSerTyrMetArgGlnAsnProGlnArgLeuAlaGluValLeu-325
SEQ. ID. NO. 12467 348-AlaLeuGlyThrProLeuMetGlyGluTyrAlaGlyAlaVal-361
SEQ. ID. NO. 12468 382-ArgLysAlaLeuAsnArg-387
Antigenic Index - Jameson-Wolf
SEQ. ID. NO. 12469 21-CysGlnSerLysSerIleGlnThr-28
SEQ. ID. NO. 12470 30-ProGlnProAspThr-34
SEQ. ID. NO. 12471 36-ValIleAsnGlyProAspArgProValGlyIleProAspProAlaGlyThr-52
SEQ. ID. NO. 12472 54-ValGlyGlyGlyGly-58
SEQ. ID. NO. 12473 76-AspPheAlaLysSerLeuGln-82
SEQ. ID. NO. 12474 87-GlyCysAlaAsnLeuLysAsnArgGlnGlyTrpGln-98
SEQ. ID. NO. 12475 121-TyrPheThrProTrp-125
SEQ. ID. NO. 12476 143-ProValLeuLysGlyAspAspArgArgThrAlaGln-154
SEQ. ID. NO. 12477 162-IleProAspAspPheIle-167
SEQ. ID. NO. 12478 173-AlaGlyLeuArgSerGlyLysAlaLeuValArgIleArgGlnThrGlyLysAsnSerGlyThrIleAspAsnThrGlyGlyThrHis-201
SEQ. ID. NO. 12479 215-ThrAlaIleLysGlyArgPheGluGlySerArgPheLeuProTyrHisThrArgAsnGlnIleAsnGlyGlyAlaLeuAspGlyLysAlaPro-245
SEQ. ID. NO. 12480 250-AlaGluAspProValGlu-255
SEQ. ID. NO. 12481 262-GlnGlySerGlyArgLeuLysThrProSerGlyLysTyrIleArg-276
SEQ. ID. NO. 12482 278-GlyTyrAlaAspLysAsnGluHisPro-286
SEQ. ID. NO. 12483 293-TyrMetAlaAspLysGlyTyrLeuLysLeuGlyGln-304
SEQ. ID. NO. 12484 308-GlnGlyIleLysSerTyrMetArgGlnAsnProGlnArgLeuAlaGlu-323
SEQ. ID. NO. 12485 326-GlyGlnAsnProSer-330
SEQ. ID. NO. 12486 337-LeuAlaGlySerSerAsnAspGlyProVal-346
SEQ. ID. NO. 12487 359-GlyAlaValAspArgHisTyr-365
SEQ. ID. NO. 12488 379-ProValThrArgLysAlaLeuAsn-386
SEQ. ID. NO. 12489 393-AspThrGlySerAlaIleLysGlyAlaValArg-403
SEQ. ID. NO. 12490 409-GlyTyrGlyAspGluAlaGlyGluLeuAlaGlyLysGlnLysThrThr-424
SEQ. ID. NO. 12491 431-LeuProAsnGlyMetLysProGluTyrArgPro-441
Hydrophilic Regions - Hopp-Woods
SEQ. ID. NO. 12492 38-AsnGlyProAspArgProValGly-45
SEQ. ID. NO. 12493 90-AsnLeuLysAsnArgGlnGlyTrp-97
SEQ. ID. NO. 12494 144-ValLeuLysGlyAspAspArgArgThrAlaGln-154
SEQ. ID. NO. 12495 175-LeuArgSerGlyLysAlaLeuValArgIleArgGlnThrGlyLysAsnSerGlyThrIleAspAsnThrGly-198
SEQ. ID. NO. 12496 215-ThrAlaIleLysGlyArgPheGluGly-223
SEQ. ID. NO. 12497 239-AlaLeuAspGlyLysAla-244
SEQ. ID. NO. 12498 250-AlaGluAspProVal-254
SEQ. ID. NO. 12499 265-GlyArgLeuLysThrProSer-271
SEQ. ID. NO. 12500 279-TyrAlaAspLysAsnGluHis-285
SEQ. ID. NO. 12501 317-AsnProGlnArgLeuAlaGlu-323
SEQ. ID. NO. 12502 337-LeuAlaGlySerSerAsnAspGlyPro-345
SEQ. ID. NO. 12503 380-ValThrArgLysAlaLeuAsn-386
SEQ. ID. NO. 12504 393-AspThrGlySerAlaIle-398
SEQ. ID. NO. 12505 412-AspGluAlaGlyGluLeuAlaGlyLysGlnLysThr-423
SEQ. ID. NO. 12506 434-GlyMetLysProGluTyrArgPro-441
920-2
AMPHI Regions - AMPHI
SEQ. ID. NO. 12507 43-GlyGluPheProGluLeuGluProIleAla-52
SEQ. ID. NO. 12508 117-GlyIleLysGluMetProAsp-123
SEQ. ID. NO. 12509 135-LysAsnIleValAsnVal-140
SEQ. ID. NO. 12510 163-LeuAspAsnProAlaAsn-168

TABLE 1-continued

| | |
|---|---|
| SEQ. ID. NO. 12511 | 190-ThrValThrAlaThrPheAspGlyPheAspThrSerAspArgSerLys-205 |
| SEQ. ID. NO. 12512 | 212-GlnAlaPheSerAspSerThr-218 |
| Antigenic Index - Jameson-Wolf | |
| SEQ. ID. NO. 12513 | 40-LeuGlyTyrGlyGluPheProGlu-47 |
| SEQ. ID. NO. 12514 | 49-GluProIleAlaLysAspArgLeu-56 |
| SEQ. ID. NO. 12515 | 66-ValThrGluLysGlyLysGluAsnMetIle-75 |
| SEQ. ID. NO. 12516 | 77-ArgGlyThrTyrAsnTyrGlnTyrArgSerAsnArgProValLysAspGlySerTyr-95 |
| SEQ. ID. NO. 12517 | 104-ThrPheTrpSerLysAsnLysAlaGlyTrp-113 |
| SEQ. ID. NO. 12518 | 116-AlaGlyIleLysGluMetProAspAlaSerTyrCysGluGlnThrArgMetPheGlyLysAsnIleValAsnValGlyHisGluSerAlaAspThr-147 |
| SEQ. ID. NO. 12519 | 152-LysProValGlyGlnAsnLeuGlu-159 |
| SEQ. ID. NO. 12520 | 162-ProLeuAspAsnProAla-167 |
| SEQ. ID. NO. 12521 | 173-GluArgPheLysVal-177 |
| SEQ. ID. NO. 12522 | 181-PheArgGlyGluProLeuProAsnAla-189 |
| SEQ. ID. NO. 12523 | 194-ThrPheAspGlyPheAspThrSerAspArgSerLysThrHisLysThrGluAla-211 |
| SEQ. ID. NO. 12524 | 213-AlaPheSerAspSerThrAspAspLysGlyGluValAsp-225 |
| SEQ. ID. NO. 12525 | 237-AsnValGluHisLysThrAspPheProAspGlnSerValCysGlnLysGlnAlaAsnTyrSer-257 |
| Hydrophilic Regions - Hopp-Woods | |
| SEQ. ID. NO. 12526 | 49-GluProIleAlaLysAspArgLeu-56 |
| SEQ. ID. NO. 12527 | 66-ValThrGluLysGlyLysGluAsnMetIle-75 |
| SEQ. ID. NO. 12528 | 85-ArgSerAsnArgProValLysAspGlySer-94 |
| SEQ. ID. NO. 12529 | 107-SerLysAsnLysAlaGlyTrp-113 |
| SEQ. ID. NO. 12530 | 116-AlaGlyIleLysGluMetProAsp-123 |
| SEQ. ID. NO. 12531 | 128-GluGlnThrArgMetPheGly-134 |
| SEQ. ID. NO. 12532 | 142-HisGluSerAlaAsp-146 |
| SEQ. ID. NO. 12533 | 173-GluArgPheLysVal-177 |
| SEQ. ID. NO. 12534 | 196-AspGlyPheAspThrSerAspArgSerLysThrHisLysThrGluAla-211 |
| SEQ. ID. NO. 12535 | 213-AlaPheSerAspSerThrAspAspLysGlyGluValAsp-225 |
| SEQ. ID. NO. 12536 | 237-AsnValGluHisLysThrAspPheProAsp-246 |
| SEQ. ID. NO. 12537 | 248-SerValCysGlnLys-252 |
| 921 | |
| AMPHI Regions - AMPHI | |
| SEQ. ID. NO. 12538 | 12-AlaValLeuSerGlyCysGlnSerIleTyrValProThrLeuThrGluIleProValAsn-31 |
| SEQ. ID. NO. 12539 | 33-IleAsnThrValLysThr-38 |
| SEQ. ID. NO. 12540 | 51-HisTrpThrAspValAlaLysIleSerAspGlu-61 |
| SEQ. ID. NO. 12541 | 72-GlyLysMetThrLysValGlnAlaAlaGlnTyrLeuAsnAsnPheArgLys-88 |
| SEQ. ID. NO. 12542 | 98-AspSerMetTyrGluIleTyrLeuArg-106 |
| SEQ. ID. NO. 12543 | 126-GlnAsnAlaLeuArgGlyTrpGlnGlnArg-135 |
| Antigenic Index - Jameson-Wolf | |
| SEQ. ID. NO. 12544 | 36-ValLysThrGluAlaProAlaLysGlyPheArg-46 |
| SEQ. ID. NO. 12545 | 56-AlaLysIleSerAspGluAlaThrArg-64 |
| SEQ. ID. NO. 12546 | 72-GlyLysMetThrLys-76 |
| SEQ. ID. NO. 12547 | 84-AsnAsnPheArgLysArgLeuValGlyArgAsnAlaValAspAspSerMet-100 |
| SEQ. ID. NO. 12548 | 108-AlaIleAspSerGlnArgGlyAlaIleAsnThrGluGlnSerLys-122 |
| SEQ. ID. NO. 12549 | 128-AlaLeuArgGlyTrpGlnGlnArgTrpLysAsnMetAspValLysProAsnAsnProAla-147 |
| Hydrophilic Regions - Hopp-Woods | |
| SEQ. ID. NO. 12550 | 36-ValLysThrGluAlaProAlaLysGlyPheArg-46 |
| SEQ. ID. NO. 12551 | 56-AlaLysIleSerAspGluAlaThrArg-64 |
| SEQ. ID. NO. 12552 | 86-PheArgLysArgLeuValGly-92 |
| SEQ. ID. NO. 12553 | 94-AsnAlaValAspAspSerMet-100 |
| SEQ. ID. NO. 12554 | 108-AlaIleAspSerGlnArgGlyAlaIleAsnThrGluGlnSerLys-122 |
| SEQ. ID. NO. 12555 | 136-TrpLysAsnMetAspValLysProAsnAsn-145 |
| 922 | |
| AMPHI Regions - AMPHI | |
| SEQ. ID. NO. 12556 | 16-LeuSerAlaCysThr-20 |
| SEQ. ID. NO. 12557 | 28-ArgAlaAsnGluAlaGlnAlaPro-35 |
| SEQ. ID. NO. 12558 | 37-AlaValGluMetLysLys-42 |
| SEQ. ID. NO. 12559 | 72-ValArgArgPheValAspAsp-78 |
| SEQ. ID. NO. 12560 | 89-GluTrpGlnAspPhePheAspLys-96 |
| SEQ. ID. NO. 12561 | 104-ValLysIleMetHis-108 |
| SEQ. ID. NO. 12562 | 144-AspAspValAlaGln-148 |
| SEQ. ID. NO. 12563 | 172-GlySerPheArgValAlaAspAlaLeu-180 |
| SEQ. ID. NO. 12564 | 196-LysGluLeuValGluLeuLeuLysLeuAla-205 |
| SEQ. ID. NO. 12565 | 222-AlaMetGlyMetPro-226 |
| SEQ. ID. NO. 12566 | 245-HisArgAspIleTrpGlyAsnValGlyAspValAlaAlaSerValAlaAsnTyrMetLysGlnHis-266 |
| SEQ. ID. NO. 12567 | 298-ArgThrValAlaAspLeuLysAlaTyr-306 |
| SEQ. ID. NO. 12568 | 335-TyrLeuGlyLeuAsnAsnPheTyrThr-343 |
| Antigenic Index - Jameson-Wolf | |
| SEQ. ID. NO. 12569 | 1-MetLysLysArgLysIleLeu-7 |
| SEQ. ID. NO. 12570 | 22-MetGluAlaArgProProArgAlaAsnGluAlaGlnAlaProArgAlaValGluMetLysLysGluSerArgProAlaPhe-48 |
| SEQ. ID. NO. 12571 | 61-ValSerAspSerGlyPhe-66 |
| SEQ. ID. NO. 12572 | 70-AlaAsnValArgArgPheValAspAspGluValGlyLysGlyAspPheSerArgAlaGluTrp-90 |
| SEQ. ID. NO. 12573 | 107-MetHisArgProSerThrSerArgPro-115 |
| SEQ. ID. NO. 12574 | 120-ArgThrGlyAsnSerGlyLysAlaLysPheArgGlyAlaArgArgPheTyrAlaGluAsnArgAlaLeuIle-143 |
| SEQ. ID. NO. 12575 | 145-AspValAlaGlnLysTyrGlyVal-152 |
| SEQ. ID. NO. 12576 | 163-IleGluThrAsnTyrGlyLysAsnThrGlySer-173 |
| SEQ. ID. NO. 12577 | 186-AspTyrProArgArgAlaGlyPhePhe-194 |
| SEQ. ID. NO. 12578 | 203-LysLeuAlaLysGluGluGlyGlyAsp-211 |
| SEQ. ID. NO. 12579 | 229-MetProSerSerTyrArgLysTrpAlaValAspTyrAspGlyAspGlyHisArgAspIle-248 |
| SEQ. ID. NO. 12580 | 266-HisGlyTrpArgThrGlyGlyLysMet-274 |
| SEQ. ID. NO. 12581 | 281-AlaProGlyAlaAsp-285 |

TABLE 1-continued

SEQ. ID. NO. 12582 290-IleGlyGluLysThrAlaLeu-296
SEQ. ID. NO. 12583 310-ProGlyGluGluLeuAlaAspAspGluLysAlaVal-321
SEQ. ID. NO. 12584 326-GluThrAlaProGly-330
SEQ. ID. NO. 12585 357-ValArgAspIleAlaAsnSerLeuGlyGlyProGlyLeu-369
Hydrophilic Regions - Hopp-Woods
SEQ. ID. NO. 12586 1-MetLysLysArgLysIleLeu-7
SEQ. ID. NO. 12587 22-MetGluAlaArgProProArgAlaAsnGluAlaGlnAlaProArgAlaValGluMetLysLysGluSerArgProAlaPhe-48
SEQ. ID. NO. 12588 70-AlaAsnValArgArgPheValAspAspGluValGlyLysGlyAspPheSerArgAlaGluTrp-90
SEQ. ID. NO. 12589 122-GlyAsnSerGlyLysAlaLysPheArgGlyAlaArgArgPheTyrAlaGluAsnArgAlaLeuIle-143
SEQ. ID. NO. 12590 166-AsnTyrGlyLysAsnThrGly-172
SEQ. ID. NO. 12591 187-TyrProArgArgAlaGlyPhePhe-194
SEQ. ID. NO. 12592 203-LysLeuAlaLysGluGluGlyGlyAsp-211
SEQ. ID. NO. 12593 240-TyrAspGlyAspGlyHisArgAspIle-248
SEQ. ID. NO. 12594 290-IleGlyGluLysThrAlaLeu-296
SEQ. ID. NO. 12595 310-ProGlyGluGluLeuAlaAspAspGluLysAlaVal-321
SEQ. ID. NO. 12596 357-ValArgAspIleAla-361
923-2
AMPHI Regions - AMPHI
SEQ. ID. NO. 12597 9-LeuMetAlaCysAlaAlaPheLeu-16
SEQ. ID. NO. 12598 26-LeuGlyAlaCysTyrAlaIleLeuSerLeuTyrAla-37
SEQ. ID. NO. 12599 63-ProAlaLeuLeuGlyGlyTrpValGlyAlaTyr-73
SEQ. ID. NO. 12600 117-GlyValAlaSerProCysArgThrIleCysThrValCysGlyPheValAlaLeu-134
Antigenic Index - Jameson-Wolf
SEQ. ID. NO. 12601 43-IleAspLysArgCysAlaIleArgGlyGlnArgArgIleProGluHisArgLeu-60
SEQ. ID. NO. 12602 79-PheLysHisLysThrAlaLysLysArgPhe-88
Hydrophilic Regions - Hopp-Woods
SEQ. ID. NO. 12603 43-IleAspLysArgCysAlaIleArgGlyGlnArgArgIleProGluHisArgLeu-60
SEQ. ID. NO. 12604 79-PheLysHisLysThrAlaLysLysArgPhe-88
925-1
AMPHI Regions - AMPHI
SEQ. ID. NO. 12605 8-ValGlyValValAlaValLeu-14
SEQ. ID. NO. 12606 116-LysCysGlyGlnThrAlaGlnAlaTyrArgAspAla-127
SEQ. ID. NO. 12607 139-GlnHisLeuAlaAlaIleGluGlnLeuLys-148
SEQ. ID. NO. 12608 155-PheAspGluLeuGlu-159
Antigenic Index - Jameson-Wolf
SEQ. ID. NO. 12609 15-AlaGlyCysGlyLysAspAlaGlyGlyTyrGluGlyTyrTrpArgGluLysSerAspLysLysGluGlyMetIleAlaValLysLysGluLysGlyAsn-47
SEQ. ID. NO. 12610 57-ThrGlyLysGluGluSerLeuLeuLeuSerGluLysAspGlyAla-71
SEQ. ID. NO. 12611 75-AsnThrGlyIleGly-79
SEQ. ID. NO. 12612 81-IleProIleLysLeuSerAspAspGlyLysGluLeuTyrValGluArgArgGlnTyrValLysThrAspAlaAlaMetLysAspLysIleIleAlaHisGlnLys LysCysGlyGlnThr-120
SEQ. ID. NO. 12613 123-AlaTyrArgAspAlaArgAsnAlaLeuProSerAsnGlnThrTyr-137
SEQ. ID. NO. 12614 145-GluGlnLeuLysArgArgPheGluAlaGluPheAspGluLeuGluLysGluIleLysCysAsnGlyArgSerProAla-170
Hydrophilic Regions - Hopp-Woods
SEQ. ID. NO. 12615 17-CysGlyLysAspAlaGlyGly-23
SEQ. ID. NO. 12616 27-TyrTrpArgGluLysSerAspLysLysGluGlyMetIleAlaValLysLysGluLysGly-46
SEQ. ID. NO. 12617 57-ThrGlyLysGluGluSerLeuLeuLeuSerGluLysAspGlyAla-71
SEQ. ID. NO. 12618 81-IleProIleLysLeuSerAspAspGlyLysGluLeuTyrValGluArgArgGlnTyrValLysThrAspAlaAlaMetLysAspLysIleIleAlaHisGln LysLysCysGlyGln-119
SEQ. ID. NO. 12619 123-AlaTyrArgAspAlaArgAsnAlaLeu-131
SEQ. ID. NO. 12620 145-GluGlnLeuLysArgArgPheGluAlaGluPheAspGluLeuGluLysGluIleLysCysAsnGlyArgSer-168
926
AMPHI Regions - AMPHI
SEQ. ID. NO. 12621 29-ProSerGluHisIleSerSerPhe-36
SEQ. ID. NO. 12622 72-LeuGlySerThrLeuGlyGln-78
SEQ. ID. NO. 12623 98-AlaGluSerAlaGluGluLeuSerArgGln-107
SEQ. ID. NO. 12624 128-AlaGlyAlaProTyrArgIleLeuProAspGlyIle-139
SEQ. ID. NO. 12625 151-AlaAspSerGlyGlyGlnVal-157
Antigenic Index - Jameson-Wolf
SEQ. ID. NO. 12626 19-LeuProGlnAsnAsnGluAsnLeuTrpGlnProSerGluHisIleSer-34
SEQ. ID. NO. 12627 37-AlaAlaGluGlyArgLeuAlaValLysAlaGluGlyLysGlySerTyrAla-53
SEQ. ID. NO. 12628 70-ThrProLeuGlySer-74
SEQ. ID. NO. 12629 79-LeuCysGlnAspArgAspGlyAlaLeu-87
SEQ. ID. NO. 12630 89-ValAspGlyLysGlyAsnValTyr-96
SEQ. ID. NO. 12631 99-GluSerAlaGluGluLeuSerArg-106
SEQ. ID. NO. 12632 121-TrpAlaAspGlyArgArgValAla-128
SEQ. ID. NO. 12633 134-IleLeuProAspGlyIleLeu-140
SEQ. ID. NO. 12634 148-GlyArgThrAlaAspSerGlyGlyGln-156
SEQ. ID. NO. 12635 177-GlyMetProSerGluThrGluThrProGluArgCysAlaAlaArgThrArg-193
Hydrophilic Regions - Hopp-Woods
SEQ. ID. NO. 12636 37-AlaAlaGluGlyArgLeuAlaValLysAlaGluGlyLysGlySer-51
SEQ. ID. NO. 12637 80-CysGlnAspArgAspGlyAlaLeu-87
SEQ. ID. NO. 12638 89-ValAspGlyLysGly-93
SEQ. ID. NO. 12639 99-GluSerAlaGluGluLeuSerArg-106
SEQ. ID. NO. 12640 123-AspGlyArgArgValAla-128
SEQ. ID. NO. 12641 149-ArgThrAlaAspSerGlyGlyGln-156
SEQ. ID. NO. 12642 180-SerGluThrGluThrProGluArgCysAlaAlaArgThrArg-193
927-2
AMPHI Regions - AMPHI
SEQ. ID. NO. 12643 13-LeuLeuThrAlaCys-17
SEQ. ID. NO. 12644 48-SerTyrAspValAlaArgAspPheTyrLysGlu-58

TABLE 1-continued

| | |
|---|---|
| SEQ. ID. NO. 12645 | 120-LysGlyTrpGlnGlnAlaLeuPro-127 |
| SEQ. ID. NO. 12646 | 145-AsnProLysGlnIleArgAspTrpAsnAspLeuAlaLysAspGly-159 |
| SEQ. ID. NO. 12647 | 197-LysLeuValAlaSerIleLeu-203 |
| SEQ. ID. NO. 12648 | 223-ArgAsnIleGlyAspValLeu-229 |
| SEQ. ID. NO. 12649 | 275-ThrGlnLysThrAlaArgAla-281 |
| SEQ. ID. NO. 12650 | 283-LeuGluTyrLeuTrpSerGluProAlaGlnGluLeu-294 |
| SEQ. ID. NO. 12651 | 325-LysLysPheGlyGlyTrpAspAsnIleMetLysThr-336 |
| Antigenic Index - Jameson-Wolf | |
| SEQ. ID. NO. 12652 | 18-SerProAlaAlaAspSerAsnHisProSerGlyGlnAsnAlaProAlaAsnThrGluSerAspGlyLysAsnIleThr-43 |
| SEQ. ID. NO. 12653 | 48-SerTyrAspValAlaArgAspPheTyrLysGluTyrAsnPro-61 |
| SEQ. ID. NO. 12654 | 67-TyrGlnSerGluHisProGlyThrSer-75 |
| SEQ. ID. NO. 12655 | 79-GlnGlnSerHisGlyGlySerSerLysGlnAla-89 |
| SEQ. ID. NO. 12656 | 104-AsnGlnSerSerAspIleAspLeuLeuGluLysLysGlyLeuVal-118 |
| SEQ. ID. NO. 12657 | 125-AlaLeuProAspHisAlaAlaProTyrThr-134 |
| SEQ. ID. NO. 12658 | 142-ArgLysAsnAsnProLysGlnIleArgAspTrpAsnAspLeuAlaLysAspGlyVal-160 |
| SEQ. ID. NO. 12659 | 166-AsnProLysThrSerGlyAsnGlyArg-174 |
| SEQ. ID. NO. 12660 | 185-LeuLysThrThrAsnGlyAsnGluGlnGluAlaGlnLys-197 |
| SEQ. ID. NO. 12661 | 203-LeuLysAsnThrProValPheGluAsnGlyGlyArgAlaAlaThr-217 |
| SEQ. ID. NO. 12662 | 220-PheThrGlnArgAsnIleGlyAsp-227 |
| SEQ. ID. NO. 12663 | 238-TyrValSerLysLysLeuThrGlnGlyGln-247 |
| SEQ. ID. NO. 12664 | 270-ValAlaLysLysGlyThrGlnLysThrAlaArgAla-281 |
| SEQ. ID. NO. 12665 | 300-LeuArgProArgAsnProGluValLeuAlaArgHisLysAlaAspPheProAspLeuAspThrPheSerProGluLysLysPheGlyGlyTrp-330 |
| SEQ. ID. NO. 12666 | 337-TyrPheAlaAspGlyGlyIle-343 |
| SEQ. ID. NO. 12667 | 347-LeuThrAlaGlnLys-351 |
| Hydrophilic Regions - Hopp-Woods | |
| SEQ. ID. NO. 12668 | 19-ProAlaAlaAspSerAsnHisProSer-27 |
| SEQ. ID. NO. 12669 | 33-AlaAsnThrGluSerAspGlyLysAsn-41 |
| SEQ. ID. NO. 12670 | 50-AspValAlaArgAspPheTyrLys-57 |
| SEQ. ID. NO. 12671 | 67-TyrGlnSerGluHisProGly-73 |
| SEQ. ID. NO. 12672 | 82-HisGlyGlySerSerLysGlnAla-89 |
| SEQ. ID. NO. 12673 | 105-GlnSerSerAspIleAspLeuLeuGluLysLysGlyLeuVal-118 |
| SEQ. ID. NO. 12674 | 142-ArgLysAsnAsnProLysGlnIleArgAspTrpAsnAspLeuAlaLysAspGlyVal-160 |
| SEQ. ID. NO. 12675 | 167-ProLysThrSerGlyAsnGly-173 |
| SEQ. ID. NO. 12676 | 187-ThrThrAsnGlyAsnGluGlnGluAlaGlnLys-197 |
| SEQ. ID. NO. 12677 | 211-AsnGlyGlyArgAlaAla-216 |
| SEQ. ID. NO. 12678 | 238-TyrValSerLysLysLeuThr-244 |
| SEQ. ID. NO. 12679 | 270-ValAlaLysLysGlyThrGlnLysThrAlaArgAla-281 |
| SEQ. ID. NO. 12680 | 300-LeuArgProArgAsnProGluValLeuAlaArgHisLysAlaAspPheProAsp-317 |
| SEQ. ID. NO. 12681 | 319-AspThrPheSerProGluLysLysPheGlyGly-329 |
| SEQ. ID. NO. 12682 | 347-LeuThrAlaGlnLys-351 |
| 929-2 | |
| AMPHI Regions - AMPHI | |
| SEQ. ID. NO. 12683 | 25-ValProAspGlyValLys-30 |
| SEQ. ID. NO. 12684 | 34-TrpThrLeuLeuAlaMetPheValGlyValIleAlaAlaIleIle-48 |
| SEQ. ID. NO. 12685 | 76-GlyAlaAlaMetSerAspAlaLeuSerAlaPhe-86 |
| SEQ. ID. NO. 12686 | 155-HisProIleMetGlnSerIleAlaGlySerTyrGlySerAsnProAlaLys-171 |
| SEQ. ID. NO. 12687 | 180-TyrLeuAlaLeuVal-184 |
| SEQ. ID. NO. 12688 | 204-ProLeuIleValAsnLeuIleAlaGluAsnLeuGly-215 |
| SEQ. ID. NO. 12689 | 233-GlyValIleAlaPhePhe-238 |
| SEQ. ID. NO. 12690 | 265-ArgLeuArgGluMetGlyLysMetSer-273 |
| SEQ. ID. NO. 12691 | 280-AlaValIlePheGlyIle-285 |
| SEQ. ID. NO. 12692 | 355-LeuGlyLeuIleLysTrpPheSerGlyValLeuAlaGluSerValGlyGlyLeu-372 |
| SEQ. ID. NO. 12693 | 398-ThrAlaHisIleThrAlaMetPheGlyAlaPhePheAla-410 |
| SEQ. ID. NO. 12694 | 452-TyrThrThrMetGlyGluTrpTrp-459 |
| Antigenic Index - Jameson-Wolf | |
| SEQ. ID. NO. 12695 | 25-ValProAspGlyValLysProGln-32 |
| SEQ. ID. NO. 12696 | 71-ThrAlaAspLysProGlyAlaAlaMet-79 |
| SEQ. ID. NO. 12697 | 122-GlyArgLysThrLeuGlyIle-128 |
| SEQ. ID. NO. 12698 | 143-ThrProSerAsnThrAlaArgGlyGlyGly-152 |
| SEQ. ID. NO. 12699 | 163-GlySerTyrGlySerAsnProAlaLysGlyThrGluGlyLysMetGlyLys-179 |
| SEQ. ID. NO. 12700 | 187-HisSerAsnProIleSer-192 |
| SEQ. ID. NO. 12701 | 213-AsnLeuGlySerSerPhe-218 |
| SEQ. ID. NO. 12702 | 248-TyrProProGluIleLysGluThrProAsn-257 |
| SEQ. ID. NO. 12703 | 261-PheAlaLysAspArgLeuArgGluMetGlyLysMetSerAlaAspGluIle-277 |
| SEQ. ID. NO. 12704 | 328-AspValLeuLysGluLysSerAlaTrp-336 |
| Hydrophilic Regions - Hopp-Woods | |
| SEQ. ID. NO. 12705 | 71-ThrAlaAspLysProGlyAlaAlaMet-79 |
| SEQ. ID. NO. 12706 | 146-AsnThrAlaArgGly-150 |
| SEQ. ID. NO. 12707 | 168-AsnProAlaLysGlyThrGluGlyLysMetGlyLys-179 |
| SEQ. ID. NO. 12708 | 250-ProGluIleLysGluThrProAsn-257 |
| SEQ. ID. NO. 12709 | 261-PheAlaLysAspArgLeuArgGluMetGlyLysMetSerAlaAspGluIle-277 |
| SEQ. ID. NO. 12710 | 328-AspValLeuLysGluLysSerAlaTrp-336 |
| 930-1 | |
| AMPHI Regions - AMPHI | |
| SEQ. ID. NO. 12711 | 8-LeuProAsnIleArg-12 |
| SEQ. ID. NO. 12712 | 69-AsnThrGlyGluThrValAsnGlnLeuMetGly-79 |
| SEQ. ID. NO. 12713 | 121-LeuHisAlaGlyAsnIleAsnGlnIleMetSerLeu-132 |
| SEQ. ID. NO. 12714 | 147-IleLeuAlaAlaPro-151 |
| SEQ. ID. NO. 12715 | 165-ProSerTyrLeuArgSerIleArgIle-173 |
| SEQ. ID. NO. 12716 | 199-AspLeuLeuAsnLeuArgAsp-205 |

TABLE 1-continued

| | |
|---|---|
| SEQ. ID. NO. 12717 | 207-GluGlnGlyLeuGluAsnLeuLysArgLeuProThr-218 |
| SEQ. ID. NO. 12718 | 280-SerAspMetPheTyr-284 |
| SEQ. ID. NO. 12719 | 288-GlyArgSerIleGlyGlyThrProAsp-296 |
| SEQ. ID. NO. 12720 | 333-ArgTyrHisGlnAlaValSerGlyLeuSerGluValTyrAsp-346 |
| SEQ. ID. NO. 12721 | 400-TrpLeuAlaGluLeu-404 |
| SEQ. ID. NO. 12722 | 427-MetLysAspAlaLeuArgAlaProGluGluAlaPheGlyGluGly-441 |
| SEQ. ID. NO. 12723 | 472-HisAlaGlnTrpAsnLys-477 |
| Antigenic Index - Jameson-Wolf | |
| SEQ. ID. NO. 12724 | 32-SerProAsnProAlaGluIleArgMetGlnGlnAspIleGlnGlnArgGlnArgGluGluGlnLeuArgGlnThrMetGlnProGluSerAspValArgLeu HisGlnLysAsnThrGlyGluThr-73 |
| SEQ. ID. NO. 12725 | 77-LeuMetGlyAspAspSerSerGln-84 |
| SEQ. ID. NO. 12726 | 93-ValLeuGluGlyGluHisHisAla-100 |
| SEQ. ID. NO. 12727 | 108-ArgAlaLeuArgGluThrGly-114 |
| SEQ. ID. NO. 12728 | 118-GlyLysCysLeuHisAlaGlyAsn-125 |
| SEQ. ID. NO. 12729 | 151-ProGlnAspLeuAsnSerGlyLysLeu-159 |
| SEQ. ID. NO. 12730 | 171-IleArgIleAspArgSerAsnAspAspGlnThrHis-182 |
| SEQ. ID. NO. 12731 | 191-AsnLysPheProThrArgSerAsnAspLeuLeuAsn-202 |
| SEQ. ID. NO. 12732 | 204-ArgAspLeuGluGlnGlyLeuGluAsnLeuLysArgLeuProThrAlaGluAlaAspLeu-223 |
| SEQ. ID. NO. 12733 | 228-ValGluGlyGluProAsnGlnSerAspVal-237 |
| SEQ. ID. NO. 12734 | 242-ArgGlnArgLeuLeuPro-247 |
| SEQ. ID. NO. 12735 | 252-ValGlyMetAspAsnSerGlySerGluAlaThrGlyLysTyrGlnGly-267 |
| SEQ. ID. NO. 12736 | 273-AlaAspAsnProLeuGlyLeu-279 |
| SEQ. ID. NO. 12737 | 287-TyrGlyArgSerIleGlyGlyThrProAspGluGluSerPheAspGlyHisArgLysGluGlyGlySerAsn-310 |
| SEQ. ID. NO. 12738 | 329-HisAsnGlyTyrArg-333 |
| SEQ. ID. NO. 12739 | 343-GluValTyrAspTyrAsnGlyLysSerTyrAsnThrAspPheGlyPhe-358 |
| SEQ. ID. NO. 12740 | 362-LeuTyrArgAspAlaLysArgLysThr-370 |
| SEQ. ID. NO. 12741 | 377-TrpMetArgGluThrLysSerTyrIleAspAspAlaGluLeuThrValGlnArgArgLysThrAla-398 |
| SEQ. ID. NO. 12742 | 408-GluTyrIleGlyArgSerThrAlaAspPheLysLeuLysTyrLysArgGlyThrGlyMetLysAspAlaLeuArgAlaProGluGluAlaPheGlyGluGly ThrSerArg-444 |
| SEQ. ID. NO. 12743 | 451-SerAlaAspValAsnThrPro-457 |
| SEQ. ID. NO. 12744 | 474-GlnTrpAsnLysThrProLeuThrSerGlnAspLysLeuAla-487 |
| SEQ. ID. NO. 12745 | 492-HisThrValArgGlyPheAspGlyGluMet-501 |
| SEQ. ID. NO. 12746 | 503-LeuSerAlaGluArgGlyTrpTyrTrpArgAsnAspLeuSerTrpGlnPheLysProGlyHis-523 |
| SEQ. ID. NO. 12747 | 535-SerGlyGlnSerAlaLys-540 |
| SEQ. ID. NO. 12748 | 572-ArgAlaLeuLysLysProGluPhePheGlnSerArgLysTrpAlaSerGly-588 |
| Hydrophilic Regions - Hopp-Woods | |
| SEQ. ID. NO. 12749 | 34-AsnProAlaGluIleArgMetGlnGlnAspIleGlnGlnArgGlnArgGluGluGlnLeuArgGln-55 |
| SEQ. ID. NO. 12750 | 57-MetGlnProGluSerAspValArgLeuHisGlnLysAsnThrGlyGluThr-73 |
| SEQ. ID. NO. 12751 | 78-MetGlyAspAspSerSerGln-84 |
| SEQ. ID. NO. 12752 | 93-ValLeuGluGlyGluHisHisAla-100 |
| SEQ. ID. NO. 12753 | 108-ArgAlaLeuArgGluThrGly-114 |
| SEQ. ID. NO. 12754 | 152-GlnAspLeuAsnSerGlyLys-158 |
| SEQ. ID. NO. 12755 | 171-IleArgIleAspArgSerAsnAspAspGlnThrHis-182 |
| SEQ. ID. NO. 12756 | 193-PheProThrArgSerAsnAsp-199 |
| SEQ. ID. NO. 12757 | 204-ArgAspLeuGluGlnGlyLeuGluAsnLeuLysArgLeuProThrAlaGluAlaAspLeu-223 |
| SEQ. ID. NO. 12758 | 228-ValGluGlyGluProAsnGlnSer-235 |
| SEQ. ID. NO. 12759 | 254-MetAspAsnSerGlySerGluAlaThrGly-263 |
| SEQ. ID. NO. 12760 | 291-IleGlyGlyThrProAspGluGluSerPheAspGlyHisArgLysGluGlyGlySer-309 |
| SEQ. ID. NO. 12761 | 345-TyrAspTyrAsnGly-349 |
| SEQ. ID. NO. 12762 | 362-LeuTyrArgAspAlaLysArgLysThr-370 |
| SEQ. ID. NO. 12763 | 377-TrpMetArgGluThrLysSerTyrIleAspAspAlaGluLeuThrValGlnArgArgLysThr-397 |
| SEQ. ID. NO. 12764 | 413-SerThrAlaAspPheLysLeuLysTyrLysArgGlyThrGlyMetLysAspAlaLeuArgAlaProGluGluAlaPheGly-439 |
| SEQ. ID. NO. 12765 | 479-ProLeuThrSerGlnAspLysLeuAla-487 |
| SEQ. ID. NO. 12766 | 495-ArgGlyPheAspGlyGluMet-501 |
| SEQ. ID. NO. 12767 | 503-LeuSerAlaGluArg-507 |
| SEQ. ID. NO. 12768 | 572-ArgAlaLeuLysLysProGluPhePheGln-581 |
| 931-2 | |
| AMPHI Regions - AMPHI | |
| SEQ. ID. NO. 12769 | 43-LysAlaProLysThrValAlaAsnPheValArgTyrAlaArgLys-57 |
| SEQ. ID. NO. 12770 | 65-PheHisArgValIleAspGly-71 |
| SEQ. ID. NO. 12771 | 81-GluAspLeuAlaGlnLysAlaSerAspLys-90 |
| SEQ. ID. NO. 12772 | 94-AsnGluSerGlyAsnGlyLeuLysAsnThr-103 |
| SEQ. ID. NO. 12773 | 142-ThrValPheGlyArgValGluSerGlyMetAsnThrValSerLysIleAlaArgValLysThrAlaThrArgGlyPhe-167 |
| Antigenic Index - Jameson-Wolf | |
| SEQ. ID. NO. 12774 | 1-MetLysProLysPhe-5 |
| SEQ. ID. NO. 12775 | 30-ThrAspMetGlyAsn-34 |
| SEQ. ID. NO. 12776 | 38-ValLeuAspGluSerLysAlaProLysThr-47 |
| SEQ. ID. NO. 12777 | 53-ArgTyrAlaArgLysGlyPheTyrAspAspThrValPhe-65 |
| SEQ. ID. NO. 12778 | 76-GlyGlyGlyLeuThrGluAspLeuAlaGlnLysAlaSerAspLysAlaValAlaAsnGluSerGlyAsnGlyLeuLysAsnThrAla-104 |
| SEQ. ID. NO. 12779 | 110-AlaArgThrThrAlaProAspSerAlaThr-119 |
| SEQ. ID. NO. 12780 | 128-AspAsnAlaSerLeuAspTyrLysAsnGlyGlnTyr-139 |
| SEQ. ID. NO. 12781 | 145-GlyArgValGluSerGlyMetAsnThrVal-154 |
| SEQ. ID. NO. 12782 | 156-LysIleAlaArgValLysThrAlaThrArgGlyPhe-167 |
| SEQ. ID. NO. 12783 | 176-ValLysIleArgArg-180 |
| Hydrophilic Regions - Hopp-Woods | |
| SEQ. ID. NO. 12784 | 1-MetLysProLysPhe-5 |
| SEQ. ID. NO. 12785 | 30-ThrAspMetGlyAsn-34 |
| SEQ. ID. NO. 12786 | 38-ValLeuAspGluSerLysAlaProLysThr-47 |
| SEQ. ID. NO. 12787 | 78-GlyLeuThrGluAspLeuAlaGlnLysAlaSerAspLysAlaValAlaAsnGluSerGlyAsnGlyLeuLysAsnThrAla-104 |
| SEQ. ID. NO. 12788 | 113-ThrAlaProAspSerAlaThr-119 |

TABLE 1-continued

SEQ. ID. NO. 12789 130-AlaSerLeuAspTyrLysAsn-136
SEQ. ID. NO. 12790 145-GlyArgValGluSerGlyMet-151
SEQ. ID. NO. 12791 156-LysIleAlaArgValLysThrAlaThr-164
SEQ. ID. NO. 12792 176-ValLysIleArgArg-180
932
AMPHI Regions - AMPHI
SEQ. ID. NO. 12793 27-AspAlaAlaSerPheTrpGluLeuLysAsn-36
SEQ. ID. NO. 12794 38-AlaAsnProTyrPro-42
SEQ. ID. NO. 12795 46-SerAlaAlaLeuAspGlnTyrProSer-54
SEQ. ID. NO. 12796 60-GlnLeuLysAspMetGlnGluCys-67
Antigenic Index - Jameson-Wolf
SEQ. ID. NO. 12797 18-PheGlyGlyPheLysProAsnProTrpAsp-27
SEQ. ID. NO. 12798 34-LeuLysAsnTyrAlaAsnProTyrProGlySer-44
SEQ. ID. NO. 12799 50-AspGlnTyrProSerLysAlaArgArgArgGlnLeuLysAspMetGlnGluCysGlyTyrAspProIleAspGlyGlyLysSerGluAlaAspAlaCysLeu ArgLysLysGlyTrpCysArgLysGlyPheAspProTyrProGluAsnLysLysTyrGluTrpProArgGluGluGlyLysThrLys-112
Hydrophilic Regions - Hopp-Woods
SEQ. ID. NO. 12800 52-TyrProSerLysAlaArgArgArgGlnLeuLysAspMetGlnGluCysGlyTyrAspProIleAspGlyGlyLysSerGluAlaAspAlaCysLeuArgLys LysGlyTrpCys-89
SEQ. ID. NO. 12801 91-LysGlyPheAspProTyrProGluAsnLysLysTyrGluTrpProArgGluGluGlyLysThrLys-112
933
AMPHI Regions - AMPHI
SEQ. ID. NO. 12802 6-LysThrSerGluTyr-10
SEQ. ID. NO. 12803 37-GlnPheGluAsnIleAsnAsnSerLysLys-46
SEQ. ID. NO. 12804 61-GlyPheAlaArgGlyLeu-66
SEQ. ID. NO. 12805 75-ThrGluGluGlnIleArgLysTyrPheLysGluCysPheAsn-88
SEQ. ID. NO. 12806 94-ArgAspTyrSerThrCysGlnAla-101
SEQ. ID. NO. 12807 133-SerValGlyAsnTyrThrGluTrpAlaAsnGlnValIleHisHisIleGluAsnTyrValSerPheAlaAlaHisLeuTyrSerGlyLeuAspProPheHisTyr IleGluVal-170
SEQ. ID. NO. 12808 261-GluAsnProIleAspAspLeuLysSerLeuAspGlyHisGlnIleIleLysValAsn-279
SEQ. ID. NO. 12809 308-GlyPhePheThrLys-312
SEQ. ID. NO. 12810 355-TrpLeuArgValIleAspGlyHisSerAsn-364
SEQ. ID. NO. 12811 373-ProValGluGlyTyrArgLysGly-380
SEQ. ID. NO. 12812 430-AlaGlyValTyrAlaThrTrpHis-437
SEQ. ID. NO. 12813 451-TrpMetGlnTyrGln-455
SEQ. ID. NO. 12814 466-GlyThrGluArgPheThr-471
SEQ. ID. NO. 12815 473-LysGlyIleThrAlaSer-478
SEQ. ID. NO. 12816 482-GlyTyrAsnAlaLeuLeuAla-488
SEQ. ID. NO. 12817 547-LeuTyrLysAsnIleAlaIleGlu-554
SEQ. ID. NO. 12818 556-PheAlaAlaValAsn-560
SEQ. ID. NO. 12819 605-PheAsnArgGlnThrGly-610
Antigenic Index - Jameson-Wolf
SEQ. ID. NO. 12820 1-LysLysLeuArgAspLysThrSerGluTyrTrpLysLysGluThr-15
SEQ. ID. NO. 12821 19-ThrGluAspAsnProLysValProPro-27
SEQ. ID. NO. 12822 32-TyrProArgThrTyrGln-37
SEQ. ID. NO. 12823 39-GluAsnIleAsnAsnSerLysLysIleSer-48
SEQ. ID. NO. 12824 50-TyrAspGlnGluTyrThrGluGlyTyr-58
SEQ. ID. NO. 12825 67-GlyValAlaLysArgAsnGlyAspThrGluGluGlnIleArgLysTyrPheLys-84
SEQ. ID. NO. 12826 86-CysPheAsnSerAsnThrLysIleArgAspTyrSerThrCysGlnAlaGluLysPheGlySerHisPro-108
SEQ. ID. NO. 12827 118-LeuGlyProLysIleLysAsnSerHisIleAsnSerGluIle-131
SEQ. ID. NO. 12828 159-TyrSerGlyLeuAspPro-164
SEQ. ID. NO. 12829 169-GluValThrAspAsnSerHis-175
SEQ. ID. NO. 12830 184-AspGluPheArgLeuGluAsnSerLeuTrpGluProArgTrpAspSerAsnValGlyLysLeuLysThrThrAsnAlaAspIleArgPheAsnThrLys SerGluSerLeuLeuValLysGluAspTyrAlaGlyGlyAlaArgPheArgPheAlaTyrAspProLysGluAlaLysAsn-243
SEQ. ID. NO. 12831 249-GluLysAsnValThrGlyThrSer-256
SEQ. ID. NO. 12832 259-IlePheGluAsnProIleAspAspLeuLysSerLeuAspGlyHisGlnIleIle-276
SEQ. ID. NO. 12833 278-ValAsnGlyThrAlaAspLysHisAlaPheArgLeuSerGlyLysHisGlnLysGly-296
SEQ. ID. NO. 12834 302-LeuGlnGlnArgProGluGlyPhe-309
SEQ. ID. NO. 12835 312-LysValGlnGluArgAspAspMet-319
SEQ. ID. NO. 12836 336-ArgLeuAsnAsnLysAsnSerAspIlePheAspArgThrLeuProArgLysGlyLeu-354
SEQ. ID. NO. 12837 359-IleAspGlyHisSerAsnGlnTrpValGlnGlyLysThrAlaProValGluGlyTyrArgLysGlyVal-381
SEQ. ID. NO. 12838 391-GlnAsnGluSerAsnGlnLeu-397
SEQ. ID. NO. 12839 402-MetGlyGlyGlnAlaGluGlnArgSerThrPheHisAsnProAspThrAspAsnLeuThr-421
SEQ. ID. NO. 12840 423-GlyAsnValLysGly-427
SEQ. ID. NO. 12841 439-LeuGlnAspLysGlnThrGlyAlaTyrAlaAspSer-450
SEQ. ID. NO. 12842 455-GlnArgPheArgHisArgIleAsnThrGluAspGlyThrGluArgPheThrSerLysGlyIleThrAla-477
SEQ. ID. NO. 12843 490-HisPheThrLysLysGlyAsnSerLeu-498
SEQ. ID. NO. 12844 513-ValAsnGlyLysPheSerAspSerGluAsnAla-523
SEQ. ID. NO. 12845 528-LeuGlySerArgGlnLeuGlnThr-535
SEQ. ID. NO. 12846 566-LysProPheGlyValGluMetAspGlyGluArgArgValIleAsnAsnLysThrAlaIleGluSer-587
SEQ. ID. NO. 12847 593-ValLysIleLysSer-597
SEQ. ID. NO. 12848 604-ThrPheAsnArgGlnThrGlyLysHisHisGlnAlaLysGlnGly-618
Hydrophilic Regions - Hopp-Woods
SEQ. ID. NO. 12849 1-LysLysLeuArgAspLysThrSerGluTyrTrpLysLysGluThr-15
SEQ. ID. NO. 12850 20-GluAspAsnProLys-24
SEQ. ID. NO. 12851 42-AsnAsnSerLysLysIleSer-48
SEQ. ID. NO. 12852 67-GlyValAlaLysArgAsnGlyAspThrGluGluGlnIleArgLysTyrPheLys-84
SEQ. ID. NO. 12853 91-ThrLysIleArgAspTyrSer-97
SEQ. ID. NO. 12854 100-GlnAlaGluLysPheGly-105

TABLE 1-continued

| | |
|---|---|
| SEQ. ID. NO. 12855 | 120-ProLysIleLysAsn-124 |
| SEQ. ID. NO. 12856 | 184-AspGluPheArgLeuGlu-189 |
| SEQ. ID. NO. 12857 | 195-ProArgTrpAspSerAsnValGlyLysLeuLysThrThrAsnAlaAspIleArgPheAsnThrLysSerGluSerLeuLeuValLysGluAspTyrAla Gly-228 |
| SEQ. ID. NO. 12858 | 236-TyrAspProLysGluAlaLysAsn-243 |
| SEQ. ID. NO. 12859 | 250-LysAsnValThrGly-254 |
| SEQ. ID. NO. 12860 | 262-AsnProIleAspAspLeuLysSerLeuAsp-271 |
| SEQ. ID. NO. 12861 | 280-GlyThrAlaAspLysHisAlaPhe-287 |
| SEQ. ID. NO. 12862 | 289-LeuSerGlyLysHisGlnLys-295 |
| SEQ. ID. NO. 12863 | 303-GlnGlnArgProGluGlyPhe-309 |
| SEQ. ID. NO. 12864 | 313-ValGlnGluArgAspAspMet-319 |
| SEQ. ID. NO. 12865 | 337-LeuAsnAsnLysAsnSerAspIlePheAsp-346 |
| SEQ. ID. NO. 12866 | 375-GluGlyTyrArgLysGlyVal-381 |
| SEQ. ID. NO. 12867 | 392-AsnGluSerAsnGln-396 |
| SEQ. ID. NO. 12868 | 405-GlnAlaGluGlnArgSerThrPheHis-413 |
| SEQ. ID. NO. 12869 | 415-ProAspThrAspAsnLeuThr-421 |
| SEQ. ID. NO. 12870 | 439-LeuGlnAspLysGlnThr-444 |
| SEQ. ID. NO. 12871 | 455-GlnArgPheArgHisArgIleAsnThrGluAspGlyThrGluArgPheThrSer-472 |
| SEQ. ID. NO. 12872 | 490-HisPheThrLysLysGlyAsnSer-497 |
| SEQ. ID. NO. 12873 | 516-LysPheSerAspSerGluAsnAla-523 |
| SEQ. ID. NO. 12874 | 568-PheGlyValGluMetAspGlyGluArgArgValIleAsn-580 |
| SEQ. ID. NO. 12875 | 593-ValLysIleLysSer-597 |
| SEQ. ID. NO. 12876 | 607-ArgGlnThrGlyLysHisHisGlnAlaLysGlnGly-618 |
| 935 | |
| AMPHI Regions - AMPHI | |
| SEQ. ID. NO. 12877 | 41-ValSerAspLysTrpAla-46 |
| SEQ. ID. NO. 12878 | 56-AlaProArgValVal-60 |
| SEQ. ID. NO. 12879 | 72-LeuGluHisSerLeuArgAsp-78 |
| SEQ. ID. NO. 12880 | 87-LeuIleAlaSerLeuAlaAspLeuTyrAlaLysLeu-98 |
| SEQ. ID. NO. 12881 | 111-AlaLeuLeuAlaLysLeuAlaGlyArgProAlaGluAlaValAlaArgTyrArgGlu-129 |
| SEQ. ID. NO. 12882 | 158-GluArgHisPheAlaGlu-163 |
| SEQ. ID. NO. 12883 | 172-ProValLeuGluAsnValGlyArgPheArgLysLysThrGlu-185 |
| SEQ. ID. NO. 12884 | 375-LysArgLeuGlyGluSerAlaThrValPheGlyGlyTrpGlnPheVal-390 |
| SEQ. ID. NO. 12885 | 415-AlaGlyTrpAlaGlnGluTrpArgGlnLeuGlyGlyLeu-427 |
| SEQ. ID. NO. 12886 | 435-TyrAlaArgArgAsnTyrLysGlyIleAlaAlaPhe-446 |
| Antigenic Index - Jameson-Wolf | |
| SEQ. ID. NO. 12887 | 27-AlaIleLeuAspAspLysAlaLeu-34 |
| SEQ. ID. NO. 12888 | 39-ArgSerValSerAspLysTrpAlaGluSerAspTrpLysValGluAsnAspAlaProArgValValAspGlyAspPhe-64 |
| SEQ. ID. NO. 12889 | 70-LysMetLeuGluHisSerLeuArgAspAlaLeuAsnGlyAsnGln-84 |
| SEQ. ID. NO. 12890 | 97-LysLeuProAspTyrAspAla-103 |
| SEQ. ID. NO. 12891 | 108-ArgAlaArgAlaLeu-112 |
| SEQ. ID. NO. 12892 | 116-LeuAlaGlyArgProAlaGluAlaValAlaArgTyrArgGluLeuHisGlyGluAsnAlaAlaAspGluArgIleLeu-141 |
| SEQ. ID. NO. 12893 | 145-AlaAlaAlaGluPheAspAspPheArgLeuLysSerAlaGluArgHisPheAlaGluAlaAlaLysLeuAspLeu-169 |
| SEQ. ID. NO. 12894 | 176-AsnValGlyArgPheArgLysLysThrGluGly-186 |
| SEQ. ID. NO. 12895 | 192-PheSerGlyGlyIle-196 |
| SEQ. ID. NO. 12896 | 199-AlaValAsnArgAsnAlaAsnAsnAlaAla-208 |
| SEQ. ID. NO. 12897 | 210-GlnTyrCysArgGlnAsnGlyGlyArgGln-219 |
| SEQ. ID. NO. 12898 | 224-SerArgAlaGluArgAlaAla-230 |
| SEQ. ID. NO. 12899 | 236-IleGluAlaGluLysLeuThrProLeuAlaAsp-246 |
| SEQ. ID. NO. 12900 | 253-ArgSerAsnIleGlyGlyThrSerTyr-261 |
| SEQ. ID. NO. 12901 | 263-PheSerLysLysSerAlaTyrAspAspGlyPheGlyArg-275 |
| SEQ. ID. NO. 12902 | 279-GlyTrpGlnTyrLysAsnAlaArgGlnThr-288 |
| SEQ. ID. NO. 12903 | 300-SerGlySerAspGlyPheAspAlaLysThrLysArgValAsnAsnArgArgLeuProProTyr-320 |
| SEQ. ID. NO. 12904 | 332-HisThrTyrArgProAsnProGlyTrp-340 |
| SEQ. ID. NO. 12905 | 347-GluHisTyrArgGlnArgTyrArgGluGlnAspArgAlaGluTyrAsnAsnGlyArgGlnAspGlyPheTyr-370 |
| SEQ. ID. NO. 12906 | 373-SerAlaLysArgLeuGlyGlu-379 |
| SEQ. ID. NO. 12907 | 392-PheValProLysArgGluThrVal-399 |
| SEQ. ID. NO. 12908 | 406-AlaAlaTyrArgArgAsnGlyValTyrAlaGly-416 |
| SEQ. ID. NO. 12909 | 425-GlyGlyLeuAsnSerArgValSerAlaSerTyrAlaArgArgAsnTyrLysGly-442 |
| SEQ. ID. NO. 12910 | 448-ThrGluAlaGlnArgAsnArgGluTrpAsn-457 |
| SEQ. ID. NO. 12911 | 463-SerHisAspLysLeuSerTyrLysGly-471 |
| SEQ. ID. NO. 12912 | 480-PheGlyArgThrGluSerAsnValProTyrAlaLysArgArgAsnSerGlu-496 |
| SEQ. ID. NO. 12913 | 501-AlaAspTrpArgPhe-505 |
| Hydrophilic Regions - Hopp-Woods | |
| SEQ. ID. NO. 12914 | 27-AlaIleLeuAspAspLysAlaLeu-34 |
| SEQ. ID. NO. 12915 | 39-ArgSerValSerAspLysTrpAlaGluSerAspTrpLysValGluAsnAspAlaProArgValValAsp-61 |
| SEQ. ID. NO. 12916 | 70-LysMetLeuGluHisSerLeuArgAspAlaLeuAsn-81 |
| SEQ. ID. NO. 12917 | 108-ArgAlaArgAlaLeu-112 |
| SEQ. ID. NO. 12918 | 116LeuAlaGlyArgProAlaGluAlaValAlaArgTyrArgGluLeuHisGly-132 |
| SEQ. ID. NO. 12919 | 134-AsnAlaAlaAspGluArgIleLeu-141 |
| SEQ. ID. NO. 12920 | 145-AlaAlaAlaGluPheAspAspPheArgLeuLysSerAlaGluArgHisPheAlaGluAlaAlaLysLeuAspLeu-169 |
| SEQ. ID. NO. 12921 | 176-AsnValGlyArgPheArgLysLysThrGluGly-186 |
| SEQ. ID. NO. 12922 | 200-ValAsnArgAsnAlaAsn-205 |
| SEQ. ID. NO. 12923 | 212-CysArgGlnAsnGlyGlyArgGln-219 |
| SEQ. ID. NO. 12924 | 224-SerArgAlaGluArgAlaAla-230 |
| SEQ. ID. NO. 12925 | 236-IleGluAlaGluLysLeuThrPro-243 |
| SEQ. ID. NO. 12926 | 265-LysLysSerAlaTyrAspAspGlyPheGly-274 |
| SEQ. ID. NO. 12927 | 283-LysAsnAlaArgGlnThr-288 |
| SEQ. ID. NO. 12928 | 303-AspGlyPheAspAlaLysThrLysArgValAsnAsnArgArgLeuPro-318 |
| SEQ. ID. NO. 12929 | 348-HisTyrArgGlnArgTyrArgGluGlnAspArgAlaGluTyrAsnAsnGlyArgGlnAsp-367 |

TABLE 1-continued

| | |
|---|---|
| SEQ. ID. NO. 12930 | 373-SerAlaLysArgLeuGlyGlu-379 |
| SEQ. ID. NO. 12931 | 393-ValProLysArgGluThrVal-399 |
| SEQ. ID. NO. 12932 | 407-AlaTyrArgArgAsnGly-412 |
| SEQ. ID. NO. 12933 | 435-TyrAlaArgArgAsnTyrLys-441 |
| SEQ. ID. NO. 12934 | 449-GluAlaGlnArgAsnArgGluTrp-456 |
| SEQ. ID. NO. 12935 | 463-SerHisAspLysLeuSerTyr-469 |
| SEQ. ID. NO. 12936 | 480-PheGlyArgThrGluSer-485 |
| SEQ. ID. NO. 12937 | 489-TyrAlaLysArgArgAsnSerGlu-496 |
| 936-1 | |
| AMPHI Regions - AMPHI | |
| SEQ. ID. NO. 12938 | 10-ThrLeuIleAlaAlaIle-15 |
| SEQ. ID. NO. 12939 | 22-GlyCysValSerAlaVal-27 |
| SEQ. ID. NO. 12940 | 100-GlnPheValGlyGlnIle-105 |
| SEQ. ID. NO. 12941 | 112-AlaGluGlyValTyrAsnTyrIleThrValAlaSerLeuProArgThrAlaGlyAspIleAlaGlyAsp-134 |
| Antigenic Index - Jameson-Wolf | |
| SEQ. ID. NO. 12942 | 1-MetLysProLysProHisThrVal-8 |
| SEQ. ID. NO. 12943 | 33-ValGlyAlaLysSerAlaValAspArgArgThrThrGlyAlaGlnThrAspAspAsnValMet-53 |
| SEQ. ID. NO. 12944 | 56-ArgIleGluThrThrAlaArgSerTyrLeuArgGlnAsnAsnGlnThrLysGlyTyr-74 |
| SEQ. ID. NO. 12945 | 94-AlaThrGluGlyGluLysGlnPhe-101 |
| SEQ. ID. NO. 12946 | 106-AlaArgSerGluGlnAlaAla-112 |
| SEQ. ID. NO. 12947 | 124-LeuProArgThrAlaGlyAspIleAlaGlyAspThrTrpAsnThrSerLysValArgAla-143 |
| SEQ. ID. NO. 12948 | 149-SerProAlaThrGlnAlaArgValLys-157 |
| SEQ. ID. NO. 12949 | 172-ThrProGluGluGlnAlaGlnIleThr-180 |
| Hydrophilic Regions - Hopp-Woods | |
| SEQ. ID. NO. 12950 | 1-MetLysProLysProHisThr-7 |
| SEQ. ID. NO. 12951 | 37-SerAlaValAspArgArgThrThrGlyAlaGlnThrAspAspAsnValMet-53 |
| SEQ. ID. NO. 12952 | 56-ArgIleGluThrThrAla-61 |
| SEQ. ID. NO. 12953 | 68-AsnAsnGlnThrLysGlyTyr-74 |
| SEQ. ID. NO. 12954 | 94-AlaThrGluGlyGluLysGlnPhe-101 |
| SEQ. ID. NO. 12955 | 106-AlaArgSerGluGlnAlaAla-112 |
| SEQ. ID. NO. 12956 | 125-ProArgThrAlaGly-129 |
| SEQ. ID. NO. 12957 | 152-ThrGlnAlaArgValLys-157 |
| SEQ. ID. NO. 12958 | 172-ThrProGluGluGlnAlaGlnIle-179 |
| 937 | |
| AMPHI Regions - AMPHI | |
| SEQ. ID. NO. 12959 | 6-LeuProAlaLeuProAlaIleLeuProLeuSerThr-17 |
| SEQ. ID. NO. 12960 | 190-AsnGlySerLysThrLeuSer-196 |
| Antigenic Index - Jameson-Wolf | |
| SEQ. ID. NO. 12961 | 27-AspIleMetThrAspLysGlyLysTrpLysLeuGluThr-39 |
| SEQ. ID. NO. 12962 | 44-LeuAsnSerGluAsnAsnArgAlaGluLeu-53 |
| SEQ. ID. NO. 12963 | 72-GluIleGlnGluAsnGlySerAsnThrAsp-81 |
| SEQ. ID. NO. 12964 | 95-GlyAsnThrAspIleTyrGlySerGlySer-104 |
| SEQ. ID. NO. 12965 | 108-HisGluGluArgLysLeuAspGlyAsnSerLysThrArgAsnLysArgMetSerAsp-126 |
| SEQ. ID. NO. 12966 | 135-PheLeuLysAspAspLysAsnProAla-143 |
| SEQ. ID. NO. 12967 | 151-ThrValTyrGluLysSerArgAsnLysAlaSerSerGlyLysSer-165 |
| SEQ. ID. NO. 12968 | 187-TyrArgIleAsnGlySerLysThrLeuSerAspGlyIleArgTyrLysSerGlyAsnTyr-206 |
| SEQ. ID. NO. 12969 | 217-AlaAsnAspArgIleSerLeuThrGlyGly-226 |
| SEQ. ID. NO. 12970 | 231-GlyArgGlnProAspArgThrAspGlyLysArgGluSerSerArgAsnThrSerThr-249 |
| SEQ. ID. NO. 12971 | 273-ValSerGlyGlnSerSerSerGluLeuLysPhe-283 |
| Hydrophilic Regions - Hopp-Woods | |
| SEQ. ID. NO. 12972 | 27-AspIleMetThrAspLysGlyLysTrpLysLeu-37 |
| SEQ. ID. NO. 12973 | 47-GluAsnAsnArgAlaGluLeu-53 |
| SEQ. ID. NO. 12974 | 72-GluIleGlnGluAsnGlySerAsnThr-80 |
| SEQ. ID. NO. 12975 | 108-HisGluGluArgLysLeuAspGlyAsnSerLysThrArgAsnLysArgMetSerAsp-126 |
| SEQ. ID. NO. 12976 | 135-PheLeuLysAspAspLysAsnPro-142 |
| SEQ. ID. NO. 12977 | 151-ThrValTyrGluLysSerArgAsnLysAlaSerSer-162 |
| SEQ. ID. NO. 12978 | 193-LysThrLeuSerAspGlyIleArgTyrLysSer-203 |
| SEQ. ID. NO. 12979 | 217-AlaAsnAspArgIleSer-222 |
| SEQ. ID. NO. 12980 | 232-ArgGlnProAspArgThrAspGlyLysArgGluSerSerArgAsnThr-247 |
| SEQ. ID. NO. 12981 | 277-SerSerSerGluLeuLysPhe-283 |
| 939-2 | |
| AMPHI Regions - AMPHI | |
| SEQ. ID. NO. 12982 | 32-AlaThrValCysAla-36 |
| SEQ. ID. NO. 12983 | 90-AspGlnAspIleLeu-94 |
| SEQ. ID. NO. 12984 | 121-LysIleTyrArgGly-125 |
| SEQ. ID. NO. 12985 | 135-CysMetSerCysHisGly-140 |
| SEQ. ID. NO. 12986 | 151-SerGluIleGlnAlaTyrProArgLeuGlyGly-161 |
| SEQ. ID. NO. 12987 | 169-GluGlnMetAsnAlaTyrLys-175 |
| SEQ. ID. NO. 12988 | 185-GluAspIleAlaAsnArgMetSer-192 |
| Antigenic Index - Jameson-Wolf | |
| SEQ. ID. NO. 12989 | 18-AlaSerProLysAlaAspValGluLysGlyLysGlnVal-30 |
| SEQ. ID. NO. 12990 | 40-AlaAlaAspGlyAsnSerGlyIle-47 |
| SEQ. ID. NO. 12991 | 66-IleGlyIleArgAspGlyLysArgThrHisGlySerAlaAlaVal-80 |
| SEQ. ID. NO. 12992 | 88-LeuSerAspGlnAspIle-93 |
| SEQ. ID. NO. 12993 | 102-LysGlnGlnProLysSerGlyGluAlaAsnProLysGluAsnProGluLeuGly-119 |
| SEQ. ID. NO. 12994 | 122-IleTyrArgGlyGlyLeuSerAspLysLysValPro-133 |
| SEQ. ID. NO. 12995 | 139-HisGlyProSerGlyAlaGlyMetProGlyGlyGlySerGluIleGlnAla-155 |

TABLE 1-continued

| | |
|---|---|
| SEQ. ID. NO. 12996 | 157-ProArgLeuGlyGlyGlnHisGln-164 |
| SEQ. ID. NO. 12997 | 172-AsnAlaTyrLysSerGlyGlnArgLysAsnThrIleMetGluAspIleAlaAsnArgMetSerGluGluAspLeuLysAla-198 |
| Hydrophilic Regions - Hopp-Woods | |
| SEQ. ID. NO. 12998 | 18-AlaSerProLysAlaAspValGluLysGlyLysGlnVal-30 |
| SEQ. ID. NO. 12999 | 40-AlaAlaAspGlyAsnSer-45 |
| SEQ. ID. NO. 13000 | 67-GlyIleArgAspGlyLysArgThrHisGly-76 |
| SEQ. ID. NO. 13001 | 89-SerAspGlnAspIle-93 |
| SEQ. ID. NO. 13002 | 103-GlnGlnProLysSerGlyGluAlaAsnProLysGluAsnProGluLeuGly-119 |
| SEQ. ID. NO. 13003 | 126-GlyLeuSerAspLysLysValPro-133 |
| SEQ. ID. NO. 13004 | 175-LysSerGlyGlnArgLysAsnThrIleMetGluAspIleAlaAsnArgMetSerGluGluAspLeuLysAla-198 |
| 950 | |
| AMPHI Regions - AMPHI | |
| SEQ. ID. NO. 13005 | 33-GlyValHisLysSerAlaHisGly-40 |
| SEQ. ID. NO. 13006 | 71-AlaThrValLysLysThrHisLysHisThrLysAla-82 |
| Antigenic Index - Jameson-Wolf | |
| SEQ. ID. NO. 13007 | 1-MetAsnLysAsnIle-5 |
| SEQ. ID. NO. 13008 | 23-AlaAlaAsnLysProAlaSerAsnAlaThrGlyValHisLysSerAlaHisGlySerCysGlyAlaSerLysSerAlaGluGlySerCysGlyAlaAlaGlySerLysAlaGlyGluGlyLysCysGlyGluGlyLysCysGlyAlaThrValLysLysThrHisLysHisThrLysAlaSerLysAlaLysAlaLysSerAlaGluGlyLysCysGlyGluGlyLysCysGlySerLys-102 |
| Hydrophilic Regions - Hopp-Woods | |
| SEQ. ID. NO. 13009 | 23-AlaAlaAsnLysProAlaSer-29 |
| SEQ. ID. NO. 13010 | 33-GlyValHisLysSerAlaHis-39 |
| SEQ. ID. NO. 13011 | 43-GlyAlaSerLysSerAlaGluGlySerCys-52 |
| SEQ. ID. NO. 13012 | 55-AlaGlySerLysAlaGlyGluGlyLysCysGlyGluGlyLysCys-69 |
| SEQ. ID. NO. 13013 | 71-AlaThrValLysLysThrHisLysHisThrLysAlaSerLysAlaLysAlaLysSerAlaGluGlyLysCysGlyGluGlyLysCysGlySerLys-102 |
| 951 | |
| AMPHI Regions - AMPHI | |
| SEQ. ID. NO. 13014 | 9-LysMetLeuThrValLeuThrAla-16 |
| SEQ. ID. NO. 13015 | 32-AspMetLysGlnProLysGluValGlyLysValPheArgLysGlnGlnArgTyr-49 |
| SEQ. ID. NO. 13016 | 64-ValGlyGluArgValAsn-69 |
| SEQ. ID. NO. 13017 | 129-TrpArgGlnIleGluProIleProGlyLys-138 |
| SEQ. ID. NO. 13018 | 157-HisLeuAspGlyLeuGluGluValLeuAla-166 |
| SEQ. ID. NO. 13019 | 191-AlaGlnLysAlaSerLysAlaValArgArg-200 |
| SEQ. ID. NO. 13020 | 206-GluHisLeuProGluAlaAla-212 |
| SEQ. ID. NO. 13021 | 230-GlyAlaLeuGlnArgLeuAlaLysLeu-238 |
| SEQ. ID. NO. 13022 | 256-LysTyrProGluIleLeuAspGlyPhePheGlu-266 |
| SEQ. ID. NO. 13023 | 280-MetGluIleMetAsnLeuValSerLeuHisArgLeuAspAspAla-294 |
| SEQ. ID. NO. 13024 | 327-ValIleAspGlyTyrAlaGluLys-334 |
| SEQ. ID. NO. 13025 | 336-TyrGlyArgGlyThrGlu-341 |
| SEQ. ID. NO. 13026 | 364-ValArgGlnTrpLeuLys-369 |
| SEQ. ID. NO. 13027 | 397-AlaLeuArgGlnIleGlyArgValArgLysLeuProGluGlnGln-411 |
| SEQ. ID. NO. 13028 | 418-AspAsnLeuSerLysIle-423 |
| SEQ. ID. NO. 13029 | 425-MetLeuAlaLeuSer-429 |
| SEQ. ID. NO. 13030 | 436-GluAlaLeuArgGlyLeuAspLysIleIleGluLys-447 |
| SEQ. ID. NO. 13031 | 479-SerAspLeuGluArgAlaPheArg-486 |
| SEQ. ID. NO. 13032 | 497-AsnLeuGlyTyrSer-501 |
| SEQ. ID. NO. 13033 | 565-HisLeuGlyGluVal-569 |
| SEQ. ID. NO. 13034 | 581-AspValTrpThrGlnAla-586 |
| SEQ. ID. NO. 13035 | 596-TrpArgGluThrLeu-600 |
| Antigenic Index - Jameson-Wolf | |
| SEQ. ID. NO. 13036 | 25-AlaAlaGlyGlyGlyAlaGlyAspMetLysGlnProLysGluValGlyLysValPheArgLysGlnGlnArgTyrSerGluGluGluIleLysAsnGluArgAlaArgLeu-61 |
| SEQ. ID. NO. 13037 | 63-AlaValGlyGluArgValAsn-69 |
| SEQ. ID. NO. 13038 | 79-ThrAlaLeuGlnLysGlyGlnAla-86 |
| SEQ. ID. NO. 13039 | 98-GluArgThrLysSerProGluValAlaGluArgAlaLeuGlu-111 |
| SEQ. ID. NO. 13040 | 128-LysTrpArgGlnIleGluProIleProGlyLysAlaGlnLysArgAlaGlyTrpLeuArgAsnValLeuArgGluArgGlyAsnGlnHisLeuAspGlyLeuGluGluValLeuAlaGlnAlaAspGluGlyGlnAsnArgArg-175 |
| SEQ. ID. NO. 13041 | 185-ValGlnGlnAspGlyLeuAlaGlnLysAlaSerLysAlaValArgArgAlaAlaLeuLys-204 |
| SEQ. ID. NO. 13042 | 221-GlnGlyArgGluLysGluLysAlaIle-229 |
| SEQ. ID. NO. 13043 | 234-ArgLeuAlaLysLeuAspThrGluIleLeuPro-244 |
| SEQ. ID. NO. 13044 | 252-LeuThrAlaArgLysTyrProGluIleLeuAspGlyPhePheGluGlnThrAspThrGlnAsn-272 |
| SEQ. ID. NO. 13045 | 289-HisArgLeuAspAspAlaTyrAla-296 |
| SEQ. ID. NO. 13046 | 302-LeuGluArgAsnProAsnAlaAsp-309 |
| SEQ. ID. NO. 13047 | 319-AlaAsnArgLysGluGlyAlaSer-326 |
| SEQ. ID. NO. 13048 | 330-GlyTyrAlaGluLysAlaTyrGlyArgGlyThrGluGluGlnArgSerArgAla-347 |
| SEQ. ID. NO. 13049 | 355-TyrAlaAspArgArgAspTyrAlaLys-363 |
| SEQ. ID. NO. 13050 | 366-GlnTrpLeuLysLysValSerAla-373 |
| SEQ. ID. NO. 13051 | 377-LeuPheAspLysGlyVal-382 |
| SEQ. ID. NO. 13052 | 389-ValGluLeuAspGlyGlyArgAlaAlaLeu-398 |
| SEQ. ID. NO. 13053 | 400-GlnIleGlyArgValArgLysLeuProGluGlnGlnGlyArgTyrPheThr-416 |
| SEQ. ID. NO. 13054 | 430-LysLeuProAspLysArgGluAlaLeuArgGlyLeuAspLysIleIleGluLysProProAlaGlySerAsnThrGluLeuGlnAla-458 |
| SEQ. ID. NO. 13055 | 470-ArgLeuGlyLysArgLysLysMetIleSerAspLeuGluArgAlaPheArgLeuAlaProAspAsn-491 |
| SEQ. ID. NO. 13056 | 504-ThrAspSerLysArgLeuAspGluGlyPhe-513 |
| SEQ. ID. NO. 13057 | 522-IleAsnProAspAspThrAlaValAsnAspSerIle-533 |
| SEQ. ID. NO. 13058 | 539-LeuLysGlyAspAlaGluSerAla-546 |
| SEQ. ID. NO. 13059 | 551-ArgTyrSerPheGluAsnAspProGluProGluVal-562 |
| SEQ. ID. NO. 13060 | 574-GlyGluArgAspGlnAla-579 |
| SEQ. ID. NO. 13061 | 588-HisLeuThrGlyAspLysLysIleTrpArgGluThrLeuLysArgHisGlyIleAlaLeuProGlnProSerArgLysProArgLys-616 |

TABLE 1-continued

| | |
|---|---|
| Hydrophilic Regions - Hopp-Woods | |
| SEQ. ID. NO. 13062 | 29-GlyAlaGlyAspMetLysGlnProLysGluValGlyLysValPheArgLysGlnGlnArgTyrSerGluGluGluIleLysAsnGluArgAlaArgLeu-61 |
| SEQ. ID. NO. 13063 | 63-AlaValGlyGluArgValAsn-69 |
| SEQ. ID. NO. 13064 | 79-ThrAlaLeuGlnLysGlyGlnAla-86 |
| SEQ. ID. NO. 13065 | 98-GluArgThrLysSerProGluValAlaGluArgAlaLeuGlu-111 |
| SEQ. ID. NO. 13066 | 135-IleProGlyLysAlaGlnLysArgAlaGlyTrp-145 |
| SEQ. ID. NO. 13067 | 149-ValLeuArgGluArgGlyAsnGlnHis-157 |
| SEQ. ID. NO. 13068 | 159-AspGlyLeuGluGluValLeuAlaGlnAlaAspGluGlyGlnAsnArgArg-175 |
| SEQ. ID. NO. 13069 | 189-GlyLeuAlaGlnLysAlaSerLysAlaValArgArgAlaAlaLeuLys-204 |
| SEQ. ID. NO. 13070 | 221-GlnGlyArgGluLysGluLysAlaIle-229 |
| SEQ. ID. NO. 13071 | 234-ArgLeuAlaLysLeuAspThrGluIle-242 |
| SEQ. ID. NO. 13072 | 252-LeuThrAlaArgLysTyrProGluIle-260 |
| SEQ. ID. NO. 13073 | 265-PheGluGlnThrAspThrGlnAsn-272 |
| SEQ. ID. NO. 13074 | 289-HisArgLeuAspAspAlaTyrAla-296 |
| SEQ. ID. NO. 13075 | 302-LeuGluArgAsnProAsn-307 |
| SEQ. ID. NO. 13076 | 319-AlaAsnArgLysGluGlyAlaSer-326 |
| SEQ. ID. NO. 13077 | 331-TyrAlaGluLysAlaTyrGlyArgGlyThrGluGluGlnArgSerArgAla-347 |
| SEQ. ID. NO. 13078 | 355-TyrAlaAspArgArgAspTyrAlaLys-363 |
| SEQ. ID. NO. 13079 | 389-ValGluLeuAspGlyGlyArgAlaAlaLeu-398 |
| SEQ. ID. NO. 13080 | 400-GlnIleGlyArgValArgLysLeuProGluGlnGlnGly-412 |
| SEQ. ID. NO. 13081 | 430-LysLeuProAspLysArgGluAlaLeuArgGlyLeuAspLysIleIleGluLysProProAla-450 |
| SEQ. ID. NO. 13082 | 452-SerAsnThrGluLeuGlnAla-458 |
| SEQ. ID. NO. 13083 | 470-ArgLeuGlyLysArgLysLysMetIleSerAspLeuGluArgAlaPheArgLeuAlaProAspAsn-491 |
| SEQ. ID. NO. 13084 | 504-ThrAspSerLysArgLeuAspGlu-511 |
| SEQ. ID. NO. 13085 | 523-AsnProAspAspThrAlaVal-529 |
| SEQ. ID. NO. 13086 | 541-GlyAspAlaGluSer-545 |
| SEQ. ID. NO. 13087 | 554-PheGluAsnAspProGluProGluVal-562 |
| SEQ. ID. NO. 13088 | 574-GlyGluArgAspGlnAla-579 |
| SEQ. ID. NO. 13089 | 590-ThrGlyAspLysLysIleTrpArgGluThrLeuLysArgHisGly-604 |
| SEQ. ID. NO. 13090 | 609-GlnProSerArgLysProArgLys-616 |
| 952 | |
| AMPHI Regions - AMPHI | |
| SEQ. ID. NO. 13091 | 63-SerValAlaThrLeuLeuAsnAsnPheTyrGlyGln-74 |
| SEQ. ID. NO. 13092 | 81-ValLeuLysLysLeuAsp-86 |
| SEQ. ID. NO. 13093 | 94-PheGluAspMetArgArgIle-100 |
| SEQ. ID. NO. 13094 | 116-GluGlnLeuAlaGlnLeu-121 |
| SEQ. ID. NO. 13095 | 138-SerValLeuArgGlyIleAsp-144 |
| SEQ. ID. NO. 13096 | 163-AlaGlnPheLeuAspAla-168 |
| SEQ. ID. NO. 13097 | 179-LysIleLeuAlaVal-183 |
| Antigenic Index - Jameson-Wolf | |
| SEQ. ID. NO. 13098 | 40-GlnSerTrpLysAlaArgArgAspPheAsnIleValLysGlnAspLeuAspPheSerCys-59 |
| SEQ. ID. NO. 13099 | 70-AsnPheTyrGlyGlnThrLeuThrGluGluGluValLeuLysLysLeuAspLysGluGlnMetArgAlaSerPheGluAspMetArgArgIleMet Pro-102 |
| SEQ. ID. NO. 13100 | 104-LeuGlyPheGluAlaLysGlyTyr-111 |
| SEQ. ID. NO. 13101 | 129-LeuLysTyrArgLysAspAspHisPheSer-138 |
| SEQ. ID. NO. 13102 | 141-ArgGlyIleAspGlyAsnThr-147 |
| SEQ. ID. NO. 13103 | 169-TrpGlnThrArgGluGlyAsnLeuAla-177 |
| SEQ. ID. NO. 13104 | 184-IleProLysLysAlaGluThrIleSer-192 |
| SEQ. ID. NO. 13105 | 199-GlnHisProLysArgGlnThrGlu-206 |
| SEQ. ID. NO. 13106 | 213-ArgGlnAlaArgAlaGlu-218 |
| Hydrophilic Regions - Hopp-Woods | |
| SEQ. ID. NO. 13107 | 41-SerTrpLysAlaArgArgAspPheAsnIleValLysGlnAspLeuAspPhe-57 |
| SEQ. ID. NO. 13108 | 76-LeuThrGluGluGluValLeuLysLysLeuAspLysGluGlnMetArgAlaSerPheGluAspMetArgArgIleMetPro-102 |
| SEQ. ID. NO. 13109 | 104-LeuGlyPheGluAlaLysGly-110 |
| SEQ. ID. NO. 13110 | 130-LysTyrArgLysAspAspHisPheSer-138 |
| SEQ. ID. NO. 13111 | 169-TrpGlnThrArgGluGlyAsnLeu-176 |
| SEQ. ID. NO. 13112 | 184-IleProLysLysAlaGluThrIleSer-192 |
| SEQ. ID. NO. 13113 | 200-HisProLysArgGlnThrGlu-206 |
| SEQ. ID. NO. 13114 | 213-ArgGlnAlaArgAlaGlu-218 |
| 953 | |
| AMPHI Regions - AMPHI | |
| SEQ. ID. NO. 13115 | 39-AsnThrSerThrAsnValGlyGlyPheTyrGlyLeuThr-51 |
| SEQ. ID. NO. 13116 | 75-GlnSerGlySerGlnHisPheThrAspHisLeuLysSerAlaAspIlePheAspAlaAlaGln-95 |
| SEQ. ID. NO. 13117 | 151-GlyAspPheSerThrThr-156 |
| Antigenic Index - Jameson-Wolf | |
| SEQ. ID. NO. 13118 | 22-TyrLysValAspGluTyrHisAla-29 |
| SEQ. ID. NO. 13119 | 38-PheAsnThrSerThrAsnVal-44 |
| SEQ. ID. NO. 13120 | 54-ValGluPheAspGlnAlaLysArgAspGlyLysIleAspIle-67 |
| SEQ. ID. NO. 13121 | 83-AspHisLeuLysSer-87 |
| SEQ. ID. NO. 13122 | 95-GlnTyrProAspIleArgPheValSer-103 |
| SEQ. ID. NO. 13123 | 105-LysPheAsnPheAsnGlyLysLysLeuValSer-115 |
| SEQ. ID. NO. 13124 | 122-MetHisGlyLysThrAlaProValLysLeuLysAlaGluLys-135 |
| SEQ. ID. NO. 13125 | 137-AsnCysTyrGlnSerProMetGluLysThrGluValCysGlyGlyAsp-152 |
| SEQ. ID. NO. 13126 | 154-SerThrThrIleAspArgThrLysTrpGly-163 |
| SEQ. ID. NO. 13127 | 174-LysSerValArgIle-17 |
| SEQ. ID. NO. 13128 | 180-IleGlnIleGluAlaAlaLysGln-187 |
| Hydrophilic Regions - Hopp-Woods | |
| SEQ. ID. NO. 13129 | 22-TyrLysValAspGluTyrHisAla-29 |
| SEQ. ID. NO. 13130 | 54-ValGluPheAspGlnAlaLysArgAspGlyLysIleAspIle-67 |
| SEQ. ID. NO. 13131 | 83-AspHisLeuLysSer-87 |

TABLE 1-continued

| | |
|---|---|
| SEQ. ID. NO. 13132 | 108-PheAsnGlyLysLysLeuValSer-115 |
| SEQ. ID. NO. 13133 | 125-LysThrAlaProValLysLeuLysAlaGluLys-135 |
| SEQ. ID. NO. 13134 | 142-ProMetGluLysThrGluValCysGly-150 |
| SEQ. ID. NO. 13135 | 155-ThrThrIleAspArgThrLysTrp-162 |
| SEQ. ID. NO. 13136 | 174-LysSerValArgIle-178 |
| SEQ. ID. NO. 13137 | 180-IleGlnIleGluAlaAlaLysGln-187 |
| 954 | |
| AMPHI Regions - AMPHI | |
| SEQ. ID. NO. 13138 | 48-ArgAlaAlaArgPheArg-53 |
| SEQ. ID. NO. 13139 | 57-GlnGlyLeuGlyGlyAspPheGluArgPheLeuLysGly-69 |
| SEQ. ID. NO. 13140 | 74-GlnGluAsnLeuAlaLysTyrArgGluAsnIle-84 |
| SEQ. ID. NO. 13141 | 100-ProTyrArgValCysLysGlnAla-107 |
| SEQ. ID. NO. 13142 | 134-TyrGlnAsnTyrArgLysSerMetGlnGluCysArgLysThrIleThr-149 |
| Antigenic Index - Jameson-Wolf | |
| SEQ. ID. NO. 13143 | 17-GlyGlnGluGlnSerGlnLysAlaAspAlaGlu-27 |
| SEQ. ID. NO. 13144 | 35-TyrGlnPheAlaAspGluLysGln-42 |
| SEQ. ID. NO. 13145 | 58-GlyLeuGlyGlyAspPheGluArgPheLeuLysGlyGluIleProAsnGlnGluAsnLeuAlaLysTyrArgGluAsnIle-84 |
| SEQ. ID. NO. 13146 | 92-AlaAspThrAsnGlyAspAspAspProTyrArgValCysLys-105 |
| SEQ. ID. NO. 13147 | 107-AlaAlaGlnAspAlaGluIleLeuMet-115 |
| SEQ. ID. NO. 13148 | 119-ValThrSerGlyGlyGlyGlyThrThrAspLeuAspLysGluSerTyrGlnAsnTyrArgLysSerMetGlnGluCysArgLysThrIleThrGluAlaGlu AlaAsnLeuProLysLys-158 |
| Hydrophilic Regions - Hopp-Woods | |
| SEQ. ID. NO. 13149 | 17-GlyGlnGluGlnSerGlnLysAlaAspAlaGlu-27 |
| SEQ. ID. NO. 13150 | 36-GlnPheAlaAspGluLysGln-42 |
| SEQ. ID. NO. 13151 | 61-GlyAspPheGluArgPheLeuLys-68 |
| SEQ. ID. NO. 13152 | 70-GluIleProAsnGlnGluAsnLeuAlaLysTyrArgGluAsnIle-84 |
| SEQ. ID. NO. 13153 | 94-ThrAsnGlyAspAspAspProTyrArgValCysLys-105 |
| SEQ. ID. NO. 13154 | 107-AlaAlaGlnAspAlaGluIleLeuMet-115 |
| SEQ. ID. NO. 13155 | 125-GlyThrThrAspLeuAspLysGluSerTyrGlnAsnTyrArgLysSerMetGlnGluCysArgLysThrIleThrGluAlaGluAlaAsnLeuProLys Lys-158 |
| 957 | |
| AMPHI Regions - AMPHI | |
| SEQ. ID. NO. 13156 | 11-SerPhePheAlaLeuValPheAla-18 |
| SEQ. ID. NO. 13157 | 39-AlaThrGluValProLysAsnPro-46 |
| SEQ. ID. NO. 13158 | 48-AlaPheValAlaLysLeuAlaArgLeuPheArgAsnAla-60 |
| SEQ. ID. NO. 13159 | 76-AsnLeuAlaGlyThrValAspAsp-83 |
| SEQ. ID. NO. 13160 | 198-GluAspValTyrGluHisCysLeuGlyCysTyrGlnMet-210 |
| SEQ. ID. NO. 13161 | 218-TyrArgAspValAlaAsnAspGlu-225 |
| SEQ. ID. NO. 13162 | 235-SerAsnArgIleAlaSer-240 |
| SEQ. ID. NO. 13163 | 249-GlnAsnMetArgGluLeuMetProArg-257 |
| SEQ. ID. NO. 13164 | 335-GluLysGluValArgArgTyrAlaGluAlaAlaAlaArg-367 |
| Antigenic Index - Jameson-Wolf | |
| SEQ. ID. NO. 13165 | 29-IleAsnProArgTrp-33 |
| SEQ. ID. NO. 13166 | 35-LeuSerAspThrAlaThrGluValProLysAsnProAsn-47 |
| SEQ. ID. NO. 13167 | 57-PheArgAsnAlaAspArgAla-63 |
| SEQ. ID. NO. 13168 | 69-GluSerIleArgThrGluGluAsnLeuAlaGlyThrValAspAspGlyProLeuGlnSerGluLysAspTyr-92 |
| SEQ. ID. NO. 13169 | 98-ArgLeuSerArgLeuLysGluLysAlaLys-107 |
| SEQ. ID. NO. 13170 | 112-ThrGluGlnGluHisGlyLys-118 |
| SEQ. ID. NO. 13171 | 125-HisIleGlyGluGlyGly-130 |
| SEQ. ID. NO. 13172 | 136-LeuSerGlnArgSerProGluAlaPheVal-145 |
| SEQ. ID. NO. 13173 | 149-TyrLeuTyrArgAsnAspArgProPheSer-158 |
| SEQ. ID. NO. 13174 | 166-ValHisGlyGluAsnTyrGluThrThrGlyGluTyrArgVal-179 |
| SEQ. ID. NO. 13175 | 182-GlnProAspGlySerVal-187 |
| SEQ. ID. NO. 13176 | 190-AlaAlaGlyArgGlyLysIleGlyGluAspValTyr-201 |
| SEQ. ID. NO. 13177 | 217-LysTyrArgAspValAlaAsnAspGluGlnLysValTrpAspPheArgLysGluSerAsnArgIleAlaSerAspSerArgAsnSerValPheTyrGlnAsn MetArgGluLeuMetProArgGlyMetLysAlaAsnSer-263 |
| SEQ. ID. NO. 13178 | 267-GlyTyrAspAlaAspGlyLeuProGlnLys-276 |
| SEQ. ID. NO. 13179 | 280-SerPheAspAsnGlyLysLysArgGlnSerPheGluTyrTyrLeuLysAsnGlyAsn-298 |
| SEQ. ID. NO. 13180 | 309-LeuLysAlaAspGlyValThr-315 |
| SEQ. ID. NO. 13181 | 329-LeuAspGlyGlyArgIleValArgGluGluLysGlnGlyAspArgLeuProAspPhe-347 |
| SEQ. ID. NO. 13182 | 352-GluAsnLeuGluLysGluValArgArgTyrAlaGluAlaAlaAlaArgArgSerGlyGlyArgArgAspLeuSerHis-377 |
| Hydrophilic Regions - Hopp-Woods | |
| SEQ. ID. NO. 13183 | 38-ThrAlaThrGluValProLysAsnPro-46 |
| SEQ. ID. NO. 13184 | 57-PheArgAsnAlaAspArgAla-63 |
| SEQ. ID. NO. 13185 | 69-GluSerIleArgThrGluGluAsnLeu-77 |
| SEQ. ID. NO. 13186 | 80-ThrValAspAspGlyProLeuGlnSerGluLysAspTyr-92 |
| SEQ. ID. NO. 13187 | 98-ArgLeuSerArgLeuLysGluLysAlaLys-107 |
| SEQ. ID. NO. 13188 | 112-ThrGluGlnGluHisGlyLys-118 |
| SEQ. ID. NO. 13189 | 136-LeuSerGlnArgSerProGlu-142 |
| SEQ. ID. NO. 13190 | 151-TyrArgAsnAspArgProPhe-157 |
| SEQ. ID. NO. 13191 | 169-GluAsnTyrGluThrThrGlyGluTyr-177 |
| SEQ. ID. NO. 13192 | 190-AlaAlaGlyArgGlyLysIleGlyGluAspValTyr-201 |
| SEQ. ID. NO. 13193 | 217-LysTyrArgAspValAlaAsnAspGluGlnLysValTrpAspPheArgLysGluSerAsnArgIleAlaSerAspSerArgAsn-244 |
| SEQ. ID. NO. 13194 | 250-AsnMetArgGluLeuMetProArgGlyMetLys-260 |
| SEQ. ID. NO. 13195 | 268-TyrAspAlaAspGlyLeuPro-274 |
| SEQ. ID. NO. 13196 | 282-AspAsnGlyLysLysArgGlnSer-289 |
| SEQ. ID. NO. 13197 | 309-LeuLysAlaAspGlyValThr-315 |

TABLE 1-continued

| | |
|---|---|
| SEQ. ID. NO. 13198 | 331-GlyGlyArgIleValArgGluGluLysGlnGlyAspArgLeuPro-345 |
| SEQ. ID. NO. 13199 | 352-GluAsnLeuGluLysGluValArgArgTyrAlaGluAlaAlaAlaArgArgSerGlyGlyArgArgAspLeuSerHis-377 |
| 958 | |
| AMPHI Regions - AMPHI | |
| SEQ. ID. NO. 13200 | 34-AspAsnProThrAlaGlyGluSerValArgSerValSerGluProIleGln-50 |
| SEQ. ID. NO. 13201 | 86-ProGluAspTyrThrArgIleValAlaAsp-95 |
| SEQ. ID. NO. 13202 | 127-TyrAspGlnSerGlyAsp-132 |
| SEQ. ID. NO. 13203 | 176-GlyArgArgLeuGlnSerValSerArgThrAlaGluMet-188 |
| SEQ. ID. NO. 13204 | 343-IleSerAspThrLeuGln-348 |
| SEQ. ID. NO. 13205 | 483-TyrTyrSerLeuAsnArgPhe-489 |
| SEQ. ID. NO. 13206 | 491-SerGlnGluAlaArgArgVal-497 |
| SEQ. ID. NO. 13207 | 500-ThrLeuProIleVal-504 |
| SEQ. ID. NO. 13208 | 521-GlyGluValLeuGlnThrLeuGluProArgLeu-531 |
| SEQ. ID. NO. 13209 | 541-GlnAsnAspLeuProAsnPheAsp-548 |
| SEQ. ID. NO. 13210 | 572-AsnThrAlaAsnSerLeuSerAlaAlaValGlnSer-583 |
| SEQ. ID. NO. 13211 | 616-ValGlyLysLysPro-620 |
| SEQ. ID. NO. 13212 | 693-AspLysLeuSerGln-697 |
| SEQ. ID. NO. 13213 | 723-LysLysProIleGlu-727 |
| SEQ. ID. NO. 13214 | 769-AspLeuSerSerValGlyArgAsnPro-777 |
| Antigenic Index - Jameson-Wolf | |
| SEQ. ID. NO. 13215 | 28-ValAlaAlaGluGluThrAspAsnProThrAlaGlyGluSerValArgSerValSerGluProIleGln-50 |
| SEQ. ID. NO. 13216 | 55-SerLeuGlySerThr-59 |
| SEQ. ID. NO. 13217 | 63-CysSerAsnGluSerGlySerProGluArgThrGluAlaAlaValGlnGlySerGlyGluAlaSerIleProGluAspTyrThrArgIleValAlaAspArgMet GluGlyGlnSerGlnValGlnValArgAlaGluGly-109 |
| SEQ. ID. NO. 13218 | 111-ValValValGluArgAsnArgThrThrLeuAsn-121 |
| SEQ. ID. NO. 13219 | 123-AspTrpAlaAspTyrAspGlnSerGlyAspThrValThrAlaGlyAspArgPheAlaLeuGlnGlnAspGlyThrLeuIleArgGlyGluThrLeu-154 |
| SEQ. ID. NO. 13220 | 158-LeuGluGlnGlnThrGlyGluAlaHisAsnValArgMetGluIleGluGlnGlyGlyArgArgLeuGlnSerValSerArgThrAlaGluMetLeuGly GluGlyHisTyrLysLeuThrGluThrGlnPheAsnThrCysSerAlaGlyAspAlaGlyTrp-211 |
| SEQ. ID. NO. 13221 | 216-AlaSerValGluAlaAspArgGluLysGlyIleGly-227 |
| SEQ. ID. NO. 13222 | 249-PheProLeuAspGlyAsnArgLysSerGlyLeu-259 |
| SEQ. ID. NO. 13223 | 265-SerAlaGlySerAspGlyVal-271 |
| SEQ. ID. NO. 13224 | 293-ValIleGlyGluArgGlyAlaValPheAspGlyGlnValArgTyrLeuArgProAspTyrAlaGlyGlnSerAsp-317 |
| SEQ. ID. NO. 13225 | 321-LeuProHisAspLysLysSerGlyArgAsnAsnArgTyrGlnAla-335 |
| SEQ. ID. NO. 13226 | 337-TrpGlnHisArgHisAspIleSerAspThrLeu-347 |
| SEQ. ID. NO. 13227 | 352-AspPheAsnGlnValSerAspSerGlyTyrTyrArgAspPheTyrGlyAsnLysGluIleAlaGlyAsnValAsnLeuAsnArgArgValTrp-382 |
| SEQ. ID. NO. 13228 | 384-AspTyrGlyGlyArgAlaAlaGlyGlySerLeu-394 |
| SEQ. ID. NO. 13229 | 407-AlaAsnGlnSerGlyTyrLysAspLysProTyr-417 |
| SEQ. ID. NO. 13230 | 425-ValGluTrpArgLysAsnThrGlyArgAla-434 |
| SEQ. ID. NO. 13231 | 444-ArgPheSerHisAspSerArgGlnAspGlySerArg-455 |
| SEQ. ID. NO. 13232 | 460-ProAspIleLysTrpAspPheSerAsnSerTrpGly-471 |
| SEQ. ID. NO. 13233 | 487-AsnArgPheGlySerGlnGluAlaArgArgValSerArg-499 |
| SEQ. ID. NO. 13234 | 507-AspSerGlyAlaThrPheGluArgAsnThrArgMetPheGly-520 |
| SEQ. ID. NO. 13235 | 538-AlaLysSerGlnAsnAspLeuProAsnPheAspSerSerGluSerSerPheGly-555 |
| SEQ. ID. NO. 13236 | 560-PheArgGluAsnLeuTyrTyrGlyAsnAspArgIleAsnThrAlaAsnSer-576 |
| SEQ. ID. NO. 13237 | 581-ValGlnSerArgIleLeuAspGlyAlaThrGlyGluGluArgPheArgAlaGlyIleGlyGlnLysPheTyrPheLysAspAspAlaValMetLeuAspGly SerValGlyLysLysProArgAsnArgSerAspTrp-626 |
| SEQ. ID. NO. 13238 | 631-SerGlySerIleGlySer-636 |
| SEQ. ID. NO. 13239 | 642-SerSerIleHisTyrAsnGlnAsnAspLysArgAlaGluAsn-655 |
| SEQ. ID. NO. 13240 | 660-AlaSerTyrArgProAlaGlnGlyLysValLeuAsnAlaArgTyrLysTyrGlyArgAsnGluLysIleTyrLeuLysSerAspGlySerTyrPhe-691 |
| SEQ. ID. NO. 13241 | 693-AspLysLeuSerGln-697 |
| SEQ. ID. NO. 13242 | 718-TyrGlyPheGluAlaLysLysProIleGlu-727 |
| SEQ. ID. NO. 13243 | 732-AlaGluTyrLysSerSerCysGlyCysTrp-741 |
| SEQ. ID. NO. 13244 | 751-ValThrGlyGluAsnThrTyrLysAsn-759 |
| SEQ. ID. NO. 13245 | 766-GlnLeuLysAspLeuSerSerValGlyArgAsnProAlaAspArgMetAspVal-783 |
| SEQ. ID. NO. 13246 | 794-LeuSerAlaGlyArgAsnLysArgPro-802 |
| Hydrophilic Regions - Hopp-Woods | |
| SEQ. ID. NO. 13247 | 28-ValAlaAlaGluGluThrAspAsnProThrAlaGlyGluSerValArgSerValSerGluProIleGln-50 |
| SEQ. ID. NO. 13248 | 65-AsnGluSerGlySerProGluArgThrGluAlaAlaVal-77 |
| SEQ. ID. NO. 13249 | 79-GlySerGlyGluAlaSerIleProGluAspTyrThr-90 |
| SEQ. ID. NO. 13250 | 93-ValAlaAspArgMetGluGlyGlnSer-101 |
| SEQ. ID. NO. 13251 | 103-ValGlnValArgAlaGluGly-109 |
| SEQ. ID. NO. 13252 | 111-ValValValGluArgAsnArgThrThrLeu-120 |
| SEQ. ID. NO. 13253 | 125-AlaAspTyrAspGlnSerGlyAspThrValThrAlaGlyAspArgPheAlaLeu-142 |
| SEQ. ID. NO. 13254 | 147-ThrLeuIleArgGlyGluThr-153 |
| SEQ. ID. NO. 13255 | 160-GlnGlnThrGlyGluAlaHisAsnValArgMetGluIleGluGlnGlyGlyArgArgLeuGlnSerValSerArgThrAlaGluMetLeuGly-190 |
| SEQ. ID. NO. 13256 | 192-GlyHisTyrLysLeuThrGlu-198 |
| SEQ. ID. NO. 13257 | 216-AlaSerValGluAlaAspArgGluLysGlyIleGly-227 |
| SEQ. ID. NO. 13258 | 250-ProLeuAspGlyAsnArgLysSerGly-258 |
| SEQ. ID. NO. 13259 | 266-AlaGlySerAspGlyVal-271 |
| SEQ. ID. NO. 13260 | 294-IleGlyGluArgGlyAlaVal-300 |
| SEQ. ID. NO. 13261 | 305-ValArgTyrLeuArg-309 |
| SEQ. ID. NO. 13262 | 323-HisAspLysLysSerGlyArgAsnAsnArgTyrGlnAla-335 |
| SEQ. ID. NO. 13263 | 337-TrpGlnHisArgHisAspIleSerAsp-345 |
| SEQ. ID. NO. 13264 | 410-SerGlyTyrLysAspLysProTyr-417 |
| SEQ. ID. NO. 13265 | 425-ValGluTrpArgLysAsnThrGlyArgAla-434 |
| SEQ. ID. NO. 13266 | 445-PheSerHisAspSerArgGlnAspGlySerArg-455 |
| SEQ. ID. NO. 13267 | 490-GlySerGlnGluAlaArgArgValSerArg-499 |
| SEQ. ID. NO. 13268 | 510-AlaThrPheGluArgAsnThrArg-517 |
| SEQ. ID. NO. 13269 | 539-LysSerGlnAsnAsp-543 |
| SEQ. ID. NO. 13270 | 548-AspSerSerGluSer-552 |

TABLE 1-continued

| | |
|---|---|
| SEQ. ID. NO. 13271 | 569-AspArgIleAsnThr-573 |
| SEQ. ID. NO. 13272 | 589-AlaThrGlyGluGluArgPheArgAla-597 |
| SEQ. ID. NO. 13273 | 604-TyrPheLysAspAspAlaValMet-611 |
| SEQ. ID. NO. 13274 | 615-SerValGlyLysLysProArgAsnArgSerAsp-625 |
| SEQ. ID. NO. 13275 | 648-GlnAsnAspLysArgAlaGluAsn-655 |
| SEQ. ID. NO. 13276 | 662-TyrArgProAlaGln-666 |
| SEQ. ID. NO. 13277 | 674-TyrLysTyrGlyArgAsnGluLysIleTyrLeuLysSerAspGly-688 |
| SEQ. ID. NO. 13278 | 720-PheGluAlaLysLysProIleGlu-727 |
| SEQ. ID. NO. 13279 | 732-AlaGluTyrLysSer-736 |
| SEQ. ID. NO. 13280 | 766-GlnLeuLysAspLeuSerSerValGlyArgAsnProAlaAspArgMetAspVal-783 |
| SEQ. ID. NO. 13281 | 795-SerAlaGlyArgAsnLysArgPro-802 |
| 959 | |
| AMPHI Regions - AMPHI | |
| SEQ. ID. NO. 13282 | 56-AlaAlaLeuAlaArgValGlyGly-63 |
| Antigenic Index - Jameson-Wolf | |
| SEQ. ID. NO. 13283 | 24-AlaHisHisAspGlyHisGlyAspAspAspHisGlyHis-36 |
| SEQ. ID. NO. 13284 | 38-AlaHisGlnHisAsnLysGlnAspLysIleIleSer-49 |
| SEQ. ID. NO. 13285 | 51-AlaGlnAlaGluLysAlaAlaLeu-58 |
| SEQ. ID. NO. 13286 | 60-ArgValGlyGlyLysIleThrAspIleAspLeuGluHisAspAsnGlyArgProHisTyrAspValGluIleValLysAsnGlyGlnGluTyr-90 |
| SEQ. ID. NO. 13287 | 94-ValAspAlaArgThrGlyArgValIleSerSerArgArgAspAsp-108 |
| Hydrophilic Regions - Hopp-Woods | |
| SEQ. ID. NO. 13288 | 27-AspGlyHisGlyAspAspAspHisGlyHis-36 |
| SEQ. ID. NO. 13289 | 40-GlnHisAsnLysGlnAspLysIleIleSer-49 |
| SEQ. ID. NO. 13290 | 51-AlaGlnAlaGluLysAlaAlaLeu-58 |
| SEQ. ID. NO. 13291 | 61-ValGlyGlyLysIleThrAspIleAspLeuGluHisAspAsnGlyArgProHisTyr-79 |
| SEQ. ID. NO. 13292 | 82-GluIleValLysAsnGlyGlnGluTyr-90 |
| SEQ. ID. NO. 13293 | 94-ValAspAlaArgThrGlyArg-100 |
| SEQ. ID. NO. 13294 | 102-IleSerSerArgArgAspAsp-108 |
| 960 | |
| AMPHI Regions - AMPHI | |
| SEQ. ID. NO. 13295 | 24-AlaProArgLeuLeuProSerPheThrAspPro-34 |
| SEQ. ID. NO. 13296 | 39-LeuSerAlaProGlyGlyTyrIleVal-47 |
| SEQ. ID. NO. 13297 | 58-IleGluLysLeuAlaLysGlnProGluTyrAlaTyrLeuLysGlnLeuGlnValAlaLysAsnValAsn-80 |
| SEQ. ID. NO. 13298 | 137-PheAlaSerLeuAlaSer-142 |
| SEQ. ID. NO. 13299 | 154-AspValGlyLysThrLeuLysGluLeuGlyArgSerArgThr-167 |
| SEQ. ID. NO. 13300 | 189-LeuAlaThrTrpSerGlu-194 |
| SEQ. ID. NO. 13301 | 230-AsnIleLeuAlaAlaLeuValAsnThrAla-239 |
| SEQ. ID. NO. 13302 | 245-SerLysIleLysGly-249 |
| SEQ. ID. NO. 13303 | 257-HisLysIleAlaHisAlaValAlaGlyCysAla-267 |
| SEQ. ID. NO. 13304 | 280-AlaIleGlyAlaAlaValGlyGluIleValGlyGlu-291 |
| SEQ. ID. NO. 13305 | 314-IleThrAlaTyrAlaLys-319 |
| SEQ. ID. NO. 13306 | 338-GlnThrAlaGlnAsnAla-343 |
| SEQ. ID. NO. 13307 | 345-GluAsnAsnAlaValLysAlaValValThr-354 |
| SEQ. ID. NO. 13308 | 359-ValTyrLysValAlaArgLysGly-366 |
| SEQ. ID. NO. 13309 | 387-AsnLeuAlaAspAsnLeuThrThrLeuPheAsp-397 |
| SEQ. ID. NO. 13310 | 418-AsnArgAlaAsnLysGlyGluAlaAlaGlnLysValLysGluValLeu-433 |
| SEQ. ID. NO. 13311 | 460-LysGlnLeuAlaGlnIle-465 |
| Antigenic Index - Jameson-Wolf | |
| SEQ. ID. NO. 13312 | 11-LeuTyrArgArgGlySerValLysProProLeu-21 |
| SEQ. ID. NO. 13313 | 23-GluAlaProArgLeuLeuProSerPheThrAsp-33 |
| SEQ. ID. NO. 13314 | 35-ValValProLysLeuSerAlaProGly-43 |
| SEQ. ID. NO. 13315 | 48-AspIleProLysGlyAsnLeuLysThrGluIleGluLysLeuAlaLysGlnProGlu-66 |
| SEQ. ID. NO. 13316 | 77-LysAsnValAsnTrp-81 |
| SEQ. ID. NO. 13317 | 87-AlaTyrAspLysTrpAspTyrLysGlnGluGlyLeuThr-99 |
| SEQ. ID. NO. 13318 | 150-AsnAsnLysGlyAspValGlyLysThrLeuLysGluLeuGlyArgSerArgThrValLys-169 |
| SEQ. ID. NO. 13319 | 180-ValSerAsnLysLeuGlyAla-186 |
| SEQ. ID. NO. 13320 | 193-SerGluThrProTrp-197 |
| SEQ. ID. NO. 13321 | 218-ValAsnGlyGlySerLeuLysAspAsnLeuGlu-228 |
| SEQ. ID. NO. 13322 | 239-AlaHisGlyGluAlaAlaSerLysIleLysGlyLeuAsp-251 |
| SEQ. ID. NO. 13323 | 270-AlaAlaAsnLysGlyLysCysGlnAspGlyAla-280 |
| SEQ. ID. NO. 13324 | 292-AlaLeuValLysAsnThrAspPheSerAspMetThrProGluGlnLeuAspLeuGluValLysLys-313 |
| SEQ. ID. NO. 13325 | 329-ThrGlyGlyAspValAsnThr-335 |
| SEQ. ID. NO. 13326 | 362-ValAlaArgLysGlyLeuLysAsnGlyLysIleAsnValArgAspLeuLysGlnThrLeuLysAspGluGlyTyrAsnLeu-388 |
| SEQ. ID. NO. 13327 | 398-GluThrLeuAspTrpAsnAspAlaLysAla-407 |
| SEQ. ID. NO. 13328 | 415-ThrGluLeuAsnArgAlaAsnLysGlyGluAlaAlaGlnLysValLysGluValLeuGluLysAsnArgProTyrIleProAsnLysGlyAlaValPro-447 |
| SEQ. ID. NO. 13329 | 451-ThrTyrMetLysAsnAsnProPheGlyLysGln-461 |
| SEQ. ID. NO. 13330 | 465-IleSerGluLysThrThrLeuProThrGlnGlnGlyGlnSer-478 |
| SEQ. ID. NO. 13331 | 483-LysArgAsnGlnGlyLeuLeuLysThrGlyAspArgPheTyrLeuAspGlyGlnHisLysAsnHisLeu-505 |
| SEQ. ID. NO. 13332 | 507-ValPheAspLysAsnGlyAsnPheLys-515 |
| SEQ. ID. NO. 13333 | 520-MetAspGlySerLeuAsnGlnMetLysThrGlyAlaAlaLysGlyArgLysLeuAsnLeu-539 |
| Hydrophilic Regions - Hopp-Woods | |
| SEQ. ID. NO. 13334 | 13-ArgArgGlySerValLys-18 |
| SEQ. ID. NO. 13335 | 49-IleProLysGlyAsnLeuLysThrGluIleGluLysLeuAlaLysGlnProGlu-66 |
| SEQ. ID. NO. 13336 | 89-AspLysTrpAspTyrLysGlnGluGlyLeuThr-99 |
| SEQ. ID. NO. 13337 | 150-AsnAsnLysGlyAspValGlyLysThrLeuLysGluLeuGlyArgSerArgThrValLys-169 |
| SEQ. ID. NO. 13338 | 221-GlySerLeuLysAspAsnLeuGlu-228 |
| SEQ. ID. NO. 13339 | 239-AlaHisGlyGluAlaAlaSerLysIleLysGlyLeuAsp-251 |
| SEQ. ID. NO. 13340 | 270-AlaAlaAsnLysGlyLysCysGlnAsp-278 |
| SEQ. ID. NO. 13341 | 292-AlaLeuValLysAsnThrAspPheSerAspMetThrProGluGlnLeuAspLeuGluValLysLys-313 |
| SEQ. ID. NO. 13342 | 362-ValAlaArgLysGlyLeuLysAsnGlyLysIleAsnValArgAspLeuLysGlnThrLeuLysAspGluGlyTyrAsn-387 |

TABLE 1-continued

| | |
|---|---|
| SEQ. ID. NO. 13343 | 398-GluThrLeuAspTrpAsnAspAlaLysAla-407 |
| SEQ. ID. NO. 13344 | 416-GluLeuAsnArgAlaAsnLysGlyGluAlaAlaGlnLysValLysGluValLeuGluLysAsnArgPro-438 |
| SEQ. ID. NO. 13345 | 465-IleSerGluLysThrThrLeu-471 |
| SEQ. ID. NO. 13346 | 483-LysArgAsnGlnGly-487 |
| SEQ. ID. NO. 13347 | 499-GlyGlnHisLysAsnHis-504 |
| SEQ. ID. NO. 13348 | 507-ValPheAspLysAsnGlyAsn-513 |
| SEQ. ID. NO. 13349 | 522-GlySerLeuAsnGln-526 |
| SEQ. ID. NO. 13350 | 528-LysThrGlyAlaAlaLysGlyArgLysLeuAsnLeu-539 |
| 961-2 | |
| AMPHI Regions - AMPHI | |
| SEQ. ID. NO. 13351 | 6-PheProSerLysVal-10 |
| SEQ. ID. NO. 13352 | 13-ThrAlaIleLeuAlaThrPheCysSerGly-22 |
| SEQ. ID. NO. 13353 | 46-AsnGlyGlnGluIleAsnGlyPheLysAlaGlyGluThrIleTyrAspIle-62 |
| SEQ. ID. NO. 13354 | 90-LysValValThrAsnLeuThrLysThrVal-99 |
| SEQ. ID. NO. 13355 | 118-GluLysLeuThrThr-122 |
| SEQ. ID. NO. 13356 | 138-LeuAspGluThrThrAsnAlaLeuAsnLysLeuGlyGluAsnIleThrThrPheAla-156 |
| SEQ. ID. NO. 13357 | 170-LeuGluAlaValAlaAspThrValAspLysHisAlaGluAlaPheAsnAspIleAlaAspSerLeuAsp-192 |
| SEQ. ID. NO. 13358 | 200-GluAlaValLysThrAlaAsnGluAlaLysGlnThrAlaGlu-213 |
| SEQ. ID. NO. 13359 | 273-AlaArgIleAspSerLeuAspLysAsnValAlaAsnLeuArgLysGluThrArgGlnGlyLeu-293 |
| SEQ. ID. NO. 13360 | 300-SerGlyLeuPheGlnProTyrAsnVal-308 |
| Antigenic Index - Jameson-Wolf | |
| SEQ. ID. NO. 13361 | 27-ThrSerAspAspAspValLysLysAlaAla-36 |
| SEQ. ID. NO. 13362 | 45-AsnAsnGlyGlnGluIleAsnGlyPheLysAlaGlyGluThr-58 |
| SEQ. ID. NO. 13363 | 60-TyrAspIleGlyGluAspGlyThrIleThrGlnLysAspAlaThrAlaAlaAspValGluAlaAspAspPheLys-84 |
| SEQ. ID. NO. 13364 | 98-ThrValAsnGluAsnLysGlnAsnValAspAlaLysValLysAlaAlaGluSerGluIleGluLysLeuThrThrLysLeuAlaAspThrAspAlaAlaLeu AlaAspThrAspAlaAlaLeuAspGluThrThrAsnAlaLeuAsnLysLeuGlyGluAsnIleThr-153 |
| SEQ. ID. NO. 13365 | 155-PheAlaGluGluThrLysThrAsnIleValLysIleAspGluLysLeuGluAlaValAlaAspThrValAspLysHisAlaGluAlaPheAsnAspIleAla AspSerLeuAspGluThrAsnThrLysAlaAspGluAlaValLysThrAlaAsnGluAlaLysGlnThrAlaGluGluThrLysGlnAsnValAspAlaLysVal LysAlaAlaGluThrAlaAlaGlyLysAlaGluAlaAlaAla-237 |
| SEQ. ID. NO. 13366 | 239-ThrAlaAsnThrAlaAlaAspLysAlaGluAlaValAla-251 |
| SEQ. ID. NO. 13367 | 253-LysValThrAspIleLysAlaAspIleAlaThrAsnLysAlaAspIleAlaLysAsnSerAlaArgIleAspSerLeuAspLysAsnValAlaAsnLeuArg LysGluThrArgGlnGlyLeuAla-294 |
| SEQ. ID. NO. 13368 | 317-ValGlyGlyTyrLysSerGluSer-324 |
| SEQ. ID. NO. 13369 | 330-ThrGlyPheArgPhe-334 |
| SEQ. ID. NO. 13370 | 348-ThrSerSerGlySerSerAla-354 |
| Hydrophilic Regions - Hopp-Woods | |
| SEQ. ID. NO. 13371 | 27-ThrSerAspAspAspValLysLysAlaAla-36 |
| SEQ. ID. NO. 13372 | 54-LysAlaGlyGluThr-58 |
| SEQ. ID. NO. 13373 | 62-IleGlyGluAspGlyThrIleThrGlnLysAspAlaThrAlaAlaAspValGluAlaAspAspPheLys-84 |
| SEQ. ID. NO. 13374 | 98-ThrValAsnGluAsnLysGlnAsnValAspAlaLysValLysAlaAlaGluSerGluIleGluLysLeuThrThrLysLeuAlaAspThrAspAlaAlaLeu AlaAspThrAspAlaAlaLeuAspGluThrThrAsnAla-144 |
| SEQ. ID. NO. 37765 | 155-PheAlaGluGluThrLysThrAsnIleValLysIleAspGluLysLeuGluAlaValAlaAspThrValAspLysHisAlaGluAlaPheAsnAspIleAla AspSerLeuAspGluThrAsnThrLysAlaAspGluAlaValLysThrAlaAsnGluAlaLysGlnThrAlaGluGluThrLysGlnAsnValAspAlaLysVal LysAlaAlaGluThrAlaAlaGlyLysAlaGluAlaAlaAla-237 |
| SEQ. ID. NO. 13375 | 242-ThrAlaAlaAspLysAlaGluAlaValAla-251 |
| SEQ. ID. NO. 13376 | 253-LysValThrAspIleLysAlaAspIleAlaThrAsnLysAlaAspIleAlaLysAsnSerAlaArgIleAspSerLeuAspLysAsnValAlaAsnLeuArg LysGluThrArgGlnGlyLeuAla-294 |
| SEQ. ID. NO. 13377 | 320-TyrLysSerGluSer-324 |
| 972-2 | |
| AMPHI Regions - AMPHI | |
| SEQ. ID. NO. 13378 | 15-SerSerGluArgMetSerGluValGluTyrPheSerHis-27 |
| SEQ. ID. NO. 13379 | 83-ArgLysLeuGluGluIleLeuGly-90 |
| SEQ. ID. NO. 13380 | 100-ArgGlyAsnLysPheTyrGluSerMetTyrArgLeu-111 |
| SEQ. ID. NO. 13381 | 154-LeuAspAspSerIleArg-159 |
| SEQ. ID. NO. 13382 | 226-PheValArgValTyrGluLysGly-233 |
| SEQ. ID. NO. 13383 | 275-IleCysArgLysPheLysAsnMetProValPro-285 |
| SEQ. ID. NO. 13384 | 308-AsnAlaValGlyLysLeuValAsnPhe-316 |
| SEQ. ID. NO. 13385 | 326-GluIleValGluSerLeuLysAla-333 |
| SEQ. ID. NO. 13386 | 336-GlyPheProLysGlyLeuGlu-342 |
| SEQ. ID. NO. 13387 | 348-LeuGluMetLeuArgAspGlyLeuLys-356 |
| SEQ. ID. NO. 13388 | 382-AsnSerAspLysPheAspArg-388 |
| Antigenic Index - Jameson-Wolf | |
| SEQ. ID. NO. 13389 | 1-LeuThrAsnArgGlyGlyAlaLysLeuLysThrAsnSerLysSerSerGluArgMetSerGlu-21 |
| SEQ. ID. NO. 13390 | 29-IleSerAspGlyLysGlyLysLeuLeuGluIleProGlnArgArgGlyLysGlnAspGlyVal-49 |
| SEQ. ID. NO. 13391 | 62-ThrLeuLeuLysValSerGly-68 |
| SEQ. ID. NO. 13392 | 83-ArgLysLeuGluGlu-87 |
| SEQ. ID. NO. 13393 | 93-IleThrArgLysCysLysSerArgGlyAsnLysPheTyrGlu-106 |
| SEQ. ID. NO. 13394 | 108-MetTyrArgLeuGlySerAspAspValAspTyrGly-119 |
| SEQ. ID. NO. 13395 | 122-HisPheGlyGlyGlnArgAsnThrVal-130 |
| SEQ. ID. NO. 13396 | 134-LeuLysGlyThrGlyCys-139 |
| SEQ. ID. NO. 13397 | 152-GlnPheLeuAspAspSerIleArgThrArgIleThrArg-164 |
| SEQ. ID. NO. 13398 | 172-PheAspGlyGluTyrThrProAspGlnAlaLeuLeuAspHisAspAsnGlyPhePheAspAsnSerAsnGlnArgProLysSerGluThrIleGly-203 |
| SEQ. ID. NO. 13399 | 205-AlaTrpArgAsnGluAspGlySerGlyLys-214 |
| SEQ. ID. NO. 13400 | 217-TyrValGlyArgLysLysAsnSerArgPhe-226 |
| SEQ. ID. NO. 13401 | 228-ArgValTyrGluLysGlyArgGlnLeuGlyAspLysGluSerLysTrpVal-244 |
| SEQ. ID. NO. 13402 | 251-AsnTyrGlyAspIleGluIle-257 |
| SEQ. ID. NO. 13403 | 263-IleAsnGlnGlySer-267 |
| SEQ. ID. NO. 13404 | 275-IleCysArgLysPheLysAsnMetProValProGluArgPheAspGlnArgLysLysLysLeu-295 |
| SEQ. ID. NO. 13405 | 321-GlyPheAspAsnSerGluIleValGluSerLeuLysAlaAspSerGlyPheProLysGlyLeuGluProGluLysTyrAla-347 |
| SEQ. ID. NO. 13406 | 350-MetLeuArgAspGlyLeuLys-356 |

TABLE 1-continued

| | |
|---|---|
| SEQ. ID. NO. 13407 | 361-HisGluGlnProAspIleAspLeuGluIleGluLeuAspGlu-374 |
| SEQ. ID. NO. 13408 | 380-PheLysAsnSerAspLysPheAspArgGluLysArgLeuPheSerProAspTyrAspValGluLysGluArgLysTyrGlnGluTyrLeu-409 |
| SEQ. ID. NO. 13409 | 417-ValAspTyrAspTyrPhe-422 |
| Hydrophilic Regions - Hopp-Woods | |
| SEQ. ID. NO. 13410 | 1-LeuThrAsnArgGlyGlyAlaLysLeuLysThrAsnSerLysSerSerGluArgMetSerGlu-21 |
| SEQ. ID. NO. 13411 | 30-SerAspGlyLysGlyLysLeuLeuGluIleProGlnArgArgGlyLysGlnAspGlyVal-49 |
| SEQ. ID. NO. 13412 | 83-ArgLysLeuGluGlu-87 |
| SEQ. ID. NO. 13413 | 93-IleThrArgLysCysLysSerArgGlyAsnLysPheTyr-105 |
| SEQ. ID. NO. 13414 | 111-LeuGlySerAspAspValAspTyrGly-119 |
| SEQ. ID. NO. 13415 | 134-LeuLysGlyThrGly-138 |
| SEQ. ID. NO. 13416 | 152-GlnPheLeuAspAspSerIleArgThrArgIleThrArg-164 |
| SEQ. ID. NO. 13417 | 181-AlaLeuLeuAspHisAspAsnGlyPhe-189 |
| SEQ. ID. NO. 13418 | 193-SerAsnGlnArgProLysSerGluThrIle-202 |
| SEQ. ID. NO. 13419 | 206-TrpArgAsnGluAspGlySerGly-213 |
| SEQ. ID. NO. 13420 | 219-GlyArgLysLysAsnSerArgPhe-226 |
| SEQ. ID. NO. 13421 | 228-ArgValTyrGluLysGlyArgGlnLeuGlyAspLysGluSerLysTrpVal-244 |
| SEQ. ID. NO. 13422 | 277-ArgLysPheLysAsn-281 |
| SEQ. ID. NO. 13423 | 283-ProValProGluArgPheAspGlnArgLysLysLysLeu-295 |
| SEQ. ID. NO. 13424 | 321-GlyPheAspAsnSerGluIleValGluSerLeuLysAlaAspSerGlyPhe-337 |
| SEQ. ID. NO. 13425 | 339-LysGlyLeuGluProGluLysTyrAla-347 |
| SEQ. ID. NO. 13426 | 350-MetLeuArgAspGlyLeuLys-356 |
| SEQ. ID. NO. 13427 | 362-GluGlnProAspIleAspLeuGluIleGluLeuAspGlu-374 |
| SEQ. ID. NO. 13428 | 381-LysAsnSerAspLysPheAspArgGluLysArgLeuPhe-393 |
| SEQ. ID. NO. 13429 | 396-AspTyrAspValGluLysGluArgLysTyrGlnGluTyrLeu-409 |
| 973-2 | |
| AMPHI Regions - AMPHI | |
| SEQ. ID. NO. 13430 | 12-GluArgLeuIleAlaArgLeuAlaArgGluProAspSerAlaGluAspValLeuAsnLeuLeuArgGlnAla-35 |
| SEQ. ID. NO. 13431 | 44-AspThrLeuLeuArgLeuGluLysValLeuAspPhe-55 |
| SEQ. ID. NO. 13432 | 77-AspSerIleGluArgIleThrAlaTyr-85 |
| SEQ. ID. NO. 13433 | 112-AspLeuLeuLysTyrMet-117 |
| SEQ. ID. NO. 13434 | 143-AlaLeuLeuLysGluPheArgGluGln-151 |
| SEQ. ID. NO. 13435 | 171-PheGluAspIleIleGluGlnIleValGlyGluIleGluAsp-184 |
| SEQ. ID. NO. 13436 | 194-AsnIleHisAlaVal-198 |
| SEQ. ID. NO. 13437 | 208-AlaThrGluIleGluAspIleAsnThrPhe-217 |
| SEQ. ID. NO. 13438 | 235-IleGlnGluLeuGly-239 |
| Antigenic Index - Jameson-Wolf | |
| SEQ. ID. NO. 13439 | 1-MetAspGlyAlaGlnProLysThrAsnPhe-10 |
| SEQ. ID. NO. 13440 | 18-LeuAlaArgGluProAspSerAlaGluAspVal-28 |
| SEQ. ID. NO. 13441 | 34-GlnAlaHisGluGlnGluValPheAspAlaAspThr-45 |
| SEQ. ID. NO. 13442 | 47-LeuArgLeuGluLysValLeuAsp-54 |
| SEQ. ID. NO. 13443 | 56-SerAspLeuGluValArgAspAlaMetIleThrArgSerArgMetAsnValLeuLysGluAsnAspSerIleGluArg-81 |
| SEQ. ID. NO. 13444 | 96-ValIleGlyGluAspLysAspGluVal-104 |
| SEQ. ID. NO. 13445 | 118-PheAsnProGluGlnPheHis-124 |
| SEQ. ID. NO. 13446 | 136-ProGluGlyLysSer-140 |
| SEQ. ID. NO. 13447 | 146-LysGluPheArgGluGlnArgAsnHis-154 |
| SEQ. ID. NO. 13448 | 159-IleAspGluTyrGlyGlyThrSerGly-167 |
| SEQ. ID. NO. 13449 | 178-IleValGlyGluIleGluAspGluPheAspGluAspAspSerAlaAspAsn-194 |
| SEQ. ID. NO. 13450 | 199-SerSerGluArgTrpArg-204 |
| SEQ. ID. NO. 13451 | 209-ThrGluIleGluAspIleAsn-215 |
| SEQ. ID. NO. 13452 | 218-PheGlyThrGluTyrSerSerGluGluAlaAspThr-229 |
| SEQ. ID. NO. 13453 | 239-GlyHisLeuProValArgGlyGluLysValLeu-249 |
| SEQ. ID. NO. 13454 | 258-AlaArgAlaAspAsnArgArgLeuHis-266 |
| Hydrophilic Regions - Hopp-Woods | |
| SEQ. ID. NO. 13455 | 1-MetAspGlyAlaGlnProLys-7 |
| SEQ. ID. NO. 13456 | 18-LeuAlaArgGluProAspSerAlaGluAspVal-28 |
| SEQ. ID. NO. 13457 | 34-GlnAlaHisGluGlnGluValPheAsp-42 |
| SEQ. ID. NO. 13458 | 47-LeuArgLeuGluLysValLeuAsp-54 |
| SEQ. ID. NO. 13459 | 56-SerAspLeuGluValArgAspAlaMetIleThrArgSerArgMetAsnValLeuLysGluAsnAspSerIleGluArg-81 |
| SEQ. ID. NO. 13460 | 96-ValIleGlyGluAspLysAspGluVal-104 |
| SEQ. ID. NO. 13461 | 136-ProGluGlyLysSer-140 |
| SEQ. ID. NO. 13462 | 146-LysGluPheArgGluGlnArgAsn-153 |
| SEQ. ID. NO. 13463 | 178-IleValGlyGluIleGluAspGluPheAspGluAspAspSerAlaAspAsn-194 |
| SEQ. ID. NO. 13464 | 199-SerSerGluArgTrpArg-204 |
| SEQ. ID. NO. 13465 | 209-ThrGluIleGluAsp-213 |
| SEQ. ID. NO. 13466 | 222-TyrSerSerGluGluAlaAspThr-229 |
| SEQ. ID. NO. 13467 | 243-ValArgGlyGluLysValLeu-249 |
| SEQ. ID. NO. 13468 | 258-AlaArgAlaAspAsnArgArgLeuHis-266 |
| 981-2 | |
| AMPHI Regions - AMPHI | |
| SEQ. ID. NO. 13469 | 33-AlaAsnProAspLysValTyrArgValAlaSer-43 |
| SEQ. ID. NO. 13470 | 48-AlaProPheGluSerLeuAsp-54 |
| SEQ. ID. NO. 13471 | 68-AsnAlaMetAlaLys-72 |
| SEQ. ID. NO. 13472 | 134-LysValSerSerSerGluAspLeuLysAsnMetAsnLysValGlyValVal-150 |
| SEQ. ID. NO. 13473 | 169-LysIleAlaArgPheGlu-174 |
| SEQ. ID. NO. 13474 | 183-LeuGluAsnGlyGlyLeuAspSerValVal-192 |
| SEQ. ID. NO. 13475 | 199-AlaAsnTyrValLysAsnAsnPro-206 |
| SEQ. ID. NO. 13476 | 209-GlyMetAspPheValThrLeuPro-216 |
| SEQ. ID. NO. 13477 | 235-ValLysMetLeuAsnAspAlaLeuGluLysValArgGluSerGlyGluTyr-251 |

TABLE 1-continued

| | |
|---|---|
| Antigenic Index - Jameson-Wolf | |
| SEQ. ID. NO. 13478 | 21-CysGlyGlyGlnGlyLysAspThrAlaAla-30 |
| SEQ. ID. NO. 13479 | 33-AlaAsnProAspLysValTyrArg-40 |
| SEQ. ID. NO. 13480 | 51-GluSerLeuAspSerLysGlyAsnValGluGlyPheAsp-63 |
| SEQ. ID. NO. 13481 | 78-IleGluPheLysHisGlnProTrpAspSer-87 |
| SEQ. ID. NO. 13482 | 92-LeuAsnAsnGlyAspAlaAspVal-99 |
| SEQ. ID. NO. 13483 | 106-IleThrAspAspArgLysGlnSerMetAspPheSerAspProTyrPhe-121 |
| SEQ. ID. NO. 13484 | 129-ValProLysGlyLysLysValSerSerSerGluAspLeuLysAsnMetAsnLys-146 |
| SEQ. ID. NO. 13485 | 162-LeuLeuGlyAsnAspAsnProLysIleAlaArg-172 |
| SEQ. ID. NO. 13486 | 181-LysGluLeuGluAsnGlyGlyLeuAspSerValValSerAspSerAla-196 |
| SEQ. ID. NO. 13487 | 203-LysAsnAsnProAlaLysGlyMetAspPhe-212 |
| SEQ. ID. NO. 13488 | 216-ProAspPheThrThr-220 |
| SEQ. ID. NO. 13489 | 227-ValArgLysGlyAspGluAlaThrVal-235 |
| SEQ. ID. NO. 13490 | 237-MetLeuAsnAspAlaLeuGluLysValArgGluSerGlyGluTyrAspLysIleTyr-255 |
| SEQ. ID. NO. 13491 | 259-PheAlaLysGluAspGlyGlnAlaAlaLys-268 |
| Hydrophilic Regions - Hopp-Woods | |
| SEQ. ID. NO. 13492 | 23-GlyGlnGlyLysAspThrAlaAla-30 |
| SEQ. ID. NO. 13493 | 33-AlaAsnProAspLysValTyrArg-40 |
| SEQ. ID. NO. 13494 | 51-GluSerLeuAspSerLysGlyAsnValGluGlyPheAsp-63 |
| SEQ. ID. NO. 13495 | 93-AsnAsnGlyAspAlaAspVal-99 |
| SEQ. ID. NO. 13496 | 106-IleThrAspAspArgLysGlnSerMetAspPheSer-117 |
| SEQ. ID. NO. 13497 | 130-ProLysGlyLysLysValSerSerSerGluAspLeuLysAsnMetAsn-145 |
| SEQ. ID. NO. 13498 | 166-AspAsnProLysIleAlaArg-172 |
| SEQ. ID. NO. 13499 | 181-LysGluLeuGluAsnGlyGlyLeu-188 |
| SEQ. ID. NO. 13500 | 205-AsnProAlaLysGlyMetAsp-211 |
| SEQ. ID. NO. 13501 | 227-ValArgLysGlyAspGluAlaThrVal-235 |
| SEQ. ID. NO. 13502 | 237-MetLeuAsnAspAlaLeuGluLysValArgGluSerGlyGluTyrAspLysIleTyr-255 |
| SEQ. ID. NO. 13503 | 259-PheAlaLysGluAspGlyGlnAlaAlaLys-268 |
| 982 | |
| AMPHI Regions - AMPHI | |
| SEQ. ID. NO. 13504 | 12-ValArgGlnLysMetValAsnGlyValAsnIleLeuAlaAsnAlaVal-27 |
| SEQ. ID. NO. 13505 | 71-AlaGlnMetValLysGluValAlaSerLysThr-81 |
| SEQ. ID. NO. 13506 | 100-ValAlaGluGlyMetLysTyr-106 |
| SEQ. ID. NO. 13507 | 115-AspLeuLysArgGlyIleAspLysAlaValAlaAlaLeuValAspGluLeuLysAsnIleAlaLysProCysAspThrSerLysGluIleAlaGlnValGly Ser-149 |
| SEQ. ID. NO. 13508 | 160-AlaIleIleAlaGluAlaMetGluLysValGly-170 |
| SEQ. ID. NO. 13509 | 185-AsnGluLeuAspValValGluGlyMet-193 |
| SEQ. ID. NO. 13510 | 209-GluLysGlnIleAlaAla-214 |
| SEQ. ID. NO. 13511 | 227-IleSerAsnIleArgAspLeuLeuProValLeuGluGlnValAlaLysAla-243 |
| SEQ. ID. NO. 13512 | 265-AsnAsnIleArgGlyIleLeuLysThrValAla-275 |
| SEQ. ID. NO. 13513 | 313-ThrLeuAspAspLeuGlyGlnAlaLysArgIle-323 |
| SEQ. ID. NO. 13514 | 331-ThrIleIleAspGlyPheGlyAspAlaAla-340 |
| SEQ. ID. NO. 13515 | 367-GluArgValAlaLysLeuAlaGlyGlyVal-376 |
| SEQ. ID. NO. 13516 | 426-LeuGluAsnLeuHisThr-431 |
| SEQ. ID. NO. 13517 | 444-LeuArgAlaValGluSerProLeuArgGlnIleValAlaAsnAla-458 |
| SEQ. ID. NO. 13518 | 484-GluTyrGlyAspMetIleGluMet-491 |
| SEQ. ID. NO. 13519 | 500-ThrArgSerAlaLeu-504 |
| Antigenic Index - Jameson-Wolf | |
| SEQ. ID. NO. 13520 | 1-MetAlaAlaLysAspValGlnPhe-8 |
| SEQ. ID. NO. 13521 | 10-AsnGluValArgGlnLysMetValAsn-18 |
| SEQ. ID. NO. 13522 | 30-ThrLeuGlyProLysGlyArgAsnValValVal-40 |
| SEQ. ID. NO. 13523 | 43-AlaPheGlyGlyProHisIleThrLysAspGlyValThrValAlaLysGluIleGluLeuLysAspLysPheGluAsnMetGly-70 |
| SEQ. ID. NO. 13524 | 73-MetValLysGluValAlaSerLysThrAsnAspValAlaGlyAspGlyThrThr-90 |
| SEQ. ID. NO. 13525 | 112-AsnProThrAspLeuLysArgGlyIleAspLysAlaVal-124 |
| SEQ. ID. NO. 13526 | 129-AspGluLeuLysAsnIleAlaLysProCysAspThrSerLysGluIleAla-145 |
| SEQ. ID. NO. 13527 | 150-IleSerAlaAsnSerAspGluGlnVal-158 |
| SEQ. ID. NO. 13528 | 164-GluAlaMetGluLysValGlyLysGluGlyValIleThrValGluAspGlyLysSerLeuGluAsnGluLeuAspVal-189 |
| SEQ. ID. NO. 13529 | 193-MetGlnPheAspArgGlyTyr-199 |
| SEQ. ID. NO. 13530 | 207-AspAlaGluLysGlnIleAla-213 |
| SEQ. ID. NO. 13531 | 223-PheAspLysLysIleSerAsnIleArgAsp-232 |
| SEQ. ID. NO. 13532 | 239-GlnValAlaLysAlaSerArg-245 |
| SEQ. ID. NO. 13533 | 252-GluAspValGluGlyGluAla-258 |
| SEQ. ID. NO. 13534 | 266-AsnIleArgGlyIleLeu-271 |
| SEQ. ID. NO. 13535 | 278-AlaProGlyPheGlyAspArgArgLysAlaMetLeu-289 |
| SEQ. ID. NO. 13536 | 303-GluGluValGlyLeuSerLeuGluLysAlaThrLeuAspAspLeuGlyGlnAlaLysArgIleGluIleGlyLysGluAsnThrThr-331 |
| SEQ. ID. NO. 13537 | 334-AspGlyPheGlyAspAlaAlaGlnIleGluAlaArgValAlaGluIleArgGlnGlnIleGluThrAlaThrSerAspTyrAspLysGluLysLeuGlnGlu ArgValAlaLysLeuAlaGly-374 |
| SEQ. ID. NO. 13538 | 385-ThrGluValGluMetLysGluLysLysAspArgValGluAspAlaLeuHis-401 |
| SEQ. ID. NO. 13539 | 405-AlaAlaValGluGluGlyVal-411 |
| SEQ. ID. NO. 13540 | 421-ArgAlaArgAlaAlaLeu-426 |
| SEQ. ID. NO. 13541 | 430-HisThrGlyAsnAlaAspGlnAspAlaGlyVal-440 |
| SEQ. ID. NO. 13542 | 446-AlaValGluSerProLeuArg-452 |
| SEQ. ID. NO. 13543 | 455-ValAlaAsnAlaGlyGlyGluProSerVal-464 |
| SEQ. ID. NO. 13544 | 469-ValLeuGluGlyLysGlyAsnTyrGlyTyr-478 |
| SEQ. ID. NO. 13545 | 480-AlaGlySerGlyGluTyrGlyAspMetIleGlu-490 |
| SEQ. ID. NO. 13546 | 495-AspProAlaLysValThrArgSerAlaLeu-504 |
| SEQ. ID. NO. 13547 | 523-GluIleProGluAspLysProAlaValProAspMetGlyGly-536 |
| Hydrophilic Regions - Hopp-Woods | |
| SEQ. ID. NO. 13548 | 1-MetAlaAlaLysAspValGlnPhe-8 |
| SEQ. ID. NO. 13549 | 10-AsnGluValArgGlnLysMet-16 |

TABLE 1-continued

| | |
|---|---|
| SEQ. ID. NO. 13550 | 33-ProLysGlyArgAsnValValVal-40 |
| SEQ. ID. NO. 13551 | 48-HisIleThrLysAspGlyValThrValAlaLysGluIleGluLeuLysAspLysPheGluAsn-68 |
| SEQ. ID. NO. 13552 | 73-MetValLysGluValAlaSerLysThrAsnAspValAlaGlyAspGlyThrThr-90 |
| SEQ. ID. NO. 13553 | 114-ThrAspLeuLysArgGlyIleAspLysAlaVal-124 |
| SEQ. ID. NO. 13554 | 129-AspGluLeuLysAsnIleAlaLysProCysAspThrSerLysGluIleAla-145 |
| SEQ. ID. NO. 13555 | 152-AlaAsnSerAspGluGlnVal-158 |
| SEQ. ID. NO. 13556 | 164-GluAlaMetGluLysValGlyLysGluGlyValIleThrValGluAspGlyLysSerLeuGluAsnGluLeuAspVal-189 |
| SEQ. ID. NO. 13557 | 207-AspAlaGluLysGlnIleAla-213 |
| SEQ. ID. NO. 13558 | 223-PheAspLysLysIleSerAsnIleArgAsp-232 |
| SEQ. ID. NO. 13559 | 239-GlnValAlaLysAlaSerArg-245 |
| SEQ. ID. NO. 13560 | 252-GluAspValGluGlyGluAla-258 |
| SEQ. ID. NO. 13561 | 280-GlyPheGlyAspArgArgLysAlaMetLeu-289 |
| SEQ. ID. NO. 13562 | 303-GluGluValGlyLeuSerLeuGluLysAlaThrLeuAspAspLeuGlyGlnAlaLysArgIleGluIleGlyLysGluAsnThrThr-331 |
| SEQ. ID. NO. 13563 | 340-AlaGlnIleGluAlaArgValAlaGluIleArgGlnGlnIleGluThrAlaThrSerAspTyrAspLysGluLysLeuGlnGluArgValAlaLys-371 |
| SEQ. ID. NO. 13564 | 385-ThrGluValGluMetLysGluLysLysAspArgValGluAspAlaLeuHis-401 |
| SEQ. ID. NO. 13565 | 405-AlaAlaValGluGluGlyVal-411 |
| SEQ. ID. NO. 13566 | 421-ArgAlaArgAlaAlaLeu-426 |
| SEQ. ID. NO. 13567 | 433-AsnAlaAspGlnAspAla-438 |
| SEQ. ID. NO. 13568 | 446-AlaValGluSerProLeu-451 |
| SEQ. ID. NO. 13569 | 458-AlaGlyGlyGluPro-462 |
| SEQ. ID. NO. 13570 | 469-ValLeuGluGlyLysGly-474 |
| SEQ. ID. NO. 13571 | 481-GlySerGlyGluTyrGlyAsp-487 |
| SEQ. ID. NO. 13572 | 495-AspProAlaLysValThrArg-501 |
| SEQ. ID. NO. 13573 | 523-GluIleProGluAspLysProAlaVal-531 |
| 986-2 | |
| AMPHI Regions - AMPHI | |
| SEQ. ID. NO. 13574 | 6-GlnTyrLeuAlaLeuAla-11 |
| SEQ. ID. NO. 13575 | 18-LeuAlaGlyCysAspLysAlaGly-25 |
| SEQ. ID. NO. 13576 | 36-SerPheValGluArgIleGluHis-43 |
| SEQ. ID. NO. 13577 | 55-ProAspPheAlaGlnLeuValGln-62 |
| SEQ. ID. NO. 13578 | 99-PheTyrGluPhePheLysArgLeuValProAsnMetProGluIleProGln-115 |
| SEQ. ID. NO. 13579 | 145-ThrGlyMetGlySerIle-150 |
| SEQ. ID. NO. 13580 | 162-AlaLysLeuIleGlySerAspVal-169 |
| SEQ. ID. NO. 13581 | 189-IleGlyAsnProLysAspLeuLysProGly-198 |
| SEQ. ID. NO. 13582 | 200-TrpValAlaAlaIleGly-205 |
| SEQ. ID. NO. 13583 | 287-AlaGluGlnLeuLysAsnThrGlyLysVal-296 |
| SEQ. ID. NO. 13584 | 393-AlaAlaGluHisIleGlyAlaSer-400 |
| SEQ. ID. NO. 13585 | 471-ArgLysAlaMetAspLysAla-477 |
| Antigenic Index - Jameson-Wolf | |
| SEQ. ID. NO. 13586 | 1-ValPheLysLysTyr-5 |
| SEQ. ID. NO. 13587 | 20-GlyCysAspLysAlaGly-25 |
| SEQ. ID. NO. 13588 | 29-GlyAlaAspLysLysGluAlaSerPheValGluArgIleGluHisThrLysAspAspGlySerVal-50 |
| SEQ. ID. NO. 13589 | 61-ValGlnSerGluGlyProAla-67 |
| SEQ. ID. NO. 13590 | 75-ProAlaProArgThrGlnAsnGlySerGlyAsnAlaGluAsnAspSerAspProIleAlaAspAsnAspProPhe-99 |
| SEQ. ID. NO. 13591 | 104-LysArgLeuValProAsnMetProGluIleProGlnGluGluAlaAspAspGlyGlyLeu-123 |
| SEQ. ID. NO. 13592 | 130-IleIleSerLysAspGlyTyr-136 |
| SEQ. ID. NO. 13593 | 154-LeuAsnAspLysArgGluTyrThr-161 |
| SEQ. ID. NO. 13594 | 165-IleGlySerAspValGlnSerAspValAla-174 |
| SEQ. ID. NO. 13595 | 179-AspAlaThrGluGluLeuPro-185 |
| SEQ. ID. NO. 13596 | 189-IleGlyAsnProLysAspLeuLysProGlyGlu-199 |
| SEQ. ID. NO. 13597 | 208-PheGlyPheAspAsnSerVal-214 |
| SEQ. ID. NO. 13598 | 219-ValSerAlaLysGlyArgSerLeuProAsnGluSerTyr-231 |
| SEQ. ID. NO. 13599 | 242-AsnProGlyAsnSerGlyGlyPro-249 |
| SEQ. ID. NO. 13600 | 265-TyrSerArgSerGlyGly-270 |
| SEQ. ID. NO. 13601 | 288-GluGlnLeuLysAsnThrGlyLysValGlnArgGlyGlnLeu-301 |
| SEQ. ID. NO. 13602 | 316-PheGlyLeuAspLysAlaGlyGly-323 |
| SEQ. ID. NO. 13603 | 330-LeuProGlySerProAlaGluArgAlaGlyLeuGlnAlaGlyAsp-344 |
| SEQ. ID. NO. 13604 | 349-LeuAspGlyGlyGluIleArgSerSerGlyAspLeu-360 |
| SEQ. ID. NO. 13605 | 368-ThrProGlyLysGluValSer-374 |
| SEQ. ID. NO. 13606 | 378-TrpArgLysGlyGluGluIleThrIle-386 |
| SEQ. ID. NO. 13607 | 397-IleGlyAlaSerSerLysThrAspGluAlaProTyrThrGluGlnGlnSerGlyThrPhe-416 |
| SEQ. ID. NO. 13608 | 427-ThrHisThrAspSerSerGlyGly-434 |
| SEQ. ID. NO. 13609 | 440-ArgValSerAspAlaAlaGluArgAlaGlyLeuArgArgGlyAspGluIleLeu-457 |
| SEQ. ID. NO. 13610 | 463-ProValAsnAspGluAlaGlyPheArgLysAlaMetAspLysAlaGlyLysAsnVal-481 |
| SEQ. ID. NO. 13611 | 486-MetArgArgGlyAsnThr-491 |
| Hydrophilic Regions - Hopp-Woods | |
| SEQ. ID. NO. 13612 | 20-GlyCysAspLysAlaGly-25 |
| SEQ. ID. NO. 13613 | 29-GlyAlaAspLysLysGluAlaSerPheValGluArgIleGluHisThrLysAspAspGlySer-49 |
| SEQ. ID. NO. 13614 | 75-ProAlaProArgThrGlnAsnGlySerGlyAsnAlaGluAsnAspSerAspProIleAlaAspAsnAspPro-98 |
| SEQ. ID. NO. 13615 | 111-ProGluIleProGlnGluGluAlaAspAspGlyGly-122 |
| SEQ. ID. NO. 13616 | 131-IleSerLysAspGly-135 |
| SEQ. ID. NO. 13617 | 154-LeuAsnAspLysArgGluTyrThr-161 |
| SEQ. ID. NO. 13618 | 179-AspAlaThrGluGluLeuPro-185 |
| SEQ. ID. NO. 13619 | 190-GlyAsnProLysAspLeuLysPro-197 |
| SEQ. ID. NO. 13620 | 221-AlaLysGlyArgSerLeuPro-227 |
| SEQ. ID. NO. 13621 | 288-GluGlnLeuLysAsnThrGlyLysValGlnArgGlyGln-300 |
| SEQ. ID. NO. 13622 | 317-GlyLeuAspLysAlaGly-322 |
| SEQ. ID. NO. 13623 | 333-SerProAlaGluArgAlaGlyLeuGln-341 |
| SEQ. ID. NO. 13624 | 350-AspGlyGlyGluIleArgSerSerGlyAsp-359 |
| SEQ. ID. NO. 13625 | 368-ThrProGlyLysGluValSer-374 |

TABLE 1-continued

| | |
|---|---|
| SEQ. ID. NO. 13626 | 379-ArgLysGlyGluGluIleThrIle-386 |
| SEQ. ID. NO. 13627 | 397-IleGlyAlaSerSerLysThrAspGluAlaProTyrThrGluGlnGlnSer-413 |
| SEQ. ID. NO. 13628 | 428-HisThrAspSerSerGly-433 |
| SEQ. ID. NO. 13629 | 440-ArgValSerAspAlaAlaGluArgAlaGlyLeuArgArgGlyAspGluIleLeu-457 |
| SEQ. ID. NO. 13630 | 463-ProValAsnAspGluAlaGlyPheArgLysAlaMetAspLysAlaGlyLys-479 |
| 987 | |
| AMPHI Regions - AMPHI | |
| SEQ. ID. NO. 13631 | 17-CysSerSerTrpLeu-21 |
| SEQ. ID. NO. 13632 | 33-PheAsnThrSerLysProValArgLeuAspAsnIleLeuGlnIle-47 |
| SEQ. ID. NO. 13633 | 65-ProHisGluAlaPhe-69 |
| SEQ. ID. NO. 13634 | 144-AsnProPheValLeuArgLysTrpArgAlaLeuGlyTyrLeuThrAspPheProArgLeuAsnArg-165 |
| SEQ. ID. NO. 13635 | 187-GlyAspGluTyrPheLysVal-193 |
| SEQ. ID. NO. 13636 | 202-LeuAspIleLeuAlaThr-207 |
| SEQ. ID. NO. 13637 | 211-ValGlyGluValSerHisAspPheAspArgTyrTrpAla-223 |
| SEQ. ID. NO. 13638 | 230-AlaThrArgIleIleArgSerGlyAspIleGlyLysGlyLeuGlnAla-245 |
| SEQ. ID. NO. 13639 | 290-AspAspProAlaLysGlyLeuAspArg-298 |
| SEQ. ID. NO. 13640 | 307-GlyArgLeuGlnAspAlaLeuLysGlnPro-316 |
| SEQ. ID. NO. 13641 | 333-GlyThrAspAlaLeuAlaLysLeuValGlnAsp-343 |
| SEQ. ID. NO. 13642 | 355-GlnAlaThrAspValAlaAla-361 |
| SEQ. ID. NO. 13643 | 443-LysIleAlaGluGlnMetGluArgThrLeu-452 |
| SEQ. ID. NO. 13644 | 486-ProGluAlaLysLeuTrpLysArgIleAlaAlaLysIleLeuSerLeuLeuProIleGluGlyLeu-507 |
| Antigenic Index - Jameson-Wolf | |
| SEQ. ID. NO. 13645 | 1-MetLysThrArgSer-5 |
| SEQ. ID. NO. 13646 | 23-ProLeuGluGluArgThrGluSerArgHisPheAsnThrSerLysProValArgLeu-41 |
| SEQ. ID. NO. 13647 | 49-HisThrProHisThrAsnGlyLeuSer-57 |
| SEQ. ID. NO. 13648 | 77-GluSerAlaGluHisSerLeu-83 |
| SEQ. ID. NO. 13649 | 90-TrpArgAsnAspIleSerGlyArgLeu-98 |
| SEQ. ID. NO. 13650 | 107-AlaGluArgGlyValArg-112 |
| SEQ. ID. NO. 13651 | 115-LeuLeuLeuAspAspAsnAsnThrArgGlyLeuAsp-126 |
| SEQ. ID. NO. 13652 | 134-SerHisProAsnIleGluValArgLeu-142 |
| SEQ. ID. NO. 13653 | 159-AspPheProArgLeuAsnArgArgMetHisAsnLysSerPheThrAlaAspAsnArgAla-178 |
| SEQ. ID. NO. 13654 | 182-GlyGlyArgAsnIleGlyAspGluTyrPheLysValGlyGluAspThrVal-198 |
| SEQ. ID. NO. 13655 | 214-ValSerHisAspPheAspArgTyrTrp-222 |
| SEQ. ID. NO. 13656 | 225-HisSerAlaHisAsn-229 |
| SEQ. ID. NO. 13657 | 232-ArgIleIleArgSerGlyAspIleGlyLysGlyLeu-243 |
| SEQ. ID. NO. 13658 | 247-GlyTyrAsnAspGluThrSerArg-254 |
| SEQ. ID. NO. 13659 | 259-ArgTyrArgGluThrValGlu-265 |
| SEQ. ID. NO. 13660 | 267-SerProLeuTyrGln-271 |
| SEQ. ID. NO. 13661 | 282-SerValArgThrArgLeuIleSerAspAspProAlaLysGlyLeuAspArgAspArgArgLysProProIle-305 |
| SEQ. ID. NO. 13662 | 308-ArgLeuGlnAspAlaLeuLysGlnProGluLysSer-319 |
| SEQ. ID. NO. 13663 | 328-ValProThrLysSerGlyThrAspAlaLeu-337 |
| SEQ. ID. NO. 13664 | 340-LeuValGlnAspGlyIleAsp-346 |
| SEQ. ID. NO. 13665 | 367-ValLysTyrArgLysProLeuLeu-374 |
| SEQ. ID. NO. 13666 | 391-AlaThrLysAspLysGlyLeuThrGlySerSer-401 |
| SEQ. ID. NO. 13667 | 412-ValAspGlyLysArgIlePhe-418 |
| SEQ. ID. NO. 13668 | 422-PheAsnLeuAspProArgSerAlaArgLeuAsnThr-433 |
| SEQ. ID. NO. 13669 | 440-GluSerProLysIleAlaGluGlnMetGluArgThrLeuAlaAspThrThrPro-457 |
| SEQ. ID. NO. 13670 | 463-ValThrLeuAspArgHisAsnArgLeuGlnTrpHisAspProAlaThrArgLysThrTyrProAsnGluProGluAlaLysLeuTrpLys-492 |
| Hydrophilic Regions - Hopp-Woods | |
| SEQ. ID. NO. 13671 | 1-MetLysThrArgSer-5 |
| SEQ. ID. NO. 13672 | 24-LeuGluGluArgThrGluSerArgHisPheAsnThr-35 |
| SEQ. ID. NO. 13673 | 37-LysProValArgLeu-41 |
| SEQ. ID. NO. 13674 | 77-GluSerAlaGluHisSerLeu-83 |
| SEQ. ID. NO. 13675 | 107-AlaGluArgGlyValArg-112 |
| SEQ. ID. NO. 13676 | 115-LeuLeuLeuAspAspAsnAsnThrArgGlyLeuAsp-126 |
| SEQ. ID. NO. 13677 | 161-ProArgLeuAsnArgArgMetHisAsn-169 |
| SEQ. ID. NO. 13678 | 172-PheThrAlaAspAsnArgAla-178 |
| SEQ. ID. NO. 13679 | 189-GluTyrPheLysValGlyGluAspThrVal-198 |
| SEQ. ID. NO. 13680 | 214-ValSerHisAspPheAspArg-220 |
| SEQ. ID. NO. 13681 | 232-ArgIleIleArgSerGlyAspIleGlyLys-241 |
| SEQ. ID. NO. 13682 | 248-TyrAsnAspGluThrSerArg-254 |
| SEQ. ID. NO. 13683 | 259-ArgTyrArgGluThrValGlu-265 |
| SEQ. ID. NO. 13684 | 282-SerValArgThrArgLeuIleSerAspAspProAlaLysGlyLeuAspArgAspArgArgLysProProIle-305 |
| SEQ. ID. NO. 13685 | 308-ArgLeuGlnAspAlaLeuLysGlnProGluLysSer-319 |
| SEQ. ID. NO. 13686 | 331-LysSerGlyThrAspAlaLeu-337 |
| SEQ. ID. NO. 13687 | 340-LeuValGlnAspGlyIleAsp-346 |
| SEQ. ID. NO. 13688 | 367-ValLysTyrArgLysProLeuLeu-374 |
| SEQ. ID. NO. 13689 | 391-AlaThrLysAspLysGlyLeuThr-398 |
| SEQ. ID. NO. 13690 | 424-LeuAspProArgSerAlaArgLeuAsnThr-433 |
| SEQ. ID. NO. 13691 | 440-GluSerProLysIleAlaGluGlnMetGluArgThrLeuAla-453 |
| SEQ. ID. NO. 13692 | 464-ThrLeuAspArgHisAsnArg-470 |
| SEQ. ID. NO. 13693 | 476-ProAlaThrArgLysThrTyrProAsnGluProGluAlaLysLeuTrpLys-492 |
| 988-2 | |
| AMPHI Regions - AMPHI | |
| SEQ. ID. NO. 13694 | 45-SerLysIleGluSerLeuAlaArg-52 |
| SEQ. ID. NO. 13695 | 125-GlnMetArgGlyIle-129 |
| SEQ. ID. NO. 13696 | 154-AspIleValGluArgAlaGlnSerLysVal-163 |
| SEQ. ID. NO. 13697 | 221-AlaLysIleIleGluValLeuGlyAspTyrAlaAsp-232 |
| SEQ. ID. NO. 13698 | 248-HisGlnPheSerGluAlaCysAlaLysAlaAlaLysLysIle-261 |
| SEQ. ID. NO. 13699 | 288-ThrAlaArgAspPheAspAsp-294 |

TABLE 1-continued

| | |
|---|---|
| SEQ. ID. NO. 13700 | 299-GluLysValGlyArgAsnTyr-305 |
| SEQ. ID. NO. 13701 | 310-AlaIleAlaAspValSerHisTyrValArgProAspAspValIleAsp-325 |
| SEQ. ID. NO. 13702 | 348-AsnLeuSerAsnGly-352 |
| SEQ. ID. NO. 13703 | 396-AsnGlnValTrpLysTrpIleSerAspGlyIleAspHisPro-409 |
| SEQ. ID. NO. 13704 | 411-LysAlaGlnIleAspThrLeuTyrLysLeuPheLysIleLeuGlnLys-426 |
| SEQ. ID. NO. 13705 | 494-LeuGlyProThrProGluLysLeuAlaThrLeu-504 |
| SEQ. ID. NO. 13706 | 526-TyrAlaAlaLeuValGluGlnPheLys-534 |
| SEQ. ID. NO. 13707 | 544-ValMetMetLeuArgSerMetGlnGlnAla-553 |
| SEQ. ID. NO. 13708 | 569-AlaTyrAlaHisPheThrSerProIleArgArgTyrProAspLeuThrValHisArgAlaIleLysAlaValLeu-593 |
| SEQ. ID. NO. 13709 | 619-AspAspAlaSerArgAspValGluAsnTrpLeuLys-630 |
| SEQ. ID. NO. 13710 | 646-IleSerGlyMetThrSerPheGlyIlePheValThrLeu-658 |
| SEQ. ID. NO. 13711 | 662-HisIleAspGlyLeuValHisIleSerAspLeuGlyGlu-674 |
| Antigenic Index - Jameson-Wolf | |
| SEQ. ID. NO. 13712 | 1-MetAsnLysAsnIleLys-6 |
| SEQ. ID. NO. 13713 | 8-LeuAsnLeuArgGluLysAspProPheLeuSerArgGluLysGlnArgTyrGluHisProLeuProSerArgGluTrpIle-34 |
| SEQ. ID. NO. 13714 | 37-LeuLeuGluArgLysGlyValProSerLysIleGluSerLeuAlaArgGluLeuSerIleThrGluAspGluTyrValPhePheGluArgArgLeuLysAla MetAlaArgAspGlyGln-76 |
| SEQ. ID. NO. 13715 | 79-IleAsnArgArgGlyAlaVal-85 |
| SEQ. ID. NO. 13716 | 87-AlaAlaAspLysLeuAspLeuValLysCysArgValGluAlaHisLysAspGlyPhe-105 |
| SEQ. ID. NO. 13717 | 111-LeuThrProAlaLysAspGlyAsp-118 |
| SEQ. ID. NO. 13718 | 124-ArgGlnMetArgGly-128 |
| SEQ. ID. NO. 13719 | 138-ArgProAlaGlyMetAspArgArgGlyArgArgGluGlyThrVal-152 |
| SEQ. ID. NO. 13720 | 155-IleValGluArgAlaGlnSerLysValVal-164 |
| SEQ. ID. NO. 13721 | 168-TyrMetAspArgGlyValAla-174 |
| SEQ. ID. NO. 13722 | 176-LeuGluProGluAspLysArgLeuAsnGln-185 |
| SEQ. ID. NO. 13723 | 189-LeuGluProAspGlyValAlaArgPheLysProGluSerGlyGln-203 |
| SEQ. ID. NO. 13724 | 210-GluValTyrProGluGlnAsnArgProAlaVal-220 |
| SEQ. ID. NO. 13725 | 227-LeuGlyAspTyrAlaAspSerGlyMetGluIle-237 |
| SEQ. ID. NO. 13726 | 239-IleAlaValArgLysHisHisLeu-246 |
| SEQ. ID. NO. 13727 | 253-AlaCysAlaLysAlaAlaLysLysIleProValHisValArgLysSerAspLeuLysGlyArgValAspLeuArgAsp-278 |
| SEQ. ID. NO. 13728 | 283-ThrIleAspGlyGluThrAlaArgAspPheAspAsp-294 |
| SEQ. ID. NO. 13729 | 299-GluLysValGlyArgAsnTyrArg-306 |
| SEQ. ID. NO. 13730 | 316-HisTyrValArgProAspAspValIleAspAlaAspAlaGlnGluArgSerThrSer-334 |
| SEQ. ID. NO. 13731 | 337-PheProArgArgVal-341 |
| SEQ. ID. NO. 13732 | 345-LeuProGluAsnLeuSerAsnGly-352 |
| SEQ. ID. NO. 13733 | 356-LeuAsnProAspValGluArgLeu-363 |
| SEQ. ID. NO. 13734 | 374-AlaGlyAsnIleLysGluTyrArgPhe-382 |
| SEQ. ID. NO. 13735 | 402-IleSerAspGlyIleAspHisProTyrLysAlaGlnIle-414 |
| SEQ. ID. NO. 13736 | 424-LeuGlnLysLysArgPheGluArgGlyAlaValGluPheGluSerValGlu-440 |
| SEQ. ID. NO. 13737 | 443-MetIlePheAspAspAsnGlyLysIleGluLys-453 |
| SEQ. ID. NO. 13738 | 458-ValArgAsnAspAlaHisLysLeuIleGlu-467 |
| SEQ. ID. NO. 13739 | 482-LeuLysAsnLysHisThrAla-488 |
| SEQ. ID. NO. 13740 | 493-HisLeuGlyProThrProGluLysLeuAlaThrLeuArgGluGlnLeu-508 |
| SEQ. ID. NO. 13741 | 516-GlyGlyGlyAspAsnProSerProLysAspTyr-526 |
| SEQ. ID. NO. 13742 | 532-GlnPheLysGlyArgProAspAlaGluLeu-541 |
| SEQ. ID. NO. 13743 | 556-GluProHisCysAspGlyHis-562 |
| SEQ. ID. NO. 13744 | 575-SerProIleArgArgTyrProAspLeuThrVal-585 |
| SEQ. ID. NO. 13745 | 597-ThrTyrThrProLysLysSerTrp-604 |
| SEQ. ID. NO. 13746 | 613-PheCysGluArgArgAlaAspAspAlaSerArgAspValGluAsn-627 |
| SEQ. ID. NO. 13747 | 633-TyrMetArgAspLysValGlyGluValPheGluGlyLysIleSerGly-648 |
| SEQ. ID. NO. 13748 | 670-SerAspLeuGlyGluAspTyrPheAsnPheArgPro-681 |
| SEQ. ID. NO. 13749 | 683-IleMetAlaIleGluGlyGluArgSerGlyIleArgPheAsnMetGlyAspArgValAlaValArgValAlaArgAlaAspLeuAspAspGlyLysIle-715 |
| SEQ. ID. NO. 13750 | 722-GlyGlySerGlyArgGlyArgLysValLysSerSerAlaSerAlaLysProAlaGlyThrAlaGlyLysGlyLysProLysThrAlaAlaGluLysLysThr AlaArgGlyGlyLysValArgGlyArgGlyAlaSerAlaAlaAlaGluSerArgLysLysAlaLysLysProValProIleLysValLysLysArgLysGlyLys Ser-791 |
| Hydrophilic Regions - Hopp-Woods | |
| SEQ. ID. NO. 13751 | 1-MetAsnLysAsnIleLys-6 |
| SEQ. ID. NO. 13752 | 8-LeuAsnLeuArgGluLysAspProPheLeuSerArgGluLysGlnArgTyrGluHis-26 |
| SEQ. ID. NO. 13753 | 37-LeuLeuGluArgLysGlyValProSerLysIleGluSerLeuAlaArgGluLeuSerIleThrGluAspGluTyrValPhePheGluArgArgLeuLysAla MetAlaArgAspGlyGln-76 |
| SEQ. ID. NO. 13754 | 79-IleAsnArgArgGlyAla-84 |
| SEQ. ID. NO. 13755 | 87-AlaAlaAspLysLeuAspLeuValLysCysArgValGluAlaHisLysAspGlyPhe-105 |
| SEQ. ID. NO. 13756 | 113-ProAlaLysAspGlyAsp-118 |
| SEQ. ID. NO. 13757 | 140-AlaGlyMetAspArgArgGlyArgArgGluGlyThrVal-152 |
| SEQ. ID. NO. 13758 | 155-IleValGluArgAlaGlnSerLysValVal-164 |
| SEQ. ID. NO. 13759 | 176-LeuGluProGluAspLysArgLeuAsn-184 |
| SEQ. ID. NO. 13760 | 189-LeuGluProAspGlyValAlaArgPheLysProGluSerGly-202 |
| SEQ. ID. NO. 13761 | 210-GluValTyrProGluGlnAsnArgProAlaVal-220 |
| SEQ. ID. NO. 13762 | 230-TyrAlaAspSerGlyMetGluIle-237 |
| SEQ. ID. NO. 13763 | 239-IleAlaValArgLysHisHis-245 |
| SEQ. ID. NO. 13764 | 253-AlaCysAlaLysAlaAlaLysLysIleProValHisValArgLysSerAspLeuLysGlyArgValAspLeuArgAsp-278 |
| SEQ. ID. NO. 13765 | 284-IleAspGlyGluThrAlaArgAspPheAspAsp-294 |
| SEQ. ID. NO. 13766 | 299-GluLysValGlyArgAsnTyr-305 |
| SEQ. ID. NO. 13767 | 318-ValArgProAspAspValIleAspAlaAspAlaGlnGluArgSerThr-333 |
| SEQ. ID. NO. 13768 | 358-ProAspValGluArg-362 |
| SEQ. ID. NO. 13769 | 376-AsnIleLysGluTyrArg-381 |
| SEQ. ID. NO. 13770 | 405-GlyIleAspHisProTyr-410 |
| SEQ. ID. NO. 13771 | 424-LeuGlnLysLysArgPheGluArgGlyAlaValGluPheGluSerValGlu-440 |
| SEQ. ID. NO. 13772 | 443-MetIlePheAspAspAsnGlyLysIleGluLys-453 |
| SEQ. ID. NO. 13773 | 458-ValArgAsnAspAlaHisLysLeuIleGlu-467 |

TABLE 1-continued

| | |
|---|---|
| SEQ. ID. NO. 13774 | 496-ProThrProGluLysLeuAlaThrLeuArgGluGlnLeu-508 |
| SEQ. ID. NO. 13775 | 517-GlyGlyAspAsnProSerProLysAspTyr-526 |
| SEQ. ID. NO. 13776 | 532-GlnPheLysGlyArgProAspAlaGluLeu-541 |
| SEQ. ID. NO. 13777 | 576-ProIleArgArgTyrProAsp-582 |
| SEQ. ID. NO. 13778 | 598-TyrThrProLysLysSerTrp-604 |
| SEQ. ID. NO. 13779 | 613-PheCysGluArgArgAlaAspAspAlaSerArgAspValGluAsn-627 |
| SEQ. ID. NO. 13780 | 633-TyrMetArgAspLysValGlyGluValPheGluGlyLysIle-646 |
| SEQ. ID. NO. 13781 | 683-IleMetAlaIleGluGlyGluArgSerGlyIle-693 |
| SEQ. ID. NO. 13782 | 696-AsnMetGlyAspArgValAlaValArgValAlaArgAlaAspLeuAspAspGlyLysIle-715 |
| SEQ. ID. NO. 13783 | 723-GlySerGlyArgGlyArgLysValLysSerSerAlaSerAlaLysProAlaGlyThrAlaGlyLysGlyLysProLysThrAlaAlaGluLysLysThrAla ArgGlyGlyLysValArgGlyArgGlyAlaSerAlaAlaAlaGluSerArgLysLysAlaLysLysProValProIleLysValLysLysArgLysGlyLys Ser-791 |
| 989 | |
| AMPHI Regions - AMPHI | |
| SEQ. ID. NO. 13784 | 58-AlaGlyLeuThrLysLeu-63 |
| SEQ. ID. NO. 13785 | 85-SerAlaThrAspPhe-89 |
| SEQ. ID. NO. 13786 | 98-LysSerGlyLysIleThr-103 |
| SEQ. ID. NO. 13787 | 109-ProHisIleTyrGlyAla-114 |
| SEQ. ID. NO. 13788 | 183-GluLeuArgLysTyrAlaAsp-189 |
| SEQ. ID. NO. 13789 | 205-LysProAsnGlyValAlaGluAla-212 |
| SEQ. ID. NO. 13790 | 273-AlaMetTrpSerThr-277 |
| SEQ. ID. NO. 13791 | 301-SerValHisGlyMetTyrLysValSer-309 |
| SEQ. ID. NO. 13792 | 320-TrpThrArgHisSerArg-325 |
| SEQ. ID. NO. 13793 | 364-SerTyrGlnIleSerGluProLeu-371 |
| SEQ. ID. NO. 13794 | 450-PheLysAsnHisAlaAsp-455 |
| Antigenic Index - Jameson-Wolf | |
| SEQ. ID. NO. 13795 | 46-GluAlaAlaAspAlaSer-51 |
| SEQ. ID. NO. 13796 | 57-ProAlaGlyLeuThrLysLeuAspSerSerGlnIle-68 |
| SEQ. ID. NO. 13797 | 81-TyrGluAlaAspSerAlaThrAspPheThr-90 |
| SEQ. ID. NO. 13798 | 95-GlnGlySerLysSerGlyLysIleThrLysThrThr-106 |
| SEQ. ID. NO. 13799 | 116-LysValAsnAspAsnLeuThr-122 |
| SEQ. ID. NO. 13800 | 132-GlySerAlaThrGluTyrGluLysAspSerValLeu-143 |
| SEQ. ID. NO. 13801 | 146-AsnIleAsnLysLeuGly-151 |
| SEQ. ID. NO. 13802 | 164-LysLeuAsnAspArgHisSerPheGly-172 |
| SEQ. ID. NO. 13803 | 180-ThrSerAlaGluLeuArgLysTyrAla-188 |
| SEQ. ID. NO. 13804 | 191-GlyIleLysSerLysAlaGluIleLeuThrAlaLysProProLysProAsnGlyValAlaGluAlaAlaLysIleGlnAlaAspGlyHisAlaAspValLysGly SerAspTrpGly-229 |
| SEQ. ID. NO. 13805 | 239-AspIleAsnAspArgAlaArgValGlyValAsnTyrArgSerLysValSerHisThrLeuLysGlyAspAlaGluTrpAlaAla-266 |
| SEQ. ID. NO. 13806 | 285-ThrAlaAsnGluLysAlaArgValLysIleValThrProGluSer-299 |
| SEQ. ID. NO. 13807 | 306-TyrLysValSerAspLysAlaAspLeu-314 |
| SEQ. ID. NO. 13808 | 319-ThrTrpThrArgHisSerArgPheAspLysAlaGluLeuValPheGluLysGluLysThrValValLysGlyLysSerAspArgThrThrIle-349 |
| SEQ. ID. NO. 13809 | 351-ProAsnTrpArgAsnThrTyrLys-358 |
| SEQ. ID. NO. 13810 | 363-GlySerTyrGlnIleSerGlu-369 |
| SEQ. ID. NO. 13811 | 377-IleAlaPheAspLysSerProValArgAsnAlaAspTyrArgMetAsnSerLeuProAspGlyAsn-398 |
| SEQ. ID. NO. 13812 | 409-HisIleGlyLysAsnHisVal-415 |
| SEQ. ID. NO. 13813 | 426-AsnAspThrSerTyrArgThrAlaLysAlaSerGlyAsnAspValAspSerLysGlyAlaSerSerAlaArgPheLysAsnHisAla-454 |
| Hydrophilic Regions - Hopp-Woods | |
| SEQ. ID. NO. 13814 | 61-ThrLysLeuAspSerSerGln-67 |
| SEQ. ID. NO. 13815 | 81-TyrGluAlaAspSerAlaThr-87 |
| SEQ. ID. NO. 13816 | 95-GlnGlySerLysSerGlyLysIleThrLys-104 |
| SEQ. ID. NO. 13817 | 135-ThrGluTyrGluLysAspSerValLeu-143 |
| SEQ. ID. NO. 13818 | 164-LysLeuAsnAspArgHisSer-170 |
| SEQ. ID. NO. 13819 | 180-ThrSerAlaGluLeuArgLysTyrAla-188 |
| SEQ. ID. NO. 13820 | 191-GlyIleLysSerLysAlaGluIleLeuThr-200 |
| SEQ. ID. NO. 13821 | 202-LysProProLysProAsnGlyValAlaGluAlaAlaLysIleGlnAla-217 |
| SEQ. ID. NO. 13822 | 219-GlyHisAlaAspValLysGlySerAsp-227 |
| SEQ. ID. NO. 13823 | 240-IleAsnAspArgAlaArgVal-246 |
| SEQ. ID. NO. 13824 | 250-TyrArgSerLysVal-254 |
| SEQ. ID. NO. 13825 | 258-LeuLysGlyAspAlaGluTrpAlaAla-266 |
| SEQ. ID. NO. 13826 | 285-ThrAlaAsnGluLysAlaArgValLysIleValThr-296 |
| SEQ. ID. NO. 13827 | 307-LysValSerAspLysAlaAspLeu-314 |
| SEQ. ID. NO. 13828 | 324-SerArgPheAspLysAlaGluLeuValPheGluLysGluLysThrValValLysGlyLysSerAspArgThrThrIle-349 |
| SEQ. ID. NO. 13829 | 377-IleAlaPheAspLysSerProValArgAsnAlaAspTyrArgMet-391 |
| SEQ. ID. NO. 13830 | 393-SerLeuProAspGlyAsn-398 |
| SEQ. ID. NO. 13831 | 428-ThrSerTyrArgThrAlaLysAlaSerGlyAsnAspValAspSerLysGlyAlaSerSerAlaArgPheLysAsnHisAla-454 |
| 990 | |
| AMPHI Regions - AMPHI | |
| SEQ. ID. NO. 13832 | 89-LysSerGlnLeuGlnAspLeuTyrLys-97 |
| SEQ. ID. NO. 13833 | 128-ThrMetProAspLeuIleAsnLysLeuVal-137 |
| SEQ. ID. NO. 13834 | 151-ThrSerLeuAsnAsnIlePhe-157 |
| SEQ. ID. NO. 13835 | 191-ArgArgHisSerAspIleHisThrLeuGluThrSerAsp-203 |
| SEQ. ID. NO. 13836 | 260-ProGluAsnLeuLysThrLeuAspGly-268 |
| SEQ. ID. NO. 13837 | 293-TyrGluLeuLeuLeuLysGlnCys-300 |
| SEQ. ID. NO. 13838 | 372-AlaAspGlyTrpArgLysGlyVal-379 |
| SEQ. ID. NO. 13839 | 423-GlyTyrGlyGlyGlyValTyrAlaAlaTrp-432 |
| SEQ. ID. NO. 13840 | 442-AlaTyrLeuAspGlyTrpLeuGlnTyr-450 |
| SEQ. ID. NO. 13841 | 472-ThrAlaSerValGluGlyGlyTyrAsnAlaLeu-482 |
| SEQ. ID. NO. 13842 | 550-GlnProPheAlaAlaPheAsnValLeuHisArg-560 |

TABLE 1-continued

| | |
|---|---|
| Antigenic Index - Jameson-Wolf | |
| SEQ. ID. NO. 13843 | 6-LeuGlySerAsnThrArgSerThrLysIleGlyAspAspAlaAspPheSerPheSerAspLysProLysProGlyThr-31 |
| SEQ. ID. NO. 13844 | 35-PheSerSerGlyLysThrAspGlnAsnSerSerGluTyrGlyTyrAspGluIleAsnIleGlnGlyLysAsnTyrAsnSerGlyIle-63 |
| SEQ. ID. NO. 13845 | 75-TyrIleThrGluLysTyrGlyAlaAspLeuLysGlnAlaVal-88 |
| SEQ. ID. NO. 13846 | 90-SerGlnLeuGlnAspLeuTyrLysThrArgProGluAlaTrpAlaGluAsnLysLysArgThrGluGluAlaTyr-114 |
| SEQ. ID. NO. 13847 | 120-ThrLysPheSerThrLeuLysGlnThrMetPro-130 |
| SEQ. ID. NO. 13848 | 145-HisSerAsnThrSerGlnThrSer-152 |
| SEQ. ID. NO. 13849 | 157-PheAsnLysLysLeuHisValLysIleGluAsnLysSerHisVal-171 |
| SEQ. ID. NO. 13850 | 179-ThrLysMetThrLeuLysAspSerLeuTrpGluProArgArgHisSerAspIleHisThrLeuGluThrSerAspAsnAlaArgIleArgLeuAsnThrLys AspGluLysLeuThrValHisLysAspTyrAlaGlyGlyAlaAsp-227 |
| SEQ. ID. NO. 13851 | 232-TyrAspValArgGluSerAspGluProAlaLeuThrPheGluAspLysValSerGlyGlnSerGlyValValLeuGluArgArgProGluAsnLeuLys ThrLeuAspGlyArgLysLeuIleAla-273 |
| SEQ. ID. NO. 13852 | 275-LysThrAlaAspSerGlySerPheAlaPheLysGlnAsnTyrArgGlnGlyLeu-292 |
| SEQ. ID. NO. 13853 | 298-LysGlnCysGluGlyGlyPhe-304 |
| SEQ. ID. NO. 13854 | 312-AlaIleProGluAlaGlu-317 |
| SEQ. ID. NO. 13855 | 335-ArgAlaAlaAspArgGlyAspAspValTyrAlaAlaAspProSerArgGlnLysLeu-353 |
| SEQ. ID. NO. 13856 | 358-IleGlyGlyArgSerHisGlnAsnIleArgGlyGlyAlaAlaAlaAspGlyTrpArgLysGlyVal-379 |
| SEQ. ID. NO. 13857 | 385-ValPheValArgGlnAsnGluGlySerArgLeuAla-396 |
| SEQ. ID. NO. 13858 | 400-MetGlyGlyArgAlaGlyGln-406 |
| SEQ. ID. NO. 13859 | 408-AlaSerValAsnGlyLysGlyGlyAlaAlaGlySerAspLeu-421 |
| SEQ. ID. NO. 13860 | 435-LeuArgAspLysGlnThrGlyAlaTyr-443 |
| SEQ. ID. NO. 13861 | 452-ArgPheLysHisArgIleAsnAspGluAsnArgAlaGluArgTyrLysThrLysGlyTrpThr-472 |
| SEQ. ID. NO. 13862 | 475-ValGluGlyGlyTyr-479 |
| SEQ. ID. NO. 13863 | 487-IleValGlyLysGlyAsnAsnValArg-495 |
| SEQ. ID. NO. 13864 | 510-AsnGlyGlyPheThrAspSerGluGlyThrAla-520 |
| SEQ. ID. NO. 13865 | 525-GlySerGlyGlnTrpGlnSerArgAlaGlyIleArgAlaLysThrArgPheAlaLeuArgAsnGlyValAsn-548 |
| SEQ. ID. NO. 13866 | 559-HisArgSerLysSerPheGlyValGluMetAspGlyGluLysGlnThrLeuAla-576 |
| SEQ. ID. NO. 13867 | 579-ThrAlaLeuGluGlyArgPheGlyIle-587 |
| SEQ. ID. NO. 13868 | 589-AlaGlyTrpLysGlyHisMet-595 |
| SEQ. ID. NO. 13869 | 600-GlyTyrGlyLysArgThrAspGlyAspLysGluAlaAlaLeu-613 |
| Hydrophilic Regions - Hopp-Woods | |
| SEQ. ID. NO. 13870 | 8-SerAsnThrArgSerThrLysIleGlyAspAspAlaAspPheSerPheSerAspLysProLysProGlyThr-31 |
| SEQ. ID. NO. 13871 | 38-GlyLysThrAspGlnAsnSerSer-45 |
| SEQ. ID. NO. 13872 | 79-LysTyrGlyAlaAspLeuLysGlnAlaVal-88 |
| SEQ. ID. NO. 13873 | 96-TyrLysThrArgProGluAlaTrpAlaGluAsnLysLysArgThrGluGluAlaTyr-114 |
| SEQ. ID. NO. 13874 | 161-LeuHisValLysIleGluAsnLysSerHisVal-171 |
| SEQ. ID. NO. 13875 | 179-ThrLysMetThrLeuLys-184 |
| SEQ. ID. NO. 13876 | 186-SerLeuTrpGluProArgArgHisSerAsp-195 |
| SEQ. ID. NO. 13877 | 200-GluThrSerAspAsnAlaArgIleArgLeuAsnThrLysAspGluLysLeuThrVal-218 |
| SEQ. ID. NO. 13878 | 220-LysAspTyrAlaGly-224 |
| SEQ. ID. NO. 13879 | 233-AspValArgGluSerAspGluProAlaLeuThrPheGluAspLysValSerGly-250 |
| SEQ. ID. NO. 13880 | 255-ValLeuGluArgArgProGluAsnLeuLysThrLeuAspGlyArgLysLeuIleAla-273 |
| SEQ. ID. NO. 13881 | 275-LysThrAlaAspSerGly-280 |
| SEQ. ID. NO. 13882 | 312-AlaIleProGluAlaGlu-317 |
| SEQ. ID. NO. 13883 | 335-ArgAlaAlaAspArgGlyAspAspValTyrAla-345 |
| SEQ. ID. NO. 13884 | 347-AspProSerArgGln-351 |
| SEQ. ID. NO. 13885 | 361-ArgSerHisGlnAsnIleArgGly-368 |
| SEQ. ID. NO. 13886 | 373-AspGlyTrpArgLys-377 |
| SEQ. ID. NO. 13887 | 385-ValPheValArgGlnAsnGluGlySerArg-394 |
| SEQ. ID. NO. 13888 | 410-ValAsnGlyLysGlyGlyAlaAlaGly-418 |
| SEQ. ID. NO. 13889 | 435-LeuArgAspLysGlnThr-440 |
| SEQ. ID. NO. 13890 | 452-ArgPheLysHisArgIleAsnAspGluAsnArgAlaGluArgTyrLysThr-468 |
| SEQ. ID. NO. 13891 | 513-PheThrAspSerGluGlyThr-519 |
| SEQ. ID. NO. 13892 | 533-AlaGlyIleArgAlaLysThrArgPheAlaLeu-543 |
| SEQ. ID. NO. 13893 | 559-HisArgSerLysSerPheGlyValGluMetAspGlyGluLysGlnThrLeuAla-576 |
| SEQ. ID. NO. 13894 | 579-ThrAlaLeuGluGly-583 |
| SEQ. ID. NO. 13895 | 600-GlyTyrGlyLysArgThrAspGlyAspLysGluAlaAlaLeu-613 |
| 992 | |
| AMPHI Regions - AMPHI | |
| SEQ. ID. NO. 13896 | 6-ArgHisLeuLysAsnMetGlnIleLysLysIleMetLysTrp-19 |
| SEQ. ID. NO. 13897 | 24-LeuSerLeuLeuGlyAlaLeuGlyTyr-32 |
| SEQ. ID. NO. 13898 | 45-AlaValLeuAspValLeuGlyAlaAla-53 |
| SEQ. ID. NO. 13899 | 72-HisArgTyrThrGlyThrValSerLysValTyr-82 |
| SEQ. ID. NO. 13900 | 158-GlnValGlnAspGly-162 |
| SEQ. ID. NO. 13901 | 179-AspPheAlaAspTyr-183 |
| Antigenic Index - Jameson-Wolf | |
| SEQ. ID. NO. 13902 | 1-MetPheArgArgHisArgHisLeuLys-9 |
| SEQ. ID. NO. 13903 | 34-GlyTyrGlySerGluAlaValArg-41 |
| SEQ. ID. NO. 13904 | 52-AlaAlaGlyAspAlaGlySerAspAlaProAlaArgArgArgAlaSerAlaLysSerGlyHisArgTyrThr-75 |
| SEQ. ID. NO. 13905 | 79-SerLysValTyrAspGlyAspThr-86 |
| SEQ. ID. NO. 13906 | 90-IleAspGlyAspGlyAlaLysHisLysIle-99 |
| SEQ. ID. NO. 13907 | 105-AspAlaProGluMetLysGlnAlaTyrGlyThrArgSerArgAspAsnLeuArgAlaAlaAlaGluGlyArgLysValSer-131 |
| SEQ. ID. NO. 13908 | 134-ValPheAspThrAspArgTyrGlnArgGluValAla-145 |
| SEQ. ID. NO. 13909 | 148-SerValGlyLysThrAspLeuAsn-155 |
| SEQ. ID. NO. 13910 | 168-LysSerTyrAlaLysGluGlnGlnAspLysAlaAspPhe-180 |
| SEQ. ID. NO. 13911 | 187-GlnIleGlnAlaGluArgGluArgLysGlyLeuTrpLysAlaLysAsnProGlnAlaPro-206 |
| SEQ. ID. NO. 13912 | 208-AlaTyrArgArgAlaGlyArgSerGlyGlyGlyAsnLysAspTrpMetAsp-224 |
| Hydrophilic Regions - Hopp-Woods | |
| SEQ. ID. NO. 13913 | 1-MetPheArgArgHisArgHisLeuLys-9 |
| SEQ. ID. NO. 13914 | 54-GlyAspAlaGlySerAspAlaProAlaArgArgArgAlaSerAlaLysSerGlyHisArg-73 |

TABLE 1-continued

| | |
|---|---|
| SEQ. ID. NO. 13915 | 90-IleAspGlyAspGlyAlaLysHisLysIle-99 |
| SEQ. ID. NO. 13916 | 105-AspAlaProGluMetLysGln-111 |
| SEQ. ID. NO. 13917 | 113-TyrGlyThrArgSerArgAspAsnLeuArgAlaAlaAlaGluGlyArgLysValSer-131 |
| SEQ. ID. NO. 13918 | 134-ValPheAspThrAspArgTyrGlnArgGluValAla-145 |
| SEQ. ID. NO. 13919 | 148-SerValGlyLysThrAspLeu-154 |
| SEQ. ID. NO. 13920 | 169-SerTyrAlaLysGluGlnGlnAspLysAlaAspPhe-180 |
| SEQ. ID. NO. 13921 | 187-GlnIleGlnAlaGluArgGluArgLysGlyLeuTrpLysAlaLysAsnPro-203 |
| SEQ. ID. NO. 13922 | 211-ArgAlaGlyArgSerGlyGlyGlyAsnLysAspTrpMet-223 |
| 993 | |
| AMPHI Regions - AMPHI | |
| SEQ. ID. NO. 13923 | 6-GlySerPheGlnGlyProLeuAspLeuLeuLeu-16 |
| SEQ. ID. NO. 13924 | 35-ThrGluGlnTyrLeuHisTyrIleAlaGlnIle-45 |
| SEQ. ID. NO. 13925 | 105-GlyLeuAspAlaLeuProArgAla-112 |
| SEQ. ID. NO. 13926 | 136-IleThrAspLeuThrGlnAlaTrpLeuGly-145 |
| SEQ. ID. NO. 13927 | 152-HisThrArgSerHisGluValIle-159 |
| SEQ. ID. NO. 13928 | 169-MetThrAlaIleLeuArgArgLeuAsnGlyHisGlyIleCysArgPheHisAspLeuPheAsn-189 |
| SEQ. ID. NO. 13929 | 199-ValAsnPheIleAlaLeuLeu-205 |
| SEQ. ID. NO. 13930 | 211-GlyLeuValArgIleValGln-217 |
| Antigenic Index - Jameson-Wolf | |
| SEQ. ID. NO. 13931 | 20-ArgLysGlnAsnIleAsp-25 |
| SEQ. ID. NO. 13932 | 70-LeuLeuLeuProArgThrGluThrValGluAspGluGluAlaAspProArgAlaGluLeuValArg-91 |
| SEQ. ID. NO. 13933 | 108-AlaLeuProArgAlaGlyArgAspPhe-116 |
| SEQ. ID. NO. 13934 | 148-SerArgAlaLysHisThrArgSerHisGluValIleLysGluThrIleSer-164 |
| SEQ. ID. NO. 13935 | 172-IleLeuArgArgLeuAsnGlyHisGlyIle-181 |
| SEQ. ID. NO. 13936 | 186-AspLeuPheAsnProLysGlnGlyAla-194 |
| SEQ. ID. NO. 13937 | 207-LeuAlaLysGluGlyLeu-212 |
| SEQ. ID. NO. 13938 | 216-ValGlnGluAspGlyPheGlyGluIleArgIle-226 |
| SEQ. ID. NO. 13939 | 228-LeuAsnHisGluGlyAlaHisSerAspGlyIleSerGlyThrArgGlyGlyArgAspValPhe-248 |
| Hydrophilic Regions - Hopp-Woods | |
| SEQ. ID. NO. 13940 | 20-ArgLysGlnAsnIleAsp-25 |
| SEQ. ID. NO. 13941 | 70-LeuLeuLeuProArgThrGluThrValGluAspGluGluAlaAspProArgAlaGluLeuValArg-91 |
| SEQ. ID. NO. 13942 | 108-AlaLeuProArgAlaGlyArg-114 |
| SEQ. ID. NO. 13943 | 148-SerArgAlaLysHisThrArgSerHisGluValIleLysGluThrIleSer-164 |
| SEQ. ID. NO. 13944 | 207-LeuAlaLysGluGlyLeu-212 |
| SEQ. ID. NO. 13945 | 216-ValGlnGluAspGlyPheGly-222 |
| SEQ. ID. NO. 13946 | 232-GlyAlaHisSerAspGlyIleSerGlyThrArgGlyGlyArgAspValPhe-248 |
| 996 | |
| AMPHI Regions - AMPHI | |
| SEQ. ID. NO. 13947 | 21-LysSerAlaArgThrHisAlaLysIlePro-30 |
| SEQ. ID. NO. 13948 | 50-ProGlyGluSerTyrProAlaGlnLeuGlnLysLeuThrGlyTrpAsn-65 |
| SEQ. ID. NO. 13949 | 75-ThrSerAlaGlnAlaLeuSerArgLeuProAla-85 |
| SEQ. ID. NO. 13950 | 104-LeuArgLysValProLysGlu-110 |
| SEQ. ID. NO. 13951 | 115-AsnIleAlaLysIleIleGluThrValGlnLys-125 |
| SEQ. ID. NO. 13952 | 140-LeuGlyAlaLeuPheGlyHisLeuSerAsp-149 |
| SEQ. ID. NO. 13953 | 167-GlyAlaTrpAlaGlu-171 |
| SEQ. ID. NO. 13954 | 186-AsnGlyLysGlyTyrArgLysPheAlaGluAspLeuAsnGlnPheLeuArgLysGlnGlyPhe-206 |
| Antigenic Index - Jameson-Wolf | |
| SEQ. ID. NO. 13955 | 1-MetAsnArgArgThrPhe-6 |
| SEQ. ID. NO. 13956 | 18-CysGlyArgLysSerAlaArgThrHisAlaLysIleProGluGlySerThr-34 |
| SEQ. ID. NO. 13957 | 46-TyrGlyAlaAsnProGlyGluSerTyrPro-55 |
| SEQ. ID. NO. 13958 | 69-GlyGlyValSerGlyAspThrSerAla-77 |
| SEQ. ID. NO. 13959 | 87-LeuAlaArgLysProLys-92 |
| SEQ. ID. NO. 13960 | 99-GlyGlyAsnAspPheLeuArgLysValProLysGluGlnThrArgAlaAsnIle-116 |
| SEQ. ID. NO. 13961 | 121-GluThrValGlnLysGluAsnIlePro-129 |
| SEQ. ID. NO. 13962 | 148-SerAspHisProLeuTyrGluAspLeuSerGluGluTyrGly-161 |
| SEQ. ID. NO. 13963 | 173-LeuGlyAspAsnAsnLeuLysSerAspGlnIleHisAlaAsnGlyLysGlyTyrArgLysPheAlaGluAspLeuAsnGlnPheLeuArgLysGlnGly PheArg-207 |
| Hydrophilic Regions - Hopp-Woods | |
| SEQ. ID. NO. 13964 | 18-CysGlyArgLysSerAlaArgThrHisAlaLysIleProGlu-31 |
| SEQ. ID. NO. 13965 | 49-AsnProGlyGluSerTyr-54 |
| SEQ. ID. NO. 13966 | 71-ValSerGlyAspThrSerAla-77 |
| SEQ. ID. NO. 13967 | 87-LeuAlaArgLysProLys-92 |
| SEQ. ID. NO. 13968 | 102-AspPheLeuArgLysValProLysGluGlnThrArgAlaAsnIle-116 |
| SEQ. ID. NO. 13969 | 121-GluThrValGlnLysGluAsnIle-128 |
| SEQ. ID. NO. 13970 | 154-GluAspLeuSerGluGluTyrGly-161 |
| SEQ. ID. NO. 13971 | 176-AsnAsnLeuLysSerAspGlnIleHisAlaAsn-186 |
| SEQ. ID. NO. 13972 | 188-LysGlyTyrArgLysPheAlaGluAspLeuAsnGlnPheLeuArg-202 |
| 997 | |
| AMPHI Regions - AMPHI | |
| SEQ. ID. NO. 13973 | 18-TrpAlaGlyLeuSerAlaAlaVal-25 |
| SEQ. ID. NO. 13974 | 70-TyrArgGlyValLeuArgLeuMetLysThrIleGly-81 |
| SEQ. ID. NO. 13975 | 107-ProLeuProAlaProLeuHisIle-114 |
| SEQ. ID. NO. 13976 | 132-LeuLeuAlaAspMetSerAspLeuGlnLysSerAlaArgLeuGly-146 |
| SEQ. ID. NO. 13977 | 164-AlaAlaValMetGlnPheTrpGlnProLeuValTrpGly-176 |
| SEQ. ID. NO. 13978 | 189-ValLeuCysAsnValLeuSerAsp-196 |
| SEQ. ID. NO. 13979 | 222-AlaLeuAlaAspLeuGlnArg-228 |
| SEQ. ID. NO. 13980 | 241-ArgLeuAsnThrLeuPro-246 |
| SEQ. ID. NO. 13981 | 275-GluGlyThrProGluHisValGlnThrAla-284 |
| SEQ. ID. NO. 13982 | 300-TyrAlaGluProValArgLeuProAlaProLeuThrGlyLeuAlaAspGly-316 |

TABLE 1-continued

| | |
|---|---|
| SEQ. ID. NO. 13983 | 355-LysAlaHisAlaAspLeuLysArgIleLeuProHisLeu-367 |
| SEQ. ID. NO. 13984 | 369-GluProGluAlaVal-373 |
| Antigenic Index - Jameson-Wolf | |
| SEQ. ID. NO. 13985 | 3-AsnThrProHisProArgProLysIle-11 |
| SEQ. ID. NO. 13986 | 37-GluAlaGlyArgGlnAlaGlyGlyArgAlaArgThrLeuAlaGlyAsnThrAspGlyPheGly-57 |
| SEQ. ID. NO. 13987 | 78-LysThrIleGlySerAspProArgAlaAla-87 |
| SEQ. ID. NO. 13988 | 122-ArgArgAlaProThr-126 |
| SEQ. ID. NO. 13989 | 132-LeuLeuAlaAspMetSerAspLeuGlnLysSerAlaArgLeuGlyGlnProAspThrThr-151 |
| SEQ. ID. NO. 13990 | 156-LeuLysGlnArgAsnValProArg-163 |
| SEQ. ID. NO. 13991 | 180-ThrProLeuGluThrAlaSer-186 |
| SEQ. ID. NO. 13992 | 197-GlyValLeuThrLysLysSerGlySerAspTyrLeuLeuProLysGlnAspLeu-214 |
| SEQ. ID. NO. 13993 | 225-AspLeuGlnArgLeuGlyAlaAspIleArgLeuGluThrArgValCysArg-241 |
| SEQ. ID. NO. 13994 | 243-AsnThrLeuProAspGlyLysVal-250 |
| SEQ. ID. NO. 13995 | 273-LeuProGluGlyThrProGluHisVal-281 |
| SEQ. ID. NO. 13996 | 312-GlyLeuAlaAspGlyThr-317 |
| SEQ. ID. NO. 13997 | 323-CysArgGlyArgLeuGlyLeuProGluAsnGluVal-334 |
| SEQ. ID. NO. 13998 | 340-ValSerAspArgValGlyAla-346 |
| SEQ. ID. NO. 13999 | 351-AlaTrpAlaAspLysAlaHisAlaAspLeuLysArgIleLeu-364 |
| SEQ. ID. NO. 14000 | 367-LeuGlyGluProGluAlaValArgValIleThrGluLysArgAlaThrThrAlaAlaAspAlaProProProAspLeu-392 |
| SEQ. ID. NO. 14001 | 402-ProAlaGlyAspTyrLeuHisProAspTyrProAla-413 |
| Hydrophilic Regions - Hopp-Woods | |
| SEQ. ID. NO. 14002 | 5-ProHisProArgProLysIle-11 |
| SEQ. ID. NO. 14003 | 37-GluAlaGlyArgGlnAlaGlyGlyArgAlaArgThrLeuAlaGlyAsn-52 |
| SEQ. ID. NO. 14004 | 80-IleGlySerAspProArgAlaAla-87 |
| SEQ. ID. NO. 14005 | 122-ArgArgAlaProThr-126 |
| SEQ. ID. NO. 14006 | 132-LeuLeuAlaAspMetSerAspLeuGlnLysSerAlaArgLeuGlyGlnProAspThrThr-151 |
| SEQ. ID. NO. 14007 | 198-ValLeuThrLysLysSerGlySer-205 |
| SEQ. ID. NO. 14008 | 208-LeuLeuProLysGlnAspLeu-214 |
| SEQ. ID. NO. 14009 | 225-AspLeuGlnArgLeuGlyAlaAspIleArgLeuGluThrArgValCysArg-241 |
| SEQ. ID. NO. 14010 | 246-ProAspGlyLysVal-250 |
| SEQ. ID. NO. 14011 | 276-GlyThrProGluHisVal-281 |
| SEQ. ID. NO. 14012 | 325-GlyArgLeuGlyLeuProGluAsnGluVal-334 |
| SEQ. ID. NO. 14013 | 340-ValSerAspArgValGly-345 |
| SEQ. ID. NO. 14014 | 351-AlaTrpAlaAspLysAlaHisAlaAspLeuLysArgIleLeu-364 |
| SEQ. ID. NO. 14015 | 368-GlyGluProGluAlaValArgValIleThrGluLysArgAlaThrThrAlaAlaAspAlaProProPro-390 |
| 999 | |
| AMPHI Regions - AMPHI | |
| SEQ. ID. NO. 14016 | 6-LeuIleSerAlaIleCysValSerIle-14 |
| SEQ. ID. NO. 14017 | 30-GluProValGlnSerIleGlnAlaAla-38 |
| SEQ. ID. NO. 14018 | 117-GlyGlnAsnLeuValAsnAsnAlaIleAsnGlyLeuHisSerIleGlnAlaValLeuSer-136 |
| SEQ. ID. NO. 14019 | 138-ThrThrThrAspLys-142 |
| SEQ. ID. NO. 14020 | 151-GlnLeuPheThrAlaLeuThrGluValValLysGluSer-163 |
| Antigenic Index - Jameson-Wolf | |
| SEQ. ID. NO. 14021 | 1-MetAsnMetLysLysLeuIle-7 |
| SEQ. ID. NO. 14022 | 18-AlaCysAsnGlnGlnSerLysThrAlaGlnAlaGluGluProValGln-33 |
| SEQ. ID. NO. 14023 | 42-AlaProMetAspIleThrVal-48 |
| SEQ. ID. NO. 14024 | 57-GlnAlaPheLysThrGlnAsnValSer-65 |
| SEQ. ID. NO. 14025 | 67-LysIleHisAsnLysAsnIleValLysThrAspCysGlyTyr-80 |
| SEQ. ID. NO. 14026 | 94-LysLeuAspGluGlnGlnLysIleArgAla-103 |
| SEQ. ID. NO. 14027 | 111-LysThrAspGlyGluLysGlyGlnAsnLeu-120 |
| SEQ. ID. NO. 14028 | 138-ThrThrThrAspLysLeuGlyGluSerGluAlaGlyLys-150 |
| SEQ. ID. NO. 14029 | 158-GluValValLysGluSerAsnGlnThrGly-167 |
| SEQ. ID. NO. 14030 | 169-ThrAlaGlnLysAspValProAlaAspGly-178 |
| SEQ. ID. NO. 14031 | 185-PheGluLysGluThrAsnThr-191 |
| SEQ. ID. NO. 14032 | 195-IleGlyArgLysGlnPro-200 |
| Hydrophilic Regions - Hopp-Woods | |
| SEQ. ID. NO. 14033 | 1-MetAsnMetLysLysLeuIle-7 |
| SEQ. ID. NO. 14034 | 21-GlnGlnSerLysThrAlaGlnAlaGluGluProValGln-33 |
| SEQ. ID. NO. 14035 | 72-AsnIleValLysThrAspCysGlyTyr-80 |
| SEQ. ID. NO. 14036 | 94-LysLeuAspGluGlnGlnLysIleArgAla-103 |
| SEQ. ID. NO. 14037 | 112-ThrAspGlyGluLysGlyGlnAsn-119 |
| SEQ. ID. NO. 14038 | 139-ThrThrAspLysLeuGlyGluSerGluAlaGlyLys-150 |
| SEQ. ID. NO. 14039 | 158-GluValValLysGluSerAsnGln-165 |
| SEQ. ID. NO. 14040 | 169-ThrAlaGlnLysAspValProAla-176 |
| SEQ. ID. NO. 14041 | 185-PheGluLysGluThrAsn-190 |
| SEQ. ID. NO. 14042 | 195-IleGlyArgLysGlnPro-200 |
| a001 | |
| AMPHI Regions - AMPHI | |
| SEQ. ID. NO. 14043 | 7-AlaAlaArgArgMet-11 |
| SEQ. ID. NO. 14044 | 69-PhePheGlySerAlaCysAsnSerAlaAla-78 |
| Antigenic Index - Jameson-Wolf | |
| SEQ. ID. NO. 14045 | 3-ProGlnGlyLysAlaAlaArgArgMetSerAlaAsnGluValCys-17 |
| SEQ. ID. NO. 14046 | 31-ThrLeuProLysArgAspThrLeuAsnGlySerGlyThr-43 |
| SEQ. ID. NO. 14047 | 53-ProArgSerLeuArgSerLysSerThr-61 |
| SEQ. ID. NO. 14048 | 68-ArgPhePheGlySerAlaCysAsnSerAlaAlaArgArgSerSerCysProSerProLysIleGly-89 |
| SEQ. ID. NO. 14049 | 100-ValProSerGluProIleLeuArgLysSerSerGlyGluLysHisSerVal-116 |
| SEQ. ID. NO. 14050 | 118-AlaAspCysProCysAlaSerGlyArgTrpAspLysThrAla-131 |
| Hydrophilic Regions - Hopp-Woods | |
| SEQ. ID. NO. 14051 | 5-GlyLysAlaAlaArgArgMetSerAla-13 |
| SEQ. ID. NO. 14052 | 32-LeuProLysArgAspThrLeuAsn-39 |

TABLE 1-continued

| | |
|---|---|
| SEQ. ID. NO. 14053 | 54-ArgSerLeuArgSerLysSer-60 |
| SEQ. ID. NO. 14054 | 76-SerAlaAlaArgArgSerSerCysProSerProLys-87 |
| SEQ. ID. NO. 14055 | 104-ProIleLeuArgLysSerSerGlyGluLysHisSerVal-116 |
| SEQ. ID. NO. 14056 | 125-GlyArgTrpAspLysThrAla-131 |
| a003 | |
| AMPHI Regions - AMPHI | |
| SEQ. ID. NO. 14057 | 72-AsnGlnValValLeu-76 |
| SEQ. ID. NO. 14058 | 82-IleValGluValPheGlnArg-88 |
| SEQ. ID. NO. 14059 | 138-ArgIleAsnAspAlaGluGluIleLeuGlnAspValValAlaGluPheValGlyIleValGlyHisPheAspGlyPheGlyVal-165 |
| SEQ. ID. NO. 14060 | 174-PheIleAlaArgIlePheArgVal-181 |
| Antigenic Index - Jameson-Wolf | |
| SEQ. ID. NO. 14061 | 91-PheAsnAsnGluGlyGln-96 |
| SEQ. ID. NO. 14062 | 104-PheGluGlyGlyGlyAspAspGlyPhe-112 |
| SEQ. ID. NO. 14063 | 137-GlyArgIleAsnAspAlaGluGluIleLeu-146 |
| SEQ. ID. NO. 14064 | 204-ProGluAlaAlaAlaGlyGluValAspGlyAlaArgValHisAsp-218 |
| Hydrophilic Regions - Hopp-Woods | |
| SEQ. ID. NO. 14065 | 106-GlyGlyGlyAspAspGlyPhe-112 |
| SEQ. ID. NO. 14066 | 137-GlyArgIleAsnAspAlaGluGluIleLeu-146 |
| SEQ. ID. NO. 14067 | 205-GluAlaAlaAlaGlyGluValAspGlyAlaArgValHisAsp-218 |
| a005 | |
| AMPHI Regions - AMPHI | |
| SEQ. ID. NO. 14068 | 14-IleGlnSerMetTrpLysGlu-20 |
| SEQ. ID. NO. 14069 | 30-LeuGluLeuLeuThrValPheGlyAlaIleAla-40 |
| SEQ. ID. NO. 14070 | 60-LeuThrAspPheSerGluAsnTyr-67 |
| SEQ. ID. NO. 14071 | 105-ArgLeuLysGluGlyGlyGluLysSerSerGlu-115 |
| SEQ. ID. NO. 14072 | 175-GlnLeuArgArgLeuArg-180 |
| SEQ. ID. NO. 14073 | 214-AlaIleValGlySerValGlyValValAlaGluValProAsnIleHisArgLeuLeuLysLys-234 |
| SEQ. ID. NO. 14074 | 247-PheLysArgThrVal-251 |
| SEQ. ID. NO. 14075 | 272-ThrHisGlnLeuPheLysGln-278 |
| SEQ. ID. NO. 14076 | 306-LeuAsnLeuIleAspGluIleSerThr-314 |
| SEQ. ID. NO. 14077 | 318-LeuLeuLeuLysAlaPhe-323 |
| Antigenic Index - Jameson-Wolf | |
| SEQ. ID. NO. 14078 | 8-MetProGluGlnGluGluIleGlnSerMetTrp-18 |
| SEQ. ID. NO. 14079 | 48-GlnSerLysLysGlnSerGluSerGlySer-57 |
| SEQ. ID. NO. 14080 | 62-AspPheSerGluAsnTyrLysLysGlnArgGlnSerPhe-74 |
| SEQ. ID. NO. 14081 | 80-SerGlyGluGluAlaLysHisGlnGluLysGluGluLysLysLysGluLysAlaGluAlaLysAlaGluLysLysArgLeuLysGluGlyGlyGluLysSer SerGluThrGlnLysSerArg-120 |
| SEQ. ID. NO. 14082 | 136-GluSerLeuArgHisGluIle-142 |
| SEQ. ID. NO. 14083 | 149-AlaLysProGluAspGluValLeuLeu-157 |
| SEQ. ID. NO. 14084 | 159-LeuGluSerProGlyGlyVal-165 |
| SEQ. ID. NO. 14085 | 175-GlnLeuArgArgLeuArgGluArgAsnIle-184 |
| SEQ. ID. NO. 14086 | 189-AlaValAspLysValAlaAla-195 |
| SEQ. ID. NO. 14087 | 230-ArgLeuLeuLysLysHisAspIleAspVal-239 |
| SEQ. ID. NO. 14088 | 245-GlyGluPheLysArgThr-250 |
| SEQ. ID. NO. 14089 | 256-GluAsnThrGluLysGlyLysGlnLysPheArgGlnGluLeuGluGluThrHisGln-274 |
| SEQ. ID. NO. 14090 | 279-PheValSerGluAsnArgProGlnLeuAspIleGluGluValAlaThr-294 |
| SEQ. ID. NO. 14091 | 310-AspGluIleSerThrSerAspAspLeuLeu-319 |
| SEQ. ID. NO. 14092 | 323-PheGluAsnLysGlnValIle-329 |
| SEQ. ID. NO. 14093 | 332-LysTyrGlnGluLysGlnSerLeu-339 |
| SEQ. ID. NO. 14094 | 349-AlaSerValGluLysLeuPhe-355 |
| SEQ. ID. NO. 14095 | 359-ValAsnArgArgAlaAspVal-365 |
| Hydrophilic Regions - Hopp-Woods | |
| SEQ. ID. NO. 14096 | 8-MetProGluGlnGluGluIleGlnSerMetTrp-18 |
| SEQ. ID. NO. 14097 | 48-GlnSerLysLysGlnSerGluSerGly-56 |
| SEQ. ID. NO. 14098 | 62-AspPheSerGluAsnTyrLysLysGlnArgGlnSerPhe-74 |
| SEQ. ID. NO. 14099 | 81-GlyGluGluAlaLysHisGlnGluLysGluGluLysLysLysGluLysAlaGluAlaLysAlaGluLysLysArgLeuLysGluGlyGlyGluLysSerSer GluThrGlnLysSerArg-120 |
| SEQ. ID. NO. 14100 | 136-GluSerLeuArgHisGluIle-142 |
| SEQ. ID. NO. 14101 | 149-AlaLysProGluAspGluValLeuLeu-157 |
| SEQ. ID. NO. 14102 | 159-LeuGluSerProGly-163 |
| SEQ. ID. NO. 14103 | 175-GlnLeuArgArgLeuArgGluArgAsnIle-184 |
| SEQ. ID. NO. 14104 | 189-AlaValAspLysValAlaAla-195 |
| SEQ. ID. NO. 14105 | 230-ArgLeuLeuLysLysHisAspIleAspVal-239 |
| SEQ. ID. NO. 14106 | 245-GlyGluPheLysArg-249 |
| SEQ. ID. NO. 14107 | 256-GluAsnThrGluLysGlyLysGlnLysPheArgGlnGluLeuGluGluThrHisGln-274 |
| SEQ. ID. NO. 14108 | 279-PheValSerGluAsnArgProGlnLeuAspIleGluGluValAlaThr-294 |
| SEQ. ID. NO. 14109 | 310-AspGluIleSerThrSerAspAspLeuLeu-319 |
| SEQ. ID. NO. 14110 | 323-PheGluAsnLysGlnValIle-329 |
| SEQ. ID. NO. 14111 | 332-LysTyrGlnGluLysGlnSerLeu-339 |
| SEQ. ID. NO. 14112 | 349-AlaSerValGluLysLeuPhe-355 |
| SEQ. ID. NO. 14113 | 359-ValAsnArgArgAlaAspVal-365 |
| a006-1 | |
| AMPHI Regions - AMPHI | |
| SEQ. ID. NO. 14114 | 40-GlnAlaTrpGlnAlaLeuLeuTyrAlaLeuValValLeu-52 |
| SEQ. ID. NO. 14115 | 61-ArgArgIleAlaAspThrArgThrPheThrArgIleTyrThrGlu-75 |
| SEQ. ID. NO. 14116 | 103-GluPheValSerPhePheGlu-109 |
| SEQ. ID. NO. 14117 | 117-ThrSerValValSerIlePheGlyAlaCysIleMetLeuLeu-130 |
| SEQ. ID. NO. 14118 | 179-GlyAspGluArgGlnLeu-184 |
| SEQ. ID. NO. 14119 | 186-ArgHisTyrGlyLeuLeuAlaArgLeu-194 |

TABLE 1-continued

| | |
|---|---|
| SEQ. ID. NO. 14120 | 228-GlyTyrSerSerAlaGlyHisValTyrSer-237 |
| SEQ. ID. NO. 14121 | 249-LeuAspAspValProArgLeuValGluGlnTyrSerAsnLeuLysAspIle-265 |
| Antigenic Index - Jameson-Wolf | |
| SEQ. ID. NO. 14122 | 1-SerGlnAsnHisArgLysArgLeu-8 |
| SEQ. ID. NO. 14123 | 59-AlaAlaArgArgIleAlaAspThrArgThrPheThr-70 |
| SEQ. ID. NO. 14124 | 82-LeuGluGlnArgGlnArgGlnValProHisSer-92 |
| SEQ. ID. NO. 14125 | 163-PheArgLeuLysAsnSerLeuGluArgAspAsnHisPheIleArgLysGlyAspGluArgGlnLeuAspArgHisTyr-188 |
| SEQ. ID. NO. 14126 | 198-IleSerAsnArgGluAlaPhe-204 |
| SEQ. ID. NO. 14127 | 227-LysGlyTyrSerSer-231 |
| SEQ. ID. NO. 14128 | 249-LeuAspAspValProArgLeuValGluGlnTyrSerAsnLeuLysAspIleGlyGln-267 |
| SEQ. ID. NO. 14129 | 269-IleGluTrpSerLysArgAsnIleLysAlaGlyThr-280 |
| Hydrophilic Regions - Hopp-Woods | |
| SEQ. ID. NO. 14130 | 1-SerGlnAsnHisArgLysArgLeu-8 |
| SEQ. ID. NO. 14131 | 59-AlaAlaArgArgIleAlaAspThrArgThrPhe-69 |
| SEQ. ID. NO. 14132 | 82-LeuGluGlnArgGlnArgGlnValPro-90 |
| SEQ. ID. NO. 14133 | 166-LysAsnSerLeuGluArgAspAsnHisPheIleArgLysGlyAspGluArgGlnLeuAspArg-186 |
| SEQ. ID. NO. 14134 | 198-IleSerAsnArgGluAla-203 |
| SEQ. ID. NO. 14135 | 249-LeuAspAspValProArgLeuValGlu-257 |
| SEQ. ID. NO. 14136 | 260-SerAsnLeuLysAspIleGlyGln-267 |
| SEQ. ID. NO. 14137 | 269-IleGluTrpSerLysArgAsnIleLysAlaGlyThr-280 |
| a007-1 | |
| AMPHI Regions - AMPHI | |
| SEQ. ID. NO. 14138 | 71-HisSerMetValLysGlyIleAsn-78 |
| SEQ. ID. NO. 14139 | 105-ValAlaThrTyrIleMetAsnAlaPheAspAsnGlyGlyGly-118 |
| Antigenic Index - Jameson-Wolf | |
| SEQ. ID. NO. 14140 | 1-MetAsnThrThrArgLeu-6 |
| SEQ. ID. NO. 14141 | 20-SerAlaAlaAspAsnSerIleMetThrLysGlyGlnLysValTyrGluSerAsnCys-38 |
| SEQ. ID. NO. 14142 | 41-CysHisGlyLysLysGlyGluGlyArgGlyThr-51 |
| SEQ. ID. NO. 14143 | 55-ProLeuTyrArgSerAspPheIleMetLysLysProGln-67 |
| SEQ. ID. NO. 14144 | 83-ValAsnGlyLysThrTyrAsnGly-90 |
| SEQ. ID. NO. 14145 | 98-SerAspAlaAspIle-102 |
| SEQ. ID. NO. 14146 | 112-AlaPheAspAsnGlyGlyGlySerValThrGluLysAspValLysGlnAlaLysAsnLysLys-132 |
| Hydrophilic Regions - Hopp-Woods | |
| SEQ. ID. NO. 14147 | 26-IleMetThrLysGlyGlnLysValTyrGlu-35 |
| SEQ. ID. NO. 14148 | 42-HisGlyLysLysGlyGluGlyArgGly-50 |
| SEQ. ID. NO. 14149 | 61-PheIleMetLysLysProGln-67 |
| SEQ. ID. NO. 14150 | 98-SerAspAlaAspIle-102 |
| SEQ. ID. NO. 14151 | 119-SerValThrGluLysAspValLysGlnAlaLysAsnLysLys-132 |
| a008 | |
| AMPHI Regions - AMPHI | |
| SEQ. ID. NO. 14152 | 15-LeuGluAsnProAlaGlnGlnValArgAlaAlaLeuAspThrLeuSer-30 |
| SEQ. ID. NO. 14153 | 54-GlnProAspPheValAsnAlaVal-61 |
| SEQ. ID. NO. 14154 | 69-AspGlyIleAlaLeuLeuAlaGluLeuAsnArg-79 |
| SEQ. ID. NO. 14155 | 90-PheArgAsnAlaPro-94 |
| SEQ. ID. NO. 14156 | 129-ArgProLeuAlaGluIleLeuProAsp-137 |
| SEQ. ID. NO. 14157 | 144-GlyLysValAlaGluLeuSerLysArgLeuGly-154 |
| Antigenic Index - Jameson-Wolf | |
| SEQ. ID. NO. 14158 | 1-MetAsnAsnArgHis-5 |
| SEQ. ID. NO. 14159 | 12-GlySerAsnLeuGluAsnProAlaGlnGlnVal-22 |
| SEQ. ID. NO. 14160 | 29-LeuSerSerHisProAspIleArgLeuLysGlnAlaSerSer-42 |
| SEQ. ID. NO. 14161 | 49-ValGlyTyrAspAsnGlnProAspPhe-57 |
| SEQ. ID. NO. 14162 | 76-GluLeuAsnArgIleGluAlaAspPheGlyArgGluArgSerPheArgAsnAlaProArgThrLeuAspLeuAspIleIleAspPheAspGlyIleSerSer AspAspProArgLeuThrLeuProHisProArgAlaHisGluArgSerPheVal-127 |
| SEQ. ID. NO. 14163 | 140-LeuGlyLysHisGlyLysValAlaGluLeuSerLysArgLeuGlyAsnGlnGlyIle-158 |
| SEQ. ID. NO. 14164 | 160-LeuLeuProAspLys-164 |
| Hydrophilic Regions - Hopp-Woods | |
| SEQ. ID. NO. 14165 | 14-AsnLeuGluAsnProAlaGlnGlnVal-22 |
| SEQ. ID. NO. 14166 | 33-ProAspIleArgLeuLysGln-39 |
| SEQ. ID. NO. 14167 | 76-GluLeuAsnArgIleGluAlaAspPheGlyArgGluArgSerPheArgAsnAlaProArgThrLeuAsp-98 |
| SEQ. ID. NO. 14168 | 105-AspGlyIleSerSerAspAspProArgLeu-114 |
| SEQ. ID. NO. 14169 | 120-ArgAlaHisGluArgSerPheVal-127 |
| SEQ. ID. NO. 14170 | 142-LysHisGlyLysValAlaGluLeuSerLysArgLeuGly-154 |
| SEQ. ID. NO. 14171 | 160-LeuLeuProAspLys-164 |
| a009 | |
| Antigenic Index - Jameson-Wolf | |
| SEQ. ID. NO. 14172 | 6-ValAlaPheGluArgHisHisHisLysSerLysAlaGluGlnAsnThrHisArgArgAlaAspAlaGluIleAlaGlu-31 |
| SEQ. ID. NO. 14173 | 37-AsnGlnHisThrGlnAlaArgLysGlnSer-46 |
| SEQ. ID. NO. 14174 | 57-PheSerAspLysVal-61 |
| SEQ. ID. NO. 14175 | 77-AlaAspGlyGlyLysThrTrpGlnLysPro-86 |
| Hydrophilic Regions - Hopp-Woods | |
| SEQ. ID. NO. 14176 | 6-ValAlaPheGluArgHisHisHisLysSerLysAlaGluGlnAsnThrHisArgArgAlaAspAlaGluIleAlaGlu-31 |
| SEQ. ID. NO. 14177 | 40-ThrGlnAlaArgLysGlnSer-46 |
| SEQ. ID. NO. 14178 | 78-AspGlyGlyLysThrTrpGln-84 |
| a010-1 | |
| AMPHI Regions - AMPHI | |
| SEQ. ID. NO. 14179 | 54-SerAlaSerLeuGly-58 |
| SEQ. ID. NO. 14180 | 70-TyrAspThrValLysGly-75 |
| SEQ. ID. NO. 14181 | 115-TyrGlnArgProPheGlyGlyHis-122 |
| SEQ. ID. NO. 14182 | 125-GluHisGlyLysArgAlaVal-131 |
| SEQ. ID. NO. 14183 | 146-LeuHisThrLeuTyrGln-151 |

TABLE 1-continued

| | |
|---|---|
| SEQ. ID. NO. 14184 | 210-AlaSerSerThrAsn-214 |
| SEQ. ID. NO. 14185 | 216-TyrMetAsnThrGlyAspGly-222 |
| SEQ. ID. NO. 14186 | 275-ArgTyrAlaProThrValLys-281 |
| SEQ. ID. NO. 14187 | 322-IleMetGluLysLeuProGlyIleArg-330 |
| SEQ. ID. NO. 14188 | 338-GlyIleAspProIleLysAspProIlePro-347 |
| SEQ. ID. NO. 14189 | 357-GlyGlyIleProThrAsnTyrHis-364 |
| SEQ. ID. NO. 14190 | 413-AlaAlaGlyAspSerMetIleLysPheIleLysGluGlnSerAspTrp-428 |
| SEQ. ID. NO. 14191 | 446-LeuAspAsnGlnThrAsp-451 |
| SEQ. ID. NO. 14192 | 453-GluAsnValAspAlaLeuArgArgGluLeu-462 |
| SEQ. ID. NO. 14193 | 479-LeuSerLysGlyValArgGluValMetAlaIleAlaGlu-491 |
| SEQ. ID. NO. 14194 | 505-TrpAsnThrAlaArg-509 |
| SEQ. ID. NO. 14195 | 514-GluLeuAspAsnLeuIleGluValAlaLys-523 |
| Antigenic Index - Jameson-Wolf | |
| SEQ. ID. NO. 14196 | 14-GlyGlyGlyGlyAlaGlyLeu-20 |
| SEQ. ID. NO. 14197 | 26-LeuSerLysSerGlyLeu-31 |
| SEQ. ID. NO. 14198 | 40-PheProThrArgSerHisThr-46 |
| SEQ. ID. NO. 14199 | 59-AsnValGlnGluAspArgTrpAsp-66 |
| SEQ. ID. NO. 14200 | 71-AspThrValLysGlySerAspTrpLeuGlyAspGlnAspAlaIle-85 |
| SEQ. ID. NO. 14201 | 104-MetProPheAspArgValGluSerGlyLysIleTyrGlnArgProPheGly-120 |
| SEQ. ID. NO. 14202 | 123-ThrAlaGluHisGlyLysArgAlaValGluArgAlaCysAlaValAlaAspArgThrGly-142 |
| SEQ. ID. NO. 14203 | 152-GlnAsnValArgAlaAsnThrGln-159 |
| SEQ. ID. NO. 14204 | 168-AspLeuIleArgAspGluAsnGlyAspVal-177 |
| SEQ. ID. NO. 14205 | 183-MetGluMetGluThrGlyGlu-189 |
| SEQ. ID. NO. 14206 | 202-ThrGlyGlyGlyGlyArgIle-208 |
| SEQ. ID. NO. 14207 | 211-SerSerThrAsnAla-215 |
| SEQ. ID. NO. 14208 | 218-AsnThrGlyAspGlyLeu-223 |
| SEQ. ID. NO. 14209 | 231-IleProLeuGluAspMetGlu-237 |
| SEQ. ID. NO. 14210 | 255-GluGlyValArgGlyGluGlyGlyIle-263 |
| SEQ. ID. NO. 14211 | 266-AsnAlaAspGlyGluArgPheMetGlu-274 |
| SEQ. ID. NO. 14212 | 276-TyrAlaProThrValLysAspLeuAlaSerArgAspValValSer-290 |
| SEQ. ID. NO. 14213 | 297-IleTyrGluGlyArgGlyCysGlyLysAsnLysAspHisVal-310 |
| SEQ. ID. NO. 14214 | 315-AspHisIleGlyAlaGluLysIleMetGluLysLeuProGlyIleArgGluIleSer-333 |
| SEQ. ID. NO. 14215 | 338-GlyIleAspProIleLysAspProIle-346 |
| SEQ. ID. NO. 14216 | 368-ValValProGlnGlyAspGluTyrGluValProVal-379 |
| SEQ. ID. NO. 14217 | 395-GlyAlaAsnArgLeuGlyThrAsnSerLeu-404 |
| SEQ. ID. NO. 14218 | 413-AlaAlaGlyAspSerMet-418 |
| SEQ. ID. NO. 14219 | 421-PheIleLysGluGlnSerAspTrpLysProLeuProAlaAsnAlaGlyGluLeuThrArgGlnArgIleGluArgLeuAspAsnGlnThrAspGlyGlu AsnValAspAlaLeuArgArgGluLeuGlnArgSer-465 |
| SEQ. ID. NO. 14220 | 473-PheArgThrAspGluIleLeuSerLysGlyValArgGlu-485 |
| SEQ. ID. NO. 14221 | 487-MetAlaIleAlaGluArgValLysArgThrGluIleLysAspLysSerLysVal-504 |
| SEQ. ID. NO. 14222 | 508-AlaArgIleGluAlaLeuGluLeu-515 |
| SEQ. ID. NO. 14223 | 529-AlaGluAlaArgLysGluSerArgGlyAlaHisAlaSerAspAspHisProGluArgAspAspGluAsnTrpMet-553 |
| SEQ. ID. NO. 14224 | 558-TyrHisSerAspAlaAsnThrLeuSerTyrLysProValHisThrLysProLeuSer-576 |
| SEQ. ID. NO. 14225 | 581-LysProAlaLysArgValTyr-587 |
| Hydrophilic Regions - Hopp-Woods | |
| SEQ. ID. NO. 14226 | 26-LeuSerLysSerGlyLeu-31 |
| SEQ. ID. NO. 14227 | 59-AsnValGlnGluAspArgTrpAsp-66 |
| SEQ. ID. NO. 14228 | 71-AspThrValLysGly-75 |
| SEQ. ID. NO. 14229 | 77-AspTrpLeuGlyAspGlnAspAlaIle-85 |
| SEQ. ID. NO. 14230 | 105-ProPheAspArgValGluSerGlyLysIleTyr-115 |
| SEQ. ID. NO. 14231 | 123-ThrAlaGluHisGlyLysArgAlaValGluArgAlaCysAlaValAlaAspArgThrGly-142 |
| SEQ. ID. NO. 14232 | 168-AspLeuIleArgAspGluAsnGlyAsp-176 |
| SEQ. ID. NO. 14233 | 183-MetGluMetGluThrGlyGlu-189 |
| SEQ. ID. NO. 14234 | 231-IleProLeuGluAspMetGlu-237 |
| SEQ. ID. NO. 14235 | 255-GluGlyValArgGlyGluGly-261 |
| SEQ. ID. NO. 14236 | 267-AlaAspGlyGluArgPheMetGlu-274 |
| SEQ. ID. NO. 14237 | 276-TyrAlaProThrValLysAspLeuAlaSerArgAspValValSer-290 |
| SEQ. ID. NO. 14238 | 297-IleTyrGluGlyArgGlyCysGlyLysAsnLysAspHisVal-310 |
| SEQ. ID. NO. 14239 | 315-AspHisIleGlyAlaGluLysIleMetGluLysLeuProGlyIleArgGluIleSer-333 |
| SEQ. ID. NO. 14240 | 340-AspProIleLysAspProIle-346 |
| SEQ. ID. NO. 14241 | 371-GlnGlyAspGluTyrGluValProVal-379 |
| SEQ. ID. NO. 14242 | 421-PheIleLysGluGlnSerAspTrpLysPro-430 |
| SEQ. ID. NO. 14243 | 434-AsnAlaGlyGluLeuThrArgGlnArgIleGluArgLeuAspAsnGlnThrAspGlyGluAsnValAspAlaLeuArgArgGluLeuGlnArg-464 |
| SEQ. ID. NO. 14244 | 473-PheArgThrAspGluIleLeuSerLysGlyValArgGlu-485 |
| SEQ. ID. NO. 14245 | 487-MetAlaIleAlaGluArgValLysArgThrGluIleLysAspLysSerLysVal-504 |
| SEQ. ID. NO. 14246 | 508-AlaArgIleGluAlaLeuGluLeu-515 |
| SEQ. ID. NO. 14247 | 529-AlaGluAlaArgLysGluSerArgGlyAlaHisAlaSerAspAspHisProGluArgAspAspGluAsnTrpMet-553 |
| SEQ. ID. NO. 14248 | 581-LysProAlaLysArgValTyr-587 |
| a011 | |
| AMPHI Regions - AMPHI | |
| SEQ. ID. NO. 14249 | 58-IleArgLeuIleAsnAlaAla-64 |
| SEQ. ID. NO. 14250 | 83-AlaIleLeuThrLys-87 |
| SEQ. ID. NO. 14251 | 116-GluValLeuHisArgTyrLeuProGlnMetLeuSerAlaGly-129 |
| SEQ. ID. NO. 14252 | 147-MetAlaXxxMetGlyLysValMetGlyVal-156 |
| Antigenic Index - Jameson-Wolf | |
| SEQ. ID. NO. 14253 | 1-MetArgThrHisArgLysThrCysSer-9 |
| SEQ. ID. NO. 14254 | 17-ThrAlaSerLysProAlaValSerIleArgHisProSerGluAsnIleMet-33 |
| SEQ. ID. NO. 14255 | 37-IleArgLeuThrGluAspMetLysThrAlaMetArgAlaLysAspGlnVal-53 |
| SEQ. ID. NO. 14256 | 66-LysGlnPheGluValAspGluArgThrGluAlaAspAspAlaLysIle-81 |
| SEQ. ID. NO. 14257 | 88-MetValLysGlnArgLysAspSerValLysIle-98 |

TABLE 1-continued

SEQ. ID. NO. 14258 100-ThrGluAlaGlyArgGlnAspLeuAlaAspLysGluAsnAlaGluIle-115
SEQ. ID. NO. 14259 127-SerAlaGlyGluIleArgThrAlaVal-135
SEQ. ID. NO. 14260 157-XxxLysThrArgLeuAlaGlyLysAlaAspMetGlyGluValAsnLysIleLeu-174
Hydrophilic Regions - Hopp-Woods
SEQ. ID. NO. 14261 1-MetArgThrHisArgLysThrCys-8
SEQ. ID. NO. 14262 37-IleArgLeuThrGluAspMetLysThrAlaMetArgAlaLysAspGlnVal-53
SEQ. ID. NO. 14263 66-LysGlnPheGluValAspGluArgThrGluAlaAspAspAlaLysIle-81
SEQ. ID. NO. 14264 88-MetValLysGlnArgLysAspSerValLysIle-98
SEQ. ID. NO. 14265 100-ThrGluAlaGlyArgGlnAspLeuAlaAspLysGluAsnAlaGluIle-115
SEQ. ID. NO. 14266 129-GlyGluIleArgThrAlaVal-135
SEQ. ID. NO. 14267 157-XxxLysThrArgLeuAlaGlyLysAlaAspMetGlyGluValAsnLysIleLeu-174
a012-1
AMPHI Regions - AMPHI
SEQ. ID. NO. 14268 19-LysLeuLeuGluGlnLeuMetArgPheLeuGlnPheLeuSerGluPheLeuPheAlaLeuPheArgIle-41
SEQ. ID. NO. 14269 48-ArgAlaLeuLysPheAlaArgArg-55
SEQ. ID. NO. 14270 89-AsnAsnPheIleArgHisThr-95
SEQ. ID. NO. 14271 160-GlnGlyPheTyrGlyVal-165
SEQ. ID. NO. 14272 179-GlyPheLeuArgPheGlyArgPheLeuProThrLeuLeuGlnThrLeu-194
Antigenic Index - Jameson-Wolf
SEQ. ID. NO. 14273 42-PheThrHisLysSerAsnArgAlaLeuLysPheAlaArgArgHisHis-57
SEQ. ID. NO. 14274 72-ArgTyrPheArgTyrAsnThrHisArgThrAspAsnArgLysArgSerGlyAsnAsnPhe-91
SEQ. ID. NO. 14275 93-ArgHisThrArgHisHis-98
SEQ. ID. NO. 14276 101-ThrAlaArgArgHisLeuIleAspGlyAspGlyGlnArgAsn-114
SEQ. ID. NO. 14277 119-GlnThrProLysLeuArgSerArgGln-127
SEQ. ID. NO. 14278 137-ThrPheGlnSerLysGlnAsnLeu-144
SEQ. ID. NO. 14279 147-ArgLeuGlyAsnGlnLysHisArgArgAsnLeuMetThrGln-160
SEQ. ID. NO. 14280 173-IleGlnHisLysLysAlaGly-179
Hydrophilic Regions - Hopp-Woods
SEQ. ID. NO. 14281 45-LysSerAsnArgAlaLeuLysPheAlaArgArgHisHis-57
SEQ. ID. NO. 14282 77-AsnThrHisArgThrAspAsnArgLysArgSerGly-88
SEQ. ID. NO. 14283 101-ThrAlaArgArgHisLeuIleAspGlyAspGlyGlnArg-113
SEQ. ID. NO. 14284 121-ProLysLeuArgSerArgGln-127
SEQ. ID. NO. 14285 149-GlyAsnGlnLysHisArgArgAsnLeu-157
SEQ. ID. NO. 14286 173-IleGlnHisLysLysAlaGly-179
a015
AMPHI Regions - AMPHI
SEQ. ID. NO. 14287 25-ValPheXxxLeuTrpLysAsnProGluLysProLeuAlaGlyPheTrpLysAlaLeuProHis-45
SEQ. ID. NO. 14288 107-MetCysCysLeuThrCys-112
Antigenic Index - Jameson-Wolf
SEQ. ID. NO. 14289 29-TrpLysAsnProGluLysProLeu-36
SEQ. ID. NO. 14290 90-MetArgAlaArgProArgSerThrLys-98
Hydrophilic Regions - Hopp-Woods
SEQ. ID. NO. 14291 30-LysAsnProGluLysProLeu-36
SEQ. ID. NO. 14292 90-MetArgAlaArgProArgSerThrLys-98
a018-2
AMPHI Regions - AMPHI
SEQ. ID. NO. 14293 6-IleGlnHisLeuArg-10
SEQ. ID. NO. 14294 100-AspGlyAlaAlaAla-104
SEQ. ID. NO. 14295 152-ArgIleGlyAsnGlyTyr-157
Antigenic Index - Jameson-Wolf
SEQ. ID. NO. 14296 1-MetValGluArgHisIleGln-7
SEQ. ID. NO. 14297 9-LeuArgAsnGlyHis-13
SEQ. ID. NO. 14298 19-ProSerGlnGlnValArg-24
SEQ. ID. NO. 14299 27-PheGlyGlyArgThrTyrAspPheCysAlaAspGluAlaAla-40
SEQ. ID. NO. 14300 67-TyrPheAlaAspAspLysPhe-73
SEQ. ID. NO. 14301 78-LeuArgGlyAsnLeuArg-83
SEQ. ID. NO. 14302 85-PheGlnThrAspLysAlaAspLeuArgThrGlyGluHisTyrAlaAspGlyAlaAla-103
SEQ. ID. NO. 14303 108-AlaAspIleArgVal-112
SEQ. ID. NO. 14304 136-ArgValAlaArgAsnLysAspMetArgAsnThrGlyLeuHisSerGlnArgIleGlyAsnGlyTyr-157
Hydrophilic Regions - Hopp-Woods
SEQ. ID. NO. 14305 1-MetValGluArgHisIleGln-7
SEQ. ID. NO. 14306 35-CysAlaAspGluAlaAla-40
SEQ. ID. NO. 14307 67-TyrPheAlaAspAspLysPhe-73
SEQ. ID. NO. 14308 85-PheGlnThrAspLysAlaAspLeuArgThrGlyGluHisTyrAla-99
SEQ. ID. NO. 14309 108-AlaAspIleArgVal-112
SEQ. ID. NO. 14310 136-ArgValAlaArgAsnLysAspMetArgAsn-145
a019-2
AMPHI Regions - AMPHI
SEQ. ID. NO. 14311 33-ProAlaAspAsnIleGlu-38
SEQ. ID. NO. 14312 55-GlyLysThrLeuAlaAspTyrGlyGlyTyrProSerAlaLeuAspAla-70
SEQ. ID. NO. 14313 80-AlaAlaTyrLeuGluAsnAlaGlyAsp-88
SEQ. ID. NO. 14314 90-AlaMetAlaGluAsnValArgAsnGluTrpLeuLysSer-102
SEQ. ID. NO. 14315 142-AlaAlaGluLeuValLysAsnThrGlyLysLeuProSerGlyCysThrLysLeuLeuGluGlnAlaAlaAlaSer-166
SEQ. ID. NO. 14316 173-AspAlaTrpArgArgValArg-179
SEQ. ID. NO. 14317 193-LeuAlaAlaAlaLeuGlySerProPheAspGlyGlyThrGlnGly-207
SEQ. ID. NO. 14318 215-AsnValIleGlyLysGluAlaArgLysSer-224
SEQ. ID. NO. 14319 229-AlaLeuLeuSerGluMet-234
SEQ. ID. NO. 14320 259-AsnValProAlaAlaLeuAspTyrTyrGly-268
SEQ. ID. NO. 14321 292-ArgArgTrpAspGluLeuAlaSerValIleSerHisMetProGluLysLeuGlnLys-310
SEQ. ID. NO. 14322 329-GlnGluAlaGluLysLeuTyrLysGlnAla-338

TABLE 1-continued

| | |
|---|---|
| SEQ. ID. NO. 14323 | 451-ArgTyrIleSerPro-455 |
| SEQ. ID. NO. 14324 | 495-GlnGlyLeuMetGlnValMet-501 |
| SEQ. ID. NO. 14325 | 582-ArgAspTyrValLysLysValMet-589 |
| Antigenic Index - Jameson-Wolf | |
| SEQ. ID. NO. 14326 | 3-ProProSerLeuLys-7 |
| SEQ. ID. NO. 14327 | 22-SerSerThrAsnThrLeuSerAlaAspLysThrProAlaAspAsnIleGluThrAlaAspLeuSerAlaSerValProThrArgProAlaGluProGluGly LysThrLeuAlaAspTyrGlyGlyTyrProSerAla-67 |
| SEQ. ID. NO. 14328 | 69-AspAlaValLysGlnLysAsnAspAla-77 |
| SEQ. ID. NO. 14329 | 85-AsnAlaGlyAspSerAlaMet-91 |
| SEQ. ID. NO. 14330 | 103-LeuGlyAlaArgArgGln-108 |
| SEQ. ID. NO. 14331 | 115-GluTyrAlaLysLeuGluProAlaGlyArgAlaGlnGluValGluCysTyrAlaAspSerSerArgAsnAspTyrThrArgAlaAlaGluLeuValLys AsnThrGlyLysLeuProSerGlyCys-156 |
| SEQ. ID. NO. 14332 | 167-GlyLeuLeuAspGlyAsnAspAlaTrpArgArgValArgGly-180 |
| SEQ. ID. NO. 14333 | 182-LeuAlaGlyArgGlnThrThrAspAlaArgAsn-192 |
| SEQ. ID. NO. 14334 | 199-SerProPheAspGlyGlyThrGlnGlySerArgGluTyr-211 |
| SEQ. ID. NO. 14335 | 217-IleGlyLysGluAlaArgLysSerProAsn-226 |
| SEQ. ID. NO. 14336 | 232-SerGluMetGluSerGlyLeuSerLeuGluGlnArgSer-244 |
| SEQ. ID. NO. 14337 | 254-GlnSerGlnAsnLeu-258 |
| SEQ. ID. NO. 14338 | 266-TyrTyrGlyLysValAlaAspArgArgGlnLeuThrAspAspGlnIle-281 |
| SEQ. ID. NO. 14339 | 287-AlaAlaLeuArgAlaArgArgTrpAspGlu-296 |
| SEQ. ID. NO. 14340 | 304-MetProGluLysLeuGlnLysSerProThr-313 |
| SEQ. ID. NO. 14341 | 320-ArgSerArgAlaAlaThrGlyAsnThrGlnGluAlaGluLysLeuTyrLys-336 |
| SEQ. ID. NO. 14342 | 339-AlaAlaThrGlyArgAsn-344 |
| SEQ. ID. NO. 14343 | 350-AlaGlyGluGluLeuGlyArgLysIleAspThrArgAsnAsnValProAspAlaGlyLysAsnSerVal-372 |
| SEQ. ID. NO. 14344 | 374-ArgMetAlaGluAspGlyAlaIleLys-382 |
| SEQ. ID. NO. 14345 | 389-ArgAsnSerArgThrAlaGlyAspAlaLysMetArgArgGlnAlaGlnAla-405 |
| SEQ. ID. NO. 14346 | 409-PheAlaThrArgGlyPheAspGluAspLysLeuLeu-420 |
| SEQ. ID. NO. 14347 | 438-SerAlaGluArgThrAspArgLysLeuAsnTyr-448 |
| SEQ. ID. NO. 14348 | 454-SerProPheLysAspThrValIle-461 |
| SEQ. ID. NO. 14349 | 464-AlaGlnAsnValAsnValAspProAla-472 |
| SEQ. ID. NO. 14350 | 478-IleArgGlnGluSerArgPhe-484 |
| SEQ. ID. NO. 14351 | 488-AlaGlnSerArgValGlyAla-494 |
| SEQ. ID. NO. 14352 | 504-ThrAlaArgGluIleAlaGly-510 |
| SEQ. ID. NO. 14353 | 520-TyrThrAlaAspGlyAsnIleArgMetGly-529 |
| SEQ. ID. NO. 14354 | 535-AspThrLysArgArgLeuGlnAsnAsnGluVal-545 |
| SEQ. ID. NO. 14355 | 550-GlyTyrAsnAlaGlyProGlyArgAlaArgArgTrpGlnAlaAspThrProLeuGlu-568 |
| SEQ. ID. NO. 14356 | 579-SerGluThrArgAspTyrValLys-586 |
| SEQ. ID. NO. 14357 | 606-LeuLysGlnArgMet-610 |
| Hydrophilic Regions - Hopp-Woods | |
| SEQ. ID. NO. 14358 | 27-LeuSerAlaAspLysThrProAlaAspAsnIleGluThrAlaAspLeu-42 |
| SEQ. ID. NO. 14359 | 46-ValProThrArgProAlaGluProGluGlyLysThrLeuAla-59 |
| SEQ. ID. NO. 14360 | 69-AspAlaValLysGlnLysAsnAspAla-77 |
| SEQ. ID. NO. 14361 | 85-AsnAlaGlyAspSerAlaMet-91 |
| SEQ. ID. NO. 14362 | 103-LeuGlyAlaArgArgGln-108 |
| SEQ. ID. NO. 14363 | 115-GluTyrAlaLysLeuGluProAlaGlyArgAlaGlnGluValGluCysTyrAlaAspSerSerArgAsnAspTyrThrArgAlaAlaGluLeuValLys AsnThrGlyLysLeuProSerGlyCys-156 |
| SEQ. ID. NO. 14364 | 170-AspGlyAsnAspAlaTrpArgArgValArgGly-180 |
| SEQ. ID. NO. 14365 | 185-ArgGlnThrThrAspAlaArgAsn-192 |
| SEQ. ID. NO. 14366 | 201-PheAspGlyGlyThrGlnGlySerArgGlu-210 |
| SEQ. ID. NO. 14367 | 217-IleGlyLysGluAlaArgLysSerProAsn-226 |
| SEQ. ID. NO. 14368 | 232-SerGluMetGluSer-236 |
| SEQ. ID. NO. 14369 | 238-LeuSerLeuGluGlnArgSer-244 |
| SEQ. ID. NO. 14370 | 270-ValAlaAspArgArgGlnLeuThrAspAspGlnIle-281 |
| SEQ. ID. NO. 14371 | 287-AlaAlaLeuArgAlaArgArgTrpAspGlu-296 |
| SEQ. ID. NO. 14372 | 304-MetProGluLysLeuGlnLys-310 |
| SEQ. ID. NO. 14373 | 320-ArgSerArgAlaAlaThr-325 |
| SEQ. ID. NO. 14374 | 327-AsnThrGlnGluAlaGluLysLeuTyrLys-336 |
| SEQ. ID. NO. 14375 | 350-AlaGlyGluGluLeuGlyArgLysIleAspThrArgAsnAsnValProAspAlaGlyLys-369 |
| SEQ. ID. NO. 14376 | 374-ArgMetAlaGluAspGlyAlaIleLys-382 |
| SEQ. ID. NO. 14377 | 389-ArgAsnSerArgThrAlaGlyAspAlaLysMetArgArgGlnAlaGlnAla-405 |
| SEQ. ID. NO. 14378 | 411-ThrArgGlyPheAspGluAspLysLeuLeu-420 |
| SEQ. ID. NO. 14379 | 438-SerAlaGluArgThrAspArgLysLeu-446 |
| SEQ. ID. NO. 14380 | 478-IleArgGlnGluSerArgPhe-484 |
| SEQ. ID. NO. 14381 | 488-AlaGlnSerArgValGly-493 |
| SEQ. ID. NO. 14382 | 504-ThrAlaArgGluIleAlaGly-510 |
| SEQ. ID. NO. 14383 | 535-AspThrLysArgArgLeuGlnAsn-542 |
| SEQ. ID. NO. 14384 | 554-GlyProGlyArgAlaArgArgTrpGlnAla-563 |
| SEQ. ID. NO. 14385 | 579-SerGluThrArgAspTyrValLys-586 |
| SEQ. ID. NO. 14386 | 606-LeuLysGlnArgMet-610 |
| a023 | |
| AMPHI Regions - AMPHI | |
| SEQ. ID. NO. 14387 | 42-LysGluTyrSerAlaTrpGlnAlaPhePheSerGlnThrTrpValLysValPheThrGlnValSerPheIleAlaValPheLeuHisAlaTrpValGly-74 |
| SEQ. ID. NO. 14388 | 82-TyrXxxLysProPhe-86 |
| Antigenic Index - Jameson-Wolf | |
| SEQ. ID. NO. 14389 | 1-MetValGluArgLysLeuThr-7 |
| SEQ. ID. NO. 14390 | 41-ProLysGluTyrSer-45 |
| SEQ. ID. NO. 14391 | 81-AspTyrXxxLysProPheGlyVal-88 |

TABLE 1-continued

Hydrophilic Regions - Hopp-Woods
SEQ. ID. NO. 14392 1-MetValGluArgLysLeuThr-7
a025
AMPHI Regions - AMPHI
SEQ. ID. NO. 14393 15-AlaAlaGlnLeuGlyGlyCysProThrGlnHis-25
SEQ. ID. NO. 14394 36-MetGlnThrValProSerAlaProValTyrAsnProTyrGlyAlaThrProTyr-53
SEQ. ID. NO. 14395 111-AspThrValTyrLysIleSerLysCysTyrHisIle-122
SEQ. ID. NO. 14396 126-AspPheArgAlaTrpAsnGlyMetThrAsp-135
SEQ. ID. NO. 14397 140-IleGlyGlnIleValLysVal-146
SEQ. ID. NO. 14398 206-AspPheArgAlaTrpAsnGlyMetThrAsp-215
SEQ. ID. NO. 14399 220-IleGlyGlnIleValLysVal-226
SEQ. ID. NO. 14400 248-AlaValGlnThrProValLysProAlaAla-257
SEQ. ID. NO. 14401 261-ValGlnSerAlaProGlnPro-267
SEQ. ID. NO. 14402 290-SerGlyThrArgSer-294
SEQ. ID. NO. 14403 307-LysValValAlaAspPhe-312
SEQ. ID. NO. 14404 343-GlyLeuArgGlyTyrGlyAsn-349
Antigenic Index - Jameson-Wolf
SEQ. ID. NO. 14405 22-ProThrGlnHisPro-26
SEQ. ID. NO. 14406 33-AsnSerGlyMetGlnThr-38
SEQ. ID. NO. 14407 58-AlaAlaAsnAspAlaPro-63
SEQ. ID. NO. 14408 108-ValArgGlyAspThrValTyrLysIleSerLys-118
SEQ. ID. NO. 14409 120-TyrHisIleSerGlnAspAspPheArgAla-129
SEQ. ID. NO. 14410 131-AsnGlyMetThrAspAsnThrLeu-138
SEQ. ID. NO. 14411 144-ValLysValLysProAlaGly-150
SEQ. ID. NO. 14412 157-AlaAlaValLysSerArgProAla-164
SEQ. ID. NO. 14413 188-ValArgGlyAspThr-192
SEQ. ID. NO. 14414 195-AsnIleSerLysArgTyrHisIleSerGlnAspAspPheArgAla-209
SEQ. ID. NO. 14415 211-AsnGlyMetThrAspAsnThrLeu-218
SEQ. ID. NO. 14416 224-ValLysValLysProAlaGly-230
SEQ. ID. NO. 14417 237-AlaAlaValLysSerArgProAla-244
SEQ. ID. NO. 14418 252-ProValLysProAlaAlaGlnProProValGlnSerAlaProGlnPro-267
SEQ. ID. NO. 14419 270-ProAlaAlaGluAsnLysAlaVal-277
SEQ. ID. NO. 14420 280-ProAlaProGlnSerProAlaAlaSerProSerGlyThrArgSerValGly-296
SEQ. ID. NO. 14421 302-ArgProThrGlnGlyLysValValAlaAspPheGlyGlyAsnAsnLysGlyValAsp-320
SEQ. ID. NO. 14422 333-AlaAspGlyLysVal-337
SEQ. ID. NO. 14423 342-SerGlyLeuArgGlyTyrGly-348
SEQ. ID. NO. 14424 363-TyrGlyHisAsnGln-367
SEQ. ID. NO. 14425 370-LeuValGlyGluGlyGlnGlnValLysArgGlyGlnGln-382
SEQ. ID. NO. 14426 387-GlyAsnThrGluAlaSerArgThrGlnLeu-396
SEQ. ID. NO. 14427 398-PheGluValArgGlnAsnGlyLysProValAsnProAsnSer-411
Hydrophilic Regions - Hopp-Woods
SEQ. ID. NO. 14428 108-ValArgGlyAspThr-112
SEQ. ID. NO. 14429 123-SerGlnAspAspPheArg-128
SEQ. ID. NO. 14430 144-ValLysValLysPro-148
SEQ. ID. NO. 14431 157-AlaAlaValLysSerArgProAla-164
SEQ. ID. NO. 14432 188-ValArgGlyAspThr-192
SEQ. ID. NO. 14433 200-TyrHisIleSerGlnAspAspPheArg-208
SEQ. ID. NO. 14434 224-ValLysValLysPro-228
SEQ. ID. NO. 14435 237-AlaAlaValLysSerArgProAla-244
SEQ. ID. NO. 14436 253-ValLysProAlaAla-257
SEQ. ID. NO. 14437 270-ProAlaAlaGluAsnLysAlaVal-277
SEQ. ID. NO. 14438 290-SerGlyThrArgSer-294
SEQ. ID. NO. 14439 313-GlyGlyAsnAsnLysGlyValAsp-320
SEQ. ID. NO. 14440 333-AlaAspGlyLysVal-337
SEQ. ID. NO. 14441 373-GluGlyGlnGlnValLysArgGlyGln-381
SEQ. ID. NO. 14442 389-ThrGluAlaSerArgThr-394
SEQ. ID. NO. 14443 400-ValArgGlnAsnGlyLysProValAsn-408
a032
AMPHI Regions - AMPHI
SEQ. ID. NO. 14444 11-LeuArgArgProLeuArgGln-17
SEQ. ID. NO. 14445 67-SerPheAlaGlyAsnValTyrProArgLeu-76
SEQ. ID. NO. 14446 114-ValHisGlyGlnIleGlnHisProValGlnProPheLeuArg-127
SEQ. ID. NO. 14447 134-LeuGlyLeuLeuArgArgPheAspVal-142
Antigenic Index - Jameson-Wolf
SEQ. ID. NO. 14448 1-MetArgArgAsnVal-5
SEQ. ID. NO. 14449 10-ValLeuArgArgProLeuArg-16
SEQ. ID. NO. 14450 28-ArgAlaValProAlaGlyLysGlnGlyPhe-37
SEQ. ID. NO. 14451 41-CysArgLeuThrGlnArgGln-47
SEQ. ID. NO. 14452 57-AlaGlyGlnArgAsnLeuPro-63
SEQ. ID. NO. 14453 104-ValIleAlaHisArgGlnArgVal-111
SEQ. ID. NO. 14454 138-ArgArgPheAspValGlyGlyArgValGlyMet-148
SEQ. ID. NO. 14455 151-ThrAlaPheAspGlnProGlyAla-158
SEQ. ID. NO. 14456 160-LeuProProArgArgGlnLeuAlaArgGlnArgProArgIleGlnThrAlaLeuArgGlnProProGlnArgArgArgLysIleAlaLeu-189
SEQ. ID. NO. 14457 203-HisLeuCysGlnGlnArgLysGln-210
SEQ. ID. NO. 14458 236-ValLysMetArgArgLysProValGlnAsnHisAsnArgProThrGlnIleSerLysLysGln-256
Hydrophilic Regions - Hopp-Woods
SEQ. ID. NO. 14459 1-MetArgArgAsnVal-5
SEQ. ID. NO. 14460 10-ValLeuArgArgProLeuArg-16
SEQ. ID. NO. 14461 28-ArgAlaValProAlaGlyLys-34
SEQ. ID. NO. 14462 41-CysArgLeuThrGln-45

TABLE 1-continued

| | |
|---|---|
| SEQ. ID. NO. 14463 | 104-ValIleAlaHisArgGlnArgVal-111 |
| SEQ. ID. NO. 14464 | 138-ArgArgPheAspValGlyGly-144 |
| SEQ. ID. NO. 14465 | 161-ProProArgArgGlnLeuAlaArgGlnArgProArgIle-173 |
| SEQ. ID. NO. 14466 | 177-LeuArgGlnProProGlnArgArgArgLysIleAlaLeu-189 |
| SEQ. ID. NO. 14467 | 203-HisLeuCysGlnGlnArgLysGln-210 |
| SEQ. ID. NO. 14468 | 236-ValLysMetArgArgLysProValGlnAsnHisAsnArgProThrGlnIleSerLysLysGln-256 |
| a033-2 | |
| AMPHI Regions - AMPHI | |
| SEQ. ID. NO. 14469 | 6-GlnTyrGlyGlyLeuAlaGlyPheProLysArgOysGluSerGlu-20 |
| SEQ. ID. NO. 14470 | 64-GlyGlnAlaPheGluAlaLeuAsnCys-72 |
| SEQ. ID. NO. 14471 | 95-ValGlyAlaLeuProLysTyrLeuAlaSerAsnValValArgAspMetHisGlyLeuLeuSerThrVal-117 |
| SEQ. ID. NO. 14472 | 120-GlnThrGlyLysValLeuAspLysIleProGlyAlaMetGlu-133 |
| SEQ. ID. NO. 14473 | 142-IleLysThrLeuAlaGlu-147 |
| SEQ. ID. NO. 14474 | 157-SerLeuPheGluAsnPhe-162 |
| SEQ. ID. NO. 14475 | 168-GlyProValAspGlyHisAsnValGluAsnLeuValAspValLeuGluAspLeuArgGlyArg-188 |
| SEQ. ID. NO. 14476 | 207-AlaGluAsnAspPro-211 |
| SEQ. ID. NO. 14477 | 213-LysTyrHisAlaValAlaAsnLeuProLysGluSerAlaAla-226 |
| SEQ. ID. NO. 14478 | 242-TyrThrGlnValPheGlyLys-248 |
| SEQ. ID. NO. 14479 | 280-PheProAspArgTyrPheAspVal-287 |
| SEQ. ID. NO. 14480 | 307-LysProValValAlaIleTyrSer-314 |
| SEQ. ID. NO. 14481 | 316-PheLeuGlnArgAlaTyrAspGlnLeu-324 |
| SEQ. ID. NO. 14482 | 357-AspLeuSerPheLeuArgCysIleProAsnMetIleVal-369 |
| SEQ. ID. NO. 14483 | 390-AlaProAlaAlaValArgTyrProArg-398 |
| SEQ. ID. NO. 14484 | 407-SerAspGlyMetGluThrValGlu-414 |
| SEQ. ID. NO. 14485 | 419-IleIleArgArgGlu-423 |
| SEQ. ID. NO. 14486 | 432-PheGlySerMetValAla-437 |
| SEQ. ID. NO. 14487 | 453-MetArgPheValLysProIleAspGluGlu-462 |
| SEQ. ID. NO. 14488 | 469-ArgSerHisAspArgIle-474 |
| SEQ. ID. NO. 14489 | 489-AlaValLeuGluValLeu-494 |
| SEQ. ID. NO. 14490 | 510-AspThrValThrGlyHisGly-516 |
| SEQ. ID. NO. 14491 | 518-ProLysLysLeuLeu-522 |
| Antigenic Index - Jameson-Wolf | |
| SEQ. ID. NO. 14492 | 11-AlaGlyPheProLysArgCysGluSerGluTyrAspAla-23 |
| SEQ. ID. NO. 14493 | 28-HisSerSerThrSerIle-33 |
| SEQ. ID. NO. 14494 | 41-AlaAlaAspLysGlnLeuGlySerAspArgArgSerVal-53 |
| SEQ. ID. NO. 14495 | 57-GlyAspGlyAlaMetThr-62 |
| SEQ. ID. NO. 14496 | 72-CysAlaGlyAspMetAspVal-78 |
| SEQ. ID. NO. 14497 | 85-AsnAspAsnGluMetSerIle-91 |
| SEQ. ID. NO. 14498 | 105-AsnValValArgAspMetHisGly-112 |
| SEQ. ID. NO. 14499 | 117-ValLysAlaGlnThrGlyLysValLeuAspLysIleProGly-130 |
| SEQ. ID. NO. 14500 | 134-PheAlaGlnLysValGluHisLysIleLysThrLeuAlaGluGluAlaGluHisAlaLysGln-154 |
| SEQ. ID. NO. 14501 | 166-TyrThrGlyProValAspGlyHisAsn-174 |
| SEQ. ID. NO. 14502 | 181-ValLeuGluAspLeuArgGlyArgLysGlyPro-191 |
| SEQ. ID. NO. 14503 | 197-IleThrLysLysGlyAsnGlyTyrLysLeuAlaGluAsnAspProValLys-213 |
| SEQ. ID. NO. 14504 | 220-LeuProLysGluSerAlaAla-226 |
| SEQ. ID. NO. 14505 | 228-MetProSerGluLysGluProLysProAlaAlaLysProThrTyr-242 |
| SEQ. ID. NO. 14506 | 253-ArgAlaAlaAlaAspSerArgLeu-260 |
| SEQ. ID. NO. 14507 | 266-AlaMetArgGluGlySerGlyLeuValGluPheGluGlnArgPheProAspArgTyrPhe-285 |
| SEQ. ID. NO. 14508 | 345-ValGlyAlaAspGlyProThrHis-352 |
| SEQ. ID. NO. 14509 | 370-AlaAlaProSerAspGluAsnGluCysArg-379 |
| SEQ. ID. NO. 14510 | 395-ArgTyrProArgGlyThrGlyThr-402 |
| SEQ. ID. NO. 14511 | 406-ValSerAspGlyMetGluThrValGluIleGlyLysGlyIleIleArgArgGluGlyGluLysThrAla-428 |
| SEQ. ID. NO. 14512 | 457-LysProIleAspGluGluLeuIle-464 |
| SEQ. ID. NO. 14513 | 467-LeuAlaArgSerHisAspArgIleValThrLeuGluGluAsnAlaGluGlnGlyGlyAlaGly-487 |
| SEQ. ID. NO. 14514 | 512-ValThrGlyHisGlyAspProLysLysLeuLeuAspAspLeuGlyLeu-527 |
| SEQ. ID. NO. 14515 | 530-GluAlaValGluArgArgValArg-537 |
| SEQ. ID. NO. 14516 | 540-LeuSerAspArgAspAlaAlaAsn-547 |
| Hydrophilic Regions - Hopp-Woods | |
| SEQ. ID. NO. 14517 | 13-PheProLysArgCysGluSerGluTyrAsp-22 |
| SEQ. ID. NO. 14518 | 41-AlaAlaAspLysGlnLeuGlySerAspArgArgSerVal-53 |
| SEQ. ID. NO. 14519 | 74-GlyAspMetAspVal-78 |
| SEQ. ID. NO. 14520 | 85-AsnAspAsnGluMetSerIle-91 |
| SEQ. ID. NO. 14521 | 106-ValValArgAspMetHis-111 |
| SEQ. ID. NO. 14522 | 123-LysValLeuAspLysIleProGly-130 |
| SEQ. ID. NO. 14523 | 134-PheAlaGlnLysValGluHisLysIleLysThrLeuAlaGluGluAlaGluHisAlaLysGln-154 |
| SEQ. ID. NO. 14524 | 181-ValLeuGluAspLeuArgGlyArgLysGlyPro-191 |
| SEQ. ID. NO. 14525 | 197-IleThrLysLysGlyAsnGly-203 |
| SEQ. ID. NO. 14526 | 205-LysLeuAlaGluAsnAspProValLys-213 |
| SEQ. ID. NO. 14527 | 220-LeuProLysGluSerAlaAla-226 |
| SEQ. ID. NO. 14528 | 228-MetProSerGluLysGluProLysProAlaAla-238 |
| SEQ. ID. NO. 14529 | 253-ArgAlaAlaAlaAspSerArgLeu-260 |
| SEQ. ID. NO. 14530 | 266-AlaMetArgGluGlySerGly-272 |
| SEQ. ID. NO. 14531 | 274-ValGluPheGluGlnArgPheProAspArgTyrPhe-285 |
| SEQ. ID. NO. 14532 | 372-ProSerAspGluAsnGluCys-378 |
| SEQ. ID. NO. 14533 | 408-AspGlyMetGluThrValGluIleGlyLysGlyIleIleArgArgGluGlyGluLysThrAla-428 |
| SEQ. ID. NO. 14534 | 457-LysProIleAspGluGluLeuIle-464 |
| SEQ. ID. NO. 14535 | 467-LeuAlaArgSerHisAspArgIleValThrLeuGluGluAsnAlaGluGlnGlyGly-485 |
| SEQ. ID. NO. 14536 | 513-ThrGlyHisGlyAspProLysLysLeuLeuAsp-523 |

TABLE 1-continued

| | |
|---|---|
| SEQ. ID. NO. 14537 | 530-GluAlaValGluArgArgValArg-537 |
| SEQ. ID. NO. 14538 | 540-LeuSerAspArgAspAlaAlaAsn-547 |
| a034 | |
| AMPHI Regions - AMPHI | |
| SEQ. ID. NO. 14539 | 35-LeuAspHisAlaAla-39 |
| SEQ. ID. NO. 14540 | 52-AsnLeuGluGlnMetArgAlaIleMetGluAlaAlaAspGln-65 |
| SEQ. ID. NO. 14541 | 94-AlaValGluGluPheProHisIlePro-102 |
| SEQ. ID. NO. 14542 | 152-ThrValValAsnPheSer-157 |
| SEQ. ID. NO. 14543 | 168-IleGlyValLeuGlyAsnLeuGluThrGly-177 |
| SEQ. ID. NO. 14544 | 186-GlyAlaValGlyLysLeuSer-192 |
| SEQ. ID. NO. 14545 | 197-LeuThrSerValGluAspAlaValArgPheValLysAspThrGly-211 |
| SEQ. ID. NO. 14546 | 226-TyrLysPheThrArgProProThrGly-234 |
| SEQ. ID. NO. 14547 | 236-ValLeuArgIleAspArgIleLysGluIleHisGlnAlaLeu-249 |
| SEQ. ID. NO. 14548 | 261-SerValProGlnGluTrpLeuLysValIleAsnGluTyrGlyGlyAsnIleGlyGluThrTyrGlyValProValGluGluIleValGluGlyIleLysHis Gly-295 |
| SEQ. ID. NO. 14549 | 314-ArgArgTyrLeuAlaGluAsn-320 |
| SEQ. ID. NO. 14550 | 330-LeuSerLysThrIleGluAlaMetLys-338 |
| SEQ. ID. NO. 14551 | 360-ValSerLeuGluLysMetAlaAsnArgTyrAlaLysGlyGluLeuAsnGlnIleVal-378 |
| Antigenic Index - Jameson-Wolf | |
| SEQ. ID. NO. 14552 | 20-LeuProLysGluThrGln-25 |
| SEQ. ID. NO. 14553 | 37-HisAlaAlaGluAsnSerTyrGly-44 |
| SEQ. ID. NO. 14554 | 54-GluGlnMetArgAlaIleMetGluAlaAlaAspGlnVal-66 |
| SEQ. ID. NO. 14555 | 75-SerAlaGlyAlaArgLysTyrAla-82 |
| SEQ. ID. NO. 14556 | 106-HisGlnAspHisGlyAlaSerProAspValCysGlnArgSerIle-120 |
| SEQ. ID. NO. 14557 | 129-MetAspGlySerLeuMetGluAspGlyLysThrProSerSerTyrGluTyr-145 |
| SEQ. ID. NO. 14558 | 164-ValGluGlyGluIle-168 |
| SEQ. ID. NO. 14559 | 173AsnLeuGluThrGlyGluAlaGlyGluGluAspGlyVal-185 |
| SEQ. ID. NO. 14560 | 191-LeuSerHisAspGln-195 |
| SEQ. ID. NO. 14561 | 199-SerValGluAspAlaValArgPheValLysAspThrGlyValAsp-213 |
| SEQ. ID. NO. 14562 | 221-ThrSerHisGlyAla-225 |
| SEQ. ID. NO. 14563 | 227-LysPheThrArgProProThrGlyAspValLeuArgIleAspArgIleLysGluIleHis-246 |
| SEQ. ID. NO. 14564 | 258-GlySerSerSerValPro-263 |
| SEQ. ID. NO. 14565 | 271-AsnGluTyrGlyGlyAsnIleGlyGlu-279 |
| SEQ. ID. NO. 14566 | 287-GluIleValGluGlyIleLysHisGlyValArgLysValAsnIleAspThrAspLeuArgLeuAlaSerThrGlyAlaVal-313 |
| SEQ. ID. NO. 14567 | 316-TyrLeuAlaGluAsnProSerAspPheAspProArgLysTyrLeuSerLysThrIleGluAlaMetLys-338 |
| SEQ. ID. NO. 14568 | 350-CysGluGlyGlnAlaGlyLysIleLysProValSerLeuGluLysMetAlaAsnArgTyrAlaLysGlyGluLeu-374 |
| Hydrophilic Regions - Hopp-Woods | |
| SEQ. ID. NO. 14569 | 54-GluGlnMetArgAlaIleMetGluAlaAlaAspGlnVal-66 |
| SEQ. ID. NO. 14570 | 76-AlaGlyAlaArgLysTyrAla-82 |
| SEQ. ID. NO. 14571 | 108-AspHisGlyAlaSerProAspValCysGln-117 |
| SEQ. ID. NO. 14572 | 132-SerLeuMetGluAspGlyLysThrProSer-141 |
| SEQ. ID. NO. 14573 | 164-ValGluGlyGluIle-168 |
| SEQ. ID. NO. 14574 | 175-GluThrGlyGluAlaGlyGluGluAspGlyVal-185 |
| SEQ. ID. NO. 14575 | 199-SerValGluAspAlaValArgPheValLysAspThrGlyVal-212 |
| SEQ. ID. NO. 14576 | 235-AspValLeuArgIleAspArgIleLysGluIleHis-246 |
| SEQ. ID. NO. 14577 | 287-GluIleValGluGlyIleLysHisGlyValArgLysValAsnIleAspThrAspLeuArgLeu-307 |
| SEQ. ID. NO. 14578 | 320-AsnProSerAspPheAspProArgLysTyrLeuSerLysThrIleGluAlaMetLys-338 |
| SEQ. ID. NO. 14579 | 352-GlyGlnAlaGlyLysIleLysProValSerLeuGluLysMetAlaAsnArgTyrAlaLysGlyGluLeu-374 |
| a036 | |
| AMPHI Regions - AMPHI | |
| SEQ. ID. NO. 14580 | 6-AlaValTyrSerAlaCysAlaAla-13 |
| SEQ. ID. NO. 14581 | 29-GlyArgCysValAsnGlnTyr-35 |
| SEQ. ID. NO. 14582 | 59-SerSerGlyArgPheCysGlnThrIleLys-68 |
| SEQ. ID. NO. 14583 | 106-AlaAlaSerAlaAlaGlnSer-112 |
| SEQ. ID. NO. 14584 | 213-SerAlaCysArgThrMetHisLysThrLeuArgProTyrVal-226 |
| SEQ. ID. NO. 14585 | 250-ArgLeuLysGluTyr-254 |
| Antigenic Index - Jameson-Wolf | |
| SEQ. ID. NO. 14586 | 16-ProAlaArgThrSerSerSerArgArgCysValSerSerGlyArgCysValAsnGlnTyrSerSerArgAlaAspAla-41 |
| SEQ. ID. NO. 14587 | 43-ProTrpArgArgHisSerGlyAla-50 |
| SEQ. ID. NO. 14588 | 55-CysSerSerAspSerSerGlyArgPhe-63 |
| SEQ. ID. NO. 14589 | 73-ProSerPheSerAlaArgLysThrCysSerAspGlyGluThrSerAlaAspSerAsnTrpArg-93 |
| SEQ. ID. NO. 14590 | 96-HisAlaAspGlyLeuGlnThrAlaSerSer-105 |
| SEQ. ID. NO. 14591 | 112-SerAlaXxxThrAlaArgArgMetPheThr-121 |
| SEQ. ID. NO. 14592 | 132-GlnSerArgArgPheCysCysGlyArgArgAlaAlaArgArgValProGlnArgArgArgGluAsnArgLeuGlnProProAspXxxGlySerArgArg ArgSerAlaTyrArgValCysLeuArgArgAlaAspGlyPheProAlaArgThrHisCysArgCysArgLeuLysArgArgIleLeu-193 |
| SEQ. ID. NO. 14593 | 199-LeuProProAspArgProAspAsnArgSerAsnGlyGlyGlySerAlaCysArgThrMetHisLysThrLeuArgProTyrValArgProGlnArgGln GlyCys-233 |
| SEQ. ID. NO. 14594 | 239-AlaAlaArgArgArgHisArgAlaArgValArgArgLeuLysGluTyrGlnThr-256 |
| SEQ. ID. NO. 14595 | 260-AsnLeuAlaProArgArgCysArgTyrAla-269 |
| Hydrophilic Regions - Hopp-Woods | |
| SEQ. ID. NO. 14596 | 18-ArgThrSerSerSerArgArgCysValSerSer-28 |
| SEQ. ID. NO. 14597 | 35-TyrSerSerArgAlaAsp-40 |
| SEQ. ID. NO. 14598 | 45-ArgArgHisSerGly-49 |
| SEQ. ID. NO. 14599 | 55-CysSerSerAspSerSerGlyArg-62 |
| SEQ. ID. NO. 14600 | 75-PheSerAlaArgLysThrCysSerAspGlyGluThrSerAla-88 |
| SEQ. ID. NO. 14601 | 114-XxxThrAlaArgArgMetPhe-120 |
| SEQ. ID. NO. 14602 | 135-ArgPheCysCysGlyArgArgAlaAlaArgArgValProGlnArgArgArgGluAsnArgLeuGlnProProAspXxxGlySerArgArgArgSerAla Tyr-168 |
| SEQ. ID. NO. 14603 | 171-CysLeuArgArgAlaAspGlyPhePro-179 |
| SEQ. ID. NO. 14604 | 182-ThrHisCysArgCysArgLeuLysArgArgIleLeu-193 |

TABLE 1-continued

| SEQ. ID. NO. 14605 | 200-ProProAspArgProAspAsnArgSerAsnGlyGly-211 |
| SEQ. ID. NO. 14606 | 217-ThrMetHisLysThrLeuArgProTyrValArgProGlnArgGlnGly-232 |
| SEQ. ID. NO. 14607 | 239-AlaAlaArgArgArgHisArgAlaArgValArgArgLeuLysGluTyrGln-255 |
| SEQ. ID. NO. 14608 | 262-AlaProArgArgCysArgTyr-268 |

a038
AMPHI Regions - AMPHI

| SEQ. ID. NO. 14609 | 100-GluAlaLysAspHis-104 |
| SEQ. ID. NO. 14610 | 157-GluLysGlyThrGlyGluLeuSerAlaValGlnGluValGluLys-171 |
| SEQ. ID. NO. 14611 | 178-AlaProIleAlaSerLeuAsn-184 |
| SEQ. ID. NO. 14612 | 195-GluPheGlyGlnPheLeuGluProValArgAlaTyrArgArgGlnTyrGlyVal-212 |

Antigenic Index - Jameson-Wolf

| SEQ. ID. NO. 14613 | 2-ThrAspPheArgGlnAspPhe-8 |
| SEQ. ID. NO. 14614 | 22-GluPheThrThrLysAlaGlyArgArgSerPro-32 |
| SEQ. ID. NO. 14615 | 38-GlyLeuPheAsnAspGlyLeu-44 |
| SEQ. ID. NO. 14616 | 58-IleGluSerGlyIleArg-63 |
| SEQ. ID. NO. 14617 | 85-LeuAlaGluLysGlyVal-90 |
| SEQ. ID. NO. 14618 | 96-TyrAsnArgLysGluAlaLysAspHisGlyGluGlyGly-108 |
| SEQ. ID. NO. 14619 | 125-ValIleSerAlaGlyThrSerValArgGluSerIleLysLeuIleGluAlaGluGlyAlaThr-145 |
| SEQ. ID. NO. 14620 | 153-LeuAspArgMetGluLysGlyThrGlyGlu-162 |
| SEQ. ID. NO. 14621 | 167-GlnGluValGluLysGlnTyrGlyLeu-175 |
| SEQ. ID. NO. 14622 | 191-GlnAsnAsnProGluPheGlyGln-198 |
| SEQ. ID. NO. 14623 | 203-ValArgAlaTyrArgArgGlnTyrGlyValGlu-213 |

Hydrophilic Regions - Hopp-Woods

| SEQ. ID. NO. 14624 | 2-ThrAspPheArgGlnAspPhe-8 |
| SEQ. ID. NO. 14625 | 22-GluPheThrThrLysAlaGlyArgArgSer-31 |
| SEQ. ID. NO. 14626 | 85-LeuAlaGluLysGlyVal-90 |
| SEQ. ID. NO. 14627 | 96-TyrAsnArgLysGluAlaLysAspHisGlyGlu-106 |
| SEQ. ID. NO. 14628 | 130-ThrSerValArgGluSerIleLysLeuIleGluAlaGluGlyAlaThr-145 |
| SEQ. ID. NO. 14629 | 153-LeuAspArgMetGluLysGlyThrGlyGlu-162 |
| SEQ. ID. NO. 14630 | 167-GlnGluValGluLysGlnTyr-173 |
| SEQ. ID. NO. 14631 | 204-ArgAlaTyrArgArgGlnTyrGly-211 |

a040
AMPHI Regions - AMPHI

| SEQ. ID. NO. 14632 | 14-AlaAlaProTyrIle-18 |
| SEQ. ID. NO. 14633 | 28-AlaGlyIleAspAsp-32 |
| SEQ. ID. NO. 14634 | 38-AspThrLeuAsnLysPhe-43 |
| SEQ. ID. NO. 14635 | 78-ProHisTyrCysArgGlyLeuArgValThrAspGlu-89 |
| SEQ. ID. NO. 14636 | 92-LeuGluGlnAlaGlnGlnPheAlaGly-100 |
| SEQ. ID. NO. 14637 | 113-SerValSerGlyPheAlaArgAlaPro-121 |
| SEQ. ID. NO. 14638 | 134-ArgProIleGlyValIleAspGly-141 |
| SEQ. ID. NO. 14639 | 146-TyrAlaGlyValIleArg-151 |
| SEQ. ID. NO. 14640 | 207-LeuSerAspGlyIleSerArgProAsp-215 |
| SEQ. ID. NO. 14641 | 226-GluAlaGlnSerLeuAlaGluHisAla-234 |
| SEQ. ID. NO. 14642 | 244-SerAlaValAlaAlaLeuGluGly-251 |
| SEQ. ID. NO. 14643 | 277-IleGlyThrSerIle-281 |
| SEQ. ID. NO. 14644 | 289-IleArgGlnAlaHisSerGlyAspIleProHisIleAlaAlaLeuIleArgProLeuGlu-308 |
| SEQ. ID. NO. 14645 | 320-TyrLeuGluAsnHisIleSerGluPheSerIle-330 |
| SEQ. ID. NO. 14646 | 338-TyrGlyCysAlaAlaLeuLysThrPheAlaGluAlaAsp-350 |
| SEQ. ID. NO. 14647 | 371-ArgLeuLeuAlaHisIle-376 |
| SEQ. ID. NO. 14648 | 386-SerArgLeuPheAla-390 |

Antigenic Index - Jameson-Wolf

| SEQ. ID. NO. 14649 | 11-PheArgGluAlaAlaProTyrIleArgGlnMetArgGlyLysThrLeu-26 |
| SEQ. ID. NO. 14650 | 29-GlyIleAspAspArgLeuLeuGluGlyAspThrLeuAsn-41 |
| SEQ. ID. NO. 14651 | 65-HisPheLeuAspArgHisAlaAlaAlaGlnGlyArgThrProHisTyrCysArgGlyLeuArgValThrAspGluThrSerLeuGluGlnAlaGln-96 |
| SEQ. ID. NO. 14652 | 101-ThrValArgSerArgPheGlu-107 |
| SEQ. ID. NO. 14653 | 119-ArgAlaProSerVal-123 |
| SEQ. ID. NO. 14654 | 140-AspGlyThrAspMetGluTyr-146 |
| SEQ. ID. NO. 14655 | 150-IleArgLysThrAspThrAlaAla-157 |
| SEQ. ID. NO. 14656 | 173-LeuGlyHisSerTyrSerGlyLysThrPhe-182 |
| SEQ. ID. NO. 14657 | 208-SerAspGlyIleSerArgProAspGlyThrLeu-218 |
| SEQ. ID. NO. 14658 | 224-AlaGlnGluAlaGlnSerLeuAlaGluHisAlaGlyGlyGluThrArgArgLeuIle-242 |
| SEQ. ID. NO. 14659 | 249-LeuGluGlyGlyVal-253 |
| SEQ. ID. NO. 14660 | 261-GlyAlaAlaAspGlySerLeuLeu-268 |
| SEQ. ID. NO. 14661 | 272-PheThrArgAsnGlyIleGlyThrSerIleAlaLysGluAlaPheVal-287 |
| SEQ. ID. NO. 14662 | 289-IleArgGlnAlaHisSerGlyAspIle-297 |
| SEQ. ID. NO. 14663 | 305-ArgProLeuGluGluGlnGly-311 |
| SEQ. ID. NO. 14664 | 313-LeuLeuHisArgSerArgGluTyrLeu-321 |
| SEQ. ID. NO. 14665 | 331-LeuGluHisAspGlyAsnLeuTyr-338 |
| SEQ. ID. NO. 14666 | 345-ThrPheAlaGluAlaAspCysGlyGlu-353 |
| SEQ. ID. NO. 14667 | 361-ProGlnAlaGlnAspGlyGlyTyrGlyGluArgLeu-372 |
| SEQ. ID. NO. 14668 | 377-IleAspLysAlaArgGly-382 |
| SEQ. ID. NO. 14669 | 393-ThrAsnThrGlyGlu-397 |
| SEQ. ID. NO. 14670 | 402-ArgGlyPheGlnThrAlaSerGluAspGluLeuProGluThrArgArgLysAspTyrArgSerAsnGlyArgAsnSerHisIleLeu-430 |

Hydrophilic Regions - Hopp-Woods

| SEQ. ID. NO. 14671 | 11-PheArgGluAlaAlaPro-16 |
| SEQ. ID. NO. 14672 | 19-ArgGlnMetArgGlyLysThr-25 |
| SEQ. ID. NO. 14673 | 29-GlyIleAspAspArgLeuLeuGluGlyAspThrLeuAsn-41 |
| SEQ. ID. NO. 14674 | 65-HisPheLeuAspArgHisAlaAlaAlaGlnGlyArgThr-77 |
| SEQ. ID. NO. 14675 | 84-LeuArgValThrAspGluThrSerLeuGluGln-94 |
| SEQ. ID. NO. 14676 | 102-ValArgSerArgPheGlu-107 |

TABLE 1-continued

| | |
|---|---|
| SEQ. ID. NO. 14677 | 140-AspGlyThrAspMetGluTyr-146 |
| SEQ. ID. NO. 14678 | 150-IleArgLysThrAspThrAlaAla-157 |
| SEQ. ID. NO. 14679 | 210-GlyIleSerArgProAspGly-216 |
| SEQ. ID. NO. 14680 | 224-AlaGlnGluAlaGlnSerLeuAlaGlu-232 |
| SEQ. ID. NO. 14681 | 234-AlaGlyGlyGluThrArgArgLeuIle-242 |
| SEQ. ID. NO. 14682 | 291-GlnAlaHisSerGlyAsp-296 |
| SEQ. ID. NO. 14683 | 305-ArgProLeuGluGluGlnGly-311 |
| SEQ. ID. NO. 14684 | 315-HisArgSerArgGluTyrLeu-321 |
| SEQ. ID. NO. 14685 | 345-ThrPheAlaGluAlaAspCysGlyGlu-353 |
| SEQ. ID. NO. 14686 | 362-GlnAlaGlnAspGlyGlyTyrGlyGlu-370 |
| SEQ. ID. NO. 14687 | 377-IleAspLysAlaArgGly-382 |
| SEQ. ID. NO. 14688 | 402-ArgGlyPheGlnThrAlaSerGluAspGluLeuProGluThrArgArgLysAspTyrArgSerAsnGlyArgAsn-426 |
| a041-1 | |
| AMPHI Regions - AMPHI | |
| SEQ. ID. NO. 14689 | 6-AspProTyrArgHisPheGluAsnLeuAspSerAlaGluThr-19 |
| SEQ. ID. NO. 14690 | 45-AspGlyIleLeuAla-49 |
| SEQ. ID. NO. 14691 | 78-LysGlyValTyrArgValCysThrAlaAla-87 |
| SEQ. ID. NO. 14692 | 102-ValAlaAspPheAspGluLeuLeu-109 |
| SEQ. ID. NO. 14693 | 117-GlyValSerHisLeuValGluGlnProAsn-126 |
| SEQ. ID. NO. 14694 | 218-MetValAsnAlaTrpArgTyrLeuAsp-226 |
| SEQ. ID. NO. 14695 | 232-IleAspLeuIleGluAlaSer-238 |
| SEQ. ID. NO. 14696 | 258-LeuAsnLeuProAsnAspCysAspValValGlyTyrLeu-270 |
| SEQ. ID. NO. 14697 | 317-GlnAlaLeuGluSerValGluThr-324 |
| SEQ. ID. NO. 14698 | 331-AlaSerLeuLeuGluAsnValGlnGlyArg-340 |
| SEQ. ID. NO. 14699 | 354-ThrGluLeuProArgLeuProSer-361 |
| SEQ. ID. NO. 14700 | 382-AspPheThrThrProLeu-387 |
| SEQ. ID. NO. 14701 | 405-GlnProGlnGlnPhe-409 |
| SEQ. ID. NO. 14702 | 451-GlyPheGlyIleProGluLeuProHisTyrLeuGlySerIleGlyLys-466 |
| SEQ. ID. NO. 14703 | 493-AlaAlaGlnGlyIleSerLysHisLysSerValAspAspLeuLeuAlaValValSer-511 |
| SEQ. ID. NO. 14704 | 519-SerSerProGluHis-523 |
| SEQ. ID. NO. 14705 | 541-ValArgGluProGlnSer-546 |
| SEQ. ID. NO. 14706 | 556-LeuThrAspMetIleArgTyr-562 |
| SEQ. ID. NO. 14707 | 571-TrpThrAspGluTyrGlyAsnProGlnLysTyrGlu-582 |
| SEQ. ID. NO. 14708 | 591-LeuSerProTyrHisAsnLeuSerAspGlyIleAspTyrProPro-605 |
| SEQ. ID. NO. 14709 | 620-AlaHisAlaLeuLys-624 |
| SEQ. ID. NO. 14710 | 645-GlyHisThrGlyAsnGlyThrGlnArgGluAla-655 |
| Antigenic Index - Jameson-Wolf | |
| SEQ. ID. NO. 14711 | 1-MetLysSerTyrProAspProTyrArgHisPheGluAsnLeuAspSerAlaGluThrGln-20 |
| SEQ. ID. NO. 14712 | 26-AlaAsnAlaGluThrArgAlaArgPheLeuAsnAsnAspLysAlaArgAlaLeuSerAspGly-46 |
| SEQ. ID. NO. 14713 | 51-LeuGlnAspThrArgGlnIleProPhe-59 |
| SEQ. ID. NO. 14714 | 61-GlnGluHisArgAlaArg-66 |
| SEQ. ID. NO. 14715 | 72-GlnAspAlaGluTyrProLysGlyVal-80 |
| SEQ. ID. NO. 14716 | 89-TyrArgSerGlyTyrProGluTrp-96 |
| SEQ. ID. NO. 14717 | 104-AspPheAspGluLeuLeuGlyAspAspValTyr-114 |
| SEQ. ID. NO. 14718 | 123-GluGlnProAsnArg-127 |
| SEQ. ID. NO. 14719 | 132-LeuSerLysSerGlyGlyAspThr-139 |
| SEQ. ID. NO. 14720 | 145-ValAspLeuGluAlaGlyGluLeuValGlu-154 |
| SEQ. ID. NO. 14721 | 161-AlaGlyLysAsnHisValSerTrpArgAspGluAsnSerVal-174 |
| SEQ. ID. NO. 14722 | 178-ProAlaTrpAspGluArgGlnLeuThrGluSerGlyTyrProArgGluValTrpLeuValGluArgGlyLysSerPheGluGluSerLeu-207 |
| SEQ. ID. NO. 14723 | 212-IleAlaGluAspGlyMet-217 |
| SEQ. ID. NO. 14724 | 223-ArgTyrLeuAspProGlnGlySerProIleAspLeuIleGluAlaSerAspGlyPheTyr-242 |
| SEQ. ID. NO. 14725 | 250-SerAlaGluGlyGluAlaLysProLeuAsnLeuProAsnAspCysAspVal-266 |
| SEQ. ID. NO. 14726 | 278-LeuArgLysAspTrpHisArgAlaAsnGlnSerTyrProSer-291 |
| SEQ. ID. NO. 14727 | 298-LysLeuAsnArgGlyGluLeuGly-305 |
| SEQ. ID. NO. 14728 | 312-AlaProAsnGluThrGlnAla-318 |
| SEQ. ID. NO. 14729 | 320-GluSerValGluThrThrLys-326 |
| SEQ. ID. NO. 14730 | 337-ValGlnGlyArgLeuLysAla-343 |
| SEQ. ID. NO. 14731 | 345-ArgPheThrAspGlyLysTrpGlnGluThrGluLeuProArgLeuProSerGly-362 |
| SEQ. ID. NO. 14732 | 365-GluMetThrAspGlnProTrpGlyGly-373 |
| SEQ. ID. NO. 14733 | 401-ValMetArgArgGlnProGlnGlnPheAspSerAspGlyIleAsn-415 |
| SEQ. ID. NO. 14734 | 422-ThrSerAlaAspGlyGluArgIle-429 |
| SEQ. ID. NO. 14735 | 435-GlyLysAsnAlaAlaProAspMet-442 |
| SEQ. ID. NO. 14736 | 479-AsnIleArgGlyGlyGlyGluPheGlyProArgTrpHis-491 |
| SEQ. ID. NO. 14737 | 496-GlyIleSerLysHisLysSerValAspAsp-505 |
| SEQ. ID. NO. 14738 | 512-AspLeuSerGluArgGlyIleSerSerProGluHis-523 |
| SEQ. ID. NO. 14739 | 528-GlyGlySerAsnGly-532 |
| SEQ. ID. NO. 14740 | 540-PheValArgGluProGlnSerIleGlyAla-549 |
| SEQ. ID. NO. 14741 | 568-GlySerSerTrpThrAspGluTyrGlyAsnProGlnLysTyrGluValCysLysArgArgLeuGlyGluLeuSerProTyr-594 |
| SEQ. ID. NO. 14742 | 596-AsnLeuSerAspGlyIleAspTyrPro-604 |
| SEQ. ID. NO. 14743 | 610-ThrSerLeuSerAspAspArgValHis-618 |
| SEQ. ID. NO. 14744 | 627-AlaLysLeuArgGluThrSerProGlnSer-636 |
| SEQ. ID. NO. 14745 | 639-TyrSerProAspGlyGlyGlyHisThrGlyAsnGlyThrGlnArgGluAlaAlaAspGluLeu-659 |
| Hydrophilic Regions - Hopp-Woods | |
| SEQ. ID. NO. 14746 | 3-SerTyrProAspProTyrArgHis-10 |
| SEQ. ID. NO. 14747 | 12-GluAsnLeuAspSerAlaGluThr-19 |
| SEQ. ID. NO. 14748 | 26-AlaAsnAlaGluThrArgAlaArgPheLeuAsnAsnAspLysAlaArgAlaLeuSer-44 |
| SEQ. ID. NO. 14749 | 52-GlnAspThrArgGln-56 |
| SEQ. ID. NO. 14750 | 61-GlnGluHisArgAlaArg-66 |
| SEQ. ID. NO. 14751 | 72-GlnAspAlaGluTyrPro-77 |
| SEQ. ID. NO. 14752 | 104-AspPheAspGluLeuLeuGly-110 |

TABLE 1-continued

| | |
|---|---|
| SEQ. ID. NO. 14753 | 134-LysSerGlyGlyAsp-138 |
| SEQ. ID. NO. 14754 | 145-ValAspLeuGluAlaGlyGluLeuValGlu-154 |
| SEQ. ID. NO. 14755 | 166-ValSerTrpArgAspGluAsnSer-173 |
| SEQ. ID. NO. 14756 | 180-TrpAspGluArgGlnLeuThr-186 |
| SEQ. ID. NO. 14757 | 198-GluArgGlyLysSerPheGluGluSerLeu-207 |
| SEQ. ID. NO. 14758 | 212-IleAlaGluAspGlyMet-217 |
| SEQ. ID. NO. 14759 | 233-AspLeuIleGluAlaSerAsp-239 |
| SEQ. ID. NO. 14760 | 251-AlaGluGlyGluAlaLysPro-257 |
| SEQ. ID. NO. 14761 | 278-LeuArgLysAspTrpHisArg-284 |
| SEQ. ID. NO. 14762 | 298-LysLeuAsnArgGlyGluLeuGly-305 |
| SEQ. ID. NO. 14763 | 320-GluSerValGluThrThrLys-326 |
| SEQ. ID. NO. 14764 | 337-ValGlnGlyArgLeuLysAla-343 |
| SEQ. ID. NO. 14765 | 350-LysTrpGlnGluThrGluLeuProArg-358 |
| SEQ. ID. NO. 14766 | 401-ValMetArgArgGlnProGlnGlnPheAspSerAspGlyIleAsn-415 |
| SEQ. ID. NO. 14767 | 424-AlaAspGlyGluArg-428 |
| SEQ. ID. NO. 14768 | 436-LysAsnAlaAlaProAsp-441 |
| SEQ. ID. NO. 14769 | 481-ArgGlyGlyGlyGluPheGly-487 |
| SEQ. ID. NO. 14770 | 496-GlyIleSerLysHisLysSerValAspAsp-505 |
| SEQ. ID. NO. 14771 | 512-AspLeuSerGluArgGlyIleSerSer-520 |
| SEQ. ID. NO. 14772 | 540-PheValArgGluProGlnSer-546 |
| SEQ. ID. NO. 14773 | 571-TrpThrAspGluTyrGlyAsn-577 |
| SEQ. ID. NO. 14774 | 579-GlnLysTyrGluValCysLysArgArgLeuGlyGlu-590 |
| SEQ. ID. NO. 14775 | 612-LeuSerAspAspArgValHis-618 |
| SEQ. ID. NO. 14776 | 627-AlaLysLeuArgGluThrSer-633 |
| SEQ. ID. NO. 14777 | 650-GlyThrGlnArgGluAlaAlaAspGluLeu-659 |
| a042-1 | |
| AMPHI Regions - AMPHI | |
| SEQ. ID. NO. 14778 | 17-AlaLeuSerAsnThrSerThr-23 |
| SEQ. ID. NO. 14779 | 33-AlaValArgSerMetMetLysIle-40 |
| SEQ. ID. NO. 14780 | 138-SerProLeuValArgIleLeuProLeuSer-147 |
| SEQ. ID. NO. 14781 | 151-SerMetValValAlaPhePheAlaAsn-159 |
| Antigenic Index - Jameson-Wolf | |
| SEQ. ID. NO. 14782 | 14-ArgThrSerAlaLeuSerAsnThrSerThrAlaAlaGlyProSerCys-29 |
| SEQ. ID. NO. 14783 | 49-TyrSerLysGluThrGlyCysProCysProSerLeuArgLysAspSerSerThrGlyGlyArgProMetSerProCys-74 |
| SEQ. ID. NO. 14784 | 77-LeuAlaAsnArgAspCysValProLysAlaAspThr-88 |
| SEQ. ID. NO. 14785 | 93-ThrAspSerThrSerProArgProLeu-101 |
| SEQ. ID. NO. 14786 | 122-AlaArgAlaSerLeuProLysIleArgAlaLysVal-133 |
| SEQ. ID. NO. 14787 | 160-CysSerTyrAlaSerAlaProGlyPro-168 |
| Hydrophilic Regions - Hopp-Woods | |
| SEQ. ID. NO. 14788 | 49-TyrSerLysGluThrGlyCys-55 |
| SEQ. ID. NO. 14789 | 59-SerLeuArgLysAspSerSerThrGlyGlyArgProMet-71 |
| SEQ. ID. NO. 14790 | 78-AlaAsnArgAspCysValProLysAlaAspThr-88 |
| SEQ. ID. NO. 14791 | 94-AspSerThrSerProArg-99 |
| SEQ. ID. NO. 14792 | 125-SerLeuProLysIleArgAlaLysVal-133 |
| a043-2 | |
| AMPHI Regions - AMPHI | |
| SEQ. ID. NO. 14793 | 24-ValGluProSerArg-28 |
| SEQ. ID. NO. 14794 | 36-HisGlyGlyLeuAspGlyAlaAlaGlyPheAspGluGlyGluArg-50 |
| SEQ. ID. NO. 14795 | 59-AlaSerGlyAspGlyPhe-64 |
| SEQ. ID. NO. 14796 | 83-AlaGlyAspPheGlyAspGlyGlnArg-91 |
| Antigenic Index - Jameson-Wolf | |
| SEQ. ID. NO. 14797 | 1-MetProProAlaPro-5 |
| SEQ. ID. NO. 14798 | 11-IleArgArgGlnLysSerValMetProSerGluArgPheValGluProSerArg-28 |
| SEQ. ID. NO. 14799 | 35-ValHisGlyGlyLeuAspGlyAlaAlaGlyPheAspGluGlyGluArgValPhe-52 |
| SEQ. ID. NO. 14800 | 56-AlaAlaGlnAlaSerGlyAspGlyPheAla-65 |
| SEQ. ID. NO. 14801 | 79-GlnSerAspAlaAlaGlyAspPheGlyAspGlyGlnArgThrGlyGlu-94 |
| SEQ. ID. NO. 14802 | 96-ValLeuGlnAspValGlyGly-102 |
| SEQ. ID. NO. 14803 | 116-AlaGluGlyGluAlaGln-121 |
| Hydrophilic Regions - Hopp-Woods | |
| SEQ. ID. NO. 14804 | 11-IleArgArgGlnLysSerValMetProSerGluArgPheValGluProSerArg-28 |
| SEQ. ID. NO. 14805 | 43-AlaGlyPheAspGluGlyGluArgValPhe-52 |
| SEQ. ID. NO. 14806 | 81-AspAlaAlaGlyAspPheGlyAspGlyGlnArgThrGly-93 |
| SEQ. ID. NO. 14807 | 116-AlaGluGlyGluAlaGln-121 |
| a046 | |
| AMPHI Regions - AMPHI | |
| SEQ. ID. NO. 14808 | 6-ArgProThrSerSerPro-11 |
| SEQ. ID. NO. 14809 | 46-ThrSerCysSerGlyLeuMetValSer-54 |
| SEQ. ID. NO. 14810 | 64-PheSerLeuPheSerSer-69 |
| SEQ. ID. NO. 14811 | 113-LysSerAlaSerSer-117 |
| SEQ. ID. NO. 14812 | 143-SerCysAsnAlaPheSerSer-149 |
| SEQ. ID. NO. 14813 | 155-ThrSerLeuLeuGlyMetAlaAlaArgPheCysAlaThrVal-168 |
| Antigenic Index - Jameson-Wolf | |
| SEQ. ID. NO. 14814 | 6-ArgProThrSerSerProProArgArgAlaCys-16 |
| SEQ. ID. NO. 14815 | 20-IleArgThrArgSerSerAlaLysArgLysThrCysAsnAlaProGlyGlnSerIleArgProAlaSerCysSer-44 |
| SEQ. ID. NO. 14816 | 57-ProAsnMetGluArgLeuPro-63 |
| SEQ. ID. NO. 14817 | 75-SerArgTyrSerLeuGluArgThrArgAlaMetArgProGlyMetLeuAsnArgSerAlaAla-95 |
| SEQ. ID. NO. 14818 | 105-SerLeuArgGluSerAlaSerSerLysSerAlaSerSerAlaProAlaArgSerAsnValLysGlyAspAlaProLeuProLysThrValTrpThrSerArgArgLeuProVal-142 |

TABLE 1-continued

| | |
|---|---|
| SEQ. ID. NO. 14819 | 169-GluProThrCysProLeuProLys-176 |
| Hydrophilic Regions - Hopp-Woods | |
| SEQ. ID. NO. 14820 | 7-ProThrSerSerProProArgArgAlaCys-16 |
| SEQ. ID. NO. 14821 | 20-IleArgThrArgSerSerAlaLysArgLysThrCysAsn-32 |
| SEQ. ID. NO. 14822 | 36-GlnSerIleArgProAlaSer-42 |
| SEQ. ID. NO. 14823 | 58-AsnMetGluArgLeuPro-63 |
| SEQ. ID. NO. 14824 | 75-SerArgTyrSerLeuGluArgThrArgAlaMetArg-86 |
| SEQ. ID. NO. 14825 | 105-SerLeuArgGluSerAlaSerSerLysSerAlaSer-116 |
| SEQ. ID. NO. 14826 | 118-AlaProAlaArgSerAsnValLysGlyAspAlaProLeu-130 |
| a047 | |
| AMPHI Regions - AMPHI | |
| SEQ. ID. NO. 14827 | 17-IleAlaAspIleAlaGlnAspLeuProAspGlyAla-28 |
| SEQ. ID. NO. 14828 | 62-AlaGluAsnIleGlyAlaVal-68 |
| SEQ. ID. NO. 14829 | 93-ArgLeuAlaLysGlnLeuGlu-99 |
| SEQ. ID. NO. 14830 | 141-TyrIleAspGluIleAspValPhe-148 |
| SEQ. ID. NO. 14831 | 161-SerAlaLeuLeuAla-165 |
| SEQ. ID. NO. 14832 | 185-LeuLeuGluGlyAsn-189 |
| SEQ. ID. NO. 14833 | 202-IleGlySerIleLeuAla-207 |
| SEQ. ID. NO. 14834 | 247-SerGlyIleLysTrpProGluGlyCys-255 |
| SEQ. ID. NO. 14835 | 257-IleAlaAlaValValArgAlaGlyThrGly-266 |
| SEQ. ID. NO. 14836 | 293-IleLeuAsnGluLeuGluLysLeuIle-301 |
| Antigenic Index - Jameson-Wolf | |
| SEQ. ID. NO. 14837 | 5-GlnAlaArgArgGlyGlyLeuLeu-12 |
| SEQ. ID. NO. 14838 | 20-IleAlaGlnAspLeuProAspGlyAlaAsp-29 |
| SEQ. ID. NO. 14839 | 36-TyrArgAsnAsnArgLeu-41 |
| SEQ. ID. NO. 14840 | 51-IleGluGlyAspGlu-55 |
| SEQ. ID. NO. 14841 | 70-ProGluLeuArgProLysGluThrSerThrArgArgIleMet-83 |
| SEQ. ID. NO. 14842 | 86-GlyGlyGlyAsnIle-90 |
| SEQ. ID. NO. 14843 | 96-LysGlnLeuGluHis-100 |
| SEQ. ID. NO. 14844 | 106-IleIleGluCysArgProArgArgAlaGluTrpIle-117 |
| SEQ. ID. NO. 14845 | 119-GluAsnLeuAspAsnThrLeu-125 |
| SEQ. ID. NO. 14846 | 130-SerAlaThrAspGluThrLeuLeuAspAsnGluTyrIleAspGluIleAsp-146 |
| SEQ. ID. NO. 14847 | 152-ThrAsnAspAspGluSerAsnIle-159 |
| SEQ. ID. NO. 14848 | 168-LeuGlyAlaLysArgVal-173 |
| SEQ. ID. NO. 14849 | 178-AsnArgSerSerTyr-182 |
| SEQ. ID. NO. 14850 | 186-LeuGluGlyAsnLysIle-191 |
| SEQ. ID. NO. 14851 | 208-HisIleArgArgGlyAspIleVal-215 |
| SEQ. ID. NO. 14852 | 219-ProIleArgArgGlyThrAlaGluAlaIleGlu-229 |
| SEQ. ID. NO. 14853 | 232-AlaHisGlyAspLysLysThrSer-239 |
| SEQ. ID. NO. 14854 | 242-IleGlyArgArgIleSerGlyIleLysTrpProGluGlyCysHis-256 |
| SEQ. ID. NO. 14855 | 262-ArgAlaGlyThrGlyGluThr-268 |
| SEQ. ID. NO. 14856 | 277-ValIleGlnAspGlyAspHis-283 |
| SEQ. ID. NO. 14857 | 288-ValSerArgArgArgIleLeuAsnGluLeuGluLys-299 |
| Hydrophilic Regions - Hopp-Woods | |
| SEQ. ID. NO. 14858 | 5-GlnAlaArgArgGlyGly-10 |
| SEQ. ID. NO. 14859 | 20-IleAlaGlnAspLeuProAspGlyAlaAsp-29 |
| SEQ. ID. NO. 14860 | 51-IleGluGlyAspGlu-55 |
| SEQ. ID. NO. 14861 | 70-ProGluLeuArgProLysGluThrSerThrArgArgIleMet-83 |
| SEQ. ID. NO. 14862 | 106-IleIleGluCysArgProArgArgAlaGluTrpIle-117 |
| SEQ. ID. NO. 14863 | 130-SerAlaThrAspGluThrLeuLeu-137 |
| SEQ. ID. NO. 14864 | 140-GluTyrIleAspGluIleAsp-146 |
| SEQ. ID. NO. 14865 | 152-ThrAsnAspAspGluSerAsnIle-159 |
| SEQ. ID. NO. 14866 | 168-LeuGlyAlaLysArgVal-173 |
| SEQ. ID. NO. 14867 | 186-LeuGluGlyAsnLysIle-191 |
| SEQ. ID. NO. 14868 | 209-IleArgArgGlyAspIle-214 |
| SEQ. ID. NO. 14869 | 219-ProIleArgArgGlyThrAlaGluAlaIleGlu-229 |
| SEQ. ID. NO. 14870 | 232-AlaHisGlyAspLysLysThrSer-239 |
| SEQ. ID. NO. 14871 | 242-IleGlyArgArgIleSer-247 |
| SEQ. ID. NO. 14872 | 277-ValIleGlnAspGlyAsp-282 |
| SEQ. ID. NO. 14873 | 289-SerArgArgArgIleLeuAsnGluLeuGluLys-299 |
| a049-2 | |
| AMPHI Regions - AMPHI | |
| SEQ. ID. NO. 14874 | 15-GlnHisLeuLeuGlu-19 |
| SEQ. ID. NO. 14875 | 33-ThrAspAspThrValAspGlyIleGlyGlnMet-43 |
| SEQ. ID. NO. 14876 | 50-GlnProPheGlyGln-54 |
| SEQ. ID. NO. 14877 | 61-GluHisPheAlaProValAspGlyPheArg-70 |
| SEQ. ID. NO. 14878 | 79-HisGlnArgPhePhe-83 |
| SEQ. ID. NO. 14879 | 103-IleGlyValPheProAlaPhe-109 |
| SEQ. ID. NO. 14880 | 202-ArgGlyAlaGlyGlnArgArgValSerArgHisCys-213 |
| SEQ. ID. NO. 14881 | 217-AlaArgLeuThrGlnValPheGlnThrPhePhe-227 |
| Antigenic Index - Jameson-Wolf | |
| SEQ. ID. NO. 14882 | 6-PheAspTyrArgThrArgLeu-12 |
| SEQ. ID. NO. 14883 | 20-LeuIleGlyLysAsnArgHis-26 |
| SEQ. ID. NO. 14884 | 29-LeuHisArgArgThrAspAspThrValAspGly-39 |
| SEQ. ID. NO. 14885 | 49-AspGlnProPheGly-53 |
| SEQ. ID. NO. 14886 | 64-AlaProValAspGlyPheArgValGlnAsnIleAspLeuAspGlyHisGlnArgPhePhe-83 |
| SEQ. ID. NO. 14887 | 90-PheArgAsnProValCysArgArgThrArgPheCys-101 |
| SEQ. ID. NO. 14888 | 122-GlyIleLysProAspSerProProArgPhe-131 |
| SEQ. ID. NO. 14889 | 135-PheArgAsnArgHisLeuGlnGlySerLeuArgVal-146 |
| SEQ. ID. NO. 14890 | 150-PheLeuLysAspAspHisArgValGly-158 |

TABLE 1-continued

| | |
|---|---|
| SEQ. ID. NO. 14891 | 182-GlnHisThrGlySer-186 |
| SEQ. ID. NO. 14892 | 193-ArgHisArgArgValArgSerGlyPheArgGlyAlaGlyGlnArgArgValSerArgHisCys-213 |
| SEQ. ID. NO. 14893 | 246-ArgGlnThrAsnProArgProLysArgGlyLeu-256 |
| Hydrophilic Regions - Hopp-Woods | |
| SEQ. ID. NO. 14894 | 21-IleGlyLysAsnArgHis-26 |
| SEQ. ID. NO. 14895 | 31-ArgArgThrAspAspThrValAsp-38 |
| SEQ. ID. NO. 14896 | 72-GlnAsnIleAspLeuAspGlyHisGlnArgPhePhe-83 |
| SEQ. ID. NO. 14897 | 93-ProValCysArgArgThrArgPheCys-101 |
| SEQ. ID. NO. 14898 | 124-LysProAspSerProProArg-130 |
| SEQ. ID. NO. 14899 | 150-PheLeuLysAspAspHisArgVal-157 |
| SEQ. ID. NO. 14900 | 193-ArgHisArgArgValArgSerGlyPheArgGlyAlaGlyGlnArgArgValSerArg-211 |
| SEQ. ID. NO. 14901 | 246-ArgGlnThrAsnProArgProLysArgGlyLeu-256 |
| a050-1 | |
| AMPHI Regions - AMPHI | |
| SEQ. ID. NO. 14902 | 10-IleGlnSerIleCysAspAlaPheGlnPheIleSerTyrTyr-23 |
| SEQ. ID. NO. 14903 | 25-ProLysAspTyrIleAspAlaLeuTyrLysAlaTrpGlnLys-38 |
| SEQ. ID. NO. 14904 | 94-ValAsnGluGlyVal-98 |
| SEQ. ID. NO. 14905 | 163-AsnProSerAspAsnIleValAspTrpValLeuLys-174 |
| SEQ. ID. NO. 14906 | 177-ProThrMetGlyAla-181 |
| SEQ. ID. NO. 14907 | 235-LeuGluLeuPheGluLysValAsnAla-243 |
| SEQ. ID. NO. 14908 | 250-GlyLeuGlyGlyLeuThrThr-256 |
| SEQ. ID. NO. 14909 | 275-AlaMetIleProAsn-279 |
| SEQ. ID. NO. 14910 | 302-ArgValGluAspTrpProAspLeuThr-310 |
| SEQ. ID. NO. 14911 | 315-AsnGlyLysArgValAspValAsp-322 |
| SEQ. ID. NO. 14912 | 353-LysArgLeuValAspMetLeuAspLys-361 |
| SEQ. ID. NO. 14913 | 367-ValAspPheThrAsnArgLeu-373 |
| SEQ. ID. NO. 14914 | 379-ProValAspProValGlyAspGlu-386 |
| SEQ. ID. NO. 14915 | 396-AlaThrArgMetAspLysPheThrArgGlnMet-406 |
| SEQ. ID. NO. 14916 | 410-ThrAspLeuLeuGlyMet-415 |
| SEQ. ID. NO. 14917 | 452-LysSerSerLysValLeuAlaPhe-459 |
| Antigenic Index - Jameson-Wolf | |
| SEQ. ID. NO. 14918 | 4-IleLysGlnGluAspPheIle-10 |
| SEQ. ID. NO. 14919 | 23-TyrHisProLysAspTyrIleAspAlaLeu-32 |
| SEQ. ID. NO. 14920 | 36-TrpGlnLysGluGluAsnProAlaAlaLysAspAlaMet-48 |
| SEQ. ID. NO. 14921 | 55-SerArgMetCysAlaGluAsnAsnArgProIleCysGlnAspThrGly-70 |
| SEQ. ID. NO. 14922 | 88-MetSerValGluGluMetValAsnGluGlyValArgArgAlaTyrThrTrpGluGlyAsnThrLeuArgAlaSerVal-113 |
| SEQ. ID. NO. 14923 | 116-AspProAlaGlyLysArgGlnAsnThrLysAspAsnThr-128 |
| SEQ. ID. NO. 14924 | 137-ValProGlyAspLysValGluVal-144 |
| SEQ. ID. NO. 14925 | 146-CysAlaAlaLysGlyGlyGlySerGluAsnLysSerLysLeu-159 |
| SEQ. ID. NO. 14926 | 163-AsnProSerAspAsnIle-168 |
| SEQ. ID. NO. 14927 | 192-GlyIleGlyGlyThrProGluLysAlaValLeuMetAlaLysGluSerLeu-208 |
| SEQ. ID. NO. 14928 | 213-AspIleGlnGluLeuGlnGluLysAlaAlaSerGlyAlaGluLeuSerThr-229 |
| SEQ. ID. NO. 14929 | 284-ArgHisValGluPheGluLeuAspGlySerGlyProValGluLeuThrProProArgValGluAspTrpProAspLeuThrTyrSerProAspAsnGly LysArgValAspValAspLysLeuThrLysGluGluValAlaSer-331 |
| SEQ. ID. NO. 14930 | 345-LeuThrGlyArgAspAlaAlaHisLysArgLeuValAspMetLeuAspLysGlyGluGluLeuPro-366 |
| SEQ. ID. NO. 14931 | 379-ProValAspProValGlyAspGluIleValGlyProAlaGlyProThrThrAlaThrArgMetAspLysPheThrArgGlnMetLeuGluGlnThr Asp-411 |
| SEQ. ID. NO. 14932 | 417-GlyLysSerGluArgGlyAlaAlaThr-425 |
| SEQ. ID. NO. 14933 | 428-AlaIleAlaAspAsnLysAla-434 |
| SEQ. ID. NO. 14934 | 450-AlaIleLysSerSerLys-455 |
| SEQ. ID. NO. 14935 | 470-PheGluValLysAspMetPro-476 |
| SEQ. ID. NO. 14936 | 481-ValAspSerLysGlyGluSerIle-488 |
| SEQ. ID. NO. 14937 | 492-AlaProProGlnTrpGln-497 |
| Hydrophilic Regions - Hopp-Woods | |
| SEQ. ID. NO. 14938 | 4-IleLysGlnGluAspPheIle-10 |
| SEQ. ID. NO. 14939 | 36-TrpGlnLysGluGluAsnProAlaAlaLysAspAlaMet-48 |
| SEQ. ID. NO. 14940 | 57-MetCysAlaGluAsnAsnArgProIleCys-66 |
| SEQ. ID. NO. 14941 | 88-MetSerValGluGluMetValAsnGluGlyValArgArg-100 |
| SEQ. ID. NO. 14942 | 117-ProAlaGlyLysArgGlnAsnThrLysAspAsnThr-128 |
| SEQ. ID. NO. 14943 | 138-ProGlyAspLysValGluVal-144 |
| SEQ. ID. NO. 14944 | 148-AlaLysGlyGlyGlySerGluAsnLysSerLysLeu-159 |
| SEQ. ID. NO. 14945 | 195-GlyThrProGluLysAlaValLeuMetAlaLysGluSerLeu-208 |
| SEQ. ID. NO. 14946 | 213-AspIleGlnGluLeuGlnGluLysAlaAlaSer-223 |
| SEQ. ID. NO. 14947 | 225-AlaGluLeuSerThr-229 |
| SEQ. ID. NO. 14948 | 284-ArgHisValGluPheGluLeuAspGly-292 |
| SEQ. ID. NO. 14949 | 299-ThrProProArgValGluAspTrpPro-307 |
| SEQ. ID. NO. 14950 | 313-ProAspAsnGlyLysArgValAspValAspLysLeuThrLysGluGluValAlaSer-331 |
| SEQ. ID. NO. 14951 | 345-LeuThrGlyArgAspAlaAlaHisLysArgLeuValAspMetLeuAspLysGlyGluGluLeuPro-366 |
| SEQ. ID. NO. 14952 | 382-ProValGlyAspGluIleVal-388 |
| SEQ. ID. NO. 14953 | 397-ThrArgMetAspLysPheThrArgGlnMetLeuGluGlnThrAsp-411 |
| SEQ. ID. NO. 14954 | 417-GlyLysSerGluArgGlyAlaAlaThr-425 |
| SEQ. ID. NO. 14955 | 428-AlaIleAlaAspAsnLysAla-434 |
| SEQ. ID. NO. 14956 | 450-AlaIleLysSerSerLys-455 |
| SEQ. ID. NO. 14957 | 470-PheGluValLysAspMetPro-476 |
| SEQ. ID. NO. 14958 | 481-ValAspSerLysGlyGluSerIle-488 |
| a052 | |

TABLE 1-continued

| | |
|---|---|
| AMPHI Regions - AMPHI | |
| SEQ. ID. NO. 14959 | 40-AlaLysAlaSerLysSerAlaThrSerProLysGlyLeuAspGlyValSerLys-57 |
| SEQ. ID. NO. 14960 | 66-ThrAlaAlaPheHisSerPheIleSerValGlyAspThrLeuThrSerMetProAsnLeuValThrMetLeu-89 |
| Antigenic Index - Jameson-Wolf | |
| SEQ. ID. NO. 14961 | 4-ValAlaGluGluThrGluIle-10 |
| SEQ. ID. NO. 14962 | 14-CysPheLysGlyGluProThrGlyAspSerArgLeuLeuSerThrThrLysSerAlaPro-33 |
| SEQ. ID. NO. 14963 | 36-CysAlaAsnSerAlaLysAlaSerLysSerAlaThrSerProLysGlyLeuAspGlyValSerLysAsnSerSer-60 |
| SEQ. ID. NO. 14964 | 95-ValValProAsnArgLeuArgLeu-102 |
| SEQ. ID. NO. 14965 | 108-ProAlaCysLysLysValLysAsnAlaAla-117 |
| Hydrophilic Regions - Hopp-Woods | |
| SEQ. ID. NO. 14966 | 4-ValAlaGluGluThrGluIle-10 |
| SEQ. ID. NO. 14967 | 15-PheLysGlyGluProThrGlyAspSerArgLeu-25 |
| SEQ. ID. NO. 14968 | 29-ThrLysSerAlaPro-33 |
| SEQ. ID. NO. 14969 | 38-AsnSerAlaLysAlaSerLysSerAlaThrSerProLysGlyLeuAspGlyValSerLysAsnSer-59 |
| SEQ. ID. NO. 14970 | 98-AsnArgLeuArgLeu-102 |
| SEQ. ID. NO. 14971 | 109-AlaCysLysLysValLysAsnAlaAla-117 |
| a075 | |
| AMPHI Regions - AMPHI | |
| SEQ. ID. NO. 14972 | 19-LysThrProThrThrIleGlnProAlaSerIleProSer-31 |
| SEQ. ID. NO. 14973 | 65-AlaProTyrLeuArgGlnValLeu-72 |
| SEQ. ID. NO. 14974 | 80-PheLysLysCysLeuAla-85 |
| SEQ. ID. NO. 14975 | 116-AspPhePheGlnThrCysValAsnArgPhePheGluValValGluIleIleGlyIleGly-135 |
| Antigenic Index - Jameson-Wolf | |
| SEQ. ID. NO. 14976 | 10-ThrMetGluLysThrLysSerAlaAlaLysThrProThr-22 |
| SEQ. ID. NO. 14977 | 25-GlnProAlaSerIlePro-30 |
| SEQ. ID. NO. 14978 | 52-AlaLysAlaArgGly-56 |
| SEQ. ID. NO. 14979 | 91-PhePheArgArgProProAsnIleArgLysSerValPheGlnLysSerGluTyrAspLys-110 |
| Hydrophilic Regions - Hopp-Woods | |
| SEQ. ID. NO. 14980 | 10-ThrMetGluLysThrLysSerAlaAlaLysThr-20 |
| SEQ. ID. NO. 14981 | 52-AlaLysAlaArgGly-56 |
| SEQ. ID. NO. 14982 | 91-PhePheArgArgProProAsnIleArgLysSerValPheGlnLysSerGluTyrAspLys-110 |
| a080 | |
| AMPHI Regions - AMPHI | |
| SEQ. ID. NO. 14983 | 6-GluAlaMetGluArgLeuThrArg-13 |
| SEQ. ID. NO. 14984 | 95-PheProAspThrValGlu-100 |
| SEQ. ID. NO. 14985 | 108-ProValAlaArgTrpGlyAspHis-115 |
| SEQ. ID. NO. 14986 | 144-SerAlaGluMetLeuArgArgTyrAspGluPheSerThrValLeu-158 |
| SEQ. ID. NO. 14987 | 195-LysArgLeuArgLeuPheThrGluAlaTrpGlnHis-206 |
| Antigenic Index - Jameson-Wolf | |
| SEQ. ID. NO. 14988 | 1-MetTrpAspAsnAlaGluAlaMetGluArgLeuThr-12 |
| SEQ. ID. NO. 14989 | 33-AsnSerAsnHisLeuPro-38 |
| SEQ. ID. NO. 14990 | 42-ValSerLeuLysGly-46 |
| SEQ. ID. NO. 14991 | 50-TyrSerAspLysLysAlaLeu-56 |
| SEQ. ID. NO. 14992 | 67-AsnIleLeuArgThrAspIleAsnGlyAlaGlnGluAlaTyrArg-81 |
| SEQ. ID. NO. 14993 | 90-MetValArgArgArgPheProAspThrValGlu-100 |
| SEQ. ID. NO. 14994 | 103-LeuThrGluArgLysProValAlaArgTrpGly-113 |
| SEQ. ID. NO. 14995 | 116-AlaLeuValAspGlyGluGlyAsnValPhe-125 |
| SEQ. ID. NO. 14996 | 127-AlaArgLeuAspArgProGlyMetPro-135 |
| SEQ. ID. NO. 14997 | 138-ArgGlyAlaGluGlyThrSer-144 |
| SEQ. ID. NO. 14998 | 146-GluMetLeuArgArgTyrAspGlu-153 |
| SEQ. ID. NO. 14999 | 163-LeuGlyIleLysGlu-167 |
| SEQ. ID. NO. 15000 | 187-ArgLeuGlyArgGluAsnGluMetLysArgLeuArgLeu-199 |
| SEQ. ID. NO. 15001 | 207-LeuLeuArgLysAsnLysAsnArgLeuSer-216 |
| SEQ. ID. NO. 15002 | 220-MetArgTyrLysAspGlyPheSer-227 |
| SEQ. ID. NO. 15003 | 230-TyrAlaProAspGlyLeuProGluLysGluSerGluGlu-242 |
| Hydrophilic Regions - Hopp-Woods | |
| SEQ. ID. NO. 15004 | 3-AspAsnAlaGluAlaMetGluArgLeuThr-12 |
| SEQ. ID. NO. 15005 | 50-TyrSerAspLysLysAlaLeu-56 |
| SEQ. ID. NO. 15006 | 69-LeuArgThrAspIleAsnGlyAlaGlnGluAlaTyrArg-81 |
| SEQ. ID. NO. 15007 | 90-MetValArgArgArgPheProAspThrVal-99 |
| SEQ. ID. NO. 15008 | 103-LeuThrGluArgLysProValAlaArgTrpGly-113 |
| SEQ. ID. NO. 15009 | 116-AlaLeuValAspGlyGluGlyAsnValPhe-125 |
| SEQ. ID. NO. 15010 | 127-AlaArgLeuAspArgProGly-133 |
| SEQ. ID. NO. 15011 | 138-ArgGlyAlaGluGlyThrSer-144 |
| SEQ. ID. NO. 15012 | 146-GluMetLeuArgArgTyrAspGlu-153 |
| SEQ. ID. NO. 15013 | 163-LeuGlyIleLysGlu-167 |
| SEQ. ID. NO. 15014 | 187-ArgLeuGlyArgGluAsnGluMetLysArgLeuArgLeu-199 |
| SEQ. ID. NO. 15015 | 208-LeuArgLysAsnLysAsnArgLeuSer-216 |
| SEQ. ID. NO. 15016 | 220-MetArgTyrLysAspGlyPheSer-227 |
| SEQ. ID. NO. 15017 | 234-GlyLeuProGluLysGluSerGluGlu-242 |
| a081 | |
| AMPHI Regions - AMPHI | |
| SEQ. ID. NO. 15018 | 22-LysProValSerArgIleValThrAspSer-31 |
| SEQ. ID. NO. 15019 | 86-ThrAlaLeuGlnMetLeuAlaLysAlaTrpArgGluAsn-98 |
| SEQ. ID. NO. 15020 | 116-LysGluMetLeuAlaAlaValLeuArgArg-125 |
| SEQ. ID. NO. 15021 | 135-ThrAlaGlyAsnPhe-139 |
| SEQ. ID. NO. 15022 | 165-MetAsnHisPheGlyGluLeuAlaValLeuThrGlnIleAlaLys-179 |
| SEQ. ID. NO. 15023 | 185-ValAsnAsnAlaMetArg-190 |
| SEQ. ID. NO. 15024 | 198-AspGlyValGlyAspIleAlaLysAla-206 |
| SEQ. ID. NO. 15025 | 303-LeuAsnAspValAlaGluGlyLeuLysGlyPheSerAsnIle-316 |

TABLE 1-continued

| | |
|---|---|
| SEQ. ID. NO. 15026 | 345-AlaAlaValAspValLeuAlaArgMetPro-354 |
| SEQ. ID. NO. 15027 | 360-ValMetGlyAspMetGlyGluLeuGlyGlu-369 |
| SEQ. ID. NO. 15028 | 399-ValGluAlaAlaGlu-403 |
| Antigenic Index - Jameson-Wolf | |
| SEQ. ID. NO. 15029 | 16-ProMetProSerGluSerLysProValSer-25 |
| SEQ. ID. NO. 15030 | 27-IleValThrAspSerArgAspIleArgAlaGlyAsp-38 |
| SEQ. ID. NO. 15031 | 44-AlaGlyGlyArgPheAspAla-50 |
| SEQ. ID. NO. 15032 | 67-ValSerArgGluAspCysValAla-74 |
| SEQ. ID. NO. 15033 | 77-GlyAlaLeuLysValAspAspThrLeu-85 |
| SEQ. ID. NO. 15034 | 94-AlaTrpArgGluAsnValAsnProPhe-102 |
| SEQ. ID. NO. 15035 | 108-GlySerGlyGlyLysThrThrValLysGluMetLeu-119 |
| SEQ. ID. NO. 15036 | 123-LeuArgArgArgPheGlyAspAsnAlaVal-132 |
| SEQ. ID. NO. 15037 | 138-AsnPheAsnAsnHisIle-143 |
| SEQ. ID. NO. 15038 | 151-LysLeuAsnGluLysHisArg-157 |
| SEQ. ID. NO. 15039 | 178-AlaLysProAspAla-182 |
| SEQ. ID. NO. 15040 | 194-GlyCysGlyPheAspGlyValGlyAspIleAlaLysAlaLysSerGluIle-210 |
| SEQ. ID. NO. 15041 | 213-GlyLeuCysSerAspGly-218 |
| SEQ. ID. NO. 15042 | 223-ProGlnGluAspAlaAsn-228 |
| SEQ. ID. NO. 15043 | 239-LeuAsnThrArgThrPheGlyIleAspSerGlyAspValHisAla-253 |
| SEQ. ID. NO. 15044 | 280-ValProGlyArgHisAsnVal-286 |
| SEQ. ID. NO. 15045 | 305-AspValAlaGluGlyLeuLys-311 |
| SEQ. ID. NO. 15046 | 313-PheSerAsnIleLysGlyArgLeuAsnValLysSerGlyIleLysGly-328 |
| SEQ. ID. NO. 15047 | 330-ThrLeuIleAspAspThrTyrAsnAlaAsnProAspSerMetLysAlaAlaVal-347 |
| SEQ. ID. NO. 15048 | 363-AspMetGlyGluLeuGlyGluAspGluAlaAla-373 |
| SEQ. ID. NO. 15049 | 381-AlaTyrAlaArgAspGlnGlyIle-388 |
| SEQ. ID. NO. 15050 | 395-GlyAspAsnSerValGluAlaAlaGluLysPheGlyAla-407 |
| SEQ. ID. NO. 15051 | 422-LeuArgHisAspLeuProGluArgAlaThrVal-432 |
| SEQ. ID. NO. 15052 | 434-ValLysGlySerArg-438 |
| SEQ. ID. NO. 15053 | 443-GluGluValValGluAlaLeuGluAspLys-452 |
| Hydrophilic Regions - Hopp-Woods | |
| SEQ. ID. NO. 15054 | 17-MetProSerGluSerLysProValSer-25 |
| SEQ. ID. NO. 15055 | 27-IleValThrAspSerArgAspIleArgAla-36 |
| SEQ. ID. NO. 15056 | 46-GlyArgPheAspAla-50 |
| SEQ. ID. NO. 15057 | 67-ValSerArgGluAspCysValAla-74 |
| SEQ. ID. NO. 15058 | 77-GlyAlaLeuLysValAspAspThrLeu-85 |
| SEQ. ID. NO. 15059 | 94-AlaTrpArgGluAsnVal-99 |
| SEQ. ID. NO. 15060 | 109-SerGlyGlyLysThrThrValLysGluMetLeu-119 |
| SEQ. ID. NO. 15061 | 123-LeuArgArgArgPheGlyAsp-129 |
| SEQ. ID. NO. 15062 | 151-LysLeuAsnGluLysHisArg-157 |
| SEQ. ID. NO. 15063 | 178-AlaLysProAspAla-182 |
| SEQ. ID. NO. 15064 | 199-GlyValGlyAspIleAlaLysAlaLysSerGluIle-210 |
| SEQ. ID. NO. 15065 | 223-ProGlnGluAspAlaAsn-228 |
| SEQ. ID. NO. 15066 | 247-AspSerGlyAspValHisAla-253 |
| SEQ. ID. NO. 15067 | 305-AspValAlaGluGlyLeuLys-311 |
| SEQ. ID. NO. 15068 | 316-IleLysGlyArgLeuAsnVal-322 |
| SEQ. ID. NO. 15069 | 335-ThrTyrAsnAlaAsnProAspSerMetLysAlaAlaVal-347 |
| SEQ. ID. NO. 15070 | 363-AspMetGlyGluLeuGlyGluAspGluAlaAla-373 |
| SEQ. ID. NO. 15071 | 381-AlaTyrAlaArgAspGlnGlyIle-388 |
| SEQ. ID. NO. 15072 | 397-AsnSerValGluAlaAlaGluLysPheGlyAla-407 |
| SEQ. ID. NO. 15073 | 422-LeuArgHisAspLeuProGluArgAlaThrVal-432 |
| SEQ. ID. NO. 15074 | 443-GluGluValValGluAlaLeuGluAspLys-452 |
| a084-2 | |
| AMPHI Regions - AMPHI | |
| SEQ. ID. NO. 15075 | 6-ArgIleLysAsnMetAspGlnThrLeuLysAsnThrLeuGly-19 |
| SEQ. ID. NO. 15076 | 21-CysAlaLeuLeuAla-25 |
| SEQ. ID. NO. 15077 | 48-AlaValGlyAlaLeuAla-53 |
| SEQ. ID. NO. 15078 | 65-PheProArgValSer-69 |
| SEQ. ID. NO. 15079 | 96-GlnIleValGlySerIleLeuGluSer-104 |
| SEQ. ID. NO. 15080 | 111-GluPheValGlyAsnLeuProGly-118 |
| Antigenic Index - Jameson-Wolf | |
| SEQ. ID. NO. 15081 | 1-MetLysGlnSerAlaArgIleLysAsnMetAspGlnThrLeuLysAsnThr-17 |
| SEQ. ID. NO. 15082 | 40-TyrGluTyrGlyTyrArgTyrSer-47 |
| SEQ. ID. NO. 15083 | 102-LeuGluSerAsnProAlaGluAlaArgGluPheValGly-114 |
| SEQ. ID. NO. 15084 | 139-ValSerGlyGlyGly-143 |
| Hydrophilic Regions - Hopp-Woods | |
| SEQ. ID. NO. 15085 | 1-MetLysGlnSerAlaArgIleLysAsnMetAspGlnThrLeu-14 |
| SEQ. ID. NO. 15086 | 105-AsnProAlaGluAlaArgGluPheVal-113 |
| a085-2 | |
| AMPHI Regions - AMPHI | |
| SEQ. ID. NO. 15087 | 41-GluArgValSerGlnIleGlyLysMetPheAspGlyLeu-53 |
| SEQ. ID. NO. 15088 | 60-LeuLysAspAlaLeuSerAsnGlyPheAsp-69 |
| SEQ. ID. NO. 15089 | 89-ArgAsnGlyGlyArgValLeuGlyAspIleGluLeuLeuAlaAspIle-104 |
| SEQ. ID. NO. 15090 | 125-ThrSerLeuValGlyTyr-130 |
| SEQ. ID. NO. 15091 | 141-IleAlaGlyAsnIleGlyAla-147 |
| SEQ. ID. NO. 15092 | 174-GluAsnThrGluSerLeu-179 |
| SEQ. ID. NO. 15093 | 193-HisLeuAspArgTyrAspAspLeuLeuAspTyr-203 |
| SEQ. ID. NO. 15094 | 212-ArgGlyAspGlyValGln-217 |
| SEQ. ID. NO. 15095 | 225-PheCysArgAlaMetLysArgAla-232 |
| SEQ. ID. NO. 15096 | 275-HisAsnAlaThrAsnValMetAlaAlaValAlaLeuCysGluAla-289 |
| SEQ. ID. NO. 15097 | 300-HisValLysThrPheGlnGlyLeuProHisArgValGluLysIleGly-315 |

TABLE 1-continued

| | |
|---|---|
| SEQ. ID. NO. 15098 | 336-AlaAlaIleAlaGlyLeu-341 |
| SEQ. ID. NO. 15099 | 353-GlyLysGlyGlnAspPheThr-359 |
| SEQ. ID. NO. 15100 | 395-AspCysAlaThrLeuGluGluAlaValGlnLysAla-406 |
| SEQ. ID. NO. 15101 | 424-SerPheAspMetPheLysGlyTyr-431 |
| Antigenic Index - Jameson-Wolf | |
| SEQ. ID. NO. 15102 | 4-GlnAsnLysLysIleLeu-9 |
| SEQ. ID. NO. 15103 | 23-TyrLeuArgLysAsnGlyAlaGluValAlaAlaTyrAspAlaGluLeuLysProGluArgValSerGlnIleGlyLysMetPheAsp-51 |
| SEQ. ID. NO. 15104 | 58-GlyArgLeuLysAspAlaLeuSerAsnGly-67 |
| SEQ. ID. NO. 15105 | 74-SerProGlyIleSerGluArgGlnProAspIleGluAlaPheLysArgAsnGlyGlyArgValLeuGly-96 |
| SEQ. ID. NO. 15106 | 104-IleValAsnArgArgGlyAspLysValIle-113 |
| SEQ. ID. NO. 15107 | 116-ThrGlySerAsnGlyLysThrThr-123 |
| SEQ. ID. NO. 15108 | 150-LeuGluAlaGluLeuGlnArgGluGlyLysLysAlaAsp-162 |
| SEQ. ID. NO. 15109 | 169-SerSerPheGlnLeuGluAsnThrGluSerLeuArgProThrAla-183 |
| SEQ. ID. NO. 15110 | 189-IleSerGluAspHisLeuAspArgTyrAspAspLeuLeu-201 |
| SEQ. ID. NO. 15111 | 204-AlaHisThrLysAlaLysIlePheArgGlyAspGlyVal-216 |
| SEQ. ID. NO. 15112 | 220-AsnAlaAspAspAlaPheCysArgAlaMetLysArgAlaGlyArgGluValLys-237 |
| SEQ. ID. NO. 15113 | 247-PheTrpLeuGluArgGluThrGlyArgLeuLysGlnGlyAsnGluAspLeuIleAla-265 |
| SEQ. ID. NO. 15114 | 291-GlyLeuProArgGluAlaLeu-297 |
| SEQ. ID. NO. 15115 | 307-LeuProHisArgValGluLysIleGlyGluLysAsnGly-319 |
| SEQ. ID. NO. 15116 | 322-PheIleAspAspSerLysGlyThrAsnVal-331 |
| SEQ. ID. NO. 15117 | 351-GlyMetGlyLysGlyGlnAspPheThrProLeuArgAspAlaLeuAlaGlyLysAlaLys-370 |
| SEQ. ID. NO. 15118 | 378-AspAlaProGlnIleArgArgAspLeuAspGlyCysAspLeuAsnMetThrAspCysAlaThrLeuGluGluAlaValGln-404 |
| SEQ. ID. NO. 15119 | 431-TyrAlaHisArgSer-435 |
| Hydrophilic Regions - Hopp-Woods | |
| SEQ. ID. NO. 15120 | 4-GlnAsnLysLysIleLeu-9 |
| SEQ. ID. NO. 15121 | 25-ArgLysAsnGlyAlaGlu-30 |
| SEQ. ID. NO. 15122 | 32-AlaAlaTyrAspAlaGluLeuLysProGluArgValSerGln-45 |
| SEQ. ID. NO. 15123 | 59-ArgLeuLysAspAlaLeu-64 |
| SEQ. ID. NO. 15124 | 76-GlyIleSerGluArgGlnProAspIleGluAlaPheLysArgAsnGlyGly-92 |
| SEQ. ID. NO. 15125 | 104-IleValAsnArgArgGlyAspLysValIle-113 |
| SEQ. ID. NO. 15126 | 118-SerAsnGlyLysThrThr-123 |
| SEQ. ID. NO. 15127 | 150-LeuGluAlaGluLeuGlnArgGluGlyLysLysAlaAsp-162 |
| SEQ. ID. NO. 15128 | 174-GluAsnThrGluSerLeuArgPro-181 |
| SEQ. ID. NO. 15129 | 189-IleSerGluAspHisLeuAspArgTyrAspAspLeuLeu-201 |
| SEQ. ID. NO. 15130 | 204-AlaHisThrLysAlaLysIlePheArgGlyAspGly-215 |
| SEQ. ID. NO. 15131 | 220-AsnAlaAspAspAlaPheCysArgAlaMetLysArgAlaGlyArgGluValLys-237 |
| SEQ. ID. NO. 15132 | 247-PheTrpLeuGluArgGluThrGlyArgLeuLysGlnGlyAsnGluAspLeuIleAla-265 |
| SEQ. ID. NO. 15133 | 291-GlyLeuProArgGluAlaLeu-297 |
| SEQ. ID. NO. 15134 | 309-HisArgValGluLysIleGlyGluLysAsnGly-319 |
| SEQ. ID. NO. 15135 | 324-AspAspSerLysGlyThrAsn-330 |
| SEQ. ID. NO. 15136 | 353-GlyLysGlyGlnAsp-357 |
| SEQ. ID. NO. 15137 | 359-ThrProLeuArgAspAlaLeuAlaGlyLysAlaLys-370 |
| SEQ. ID. NO. 15138 | 380-ProGlnIleArgArgAspLeuAspGlyCysAsp-390 |
| SEQ. ID. NO. 15139 | 397-AlaThrLeuGluGluAlaValGln-404 |
| SEQ. ID. NO. 15140 | 431-TyrAlaHisArgSer-435 |
| a086 | |
| AMPHI Regions - AMPHI | |
| SEQ. ID. NO. 15141 | 55-MetArgThrTrpArgArgLeuValPro-63 |
| SEQ. ID. NO. 15142 | 83-IleAsnGlyAlaThrArg-88 |
| SEQ. ID. NO. 15143 | 99-ProThrGluLeuPheLysLeuAlaVal-107 |
| SEQ. ID. NO. 15144 | 120-GluValLeuArgSerMetGluSerLeuGlyTrpGlnSerIleTrpArgGlyThrAlaAsn-139 |
| SEQ. ID. NO. 15145 | 155-GluMetTyrGlyArgPhe-160 |
| SEQ. ID. NO. 15146 | 185-SerPheValValIle-189 |
| SEQ. ID. NO. 15147 | 228-ArgValGlnArgValValAlaPheLeuAspProTrpLysAspProGln-243 |
| SEQ. ID. NO. 15148 | 293-GlyPhePheGlyMetCys-298 |
| SEQ. ID. NO. 15149 | 336-TrpIleGlyIleGlnSerPhe-342 |
| Antigenic Index - Jameson-Wolf | |
| SEQ. ID. NO. 15150 | 20-LeuAlaSerLysGluGlyGlyAsp-27 |
| SEQ. ID. NO. 15151 | 55-MetArgThrTrpArgArg-60 |
| SEQ. ID. NO. 15152 | 79-AlaGlyArgGluIleAsnGlyAlaThr-87 |
| SEQ. ID. NO. 15153 | 115-PheThrArgArgGluGluValLeuArgSerMetGlu-126 |
| SEQ. ID. NO. 15154 | 134-TrpArgGlyThrAla-138 |
| SEQ. ID. NO. 15155 | 144-AlaThrAsnProGlnAlaArgArgGluThrLeuGluMet-156 |
| SEQ. ID. NO. 15156 | 225-AlaProTyrArgVal-229 |
| SEQ. ID. NO. 15157 | 236-LeuAspProTrpLysAspProGlnGlyAla-245 |
| SEQ. ID. NO. 15158 | 265-GlyLeuGlyAlaSerLeuSerLysArgGlyPheLeu-276 |
| SEQ. ID. NO. 15159 | 313-SerIleGlyLysGlnSerArgAspLeuGly-322 |
| SEQ. ID. NO. 15160 | 352-LeuProThrLysGlyLeu-357 |
| SEQ. ID. NO. 15161 | 382-IleAspTyrGluAsnArgArgLysMetArgGlyTyrArgValGlu-396 |
| Hydrophilic Regions - Hopp-Woods | |
| SEQ. ID. NO. 15162 | 21-AlaSerLysGluGlyGlyAsp-27 |
| SEQ. ID. NO. 15163 | 79-AlaGlyArgGluIleAsnGly-85 |
| SEQ. ID. NO. 15164 | 115-PheThrArgArgGluGluValLeuArgSerMetGlu-126 |
| SEQ. ID. NO. 15165 | 147-ProGlnAlaArgArgGluThrLeuGluMet-156 |
| SEQ. ID. NO. 15166 | 238-ProTrpLysAspProGlnGly-244 |

TABLE 1-continued

| | |
|---|---|
| SEQ. ID. NO. 15167 | 270-LeuSerLysArgGlyPheLeu-276 |
| SEQ. ID. NO. 15168 | 316-LysGlnSerArgAspLeu-321 |
| SEQ. ID. NO. 15169 | 382-IleAspTyrGluAsnArgArgLysMetArgGlyTyrArgValGlu-396 |
| a087 | |
| AMPHI Regions - AMPHI | |
| SEQ. ID. NO. 15170 | 23-ValAlaAspSerLeuArg-28 |
| SEQ. ID. NO. 15171 | 80-GlnThrValArgGluAlaGlnGlnIle-88 |
| SEQ. ID. NO. 15172 | 99-GlyPheGlyGlyPheValThrPheProGlyGlyLeuAlaAlaLysLeuLeu-115 |
| SEQ. ID. NO. 15173 | 129-GlyLeuSerAsnArgHisLeuSerArgTrpAlaLysArgValLeuTyrAlaPheProLys-148 |
| SEQ. ID. NO. 15174 | 157-ValGlyAsnProValArg-162 |
| SEQ. ID. NO. 15175 | 192-GlyAlaAspValLeuAsnLysThrVal-200 |
| SEQ. ID. NO. 15176 | 239-GluCysValGluPheIleThrAspMetValSerAlaTyr-251 |
| SEQ. ID. NO. 15177 | 313-GluLysLeuAlaGluIleLeuGly-320 |
| SEQ. ID. NO. 15178 | 330-TrpAlaGluAsnAla-334 |
| Antigenic Index - Jameson-Wolf | |
| SEQ. ID. NO. 15179 | 25-AspSerLeuArgAlaArgGly-31 |
| SEQ. ID. NO. 15180 | 37-LeuGlySerLysAspSerMetGluGluArgIleValPro-49 |
| SEQ. ID. NO. 15181 | 61-LysGlyValArgGlyAsnGlyIleLysArgLysLeu-72 |
| SEQ. ID. NO. 15182 | 81-ThrValArgGluAlaGlnGlnIleIleArgLysHisArgVal-94 |
| SEQ. ID. NO. 15183 | 130-LeuSerAsnArgHisLeuSerArgTrpAlaLys-140 |
| SEQ. ID. NO. 15184 | 150-PheSerHisGluGlyGlyLeu-156 |
| SEQ. ID. NO. 15185 | 159-AsnProValArgAlaAspIleSer-166 |
| SEQ. ID. NO. 15186 | 171-ProAlaGluArgPheGlnGlyArgGluGlyArgLeu-182 |
| SEQ. ID. NO. 15187 | 195-ValLeuAsnLysThrVal-200 |
| SEQ. ID. NO. 15188 | 207-LeuProAspAsnAlaArgProGlnMetTyrHisGlnSerGlyArgGlyLysLeuGly-225 |
| SEQ. ID. NO. 15189 | 229-AlaAspTyrAspAla-233 |
| SEQ. ID. NO. 15190 | 249-SerAlaTyrArgAspAlaAsp-255 |
| SEQ. ID. NO. 15191 | 284-AlaValAspAspHisGlnThrAla-291 |
| SEQ. ID. NO. 15192 | 309-GlnLeuThrAlaGluLysLeuAlaGlu-317 |
| SEQ. ID. NO. 15193 | 321-GlyLeuAsnArgGluLysCysLeuLys-329 |
| SEQ. ID. NO. 15194 | 331-AlaGluAsnAlaArgThr-336 |
| SEQ. ID. NO. 15195 | 341-HisSerAlaAspAspValAlaGlu-348 |
| Hydrophilic Regions - Hopp-Woods | |
| SEQ. ID. NO. 15196 | 25-AspSerLeuArgAlaArgGly-31 |
| SEQ. ID. NO. 15197 | 39-SerLysAspSerMetGluGluArgIleValPro-49 |
| SEQ. ID. NO. 15198 | 66-AsnGlyIleLysArgLysLeu-72 |
| SEQ. ID. NO. 15199 | 81-ThrValArgGluAlaGlnGlnIleIleArgLysHisArgVal-94 |
| SEQ. ID. NO. 15200 | 134-HisLeuSerArgTrpAlaLys-140 |
| SEQ. ID. NO. 15201 | 161-ValArgAlaAspIle-165 |
| SEQ. ID. NO. 15202 | 171-ProAlaGluArgPheGlnGlyArgGluGlyArgLeu-182 |
| SEQ. ID. NO. 15203 | 219-SerGlyArgGlyLysLeu-224 |
| SEQ. ID. NO. 15204 | 249-SerAlaTyrArgAspAlaAsp-255 |
| SEQ. ID. NO. 15205 | 284-AlaValAspAspHisGlnThrAla-291 |
| SEQ. ID. NO. 15206 | 310-LeuThrAlaGluLysLeuAlaGlu-317 |
| SEQ. ID. NO. 15207 | 322-LeuAsnArgGluLysCysLeuLys-329 |
| SEQ. ID. NO. 15208 | 331-AlaGluAsnAlaArg-335 |
| SEQ. ID. NO. 15209 | 341-HisSerAlaAspAspValAlaGlu-348 |
| a088-2 | |
| AMPHI Regions - AMPHI | |
| SEQ. ID. NO. 15210 | 7-HisPheSerAsnTrpLeuThrGlyLeuAsnIlePheGlnTyrThrThr-22 |
| SEQ. ID. NO. 15211 | 24-ArgAlaValMetAlaAlaLeu-30 |
| SEQ. ID. NO. 15212 | 43-ThrIleArgArgLeuThrAlaLeuLysCysGlyGln-54 |
| SEQ. ID. NO. 15213 | 88-LeuTrpGlyAsnTrpAlaAsn-94 |
| SEQ. ID. NO. 15214 | 111-GlyPheTyrAspAspTrpArgLysValValTyr-121 |
| SEQ. ID. NO. 15215 | 140-AlaIleIleAlaGlyLeuAlaLeu-147 |
| SEQ. ID. NO. 15216 | 175-GlyPheLeuValLeuSerTyrLeuThrIle-184 |
| SEQ. ID. NO. 15217 | 187-ThrSerAsnAlaValAsnLeuThrAspGlyLeuAspGlyLeuAlaThr-202 |
| SEQ. ID. NO. 15218 | 221-HisSerGlnPheAlaGlnTyrLeuGlnLeuProTyr-232 |
| SEQ. ID. NO. 15219 | 245-AlaMetCysGlyAlaCysLeuGlyPhe-253 |
| Antigenic Index - Jameson-Wolf | |
| SEQ. ID. NO. 15220 | 48-ThrAlaLeuLysCysGlyGlnAlaValArgThrAspGlyProGln-62 |
| SEQ. ID. NO. 15221 | 66-ValLysAsnGlyThrProThrMet-73 |
| SEQ. ID. NO. 15222 | 114-AspAspTrpArgLysValValTyrLysAspProAsnGlyValSerAlaLysPhe-131 |
| SEQ. ID. NO. 15223 | 193-LeuThrAspGlyLeuAsp-198 |
| SEQ. ID. NO. 15224 | 312-LysLysThrLysLysArgIle-318 |
| SEQ. ID. NO. 15225 | 328-TyrGluGlnLysGlyTrpLysGluThrGlnVal-338 |
| Hydrophilic Regions - Hopp-Woods | |
| SEQ. ID. NO. 15226 | 56-ValArgThrAspGlyProGln-62 |
| SEQ. ID. NO. 15227 | 114-AspAspTrpArgLysValValTyrLysAspProAsnGlyVal-127 |
| SEQ. ID. NO. 15228 | 312-LysLysThrLysLysArgIle-318 |
| SEQ. ID. NO. 15229 | 331-LysGlyTrpLysGlu-335 |
| a089 | |
| AMPHI Regions - AMPHI | |
| SEQ. ID. NO. 15230 | 44-CysGlyArgProXxxLysVal-50 |
| SEQ. ID. NO. 15231 | 73-ThrLeuValAlaLeuCysLysProCysSerGlyIle-84 |
| SEQ. ID. NO. 15232 | 118-SerArgProAlaArgPhe-123 |
| Antigenic Index - Jameson-Wolf | |
| SEQ. ID. NO. 15233 | 1-MetProProLysIleThrLysSerGlyPhe-10 |
| SEQ. ID. NO. 15234 | 40-PheSerThrArgCysGlyArgProXxxLys-49 |
| SEQ. ID. NO. 15235 | 54-SerSerAsnAlaSerArgGlyLysProThrAlaSerHisLysAla-68 |

TABLE 1-continued

| | |
|---|---|
| SEQ. ID. NO. 15236 | 80-ProCysSerGlyIle-84 |
| SEQ. ID. NO. 15237 | 95-CysPheArgArgProValSerArgSerAsnGlnLysSerAlaSerTyrSerAsnGluAsnHisPheThrSerArgProAlaArgPheIleAlaArgGlnAsn AlaSerSerAlaPheLysThrCysThrProSerProArgLysIleLeu-144 |
| Hydrophilic Regions - Hopp-Woods | |
| SEQ. ID. NO. 15238 | 43-ArgCysGlyArgProXxxLys-49 |
| SEQ. ID. NO. 15239 | 56-AsnAlaSerArgGlyLysProThrAlaSerHisLysAla-68 |
| SEQ. ID. NO. 15240 | 95-CysPheArgArgProValSerArgSerAsnGlnLysSerAlaSerTyrSerAsn-112 |
| SEQ. ID. NO. 15241 | 119-ArgProAlaArgPheIleAla-125 |
| SEQ. ID. NO. 15242 | 137-ThrProSerProArgLysIle-143 |
| a090-1 | |
| AMPHI Regions - AMPHI | |
| SEQ. ID. NO. 15243 | 10-SerGlnSerLeuLysArgProAspLysHisPheArg-21 |
| SEQ. ID. NO. 15244 | 142-AspPhePheHisAlaValArgGlnAlaLeuLysGlyPheAspValPheGluGlnCysPheAla-162 |
| SEQ. ID. NO. 15245 | 164-GlnThrAspGlyPhe-168 |
| SEQ. ID. NO. 15246 | 177-ValSerGlyValValGlnAlaLeuGlnArg-186 |
| SEQ. ID. NO. 15247 | 226-LeuHisArgThrThrGluArgIleValArgIleGlnAsnLeuHisThrVal-242 |
| SEQ. ID. NO. 15248 | 253-ValValGluGlnVal-257 |
| SEQ. ID. NO. 15249 | 268-ValGlnHisCysArgArgSerArg-275 |
| SEQ. ID. NO. 15250 | 381-GlyAlaGluCysGlnAsnIleGluThrValGlyGluArg-393 |
| SEQ. ID. NO. 15251 | 404-ProValLysHisLeuThrAspLeuArg-412 |
| SEQ. ID. NO. 15252 | 425-AsnLeuArgAlaValPheAlaGlnValGlyAsnHisGlyAsnThrArgAlaAlaLysSer-444 |
| Antigenic Index - Jameson-Wolf | |
| SEQ. ID. NO. 15253 | 9-ValSerGlnSerLeuLysArgProAspLysHisPheArg-21 |
| SEQ. ID. NO. 15254 | 29-HisIleGluThrArgAlaGlyGlyAlaGluGlnHisAspIleAla-43 |
| SEQ. ID. NO. 15255 | 56-PheGlnSerGlyAla-60 |
| SEQ. ID. NO. 15256 | 73-AlaAspLeuArgArgIleAspThrAspGlnGluHis-84 |
| SEQ. ID. NO. 15257 | 89-AlaGlyLysArgValAlaGlnGlyArgGluVal-99 |
| SEQ. ID. NO. 15258 | 107-XxxAsnHisGluGluArgIleLeuGlnThrGlyAsnArgGlyGlyGlyArgThrAspValArg-127 |
| SEQ. ID. NO. 15259 | 149-GlnAlaLeuLysGlyPheAsp-155 |
| SEQ. ID. NO. 15260 | 161-PheAlaArgGlnThrAspGlyPheAlaGlnGlyAsnGlySerHisHisValSer-178 |
| SEQ. ID. NO. 15261 | 187-AsnIleLeuArgGlyAsnGln-193 |
| SEQ. ID. NO. 15262 | 215-GlnArgLysProPheHisLeuAla-222 |
| SEQ. ID. NO. 15263 | 228-ArgThrThrGluArgIleValArg-235 |
| SEQ. ID. NO. 15264 | 269-GlnHisCysArgArgSerArgAlaGln-277 |
| SEQ. ID. NO. 15265 | 285-GluThrGlyLysLeuGlnHis-291 |
| SEQ. ID. NO. 15266 | 305-LeuGlnAsnArgArgAlaAspIleAlaArgAspAsnGlyIle-318 |
| SEQ. ID. NO. 15267 | 320-ProThrLeuAspAlaGluIleAlaAspGlnAlaArgTyrArgGly-334 |
| SEQ. ID. NO. 15268 | 339-AlaGlyAsnArgAsnHis-344 |
| SEQ. ID. NO. 15269 | 353-ValArgGlnGlnPhe-357 |
| SEQ. ID. NO. 15270 | 369-LysGlyLeuAspIle-373 |
| SEQ. ID. NO. 15271 | 380-AlaGlyAlaGluCysGlnAsn-386 |
| SEQ. ID. NO. 15272 | 398-AlaArgValLysHisGlnProVal-405 |
| SEQ. ID. NO. 15273 | 407-HisLeuThrAspLeuArgHis-413 |
| SEQ. ID. NO. 15274 | 421-IleIleArgSerAsnLeuArg-427 |
| SEQ. ID. NO. 15275 | 434-GlyAsnHisGlyAsnThrArgAlaAlaLysSerGlyAspGluAspPhePhe-450 |
| Hydrophilic Regions - Hopp-Woods | |
| SEQ. ID. NO. 15276 | 11-GlnSerLeuLysArgProAspLysHisPheArg-21 |
| SEQ. ID. NO. 15277 | 29-HisIleGluThrArgAlaGlyGlyAlaGluGlnHisAspIleAla-43 |
| SEQ. ID. NO. 15278 | 73-AlaAspLeuArgArgIleAspThrAspGlnGluHis-84 |
| SEQ. ID. NO. 15279 | 89-AlaGlyLysArgValAlaGlnGlyArgGluVal-99 |
| SEQ. ID. NO. 15280 | 107-XxxAsnHisGluGluArgIleLeu-114 |
| SEQ. ID. NO. 15281 | 117-GlyAsnArgGlyGlyGlyArgThrAspValArg-127 |
| SEQ. ID. NO. 15282 | 228-ArgThrThrGluArgIleValArg-235 |
| SEQ. ID. NO. 15283 | 269-GlnHisCysArgArgSerArgAla-276 |
| SEQ. ID. NO. 15284 | 285-GluThrGlyLysLeuGln-290 |
| SEQ. ID. NO. 15285 | 305-LeuGlnAsnArgArgAlaAspIleAlaArgAspAsnGlyIle-318 |
| SEQ. ID. NO. 15286 | 322-LeuAspAlaGluIleAlaAspGlnAlaArgTyrArg-333 |
| SEQ. ID. NO. 15287 | 369-LysGlyLeuAspIle-373 |
| SEQ. ID. NO. 15288 | 380-AlaGlyAlaGluCysGlnAsn-386 |
| SEQ. ID. NO. 15289 | 398-AlaArgValLysHisGlnPro-404 |
| SEQ. ID. NO. 15290 | 409-ThrAspLeuArgHis-413 |
| SEQ. ID. NO. 15291 | 421-IleIleArgSerAsnLeu-426 |
| SEQ. ID. NO. 15292 | 437-GlyAsnThrArgAlaAlaLysSerGlyAspGluAspPhePhe-450 |
| a091 | |
| AMPHI Regions - AMPHI | |
| SEQ. ID. NO. 15293 | 39-ProLeuSerAspGlyIleAlaSerCys-47 |
| SEQ. ID. NO. 15294 | 49-IleThrArgPheGlnAlaLeuVal-56 |
| SEQ. ID. NO. 15295 | 61-ValLeuValSerValLeuThrSerLeuAlaLys-71 |
| Antigenic Index - Jameson-Wolf | |
| SEQ. ID. NO. 15296 | 5-ValProProSerProAlaThr-11 |
| SEQ. ID. NO. 15297 | 38-LysProLeuSerAspGlyIleAla-45 |
| a092 | |
| AMPHI Regions - AMPHI | |
| SEQ. ID. NO. 15298 | 55-GlyMetSerGlyIleAlaGluValLeuHis-64 |
| SEQ. ID. NO. 15299 | 76-AlaArgAsnAlaAlaThrGluHisLeu-84 |
| SEQ. ID. NO. 15300 | 95-HisThrAlaGluHisValAsnGly-102 |
| SEQ. ID. NO. 15301 | 120-ValAlaAlaLeuGlu-124 |
| SEQ. ID. NO. 15302 | 137-AlaGluLeuMetArgPheArgAsp-144 |
| SEQ. ID. NO. 15303 | 209-LeuThrProIleMetSerValValThrAsnIleAsp-220 |
| SEQ. ID. NO. 15304 | 226-ThrTyrGlyHisSerValGluLysLeuHisGlnAlaPheIleAspPheIleHisArg-244 |

TABLE 1-continued

| | |
|---|---|
| SEQ. ID. NO. 15305 | 259-HisValArgAlaIleLeuProLysValSerLysProTyr-271 |
| SEQ. ID. NO. 15306 | 273-ThrTyrGlyLeuAspAspThrAla-280 |
| SEQ. ID. NO. 15307 | 321-AsnValLeuAsnAlaLeuAlaAlaIle-329 |
| SEQ. ID. NO. 15308 | 339-ValGluAlaIleGlnLysGly-345 |
| SEQ. ID. NO. 15309 | 353-GlyArgArgPheGlnLysTyrGlyAspIleLys-363 |
| SEQ. ID. NO. 15310 | 407-ArgTyrThrArgThrArgAspLeuPheGluAspPheThrLysValLeuAsnThrValAspAlaLeu-428 |
| SEQ. ID. NO. 15311 | 449-LeuAlaArgAlaIleArgValLeuGlyLysLeu-459 |
| SEQ. ID. NO. 15312 | 464-CysGluAsnValAlaAspLeuProGluMetLeuLeuAsn-476 |
| Antigenic Index - Jameson-Wolf | |
| SEQ. ID. NO. 15313 | 14-LeuTrpArgAlaAsnGlyGlnProPheLys-23 |
| SEQ. ID. NO. 15314 | 25-ThrProLeuArgIleGluAsnProProGluArgAsnIleMetMetLysAsnArgVal-43 |
| SEQ. ID. NO. 15315 | 70-ValSerGlySerAspGlnAlaArgAsnAlaAla-80 |
| SEQ. ID. NO. 15316 | 111-AlaValLysLysGluAsnProGluVal-119 |
| SEQ. ID. NO. 15317 | 140-MetArgPheArgAspGlyIle-146 |
| SEQ. ID. NO. 15318 | 150-GlyThrHisGlyLysThrThrThr-157 |
| SEQ. ID. NO. 15319 | 184-GlyThrAsnAlaArgLeuGlyLysGlyGluTyr-194 |
| SEQ. ID. NO. 15320 | 198-GluAlaAspGluSerAspAla-204 |
| SEQ. ID. NO. 15321 | 218-AsnIleAspGluAspHisMetAspThrTyrGly-228 |
| SEQ. ID. NO. 15322 | 230-SerValGluLysLeuHis-235 |
| SEQ. ID. NO. 15323 | 255-IleAspSerGluHisVal-260 |
| SEQ. ID. NO. 15324 | 263-IleLeuProLysValSerLysProTyrAla-272 |
| SEQ. ID. NO. 15325 | 275-GlyLeuAspAspThrAlaAsp-281 |
| SEQ. ID. NO. 15326 | 286-AspIleGluAsnValGlyAla-292 |
| SEQ. ID. NO. 15327 | 302-MetLysGlyHisGluGlnGlySerPhe-310 |
| SEQ. ID. NO. 15328 | 351-GlyValGlyArgArgPheGlnLysTyrGlyAspIleLysLeuProAsnGlyGly-368 |
| SEQ. ID. NO. 15329 | 374-AspAspTyrGlyHisHisPro-380 |
| SEQ. ID. NO. 15330 | 393-AlaTyrProGluLysArgLeu-399 |
| SEQ. ID. NO. 15331 | 404-GlnProHisArgTyrThrArgThrArgAspLeuPheGluAspPheThrLys-420 |
| SEQ. ID. NO. 15332 | 435-AlaAlaGlyGluGluProIleAlaAlaAlaAspSerArgAlaLeuAlaArg-451 |
| SEQ. ID. NO. 15333 | 466-AsnValAlaAspLeuPro-471 |
| SEQ. ID. NO. 15334 | 478-LeuGlnAspGlyAspIle-483 |
| SEQ. ID. NO. 15335 | 488-GlyAlaGlySerIleAsn-493 |
| Hydrophilic Regions - Hopp-Woods | |
| SEQ. ID. NO. 15336 | 26-ProLeuArgIleGluAsnProProGluArgAsnIleMetMetLysAsnArgVal-43 |
| SEQ. ID. NO. 15337 | 71-SerGlySerAspGlnAlaArgAsnAlaAla-80 |
| SEQ. ID. NO. 15338 | 111-AlaValLysLysGluAsnProGlu-118 |
| SEQ. ID. NO. 15339 | 140-MetArgPheArgAsp-144 |
| SEQ. ID. NO. 15340 | 152-HisGlyLysThrThr-156 |
| SEQ. ID. NO. 15341 | 187-AlaArgLeuGlyLysGlyGlu-193 |
| SEQ. ID. NO. 15342 | 198-GluAlaAspGluSerAspAla-204 |
| SEQ. ID. NO. 15343 | 218-AsnIleAspGluAspHisMetAsp-225 |
| SEQ. ID. NO. 15344 | 230-SerValGluLysLeuHis-235 |
| SEQ. ID. NO. 15345 | 256-AspSerGluHisVal-260 |
| SEQ. ID. NO. 15346 | 275-GlyLeuAspAspThrAlaAsp-281 |
| SEQ. ID. NO. 15347 | 303-LysGlyHisGluGlnGlySer-309 |
| SEQ. ID. NO. 15348 | 351-GlyValGlyArgArgPheGlnLys-358 |
| SEQ. ID. NO. 15349 | 360-GlyAspIleLysLeu-364 |
| SEQ. ID. NO. 15350 | 393-AlaTyrProGluLysArgLeu-399 |
| SEQ. ID. NO. 15351 | 407-ArgTyrThrArgThrArgAspLeuPheGluAspPheThrLys-420 |
| SEQ. ID. NO. 15352 | 435-AlaAlaGlyGluGluProIleAlaAlaAlaAspSerArgAlaLeuAlaArg-451 |
| SEQ. ID. NO. 15353 | 466-AsnValAlaAspLeuPro-471 |
| SEQ. ID. NO. 15354 | 479-GlnAspGlyAspIle-483 |
| a093-2 | |
| AMPHI Regions - AMPHI | |
| SEQ. ID. NO. 15355 | 26-ThrAlaIleLeuAsn-30 |
| SEQ. ID. NO. 15356 | 59-ThrAlaPheAsnIleLeuHisGly-66 |
| SEQ. ID. NO. 15357 | 159-LysSerValTyrGluGluLeuLysHisPhe-168 |
| SEQ. ID. NO. 15358 | 196-IleHisIleIleProAlaThrGluPhe-204 |
| SEQ. ID. NO. 15359 | 254-PheLeuLysAspThr-258 |
| SEQ. ID. NO. 15360 | 267-IleAsnThrLeuProGlyMetThrGly-275 |
| Antigenic Index - Jameson-Wolf | |
| SEQ. ID. NO. 15361 | 12-GlyGlyPheSerSerGluArgGluIleSerLeuAspSerGlyThr-26 |
| SEQ. ID. NO. 15362 | 32-LeuLysSerLysGlyIleAsp-38 |
| SEQ. ID. NO. 15363 | 41-AlaPheAspProLysGluThrProLeuSerGluLeuLysAlaGlnGly-56 |
| SEQ. ID. NO. 15364 | 66-GlyThrTyrGlyGluAspGlyAlaVal-74 |
| SEQ. ID. NO. 15365 | 96-GlyMetAspLysTyrArgCys-102 |
| SEQ. ID. NO. 15366 | 120-HisAspAspThrAspPheAspAlaValGluGluLysLeuGly-133 |
| SEQ. ID. NO. 15367 | 140-ProAlaAlaGluGlySerSer-146 |
| SEQ. ID. NO. 15368 | 151-LysValLysGlyLysGlyArgLeuLysSerValTyrGluGluLeuLysHisPheGln-169 |
| SEQ. ID. NO. 15369 | 176-ArgPheIleGlyGlyGlyGluTyrSer-184 |
| SEQ. ID. NO. 15370 | 189-AsnGlyLysGlyLeuPro-194 |
| SEQ. ID. NO. 15371 | 203-GluPheTyrAspTyrGluAlaLysTyrAsnArgAsnAspThr-216 |
| SEQ. ID. NO. 15372 | 218-TyrGlnCysProSerGluAspLeuThrGluAlaGluGluSerLeuMetArg-234 |
| SEQ. ID. NO. 15373 | 245-GlyAlaGluGlyCysVal-250 |
| SEQ. ID. NO. 15374 | 253-AspPheLeuLysAspThrAspGly-260 |
| SEQ. ID. NO. 15375 | 269-ThrLeuProGlyMetThr-274 |
| Hydrophilic Regions - Hopp-Woods | |
| SEQ. ID. NO. 15376 | 15-SerSerGluArgGluIleSerLeu-22 |
| SEQ. ID. NO. 15377 | 32-LeuLysSerLysGlyIleAsp-38 |
| SEQ. ID. NO. 15378 | 41-AlaPheAspProLysGluThrProLeuSerGluLeuLysAla-54 |

TABLE 1-continued

| | |
|---|---|
| SEQ. ID. NO. 15379 | 68-TyrGlyGluAspGlyAlaVal-74 |
| SEQ. ID. NO. 15380 | 96-GlyMetAspLysTyrArgCys-102 |
| SEQ. ID. NO. 15381 | 120-HisAspAspThrAspPheAspAlaValGluGluLysLeuGly-133 |
| SEQ. ID. NO. 15382 | 140-ProAlaAlaGluGlySerSer-146 |
| SEQ. ID. NO. 15383 | 151-LysValLysGlyLysGlyArgLeuLysSerValTyrGluGluLeuLysHisPheGln-169 |
| SEQ. ID. NO. 15384 | 205-TyrAspTyrGluAlaLysTyrAsnArgAsnAspThr-216 |
| SEQ. ID. NO. 15385 | 221-ProSerGluAspLeuThrGluAlaGluGluSerLeuMetArg-234 |
| SEQ. ID. NO. 15386 | 253-AspPheLeuLysAspThrAspGly-260 |
| a094 | |
| AMPHI Regions - AMPHI | |
| SEQ. ID. NO. 15387 | 17-LeuProProIleThrLysValGlySer-25 |
| SEQ. ID. NO. 15388 | 80-PheSerPheLeuThrAlaVal-86 |
| Antigenic Index - Jameson-Wolf | |
| SEQ. ID. NO. 15389 | 3-SerProLeuProLysArgAlaLeu-10 |
| SEQ. ID. NO. 15390 | 24-GlySerSerProAlaAlaProArgMetGluAla-34 |
| SEQ. ID. NO. 15391 | 50-MetProSerArgLysArgIleAsnSerAlaAsnIleArgAlaArgGlyIleThr-67 |
| Hydrophilic Regions - Hopp-Woods | |
| SEQ. ID. NO. 15392 | 5-LeuProLysArgAlaLeu-10 |
| SEQ. ID. NO. 15393 | 28-AlaAlaProArgMetGluAla-34 |
| SEQ. ID. NO. 15394 | 51-ProSerArgLysArgIleAsn-57 |
| SEQ. ID. NO. 15395 | 60-AsnIleArgAlaArgGly-65 |
| a095-2 | |
| AMPHI Regions - AMPHI | |
| SEQ. ID. NO. 15396 | 9-CysAlaSerAsnLeuPheArgGlnPheGlnGlnArgGlyGlyAspAlaValAsp-26 |
| SEQ. ID. NO. 15397 | 38-ValLeuGlnAsnValGlnGlnHisPheGlyGlnIleGlyAsnValPheAlaVal-55 |
| SEQ. ID. NO. 15398 | 86-PheGlyGlnHisGlnArgValAsnGlyIleGluAspPheGlyLysValPheLysGlnIleAlaArg-107 |
| SEQ. ID. NO. 15399 | 132-GlyArgArgHisPheAspGlyValValSer-141 |
| SEQ. ID. NO. 15400 | 174-PheLeuAspArgPheAsnArgCysAlaAspPheGlnArgHisAlaAspGlyCysGlnCysValGlnHisVal-197 |
| SEQ. ID. NO. 15401 | 204-GlnHisAspPheLys-208 |
| SEQ. ID. NO. 15402 | 236-AspValGlyGlyIleValGlnThrValSerSerIle-247 |
| SEQ. ID. NO. 15403 | 274-ThrValAspGluIleAspLysArgLeuMetGlnLeuLeuAsnThrVal-289 |
| SEQ. ID. NO. 15404 | 313-GlyCysIleArgLeuValGly-319 |
| SEQ. ID. NO. 15405 | 370-AsnGlyAspAlaValThrGluAlaHisGlnLeuArgGlnHisGlnGlyAla-386 |
| SEQ. ID. NO. 15406 | 417-ValAsnValPheCysGly-422 |
| SEQ. ID. NO. 15407 | 435-MetLeuGlySerGlyIleSerArgLeuIleArgThrGly-447 |
| SEQ. ID. NO. 15408 | 451-ThrGlnIleValGlnAspPheGlyAspThrAlaHisAla-463 |
| Antigenic Index - Jameson-Wolf | |
| SEQ. ID. NO. 15409 | 6-SerGlyGlyCysAlaSerAsnLeu-13 |
| SEQ. ID. NO. 15410 | 17-PheGlnGlnArgGlyGlyAspAlaValAspAlaSerArgThrHisIle-32 |
| SEQ. ID. NO. 15411 | 62-GlnHisAlaAspGlyAlaGlyLysSerAlaGlyIleSerGlyGlyAsnArgLeuPhe-80 |
| SEQ. ID. NO. 15412 | 88-GlnHisGlnArgValAsnGlyIleGluAspPheGlyLys-100 |
| SEQ. ID. NO. 15413 | 112ValArgLeuGluGlyGluTyr-118 |
| SEQ. ID. NO. 15414 | 126-AlaAlaCysGlyGlyLysGlyArgArgHisPheAspGly-138 |
| SEQ. ID. NO. 15415 | 144-ValHisGlnGluArgGlySerThr-151 |
| SEQ. ID. NO. 15416 | 163-AlaAlaAlaAspThrPheLysAlaGluGlnAlaPhe-174 |
| SEQ. ID. NO. 15417 | 176-AspArgPheAsnArgCysAlaAspPheGlnArgHisAlaAspGlyCysGln-192 |
| SEQ. ID. NO. 15418 | 205-HisAspPheLysArg-209 |
| SEQ. ID. NO. 15419 | 253-GlyGlnAsnArgAlaAspVal-259 |
| SEQ. ID. NO. 15420 | 263-AsnThrGlnLysGlyPheAlaVal-270 |
| SEQ. ID. NO. 15421 | 273-HisThrValAspGluIleAspLysArgLeu-282 |
| SEQ. ID. NO. 15422 | 300-IleGlyAsnAspGlyHisAsnArgCysGlnValGlnLysGlyCys-314 |
| SEQ. ID. NO. 15423 | 339-PheAlaAlaAspAsnGluSerArgValLysSerCysArgAlaGluAspGlyGlyGlyGlnAlaGlyGlyArgGlyPheAlaValArgAlaGlyAsn GlyAspAlaValThr-375 |
| SEQ. ID. NO. 15424 | 378-HisGlnLeuArgGlnHisGlnGlyAlaArgAsnAsnGlyAsn-391 |
| SEQ. ID. NO. 15425 | 394-LeuGlnArgSerAspAsnPheGly-401 |
| SEQ. ID. NO. 15426 | 405-PheAspGlyGlyArgGlyAsnAspAspIleArgThr-416 |
| SEQ. ID. NO. 15427 | 442-ArgLeuIleArgThrGlyAsnPheLysThr-451 |
| SEQ. ID. NO. 15428 | 455-GlnAspPheGlyAspThrAlaHisAlaAspAlaAlaAspThrAspLysMetAspVal-473 |
| Hydrophilic Regions - Hopp-Woods | |
| SEQ. ID. NO. 15429 | 17-PheGlnGlnArgGlyGlyAspAlaValAspAlaSerArgThrHisIle-32 |
| SEQ. ID. NO. 15430 | 64-AlaAspGlyAlaGlyLysSerAlaGly-72 |
| SEQ. ID. NO. 15431 | 93-AsnGlyIleGluAspPheGlyLys-100 |
| SEQ. ID. NO. 15432 | 112-ValArgLeuGluGlyGluTyr-118 |
| SEQ. ID. NO. 15433 | 128-CysGlyGlyLysGlyArgArgHisPhe-136 |
| SEQ. ID. NO. 15434 | 145-HisGlnGluArgGlySer-150 |
| SEQ. ID. NO. 15435 | 163-AlaAlaAlaAspThrPheLysAlaGluGlnAlaPhe-174 |
| SEQ. ID. NO. 15436 | 182-AlaAspPheGlnArgHisAlaAspGly-190 |
| SEQ. ID. NO. 15437 | 205-HisAspPheLysArg-209 |
| SEQ. ID. NO. 15438 | 273-HisThrValAspGluIleAspLysArgLeu-282 |
| SEQ. ID. NO. 15439 | 300-IleGlyAsnAspGlyHisAsnArgCysGlnVal-310 |
| SEQ. ID. NO. 15440 | 339-PheAlaAlaAspAsnGluSerArgValLysSerCysArgAlaGluAspGlyGlyGly-357 |
| SEQ. ID. NO. 15441 | 368-AlaGlyAsnGlyAspAlaValThr-375 |
| SEQ. ID. NO. 15442 | 378-HisGlnLeuArgGlnHisGlnGlyAlaArgAsnAsnGly-390 |
| SEQ. ID. NO. 15443 | 395-GlnArgSerAspAsn-399 |
| SEQ. ID. NO. 15444 | 407-GlyGlyArgGlyAsnAspAspIleArgThr-416 |
| SEQ. ID. NO. 15445 | 461-AlaHisAlaAspAlaAlaAspThrAspLysMetAspVal-473 |
| a096-2 | |
| AMPHI Regions - AMPHI | |
| SEQ. ID. NO. 15446 | 19-GlyIlePheGluGluIleAspAlaHis-27 |
| SEQ. ID. NO. 15447 | 37-AlaAlaAsnArgGln-41 |

TABLE 1-continued

| | |
|---|---|
| SEQ. ID. NO. 15448 | 61-GlyValValAlaVal-65 |
| SEQ. ID. NO. 15449 | 112-GlnPhePheValAsnAlaPheGln-119 |
| SEQ. ID. NO. 15450 | 129-AlaTyrAlaAlaAlaPheGlyArg-136 |
| SEQ. ID. NO. 15451 | 172-AsnGlnPheAlaAla-176 |
| SEQ. ID. NO. 15452 | 187-AspThrAlaAlaGlyIleGlyAsnAlaGln-196 |
| SEQ. ID. NO. 15453 | 228-GlnTrpGlyPheLeu-232 |
| Antigenic Index - Jameson-Wolf | |
| SEQ. ID. NO. 15454 | 4-HisThrGlyGlnGly-8 |
| SEQ. ID. NO. 15455 | 22-GluGluIleAspAla-26 |
| SEQ. ID. NO. 15456 | 30-PheArgThrAspCysLeuArgAlaAlaAsn-39 |
| SEQ. ID. NO. 15457 | 73-LysLeuGlyArgGlyAspAspValTyrAla-82 |
| SEQ. ID. NO. 15458 | 97-AlaAlaAspLysProPheGlyAsnAspPhe-106 |
| SEQ. ID. NO. 15459 | 137-ArgPheHisLysHisArgGln-143 |
| SEQ. ID. NO. 15460 | 157-ValGlnAspGlyGluLeuGlyAsnGlyGlnSerGlnCysLeu-170 |
| SEQ. ID. NO. 15461 | 181-AlaAspGlyGlyCysGlyAspThr-188 |
| SEQ. ID. NO. 15462 | 211-ThrValLysAspValGluCysArgLeu-219 |
| Hydrophilic Regions - Hopp-Woods | |
| SEQ. ID. NO. 15463 | 22-GluGluIleAspAla-26 |
| SEQ. ID. NO. 15464 | 33-AspCysLeuArgAlaAlaAsn-39 |
| SEQ. ID. NO. 15465 | 74-LeuGlyArgGlyAspAspValTyr-81 |
| SEQ. ID. NO. 15466 | 97-AlaAlaAspLysProPheGly-103 |
| SEQ. ID. NO. 15467 | 137-ArgPheHisLysHisArgGln-143 |
| SEQ. ID. NO. 15468 | 158-GlnAspGlyGluLeuGlyAsn-164 |
| SEQ. ID. NO. 15469 | 183-GlyGlyCysGlyAspThr-188 |
| SEQ. ID. NO. 15470 | 211-ThrValLysAspValGluCysArgLeu-219 |
| a097 | |
| AMPHI Regions - AMPHI | |
| SEQ. ID. NO. 15471 | 28-AlaGlyLeuThrThrPheLeuThrMetCysTyrIleVal-40 |
| SEQ. ID. NO. 15472 | 72-MetGlyPheValGly-76 |
| SEQ. ID. NO. 15473 | 166-AlaThrLeuValGlyLeuGlyAspIleHisGlnProSerAlaLeuLeuAlaLeuPheGly-185 |
| SEQ. ID. NO. 15474 | 207-ThrIleThrValIleAlaSerLeuMetGlyLeuAsnGluPheHisGlyIleIleGlyGluValProSerIle-230 |
| SEQ. ID. NO. 15475 | 242-LeuPheThrValSer-246 |
| SEQ. ID. NO. 15476 | 260-PheAspSerThrGlyThr-265 |
| SEQ. ID. NO. 15477 | 342-LeuAlaLysSerValProAlaPheAlaThr-351 |
| SEQ. ID. NO. 15478 | 362-MetLeuArgSerAlaArgAspIle-369 |
| Antigenic Index - Jameson-Wolf | |
| SEQ. ID. NO. 15479 | 1-MetAspThrSerLysGlnThrLeu-8 |
| SEQ. ID. NO. 15480 | 13-PheLysLeuLysAlaAsnGlyThrThrValArgThrGluLeu-26 |
| SEQ. ID. NO. 15481 | 125-LysValArgGluMetLeu-130 |
| SEQ. ID. NO. 15482 | 260-PheAspSerThrGly-264 |
| SEQ. ID. NO. 15483 | 277-ValAspGlyLysLeuProArgLeuLysArg-286 |
| SEQ. ID. NO. 15484 | 317-SerAlaGlyGlyArgThrGly-323 |
| SEQ. ID. NO. 15485 | 364-ArgSerAlaArgAspIleAspTrpAspAspMetThrGlu-376 |
| SEQ. ID. NO. 15486 | 410-LeuCysArgArgThrLysAspValProPro-419 |
| Hydrophilic Regions - Hopp-Woods | |
| SEQ. ID. NO. 15487 | 1-MetAspThrSerLys-5 |
| SEQ. ID. NO. 15488 | 16-LysAlaAsnGlyThrThrValArgThrGluLeu-26 |
| SEQ. ID. NO. 15489 | 125-LysValArgGluMetLeu-130 |
| SEQ. ID. NO. 15490 | 279-GlyLysLeuProArgLeuLysArg-286 |
| SEQ. ID. NO. 15491 | 318-AlaGlyGlyArgThr-322 |
| SEQ. ID. NO. 15492 | 364-ArgSerAlaArgAspIleAspTrpAspAspMetThrGlu-376 |
| SEQ. ID. NO. 15493 | 410-LeuCysArgArgThrLysAspValPro-418 |
| a098-2 | |
| AMPHI Regions - AMPHI | |
| SEQ. ID. NO. 15494 | 28-AlaAlaGluAlaGlyGluGlnPheValGlyAsp-38 |
| SEQ. ID. NO. 15495 | 110-ValGlyAspPhePheLysLeuAlaPhe-118 |
| SEQ. ID. NO. 15496 | 120-CysGlnIleGlnAsnValValThrAlaIleAlaGlnIleValAla-134 |
| SEQ. ID. NO. 15497 | 163-LeuSerSerPheSerHisGly-169 |
| Antigenic Index - Jameson-Wolf | |
| SEQ. ID. NO. 15498 | 24-ValGlnGluAspAlaAlaGluAlaGlyGlu-33 |
| SEQ. ID. NO. 15499 | 68-MetGlyMetCysArg-72 |
| SEQ. ID. NO. 15500 | 78-PheAsnHisThrAspArgGlnAlaAla-86 |
| SEQ. ID. NO. 15501 | 136-ThrAlaAsnGlyThrGlnSerGlyIleThrGlyArgAsnAlaArgLysArgAsnGlyPhe-155 |
| SEQ. ID. NO. 15502 | 158-PheGluGlyArgGlyLeuSerSerPheSerHisGlyIle-170 |
| SEQ. ID. NO. 15503 | 180-ValPheArgArgProMetArgIleCys-188 |
| Hydrophilic Regions - Hopp-Woods | |
| SEQ. ID. NO. 15504 | 24-ValGlnGluAspAlaAlaGluAlaGlyGlu-33 |
| SEQ. ID. NO. 15505 | 79-AsnHisThrAspArgGlnAla-85 |
| SEQ. ID. NO. 15506 | 144-IleThrGlyArgAsnAlaArgLysArgAsnGly-154 |
| SEQ. ID. NO. 15507 | 158-PheGluGlyArgGly-162 |
| SEQ. ID. NO. 15508 | 180-ValPheArgArgProMetArg-186 |
| a099 | |
| AMPHI Regions - AMPHI | |
| SEQ. ID. NO. 15509 | 6-SerMetMetArgLeuProAspIle-13 |
| SEQ. ID. NO. 15510 | 47-AlaPheValGluPhePheGlyGluGly-55 |
| SEQ. ID. NO. 15511 | 102-LysLeuValGluThrTyrAlaLysThr-110 |
| SEQ. ID. NO. 15512 | 114-TrpAlaAspAlaLeuLysThrAla-121 |
| SEQ. ID. NO. 15513 | 135-ThrArgAsnMetAlaGlyProSerAsn-143 |
| SEQ. ID. NO. 15514 | 154-AlaGlyLysGlyLeuAlaLysProTyrGluGluProSerAspGlyGln-169 |
| SEQ. ID. NO. 15515 | 178-AlaAlaIleThrSerCysThrAsnThrSerAsnProArgAsnVal-192 |

TABLE 1-continued

| | |
|---|---|
| SEQ. ID. NO. 15516 | 251-ThrCysAsnGlyMetSer-256 |
| SEQ. ID. NO. 15517 | 341-IleAspAlaIleValAlaGluTyr-348 |
| SEQ. ID. NO. 15518 | 350-LysProGlnGlnPheArgAspVal-357 |
| SEQ. ID. NO. 15519 | 371-ProSerProLeuTyrAspTrpArg-378 |
| SEQ. ID. NO. 15520 | 381-SerThrTyrIleArg-385 |
| SEQ. ID. NO. 15521 | 400-LeuSerGlyMetArgProLeu-406 |
| SEQ. ID. NO. 15522 | 443-AspPheAsnSerTyrAlaThr-449 |
| SEQ. ID. NO. 15523 | 468-PheAsnGluMetValArg-473 |
| SEQ. ID. NO. 15524 | 494-MetArgMetTrpGluAlaIleGluThrTyrMet-504 |
| SEQ. ID. NO. 15525 | 532-ArgLeuAlaGlyVal-536 |
| SEQ. ID. NO. 15526 | 539-IleValAlaGluGlyPheGluArgIleHisArgThrAsn-551 |
| SEQ. ID. NO. 15527 | 575-GlyThrGluThrTyr-579 |
| Antigenic Index -Jameson-Wolf | |
| SEQ. ID. NO. 15528 | 18-LeuAsnGlyLysArgLysAlaGly-25 |
| SEQ. ID. NO. 15529 | 38-PheLeuArgLysGluArgValVal-45 |
| SEQ. ID. NO. 15530 | 53-GlyGluGlyAlaArgSer-58 |
| SEQ. ID. NO. 15531 | 60-SerIleGlyAspArgAlaThr-66 |
| SEQ. ID. NO. 15532 | 70-MetThrProGluPhe-74 |
| SEQ. ID. NO. 15533 | 83-IleAspGluGlnThr-87 |
| SEQ. ID. NO. 15534 | 94-ThrGlyArgAspAspAlaGlnValLysLeu-103 |
| SEQ. ID. NO. 15535 | 133-SerValThrArgAsnMetAlaGlyProSerAsnProHis-145 |
| SEQ. ID. NO. 15536 | 153-LeuAlaGlyLysGlyLeuAlaLysProTyrGluGluProSerAspGlyGlnMetProAspGlyAla-174 |
| SEQ. ID. NO. 15537 | 183-CysThrAsnThrSerAsnProArgAsnVal-192 |
| SEQ. ID. NO. 15538 | 206-GlyLeuGlnArgLysProTrpValLysSerSerPheAlaProGlySerLysValAla-224 |
| SEQ. ID. NO. 15539 | 227-TyrLeuLysGluAlaAspLeuLeuProGluMetGluLysLeu-240 |
| SEQ. ID. NO. 15540 | 251-ThrCysAsnGlyMetSerGlyAlaLeuAspProLysIleGlnLysGluIleIleAspArgAspLeuTyr-273 |
| SEQ. ID. NO. 15541 | 279-SerGlyAsnArgAsnPheAspGlyArgIleHisProTyrAlaLys-293 |
| SEQ. ID. NO. 15542 | 312-IleArgPheAspIleGluAsnAspVal-320 |
| SEQ. ID. NO. 15543 | 322-GlyValAlaAspGlyLysGluIleArgLeuLysAspIleTrpProThrAspGluGluIleAsp-342 |
| SEQ. ID. NO. 15544 | 348-TyrValLysProGlnGlnPheArgAsp-356 |
| SEQ. ID. NO. 15545 | 363-AspThrGlyThrAlaGlnLysAlaProSerProLeuTyrAspTrpArgProMetSerThrTyrIleArgArgProProTyrTrp-390 |
| SEQ. ID. NO. 15546 | 394-LeuAlaGlyGluArgThrLeuSerGlyMetArg-404 |
| SEQ. ID. NO. 15547 | 409-LeuProAspAsnIleThrThrAspHisLeuSerProSerAsn-422 |
| SEQ. ID. NO. 15548 | 438-GlyLeuProGluGluAspPheAsnSerTyrAlaThrHisArgGlyAspHisLeuThr-456 |
| SEQ. ID. NO. 15549 | 463-AlaAsnProLysLeuPhe-468 |
| SEQ. ID. NO. 15550 | 471-MetValArgAsnGluAspGlySerValArgGlnGlySerLeuAlaArgValGluProGluGlyGlnThr-493 |
| SEQ. ID. NO. 15551 | 503-TyrMetAsnArgLysGlnPro-509 |
| SEQ. ID. NO. 15552 | 516-AlaAspTyrGlyGlnGlySerSerArgAspTrpAlaAlaLysGlyValArg-532 |
| SEQ. ID. NO. 15553 | 543-GlyPheGluArgIleHisArgThrAsnLeu-552 |
| SEQ. ID. NO. 15554 | 562-PheLysProGlyThrAsnArgHisThrLeuGlnLeuAspGlyThrGluThrTyrAspValValGlyGluArgThrProArgCysAspLeu-591 |
| SEQ. ID. NO. 15555 | 595-IleHisArgLysAsnGlyGluThrValGlu-604 |
| SEQ. ID. NO. 15556 | 609-CysArgLeuAspThrAlaGluGlu-616 |
| Hydrophilic Regions - Hopp-Woods | |
| SEQ. ID. NO. 15557 | 18-LeuAsnGlyLysArgLysAlaGly-25 |
| SEQ. ID. NO. 15558 | 38-PheLeuArgLysGluArgValVal-45 |
| SEQ. ID. NO. 15559 | 53-GlyGluGlyAlaArg-57 |
| SEQ. ID. NO. 15560 | 60-SerIleGlyAspArgAlaThr-66 |
| SEQ. ID. NO. 15561 | 83-IleAspGluGlnThr-87 |
| SEQ. ID. NO. 15562 | 94-ThrGlyArgAspAspAlaGlnValLysLeu-103 |
| SEQ. ID. NO. 15563 | 157-GlyLeuAlaLysProTyrGluGluProSerAspGlyGlnMetPro-171 |
| SEQ. ID. NO. 15564 | 227-TyrLeuLysGluAlaAspLeuLeuProGluMetGluLysLeu-240 |
| SEQ. ID. NO. 15565 | 259-LeuAspProLysIleGlnLysGluIleIleAspArgAspLeuTyr-273 |
| SEQ. ID. NO. 15566 | 282-ArgAsnPheAspGlyArgIle-288 |
| SEQ. ID. NO. 15567 | 312-IleArgPheAspIleGluAsnAspVal-320 |
| SEQ. ID. NO. 15568 | 324-AlaAspGlyLysGluIleArgLeuLysAsp-333 |
| SEQ. ID. NO. 15569 | 335-TrpProThrAspGluGluIleAsp-342 |
| SEQ. ID. NO. 15570 | 366-ThrAlaGlnLysAlaPro-371 |
| SEQ. ID. NO. 15571 | 394-LeuAlaGlyGluArgThrLeuSer-401 |
| SEQ. ID. NO. 15572 | 438-GlyLeuProGluGluAspPheAsn-445 |
| SEQ. ID. NO. 15573 | 450-HisArgGlyAspHisLeuThr-456 |
| SEQ. ID. NO. 15574 | 471-MetValArgAsnGluAspGlySerValArgGln-481 |
| SEQ. ID. NO. 15575 | 485-AlaArgValGluProGluGlyGlnThr-493 |
| SEQ. ID. NO. 15576 | 503-TyrMetAsnArgLysGlnPro-509 |
| SEQ. ID. NO. 15577 | 518-TyrGlyGlnGlySerSerArgAspTrpAlaAlaLysGlyValArg-532 |
| SEQ. ID. NO. 15578 | 543-GlyPheGluArgIleHisArg-549 |
| SEQ. ID. NO. 15579 | 564-ProGlyThrAsnArgHis-569 |
| SEQ. ID. NO. 15580 | 574-AspGlyThrGluThr-578 |
| SEQ. ID. NO. 15581 | 580-AspValValGlyGluArgThrProArgCysAsp-590 |
| SEQ. ID. NO. 15582 | 595-IleHisArgLysAsnGlyGluThrValGlu-604 |
| SEQ. ID. NO. 15583 | 609-CysArgLeuAspThrAlaGluGlu-616 |
| a102 | |
| AMPHI Regions - AMPHI | |
| SEQ. ID. NO. 15584 | 42-ValLeuLeuTyrThrTrpPheSerMetLeu-51 |
| SEQ. ID. NO. 15585 | 67-GlyAlaXxxPheAspThrMetValLysAspLeuLeuGlyArgSerTrpAsnIleIleAsnGlyIleAla-89 |
| SEQ. ID. NO. 15586 | 109-ThrAlaLysGlyLeuGlySerAlaAla-117 |
| SEQ. ID. NO. 15587 | 128-LeuValPhePheGlyIleLeuAlaPheCys-137 |
| SEQ. ID. NO. 15588 | 144-LeuValAspArgPheThrSerValLeu-152 |
| SEQ. ID. NO. 15589 | 155-GlyMetValLeuThr-159 |
| SEQ. ID. NO. 15590 | 207-AsnValSerSerLeuLeuLysTyrPheLys-216 |
| SEQ. ID. NO. 15591 | 221-LysValAlaLysSerIle-226 |

TABLE 1-continued

| | |
|---|---|
| SEQ. ID. NO. 15592 | 267-IleGluThrLeuSerLysPheAlaGlnThrGlyAsnMetAspLysIleLeuSerLeuPheSerTyrMetAla-290 |
| SEQ. ID. NO. 15593 | 303-PheAspTyrIleAlaAspIlePheLysTrpAsnAsp-314 |
| SEQ. ID. NO. 15594 | 341-PheValThrAlaIleGlyTyr-347 |
| SEQ. ID. NO. 15595 | 352-AlaThrValTrpThrGlyIleIlePro-360 |
| SEQ. ID. NO. 15596 | 374-GlyLysThrTyrLysVal-379 |
| Antigenic Index - Jameson-Wolf | |
| SEQ. ID. NO. 15597 | 1-MetProThrLysThrProSerLeu-8 |
| SEQ. ID. NO. 15598 | 77-LeuLeuGlyArgSer-81 |
| SEQ. ID. NO. 15599 | 107-AspLeuThrAlaLysGlyLeuGlySerAlaAlaGlyGly-119 |
| SEQ. ID. NO. 15600 | 143-ArgLeuValAspArgPheThr-149 |
| SEQ. ID. NO. 15601 | 179-ThrGlnAlaProThrGlyThrAsn-186 |
| SEQ. ID. NO. 15602 | 214-TyrPheLysGlyAspAlaProLysValAla-223 |
| SEQ. ID. NO. 15603 | 246-XxxAsnLeuProArgAsnGluPhe-253 |
| SEQ. ID. NO. 15604 | 274-AlaGlnThrGlyAsnMetAspLysIle-282 |
| SEQ. ID. NO. 15605 | 311-LysTrpAsnAspSerValSerGlyArgThrLysThr-322 |
| SEQ. ID. NO. 15606 | 364-LeuTyrArgSerArgLysLysPheGlyAlaGlyLysThrTyrLysVal-379 |
| Hydrophilic Regions - Hopp-Woods | |
| SEQ. ID. NO. 15607 | 1-MetProThrLysThr-5 |
| SEQ. ID. NO. 15608 | 143-ArgLeuValAspArgPheThr-149 |
| SEQ. ID. NO. 15609 | 215-PheLysGlyAspAlaProLysValAla-223 |
| SEQ. ID. NO. 15610 | 248-LeuProArgAsnGluPhe-253 |
| SEQ. ID. NO. 15611 | 277-GlyAsnMetAspLys-281 |
| SEQ. ID. NO. 15612 | 316-ValSerGlyArgThrLysThr-322 |
| SEQ. ID. NO. 15613 | 366-ArgSerArgLysLysPheGlyAla-373 |
| a105 | |
| AMPHI Regions - AMPHI | |
| SEQ. ID. NO. 15614 | 11-TrpIleGlyLeuGly-15 |
| SEQ. ID. NO. 15615 | 22-ValThrArgLeuLeuAsp-27 |
| SEQ. ID. NO. 15616 | 51-LysValTyrGlyAsnThrAlaGluLeu-59 |
| SEQ. ID. NO. 15617 | 74-AlaAlaValCysAspIleLeuAsnGlyValArgAspGlyLeu-87 |
| SEQ. ID. NO. 15618 | 97-ThrIleSerProThr-101 |
| SEQ. ID. NO. 15619 | 110-ValGluAlaAlaGlyGlyGlnPheAlaGluAlaProVal-122 |
| SEQ. ID. NO. 15620 | 143-AlaValLeuAsnProLeuGlnLysIlePheSer-153 |
| SEQ. ID. NO. 15621 | 162-PheGlyAspValGlyLysGlySer-169 |
| SEQ. ID. NO. 15622 | 176-AsnSerLeuLeuGlyIlePheGlyGluAlaTyr-186 |
| SEQ. ID. NO. 15623 | 203-IleValGluAlaIleGlyGlySerAla-211 |
| SEQ. ID. NO. 15624 | 249-LeuGluGlnAlaGlyAsnThrLeuProAlaValGlu-260 |
| SEQ. ID. NO. 15625 | 263-AlaAlaSerTyrArgLysAlaValGluAla-272 |
| Antigenic Index - Jameson-Wolf | |
| SEQ. ID. NO. 15626 | 2-SerAlaAsnGluTyrThr-7 |
| SEQ. ID. NO. 15627 | 25-LeuLeuAspGlyGlyIleGlu-31 |
| SEQ. ID. NO. 15628 | 34-ValTyrAsnArgSerProAspLysThrAlaProIleSerAlaLysGlyAlaLysValTyrGlyAsnThr-56 |
| SEQ. ID. NO. 15629 | 81-AsnGlyValArgAspGlyLeuAla-88 |
| SEQ. ID. NO. 15630 | 96-SerThrIleSerProThrGluAsnLeuAla-105 |
| SEQ. ID. NO. 15631 | 121-ProValSerGlySerValGlyProAlaThr-130 |
| SEQ. ID. NO. 15632 | 139-GlyGlySerGluAla-143 |
| SEQ. ID. NO. 15633 | 155-ValGlyLysLysThrPheHisPheGlyAspValGlyLysGlySerGly-170 |
| SEQ. ID. NO. 15634 | 196-PheGlyIleAspThrAspThrIleVal-204 |
| SEQ. ID. NO. 15635 | 210-SerAlaMetAspSerProMetPheGlnThrLysLysSerLeuTrpAlaAsnArgGluPheProPro-231 |
| SEQ. ID. NO. 15636 | 237-HisAlaSerLysAspLeuAsnLeuAlaValLysGluLeuGluGlnAlaGlyAsnThrLeuPro-257 |
| SEQ. ID. NO. 15637 | 264-AlaSerTyrArgLysAlaValGluAlaGlyTyrGlyGluGlnAspValSerGly-281 |
| Hydrophilic Regions - Hopp-Woods | |
| SEQ. ID. NO. 15638 | 25-LeuLeuAspGlyGlyIle-30 |
| SEQ. ID. NO. 15639 | 37-ArgSerProAspLysThrAlaProIleSerAlaLysGlyAlaLys-51 |
| SEQ. ID. NO. 15640 | 81-AsnGlyValArgAspGlyLeuAla-88 |
| SEQ. ID. NO. 15641 | 164-AspValGlyLysGlySerGly-170 |
| SEQ. ID. NO. 15642 | 196-PheGlyIleAspThrAspThrIle-203 |
| SEQ. ID. NO. 15643 | 218-GlnThrLysLysSerLeuTrpAla-225 |
| SEQ. ID. NO. 15644 | 237-HisAlaSerLysAspLeuAsnLeuAlaValLysGluLeuGluGlnAlaGly-253 |
| SEQ. ID. NO. 15645 | 265-SerTyrArgLysAlaValGlu-271 |
| SEQ. ID. NO. 15646 | 273-GlyTyrGlyGluGlnAspVal-279 |
| a109-2 | |
| AMPHI Regions - AMPHI | |
| SEQ. ID. NO. 15647 | 6-GlyThrTyrArgAspLeuHisArgProAlaSerGlu-17 |
| SEQ. ID. NO. 15648 | 53-LeuIleProAlaMetAlaGlyThrIleGly-62 |
| SEQ. ID. NO. 15649 | 69-AlaValAlaAlaAlaPhe-74 |
| SEQ. ID. NO. 15650 | 145-GlyLeuLeuMetAla-149 |
| SEQ. ID. NO. 15651 | 156-IleMetAlaLysLeuThrSer-162 |
| SEQ. ID. NO. 15652 | 177-GlyThrThrGlyGlnValLysLysLeuPheSerTrpAlaGly-190 |
| SEQ. ID. NO. 15653 | 207-ValMetTyrAlaLeuLeuGluHisTrpLysLysArgTrpLeu-220 |
| SEQ. ID. NO. 15654 | 222-ValProLeuGlyCys-226 |
| SEQ. ID. NO. 15655 | 294-HisGlnValPheGlnLysIle-300 |
| SEQ. ID. NO. 15656 | 326-ValGlySerIleLeuGly-331 |
| SEQ. ID. NO. 15657 | 336-ThrSerSerTrpGlyThr-341 |
| SEQ. ID. NO. 15658 | 471-AlaValGlyMetLeuProGlyIleProProPheLeuGluHisPheLysSerLeu-488 |
| Antigenic Index - Jameson-Wolf | |
| SEQ. ID. NO. 15659 | 1-MetGluLysHisAsnGlyThrTyrArgAspLeuHisArgProAlaSer-16 |
| SEQ. ID. NO. 15660 | 18-PheAlaThrArgAspGluTyrLeuGlu-26 |
| SEQ. ID. NO. 15661 | 32-MetGlnProLysArgTrpArgProAsnLeuProPheArgAspTyrArgPheGluTrp-50 |
| SEQ. ID. NO. 15662 | 78-LeuGlyLeuProAsp-82 |

TABLE 1-continued

| | |
|---|---|
| SEQ. ID. NO. 15663 | 109-ProGlyAlaAsnLeuProGlyThrHis-117 |
| SEQ. ID. NO. 15664 | 160-LeuThrSerAsnGlyVal-165 |
| SEQ. ID. NO. 15665 | 179-ThrGlyGlnValLysLys-184 |
| SEQ. ID. NO. 15666 | 245-AlaProGlyLeuProPro-250 |
| SEQ. ID. NO. 15667 | 259-GluAsnSerGlyTrp-263 |
| SEQ. ID. NO. 15668 | 301-SerTyrProGluLysThrAspLysVal-309 |
| SEQ. ID. NO. 15669 | 312-AsnIleAspAspThrMetThr-318 |
| SEQ. ID. NO. 15670 | 348-IleAlaLysArgProIleProGlyGly-356 |
| SEQ. ID. NO. 15671 | 398-AlaGlyMetGluMetThrArgLysGlyLysThrThrGlnSer-411 |
| SEQ. ID. NO. 15672 | 441-GlyCysLysGluArgSerAla-447 |
| Hydrophilic Regions - Hopp-Woods | |
| SEQ. ID. NO. 15673 | 1-MetGluLysHisAsnGlyThrTyrArgAspLeuHisArgProAlaSer-16 |
| SEQ. ID. NO. 15674 | 18-PheAlaThrArgAspGluTyrLeuGlu-26 |
| SEQ. ID. NO. 15675 | 35-LysArgTrpArgPro-39 |
| SEQ. ID. NO. 15676 | 44-ArgAspTyrArgPheGluTrp-50 |
| SEQ. ID. NO. 15677 | 180-GlyGlnValLysLys-184 |
| SEQ. ID. NO. 15678 | 301-SerTyrProGluLysThrAspLysVal-309 |
| SEQ. ID. NO. 15679 | 313-IleAspAspThrMetThr-318 |
| SEQ. ID. NO. 15680 | 348-IleAlaLysArgProIlePro-354 |
| SEQ. ID. NO. 15681 | 398-AlaGlyMetGluMetThrArgLysGlyLysThrThrGln-410 |
| SEQ. ID. NO. 15682 | 441-GlyCysLysGluArgSerAla-447 |
| a111 | |
| AMPHI Regions - AMPHI | |
| SEQ. ID. NO. 15683 | 6-ArgLeuProAsnPheIleArgThrLeu-14 |
| SEQ. ID. NO. 15684 | 58-ProSerProAlaGluIleGlnLysArgIleAspAspAlaLeuLysGluValAsnArgGlnMetSer-79 |
| SEQ. ID. NO. 15685 | 90-PheAsnGlnHisThrAlaGly-96 |
| SEQ. ID. NO. 15686 | 128-GlyProLeuValAsnLeuTrp-134 |
| SEQ. ID. NO. 15687 | 151-IleLysGlnAlaAlaSerTyrThrGly-159 |
| SEQ. ID. NO. 15688 | 170-AspTyrAlaSerLeu-174 |
| SEQ. ID. NO. 15689 | 183-LeuAspLeuSerSerIleAlaLys-190 |
| SEQ. ID. NO. 15690 | 209-TyrLeuValGluIleGlyGly-215 |
| SEQ. ID. NO. 15691 | 314-GluThrGluAlaLeu-318 |
| Antigenic Index - Jameson-Wolf | |
| SEQ. ID. NO. 15692 | 1-MetProSerGluThrArgLeuProAsnPhe-10 |
| SEQ. ID. NO. 15693 | 26-CysSerGluGlnThrAla-31 |
| SEQ. ID. NO. 15694 | 37-GlnGlyGluThrMetGly-42 |
| SEQ. ID. NO. 15695 | 49-TyrLeuSerAsnAsnArgAspLysLeuProSerProAlaGluIleGlnLysArgIleAspAspAlaLeuLysGluValAsnArgGlnMetSerThr TyrGlnProAspSerGluIleSerArgPheAsnGlnHisThrAlaGlyLysProLeuArgIleSerSerAspPhe-105 |
| SEQ. ID. NO. 15696 | 135-GlyPheGlyProAspLysSerValThrArgGluProSerProGluGlnIleLysGln-153 |
| SEQ. ID. NO. 15697 | 163-IleIleLeuLysGlnGlyLysAspTyrAlaSerLeuSerLysThrHisProLysAla-181 |
| SEQ. ID. NO. 15698 | 192-PheGlyValAspLysValAlaGlyGluLeuGluLysTyrGly-205 |
| SEQ. ID. NO. 15699 | 213-IleGlyGlyGluLeuHisGlyLysGlyLysAsnAlaArgGlyGluProTrpArgIleGlyIleGluGlnProAsnIle-238 |
| SEQ. ID. NO. 15700 | 250-LeuAsnAsnArgSerLeuAlaThrSerGlyAspTyrArg-262 |
| SEQ. ID. NO. 15701 | 264-PheHisValAspLysSerGlyLysArgLeuSer-274 |
| SEQ. ID. NO. 15702 | 277-IleAsnProAsnAsnLysArgProIleSer-286 |
| SEQ. ID. NO. 15703 | 299-AlaMetThrAlaAspGlyLeuSer-306 |
| SEQ. ID. NO. 15704 | 314-GluThrGluAlaLeuLysLeuAlaGluArgGluLysLeu-326 |
| SEQ. ID. NO. 15705 | 332-ValArgAspLysGlyGlyTyrArg-339 |
| SEQ. ID. NO. 15706 | 342-MetSerSerGluPheGluLysLeuLeuArg-351 |
| Hydrophilic Regions - Hopp-Woods | |
| SEQ. ID. NO. 15707 | 1-MetProSerGluThrArgLeu-7 |
| SEQ. ID. NO. 15708 | 26-CysSerGluGlnThrAla-31 |
| SEQ. ID. NO. 15709 | 51-SerAsnAsnArgAspLysLeuProSer-59 |
| SEQ. ID. NO. 15710 | 61-AlaGluIleGlnLysArgIleAspAspAlaLeuLysGluValAsnArgGln-77 |
| SEQ. ID. NO. 15711 | 82-GlnProAspSerGluIleSerArg-89 |
| SEQ. ID. NO. 15712 | 97-LysProLeuArgIleSerSer-103 |
| SEQ. ID. NO. 15713 | 137-GlyProAspLysSerValThrArgGluProSerProGluGlnIleLysGln-153 |
| SEQ. ID. NO. 15714 | 163-IleIleLeuLysGlnGlyLysAspTyrAlaSer-173 |
| SEQ. ID. NO. 15715 | 175-SerLysThrHisPro-179 |
| SEQ. ID. NO. 15716 | 192-PheGlyValAspLysValAlaGlyGluLeuGluLysTyrGly-205 |
| SEQ. ID. NO. 15717 | 217-LeuHisGlyLysGlyLysAsnAlaArgGlyGluProTrp-229 |
| SEQ. ID. NO. 15718 | 265-HisValAspLysSerGlyLysArgLeuSer-274 |
| SEQ. ID. NO. 15719 | 279-ProAsnAsnLysArgProIle-285 |
| SEQ. ID. NO. 15720 | 314-GluThrGluAlaLeuLysLeuAlaGluArgGluLysLeu-326 |
| SEQ. ID. NO. 15721 | 332-ValArgAspLysGlyGlyTyr-338 |
| SEQ. ID. NO. 15722 | 344-SerGluPheGluLysLeuLeuArg-351 |
| a117-1 | |
| AMPHI Regions - AMPHI | |
| SEQ. ID. NO. 15723 | 6-ProIleGlnAspThrGlnSerAla-13 |
| SEQ. ID. NO. 15724 | 15-LeuGlnGluLeuArgGluTrpPheAspSerTyrCysThr-27 |
| SEQ. ID. NO. 15725 | 57-GlyGluProLeuProAspHis-63 |
| SEQ. ID. NO. 15726 | 72-HisGluLeuAspLeuLeu-77 |
| SEQ. ID. NO. 15727 | 79-AspAlaValAlaAlaThrLeuLeuAlaAspIleGlyArgTyr-92 |
| SEQ. ID. NO. 15728 | 104-CysAsnSerThrValAlaGluLeuValLysGlyValAspGluValGlnLysLeuThrHisPheAlaArgValAspSerLeu-130 |
| SEQ. ID. NO. 15729 | 145-LysMetLeuLeuAlaMet-150 |
| SEQ. ID. NO. 15730 | 170-PheLeuSerAsnAlaProAspSerProGluLys-180 |
| SEQ. ID. NO. 15731 | 216-GluProGluLysTyrArg-221 |
| SEQ. ID. NO. 15732 | 234-ArgLeuGluTyrIleGluAsnPheLeuAsnIleLeuArg-246 |
| SEQ. ID. NO. 15733 | 260-GlyArgProLysHisIleTyrSerIleTyrLys-270 |
| SEQ. ID. NO. 15734 | 282-LeuPheAspIleArg-286 |

TABLE 1-continued

| | |
|---|---|
| SEQ. ID. NO. 15735 | 290-IleLeuValAspThrValProGluCysTyrThrThrLeuGlyIleValHisSerLeuTrpGlnProIleProGlyGluPheAspAspTyrIleAla-321 |
| SEQ. ID. NO. 15736 | 327-GlyTyrLysSerLeuHisThr-333 |
| SEQ. ID. NO. 15737 | 351-AspMetHisGlnPheAsnGluPheGlyValAla-361 |
| SEQ. ID. NO. 15738 | 385-GlnLeuLeuAspTrp-389 |
| SEQ. ID. NO. 15739 | 440-HisSerSerIleGlyAspArg-446 |
| SEQ. ID. NO. 15740 | 493-LysAlaIleGlyLysIleArgAlaTyr-501 |
| SEQ. ID. NO. 15741 | 504-GlnGlnAsnAlaAsp-508 |
| SEQ. ID. NO. 15742 | 521-GlnLeuAlaLysLeu-525 |
| SEQ. ID. NO. 15743 | 532-GlnGluLeuAlaGlu-536 |
| SEQ. ID. NO. 15744 | 539-GlyTyrLysLysProGluAspLeuTyrThr-548 |
| SEQ. ID. NO. 15745 | 557-AsnArgAlaIleGlnLysAlaCysGlyThrLeuAsnGluProPro-571 |
| SEQ. ID. NO. 15746 | 585-LysIleLysLysGlyGly-590 |
| SEQ. ID. NO. 15747 | 603-MetThrThrLeuAlaLysCysCysLysProAla-613 |
| SEQ. ID. NO. 15748 | 616-AspAspIleValGly-620 |
| SEQ. ID. NO. 15749 | 637-SerPheArgHisLeuAlaGluHisAlaProGluLysValLeuAspAla-652 |
| SEQ. ID. NO. 15750 | 679-ArgAspValSerAspAla-684 |
| SEQ. ID. NO. 15751 | 714-GlnValThrAspLeuProArgValLeuAlaSerLeuGlyAspValLysGlyValLeuSerValThrArg-736 |
| Antigenic Index - Jameson-Wolf | |
| SEQ. ID. NO. 15752 | 5-SerProIleGlnAspThrGlnSerAlaThr-14 |
| SEQ. ID. NO. 15753 | 16-GlnGluLeuArgGluTrpPheAspSerTyrCysThrAlaLeuProAsnAsnAspLysLysLeu-36 |
| SEQ. ID. NO. 15754 | 52-AlaAlaThrProTyrGlyGluProLeuProAspHisPhe-64 |
| SEQ. ID. NO. 15755 | 88-AspIleGlyArgTyrValProAspTrp-96 |
| SEQ. ID. NO. 15756 | 100-ValSerGluArgCysAsnSerThrVal-108 |
| SEQ. ID. NO. 15757 | 110-GluLeuValLysGlyValAspGluValGlnLys-120 |
| SEQ. ID. NO. 15758 | 125-AlaArgValAspSerLeuAlaThrProGluGluArgAlaGlnGlnAlaGluThrMetArg-144 |
| SEQ. ID. NO. 15759 | 162-AlaMetArgThrArgThr-167 |
| SEQ. ID. NO. 15760 | 173-AsnAlaProAspSerProGluLysArgAlaValAlaLysGluThrLeu-188 |
| SEQ. ID. NO. 15761 | 209-AspLeuGlyPheArgHisGlnGluProGluLysTyrArgGlu-222 |
| SEQ. ID. NO. 15762 | 227-LeuAspGluLysArgThrGluArgLeuGluTyr-237 |
| SEQ. ID. NO. 15763 | 245-LeuArgThrGluLeuLysLys-251 |
| SEQ. ID. NO. 15764 | 258-ValAlaGlyArgProLysHis-264 |
| SEQ. ID. NO. 15765 | 271-LysMetValLysLysLysLeuSerPhe-279 |
| SEQ. ID. NO. 15766 | 294-ThrValProGluCysTyr-299 |
| SEQ. ID. NO. 15767 | 311-ProIleProGlyGluPheAspAspTyrIleAlaAsnProLysGlyAsnGlyTyrLysSer-330 |
| SEQ. ID. NO. 15768 | 335-IleValGlyProGluAspLysGlyValGluValGlnIleArgThr-349 |
| SEQ. ID. NO. 15769 | 364-TrpArgTyrLysGluGlyGlyLysGlyAspSerAlaTyrGluGlnLys-379 |
| SEQ. ID. NO. 15770 | 387-LeuAspTrpArgGluAsnMetAlaGluSerGlyLysGluAspLeuAlaAla-403 |
| SEQ. ID. NO. 15771 | 418-ThrProHisGlyLys-422 |
| SEQ. ID. NO. 15772 | 440-HisSerSerIleGlyAspArgCysArgGlyAlaLysValGluGly-454 |
| SEQ. ID. NO. 15773 | 461-ThrProLeuGluAsnGlyGlnArgValGluIleIleThrAlaLysGluGlyHisProSerValAsn-482 |
| SEQ. ID. NO. 15774 | 487-GlyTrpValLysSerAsnLysAlaIleGlyLys-497 |
| SEQ. ID. NO. 15775 | 502-IleArgGlnGlnAsnAlaAspThrValArgGluGluGlyArgValGlnLeuAspLysGlnLeuAla-523 |
| SEQ. ID. NO. 15776 | 525-LeuThrProLysProAsnLeuGlnGluLeuAlaGlu-536 |
| SEQ. ID. NO. 15777 | 538-LeuGlyTyrLysLysProGluAspLeu-546 |
| SEQ. ID. NO. 15778 | 551-GlyGlnGlyGluIleSerAsnArgAlaIleGlnLysAlaCysGlyThrLeuAsnGluProProProValPro-574 |
| SEQ. ID. NO. 15779 | 582-LysGlnSerLysIleLysLysGlyGlyLysAsnGlyVal-594 |
| SEQ. ID. NO. 15780 | 596-IleAspGlyGluAspGlyLeu-602 |
| SEQ. ID. NO. 15781 | 608-LysCysCysLysProAlaProProAspAspIleVal-619 |
| SEQ. ID. NO. 15782 | 622-ValThrArgAspArgGlyIleSerValHisArgLysThrCysProSerPhe-638 |
| SEQ. ID. NO. 15783 | 644-HisAlaProGluLysValLeuAsp-651 |
| SEQ. ID. NO. 15784 | 667-IleGluIleArgAlaGlnAspArgSerGlyLeuLeuArgAspValSerAspAlaLeuAlaArgHisLysLeu-690 |
| SEQ. ID. NO. 15785 | 696-GlnThrGlnSerArgAspLeuGluAlaSerMet-706 |
| SEQ. ID. NO. 15786 | 710-LeuGluValLysGlnValThrAspLeuProArg-720 |
| SEQ. ID. NO. 15787 | 726-GlyAspValLysGly-730 |
| Hydrophilic Regions- Hopp-Woods | |
| SEQ. ID. NO. 15788 | 8-GlnAspThrGlnSer-12 |
| SEQ. ID. NO. 15789 | 16-GlnGluLeuArgGluTrpPhe-22 |
| SEQ. ID. NO. 15790 | 30-ProAsnAsnAspLysLysLeu-36 |
| SEQ. ID. NO. 15791 | 100-ValSerGluArgCysAsnSerThr-107 |
| SEQ. ID. NO. 15792 | 110-GluLeuValLysGlyValAspGluValGlnLys-120 |
| SEQ. ID. NO. 15793 | 125-AlaArgValAspSer-129 |
| SEQ. ID. NO. 15794 | 131-AlaThrProGluGluArgAlaGlnGlnAlaGluThrMetArg-144 |
| SEQ. ID. NO. 15795 | 162-AlaMetArgThrArgThr-167 |
| SEQ. ID. NO. 15796 | 174-AlaProAspSerProGluLysArgAlaValAlaLysGluThrLeu-188 |
| SEQ. ID. NO. 15797 | 209-AspLeuGlyPheArgHisGlnGluProGluLysTyrArgGlu-222 |
| SEQ. ID. NO. 15798 | 227-LeuAspGluLysArgThrGluArgLeuGluTyr-237 |
| SEQ. ID. NO. 15799 | 245-LeuArgThrGluLeuLysLys-251 |
| SEQ. ID. NO. 15800 | 258-ValAlaGlyArgProLysHis-264 |
| SEQ. ID. NO. 15801 | 271-LysMetValLysLysLysLeuSerPhe-279 |
| SEQ. ID. NO. 15802 | 314-GlyGluPheAspAsp-318 |
| SEQ. ID. NO. 15803 | 323-ProLysGlyAsnGly-327 |
| SEQ. ID. NO. 15804 | 337-GlyProGluAspLysGlyValGluValGlnIleArgThr-349 |
| SEQ. ID. NO. 15805 | 365-ArgTyrLysGluGlyGlyLysGlyAspSerAlaTyrGluGln-378 |
| SEQ. ID. NO. 15806 | 387-LeuAspTrpArgGluAsnMetAlaGluSerGlyLysGluAspLeuAlaAla-403 |
| SEQ. ID. NO. 15807 | 443-IleGlyAspArgCysArgGlyAlaLysValGluGly-454 |
| SEQ. ID. NO. 15808 | 463-LeuGluAsnGlyGlnArgValGluIleIleThrAlaLysGluGlyHisPro-479 |
| SEQ. ID. NO. 15809 | 489-ValLysSerAsnLysAlaIleGlyLys-497 |
| SEQ. ID. NO. 15810 | 505-GlnAsnAlaAspThrValArgGluGluGlyArgValGlnLeuAspLysGlnLeuAla-523 |
| SEQ. ID. NO. 15811 | 538-LeuGlyTyrLysLysProGluAspLeu-546 |
| SEQ. ID. NO. 15812 | 553-GlyGluIleSerAsn-557 |

TABLE 1-continued

| | |
|---|---|
| SEQ. ID. NO. 15813 | 582-LysGlnSerLysIleLysLysGlyGlyLys-591 |
| SEQ. ID. NO. 15814 | 596-IleAspGlyGluAspGlyLeu-602 |
| SEQ. ID. NO. 15815 | 608-LysCysCysLysProAlaProProAspAspIle-618 |
| SEQ. ID. NO. 15816 | 622-ValThrArgAspArgGlyIleSerValHisArgLysThrCysPro-636 |
| SEQ. ID. NO. 15817 | 644-HisAlaProGluLysValLeu-650 |
| SEQ. ID. NO. 15818 | 667-IleGluIleArgAlaGlnAspArgSerGlyLeuLeuArgAspValSerAspAlaLeuAlaArgHisLysLeu-690 |
| SEQ. ID. NO. 15819 | 697-ThrGlnSerArgAspLeuGluAlaSerMet-706 |
| SEQ. ID. NO. 15820 | 710-LeuGluValLysGlnValThrAspLeuProArg-720 |
| SEQ. ID. NO. 15821 | 726-GlyAspValLysGly-730 |
| a118 | |
| AMPHI Regions - AMPHI | |
| SEQ. ID. NO. 15822 | 24-GlyLysTrpTyrAsp-28 |
| SEQ. ID. NO. 15823 | 57-IleProArgAspIle-61 |
| SEQ. ID. NO. 15824 | 65-IleGlyThrIleIleAspPheLeuMetValProAsn-76 |
| SEQ. ID. NO. 15825 | 94-IleHisGluArgTyrGluArgPheThrThrMetLeuArg-106 |
| Antigenic Index - Jameson-Wolf | |
| SEQ. ID. NO. 15826 | 2-CysGluPheLysAspPheArgArgAsnIleProCys-13 |
| SEQ. ID. NO. 15827 | 15-GluGluTyrAspGluAsnSerPhe-22 |
| SEQ. ID. NO. 15828 | 24-GlyLysTrpTyrAspAspGlyValTrpAspAspGluGluTyrTrpLysLeuGluAsnAspLeuIleGluValArgLysLysTyrProTyrProMet AspIleProArgAspIle-61 |
| SEQ. ID. NO. 15829 | 86-ProTrpLeuProAspSer-91 |
| SEQ. ID. NO. 15830 | 93-GlyIleHisGluArgTyrGluArg-100 |
| SEQ. ID. NO. 15831 | 109-PheThrGluLysAspIleVal-115 |
| SEQ. ID. NO. 15832 | 119-PheAspTyrTyrAsnLysLys-125 |
| Hydrophilic Regions - Hopp-Woods | |
| SEQ. ID. NO. 15833 | 2-CysGluPheLysAspPheArgArgAsnIleProCys-13 |
| SEQ. ID. NO. 15834 | 15-GluGluTyrAspGlu-19 |
| SEQ. ID. NO. 15835 | 30-GlyValTrpAspAspGluGluTyrTrpLysLeuGluAsnAspLeuIleGluValArgLysLysTyrProTyr-53 |
| SEQ. ID. NO. 15836 | 96-GluArgTyrGluArg-100 |
| SEQ. ID. NO. 15837 | 109-PheThrGluLysAspIleVal-115 |
| SEQ. ID. NO. 15838 | 121-TyrTyrAsnLysLys-125 |
| a120 | |
| AMPHI Regions - AMPHI | |
| SEQ. ID. NO. 15839 | 6-LysAsnIlePheSerAla-11 |
| SEQ. ID. NO. 15840 | 49-SerGlyAsnAlaTyrLysIleValSerThrIleLys-60 |
| SEQ. ID. NO. 15841 | 77-AsnThrLeuHisProThrTyrTyrArgAspIleArgArg-89 |
| SEQ. ID. NO. 15842 | 142-IleThrAsnGlyLysLysLeuTyrSerValGlyGlyLeuAsnLysAlaGly-158 |
| SEQ. ID. NO. 15843 | 189-ProSerLeuAsnAsnIleProAla-196 |
| Antigenic Index - Jameson-Wolf | |
| SEQ. ID. NO. 15844 | 35-SerGlySerTyrGly-39 |
| SEQ. ID. NO. 15845 | 45-ThrPheGluArgSerGlyAsnAlaTyrLys-54 |
| SEQ. ID. NO. 15846 | 68-PheGluSerGlyGlyThrValVal-75 |
| SEQ. ID. NO. 15847 | 85-ArgAspIleArgArgGlyLysLeuTyrAlaGlu-95 |
| SEQ. ID. NO. 15848 | 97-LysPheAlaAspGlySerValThrTyrGlyLysAlaGlyGluSerLysThrGluGlnSerProLysAla-119 |
| SEQ. ID. NO. 15849 | 131-AlaAsnAspAlaLysLeuProProGlyLeuLysIleThrAsnGlyLysLysLeuTyrSer-150 |
| SEQ. ID. NO. 15850 | 153-GlyLeuAsnLysAlaGlyThrGlyLysTyrSerIleGlyGlyValGluThrGluValValLysTyrArgValArgArgGlyAspAspAlaVal-183 |
| SEQ. ID. NO. 15851 | 199-GlyTyrThrAspAspGlyLysThrTyr-207 |
| SEQ. ID. NO. 15852 | 218-GlyGlnAlaAlaLysPro-223 |
| Hydrophilic Regions - Hopp-Woods | |
| SEQ. ID. NO. 15853 | 45-ThrPheGluArgSerGlyAsn-51 |
| SEQ. ID. NO. 15854 | 85-ArgAspIleArgArgGlyLysLeuTyrAla-94 |
| SEQ. ID. NO. 15855 | 107-LysAlaGlyGluSerLysThrGluGlnSerProLysAla-119 |
| SEQ. ID. NO. 15856 | 131-AlaAsnAspAlaLysLeu-136 |
| SEQ. ID. NO. 15857 | 143-ThrAsnGlyLysLysLeuTyr-149 |
| SEQ. ID. NO. 15858 | 155-AsnLysAlaGlyThrGly-160 |
| SEQ. ID. NO. 15859 | 167-ValGluThrGluValValLysTyrArgValArgArgGlyAspAspAla-182 |
| SEQ. ID. NO. 15860 | 200-TyrThrAspAspGlyLysThrTyr-207 |
| SEQ. ID. NO. 15861 | 219-GlnAlaAlaLysPro-223 |
| a121-1 | |
| AMPHI Regions - AMPHI | |
| SEQ. ID. NO. 15862 | 68-GlnGluLeuSerArgLeuTyrAlaGlnThr-77 |
| SEQ. ID. NO. 15863 | 101-ThrValArgHisAlaPro-106 |
| SEQ. ID. NO. 15864 | 148-ProAlaPheHisGlu-152 |
| SEQ. ID. NO. 15865 | 165-LeuAsnIleGlyGlyIleAlaAsnIle-173 |
| SEQ. ID. NO. 15866 | 189-ProGlyAsnMetLeuMetAspAlaTrpMetGlnAla-200 |
| SEQ. ID. NO. 15867 | 216-GlyAsnIleLeuProGlnLeuLeuAspArgLeuLeu-227 |
| SEQ. ID. NO. 15868 | 237-ProLysSerThrGly-241 |
| SEQ. ID. NO. 15869 | 251-GluThrTyrLeuAsp-255 |
| SEQ. ID. NO. 15870 | 262-AspValLeuArgThrLeuSerArgPheThrAlaGlnThrValPheAspAlaValSerHis-281 |
| SEQ. ID. NO. 15871 | 303-AlaAspLeuAlaGluCysPhe-309 |
| SEQ. ID. NO. 15872 | 341-ValAsnArgIleProGlySerPro-348 |
| Antigenic Index - Jameson-Wolf | |
| SEQ. ID. NO. 15873 | 13-ThrSerMetAspGlyAlaAsp-19 |
| SEQ. ID. NO. 15874 | 23-IleArgMetAspGlyGlyLysTrpLeuGly-32 |
| SEQ. ID. NO. 15875 | 40-ProTyrProGlyArgLeuArgArgLysLeuLeuAspLeuGlnAspThrGlyAlaAspGluLeuHisArgSerArgMetLeuSer-67 |
| SEQ. ID. NO. 15876 | 86-AsnLeuAlaProSerAspIleThrAla-94 |
| SEQ. ID. NO. 15877 | 97-CysHisGlyGlnThrValArgHisAlaProGluHisSerTyrSer-111 |
| SEQ. ID. NO. 15878 | 119-LeuLeuAlaGluArgThrGln-125 |
| SEQ. ID. NO. 15879 | 129-ValGlyAspPheArgSerArgAspLeuAlaAlaGlyGlyGlnGly-143 |
| SEQ. ID. NO. 15880 | 154-LeuPheArgAspAspArgGluThrArgAla-163 |

TABLE 1-continued

| | |
|---|---|
| SEQ. ID. NO. 15881 | 177-ProProAspAlaPro-181 |
| SEQ. ID. NO. 15882 | 184-GlyPheAspThrGlyProGlyAsn-191 |
| SEQ. ID. NO. 15883 | 205-ProTyrAspLysAsnGlyAlaLysAlaAlaGlnGlyAsn-217 |
| SEQ. ID. NO. 15884 | 235-ProHisProLysSerThrGlyArgGlu-243 |
| SEQ. ID. NO. 15885 | 253-TyrLeuAspGlyGlyGluAsnArgTyrAspValLeuArgThrLeuSer-268 |
| SEQ. ID. NO. 15886 | 283-AlaAlaAspAlaArgGln-288 |
| SEQ. ID. NO. 15887 | 293-GlyGlyGlyIleArgAsnProValLeu-301 |
| SEQ. ID. NO. 15888 | 344-IleProGlySerProHisLysAlaThrGlyAlaSerLysProCysIle-359 |
| Hydrophilic Regions - Hopp-Woods | |
| SEQ. ID. NO. 15889 | 13-ThrSerMetAspGlyAlaAsp-19 |
| SEQ. ID. NO. 15890 | 43-GlyArgLeuArgArgLysLeuLeuAspLeuGlnAspThrGlyAlaAspGluLeuHisArgSerArgMetLeuSer-67 |
| SEQ. ID. NO. 15891 | 101-ThrValArgHisAlaPro-106 |
| SEQ. ID. NO. 15892 | 119-LeuLeuAlaGluArgThrGln-125 |
| SEQ. ID. NO. 15893 | 131-AspPheArgSerArgAspLeuAlaAla-139 |
| SEQ. ID. NO. 15894 | 154-LeuPheArgAspAspArgGluThrArgAla-163 |
| SEQ. ID. NO. 15895 | 206-TyrAspLysAsnGlyAlaLysAlaAlaGln-215 |
| SEQ. ID. NO. 15896 | 236-HisProLysSerThrGlyArgGlu-243 |
| SEQ. ID. NO. 15897 | 254-LeuAspGlyGlyGluAsnArgTyrAspVal-263 |
| SEQ. ID. NO. 15898 | 283-AlaAlaAspAlaArgGln-288 |
| SEQ. ID. NO. 15899 | 344-IleProGlySerProHisLysAlaThrGlyAlaSer-355 |
| a122-1 | |
| AMPHI Regions - AMPHI | |
| SEQ. ID. NO. 15900 | 6-AsnIleHisLysThrPhe-11 |
| SEQ. ID. NO. 15901 | 42-ThrPheLeuArgCysLeuAsnAlaLeuGluMetProGlu-54 |
| SEQ. ID. NO. 15902 | 102-LeuGluAsnValMetGlu-107 |
| SEQ. ID. NO. 15903 | 126-LysLeuLeuGluLys-130 |
| SEQ. ID. NO. 15904 | 176-ProGluLeuValGlnAspValLeuAsnAlaMetLysGluLeuAlaArgGluGly-193 |
| SEQ. ID. NO. 15905 | 227-ProLysGluLeuPheAspHisPro-234 |
| Antigenic Index - Jameson-Wolf | |
| SEQ. ID. NO. 15906 | 5-ArgAsnIleHisLysThrPheGlyLysAsnThrIle-16 |
| SEQ. ID. NO. 15907 | 23-AspValCysLysGlyGln-28 |
| SEQ. ID. NO. 15908 | 34-GlyProSerGlySerGlyLysThrThr-42 |
| SEQ. ID. NO. 15909 | 51-GluMetProGluAspGlyGlnIleGluPheAspAsnGluArgProLeuLysIleAspPheSerLysLysProSerLysHisAspIle-79 |
| SEQ. ID. NO. 15910 | 81-AlaLeuArgArgLysSerGlyMet-88 |
| SEQ. ID. NO. 15911 | 96-PheProHisLysThrAlaLeu-102 |
| SEQ. ID. NO. 15912 | 114-GlyLysProAlaAlaGlnAlaArgGluGluAlaLeuLysLeuLeuGlu-129 |
| SEQ. ID. NO. 15913 | 131-ValGlyLeuGlyAspLysValAspLeu-139 |
| SEQ. ID. NO. 15914 | 145-SerGlyGlyGlnGlnGlnArgValGlyIle-154 |
| SEQ. ID. NO. 15915 | 168-AspGluProThrSerAlaLeuAspProGluLeuVal-179 |
| SEQ. ID. NO. 15916 | 184-AsnAlaMetLysGluLeuAlaArgGluGlyTrp-194 |
| SEQ. ID. NO. 15917 | 222-ValGluGlnGlySerProLysGluLeuPheAspHisProLysHisGluArgThrArgArgPheLeuSer-244 |
| Hydrophilic Regions - Hopp-Woods | |
| SEQ. ID. NO. 15918 | 51-GluMetProGluAspGlyGlnIleGluPheAspAsnGluArgProLeuLysIleAspPheSerLysLysProSerLysHisAsp-78 |
| SEQ. ID. NO. 15919 | 81-AlaLeuArgArgLysSerGly-87 |
| SEQ. ID. NO. 15920 | 114-GlyLysProAlaAlaGlnAlaArgGluGluAlaLeuLysLeuLeuGlu-129 |
| SEQ. ID. NO. 15921 | 131-ValGlyLeuGlyAspLysValAsp-138 |
| SEQ. ID. NO. 15922 | 168-AspGluProThrSerAlaLeuAspProGluLeuVal-179 |
| SEQ. ID. NO. 15923 | 184-AsnAlaMetLysGluLeuAlaArg-191 |
| SEQ. ID. NO. 15924 | 224-GlnGlySerProLysGluLeuPheAspHisProLysHisGluArgThrArgArgPheLeu-243 |
| a126-1 | |
| AMPHI Regions - AMPHI | |
| SEQ. ID. NO. 15925 | 26-LeuLysGlnSerValArg-31 |
| SEQ. ID. NO. 15926 | 73-GlyCysGlnSerValGlnGluAla-80 |
| SEQ. ID. NO. 15927 | 112-PheGlnLeuValGluAla-117 |
| SEQ. ID. NO. 15928 | 143-LeuAspAlaGlyCysGln-148 |
| SEQ. ID. NO. 15929 | 150-LeuMetProTrpAlaAlaProIleGlyThrGlyLeuGlyAlaVal-164 |
| SEQ. ID. NO. 15930 | 213-SerGlyAspProValAsnMetAlaArgAlaPhe-223 |
| Antigenic Index - Jameson-Wolf | |
| SEQ. ID. NO. 15931 | 7-GluThrPheProSerArgLeu-13 |
| SEQ. ID. NO. 15932 | 24-GluIleLeuLysGlnSerValArgThrAlaArg-34 |
| SEQ. ID. NO. 15933 | 41-SerLeuArgArgAlaGlyCysGlyGlyGluAlaHisGlyGlnGlyPhe-56 |
| SEQ. ID. NO. 15934 | 85-GlnMetAlaArgGluValPheGlu-92 |
| SEQ. ID. NO. 15935 | 99-GluLeuIleGlyAspAspAspThrLeuGln-108 |
| SEQ. ID. NO. 15936 | 121-LeuIleLysAspGlyPheLysValLeu-129 |
| SEQ. ID. NO. 15937 | 141-ArgLeuLeuAspAlaGlyCys-147 |
| SEQ. ID. NO. 15938 | 171-ValLeuArgGluArgLeuProAspThrProLeu-181 |
| SEQ. ID. NO. 15939 | 209-AlaValSerArgSerGlyAspProValAsn-218 |
| SEQ. ID. NO. 15940 | 228-GluSerGlyArgLeuAlaPhe-234 |
| SEQ. ID. NO. 15941 | 237-GlyProValGluAlaArgAspLysAlaGlnAlaSerThrProThrVal-252 |
| Hydrophilic Regions - Hopp-Woods | |
| SEQ. ID. NO. 15942 | 24-GluIleLeuLysGlnSerValArgThrAlaArg-34 |
| SEQ. ID. NO. 15943 | 41-SerLeuArgArgAlaGlyCysGlyGlyGluAlaHis-52 |
| SEQ. ID. NO. 15944 | 85-GlnMetAlaArgGluValPheGlu-92 |
| SEQ. ID. NO. 15945 | 100-LeuIleGlyAspAspAspThrLeuGln-108 |
| SEQ. ID. NO. 15946 | 171-ValLeuArgGluArgLeuProAsp-178 |

TABLE 1-continued

| | |
|---|---|
| SEQ. ID. NO. 15947 | 210-ValSerArgSerGlyAspPro-216 |
| SEQ. ID. NO. 15948 | 228-GluSerGlyArgLeuAlaPhe-234 |
| SEQ. ID. NO. 15949 | 237-GlyProValGluAlaArgAspLysAlaGlnAla-247 |
| a127 | |
| AMPHI Regions - AMPHI | |
| SEQ. ID. NO. 15950 | 6-MetLeuAspThrTrpLeuGlyAla-13 |
| SEQ. ID. NO. 15951 | 22-GluSerValAlaVal-26 |
| SEQ. ID. NO. 15952 | 119-ValGlyAspTyrIleGluIle-125 |
| SEQ. ID. NO. 15953 | 135-IleAsnLeuLeuAsnThrLeuMet-142 |
| SEQ. ID. NO. 15954 | 147-ProAsnProLeuValGlyGlnLeuAla-155 |
| SEQ. ID. NO. 15955 | 206-LeuGluProLeuCysAlaPro-212 |
| SEQ. ID. NO. 15956 | 214-IleProAlaIleGlnArgHisLeuGluAsnValGln-225 |
| SEQ. ID. NO. 15957 | 250-ArgIleIleValArgPheAlaSerProVal-259 |
| SEQ. ID. NO. 15958 | 268-AlaValMetAspGluPheLeuArgVal-276 |
| Antigenic Index - Jameson-Wolf | |
| SEQ. ID. NO. 15959 | 16-IleArgAlaGluAlaValGlu-22 |
| SEQ. ID. NO. 15960 | 41-HisPheLysArgHisProAspPheGlyIleGluSerLysArgArgPheLeuVal-58 |
| SEQ. ID. NO. 15961 | 112-SerAlaThrGlnGlnTyrSerVal-119 |
| SEQ. ID. NO. 15962 | 126-AsnGlyLeuArgGlyArgValValAsp-134 |
| SEQ. ID. NO. 15963 | 169-HisProValArgArgAspAsnIleLeu-177 |
| SEQ. ID. NO. 15964 | 193-LeuAspSerAspGluAlaValCysArg-201 |
| SEQ. ID. NO. 15965 | 233-ProAlaAlaLysProArgValThrArgValProTyrAspAspLysAlaTyr-249 |
| SEQ. ID. NO. 15966 | 257-SerProValSerLysArgLeuGluIle-265 |
| SEQ. ID. NO. 15967 | 283-TyrProAlaGlySerGluThrLeu-290 |
| Hydrophilic Regions - Hopp-Woods | |
| SEQ. ID. NO. 15968 | 16-IleArgAlaGluAlaValGlu-22 |
| SEQ. ID. NO. 15969 | 42-PheLysArgHisProAspPheGlyIleGluSerLysArgArgPheLeuVal-58 |
| SEQ. ID. NO. 15970 | 126-AsnGlyLeuArgGlyArgValVal-133 |
| SEQ. ID. NO. 15971 | 170-ProValArgArgAspAsnIleLeu-177 |
| SEQ. ID. NO. 15972 | 193-LeuAspSerAspGluAlaValCysArg-201 |
| SEQ. ID. NO. 15973 | 235-AlaLysProArgValThrArgValProTyrAspAspLysAlaTyr-249 |
| SEQ. ID. NO. 15974 | 259-ValSerLysArgLeuGluIle-265 |
| SEQ. ID. NO. 15975 | 285-AlaGlySerGluThrLeu-290 |
| a128-1 | |
| AMPHI Regions - AMPHI | |
| SEQ. ID. NO. 15976 | 43-AlaGlnThrHisThrGlyTrpAlaAsnThrValGluProLeuThrGlyIleThrGluArgValGlyArgIleTrpGlyValValSerHisLeuAsnSer ValThrAspThrProGlu-81 |
| SEQ. ID. NO. 15977 | 85-AlaTyrAsnGluLeuMetProGluIle-93 |
| SEQ. ID. NO. 15978 | 102-GlnAspIleGluLeuTyrAsnArgPheLysThrIleLysAsnSerProGluPheAsp-120 |
| SEQ. ID. NO. 15979 | 166-PheSerGlnAsnValLeuAspAlaThrAsp-175 |
| SEQ. ID. NO. 15980 | 189-GlyIleProGluAspAla-194 |
| SEQ. ID. NO. 15981 | 2118-HisTyrLeuAlaVal-222 |
| SEQ. ID. NO. 15982 | 231-LeuArgGluGlnIleTyr-236 |
| SEQ. ID. NO. 15983 | 245-GluLeuSerAspAspGlyLysPheAspAsnThrAlaAsnIleAspArgThrLeuGluAsnAlaLeu-266 |
| SEQ. ID. NO. 15984 | 269-AlaLysLeuLeuGlyPheLysAsnTyrAlaGlu-279 |
| SEQ. ID. NO. 15985 | 286-MetAlaAspThrProGluGlnValLeuAsnPheLeuHisAspLeuAlaArgArgAla-304 |
| SEQ. ID. NO. 15986 | 313-AlaGluValLysAlaPhe-318 |
| SEQ. ID. NO. 15987 | 359-GlyLysValLeuAsnGlyLeuPheAlaGlnIleLysLysLeuTyrGly-374 |
| SEQ. ID. NO. 15988 | 425-GlyArgArgArgPhe-429 |
| SEQ. ID. NO. 15989 | 472-LeuHisHisLeuLeuThrGlnValAspGluLeu-482 |
| SEQ. ID. NO. 15990 | 496-GluLeuProSerGlnPhe-501 |
| SEQ. ID. NO. 15991 | 565-GlyArgLeuLysAsnTrpGlnGlnValLeuAspSerVal-577 |
| SEQ. ID. NO. 15992 | 584-ValArgProProGluTyrAsnArgPheAlaAsnSerPheGlyHisIlePheAlaGlyGly-603 |
| SEQ. ID. NO. 15993 | 610-SerTyrAlaTrpAlaGlu-615 |
| SEQ. ID. NO. 15994 | 623-AlaAlaPheGluGluSerAspAsp-630 |
| SEQ. ID. NO. 15995 | 636-LysArgPheTrpGlnGluIleLeuAla-644 |
| SEQ. ID. NO. 15996 | 651-AlaAlaGluSerPheLysAlaPheArg-659 |
| Antigenic Index -Jameson-Wolf | |
| SEQ. ID. NO. 15997 | 9-LeuGlyGluGluProArgPheAspGlnIleLysThrGluAspIleLysProAlaLeu-27 |
| SEQ. ID. NO. 15998 | 32-AlaGluAlaArgGluGlnIleAla-39 |
| SEQ. ID. NO. 15999 | 43-AlaGlnThrHisThrGlyTrp-49 |
| SEQ. ID. NO. 16000 | 51-AsnThrValGluProLeuThr-57 |
| SEQ. ID. NO. 16001 | 59-IleThrGluArgValGlyArgIleTrp-67 |
| SEQ. ID. NO. 16002 | 75-SerValThrAspThrProGluLeuArgAlaAlaTyr-86 |
| SEQ. ID. NO. 16003 | 100-IleGlyGlnAspIleGluLeuTyrAsnArgPheLysThrIleLysAsnSerProGluPheAspThr-121 |
| SEQ. ID. NO. 16004 | 123-SerHisAlaGlnLysThrLysLeuAsnHisAspLeuArgAsp-136 |
| SEQ. ID. NO. 16005 | 140-SerGlyAlaGluLeuProProGluGlnGlnAlaGluLeuAlaLysLeuGlnThrGluGlyAlaGlnLeu-162 |
| SEQ. ID. NO. 16006 | 165-LysPheSerGlnAsnVal-170 |
| SEQ. ID. NO. 16007 | 172-AspAlaThrAspAla-176 |
| SEQ. ID. NO. 16008 | 190-IleProGluAspAla-194 |
| SEQ. ID. NO. 16009 | 202-AlaGlnSerGluGlyLysThrGlyTyrLys-211 |
| SEQ. ID. NO. 16010 | 226-AlaAspAsnArgLysLeuArgGluGlnIle-235 |
| SEQ. ID. NO. 16011 | 240-ValThrArgAlaSerGluLeuSerAspAspGlyLysPheAspAsnThrAlaAsnIleAspArgThrLeuGlu-263 |
| SEQ. ID. NO. 16012 | 285-LysMetAlaAspThrProGluGln-292 |
| SEQ. ID. NO. 16013 | 300-LeuAlaArgArgAlaLysProTyrAlaGluLysAspLeuAlaGlu-314 |
| SEQ. ID. NO. 16014 | 316-LysAlaPheAlaArgGluSerLeuGly-324 |
| SEQ. ID. NO. 16015 | 335-TyrAlaGlyGluLysLeuArgGluAlaLysTyrAlaPheSerGluThrGluValLysLys-354 |
| SEQ. ID. NO. 16016 | 376-GlyPheThrGluLysThrVal-382 |
| SEQ. ID. NO. 16017 | 387-LysAspValArgTyrPheGluLeuGlnGlnAsnGlyGluThrIle-401 |
| SEQ. ID. NO. 16018 | 409-TyrAlaArgGluGlyLysArgGlyGlyAla-418 |

TABLE 1-continued

| | |
|---|---|
| SEQ. ID. NO. 16019 | 420-MetAsnAspTyrLysGlyArgArgArgPheSerAspGlyThrLeu-434 |
| SEQ. ID. NO. 16020 | 446-ThrProProValGlyGlyLysGluAlaArgLeuSerHisAspGlu-460 |
| SEQ. ID. NO. 16021 | 478-GlnValAspGluLeuGlyVal-484 |
| SEQ. ID. NO. 16022 | 496-GluLeuProSerGln-500 |
| SEQ. ID. NO. 16023 | 516-SerAlaHisGluGluThrGlyVal-523 |
| SEQ. ID. NO. 16024 | 560-SerGluAspAspGluGlyArgLeuLysAsn-569 |
| SEQ. ID. NO. 16025 | 575-AspSerValArgLysGluValAlaValValArgProProGluTyrAsnArgPhe-592 |
| SEQ. ID. NO. 16026 | 605-SerAlaGlyTyrTyrSerTyr-611 |
| SEQ. ID. NO. 16027 | 625-PheGluGluSerAspAspValAlaAlaThrGlyLysArgPheTrp-639 |
| SEQ. ID. NO. 16028 | 646-GlyGlySerArgSerAlaAlaGluSerPheLysAlaPheArgGlyArgGluProSerIle-665 |
| SEQ. ID. NO. 16029 | 669-LeuArgHisSerGlyPheAspAsnAlaAla-678 |
| Hydrophilic Regions - Hopp-Woods | |
| SEQ. ID. NO. 16030 | 9-LeuGlyGluGluProArgPheAspGlnIleLysThrGluAspIleLysPro-25 |
| SEQ. ID. NO. 16031 | 32-AlaGluAlaArgGluGlnIleAla-39 |
| SEQ. ID. NO. 16032 | 59-IleThrGluArgValGly-64 |
| SEQ. ID. NO. 16033 | 77-ThrAspThrProGluLeuArgAlaAlaTyr-86 |
| SEQ. ID. NO. 16034 | 100-IleGlyGlnAspIleGluLeu-106 |
| SEQ. ID. NO. 16035 | 111-LysThrIleLysAsnSerProGluPheAspThr-121 |
| SEQ. ID. NO. 16036 | 123-SerHisAlaGlnLysThrLysLeuAsnHisAspLeuArgAsp-136 |
| SEQ. ID. NO. 16037 | 143-GluLeuProProGluGlnGlnAlaGluLeuAlaLysLeuGlnThrGluGlyAlaGlnLeu-162 |
| SEQ. ID. NO. 16038 | 190-IleProGluAspAla-194 |
| SEQ. ID. NO. 16039 | 202-AlaGlnSerGluGlyLysThrGlyTyr-210 |
| SEQ. ID. NO. 16040 | 226-AlaAspAsnArgLysLeuArgGluGlnIle-235 |
| SEQ. ID. NO. 16041 | 242-ArgAlaSerGluLeuSerAspAspGlyLysPheAspAsn-254 |
| SEQ. ID. NO. 16042 | 256-AlaAsnIleAspArgThrLeuGlu-263 |
| SEQ. ID. NO. 16043 | 285-LysMetAlaAspThrProGlu-291 |
| SEQ. ID. NO. 16044 | 300-LeuAlaArgArgAlaLysProTyrAlaGluLysAspLeuAlaGlu-314 |
| SEQ. ID. NO. 16045 | 316-LysAlaPheAlaArgGluSerLeuGly-324 |
| SEQ. ID. NO. 16046 | 335-TyrAlaGlyGluLysLeuArgGluAlaLysTyrAlaPheSerGluThrGluValLysLys-354 |
| SEQ. ID. NO. 16047 | 377-PheThrGluLysThr-381 |
| SEQ. ID. NO. 16048 | 387-LysAspValArgTyr-391 |
| SEQ. ID. NO. 16049 | 396-GlnAsnGlyGluThr-400 |
| SEQ. ID. NO. 16050 | 409-TyrAlaArgGluGlyLysArgGlyGly-417 |
| SEQ. ID. NO. 16051 | 423-TyrLysGlyArgArgArgPheSerAsp-431 |
| SEQ. ID. NO. 16052 | 449-ValGlyGlyLysGluAlaArgLeuSerHisAspGlu-460 |
| SEQ. ID. NO. 16053 | 478-GlnValAspGluLeuGly-483 |
| SEQ. ID. NO. 16054 | 516-SerAlaHisGluGluThrGly-522 |
| SEQ. ID. NO. 16055 | 560-SerGluAspAspGluGlyArgLeuLysAsn-569 |
| SEQ. ID. NO. 16056 | 575-AspSerValArgLysGluValAlaVal-583 |
| SEQ. ID. NO. 16057 | 585-ArgProProGluTyrAsnArg-591 |
| SEQ. ID. NO. 16058 | 625-PheGluGluSerAspAspValAlaAlaThrGly-635 |
| SEQ. ID. NO. 16059 | 647-GlySerArgSerAlaAlaGluSerPheLysAlaPheArgGlyArgGluProSerIle-665 |
| a130 | |
| AMPHI Regions - AMPHI | |
| SEQ. ID. NO. 16060 | 16-ThrLeuValSerGlyIle-21 |
| SEQ. ID. NO. 16061 | 36-GlySerGlySerPheGly-41 |
| SEQ. ID. NO. 16062 | 56-GlnProValGlyGlnLeu-61 |
| SEQ. ID. NO. 16063 | 91-AsnValProAsnAlaPro-96 |
| SEQ. ID. NO. 16064 | 110-GlnGlyPheAspThrLeuPheGlnHisAlaLeuAsnGlyPheAsnAlaMet-126 |
| SEQ. ID. NO. 16065 | 171-ThrAlaSerAlaPro-175 |
| SEQ. ID. NO. 16066 | 204-PheGluAlaThrCysGln-209 |
| SEQ. ID. NO. 16067 | 211-CysHisGlyGlySerIleProGlyIlePro-220 |
| SEQ. ID. NO. 16068 | 234-LysGlyLysGluThr-238 |
| SEQ. ID. NO. 16069 | 245-GluGlyPheAsnAlaMet-250 |
| Antigenic Index - Jameson-Wolf | |
| SEQ. ID. NO. 16070 | 1-MetLysGlnLeuArgAspAsnLysAlaGlnGlySer-12 |
| SEQ. ID. NO. 16071 | 35-AlaGlySerGlySerPheGlyAspValAspAlaThrThrGluAlaAlaThrGlnThrArgIleGlnProValGly-59 |
| SEQ. ID. NO. 16072 | 63-MetGlyAspGlyIleProValGlyGluArgGlnGlyGlu-75 |
| SEQ. ID. NO. 16073 | 87-AlaAlaAspSerAsnValProAsnAlaProLysLeuGluHisAsnGlyAspTrpAla-105 |
| SEQ. ID. NO. 16074 | 108-IleAlaGlnGlyPhe-112 |
| SEQ. ID. NO. 16075 | 126-MetProAlaLysGlyGlyAla-132 |
| SEQ. ID. NO. 16076 | 134-AspLeuThrAspGlnGluLeuLysArg-142 |
| SEQ. ID. NO. 16077 | 148-AlaAsnLysSerGlyGlySerPheProAsnProAspGluAlaAlaProAlaAspAsnAlaAlaSerGlyThrAlaSerAlaProAlaAspSerAlaAla ProAlaGluAlaLysAlaGluAspLysGlyAlaAla-192 |
| SEQ. ID. NO. 16078 | 197-GlyValAspGlyLysLysValPheGlu-205 |
| SEQ. ID. NO. 16079 | 221-GlyIleGlyLysLysAspAspTrpAlaProArgIleLysLysGlyLysGluThrLeuHis-240 |
| SEQ. ID. NO. 16080 | 251-ProAlaLysGlyGlyAsnAlaGlyLeuSerAspAspGluValLysAla-266 |
| SEQ. ID. NO. 16081 | 274-GlnSerGlyAlaLys-278 |
| Hydrophilic Regions - Hopp-Woods | |
| SEQ. ID. NO. 16082 | 1-MetLysGlnLeuArgAspAsnLysAlaGlnGly-11 |
| SEQ. ID. NO. 16083 | 41-GlyAspValAspAlaThrThrGluAlaAlaThr-51 |
| SEQ. ID. NO. 16084 | 68-ProValGlyGluArgGlnGlyGlu-75 |
| SEQ. ID. NO. 16085 | 87-AlaAlaAspSerAsnVal-92 |
| SEQ. ID. NO. 16086 | 96-ProLysLeuGluHisAsnGly-102 |
| SEQ. ID. NO. 16087 | 127-ProAlaLysGlyGlyAla-132 |
| SEQ. ID. NO. 16088 | 134-AspLeuThrAspGlnGluLeuLysArg-142 |
| SEQ. ID. NO. 16089 | 156-ProAsnProAspGluAlaAlaProAlaAspAsnAlaAla-168 |
| SEQ. ID. NO. 16090 | 174-AlaProAlaAspSerAlaAlaProAlaGluAlaLysAlaGluAspLysGlyAlaAla-192 |
| SEQ. ID. NO. 16091 | 198-ValAspGlyLysLysValPheGlu-205 |
| SEQ. ID. NO. 16092 | 222-IleGlyLysLysAspAspTrpAlaProArgIleLysLysGlyLysGluThrLeuHis-240 |

TABLE 1-continued

| | |
|---|---|
| SEQ. ID. NO. 16093 | 251-ProAlaLysGlyGlyAsn-256 |
| SEQ. ID. NO. 16094 | 258-GlyLeuSerAspAspGluValLysAla-266 |
| a132-2 | |
| AMPHI Regions - AMPHI | |
| SEQ. ID. NO. 16095 | 13-IleIleSerAlaLeuAlaVal-19 |
| SEQ. ID. NO. 16096 | 70-AlaThrCysMetAlaMetVal-76 |
| SEQ. ID. NO. 16097 | 92-ValGlnGlnThrGlnGlnAlaProLysProValSerAsnThr-105 |
| Antigenic Index - Jameson-Wolf | |
| SEQ. ID. NO. 16098 | 26-GlnHisGlyLysGlyAlaAspAla-33 |
| SEQ. ID. NO. 16099 | 38-GlySerGlySerGlySerAla-44 |
| SEQ. ID. NO. 16100 | 81-HisThrThrLysHisGlyLeuAspPhe-89 |
| SEQ. ID. NO. 16101 | 91-AsnValGlnGlnThrGlnGlnAlaProLysProValSerAsnThrGluProSerAlaProValProGlnGlnGlnLys-116 |
| Hydrophilic Regions - Hopp-Woods | |
| SEQ. ID. NO. 16102 | 28-GlyLysGlyAlaAspAla-33 |
| SEQ. ID. NO. 16103 | 97-GlnAlaProLysProValSerAsnThrGluProSerAla-109 |
| a134 | |
| AMPHI Regions - AMPHI | |
| SEQ. ID. NO. 16104 | 39-IleGlnSerAlaGlyThrVal-45 |
| SEQ. ID. NO. 16105 | 47-GlyLysLysThrGly-51 |
| SEQ. ID. NO. 16106 | 56-SerAspTrpMetAspIleGluLysGlnArg-65 |
| SEQ. ID. NO. 16107 | 83-ValAsnLeuLeuAspThrProGlyHis-91 |
| SEQ. ID. NO. 16108 | 97-AspThrTyrArgValLeuThrAlaVal-105 |
| SEQ. ID. NO. 16109 | 114-AlaAlaLysGlyValGlu-119 |
| SEQ. ID. NO. 16110 | 123-IleLysLeuLeuAsnValCysArg-130 |
| SEQ. ID. NO. 16111 | 142-LysTyrAspArgGluVal-147 |
| SEQ. ID. NO. 16112 | 149-AspSerLeuGluLeuLeuAspGluValGluAsnIleLeuGln-162 |
| SEQ. ID. NO. 16113 | 176-LysAsnPheLysGlyValTyrHisIleLeu-185 |
| SEQ. ID. NO. 16114 | 201-HisGluPheAspIleIleLysGlyIleAspAsn-211 |
| SEQ. ID. NO. 16115 | 254-PheGlySerAlaIle-258 |
| SEQ. ID. NO. 16116 | 265-GluIleLeuAsnSerLeuIleGluTrpAla-274 |
| SEQ. ID. NO. 16117 | 322-LysPheGluArgGlyMetLys-328 |
| SEQ. ID. NO. 16118 | 361-AspIleIleGlyIleProAsnHis-368 |
| SEQ. ID. NO. 16119 | 377-PheSerGluGlyGlu-381 |
| SEQ. ID. NO. 16120 | 395-LeuPheArgSerValArgIleLys-402 |
| SEQ. ID. NO. 16121 | 404-ProLeuLysIleLysGln-409 |
| SEQ. ID. NO. 16122 | 411-GlnLysGlyLeuGlnGlnLeuGlyGlu-419 |
| SEQ. ID. NO. 16123 | 423-ValGlnValPheLysProMetSer-430 |
| SEQ. ID. NO. 16124 | 449-SerArgLeuAlaAsnGluTyr-455 |
| SEQ. ID. NO. 16125 | 481-AlaGluPheGluLysAlaAsn-487 |
| SEQ. ID. NO. 16126 | 515-ArgTrpProAspIle-519 |
| Antigenic Index - Jameson-Wolf | |
| SEQ. ID. NO. 16127 | 4-GluIleLeuAspGlnValArgArgArgArgThrPhe-15 |
| SEQ. ID. NO. 16128 | 19-SerHisProAspAlaGlyLysThrThrLeuThr-29 |
| SEQ. ID. NO. 16129 | 43-GlyThrValLysGlyLysLysThrGlyLysPheAlaThr-55 |
| SEQ. ID. NO. 16130 | 57-AspTrpMetAspIleGluLysGlnArgGly-66 |
| SEQ. ID. NO. 16131 | 76-PheAspTyrLysAspHisThrVal-83 |
| SEQ. ID. NO. 16132 | 85-LeuLeuAspThrProGlyHisGlnAspPheSerGluAspThrTyrArg-100 |
| SEQ. ID. NO. 16133 | 113-AspAlaAlaLysGlyValGlu-119 |
| SEQ. ID. NO. 16134 | 129-CysArgLeuArgAsnThrPro-135 |
| SEQ. ID. NO. 16135 | 140-MetAsnLysTyrAspArgGluValArgAspSerLeuGluLeuLeuAspGluValGluAsn-159 |
| SEQ. ID. NO. 16136 | 173-GlyMetGlyLysAsnPheLys-179 |
| SEQ. ID. NO. 16137 | 194-AlaGlyGlyGluArgLeuProHis-201 |
| SEQ. ID. NO. 16138 | 207-LysGlyIleAspAsnProGluLeuGluGlnArgPheProLeu-220 |
| SEQ. ID. NO. 16139 | 223-GlnGlnLeuArgAspGluIleGluLeu-231 |
| SEQ. ID. NO. 16140 | 235-AlaSerAsnGluPheAsnLeu-241 |
| SEQ. ID. NO. 16141 | 275-ProAlaProLysProArgAspAlaThrValArgMetValGluProAspGluProLysPhe-294 |
| SEQ. ID. NO. 16142 | 302-GlnAlaAsnMetAspProLysHisArgAspArgIleAla-314 |
| SEQ. ID. NO. 16143 | 317-ArgValCysSerGlyLysPheGluArgGlyMetLysMetLysHisLeuArgIleAsnArgGluIleAla-339 |
| SEQ. ID. NO. 16144 | 348-SerHisAspArgGluLeuValGlu-355 |
| SEQ. ID. NO. 16145 | 365-IleProAsnHisGly-369 |
| SEQ. ID. NO. 16146 | 373-IleGlyAspSerPheSerGluGlyGluGln-382 |
| SEQ. ID. NO. 16147 | 399-ValArgIleLysAsnProLeuLysIleLysGlnLeuGlnLysGlyLeuGlnGlnLeuGlyGluGluGlyAla-422 |
| SEQ. ID. NO. 16148 | 450-ArgLeuAlaAsnGluTyrGlyVal-457 |
| SEQ. ID. NO. 16149 | 473-SerCysAspAspLysLysLysLeuAlaGluPheGluLysAlaAsnAla-488 |
| SEQ. ID. NO. 16150 | 503-AlaProAsnArgValAsnLeu-509 |
| SEQ. ID. NO. 16151 | 511-LeuThrGlnGluArgTrpProAspIleVal-520 |
| SEQ. ID. NO. 16152 | 523-GluThrArgGluHisSerVal-529 |
| Hydrophilic Regions - Hopp-Woods | |
| SEQ. ID. NO. 16153 | 4-GluIleLeuAspGlnValArgArgArgArgThr-14 |
| SEQ. ID. NO. 16154 | 21-ProAspAlaGlyLys-25 |
| SEQ. ID. NO. 16155 | 43-GlyThrValLysGlyLysLysThrGlyLys-52 |
| SEQ. ID. NO. 16156 | 59-MetAspIleGluLysGlnArgGly-66 |
| SEQ. ID. NO. 16157 | 77-AspTyrLysAspHisThr-82 |
| SEQ. ID. NO. 16158 | 92-GlnAspPheSerGluAspThrTyr-99 |
| SEQ. ID. NO. 16159 | 113-AspAlaAlaLysGlyValGlu-119 |
| SEQ. ID. NO. 16160 | 129-CysArgLeuArgAsn-133 |
| SEQ. ID. NO. 16161 | 142-LysTyrAspArgGluValArgAspSerLeuGluLeuLeuAspGluValGluAsn-159 |
| SEQ. ID. NO. 16162 | 194-AlaGlyGlyGluArgLeuProHis-201 |
| SEQ. ID. NO. 16163 | 207-LysGlyIleAspAsnProGluLeuGluGlnArgPheProLeu-220 |
| SEQ. ID. NO. 16164 | 223-GlnGlnLeuArgAspGluIleGluLeu-231 |

TABLE 1-continued

| | |
|---|---|
| SEQ. ID. NO. 16165 | 277-ProLysProArgAspAlaThrValArgMetValGluProAspGluProLysPhe-294 |
| SEQ. ID. NO. 16166 | 305-MetAspProLysHisArgAspArgIleAla-314 |
| SEQ. ID. NO. 16167 | 319-CysSerGlyLysPheGluArgGlyMetLysMetLysHisLeuArgIleAsnArgGluIleAla-339 |
| SEQ. ID. NO. 16168 | 348-SerHisAspArgGluLeuValGlu-355 |
| SEQ. ID. NO. 16169 | 376-SerPheSerGluGlyGluGln-382 |
| SEQ. ID. NO. 16170 | 399-ValArgIleLysAsnProLeuLysIleLysGlnLeuGlnLysGlyLeu-414 |
| SEQ. ID. NO. 16171 | 417-LeuGlyGluGluGlyAla-422 |
| SEQ. ID. NO. 16172 | 473-SerCysAspAspLysLysLysLeuAlaGluPheGluLysAlaAsnAla-488 |
| SEQ. ID. NO. 16173 | 512-ThrGlnGluArgTrpPro-517 |
| SEQ. ID. NO. 16174 | 523-GluThrArgGluHisSerVal-529 |
| a135 | |
| AMPHI Regions - AMPHI | |
| SEQ. ID. NO. 16175 | 29-ThrIleThrArgGlnLeuAlaAlaLeu-37 |
| SEQ. ID. NO. 16176 | 85-GluTyrThrAlaAsnLeu-90 |
| SEQ. ID. NO. 16177 | 169-AspIleAspGlyLeuTyrThr-175 |
| SEQ. ID. NO. 16178 | 185-ValArgLeuAspLysIleGluHis-192 |
| SEQ. ID. NO. 16179 | 212-GlyMetLeuThrLysIle-217 |
| SEQ. ID. NO. 16180 | 236-LeuLysProAspAla-240 |
| SEQ. ID. NO. 16181 | 242-AlaGluAlaAlaAspAsnGln-248 |
| SEQ. ID. NO. 16182 | 284-AlaGluHisAlaLeuSer-289 |
| SEQ. ID. NO. 16183 | 300-IleAlaGlyIleGluGly-305 |
| SEQ. ID. NO. 16184 | 308-SerArgMetAspThrValThrValTyr-316 |
| SEQ. ID. NO. 16185 | 318-LysAlaThrLysGlnPro-323 |
| SEQ. ID. NO. 16186 | 335-AlaAlaGluAspLeuLeuLysLeuArg-343 |
| Antigenic Index - Jameson-Wolf | |
| SEQ. ID. NO. 16187 | 1-MetLysTyrLysArgIleVal-7 |
| SEQ. ID. NO. 16188 | 11-GlyThrSerSerIleThrHisSerAspGlySerLeuSerArgGlyLysIle-27 |
| SEQ. ID. NO. 16189 | 60-GlyPheLysLysArgProValLysIleAlaAspLysGlnAlaSer-74 |
| SEQ. ID. NO. 16190 | 90-LeuSerSerAspGlyIle-95 |
| SEQ. ID. NO. 16191 | 105-AlaAspPheAlaAspLysArgArgTyrGlnAsnAlaGlyGly-118 |
| SEQ. ID. NO. 16192 | 124-LeuGlnArgArgAlaVal-129 |
| SEQ. ID. NO. 16193 | 132-IleAsnGluAsnAspThrValSerValGluGluLeuLysIleGlyAspAsnAspThrLeu-151 |
| SEQ. ID. NO. 16194 | 176-GlyAsnProAsnSerAsnProAspAlaValArgLeuAspLysIleGluHisIleAsn-194 |
| SEQ. ID. NO. 16195 | 202-GlyGlySerGlySerAlaAsnGlyThrGly-211 |
| SEQ. ID. NO. 16196 | 215-ThrLysIleLysAla-219 |
| SEQ. ID. NO. 16197 | 224-ThrGluSerGlyVal-228 |
| SEQ. ID. NO. 16198 | 233-CysSerSerLeuLysProAspAlaLeuAlaGluAlaAlaAspAsnGlnAlaAspGly-251 |
| SEQ. ID. NO. 16199 | 257-ArgAlaLysGlyLeuArgThrGlnLysGln-266 |
| SEQ. ID. NO. 16200 | 271-TyrSerGluSerArgGlyGlyValTyrValAspGluGlyAlaGluHisAlaLeuSerGluGlnGlyLysSerLeuLeu-296 |
| SEQ. ID. NO. 16201 | 305-GlyHisPheSerArgMetAspThr-312 |
| SEQ. ID. NO. 16202 | 317-SerLysAlaThrLysGlnProLeuGlyLysGlyArgVal-329 |
| SEQ. ID. NO. 16203 | 335-AlaAlaGluAspLeuLeuLysLeuArgLysAlaLys-346 |
| SEQ. ID. NO. 16204 | 350-IleHisArgAspAspTrpIleSer-357 |
| Hydrophilic Regions - Hopp-Woods | |
| SEQ. ID. NO. 16205 | 1-MetLysTyrLysArgIleVal-7 |
| SEQ. ID. NO. 16206 | 16-ThrHisSerAspGlySerLeuSerArgGlyLysIle-27 |
| SEQ. ID. NO. 16207 | 60-GlyPheLysLysArgProValLysIleAlaAspLysGlnAlaSer-74 |
| SEQ. ID. NO. 16208 | 105-AlaAspPheAlaAspLysArgArgTyrGlnAsn-115 |
| SEQ. ID. NO. 16209 | 124-LeuGlnArgArgAlaVal-129 |
| SEQ. ID. NO. 16210 | 133-AsnGluAsnAspThrValSerValGluGluLeuLysIleGlyAspAsnAspThrLeu-151 |
| SEQ. ID. NO. 16211 | 178-ProAsnSerAsnProAspAlaValArgLeuAspLysIleGluHisIleAsn-194 |
| SEQ. ID. NO. 16212 | 215-ThrLysIleLysAla-219 |
| SEQ. ID. NO. 16213 | 236-LeuLysProAspAlaLeuAlaGluAlaAlaAspAsnGlnAlaAsp-250 |
| SEQ. ID. NO. 16214 | 257-ArgAlaLysGlyLeuArgThrGlnLys-265 |
| SEQ. ID. NO. 16215 | 272-SerGluSerArgGly-276 |
| SEQ. ID. NO. 16216 | 278-ValTyrValAspGluGlyAlaGluHisAlaLeuSerGluGlnGlyLys-293 |
| SEQ. ID. NO. 16217 | 306-HisPheSerArgMetAspThr-312 |
| SEQ. ID. NO. 16218 | 318-LysAlaThrLysGlnProLeuGlyLysGlyArgVal-329 |
| SEQ. ID. NO. 16219 | 335-AlaAlaGluAspLeuLeuLysLeuArgLysAlaLys-346 |
| SEQ. ID. NO. 16220 | 351-HisArgAspAspTrp-355 |
| a136 | |
| AMPHI Regions - AMPHI | |
| SEQ. ID. NO. 16221 | 50-IleArgGlnCysIleArgGln-56 |
| SEQ. ID. NO. 16222 | 84-GlnCysHisAspGlyIleLysGlnLeuPheLysArgPheIleIleAspGlyPheLysProIleGlyArgHis-107 |
| SEQ. ID. NO. 16223 | 119-CysValLysIleAla-123 |
| SEQ. ID. NO. 16224 | 148-ArgHisCysGlnAsn-152 |
| SEQ. ID. NO. 16225 | 170-GlnHisPheGlyGlnPro-175 |
| SEQ. ID. NO. 16226 | 177-GluArgCysGlnPheVal-182 |
| SEQ. ID. NO. 16227 | 194-AsnLeuValAlaThr-198 |
| SEQ. ID. NO. 16228 | 210-GlnPheAlaGlnPro-214 |
| SEQ. ID. NO. 16229 | 216-PheGlyCysPheGlyLysPheSerGlyIleHisHisPhe-228 |
| SEQ. ID. NO. 16230 | 247-LysAlaThrLysProGlnThrValGlnIleValArg-258 |
| Antigenic Index - Jameson-Wolf | |
| SEQ. ID. NO. 16231 | 1-MetGluThrAsnAla-5 |
| SEQ. ID. NO. 16232 | 34-AlaAspGlyLeuArgLeuValAspAspArgLeuProVal-46 |
| SEQ. ID. NO. 16233 | 48-ValAspIleArgGlnCysIle-54 |
| SEQ. ID. NO. 16234 | 69-LeuGlnThrAspSer-73 |
| SEQ. ID. NO. 16235 | 84-GlnCysHisAspGlyIleLysGlnLeuPhe-93 |
| SEQ. ID. NO. 16236 | 99-AspGlyPheLysProIleGlyArgHisAsnIle-109 |
| SEQ. ID. NO. 16237 | 139-IleArgHisArgGlyGlyCysPheHisArgHisCysGlnAsnGlnProPheAsp-156 |

TABLE 1-continued

| | |
|---|---|
| SEQ. ID. NO. 16238 | 159-ThrPheGlyGlyGlyLysLeuArg-166 |
| SEQ. ID. NO. 16239 | 171-HisPheGlyGlnProValGluArg-178 |
| SEQ. ID. NO. 16240 | 184-ProAlaGlnGlnArgArgHisLysThr-192 |
| SEQ. ID. NO. 16241 | 214-ProProPheGlyCysPheGlyLysPheSerGly-224 |
| SEQ. ID. NO. 16242 | 242-AsnLeuAsnGlnAspLysAlaThrLysProGln-252 |
| SEQ. ID. NO. 16243 | 257-ValArgGlnGlyGluAlaThrProTyr-265 |
| SEQ. ID. NO. 16244 | 270-AsnProLeuTyrArgArgAsnAlaVal-278 |
| Hydrophilic Regions - Hopp-Woods | |
| SEQ. ID. NO. 16245 | 35-AspGlyLeuArgLeuValAspAspArgLeuProVal-46 |
| SEQ. ID. NO. 16246 | 48-ValAspIleArgGlnCysIle-54 |
| SEQ. ID. NO. 16247 | 87-AspGlyIleLysGlnLeuPhe-93 |
| SEQ. ID. NO. 16248 | 185-AlaGlnGlnArgArgHisLysThr-192 |
| SEQ. ID. NO. 16249 | 244-AsnGlnAspLysAlaThrLysProGln-252 |
| SEQ. ID. NO. 16250 | 273-TyrArgArgAsnAlaVal-278 |
| a137 | |
| AMPHI Regions - AMPHI | |
| SEQ. ID. NO. 16251 | 24-LeuSerTyrIleLeuGlyPhe-30 |
| SEQ. ID. NO. 16252 | 49-ThrLysGluSerLeu-53 |
| SEQ. ID. NO. 16253 | 55-AspPheLeuThrTrpGly-60 |
| SEQ. ID. NO. 16254 | 78-PheSerAspTyrLeuAlaHisProLeuAspIlePheLysValTrpGluGlyGly-95 |
| SEQ. ID. NO. 16255 | 101-GlyPheLeuGlyValValIle-107 |
| SEQ. ID. NO. 16256 | 120-PheLeuLysLeuMetAspThrValAlaProLeuValPro-132 |
| SEQ. ID. NO. 16257 | 139-ArgIleGlyAsnPheIle-144 |
| SEQ. ID. NO. 16258 | 149-TrpGlyArgValThrAspIleAsnAlaPhe-158 |
| SEQ. ID. NO. 16259 | 178-ProLeuTrpAlaGluTrpLeuGlnGlnTyr-187 |
| SEQ. ID. NO. 16260 | 190-LeuProArgHisProSerGlnLeu-197 |
| SEQ. ID. NO. 16261 | 232-TyrGlyIlePheArgPheIleAlaGluPheAlaArgGlnProAspAspTyrLeuGly-250 |
| Antigenic Index - Jameson-Wolf | |
| SEQ. ID. NO. 16262 | 36-LeuGlyArgArgArgIleAlaGln-43 |
| SEQ. ID. NO. 16263 | 48-PheThrLysGluSerLeuAspAsp-55 |
| SEQ. ID. NO. 16264 | 92-TrpGluGlyGlyMet-96 |
| SEQ. ID. NO. 16265 | 113-GlyArgLysHisGlyIle-118 |
| SEQ. ID. NO. 16266 | 136-AlaSerGlyArgIle-140 |
| SEQ. ID. NO. 16267 | 164-ProGlnAlaArgTyrGluAspLeuGluAla-173 |
| SEQ. ID. NO. 16268 | 191-ProArgHisProSerGlnLeu-197 |
| SEQ. ID. NO. 16269 | 214-PheSerLysLysGlnArgProThrGly-222 |
| SEQ. ID. NO. 16270 | 241-PheAlaArgGlnProAspAspTyrLeu-249 |
| SEQ. ID. NO. 16271 | 277-PheGlyMetLysLysGlnHis-283 |
| Hydrophilic Regions - Hopp-Woods | |
| SEQ. ID. NO. 16272 | 37-GlyArgArgArgIleAla-42 |
| SEQ. ID. NO. 16273 | 48-PheThrLysGluSerLeuAsp-54 |
| SEQ. ID. NO. 16274 | 166-AlaArgTyrGluAspLeuGluAla-173 |
| SEQ. ID. NO. 16275 | 216-LysLysGlnArgProThrGly-222 |
| SEQ. ID. NO. 16276 | 241-PheAlaArgGlnProAspAspTyr-248 |
| SEQ. ID. NO. 16277 | 278-GlyMetLysLysGlnHis-283 |
| a138 | |
| AMPHI Regions - AMPHI | |
| SEQ. ID. NO. 16278 | 21-ProTyrIleArgArgPheSerGlySer-29 |
| SEQ. ID. NO. 16279 | 74-AsnAlaMetLeuGluLysVal-80 |
| SEQ. ID. NO. 16280 | 85-GluPheValGlnGlyMet-90 |
| SEQ. ID. NO. 16281 | 109-ValAsnLysGluIleValSerMetIleAsnThrTyrGly-121 |
| SEQ. ID. NO. 16282 | 152-IleGlyGlnValGlyThrValGluSerIle-161 |
| SEQ. ID. NO. 16283 | 163-ThrGlyLeuValLysGlyLeu-169 |
| SEQ. ID. NO. 16284 | 199-GlyLysLeuAlaGluGluLeu-205 |
| SEQ. ID. NO. 16285 | 213-MetThrAsnIleAlaGlyValMetAspLysThrGlyAsnLeuLeuThrLysLeuThr-231 |
| SEQ. ID. NO. 16286 | 234-ArgIleAspGluLeuIle-239 |
| SEQ. ID. NO. 16287 | 247-GlyMetLeuProLysIleAlaSerAlaValGluAlaAlaValAsn-261 |
| SEQ. ID. NO. 16288 | 276-AlaLeuLeuLeuGluIlePheThrAspAla-285 |
| Antigenic Index - Jameson-Wolf | |
| SEQ. ID. NO. 16289 | 1-MetGluSerGluAsnIle-6 |
| SEQ. ID. NO. 16290 | 9-AlaAlaAspLysAlaArgIleLeu-16 |
| SEQ. ID. NO. 16291 | 23-IleArgArgPheSerGlySer-29 |
| SEQ. ID. NO. 16292 | 35-TyrGlyGlyAsnAlaMetThr-41 |
| SEQ. ID. NO. 16293 | 43-ProAlaLeuLysGluGlyPheAla-50 |
| SEQ. ID. NO. 16294 | 68-GlyGlyGlyProGln-72 |
| SEQ. ID. NO. 16295 | 76-MetLeuGluLysValGlyLysLysGlyGluPhe-86 |
| SEQ. ID. NO. 16296 | 91-ArgValThrAspLysGluAlaMetAsp-99 |
| SEQ. ID. NO. 16297 | 109-ValAsnLysGluIle-113 |
| SEQ. ID. NO. 16298 | 128-SerGlyArgAspAspHisPheIleLysAlaLysLysLeuLeuIleAspThrProGluGlnAsnGlyValAspIleGlyGln-154 |
| SEQ. ID. NO. 16299 | 159-GluSerIleAspThrGlyLeu-165 |
| SEQ. ID. NO. 16300 | 169-LeuIleGluArgGlyCysIle-175 |
| SEQ. ID. NO. 16301 | 182-GlyValGlyGluLysGlyGluAla-189 |
| SEQ. ID. NO. 16302 | 200-LysLeuAlaGluGluLeuAsnAlaGluLys-209 |
| SEQ. ID. NO. 16303 | 219-ValMetAspLysThrGlyAsnLeuLeuThrLysLeuThrProLysArgIleAspGluLeuIleAla-240 |
| SEQ. ID. NO. 16304 | 259-AlaValAsnGlyValLys-264 |
| SEQ. ID. NO. 16305 | 269-IleAspGlyArgValProAsnAla-276 |
| SEQ. ID. NO. 16306 | 292-LeuGlyGlyGlyGluAspAla-298 |
| Hydrophilic Regions - Hopp-Woods | |
| SEQ. ID. NO. 16307 | 1-MetGluSerGluAsn-5 |
| SEQ. ID. NO. 16308 | 9-AlaAlaAspLysAlaArgIleLeu-16 |

TABLE 1-continued

SEQ. ID. NO. 16309 43-ProAlaLeuLysGluGlyPheAla-50
SEQ. ID. NO. 16310 76-MetLeuGluLysValGlyLysLysGlyGluPhe-86
SEQ. ID. NO. 16311 91-ArgValThrAspLysGluAlaMetAsp-99
SEQ. ID. NO. 16312 109-ValAsnLysGluIle-113
SEQ. ID. NO. 16313 128-SerGlyArgAspAspHisPheIleLysAlaLysLysLeuLeuIleAspThrProGluGlnAsnGlyValAsp-151
SEQ. ID. NO. 16314 183-ValGlyGluLysGlyGluAla-189
SEQ. ID. NO. 16315 200-LysLeuAlaGluGluLeuAsnAlaGluLys-209
SEQ. ID. NO. 16316 219-ValMetAspLysThrGly-224
SEQ. ID. NO. 16317 230-LeuThrProLysArgIleAspGluLeuIleAla-240
SEQ. ID. NO. 16318 269-IleAspGlyArgVal-273
SEQ. ID. NO. 16319 294-GlyGlyGluAspAla-298
a140
AMPHI Regions - AMPHI
SEQ. ID. NO. 16320 10-TyrLeuAsnArgThr-14
SEQ. ID. NO. 16321 26-IleGlyArgAspTyrSerPhePhe-33
SEQ. ID. NO. 16322 45-SerLeuAspSerValGluLysThrAlaGly-54
SEQ. ID. NO. 16323 68-AsnAlaAlaArgThrAlaSer-74
SEQ. ID. NO. 16324 108-SerAlaThrProGluThrValGluThrAlaAla-118
SEQ. ID. NO. 16325 135-ArgAlaAlaAlaAlaValGlnHisAlaAsnAlaAlaAspGlyValArgIlePheAsnAsnLeuAlaAlaThrVal-159
SEQ. ID. NO. 16326 175-LeuLysAlaValSerAspGlyLeuAsp-183
SEQ. ID. NO. 16327 189-LeuArgValIleAlaGln-194
SEQ. ID. NO. 16328 254-SerLeuPheAlaGly-258
SEQ. ID. NO. 16329 266-IleGlyTyrLeuLysGlyLeuPheSerTyr-275
SEQ. ID. NO. 16330 290-GluHisAlaGluGlySer-295
SEQ. ID. NO. 16331 303-LeuGlyAlaLeuGly-307
SEQ. ID. NO. 16332 352-GlyThrLeuValGlyLeu-357
SEQ. ID. NO. 16333 391-GlyGlyPheThrGlyAlaThr-397
SEQ. ID. NO. 16334 412-ArgLeuValAlaGlyLeu-417
SEQ. ID. NO. 16335 425-AsnGlyTrpAsnGlyLeuAlaArg-432
Antigenic Index - Jameson-Wolf
SEQ. ID. NO. 16336 2-SerAlaGlyGlyLysGlyAlaGlyTyrLeuAsnArgThrGlyGlnArgValPro-19
SEQ. ID. NO. 16337 25-LysIleGlyArgAspTyrSer-31
SEQ. ID. NO. 16338 35-AsnIleGluThrAspGlyGlyLeu-42
SEQ. ID. NO. 16339 47-AspSerValGluLysThrAlaGlySerGluGlyAspThrLeu-60
SEQ. ID. NO. 16340 63-TyrValArgArgGlyAsnAlaAlaArgThrAlaSer-74
SEQ. ID. NO. 16341 86-HisAlaValGluGlnGlyGlySerAsnLeuGlu-96
SEQ. ID. NO. 16342 102-LeuAspAlaSerGluSerSerAlaThrProGluThrValGlu-115
SEQ. ID. NO. 16343 117-AlaAlaAlaAspArgThrAspMetProGlyIleArgProTyrGly-131
SEQ. ID. NO. 16344 144-AsnAlaAlaAspGly-148
SEQ. ID. NO. 16345 160-TyrAlaAspSerThrAlaAla-166
SEQ. ID. NO. 16346 169-AspMetGlnGlyArgArgLeuLysAlaValSerAspGlyLeuAspHisAsnAlaThrGly-188
SEQ. ID. NO. 16347 195-ThrGlnGlnAspGlyGlyThrTrpGluGlnGlyGlyValGluGlyLysMetArgGlySerThrGln-216
SEQ. ID. NO. 16348 221-AlaAlaLysThrGlyGluAsnThrThr-229
SEQ. ID. NO. 16349 240-ThrTrpSerGluAsnSerAlaAsnAlaLysThrAspSer-252
SEQ. ID. NO. 16350 259-IleArgHisAspAlaGlyAsp-265
SEQ. ID. NO. 16351 274-SerTyrGlyArgTyrLysAsnSerIleSerArgSerThrGlyAlaAspGluHisAlaGluGlySerValAsn-297
SEQ. ID. NO. 16352 315-AlaThrGlyAspLeuThrValGluGlyGlyLeuArg-326
SEQ. ID. NO. 16353 333-AspAlaPheAlaGluLysGlySerAlaLeuGlyTrpSerGlyAsnSerIleThrGluGlyThr-353
SEQ. ID. NO. 16354 362-LeuSerGlnProLeuSerAspLysAla-370
SEQ. ID. NO. 16355 377-GlyValGluArgAspLeuAsnGlyArgAspTyrThrVal-389
SEQ. ID. NO. 16356 399-AlaThrGlyLysThrGlyAlaArgAsnMetProHisThr-411
SEQ. ID. NO. 16357 421-ValGluPheGlyAsnGlyTrp-427
SEQ. ID. NO. 16358 434-SerTyrAlaGlySerLysGlnTyrGlyAsnHisSerGlyArgValGlyVal-450
Hydrophilic Regions- Hopp-Woods
SEQ. ID. NO. 16359 3-AlaGlyGlyLysGly-7
SEQ. ID. NO. 16360 36-IleGluThrAspGly-40
SEQ. ID. NO. 16361 47-AspSerValGluLysThrAlaGlySerGluGlyAspThr-59
SEQ. ID. NO. 16362 64-ValArgArgGlyAsnAlaAlaArgThrAlaSer-74
SEQ. ID. NO. 16363 86-HisAlaValGluGlnGlyGlySerAsnLeu-95
SEQ. ID. NO. 16364 102-LeuAspAlaSerGluSerSerAlaThrProGluThrValGlu-115
SEQ. ID. NO. 16365 117-AlaAlaAlaAspArgThrAspMetProGly-126
SEQ. ID. NO. 16366 144-AsnAlaAlaAspGly-148
SEQ. ID. NO. 16367 169-AspMetGlnGlyArgArgLeuLysAlaValSerAspGlyLeuAspHisAsnAlaThr-187
SEQ. ID. NO. 16368 205-GlyGlyValGluGlyLysMetArgGlySerThr-215
SEQ. ID. NO. 16369 223-LysThrGlyGluAsnThrThr-229
SEQ. ID. NO. 16370 244-AsnSerAlaAsnAlaLysThrAspSer-252
SEQ. ID. NO. 16371 259-IleArgHisAspAlaGlyAsp-265
SEQ. ID. NO. 16372 277-ArgTyrLysAsnSerIleSerArgSerThrGlyAlaAspGluHisAlaGluGlySerVal-296
SEQ. ID. NO. 16373 333-AspAlaPheAlaGluLysGlySer-340
SEQ. ID. NO. 16374 364-GlnProLeuSerAspLysAla-370
SEQ. ID. NO. 16375 377-GlyValGluArgAspLeuAsnGlyArgAspTyrThr-388
SEQ. ID. NO. 16376 399-AlaThrGlyLysThrGlyAlaArgAsnMetPro-409
a141
AMPHI Regions - AMPHI
SEQ. ID. NO. 16377 11-GlnSerSerThrMetArgProIleGlyGluIle-21
SEQ. ID. NO. 16378 32-IleGluProTyrGly-36
SEQ. ID. NO. 16379 44-ProAlaGluAlaPheLysLeuPro-51
SEQ. ID. NO. 16380 80-AlaAspAlaLeuArgHisIle-86
SEQ. ID. NO. 16381 131-PheHisAlaIleGlyAla-136
SEQ. ID. NO. 16382 139-AsnLeuLeuAlaAlaMetLeuAspAsn-147

TABLE 1-continued

| | |
|---|---|
| SEQ. ID. NO. 16383 | 174-GlnLeuArgAsnIleIleAspGlyMetGlyLysProValAspGlyValMetArgPro-192 |
| SEQ. ID. NO. 16384 | 212-AspIleSerAspLeuLysGluArgLeuGly-221 |
| SEQ. ID. NO. 16385 | 245-MetAlaAlaLeuLeuLysAspAlaIleLysProAsnLeu-257 |
| SEQ. ID. NO. 16386 | 259-GlnThrIleGluGlyThrPro-265 |
| SEQ. ID. NO. 16387 | 272-ProPheAlaAsnIleAlaHisGlyCysAsnSerValThrAlaThrArgLeuAlaLysHisLeuAlaAspTyrAla-296 |
| SEQ. ID. NO. 16388 | 330-AlaThrValArgAla-334 |
| SEQ. ID. NO. 16389 | 351-LeuAspAlaLeuGluLysGlyLeuProAsnLeuLeuLysHisIleSerAsnLeuLysAsnValPheGly-373 |
| SEQ. ID. NO. 16390 | 406-SerLeuThrGluValTrpGlyLys-413 |
| SEQ. ID. NO. 16391 | 420-AspLeuAlaArgLysValValAsnAlaIleGluSerGln-432 |
| SEQ. ID. NO. 16392 | 473-IleAlaSerLeuGluLys-478 |
| SEQ. ID. NO. 16393 | 525-ValAlaLeuCysGlyAsnMetMetLysMetProGlyLeuProLysValProAlaAla-543 |
| Antigenic Index - Jameson-Wolf | |
| SEQ. ID. NO. 16394 | 3-PheLysThrAspAlaGluIleAlaGlnSerSerThrMetArgProIleGly-19 |
| SEQ. ID. NO. 16395 | 27-LeuAsnValAspAsnIleGluProTyrGly-36 |
| SEQ. ID. NO. 16396 | 38-TyrLysAlaLysIleAsnProAlaGluAlaPheLysLeuProGlnLysGlnGlyArg-56 |
| SEQ. ID. NO. 16397 | 64-AsnProThrProAlaGlyGluGlyLysThrThr-74 |
| SEQ. ID. NO. 16398 | 81-AspAlaLeuArgHisIleGlyLysAspSerValIleAlaLeuArgGluProSerLeuGlyPro-101 |
| SEQ. ID. NO. 16399 | 105-ValLysGlyGlyAlaAlaGlyGlyGly-113 |
| SEQ. ID. NO. 16400 | 151-GlnGlyAsnGluLeuAsnIleAspProLysArgValLeuTrp-164 |
| SEQ. ID. NO. 16401 | 166-ArgValValAspMetAsnAspArgGlnLeuArgAsnIleIleAspGlyMetGlyLysProValAspGlyValMetArgProAspGlyPheAspIle-197 |
| SEQ. ID. NO. 16402 | 211-LysAspIleSerAspLeuLysGluArgLeuGly-221 |
| SEQ. ID. NO. 16403 | 227-TyrAlaLysAspGlySerProValTyr-235 |
| SEQ. ID. NO. 16404 | 237-LysAspLeuLysAlaAsnGly-243 |
| SEQ. ID. NO. 16405 | 251-AspAlaIleLysProAsnLeu-257 |
| SEQ. ID. NO. 16406 | 287-ArgLeuAlaLysHisLeuAla-293 |
| SEQ. ID. NO. 16407 | 306-LeuGlyAlaGluLysPheCysAspIleLysCysArgLeuAlaGlyLeuLysProAspAla-325 |
| SEQ. ID. NO. 16408 | 335-LeuLysTyrAsnGlyGlyValGluArgAlaAsnLeuGlyGluGluAsnLeuAspAlaLeuGluLysGlyLeuProAsnLeu-361 |
| SEQ. ID. NO. 16409 | 383-PheValSerAspSerAspAlaGluLeuAlaMetIleGluLysAlaCysAla-399 |
| SEQ. ID. NO. 16410 | 411-TrpGlyLysGlyGlyAlaGlyGlyAlaAspLeuAlaArgLysValValAsn-427 |
| SEQ. ID. NO. 16411 | 429-IleGluSerGlnThrAsnAsnPheGly-437 |
| SEQ. ID. NO. 16412 | 444-LeuGlyIleLysAspLysIleArgAlaIleAla-454 |
| SEQ. ID. NO. 16413 | 458-TyrGlyAlaGluAspValAspPheSerAla-467 |
| SEQ. ID. NO. 16414 | 474-AlaSerLeuGluLysLeuGlyLeuAspLysMetPro-485 |
| SEQ. ID. NO. 16415 | 494-SerLeuSerAspAsnAlaLysLeu-501 |
| SEQ. ID. NO. 16416 | 503-GlyCysProGluAspPheArgIle-510 |
| SEQ. ID. NO. 16417 | 534-MetProGlyLeuPro-538 |
| SEQ. ID. NO. 16418 | 541-ProAlaAlaGluLysIleAspValAspAlaGluGly-552 |
| Hydrophilic Regions - Hopp-Woods | |
| SEQ. ID. NO. 16419 | 3-PheLysThrAspAlaGluIleAlaGln-11 |
| SEQ. ID. NO. 16420 | 38-TyrLysAlaLysIleAsnPro-44 |
| SEQ. ID. NO. 16421 | 46-GluAlaPheLysLeuProGlnLysGlnGlyArg-56 |
| SEQ. ID. NO. 16422 | 67-ProAlaGlyGluGlyLysThr-73 |
| SEQ. ID. NO. 16423 | 81-AspAlaLeuArgHisIleGlyLysAspSerValIleAlaLeuArgGluProSer-98 |
| SEQ. ID. NO. 16424 | 155-LeuAsnIleAspProLysArgValLeuTrp-164 |
| SEQ. ID. NO. 16425 | 166-ArgValValAspMetAsnAspArgGlnLeuArgAsnIleIle-179 |
| SEQ. ID. NO. 16426 | 181-GlyMetGlyLysProValAspGlyValMetArgProAspGlyPhe-195 |
| SEQ. ID. NO. 16427 | 211-LysAspIleSerAspLeuLysGluArgLeuGly-221 |
| SEQ. ID. NO. 16428 | 228-AlaLysAspGlySer-232 |
| SEQ. ID. NO. 16429 | 237-LysAspLeuLysAla-241 |
| SEQ. ID. NO. 16430 | 287-ArgLeuAlaLysHisLeuAla-293 |
| SEQ. ID. NO. 16431 | 306-LeuGlyAlaGluLysPheCysAspIleLysCysArgLeuAlaGlyLeuLysProAspAla-325 |
| SEQ. ID. NO. 16432 | 339-GlyGlyValGluArgAlaAsnLeuGlyGluGluAsnLeuAspAlaLeuGluLysGlyLeu-358 |
| SEQ. ID. NO. 16433 | 383-PheValSerAspSerAspAlaGluLeuAlaMetIleGluLysAlaCysAla-399 |
| SEQ. ID. NO. 16434 | 420-AspLeuAlaArgLysValValAsn-427 |
| SEQ. ID. NO. 16435 | 444-LeuGlyIleLysAspLysIleArgAlaIleAla-454 |
| SEQ. ID. NO. 16436 | 458-TyrGlyAlaGluAspValAspPheSerAla-467 |
| SEQ. ID. NO. 16437 | 474-AlaSerLeuGluLysLeuGlyLeuAspLysMetPro-485 |
| SEQ. ID. NO. 16438 | 503-GlyCysProGluAspPheArgIle-510 |
| SEQ. ID. NO. 16439 | 541-ProAlaAlaGluLysIleAspValAspAlaGluGly-552 |
| a142 | |
| AMPHI Regions - AMPHI | |
| SEQ. ID. NO. 16440 | 26-ArgPheAlaAlaMetProAspValValGlyLys-36 |
| SEQ. ID. NO. 16441 | 44-GlyGlnProGlyLysMetPhe-50 |
| SEQ. ID. NO. 16442 | 100-AlaValThrProCysArg-105 |
| SEQ. ID. NO. 16443 | 107-ValCysArgAspAspMetAsn-113 |
| SEQ. ID. NO. 16444 | 118-GlyCysHisArgIleThrGluArgSerLeuLysSerPheLeuGlnIleArgHisPheSerProLeu-139 |
| SEQ. ID. NO. 16445 | 174-LeuArgValGlnArgIleLeuAspPheGlyLysPheCysGlnGlnVal-189 |
| SEQ. ID. NO. 16446 | 202-LeuAspSerValValThrLeuValHisPhePheAlaAspPheLeuIle-217 |
| SEQ. ID. NO. 16447 | 239-AlaAspAsnGlnThrArgPhePheLysAlaGly-249 |
| SEQ. ID. NO. 16448 | 259-AsnAlaArgLeuIleArgGlnIleLeuLys-268 |
| Antigenic Index - Jameson-Wolf | |
| SEQ. ID. NO. 16449 | 31-ProAspValValGly-35 |
| SEQ. ID. NO. 16450 | 38-LeuPheGlyArgGlnAlaGlyGlnProGlyLysMet-49 |
| SEQ. ID. NO. 16451 | 59-GlnArgIleAspAlaGluAlaAlaValPheArgGlnAspArgAsnAspSerArgThrProValAspAlaGlnHisHisGlyArgArgLeuValArg AsnArgArgAsnArgArgHisCysAsnAla-100 |
| SEQ. ID. NO. 16452 | 102-ThrProCysArgThrValCysArgAspAspMetAsnAlaCysArgThrGlyCysHisArgIleThrGluArgSerLeuLys-128 |
| SEQ. ID. NO. 16453 | 147-AlaAlaHisLysAla-151 |
| SEQ. ID. NO. 16454 | 153-ProMetCysSerSerSerAspSerLysSerArgArgSerAspIleSerAlaArgTyr-171 |
| SEQ. ID. NO. 16455 | 180-LeuAspPheGlyLysPheCys-186 |
| SEQ. ID. NO. 16456 | 225-GlnLeuGlnLysAsnThrSer-231 |

TABLE 1-continued

| | |
|---|---|
| SEQ. ID. NO. 16457 | 237-PheGlnAlaAspAsnGlnThrArgPhePheLysAlaGlyGlnAspThrGlyGlnAlaGlyAlaGlnAsn-259 |
| SEQ. ID. NO. 16458 | 267-LeuLysValGlnArgAlaValPheArgGlnLysThrAspAsnProPro-282 |
| SEQ. ID. NO. 16459 | 291-IleGlnAsnArgProGluLeuGlyHisGlnGly-301 |
| SEQ. ID. NO. 16460 | 307-GlnThrAspIleAspArgArgMetPhe-315 |
| Hydrophilic Regions - Hopp-Woods | |
| SEQ. ID. NO. 16461 | 42-GlnAlaGlyGlnPro-46 |
| SEQ. ID. NO. 16462 | 59-GlnArgIleAspAlaGluAlaAlaValPheArgGlnAspArgAsnAspSerArgThrProValAspAlaGlnHisHisGlyArgArgLeuValArgAsnArgArgAsnArgArgHisCys-98 |
| SEQ. ID. NO. 16463 | 106-ThrValCysArgAspAspMetAsnAlaCysArg-116 |
| SEQ. ID. NO. 16464 | 121-ArgIleThrGluArgSerLeuLys-128 |
| SEQ. ID. NO. 16465 | 147-AlaAlaHisLysAla-151 |
| SEQ. ID. NO. 16466 | 156-SerSerSerAspSerLysSerArgArgSerAspIleSerAla-169 |
| SEQ. ID. NO. 16467 | 237-PheGlnAlaAspAsnGlnThrArgPhePheLysAlaGlyGlnAspThrGlyGln-254 |
| SEQ. ID. NO. 16468 | 267-LeuLysValGlnArgAlaValPheArgGlnLysThrAspAsn-280 |
| SEQ. ID. NO. 16469 | 291-IleGlnAsnArgProGluLeuGly-298 |
| SEQ. ID. NO. 16470 | 309-AspIleAspArgArgMetPhe-315 |
| a144 | |
| AMPHI Regions - AMPHI | |
| SEQ. ID. NO. 16471 | 36-LeuGlyGlyIleValGlnGluPhe-43 |
| SEQ. ID. NO. 16472 | 45-ValLeuAlaAspGlyValArg-51 |
| SEQ. ID. NO. 16473 | 71-IleAsnLysGlnIleGlyArgValAlaGlyArg-81 |
| SEQ. ID. NO. 16474 | 136-ValGlyArgArgLeu-140 |
| SEQ. ID. NO. 16475 | 159-TyrArgTyrLeuSerArgHis-165 |
| SEQ. ID. NO. 16476 | 185-GlyProAlaArgCysGlySerAlaTyrSerAlaGly-196 |
| SEQ. ID. NO. 16477 | 200-SerGlyArgCysArgLysThrAlaArgLeuAsnGlyPheArgArgProArgSer-217 |
| Antigenic Index - Jameson-Wolf | |
| SEQ. ID. NO. 16478 | 1-MetSerAspThrProAlaThrArgAspPheGlyLeuIleAspGlyArgAla-17 |
| SEQ. ID. NO. 16479 | 23-LeuSerAsnArgArgGlyThrArg-30 |
| SEQ. ID. NO. 16480 | 48-AspGlyValArgGlu-52 |
| SEQ. ID. NO. 16481 | 58-PheAspAspAlaAlaSerTyrAlaAspAsnProPheGlnIleAsn-72 |
| SEQ. ID. NO. 16482 | 78-ValAlaGlyArgIleArgGlyAlaAla-86 |
| SEQ. ID. NO. 16483 | 88-AspIleAsnGlyArgThrTyrArgValGluAlaAsnGluGlyArgAsnAlaLeuHisGlyGlySerHis-110 |
| SEQ. ID. NO. 16484 | 121-AlaAlaAspGlyArgSerValValLeu-129 |
| SEQ. ID. NO. 16485 | 135-ThrValGlyArgArgLeuSerGlnArgPheGly-145 |
| SEQ. ID. NO. 16486 | 151-ProLeuGlyArgGlyArgProAlaTyr-159 |
| SEQ. ID. NO. 16487 | 161-TyrLeuSerArgHisArgAlaArgArgHisGlyValArgProAspAlaAlaHis-178 |
| SEQ. ID. NO. 16488 | 182-AlaGlyArgGlyProAlaArgCysGlySer-191 |
| SEQ. ID. NO. 16489 | 194-SerAlaGlyArgThrTyrSerGlyArgCysArgLysThrAlaArgLeuAsnGlyPheArgArgProArgSerIle-218 |
| Hydrophilic Regions - Hopp-Woods | |
| SEQ. ID. NO. 16490 | 1-MetSerAspThrProAlaThrArgAsp-9 |
| SEQ. ID. NO. 16491 | 24-SerAsnArgArgGlyThrArg-30 |
| SEQ. ID. NO. 16492 | 48-AspGlyValArgGlu-52 |
| SEQ. ID. NO. 16493 | 58-PheAspAspAlaAlaSer-63 |
| SEQ. ID. NO. 16494 | 78-ValAlaGlyArgIleArgGlyAlaAla-86 |
| SEQ. ID. NO. 16495 | 89-IleAsnGlyArgThrTyrArgValGluAlaAsnGluGlyArgAsnAlaLeu-105 |
| SEQ. ID. NO. 16496 | 121-AlaAlaAspGlyArgSerValValLeu-129 |
| SEQ. ID. NO. 16497 | 135-ThrValGlyArgArgLeuSerGln-142 |
| SEQ. ID. NO. 16498 | 153-GlyArgGlyArgProAla-158 |
| SEQ. ID. NO. 16499 | 163-SerArgHisArgAlaArgArgHisGlyValArgProAspAla-176 |
| SEQ. ID. NO. 16500 | 183-GlyArgGlyProAlaArgCys-189 |
| SEQ. ID. NO. 16501 | 197-ArgThrTyrSerGlyArgCysArgLysThrAlaArg-208 |
| SEQ. ID. NO. 16502 | 210-AsnGlyPheArgArgProArgSerIle-218 |
| a146 | |
| AMPHI Regions - AMPHI | |
| SEQ. ID. NO. 16503 | 19-GluGlnTyrGlyLeuPheAspPheMetProCys-29 |
| SEQ. ID. NO. 16504 | 34-ProLeuAspAsnPheProThrVal-41 |
| SEQ. ID. NO. 16505 | 64-GlyPheGlyGlnArgIleSerAsnLeuSerArg-74 |
| SEQ. ID. NO. 16506 | 95-LeuArgAlaCysAla-99 |
| SEQ. ID. NO. 16507 | 105-HisValArgValPheGlnLys-111 |
| SEQ. ID. NO. 16508 | 140-ThrArgArgValArg-144 |
| SEQ. ID. NO. 16509 | 158-ArgHisGlnArgGlyPheAlaArg-165 |
| Antigenic Index - Jameson-Wolf | |
| SEQ. ID. NO. 16510 | 6-LeuArgProArgGlnValIleIleAspHisAspLysIleGluGln-20 |
| SEQ. ID. NO. 16511 | 29-CysLeuArgGlnProProLeuAspAsn-37 |
| SEQ. ID. NO. 16512 | 41-ValArgProAlaSerValGluThrArgSerLysHisIleGluArgArgArgGlnAspLysAspAlaAspGlyPheGlyGlnArgIleSerAsnLeuSer-73 |
| SEQ. ID. NO. 16513 | 86-ThrCysArgArgGlnArgIleHisThr-94 |
| SEQ. ID. NO. 16514 | 112-SerLeuLeuArgAspLysArgLeuLys-120 |
| SEQ. ID. NO. 16515 | 138-ArgArgThrArgArgValArgHisGlyAsnAlaGln-149 |
| SEQ. ID. NO. 16516 | 155-GlnGlnProArgHisGlnArgGlyPheAla-164 |
| SEQ. ID. NO. 16517 | 166-AlaGlySerGlyArgAsnAspLysAspValAlaPheSerIle-179 |
| SEQ. ID. NO. 16518 | 195-GlnArgThrProGlyPhe-200 |
| Hydrophilic Regions - Hopp-Woods | |
| SEQ. ID. NO. 16519 | 6-LeuArgProArgGlnValIleIleAspHisAspLysIleGluGln-20 |
| SEQ. ID. NO. 16520 | 44-AlaSerValGluThrArgSerLysHisIleGluArgArgArgGlnAspLysAspAlaAspGlyPheGly-66 |
| SEQ. ID. NO. 16521 | 86-ThrCysArgArgGlnArgIleHisThr-94 |
| SEQ. ID. NO. 16522 | 112-SerLeuLeuArgAspLysArgLeuLys-120 |
| SEQ. ID. NO. 16523 | 138-ArgArgThrArgArgValArgHisGlyAsn-147 |

TABLE 1-continued

| | |
|---|---|
| SEQ. ID. NO. 16524 | 156-GlnProArgHisGlnArgGlyPheAla-164 |
| SEQ. ID. NO. 16525 | 167-GlySerGlyArgAsnAspLysAspValAla-176 |
| a148 | |
| AMPHI Regions - AMPHI | |
| SEQ. ID. NO. 16526 | 25-AlaAspLysIleArgLysIleGluAsnTrpPro-35 |
| SEQ. ID. NO. 16527 | 49-GlnSerAlaGluTyrPheArgLeuLeuValAspLeu-60 |
| SEQ. ID. NO. 16528 | 150-AlaGlyLeuGluLeuIleArgLysLeuGlyGlyGluIle-162 |
| SEQ. ID. NO. 16529 | 165-AlaAlaAlaIleLeuGluPheThrAspLeuGlnGlyGlyLysAsnIleArg-181 |
| Antigenic Index - Jameson-Wolf | |
| SEQ. ID. NO. 16530 | 4-LysThrSerAsnLeu-8 |
| SEQ. ID. NO. 16531 | 24-LeuAlaAspLysIleArgLysIleGluAsnTrpProGlnLysGly-38 |
| SEQ. ID. NO. 16532 | 66-MetAspGlnLysIleAspIle-72 |
| SEQ. ID. NO. 16533 | 76-LeuAspAlaArgGly-80 |
| SEQ. ID. NO. 16534 | 97-ProIleArgLysLysGlyLysLeuPro-105 |
| SEQ. ID. NO. 16535 | 117-TyrGlyGluAlaAlaVal-122 |
| SEQ. ID. NO. 16536 | 124-IleHisThrAspAlaValLysLeuGlySer-133 |
| SEQ. ID. NO. 16537 | 153-GluLeuIleArgLysLeuGlyGlyGluIleValGlu-164 |
| SEQ. ID. NO. 16538 | 172-ThrAspLeuGlnGlyGlyLysAsnIleArgAlaSerGlyAlaPro-186 |
| SEQ. ID. NO. 16539 | 192-GlnAsnGluGlyCysMetLysGly-199 |
| Hydrophilic Regions - Hopp-Woods | |
| SEQ. ID. NO. 16540 | 24-LeuAlaAspLysIleArgLysIleGluAsnTrpPro-35 |
| SEQ. ID. NO. 16541 | 66-MetAspGlnLysIleAspIle-72 |
| SEQ. ID. NO. 16542 | 97-ProIleArgLysLysGlyLysLeuPro-105 |
| SEQ. ID. NO. 16543 | 117-TyrGlyGluAlaAlaVal-122 |
| SEQ. ID. NO. 16544 | 124-IleHisThrAspAlaValLysLeuGlySer-133 |
| SEQ. ID. NO. 16545 | 153-GluLeuIleArgLysLeuGlyGlyGluIleValGlu-164 |
| SEQ. ID. NO. 16546 | 178-LysAsnIleArgAlaSerGly-184 |
| SEQ. ID. NO. 16547 | 195-GlyCysMetLysGly-199 |
| a149 | |
| AMPHI Regions - AMPHI | |
| SEQ. ID. NO. 16548 | 72-AsnLeuGlyAspAlaLeuAspGlyValProGlyIle-83 |
| SEQ. ID. NO. 16549 | 101-ThrGlyArgArgIleLysValLeuAsnHisHisGlyGluThrGlyAspMet-117 |
| SEQ. ID. NO. 16550 | 135-GlnValGluIleLeuArgGlyProValThr-144 |
| SEQ. ID. NO. 16551 | 152-ValAlaGlyLeuValAsp-157 |
| SEQ. ID. NO. 16552 | 164-ProGluLysMetProGluAsnGlyVal-172 |
| SEQ. ID. NO. 16553 | 184-AsnLeuGluLysLeu-188 |
| SEQ. ID. NO. 16554 | 220-TyrArgAsnLeuLysArgLeuProAspSerHis-230 |
| SEQ. ID. NO. 16555 | 345-PheProGlyPheGlu-349 |
| SEQ. ID. NO. 16556 | 366-AlaGlyAspAlaValGluAsnPhePheAsnAsn-376 |
| SEQ. ID. NO. 16557 | 389-ProIleGlyArgLeuLys-394 |
| SEQ. ID. NO. 16558 | 411-AlaThrSerGluAla-415 |
| SEQ. ID. NO. 16559 | 565-ArgPheGlyAsnTyrIleTyrAlaGln-573 |
| SEQ. ID. NO. 16560 | 576-AsnAspGlyArgGlyProLysSerIleGluAsp-586 |
| SEQ. ID. NO. 16561 | 627-ArgGlyArgLeuLysAsnLeuProSer-635 |
| Antigenic Index -Jameson-Wolf | |
| SEQ. ID. NO. 16562 | 23-GlnAlaHisGlyThrGluGlnSerVal-31 |
| SEQ. ID. NO. 16563 | 40-GlyLysSerArgProArgAlaThrSerGly-49 |
| SEQ. ID. NO. 16564 | 55-ThrAlaSerAspLysIleIleSerGlyAspThrLeuArgGlnLysAla-70 |
| SEQ. ID. NO. 16565 | 97-IleArgGlyGlnThrGlyArgArgIleLysVal-107 |
| SEQ. ID. NO. 16566 | 109-AsnHisHisGlyGluThrGlyAspMetAlaAspPheSerProAspHis-124 |
| SEQ. ID. NO. 16567 | 137-GluIleLeuArgGlyPro-142 |
| SEQ. ID. NO. 16568 | 157-AspValAlaAspGlyLysIleProGluLysMetProGluAsnGlyValSerGlyGluLeuGlyLeu-178 |
| SEQ. ID. NO. 16569 | 180-LeuSerSerGlyAsnLeuGluLysLeuThrSerGlyGly-192 |
| SEQ. ID. NO. 16570 | 207-GlyLeuTyrArgLysSerGlyAspTyrAlaValProArgTyrArgAsnLeuLysArgLeuProAspSerHisAlaAspSerGlnThrGly-236 |
| SEQ. ID. NO. 16571 | 244-GlyGluLysGlyPhe-248 |
| SEQ. ID. NO. 16572 | 252-AlaTyrSerAspArgArgAspGlnTyrGly-261 |
| SEQ. ID. NO. 16573 | 263-ProAlaHisSerHisGluTyrAspAspCysHisAla-274 |
| SEQ. ID. NO. 16574 | 281-SerLeuIleAsnLysArgTyrLeu-288 |
| SEQ. ID. NO. 16575 | 295-LeuThrGluGluAspIleAspTyrAspAsnProGlyLeu-307 |
| SEQ. ID. NO. 16576 | 310-GlyPheHisAspAspAspAspAlaHis-318 |
| SEQ. ID. NO. 16577 | 321-AlaHisAsnGlyLysProTrpIleAspLeuArgAsnLysArgTyrGluLeuArgAlaGluTrpLysGlnProPheProGly-347 |
| SEQ. ID. NO. 16578 | 354-HisLeuAsnArgAsnAspTyrArgHisAspGluLysAlaGlyAspAlaVal-370 |
| SEQ. ID. NO. 16579 | 374-PheAsnAsnGlnThrGlnAsnAlaArgIleGluLeuArgHisGlnProIleGlyArgLeuLysGlySerTrp-397 |
| SEQ. ID. NO. 16580 | 402-LeuGlyGlnLysSerSerAlaLeu-409 |
| SEQ. ID. NO. 16581 | 411-AlaThrSerGluAlaValLys-417 |
| SEQ. ID. NO. 16582 | 422-LeuAspAsnLysVal-426 |
| SEQ. ID. NO. 16583 | 437-AlaAsnTrpAspAsnPheThrLeuGluGlyGlyValArgValGluLysGlnLysAlaSerIleArgTyrAspLysAlaLeuIleAspArgGluAsn TyrTyrAsnHisProLeuProAsp-476 |
| SEQ. ID. NO. 16584 | 478-GlyAlaHisArgGlnThrAla-484 |
| SEQ. ID. NO. 16585 | 506-SerHisGlnGluArgLeuProSerThrGlnGluLeuTyrAlaHisGly-521 |
| SEQ. ID. NO. 16586 | 531-ValGlyAsnLysHisLeuAsnLysGluArgSerAsnAsnIle-544 |
| SEQ. ID. NO. 16587 | 550-TyrGluGlyAspArgTrpGln-556 |
| SEQ. ID. NO. 16588 | 562-TyrArgAsnArgPheGlyAsn-568 |
| SEQ. ID. NO. 16589 | 574-ThrLeuAsnAspGlyArgGlyProLysSerIleGluAspAspSerGluMetLysLeu-592 |
| SEQ. ID. NO. 16590 | 594-ArgTyrAsnGlnSerGlyAlaAspPheTyrGlyAlaGluGly-607 |
| SEQ. ID. NO. 16591 | 609-IleTyrPheLysProThrProArgTyrArgIle-619 |
| SEQ. ID. NO. 16592 | 621-ValSerGlyAspTyrValArgGlyArgLeuLysAsnLeuProSerLeuProGlyArgGluAspAlaTyrGlyAsnArg-646 |
| SEQ. ID. NO. 16593 | 651-GlnAlaAspGlnAsnAlaProArgValProAla-661 |
| SEQ. ID. NO. 16594 | 671-SerLeuThrAspArgIleAspAla-678 |
| SEQ. ID. NO. 16595 | 689-AsnLysLeuAlaArgTyrGluThrArgThrProGlyHis-701 |

TABLE 1-continued

SEQ. ID. NO. 16596 707-GlyAlaAsnTyrArgArgAsnThrArgTyrGlyGluTrp-719
SEQ. ID. NO. 16597 725-AlaAspAsnLeuLeu-729
SEQ. ID. NO. 16598 739-PheLeuSerAspThrProGlnMetGlyArgSerPheThrGlyGlyVal-754
Hydrophilic Regions - Hopp-Woods
SEQ. ID. NO. 16599 25-HisGlyThrGluGln-29
SEQ. ID. NO. 16600 40-GlyLysSerArgProArgAlaThr-47
SEQ. ID. NO. 16601 55-ThrAlaSerAspLysIleIleSer-62
SEQ. ID. NO. 16602 64-AspThrLeuArgGlnLysAla-70
SEQ. ID. NO. 16603 100-GlnThrGlyArgArgIleLysVal-107
SEQ. ID. NO. 16604 112-GlyGluThrGlyAspMetAlaAspPheSerPro-122
SEQ. ID. NO. 16605 157-AspValAlaAspGlyLysIleProGluLysMetProGluAsnGlyValSer-173
SEQ. ID. NO. 16606 181-SerSerGlyAsnLeuGluLysLeuThr-189
SEQ. ID. NO. 16607 207-GlyLeuTyrArgLysSerGlyAsp-214
SEQ. ID. NO. 16608 219-ArgTyrArgAsnLeuLysArgLeuProAspSerHisAlaAspSerGlnThr-235
SEQ. ID. NO. 16609 253-TyrSerAspArgArgAspGlnTyr-260
SEQ. ID. NO. 16610 267-HisGluTyrAspAspCysHisAla-274
SEQ. ID. NO. 16611 295-LeuThrGluGluAspIleAspTyrAspAsn-304
SEQ. ID. NO. 16612 311-PheHisAspAspAspAspAlaHis-318
SEQ. ID. NO. 16613 330-LeuArgAsnLysArgTyrGluLeuArgAlaGluTrp-341
SEQ. ID. NO. 16614 354-HisLeuAsnArgAsnAspTyrArgHisAspGluLysAlaGlyAspAlaVal-370
SEQ. ID. NO. 16615 378-ThrGlnAsnAlaArgIleGluLeuArgHis-387
SEQ. ID. NO. 16616 391-GlyArgLeuLysGly-395
SEQ. ID. NO. 16617 411-AlaThrSerGluAlaValLys-417
SEQ. ID. NO. 16618 446-GlyGlyValArgValGluLysGlnLysAlaSerIleArgTyrAspLysAlaLeuIleAspArgGluAsnTyr-469
SEQ. ID. NO. 16619 478-GlyAlaHisArgGlnThrAla-484
SEQ. ID. NO. 16620 506-SerHisGlnGluArgLeuProSer-513
SEQ. ID. NO. 16621 535-HisLeuAsnLysGluArgSerAsnAsn-543
SEQ. ID. NO. 16622 550-TyrGluGlyAspArgTrp-555
SEQ. ID. NO. 16623 575-LeuAsnAspGlyArgGlyProLysSerIleGluAspAspSerGluMetLysLeu-592
SEQ. ID. NO. 16624 603-TyrGlyAlaGluGly-607
SEQ. ID. NO. 16625 613-ProThrProArgTyrArgIle-619
SEQ. ID. NO. 16626 624-AspTyrValArgGlyArgLeuLysAsn-632
SEQ. ID. NO. 16627 637-ProGlyArgGluAspAlaTyrGly-644
SEQ. ID. NO. 16628 652-AlaAspGlnAsnAlaProArgValProAla-661
SEQ. ID. NO. 16629 671-SerLeuThrAspArgIleAspAla-678
SEQ. ID. NO. 16630 690-LysLeuAlaArgTyrGluThrArgThrProGly-700
SEQ. ID. NO. 16631 709-AsnTyrArgArgAsnThrArgTyrGly-717
a150
AMPHI Regions - AMPHI
SEQ. ID. NO. 16632 1-MetGlnAsnThrAsnProProLeuProProMetProProGluIleThrGlnLeuLeuSerGlyLeuAspAlaAlaGlnTrpAlaTrpLeuSerGlyTyrAla
TrpAlaLysAlaGlyAsnGlyAlaSerAlaGlyLeuProAlaLeuGlnThrAlaLeuProThrAlaGluProPheSerValThrValLeuSerAlaSerGlnThr
GlyAsnAlaLysSerValAlaAspLysAlaAlaAspSerLeuGluAlaAlaGlyIleGlnValSerArgAlaGluLeuLysAspTyrLysAlaLysAsnIle
AlaGlyGluArgArgLeuLeuLeuValThrSerThrGlnGlyGluGlyGluProProGluGluAlaValValLeuHisLysLeuLeuAsnGlyLysLys
AlaProLysLeuAspLysLeuGlnPheAlaValLeuGlyLeuGlyAspSerSerTyrProAsnPheCysArgAlaGlyLysAspPheAspLysArgPhe
GluGluLeuGlyAlaLysArgLeuLeuGluArgValAspAlaAspLeuAspPheAlaAlaAlaAlaAspGlyTrpThrAspAsnIleAlaAlaLeuLeu
LysGluGluAlaAlaLysAsnArgAlaThrProAlaProGlnThrThrProProAlaGlyLeuGlnThrAlaProAspGlyArgTyrCysLysAlaAspPro
PheProAlaAlaLeuLeuAlaAsnGlnLysIleThrAlaArgGlnSerAspLysAspValArgHisIleGluIleAspLeuSerGlySerAspLeuHisTyrLeu
ProGlyAspAlaLeuGlyValTrpPheAspAsnAspProAlaLeuValArgGluIleLeuAspLeuLeuGlyIleAspGlnAlaThrGluIleGlnAlaGly
GlyLysThrLeuProValAlaSerAlaLeuLeuSerHisPheGluLeuThrGlnAsnThrProAlaPheValLysGlyTyrAlaProPheAlaAspAspAsp
GluLeuAspArgIleAlaAlaAspAsnAlaValLeuGlnGlyPheValGlnSerThrProIleAlaAspValLeuHisArgPheProAlaLysLeuThrAla
GluGlnPheAlaGlyLeuLeuArgProLeuAlaProArgLeuTyrSerIleSerSerSerGlnAlaGluValGlyAspGluValHisLeuThrValGlyAla
ValArgPheGluHisGluGlyArgAlaArgAlaGlyGlyAlaSerGlyPheLeuAlaAspArgLeuGluGluAspGlyThrValArgValPheValGlu
ArgAsnAspGlyPheArgLeuProGluAspSerArgLysProIleValMetIleGlySerGlyThrGlyValAlaProPheArgAlaPheValGlnGlnArg
AlaAlaGluAsnAlaGluGlyLysAsnTrpLeuPhePheGlyAsnProHisPheAlaArgAspPheLeuTyrGlnThrGluTrpGlnGlnPheAlaLys
AspGlyPheLeuHisArgTyrAspPheAlaTrpSerArgAspGlnGluGluLysIleTyrValGlnAspLysIleArgGluGlnAlaGluGlyLeuTrpGln
TrpLeuGlnGluGlyAlaHisIleTyrValCysGlyAspAlaAlaLysMetAlaLysAspValGluAlaAlaLeuLeuAspValIleIleGlyAlaGlyHis
LeuAspGluGluGlyAlaGluGluTyrLeuAspMetLeuArgGluGluLysArgTyrGlnArgAspValTyr-599
Antigenic Index - Jameson-Wolf (SEQ. ID. NO. 16633)
1-MetGlnAsnThrAsnProProLeuProProMetProProGluIleThrGlnLeuLeuSerGlyLeuAspAlaAlaGlnTrpAlaTrpLeuSerGlyTyrAlaTrpAlaLysAlaGlyAsnGlyAla
SerAlaGlyLeuProAlaLeuGlnThrAlaLeuProThrAlaGluProPheSerValThrValLeuSerAlaSerGlnThrGlyAsnAlaLysSerValAlaAspLysAlaAlaAspSerLeuGlu
AlaAlaGlyIleGlnValSerArgAlaGluLeuLysAspTyrLysAlaLysAsnIleAlaGlyGluArgArgLeuLeuLeuValThrSerThrGlnGlyGluGlyGluProProGluGluAlaValVal
LeuHisLysLeuLeuAsnGlyLysLysAlaProLysLeuAspLysLeuGlnPheAlaValLeuGlyLeuGlyAspSerSerTyrProAsnPheCysArgAlaGlyLysAspPheAspLysArgPhe
GluGluLeuGlyAlaLysArgLeuLeuGluArgValAspAlaAspLeuAspPheAlaAlaAlaAlaAspGlyTrpThrAspAsnIleAlaAlaLeuLeuLysGluGluAlaAlaLysAsnArg
AlaThrProAlaProGlnThrThrProProAlaGlyLeuGlnThrAlaProAspGlyArgTyrCysLysAlaAspProPheProAlaAlaLeuLeuAlaAsnGlnLysIleThrAlaArgGlnSer
AspLysAspValArgHisIleGluIleAspLeuSerGlySerAspLeuHisTyrLeuProGlyAspAlaLeuGlyValTrpPheAspAsnAspProAlaLeuValArgGluIleLeuAspLeuLeu
GlyIleAspGlnAlaThrGluIleGlnAlaGlyGlyLysThrLeuProValAlaSerAlaLeuLeuSerHisPheGluLeuThrGlnAsnThrProAlaPheValLysGlyTyrAlaProPheAlaAsp
AspAspGluLeuAspArgIleAlaAlaAspAsnAlaValLeuGlnGlyPheValGlnSerThrProIleAlaAspValLeuHisArgPheProAlaLysLeuThrAlaGluGlnPheAlaGlyLeu
LeuArgProLeuAlaProArgLeuTyrSerIleSerSerSerGlnAlaGluValGlyAspGluValHisLeuThrValGlyAlaValArgPheGluHisGluGlyArgAlaArgAlaGlyGlyAla
SerGlyPheLeuAlaAspArgLeuGluGluAspGlyThrValArgValPheValGluArgAsnAspGlyPheArgLeuProGluAspSerArgLysProIleValMetIleGlySerGlyThrGly
ValAlaProPheArgAlaPheValGlnGlnArgAlaAlaGluAsnAlaGluGlyLysAsnTrpLeuPhePheGlyAsnProHisPheAlaArgAspPheLeuTyrGlnThrGluTrpGlnGlnPhe
AlaLysAspGlyPheLeuHisArgTyrAspPheAlaTrpSerArgAspGlnGluGluLysIleTyrValGlnAspLysIleArgGluGlnAlaGluGlyLeuTrpGlnTrpLeuGlnGluGlyAla
HisIleTyrValCysGlyAspAlaAlaLysMetAlaLysAspValGluAlaAlaLeuLeuAspValIleIleGlyAlaGlyHisLeuAspGluGluGlyAlaGluGluTyrLeuAspMetLeuArg
GluGluLysArgTyrGlnArgAspValTyr-599
Hydrophilic Regions - Hopp-Woods (SEQ. ID. NO. 16633)
1-MetGlnAsnThrAsnProProLeuProProMetProProGluIleThrGlnLeuLeuSerGlyLeuAspAlaAlaGlnTrpAlaTrpLeuSerGlyTyrAlaTrpAlaLysAlaGlyAsnGlyAla
SerAlaGlyLeuProAlaLeuGlnThrAlaLeuProThrAlaGluProPheSerValThrValLeuSerAlaSerGlnThrGlyAsnAlaLysSerValAlaAspLysAlaAlaAspSerLeuGlu
AlaAlaGlyIleGlnValSerArgAlaGluLeuLysAspTyrLysAlaLysAsnIleAlaGlyGluArgArgLeuLeuLeuValThrSerThrGlnGlyGluGlyGluProProGluGluAlaValVal
LeuHisLysLeuLeuAsnGlyLysLysAlaProLysLeuAspLysLeuGlnPheAlaValLeuGlyLeuGlyAspSerSerTyrProAsnPheCysArgAlaGlyLysAspPheAspLysArgPhe
GluGluLeuGlyAlaLysArgLeuLeuGluArgValAspAlaAspLeuAspPheAlaAlaAlaAlaAspGlyTrpThrAspAsnIleAlaAlaLeuLeuLysGluGluAlaAlaLysAsnArgAla
ThrProAlaProGlnThrThrProProAlaGlyLeuGlnThrAlaProAspGlyArgTyrCysLysAlaAspProPheProAlaAlaLeuLeuAlaAsnGlnLysIleThrAlaArgGlnSerAspLys TABLE 1-continued AspValArgHisIleGluIleAspLeuSerGlySerAspLeuHisTyrLeuProGlyAspAlaLeuGlyValTrpPheAspAsnAspProAlaLeuValArgGluIleLeuAspLeuLeuGlyIleAsp
GlnAlaThrGluIleGlnAlaGlyGlyLysThrLeuProValAlaSerAlaLeuLeuSerHisPheGluLeuThrGlnAsnThrProAlaPheValLysGlyTyrAlaProPheAlaAspAspAspGlu
LeuAspArgIleAlaAlaAspAsnAlaValLeuGlnGlyPheValGlnSerThrProIleAlaAspValLeuHisArgPheProAlaLysLeuThrAlaGluGlnPheAlaGlyLeuLeuArgProLeu
AlaProArgLeuTyrSerIleSerSerSerGlnAlaGluValGlyAspGluValHisLeuThrValGlyAlaValArgPheGluHisGluGlyArgAlaArgAlaGlyGlyAlaSerGlyPheLeuAla
AspArgLeuGluGluAspGlyThrValArgValPheValGluArgAsnAspGlyPheArgLeuProGluAspSerArgLysProIleValMetIleGlySerGlyThrGlyValAlaProPheArg
AlaPheValGlnGlnArgAlaAlaGluAsnAlaGluGlyLysAsnTrpLeuPhePheGlyAsnProHisPheAlaArgAspPheLeuTyrGlnThrGluTrpGlnGlnPheAlaLysAspGlyPhe
LeuHisArgTyrAspPheAlaTrpSerArgAspGlnGluGluLysIleTyrValGlnAspLysIleArgGluGlnAlaGluGlyLeuTrpGlnTrpLeuGlnGluGlyAlaHisIleTyrValCys
GlyAspAlaAlaLysMetAlaLysAspValGluAlaAlaLeuLeuAspValIleIleGlyAlaGlyHisLeuAspGluGluGlyAlaGluGluTyrLeuAspMetLeuArgGluGluLysArg
TyrGlnArgAspValTyr-599 a151

AMPHI Regions - AMPHI

| | |
|---|---|
| SEQ. ID. NO. 16633 | 6-AsnIleAlaIleIleAla-11 |
| SEQ. ID. NO. 16634 | 22-AspGlnLeuLeuArg-26 |
| SEQ. ID. NO. 16635 | 72-ValAspThrProGlyHis-77 |
| SEQ. ID. NO. 16636 | 81-GlyGlyGluValGluArgValLeuGlyMetValAspCysVal-94 |
| SEQ. ID. NO. 16637 | 128-LysIleAspLysPro-132 |
| SEQ. ID. NO. 16638 | 144-PheGluLeuPheAspAsnLeuGlyAlaThr-153 |
| SEQ. ID. NO. 16639 | 165-SerGlyLeuSerGlyPheAlaLysLeuGluGluThrAspGluSerAsn-180 |
| SEQ. ID. NO. 16640 | 184-ProLeuPheAspThrIleLeuLysTyrThr-193 |
| SEQ. ID. NO. 16641 | 248-GlyArgIleAsnGlnLeuLeuGlyPheLysGlyLeuGluArgVal-262 |
| SEQ. ID. NO. 16642 | 273-ValIleIleSerGlyIleGlu-279 |
| SEQ. ID. NO. 16643 | 330-IleArgAspArgLeuGlnLysGluLeu-338 |
| SEQ. ID. NO. 16644 | 348-AspThrAlaAspAla-352 |
| SEQ. ID. NO. 16645 | 396-CysGluProTyrGluAsnLeuThrValAsp-405 |
| SEQ. ID. NO. 16646 | 457-LeuThrArgGlyValGly-462 |
| SEQ. ID. NO. 16647 | 464-MetSerHisValPheAsp-469 |
| SEQ. ID. NO. 16648 | 537-LysGlyLysLysLeuThrAsnIle-544 |
| SEQ. ID. NO. 16649 | 551-GluAlaValArgLeuThrThr-557 |

Antigenic Index - Jameson-Wolf

| | |
|---|---|
| SEQ. ID. NO. 16650 | 1-MetLysGlnIleArg-5 |
| SEQ. ID. NO. 16651 | 13-ValAspHisGlyLysThrThrLeu-20 |
| SEQ. ID. NO. 16652 | 24-LeuLeuArgGlnSerGlyThrPheArgAlaAsnGlnGlnValAspGluArgValMetAspSerAsnAspLeuGluLysGluArgGlyIle-53 |
| SEQ. ID. NO. 16653 | 59-AsnThrAlaIleAspTyrGluGlyTyr-67 |
| SEQ. ID. NO. 16654 | 72-ValAspThrProGlyHisAlaAspPheGlyGlyGluValGluArg-86 |
| SEQ. ID. NO. 16655 | 99-AspAlaGlnGluGlyProMetProGlnThrArgPheValThr-112 |
| SEQ. ID. NO. 16656 | 128-LysIleAspLysProSerAlaArgProSerTrp-138 |
| SEQ. ID. NO. 16657 | 151-GlyAlaThrAspGluGlnLeuAsp-158 |
| SEQ. ID. NO. 16658 | 171-AlaLysLeuGluGluThrAspGluSerAsnAspMetArgProLeu-185 |
| SEQ. ID. NO. 16659 | 193-ThrProAlaProSerGlySerAlaAspGluThrLeu-204 |
| SEQ. ID. NO. 16660 | 211-LeuAspTyrAspAsnTyrThrGly-218 |
| SEQ. ID. NO. 16661 | 226-LeuAsnGlyArgIleLysProGlyGln-234 |
| SEQ. ID. NO. 16662 | 240-AsnHisAspGlnGlnIleAla-246 |
| SEQ. ID. NO. 16663 | 257-LysGlyLeuGluArgValProLeuGluGluAlaGluAlaGlyAsp-271 |
| SEQ. ID. NO. 16664 | 277-GlyIleGluAspIleGly-282 |
| SEQ. ID. NO. 16665 | 287-IleThrAspLysAspAsnProLysGlyLeuPro-297 |
| SEQ. ID. NO. 16666 | 300-SerValAspGluProThrLeu-306 |
| SEQ. ID. NO. 16667 | 314-ThrSerProLeuAlaGlyThrGluGlyLysPheValThrSerArgGlnIleArgAspArgLeuGlnLysGluLeuLeu-339 |
| SEQ. ID. NO. 16668 | 344-LeuArgValGluAspThrAlaAspAlaAspValPheArgValSerGlyArgGlyGluLeu-363 |
| SEQ. ID. NO. 16669 | 371-AsnMetArgArgGluGlyTyr-377 |
| SEQ. ID. NO. 16670 | 381-ValGlyLysProArgValValTyrArgAspIleAspGlyGlnLysCysGluProTyrGluAsnLeuThrValAspValProAspAspAsnGlnGlyAla ValMetGluGluLeuGlyArgArgArgGlyGluLeuThrAsnMetGluSerAspGlyAsnGlyArgThrArgLeuGluTyr-440 |
| SEQ. ID. NO. 16671 | 467-ValPheAspAspTyrAlaProValLysProAspMetProGlyArgHisAsnGly-484 |
| SEQ. ID. NO. 16672 | 489-GlnGluGlnGlyGlu-493 |
| SEQ. ID. NO. 16673 | 501-AsnLeuGluAspArgGlyArgMetPheValSerProAsnAspLysIleTyr-517 |
| SEQ. ID. NO. 16674 | 524-IleHisSerArgAspAsnAspLeu-531 |
| SEQ. ID. NO. 16675 | 535-ProLeuLysGlyLysLysLeuThrAsnIleArgAlaSerGlyThrAspGluAlaValArg-554 |
| SEQ. ID. NO. 16676 | 569-PheIleAspAspAspGluLeuValGlu-577 |
| SEQ. ID. NO. 16677 | 579-ThrProGlnSerIleArgLeuArgLysArgTyrLeuSerGluLeuGluArgArgArgHisPheLysLysLeuAsp-603 |

Hydrophilic Regions- Hopp-Woods

| | |
|---|---|
| SEQ. ID. NO. 16678 | 1-MetLysGlnIleArg-5 |
| SEQ. ID. NO. 16679 | 29-GlyThrPheArgAla-33 |
| SEQ. ID. NO. 16680 | 35-GlnGlnValAspGluArgValMetAspSerAsnAspLeuGluLysGluArgGlyIle-53 |
| SEQ. ID. NO. 16681 | 80-PheGlyGlyGluValGluArg-86 |
| SEQ. ID. NO. 16682 | 99-AspAlaGlnGluGlyProMetPro-106 |
| SEQ. ID. NO. 16683 | 128-LysIleAspLysProSerAla-134 |
| SEQ. ID. NO. 16684 | 151-GlyAlaThrAspGluGlnLeuAsp-158 |
| SEQ. ID. NO. 16685 | 171-AlaLysLeuGluGluThrAspGluSerAsnAspMetArgProLeu-185 |
| SEQ. ID. NO. 16686 | 198-GlySerAlaAspGluThrLeu-204 |
| SEQ. ID. NO. 16687 | 226-LeuAsnGlyArgIleLysPro-232 |
| SEQ. ID. NO. 16688 | 241-HisAspGlnGlnIleAla-246 |
| SEQ. ID. NO. 16689 | 258-GlyLeuGluArgValProLeuGluGluAlaGluAlaGlyAsp-271 |
| SEQ. ID. NO. 16690 | 277-GlyIleGluAspIleGly-282 |
| SEQ. ID. NO. 16691 | 287-IleThrAspLysAspAsnProLysGly-295 |
| SEQ. ID. NO. 16692 | 300-SerValAspGluProThrLeu-306 |
| SEQ. ID. NO. 16693 | 318-AlaGlyThrGluGlyLysPheValThr-326 |
| SEQ. ID. NO. 16694 | 328-ArgGlnIleArgAspArgLeuGlnLysGluLeuLeu-339 |
| SEQ. ID. NO. 16695 | 344-LeuArgValGluAspThrAlaAspAlaAspValPheArgValSerGlyArgGlyGluLeu-363 |
| SEQ. ID. NO. 16696 | 371-AsnMetArgArgGluGlyTyr-377 |

TABLE 1-continued

| | |
|---|---|
| SEQ. ID. NO. 16697 | 381-ValGlyLysProArgValValTyrArgAspIleAspGlyGlnLysCysGluProTyrGlu-400 |
| SEQ. ID. NO. 16698 | 405-AspValProAspAspAsnGlnGlyAlaValMetGluGluLeuGlyArgArgArgGlyGluLeuThrAsnMetGluSerAspGlyAsnGlyArgThrArgLeu-438 |
| SEQ. ID. NO. 16699 | 472-AlaProValLysProAspMetProGlyArgHis-482 |
| SEQ. ID. NO. 16700 | 489-GlnGluGlnGlyGlu-493 |
| SEQ. ID. NO. 16701 | 502-LeuGluAspArgGlyArgMet-508 |
| SEQ. ID. NO. 16702 | 512-ProAsnAspLysIleTyr-517 |
| SEQ. ID. NO. 16703 | 525-HisSerArgAspAsnAspLeu-531 |
| SEQ. ID. NO. 16704 | 536-LeuLysGlyLysLysLeuThrAsn-543 |
| SEQ. ID. NO. 16705 | 545-ArgAlaSerGlyThrAspGluAlaValArg-554 |
| SEQ. ID. NO. 16706 | 569-PheIleAspAspAspGluLeuValGlu-577 |
| SEQ. ID. NO. 16707 | 583-IleArgLeuArgLysArgTyrLeuSerGluLeuGluArgArgArgHisPheLysLysLeuAsp-603 |
| a152 | |
| AMPHI Regions - AMPHI | |
| SEQ. ID. NO. 16708 | 10-PheProThrArgLeuPhe-15 |
| SEQ. ID. NO. 16709 | 66-ArgPheSerArgPheValArgGlyTrpSerGlyIleArgGluTyrMetLysAsnGlyIleProGluHisValGlnProGlyHisAsnProLeu-96 |
| SEQ. ID. NO. 16710 | 103-AlaLeuLeuAlaAla-107 |
| SEQ. ID. NO. 16711 | 130-LeuAsnHisLeuValSerGluHisThrGlySerLeu-141 |
| SEQ. ID. NO. 16712 | 150-PheLysLeuLeuAlaValPheSerAlaValHisIleAlaXxxValAlaAlaTyr-167 |
| Antigenic Index - Jameson-Wolf | |
| SEQ. ID. NO. 16713 | 1-MetLysAsnLysThrLysValTrp-8 |
| SEQ. ID. NO. 16714 | 28-TyrSerAlaLysThrGlyGlyAsp-35 |
| SEQ. ID. NO. 16715 | 61-GlySerAspThrAlaArgPhe-67 |
| SEQ. ID. NO. 16716 | 74-TrpSerGlyIleArgGluTyrMetLysAsnGlyIleProGluHisValGlnProGlyHisAsnProLeu-96 |
| SEQ. ID. NO. 16717 | 125-SerThrAsnGlyTyr-129 |
| SEQ. ID. NO. 16718 | 137-HisThrGlySerLeuMetArg-143 |
| SEQ. ID. NO. 16719 | 169-ValPheLysLysLysAsnLeu-175 |
| SEQ. ID. NO. 16720 | 186-IleGluGlyLysThrSerIle-192 |
| Hydrophilic Regions - Hopp-Woods | |
| SEQ. ID. NO. 16721 | 1-MetLysAsnLysThrLysVal-7 |
| SEQ. ID. NO. 16722 | 63-AspThrAlaArgPhe-67 |
| SEQ. ID. NO. 16723 | 78-ArgGluTyrMetLys-82 |
| SEQ. ID. NO. 16724 | 169-ValPheLysLysLysAsnLeu-175 |
| SEQ. ID. NO. 16725 | 186-IleGluGlyLysThrSerIle-192 |
| a153 | |
| AMPHI Regions - AMPHI | |
| SEQ. ID. NO. 16726 | 17-AlaAlaSerValLeuSerLeuProGluMetMetArgLeuMetValPhe-32 |
| SEQ. ID. NO. 16727 | 96-ThrLeuValAlaTyrIleLysLeuSerSerValAlaGlu-108 |
| SEQ. ID. NO. 16728 | 130-ValSerValProGlnHisTrp-136 |
| SEQ. ID. NO. 16729 | 222-ValAsnThrIleLeuAsnGlyIleAlaTyr-231 |
| SEQ. ID. NO. 16730 | 274-AlaLysLysLeuSerHisLeuTyrArgIleThrGluAlaValGlyArgTrpSerMetIleAspIlePheValIle-298 |
| Antigenic Index - Jameson-Wolf | |
| SEQ. ID. NO. 16731 | 65-IleArgLysGlnAla-69 |
| SEQ. ID. NO. 16732 | 81-ValArgLeuArgGln-85 |
| SEQ. ID. NO. 16733 | 107-AlaGluValArgPhe-111 |
| SEQ. ID. NO. 16734 | 143-ArgLeuThrGlyAspAsnAlaValGlnThrAlaSerGluGlyLysThrCysCysSer-161 |
| SEQ. ID. NO. 16735 | 165-TyrPheArgAspSerAlaGluSerProCysGly-175 |
| SEQ. ID. NO. 16736 | 180-GluLeuTyrArgArgArgProLysSerLeuSer-190 |
| SEQ. ID. NO. 16737 | 215-SerAsnProAlaAlaThr-220 |
| SEQ. ID. NO. 16738 | 234-AspGluGlyAspArgLeu-239 |
| SEQ. ID. NO. 16739 | 272-ThrGlyAlaLysLysLeu-277 |
| SEQ. ID. NO. 16740 | 339-LeuLeuTrpAspLysArgAlaSerAspGlyIleAla-350 |
| SEQ. ID. NO. 16741 | 352-AsnGluThrGluLysHisAsp-358 |
| Hydrophilic Regions - Hopp-Woods | |
| SEQ. ID. NO. 16742 | 81-ValArgLeuArgGln-85 |
| SEQ. ID. NO. 16743 | 107-AlaGluValArgPhe-111 |
| SEQ. ID. NO. 16744 | 152-ThrAlaSerGluGlyLysThrCysCys-160 |
| SEQ. ID. NO. 16745 | 168-AspSerAlaGluSerPro-173 |
| SEQ. ID. NO. 16746 | 180-GluLeuTyrArgArgArgProLysSerLeuSer-190 |
| SEQ. ID. NO. 16747 | 234-AspGluGlyAspArgLeu-239 |
| SEQ. ID. NO. 16748 | 273-GlyAlaLysLysLeu-277 |
| SEQ. ID. NO. 16749 | 339-LeuLeuTrpAspLysArgAlaSerAsp-347 |
| SEQ. ID. NO. 16750 | 352-AsnGluThrGluLysHisAsp-358 |
| a154 | |
| AMPHI Regions - AMPHI | |
| SEQ. ID. NO. 16751 | 122-GlyValThrGlyLeuGlyThrLeuLeu-130 |
| SEQ. ID. NO. 16752 | 152-GlnAspIleProProValThr-158 |
| SEQ. ID. NO. 16753 | 262-ThrLysAsnSerLysAsnValLysSer-270 |
| SEQ. ID. NO. 16754 | 298-PheLysGlnSerVal-302 |
| SEQ. ID. NO. 16755 | 360-SerLysGluHisTrpLysGlnGlnPheGlnThrAlaLeuAsnLysGlyLeuThrAla-378 |
| SEQ. ID. NO. 16756 | 389-SerLysMetIleGluLeuAsnAsp-396 |
| SEQ. ID. NO. 16757 | 429-LysLeuAlaAspLeuLeuAspLysPheAspLysLeuPro-441 |
| SEQ. ID. NO. 16758 | 446-ValAlaGluLeuAsnGly-451 |
| SEQ. ID. NO. 16759 | 467-LeuSerSerIleAspLysLeuValGlyLysProGlnThrGlnAsnIleProAsnGluLeuAsnGlnThrLeuLysGluLeuArgThrThr-496 |
| SEQ. ID. NO. 16760 | 506-IleTyrGlyAspValGlnAsnThrLeuGlnSerLeuAspLysThrLeuLysAspValGlnProValIleAsnThrLeuLysGluLys-534 |
| Antigenic Index - Jameson-Wolf | |
| SEQ. ID. NO. 16761 | 1-MetThrAspAsnSerProProProAsnGlyHisAlaGlnAlaArgValArgLysAsnAsnThr-21 |
| SEQ. ID. NO. 16762 | 43-LysGluIleArgAsnArgGlyProVal-51 |
| SEQ. ID. NO. 16763 | 57-AspSerAlaGluGlyIleGluValAsnAsnThr-67 |
| SEQ. ID. NO. 16764 | 75-AspValGlyArgValThrArgIleLysLeuArgAspAspGlnLysGlyValGlu-92 |

TABLE 1-continued

| | |
|---|---|
| SEQ. ID. NO. 16765 | 100-AspValSerGlyLeuIleArgSerAspThrGln-110 |
| SEQ. ID. NO. 16766 | 114-ValLysProArgIleAspGlnSerGly-122 |
| SEQ. ID. NO. 16767 | 138-ThrProGlyLysSerAspGluAlaLysAspValPheGln-150 |
| SEQ. ID. NO. 16768 | 169-LeuIleGlyLysAsnAspArgIleLeuAsn-178 |
| SEQ. ID. NO. 16769 | 196-AlaHisPheAspProSerAspGlnSer-204 |
| SEQ. ID. NO. 16770 | 212-GlnSerProAsnAspLysLeuIle-219 |
| SEQ. ID. NO. 16771 | 228-GluSerGlyIleAsnIleGluThrThrGlySerGlyIleLysLeuAsnSer-244 |
| SEQ. ID. NO. 16772 | 256-SerPheAspSerProLysThrLysAsnSerLysAsnValLysSerGluAspSer-273 |
| SEQ. ID. NO. 16773 | 275-ThrLeuTyrAspSerArgSerGluValAlaAsnLeuProAspAspArgSerLeu-292 |
| SEQ. ID. NO. 16774 | 300-GlnSerValArgGlyLeu-305 |
| SEQ. ID. NO. 16775 | 311-ValGluTyrLysGlyLeuAsn-317 |
| SEQ. ID. NO. 16776 | 325-ProTyrPheAspArgAsnAspSer-332 |
| SEQ. ID. NO. 16777 | 345-IleArgIleGluProSerArgLeuGluIleAsnAlaAspGluGlnSerLysGluHisTrpLysGlnGlnPhe-368 |
| SEQ. ID. NO. 16778 | 371-AlaLeuAsnLysGlyLeu-376 |
| SEQ. ID. NO. 16779 | 386-LeuThrGlySerLysMetIleGluLeuAsnAspGlnProSerAlaSerProLysLeuArgPro-406 |
| SEQ. ID. NO. 16780 | 419-GlnGlyGlyGlyLeuAspAspLeuGlnValLysLeu-430 |
| SEQ. ID. NO. 16781 | 432-AspLeuLeuAspLysPheAspLysLeuProLeuAspLysThrValAla-447 |
| SEQ. ID. NO. 16782 | 450-AsnGlySerLeuAlaGluLeuLysSerThrLeuLysSerAlaAsn-464 |
| SEQ. ID. NO. 16783 | 469-SerIleAspLysLeuValGlyLysProGlnThrGlnAsnIleProAsnGluLeuAsnGlnThrLeuLysGluLeuArgThrThr-496 |
| SEQ. ID. NO. 16784 | 500-ValSerProGlnSer-504 |
| SEQ. ID. NO. 16785 | 516-SerLeuAspLysThrLeuLysAspValGln-525 |
| SEQ. ID. NO. 16786 | 530-ThrLeuLysGluLysProAsn-536 |
| SEQ. ID. NO. 16787 | 541-AsnSerSerSerLysAspProIleProLysGlySerArg-553 |
| Hydrophilic Regions- Hopp-Woods | |
| SEQ. ID. NO. 16788 | 1-MetThrAspAsnSerProProPro-8 |
| SEQ. ID. NO. 16789 | 12-AlaGlnAlaArgValArgLysAsnAsn-20 |
| SEQ. ID. NO. 16790 | 43-LysGluIleArgAsnArgGly-49 |
| SEQ. ID. NO. 16791 | 57-AspSerAlaGluGlyIleGlu-63 |
| SEQ. ID. NO. 16792 | 75-AspValGlyArgValThrArgIleLysLeuArgAspAspGlnLysGlyValGlu-92 |
| SEQ. ID. NO. 16793 | 105-IleArgSerAspThr-109 |
| SEQ. ID. NO. 16794 | 116-ProArgIleAspGln-120 |
| SEQ. ID. NO. 16795 | 140-GlyLysSerAspGluAlaLysAspValPheGln-150 |
| SEQ. ID. NO. 16796 | 171-GlyLysAsnAspArgIleLeu-177 |
| SEQ. ID. NO. 16797 | 196-AlaHisPheAspProSerAspGln-203 |
| SEQ. ID. NO. 16798 | 214-ProAsnAspLysLeuIle-219 |
| SEQ. ID. NO. 16799 | 258-AspSerProLysThrLysAsnSerLysAsnValLysSerGluAspSer-273 |
| SEQ. ID. NO. 16800 | 278-AspSerArgSerGluVal-283 |
| SEQ. ID. NO. 16801 | 285-AsnLeuProAspAspArgSer-291 |
| SEQ. ID. NO. 16802 | 311-ValGluTyrLysGly-315 |
| SEQ. ID. NO. 16803 | 328-AspArgAsnAspSer-332 |
| SEQ. ID. NO. 16804 | 345-IleArgIleGluProSerArgLeuGluIleAsnAlaAspGluGlnSerLysGluHisTrpLys-365 |
| SEQ. ID. NO. 16805 | 390-LysMetIleGluLeuAsnAspGlnProSerAlaSerProLysLeuArgPro-406 |
| SEQ. ID. NO. 16806 | 421-GlyGlyLeuAspAspLeuGlnValLysLeu-430 |
| SEQ. ID. NO. 16807 | 432-AspLeuLeuAspLysPheAspLysLeuProLeuAspLysThrValAla-447 |
| SEQ. ID. NO. 16808 | 454-AlaGluLeuLysSerThrLeuLysSerAlaAsn-464 |
| SEQ. ID. NO. 16809 | 469-SerIleAspLysLeuValGly-475 |
| SEQ. ID. NO. 16810 | 482-IleProAsnGluLeu-486 |
| SEQ. ID. NO. 16811 | 488-GlnThrLeuLysGluLeuArgThr-495 |
| SEQ. ID. NO. 16812 | 516-SerLeuAspLysThrLeuLysAspValGln-525 |
| SEQ. ID. NO. 16813 | 530-ThrLeuLysGluLysProAsn-536 |
| SEQ. ID. NO. 16814 | 543-SerSerLysAspProIleProLysGlySerArg-553 |
| a155 | |
| AMPHI Regions - AMPHI | |
| SEQ. ID. NO. 16815 | 28-LysLeuGlyPheGlu-32 |
| SEQ. ID. NO. 16816 | 42-AlaAlaSerLeuAsp-46 |
| SEQ. ID. NO. 16817 | 105-LeuArgAlaLysLysVal-110 |
| SEQ. ID. NO. 16818 | 118-ValProArgIleSerArgAlaGlnAlaLeuAspXxxLeuSerXxxMetAlaAsnIleSerGlyTyrArgAlaValIleGluAlaAlaAsnAlaPheGlyArg XxxPheThrGlyGlnIleThrAlaAlaGly-161 |
| SEQ. ID. NO. 16819 | 175-ValAlaGlyLeuAlaAlaIleGlyThrAlaAsnSerLeuGlyAlaValValArgValPhe-194 |
| SEQ. ID. NO. 16820 | 201-AlaGluGlnLeuGluSerMetGlyGly-209 |
| SEQ. ID. NO. 16821 | 225-AspGlyTyrAlaLysValMet-231 |
| SEQ. ID. NO. 16822 | 264-AlaProLysXxxXxxXxxLysGluMetValGluSerMetLys-277 |
| SEQ. ID. NO. 16823 | 281-ValIleValAspLeu-285 |
| SEQ. ID. NO. 16824 | 307-GlyValLysIleIleGlyTyrThrAspMetAlaAsnArgLeuAlaGlyGln-323 |
| SEQ. ID. NO. 16825 | 330-ThrAsnLeuValAsnLeuThrLysLeuLeuSer-340 |
| SEQ. ID. NO. 16826 | 404-LysLeuAlaProAlaXxxIle-410 |
| SEQ. ID. NO. 16827 | 428-AsnHisPheIleVal-432 |
| SEQ. ID. NO. 16828 | 451-LeuHisThrProLeuMetSerValThrAsnAlaIleSerGlyIleIle-466 |
| SEQ. ID. NO. 16829 | 469-GlyAlaLeuLeuGln-473 |
| SEQ. ID. NO. 16830 | 478-AsnGlyPheValSerLeuLeuSerPheValAla-488 |
| SEQ. ID. NO. 16831 | 494-IleAsnIlePheGlyGly-499 |
| Antigenic Index - Jameson-Wolf | |
| SEQ. ID. NO. 16832 | 4-GlyIleProArgGluSerLeuSerGlyGluThrArgVal-16 |
| SEQ. ID. NO. 16833 | 44-SerLeuAspAspAlaAla-49 |
| SEQ. ID. NO. 16834 | 72-ValAsnAlaProSerGluAspGluLeuProLeuLeuLysGluGlyGln-87 |
| SEQ. ID. NO. 16835 | 94-TrpProArgGlnAsnGluAlaLeu-101 |
| SEQ. ID. NO. 16836 | 105-LeuArgAlaLysLysValAsn-111 |
| SEQ. ID. NO. 16837 | 117-MetValProArgIleSerArg-123 |
| SEQ. ID. NO. 16838 | 159-AlaAlaGlyLysValProProAla-166 |
| SEQ. ID. NO. 16839 | 202-GluGlnLeuGluSerMetGlyGlyLys-210 |

TABLE 1-continued

SEQ. ID. NO. 16840 215-AspPheProGlnGluSerGlyGlySerGlyAspGlyTyrAlaLysValMetSer-232
SEQ. ID. NO. 16841 242-LeuPheAlaGluGlnAlaLysGluValAsp-251
SEQ. ID. NO. 16842 259-IleProGlyLysProAlaProLysXxxXxxXxxLysGluMetValGluSerMetLysProGlySer-280
SEQ. ID. NO. 16843 290-GlyGlyAsnCysGluLeuThrLysGlnGlyGlu-300
SEQ. ID. NO. 16844 320-LeuAlaGlyGlnSerSer-325
SEQ. ID. NO. 16845 338-LeuLeuSerProAsnLysAspGlyGluIle-347
SEQ. ID. NO. 16846 349-LeuAspPheGluAspValIle-355
SEQ. ID. NO. 16847 360-ThrValThrArgAspGlyGluIleThrPhePro-370
SEQ. ID. NO. 16848 378-AlaGlnProGlnGlnThrProSerGluLysAlaAlaProAlaAlaLysProGluProLysPro-398
SEQ. ID. NO. 16849 509-MetPheArgLysGly-513
Hydrophilic Regions - Hopp-Woods
SEQ. ID. NO. 16850 4-GlyIleProArgGluSerLeuSerGlyGluThrArgVal-16
SEQ. ID. NO. 16851 44-SerLeuAspAspAlaAla-49
SEQ. ID. NO. 16852 74-AlaProSerGluAspGluLeuProLeuLeuLysGluGlyGln-87
SEQ. ID. NO. 16853 96-ArgGlnAsnGluAlaLeu-101
SEQ. ID. NO. 16854 105-LeuArgAlaLysLysValAsn-111
SEQ. ID. NO. 16855 117-MetValProArgIleSerArg-123
SEQ. ID. NO. 16856 202-GluGlnLeuGluSerMetGly-208
SEQ. ID. NO. 16857 215-AspPheProGlnGluSerGlyGlySerGlyAspGlyTyrAla-228
SEQ. ID. NO. 16858 242-LeuPheAlaGluGlnAlaLysGluValAsp-251
SEQ. ID. NO. 16859 260-ProGlyLysProAlaProLysXxxXxxXxxLysGluMetValGluSerMetLysPro-278
SEQ. ID. NO. 16860 291-GlyAsnCysGluLeuThrLysGlnGlyGlu-300
SEQ. ID. NO. 16861 340-SerProAsnLysAspGlyGluIle-347
SEQ. ID. NO. 16862 349-LeuAspPheGluAspValIle-355
SEQ. ID. NO. 16863 360-ThrValThrArgAspGlyGluIle-367
SEQ. ID. NO. 16864 382-GlnThrProSerGluLysAlaAlaProAlaAlaLysProGluProLysPro-398
a156
AMPHI Regions - AMPHI
SEQ. ID. NO. 16865 56-AsnGlyPheGluAlaPheAlaProPhe-64
SEQ. ID. NO. 16866 80-AlaThrValAsnThr-84
Antigenic Index - Jameson-Wolf
SEQ. ID. NO. 16867 21-TyrAlaLysLysAlaGlyGlyPheArgPheLysAspAsnHisAsnProArgAspPheLeuAlaArgThrGlnGlyThrAlaAlaArgAlaHisAlaAla GlnGlnAsnGlyPheGlu-59
SEQ. ID. NO. 16868 73-AlaThrGlyAsnAlaGlyGln-79
SEQ. ID. NO. 16869 103-AspLysAlaAlaLeu-107
Hydrophilic Regions - Hopp-Woods
SEQ. ID. NO. 16870 21-TyrAlaLysLysAlaGlyGlyPheArgPheLysAspAsnHisAsnProArgAspPheLeuAla-41
SEQ. ID. NO. 16871 43-ThrGlnGlyThrAlaAlaArgAlaHisAla-52
SEQ. ID. NO. 16872 103-AspLysAlaAlaLeu-107
a157
AMPHI Regions - AMPHI
SEQ. ID. NO. 16873 10-ArgArgGluLeuArgArgAla-16
SEQ. ID. NO. 16874 32-IleAsnArgLeuLeuLysArgTyrIleLysArgGly-43
SEQ. ID. NO. 16875 61-PheValArgAlaAlaGln-66
SEQ. ID. NO. 16876 137-LeuGlyGlnAlaGlyGly-142
SEQ. ID. NO. 16877 167-GlnPheValAspArgLeuProArgGluProHisAspLeuLeuLeuAspGly-183
Antigenic Index - Jameson-Wolf
SEQ. ID. NO. 16878 1-MetArgAsnGluGluLysHisAlaLeuArgArgGluLeuArgArgAlaArgAlaGlnMetGlyHisGlnGlyArgLeuAlaAla-28
SEQ. ID. NO. 16879 34-ArgLeuLeuLysArgTyrIleLysArgGlyArgLysIle-46
SEQ. ID. NO. 16880 51-ProMetGlyLysGluLeuArgLeuAspGlyPheVal-62
SEQ. ID. NO. 16881 64-AlaAlaGlnLysArgGlyAlaLysLeu-72
SEQ. ID. NO. 16882 77-IleGluProArgSerArgArgMetTrp-85
SEQ. ID. NO. 16883 88-ProTyrProGluSerGlyMetGluArgGluArgIleArgGlyArgAlaLysLeuAsnVal-107
SEQ. ID. NO. 16884 110-PheAlaGlyArgLysIleArgVal-117
SEQ. ID. NO. 16885 129-GlyIleAspArgGluGlyTyrArgLeuGlyGln-139
SEQ. ID. NO. 16886 153-TyrArgLeuGlnAla-157
SEQ. ID. NO. 16887 168-PheValAspArgLeuProArgGluProHisAspLeuLeuLeu-181
Hydrophilic Regions - Hopp-Woods
SEQ. ID. NO. 16888 1-MetArgAsnGluGluLysHisAlaLeuArgArgGluLeuArgArgAlaArgAlaGlnMet-20
SEQ. ID. NO. 16889 34-ArgLeuLeuLysArgTyrIleLysArgGlyArgLysIle-46
SEQ. ID. NO. 16890 54-LysGluLeuArgLeu-58
SEQ. ID. NO. 16891 64-AlaAlaGlnLysArgGlyAla-70
SEQ. ID. NO. 16892 77-IleGluProArgSerArgArg-83
SEQ. ID. NO. 16893 92-SerGlyMetGluArgGluArgIleArgGlyArgAlaLysLeu-105
SEQ. ID. NO. 16894 111-AlaGlyArgLysIleArgVal-117
SEQ. ID. NO. 16895 129-GlyIleAspArgGluGlyTyrArg-136
SEQ. ID. NO. 16896 153-TyrArgLeuGlnAla-157
SEQ. ID. NO. 16897 170-AspArgLeuProArgGluProHisAspLeuLeu-180
a158
AMPHI Regions - AMPHI
SEQ. ID. NO. 16898 20-PheSerArgAlaAlaGluGlnLeu-27
SEQ. ID. NO. 16899 33-AlaValSerArgIleValLysArgLeuGlu-42
SEQ. ID. NO. 16900 46-GlyValAsnLeuLeuAsnArgThr-53
SEQ. ID. NO. 16901 63-GlyAlaGlnTyrPheArgArgAlaGlnArgIleLeuGlnGlu-76
SEQ. ID. NO. 16902 85-LeuAlaValHisGluIleProGln-92
SEQ. ID. NO. 16903 166-ValIleAlaSerPro-170

TABLE 1-continued

| | |
|---|---|
| SEQ. ID. NO. 16904 | 178-ThrProGlnSerThrGluGluLeu-185 |
| SEQ. ID. NO. 16905 | 188-HisGlnCysLeuGlyPheThrGluProGlySerLeuAsnThrTrpAlaVal-204 |
| Antigenic Index - Jameson-Wolf | |
| SEQ. ID. NO. 16906 | 1-MetLysThrAsnSerGluGluLeu-8 |
| SEQ. ID. NO. 16907 | 16-GluSerGlySerPheSerArgAlaAlaGlu-25 |
| SEQ. ID. NO. 16908 | 36-ArgIleValLysArgLeuGluGluLysLeuGly-46 |
| SEQ. ID. NO. 16909 | 49-LeuLeuAsnArgThrThrArgGlnLeuSerLeuThrGluGluGlyAlaGlnTyrPheArgArgAlaGlnArgIleLeuGln-75 |
| SEQ. ID. NO. 16910 | 78-AlaAlaAlaGluThrGluMet-84 |
| SEQ. ID. NO. 16911 | 90-IleProGlnGlyValLeuArgValAspSer-99 |
| SEQ. ID. NO. 16912 | 114-LysPheAsnGluArgTyrProHisIleArg-123 |
| SEQ. ID. NO. 16913 | 136-IleGluArgLysValAspIle-142 |
| SEQ. ID. NO. 16914 | 144-LeuArgAlaGlyGluLeuAspAspSerGlyLeuArgAla-156 |
| SEQ. ID. NO. 16915 | 158-HisLeuPheAspSerArgPheArgVal-166 |
| SEQ. ID. NO. 16916 | 168-AlaSerProGluTyrLeuAlaLysHisGlyThrProGlnSerThrGluGluLeuAla-186 |
| SEQ. ID. NO. 16917 | 192-GlyPheThrGluProGlySerLeuAsn-200 |
| SEQ. ID. NO. 16918 | 207-AlaGlnGlyAsnProTyrLysIle-214 |
| SEQ. ID. NO. 16919 | 216-ProHisPheThrAlaSerSerGlyGluIleLeu-226 |
| SEQ. ID. NO. 16920 | 229-LeuCysLeuSerGlyCysGly-235 |
| SEQ. ID. NO. 16921 | 243-LeuValAspAsnAspIleAlaGluGlyLysLeu-253 |
| SEQ. ID. NO. 16922 | 258-AlaGluGlnThrSerAsnLysThrHisProPhe-268 |
| SEQ. ID. NO. 16923 | 273-TyrSerAspLysAlaValAsnLeu-280 |
| SEQ. ID. NO. 16924 | 292-GluLeuGlyAsnAsnLeuCysGly-299 |
| Hydrophilic Regions - Hopp-Woods | |
| SEQ. ID. NO. 16925 | 1-MetLysThrAsnSerGluGluLeu-8 |
| SEQ. ID. NO. 16926 | 19-SerPheSerArgAlaAlaGlu-25 |
| SEQ. ID. NO. 16927 | 36-ArgIleValLysArgLeuGluGluLysLeuGly-46 |
| SEQ. ID. NO. 16928 | 58-SerLeuThrGluGluGlyAlaGlnTyrPheArgArgAlaGlnArgIleLeuGln-75 |
| SEQ. ID. NO. 16929 | 78-AlaAlaAlaGluThrGluMet-84 |
| SEQ. ID. NO. 16930 | 95-LeuArgValAspSer-99 |
| SEQ. ID. NO. 16931 | 114-LysPheAsnGluArgTyrPro-120 |
| SEQ. ID. NO. 16932 | 136-IleGluArgLysValAspIle-142 |
| SEQ. ID. NO. 16933 | 144-LeuArgAlaGlyGluLeuAspAspSerGlyLeuArgAla-156 |
| SEQ. ID. NO. 16934 | 162-SerArgPheArgVal-166 |
| SEQ. ID. NO. 16935 | 180-GlnSerThrGluGluLeuAla-186 |
| SEQ. ID. NO. 16936 | 246-AsnAspIleAlaGluGlyLysLeu-253 |
| SEQ. ID. NO. 16937 | 260-GlnThrSerAsnLysThrHis-266 |
| SEQ. ID. NO. 16938 | 276-LysAlaValAsnLeu-280 |
| a160 | |
| AMPHI Regions - AMPHI | |
| SEQ. ID. NO. 16939 | 6-LysLeuValAspPheAlaGlnLeuThrGly-15 |
| SEQ. ID. NO. 16940 | 72-GlyLeuGlyHisVal-76 |
| SEQ. ID. NO. 16941 | 121-AlaAspLeuMetAsnGlyLeuProGluThr-130 |
| SEQ. ID. NO. 16942 | 157-GlyThrValSerMetValAsnAlaLeuSerSer-167 |
| SEQ. ID. NO. 16943 | 186-LeuSerGlyValLeuLysGlyTrpGlnAspLysArg-197 |
| SEQ. ID. NO. 16944 | 200-HisLeuIleGlnLysValIleAspLysProGlu-210 |
| SEQ. ID. NO. 16945 | 218-MetValAlaAlaAlaAsn-223 |
| SEQ. ID. NO. 16946 | 229-LeuMetArgArgPhe-233 |
| SEQ. ID. NO. 16947 | 242-HisAlaPheValAsnHisIleArg-249 |
| SEQ. ID. NO. 16948 | 279-PheGlyLysAlaPheLys-284 |
| Antigenic Index - Jameson-Wolf | |
| SEQ. ID. NO. 16949 | 2-AspIleLeuAspLysLeuVal-8 |
| SEQ. ID. NO. 16950 | 28-SerValArgHisGluThrLeuGlnArgGluGlyLeu-39 |
| SEQ. ID. NO. 16951 | 51-CysIleAspGlyGluThrSerProArgProValSerThrGlyAsp-65 |
| SEQ. ID. NO. 16952 | 77-LeuSerHisAspGlyLysCysGlyGluSerLeuGlnProAspMetArgGlnHisGly-95 |
| SEQ. ID. NO. 16953 | 101-GlnCysGlyAsnGlyGlnAspMet-108 |
| SEQ. ID. NO. 16954 | 115-PheArgTyrAspThrHisAla-121 |
| SEQ. ID. NO. 16955 | 123-LeuMetAsnGlyLeu-127 |
| SEQ. ID. NO. 16956 | 149-LeuGluSerLysLysProLeu-155 |
| SEQ. ID. NO. 16957 | 178-LeuGluGlnAspLysAspValGluLeu-186 |
| SEQ. ID. NO. 16958 | 192-GlyTrpGlnAspLysArgLeuGly-199 |
| SEQ. ID. NO. 16959 | 205-ValIleAspLysProGluAspGluTrpAsnValAspLysMetVal-219 |
| SEQ. ID. NO. 16960 | 228-GlnLeuMetArgArgPheLysSerArgValGlyLeuSerProHis-242 |
| SEQ. ID. NO. 16961 | 255-LeuLeuLeuLysLysAsnProAspSerVal-264 |
| SEQ. ID. NO. 16962 | 274-GlnSerGluThrHisPhe-279 |
| SEQ. ID. NO. 16963 | 281-LysAlaPheLysArg-285 |
| SEQ. ID. NO. 16964 | 290-SerProGlyGlnTyrArgLysGluGlyGlyGlnLys-301 |
| Hydrophilic Regions - Hopp-Woods | |
| SEQ. ID. NO. 16965 | 2-AspIleLeuAspLysLeuVal-8 |
| SEQ. ID. NO. 16966 | 29-ValArgHisGluThrLeuGlnArgGluGlyLeu-39 |
| SEQ. ID. NO. 16967 | 53-AspGlyGluThrSerProArgProValSer-62 |
| SEQ. ID. NO. 16968 | 79-HisAspGlyLysCysGlyGluSerLeuGlnProAspMetArgGln-93 |
| SEQ. ID. NO. 16969 | 101-GlnCysGlyAsnGlyGlnAsp-107 |
| SEQ. ID. NO. 16970 | 149-LeuGluSerLysLysProLeu-155 |
| SEQ. ID. NO. 16971 | 178-LeuGluGlnAspLysAspValGluLeu-186 |
| SEQ. ID. NO. 16972 | 193-TrpGlnAspLysArgLeuGly-199 |
| SEQ. ID. NO. 16973 | 205-ValIleAspLysProGluAspGluTrpAsnVal-215 |
| SEQ. ID. NO. 16974 | 228-GlnLeuMetArgArgPheLysSerArgValGly-238 |
| SEQ. ID. NO. 16975 | 255-LeuLeuLeuLysLysAsnProAspSer-263 |

TABLE 1-continued

| | |
|---|---|
| SEQ. ID. NO. 16976 | 281-LysAlaPheLysArg-285 |
| SEQ. ID. NO. 16977 | 293-GlnTyrArgLysGluGlyGlyGlnLys-301 |
| a163 | |
| AMPHI Regions - AMPHI | |
| SEQ. ID. NO. 16978 | 60-SerSerLeuGlyAsnIle-65 |
| SEQ. ID. NO. 16979 | 67-LeuGlyArgAspGluAsp-72 |
| SEQ. ID. NO. 16980 | 76-PheGlyPheLeuSerTrpLeuAlaMetLeuPhe-86 |
| SEQ. ID. NO. 16981 | 100-AlaGluProLeuMetHisTyrPheSerAspIleThrAla-112 |
| SEQ. ID. NO. 16982 | 170-IleSerGlyArgPheGlyAspAlaIleAspIleMetAlaLeuLeuAlaThrPhePheGlyIleIleThrThr-193 |
| SEQ. ID. NO. 16983 | 227-MetSerLeuAlaValValSerAlaIleSerGlyValGlyLysGlyValLysValLeuSer-246 |
| SEQ. ID. NO. 16984 | 272-AlaPheGlyAspAsnIleGlyAsnTyrLeuGlyAsnLeuValArg-286 |
| SEQ. ID. NO. 16985 | 313-TrpCysSerTrpAlaProPheValGlyLeuPheIleAla-325 |
| SEQ. ID. NO. 16986 | 346-LeuPheGlyValLeuTrpPhe-352 |
| SEQ. ID. NO. 16987 | 367-AlaGlyGlyValLeuGluLysMetThrSerSer-377 |
| SEQ. ID. NO. 16988 | 380-ThrLeuLeuPheLysPhePheAsnTyrLeuProLeuProGluLeuThrSerIleValSerLeuLeu-401 |
| SEQ. ID. NO. 16989 | 438-TrpGlyValLeuMetSerAla-444 |
| SEQ. ID. NO. 16990 | 454-GlyLeuGlyAsnLeuGlnSerMetThrLeu-463 |
| SEQ. ID. NO. 16991 | 520-GluGlnAspIleLeuLysPheLeuLysHisThrAla-531 |
| SEQ. ID. NO. 16992 | 535-MetHisGluLeuGlnArgGluLeu-542 |
| SEQ. ID. NO. 16993 | 574-AspPheMetTyrGlyIle-579 |
| SEQ. ID. NO. 16994 | 583-GlyGlnAspValSerAspGlnLeu-590 |
| SEQ. ID. NO. 16995 | 630-AlaAspIleLeuLysAsnTyr-636 |
| Antigenic Index - Jameson-Wolf | |
| SEQ. ID. NO. 16996 | 29-AspArgAlaLysGlu-33 |
| SEQ. ID. NO. 16997 | 65-IleArgLeuGlyArgAspGluAspValPro-74 |
| SEQ. ID. NO. 16998 | 111-ThrAlaGlyThrProGluHisArgGlnGln-120 |
| SEQ. ID. NO. 16999 | 166-LeuLysGluLysIleSerGlyArgPheGlyAspAlaIleAsp-179 |
| SEQ. ID. NO. 17000 | 200-GlnLeuGlyAlaGlyLeu-205 |
| SEQ. ID. NO. 17001 | 237-GlyValGlyLysGlyValLysVal-244 |
| SEQ. ID. NO. 17002 | 293-AlaTyrGluArgGluHisLysProTrpPhe-302 |
| SEQ. ID. NO. 17003 | 326-ArgIleSerLysGlyArgThrIleArg-334 |
| SEQ. ID. NO. 17004 | 370-ValLeuGluLysMetThrSerSerProGluThr-380 |
| SEQ. ID. NO. 17005 | 409-ThrSerAlaAspSerGlyIle-415 |
| SEQ. ID. NO. 17006 | 421-IleThrSerArgAspLysGlyLeuSerAlaProArgTrp-433 |
| SEQ. ID. NO. 17007 | 451-ArgSerGlyGlyLeuGlyAsn-457 |
| SEQ. ID. NO. 17008 | 484-LeuSerAlaAspLysLysTyrPheGluThrArgValAsnProThrSer-499 |
| SEQ. ID. NO. 17009 | 503-ThrGlyGlyLysTrpLysGluArgLeu-511 |
| SEQ. ID. NO. 17010 | 516-SerGlnThrGlnGluGlnAspIle-523 |
| SEQ. ID. NO. 17011 | 537-GluLeuGlnArgGluLeuSerGluGluTyrGlyLeu-548 |
| SEQ. ID. NO. 17012 | 550-ValArgValAspLysMetPheHisGlnAspGluProAla-562 |
| SEQ. ID. NO. 17013 | 566-ValIleArgLysGluThrMetArg-573 |
| SEQ. ID. NO. 17014 | 581-SerValGlyGlnAspValSerAspGlnLeuIleAsnAspGlyLysLeuProHisIleArgHisGlnThrThrTyrLysProTyr-608 |
| SEQ. ID. NO. 17015 | 612-PheAspGlyArgValGlyTyr-618 |
| SEQ. ID. NO. 17016 | 622-TyrMetAsnLysAspGluLeuIle-629 |
| SEQ. ID. NO. 17017 | 632-IleLeuLysAsnTyrGlu-637 |
| SEQ. ID. NO. 17018 | 654-GluGlnValGluLeuAlaGlu-660 |
| Hydrophilic Regions - Hopp-Woods | |
| SEQ. ID. NO. 17019 | 29-AspArgAlaLysGlu-33 |
| SEQ. ID. NO. 17020 | 66-ArgLeuGlyArgAspGluAspValPro-74 |
| SEQ. ID. NO. 17021 | 114-ThrProGluHisArgGlnGln-120 |
| SEQ. ID. NO. 17022 | 166-LeuLysGluLysIleSerGlyArgPheGlyAsp-176 |
| SEQ. ID. NO. 17023 | 238-ValGlyLysGlyValLysVal-244 |
| SEQ. ID. NO. 17024 | 293-AlaTyrGluArgGluHisLysPro-300 |
| SEQ. ID. NO. 17025 | 327-IleSerLysGlyArgThrIleArg-334 |
| SEQ. ID. NO. 17026 | 370-ValLeuGluLysMetThrSerSerPro-378 |
| SEQ. ID. NO. 17027 | 422-ThrSerArgAspLysGlyLeuSer-429 |
| SEQ. ID. NO. 17028 | 484-LeuSerAlaAspLysLysTyrPheGlu-492 |
| SEQ. ID. NO. 17029 | 506-LysTrpLysGluArgLeu-511 |
| SEQ. ID. NO. 17030 | 517-GlnThrGlnGluGlnAspIle-523 |
| SEQ. ID. NO. 17031 | 537-GluLeuGlnArgGluLeuSerGluGluTyrGlyLeu-548 |
| SEQ. ID. NO. 17032 | 550-ValArgValAspLysMetPheHisGlnAspGluProAla-562 |
| SEQ. ID. NO. 17033 | 566-ValIleArgLysGluThrMetArg-573 |
| SEQ. ID. NO. 17034 | 581-SerValGlyGlnAspValSerAsp-588 |
| SEQ. ID. NO. 17035 | 590-LeuIleAsnAspGlyLysLeuProHis-598 |
| SEQ. ID. NO. 17036 | 622-TyrMetAsnLysAspGluLeuIle-629 |
| SEQ. ID. NO. 17037 | 654-GluGlnValGluLeuAlaGlu-660 |
| a164 | |
| AMPHI Regions - AMPHI | |
| SEQ. ID. NO. 17038 | 6-AlaAsnPheTyrGluMetLeuThrAlaAla-15 |
| SEQ. ID. NO. 17039 | 33-AlaTyrArgAlaLeuLysGlnGlu-40 |
| SEQ. ID. NO. 17040 | 75-AlaValSerAlaIleGlyAlaVal-82 |
| SEQ. ID. NO. 17041 | 97-TyrIleLeuAsnAspCys-102 |
| SEQ. ID. NO. 17042 | 113-LeuSerLysGluLeuAlaGlyLeuLysAla-122 |
| SEQ. ID. NO. 17043 | 148-PheGluAspValArgArgPheProGlu-156 |
| SEQ. ID. NO. 17044 | 160-LeuGlyArgGlnProArgIleAsnAspLeuAlaHis-171 |
| SEQ. ID. NO. 17045 | 189-TyrAlaAsnLeuPheAlaAsnLeuAsnGlyIleGluArgIlePheLys-204 |
| SEQ. ID. NO. 17046 | 264-ValProAlaIleTyrThr-269 |
| SEQ. ID. NO. 17047 | 282-TrpPheAsnArgIle-286 |
| SEQ. ID. NO. 17048 | 311-AlaLysLeuLeuGluGlyTyrGlyLeuSer-320 |
| SEQ. ID. NO. 17049 | 362-GluValGlyGluLeuIle-367 |

TABLE 1-continued

| | |
|---|---|
| SEQ. ID. NO. 17050 | 374-MetArgGlyTyrLeuAsn-379 |
| SEQ. ID. NO. 17051 | 387-ThrIleValAsnGlyTrpLeuLys-394 |
| SEQ. ID. NO. 17052 | 424-ValTyrProArgGluIleGluGluGlu-432 |
| SEQ. ID. NO. 17053 | 459-PheValGlnLeuLysGluGlyMet-466 |
| SEQ. ID. NO. 17054 | 472-GluIleArgArgHisLeuArgThrVal-480 |
| SEQ. ID. NO. 17055 | 484-PheLysIleProLysGln-489 |
| SEQ. ID. NO. 17056 | 499-AsnAlaThrGlyLysValLeuLysArgValLeuLysGluGlnPheAspGlyAsn-516 |
| Antigenic Index - Jameson-Wolf | |
| SEQ. ID. NO. 17057 | 1-MetAsnArgThrTyr-5 |
| SEQ. ID. NO. 17058 | 15-AlaCysArgLysAsnGlyAsnGly-22 |
| SEQ. ID. NO. 17059 | 26-PheAspGlyLysGluLysThrAlaTyrArgAlaLeuLysGlnGluAlaGluAla-43 |
| SEQ. ID. NO. 17060 | 63-ValSerAsnSerThrGlu-68 |
| SEQ. ID. NO. 17061 | 88-ThrPheLeuLysAsnSerGlu-94 |
| SEQ. ID. NO. 17062 | 100-AsnAspCysLysAla-104 |
| SEQ. ID. NO. 17063 | 112-GlyLeuSerLysGluLeuAlaGly-119 |
| SEQ. ID. NO. 17064 | 121-LysAlaGlnThrProValGlu-127 |
| SEQ. ID. NO. 17065 | 133-GlyGlnSerArgProAspGlyGluMetAlaGluGlyAspAlaPhePheGluAspValArgArgPheProGluLysProAspLeuGlyArgGlnPro ArgIleAsnAsp-168 |
| SEQ. ID. NO. 17066 | 176-SerGlyThrThrGlyHisProLysGlyAla-185 |
| SEQ. ID. NO. 17067 | 196-LeuAsnGlyIleGluArgIlePheLysIleSerLysArgAspArgPhe-211 |
| SEQ. ID. NO. 17068 | 270-AlaMetSerLysThrLysIle-276 |
| SEQ. ID. NO. 17069 | 291-SerGlyGlyAlaProLeuAla-297 |
| SEQ. ID. NO. 17070 | 304-PheLysAlaLysPheProArg-310 |
| SEQ. ID. NO. 17071 | 317-TyrGlyLeuSerGluAlaSer-323 |
| SEQ. ID. NO. 17072 | 330-ThrProGluArgGlnLysAlaArgSer-338 |
| SEQ. ID. NO. 17073 | 343-LeuProGlyLeuGluValLysAlaValAspGluGluLeuValGluValProArgGlyGluValGly-364 |
| SEQ. ID. NO. 17074 | 367-IleValArgGlyGlySerValMet-374 |
| SEQ. ID. NO. 17075 | 382-AlaAlaThrAspGluThrIle-388 |
| SEQ. ID. NO. 17076 | 393-LeuLysThrGlyAsp-397 |
| SEQ. ID. NO. 17077 | 400-ThrIleAspGluAspGly-405 |
| SEQ. ID. NO. 17078 | 410-ValAspArgLysLysAspLeuIleIleSerLysGlyGlnAsnValTyrProArgGluIleGluGluGluIleTyrLys-435 |
| SEQ. ID. NO. 17079 | 446-GlyValLysAspArgTyrAlaAspGluGluIle-456 |
| SEQ. ID. NO. 17080 | 462-LeuLysGluGlyMetAspLeuGlyGluAsnGluIleArgArgHisLeuArg-478 |
| SEQ. ID. NO. 17081 | 490-IleHisPheLysAspGlyLeuProArgAsnAlaThrGlyLysValLeuLysArgValLeuLysGluGlnPheAspGlyAsnLys-517 |
| Hydrophilic Regions - Hopp-Woods | |
| SEQ. ID. NO. 17082 | 15-AlaCysArgLysAsnGlyAsn-21 |
| SEQ. ID. NO. 17083 | 26-PheAspGlyLysGluLysThrAlaTyrArgAlaLeuLysGlnGluAlaGluAla-43 |
| SEQ. ID. NO. 17084 | 112-GlyLeuSerLysGluLeuAlaGly-119 |
| SEQ. ID. NO. 17085 | 135-SerArgProAspGlyGluMetAlaGluGlyAspAlaPhePheGluAspValArgArgPheProGluLysProAspLeuGlyArgGlnProArgIle AsnAsp-168 |
| SEQ. ID. NO. 17086 | 198-GlyIleGluArgIlePheLysIleSerLysArgAspArgPhe-211 |
| SEQ. ID. NO. 17087 | 304-PheLysAlaLysPheProArg-310 |
| SEQ. ID. NO. 17088 | 330-ThrProGluArgGlnLysAlaArgSer-338 |
| SEQ. ID. NO. 17089 | 346-LeuGluValLysAlaValAspGluGluLeuValGluValProArgGlyGluValGly-364 |
| SEQ. ID. NO. 17090 | 382-AlaAlaThrAspGluThrIle-388 |
| SEQ. ID. NO. 17091 | 400-ThrIleAspGluAspGly-405 |
| SEQ. ID. NO. 17092 | 410-ValAspArgLysLysAspLeuIleIle-418 |
| SEQ. ID. NO. 17093 | 425-TyrProArgGluIleGluGluGluIleTyrLys-435 |
| SEQ. ID. NO. 17094 | 446-GlyValLysAspArgTyrAlaAspGluGluIle-456 |
| SEQ. ID. NO. 17095 | 462-LeuLysGluGlyMetAspLeuGlyGluAsnGluIleArgArgHisLeuArg-478 |
| SEQ. ID. NO. 17096 | 494-AspGlyLeuProArgAsnAlaThr-501 |
| SEQ. ID. NO. 17097 | 503-LysValLeuLysArgValLeuLysGluGlnPheAspGlyAsnLys-517 |
| a165-1 | |
| AMPHI Regions - AMPHI | |
| SEQ. ID. NO. 17098 | 17-AlaThrLeuGlyValLeuLeuLysGluLeu-26 |
| SEQ. ID. NO. 17099 | 33-ThrLeuIleGluArgLeuGluAsp-40 |
| SEQ. ID. NO. 17100 | 72-IleIleAspProAlaArgAlaLeuAsnIleAla-82 |
| SEQ. ID. NO. 17101 | 90-GlnPheTrpAlaThr-94 |
| SEQ. ID. NO. 17102 | 108-AsnAlaValProHis-112 |
| SEQ. ID. NO. 17103 | 125-LeuGlnLysArgTyrAspAlaPheLysThrGlnLysLeuPheGluAsnMet-141 |
| SEQ. ID. NO. 17104 | 182-ArgLeuThrArgGlnMetValLysTyrLeuGlnGly-193 |
| SEQ. ID. NO. 17105 | 198-ThrGluPheAsnArgHisValGluAspIleLysArgGlu-210 |
| SEQ. ID. NO. 17106 | 364-LysThrLysGluGlu-368 |
| SEQ. ID. NO. 17107 | 371-AlaSerLeuLeuGluTyrTyr-377 |
| SEQ. ID. NO. 17108 | 456-ArgLeuLysGluLeu-460 |
| Antigenic Index - Jameson-Wolf | |
| SEQ. ID. NO. 17109 | 1-MetAlaGluAlaThrAsp-6 |
| SEQ. ID. NO. 17110 | 24-LysGluLeuGluProSerTrp-30 |
| SEQ. ID. NO. 17111 | 36-GluArgLeuGluAspValAlaLeuGluSerSerAsnAlaTrpAsnAsnAlaGlyThrGly-55 |
| SEQ. ID. NO. 17112 | 97-AlaGluGlyLysLeuGluAspAsnSer-105 |
| SEQ. ID. NO. 17113 | 117-MetAsnGluAspHisCysSerTyrLeuGlnLysArgTyrAspAlaPheLysThrGlnLysLeuPheGlu-139 |
| SEQ. ID. NO. 17114 | 141-MetGluPheSerThrAspArgAsnLysIleSerAsp-152 |
| SEQ. ID. NO. 17115 | 157-MetMetArgGlyArgAspGluAsnGlnPro-166 |
| SEQ. ID. NO. 17116 | 169-AlaAsnTyrSerAlaGluGlyThrAspValAspPheGlyArgLeuThrArgGlnMet-187 |
| SEQ. ID. NO. 17117 | 191-LeuGlnGlyLysGlyValLysThrGluPheAsnArgHisValGluAspIleLysArgGluSerAspGly-213 |
| SEQ. ID. NO. 17118 | 219-ThrAlaAspThrArgAsnProAspGlyGlnLeu-229 |
| SEQ. ID. NO. 17119 | 249-GlnLysSerGlyIleProGluGlyLysGlyTyrGly-260 |
| SEQ. ID. NO. 17120 | 269-PheArgAsnSerAsnProGluThrAlaGluGlnHisAsn-281 |
| SEQ. ID. NO. 17121 | 300-LeuAspThrArgAsnValAspGlyLysArgHisLeu-311 |
| SEQ. ID. NO. 17122 | 322-AsnPheLeuLysGlnGlySerLeuMet-330 |

TABLE 1-continued

| | |
|---|---|
| SEQ. ID. NO. 17123 | 361-GluLeuArgLysThrLysGluGluArgPhe-370 |
| SEQ. ID. NO. 17124 | 377-TyrProGluAlaAsnProAspAspTrpGlu-386 |
| SEQ. ID. NO. 17125 | 395-GlnIleIleLysLysAspSerGluLysGlyGly-405 |
| SEQ. ID. NO. 17126 | 415-AlaHisAlaAspGlySer-420 |
| SEQ. ID. NO. 17127 | 428-SerProGlyAlaSerThr-433 |
| SEQ. ID. NO. 17128 | 446-PheProGluArgThrProSerTrpGluGlyArgLeuLysGluLeuValProGlyTyr-464 |
| SEQ. ID. NO. 17129 | 467-LysLeuAsnGluAsnProGluArgAlaAspGlu-477 |
| Hydrophilic Regions - Hopp-Woods | |
| SEQ. ID. NO. 17130 | 1-MetAlaGluAlaThrAsp-6 |
| SEQ. ID. NO. 17131 | 24-LysGluLeuGluPro-28 |
| SEQ. ID. NO. 17132 | 36-GluArgLeuGluAspValAlaLeuGluSer-45 |
| SEQ. ID. NO. 17133 | 97-AlaGluGlyLysLeuGluAspAsnSer-105 |
| SEQ. ID. NO. 17134 | 117-MetAsnGluAspHisCys-122 |
| SEQ. ID. NO. 17135 | 125-LeuGlnLysArgTyrAspAlaPheLysThr-134 |
| SEQ. ID. NO. 17136 | 141-MetGluPheSerThrAspArgAsnLysIleSerAsp-152 |
| SEQ. ID. NO. 17137 | 158-MetArgGlyArgAspGluAsnGlnPro-166 |
| SEQ. ID. NO. 17138 | 172-SerAlaGluGlyThrAspValAspPhe-180 |
| SEQ. ID. NO. 17139 | 182-ArgLeuThrArgGlnMet-187 |
| SEQ. ID. NO. 17140 | 194-LysGlyValLysThrGluPheAsnArgHisValGluAspIleLysArgGluSerAspGly-213 |
| SEQ. ID. NO. 17141 | 219-ThrAlaAspThrArgAsnProAspGly-227 |
| SEQ. ID. NO. 17142 | 252-GlyIleProGluGlyLysGly-258 |
| SEQ. ID. NO. 17143 | 272-SerAsnProGluThrAlaGluGlnHisAsn-281 |
| SEQ. ID. NO. 17144 | 300-LeuAspThrArgAsnValAspGlyLysArg-309 |
| SEQ. ID. NO. 17145 | 361-GluLeuArgLysThrLysGluGluArgPhe-370 |
| SEQ. ID. NO. 17146 | 380-AlaAsnProAspAspTrpGlu-386 |
| SEQ. ID. NO. 17147 | 395-GlnIleIleLysLysAspSerGluLysGlyGly-405 |
| SEQ. ID. NO. 17148 | 446-PheProGluArgThrProSerTrpGluGlyArgLeuLysGluLeuVal-461 |
| SEQ. ID. NO. 17149 | 467-LysLeuAsnGluAsnProGluArgAlaAspGlu-477 |
| a205-1 | |
| AMPHI Regions - AMPHI | |
| SEQ. ID. NO. 17150 | 6-ProGluGlnAsnValValArgLeuThrGlyLysHisProAsnAspLeuGluAlaValValGlyLys-27 |
| SEQ. ID. NO. 17151 | 46-CysHisThrLeuPheAlaLysLeuValGlyAsnIleAlaGluAspGlyGlyLys-63 |
| SEQ. ID. NO. 17152 | 75-GlnProTyrGlnAla-79 |
| Antigenic Index - Jameson-Wolf | |
| SEQ. ID. NO. 17153 | 1-ProLeuLysGlyLeuProGluGlnAsnVal-10 |
| SEQ. ID. NO. 17154 | 13-LeuThrGlyLysHisProAsnAspLeuGluAlaValVal-25 |
| SEQ. ID. NO. 17155 | 27-LysCysMetGluThrAspGlyLysGlyAlaProSerGly-39 |
| SEQ. ID. NO. 17156 | 57-IleAlaGluAspGlyGlyLysLeuThr-65 |
| SEQ. ID. NO. 17157 | 77-TyrGlnAlaGlyLysSerGlyTyr-84 |
| SEQ. ID. NO. 17158 | 96-IleAspSerGluGly-100 |
| SEQ. ID. NO. 17159 | 103-TyrPheArgArgArgHisTyr-109 |
| Hydrophilic Regions - Hopp-Woods | |
| SEQ. ID. NO. 17160 | 13-LeuThrGlyLysHisProAsnAspLeuGluAlaValVal-25 |
| SEQ. ID. NO. 17161 | 27-LysCysMetGluThrAspGlyLysGlyAla-36 |
| SEQ. ID. NO. 17162 | 57-IleAlaGluAspGlyGlyLysLeu-64 |
| SEQ. ID. NO. 17163 | 78-GlnAlaGlyLysSerGly-83 |
| SEQ. ID. NO. 17164 | 96-IleAspSerGluGly-100 |
| SEQ. ID. NO. 17165 | 104-PheArgArgArgHisTyr-109 |
| a206 | |
| AMPHI Regions - AMPHI | |
| SEQ. ID. NO. 17166 | 32-ProLysGlnThrValArgGlnIleGlnAlaVal-42 |
| SEQ. ID. NO. 17167 | 44-IleSerHisIleAspArgThrGlnGly-52 |
| SEQ. ID. NO. 17168 | 81-CysSerGlyMetIleGln-86 |
| SEQ. ID. NO. 17169 | 99-ArgThrAlaArgAspMet-104 |
| SEQ. ID. NO. 17170 | 150-SerGlyLysThrIleLysThrGlu-157 |
| Antigenic Index - Jameson-Wolf | |
| SEQ. ID. NO. 17171 | 2-PheProProAspLysThrLeu-8 |
| SEQ. ID. NO. 17172 | 21-GlyThrThrSerGlyLysHisArgGlnProLysProLysGlnThrValArg-37 |
| SEQ. ID. NO. 17173 | 45-SerHisIleAspArgThrGlnGlySerGln-54 |
| SEQ. ID. NO. 17174 | 66-ThrProTyrLysTrpGlyGlySerSerThr-75 |
| SEQ. ID. NO. 17175 | 96-LysLeuProArgThrAlaArgAspMetAlaAlaAlaSerArgLysIleProAspSerArgLeuLysAlaGly-119 |
| SEQ. ID. NO. 17176 | 126-ThrGlyGlyAlaHisArgTyrSer-133 |
| SEQ. ID. NO. 17177 | 148-ProSerSerGlyLysThrIleLysThrGluLysLeuSer-160 |
| Hydrophilic Regions - Hopp-Woods | |
| SEQ. ID. NO. 17178 | 23-ThrSerGlyLysHisArgGlnProLysProLysGlnThrVal-36 |
| SEQ. ID. NO. 17179 | 45-SerHisIleAspArgThrGlnGlySerGln-54 |
| SEQ. ID. NO. 17180 | 96-LysLeuProArgThrAlaArgAspMetAlaAlaAlaSerArgLysIleProAspSerArgLeuLysAlaGly-119 |
| SEQ. ID. NO. 17181 | 149-SerSerGlyLysThrIleLysThrGluLysLeuSer-160 |
| a211 | |
| AMPHI Regions - AMPHI | |
| SEQ. ID. NO. 17182 | 18-ValGlyAsnGlyValAspGluPheGlyArgGlyAla-29 |
| SEQ. ID. NO. 17183 | 57-GlnPheGluArgAla-61 |
| SEQ. ID. NO. 17184 | 98-IleGluGlyPheAspLysIleAsnProAla-107 |
| Antigenic Index - Jameson-Wolf | |
| SEQ. ID. NO. 17185 | 8-AsnGlnLeuGlyGlyArgAsnGlyThrAlaValGlyAsnGlyValAspGluPheGlyArgGlyAlaAspAsnGlnValGluPheLeuGlu-37 |
| SEQ. ID. NO. 17186 | 44-GlyAlaSerGlyArgAlaAla-50 |
| SEQ. ID. NO. 17187 | 73-GlyGluAspAspValVal-78 |
| SEQ. ID. NO. 17188 | 100-GlyPheAspLysIleAsnProAlaVal-108 |
| SEQ. ID. NO. 17189 | 141-ArgTyrHisProLysLeuHisAspGlyAsnGlnAsnGlyLysArgHisGlyLysLeuHisHisArgAla-163 |
| SEQ. ID. NO. 17190 | 169-CysGlnSerAlaGly-173 |

TABLE 1-continued

| | |
|---|---|
| Hydrophilic Regions - Hopp-Woods | |
| SEQ. ID. NO. 17191 | 10-LeuGlyGlyArgAsnGlyThr-16 |
| SEQ. ID. NO. 17192 | 21-GlyValAspGluPheGlyArgGlyAlaAspAsnGlnValGluPheLeuGlu-37 |
| SEQ. ID. NO. 17193 | 73-GlyGluAspAspValVal-78 |
| SEQ. ID. NO. 17194 | 100-GlyPheAspLysIleAsn-105 |
| SEQ. ID. NO. 17195 | 142-TyrHisProLysLeuHisAspGlyAsnGlnAsnGlyLysArgHisGlyLysLeuHisHis-161 |
| a212 | |
| AMPHI Regions - AMPHI | |
| SEQ. ID. NO. 17196 | 6-TrpAsnGlyIleProAspIleArgThr-14 |
| SEQ. ID. NO. 17197 | 16-AspGlnThrIleArgLysHisAlaHls-24 |
| SEQ. ID. NO. 17198 | 40-PheGlnThrAlaGlnAsp-45 |
| SEQ. ID. NO. 17199 | 63-CysLeuGlnPheAspSerIleAsnLeuIleGluHisIle-75 |
| SEQ. ID. NO. 17200 | 89-ThrArgArgLeuHisGluHis-95 |
| SEQ. ID. NO. 17201 | 199-ArgLeuLeuGlyHis-203 |
| SEQ. ID. NO. 17202 | 238-HisAsnHisLeuTyrArgSerIleThrGlnAlaGluAlaGluLysIle-253 |
| SEQ. ID. NO. 17203 | 262-TyrAlaGluProLeuCysGlyLeu-269 |
| SEQ. ID. NO. 17204 | 397-TrpAsnGluAlaGluGluAla-403 |
| SEQ. ID. NO. 17205 | 439-AspSerProAspHis-443 |
| SEQ. ID. NO. 17206 | 445-ProLeuValGlyAlaLeuGlyAspIleAlaAlaMetGlnGlnThr-459 |
| SEQ. ID. NO. 17207 | 481-AlaTyrAlaAsnThrAlaHisGlyThrArgGlyLeu-492 |
| SEQ. ID. NO. 17208 | 506-IleLeuGlyLeuPro-510 |
| SEQ. ID. NO. 17209 | 512-ProLeuSerLysArgLeuArg-518 |
| Antigenic Index - Jameson-Wolf | |
| SEQ. ID. NO. 17210 | 10-ProAspIleArgThrLeuAspGlnThrIleArgLysHisAlaHisProLeu-26 |
| SEQ. ID. NO. 17211 | 33-ProAspAsnGlnIleProAsnPhe-40 |
| SEQ. ID. NO. 17212 | 42-ThrAlaGlnAspAlaSerAspAlaGluCysArgLeuLysHisArgLeuAspGln-59 |
| SEQ. ID. NO. 17213 | 85-ProProSerArgThrArgArgLeuHisGlu-94 |
| SEQ. ID. NO. 17214 | 105-AlaIleProGlnThrGluSerLysProAspLysProTrp-117 |
| SEQ. ID. NO. 17215 | 120-LeuProGlnThrSerGluArgGlnLysProGluHis-131 |
| SEQ. ID. NO. 17216 | 158-LeuGluAlaArgLysAlaAlaGln-165 |
| SEQ. ID. NO. 17217 | 168-SerGlyAsnArgGlnGly-173 |
| SEQ. ID. NO. 17218 | 178-LysIleSerProHisAspThrGluGlnThrGlu-188 |
| SEQ. ID. NO. 17219 | 193-GlyTyrGlyTyrThrLys-198 |
| SEQ. ID. NO. 17220 | 205-LeuProGluSerGluThrTrpGlyGlyAsnGly-215 |
| SEQ. ID. NO. 17221 | 220-AsnTyrSerArgThrGluGlnGlnArgAsnHisGluLeuGlyLeu-234 |
| SEQ. ID. NO. 17222 | 236-LysHisHisAsnHisLeu-241 |
| SEQ. ID. NO. 17223 | 245-IleThrGlnAlaGluAlaGluLysIleAla-254 |
| SEQ. ID. NO. 17224 | 258-LeuAsnThrProTyrAla-263 |
| SEQ. ID. NO. 17225 | 294-LeuHisGluAspThrProLeu-300 |
| SEQ. ID. NO. 17226 | 302-AspIleSerHisAspGlyGluLysTrpIle-311 |
| SEQ. ID. NO. 17227 | 328-ThrGlyAlaAsnSerProTyrLeuPro-336 |
| SEQ. ID. NO. 17228 | 346-ArgGlnIleArgGlyGlnThrGlyLeuThrProSerThrProPheSerGluGlnLeuArg-365 |
| SEQ. ID. NO. 17229 | 376-ProSerTrpHisGly-380 |
| SEQ. ID. NO. 17230 | 391-AsnSerSerHisThrGlyTrpAsnGluAlaGluGluAlaSerAsnArgGlnAla-408 |
| SEQ. ID. NO. 17231 | 424-AsnProAsnProGlnLysHisGlnGly-432 |
| SEQ. ID. NO. 17232 | 436-IleArgCysAspSerProAspHisLeuPro-445 |
| SEQ. ID. NO. 17233 | 464-AlaLeuAspLysAsnTyrArgIleAspAla-473 |
| SEQ. ID. NO. 17234 | 486-AlaHisGlyThrArgGlyLeuAla-493 |
| SEQ. ID. NO. 17235 | 511-HisProLeuSerLysArgLeuArgHis-519 |
| SEQ. ID. NO. 17236 | 522-HisProAsnArgAlaIle-527 |
| SEQ. ID. NO. 17237 | 531-IleValArgArgLysAspLeuThrPro-539 |
| Hydrophilic Regions - Hopp-Woods | |
| SEQ. ID. NO. 17238 | 10-ProAspIleArgThrLeuAspGlnThrIleArgLysHisAla-23 |
| SEQ. ID. NO. 17239 | 44-GlnAspAlaSerAspAlaGluCysArgLeuLysHisArgLeuAspGln-59 |
| SEQ. ID. NO. 17240 | 87-SerArgThrArgArgLeuHisGlu-94 |
| SEQ. ID. NO. 17241 | 105-AlaIleProGlnThrGluSerLysProAspLys-115 |
| SEQ. ID. NO. 17242 | 122-GlnThrSerGluArgGlnLysProGluHis-131 |
| SEQ. ID. NO. 17243 | 158-LeuGluAlaArgLysAlaAlaGln-165 |
| SEQ. ID. NO. 17244 | 180-SerProHisAspThrGluGlnThrGlu-188 |
| SEQ. ID. NO. 17245 | 206-ProGluSerGluThr-210 |
| SEQ. ID. NO. 17246 | 222-SerArgThrGluGlnGlnArgAsnHisGlu-231 |
| SEQ. ID. NO. 17247 | 246-ThrGlnAlaGluAlaGluLysIleAla-254 |
| SEQ. ID. NO. 17248 | 294-LeuHisGluAspThrProLeu-300 |
| SEQ. ID. NO. 17249 | 303-IleSerHisAspGlyGluLysTrpIle-311 |
| SEQ. ID. NO. 17250 | 346-ArgGlnIleArgGly-350 |
| SEQ. ID. NO. 17251 | 398-AsnGluAlaGluGluAlaSerAsnArgGlnAla-408 |
| SEQ. ID. NO. 17252 | 426-AsnProGlnLysHisGlnGly-432 |
| SEQ. ID. NO. 17253 | 436-IleArgCysAspSerProAsp-442 |
| SEQ. ID. NO. 17254 | 467-LysAsnTyrArgIleAspAla-473 |
| SEQ. ID. NO. 17255 | 513-LeuSerLysArgLeuArgHis-519 |
| SEQ. ID. NO. 17256 | 531-IleValArgArgLysAspLeuThrPro-539 |
| a214-1 | |
| AMPHI Regions - AMPHI | |
| SEQ. ID. NO. 17257 | 6-CysLysLeuPheValLeuIle-12 |
| SEQ. ID. NO. 17258 | 69-ValThrArgGlyGlyLysGlyGlyGluSerVal-79 |
| SEQ. ID. NO. 17259 | 88-PheSerGlnThrLeuAsp-93 |

TABLE 1-continued

| | |
|---|---|
| SEQ. ID. NO. 17260 | 122-LysValGlnArgGlyGlyAspVal-129 |
| SEQ. ID. NO. 17261 | 150-ThrLysSerGlyAlaLysSerAlaSerLys-159 |
| Antigenic Index - Jameson-Wolf | |
| SEQ. ID. NO. 17262 | 23-LeuGlnSerAspSerArgGlnProIle-31 |
| SEQ. ID. NO. 17263 | 33-IleGluAlaAspGlnGlySerLeuAspGlnAlaAsnGlnSerThrThrPheSerGlyAsn-52 |
| SEQ. ID. NO. 17264 | 71-ArgGlyGlyLysGlyGlyGluSerValArgAlaGluGlySerProValArgPheSerGlnThrLeuAspGlyGlyLysGlyThrValArgGlyGlnAla AsnAsn-105 |
| SEQ. ID. NO. 17265 | 119-GlyAsnAlaLysValGlnArgGlyGlyAspValAlaGlu-131 |
| SEQ. ID. NO. 17266 | 137-TyrAsnThrLysThrGluVal-143 |
| SEQ. ID. NO. 17267 | 148-GlySerThrLysSerGlyAlaLysSerAlaSerLysSerGlyArgValSerVal-165 |
| SEQ. ID. NO. 17268 | 168-GlnProSerSerThrGlnLysSerGlu-176 |
| Hydrophilic Regions - Hopp-Woods | |
| SEQ. ID. NO. 17269 | 25-SerAspSerArgGlnProIle-31 |
| SEQ. ID. NO. 17270 | 33-IleGluAlaAspGlnGlySerLeuAspGlnAlaAsn-44 |
| SEQ. ID. NO. 17271 | 71-ArgGlyGlyLysGlyGlyGluSerValArgAlaGluGlySerPro-85 |
| SEQ. ID. NO. 17272 | 92-LeuAspGlyGlyLysGlyThrValArgGlyGlnAla-103 |
| SEQ. ID. NO. 17273 | 121-AlaLysValGlnArgGlyGlyAspValAlaGlu-131 |
| SEQ. ID. NO. 17274 | 148-GlySerThrLysSerGlyAlaLysSerAlaSerLysSerGlyArg-162 |
| SEQ. ID. NO. 17275 | 171-SerThrGlnLysSerGlu-176 |
| a215 | |
| AMPHI Regions - AMPHI | |
| SEQ. ID. NO. 17276 | 21-SerLeuSerAlaTrpLeuGlyArgIle-29 |
| SEQ. ID. NO. 17277 | 67-SerSerLysGlyAlaLysGlnPheProGlu-76 |
| Antigenic Index - Jameson-Wolf | |
| SEQ. ID. NO. 17278 | 3-ValArgTrpArgTyrGly-8 |
| SEQ. ID. NO. 17279 | 28-ArgIleSerGluValGluIleGluGluValArgLeuAsnProAspGluProGlnTyrThrMetAspGlyLeuAspGlyArgArgPheAspGluGlnGlyTyr LeuLys-63 |
| SEQ. ID. NO. 17280 | 65-HisLeuSerSerLysGlyAlaLysGlnPheProGluSerSerAspIleHisPheAspSerProHisLeu-87 |
| SEQ. ID. NO. 17281 | 99-ValGlySerAspGluAlaValTyrHisThrGluAsnLysGlnValLeuPhe-115 |
| SEQ. ID. NO. 17282 | 123-LysThrAlaAspGlyLysArgGlnAlaGlyLysValGluAlaGluLysLeuHisValAspThrGluSerGlnTyrAlaGlnThrAspThrProVal-154 |
| SEQ. ID. NO. 17283 | 160-AlaSerHisGlyGlnAlaGlyGlyMetThrTyrAspHisLysThrGly-175 |
| SEQ. ID. NO. 17284 | 179-PheSerSerLysValLys-184 |
| SEQ. ID. NO. 17285 | 187-IleTyrAspThrLysAspMet-193 |
| Hydrophilic Regions - Hopp-Woods | |
| SEQ. ID. NO. 17286 | 29-IleSerGluValGluIleGluGluValArgLeuAsnProAspGluProGlnTyr-46 |
| SEQ. ID. NO. 17287 | 49-AspGlyLeuAspGlyArgArgPheAspGlu-58 |
| SEQ. ID. NO. 17288 | 65-HisLeuSerSerLysGlyAlaLysGlnPheProGluSerSerAspIleHisPhe-82 |
| SEQ. ID. NO. 17289 | 99-ValGlySerAspGluAlaValTyr-106 |
| SEQ. ID. NO. 17290 | 108-ThrGluAsnLysGlnValLeu-114 |
| SEQ. ID. NO. 17291 | 123-LysThrAlaAspGlyLysArgGlnAlaGlyLysValGluAlaGluLysLeuHisValAspThrGluSerGlnTyrAla-148 |
| SEQ. ID. NO. 17292 | 170-TyrAspHisLysThr-174 |
| SEQ. ID. NO. 17293 | 187-IleTyrAspThrLysAspMet-193 |
| a216 | |
| AMPHI Regions - AMPHI | |
| SEQ. ID. NO. 17294 | 21-AlaGluGlyLeuArgGluIleAlaAlaAspLeu-31 |
| SEQ. ID. NO. 17295 | 62-ArgLysMetAlaAla-66 |
| SEQ. ID. NO. 17296 | 167-LeuGlyAspAlaLeuAlaVal-173 |
| SEQ. ID. NO. 17297 | 203-ValAlaAspIleMetHis-208 |
| SEQ. ID. NO. 17298 | 218-LeuGlyThrProLeuLysGlu-224 |
| SEQ. ID. NO. 17299 | 244-GlyArgLeuLysGlyVal-249 |
| SEQ. ID. NO. 17300 | 253-GlyAspLeuArgArgLeuPheGlnGluCysAspAsnPheThrGlyLeuSerIle-270 |
| SEQ. ID. NO. 17301 | 274-MetHisThrHisProLysThrIleSerAla-283 |
| SEQ. ID. NO. 17302 | 292-LysValMetGlnAlaAsn-297 |
| Antigenic Index - Jameson-Wolf | |
| SEQ. ID. NO. 17303 | 4-AlaGlyAsnGluLysTyrLeuAspTrpAlaArg-14 |
| SEQ. ID. NO. 17304 | 16-ValLeuHisThrGluAlaGluGlyLeuArgGluIleAlaAlaAspLeuAspGlu-33 |
| SEQ. ID. NO. 17305 | 45-CysLysGlyArgVal-49 |
| SEQ. ID. NO. 17306 | 53-GlyMetGlyLysSerGlyHisIleGlyArgLysMetAla-65 |
| SEQ. ID. NO. 17307 | 82-GluAlaAlaHisGlyAspLeu-88 |
| SEQ. ID. NO. 17308 | 92-ValAspAsnAspVal-96 |
| SEQ. ID. NO. 17309 | 101-SerAsnSerGlyGluSerAspGluIle-109 |
| SEQ. ID. NO. 17310 | 115-AlaLeuLysArgLysAspIle-121 |
| SEQ. ID. NO. 17311 | 127-ThrAlaArgProAspSerThrMetAlaArgHisAlaAsp-139 |
| SEQ. ID. NO. 17312 | 146-ValSerLysGluAlaCysPro-152 |
| SEQ. ID. NO. 17313 | 179-ArgAlaPheThrProAspAspPheAla-187 |
| SEQ. ID. NO. 17314 | 190-HisProAlaGlySerLeuGlyLys-197 |
| SEQ. ID. NO. 17315 | 205-AspIleMetHisLysGlyGlyGlyLeuProAla-215 |
| SEQ. ID. NO. 17316 | 218-LeuGlyThrProLeuLysGluAlaIle-226 |
| SEQ. ID. NO. 17317 | 229-MetSerGluLysGlyLeu-234 |
| SEQ. ID. NO. 17318 | 239-ValThrAspGlyGlnGlyArgLeuLysGly-248 |
| SEQ. ID. NO. 17319 | 250-PheThrAspGlyAspLeuArgArgLeuPheGlnGluCysAspAsnPheThr-266 |
| SEQ. ID. NO. 17320 | 277-HisProLysThrIleSerAlaGluArgLeuAlaThrGluAlaLeuLys-292 |
| SEQ. ID. NO. 17321 | 305-ThrAspAlaAspGly-309 |
| Hydrophilic Regions - Hopp-Woods | |
| SEQ. ID. NO. 17322 | 5-GlyAsnGluLysTyrLeuAspTrpAlaArg-14 |
| SEQ. ID. NO. 17323 | 16-ValLeuHisThrGluAlaGluGlyLeuArgGluIleAlaAlaAspLeuAspGlu-33 |
| SEQ. ID. NO. 17324 | 45-CysLysGlyArgVal-49 |
| SEQ. ID. NO. 17325 | 58-GlyHisIleGlyArgLysMetAla-65 |
| SEQ. ID. NO. 17326 | 102-AsnSerGlyGluSerAspGluIle-109 |
| SEQ. ID. NO. 17327 | 115-AlaLeuLysArgLysAspIle-121 |

TABLE 1-continued

| | |
|---|---|
| SEQ. ID. NO. 17328 | 128-AlaArgProAspSerThrMetAlaArgHisAlaAsp-139 |
| SEQ. ID. NO. 17329 | 146-ValSerLysGluAlaCys-151 |
| SEQ. ID. NO. 17330 | 179-ArgAlaPheThrProAspAspPheAla-187 |
| SEQ. ID. NO. 17331 | 220-ThrProLeuLysGluAlaIle-226 |
| SEQ. ID. NO. 17332 | 229-MetSerGluLysGlyLeu-234 |
| SEQ. ID. NO. 17333 | 241-AspGlyGlnGlyArgLeuLys-247 |
| SEQ. ID. NO. 17334 | 253-GlyAspLeuArgArgLeuPheGlnGluCysAspAsn-264 |
| SEQ. ID. NO. 17335 | 279-LysThrIleSerAlaGluArgLeuAlaThrGluAlaLeuLys-292 |
| SEQ. ID. NO. 17336 | 305-ThrAspAlaAspGly-309 |
| a218 | |
| AMPHI Regions - AMPHI | |
| SEQ. ID. NO. 17337 | 9-AlaLysValValSerThrMet-15 |
| SEQ. ID. NO. 17338 | 24-AlaMetAspGluIleHisSer-30 |
| SEQ. ID. NO. 17339 | 78-AlaArgSerTrpTrpArgAsnLeuHisGlyAlaPheGlyThrTrpValSerLeuIleLeu-97 |
| SEQ. ID. NO. 17340 | 111-TrpGlyGlyLysPheValGlnAlaTrpSerGlnPhePro-123 |
| SEQ. ID. NO. 17341 | 176-AspGluProMetThrLeuGluThrValAspArgPheAlaArgXxxAsnArgPheGlnArgAlaLeuSerAla-199 |
| Antigenic Index - Jameson-Wolf | |
| SEQ. ID. NO. 17342 | 13-SerThrMetProArgAsnGlnGlyTrp-21 |
| SEQ. ID. NO. 17343 | 35-GlySerThrGlyAsp-39 |
| SEQ. ID. NO. 17344 | 62-ValLysArgArgGlyIleLysAla-69 |
| SEQ. ID. NO. 17345 | 71-LeuLeuProProLysGlyArgAlaArgSerTrpTrp-82 |
| SEQ. ID. NO. 17346 | 86-HisGlyAlaPheGly-90 |
| SEQ. ID. NO. 17347 | 123-ProAlaGlyLysTrpGlyValGluProAsnProVal-134 |
| SEQ. ID. NO. 17348 | 143-ValLeuAsnAspGlyLysValLysGlu-151 |
| SEQ. ID. NO. 17349 | 167-ThrValGlyLysAspGlyIleAsnProAspGluProMetThr-180 |
| SEQ. ID. NO. 17350 | 182-GluThrValAspArgPheAlaArgXxxAsnArgPheGlnArg-195 |
| SEQ. ID. NO. 17351 | 201-PheAlaGlnArgArgGlyArgArgMetAspPhe-211 |
| Hydrophilic Regions - Hopp-Woods | |
| SEQ. ID. NO. 17352 | 63-LysArgArgGlyIleLys-68 |
| SEQ. ID. NO. 17353 | 74-ProLysGlyArgAla-78 |
| SEQ. ID. NO. 17354 | 143-ValLeuAsnAspGlyLysValLysGlu-151 |
| SEQ. ID. NO. 17355 | 167-ThrValGlyLysAspGlyIleAsnProAspGluProMetThr-180 |
| SEQ. ID. NO. 17356 | 182-GluThrValAspArgPheAlaArgXxxAsnArgPheGlnArg-195 |
| SEQ. ID. NO. 17357 | 201-PheAlaGlnArgArgGlyArgArgMetAspPhe-211 |
| a225-1 | |
| AMPHI Regions - AMPHI | |
| SEQ. ID. NO. 17358 | 23-LeuAlaAspGluLeuThrAsn-29 |
| SEQ. ID. NO. 17359 | 37-IleLeuArgGlnPhe-41 |
| SEQ. ID. NO. 17360 | 155-AsnAlaMetGlyLeu-159 |
| SEQ. ID. NO. 17361 | 180-PheMetGlnHisIlePheLys-186 |
| SEQ. ID. NO. 17362 | 215-GlyAspMetValXxxPheArgThrLeuGlyGlySerArg-227 |
| SEQ. ID. NO. 17363 | 246-ThrGlyLysAsnIle-250 |
| Antigenic Index - Jameson-Wolf | |
| SEQ. ID. NO. 17364 | 22-AlaLeuAlaAspGluLeuThr-28 |
| SEQ. ID. NO. 17365 | 32-SerSerArgGluGlnIleLeu-38 |
| SEQ. ID. NO. 17366 | 41-PheAlaGluAspGluGlnProVal-48 |
| SEQ. ID. NO. 17367 | 52-AsnArgXxxProAlaArgArgAlaGlyAsnAlaAspGluLeuIle-66 |
| SEQ. ID. NO. 17368 | 71-GlyLeuAsnGluGlnProVal-77 |
| SEQ. ID. NO. 17369 | 81-AsnArgXxxProAlaArgArgAlaGlyAsnAlaAspXxx-93 |
| SEQ. ID. NO. 17370 | 100-GlyLeuAsnGluGlnProVal-106 |
| SEQ. ID. NO. 17371 | 110-AsnArgValProAlaArgArgAlaGlyAsnAlaAspGluLeuIle-124 |
| SEQ. ID. NO. 17372 | 129-GlyLeuAsnGluGlnProVal-135 |
| SEQ. ID. NO. 17373 | 137-ProValAsnArgAlaProAlaArgArgAlaGlyAsnAlaAspGluLeuIle-153 |
| SEQ. ID. NO. 17374 | 173-ThrGlyPheAspCysSerGly-179 |
| SEQ. ID. NO. 17375 | 193-LeuProArgThrSerAlaGluGlnAlaArgMet-203 |
| SEQ. ID. NO. 17376 | 205-ThrProValAlaArgSerGluLeuGlnProGlyAspMetValXxx-219 |
| SEQ. ID. NO. 17377 | 222-ThrLeuGlyGlySerArgIle-228 |
| SEQ. ID. NO. 17378 | 242-HisAlaProArgThrGlyLysAsnIleGlu-251 |
| SEQ. ID. NO. 17379 | 254-SerLeuSerHisLysTyrTrpSerGlyLys-263 |
| SEQ. ID. NO. 17380 | 268-ArgArgValLysLysAsnAspProSerArgPhe-278 |
| Hydrophilic Regions - Hopp-Woods | |
| SEQ. ID. NO. 17381 | 22-AlaLeuAlaAspGluLeuThr-28 |
| SEQ. ID. NO. 17382 | 32-SerSerArgGluGlnIleLeu-38 |
| SEQ. ID. NO. 17383 | 41-PheAlaGluAspGluGlnPro-47 |
| SEQ. ID. NO. 17384 | 53-ArgXxxProAlaArgArgAlaGlyAsnAlaAspGluLeuIle-66 |
| SEQ. ID. NO. 17385 | 82-ArgXxxProAlaArgArgAlaGlyAsnAla-91 |
| SEQ. ID. NO. 17386 | 112-ValProAlaArgArgAlaGlyAsnAlaAspGluLeuIle-124 |
| SEQ. ID. NO. 17387 | 140-ArgAlaProAlaArgArgAlaGlyAsnAlaAspGluLeuIle-153 |
| SEQ. ID. NO. 17388 | 195-ArgThrSerAlaGluGlnAlaArgMet-203 |
| SEQ. ID. NO. 17389 | 207-ValAlaArgSerGluLeuGlnPro-214 |
| SEQ. ID. NO. 17390 | 245-ArgThrGlyLysAsnIleGlu-251 |
| SEQ. ID. NO. 17391 | 268-ArgArgValLysLysAsnAspProSerArg-277 |
| a226 | |
| AMPHI Regions - AMPHI | |
| SEQ. ID. NO. 17392 | 44-LeuIleAlaTyrLeuLys-49 |
| SEQ. ID. NO. 17393 | 61-AlaAlaGlnPheIleAspPheTrpLeu-69 |
| SEQ. ID. NO. 17394 | 98-GlnLeuAlaGlySerValThrGlyIleValThr-108 |
| SEQ. ID. NO. 17395 | 141-ArgSerIleGlyGlyIleProAlaIleThr-150 |
| SEQ. ID. NO. 17396 | 157-AlaGlyLeuValGlyGlnIleAlaGlyTyrLys-167 |
| SEQ. ID. NO. 17397 | 197-GluArgSerArgArg-201 |

TABLE 1-continued

| | |
|---|---|
| Antigenic Index - Jameson-Wolf | |
| SEQ. ID. NO. 17398 | 3-GluIleLeuArgGlnProSer-9 |
| SEQ. ID. NO. 17399 | 25-ValArgThrArgThrGlyAsnIle-32 |
| SEQ. ID. NO. 17400 | 81-TyrGlnAsnArgArgLysIle-87 |
| SEQ. ID. NO. 17401 | 117-GlyAlaGluArgGluVal-122 |
| SEQ. ID. NO. 17402 | 128-SerLysSerValThrAsn-133 |
| SEQ. ID. NO. 17403 | 139-IleThrArgSerIleGlyGly-145 |
| SEQ. ID. NO. 17404 | 167-LysMetLeuLysAsnThrVal-173 |
| SEQ. ID. NO. 17405 | 195-SerLeuGluArgSerArgArgMetAla-203 |
| Hydrophilic Regions - Hopp-Woods | |
| SEQ. ID. NO. 17406 | 25-ValArgThrArgThr-29 |
| SEQ. ID. NO. 17407 | 82-GlnAsnArgArgLysIle-87 |
| SEQ. ID. NO. 17408 | 117-GlyAlaGluArgGluVal-122 |
| SEQ. ID. NO. 17409 | 195-SerLeuGluArgSerArgArgMetAla-203 |
| a227 | |
| AMPHI Regions - AMPHI | |
| SEQ. ID. NO. 17410 | 36-GlyValLeuPheAlaLeuLeuGlnAla-44 |
| SEQ. ID. NO. 17411 | 52-LeuGlnGlnLeuThrAspAlaLeu-59 |
| SEQ. ID. NO. 17412 | 74-ValIleSerTyrLeuAspLeuIleAlaAspAspTrpPheSer-87 |
| a228 | |
| AMPHI Regions - AMPHI | |
| SEQ. ID. NO. 17413 | 24-GluValLysGluAlaValGlnAlaValGlu-33 |
| SEQ. ID. NO. 17414 | 40-AlaAlaSerAlaAlaGluSerAlaAlaSerAlaValGluGluAlaLysAspGlnValLysAspAla-61 |
| SEQ. ID. NO. 17415 | 78-GluAlaValThrGluAlaAlaLysAspThrLeuAsnLysAlaAlaAspAlaThrGlnGluAlaAlaAspLysMetLysAspAlaAla-106 |
| Antigenic Index - Jameson-Wolf | |
| SEQ. ID. NO. 17416 | 18-SerGlnGluAlaLysGlnGluValLysGluAlaValGln-30 |
| SEQ. ID. NO. 17417 | 32-ValGluSerAspValLysAspThrAlaAlaSerAlaAlaGluSerAlaAlaSerAlaValGluGluAlaLysAspGlnValLysAspAlaAlaAlaAspAla LysAlaSerAlaGluGluAlaValThrGluAlaLysGluAlaValThrGluAlaAlaLysAspThrLeuAsnLysAlaAlaAspAlaThrGlnGluAlaAla AspLysMetLysAspAlaAlaLys-107 |
| Hydrophilic Regions - Hopp-Woods | |
| (SEQ. ID. NO. 17416) | |
| 18-SerGlnGluAlaLysGlnGluValLysGluAlaValGln-30 | |
| (SEQ. ID. NO. 17417) | |
| 32-ValGluSerAspValLysAspThrAlaAlaSerAlaAlaGluSerAlaAlaSerAlaValGluGluAlaLysAspGlnValLysAspAlaAlaAlaAspAlaLysAlaSerAlaGluGluAlaVal ThrGluAlaLysGluAlaValThrGluAlaAlaLysAspThrLeuAsnLysAlaAlaAspAlaThrGlnGluAlaAlaAspLysMetLysAspAlaAlaLys-107 | |
| a230-1 | |
| AMPHI Regions - AMPHI | |
| SEQ. ID. NO. 17418 | 6-GluLysTyrArgThr-10 |
| SEQ. ID. NO. 17419 | 49-AspHisSerIleAsnAsn-54 |
| SEQ. ID. NO. 17420 | 56-IleGlnAsnGluGln-60 |
| SEQ. ID. NO. 17421 | 73-GlnSerLeuLeuGln-77 |
| SEQ. ID. NO. 17422 | 81-LeuLysGlnGlyAlaLys-86 |
| SEQ. ID. NO. 17423 | 96-GlnIleLysGlnIleIle-101 |
| SEQ. ID. NO. 17424 | 133-PheValGluGluIleArgAspGlnPhe-141 |
| SEQ. ID. NO. 17425 | 144-GlnAsnLeuValAsnLeuVal-150 |
| SEQ. ID. NO. 17426 | 161-AlaGluGlnLeuIleArgLeuThrGlnValAsnArgThrIleArg-175 |
| SEQ. ID. NO. 17427 | 184-PheIleAlaGlnVal-188 |
| SEQ. ID. NO. 17428 | 194-AspLeuGlnLysPheTyrAsn-200 |
| SEQ. ID. NO. 17429 | 234-GluValLysAsnAlaPheGluGluArgValAlaArgLeu-246 |
| SEQ. ID. NO. 17430 | 272-ValAlaAspPheAsnLys-277 |
| SEQ. ID. NO. 17431 | 284-AspAspAlaPheAsnHisProSerSerLeuAlaGluAla-296 |
| SEQ. ID. NO. 17432 | 319-SerGlyMetProGluAsnLeuIleAsnAlaVal-329 |
| SEQ. ID. NO. 17433 | 398-LeuAsnGlyGlyLys-402 |
| SEQ. ID. NO. 17434 | 426-GluAlaTyrAlaGluLeu-431 |
| SEQ. ID. NO. 17435 | 444-ValArgLeuIleGlyLeuProAlaPro-452 |
| SEQ. ID. NO. 17436 | 456-GluValGlnAlaValThrProProAspAspIleAla-467 |
| SEQ. ID. NO. 17437 | 488-LeuLeuIleArgTyrPheAsn-494 |
| Antigenic Index - Jameson-Wolf | |
| SEQ. ID. NO. 17438 | 4-SerIleGluLysTyrArgThrProAla-12 |
| SEQ. ID. NO. 17439 | 32-SerHisProGlyAlaAsp-37 |
| SEQ. ID. NO. 17440 | 42-ValGlyAspGluLysIleSerAspHisSerIle-52 |
| SEQ. ID. NO. 17441 | 56-IleGlnAsnGluGlnAlaAspGlyGlyGlyProSerArgAspAlaVal-71 |
| SEQ. ID. NO. 17442 | 80-TyrLeuLysGlnGlyAla-85 |
| SEQ. ID. NO. 17443 | 92-ValSerSerGluGlnIleLys-98 |
| SEQ. ID. NO. 17444 | 101-IleValAspAspProAsnPheHisAspAlaAsnGlyLysPheAsp-115 |
| SEQ. ID. NO. 17445 | 122-TyrLeuSerGlnArgHisMetSerGluAspGlnPheValGluGluIleArgAsp-139 |
| SEQ. ID. NO. 17446 | 169-GlnValAsnArgThrIleArgSerHisThrPheAsnProAspGluPhe-184 |
| SEQ. ID. NO. 17447 | 189-LysValSerGluAlaAspLeu-195 |
| SEQ. ID. NO. 17448 | 199-TyrAsnAlaAsnLysLysAspTyrLeu-207 |
| SEQ. ID. NO. 17449 | 223-AspPheAlaAspLysGlnThrValSerGluThrGluValLysAsnAlaPheGluGluArgValAlaArg-245 |
| SEQ. ID. NO. 17450 | 247-ProAlaAsnGluAlaLysProSerPheGluGlnGluLysAlaAlaValGluAsnGluLeuLysMetLysLysAlaValAlaAspPheAsnLysAlaLys GluLysLeuGlyAspAspAlaPheAsnHisProSerSerLeuAlaGluAlaAlaLysAsnSerGlyLeuLysValGluThrGlnGluThrTrpLeuSerArgGln AspAlaGlnMetSerGlyMetProGluAsn-324 |
| SEQ. ID. NO. 17451 | 330-PheSerAspAspValLeuLysLysLysHisAsnSerGlu-342 |
| SEQ. ID. NO. 17452 | 355-ArgAlaLysGluValArgGluGluLysThrLeuPro-366 |
| SEQ. ID. NO. 17453 | 368-AlaGluAlaLysAspAlaValArg-375 |
| SEQ. ID. NO. 17454 | 377-AlaTyrIleArgThrGluAlaAlaLysLeuAlaGluAsnLysAlaLysAspValLeu-395 |
| SEQ. ID. NO. 17455 | 399-AsnGlyGlyLysAlaValAsp-405 |
| SEQ. ID. NO. 17456 | 417-GlnGlnAlaArgGlnSerMetProProGluAlaTyr-428 |
| SEQ. ID. NO. 17457 | 432-LeuLysAlaLysProAlaAsnGlyLysProAla-442 |

TABLE 1-continued

SEQ. ID. NO. 17458 459-AlaValThrProProAspAspIleAla-467
SEQ. ID. NO. 17459 476-AlaLeuAlaGlnGlnGlnSerAlaAsnThrPhe-486
SEQ. ID. NO. 17460 493-PheAsnGlyLysIleLysGlnThrLysGlyAlaGlnSerValAspAsnGlyAspGlyGln-512
Hydrophilic Regions- Hopp-Woods
SEQ. ID. NO. 17461 6-GluLysTyrArgThr-10
SEQ. ID. NO. 17462 42-ValGlyAspGluLysIleSerAsp-49
SEQ. ID. NO. 17463 56-IleGlnAsnGluGlnAlaAspGlyGlyGlyProSerArgAspAlaVal-71
SEQ. ID. NO. 17464 92-ValSerSerGluGlnIleLys-98
SEQ. ID. NO. 17465 101-IleValAspAspProAsnPhe-107
SEQ. ID. NO. 17466 110-AlaAsnGlyLysPheAsp-115
SEQ. ID. NO. 17467 126-ArgHisMetSerGluAspGlnPheValGluGluIleArgAsp-139
SEQ. ID. NO. 17468 189-LysValSerGluAlaAspLeu-195
SEQ. ID. NO. 17469 200-AsnAlaAsnLysLysAspTyrLeu-207
SEQ. ID. NO. 17470 223-AspPheAlaAspLysGlnThrValSerGluThrGluValLysAsnAlaPheGluGluArgValAlaArg-245
SEQ. ID. NO. 17471 247-ProAlaAsnGluAlaLysProSerPheGluGlnGluLysAlaAlaValGluAsnGluLeuLysMetLysLysAlaValAlaAspPheAsnLysAlaLys GluLysLeuGlyAspAspAlaPheAsn-288
SEQ. ID. NO. 17472 292-SerLeuAlaGluAlaAlaLysAsnSerGlyLeuLysValGluThrGlnGlu-308
SEQ. ID. NO. 17473 310-TrpLeuSerArgGlnAspAlaGlnMet-318
SEQ. ID. NO. 17474 333-AspValLeuLysLysLysHisAsnSer-341
SEQ. ID. NO. 17475 355-ArgAlaLysGluValArgGluGluLysThrLeuPro-366
SEQ. ID. NO. 17476 368-AlaGluAlaLysAspAlaValArg-375
SEQ. ID. NO. 17477 377-AlaTyrIleArgThrGluAlaAlaLysLeuAlaGluAsnLysAlaLysAspValLeu-395
SEQ. ID. NO. 17478 417-GlnGlnAlaArgGlnSerMetPro-424
SEQ. ID. NO. 17479 432-LeuLysAlaLysProAlaAsnGly-439
SEQ. ID. NO. 17480 461-ThrProProAspAspIleAla-467
SEQ. ID. NO. 17481 496-LysIleLysGlnThrLysGlyAlaGlnSerValAspAsnGlyAspGlyGln-512
a231-1
AMPHI Regions - AMPHI
SEQ. ID. NO. 17482 7-IleAsnArgProTyrGlnLysProAlaGluLeu-17
SEQ. ID. NO. 17483 98-ArgIlePheSerPheProGln-104
SEQ. ID. NO. 17484 209-AlaValAspAsnValLysGlyValAlaVal-218
SEQ. ID. NO. 17485 228-AlaValAlaGlyPheArgArgCysSerAlaAla-238
SEQ. ID. NO. 17486 263-LeuAlaAlaValProArgIleThrGln-271
SEQ. ID. NO. 17487 281-LysProPheHisAspPhePheAsnLeu-289
Antigenic Index - Jameson-Wolf
SEQ. ID. NO. 17488 1-MetSerLysArgLysSerIleAsnArgProTyrGlnLysProAlaGlu-16
SEQ. ID. NO. 17489 18-ProProLeuGlnAsnAsnProProPheTyrArgLysAsnArgArgLeuAsn-34
SEQ. ID. NO. 17490 39-AlaAspGlyGlyCysAlaSerProGlnLysCysArgAlaArgGlyPheGln-55
SEQ. ID. NO. 17491 90-ProAlaValArgProArgArgLeuArg-98
SEQ. ID. NO. 17492 135-MetProArgArgProVal-140
SEQ. ID. NO. 17493 150-PheAlaAspArgAsnLeuArg-156
SEQ. ID. NO. 17494 166-GluHisAlaAspAlaAsp-171
SEQ. ID. NO. 17495 174-AlaPheArgArgArgAlaGlnVal-181
SEQ. ID. NO. 17496 183-AlaArgThrArgAla-187
SEQ. ID. NO. 17497 194-ArgArgValAspIleArgHisProAspPhe-203
SEQ. ID. NO. 17498 211-AspAsnValLysGly-215
SEQ. ID. NO. 17499 231-GlyPheArgArgCysSerAlaAlaGlyGlyArgValGlyThr-244
SEQ. ID. NO. 17500 246-ValProCysArgAlaGluTyrValGluTyrGlyAsnArgArgProHisArgLeuAlaAla-265
SEQ. ID. NO. 17501 269-IleThrGlnArgThrGlnLysArgGlnGlyAspGlyLysProPhe-283
SEQ. ID. NO. 17502 294-MetProMetProSerGluHis-300
Hydrophilic Regions - Hopp-Woods
SEQ. ID. NO. 17503 1-MetSerLysArgLysSerIleAsn-8
SEQ. ID. NO. 17504 10-ProTyrGlnLysProAlaGlu-16
SEQ. ID. NO. 17505 26-PheTyrArgLysAsnArgArg-32
SEQ. ID. NO. 17506 45-SerProGlnLysCysArgAlaArgGly-53
SEQ. ID. NO. 17507 92-ValArgProArgArgLeuArg-98
SEQ. ID. NO. 17508 136-ProArgArgProVal-140
SEQ. ID. NO. 17509 150-PheAlaAspArgAsnLeuArg-156
SEQ. ID. NO. 17510 166-GluHisAlaAspAlaAsp-171
SEQ. ID. NO. 17511 174-AlaPheArgArgArgAlaGlnVal-181
SEQ. ID. NO. 17512 183-AlaArgThrArgAla-187
SEQ. ID. NO. 17513 194-ArgArgValAspIleArgHis-200
SEQ. ID. NO. 17514 231-GlyPheArgArgCysSerAlaAlaGlyGlyArgValGlyThr-244
SEQ. ID. NO. 17515 246-ValProCysArgAlaGluTyr-252
SEQ. ID. NO. 17516 254-GluTyrGlyAsnArgArgProHisArg-262
SEQ. ID. NO. 17517 269-IleThrGlnArgThrGlnLysArgGlnGlyAspGlyLysProPhe-283
a232
AMPHI Regions - AMPHI
SEQ. ID. NO. 17518 23-GlnPheLeuGlyAlaPheAsnAspAsnVal-32
SEQ. ID. NO. 17519 55-GlyGlnMetLeuAsn-59
SEQ. ID. NO. 17520 74-SerLeuSerGlyGlnLeuGlyAsnLysPheAspLysAlaValLeuAlaArgTrpAlaLysValLeuGluMetIleIleMet-100
SEQ. ID. NO. 17521 127-ThrLeuPheGlyProLeuLysTyr-134
SEQ. ID. NO. 17522 160-AlaIleLeuPheGly-164
SEQ. ID. NO. 17523 167-LeuGlyThrAlaValAlaGlyValProProTyrIleValGlyIleLeuVal-183
SEQ. ID. NO. 17524 214-ValArgGlyThrLysSerLeuLeuArgGlu-223
SEQ. ID. NO. 17525 251-LeuProThrPheThrGln-256

TABLE 1-continued

SEQ. ID. NO. 17526 319-ArgPheGluGlyLeuAsn-324
SEQ. ID. NO. 17527 340-AlaValMetThrLeuIleGlyPhePheGlyGlyPhePheSerValProLeuTyrThrTrpLeu-360
Antigenic Index - Jameson-Wolf
SEQ. ID. NO. 17528 1-MetTyrAlaLysLysGlyGlyLeuGlyLeuValLysSerArgArgPhe-16
SEQ. ID. NO. 17529 75-LeuSerGlyGlnLeuGlyAsnLysPheAspLys-85
SEQ. ID. NO. 17530 139-AspTyrLeuAspAspLysGluLeuMetMet-148
SEQ. ID. NO. 17531 200-ValProAlaLysAlaAlaAspThrGlnIle-209
SEQ. ID. NO. 17532 215-ArgGlyThrLysSerLeuLeuArgGluThrValArgHisLysPro-229
SEQ. ID. NO. 17533 258-HisLeuGlyGlyAsnAspAsnVal-265
SEQ. ID. NO. 17534 286-LysPheSerArgGluArgLeuArg-293
SEQ. ID. NO. 17535 316-HisGlyHisArgPheGluGly-322
SEQ. ID. NO. 17536 363-AlaSerSerGluThrPheArgAlaArgAla-372
SEQ. ID. NO. 17537 420-IleLysArgGluArgArgPheLeu-427
SEQ. ID. NO. 17538 431-AlaIleArgLysLysPro-436
Hydrophilic Regions - Hopp-Woods
SEQ. ID. NO. 17539 2-TyrAlaLysLysGlyGly-7
SEQ. ID. NO. 17540 11-ValLysSerArgArgPhe-16
SEQ. ID. NO. 17541 81-AsnLysPheAspLys-85
SEQ. ID. NO. 17542 140-TyrLeuAspAspLysGluLeuMet-147
SEQ. ID. NO. 17543 201-ProAlaLysAlaAlaAspThrGlnIle-209
SEQ. ID. NO. 17544 215-ArgGlyThrLysSerLeuLeuArgGluThrValArgHis-227
SEQ. ID. NO. 17545 286-LysPheSerArgGluArgLeuArg-293
SEQ. ID. NO. 17546 318-HisArgPheGluGly-322
SEQ. ID. NO. 17547 366-GluThrPheArgAlaArgAla-372
SEQ. ID. NO. 17548 420-IleLysArgGluArgArgPheLeu-427
SEQ. ID. NO. 17549 431-AlaIleArgLysLysPro-436
a233
AMPHI Regions - AMPHI
SEQ. ID. NO. 17550 61-PheAlaAspLysValGlnThr-67
SEQ. ID. NO. 17551 71-GlnValArgValTrpLysAsn-77
SEQ. ID. NO. 17552 88-AsnGlyValAlaLysLeuLeuGluThr-96
SEQ. ID. NO. 17553 119-AlaLeuThrArgLeuIleGluGlnAlaGlyAsnAla-130
SEQ. ID. NO. 17554 139-ProValAlaAspThrLeuLysCysAlaAspGlyGlyAsn-151
SEQ. ID. NO. 17555 180-AlaAlaGluAsnLeuAspGlyIleThrAsp-189
Antigenic Index - Jameson-Wolf
SEQ. ID. NO. 17556 1-MetLysArgLysAsnIle-6
SEQ. ID. NO. 17557 16-AlaArgPheGlyAlaAspLysProLysGlnTyrValGluIleGlySerLysThrValLeu-35
SEQ. ID. NO. 17558 43-GluArgHisGluAlaValAsp-49
SEQ. ID. NO. 17559 56-SerProGluAspThrPheAlaAspLysValGln-66
SEQ. ID. NO. 17560 75-TrpLysAsnGlyGlyGlnThrArgAlaGluThrValArgAsnGlyVal-90
SEQ. ID. NO. 17561 100-AlaGluThrAspAsn-104
SEQ. ID. NO. 17562 109-AspAlaAlaArgCys-113
SEQ. ID. NO. 17563 115-LeuProSerGluAlaLeu-120
SEQ. ID. NO. 17564 123-LeuIleGluGlnAlaGlyAsnAlaAlaGluGlyGly-134
SEQ. ID. NO. 17565 142-AspThrLeuLysCysAlaAspGlyGlyAsnIle-152
SEQ. ID. NO. 17566 155-ThrValGluArgThrSerLeu-161
SEQ. ID. NO. 17567 182-GluAsnLeuAspGlyIleThrAspGluAlaSerAlaValGluLysLeuGlyIle-199
SEQ. ID. NO. 17568 206-GlyAspAlaArgAsnLeuLysLeuThrGlnProGlnAspAlaTyr-220
Hydrophilic Regions - Hopp-Woods
SEQ. ID. NO. 17569 1-MetLysArgLysAsnIle-6
SEQ. ID. NO. 17570 18-PheGlyAlaAspLysProLysGlnTyrVal-27
SEQ. ID. NO. 17571 43-GluArgHisGluAlaValAsp-49
SEQ. ID. NO. 17572 56-SerProGluAspThrPheAlaAspLysValGln-66
SEQ. ID. NO. 17573 79-GlyGlnThrArgAlaGluThrValArg-87
SEQ. ID. NO. 17574 100-AlaGluThrAspAsn-104
SEQ. ID. NO. 17575 127-AlaGlyAsnAlaAlaGlu-132
SEQ. ID. NO. 17576 142-AspThrLeuLysCysAlaAsp-148
SEQ. ID. NO. 17577 182-GluAsnLeuAspGlyIleThrAspGluAlaSerAlaValGluLysLeuGlyIle-199
SEQ. ID. NO. 17578 206-GlyAspAlaArgAsnLeuLys-212
a234-2
AMPHI Regions - AMPHI
SEQ. ID. NO. 17579 26-ArgSerLeuGluValGluLysValAlaSer-35
SEQ. ID. NO. 17580 68-AspArgLeuGlySerGln-73
SEQ. ID. NO. 17581 83-GlnGlnThrAsnArgPheAsnValLeuAsnArgThrAsn-95
SEQ. ID. NO. 17582 121-GlyAspValThrGluPhe-126
SEQ. ID. NO. 17583 206-AlaValAsnSerLeuValGlnAlaValAsp-215
Antigenic Index - Jameson-Wolf
SEQ. ID. NO. 17584 21-AlaThrGluSerSerArgSerLeuGluValGluLysValAlaSer-35
SEQ. ID. NO. 17585 51-ThrPheAspAsnArgSerSerPhe-58
SEQ. ID. NO. 17586 62-IlePheSerAspGlyGluAspArgLeuGlySerGlnAla-74
SEQ. ID. NO. 17587 83-GlnGlnThrAsnArgPheAsnValLeuAsnArgThrAsn-95
SEQ. ID. NO. 17588 99-LeuLysGlnGluSerGlyIleSerGlyLysAlaHisAsnLeuLysGlyAla
AspTyr-117
SEQ. ID. NO. 17589 121-GlyAspValThrGluPheGlyArgArgAspValGlyAsp-133
SEQ. ID. NO. 17590 140-LeuGlyArgGlyLysSerGlnIle-147
SEQ. ID. NO. 17591 160-AsnThrSerGluIle-164
SEQ. ID. NO. 17592 169-GlnGlyAlaGlyGlu-173
SEQ. ID. NO. 17593 175-AlaLeuSerAsnArgGluIle-181
SEQ. ID. NO. 17594 185-GlyGlyThrSerGlyTyrAspAlaThrLeuAsnGlyLysValLeu-199
SEQ. ID. NO. 17595 214-ValAspAsnGlyAlaTrpGlnProAsnArg-223

TABLE 1-continued

Hydrophilic Regions - Hopp-Woods
SEQ. ID. NO. 17596 21-AlaThrGluSerSerArgSerLeuGluValGluLysValAla-34
SEQ. ID. NO. 17597 52-PheAspAsnArgSerSerPhe-58
SEQ. ID. NO. 17598 62-IlePheSerAspGlyGluAspArgLeuGlySerGlnAla-74
SEQ. ID. NO. 17599 99-LeuLysGlnGluSerGlyIleSerGlyLysAlaHisAsn-111
SEQ. ID. NO. 17600 122-AspValThrGluPheGlyArgArgAspValGlyAsp-133
SEQ. ID. NO. 17601 141-GlyArgGlyLysSer-145
SEQ. ID. NO. 17602 176-LeuSerAsnArgGluIle-181
a235
AMPHI Regions - AMPHI
SEQ. ID. NO. 17603 8-LeuAlaAlaValLeuAlaLeu-14
SEQ. ID. NO. 17604 18-GlnValGlnLysAlaProAsp-24
SEQ. ID. NO. 17605 86-LeuThrAsnAlaAlaAspIle-92
SEQ. ID. NO. 17606 95-ValArgProGluLysLeuHisGlnIlePhe-104
SEQ. ID. NO. 17607 120-SerTyrGlnIleLeuAspSerValThrThr-129
SEQ. ID. NO. 17608 165-GlyAlaLeuValSerAlaValValAsnGlnIleAlaAsnSerLeuThr-180
SEQ. ID. NO. 17609 187-SerLysThrAlaAlaTyrAsnLeuLeuSerProTyr-198
Antigenic Index - Jameson-Wolf
SEQ. ID. NO. 17610 20-GlnLysAlaProAspPheAspTyrThrSerPheLysGluSerLysProAla-36
SEQ. ID. NO. 17611 43-ProLeuAsnGluSerProAspValAsnGlyThr-53
SEQ. ID. NO. 17612 62-AlaProLeuSerGlu-66
SEQ. ID. NO. 17613 79-GluThrPheLysGlnAsnGlyLeuThrAsn-88
SEQ. ID. NO. 17614 93-HisAlaValArgProGluLysLeu-100
SEQ. ID. NO. 17615 131-SerAlaLysAlaArgLeuValAspSerArgAsnGlyLysGluLeuTrpSerGlySerAlaSerIleArgGluGlySerAsnAsnSerAsnSer-161
SEQ. ID. NO. 17616 178-SerLeuThrAspArgGlyTyrGlnValSerLysThrAla-190
SEQ. ID. NO. 17617 202-GlyIleLeuLysGlyProArgPheValGluGluGlnProLys-215
Hydrophilic Regions - Hopp-Woods
SEQ. ID. NO. 17618 20-GlnLysAlaProAspPheAsp-26
SEQ. ID. NO. 17619 29-SerPheLysGluSerLysPro-35
SEQ. ID. NO. 17620 44-LeuAsnGluSerProAspVal-50
SEQ. ID. NO. 17621 93-HisAlaValArgProGluLysLeu-100
SEQ. ID. NO. 17622 131-SerAlaLysAlaArgLeuValAspSerArgAsnGlyLysGluLeuTrp-146
SEQ. ID. NO. 17623 150-AlaSerIleArgGluGlySerAsnAsnSer-159
SEQ. ID. NO. 17624 179-LeuThrAspArgGlyTyrGln-185
SEQ. ID. NO. 17625 207-ProArgPheValGluGluGlnProLys-215
a236
AMPHI Regions - AMPHI
SEQ. ID. NO. 17626 11-LeuCysThrAlaPheAlaAspGlyPhe-19
SEQ. ID. NO. 17627 107-PheAlaGlyPheAlaAspCysArgProPhe-116
SEQ. ID. NO. 17628 145-AlaAspAspValProArgPhePheAlaGlyGlu-155
SEQ. ID. NO. 17629 168-ArgAspValValGlnGlyGlyLeu-175
SEQ. ID. NO. 17630 215-ValGluGlyIleThrArgIle-221
SEQ. ID. NO. 17631 245-IleArgLeuLeuHisGlyIlePheAsnArgIleGluValAla-258
SEQ. ID. NO. 17632 316-ValAlaAspGlyPheArgHisPhe-323
Antigenic Index - Jameson-Wolf
SEQ. ID. NO. 17633 42-GlyPheSerGlyAsnGlyLysPhe-49
SEQ. ID. NO. 17634 58-ArgHisGlnGlnSerLysAlaGln-65
SEQ. ID. NO. 17635 77-PhePheArgArgGlyAsnPheGlyPheGlyLeuGlnGlyArgThrAspGly
Phe-94
SEQ. ID. NO. 17636 98-GlnArgLeuAspGlyGlyGlyTyr-105
SEQ. ID. NO. 17637 109-GlyPheAlaAspCysArgProPhe-116
SEQ. ID. NO. 17638 126-ValAspGlyArgGluLeuValProSerMetGluLys-137
SEQ. ID. NO. 17639 144-AlaAlaAspAspValPro-149
SEQ. ID. NO. 17640 155-GluAlaGlnAsnArgCysAsnGlnGluAsnGlnAlaAlaArgAspValValGlnGlyGlyLeu-175
SEQ. ID. NO. 17641 195-IleGluValGluArgAlaGlnValPheArgAlaGluArgAsnHis-209
SEQ. ID. NO. 17642 213-GlyLysValGluGlyIleThrArg-220
SEQ. ID. NO. 17643 222-LysIleThrGlyAsnAlaPheLeu-229
SEQ. ID. NO. 17644 261-GlyLysGlnLysAlaGlnGly-267
SEQ. ID. NO. 17645 292-IleGlyGlyCysArgProGlnAlaGlnAspValArgAla-304
SEQ. ID. NO. 17646 310-PheLeuArgArgAspAspValAlaAspGly-319
Hydrophilic Regions - Hopp-Woods
SEQ. ID. NO. 17647 89-GlyArgThrAspGly-93
SEQ. ID. NO. 17648 98-GlnArgLeuAspGlyGlyGly-104
SEQ. ID. NO. 17649 127-AspGlyArgGluLeuValProSerMetGluLys-137
SEQ. ID. NO. 17650 144-AlaAlaAspAspValPro-149
SEQ. ID. NO. 17651 156-AlaGlnAsnArgCysAsnGlnGluAsnGlnAlaAlaArgAspValVal-171
SEQ. ID. NO. 17652 195-IleGluValGluArgAlaGlnValPheArgAlaGluArgAsnHis-209
SEQ. ID. NO. 17653 214-LysValGluGlyIleThrArg-220
SEQ. ID. NO. 17654 261-GlyLysGlnLysAlaGlnGly-267
SEQ. ID. NO. 17655 295-CysArgProGlnAlaGlnAspValArgAla-304
SEQ. ID. NO. 17656 311-LeuArgArgAspAspValAlaAspGly-319
a239
AMPHI Regions - AMPHI
SEQ. ID. NO. 17657 49-PheArgLeuIleGlnSerCys-55
SEQ. ID. NO. 17658 72-AsnAlaHisArgLysGln-77
SEQ. ID. NO. 17659 123-ProGlyPheAsnAlaLeuProAlaIlePhe-132
SEQ. ID. NO. 17660 165-SerSerAsnGluTrp-169
SEQ. ID. NO. 17661 221-PheCysAlaThrIleCysAlaSerLeuArg-230

TABLE 1-continued

| | |
|---|---|
| Antigenic Index - Jameson-Wolf | |
| SEQ. ID. NO. 17662 | 6-GlyIleAlaArgAsnArgArgMetGlu-14 |
| SEQ. ID. NO. 17663 | 19-CysArgArgProAspArgPheValValArgGlnThrArgLeuLeu-33 |
| SEQ. ID. NO. 17664 | 52-IleGlnSerCysGluValGluPro-59 |
| SEQ. ID. NO. 17665 | 66-HisAsnGlyLysSerGlyAsnAlaHisArgLysGlnGlnLysGluIle-81 |
| SEQ. ID. NO. 17666 | 100-ProAlaValArgSerAlaThrArgLysThrAla-110 |
| SEQ. ID. NO. 17667 | 132-PheArgGlyGlySerGlyLysSerAlaSer-141 |
| SEQ. ID. NO. 17668 | 144-AlaAlaGlnArgGlyArgGlyAlaCys-152 |
| SEQ. ID. NO. 17669 | 164-ArgSerSerAsnGluTrpLys-170 |
| SEQ. ID. NO. 17670 | 173-ThrAlaLysArgProProSerPheArgArgHisMetThrCysGlyAsnThrAlaProThrSerSerSerSerArgLeuIleLys-200 |
| SEQ. ID. NO. 17671 | 209-ValAlaGlySerCysProArgSerArgValArgThr-220 |
| SEQ. ID. NO. 17672 | 248-TrpArgLeuAsnArgSerSerPro-255 |
| Hydrophilic Regions - Hopp-Woods | |
| SEQ. ID. NO. 17673 | 6-GlyIleAlaArgAsnArgArgMetGlul4 |
| SEQ. ID. NO. 17674 | 20-ArgArgProAspArgPheValValArgGlnThrArg-31 |
| SEQ. ID. NO. 17675 | 67-AsnGlyLysSerGlyAsnAlaHisArgLysGlnGlnLysGluIle-81 |
| SEQ. ID. NO. 17676 | 102-ValArgSerAlaThrArgLysThrAla-110 |
| SEQ. ID. NO. 17677 | 135-GlySerGlyLysSerAlaSer-141 |
| SEQ. ID. NO. 17678 | 146-GlnArgGlyArgGlyAlaCys-152 |
| SEQ. ID. NO. 17679 | 165-SerSerAsnGluTrpLys-170 |
| SEQ. ID. NO. 17680 | 173-ThrAlaLysArgProProSerPheArgArgHisMet-184 |
| SEQ. ID. NO. 17681 | 193-SerSerSerSerArgLeuIleLys-200 |
| SEQ. ID. NO. 17682 | 211-GlySerCysProArgSerArgValArgThr-220 |
| SEQ. ID. NO. 17683 | 251-AsnArgSerSerPro-255 |
| a240 | |
| AMPHI Regions - AMPHI | |
| SEQ. ID. NO. 17684 | 19-AlaAspValGlyArgPheLeuHis-26 |
| SEQ. ID. NO. 17685 | 63-IleGlnCysLeuArgAsnHis-69 |
| SEQ. ID. NO. 17686 | 87-AlaProLeuPheAlaValCysPro-94 |
| SEQ. ID. NO. 17687 | 107-GlnGlyGluAspPheProArgAlaGlyIleGlnAsnHis-119 |
| SEQ. ID. NO. 17688 | 154-ValPheArgGlyPheIleAlaArgGlyValGlnAlaValHisAsn-168 |
| SEQ. ID. NO. 17689 | 188-PheLysArgLysPheGln-193 |
| Antigenic Index - Jameson-Wolf | |
| SEQ. ID. NO. 17690 | 9-GlyThrGluThrArgArgGlnPheAla-17 |
| SEQ. ID. NO. 17691 | 39-IleAlaHisGlyArgArgSerAspPheIleArg-49 |
| SEQ. ID. NO. 17692 | 67-ArgAsnHisLysArgPheAspCysArgThrGlyPheAsp-79 |
| SEQ. ID. NO. 17693 | 101-ValGlyGlyArgIleGlyGlnGlyGluAspPheProArgAlaGlyIleGlnAsnHisHisArgSerGly-123 |
| SEQ. ID. NO. 17694 | 139-GlnGlyLeuAsnProLeuIleGluGlyLysAspAspVal-151 |
| SEQ. ID. NO. 17695 | 173-ValProGlnAsnAspPheArg-179 |
| SEQ. ID. NO. 17696 | 187-ValPheLysArgLysPhe-192 |
| SEQ. ID. NO. 17697 | 201-AsnIleGlyLysSerAspAspValCysLys-210 |
| Hydrophilic Regions - Hopp-Woods | |
| SEQ. ID. NO. 17698 | 10-ThrGluThrArgArgGlnPheAla-17 |
| SEQ. ID. NO. 17699 | 41-HisGlyArgArgSerAspPheIleArg-49 |
| SEQ. ID. NO. 17700 | 67-ArgAsnHisLysArgPheAspCys-74 |
| SEQ. ID. NO. 17701 | 105-IleGlyGlnGlyGluAspPheProArg-113 |
| SEQ. ID. NO. 17702 | 145-IleGluGlyLysAspAspVal-151 |
| SEQ. ID. NO. 17703 | 187-ValPheLysArgLysPhe-192 |
| SEQ. ID. NO. 17704 | 203-GlyLysSerAspAspValCysLys-210 |
| a241-1 | |
| AMPHI Regions - AMPHI | |
| SEQ. ID. NO. 17705 | 6-ThrArgAlaAlaLysHis-11 |
| SEQ. ID. NO. 17706 | 35-ThrHisThrProHisGluProAlaSerSer-44 |
| SEQ. ID. NO. 17707 | 71-LysMetProSerGluMetGluGlnThrLeu-80 |
| SEQ. ID. NO. 17708 | 109-PheLeuIleGlyCysIleAlaHisThrPheAsnArgSerLeuLys-123 |
| SEQ. ID. NO. 17709 | 126-PheHisAlaCysGlnArgMetValAlaVal-135 |
| SEQ. ID. NO. 17710 | 195-HisIleAspArgIleAlaGlyIleLeuThrValGln-206 |
| SEQ. ID. NO. 17711 | 229-PheValGlnLysLeuIleValGlyIleIleHis-239 |
| Antigenic Index - Jameson-Wolf | |
| SEQ. ID. NO. 17712 | 1-MetProThrArgProThrArgAlaAlaLysHisProThrProProThrTrp-17 |
| SEQ. ID. NO. 17713 | 23-CysProArgProProTyrArgProProSerValGlnThrHisThrProHisGluProAlaSerSerThrCysAlaAlaLysSerAlaAsnArgArgGlu AsnPheHis-58 |
| SEQ. ID. NO. 17714 | 68-ProSerAsnLysMetProSerGluMetGluGlnThrLeuPheArgArgHisGlnIleProProSerCysArgGlnSer-93 |
| SEQ. ID. NO. 17715 | 119-AsnArgSerLeuLysAlaAspPhe-126 |
| SEQ. ID. NO. 17716 | 147-ThrIleAspAspAsnIleAla-153 |
| SEQ. ID. NO. 17717 | 166-PheAspPheAsnArgGluHisAlaArg-174 |
| SEQ. ID. NO. 17718 | 176-PheAsnThrAspGlnLeu181 |
| SEQ. ID. NO. 17719 | 188-ArgIleValGlyArgLysArgHisIleAspArgIleAla-200 |
| SEQ. ID. NO. 17720 | 209-PheHisGlnArgGluAsnAla-215 |
| SEQ. ID. NO. 17721 | 244-ArgAsnHisGlyIle-248 |
| SEQ. ID. NO. 17722 | 251-AspSerHisIleCysProPheArgAsnSerArgLeuIle-263 |
| Hydrophilic Regions - Hopp-Woods | |
| SEQ. ID. NO. 17723 | 1-MetProThrArgProThrArgAlaAlaLysHisProThr-13 |
| SEQ. ID. NO. 17724 | 37-ThrProHisGluProAlaSer-43 |
| SEQ. ID. NO. 17725 | 46-CysAlaAlaLysSerAlaAsnArgArgGluAsnPheHis-58 |
| SEQ. ID. NO. 17726 | 70-AsnLysMetProSerGluMetGluGlnThrLeuPheArg-82 |
| SEQ. ID. NO. 17727 | 120-ArgSerLeuLysAlaAspPhe-126 |
| SEQ. ID. NO. 17728 | 166-PheAspPheAsnArgGluHisAlaArg-174 |

TABLE 1-continued

| | |
|---|---|
| SEQ. ID. NO. 17729 | 188-ArgIleValGlyArgLysArgHisIleAspArgIleAla-200 |
| SEQ. ID. NO. 17730 | 209-PheHisGlnArgGluAsnAla-215 |
| a242 | |
| AMPHI Regions - AMPHI | |
| SEQ. ID. NO. 17731 | 23-ProGluValAlaXxxGlnPheValAspPheValGlu-34 |
| SEQ. ID. NO. 17732 | 43-GlyPheCysHisIleLeuGlnAsnLeuThrGly-53 |
| SEQ. ID. NO. 17733 | 122-AsnProPhePheAspPhePheGlnAlaValVal-132 |
| SEQ. ID. NO. 17734 | 137-HisGlnSerGlyPheGlyAspValPhe-145 |
| SEQ. ID. NO. 17735 | 156-PheGluGlnGlyVal-160 |
| SEQ. ID. NO. 17736 | 191-PheGlyHisThrArgLeuPheAspIleCys-200 |
| SEQ. ID. NO. 17737 | 262-HisProPheAlaAspPheGlyAsnPheGlnAsnLeuLeuAlaLeu-276 |
| Antigenic Index - Jameson-Wolf | |
| SEQ. ID. NO. 17738 | 13-HisPheGluGlnArgAlaGlyGlyIleAla-22 |
| SEQ. ID. NO. 17739 | 52-ThrGlyHisGlyAla-56 |
| SEQ. ID. NO. 17740 | 75-SerHisAlaAspIlePheProProArgCysPheGlyAspGlyPheAlaGlnArgGlyPhe-94 |
| SEQ. ID. NO. 17741 | 98-TrpArgAlaAspGlnAlaGlnAsnArgAla-107 |
| SEQ. ID. NO. 17742 | 137-HisGlnSerGlyPhe-141 |
| SEQ. ID. NO. 17743 | 152-LeuProArgGlnPheGluGlnGlyVal-160 |
| SEQ. ID. NO. 17744 | 164-AlaTyrAspGlyGlyPheGlyArgHisArgArgHisHis-176 |
| SEQ. ID. NO. 17745 | 283-MetArgCysAspArgIleGly-289 |
| Hydrophilic Regions - Hopp-Woods | |
| SEQ. ID. NO. 17746 | 13-HisPheGluGlnArgAlaGlyGlyIle-21 |
| SEQ. ID. NO. 17747 | 98-TrpArgAlaAspGlnAlaGlnAsnArgAla-107 |
| SEQ. ID. NO. 17748 | 155-GlnPheGluGlnGlyVal-160 |
| SEQ. ID. NO. 17749 | 168-GlyPheGlyArgHisArgArgHisHis-176 |
| SEQ. ID. NO. 17750 | 283-MetArgCysAspArgIleGly-289 |
| a243 | |
| AMPHI Regions - AMPHI | |
| SEQ. ID. NO. 17751 | 25-IlePheSerMetLeu-29 |
| SEQ. ID. NO. 17752 | 35-IleThrArgLeuAlaArgLysAlaValGlnArgLeuThrAlaSerHisIleGlnArgPheLeu-55 |
| SEQ. ID. NO. 17753 | 80-AspSerSerArgIleThrSerThrIleSerSer-90 |
| Antigenic Index - Jameson-Wolf | |
| SEQ. ID. NO. 17754 | 29-LeuProSerAsnAlaPro-34 |
| SEQ. ID. NO. 17755 | 37-ArgLeuAlaArgLysAlaValGln-44 |
| SEQ. ID. NO. 17756 | 55-LeuThrGluSerLysThrGlyAlaAsnLysSerSerSerSerCysLysPro-71 |
| SEQ. ID. NO. 17757 | 77-SerAlaSerAspSerSerArgIle-84 |
| SEQ. ID. NO. 17758 | 102-SerThrThrGlyAlaValThrLysSer-110 |
| Hydrophilic Regions - Hopp-Woods | |
| SEQ. ID. NO. 17759 | 37-ArgLeuAlaArgLysAlaValGln-44 |
| SEQ. ID. NO. 17760 | 55-LeuThrGluSerLysThrGlyAlaAsnLysSerSerSerSerCysLys-70 |
| SEQ. ID. NO. 17761 | 78-AlaSerAspSerSerArgIle-84 |
| a244-1 | |
| AMPHI Regions - AMPHI | |
| SEQ. ID. NO. 17762 | 13-IleAlaAlaLeuLeuArg-18 |
| SEQ. ID. NO. 17763 | 24-AsnAlaLeuGlnGluIleAsnGlnIleIleProGlnThr-36 |
| SEQ. ID. NO. 17764 | 72-PheAlaCysHisArgLeuHisArgLeu-80 |
| SEQ. ID. NO. 17765 | 102-LysCysPheLeuGlnLeuValGln-109 |
| SEQ. ID. NO. 17766 | 111-HisLeuHisAlaHis-115 |
| SEQ. ID. NO. 17767 | 189-IleSerArgLeuCysGlySerLeuPhe-197 |
| SEQ. ID. NO. 17768 | 206-CysLeuAspGlyPheHisArgLeuHis-214 |
| SEQ. ID. NO. 17769 | 217-AsnArgPhePheThr-221 |
| SEQ. ID. NO. 17770 | 245-TyrProArgLysIleArgThrPheSerArgAsnPheLysGlnArg-259 |
| Antigenic Index - Jameson-Wolf | |
| SEQ. ID. NO. 17771 | 1-MetProSerGluAlaArgGlnAlaGlySerAspGly-12 |
| SEQ. ID. NO. 17772 | 20-ValTyrThrGlnAsnAla-25 |
| SEQ. ID. NO. 17773 | 35-GlnThrProSerGly-39 |
| SEQ. ID. NO. 17774 | 44-HisArgAsnHisSerArgAlaGlnHis-52 |
| SEQ. ID. NO. 17775 | 81-MetAspIleArgIle-85 |
| SEQ. ID. NO. 17776 | 91-PheArgIleAspPheLeuAsp-97 |
| SEQ. ID. NO. 17777 | 125-IleGlnLysArgHis-129 |
| SEQ. ID. NO. 17778 | 134-LeuAspArgGlnHisPheHisGlyLysLeuLeuSerGlyGluLeuValArg-150 |
| SEQ. ID. NO. 17779 | 179-GlnLeuGlyAsnProArgLeu-185 |
| SEQ. ID. NO. 17780 | 234-LeuLysThrAsnTrpLysSerLysSerSerTyrTyrProArgLysIleArgThrPheSerArgAsnPheLysGlnArgGlnArgIleSerAsnSerPhe SerAsnProLeuProLysLys-273 |
| Hydrophilic Regions - Hopp-Woods | |
| SEQ. ID. NO. 17781 | 1-MetProSerGluAlaArgGlnAlaGlySerAspGly-12 |
| SEQ. ID. NO. 17782 | 46-AsnHisSerArgAlaGlnHis-52 |
| SEQ. ID. NO. 17783 | 81-MetAspIleArgIle-85 |
| SEQ. ID. NO. 17784 | 91-PheArgIleAspPheLeuAsp-97 |
| SEQ. ID. NO. 17785 | 236-ThrAsnTrpLysSerLysSer-242 |
| SEQ. ID. NO. 17786 | 247-ArgLysIleArgThrPheSerArgAsnPheLysGlnArgGlnArgIle-262 |
| a246-2 | |
| AMPHI Regions - AMPHI | |
| SEQ. ID. NO. 17787 | 39-AlaValAsnIleAlaGlnCysPheThr-47 |
| SEQ. ID. NO. 17788 | 60-ArgCysAlaGluValLeuValGluGlnPheAlaAsnLeuPhePhe-74 |
| SEQ. ID. NO. 17789 | 83-AspMetGlyArgPhe-87 |
| SEQ. ID. NO. 17790 | 132-PheGlyCysAspAspValValAspAspPheAlaGlyPheGlyArgCysPheArgProVal-151 |
| SEQ. ID. NO. 17791 | 156-GlnLeuGlyGlnValPhePheGln-163 |

TABLE 1-continued

Antigenic Index - Jameson-Wolf
SEQ. ID. NO. 17792 1-MetHisGlyArgAsnGlyGlyThrGln-9
SEQ. ID. NO. 17793 18-GlnThrGlnArgThrCysPheSerAsnGlyGluValHisAlaThrGlnThrAspIleGlySer-38
SEQ. ID. NO. 17794 78-AspCysGlyHisHisAspMetGlyArg-86
SEQ. ID. NO. 17795 92-LeuAspAspGluLeuAla-97
SEQ. ID. NO. 17796 133-GlyCysAspAspValValAspAspPheAlaGlyPheGlyArgCysPheArg-149
SEQ. ID. NO. 17797 166-GlnGlnGlyArgGlnPheArgGln-173
Hydrophilic Regions - Hopp-Woods
SEQ. ID. NO. 17798 1-MetHisGlyArgAsnGlyGly-7
SEQ. ID. NO. 17799 92-LeuAspAspGluLeuAla-97
SEQ. ID. NO. 17800 136-AspValValAspAsp-140
SEQ. ID. NO. 17801 169-ArgGlnPheArgGln-173
a247-1
AMPHI Regions - AMPHI
SEQ. ID. NO. 17802 44-ValValSerSerCysSerLysIleAlaLysProGlyLysLysIleSerThrLeuGlnGlu-63
SEQ. ID. NO. 17803 153-PheAspSerSerThr-157
Antigenic Index - Jameson-Wolf
SEQ. ID. NO. 17804 11-GluSerThrAspIleLysTyrProGly-19
SEQ. ID. NO. 17805 33-IleAspAspLeuAspAlaSerAla-40
SEQ. ID. NO. 17806 47-SerCysSerLysIleAlaLysProGlyLysLysIleSerThrLeuGlnGluAlaLysSer-66
SEQ. ID. NO. 17807 70-IleThrAsnAspAspLysGlnAsnGlyAsnIleThrArgGlnArgHis-85
SEQ. ID. NO. 17808 95-IleAlaGlyGluGluGlyLeu-101
SEQ. ID. NO. 17809 104-PheGlnLeuAspAspLysGlyLysTrpGlyAsn-114
SEQ. ID. NO. 17810 120-LysLysIleArgHisMetLys-126
SEQ. ID. NO. 17811 133-SerAspCysProGluAspAspAspAlaGlyLysGluGluLysPheLysTyrThrGlyThrPheAspSerSerThrAsnAla-159
SEQ. ID. NO. 17812 171-SerGlyThrAspThrLysIleAlaAlaSerSerAspAsnHis-184
SEQ. ID. NO. 17813 192-AlaThrIleArgGlyGlyAsnValCysAlaAsnArgThrLeu-205
Hydrophilic Regions - Hopp-Woods
SEQ. ID. NO. 17814 11-GluSerThrAspIleLys-16
SEQ. ID. NO. 17815 33-IleAspAspLeuAspAlaSerAla-40
SEQ. ID. NO. 17816 49-SerLysIleAlaLysProGlyLysLysIleSerThr-60
SEQ. ID. NO. 17817 62-GlnGluAlaLysSer-66
SEQ. ID. NO. 17818 71-ThrAsnAspAspLysGlnAsnGlyAsnIleThrArgGlnArgHis-85
SEQ. ID. NO. 17819 95-IleAlaGlyGluGluGlyLeu-101
SEQ. ID. NO. 17820 105-GlnLeuAspAspLysGlyLysTrpGly-113
SEQ. ID. NO. 17821 120-LysLysIleArgHisMetLys-126
SEQ. ID. NO. 17822 134-AspCysProGluAspAspAspAlaGlyLysGluGluLysPheLysTyr-149
SEQ. ID. NO. 17823 153-PheAspSerSerThr-157
SEQ. ID. NO. 17824 172-GlyThrAspThrLysIleAlaAlaSerSerAsp-182
a248-1
AMPHI Regions - AMPHI
SEQ. ID. NO. 17825 88-GluAsnCysGlyLysGlyLeu-94
SEQ. ID. NO. 17826 121-ValGluAlaValLysArg-126
SEQ. ID. NO. 17827 148-ThrGlnSerValSerLysMetProArgTyrIleIleGlu-160
SEQ. ID. NO. 17828 168-GluAsnValTyrArgValThrAlaLysAlaTrpGlyLysAsn-181
Antigenic Index - Jameson-Wolf
SEQ. ID. NO. 17829 1-MetArgLysGlnAsnThrLeuThr-8
SEQ. ID. NO. 17830 11-ProThrSerAspGlyGlnArgGly-18
SEQ. ID. NO. 17831 40-GlnSerTyrAsnThrGluGlnArgIleSerAlaAsnGluSerAspArgLysLeuAla-58
SEQ. ID. NO. 17832 64-AlaAlaLeuArgGluGlyGluLeuGln-72
SEQ. ID. NO. 17833 76-LeuGluTyrAspThrAspSerLysValThrPheSerGluAsnCysGlyLysGlyLeu-94
SEQ. ID. NO. 17834 99-AsnValArgThrAsnAsnAspAsnGluGluAlaPhe-110
SEQ. ID. NO. 17835 116-GlnGlyLysProThrValGluAlaValLysArgSerCysThrAlaLysSerThrGlyLeu-135
SEQ. ID. NO. 17836 137-IleAspAsnLysGlyMetGluTyrLysLysGlyThrGlnSerValSerLysMetProArgTyr-157
SEQ. ID. NO. 17837 162-LeuGlyValLysAsnGlyGluAsnValTyr-171
SEQ. ID. NO. 17838 177-AlaTrpGlyLysAsnAlaAsnThr-184
SEQ. ID. NO. 17839 192-ValSerAsnAsnAspGlu-197
Hydrophilic Regions - Hopp-Woods
SEQ. ID. NO. 17840 1-MetArgLysGlnAsnThr-6
SEQ. ID. NO. 17841 11-ProThrSerAspGlyGlnArg-17
SEQ. ID. NO. 17842 42-TyrAsnThrGluGlnArgIleSerAlaAsnGluSerAspArgLysLeuAla-58
SEQ. ID. NO. 17843 64-AlaAlaLeuArgGluGlyGluLeuGln-72
SEQ. ID. NO. 17844 76-LeuGluTyrAspThrAspSerLysValThrPhe-86
SEQ. ID. NO. 17845 101-ArgThrAsnAsnAspAsnGluGluAlaPhe-110
SEQ. ID. NO. 17846 119-ProThrValGluAlaValLysArgSerCysThrAlaLysSer-132
SEQ. ID. NO. 17847 137-IleAspAsnLysGlyMetGluTyrLysLysGlyThrGlnSerValSerLysMetPro-155
SEQ. ID. NO. 17848 165-LysAsnGlyGluAsnValTyr-171
SEQ. ID. NO. 17849 193-SerAsnAsnAspGlu-197
a249-1
AMPHI Regions - AMPHI
SEQ. ID. NO. 17850 6-CysPheArgLeuLys-10
SEQ. ID. NO. 17851 15-GlyMetAlaLeuIleGluValLeuVal-23
SEQ. ID. NO. 17852 42-ThrValAlaSerValArgGluAla-49
SEQ. ID. NO. 17853 53-ThrIleValSerGlnIleThrGlnAsnLeuMetGluGlyMet-66
Antigenic Index - Jameson-Wolf
SEQ. ID. NO. 17854 1-MetLysAsnAsnAspCysPheArgLeuLysAsnProGlnSerGly-15
SEQ. ID. NO. 17855 44-AlaSerValArgGluAlaGluThr-51
SEQ. ID. NO. 17856 70-ProThrIleAspSerAspSerAsnLysLysAsnTyr-81
SEQ. ID. NO. 17857 94-ValAspGlyAspPheGln-99
SEQ. ID. NO. 17858 102-AlaIleLysThrLysThrGlnLeuAla-110

TABLE 1-continued

| | |
|---|---|
| SEQ. ID. NO. 17859 | 135-ValCysLysAspSerSerGlyValAla-143 |
| SEQ. ID. NO. 17860 | 154-SerAsnCysAspGlySerAlaAsnGlyAspThrLeu-165 |
| SEQ. ID. NO. 17861 | 173-AspSerAlaGlyAspSerAspIleAlaArgThrAsnLeuGluThrAsnGlyAsnAsn-191 |
| SEQ. ID. NO. 17862 | 198-AlaArgValGlyGlyArgGlu-204 |
| Hydrophilic Regions - Hopp-Woods | |
| SEQ. ID. NO. 17863 | 1-MetLysAsnAsnAspCysPheArgLeuLysAsnProGln-13 |
| SEQ. ID. NO. 17864 | 44-AlaSerValArgGluAlaGluThr-51 |
| SEQ. ID. NO. 17865 | 72-IleAspSerAspSerAsnLysLysAsn-80 |
| SEQ. ID. NO. 17866 | 94-ValAspGlyAspPheGln-99 |
| SEQ. ID. NO. 17867 | 102-AlaIleLysThrLysThrGlnLeuAla-110 |
| SEQ. ID. NO. 17868 | 135-ValCysLysAspSerSerGly-141 |
| SEQ. ID. NO. 17869 | 155-AsnCysAspGlySerAlaAsnGly-162 |
| SEQ. ID. NO. 17870 | 174-SerAlaGlyAspSerAspIleAlaArgThrAsnLeuGluThrAsnGly-189 |
| SEQ. ID. NO. 17871 | 200-ValGlyGlyArgGlu-204 |
| a250 | |
| AMPHI Regions - AMPHI | |
| SEQ. ID. NO. 17872 | 8-ArgAsnGluPheIleArgGlyIleLysGlu-17 |
| SEQ. ID. NO. 17873 | 54-PheAlaGlyGlySerGlu-59 |
| SEQ. ID. NO. 17874 | 61-AlaThrValAsnLeuTrpAlaGluPro-69 |
| Antigenic Index - Jameson-Wolf | |
| SEQ. ID. NO. 17875 | 5-SerSerProArgAsnGluPheIleArgGlyIleLysGluSerSer-19 |
| SEQ. ID. NO. 17876 | 34-MetGlnGlyGlyGlnLysGlyMetSer-42 |
| SEQ. ID. NO. 17877 | 54-PheAlaGlyGlySerGlu-59 |
| SEQ. ID. NO. 17878 | 90-GlyXxxGlyThrCysProAlaProGluArgAsnThrAlaGluLysSerArgAlaArg-108 |
| Hydrophilic Regions - Hopp-Woods | |
| SEQ. ID. NO. 17879 | 5-SerSerProArgAsnGluPheIleArgGlyIleLysGluSerSer-19 |
| SEQ. ID. NO. 17880 | 95-ProAlaProGluArgAsnThrAlaGluLysSerArgAlaArg-108 |
| a251 | |
| AMPHI Regions - AMPHI | |
| SEQ. ID. NO. 17881 | 47-GlnAlaAlaAspLeuProArgAsnHisIleSerProAlaTyr-60 |
| SEQ. ID. NO. 17882 | 81-ArgArgIleGlyAla-85 |
| SEQ. ID. NO. 17883 | 110-GlnValValAlaAspPheGlyGlyIleGluGlyPhe-121 |
| SEQ. ID. NO. 17884 | 156-ArgThrValGlyArgThrValArgLeuLeuLysMetIle-168 |
| SEQ. ID. NO. 17885 | 211-AlaArgThrValPheArgAlaHis-218 |
| SEQ. ID. NO. 17886 | 255-LeuGlyGlnGluCysArg-260 |
| SEQ. ID. NO. 17887 | 262-ArgHisIleAlaArgValGluSerLeuLeuArgValPheGluTyrAlaAlaAsp-279 |
| Antigenic Index - Jameson-Wolf | |
| SEQ. ID. NO. 17888 | 9-GlnProArgAlaAspIleArgProProAlaGlnThrAspIleValProAsnCys-26 |
| SEQ. ID. NO. 17889 | 34-AspAlaAlaArgArgAlaValArg-41 |
| SEQ. ID. NO. 17890 | 50-AspLeuProArgAsnHisIleSer-57 |
| SEQ. ID. NO. 17891 | 74-GlyGlyPheArgGlyArgPheArgArg-82 |
| SEQ. ID. NO. 17892 | 98-IleArgValLysAlaValLysThrGluIle-107 |
| SEQ. ID. NO. 17893 | 145-ArgLeuValGlyThr-149 |
| SEQ. ID. NO. 17894 | 157-ThrValGlyArgThrValArg-163 |
| SEQ. ID. NO. 17895 | 175-ProValValArgGluAlaGly-181 |
| SEQ. ID. NO. 17896 | 208-ValLysHisAlaArgThrValPhe-215 |
| SEQ. ID. NO. 17897 | 251-IleLysAsnArgLeuGlyGlnGluCysArgAsnArgHisIleAlaArgValGluSer-269 |
| SEQ. ID. NO. 17898 | 286-LysThrLysThrArgAlaGluGlnProArgSerAla-297 |
| Hydrophilic Regions - Hopp-Woods | |
| SEQ. ID. NO. 17899 | 10-ProArgAlaAspIleArgProProAlaGln-19 |
| SEQ. ID. NO. 17900 | 34-AspAlaAlaArgArgAlaValArg-41 |
| SEQ. ID. NO. 17901 | 76-PheArgGlyArgPheArgArg-82 |
| SEQ. ID. NO. 17902 | 98-IleArgValLysAlaValLysThrGluIle-107 |
| SEQ. ID. NO. 17903 | 157-ThrValGlyArgThrValArg-163 |
| SEQ. ID. NO. 17904 | 175-ProValValArgGluAlaGly-181 |
| SEQ. ID. NO. 17905 | 208-ValLysHisAlaArgThrValPhe-215 |
| SEQ. ID. NO. 17906 | 253-AsnArgLeuGlyGlnGluCysArgAsnArgHisIleAlaArgValGluSer-269 |
| SEQ. ID. NO. 17907 | 287-ThrLysThrArgAlaGluGlnProArg-295 |
| a254 | |
| AMPHI Regions - AMPHI | |
| SEQ. ID. NO. 17908 | 6-ArgPheAsnThrTyrSerHis-12 |
| SEQ. ID. NO. 17909 | 32-GlyHisGlyAspGlyTyrArg-38 |
| SEQ. ID. NO. 17910 | 66-LysLeuLysSerIleLeuLys-72 |
| SEQ. ID. NO. 17911 | 142-ValLeuAlaValMetLysSerLeuThrAlaSer-152 |
| Antigenic Index - Jameson-Wolf | |
| SEQ. ID. NO. 17912 | 2-TyrThrGlyGluArgPheAsnThrTyrSer-11 |
| SEQ. ID. NO. 17913 | 32-GlyHisGlyAspGlyTyrArg-38 |
| SEQ. ID. NO. 17914 | 65-GlyLysLeuLysSerIleLeuLysLysThrAspHis-76 |
| SEQ. ID. NO. 17915 | 94-SerLeuArgAsnGlyProGly-100 |
| SEQ. ID. NO. 17916 | 120-ThrIleGlyArgLysSerGluLysArgLeuLeu-130 |
| SEQ. ID. NO. 17917 | 177-AsnAspGluLysIleArgHisGlyHisGly-186 |
| Hydrophilic Regions - Hopp-Woods | |
| SEQ. ID. NO. 17918 | 65-GlyLysLeuLysSerIleLeuLysLysThrAspHis-76 |
| SEQ. ID. NO. 17919 | 120-ThrIleGlyArgLysSerGluLysArgLeuLeu-130 |
| SEQ. ID. NO. 17920 | 177-AsnAspGluLysIleArgHis-183 |
| a255 | |
| AMPHI Regions - AMPHI | |
| SEQ. ID. NO. 17921 | 23-ValLysThrCysAlaAspPheHisAlaPheAspGlyValAspAlaHisHisGly-40 |
| SEQ. ID. NO. 17922 | 71-GlyIleGlnGlyPheAlaHis-77 |
| SEQ. ID. NO. 17923 | 139-AlaGlyGlyGlyPhe-143 |

TABLE 1-continued

| | |
|---|---|
| Antigenic Index - Jameson-Wolf | |
| SEQ. ID. NO. 17924 | 40-GlyValGlyAspPheGly-45 |
| SEQ. ID. NO. 17925 | 54-AlaGlnAlaAspGlyAspValGlyGly-62 |
| SEQ. ID. NO. 17926 | 67-LeuArgAlaAspGlyIleGln-73 |
| SEQ. ID. NO. 17927 | 91-ValGlyGlyLysLysArgIleLeu-98 |
| SEQ. ID. NO. 17928 | 115-GlyAsnValGlyGlyAspPheArgAla-123 |
| SEQ. ID. NO. 17929 | 130-PhePheGlyAsnGlySerGlyGlyAsnAlaGly-140 |
| SEQ. ID. NO. 17930 | 145-GlyGlyThrProAla-149 |
| Hydrophilic Regions - Hopp-Woods | |
| SEQ. ID. NO. 17931 | 56-AlaAspGlyAspVal-60 |
| SEQ. ID. NO. 17932 | 67-LeuArgAlaAspGly-71 |
| SEQ. ID. NO. 17933 | 92-GlyGlyLysLysArgIleLeu-98 |
| SEQ. ID. NO. 17934 | 119-GlyAspPheArgAla-123 |
| a256-1 | |
| AMPHI Regions - AMPHI | |
| SEQ. ID. NO. 17935 | 90-GlyValValValHisPheArgSerCysGlyGlyValAla-102 |
| SEQ. ID. NO. 17936 | 127-ArgTyrArgGluIleTyrAlaVal-134 |
| SEQ. ID. NO. 17937 | 141-AsnAlaLeuAlaLysTyrLeuGlyGluGln-150 |
| SEQ. ID. NO. 17938 | 174-ArgPheAspSerGlyIleThrArgLeuLeu-183 |
| SEQ. ID. NO. 17939 | 197-ArgSerLeuGlnGlyPheGlnThrAla-205 |
| SEQ. ID. NO. 17940 | 207-AlaAlaGlyCysLysThrLeuGlyGluPheAspAspArgPheThrAlaProLeuHisGly-226 |
| SEQ. ID. NO. 17941 | 233-TyrTyrArgGlnThrSerCysLysProLeuLeuLysHisValAla-247 |
| SEQ. ID. NO. 17942 | 267-ProArgAlaAspGluValSer-273 |
| Antigenic Index - Jameson-Wolf | |
| SEQ. ID. NO. 17943 | 4-ThrProProAspThrProPhe-10 |
| SEQ. ID. NO. 17944 | 12-LeuArgAsnGlyAsnAlaAspThrIleAla-21 |
| SEQ. ID. NO. 17945 | 24-PheLeuGlnArgSerAlaProAlaTyrArgArgGluLeuLeuProAspSerThrGlyLysThrLysThrAlaTyrAspPheSerAspGlyIleSer ProAspAla-58 |
| SEQ. ID. NO. 17946 | 67-LeuGluGlyGlySerGlySer-73 |
| SEQ. ID. NO. 17947 | 82-AlaValArgAspArgGlyTrpAsn-89 |
| SEQ. ID. NO. 17948 | 97-SerCysGlyGlyValAlaAsn-103 |
| SEQ. ID. NO. 17949 | 112-GlyAspThrAlaGlu-116 |
| SEQ. ID. NO. 17950 | 124-LeuAlaAlaArgTyrArgGlu-130 |
| SEQ. ID. NO. 17951 | 147-LeuGlyGluGlnGlyGluAsnAlaLeu-155 |
| SEQ. ID. NO. 17952 | 166-ValAspAlaGluAlaAlaGlyAsnArgPheAspSerGlyIle-179 |
| SEQ. ID. NO. 17953 | 192-LeuIleProLysAlaArgSerLeuGln-200 |
| SEQ. ID. NO. 17954 | 212-ThrLeuGlyGluPheAspAspArgPheThr-221 |
| SEQ. ID. NO. 17955 | 227-PheAlaAspArgHisAspTyrTyrArgGlnThrSerCysLysProLeuLeu-243 |
| SEQ. ID. NO. 17956 | 259-ProPheLeuProProGluAlaLeuProArgAlaAspGluValSerGlu-274 |
| SEQ. ID. NO. 17957 | 292-SerThrGlyGlyArgLeu-297 |
| SEQ. ID. NO. 17958 | 311-AspSerPheArgThrAsnArgArg-318 |
| Hydrophilic Regions - Hopp-Woods | |
| SEQ. ID. NO. 17959 | 28-SerAlaProAlaTyrArgArgGluLeuLeuPro-38 |
| SEQ. ID. NO. 17960 | 40-SerThrGlyLysThrLysThr-46 |
| SEQ. ID. NO. 17961 | 83-ValArgAspArgGlyTrp-88 |
| SEQ. ID. NO. 17962 | 124-LeuAlaAlaArgTyrArgGlu-130 |
| SEQ. ID. NO. 17963 | 147-LeuGlyGluGlnGlyGluAsnAlaLeu-155 |
| SEQ. ID. NO. 17964 | 166-ValAspAlaGluAlaAlaGlyAsnArgPheAspSerGlyIle-179 |
| SEQ. ID. NO. 17965 | 192-LeuIleProLysAlaArgSer-198 |
| SEQ. ID. NO. 17966 | 212-ThrLeuGlyGluPheAspAspArgPheThr-221 |
| SEQ. ID. NO. 17967 | 227-PheAlaAspArgHisAspTyrTyrArg-235 |
| SEQ. ID. NO. 17968 | 265-AlaLeuProArgAlaAspGluValSerGlu-274 |
| SEQ. ID. NO. 17969 | 313-PheArgThrAsnArgArg-318 |
| a257 | |
| AMPHI Regions - AMPHI | |
| SEQ. ID. NO. 17970 | 24-SerPheLeuProAsn-28 |
| SEQ. ID. NO. 17971 | 73-AspLeuValAsnLysValLeuAlaGluValAlaArgLeuGluLysMetPhe-89 |
| SEQ. ID. NO. 17972 | 109-SerProProAlaAspPheLeuGluLeuLeuSerLeuAlaValIlePheThr-125 |
| Antigenic Index - Jameson-Wolf | |
| SEQ. ID. NO. 17973 | 1-MetGlyArgHisPheGlyArgArgArgPhe-10 |
| SEQ. ID. NO. 17974 | 31-AlaAlaAspAspGluLysArgAsnLysAspGluLysArgAsnGluAsn-46 |
| SEQ. ID. NO. 17975 | 56-GlySerGlyAlaGlu-60 |
| SEQ. ID. NO. 17976 | 65-GlyValAspAspArgArgAlaAlaAspLeuVal-75 |
| SEQ. ID. NO. 17977 | 83-AlaArgLeuGluLys-87 |
| SEQ. ID. NO. 17978 | 92-TyrArgGluAspSerLeuIleSerArgLeuAsnArgAspGlyTyrLeuThrSerProProAlaAspPhe-114 |
| Hydrophilic Regions - Hopp-Woods | |
| SEQ. ID. NO. 17979 | 4-HisPheGlyArgArgArgPhe-10 |
| SEQ. ID. NO. 17980 | 31-AlaAlaAspAspGluLysArgAsnLysAspGluLysArgAsnGlu-45 |
| SEQ. ID. NO. 17981 | 65-GlyValAspAspArgArgAlaAlaAspLeuVal-75 |
| SEQ. ID. NO. 17982 | 83-AlaArgLeuGluLys-87 |
| SEQ. ID. NO. 17983 | 92-TyrArgGluAspSerLeuIle-98 |
| SEQ. ID. NO. 17984 | 100-ArgLeuAsnArgAspGlyTyr-106 |
| a259-1 | |
| AMPHI Regions - AMPHI | |
| SEQ. ID. NO. 17985 | 154-TyrGlyArgValPheAlaAspIlePheGluLeuSer-165 |
| SEQ. ID. NO. 17986 | 172-AlaPheLysGlyMetLeuLysLeuThrAlaGluTyrLysAsnIlePheGlyAspAlaCysArg-192 |
| SEQ. ID. NO. 17987 | 203-AsnGlnAlaLeuGlnGluIleSerLysThrSerGlu-214 |
| Antigenic Index - Jameson-Wolf | |
| SEQ. ID. NO. 17988 | 34-LysAlaTyrThrGluGluLeuProPro-42 |
| SEQ. ID. NO. 17989 | 61-SerAlaArgSerLysAlaLysAlaGluLysPheTyrArgGluLysMetIleGln-78 |

TABLE 1-continued

| | |
|---|---|
| SEQ. ID. NO. 17990 | 93-LeuGluHisLysPro-97 |
| SEQ. ID. NO. 17991 | 105-LysAsnHisGlyLysGlyMetAlaGluGlnValArgPheLysAla-119 |
| SEQ. ID. NO. 17992 | 121-ValLeuProAspAspGluAspAlaArgThrIleAla-132 |
| SEQ. ID. NO. 17993 | 144-GlyThrAspAlaValAlaSerGlyGluThrTyrGlyArgVal-157 |
| SEQ. ID. NO. 17994 | 168-LeuGluGlyArgAlaPhe-173 |
| SEQ. ID. NO. 17995 | 189-AspAlaCysArgSerGluThrAlaLeu-197 |
| SEQ. ID. NO. 17996 | 208-GluIleSerLysThrSerGluLysSerLysArg-218 |
| Hydrophilic Regions - Hopp-Woods | |
| SEQ. ID. NO. 17997 | 35-AlaTyrThrGluGluLeuPro-41 |
| SEQ. ID. NO. 17998 | 62-AlaArgSerLysAlaLysAlaGluLysPheTyrArgGluLysMetIleGln-78 |
| SEQ. ID. NO. 17999 | 93-LeuGluHisLysPro-97 |
| SEQ. ID. NO. 18000 | 106-AsnHisGlyLysGlyMetAlaGluGlnValArgPheLysAla-119 |
| SEQ. ID. NO. 18001 | 121-ValLeuProAspAspGluAspAlaArgThrIleAla-132 |
| SEQ. ID. NO. 18002 | 168-LeuGluGlyArgAlaPhe-173 |
| SEQ. ID. NO. 18003 | 189-AspAlaCysArgSerGluThrAlaLeu-197 |
| SEQ. ID. NO. 18004 | 208-GluIleSerLysThrSerGluLysSerLysArg-218 |
| a260 | |
| AMPHI Regions - AMPHI | |
| SEQ. ID. NO. 18005 | 12-ProPheSerSerLeuPheArgAlaLeuPhe-21 |
| SEQ. ID. NO. 18006 | 53-PheIleAspSerValGlyGlnValAlaAlaArgLeuPheGlnAlaPhe-68 |
| SEQ. ID. NO. 18007 | 154-ValGlnIleAsnGlnValGlyIleValAspLeuIlePro-166 |
| SEQ. ID. NO. 18008 | 176-AlaThrGlyCysThrGlyIleCysProLysCysProThrGlyCysArgPro-192 |
| Antigenic Index - Jameson-Wolf | |
| SEQ. ID. NO. 18009 | 20-LeuPheGluAspArgValGlyIle-27 |
| SEQ. ID. NO. 18010 | 30-GlyAlaHisAspAlaAlaGlu-36 |
| SEQ. ID. NO. 18011 | 38-AspPheLeuProGluGluPheThrArg-46 |
| SEQ. ID. NO. 18012 | 80-ProAlaPheArgAlaArgGluGlnAlaArgArgGlySerGly-93 |
| SEQ. ID. NO. 18013 | 96-AlaGlyAsnAspLeuArgValProHisLysAspAlaValGluValAspIleAspGlyGlyAsnThrVal-118 |
| SEQ. ID. NO. 18014 | 126-ThrHisPheAspAspGlyAspAla-133 |
| SEQ. ID. NO. 18015 | 139-AlaGluAlaArgPhe-143 |
| SEQ. ID. NO. 18016 | 184-ProLysCysProThrGlyCysArgProVal-193 |
| Hydrophilic Regions - Hopp-Woods | |
| SEQ. ID. NO. 18017 | 20-LeuPheGluAspArgValGlyIle-27 |
| SEQ. ID. NO. 18018 | 30-GlyAlaHisAspAlaAlaGlu-36 |
| SEQ. ID. NO. 18019 | 82-PheArgAlaArgGluGlnAlaArgArgGlySer-92 |
| SEQ. ID. NO. 18020 | 98-AsnAspLeuArgValProHisLysAspAlaValGluValAspIleAspGly-114 |
| SEQ. ID. NO. 18021 | 127-HisPheAspAspGlyAspAla-133 |
| SEQ. ID. NO. 18022 | 139-AlaGluAlaArgPhe-143 |
| SEQ. ID. NO. 18023 | 186-CysProThrGlyCysArgProVal-193 |
| a261 | |
| AMPHI Regions - AMPHI | |
| SEQ. ID. NO. 18024 | 22-GlnIlePheArgGln-26 |
| SEQ. ID. NO. 18025 | 32-AspThrAlaArgAlaPheAlaAlaAla-40 |
| SEQ. ID. NO. 18026 | 50-GlyLeuLeuAlaAspIleVal-56 |
| SEQ. ID. NO. 18027 | 92-ValHisGlyPheAspLysHis-98 |
| SEQ. ID. NO. 18028 | 137-AlaValTyrLysGlyIleArgAsnAlaValPhe-147 |
| SEQ. ID. NO. 18029 | 158-GlnGlyIleValArgAsnLeu-164 |
| SEQ. ID. NO. 18030 | 203-AspValPheAlaProVal-208 |
| SEQ. ID. NO. 18031 | 212-CysLeuAsnGlnAlaGlyGly-218 |
| Antigenic Index - Jameson-Wolf | |
| SEQ. ID. NO. 18032 | 40-AlaAlaAspAspAlaVal-45 |
| SEQ. ID. NO. 18033 | 60-HisPheValArgGlnArgProSerLeuArgLeu-70 |
| SEQ. ID. NO. 18034 | 74-HisGlnArgArgValAspLeu-80 |
| SEQ. ID. NO. 18035 | 86-ArgGlnIleLysGlyAsnValHisGlyPheAspLysHisVal-99 |
| SEQ. ID. NO. 18036 | 111-AlaHisAlaArgAspAspValProTyr-119 |
| SEQ. ID. NO. 18037 | 126-AsnArgGlyIleGluGlnGluLysArgVal-135 |
| SEQ. ID. NO. 18038 | 149-SerPheAspGlyGlyGly-154 |
| SEQ. ID. NO. 18039 | 181-ArgAsnProAlaGly-185 |
| SEQ. ID. NO. 18040 | 197-LeuGluSerAsnGlyLeuAsp-203 |
| SEQ. ID. NO. 18041 | 214-AsnGlnAlaGlyGlyArgIleLeuThrAlaArgLysAspAspGlnGlyPhe-230 |
| Hydrophilic Regions - Hopp-Woods | |
| SEQ. ID. NO. 18042 | 40-AlaAlaAspAspAlaVal-45 |
| SEQ. ID. NO. 18043 | 60-HisPheValArgGlnArgProSerLeu-68 |
| SEQ. ID. NO. 18044 | 74-HisGlnArgArgValAspLeu-80 |
| SEQ. ID. NO. 18045 | 94-GlyPheAspLysHisVal-99 |
| SEQ. ID. NO. 18046 | 112-HisAlaArgAspAspValPro-118 |
| SEQ. ID. NO. 18047 | 127-ArgGlyIleGluGlnGluLysArgVal-135 |
| SEQ. ID. NO. 18048 | 221-LeuThrAlaArgLysAspAspGlnGly-229 |
| a263 | |
| AMPHI Regions - AMPHI | |
| SEQ. ID. NO. 18049 | 32-AsnLeuIleGlyValLeuSerAsnAla-40 |
| SEQ. ID. NO. 18050 | 42-GluAlaLeuAlaPheTyrGlnGluValGlyLysLeuAsnAlaAlaAsnSerLeuThr-60 |
| SEQ. ID. NO. 18051 | 86-LysLeuAlaThrLeuLysLys-92 |
| SEQ. ID. NO. 18052 | 100-LysAlaAlaArgAlaLeuAlaAlaGlyGlu-109 |
| SEQ. ID. NO. 18053 | 115-LeuGlyAlaLeuAlaAlaPheThrGln-123 |
| SEQ. ID. NO. 18054 | 135-GluGluLeuLysAlaPhePheAspAla-143 |
| SEQ. ID. NO. 18055 | 157-ValAlaLeuAlaThrLeuCysAsnTyrValAsnAsnLeuGly-170 |
| Antigenic Index - Jameson-Wolf | |
| SEQ. ID. NO. 18056 | 10-GluThrAlaProGluAlaAlaLysAlaArgValGluAla-22 |
| SEQ. ID. NO. 18057 | 37-LeuSerAsnAlaPro-41 |

TABLE 1-continued

| | |
|---|---|
| SEQ. ID. NO. 18058 | 72-AlaArgThrAsnGlnCysGly-78 |
| SEQ. ID. NO. 18059 | 97-GlnSerValLysAlaAlaArg-103 |
| SEQ. ID. NO. 18060 | 108-GlyGluPheAspAspAlaLysLeu-115 |
| SEQ. ID. NO. 18061 | 126-MetAlaLysLysGlyAlaValSerAspGluGluLeuLysAla-139 |
| SEQ. ID. NO. 18062 | 170-GlyGlnThrGluIleAsnProGluLeu-178 |
| Hydrophilic Regions - Hopp-Woods | |
| SEQ. ID. NO. 18063 | 11-ThrAlaProGluAlaAlaLysAlaArgValGluAla-22 |
| SEQ. ID. NO. 18064 | 97-GlnSerValLysAlaAlaArg-103 |
| SEQ. ID. NO. 18065 | 108-GlyGluPheAspAspAlaLysLeu-115 |
| SEQ. ID. NO. 18066 | 126-MetAlaLysLysGlyAlaValSerAspGluGluLeuLysAla-139 |
| a264 | |
| AMPHI Regions - AMPHI | |
| SEQ. ID. NO. 18067 | 55-ValAlaGluPheThrGlnThrGly-62 |
| SEQ. ID. NO. 18068 | 96-IleProSerTyrValArgValThrAsnThrLys-106 |
| SEQ. ID. NO. 18069 | 124-AsnArgIleIleAspValSer-130 |
| SEQ. ID. NO. 18070 | 183-LeuAsnGlnAlaAlaGlnAsnLeuAlaSerSer-193 |
| Antigenic Index - Jameson-Wolf | |
| SEQ. ID. NO. 18071 | 27-AlaValValArgAlaGluLysLeuHisAlaSerAlaAsnArgSerTyrLysValAlaGlyLysArgTyrThrProLysAsnGlnVal-55 |
| SEQ. ID. NO. 18072 | 57-GluPheThrGlnThrGlyAsnAlaSerTrp-66 |
| SEQ. ID. NO. 18073 | 68-GlyGlyArgPheHisGlyArgLysThrSerGlyGlyGluArgTyrAsp-83 |
| SEQ. ID. NO. 18074 | 103-ThrAsnThrLysAsnGlyLysSerVal-111 |
| SEQ. ID. NO. 18075 | 114-ArgValAsnAspArgGlyProPheHisGlyAsnArgIleIleAspValSerLysAlaAlaAla-134 |
| SEQ. ID. NO. 18076 | 153-ValProGlyGlnSerAlaProValAlaGluAsnLysAspIlePheIle-168 |
| SEQ. ID. NO. 18077 | 170-LeuLysSerPheGlyThrGluHisGluAla-179 |
| SEQ. ID. NO. 18078 | 192-SerSerAlaSerAsnProAsnLeuSerValGluLysArgArgTyrGluTyr-208 |
| SEQ. ID. NO. 18079 | 216-AlaSerGlnGluArgAlaAlaGluAlaGluAlaGlnAla-228 |
| Hydrophilic Regions - Hopp-Woods | |
| SEQ. ID. NO. 18080 | 27-AlaValValArgAlaGluLysLeuHisAlaSerAlaAsnArgSerTyrLysValAlaGlyLysArgTyrThrPro-51 |
| SEQ. ID. NO. 18081 | 71-PheHisGlyArgLysThrSerGlyGlyGluArgTyrAsp-83 |
| SEQ. ID. NO. 18082 | 103-ThrAsnThrLysAsnGlyLys-109 |
| SEQ. ID. NO. 18083 | 115-ValAsnAspArgGlyProPheHis-122 |
| SEQ. ID. NO. 18084 | 125-ArgIleIleAspValSerLysAlaAlaAla-134 |
| SEQ. ID. NO. 18085 | 159-ProValAlaGluAsnLysAspIlePheIle-168 |
| SEQ. ID. NO. 18086 | 171-LysSerPheGlyThrGluHisGluAla-179 |
| SEQ. ID. NO. 18087 | 199-LeuSerValGluLysArgArgTyrGluTyr-208 |
| SEQ. ID. NO. 18088 | 216-AlaSerGlnGluArgAlaAlaGluAlaGluAlaGlnAla-228 |
| a266 | |
| Antigenic Index - Jameson-Wolf | |
| SEQ. ID. NO. 18089 | 5-AsnAlaPheArgArgHisArgArgArgGlnCysProAsnArgLysProAlaMet-22 |
| SEQ. ID. NO. 18090 | 51-ProLeuLysArgLysHisPhe-57 |
| SEQ. ID. NO. 18091 | 80-SerArgAlaGlyAlaValHisAspGlnGlyTrpGlu-91 |
| SEQ. ID. NO. 18092 | 114-TrpHisThrArgAsnArgGlu-120 |
| Hydrophilic Regions - Hopp-Woods | |
| SEQ. ID. NO. 18093 | 5-AsnAlaPheArgArgHisArgArgArgGlnCysProAsnArgLysProAlaMet-22 |
| SEQ. ID. NO. 18094 | 51-ProLeuLysArgLysHisPhe-57 |
| SEQ. ID. NO. 18095 | 80-SerArgAlaGlyAlaValHis-86 |
| a268-1 | |
| AMPHI Regions - AMPHI | |
| SEQ. ID. NO. 18096 | 6-AspGlyLeuHisLysPheLysHisIleCysSerAlaAla-18 |
| SEQ. ID. NO. 18097 | 22-IleLysGluProLeuAspLys-28 |
| SEQ. ID. NO. 18098 | 52-GlnGluValAspArgValSerGluTrp-60 |
| SEQ. ID. NO. 18099 | 70-GluPheGluGlnPheTrpLysGlyLeuProGlnThrValGlnAsn-84 |
| SEQ. ID. NO. 18100 | 89-SerGlnLysThrTrpLysSerGlyMetAspLys-99 |
| SEQ. ID. NO. 18101 | 110-GluThrProAsnGlyIleLys-116 |
| Antigenic Index - Jameson-Wolf | |
| SEQ. ID. NO. 18102 | 1-ValGlnSerArgTyrAspGly-7 |
| SEQ. ID. NO. 18103 | 21-LeuIleLysGluProLeuAspLysAlaLysGlnArgAsnGluGluLeuGluAlaAlaGluGluAlaAlaAla-44 |
| SEQ. ID. NO. 18104 | 47-AlaLeuGlyArgGluGlnGluValAspArgValSerGluTrpGluGluArgTyrLysLeuSerArgSerGluPhe-71 |
| SEQ. ID. NO. 18105 | 82-ValGlnAsnLysLeuGlnAlaSerGlnLysThrTrpLysSerGlyMetAspLysIleCysAlaAsnAsnAlaLysAlaGluGlyGluThrProAsnGly-114 |
| SEQ. ID. NO. 18106 | 119-GluLeuAlaCysLysThrAlaGluThrGluAlaArgLeuGluGluLeuHisAsnArgLysLysAlaLeuLeuAspGluMetAlaArgGluAlaAspLys LysGluLeuProLysArgLeu-158 |
| Hydrophilic Regions - Hopp-Woods | |
| SEQ. ID. NO. 18107 | 3-SerArgTyrAspGly-7 |
| SEQ. ID. NO. 18108 | 21-LeuIleLysGluProLeuAspLysAlaLysGlnArgAsnGluGluLeuGluAlaAlaGluGluAlaAlaAla-44 |
| SEQ. ID. NO. 18109 | 47-AlaLeuGlyArgGluGlnGluValAspArgValSerGluTrpGluGluArgTyrLysLeuSerArgSerGluPhe-71 |
| SEQ. ID. NO. 18110 | 91-LysThrTrpLysSerGlyMetAspLysIleCys-101 |
| SEQ. ID. NO. 18111 | 104-AsnAlaLysAlaGluGlyGluThrProAsn-113 |
| SEQ. ID. NO. 18112 | 119-GluLeuAlaCysLysThrAlaGluThrGluAlaArgLeuGluGluLeuHisAsnArgLysLysAlaLeuLeuAspGluMetAlaArgGluAlaAspLys LysGluLeuProLysArgLeu-158 |
| a269 | |
| AMPHI Regions - AMPHI | |
| SEQ. ID. NO. 18113 | 54-TrpAspPheIleGlnAsnThr-60 |
| SEQ. ID. NO. 18114 | 73-PheLysThrArgAlaLeuGlyArgPheSerSerPro-84 |
| Antigenic Index - Jameson-Wolf | |
| SEQ. ID. NO. 18115 | 42-ProAlaSerSerAla-46 |
| SEQ. ID. NO. 18116 | 60-ThrAlaSerProLysValSer-66 |
| SEQ. ID. NO. 18117 | 73-PheLysThrArgAlaLeuGlyArgPheSerSerPro-84 |
| SEQ. ID. NO. 18118 | 90-LeuSerGlyArgGlyValLysLysProLeu-99 |
| SEQ. ID. NO. 18119 | 107-GlnValAspThrSerAla-112 |

TABLE 1-continued

| | |
|---|---|
| Hydrophilic Regions - Hopp-Woods | |
| SEQ. ID. NO. 18120 | 61-AlaSerProLysVal-65 |
| SEQ. ID. NO. 18121 | 73-PheLysThrArgAlaLeuGly-79 |
| SEQ. ID. NO. 18122 | 93-ArgGlyValLysLysProLeu-99 |
| a270 | |
| AMPHI Regions - AMPHI | |
| SEQ. ID. NO. 18123 | 41-AspLeuThrGluGlyCys-46 |
| SEQ. ID. NO. 18124 | 49-ProAspGlySerArg-53 |
| SEQ. ID. NO. 18125 | 100-GlnProSerGlyThrTrp-105 |
| Antigenic Index - Jameson-Wolf | |
| SEQ. ID. NO. 18126 | 1-MetAsnLysAsnArgLysLeu-7 |
| SEQ. ID. NO. 18127 | 41-AspLeuThrGluGlyCysThrLeuProAspGlySerArgValArgAlaAlaAlaValSerThrLysLysProPhe-65 |
| SEQ. ID. NO. 18128 | 71-HisAlaProAlaGlyThrGlu-77 |
| SEQ. ID. NO. 18129 | 86-LysAsnMetAspMetGlyPhe-92 |
| SEQ. ID. NO. 18130 | 95-TyrMetPhGluArgGlnProSerGlyThr-104 |
| SEQ. ID. NO. 18131 | 116-ValGluGlyArgArgAspPheThrAla-124 |
| SEQ. ID. NO. 18132 | 128-IleGlySerArgThrPhe-133 |
| Hydrophilic Regions - Hopp-Woods | |
| SEQ. ID. NO. 18133 | 1-MetAsnLysAsnArgLysLeu-7 |
| SEQ. ID. NO. 18134 | 49-ProAspGlySerArgValArgAla-56 |
| SEQ. ID. NO. 18135 | 60-SerThrLysLysProPhe-65 |
| SEQ. ID. NO. 18136 | 73-ProAlaGlyThrGlu-77 |
| SEQ. ID. NO. 18137 | 96-MetPheGluArgGlnPro-101 |
| SEQ. ID. NO. 18138 | 116-ValGluGlyArgArgAspPheThrAla-124 |
| a271-2 | |
| AMPHI Regions - AMPHI | |
| SEQ. ID. NO. 18139 | 6-MetAlaArgIleTrp-10 |
| SEQ. ID. NO. 18140 | 20-SerProCysProAla-24 |
| SEQ. ID. NO. 18141 | 29-ProLysSerLeuAlaLysCysAla-36 |
| Antigenic Index - Jameson-Wolf | |
| SEQ. ID. NO. 18142 | 26-ThrThrLysProLysSerLeuAlaLys-34 |
| SEQ. ID. NO. 18143 | 41-ArgSerAsnCysLeu-45 |
| SEQ. ID. NO. 18144 | 60-CysSerSerThrThrGlyAlaProThrSerArg-70 |
| SEQ. ID. NO. 18145 | 78-SerAlaSerIleAsnLysAspThrArgMetProAlaSerVal-91 |
| SEQ. ID. NO. 18146 | 102-CysCysAlaAsnThrSerLysProProSer-111 |
| Hydrophilic Regions - Hopp-Woods | |
| SEQ. ID. NO. 18147 | 27-ThrLysProLysSerLeuAla-33 |
| SEQ. ID. NO. 18148 | 80-SerIleAsnLysAspThrArgMet-87 |
| SEQ. ID. NO. 18149 | 105-AsnThrSerLysProPro-110 |
| a272-2 | |
| AMPHI Regions - AMPHI | |
| SEQ. ID. NO. 18150 | 44-IleThrArgIleThrAspGlu-50 |
| SEQ. ID. NO. 18151 | 70-AlaGluGluPheSerSerThrAsn-77 |
| SEQ. ID. NO. 18152 | 106-PheArgAlaIleThrSer-111 |
| SEQ. ID. NO. 18153 | 165-IleIleThrIleGluAspProIleGlu-173 |
| SEQ. ID. NO. 18154 | 194-AsnTrpMetAlaAlaLeuLysAsnThrLeuArgGlnAla-206 |
| SEQ. ID. NO. 18155 | 244-AsnGlnAlaLeuAspArgIleIleAsn-252 |
| SEQ. ID. NO. 18156 | 307-GlyAsnIleHisGluIleLysGluValMetLys-317 |
| SEQ. ID. NO. 18157 | 328-AspGlnHisLeuTyrGln-333 |
| SEQ. ID. NO. 18158 | 343-GlnAspAlaLeuLysAsnAlaAspSer-351 |
| Antigenic Index - Jameson-Wolf | |
| SEQ. ID. NO. 18159 | 2-PheThrAspGluAsnMetThrAlaLysGluGluLeu-13 |
| SEQ. ID. NO. 18160 | 19-HisMetAsnLysAsnLysGlySerAsp-27 |
| SEQ. ID. NO. 18161 | 38-MetLysLeuAspGlyLysIleThrArgIleThrAspGluProLeuThrAlaGluLysCysMet-58 |
| SEQ. ID. NO. 18162 | 68-LysGlnAlaGluGluPheSerSerThrAsnGlu-78 |
| SEQ. ID. NO. 18163 | 85-LeuProAspThrSerArgPheArgVal-93 |
| SEQ. ID. NO. 18164 | 109-IleThrSerLysIleProLysPheGluSerLeuAsn-120 |
| SEQ. ID. NO. 18165 | 128-ValAlaLeuLysLysArgGly-134 |
| SEQ. ID. NO. 18166 | 142-ThrGlySerGlyLysSerThrSerLeu-150 |
| SEQ. ID. NO. 18167 | 154-IleAspTyrArgAsnGluAsnSerPheGly-163 |
| SEQ. ID. NO. 18168 | 168-IleGluAspProIle-172 |
| SEQ. ID. NO. 18169 | 176-HisGluHisLysAsnCys-181 |
| SEQ. ID. NO. 18170 | 184-ThrGlnArgGluValGlyValAspThrGluAsn-194 |
| SEQ. ID. NO. 18171 | 199-LeuLysAsnThrLeuArgGlnAlaProAsp-208 |
| SEQ. ID. NO. 18172 | 214-GluIleArgAspArgGluThrMet-221 |
| SEQ. ID. NO. 18173 | 241-AsnSerThrAsnGlnAlaLeuAspArg-249 |
| SEQ. ID. NO. 18174 | 254-PheProGluGluArgArgGluGlnLeuLeu-263 |
| SEQ. ID. NO. 18175 | 278-LeuValProArgAspGlyGlyLysGlyArgValAlaAla-290 |
| SEQ. ID. NO. 18176 | 310-HisGluIleLysGluValMetLysLysSerThr-320 |
| SEQ. ID. NO. 18177 | 336-GluLysGlyGluIleSerLeu-342 |
| SEQ. ID. NO. 18178 | 344-AspAlaLeuLysAsnAlaAspSerAlaHisAspLeu-355 |
| SEQ. ID. NO. 18179 | 361-LeuArgSerArgGlnAlaGlnSerSerGlyProAspLeuGluLeuLeu-376 |
| Hydrophilic Regions - Hopp-Woods | |
| SEQ. ID. NO. 18180 | 2-PheThrAspGluAsnMetThrAlaLysGluGluLeu-13 |
| SEQ. ID. NO. 18181 | 20-MetAsnLysAsnLysGlySerAsp-27 |
| SEQ. ID. NO. 18182 | 38-MetLysLeuAspGlyLysIleThrArgIleThrAspGluProLeuThrAlaGluLysCysMet-58 |
| SEQ. ID. NO. 18183 | 68-LysGlnAlaGluGluPheSerSer-75 |
| SEQ. ID. NO. 18184 | 87-AspThrSerArgPheArgVal-93 |
| SEQ. ID. NO. 18185 | 112-LysIleProLysPheGluSer-118 |
| SEQ. ID. NO. 18186 | 128-ValAlaLeuLysLysArgGly-134 |

TABLE 1-continued

| | |
|---|---|
| SEQ. ID. NO. 18187 | 143-GlySerGlyLysSerThrSer-149 |
| SEQ. ID. NO. 18188 | 155-AspTyrArgAsnGluAsnSer-161 |
| SEQ. ID. NO. 18189 | 168-IleGluAspProIle-172 |
| SEQ. ID. NO. 18190 | 176-HisGluHisLysAsn-180 |
| SEQ. ID. NO. 18191 | 184-ThrGlnArgGluValGlyValAspThr-192 |
| SEQ. ID. NO. 18192 | 201-AsnThrLeuArgGlnAlaPro-207 |
| SEQ. ID. NO. 18193 | 214-GluIleArgAspArgGluThrMet-221 |
| SEQ. ID. NO. 18194 | 245-GlnAlaLeuAspArg-249 |
| SEQ. ID. NO. 18195 | 255-ProGluGluArgArgGluGlnLeuLeu-263 |
| SEQ. ID. NO. 18196 | 278-LeuValProArgAspGlyGlyLysGlyArgValAlaAla-290 |
| SEQ. ID. NO. 18197 | 310-HisGluIleLysGluValMetLysLysSerThr-320 |
| SEQ. ID. NO. 18198 | 336-GluLysGlyGluIleSerLeu-342 |
| SEQ. ID. NO. 18199 | 344-AspAlaLeuLysAsnAlaAspSerAlaHisAspLeu-355 |
| SEQ. ID. NO. 18200 | 361-LeuArgSerArgGlnAlaGlnSerSerGlyProAspLeuGluLeu-375 |
| a274 | |
| AMPHI Regions - AMPHI | |
| SEQ. ID. NO. 18201 | 31-TyrLysAspGlyLys-35 |
| SEQ. ID. NO. 18202 | 111-GluAlaValPheLysThrLeuSerPro-119 |
| Antigenic Index - Jameson-Wolf | |
| SEQ. ID. NO. 18203 | 25-LeuValThrAspAspTyrTyrLysAspGlyLysHisIleAsp-38 |
| SEQ. ID. NO. 18204 | 40-GlnLeuHisArgAspGluGluAlaValArgArgHisIle-52 |
| SEQ. ID. NO. 18205 | 60-ProAspMetAsnAla-64 |
| SEQ. ID. NO. 18206 | 71-GlyGluPheAspGlyLysGlnPro-78 |
| SEQ. ID. NO. 18207 | 85-HisProThrArgLysAlaAspAspGlnThrVal-95 |
| SEQ. ID. NO. 18208 | 99-ProValGlySerAlaGlnAsnGlyArgAlaGluTyr-110 |
| SEQ. ID. NO. 18209 | 117-LeuSerProThrAsnHis-122 |
| SEQ. ID. NO. 18210 | 126-ArgValGluAspAlaAlaGly-132 |
| SEQ. ID. NO. 18211 | 136-ValGluAsnLysTrpIleThrSerGlnGlyAsnAlaValAspLeuThrProMetAspLysLeuPheAsnAsnThrGluSerLys-163 |
| Hydrophilic Regions - Hopp-Woods | |
| SEQ. ID. NO. 18212 | 29-AspTyrTyrLysAspGlyLysHisIleAsp-38 |
| SEQ. ID. NO. 18213 | 40-GlnLeuHisArgAspGluGluAlaValArgArgHisIle-52 |
| SEQ. ID. NO. 18214 | 72-GluPheAspGlyLysGln-77 |
| SEQ. ID. NO. 18215 | 86-ProThrArgLysAlaAspAspGlnThrVal-95 |
| SEQ. ID. NO. 18216 | 104-GlnAsnGlyArgAlaGluTyr-110 |
| SEQ. ID. NO. 18217 | 126-ArgValGluAspAlaAlaGly-132 |
| SEQ. ID. NO. 18218 | 151-ThrProMetAspLysLeuPheAsn-158 |
| a276 | |
| AMPHI Regions - AMPHI | |
| SEQ. ID. NO. 18219 | 9-MetMetArgSerAlaProSerMetValValArgArgTrpAlaThrMetMet-25 |
| SEQ. ID. NO. 18220 | 60-SerPheLysMetAlaArg-65 |
| SEQ. ID. NO. 18221 | 80-ProPheAspProMetGlyTrp-86 |
| SEQ. ID. NO. 18222 | 115-GlyArgLeuTyrArgThrPheSerAsn-123 |
| SEQ. ID. NO. 18223 | 164-ThrLysArgGlySerArgLeu-170 |
| SEQ. ID. NO. 18224 | 207-SerThrSerThrLeuArgLysLeuMetArgProSerThr-219 |
| Antigenic Index - Jameson-Wolf | |
| SEQ. ID. NO. 18225 | 10-MetArgSerAlaProSerMetVal-17 |
| SEQ. ID. NO. 18226 | 29-PheSerIleArgArgSerSerAlaCysTrpThrArgArgSerAspSerLeuSer-46 |
| SEQ. ID. NO. 18227 | 52-SerSerAsnAsnAsnIle-57 |
| SEQ. ID. NO. 18228 | 67-MetAlaThrArgCysArgCysProProAspLysLeuLeuPro-80 |
| SEQ. ID. NO. 18229 | 82-AspProMetGlyTrp-86 |
| SEQ. ID. NO. 18230 | 88-SerProSerGlyAspAlaSerIleArg-96 |
| SEQ. ID. NO. 18231 | 103-TrpArgAlaAspArgThrSerAlaSerProAlaSerGlyArgLeuTyr-118 |
| SEQ. ID. NO. 18232 | 121-PheSerAsnArgValSerSerAsnArgAsnThrSerTrpGluThrArgAlaAsnTrpAlaArgArgGlnSerSerLeu-146 |
| SEQ. ID. NO. 18233 | 158-LeuProAlaAspGlySerThrLysArgGlySerArgLeuThrThr-172 |
| SEQ. ID. NO. 18234 | 176-ProLeuProGluArgProThrArgAlaThrArgSerProCysLeuMetSerArgLeuLysProSerArgAlaLeuMetProSerGluArgTyrSerThrSer ThrLeuArgLysLeuMetArgProSerThrArgCysGlyAla-223 |
| SEQ. ID. NO. 18235 | 229-CysSerGlyGlyValSerArgAsnAlaHisThrProSerAlaAlaArgAsn-245 |
| Hydrophilic Regions - Hopp-Woods | |
| SEQ. ID. NO. 18236 | 29-PheSerIleArgArgSerSer-35 |
| SEQ. ID. NO. 18237 | 38-TrpThrArgArgSerAspSerLeu-45 |
| SEQ. ID. NO. 18238 | 67-MetAlaThrArgCysArgCysProProAspLys-77 |
| SEQ. ID. NO. 18239 | 90-SerGlyAspAlaSerIleArg-96 |
| SEQ. ID. NO. 18240 | 104-ArgAlaAspArgThrSerAla-110 |
| SEQ. ID. NO. 18241 | 124-ArgValSerSerAsnArgAsnThrSerTrpGluThr-135 |
| SEQ. ID. NO. 18242 | 137-AlaAsnTrpAlaArgArgGlnSerSer-145 |
| SEQ. ID. NO. 18243 | 161-AspGlySerThrLysArgGlySerArg-169 |
| SEQ. ID. NO. 18244 | 176-ProLeuProGluArgProThrArgAlaThrArg-186 |
| SEQ. ID. NO. 18245 | 192-SerArgLeuLysProSerArg-198 |
| SEQ. ID. NO. 18246 | 200-LeuMetProSerGluArgTyrSer-207 |
| SEQ. ID. NO. 18247 | 210-ThrLeuArgLysLeuMetArgProSerThrArgCys-221 |
| SEQ. ID. NO. 18248 | 232-GlyValSerArgAsnAlaHis-238 |
| a277 | |
| AMPHI Regions - AMPHI | |
| SEQ. ID. NO. 18249 | 43-PheGluValValGlyGlyLeuPheAspPheValLeu-54 |
| SEQ. ID. NO. 18250 | 70-CysProAsnGluValIleAspValPheHisAlaLeuGln-82 |
| SEQ. ID. NO. 18251 | 87-AlaPheAspAlaValGlyAspPheAlaGluTyrGlyGlyAlaValAspAlaAlaAspLeuLeuGluIleGlyGluLeuGlyTyrPheHis-116 |
| SEQ. ID. NO. 18252 | 180-AlaValGlyValValAlaValAla-187 |
| Antigenic Index - Jameson-Wolf | |
| SEQ. ID. NO. 18253 | 2-ProArgPheGluAspLysLeuValGlyArgGlnGlyGluGlyGlyVal-17 |
| SEQ. ID. NO. 18254 | 69-PheCysProAsnGluVal-74 |

TABLE 1-continued

| | |
|---|---|
| SEQ. ID. NO. 18255 | 95-AlaGluTyrGlyGly-99 |
| SEQ. ID. NO. 18256 | 118-ValGluProAspPheProAlaGlnThrProArgAlaGluGlyGly-132 |
| SEQ. ID. NO. 18257 | 138-PheAspLysAlaAsp-142 |
| SEQ. ID. NO. 18258 | 162-AspIleGlyGlySerGlyLeuGluGlyAspLeu-172 |
| SEQ. ID. NO. 18259 | 196-LeuAspValGlyGlyLysProArgLeuGlyAla-206 |
| SEQ. ID. NO. 18260 | 208-CysAlaGlnThrGlyGlyGlyMetGly-216 |
| SEQ. ID. NO. 18261 | 219-GlyThrAspPheHis-223 |
| SEQ. ID. NO. 18262 | 226-GlyLeuAspAspGlyAla-231 |
| SEQ. ID. NO. 18263 | 239-LeuGlnPheGluAspAspLeuLeuGluGlyLysHisGlyLeu-252 |
| Hydrophilic Regions - Hopp-Woods | |
| SEQ. ID. NO. 18264 | 2-ProArgPheGluAspLysLeuValGlyArgGlnGlyGlu-14 |
| SEQ. ID. NO. 18265 | 118-ValGluProAspPhe-122 |
| SEQ. ID. NO. 18266 | 126-ThrProArgAlaGluGly-131 |
| SEQ. ID. NO. 18267 | 138-PheAspLysAlaAsp-142 |
| SEQ. ID. NO. 18268 | 167-GlyLeuGluGlyAspLeu-172 |
| SEQ. ID. NO. 18269 | 198-ValGlyGlyLysProArgLeuGlyAla-206 |
| SEQ. ID. NO. 18270 | 226-GlyLeuAspAspGlyAla-231 |
| SEQ. ID. NO. 18271 | 239-LeuGlnPheGluAspAspLeuLeuGluGlyLysHisGlyLeu-252 |
| a278 | |
| AMPHI Regions - AMPHI | |
| SEQ. ID. NO. 18272 | 7-GlyAlaIlePheSerIleGly-13 |
| SEQ. ID. NO. 18273 | 20-IleGlyProLeuProSerIleGlyArg-28 |
| SEQ. ID. NO. 18274 | 42-ThrGlyThrSerLys-46 |
| SEQ. ID. NO. 18275 | 101-ArgThrIleProSerValThrGluIle-109 |
| SEQ. ID. NO. 18276 | 123-PheSerIleLeuAlaLeuIleLysSerLeuIleSer-134 |
| SEQ. ID. NO. 18277 | 157-LeuTyrArgGlnIleGlnAsnLeuIleThrHisPheAsnPheTyrAlaAla-173 |
| SEQ. ID. NO. 18278 | 189-GluThrLeuIleGlnHisLeuArgGlnLeuAlaAsp-200 |
| Antigenic Index - Jameson-Wolf | |
| SEQ. ID. NO. 18279 | 25-SerIleGlyArgProAsnAlaSerThrThrArgProThrSerSerArgProThrGlyThrSerLysIleArgPro-49 |
| SEQ. ID. NO. 18280 | 63-SerProAsnThrThrAlaProThrGluSerArgSerArgPheIleAla-78 |
| SEQ. ID. NO. 18281 | 80-ProLysValLeuProGlyAsnSerSerIle-89 |
| SEQ. ID. NO. 18282 | 93-IleAlaSerAspLysProTrpMetArg-101 |
| SEQ. ID. NO. 18283 | 110-ThrValProArgValArgThrSerAlaPheThrAspArgPheSer-124 |
| SEQ. ID. NO. 18284 | 146-ArgHisSerArgValGlnGlyThr-153 |
| SEQ. ID. NO. 18285 | 178-PheAspPheAspArgAspPhe-184 |
| SEQ. ID. NO. 18286 | 209-ThrValAsnAspGlyArgPheAspMetValGlu-219 |
| Hydrophilic Regions - Hopp-Woods | |
| SEQ. ID. NO. 18287 | 27-GlyArgProAsnAlaSerThrThrArgProThrSerSerArgProThrGlyThrSerLysIleArgPro-49 |
| SEQ. ID. NO. 18288 | 68-AlaProThrGluSerArgSerArgPheIleAla-78 |
| SEQ. ID. NO. 18289 | 93-IleAlaSerAspLysProTrp-99 |
| SEQ. ID. NO. 18290 | 110-ThrValProArgValArgThr-116 |
| SEQ. ID. NO. 18291 | 146-ArgHisSerArgValGln-151 |
| SEQ. ID. NO. 18292 | 178-PheAspPheAspArgAspPhe-184 |
| SEQ. ID. NO. 18293 | 211-AsnAspGlyArgPheAspMetValGlu-219 |
| a279 | |
| AMPHI Regions - AMPHI | |
| SEQ. ID. NO. 18294 | 6-GlyCysLeuIleSer-10 |
| SEQ. ID. NO. 18295 | 47-AlaAlaSerIleAlaArgSerThrAla-55 |
| SEQ. ID. NO. 18296 | 58-LeuProAlaIleThrThr-63 |
| SEQ. ID. NO. 18297 | 74-ThrThrSerSerCysAlaAsp-80 |
| Antigenic Index - Jameson-Wolf | |
| SEQ. ID. NO. 18298 | 13-XxxArgAlaSerAla-17 |
| SEQ. ID. NO. 18299 | 29-TrpGluGlyThrAspThrGlySerGlyArgAlaArgLeuAla-42 |
| SEQ. ID. NO. 18300 | 64-CysProGlyGluLeuLysLeuThr-71 |
| SEQ. ID. NO. 18301 | 74-ThrThrSerSerCysAlaAspSer-81 |
| SEQ. ID. NO. 18302 | 88-CysSerSerSerLysProArgIle-95 |
| SEQ. ID. NO. 18303 | 101-ThrProCysGlyThrAlaAspCysIleSerSerAlaArgXxxArgThrSerLeu-118 |
| SEQ. ID. NO. 18304 | 120-AlaSerAlaLysSerAsnAlaProAla-128 |
| SEQ. ID. NO. 18305 | 148-ProProAlaSerGlu-152 |
| Hydrophilic Regions - Hopp-Woods | |
| SEQ. ID. NO. 18306 | 13-XxxArgAlaSerAla-17 |
| SEQ. ID. NO. 18307 | 29-TrpGluGlyThrAspThrGlySerGlyArgAlaArgLeuAla-42 |
| SEQ. ID. NO. 18308 | 66-GlyGluLeuLysLeu-70 |
| SEQ. ID. NO. 18309 | 89-SerSerSerLysProArgIle-95 |
| SEQ. ID. NO. 18310 | 110-SerSerAlaArgXxxArgThrSerLeu-118 |
| SEQ. ID. NO. 18311 | 120-AlaSerAlaLysSerAsnAla-126 |
| a280 | |
| AMPHI Regions - AMPHI | |
| SEQ. ID. NO. 18312 | 27-SerPheSerIleLeuGlyAspValAlaLys-36 |
| SEQ. ID. NO. 18313 | 64-AspIleLysLysIleArgSerAla-71 |
| SEQ. ID. NO. 18314 | 85-AspIleGlnArgAlaValLys-91 |
| SEQ. ID. NO. 18315 | 97-TyrAlaGluAlaThrLysGlyIleGlnProLeuLys-108 |
| SEQ. ID. NO. 18316 | 150-AlaTyrAlaGlnAsnValAlaGluAlaLeuIleLys-161 |
| SEQ. ID. NO. 18317 | 237-ValAlaAlaIleIleArgGlnIleLys-245 |
| SEQ. ID. NO. 18318 | 247-GluGlyIleLysAlaValPheThrGlu-255 |
| SEQ. ID. NO. 18319 | 258-LysAspThrArgMetValAspArgIleAlaLysGluThr-270 |
| SEQ. ID. NO. 18320 | 278-LeuTyrSerAspAlaLeuGlyAsnAlaProAlaAspThrTyrIle-292 |
| Antigenic Index - Jameson-Wolf | |
| SEQ. ID. NO. 18321 | 1-MetLysHisProLys-5 |
| SEQ. ID. NO. 18322 | 38-IleGlyGlyGluArgValSer-44 |

TABLE 1-continued

| | |
|---|---|
| SEQ. ID. NO. 18323 | 51-AlaAsnGlnAspThrHis-56 |
| SEQ. ID. NO. 18324 | 61-ThrSerGlyAspIleLysLysIleArgSerAlaLys-72 |
| SEQ. ID. NO. 18325 | 82-GluAlaAlaAspIleGlnArgAlaValLysGlnSerLysValSerTyrAlaGluAlaThrLysGlyIleGln-105 |
| SEQ. ID. NO. 18326 | 107-LeuLysAlaGluGluGluGlyGlyHisHisHisAspHisAspHisAspHisAspHisAspHisGluGlyHisHisHisAspHisGlyGluTyrAspProHisValTrpAsnAspPro-145 |
| SEQ. ID. NO. 18327 | 159-LeuIleLysAlaAspProGluGlyLysValTyrTyr-170 |
| SEQ. ID. NO. 18328 | 180-GlnLeuLysLysLeuHisSerAspAla-188 |
| SEQ. ID. NO. 18329 | 196-ProAlaAlaLysArgLysValLeuThr-204 |
| SEQ. ID. NO. 18330 | 212-MetGlyLysArgTyrHis-217 |
| SEQ. ID. NO. 18331 | 222-AlaProGlnGlyValSerSerGluAlaGluProSerAlaLysGln-236 |
| SEQ. ID. NO. 18332 | 242-ArgGlnIleLysArgGluGlyIle-249 |
| SEQ. ID. NO. 18333 | 255-GluAsnIleLysAspThrArgMetValAspArgIleAlaLysGluThrGlyVal-272 |
| SEQ. ID. NO. 18334 | 274-ValSerGlyLysLeuTyrSer-280 |
| SEQ. ID. NO. 18335 | 286-AlaProAlaAspThr-290 |
| SEQ. ID. NO. 18336 | 295-TyrArgHisAsnIle-299 |
| Hydrophilic Regions - Hopp-Woods | |
| SEQ. ID. NO. 18337 | 1-MetLysHisProLys-5 |
| SEQ. ID. NO. 18338 | 38-IleGlyGlyGluArgValSer-44 |
| SEQ. ID. NO. 18339 | 63-GlyAspIleLysLysIleArgSerAlaLys-72 |
| SEQ. ID. NO. 18340 | 82-GluAlaAlaAspIleGlnArgAlaValLysGlnSerLys-94 |
| SEQ. ID. NO. 18341 | 99-GluAlaThrLysGly-103 |
| SEQ. ID. NO. 18342 | 107-LeuLysAlaGluGluGluGlyGlyHisHisHisAspHisAspHisAspHisAspHisAspHisGluGlyHisHisHisAspHisGlyGluTyrAsp-138 |
| SEQ. ID. NO. 18343 | 159-LeuIleLysAlaAspProGluGly-166 |
| SEQ. ID. NO. 18344 | 180-GlnLeuLysLysLeuHisSerAspAla-188 |
| SEQ. ID. NO. 18345 | 196-ProAlaAlaLysArgLysValLeuThr-204 |
| SEQ. ID. NO. 18346 | 226-ValSerSerGluAlaGluProSerAlaLysGln-236 |
| SEQ. ID. NO. 18347 | 242-ArgGlnIleLysArgGluGlyIle-249 |
| SEQ. ID. NO. 18348 | 255-GluAsnIleLysAspThrArgMetValAspArgIleAlaLysGluThrGlyVal-272 |
| a281 | |
| AMPHI Regions - AMPHI | |
| SEQ. ID. NO. 18349 | 62-AlaAlaGlyMetLeuMetAlaLeuLeuAlaGlyLeuValSerArgPhe-77 |
| SEQ. ID. NO. 18350 | 126-LeuGlnLeuIleAlaAlaValSerThrLeuThr-136 |
| SEQ. ID. NO. 18351 | 140-LeuAlaValIleTyrArg-145 |
| SEQ. ID. NO. 18352 | 179-LeuValSerGlyPheGlnAlaLeuGlyThrLeuMetSerVal-192 |
| SEQ. ID. NO. 18353 | 205-TrpAlaLysHisMet-209 |
| SEQ. ID. NO. 18354 | 216-SerValLeuThrAlaLeuLeuCysGly-224 |
| Antigenic Index - Jameson-Wolf | |
| SEQ. ID. NO. 18355 | 25-ArgArgMetSerLeu-29 |
| SEQ. ID. NO. 18356 | 78-ThrThrLeuLysGluAspAlaAsn-85 |
| SEQ. ID. NO. 18357 | 102-SerLysAsnGlySerSerVal-108 |
| SEQ. ID. NO. 18358 | 159-SerValGlyGlyLysGlyGly-165 |
| SEQ. ID. NO. 18359 | 236-IleProSerGlyPro-240 |
| SEQ. ID. NO. 18360 | 256-LeuGlyLysGluGlyGlyIle-262 |
| SEQ. ID. NO. 18361 | 266-TrpLeuLysAsnHisArgHisHisThrThr-275 |
| Hydrophilic Regions - Hopp-Woods | |
| SEQ. ID. NO. 18362 | 25-ArgArgMetSerLeu-29 |
| SEQ. ID. NO. 18363 | 78-ThrThrLeuLysGluAspAlaAsn-85 |
| SEQ. ID. NO. 18364 | 103-LysAsnGlySerSer-107 |
| SEQ. ID. NO. 18365 | 256-LeuGlyLysGluGlyGlyIle-262 |
| SEQ. ID. NO. 18366 | 267-LeuLysAsnHisArgHisHisThr-274 |
| a282 | |
| AMPHI Regions - AMPHI | |
| SEQ. ID. NO. 18367 | 10-LeuIleValAlaPheLeuValLeuIleAsnProPheSerAlaLeu-24 |
| SEQ. ID. NO. 18368 | 50-ValPheAlaValIleAlaValPheAlaLeuIleGlyGlyThrLeu-64 |
| SEQ. ID. NO. 18369 | 111-ValArgProAlaArgAsn-116 |
| SEQ. ID. NO. 18370 | 176-ValSerArgLeuLeu-180 |
| SEQ. ID. NO. 18371 | 186-ThrIleLeuAsnArgIleMetGlyMet-194 |
| Antigenic Index - Jameson-Wolf | |
| SEQ. ID. NO. 18372 | 31-ThrAsnGlyHisSerThrLysGluArgArgLysValAlaArg-44 |
| SEQ. ID. NO. 18373 | 92-AsnGlyAsnAspAsnProAlaLysGlnAsnLeuGlyAlaGlnProGluThrGlyGlnValArgProAlaArgAsnAlaGlyAla-119 |
| Hydrophilic Regions - Hopp-Woods | |
| SEQ. ID. NO. 18374 | 34-HisSerThrLysGluArgArgLysValAlaArg-44 |
| SEQ. ID. NO. 18375 | 92-AsnGlyAsnAspAsnProAlaLysGlnAsnLeu-102 |
| SEQ. ID. NO. 18376 | 104-AlaGlnProGluThrGlyGlnValArgProAlaArgAsn-116 |
| a283 | |
| AMPHI Regions - AMPHI | |
| SEQ. ID. NO. 18377 | 11-ThrLeuAlaSerPheLeuPro-17 |
| SEQ. ID. NO. 18378 | 32-GlyGlyAsnSerTyrSerAspValProLysGlnLeuHis-44 |
| SEQ. ID. NO. 18379 | 67-AlaAspAlaGlyLysArgThr-73 |

TABLE 1-continued

Antigenic Index - Jameson-Wolf
SEQ. ID. NO. 18380 28-TrpLysAspGlyGlyGlyAsnSerTyrSerAspValProLysGlnLeuHisProAspGlnSerGln-49
SEQ. ID. NO. 18381 53-LeuArgThrArgGlnThrLysProAlaValLysProAlaGlnAlaAspAlaGlyLysArgThrAspGlyAlaAlaGlnGluAsnAsnPro AspThrAlaGluLysAsnArgGlnLeuGluGluGluLysLysArgIleAlaGluThrGluArgGlnAsnLysGluGluAsnCysArgIleSerLysMet AsnLeu-117
SEQ. ID. NO. 18382 121-GlyAsnSerAsnAlaLysAsnLysAspAspLeuIleArgLysTyrAsnAsnAlaValAsnLysTyrCysArg-144
Hydrophilic Regions - Hopp-Woods
SEQ. ID. NO. 18383 35-SerTyrSerAspValProLys-41
SEQ. ID. NO. 18384 43-LeuHisProAspGlnSerGln-49
(SEQ. ID. NO. 18381)
53-LeuArgThrArgGlnThrLysProAlaValLysProAlaGlnAlaAspAlaGlyLysArgThrAspGlyAlaAlaGlnGluAsnAsnProAspThrAla GluLysAsnArgGlnLeuGluGluGluLysLysArgIleAlaGluThrGluArgGlnAsnLysGluGluAsnCysArgIleSerLysMetAsnLeu-117
SEQ. ID. NO. 18385 123-SerAsnAlaLysAsnLysAspAspLeuIleArgLysTyrAsn-136
a284
AMPHI Regions - AMPHI
SEQ. ID. NO. 18386 43-GluAlaPheAlaGlyPhePheGluThrVal-52
SEQ. ID. NO. 18387 61-ThrPheAlaAlaArgPhe-66
SEQ. ID. NO. 18388 125-ValAspPheAspValPhe-130
SEQ. ID. NO. 18389 154-ValValPheArgLeuPheArgGlnValValValAsp-165
SEQ. ID. NO. 18390 174-AspThrAlaCysGlyAsnValGlyGly-182
SEQ. ID. NO. 18391 187-AlaAlaAlaPheAlaGlnIleHisGln-195
SEQ. ID. NO. 18392 216-PheValGlnPheIleArgAspAspPheGlyHisGly-227
SEQ. ID. NO. 18393 277-PheArgValPheGlyGlnPheAlaArgGlnPheAla-288
SEQ. ID. NO. 18394 304-PheArgArgGlyPheAspAspGlyPheAspValValAspLys-317
SEQ. ID. NO. 18395 340-AlaAlaLeuHisGlnValHisGlnThrAla-349
SEQ. ID. NO. 18396 352-GlyAspAsnGlnIleAspArgPheAlaGln-361
SEQ. ID. NO. 18397 407-AlaArgAlaPheAlaArgPhePheAlaAlaPheGlyGlnSerLeuGlnSer-423
Antigenic Index - Jameson-Wolf
SEQ. ID. NO. 18398 1-MetProSerGluThrArgAsnArgPhe-9
SEQ. ID. NO. 18399 109-PheAspGlyGlnPhe-113
SEQ. ID. NO. 18400 132-HisPheGlyLysArgAsnArgAsnThrArgAla-142
SEQ. ID. NO. 18401 147-GlyAlaProAspAlaVal-152
SEQ. ID. NO. 18402 166-AsnValGlyAsnGlyArgTyrValAspThrAlaCysGlyAsnValGlyGlyAsnGlnAsn-185
SEQ. ID. NO. 18403 209-AlaValGlyGlyGlu-213
SEQ. ID. NO. 18404 219-PheIleArgAspAspPheGlyHisGlyPheGlyGlyArgGluAsnHisAla-235
SEQ. ID. NO. 18405 273-AspPheAspAspPheArg-278
SEQ. ID. NO. 18406 286-GlnPheAlaAspArgAlaValProSerGlyGlyGluGlnGlnSer-300
SEQ. ID. NO. 18407 303-ValPheArgArgGlyPheAspAspGlyPheAspValValAspLysAlaHis-319
SEQ. ID. NO. 18408 347-GlnThrAlaArgArgGlyAspAsnGlnIleAspArgPheAla-360
SEQ. ID. NO. 18409 362-GlyAlaGlyLeuValAlaGluArgCysThrThrAspAspAlaAspGlyThrGluProThr-381
SEQ. ID. NO. 18410 398-PheAlaGlyArgArgGlnHisGlnArgAlaArgAla-409
SEQ. ID. NO. 18411 419-GlnSerLeuGlnSerArg-424
Hydrophilic Regions - Hopp-Woods
SEQ. ID. NO. 18412 1-MetProSerGluThrArgAsnArgPhe-9
SEQ. ID. NO. 18413 134-GlyLysArgAsnArgAsnThrArgAla-142
SEQ. ID. NO. 18414 220-IleArgAspAspPheGly-225
SEQ. ID. NO. 18415 229-GlyGlyArgGluAsnHisAla-235
SEQ. ID. NO. 18416 286-GlnPheAlaAspArgAlaValProSerGlyGlyGluGlnGln-299
SEQ. ID. NO. 18417 306-ArgGlyPheAspAspGlyPheAspValValAspLysAlaHis-319
SEQ. ID. NO. 18418 347-GlnThrAlaArgArgGlyAspAsnGlnIleAspArgPheAla-360
SEQ. ID. NO. 18419 366-ValAlaGluArgCysThrThrAspAspAlaAspGlyThrGlu-379
SEQ. ID. NO. 18420 398-PheAlaGlyArgArgGlnHisGlnArgAlaArgAla-409
a285-1
AMPHI Regions - AMPHI
SEQ. ID. NO. 18421 15-ValCysPheLeuGly-19
SEQ. ID. NO. 18422 34-GlnIleProSerTrp-38
SEQ. ID. NO. 18423 50-GlyThrLeuLeuAspGlyPheAsp-57
SEQ. ID. NO. 18424 116-SerLeuProAspSerIleAspLeuPro-124
SEQ. ID. NO. 18425 208-HisSerThrAlaArg-212
SEQ. ID. NO. 18426 240-HisProPheAlaGluSerLeuAspLysThrLeuGluGluValLeu-254
SEQ. ID. NO. 18427 266-ValProSerLeuPro-270
SEQ. ID. NO. 18428 280-AlaIleProSerPheSerAsp-286
SEQ. ID. NO. 18429 313-GlnValLeuGlySer-317
SEQ. ID. NO. 18430 592-IleGlyLysAlaAlaAspIle-598
SEQ. ID. NO. 18431 609-ProAspThrSerArg-613
SEQ. ID. NO. 18432 629-GlyAlaGluValValAsp-634
SEQ. ID. NO. 18433 671-GlyIleAsnArgGluLeuThrArgTrp-679
SEQ. ID. NO. 18434 747-IleAlaGluLeuHisAsnPhePheLysProProPhe-758
SEQ. ID. NO. 18435 776-AlaArgGlyTyrLeu-780
SEQ. ID. NO. 18436 836-PheGlyGlyAsnMetAlaAsn-842
SEQ. ID. NO. 18437 848-ArgIleThrAlaSerLeuProAspLeuGlyThrLeu-859
SEQ. ID. NO. 18438 868-GlnAsnIleThrGlySerLeuAsnAlaAla-877
SEQ. ID. NO. 18439 955-GlySerIleAlaAsp-959
SEQ. ID. NO. 18440 1008-ThrAlaGluLeuSer-1012
SEQ. ID. NO. 18441 1061-ValThrGlyMetIleLys-1066
SEQ. ID. NO. 18442 1135-SerGlyGlySerValArgGlyValGlyThrValArg-1146
SEQ. ID. NO. 18443 1165-ThrValSerPheValGlyProLeuAsn-1173
SEQ. ID. NO. 18444 1190-AlaGlyValGluIleLeuGlySerLeuAsn-1199
SEQ. ID. NO. 18445 1244-LeuAlaGlyGlnIle-1248
SEQ. ID. NO. 18446 1305-ValLysLeuIleTyrArgLeuThrArgAlaIleGlnAlaValAlaArgIleGlySer-1323

TABLE 1-continued

| | |
|---|---|
| Antigenic Index - Jameson-Wolf | |
| SEQ. ID. NO. 18447 | 43-IleSerSerGlnAsnLeuLysGlyThrLeuLeuAspGlyPheAspGlyAspAsnTrpSerIleGluThrGluGlyAlaAspLeuLysIleSerArg-74 |
| SEQ. ID. NO. 18448 | 80-LysProSerGluLeuMetArgArgSerLeuHis-90 |
| SEQ. ID. NO. 18449 | 104-LysProThrProProLysGluGluArgProProLeuSerLeuProAspSerIleAsp-122 |
| SEQ. ID. NO. 18450 | 130-AspArgPheGluThrGlyLysIleSerMetGlyLysAlaPheAspLysGlnThrValTyr-149 |
| SEQ. ID. NO. 18451 | 151-GluArgLeuAspAlaSerTyrArgTyrAspArgLysGlyHisArgLeuAspLeuLysAlaAlaAspThrProTrpSerSerSerSerGlySerAla-182 |
| SEQ. ID. NO. 18452 | 185-GlyLeuLysLysProPheAla-191 |
| SEQ. ID. NO. 18453 | 198-ThrLysGlyGlyLeuGluGlyLysThrIle-207 |
| SEQ. ID. NO. 18454 | 209-SerThrAlaArgLeuSerGlySerLeuLysAspValArgAla-222 |
| SEQ. ID. NO. 18455 | 224-LeuAlaIleAspGlyGlyAsnIleArgLeuSerGlyLysSer-237 |
| SEQ. ID. NO. 18456 | 244-GluSerLeuAspLysThrLeuGlu-251 |
| SEQ. ID. NO. 18457 | 268-SerLeuProAspAla-272 |
| SEQ. ID. NO. 18458 | 292-GlySerLeuAspLeuGluAsnThrLys-300 |
| SEQ. ID. NO. 18459 | 302-GlyPheAlaAspArgAsnGlyIleProVal-311 |
| SEQ. ID. NO. 18460 | 320-IleArgGlnAspGlyThrValHis-327 |
| SEQ. ID. NO. 18461 | 337-GlyArgGlyGlyIleArgLeuSerGlyLysIleAspThrGluLysAspIleLeu-354 |
| SEQ. ID. NO. 18462 | 362-SerValGlyAlaGluAspValLeu-369 |
| SEQ. ID. NO. 18463 | 372-AlaPheLysGlyArgLeuAspGlySerIle-381 |
| SEQ. ID. NO. 18464 | 387-ThrAlaSerProLysIle-392 |
| SEQ. ID. NO. 18465 | 400-ThrAlaArgThrAspGlySerLeu-407 |
| SEQ. ID. NO. 18466 | 411-SerAspProAlaAsnGlyGlnArgLysLeuVal-421 |
| SEQ. ID. NO. 18467 | 430-GlyGlnGlySerLeuThr-435 |
| SEQ. ID. NO. 18468 | 442-LeuPheLysAspArgLeuLeuLysLeuAspIleArgSerArgAlaPheAspProSerArgIleAspProGlnLeu-466 |
| SEQ. ID. NO. 18469 | 480-GluLeuAlaLysGluLysPheThrGlyLys-489 |
| SEQ. ID. NO. 18470 | 508-IleValTyrGluSerArgHisLeuProArgAlaAlaVal-520 |
| SEQ. ID. NO. 18471 | 522-LeuArgLeuGlyArgAsnIleIleLysThrAspGlyGlyPheGlyLysLysGlyAspArgLeuAsn-543 |
| SEQ. ID. NO. 18472 | 548-AlaProAspLeuSerArgPheGly-555 |
| SEQ. ID. NO. 18473 | 563-AsnValArgGlyHisLeuSerGlyAspLeuAspGlyGlyIleArgThrPheGluThrAspLeuSerGlyAlaAla-587 |
| SEQ. ID. NO. 18474 | 594-LysAlaAlaAspIleArgSer-600 |
| SEQ. ID. NO. 18475 | 605-LeuLysGlySerProAspThrSerArgProIleArgAlaAspIleLysGlySerArgLeuSerLeuSerGlyGlyAlaGluValValAspThrAlaAspLeu MetLeuAspGlyThrGlyVal-645 |
| SEQ. ID. NO. 18476 | 647-HisArgIleArgThr-651 |
| SEQ. ID. NO. 18477 | 656-ThrLeuAspGlyLysProPheLysPheAspLeuAspAlaSerGlyGlyIleAsnArgGluLeuThrArgTrpLysGlySerIle-683 |
| SEQ. ID. NO. 18478 | 696-LeuGlnAsnArgMetThrLeu-702 |
| SEQ. ID. NO. 18479 | 704-AlaGlyAlaGluArgValAla-710 |
| SEQ. ID. NO. 18480 | 729-SerTrpAspLysLysThrGlyIleSerAlaLysGlyGlyAla-742 |
| SEQ. ID. NO. 18481 | 764-LeuAsnGlyAspTrp-768 |
| SEQ. ID. NO. 18482 | 772-TyrGlyArgAsnAlaArgGly-778 |
| SEQ. ID. NO. 18483 | 782-IleSerArgGlnSerGlyAspAlaValLeu-791 |
| SEQ. ID. NO. 18484 | 803-SerLeuLysThrArgPheGlnAsnAspArgIleGly-814 |
| SEQ. ID. NO. 18485 | 817-LeuAspGlyGlyAlaArgPheGlyArgIleAsnAlaAspLeuAspIle-832 |
| SEQ. ID. NO. 18486 | 844-ProLeuGlyGlyArgIleThr-850 |
| SEQ. ID. NO. 18487 | 882-GlyArgValGlySerProSerVal-889 |
| SEQ. ID. NO. 18488 | 893-ValAsnGlySerSerAsnTyrGlyLysIleAsnGly-904 |
| SEQ. ID. NO. 18489 | 908-ValGlyGlnSerArgSerPheAspThrAlaProLeuGlyGlyArgLeuAsn-924 |
| SEQ. ID. NO. 18490 | 941-GlnThrValLysGlySerLeu-947 |
| SEQ. ID. NO. 18491 | 956-SerIleAlaAspProHisLeuGlyGly-964 |
| SEQ. ID. NO. 18492 | 966-IleAsnGlyAspLysLeuTyrTyrArgAsnGlnThr-977 |
| SEQ. ID. NO. 18493 | 982-LeuAspAsnGlySerLeuArg-988 |
| SEQ. ID. NO. 18494 | 991-IleAlaGlyArgLysTrpVal-997 |
| SEQ. ID. NO. 18495 | 1001-LeuLysPheArgHisGluGlyThrAlaGluLeuSerGly-1013 |
| SEQ. ID. NO. 18496 | 1015-ValGlyMetGluAsnSerGlyProAspValAspIle-1026 |
| SEQ. ID. NO. 18497 | 1031-AspLysTyrArgIleLeuSerArgProAsnArgArgLeuThr-1044 |
| SEQ. ID. NO. 18498 | 1047-GlyAsnThrArgLeuArgTyrSerProGlnLysGlyIle-1059 |
| SEQ. ID. NO. 18499 | 1065-IleLysThrAspGlnGlyLeuPheGlySerGlnLysSerSerMetProSerValGlyAspAspVal-1086 |
| SEQ. ID. NO. 18500 | 1091-GluValLysLysGluAlaAla-1097 |
| SEQ. ID. NO. 18501 | 1109-AspLeuAsnAspGlyIleArg-1115 |
| SEQ. ID. NO. 18502 | 1134-GlnSerGlyGlySerValArgGlyValGly-1143 |
| SEQ. ID. NO. 18503 | 1146-ArgValIleLysGlyArgTyrLysAlaTyrGlyGlnAspLeuAspIleThrLysGlyThr-1165 |
| SEQ. ID. NO. 18504 | 1171-ProLeuAsnAspProAsnLeuAsnIleArgAlaGluArgArgLeuSerProValGly-1189 |
| SEQ. ID. NO. 18505 | 1197-SerLeuAsnSerProArgIle-1203 |
| SEQ. ID. NO. 18506 | 1207-AlaAsnGluProMetSerGluLysAspLysLeu-1217 |
| SEQ. ID. NO. 18507 | 1225-AlaGlySerGlySerSerGlyAspAsnAlaAla-1235 |
| SEQ. ID. NO. 18508 | 1246-GlyGlnIleAsnAspArgIleGlyLeu-1254 |
| SEQ. ID. NO. 18509 | 1256-AspAspLeuGlyPheThrSerLysArgSerArgAsnAlaGlnThrGlyGluLeuAsnProAlaGlu-1277 |
| SEQ. ID. NO. 18510 | 1283-GlyLysGlnLeuThrGlyLys-1289 |
| SEQ. ID. NO. 18511 | 1299-SerSerAlaGluGlnSerVal-1305 |
| SEQ. ID. NO. 18512 | 1321-IleGlySerArgSerSerGlyGlyGluLeu-1330 |
| SEQ. ID. NO. 18513 | 1335-ArgPheAspArgPheSerGlySerAspLysLysAspSerAlaGlyAsnSerLysGlyLys-1354 |
| Hydrophilic Regions- Hopp-Woods | |
| SEQ. ID. NO. 18514 | 56-PheAspGlyAspAsnTrpSerIleGluThrGluGlyAlaAspLeuLysIleSerArg-74 |
| SEQ. ID. NO. 18515 | 83-GluLeuMetArgArgSerLeuHis-90 |
| SEQ. ID. NO. 18516 | 105-ProThrProProLysGluGluArgProPro-114 |
| SEQ. ID. NO. 18517 | 130-AspArgPheGluThrGlyLys-136 |
| SEQ. ID. NO. 18518 | 141-LysAlaPheAspLys-145 |
| SEQ. ID. NO. 18519 | 151-GluArgLeuAspAla-155 |
| SEQ. ID. NO. 18520 | 157-TyrArgTyrAspArgLysGlyHisArgLeuAspLeuLysAlaAlaAsp-172 |
| SEQ. ID. NO. 18521 | 200-GlyGlyLeuGluGlyLysThrIle-207 |
| SEQ. ID. NO. 18522 | 215-GlySerLeuLysAspValArgAla-222 |
| SEQ. ID. NO. 18523 | 244-GluSerLeuAspLysThrLeuGlu-251 |

TABLE 1-continued

| | |
|---|---|
| SEQ. ID. NO. 18524 | 292-GlySerLeuAspLeuGluAsnThrLys-300 |
| SEQ. ID. NO. 18525 | 302-GlyPheAlaAspArgAsnGlyIlePro-310 |
| SEQ. ID. NO. 18526 | 320-IleArgGlnAspGly-324 |
| SEQ. ID. NO. 18527 | 343-LeuSerGlyLysIleAspThrGluLysAspIleLeu-354 |
| SEQ. ID. NO. 18528 | 364-GlyAlaGluAspValLeu-369 |
| SEQ. ID. NO. 18529 | 373-PheLysGlyArgLeuAspGly-379 |
| SEQ. ID. NO. 18530 | 401-AlaArgThrAspGly-405 |
| SEQ. ID. NO. 18531 | 412-AspProAlaAsnGlyGlnArgLysLeuVal-421 |
| SEQ. ID. NO. 18532 | 442-LeuPheLysAspArgLeuLeuLysLeuAspIleArgSerArgAlaPheAspProSerArgIleAspPro-464 |
| SEQ. ID. NO. 18533 | 480-GluLeuAlaLysGluLysPheThrGly-488 |
| SEQ. ID. NO. 18534 | 508-IleValTyrGluSerArgHisLeuPro-516 |
| SEQ. ID. NO. 18535 | 522-LeuArgLeuGlyArgAsnIleIleLysThrAspGlyGlyPheGlyLysLysGlyAspArgLeuAsn-543 |
| SEQ. ID. NO. 18536 | 570-GlyAspLeuAspGlyGlyIleArgThrPheGluThrAspLeuSerGlyAlaAla-587 |
| SEQ. ID. NO. 18537 | 594-LysAlaAlaAspIleArgSer-600 |
| SEQ. ID. NO. 18538 | 607-GlySerProAspThrSerArgProIleArgAlaAspIleLysGlySerArgLeuSerLeu-626 |
| SEQ. ID. NO. 18539 | 631-GluValValAspThrAlaAspLeuMetLeu-640 |
| SEQ. ID. NO. 18540 | 647-HisArgIleArgThr-651 |
| SEQ. ID. NO. 18541 | 657-LeuAspGlyLysProPheLysPheAspLeuAspAla-668 |
| SEQ. ID. NO. 18542 | 670-GlyGlyIleAsnArgGluLeuThrArgTrpLysGly-681 |
| SEQ. ID. NO. 18543 | 704-AlaGlyAlaGluArgValAla-710 |
| SEQ. ID. NO. 18544 | 729-SerTrpAspLysLysThrGlyIleSerAlaLysGlyGlyAla-742 |
| SEQ. ID. NO. 18545 | 783-SerArgGlnSerGly-787 |
| SEQ. ID. NO. 18546 | 806-ThrArgPheGlnAsnAspArgIle-813 |
| SEQ. ID. NO. 18547 | 819-GlyGlyAlaArgPheGlyArgIleAsnAlaAspLeuAspIle-832 |
| SEQ. ID. NO. 18548 | 1001-LeuLysPheArgHisGluGlyThrAlaGluLeu-1011 |
| SEQ. ID. NO. 18549 | 1017-MetGluAsnSerGlyProAspValAspIle-1026 |
| SEQ. ID. NO. 18550 | 1031-AspLysTyrArgIleLeuSerArgProAsnArgArgLeuThr-1044 |
| SEQ. ID. NO. 18551 | 1049-ThrArgLeuArgTyrSerPro-1055 |
| SEQ. ID. NO. 18552 | 1065-IleLysThrAspGln-1069 |
| SEQ. ID. NO. 18553 | 1075-GlnLysSerSerMet-1079 |
| SEQ. ID. NO. 18554 | 1091-GluValLysLysGluAlaAla-1097 |
| SEQ. ID. NO. 18555 | 1109-AspLeuAsnAspGlyIleArg-1115 |
| SEQ. ID. NO. 18556 | 1146-ArgValIleLysGlyArgTyrLysAlaTyrGlyGlnAspLeuAspIleThrLys-1163 |
| SEQ. ID. NO. 18557 | 1179-IleArgAlaGluArgArgLeuSer-1186 |
| SEQ. ID. NO. 18558 | 1209-GluProMetSerGluLysAspLysLeu-1217 |
| SEQ. ID. NO. 18559 | 1225-AlaGlySerGlySerSerGlyAspAsnAlaAla-1235 |
| SEQ. ID. NO. 18560 | 1248-IleAsnAspArgIleGlyLeu-1254 |
| SEQ. ID. NO. 18561 | 1259-GlyPheThrSerLysArgSerArgAsnAlaGlnThrGlyGluLeuAsnPro-1275 |
| SEQ. ID. NO. 18562 | 1300-SerAlaGluGlnSerVal-1305 |
| SEQ. ID. NO. 18563 | 1321-IleGlySerArgSerSerGlyGly-1328 |
| SEQ. ID. NO. 18564 | 1335-ArgPheAspArgPheSerGlySerAspLysLysAspSerAlaGlyAsnSerLysGlyLys-1354 |
| a286 | |
| AMPHI Regions - AMPHI | |
| SEQ. ID. NO. 18565 | 69-GluIleLysAspMetVal-74 |
| SEQ. ID. NO. 18566 | 102-ProAspAsnValLysThr-107 |
| SEQ. ID. NO. 18567 | 145-ValAlaIleLeuGlyAsp-150 |
| SEQ. ID. NO. 18568 | 157-LeuAlaGluTyrTyrArgAsnAlaLeuGluAsnTrpGlnGlnProValGlySer-174 |
| SEQ. ID. NO. 18569 | 198-ProLeuAlaLysLeuGlyAsn-204 |
| SEQ. ID. NO. 18570 | 238-ThrGlnArgTyrProGluGlnIleValSerGlyLeuAlaArgPheGlnProGlyThr-256 |
| SEQ. ID. NO. 18571 | 326-AspTyrTyrAsnLeuPheAsnLys-333 |
| SEQ. ID. NO. 18572 | 354-IleSerGlnProArg-358 |
| SEQ. ID. NO. 18573 | 375-ThrThrGlnAsnLeu-379 |
| SEQ. ID. NO. 18574 | 428-ThrAlaSerTrpLysArgGlnLeuLeu-436 |
| SEQ. ID. NO. 18575 | 455-ThrLeuGlyAlaPhe-459 |
| SEQ. ID. NO. 18576 | 513-GlyAlaSerSerVal-517 |
| SEQ. ID. NO. 18577 | 555-LeuSerGlyAlaValPheHisAspMetGlyAspAlaAlaAlaAsn-569 |
| SEQ. ID. NO. 18578 | 584-ArgTrpPheSerProLeu-589 |
| Antigenic Index - Jameson-Wolf | |
| SEQ. ID. NO. 18579 | 1-MetHisAspThrArgThrMetMet-8 |
| SEQ. ID. NO. 18580 | 30-AlaAspLeuSerGluAsnLysAla-37 |
| SEQ. ID. NO. 18581 | 43-PheLysAsnLysSerProAspThrGluSerValLysLeuLysProLysPheProVal-61 |
| SEQ. ID. NO. 18582 | 63-IleAspThrGlnAspSerGluIleLysAspMetValGluGluHisLeu-78 |
| SEQ. ID. NO. 18583 | 83-GlnGlnGlnGluGluValLeuAspLysGluGlnThr-94 |
| SEQ. ID. NO. 18584 | 97-LeuAlaGluGluAlaProAspAsnValLysThrMetLeuArgSerLysGlyTyrPheSerSerLysValSerLeuThrGluLysAspGlyAla-127 |
| SEQ. ID. NO. 18585 | 133-ThrProGlyProArgThrLysIle-140 |
| SEQ. ID. NO. 18586 | 151-IleLeuSerAspGlyAsnLeuAlaGluTyrTyrArgAsnAlaLeuGluAsnTrpGln-169 |
| SEQ. ID. NO. 18587 | 172-ValGlySerAspPheAspGlnAspSerTrpGluAsnSerLysThrSerVal-188 |
| SEQ. ID. NO. 18588 | 192-ValThrArgLysAlaTyrPro-198 |
| SEQ. ID. NO. 18589 | 201-LysLeuGlyAsnThrArgAlaAlaValAsnProAspThrAlaThrAla-216 |
| SEQ. ID. NO. 18590 | 223-AspSerGlyArgProIleAla-229 |
| SEQ. ID. NO. 18591 | 234-GluIleThrGlyThrGlnArgTyrProGluGlnIle-245 |
| SEQ. ID. NO. 18592 | 252-PheGlnProGlyThrProTyrAspLeu-260 |
| SEQ. ID. NO. 18593 | 270-LeuGluGlnAsnGlyHisTyrSerGly-278 |
| SEQ. ID. NO. 18594 | 283-AlaAspPheAspArgLeuGlnGlyAspArgValProVal-295 |
| SEQ. ID. NO. 18595 | 298-SerValThrGluValLysArgHisLysLeuGluThrGlyIleArgLeuAspSerGluTyrGlyLeuGlyGly-321 |
| SEQ. ID. NO. 18596 | 342-AspMetAspLysTyrGluThr-348 |
| SEQ. ID. NO. 18597 | 355-SerGlnProArgAsnTyrArgGlyAsnTyrTrp-365 |
| SEQ. ID. NO. 18598 | 368-AsnValSerTyrAsnArgSerThrThrGlnAsnLeuGluLysArgAlaPheSerGlyGly-387 |
| SEQ. ID. NO. 18599 | 391-ValArgAspArgAlaGlyIleAspAlaArgLeuGly-402 |
| SEQ. ID. NO. 18600 | 405-PheLeuAlaGluGlyArgLysIleProGlySerAspIleAspLeuGlyAsnSerHisAla-424 |

TABLE 1-continued

| | |
|---|---|
| SEQ. ID. NO. 18601 | 430-SerTrpLysArgGlnLeu-435 |
| SEQ. ID. NO. 18602 | 441-HisProGluAsnGlyHisTyrLeuAspGlyLysIle-452 |
| SEQ. ID. NO. 18603 | 468-ThrSerAlaArgAlaGly-473 |
| SEQ. ID. NO. 18604 | 476-PheThrProGluAsnLysLysLeu-483 |
| SEQ. ID. NO. 18605 | 496-ValAlaArgAspAsnAlaAsnValPro-504 |
| SEQ. ID. NO. 18606 | 509-PheArgSerGlyGlyAlaSerSerValArgGlyTyrGluLeuAspSer-524 |
| SEQ. ID. NO. 18607 | 534-ValLeuProGluArgAlaLeu-540 |
| SEQ. ID. NO. 18608 | 562-AspMetGlyAspAla-566 |
| SEQ. ID. NO. 18609 | 568-AlaAsnPheLysArgMetLysLeuLysHisGlySerGlyLeu-581 |
| SEQ. ID. NO. 18610 | 598-TyrGlyHisSerAspLysLysIleArg-606 |
| Hydrophilic Regions - Hopp-Woods | |
| SEQ. ID. NO. 18611 | 1-MetHisAspThrArgThrMetMet-8 |
| SEQ. ID. NO. 18612 | 30-AlaAspLeuSerGluAsnLysAla-37 |
| SEQ. ID. NO. 18613 | 44-LysAsnLysSerProAspThrGluSerValLysLeuLysProLysPheProVal-61 |
| SEQ. ID. NO. 18614 | 63-IleAspThrGlnAspSerGluIleLysAspMetValGluGluHisLeu-78 |
| SEQ. ID. NO. 18615 | 84-GlnGlnGluGluValLeuAspLysGluGlnThr-94 |
| SEQ. ID. NO. 18616 | 97-LeuAlaGluGluAlaProAspAsnValLysThrMetLeuArgSer-111 |
| SEQ. ID. NO. 18617 | 119-ValSerLeuThrGluLysAspGlyAla-127 |
| SEQ. ID. NO. 18618 | 134-ProGlyProArgThrLysIle-140 |
| SEQ. ID. NO. 18619 | 174-SerAspPheAspGlnAspSerTrpGluAsnSerLysThr-186 |
| SEQ. ID. NO. 18620 | 192-ValThrArgLysAlaTyrPro-198 |
| SEQ. ID. NO. 18621 | 206-ArgAlaAlaValAsnProAspThrAlaThr-215 |
| SEQ. ID. NO. 18622 | 239-GlnArgTyrProGlu-243 |
| SEQ. ID. NO. 18623 | 283-AlaAspPheAspArgLeuGlnGlyAspArgValProVal-295 |
| SEQ. ID. NO. 18624 | 298-SerValThrGluValLysArgHisLysLeuGluThrGlyIleArgLeuAspSerGluTyr-317 |
| SEQ. ID. NO. 18625 | 342-AspMetAspLysTyrGluThr-348 |
| SEQ. ID. NO. 18626 | 373-ArgSerThrThrGlnAsnLeuGluLysArgAlaPhe-384 |
| SEQ. ID. NO. 18627 | 392-ArgAspArgAlaGlyIleAspAlaArgLeuGly-402 |
| SEQ. ID. NO. 18628 | 405-PheLeuAlaGluGlyArgLysIleProGlySerAspIleAspLeu-419 |
| SEQ. ID. NO. 18629 | 478-ProGluAsnLysLysLeu-483 |
| SEQ. ID. NO. 18630 | 496-ValAlaArgAspAsnAlaAsn-502 |
| SEQ. ID. NO. 18631 | 518-ArgGlyTyrGluLeuAspSer-524 |
| SEQ. ID. NO. 18632 | 534-ValLeuProGluArgAlaLeu-540 |
| SEQ. ID. NO. 18633 | 562-AspMetGlyAspAla-566 |
| SEQ. ID. NO. 18634 | 568-AlaAsnPheLysArgMetLysLeuLysHis-577 |
| SEQ. ID. NO. 18635 | 600-HisSerAspLysLysIleArg-606 |
| a287 | |
| AMPHI Regions - AMPHI | |
| SEQ. ID. NO. 18636 | 29-LysSerAlaAspThrLeuSerLysProAlaAla-39 |
| SEQ. ID. NO. 18637 | 77-GlyGlyGlnAspMet-81 |
| SEQ. ID. NO. 18638 | 109-AsnAspMetProGlnAsn-114 |
| SEQ. ID. NO. 18639 | 131-MetProThrArgAspMetGlyAsnGlnAlaProAspAlaGlyGluSerAlaGlnProAlaAsnGlnProAspMetAlaAsnAlaAlaAspGlyMet-162 |
| SEQ. ID. NO. 18640 | 171-GluAsnAlaGlyAsnThrAlaAspGlnAlaAlaAsnGlnAlaGluAsn-186 |
| SEQ. ID. NO. 18641 | 192-SerGlnAsnProAla-196 |
| SEQ. ID. NO. 18642 | 206-GlyGlySerAspPhe-210 |
| SEQ. ID. NO. 18643 | 213-IleAsnValAlaAsnGly-218 |
| SEQ. ID. NO. 18644 | 256-LeuSerAspGluGluLysIleAsnLysTyrLysLys-267 |
| SEQ. ID. NO. 18645 | 306-PheArgArgSerAlaArg-311 |
| SEQ. ID. NO. 18646 | 419-LysSerValAspGlyIleIleAspSer-427 |
| SEQ. ID. NO. 18647 | 447-PheLysGlyThrTrpThr-452 |
| SEQ. ID. NO. 18648 | 459-ValSerGlyArgPheTyr-464 |
| Antigenic Index - Jameson-Wolf | |
| SEQ. ID. NO. 18649 | 17-AlaCysGlyGlyGlyGlyGlyGlySerProAspValLysSerAlaAspThrLeuSerLysProAla-38 |
| SEQ. ID. NO. 18650 | 42-ValThrGluAspValGlyGluGluValLeuProLysGluLysLysAspGluGluAlaValSerGlyAlaProGlnAlaAspThrGlnAspAlaThrAlaGly LysGlyGlyGlnAspMet-81 |
| SEQ. ID. NO. 18651 | 85-SerAlaGluAsnThrGlyAsnGlyGlyAlaAlaThrThrAspAsnProGluAsnLysAspGluGlyProGlnAsnAspMetProGlnAsnAlaAlaAsp ThrAspSerSerThrProAsnHisThrProAlaProAsnMetProThrArgAspMetGlyAsnGlnAlaProAspAlaGlyGluSerAlaGlnProAlaAsnGln ProAspMetAlaAsnAlaAlaAspGlyMetGlnGlyAspAspProSerAlaGlyGluAsnAlaGlyAsnThrAlaAspGlnAlaAlaAsnGlnAlaGluAsn AsnGlnValGlyGlySerGlnAsnProAlaSerSerThrAsnProAsnAlaThrAsnGlyGlySerAspPheGlyArg-212 |
| SEQ. ID. NO. 18652 | 214-AsnValAlaAsnGlyIleLysLeuAspSerGlySerGluAsnVal-228 |
| SEQ. ID. NO. 18653 | 232-HisCysLysAspLysValCysAspArgAspPheLeuAspGluGluAlaProProLysSerGluPheGluLysLeuSerAspGluGluLysIleAsnLys TyrLysLysAspGluGlnArgGluAsnPhe-274 |
| SEQ. ID. NO. 18654 | 278-ValAlaAspArgValGluLysAsnGlyThrAsnLys-289 |
| SEQ. ID. NO. 18655 | 293-IleTyrLysAspLysSerAlaSerSerSerSerAlaArgPheArgArgSerAlaArgSerArgArgSerLeuProAla-318 |
| SEQ. ID. NO. 18656 | 332-IleValAspGlyGluAla-337 |
| SEQ. ID. NO. 18657 | 342-GlyHisSerGlyAsn-346 |
| SEQ. ID. NO. 18658 | 349-AlaProGluGlyAsnTyrArgTyrLeu-357 |
| SEQ. ID. NO. 18659 | 360-GlyAlaGluLysLeuSerGlyGlySer-368 |
| SEQ. ID. NO. 18660 | 374-GlnGlyGluProAlaLysGlyGluMet-382 |
| SEQ. ID. NO. 18661 | 397-HisMetGluAsnGlyArgProSerProSerGlyGlyArgPheAlaAla-412 |
| SEQ. ID. NO. 18662 | 414-ValAspPheGlySerLysSerValAspGlyIleIleAspSerGlyAspAspLeuHisMetGlyThrGlnLysPhe-438 |
| SEQ. ID. NO. 18663 | 442-IleAspGlyAsnGlyPheLysGlyThrTrpThrGluAsnGlyGlyGlyAspValSerGly-461 |
| SEQ. ID. NO. 18664 | 463-PheTyrGlyProAlaGlyGluGluValAlaGlyLysTyrSerTyrArgProThrAspAlaGluLysGlyGlyPhe-487 |
| SEQ. ID. NO. 18665 | 491-AlaGlyLysLysGluGlnAsp-497 |
| Hydrophilic Regions- Hopp-Woods | |
| SEQ. ID. NO. 18666 | 22-GlyGlyGlySerProAspValLysSerAlaAspThrLeuSerLysProAla-38 |
| SEQ. ID. NO. 18667 | 42-ValThrGluAspValGlyGluGluValLeuProLysGluLysLysAspGluGluAlaValSer-62 |
| SEQ. ID. NO. 18668 | 65-ProGlnAlaAspThrGlnAspAlaThrAlaGlyLysGlyGlyGlnAsp-80 |
| SEQ. ID. NO. 18669 | 85-SerAlaGluAsnThrGly-90 |
| SEQ. ID. NO. 18670 | 95-AlaThrThrAspAsnProGluAsnLysAspGluGlyProGlnAsnAspMetProGlnAsnAlaAlaAspThrAspSerSerThr-122 |

TABLE 1-continued

| | |
|---|---|
| SEQ. ID. NO. 18671 | 131-MetProThrArgAspMetGlyAsnGlnAlaProAspAlaGlyGluSerAlaGln-148 |
| SEQ. ID. NO. 18672 | 151-AsnGlnProAspMetAlaAsnAlaAlaAspGlyMetGlnGlyAspAspProSerAlaGlyGluAsnAlaGlyAsnThrAlaAspGlnAlaAlaAsnGlnAlaGluAsnAsnGln-188 |
| SEQ. ID. NO. 18673 | 193-GlnAsnProAlaSer-197 |
| SEQ. ID. NO. 18674 | 206-GlyGlySerAspPheGlyArg-212 |
| SEQ. ID. NO. 18675 | 219-IleLysLeuAspSerGlySerGlu-226 |
| SEQ. ID. NO. 18676 | 232-HisCysLysAspLysValCysAspArgAspPheLeuAspGluGluAlaProProLysSerGluPheGluLysLeuSerAspGluGluLysIleAsnLysTyrLysLysAspGluGlnArgGluAsnPhe-274 |
| SEQ. ID. NO. 18677 | 278-ValAlaAspArgValGluLysAsnGlyThr-287 |
| SEQ. ID. NO. 18678 | 294-TyrLysAspLysSerAlaSerSerSerSerAlaArgPheArgArgSerAlaArgSerArgArgSerLeuPro-317 |
| SEQ. ID. NO. 18679 | 332-IleValAspGlyGluAla-337 |
| SEQ. ID. NO. 18680 | 360-GlyAlaGluLysLeuSer-365 |
| SEQ. ID. NO. 18681 | 374-GlnGlyGluProAlaLysGlyGluMet-382 |
| SEQ. ID. NO. 18682 | 399-GluAsnGlyArgProSerProSerGlyGly-408 |
| SEQ. ID. NO. 18683 | 414-ValAspPheGlySerLysSerValAspGlyIleIleAspSerGlyAspAspLeuHis-432 |
| SEQ. ID. NO. 18684 | 455-GlyGlyGlyAspValSer-460 |
| SEQ. ID. NO. 18685 | 467-AlaGlyGluGluValAlaGly-473 |
| SEQ. ID. NO. 18686 | 475-TyrSerTyrArgProThrAspAlaGluLysGlyGly-486 |
| SEQ. ID. NO. 18687 | 491-AlaGlyLysLysGluGlnAsp-497 |
| a288 | |
| AMPHI Regions- AMPHI | |
| SEQ. ID. NO. 18688 | 7-ValSerArgValLeu-11 |
| SEQ. ID. NO. 18689 | 54-IleValThrLysCysAla-59 |
| SEQ. ID. NO. 18690 | 61-ArgProTyrArgThrPheSerProLeuProVal-71 |
| SEQ. ID. NO. 18691 | 97-HisSerThrLeuArg-101 |
| SEQ. ID. NO. 18692 | 150-AlaLeuPheGlnAlaGlyPheAspLysAlaValGln-161 |
| Antigenic Index - Jameson-Wolf | |
| SEQ. ID. NO. 18693 | 2-HisThrGlyGlnAla-6 |
| SEQ. ID. NO. 18694 | 28-AsnLeuProGluArgSerAlaGlySer-36 |
| SEQ. ID. NO. 18695 | 58-CysAlaValArgProTyrArgThrPheSerPro-68 |
| SEQ. ID. NO. 18696 | 72-LeuProLysGlnProSerAla-78 |
| SEQ. ID. NO. 18697 | 89-LeuProArgProAlaValAsnArgHisSerThrLeuArgSerProAspPheProProArgMet-109 |
| SEQ. ID. NO. 18698 | 113-IleArgGlyAspCysLeuPro-119 |
| SEQ. ID. NO. 18699 | 126-IleIleThrArgAsnAlaLysMetProSerGluThrValGlnValSerAspGlyIleGlnProLys-147 |
| SEQ. ID. NO. 18700 | 155-GlyPheAspLysAlaVal-160 |
| Hydrophilic Regions - Hopp-Woods | |
| SEQ. ID. NO. 18701 | 28-AsnLeuProGluArgSerAla-34 |
| SEQ. ID. NO. 18702 | 58-CysAlaValArgPro-62 |
| SEQ. ID. NO. 18703 | 98-SerThrLeuArgSerProAspPheProPro-107 |
| SEQ. ID. NO. 18704 | 113-IleArgGlyAspCys-117 |
| SEQ. ID. NO. 18705 | 126-IleIleThrArgAsnAlaLysMetProSerGluThrValGlnVal-140 |
| SEQ. ID. NO. 18706 | 155-GlyPheAspLysAlaVal-160 |
| a292 | |
| AMPHI Regions- AMPHI | |
| SEQ. ID. NO. 18707 | 7-LysIleLeuThrProPheThrValLeuProLeu-17 |
| SEQ. ID. NO. 18708 | 40-GlyLysSerValAla-44 |
| SEQ. ID. NO. 18709 | 62-ValLeuSerValSerGlu-67 |
| SEQ. ID. NO. 18710 | 69-ProValLysGlyIleTyrGlu-75 |
| SEQ. ID. NO. 18711 | 110-GluArgAlaAlaAspLeu-115 |
| SEQ. ID. NO. 18712 | 124-ProLeuAspLysAlaIleLysGluValArgGly-134 |
| SEQ. ID. NO. 18713 | 150-PheCysLysArgLeuGluHisGluPheGluLysMetThrAspValThr-165 |
| SEQ. ID. NO. 18714 | 195-LysAlaTrpThrAspTrpMetArg-202 |
| SEQ. ID. NO. 18715 | 212-IleCysAspAsnProVal-217 |
| Antigenic Index - Jameson-Wolf | |
| SEQ. ID. NO. 18716 | 1-MetLysThrLysLeu-5 |
| SEQ. ID. NO. 18717 | 23-ThrProValSerAsnAlaAsnAlaGluProAlaValLysAlaGluSerAlaGlyLysSerVal-43 |
| SEQ. ID. NO. 18718 | 47-LeuLysAlaArgLeuGluLysThrTyrSerAlaGlnAspLeuLys-61 |
| SEQ. ID. NO. 18719 | 66-SerGluThrProValLysGlyIle-73 |
| SEQ. ID. NO. 18720 | 85-TyrThrAspAlaGluGlyGlyTyr-92 |
| SEQ. ID. NO. 18721 | 99-IleAsnIleAspThrArgLysAsnLeuThrGluGluArgAlaAlaAspLeuAsnLys-117 |
| SEQ. ID. NO. 18722 | 124-ProLeuAspLysAlaIleLysGluValArgGlyAsnGlyLysLeuLysVal-140 |
| SEQ. ID. NO. 18723 | 142-ValPheSerAspProAspCysProPhe-150 |
| SEQ. ID. NO. 18724 | 152-LysArgLeuGluHisGluPheGluLysMetThrAsp-163 |
| SEQ. ID. NO. 18725 | 177-HisProAspAlaAlaArgLysAla-184 |
| SEQ. ID. NO. 18726 | 189-CysGlnProAspArgAlaLysAla-196 |
| SEQ. ID. NO. 18727 | 200-TrpMetArgLysGlyLysPheProVal-208 |
| SEQ. ID. NO. 18728 | 210-GlySerIleCysAspAsnProValAlaGluThrThrSerLeuGlyGlu-225 |
| SEQ. ID. NO. 18729 | 237-PheProAsnGlyArgSerGlnSerGlyTyrSerPro-248 |
| SEQ. ID. NO. 18730 | 250-ProGlnLeuGluGluIleIleArgLysAsnGln-260 |
| Hydrophilic Regions - Hopp-Woods | |
| SEQ. ID. NO. 18731 | 1-MetLysThrLysLeu-5 |
| SEQ. ID. NO. 18732 | 28-AlaAsnAlaGluProAlaValLysAlaGluSerAlaGlyLysSerVal-43 |
| SEQ. ID. NO. 18733 | 47-LeuLysAlaArgLeuGluLysThrTyrSer-56 |
| SEQ. ID. NO. 18734 | 99-IleAsnIleAspThrArgLysAsnLeuThrGluGluArgAlaAlaAspLeuAsnLys-117 |
| SEQ. ID. NO. 18735 | 124-ProLeuAspLysAlaIleLysGluValArgGlyAsnGlyLysLeuLys-139 |
| SEQ. ID. NO. 18736 | 144-SerAspProAspCysProPhe-150 |
| SEQ. ID. NO. 18737 | 152-LysArgLeuGluHisGluPheGluLysMetThrAsp-163 |
| SEQ. ID. NO. 18738 | 179-AspAlaAlaArgLysAla-184 |
| SEQ. ID. NO. 18739 | 190-GlnProAspArgAlaLysAla-196 |
| SEQ. ID. NO. 18740 | 200-TrpMetArgLysGlyLysPhe-206 |

TABLE 1-continued

| | |
|---|---|
| SEQ. ID. NO. 18741 | 240-GlyArgSerGlnSer-244 |
| SEQ. ID. NO. 18742 | 250-ProGlnLeuGluGluIleIleArgLysAsnGln-260 |
| a294 | |
| AMPHI Regions - AMPHI | |
| SEQ. ID. NO. 18743 | 27-ArgPheProAlaAlaPheArgArgTyrSer-36 |
| SEQ. ID. NO. 18744 | 45-LysProAlaGlyThr-49 |
| SEQ. ID. NO. 18745 | 51-TrpHisArgValArgArgPheLysSerAsnArgArgThr-63 |
| SEQ. ID. NO. 18746 | 65-GlyGlyLysProLeuLysLysThrTyrArg-74 |
| SEQ. ID. NO. 18747 | 92-AsnIleAlaGluArgAlaArgGluSerProArgArgTyrGlyLysArgTyrAlaAspIleGlyAspAsp-114 |
| SEQ. ID. NO. 18748 | 133-AlaValAlaHisIleValHisLeu-140 |
| SEQ. ID. NO. 18749 | 176-AlaMetSerTyrArg-180 |
| SEQ. ID. NO. 18750 | 206-SerIleLeuGlyGluProPheAlaThrSerPheGly-217 |
| SEQ. ID. NO. 18751 | 227-AlaPheSerValLeuAlaHisPhe-234 |
| SEQ. ID. NO. 18752 | 247-ThrValGlyTrpSerLysTyrIleHisThrVal-257 |
| Antigenic Index - Jameson-Wolf | |
| SEQ. ID. NO. 18753 | 20-AlaValArgThrSerSerAsnArgPhe-28 |
| SEQ. ID. NO. 18754 | 32-PheArgArgTyrSerAlaPheArg-39 |
| SEQ. ID. NO. 18755 | 44-ProLysProAlaGlyThrProTrpHisArgValArgArgPheLysSerAsnArgArgThrArgGlyGlyLysProLeuLysLysThrTyrArgProArgArg AlaGluCysArgCysArgArgAlaArgThr-87 |
| SEQ. ID. NO. 18756 | 93-IleAlaGluArgAlaArgGluSerProArgArgTyrGlyLysArgTyrAlaAspIleGlyAspAspSerAspThrIleArg-119 |
| SEQ. ID. NO. 18757 | 121-ArgValPheArgLeuGluTyr-127 |
| SEQ. ID. NO. 18758 | 161-HisThrGlyArgValSerCysGluAlaArgArgGluValGluLysAlaMetSer-178 |
| SEQ. ID. NO. 18759 | 240-LysMetAlaArgSer-244 |
| Hydrophilic Regions - Hopp-Woods | |
| SEQ. ID. NO. 18760 | 20-AlaValArgThrSerSerAsnArg-27 |
| SEQ. ID. NO. 18761 | 52-HisArgValArgArgPheLysSerAsnArgArgThrArgGlyGlyLysProLeuLysLysThrTyrArgProArgArgAlaGluCysArgCysArgArg AlaArgThr-87 |
| SEQ. ID. NO. 18762 | 93-IleAlaGluArgAlaArgGluSerProArgArgTyrGlyLysArgTyrAlaAspIleGlyAspAspSerAspThrIleArg-119 |
| SEQ. ID. NO. 18763 | 121-ArgValPheArgLeuGluTyr-127 |
| SEQ. ID. NO. 18764 | 165-ValSerCysGluAlaArgArgGluValGluLysAlaMetSer-178 |
| a295 | |
| AMPHI Regions - AMPHI | |
| SEQ. ID. NO. 18765 | 79-PheArgGlnProArg-83 |
| SEQ. ID. NO. 18766 | 112-ArgPhePheArgGlnPro-117 |
| SEQ. ID. NO. 18767 | 130-AlaPheLeuHisGlnIle-135 |
| SEQ. ID. NO. 18768 | 175-AsnLeuArgGlyPhePro-180 |
| SEQ. ID. NO. 18769 | 188-HisGlnGlnArgArgIleGlyLysThrLeuProGlnLeu-200 |
| SEQ. ID. NO. 18770 | 232-ThrLeuAlaProMetArgProIleCysArgGlyThrSerGly-245 |
| SEQ. ID. NO. 18771 | 262-TyrIleIleLysProLeuGluHis-269 |
| Antigenic Index - Jameson-Wolf | |
| SEQ. ID. NO. 18772 | 4-MetAlaArgHisAspAspGlnGlnGly-12 |
| SEQ. ID. NO. 18773 | 18-LeuProArgArgGlnGln-23 |
| SEQ. ID. NO. 18774 | 49-PheLysLeuProArgGlnArgPheHisLeu-58 |
| SEQ. ID. NO. 18775 | 73-HisGlyCysArgAlaGlnPheArgGlnProArgArgIleArgLeu-87 |
| SEQ. ID. NO. 18776 | 91-GlnThrAlaArgGlnArgSerGlyGlyArgThrAspGlnAlaAla-105 |
| SEQ. ID. NO. 18777 | 114-PheArgGlnProArgIleArgGlnLysGlnArgHisThrArg-127 |
| SEQ. ID. NO. 18778 | 136-GlyProAspPheGly-140 |
| SEQ. ID. NO. 18779 | 143-GlnAsnAlaGluHisArgAla-149 |
| SEQ. ID. NO. 18780 | 170-CysIleArgLysGlnAsnLeuArgGlyPheProSerArgArgGlyHisLeuArgHisGlnGlnArgArgIleGlyLysThrLeu-197 |
| SEQ. ID. NO. 18781 | 205-LeuGlyGlyThrArgPheProAspArgAsnGlyValTyrProAsnArgAlaGlyAsnGlyIleArgIleArgLeu-229 |
| SEQ. ID. NO. 18782 | 238-ProIleCysArgGlyThrSerGly-245 |
| SEQ. ID. NO. 18783 | 252-ProTyrProTyrArgArgLysGlnProGlnTyr-262 |
| SEQ. ID. NO. 18784 | 273-SerCysLysThrAsnAlaValArgThrValArgThrAlaPheArgGlnArgAsnGlnIleSer-293 |
| Hydrophilic Regions - Hopp-Woods | |
| SEQ. ID. NO. 18785 | 5-AlaArgHisAspAspGlnGlnGly-12 |
| SEQ. ID. NO. 18786 | 18-LeuProArgArgGlnGln-23 |
| SEQ. ID. NO. 18787 | 77-AlaGlnPheArgGlnProArgArgIleArgLeu-87 |
| SEQ. ID. NO. 18788 | 93-AlaArgGlnArgSerGlyGlyArgThrAspGlnAlaAla-105 |
| SEQ. ID. NO. 18789 | 117-ProArgIleArgGlnLysGlnArgHisThrArg-127 |
| SEQ. ID. NO. 18790 | 145-AlaGluHisArgAla-149 |
| SEQ. ID. NO. 18791 | 170-CysIleArgLysGlnAsnLeu-176 |
| SEQ. ID. NO. 18792 | 179-PheProSerArgArgGlyHisLeuArgHisGlnGlnArgArgIleGlyLys-195 |
| SEQ. ID. NO. 18793 | 209-ArgPheProAspArgAsnGly-215 |
| SEQ. ID. NO. 18794 | 225-IleArgIleArgLeu-229 |
| SEQ. ID. NO. 18795 | 238-ProIleCysArgGlyThr-243 |
| SEQ. ID. NO. 18796 | 254-ProTyrArgArgLysGlnPro-260 |
| SEQ. ID. NO. 18797 | 280-ArgThrValArgThrAlaPheArgGlnArgAsnGlnIle-292 |
| a297 | |
| AMPHI Regions - AMPHI | |
| SEQ. ID. NO. 18798 | 35-ArgThrGluArgVal-39 |
| SEQ. ID. NO. 18799 | 69-GlnProGlyAspSerLeuAlaAspValLeuAla-79 |
| SEQ. ID. NO. 18800 | 86-AspGluIleAlaArgIleThrGluLysTyr-95 |
| SEQ. ID. NO. 18801 | 157-LeuProThrLeuArg-161 |
| SEQ. ID. NO. 18802 | 199-LeuLysGluGlyAspAla-204 |
| SEQ. ID. NO. 18803 | 272-LeuValTyrThrArgIleSerSer-279 |
| SEQ. ID. NO. 18804 | 333-HisAlaAsnGlyValGluThrLeuTyrAlaHisLeuSerAlaPheSer-348 |
| Antigenic Index - Jameson-Wolf | |
| SEQ. ID. NO. 18805 | 8-AlaLysHisArgLysTyrAla-14 |
| SEQ. ID. NO. 18806 | 32-SerThrGluArgThrGluArgValArgProGlnArgValGluGlnLysLeuPro-49 |
| SEQ. ID. NO. 18807 | 52-SerTrpGlyGlySerGly-57 |

TABLE 1-continued

| | |
|---|---|
| SEQ. ID. NO. 18808 | 67-AlaValGlnProGlyAspSerLeuAla-75 |
| SEQ. ID. NO. 18809 | 78-LeuAlaArgSerGlyMetAlaArgAspGluIleAlaArgIleThrGluLysTyrGlyGlyGluAlaAspLeuArgHisLeuArgAlaAspGlnSerVal-110 |
| SEQ. ID. NO. 18810 | 115-GlyGlyAspGlyGlyAlaArgGluVal-123 |
| SEQ. ID. NO. 18811 | 127-ThrAspGluAspGlyGluArgAsnLeuValAlaLeuGluLysLysGlyGlyIleTrpArgArgSerAlaSerGluAlaAspMetLysVal-156 |
| SEQ. ID. NO. 18812 | 167-ThrSerAlaArgGlySerLeuAlaArgAlaGluValProValGluIleArgGluSerLeuSer-187 |
| SEQ. ID. NO. 18813 | 194-PheSerLeuAspGlyLeuLysGluGlyAspAlaVal-205 |
| SEQ. ID. NO. 18814 | 228-GluValValLysGlyGlyThrArgHis-236 |
| SEQ. ID. NO. 18815 | 240-TyrTyrArgSerAspLysGluGlyGlyGlyGlyGlyAsnTyrTyrAspGluAspGlyArgValLeuGlnGluLysGlyGlyPheAsn-268 |
| SEQ. ID. NO. 18816 | 276-ArgIleSerSerProPheGlyTyr-283 |
| SEQ. ID. NO. 18817 | 295-HisThrGlyIleAspTyrAla-301 |
| SEQ. ID. NO. 18818 | 303-ProGlnGlyThrProValArgAlaSerAlaAspGly-314 |
| SEQ. ID. NO. 18819 | 318-PheLysGlyArgLysGlyGlyTyrGly-326 |
| SEQ. ID. NO. 18820 | 333-HisAlaAsnGlyValGlu-338 |
| SEQ. ID. NO. 18821 | 350-AlaGluGlyAsnValArgGlyGlyGlu-358 |
| SEQ. ID. NO. 18822 | 365-SerThrGlyArgSerThrGlyProHisLeu-374 |
| SEQ. ID. NO. 18823 | 376-TyrGluAlaArgIleAsnGlyGlnProValAsn-386 |
| SEQ. ID. NO. 18824 | 393-ProThrProGluLeuThrGlnAlaAspLysAlaAla-404 |
| SEQ. ID. NO. 18825 | 408-GlnLysGlnLysAlaAspAlaLeu-415 |
| SEQ. ID. NO. 18826 | 426-ValSerGlnSerAsp-430 |
| Hydrophilic Regions - Hopp-Woods | |
| SEQ. ID. NO. 18827 | 8-AlaLysHisArgLysTyrAla-14 |
| SEQ. ID. NO. 18828 | 32-SerThrGluArgThrGluArgValArgProGlnArgValGluGlnLysLeu-48 |
| SEQ. ID. NO. 18829 | 68-ValGlnProGlyAspSerLeuAla-75 |
| SEQ. ID. NO. 18830 | 82-GlyMetAlaArgAspGluIleAlaArgIleThrGluLysTyrGlyGlyGluAlaAspLeuArgHisLeuArgAlaAspGln-108 |
| SEQ. ID. NO. 18831 | 117-AspGlyGlyAlaArgGlu-122 |
| SEQ. ID. NO. 18832 | 127-ThrAspGluAspGlyGluArgAsnLeuValAlaLeuGluLysLysGlyGlyIleTrpArgArgSerAlaSerGluAlaAspMetLysVal-156 |
| SEQ. ID. NO. 18833 | 167-ThrSerAlaArgGlySerLeuAlaArgAlaGluValProValGluIleArgGluSerLeu-186 |
| SEQ. ID. NO. 18834 | 194-PheSerLeuAspGlyLeuLysGluGlyAspAlaVal-205 |
| SEQ. ID. NO. 18835 | 228-GluValValLysGlyGlyThrArg-235 |
| SEQ. ID. NO. 18836 | 242-ArgSerAspLysGluGlyGlyGly-249 |
| SEQ. ID. NO. 18837 | 253-TyrTyrAspGluAspGlyArgValLeuGlnGluLysGlyGlyPhe-267 |
| SEQ. ID. NO. 18838 | 306-ThrProValArgAlaSerAla-312 |
| SEQ. ID. NO. 18839 | 319-LysGlyArgLysGlyGlyTyr-325 |
| SEQ. ID. NO. 18840 | 350-AlaGluGlyAsnValArgGlyGlyGlu-358 |
| SEQ. ID. NO. 18841 | 366-ThrGlyArgSerThrGly-371 |
| SEQ. ID. NO. 18842 | 378-AlaArgIleAsnGly-382 |
| SEQ. ID. NO. 18843 | 396-GluLeuThrGlnAlaAspLysAlaAla-404 |
| SEQ. ID. NO. 18844 | 408-GlnLysGlnLysAlaAspAlaLeu-415 |
| a298 | |
| AMPHI Regions - AMPHI | |
| SEQ. ID. NO. 18845 | 6-SerLeuPheAlaSerIleLeuMetSerAlaLeuIleAla-18 |
| SEQ. ID. NO. 18846 | 26-IleAsnAlaTyrTrpGlnGln-32 |
| SEQ. ID. NO. 18847 | 42-ProLeuAlaAlaTyr-46 |
| SEQ. ID. NO. 18848 | 62-LeuSerAspGlyIleLysAlaPhe-69 |
| SEQ. ID. NO. 18849 | 82-GlySerAlaAspMetPro-87 |
| SEQ. ID. NO. 18850 | 134-ValGlnLysSerLeuLys-139 |
| SEQ. ID. NO. 18851 | 157-SerTyrProSerPhePheAspTrpProLysThrIleGluGluThrLeuLysLysHisProGlu-177 |
| SEQ. ID. NO. 18852 | 188-AsnAspProTrpAsp-192 |
| SEQ. ID. NO. 18853 | 208-AlaGlnGluTyrLeuLysArgValAspArgIleLeuGluAlaAlaHis-223 |
| SEQ. ID. NO. 18854 | 245-GlnMetArgTyrLeuAspLysLeuLeuSerGluTyrLeu-257 |
| SEQ. ID. NO. 18855 | 276-ArgTyrThrAspSer-280 |
| SEQ. ID. NO. 18856 | 308-AlaLysIleMetGluLys-313 |
| Antigenic Index - Jameson-Wolf | |
| SEQ. ID. NO. 18857 | 22-SerGlnAsnProIleAsnAlaTyr-29 |
| SEQ. ID. NO. 18858 | 34-TyrHisArgAsnSerProLeuGluPro-42 |
| SEQ. ID. NO. 18859 | 47-GlyTrpTrpArgSerGlyAlaAlaLeuGlnGlu-57 |
| SEQ. ID. NO. 18860 | 70-LeuSerGlyGluThrProProThrAlaGlnAspGlyGlySerAlaAspMetProSerGluAlaAlaAlaProGluThrAlaProGlnThrGlyGluThrGlu TrpLysGlnAsnThrGlu-109 |
| SEQ. ID. NO. 18861 | 114-ArgThrGlyAspLys-118 |
| SEQ. ID. NO. 18862 | 136-LysSerLeuLysGlnGlnTyrGlyIleGluSerValAsnLeuSerLysGlnSerThrGly-155 |
| SEQ. ID. NO. 18863 | 162-PheAspTrpProLysThrIleGluGluThrLeuLysLysHisProGlu-177 |
| SEQ. ID. NO. 18864 | 186-GlyProAsnAspProTrp-191 |
| SEQ. ID. NO. 18865 | 194-ProValGlyLysArgTyrLeu-200 |
| SEQ. ID. NO. 18866 | 203-AlaSerAspGluTrpAla-208 |
| SEQ. ID. NO. 18867 | 211-TyrLeuLysArgValAspArgIleLeuGlu-220 |
| SEQ. ID. NO. 18868 | 236-TyrMetLysLysAlaLysLeuAspGlyGlnMetArgTyrLeuAsp-250 |
| SEQ. ID. NO. 18869 | 270-LeuSerGlyGlyLysAspArgTyrThrAspSerValAsnValAsnGlyLysProValArgTyrArgSerLysAspGlyIle-296 |
| SEQ. ID. NO. 18870 | 318-ProSerThrGlnProSerSerThrGlnPro-327 |
| Hydrophilic Regions - Hopp-Woods | |
| SEQ. ID. NO. 18871 | 73-GluThrProProThrAlaGlnAspGlyGlySerAlaAspMetProSerGluAlaAlaAlaProGluThrAlaProGlnThrGlyGluThrGluTrpLysGln AsnThrGlu-109 |
| SEQ. ID. NO. 18872 | 148-AsnLeuSerLysGlnSerThr-154 |
| SEQ. ID. NO. 18873 | 166-LysThrIleGluGluThrLeuLysLysHisProGlu-177 |
| SEQ. ID. NO. 18874 | 211-TyrLeuLysArgValAspArgIleLeuGlu-220 |
| SEQ. ID. NO. 18875 | 236-TyrMetLysLysAlaLysLeuAspGlyGlnMetArgTyrLeuAsp-250 |
| SEQ. ID. NO. 18876 | 271-SerGlyGlyLysAspArgTyrThrAsp-279 |

TABLE 1-continued

SEQ. ID. NO. 18877 281-ValAsnValAsnGlyLysProValArgTyrArgSerLysAspGlyIle-296
SEQ. ID. NO. 18878 319-SerThrGlnProSerSerThrGlnPro-327
a299
AMPHI Regions - AMPHI
SEQ. ID. NO. 18879 54-AlaSerProTrpMetLysLysLeuGlnSerValAlaGlnGlySer-68
SEQ. ID. NO. 18880 71-ThrPheArgIleLeuGlnIleGly-78
SEQ. ID. NO. 18881 85-AspPhePheThrAspSerLeuArgLysArgLeuGlnLysThrTrpGly-100
SEQ. ID. NO. 18882 238-GlnLeuThrGlnTrpSerLysTrp-245
SEQ. ID. NO. 18883 247-AlaAspArgMetAsnAspLeuAlaGlnThr-256
SEQ. ID. NO. 18884 281-GluGlnLysTrpLeuAspThrValArgGlnIleArgAspSerLeu-295
SEQ. ID. NO. 18885 307-GluSerLeuLysAsnThrLeu-313
SEQ. ID. NO. 18886 322-ArgLeuThrGluValGlnGlnMetGlnArgArgIleAlaArgGln-336
SEQ. ID. NO. 18887 375-TyrGlnArgSerAlaGluMetLeuAlaAspSerLeuGluGluLeuValArgSerAlaAlaIleArg-396
Antigenic Index - Jameson-Wolf
SEQ. ID. NO. 18888 1-MetAsnProLysHis-5
SEQ. ID. NO. 18889 35-ProSerAlaProTyrThrAspThrAsnGlyLeu-45
SEQ. ID. NO. 18890 48-AspTyrGlyAsnAlaSerAlaSerProTrpMetLysLysLeuGln-62
SEQ. ID. NO. 18891 65-AlaGlnGlySerGlyGluThr-71
SEQ. ID. NO. 18892 78-GlyAspSerHisThrAlaGlyAspPhePheThrAspSerLeuArgLysArgLeuGlnLysThrTrpGlyAspGlyGly-103
SEQ. ID. NO. 18893 110-AlaAsnValLysGlyGlnArg-116
SEQ. ID. NO. 18894 121-ArgHisAsnGlyAsnTrpGlnSerLeuThrSerArgAsnAsnThrGlyAspPheProLeu-140
SEQ. ID. NO. 18895 157-AlaSerAspGlyIleAlaSerLysGlnArgVal-167
SEQ. ID. NO. 18896 184-GlyAsnThrValSerAlaAsnGlyGlyGly-193
SEQ. ID. NO. 18897 221-GluAsnProAlaGlyGly-226
SEQ. ID. NO. 18898 241-GlnTrpSerLysTrpArgAlaAspArgMetAsnAspLeuAlaGlnThrGlyAla-258
SEQ. ID. NO. 18899 266-GlyThrAsnGluAlaPheGlyAspAsnIleAspIleAlaAspThrGluGlnLysTrp-284
SEQ. ID. NO. 18900 286-AspThrValArgGlnIleArgAspSerLeuPro-296
SEQ. ID. NO. 18901 305-AlaProGluSerLeuLysAsnThr-312
SEQ. ID. NO. 18902 319-ArgProValArgLeuThrGluValGlnGlnMetGlnArgArgIleAlaArgGlnGlyGlnThr-339
SEQ. ID. NO. 18903 361-GlyTrpAlaAlaLysAspGlyVal-368
SEQ. ID. NO. 18904 371-SerAlaLysGlyTyrGlnArgSerAlaGluMetLeuAlaAspSerLeuGluGluLeuValArg-391
SEQ. ID. NO. 18905 393-AlaAlaIleArgGln-397
Hydrophilic Regions - Hopp-Woods
SEQ. ID. NO. 18906 67-GlySerGlyGluThr-71
SEQ. ID. NO. 18907 90-SerLeuArgLysArgLeuGlnLysThrTrpGly-100
SEQ. ID. NO. 18908 112-ValLysGlyGlnArg-116
SEQ. ID. NO. 18909 130-ThrSerArgAsnAsnThrGly-136
SEQ. ID. NO. 18910 159-AspGlyIleAlaSerLysGlnArgVal-167
SEQ. ID. NO. 18911 245-TrpArgAlaAspArgMetAsnAsp-252
SEQ. ID. NO. 18912 270-AlaPheGlyAspAsnIleAspIleAlaAspThrGluGlnLysTrp-284
SEQ. ID. NO. 18913 288-ValArgGlnIleArgAspSerLeuPro-296
SEQ. ID. NO. 18914 319-ArgProValArgLeuThrGlu-325
SEQ. ID. NO. 18915 327-GlnGlnMetGlnArgArgIleAlaArgGlnGly-337
SEQ. ID. NO. 18916 363-AlaAlaLysAspGlyVal-368
SEQ. ID. NO. 18917 374-GlyTyrGlnArgSerAlaGluMetLeuAlaAspSerLeuGluGluLeuValArg-391
SEQ. ID. NO. 18918 393-AlaAlaIleArgGln-397
a302
AMPHI Regions - AMPHI
SEQ. ID. NO. 18919 20-AspGlyArgPheLeuArgThrValGluTrpLeuGlyAsnMetLeuProHisPro-37
SEQ. ID. NO. 18920 81-ValValSerLeuLeuAspAlaAspGlyLeuIleLysIleLeuThrHisThrValLysAsnPheThrGlyPheAlaProLeuGlyThrValLeuVal SerLeu-114
SEQ. ID. NO. 18921 127-SerAlaLeuMetArg-131
SEQ. ID. NO. 18922 176-GlyArgHisProLeuAlaGlyLeuAlaAlaAlaPheAlaGlyValSerGly-192
SEQ. ID. NO. 18923 201-GlyThrIleAspProLeuLeuAlaGlyIleThrGlnGlnAla-214
SEQ. ID. NO. 18924 239-ValIleAlaLeuIleGly-244
SEQ. ID. NO. 18925 271-ArgHisSerAsnGluIle-276
SEQ. ID. NO. 18926 294-LeuSerAlaLeuLeuAlaTrp-300
SEQ. ID. NO. 18927 308-IleLeuArgHisProGluThrGly-315
SEQ. ID. NO. 18928 341-TyrGlyArgValThrArgSerLeuArgGlyGluGlnGluValValAsnAlaMetAlaGluSerMetSer-363
SEQ. ID. NO. 18929 378-PheValAlaPhePheAsnTrpThrAsnIleGlyGlnTyrIle-391
SEQ. ID. NO. 18930 448-AlaProGluValIleGlnAlaAlaTyrArgIleGlyAspSerValThrAsnIleIleThrProMetMetSerTyrPheGlyLeuIleMetAla-478
SEQ. ID. NO. 18931 505-IleAlaTrpIleAlaLeuPheCysIle-513
Antigenic Index - Jameson-Wolf
SEQ. ID. NO. 18932 8-LysGluLysGlnMetSerGlnThrAspThrGlnArgAspGlyArgPhe-23
SEQ. ID. NO. 18933 61-SerValProAspProArgProValGlyAlaLysGlyArgAlaAspAspGlyLeu-78
SEQ. ID. NO. 18934 85-LeuAspAlaAspGlyLeu-90
SEQ. ID. NO. 18935 119-IleAlaGluLysSerGly-124
SEQ. ID. NO. 18936 134-LeuThrLysSerProArgLysLeuThr-142
SEQ. ID. NO. 18937 152-LeuSerAsnThrAlaSerGlu-158
SEQ. ID. NO. 18938 175-LeuGlyArgHisProLeu-180
SEQ. ID. NO. 18939 250-LysIleValGluProGlnLeuGlyProTyrGlnSerAspLeuSerGlnGluGluLysAspIleArgHisSerAsnGluIleThrProLeuGluTyrLys-282
SEQ. ID. NO. 18940 304-ProAlaAspGlyIleLeuArgHisProGluThrGlyLeuValSer-318
SEQ. ID. NO. 18941 343-ArgValThrArgSerLeuArgGlyGluGlnGluVal-354
SEQ. ID. NO. 18942 402-ValGlyLeuGlyGly-406
SEQ. ID. NO. 18943 482-LysTyrLysLysAspAlaGlyVal-489
Hydrophilic Regions - Hopp-Woods
SEQ. ID. NO. 18944 8-LysGluLysGlnMetSerGlnThrAspThrGlnArgAspGlyArgPhe-23
SEQ. ID. NO. 18945 63-ProAspProArgProValGlyAlaLysGlyArgAlaAspAspGlyLeu-78
SEQ. ID. NO. 18946 85-LeuAspAlaAspGlyLeu-90
SEQ. ID. NO. 18947 119-IleAlaGluLysSerGly-124

TABLE 1-continued

| | |
|---|---|
| SEQ. ID. NO. 18948 | 136-LysSerProArgLysLeu-141 |
| SEQ. ID. NO. 18949 | 263-LeuSerGlnGluGluLysAspIleArgHisSerAsnGlu-275 |
| SEQ. ID. NO. 18950 | 307-GlyIleLeuArgHisProGlu-313 |
| SEQ. ID. NO. 18951 | 343-ArgValThrArgSerLeuArgGlyGluGlnGluVal-354 |
| SEQ. ID. NO. 18952 | 482-LysTyrLysLysAspAlaGly-488 |
| a305 | |
| AMPHI Regions - AMPHI | |
| SEQ. ID. NO. 18953 | 10-LeuMetMetGlyLeuValGluGlyPheThrGluPheLeuPro-23 |
| SEQ. ID. NO. 18954 | 33-PheGlyAsnLeuIleAspPheHisSer-41 |
| SEQ. ID. NO. 18955 | 66-PheSerAsnValLeuHis-71 |
| SEQ. ID. NO. 18956 | 93-AlaAlaValMetGly-97 |
| SEQ. ID. NO. 18957 | 99-LeuPheGlyLysGlnIleLysGluTyrLeuPhe-109 |
| SEQ. ID. NO. 18958 | 141-AspValAspAlaLeuArgProIleAspAla-150 |
| SEQ. ID. NO. 18959 | 155-ValAlaGlnValPheAla-160 |
| SEQ. ID. NO. 18960 | 202-AlaTyrAspValLeuLysHisTyrArgPhePheThrLeuHis-215 |
| SEQ. ID. NO. 18961 | 222-IleGlyPheValAlaAlaPheValSer-230 |
| SEQ. ID. NO. 18962 | 235-ValLysAlaLeuLeuArg-240 |
| Antigenic Index - Jameson-Wolf | |
| SEQ. ID. NO. 18963 | 40-HisSerAsnHisLys-44 |
| SEQ. ID. NO. 18964 | 61-GluTyrArgGlnArgPheSerAsn-68 |
| SEQ. ID. NO. 18965 | 72-GlyValGlyLysAspArgLysAlaAsn-80 |
| SEQ. ID. NO. 18966 | 128-ValGluLysArgGlnSerArgAlaGluProLysIleValAsp-141 |
| SEQ. ID. NO. 18967 | 143-AspAlaLeuArgProIleAsp-149 |
| SEQ. ID. NO. 18968 | 163-ProGlyThrSerArgSerGlySer-170 |
| SEQ. ID. NO. 18969 | 180-IleGluArgLysThrAlaThr-186 |
| SEQ. ID. NO. 18970 | 241-PheValSerLysLysAsnTyr-247 |
| Hydrophilic Regions - Hopp-Woods | |
| SEQ. ID. NO. 18971 | 62-TyrArgGlnArgPhe-66 |
| SEQ. ID. NO. 18972 | 73-ValGlyLysAspArgLysAlaAsn-80 |
| SEQ. ID. NO. 18973 | 128-ValGluLysArgGlnSerArgAlaGluProLysIleValAsp-141 |
| SEQ. ID. NO. 18974 | 143-AspAlaLeuArgProIleAsp-149 |
| SEQ. ID. NO. 18975 | 165-ThrSerArgSerGlySer-170 |
| SEQ. ID. NO. 18976 | 180-IleGluArgLysThrAlaThr-186 |
| SEQ. ID. NO. 18977 | 242-ValSerLysLysAsn-246 |
| a308-2 | |
| AMPHI Regions - AMPHI | |
| SEQ. ID. NO. 18978 | 6-PheTyrArgIleLeuGlyValAlaAspAsnLeuTyrProTyrLeu-20 |
| SEQ. ID. NO. 18979 | 27-ThrIleIleAlaGlyLeu-32 |
| SEQ. ID. NO. 18980 | 64-AlaLeuGluLeuLeuArgAlaGlnAsp-72 |
| SEQ. ID. NO. 18981 | 83-AlaGluMetAlaArgAlaSerGlu-90 |
| SEQ. ID. NO. 18982 | 101-LeuAlaAspPheValHisProIleGlyAsnIleGlyAlaCys-114 |
| SEQ. ID. NO. 18983 | 131-SerMetArgThrLeuAlaSerValValHisGlyPheGlyAsp-144 |
| SEQ. ID. NO. 18984 | 172-LeuAlaHisLeuAspAsnMetLysArgValThrGlu-183 |
| Antigenic Index - Jameson-Wolf | |
| SEQ. ID. NO. 18985 | 39-TrpGluArgArgMetMetVal-45 |
| SEQ. ID. NO. 18986 | 68-LeuArgAlaGlnAspIleGluThr-75 |
| SEQ. ID. NO. 18987 | 80-SerLysGlyAlaGluMetAlaArgAlaSerGluThrAlaTyrAlaArgAspGluVal-98 |
| SEQ. ID. NO. 18988 | 118-GlyThrPheLysThrAspGlyMet-125 |
| SEQ. ID. NO. 18989 | 142-PheGlyAspAsnLeuLeu-147 |
| SEQ. ID. NO. 18990 | 149-ArgAlaAlaAspValValLeuLysGluArgArgArgLeu-161 |
| SEQ. ID. NO. 18991 | 166-ArgGluThrProLeu-170 |
| SEQ. ID. NO. 18992 | 176-AspAsnMetLysArgValThrGluMetGly-185 |
| SEQ. ID. NO. 18993 | 195-MetTyrArgLysProGlnThrAlaAspAspIleVal-206 |
| SEQ. ID. NO. 18994 | 219-IleAspThrProAspSerAlaGlu-226 |
| Hydrophilic Regions - Hopp-Woods | |
| SEQ. ID. NO. 18995 | 39-TrpGluArgArgMetMetVal-45 |
| SEQ. ID. NO. 18996 | 68-LeuArgAlaGlnAspIleGluThr-75 |
| SEQ. ID. NO. 18997 | 81-LysGlyAlaGluMetAlaArgAlaSerGlu-90 |
| SEQ. ID. NO. 18998 | 92-AlaTyrAlaArgAspGluVal-98 |
| SEQ. ID. NO. 18999 | 120-PheLysThrAspGly-124 |
| SEQ. ID. NO. 19000 | 149-ArgAlaAlaAspValValLeuLysGluArgArgArgLeu-161 |
| SEQ. ID. NO. 19001 | 176-AspAsnMetLysArgValThrGlu-183 |
| SEQ. ID. NO. 19002 | 195-MetTyrArgLysProGlnThrAlaAspAspIleVal-206 |
| SEQ. ID. NO. 19003 | 220-AspThrProAspSerAlaGlu-226 |
| a311-1 | |
| AMPHI Regions - AMPHI | |
| SEQ. ID. NO. 19004 | 7-SerHisTrpArgValLeuAlaGluLeuAlaAspGlyLeuProGlnHisValSerGlnLeuAlaArgMetAlaAsp-31 |
| SEQ. ID. NO. 19005 | 37-LeuAsnGlyPheTrpGlnGlnMetProAlaHisIleArgGlyLeuLeuArg-53 |
| SEQ. ID. NO. 19006 | 55-HisAspGlyTyrTrpArgLeuValArgProLeuAlaValPheAspAlaGluGlyLeuArgGluLeuGly-77 |
| SEQ. ID. NO. 19007 | 124-ArgGlnGlyArgLysTrpSerHisArgLeu-133 |
| SEQ. ID. NO. 19008 | 165-ArgAlaLeuSerArgLeu-170 |
| SEQ. ID. NO. 19009 | 219-ValGluAsnAlaAlaSerValGlnSerLeuPheGln-230 |
| SEQ. ID. NO. 19010 | 245-GluThrLeuLeuAlaGlu-250 |
| SEQ. ID. NO. 19011 | 291-PheGluGlyThrValLysGlyValAspGlyGlnGlyVal-303 |
| SEQ. ID. NO. 19012 | 362-ThrValGlySerAlaProTyrArgAspLeuSerProLeu-374 |
| SEQ. ID. NO. 19013 | 376-AlaGluTrpAlaGluLysVal-382 |
| SEQ. ID. NO. 19014 | 391-CysAlaValCysGlyGluPheLysLys-399 |
| SEQ. ID. NO. 19015 | 426-TyrArgHisProGluGluHisGlySerAspArgTrpPheAsnAlaLeuGlySer-443 |
| SEQ. ID. NO. 19016 | 493-AsnLeuAsnArgHisAla-498 |
| SEQ. ID. NO. 19017 | 511-AlaValAlaSerGlyMetMetAspAlaValCys-521 |

TABLE 1-continued

| | |
|---|---|
| SEQ. ID. NO. 19018 | 550-AlaAlaLysValAlaGluAlaLeuProPro-559 |
| SEQ. ID. NO. 19019 | 576-HisGlyLeuLeuAsnLeu-581 |
| AntigenicIndex -Jameson-Wolf | |
| SEQ. ID. NO. 19020 | 28-ArgMetAlaAspMetLysProGlnGln-36 |
| SEQ. ID. NO. 19021 | 50-GlyLeuLeuArgGlnHisAspGlyTyr-58 |
| SEQ. ID. NO. 19022 | 71-GluGlyLeuArgGluLeuGlyGluArgSerGlyPhe-82 |
| SEQ. ID. NO. 19023 | 86-LeuLysHisGluCysAlaSerSerAsnAspGluIleLeuGlu-99 |
| SEQ. ID. NO. 19024 | 102-ArgIleAlaProAspLysAlaHisLys-110 |
| SEQ. ID. NO. 19025 | 116-HisLeuGlnSerLysGlyArgGlyArgGlnGlyArgLysTrpSerHisArgLeuGlyGlu-135 |
| SEQ. ID. NO. 19026 | 145-PheAspArgProGlnTyrGluLeuGlySer-154 |
| SEQ. ID. NO. 19027 | 162-AlaCysArgArgAlaLeuSer-168 |
| SEQ. ID. NO. 19028 | 174-ThrGlnIleLysTrpProAsn-180 |
| SEQ. ID. NO. 19029 | 182-LeuValValGlyArgAspLysLeuGly-190 |
| SEQ. ID. NO. 19030 | 196-ThrValArgThrGlyGlyLysThrVal-204 |
| SEQ. ID. NO. 19031 | 215-LeuProLysGluValGluAsn-221 |
| SEQ. ID. NO. 19032 | 231-ThrAlaSerArgArgGlyAsnAlaAsp-239 |
| SEQ. ID. NO. 19033 | 258-TyrAlaArgAspGlyPheAla-264 |
| SEQ. ID. NO. 19034 | 272-AlaAlaAsnArgAspHisGlyLys-279 |
| SEQ. ID. NO. 19035 | 284-LeuArgAspGlyGluThrValPhe-291 |
| SEQ. ID. NO. 19036 | 293-GlyThrValLysGlyValAspGlyGlnGly-302 |
| SEQ. ID. NO. 19037 | 307-GluThrAlaGluGlyLysGlnThrValValSerGlyGluIleSerLeuArgSerAspAspArgProValSerValProLysArgArgAspSerGluArg-339 |
| SEQ. ID. NO. 19038 | 344-AspGlyGlyAsnSerArgLeu-350 |
| SEQ. ID. NO. 19039 | 364-GlySerAlaProTyrArgAspLeuSerProLeuGly-375 |
| SEQ. ID. NO. 19040 | 378-TrpAlaGluLysValAspGlyAsnValArgIle-388 |
| SEQ. ID. NO. 19041 | 395-GlyGluPheLysLysAlaGlnValGln-403 |
| SEQ. ID. NO. 19042 | 405-GlnLeuAlaArgLysIleGlu-411 |
| SEQ. ID. NO. 19043 | 424-AsnHisTyrArgHisProGluGluHisGlySerAspArgTrp-437 |
| SEQ. ID. NO. 19044 | 440-AlaLeuGlySerArgArgPheSerArgAsnAla-450 |
| SEQ. ID. NO. 19045 | 464-AlaLeuThrAspAspGlyHisTyrLeuGly-473 |
| SEQ. ID. NO. 19046 | 483-MetLysGluSerLeuAla-488 |
| SEQ. ID. NO. 19047 | 492-AlaAsnLeuAsnArgHisAlaGlyLysArgTyrPro-503 |
| SEQ. ID. NO. 19048 | 529-GlyArgLeuLysGluLysThrGlyAlaGlyLysProVal-541 |
| SEQ. ID. NO. 19049 | 547-GlyGlyGlyAlaAlaLysValAlaGlu-555 |
| SEQ. ID. NO. 19050 | 565-AsnThrValArgValAlaAsp-571 |
| SEQ. ID. NO. 19051 | 584-AlaGluGlyGlyGluSerGluHisThr-592 |
| Hydrophilic Regions -Hopp-Woods | |
| SEQ. ID. NO. 19052 | 28-ArgMetAlaAspMetLysProGlnGln-36 |
| SEQ. ID. NO. 19053 | 50-GlyLeuLeuArgGlnHis-55 |
| SEQ. ID. NO. 19054 | 71-GluGlyLeuArgGluLeuGlyGluArgSerGlyPhe-82 |
| SEQ. ID. NO. 19055 | 86-LeuLysHisGluCysAlaSerSerAsnAspGluIleLeuGlu-99 |
| SEQ. ID. NO. 19056 | 102-ArgIleAlaProAspLysAlaHisLys-110 |
| SEQ. ID. NO. 19057 | 118-GlnSerLysGlyArgGlyArgGlnGlyArgLysTrpSerHisArgLeuGlyGlu-135 |
| SEQ. ID. NO. 19058 | 162-AlaCysArgArgAlaLeuSer-168 |
| SEQ. ID. NO. 19059 | 183-ValValGlyArgAspLysLeuGly-190 |
| SEQ. ID. NO. 19060 | 196-ThrValArgThrGlyGlyLys-202 |
| SEQ. ID. NO. 19061 | 217-LysGluValGluAsn-221 |
| SEQ. ID. NO. 19062 | 232-AlaSerArgArgGlyAsnAlaAsp-239 |
| SEQ. ID. NO. 19063 | 259-AlaArgAspGlyPhe-263 |
| SEQ. ID. NO. 19064 | 272-AlaAlaAsnArgAspHisGlyLys-279 |
| SEQ. ID. NO. 19065 | 285-ArgAspGlyGluThrValPhe-291 |
| SEQ. ID. NO. 19066 | 293-GlyThrValLysGlyValAspGly-300 |
| SEQ. ID. NO. 19067 | 307-GluThrAlaGluGlyLysGlnThrValVal-316 |
| SEQ. ID. NO. 19068 | 320-IleSerLeuArgSerAspAspArgProValSerValProLysArgArgAspSerGluArg-339 |
| SEQ. ID. NO. 19069 | 346-GlyAsnSerArgLeu-350 |
| SEQ. ID. NO. 19070 | 367-ProTyrArgAspLeuSer-372 |
| SEQ. ID. NO. 19071 | 378-TrpAlaGluLysValAspGlyAsnVal-386 |
| SEQ. ID. NO. 19072 | 395-GlyGluPheLysLysAlaGlnVal-402 |
| SEQ. ID. NO. 19073 | 405-GlnLeuAlaArgLysIleGlu-411 |
| SEQ. ID. NO. 19074 | 424-AsnHisTyrArgHisProGluGluHisGlySer-434 |
| SEQ. ID. NO. 19075 | 442-GlySerArgArgPheSerArg-448 |
| SEQ. ID. NO. 19076 | 464-AlaLeuThrAspAspGlyHis-470 |
| SEQ. ID. NO. 19077 | 483-MetLysGluSerLeuAla-488 |
| SEQ. ID. NO. 19078 | 493-AsnLeuAsnArgHisAlaGlyLysArgTyrPro-503 |
| SEQ. ID. NO. 19079 | 529-GlyArgLeuLysGluLysThrGlyAlaGlyLysProVal-541 |
| SEQ. ID. NO. 19080 | 549-GlyAlaAlaLysValAlaGlu-555 |
| SEQ. ID. NO. 19081 | 565-AsnThrValArgValAlaAsp-571 |
| SEQ. ID. NO. 19082 | 585-GluGlyGlyGluSerGluHisThr-592 |
| a312 | |
| AMPHIRegions - AMPHI | |
| SEQ. ID. NO. 19083 | 6-GlyGluIleLeuGluThrValLysMetValAla-16 |
| SEQ. ID. NO. 19084 | 44-GlnAsnIleTyrAsnLysIleThrThrValGlyLys-55 |
| SEQ. ID. NO. 19085 | 82-IleAlaGlnIleAlaAlaAlaThr-89 |
| SEQ. ID. NO. 19086 | 95-ValSerValAlaGlnThrLeuAspLysAlaAlaLys-106 |
| SEQ. ID. NO. 19087 | 109-GlyValSerPheIleGlyGlyPheSerAlaLeuValGln-121 |
| SEQ. ID. NO. 19088 | 133-ArgSerIleProGluAlaMetLysThr-141 |
| SEQ. ID. NO. 19089 | 167-GlyGluThrIleLysArgThr-173 |
| SEQ. ID. NO. 19090 | 182-GlyCysAlaLysIleValValPheCys-190 |
| SEQ. ID. NO. 19091 | 230-SerAspAlaThrThrLeuThrGluValAlaGluValValLysLys-244 |
| SEQ. ID. NO. 19092 | 249-IleThrArgValGlyGluLeuIleGlyArgGluAlaSerLys-262 |
| SEQ. ID. NO. 19093 | 281-ValGlyAspSerValAlaArgIleLeuGluGluMetGly-293 |

TABLE 1-continued

| | |
|---|---|
| SEQ. ID. NO. 19094 | 309-LeuAsnAspAlaVal-313 |
| SEQ. ID. NO. 19095 | 322-SerAlaValGlyGlyLeuSerGly-329 |
| SEQ. ID. NO. 19096 | 349-LeuThrLeuAspLysLeuGluAlaMetThrAla-359 |
| SEQ. ID. NO. 19097 | 374-ThrProAlaHisThrIleSerGlyIleIle-383 |
| SEQ. ID. NO. 19098 | 409-ValGlyAspSerValGluPheGlyGlyLeuLeuGly-420 |
| Antigenic Index - Jameson-Wolf | |
| SEQ. ID. NO. 19099 | 4-GlnSerGlyGluIleLeuGlu-10 |
| SEQ. ID. NO. 19100 | 13-LysMetValAlaAspGlnAsnPheAspVal-22 |
| SEQ. ID. NO. 19101 | 35-IleSerThrAspIleAspVal-41 |
| SEQ. ID. NO. 19102 | 52-ThrValGlyLysAspLeuValAla-59 |
| SEQ. ID. NO. 19103 | 89-ThrHisAlaAspSer-93 |
| SEQ. ID. NO. 19104 | 100-ThrLeuAspLysAlaAlaLys-106 |
| SEQ. ID. NO. 19105 | 121-GlnLysGlyMetSerProSerAspGluValLeu-131 |
| SEQ. ID. NO. 19106 | 134-SerIleProGluAlaMetLysThrThrAsp-143 |
| SEQ. ID. NO. 19107 | 152-GlySerThrArgAla-156 |
| SEQ. ID. NO. 19108 | 161-AspAlaValArgLeuAlaGlyGluThrIleLysArgThrAlaGluIleThr-177 |
| SEQ. ID. NO. 19109 | 192-AlaValGluAspAsnProPhe-198 |
| SEQ. ID. NO. 19110 | 204-HisGlySerGlyGluAlaAspAla-211 |
| SEQ. ID. NO. 19111 | 225-AlaAlaLeuGluAsnSerAspAla-232 |
| SEQ. ID. NO. 19112 | 237-GluValAlaGluValValLys-243 |
| SEQ. ID. NO. 19113 | 251-ArgValGlyGluLeuIleGlyArgGluAlaSerLys-262 |
| SEQ. ID. NO. 19114 | 280-AlaValGlyAspSerValAlaArgIleLeuGlu-290 |
| SEQ. ID. NO. 19115 | 311-AspAlaValLysLysGlyGlyMet-318 |
| SEQ. ID. NO. 19116 | 334-ValSerGluAspGluGlyMet-340 |
| SEQ. ID. NO. 19117 | 352-AspLysLeuGluAla-356 |
| SEQ. ID. NO. 19118 | 370-ValProGlyAspThrProAla-376 |
| SEQ. ID. NO. 19119 | 383-IleAlaAspGluAlaAla-388 |
| SEQ. ID. NO. 19120 | 392-IleAsnSerLysThrThrAla-398 |
| SEQ. ID. NO. 19121 | 405-ThrGlyLysThrValGlyAspSerValGlu-414 |
| SEQ. ID. NO. 19122 | 426-ProValLysGluGlySerCys-432 |
| SEQ. ID. NO. 19123 | 435-PheValAsnArgGlyGlyArgIle-442 |
| SEQ. ID. NO. 19124 | 447-GlnSerMetLysAsn-451 |
| Hydrophilic Regions- Hopp-Woods | |
| SEQ. ID. NO. 19125 | 18-GlnAsnPheAspVal-22 |
| SEQ. ID. NO. 19126 | 35-IleSerThrAspIleAspVal-41 |
| SEQ. ID. NO. 19127 | 52-ThrValGlyLysAspLeuValAla-59 |
| SEQ. ID. NO. 19128 | 100-ThrLeuAspLysAlaAlaLys-106 |
| SEQ. ID. NO. 19129 | 123-GlyMetSerProSerAspGluValLeu-131 |
| SEQ. ID. NO. 19130 | 134-SerIleProGluAlaMetLysThrThrAsp-143 |
| SEQ. ID. NO. 19131 | 161-AspAlaValArgLeuAlaGlyGluThrIleLysArgThrAlaGluIleThr-177 |
| SEQ. ID. NO. 19132 | 192-AlaValGluAspAsnPro-197 |
| SEQ. ID. NO. 19133 | 207-GlyGluAlaAspAla-211 |
| SEQ. ID. NO. 19134 | 225-AlaAlaLeuGluAsnSerAspAla-232 |
| SEQ. ID. NO. 19135 | 237-GluValAlaGluValValLys-243 |
| SEQ. ID. NO. 19136 | 251-ArgValGlyGluLeuIleGlyArgGluAlaSerLys-262 |
| SEQ. ID. NO. 19137 | 284-SerValAlaArgIleLeuGlu-290 |
| SEQ. ID. NO. 19138 | 311-AspAlaValLysLysGlyGlyMet-318 |
| SEQ. ID. NO. 19139 | 334-ValSerGluAspGluGlyMet-340 |
| SEQ. ID. NO. 19140 | 352-AspLysLeuGluAla-356 |
| SEQ. ID. NO. 19141 | 383-IleAlaAspGluAlaAla-388 |
| SEQ. ID. NO. 19142 | 408-ThrValGlyAspSerValGlu-414 |
| SEQ. ID. NO. 19143 | 426-ProValLysGluGlySerCys-432 |
| SEQ. ID. NO. 19144 | 438-ArgGlyGlyArgIle-442 |
| SEQ. ID. NO. 19145 | 447-GlnSerMetLysAsn-451 |
| a313-2 | |
| AMPHI Regions - AMPHI | |
| SEQ. ID. NO. 19146 | 27-GlyMetAspAspProArgThrTyrGlySerGly-37 |
| SEQ. ID. NO. 19147 | 41-AlaThrAsnValLeu-45 |
| SEQ. ID. NO. 19148 | 60-AspAlaAlaLysGly-64 |
| SEQ. ID. NO. 19149 | 66-ValAlaValLeuLeuAlaArgValLeuGlnGluPro-77 |
| SEQ. ID. NO. 19150 | 88-ValAlaLeuAlaAlaLeuValGlyHisMetTrpPro-99 |
| SEQ. ID. NO. 19151 | 143-SerLeuAlaAlaLeuThrAlaThrIleAlaAlaProLeuAlaAla-157 |
| Antigenic Index - Jameson-Wolf | |
| SEQ. ID. NO. 19152 | 26-TyrGlyMetAspAspProArgThrTyrGlySerGlyAsnProGlyAla-41 |
| SEQ. ID. NO. 19153 | 46-ArgSerGlyLysLysLysAlaAla-53 |
| SEQ. ID. NO. 19154 | 73-ValLeuGlnGluProLeuGlyLeuSerAspSerAla-84 |
| SEQ. ID. NO. 19155 | 104-PheLysGlyGlyLysGlyVal-110 |
| SEQ. ID. NO. 19156 | 180-ArgHisLysSerAsn-184 |
| SEQ. ID. NO. 19157 | 189-IleLysGlyLysGluSerLysIleGlyGluLysArg-200 |
| Hydrophilic Regions - Hopp-Woods | |
| SEQ. ID. NO. 19158 | 26-TyrGlyMetAspAspProArgThrTyrGly-35 |
| SEQ. ID. NO. 19159 | 46-ArgSerGlyLysLysLysAlaAla-53 |
| SEQ. ID. NO. 19160 | 105-LysGlyGlyLysGlyVal-110 |
| SEQ. ID. NO. 19161 | 189-IleLysGlyLysGluSerLysIleGlyGluLysArg-200 |
| a401 | |
| AMPHI Regions - AMPHI | |
| SEQ. ID. NO. 19162 | 44-SerGlyValLysProTyrAsnAlaLeu-52 |
| SEQ. ID. NO. 19163 | 65-CysTyrAsnCysHisSerGlnMetIleArgProPheArg-77 |
| SEQ. ID. NO. 19164 | 112-ValGlyGlyArgTyrSerAspGluTrpHisArgIle-123 |

TABLE 1-continued

SEQ. ID. NO. 19165 157-MetLysAlaLeuArgLysValGlyThr-165
SEQ. ID. NO. 19166 172-IleAlaLysAlaProGluAlaLeu-179
Antigenic Index - Jameson-Wolf
SEQ. ID. NO. 19167 5-GlnLeuAlaGluGluLysIle-11
SEQ. ID. NO. 19168 38-AlaAlaThrGlnProAlaSerGlyValLysProTyrAsn-50
SEQ. ID. NO. 19169 55-AlaGlyArgAspIleTyrIleArgGluGlyCysTyrAsnCysHis-69
SEQ. ID. NO. 19170 74-ArgProPheArgAlaGluThrGluArgTyrGlyHis-85
SEQ. ID. NO. 19171 90-GlyGluSerValTyr-94
SEQ. ID. NO. 19172 98-PheGlnTrpGlySerLysArgThrGlyProAspLeuAlaArgValGlyGlyArgTyrSerAspGluTrpHis-121
SEQ. ID. NO. 19173 125-LeuLeuAsnProArgAspValValProGluSerAsnMetPro-138
SEQ. ID. NO. 19174 146-AsnLysValAspValAspAla-152
SEQ. ID. NO. 19175 158-LysAlaLeuArgLysValGlyThrProTyrSerAspGluGluIleAlaLysAlaProGlu-177
SEQ. ID. NO. 19176 179-LeuAlaAsnLysSerGluLeuAspAla-187
Hydrophilic Regions - Hopp-Woods
SEQ. ID. NO. 19177 5-GlnLeuAlaGluGluLysIle-11
SEQ. ID. NO. 19178 76-PheArgAlaGluThrGluArgTyrGly-84
SEQ. ID. NO. 19179 101-GlySerLysArgThrGlyProAspLeuAlaArgValGlyGlyArgTyrSerAspGluTrpHis-121
SEQ. ID. NO. 19180 127-AsnProArgAspValValPro-133
SEQ. ID. NO. 19181 146-AsnLysValAspValAspAla-152
SEQ. ID. NO. 19182 158-LysAlaLeuArgLysValGly-164
SEQ. ID. NO. 19183 167-TyrSerAspGluGluIleAlaLysAlaProGlu-177
SEQ. ID. NO. 19184 179-LeuAlaAsnLysSerGluLeuAspAla-187
a402
AMPHI Regions - AMPHI
SEQ. ID. NO. 19185 18-PheLeuSerGlyLeu-22
SEQ. ID. NO. 19186 85-AlaGlyIleAlaAspPhe-90
SEQ. ID. NO. 19187 100-ThrGlyPheSerGlyPheValHis-107
SEQ. ID. NO. 19188 117-AlaValValArgGlyLeu-122
SEQ. ID. NO. 19189 136-LysSerGlyArgGln-140
SEQ. ID. NO. 19190 146-PheAlaAsnValAlaGly-151
SEQ. ID. NO. 19191 218-ValPheGlnAsnIleAlaAspArgProAspArgLeuIle-230
SEQ. ID. NO. 19192 261-AspValPheAsnSerValAsnGlyIleGlu-270
SEQ. ID. NO. 19193 279-LysSerGlyIleArg-283
SEQ. ID. NO. 19194 294-SerTrpAlaArgValLeuSerAlaIleProGluMetGln-306
SEQ. ID. NO. 19195 344-ArgLysTrpLeuArgArgHisPro-351
SEQ. ID. NO. 19196 376-AlaGluPheLeuLysGlnValGlnSerHisLeu-386
SEQ. ID. NO. 19197 398-HisSerProHisAlaPheAlaThrAlaValHisSerIlePro-411
SEQ. ID. NO. 19198 437-GlnArgLeuSerArgLeu-442
SEQ. ID. NO. 19199 460-AlaAlaGlnLysVal-464
Antigenic Index - Jameson-Wolf
SEQ. ID. NO. 19200 4-ValAsnThrLysProAsnThrSer-11
SEQ. ID. NO. 19201 66-ArgIleCysArgSerArgPheValAsp-74
SEQ. ID. NO. 19202 130-ValGlyThrAspGlyAsnLysSerGlyArgGlnValSer-142
SEQ. ID. NO. 19203 222-IleAlaAspArgProAspArgLeuIleGluAsnLysHisGly-235
SEQ. ID. NO. 19204 240-TyrHisArgAspGlyAspLysValVal-248
SEQ. ID. NO. 19205 264-AsnSerValAsnGlyIleGluArg-271
SEQ. ID. NO. 19206 277-SerLeuLysSerGlyIleArgArg-284
SEQ. ID. NO. 19207 321-IleAlaAspGluProGln-326
SEQ. ID. NO. 19208 331-LeuGlnAspLysArgValGluIleValLeuAspAspGlyArgLysTrpLeuArgArgHisProAspGluLysPheAsp-356
SEQ. ID. NO. 19209 385-HisLeuThrProAspGly-390
SEQ. ID. NO. 19210 429-PheProAsnLysGluLeuLeuLysGlnArgLeuSer-440
SEQ. ID. NO. 19211 444-TrpProGluSerGlyArgHisValPheAspSerSerThrVal-457
SEQ. ID. NO. 19212 472-MetThrGluProSerAlaGly-478
SEQ. ID. NO. 19213 481-ValIleThrAspAspAsnMet-487
SEQ. ID. NO. 19214 489-ValGluTyrLysTyrGlyArgGlyIle-497
Hydrophilic Regions - Hopp-Woods
SEQ. ID. NO. 19215 131-GlyThrAspGlyAsnLysSerGlyArgGlnVal-141
SEQ. ID. NO. 19216 222-IleAlaAspArgProAspArgLeuIleGluAsnLysHis-234
SEQ. ID. NO. 19217 241-HisArgAspGlyAspLysValVal-248
SEQ. ID. NO. 19218 278-LeuLysSerGlyIleArg-283
SEQ. ID. NO. 19219 321-IleAlaAspGluProGln-326
SEQ. ID. NO. 19220 331-LeuGlnAspLysArgValGluIleValLeuAspAspGlyArgLysTrpLeuArgArgHisProAspGluLysPheAsp-356
SEQ. ID. NO. 19221 430-ProAsnLysGluLeuLeuLysGlnArgLeuSer-440
SEQ. ID. NO. 19222 446-GluSerGlyArgHisValPhe-452
SEQ. ID. NO. 19223 473-ThrGluProSerAlaGly-478
SEQ. ID. NO. 19224 481-ValIleThrAspAspAsnMet-487
a501
AMPHI Regions - AMPHI
SEQ. ID. NO. 19225 63-ValGluValLeuGlnGluLeuPheArgGlnTyrArgValAlaArgGlnLeu-79
SEQ. ID. NO. 19226 88-ValPheAlaAlaPheGlnAlaVal-95
SEQ. ID. NO. 19227 97-PheGlnGlyPheAspAsnGlyPhe-104
SEQ. ID. NO. 19228 126-AlaAspAlaPheGlnGly-131
SEQ. ID. NO. 19229 139-ValPheGluValValGlyAspIleThrArgArgThrThrGluAla-153
SEQ. ID. NO. 19230 183-AspGlyPheThrArgIleAsnArgCysGlyGlnCys-194
SEQ. ID. NO. 19231 196-HisAlaPheGlyAspPheIleAsp-203
SEQ. ID. NO. 19232 252-AlaPheAlaGlyGlnVal-257
SEQ. ID. NO. 19233 270-HisHisAspPheTyrArgCysPheArgHisValValGlnSerAsnIleGlyAsnLeu-288
SEQ. ID. NO. 19234 306-TyrGlyAsnPheLeuThrValPheGlnGlnPheGlyCys-318
SEQ. ID. NO. 19235 364-GlyAsnGlnTyrValAlaGlyPhe-371
SEQ. ID. NO. 19236 438-AlaSerProPheAsp-442

TABLE 1-continued

| | |
|---|---|
| SEQ. ID. NO. 19237 | 458-ArgGlnLeuGlyAspPhe-463 |
| SEQ. ID. NO. 19238 | 511-PheGlnArgGlyPheGluHisIleGlu-519 |
| SEQ. ID. NO. 19239 | 528-TyrAspValPheAlaGln-533 |
| Antigenic Index - Jameson-Wolf | |
| SEQ. ID. NO. 19240 | 6-LeuThrAlaAspAla-10 |
| SEQ. ID. NO. 19241 | 17-AlaAlaGlyGlyAspGlyLysVal-24 |
| SEQ. ID. NO. 19242 | 26-HisHisPheAspGly-30 |
| SEQ. ID. NO. 19243 | 46-ValGluThrGluGlyGln-51 |
| SEQ. ID. NO. 19244 | 56-ValArgAlaAspGlyGluAlaValGluVal-65 |
| SEQ. ID. NO. 19245 | 100-PheAspAsnGlyPhe-104 |
| SEQ. ID. NO. 19246 | 108-GlnSerAlaAspGluArgAsnHisAspPheAsnValGlyGln-121 |
| SEQ. ID. NO. 19247 | 144-GlyAspIleThrArgArgThrThrGluAlaGlnHis-155 |
| SEQ. ID. NO. 19248 | 179-GlyHisThrAspAspGlyPheThrArgIleAsnArgCysGlyGlnCys-l94 |
| SEQ. ID. NO. 19249 | 202-IleAspValGluValAspArgGlyArgValThrGlyAspThrAlaGlyAsnPhe-219 |
| SEQ. ID. NO. 19250 | 230-GlnGlnGlyPheGlyValAspThrAspLeuAlaValAspAspLysPheHisThrArgGlnAlaAsp-251 |
| SEQ. ID. NO. 19251 | 257-ValGlyGluAlaGluCysGluPheGly-265 |
| SEQ. ID. NO. 19252 | 269-ValHisHisAspPheTyrArgCys-276 |
| SEQ. ID. NO. 19253 | 294-GlyValAspGluAlaGly-299 |
| SEQ. ID. NO. 19254 | 320-AlaAlaAlaAspAsnGlyArgAsnThrGlnPheAlaArgAspAspGlyGlyValAlaGlyThrSerAlaProValGlyHisAspGlyGlySer-350 |
| SEQ. ID. NO. 19255 | 405-ValAspArgLysAlaAla-410 |
| SEQ. ID. NO. 19256 | 420-PheAspGlyPheGlyThrGlyLeuGlnAsp-429 |
| SEQ. ID. NO. 19257 | 439-SerProPheAspValHisArg-445 |
| SEQ. ID. NO. 19258 | 477-AspIleAspValGlyTyr-482 |
| SEQ. ID. NO. 19259 | 490-ValGlyLysAsnHisPheAsp-496 |
| SEQ. ID. NO. 19260 | 502-PheAlaGlnAspGlyArgPhe-508 |
| SEQ. ID. NO. 19261 | 512-GlnArgGlyPheGluHis-517 |
| SEQ. ID. NO. 19262 | 535-ValGlySerAspLysAspAspLeuVal-543 |
| SEQ. ID. NO. 19263 | 548-GlyIleGluGlyGluHisHisThr-555 |
| Hydrophilic Regions - Hopp-Woods | |
| SEQ. ID. NO. 19264 | 6-LeuThrAlaAspAla-10 |
| SEQ. ID. NO. 19265 | 19-GlyGlyAspGlyLysVal-24 |
| SEQ. ID. NO. 19266 | 46-ValGluThrGluGlyGln-51 |
| SEQ. ID. NO. 19267 | 56-ValArgAlaAspGlyGluAlaValGluVal-65 |
| SEQ. ID. NO. 19268 | 108-GlnSerAlaAspGluArgAsnHisAsp-116 |
| SEQ. ID. NO. 19269 | 144-GlyAspIleThrArgArgThrThrGluAlaGlnHis-155 |
| SEQ. ID. NO. 19270 | 179-GlyHisThrAspAspGlyPheThrArgIleAsnArg-l90 |
| SEQ. ID. NO. 19271 | 202-IleAspValGluValAspArgGlyArgValThrGlyAspThr-215 |
| SEQ. ID. NO. 19272 | 237-ThrAspLeuAlaValAspAspLysPheHisThrArgGlnAlaAsp-251 |
| SEQ. ID. NO. 19273 | 257-ValGlyGluAlaGluCysGluPheGly-265 |
| SEQ. ID. NO. 19274 | 294-GlyValAspGluAlaGly-299 |
| SEQ. ID. NO. 19275 | 323-AspAsnGlyArgAsnThrGlnPheAlaArgAspAspGlyGlyVal-337 |
| SEQ. ID. NO. 19276 | 344-ValGlyHisAspGly-348 |
| SEQ. ID. NO. 19277 | 405-ValAspArgLysAlaAla-410 |
| SEQ. ID. NO. 19278 | 535-ValGlySerAspLysAspAspLeuVal-543 |
| SEQ. ID. NO. 19279 | 549-1leGluGlyGluHisHisThr-555 |
| a502-l | |
| AMPHI Regions - AMPHI | |
| SEQ. ID. NO. 19280 | 6-AsnLeuPheGlnPheLeuAlaVal-13 |
| SEQ. ID. NO. 19281 | 26-GlyAlaValAspAlaLeuLysGlnPheAsnAsnAspAlaAspGlyIleSerGlySerPheThrGln-47 |
| SEQ. ID. NO. 19282 | 98-GlnValThrLysSerSerGlnAsp-105 |
| Antigenic Index - Jameson-Wolf | |
| SEQ. ID. NO. 19283 | 32-LysGlnPheAsnAsnAspAlaAspGlyIleSerGlySer-44 |
| SEQ. ID. NO. 19284 | 48-ThrValGlnSerLysLysLysThrGlnThrAlaHisGlyThr-61 |
| SEQ. ID. NO. 19285 | 74-TyrThrSerProTyrLysGlnThrIle-82 |
| SEQ. ID. NO. 19286 | 98-GlnValThrLysSerSerGlnAspGlnAlaIleGlyGlySerPro-112 |
| SEQ. ID. NO. 19287 | 116-LeuSerAsnLysThrAlaLeuGluSerSerTyrThrLeuLysGluAspGlySerSerAsnGly-136 |
| SEQ. ID. NO. 19288 | 142-AlaThrProLysArgAsnAsnAlaGly-150 |
| SEQ. ID. NO. 19289 | 158-PheLysGlyGlyAsn-162 |
| SEQ. ID. NO. 19290 | 167-GlnLeuLysAspSerPheGlyAsnGlnThr-176 |
| SEQ. ID. NO. 19291 | 184-AsnThrAsnProGlnLeuSerArgGlyAlaPhe-194 |
| SEQ. ID. NO. 19292 | 196-PheThrProProLysGlyValAspVal-204 |
| Hydrophilic Regions - Hopp-Woods | |
| SEQ. ID. NO. 19293 | 34-PheAsnAsnAspAlaAspGlyIle-41 |
| SEQ. ID. NO. 19294 | 49-ValGlnSerLysLysLysThrGlnThr-57 |
| SEQ. ID. NO. 19295 | 100-ThrLysSerSerGlnAspGlnAlaIle-108 |
| SEQ. ID. NO. 19296 | 126-TyrThrLeuLysGluAspGlySerSerAsn-135 |
| SEQ. ID. NO. 19297 | 143-ThrProLysArgAsnAsnAla-149 |
| SEQ. ID. NO. 19298 | 167-GlnLeuLysAspSerPheGly-173 |
| a503-l | |
| AMPHI Regions - AMPHI | |
| SEQ. ID. NO. 19299 | 6-TyrArgGluAlaAsnThrTrp-12 |
| SEQ. ID. NO. 19300 | 96-SerSerThrSerAsnPheAlaSerAlaAlaGluMetArgSerLeu-110 |
| Antigenic Index - Jameson-Wolf | |
| SEQ. ID. NO. 19301 | 4-SerLeuTyrArgGluAlaAsnThr-11 |
| SEQ. ID. NO. 19302 | 26-ArgLysValSerCys-30 |
| SEQ. ID. NO. 19303 | 32-ProAlaAsnAspAlaSerGlyArgSerSerAlaValAlaGluGluArgThrAlaThrGluMetSerAlaProProAla-57 |
| SEQ. ID. NO. 19304 | 69-SerAlaSerSerCysSerGlyLysGlyValSer-79 |
| SEQ. ID. NO. 19305 | 87-LeuProThrArgAlaSerSerAlaThrSerSerThrSerAsn-100 |
| SEQ. ID. NO. 19306 | 105-AlaGluMetArgSerLeuArg-111 |
| SEQ. ID. NO. 19307 | 113-LeuCysAlaArgAsnAlaArg-119 |

TABLE 1-continued

| | |
|---|---|
| Hydrophilic Regions - Hopp-woods | |
| SEQ. ID. NO. 19308 | 4-SerLeuTyrArgGlu-8 |
| SEQ. ID. NO. 19309 | 35-AspAlaSerGlyArgSerSerAlaValAlaGluGluArgThrAlaThrGluMetSerAla-54 |
| SEQ. ID. NO. 19310 | 73-CysSerGlyLysGlyValSer-79 |
| SEQ. ID. NO. 19311 | 89-ThrArgAlaSerSer-93 |
| SEQ. ID. NO. 19312 | 105-AlaGluMetArgSerLeuArg-111 |
| a505 | |
| AMPHI Regions - AMPHI | |
| SEQ. ID. NO. 19313 | 20-LeuThrAlaLeuLeuLysCysLeuSerLeuLeuProLeuSerCysLeu-35 |
| SEQ. ID. NO. 19314 | 37-ThrLeuGlyAsnArg-41 |
| SEQ. ID. NO. 19315 | 89-ProAlaPhePheArgLysProGluAspIleGluThrMetPheLysAlaValHisGlyTrpGluHisValGlnGlnAlaLeuAsp-116 |
| SEQ. ID. NO. 19316 | 148-AlaMetTyrLysProProLysIleLysAlaIleAspLysIleMetGlnAlaGly-165 |
| SEQ. ID. NO. 19317 | 178-IleGlnGlyValLysGlnIleIleLysAlaLeuArg-189 |
| SEQ. ID. NO. 19318 | 210-GlyValTrpValAspPhePheGlyLysPro-219 |
| Antigenic Index - Jameson-Wolf | |
| SEQ. ID. NO. 19319 | 38-LeuGlyAsnArgLeuGly-43 |
| SEQ. ID. NO. 19320 | 50-LeuLysGluAspArgAlaArgIle-57 |
| SEQ. ID. NO. 19321 | 62-ArgGlnAlaGlyMetAsnProAspProLysThrVal-73 |
| SEQ. ID. NO. 19322 | 79-GluThrAlaLysGlyGlyLeu-85 |
| SEQ. ID. NO. 19323 | 92-PheArgLysProGluAspIleGluThr-100 |
| SEQ. ID. NO. 19324 | 114-AlaLeuAspLysHisGlu-119 |
| SEQ. ID. NO. 19325 | 129-GlySerTyrAspLeuGlyGlyArgTyrIleSer-l39 |
| SEQ. ID. NO. 19326 | 142-LeuProPheProLeu-146 |
| SEQ. ID. NO. 19327 | 150-TyrLysProProLysIleLysAlaIleAspLysIleMetGln-163 |
| SEQ. ID. NO. 19328 | 165-GlyArgValArgGlyLysGlyLysThrAlaProThrSer-177 |
| SEQ. ID. NO. 19329 | 183-GlnIleIleLysAlaLeuArgSerGlyGluAlaThr-194 |
| SEQ. ID. NO. 19330 | 198-ProAspHisValProSerProGlnGluGlyGlyGluGlyVal-211 |
| SEQ. ID. NO. 19331 | 242-CysGluArgLeuProGlyGlyGlnGly-250 |
| SEQ. ID. NO. 19332 | 257-ProValGlnGlyGluLeuAsnGlyAspLysAlaHisAsp-269 |
| SEQ. ID. NO. 19333 | 292-TyrAsnArgTyrLysMetPro-298 |
| Hydrophilic Regions - Hopp-Woods | |
| SEQ. ID. NO. 19334 | 50-LeuLysGluAspArgAlaArgIle-57 |
| SEQ. ID. NO. 19335 | 62-ArgGlnAlaGlyMetAsnProAspProLysThrVal-73 |
| SEQ. ID. NO. 19336 | 79-GluThrAlaLysGlyGlyLeu-85 |
| SEQ. ID. NO. 19337 | 92-PheArgLysProGluAspIleGluThr-100 |
| SEQ. ID. NO. 19338 | 114-AlaLeuAspLysHisGlu-119 |
| SEQ. ID. NO. 19339 | 151-LysProProLysIleLysAlaIleAspLysIleMetGln-163 |
| SEQ. ID. NO. 19340 | 165-GlyArgValArgGlyLysGlyLysThrAlaPro-175 |
| SEQ. ID. NO. 19341 | 183-GlnIleIleLysAlaLeuArgSerGlyGlu-192 |
| SEQ. ID. NO. 19342 | 201-ValProSerProGlnGluGlyGlyGlu-209 |
| SEQ. ID. NO. 19343 | 258-ValGlnGlyGluLeuAsnGlyAspLysAlaHisAsp-269 |
| a506 | |
| AMPHI Regions - AMPHI | |
| SEQ. ID. NO. 19344 | 6-GluValGlyArgValAlaHisCysGlyGlyGlyVal-17 |
| SEQ. ID. NO. 19345 | 25-ArgValValHisGlnValGluGlnGlyAlaArg-35 |
| SEQ. ID. NO. 19346 | 53-AlaValAspPheGlnArgArgPhe-60 |
| SEQ. ID. NO. 19347 | 99-AlaThrArgThrValAspArgAspLeuAlaGluVal-110 |
| SEQ. ID. NO. 19348 | 138-GlyAsnGluValAlaArgCys-144 |
| SEQ. ID. NO. 19349 | 180-GlnValLysArgMetIleArgHisPhePheArg-190 |
| SEQ. ID. NO. 19350 | 199-ValHisArgProPheArgLysLeuAlaAlaLeuAspGlyPheValGlnVal-215 |
| SEQ. ID. NO. 19351 | 224-GlyAspAspPheGlyGlyPhePheValGlyGlnValPheAsnAlaLeuLeu-240 |
| SEQ. ID. NO. 19352 | 313-PheValGlnValGlyGluLeuThrArgValAlaGlnGluGlu-326 |
| SEQ. ID. NO. 19353 | 372-GlyPhePheAlaAspPheAlaGluAspPheGlyAlaGlyValPheGlyAspValValArgTyrGlyLysArgThr-396 |
| SEQ. ID. NO. 19354 | 408-PheGlyAspAspPheAlaHisGluValGlyGlu-418 |
| SEQ. ID. NO. 19355 | 427-ArgGlnGlnArgAlaAlaArgThr-434 |
| Antigenic Index - Jameson-Wolf | |
| SEQ. ID. NO. 19356 | 13-CysGlyGlyGlyValAla-18 |
| SEQ. ID. NO. 19357 | 31-GluGlnGlyAlaArgLeu-36 |
| SEQ. ID. NO. 19358 | 48-ProValArgArgValAlaValAspPheGlnArgArgPheGlyGluVal-63 |
| SEQ. ID. NO. 19359 | 98-ArgAlaThrArgThrValAspArgAspLeuAlaGlu-109 |
| SEQ. ID. NO. 19360 | 134-GlyAlaAspThrGlyAsnGluValAlaArgCysGluGly-146 |
| SEQ. ID. NO. 19361 | 176-ProAsnPheGlyGlnValLysArgMetIle-185 |
| SEQ. ID. NO. 19362 | 192-GlyPheArgHisAspLeuAspValHisArgProPheArgLys-205 |
| SEQ. ID. NO. 19363 | 223-ValGlyAspAspPheGlyGly-229 |
| SEQ. ID. NO. 19364 | 244-MetGluPheHisProLysThr-250 |
| SEQ. ID. NO. 19365 | 259-ValGlyMetArgThrGluAla-265 |
| SEQ. ID. NO. 19366 | 289-GlyGlnGlnArgProGluValProVal-297 |
| SEQ. ID. NO. 19367 | 318-GluLeuThrArgValAlaGlnGluGluHisGlyArgValValAla-332 |
| SEQ. ID. NO. 19368 | 343-GluLeuGlnArgLysThrAlaAsp-350 |
| SEQ. ID. NO. 19369 | 362-CysHisGlyGlyGluThrGlyGlu-369 |
| SEQ. ID. NO. 19370 | 377-PheAlaGluAspPheGly-382 |
| SEQ. ID. NO. 19371 | 389-ValValArgTyrGlyLysArgThrGluArgAlaArgThr-401 |
| SEQ. ID. NO. 19372 | 408-PheGlyAspAspPheAlaHisGluVal-416 |
| SEQ. ID. NO. 19373 | 424-GlnIleLeuArgGlnGlnArgAlaAlaArgThrGlyGlyGln-437 |
| SEQ. ID. NO. 19374 | 442-ValGlyAsnArgArgAlaVal-448 |
| SEQ. ID. NO. 19375 | 458-PheGlyGlyXxxHisArgSerCysSer-466 |
| SEQ. ID. NO. 19376 | 471-GlyGlnXxxGlyGlyLysArgLeuThrValArgPheGlyGlyLysArgIleArgAsnArgPheLeuAspCysAsnLysPheLeuGlu-499 |
| SEQ. ID. NO. 19377 | 510-MetAspAlaThrIleArgGlnAspPheArgTyr-520 |

TABLE 1-continued

| | |
|---|---|
| Hydrophilic Regions - Hopp-Woods | |
| SEQ. ID. NO. 19378 | 31-GluGlnGlyAlaArgLeu-36 |
| SEQ. ID. NO. 19379 | 48-ProValArgArgValAlaValAspPheGlnArgArgPheGlyGlu-62 |
| SEQ. ID. NO. 19380 | 98-ArgAlaThrArgThrValAspArgAspLeuAlaGlu-109 |
| SEQ. ID. NO. 19381 | 136-AspThrGlyAsnGluValAlaArgCysGluGly-146 |
| SEQ. ID. NO. 19382 | 180-GlnValLysArgMetIle-185 |
| SEQ. ID. NO. 19383 | 195-HiGAspLeuAspVal-199 |
| SEQ. ID. NO. 19384 | 201-ArgProPheArgLys-205 |
| SEQ. ID. NO. 19385 | 223-ValGlyAspAspPhe-227 |
| SEQ. ID. NO. 19386 | 244-MetGluPheHisPro-248 |
| SEQ. ID. NO. 19387 | 259-ValGlyMetArgThrGluAla-265 |
| SEQ. ID. NO. 19388 | 291-GlnArgProGluVal-295 |
| SEQ. ID. NO. 19389 | 318-GluLeuThrArgValAlaGlnGluGluHisGlyArgValValAla-332 |
| SEQ. ID. NO. 19390 | 343-GluLeuGlnArgLysThrAlaAsp-350 |
| SEQ. ID. NO. 19391 | 364-GlyGlyGluThrGlyGlu-369 |
| SEQ. ID. NO. 19392 | 377-PheAlaGluAspPheGly-382 |
| SEQ. ID. NO. 19393 | 390-ValArgTyrGlyLysArgThrGluArgAlaArgThr-401 |
| SEQ. ID. NO. 19394 | 408-PheGlyAspAspPheAlaHisGluVal-416 |
| SEQ. ID. NO. 19395 | 425-1leLeuArgGlnGlnArgAlaAlaArgThrGlyGly-436 |
| SEQ. ID. NO. 19396 | 443-GlyAsnArgArgAlaVal-448 |
| SEQ. ID. NO. 19397 | 473-XxxGlyGlyLysArgLeuThr-479 |
| SEQ. ID. NO. 19398 | 482-PheGlyGlyLysArgIleArgAsnArgPheLeuAsp-493 |
| SEQ. ID. NO. 19399 | 510-MetAspAlaThrIleArgGlnAspPheAcgTyr-520 |
| a513 | |
| AMPHI Regions AMPHI | |
| SEQ. ID. NO. 19400 | 6-ThrGluTrpLeuHisGlyTrpValGlyAlaIleAsnAspProMetTrp |
| SEQ. ID. NO. 19401 | 23-TyrLeuValTyrXxxLeu-28 |
| SEQ. ID. NO. 19402 | 48-GlyArgSerIleLysGlu-53 |
| SEQ. ID. NO. 19403 | 66-GlyIleThrProPheGlnAlaPheValThrGlyLeuAla-78 |
| SEQ. ID. NO. 19404 | 119-SerSerLeuAlaGlnLeuPheLy3ValArgAsp-129 |
| SEQ. ID. NO. 19405 | 146-GlyLeuGlyGlnLysTrpLeuGlyVal-154 |
| SEQ. ID. NO. 19406 | 176-IleAlaAspThrVal-180 |
| SEQ. ID. NO. 19407 | 205-GlyGlyIleArgArgIleSerLy3AlaAla-214 |
| SEQ. ID. NO. 19408 | 243-ValPheGlyGlnIlePheSer-249 |
| SEQ. ID. NO. 19409 | 259-GlyGlyLeuLeuGlyGlyLeuIle-266 |
| SEQ. ID. NO. 19410 | 288-AlaProAsnAlaAlaAlaAlaAla-295 |
| SEQ. ID. NO. 19411 | 303-GlnGlyMetIleGlnMetLeuGlyValPheValAsp-314 |
| SEQ. ID. NO. 19412 | 332-ProTyrGlyAspLeu-336 |
| SEQ. ID. NO. 19413 | 347-ValSerGlnValGlyGlnTrp-353 |
| SEQ. ID. NO. 19414 | 391-ThrAlaValPheArgMet-396 |
| SEQ. ID. NO. 19415 | 403-TyiPheGlyAlaValAla-408 |
| SEQ. ID. NO. 19416 | 423-IleMetAlaTrpIleAsnLeuValAlaIleLeuLeuLeuSer-436 |
| Antigenic Index - Jameson-Wolf | |
| SEQ. ID. NO. 19417 | 1-MetAsnGluAsnPhe-5 |
| SEQ. ID. NO. 19418 | 48-GlyArgSerIleLysGluMetLeuGlyGlyArgLysGlnGlyAspAspProHisGly-66 |
| SEQ. ID. NO. 19419 | 126-LysValArgAspTyrAspAsnHisHisPheArgGlyGlyProAla-140 |
| SEQ. ID. NO. 19420 | 208-ArgArgIleSerLysAlaAlaGlu-215 |
| SEQ. ID. NO. 19421 | 273-GlyIleLysArgGlyLeuTyrSerAsnGluAlaGlyMetGlySerAlaProAsnAla-291 |
| SEQ. ID. NO. 19422 | 295-AlaGluValLysHisProVal-301 |
| SEQ. ID. NO. 19423 | 331-GlnProTyrGlyAspLeuSerGly |
| SEQ. ID. NO. 19424 | 375-AlaTyrAlaGluSerAsnVal-381 |
| SEQ. ID. NO. 19425 | 444-ArgAspTyrThrAlaLysLeuLysMetGlyLysAspProGluPheLysLeuSerGluHisProGlyLeuLysArgArgIleLysSerAspValTrp-475 |
| Hydrophilic Regions - Hopp-Woods | |
| SEQ. ID. NO. 19426 | 48-GlyArgSerIleLysGluMetLeuGlyGlyArgLysGlnGlyAspAspProHisGly-66 |
| SEQ. ID. NO. 19427 | 126-LysValArgAspTyrAspAsnHisHis-134 |
| SEQ. ID. NO. 19428 | 208-ArgArgIleSerLysAlaAlaGlu-215 |
| SEQ. ID. NO. 19429 | 273-GlyIleLysArgGlyLeuTyr-279 |
| SEQ. ID. NO. 19430 | 295-AlaGluValLysHis-299 |
| SEQ. ID. NO. 19431 | 450-LeuLysMetGlyLysAspProGluPheLysLeuSerGlu-462 |
| SEQ. ID. NO. 19432 | 464-ProGlyLeuLysArgArgIleLysSer-472 |
| a515-l | |
| AMPHI Regions - AMPHI | |
| SEQ. ID. NO. 19433 | 8-ArgAlaAlaGlyValAlaArgGlyLeuHisSerGluPheAlaArg-22 |
| SEQ. ID. NO. 19434 | 59-AspValArgPhePheAlaGlnValGluGluIleGlyGlnAspPhePheAlaAspAla-77 |
| SEQ. ID. NO. 19435 | 90-AlaGlyGluCysAlaAspGluValSerAspLysThr-101 |
| SEQ. ID. NO. 19436 | 122-GluSerAlaGlnSerAlaAlaGlyGlyGlyLeuThrAspGlyPheGly-l37 |
| SEQ. ID. NO. 19437 | 176-CysGlyLysThrValGlyVal-182 |
| SEQ. ID. NO. 19438 | 198-GlyValPheAspAla-202 |
| SEQ. ID. NO. 19439 | 233-ValAlaAspValLeuArg-238 |
| SEQ. ID. NO. 19440 | 251-PheGlyGlyValAlaGlyAspValGlyGlyGlyAlaAspGlyValAlaGlnGlyLeuPheGlyGluIleGlyGlyAla-276 |
| Antigenic Index - Jameson-Wolf | |
| SEQ. ID. NO. 19441 | 24-ValThrAlaGluGluIleAlaPhe-31 |
| SEQ. ID. NO. 19442 | 38-HisGluAlaArgCysGlyGlyAsn-45 |
| SEQ. ID. NO. 19443 | 51-IleAlaAlaAlaGluArgAlaGlyAsp-59 |
| SEQ. ID. NO. 19444 | 67-GluGluIleGlyGln-71 |
| SEQ. ID. NO. 19445 | 77-AlaValAspGlnGluThr-82 |
| SEQ. ID. NO. 19446 | 84-LeuAlaValGluArgSerAlaGlyGluCysAlaAspGluValSerAspLysThrAlaArgAsnGlyGlyIleGluGluAspGlyValValAlaCys ArgAspAlaAlaAlaAlaGluSerAlaGln-125 |
| SEQ. ID. NO. 19447 | 128-AlaGlyGlyGlyLeuThrAspGly-135 |
| SEQ. ID. NO. 19448 | 160-GlyGlyAsnAspAlaAlaGlyAsn-167 |

TABLE 1-continued

| | |
|---|---|
| SEQ. ID. NO. 19449 | 192-LeuHisArgArgAla-196 |
| SEQ. ID. NO. 19450 | 217-AlaAspGlyGlyPheArg-222 |
| SEQ. ID. NO. 19451 | 242-GlyValGlyLysSerGlyAla-248 |
| SEQ. ID. NO. 19452 | 257-AspValGlyGlyGlyAlaAspGlyVal-265 |
| SEQ. ID. NO. 19453 | 284-AspValAsnGlyAsnValGln-290 |
| Hydrophilic Regions - Hopp-Woods | |
| SEQ. ID. NO. 19454 | 24-ValThrAlaGluGluIleAlaPhe-31 |
| SEQ. ID. NO. 19455 | 38-HisGluAlaArgCysGly-43 |
| SEQ. ID. NO. 19456 | 51-IleAlaAlaAlaGluArgAlaGlyAsp-59 |
| SEQ. ID. NO. 19457 | 77-AlaValAspGlnGluThr-82 |
| SEQ. ID. NO. 19458 | 84-LeuAlaValGluArgSerAlaGlyGluCysAlaAspGluValSerAspLysThrAlaArgAsnGlyGlyIleGluGluAspGlyValValAlaCys ArgAspAlaAlaAlaAlaGluSerAlaGln-125 |
| SEQ. ID. NO. 19459 | 162-AsnAspAlaAlaGly-166 |
| SEQ. ID. NO. 19460 | 192-LeuHisArgArgAla-196 |
| SEQ. ID. NO. 19461 | 258-ValGlyGlyGlyAlaAcpGlyVal-265 |
| a519-l | |
| AMPHI Regions - AMPHI | |
| SEQ. ID. NO. 19462 | 29-ValValGluArgLeuGlyArgPheHisArgAlaLeuThrAlaGly-43 |
| SEQ. ID. NO. 19463 | 105-MetAlaIleThrGlnLeuAlaGlnThrThrLeuArgSerVal-118 |
| SEQ. ID. NO. 19464 | 139-ValSerAlaLeuAspGluAlaAla-146 |
| SEQ. ID. NO. 19465 | 166-GluIleLeuArgSerMetGlnAla-173 |
| SEQ. ID. NO. 19466 | 192-LysIleGluGlnIle-196 |
| SEQ. ID. NO. 19467 | 221-SerAsnAlaGluLysIleAlaArgIleAsn-230 |
| SEQ. ID. NO. 19468 | 249-AlaIleArgGlnIleAlaAlaAla-256 |
| SEQ. ID. NO. 19469 | 273-GlnTyrValAlaAlaPheAsnAsnLeuAlaLys-283 |
| SEQ. ID. NO. 19470 | 292-AlaAsnValAlaAspIleGlySerLeuIleSerAlaGlyMetLysIleIleAspSerSerLysThrAla-314 |
| Antigenic Index - Jameson-Wolf | |
| SEQ. ID. NO. 19471 | 31-GluArgLeuGlyArgPheHisArg-38 |
| SEQ. ID. NO. 19472 | 58-HisSerLeuLysGluIleProLeuAspValProSerGln-70 |
| SEQ. ID. NO. 19473 | 72-CysIleThrArgAspAsnThrGlnLeuThrVal-82 |
| SEQ. ID. NO. 19474 | 91-ThrAspProLysLeuAlaSer-97 |
| SEQ. ID. NO. 19475 | 122-MetGluLeuAspLysThrPheGluGluArgAspGluIleAsn-135 |
| SEQ. ID. NO. 19476 | 141-AlaLeuAspGluAlaAlaGly-147 |
| SEQ. ID. NO. 19477 | 154-LeuArgTyrGluIleLysAspLeuValPro-163 |
| SEQ. ID. NO. 19478 | 175-IleThrAlaGluArgGluLysArgAlaArgIleAlaGluSerGluGlyAr gLysIleGluGln-195 |
| SEQ. ID. NO. 19479 | 197-AsnLeuAlaSerGlyGlnArgGluAlaGluIleGlnGlnSerGluGlyGluAlaGlnAla-216 |
| SEQ. ID. NO. 19480 | 219-AsnAlaSerAsnAlaGluLysIleAlaArgIleA5nArgAlaLysGlyGluAlaGluSerLeuArgLeu-241 |
| SEQ. ID. NO. 19481 | -AlaAsnAlaGluAlaIleArg-251 |
| SEQ. ID. NO. 19482 | -GlnThrGlnGlyGlyAlaAspAlaValAsn-267 |
| SEQ. ID. NO. 19483 | -LeuAlaLysGluSerAsnThr-287 |
| SEQ. ID. NO. 19484 | -AlaGlyMetLysIleIleAspSerSerLysThrAlaLys-315 |
| Hydrophilic Regions - Hopp-Woods | |
| SEQ. ID. NO. 19485 | 31-GluAlyLeuGlyAlyPheHisArg-38 |
| SEQ. ID. NO. 19486 | 58-HisSerLeuLysGluIleProLeu-65 |
| SEQ. ID. NO. 19487 | 73-IleThrArgAspAsnThr-78 |
| SEQ. ID. NO. 19488 | 91-ThrAspProLysLeu-95 |
| SEQ. ID. NO. 19489 | l22-MetGluLeuAspLysThrPheGluGluArgAspGluIleAsn-135 |
| SEQ. ID. NO. 19490 | 141-AlaLeuAspGluAlaAla-146 |
| SEQ. ID. NO. 19491 | 154-LeuArgTyrGluIleLysAspLeuValPro-163 |
| SEQ. ID. NO. 19492 | 175-IleThrAlaGluArgGluLysArgAlaArgIleAlaGluSerGluGlyAr gLysIleGluGln-195 |
| SEQ. ID. NO. 19493 | 200-SerGlyGlnArgGluAlaGluIleGlnGlnSerGluGlyGluAlaGlnAla-216 |
| SEQ. ID. NO. 19494 | 221-SerAsnAlaGluLysIleAlaArgIleAsnArgAlaLysGlyGluAlaGluSerLeuArgLeu-241 |
| SEQ. ID. NO. 19495 | 245-AlaAsnAlaGluAlaTleArg-251 |
| SEQ. ID. NO. 19496 | 281-LeuAlaLy3GluSerAsn-286 |
| SEQ. ID. NO. 19497 | 306-LysIleIleAspSerSerLysThrAlaLys-315 |
| a520-l | |
| AMPHI Regions - AMPHI | |
| SEQ ID. NO. 19498 | 104-LeuThrLysAlaAlaAspGlyGlnValCysArgAlaPheSerSerLeu-119 |
| Antigenic Index - Jameson-wolf | |
| SEQ. ID. NO. 19499 | 20-LysProSerArgArgAlaLeu-26 |
| SEQ. ID. NO. 19500 | 47-AlaSerGlyLysIleSerLeuPro-54 |
| SEQ. ID. NO. 19501 | 84-ProProAsnAsnSerThrThrThrSerThrSerSerArgAlaThrSerSerAsnGlySerLeuThrLysAlaAlaAspGlyGlnVal-112 |
| SEQ. ID. NO. 19502 | 117-SerSerLeuLysSerHisThrAlaGluIleArgIleSerArgProLysArgArgGluIleSerSerAlaLeuSerArgAsnThrAlaAla-146 |
| SEQ. ID. NO. 19503 | 150-ProThrValProLysProLysArgProMet-159 |
| SEQ. ID. NO. 19504 | 166-SerProCysLysProThrGluMet-173 |
| Hydrophilic Regions - Hopp-woods | |
| SEQ. ID. NO. 19505 | 20-LysProSerArgArgAlaLeu-26 |
| SEQ. ID. NO. 19506 | 93-ThrSerSerArgAlaThrSerSer-100 |
| SEQ. ID. NO. 19507 | 103-SerLeuThrLysAlaAlaAsp-109 |
| SEQ. ID. NO. 19508 | 120-LysSerHisThrAlaGluIleArgIleSerArgProLysArgArgGluIleSer-137 |
| SEQ. ID. NO. 19509 | 140-LeuSerArgAsnThrAla-145 |
| SEQ. ID. NO. 19510 | 151-ThrValProLysProLysArgProMet-159 |
| SEQ. ID. NO. 19511 | 168-CysLysProThrGluMet-173 |
| a521 | |
| AMPHI Regions - AMPHI | |
| SEQ. ID. NO. 19512 | 86-ValLysThrValSerLysProAlaLys-94 |
| SEQ. ID. NO. 19513 | 133-GlnAlaArgLeuAlaLysGlyGlyAsn-141 |
| SEQ. ID. NO. 19514 | 147-IleAsnAlaLeuGlnSerValLeuAsp-155 |

TABLE 1-continued

| | |
|---|---|
| Antigenic Index - Jameson-Wolf | |
| SEQ. ID. NO. 19515 | 1-MetLysSerLysLeu-5 |
| SEQ. ID. NO. 19516 | 36-ValTyrThrThrLysProSerLysSerCysLeuSerThrAspLeuProProIle-53 |
| SEQ. ID. NO. 19517 | 55-AsnTyrSerSerGluArgTyrIleProProGlnThrSerGluProThrProSerProSerAsnGlyGlyGln-78 |
| SEQ. ID. NO. 19518 | 80-ValLysTyrLysAlaProVal-86 |
| SEQ. ID. NO. 19519 | 88-ThrValSerLysProAlaLysSerAsnThrProProProGlnGlnAlaProSerAsnAsnSerArgArgSerIleLeuGluThrGluLeuSerAsn GluArgLys AlaLeuValGluAlaGlnLysMetLeuSer-132 |
| SEQ. ID. NO. 19520 | 135-ArgLeuAlaLysGlyGlyAsnIleAsn-143 |
| SEQ. ID. NO. 19521 | 153-ValLeuAspArgGlnGlnAsn-159 |
| SEQ. ID. NO. 19522 | 163-LeuGlnArgGluLeuGlyArg-169 |
| Hydrophilic Regions - Hopp-woods | |
| SEQ. ID. NO. 19523 | 1-MetLysSerLysLeu-5 |
| SEQ. ID. NO. 19524 | 40-LysProSerLysSerCysLeu-46 |
| SEQ. ID. NO. 19525 | 57-SerSerGluArgTyrIle-62 |
| SEQ. ID. NO. 19526 | 65-GlnThrSerGluProThrProSerProSerAsnGly-76 |
| SEQ. ID. NO. 19527 | 80-ValLysTyrLysAlaProVal-86 |
| SEQ. ID. NO. 19528 | 88-ThrValSerLysProAlaLysSerAsnThrProPro-99 |
| SEQ. ID. NO. 19529 | 102-GlnAlaProSerAsnAsnSerArgArgSerIleLeuGluThrGluLeuSerAsnGluArgLysAlaLeuValGluAlaGlnLysMetLeuSer-132 |
| SEQ. ID. NO. 19530 | 153-ValLeuAspArgGlnGlnAsn-159 |
| SEQ. ID. NO. 19531 | 163-LeuGlnArgGluLeuGlyArg-169 |
| a522 | |
| AMPHI Regions - AMPHI | |
| SEQ. ID. NO. 19532 | 57-LysIleValGluSerCysValLys-64 |
| SEQ. ID. NO. 19533 | 96-MetTrpGluGlnProLeuAspArgLeuSerGluLysGlnIleSerSerPheGlyLysLeuGlyAlaGlnGluGlnLeuAspLeuLeuGlyGlyAla-127 |
| Antigenic Index - Jameson-Wolf | |
| SEQ. ID. NO. 19534 | 1-MetThrGluProLysHisGluMetProThrGluGluGlnValAlaAlaArgLysLysAlaLysAlaLysIleArgThr-26 |
| SEQ. ID. NO. 19535 | 48-AlaMetSerLysProGlnAlaLysGlnLysIleValGluSerCysValLys-64 |
| SEQ. ID. NO. 19536 | 71-LysTrpGlnAsnAspLeuArgAlaArgGlyLeuAspSerAsnAsnThrArgLeuThr-89 |
| SEQ. ID. NO. 19537 | 99-GlnProLeuAspArgLeuSerGluLysGlnIleSerSerPheGlyLysLeuGlyAla-117 |
| SEQ. ID. NO. 19538 | 128-AsnAlaPheGluThrArgAspLysGlnCysValAlaAspLeuLysSerGlu-144 |
| Hydrophilic Regions - Hopp-Woods | |
| SEQ. ID. NO. 19539 | 1-MetThrGluProLysHisGluMetProThrGluGluGlnValAlaAlaArgLysLysAlaLysAlaLysIleArgThr-26 |
| SEQ. ID. NO. 19540 | 48-AlaMetSerLysProGlnAlaLysGlnLysIleValGluSerCysVal-63 |
| SEQ. ID. NO. 19541 | 72-TrpGlnAsnAspLeuArgAlaArgGlyLeuAspSerAsnAsnThr-86 |
| SEQ. ID. NO. 19542 | 100-ProLeuAspArgLeuSerGluLysGlnIle-109 |
| SEQ. ID. NO. 19543 | 130-PheGluThrArgAspLysGlnCysValAlaAspLeuLysSerGlu-144 |
| a525-l | |
| AMPHI Regions - AMPHI | |
| SEQ. ID. NO. 19544 | 59-GluPheAlaGluPheValAsnSerHisProGln-69 |
| SEQ. ID. NO. 19545 | 86-LysHisTrpMetLysAsnGly-92 |
| SEQ. ID. NO. 19546 | 125-ArgLeuProThrIleAspGluTrpGluPhe-134 |
| SEQ. ID. NO. 19547 | 166-AspLeuHisAspValGly-171 |
| SEQ. ID. NO. 19548 | 178-TrpGlyValTyrAsp-182 |
| SEQ. ID. NO. 19549 | 188-TrpGluTrpThrGlu-192 |
| Antigenic Index - Jameson-Wolf | |
| SEQ. ID. NO. 19550 | 24-ValGlnIleGluGlyGlySerTyrArgProLeuTyrLeuLysLysAspThrGlyLeuIleLys-44 |
| SEQ. ID. NO. 19551 | 46-LysProPheLysLeuAspLysTyrProValThr-56 |
| SEQ. ID. NO. 19552 | 67-HisProGlnTrpGlnLysGlyArgIleGlySerLysGlnAlaGlu-81 |
| SEQ. ID. NO. 19553 | 88-TrpMetLysAsnGlySerArgSerTyrAlaProLysAlaGlyAspLeuLysGlnPro-106 |
| SEQ. ID. NO. 19554 | 122-GlnGlyLysArgLeuProThrIleAspGluTrpGlu-133 |
| SEQ. ID. NO. 19555 | 140-AlaThrGlnLysAsnGlySerAsnGluProGlyTyrAsnArgThr-154 |
| SEQ. ID. NO. 19556 | 159-TyrAlaAspGlyAspArgLysAspLeuHisAspValGlyLysGlyArgProAsnTyr-177 |
| SEQ. ID. NO. 19557 | 190-TrpThrGluAspPheAGnSerSerLeuLeuSerSerGlyAsnAla-204 |
| SEQ. ID. NO. 19558 | 213-AlaSerIleGlySerSerAspSerSerAsnTyr-223 |
| SEQ. ID. NO. 19559 | 234-SerLeuGlnSerLysTyr-239 |
| Hydrophilic Regions - Hopp-Woods | |
| SEQ. ID. NO. 19560 | 35-TyrLeuLysLysAspThrGlyLeuIleLys-44 |
| SEQ. ID. NO. 19561 | 46-LysProPheLysLeuAspLysTyrPro-54 |
| SEQ. ID. NO. 19562 | 71-GlnLysGlyArgIleGlySerLysGlnAlaGlu-81 |
| SEQ. ID. NO. 19563 | 91-AsnGlySerArgSerTyrAla-97 |
| SEQ. ID. NO. 19564 | 99-LysAlaGlyAspLeuLysGln-105 |
| SEQ. ID. NO. 19565 | 122-GlnGlyLysArgLeuProThr-128 |
| SEQ. ID. NO. 19566 | 140-AlaThrGlnLysAsnGlySerAsnGluProGlyTyr-151 |
| SEQ. ID. NO. 19567 | 160-AlaAspGlyAspArgLysAspLeuHisAspValGlyLysGlyArgPro-175 |
| SEQ. ID. NO. 19568 | 216-GlySerSerAspSerSerAsn-222 |
| a527 | |
| AMPHI Regions - AMPHI | |
| SEQ. ID. NO. 19569 | 7-PhePheGlnProValGln-12 |
| SEQ. ID. NO. 19570 | 28-SerAspAlaAlaGluLeuValGluLeuPheAlaLeuPhePro-41 |
| SEQ. ID. NO. 19571 | 73-GlyLysGlyIleGluArgGlnValAspAsnIleAlaAspValTyrGlyPhe-89 |
| Antigenic Index - Jameson-Wolf | |
| SEQ. ID. NO. 19572 | 26-GlyGlySerAspAlaAlaGlu-32 |
| SEQ. ID. NO. 19573 | 52-GlnLysProArgLeuGlyCys-58 |
| SEQ. ID. NO. 19574 | 71-pheIleGlyLysGlyIleGluArgGlnValAspAsnIleAla-84 |
| SEQ. ID. NO. 19575 | 107-LeuLeuArgLysGlyThrGlyLeuGluLysThrCysArgProLysProPheValGlnProHisGlyGlyArg-130 |
| Hydrophilic Regions - Hopp-woods | |
| SEQ. ID. NO. 19576 | 27-GlySerAspAlaAlaGlu-32 |
| SEQ. ID. NO. 19577 | 52-GlnLysProArgLeuGlyCys-58 |
| SEQ. ID. NO. 19578 | 75-GlyIleGluArgGlnValAspAsnIleAla-84 |

| | |
|---|---|
| SEQ. ID. NO. 19579 | 107-LeuLeuArgLysGlyThrGlyLeuGluLysThrCysArgProLysPro-l22 |
| a528 | |
| AMPHI Regions - AMPHI | |
| SEQ. ID. NO. 19580 | 7-LysTyrThrAlaMetAlaAlaLeuLeuAlaPhe-17 |
| SEQ. ID. NO. 19581 | 23-ArgLeuAlaGlyTrpTyrGluCysSerSerLeuSerGlyTrpCysLysProArgLysProAlaAlaIle-45 |
| SEQ. ID. NO. 19582 | 69-AsnArgSerValArg-73 |
| SEQ. ID. NO. 19583 | 86-TyrArgLysIleGlyLysPhe-92 |
| SEQ. ID. NO. 19584 | 106-ProLeuIleGluThrPheLys-112 |
| Antigenic Index - Jameson-Wolf | |
| SEQ. ID. NO. 19585 | 1-MetGluIleArgAla-5 |
| SEQ. ID. NO. 19586 | 29-GluCysSerSerLeuSerGlyTrpCysLysProArgLysProAlaAla-44 |
| SEQ. ID. NO. 19587 | 49-AspIleGlyGlyGluSerProProSerLeuGluAspTyrGluIleProLeuSerAspGlyAsnArgSerValArgAlaAsnGluTyrGluSerAla GlnGlnSer-83 |
| SEQ. ID. NO. 19588 | 88-LysIleGlyLysPheGluAlaCysGlyLeuAspTrpArgThrArgAspGlyLysProLeu-107 |
| SEQ. ID. NO. 19589 | 110-ThrPheLyoGlnGluGlyPheAspCysLeuLysLysGlnGlyLeuArgArgAsnGlyLeuSerGluArgValArgTrp-135 |
| Hydrophilic Regions - Hopp-Woods | |
| SEQ. ID. NO. 19590 | 1-MetGluIleArgAla-5 |
| SEQ. ID. NO. 19591 | 37-CysLysProArgLysProAlaAla-44 |
| SEQ. ID. NO. 19592 | 51-GlyGlyGluSerProProSerLeuGluAspTyrGluIleProLeu-65 |
| SEQ. ID. NO. 19593 | 67-AspGlyAsnArgSerValArgAlaAsnGluTyrGluSecAlaGln-81 |
| SEQ. ID. NO. 19594 | 88-LysIleGlyLysPheGluAlaCys-95 |
| SEQ. ID. NO. 19595 | 99-TrpArgThrArgAspGlyLysProLeu-107 |
| SEQ. ID. NO. 19596 | 111-PheLysGlnGluGlyPheAspCysLeuLysLysGlnGlyLeuArgArgAsnGlyLeuSerGluArgValArgTrp-135 |
| a529 | |
| AMPHI Regions - AMPHI | |
| SEQ. ID. NO. 19597 | 11-LeuAlaLeuIleGlyLeuAlaAlaCysSer-20 |
| SEQ. ID. NO. 19598 | 35-SerHisArgLeuIle-39 |
| SEQ. ID. NO. 19599 | 49-AsnProAspGlnGlyAsnLeuTyrArgLeuProAla-60 |
| SEQ. ID. NO. 19600 | 79-GlnGlnProAlaAspAlaGluValLeuLysSerValLysGlyValArg-94 |
| SEQ. ID. NO. 19601 | 152-GlnAspSerLeuArgArgLeuPheAsp-160 |
| SEQ. ID. NO. 19602 | 162-ValGlyLeuGlyGlyIleTyr-168 |
| SEQ. ID. NO. 19603 | 196-AlaMetLysGluVal-200 |
| SEQ. ID. NO. 19604 | 223-AlaPheLeuThrArgPheMetGlnTyrLeu-232 |
| SEQ. ID. NO. 19605 | 252-AlaAsnGluMetAla-256 |
| SEQ. ID. NO. 19606 | 270-GlyArgAcnTrpArg-274 |
| Antigenic Index - Jameson-Wolf | |
| SEQ. ID. NO. 19607 | 19-CysSerGlySerLysThrGluGlnProLysLeuAspTyrGlnSerArgSerHisArgLeuIleLys-40 |
| SEQ. ID. NO. 19608 | 42-GluValProProAspLeuAsnAsnProAspGlnGlyAsnLeuTyr-56 |
| SEQ. ID. NO. 19609 | 60-AlaGlySerGlyAlaValArgAlaSerAspLeuGluLysArgArgThrProAlaVal-78 |
| SEQ. ID. NO. 19610 | 80-GlnProAlaAspAlaGluValLeuLysSerValLysGlyValArgLeuGluArgAspGlySerGln-101 |
| SEQ. ID. NO. 19611 | 105-ValValAspGlyLysSerHisAla-112 |
| SEQ. ID. NO. 19612 | 123-GlnGluAsnGlyPheAspIleLysSerGluGluProAls-135 |
| SEQ. ID. NO. 19613 | 139-MetGluThrGluTrpAlaGluAsnArgAlaLysIleProGlnAspSerLeuArgArgLeuPhe-159 |
| SEQ. ID. NO. 19614 | 169-SerThrGlyGluArgAspLysPheIleValArgIleGluGlnGlyLysAsnGlyValSer-188 |
| SEQ. ID. NO. 19615 | 195-LysAlaMetLysGluValTyrGlyGlyLysAspLysAspThrThr-209 |
| SEQ. ID. NO. 19616 | 212-GlnProSerProSerAspProAsnLeu-220 |
| SEQ. ID. NO. 19617 | 233-GlyValAspGlyGlnGlnAlaGluAsnAlaSerAlaLysLysProThrLeu-249 |
| SEQ. ID. NO. 19618 | 253-AsnGluMetAlaArgIleGluGlyLysSer-262 |
| SEQ. ID. NO. 19619 | 268-AspTyrGlyArgAsnTrpArgArgThrAlaLeuAla-279 |
| SEQ. ID. NO. 19620 | 289-GlyGlnAsnThrGluArgHisAla-296 |
| SEQ. ID. NO. 19621 | 300-GlnLysAlaProAsnGluSerAsnAlaValThrGluGlnLysProGlyLeu-316 |
| SEQ. ID. NO. 19622 | 320-LeuLeuGlyLysGlyLysAlaGluLysProAlaGluGlnProGlu-334 |
| SEQ. ID. NO. 19623 | 342-ValAlaAsnGlySerArg-347 |
| SEQ. ID. NO. 19624 | 350-LeuLeuAsnLysAspGlySerAlaTyrAlaGlyLysAspAlaSer-364 |
| SEQ. ID. NO. 19625 | 370-LeuHisSerGluLeuArg-375 |
| Hydrophilic Regions - Hopp-Woods | |
| SEQ. ID. NO. 19626 | 20-SerGlySerLysThrGluGlnProLysLeuAspTyrGlnSerArgSerHisArgLeuIleLys-40 |
| SEQ. ID. NO. 19627 | 42-GluValProProAspLeuAsnAsnProAspGln-52 |
| SEQ. ID. NO. 19628 | 63-GlyAlaValArgAlaSerAspLeuGluLysArgArgThrProAla-77 |
| SEQ. ID. NO. 19629 | 80-GlnProAlaAspAlaGluValLeuLysSerValLysGlyValArgLeuGluArgAspGlySerGln-101 |
| SEQ. ID. NO. 19630 | 107-AspGlyLysSerHisAla-112 |
| SEQ. ID. NO. 19631 | 125-AsnGlyPheAspIleLysSerGluGluProAla-135 |
| SEQ. ID. NO. 19632 | 139-MetGluThrGluTrpAlaGluAsnArgAlaLysIleProGlnAspSerLeuArgArgLeuPhe-159 |
| SEQ. ID. NO. 19633 | 170-ThrGlyGluArgAspLysPheIleVal-178 |
| SEQ. ID. NO. 19634 | 180-IleGluGlnGlyLysAsnGlyVal-187 |
| SEQ. ID. NO. 19635 | 195-LysAlaMetLysGluValTyrGlyGlyLysAspLysAspThrThr-209 |
| SEQ. ID. NO. 19636 | 214-SerProSerAspProAsnLeu-220 |
| SEQ. ID. NO. 19637 | 235-AspGlyGlnGlnAlaGluAsnAlaSerAlaLysLysProThr-248 |
| SEQ. ID. NO. 19638 | 253-AsnGluMetAlaArgIleGluGlyLysSer-262 |
| SEQ. ID. NO. 19639 | 269-TyrGlyArgAsnTrpArgArg-275 |
| SEQ. ID. NO. 19640 | 291-AsnThrGluArgHis-295 |
| SEQ. ID. NO. 19641 | 302-AlaProAsnGluSerAsnAlaValThrGluGlnLysProGlyLeu-316 |
| SEQ. ID. NO. 19642 | 320-LeuLeuGlyLysGlyLysAlaGluLysProAlaGluGlnProGlu-334 |
| SEQ. ID. NO. 19643 | 352-AsnLysAspGlySer-356 |
| SEQ. ID. NO. 19644 | 359-AlaGlyLysAspAlaSer-364 |
| SEQ. ID. NO. 19645 | 370-LeuHisSerGluLeuArg-375 |
| a531 | |
| AMPHI Regions - AMPHI | |
| SEQ. ID. NO. 19646 | 59-SerLeuAlaGlyIleLeuAlaAspTyrValAlaGlyIleTrpGlyThr-74 |
| SEQ. ID. NO. 19647 | 90-GlySerIleIleGlyIlePhePheSerLeuProGlyLeuIleLeuGly-105 |

TABLE 1-continued

| | |
|---|---|
| SEQ. ID. NO. 19648 | 108-1leGlyAlaAlaAlaGly-113 |
| SEQ. ID. NO. 19649 | 131-ThrLeuLeuGlyLeuIleVal-137 |
| Antigenic Index - Jameson-Wolf | |
| SEQ. ID. NO. 19650 | 74-ThrLysTyrThrGlyAlaGlyLysLeuAlaVal-84 |
| SEQ. ID. NO. 19651 | 114-GluLeuIleGluArgArgAsnMet-121 |
| Hydrophilic Regions - Hopp-Woods | |
| SEQ. ID. NO. 19652 | 114-GluLeuIleGluArgArgAsnMet-121 |
| a532 | |
| AMPHI Regions - AMPHI | |
| SEQ. ID. NO. 19653 | 6-GlyLysGlyAlaAsp-10 |
| SEQ. ID. NO. 19654 | 27-AlaLeuLeuSerAlaValThrHisLeuLeuAlaIlePheValProMetIleThr-44 |
| SEQ. ID. NO. 19655 | 76-TyrLeuGlnValAsnArgPheGlyPro-84 |
| SEQ. ID. NO. 19656 | 122-SerThrLeuLeuGly-126 |
| SEQ. ID. NO. 19657 | 147-LysValIleThrProThrVal-153 |
| SEQ. ID. NO. 19658 | 184-ThrPheGlySerMetGluAsnLeuGly-192 |
| SEQ. ID. NO. 19659 | 206-CysMetLysAsnPro-210 |
| SEQ. ID. NO. 19660 | 224-GlyTyrIleValAlaLeu-229 |
| SEQ. ID. NO. 19661 | 236-PheSerAlaLeuGlnAsnLeuPro-243 |
| SEQ. ID. NO. 19662 | 271-LeuSerValPheGluAlaValGlyAspLeuThrAla-282 |
| SEQ. ID. NO. 19663 | 297-ThrLysArgLeuArgGlyGlyVal-304 |
| SEQ. ID. NO. 19664 | 307-AspGlyLeuValSerValIleAlaThrAlaLeuGly-318 |
| SEQ. ID. NO. 19665 | 338-AlaSerArgHisValGlyLysTyr-345 |
| SEQ. ID. NO. 19666 | 361-ArgAlaPheThrThrIleProSerProVal-370 |
| Antigenic Index - Jameson-Wolf | |
| SEQ. ID. NO. 19667 | 1-MetSerGlyGlnLeuGlyLysGlyAlaAspAlaPro-12 |
| SEQ. ID. NO. 19668 | 18-LeuGluAspArgProProPheGlyAsn-26 |
| SEQ. ID. NO. 19669 | 80-AsnArgPheGlyPro-84 |
| SEQ. ID. NO. 19670 | 108-AlaGlyMetLysGluGlyGlyLeuThrLysAspAlaMet-120 |
| SEQ. ID. NO. 19671 | 177-PheGlyAlaLysAlaAspGlyThrPheGlySer-187 |
| SEQ. ID. NO. 19672 | 207-MetLysAsnProLeuLeuArg-213 |
| SEQ. ID. NO. 19673 | 286-ValSerAspGlnProIleGluGlyGluGluTyrThrLysArgLeuArgGlyGlyValLeu-305 |
| SEQ. ID. NO. 19674 | 391-ValSerHisGlyIleArgArgArgGluAlaVal-401 |
| SEQ. ID. NO. 19675 | 445-LeuProGluAspLysThrGluAlaAlaValLysPheAspThrAspHisLeuGluHis-463 |
| Hydrophilic Regions - Hopp-Woods | |
| SEQ. ID. NO. 19676 | 4-GlnLeuGlyLysGlyAlaAspAlaPro-12 |
| SEQ. ID. NO. 19677 | 18-LeuGluAspArgProProPhe-24 |
| SEQ. ID. NO. 19678 | 109-GlyMetLysGluGlyGlyLeuThrLysAspAlaMet-120 |
| SEQ. ID. NO. 19679 | 179-AlaLysAlaAspGly-183 |
| SEQ. ID. NO. 19680 | 289-GlnProIleGluGlyGluGluTyrThrLysArgLeuArgGly-302 |
| SEQ. ID. NO. 19681 | 394-GlyIleArgArgArgGluAlaVal-401 |
| SEQ. ID. NO. 19682 | 445-LeuProGluAspLysThrGluAlaAlaValLysPheAspThrAspHisLeuGluHis-463 |
| a537 | |
| AMPHI Regions - AMPHI | |
| SEQ. ID. NO. 19683 | 38-GlnIleArgAspGlyGlyAspAlaLeuHisTyrLeuAsnArgIle-52 |
| SEQ. ID. NO. 19684 | 86-HisGlyGluHisHis-90 |
| SEQ. ID. NO. 19685 | 109-GlyTyrLeuTyrAsnGlyValHisGlu-117 |
| SEQ. ID. NO. 19686 | 138-ArgGlnValAspGlyLeuMetSerAlaIleTyr-148 |
| SEQ. ID. NO. 19687 | 182-ArgPheGluArgHisCys-187 |
| SEQ. ID. NO. 19688 | 194-ProGluAlaGlyArgLysTyrTyrArgAsnAla-204 |
| SEQ. ID. NO. 19689 | 281-ArgProValArgValLeuThrAlaGly-289 |
| SEQ. ID. NO. 19690 | 315-TyrThrAlaValPheAspTyrValArgAsnGlyArgArgAla-328 |
| Antigenic Index - Jameson-Wolf | |
| SEQ. ID. NO. 19691 | 21-ThrGlnAsnGlnSerLeuProAlaGly-29 |
| SEQ. ID. NO. 19692 | 32-ValTyrProSerAlaProGlnIleArgAspGlyGlyAspAla-45 |
| SEQ. ID. NO. 19693 | 69-AsnSerAlaArgArgHisAlaArg-76 |
| SEQ. ID. NO. 19694 | 80-LeuAsnProGluAspGlyHisGlyGluHisHisProAspAsnProHis-95 |
| SEQ. ID. NO. 19695 | 99-GlnLysLeuThrGluArgThrArgLeu-107 |
| SEQ. ID. NO. 19696 | 115-ValHisGluAsnIleSerThrGluGluGluAlaAlaGluSerSerAspSerAspIleArgThrGlnGlnArgGlnValAspGlyLeu-143 |
| SEQ. ID. NO. 19697 | 152-SerLeuLeuAspArgHisThrAspGluAlaGly-162 |
| SEQ. ID. NO. 19698 | 165-PheValArgGluAsnGlyLysThr-172 |
| SEQ. ID. NO. 19699 | 178-GlnGlyAsnGlyArgPheGluArgHisCysAlaGlnGlyArgAsnGlnProGluAlaGlyArgLysTyrTyrArgAsnAlaCysHisAsnGly-208 |
| SEQ. ID. NO. 19700 | 212-TyrThrAspGluAlaMetPro-218 |
| SEQ. ID. NO. 19701 | 237-PheHisGlyGluArgProAspProValProGluTyrGluIleThrGlyAsnProAlaSer-256 |
| SEQ. ID. NO. 19702 | 258-AspPheSerGluAlaAlaGly-264 |
| SEQ. ID. NO. 19703 | 266-IleThrMetLysSer-270 |
| SEQ. ID. NO. 19704 | 274-TyrGlnGlyLysAsnGluIleArgPro-282 |
| SEQ. ID. NO. 19705 | 287-ThrAlaGlyAsnAspProAsnGlyArgLeuThr-297 |
| SEQ. ID. NO. 19706 | 320-AspTyrValArgAsnGlyArgArgAlaGlnAla-330 |
| SEQ. ID. NO. 19707 | 334-PheArgThrArgLysProAspTyrProTyr-343 |
| SEQ. ID. NO. 19708 | 345-GluValAsnGlyGlyGluThrLeuAlaValArgLysGlyGluLys-359 |
| SEQ. ID. NO. 19709 | 364-TrpArgGlyArgTrpCysLeu-370 |
| SEQ. ID. NO. 19710 | 376-TyrThrTyrArgGlnArgProGlySerArgLeuSerIleGlyArgHisLysAlaGlyGly-395 |
| SEQ. ID. NO. 19711 | 401-AspGlyMetAlaGlySer-406 |
| SEQ. ID. NO. 19712 | 408-IleThrLeuAlaProGluGlyGluThrGluArgGly-419 |
| Hydrophilic Regions - Hopp-Woods | |
| SEQ. ID. NO. 19713 | 37-ProGlnIleArgAspGlyGlyAsp-44 |
| SEQ. ID. NO. 19714 | 69-AsnSerAlaArgArgHisALaArg-76 |
| SEQ. ID. NO. 19715 | 81-AsnProGluAspGlyHisGlyGluHisHisProAsp-92 |
| SEQ. ID. NO. 19716 | 100-LysLeuThrGluArgThrArgLeu-107 |
| SEQ. ID. NO. 19717 | 119-IleSerThrGluGluGluAlaAlaGluSerSerAspSerAspIleArgThrGlnGlnArgGlnValAsp-141 |

TABLE 1-continued

| | |
|---|---|
| SEQ. ID. NO. 19718 | 152-SerLeuLeuAspArgHisThrAspGluAlaGly-162 |
| SEQ. ID. NO. 19719 | 165-PheValArgGluAsnGlyLys-171 |
| SEQ. ID. NO. 19720 | 179-GlyAsnGlyArgPheGluArgHisCysAlaGlnGlyArgAsnGlnProGluAlaGlyArgLysTyrTyrArg-202 |
| SEQ. ID. NO. 19721 | 238-HisGlyGluArgProAspProValProGlu-247 |
| SEQ. ID. NO. 19722 | 258-AspPheSerGluAlaAlaGly-264 |
| SEQ. ID. NO. 19723 | 266--IleThrMetLysSer-270 |
| SEQ. ID. NO. 19724 | 275-GlnGlyLysAsnGluIleArgPro-282 |
| SEQ. ID. NO. 19725 | 289-GlyAsnAspProAsnGlyArg-295 |
| SEQ. ID. NO. 19726 | 323-ArgAsnGlyArgArgAlaGlnAla-330 |
| SEQ. ID. NO. 19727 | 334-PheArgThcArgLysProAsp-340 |
| SEQ. ID. NO. 19728 | 352-LeuAlaValArgLysGlyGluLys-359 |
| SEQ. ID. NO. 19729 | 377-ThrTyrArgGlnArgProGlySer-384 |
| SEQ. ID. NO. 19730 | 387-SerIleGlyArgHisLysAla-393 |
| SEQ. ID. NO. 19731 | 412-ProGluGlyGluThrGluArgGly-419 |
| a538 | |
| AMPHI Regions - AMPHI | |
| SEQ. ID. NO. 19732 | 42-ThrAlaLeuAlaGluAlaValGluLeuValLysAlaAlaGly-55 |
| SEQ. ID. NO. 19733 | 79-LysAlaAlaGluLeuSerGluAlaValAla-88 |
| SEQ. ID. NO. 19734 | 105-GlnGluArgAsnLeuGluLysIleLeuGlnCysArgValLeuAspArgVal-121 |
| SEQ. ID. NO. 19735 | 145-GlnLeuSerHisLeuAlaGlyArgLeuIleArgGlyTyrGlyHisLeuGln-161 |
| SEQ. ID. NO. 19736 | 188-IleAsnAlaLeuLysLysGlnLeuAla-196 |
| SEQ. ID. NO. 19737 | 211-SerGlyThrIleLysThrPheAlaLeuValGlyTyrThrAsn-224 |
| SEQ. ID. NO. 19738 | 231-PheAsnArgLeuThrLys-236 |
| SEQ. ID. NO. 19739 | 271-GlyPheValSerAspLeuProHisLysLeuIleSerAlaPheSerAlaThrLeuGlu-289 |
| SEQ. ID. NO. 19740 | 307-AsnSerGlyGlnGlnIleGluAspValGluAsnValLeuGlnGluIleHis-323 |
| SEQ. ID. NO. 19741 | 365-GluAsnThrGlyIleAspAlaLeuArgGluAlaIleAlaGluTyrCysAla-381 |
| Antigenic Index - Jameson-Wolf | |
| SEQ. ID. NO. 19742 | 1-MetThrGlyArgThrGlyArgAsnGlySerThrGlnAlaGlnProGluArgVal-18 |
| SEQ. ID. NO. 19743 | 24- MetLeuAspLysAspGlyThrGlySerSerAlaThrArgLeuAsnGly-39 |
| SEQ. ID. NO. 19744 | 48-ValGluLeuValLys-52 |
| SEQ. ID. NO. 19745 | 54-AlaGlyGlyAspSerValArgValGluThrAlaLysArgAspArgProHisThr-71 |
| SEQ. ID. NO. 19746 | 77- ThrGlyLysAlaAlaGluLeuSerGlu-85 |
| SEQ. ID. NO. 19747 | 100- GluLeuThrProThrGlnGluArgAsnLeuGluLys-111 |
| SEQ. ID. NO. 19748 | 129-AlaArgArgAlaArgThrGlnGluGlyArgLeuGlnVal-141 |
| SEQ. ID. NO. 19749 | 161-GlnSerGlnArgGlyGlyIleGlyMetLysGlyProGlyGluThrLysLeuGluThrAspArgArgLeuIle-184 |
| SEQ. ID. NO. 19750 | 189-AsnAlaLeuLysLysGlnLeuAlaAsnLeuLysLysGlnArgAlaLeuArgArgLysSerArgGluSerGlyThrIleLysThr-216 |
| SEQ. ID. NO. 19751 | 224-AsnValGlyLysSerSerLeu-230 |
| SEQ. ID. NO. 19752 | 233-ArgLeuThrLysSerGlyIleTyrAla-241 |
| SEQ. ID. NO. 19753 | 257-TyrIleSerProGluCys-262 |
| SEQ. ID. NO. 19754 | 287-ThrLeuGluGluThrAlaGln-293 |
| SEQ. ID. NO. 19755 | 304-AlaAlaProAsnSerGlyGlnGlnIleGluAspValGluAsnValLeu-319 |
| SEQ. ID. NO. 19756 | 323-HisAlaGlyAspIlePro-328 |
| SEQ. ID. NO. 19757 | 333-TyrAsnLysThrAspLeuLeuProSerGluGluGlnAsnThrGlyIle-348 |
| SEQ. ID. NO. 19758 | 365-GluAsnThrGlyIleAspAlaLeuArgGluAlaIle-376 |
| SEQ. ID. NO. 19759 | 381-AlaAlaAlaProAsnThrAspGluThrGluMetPro-392 |
| Hydrophilic Regions - Hopp-Woods | |
| SEQ. ID. NO. 19760 | 1-MetThrGlyArgThrGlyArgAsnGlySerThr-11 |
| SEQ. ID. NO. 19761 | 13-AlaGlnProGluArg-17 |
| SEQ. ID. NO. 19762 | 25- LeuAspLysAspGlyThrGly-31 |
| SEQ. ID. NO. 19763 | 48-ValGluLeuValLys-52 |
| SEQ. ID. NO. 19764 | 54-AlaGlyGlyAspSerValArgValGluThrAlaLysArgAspArgProHis-70 |
| SEQ. ID. NO. 19765 | 78- GlyLysAlaAlaGluLeuSerGlu-85 |
| SEQ. ID. NO. 19766 | 101- LeuThrProThrGlnGluArgAsnLeuGluLys-111 |
| SEQ. ID. NO. 19767 | 129-AlaArgArgAlaArgThrGlnGluGlyArgLeuGlnVal-141 |
| SEQ. ID. NO. 19768 | 161-GlnSerGlnArgGlyGlyrle-167 |
| SEQ. ID. NO. 19769 | 171-GlyProGlyGluThrLysLeuGluThrAspArgArgLeuIle-184 |
| SEQ. ID. NO. 19770 | 189-AsnAlaLeuLysLysGlnLeuAlaAsnLeuLysLysGlnArgAlaLeuArgArgLysSerArgGluSerGlyThr-213 |
| SEQ. ID. NO. 19771 | 287-ThrLeuGluGluThrAlaGln-293 |
| SEQ. ID. NO. 19772 | 310-GlnGlnIleGluAspValGluAsnValLeu-319 |
| SEQ. ID. NO. 19773 | 337-AspLeuLeuProSerGluGluGlnAsn-345 |
| SEQ. ID. NO. 19774 | 370-AspAlaLeuArgGluAlaIle-376 |
| SEQ. ID. NO. 19775 | 384-ProAsnThrAspGluThrGluMetPro-392 |
| a539-2 | |
| AMPHI Regions - AMPHI | |
| SEQ. ID. NO. 19776 | 18-ArgGlnArgGluHisHisArgLeu-25 |
| SEQ. ID. NO. 19777 | 44-LeuValGlyGlyPheAspPheLeuArgValIleGlyCysGlyGlyValAlaTyrLeuProAspPheGlnGln-67 |
| Antigenic Index - Jameson-Wolf | |
| SEQ. ID. NO. 19778 | 1-MetGluAspLeuGlnGluIleGly-8 |
| SEQ. ID. NO. 19779 | 15-LysValGlyArgGlnArgGluHisHisArgLeuHisHisPrcGlnProGlyAsnGlyGluAlaAspAsp-37 |
| SEQ. ID. NO. 19780 | 63-ProAspPheGlnGlnAsnValGlyLysAlaAsp-73 |
| SEQ. ID. NO. 19781 | 77-ValProAspAspAlaAlaAla-83 |
| SEQ. ID. NO. 19782 | 88-IleGluValAspAlaAspAspAlaValCys-97 |
| SEQ. ID. NO. 19783 | 102-LeuPheAspGlnProAspAlaGlyGlyAlaGlyAspAlaAlaGluHis-117 |
| Hydrophilic Regions - Hopp-Woods | |
| SEQ. ID. NO. 19784 | 1-MetGluAspLeuGlnGluIleGly-8 |
| SEQ. ID. NO. 19785 | 15-LysValGlyArgGlnArgGluHisHisArg-24 |
| SEQ. ID. NO. 19786 | 31-GlyAsnGlyGluAlaAspAsp-37 |
| SEQ. ID. NO. 19787 | 69-ValGlyLysAlaAsp-73 |

TABLE 1-continued

| | |
|---|---|
| SEQ. ID. NO. 19788 | 78-ProAspAspAlaAlaAla-83 |
| SEQ. ID. NO. 19789 | 88-IleGluValAspAlaAspAspAlaValCys-97 |
| SEQ. ID. NO. 19790 | 102-LeuPheAspGlnProAspAlaGlyGlyAlaGlyAspAlaAlaGluHis-117 |
| a542 | |
| AMPHI Regions - AMPHI | |
| SEQ. ID. NO. 19791 | 6-ArgIleArgArgCysSerVal-12 |
| Antigenic Index - Jameson-Wolf | |
| SEQ. ID. NO. 19792 | 1-MetProLysTrpSerArgIleArgArgCysSerVal-12 |
| SEQ. ID. NO. 19793 | 20-SerAlaSerArgLeuThrCys-26 |
| SEQ. ID. NO. 19794 | 36-MetArgLeuLysSerSerAspGlyIleAlaSer-46 |
| SEQ. ID. NO. 19795 | 55-GlyProMetProSerGluThrValSerHisLysSerAspSerSerArgAsnThrSerAlaSerArgArgAsnValSerProLysCysProPhe-85 |
| SEQ. ID. NO. 19796 | 89-PheArgGlnAspAlaAlaLysProArgArgPheGlyGlyLys-102 |
| SEQ. ID. NO. 19797 | 106-LeuThrGlySerArg-110 |
| Hydrophilic Regions - Hopp-Woods | |
| SEQ. ID. NO. 19798 | 5-SerArgIleArgArgCysSer-11 |
| SEQ. ID. NO. 19799 | 36-MetArgLeuLysSerSerAspGlyIleAla-45 |
| SEQ. ID. NO. 19800 | 57-MetProSerGluThrValSerHisLysSerAspSerSerArgAsnThrSerAlaSerArgArgAsnValSerPro-81 |
| SEQ. ID. NO. 19801 | 89-PheArgGlnAspAlaAlaLysProArgArgPheGlyGly-101 |
| a544-2 | |
| AMPHI Regions - AMPHI | |
| SEQ. ID. NO. 19802 | 11-AlaLeuIleGlyIleLeu-16 |
| SEQ. ID. NO. 19803 | 55-PheTrpPheProSerCysProGlyCysValSerGluMetPrcLysIleIleLysThrAla-74 |
| SEQ. ID. NO. 19804 | 85-LeuAlaValAlaGlnProIleAspProIleGluSerValArgGlnTyrVal-101 |
| SEQ. ID. NO. 19805 | 116-LysAlaValGlyGlnAlaPhe-122 |
| Antigenic Index - Jameson-Wolf | |
| SEQ. ID. NO. 19806 | 1-MetLysLysIleLeu-5 |
| SEQ. ID. NO. 19807 | 22-IleProAspSerLysThrAlaPro-29 |
| SEQ. ID. NO. 19808 | 35-AspLeuHisGlyLysThrValSerAsnAlaAspLeuGlnGly-48 |
| SEQ. ID. NO. 19809 | 59-SerCysProGlyCys-63 |
| SEQ. ID. NO. 19810 | 66-GluMetProLysIleIleLysThrAlaAsnAspTyrLysAsnLysAsnPhe-82 |
| SEQ. ID. NO. 19811 | 90-ProIleAspProIleGluSerValArgGlnTyrValLysAspTyrGly-105 |
| SEQ. ID. NO. 19812 | 113-AspAlaAspLysAlaVal-118 |
| SEQ. ID. NO. 19813 | 133-IleGlyLysLysGlyGluIleLeu-140 |
| SEQ. ID. NO. 19814 | 144-ValGlyGluProAspPheGlyLysLeuTyrGlnGluIleAspThr-158 |
| Hydrophilic Regions - Hopp-Woods | |
| SEQ. ID. NO. 19815 | 1-MetLysLysIleLeu-5 |
| SEQ. ID. NO. 19816 | 23-ProAspSerLysThr-27 |
| SEQ. ID. NO. 19817 | 66-GluMetProLysIleIleLysThrAlaAsnAspTyrLysAsnLysAsn-81 |
| SEQ. ID. NO. 19818 | 92-AspProIleGluSerValArgGlnTyrValLys-102 |
| SEQ. ID. NO. 19819 | 113-AspAlaAspLysAlaVal-118 |
| SEQ. ID. NO. 19820 | 133-IleGlyLysLy3GlyGluIle-139 |
| a547 | |
| AMPHI Regions - AMPHI | |
| SEQ. ID. NO. 19821 | 7-PheAsnLysThrValAlaSerPheAlaGlnIleValGluThrPheAspVal-23 |
| SEQ. ID. NO. 19822 | 62-AsnArgSerPheLys-66 |
| SEQ. ID. NO. 19823 | 105-LeuHisIlePheThrAsnIleLys-112 |
| Antigenic Index - Jameson-Wolf | |
| SEQ. ID. NO. 19824 | 3-ValAspAsnGlyPheAsnLysThrVal-11 |
| SEQ. ID. NO. 19825 | 35-GlnMetLysGlnArgCysGlyTrp-42 |
| SEQ. ID. NO. 19826 | 53-PheProArgCysGlyPheGluIleProAsnArgSerPheLysGlu-67 |
| SEQ. ID. NO. 19827 | 76-LeuSerGluArgPheArgThrAsnAlaGluValGluIle-88 |
| Hydrophilic Regions - Hopp-Woods | |
| SEQ. ID. NO. 19828 | 36-MetLysGlnArgCys-40 |
| SEQ. ID. NO. 19829 | 60-IleProAsnArgSerPheLysGlu-67 |
| SEQ. ID. NO. 19830 | 76-LeuSerGluArgPheArgThrAsnAlaGluValGluIle-88 |
| a548 | |
| AMPHI Regions - AMPHI | |
| SEQ. ID. NO. 19831 | 14-ValLeuAlaAlaLeuAlaAlaCysLys-22 |
| SEQ. ID. NO. 19832 | 39-SerAlaAlaGluAsnAlaAlaLysPro-47 |
| SEQ. ID. NO. 19833 | 89-PheThrHisCysProAspValCysProThr-98 |
| SEQ. ID. NO. 19834 | 103-TyrSerAspThrLeuLysGlnLeuGlyGlyGln-113 |
| SEQ. ID. NO. 19835 | 132-GluIleIleGlyLysTyrAlaLys-139 |
| Antigenic Index Jameson-Wolf | |
| SEQ. ID. NO. 19836 | 21-CysLysProGlnAspAsnSerAlaAla-29 |
| SEQ. ID. NO. 19837 | 39-SerAlaAlaGluAsnAlaAlaLysProGlnThrArgGlyThrAspMetArgLysGluAspIleGlyGlyAspPheThrLeuThrAspGlyGluGlyLys ProPheAsn-74 |
| SEQ. ID. NO. 19838 | 76-SerAspLeuLysGly-80 |
| SEQ. ID. NO. 19839 | 91-HisCysProAspValCysPro-97 |
| SEQ. ID. NO. 19840 | 104-SerAspThrLeuLysGlnLeuGlyGlyGlnAlaLysAspValLys-118 |
| SEQ. ID. NO. 19841 | 124-1leAspProGluArgAspThrProGluIleIleGlyLysTyrAlaLysGlnPheAsnProAspPhe-145 |
| SEQ. ID. NO. 19842 | 150-AlaThrGlyAspGlnAsnLeu-156 |
| SEQ. ID. NO. 19843 | 169-LysValAsnGlnLysAspAspSerGluAsnTyrLeu-180 |
| SEQ. ID. NO. 19844 | 189-LeuIleAspLysAsnGlyGlu-195 |
| SEQ. ID. NO. 19845 | 200-SerProTyrGlySerGluProGluThrIleAlaAlaAspVal-213 |
| Hydrophilic Regions - Hopp-Woods | |
| SEQ. ID. NO. 19846 | 22-LysProGlnAspAsnSerAla-28 |
| SEQ. ID. NO 19847 | 39-SerAlaAlaGluAsnAlaAlaLysProGlnThrArgGlyThrAspMetArgLysGluAspIleGlyGly-61 |
| SEQ. ID. NO. 19848 | 64-ThrLeuThrAspGlyGluGlyLysPro-72 |

TABLE 1-continued

| | |
|---|---|
| SEQ. ID. NO. 19849 | 76-SerAspLeuLysGly-80 |
| SEQ. ID. NO. 19850 | 111-GlyGlyGlnAlaLysAspValLys-118 |
| SEQ. ID. NO. 19851 | 124-IleAspProGluArgAspThrProGluIleIle-134 |
| SEQ. ID. NO. 19852 | 151-ThrGlyAspGlnAsn-155 |
| SEQ. ID. NO. 19853 | 169-LysValAsnGlnLysAspAspSerGluAsnTyrLeu-180 |
| SEQ. ID. NO. 19854 | 191-AspLysAsnGlyGlu-195 |
| SEQ. ID. NO. 19855 | 203-GlySerGluProGluThrIleAlaAlaAspVal-213 |
| a552-1 | |
| AMPHI Regions - AMPHI | |
| SEQ. ID. NO. 19856 | 18-CysThrAsnAlaPheAlaAlaPro-25 |
| SEQ. ID. NO. 19857 | 29-AlaSerLeuAlaArgTrpLeuAspThr-37 |
| SEQ. ID. NO. 19858 | 41-AspArgAspIleGluLysAsnMetIleGluGlyPheAsnAlaGlyPheLysProTyrAlaAspLysAlaLeuAlaGluMet-67 |
| SEQ. ID. NO. 19859 | 75-AlaAlaGluAlaPheAsnArgTyrArgGluAsnVal-86 |
| SEQ. ID. NO. 19860 | 89-AspLeuIleThrProGluValLys-96 |
| SEQ. ID. NO. 19861 | H6-IleAspGlyMetIleAla-121 |
| SEQ. ID. NO. 19862 | 139-IleLysLysSerMetSerGluIle-146 |
| SEQ. ID. NO. 19863 | 154-SerGlyLysIleAlaGlnHisHisLeuProGluPheThrGluGluLeuArgArg-171 |
| Antigenic Index - Jameson-Wolf | |
| SEQ. ID. NO. 19864 | 25-ProProSerAspAlaSerLeu-31 |
| SEQ. ID. NO. 19865 | 35-LeuAspThrGlnAsnPheAspArgAspIleGluLysAsnMetIle-49 |
| SEQ. ID. NO. 19866 | 53-AsnAlaGlyPheLysProTyrAlaAspLysAlaLeuAlaGluMetProGluAlaLysLysAspGlnAlaAla-76 |
| SEQ. ID. NO. 19867 | 78-AlaPheAsnArgTyrArgGluAsnValLeu-87 |
| SEQ. ID. NO. 19868 | 90-LeuIleThrProGluValLysGlnAlaVal-99 |
| SEQ. ID. NO. 19869 | 105-LysAsnAlaArgGluIleTyrThrGlnGluGluIleAspGly-118 |
| SEQ. ID. NO. 19870 | 131-ValValAlaLysAsnProArgLeuIleLysLysSerMetSer-144 |
| SEQ. ID. NO. 19871 | 153-LeuSerGlyLysIle-157 |
| SEQ. ID. NO. 19872 | 164-GluPheThrGluGluLeuArgArg-171 |
| SEQ. ID. NO. 19873 | 173-IleCysGlyGlyLysAsnProAspAlaGlyCysLysGlnAlaGlyGlnValGlyLysArgHisGlnLys-195 |
| Hydrophilic Regions - Hopp-Woods | |
| SEQ. ID. NO. 19874 | 26-ProSerAspAlaSerLeu-31 |
| SEQ. ID. NO. 19875 | 38-GlnAsnPheAspArgAspIleGluLysAsnMetIle-49 |
| SEQ. ID. NO. 19876 | 58-ProTyrAlaAspLysAlaLeuAlaGluMetProGluAlaLysLysAspGlnAlaAla-76 |
| SEQ. ID. NO. 19877 | 78-AlaPheAsnArgTyrArgGluAsnValLeu-87 |
| SEQ. ID. NO. 19878 | 90-LeuIleThrProGluValLysGlnAlaVal-99 |
| SEQ. ID. NO. 19879 | 105-LysAsnAlaArgGluIleTyrThr-112 |
| SEQ. ID. NO. 19880 | 114-GluGluIleAspGly-118 |
| SEQ. ID. NO. 19881 | 131-ValValAlaLysAsnProArgLeuIleLysLysSerMetSer-144 |
| SEQ. ID. NO. 19882 | 164-GluPheThrGluGluLeuArgArg-171 |
| SEQ. ID. NO. 19883 | 176-GlyLysAsnProAspAlaGlyCysLysGlnAlaGlyGlnValGlyLysArgHisGlnLys-195 |
| a554 | |
| AMPHI Regions - AMPHI | |
| SEQ. ID. NO. 19884 | 38-PheGlnThrProGluThrLeu-44 |
| SEQ. ID. NO. 19885 | 71-AlaAlaLeuThrGlnLeuMet-77 |
| SEQ. ID. NO. 19886 | 110-ArgMetPheValArgProGlyAspThrVal-119 |
| SEQ. ID. NO. 19887 | 124-LeuLeuLysGlyMet-128 |
| SEQ. ID. NO. 19888 | 148-SerIleGluAsnPheValGlnGlnMetAsnLysGlu-159 |
| SEQ. ID. NO. 19889 | 185-AlaLysAspLeuAlaGlnLeuSerGluAlaLeuMetArgAspPheProGluTyrTyrProLeuPheSer-207 |
| SEQ. ID. NO. 19890 | 296-ThrValAlaGlnIle-300 |
| SEQ. ID. NO. 19891 | 331-GluGlnIleLeuGluThrIleGlnProIleProAla-342 |
| Antigenic Index - Jameson-Wolf | |
| SEQ. ID. NO. 19892 | 23-AlaSerProAlaProAsnArgProThrAla-32 |
| SEQ. ID. NO. 19893 | 37-ThrPheGlnThrProGluThr-43 |
| SEQ. ID. NO. 19894 | 53-LeuGlnSerLysGln-57 |
| SEQ. ID. NO. 19895 | 61-AlaLysAsnIleAsnThrProValGlu-69 |
| SEQ. ID. NO. 19896 | 84-LysAsnMetLysSerGlyAsnIleArgSerGluGluAsnLeuLysIleProGlu-101 |
| SEQ. ID. NO. 19897 | 104-TrpAlaSer GluGlySerArgMetPheValArgProGlyAspThrValSerThrAspLysLeuLeu-125 |
| SEQ. ID. NO. 19898 | 143-ArgLeuGlyAsnGlySerIleGluAsnPhe-152 |
| SEQ. ID. NO. 19899 | 156-MetAsnLysGluAlaArgArgLeuGlyMetLysAsnThrValPheLysAsnProThrGlyLeuSerArgGluGlyGlnValSerThrAlaLysAsp LeuAlaGln-190 |
| SEQ. ID. NO. 19900 | 194-AlaLeuMetArgAspPheProGluTyrTyr-203 |
| SEQ. ID. NO. 19901 | 214-LysAsnIleGluGlnAsnAsnArgAsnIleLeu-224 |
| SEQ. ID. NO. 19902 | 226-TyrArgAspAsnAsnValAsnGlyLeuLysAlaGlyHisThrGluSerGlyGlyTyrAsn-245 |
| SEQ. ID. NO. 19903 | 250-TyrSerGlyAsnGlyArgHis-256 |
| SEQ. ID. NO. 19904 | 262-LeuGlySerGluSerAlaGluThrArgAlaSerAspAsnSerLys-276 |
| SEQ. ID. NO. 19905 | 285-PheAspThrProLysIleTyrProLysGlyLysThr-296 |
| SEQ. ID. NO. 19906 | 302-IleSerGlyGlySerLysLysThrValArg-311 |
| SEQ. ID. NO. 19907 | 323-ProHisLysGluAlaLysMetAlaGluGlnIleLeu-334 |
| SEQ. ID. NO. 19908 | 342-AlaProValLysLysGlyGlnIleLeuGlyLysIleLysIleArgGlnAsnGlyTyr-360 |
| SEQ. ID. NO. 19909 | 362-IleAlaGluLysGluIleValAla-369 |
| SEQ. ID. NO. 19910 | 371-GluAsnValLysLysArgSerArgTrpGlnArg-381 |
| Hydrophilic Regions - Hopp-Woods | |
| SEQ. ID. NO. 19911 | 26-AlaProAsnArgProThrAla-32 |
| SEQ. ID. NO. 19912 | 85-AsnMetLysSerGlyAsnIleArgSerGluGluAsnLeuLysIleProGlu-101 |
| SEQ. ID. NO. 19913 | 107-GluGlySerArgMetPheValArgProGlyAspThrValSerThrAspLysLeuLeu-125 |
| SEQ. ID. NO. 19914 | 156-MetAsnLysGluAlaArgArgLeuGlyMet-165 |
| SEQ. ID. NO. 19915 | 174-ThrGlyLeuSerArgGluGlyGlnValSerThrAlaLysAspLeuAlaGln-190 |
| SEQ. ID. NO. 19916 | 214-LysAsnIleGluGlnAsnAsnArg-221 |
| SEQ. ID. NO. 19917 | 227-ArgAspAsnAsnValAsn-232 |
| SEQ. ID. NO. 19918 | 237-GlyHisThrGluSerGly-242 |
| SEQ. ID. NO. 19919 | 264-SerGluSerAlaGluThrArgAlaSerAspAsnSerLys-276 |

TABLE 1-continued

SEQ. ID. NO. 19920 289-LysIleTyrProLysGlyLysThr-296
SEQ. ID. NO. 19921 304-GlyGlySerLysLysThrValArg-311
SEQ. ID. NO. 19922 323-ProHisLysGluAlaLysMetAlaGluGlnIleLeu-334
SEQ. ID. NO. 19923 343-ProValLysLysGlyGlnIle-349
SEQ. ID. NO. 19924 353-IleLysIleArgGln-357
SEQ. ID. NO. 19925 362-IleAlaGluLysGluIleValAla-369
SEQ. ID. NO. 19926 371-GluAsnValLysLysArgSerArgTrp-379
a556
AMPHI Regions - AMPHI
SEQ. ID. NO. 19927 61-IleGluArgLeuLys-65
Antigenic Index - Jameson-Wolf
SEQ. ID. NO. 19928 1-MetAspAsnLysThrLysLeuArgLeu-9
SEQ. ID. NO. 19929 52-ThrSerArgArgGlnGlnArgGlnPheIleGluArgLeuLysLysPheAspIleAspProGluLysGlyArgIleAsnGluAlaAsnLeuArgArgMet TyrHisSerGlyGlyGlnHisGlnLysAspAla-95
SEQ. ID. NO. 19930 102-SerGlnLysCysSerValAspGluAlaHisAlaMetPheLysLysArgProThrArgGlnGluIleAsn-124
SEQ. ID. NO. 19931 127-AlaAlaLysGlnSerArgGlyGlnLysArgProHisArg-139
Hydrophilic Regions - Hopp-Wood
SEQ. ID. NO. 19932 1-MetAspAsnLysThrLysLeuArgLeu-9
SEQ. ID. NO. 19933 53-SerArgArgGlnGlnArgGlnPheIleGluArgLeuLysLysPheAspIleAspProGluLysGlyArgIleAsnGluAlaAsnLeuArgArg MetTyr-85
SEQ. ID. NO. 19934 90-GlnHisGlnLysAspAla-95
SEQ. ID. NO. 19935 105-CysSerValAspGluAlaHisAlaMetPheLysLysArgProThrArgGlnGluIleAsn-124
SEQ. ID. NO. 19936 127-AlaAlaLysGlnSerArgGlyGlnLysArgProHisArg-139
a557
AMPHI Regions - AMPHI
SEQ. ID. NO. 19937 22-GlyAlaAspGlyIle-26
SEQ. ID. NO. 19938 55-SerGlyArgValAspAspAlaAla-62
Antigenic Index - Jameson-Wolf
SEQ. ID. NO. 19939 20-LeuLysGlyAlaAspGlyIleSerProProLeuThrTyrArgSerTrpHisIleGluGlyGlyGlnAlaLeu-43
SEQ. ID. NO. 19940 54-AlaSerGlyArgValAspAspAlaAlaGly-63
SEQ. ID. NO. 19941 68-LeuArgIleAspSerValSerGlnAsnLysGluThrTyrThr-81
SEQ. ID. NO. 19942 100-GlnValLeuLysArgGlyGluProValGlyLysProMet-112
SEQ. ID. NO. 19943 123-AlaAspAsnGluIieLeuGlyLysGlnGluGluGluAla-135
SEQ. ID. NO. 19944 141-MetArgGlnAspAlaAlaGluGlnIleValArg-151
Hydrophilic Regions - Hopp-Woods
SEQ. ID. NO. 19945 21-LysGlyAlaAspGlyIle-26
SEQ. ID. NO. 19946 56-GlyArgValAapAspAlaAlaGly-63
SEQ. ID. NO. 19947 68-LeuArgIleAspSerValSerGlnAsnLysGluThrTyrThr-81
SEQ. ID. NO. 19948 100-GlnValLeuLysArgGlyGluProValGly-109
SEQ. ID. NO. 19949 126-GluIleLeuGlyLysGlnGluGluGluAla-135
SEQ. ID. NO. 19950 141-MetArgGlnAspAlaAlaGluGlnIleValArg-151
a560
AMPHI Regions - AMPHI
SEQ. ID. NO. 19951 30-PheArgAspGlyAlaHisLysMetAlaArgValTrpValLysIleLeu-45
SEQ. ID. NO. 19952 167-ArgMetAlaLysMetPhe-172
SEQ. ID. NO. 19953 192-PheLeuLysTyrProGlyGlu-198
SEQ. ID. NO. 19954 218-MetGlyLysCysGluHisLeuIleGlu-226
Antigenic Index - Jameson-Wolf
SEQ. ID. NO. 19955 29-ProPheArgAspGlyAlaHisLysMet-37
SEQ. ID. NO. 19956 61-GlyAlaGluAsnIleProAspArgProAla-70
SEQ. ID. NO. 19957 76-HisGlnSerGlyTrpGlu-81
SEQ. ID. NO. 19958 95-ValAlaLysArgGluLeuPhe-101
SEQ. ID. NO. 19959 116-IleGlyIleAspArgAsnAsnArgArgGluAlaAsnGluGlnLeuIle-131
SEQ. ID. NO. 19960 134-GlyLeuAlaArgLysAsnGluGlyTyr-142
SEQ. ID. NO. 19961 148-ProGluGlyThrArgLeuAlaProGlyLysArgGlyLysTyrLysLeuGlyGly-165
SEQ. ID. NO. 19962 182-AsnSerGlyGluPheTrpProLysAsnSerPheLeuLysTyrProGlyGluIle-199
SEQ. ID. NO. 19963 209-HisAlaSerGlySerGluAlaGluLeuMetGlyLysCysGluHisLeuIle-225
SEQ. ID. NO. 19964 242-MetProSerGluThrAla-247
Hydrophilic Regions - Hopp-Woods
SEQ. ID. NO. 19965 29-ProPheArgAspGlyAlaHisLysMet-37
SEQ. ID. NO. 19966 64-AsnIleProAapArgProAla-70
SEQ. ID. NO. 19967 95-ValAlaLysArgGluLeuPhe-101
SEQ. ID. NO. 19968 116-IleGlyIleAspArgAsnAsnArgArgGluAlaAsnGluGlnLeuIle-131
SEQ. ID. NO. 19969 134-GlyLeuAlaArgLysAsnGlu-140
SEQ. ID. NO. 19970 149-GluGlyThrArgLeuAlaProGlyLysArgGlyLysTyrLysLeuGlyGly-165
SEQ. ID. NO. 19971 211-SerGlySerGluAlaGluLeuMetGlyLysCysGluHisLeuIle-225
SEQ. ID. NO. 19972 242-MetProSerGluThrAla-247
a561
AMPHI Regions - AMPHI
SEQ. ID. NO. 19973 22-GlyLeuTrpValGlyLeuAlaAla-29
SEQ. ID. NO. 19974 46-AlaSerValIleGluGluAlaGlyAsn-54
SEQ. ID. NO. 19975 79-ValAlaGluPheGluLysSerLeuLysArgIleAlaGln-91
SEQ. ID. NO. 19976 128-SerTyrArgArgProThrGlnVal-135
SEQ. ID. NO. 19977 172-MetThrLeuValSerSer-177
SEQ. ID. NO. 19978 188-ValIleArgProLeuGlnAlaLeuArgGluGlyAlaGluArgIleGlyArgArgCysPheAspIle-209
SEQ. ID. NO. 19979 219-PheLysGlnValGlyArgCysPheAsnGlnMet-229
SEQ. ID. NO. 19980 238-AspAspLeuGluGlyGlnValAlaGluGlnThrArgSerLeuGluLysGln-254
SEQ. ID. NO. 19581 265-ThrArgAspLeuHisCilnser-271
SEQ. ID. NO. 19982 275-GlnGlnAlaAlaGluHisPhe-281
SEQ. ID. NO. 19983 283-AsnArgIleLeuPro-287

TABLE 1-continued

| | |
|---|---|
| SEQ. ID. NO. 19984 | 317-AlaSerAspLeuGlyLysTyrHisGlu-325 |
| SEQ. ID. NO. 19985 | 339-ArgLeuLeuLeuSerPheProAsnGly-347 |
| SEQ. ID. NO. 19986 | 358-LeuGlnThrLeuGlyArgGlnLeuGly-366 |
| SEQ. ID. NO. 19987 | 392-GlnGlyLeuHisAspSerIleAlaGlnAlaLeuThr-403 |
| SEQ. ID. NO. 19988 | 434-GlyValGlnGluCysTyrGluAspValArgGluLeu-445 |
| SEQ. ID. NO. 19989 | 456-LysGluPheProGluAlaValAlaAspLeuPheSerArgPheThrGlnGlnThrGly-474 |
| SEQ. ID. NO. 19990 | 504-LeuSerAsnIleArgLysHisAla-511 |
| SEQ. ID. NO. 19991 | 540-ThrGluAsnIleGlyGluProSer-547 |
| Antigenic Index - Jameson-Wolf | |
| SEQ. ID. NO. 19992 | 6-ArgPheSerAspGlyIleSer-12 |
| SEQ. ID. NO. 19993 | 48-ValIleGluGluAlaGlyAsn-54 |
| SEQ. ID. NO. 19994 | 66-AlaGlyGluGlySerProArgAlaGlnIleAspAsnGlnValAlaGluPheGluLysSerLeuLysArgIleAlaGlnSerAspAlaIleHisPro-97 |
| SEQ. ID. NO. 19995 | 99-IleProSerAspThrProLeu-105 |
| SEQ. ID. NO. 19996 | 124-ProProLeuGlnSerTyrArgArgProThrGlnValAspLeu-137 |
| SEQ. ID. NO. 19997 | 152-GluAsnAlaAsnGluLysAsnThr-159 |
| SEQ. ID. NO. 19998 | 193-GlnAlaLeuArgGluGlyAlaGluArgIleGlyArgArgCysPheAsp-208 |
| SEQ. ID. NO. 19999 | 210-ProValProGluGlyGlyThrProGluPheLysGlnValGlyArgCysPheAsnGlnMetGlyGlyArgLeuLysIleLeuTyrAspAspLeuGlu GlyGlnValAlaGluGlnThrArgSerLeuGluLysGlnAsnGlnAsnLeu-258 |
| SEQ. ID. NO. 20000 | 263-GlnThrThrArgAspLeuHisGlnSerTyrIle-273 |
| SEQ. ID. NO. 20001 | 289-ValGlyAlaAspSerGlyArgValCysLeuAspGlyGlySerAsp-303 |
| SEQ. ID. NO. 20002 | 310-HisAlaAspCysGlyThrAlaAlaSerAspLeuGlyLysTyrHisGlu-325 |
| SEQ. ID. NO. 20003 | 332-TyrGlnAsnGluThrLeuGly-338 |
| SEQ. ID. NO. 20004 | 344-PheProAsnGlyIleSerLeuAspGluAspAspArgIleLeu-357 |
| SEQ. ID. NO. 20005 | 360-ThrLeuGlyArgGlnLeu-365 |
| SEQ. ID. NO. 20006 | 371-GlyAlaLysGlnGluGluGluLysArgLeu-380 |
| SEQ. ID. NO. 20007 | 384-LeuGlnGluArgAsnLeu-389 |
| SEQ. ID. NO. 20008 | 394-LeuHisAspSerIle-398 |
| SEQ. ID. NO. 20009 | 415-AlaPheAlaGluAsnLysArgGluGluAlaAlaGlu-426 |
| SEQ. ID. NO. 20010 | 434-GlyValGlnGluCysTyrGluAspValArgGlu-444 |
| SEQ. ID. NO. 20011 | 450-ArgThrLysIleSerAsnLysGluPheProGluAlaVal-462 |
| SEQ. ID. NO. 20012 | 468-ArgPheThrGlnGlnThrGlyThrThrVal-477 |
| SEQ. ID. NO. 20013 | 480-AlaTrpGluAsnGlyThrHisLeuProThrGlnAspGluGlnLeu-494 |
| SEQ. ID. NO. 20014 | 503-SerLeuSerAsnIleArgLysHisAlaHis-512 |
| SEQ. ID. NO. 20015 | 519-ArgLeuLeuLysGlnAspGlySerPheThr-528 |
| SEQ. ID. NO. 20016 | 531-IleGlnAspAsnGlyGlnGlyPheAspThrGluAsnIleGlyGluProSerGlySerHis-550 |
| SEQ. ID. NO. 20017 | 556-MetGlnGluArgAlaLysArgIle-563 |
| SEQ. ID. NO. 20018 | 568-GluIleArgSerGlnAlaGlnGlnGlyThrThr-578 |
| SEQ. ID. NO. 20019 | 584-AlaSerGluGluSerLeuLys-590 |
| Hydrophilic Regions - Hopp-Woods | |
| SEQ. ID. NO. 20020 | 48-ValIleGluGluAlaGlyAsn-54 |
| SEQ. ID. NO. 20021 | 68-GluGlySerProArgAlaGlnile-75 |
| SEQ. ID. NO. 20022 | 78-GlnValAlaGluPheGluLysSerLeuLysArgIleAlaGln-91 |
| SEQ. ID. NO. 20023 | 128-SerTyrArgArgProThrGln-134 |
| SEQ. ID. NO. 20024 | 152-GluAsnAlaAsnGluLys-157 |
| SEQ. ID. NO. 20025 | 193-GlnAlaLeuArgGluGlyAlaGluArgIleGlyArgArgCysPhe-207 |
| SEQ. ID. NO. 20026 | 213-GluGlyGlyThrProGluPheLysGlnValGly-223 |
| SEQ. ID. NO. 20027 | 235-1leLeuTyrAspAspLeuGluGlyGlnValAlaGluGlnThrArgSerLeuGluLysGlnAsnGln-256 |
| SEQ. ID. NO. 20028 | 264-ThrThrArgAGpLeuHis-269 |
| SEQ. ID. NO. 20029 | 290-GlyAlaAspSerGlyArgValCysLeu-298 |
| SEQ. ID. NO. 20030 | 312-AspCysGlyThrAlaAlaSerAspLeuGlyLysTyrHisGlu-325 |
| SEQ. ID. NO. 20031 | 349-SerLeuAspGluAspAspArgIleLeu-357 |
| SEQ. ID. NO. 20032 | 371-GlyAlaLysGlnGluGluGluLysArgLeu-380 |
| SEQ. ID. NO. 20033 | 384-LeuGlnGluArgAsnLeu-389 |
| SEQ. ID. NO. 20034 | 415-AlaPheAlaGluAsnLysArgGluGluAlaAlaGlu-426 |
| SEQ. ID. NO. 20035 | 437-GluCysTyrGluAspValArgGlu-444 |
| SEQ. ID. NO. 20036 | 451-ThrLysIleSerAsnLysGluPheProGluAlaVal-462 |
| SEQ. ID. NO. 20037 | 488-ProThrGlnAspGluGlnLeu-494 |
| SEQ. ID. NO. 20038 | 503-SerLeuSerAsnIleArgLysHisAlaHis-512 |
| SEQ. ID. NO. 20039 | 519-ArgLeuLeuLysGlnAspGly-525 |
| SEQ. ID. NO. 20040 | 533-AspAsnGlyGlnGlyPheAspThrGluAsnIleGlyGluProSerGly-548 |
| SEQ. ID. NO. 20041 | 556-MetGlnGluArgAlaLysArgIle-563 |
| SEQ. ID. NO. 20042 | 568-GluIleArgSerGlnAlaGln-574 |
| SEQ. ID. NO. 20043 | 584-AlaSerGluGluSerLeuLys-590 |
| a562 | |
| AMPHI Regions - AMPHI | |
| SEQ. ID. NO. 20044 | 48-TrpSerLeuValSerAlaTrpMetValValIle-58 |
| SEQ. ID. NO. 20045 | 84-LeuGluThrThrVal-88 |
| SEQ. ID. NO. 20046 | 90-SerAlaValArgMetLeu-95 |
| SEQ. ID. NO. 20047 | 97-PheThrProTyrThrThrValAlaSerThrSer-107 |
| SEQ. ID. NO. 20048 | 116-ThrPhePheAlaProLeuSerArgThrLeu-125 |
| SEQ. ID. NO. 20049 | 132-AsnAlaProValHisSerMetThrLysSerThrProSerSerPheHis-147 |
| SEQ. ID. NO. 20050 | 183-ValSerAsnLeuValArgTrpAlaLeu-191 |
| Antigenic Index - Jameson-Wolf | |
| SEQ. ID. NO. 20051 | 10-AsnSerGlySerThrLysProThr-17 |
| SEQ. ID. NO. 20052 | 32-ProLeuArgAlaArgArgArgSerLeuTrpArg-42 |
| SEQ. ID. NO. 20053 | 72-AlaThrGlyGluArgGlnLeuVal-79 |
| SEQ. ID. NO. 20054 | 105-SerThrSerSerProProGlyAlaGluMet-114 |
| SEQ. ID. NO. 20055 | 138-MetThrLysSerThrProSerSerPheHisGlySerSerAla-151 |
| SEQ. ID. NO. 20056 | 154-ArgValXxxLysXxxGlyIle-160 |
| SEQ. ID. NO. 20057 | 167-ArgLeuProProSerTrpAspThrSerAlaSerLysArgProCysThr-182 |

TABLE 1-continued

| | |
|---|---|
| Hydrophilic Regions - Hopp-Woods | |
| SEQ. ID. NO. 20058 | 33-LeuArgAlaArgArgArgSerLeuTrp-41 |
| SEQ. ID. NO. 20059 | 72-AlaThrGlyGluArgGlnLeuVal-79 |
| SEQ. ID. NO. 20060 | 110-ProGlyAlaGluMet-114 |
| SEQ. ID. NO. 20061 | 139-ThrLysSerThrPro-143 |
| SEQ. ID. NO. 20062 | 175-SerAlaSerLysArgProCysThr-182 |
| a565 | |
| AMPHI Regions - AMPHI | |
| SEQ. ID. NO. 20063 | 50-AlaThrCysThrArgAlaMetSerLysSer-59 |
| SEQ. ID. NO. 20064 | 66-SerSerTrpAlaArg-70 |
| SEQ. ID. NO. 20065 | 84-IleSerThrTrpSerAspLeu-90 |
| SEQ. ID. NO. 20066 | 103-AspPheMetSerGlnLeuAspLeuThr-111 |
| SEQ. ID. NO. 20067 | 140-SerHisSerSerGluThrIleSerSerCysProAlaMetAlaSerIleThrLysProAsn-159 |
| SEQ. ID. NO. 20068 | 184-AlaAsnThrThrSerAlaPhe-190 |
| Antigenic Index - Jameson-Wolf | |
| SEQ. ID. NO. 20069 | 1-MetAspSerThrLeuSerLysThrCys-9 |
| SEQ. ID. NO. 20070 | 23-PheAlaArgProArgProALaAlaSerAsnThrSerLeu-35 |
| SEQ. ID. NO. 20071 | 37-PheAlaSerProAsnAspThrGlySer-45 |
| SEQ. ID. NO. 20072 | 55-AlaMetSerLysSerSerAlaLysTyrGly-64 |
| SEQ. ID. NO. 20073 | 67-SerTrpAlaArgThrArgProThrValCysProProLeuProLysProThrIle-84 |
| SEQ. ID. NO. 20074 | 99-CysArgSerSerAspPheMetSer-106 |
| SEQ. ID. NO. 20075 | 109-AspLeuThrLysArgProThrSerAlaSerLeuProProLysArgLysGlyAlaIle-127 |
| SEQ. ID. NO. 20076 | 129-IleAspSerArgThrAlaAla-135 |
| SEQ. ID. NO. 20077 | 140-SerHisSerSerGluThrIleSerSerCysProAla-151 |
| SEQ. ID. NO. 20078 | 155-1leThrLysProAsnSerProProCysAlaArgTyr-166 |
| SEQ. ID. NO. 20079 | 170-LeuArgLeuSerProThrGlu-176 |
| SEQ. ID. NO. 20080 | l94-SerIleAlaAsnSerIleAsnThrCysArgGlnProPro-206 |
| Hydrophilic Regions - Hopp-Woods | |
| SEQ. ID. NO. 20081 | 24-AlaArgProArgProAlaAla-30 |
| SEQ. ID. NO. 20082 | 39-SerProAsnAspThrGlySer-45 |
| SEQ. ID. NO. 20083 | 55-AlaMetSerLysSerSerAla-61 |
| SEQ. ID. NO. 20084 | 69-AlaArgThrArgPro-73 |
| SEQ. ID. NO. 20085 | 100-ArgSerSerAspPhe-104 |
| SEQ. ID. NO. 20086 | 109-AspLeuThrLysArgProThrSer-116 |
| SEQ. ID. NO. 20087 | 119-LeuProProLysArgLysGlyAlaIle-127 |
| SEQ. ID. NO. 20088 | 129-IleAspSerArgThr-133 |
| SEQ. ID. NO. 20089 | 141-HisSerSerGluThrIleSer-147 |
| SEQ. ID. NO. 20090 | 156-ThrLysProAsnSer-160 |
| a566 | |
| Antigenic Index - Jameson-Wolf | |
| SEQ. ID. NO. 20091 | 35-TyrProAsnCysGlyAlaAspGlyAlaGlyGlyLysGlyHis-48 |
| SEQ. ID. NO. 20092 | 61-AlaValGlyGlyGluGluGlyGlyValValAlaAspAspValAlaArgAlaAspGlyGlyLysAlaAspGlyGlyArgIleAlaArg-89 |
| SEQ. ID. NO. 20093 | 105-SerAlaGluArgAlaGlyAspAspPheAla-114 |
| Hydrophilic Regions - Hopp-Woods | |
| SEQ. ID. NO. 20094 | 39-GlyAlaAspGlyAlaGlyGlyLysGlyHis-48 |
| SEQ. ID. NO. 20095 | 63-GlyGlyGluGluGlyGlyValValAlaAspAspValAlaArgAlaAspGlyGlyLysAlaAspGlyGlyArgIleAlaArg-89 |
| SEQ. ID. NO. 20096 | 105-SerAlaGluArgAlaGlyAspAspPheAla-114 |
| a567 | |
| AMPHI Regions - AMPHI | |
| SEQ. ID. NO. 20097 | 60-GlyValTyrGlnVal-64 |
| SEQ. ID. NO. 20098 | 98-GluLeuValGlnGluIleAlaArgGluVal-107 |
| SEQ. ID. NO. 20099 | 112-AlaLeuLysAlaVal-116 |
| SEQ. ID. NO. 20100 | 154-TyrAlaLeuGluGlyIleSerAspLeuIleAlaThrValArgLysIleArgGln-171 |
| SEQ. ID. NO. 20101 | 180-ThrGlyIleValArg-184 |
| SEQ. ID. NO. 20102 | 195-AlaGluValSerGluGlnLeuArgSerHisPheGlyAspLeuLeu-209 |
| Antigenic index - Jameson-Wolf | |
| SEQ. ID. NO. 20103 | 10-AsnGlnLysGlyGlyValGlyLysThrThrThr-20 |
| SEQ. ID. NO. 20104 | 28-LeuAlaSerArgGlyLysArg-34 |
| SEQ. ID. NO. 20105 | 38-ValAspLeuAspProGlnGlyAsnAlaThrThrGlySerGlyIleAspLysAlaSerLeuGlnSerGly-60 |
| SEQ. ID. NO. 20106 | 67-GlyAspAlaAspValLysSerAlaAlaValArgSerLysGluGlyGlyTyr-83 |
| SEQ. ID. NO. 20107 | 95-AlaGluIleGluLeu-99 |
| SEQ. ID. NO. 20108 | 101-GlnGluIleAlaArgGluValArgLeuLysAsnAlaLeu-113 |
| SEQ. ID. NO. 20109 | 115-AlaValAlaGluAspTyrAsp-121 |
| SEQ. ID. NO. 20110 | 127-CysProProSerLeu-131 |
| SEQ. ID. NO. 20111 | 164-AlaThrValArgLysIleArgGlnAlaValAsnProAspLeuAspIle-179 |
| SEQ. ID. NO. 20112 | 185-ThrMetTyrAspSerArgSerArgLeuValAlaGluValSerGluGlnLeuArgSerHisPheGlyAspLeu-208 |
| SEQ. ID. NO. 20113 | 214-IleProArgAsnIleArgLeuAlaGluAlaProSerHisGly-227 |
| SEQ. ID. NO. 20114 | 235-AlaGlnAlaLysGlyAlaLys-241 |
| SEQ. ID. NO. 20115 | 248-AspGluLeuMetAla-252 |
| Hydrophilic Regions - Hopp-Woods | |
| SEQ. ID. NO. 20116 | 10-AsnGlnLysGlyGlyValGlyLys-17 |
| SEQ. ID. NO. 20117 | 28-LeuAlaSerArgGlyLysArg-34 |
| SEQ. ID. NO. 20118 | 40-LeuAspProGlnGly-44 |
| SEQ. ID. NO. 20119 | 50-SerGlyIleAspLysAlaSerLeu-57 |
| SEQ. ID. NO. | 2012067-GlyAspAlaAspValLysSerAlaAlaValArgSerLysGluGlyGly-82 |
| SEQ. ID. NO. 20121 | 95-AlaGluIleGluLeu-99 |
| SEQ. ID. NO. 20122 | 101-GlnGluIleAlaArgGluValArgLeuLysAsnAlaLeu-113 |
| SEQ. ID. NO. 20123 | 115-AlaValAlaGluAspTyrAsp-121 |
| SEQ. ID. NO. 20124 | 164-AlaThrValArgLysIleArgGln-171 |

TABLE 1-continued

| | |
|---|---|
| SEQ. ID. NO. 20125 | 175-ProAspLeuAspIle-179 |
| SEQ. ID. NO. 20126 | 186-MetTyrAspSerArgSerArgLeuValAlaGluValSerGluGlnLeuArg-202 |
| SEQ. ID. NO. 20127 | 216-ArgAsnIleArgLeuAlaGluAlaProSer-225 |
| SEQ. ID. NO. 20128 | 235-AlaGlnAlaLysGlyAlaLys-241 |
| SEQ. ID. NO. 20129 | 248-AspGluLeuMetAla-252 |
| a568 | |
| AMPHI Regions - AMPHI | |
| SEQ. ID. NO. 20130 | 31-SerIlePheArgArg-35 |
| SEQ. ID. NO. 20131 | 48-LysAlaCysLysAsn-52 |
| SEQ. ID. NO. 20132 | 70-GluLysAlaAsnThrValArgTyr-77 |
| SEQ. ID. NO. 20133 | 81-SerLeuAlaGlnCysPheThr-87 |
| SEQ. ID. NO. 20134 | 111-ArgProLeuProSerIleIleThrAla-119 |
| SEQ. ID. NO. 20135 | 168-GluPheValGlyPheGlyAsnValPheValGlyGlnPheLeuAsnArgPhePhe-185 |
| SEQ. ID. NO. 20136 | 199-GluGluPhePheAspValValVal-206 |
| SEQ. ID. NO. 20137 | 227-PheAsnGlnValPheAlaAlaPheLeu-235 |
| SEQ. ID. NO. 20138 | 240-HisArgHisAlaAspGlnValAlaAspSerCysArgValGlnSerGln-255 |
| Antigenic Index - Jameson-Wolf | |
| SEQ. ID. NO. 20139 | 22-IleArgLeuLysArgSerArgLeuProSerIlePhe-33 |
| SEQ. ID. NO. 20140 | 38-PheSerCysArgArgArgThrCysPheCysLysAlaCysLysAsnSerProIleArgAsnGluThrSerSerSerGlyArgArgGlnPheSerValGlu LysAlaAsnThr-74 |
| SEQ. ID. NO. 20141 | 90-SerAsnAlaSerLysProArgLeu-97 |
| SEQ. ID. NO. 20142 | 99-ProIleMetArgGlyArgLysArgPhePheAla-109 |
| SEQ. ID. NO. 20143 | 140-PheArgGlySerAlaPheLysCysArgLeuAsnAlaGluProCysArg-155 |
| SEQ. ID. NO. 20144 | 213-AlaAspGlyAspAla-217 |
| SEQ. ID. NO. 20145 | 236-GlyGlnHisGlyHisArgHisAlaAspGlnValAlaAspSerCysArgValGlnSerGln-255 |
| Hydrophilic Regions - Hopp-Woods | |
| SEQ. ID. NO. 20146 | 22-IleArgLeuLysArgSerArgLeu-29 |
| SEQ. ID. NO. 20147 | 40-CysArgArgArgThrCysPhe-46 |
| SEQ. ID. NO. 20148 | 48-LysAlaCysLysAsnSerProIleArgAsnGluThrSerSerSerGlyArgArgGlnPheSerValGluLysAlaAsnThr-74 |
| SEQ. ID. NO. 20149 | 92-AlaSerLysProArgLeu-97 |
| SEQ. ID. NO. 20150 | 101-MetArgGlyArgLysArgPhePheAla-109 |
| SEQ. ID. NO. 20151 | 143-SerAlaPheLysCysArgLeuAsnAlaGluProCysArg-155 |
| SEQ. ID. NO. 20152 | 238-HisGlyHisArgHisAlaAspGlnValAlaAspSerCysArgVal-252 |
| a569-2 | |
| AMPHI Regions - AMPHI | |
| SEQ. ID. NO. 20153 | 29-AlaAlaPheCysGlyLeuIleAlaLeuThrAlaLeuTrpGluTyrAlaArgMetAlaGlyLeuCysLys-51 |
| SEQ. ID. NO. 20154 | 86-PheTrpLeuAlaValMetPro-92 |
| SEQ. ID. NO. 20155 | 161-IleAlaArgAlaIleSerProGlyLysSerTrpGluGlyAlaIle-175 |
| SEQ. ID. NO. 20156 | 203-ThrValLeuIleGlyLeu-208 |
| SEQ. ID. NO. 20157 | 210-LeuThrValValSerValCysGlyAspLeuLeuGluSerTrpLeuLys-225 |
| Antigenic Index - Jameson-Wolf | |
| SEQ. ID. NO. 20158 | 50-CysLysThrGluThrAsnHis-56 |
| SEQ. ID. NO. 20159 | 98-LysTrpArgLeuAsnGlyGlyTrp-105 |
| SEQ. ID. NO. 20160 | 124-SerLeuArgProHisProAspAspAlaLeu-133 |
| SEQ. ID. NO. 20161 | 154-LysAlaLeuGlyLysHisLysIleAlaArg-163 |
| SEQ. ID. NO. 20162 | 165-IleSerProGlyLysSerTrpGlu-172 |
| SEQ. ID. NO. 20163 | 227-AlaAlaGlyIleLysAspSerSerAsnLeuLeuProGlyHis-240 |
| SEQ. ID. NO. 20164 | 242-GlyValPheAspArgThrAspSer-249 |
| Hydrophilic Regions - Hopp-Woods | |
| SEQ. ID. NO. 20165 | 50-CysLysThrGluThr-54 |
| SEQ. ID. NO. 20166 | 127-proHisProAspAspAlaLeu-133 |
| SEQ. ID. NO. 20167 | 155-AlaLeuGlyLysHisLysIleAlaArg-163 |
| SEQ. ID. NO. 20168 | 227-AlaAlaGlyIleLysAspSerSerAsn-235 |
| SEQ. ID. NO. 20169 | 243-ValPheAspArgThrAspSer-249 |
| a570 | |
| AMPHI Regions - AMPHI | |
| SEQ. ID. NO. 20170 | 6-ArgAlaPheAlaAlaAlaLeuIleGlyLeu-15 |
| SEQ. ID. NO. 20171 | 22-HisAlaAspThrPheGlnLysIleGlyPheIleAsn-33 |
| SEQ. ID. NO. 20172 | 43-GlnAlaArgLysIleGlnLysThrLeuAspSer-53 |
| SEQ. ID. NO. 20173 | 60-AspGluLeuGlnLysLeuGln-66 |
| SEQ. ID. NO. 20174 | 81-LeuLysAspAlaLysLys-86 |
| SEQ. ID. NO. 20175 | 122-LeuGlnGlnAsnAlaAsnArgValIleValLysIle-133 |
| Antigenic Index - Jameson-Wolf | |
| SEQ. ID. NO. 20176 | 33-AsnThrGluArgIleTyrLeuGluSerLysGlnAlaArgLysIleGlnLysThrLeuAspSerGluPheSerAlaArgGlnAspGluLeuGlnLysLeu GlnArgGluGlyLeuAspLeuGluArgGlnLeuAlaGluGlyLysLeuLysAspAlaLysLysAlaGlnAlaGluGluLysTrp-93 |
| SEQ. ID. NO. 20177 | 100-PheArgLysLysGlnAlaGlnPheGluGluAspTyrAsnLeuArgArgAsnGluGluPheAla-120 |
| SEQ. ID. NO. 20178 | 123-GlnGlnAsnAlaAsnArgVal-129 |
| SEQ. ID. NO. 20179 | 133-IleAlaLysGlnGluGlyTyrAspValIle-142 |
| SEQ. ID. NO. 20180 | 150-AsnThrGlnTyrAspValThrAspSerValIleLysGluMetAsnAlaArg-166 |
| Hydrophilic Regions - Hopp-Woods | |
| SEQ. ID. NO. 20181 | 37-IleTyrLeuGluSerLysGlnAlaArgLysIleGlnLysThrLeuAspSerGluPheSerAlaArgGlnAspGluLeuGlnLysLeuGlnArgGlu GlyLeuAspLeuGluArgGlnLeuAlaGluGlyLysLeuLysAspAlaLysLysAlaGlnAlaGluGluLysTrp-93 |

TABLE 1-continued

SEQ. ID. NO. 20182 100-PheArgLysLysGlnAlaGlnPheGluGluAspTyrAsnLeuArgArgAsnGluGluPheAla-120
SEQ. ID. NO. 20183 133-IleAlaLysGlnGluGlyTyr-139
SEQ. ID. NO. 20184 154-AspValThrAspSerValrIeLysGluMetAsnAlaArg-166
a571
AMPHI Regions - AMPHI
SEQ. ID. NO. 20185 6-AlaValAsnValLeu-10
SEQ. ID. NO. 20186 40-AspGlyAlaArgValPheArgAlaGly-48
SEQ. ID. NO. 20187 63-AlaAlaValAlaAspPhePheAlaVal-71
SEQ. ID. NO. 20188 94-ValGluValPheLysGlu-99
Antigenic Index - Jameson-Wolf
SEQ. ID. NO. 20189 13-AlaAlaGlyArgGlyThr-18
SEQ. ID. NO. 20190 35-LysGlnAlaGlnAlaAspGlyAlaArgValPheArgAlaGlyHisArgGluGluGlnLeuGlyGlyAspVal-58
SEQ. ID. NO. 20191 77-ArgThrGluArgAlaAla-82
SEQ. ID. NO. 20192 96-ValPheLysGluGlyAspPhe-102
SEQ. ID. NO. 20193 110-ArgAsnAlaAspPheAlaAlaGluHisGlnArgGluGlyPheAlaGlyGluGluProGlyLeuValValGly-133
SEQ. ID. NO. 20194 143-GlyGlnGlyAspPheGlyVal-149
SEQ. ID. NO. 20195 154-ValAlaAlaArgArgPro-159
Hydrophilic Regions - Hopp-Woods
SEQ. ID. NO. 20196 13-AlaAlaGlyArgGly-17
SEQ. ID. NO. 20197 35-LysGlnAlaGlnAlaAspGlyAlaArgValPheArgAlaGlyHisArgGluGluGlnLeuGly-55
SEQ. ID. NO. 20198 77-ArgThrGluArgAlaAla-82
SEQ. ID. NO. 20199 96-ValPheLysGluGlyAspPhe-102
SEQ. ID. NO. 20200 110-ArgAsnAlaAspPheAlaAlaGluHisGlnArgGluGlyPheAlaGlyGluGluProGly-129
SEQ. ID. NO. 20201 154-ValAlaAlaArgArgPro-159
a572
AMPHI Regions - AMPHI
SEQ. ID. NO. 20202 6-GlyAlaValGlyLeuProSerAlaLeuAla-15
SEQ. ID. NO. 20203 61-GlnValLeuProArgAspTyrThrGlyArg-70
SEQ. ID. NO. 20204 94-AsnThrPheAspSerIle-99
SEQ. ID. NO. 20205 126-LysGlyLeuGluLeu-130
SEQ. ID. NO. 20206 154-IleHisSerMetValArg-159
SEQ. ID. NO. 20207 183-GlyLeuProGluArgIleAspSerGly-191
SEQ. ID. NO. 20208 200-LeuSerAlaLeuThr-204
SEQ. ID. NO. 20209 241-ValAlaAlaPheLeu-245
SEQ. ID. NO. 20210 251-PheThrAspIleAlaLysThrValAlaHisCysLeuSerGlnAspPheSerAspGlyIleGlyAspIleGlyGly-275
Antigenic Index - Jameson-Wolf
SEQ. ID. NO. 20211 18-GlnLysGlyLysThr-22
SEQ. ID. NO. 20212 26-AlaAsnLysGluThrLeu-31
SEQ. ID. NO. 20213 41-ThrAlaArgAlaAsnGly-46
SEQ. ID. NO. 20214 51-ProValAspSerGluHis-56
SEQ. ID. NO. 20215 63-LeuProArgAspTyrThrGlyArgLeuAsnGluHisGly-75
SEQ. ID. NO. 20216 94-AsnThrPheAspSerIleThrProAspGlnAlaValLysHisProAsnTrp ArgMetGlyArgLysIleSerValAspSer-120
SEQ. ID. NO. 20217 125-AsnLysGlyLeuGluLeu-130
SEQ. ID. NO. 20218 138-AsnCysProProAspLysLeuGluVal-146
SEQ. ID. NO. 20219 158-ValArgTyrArgAspGlySerVal-165
SEQ. ID. NO. 20220 170-GlyAsnProAspMetArgThr-176
SEQ. ID. NO. 20221 184-LeuProGluArgIleAspSerGlyValGlyAspLeuAspPhe-197
SEQ. ID. NO. 20222 204-ThrPheGlnLysProAspPheAspArg-212
SEQ. ID. NO. 20223 263-SerGlnAspPheSerAspGlyIleGlyAspIleGly-274
SEQ. ID. NO. 20224 279-GlnAspAlaArgThrArgAlaGlnAla-287
Hydrophilic Regions - Hopp-Woods
SEQ. ID. NO. 20225 27-AsnLysGluThrLeu-31
SEQ. ID. NO. 20226 41-ThrAlaArgAlaAsnGly-46
SEQ. ID. NO. 20227 52-ValAspSerGluHis-56
SEQ. ID. NO. 20228 66-AspTyrThrGlyArgLeuAsnGlu-73
SEQ. ID. NO. 20229 111-ArgMetGlyArgLysIleSerVal-118
SEQ. ID. NO. 20230 126-LysGlyLeuGluLeu-130
SEQ. ID. NO. 20231 140-ProProAcpLysLeuGlu-145
SEQ. ID. NO. 20232 158-ValArgTyrArgAspGlySer-164
SEQ. ID. NO. 20233 170-GlyAsnProAspMetArgThr-176
SEQ. ID. NO. 20234 184-LeuProGluArgIleAspSerGlyValGlyAspLeuAspPhe
SEQ. ID. NO. 20235 206-GlnLysProAspPheAspArg-212
SEQ. ID. NO. 20236 265-AspPheSerAspGlyIleGly-271
SEQ. ID. NO. 20237 279-GlnAspAlaArgThrArgAlaGlnAla-287
a574
AMPHI Regions - AMPHI
SEQ. ID. NO. 20238 6-ProAsnSerLeuGluLys-11
SEQ. ID. NO. 20239 47-LeuLysGlnAlaLysSerIleProSerGlyPheTyrLysSerLeuAspAlaLeuValAspArgAsnSerGlyArgAlaAlaArgGluLeuAlaGlu ValValAsp-81
SEQ. ID. NO. 20240 94-GlyLysLeuTyrArgGln-99
SEQ. ID. NO. 20241 110-HisGlnThrLeuLeuAspSerProAspThrThrGly-121
SEQ. ID. NO. 20242 175-GluLysAlaValGluThrAlaArgLeu-183
SEQ. ID. NO. 20243 218-AsnValGlyLysAlaLeuGluAlaAsnLysLysCys-229
SEQ. ID. NO. 20244 246-PheProAlaAlaValGluAlaTyrAlaAlaIleGlu-257
SEQ. ID. NO. 20245 266-MetValGlyGluLysLeuTyrGluAlaTyrAla-276

TABLE 1-continued

| | |
|---|---|
| SEQ. ID. NO. 20246 | 281-ProGluGluGlyLeuAsnArgLeuThrGlyTyrMetGlnThrPheProGl uLeuAspLeu-300 |
| SEQ. ID. NO. 20247 | 332-AsnGlyValTyrArg-336 |
| SEQ. ID. NO. 20248 | 357-ArgSerValIleGlyArgGlnLeuGlnArgSer-367 |
| Antigenic index - Jameson-Wolf | |
| SEQ. ID. NO. 20249 | 1-MetArgProAGnLeuProAsnSerLeuGluLysAlaAspMetAspAsn-16 |
| SEQ. ID. NO. 20250 | 45-ThrValLeuLysGlnAlaLysSerIleProSerGlyPheTyrLysSerLeu AspAlaLeuValAspArgAsnSerGlyArgAlaAlaArgGluLeuAla GluVal ValAspGlyArgProGlnSerTyrAsp-88 |
| SEQ. ID. NO. 20251 | 96-LeuTyrArgGlnArgGlyGluAsnAspLysAlaIle-107 |
| SEQ. ID. NO. 20252 | 113-LeuLeuAspSerProAspThrThrGlyAlaLysArgAlaArgVal-127 |
| SEQ. ID. NO. 20253 | 135-TyrGlnSerAlaGlyLeuValAspArgAlaGlu-145 |
| SEQ. ID. NO. 20254 | 151-LeuGlnAspGlyGluMetAlaArgGluAlaArgGln-162 |
| SEQ. ID. NO. 20255 | 168-TyrGlnGlnAspArgAspTrpGluLysAlaValGluThr-180 |
| SEQ. ID. NO. 20256 | 182-ArgLeuLeuSerHisAspAspGlnThrTyr-191 |
| SEQ. ID. NO. 20257 | 210-SerAsnPheAspAlaAlaArg-216 |
| SEQ. ID. NO. 20258 | 221-LysAlaLeuGluAlaAsnLysLysCysThrArg-231 |
| SEQ. ID. NO. 20259 | 238-AspIleGluHisArgGlnGlyAsn-245 |
| SEQ. ID. NO. 20260 | 277-AlaGlnGlyLysProGluGluGlyLeuAsnArgLeuThrGlyTyr-291 |
| SEQ. ID. NO. 20261 | 312-LysCysGluLysGluAlaAla-318 |
| SEQ. ID. NO. 20262 | 323-GluLeuValArgArgLysProAspLeuAsnGly-333 |
| SEQ. ID. NO. 20263 | 341-LysLeuSerAspLeuAspProAlaTrpLysAlaAspAlaAspMetMetArg-357 |
| SEQ. ID. NO. 20264 | 368-ValMetTyrArgCysArgAsnCysHisPheLys-378 |
| SEQ. ID. NO. 20265 | 386-CysProAlaCysAsnLysTrpGlnThrPheThrProAsnLysIleGluVal-402 |
| Hydrophilic Regions - Hopp-Woods | |
| SEQ. ID. NO. 20266 | 1-MetArgProAsnLeu-5 |
| SEQ. ID. NO. 20267 | 7-AsnSerLeuGluLysAlaAspMetAspAsn-16 |
| SEQ. ID. NO. 20268 | 45-ThrValLeuLysGlnAlaLysSerIle-53 |
| SEQ. ID. NO. 20269 | 62-AspAlaLeuValAspArgAsnSerGlyArgAlaAlaArgGluLeuAlaGluValValAspGlyArgProGlnSer-86 |
| SEQ. ID. NO. 20270 | 96-LeuTyrArgGlnArgGlyGluAsnAspLysAlaIle-107 |
| SEQ. ID. NO. 20271 | 115-AspSerProAspThrThrGlyAlaLysArgAlaArgVal-127 |
| SEQ. ID. NO. 20272 | 140-LeuValAspArgAlaGlu-145 |
| SEQ. ID. NO. 20273 | 152-GlnAspGlyGluMetAlaArgGluAlaArgGln-162 |
| SEQ. ID. NO. 20274 | 169-GlnGlnAspArgAspTrpGluLysAlaValGluThr-180 |
| SEQ. ID. NO. 20275 | 184-LeuSerHisAspAspGlnThrTyr-191 |
| SEQ. ID. NO. 20276 | 211-AsnPheAspAlaAlaArg-216 |
| SEQ. ID. NO. 20277 | 221-LysAlaLeuGluAlaAsnLysLysCysThrArg-231 |
| SEQ. ID. NO. 20278 | 238-AspIleGluHisArgGlnGlyAsn-245 |
| SEQ. ID. NO. 20279 | 279-GlyLysProGluGluGlyLeuAsn-286 |
| SEQ. ID. NO. 20280 | 312-LysCysGluLysGluAlaAla-318 |
| SEQ. ID. NO. 20281 | 323-GluLeuValArgArgLysProAspLeu-331 |
| SEQ. ID. NO. 20282 | 341-LysLeuSerAspLeuAspPro-347 |
| SEQ. ID. NO. 20283 | 349-TrpLysAlaAspAlaAspMetMetArg-357 |
| SEQ. ID. NO. 20284 | 368-ValMetTyrArgCysArgAsnCysHis-376 |
| SEQ. ID. NO. 20285 | 398-AsnLysIleGluVal-402 |
| a575 | |
| AMPHI Regions - AMPHI | |
| SEQ. ID. NO. 20286 | 8-PheArgLysProAlaSer-13 |
| SEQ. ID. NO. 20287 | 20-PheAlaGluAlaVal-24 |
| SEQ. ID. NO. 20288 | 42-SerThrValSerGlyLeuPheSerAla-50 |
| SEQ. ID. NO. 20289 | 114-LeuSerLysSerLysSer-119 |
| SEQ. ID. NO. 20290 | 139-SerSerAspSerPro-143 |
| SEQ. ID. NO. 20291 | 150-PheThrSerPhePheGly-155 |
| SEQ. ID. NO. 20292 | 163-ValSerThrSerAlaLysValIleSerMetPro-173 |
| SEQ. ID. NO. 20293 | 217-SerLysValTyrGluProProAsn-224 |
| SEQ. ID. NO. 20294 | 233-AlaGluThrCysSerThr-238 |
| SEQ. ID. NO. 20295 | 283-AlaGlyPheSerAlaPheAlaSerGlyAla-292 |
| SEQ. ID. NO. 20296 | 294-ThrPheAlaSerGlyPheSerThrGly-302 |
| SEQ. ID. NO. 20297 | 304-SerThrValAlaCys-308 |
| SEQ. ID. NO. 20298 | 311-GlySerAspGlyMetAspAlaValSerAlaLeu-321 |
| Antigenic Index - Jameson-Wolf | |
| SEQ. ID. NO. 20299 | 2-ValSerGlyGluGluAlaPheArgLysProAlaSerProGluGlyGluAlaGlyPhe-20 |
| SEQ. ID. NO. 20300 | 34-GlyArgLeuSerGluLysSerValSer-42 |
| SEQ. ID. NO. 20301 | 54-ThrAspSerGlySerGlyVal-60 |
| SEQ. ID. NO. 20302 | 96-SerSerSerCysValSerAlaProAspLysMetProPhe-108 |
| SEQ. ID. NO. 20303 | 113-ArgLeuSerLysSerLysSerMetArgLeuGluGly-124 |
| SEQ. ID. NO. 20304 | 134-PheAlaAspAsnSerSerSerAspSerProSerLysAlaSerVal-148 |
| SEQ. ID. NO. 20305 | 155-GlyAlaGlySerGly-159 |
| SEQ. ID. NO. 20306 | 173-ProSerSerAlaAlaSerSerArgSerGlySerSerSerGlyThrAspSe rSerValArgArgAlaArgLeuAspTrpAlaArgArgLysSerSerSer ArgAlaIle-208 |
| SEQ. ID. NO. 20307 | 211-AlaProProProAlaSer-216 |
| SEQ. ID. NO. 20308 | 218-LysValTyrGluProProAsnSerProLeu-227 |
| SEQ. ID. NO. 20309 | 230-SerSerSerAlaGluThrCysSerThrGlySerGluThr-242 |
| SEQ. ID. NO. 20310 | 261-GlyAlaAspSerAlaAlaVal-267 |
| SEQ. ID. NO. 20311 | 276-GlyThrGlySerGlyArgThrAla-283 |
| SEQ. ID. NO. 20312 | 299-PheSerThrGlyPhe-303 |
| SEQ. ID. NO. 20313 | 309-LeuAspGlySerAspGlyMetAsp-316 |
| Hydrophilic Regions - Hopp-woods | |
| SEQ. ID. NO. 20314 | 2-ValSerGlyGluGluAlaPheArgLysProAlaSerProGluGlyGluAlaGlyPhe-20 |
| SEQ. ID. NO. 20315 | 34-GlyArgLeuSerGluLysSerValSer-42 |
| SEQ. ID. NO. 20316 | 101-SerAlaProAspLysMetPro-107 |
| SEQ. ID. NO. 20317 | 113-ArgLeuSerLysSerLysSerMetArgLeuGluGly-124 |

TABLE 1-continued

| | |
|---|---|
| SEQ. ID. NO. 20318 | 137-AsnSerSerSerAspSerProSerLysAla-146 |
| SEQ. ID. NO. 20319 | 176-AlaAlaSerSerArgSerGlySerSerSerGlyThrAspSerSerValArgArgAlaArgLeuAspTrpAlaArgArgLysSerSerSer ArgAlaIle-208 |
| SEQ. ID. NO. 20320 | 231-SerSerAlaGluThrCysSerThrGlySerGluThr-242 |
| SEQ. ID. NO. 20321 | 310-AspGlySerAspGlyMetAsp-316 |
| a576-l | |
| AMPHI Regions - AMPHI | |
| SEQ. ID. NO. 20322 | 31-AlaSerGluProAlaAlaAla-37 |
| SEQ. ID. NO. 20323 | 46-SerIleGlySerThr-50 |
| SEQ. ID. NO. 20324 | 63-GlyArgSerLeuLysGlnMetLys-70 |
| SEQ. ID. NO. 20325 | 82-ThrGluAlaMetGln-86 |
| SEQ. ID. NO. 20326 | 102-GlnGluValMetMetLysPheLeuGlnGluGlnGlnAlaLysAlaValGluLysHis-120 |
| SEQ. ID. NO. 20327 | 140-AlaLysAspGlyValLysThrThr-147 |
| SEQ. ID. NO. 20328 | 202-IleLeuGlyTrpThrGluGlyVal-209 |
| Antigenic Index - Jameson-Wolf | |
| SEQ. ID. NO. 20329 | 20-AlaCysGlyLysLysGluAlaAlaPro-28 |
| SEQ. ID. NO. 20330 | 30-SerAlaSerGluProAlaAla-36 |
| SEQ. ID. NO. 20331 | 38-SerSerAlaGlnGlyAspThrSerSerIleGly-48 |
| SEQ. ID. NO. 20332 | 61-AspIleGlyArgSerLeuLysGlnMetLysGluGlnGlyAlaGluIleAspLeu-78 |
| SEQ. ID. NO. 20333 | 89-TyrAspGlyLysGluIleLysMetThrGluGluGlnAlaGln-102 |
| SEQ. ID. NO. 20334 | 109-LeuGlnGluGlnGlnAlaLysAlaValGluLysHisLysAlaAspAlaLysAlaAsnLysGluLysGlyGluAlaPheLeuLysGluAsnAla AlaLysAspGlyValLysThrThrAlaSerGlyLeu-151 |
| SEQ. ID. NO. 20335 | 154-LysIleThrLysGlnGlyGluGlyLysGlnProThrLysAspAspIleVal-170 |
| SEQ. ID. NO. 20336 | 173-GluTyrGluGlyArgLeuIleAsp-180 |
| SEQ. ID. NO. 20337 | 183-ValPheAspSerSerLysAlaAsnGlyGly-192 |
| SEQ. ID. NO. 20338 | 210-GlnLeuLeuLysGluGlyGlyGlu-217 |
| SEQ. ID. NO. 20339 | 224-SerAsnLeuAlaTyrArgGluGlnGlyAlaGlyAspLysIleGlyProAsnAla-241 |
| SEQ. ID. NO. 20340 | 253-GlyAlaProGluAsnAlaProAlaLysGlnProAla-264 |
| SEQ. ID. NO. 20341 | 266-ValAspIleLysLysValAsn-272 |
| Hydrophilic Regions - Hopp-Woods | |
| SEQ. ID. NO. 20342 | 21-CysGlyLy3LysGluAlaAlaPro-28 |
| SEQ. ID. NO. 20343 | 30-SerAlaSerGluProAlaAla-36 |
| SEQ. ID. NO. 20344 | 40-AlaGlnGlyAspThrSerSer-46 |
| SEQ. ID. NO. 20345 | 61-AspIleGlyArgSerLeuLysGlnMetLysGluGlnGlyAlaGluIleAspLeu-78 |
| SEQ. ID. NO. 20346 | 89-TyrAspGlyLysGluIleLysMetThrGluGluGlnAlaGln-102 |
| SEQ. ID. NO. 20347 | 112-GlnGlnAlaLysAlaValGluLysHisLysAlaAspAlaLysAlaAsnLysGluLysGlyGluAlaPheLeuLysGluAsnAlaAlaLysAsp GlyValLysThrThrAla-148 |
| SEQ. ID. NO. 20348 | 155-IleThrLysGlnGlyGluGlyLysGlnProThrLysAspAspIleVal-l70 |
| SEQ. ID. NO. 20349 | 173-GluTyrGluGlyArgLeuIleAsp-180 |
| SEQ. ID. NO. 20350 | 185-AspSerSerLysAlaAsnGly-191 |
| SEQ. ID. NO. 20351 | 210-GlnLeuLeuLysGluGlyGlyGlu-217 |
| SEQ. ID. NO. 20352 | 227-AlaTyrArgGluGlnGlyAlaGlyAspLysIleGlyPro-239 |
| SEQ. ID. NO. 20353 | 253-GlyAlaProGluAsnAlaProAlaLysGlnProAla-264 |
| SEQ. ID. NO. 20354 | 266-ValAspIleLysLysValAsn-272 |
| a577 | |
| AMPHI Regions - AMPHI | |
| SEQ. ID. NO. 20355 | 8-GlyLysIleValGlyAsn-13 |
| SEQ. ID. NO. 20356 | 24-AlaAlaSerTyrProLysProCysLysSerPheLysLeuAla-37 |
| SEQ. ID. NO. 20357 | 62-ThrValIleLysIleIle-67 |
| SEQ. ID. NO. 20358 | 104-AlaPheValValGlyile-109 |
| SEQ. ID. NO. 20359 | 112-GlyMetPheAlaLeuPheGlyArg-119 |
| SEQ. ID. NO. 20360 | 144-GluLeuThrAlaProProAlaGln-151 |
| Antigenic Index - Jameson-Wolf | |
| SEQ. ID. NO. 20361 | 1-MetGluArgAsnGlyVal-6 |
| SEQ. ID. NO. 20362 | 14-ArgIleLeuArgMetSerSerGluHisAla-23 |
| SEQ. ID. NO. 20363 | 26-SerTyrProLysProCysLysSerPheLys-35 |
| SEQ. ID. NO. 20364 | 44-ArgSerCysProGlyGly-49 |
| SEQ. ID. NO. 20365 | 88-LeuProGlyGlnLysPheAspLeu-95 |
| SEQ. ID. NO. 20366 | 121-LeuSerLeuArgGlyGluAsnGlyArgLeuArgAlaGluValLysLysAsnAlaArgLeuThrGlyLysGluLeuThrAlaProProAlaGlnAsn AlaProGluSerAlaLysGlnPro-160 |
| Hydrophilic Regions - Hopp-Woods | |
| SEQ. ID. NO. 20367 | 1-MetGluArgAsnGlyVal-6 |
| SEQ. ID. NO. 20368 | 14-ArgIleLeuArgMetSerSerGluHisAla-23 |
| SEQ. ID. NO. 20369 | 29-LysProCysLysSerPheLys-35 |
| SEQ. ID. NO. 20370 | 121-LeuSerLeuArgGlyGluAsnGlyArgLeuArgAlaGluValLysLysAsnAlaArgLeuThrGlyLysGluLeuThr-146 |
| SEQ. ID. NO. 20371 | 152-AsnAlaProGluSerAlaLysGlnPro-160 |
| a578 | |
| AMPHI Regions - AMPHI | |
| SEQ. ID. NO. 20372 | 10-PheAlaAspPhePheLysAspPheAlaProGlnPheGlyGlyPheGlnAsn-26 |
| SEQ. ID. NO. 20373 | 34-AspPhePheAlaAlaPheLeuGlyGlyLeuGlu-44 |
| SEQ. ID. NO. 20374 | 71-AsnThrAspAlaAlaArgPhe-77 |
| Antigenic Index - Jameson-Wolf | |
| SEQ. ID. NO. 20375 | 2-GlyLysLeuAspIle-6 |
| SEQ. ID. NO. 20376 | 13-PhePheLysAspPheAlaProGlnPheGlyGly-23 |
| SEQ. ID. NO. 20377 | 43-LeuGluGlyAspValGlyAsnThrAla-51 |
| SEQ. ID. NO. 20378 | 71-AsnThrAspAlaAlaArgPheAla-78 |
| SEQ. ID. NO. 20379 | 88-HisAsnGlnAsnIleGlnThrArgAsnAspPheArgLeuGluArgGlyGlyValGly-106 |
| Hydrophilic Regions - Hopp-Woods | |
| SEQ. ID. NO. 20380 | 2-GlyLysLeuAspIle-6 |
| SEQ. ID. NO. 20381 | 43-LeuGluGlyAspValGlyAsn-49 |

TABLE 1-continued

| | |
|---|---|
| SEQ. ID. NO. 20382 | 73-AspAlaAlaArgPheAla-18 |
| SEQ. ID. NO. 20383 | 92-IleGlnThrArgAsnAspPheArgLeuGluArgGlyGlyVal-105 |
| a579 | |
| AMPHI Regions - AMPHI | |
| SEQ. ID. NO. 20384 | 6-PheAspPheLeuHisLeuIleSerAlaSerGlyTrpGluHisLeuALaGlu-22 |
| SEQ. ID. NO. 20385 | 49-ValAlaValMetArg-53 |
| SEQ. ID. NO. 20386 | 66-IleSerPheLeuCysAsn-71 |
| SEQ. ID. NO. 20387 | 115-LeuSerAsnPheAla-119 |
| SEQ. ID. NO. 20388 | 129-ProPheLysValGlyAspPheIleArgValGlyGlyPheGluGlyTyrValArgGluIleLys-149 |
| SEQ. ID. NO. 20389 | 258-GlnValValGluAsnLeuArg-264 |
| Antigenic Index - Jameson-Wolf | |
| SEQ. ID. NO. 20390 | 110-SerLeuLysAspGlnLeuSer-116 |
| SEQ. ID. NO. 20391 | 128-ArgProPheLysVal-l32 |
| SEQ. ID. NO. 20392 | 136-IleArgValGlyGlyPheGluGlyTyrValArgGluIleLysMet-150 |
| SEQ. ID. NO. 20393 | 154-SerLeuArgThrThrAspAsnGluGluValValLeu-l65 |
| SEQ. ID. NO. 20394 | 175-IleValAsnArgSerThrLeu-181 |
| SEQ. ID. NO. 20395 | 198-LeuLysValAlaLysGluAlaValLeu-206 |
| SEQ. ID. NO. 20396 | 216-ValGlnAsnGluGluArgGlnAla-223 |
| SEQ. ID. NO. 20397 | 231-GlyAspAsnAlaIle-235 |
| SEQ. ID. NO. 20398 | 244-AsnGluAlaAspArgTrpThrLeu-251 |
| SEQ. ID. NO. 20399 | 253-CysAspLeuAsnGluGlnValValGluAsnLeuArgLysValAsn-267 |
| SEQ. ID. NO. 20400 | 271-ProPheProGlnArgAspIleHis-278 |
| Hydrophilic Regions - Hopp-Woods | |
| SEQ. ID. NO. 20401 | 110-SerLeuLysAspGlnLeu-115 |
| SEQ. ID. NO. 20402 | 144-TyrValArgGluIleLysMet-150 |
| SEQ. ID. NO. 20403 | 155-LeuArgThrThrAspAsnGluGluValVal-164 |
| SEQ. ID. NO. 20404 | 198-LeuLysValAlaLysGluAlaValLeu-206 |
| SEQ. ID. NO. 20405 | 216-ValGlnAsnGluGluArgGlnAla-223 |
| SEQ. ID. NO. 20406 | 244-AsnGluAlaAspArgTrp-249 |
| SEQ. ID. NO. 20407 | 254-AspLeuAsnGluGlnValValGluAsnLeuArgLysValAsn-267 |
| SEQ. ID. NO. 20408 | 273-ProGlnArgAspIleHis-278 |
| a580 | |
| AMPHI Regions - AMPHI | |
| SEQ. ID. NO. 20409 | 47-ProValSerAlaSerLys-52 |
| SEQ. ID. NO. 20410 | 54-SerLeuValLysProLeuSerGlnProLeuAla-64 |
| Antigenic Index - Jameson-Wolf | |
| SEQ. ID. NO. 20411 | 1-MetAspSerProLysValGlyCysGly-9 |
| SEQ. ID. NO. 20412 | 48-ValSerAlaSerLys-52 |
| SEQ. ID. NO. 20413 | 66-AlaArgProGluAlaAlaHis-72 |
| SEQ. ID. NO. 20414 | 81-ArgProGluAlaLeuAlaAspAsnSerValSerProThrHisAlaThrSerGlyGluVal-100 |
| Hydrophilic Regions - Hopp-Woods | |
| SEQ. ID. NO. 20415 | 1-MetAspSerProLysVal-6 |
| SEQ. ID. NO. 20416 | 66-AlaArgProGluAlaAlaHis-72 |
| SEQ. ID. NO. 20417 | 81-ArgProGluAlaLeuAla-86 |
| SEQ. ID. NO. 20418 | 96-ThrSerGlyGluVal-100 |
| a581 | |
| AMPHI Regions - AMPHI | |
| SEQ. ID. NO. 20419 | 43-SerHisPheIleSerLeu-48 |
| SEQ. ID. NO. 20420 | 56-ArgGluCysPheValGlyPhe-62 |
| SEQ. ID. NO. 20421 | 76-AlaThrAlaPheGlyArgIleAsnGln-84 |
| SEQ. ID. NO. 20422 | 91-ValHisGlyPheLeuThrThrPheAla-99 |
| Antigenic Index - Jameson-Wolf | |
| SEQ. ID. NO. 20423 | 8-GlyGlnThrGlyIleGluGlnAsnThrPheCysArgArgGlyPheThrArgIleAspMetGlyGlyAsnThrAspVal-33 |
| SEQ. ID. NO. 20424 | 35-ValGlnAlaAspArgGlyLeuThrSer-43 |
| SEQ. ID. NO. 20425 | 49-SerLysLeuGluThrGluValArgGluCysPhe-59 |
| SEQ. ID. NO. 20426 | 98-PheAlaGlyArgIleAsnProAlaHisCysGlnSerGlnThrAla-112 |
| Hydrophilic Regions - Hopp-Woods | |
| SEQ. ID. NO. 20427 | 35-ValGlnAlaAspArgGlyLeu-41 |
| SEQ. ID. NO. 20428 | 49-SerLysLeuGluThrGluValArgGlu-57 |
| a582 | |
| AMPHI Regions - AMPHI | |
| SEQ. ID. NO. 20429 | 27-ThrAspAsnValThrArgLeuAla-34 |
| SEQ. ID. NO. 20430 | 65-ValArgSerSerLeu-69 |
| SEQ. ID. NO. 20431 | 91-GlyGluThrAlaAspIleTyrThrProLeuSer-101 |
| SEQ. ID. NO. 20432 | 139-GlySerProThrArg-143 |
| SEQ. ID. NO. 20433 | 169-IleAlaGluAspLeuPhe-174 |
| SEQ. ID. NO. 20434 | 246-SerArgSerTrpAsnArgIleTyrAlaMet-255 |
| SEQ. ID. NO. 20435 | 263-LeuThrValIleProArgValTrpValArgAlaPheAspGlnSer-277 |
| SEQ. ID. NO. 20436 | 286-IleAlaAspTyrMetGlyTyr-292 |
| SEQ. ID. NO. 20437 | 334-LeuLysGlyValValArgGlyPheHisGlyTyrGlyGlu-346 |
| Antigenic Index - Jameson-Wolf | |
| SEQ. ID. NO. 20438 | 26-LeuThrAspAsnValThr-31 |
| SEQ. ID. NO. 20439 | 34-AlaCysTyrAspArg-38 |
| SEQ. ID. NO. 20440 | 44-LeuProSerSerAlaGlyGlnGluGlyGlnGluSerLysAla-57 |
| SEQ. ID. NO. 20441 | 63-GluThrValArgSerSerLeuAspLysGlyGluAla-74 |
| SEQ. ID. NO. 20442 | 77-ValValGluLysGlyGlyAspAlaLeuProAlaAspSerAlaGlyGluThrAlaAsp-95 |
| SEQ. ID. NO. 20443 | 105-AspLeuAspLysAsnAspLeuArgGly-113 |
| SEQ. ID. NO. 20444 | 115-LeuGlyValArgGluHisAsnProMetTyr-124 |
| SEQ. ID. NO. 20445 | 131-AsnAsnSerProAsnTyrAlaProGlySerProThrArgGlyThrThrValGlnGluLysPheGlyGlnGlnLysArgAlaGluThrLysLeu-161 |
| SEQ. ID. NO. 20446 | 165-PheLysSerLysIleAlaGluAspLeuPheLysThrArgAla-178 |

TABLE 1-continued

SEQ. ID. NO. 20447 183-GlyTyrThrGlnArgSerAspTrpGlnIleTyrAsnGlnGlyArgLysSerAlaProPheArgAsnThrAspTyrLysPro-209
SEQ. ID. NO. 20448 216-ProValLysAlaAspLeuProPheGlyGlyArgLeuArgMet-229
SEQ. ID. NO. 20449 237-GlnSerAsnGlyGlnSerArgProGluSerArgSerTrpAsn-250
SEQ. ID. NO. 20450 273-AlaPheAspGlnSerGlyAspLysAsnAspAsnProAspIleAlaAsp-288
SEQ. ID. NO. 20451 291-GlyTyrGlyAspValLysLeuGlnTyrArgLeuAsnAspArgGlnAsnVal-307
SEQ. ID. NO. 20452 312-ArgTyrAsnProLysThrGlyTyr-319
SEQ. ID. NO. 20453 330-IleLysGlyLysLeuLysGlyValVal-338
SEQ. ID. NO. 20454 342-HisGlyTyrGlyGluSerLeuIleAspTyrAsnHisLysGlnAsnGly-357
SEQ. ID. NO. 20455 365-AsnAspLeuAspGlyIle-370
Hydrophilic Regions - Hopp-Woods
SEQ. ID. NO. 20456 48-AlaGlyGlnGluGlyGlnGluSerLysAla-57
SEQ. ID. NO. 20457 63-GluThrValArgSerSerLeuAspLysGlyGluAla-74
SEQ. ID. NO. 20458 79-GluLysGlyGlyAspAlaLeuPro-86
SEQ. ID. NO. 20459 88-AspSerAlaGlyGluThrAlaAsp-95
SEQ. ID. NO. 20460 105-AspLeuAspLysAsnAspLeuArgGly-113
SEQ. ID. NO. 20461 115-LeuGlyValArgGluHisAsn-121
SEQ. ID. NO. 20462 140-SerProThrArgGlyThrThrValGlnGluLysPheGlyGlnGlnLysArgAlaGluThrLysLeu-161
SEQ. ID. NO. 20463 165-PheLysSerLysIleAlaGluAspLeuPheLysThrArgAla-178
SEQ. ID. NO. 20464 195-GlnGlyArgLysSerAlaProPheArgAsnThrAspTyrLysPro-209
SEQ. ID. NO. 20465 225-GlyArgLeuArgMet-229
SEQ. ID. NO. 20466 239-AsnGlyGlnSerArgProGluSerArgSerTrp-249
SEQ. ID. NO. 20467 274-PheAspGlnSerGlyAspLysAsnAspAsnProAspIleAlaAsp-288
SEQ. ID. NO. 20468 293-GlyAspValLysLeu-297
SEQ. ID. NO. 20469 299-TyrArgLeuAsnAspArgGlnAsn-306
SEQ. ID. NO. 20470 332-GlyLysLeuLysGlyValVal-338
SEQ. ID. NO. 20471 352-AsnHisLysGlnAsn-356
a583
AMPHI Regions - AMPHI
SEQ. ID. NO. 20472 11-HisLeuAlaPheCysAlaPheCysGlyIle-20
SEQ. ID. NO. 20473 28-ArgLeuHisAsnArgMetTyrAsnAlaAlaAlaAlaArg-40
SEQ. ID. NO. 20474 58-ValThrAspAlaGln-62
SEQ. ID. NO. 20475 66-SerLysAsnGlyAspLysGlnIle-73
SEQ. ID. NO. 20476 75-AspThrHisProGlnPro-80
SEQ. ID. NO. 20477 117-GlyTyrAlaGlyTyrCysAspGln-124
SEQ. ID. NO. 20478 140-AspAsnGlyGlyAsnHisThrAsp-147
SEQ. ID. NO. 20479 162-GlyTyrGlyGlnCysGlnAsnGlnGlyAla-171
Antigenic Index - Jameson-Wolf
SEQ. ID. NO. 20480 24-ThrAlaGlyAsnArgLeuHisAsnArgMetTyr-34
SEQ. ID. NO. 20481 41-GlyIleGlyArgGlyAsnGlySerGlnGlnGlnPheGlyLysSerGluThr
ValThrAspAlaGlnArgPheSerSerLysAsnGlyAspLysGlnIleSerAsp
ThrHisProGlnProCysPheGluGlnThrAlaArgAsnHisAsnCysAspGly
AsnGlnProAsnGlnArgIleGlyGluArgThrGlnArgIleAlaHisArgArg
ThrArgPheValGlyGlyTyrAlaGlyTyrCysAspGlnProAspGlyAsnAsn
ArgGlnArgThrGlnArgHisGlyLeuAlaAspAsnGlyGlyAsnHisThrAsp
LysHisGlyGlnGlnArgProSerLeuArgLeuAspProValGlyTyrGlyGln
CysGlnAsnGlnGlyAlaGlnTyrCysGlyAsnGlyGluGlyTyrArgPhe-182
SEQ. ID. NO. 20482 190-AspLeuArgLysLysAspArgProGluLysSerGluLys-202
Hydrophilic Regions - Hopp-Woods
SEQ. ID. NO. 20483 27-AsnArgLeuHisAsn-31
SEQ. ID. NO. 20484 41-GlyIleGlyArgGlyAsnGlySer-48
SEQ. ID. NO. 20485 51-GlnPheGlyLysSerGluThrValThrAspAlaGlnArgPheSerSerLysAsnGlyAspLysGlnIleSerAspThrHisPro-78
SEQ. ID. NO. 20486 84-GlnThrAlaArgAsnHisAsnCysAspGlyAsnGlnProAsnGlnArgIleGlyGluArgThrGlnArgIleAlaHisArgArgThrArgPhe-114
SEQ. ID. NO. 20487 123-AspGlnProAspGlyAsnAsnArgGlnArgThrGlnArg-135
SEQ. ID. NO. 20488 137-GlyLeuAlaAspAsnGlyGlyAsnHisThrAspLysHisGlyGlnGlnArgProSerLeuArgLeuAspPro-160
SEQ. ID. NO. 20489 178-GluGlyTyrArgPhe-182
SEQ. ID. NO. 20490 190-AspLeuArgLysLysAspArgProGluLysSerGluLys-202
a584-2
AMPHI Regions - AMPHI
SEQ. ID. NO. 20491 28-GluPheSerGluSerAlaGlyValGluAlaValGlnAspThrMet-42
SEQ. ID. NO. 20492 60-AlaGluPheValLysLysPheAsnAsnPheThrArgLys-72
SEQ. ID. NO. 20493 116-PheAspAlaLeuAsnArgPheIleAlaAspVal-126
SEQ. ID. NO. 20494 148-IleAspGlnValSerLysAsp-154
SEQ. ID. NO. 20495 166-LeuAlaGlyValLeuGly-171
SEQ. ID. NO. 20496 186-GlySerHisIleAla-190
SEQ. ID. NO. 20497 196-GlnAlaLysMetLeuArgAlaMet-203
Antigenic Index - Jameson-Wolf
SEQ. ID. NO. 20498 50-AlaGluGlyArgAspLysAsnAlaVal-58
SEQ. ID. NO. 20499 61-GluPheValLysLysPheAsnAsnPheThrArgLysSerLysAsnGlySer
PheLysThrGluLeuValSerArgSerAlaMetProArgTyrGlnTyrThrAsn
GlyArgArgIleGlnThrGlyTrpGluGluArgAlaGluPheLysValGluGlyArgAsnPheAspAla-118
SEQ. ID. NO. 20500 138-HisValSerArgGluArgArgAsnGluValIleAspGlnValSerLysAspAlaValLeu-157
SEQ. ID. NO. 20501 159-PheLysAlaArgAlaGluLysLeuAla-167
SEQ. ID. NO. 20502 189-IleAlaGlyGlyGly-193
SEQ. ID. NO. 20503 210-AsnMetGluGlyAlaAspSerAlaAlaProGlyValGluGluIleSer-225
Hydrophilic Regions - Hopp-Woods
SEQ. ID. NO. 20504 50-AlaGluGlyArgAspLysAsnAlaVal-58
SEQ. ID. NO. 20505 67-AsnAsnPheThrArgLysSerLysAsnGlySerPheLysThrGluLeuValSer-84
SEQ. ID. NO. 20506 95-AsnGlyArgArgIleGlnThrGlyTrpGluGluArgAlaGluPheLysValGluGlyArgAsnPheAspAla-118
SEQ. ID. NO. 20507 138-HisValSerArgGluArgArgAsnGluValIleAspGlnValSerLysAspAlaValLeu-157

TABLE 1-continued

| | |
|---|---|
| SEQ. ID. NO. 20508 | 159-PheLysAlaArgAlaGluLysLeuAla-167 |
| SEQ. ID. NO. 20509 | 210-AsnMetGluGlyAlaAspSerAlaAlaProGlyValGluGluIleSer-225 |
| a585 | |
| AMPHI Regions - AMPHI | |
| SEQ. ID. NO. 20510 | 6-ArgIlePheAlaThrPheCysAlaValIleValCys-17 |
| SEQ. ID. NO. 20511 | 46-ThrThrLeuMetGlySerIleIleSer-54 |
| SEQ. ID. NO. 20512 | 65-ArgGluIleLeuThrGluTrpLysAsp-73 |
| SEQ. ID. NO. 20513 | 93-HisArgTyrIleAspSer-98 |
| SEQ. ID. NO. 20514 | 133-LysAspTrpAspLysLeuGlnAlaArgArg-142 |
| SEQ. ID. NO. 20515 | 153-ProLeuAlaProIleTrp-158 |
| SEQ. ID. NO. 20516 | 178-LeuAlaGlyAsnIleAlaLysProIleArgIleLeuGlyAsnGlyMetAspArgValAla-197 |
| SEQ. ID. NO. 20517 | 223-PheAspLysMetValGluLysLeuGluLysLeuVal-234 |
| SEQ. ID. NO. 20518 | 247-GluMetArgSerPro-251 |
| SEQ. ID. NO. 20519 | 255-MetGlnAlaIleValGlyLeuIle-262 |
| SEQ. ID. NO. 20520 | 273-LeuLysArgLeuGluGly-278 |
| SEQ. ID. NO. 20521 | 353-LeuTyrArgAlaPheAspAsnValIleArgAsnAlaValAsn-366 |
| SEQ. ID. NO. 20522 | 430-IleIleGluGlnHisCysGlyLysIleIleAlaGlu-441 |
| Antigenic Index - Jameson-Wolf | |
| SEQ. ID. NO. 20523 | 36-AsnGlnPheAsnGlnArgArgThrIleGlu-45 |
| SEQ. ID. NO. 20524 | 56-PheArgAlaArgGlyAspAlaGlyAlaArgGluIleLeuThrGluTrpLysAspSerProValSer-77 |
| SEQ. ID. NO. 20525 | 84-GlnGlyAspGluLysLysAspIleLeu-92 |
| SEQ. ID. NO. 20526 | 97-AspSerTyrThrIleGluArgAlaArgLeu-106 |
| SEQ. ID. NO. 20527 | 120-GluTyrAspArgPheGlyGlu-126 |
| SEQ. ID. NO. 20528 | 133-LysAspTrpAspLysLeuGlnAlaArgArgLeuProSerPro-146 |
| SEQ. ID. NO. 20529 | 189-LeuGlyAsnGlyMetAspArgValAlaAsnGlyGluLeuGluThrArgIle-205 |
| SEQ. ID. NO. 20530 | 207-GlnGlnValAspAspArgAspAspGluLeuSer-217 |
| SEQ. ID. NO. 20531 | 225-LysMetValGluLysLeuGluLysLeuValAlaLysGluArgHisLeu-240 |
| SEQ. ID. NO. 20532 | 246-HisGluMetArgSerProLeuAla-253 |
| SEQ. ID. NO. 20533 | 264-AlaGlnProGlnLysGlnGluGlnTyrLeuLysArgLeuGluGlyGluLeuThrArgMetAspThrLeuAla-287 |
| SEQ. ID. NO. 20534 | 294-SerArgLeuGluThrSerAsnMetAlaLeuGluLysGluSerLeuLys-309 |
| SEQ. ID. NO. 20535 | 317-LeuValGluAspAsnGlnSerIleAlaGlnLysAsnGlyGln-330 |
| SEQ. ID. NO. 20536 | 335-SerAlaAspGlyLysIleProGluAsnThr-344 |
| SEQ. ID. NO. 20537 | 367-TyrSerProGluGlySerThr-373 |
| SEQ. ID. NO. 20538 | 377-AsnIleGlyGlnAspHisLysHis-384 |
| SEQ. ID. NO. 20539 | 388-AspValThrAspAsnGlyProGlyValAspGluMetGln-400 |
| SEQ. ID. NO. 20540 | 409-TyrArgAlaAspSerSerAlaAsnLysProGlyThrGly-421 |
| SEQ. ID. NO. 20541 | 432-GluGlnHisCysGlyLysIleIleAlaGluAsnIleLysProAsnGlyLeuArg-449 |
| SEQ. ID. NO. 20542 | 453-IleLeuProLysLysLysThrGlySerLysThrGluLysSerAlaAsn-468 |
| Hydrophilic Regions - Hopp-Woods | |
| SEQ. ID. NO. 20543 | 37-GlnPheAsnGlnArgArgThrIleGlu-45 |
| SEQ. ID. NO. 20544 | 56-PheArgAlaArgGlyAspAlaGlyAlaArgGluIleLeuThrGluTrpLysAspSerProVal-76 |
| SEQ. ID. NO. 20545 | 84-GlnGlyAspGluLysLysAspIleLeu-92 |
| SEQ. ID. NO. 20546 | 100-ThrIleGluArgAlaArgLeu-106 |
| SEQ. ID. NO. 20547 | 120-GluTyrAspArgPheGlyGlu-126 |
| SEQ. ID. NO. 20548 | 133-LysAspTrpAspLysLeuGlnAlaArgArgLeuPro-144 |
| SEQ. ID. NO. 20549 | 192-GlyMetAspArgValAlaAsnGlyGluLeuGluThrArgIle-205 |
| SEQ. ID. NO. 20550 | 207-GlnGlnValAspAspArgAspAspGluLeuSer-217 |
| SEQ. ID. NO. 20551 | 225-LysMetValGluLysLeuGluLysLeuValAlaLysGluArgHisLeu-240 |
| SEQ. ID. NO. 20552 | 246-HisGluMetArgSerProLeu-252 |
| SEQ. ID. NO. 20553 | 265-GlnProGlnLysGlnGluGlnTyrLeuLysArgLeuGluGlyGluLeuThrArgMetAspThrLeuAla-287 |
| SEQ. ID. NO. 20554 | 294-SerArgLeuGluThr-298 |
| SEQ. ID. NO. 20555 | 302-AlaLeuGluLysGluSerLeuLys-309 |
| SEQ. ID. NO. 20556 | 317-LeuValGluAspAsnGlnSerIleAlaGlnLysAsnGlyGln-330 |
| SEQ. ID. NO. 20557 | 336-AlaAspGlyLysIleProGlu-342 |
| SEQ. ID. NO. 20558 | 389-ValThrAspAsnGlyProGlyValAspGluMetGln-400 |
| SEQ. ID. NO. 20559 | 410-ArgAlaAspSerSerAlaAsnLysProGlyThr-420 |
| SEQ. ID. NO. 20560 | 438-IleIleAlaGluAsnIleLys-444 |
| SEQ. ID. NO. 20561 | 454-LeuProLysLysLysThrGlySerLysThrGluLysSerAlaAsn-468 |
| a586 | |
| AMPHI Regions - AMPHI | |
| SEQ. ID. NO. 20562 | 12-AspAsnPheLysTyrPheTrpLysThr-20 |
| SEQ. ID. NO. 20563 | 30-IleLeuAlaAlaLeuGly-35 |
| SEQ. ID. NO. 20564 | 56-ValLeuAlaAsnIleValGluLysAlaGlnAsnLysAlaPro-69 |
| SEQ. ID. NO. 20565 | 80-LeuGlnGlnSerTyrProHisSerIleSer-89 |
| SEQ. ID. NO. 20566 | 177-SerGlnGluAlaLeuLysAsnTyrGlyGlnAlaLeuGluLysMetProGlnAspSerValGlyArg-198 |
| Antigenic Index - Jameson-Wolf | |
| SEQ. ID. NO. 20567 | 4-HisLeuGluGluGlnGlnGluLeuAspAsn-13 |
| SEQ. ID. NO. 20568 | 43-GlnAsnArgAlaAlaSerGlnAsnGlnGluAla-53 |
| SEQ. ID. NO. 20569 | 60-IleValGluLysAlaGlnAsnLysAlaProGlnSerGluIleAsnAlaGluLeuAlaLysLeuGlnGln-82 |
| SEQ. ID. NO. 20570 | 100-ThrGluPheAspAlaGlnArgTyrAspValAlaGluGly-112 |
| SEQ. ID. NO. 20571 | 118-LeuSerAsnGlnLysAspSerLeu-125 |
| SEQ. ID. NO. 20572 | 140-GlnGlnLysLysTyrAspAla-146 |
| SEQ. ID. NO. 20573 | 153-ThrProValGluAlaAspPhe-159 |
| SEQ. ID. NO. 20574 | 164-MetGluThrLysGlyAspVal-170 |
| SEQ. ID. NO. 20575 | 173-AlaGlnGlyLysSerGlnGluAlaLeuLysAsnTyrGlyGlnAlaLeuGluLysMetProGlnAspSerValGlyArgGluLeuVal-201 |
| SEQ. ID. NO. 20576 | 204-LysLeuAspSerLeuLys-209 |
| Hydrophilic Regions - Hopp-Woods | |
| SEQ. ID. NO. 20577 | 4-HisLeuGluGluGlnGlnGluLeuAspAsn-13 |
| SEQ. ID. NO. 20578 | 45-ArgAlaAlaSerGlnAsnGlnGluAla-53 |
| SEQ. ID. NO. 20579 | 60-IleValGluLysAlaGlnAsnLysAlaProGlnSerGluIleAsnAlaGluLeuAlaLys-79 |

TABLE 1-continued

SEQ. ID. NO. 20580 100-ThrGluPheAspAlaGlnArgTyrAspValAlaGluGly-112
SEQ. ID. NO. 20581 120-AsnGlnLysAspSerLeu-125
SEQ. ID. NO. 20582 140-GlnGlnLysLysTyrAspAla-146
SEQ. ID. NO. 20583 153-ThrProValGluAlaAspPhe-159
SEQ. ID. NO. 20584 164-MetGluThrLysGlyAspVal-170
SEQ. ID. NO. 20585 174-GlnGlyLysSerGlnGluAlaLeuLys-182
SEQ. ID. NO. 20586 187-AlaLeuGluLysMetProGlnAspSerValGlyArgGluLeuVal-201
SEQ. ID. NO. 20587 204-LysLeuAspSerLeuLys-209
a587
AMPHI Regions - AMPHI
SEQ. ID. NO. 20588 6-LeuProAlaLeuProAlaIleLeuProLeuSerAla-17
SEQ. ID. NO. 20589 232-LysGlnProAspArgLeuAsp-238
Antigenic Index - Jameson-Wolf
SEQ. ID. NO. 20590 27-AspIleMetThrAspLysGlyLysTrpLysLeuGluThr-39
SEQ. ID. NO. 20591 44-LeuAsnSerGluAsnAsnArgAlaGluLeu-53
SEQ. ID. NO. 20592 71-ThrGluIleGlnGluAsnGlySerAsnThr-80
SEQ. ID. NO. 20593 95-GlyAsnThrAspIleTyrGlySerGlySer-104
SEQ. ID. NO. 20594 108-HisGluGluArgLysLeuAspGlyAsnGlyLysThrArgAsnLysArgMetSerAsp-126
SEQ. ID. NO. 20595 135-PheLeuLysAspAspLysAsnProAla-143
SEQ. ID. NO. 20596 151-ThrValTyrGluLysSerArgAsnLysAlaSerSerGlyLysSer-165
SEQ. ID. NO. 20597 187-TyrArgIleAsnGlySerLysThrLeuSerSerAsnThrLysTyrLysAlaGly-204
SEQ. ID. NO. 20598 217-AlaAsnAspArgIleSerLeuThrGlyGly-226
SEQ. ID. NO. 20599 231-GlyLysGlnProAspArgLeuAspGlyLysLysGluSerAlaArgAsnThrSerThr-249
SEQ. ID. NO. 20600 273-ValSerGlyGlnSerSerSerGluLeuLysPhe-283
Hydrophilic Regions - Hopp-Woods
SEQ. ID. NO. 20601 27-AspIleMetThrAspLysGlyLysTrpLysLeu-37
SEQ. ID. NO. 20602 47-GluAsnAsnArgAlaGluLeu-53
SEQ. ID. NO. 20603 72-GluIleGlnGluAsnGlySerAsn-79
SEQ. ID. NO. 20604 108-HisGluGluArgLysLeuAspGlyAsnGlyLysThrArgAsnLysArgMetSerAsp-126
SEQ. ID. NO. 20605 135-PheLeuLysAspAspLysAsnPro-142
SEQ. ID. NO. 20606 151-ThrValTyrGluLysSerArgAsnLysAlaSerSerGly-163
SEQ. ID. NO. 20607 193-LysThrLeuSerSer-197
SEQ. ID. NO. 20608 199-ThrLysTyrLysAla-203
SEQ. ID. NO. 20609 217-AlaAsnAspArgIleSer-222
SEQ. ID. NO. 20610 232-LysGlnProAspArgLeuAspGlyLysLysGluSerAlaArgAsn-246
SEQ. ID. NO. 20611 277-SerSerSerGluLeuLysPhe-283
a588
AMPHI Regions - AMPHI
SEQ. ID. NO. 20612 52-GlnAspGlyArgAsnTyrThrGlySerPhe-61
SEQ. ID. NO. 20613 99-GlyThrPheLysLys-103
Antigenic Index - Jameson-Wolf
SEQ. ID. NO. 20614 25-SerTyrGlnGluProGlyCysThrTyrGluGlyAspValGlyLysAspGly
LysProAlaGlyLysGlyThrTrpArgCysGlnAspGlyArgAsnTyrThrGlySerPheLysAsnGlyLysPheAspGlyGlnGly-70
SEQ. ID. NO. 20615 80-IlePheIleGluProPheAsnSerAspSerThrLysPheArg-93
SEQ. ID. NO. 20616 100-ThrPheLysLysGlyLeuAlaHisGlyArgPheThrValSerGlnAsnGlyGluThr-118
SEQ. ID. NO. 20617 124-CysGluAsnGlyMetIleLysGluValLysLeuProLysAsnLys-138
Hydrophilic Regions - Hopp-Woods
SEQ. ID. NO. 20618 33-TyrGluGlyAspValGlyLysAspGlyLysProAlaGly-45
SEQ. ID. NO. 20619 47-GlyThrTrpArgCysGlnAspGlyArgAsnTyr-57
SEQ. ID. NO. 20620 61-PheLysAsnGlyLysPheAspGly-68
SEQ. ID. NO. 20621 85-PheAsnSerAspSerThrLysPheArg-93
SEQ. ID. NO. 20622 100-ThrPheLysLysGlyLeuAla-106
SEQ. ID. NO. 20623 124-CysGluAsnGlyMetIleLysGluValLysLeuProLysAsnLys-138
a589
AMPHI Regions - AMPHI
SEQ. ID. NO. 20624 18-AlaSerArgIleGluLysValLeu-25
SEQ. ID. NO. 20625 54-ValAlaAspIleAlaLysIleIleGluLys-63
SEQ. ID. NO. 20626 103-MetValGlyMetMet-107
SEQ. ID. NO. 20627 128-LeuAlaSerValValGlnLeuTrp-135
SEQ. ID. NO. 20628 155-MetAspValLeuValThrIle-161
SEQ. ID. NO. 20629 198-PheValSerLeuGlyLysPheLeuGluHisArg-208
SEQ. ID. NO. 20630 230-ValGlnArgAspGlyGlu-235
SEQ. ID. NO. 20631 245-GlnIleGlyAspLeuIleArg-251
SEQ. ID. NO. 20632 315-LeuGlyAspMetMetAsnAlaLeuSerGluAlaGln-326
SEQ. ID. NO. 20633 330-AlaProIleAlaArgValAlaAspLys-338
SEQ. ID. NO. 20634 349-GlyIleAlaLeuLeuThrPheIleAlaThr-358
SEQ. ID. NO. 20635 396-MetGlyLysAlaVal-400
SEQ. ID. NO. 20636 471-IleValSerAlaAlaGln-476
SEQ. ID. NO. 20637 482-IleProThrAlaGln-486
SEQ. ID. NO. 20638 502-GlyAlaGlyLeuValLys-507
SEQ. ID. NO. 20639 539-LysProIleGlyAlaPheAlaLeuAlaAspAlaLeuLys-551
SEQ. ID. NO. 20640 553-AspThrAlaGluAlaIleGlyArgLeu-561
SEQ. ID. NO. 20641 603-GluValGlnLysLeuLysAlaAla-610
SEQ. ID. NO. 20642 617-ValGlyAspGlyIleAsnAspAlaPro-625
SEQ. ID. NO. 20643 640-AlaAspValAlaGluHisThr-646
SEQ. ID. NO. 20644 653-GlnHisSerValAsnGlnLeuAlaAspAlaLeuSer-664
SEQ. ID. NO. 20645 680-AlaPhePheTyrAsnIleLeu-686
Antigenic Index - Jameson-Wolf
SEQ. ID. NO. 20646 1-MetGlnGlnLysValArgPheGlnIleGluGlyMetThr-13
SEQ. ID. NO. 20647 17-CysAlaSerArgIleGluLysValLeuAsnLysLysAspPheValGluSer-33

TABLE 1-continued

| | |
|---|---|
| SEQ. ID. NO. 20648 | 39-AlaSerGluGluAlaGlnValValPheAspAspSerLysThrSerVal-54 |
| SEQ. ID. NO. 20649 | 59-LysIleIleGluLysThrGlyTyrGlyAlaLysGluLysThrGluAspThrLeuProGlnProGluAlaGluHis-83 |
| SEQ. ID. NO. 20650 | 114-ThrArgHisAspTrp-118 |
| SEQ. ID. NO. 20651 | 148-IleLysGlyGlyLeu-152 |
| SEQ. ID. NO. 20652 | 205-LeuGluHisArgThrLysLysSerSerLeuAsn-215 |
| SEQ. ID. NO. 20653 | 228-ValAsnValGlnArgAspGlyGluTrpArg-237 |
| SEQ. ID. NO. 20654 | 253-AsnHisGlyGluArgIleAlaAla-260 |
| SEQ. ID. NO. 20655 | 262-GlyIleIleGluSerGlySerGlyTrpAlaAspGluSerHisLeuThrGlyGluSerAsnProGluGluLysLysAlaGlyGly-289 |
| SEQ. ID. NO. 20656 | 298-ThrGluGlySerVal-302 |
| SEQ. ID. NO. 20657 | 323-SerGluAlaGlnGlySerLysAlaProIle-332 |
| SEQ. ID. NO. 20658 | 334-ArgValAlaAspLysAlaAla-340 |
| SEQ. ID. NO. 20659 | 361-IleLysGlyAspTrp-365 |
| SEQ. ID. NO. 20660 | 396-MetGlyLysAlaValLys-401 |
| SEQ. ID. NO. 20661 | 409-AlaAlaAlaMetGluGluAlaAlaHis-417 |
| SEQ. ID. NO. 20662 | 422-ValLeuAspLysThrGlyThrLeuThrGluGlyLysProGlnVal-436 |
| SEQ. ID. NO. 20663 | 443-ProAspSerGlyPheAspGluAspAlaLeu-452 |
| SEQ. ID. NO. 20664 | 459-ValGluGlnAsnAla-463 |
| SEQ. ID. NO. 20665 | 498-AlaGluValLysGlyAlaGlyLeu-505 |
| SEQ. ID. NO. 20666 | 507-LysAlaGlyLysAlaGluPheAla-514 |
| SEQ. ID. NO. 20667 | 520-LysPheSerAspGlyVal-525 |
| SEQ. ID. NO. 20668 | 535-SerValAsnGlyLysProIle-541 |
| SEQ. ID. NO. 20669 | 548-AspAlaLeuLysAlaAspThrAlaGluAlaIleGlyArgLeuLysLysHisAsnIle-566 |
| SEQ. ID. NO. 20670 | 572-SerGlyAspAsnGlnGlyThrValGluTyrValAla-583 |
| SEQ. ID. NO. 20671 | 593-GlyAsnMetSerProArgAspLysAlaAlaGluValGlnLysLeuLysAlaAlaGly-611 |
| SEQ. ID. NO. 20672 | 617-ValGlyAspGlyIleAsnAspAla-624 |
| SEQ. ID. NO. 20673 | 636-MetLysGlyGlyAlaAspValAlaGlu-644 |
| SEQ. ID. NO. 20674 | 668-AlaThrLeuLysAsnIleLys-674 |
| SEQ. ID. NO. 20675 | 715-AsnAlaLeuArgLeuLysArgValLysIleAsp-725 |
| Hydrophilic Regions- Hopp-Woods | |
| SEQ. ID. NO. 20676 | 1-MetGlnGlnLysValArgPheGlnIle-9 |
| SEQ. ID. NO. 20677 | 19-SerArgIleGluLysValLeuAsnLysLysAspPheValGlu-32 |
| SEQ. ID. NO. 20678 | 39-AlaSerGluGluAlaGlnValValPheAspAspSerLysThrSerVal-54 |
| SEQ. ID. NO. 20679 | 64-ThrGlyTyrGlyAlaLysGluLysThrGluAspThrLeuProGlnProGluAlaGluHis-83 |
| SEQ. ID. NO. 20680 | 205-LeuGluHisArgThrLysLysSerSerLeu-214 |
| SEQ. ID. NO. 20681 | 229-AsnValGlnArgAspGlyGluTrpArg-237 |
| SEQ. ID. NO. 20682 | 253-AsnHisGlyGluArgIleAlaAla-260 |
| SEQ. ID. NO. 20683 | 262-GlyIleIleGluSer-266 |
| SEQ. ID. NO. 20684 | 270-TrpAlaAspGluSerHisLeuThrGlyGluSerAsnProGluGluLysLysAlaGlyGly-289 |
| SEQ. ID. NO. 20685 | 323-SerGluAlaGlnGlySerLysAlaProIle-332 |
| SEQ. ID. NO. 20686 | 334-ArgValAlaAspLysAlaAla-340 |
| SEQ. ID. NO. 20687 | 409-AlaAlaAlaMetGluGluAlaAlaHis-417 |
| SEQ. ID. NO. 20688 | 422-ValLeuAspLysThrGlyThr-428 |
| SEQ. ID. NO. 20689 | 430-ThrGluGlyLysProGln-435 |
| SEQ. ID. NO. 20690 | 445-SerGlyPheAspGluAspAlaLeu-452 |
| SEQ. ID. NO. 20691 | 459-ValGluGlnAsnAla-463 |
| SEQ. ID. NO. 20692 | 498-AlaGluValLysGly-502 |
| SEQ. ID. NO. 20693 | 507-LysAlaGlyLysAlaGluPheAla-514 |
| SEQ. ID. NO. 20694 | 548-AspAlaLeuLysAlaAspThrAlaGluAlaIleGlyArgLeuLysLysHisAsnIle-566 |
| SEQ. ID. NO. 20695 | 573-GlyAspAsnGlnGly-577 |
| SEQ. ID. NO. 20696 | 596-SerProArgAspLysAlaAlaGluValGlnLysLeuLysAlaAlaGly-611 |
| SEQ. ID. NO. 20697 | 638-GlyGlyAlaAspValAlaGlu-644 |
| SEQ. ID. NO. 20698 | 668-AlaThrLeuLysAsnIleLys-674 |
| SEQ. ID. NO. 20699 | 717-LeuArgLeuLysArgValLysIleAsp-725 |
| a590 | |
| AMPHI Regions - AMPHI | |
| SEQ. ID. NO. 20700 | 77-TyrLeuProAspAsnLeuLysThrValLeuGluGlnProValThrLeuValAsnHisIleThrHis-98 |
| SEQ. ID. NO. 20701 | 100-ProPheAlaGlyGlyPhe-105 |
| SEQ. ID. NO. 20702 | 123-LysValLeuGluArgPhePhe-129 |
| SEQ. ID. NO. 20703 | 132-GlnValProValSerLeu-137 |
| SEQ. ID. NO. 20704 | 177-TyrGlnLysGlyPheLysSerTyrArgAsnGly-187 |
| SEQ. ID. NO. 20705 | 214-ThrSerAspGlyIleAsnProLeu-221 |
| SEQ. ID. NO. 20706 | 248-AsnGluLeuValAsnLeuVal-254 |
| SEQ. ID. NO. 20707 | 331-LysArgLysPheAlaArgIle-337 |
| SEQ. ID. NO. 20708 | 420-LysMetLeuGluAsp-424 |
| SEQ. ID. NO. 20709 | 450-AspIleAsnGluThrLeuArgLeuMet-458 |
| SEQ. ID. NO. 20710 | 460-AspSerThrValGln-464 |
| Antigenic Index - Jameson-Wolf | |
| SEQ. ID. NO. 20711 | 1-MetLysLysProLeu-5 |
| SEQ. ID. NO. 20712 | 26-LysAlaGluGluSerLeuThrGlnGlnGlnLysIleLeuGln-39 |
| SEQ. ID. NO. 20713 | 48-SerHisGlnTyrGluArgGlyTrpPheThrSerThrGluThrThrValIleArgLeuLysProGluLeu-70 |
| SEQ. ID. NO. 20714 | 75-GlnLysTyrLeuProAspAsnLeuLysThrValLeu-86 |
| SEQ. ID. NO. 20715 | 113-ThrGluPheLysTyrAlaProGluThrGluLysValLeuGlu-126 |
| SEQ. ID. NO. 20716 | 128-PhePheGlyLysGlnVal-133 |
| SEQ. ID. NO. 20717 | 144-AsnGlySerGlyLysMetGluVal-151 |
| SEQ. ID. NO. 20718 | 157-AspTyrGluGluLeuSerGly-163 |
| SEQ. ID. NO. 20719 | 175-ThrValTyrGlnLysGlyPheLysSerTyrArgAsnGlyTyrAspAlaPro-191 |
| SEQ. ID. NO. 20720 | 196-LysLeuAlaAspLysGlyAspAlaAlaPheGlu-206 |
| SEQ. ID. NO. 20721 | 208-ValHisPheAspSerGluThrSerAspGlyIleAsn-219 |
| SEQ. ID. NO. 20722 | 233-PheSerLeuGluTrpLysGluGlyValAspTyr-243 |
| SEQ. ID. NO. 20723 | 264-AsnProAsnGlySerIleAlaProSerLysIleGluValGly-277 |

TABLE 1-continued

SEQ. ID. NO. 20724 281-PheSerThrLysThrGlyGluSerGlyAla-290
SEQ. ID. NO. 20725 292-IleAspSerGluGlyGlnPheArgPhe-300
SEQ. ID. NO. 20726 305-TyrGlyAspGluLysTyrGlyPro-312
SEQ. ID. NO. 20727 330-LeuLysArgLysPheAlaArgIleSerAlaLysLysMetThrGluGluGlnIleArgAsnAspLeu-351
SEQ. ID. NO. 20728 355-ValLysGlyGluAlaSerGly-361
SEQ. ID. NO. 20729 366-AsnProValLeuAsp-370
SEQ. ID. NO. 20730 378-LeuProSerGlyLysIleAspValGlyGly-387
SEQ. ID. NO. 20731 389-IleMetPheLysAspMetLysLysGluAspLeuAsnGln-401
SEQ. ID. NO. 20732 406-LeuLysLysThrGluAlaAspIleArgMet-415
SEQ. ID. NO. 20733 437-AsnAlaGluAspGluAlaGluGlyArgAlaSerLeuAspAspIleAsnGluThrLeu-455
SEQ. ID. NO. 20734 466-MetAlaArgGluLysTyr-471
SEQ. ID. NO. 20735 475-AsnGlyAspGlnIleAsp-480
SEQ. ID. NO. 20736 485-LeuLysAsnAsnGlnLeuLysLeuAsnGlyLysThrLeuGlnAsnGluProGluProAspPheAspGluGlyGlyMetValSerGlu ProGlnGln-516
Hydrophilic Regions - Hopp-Woods
SEQ. ID. NO. 20737 1-MetLysLysProLeu-5
SEQ. ID. NO. 20738 26-LysAlaGluGluSerLeuThrGln-33
SEQ. ID. NO. 20739 62-ThrValIleArgLeuLysProGluLeu-70
SEQ. ID. NO. 20740 77-TyrLeuProAspAsnLeuLysThrValLeu-86
SEQ. ID. NO. 20741 113-ThrGluPheLysTyrAlaProGluThrGluLysValLeuGlu-126
SEQ. ID. NO. 20742 147-GlyLysMetGluVal-151
SEQ. ID. NO. 20743 157-AspTyrGluGluLeuSerGly-163
SEQ. ID. NO. 20744 180-GlyPheLysSerTyrArgAsnGlyTyr-188
SEQ. ID. NO. 20745 196-LysLeuAlaAspLysGlyAspAlaAlaPheGlu-206
SEQ. ID. NO. 20746 208-ValHisPheAspSerGluThrSerAspGly-217
SEQ. ID. NO. 20747 233-PheSerLeuGluTrpLysGluGlyValAspTyr-243
SEQ. ID. NO. 20748 272-SerLysIleGluValGly-277
SEQ. ID. NO. 20749 292-IleAspSerGluGlyGlnPhe-298
SEQ. ID. NO. 20750 306-GlyAspGluLysTyrGlyPro-312
SEQ. ID. NO. 20751 330-LeuLysArgLysPheAlaArgIleSerAlaLysLysMetThrGluGluGlnIleArgAsnAspLeu-351
SEQ. ID. NO. 20752 355-ValLysGlyGluAla-359
SEQ. ID. NO. 20753 381-GlyLysIleAspValGlyGly-387
SEQ. ID. NO. 20754 389-IleMetPheLysAspMetLysLysGluAspLeuAsn-400
SEQ. ID. NO. 20755 406-LeuLysLysThrGluAlaAspIleArgMet-415
SEQ. ID. NO. 20756 437-AsnAlaGluAspGluAlaGluGlyArgAlaSerLeuAspAspIleAsnGluThrLeu-455
SEQ. ID. NO. 20757 466-MetAlaArgGluLysTyr-471
SEQ. ID. NO. 20758 486-LysAsnAsnGlnLeuLysLeuAsnGly-494
SEQ. ID. NO. 20759 496-ThrLeuGlnAsnGluProGluProAspPheAspGluGlyGlyMetValSerGluProGlnGln-516
a591
AMPHI Regions - AMPHI
SEQ. ID. NO. 20760 6-AlaPheIlePheAla-10
SEQ. ID. NO. 20761 17-LeuHisGluPheGlyHisTyrIleValAla-26
SEQ. ID. NO. 20762 61-LeuGlyGlyTyrValLysMetValAsp-69
SEQ. ID. NO. 20763 143-GlyAspLysIleGlnSerValAsnGlyThrProValAlaAspTrp-157
SEQ. ID. NO. 20764 181-SerGlyAlaGlnThrValArgThrIleAspAlaAlaGlyThrProGluAlaGlyLysIleAlaLys-202
SEQ. ID. NO. 20765 218-AlaGlyGlyValGluLys-223
SEQ. ID. NO. 20766 234-ProGlyAspArgLeu-238
SEQ. ID. NO. 20767 245-ProIleAlaSerTrpGlnGluTrpAlaAsnLeuThrArg-257
SEQ. ID. NO. 20768 304-AlaTrpAspAlaGlnIleArg-310
SEQ. ID. NO. 20769 313-TyrArgProSerValValArgAlaPheGly-322
SEQ. ID. NO. 20770 324-GlyTrpGluLysThrValSerHis-331
SEQ. ID. NO. 20771 335-ThrLeuLysPhePheGlyLysLeuIle-343
SEQ. ID. NO. 20772 351-HisIleSerGlyProLeuThrIleAla-359
SEQ. ID. NO. 20773 373-TyrLeuGluPheLeuAlaLeu-379
Antigenic Index - Jameson-Wolf
SEQ. ID. NO. 20774 44-PhePheThrArgLysArgGlyAspThrGlu-53
SEQ. ID. NO. 20775 68-ValAspThrArgGluGlyGluValSerGluAlaAspLeu-80
SEQ. ID. NO. 20776 84-PheAspLysGlnHisProAlaLysArg-92
SEQ. ID. NO. 20777 129-ValGluProAspThrIleAla-135
SEQ. ID. NO. 20778 139-GlyPheGlnSerGlyAspLysIleGlnSer-148
SEQ. ID. NO. 20779 157-TrpGlySerAlaGln-161
SEQ. ID. NO. 20780 187-ArgThrIleAspAlaAlaGlyThrProGluAlaGlyLysIleAlaLysAsnGlnGly-205
SEQ. ID. NO. 20781 219-GlyGlyValGluLysGlySerProAlaGluLysAlaGlyLeuLysProGlyAspArgLeuThrAlaAlaAspGlyLysProIle-246
SEQ. ID. NO. 20782 254-AsnLeuThrArgGlnSerProGlyLysLysIle-264
SEQ. ID. NO. 20783 268-TyrGluArgAlaGlyGlnThrHisThrAlaAspIleArgProAspThrValGluGlnProAspHisThrLeu-291
SEQ. ID. NO. 20784 295-ValGlyLeuArgProGlnProAspArgAlaTrp-305
SEQ. ID. NO. 20785 307-AlaGlnIleArgArgSerTyrArgProSerVal-317
SEQ. ID. NO. 20786 327-LysThrValSerHisSer-332
SEQ. ID. NO. 20787 343-IleSerGlyAsnAla-347
SEQ. ID. NO. 20788 362-AlaGlyGlnSerAla-366
SEQ. ID. NO. 20789 408-IleArgGlyLysProLeuGlyGluArgValGln-418
Hydrophilic Regions - Hopp-Woods
SEQ. ID. NO. 20790 44-PhePheThrArgLysArgGlyAspThr-52
SEQ. ID. NO. 20791 68-ValAspThrArgGluGlyGluValSerGluAlaAspLeu-80
SEQ. ID. NO. 20792 84-PheAspLysGlnHisProAlaLysArg-92
SEQ. ID. NO. 20793 129-ValGluProAspThrIleAla-135
SEQ. ID. NO. 20794 139-GlyPheGlnSerGlyAspLysIleGlnSer-148
SEQ. ID. NO. 20795 193-GlyThrProGluAlaGlyLysIleAlaLys-202
SEQ. ID. NO. 20796 220-GlyValGluLysGlySerProAlaGluLysAlaGlyLeuLysProGlyAspArgLeuThrAlaAlaAspGlyLysPro-245
SEQ. ID. NO. 20797 256-ThrArgGlnSerProGlyLysLysIle-264

TABLE 1-continued

| | |
|---|---|
| SEQ. ID. NO. 20798 | 268-TyrGluArgAlaGlyGln-273 |
| SEQ. ID. NO. 20799 | 277-AlaAspIleArgProAspThrValGluGlnProAsp-288 |
| SEQ. ID. NO. 20800 | 299-ProGlnProAspArgAlaTrp-305 |
| SEQ. ID. NO. 20801 | 308-GlnIleArgArgSerTyrArg-314 |
| SEQ. ID. NO. 20802 | 362-AlaGlyGlnSerAla-366 |
| SEQ. ID. NO. 20803 | 411-LysProLeuGlyGluArgValGln-418 |
| a592 | |
| AMPHI Regions - AMPHI | |
| SEQ. ID. NO. 20804 | 6-PheGlyGlnIlePheSer-11 |
| SEQ. ID. NO. 20805 | 21-GlyGlyLeuLeuGlyGlyLeuIle-28 |
| SEQ. ID. NO. 20806 | 50-AlaProAsnAlaAlaAlaAlaAla-57 |
| SEQ. ID. NO. 20807 | 65-GlnGlyMetIleGlnMetLeuGlyValPheValAsp-76 |
| SEQ. ID. NO. 20808 | 94-ProTyrGlyAspLeu-98 |
| SEQ. ID. NO. 20809 | 109-ValSerGlnValGlyGlnTrp-115 |
| SEQ. ID. NO. 20810 | 153-ThrAlaValPheArgMet-158 |
| SEQ. ID. NO. 20811 | 165-TyrPheGlyAlaValAla-170 |
| SEQ. ID. NO. 20812 | 185-IleMetAlaTrpIleAsnLeuValAlaIleLeuLeuLeuSer-198 |
| Antigenic Index - Jameson-Wolf | |
| SEQ. ID. NO. 20813 | 35-GlyIleLysArgGlyLeuTyrSerAsnGluAlaGlyMetGlySerAlaProAsnAla-53 |
| SEQ. ID. NO. 20814 | 57-AlaGluValLysHisProValSer-64 |
| SEQ. ID. NO. 20815 | 93-GlnProTyrGlyAspLeuSerGly-100 |
| SEQ. ID. NO. 20816 | 137-AlaTyrAlaGluSerAsnVal-143 |
| SEQ. ID. NO. 20817 | 206-ArgAspTyrThrAlaLysLeuLysMetGlyLysAspProGluPheLysLeuSerGluHisProGlyLeuLysArgArgIleLysSerAsp ValTrp-237 |
| Hydrophilic Regions - Hopp-Woods | |
| SEQ. ID. NO. 20818 | 35-GlyIleLysArgGlyLeuTyr-41 |
| SEQ. ID. NO. 20819 | 57-AlaGluValLysHisProVal-63 |
| SEQ. ID. NO. 20820 | 212-LeuLysMetGlyLysAspProGluPheLysLeuSerGlu-224 |
| SEQ. ID. NO. 20821 | 226-ProGlyLeuLysArgArgIleLysSer-234 |
| a593 | |
| AMPHI Regions - AMPHI | |
| SEQ. ID. NO. 20822 | 6-GlyLeuCysLysArgPheGlyGlyLysThr-15 |
| SEQ. ID. NO. 20823 | 41-SerThrLeuLeuAsnMetIleAlaGlyIleValArg-52 |
| SEQ. ID. NO. 20824 | 87-HisMetSerAlaLeuGlu-92 |
| SEQ. ID. NO. 20825 | 102-LysMetProLysAla-106 |
| SEQ. ID. NO. 20826 | 125-AlaHisArgLysProXxxLysLeuSerGlyGlyGlu-136 |
| SEQ. ID. NO. 20827 | 159-PheSerSerLeuAsp-163 |
| SEQ. ID. NO. 20828 | 165-HisLeuArgAspArgLeuArgArgMet-173 |
| SEQ. ID. NO. 20829 | 213-CysGlyThrProGluThrLeuValGlnThrProAlaGlyValGlnValAlaHisLeuMetGly-233 |
| Antigenic Index - Jameson-Wolf | |
| SEQ. ID. NO. 20830 | 6-GlyLeuCysLysArgPheGlyGlyLysThrValAlaAsp-18 |
| SEQ. ID. NO. 20831 | 24-ValGlyArgGlyLysIle-29 |
| SEQ. ID. NO. 20832 | 33-LeuGlyArgSerGlyCysGlyLysSerThr-42 |
| SEQ. ID. NO. 20833 | 50-IleValArgProAspGlyGlyGlu-57 |
| SEQ. ID. NO. 20834 | 61-AsnGlyGluAsnIleThrArgMetProProGluLysArgArgIle-75 |
| SEQ. ID. NO. 20835 | 99-LysMetGlnLysMetProLysAlaGluAlaGluSer-110 |
| SEQ. ID. NO. 20836 | 119-ValGlyLeuGluAsnGluAlaHisArgLysProXxxLysLeuSerGlyGlyGluLysGlnArgLeuAlaLeu-142 |
| SEQ. ID. NO. 20837 | 157-GluSerPheSerSerLeu-162 |
| SEQ. ID. NO. 20838 | 164-ThrHisLeuArgAspArgLeuArgArgMetThrAlaGluArgIleArgLysGlyGlyIle-183 |
| SEQ. ID. NO. 20839 | 190-HisSerProGluGluAlaCysThrAlaAlaAspGluIleAlaVal-204 |
| SEQ. ID. NO. 20840 | 206-HisGluGlyLysIleLeuGlnCysGlyThrProGluThrLeu-219 |
| SEQ. ID. NO. 20841 | 233-GlyLeuProAsnThrAspAspAspArgHisIle-243 |
| SEQ. ID. NO. 20842 | 248-ValArgPheAspGlnAspGlyMetGluCysArgValLeuSer-261 |
| SEQ. ID. NO. 20843 | 263-ThrCysLeuProGluSer-268 |
| SEQ. ID. NO. 20844 | 291-GlyGluIleSerGlyAsnAspThrValArgIleHisIleGluAspArgGluIleValArgPheArg-312 |
| Hydrophilic Regions - Hopp-Woods | |
| SEQ. ID. NO. 20845 | 6-GlyLeuCysLysArgPheGlyGly-13 |
| SEQ. ID. NO. 20846 | 25-GlyArgGlyLysIle-29 |
| SEQ. ID. NO. 20847 | 36-SerGlyCysGlyLys-40 |
| SEQ. ID. NO. 20848 | 51-ValArgProAspGlyGly-56 |
| SEQ. ID. NO. 20849 | 68-MetProProGluLysArgArgIle-75 |
| SEQ. ID. NO. 20850 | 99-LysMetGlnLysMetProLysAlaGluAlaGluSer-110 |
| SEQ. ID. NO. 20851 | 119-ValGlyLeuGluAsnGluAlaHisArgLysProXxxLysLeuSerGlyGlyGluLysGlnArgLeuAlaLeu-142 |
| SEQ. ID. NO. 20852 | 164-ThrHisLeuArgAspArgLeuArgArgMetThrAlaGluArgIleArgLysGlyGly-182 |
| SEQ. ID. NO. 20853 | 191-SerProGluGluAlaCysThrAlaAlaAspGluIleAlaVal-204 |
| SEQ. ID. NO. 20854 | 206-HisGluGlyLysIle-210 |
| SEQ. ID. NO. 20855 | 236-AsnThrAspAspAspArgHisIle-243 |
| SEQ. ID. NO. 20856 | 248-ValArgPheAspGlnAspGlyMetGluCysArgValLeuSer-261 |
| SEQ. ID. NO. 20857 | 291-GlyGluIleSerGly-295 |
| SEQ. ID. NO. 20858 | 297-AspThrValArgIleHisIleGluAspArgGluIleValArgPheArg-312 |
| a594 | |
| AMPHI Regions - AMPHI | |
| SEQ. ID. NO. 20859 | 21-SerIleLeuArgLeu-25 |
| SEQ. ID. NO. 20860 | 108-AlaGlyArgGluCysGlnGluThrAlaAlaAla-118 |
| SEQ. ID. NO. 20861 | 138-AlaIleLysArgCysAsn-143 |
| Antigenic Index - Jameson-Wolf | |
| SEQ. ID. NO. 20862 | 1-MetGlyAlaAspThrAspGlyAspLysAspValArgLeuAsnArgThr-16 |
| SEQ. ID. NO. 20863 | 51-ValGluHisProAsnArgPhe-57 |
| SEQ. ID. NO. 20864 | 75-HisLeuAspGlySerThrGlyGly-82 |
| SEQ. ID. NO. 20865 | 86-PheArgArgGluLysThrGlyHisLysArgArgCysHisThrGlnCys-101 |

TABLE 1-continued

| | |
|---|---|
| SEQ. ID. NO. 20866 | 103-HisSerAlaArgAlaAlaGlyArgGluCysGlnGluThr-115 |
| SEQ. ID. NO. 20867 | 137-ArgAlaIleLysArgCysAsn-143 |
| Hydrophilic Regions - Hopp-Woods | |
| SEQ. ID. NO. 20868 | 1-MetGlyAlaAspThrAspGlyAspLysAspValArgLeuAsnArg-15 |
| SEQ. ID. NO. 20869 | 86-PheArgArgGluLysThrGlyHisLysArgArgCysHis-98 |
| SEQ. ID. NO. 20870 | 105-AlaArgAlaAlaGlyArgGluCysGlnGluThr-115 |
| SEQ. ID. NO. 20871 | 137-ArgAlaIleLysArgCysAsn-143 |
| a595 | |
| AMPHI Regions - AMPHI | |
| SEQ. ID. NO. 20872 | 20-CysGlnProProGluAla-25 |
| SEQ. ID. NO. 20873 | 140-AlaAspLeuGluLysLeuSerGlnProLeuAla-150 |
| SEQ. ID. NO. 20874 | 157-GlnGlyGluValLysGluLeuVal-164 |
| SEQ. ID. NO. 20875 | 169-ThrPheThrGluAlaValLysAlaGlyAspIleGluLysAla-182 |
| SEQ. ID. NO. 20876 | 196-IleGluProIleAlaGluLeuPheSerGluLeuAspPro-208 |
| SEQ. ID. NO. 20877 | 224-AlaGlyPheThrGlyPheHisArg-231 |
| SEQ. ID. NO. 20878 | 243-SerGlyValLysGluIleAlaAlaLysLeuMetThrAspValGluAlaLeuGlnLysGluIleAsp-264 |
| SEQ. ID. NO. 20879 | 274-ValGlyGlyAlaSerGluLeuIleGluGluValAlaGly-286 |
| SEQ. ID. NO. 20880 | 309-AspGlySerLysLysIleValAspLeuPheArgProLeu-321 |
| SEQ. ID. NO. 20881 | 337-PheLysGlnValAsnGluIleLeuAlaLys-346 |
| SEQ. ID. NO. 20882 | 351-AspGlyPheGluThrTyrAspLysLeuGlyGlu-361 |
| SEQ. ID. NO. 20883 | 366-AlaLeuGlnAlaSerIleAsnAlaLeuAlaGluAspLeuAlaGlnLeuArgGlyIleLeuGlyLeu-387 |
| Antigenic Index - Jameson-Wolf | |
| SEQ. ID. NO. 20884 | 1-MetArgLysPheAsn-5 |
| SEQ. ID. NO. 20885 | 21-GlnProProGluAlaGluLysAlaAlaPro-30 |
| SEQ. ID. NO. 20886 | 32-AlaSerGlyGluAlaGlnThrAlaAsnGluGlyGlySer-44 |
| SEQ. ID. NO. 20887 | 50-AsnAspAsnAlaCysGluProMetGlu-58 |
| SEQ. ID. NO. 20888 | 70-IleLysAsnAsnSerGlyArgLysLeuGluTrpGluIle-82 |
| SEQ. ID. NO. 20889 | 87-MetValValAspGluArgGluAsnIleAla-96 |
| SEQ. ID. NO. 20890 | 98-GlyLeuSerAspLysMetThr-104 |
| SEQ. ID. NO. 20891 | 108-LeuProGlyGluTyrGluMet-114 |
| SEQ. ID. NO. 20892 | 120-ThrAsnProArgGlyLysLeuValValThrAspSerGlyPheLysAspThrAlaAsnGluAlaAspLeuGluLysLeuSer-146 |
| SEQ. ID. NO. 20893 | 158-GlyGluValLysGluLeuValAlaLysThrLysThrPheThrGluAlaValLysAlaGlyAspIleGluLysAlaLysSerLeuPheAla-187 |
| SEQ. ID. NO. 20894 | 189-ThrArgValHisTyrGluArgIleGluProIle-199 |
| SEQ. ID. NO. 20895 | 204-SerGluLeuAspProValIleAspAlaArgGluAspAspPheLysAspGlyAlaLysAspAlaGly-225 |
| SEQ. ID. NO. 20896 | 238-ValGluLysAspValSerGlyValLysGluIleAlaAla-250 |
| SEQ. ID. NO. 20897 | 252-LeuMetThrAspValGluAlaLeuGlnLysGluIleAsp-264 |
| SEQ. ID. NO. 20898 | 269-ProProGlyLysValValGlyGlyAla-277 |
| SEQ. ID. NO. 20899 | 279-GluLeuIleGluGluValAlaGlySerLysIleSerGlyGluGluAspArgTyrSerHisThrAspLeuSerAspPheGlnAlaAsnValAspGly SerLysLysIleValAsp-316 |
| SEQ. ID. NO. 20900 | 322-IleGluThrLysAsnLysAlaLeuLeuGluLysThrAspThrAsnPheLysGlnValAsn-341 |
| SEQ. ID. NO. 20901 | 345-AlaLysTyrArgThrLysAspGlyPheGluThrTyrAspLysLeuGlyGluAlaAspArgLysAlaLeu-367 |
| SEQ. ID. NO. 20902 | 374-LeuAlaGluAspLeuAlaGln-380 |
| Hydrophilic Regions- Hopp-Woods | |
| SEQ. ID. NO. 20903 | 1-MetArgLysPheAsn-5 |
| SEQ. ID. NO. 20904 | 21-GlnProProGluAlaGluLysAlaAlaPro-30 |
| SEQ. ID. NO. 20905 | 32-AlaSerGlyGluAlaGlnThrAlaAsnGluGlyGlySer-44 |
| SEQ. ID. NO. 20906 | 52-AsnAlaCysGluProMetGlu-58 |
| SEQ. ID. NO. 20907 | 72-AsnAsnSerGlyArgLysLeuGluTrpGluIle-82 |
| SEQ. ID. NO. 20908 | 87-MetValValAspGluArgGluAsnIle-95 |
| SEQ. ID. NO. 20909 | 99-LeuSerAspLysMetThr-104 |
| SEQ. ID. NO. 20910 | 110-GlyGluTyrGluMet-114 |
| SEQ. ID. NO. 20911 | 122-ProArgGlyLysLeuValVal-128 |
| SEQ. ID. NO. 20912 | 131-SerGlyPheLysAspThrAlaAsnGluAlaAspLeuGluLysLeuSer-146 |
| SEQ. ID. NO. 20913 | 158-GlyGluValLysGluLeuValAlaLysThrLysThrPheThrGluAlaValLysAlaGlyAspIleGluLysAlaLysSerLeuPheAla-187 |
| SEQ. ID. NO. 20914 | 189-ThrArgValHisTyrGluArgIleGluProIle-199 |
| SEQ. ID. NO. 20915 | 204-SerGluLeuAspProValIleAspAlaArgGluAspAspPheLysAspGlyAlaLysAspAlaGly-225 |
| SEQ. ID. NO. 20916 | 238-ValGluLysAspValSerGlyValLysGluIleAlaAla-250 |
| SEQ. ID. NO. 20917 | 252-LeuMetThrAspValGluAlaLeuGlnLysGluIleAsp-264 |
| SEQ. ID. NO. 20918 | 279-GluLeuIleGluGluValAlaGly-286 |
| SEQ. ID. NO. 20919 | 288-LysIleSerGlyGluGluAspArgTyrSerHis-298 |
| SEQ. ID. NO. 20920 | 308-ValAspGlySerLysLysIleValAsp-316 |
| SEQ. ID. NO. 20921 | 322-IleGluThrLysAsnLysAlaLeuLeuGluLysThrAspThrAsnPhe-337 |
| SEQ. ID. NO. 20922 | 347-TyrArgThrLysAspGlyPheGluThrTyrAspLysLeuGlyGluAlaAspArgLysAlaLeu-367 |
| SEQ. ID. NO. 20923 | 374-LeuAlaGluAspLeuAlaGln-380 |
| a596 | |
| AMPHIRegions- AMPHI | |
| SEQ. ID. NO. 20924 | 9-MetLeuArgValSerLysValVal-16 |
| SEQ. ID. NO. 20925 | 50-LeuArgIleMetAlaGlyValAspLys-58 |
| SEQ. ID. NO. 20926 | 87-ValArgGluGluValGluSerGlyLeuGlyGluValAlaAlaAlaGlnLysArgLeuGluGluValTyrAlaGluTyr-112 |
| SEQ. ID. NO. 20927 | 192-ProThrAsnHisLeuAsp-197 |
| SEQ. ID. NO. 20928 | 202-GluTrpLeuGluGlnPheLeuValArgPheProGly-213 |
| SEQ. ID. NO. 20929 | 295-AlaArgPheGluGluMetSerAsnTyr-303 |
| SEQ. ID. NO. 20930 | 322-LeuGlyAsnGluValIleGluPheValAsnValSerLysSerPhe-336 |
| SEQ. ID. NO. 20931 | 366-SerThrLeuPheLysMet-371 |
| SEQ. ID. NO. 20932 | 409-AspAsnIleAlaGlu-413 |
| SEQ. ID. NO. 20933 | 444-IleThrGlyGlnLeuSer-449 |
| SEQ. ID. NO. 20934 | 483-LeuArgAlaLeuGluAspAlaLeuLeuGluPheAla-494 |
| AntigenicIndex -Jameson-Wolf | |
| SEQ. ID. NO. 20935 | 16-ValProProGlnLysThrIleIleLysAspIleSer-27 |
| SEQ. ID. NO. 20936 | 41-LeuAsnGlyAlaGlyLysSerThrVal-49 |

TABLE 1-continued

| | |
|---|---|
| SEQ. ID. NO. 20937 | 54-AlaGlyValAspLysGluPheGluGlyGluAla-64 |
| SEQ. ID. NO. 20938 | 75-LeuProGlnGluProGluLeuAspProGluLysThrValArgGluGluValGluSerGlyLeu-95 |
| SEQ. ID. NO. 20939 | 99-AlaAlaAlaGlnLysArgLeuGluGluValTyr-109 |
| SEQ. ID. NO. 20940 | 112-TyrAlaAsnProAspAlaAspPheAspAlaLeuAlaGluGluGlnGlyArgLeuGlu-130 |
| SEQ. ID. NO. 20941 | 136-GlySerSerThrGlyGlyGlyAlaGluHisGluLeuGluIleAlaAlaAspAlaLeuArg-155 |
| SEQ. ID. NO. 20942 | 157-ProGluTrpAspAlaLysIleAspAsnLeuSerGlyGlyGluLysArgArgValAla-175 |
| SEQ. ID. NO. 20943 | 181-LeuSerLysProAspMet-186 |
| SEQ. ID. NO. 20944 | 190-AspGluProThrAsnHisLeuAspAlaGluSer-200 |
| SEQ. ID. NO. 20945 | 219-ThrHisAspArgTyrPhe-224 |
| SEQ. ID. NO. 20946 | 233-LeuGluLeuAspArgGlyHisGlyIleProTrpLysGlyAsnTyrSerSer-249 |
| SEQ. ID. NO. 20947 | 251-LeuGluGlnLysGluLysArgLeuGluAsnGluAlaLysSerGluAlaAlaArgValLysAlaMetLysGlnGluLeuGluTrp-278 |
| SEQ. ID. NO. 20948 | 280-ArgGlnAsnAlaLysGlyArgGlnAlaLysSerLysAlaArgLeuAlaArgPheGluGluMetSerAsnTyrGluTyrGlnLysArgAsnGlu ThrGlnGlu-313 |
| SEQ. ID. NO. 20949 | 319-AlaGluArgLeuGlyAsnGluVal-326 |
| SEQ. ID. NO. 20950 | 333-SerLysSerPheGlyAsp-338 |
| SEQ. ID. NO. 20951 | 359-GlyProAsnGlyAlaGlyLysSerThrLeu-368 |
| SEQ. ID. NO. 20952 | 373-AlaGlyLysGluGlnProAspSerGlyGluValLysIle-385 |
| SEQ. ID. NO. 20953 | 395-AspGlnSerArgGluGlyLeuGlnAsnAspLysThrValPhe-408 |
| SEQ. ID. NO. 20954 | 411-IleAlaGluGlyArgAspIleLeu-418 |
| SEQ. ID. NO. 20955 | 421-GlyGlnPheGluIleProAlaArgGlnTyrLeuGlyArgPheAsnPheLysGlySerAspGlnSerLysIle-444 |
| SEQ. ID. NO. 20956 | 446-GlyGlnLeuSerGlyGlyGluArgGlyArgLeuHisLeu-458 |
| SEQ. ID. NO. 20957 | 462-LeuLeuGlyGlyGlyAsn-467 |
| SEQ. ID. NO. 20958 | 471-LeuAspGluProSerAsnAspLeuAspValGluThr-482 |
| SEQ. ID. NO. 20959 | 501-SerHisAspArgTrpPhe-506 |
| SEQ. ID. NO. 20960 | 516-AlaCysGluGlyAspSerLysTrp-523 |
| SEQ. ID. NO. 20961 | 526-PheAspGlyAsnTyrGlnGluTyrGluAlaAspLysLysArgArgLeuGlyGluGluGlyThrLysProLysArgIleLysTyrLysProVal ThrArg-558 |
| Hydrophilic Regions - Hopp-Woods | |
| SEQ. ID. NO. 20962 | 54-AlaGlyValAspLysGluPheGluGlyGluAla-64 |
| SEQ. ID. NO. 20963 | 77-GlnGluProGluLeuAspProGluLysThrValArgGluGluValGluSerGlyLeu-95 |
| SEQ. ID. NO. 20964 | 99-AlaAlaAlaGlnLysArgLeuGluGluValTyr-109 |
| SEQ. ID. NO. 20965 | 113-AlaAsnProAspAlaAspPheAspAlaLeuAlaGluGluGlnGlyArgLeuGlu-130 |
| SEQ. ID. NO. 20966 | 141-GlyGlyAlaGluHisGluLeuGluIleAlaAlaAspAlaLeuArg-155 |
| SEQ. ID. NO. 20967 | 157-ProGluTrpAspAlaLysIleAspAsn-165 |
| SEQ. ID. NO. 20968 | 167-SerGlyGlyGluLysArgArgValAla-175 |
| SEQ. ID. NO. 20969 | 181-LeuSerLysProAsp-185 |
| SEQ. ID. NO. 20970 | 190-AspGluProThrAsnHisLeuAspAlaGluSer-200 |
| SEQ. ID. NO. 20971 | 233-LeuGluLeuAspArgGlyHis-239 |
| SEQ. ID. NO. 20972 | 251-LeuGluGlnLysGluLysArgLeuGluAsnGluAlaLysSerGluAlaAlaArgValLysAlaMetLysGlnGluLeuGluTrp-278 |
| SEQ. ID. NO. 20973 | 280-ArgGlnAsnAlaLysGlyArgGlnAlaLysSerLysAlaArgLeuAlaArgPheGluGluMetSerAsn-302 |
| SEQ. ID. NO. 20974 | 304-GluTyrGlnLysArgAsnGluThrGln-312 |
| SEQ. ID. NO. 20975 | 319-AlaGluArgLeuGlyAsnGluVal-326 |
| SEQ. ID. NO. 20976 | 373-AlaGlyLysGluGlnProAspSerGlyGluValLysIle-385 |
| SEQ. ID. NO. 20977 | 395-AspGlnSerArgGluGlyLeuGlnAsnAspLysThrValPhe-408 |
| SEQ. ID. NO. 20978 | 411-IleAlaGluGlyArgAspIleLeu-418 |
| SEQ. ID. NO. 20979 | 435-AsnPheLysGlySerAspGlnSerLysIle-444 |
| SEQ. ID. NO. 20980 | 449-SerGlyGlyGluArgGlyArgLeuHisLeu-458 |
| SEQ. ID. NO. 20981 | 472-AspGluProSerAsnAspLeuAspValGluThr-482 |
| SEQ. ID. NO. 20982 | 517-CysGluGlyAspSer-521 |
| SEQ. ID. NO. 20983 | 529-AsnTyrGlnGluTyrGluAlaAspLysLysArgArgLeuGlyGluGluGlyThrLysProLysArgIleLysTyr-553 |
| a597 | |
| AMPHI Regions - AMPHI | |
| SEQ. ID. NO. 20984 | 6-SerAsnSerLeuLysGlnLeuGlnGlu-14 |
| SEQ. ID. NO. 20985 | 45-TrpAspLysPheGlnLysLeu-51 |
| SEQ. ID. NO. 20986 | 68-GlnIleSerArgPheValSerGly-75? |
| SEQ. ID. NO. 20987 | 101-LeuArgTyrThrArgTyrValAsnAla-109 |
| SEQ. ID. NO. 20988 | 111-AsnArgGluValValLysAspLeuGluLysGlnGln-122 |
| SEQ. ID. NO. 20989 | 132-IleAsnAsnGluLeuAlaArgLeuLysLys-141 |
| SEQ. ID. NO. 20990 | 144-AlaAsnValGlnSerLeu-149 |
| SEQ. ID. NO. 20991 | 157-AspAlaAlaGluGlnThrGlu-163 |
| SEQ. ID. NO. 20992 | 169-AlaLysIleAlaLysAspAlaArg-176 |
| SEQ. ID. NO. 20993 | 189-AsnLysLeuLeuSer-193 |
| SEQ. ID. NO. 20994 | 253-ProSerValMetGlyIleGlySerAlaAspGlyPheSerArgMetGlnGlyArgLeuLysLysProValAspGlyValProThrGly-281 |
| SEQ. ID. NO. 20995 | 302-ProAlThrValGluSerIleAla-309 |
| SEQ. ID. NO. 20996 | 314-SerTyrAlaAspGluLeuAspGlyTyrGlyLys-324 |
| SEQ. ID. NO. 20997 | 336-SerIleTyrAlaGlyLeu-341 |
| Antigenic Index - Jameson-Wolf | |
| SEQ. ID. NO. 20998 | 7-AsnSerLeuLysGlnLeuGlnGluGluArgIleArgGlnGluArgIleArgGlnGluArgIleArgGlnAlaArgGlyAsnLeu-34 |
| SEQ. ID. NO. 20999 | 36-SerValAsnArgLysGlnArgGluAlaTrpAspLysPheGlnLysLeuAsnThrGluLeuAsnArgLeuLysThrGluValAlaAla-64 |
| SEQ. ID. NO. 21000 | 74-SerGlyAsnTyrLysAsnSerGlnProAsn-83 |
| SEQ. ID. NO. 21001 | 91-AsnAlaGluProGlyGlnLysAsnArgPhe-100 |
| SEQ. ID. NO. 21002 | 107-ValAsnAlaSerAsnArgGluValValLysAspLeuGluLysGlnGlnLys-123 |
| SEQ. ID. NO. 21003 | 128-GlnGluGlnLysIleAsnAsnGluLeuAlaArgLeuLysLysIleGln-143 |
| SEQ. ID. NO. 21004 | 149-LeuLeuLysLysGlnGlyValThrAspAlaAlaGluGlnThrGluSerArgArgGlnAsnAlaLysIleAlaLysAspAlaArgLysLeuLeu GluGlnLysGlyAsnGluGlnGlnLeu-188 |
| SEQ. ID. NO. 21005 | 191-LeuLeuSerAsnLeuGluLysLysLysAlaGluHisArgIleGlnAspAlaGluAlaLysArgLysLeuAlaGluAlaArgLeuAlaAlaAla GluLysAlaArgLysGluAlaAlaGlnGlnLysAlaGluAlaArgArgAlaGluMetSerAsnLeuThrAlaGluAspArgAsnIleGlnAlaPro Ser-254 |
| SEQ. ID. NO. 21006 | 259-GlySerAlaAspGlyPheSerArgMetGlnGlyArgLeuLysLysProValAspGlyValProThr-280 |
| SEQ. ID. NO. 21007 | 284-GlyGlnAsnArgSerGlyGlyAspVal-292 |

TABLE 1-continued

| | |
|---|---|
| SEQ. ID. NO. 21008 | 314-SerTyrAlaAspGluLeuAspGlyTyrGly-323 |
| SEQ. ID. NO. 21009 | 329-AspHisGlyGluAsnTyr-334 |
| SEQ. ID. NO. 21010 | 345-SerValGlyLysGlyTyr-350 |
| SEQ. ID. NO. 21011 | 354-AlaGlySerLysIleGlySerSerGlySerLeuProAspGlyGluGluGlyLeu-371 |
| SEQ. ID. NO. 21012 | 381-ValLeuAsnProSerSerTrp-387 |
| Hydrophilic Regions- Hopp-Woods | |
| SEQ. ID. NO. 21013 | 7-AsnSerLeuLysGlnLeuGlnGluGluArgIleArgGlnGluArgIleArgGlnGluArgIleArgGlnAlaArgGlyAsn-33 |
| SEQ. ID. NO. 21014 | 37-ValAsnArgLysGlnArgGluAlaTrpAspLysPheGlnLysLeuAsnThrGluLeuAsnArgLeuLysThrGluValAlaAla-64 |
| SEQ. ID. NO. 21015 | 77-TyrLysAsnSerGln-81 |
| SEQ. ID. NO. 21016 | 91-AsnAlaGluProGlyGlnLysAsnArgPhe-100 |
| SEQ. ID. NO. 21017 | 110-SerAsnArgGluValValLysAspLeuGluLysGlnGlnLys-123 |
| SEQ. ID. NO. 21018 | 128-GlnGluGlnLysIleAsnAsnGluLeuAlaArgLeuLysLysIleGln-143 |
| SEQ. ID. NO. 21019 | 149-LeuLeuLysLysGlnGlyValThrAspAlaAlaGluGlnThrGluSerArgArgGlnAsnAlaLysIleAlaLysAspAlaArgLysLeuLeu GluGlnLysGlyAsnGluGlnGlnLeu-188 |
| SEQ. ID. NO. 21020 | 193-SerAsnLeuGluLysLysLysAlaGluHisArgIleGlnAspAlaGluAlaLysArgLysLeuAlaGluAlaArgLeuAlaAlaAlaGluLysAla ArgLysGluAlaAlaGlnGlnLysAlaGluAlaArgArgAlaGluMet-240 |
| SEQ. ID. NO. 21021 | 244-ThrAlaGluAspArgAsnIleGln-251 |
| SEQ. ID. NO. 21022 | 267-MetGlnGlyArgLeuLysLysProValAsp-276 |
| SEQ. ID. NO. 21023 | 286-AsnArgSerGlyGlyAspVal-292 |
| SEQ. ID. NO. 21024 | 315-TyrAlaAspGluLeuAspGlyTyrGly-323 |
| SEQ. ID. NO. 21025 | 356-SerLysIleGlySer-360 |
| SEQ. ID. NO. 21026 | 363-SerLeuProAspGlyGluGluGlyLeu-371 |
| a601 | |
| AMPHI Regions - AMPHI | |
| SEQ. ID. NO. 21027 | 7-LeuValAspGluIleAspValProAsnIleGlyArg-18 |
| SEQ. ID. NO. 21028 | 26-AlaGlyIleProThrValPhe-32 |
| SEQ. ID. NO. 21029 | 42-GlyLysGluLeuGlnAspAspIleAsnAsnAspAlaAlaAlaLeuGluLysPheGluLysIleArgAlaTyrGlyAlaLeu-68 |
| SEQ. ID. NO. 21030 | 70-MetGlyLeuIleSerAspValSerGluAlaAla-80 |
| SEQ. ID. NO. 21031 | 100-SerSerGlyLysThrValAsn-106 |
| SEQ. ID. NO. 21032 | 137-AlaAlaAlaValProGlyThrLeuValAsnLeuAlaAla-149 |
| SEQ. ID. NO. 21033 | 169-GlyAlaAlaAlaGlu-173 |
| Antigenic Index - Jameson-Wolf | |
| SEQ. ID. NO. 21034 | 3-ProThrGlyAsnLeuValAspGluIleAspValProAsnIleGlyArgLeuLys-20 |
| SEQ. ID. NO. 21035 | 39-GlyTyrThrGlyLysGluLeuGlnAspAspIleAsnAsnAspAlaAlaAlaLeuGluLysPheGluLysIleArgAla-64 |
| SEQ. ID. NO. 21036 | 75-AspValSerGluAlaAlaAlaArgAlaHisThrPro-86 |
| SEQ. ID. NO. 21037 | 97-TyrThrAlaSerSerGlyLysThrValAsn-106 |
| SEQ. ID. NO. 21038 | 149-AlaGlyGlyGlyThrArgLysGluValArgPheGlyHisProSerGlyThrLeuArg-167 |
| SEQ. ID. NO. 21039 | 172-AlaGluCysGlnAspGlyGln-178 |
| SEQ. ID. NO. 21040 | 185-ValMetSerArgSerAlaArgValMet-193 |
| SEQ. ID. NO. 21041 | 198-ValArgValProGluAspCysPhe-205 |
| Hydrophilic Regions - Hopp-Woods | |
| SEQ. ID. NO. 21042 | 7-LeuValAspGluIleAspVal-13 |
| SEQ. ID. NO. 21043 | 40-TyrThrGlyLysGluLeuGlnAspAspIleAsnAsnAspAlaAlaAlaLeuGluLysPheGluLysIleArgAla-64 |
| SEQ. ID. NO. 21044 | 75-AspValSerGluAlaAlaAlaArgAlaHisThr-85 |
| SEQ. ID. NO. 21045 | 99-AlaSerSerGlyLysThrValAsn-106 |
| SEQ. ID. NO. 21046 | 151-GlyGlyThrArgLysGluValArgPhe-159 |
| SEQ. ID. NO. 21047 | 172-AlaGluCysGlnAsp-176 |
| SEQ. ID. NO. 21048 | 188-ArgSerAlaArgValMet-193 |
| SEQ. ID. NO. 21049 | 200-ValProGluAspCysPhe-205 |
| a602 | |
| AMPHI Regions - AMPHI | |
| SEQ. ID. NO. 21050 | 7-AspLysAlaArgHis-11 |
| SEQ. ID. NO. 21051 | 21-ValAsnArgHisGlyGln-26 |
| SEQ. ID. NO. 21052 | 54-ArgGlnIleAlaGlnIle-59 |
| SEQ. ID. NO. 21053 | 61-AlaGlyLeuHisValCysAsnSerVal-69 |
| SEQ. ID. NO. 21054 | 78-HisValIleValGluMetCysAlaTrpTyr-87 |
| Antigenic Index - Jameson-Wolf | |
| SEQ. ID. NO. 21055 | 5-GlnCysAspLysAlaArgHisMetArg-13 |
| SEQ. ID. NO. 21056 | 20-GlnValAsnArgHisGlyGlnThrGlyAsnCysGly-31 |
| SEQ. ID. NO. 21057 | 36-CysSerLeuGlnGlyAsnArgLysAlaGlnValPheAspThrAspLeuIleAspArgGlnIle-56 |
| SEQ. ID. NO. 21058 | 90-SerThrGlyGluTyr-94 |
| SEQ. ID. NO. 21059 | 99-GlnMetArgAspTyrIle-104 |
| Hydrophilic Regions - Hopp-Woods | |
| SEQ. ID. NO. 21060 | 5-GlnCysAspLysAlaArgHisMetArg-13 |
| SEQ. ID. NO. 21061 | 20-GlnValAsnArgHisGlyGln-26 |
| SEQ. ID. NO. 21062 | 39-GlnGlyAsnArgLysAlaGlnValPheAsp-48 |
| SEQ. ID. NO. 21063 | 50-AspLeuIleAspArgGlnIle-56 |
| a603 | |
| AMPHI Regions - AMPHI | |
| SEQ. ID. NO. 21064 | 158-ValMetAspGluLeuAsnAlaCysIlePro-167 |
| SEQ. ID. NO. 21065 | 172-HisAsnProAlaAsnIleSerGlyIleLeuAla-182 |
| SEQ. ID. NO. 21066 | 186-HisPheProGlyLeuProAsnValGly-194 |
| SEQ. ID. NO. 21067 | 199-SerPheHisGlnThrMetPro-205 |
| SEQ. ID. NO. 21068 | 212-AlaValProArgGluLeu-217 |
| SEQ. ID. NO. 21069 | 245-GlyLysProLeuGluAspIleArgMetIleIleAlaHis-257 |
| SEQ. ID. NO. 21070 | 260-AsnGlyAlaSerIleThrAlaIleLysAsnGlyLysSerVal-273 |
| SEQ. ID. NO. 21071 | 280-ThrProIleGluGly-284 |
| SEQ. ID. NO. 21072 | 299-TyrSerTyrLeuThrSer-304 |
| SEQ. ID. NO. 21073 | 324-LeuGlyIleSerGlu-328 |
| SEQ. ID. NO. 21074 | 330-SerAsnAspCysArg-334 |

TABLE 1-continued

| | |
|---|---|
| SEQ. ID. NO. 21075 | 357-ArgLeuAlaLysTyrIleAlaSerMet-365 |
| SEQ. ID. NO. 21076 | 393-ValSerTyrLeuAsp-397 |
| Antigenic Index - Jameson-Wolf | |
| SEQ. ID. NO. 21077 | 1-LeuSerSerArgArgArgGlyArgAsnAsnAspArgLysCysGlyIle-16 |
| SEQ. ID. NO. 21078 | 18-PheAlaGlnArgGlyArgLeuLysHisThrProProAsnAlaHisProPheSerAspAspProThrXxxLysLysGlnProGlnThrThrArg ArgAsnIleMetSer-53 |
| SEQ. ID. NO. 21079 | 63-GlySerSerSerLeuLysGlyAlaValIleAspArgLysSerGlySer-78 |
| SEQ. ID. NO. 21080 | 84-LeuGlyGluArgLeuThrThrProGluAla-93 |
| SEQ. ID. NO. 21081 | 96-ThrPheSerLysAspGlyAsnLysArgGlnValProLeuSerGlyArgAsnCysHis-114 |
| SEQ. ID. NO. 21082 | 124-GluLeuGluLysHisGluLeuHisAspArgIleGln-135 |
| SEQ. ID. NO. 21083 | 142-AlaHisGlyGlyGluLysTyrSerGlu-150 |
| SEQ. ID. NO. 21084 | 157-AlaValMetAspGluLeuAsn-163 |
| SEQ. ID. NO. 21085 | 203-ThrMetProGluArgAlaTyr-209 |
| SEQ. ID. NO. 21086 | 215-ArgGluLeuArgLysLysTyrAlaPheArgArgTyrGlyPheHisGlyThrSerMetArg-234 |
| SEQ. ID. NO. 21087 | 246-LysProLeuGluAspIleArg-252 |
| SEQ. ID. NO. 21088 | 258-LeuGlyAsnGlyAla-262 |
| SEQ. ID. NO. 21089 | 265-ThrAlaIleLysAsnGlyLysSerValAspThrSerMetGly-278 |
| SEQ. ID. NO. 21090 | 289-ThrArgCysGlyAspIleAspProGlyVal-298 |
| SEQ. ID. NO. 21091 | 311-AlaGlnValAspGluMetLeuAsnLysLysSerGly-322 |
| SEQ. ID. NO. 21092 | 327-SerGluLeuSerAsnAspCysArgThrLeuGluIleAlaAlaAspGluGlyHisGluGlyAlaArgLeu-349 |
| SEQ. ID. NO. 21093 | 380-GlyIleGlyGluAsnSerArgAsnIleArgAlaLysThr-392 |
| SEQ. ID. NO. 21094 | 403-IleAspThrLysAlaAsnMetGluLysArgTyrGlyAsnSerGlyIle-418 |
| SEQ. ID. NO. 21095 | 420-SerProThrAspSerSerPro-426 |
| SEQ. ID. NO. 21096 | 432-ProThrAsnGluGluLeu-437 |
| Hydrophilic Regions - Hopp-Woods | |
| SEQ. ID. NO. 21097 | 1-LeuSerSerArgArgArgGlyArgAsnAsnAspArgLysCysGlyIle-16 |
| SEQ. ID. NO. 21098 | 18-PheAlaGlnArgGlyArgLeuLysHisThrPro-28 |
| SEQ. ID. NO. 21099 | 34-PheSerAspAspProThrXxxLysLysGlnProGlnThrThrArgArgAsnIleMet-52 |
| SEQ. ID. NO. 21100 | 70-AlaValIleAspArgLysSerGly-77 |
| SEQ. ID. NO. 21101 | 84-LeuGlyGluArgLeuThrThr-90 |
| SEQ. ID. NO. 21102 | 97-PheSerLysAspGlyAsnLysArgGlnValProLeuSerGlyArgAsnCysHis-114 |
| SEQ. ID. NO. 21103 | 124-GluLeuGluLysHisGluLeuHisAspArgIleGln-135 |
| SEQ. ID. NO. 21104 | 143-HisGlyGlyGluLysTyrSerGlu-150 |
| SEQ. ID. NO. 21105 | 157-AlaValMetAspGluLeuAsn-163 |
| SEQ. ID. NO. 21106 | 204-MetProGluArgAlaTyr-209 |
| SEQ. ID. NO. 21107 | 215-ArgGluLeuArgLysLysTyrAlaPhe-223 |
| SEQ. ID. NO. 21108 | 246-LysProLeuGluAspIleArg-252 |
| SEQ. ID. NO. 21109 | 268-LysAsnGlyLysSerValAspThr-275 |
| SEQ. ID. NO. 21110 | 290-ArgCysGlyAspIleAspPro-296 |
| SEQ. ID. NO. 21111 | 311-AlaGlnValAspGluMetLeuAsnLysLysSerGly-322 |
| SEQ. ID. NO. 21112 | 328-GluLeuSerAsnAspCysArgThrLeuGluIleAlaAlaAspGluGlyHisGluGlyAlaArgLeu-349 |
| SEQ. ID. NO. 21113 | 381-IleGlyGluAsnSerArgAsnIleArgAlaLysThr-392 |
| SEQ. ID. NO. 21114 | 403-IleAspThrLysAlaAsnMetGluLysArgTyrGly-414 |
| SEQ. ID. NO. 21115 | 433-ThrAsnGluGluLeu-437 |
| a604 | |
| AMPHI Regions - AMPHI | |
| SEQ. ID. NO. 21116 | 36-HisArgValValGlnPheAla-42 |
| SEQ. ID. NO. 21117 | 53-ValGlyGlyIleHisGlyPheAlaThr-61 |
| SEQ. ID. NO. 21118 | 78-ValArgAlaGlyGlySerPhe-84 |
| SEQ. ID. NO. 21119 | 95-ArgThrValSerAlaAspPheLeuGluPhePheGlnSerCysGlyIle-110 |
| SEQ. ID. NO. 21120 | 114-ValValLeuGlnLeuPheAlaArgValAlaGlnValGlyGlyIleGlnGluAsn-131 |
| SEQ. ID. NO. 21121 | 148-ArgHisIleAsnPheIleAspGlnIleAlaGlyTrpGlu-160 |
| SEQ. ID. NO. 21122 | 166-ValGlyTrpIleLysLysPheAsp-173 |
| SEQ. ID. NO. 21123 | 191-PheGlnAsnCysAlaValLeuHisArg-199 |
| Antigenic Index - Jameson-Wolf | |
| SEQ. ID. NO. 21124 | 11-AlaAlaCysGlyLysValAspGlnArgThrGlyHisGlyGlyGlyGlyArgAsnGlyAsnArgGlyGlyThrHis-35 |
| SEQ. ID. NO. 21125 | 67-GlyGlyGlyArgAspGluGlyAspPheArgArgValArgAlaGlyGlySerPhe-84 |
| SEQ. ID. NO. 21126 | 127-GlyIleGlnGluAsnGlyArgAsnAlaArgValAspGluArgGlyPheGln-143 |
| SEQ. ID. NO. 21127 | 175-TyrPheGlyCysArgGluArgTyrAlaVal-184 |
| SEQ. ID. NO. 21128 | 201-MetGlyAsnAsnGly-205 |
| SEQ. ID. NO. 21129 | 211-LeuProAspPheAspCysAlaAsp-218 |
| Hydrophilic Regions - Hopp-Woods | |
| SEQ. ID. NO. 21130 | 14-GlyLysValAspGlnArgThrGlyHis-22 |
| SEQ. ID. NO. 21131 | 24-GlyGlyGlyArgAsnGlyAsnArgGlyGlyThrHis-35 |
| SEQ. ID. NO. 21132 | 68-GlyGlyArgAspGluGlyAspPheArgArgValArgAla-80 |
| SEQ. ID. NO. 21133 | 127-GlyIleGlnGluAsnGlyArgAsnAlaArgValAspGluArgGlyPhe-142 |
| SEQ. ID. NO. 21134 | 178-CysArgGluArgTyrAlaVal-184 |
| SEQ. ID. NO. 21135 | 214-PheAspCysAlaAsp-218 |
| a605 | |
| AMPHI Regions - AMPHI | |
| SEQ. ID. NO. 21136 | 13-ArgGlnIleTrpLysIleAlaAsp-20 |
| SEQ. ID. NO. 21137 | 38-ThrLeuPheTyrArgPheIleSerGluAsnPheThrAspTyrMetGln-53 |
| SEQ. ID. NO. 21138 | 107-LysLeuLysGluIlePheThrAlaIle-115 |
| SEQ. ID. NO. 21139 | 128-IleLysGlyLeuPheAspAspPheAsp-136 |
| SEQ. ID. NO. 21140 | 141-ArgLeuGlySerThr-145 |
| SEQ. ID. NO. 21141 | 155-AlaValLeuLysGlyValAlaGluLeu-163 |
| SEQ. ID. NO. 21142 | 173-IleAspLeuPheGlyAspAlaTyrGluTyrLeuIleSerAsn-186 |
| SEQ. ID. NO. 21143 | 188-AlaAlaAsnAlaGlyLys-193 |
| SEQ. ID. NO. 21144 | 204-ValSerLysLeuIleAlaArg-210 |
| SEQ. ID. NO. 21145 | 217-GluLysValAsnLysIleTyrAspPro-225 |

TABLE 1-continued

| | |
|---|---|
| SEQ. ID. NO. 21146 | 240-PheAspGluHisIle-244 |
| SEQ. ID. NO. 21147 | 291-AspSerLysProPheAspAlaValValSerAsn-301 |
| SEQ. ID. NO. 21148 | 341-HisAlaLeuAsnTyr-345 |
| SEQ. ID. NO. 21149 | 355-ValSerPheProGly-359 |
| SEQ. ID. NO. 21150 | 433-GluHisIleAlaGluIleValLysLeuPheAla-443 |
| SEQ. ID. NO. 21151 | 452-AlaGlnAsnAlaAlaGlnGlnThr-459 |
| SEQ. ID. NO. 21152 | 471-SerTyrValGluProGlu-476 |
| SEQ. ID. NO. 21153 | 478-ThrArgGluIleIleAspIle-484 |
| SEQ. ID. NO. 21154 | 489-AlaGluIleSerGluThrValAlaLysIleGluArgLeuArgArgGluIleAspGluValIleAlaGluIleGlu-513 |
| Antigenic Index - Jameson-Wolf | |
| SEQ. ID. NO. 21155 | 5-IleGlnGlnArgAlaGlnLeu-11 |
| SEQ. ID. NO. 21156 | 18-IleAlaAspGluValArgGlyAlaValAspGlyTrpAsp-30 |
| SEQ. ID. NO. 21157 | 44-IleSerGluAsnPheThrAspTyrMetGlnAlaGlyAspSerSerIleAsp-60 |
| SEQ. ID. NO. 21158 | 63-AlaMetProAspSer-67 |
| SEQ. ID. NO. 21159 | 71-ProGluIleLysAspAspAlaValLysVal-80 |
| SEQ. ID. NO. 21160 | 98-AlaHisGlnAsnGluGluLeuAsnThrLysLeuLysGlu-110 |
| SEQ. ID. NO. 21161 | 116-GluSerSerAlaSerGlyTyrProSerGluGlnAspIleLysGlyLeuPheAspAspPheAspThrThrSerSerArgLeu-142 |
| SEQ. ID. NO. 21162 | 146-ValAlaAspLysAsnLysArgLeu-153 |
| SEQ. ID. NO. 21163 | 164-AspPheGlySerPheGluAspHisHis-172 |
| SEQ. ID. NO. 21164 | 190-AsnAlaGlyLysSerGlyGlyGluPhePheThr-200 |
| SEQ. ID. NO. 21165 | 215-GlyGlnGluLysValAsnLysIleTyrAspProAlaCysGlySerGlySer-231 |
| SEQ. ID. NO. 21166 | 235-GlnAlaLysLysGlnPheAsp-241 |
| SEQ. ID. NO. 21167 | 253-GluIleAsnHisThrThrTyrAsn-260 |
| SEQ. ID. NO. 21168 | 280-LeuGlyAspThrLeuThrAsnProLysLeuLysAspSerLysProPheAspAla-297 |
| SEQ. ID. NO. 21169 | 310-GlySerGlyAspProThrLeuIleAsnAspAspArgPheAlaPro-324 |
| SEQ. ID. NO. 21170 | 330-ProLysSerLysAlaAsp-335 |
| SEQ. ID. NO. 21171 | 345-TyrLeuSerGlyArgGlyArgAlaAla-353 |
| SEQ. ID. NO. 21172 | 362-TyrArgGlyGlyAlaGluGlnLysIleArg-371 |
| SEQ. ID. NO. 21173 | 403-LeuSerLysHisLysAspAsnThrAsp-411 |
| SEQ. ID. NO. 21174 | 418-GlyGlyPhePheLysLysGluThrAsnAsnAsnValLeuThrGluGluHisIle-435 |
| SEQ. ID. NO. 21175 | 442-PheAlaAspLysAlaAspVal-448 |
| SEQ. ID. NO. 21176 | 458-GlnThrValLysAspAsnGlyTyr-465 |
| SEQ. ID. NO. 21177 | 473-ValGluProGluAspThrArgGluIleIleAsp-483 |
| SEQ. ID. NO. 21178 | 490-GluIleSerGluThrValAlaLysIleGluArgLeuArgArgGluIleAspGluValIleAla-510 |
| Hydrophilic Regions - Hopp-Woods | |
| SEQ. ID. NO. 21179 | 18-IleAlaAspGluValArgGlyAlaValAsp-27 |
| SEQ. ID. NO. 21180 | 55-GlyAspSerSerIle-59 |
| SEQ. ID. NO. 21181 | 71-ProGluIleLysAspAspAlaValLysVal-80 |
| SEQ. ID. NO. 21182 | 98-AlaHisGlnAsnGluGluLeuAsnThrLysLeuLysGlu-110 |
| SEQ. ID. NO. 21183 | 122-TyrProSerGluGlnAspIleLysGlyLeuPheAspAspPheAspThrThrSerSerArgLeu-142 |
| SEQ. ID. NO. 21184 | 146-ValAlaAspLysAsnLysArgLeu-153 |
| SEQ. ID. NO. 21185 | 167-SerPheGluAspHisHis-172 |
| SEQ. ID. NO. 21186 | 191-AlaGlyLysSerGlyGly-196 |
| SEQ. ID. NO. 21187 | 215-GlyGlnGluLysValAsnLysIleTyrAsp-224 |
| SEQ. ID. NO. 21188 | 235-GlnAlaLysLysGlnPheAsp-241 |
| SEQ. ID. NO. 21189 | 287-ProLysLeuLysAspSerLysProPhe-295 |
| SEQ. ID. NO. 21190 | 316-LeuIleAsnAspAspArgPheAla-323 |
| SEQ. ID. NO. 21191 | 330-ProLysSerLysAlaAsp-335 |
| SEQ. ID. NO. 21192 | 348-GlyArgGlyArgAla-352 |
| SEQ. ID. NO. 21193 | 364-GlyGlyAlaGluGlnLysIleArg-371 |
| SEQ. ID. NO. 21194 | 404-SerLysHisLysAspAsnThrAsp-411 |
| SEQ. ID. NO. 21195 | 419-GlyPhePheLysLysGluThrAsn-426 |
| SEQ. ID. NO. 21196 | 430-LeuThrGluGluHisIle-435 |
| SEQ. ID. NO. 21197 | 442-PheAlaAspLysAlaAspVal-448 |
| SEQ. ID. NO. 21198 | 458-GlnThrValLysAspAsnGly-464 |
| SEQ. ID. NO. 21199 | 473-ValGluProGluAspThrArgGluIleIleAsp-483 |
| SEQ. ID. NO. 21200 | 490-GluIleSerGluThrValAlaLysIleGluArgLeuArgArgGluIleAspGluValIleAla-510 |
| a606 | |
| AMPHI Regions - AMPHI | |
| SEQ. ID. NO. 21201 | 72-LeuLeuAspHisMetThrArgAspGlu-80 |
| SEQ. ID. NO. 21202 | 90-AlaHisValGlyAsnGlyAsp-96 |
| SEQ. ID. NO. 21203 | 100-LeuThrLeuIleGlnGlyValValAsnThrPhe-110 |
| SEQ. ID. NO. 21204 | 116-ArgIleIleAlaAsn-120 |
| SEQ. ID. NO. 21205 | 139-SerMetValPheGlnIleLeuPheGlyPheLeuAlaSerLeuIleVal-154 |
| SEQ. ID. NO. 21206 | 171-LysLeuValGlyAlaProLysMetIleSerAlaLeuGlnArg-184 |
| SEQ. ID. NO. 21207 | 191-AspLeuProGluGluMetAsnAla-198 |
| Antigenic Index - Jameson-Wolf | |
| SEQ. ID. NO. 21208 | 13-GluValIleAspThrProArgThrGluGluGluAla-24 |
| SEQ. ID. NO. 21209 | 31-GluAlaGlnAlaArgGlnTrpAsnLeuLysThrProGlu-43 |
| SEQ. ID. NO. 21210 | 48-HisSerProGluProAsnAla-54 |
| SEQ. ID. NO. 21211 | 57-ThrGlyAlaSerArgAsnSerSer-64 |
| SEQ. ID. NO. 21212 | 75-HisMetThrArgAspGluValGluAla-83 |
| SEQ. ID. NO. 21213 | 92-ValGlyAsnGlyAsp-96 |
| SEQ. ID. NO. 21214 | 122-IleAlaArgAsnAsnAspGlySerGlnSerGlnGlyThr-134 |
| SEQ. ID. NO. 21215 | 159-ArgGlnArgGluTyrArgAlaAspAlaGlyAla-169 |
| SEQ. ID. NO. 21216 | 182-LeuGlnArgLeuLysGlyAsnProValAspLeuProGluGluMetAsn-197 |
| SEQ. ID. NO. 21217 | 203-GlyAspThrArgAspSerLeuLeuSerThrHisProSerLeuAspAsnArgIleAlaArgLeuLysSer-225 |
| Hydrophilic Regions - Hopp-Woods | |
| SEQ. ID. NO. 21218 | 13-GluValIleAspThrProArgThrGluGluGluAla-24 |
| SEQ. ID. NO. 21219 | 59-AlaSerArgAsnSer-63 |

TABLE 1-continued

| | |
|---|---|
| SEQ. ID. NO. 21220 | 75-HisMetThrArgAspGluValGluAla-83 |
| SEQ. ID. NO. 21221 | 124-ArgAsnAsnAspGlySerGlnSer-131 |
| SEQ. ID. NO. 21222 | 159-ArgGlnArgGluTyrArgAlaAspAlaGlyAla-169 |
| SEQ. ID. NO. 21223 | 183-GlnArgLeuLysGlyAsnPro-189 |
| SEQ. ID. NO. 21224 | 191-AspLeuProGluGluMetAsn-197 |
| SEQ. ID. NO. 21225 | 203-GlyAspThrArgAspSerLeu-209 |
| SEQ. ID. NO. 21226 | 214-ProSerLeuAspAsnArgIleAlaArgLeuLysSer-225 |
| a607 | |
| AMPHI Regions - AMPHI | |
| SEQ. ID. NO. 21227 | 18-ArgLeuLeuThrAlaLeuAlaLeu-25 |
| SEQ. ID. NO. 21228 | 70-PheMetGlyIleMetAlaAlaLeuAsnProMetIleAlaGln-83 |
| SEQ. ID. NO. 21229 | 90-ThrAspGluValGlyGluThr-96 |
| SEQ. ID. NO. 21230 | 104-GlyLeuPheLeuGlyValPheGlyMetValLeuMetTrpAlaAlaIleThrProPheArgAsnTrpLeuThrLeuSerAspTyrValGluGlyThrMet-136 |
| SEQ. ID. NO. 21231 | 151-MetValHisArgAlaLeuHisAlaTyrAlaSerSer-162 |
| SEQ. ID. NO. 21232 | 226-PhePheArgProPheGly-231 |
| SEQ. ID. NO. 21233 | 244-PheLysGlnIleTrpLysIleGlyAla-252 |
| SEQ. ID. NO. 21234 | 320-AlaArgTyrIleSerGlyValSerLeu-328 |
| SEQ. ID. NO. 21235 | 337-IleThrValLeuSerLeuVal-343 |
| SEQ. ID. NO. 21236 | 373-PheGlnProAlaAspPheThrGlnCysIleAlaSerTyrAla-386 |
| SEQ. ID. NO. 21237 | 424-TyrGlyPheTrpThrAlaLeuIleAla-432 |
| Antigenic Index - Jameson-Wolf | |
| SEQ. ID. NO. 21238 | 15-LysGluValArgLeu-19 |
| SEQ. ID. NO. 21239 | 47-GlyAlaGlyLysGluAspLeuAla-54 |
| SEQ. ID. NO. 21240 | 86-GlyAlaGlyLysThrAspGluValGlyGluThrGlyArgGlnGlyIle-101 |
| SEQ. ID. NO. 21241 | 121-ProPheArgAsnTrp-125 |
| SEQ. ID. NO. 21242 | 128-LeuSerAspTyrValGluGlyThr-135 |
| SEQ. ID. NO. 21243 | 160-AlaSerSerLeuAsnArgProArgLeu-168 |
| SEQ. ID. NO. 21244 | 234-AlaLysPheGlyLysProAspTrp-241 |
| SEQ. ID. NO. 21245 | 311-SerLeuGlyArgArgGluPheSerArgAlaArgTyrIleSer-324 |
| SEQ. ID. NO. 21246 | 353-TyrAsnAsnAspPro-357 |
| SEQ. ID. NO. 21247 | 388-ArgGlyTyrLysValThrLys-394 |
| SEQ. ID. NO. 21248 | 447-LeuCysSerArgGluMetValArgSerHisLysAlaVal-459 |
| Hydrophilic Regions - Hopp-Woods | |
| SEQ. ID. NO. 21249 | 15-LysGluValArgLeu-19 |
| SEQ. ID. NO. 21250 | 47-GlyAlaGlyLysGluAspLeuAla-54 |
| SEQ. ID. NO. 21251 | 88-GlyLysThrAspGluValGlyGluThrGlyArg-98 |
| SEQ. ID. NO. 21252 | 163-LeuAsnArgProArg-167 |
| SEQ. ID. NO. 21253 | 312-LeuGlyArgArgGluPheSerArg-319 |
| SEQ. ID. NO. 21254 | 390-TyrLysValThrLys-394 |
| SEQ. ID. NO. 21255 | 447-LeuCysSerArgGluMetValArgSerHisLysAlaVal-459 |
| a608 | |
| AMPHI Regions - AMPHI | |
| SEQ. ID. NO. 21256 | 66-AlaValGlnLysIleLeuGln-72 |
| SEQ. ID. NO. 21257 | 93-ValLeuSerLeuLeu-97 |
| SEQ. ID. NO. 21258 | 103-ArgAlaSerAspGluLeuAlaArgIlePheGlyThrGln-115 |
| SEQ. ID. NO. 21259 | 124-AspIleGlyHisGlyIleLysGlnIleGlyArgAsnIleAlaGluGlnIleGlyArgPheSerArgGluProGluSerAla-150 |
| SEQ. ID. NO. 21260 | 154-AsnGluAlaLeuAlaAspCysLeuAspGluIleSerArgLeuArgAspGlyValGluArgLeuAsnGluArgLeuAspArgLeu-181 |
| Antigenic Index - Jameson-Wolf | |
| SEQ. ID. NO. 21261 | 13-LeuGlnSerProAspSerArgSerGluLeu-22 |
| SEQ. ID. NO. 21262 | 39-LeuAlaGlyArgIleThrGluAspGlyLeuLeuSerAlaGlyAsnGlyPheAlaAspThrGluIleThrPheArgAsnSerAla-66 |
| SEQ. ID. NO. 21263 | 71-LeuGlnGlyGlyGluProGlyAlaGlyAspIleGlyLeuGluGly-85 |
| SEQ. ID. NO. 21264 | 98-GlySerLeuArgSerArgAlaSerAspGluLeuAla-109 |
| SEQ. ID. NO. 21265 | 114-ThrGlnAlaAspIleGlySerArgAlaAlaAsp-124 |
| SEQ. ID. NO. 21266 | 131-GlnIleGlyArgAsnIleAla-137 |
| SEQ. ID. NO. 21267 | 139-GlnIleGlyArgPheSerArgGluProGluSerAlaAsnIleGlyAsn-154 |
| SEQ. ID. NO. 21268 | 156-AlaLeuAlaAspCysLeuAspGluIleSerArgLeuArgAspGlyValGluArgLeuAsnGluArgLeuAspArgLeuGluArgAspIleTrp-186 |
| Hydrophilic Regions - Hopp-Woods | |
| SEQ. ID. NO. 21269 | 15-SerProAspSerArgSerGluLeu-22 |
| SEQ. ID. NO. 21270 | 39-LeuAlaGlyArgIleThrGluAspGlyLeu-48 |
| SEQ. ID. NO. 21271 | 56-AlaAspThrGluIleThrPhe-62 |
| SEQ. ID. NO. 21272 | 74-GlyGluProGlyAlaGly-79 |
| SEQ. ID. NO. 21273 | 81-IleGlyLeuGluGly-85 |
| SEQ. ID. NO. 21274 | 100-LeuArgSerArgAlaSerAspGluLeuAla-109 |
| SEQ. ID. NO. 21275 | 116-AlaAspIleGlySerArgAlaAlaAsp-124 |
| SEQ. ID. NO. 21276 | 139-GlnIleGlyArgPheSerArgGluProGluSerAlaAsnIleGly-153 |
| SEQ. ID. NO. 21277 | 156-AlaLeuAlaAspCysLeuAspGluIleSerArgLeuArgAspGlyValGluArgLeuAsnGluArgLeuAspArgLeuGluArgAspIleTrp-186 |
| a609 | |
| AMPHI Regions - AMPHI | |
| SEQ. ID. NO. 21278 | 15-ThrLeuAspAlaPheVal-20 |
| SEQ. ID. NO. 21279 | 30-HisHisIlePheHisGluPheArgValPheValGlyPhePhe-43 |
| SEQ. ID. NO. 21280 | 52-PheGluGlnAlaValGlu-57 |
| SEQ. ID. NO. 21281 | 67-IleAspAspPheLeu-71 |
| SEQ. ID. NO. 21282 | 114-ValAlaValCysThrVal-119 |
| Antigenic Index - Jameson-Wolf | |
| SEQ. ID. NO. 21283 | 10-AlaLeuAspAspGluThrLeu-16 |
| SEQ. ID. NO. 21284 | 20-ValGlyAsnGlnArgSerSerAspIleAla-29 |
| SEQ. ID. NO. 21285 | 69-AspPheLeuAspThrAspPheGlyIle-77 |

TABLE 1-continued

| | |
|---|---|
| SEQ. ID. NO. 21286 | 79-SerGlnAlaAspGlyAsnValArg-86 |
| SEQ. ID. NO. 21287 | 99-GlyThrArgAlaLysArgGlyTyrGlyAsnHisAspLeu-111 |
| SEQ. ID. NO. 21288 | 124-ArgGluAlaAspIle-128 |
| Hydrophilic Regions - Hopp-Woods | |
| SEQ. ID. NO. 21289 | 10-AlaLeuAspAspGluThrLeu-16 |
| SEQ. ID. NO. 21290 | 23-GlnArgSerSerAspIle-28 |
| SEQ. ID. NO. 21291 | 79-SerGlnAlaAspGlyAsnVal-85 |
| SEQ. ID. NO. 21292 | 100-ThrArgAlaLysArgGlyTyrGly-107 |
| SEQ. ID. NO. 21293 | 124-ArgGluAlaAspIle-128 |
| a610 | |
| AMPHI Regions - AMPHI | |
| SEQ. ID. NO. 21294 | 6-MetGlnPheProTyr-10 |
| SEQ. ID. NO. 21295 | 14-SerAlaSerArgMetArgArgMetArgArg-23 |
| SEQ. ID. NO. 21296 | 98-GluArgAlaGlnGluAlaTyr-104 |
| SEQ. ID. NO. 21297 | 111-ProSerThrValArgAlaLeuArgGluArg-120 |
| SEQ. ID. NO. 21298 | 187-IleArgGluAlaLeuGlu-192 |
| SEQ. ID. NO. 21299 | 208-TyrAlaSerAlaPheTyrGlyProPheArgAsp-218 |
| SEQ. ID. NO. 21300 | 223-SerGlyAsnLeuGlyLysAlaAsp-230 |
| SEQ. ID. NO. 21301 | 268-LeuAspValValArgArgValLysAspGlu-277 |
| SEQ. ID. NO. 21302 | 296-AlaAlaValAlaAsn-300 |
| Antigenic Index - Jameson-Wolf | |
| SEQ. ID. NO. 21303 | 11-ArgAsnValSerAlaSerArgMetArgArgMetArgArgAspAspPheSerArgArgLeuMetArgGluHisThrLeuThrAlaAspAsp-40 |
| SEQ. ID. NO. 21304 | 50-GlySerAlaArgGluGluAspValProSerMetProGlyValLysArgGlnSerLeuAsp-69 |
| SEQ. ID. NO. 21305 | 75-AlaGluGluAlaValLys-80 |
| SEQ. ID. NO. 21306 | 94-AlaAsnLysThrGluArgAlaGlnGluAlaTyrAsnProGluGlyLeuVal-110 |
| SEQ. ID. NO. 21307 | 115-ArgAlaLeuArgGluArgPhePro-122 |
| SEQ. ID. NO. 21308 | 139-GlyGlnAspGlyLeuThrAspGluAsnGlyTyrValMetAsnAspGluThrVal-156 |
| SEQ. ID. NO. 21309 | 175-AlaProSerAspMetMetAspGlyArgIleGlyAlaIleArgGluAlaLeuGluAspAlaGlyHis-196 |
| SEQ. ID. NO. 21310 | 215-ProPheArgAspAlaValGlySerSerGlyAsnLeuGlyLysAlaAspLysLysThrTyrGlnMetAspProAlaAsnThrAspGluAla LeuHis-246 |
| SEQ. ID. NO. 21311 | 250-LeuAspIleGlnGluGlyAlaAsp-257 |
| SEQ. ID. NO. 21312 | 270-ValValArgArgValLysAspGluPheGlyVal-280 |
| SEQ. ID. NO. 21313 | 302-TrpLeuAspGlyGlyLysValVal-309 |
| SEQ. ID. NO. 21314 | 317-LysArgAlaGlyAlaAspGly-323 |
| SEQ. ID. NO. 21315 | 331-GluAlaAlaLysMetLeuLysArg-338 |
| Hydrophilic Regions - Hopp-Woods | |
| SEQ. ID. NO. 21316 | 14-SerAlaSerArgMetArgArgMetArgArgAspAspPheSerArgArgLeuMetArgGluHisThrLeuThrAla-38 |
| SEQ. ID. NO. 21317 | 50-GlySerAlaArgGluGluAspValProSer-59 |
| SEQ. ID. NO. 21318 | 61-ProGlyValLysArgGlnSerLeuAsp-69 |
| SEQ. ID. NO. 21319 | 75-AlaGluGluAlaValLys-80 |
| SEQ. ID. NO. 21320 | 95-AsnLysThrGluArgAlaGlnGluAlaTyrAsn-105 |
| SEQ. ID. NO. 21321 | 115-ArgAlaLeuArgGluArgPhePro-122 |
| SEQ. ID. NO. 21322 | 141-AspGlyLeuThrAspGluAsnGly-148 |
| SEQ. ID. NO. 21323 | 151-MetAsnAspGluThrVal-156 |
| SEQ. ID. NO. 21324 | 178-AspMetMetAspGlyArgIleGlyAlaIleArgGluAlaLeuGluAspAlaGly-195 |
| SEQ. ID. NO. 21325 | 216-PheArgAspAlaValGly-221 |
| SEQ. ID. NO. 21326 | 225-AsnLeuGlyLysAlaAspLysLysThrTyrGln-235 |
| SEQ. ID. NO. 21327 | 238-ProAlaAsnThrAspGluAlaLeuHis-246 |
| SEQ. ID. NO. 21328 | 250-LeuAspIleGlnGluGlyAlaAsp-257 |
| SEQ. ID. NO. 21329 | 270-ValValArgArgValLysAspGluPheGly-279 |
| SEQ. ID. NO. 21330 | 317-LysArgAlaGlyAla-321 |
| SEQ. ID. NO. 21331 | 331-GluAlaAlaLysMetLeuLysArg-338 |
| a611 | |
| AMPHI Regions - AMPHI | |
| SEQ. ID. NO. 21332 | 15-CysArgLeuPheGlyLysLeuSerLeu-23 |
| SEQ. ID. NO. 21333 | 26-ArgLeuLeuLeuGlyLeu-31 |
| SEQ. ID. NO. 21334 | 48-ArgSerValArgArgValIle-54 |
| SEQ. ID. NO. 21335 | 63-GlnValValAlaVal-67 |
| SEQ. ID. NO. 21336 | 104-ValPheIleGluAspPheVal-110 |
| SEQ. ID. NO. 21337 | 129-LeuGlyPheLeuGlyAsnValLeuArgThr-138 |
| Antigenic Index - Jameson-Wolf | |
| SEQ. ID. NO. 21338 | 1-MetProSerGluAsnArgMetGlyLysArgGlnLeuAla-13 |
| SEQ. ID. NO. 21339 | 32-CysArgSerGlyValCysArgGlyArgCys-41 |
| SEQ. ID. NO. 21340 | 45-PheProSerArgSerValArgArgValIlePheArgArgValArgIle-60 |
| SEQ. ID. NO. 21341 | 119-AsnProAlaAspPheArgIle-125 |
| SEQ. ID. NO. 21342 | 142-AlaSerGlnGluAsp-146 |
| Hydrophilic Regions - Hopp-Woods | |
| SEQ. ID. NO. 21343 | 1-MetProSerGluAsnArgMetGlyLysArgGlnLeuAla-13 |
| SEQ. ID. NO. 21344 | 35-GlyValCysArgGlyArgCys-41 |
| SEQ. ID. NO. 21345 | 53-ValIlePheArgArgValArgIle-60 |
| SEQ. ID. NO. 21346 | 121-AlaAspPheArgIle-125 |
| SEQ. ID. NO. 21347 | 142-AlaSerGlnGluAsp-146 |
| a612 | |
| AMPHI Regions - AMPHI | |
| SEQ. ID. NO. 21348 | 6-AsnIleAlaLysLysLeuAlaGlyVal-14 |
| SEQ. ID. NO. 21349 | 55-AlaAspLysAlaValGluLysCysAlaGluAsnValLeu-67 |
| SEQ. ID. NO. 21350 | 81-GlyAsnPheProAsn-85 |
| SEQ. ID. NO. 21351 | 101-AsnProTyrXxxLysLeuAsnLysSerLysSerProAspIlePheArgArgPhePheXxxGlyHisSer-123 |

TABLE 1-continued

Antigenic Index - Jameson-Wolf
SEQ. ID. NO. 21352 7-IleAlaLysLysLeuAlaGlyValAsp-15
SEQ. ID. NO. 21353 17-IleAlaPheAspPheAspGly-23
SEQ. ID. NO. 21354 27-AspPheGlyArgAspAspAlaValArgHisSerGlyVal-39
SEQ. ID. NO. 21355 57-LysAlaValGluLysCysAlaGlu-64
SEQ. ID. NO. 21356 97-GlyHisHisArgAsnProTyrXxxLysLeuAsnLysSerLysSerProAspIlePheArg-116
Hydrophilic Regions - Hopp-Woods
SEQ. ID. NO. 21357 7-IleAlaLysLysLeuAlaGlyValAsp-15
SEQ. ID. NO. 21358 28-PheGlyArgAspAspAlaValArg-35
SEQ. ID. NO. 21359 57-LysAlaValGluLysCysAlaGlu-64
SEQ. ID. NO. 21360 105-LysLeuAsnLysSerLysSerProAspIlePhe-115
a613
AMPHI Regions - AMPHI
SEQ. ID. NO. 21361 7-SerArgArgSerLeu-11
SEQ. ID. NO. 21362 95-MetProArgMetArgSer-100
SEQ. ID. NO. 21363 103-SerProMetSerProAla-108
SEQ. ID. NO. 21364 115-ArgIlePheCysThrAlaLeuLeuArgLys-124
SEQ. ID. NO. 21365 140-SerSerValMetArgPro-145
SEQ. ID. NO. 21366 168-LeuSerGlyLeuCysArgIle-174
Antigenic Index - Jameson-Wolf
SEQ. ID. NO. 21367 1-MetSerArgSerSerArgSerArgArgSerLeuArgArgSerThrProSerArg-18
SEQ. ID. NO. 21368 23-SerSerArgGlnSerAlaArgAla-30
SEQ. ID. NO. 21369 35-PheAlaAspSerGlySerArgGluAsnLeu-44
SEQ. ID. NO. 21370 73-ProLysIleArgAlaAsnSerSerAspAlaArgGluArgArgLeuProSerArgAspSerThrAla-94
SEQ. ID. NO. 21371 96-ProArgMetArgSerProSerSerProMetSerProAlaProGlySerProProTrp-114
SEQ. ID. NO. 21372 130-AlaLysProPheProAlaGluSerLysProSerSerValMetArgProAlaSer-147
SEQ. ID. NO. 21373 161-LysAlaAlaSerSerGluArgLeuSerGlyLeuCysArgIleArgArg-176
SEQ. ID. NO. 21374 178-MetMetGlyArgArgAlaAspIlePheSerAspArgGlyGlyGlu-192
Hydrophilic Regions - Hopp-Woods
SEQ. ID. NO. 21375 1-MetSerArgSerSerArgSerArgArgSerLeuArgArgSerThrProSer-17
SEQ. ID. NO. 21376 24-SerArgGlnSerAlaArgAla-30
SEQ. ID. NO. 21377 38-SerGlySerArgGluAsnLeu-44
SEQ. ID. NO. 21378 73-ProLysIleArgAlaAsnSerSerAspAlaArgGluArgArgLeuProSerArgAspSerThrAla-94
SEQ. ID. NO. 21379 96-ProArgMetArgSerProSer-102
SEQ. ID. NO. 21380 133-PheProAlaGluSerLysProSerSerValMetArg-144
SEQ. ID. NO. 21381 161-LysAlaAlaSerSerGluArgLeuSerGly-170
SEQ. ID. NO. 21382 172-CysArgIleArgArg-176
SEQ. ID. NO. 21383 178-MetMetGlyArgArgAlaAspIlePheSerAspArgGlyGlyGlu-192
a614
AMPHI Regions - AMPHI
SEQ. ID. NO. 21384 20-SerGlnPheIleGlnGlnVal-26
SEQ. ID. NO. 21385 65-AsnLeuIleLysThrLeuLeuAsp-72
SEQ. ID. NO. 21386 90-AlaLeuPheTyrSerLeuLeuProValLeu-99
SEQ. ID. NO. 21387 144-ValAlaGlyCysAspGluAlaLysGluGluValGlnGluIleValAspTyrLeuLysAlaProAsnArgTyrGlnSerLeu-170
SEQ. ID. NO. 21388 210-AspPheValGluMetPheVal-216
SEQ. ID. NO. 21389 222-ArgValArgAspMetPheGluGln-229
SEQ. ID. NO. 21390 242-GluIleAspAlaValGlyArg-248
SEQ. ID. NO. 21391 295-ProAlaLeuGlnArgProGlyArgPheAsp-304
SEQ. ID. NO. 21392 333-SerValAspLeuLeuSerLeuAla-340
SEQ. ID. NO. 21393 349-AlaAspLeuAlaAsnLeuValAsn-356
Antigenic Index - Jameson-Wolf
SEQ. ID. NO. 21394 7-LeuAspGlyLysLysGluAspAsnGlyGlnIleGlu-18
SEQ. ID. NO. 21395 26-ValAsnAsnGlyGluValSerGly-33
SEQ. ID. NO. 21396 45-LeuIleLysGlyGluArgThrAspLysSerThrPhe-56
SEQ. ID. NO. 21397 60-AlaProLeuAspAspAsnLeuIle-67
SEQ. ID. NO. 21398 70-LeuLeuAspLysAsnValArgValLysValThrProGluGluLysProSerAla-87
SEQ. ID. NO. 21399 111-MetGlnThrGlyGlyGlyGlyLysGlyGly-120
SEQ. ID. NO. 21400 123-SerPheGlyLysSerArgAlaArgLeuLeuAspLysAspAlaAsnLys-138
SEQ. ID. NO. 21401 145-AlaGlyCysAspGluAlaLysGluGluValGlnGlu-156
SEQ. ID. NO. 21402 161-LeuLysAlaProAsnArgTyrGlnSerLeuGlyGlyArgValProArgGly-177
SEQ. ID. NO. 21403 182-GlySerProGlyThrGlyLysThrLeuLeu-191
SEQ. ID. NO. 21404 207-SerGlySerAspPhe-211
SEQ. ID. NO. 21405 219-GlyAlaSerArgValArgAspMetPheGluGlnAlaLysLysAsnAla-234
SEQ. ID. NO. 21406 241-AspGluIleAspAlaValGlyArgGlnArgGlyAlaGlyLeuGlyGlyGlyAsnAspGluArgGluGlnThrLeu-265
SEQ. ID. NO. 21407 272-MetAspGlyPheGluSerAsnGln-279
SEQ. ID. NO. 21408 287-ThrAsnArgProAspValLeuAspProAlaLeuGlnArgProGlyArgPheAspArg-305
SEQ. ID. NO. 21409 311-LeuProAspIleArgGlyArgGluGlnIle-320
SEQ. ID. NO. 21410 323-ValHisSerLysLysValProLeuAspLysSerValAsp-335
SEQ. ID. NO. 21411 341-ArgGlyThrProGlyPheSerGly-348
SEQ. ID. NO. 21412 362-AlaGlyArgArgAsnLysValLysValAspGlnSerAspLeuLysThrProLysThrLysSer-382
Hydrophilic Regions- Hopp-Woods
SEQ. ID. NO. 21413 7-LeuAspGlyLysLysGluAspAsnGlyGln-16
SEQ. ID. NO. 21414 27-AsnAsnGlyGluValSer-32
SEQ. ID. NO. 21415 46-IleLysGlyGluArgThrAspLysSerThr-55
SEQ. ID. NO. 21416 61-ProLeuAspAspAsnLeuIle-67
SEQ. ID. NO. 21417 70-LeuLeuAspLysAsnValArgValLysValThrProGluGluLysProSer-86
SEQ. ID. NO. 21418 125-GlyLysSerArgAlaArgLeuLeuAspLysAspAlaAsnLys-138
SEQ. ID. NO. 21419 145-AlaGlyCysAspGluAlaLysGluGluValGlnGlu-156
SEQ. ID. NO. 21420 162-LysAlaProAsnArg-166
SEQ. ID. NO. 21421 171-GlyGlyArgValProArg-176

TABLE 1-continued

| | |
|---|---|
| SEQ. ID. NO. 21422 | 221-SerArgValArgAspMetPheGluGlnAlaLysLysAsnAla-234 |
| SEQ. ID. NO. 21423 | 241-AspGluIleAspAlaValGlyArgGlnArgGlyAlaGly-253 |
| SEQ. ID. NO. 21424 | 256-GlyGlyAsnAspGluArgGluGlnThr-264 |
| SEQ. ID. NO. 21425 | 273-AspGlyPheGluSer-277 |
| SEQ. ID. NO. 21426 | 287-ThrAsnArgProAspValLeuAsp-294 |
| SEQ. ID. NO. 21427 | 296-AlaLeuGlnArgProGlyArgPheAspArg-305 |
| SEQ. ID. NO. 21428 | 312-ProAspIleArgGlyArgGluGlnIle-320 |
| SEQ. ID. NO. 21429 | 324-HisSerLysLysValProLeuAspLysSerValAsp-335 |
| SEQ. ID. NO. 21430 | 362-AlaGlyArgArgAsnLysValLysValAspGlnSerAspLeuLysThrProLysThrLys-381 |
| a616 | |
| AMPHI Regions - AMPHI | |
| SEQ. ID. NO. 21431 | 6-LysMetValValGlyLeu-11 |
| SEQ. ID. NO. 21432 | 13-AsnProGlyLysGluTyrGlu-19 |
| SEQ. ID. NO. 21433 | 48-PheGlyGluValAlaArgAla-54 |
| SEQ. ID. NO. 21434 | 77-ValAlaAlaLeuAlaGlnPheTyrLys-85 |
| SEQ. ID. NO. 21435 | 115-GlyHisAsnGlyLeuLysAspIle-122 |
| SEQ. ID. NO. 21436 | 161-ProThrAspArgCysArgArgGlnIlePro-170 |
| SEQ. ID. NO. 21437 | 174-ThrArgHisProCysArgGlnMetArgGly-183 |
| SEQ. ID. NO. 21438 | 201-ThrAlaCysSerArgPheProTyr-208 |
| SEQ. ID. NO. 21439 | 265-AlaProValGlnAsnLeuProAsnValAla-274 |
| SEQ. ID. NO. 21440 | 297-GlyGlyIleTyrSerLeuLeuPhe-304 |
| SEQ. ID. NO. 21441 | 317-PheAspLysAlaAla-321 |
| SEQ. ID. NO. 21442 | 355-CysPheAlaLeuPheSerGluCysAlaGlnAlaPhe-366 |
| SEQ. ID. NO. 21443 | 368-AlaThrArgThrGlySerLeuGlyAspValLeuAlaAspMetAlaGlyThrValLeu-386 |
| Antigenic Index - Jameson-Wolf | |
| SEQ. ID. NO. 21444 | 11-LeuGlyAsnProGlyLysGluTyrGluGlnThrArgHisAsnAlaGlyPhe-27 |
| SEQ. ID. NO. 21445 | 39-AlaSerPheLysGluGluLysLysPhePhe-48 |
| SEQ. ID. NO. 21446 | 51-ValAlaArgAlaThrLeuProAspGlyAsp-60 |
| SEQ. ID. NO. 21447 | 65-LysProThrThrPheMetAsnArgSerGlyGlnAla-76 |
| SEQ. ID. NO. 21448 | 86-IleLysProGluGlu-90 |
| SEQ. ID. NO. 21449 | 96-AspGluLeuAspIleProCysGlyArgIleLysPhe-107 |
| SEQ. ID. NO. 21450 | 109-LeuGlyGlyGlyAsnGlyGlyHisAsnGlyLeuLysAspIleGlnAla-124 |
| SEQ. ID. NO. 21451 | 127-GlyThrAlaAspTyrTyrArg-133 |
| SEQ. ID. NO. 21452 | 138-IleGlyHisProGlyAspArgAsnLeu-146 |
| SEQ. ID. NO. 21453 | 152-LeuAsnLysProSerThrGluXxxProProThrAspArgCysArgArgGlnIleProAlaSerHisThrArgHisProCysArgGlnMetArg GlyAsnProLeuPro-187 |
| SEQ. ID. NO. 21454 | 190-GlnMetThrArgCysArgLeuLysProPheGlnThrAlaCysSerArgPheProTyrProAsnSerHisAspArgThrGlnAla-217 |
| SEQ. ID. NO. 21455 | 219-TyrProAsnArgIleHisProArgHisArgArgAsnProArgPheProAla-235 |
| SEQ. ID. NO. 21456 | 238-MetGlnHisArgArgArgThrIleArgArgArgSerGlyThrMetAlaArgHisThrCysArgThrArgArgGlnIlePro-264 |
| SEQ. ID. NO. 21457 | 266-ProValGlnAsnLeuProAsnValAlaGlyArgGlyGlyGlyMetLysLeuProArgAsnArgPheSer-288 |
| SEQ. ID. NO. 21458 | 306-AlaAlaAspThrAlaProProProPheProHisPheAspLysAlaAla-321 |
| SEQ. ID. NO. 21459 | 336-AlaPheLysThrGlyLysLeuProIle-344 |
| SEQ. ID. NO. 21460 | 368-AlaThrArgThrGlySerLeuGly-375 |
| SEQ. ID. NO. 21461 | 392-ArgAlaAlaAspArgProAsp-398 |
| Hydrophilic Regions - Hopp-Woods | |
| SEQ. ID. NO. 21462 | 13-AsnProGlyLysGluTyrGluGlnThrArgHis-23 |
| SEQ. ID. NO. 21463 | 39-AlaSerPheLysGluGluLysLysPhePhe-48 |
| SEQ. ID. NO. 21464 | 86-IleLysProGluGlu-90 |
| SEQ. ID. NO. 21465 | 96-AspGluLeuAspIleProCysGlyArgIleLysPhe-107 |
| SEQ. ID. NO. 21466 | 117-AsnGlyLeuLysAspIleGlnAla-124 |
| SEQ. ID. NO. 21467 | 140-HisProGlyAspArgAsnLeu-146 |
| SEQ. ID. NO. 21468 | 155-ProSerThrGluXxxProProThrAspArgCysArgArgGlnIlePro-170 |
| SEQ. ID. NO. 21469 | 172-SerHisThrArgHisProCysArgGlnMetArgGlyAsnPro-185 |
| SEQ. ID. NO. 21470 | 190-GlnMetThrArgCysArgLeuLysPro-198 |
| SEQ. ID. NO. 21471 | 210-AsnSerHisAspArgThrGln-216 |
| SEQ. ID. NO. 21472 | 223-IleHisProArgHisArgArgAsnProArg-232 |
| SEQ. ID. NO. 21473 | 238-MetGlnHisArgArgArgThrIleArgArgArgSerGlyThrMet-252 |
| SEQ. ID. NO. 21474 | 255-HisThrCysArgThrArgArgGlnIle-263 |
| SEQ. ID. NO. 21475 | 274-AlaGlyArgGlyGlyGly-279 |
| SEQ. ID. NO. 21476 | 281-LysLeuProArgAsnArgPhe-287 |
| SEQ. ID. NO. 21477 | 306-AlaAlaAspThrAla-310 |
| SEQ. ID. NO. 21478 | 316-HisPheAspLysAlaAla-321 |
| SEQ. ID. NO. 21479 | 336-AlaPheLysThrGlyLys-341 |
| SEQ. ID. NO. 21480 | 392-ArgAlaAlaAspArgProAsp-398 |
| a619 | |
| AMPHI Regions - AMPHI | |
| SEQ. ID. NO. 21481 | 50-LysLeuAlaAlaLeuLeu-55 |
| SEQ. ID. NO. 21482 | 66-GlnLeuPheGlnThrLeuThrAsn-73 |
| SEQ. ID. NO. 21483 | 134-GlnGlyGlyArgAspLeu-139 |
| SEQ. ID. NO. 21484 | 146-GlyValIlePheGlyIleLeuPheArgSerLeuSerSerLeuLeuSerArg-162 |
| SEQ. ID. NO. 21485 | 165-AspProGluGluPhe-169 |
| SEQ. ID. NO. 21486 | 175-AsnMetPheAlaGlyPheAsnThrValHisSer-185 |
| SEQ. ID. NO. 21487 | 246-AlaValValGlyProValSerPhePheGlyLeuLeuAlaAlaSerLeuAlaAsnHisPheSer-266 |
| SEQ. ID. NO. 21488 | 303-LeuSerValValValGluPhe-309 |
| Antigenic Index - Jameson-Wolf | |
| SEQ. ID. NO. 21489 | 1-MetProSerGluLysAsnIle-7 |
| SEQ. ID. NO. 21490 | 11-AlaGlySerSerArgPro-16 |
| SEQ. ID. NO. 21491 | 35-AsnValLysGlyAspTrpAsp-41 |
| SEQ. ID. NO. 21492 | 132-IleLysGlnGlyGlyArgAspLeuPro-140 |
| SEQ. ID. NO. 21493 | 163-MetIleAspProGluGluPheThr-170 |

TABLE 1-continued

| SEQ. ID. NO. 21494 | 203-TrpArgGluArgTyrArgLeu-209 |
| --- | --- |
| SEQ. ID. NO. 21495 | 213-LeuLeuGlyArgAspGlnAla-219 |
| SEQ. ID. NO. 21496 | 265-PheSerProSerValLysHisSerVal-273 |

Hydrophilic Regions - Hopp-Woods

| SEQ. ID. NO. 21497 | 1-MetProSerGluLysAsnIle-7 |
| --- | --- |
| SEQ. ID. NO. 21498 | 134-GlnGlyGlyArgAspLeuPro-140 |
| SEQ. ID. NO. 21499 | 163-MetIleAspProGluGluPheThr-170 |
| SEQ. ID. NO. 21500 | 203-TrpArgGluArgTyrArgLeu-209 |
| SEQ. ID. NO. 21501 | 213-LeuLeuGlyArgAspGlnAla-219 |
| SEQ. ID. NO. 21502 | 269-ValLysHisSerVal-273 |

a620
AMPHI Regions - AMPHI

| SEQ. ID. NO. 21503 | 9-ValAlaValSerAlaLeuSerAlaCysArgGlnAla-20 |
| --- | --- |
| SEQ. ID. NO. 21504 | 31-IleSerAspArgSerVal-36 |
| SEQ. ID. NO. 21505 | 67-SerThrIleLysGlnMetPheGlyTyrThrLysLeuProGluGluProLysGlyIleArgValIleTyrValThrAspMetGlyAsnValThrAspTrpThr-100 |
| SEQ. ID. NO. 21506 | 139-GlnAlaGluLysPhe-143 |

Antigenic Index - Jameson-Wolf

| SEQ. ID. NO. 21507 | 15-SerAlaCysArgGlnAlaGluGluGlyProProProLeuProArgGlnIleSerAspArgSerValGlyHis-38 |
| --- | --- |
| SEQ. ID. NO. 21508 | 43-AsnLeuThrGluHisAsnGlyProLysAla-52 |
| SEQ. ID. NO. 21509 | 57-AsnGlyLysProAspGlnProVal-64 |
| SEQ. ID. NO. 21510 | 75-TyrThrLysLeuProGluGluProLysGlyIle-85 |
| SEQ. ID. NO. 21511 | 97-ThrAspTrpThrAsnProAsnAlaAspThrGluTrpMetAspAlaLysLys-113 |
| SEQ. ID. NO. 21512 | 125-GlyMetGlyAlaGluAspAlaLeuProPheGlyAsnLysGluGlnAlaGluLysPheAlaLysAspLysGlyGlyLysValValGlyPheAspAspMetProAspThrTyr-161 |

Hydrophilic Regions - Hopp-Woods

| SEQ. ID. NO. 21513 | 18-ArgGlnAlaGluGluGlyProProProLeu-27 |
| --- | --- |
| SEQ. ID. NO. 21514 | 30-GlnIleSerAspArgSerVal-36 |
| SEQ. ID. NO. 21515 | 46-GluHisAsnGlyProLys-51 |
| SEQ. ID. NO. 21516 | 58-GlyLysProAspGln-62 |
| SEQ. ID. NO. 21517 | 77-LysLeuProGluGluProLysGlyIle-85 |
| SEQ. ID. NO. 21518 | 103-AsnAlaAspThrGluTrpMetAspAlaLysLys-113 |
| SEQ. ID. NO. 21519 | 127-GlyAlaGluAspAlaLeu-132 |
| SEQ. ID. NO. 21520 | 135-GlyAsnLysGluGlnAlaGluLysPheAlaLysAspLysGlyGlyLys-150 |
| SEQ. ID. NO. 21521 | 155-AspAspMetProAsp-159 |

a622
AMPHI Regions - AMPHI

| SEQ. ID. NO. 21522 | 28-LeuProGluAlaValArgAsnLeuAlaArg-37 |
| --- | --- |
| SEQ. ID. NO. 21523 | 62-GluGluIleIleArgTrpLeuAlaAsp-70 |
| SEQ. ID. NO. 21524 | 112-IleLeuGlyGlnIleLysAspAlaValArgValAlaGln-124 |
| SEQ. ID. NO. 21525 | 131-LysLysLeuAsnAlaLeuPheGlnLys-139 |
| SEQ. ID. NO. 21526 | 142-SerValAlaLysGluVal-147 |
| SEQ. ID. NO. 21527 | 169-GluGlnIlePheProAspIleGlyAsp-177 |
| SEQ. ID. NO. 21528 | 187-GluMetIleGluLeuValAla-193 |
| SEQ. ID. NO. 21529 | 214-AlaGlnGluLeuCysAspLys-220 |
| SEQ. ID. NO. 21530 | 232-AspLeuProAlaIleLeuHis-238 |
| SEQ. ID. NO. 21531 | 288-AspLeuAsnAspAla-292 |
| SEQ. ID. NO. 21532 | 297-ValAspAspMetValAsnIleValGlnSerGly-307 |
| SEQ. ID. NO. 21533 | 324-GluLysValAlaGluPheValArgGlnGln-333 |
| SEQ. ID. NO. 21534 | 345-LeuArgAspGluGlyGluLys-351 |
| SEQ. ID. NO. 21535 | 354-LysGlnValLeuGluAsnAlaMetLysGlnLeuAlaLys-366 |
| SEQ. ID. NO. 21536 | 384-LysLeuLeuHisSerProThrGlnThrLeuAsnLysAlaGlyGlu-398 |

Antigenic Index - Jameson-Wolf

| SEQ. ID. NO. 21537 | 16-SerIleArgGluLysLeuAla-22 |
| --- | --- |
| SEQ. ID. NO. 21538 | 30-GluAlaValArgAsnLeuAlaArgSerAsnAlaAla-41 |
| SEQ. ID. NO. 21539 | 49-ThrCysAsnArgThrGlu-54 |
| SEQ. ID. NO. 21540 | 57-CysValGlyAspSerGluGluIleIle-65 |
| SEQ. ID. NO. 21541 | 75-ProIleGluGluIleSerProTyrLeu-83 |
| SEQ. ID. NO. 21542 | 90-GluThrValArgHis-94 |
| SEQ. ID. NO. 21543 | 115-GlnIleLysAspAlaValArgValAlaGlnGluGlnGluSerMetGlyLysLysLeu-133 |
| SEQ. ID. NO. 21544 | 142-SerValAlaLysGluValArgThrAspThrAlaValGlyGluAsnSerVal-158 |
| SEQ. ID. NO. 21545 | 174-AspIleGlyAspLeuAsn-179 |
| SEQ. ID. NO. 21546 | 199-LysSerProArgLeu-203 |
| SEQ. ID. NO. 21547 | 210-ThrLeuAlaArgAlaGlnGluLeuCysAspLysLeuGlyValAsnAlaGlu-226 |
| SEQ. ID. NO. 21548 | 257-GlyMetValGluArgAlaLeuLysGlnArgGlnSer-268 |
| SEQ. ID. NO. 21549 | 277-AlaValProArgAspIleGluAlaGluValGlyAspLeuAsnAsp-291 |
| SEQ. ID. NO. 21550 | 305-GlnSerGlyLysGluAlaArgGlnLysAlaAlaAlaAla-317 |
| SEQ. ID. NO. 21551 | 321-LeuValSerGluLysValAlaGluPheValArgGlnGlnGlnGlyArgGlnSerVal-339 |
| SEQ. ID. NO. 21552 | 343-ArgAlaLeuArgAspGluGlyGluLysAlaArgLysGlnValLeu-357 |
| SEQ. ID. NO. 21553 | 368-AlaThrAlaGluGluValLeuGlu-375 |
| SEQ. ID. NO. 21554 | 381-LeuThrAsnLysLeuLeuHisSerProThrGlnThrLeuAsnLysAlaGlyGluGluAspLysAspLeuVal-404 |

Hydrophilic Regions - Hopp-Woods

| SEQ. ID. NO. 21555 | 16-SerIleArgGluLysLeuAla-22 |
| --- | --- |
| SEQ. ID. NO. 21556 | 30-GluAlaValArgAsnLeuAlaArgSerAsnAlaAla-41 |
| SEQ. ID. NO. 21557 | 59-GlyAspSerGluGluIleIle-65 |
| SEQ. ID. NO. 21558 | 75-ProIleGluGluIleSer-80 |
| SEQ. ID. NO. 21559 | 90-GluThrValArgHis-94 |
| SEQ. ID. NO. 21560 | 115-GlnIleLysAspAlaValArgValAlaGlnGluGlnGluSerMetGlyLysLysLeu-133 |
| SEQ. ID. NO. 21561 | 142-SerValAlaLysGluValArgThrAspThrAlaValGlyGluAsnSerVal-158 |
| SEQ. ID. NO. 21562 | 210-ThrLeuAlaArgAlaGlnGluLeuCysAsp-219 |

TABLE 1-continued

SEQ. ID. NO. 21563 257-GlyMetValGluArgAlaLeuLysGlnArgGlnSer-268
SEQ. ID. NO. 21564 277-AlaValProArgAspIleGluAlaGluValGlyAspLeuAsn-290
SEQ. ID. NO. 21565 305-GlnSerGlyLysGluAlaArgGlnLysAlaAlaAlaAla-317
SEQ. ID. NO. 21566 321-LeuValSerGluLysValAlaGluPheValArg-331
SEQ. ID. NO. 21567 333-GlnGlnGlyArgGlnSer-338
SEQ. ID. NO. 21568 343-ArgAlaLeuArgAspGluGlyGluLysAlaArgLysGlnValLeu-357
SEQ. ID. NO. 21569 368-AlaThrAlaGluGluValLeuGlu-375
SEQ. ID. NO. 21570 392-ThrLeuAsnLysAlaGlyGluGluAspLysAspLeuVal-404
a624
AMPHI Regions - AMPHI
SEQ. ID. NO. 21571 14-LeuLeuLeuGlyIleIleGlyIlePheLeuPro-24
SEQ. ID. NO. 21572 45-ArgPheHisArgTrpLeuHis-51
SEQ. ID. NO. 21573 58-ProMetValHisAsn-62
SEQ. ID. NO. 21574 92-PheProGlnArgTrpTrpValGlyAla-100
SEQ. ID. NO. 21575 102-SerSerValPheCysSerLeuValAlaIle-111
Antigenic Index - Jameson-Wolf
SEQ. ID. NO. 21576 41-LysAlaSerProArgPheHisArgTrp-49
SEQ. ID. NO. 21577 51-HisArgHisArgTyrPheGlyProMet-59
SEQ. ID. NO. 21578 63-TrpGluGlnAsnGlyAlaValProArgLysAlaLys-74
SEQ. ID. NO. 21579 115-ArgArgProGluSer-119
Hydrophilic Regions - Hopp-Woods
SEQ. ID. NO. 21580 67-GlyAlaValProArgLysAlaLys-74
SEQ. ID. NO. 21581 115-ArgArgProGluSer-119
a625
AMPHI Regions - AMPHI
SEQ. ID. NO. 21582 25-SerGlyArgIleIleSerIleAlaAla-33
SEQ. ID. NO. 21583 64-LysMetProProGluMetValTyrArgAla-73
Antigenic Index - Jameson-Wolf
SEQ. ID. NO. 21584 5-ArgLysMetLysLysMetThrMetCysThrArgArgVal-17
SEQ. ID. NO. 21585 57-ProPheLysSerProGlnThrLysMetProPro-67
SEQ. ID. NO. 21586 73-AlaSerSerSerArgMetLysGly-80
SEQ. ID. NO. 21587 96-AspAlaProLysThrLysLeuAsnGlyMetArgLysSerAsnValGln-11
Hydrophilic Regions - Hopp-Woods
SEQ. ID. NO. 21588 5-ArgLysMetLysLysMetThrMetCysThrArgArgVal-17
SEQ. ID. NO. 21589 60-SerProGlnThrLysMetProPro-67
SEQ. ID. NO. 21590 74-SerSerSerArgMetLysGly-80
SEQ. ID. NO. 21591 96-AspAlaProLysThrLysLeuAsnGlyMetArgLysSerAsnValGln-111
a627
AMPHI Regions - AMPHI
SEQ. ID. NO. 21592 21-LeuGlnAsnLeuVal-25
SEQ. ID. NO. 21593 56-IleAlaGluValGlyLysLeuPheLeuGlyIlePheIleThrIlePheProValLeuSerIleLeuLysAlaGlyGluAlaGlyAlaLeuGlyGlyVal ValSerLeuValHisAspThrAlaGlyHisProIle-100
SEQ. ID. NO. 21594 109-GlyIleLeuSerAlaPheLeuAspAsnAla-118
SEQ. ID. NO. 21595 141-PheHisSerLeuLeuAlaValSer-148
SEQ. ID. NO. 21596 153-PheMetGlyAlaLeuThrTyrIleGlyAsnAlaProAsnPheMetValLys-169
SEQ. ID. NO. 21597 181-ThrPhePheGlyTyr-185
Antigenic Index - Jameson-Wolf
SEQ. ID. NO. 21598 3-GlyLeuTrpLysProGluHisProGlyPhe-12
SEQ. ID. NO. 21599 41-ThrProLysGlnValArgAlaGlyAsnGluPheAsnPhe-53
SEQ. ID. NO. 21600 94-AspThrAlaGlyHis-98
SEQ. ID. NO. 21601 128-AlaGlyGlyAspAla-132
SEQ. ID. NO. 21602 170-AlaIleAlaGluGlnArgGlyValPro-178
Hydrophilic Regions - Hopp-Woods
SEQ. ID. NO. 21603 5-TrpLysProGluHisProGly-11
SEQ. ID. NO. 21604 43-LysGlnValArgAlaGlyAsn-49
SEQ. ID. NO. 21605 170-AlaIleAlaGluGlnArgGlyVal-177
a628
AMPHI Regions - AMPHI
SEQ. ID. NO. 21606 10-CysGlyProProAsnSerCysValSerMetLeuAlaAlaPheSerAspGlyThrSerAlaProAlaAla-32
SEQ. ID. NO. 21607 34-HisThrTrpIleLeuArgSer-40
Antigenic Index - Jameson-Wolf
SEQ. ID. NO. 21608 6-LysProAlaGlyCysGlyProProAsnSer-15
SEQ. ID. NO. 21609 23-PheSerAspGlyThrSerAla-29
SEQ. ID. NO. 21610 40-SerValLysArgLeuAsnThrSerLysProArgLeuLysSerSerAla-55
SEQ. ID. NO. 21611 77-MetAlaAsnGlySerAlaSerThr-84
SEQ. ID. NO. 21612 91-GlyArgValArgSerAlaValHisLysProAspTrpIleArgLeuArgArg
ThrSerSerProLeuLys-113
SEQ. ID. NO. 21613 116-AsnAlaSerGlyAla-120
Hydrophilic Regions - Hopp-Woods
SEQ. ID. NO. 21614 40-SerValLysArgLeuAsnThrSerLysProArgLeuLysSerSerAla-55
SEQ. ID. NO. 21615 91-GlyArgValArgSerAlaValHisLys-99
SEQ. ID. NO. 21616 101-AspTrpIleArgLeuArgArgThrSerSer-110
a629
AMPHI Regions - AMPHI
SEQ. ID. NO. 21617 32-ArgTrpSerAspValPheSer-38
SEQ. ID. NO. 21618 48-IleSerArgLeuProArgThrPhe-55
SEQ. ID. NO. 21619 116-ValAlaAlaLeuIleGlyMetLeuValPhe-125
SEQ. ID. NO. 21620 146-IlePheGlyGlyValValGluAlaValAlaThr-156
SEQ. ID. NO. 21621 167-MetLeuGlyValTrpGlnGlnGlyAsp-175
SEQ. ID. NO. 21622 191-GlyIleLeuAlaLeuPheAla-197

TABLE 1-continued

| | |
|---|---|
| SEQ. ID. NO. 21623 | 205-ThrIleLeuGlyLeuGlyGlu-211 |
| SEQ. ID. NO. 21624 | 252-ValValProAsnIleIleSerArgLeuIleGlyAspArgLeuArgGlnSer-268 |
| SEQ. ID. NO. 21625 | 285-IleIleGlyArgVal-289 |
| SEQ. ID. NO. 21626 | 300-ThrValPheGlyValLeu-305 |
| Antigenic Index - Jameson-Wolf | |
| SEQ. ID. NO. 21627 | 38-SerLeuSerAspSerGln-43 |
| SEQ. ID. NO. 21628 | 50-ArgLeuProArgThr-54 |
| SEQ. ID. NO. 21629 | 77-AsnArgPheValGluProSerMetAlaGlyAlaGlyGln-89 |
| SEQ. ID. NO. 21630 | 131-ArgLeuProProThrAla-136 |
| SEQ. ID. NO. 21631 | 174-GlyAspPheSerGly-178 |
| SEQ. ID. NO. 21632 | 260-LeuIleGlyAspArgLeuArgGlnSer-268 |
| SEQ. ID. NO. 21633 | 316-ArgLysProAlaHis-320 |
| Hydrophilic Regions - Hopp-Woods | |
| SEQ. ID. NO. 21634 | 260-LeuIleGlyAspArgLeuArgGln-267 |
| SEQ. ID. NO. 21635 | 316-ArgLysProAlaHis-320 |
| a630 | |
| AMPHI Regions - AMPHI | |
| SEQ. ID. NO. 21636 | 9-LeuPheProAlaMetPheTyrGlyMetTyrAsn-19 |
| SEQ. ID. NO. 21637 | 30-ProAspLeuLeuGlnGlnSerIleAlaAsnAspTrpHisTyrAlaLeu-45 |
| SEQ. ID. NO. 21638 | 81-GlyGlyPheTrpGluValLeuPheAla-89 |
| SEQ. ID. NO. 21639 | 135-PheGlyGlyThrGlyLysAsnPhe-142 |
| SEQ. ID. NO. 21640 | 169-AlaValAspGlyTyrSerGlyAlaThrAlaLeuAlaGlnTrp-182 |
| SEQ. ID. NO. 21641 | 187-AlaAspGlyLeuLysAsnAlaIle-194 |
| SEQ. ID. NO. 21642 | 203-AspAlaPheIleGlyLysLeuProGlySerIleGlyGluValSer-217 |
| SEQ. ID. NO. 21643 | 230-PheAlaArgIleAlaSerTrpArgIleIleAlaGlyValMet-243 |
| SEQ. ID. NO. 21644 | 247-IleAlaMetSerSerLeuPheAsnPhe-255 |
| SEQ. ID. NO. 21645 | 289-ValSerAlaSerPheThrAsnValGlyLysTrpTrpTyrGlyAlaLeuIleGlyValMetCysValLeuIleArgVal-314 |
| SEQ. ID. NO. 21646 | 327-IleLeuPheAlaAsnLeuPheAlaProIlePheAspTyrPhe-340 |
| Antigenic Index - Jameson-Wolf | |
| SEQ. ID. NO. 21647 | 91-ValArgLysHisGluIleAsnGlu-98 |
| SEQ. ID. NO. 21648 | 133-GluValPheGlyGlyThrGlyLysAsnPheMet-143 |
| SEQ. ID. NO. 21649 | 157-TyrProAlaAsnLeuSerGlyAspAla-165 |
| SEQ. ID. NO. 21650 | 186-GlyAlaAspGlyLeuLys-191 |
| SEQ. ID. NO. 21651 | 209-LeuProGlySerIleGly-214 |
| SEQ. ID. NO. 21652 | 257-GlySerAspThrAsnAla-262 |
| SEQ. ID. NO. 21653 | 345-AsnIleLysArgArgLysAlaArgSerAsnGly-355 |
| Hydrophilic Regions - Hopp-Woods | |
| SEQ. ID. NO. 21654 | 91-ValArgLysHisGluIleAsn-97 |
| SEQ. ID. NO. 21655 | 345-AsnIleLysArgArgLysAlaArgSerAsnGly-355 |
| a638 | |
| AMPHI Regions - AMPHI | |
| SEQ. ID. NO. 21656 | 17-LeuAlaArgPheValAspAsnVal-24 |
| SEQ. ID. NO. 21657 | 30-IleValAspIleValGluHis-36 |
| SEQ. ID. NO. 21658 | 46-AspIleValLysHisPheGluProLeuGlyLys-56 |
| SEQ. ID. NO. 21659 | 118-ArgAlaGlyArgValPro-123 |
| SEQ. ID. NO. 21660 | 149-IleGlyArgThrMetGln-154 |
| SEQ. ID. NO. 21661 | 198-GluArgTyrValArgArgValTyrGlyTyrGlyThrPro-210 |
| SEQ. ID. NO. 21662 | 212-ProValSerPheAspGlyCysArgThrValGlyArgPro-224 |
| SEQ. ID. NO. 21663 | 242-SerGlnPheGluArgIleAlaArgProGly-251 |
| Antigenic Index - Jameson-Wolf | |
| SEQ. ID. NO. 21664 | 13-GlyLysAsnAlaLeu-17 |
| SEQ. ID. NO. 21665 | 43-AlaAspGlyAspIle-47 |
| SEQ. ID. NO. 21666 | 52-GluProLeuGlyLysHisGln-58 |
| SEQ. ID. NO. 21667 | 81-ValAspGlyGluThrGlnIle-87 |
| SEQ. ID. NO. 21668 | 99-AlaGlyIleGlyLysAsnAlaVal-106 |
| SEQ. ID. NO. 21669 | 113-ValAlaAspAspLeuArgAlaGlyArgValProAsnGlyAsn-126 |
| SEQ. ID. NO. 21670 | 135-GlnSerArgValAlaAsp-140 |
| SEQ. ID. NO. 21671 | 153-MetGlnIleAspAlaAspArgIleIle-161 |
| SEQ. ID. NO. 21672 | 168-AsnGlnGlyAlaArgGlySerPhe-175 |
| SEQ. ID. NO. 21673 | 178-IleAsnThrGlyIleHis-183 |
| SEQ. ID. NO. 21674 | 188-HisThrGlyThrGlyAsnGlyGlnValAlaGluArgTyrValArg-202 |
| SEQ. ID. NO. 21675 | 213-ValSerPheAspGlyCysArgThrValGlyArgProPheAsnArgAsnArgPheValAsp-232 |
| SEQ. ID. NO. 21676 | 240-AlaGlySerGlnPheGluArgIleAlaArgProGlyAlaGlyLysCysGly-256 |
| Hydrophilic Regions - Hopp-Woods | |
| SEQ. ID. NO. 21677 | 43-AlaAspGlyAspIle-47 |
| SEQ. ID. NO. 21678 | 52-GluProLeuGlyLys-56 |
| SEQ. ID. NO. 21679 | 81-ValAspGlyGluThrGlnIle-87 |
| SEQ. ID. NO. 21680 | 113-ValAlaAspAspLeuArgAlaGlyArgValProAsn-124 |
| SEQ. ID. NO. 21681 | 136-SerArgValAlaAsp-140 |
| SEQ. ID. NO. 21682 | 153-MetGlnIleAspAlaAspArgIleIle-161 |
| SEQ. ID. NO. 21683 | 195-GlnValAlaGluArgTyrValArg-202 |
| SEQ. ID. NO. 21684 | 216-AspGlyCysArgThrValGly-222 |
| SEQ. ID. NO. 21685 | 243-GlnPheGluArgIleAlaArgProGlyAlaGly-253 |
| a639-1 | |
| AMPHI Regions - AMPHI | |
| SEQ. ID. NO. 21686 | 95-TyrLysAsnAsnArg-99 |
| SEQ. ID. NO. 21687 | 137-LeuLysValPheAspAsnIle-143 |
| SEQ. ID. NO. 21688 | 157-ValAsnTyrSerAspIleHisAspAsnIleIleAsnLysAla-170 |
| SEQ. ID. NO. 21689 | 269-AlaProValSerArg-273 |

TABLE 1-continued

| | |
|---|---|
| SEQ. ID. NO. 21690 | 290-GlnPheProAlaValLeuProGly-297 |
| SEQ. ID. NO. 21691 | 322-AspGlyLeuLeuLysLysValGlu-329 |
| Antigenic Index - Jameson-Wolf | |
| SEQ. ID. NO. 21692 | 13-GluGluThrAlaPro-17 |
| SEQ. ID. NO. 21693 | 23-HisAsnAsnIleLeuAspAsnSer-30 |
| SEQ. ID. NO. 21694 | 41-AlaMetValArgGluAsnLysIleValGly-50 |
| SEQ. ID. NO. 21695 | 52-AlaThrLeuArgValAsnGluArgGlyAsnGly-62 |
| SEQ. ID. NO. 21696 | 75-GlyAsnAspIleSerLysGlyArgAspGlyIlePheSerAsnThrSerThrHisAsnThrTyrLysAsnAsnArgPheSerAsp-102 |
| SEQ. ID. NO. 21697 | 111-TyrThrAsnAspSerGluIleSerGly-119 |
| SEQ. ID. NO. 21698 | 121-IleSerValGlyAsnAsn-126 |
| SEQ. ID. NO. 21699 | 135-GluArgLeuLysVal-139 |
| SEQ. ID. NO. 21700 | 145-ValGlySerArgAspGlnGlyIle-152 |
| SEQ. ID. NO. 21701 | 160-SerAspIleHisAspAsnIleIleAsnLysAlaGlyLys-172 |
| SEQ. ID. NO. 21702 | 179-AlaAsnTyrAspLysLeuSerAlaAsnHis-188 |
| SEQ. ID. NO. 21703 | 203-GluGlyThrSerLeuHisAspAsnSerPheIleAsnAsnGluSerGlnValLysTyrVal-222 |
| SEQ. ID. NO. 21704 | 228-AspTrpSerGluGlyGlyHisGlyAsnTyrTrpSerAspAsnSerAla-243 |
| SEQ. ID. NO. 21705 | 246-LeuAsnGlyAspGlyPheGlyAspSerAlaTyrArgProAsnGlyIleIle-262 |
| SEQ. ID. NO. 21706 | 297-GlyGlyValValAspSerLysProLeuMetLysProTyrAlaProLysIleGlnThr-315 |
| SEQ. ID. NO. 21707 | 318-GlnAlaMetLysAspGlyLeuLeuLysLysValGluThrArgGlnLeuGluTrpGlyArgAlaGluAsnGlySerLeuAsn-344 |
| Hydrophilic Regions - Hopp-Woods | |
| SEQ. ID. NO. 21708 | 41-AlaMetValArgGluAsnLysIleValGly-50 |
| SEQ. ID. NO. 21709 | 52-AlaThrLeuArgValAsnGluArgGlyAsn-61 |
| SEQ. ID. NO. 21710 | 77-AspIleSerLysGlyArgAspGlyIle-85 |
| SEQ. ID. NO. 21711 | 95-TyrLysAsnAsnArgPheSerAsp-102 |
| SEQ. ID. NO. 21712 | 113-AsnAspSerGluIleSerGly-119 |
| SEQ. ID. NO. 21713 | 135-GluArgLeuLysVal-139 |
| SEQ. ID. NO. 21714 | 146-GlySerArgAspGlnGly-151 |
| SEQ. ID. NO. 21715 | 180-AsnTyrAspLysLeuSer-185 |
| SEQ. ID. NO. 21716 | 299-ValValAspSerLysProLeuMet-306 |
| SEQ. ID. NO. 21717 | 318-GlnAlaMetLysAspGlyLeuLeuLysLysValGluThrArgGlnLeuGluTrpGlyArgAlaGluAsnGlySer-342 |
| a640 | |
| AMPHI Regions - AMPHI | |
| SEQ. ID. NO. 21718 | 6-SerIleLeuLysSerIleGlyIle-13 |
| SEQ. ID. NO. 21719 | 22-SerIleLysArgMetSer-27 |
| SEQ. ID. NO. 21720 | 47-LeuProAlaTyrAlaGluArgLeuProAspPheLeuAlaLysIleGlnPro-63 |
| SEQ. ID. NO. 21721 | 72-ArgTyrSerLysPro-76 |
| SEQ. ID. NO. 21722 | 109-SerLysProIleAspThrLeuMetAla-117 |
| SEQ. ID. NO. 21723 | 127-AlaLysLeuValAspHis-132 |
| Antigenic Index - Jameson-Wolf | |
| SEQ. ID. NO. 21724 | 24-LysArgMetSerAlaPheArgAlaArgIle-33 |
| SEQ. ID. NO. 21725 | 50-TyrAlaGluArgLeuProAspPheLeuAlaLysIleGlnProSerGluIleValProGlyAlaAspArgTyrSerLysProGluGlyLysPro MetVal-82 |
| SEQ. ID. NO. 21726 | 85-ValTyrLysGlyAspGluGlnLeu-92 |
| SEQ. ID. NO. 21727 | 101-AlaValAsnThrArgGlyTyrSerSerLysProIleAsp-113 |
| SEQ. ID. NO. 21728 | 118-LeuAlaLysAspGlyThr-123 |
| SEQ. ID. NO. 21729 | 128-LysLeuValAspHisHisGlu-134 |
| Hydrophilic Regions - Hopp-Woods | |
| SEQ. ID. NO. 21730 | 24-LysArgMetSerAlaPheArgAlaArgIle-33 |
| SEQ. ID. NO. 21731 | 50-TyrAlaGluArgLeuPro-55 |
| SEQ. ID. NO. 21732 | 68-ProGlyAlaAspArgTyrSerLysProGluGlyLysProMetVal-82 |
| SEQ. ID. NO. 21733 | 85-ValTyrLysGlyAspGluGlnLeu-92 |
| SEQ. ID. NO. 21734 | 118-LeuAlaLysAspGlyThr-123 |
| SEQ. ID. NO. 21735 | 128-LysLeuValAspHisHisGlu-134 |
| a642 | |
| AMPHI Regions - AMPHI | |
| SEQ. ID. NO. 21736 | 6-CysProLeuSerAlaIleSerAlaVal-14 |
| SEQ. ID. NO. 21737 | 116-IleLysHisIleValArgAlaPhe-123 |
| SEQ. ID. NO. 21738 | 138-GlyValSerAlaPheLysThrLeuArgAlaGlnGluPheLeuGlnHisLeuArgGlyGlyVal-158 |
| SEQ. ID. NO. 21739 | 161-PheArgGlyGluGly-165 |
| SEQ. ID. NO. 21740 | 167-AspAspValArgLeu-171 |
| SEQ. ID. NO. 21741 | 186-AlaAspValAlaValLysAsnLeuGlyAsnLeuMetAlaAlaProAsp-201 |
| SEQ. ID. NO. 21742 | 220-ValPheLysGlyValPheHisAsnAlaValArgHisAlaAspGlnLeuGln-236 |
| SEQ. ID. NO. 21743 | 270-ValAspGlyValThrAspGlyAla-277 |
| SEQ. ID. NO. 21744 | 296-GlnValAspAspPheGlyGluPheAlaValPhe-306 |
| SEQ. ID. NO. 21745 | 325-PheArgGlyValAsp-329 |
| SEQ. ID. NO. 21746 | 378-AlaGluLeuLeuGlnTrpLeuGlnHisGlnArgAlaPheAspAlaGlyThr-394 |
| Antigenic Index - Jameson-Wolf | |
| SEQ. ID. NO. 21747 | 1-AlaCysArgArgIleCysPro-7 |
| SEQ. ID. NO. 21748 | 22-ValGlnGlnGluGlyCysGly-28 |
| SEQ. ID. NO. 21749 | 34-LeuTyrGluAspLysGluSerGlyAspAspPheAlaAspLysAspPheLeuGln-51 |
| SEQ. ID. NO. 21750 | 73-ValAlaGlyAspGlyGlyLysAlaGly-81 |
| SEQ. ID. NO. 21751 | 103-PheGlyGlyGlyAlaAspLysLeu-110 |
| SEQ. ID. NO. 21752 | 123-PheLysAsnArgGluGlyAlaAspValAspSerAspIleAla-136 |
| SEQ. ID. NO. 21753 | 143-LysThrLeuArgAla-147 |
| SEQ. ID. NO. 21754 | 161-PheArgGlyGluGlyPheAspAspValArgLeu-171 |
| SEQ. ID. NO. 21755 | 175-MetGlyAspGlyCysAsnGlyArgAsnGlyMet-185 |
| SEQ. ID. NO. 21756 | 208-AspGluSerAspValValAla-214 |
| SEQ. ID. NO. 21757 | 230-ArgHisAlaAspGlnLeuGlnAlaAlaAlaAspLysAspValLeuGluArgAlaGlnThrGly-250 |
| SEQ. ID. NO. 21758 | 259-HisGlyGlyCysArg-263 |
| SEQ. ID. NO. 21759 | 265-PheGlyIleAspAlaValAspGlyValThrAspGly-276 |

TABLE 1-continued

| | |
|---|---|
| SEQ. ID. NO. 21760 | 290-CysPheGlyAspGluGlnGlnValAspAspPheGly-301 |
| SEQ. ID. NO. 21761 | 309-PheGlyGlyAsnGluGluGluValAlaLeu-318 |
| SEQ. ID. NO. 21762 | 328-ValAspValAsnGly-332 |
| SEQ. ID. NO. 21763 | 344-PheSerGlyAsnArgArgAlaGlyGly-352 |
| SEQ. ID. NO. 21764 | 388-ArgAlaPheAspAlaGlyThrGlnArgAsnGly-398 |
| SEQ. ID. NO. 21765 | 401-ValMetProArgAsnPro-406 |
| Hydrophilic Regions - Hopp-Woods | |
| SEQ. ID. NO. 21766 | 1-AlaCysArgArgIleCys-6 |
| SEQ. ID. NO. 21767 | 34-LeuTyrGluAspLysGluSerGlyAspAspPheAlaAspLysAspPheLeu-50 |
| SEQ. ID. NO. 21768 | 76-AspGlyGlyLysAla-80 |
| SEQ. ID. NO. 21769 | 106-GlyAlaAspLysLeu-110 |
| SEQ. ID. NO. 21770 | 123-PheLysAsnArgGluGlyAlaAspValAspSerAspIle-135 |
| SEQ. ID. NO. 21771 | 143-LysThrLeuArgAla-147 |
| SEQ. ID. NO. 21772 | 164-GluGlyPheAspAspValArgLeu-171 |
| SEQ. ID. NO. 21773 | 178-GlyCysAsnGlyArgAsnGlyMet-185 |
| SEQ. ID. NO. 21774 | 208-AspGluSerAspValValAla-214 |
| SEQ. ID. NO. 21775 | 230-ArgHisAlaAspGlnLeuGlnAlaAlaAlaAspLysAspValLeuGluArgAlaGlnThr-249 |
| SEQ. ID. NO. 21776 | 269-AlaValAspGlyValThrAspGly-276 |
| SEQ. ID. NO. 21777 | 290-CysPheGlyAspGluGlnGlnValAspAspPheGly-301 |
| SEQ. ID. NO. 21778 | 311-GlyAsnGluGluGluValAlaLeu-318 |
| SEQ. ID. NO. 21779 | 346-GlyAsnArgArgAlaGly-351 |
| SEQ. ID. NO. 21780 | 393-GlyThrGlnArgAsnGly-398 |
| a644 | |
| AMPHI Regions - AMPHI | |
| SEQ. ID. NO. 21781 | 25-CysGlyArgArgPheAspArgPro-32 |
| SEQ. ID. NO. 21782 | 55-MetAspThrAlaAlaPheLeuLysHisIleGluSerAlaPheArgArgIlePheAlaAspGlyIleAspLeuMetArgTyrLeu-82 |
| SEQ. ID. NO. 21783 | 111-GlnPheGluIleGlnGluValLeuArgIleAlaGly-122 |
| SEQ. ID. NO. 21784 | 141-GlnProLeuGlnGluPheGlyAsp-148 |
| SEQ. ID. NO. 21785 | 181-ArgGluMetGlnSerTyrTyrGluTyrThrAsp-191 |
| SEQ. ID. NO. 21786 | 202-TyrTrpGlnGlyAsn-206 |
| SEQ. ID. NO. 21787 | 224-LeuAlaLysValIleAspLeuLeu-231 |
| SEQ. ID. NO. 21788 | 276-AlaGlyLeuArgAlaPheGlnAsn-283 |
| SEQ. ID. NO. 21789 | 304-LeuGluAsnLeuGluArgTyrValArgAsn-313 |
| SEQ. ID. NO. 21790 | 333-GluIleLeuTyrArgTyrValCysHis-341 |
| SEQ. ID. NO. 21791 | 343-ValSerProValAlaProValAlaHis-351 |
| SEQ. ID. NO. 21792 | 356-AlaAsnIleValLysThrLeuAla-363 |
| SEQ. ID. NO. 21793 | 372-GlnMetLeuGlnLys-376 |
| SEQ. ID. NO. 21794 | 399-PheThrIlePheGluGlyProAsn-406 |
| SEQ. ID. NO. 21795 | 408-MetLeuTyrAlaGluIleTyrAspGlnPheValArgAla-420 |
| SEQ. ID. NO. 21796 | 439-AspArgLeuGlnThr-443 |
| SEQ. ID. NO. 21797 | 456-LeuProGluAspIleArgSerPhe-463 |
| SEQ. ID. NO. 21798 | 481-GlyLysIleIleAlaArgLeu-487 |
| Antigenic Index - Jameson-Wolf | |
| SEQ. ID. NO. 21799 | 1-MetProSerGluArgSerAlaAspCysCysPro-11 |
| SEQ. ID. NO. 21800 | 16-ValLysPheArgLysSerThrLeuAsnCysGlyArgArgPheAspArgProProIleAsnGlyAsnArgGlnArgLysProMetIleHisThrGlu ProSerAlaGlnProSerThrMetAsp-56 |
| SEQ. ID. NO. 21801 | 64-IleGluSerAlaPhe-68 |
| SEQ. ID. NO. 21802 | 71-IlePheAlaAspGlyIleAsp-77 |
| SEQ. ID. NO. 21803 | 82-LeuProGluAspLysTrpLeu-88 |
| SEQ. ID. NO. 21804 | 99-PheLeuAspLysLysTyrGlyGlyArgLysGlySerGlnPheGluIle-114 |
| SEQ. ID. NO. 21805 | 132-XxxXxxXxxGluGly-136 |
| SEQ. ID. NO. 21806 | 145-GluPheGlyAspGluAlaGlnIle-152 |
| SEQ. ID. NO. 21807 | 159-ValPheLysGlyGluGlyGlyGlyLeu-167 |
| SEQ. ID. NO. 21808 | 170-ThrGluProGluThrSerGly-176 |
| SEQ. ID. NO. 21809 | 178-AlaIleAlaArgGluMetGlnSerTyrTyrGluTyrThrAspGlyGlnThr-194 |
| SEQ. ID. NO. 21810 | 202-TyrTrpGlnGlyAsnSerGlnSerAspPhe-211 |
| SEQ. ID. NO. 21811 | 216-AlaLysGluArgLysAsnGlyLysLeuAlaLys-226 |
| SEQ. ID. NO. 21812 | 235-LysThrTyrIleArg-239 |
| SEQ. ID. NO. 21813 | 241-GluThrLeuAlaSerGluGlyLeuArg-249 |
| SEQ. ID. NO. 21814 | 254-AlaValAsnArgIleAspAlaGluMet-262 |
| SEQ. ID. NO. 21815 | 270-LeuSerGlnSerAspAlaAlaGly-277 |
| SEQ. ID. NO. 21816 | 306-AsnLeuGluArgTyrValArgAsnAspIleArgPheValAspTyrGluArgArgGluIleArgArgArgHisGlnVal-331 |
| SEQ. ID. NO. 21817 | 381-LysGlyPheGluArgGlyHisThrAlaGlyAsn-391 |
| SEQ. ID. NO. 21818 | 403-GluGlyProAsnAspMetLeu-409 |
| SEQ. ID. NO. 21819 | 420-AlaThrAlaGluGluLysGluAlaGlyMetLysLeuAspLysAsnGlnThrLeuLeuAspArgLeuGlnThrAspAlaArgPhe-447 |
| SEQ. ID. NO. 21820 | 449-AlaValAlaArgAspTyrThrLeuProGluAspIleArgSerPheLeu-464 |
| SEQ. ID. NO. 21821 | 493-AlaGluHisGluAspThrAla-499 |
| SEQ. ID. NO. 21822 | 505-AspIleArgLysAspIleLeuAspCysArgTyrCysGly-517 |
| Hydrophilic Regions- Hopp-Woods | |
| SEQ. ID. NO. 21823 | 1-MetProSerGluArgSerAlaAspCys-9 |
| SEQ. ID. NO. 21824 | 17-LysPheArgLysSerThrLeuAsnCysGlyArgArgPheAspArgProProIleAsnGlyAsnArgGlnArgLysProMetIle-44 |
| SEQ. ID. NO. 21825 | 64-IleGluSerAlaPhe-68 |
| SEQ. ID. NO. 21826 | 82-LeuProGluAspLysTrpLeu-88 |
| SEQ. ID. NO. 21827 | 100-LeuAspLysLysTyrGlyGlyArgLysGlySerGln-111 |
| SEQ. ID. NO. 21828 | 145-GluPheGlyAspGluAlaGlnIle-152 |
| SEQ. ID. NO. 21829 | 160-PheLysGlyGluGlyGly-165 |
| SEQ. ID. NO. 21830 | 170-ThrGluProGluThrSerGly-176 |
| SEQ. ID. NO. 21831 | 178-AlaIleAlaArgGluMetGlnSer-185 |
| SEQ. ID. NO. 21832 | 216-AlaLysGluArgLysAsnGlyLysLeuAlaLys-226 |
| SEQ. ID. NO. 21833 | 254-AlaValAsnArgIleAspAlaGluMet-262 |

TABLE 1-continued

| | |
|---|---|
| SEQ. ID. NO. 21834 | 271-SerGlnSerAspAlaAlaGly-277 |
| SEQ. ID. NO. 21835 | 306-AsnLeuGluArgTyrValArgAsnAspIleArgPheValAspTyrGluArgArgGluIleArgArgArgHisGlnVal-331 |
| SEQ. ID. NO. 21836 | 381-LysGlyPheGluArgGlyHisThr-388 |
| SEQ. ID. NO. 21837 | 420-AlaThrAlaGluGluLysGluAlaGlyMetLysLeuAspLysAsnGlnThrLeuLeuAspArgLeuGlnThrAspAlaArgPhe-447 |
| SEQ. ID. NO. 21838 | 458-GluAspIleArgSerPheLeu-464 |
| SEQ. ID. NO. 21839 | 493-AlaGluHisGluAspThrAla-499 |
| SEQ. ID. NO. 21840 | 505-AspIleArgLysAspIleLeuAsp-512 |
| a645 | |
| AMPHI Regions - AMPHI | |
| SEQ. ID. NO. 21841 | 21-AsnThrLeuAsnArgCysCysLys-28 |
| SEQ. ID. NO. 21842 | 87-ArgThrLeuProSerLeuAsnGlyLeuThrLys-97 |
| SEQ. ID. NO. 21843 | 149-ThrProLysArgCysSerSerSerIle-157 |
| SEQ. ID. NO. 21844 | 163-PheLeuAsnPheMetSerSerCysThrSerLeu-173 |
| SEQ. ID. NO. 21845 | 210-SerAlaLysArgSer-214 |
| SEQ. ID. NO. 21846 | 249-SerValLeuProLysPro-254 |
| Antigenic Index - Jameson-Wolf | |
| SEQ. ID. NO. 21847 | 18-GluGlnSerAsnThrLeuAsnArgCysCysLysLysSerArgMetThrCysSerSerSerArgSerArgSerCysProCys-44 |
| SEQ. ID. NO. 21848 | 47-ProMetArgAlaSerGlySerArgValSerSerArgSerArgMet-61 |
| SEQ. ID. NO. 21849 | 68-SerLeuCysArgLysAsnThrCysProProArgLeuSerSerArgAsnThrAlaSerArgThrLeuProSer-91 |
| SEQ. ID. NO. 21850 | 99-LeuThrAlaArgArgArgLeuGly-106 |
| SEQ. ID. NO. 21851 | 110-IleSerGluLysSerArgSerProSerSer-119 |
| SEQ. ID. NO. 21852 | 137-ThrLeuAlaArgArgArgLeuSerCysSerPheArgThrProLysArgCysSerSer-155 |
| SEQ. ID. NO. 21853 | 184-SerAlaMetProSer-188 |
| SEQ. ID. NO. 21854 | 198-LeuLysArgGluArgLeuAla-204 |
| SEQ. ID. NO. 21855 | 207-ThrGlyLysSerAlaLysArgSerAlaLys-216 |
| SEQ. ID. NO. 21856 | 221-CysSerThrArgSerValValGlyAla-229 |
| SEQ. ID. NO. 21857 | 242-AsnAlaAlaArgArgAlaThr-248 |
| SEQ. ID. NO. 21858 | 250-ValLeuProLysProThrSerProHisThrArgArgSerIle-263 |
| Hydrophilic Regions - Hopp-Woods | |
| SEQ. ID. NO. 21859 | 19-GlnSerAsnThrLeu-23 |
| SEQ. ID. NO. 21860 | 25-ArgCysCysLysLysSerArgMetThrCysSerSerSerArgSerArgSerCysPro-43 |
| SEQ. ID. NO. 21861 | 48-MetArgAlaSerGlySerArgValSerSerArgSerArgMet-61 |
| SEQ. ID. NO. 21862 | 69-LeuCysArgLysAsnThrCysProProArgLeuSerSerArgAsnThrAlaSerArgThr-88 |
| SEQ. ID. NO. 21863 | 99-LeuThrAlaArgArgArgLeuGly-106 |
| SEQ. ID. NO. 21864 | 110-IleSerGluLysSerArgSerProSer-118 |
| SEQ. ID. NO. 21865 | 137-ThrLeuAlaArgArgArgLeuSerCys-145 |
| SEQ. ID. NO. 21866 | 148-ArgThrProLysArgCysSer-154 |
| SEQ. ID. NO. 21867 | 198-LeuLysArgGluArgLeuAla-204 |
| SEQ. ID. NO. 21868 | 209-LysSerAlaLysArgSerAlaLys-216 |
| SEQ. ID. NO. 21869 | 242-AsnAlaAlaArgArgAlaThr-248 |
| SEQ. ID. NO. 21870 | 254-ProThrSerProHisThrArgArgSerIle-263 |
| a647 | |
| AMPHI Regions - AMPHI | |
| SEQ. ID. NO. 21871 | 38-GlyLysValCysArgCysPheGluGlnVal-47 |
| SEQ. ID. NO. 21872 | 69-ThrValPheArgGlnIleIleArgIleValAspHisAla-81 |
| Antigenic Index - Jameson-Wolf | |
| SEQ. ID. NO. 21873 | 26-GlyLeuValLysGluArgAlaArg-33 |
| SEQ. ID. NO. 21874 | 39-LysValCysArgCysPhe-44 |
| SEQ. ID. NO. 21875 | 54-GlyThrValGlyGlnThrGluArgGlyAla-63 |
| SEQ. ID. NO. 21876 | 79-AspHisAlaAspThrGluArgThrAlaAlaHisSerGlyGlyThrArgGly-95 |
| Hydrophilic Regions - Hopp-Woods | |
| SEQ. ID. NO. 21877 | 26-GlyLeuValLysGluArgAlaArg-33 |
| SEQ. ID. NO. 21878 | 40-ValCysArgCysPhe-44 |
| SEQ. ID. NO. 21879 | 56-ValGlyGlnThrGluArgGlyAla-63 |
| SEQ. ID. NO. 21880 | 79-AspHisAlaAspThrGluArgThrAlaAla-88 |
| a648 | |
| AMPHI Regions - AMPHI | |
| SEQ. ID. NO. 21881 | 7-ArgIleGluArgAlaValArg-13 |
| SEQ. ID. NO. 21882 | 15-AlaValIleAspValLeuAsnValAsp-23 |
| SEQ. ID. NO. 21883 | 44-AlaLeuAlaAspIleArgValLeu-51 |
| SEQ. ID. NO. 21884 | 94-AlaValAspLeuHisAlaValIleLysLeuThrAspThrVal-107 |
| SEQ. ID. NO. 21885 | 127-GlnGlyValGluGlnGly-132 |
| SEQ. ID. NO. 21886 | 152-PheLysGluGlyAsn-156 |
| SEQ. ID. NO. 21887 | 182-AlaArgThrLeuGlyAsnValPheHis-190 |
| SEQ. ID. NO. 21888 | 194-GlySerGlyValAspGlyIleGlnAlaValValAlaPheAspGlnTyrAla-210 |
| Antigenic Index - Jameson-Wolf | |
| SEQ. ID. NO. 21889 | 1-MetAsnArgArgAsnAlaArgIleGluArgAlaValArg-13 |
| SEQ. ID. NO. 21890 | 23-AspAlaProGlySerGlyThrLeuLeuHisGlnArgGlyLysGlnValGlySerArgAsnAspAlaLeuAla-46 |
| SEQ. ID. NO. 21891 | 65-GlyLysLysArgPheValGlnSerArgAsnLeuValGlyArgLysGlnArgAsn-82 |
| SEQ. ID. NO. 21892 | 125-MetProGlnGlyValGluGlnGlyCysArg-134 |
| SEQ. ID. NO. 21893 | 142-ArgThrGlyPheAspCysArgLeuLysHisPheLysGluGlyAsnAla-157 |
| SEQ. ID. NO. 21894 | 172-SerAlaAspThrSerGlyIleAspAlaAspAlaArgThr-184 |
| SEQ. ID. NO. 21895 | 191-AsnArgAlaGlySerGlyValAspGly-199 |
| Hydrophilic Regions - Hopp-Woods | |
| SEQ. ID. NO. 21896 | 1-MetAsnArgArgAsnAlaArgIleGluArgAlaValArg-13 |
| SEQ. ID. NO. 21897 | 33-GlnArgGlyLysGlnValGlySerArgAsnAspAlaLeuAla-46 |
| SEQ. ID. NO. 21898 | 65-GlyLysLysArgPheValGln-71 |
| SEQ. ID. NO. 21899 | 74-AsnLeuValGlyArgLysGlnArgAsn-82 |

TABLE 1-continued

| | |
|---|---|
| SEQ. ID. NO. 21900 | 127-GlnGlyValGluGlnGlyCysArg-134 |
| SEQ. ID. NO. 21901 | 143-ThrGlyPheAspCysArgLeuLysHisPheLysGluGlyAsnAla-157 |
| SEQ. ID. NO. 21902 | 172-SerAlaAspThrSerGlyIleAspAlaAspAlaArgThr-184 |
| a649 | |
| AMPHI Regions - AMPHI | |
| SEQ. ID. NO. 21903 | 6-LeuSerAlaIleLeuGlyLeuVal-13 |
| SEQ. ID. NO. 21904 | 27-ArgAspThrLysHisIleArgLysAlaAsn-36 |
| SEQ. ID. NO. 21905 | 57-SerGlnGlyAsnVal-61 |
| SEQ. ID. NO. 21906 | 63-GluLeuArgGluAsnLys-68 |
| SEQ. ID. NO. 21907 | 71-ArgLysAlaPheArgSerLeu-77 |
| Antigenic Index - Jameson-Wolf | |
| SEQ. ID. NO. 21908 | 20-GlyThrSerGluProAlaHisArgAspThrLysHisIleArgLysAlaAsnLys-37 |
| SEQ. ID. NO. 21909 | 40-LeuHisProGluCysArgLysTyrLeuGluArgArgAlaAla-53 |
| SEQ. ID. NO. 21910 | 56-ArgSerGlnGlyAsnValGlnGluLeuArgGluAsnLysLysAlaArgLysAlaPheArgSerLeuProTyrLysGluGlnLysThrGlnCys-86 |
| SEQ. ID. NO. 21911 | 92-AlaPheAspAspPheAspGlySerArgPheArgArg-103 |
| Hydrophilic Regions - Hopp-Woods | |
| SEQ. ID. NO. 21912 | 20-GlyThrSerGluProAlaHisArgAspThrLysHisIleArgLysAlaAsnLys-37 |
| SEQ. ID. NO. 21913 | 42-ProGluCysArgLysTyrLeuGluArgArgAlaAla-53 |
| SEQ. ID. NO. 21914 | 59-GlyAsnValGlnGluLeuArgGluAsnLysLysAlaArgLysAlaPheArg-75 |
| SEQ. ID. NO. 21915 | 78-ProTyrLysGluGlnLysThrGlnCys-86 |
| SEQ. ID. NO. 21916 | 92-AlaPheAspAspPheAspGlySerArgPheArgArg-103 |
| a650 | |
| AMPHI Regions - AMPHI | |
| SEQ. ID. NO. 21917 | 15-SerValCysProGly-19 |
| SEQ. ID. NO. 21918 | 57-LeuTrpSerGluLeuArgGln-63 |
| SEQ. ID. NO. 21919 | 72-ProGluLeuValArgArgHisGlu-79 |
| SEQ. ID. NO. 21920 | 89-PheAsnArgValIleAsn-94 |
| SEQ. ID. NO. 21921 | 137-SerGlyLeuTrpGln-141 |
| SEQ. ID. NO. 21922 | 173-AsnTyrLeuGlnTyrLeuTyrGlyLeuPheGlyAspTrpPro-186 |
| SEQ. ID. NO. 21923 | 198-AsnValGlyArgAlaIleAsnArgAlaArg-207 |
| SEQ. ID. NO. 21924 | 218-LeuArgMetProAsnGluThr-224 |
| SEQ. ID. NO. 21925 | 269-GluAlaIleAlaArgLeuAlaGlyIleThrGlnSer-280 |
| SEQ. ID. NO. 21926 | 314-SerAsnTyrLeuAsnAlaAlaProAsp-322 |
| SEQ. ID. NO. 21927 | 341-IleSerThrAlaThrGlyMet-347 |
| SEQ. ID. NO. 21928 | 349-IleAlaAspIleLysArgLeuAsnAsnLeu-358 |
| SEQ. ID. NO. 21929 | 376-LysThrLeuGlnThrAlaSerGlu-383 |
| SEQ. ID. NO. 21930 | 433-ValArgThrXxxThr-437 |
| Antigenic Index - Jameson-Wolf | |
| SEQ. ID. NO. 21931 | 1-MetSerLysLeuLys-5 |
| SEQ. ID. NO. 21932 | 24-GlnAsnThrSerSerHis-29 |
| SEQ. ID. NO. 21933 | 38-LeuAsnSerSerIleLeuAspLeuProProThrLysGlnTyrPhe-52 |
| SEQ. ID. NO. 21934 | 59-SerGluLeuArgGlnGlyPheArgMetGlyGluValAsnProGluLeuValArgArgHisGluSerLysPheIle-83 |
| SEQ. ID. NO. 21935 | 92-ValIleAsnArgSerArgProTyr-99 |
| SEQ. ID. NO. 21936 | 105-AsnGluValLysLysArgAsnMetProAla-114 |
| SEQ. ID. NO. 21937 | 128-ThrLysAlaLysSerHisValGlyAlaSerGly-138 |
| SEQ. ID. NO. 21938 | 145-AlaThrGlyArgHisTyrGlyLeuGluLysThrProValTyrAspGlyArgHisAspIle-164 |
| SEQ. ID. NO. 21939 | 192-TyrAsnTrpGlyGluGlyAsnValGlyArgAlaIleAsnArgAlaArgAlaGlnGlyLeuGluProThrTyrGluAsnLeuArgMetProAsn GluThrArgAsnTyrVal-228 |
| SEQ. ID. NO. 21940 | 247-AsnIleSerAspIleAspAsnLysProTyr-256 |
| SEQ. ID. NO. 21941 | 259-AlaValGluProAspArgProLeuAspAsnGluAlaIleAla-272 |
| SEQ. ID. NO. 21942 | 294-PheIleProLysSerLysArgLysLeu-302 |
| SEQ. ID. NO. 21943 | 318-AsnAlaAlaProAspSer-323 |
| SEQ. ID. NO. 21944 | 332-ProAlaAlaLysThrSerLeuSerAspIleSerThr-343 |
| SEQ. ID. NO. 21945 | 350-AlaAspIleLysArgLeuAsnAsnLeuAsnGly-360 |
| SEQ. ID. NO. 21946 | 370-LeuValAlaLysAsnGlyLysThrLeuGlnThrAlaSer-382 |
| SEQ. ID. NO. 21947 | 388-IleAspIleAspAsnThrProAsnThrTyrArgSerAsnMetProAlaGlyThr-405 |
| SEQ. ID. NO. 21948 | 411-AlaArgIleArgProAlaAla-417 |
| SEQ. ID. NO. 21949 | 428-LeuProGlnLysThrValArgThrXxxThrArgSerProCysProTyrCys-444 |
| SEQ. ID. NO. 21950 | 446-ThrCysProCysAspSerArgSerAlaThrSerAsnArgLysThrAspArgHisAlaVal-465 |
| Hydrophilic Regions - Hopp-Woods | |
| SEQ. ID. NO. 21951 | 1-MetSerLysLeuLys-5 |
| SEQ. ID. NO. 21952 | 61-LeuArgGlnGlyPheArgMetGlyGluValAsnProGluLeuValArgArgHisGluSerLysPhe-82 |
| SEQ. ID. NO. 21953 | 92-ValIleAsnArgSerArgPro-98 |
| SEQ. ID. NO. 21954 | 105-AsnGluValLysLysArgAsnMetProAla-114 |
| SEQ. ID. NO. 21955 | 128-ThrLysAlaLysSerHisVal-134 |
| SEQ. ID. NO. 21956 | 150-TyrGlyLeuGluLysThrProValTyrAspGlyArgHisAspIle-164 |
| SEQ. ID. NO. 21957 | 202-AlaIleAsnArgAlaArgAlaGlnGlyLeu-211 |
| SEQ. ID. NO. 21958 | 213-ProThrTyrGluAsnLeuArgMetProAsnGluThrArgAsnTyrVal-228 |
| SEQ. ID. NO. 21959 | 249-SerAspIleAspAsn-253 |
| SEQ. ID. NO. 21960 | 260-ValGluProAspArgProLeuAspAsnGluAlaIleAla-272 |
| SEQ. ID. NO. 21961 | 296-ProLysSerLysArgLysLeu-302 |
| SEQ. ID. NO. 21962 | 334-AlaLysThrSerLeu-338 |
| SEQ. ID. NO. 21963 | 350-AlaAspIleLysArgLeuAsn-356 |
| SEQ. ID. NO. 21964 | 373-LysAsnGlyLysThrLeuGlnThrAlaSer-382 |
| SEQ. ID. NO. 21965 | 389-AspIleAspAsnThrProAsnThrTyr-397 |
| SEQ. ID. NO. 21966 | 411-AlaArgIleArgPro-415 |

TABLE 1-continued

| | |
|---|---|
| SEQ. ID. NO. 21967 | 431-LysThrValArgThrXxxThrArgSer-439 |
| SEQ. ID. NO. 21968 | 447-CysProCysAspSerArgSerAlaThrSerAsnArgLysThrAspArgHisAlaVal-465 |
| a652-1 | |
| AMPHI Regions - AMPHI | |
| SEQ. ID. NO. 21969 | 6-AspIlePheAlaArg-10 |
| SEQ. ID. NO. 21970 | 52-ArgAspGlyAspLys-56 |
| SEQ. ID. NO. 21971 | 62-LysGlyValLeuLysAlaValGluHisValAsnAsnGlnIleAlaGlnAla-78 |
| SEQ. ID. NO. 21972 | 130-LeuTyrArgTyrLeuGlyGlyAlaGlyPro-39 |
| SEQ. ID. NO. 21973 | 149-ValIleAsnGlyGly-153 |
| SEQ. ID. NO. 21974 | 173-LysSerPheArgGluAlaLeuArgCys-181 |
| SEQ. ID. NO. 21975 | 184-GluIlePheHisAlaLeuLysLys-191 |
| SEQ. ID. NO. 21976 | 266-AlaGluPheAlaGluTyrLeuGluGlyLeuValAsn-277 |
| SEQ. ID. NO. 21977 | 323-AlaGluGlyIleGluLysGlyVal-330 |
| SEQ. ID. NO. 21978 | 338-ValAsnGlnIleGlyThrLeuSerGluThrLeuLysAlaValAspLeuAlaLys-355 |
| SEQ. ID. NO. 21979 | 377-AspLeuAlaValAla-381 |
| SEQ. ID. NO. 21980 | 391-SerLeuSerArgSerAspArgMetAlaLysTyrAsnGlnLeuLeuArgIleGluGluLeuAlaGluAlaAlaAspTyr-417 |
| Antigenic Index - Jameson-Wolf | |
| SEQ. ID. NO. 21981 | 11-GluIleLeuAspSerArgGlyAsnProThrValGlu-22 |
| SEQ. ID. NO. 21982 | 36-AlaValProSerGlyAlaSerThrGlyGlnLysGluAlaLeuGluLeuArgAspGlyAspLysSerArgTyrSerGlyLysGlyValLeuLysAla ValGluHisValAsn-72 |
| SEQ. ID. NO. 21983 | 83-AspAlaAsnGluGlnSerTyr-89 |
| SEQ. ID. NO. 21984 | 97-LeuAspGlyThrGluAsnLysGlyAsnLeuGly-107 |
| SEQ. ID. NO. 21985 | 121-AlaAlaAlaGluAspSerGlyLeuPro-129 |
| SEQ. ID. NO. 21986 | 135-GlyGlyAlaGlyProMet-140 |
| SEQ. ID. NO. 21987 | 151-AsnGlyGlyGluHisAlaAsnAsnSerAsn-161 |
| SEQ. ID. NO. 21988 | 173-LysSerPheArgGluAlaLeuArgCysGlyAla-183 |
| SEQ. ID. NO. 21989 | 190-LysLysLeuCysAspSerLysGlyPheProThrThrValGlyAspGluGlyGlyPhe-208 |
| SEQ. ID. NO. 21990 | 211-AsnLeuAsnSerHisLysGluAlaLeu-219 |
| SEQ. ID. NO. 21991 | 243-CysAlaSerSerGluPheTyrLysAspGlyLysTyrHisLeuGluAlaGluGlyArgSerTyrThrAsn-265 |
| SEQ. ID. NO. 21992 | 283-SerIleGluAspGlyMetAspGluAsnAspTrpGluGly-295 |
| SEQ. ID. NO. 21993 | 299-LeuThrGluLysLeuGlyGlyLys-306 |
| SEQ. ID. NO. 21994 | 309-LeuValGlyAspAspLeu-314 |
| SEQ. ID. NO. 21995 | 318-AsnProLysIleLeuAlaGluGlyIleGluLysGlyVal-330 |
| SEQ. ID. NO. 21996 | 352-AspLeuAlaLysArgAsnArgTyrAla-360 |
| SEQ. ID. NO. 21997 | 363-MetSerHisArgSerGlyGluThrGluAspSerThrIle-375 |
| SEQ. ID. NO. 21998 | 388-LysThrGlySerLeuSerArgSerAspArgMetAlaLys-400 |
| SEQ. ID. NO. 21999 | 405-LeuArgIleGluGluGluLeuAlaGluAlaAlaAspTyrProSerLys-420 |
| Hydrophilic Regions - Hopp-Woods | |
| SEQ. ID. NO. 22000 | 11-GluIleLeuAspSerArgGlyAsnProThrValGlu-22 |
| SEQ. ID. NO. 22001 | 43-ThrGlyGlnLysGluAlaLeuGluLeuArgAspGlyAspLysSerArgTyrSerGly-61 |
| SEQ. ID. NO. 22002 | 63-GlyValLeuLysAlaValGlu-69 |
| SEQ. ID. NO. 22003 | 97-LeuAspGlyThrGluAsnLysGlyAsnLeu-106 |
| SEQ. ID. NO. 22004 | 121-AlaAlaAlaGluAspSerGly-127 |
| SEQ. ID. NO. 22005 | 153-GlyGluHisAlaAsn-157 |
| SEQ. ID. NO. 22006 | 173-LysSerPheArgGluAlaLeuArgCysGlyAla-183 |
| SEQ. ID. NO. 22007 | 190-LysLysLeuCysAspSerLysGly-197 |
| SEQ. ID. NO. 22008 | 202-ValGlyAspGluGlyGlyPhe-208 |
| SEQ. ID. NO. 22009 | 213-AsnSerHisLysGluAlaLeu-219 |
| SEQ. ID. NO. 22010 | 247-GluPheTyrLysAspGlyLysTyrHisLeuGluAlaGluGlyArgSerTyrThr-264 |
| SEQ. ID. NO. 22011 | 283-SerIleGluAspGlyMetAspGluAsnAspTrpGluGly-295 |
| SEQ. ID. NO. 22012 | 299-LeuThrGluLysLeuGlyGly-305 |
| SEQ. ID. NO. 22013 | 321-IleLeuAlaGluGlyIleGluLysGlyVal-330 |
| SEQ. ID. NO. 22014 | 352-AspLeuAlaLysArgAsnArgTyr-359 |
| SEQ. ID. NO. 22015 | 364-SerHisArgSerGlyGluThrGluAspSerThrIle-375 |
| SEQ. ID. NO. 22016 | 391-SerLeuSerArgSerAspArgMetAlaLys-400 |
| SEQ. ID. NO. 22017 | 405-LeuArgIleGluGluGluLeuAlaGluAlaAlaAspTyrProSer-419 |
| a653 | |
| AMPHI Regions - AMPHI | |
| SEQ. ID. NO. 22018 | 6-MetArgMetProGluValThrLysGlyPheSerGlySer-18 |
| SEQ. ID. NO. 22019 | 60-ThrMetArgLysProArgLeuThr-67 |
| SEQ. ID. NO. 22020 | 75-AlaLeuIlePheThrCysPheAla-82 |
| SEQ. ID. NO. 22021 | 96-ThrAlaLeuAlaAlaIleThrCysIle-104 |
| SEQ. ID. NO. 22022 | 111-LeuGlyLysMetGluGluPheAsn-118 |
| Antigenic Index - Jameson-Wolf | |
| SEQ. ID. NO. 22023 | 4-GluProMetArgMetProGluValThrLysGlyPheSerGlySer-18 |
| SEQ. ID. NO. 22024 | 45-GlyCysArgSerThrArgLysThr-52 |
| SEQ. ID. NO. 22025 | 56-ValArgProGluThrMetArgLysProArgLeuThrAsnSerSerAla-71 |
| SEQ. ID. NO. 22026 | 86-AsnSerGlyCysAsnAla-91 |
| SEQ. ID. NO. 22027 | 103-CysIleSerGlyProProCysArgLeuGlyLysMetGluGlu-116 |
| SEQ. ID. NO. 22028 | 125-SerArgHisLysIleThrProProArgGlyProArgArgVal-138 |
| SEQ. ID. NO. 22029 | 145-ThrLysSerGlnAsnGlyThrGly-152 |
| SEQ. ID. NO. 22030 | 154-GlyTyrSerProProAlaThrArgProAla-163 |
| Hydrophilic Regions - Hopp-Woods | |
| SEQ. ID. NO. 22031 | 4-GluProMetArgMetProGluValThrLys-13 |
| SEQ. ID. NO. 22032 | 47-ArgSerThrArgLysThr-52 |
| SEQ. ID. NO. 22033 | 57-ArgProGluThrMetArgLysProArgLeuThrAsn-68 |
| SEQ. ID. NO. 22034 | 107-ProProCysArgLeuGlyLysMetGluGlu-116 |

TABLE 1-continued

SEQ. ID. NO. 22035 126-ArgHisLysIleThrProProArgGlyProArg-136
SEQ. ID. NO. 22036 158-ProAlaThrArgProAla-163
a656
AMPHI Regions - AMPHI
SEQ. ID. NO. 22037 14-MetAlaArgThrLeuGlyAlaProGlu-22
SEQ. ID. NO. 22038 42-ArgArgProSerThr-46
SEQ. ID. NO. 22039 92-LeuAlaSerLeuAsnLysSerCys-99
Antigenic Index - Jameson-Wolf
SEQ. ID. NO. 22040 6-GlySerThrSerSer-10
SEQ. ID. NO. 22041 19-GlyAlaProGluSerValProAlaGlyLysValAlaAla-31
SEQ. ID. NO. 22042 40-SerPheArgArgProSerThrLeuGlu-48
SEQ. ID. NO. 22043 74-ArgProThrSerLeuArgProLysSerIleAsn-84
SEQ. ID. NO. 22044 94-SerLeuAsnLysSerCysSerLeuAlaArgSerSerAlaGlyValLeuProArgArgArgValProAla-116
SEQ. ID. NO. 22045 120-ThrMetThrSerSerArgSerArgArgThrArgIleSerGlyGluGluProThrMetTrpLysSerProLysSer-144
Hydrophilic Regions - Hopp-Woods
SEQ. ID. NO. 22046 40-SerPheArgArgProSerThr-46
SEQ. ID. NO. 22047 76-ThrSerLeuArgProLysSer-82
SEQ. ID. NO. 22048 99-CysSerLeuAlaArgSerSer-105
SEQ. ID. NO. 22049 109-LeuProArgArgArgValProAla-116
SEQ. ID. NO. 22050 121-MetThrSerSerArgSerArgArgThrArgIleSerGlyGluGluProThrMet-138
SEQ. ID. NO. 22051 140-LysSerProLysSer-144
a657
AMPHI Regions - AMPHI
SEQ. ID. NO. 22052 9-ProAlaMetLeuGly-13
SEQ. ID. NO. 22053 20-LeuGlyArgMetPheThr-25
SEQ. ID. NO. 22054 62-ThrAlaLeuGluGluLeuAlaLysCysAlaAla-72
SEQ. ID. NO. 22055 85-MetArgPheLeuAlaLys-90
SEQ. ID. NO. 22056 140-PheLeuProGlyIleLeuLysThr-147
SEQ. ID. NO. 22057 161-LysThrValAspGluLeuLysAla-168
SEQ. ID. NO. 22058 178-CysValLeuGluLysMetValAsp-185
SEQ. ID. NO. 22059 203-GlnThrPheAspProAlaGluAsnIle-211
SEQ. ID. NO. 22060 232-GlnGlnAlaArgGlnMetAlaGlnArgLeuAlaAspGluLeuAsnTyrValGlyValLeu-251
SEQ. ID. NO. 22061 279-HisThrValAspAlaCysAlaAla-286
SEQ. ID. NO. 22062 314-AsnIleLeuGlyAsp-318
Antigenic Index - Jameson-Wolf
SEQ. ID. NO. 22063 1-MetLysAsnIleSerLeu-6
SEQ. ID. NO. 22064 16-GlyGlyGlyGlnLeuGlyArg-22
SEQ. ID. NO. 22065 37-ValLeuAspProAsnProAsnAlaPro-45
SEQ. ID. NO. 22066 57-ProPheAspAsnGlnThrAlaLeuGluGluLeuAlaLys-69
SEQ. ID. NO. 22067 75-ThrGluPheGluAsnValAsnAlaAspAla-84
SEQ. ID. NO. 22068 91-HisThrAsnValSerProSerGlyAsp-99
SEQ. ID. NO. 22069 106-AsnArgIleGlnGluLysAlaTrpIle-114
SEQ. ID. NO. 22070 128-CysLysAlaGluAspIleThrGluGluSerIle-138
SEQ. ID. NO. 22071 150-LeuGlyTyrAspGlyLysGlyGlnIleArgValLysThrValAspGluLeuLysAlaAlaPheAlaGluHisArgGlyValAspCysValLeu-180
SEQ. ID. NO. 22072 182-LysMetValAspLeuArgGlyGluIle-190
SEQ. ID. NO. 22073 196-ArgLeuAsnAsnAspAsnValGlnThrPheAspProAlaGluAsnIleHisGluAsnGly-215
SEQ. ID. NO. 22074 230-IleGlnGlnGlnAlaArgGlnMetAla-238
SEQ. ID. NO. 22075 269-IleAlaProArgProHisAsnSerGlyHisHis-279
SEQ. ID. NO. 22076 288-GlnPheGlnGlnGlnVal-293
SEQ. ID. NO. 22077 300-ProProAlaAspThrLysLeuLeuSer-308
SEQ. ID. NO. 22078 319-ValTrpGlnGluAspGlyGlyGluProAspTrp-329
SEQ. ID. NO. 22079 331-ProLeuGlnSerArgProAspAlaHis-339
SEQ. ID. NO. 22080 344-GlyLysLysThrAlaHisLysGlyArgLysMetGly-355
SEQ. ID. NO. 22081 360-LeuSerThrAspSerAspThrAlaPheGlnGluAlaLysLysLeuHis-375
Hydrophilic Regions - Hopp-Woods
SEQ. ID. NO. 22082 62-ThrAlaLeuGluGluLeuAlaLys-69
SEQ. ID. NO. 22083 75-ThrGluPheGluAsnValAsn-81
SEQ. ID. NO. 22084 128-CysLysAlaGluAspIleThrGluGluSerIle-138
SEQ. ID. NO. 22085 152-TyrAspGlyLysGlyGlnIleArgValLysThrValAspGluLeuLysAlaAlaPheAlaGluHisArgGlyValAspCysValLeu-180
SEQ. ID. NO. 22086 182-LysMetValAspLeuArgGlyGluIle-190
SEQ. ID. NO. 22087 197-LeuAsnAsnAspAsn-201
SEQ. ID. NO. 22088 206-AspProAlaGluAsnIleHis-212
SEQ. ID. NO. 22089 230-IleGlnGlnGlnAlaArgGlnMetAla-238
SEQ. ID. NO. 22090 269-IleAlaProArgProHisAsn-275
SEQ. ID. NO. 22091 301-ProAlaAspThrLysLeu-306
SEQ. ID. NO. 22092 320-TrpGlnGluAspGlyGlyGluProAsp-328
SEQ. ID. NO. 22093 334-SerArgProAspAla-338
SEQ. ID. NO. 22094 344-GlyLysLysThrAlaHisLysGlyArgLysMetGly-355
SEQ. ID. NO. 22095 362-ThrAspSerAspThrAlaPheGlnGluAlaLysLysLeuHis-375
a658
AMPHI Regions - AMPHI
SEQ. ID. NO. 22096 28-ArgGlnTyrAlaAspValValGlnPheIleGlyGlnThrLeuArgHisLeuSerArgLeuLeuLeuAsn-50
SEQ. ID. NO. 22097 57-TrpAspAspGlyVal-61
SEQ. ID. NO. 22098 68-ValAsnValPheGlyArgIleGluSer-76
SEQ. ID. NO. 22099 94-GlnValHisHisPhePheGlnAsnAlaIleHisAla-105
SEQ. ID. NO. 22100 128-IleAlaGlnCysSerGlyPheGlnAspAlaGlyGln-139
SEQ. ID. NO. 22101 143-AlaPhePheSerAspValPheGly-150
Antigenic Index - Jameson-Wolf
SEQ. ID. NO. 22102 6-ValArgThrArgArgAspPheValAspAspGlnPheMetArgValAlaAspAsnLysHisPhe-26
SEQ. ID. NO. 22103 55-SerGlyTrpAspAspGlyValGlyGluAspThrVal-66

TABLE 1-continued

SEQ. ID. NO. 22104 72-GlyArgIleGluSer-76
SEQ. ID. NO. 22105 84-ThrAlaTyrAspAsnGlyAsn-90
SEQ. ID. NO. 22106 108-PheGlyLysArgGlyPhe-113
SEQ. ID. NO. 22107 131-CysSerGlyPheGlnAspAlaGlyGlnLys-140
SEQ. ID. NO. 22108 155-LeuIleArgArgGlyLeuGln-161
SEQ. ID. NO. 22109 174-ValLeuArgAspGlyAsnAla-180
SEQ. ID. NO. 22110 189-MetPheGlyGluLysThrHisArgIleGly-198
SEQ. ID. NO. 22111 202-PheGluLeuGlyArgAsnSerArgThr-210
SEQ. ID. NO. 22112 216-GlnSerGlyLeuValValLysArgArgThrGln-226
SEQ. ID. NO. 22113 230-GlyLysPheArgCysArgArgIleArgVal-239
SEQ. ID. NO. 22114 251-PheGlySerAsnSerLysHisSerAla-259
Hydrophilic Regions - Hopp-Woods
SEQ. ID. NO. 22115 6-ValArgThrArgArgAspPheValAsp-14
SEQ. ID. NO. 22116 16-GlnPheMetArgValAlaAspAsnLysHisPhe-26
SEQ. ID. NO. 22117 56-GlyTrpAspAspGlyValGlyGluAspThrVal-66
SEQ. ID. NO. 22118 72-GlyArgIleGluSer-76
SEQ. ID. NO. 22119 135-GlnAspAlaGlyGln-139
SEQ. ID. NO. 22120 174-ValLeuArgAspGlyAsnAla-180
SEQ. ID. NO. 22121 190-PheGlyGluLysThrHisArgIleGly-198
SEQ. ID. NO. 22122 203-GluLeuGlyArgAsnSerArg-209
SEQ. ID. NO. 22123 220-ValValLysArgArgThrGln-226
SEQ. ID. NO. 22124 230-GlyLysPheArgCysArgArgIleArgVal-239
SEQ. ID. NO. 22125 253-SerAsnSerLysHisSerAla-259
a661
AMPHI Regions - AMPHI
SEQ. ID. NO. 22126 19-GlyIleThrAspLysProPheArgArgLeuCysArgAspPheGlyAlaGly-35
SEQ. ID. NO. 22127 37-AlaValCysGluMetLeu-42
SEQ. ID. NO. 22128 75-AspProGlnGlnMetAlaAspAlaAla-83
SEQ. ID. NO. 22129 122-AlaAlaIleLeuGluAlaValValLys-130
SEQ. ID. NO. 22130 152-ProValIleAlaLysIleAlaGlu-159
SEQ. ID. NO. 22131 222-TyrAspArgAlaArgArg-227
SEQ. ID. NO. 22132 235-ProArgPheGluThrLeuArgArgThrArgCys-245
SEQ. ID. NO. 22133 248-AlaCysLeuGluPheGlyArgMetTyrArgHisTyrPheGluPro-262
SEQ. ID. NO. 22134 267-AlaArgValLeuArgArgHis-273
Antigenic Index - Jameson-Wolf
SEQ. ID. NO. 22135 20-IleThrAspLysProPheArgArgLeuCysArgAspPheGlyAlaGly-35
SEQ. ID. NO. 22136 42-LeuThrSerAspProThrLeuArgAsnThrArgLysThrLeuHisArgSerAspPheAlaAspGluGlyGly-65
SEQ. ID. NO. 22137 72-AlaGlySerAspProGlnGlnMetAlaAspAlaAlaArg-84
SEQ. ID. NO. 22138 97-AsnMetGlyCysProAlaLysLysValCys-106
SEQ. ID. NO. 22139 143-GlyTrpHisAspAspHisGlnAsnLeu-151
SEQ. ID. NO. 22140 157-IleAlaGluAspCysGly-162
SEQ. ID. NO. 22141 168-XxxProArgThrHisAla-173
SEQ. ID. NO. 22142 176-AsnValGlnArgArgSerGlyLeuArgProAspCysArgAsnGlnMetProSerGluHisProGlyLeuGlyGlnArgArgHisTyrLeuAla AlaLysSerProSerArgProGlnThrAsnArgArgArgArgHisTyrAspArgAlaArgArgAlaArgGln-230
SEQ. ID. NO. 22143 235-ProArgPheGluThrLeuArgArgThrArgCysPhe-246
SEQ. ID. NO. 22144 256-TyrArgHisTyrPheGluProHisProSerHisAlaArgValLeuArgArgHisArgArgCysAlaHisArgThrGlnThrHisArgLeuVal HisArgArgAsnAlaArgArgArgThrAspThrSer-298
Hydrophilic Regions - Hopp-Woods
SEQ. ID. NO. 22145 20-IleThrAspLysProPheArgArgLeuCysArgAspPhe-32
SEQ. ID. NO. 22146 46-ProThrLeuArgAsnThrArgLysThrLeuHisArgSerAspPheAlaAsp
GluGlyGly-65
SEQ. ID. NO. 22147 73-GlySerAspProGlnGlnMetAlaAspAlaAlaArg-84
SEQ. ID. NO. 22148 100-CysProAlaLysLysValCys-106
SEQ. ID. NO. 22149 157-IleAlaGluAspCysGly-162
SEQ. ID. NO. 22150 176-AsnValGlnArgArgSerGlyLeuArgProAspCysArgAsnGlnMetProSerGluHisProGlyLeuGlyGlnArgArgHisTyrLeu-205
SEQ. ID. NO. 22151 208-LysSerProSerArgProGlnThrAsnArgArgArgArgHisTyrAspArgAlaArgArgAlaArgGln-230
SEQ. ID. NO. 22152 238-GluThrLeuArgArgThrArgCys-245
SEQ. ID. NO. 22153 268-ArgValLeuArgArgHisArgArgCysAlaHisArgThrGlnThr-282
SEQ. ID. NO. 22154 285-LeuValHisArgArgAsnAlaArgArgArgThrAspThrSer-298
a663
AMPHI Regions - AMPHI
SEQ. ID. NO. 22155 19-ProPheAlaLeuLeuHisLysLeuAlaAspLeuThrGlyLeuLeuAlaTyr-35
SEQ. ID. NO. 22156 66-LysGlnHisPheLysHisMetAlaLysLeu-75
SEQ. ID. NO. 22157 87-AlaGlyArgLeuLysSerLeuValArg-95
SEQ. ID. NO. 22158 168-GluGlyLeuArgAlaLeuValLysGlnPheArgLys-179
SEQ. ID. NO. 22159 209-ThrIleThrGlyLeuSerArgIleAlaAlaLeuAlaAsn-221
SEQ. ID. NO. 22160 243-ProAlaTrpGluSer-247
SEQ. ID. NO. 22161 258-GlnArgMetAsnArgPheIleGluGluArgValArgGluHis-271
Antigenic Index - Jameson-Wolf
SEQ. ID. NO. 22162 38-ValLysProArgArgArgIleGlyGlu-46
SEQ. ID. NO. 22163 56-TrpAspGlyLysLysArgLysThrValLeu-65
SEQ. ID. NO. 22164 87-AlaGlyArgLeuLysSer-92
SEQ. ID. NO. 22165 94-ValArgTyrArgAsnLysHisTyrLeuAsp-103
SEQ. ID. NO. 22166 105-AlaLeuAlaAlaGlyGluLys-111
SEQ. ID. NO. 22167 139-TyrSerHisGlnLysAsnLysIleLeuAsp-148
SEQ. ID. NO. 22168 150-GlnIleLeuLysGlyArgAsnArgTyr-158
SEQ. ID. NO. 22169 166-ArgThrGluGlyLeuArgAlaLeu-173
SEQ. ID. NO. 22170 175-LysGlnPheArgLysSerSerAla-182
SEQ. ID. NO. 22171 188-ProAspGlnAspPheGlyArgAsnAspSerVal-198
SEQ. ID. NO. 22172 229-ProValArgGluAlaAspAsnThr-236

TABLE 1-continued

| | |
|---|---|
| SEQ. ID. NO. 22173 | 243-ProAlaTrpGluSerPheProSerGluAspAlaGlnAlaAspAlaGlnArgMetAsnArgPheIleGluGluArgValArgGluHisProGlu-273 |
| SEQ. ID. NO. 22174 | 280-LysArgPheLysThrArgProGluGlySerProAspPheTyr-293 |
| Hydrophilic Regions - Hopp-Woods | |
| SEQ. ID. NO. 22175 | 39-LysProArgArgArgIleGlyGlu-46 |
| SEQ. ID. NO. 22176 | 56-TrpAspGlyLysLysArgLysThrValLeu-65 |
| SEQ. ID. NO. 22177 | 88-GlyArgLeuLysSer-92 |
| SEQ. ID. NO. 22178 | 94-ValArgTyrArgAsn-98 |
| SEQ. ID. NO. 22179 | 105-AlaLeuAlaAlaGlyGluLys-111 |
| SEQ. ID. NO. 22180 | 142-GlnLysAsnLysIleLeuAsp-148 |
| SEQ. ID. NO. 22181 | 150-GlnIleLeuLysGlyArgAsnArgTyr-158 |
| SEQ. ID. NO. 22182 | 166-ArgThrGluGlyLeuArgAlaLeu-173 |
| SEQ. ID. NO. 22183 | 176-GlnPheArgLysSerSer-181 |
| SEQ. ID. NO. 22184 | 190-GlnAspPheGlyArgAsnAspSerVal-198 |
| SEQ. ID. NO. 22185 | 229-ProValArgGluAlaAspAsn-235 |
| SEQ. ID. NO. 22186 | 248-PheProSerGluAspAlaGlnAlaAspAlaGlnArgMetAsnArgPheIleGluGluArgValArgGluHisProGlu-273 |
| SEQ. ID. NO. 22187 | 280-LysArgPheLysThrArgProGluGlySerPro-290 |
| a664 | |
| AMPHI Regions - AMPHI | |
| SEQ. ID. NO. 22188 | 28-AlaHisArgMetCys-32 |
| SEQ. ID. NO. 22189 | 47-AlaAspValPheAspThrAlaHisGlyAlaAlaGly-58 |
| SEQ. ID. NO. 22190 | 88-AlaArgProValValGluIle-94 |
| Antigenic Index - Jameson-Wolf | |
| SEQ. ID. NO. 22191 | 25-SerGlyGlyAlaHisArgMetCysGlyArg-34 |
| SEQ. ID. NO. 22192 | 48-AspValPheAspThrAlaHisGly-55 |
| SEQ. ID. NO. 22193 | 73-PheLeuGlnArgLysLeuGluPro-80 |
| SEQ. ID. NO. 22194 | 108-IleGlyGlyGlyThrAlaValGlyLysAspGluLeuGlyValLysAspValGln-125 |
| SEQ. ID. NO. 22195 | 137-AlaHisGlyAspAspHisGluAsn-144 |
| SEQ. ID. NO. 22196 | 164-AlaIleProArgGlnSerArgProTrp-172 |
| SEQ. ID. NO. 22197 | 175-ProLeuArgTrpCysLysThrArgPhe-183 |
| Hydrophilic Regions - Hopp-Woods | |
| SEQ. ID. NO. 22198 | 74-LeuGlnArgLysLeuGluPro-80 |
| SEQ. ID. NO. 22199 | 113-AlaValGlyLysAspGluLeuGlyValLysAspValGln-125 |
| SEQ. ID. NO. 22200 | 137-AlaHisGlyAspAspHisGluAsn-144 |
| SEQ. ID. NO. 22201 | 166-ProArgGlnSerArg-170 |
| a665-1 | |
| AMPHI Regions - AMPHI | |
| SEQ. ID. NO. 22202 | 6-HisTyrLeuLysAspTyrGln-12 |
| SEQ. ID. NO. 22203 | 105-LeuTyrAlaSerAla-109 |
| SEQ. ID. NO. 22204 | 111-AsnLeuPheThrGlnCysGluProGluGlyPheArgLysIleThr-125 |
| SEQ. ID. NO. 22205 | 132-AspValMetSerLysPheThrThrThr-140 |
| SEQ. ID. NO. 22206 | 167-ArgHisTrpValLysTrpGluAspProPhe-176 |
| SEQ. ID. NO. 22207 | 225-SerLeuLysAsnAlaMetLys-231 |
| SEQ. ID. NO. 22208 | 286-GlyIleGluSerValVal-291 |
| SEQ. ID. NO. 22209 | 294-GluTyrPheHisAsnTrpThr-300 |
| SEQ. ID. NO. 22210 | 307-ArgAspTrpPheGlnLeuSerLeu-314 |
| SEQ. ID. NO. 22211 | 329-AspArgAlaSerArgAlaValArgArgIleGluAsnIleArgLeuLeuArgGln-346 |
| SEQ. ID. NO. 22212 | 360-ValArgProAlaArgTyrGluGluMetAsnAsnPheTyrThr-373 |
| SEQ. ID. NO. 22213 | 380-GlyAlaGluValValArgMetTyrHisThrLeu-390 |
| SEQ. ID. NO. 22214 | 396-PheGlnLysGlyMetLys-401 |
| SEQ. ID. NO. 22215 | 520-ThrGluAlaValValProSerLeuLeuArgGlyPheSerAlaPro-534 |
| SEQ. ID. NO. 22216 | 555-AspAlaPheThrArgTrpGluAlaAlaGln-564 |
| SEQ. ID. NO. 22217 | 575-LeuAlaAlaLeuSerAspGlyValGluLeuProLysHisGluLysLeuLeuAlaAlaValGlu-595 |
| SEQ. ID. NO. 22218 | 603-LeuAspAsnAlaPheLysAlaLeu-610 |
| SEQ. ID. NO. 22219 | 622-AspGlyAlaGluAsnIleAspProLeu-630 |
| SEQ. ID. NO. 22220 | 648-LeuProLysTrpHisGluLeuAsnArg-656 |
| SEQ. ID. NO. 22221 | G674-lyTrpArgThrLeuArgAsnValCysArgAla-684 |
| SEQ. ID. NO. 22222 | 696-ThrValAlaGluLysTyrAlaGluMetAlaGlnAsnMet-708 |
| SEQ. ID. NO. 22223 | 712-TrpGlyIleLeuSer-716 |
| SEQ. ID. NO. 22224 | 728-ArgLeuLeuAlaGlnPheAlaAspLysPheSer-738 |
| SEQ. ID. NO. 22225 | 758-AspThrLeuGlnGlnValGlnThrAla-766 |
| SEQ. ID. NO. 22226 | 782-SerLeuIleGlySerPheSerArgAsnVal-791 |
| SEQ. ID. NO. 22227 | 822-ArgLeuValGlnAlaPheAsnLeuCysAsnLysLeu-833 |
| Antigenic Index - Jameson-Wolf | |
| SEQ. ID. NO. 22228 | 8-LeuLysAspTyrGlnThrProAlaTyr-16 |
| SEQ. ID. NO. 22229 | 26-AspIleAsnGluPro-30 |
| SEQ. ID. NO. 22230 | 34-ValLysSerArgLeuThrValGluProLysArgValGlyGlu-47 |
| SEQ. ID. NO. 22231 | 49-LeuValLeuAspGlySerAla-55 |
| SEQ. ID. NO. 22232 | 79-AlaAspValProSerGluArgPheThrVal-88 |
| SEQ. ID. NO. 22233 | 90-ValGluThrGluIleLeuProAlaGluAsnLysSerLeu-102 |
| SEQ. ID. NO. 22234 | 114-ThrGlnCysGluProGluGlyPheArgLys-123 |
| SEQ. ID. NO. 22235 | 128-IleAspArgProAspValMetSer-135 |
| SEQ. ID. NO. 22236 | 142-ValAlaAspLysLysArgTyrPro-149 |
| SEQ. ID. NO. 22237 | 154-AsnGlyAsnLysIleAspGlyGlyGluTyrSerAspGlyArgHisTrpValLysTrpGluAspProPheAlaLysProSer-180 |
| SEQ. ID. NO. 22238 | 191-AlaValThrGluAspTyr-196 |
| SEQ. ID. NO. 22239 | 200-MetSerGlyArgAsnValLysIle-207 |
| SEQ. ID. NO. 22240 | 211-ThrThrGluAlaAspLysProLysVal-219 |
| SEQ. ID. NO. 22241 | 230-MetLysTrpAspGluThrArgPhe-237 |
| SEQ. ID. NO. 22242 | 255-AsnMetGlyAlaMetGluAsnLysGlyLeu-264 |
| SEQ. ID. NO. 22243 | 275-AspSerArgThrAlaThrAspThrAspPheGluGlyIleGlu-288 |
| SEQ. ID. NO. 22244 | 295-TyrPheHisAsnTrpThrGlyAsnArgValThrCysArgAspTrp-309 |

TABLE 1-continued

| | |
|---|---|
| SEQ. ID. NO. 22245 | 313-SerLeuLysGluGly-317 |
| SEQ. ID. NO. 22246 | 322-ArgAspGlnGluPheSerGlyAspArgAlaSerArgAlaValArgArgIleGluAsn-340 |
| SEQ. ID. NO. 22247 | 347-HisGlnPheProGluAspAlaGlyProThrAlaHisProValArgProAlaArgTyrGluGluMetAsn-369 |
| SEQ. ID. NO. 22248 | 376-ValTyrGluLysGlyAlaGluVal-383 |
| SEQ. ID. NO. 22249 | 394-GluGlyPheGlnLysGlyMet-400 |
| SEQ. ID. NO. 22250 | 404-PheGlnArgHisAspGlyGlnAlaValThrCysAspAspPheArg-418 |
| SEQ. ID. NO. 22251 | 437-SerGlnAlaGlyThrPro-442 |
| SEQ. ID. NO. 22252 | 446-AlaGlnGlyArgLeuLysAsnAsnVal-454 |
| SEQ. ID. NO. 22253 | 459-IleLysGlnThrValProProThrProAspMetAlaAspLysGlnPro-474 |
| SEQ. ID. NO. 22254 | 485-AsnCysAsnGlyGluAlaVal-491 |
| SEQ. ID. NO. 22255 | 494-AspTyrGlnGlyLysArgAlaThrGlu-502 |
| SEQ. ID. NO. 22256 | 509-GluAlaGluGlnThrPhe-514 |
| SEQ. ID. NO. 22257 | 537-LeuAsnTyrProTyrSerAspAspAspLeu-546 |
| SEQ. ID. NO. 22258 | 552-HisAspSerAspAla-556 |
| SEQ. ID. NO. 22259 | 578-LeuSerAspGlyValGluLeuProLysHisGluLysLeu-590 |
| SEQ. ID. NO. 22260 | 594-ValGluLysValIleSerAspAspLeuLeu-603 |
| SEQ. ID. NO. 22261 | 614-ValProSerGluAlaGluLeuTrpAspGlyAlaGluAsnIleAspProLeuArg-631 |
| SEQ. ID. NO. 22262 | 633-HisGlnAlaArgGluAlaLeu-639 |
| SEQ. ID. NO. 22263 | 652-HisGluLeuAsnArgGlnAlaAlaLysGlnGluAsnGlnSerTyrGluTyrSerProGluAlaAlaGly-674 |
| SEQ. ID. NO. 22264 | 677-ThrLeuArgAsnValCys-682 |
| SEQ. ID. NO. 22265 | 689-AlaAspProAlaHis-693 |
| SEQ. ID. NO. 22266 | 696-ThrValAlaGluLysTyrAlaGlu-703 |
| SEQ. ID. NO. 22267 | 719-AsnGlyAsnGluSerAspThrArgAsnArgLeu-729 |
| SEQ. ID. NO. 22268 | 733-PheAlaAspLysPheSerAspAspAlaLeuVal-743 |
| SEQ. ID. NO. 22269 | 752-GlySerSerArgArgSerAspThrLeuGln-761 |
| SEQ. ID. NO. 22270 | 768-GlnHisProLysPheSerLeuGluAsnProAsnLysAlaArgSer-782 |
| SEQ. ID. NO. 22271 | 785-GlySerPheSerArgAsnValPro-792 |
| SEQ. ID. NO. 22272 | 795-HisAlaGluAspGlySerGlyTyrArgPheIleAla-806 |
| SEQ. ID. NO. 22273 | 808-LysValIleGluIleAspArgPheAsnProGlnVal-819 |
| SEQ. ID. NO. 22274 | 831-AsnLysLeuGluProHisArgLysAsnLeuVal-841 |
| SEQ. ID. NO. 22275 | 844-AlaLeuGlnArgIleArgAlaGlnGluGlyLeuSerLysAspValGlyGluIleVal-862 |
| Hydrophilic Regions- Hopp-Woods | |
| SEQ. ID. NO. 22276 | 34-ValLysSerArgLeuThrValGluProLysArgValGlyGlu-47 |
| SEQ. ID. NO. 22277 | 81-ValProSerGluArgPheThrVal-88 |
| SEQ. ID. NO. 22278 | 90-ValGluThrGluIleLeuProAlaGluAsnLysSer-101 |
| SEQ. ID. NO. 22279 | 116-CysGluProGluGlyPheArg-122 |
| SEQ. ID. NO. 22280 | 129-AspArgProAspValMetSer-135 |
| SEQ. ID. NO. 22281 | 142-ValAlaAspLysLysArgTyr-148 |
| SEQ. ID. NO. 22282 | 154-AsnGlyAsnLysIleAspGlyGlyGluTyrSerAspGlyArgHis-168 |
| SEQ. ID. NO. 22283 | 170-ValLysTrpGluAspProPheAla-177 |
| SEQ. ID. NO. 22284 | 201-SerGlyArgAsnValLys-206 |
| SEQ. ID. NO. 22285 | 213-GluAlaAspLysProLysVal-219 |
| SEQ. ID. NO. 22286 | 230-MetLysTrpAspGluThrArgPhe-237 |
| SEQ. ID. NO. 22287 | 258-AlaMetGluAsnLysGly-263 |
| SEQ. ID. NO. 22288 | 275-AspSerArgThrAlaThrAspThrAspPheGluGlyIleGlu-288 |
| SEQ. ID. NO. 22289 | 313-SerLeuLysGluGly-317 |
| SEQ. ID. NO. 22290 | 322-ArgAspGlnGluPheSerGlyAspArgAlaSerArgAlaValArgArgIleGluAsn-340 |
| SEQ. ID. NO. 22291 | 348-GlnPheProGluAspAlaGlyPro-355 |
| SEQ. ID. NO. 22292 | 361-ArgProAlaArgTyrGluGluMetAsn-369 |
| SEQ. ID. NO. 22293 | 376-ValTyrGluLysGlyAlaGluVal-383 |
| SEQ. ID. NO. 22294 | 394-GluGlyPheGlnLysGlyMet-400 |
| SEQ. ID. NO. 22295 | 406-ArgHisAspGlyGln-410 |
| SEQ. ID. NO. 22296 | 413-ThrCysAspAspPheArg-418 |
| SEQ. ID. NO. 22297 | 446-AlaGlnGlyArgLeuLysAsnAsnVal-454 |
| SEQ. ID. NO. 22298 | 467-ProAspMetAlaAspLysGlnPro-474 |
| SEQ. ID. NO. 22299 | 495-TyrGlnGlyLysArgAlaThrGlu-502 |
| SEQ. ID. NO. 22300 | 541-TyrSerAspAspAspLeu-546 |
| SEQ. ID. NO. 22301 | 552-HisAspSerAspAla-556 |
| SEQ. ID. NO. 22302 | 580-AspGlyValGluLeuProLysHisGluLysLeu-590 |
| SEQ. ID. NO. 22303 | 594-ValGluLysValIleSer-599 |
| SEQ. ID. NO. 22304 | 616-SerGluAlaGluLeu-620 |
| SEQ. ID. NO. 22305 | 622-AspGlyAlaGluAsnIleAspPro-629 |
| SEQ. ID. NO. 22306 | 633-HisGlnAlaArgGluAlaLeu-639 |
| SEQ. ID. NO. 22307 | 652-HisGluLeuAsnArgGlnAlaAlaLysGlnGluAsnGlnSer-665 |
| SEQ. ID. NO. 22308 | 689-AlaAspProAlaHis-693 |
| SEQ. ID. NO. 22309 | 696-ThrValAlaGluLysTyrAlaGlu-703 |
| SEQ. ID. NO. 22310 | 719-AsnGlyAsnGluSerAspThrArgAsnArgLeu-729 |
| SEQ. ID. NO. 22311 | 733-PheAlaAspLysPheSerAsp-739 |
| SEQ. ID. NO. 22312 | 753-SerSerArgArgSerAspThr-759 |
| SEQ. ID. NO. 22313 | 776-AsnProAsnLysAlaArgSer-782 |
| SEQ. ID. NO. 22314 | 795-HisAlaGluAspGlySerGly-801 |
| SEQ. ID. NO. 22315 | 808-LysValIleGluIleAspArgPheAsn-816 |
| SEQ. ID. NO. 22316 | 831-AsnLysLeuGluProHisArgLysAsnLeuVal-841 |
| SEQ. ID. NO. 22317 | 844-AlaLeuGlnArgIleArgAlaGlnGluGlyLeuSerLysAspValGlyGluIleVal-862 |
| a666 | |
| AMPHI Regions - AMPHI | |
| SEQ. ID. NO. 22318 | 89-GlyTyrAspIleLeuLysGlnGlyGlySer-98 |
| SEQ. ID. NO. 22319 | 162-LeuLysPheMetGluAlaVal-168 |

TABLE 1-continued

Antigenic Index - Jameson-Wolf
SEQ. ID. NO. 22320 5-AsnHisGlnSerAsnSerGlyGluGlyValLeu-15
SEQ. ID. NO. 22321 40-AsnGlnGlyLysValAsnThr-46
SEQ. ID. NO. 22322 54-AlaAspAlaHisThrProGluHisAlaThr-63
SEQ. ID. NO. 22323 65-LeuThrGluGlnLysGln-70
SEQ. ID. NO. 22324 92-IleLeuLysGlnGlyGlySerAlaAla-100
SEQ. ID. NO. 22325 114-GluProGlnSerSerGlyLeuGlyGly-122
SEQ. ID. NO. 22326 130-AspAsnThrAlaLysThr-135
SEQ. ID. NO. 22327 137-ThrThrPheAspGlyArgGluThrAlaPro-146
SEQ. ID. NO. 22328 154-PheLeuAspLysAspGlyGlnPro-161
Hydrophilic Regions - Hopp-Woods
SEQ. ID. NO. 22329 8-SerAsnSerGlyGlu-12
SEQ. ID. NO. 22330 40-AsnGlnGlyLysValAsnThr-46
SEQ. ID. NO. 22331 55-AspAlaHisThrProGluHis-61
SEQ. ID. NO. 22332 65-LeuThrGluGlnLysGln-70
SEQ. ID. NO. 22333 96-GlyGlySerAlaAla-100
SEQ. ID. NO. 22334 139-PheAspGlyArgGluThrAlaPro-146
SEQ. ID. NO. 22335 154-PheLeuAspLysAspGlyGlnPro-161
a667
AMPHI Regions - AMPHI
SEQ. ID. NO. 22336 49-IleAlaAspPheLeuGlnProAlaArgValGluArgLeuProHisLeuAlaAla-66
SEQ. ID. NO. 22337 74-LysThrAlaGlnPhe-78
SEQ. ID. NO. 22338 115-IleAlaAlaValAlaGluIle-121
SEQ. ID. NO. 22339 128-IleAlaArgGlyValAspAlaValGlnArg-137
SEQ. ID. NO. 22340 152-ThrAspGlnLeuArgArgMetPhePheAsnGlnLeuGluLysPheGlyAspAsnHis-170
SEQ. ID. NO. 22341 174-ValIleHisLeuAlaAspCysThrAsp-182
SEQ. ID. NO. 22342 201-LysMetMetLeuHisLysIleProThrArgLeu-211
Antigenic Index - Jameson-Wolf
SEQ. ID. NO. 22343 11-IleValSerAspProLeuAsp-17
SEQ. ID. NO. 22344 27-SerAlaAlaAspGlnThrGluThrGln-35
SEQ. ID. NO. 22345 56-AlaArgValGluArgLeuPro-62
SEQ. ID. NO. 22346 71-LeuAlaArgLysThrAlaGln-77
SEQ. ID. NO. 22347 84-ArgHisIleArgProArgLeuValLysArgGluGlnIle-96
SEQ. ID. NO. 22348 130-ArgGlyValAspAlaValGln-136
SEQ. ID. NO. 22349 139-ValMetGlnAsnArgGlnValGlu-146
SEQ. ID. NO. 22350 151-ProThrAspGlnLeuArg-156
SEQ. ID. NO. 22351 163-LeuGluLysPheGlyAsp-168
SEQ. ID. NO. 22352 179-AspCysThrAspMet-183
SEQ. ID. NO. 22353 188-ProProThrHisAlaAlaArgAsnArgHisAsnLeu-199
SEQ. ID. NO. 22354 207-IleProThrArgLeu-211
SEQ. ID. NO. 22355 226-GlyGlnArgGlyArgGlnValIleGlnArgThrAspThrLeu-239
SEQ. ID. NO. 22356 247-IleGluSerGlnAsnArgGlyHisAspSer-256
Hydrophilic Regions - Hopp-Woods
SEQ. ID. NO. 22357 11-IleValSerAspProLeu-16
SEQ. ID. NO. 22358 27-SerAlaAlaAspGlnThrGluThrGln-35
SEQ. ID. NO. 22359 56-AlaArgValGluArgLeuPro-62
SEQ. ID. NO. 22360 71-LeuAlaArgLysThrAlaGln-77
SEQ. ID. NO. 22361 84-ArgHisIleArgProArgLeuValLysArgGluGlnIle-96
SEQ. ID. NO. 22362 130-ArgGlyValAspAlaValGln-136
SEQ. ID. NO. 22363 164-GluLysPheGlyAsp-168
SEQ. ID. NO. 22364 191-HisAlaAlaArgAsnArgHisAsnLeu-199
SEQ. ID. NO. 22365 227-GlnArgGlyArgGlnValIleGlnArgThrAspThr-238
SEQ. ID. NO. 22366 249-SerGlnAsnArgGlyHisAsp-255
a669
AMPHI Regions - AMPHI
SEQ. ID. NO. 22367 24-LysLeuHisArgAlaPhe-29
SEQ. ID. NO. 22368 59-GlnIlePheArgHisValGlnSer-66
SEQ. ID. NO. 22369 79-LysProProAsnThrAla-84
Antigenic Index - Jameson-Wolf
SEQ. ID. NO. 22370 1-MetArgArgIleIleLysLysHisGlnProValAsn-12
SEQ. ID. NO. 22371 33-GlyArgLysArgProHisHisHisAspArgSerLeuArgArgGlnHisGlyIle-50
SEQ. ID. NO. 22372 64-ValGlnSerSerAsnArgGlnAsnGlyArgGlnProValCysThrLysProProAsnThrAlaSer-85
SEQ. ID. NO. 22373 100-AlaAspIleLysArgIleLeu-106
Hydrophilic Regions - Hopp-Woods
SEQ. ID. NO. 22374 1-MetArgArgIleIleLysLysHisGlnPro-10
SEQ. ID. NO. 22375 33-GlyArgLysArgProHisHisHisAspArgSerLeuArgArgGlnHisGly-49
SEQ. ID. NO. 22376 65-GlnSerSerAsnArgGlnAsnGlyArgGlnProValCysThrLysProProAsn-82
SEQ. ID. NO. 22377 100-AlaAspIleLysArgIleLeu-106
a670
AMPHI Regions - AMPHI
SEQ. ID. NO. 22378 10-ArgSerCysPheGly-14
SEQ. ID. NO. 22379 16-ValLysAsnAlaSerGlyValSer-23
SEQ. ID. NO. 22380 34-IleThrArgSerAla-38
SEQ. ID. NO. 22381 77-ValGlySerSerAsnAsnIle-83
SEQ. ID. NO. 22382 126-PheSerAlaCysSer-130
Antigenic Index - Jameson-Wolf
SEQ. ID. NO. 22383 4-CysArgAsnCysLeuAlaArgSerCys-12
SEQ. ID. NO. 22384 18-AsnAlaSerGlyValSerSerSerArgIleCysProLeuSer-31
SEQ. ID. NO. 22385 33-LysIleThrArgSerAlaThrSerArgAlaAsnProIle-45
SEQ. ID. NO. 22386 65-AsnThrSerProThrIleSerGlySerSerAlaGluValGlySerSerAsnAsnIleThrArgGlySerIleAlaLysProArgAlaIleAla-95

TABLE 1-continued

| | |
|---|---|
| SEQ. ID. NO. 22387 | 98-CysCysTrpProProGluSerTrpGluGlyLysAla-109 |
| SEQ. ID. NO. 22388 | 114-AlaSerProThrArgSerLysSerSer-122 |
| SEQ. ID. NO. 22389 | 145-AsnThrValArgCysGly-150 |
| Hydrophilic Regions - Hopp-Woods | |
| SEQ. ID. NO. 22390 | 33-LysIleThrArgSerAlaThrSerArgAlaAsn-43 |
| SEQ. ID. NO. 22391 | 73-SerSerAlaGluValGlySer-79 |
| SEQ. ID. NO. 22392 | 87-SerIleAlaLysProArgAlaIleAla-95 |
| SEQ. ID. NO. 22393 | 116-ProThrArgSerLysSer-121 |
| a671 | |
| AMPHI Regions - AMPHI | |
| SEQ. ID. NO. 22394 | 96-ThrProArgIleAla-100 |
| SEQ. ID. NO. 22395 | 119-ArgLeuPheIleArgTyr-124 |
| Antigenic Index - Jameson-Wolf | |
| SEQ. ID. NO. 22396 | 11-PheAsnAlaProAsnThrProProLysMetArgLeuAlaLysProLysProThrAlaGluThrAlaProValSerSerGluArg-38 |
| SEQ. ID. NO. 22397 | 45-GlnAlaMetThrAsnArgGluMetAsnAspArgAlaAsnAlaAsnArgArgGlyTrpAsnAspAlaLysAlaMetSerAlaLysGlyAlaAla LysSerLeuAlaLysLysLysAlaThrThr-85 |
| SEQ. ID. NO. 22398 | 98-ArgIleAlaAspSerThrMet-104 |
| SEQ. ID. NO. 22399 | 110-AlaGluThrArgArgSerAlaThrGlyArgLeu-120 |
| SEQ. ID. NO. 22400 | 125-LeuThrGlyAspThr-129 |
| Hydrophilic Regions - Hopp-Woods | |
| SEQ. ID. NO. 22401 | 16-ThrProProLysMetArgLeuAlaLysProLysProThrAlaGlu-30 |
| SEQ. ID. NO. 22402 | 32-AlaProValSerSerGluArg-38 |
| SEQ. ID. NO. 22403 | 47-MetThrAsnArgGluMetAsnAspArgAlaAsnAlaAsnArgArgGlyTrpAsnAspAlaLysAlaMetSerAlaLysGlyAlaAlaLysSer LeuAlaLysLysLysAlaThrThr-85 |
| SEQ. ID. NO. 22404 | 110-AlaGluThrArgArgSerAlaThr-117 |
| a672 | |
| AMPHI Regions - AMPHI | |
| SEQ. ID. NO. 22405 | 38-ArgAlaValAspIleIleLysAlaGlnLys-47 |
| SEQ. ID. NO. 22406 | 50-AlaAlaLeuProProPheValSerValVal-59 |
| SEQ. ID. NO. 22407 | 67-AlaGlnAsnIleArgArgIleLeuAlaGluValPro-78 |
| SEQ. ID. NO. 22408 | 91-AlaPheCysArgGlnPheHisArgProTyr-100 |
| SEQ. ID. NO. 22409 | 105-ArgValGlnThrAlaSerAspIleArgAsnAlaAlaAspArgPhe-119 |
| SEQ. ID. NO. 22410 | 131-HisProSerGluTyrGly-136 |
| SEQ. ID. NO. 22411 | 165-AsnValAspGluAlaIle-170 |
| SEQ. ID. NO. 22412 | 173-ThrGlyAlaGluAla-177 |
| Antigenic Index - Jameson-Wolf | |
| SEQ. ID. NO. 22413 | 1-MetArgLysIleArgThrLysIleCysGlyIleThrThrProGluAspAlaLeu-18 |
| SEQ. ID. NO. 22414 | 34-ProGlnSerProArgAlaValAspIleIleLysAlaGlnLys-47 |
| SEQ. ID. NO. 22415 | 65-GluSerAlaGlnAsnIleArgArgIleLeuAla-75 |
| SEQ. ID. NO. 22416 | 84-PheHisGlyAspGluAspAspAlaPhe-92 |
| SEQ. ID. NO. 22417 | 107-GlnThrAlaSerAspIleArgAsnAlaAlaAspArgPheProAspAla-122 |
| SEQ. ID. NO. 22418 | 130-TyrHisProSerGluTyrGlyGlyThrGlyHisArgPheAsp-143 |
| SEQ. ID. NO. 22419 | 149-GluTyrSerGlyLysPro-154 |
| SEQ. ID. NO. 22420 | 159-GlyGlyLeuThrProGluAsnValAspGluAlaIleArg-171 |
| SEQ. ID. NO. 22421 | 176-GluAlaValAspValSerGlyGlyValGluAlaSerLysGlyLysLysAspProAlaLys-195 |
| SEQ. ID. NO. 22422 | 202-ThrAlaAsnArgLeuSerArg-208 |
| Hydrophilic Regions - Hopp-Woods | |
| SEQ. ID. NO. 22423 | 1-MetArgLysIleArgThrLysIle-8 |
| SEQ. ID. NO. 22424 | 13-ThrProGluAspAlaLeu-18 |
| SEQ. ID. NO. 22425 | 36-SerProArgAlaValAsp-41 |
| SEQ. ID. NO. 22426 | 43-IleLysAlaGlnLys-47 |
| SEQ. ID. NO. 22427 | 66-SerAlaGlnAsnIleArgArgIleLeuAla-75 |
| SEQ. ID. NO. 22428 | 85-HisGlyAspGluAspAspAlaPhe-92 |
| SEQ. ID. NO. 22429 | 110-SerAspIleArgAsnAlaAlaAspArgPheProAsp-121 |
| SEQ. ID. NO. 22430 | 164-GluAsnValAspGluAlaIleArg-171 |
| SEQ. ID. NO. 22431 | 184-ValGluAlaSerLysGlyLysLysAspProAlaLys-195 |
| SEQ. ID. NO. 22432 | 204-AsnArgLeuSerArg-208 |
| a673 | |
| AMPHI Regions - AMPHI | |
| SEQ. ID. NO. 22433 | 84-LeuAsnAspArgLeuAsnGlnAsnValThrGluAlaLeuGlyGlyValAspVal-101 |
| SEQ. ID. NO. 22434 | 110-ArgPheThrAspAla-114 |
| SEQ. ID. NO. 22435 | 117-ValValLeuLysGlnLeuProLys-124 |
| SEQ. ID. NO. 22436 | 172-ArgIleAlaAsnLeuLeuGluLeuIleLysProTyrLeu-184 |
| SEQ. ID. NO. 22437 | 212-LysLeuPheArgTyrLeuGlyGluGlu-220 |
| SEQ. ID. NO. 22438 | 261-GlyGluArgLeuLysLysIleSerThr-269 |
| SEQ. ID. NO. 22439 | 275-MetGluLysLeuPhe-279 |
| SEQ. ID. NO. 22440 | 285-LeuLysValTrpValLysValLys-292 |
| Antigenic Index - Jameson-Wolf | |
| SEQ. ID. NO. 22441 | 7-LeuAlaGlyGluArgAlaAlaAspGlyTyrArg-17 |
| SEQ. ID. NO. 22442 | 24-ValGlyArgProAsnValGlyLysSerThr-33 |
| SEQ. ID. NO. 22443 | 44-SerIleThrSerLysLysAlaGlnThrThrArgAsnArgValThr-58 |
| SEQ. ID. NO. 22444 | 61-TyrThrAspAspThrAla-66 |
| SEQ. ID. NO. 22445 | 73-ThrProGlyPheGlnThrAspHisArgAsnAlaLeuAsnAspArgLeuAsnGlnAsnValThrGlu-94 |
| SEQ. ID. NO. 22446 | 110-ArgPheThrAspAlaAspArgValVal-118 |
| SEQ. ID. NO. 22447 | 121-GlnLeuProLysHisThr-126 |
| SEQ. ID. NO. 22448 | 134-LysIleAspLysAspLysAlaLysAspArgTyrAla-145 |
| SEQ. ID. NO. 22449 | 153-ValArgAlaGluPhe-157 |
| SEQ. ID. NO. 22450 | 180-IleLysProTyrLeuProGluSerVal-188 |
| SEQ. ID. NO. 22451 | 190-MetTyrProGluAspMetValThrAspLysSerAlaArg-202 |
| SEQ. ID. NO. 22452 | 208-IleValArgGluLysLeuPhe-214 |

TABLE 1-continued

| | |
|---|---|
| SEQ. ID. NO. 22453 | 217-LeuGlyGluGluLeuPro-222 |
| SEQ. ID. NO. 22454 | 227-ValGluValGluGlnPheGluGluGluAspGlyLeuAsn-239 |
| SEQ. ID. NO. 22455 | 247-ValAspLysGluSerGlnLys-253 |
| SEQ. ID. NO. 22456 | 258-GlyLysGlyGlyGluArgLeuLysLysIleSerThrGluAlaArgLeuAspMetGluLysLeuPheAsp-280 |
| SEQ. ID. NO. 22457 | 291-ValLysSerGlyTrpAlaAspAspIleArgPheLeuArg-303 |
| Hydrophilic Regions - Hopp-Woods | |
| SEQ. ID. NO. 22458 | 7-LeuAlaGlyGluArgAlaAlaAspGlyTyrArg-17 |
| SEQ. ID. NO. 22459 | 45-IleThrSerLysLysAlaGlnThrThrArgAsnArgVal-57 |
| SEQ. ID. NO. 22460 | 61-TyrThrAspAspThrAla-66 |
| SEQ. ID. NO. 22461 | 78-ThrAspHisArgAsnAlaLeuAsnAspArgLeuAsn-89 |
| SEQ. ID. NO. 22462 | 110-ArgPheThrAspAlaAspArgValVal-118 |
| SEQ. ID. NO. 22463 | 134-LysIleAspLysAspLysAlaLysAspArgTyrAla-145 |
| SEQ. ID. NO. 22464 | 153-ValArgAlaGluPhe-157 |
| SEQ. ID. NO. 22465 | 194-AspMetValThrAspLysSerAlaArg-202 |
| SEQ. ID. NO. 22466 | 208-IleValArgGluLysLeuPhe-214 |
| SEQ. ID. NO. 22467 | 217-LeuGlyGluGluLeuPro-222 |
| SEQ. ID. NO. 22468 | 227-ValGluValGluGlnPheGluGluGluAspGlyLeuAsn-239 |
| SEQ. ID. NO. 22469 | 247-ValAspLysGluSerGlnLys-253 |
| SEQ. ID. NO. 22470 | 259-LysGlyGlyGluArgLeuLysLysIleSerThrGluAlaArgLeuAspMetGluLysLeuPheAsp-280 |
| SEQ. ID. NO. 22471 | 293-SerGlyTrpAlaAspAspIleArgPheLeuArg-303 |
| a674 | |
| AMPHI Regions - AMPHI | |
| SEQ. ID. NO. 22472 | 16-ValTyrGlnSerLeuIle-21 |
| SEQ. ID. NO. 22473 | 24-ThrAlaAlaProGluIleAlaLysAsnIleArgGluMetProAspPheAlaLys-41 |
| SEQ. ID. NO. 22474 | 58-AlaAlaGluTyrIleArgGlnIleArgPro-67 |
| SEQ. ID. NO. 22475 | 86-ThrAlaCysHisGluLeuSerAlaMetProGluThr-97 |
| SEQ. ID. NO. 22476 | 107-IleGluValThrLysThrPheGlyGlyThrAspGlyHisLysPheValAsnGlyIleLeuAspLysLeuAla-130 |
| Antigenic Index - Jameson-Wolf | |
| SEQ. ID. NO. 22477 | 1-MetLysThrAlaArgArgArgSerArgGluLeuAla-12 |
| SEQ. ID. NO. 22478 | 28-GluIleAlaLysAsnIleArgGluMetProAspPheAlaLysAlaAspGluGluLeuPhe-47 |
| SEQ. ID. NO. 22479 | 54-ThrGlnThrAsnAla-58 |
| SEQ. ID. NO. 22480 | 63-ArgGlnIleArgProLeuLeuAspArgAspGluLysAspLeuAsnProIleGluArg-81 |
| SEQ. ID. NO. 22481 | 93-AlaMetProGluThrProTyr-99 |
| SEQ. ID. NO. 22482 | 105-GluAlaIleGluValThrLysThrPheGlyGlyThrAspGlyHisLysPhe-121 |
| SEQ. ID. NO. 22483 | 129-LeuAlaAlaGlnIleArgProAspGluProLysArgArg-141 |
| Hydrophilic Regions - Hopp-Woods | |
| SEQ. ID. NO. 22484 | 1-MetLysThrAlaArgArgArgSerArgGluLeuAla-12 |
| SEQ. ID. NO. 22485 | 28-GluIleAlaLysAsnIleArgGluMetProAspPheAlaLysAlaAspGluGluLeuPhe-47 |
| SEQ. ID. NO. 22486 | 63-ArgGlnIleArgProLeuLeuAspArgAspGluLysAspLeuAsnProIleGluArg-81 |
| SEQ. ID. NO. 22487 | 105-GluAlaIleGluVal-109 |
| SEQ. ID. NO. 22488 | 133-IleArgProAspGluProLysArgArg-141 |
| a675 | |
| AMPHI Regions - AMPHI | |
| SEQ. ID. NO. 22489 | 21-ArgPheThrAsnGluIleGlySerGluMetLeuLysValCysCysArgThrLeuGlnGluLeuGly-42 |
| SEQ. ID. NO. 22490 | 74-AlaLeuIleAlaIle-78 |
| SEQ. ID. NO. 22491 | 123-GlnAlaIleGluArgIleGluGluLysAlaSerAsp-134 |
| SEQ. ID. NO. 22492 | 141-GluCysAlaAsnLeuValAsnLeuLeuLeuGlu-151 |
| Antigenic Index - Jameson-Wolf | |
| SEQ. ID. NO. 22493 | 6-ProAsnLeuAspGlyLysHisLeuArg-14 |
| SEQ. ID. NO. 22494 | 26-IleGlySerGluMetLeu-31 |
| SEQ. ID. NO. 22495 | 42-GlyValAlaAspGluAsnIle-48 |
| SEQ. ID. NO. 22496 | 68-SerSerGluLysPheAsp-73 |
| SEQ. ID. NO. 22497 | 82IleArgGlyGluThrTyr-87 |
| SEQ. ID. NO. 22498 | 92-ValSerAsnGluSerGlyAlaGlyVal-100 |
| SEQ. ID. NO. 22499 | 118-ThrGluAsnAspAlaGlnAlaIleGluArgIleGluGluLysAlaSerAspAlaAlaLysValAlaVal-140 |
| SEQ. ID. NO. 22500 | 152-GluGlnPheGluAspGluGlu-158 |
| Hydrophilic Regions - Hopp-Woods | |
| SEQ. ID. NO. 22501 | 8-LeuAspGlyLysHisLeuArg-14 |
| SEQ. ID. NO. 22502 | 26-IleGlySerGluMetLeu-31 |
| SEQ. ID. NO. 22503 | 42-GlyValAlaAspGluAsnIle-48 |
| SEQ. ID. NO. 22504 | 68-SerSerGluLysPheAsp-73 |
| SEQ. ID. NO. 22505 | 82-IleArgGlyGluThrTyr-87 |
| SEQ. ID. NO. 22506 | 92-ValSerAsnGluSerGlyAlaGly-99 |
| SEQ. ID. NO. 22507 | 118-ThrGluAsnAspAlaGlnAlaIleGluArgIleGluGluLysAlaSerAspAlaAlaLysValAlaVal-140 |
| SEQ. ID. NO. 22508 | 152-GluGlnPheGluAspGluGlu-158 |
| a677 | |
| AMPHI Regions - AMPHI | |
| SEQ. ID. NO. 22509 | 20-AlaArgLeuCysArgPheArgArg-27 |
| SEQ. ID. NO. 22510 | 45-LeuThrProPheArgArgValAsnHisPheValAlaPheThrArgPheAsnGln-62 |
| SEQ. ID. NO. 22511 | 78-IleAspPheIleAspAlaAsp-84 |
| SEQ. ID. NO. 22512 | 86-PheAspGlyLeuLeuAla-91 |
| SEQ. ID. NO. 22513 | 105-HisLeuValGlyArgPhe-110 |
| SEQ. ID. NO. 22514 | 154-CysArgProValAspAspLeuAspAsp-162 |
| SEQ. ID. NO. 22515 | 165-AlaPhePheIleAsnGlnLeuIleLysLeuValPheGlnCys-178 |
| Antigenic Index - Jameson-Wolf | |
| SEQ. ID. NO. 22516 | 23-CysArgPheArgArgHisSerArgSerValAsp-33 |
| SEQ. ID. NO. 22517 | 35-AspValPheAspArgLysAspPheAsn-43 |
| SEQ. ID. NO. 22518 | 59-ArgPheAsnGlnThrThrSerGlnArgArgAsnProArgAsnPheVal-74 |
| SEQ. ID. NO. 22519 | 81-IleAspAlaAspAspPheAspGly-88 |
| SEQ. ID. NO. 22520 | 96-GlnGlnThrAspGlyArgAlaGluLysHisLeu-106 |

TABLE 1-continued

SEQ. ID. NO. 22521 114-GlyIleAsnAspAspGlyGlyPhe-121
SEQ. ID. NO. 22522 124-LeuGlyGlnGluThrAspAlaAlaVal-132
SEQ. ID. NO. 22523 155-ArgProValAspAspLeuAspAspPheGly-164
SEQ. ID. NO. 22524 180-ProSerGlyGlyArgAsn-185
Hydrophilic Regions - Hopp-Woods
SEQ. ID. NO. 22525 23-CysArgPheArgArgHisSerArgSerValAsp-33
SEQ. ID. NO. 22526 35-AspValPheAspArgLysAspPhe-42
SEQ. ID. NO. 22527 64-ThrSerGlnArgArgAsnProArg-71
SEQ. ID. NO. 22528 81-IleAspAlaAspAspPheAsp-87
SEQ. ID. NO. 22529 96-GlnGlnThrAspGlyArgAlaGluLysHisLeu-106
SEQ. ID. NO. 22530 115-IleAsnAspAspGlyGly-120
SEQ. ID. NO. 22531 125-GlyGlnGluThrAspAlaAlaVal-132
SEQ. ID. NO. 22532 155-ArgProValAspAspLeuAspAsp-162
a678
AMPHI Regions - AMPHI
SEQ. ID. NO. 22533 10-LeuValSerAlaIleIle-15
SEQ. ID. NO. 22534 24-MetArgGlyValIle-28
SEQ. ID. NO. 22535 47-PheAlaAlaProPhe-51
SEQ. ID. NO. 22536 79-LeuIleGlnLysIleLeuArgSerLeuLeuThrGlyAla-91
SEQ. ID. NO. 22537 102-ArgIleLeuGlyGlyValPheGlyAlaLeuLysGlyIleLeu-115
SEQ. ID. NO. 22538 130-ProAspThrGluGlu-134
Antigenic Index - Jameson-Wolf
SEQ. ID. NO. 22539 125-SerLysThrAspLeuProAspThrGluGluTrpArgGlnSerTyrThr-140
SEQ. ID. NO. 22540 154-HisSerGlyGlyThrAlaGluThrProGluAspAsp-165
Hydrophilic Regions - Hopp-Woods
SEQ. ID. NO. 22541 125-SerLysThrAspLeuProAspThrGluGluTrpArgGln-137
SEQ. ID. NO. 22542 157-GlyThrAlaGluThrProGluAspAsp-165
a681
AMPHI Regions - AMPHI
SEQ. ID. NO. 22543 12-PheSerGluGluAlaLysPheIleSerAlaMet-22
SEQ. ID. NO. 22544 102-LeuProValGlyAsp-106
SEQ. ID. NO. 22545 122-ArgLeuGlyGluGlnCys-127
SEQ. ID. NO. 22546 137-IleGlyGluAlaAspAspAlaGluValValArgValValGlyValPheValGly-154
SEQ. ID. NO. 22547 202-LysCysValHisCysGly-207
SEQ. ID. NO. 22548 210-XxxGlyGlyLysLeuAlaAspPheThrThrIle-220
SEQ. ID. NO. 22549 234-CysAlaProPheAlaAlaLeuArgCysPheCysIlePheGlyValTrpLysArgIleArgAlaValPheCysGlyArg-259
Antigenic Index - Jameson-Wolf
SEQ. ID. NO. 22550 11-AsnPheSerGluGluAlaLysPhe-18
SEQ. ID. NO. 22551 39-AlaThrProAsnSerTrpArgValArgGlnGln-49
SEQ. ID. NO. 22552 59-LeuValLysArgAlaCys-64
SEQ. ID. NO. 22553 67-ProMetArgArgCysLeuProSerArgLeu-76
SEQ. ID. NO. 22554 89-GlyGlyPheGlyMetProSerGluGlySerVal-99
SEQ. ID. NO. 22555 103-ProValGlyAspGlyLeuGlu-109
SEQ. ID. NO. 22556 120-AlaPheArgLeuGlyGluGlnCysGlyGlyPhe-130
SEQ. ID. NO. 22557 136-AspIleGlyGluAlaAspAspAlaGluVal-145
SEQ. ID. NO. 22558 157-AlaAlaGluGluThrPro-162
SEQ. ID. NO. 22559 167-PheLysAsnGlyGly-171
SEQ. ID. NO. 22560 173-AlaValGluGluAlaAspGly-179
SEQ. ID. NO. 22561 185-AspGlyValGlyGlyAspAlaAlaValGluCysArgGlyLysCysLeuCys-201
SEQ. ID. NO. 22562 207-GlyAsnThrXxxGlyGlyLysLeuAlaAsp-216
SEQ. ID. NO. 22563 224-SerAlaAspGlyGlyGly-229
SEQ. ID. NO. 22564 256-PheCysGlyArgArg-260
Hydrophilic Regions - Hopp-Woods
SEQ. ID. NO. 22565 11-AsnPheSerGluGluAlaLysPhe-18
SEQ. ID. NO. 22566 44-TrpArgValArgGln-48
SEQ. ID. NO. 22567 59-LeuValLysArgAlaCys-64
SEQ. ID. NO. 22568 67-ProMetArgArgCysLeuPro-73
SEQ. ID. NO. 22569 95-SerGluGlySerVal-99
SEQ. ID. NO. 22570 120-AlaPheArgLeuGlyGluGln-126
SEQ. ID. NO. 22571 136-AspIleGlyGluAlaAspAspAlaGluVal-145
SEQ. ID. NO. 22572 157-AlaAlaGluGluThrPro-162
SEQ. ID. NO. 22573 173-AlaValGluGluAlaAspGly-179
SEQ. ID. NO. 22574 191-AlaAlaValGluCysArgGlyLysCysLeu-200
SEQ. ID. NO. 22575 210-XxxGlyGlyLysLeuAlaAsp-216
SEQ. ID. NO. 22576 256-PheCysGlyArgArg-260
a682
AMPHI Regions - AMPHI
SEQ. ID. NO. 22577 33-ArgLeuArgLysCysGlyArgIleLeuSerGlyIleCysGluProPhe-48
Antigenic Index - Jameson-Wolf
SEQ. ID. NO. 22578 9-SerTyrGlyLysTrpArgLysAsnTrpAspIle-19
SEQ. ID. NO. 22579 30-SerSerThrArgLeuArgLysCysGlyArg-39
SEQ. ID. NO. 22580 95-ArgPheProThrAspArgProIleLeu-103
SEQ. ID. NO. 22581 112-IleSerProArgThrGlyPheArgTyrProThrArgSerLeuProLysSerLysLysAlaTyrGly-133
Hydrophilic Regions - Hopp-Woods
SEQ. ID. NO. 22582 12-LysTrpArgLysAsnTrpAsp-18
SEQ. ID. NO. 22583 32-ThrArgLeuArgLysCysGlyArg-39

TABLE 1-continued

| | |
|---|---|
| SEQ. ID. NO. 22584 | 97-ProThrAspArgProIleLeu-103 |
| SEQ. ID. NO. 22585 | 124-SerLeuProLysSerLysLysAlaTyrGly-133 |
| a683 | |
| AMPHI Regions - AMPHI | |
| SEQ. ID. NO. 22586 | 26-ThrProAspLysSerAlaArgTrpGluAsnIleGlyThrIleSerAsn-41 |
| SEQ. ID. NO. 22587 | 101-SerSerLeuGlnLeuPhe-106 |
| SEQ. ID. NO. 22588 | 124-ArgProMetSerIleLeuSerGly-131 |
| Antigenic Index - Jameson-Wolf | |
| SEQ. ID. NO. 22589 | 24-CysSerThrProAspLysSerAlaArgTrpGluAsn-35 |
| SEQ. ID. NO. 22590 | 37-GlyThrIleSerAsnGly-42 |
| SEQ. ID. NO. 22591 | 48-IleAsnLysAspSerValArgLysAsnGlyAsn-58 |
| SEQ. ID. NO. 22592 | 63-XxxAspLysLysValValThrAsnLeuLysGlnGluArgPheAla-77 |
| SEQ. ID. NO. 22593 | 93-CysAsnAsnLysThrTyrArgLeu-100 |
| SEQ. ID. NO. 22594 | 106-PheAspThrLysAsnThrGluIleSerThr-115 |
| SEQ. ID. NO. 22595 | 119-ThrAlaSerSerLeuArgPro-125 |
| SEQ. ID. NO. 22596 | 131-GlyThrLeuThrGluLysGlnTyrGlu-139 |
| SEQ. ID. NO. 22597 | 141-ValCysGlyLysLysLeu-146 |
| Hydrophilic Regions - Hopp-Woods | |
| SEQ. ID. NO. 22598 | 25-SerThrProAspLysSerAlaArgTrpGluAsn-35 |
| SEQ. ID. NO. 22599 | 48-IleAsnLysAspSerValArgLysAsnGly-57 |
| SEQ. ID. NO. 22600 | 63-XxxAspLysLysValValThr-69 |
| SEQ. ID. NO. 22601 | 71-LeuLysGlnGluArgPheAla-77 |
| SEQ. ID. NO. 22602 | 107-AspThrLysAsnThrGluIleSer-114 |
| SEQ. ID. NO. 22603 | 133-LeuThrGluLysGlnTyrGlu-139 |
| SEQ. ID. NO. 22604 | 141-ValCysGlyLysLysLeu-146 |
| a684 | |
| AMPHI Regions - AMPHI | |
| SEQ. ID. NO. 22605 | 13-AlaAlaCysGlyThrValGln-19 |
| SEQ. ID. NO. 22606 | 47-LeuAlaGluProLeu-51 |
| SEQ. ID. NO. 22607 | 73-TrpAlaAspThrLeuAspAspMetLeuGluAlaAlaLeuSerAsnAlaPheAsnArgLeuAspSerThr-95 |
| SEQ. ID. NO. 22608 | 110-TrpThrValTyrIleAspAlaPheGlnGlySerTyr-121 |
| SEQ. ID. NO. 22609 | 154-AlaMetThrAlaAlaLeuGluGlnGlyLeuLysGlnAlaAlaGlnGlnMetVal-171 |
| Antigenic Index - Jameson-Wolf | |
| SEQ. ID. NO. 22610 | 26-LeuProAspSerArgTyrIleArgProAlaThrGlnGlyGlyGluThrAlaValGluValArgLeuAlaGluProLeuLysArgGlyGlyLeu-56 |
| SEQ. ID. NO. 22611 | 60-ThrAspProTyrArgLeuAsnThrAlaGln-69 |
| SEQ. ID. NO. 22612 | 76-ThrLeuAspAspMetLeuGlu-82 |
| SEQ. ID. NO. 22613 | 90-AsnArgLeuAspSerThrArg-96 |
| SEQ. ID. NO. 22614 | 101-AlaSerArgSerGlySerThrGluLys-109 |
| SEQ. ID. NO. 22615 | 117-PheGlnGlySerTyrThrGlyLysThrLeu-126 |
| SEQ. ID. NO. 22616 | 133-LeuProAspGlyThrAsnArgProPheHisIleGluThrGluGlnGlnGlyAspGlyTyrAla-153 |
| SEQ. ID. NO. 22617 | 161-GlnGlyLeuLysGlnAlaAla-167 |
| Hydrophilic Regions - Hopp-Woods | |
| SEQ. ID. NO. 22618 | 27-ProAspSerArgTyrIleArg-33 |
| SEQ. ID. NO. 22619 | 35-AlaThrGlnGlyGlyGluThrAlaValGluValArgLeuAlaGluProLeuLysArgGlyGly-55 |
| SEQ. ID. NO. 22620 | 76-ThrLeuAspAspMetLeuGlu-82 |
| SEQ. ID. NO. 22621 | 90-AsnArgLeuAspSer-94 |
| SEQ. ID. NO. 22622 | 102-SerArgSerGlySerThrGluLys-109 |
| SEQ. ID. NO. 22623 | 141-PheHisIleGluThrGluGlnGlnGlyAsp-150 |
| SEQ. ID. NO. 22624 | 161-GlnGlyLeuLysGlnAlaAla-167 |
| a685 | |
| AMPHI Regions - AMPHI | |
| SEQ. ID. NO. 22625 | 7-AsnPheAlaPheCysGlyValVal-14 |
| SEQ. ID. NO. 22626 | 44-CysAlaValLeuLeu-48 |
| SEQ. ID. NO. 22627 | 94-TrpAlaAlaLeuAspThrLeuThrGluLeu-103 |
| SEQ. ID. NO. 22628 | 137-TyrGluAlaLeuHisArgTyr-143 |
| SEQ. ID. NO. 22629 | 154-GlyAlaGluAlaTyrGluGlnLeuAlaLysAsn-164 |
| SEQ. ID. NO. 22630 | 182-GluLysGlnMetGluThrLeuAlaArgIlePheGlyLysGlu-195 |
| SEQ. ID. NO. 22631 | 206-AspAlaLeuPheAla-210 |
| SEQ. ID. NO. 22632 | 296-AlaValGluValLeuAspAsnAlaLeuVal-305 |
| SEQ. ID. NO. 22633 | 336-AlaAlaGluGlnLeuLysGluAlaPhe-344 |
| Antigenic Index - Jameson-Wolf | |
| SEQ. ID. NO. 22634 | 20-LeuAsnAsnLysHisSerTyrSerTyrAlaLysGluProHisThrValLys ProArgPhe-39 |
| SEQ. ID. NO. 22635 | 52-SerProGluProAlaAlaGluLysThrValSer-62 |
| SEQ. ID. NO. 22636 | 74-ProThrAlaArgGlyAspAlaValValProLysAsnProGluArgValAla-90 |
| SEQ. ID. NO. 22637 | 122-AlaPheAspLysAlaAla-127 |
| SEQ. ID. NO. 22638 | 133-PheGluProAspTyrGluAlaLeuHisArgTyrAsn-144 |
| SEQ. ID. NO. 22639 | 151-GlyGlyProGlyAlaGluAlaTyrGluGlnLeuAlaLysAsnAlaThr-166 |
| SEQ. ID. NO. 22640 | 170-LeuThrValAspAsnGlyAsnIleArgThrSerGlyGluLysGlnMetGluThrLeu-188 |
| SEQ. ID. NO. 22641 | 192-PheGlyLysGluAlaArgAlaAlaGluLeuLysAlaGlnIle-205 |
| SEQ. ID. NO. 22642 | 211-GlnThrArgGluAlaAlaLysGlyLysGlyArgGlyLeu-223 |
| SEQ. ID. NO. 22643 | 227-ValThrGlyAsnLysValSerAlaPheGlyThrGlnSerArgLeu-241 |
| SEQ. ID. NO. 22644 | 247-GlyAspIleGlyLeuProProValAspGluSerLeuArgAsnGluGlyHisGlyGln-265 |
| SEQ. ID. NO. 22645 | 271-TyrIleLysGluLysAsnProAspTrpIle-280 |
| SEQ. ID. NO. 22646 | 285-ArgThrAlaAlaIleGlyGlnGluGlyProAla-295 |
| SEQ. ID. NO. 22647 | 307-GlyThrAsnAlaTrpLysArgLysGln-315 |

TABLE 1-continued

| | |
|---|---|
| SEQ. ID. NO. 22648 | 328-GlyGlySerArgGlnLeu-333 |
| SEQ. ID. NO. 22649 | 338-GluGlnLeuLysGluAlaPheGluLysAlaGluPro-349 |
| SEQ. ID. NO. 22650 | 351-AlaAlaGlyLysGlu-355 |
| Hydrophilic Regions - Hopp-Woods | |
| SEQ. ID. NO. 22651 | 28-TyrAlaLysGluProHisThrValLys-36 |
| SEQ. ID. NO. 22652 | 52-SerProGluProAlaAlaGluLysThrValSer-62 |
| SEQ. ID. NO. 22653 | 75-ThrAlaArgGlyAspAlaValVal-82 |
| SEQ. ID. NO. 22654 | 84-LysAsnProGluArgValAla-90 |
| SEQ. ID. NO. 22655 | 122-AlaPheAspLysAlaAla-127 |
| SEQ. ID. NO. 22656 | 135-ProAspTyrGluAla-139 |
| SEQ. ID. NO. 22657 | 156-GluAlaTyrGluGlnLeuAlaLys-163 |
| SEQ. ID. NO. 22658 | 175-GlyAsnIleArgThrSerGlyGluLysGlnMetGluThrLeu-188 |
| SEQ. ID. NO. 22659 | 192-PheGlyLysGluAlaArgAlaAlaGluLeuLysAlaGlnIle-205 |
| SEQ. ID. NO. 22660 | 211-GlnThrArgGluAlaAlaLysGlyLysGlyArgGly-222 |
| SEQ. ID. NO. 22661 | 253-ProValAspGluSerLeuArgAsnGluGlyHisGly-264 |
| SEQ. ID. NO. 22662 | 271-TyrIleLysGluLysAsnPro-277 |
| SEQ. ID. NO. 22663 | 290-GlyGlnGluGlyProAla-295 |
| SEQ. ID. NO. 22664 | 309-AsnAlaTrpLysArgLysGln-315 |
| SEQ. ID. NO. 22665 | 338-GluGlnLeuLysGluAlaPheGluLysAlaGluPro-349 |
| SEQ. ID. NO. 22666 | 351-AlaAlaGlyLysGlu-355 |
| a686 | |
| AMPHI Regions - AMPHI | |
| SEQ. ID. NO. 22667 | 10-AspValPheAspAspIleCysSerAlaValGluSerPheGlyGlyIleAlaArgSerValGlnLeu-31 |
| SEQ. ID. NO. 22668 | 50-ThrThrGlyIleValGluThrValAspLysProLeu-61 |
| SEQ. ID. NO. 22669 | 70-ValGluAlaAspIle-74 |
| SEQ. ID. NO. 22670 | 86-IleProArgAlaPheGlySerGlyIleAlaAlaAlaLeu-98 |
| Antigenic Index - Jameson-Wolf | |
| SEQ. ID. NO. 22671 | 1-TerTerAsnPheSerCysArgAlaAspAspValPheAsp-13 |
| SEQ. ID. NO. 22672 | 46-LeuArgGlnHisThrThrGlyIle-53 |
| SEQ. ID. NO. 22673 | 55-GluThrValAspLysProLeuSerGlyAla-64 |
| SEQ. ID. NO. 22674 | 70-ValGluAlaAspIle-74 |
| SEQ. ID. NO. 22675 | 115-AspAlaValLysAlaGluSerValAsnGlyThrThrGly-127 |
| Hydrophilic Regions - Hopp-Woods | |
| SEQ. ID. NO. 22676 | 6-CysArgAlaAspAspValPheAsp-13 |
| SEQ. ID. NO. 22677 | 55-GluThrValAspLysProLeuSer-62 |
| SEQ. ID. NO. 22678 | 70-ValGluAlaAspIle-74 |
| SEQ. ID. NO. 22679 | 115-AspAlaValLysAlaGluSerValAsn-123 |
| a687 | |
| AMPHI Regions - AMPHI | |
| SEQ. ID. NO. 22680 | 11-AlaAlaLeuPheAlaLeu-16 |
| SEQ. ID. NO. 22681 | 64-LysValGluValLeuGluPhePheGlyTyrPheCysPro-76 |
| SEQ. ID. NO. 22682 | 78-CysAlaHisLeuGluProValLeuSerLysHisAlaLysSerPhe-92 |
| SEQ. ID. NO. 22683 | 112-LeuAlaArgLeuAlaAlaAla-118 |
| SEQ. ID. NO. 22684 | 135-PheAspAlaMetVal-139 |
| SEQ. ID. NO. 22685 | 148-ProGluValLeuLysLysTrpLeu-155 |
| SEQ. ID. NO. 22686 | 176-GlnAlaArgAlaAspLysMetGlnGluLeuThrGluThrPhe-189 |
| Antigenic Index - Jameson-Wolf | |
| SEQ. ID. NO. 22687 | 1-MetLysSerLysHis-5 |
| SEQ. ID. NO. 22688 | 19-CysAspSerLysValGlnThrSerValProAlaAspSerAlaPro-33 |
| SEQ. ID. NO. 22689 | 43-GlyLeuValGluGlyGlnAsnTyr-50 |
| SEQ. ID. NO. 22690 | 56-ProIleProGlnGlnGlnAlaGlyLysValGluVal-67 |
| SEQ. ID. NO. 22691 | 87-LysHisAlaLysSerPheLysAspAspMetTyrLeu-98 |
| SEQ. ID. NO. 22692 | 122-AlaAlaAlaAspSerLysAspValAlaAsn-131 |
| SEQ. ID. NO. 22693 | 141-GlnLysIleLysLeuGlnGluProGluValLeuLys-152 |
| SEQ. ID. NO. 22694 | 159-ThrAlaPheAspGlyLysLysVal-166 |
| SEQ. ID. NO. 22695 | 171-GluSerProGluSerGlnAlaArgAlaAspLysMetGlnGluLeuThrGlu-187 |
| SEQ. ID. NO. 22696 | 189-PheGlnIleAspGlyThrPro-195 |
| SEQ. ID. NO. 22697 | 199-ValGlyGlyLysTyrLysValGluPheAlaAsp-209 |
| SEQ. ID. NO. 22698 | 211-GluSerGlyMetAsnThr-216 |
| SEQ. ID. NO. 22699 | 220-LeuAlaAspLysValArgGluGluGlnLysAlaAlaHis-232 |
| Hydrophilic Regions - Hopp-Woods | |
| SEQ. ID. NO. 22700 | 1-MetLysSerLysHis-5 |
| SEQ. ID. NO. 22701 | 19-CysAspSerLysValGlnThr-25 |
| SEQ. ID. NO. 22702 | 27-ValProAlaAspSerAlaPro-33 |
| SEQ. ID. NO. 22703 | 61-GlnAlaGlyLysValGluVal-67 |
| SEQ. ID. NO. 22704 | 87-LysHisAlaLysSerPheLysAspAspMetTyrLeu-98 |
| SEQ. ID. NO. 22705 | 122-AlaAlaAlaAspSerLysAspValAla-130 |
| SEQ. ID. NO. 22706 | 141-GlnLysIleLysLeuGlnGluProGluValLeuLys-152 |
| SEQ. ID. NO. 22707 | 159-ThrAlaPheAspGlyLysLysVal-166 |
| SEQ. ID. NO. 22708 | 171-GluSerProGluSerGlnAlaArgAlaAspLysMetGlnGluLeuThrGlu-187 |
| SEQ. ID. NO. 22709 | 201-GlyLysTyrLysValGluPheAlaAsp-209 |
| SEQ. ID. NO. 22710 | 220-LeuAlaAspLysValArgGluGluGlnLysAlaAlaHis-232 |
| a688 | |
| AMPHI Regions - AMPHI | |
| SEQ. ID. NO. 22711 | 23-LeuSerAlaLeuLeuGlyLeu-29 |
| SEQ. ID. NO. 22712 | 120-GlyAsnAlaLeuGlnAsnAlaAla-127 |
| Antigenic Index - Jameson-Wolf | |
| SEQ. ID. NO. 22713 | 4-TyrProSerArgPheAlaGln-10 |
| SEQ. ID. NO. 22714 | 13-IleSerValAsnLys-17 |
| SEQ. ID. NO. 22715 | 47-IleIleGlnGlyAsnGluLeuGluProArgAla-57 |

TABLE 1-continued

| | |
|---|---|
| SEQ. ID. NO. 22716 | 61-LeuArgProGlyMetThrLysAspGln-69 |
| SEQ. ID. NO. 22717 | 82-AlaPheHisThrAspArgTrpAspTyr-90 |
| SEQ. ID. NO. 22718 | 93-AsnThrSerArgAsnGlyIleIleLysAspArgSerAsn-105 |
| SEQ. ID. NO. 22719 | 116-ValArgThrGluGlyAsnAla-122 |
| SEQ. ID. NO. 22720 | 125-AsnAlaAlaGluAlaLeuArgValLysGlnAsnAlaAspLysGln-139 |
| Hydrophilic Regions - Hopp-Woods | |
| SEQ. ID. NO. 22721 | 51-AsnGluLeuGluProArgAla-57 |
| SEQ. ID. NO. 22722 | 64-GlyMetThrLysAspGln-69 |
| SEQ. ID. NO. 22723 | 98-GlyIleIleLysAspArgSerAsn-105 |
| SEQ. ID. NO. 22724 | 116-ValArgThrGluGlyAsnAla-122 |
| SEQ. ID. NO. 22725 | 125-AsnAlaAlaGluAlaLeuArgValLysGlnAsnAlaAspLysGln-139 |
| a689 | |
| AMPHI Regions - AMPHI | |
| SEQ. ID. NO. 22726 | 55-TyrProGluMetSerGluLysLeuMet-63 |
| SEQ. ID. NO. 22727 | 65-ValLeuMetAlaMetLeuValThrLeu-73 |
| SEQ. ID. NO. 22728 | 82-LeuProAlaIleProGluMetAlaGln-90 |
| SEQ. ID. NO. 22729 | 111-AlaPheGlyGlnValValGlyGly-118 |
| SEQ. ID. NO. 22730 | 123-IleLysGlyArgLys-127 |
| SEQ. ID. NO. 22731 | 154-LeuAsnLeuArgValValGlnAlaPheGlyAlaGly-165 |
| SEQ. ID. NO. 22732 | 188-PheAlaLeuIleGlyIleIleLeu-195 |
| SEQ. ID. NO. 22733 | 203-ProMetValGlyAlaLeuLeuGlnGlyLeuGlyGlyTrpGlnAlaIlePheVal-220 |
| SEQ. ID. NO. 22734 | 230-LeuGlyLeuValGlnTyrPhe-236 |
| SEQ. ID. NO. 22735 | 245-LysIleGlyArgAspVal-250 |
| SEQ. ID. NO. 22736 | 257-ArgPheLysArgValLeu-262 |
| SEQ. ID. NO. 22737 | 277-SerPheGlySerMetPheAla-283 |
| SEQ. ID. NO. 22738 | 314-MetMetPhePheAsnArgIleThr-321 |
| SEQ. ID. NO. 22739 | 344-AlaAlaAsnLeuSerGlnLeuAlaAlaValLeuPhe-355 |
| SEQ. ID. NO. 22740 | 400-ValLeuGlyValPheGlnSerLeuIleGly-409 |
| Antigenic Index - Jameson-Wolf | |
| SEQ. ID. NO. 22741 | 36-PheArgArgArgAlaVal-41 |
| SEQ. ID. NO. 22742 | 45-IleGlyArgGluPheMetProSer-52 |
| SEQ. ID. NO. 22743 | 57-GluMetSerGluLysLeu-62 |
| SEQ. ID. NO. 22744 | 95-AspValHisArgIleGluGln-101 |
| SEQ. ID. NO. 22745 | 119-SerValSerAspIleLysGlyArgLysProVal-129 |
| SEQ. ID. NO. 22746 | 174-MetValArgAspTyrTyrSerGlyArgLysAlaAla-185 |
| SEQ. ID. NO. 22747 | 238-ProLysProAlaValGlyGlyLysIleGlyArgAspValPhe-251 |
| SEQ. ID. NO. 22748 | 257-ArgPheLysArgValLeuLysThrArgAla-266 |
| SEQ. ID. NO. 22749 | 325-LeuLysThrGlyValHis-330 |
| SEQ. ID. NO. 22750 | 390-PheLysGluGluGlyGlySer-396 |
| SEQ. ID. NO. 22751 | 448-ArgAlaTrpLysGluAsnGlyGlnSerGluTyrLeu-459 |
| Hydrophilic Regions - Hopp-Woods | |
| SEQ. ID. NO. 22752 | 36-PheArgArgArgAlaVal-41 |
| SEQ. ID. NO. 22753 | 45-IleGlyArgGluPheMet-50 |
| SEQ. ID. NO. 22754 | 57-GluMetSerGluLysLeu-62 |
| SEQ. ID. NO. 22755 | 95-AspValHisArgIleGluGln-101 |
| SEQ. ID. NO. 22756 | 119-SerValSerAspIleLysGlyArgLysProVal-129 |
| SEQ. ID. NO. 22757 | 178-TyrTyrSerGlyArgLysAlaAla-185 |
| SEQ. ID. NO. 22758 | 245-LysIleGlyArgAspVal-250 |
| SEQ. ID. NO. 22759 | 257-ArgPheLysArgValLeuLysThrArgAla-266 |
| SEQ. ID. NO. 22760 | 390-PheLysGluGluGlyGlySer-396 |
| SEQ. ID. NO. 22761 | 448-ArgAlaTrpLysGluAsnGlyGln-455 |
| a690 | |
| AMPHI Regions - AMPHI | |
| SEQ. ID. NO. 22762 | 36-AlaSerSerThrAlaSerAla-42 |
| SEQ. ID. NO. 22763 | 57-SerAlaProAspAsnValLysGlnAlaGlu-66 |
| SEQ. ID. NO. 22764 | 68-ValProProSerAsnCysThrAspLeuHisProAlaThrGlyIleAspAspLeuMetGlnGlnIleAlaGluHisIle-93 |
| SEQ. ID. NO. 22765 | 116-GlyTyrAspAsnIleGlnArgLeu-123 |
| SEQ. ID. NO. 22766 | 151-ArgThrIleSerArgGlnAlaGlnAspAla-160 |
| SEQ. ID. NO. 22767 | 189-ProLysArgThrArgTyrPhe-195 |
| SEQ. ID. NO. 22768 | 213-GlyAsnPheGlnTyrIleGlyGlnLeuProGlyTyrLeuLys-226 |
| Antigenic Index - Jameson-Wolf | |
| SEQ. ID. NO. 22769 | 1-MetLysAsnLysThrSer-6 |
| SEQ. ID. NO. 22770 | 21-SerProSerLysGluAspLysThrLysGluAsnGlyAla-33 |
| SEQ. ID. NO. 22771 | 43-AlaSerSerSerAlaProGlnThrAspLeu-52 |
| SEQ. ID. NO. 22772 | 57-SerAlaProAspAsnValLysGlnAlaGluSerValProProSerAsnCysThrAspLeuHisProAlaThrGlyIleAspAspLeuMet-86 |
| SEQ. ID. NO. 22773 | 91-GluHisIleAspSerAspCys-97 |
| SEQ. ID. NO. 22774 | 104-HisGluLeuGluThrArgPhe-110 |
| SEQ. ID. NO. 22775 | 112-LeuProGlyGlyGlyTyrAspAsnIleGln-121 |
| SEQ. ID. NO. 22776 | 126-ProAspIleArgProGluAspProAspTyrHisGln-137 |
| SEQ. ID. NO. 22777 | 144-GluAspLeuArgTyrGlyLysArgThrIleSerArgGlnAlaGln-158 |
| SEQ. ID. NO. 22778 | 160-AlaLeuMetGluGlnGluArgArgLeuArgGlu-170 |
| SEQ. ID. NO. 22779 | 177-GlnGlySerGlnGluThrArgGlyGlnGlyGluGluProLysArgThrArgTyr-194 |
| SEQ. ID. NO. 22780 | 198-SerAlaThrProAlaTyrSerSerArgHisAsnAsnGlyLeuGlyGlyAsn-214 |
| SEQ. ID. NO. 22781 | 228-HisGlyGluMetLeuGluAsnGlnSerLeu-237 |
| SEQ. ID. NO. 22782 | 239-ArgLeuSerAsnArgGluArgAsnProAspLysProPheLeu-252 |
| SEQ. ID. NO. 22783 | 255-HisPheAspGluAsnGlyLysIleThr-263 |
| SEQ. ID. NO. 22784 | 267-ValTyrGluLysAsnIleTyrPheAsnProAsnLeuGlyArgArg-281 |
| Hydrophilic Regions - Hopp-Woods | |
| SEQ. ID. NO. 22785 | 1-MetLysAsnLysThr-5 |
| SEQ. ID. NO. 22786 | 21-SerProSerLysGluAspLysThrLysGluAsnGlyAla-33 |

TABLE 1-continued

| | |
|---|---|
| SEQ. ID. NO. 22787 | 46-SerAlaProGlnThrAspLeu-52 |
| SEQ. ID. NO. 22788 | 57-SerAlaProAspAsnValLysGlnAlaGluSerValPro-69 |
| SEQ. ID. NO. 22789 | 81-GlyIleAspAspLeuMet-86 |
| SEQ. ID. NO. 22790 | 91-GluHisIleAspSer-95 |
| SEQ. ID. NO. 22791 | 104-HisGluLeuGluThr-108 |
| SEQ. ID. NO. 22792 | 128-IleArgProGluAspProAspTyrHis-136 |
| SEQ. ID. NO. 22793 | 144-GluAspLeuArgTyrGlyLysArgThrIleSerArgGlnAlaGln-158 |
| SEQ. ID. NO. 22794 | 160-AlaLeuMetGluGlnGluArgArgLeuArgGlu-170 |
| SEQ. ID. NO. 22795 | 178-GlySerGlnGluThrArgGlyGlnGlyGluGluProLysArgThrArgTyr-194 |
| SEQ. ID. NO. 22796 | 203-TyrSerSerArgHisAsnAsn-209 |
| SEQ. ID. NO. 22797 | 228-HisGlyGluMetLeuGlu-233 |
| SEQ. ID. NO. 22798 | 240-LeuSerAsnArgGluArgAsnProAspLysProPhe-251 |
| SEQ. ID. NO. 22799 | 255-HisPheAspGluAsnGlyLysIleThr-263 |
| a691 | |
| AMPHI Regions - AMPHI | |
| SEQ. ID. NO. 22800 | 11-LysProAlaAlaSer-15 |
| SEQ. ID. NO. 22801 | 55-HisAsnGluLeuArgLysIleArgAla-63 |
| SEQ. ID. NO. 22802 | 108-ArgTyrLeuSerGly-112 |
| Antigenic Index - Jameson-Wolf | |
| SEQ. ID. NO. 22803 | 7-CysArgPheAlaLys-11 |
| SEQ. ID. NO. 22804 | 36-LeuAsnAspPheGlnProAsnCysAspIleArgArgLeuGlyLeuThrGlnGlyGlnHisAsnGluLeuArgLysIleArgAla-63 |
| SEQ. ID. NO. 22805 | 67-MetAlaGlyAspArgAlaArgLeuLysValMetHis-78 |
| SEQ. ID. NO. 22806 | 80-GluHisSerArgArgArgSerVal-87 |
| SEQ. ID. NO. 22807 | 91-IleSerSerAspValPheAsnArgAsnGluAlaArgAspTyrValGluSerArgTyrLeuSerGlyMetAspPheAlaValAspGluLeuGluIle-122 |
| SEQ. ID. NO. 22808 | 131-ThrProGlnGlnGlnGln-136 |
| SEQ. ID. NO. 22809 | 140-SerSerCysLeuLys-144 |
| Hydrophilic Regions - Hopp-Woods | |
| SEQ. ID. NO. 22810 | 43-CysAspIleArgArgLeuGly-49 |
| SEQ. ID. NO. 22811 | 54-GlnHisAsnGluLeuArgLysIleArgAla-63 |
| SEQ. ID. NO. 22812 | 67-MetAlaGlyAspArgAlaArgLeuLysValMetHis-78 |
| SEQ. ID. NO. 22813 | 80-GluHisSerArgArgArgSerVal-87 |
| SEQ. ID. NO. 22814 | 95-ValPheAsnArgAsnGluAlaArgAspTyrValGlu-106 |
| SEQ. ID. NO. 22815 | 115-PheAlaValAspGluLeuGluIle-122 |
| a692 | |
| AMPHI Regions - AMPHI | |
| SEQ. ID. NO. 22816 | 6-CysArgCysSerGluSerIleArgArgIleArgArgAsn-18 |
| SEQ. ID. NO. 22817 | 77-LeuGlyTyrValPheLysProLeuAlaValPheVal-88 |
| SEQ. ID. NO. 22818 | 106-GlnGlyPheGlyGlnLeuHis-112 |
| SEQ. ID. NO. 22819 | 132-ThrArgGlnLeuArgGlyPheLys-139 |
| SEQ. ID. NO. 22820 | 143-PheAspValPheGlnValPheGlyAsn-151 |
| SEQ. ID. NO. 22821 | 170-GlnPheValGluHisHis-175 |
| SEQ. ID. NO. 22822 | 177-AspAlaGlyGluValGlyArgValValGlyArgGlyTyrGlyAlaAlaValPheAspPhePheGlnArgPheGlnLeu-202 |
| SEQ. ID. NO. 22823 | 205-ValGlnSerGlnArgArgGlyArgHisLeuGluAspPheGlyAsp-219 |
| SEQ. ID. NO. 22824 | 254-ValGlyLysLeuAspGlnPheAspGlyVal-263 |
| SEQ. ID. NO. 22825 | 275-PheAspHisIleAlaGluValAlaAsp-283 |
| Antigenic Index - Jameson-Wolf | |
| SEQ. ID. NO. 22826 | 6-CysArgCysSerGluSerIleArgArgIleArgArgAsnGlyArgGluTrpArgIleLysGlyGlnLysCysArgLeuAsnThrAspThrValGln-37 |
| SEQ. ID. NO. 22827 | 89-GlyGlyPheAspGlyArgProValAspIleGlyLysAlaArgPheLeu-104 |
| SEQ. ID. NO. 22828 | 120-AlaValAspAspGlyLysIle-126 |
| SEQ. ID. NO. 22829 | 131-AlaThrArgGlnLeuArgGlyPheLysLeuAspAspPheAspVal-145 |
| SEQ. ID. NO. 22830 | 153-ArgPheGlyCysGlyGlnArgIleAspAla-162 |
| SEQ. ID. NO. 22831 | 174-HisHisGlnAspAlaGlyGluValGlyArgValValGlyArgGlyTyr-189 |
| SEQ. ID. NO. 22832 | 204-ArgValGlnSerGlnArgArgGlyArgHisLeuGluAspPheGlyAsp-219 |
| SEQ. ID. NO. 22833 | 236-GluAspValAspVal-240 |
| SEQ. ID. NO. 22834 | 255-GlyLysLeuAspGlnPheAspGly-262 |
| SEQ. ID. NO. 22835 | 279-AlaGluValAlaAspGlyArgAlaGluAspAspPhePhePhe-292 |
| SEQ. ID. NO. 22836 | 295-AlaValValGlyGlyGlyArgSerGlyCysGlyGlyArg-307 |
| SEQ. ID. NO. 22837 | 313-AlaAlaGlyGlyGluAspGluArgGluCysGlyGlyGlyLysGlyPheGluGlu-330 |
| Hydrophilic Regions - Hopp-Woods | |
| SEQ. ID. NO. 22838 | 7-ArgCysSerGluSerIleArgArgIleArgArgAsnGlyArgGluTrpArgIleLysGlyGlnLysCysArgLeuAsnThr-33 |
| SEQ. ID. NO. 22839 | 91-PheAspGlyArgProValAspIleGlyLys-100 |
| SEQ. ID. NO. 22840 | 120-AlaValAspAspGlyLysIle-126 |
| SEQ. ID. NO. 22841 | 131-AlaThrArgGlnLeuArgGlyPheLysLeuAspAspPheAsp-144 |
| SEQ. ID. NO. 22842 | 174-HisHisGlnAspAlaGlyGluValGlyArgValValGly-186 |
| SEQ. ID. NO. 22843 | 206-GlnSerGlnArgArgGlyArgHisLeuGluAspPheGlyAsp-219 |
| SEQ. ID. NO. 22844 | 236-GluAspValAspVal-240 |
| SEQ. ID. NO. 22845 | 255-GlyLysLeuAspGlnPheAsp-261 |
| SEQ. ID. NO. 22846 | 279-AlaGluValAlaAspGlyArgAlaGluAspAspPhePhePhe-292 |
| SEQ. ID. NO. 22847 | 299-GlyGlyArgSerGlyCysGly-305 |
| SEQ. ID. NO. 22848 | 315-GlyGlyGluAspGluArgGluCysGlyGly-324 |
| SEQ. ID. NO. 22849 | 326-LysGlyPheGluGlu-330 |
| a694 | |
| AMPHI Regions - AMPHI | |
| SEQ. ID. NO. 22850 | 82-ArgGlyArgAlaCysArg-87 |
| SEQ. ID. NO. 22851 | 116-CysArgHisPheAlaGln-121 |
| SEQ. ID. NO. 22852 | 123-ValAlaValGlyArgIleGly-129 |
| SEQ. ID. NO. 22853 | 140-PheCysGlnLeuPheAsp-145 |
| SEQ. ID. NO. 22854 | 156-AspIlePheLeuVal-160 |
| SEQ. ID. NO. 22855 | 162-IleAlaAspIleGlyGlu-167 |
| SEQ. ID. NO. 22856 | 184-ArgGlyLeuAlaAspIleGlyGluPheValGlyValSerAsp-197 |

TABLE 1-continued

| | |
|---|---|
| SEQ. ID. NO. 22857 | 251-HisGlnArgAlaSerArgIleLys-258 |
| SEQ. ID. NO. 22858 | 283-ArgAlaArgArgHisPheArgGlnValPheAsn-293 |
| SEQ. ID. NO. 22859 | 311-AspPheValAlaHisIle-316 |
| SEQ. ID. NO. 22860 | 340-AlaAlaArgIleGly-344 |
| Antigenic Index - Jameson-Wolf | |
| SEQ. ID. NO. 22861 | 3-SerAlaSerGlyThrArgGlnLysCysArgLeuLysProVal-16 |
| SEQ. ID. NO. 22862 | 23-ProLysHisSerThrProAlaSer-30 |
| SEQ. ID. NO. 22863 | 47-GlyGlnAspGluHisAsnAla-53 |
| SEQ. ID. NO. 22864 | 66-ProProSerAlaTyrGly-71 |
| SEQ. ID. NO. 22865 | 79-HisPheGlyArgGlyArgAlaCysArgTyr-88 |
| SEQ. ID. NO. 22866 | 110-ArgIleAspSerAlaArgCysArgHis-118 |
| SEQ. ID. NO. 22867 | 127-ArgIleGlyArgThrAspHisAsnHisAsp-136 |
| SEQ. ID. NO. 22868 | 144-PheAspGlyGlyLeuProValGlyArgArgIleAla-155 |
| SEQ. ID. NO. 22869 | 163-AlaAspIleGlyGluThrArgValGlnArgGlyAspAspValPhe-177 |
| SEQ. ID. NO. 22870 | 180-IleAspArgGluArgGlyLeuAlaAsp-188 |
| SEQ. ID. NO. 22871 | 202-HisIleSerAspArgPheAspGlnLysHisPheAlaArgArgLysLeuProHisArgSerPheAspLeu-224 |
| SEQ. ID. NO. 22872 | 228-LeuMetProAspHisAspAspPheThr-236 |
| SEQ. ID. NO. 22873 | 250-ArgHisGlnArgAlaSerArgIleLysHisAlaGluThrAlaLeu-264 |
| SEQ. ID. NO. 22874 | 268-LeuProHisArgLeuArgTyrAla-275 |
| SEQ. ID. NO. 22875 | 280-AsnGlnCysArgAlaArgArgHisPhe-288 |
| SEQ. ID. NO. 22876 | 291-ValPheAsnLysHisArgThr-297 |
| SEQ. ID. NO. 22877 | 316-IleAsnArgArgAlaGluLeu-322 |
| SEQ. ID. NO. 22878 | 326-ThrPheAspAsnThrAspCysPro-333 |
| SEQ. ID. NO. 22879 | 336-ThrSerAlaGluAlaAlaArgIleGlyLysAspAspGlyPhe-349 |
| SEQ. ID. NO. 22880 | 370-TyrGlyGlyArgCysCysProThrProProThrProHisArgArgArg-385 |
| Hydrophilic Regions - Hopp-Woods | |
| SEQ. ID. NO. 22881 | 5-SerGlyThrArgGlnLysCysArgLeuLysPro-15 |
| SEQ. ID. NO. 22882 | 47-GlyGlnAspGluHisAsnAla-53 |
| SEQ. ID. NO. 22883 | 81-GlyArgGlyArgAlaCysArg-87 |
| SEQ. ID. NO. 22884 | 110-ArgIleAspSerAlaArgCysArgHis-118 |
| SEQ. ID. NO. 22885 | 127-ArgIleGlyArgThrAspHisAsnHis-135 |
| SEQ. ID. NO. 22886 | 150-ValGlyArgArgIleAla-155 |
| SEQ. ID. NO. 22887 | 163-AlaAspIleGlyGluThrArgValGlnArgGlyAspAsp-175 |
| SEQ. ID. NO. 22888 | 180-IleAspArgGluArgGlyLeuAlaAsp-188 |
| SEQ. ID. NO. 22889 | 202-HisIleSerAspArgPheAspGlnLysHisPheAlaArgArgLysLeuProHisArgSerPheAspLeu-224 |
| SEQ. ID. NO. 22890 | 230-ProAspHisAspAsp-234 |
| SEQ. ID. NO. 22891 | 250-ArgHisGlnArgAlaSerArgIleLysHisAlaGluThrAlaLeu-264 |
| SEQ. ID. NO. 22892 | 280-AsnGlnCysArgAlaArgArgHisPhe-288 |
| SEQ. ID. NO. 22893 | 292-PheAsnLysHisArg-296 |
| SEQ. ID. NO. 22894 | 316-IleAsnArgArgAlaGluLeu-322 |
| SEQ. ID. NO. 22895 | 327-PheAspAsnThrAsp-331 |
| SEQ. ID. NO. 22896 | 338-AlaGluAlaAlaArgIleGlyLysAspAspGly-348 |
| SEQ. ID. NO. 22897 | 380-ThrProHisArgArgArg-385 |
| a695 | |
| AMPHI Regions - AMPHI | |
| SEQ. ID. NO. 22898 | 36-HisProGlnArgPheSerLysProAlaGluArgTyrAlaAspCysProHis-52 |
| SEQ. ID. NO. 22899 | 85-CysSerSerProValSerArgAsn-92 |
| SEQ. ID. NO. 22900 | 119-AspArgLeuAspTyr-123 |
| SEQ. ID. NO. 22901 | 129-ValArgLeuSerAsnGluValGlu-136 |
| SEQ. ID. NO. 22902 | 144-AlaLeuGluHisAla-148 |
| SEQ. ID. NO. 22903 | 158-ValGlnLysLeuAsp-162 |
| SEQ. ID. NO. 22904 | 183-ValGluThrAlaGlnAsnLeuTyrAsnGlnAlaLeuLysHisTyrLysSerGly-200 |
| SEQ. ID. NO. 22905 | 205-AlaAlaSerLeuLeuLysGlyAla-212 |
| SEQ. ID. NO. 22906 | 238-CysGluSerValIleGluIle-244 |
| SEQ. ID. NO. 22907 | 248-TyrAlaAsnArgPheLysAspSer-255 |
| SEQ. ID. NO. 22908 | 278-AlaArgAlaThrTrpArgSerLeuIleGlnThrTyrProGly-291 |
| Antigenic Index - Jameson-Wolf | |
| SEQ. ID. NO. 22909 | 5-CysProAlaArgArgHisHisCysHis-13 |
| SEQ. ID. NO. 22910 | 17-PheValGluArgLysGlyAspAlaArgSerGlyPhe-28 |
| SEQ. ID. NO. 22911 | 31-AlaAlaGlnArgArgHisProGlnArgPheSerLysProAlaGluArgTyrAlaAspCysProHisHisProAlaArgArgArgArgPheAspPro AlaSerGluLysIleMetLysThrLys-71 |
| SEQ. ID. NO. 22912 | 87-SerProValSerArgAsnIleGlnAspMetArgLeuGluProGlnAlaGluAlaGlySerSerAspAlaIleProTyr-112 |
| SEQ. ID. NO. 22913 | 117-LeuGlnAspArgLeuAspTyr-123 |
| SEQ. ID. NO. 22914 | 131-LeuSerAsnGluValGluThrLeuAsnGlyLysValLysAlaLeuGluHisAlaLysThrHisProSerSerArgAlaTyrValGlnLysLeuAsp AspArgLysLeuLysGlu-168 |
| SEQ. ID. NO. 22915 | 170-TyrLeuAsnThrGluGlyGlySerAla-178 |
| SEQ. ID. NO. 22916 | 193-AlaLeuLysHisTyrLysSerGlyArgPhe-202 |
| SEQ. ID. NO. 22917 | 210-LysGlyAlaAspGlyGlyAspGlyGlySerIleAlaGln-222 |
| SEQ. ID. NO. 22918 | 230-GlnSerArgAlaArgMetGlyAsnCys-238 |
| SEQ. ID. NO. 22919 | 244-IleGlyGlyArgTyrAlaAsnArgPheLysAspSerProThrAlaPro-259 |
| SEQ. ID. NO. 22920 | 266-GlyGluCysGlnTyr-270 |
| SEQ. ID. NO. 22921 | 272-LeuGlnGlnLysAspIleAla-278 |
| SEQ. ID. NO. 22922 | 289-TyrProGlySerProAlaAlaLysArgAlaAlaAlaAlaValArgLysArg-305 |
| Hydrophilic Regions - Hopp-Woods | |
| SEQ. ID. NO. 22923 | 5-CysProAlaArgArgHisHisCys-12 |
| SEQ. ID. NO. 22924 | 17-PheValGluArgLysGlyAspAlaArgSerGlyPhe-28 |
| SEQ. ID. NO. 22925 | 31-AlaAlaGlnArgArgHisProGlnArgPheSerLysProAlaGluArgTyrAlaAsp-49 |
| SEQ. ID. NO. 22926 | 51-ProHisHisProAlaArgArgArgArgPheAspProAlaSerGluLysIleMetLysThrLys71 |
| SEQ. ID. NO. 22927 | 88-ProValSerArgAsnIleGlnAspMetArgLeuGluProGlnAlaGluAlaGlySerSerAsp-108 |
| SEQ. ID. NO. 22928 | 117-LeuGlnAspArgLeuAspTyr-123 |

TABLE 1-continued

| | |
|---|---|
| SEQ. ID. NO. 22929 | 131-LeuSerAsnGluValGluThrLeuAsnGlyLysValLysAlaLeuGluHisAlaLysThrHisProSerSer-154 |
| SEQ. ID. NO. 22930 | 157-TyrValGlnLysLeuAspAspArgLysLeuLysGlu-168 |
| SEQ. ID. NO. 22931 | 195-LysHisTyrLysSerGlyArgPhe-202 |
| SEQ. ID. NO. 22932 | 210-LysGlyAlaAspGlyGlyAspGlyGlySerIleAlaGln-222 |
| SEQ. ID. NO. 22933 | 231-SerArgAlaArgMetGlyAsn-237 |
| SEQ. ID. NO. 22934 | 248-TyrAlaAsnArgPheLysAspSerProThrAlaPro-259 |
| SEQ. ID. NO. 22935 | 266-GlyGluCysGlnTyr-270 |
| SEQ. ID. NO. 22936 | 272-LeuGlnGlnLysAspIleAla-278 |
| SEQ. ID. NO. 22937 | 293-ProAlaAlaLysArgAlaAlaAlaAlaValArgLysArg-305 |
| a696 | |
| AMPHI Regions - AMPHI | |
| SEQ. ID. NO. 22938 | 18-PheGlyGlyIlePheHisPheValCysArgPheLeuSerArgValGlySerPheValGlnSerIlePheSerCysPheSer-44 |
| SEQ. ID. NO. 22939 | 65-IlePheAspLeuValPhe-70 |
| SEQ. ID. NO. 22940 | 94-GlyLeuAsnArgPheLeuAsnLeuLeuPheGlyPheLeuArg-107 |
| Antigenic Index - Jameson-Wolf | |
| SEQ. ID. NO. 22941 | 12-CysGlnGlyAsnLysLeu-17 |
| SEQ. ID. NO. 22942 | 73-PheAspGlyArgSerGlyArgLeuGlyGlyArgSerArgSer-86 |
| SEQ. ID. NO. 22943 | 108-ThrSerCysGlnGlySerArgHisHisCysGlyAsnGln-120 |
| Hydrophilic Regions - Hopp-Woods | |
| SEQ. ID. NO. 22944 | 73-PheAspGlyArgSerGlyArgLeuGlyGlyArgSerArgSer-86 |
| SEQ. ID. NO. 22945 | 109-SerCysGlnGlySerArgHisHisCys-117 |
| a700 | |
| AMPHI Regions - AMPHI | |
| SEQ. ID. NO. 22946 | 6-ThrLeuLeuSerValLeuIleProMetPheAlaGlyPhePheIleArgValProLys-24 |
| SEQ. ID. NO. 22947 | 27-LeuProAlaLeuAspLysValLeuSerValLeu-37 |
| SEQ. ID. NO. 22948 | 51-ArgValGluAspLeuGlySerArg-58 |
| SEQ. ID. NO. 22949 | 80-AlaLeuAlaValLeuGlyLysLeu-87 |
| SEQ. ID. NO. 22950 | 191-SerTrpValLysGlyLeu-196 |
| SEQ. ID. NO. 22951 | 204-TrpTyrSerLeuSerGlyLeuVal-211 |
| SEQ. ID. NO. 22952 | 216-TyrGlyAlaValTrpGlySerIleAlaLeuLeuAsnAspLeuAlaArgGluLeu-233 |
| SEQ. ID. NO. 22953 | 267-ArgGlyAlaGlyGlyLeu-272 |
| Antigenic Index - Jameson-Wolf | |
| SEQ. ID. NO. 22954 | 21-ArgValProLysProTyrLeu-27 |
| SEQ. ID. NO. 22955 | 50-SerArgValGluAspLeuGlySerArgLeuAspAspMetAla-63 |
| SEQ. ID. NO. 22956 | 90-TrpArgIleLysGlyLysGlyLysGlyVal-99 |
| SEQ. ID. NO. 22957 | 118-AlaSerGlyLysLeuMetArg-124 |
| SEQ. ID. NO. 22958 | 128-MetProSerGluAsnAlaGlyMet-135 |
| SEQ. ID. NO. 22959 | 149-LeuLysSerSerGlyValSerLeu-156 |
| SEQ. ID. NO. 22960 | 160-LeuValAsnArgArgGlyIleArgLeu-168 |
| SEQ. ID. NO. 22961 | 245-ArgPheProAspAla-249 |
| SEQ. ID. NO. 22962 | 268-GlyAlaGlyGlyLeuGluAla-274 |
| Hydrophilic Regions - Hopp-Woods | |
| SEQ. ID. NO. 22963 | 50-SerArgValGluAspLeuGlySerArgLeuAspAspMetAla-63 |
| SEQ. ID. NO. 22964 | 92-IleLysGlyLysGlyLysGlyVal-99 |
| SEQ. ID. NO. 22965 | 149-LeuLysSerSerGlyValSer-155 |
| SEQ. ID. NO. 22966 | 160-LeuValAsnArgArgGlyIleArg-167 |
| a701 | |
| AMPHI Regions - AMPHI | |
| SEQ. ID. NO. 22967 | 6-PheGlnValAlaGly-10 |
| SEQ. ID. NO. 22968 | 45-ProAsnSerPheAlaSerPheLysArgPheSerSerIle-57 |
| Antigenic Index - Jameson-Wolf | |
| SEQ. ID. NO. 22969 | 18-GlnSerThrProSerSerProThr-25 |
| SEQ. ID. NO. 22970 | 33-ThrSerProGluAlaGly-38 |
| SEQ. ID. NO. 22971 | 52LysArgPheSerSerIleSer-58 |
| SEQ. ID. NO. 22972 | 72-GlyLysAlaAspIleProThr-78 |
| SEQ. ID. NO. 22973 | 105-LysAlaSerLeuAsnAsnArgAlaThrSerSer-115 |
| SEQ. ID. NO. 22974 | 119-SerGlySerGlyThrArgLeu-125 |
| Hydrophilic Regions - Hopp-Woods | |
| SEQ. ID. NO. 22975 | 72-GlyLysAlaAspIle-76 |
| SEQ. ID. NO. 22976 | 107-SerLeuAsnAsnArgAlaThrSer-114 |
| a702 | |
| AMPHI Regions - AMPHI | |
| SEQ. ID. NO. 22977 | 51-CysSerGlyLeuValThrVal-57 |
| SEQ. ID. NO. 22978 | 118-LysIleSerArgGly-122 |
| Antigenic Index - Jameson-Wolf | |
| SEQ. ID. NO. 22979 | 1-MetProCysSerLysAlaSer-7 |
| SEQ. ID. NO. 22980 | 28-LeuAlaArgAspSerCysSerProGlyLeu-37 |
| SEQ. ID. NO. 22981 | 41-ThrAlaProAlaSerSer-46 |
| SEQ. ID. NO. 22982 | 68-LeuAlaIleArgArgMetAlaSerArgProThrGlyValArgArgValIleSer-85 |
| SEQ. ID. NO. 22983 | 88-GlyMetProProSerThrArgAlaTrpAspLysSerMetAla-101 |
| SEQ. ID. NO. 22984 | 118-LysIleSerArgGlyValSer-124 |
| SEQ. ID. NO. 22985 | 139-ArgTrpAspArgLeu-143 |
| Hydrophilic Regions - Hopp-Woods | |
| SEQ. ID. NO. 22986 | 29-AlaArgAspSerCysSer-34 |
| SEQ. ID. NO. 22987 | 69-AlaIleArgArgMetAlaSerArgProThrGlyValArgArgValIleSer-85 |

TABLE 1-continued

| | |
|---|---|
| SEQ. ID. NO. 22988 | 94-ArgAlaTrpAspLys-98 |
| SEQ. ID. NO. 22989 | 139-ArgTrpAspArgLeu-143 |
| a703 | |
| AMPHI Regions - AMPHI | |
| SEQ. ID. NO. 22990 | 21-GlnThrLeuAlaThrValAsnGly-28 |
| SEQ. ID. NO. 22991 | 64-GluValValAsnThrValValAlaGlnGlu-73 |
| SEQ. ID. NO. 22992 | 79-LeuAspArgSerAlaGlu-84 |
| SEQ. ID. NO. 22993 | 140-AlaAlaTyrAspAsnIleSerGlyPheTyrLysGly-151 |
| SEQ. ID. NO. 22994 | 181-PheAspAlaValLeu-185 |
| SEQ. ID. NO. 22995 | 204-ValProLeuLysAspLeuGluGlnGlyValProProLeuTyrGlnAlaIleLysAspLeuLysLys-225 |
| SEQ. ID. NO. 22996 | 252-ValProSerPheAsp-256 |
| SEQ. ID. NO. 22997 | 270-ArgIleAspArgAlaValGlyAlaLeu-278 |
| Antigenic Index - Jameson-Wolf | |
| SEQ. ID. NO. 22998 | 1-MetLysAlaLysIle-5 |
| SEQ. ID. NO. 22999 | 26-ValAsnGlyGlnLysIleAspSerSerVal-35 |
| SEQ. ID. NO. 23000 | 43-PheArgAlaGluAsnSerArgAlaGluAspThrProGlnLeuArg-57 |
| SEQ. ID. NO. 23001 | 72-GlnGluValLysArgLeuLysLeuAspArgSerAlaGluPheLysAsnAlaLeuAlaLysLeuArgAlaGluAlaLysLysSerGlyAsp AspLysLysProSerPheLysThr-109 |
| SEQ. ID. NO. 23002 | 129-LysThrGlnProValSerGluGlnGluValLysAlaAlaTyr-142 |
| SEQ. ID. NO. 23003 | 144-AsnIleSerGlyPheTyrLysGlyThrGlnGluValGlnLeu-157 |
| SEQ. ID. NO. 23004 | 160-IleLeuThrAspLysGluGluAsnAlaLysLysAlaValAlaAspLeuLysAlaLysLysGlyPhe-181 |
| SEQ. ID. NO. 23005 | 188-TyrSerLeuAsnAspArgThrLysGlnThrGlyAlaProValGly-202 |
| SEQ. ID. NO. 23006 | 207-LysAspLeuGluGlnGlyValProPro-215 |
| SEQ. ID. NO. 23007 | 221-LysAspLeuLysLysGlyGluPheThrAlaThrProLeuLysAsnGlyAspPhe-238 |
| SEQ. ID. NO. 23008 | 243-TyrValAsnAspSerArgGluValLysValProSerPheAspGluMetLysGly-260 |
| SEQ. ID. NO. 23009 | 266-LeuGlnAlaGluArgIleAspArgAlaVal-275 |
| SEQ. ID. NO. 23010 | 282-AlaAsnIleLysProAlaLys-288 |
| Hydrophilic Regions - Hopp-Woods | |
| SEQ. ID. NO. 23011 | 1-MetLysAlaLysIle-5 |
| SEQ. ID. NO. 23012 | 29-GlnLysIleAspSerSerVal-35 |
| SEQ. ID. NO. 23013 | 43-PheArgAlaGluAsnSerArgAlaGluAspThrProGlnLeuArg-57 |
| SEQ. ID. NO. 23014 | 72-GlnGluValLysArgLeuLysLeuAspArgSerAlaGluPheLysAsnAlaLeuAlaLysLeuArgAlaGluAlaLysLysSerGlyAspAsp LysLysProSerPhe-107 |
| SEQ. ID. NO. 23015 | 131-GlnProValSerGluGlnGluValLysAlaAlaTyr-142 |
| SEQ. ID. NO. 23016 | 160-IleLeuThrAspLysGluGluAsnAlaLysLysAlaValAlaAspLeuLysAlaLysLysGlyPhe-181 |
| SEQ. ID. NO. 23017 | 189-SerLeuAsnAspArgThrLysGlnThrGly-198 |
| SEQ. ID. NO. 23018 | 207-LysAspLeuGluGln-211 |
| SEQ. ID. NO. 23019 | 221-LysAspLeuLysLysGlyGluPhe-228 |
| SEQ. ID. NO. 23020 | 245-AsnAspSerArgGluValLysValProSerPheAspGluMetLysGly-260 |
| SEQ. ID. NO. 23021 | 266-LeuGlnAlaGluArgIleAspArgAlaVal-275 |
| SEQ. ID. NO. 23022 | 282-AlaAsnIleLysProAlaLys-288 |
| a704 | |
| AMPHI Regions - AMPHI | |
| SEQ. ID. NO. 23023 | 33-GlyCysGlnAlaValAlaGlnSerIleIleAspAlaGlyLeuGly-47 |
| SEQ. ID. NO. 23024 | 65-GlnGluIleLeuAspGlnIleArgLeuTyrAspLeuProGluValGlnSerAspPheValGluThrHis-87 |
| SEQ. ID. NO. 23025 | 184-LeuGlyMetMetGln-188 |
| SEQ. ID. NO. 23026 | 208-LeuGlnIleLeuHisTrpGlyGlyPheLeuMetValLeuPro-221 |
| SEQ. ID. NO. 23027 | 232-GlnGlyAlaLeuArgAspLeuLys-239 |
| SEQ. ID. NO. 23028 | 252-AlaIleIleMetThrPheIleAlaGlyValTyrSer-263 |
| SEQ. ID. NO. 23029 | 289-PheMetGluHisIleAlaArg-295 |
| SEQ. ID. NO. 23030 | 298-AlaGlyAspAlaAlaGluArgLeuValLysLeuIleProAlaPheCysHisHisMetProAspTyrProAspThrGlnGluThr-325 |
| SEQ. ID. NO. 23031 | 400-GlyGlyThrArgLeuSerHisIleValArgLeuLeuAspArgAlaLeuAla-416 |
| SEQ. ID. NO. 23032 | 423-GluLeuAlaGluGlnTyr-428 |
| SEQ. ID. NO. 23033 | 499-AlaIleGluThrLeuAlaGln-505 |
| SEQ. ID. NO. 23034 | 527-IleSerLeuLeuArg-531 |
| SEQ. ID. NO. 23035 | 576-LeuAsnArgIleGlyGluGlyValGly-584 |
| SEQ. ID. NO. 23036 | 639-LeuLysAspSerAlaAlaGluAlaValArgGlnLeuAla-651 |
| SEQ. ID. NO. 23037 | 670-GluThrAlaArgAlaLeuGlyVal-677 |
| SEQ. ID. NO. 23038 | 691-GluTyrValLysAlaLeuGlnLysGlu-699 |
| SEQ. ID. NO. 23039 | 744-AspLeuArgThrValAlaHisLeuLeuAsp-753 |
| SEQ. ID. NO. 23040 | 780-AlaValLeuGlyTyrValGlnProTrpIleAlaAla-791 |
| SEQ. ID. NO. 23041 | 799-LeuAlaValLeuGly-803 |
| SEQ. ID. NO. 23042 | 805-AlaLeuArgLeuHisLysArg-811 |
| Antigenic Index -Jameson-Wolf | |
| SEQ. ID. NO. 23043 | 1-MetLysLysThrCys-5 |
| SEQ. ID. NO. 23044 | 9-GlyLeuAspValProGluAsn-15 |
| SEQ. ID. NO. 23045 | 21-ArgTyrGluAsnGluAspArgGluThrCysCys-31 |
| SEQ. ID. NO. 23046 | 46-LeuGlySerTyrTyrLysGlnArgThrAlaAspAlaGlnLysThrGluLeuProProGlnGluIleLeuAsp-69 |
| SEQ. ID. NO. 23047 | 77-ProGluValGlnSerAspPheValGluThrHisGlyGlyThrArgGluAla-93 |
| SEQ. ID. NO. 23048 | 112-GlnLeuLeuArgThrAspGlyIleVal-120 |
| SEQ. ID. NO. 23049 | 124-LeuAsnTyrSerThrHisArgCys-131 |
| SEQ. ID. NO. 23050 | 133-ValValTrpAspAspGlyLysIleArgLeu-142 |
| SEQ. ID. NO. 23051 | 158-ProTyrAspAlaGlnLysIleGluAlaAlaAsnGlnLysGluArgLysGlnTyr-175 |
| SEQ. ID. NO. 23052 | 199-TyrGlyGlyAspIleGluProAspPhe-207 |
| SEQ. ID. NO. 23053 | 234-AlaLeuArgAspLeuLysAsnArgArgValGlyMetAspThrProIle-249 |
| SEQ. ID. NO. 23054 | 293-IleAlaArgArgLysAlaGlyAspAlaAlaGluArgLeuVal-306 |
| SEQ. ID. NO. 23055 | 316-MetProAspTyrProAspThrGlnGluThrCysGlu-327 |
| SEQ. ID. NO. 23056 | 329-AlaValValLysLeuLysAlaGlyAsp-337 |
| SEQ. ID. NO. 23057 | 342-LysProGlyGluThrIleProValAspGlyThrVal-353 |
| SEQ. ID. NO. 23058 | 356-GlySerSerAlaValAsnGluSer-363 |

TABLE 1-continued

| | |
|---|---|
| SEQ. ID. NO. 23059 | 365-LeuThrGlyGluSer-369 |
| SEQ. ID. NO. 23060 | 374-LysMetProSerGluLysValThrAla-382 |
| SEQ. ID. NO. 23061 | 393-IleArgThrAspArgThrGlyGlyGlyThrArg-403 |
| SEQ. ID. NO. 23062 | 414-AlaLeuAlaGlnLysProArgThrAlaGluLeuAlaGlu-426 |
| SEQ. ID. NO. 23063 | 486-ThrLeuAlaArgGluGlyIle-492 |
| SEQ. ID. NO. 23064 | 495-GlyGlyLysGlnAlaIle-500 |
| SEQ. ID. NO. 23065 | 510-IlePheAspLysThrGlyThrLeuThrGlnGlyLysProAlaValArgArg-526 |
| SEQ. ID. NO. 23066 | 528-SerLeuLeuArgGlyThrAspGluAlaPhe-537 |
| SEQ. ID. NO. 23067 | 545-LeuGluGlnGlnSerGluHisProLeu-553 |
| SEQ. ID. NO. 23068 | 560-CysArgIleSerAspGlySerValPro-568 |
| SEQ. ID. NO. 23069 | 570-IleAlaIleLysGlnArgLeuAsnArgIleGlyGluGlyVal-583 |
| SEQ. ID. NO. 23070 | 589-ValAsnGlyGluThrGln-594 |
| SEQ. ID. NO. 23071 | 605-AlaGluIleSerGlyLysGluProGlnThrGluGlyGlyGlySer-619 |
| SEQ. ID. NO. 23072 | 635-LeuGlnAspProLeuLysAspSerAlaAlaGluAlaValArg-648 |
| SEQ. ID. NO. 23073 | 650-LeuAlaGlyLysAsnLeu-655 |
| SEQ. ID. NO. 23074 | 659-IleLeuSerGlyAspArgGluThrAlaVal-668 |
| SEQ. ID. NO. 23075 | 684-AlaMetProGluAspLysLeuGluTyr-692 |
| SEQ. ID. NO. 23076 | 694-LysAlaLeuGlnLysGluGlyLysLys-702 |
| SEQ. ID. NO. 23077 | 707-GlyAspGlyIleAsnAspAla-713 |
| SEQ. ID. NO. 23078 | 725-AlaAlaGlyGlyThrAspIleAlaArgAspGlyAlaAsp-737 |
| SEQ. ID. NO. 23079 | 743-GluAspLeuArgThr-747 |
| SEQ. ID. NO. 23080 | 753-AspGlnAlaArgArgThrArgHisIleIle-762 |
| SEQ. ID. NO. 23081 | 807-ArgLeuHisLysArgGlyLysMetGlnSerGluLysMetProSerGluGln-823 |
| Hydrophilic Regions - Hopp-Woods | |
| SEQ. ID. NO. 23082 | 1-MetLysLysThrCys-5 |
| SEQ. ID. NO. 23083 | 21-ArgTyrGluAsnGluAspArgGluThrCys-30 |
| SEQ. ID. NO. 23084 | 50-TyrLysGlnArgThrAlaAspAlaGlnLysThrGluLeuProPro-64 |
| SEQ. ID. NO. 23085 | 77-ProGluValGlnSerAspPheValGlu-85 |
| SEQ. ID. NO. 23086 | 87-HisGlyGlyThrArgGluAla-93 |
| SEQ. ID. NO. 23087 | 112-GlnLeuLeuArgThrAspGlyIleVal-120 |
| SEQ. ID. NO. 23088 | 133-ValValTrpAspAspGlyLysIleArgLeu-142 |
| SEQ. ID. NO. 23089 | 160-AspAlaGlnLysIleGluAlaAlaAsnGlnLysGluArgLysGlnTyr-175 |
| SEQ. ID. NO. 23090 | 201-GlyAspIleGluProAspPhe-207 |
| SEQ. ID. NO. 23091 | 234-AlaLeuArgAspLeuLysAsnArgArgValGlyMet-245 |
| SEQ. ID. NO. 23092 | 293-IleAlaArgArgLysAlaGlyAspAlaAlaGluArgLeuVal-306 |
| SEQ. ID. NO. 23093 | 318-AspTyrProAspThrGlnGluThrCysGlu-327 |
| SEQ. ID. NO. 23094 | 329-AlaValValLysLeuLysAlaGlyAsp-337 |
| SEQ. ID. NO. 23095 | 375-MetProSerGluLysValThr-381 |
| SEQ. ID. NO. 23096 | 393-IleArgThrAspArgThrGlyGlyGlyThrArg-403 |
| SEQ. ID. NO. 23097 | 414-AlaLeuAlaGlnLysProArgThrAlaGluLeuAlaGlu-426 |
| SEQ. ID. NO. 23098 | 486-ThrLeuAlaArgGluGlyIle-492 |
| SEQ. ID. NO. 23099 | 518-ThrGlnGlyLysProAlaValArgArg-526 |
| SEQ. ID. NO. 23100 | 531-ArgGlyThrAspGlu-535 |
| SEQ. ID. NO. 23101 | 545-LeuGluGlnGlnSerGluHisProLeu-553 |
| SEQ. ID. NO. 23102 | 561-ArgIleSerAspGlySerVal-567 |
| SEQ. ID. NO. 23103 | 570-IleAlaIleLysGlnArgLeuAsnArgIleGlyGlu-581 |
| SEQ. ID. NO. 23104 | 607-IleSerGlyLysGluProGlnThrGluGlyGlyGly-618 |
| SEQ. ID. NO. 23105 | 637-AspProLeuLysAspSerAlaAlaGluAlaValArg-648 |
| SEQ. ID. NO. 23106 | 661-SerGlyAspArgGluThrAlaVal-668 |
| SEQ. ID. NO. 23107 | 684-AlaMetProGluAspLysLeuGluTyr-692 |
| SEQ. ID. NO. 23108 | 694-LysAlaLeuGlnLysGluGlyLysLys-702 |
| SEQ. ID. NO. 23109 | 730-AspIleAlaArgAspGlyAlaAsp-737 |
| SEQ. ID. NO. 23110 | 743-GluAspLeuArgThr-747 |
| SEQ. ID. NO. 23111 | 753-AspGlnAlaArgArgThrArgHisIleIle-762 |
| SEQ. ID. NO. 23112 | 807-ArgLeuHisLysArgGlyLysMetGlnSerGluLysMetProSerGluGln-823 |
| a705 | |
| AMPHI Regions - AMPHI | |
| SEQ. ID. NO. 23113 | 67-LysIleLeuLeuLysLeu-72 |
| SEQ. ID. NO. 23114 | 104-AspProIleProAla-108 |
| SEQ. ID. NO. 23115 | 147-TyrMetGlnThrPheArgArgIleValAlaProGln-158 |
| SEQ. ID. NO. 23116 | 169-AsnGluPheIleGlyLeuPheLysAsn-177 |
| SEQ. ID. NO. 23117 | 183-ValValThrValThrGluLeuPheArgValAlaGln-194 |
| SEQ. ID. NO. 23118 | 196-ThrAlaAsnArgThr-200 |
| Antigenic Index - Jameson-Wolf | |
| SEQ. ID. NO. 23119 | 13-ThrGluThrArgAlaAspMet-19 |
| SEQ. ID. NO. 23120 | 132-ValProLysGlyGlnTrpGlu-138 |
| SEQ. ID. NO. 23121 | 165-ProProLeuSerAsnGlu-170 |
| SEQ. ID. NO. 23122 | 193-AlaGlnGluThrAlaAsnArgThrTyrAsp-202 |
| SEQ. ID. NO. 23123 | 226-AlaArgLeuGluLysArgPheAspArgTyrValAla-237 |
| Hydrophilic Regions - Hopp-Woods | |
| SEQ. ID. NO. 23124 | 13-ThrGluThrArgAlaAspMet-19 |
| SEQ. ID. NO. 23125 | 193-AlaGlnGluThrAlaAsnArgThr-200 |
| SEQ. ID. NO. 23126 | 226-AlaArgLeuGluLysArgPheAspArgTyrValAla-237 |
| a706 | |
| AMPHI Regions - AMPHI | |
| SEQ. ID. NO. 23127 | 9-LeuValSerArgTrpLeuAsnSerTyr-17 |
| SEQ. ID. NO. 23128 | 24-ArgLeuIleHisAlaValArg-30 |
| SEQ. ID. NO. 23129 | 70-IleTyrSerLysAlaValGluArgMetLeuGlyThrValIleGly-84 |
| SEQ. ID. NO. 23130 | 111-ThrAlaSerAlaLeuAlaGlyTrpAlaAla-120 |
| SEQ. ID. NO. 23131 | 153-ArgAlaMetAsnValLeu-158 |

TABLE 1-continued

| | |
|---|---|
| SEQ. ID. NO. 23132 | 183-LeuAlaAspAsnLeuThrAspCysSerLysMetIleAlaGluIleSerAsnGlyArg-201 |
| SEQ. ID. NO. 23133 | 204-ThrArgGluArgLeuGluGluAsn-211 |
| SEQ. ID. NO. 23134 | 243-MetGluAlaMetGlnHisAlaHisArgLysIleVal-254 |
| SEQ. ID. NO. 23135 | 318-AlaLeuAlaGluHisLeuHis-324 |
| Antigenic Index - Jameson-Wolf | |
| SEQ. ID. NO. 23136 | 1-MetAsnThrSerGlnArgAsnArgLeu-9 |
| SEQ. ID. NO. 23137 | 11-SerArgTrpLeuAsnSerTyrGluArgTyrArgTyrArgArg-24 |
| SEQ. ID. NO. 23138 | 73-LysAlaValGluArgMetLeu-79 |
| SEQ. ID. NO. 23139 | 97-HisTyrPheHisGlyAsnLeu-103 |
| SEQ. ID. NO. 23140 | 122-GlyLysAsnGlyTyrVal-127 |
| SEQ. ID. NO. 23141 | 140-GlyAspAsnGlySerGluTrpPheAsp-148 |
| SEQ. ID. NO. 23142 | 186-AsnLeuThrAspCysSerLysMetIleAlaGluIleSerAsnGlyArgArgMetThrArgGluArgLeuGluGluAsnMetAlaLysMetArgGlnIle Asn-219 |
| SEQ. ID. NO. 23143 | 221-ArgMetValLysSerArgSerHisLeuAlaAlaThrSerGlyGluSerArgIleSer-239 |
| SEQ. ID. NO. 23144 | 249-AlaHisArgLysIleValAsn-255 |
| SEQ. ID. NO. 23145 | 266-LysLeuGlnSerProLysLeuAsnGlySerGluIleArgLeuLeuAsp-281 |
| SEQ. ID. NO. 23146 | 300-GlyArgHisAlaArgArgIleArgIleAspThrAlaIleAsnProGluLeuGluAlaLeuAla-320 |
| SEQ. ID. NO. 23147 | 334-SerThrAsnMetArgGlnGluIle-341 |
| SEQ. ID. NO. 23148 | 349-GlnArgThrArgArgLysTrpLeuAspAlaHisGluArgGlnHisLeu-364 |
| SEQ. ID. NO. 23149 | 367-SerLeuLeuGluThrArgGluHisSer-375 |
| Hydrophilic Regions - Hopp-Woods | |
| SEQ. ID. NO. 23150 | 3-ThrSerGlnArgAsnArgLeu-9 |
| SEQ. ID. NO. 23151 | 17-TyrGluArgTyrArgTyrArgArg-24 |
| SEQ. ID. NO. 23152 | 73-LysAlaValGluArgMetLeu-79 |
| SEQ. ID. NO. 23153 | 142-AsnGlySerGluTrpPhe-147 |
| SEQ. ID. NO. 23154 | 186-AsnLeuThrAspCysSerLysMetIleAla-195 |
| SEQ. ID. NO. 23155 | 198-SerAsnGlyArgArgMetThrArgGluArgLeuGluGluAsnMetAlaLysMetArgGlnIleAsn-219 |
| SEQ. ID. NO. 23156 | 221-ArgMetValLysSerArgSerHis-228 |
| SEQ. ID. NO. 23157 | 232-ThrSerGlyGluSerArgIle-238 |
| SEQ. ID. NO. 23158 | 249-AlaHisArgLysIleValAsn-255 |
| SEQ. ID. NO. 23159 | 266-LysLeuGlnSerProLysLeuAsnGlySerGluIleArgLeuLeuAsp-281 |
| SEQ. ID. NO. 23160 | 301-ArgHisAlaArgArgIleArgIle-308 |
| SEQ. ID. NO. 23161 | 314-ProGluLeuGluAlaLeuAla-320 |
| SEQ. ID. NO. 23162 | 336-AsnMetArgGlnGluIle-341 |
| SEQ. ID. NO. 23163 | 349-GlnArgThrArgArgLysTrpLeuAspAlaHisGluArgGlnHisLeu-364 |
| SEQ. ID. NO. 23164 | 367-SerLeuLeuGluThrArgGluHisSer-375 |
| a707 | |
| AMPHI Regions - AMPHI | |
| SEQ. ID. NO. 23165 | 16-AsnLeuSerArgLeuGlnLysAla-23 |
| SEQ. ID. NO. 23166 | 98-GluGlnGlyLeuGluAsnLeuArgArgLeuProSerVal-110 |
| SEQ. ID. NO. 23167 | 147-GlyGlyLysThrThrGlyLysTyr-154 |
| SEQ. ID. NO. 23168 | 222-ArgTyrHisGluAlaThrGlu-228 |
| SEQ. ID. NO. 23169 | 267-ThrArgGlnThrTyrLysTyrIleAspAsp-276 |
| SEQ. ID. NO. 23170 | 467-HisLysProLysGlyPheGlnThrThrAsnThr-477 |
| Antigenic Index - Jameson-Wolf | |
| SEQ. ID. NO. 23171 | 1-XxxLysGluThrAlaPhe-6 |
| SEQ. ID. NO. 23172 | 13-GlySerAsnAsnLeuSerArgLeuGlnLysAlaAla-24 |
| SEQ. ID. NO. 23173 | 42-ProGlnAsnMetAspSerGlyIleLeu-50 |
| SEQ. ID. NO. 23174 | 53-ArgValSerAlaGlyGluIleGlyAspIleArgTyrGluGluLysArgAspXxxLysSerAlaGluGlySerIle-77 |
| SEQ. ID. NO. 23175 | 79-AlaPheAsnAsnLysXxxProLeuTyrArgAsnLysIleLeuAsn-93 |
| SEQ. ID. NO. 23176 | 95-ArgAspValGluGlnGlyLeuGluAsnLeuArgArgLeuProSerValLysThrAspIle-114 |
| SEQ. ID. NO. 23177 | 117-IleProSerGluGluGluGlyLysSerAspLeu-127 |
| SEQ. ID. NO. 23178 | 130-LysTrpGlnGlnAsnLysProIleArg-138 |
| SEQ. ID. NO. 23179 | 141-IleGlyIleAspAspAlaGlyGlyLysThrThrGlyLysTyrGlnGly-156 |
| SEQ. ID. NO. 23180 | 162-XxxAspAsnProLeuGlyLeuSer-169 |
| SEQ. ID. NO. 23181 | 180-LeuValHisLysThrAspLeuThrXxxAlaThrGlyThrGluThrGluSerGlySerArgSerTyr-201 |
| SEQ. ID. NO. 23182 | 216-PheAsnHisAsnGlyHisArgTyrHisGluAlaThrGluGlyTyrSerValAsnTyrAspTyrAsnGlyLysGlnTyrGln-242 |
| SEQ. ID. NO. 23183 | 269-GlnThrTyrLysTyrIleAspAspAlaGluIleGluValGlnArgArgArgSerAlaGlyTrpGluAlaGluLeuArgHis-295 |
| SEQ. ID. NO. 23184 | 303-GlnLeuAspGlyLysLeuSerTyrLysArgGlyThrGlyMetArgGlnSerMetProAlaProGluGluAsnGlyGlyGlyThrIleProXxxXxxSer ArgMetLysIle-339 |
| SEQ. ID. NO. 23185 | 366-GlnTrpAsnLysThrPro-371 |
| SEQ. ID. NO. 23186 | 374-AlaGlnAspLysLeuSerIleGlySerArgTyrThrValArgGlyPheAspGlyGluGlnSerLeuPheGlyGluArgGlyPheTyrTrpGlnAsnThr-406 |
| SEQ. ID. NO. 23187 | 421-AlaAspTyrGlyArgValSerGlyGluSerAla-431 |
| SEQ. ID. NO. 23188 | 434-ValSerGlyLysGln-438 |
| SEQ. ID. NO. 23189 | 446-PheArgGlyGlyHisLysValGlyGly-454 |
| SEQ. ID. NO. 23190 | 464-LysProLeuHisLysProLysGlyPheGln-473 |
| Hydrophilic Regions - Hopp-Woods | |
| SEQ. ID. NO. 23191 | 1-XxxLysGluThrAlaPhe-6 |
| SEQ. ID. NO. 23192 | 16-AsnLeuSerArgLeuGlnLysAlaAla-24 |
| SEQ. ID. NO. 23193 | 58-GluIleGlyAspIleArgTyrGluGluLysArgAspXxxLysSerAlaGluGlySer-76 |
| SEQ. ID. NO. 23194 | 95-ArgAspValGluGlnGlyLeuGluAsnLeuArgArgLeuProSerValLysThrAspIle-114 |
| SEQ. ID. NO. 23195 | 118-ProSerGluGluGluGlyLysSerAspLeu-127 |
| SEQ. ID. NO. 23196 | 141-IleGlyIleAspAspAlaGlyGlyLysThrThrGlyLysTyr-154 |
| SEQ. ID. NO. 23197 | 180-LeuValHisLysThrAspLeu-186 |
| SEQ. ID. NO. 23198 | 190-ThrGlyThrGluThrGluSerGlySerArgSer-200 |
| SEQ. ID. NO. 23199 | 222-ArgTyrHisGluAlaThrGlu-228 |
| SEQ. ID. NO. 23200 | 273-TyrIleAspAspAlaGluIleGluValGlnArgArgArgSerAlaGlyTrp-289 |
| SEQ. ID. NO. 23201 | 291-AlaGluLeuArgHis-295 |
| SEQ. ID. NO. 23202 | 306-GlyLysLeuSerTyrLysArgGlyThrGlyMetArgGlnSerMetProAlaProGluGluAsnGlyGly-328 |

TABLE 1-continued

| | |
|---|---|
| SEQ. ID. NO. 23203 | 333-XxxXxxSerArgMetLysIle-339 |
| SEQ. ID. NO. 23204 | 374-AlaGlnAspLysLeuSerIle-380 |
| SEQ. ID. NO. 23205 | 388-GlyPheAspGlyGluGln-393 |
| SEQ. ID. NO. 23206 | 422-AspTyrGlyArgValSerGlyGluSer-430 |
| SEQ. ID. NO. 23207 | 465-ProLeuHisLysProLysGly-471 |
| a708 | |
| AMPHI Regions - AMPHI | |
| SEQ. ID. NO. 23208 | 26-ProSerArgAlaGluLysAlaAsnGlnValSerAsnIle-38 |
| SEQ. ID. NO. 23209 | 57-AlaSerIleGluAspAlaLeuLysSerAspPro-67 |
| SEQ. ID. NO. 23210 | 79-IleTyrGlnTyrLeuLys-84 |
| SEQ. ID. NO. 23211 | 89-AlaGlnGluSerPhe-93 |
| SEQ. ID. NO. 23212 | 119-AsnArgProAlaGluSerMetAla-126 |
| SEQ. ID. NO. 23213 | 128-PheAspLysAlaLeu-132 |
| SEQ. ID. NO. 23214 | 142-IleAlaAsnLeuAsnLys-147 |
| SEQ. ID. NO. 23215 | 176-ProAlaPheLysGluLeuAlaArg-183 |
| SEQ. ID. NO. 23216 | 221-LysAlaLeuGlyAsnAlaGln-227 |
| Antigenic Index - Jameson-Wolf | |
| SEQ. ID. NO. 23217 | 2-ProPheLysProSerLysArgIleSer-10 |
| SEQ. ID. NO. 23218 | 19-AlaCysSerThrSerTyrArgProSerArgAlaGluLysAlaAsnGln-34 |
| SEQ. ID. NO. 23219 | 46-TyrMetArgGlyGlnAspTyrArgGlnXxxThrAlaSerIleGluAspAlaLeuLysSerAspProLysAsnGlu-70 |
| SEQ. ID. NO. 23220 | 84-LysValAsnAspLysAlaGlnGluSerPheArg-94 |
| SEQ. ID. NO. 23221 | 97-LeuSerIleLysProAspSerAlaGluIleAsnAsnAsnTyr-110 |
| SEQ. ID. NO. 23222 | 115-CysGlyArgLeuAsnArgProAlaGlu-123 |
| SEQ. ID. NO. 23223 | 131-AlaLeuAlaAspProThrTyrProXxx-139 |
| SEQ. ID. NO. 23224 | 146-AsnLysGlyIleCysSerAlaLysGlnGlyGln-156 |
| SEQ. ID. NO. 23225 | 176-ProAlaPheLysGluLeuAlaArgThrLysMet-186 |
| SEQ. ID. NO. 23226 | 191-LeuGlyAspAlaAspTyrTyrPheLysLysTyrGlnSerArgValGluValLeuGlnAlaAspAspLeu-213 |
| SEQ. ID. NO. 23227 | 240-PheProTyrSerGluGluLeuGln-247 |
| Hydrophilic Regions - Hopp-Woods | |
| SEQ. ID. NO. 23228 | 4-LysProSerLysArgIle-9 |
| SEQ. ID. NO. 23229 | 24-TyrArgProSerArgAlaGluLysAlaAsnGln-34 |
| SEQ. ID. NO. 23230 | 46-TyrMetArgGlyGlnAspTyrArgGlnXxxThrAlaSerIleGluAspAlaLeuLysSerAspProLysAsnGlu-70 |
| SEQ. ID. NO. 23231 | 84-LysValAsnAspLysAlaGlnGluSerPheArg-94 |
| SEQ. ID. NO. 23232 | 99-IleLysProAspSerAlaGluIle-106 |
| SEQ. ID. NO. 23233 | 117-ArgLeuAsnArgProAlaGlu-123 |
| SEQ. ID. NO. 23234 | 149-IleCysSerAlaLysGlnGly-155 |
| SEQ. ID. NO. 23235 | 177-AlaPheLysGluLeuAlaArgThrLysMet-186 |
| SEQ. ID. NO. 23236 | 201-TyrGlnSerArgValGluValLeuGlnAlaAspAspLeu-213 |
| a709 | |
| AMPHI Regions - AMPHI | |
| SEQ. ID. NO. 23237 | 6-SerLeuLeuAspMetProArgGlyGlu-14 |
| SEQ. ID. NO. 23238 | 18-ValValValAlaLeuIleAlaAlaMetGly-27 |
| SEQ. ID. NO. 23239 | 37-ProHisMetSerIleIleAlaAlaIleValValLeu-48 |
| SEQ. ID. NO. 23240 | 54-AlaArgGlyLeuLysTyrAsn-60 |
| SEQ. ID. NO. 23241 | 64-GlnGlyMetIleGlyAlaLeuAsnGlnGly-73 |
| SEQ. ID. NO. 23242 | 115-SerAlaPheAlaLeuCysSerVal-122 |
| SEQ. ID. NO. 23243 | 130-SerLeuThrThrCysAlaThrVal-137 |
| SEQ. ID. NO. 23244 | 168-LysMetSerProLeuSerAspThrXxx-176 |
| SEQ. ID. NO. 23245 | 185-IleAspLeuPheGluHisIleLysAsnMetMetTyrThrThr-198 |
| SEQ. ID. NO. 23246 | 209-MetLeuXxxLeuLeuPro-214 |
| SEQ. ID. NO. 23247 | 221-LeuAsnSerValGluSerPheArg-228 |
| SEQ. ID. NO. 23248 | 234-ThrGlyLeuValHisCysTyrSerLeuIleProPheAlaLeuLeuValValLeu-251 |
| SEQ. ID. NO. 23249 | 261-AlaMetLeuPheThrValIleAlaAlaValAlaValThrTyr-274 |
| SEQ. ID. NO. 23250 | 278-ThrProAspLeuArgGlnLeuGlyAlaTrpPhe-288 |
| SEQ. ID. NO. 23251 | 299-XxxXxxAspIleAlaLysLeuIleSerArgGlyGly-310 |
| SEQ. ID. NO. 23252 | 334-LeuGlyAlaIleProSerLeuLeuAspAlaValArgSerPheLeuThr-349 |
| SEQ. ID. NO. 23253 | 382-ThrPheLysProVal-386 |
| SEQ. ID. NO. 23254 | 395-ArgAsnLeuSerArgThrLeuGluAspAlaGlyThrValIleAsnProLeuValProTrpSerValCysGlyValPheIleXxxHis-423 |
| Antigenic Index - Jameson-Wolf | |
| SEQ. ID. NO. 23255 | 9-AspMetProArgGlyGluAla-15 |
| SEQ. ID. NO. 23256 | 55-ArgGlyLeuLysTyrAsnAspMetGln-63 |
| SEQ. ID. NO. 23257 | 164-XxxXxxGlyXxxLysMetSerProLeuSerAspThrXxxGlyXxxSer-179 |
| SEQ. ID. NO. 23258 | 222-AsnSerValGluSerPheArgSerGlnLeuGlu-232 |
| SEQ. ID. NO. 23259 | 277-SerThrProAspLeuArgGln-283 |
| SEQ. ID. NO. 23260 | 290-GlyGlyTyrLysLeuGluGlyGluAlaXxxXxxAspIleAlaLysLeuIleSerArgGlyGlyLeuGlu-312 |
| SEQ. ID. NO. 23261 | 349-ThrAsnAlaGlyArgXxxThr-355 |
| SEQ. ID. NO. 23262 | 378-LeuSerGlyGluThrPheLysProValTyrAspLysLeuGlyLeuHisSerArgAsnLeuSerArgThrLeuGluAspAlaGlyThr-406 |
| Hydrophilic Regions - Hopp-Woods | |
| SEQ. ID. NO. 23263 | 9-AspMetProArgGlyGluAla-15 |
| SEQ. ID. NO. 23264 | 57-LeuLysTyrAsnAspMetGln-63 |
| SEQ. ID. NO. 23265 | 165-XxxGlyXxxLysMetSerProLeuSerAspThrXxxGly-177 |
| SEQ. ID. NO. 23266 | 225-GluSerPheArgSerGlnLeuGlu-232 |

TABLE 1-continued

| | |
|---|---|
| SEQ. ID. NO. 23267 | 279-ProAspLeuArgGln-283 |
| SEQ. ID. NO. 23268 | 293-LysLeuGluGlyGluAlaXxxXxxAspIleAlaLysLeuIleSer-307 |
| SEQ. ID. NO. 23269 | 396-AsnLeuSerArgThrLeuGluAspAlaGly-405 |
| a710 | |
| AMPHI Regions - AMPHI | |
| SEQ. ID. NO. 23270 | 6-LysIleArgLeuMetArgGluLeuAsnLysTrpSerGln-18 |
| SEQ. ID. NO. 23271 | 31-GlyTyrAlaLysIleGlu-36 |
| SEQ. ID. NO. 23272 | 45-ProArgLeuGluGlnLeuAlaGlnIlePheLysIleAspMetTrpAspLeuLeuLys-63 |
| SEQ. ID. NO. 23273 | 105-CysLysGluMetLeuGlu-110 |
| Antigenic Index - Jameson-Wolf | |
| SEQ. ID. NO. 23274 | 1-MetGluThrHisGluLysIleArgLeuMetArgGluLeuAsnLysTrpSerGlnGluAspMetAlaGluLysLeuAla-26 |
| SEQ. ID. NO. 23275 | 33-AlaLysIleGluArgGlyGluThrGlnLeuAsnIleProArgLeuGluGln-49 |
| SEQ. ID. NO. 23276 | 62-LeuLysSerGlyGlyGlyGly-68 |
| SEQ. ID. NO. 23277 | 74-AsnAspValAspThrAsnSerGlyGlu-82 |
| SEQ. ID. NO. 23278 | 88-AlaGlnAspAlaSerGlyLys-94 |
| SEQ. ID. NO. 23279 | 100-MetGluLeuLysHisCysLysGluMetLeuGluHisLysAspLysGluIleGluLeuLeuArgLysLeuThrGlu-124 |
| Hydrophilic Regions - Hopp-Woods | |
| SEQ. ID. NO. 23280 | 1-MetGluThrHisGluLysIleArgLeuMetArgGluLeuAsnLysTrpSerGlnGluAspMetAlaGluLysLeuAla-26 |
| SEQ. ID. NO. 23281 | 33-AlaLysIleGluArgGlyGluThr-40 |
| SEQ. ID. NO. 23282 | 45-ProArgLeuGluGln-49 |
| SEQ. ID. NO. 23283 | 74-AsnAspValAspThrAsnSerGly-81 |
| SEQ. ID. NO. 23284 | 100-MetGluLeuLysHisCysLysGluMetLeuGluHisLysAspLysGluIleGluLeuLeuArgLysLeuThrGlu-124 |
| a711 | |
| AMPHI Regions - AMPHI | |
| SEQ. ID. NO. 23285 | 28-AlaGluSerTyrArgAsnLeuThrAlaSerGluIleAlaLysValTyrThrIleAlaArgMetThr 49 * |
| SEQ. ID. NO. 23286 | AspLeuAspMetLeuAsnAspIleLys-58 |
| SEQ. ID. NO. 23287 | 67-SerGlyGlnSerPheAspAspTrpArgLysGlyIleLeu-79 |
| SEQ. ID. NO. 23288 | 95-GlyLysAspIleIleAspProAlaThrGlyGluValPheGlySerProArgArgLeuGluThrIleTyrArgThrAsnMet-121 |
| SEQ. ID. NO. 23289 | 128-GlyGlnTyrGlnGlyTyrMet-134 |
| SEQ. ID. NO. 23290 | 158-SerAlaIleAspGly-162 |
| SEQ. ID. NO. 23291 | 195-ValGluArgGlnGly-199 |
| SEQ. ID. NO. 23292 | 207-SerAspAsnLeuValGluThrHis-214 |
| SEQ. ID. NO. 23293 | 258-LysTyrAspArgAlaLeuAlaHisGlnPheAla-268 |
| SEQ. ID. NO. 23294 | 281-PheLysGlnLeuGluLysGluPheTyr-289 |
| SEQ. ID. NO. 23295 | 329-GlnGluLeuAlaGlyMetThr-335 |
| SEQ. ID. NO. 23296 | 352-SerArgGluGlyGlnAsnPhe-358 |
| SEQ. ID. NO. 23297 | 360-AspSerTyrTyrAlaPheLeuProAspMetLeuGlnAsnProGlu-374 |
| SEQ. ID. NO. 23298 | 395-TrpAlaValLeuLysTyrIleLysGluValAspGluIle-407 |
| SEQ. ID. NO. 23299 | 413-ArgIleSerAsnAspLysGluIleAlaLys-422 |
| Antigenic Index - Jameson-Wolf | |
| SEQ. ID. NO. 23300 | 11-SerLeuProProLysLysAlaIleGlu-19 |
| SEQ. ID. NO. 23301 | 21-LeuGluSerLysLysValThrAlaGluSerTyrArgAsnLeuThr-35 |
| SEQ. ID. NO. 23302 | 55-AsnAspIleLysThrSerMet-61 |
| SEQ. ID. NO. 23303 | 63-GluSerAlaLysSerGlyGlnSerPheAspAspTrpArgLysGlyIle-78 |
| SEQ. ID. NO. 23304 | 82-LeuSerAsnLysGlyTrpLeuHisProAsnGlyHisAsnGlyLysAspIleIleAspProAlaThrGlyGluValPheGlySerProArgArgLeuGluThr IleTyrArgThrAsnMet-121 |
| SEQ. ID. NO. 23305 | 126-AsnAlaGlyGlnTyrGlnGly-132 |
| SEQ. ID. NO. 23306 | 135-AlaAsnIleAspAlaArgProTyrTrp-143 |
| SEQ. ID. NO. 23307 | 147-AlaValGlyAspSerArgThrArgProAlaHisSerAla-159 |
| SEQ. ID. NO. 23308 | 165-TyrArgTyrAspAspProPheTrp-172 |
| SEQ. ID. NO. 23309 | 177-ProProAsnGlyTyrAsnCysArgCysSer-186 |
| SEQ. ID. NO. 23310 | 190-LeuSerGluArgAspValGluArgGlnGlyArgIleValGlyGlnSerThrSerAspAsnLeuValGlu-212 |
| SEQ. ID. NO. 23311 | 215-LysIleTyrAsnLysLysGlyAspThr-223 |
| SEQ. ID. NO. 23312 | 229-TyrLysAlaProAspGlySerLeuTyrThrThrAspArgGlyPheAspTyrAsnAlaGlyArgMetAsnTyrArgProAspLeuAspLysTyrAsp ArgAlaLeu-263 |
| SEQ. ID. NO. 23313 | 268-AlaLysAlaGluMetGlyGlyAlaAspPheLysThrSerPheLysGlnLeuGluLysGluPheTyrGluValLysGlnArgLeuAspIleAspGlyLys ProAspLysGluGlnLysIleLysIleArgAsnAlaLeu-313 |
| SEQ. ID. NO. 23314 | 324-LeuSerLysGluThrGlnGlu-330 |
| SEQ. ID. NO. 23315 | 342-SerAspAspThrLeuValLysGlnValAspSerArgGluGlyGlnAsnPheAspAspSerTyrTyr-363 |
| SEQ. ID. NO. 23316 | 370-LeuGlnAsnProGluHisValIleArgAspAsnArgGlu-382 |
| SEQ. ID. NO. 23317 | 387-AlaArgTyrLysGlySer-392 |
| SEQ. ID. NO. 23318 | 400-TyrIleLysGluValAspGlu-406 |
| SEQ. ID. NO. 23319 | 411-SerTyrArgIleSerAsnAspLysGluIleAla-421 |
| SEQ. ID. NO. 23320 | 424-MetAlaLysLysLysValLeuLys-431 |
| Hydrophilic Regions - Hopp-Woods | |
| SEQ. ID. NO. 23321 | 13-ProProLysLysAlaIleGlu-19 |
| SEQ. ID. NO. 23322 | 21-LeuGluSerLysLysValThrAlaGluSerTyrArg-32 |
| SEQ. ID. NO. 23323 | 55-AsnAspIleLysThrSerMet-61 |
| SEQ. ID. NO. 23324 | 63-GluSerAlaLysSerGlyGlnSerPheAspAspTrpArgLys-76 |
| SEQ. ID. NO. 23325 | 93-HisAsnGlyLysAspIleIleAsp-100 |
| SEQ. ID. NO. 23326 | 108-GlySerProArgArgLeuGluThr-115 |
| SEQ. ID. NO. 23327 | 147-AlaValGlyAspSerArgThrArgProAla-156 |
| SEQ. ID. NO. 23328 | 190-LeuSerGluArgAspValGluArgGlnGlyArgIleVal-202 |
| SEQ. ID. NO. 23329 | 205-SerThrSerAspAsnLeuValGlu-212 |
| SEQ. ID. NO. 23330 | 215-LysIleTyrAsnLysLysGlyAspThr-223 |
| SEQ. ID. NO. 23331 | 238-ThrThrAspArgGlyPheAsp-244 |
| SEQ. ID. NO. 23332 | 250-MetAsnTyrArgProAspLeuAspLysTyrAspArgAlaLeu-263 |
| SEQ. ID. NO. 23333 | 268-AlaLysAlaGluMetGlyGlyAlaAspPheLysThrSerPheLysGlnLeuGluLysGluPheTyrGluValLysGlnArgLeuAspIleAspGlyLys ProAspLysGluGlnLysIleLysIleArgAsnAlaLeu-313 |

TABLE 1-continued

| | |
|---|---|
| SEQ. ID. NO. 23334 | 324-LeuSerLysGluThrGlnGlu-330 |
| SEQ. ID. NO. 23335 | 344-AspThrLeuValLysGlnValAspSerArgGluGlyGlnAsnPheAsp-359 |
| SEQ. ID. NO. 23336 | 375-HisValIleArgAspAsnArgGlu-382 |
| SEQ. ID. NO. 23337 | 400-TyrIleLysGluValAspGlu-406 |
| SEQ. ID. NO. 23338 | 414-IleSerAsnAspLysGluIleAla-421 |
| SEQ. ID. NO. 23339 | 424-MetAlaLysLysLysValLeuLys-431 |
| a713 | |
| AMPHI Regions - AMPHI | |
| SEQ. ID. NO. 23340 | 18-GluHisArgHisTrpGlu-23 |
| SEQ. ID. NO. 23341 | 115-AspAlaAlaLysLysLeuAlaAlaProTrpProGlnIle-127 |
| SEQ. ID. NO. 23342 | 150-ThrValTrpGlnAlaLeuThrHisIleAlaAsnSerVal-162 |
| SEQ. ID. NO. 23343 | 257-AspAsnLeuAlaAlaLeuGln-263 |
| SEQ. ID. NO. 23344 | 265-GlnAlaLysLysGln-269 |
| Antigenic Index - Jameson-Wolf | |
| SEQ. ID. NO. 23345 | 1-MetGlnAsnAsnSerTyrGly-7 |
| SEQ. ID. NO. 23346 | 13-ArgValGlyGlyLysGluHisArgHisTrpGluArgTyrAspIleAspSerAspPhe-31 |
| SEQ. ID. NO. 23347 | 44-ArgLeuGlyProGluAlaAlaIleProAspLeuSerGlyGluSerCysGluValValIle-63 |
| SEQ. ID. NO. 23348 | 74-GlySerGlnArgHisGlyLysSerLysGlyGlyArgGluLeuSerLeuSerGlyArgAspLeu-94 |
| SEQ. ID. NO. 23349 | 106-LeuAsnValLysGly-110 |
| SEQ. ID. NO. 23350 | 115-AspAlaAlaLysLysLeu-120 |
| SEQ. ID. NO. 23351 | 134-ValGluAsnAsnProAlaLeuAspLysIleAspIleGluProGlyGluThrVal-151 |
| SEQ. ID. NO. 23352 | 167-TrpLeuGluProAspGlyThrLeu-174 |
| SEQ. ID. NO. 23353 | 192-SerArgThrAspSerArgArgAsnIleGluArgMetAspIleGluTrpAspThrAspAsnArgPheSerGlu-215 |
| SEQ. ID. NO. 23354 | 222-SerHisGlyArgSerGlyAspSerAlaLysHisAspLeu-234 |
| SEQ. ID. NO. 23355 | 236-TrpValTyrLysAspProThrMetThrLeuHisArgProLysThrValVal-252 |
| SEQ. ID. NO. 23356 | 254-SerAspAlaAspAsn-258 |
| SEQ. ID. NO. 23357 | 263-GlnLysGlnAlaLysLysGlnLeuAla-271 |
| SEQ. ID. NO. 23358 | 284-ValGlyGlyHisLysThrArgAspGly-292 |
| SEQ. ID. NO. 23359 | 302-HisValIleAspAspGluHisGlyIle-310 |
| SEQ. ID. NO. 23360 | 321-PheMetLeuSerArgMetAspGlyThrGlnThrGluLeuArgLeuLysGluAspGlyIleTrpThrProAspAlaTyrProLysLysAlaGluAlaAla ArgLysArgLysGlyLysArgLysGlyValSerHisLysGlyLysLysGlyGlyLysLysGlnAlaGlu-376 |
| Hydrophilic Regions - Hopp-Woods | |
| SEQ. ID. NO. 23361 | 14-ValGlyGlyLysGluHisArgHisTrpGluArgTyrAspIleAspSer-29 |
| SEQ. ID. NO. 23362 | 54-LeuSerGlyGluSerCysGluValValIle-63 |
| SEQ. ID. NO. 23363 | 76-GlnArgHisGlyLysSerLysGlyGlyArgGluLeuSerLeuSerGlyArgAspLeu-94 |
| SEQ. ID. NO. 23364 | 115-AspAlaAlaLysLysLeu-120 |
| SEQ. ID. NO. 23365 | 138-ProAlaLeuAspLysIleAspIleGluProGlyGlu-149 |
| SEQ. ID. NO. 23366 | 168-LeuGluProAspGly-172 |
| SEQ. ID. NO. 23367 | 193-ArgThrAspSerArgArgAsnIleGluArgMetAspIleGluTrpAspThrAspAsnArgPheSer-214 |
| SEQ. ID. NO. 23368 | 222-SerHisGlyArgSerGlyAspSerAlaLysHisAspLeu-234 |
| SEQ. ID. NO. 23369 | 246-HisArgProLysThr-250 |
| SEQ. ID. NO. 23370 | 254-SerAspAlaAspAsn-258 |
| SEQ. ID. NO. 23371 | 263-GlnLysGlnAlaLysLysGlnLeuAla-271 |
| SEQ. ID. NO. 23372 | 286-GlyHisLysThrArgAsp-291 |
| SEQ. ID. NO. 23373 | 302-HisValIleAspAspGluHisGlyIle-310 |
| SEQ. ID. NO. 23374 | 325-ArgMetAspGlyThrGlnThrGluLeuArgLeuLysGluAspGlyIleTrp-341 |
| SEQ. ID. NO. 23375 | 345-AlaTyrProLysLysAlaGluAlaAlaArgLysArgLysGlyLysArgLysGlyValSerHisLysGlyLysLysGlyGlyLysLysGlnAlaGlu-376 |
| a714 | |
| AMPHI Regions - AMPHI | |
| SEQ. ID. NO. 23376 | 6-IleLeuArgGlyLeuLeuPro-12 |
| SEQ. ID. NO. 23377 | 34-LeuAspAlaValAlaGluSerAlaGlnSerValAlaAspAlaValAspProSer-51 |
| SEQ. ID. NO. 23378 | 55-GlnMetLeuAlaAspTrpGluArgValLeuGlyLeu-66 |
| SEQ. ID. NO. 23379 | 79-AlaValMetAlaLysLeuAsnGluThrGly-88 |
| SEQ. ID. NO. 23380 | 98-LeuAlaGluAlaAla-102 |
| SEQ. ID. NO. 23381 | 110-GluProGlnProPhe-114 |
| SEQ. ID. NO. 23382 | 116-AlaGlyValAsnArgAlaGlyAspArgLeu-125 |
| SEQ. ID. NO. 23383 | 155-AlaGlyAspArgLeuThrAspTyrSerAspAlaValIleGluSerLeuPheAsnArgLeuLys-175 |
| Antigenic Index - Jameson-Wolf | |
| SEQ. ID. NO. 23384 | 15-SerTyrAlaArgAsnAlaProArgValArgAlaGlnAlaGluIleAspGlyAlaAla-33 |
| SEQ. ID. NO. 23385 | 36-AlaValAlaGluSerAlaGlnSerVal-44 |
| SEQ. ID. NO. 23386 | 46-AspAlaValAspProSerSerAlaGly-54 |
| SEQ. ID. NO. 23387 | 64-LeuGlyLeuAspGlyThrGlyLysAsnArgGlnArgArgVal-77 |
| SEQ. ID. NO. 23388 | 83-LysLeuAsnGluThrGlyGlyLeu-90 |
| SEQ. ID. NO. 23389 | 107-GlnIleAspGluProGlnProPheArgAlaGlyValAsnArgAlaGlyAspArgLeuAlaPro-127 |
| SEQ. ID. NO. 23390 | 138-ValArgGlyGlyAsnAsnArgIleThrArgPheArgAlaGlyIle-152 |
| SEQ. ID. NO. 23391 | 154-AlaAlaGlyAspArgLeuThrAspTyrSerAspAlaValIle-167 |
| SEQ. ID. NO. 23392 | 170-LeuPheAsnArgLeuLysPro-176 |
| Hydrophilic Regions - Hopp-Woods | |
| SEQ. ID. NO. 23393 | 18-ArgAsnAlaProArgValArgAlaGlnAlaGluIleAspGlyAlaAla-33 |
| SEQ. ID. NO. 23394 | 36-AlaValAlaGluSerAlaGlnSerVal-44 |
| SEQ. ID. NO. 23395 | 46-AspAlaValAspProSerSer-52 |
| SEQ. ID. NO. 23396 | 68-GlyThrGlyLysAsnArgGlnArgArgVal-77 |
| SEQ. ID. NO. 23397 | 107-GlnIleAspGluProGlnProPhe-114 |
| SEQ. ID. NO. 23398 | 117-GlyValAsnArgAlaGlyAspArgLeuAlaPro-127 |

TABLE 1-continued

| | |
|---|---|
| SEQ. ID. NO. 23399 | 139-ArgGlyGlyAsnAsnArgIleThrArgPheArgAla-150 |
| SEQ. ID. NO. 23400 | 154-AlaAlaGlyAspArgLeuThrAspTyrSerAspAlaValIle-167 |
| SEQ. ID. NO. 23401 | 170-LeuPheAsnArgLeuLysPro-176 |
| a715 | |
| AMPHI Regions - AMPHI | |
| SEQ. ID. NO. 23402 | 15-GlnIleGluArgLeuGlyAsnGlyIle-23 |
| SEQ. ID. NO. 23403 | 31-ArgArgLeuSerGluThrMetHis-38 |
| SEQ. ID. NO. 23404 | 64-LeuSerAspSerGlyArgLeuLysAspSerPheSer-75 |
| SEQ. ID. NO. 23405 | 94-IleHisAsnPheGlyGly-99 |
| Antigenic Index - Jameson-Wolf | |
| SEQ. ID. NO. 23406 | 15-GlnIleGluArgLeuGlyAsnGlyIleGluAsnArgTyrLeuLeu-29 |
| SEQ. ID. NO. 23407 | 47-TyrAlaGlyArgProLysTrpLeuGlyLeuLysTyrArgAspGlyLysProLeuSerAspSerGlyArgLeuLysAspSerPheSerThrLeuSerAsp AsnAspThrAla-83 |
| SEQ. ID. NO. 23408 | 98-GlyGlyMetAlaGlyArgAsnArgLysValArgIleProGlnArgGluPhe-114 |
| SEQ. ID. NO. 23409 | 118-ThrAspAspAspLysGlnAlaLeuMetAspAspValGlnAsp-131 |
| Hydrophilic Regions - Hopp-Woods | |
| SEQ. ID. NO. 23410 | 15-GlnIleGluArgLeuGlyAsn-21 |
| SEQ. ID. NO. 23411 | 57-LysTyrArgAspGlyLysProLeuSerAspSerGlyArgLeuLysAspSerPhe-74 |
| SEQ. ID. NO. 23412 | 78-SerAspAsnAspThr-82 |
| SEQ. ID. NO. 23413 | 101-AlaGlyArgAsnArgLysValArgIleProGlnArgGlu-113 |
| SEQ. ID. NO. 23414 | 118-ThrAspAspAspLysGlnAlaLeuMetAspAspValGlnAsp-131 |
| a716 | |
| AMPHI Regions - AMPHI | |
| SEQ. ID. NO. 23415 | 33-GlyValHisLysSerAlaHisGly-40 |
| SEQ. ID. NO. 23416 | 71-AlaThrValLysLysThrHisLysHisThrLysAla-82 |
| Antigenic Index - Jameson-Wolf | |
| SEQ. ID. NO. 23417 | 1-MetAsnLysAsnIle-5 |
| SEQ. ID. NO. 23418 | 23-AlaAlaAsnLysProAlaSerAsnAlaThrGlyValHisLysSerAlaHisGlySerCysGlyAlaSerLysSerAlaGluGlySerCysGlyAlaAlaGly SerLysAlaGlyGluGlyLysCysGlyGluGlyLysCysGlyAlaThrValLysLysThrHisLysHisThrLysAlaSerLysAlaLysAlaLysSerAlaGlu GlyLysCysGlyGluGlyLysCysGlySerLys-102 |
| Hydrophilic Regions - Hopp-Woods | |
| SEQ. ID. NO. 23419 | 23-AlaAlaAsnLysProAlaSer-29 |
| SEQ. ID. NO. 23420 | 33-GlyValHisLysSerAlaHis-39 |
| SEQ. ID. NO. 23421 | 43-GlyAlaSerLysSerAlaGluGlySerCys-52 |
| SEQ. ID. NO. 23422 | 55-AlaGlySerLysAlaGlyGluGlyLysCysGlyGluGlyLysCys-69 |
| SEQ. ID. NO. 23423 | 71-AlaThrValLysLysThrHisLysHisThrLysAlaSerLysAlaLysAlaLysSerAlaGluGlyLysCysGlyGluGlyLysCysGlySerLys-102 |
| a717 | |
| AMPHI Regions - AMPHI | |
| SEQ. ID. NO. 23424 | 175-AlaValTyrAlaLeuAlaAsn-181 |
| SEQ. ID. NO. 23425 | 209-LeuHisArgGlyLeu-213 |
| SEQ. ID. NO. 23426 | 223-SerIleAlaTyrTrp-227 |
| SEQ. ID. NO. 23427 | 241-AlaGlyLeuGluGlnLeuGly-247 |
| SEQ. ID. NO. 23428 | 263-GlnSerIlePheSerThrValTrpThrProTyrIlePheArgAlaIleGluAla-280 |
| SEQ. ID. NO. 23429 | 305-ThrGlyIlePheSerProLeuAlaSer-313 |
| SEQ. ID. NO. 23430 | 347-LeuAsnValValArgLysThr-353 |
| SEQ. ID. NO. 23431 | 358-LeuAlaThrLeuGlyAlaLeuAla-365 |
| SEQ. ID. NO. 23432 | 401-SerSerCysArgLeuTrpGlnProLeuLysArgLeu-412 |
| SEQ. ID. NO. 23433 | 430-CysPheGlyThrPro-434 |
| SEQ. ID. NO. 23434 | 442-GlyValTrpAlaValTyrLeuAla-449 |
| SEQ. ID. NO. 23435 | 457-LysAspLeuHisLysLeuPheHisTyr-465 |
| Antigenic Index - Jameson-Wolf | |
| SEQ. ID. NO. 23436 | 1-MetAspThrLysGlu-5 |
| SEQ. ID. NO. 23437 | 32-ProAlaAspAspIleGlyArg-38 |
| SEQ. ID. NO. 23438 | 69-AlaAspLysAspThrLeu-74 |
| SEQ. ID. NO. 23439 | 95-SerArgProSerLeuProSerGluIle-103 |
| SEQ. ID. NO. 23440 | 135-MetGluGlyArgAla-139 |
| SEQ. ID. NO. 23441 | 192-AsnArgCysArgLeuLysAlaValArgArgAlaProPheSerSer-206 |
| SEQ. ID. NO. 23442 | 231-SerAlaAspArgLeuPheLeu-237 |
| SEQ. ID. NO. 23443 | 278-IleGluAlaAsnAlaProProAlaArgLeu-287 |
| SEQ. ID. NO. 23444 | 289-AlaThrAlaGluSer-293 |
| SEQ. ID. NO. 23445 | 317-ProGluAsnTyrAla-321 |
| SEQ. ID. NO. 23446 | 349-ValValArgLysThrArgProIleAla-357 |
| SEQ. ID. NO. 23447 | 376-ProSerGlyGlyAlaArgGly-382 |
| SEQ. ID. NO. 23448 | 398-LysThrGluSerSerCysArgLeu-405 |
| SEQ. ID. NO. 23449 | 453-LeuArgHisArgLysAspLeuHis-460 |
| Hydrophilic Regions - Hopp-Woods | |
| SEQ. ID. NO. 23450 | 1-MetAspThrLysGlu-5 |
| SEQ. ID. NO. 23451 | 69-AlaAspLysAspThrLeu-74 |
| SEQ. ID. NO. 23452 | 135-MetGluGlyArgAla-139 |
| SEQ. ID. NO. 23453 | 192-AsnArgCysArgLeuLysAlaValArgArgAlaProPhe-204 |
| SEQ. ID. NO. 23454 | 281-AsnAlaProProAlaArgLeu-287 |
| SEQ. ID. NO. 23455 | 289-AlaThrAlaGluSer-293 |
| SEQ. ID. NO. 23456 | 349-ValValArgLysThrArgPro-355 |
| SEQ. ID. NO. 23457 | 378-GlyGlyAlaArgGly-382 |
| SEQ. ID. NO. 23458 | 399-ThrGluSerSerCys-403 |
| SEQ. ID. NO. 23459 | 453-LeuArgHisArgLysAspLeuHis-460 |
| a718-1 | |
| AMPHI Regions - AMPHI | |
| SEQ. ID. NO. 23460 | 28-IleThrAlaThrGlyArgValIleAlaGluHisProSerAsnPheIleThrProGln-46 |
| SEQ. ID. NO. 23461 | 49-ArgAlaLeuPheGlu-53 |

TABLE 1-continued

| | |
|---|---|
| SEQ. ID. NO. 23462 | 110-AspGlnAlaTyrGluMetMetAspSerLeuProThr-121 |
| SEQ. ID. NO. 23463 | 124-AspLeuIleMetAspLeuMetAspAlaValGlyHisGly-136 |
| SEQ. ID. NO. 23464 | 160-ProGlnSerTrpPheLys-165 |
| SEQ. ID. NO. 23465 | 198-ArgSerValGlnGln-202 |
| SEQ. ID. NO. 23466 | 210-ThrLeuSerTrpLeuTyrMetPhe-217 |
| SEQ. ID. NO. 23467 | 219-HisTyrAlaValHisAspPheAlaGluPheLeuGluLeu-231 |
| SEQ. ID. NO. 23468 | 255-ArgAlaValAlaGluIle-260 |
| SEQ. ID. NO. 23469 | 279-AlaAlaAsnGlyMetThrSer-285 |
| SEQ. ID. NO. 23470 | 320-ThrAsnAlaLeuGlyAsnIleHisAsnGluIleArg-331 |
| SEQ. ID. NO. 23471 | 341-GlnValAlaGlnThrIleThrSerGlnIleIleGlyProPhe-354 |
| SEQ. ID. NO. 23472 | 363-AspProAsnArgVal-367 |
| SEQ. ID. NO. 23473 | 376-GluProLysAspIleAlaValPheAlaAspAlaIleProLysLeuValAsp-392 |
| SEQ. ID. NO. 23474 | 395-ValGlnIleProGlu-399 |
| SEQ. ID. NO. 23475 | 420-ArgGlnValProAspAsnPro-426 |
| SEQ. ID. NO. 23476 | 448-HisGlnGluIleLeuAspGlyAlaLeuAspAsp-458 |
| SEQ. ID. NO. 23477 | 469-LeuAsnProMetValArgGlnAlaValAlaAlaLeuAsnAlaCysAsnSerTyrGlu-487 |
| Antigenic Index - Jameson-Wolf | |
| SEQ. ID. NO. 23478 | 4-IleMetAlaLysLysAsnAsnLysThrLysIleGlnLysProGluAlaAlaLeu-21 |
| SEQ. ID. NO. 23479 | 30-AlaThrGlyArgValIleAla-36 |
| SEQ. ID. NO. 23480 | 38-HisProSerAsnPhe-42 |
| SEQ. ID. NO. 23481 | 44-ThrProGlnLysMetArgAlaLeuPheGluAspAlaGluSerGlyAspIleArgAlaGlnHis-64 |
| SEQ. ID. NO. 23482 | 68-AlaAspIleGluGluArgAspSerAspIle-77 |
| SEQ. ID. NO. 23483 | 81-MetGlyThrArgLysArgAla-87 |
| SEQ. ID. NO. 23484 | 95-ValAlaProProArgAsnAlaThrProGluGluGluLysLeuSerAspGlnAlaTyrGluMet-115 |
| SEQ. ID. NO. 23485 | 119-LeuProThrLeuGlu-123 |
| SEQ. ID. NO. 23486 | 148-AspGlyLeuTyrLeuProArgAsnPheIleHisArgProGlnSerTrpPheLysTrpAspLysAspAsnGlyLeu-172 |
| SEQ. ID. NO. 23487 | 174-LeuArgThrArgGluAsnProGluGlyGluAla-184 |
| SEQ. ID. NO. 23488 | 193-HisThrGlnLysSerArgSerValGlnGlnAlaArgAsnGlyLeuPhe-208 |
| SEQ. ID. NO. 23489 | 237-ArgIleGlyLysTyrGlyAlaGlyAlaThrLysGluGluLysAsnThrLeu-253 |
| SEQ. ID. NO. 23490 | 268-MetProGluGlyMetGluIleGluLeu-276 |
| SEQ. ID. NO. 23491 | 280-AlaAsnGlyMetThrSerAla-286 |
| SEQ. ID. NO. 23492 | 295-AspTrpCysGluLysSerAlaAla-302 |
| SEQ. ID. NO. 23493 | 310-LeuThrSerGlyAlaAspGlyLysSerSerThrAsnAlaLeuGly-324 |
| SEQ. ID. NO. 23494 | 328-AsnGluIleArgArgAspLeuLeuValSerAspAlaLysGlnVal-342 |
| SEQ. ID. NO. 23495 | 359-TyrProHisAlaAspProAsnArgValProLysPheGluPheAspThrArgGluProLysAspIle-380 |
| SEQ. ID. NO. 23496 | 397-IleProGluSerTrpValArgAspLysLeuVal-407 |
| SEQ. ID. NO. 23497 | 410-AspValGlnGluGlyGluAlaValLeu-418 |
| SEQ. ID. NO. 23498 | 420-ArgGlnValProAspAsnProValAsnArg-429 |
| SEQ. ID. NO. 23499 | 440-ValProSerLysAlaThrGlyArgHisGlnGluIleLeuAspGlyAlaLeuAsp-457 |
| SEQ. ID. NO. 23500 | 459-AlaLeuValGluProAspPheAsnSerGlnLeu-469 |
| SEQ. ID. NO. 23501 | 484-AsnSerTyrGluGluAlaAspAla-491 |
| SEQ. ID. NO. 23502 | 499-AsnLeuAspAsnAlaLysLeuArgThr-507 |
| SEQ. ID. NO. 23503 | 519-LeuGlyGlnAspHisAlaArgAla-526 |
| Hydrophilic Regions - Hopp-Woods | |
| SEQ. ID. NO. 23504 | 4-IleMetAlaLysLysAsnAsnLysThrLysIleGlnLysProGluAlaAlaLeu-21 |
| SEQ. ID. NO. 23505 | 46-GlnLysMetArgAlaLeuPheGluAspAlaGluSerGlyAspIleArgAlaGlnHis-64 |
| SEQ. ID. NO. 23506 | 68-AlaAspIleGluGluArgAspSerAspIle-77 |
| SEQ. ID. NO. 23507 | 81-MetGlyThrArgLysArgAla-87 |
| SEQ. ID. NO. 23508 | 96-AlaProProArgAsnAlaThrProGluGluGluLysLeuSerAspGlnAlaTyrGluMet-115 |
| SEQ. ID. NO. 23509 | 165-LysTrpAspLysAspAsnGlyLeu-172 |
| SEQ. ID. NO. 23510 | 174-LeuArgThrArgGluAsnProGluGlyGluAla-184 |
| SEQ. ID. NO. 23511 | 195-GlnLysSerArgSerValGlnGlnAlaArg-204 |
| SEQ. ID. NO. 23512 | 245-AlaThrLysGluGluLysAsnThrLeu-253 |
| SEQ. ID. NO. 23513 | 270-GluGlyMetGluIleGluLeu-276 |
| SEQ. ID. NO. 23514 | 295-AspTrpCysGluLysSerAlaAla-302 |
| SEQ. ID. NO. 23515 | 312-SerGlyAlaAspGlyLysSerSerThr-320 |
| SEQ. ID. NO. 23516 | 328-AsnGluIleArgArgAspLeuLeuValSerAspAlaLysGlnVal-342 |
| SEQ. ID. NO. 23517 | 363-AspProAsnArgValProLysPheGluPheAspThrArgGluProLysAsp-379 |
| SEQ. ID. NO. 23518 | 401-TrpValArgAspLysLeuVal-407 |
| SEQ. ID. NO. 23519 | 410-AspValGlnGluGlyGluAlaValLeu-418 |
| SEQ. ID. NO. 23520 | 421-GlnValProAspAsnProValAsn-428 |
| SEQ. ID. NO. 23521 | 440-ValProSerLysAlaThrGlyArgHisGlnGluIleLeuAspGlyAlaLeuAsp-457 |
| SEQ. ID. NO. 23522 | 485-SerTyrGluGluAlaAspAla-491 |
| SEQ. ID. NO. 23523 | 501-AspAsnAlaLysLeu-505 |
| SEQ. ID. NO. 23524 | 522-AspHisAlaArgAla-526 |
| a720 | |
| AMPHI Regions - AMPHI | |
| SEQ. ID. NO. 23525 | 19-GlnAlaValArgLeuLeuSerThrSer-27 |
| SEQ. ID. NO. 23526 | 46-AlaProAspLeuIleGluValAsn-53 |
| SEQ. ID. NO. 23527 | 66-AlaLeuArgAlaValGlnThrAla-73 |
| SEQ. ID. NO. 23528 | 91-GlnThrAlaGluSerLeu-96 |
| SEQ. ID. NO. 23529 | 102-ArgLeuAsnAlaLeuValAla-108 |
| SEQ. ID. NO. 23530 | 126-GlyThrIleHisGlnIleAlaHisGluPheTyrGlyAspIleAlaArgAlaAlaGluLeuVal-146 |
| Antigenic Index - Jameson-Wolf | |
| SEQ. ID. NO. 23531 | 1-GlyLeuGlnAsnArgLeuAsnArgLeuThrAlaLysGlnVal-14 |
| SEQ. ID. NO. 23532 | 39-AlaHisGlyGluGluMetThrAla-46 |
| SEQ. ID. NO. 23533 | 48-AspLeuIleGluValAsnArgAlaMetArgArgArgMetGlnAla-62 |
| SEQ. ID. NO. 23534 | 74-AlaAlaGluSerGlyGlyLeuThrAla-82 |
| SEQ. ID. NO. 23535 | 91-GlnThrAlaGluSerLeuArgAlaAlaAla-100 |
| SEQ. ID. NO. 23536 | 112-AsnGlnLysProProLeu-117 |

TABLE 1-continued

SEQ. ID. NO. 23537 121-GlnAlaProIleAspGlyThr-127
SEQ. ID. NO. 23538 139-IleAlaArgAlaAlaGlu-144
SEQ. ID. NO. 23539 157-PheIleLysArgGlyThrLeuValAsnSerTyrAlaLys-169
Hydrophilic Regions - Hopp-Woods
SEQ. ID. NO. 23540 4-AsnArgLeuAsnArgLeuThrAla-11
SEQ. ID. NO. 23541 39-AlaHisGlyGluGluMetThrAla-46
SEQ. ID. NO. 23542 48-AspLeuIleGluValAsnArgAlaMetArgArgArgMetGlnAla-62
SEQ. ID. NO. 23543 74-AlaAlaGluSerGlyGly-79
SEQ. ID. NO. 23544 94-GluSerLeuArgAlaAlaAla-100
SEQ. ID. NO. 23545 139-IleAlaArgAlaAlaGlu-144
a721
AMPHI Regions - AMPHI
SEQ. ID. NO. 23546 86-AlaGlyTrpMetArgTrpLeuGlu-93
SEQ. ID. NO. 23547 119-ArgTyrIleSerAlaVal-124
SEQ. ID. NO. 23548 134-SerLysIlePheHisAlaAlaLeuThrAsnPheProAlaLeuAspGlyMetAspGluValLeuAla-155
SEQ. ID. NO. 23549 169-AsnProMetLysGluLeuLeuGlnGlnLeuPheGlyLeu-181
SEQ. ID. NO. 23550 209-AspValPheAlaGln-213
SEQ. ID. NO. 23551 235-LysTyrAlaProIleSerValValGlnGluLeuGln-246
SEQ. ID. NO. 23552 281-TrpAlaGluGlyValLeuLysGlnProGlyGly-291
SEQ. ID. NO. 23553 293-AlaPheLeuThrGlyPheIleGlu-300
Antigenic Index - Jameson-Wolf
SEQ. ID. NO. 23554 1-MetSerLysAsnAlaGln-6
SEQ. ID. NO. 23555 16-GluValGlnProLysAspGlyArgIle-24
SEQ. ID. NO. 23556 27-LeuProTyrGlyGlu-31
SEQ. ID. NO. 23557 33-ArgAlaValAspGlyArgProThrAspValProAla-44
SEQ. ID. NO. 23558 48-ThrGluGluAsnGlyHisAsp-54
SEQ. ID. NO. 23559 58-LeuAlaAsnSerSerArgAsnGlnLeu-66
SEQ. ID. NO. 23560 74-LeuTyrLysGluLysAsnGlyGlnProAlaPro-84
SEQ. ID. NO. 23561 93-GluPheThrProLysGlyMetPheAla-101
SEQ. ID. NO. 23562 104-GluTrpThrAspLysAlaAla-110
SEQ. ID. NO. 23563 114-AlaAlaLysGluTyrArg-119
SEQ. ID. NO. 23564 125-PheSerTyrAspThrLysGlyTyrVal-133
SEQ. ID. NO. 23565 148-AspGlyMetAspGluValLeu-154
SEQ. ID. NO. 23566 160-GlnIleLeuLysProGluThrGluGlnAsnProMetLysGluLeuLeu-175
SEQ. ID. NO. 23567 182-ProAspAlaGlyGluGluGluLeuLysAla-191
SEQ. ID. NO. 23568 197-ValGluAlaLysProLysAspValAlaLeu-206
SEQ. ID. NO. 23569 214-LeuAlaGluLysAspSerArgIle-221
SEQ. ID. NO. 23570 227-GlnThrAlaLysProAspLeuThrLysTyrAla-237
SEQ. ID. NO. 23571 254-AlaLysGlnGluAlaAspLysGlyAsnGlu-263
SEQ. ID. NO. 23572 276-ProAlaGlnLysGluTrpAla-282
SEQ. ID. NO. 23573 285-ValLeuLysGlnProGlyGly-291
SEQ. ID. NO. 23574 310-GlySerGlnThrGlyGlyLysAlaProAspGluArgValAla-323
SEQ. ID. NO. 23575 326-ThrAlaGluGluAlaAlaAla-332
SEQ. ID. NO. 23576 337-GlyMetSerGlyGluGluPheValLysIleLysGluSerGluGlyLys-352
Hydrophilic Regions - Hopp-Woods
SEQ. ID. NO. 23577 1-MetSerLysAsnAlaGln-6
SEQ. ID. NO. 23578 17-ValGlnProLysAspGlyArgIle-24
SEQ. ID. NO. 23579 33-ArgAlaValAspGlyArgProThrAsp-41
SEQ. ID. NO. 23580 49-GluGluAsnGlyHis-53
SEQ. ID. NO. 23581 74-LeuTyrLysGluLysAsnGlyGln-81
SEQ. ID. NO. 23582 104-GluTrpThrAspLysAlaAla-110
SEQ. ID. NO. 23583 114-AlaAlaLysGluTyrArg-119
SEQ. ID. NO. 23584 148-AspGlyMetAspGluValLeu-154
SEQ. ID. NO. 23585 162-LeuLysProGluThrGluGlnAsnProMetLysGluLeuLeu-175
SEQ. ID. NO. 23586 183-AspAlaGlyGluGluGluLeuLysAla-191
SEQ. ID. NO. 23587 197-ValGluAlaLysProLysAspValAlaLeu-206
SEQ. ID. NO. 23588 214-LeuAlaGluLysAspSerArgIle-221
SEQ. ID. NO. 23589 228-ThrAlaLysProAspLeuThrLys-235
SEQ. ID. NO. 23590 254-AlaLysGlnGluAlaAspLysGlyAsnGlu-263
SEQ. ID. NO. 23591 276-ProAlaGlnLysGluTrpAla-282
SEQ. ID. NO. 23592 313-ThrGlyGlyLysAlaProAspGluArgValAla-323
SEQ. ID. NO. 23593 326-ThrAlaGluGluAlaAlaAla-332
SEQ. ID. NO. 23594 339-SerGlyGluGluPheValLysIleLysGluSerGluGlyLys-352
a724
AMPHI Regions - AMPHI
SEQ. ID. NO. 23595 6-LeuAlaLysLysThr-10
SEQ. ID. NO. 23596 12-GlnThrAlaLysAsnIleGlyGluThrLeuArg-22
SEQ. ID. NO. 23597 40-ArgValGlnLeuSer-44
SEQ. ID. NO. 23598 47-AlaAspGluThrLeuGlnAspLeuGluHisLeuGlnGlu-59
Antigenic Index - Jameson-Wolf
SEQ. ID. NO. 23599 5-LysLeuAlaLysLysThrAlaGlnThrAlaLysAsnIleGlyGluThrLeuArgAlaAlaPheArgGlyLysIle-29
SEQ. ID. NO. 23600 34-SerSerGluProIleGlnArgValGlnLeuSerGlyLeuAlaAspGluThrLeuGlnAspLeuGluHis-56
SEQ. ID. NO. 23601 60-TyrGlyPheAlaSerHisProProAspGlySerGluAla-72
SEQ. ID. NO. 23602 77-LeuGlyGlyAsnThrSer-82
SEQ. ID. NO. 23603 90-GlnHisGlySerTyrArgIleLysAsnLeuLysProGlyGluThr-104
SEQ. ID. NO. 23604 108-AsnHisGluGlyAlaLysIleValIleLysGlnGlyLysIleIleGluAlaAspCysAspVal-128
SEQ. ID. NO. 23605 130-ArgValAsnCysLysGlnTyrGlu-137
SEQ. ID. NO. 23606 142-ThrAspAlaLysPhe-146

TABLE 1-continued

| | |
|---|---|
| SEQ. ID. NO. 23607 | 162-GlnIleAsnGlyAsnGly-167 |
| SEQ. ID. NO. 23608 | 170-AlaValGluGlyGlyAspGlyAlaThrPheSerGlyAspValAsnGlnThrGlyGlySerPheAsnThrAspGlyAspValValAla-198 |
| SEQ. ID. NO. 23609 | 205-GlnHisProHisThrAspSerIleGlyGlyLysThrLeuProAlaGluProAla-222 |
| Hydrophilic Regions - Hopp-Woods | |
| SEQ. ID. NO. 23610 | 5-LysLeuAlaLysLysThrAlaGlnThrAlaLysAsnIleGlyGluThrLeuArgAlaAlaPheArgGly-27 |
| SEQ. ID. NO. 23611 | 46-LeuAlaAspGluThrLeuGlnAspLeuGluHis-56 |
| SEQ. ID. NO. 23612 | 66-ProProAspGlySerGlu-71 |
| SEQ. ID. NO. 23613 | 94-TyrArgIleLysAsnLeuLysProGlyGlu-103 |
| SEQ. ID. NO. 23614 | 110-GluGlyAlaLysIleValIleLysGlnGlyLysIleIleGluAlaAspCysAspVal-128 |
| SEQ. ID. NO. 23615 | 132-AsnCysLysGlnTyrGlu-137 |
| SEQ. ID. NO. 23616 | 142-ThrAspAlaLysPhe-146 |
| SEQ. ID. NO. 23617 | 190-PheAsnThrAspGlyAspVal-196 |
| SEQ. ID. NO. 23618 | 207-ProHisThrAspSerIleGly-213 |
| a726 | |
| AMPHI Regions - AMPHI | |
| SEQ. ID. NO. 23619 | 12-AspThrLeuGlySerIleProGlu-19 |
| SEQ. ID. NO. 23620 | 55-ProArgProSerGluTyrHisGlu-62 |
| SEQ. ID. NO. 23621 | 74-AlaAlaAlaAlaArg-78 |
| SEQ. ID. NO. 23622 | 110-IleAspSerPheTyrArg-115 |
| SEQ. ID. NO. 23623 | 122-AlaArgGlnAlaAsp-126 |
| SEQ. ID. NO. 23624 | 137-IleAlaAlaAlaArg-141 |
| SEQ. ID. NO. 23625 | 180-IleGluThrAlaProGlyLeuAspAlaLeuGluLysGluIleGlu-194 |
| Antigenic Index - Jameson-Wolf | |
| SEQ. ID. NO. 23626 | 5-PheLysAsnGlyPheTyrAspAspThrLeuGlySerIleProGluGly-20 |
| SEQ. ID. NO. 23627 | 24-ValArgAlaGluGluTyr-29 |
| SEQ. ID. NO. 23628 | 37-AlaGlnGlyGlyGlnIleAlaAlaAspSerAspGlyArgProValLeuThrProProArgProSerGluTyrHisGluTrpAspGlyLysLysTrpGluIle-70 |
| SEQ. ID. NO. 23629 | 78-ArgPheAlaGluGlnLysThr-84 |
| SEQ. ID. NO. 23630 | 90-LeuAlaAlaLysAlaAspGluLeuLysAsnSer-100 |
| SEQ. ID. NO. 23631 | 106-ProGlnValGluIleAspSerPheTyrArgGlnGluLysGluAlaLeuAlaArgGlnAlaAspAsnAsnAlaProThr-131 |
| SEQ. ID. NO. 23632 | 151-LysValValGluLysSerAlaArg-158 |
| SEQ. ID. NO. 23633 | 167-IleGlyLysArgGlnGlnLeuGluAspLysLeuAsnThr-179 |
| SEQ. ID. NO. 23634 | 181-GluThrAlaProGlyLeuAspAlaLeuGluLysGluIleGluGlu-195 |
| Hydrophilic Regions - Hopp-Woods | |
| SEQ. ID. NO. 23635 | 24-ValArgAlaGluGluTyr-29 |
| SEQ. ID. NO. 23636 | 42-IleAlaAlaAspSerAspGlyArgPro-50 |
| SEQ. ID. NO. 23637 | 55-ProArgProSerGluTyrHisGluTrpAspGlyLysLysTrpGluIle-70 |
| SEQ. ID. NO. 23638 | 78-ArgPheAlaGluGlnLysThr-84 |
| SEQ. ID. NO. 23639 | 90-LeuAlaAlaLysAlaAspGluLeuLysAsn-99 |
| SEQ. ID. NO. 23640 | 114-TyrArgGlnGluLysGluAlaLeuAlaArgGlnAlaAspAsnAsnAla-129 |
| SEQ. ID. NO. 23641 | 151-LysValValGluLysSerAlaArg-158 |
| SEQ. ID. NO. 23642 | 167-IleGlyLysArgGlnGlnLeuGluAspLysLeuAsnThr-179 |
| SEQ. ID. NO. 23643 | 187-AspAlaLeuGluLysGluIleGluGlu-195 |
| a727 | |
| AMPHI Regions - AMPHI | |
| SEQ. ID. NO. 23644 | 6-LeuLeuAlaAsnAsn-10 |
| SEQ. ID. NO. 23645 | 12-GlnProIleAlaIleIleAla-18 |
| SEQ. ID. NO. 23646 | 61-TyrAlaArgGluLeuGlu-66 |
| SEQ. ID. NO. 23647 | 118-GlyCysIleAspGlyPheGly-124 |
| Antigenic Index - Jameson-Wolf | |
| SEQ. ID. NO. 23648 | 28-HisHisGlnGlyTyrLysSerAlaPheAlaLysGln-39 |
| SEQ. ID. NO. 23649 | 41-AlaValIleGluLysMetLysArgAspLysAlaGln-52 |
| SEQ. ID. NO. 23650 | 60-AsnTyrAlaArgGluLeuGluGlnAlaArgAlaGluAlaLysLysTyrGluValLysAla-79 |
| SEQ. ID. NO. 23651 | 86-LeuAlaLysLysGlnAlaGluValSerArgLeuLysThrGluAsnLysLysGluIleGluAsn-106 |
| SEQ. ID. NO. 23652 | 108-LeuThrGlnAspArgLysAsnAlaGlyGlyGlyCysIleAspGlyPheGly-124 |
| SEQ. ID. NO. 23653 | 135-LeuGlyTyrGlyAsn-139 |
| Hydrophilic Regions - Hopp-Woods | |
| SEQ. ID. NO. 23654 | 41-AlaValIleGluLysMetLysArgAspLysAlaGln-52 |
| SEQ. ID. NO. 23655 | 60-AsnTyrAlaArgGluLeuGluGlnAlaArgAlaGluAlaLysLysTyrGluValLysAla-79 |
| SEQ. ID. NO. 23656 | 86-LeuAlaLysLysGlnAlaGluValSerArgLeuLysThrGluAsnLysLysGluIleGluAsn-106 |
| SEQ. ID. NO. 23657 | 108-LeuThrGlnAspArgLysAsnAlaGly-116 |
| a728 | |
| AMPHI Regions - AMPHI | |
| SEQ. ID. NO. 23658 | 11-SerPhePheAlaLeuValPheAla-18 |
| SEQ. ID. NO. 23659 | 39-AlaThrGluValProLysAsnPro-46 |
| SEQ. ID. NO. 23660 | 48-AlaPheValAlaLysLeuAlaArgLeuPheArgAsnAla-60 |
| SEQ. ID. NO. 23661 | 76-AsnLeuAlaGlyThrValAspAsp-83 |
| SEQ. ID. NO. 23662 | 198-GluAspValTyrGluHisCysLeuGlyCysTyrGlnMet-210 |
| SEQ. ID. NO. 23663 | 218-TyrArgAspValAlaAsnAspGlu-225 |
| SEQ. ID. NO. 23664 | 235-SerAsnArgIleAlaSer-240 |
| SEQ. ID. NO. 23665 | 249-GlnAsnMetArgGluLeuMetProArg-257 |
| SEQ. ID. NO. 23666 | 355-GluLysGluValArgArgTyrAlaGluAlaAlaAlaArg-367 |
| Antigenic Index - Jameson-Wolf | |
| SEQ. ID. NO. 23667 | 29-IleAsnProArgTrp-33 |
| SEQ. ID. NO. 23668 | 35-LeuSerAspThrAlaThrGluValProLysAsnProAsn-47 |
| SEQ. ID. NO. 23669 | 57-PheArgAsnAlaAspArgAla-63 |
| SEQ. ID. NO. 23670 | 69-GluSerIleArgThrGluGluAsnLeuAlaGlyThrValAspAspGlyProLeuGlnSerGluLysAspTyr-92 |
| SEQ. ID. NO. 23671 | 98-ArgLeuSerArgLeuLysGluLysAlaLys-107 |
| SEQ. ID. NO. 23672 | 112-ThrGluGlnGluHisGlyLys-118 |
| SEQ. ID. NO. 23673 | 125-HisIleGlyGluGlyGly-130 |

TABLE 1-continued

| | |
|---|---|
| SEQ. ID. NO. 23674 | 136-LeuSerGlnArgSerProGluAlaPheVal-145 |
| SEQ. ID. NO. 23675 | 149-TyrLeuTyrArgAsnAspArgProPheSer-158 |
| SEQ. ID. NO. 23676 | 166-ValHisGlyGluAsnTyrGluThrThrGlyGluTyrArgVal-179 |
| SEQ. ID. NO. 23677 | 182-GlnProAspGlySerVal-187 |
| SEQ. ID. NO. 23678 | 190-AlaAlaGlyArgGlyLysIleGlyGluAspValTyr-201 |
| SEQ. ID. NO. 23679 | 217-LysTyrArgAspValAlaAsnAspGluGlnLysValTrpAspPheArgLysGluSerAsnArgIleAlaSerAspSerArgAsnSerValPheTyrGln AsnMetArgGluLeuMetProArgGlyMetLysAlaAsnSer-263 |
| SEQ. ID. NO. 23680 | 267-GlyTyrAspAlaAspGlyLeuProGlnLys-276 |
| SEQ. ID. NO. 23681 | 280-SerPheAspAsnGlyLysLysArgGlnSerPheGluTyrTyrLeuLysAsnGlyAsn-298 |
| SEQ. ID. NO. 23682 | 309-LeuLysAlaAspGlyValThr-315 |
| SEQ. ID. NO. 23683 | 329-LeuAspGlyGlyArgIleValArgGluGluLysGlnGlyAspArgLeuProAspPhe-347 |
| SEQ. ID. NO. 23684 | 352-GluAsnLeuGluLysGluValArgArgTyrAlaGluAlaAlaAlaArgArgSerGlyGlyArgArgAspLeuSerHis-377 |
| Hydrophilic Regions - Hopp-Woods | |
| SEQ. ID. NO. 23685 | 38-ThrAlaThrGluValProLysAsnPro-46 |
| SEQ. ID. NO. 23686 | 57-PheArgAsnAlaAspArgAla-63 |
| SEQ. ID. NO. 23687 | 69-GluSerIleArgThrGluGluAsnLeu-77 |
| SEQ. ID. NO. 23688 | 80-ThrValAspAspGlyProLeuGlnSerGluLysAspTyr-92 |
| SEQ. ID. NO. 23689 | 98-ArgLeuSerArgLeuLysGluLysAlaLys-107 |
| SEQ. ID. NO. 23690 | 112-ThrGluGlnGluHisGlyLys-118 |
| SEQ. ID. NO. 23691 | 136-LeuSerGlnArgSerProGlu-142 |
| SEQ. ID. NO. 23692 | 151-TyrArgAsnAspArgProPhe-157 |
| SEQ. ID. NO. 23693 | 169-GluAsnTyrGluThrThrGlyGluTyr-177 |
| SEQ. ID. NO. 23694 | 190-AlaAlaGlyArgGlyLysIleGlyGluAspValTyr-201 |
| SEQ. ID. NO. 23695 | 217-LysTyrArgAspValAlaAsnAspGluGlnLysValTrpAspPheArgLysGluSerAsnArgIleAlaSerAspSerArgAsn-244 |
| SEQ. ID. NO. 23696 | 250-AsnMetArgGluLeuMetProArgGlyMetLys-260 |
| SEQ. ID. NO. 23697 | 268-TyrAspAlaAspGlyLeuPro-274 |
| SEQ. ID. NO. 23698 | 282-AspAsnGlyLysLysArgGlnSer-289 |
| SEQ. ID. NO. 23699 | 309-LeuLysAlaAspGlyValThr-315 |
| SEQ. ID. NO. 23700 | 331-GlyGlyArgIleValArgGluGluLysGlnGlyAspArgLeuPro-345 |
| SEQ. ID. NO. 23701 | 352-GluAsnLeuGluLysGluValArgArgTyrAlaGluAlaAlaAlaArgArgSerGlyGlyArgArgAspLeuSerHis-377 |
| a729 | |
| AMPHI Regions - AMPHI | |
| SEQ. ID. NO. 23702 | 21-CysThrMetIleProGlnTyr-27 |
| SEQ. ID. NO. 23703 | 33-GluValAlaGluThrPheLysAsnAspThr-42 |
| SEQ. ID. NO. 23704 | 55-HisAspTyrPheAla-59 |
| SEQ. ID. NO. 23705 | 61-ProArgLeuGlnLysLeuIleAspIle-69 |
| SEQ. ID. NO. 23706 | 149-GlnGlyTyrPheAla-153 |
| SEQ. ID. NO. 23707 | 164-SerLeuIleAlaThrValAlaLys-171 |
| SEQ. ID. NO. 23708 | 242-LeuAlaThrLeuIleAsn-247 |
| SEQ. ID. NO. 23709 | 268-LysLeuProAlaGlyLeu-273 |
| SEQ. ID. NO. 23710 | 322-LeuGlyGlyLeuPheLysSer-328 |
| SEQ. ID. NO. 23711 | 371-ValGlnSerAlaPheGlnAspValAlaAsnAla-381 |
| SEQ. ID. NO. 23712 | 388-LeuAspLysAlaTyrAspAlaLeuSerLysGlnSerArg-400 |
| SEQ. ID. NO. 23713 | 419-GlyAlaLeuAspLeuLeuAspAla-426 |
| SEQ. ID. NO. 23714 | 442-LeuThrArgAlaGluAsnLeuAlaAspLeuTyrLysAlaLeuGlyGlyGlyLeuLys-460 |
| Antigenic Index - Jameson-Wolf | |
| SEQ. ID. NO. 23715 | 25-ProGlnTyrGluGlnProLysValGluVal-34 |
| SEQ. ID. NO. 23716 | 36-GluThrPheLysAsnAspThrAlaAspSerGlyIleArgAlaValAsp-51 |
| SEQ. ID. NO. 23717 | 53-GlyTrpHisAspTyrPheAlaAspProArgLeuGlnLys-65 |
| SEQ. ID. NO. 23718 | 70-AlaLeuGluArgAsnThrSerLeuArgThr-79 |
| SEQ. ID. NO. 23719 | 85-GluIleTyrArgLysGlnTyrMetIleGluArgAsnAsnLeuLeuPro-100 |
| SEQ. ID. NO. 23720 | 105-AsnAlaAsnAspSerArgGlnGlySerLeuSerGlyGlyAsnValSerSerSerTyrLysVal-125 |
| SEQ. ID. NO. 23721 | 138-GlyArgValArgSerSerSerGluAlaAla-147 |
| SEQ. ID. NO. 23722 | 155-ThrAlaAsnArgAspAlaAla-161 |
| SEQ. ID. NO. 23723 | 173-TyrPheAsnGluArgTyrAlaGluGluAlaMet-183 |
| SEQ. ID. NO. 23724 | 188-ArgValLeuLysThrArgGluGluThrTyrLysLeuSerGluLeuArgTyr-204 |
| SEQ. ID. NO. 23725 | 215-ArgGlnGlnGluAlaLeuIleGluSerAlaLysAlaAspTyr-228 |
| SEQ. ID. NO. 23726 | 232-AlaArgSerArgGluGlnAlaArgAsn-240 |
| SEQ. ID. NO. 23727 | 248-GlnProIleProAspAspLeuProAla-256 |
| SEQ. ID. NO. 23728 | 277-ValLeuLeuAspArgProAspIleArgAlaAlaGluHisAlaLeuLysGlnAlaAsnAla-296 |
| SEQ. ID. NO. 23729 | 310-ArgLeuThrGlySerValAspThrHisSerAlaGlu-321 |
| SEQ. ID. NO. 23730 | 325-LeuPheLysSerGlyThr-330 |
| SEQ. ID. NO. 23731 | 347-GlyThrAsnLysAlaAsnLeuAspValAlaLysLeuArgGlnGln-361 |
| SEQ. ID. NO. 23732 | 383-ThrAlaArgGluGlnLeuAspLysAlaTyrAspAlaLeuSerLysGlnSerArgAlaSerLysGluAlaLeuArg-407 |
| SEQ. ID. NO. 23733 | 411-LeuArgTyrLysHisGlyValSer-418 |
| SEQ. ID. NO. 23734 | 424-LeuAspAlaGluArgSerSerTyrSerAla-433 |
| SEQ. ID. NO. 23735 | 442-LeuThrArgAlaGluAsnLeu-448 |
| SEQ. ID. NO. 23736 | 455-LeuGlyGlyGlyLeuLysArgAspThrGlnThrAspLys-467 |
| Hydrophilic Regions - Hopp-Woods | |
| SEQ. ID. NO. 23737 | 28-GluGlnProLysValGluVal-34 |
| SEQ. ID. NO. 23738 | 36-GluThrPheLysAsnAspThrAlaAspSerGlyIleArgAlaVal-50 |
| SEQ. ID. NO. 23739 | 61-ProArgLeuGlnLys-65 |
| SEQ. ID. NO. 23740 | 70-AlaLeuGluArgAsnThrSerLeu-77 |
| SEQ. ID. NO. 23741 | 91-TyrMetIleGluArgAsnAsn-97 |
| SEQ. ID. NO. 23742 | 105-AsnAlaAsnAspSerArgGlnGlySer-113 |
| SEQ. ID. NO. 23743 | 138-GlyArgValArgSerSerSerGluAlaAla-147 |
| SEQ. ID. NO. 23744 | 156-AlaAsnArgAspAlaAla-161 |
| SEQ. ID. NO. 23745 | 177-ArgTyrAlaGluGluAlaMet-183 |
| SEQ. ID. NO. 23746 | 188-ArgValLeuLysThrArgGluGluThrTyrLysLeuSerGluLeuArgTyr-204 |
| SEQ. ID. NO. 23747 | 215-ArgGlnGlnGluAlaLeuIleGluSerAlaLysAlaAspTyr-228 |

TABLE 1-continued

| | |
|---|---|
| SEQ. ID. NO. 23748 | 232-AlaArgSerArgGluGlnAlaArgAsn-240 |
| SEQ. ID. NO. 23749 | 250-IleProAspAspLeuPro-255 |
| SEQ. ID. NO. 23750 | 277-ValLeuLeuAspArgProAspIleArgAlaAlaGluHisAlaLeuLysGlnAlaAsn-295 |
| SEQ. ID. NO. 23751 | 315-ValAspThrHisSerAlaGlu-321 |
| SEQ. ID. NO. 23752 | 350-LysAlaAsnLeuAspValAlaLysLeuArgGln-360 |
| SEQ. ID. NO. 23753 | 383-ThrAlaArgGluGlnLeuAspLysAlaTyrAspAlaLeuSerLysGlnSerArgAlaSerLysGluAlaLeuArg-407 |
| SEQ. ID. NO. 23754 | 424-LeuAspAlaGluArgSerSerTyrSerAla-433 |
| SEQ. ID. NO. 23755 | 442-LeuThrArgAlaGluAsnLeu-448 |
| SEQ. ID. NO. 23756 | 458-GlyLeuLysArgAspThrGlnThrAspLys-467 |
| a730 | |
| AMPHI Regions - AMPHI | |
| SEQ. ID. NO. 23757 | 6-ArgLeuIleLysLeuLeuAlaAlaCys-14 |
| SEQ. ID. NO. 23758 | 26-LeuAlaAlaAspLeu-30 |
| SEQ. ID. NO. 23759 | 67-GlnIleAsnValIleGlnAspTyrThrHisArg-77 |
| SEQ. ID. NO. 23760 | 111-AsnHisAlaAlaAsp-115 |
| SEQ. ID. NO. 23761 | 141-HisProAlaAspAlaTyrAspGlyProLysGlyGlyAsnTyrProLysProThr-158 |
| SEQ. ID. NO. 23762 | 187-GlnArgIleSerAspAsnTyrSerAsnLeuGlySerAsnPheSerAspArgAlaAspGlu-206 |
| SEQ. ID. NO. 23763 | 214-HisAsnAlaLysLeu-218 |
| SEQ. ID. NO. 23764 | 220-ArgTrpGlyAsnSerMetGluPheIleAsnGlyValAla-232 |
| SEQ. ID. NO. 23765 | 234-GlyAlaLeuAsnProPheIleSer-241 |
| SEQ. ID. NO. 23766 | 262-AlaAlaMetArgAsnIleAla-268 |
| SEQ. ID. NO. 23767 | 277-AlaValIleGlyGlyLeuGlySerValAlaGlyPheGluLysAsnThrArgGluAlaValAspArgTrpIleGlnGlu-302 |
| SEQ. ID. NO. 23768 | 305-AsnAlaAlaGluThrValGluAlaLeuValAsnValLeuProPheAlaLysValLysAsnLeuThrLysAlaAlaLysPro-331 |
| SEQ. ID. NO. 23769 | 347-ArgThrThrArgLysValThr-353 |
| SEQ. ID. NO. 23770 | 355-GluThrGluGlyLeuAsnArgIleArgGln-364 |
| SEQ. ID. NO. 23771 | 384-IleAsnValLeuSerGlyAsnSerIleGlnHis-394 |
| SEQ. ID. NO. 23772 | 426-ThrHisGluIleSerAspIleValThr-434 |
| SEQ. ID. NO. 23773 | 475-GluProAlaThrGlyLysValValThrAlaPheProAsp-487 |
| Antigenic Index - Jameson-Wolf | |
| SEQ. ID. NO. 23774 | 2-LysProLeuArgArgLeuIle-8 |
| SEQ. ID. NO. 23775 | 35-PheIleThrAspAsnAlaGlnArgGlnHisTyrGluProGlyGlyLys-50 |
| SEQ. ID. NO. 23776 | 55-GlyAspProArgGlySerValSerAspArgThrGlyGlnIle-68 |
| SEQ. ID. NO. 23777 | 74-TyrThrHisArgMetGly-79 |
| SEQ. ID. NO. 23778 | 97-ArgPheSerGlyHisGlyTyrGluGluHisAlaProPheAsp-110 |
| SEQ. ID. NO. 23779 | 112-HisAlaAlaAspSerAlaSerGluGluLysGlyAsnValAspGluGlyPhe-128 |
| SEQ. ID. NO. 23780 | 133-LeuAsnTrpGluGlyHisGluHisHisProAlaAspAlaTyrAspGlyProLysGlyGlyAsnTyrProLysProThrGlyAlaArgAspGluTyrThr TyrHisVal-168 |
| SEQ. ID. NO. 23781 | 170-GlyThrAlaArgSerIleLysLeuAsnProThrAspThrArgSerIleArgGlnArgIleSerAspAsnTyrSerAsn-195 |
| SEQ. ID. NO. 23782 | 197-GlySerAsnPheSerAspArgAlaAspGluAlaAsnArgLysMetPheGluHisAsnAlaLysLeuAspArgTrpGlyAsnSer-224 |
| SEQ. ID. NO. 23783 | 257-TyrAlaIleAspLysAlaAlaMet-264 |
| SEQ. ID. NO. 23784 | 271-ProAlaGluGlyLys-275 |
| SEQ. ID. NO. 23785 | 287-GlyPheGluLysAsnThrArgGluAlaValAsp-297 |
| SEQ. ID. NO. 23786 | 299-TrpIleGlnGluAsnProAsnAlaAlaGluThrValGlu-311 |
| SEQ. ID. NO. 23787 | 323-LysAsnLeuThrLysAlaAlaLysProGlyLysAlaAlaValSerGlyAspPhe-340 |
| SEQ. ID. NO. 23788 | 344-TyrAsnThrArgThrThrArgLysValThrThrGluThrGluGlyLeuAsnArgIleArgGlnAsnGlnLysAsnSerAsnIleHisGluLysAsnTyr GlyArgAspAsnProAsnHisIle-384 |
| SEQ. ID. NO. 23789 | 397-TyrGlyAspGluAlaGlyGlyGly-404 |
| SEQ. ID. NO. 23790 | 407-PheProGlyLysProGlyLysThrThrPhePro-417 |
| SEQ. ID. NO. 23791 | 419-HisTrpSerAlaSerLysIleThrHisGluIleSerAsp-431 |
| SEQ. ID. NO. 23792 | 433-ValThrSerProLysThrGln-439 |
| SEQ. ID. NO. 23793 | 450-TyrIleAlaLysGlyArgProAlaArg-458 |
| SEQ. ID. NO. 23794 | 461-SerTyrGluThrArgAspGlyIleArgIle-470 |
| SEQ. ID. NO. 23795 | 472-ThrValTyrGluProAlaThrGlyLys-480 |
| SEQ. ID. NO. 23796 | 485-PheProAspArgThrSerAsnProLysTyrAsnProValLys-498 |
| Hydrophilic Regions - Hopp-Woods | |
| SEQ. ID. NO. 23797 | 2-LysProLeuArgArgLeuIle-8 |
| SEQ. ID. NO. 23798 | 39-AsnAlaGlnArgGlnHisTyrGluProGlyGly-49 |
| SEQ. ID. NO. 23799 | 55-GlyAspProArgGlySerValSerAspArgThrGly-66 |
| SEQ. ID. NO. 23800 | 102-GlyTyrGluGluHisAlaPro-108 |
| SEQ. ID. NO. 23801 | 112-HisAlaAlaAspSerAlaSerGluGluLysGlyAsnValAspGluGly-127 |
| SEQ. ID. NO. 23802 | 135-TrpGluGlyHisGluHisHisPro-142 |
| SEQ. ID. NO. 23803 | 144-AspAlaTyrAspGlyProLysGlyGlyAsnTyrProLys-156 |
| SEQ. ID. NO. 23804 | 158-ThrGlyAlaArgAspGluTyr-164 |
| SEQ. ID. NO. 23805 | 170-GlyThrAlaArgSerIleLys-176 |
| SEQ. ID. NO. 23806 | 178-AsnProThrAspThrArgSerIleArgGlnArgIleSerAsp-191 |
| SEQ. ID. NO. 23807 | 200-PheSerAspArgAlaAspGluAlaAsnArgLysMetPheGluHisAsnAlaLysLeuAspArgTrpGlyAsn-223 |
| SEQ. ID. NO. 23808 | 257-TyrAlaIleAspLysAlaAlaMet-264 |
| SEQ. ID. NO. 23809 | 271-ProAlaGluGlyLys-275 |
| SEQ. ID. NO. 23810 | 287-GlyPheGluLysAsnThrArgGluAlaValAsp-297 |
| SEQ. ID. NO. 23811 | 303-AsnProAsnAlaAlaGluThrValGlu-311 |
| SEQ. ID. NO. 23812 | 323-LysAsnLeuThrLysAlaAlaLysProGlyLysAlaAlaVal-336 |
| SEQ. ID. NO. 23813 | 347-ArgThrThrArgLysValThrThrGluThrGluGlyLeuAsnArgIleArgGlnAsnGlnLysAsnSerAsnIleHisGluLysAsnTyrGlyArgAsp AsnProAsn-382 |
| SEQ. ID. NO. 23814 | 399-AspGluAlaGlyGly-403 |
| SEQ. ID. NO. 23815 | 424-LysIleThrHisGluIleSerAsp-431 |

TABLE 1-continued

SEQ. ID. NO. 23816 450-TyrIleAlaLysGlyArgProAlaArg-458
SEQ. ID. NO. 23817 463-GluThrArgAspGlyIleArgIle-470
SEQ. ID. NO. 23818 485-PheProAspArgThrSerAsnProLys-493
a731
AMPHI Regions - AMPHI
SEQ. ID. NO. 23819 17-AlaCysAlaValPro-21
Antigenic Index - Jameson-Wolf
SEQ. ID. NO. 23820 22-GluAlaTyrAspAspGlyGlyArgGlyHis-31
SEQ. ID. NO. 23821 34-ProValGlnAsnGlnAlaGlyThrAlaAsp-43
SEQ. ID. NO. 23822 45-ArgAlaPheSerCysGluAsnGly-52
SEQ. ID. NO. 23823 56-HisValArgArgLeuAspGlyGlyArgIleAlaLeuArgLeuAspGlyArgArgAlaValLeuSerSerAspValAlaAlaSerGlyGluArgTyrThrAla-89
SEQ. ID. NO. 23824 92-GlyLeuPheGlyAsnGlyThrGluTrpHisGlnLysGlyGlyGluAla-107
SEQ. ID. NO. 23825 113-AspAlaTyrGlyAsnSerValGluThrSerCysArgAlaArg-126
Hydrophilic Regions - Hopp-Woods
SEQ. ID. NO. 23826 22-GluAlaTyrAspAspGlyGlyArgGlyHis-31
SEQ. ID. NO. 23827 56-HisValArgArgLeuAspGlyGlyArgIleAlaLeuArgLeuAspGlyArgArgAlaValLeu-76
SEQ. ID. NO. 23828 80-ValAlaAlaSerGlyGluArgTyrThrAla-89
SEQ. ID. NO. 23829 100-TrpHisGlnLysGlyGlyGlu-106
SEQ. ID. NO. 23830 119-ValGluThrSerCysArgAlaArg-126
a732
AMPHI Regions - AMPHI
SEQ. ID. NO. 23831 14-LeuGlyAlaIleSer-18
SEQ. ID. NO. 23832 43-ValGlnSerIleArgThrMetAlaGluValTyrGly-54
SEQ. ID. NO. 23833 66-AspAlaAspLeuPheGluGlyAlaMetLysGlyMetVal-78
SEQ. ID. NO. 23834 95-GluIleLysGluSerThrSerGly-102
SEQ. ID. NO. 23835 115-AspGlyPheValLysValValSerProIleGluAsp-126
SEQ. ID. NO. 23836 155-GluAlaValLysLysMet-160
SEQ. ID. NO. 23837 183-ValAsnLeuThrArg-187
SEQ. ID. NO. 23838 214-GluArgThrValGluSerValAsnThrAlaAlaLys-225
SEQ. ID. NO. 23839 283-LysAlaValProGluAspTyrValTyr-291
SEQ. ID. NO. 23840 297-SerLeuAlaGlyIleProAlaGluLeu-305
SEQ. ID. NO. 23841 322-SerGluIleValAlaGly-327
SEQ. ID. NO. 23842 400-LeuValGlyHisIleGlyAsn-406
SEQ. ID. NO. 23843 446-ArgArgIleProAsnProAlaLysAsp-454
SEQ. ID. NO. 23844 459-LysAlaLeuAspLeuValLysSerProGluGlnTrpGlnLysSerLeu-474
Antigenic Index - Jameson-Wolf
SEQ. ID. NO. 23845 30-AlaAlaGluLysAspArgArgAspAsnGluVal-40
SEQ. ID. NO. 23846 59-AsnTyrTyrGlnAspLysProAspAlaAspLeuPhe-70
SEQ. ID. NO. 23847 82-AspProHisSerGluTyrMetAspLysLysGlyTyrAlaGluIleLysGluSerThrSerGlyGluPheGlyGly-106
SEQ. ID. NO. 23848 111-IleGlyGlnGluAspGlyPhe-117
SEQ. ID. NO. 23849 122-SerProIleGluAspThrProAlaGluArgAlaGlyValLysSerGlyAspPhe-139
SEQ. ID. NO. 23850 144-AspAsnValSerThrArgGlyMetThr-152
SEQ. ID. NO. 23851 155-GluAlaValLysLysMetArgGlyLysProGlyThrLysIle-168
SEQ. ID. NO. 23852 172-LeuSerArgLysAsnAlaAspLysProIle-181
SEQ. ID. NO. 23853 199-LeuIleGluProAspTyrGlyTyr-206
SEQ. ID. NO. 23854 211-GlnPheGlnGluArgThrValGlu-218
SEQ. ID. NO. 23855 221-AsnThrAlaAlaLysGluLeuValLysGluAsnLysGlyLysProLeuLys-237
SEQ. ID. NO. 23856 242-AspLeuArgAspAspProGlyGlyLeu-250
SEQ. ID. NO. 23857 269-ValSerThrLysGlyArgAspGlyLysAspArgMetVal-281
SEQ. ID. NO. 23858 284-AlaValProGluAspTyrVal-290
SEQ. ID. NO. 23859 293-MetGlyGlyAspSerLeuAla-299
SEQ. ID. NO. 23860 303-AlaGluLeuLysThr-307
SEQ. ID. NO. 23861 316-SerGlySerAlaSerAla-321
SEQ. ID. NO. 23862 330-GlnAspHisLysArgAlaVal-336
SEQ. ID. NO. 23863 340-ThrGlnSerPheGlyLysGlySerVal-348
SEQ. ID. NO. 23864 354-LeuSerAsnGlySer-358
SEQ. ID. NO. 23865 368-TyrThrProAsnAspArgSerIleGln-376
SEQ. ID. NO. 23866 384-ValGluValLysAspLysGluArgIlePheGluSerArgGluAlaAspLeu-400
SEQ. ID. NO. 23867 405-GlyAsnProLeuGlyGlyGluAspValAsnSerGlu-416
SEQ. ID. NO. 23868 421-ProLeuGluLysAspAlaAspLysProAlaValLysGluLysGlyLysLysLysLysAspGluAspLeuSerSerArgArgIleProAsnProAlaLysAspAspGlnLeuArgLysAlaLeuAspLeuValLysSerProGluGlnTrpGlnLys-472
SEQ. ID. NO. 23869 477-AlaAlaLysLysProValSerAsnLysAspLysLysAspLysLysAspLysLys-494
Hydrophilic Regions - Hopp-Woods
SEQ. ID. NO. 23870 30-AlaAlaGluLysAspArgArgAspAsnGluVal-40
SEQ. ID. NO. 23871 60-TyrTyrGlnAspLysProAspAlaAspLeuPhe-70
SEQ. ID. NO. 23872 82-AspProHisSerGluTyrMetAspLysLysGlyTyrAlaGluIleLysGluSerThrSerGlyGlu-103
SEQ. ID. NO. 23873 111-IleGlyGlnGluAspGlyPhe-117
SEQ. ID. NO. 23874 122-SerProIleGluAspThrProAlaGluArgAlaGlyValLysSerGlyAspPhe-139
SEQ. ID. NO. 23875 144-AspAsnValSerThr-148
SEQ. ID. NO. 23876 155-GluAlaValLysLysMetArgGlyLysProGlyThr-166
SEQ. ID. NO. 23877 172-LeuSerArgLysAsnAlaAspLysProIle-181
SEQ. ID. NO. 23878 211-GlnPheGlnGluArgThrValGlu-218
SEQ. ID. NO. 23879 221-AsnThrAlaAlaLysGluLeuValLysGluAsnLysGlyLysProLeuLys-237
SEQ. ID. NO. 23880 242-AspLeuArgAspAspProGly-248
SEQ. ID. NO. 23881 271-ThrLysGlyArgAspGlyLysAspArgMetVal-281
SEQ. ID. NO. 23882 303-AlaGluLeuLysThr-307
SEQ. ID. NO. 23883 330-GlnAspHisLysArgAlaVal-336
SEQ. ID. NO. 23884 370-ProAsnAspArgSerIleGln-376
SEQ. ID. NO. 23885 384-ValGluValLysAspLysGluArgIlePheGluSerArgGluAlaAspLeu-400

TABLE 1-continued

| | |
|---|---|
| SEQ. ID. NO. 23886 | 408-LeuGlyGlyGluAspValAsnSer-415 |
| SEQ. ID. NO. 23887 | 421-ProLeuGluLysAspAlaAspLysProAlaValLysGluLysGlyLysLysLysLysAspGluAspLeuSerSerArgArgIleProAsnProAlaLys AspAspGlnLeuArgLysAlaLeuAspLeuValLysSerProGluGlnTrpGln-471 |
| SEQ. ID. NO. 23888 | 477-AlaAlaLysLysProValSerAsnLysAspLysLysAspLysLysAspLysLys-494 |
| a733 | |
| AMPHI Regions - AMPHI | |
| SEQ. ID. NO. 23889 | 6-ThrLeuSerArgLeuSer-11 |
| SEQ. ID. NO. 23890 | 33-TyrGlyGlyTyrProAspThrValTyrGluGly-43 |
| SEQ. ID. NO. 23891 | 53-LysGlnThrGluLysMetGluLysTyrPheVal-63 |
| SEQ. ID. NO. 23892 | 92-GlyAlaPheArgGlnPheGluGlu-99 |
| Antigenic Index - Jameson-Wolf | |
| SEQ. ID. NO. 23893 | 2-MetAsnProLysThrLeuSer-8 |
| SEQ. ID. NO. 23894 | 22-CysGlyGlyAsnGlyGlnLysSer-29 |
| SEQ. ID. NO. 23895 | 33-TyrGlyGlyTyrProAspThrValTyrGluGlyLeuLysAsnAspAspThrSerLeuGlyLysGlnThrGluLysMetGluLysTyrPhe-62 |
| SEQ. ID. NO. 23896 | 65-AlaGlyAsnLysLysMetAsnAlaAlaProGlyAla-76 |
| SEQ. ID. NO. 23897 | 84-LeuSerArgSerGlyAspLysGluGlyAlaPheArgGlnPheGluGluGluLysArgLeuPheProGlu-106 |
| SEQ. ID. NO. 23898 | 115-MetLysThrGlyLysGlyGlyLysArg-123 |
| Hydrophilic Regions - Hopp-Woods | |
| SEQ. ID. NO. 23899 | 40-ValTyrGluGlyLeuLysAsnAspAspThrSerLeuGlyLysGlnThrGluLysMetGluLysTyrPhe-62 |
| SEQ. ID. NO. 23900 | 65-AlaGlyAsnLysLysMetAsnAla-72 |
| SEQ. ID. NO. 23901 | 86-ArgSerGlyAspLysGluGlyAlaPheArgGlnPheGluGluGluLysArgLeuPhePro-105 |
| SEQ. ID. NO. 23902 | 115-MetLysThrGlyLysGlyGlyLysArg-123 |
| a734 | |
| AMPHI Regions - AMPHI | |
| SEQ. ID. NO. 23903 | 19-ArgAlaAlaAspThrTyr-24 |
| SEQ. ID. NO. 23904 | 26-TyrLeuAlaValTrpGlnAsnProGlnAsnAlaAsnAspValLeuGlnVal-42 |
| SEQ. ID. NO. 23905 | 53-GluAlaPheAlaGluLeuGluAlaPheCysLys-63 |
| SEQ. ID. NO. 23906 | 77-ThrGlyCysArgSerValValSer-84 |
| SEQ. ID. NO. 23907 | 92-LeuAlaTyrProLysAlaLeuGlyAlaMetArg-102 |
| SEQ. ID. NO. 23908 | 113-ArgPheThrSerVal-117 |
| SEQ. ID. NO. 23909 | 119-GlnValAlaLeuAsnGlnCysIleLysLys-128 |
| Antigenic Index - Jameson-Wolf | |
| SEQ. ID. NO. 23910 | 18-AlaArgAlaAlaAsp-22 |
| SEQ. ID. NO. 23911 | 31-GlnAsnProGlnAsnAlaAsnAsp-38 |
| SEQ. ID. NO. 23912 | 43-LysThrThrLysGluAspSerThrLysSerGluAlaPheAlaGlu-57 |
| SEQ. ID. NO. 23913 | 60-AlaPheCysLysGlyGlnAspThr-67 |
| SEQ. ID. NO. 23914 | 71-IleAlaGluAspGluProThrGlyCysArgSer-81 |
| SEQ. ID. NO. 23915 | 101-MetArgValGluAsn-105 |
| SEQ. ID. NO. 23916 | 125-CysIleLysLysTyrGlyAlaGlnGly-133 |
| SEQ. ID. NO. 23917 | 145-SerSerTyrTyrGly-149 |
| Hydrophilic Regions - Hopp-Woods | |
| SEQ. ID. NO. 23918 | 18-AlaArgAlaAlaAsp-22 |
| SEQ. ID. NO. 23919 | 43-LysThrThrLysGluAspSerThrLysSerGluAlaPheAlaGlu-57 |
| SEQ. ID. NO. 23920 | 60-AlaPheCysLysGlyGlnAspThr-67 |
| SEQ. ID. NO. 23921 | 71-IleAlaGluAspGluProThrGlyCys-79 |
| SEQ. ID. NO. 23922 | 101-MetArgValGluAsn-105 |
| SEQ. ID. NO. 23923 | 125-CysIleLysLysTyrGlyAla-131 |
| a735 | |
| AMPHI Regions - AMPHI | |
| SEQ. ID. NO. 23924 | 6-LeuLeuAlaAsnAsn-10 |
| SEQ. ID. NO. 23925 | 12-GlnProIleAlaIleIleAla-18 |
| SEQ. ID. NO. 23926 | 61-TyrAlaArgGluLeuGlu-66 |
| SEQ. ID. NO. 23927 | 118-GlyCysIleAspGlyPheGly-124 |
| Antigenic Index - Jameson-Wolf | |
| SEQ. ID. NO. 23928 | 28-HisHisGlnGlyTyrLysSerAlaPheAlaLysGln-39 |
| SEQ. ID. NO. 23929 | 41-AlaValIleGluLysMetLysArgAspLysAlaGln-52 |
| SEQ. ID. NO. 23930 | 60-AsnTyrAlaArgGluLeuGluGlnAlaArgAlaGluAlaLysLysTyrGluValLysAla-79 |
| SEQ. ID. NO. 23931 | 86-LeuAlaLysLysGlnAlaGluValSerArgLeuLysThrGluAsnLysLysGluIleGluAsn-106 |
| SEQ. ID. NO. 23932 | 108-LeuThrGlnAspArgLysAsnAlaGlyGlyGlyCysIleAspGlyPheGly-124 |
| SEQ. ID. NO. 23933 | 135-LeuGlyTyrGlyAsn-139 |
| Hydrophilic Regions - Hopp-Woods | |
| SEQ. ID. NO. 23934 | 41-AlaValIleGluLysMetLysArgAspLysAlaGln-52 |
| SEQ. ID. NO. 23935 | 60-AsnTyrAlaArgGluLeuGluGlnAlaArgAlaGluAlaLysLysTyrGluValLysAla-79 |
| SEQ. ID. NO. 23936 | 86-LeuAlaLysLysGlnAlaGluValSerArgLeuLysThrGluAsnLysLysGluIleGluAsn-106 |
| SEQ. ID. NO. 23937 | 108-LeuThrGlnAspArgLysAsnAlaGly-116 |
| a736 | |
| AMPHI Regions - AMPHI | |
| SEQ. ID. NO. 23938 | 13-GlyLeuIleGlnSerLeuGlySer-20 |
| SEQ. ID. NO. 23939 | 50-GlyValLeuSerVal-54 |
| SEQ. ID. NO. 23940 | 61-GlyLeuPheValGly-65 |
| SEQ. ID. NO. 23941 | 70-LeuGlnGlyTyrThrGlnLeuSerLysPheLysSerAlaAspIle-84 |
| SEQ. ID. NO. 23942 | 93-LeuLeuArgGluLeuGlyProVal-100 |
| SEQ. ID. NO. 23943 | 120-LeuMetLysThrThrGluGlnLeuGluAlaMetAsnValMet-133 |
| SEQ. ID. NO. 23944 | 135-ValAsnProValAlaArgValVal-142 |
| SEQ. ID. NO. 23945 | 144-ProArgPheTrpAlaGlyValPheSerMetPro-154 |

TABLE 1-continued

| | |
|---|---|
| SEQ. ID. NO. 23946 | 156-LeuAlaSerIlePheAsnValAlaGlyIlePheGlyAla-168 |
| SEQ. ID. NO. 23947 | 196-AspValIleAsnGlyLeu-201 |
| SEQ. ID. NO. 23948 | 230-LeuArgAlaSerThrArgThr-236 |
| Antigenic Index - Jameson-Wolf | |
| SEQ. ID. NO. 23949 | 37-ValArgProArgLeuSerVal-43 |
| SEQ. ID. NO. 23950 | 77-SerLysPheLysSer-81 |
| SEQ. ID. NO. 23951 | 93-LeuLeuArgGluLeuGly-98 |
| SEQ. ID. NO. 23952 | 109-SerAlaGlyGlyAlaMetThrSer-116 |
| SEQ. ID. NO. 23953 | 122-LysThrThrGluGlnLeuGlu-128 |
| SEQ. ID. NO. 23954 | 186-GlnMetGlnAsnAsn-190 |
| SEQ. ID. NO. 23955 | 224-ProThrSerGluGlyIleLeuArgAlaSerThr-234 |
| Hydrophilic Regions - Hopp-Woods | |
| SEQ. ID. NO. 23956 | 39-ProArgLeuSerVal-43 |
| SEQ. ID. NO. 23957 | 77-SerLysPheLysSer-81 |
| SEQ. ID. NO. 23958 | 93-LeuLeuArgGluLeuGly-98 |
| SEQ. ID. NO. 23959 | 122-LysThrThrGluGlnLeuGlu-128 |
| a737 | |
| AMPHI Regions - AMPHI | |
| SEQ. ID. NO. 23960 | 56-AlaAlaLeuAlaArgValGlyGly-63 |
| Antigenic Index - Jameson-Wolf | |
| SEQ. ID. NO. 23961 | 24-AlaHisHisAspGlyHisGlyAspAspAspHisGlyHis-36 |
| SEQ. ID. NO. 23962 | 40-GlnHisSerLysGlnAspLysIleIleSer-49 |
| SEQ. ID. NO. 23963 | 51-AlaGlnAlaGluLysAlaAlaLeu-58 |
| SEQ. ID. NO. 23964 | 60-ArgValGlyGlyLysIleThrAspIleAspLeuGluHisAspAsnGlyArgProHisTyrAspValGluIleValLysAsnGlyGlnGluTyr-90 |
| SEQ. ID. NO. 23965 | 94-ValAspAlaArgThrGlyArgValIleSerSerArgArgAspAsp-108 |
| Hydrophilic Regions - Hopp-Woods | |
| SEQ. ID. NO. 23966 | 27-AspGlyHisGlyAspAspAspHisGlyHis-36 |
| SEQ. ID. NO. 23967 | 40-GlnHisSerLysGlnAspLysIleIleSer-49 |
| SEQ. ID. NO. 23968 | 51-AlaGlnAlaGluLysAlaAlaLeu-58 |
| SEQ. ID. NO. 23969 | 61-ValGlyGlyLysIleThrAspIleAspLeuGluHisAspAsnGlyArgProHisTyr-79 |
| SEQ. ID. NO. 23970 | 82-GluIleValLysAsnGlyGlnGluTyr-90 |
| SEQ. ID. NO. 23971 | 94-ValAspAlaArgThrGlyArg-100 |
| SEQ. ID. NO. 23972 | 102-IleSerSerArgArgAspAsp-108 |
| a738 | |
| AMPHI Regions - AMPHI | |
| SEQ. ID. NO. 23973 | 91-LeuMetAsnLeuIleTyrProGlyMetAsnAsp-101 |
| SEQ. ID. NO. 23974 | 139-IleGlySerLeuLeuGlnSerCysIle-147 |
| SEQ. ID. NO. 23975 | 228-ThrTyrIleAlaAlaIleAlaLeuIle-236 |
| SEQ. ID. NO. 23976 | 271-ThrIleLeuGluThrPheThrGlyIle-279 |
| SEQ. ID. NO. 23977 | 285-ValGluArgValAlaAsnGlyGlyPheThrAspLeuProArgGlnIle-300 |
| SEQ. ID. NO. 23978 | 306-LeuAlaAlaPheGlnSer-311 |
| SEQ. ID. NO. 23979 | 316-GlyHisGlyTrpAsnSerPheAla-323 |
| SEQ. ID. NO. 23980 | 338-AspAsnLeuLeuSerAsnLeuPheThr-346 |
| SEQ. ID. NO. 23981 | 371-LeuLeuThrGlyIleAlaGlyLeuLeuLysArg-381 |
| SEQ. ID. NO. 23982 | 398-MetCysHisSerMetLeu-403 |
| SEQ. ID. NO. 23983 | 461-ArgMetValAsnAlaPheSerPro-468 |
| SEQ. ID. NO. 23984 | 472-AspSerAlaLysThrLeuAsnArgLys-480 |
| SEQ. ID. NO. 23985 | 482-AsnGluLeuArgTyrIleSer-488 |
| SEQ. ID. NO. 23986 | 507-LeuProGluTyrProGluThr-513 |
| SEQ. ID. NO. 23987 | 549-AlaLysGlnTrpMetArgAlaThr-556 |
| SEQ. ID. NO. 23988 | 567-TyrAlaAspGluIleArgLysLeuProVal-576 |
| SEQ. ID. NO. 23989 | 579-ProLeuLeuProGluLeuLeuLysAspCysLysAlaPheAlaAlaAlaPro-595 |
| Antigenic Index - Jameson-Wolf | |
| SEQ. ID. NO. 23990 | 38-LeuGlnProSerProAspPheTyrHis-46 |
| SEQ. ID. NO. 23991 | 62-AlaGlyLysLysLeuPheAsp-68 |
| SEQ. ID. NO. 23992 | 123-HisTyrGlyGlnGluArgIle-129 |
| SEQ. ID. NO. 23993 | 154-GlyTrpGluAspThrProLeu-160 |
| SEQ. ID. NO. 23994 | 177-GlyGlnArgAsnAsnLeuGly-183 |
| SEQ. ID. NO. 23995 | 196-LeuAsnGlyGlnArgLysIleProPro-204 |
| SEQ. ID. NO. 23996 | 242-PheArgSerAspLysSerAsnArgArgThrIle-252 |
| SEQ. ID. NO. 23997 | 283-ThrAlaValGluArgValAlaAsnGlyGlyPheThrAspLeuProArgGlnIleGluTrpArgLys-304 |
| SEQ. ID. NO. 23998 | 316-GlyHisGlyTrpAsnSerPheAla-323 |
| SEQ. ID. NO. 23999 | 332-GluGlnHisAsnIleHisAspAsnLeuLeu-341 |
| SEQ. ID. NO. 24000 | 378-LeuLeuLysArgProLeuThr-384 |
| SEQ. ID. NO. 24001 | 424-ProAlaGluAlaSerAspGlyIleAlaPheLysLysAlaAla-437 |
| SEQ. ID. NO. 24002 | 468-ProAlaThrAspAspSerAlaLysThrLeuAsnArgLysIleAsnGlu-483 |
| SEQ. ID. NO. 24003 | 508-ProGluTyrProGluThrGlnThrTrpAlaGlu-518 |
| SEQ. ID. NO. 24004 | 520-AlaThrLeuLysSerLeuLysTyrArgProHisSerAla-532 |
| SEQ. ID. NO. 24005 | 542-ArgGlnGlyLysValAlaGluAlaLysGlnTrpMet-553 |
| SEQ. ID. NO. 24006 | 555-AlaThrGlnSerTyr-559 |
| SEQ. ID. NO. 24007 | 566-ArgTyrAlaAspGluIleArgLys-573 |
| SEQ. ID. NO. 24008 | 584-LeuLeuLysAspCysLysAla-590 |
| SEQ. ID. NO. 24009 | 595-ProGlyHisProGluAlaLysProCysLys-604 |
| Hydrophilic Regions - Hopp-Woods | |
| SEQ. ID. NO. 24010 | 62-AlaGlyLysLysLeuPheAsp-68 |
| SEQ. ID. NO. 24011 | 125-GlyGlnGluArgIle-129 |
| SEQ. ID. NO. 24012 | 198-GlyGlnArgLysIlePro-203 |
| SEQ. ID. NO. 24013 | 243-ArgSerAspLysSerAsnArgArgThrIle-252 |
| SEQ. ID. NO. 24014 | 283-ThrAlaValGluArgValAla-289 |
| SEQ. ID. NO. 24015 | 300-IleGluTrpArgLys-304 |

TABLE 1-continued

| | |
|---|---|
| SEQ. ID. NO. 24016 | 332-GluGlnHisAsnIle-336 |
| SEQ. ID. NO. 24017 | 378-LeuLeuLysArgProLeuThr-384 |
| SEQ. ID. NO. 24018 | 425-AlaGluAlaSerAsp-429 |
| SEQ. ID. NO. 24019 | 431-IleAlaPheLysLysAlaAla-437 |
| SEQ. ID. NO. 24020 | 469-AlaThrAspAspSerAlaLysThrLeuAsnArgLysIleAsnGlu-483 |
| SEQ. ID. NO. 24021 | 525-LeuLysTyrArgPro-529 |
| SEQ. ID. NO. 24022 | 542-ArgGlnGlyLysValAlaGluAlaLysGlnTrpMet-553 |
| SEQ. ID. NO. 24023 | 566-ArgTyrAlaAspGluIleArgLys-573 |
| SEQ. ID. NO. 24024 | 584-LeuLeuLysAspCysLysAla-590 |
| SEQ. ID. NO. 24025 | 596-GlyHisProGluAlaLysProCysLys-604 |
| a739 | |
| AMPHI Regions - AMPHI | |
| SEQ. ID. NO. 24026 | 6-AsnLysProPheArgLeu-11 |
| SEQ. ID. NO. 24027 | 53-HisThrAspSerPro-57 |
| SEQ. ID. NO. 24028 | 86-ProAlaGlnProAspGlyThrAsp-93 |
| SEQ. ID. NO. 24029 | 120-ThrAspArgGlnProAspAspAlaGlyAla-129 |
| SEQ. ID. NO. 24030 | 131-AlaGluAsnThrLeu-135 |
| Antigenic Index - Jameson-Wolf | |
| SEQ. ID. NO. 24031 | 1-MetAlaLysLysProAsnLysProPheArgLeuThrPro-13 |
| SEQ. ID. NO. 24032 | 39-PheAsnProAsnGlyAspLysThrLeuGlnThrGluProGlnHisThrAspSerProArgGluThrGluPhe-62 |
| SEQ. ID. NO. 24033 | 64-LeuProAsnGlyValValGlyGlnAspAlaAlaGlnProGluHisHisHisAlaSerSerSerAlaProAlaGlnProAspGlyThrAspGluSerGlySer GlyLeuProSerProAlaAlaProLysLysAsnArgValLysProGlnProAlaAspThrAlaGlnThrAspArgGlnProAspAspAlaGlyAlaGlnAla GluAsnThrLeuLysGluThrProValLeuProThrAsnValProArgProGluProArgLysGluThrProGluLysGlnAlaGlnProLysGluThrPro LysGluLysGluThrProLysGluAsnHisThrLysProAspThrProLysAsnThrProProLysProHisLysGluIleLeu-193 |
| Hydrophilic Regions - Hopp-Woods | |
| SEQ. ID. NO. 24034 | 1-MetAlaLysLysProAsnLysProPheArgLeu-11 |
| SEQ. ID. NO. 24035 | 41-ProAsnGlyAspLysThrLeuGlnThrGluProGlnHisThrAspSerProArgGluThrGlu-61 |
| SEQ. ID. NO. 24036 | 72-AspAlaAlaGlnProGluHisHisHis-80 |
| SEQ. ID. NO. 24037 | 87-AlaGlnProAspGlyThrAspGluSerGlySer-97 |
| SEQ. ID. NO. 24038 | 103-AlaAlaProLysLysAsnArgValLysProGlnProAlaAspThrAlaGlnThrAspArgGlnProAspAspAlaGlyAlaGlnAlaGluAsnThrLeu LysGluThrPro-139 |
| SEQ. ID. NO. 24039 | 145-ValProArgProGluProArgLysGluThrProGluLysGlnAlaGlnProLysGluThrProLysGluLysGluThrProLysGluAsnHisThrLys ProAspThrProLysAsnThrProProLysProHisLysGluIleLeu-193 |
| a740 | |
| Antigenic Index - Jameson-Wolf | |
| SEQ. ID. NO. 24040 | 25-AlaAsnProProGluAspLysProGln-33 |
| SEQ. ID. NO. 24041 | 57-IleLysHisHisLeuLysGlnGluPheAspLeuLysArgGlnThr-71 |
| Hydrophilic Regions - Hopp-Woods | |
| SEQ. ID. NO. 24042 | 27-ProProGluAspLysProGln-33 |
| SEQ. ID. NO. 24043 | 57-IleLysHisHisLeuLysGlnGluPheAspLeuLysArgGlnThr-71 |
| a741 | |
| AMPHI Regions - AMPHI | |
| SEQ. ID. NO. 24044 | 30-AspIleGlyAlaValLeuAlaAspAlaLeuThrAla-41 |
| SEQ. ID. NO. 24045 | 93-SerArgPheAspPheIleArgGlnIleGlu-102 |
| SEQ. ID. NO. 24046 | 158-ThrSerPheAspLysLeuProGluGlyGlyArg-168 |
| SEQ. ID. NO. 24047 | 200-IleGluHisLeuLys-204 |
| SEQ. ID. NO. 24048 | 251-GlnGluValAlaGlySerAlaGlu-258 |
| Antigenic Index - Jameson-Wolf | |
| SEQ. ID. NO. 24049 | 21-SerSerGlyGlyGly-25 |
| SEQ. ID. NO. 24050 | 43-LeuAspHisLysAspLysSerLeu-50 |
| SEQ. ID. NO. 24051 | 56-AspGlnSerValArgLysAsnGluLysLeuLysLeu-67 |
| SEQ. ID. NO. 24052 | 71-GlyAlaGluLysThrTyrGlyAsnGlyAspSerLeuAsnThrGlyLysLeuLysAsnAspLysValSerArgPheAspPhe-97 |
| SEQ. ID. NO. 24053 | 101-IleGluValAspGlyGlnLeu-107 |
| SEQ. ID. NO. 24054 | 117-ValTyrLysGlnSerHisSerAla-124 |
| SEQ. ID. NO. 24055 | 129-GlnThrGluGlnValGlnAspSerGluHisSerGlyLysMetValAlaLysArgGlnPheArgIleGlyAspIleAlaGlyGluHisThrSerPheAsp LysLeuProGluGlyGlyArgAlaThrTyrArg-172 |
| SEQ. ID. NO. 24056 | 174-ThrAlaPheGlySerAspAspAlaSerGlyLysLeu-185 |
| SEQ. ID. NO. 24057 | 191-PheAlaAlaLysGlnGlyHisGlyLysIleGluHisLeuLysSerProGluLeuAsnVal-210 |
| SEQ. ID. NO. 24058 | 213-AlaAlaSerAspIleLysProAspLysLysArgHisAla-225 |
| SEQ. ID. NO. 24059 | 234-AsnGlnAlaGluLysGlySerTyrSer-242 |
| SEQ. ID. NO. 24060 | 247-GlyGlyGlnAlaGlnGluValAlaGly-255 |
| SEQ. ID. NO. 24061 | 257-AlaGluValGluThrAlaAsnGly-264 |
| Hydrophilic Regions - Hopp-Woods | |
| SEQ. ID. NO. 24062 | 43-LeuAspHisLysAspLysSerLeu-50 |
| SEQ. ID. NO. 24063 | 57-GlnSerValArgLysAsnGluLysLeuLysLeu-67 |
| SEQ. ID. NO. 24064 | 71-GlyAlaGluLysThrTyrGlyAsn-78 |
| SEQ. ID. NO. 24065 | 85-GlyLysLeuLysAsnAspLysValSerArg-94 |
| SEQ. ID. NO. 24066 | 101-IleGluValAspGly-105 |
| SEQ. ID. NO. 24067 | 132-GlnValGlnAspSerGluHisSerGly-140 |
| SEQ. ID. NO. 24068 | 142-MetValAlaLysArgGlnPheArgIle-150 |
| SEQ. ID. NO. 24069 | 152-AspIleAlaGlyGlu-156 |
| SEQ. ID. NO. 24070 | 158-ThrSerPheAspLysLeuProGluGlyGlyArgAlaThrTyr-171 |
| SEQ. ID. NO. 24071 | 177-GlySerAspAspAlaSerGly-183 |
| SEQ. ID. NO. 24072 | 195-GlnGlyHisGlyLysIleGluHisLeuLysSerProGluLeuAsnVal-210 |
| SEQ. ID. NO. 24073 | 213-AlaAlaSerAspIleLysProAspLysLysArgHisAla-225 |

TABLE 1-continued

| | |
|---|---|
| SEQ. ID. NO. 24074 | 235-GlnAlaGluLysGlySer-240 |
| SEQ. ID. NO. 24075 | 249-GlnAlaGlnGluValAlaGly-255 |
| SEQ. ID. NO. 24076 | 257-AlaGluValGluThr-261 |
| a742 | |
| AMPHI Regions - AMPHI | |
| SEQ. ID. NO. 24077 | 26-ArgGluValProAsp-30 |
| SEQ. ID. NO. 24078 | 53-AsnArgProLeuGln-57 |
| SEQ. ID. NO. 24079 | 66-GluAspTrpSerArgLeu-71 |
| SEQ. ID. NO. 24080 | 77-AsnLeuPheSerGlyPheLysHisValPheAsp-87 |
| SEQ. ID. NO. 24081 | 143-LysAlaLeuGluLysLeuLysAla-150 |
| SEQ. ID. NO. 24082 | 153-AspGluThrAlaLysGluTyrArg-160 |
| SEQ. ID. NO. 24083 | 234-AsnAlaAlaGlnArgPheProAsnSerLeuTyrAsp-245 |
| SEQ. ID. NO. 24084 | 326-ValTyrAlaGlySer-330 |
| SEQ. ID. NO. 24085 | 340-SerSerProLeuVal-344 |
| SEQ. ID. NO. 24086 | 369-ArgAsnAlaLysLysIle-374 |
| SEQ. ID. NO. 24087 | 422-ThrProAlaPheThrGlyPheSerGlyThrValProValTrpLysThrValLys-439 |
| SEQ. ID. NO. 24088 | 448-LeuTyrAsnTyrAlaLysTyrLeuAsnThrAsn-458 |
| SEQ. ID. NO. 24089 | 475-LeuHisLeuLeuGlyGlyLeuHisTyr-483 |
| SEQ. ID. NO. 24090 | 505-PheGlnThrAlaSerSer-510 |
| SEQ. ID. NO. 24091 | 543-IleTyrGlySerTyrThrLysIlePheLysGlnGlnAspAsn-556 |
| SEQ. ID. NO. 24092 | 616-GlySerPheGlnThrValAlaLysProIleGlyLysValValSerArg-631 |
| SEQ. ID. NO. 24093 | 643-GluAspTrpLysValPheAlaGly-650 |
| SEQ. ID. NO. 24094 | 657-ArgTyrLysAsnAla-661 |
| SEQ. ID. NO. 24095 | 670-AlaLysAsnThrGly-674 |
| SEQ. ID. NO. 24096 | 677-ProTyrAsnPheSerAsnPheThrProValHisIle-688 |
| SEQ. ID. NO. 24097 | 714-ThrSerSerLeuTyrAsnIle-720 |
| SEQ. ID. NO. 24098 | 725-TyrGlyLeuIleAspGlyPheValArgTyr-734 |
| SEQ. ID. NO. 24099 | 736-LeuGlyLysHisAlaLysLeu-742 |
| SEQ. ID. NO. 24100 | 759-TyrAsnArgThrArgGlyAlaAsnAsnPheTyrGlyGluPro-772 |
| Antigenic Index -Jameson-Wolf | |
| SEQ. ID. NO. 24101 | 6-AlaGluAlaAspAlaGlyAsp-12 |
| SEQ. ID. NO. 24102 | 21-MetTyrGlnLysSerArgGluValProAspPheSerGly-33 |
| SEQ. ID. NO. 24103 | 37-SerCysGluAsnGlnLysThrAlaProPheSerSerThrProAlaCysAsnArgProLeuGlnLeuProArgAsnThrTyrLeuGlyGluAspTrpSer ArgLeuSerAlaAspLysTyrAsn-77 |
| SEQ. ID. NO. 24104 | 86-PheAspAsnGlyTrp-90 |
| SEQ. ID. NO. 24105 | 97-SerTyrThrLysAsnGluSerAspAlaLysVal-107 |
| SEQ. ID. NO. 24106 | 120-LeuSerAspGluAspAla-125 |
| SEQ. ID. NO. 24107 | 130-ThrGluLysAsnGluValIleProPheGluProLysAspLysAlaLeuGluLysLeuLysAlaTyrArgAspGluThrAlaLysGluTyrArgGluArg LysAspAspPheValLysAsnArgPheAspAsnThrAla-175 |
| SEQ. ID. NO. 24108 | 177-GluGlnTyrArgSerArgArgAlaAlaGluArgLysAlaGlyPheAspGluCysMet-195 |
| SEQ. ID. NO. 24109 | 205-CysGlnGlySerTrpGlyAspProGlyValAspAlaAspLysSerGluPheValAsp-223 |
| SEQ. ID. NO. 24110 | 235-AlaAlaGlnArgPheProAsnSerLeuTyrAspSerSerPheAsnArgLysAlaThrAlaAsnArgArgTyrSerTyrMetPro-262 |
| SEQ. ID. NO. 24111 | 264-ArgHisThrLysAspAspArgGlnTrp-272 |
| SEQ. ID. NO. 24112 | 286-GlyArgGluHisAsp-290 |
| SEQ. ID. NO. 24113 | 295-TyrAlaTyrGlyAspGluLysIleArgSerGluTyr-306 |
| SEQ. ID. NO. 24114 | 308-GluIleTyrGluArgArgHisArgValArgProAsnThrGlyAla-322 |
| SEQ. ID. NO. 24115 | 331-CysGlnGlyGluProAspGlyAspLeuSer-340 |
| SEQ. ID. NO. 24116 | 345-ArgGlyHisLysGluProAspTrpGlnAlaTyrAspGluLysGlyAsnArgThrValTyrAlaGluGluCysArgAsnAlaLysLysIleLysThrGlu ProLysLeuAspAlaGluGlyLysGln-386 |
| SEQ. ID. NO. 24117 | 389-TyrTyrAspGluTyrSerGlySerArgThr-398 |
| SEQ. ID. NO. 24118 | 405-TyrGluLeuAspGluLysGlyAsnLysIleGlnGluThrAsnProAspGlyThrPro-423 |
| SEQ. ID. NO. 24119 | 439-LysValAlaAspAspHisVal-445 |
| SEQ. ID. NO. 24120 | 454-TyrLeuAsnThrAsnLysThrHis-461 |
| SEQ. ID. NO. 24121 | 485-ArgTyrGluThrSerGlnThrLysAspMetProValArgTyrGlyGlnProAlaSerAspPheGlnThr-507 |
| SEQ. ID. NO. 24122 | 509-SerSerIleLysAlaAspGlnAspHisTyrThr-519 |
| SEQ. ID. NO. 24123 | 521-LysMetGlnGlyHisLysLeuThrPro-529 |
| SEQ. ID. NO. 24124 | 545-GlySerTyrThrLys-549 |
| SEQ. ID. NO. 24125 | 551-PheLysGlnGlnAspAsnValAspValSerAla-561 |
| SEQ. ID. NO. 24126 | 584-GlyArgLeuAsnAla-588 |
| SEQ. ID. NO. 24127 | 595-LeuGluGlnLysAsnArgThrValVal-603 |
| SEQ. ID. NO. 24128 | 610-GlyAlaGlyGlyLysGlnGlySer-617 |
| SEQ. ID. NO. 24129 | 628-ValValSerArgGlyAlaGluPheGluLeuSerGlyGluLeuAsnGluAspTrpLys-646 |
| SEQ. ID. NO. 24130 | 652-ThrTyrAsnLysSerArgTyrLysAsnAlaAlaGluValAsnAlaGluArgLeuAlaLysAsnThrGlyAlaAspProTyrAsnPheSerAsn-682 |
| SEQ. ID. NO. 24131 | 708-ValSerAlaGlnSerGlyThrSerSerLeuTyrAsnIleArgGlnGlyGly-724 |
| SEQ. ID. NO. 24132 | 735-GluLeuGlyLysHisAlaLys-741 |
| SEQ. ID. NO. 24133 | 746-GlyThrAsnLeuAsnGlyArgThrTyrPheGluAsnAsnTyrAsnArgThrArgGlyAlaAsnAsnPheTyrGlyGluProArgThrValSerMet-777 |
| Hydrophilic Regions - Hopp-Woods | |
| SEQ. ID. NO. 24134 | 6-AlaGluAlaAspAlaGlyAsp-12 |
| SEQ. ID. NO. 24135 | 23-GlnLysSerArgGluValProAsp-30 |
| SEQ. ID. NO. 24136 | 67-AspTrpSerArgLeuSerAlaAspLys-75 |
| SEQ. ID. NO. 24137 | 97-SerTyrThrLysAsnGluSerAspAlaLysVal-107 |
| SEQ. ID. NO. 24138 | 120-LeuSerAspGluAspAla-125 |
| SEQ. ID. NO. 24139 | 130-ThrGluLysAsnGluValIleProPheGluProLysAspLysAlaLeuGluLysLeuLysAlaTyrArgAspGluThrAlaLysGluTyrArgGluArg LysAspAspPheValLysAsnArgPheAspAsnThrAla-175 |
| SEQ. ID. NO. 24140 | 177-GluGlnTyrArgSerArgArgAlaAlaGluArgLysAlaGlyPheAspGluCysMet-195 |
| SEQ. ID. NO. 24141 | 212-ProGlyValAspAlaAspLysSerGluPheValAsp-223 |
| SEQ. ID. NO. 24142 | 247-SerPheAsnArgLysAlaThrAlaAsnArgArgTyrSer-259 |
| SEQ. ID. NO. 24143 | 264-ArgHisThrLysAspAspArgGlnTrp-272 |
| SEQ. ID. NO. 24144 | 286-GlyArgGluHisAsp-290 |

TABLE 1-continued

| | |
|---|---|
| SEQ. ID. NO. 24145 | 297-TyrGlyAspGluLysIleArgSerGluTyr-306 |
| SEQ. ID. NO. 24146 | 308-GluIleTyrGluArgArgHisArgValArgProAsnThr-320 |
| SEQ. ID. NO. 24147 | 331-CysGlnGlyGluProAspGlyAspLeu-339 |
| SEQ. ID. NO. 24148 | 345-ArgGlyHisLysGluProAsp-351 |
| SEQ. ID. NO. 24149 | 354-AlaTyrAspGluLysGlyAsnArg-361 |
| SEQ. ID. NO. 24150 | 363-ValTyrAlaGluGluCysArgAsnAlaLysLysIleLysThrGluProLysLeuAspAlaGluGlyLysGln-386 |
| SEQ. ID. NO. 24151 | 393-TyrSerGlySerArg-397 |
| SEQ. ID. NO. 24152 | 405-TyrGluLeuAspGluLysGlyAsnLysIleGlnGluThrAsnProAspGly-421 |
| SEQ. ID. NO. 24153 | 439-LysValAlaAspAspHisVal-445 |
| SEQ. ID. NO. 24154 | 485-ArgTyrGluThrSerGlnThrLysAspMetProVal-496 |
| SEQ. ID. NO. 24155 | 500-GlnProAlaSerAsp-504 |
| SEQ. ID. NO. 24156 | 509-SerSerIleLysAlaAspGlnAspHisTyrThr-519 |
| SEQ. ID. NO. 24157 | 551-PheLysGlnGlnAspAsnValAspValSerAla-561 |
| SEQ. ID. NO. 24158 | 597-GlnLysAsnArgThrValVal-603 |
| SEQ. ID. NO. 24159 | 611-AlaGlyGlyLysGlnGlySer-617 |
| SEQ. ID. NO. 24160 | 628-ValValSerArgGlyAlaGluPheGluLeuSerGlyGluLeuAsnGluAspTrpLys-646 |
| SEQ. ID. NO. 24161 | 654-AsnLysSerArgTyrLysAsnAlaAlaGluValAsnAlaGluArgLeuAlaLys-671 |
| SEQ. ID. NO. 24162 | 735-GluLeuGlyLysHisAlaLys-741 |
| SEQ. ID. NO. 24163 | 758-AsnTyrAsnArgThrArgGly-764 |
| SEQ. ID. NO. 24164 | 770-GlyGluProArgThrValSerMet-777 |
| a743 | |
| AMPHI Regions - AMPHI | |
| SEQ. ID. NO. 24165 | 19-TyrGlyGlySerPhe-23 |
| SEQ. ID. NO. 24166 | 58-SerTyrThrIleAsp-62 |
| SEQ. ID. NO. 24167 | 64-MetSerThrAlaThrGly-69 |
| SEQ. ID. NO. 24168 | 96-ThrLeuGluGluAlaMetLysAsnThrThrGlyValAsnValValArgAsp-112 |
| SEQ. ID. NO. 24169 | 158-ValTyrAspHisIleGluValValArgGlyAlaThrGly-170 |
| Antigenic Index - Jameson-Wolf | |
| SEQ. ID. NO. 24170 | 1-MetAsnGlnAsnHis-5 |
| SEQ. ID. NO. 24171 | 30-ValSerAspGlyAsnThrVal-36 |
| SEQ. ID. NO. 24172 | 41-ValAsnValArgGlySerHisAlaLeuSerGlyLysThrGluLysThrArgSerTyrThrIleAspArgMetSerThr-66 |
| SEQ. ID. NO. 24173 | 72-IleAlaGlyLysAspThrProGlnSer-80 |
| SEQ. ID. NO. 24174 | 85-ThrArgSerArgLeuAspAspLysAlaValHisThrLeuGluGluAlaMetLysAsnThrThrGly-106 |
| SEQ. ID. NO. 24175 | 109-ValValArgAspSerGlyLeuGlnThrArgPheLeuSerArgGlyPhe-124 |
| SEQ. ID. NO. 24176 | 128-GlnIleGlyGluAspGlyIle-134 |
| SEQ. ID. NO. 24177 | 140-GlyArgSerGlyTyrThrAlaLysIleAspValSerProSerThrAsp-155 |
| SEQ. ID. NO. 24178 | 163-GluValValArgGlyAlaThrGlyLeuThrGlnSerAsnSerGluProGlyGly-180 |
| SEQ. ID. NO. 24179 | 184-LeuIleArgLysArg-188 |
| Hydrophilic Regions - Hopp-Woods | |
| SEQ. ID. NO. 24180 | 49-LeuSerGlyLysThrGluLysThrArgSerTyrThrIleAspArgMetSerThr-66 |
| SEQ. ID. NO. 24181 | 72-IleAlaGlyLysAspThrProGln-79 |
| SEQ. ID. NO. 24182 | 85-ThrArgSerArgLeuAspAspLysAlaValHisThrLeuGluGluAlaMetLysAsn-103 |
| SEQ. ID. NO. 24183 | 109-ValValArgAspSerGlyLeu-115 |
| SEQ. ID. NO. 24184 | 128-GlnIleGlyGluAspGlyIle-134 |
| SEQ. ID. NO. 24185 | 174-SerAsnSerGluProGlyGly-180 |
| SEQ. ID. NO. 24186 | 184-LeuIleArgLysArg-188 |
| a746 | |
| AMPHI Regions - AMPHI | |
| SEQ. ID. NO. 24187 | 10-LeuSerGlyTyrGluGlnLeuLys-17 |
| SEQ. ID. NO. 24188 | 42-LeuSerSerGlyProAlaGluGlnThrAla-51 |
| SEQ. ID. NO. 24189 | 72-SerAlaAlaAspLysProGlnAsp-79 |
| SEQ. ID. NO. 24190 | 94-SerGluProGluAsn-98 |
| SEQ. ID. NO. 24191 | 118-LeuGluAlaSerGluLysLeuGlnGlnAlaGluThrAlaLysThrAlaPro-134 |
| SEQ. ID. NO. 24192 | 153-AspThrValAlaValGlu-158 |
| SEQ. ID. NO. 24193 | 160-ProLysArgThrAlaGluThr-166 |
| SEQ. ID. NO. 24194 | 170-LysAlaGluArgThr-174 |
| SEQ. ID. NO. 24195 | 184-ThrLysThrAlaGluLysValAlaAspLysProLys-195 |
| SEQ. ID. NO. 24196 | 210-SerAlaValLysGluAlaLysLysAlaAspLysAlaGluSer-223 |
| SEQ. ID. NO. 24197 | 238-GluThrAlaGlnLysThrAspLysAlaAspLysThrLysThrAlaGluLys-254 |
| SEQ. ID. NO. 24198 | 287-SerThrIleThrGluIleMetThr-294 |
| SEQ. ID. NO. 24199 | 307-TyrLysAsnAlaArgAspAlaGluArgAspLeu-317 |
| Antigenic Index - Jameson-Wolf | |
| SEQ. ID. NO. 24200 | 1-MetSerGluAsnLysGlnAsnGluValLeuSerGlyTyrGluGlnLeuLysArgArgAsnArgArgArgLeuValThr-26 |
| SEQ. ID. NO. 24201 | 43-SerSerGlyProAlaGluGlnThrAlaGlyGluThrSerGlyValGluAsnLysAlaAlaGly-63 |
| SEQ. ID. NO. 24202 | 72-SerAlaAlaAspLysProGlnAspLeuAlaGlyGluAspLysProSerAlaAlaAspSerGluIleSerGluProGluAsnVal-99 |
| SEQ. ID. NO. 24203 | 107-AsnAspArgLeuGluAspSerAsnIleLysGlyLeuGluAlaSerGluLysLeuGlnGlnAlaGluThrAlaLysThrAlaProLysGlnAlaLysGln ArgAlaAlaGluLysValProAlaThrAlaAspSerThrAspThrValAlaValGluLysProLysArgThrAlaGluThrLysProGlnLysAlaGluArgThr AlaLysAlaLysProLysAlaLysGluThrLysThrAlaGluLysValAlaAspLysProLysThrAlaAlaGluLysThrLysProAspThrAlaLysSerAsp SerAlaValLysGluAlaLysLysAlaAspLysAlaGluSerLysLysThrAlaGluLysAspArgSerAspGlyLysLysHisGluThrAlaGlnLysThr AspLysAlaAspLysThrLysThrAlaGluLysGluLysSerGlyLysLysAlaAla-262 |
| SEQ. ID. NO. 24204 | 266-GlyTyrAlaGluLysGluArgAlaLeuSerLeuGlnArgLysMetLysAlaAlaGlyIle-285 |
| SEQ. ID. NO. 24205 | 292-IleMetThrAspAsnGlyLysValTyrArgValLysSerSerAsnTyrLysAsnAlaArgAspAlaGluArgAspLeuAsnLysLeuArgVal-322 |
| Hydrophilic Regions - Hopp-Woods | |
| SEQ. ID. NO. 24206 | 1-MetSerGluAsnLysGlnAsnGluVal-9 |
| SEQ. ID. NO. 24207 | 14-GluGlnLeuLysArgArgAsnArgArgArgLeuVal-25 |
| SEQ. ID. NO. 24208 | 45-GlyProAlaGluGlnThrAlaGlyGluThrSerGlyValGluAsnLysAlaAlaGly-63 |
| SEQ. ID. NO. 24209 | 72-SerAlaAlaAspLysProGlnAspLeuAlaGlyGluAspLysProSerAlaAlaAspSerGluIleSerGluProGluAsnVal-99 |
| SEQ. ID. NO. 24210 | 108-AspArgLeuGluAspSerAsnIleLysGlyLeuGluAlaSerGluLysLeuGlnGlnAlaGluThrAlaLysThrAlaProLysGlnAlaLysGlnArg AlaAlaGluLysValProAlaThrAlaAspSerThrAsp-153 |

TABLE 1-continued

| | |
|---|---|
| SEQ. ID. NO. 24211 | 155-ValAlaValGluLysProLysArgThrAlaGluThrLysProGlnLysAlaGluArgThrAlaLysAlaLysProLysAlaLysGluThrLysThrAla GluLysValAlaAspLysProLysThrAlaAlaGluLysThrLysProAspThrAlaLysSerAspSerAlaValLysGluAlaLysLysAlaAspLysAla GluSerLysLysThrAlaGluLysAspArgSerAspGlyLysLysHisGluThrAlaGlnLysThrAspLysAlaAspLysThrLysThrAlaGluLysGlu LysSerGlyLysLysAlaAla-262 |
| SEQ. ID. NO. 24212 | 267-TyrAlaGluLysGluArgAlaLeuSerLeuGlnArgLysMetLysAlaAlaGlyIle-285 |
| SEQ. ID. NO. 24213 | 292-IleMetThrAspAsnGlyLysValTyrArgValLysSerSerAsnTyrLysAsnAlaArgAspAlaGluArgAspLeuAsnLysLeuArgVal-322 |
| a747 | |
| AMPHI Regions - AMPHI | |
| SEQ. ID. NO. 24214 | 28-ValSerLysSerAlaLysGlyTrp-35 |
| Antigenic Index - Jameson-Wolf | |
| SEQ. ID. NO. 24215 | 8-TyrAlaAspLeuArgGlyLysThrLysVal-17 |
| SEQ. ID. NO. 24216 | 23-CysAlaSerArgAspValSerLysSerAlaLysGlyTrp-35 |
| SEQ. ID. NO. 24217 | 42-AsnValGlyLysGlnLeuThrAspSerValGlyLeuGluPheAspProTyrTyrArgHisLysThrIleCysLysProArgGluIleValLeuAspGlyAsp LysThrLysMetGlyArgSerLysSerAsnGluTyrGly-88 |
| SEQ. ID. NO. 24218 | 97-SerGlnLeuLysSerLys-102 |
| Hydrophilic Regions - Hopp-Woods | |
| SEQ. ID. NO. 24219 | 8-TyrAlaAspLeuArgGlyLysThrLysVal-17 |
| SEQ. ID. NO. 24220 | 23-CysAlaSerArgAspValSerLysSerAlaLys-33 |
| SEQ. ID. NO. 24221 | 63-ThrIleCysLysProArgGluIleValLeuAspGlyAspLysThrLysMetGlyArgSerLysSerAsnGluTyr-87 |
| a748 | |
| AMPHI Regions - AMPHI | |
| SEQ. ID. NO. 24222 | 22-GlyAlaValGlyAlaIleGlyGly-29 |
| SEQ. ID. NO. 24223 | 40-AlaGluArgThrAlaGluSerGlnHis-48 |
| SEQ. ID. NO. 24224 | 82-SerAlaLysGlnLeuGluAsnLeuPheArgThrLeu-93 |
| SEQ. ID. NO. 24225 | 155-LeuGlnGluMetArgAspPheSerAsnAspLysLeuGlnLysSerTrp-170 |
| SEQ. ID. NO. 24226 | 188-GlnAlaAlaLeuArgAspIleIleLysHisThrValGln-200 |
| SEQ. ID. NO. 24227 | 250-GlyValAlaAlaAsnSer-255 |
| SEQ. ID. NO. 24228 | 257-AspGluProGluTrp-261 |
| SEQ. ID. NO. 24229 | 268-GlnAlaValArgLeuIleArgHisPheValGluPheTrpAspArg-282 |
| SEQ. ID. NO. 24230 | 310-GlnProAspPheAlaLys-315 |
| SEQ. ID. NO. 24231 | 334-ArgAspProGluPheLeu-339 |
| SEQ. ID. NO. 24232 | 390-LeuGluGluTyrIleSerProPhe-397 |
| Antigenic Index - Jameson-Wolf | |
| SEQ. ID. NO. 24233 | 1-MetSerLysAsnGlnProAlaGlnProThrArgArgThrLeuPhe-15 |
| SEQ. ID. NO. 24234 | 29-GlyTyrLeuGlyGlyLysLysArgGlyGluThrAlaGluArgThrAlaGluSerGlnHisSerProGlnAla-52 |
| SEQ. ID. NO. 24235 | 80-AlaGlnSerAlaLysGlnLeuGluAsn-88 |
| SEQ. ID. NO. 24236 | 101-ThrGlnGlyGlyGluTyrGlnAspGlyAspAspLysLeuProProAlaGlySerGly-119 |
| SEQ. ID. NO. 24237 | 125-PheAsnProAspGlyLeuThr-131 |
| SEQ. ID. NO. 24238 | 139-SerLeuPheAspGlyArgPheGlyLeuLysAspLysLysProIleHis-154 |
| SEQ. ID. NO. 24239 | 156-GlnGluMetArgAspPheSerAsnAspLysLeuGlnLysSerTrpCysAspGlyAspLeuSer-176 |
| SEQ. ID. NO. 24240 | 183-ThrProGluThrCys-187 |
| SEQ. ID. NO. 24241 | 208-IleAspGlyTrpGlnProLysSerGluProGlyAlaMetAla-221 |
| SEQ. ID. NO. 24242 | 226-LeuGlyPheArgAspGlyThrGlyAsnProLysValSerAspProLysThrAlaAspGlu-245 |
| SEQ. ID. NO. 24243 | 255-SerLeuAspGluProGluTrpAlaLysAsnGlySerTyrGlnAla-269 |
| SEQ. ID. NO. 24244 | 279-PheTrpAspArgThrProLeuGlnGluGlnThrAspIlePheGlyArgArgLysTyrSerGlyAlaProMetAspGlyLysLysGluAlaAspGlnPro AspPheAlaLysAspProGluGlyAsnThrThrProLysAspSerHisIleArgLeuAlaAsnProArgAspProGluPheLeuLysLysHisArgLeuPhe Arg-346 |
| SEQ. ID. NO. 24245 | 348-AlaTyrSerTyrSerArgGlyLeuAlaSerSerGlyGlnLeu-361 |
| SEQ. ID. NO. 24246 | 385-LeuAsnGlyGluProLeuGluGluTyr-393 |
| SEQ. ID. NO. 24247 | 406-ProGlyValGluLysGlyGlyPhe-413 |
| Hydrophilic Regions - Hopp-Woods | |
| SEQ. ID. NO. 24248 | 1-MetSerLysAsnGlnPro-6 |
| SEQ. ID. NO. 24249 | 8-GlnProThrArgArgThrLeuPhe-15 |
| SEQ. ID. NO. 24250 | 32-GlyGlyLysLysArgGlyGluThrAlaGluArgThrAlaGluSerGlnHis-48 |
| SEQ. ID. NO. 24251 | 80-AlaGlnSerAlaLysGlnLeuGluAsn-88 |
| SEQ. ID. NO. 24252 | 104-GlyGluTyrGlnAspGlyAspAspLysLeuProPro-115 |
| SEQ. ID. NO. 24253 | 145-PheGlyLeuLysAspLysLysProIleHis-154 |
| SEQ. ID. NO. 24254 | 156-GlnGluMetArgAspPheSerAsnAspLysLeuGlnLysSerTrpCysAspGlyAspLeu-175 |
| SEQ. ID. NO. 24255 | 211-TrpGlnProLysSerGluProGlyAlaMetAla-221 |
| SEQ. ID. NO. 24256 | 229-ArgAspGlyThrGlyAsnProLysValSerAspProLysThrAlaAsp-244 |
| SEQ. ID. NO. 24257 | 255-SerLeuAspGluProGluTrpAlaLys-263 |
| SEQ. ID. NO. 24258 | 283-ThrProLeuGlnGluGlnThrAspIlePheGlyArgArgLysTyrSer-298 |
| SEQ. ID. NO. 24259 | 301-ProMetAspGlyLysLysGluAlaAspGlnProAspPheAlaLysAspProGluGlyAsnThrThrProLysAspSerHisIle-328 |
| SEQ. ID. NO. 24260 | 331-AlaAsnProArgAspProGluPheLeuLysLysHisArgLeuPheArg-346 |
| SEQ. ID. NO. 24261 | 388-GluProLeuGluGluTyr-393 |
| SEQ. ID. NO. 24262 | 407-GlyValGluLysGlyGly-412 |
| a749 | |
| AMPHI Regions - AMPHI | |
| SEQ. ID. NO. 24263 | 1-MetArgLysPheAsnLeuThrAlaLeuSerValMetLeuAlaLeuGlyLeuThrAlaCysGlnProProGluAlaGluLysAlaAlaProAlaAlaSerGly GluAlaGlnThrAlaAsnGluGlyGlySerValSerIleAlaValAsnAspAsnAlaCysGluProMetGluLeuThrValProSerGlyGlnValValPheAsn IleLysAsnAsnSerGlyArgLysLeuGluTrpGluIleLeuLysGlyValMetValValAspGluArgGluAsnIleAlaProGlyLeuSerAspLysMet ThrValThrLeuLeuProGlyGluTyrGluMetThrCysGlyLeuLeuThrAsnProArgGlyLysLeuValValThrAspSerGlyPheLysAspThrAla AsnGluAlaAspLeuGluLysLeuSerGlnProLeuAlaAspTyrLysAlaTyrValGlnGlyGluValLysGluLeuValAlaLysThrLysThrPheThr GluAlaValLysAlaGlyAspIleGluLysAlaLysSerLeuPheAlaAspThrArgValHisTyrGluArgIleGluProIleAlaGluLeuPheSerGluLeu AspProValIleAspAlaArgGluAspAspPheLysAspGlyAlaLysAspAlaGlyPheThrGlyPheHisArgIleGluTyrAlaLeuTrpValGluLys AspValSerGlyValLysGluIleAlaAlaLysLeuMetThrAspValGluAlaLeuGlnLysGluIleAspAlaLeuAlaPheProProGlyLysValValGly GlyAlaSerGluLeuIleGluGluValAlaGlySerLysIleSerGlyGluGluAspArgTyrSerHisThrAspLeuSerAspPheGlnAlaAsnValAspGly SerLysLysIleValAspLeuPheArgProLeuIleGluThrLysAsnLysAlaLeuLeuGluLysThrAspThrAsnPheLysGlnValAsnGluIleLeu |

TABLE 1-continued

AlaLysTyrArgThrLysAspGlyPheGluThrTyrAspLysLeuGlyGluAlaAspArgLysAlaLeuGlnAlaSerIleAsnAlaLeuAlaGluAspLeu AlaGlnLeuArgGlyIleLeuGlyLeuLys-388

Antigenic Index - Jameson-Wolf
(SEQ. ID. NO. 24263)
1-MetArgLysPheAsnLeuThrAlaLeuSerValMetLeuAlaLeuGlyLeuThrAlaCysGlnProProGluAlaGluLysAlaAlaProAlaAlaSerGlyGluAlaGlnThrAlaAsnGlu GlyGlySerValSerIleAlaValAsnAspAsnAlaCysGluProMetGluLeuThrValProSerGlyGlnValValPheAsnIleLysAsnAsnSerGlyArgLysLeuGluTrpGluIleLeuLys GlyValMetValValAspGluArgGluAsnIleAlaProGlyLeuSerAspLysMetThrValThrLeuLeuProGlyGluTyrGluMetThrCysGlyLeuLeuThrAsnProArgGlyLysLeu ValValThrAspSerGlyPheLysAspThrAlaAsnGluAlaAspLeuGluLysLeuSerGlnProLeuAlaAspTyrLysAlaTyrValGlnGlyGluValLysGluLeuValAlaLysThrLys ThrPheThrGluAlaValLysAlaGlyAspIleGluLysAlaLysSerLeuPheAlaAspThrArgValHisTyrGluArgIleGluProIleAlaGluLeuPheSerGluLeuAspProValIleAsp AlaArgGluAspAspPheLysAspGlyAlaLysAspAlaGlyPheThrGlyPheHisArgIleGluTyrAlaLeuTrpValGluLysAspValSerGlyValLysGluIleAlaAlaLysLeuMet ThrAspValGluAlaLeuGlnLysGluIleAspAlaLeuAlaPheProProGlyLysValValGlyGlyAlaSerGluLeuIleGluGluValAlaGlySerLysIleSerGlyGluGluAspArgTyr SerHisThrAspLeuSerAspPheGlnAlaAsnValAspGlySerLysLysIleValAspLeuPheArgProLeuIleGluThrLysAsnLysAlaLeuLeuGluLysThrAspThrAsnPheLys GlnValAsnGluIleLeuAlaLysTyrArgThrLysAspGlyPheGluThrTyrAspLysLeuGlyGluAlaAspArgLysAlaLeuGlnAlaSerIleAsnAlaLeuAlaGluAspLeuAlaGln LeuArgGlyIleLeuGlyLeuLys-388

Hydrophilic Regions - Hopp-Woods
(SEQ. ID. NO. 24263)
1-MetArgLysPheAsnLeuThrAlaLeuSerValMetLeuAlaLeuGlyLeuThrAlaCysGlnProProGluAlaGluLysAlaAlaProAlaAlaSerGlyGluAlaGlnThrAlaAsnGlu GlyGlySerValSerIleAlaValAsnAspAsnAlaCysGluProMetGluLeuThrValProSerGlyGlnValValPheAsnIleLysAsnAsnSerGlyArgLysLeuGluTrpGluIleLeu LysGlyValMetValValAspGluArgGluAsnIleAlaProGlyLeuSerAspLysMetThrValThrLeuLeuProGlyGluTyrGluMetThrCysGlyLeuLeuThrAsnProArgGly LysLeuValValThrAspSerGlyPheLysAspThrAlaAsnGluAlaAspLeuGluLysLeuSerGlnProLeuAlaAspTyrLysAlaTyrValGlnGlyGluValLysGluLeuValAla LysThrLysThrPheThrGluAlaValLysAlaGlyAspIleGluLysAlaLysSerLeuPheAlaAspThrArgValHisTyrGluArgIleGluProIleAlaGluLeuPheSerGluLeuAsp ProValIleAspAlaArgGluAspAspPheLysAspGlyAlaLysAspAlaGlyPheThrGlyPheHisArgIleGluTyrAlaLeuTrpValGluLysAspValSerGlyValLysGluIleAla AlaLysLeuMetThrAspValGluAlaLeuGlnLysGluIleAspAlaLeuAlaPheProProGlyLysValValGlyGlyAlaSerGluLeuIleGluGluValAlaGlySerLysIleSerGly GluGluAspArgTyrSerHisThrAspLeuSerAspPheGlnAlaAsnValAspGlySerLysLysIleValAspLeuPheArgProLeuIleGluThrLysAsnLysAlaLeuLeuGluLys ThrAspThrAsnPheLysGlnValAsnGluIleLeuAlaLysTyrArgThrLysAspGlyPheGluThrTyrAspLysLeuGlyGluAlaAspArgLysAlaLeuGlnAlaSerIleAsnAla LeuAlaGluAspLeuAlaGlnLeuArgGlyIleLeuGlyLeuLys-388 a750

AMPHI Regions - AMPHI

SEQ. ID. NO. 24264 1-ValLysProArgPheTyrTrpAlaAlaCysAlaValLeuLeuThrAlaCysSerProGluProAlaAlaGluLysThrValSerAlaAlaSerAlaSerAlaAla ThrLeuThrValProThrAlaArgGlyAspAlaValValProLysAsnProGluArgValAlaValTyrAspTrpAlaAlaLeuAspThrLeuThrGluLeu GlyValAsnValGlyAlaThrThrAlaProValArgValAspTyrLeuGlnProAlaPheAspLysAlaAlaThrValGlyThrLeuPheGluProAspTyr GluAlaLeuHisArgTyrAsnProGlnLeuValIleThrGlyGlyProGlyAlaGluAlaTyrGluGlnLeuAlaLysAsnAlaThrThrIleAspLeuThrVal AspAsnGlyAsnIleArgThrSerGlyGluLysGlnMetGluThrLeuAlaArgIlePheGlyLysGluAlaArgAlaAlaGluLeuLysAlaGlnIleAsp AlaLeuPheAlaGlnThrArgGluAlaAlaLysGlyLysGlyArgGlyLeuValLeuSerValThrGlyAsnLysValSerAlaPheGlyThrGlnSerArg LeuAlaSerTrpIleHisGlyAspIleGlyLeuProProValAspGluSerLeuArgAsnGluGlyHisGlyGlnProValSerPheGluTyrIleLysGluLys AsnProAspTrpIlePheIleIleAspArgThrAlaAlaIleGlyGlnGluGlyProAlaAlaValGluValLeuAspAsnAlaLeuValArgGlyThrAsnAla TrpLysArgLysGlnIleIleValMetProAlaAlaAsnTyrIleValAlaGlyGlySerArgGlnLeuIleGlnAlaAlaGluGlnLeuLysGluAlaPheGlu LysAlaGluProValAlaAlaGlyLysGlu-321

Antigenic Index - Jameson-Wolf
(SEQ. ID. NO. 24264)
1-ValLysProArgPheTyrTrpAlaAlaCysAlaValLeuLeuThrAlaCysSerProGluProAlaAlaGluLysThrValSerAlaAlaSerAlaSerAlaAlaThrLeuThrValProThrAla ArgGlyAspAlaValValProLysAsnProGluArgValAlaValTyrAspTrpAlaAlaLeuAspThrLeuThrGluLeuGlyValAsnValGlyAlaThrThrAlaProValArgValAsp TyrLeuGlnProAlaPheAspLysAlaAlaThrValGlyThrLeuPheGluProAspTyrGluAlaLeuHisArgTyrAsnProGlnLeuValIleThrGlyGlyProGlyAlaGluAlaTyr GluGlnLeuAlaLysAsnAlaThrThrIleAspLeuThrValAspAsnGlyAsnIleArgThrSerGlyGluLysGlnMetGluThrLeuAlaArgIlePheGlyLysGluAlaArgAlaAla GluLeuLysAlaGlnIleAspAlaLeuPheAlaGlnThrArgGluAlaAlaLysGlyLysGlyArgGlyLeuValLeuSerValThrGlyAsnLysValSerAlaPheGlyThrGlnSerArg LeuAlaSerTrpIleHisGlyAspIleGlyLeuProProValAspGluSerLeuArgAsnGluGlyHisGlyGlnProValSerPheGluTyrIleLysGluLysAsnProAspTrpIlePheIleIle AspArgThrAlaAlaIleGlyGlnGluGlyProAlaAlaValGluValLeuAspAsnAlaLeuValArgGlyThrAsnAlaTrpLysArgLysGlnIleIleValMetProAlaAlaAsnTyrIle ValAlaGlyGlySerArgGlnLeuIleGlnAlaAlaGluGlnLeuLysGluAlaPheGluLysAlaGluProValAlaAlaGlyLysGlu-321

Hydrophilic Regions - Hopp-Woods
(SEQ. ID. NO. 24264)
1-ValLysProArgPheTyrTrpAlaAlaCysAlaValLeuLeuThrAlaCysSerProGluProAlaAlaGluLysThrValSerAlaAlaSerAlaSerAlaAlaThrLeuThrValProThrAla ArgGlyAspAlaValValProLysAsnProGluArgValAlaValTyrAspTrpAlaAlaLeuAspThrLeuThrGluLeuGlyValAsnValGlyAlaThrThrAlaProValArgValAspTyr LeuGlnProAlaPheAspLysAlaAlaThrValGlyThrLeuPheGluProAspTyrGluAlaLeuHisArgTyrAsnProGlnLeuValIleThrGlyGlyProGlyAlaGluAlaTyrGluGln LeuAlaLysAsnAlaThrThrIleAspLeuThrValAspAsnGlyAsnIleArgThrSerGlyGluLysGlnMetGluThrLeuAlaArgIlePheGlyLysGluAlaArgAlaAlaGluLeuLys AlaGlnIleAspAlaLeuPheAlaGlnThrArgGluAlaAlaLysGlyLysGlyArgGlyLeuValLeuSerValThrGlyAsnLysValSerAlaPheGlyThrGlnSerArgLeuAlaSerTrp IleHisGlyAspIleGlyLeuProProValAspGluSerLeuArgAsnGluGlyHisGlyGlnProValSerPheGluTyrIleLysGluLysAsnProAspTrpIlePheIleIleAspArgThrAla AlaIleGlyGlnGluGlyProAlaAlaValGluValLeuAspAsnAlaLeuValArgGlyThrAsnAlaTrpLysArgLysGlnIleIleValMetProAlaAlaAsnTyrIleValAlaGlyGlySer ArgGlnLeuIleGlnAlaAlaGluGlnLeuLysGluAlaPheGluLysAlaGluProValAlaAlaGlyLysGlu-321 a756

AMPHI Regions - AMPHI

SEQ. ID. NO. 24265 1-MetThrAlaAsnPheAlaGlnThrLeuValGluIleGlnAspSerLeuXxxArgValValSerThrValGlnTyrGlyAspAspAsnLeuLysArgLeuThr AlaAspLysArgLysGlnTyrGluLeuAsnPheLysIleSerGluGlySerThrArgValGluSerAspPheLysGluThrLeuValArgPheGlyArgAsp MetLeuGlnAspMetProProLysIleArgSerAlaThrLeuValAlaLeuThrThrLeuLeuValGlyGlyAlaLeuGlyTyrGlyTyrLeuGluTyrLeu LysGlnValAlaSerGluGlyTyrGlnThrGluArgLeuTyrAsnAlaValAspArgLeuAlaGluSerGlnGluArgIleThrSerAlaIleLeuLysGlyAla ArgGlyAlaAspPheValGlnIleGlyArgArgSerTyrSerArgGluAspIleSerGluAlaAsnArgArgAlaGluArgValProTyrGlyAlaGluLeuVal SerAspGlyAsnPheThrAlaValLeuSerAspIleGlyAsp-186

Antigenic Index - Jameson-Wolf
(SEQ. ID. NO. 24265)
1-MetThrAlaAsnPheAlaGlnThrLeuValGluIleGlnAspSerLeuXxxArgValValSerThrValGlnTyrGlyAspAspAsnLeuLysArgLeuThrAlaAspLysArgLysGlnTyr GluLeuAsnPheLysIleSerGluGlySerThrArgValGluSerAspPheLysGluThrLeuValArgPheGlyArgAspMetLeuGlnAspMetProProLysIleArgSerAlaThrLeuVal AlaLeuThrThrLeuLeuValGlyGlyAlaLeuGlyTyrGlyTyrLeuGluTyrLeuLysGlnValAlaSerGluGlyTyrGlnThrGluArgLeuTyrAsnAlaValAspArgLeuAlaGlu SerGlnGluArgIleThrSerAlaIleLeuLysGlyAlaArgGlyAlaAspPheValGlnIleGlyArgArgSerTyrSerArgGluAspIleSerGluAlaAsnArgArgAlaGluArgValProTyr GlyAlaGluLeuValSerAspGlyAsnPheThrAlaValLeuSerAspIleGlyAsp-186

Hydrophilic Regions - Hopp-Woods
(SEQ. ID. NO. 24265)
1-MetThrAlaAsnPheAlaGlnThrLeuValGluIleGlnAspSerLeuXxxArgValValSerThrValGlnTyrGlyAspAspAsnLeuLysArgLeuThrAlaAspLysArgLysGlnTyr GluLeuAsnPheLysIleSerGluGlySerThrArgValGluSerAspPheLysGluThrLeuValArgPheGlyArgAspMetLeuGlnAspMetProProLysIleArgSerAlaThrLeuVal TABLE 1-continued AlaLeuThrThrLeuLeuValGlyGlyAlaLeuGlyTyrGlyTyrLeuGluTyrLeuLysGlnValAlaSerGluGlyTyrGlnThrGluArgLeuTyrAsnAlaValAspArgLeuAlaGluSer
GlnGluArgIleThrSerAlaIleLeuLysGlyAlaArgGlyAlaAspPheValGlnIleGlyArgArgSerTyrSerArgGluAspIleSerGluAlaAsnArgArgAlaGluArgValProTyrGly
AlaGluLeuValSerAspGlyAsnPheThrAlaValLeuSerAspIleGlyAsp-186
a758
AMPHI Regions - AMPHI
SEQ. ID. NO. 24266 1-MetAsnAsnLeuThrValPheThrArgPheAspThrAspLeuAlaThrLeuAlaAspGluLeuGlnTyrValTrpGluHisThrAlaValThrAspHis
GlnGlyLysLeuValGluIleProValCysTyrGlyGlyGluTyrGlyProAspLeuAlaGluValAlaAlaPheHisGlnThrValIleSerGluIleValArg
ArgHisThrAlaGlnThrTyrThrValPheMetMetGlyPheGlnProGlyPheProTyrLeuGlyGlyLeuProGluAlaLeuHisThrProArgArgAla
ValProArgThrSerValProAlaGlySerValGlyIleGlyGlySerGlnThrGlyValTyrProPheAlaSerProGlyGlyTrpGlnIleIleGlyArgThr
GluLeuProLeuPheArgAlaAspLeuAsnProProThrLeuLeuAlaAlaGlyAspGlnValArgPheValAlaGluArgIleGluPro-167
Antigenic Index - Jameson-Wolf
(SEQ. ID. NO. 24266)
1-MetAsnAsnLeuThrValPheThrArgPheAspThrAspLeuAlaThrLeuAlaAspGluLeuGlnTyrValTrpGluHisThrAlaValThrAspHisGlnGlyLysLeuValGluIlePro
ValCysTyrGlyGlyGluTyrGlyProAspLeuAlaGluValAlaAlaPheHisGlnThrValIleSerGluIleValArgArgHisThrAlaGlnThrTyrThrValPheMetMetGlyPheGlnPro
GlyPheProTyrLeuGlyGlyLeuProGluAlaLeuHisThrProArgArgAlaValProArgThrSerValProAlaGlySerValGlyIleGlyGlySerGlnThrGlyValTyrProPheAlaSer
ProGlyGlyTrpGlnIleIleGlyArgThrGluLeuProLeuPheArgAlaAspLeuAsnProProThrLeuLeuAlaAlaGlyAspGlnValArgPheValAlaGluArgIleGluPro-167
Hydrophilic Regions - Hopp-Woods
(SEQ. ID. NO. 24266)
1-MetAsnAsnLeuThrValPheThrArgPheAspThrAspLeuAlaThrLeuAlaAspGluLeuGlnTyrValTrpGluHisThrAlaValThrAspHisGlnGlyLysLeuValGluIlePro
ValCysTyrGlyGlyGluTyrGlyProAspLeuAlaGluValAlaAlaPheHisGlnThrValIleSerGluIleValArgArgHisThrAlaGlnThrTyrThrValPheMetMetGlyPheGlnPro
GlyPheProTyrLeuGlyGlyLeuProGluAlaLeuHisThrProArgArgAlaValProArgThrSerValProAlaGlySerValGlyIleGlyGlySerGlnThrGlyValTyrProPheAlaSer
ProGlyGlyTrpGlnIleIleGlyArgThrGluLeuProLeuPheArgAlaAspLeuAsnProProThrLeuLeuAlaAlaGlyAspGlnValArgPheValAlaGluArgIleGluPro-167
a761
AMPHI Regions - AMPHI
SEQ. ID. NO. 24267 1-MetLysIleSerPheHisLeuAlaLeuLeuProThrLeuIleIleAlaSerPheProValAlaAlaAlaAspThrGlnAspAsnGlyGluHisTyrThrAlaThr
LeuProThrValSerValValGlyGlnSerAspThrSerValLeuLysGlyTyrIleAsnTyrAspGluAlaAlaValThrArgAsnGlyGlnLeuIleLysGlu
ThrProGlnThrIleAspThrLeuAsnIleGlnLysAsnLysAsnTyrGlyThrAsnAspLeuSerSerIleLeuGluGlyAsnAlaGlyIleAspAlaAlaTyr
AspMetArgGlyGluSerIlePheLeuArgGlyPheGlnAlaAspAlaSerAspIleTyrArgAspGlyValArgGluSerGlyGlnValArgArgSerThr
AlaAsnIleGluArgValGluIleLeuLysGlyProSerSerValLeuTyrGlyArgThrAsnGlyGlyGlyValIleAsnMetValSerLysTyrAlaAsnPhe
LysGlnSerArgAsnIleGlyThrValTyrGlySerTrpAlaAsnArgSerLeuAsnMetAspIleAsnGluValLeuAsnLysAsnValAlaIleArgLeu
ThrGlyGluValGlyArgAlaAsnSerPheArgSerGlyIleAspSerLysAsnValMetValSerProSerIleThrValLysLeuAspAsnGlyLeuLysTrp
ThrGlyGlnTyrThrTyrAspAsnValGluArgThrProAspArgSerProThrLysSerValTyrAspArgPheGlyLeuProTyrArgMetGlyPheAla
HisArgAsnAspPheValLysAspLysLeuGlnValTrpArgSerAspLeuGluTyrAlaPheAsnAspLysTrpArgAlaGlnTrpGlnLeuAlaHisArg
ThrAlaAlaGlnAspPheAspHisPheTyrAlaGlySerGluAsnGlyAsnLeuIleLysArgAsnTyrAlaTrpGlnGlnThrAspAsnLysThrLeuSer
SerAsnLeuThrLeuAsnGlyAspTyrThrIleGlyArgPheGluAsnHisLeuThrValGlyMetAspTyrSerArgGluHisArgAsnProThrLeuGly
PheSerSerAlaPheSerAlaSerIleAsnProTyrAspArgAlaSerTrpProAlaSerGlyArgLeuGlnProIleLeuThrGlnAsnArgHisLysAlaAsp
SerTyrGlyIlePheValGlnAsnIlePheSerAlaThrProAspLeuLysPheValLeuGlyGlyArgTyrAspLysTyrThrPheAsnSerGluAsnLys
LeuThrGlySerSerArgGlnTyrSerGlyHisSerPheSerProAsnIleGlyAlaValTrpAsnIleAsnProValHisThrLeuTyrAlaSerTyrAsnLys
GlyPheAlaProTyrGlyGlyArgGlyGlyTyrLeuSerIleAspThrLeuSerSerAlaValPheAsnAlaAspProGluTyrThrArgGlnTyrGluThr
GlyValLysSerSerTrpLeuAspAspArgLeuSerThrThrLeuSerAlaTyrGlnIleGluArgPheAsnIleArgTyrArgProAspProLysAsnAsn
ProTyrIleTyrAlaValSerGlyLysHisArgSerArgGlyValGluLeuSerAlaIleGlyGlnIleIleProLysLysLeuTyrLeuArgGlySerLeuGly
ValMetGlnAlaLysValValGluAspLysGluAsnProAspArgValGlyIleHisLeuAsnAsnThrSerAsnValThrGlyAsnLeuPhePheArg
TyrThrProThrGluAsnLeuTyrGlyGluIleGlyValThrGlyThrGlyLysArgTyrGlyTyrAspSerArgAsnLysGluValThrThrLeuProGly
PheAlaArgValAspAlaMetLeuGlyTrpAsnHisLysAsnValAsnValThrPheAlaAlaAlaAsnLeuPheAsnGlnLysTyrTrpArgSerAsp
SerMetProGlyAsnProArgGlyTyrThrAlaArgValAsnTyrArgPhe-703
Antigenic Index - Jameson-Wolf
(SEQ. ID. NO. 24267)
1-MetLysIleSerPheHisLeuAlaLeuLeuProThrLeuIleIleAlaSerPheProValAlaAlaAlaAspThrGlnAspAsnGlyGluHisTyrThrAlaThrLeuProThrValSerValValGly
GlnSerAspThrSerValLeuLysGlyTyrIleAsnTyrAspGluAlaAlaValThrArgAsnGlyGlnLeuIleLysGluThrProGlnThrIleAspThrLeuAsnIleGlnLysAsnLysAsnTyr
GlyThrAsnAspLeuSerSerIleLeuGluGlyAsnAlaGlyIleAspAlaAlaTyrAspMetArgGlyGluSerIlePheLeuArgGlyPheGlnAlaAspAlaSerAspIleTyrArgAspGlyVal
ArgGluSerGlyGlnValArgArgSerThrAlaAsnIleGluArgValGluIleLeuLysGlyProSerSerValLeuTyrGlyArgThrAsnGlyGlyGlyValIleAsnMetValSerLysTyrAla
AsnPheLysGlnSerArgAsnIleGlyThrValTyrGlySerTrpAlaAsnArgSerLeuAsnMetAspIleAsnGluValLeuAsnLysAsnValAlaIleArgLeuThrGlyGluValGlyArg
AlaAsnSerPheArgSerGlyIleAspSerLysAsnValMetValSerProSerIleThrValLysLeuAspAsnGlyLeuLysTrpThrGlyGlnTyrThrTyrAspAsnValGluArgThrProAsp
ArgSerProThrLysSerValTyrAspArgPheGlyLeuProTyrArgMetGlyPheAlaHisArgAsnAspPheValLysAspLysLeuGlnValTrpArgSerAspLeuGluTyrAlaPheAsn
AspLysTrpArgAlaGlnTrpGlnLeuAlaHisArgThrAlaAlaGlnAspPheAspHisPheTyrAlaGlySerGluAsnGlyAsnLeuIleLysArgAsnTyrAlaTrpGlnGlnThrAspAsn
LysThrLeuSerSerAsnLeuThrLeuAsnGlyAspTyrThrIleGlyArgPheGluAsnHisLeuThrValGlyMetAspTyrSerArgGluHisArgAsnProThrLeuGlyPheSerSerAla
PheSerAlaSerIleAsnProTyrAspArgAlaSerTrpProAlaSerGlyArgLeuGlnProIleLeuThrGlnAsnArgHisLysAlaAspSerTyrGlyIlePheValGlnAsnIlePheSerAlaThr
ProAspLeuLysPheValLeuGlyGlyArgTyrAspLysTyrThrPheAsnSerGluAsnLysLeuThrGlySerSerArgGlnTyrSerGlyHisSerPheSerProAsnIleGlyAlaValTrp
AsnIleAsnProValHisThrLeuTyrAlaSerTyrAsnLysGlyPheAlaProTyrGlyGlyArgGlyGlyTyrLeuSerIleAspThrLeuSerSerAlaValPheAsnAlaAspProGluTyrThr
ArgGlnTyrGluThrGlyValLysSerSerTrpLeuAspAspArgLeuSerThrThrLeuSerAlaTyrGlnIleGluArgPheAsnIleArgTyrArgProAspProLysAsnAsnProTyrIleTyr
AlaValSerGlyLysHisArgSerArgGlyValGluLeuSerAlaIleGlyGlnIleIleProLysLysLeuTyrLeuArgGlySerLeuGlyValMetGlnAlaLysValValGluAspLysGluAsn
ProAspArgValGlyIleHisLeuAsnAsnThrSerAsnValThrGlyAsnLeuPhePheArgTyrThrProThrGluAsnLeuTyrGlyGluIleGlyValThrGlyThrGlyLysArgTyrGly
TyrAspSerArgAsnLysGluValThrThrLeuProGlyPheAlaArgValAspAlaMetLeuGlyTrpAsnHisLysAsnValAsnValThrPheAlaAlaAlaAsnLeuPheAsnGlnLysTyr
TrpArgSerAspSerMetProGlyAsnProArgGlyTyrThrAlaArgValAsnTyrArgPhe-703
Hydrophilic Regions - Hopp-Woods
(SEQ. ID. NO. 24267)
1-MetLysIleSerPheHisLeuAlaLeuLeuProThrLeuIleIleAlaSerPheProValAlaAlaAlaAspThrGlnAspAsnGlyGluHisTyrThrAlaThrLeuProThrValSerValValGly
GlnSerAspThrSerValLeuLysGlyTyrIleAsnTyrAspGluAlaAlaValThrArgAsnGlyGlnLeuIleLysGluThrProGlnThrIleAspThrLeuAsnIleGlnLysAsnLysAsnTyr
GlyThrAsnAspLeuSerSerIleLeuGluGlyAsnAlaGlyIleAspAlaAlaTyrAspMetArgGlyGluSerIlePheLeuArgGlyPheGlnAlaAspAlaSerAspIleTyrArgAspGlyVal
ArgGluSerGlyGlnValArgArgSerThrAlaAsnIleGluArgValGluIleLeuLysGlyProSerSerValLeuTyrGlyArgThrAsnGlyGlyGlyValIleAsnMetValSerLysTyrAla
AsnPheLysGlnSerArgAsnIleGlyThrValTyrGlySerTrpAlaAsnArgSerLeuAsnMetAspIleAsnGluValLeuAsnLysAsnValAlaIleArgLeuThrGlyGluValGlyArg
AlaAsnSerPheArgSerGlyIleAspSerLysAsnValMetValSerProSerIleThrValLysLeuAspAsnGlyLeuLysTrpThrGlyGlnTyrThrTyrAspAsnValGluArgThrProAsp
ArgSerProThrLysSerValTyrAspArgPheGlyLeuProTyrArgMetGlyPheAlaHisArgAsnAspPheValLysAspLysLeuGlnValTrpArgSerAspLeuGluTyrAlaPheAsn
AspLysTrpArgAlaGlnTrpGlnLeuAlaHisArgThrAlaAlaGlnAspPheAspHisPheTyrAlaGlySerGluAsnGlyAsnLeuIleLysArgAsnTyrAlaTrpGlnGlnThrAspAsn
LysThrLeuSerSerAsnLeuThrLeuAsnGlyAspTyrThrIleGlyArgPheGluAsnHisLeuThrValGlyMetAspTyrSerArgGluHisArgAsnProThrLeuGlyPheSerSerAla
PheSerAlaSerIleAsnProTyrAspArgAlaSerTrpProAlaSerGlyArgLeuGlnProIleLeuThrGlnAsnArgHisLysAlaAspSerTyrGlyIlePheValGlnAsnIlePheSerAlaThr
ProAspLeuLysPheValLeuGlyGlyArgTyrAspLysTyrThrPheAsnSerGluAsnLysLeuThrGlySerSerArgGlnTyrSerGlyHisSerPheSerProAsnIleGlyAlaValTrpAsn
IleAsnProValHisThrLeuTyrAlaSerTyrAsnLysGlyPheAlaProTyrGlyGlyArgGlyGlyTyrLeuSerIleAspThrLeuSerSerAlaValPheAsnAlaAspProGluTyrThrArg
GlnTyrGluThrGlyValLysSerSerTrpLeuAspAspArgLeuSerThrThrLeuSerAlaTyrGlnIleGluArgPheAsnIleArgTyrArgProAspProLysAsnAsnProTyrIleTyrAla
ValSerGlyLysHisArgSerArgGlyValGluLeuSerAlaIleGlyGlnIleIleProLysLysLeuTyrLeuArgGlySerLeuGlyValMetGlnAlaLysValValGluAspLysGluAsnPro AspArgValGlyIleHisLeuAsnAsnThrSerAsnValThrGlyAsnLeuPhePheArgTyrThrProThrGluAsnLeuTyrGlyGluIleGlyValThrGlyThrGlyLysArgTyrGlyTyr AspSerArgAsnLysGluValThrThrLeuProGlyPheAlaArgValAspAlaMetLeuGlyTrpAsnHisLysAsnValAsnValThrPheAlaAlaAlaAsnLeuPheAsnGlnLysTyrTrp ArgSerAspSerMetProGlyAsnProArgGlyTyrThrAlaArgValAsnTyrArgPhe-703 a762

AMPHI Regions - AMPHI

SEQ. ID. NO. 24268 1-MetLysTrpLeuLeuAsnMetIleMetArgProIleLysPheSerMetValAsnThrLeuLeuPheIleValIleCysSerSerPhePheAspLeuLeuValGln LeuCysThrIleLeuPheHisSerGlnLysIleTyrPheIleThrLeuPheLeuLeuPheIlePheAsnPheValThrLysSerIleTyrMetAlaIleIleTyrPro IleLeuTyrPhePheThrIleLysLysTyrTyrProTyrSerArgLysValIleIleLeuLeuSerLeuAlaLeuSerIleTyrPheSerPheMetAspPheTyrPhe PheSerIleTyrSerAspAsnLeuSerTyrGluThrGluProLeuHisLeuTyrIleProIleIleAsnPhePheSerLeuLeuValSerAsnPheIleLeuSer PheIleAsnLys-147

Antigenic Index - Jameson-Wolf (SEQ. ID. NO. 24268)

1-MetLysTrpLeuLeuAsnMetIleMetArgProIleLysPheSerMetValAsnThrLeuLeuPheIleValIleCysSerSerPhePheAspLeuLeuValGlnLeuCysThrIleLeuPheHis SerGlnLysIleTyrPheIleThrLeuPheLeuLeuPheIlePheAsnPheValThrLysSerIleTyrMetAlaIleIleTyrProIleLeuTyrPhePheThrIleLysLysTyrTyrProTyrSerArgLys ValIleIleLeuLeuSerLeuAlaLeuSerIleTyrPheSerPheMetAspPheTyrPhePheSerIleTyrSerAspAsnLeuSerTyrGluThrGluProLeuHisLeuTyrIleProIleIleIleAsn PhePheSerLeuLeuValSerAsnPheIleLeuSerPheIleAsnLys-147

Hydrophilic Regions - Hopp-Woods (SEQ. ID. NO. 24268)

1-MetLysTrpLeuLeuAsnMetIleMetArgProIleLysPheSerMetValAsnThrLeuLeuPheIleValIleCysSerSerPhePheAspLeuLeuValGlnLeuCysThrIleLeuPheHis SerGlnLysIleTyrPheIleThrLeuPheLeuLeuPheIlePheAsnPheValThrLysSerIleTyrMetAlaIleIleTyrProIleLeuTyrPhePheThrIleLysLysTyrTyrProTyrSerArgLys ValIleIleLeuLeuSerLeuAlaLeuSerIleTyrPheSerPheMetAspPheTyrPhePheSerIleTyrSerAspAsnLeuSerTyrGluThrGluProLeuHisLeuTyrIleProIleIleIleAsn PhePheSerLeuLeuValSerAsnPheIleLeuSerPheIleAsnLys-147 a763

AMPHI Regions - AMPHI

SEQ. ID. NO. 24269 1-MetThrLeuLeuAsnLeuMetIleMetGlnAspTyrGlyIleSerValCysLeuThrLeuThrProTyrLeuGlnHisGluLeuPheSerAlaMetLysSer TyrPheSerLysTyrIleLeuProValSerLeuPheThrLeuProLeuSerLeuSerProSerValSerAlaPheThrLeuProGluAlaTrpArgAlaAlaGlnGln HisSerAlaAspPheGlnAlaSerHisTyrGlnArgAspAlaValArgAlaArgGlnGlnGlnAlaLysAlaAlaPheLeuProHisValSerAlaAsnAlaSer TyrGlnArgGlnProProSerIleSerSerThrArgGluThrGlnGlyTrpSerValGlnValGlyGlnThrLeuPheAspAlaAlaLysPheAlaGlnTyrArg GlnSerArgPheAspThrGlnAlaAlaGluGlnArgPheAspAlaAlaArgGluGluLeuLeuLeuLysValAlaGluSerTyrPheAsnValLeuLeuSer ArgAspThrValAlaAlaHisAlaAlaGluLysGluAlaTyrAlaGlnGlnValArgGlnAlaGlnAlaLeuPheAsnLysGlyAlaAlaThrAlaLeuAsp IleHisGluAlaLysAlaGlyTyrAspAsnAlaLeuAlaGlnGluIleAlaValLeuAlaGluLysGlnThrTyrGluAsnGlnLeuAsnAspTyrThrGlyLeu AspSerLysGlnIleGluAlaIleAspThrAlaAsnLeuLeuAlaArgTyrLeuProLysLeuGluArgTyrSerLeuAspGluTrpGlnArgIleAlaLeuSer AsnAsnHisGluTyrArgMetGlnGlnLeuAlaLeuGlnSerSerGlyGlnAlaLeuArgAlaAlaGlnAsnSerArgTyrProThrValSerAlaHisVal GlyTyrGlnAsnAsnLeuTyrThrSerSerAlaGlnAsnAsnAspTyrHisTyrArgGlyLysGlyMetSerValGlyValGlnLeuAsnLeuProLeuTyr ThrGlyGlyGluLeuSerGlyLysIleHisGluAlaGluAlaGlnTyrGlyAlaAlaGluAlaGlnLeuThrAlaThrGluArgHisIleLysLeuAlaValArg GlnAlaTyrThrGluSerGlyAlaAlaArgTyrGlnIleMetAlaGlnGluArgValLeuGluSerSerArgLeuLysLeuLysSerThrGluThrGlyGlnGln TyrGlyIleArgAsnArgLeuGluValIleArgAlaArgGlnGluValAlaGlnAlaGluGlnLysLeuAlaGlnAlaArgTyrLysPheMetLeuAlaTyrLeu ArgLeuValLysGluSerGlyLeuGlyLeuGluThrValPheAlaGlu-467

Antigenic Index - Jameson-Wolf (SEQ. ID. NO. 24269)

1-MetThrLeuLeuAsnLeuMetIleMetGlnAspTyrGlyIleSerValCysLeuThrLeuThrProTyrLeuGlnHisGluLeuPheSerAlaMetLysSerTyrPheSerLysTyrIleLeuPro ValSerLeuPheThrLeuProLeuSerLeuSerProSerValSerAlaPheThrLeuProGluAlaTrpArgAlaAlaGlnGlnHisSerAlaAspPheGlnAlaSerHisTyrGlnArgAspAlaVal ArgAlaArgGlnGlnGlnAlaLysAlaAlaPheLeuProHisValSerAlaAsnAlaSerTyrGlnArgGlnProProSerIleSerSerThrArgGluThrGlnGlyTrpSerValGlnValGlyGln ThrLeuPheAspAlaAlaLysPheAlaGlnTyrArgGlnSerArgPheAspThrGlnAlaAlaGluGlnArgPheAspAlaAlaArgGluGluLeuLeuLeuLysValAlaGluSerTyrPheAsn ValLeuLeuSerArgAspThrValAlaAlaHisAlaAlaGluLysGluAlaTyrAlaGlnGlnValArgGlnAlaGlnAlaLeuPheAsnLysGlyAlaAlaThrAlaLeuAspIleHisGluAla LysAlaGlyTyrAspAsnAlaLeuAlaGlnGluIleAlaValLeuAlaGluLysGlnThrTyrGluAsnGlnLeuAsnAspTyrThrGlyLeuAspSerLysGlnIleGluAlaIleAspThrAla AsnLeuLeuAlaArgTyrLeuProLysLeuGluArgTyrSerLeuAspGluTrpGlnArgIleAlaLeuSerAsnAsnHisGluTyrArgMetGlnGlnLeuAlaLeuGlnSerSerGlyGlnAla LeuArgAlaAlaGlnAsnSerArgTyrProThrValSerAlaHisValGlyTyrGlnAsnAsnLeuTyrThrSerSerAlaGlnAsnAsnAspTyrHisTyrArgGlyLysGlyMetSerValGly ValGlnLeuAsnLeuProLeuTyrThrGlyGlyGluLeuSerGlyLysIleHisGluAlaGluAlaGlnTyrGlyAlaAlaGluAlaGlnLeuThrAlaThrGluArgHisIleLysLeuAlaVal ArgGlnAlaTyrThrGluSerGlyAlaAlaArgTyrGlnIleMetAlaGlnGluArgValLeuGluSerSerArgLeuLysLeuLysSerThrGluThrGlyGlnGlnTyrGlyIleArgAsnArg LeuGluValIleArgAlaArgGlnGluValAlaGlnAlaGluGlnLysLeuAlaGlnAlaArgTyrLysPheMetLeuAlaTyrLeuArgLeuValLysGluSerGlyLeuGlyLeuGluThrVal PheAlaGlu-467

Hydrophilic Regions - Hopp-Woods (SEQ. ID. NO. 24269)

1-MetThrLeuLeuAsnLeuMetIleMetGlnAspTyrGlyIleSerValCysLeuThrLeuThrProTyrLeuGlnHisGluLeuPheSerAlaMetLysSerTyrPheSerLysTyrIleLeuPro ValSerLeuPheThrLeuProLeuSerLeuSerProSerValSerAlaPheThrLeuProGluAlaTrpArgAlaAlaGlnGlnHisSerAlaAspPheGlnAlaSerHisTyrGlnArgAspAlaVal ArgAlaArgGlnGlnGlnAlaLysAlaAlaPheLeuProHisValSerAlaAsnAlaSerTyrGlnArgGlnProProSerIleSerSerThrArgGluThrGlnGlyTrpSerValGlnValGlyGln ThrLeuPheAspAlaAlaLysPheAlaGlnTyrArgGlnSerArgPheAspThrGlnAlaAlaGluGlnArgPheAspAlaAlaArgGluGluLeuLeuLeuLysValAlaGluSerTyrPheAsn ValLeuLeuSerArgAspThrValAlaAlaHisAlaAlaGluLysGluAlaTyrAlaGlnGlnValArgGlnAlaGlnAlaLeuPheAsnLysGlyAlaAlaThrAlaLeuAspIleHisGluAla LysAlaGlyTyrAspAsnAlaLeuAlaGlnGluIleAlaValLeuAlaGluLysGlnThrTyrGluAsnGlnLeuAsnAspTyrThrGlyLeuAspSerLysGlnIleGluAlaIleAspThrAla AsnLeuLeuAlaArgTyrLeuProLysLeuGluArgTyrSerLeuAspGluTrpGlnArgIleAlaLeuSerAsnAsnHisGluTyrArgMetGlnGlnLeuAlaLeuGlnSerSerGlyGlnAla LeuArgAlaAlaGlnAsnSerArgTyrProThrValSerAlaHisValGlyTyrGlnAsnAsnLeuTyrThrSerSerAlaGlnAsnAsnAspTyrHisTyrArgGlyLysGlyMetSerValGly ValGlnLeuAsnLeuProLeuTyrThrGlyGlyGluLeuSerGlyLysIleHisGluAlaGluAlaGlnTyrGlyAlaAlaGluAlaGlnLeuThrAlaThrGluArgHisIleLysLeuAlaValArg GlnAlaTyrThrGluSerGlyAlaAlaArgTyrGlnIleMetAlaGlnGluArgValLeuGluSerSerArgLeuLysLeuLysSerThrGluThrGlyGlnGlnTyrGlyIleArgAsnArgLeuGlu ValIleArgAlaArgGlnGluValAlaGlnAlaGluGlnLysLeuAlaGlnAlaArgTyrLysPheMetLeuAlaTyrLeuArgLeuValLysGluSerGlyLeuGlyLeuGluThrValPheAla Glu-467 a764

AMPHI Regions - AMPHI

SEQ. ID. NO. 24270 1-MetPhePheSerAlaLeuLysSerPheLeuSerArgTyrIleThrValTrpArgAsnValTrpAlaValArgAspGlnLeuGluProProLysArgThrAla GluGluGlnAlaPheLeuProAlaHisLeuGluLeuThrAspThrProValSerAlaAlaProLysTrpAlaAlaArgPheIleMetAlaPheAlaLeuLeuAla LeuLeuTrpSerTrpPheGlyLysIleAspIleValAlaAlaAlaSerGlyLysThrValSerGlyGlyArgSerLysThrIleGlnProLeuGluThrValValVal LysAlaValHisValArgAspGlyGlnHisValLysGlnGlyGluThrLeuAlaGluLeuGluAlaValGlyThrAspSerAspValValGlnSerGluGln AlaLeuGlnAlaAlaGlnLeuSerLysLeuArgTyrGluAlaValLeuAlaAlaLeuGluSerArgThrValProHisIleAspMetAlaGlnAlaArgSerLeu GlyLeuSerAspAlaAspValGlnSerAlaGlnValLeuAlaGlnHisGlnTyrGlnAlaTrpAlaAlaGlnAspAlaGlnLeuGlnSerAlaLeuArgGly HisGlnAlaGluLeuGlnSerAlaLysAlaGlnGluGlnLysLeuValSerValGlyAlaIleGluGlnGlnLysThrAlaAspTyrArgArgLeuArgAlaAsp AsnPheIleSerGluHisAlaPheLeuGluGlnGlnSerLysSerValSerAsnTrpAsnAspLeuGluSerThrArgGlyGlnMetArgGlnIleGlnAlaAla IleAlaGlnAlaGluGlnAsnArgValLeuAsnThrGlnAsnLeuLysArgAspThrLeuAspAlaLeuArgGlnAlaAsnGluGlnIleAspGlnTyrArg GlyGlnThrAspLysAlaLysGlnArgGlnGlnLeuMetThrIleGlnSerProAlaAspGlyThrValGlnGluLeuAlaThrTyrThrValGlyGlyValVal GlnAlaAlaGlnLysMetMetValValAlaProAspAspAspLysMetAspValGluValLeuValLeuAsnLysAspIleGlyPheValGluGlnGlyGln

AspAlaValValLysIleGluSerPheProTyrThrArgTyrGlyTyrLeuThrGlyLysValLysSerValSerHisAspAlaValSerHisGluGlnLeuGly LeuValTyrThrAlaValValSerLeuAspLysHisThrLeuAsnIleAspGlyLys-435
Antigenic Index - Jameson-Wolf
(SEQ. ID. NO. 24270)
1-MetPhePheSerAlaLeuLysSerPheLeuSerArgTyrIleThrValTrpArgAsnValTrpAlaValArgAspGlnLeuGluProProLysArgThrAlaGluGluGlnAlaPheLeuProAla HisLeuGluLeuThrAspThrProValSerAlaAlaProLysTrpAlaAlaArgPheIleMetAlaPheAlaLeuLeuAlaLeuLeuTrpSerTrpPheGlyLysIleAspIleValAlaAlaAlaSer GlyLysThrValSerGlyGlyArgSerLysThrIleGlnProLeuGluThrValValValLysAlaValHisValArgAspGlyGlnHisValLysGlnGlyGluThrLeuAlaGluLeuGluAla ValGlyThrAspSerAspValValGlnSerGluGlnAlaLeuGlnAlaAlaGlnLeuSerLysLeuArgTyrGluAlaValLeuAlaAlaLeuGluSerArgThrValProHisIleAspMetAla GlnAlaArgSerLeuGlyLeuSerAspAlaAspValGlnSerAlaGlnValLeuAlaGlnHisGlnTyrGlnAlaTrpAlaAlaGlnAspAlaGlnLeuGlnSerAlaLeuArgGlyHisGlnAla GluLeuGlnSerAlaLysAlaGlnGluGlnLysLeuValSerValGlyAlaIleGluGlnGlnLysThrAlaAspTyrArgArgLeuArgAlaAspAsnPheIleSerGluHisAlaPheLeuGlu GlnGlnSerLysSerValSerAsnTrpAsnAspLeuGluSerThrArgGlyGlnMetArgGlnIleGlnAlaAlaIleAlaGlnAlaGluGlnAsnArgValLeuAsnThrGlnAsnLeuLysArg AspThrLeuAspAlaLeuArgGlnAlaAsnGluGlnIleAspGlnTyrArgGlyGlnThrAspLysAlaLysGlnArgGlnGlnLeuMetThrIleGlnSerProAlaAspGlyThrValGln GluLeuAlaThrTyrThrValGlyGlyValValGlnAlaAlaGlnLysMetMetValValAlaProAspAspAspLysMetAspValGluValLeuValLeuAsnLysAspIleGlyPheVal GluGlnGlyGlnAspAlaValValLysIleGluSerPheProTyrThrArgTyrGlyTyrLeuThrGlyLysValLysSerValSerHisAspAlaValSerHisGluGlnLeuGlyLeuValTyr ThrAlaValValSerLeuAspLysHisThrLeuAsnIleAspGlyLys-435
Hydrophilic Regions - Hopp-Woods
(SEQ. ID. NO. 24270)
1-MetPhePheSerAlaLeuLysSerPheLeuSerArgTyrIleThrValTrpArgAsnValTrpAlaValArgAspGlnLeuGluProProLysArgThrAlaGluGluGlnAlaPheLeuProAla HisLeuGluLeuThrAspThrProValSerAlaAlaProLysTrpAlaAlaArgPheIleMetAlaPheAlaLeuLeuAlaLeuLeuTrpSerTrpPheGlyLysIleAspIleValAlaAlaAlaSer GlyLysThrValSerGlyGlyArgSerLysThrIleGlnProLeuGluThrValValValLysAlaValHisValArgAspGlyGlnHisValLysGlnGlyGluThrLeuAlaGluLeuGluAla ValGlyThrAspSerAspValValGlnSerGluGlnAlaLeuGlnAlaAlaGlnLeuSerLysLeuArgTyrGluAlaValLeuAlaAlaLeuGluSerArgThrValProHisIleAspMetAla GlnAlaArgSerLeuGlyLeuSerAspAlaAspValGlnSerAlaGlnValLeuAlaGlnHisGlnTyrGlnAlaTrpAlaAlaGlnAspAlaGlnLeuGlnSerAlaLeuArgGlyHisGlnAla GluLeuGlnSerAlaLysAlaGlnGluGlnLysLeuValSerValGlyAlaIleGluGlnGlnLysThrAlaAspTyrArgArgLeuArgAlaAspAsnPheIleSerGluHisAlaPheLeuGlu GlnGlnSerLysSerValSerAsnTrpAsnAspLeuGluSerThrArgGlyGlnMetArgGlnIleGlnAlaAlaIleAlaGlnAlaGluGlnAsnArgValLeuAsnThrGlnAsnLeuLysArg AspThrLeuAspAlaLeuArgGlnAlaAsnGluGlnIleAspGlnTyrArgGlyGlnThrAspLysAlaLysGlnArgGlnGlnLeuMetThrIleGlnSerProAlaAspGlyThrValGln GluLeuAlaThrTyrThrValGlyGlyValValGlnAlaAlaGlnLysMetMetValValAlaProAspAspAspLysMetAspValGluValLeuValLeuAsnLysAspIleGlyPheVal GluGlnGlyGlnAspAlaValValLysIleGluSerPheProTyrThrArgTyrGlyTyrLeuThrGlyLysValLysSerValSerHisAspAlaValSerHisGluGlnLeuGlyLeuValTyr ThrAlaValValSerLeuAspLysHisThrLeuAsnIleAspGlyLys-435
a765
AMPHI Regions - AMPHI
SEQ. ID. NO. 24271 36-SerAlaIleSerSerPheCys-42
SEQ. ID. NO. 24272 45-LysIleIleHisThrTyr-50
SEQ. ID. NO. 24273 59-ValIleGlyIleIleAsnGly-65
SEQ. ID. NO. 24274 105-ArgPheLeuAsnArgGly-110
SEQ. ID. NO. 24275 147-PheGlyLeuCysTyrPro-152
Antigenic Index - Jameson-Wolf
SEQ. ID. NO. 24276 10-GlyAsnPheLysLysIleAlaThr-17
SEQ. ID. NO. 24277 19-GlnGlyLeuAspArgLysTyr-25
SEQ. ID. NO. 24278 76-ValLysAsnLysGlnLysPheLeu-83
SEQ. ID. NO. 24279 106-PheLeuAsnArgGlyMetLys-112
SEQ. ID. NO. 24280 132-LeuAsnGluGluGlyGlyTrpMet-139
SEQ. ID. NO. 24281 160-LeuSerArgAspTyrLysHisIle-167
Hydrophilic Regions - Hopp-Woods
SEQ. ID. NO. 24282 11-AsnPheLysLysIleAlaThr-17
SEQ. ID. NO. 24283 19-GlnGlyLeuAspArgLys-24
SEQ. ID. NO. 24284 76-ValLysAsnLysGlnLysPheLeu-83
SEQ. ID. NO. 24285 133-AsnGluGluGlyGly-137
SEQ. ID. NO. 24286 162-ArgAspTyrLysHis-166
a767
AMPHI Regions - AMPHI
SEQ. ID. NO. 24287 42-LysIleGluValLeuGluPhePheGlyTyrPheCysVal-54
SEQ. ID. NO. 24288 89-GlyLeuAlaArgMetAlaAlaAlaValLys-98
SEQ. ID. NO. 24289 140-LysLysLeuMetArgAlaTyrAspSerProAlaAla-151
SEQ. ID. NO. 24290 156-SerLysMetGlnGlnLeuThrGluGlnTyrArg-166
SEQ. ID. NO. 24291 187-PheAspGlyGlyValHisThrIleLysGluLeuValAla-199
Antigenic Index - Jameson-Wolf
SEQ. ID. NO. 24292 23-ThrGluGlyGluAspTyrLeuVal-30
SEQ. ID. NO. 24293 33-LysProIleProGlnLysGlnSerGlyLysIleGluVal-45
SEQ. ID. NO. 24294 70-LeuProSerAspAlaTyrLeuArg-77
SEQ. ID. NO. 24295 99-LeuSerGlyLeuLysTyrGlnAla-106
SEQ. ID. NO. 24296 115-TyrGluGlnLysIleArgLeuGluAsnArgSerValAlaGlu-128
SEQ. ID. NO. 24297 130-TrpAlaLeuSerGlnLysGlyPheAspGlyLysLysLeuMetArgAlaTyrAspSerProAla-150
SEQ. ID. NO. 24298 156-SerLysMetGlnGlnLeuThrGluGlnTyrArgIleAspSerThrProThr-172
SEQ. ID. NO. 24299 175-ValGlyGlyLysTyrArgVal-181
SEQ. ID. NO. 24300 183-PheAsnAsnGlyPheAspGlyGly-190
SEQ. ID. NO. 24301 197-LeuValAlaLysValArgGluGluArgLysArgGlnThrProAlaValGlnLys-214
Hydrophilic Regions - Hopp-Woods
SEQ. ID. NO. 24302 23-ThrGluGlyGluAsp-27
SEQ. ID. NO. 24303 33-LysProIleProGlnLysGlnSerGlyLysIleGluVal-45
SEQ. ID. NO. 24304 115-TyrGluGlnLysIleArgLeuGluAsnArgSerValAlaGlu-128
SEQ. ID. NO. 24305 135-LysGlyPheAspGlyLysLysLeuMetArgAlaTyrAsp-147
SEQ. ID. NO. 24306 156-SerLysMetGlnGlnLeu-161
SEQ. ID. NO. 24307 165-TyrArgIleAspSer-169
SEQ. ID. NO. 24308 197-LeuValAlaLysValArgGluGluArgLysArgGlnThrProAlaValGlnLys-214
a768
AMPHI Regions - AMPHI
SEQ. ID. NO. 24309 1-MetAsnIleLysHisLeuIleThrAlaAlaLeuIleAlaSerAlaAlaPheAlaAlaGlnAlaAlaProGlnLysProValSerAlaAlaGlnThrAlaGlnHis SerAlaValTrpIleAspValArgSerGluGlnGluPheSerGluGlyHisLeuHisAsnAlaValAsnIleProValAspGlnIleValArgArgIleHisGluAla TABLE 1-continued AlaProAspLysAspThrProValAsnLeuTyrCysArgSerGlyArgArgAlaGluAlaAlaLeuGlnGluLeuLysLysAlaGlyTyrThrAsnValAla
AsnHisGlyGlyTyrGluAspLeuLeuLysLysGlyMetLys
Antigenic Index - Jameson-Wolf
(SEQ. ID. NO. 24309)
1-MetAsnIleLysHisLeuIleThrAlaAlaLeuIleAlaSerAlaAlaPheAlaAlaGlnAlaAlaProGlnLysProValSerAlaAlaGlnThrAlaGlnHisSerAlaValTrpIleAspValArg
SerGluGlnGluPheSerGluGlyHisLeuHisAsnAlaValAsnIleProValAspGlnIleValArgArgIleHisGluAlaAlaProAspLysAspThrProValAsnLeuTyrCysArgSerGly
ArgArgAlaGluAlaAlaLeuGlnGluLeuLysLysAlaGlyTyrThrAsnValAlaAsnHisGlyGlyTyrGluAspLeuLeuLysLysGlyMetLys
Hydrophilic Regions - Hopp-Woods
(SEQ. ID. NO. 24309)
1-MetAsnIleLysHisLeuIleThrAlaAlaLeuIleAlaSerAlaAlaPheAlaAlaGlnAlaAlaProGlnLysProValSerAlaAlaGlnThrAlaGlnHisSerAlaValTrpIleAspValArg
SerGluGlnGluPheSerGluGlyHisLeuHisAsnAlaValAsnIleProValAspGlnIleValArgArgIleHisGluAlaAlaProAspLysAspThrProValAsnLeuTyrCysArgSerGly
ArgArgAlaGluAlaAlaLeuGlnGluLeuLysLysAlaGlyTyrThrAsnValAlaAsnHisGlyGlyTyrGluAspLeuLeuLysLysGlyMetLys-119
a769
AMPHI Regions - AMPHI
SEQ. ID. NO. 24310 1-LeuIleMetValIlePheTyrPheCysGlyLysThrPheMetProAlaArgAsnArgTrpMetLeuLeuLeuProLeuLeuAlaSerAlaAlaTyrAlaGlu
GluThrProArgGluProAspLeuArgSerArgProGluPheArgLeuHisGluAlaGluValLysProIleAspArgGluLysValProGlyGlnValArgGlu
LysGlyLysValLeuGlnIleAspGlyGluThrLeuLeuLysAsnProGluLeuLeuSerArgAlaMetTyrSerAlaValValSerAsnAsnIleAlaGlyIle
ArgValIleLeuProIleTyrLeuGlnGlnAlaGlnGlnAspLysMetLeuAlaLeuTyrAlaGlnGlyIleLeuAlaGlnAlaAspGlyArgValLysGluAla
IleSerHisTyrArgGluLeuIleValAlaGlnProAspAlaProAlaValArgMetArgLeuAlaAlaAlaLeuPheGluAsnArgGlnAsnGluAlaAlaAla
AspGlnPheAspArgLeuLysAlaGluAsnLeuProProGlnLeuMetGluGlnValGluLeuTyrArgLysAlaLeuArgGluArgAspAlaTrpLysVal
AsnGlyGlyPheSerValThrArgGluHisAsnIleAsnGlnAlaProLysArgGlnGlnTyrGlyLysTrpThrPheProLysGlnValAspGlyThrAlaVal
AsnTyrArgLeuGlyAlaGluLysLysTrpSerLeuLysAsnGlyTrpTyrThrThrAlaGlyGlyAspValSerGlyArgValTyrProGlyAsnLysLys
PheAsnAspMetThrAlaGlyValSerGlyGlyIleGlyPheAlaAspArgArgLysAspAlaGlyLeuAlaValPheHisGluArgArgThrTyrGlyAsn
AspAlaTyrSerTyrThrAsnGlyAlaArgLeuTyrPheAsnArgTrpGlnThrProLysTrpGlnThrLeuSerSerAlaGluTrpGlyArgLeuLysAsn
ThrArgArgAlaArgSerAspAsnThrHisLeuGlnIleSerAsnSerLeuValPheTyrArgAsnAlaArgGlnTyrTrpMetGlyGlyLeuAspPheTyr
ArgGluArgAsnProAlaAspArgGlyAspAsnPheAsnArgTyrGlyLeuArgPheAlaTrpGlyGlnGluTrpGlyGlySerGlyLeuSerSerLeuLeu
ArgLeuGlyAlaAlaLysArgHisTyrGluLysProGlyPhePheSerGlyPheLysGlyGluArgArgArgAspLysGluLeuAsnThrSerLeuSerLeu
TrpHisArgAlaLeuHisPheLysGlyIleThrProArgLeuThrLeuSerHisArgGluThrArgSerAsnAspValPheAsnGluTyrGluLysAsnArg
AlaPheValGluPheAsnLysThrPhe-490
Antigenic Index - Jameson-Wolf
(SEQ. ID. NO. 24310)
1-LeuIleMetValIlePheTyrPheCysGlyLysThrPheMetProAlaArgAsnArgTrpMetLeuLeuLeuProLeuLeuAlaSerAlaAlaTyrAlaGluGluThrProArgGluProAsp
LeuArgSerArgProGluPheArgLeuHisGluAlaGluValLysProIleAspArgGluLysValProGlyGlnValArgGluLysGlyLysValLeuGlnIleAspGlyGluThrLeuLeu
LysAsnProGluLeuLeuSerArgAlaMetTyrSerAlaValValSerAsnAsnIleAlaGlyIleArgValIleLeuProIleTyrLeuGlnGlnAlaGlnGlnAspLysMetLeuAlaLeuTyr
AlaGlnGlyIleLeuAlaGlnAlaAspGlyArgValLysGluAlaIleSerHisTyrArgGluLeuIleValAlaGlnProAspAlaProAlaValArgMetArgLeuAlaAlaAlaLeuPheGlu
AsnArgGlnAsnGluAlaAlaAlaAspGlnPheAspArgLeuLysAlaGluAsnLeuProProGlnLeuMetGluGlnValGluLeuTyrArgLysAlaLeuArgGluArgAspAlaTrp
LysValAsnGlyGlyPheSerValThrArgGluHisAsnIleAsnGlnAlaProLysArgGlnGlnTyrGlyLysTrpThrPheProLysGlnValAspGlyThrAlaValAsnTyrArgLeu
GlyAlaGluLysLysTrpSerLeuLysAsnGlyTrpTyrThrThrAlaGlyGlyAspValSerGlyArgValTyrProGlyAsnLysLysPheAsnAspMetThrAlaGlyValSerGlyGly
IleGlyPheAlaAspArgArgLysAspAlaGlyLeuAlaValPheHisGluArgArgThrTyrGlyAsnAspAlaTyrSerTyrThrAsnGlyAlaArgLeuTyrPheAsnArgTrpGlnThr
ProLysTrpGlnThrLeuSerSerAlaGluTrpGlyArgLeuLysAsnThrArgArgAlaArgSerAspAsnThrHisLeuGlnIleSerAsnSerLeuValPheTyrArgAsnAlaArgGln
TyrTrpMetGlyGlyLeuAspPheTyrArgGluArgAsnProAlaAspArgGlyAspAsnPheAsnArgTyrGlyLeuArgPheAlaTrpGlyGlnGluTrpGlyGlySerGlyLeuSe
rSerLeuLeuArgLeuGlyAlaAlaLysArgHisTyrGluLysProGlyPhePheSerGlyPheLysGlyGluArgArgArgAspLysGluLeuAsnThrSerLeuSerLeuTrpHisArgAla
LeuHisPheLysGlyIleThrProArgLeuThrLeuSerHisArgGluThrArgSerAsnAspValPheAsnGluTyrGluLysAsnArgAlaPheValGluPheAsnLysThrPhe-490
Hydrophilic Regions - Hopp-Woods
(SEQ. ID. NO. 24310)
1-LeuIleMetValIlePheTyrPheCysGlyLysThrPheMetProAlaArgAsnArgTrpMetLeuLeuLeuProLeuLeuAlaSerAlaAlaTyrAlaGluGluThrProArgGluProAsp
LeuArgSerArgProGluPheArgLeuHisGluAlaGluValLysProIleAspArgGluLysValProGlyGlnValArgGluLysGlyLysValLeuGlnIleAspGlyGluThrLeuLeuLys
AsnProGluLeuLeuSerArgAlaMetTyrSerAlaValValSerAsnAsnIleAlaGlyIleArgValIleLeuProIleTyrLeuGlnGlnAlaGlnGlnAspLysMetLeuAlaLeuTyrAla
GlnGlyIleLeuAlaGlnAlaAspGlyArgValLysGluAlaIleSerHisTyrArgGluLeuIleValAlaGlnProAspAlaProAlaValArgMetArgLeuAlaAlaAlaLeuPheGluAsn
ArgGlnAsnGluAlaAlaAlaAspGlnPheAspArgLeuLysAlaGluAsnLeuProProGlnLeuMetGluGlnValGluLeuTyrArgLysAlaLeuArgGluArgAspAlaTrpLys
ValAsnGlyGlyPheSerValThrArgGluHisAsnIleAsnGlnAlaProLysArgGlnGlnTyrGlyLysTrpThrPheProLysGlnValAspGlyThrAlaValAsnTyrArgLeuGly
AlaGluLysLysTrpSerLeuLysAsnGlyTrpTyrThrThrAlaGlyGlyAspValSerGlyArgValTyrProGlyAsnLysLysPheAsnAspMetThrAlaGlyValSerGlyGlyIle
GlyPheAlaAspArgArgLysAspAlaGlyLeuAlaValPheHisGluArgArgThrTyrGlyAsnAspAlaTyrSerTyrThrAsnGlyAlaArgLeuTyrPheAsnArgTrpGlnThrPro
LysTrpGlnThrLeuSerSerAlaGluTrpGlyArgLeuLysAsnThrArgArgAlaArgSerAspAsnThrHisLeuGlnIleSerAsnSerLeuValPheTyrArgAsnAlaArgGlnTyr
TrpMetGlyGlyLeuAspPheTyrArgGluArgAsnProAlaAspArgGlyAspAsnPheAsnArgTyrGlyLeuArgPheAlaTrpGlyGlnGluTrpGlyGlySerGlyLeuSerSer
LeuLeuArgLeuGlyAlaAlaLysArgHisTyrGluLysProGlyPhePheSerGlyPheLysGlyGluArgArgArgAspLysGluLeuAsnThrSerLeuSerLeuTrpHisArgAlaLeu
HisPheLysGlyIleThrProArgLeuThrLeuSerHisArgGluThrArgSerAsnAspValPheAsnGluTyrGluLysAsnArgAlaPheValGluPheAsnLysThrPhe-490
a770
AMPHI Regions - AMPHI
SEQ. ID. NO. 24311 1-MetAsnArgLeuLeuLeuLeuSerAlaAlaValLeuLeuThrAlaCysGlySerGlyGluThrAspLysIleGlyArgAlaSerThrValPheAsnIleLeu
GlyLysAsnAspArgIleGluValGluGlyPheAspAspProAspValGlnGlyValAlaCysTyrIleSerTyrAlaLysLysGlyGlyLeuLysGluMetVal
AsnLeuGluGluAspAlaSerAspAlaSerValSerCysValGlnThrAlaSerSerIleSerPheAspGluThrAlaValArgLysProLysGluValPheLys
HisGlyAlaSerPheAlaPheLysSerArgGlnIleValArgTyrTyrAspProLysArgLysThrPheAlaTyrLeuValTyrSerAspLysIleIleGlnGly
SerProLysAsnSerLeuSerAlaValSerCysPheGlyGlyGlyIleProGlnThrAspGlyValGlnAlaAspThrSerGlyAsnLeuLeuAlaGlyAla
CysMetIleSerAsnProIleGluAsnProAspLysArg-186
Antigenic Index - Jameson-Wolf
(SEQ. ID. NO. 24311)
1-MetAsnArgLeuLeuLeuLeuSerAlaAlaValLeuLeuThrAlaCysGlySerGlyGluThrAspLysIleGlyArgAlaSerThrValPheAsnIleLeuGlyLysAsnAspArgIleGlu
ValGluGlyPheAspAspProAspValGlnGlyValAlaCysTyrIleSerTyrAlaLysLysGlyGlyLeuLysGluMetValAsnLeuGluGluAspAlaSerAspAlaSerValSerCys
ValGlnThrAlaSerSerIleSerPheAspGluThrAlaValArgLysProLysGluValPheLysHisGlyAlaSerPheAlaPheLysSerArgGlnIleValArgTyrTyrAspProLysArg
LysThrPheAlaTyrLeuValTyrSerAspLysIleIleGlnGlySerProLysAsnSerLeuSerAlaValSerCysPheGlyGlyGlyIleProGlnThrAspGlyValGlnAlaAspThrSer
GlyAsnLeuLeuAlaGlyAlaCysMetIleSerAsnProIleGluAsnProAspLysArg-186
Hydrophilic Regions - Hopp-Woods
(SEQ. ID. NO. 24311)
1-MetAsnArgLeuLeuLeuLeuSerAlaAlaValLeuLeuThrAlaCysGlySerGlyGluThrAspLysIleGlyArgAlaSerThrValPheAsnIleLeuGlyLysAsnAspArgIleGlu
ValGluGlyPheAspAspProAspValGlnGlyValAlaCysTyrIleSerTyrAlaLysLysGlyGlyLeuLysGluMetValAsnLeuGluGluAspAlaSerAspAlaSerValSerCys TABLE 1-continued ValGlnThrAlaSerSerIleSerPheAspGluThrAlaValArgLysProLysGluValPheLysHisGlyAlaSerPheAlaPheLysSerArgGlnIleValArgTyrTyrAspProLysArg
LysThrPheAlaTyrLeuValTyrSerAspLysIleIleGlnGlySerProLysAsnSerLeuSerAlaValSerCysPheGlyGlyGlyIleProGlnThrAspGlyValGlnAlaAspThrSer
GlyAsnLeuLeuAlaGlyAlaCysMetIleSerAsnProIleGluAsnProAspLysArg-186 a771

AMPHI Regions - AMPHI

SEQ. ID. NO. 24312 1-MetAspLeuLeuSerValPheHisLysTyrArgLeuLysTyrAlaValAlaValLeuThrIleLeuLeuLeuAlaAlaIleGlyLeuHisAlaSerValTyr
ArgIlePheThrProGluAsnIleArgSerArgLeuGlnGlnSerIleAlaHisThrHisArgLysIleSerPheAspAlaAspIleGlnArgArgLeuLeuPro
ArgProThrValIleLeuLysAsnLeuThrIleThrGluProGlyGlyAspArgThrAlaValSerValGlnGluThrLysIleGlyLeuSerTrpLysAsnLeu
TrpSerAspGlnIleGlnIleGluLysTrpValValSerSerAlaGluLeuAlaLeuThrArgAspGlyLysGlyValTrpAsnIleGlnAspLeuIleAspSer
GlnLysArgGlnAlaSerValAsnArgIleIleValGluAsnSerThrValArgLeuAsnPheLeuGlnGluGlnLeuIleLeuLysGluIleAsnLeuAsnLeu
GlnSerProAspSerSerGlyGlnProPheGluSerSerGlyIleLeuValTrpGlyLysLeuSerValProTrpLysSerArgGlyLeuPheLeuSerAspGly
IleGlyThrProLysIleSerProPheHisPheGluAlaSerThrSerLeuAspGlyHisGlyIleThrIleSerThrThrGlySerProSerValArgPheAsnAla
GlyGlyAlaAspAlaAlaGlyLeuGlyLeuArgAlaAspThrSerPheArgAsnLeuHisLeuThrAlaGlnIleProThrLeuAlaLeuArgAsnAsn
SerIleLysIleGluThrValAsnGlyAlaPheThrAlaGlyGlyGluTyrAlaGlnTrpAspGlySerPheLysLeuAspLysAlaAsnLeuHisSerGlyIle
AlaAsnIleGlyAsnAlaGluIleSerGlySerPheLysThrProArgHisGlnThrAsnPheSerLeuAsnSerProLeuValTrpThrGluAsnLysGlyLeu
AspAlaProArgLeuTyrValSerThrLeuGlnAspThrValAsnArgLeuProGlnProArgPheIleSerArgLeuAspGlySerLeuSerValProAsn
LeuGlnAsnTrpAsnAlaGluLeuAsnGlyThrPheAspArgGlnThrValAlaAlaLysPheArgTyrThrHisGluAspAlaProHisLeuGluAlaAla
ValAlaLeuGlnLysLeuAsnLeuThrProTyrLeuAspAspValArgGlnGlnAsnGlyLysIlePheProAspThrLeuAlaLysLeuSerGlyAspIle
GluAlaHisLeuLysIleGlyLysValGlnLeuProGlyLeuGlnLeuAspAspMetGluThrTyrLeuHisAlaAspLysGlyHisIleAlaLeuSerArg
PheLysSerGlyLeuTyrGlyGlyHisThrGluGlyGlyIleSerIleAlaAsnThrArgProAlaThrTyrArgLeuGlnGlnAsnAlaSerAsnIleGlnIle
GlnProLeuLeuGlnAspLeuPheGlyPheHisSerPheSerGlyAsnGlyAspAlaValIleAspLeuThrAlaGlyGlyGluThrArgLysGluLeuIle
ArgSerLeuGlnGlySerLeuSerLeuAsnIleSerAsnGlyAlaTrpHisGlyIleAspMetAspAsnIleLeuLysAsnGlyIleSerGlyLysThrAla
AspAsnAlaAlaProSerThrProPheHisArgPheThrLeuAsnSerGluIleSerAspGlyIleSerArgHisIleAspThrGluLeuPheSerAspSerLeu
TyrValThrSerAsnGlyTyrThrAsnLeuAspThrGlnGluLeuSerGluAspValLeuIleArgAsnAlaValHisProLysAsnLysProIleProLeu
LysIleThrGlyThrValAspLysProSerIleThrValAspTyrGlyArgLeuThrGlyGlyIleAsnSerArgLysGluLysGlnLysIleLeuGluAsp
ThrLeuLeuGluGlnTrpGlnTrpLeuLysProLysGluPro-704

Antigenic Index - Jameson-Wolf (SEQ. ID. NO. 24312)

1-MetAspLeuLeuSerValPheHisLysTyrArgLeuLysTyrAlaValAlaValLeuThrIleLeuLeuLeuAlaAlaIleGlyLeuHisAlaSerValTyrArgIlePheThrProGluAsnIle
ArgSerArgLeuGlnGlnSerIleAlaHisThrHisArgLysIleSerPheAspAlaAspIleGlnArgArgLeuLeuProArgProThrValIleLeuLysAsnLeuThrIleThrGluProGlyGly
AspArgThrAlaValSerValGlnGluThrLysIleGlyLeuSerTrpLysAsnLeuTrpSerAspGlnIleGlnIleGluLysTrpValValSerSerAlaGluLeuAlaLeuThrArgAspGlyLys
GlyValTrpAsnIleGlnAspLeuIleAspSerGlnLysArgGlnAlaSerValAsnArgIleIleValGluAsnSerThrValArgLeuAsnPheLeuGlnGluGlnLeuIleLeuLysGluIleAsn
LeuAsnLeuGlnSerProAspSerSerGlyGlnProPheGluSerSerGlyIleLeuValTrpGlyLysLeuSerValProTrpLysSerArgGlyLeuPheLeuSerAspGlyIleGlyThrProLys
IleSerProPheHisPheGluAlaSerThrSerLeuAspGlyHisGlyIleThrIleSerThrThrGlySerProSerValArgPheAsnAlaGlyGlyAlaAspAlaAlaGlyLeuGlyLeuArgAla
AspThrSerPheArgAsnLeuHisLeuThrAlaGlnIleProThrLeuAlaLeuArgAsnAsnSerIleLysIleGluThrValAsnGlyAlaPheThrAlaGlyGlyGluTyrAlaGlnTrpAsp
GlySerPheLysLeuAspLysAlaAsnLeuHisSerGlyIleAlaAsnIleGlyAsnAlaGluIleSerGlySerPheLysThrProArgHisGlnThrAsnPheSerLeuAsnSerProLeuValTrp
ThrGluAsnLysGlyLeuAspAlaProArgLeuTyrValSerThrLeuGlnAspThrValAsnArgLeuProGlnProArgPheIleSerArgLeuAspGlySerLeuSerValProAsnLeuGln
AsnTrpAsnAlaGluLeuAsnGlyThrPheAspArgGlnThrValAlaAlaLysPheArgTyrThrHisGluAspAlaProHisLeuGluAlaAlaValAlaLeuGlnLysLeuAsnLeuThrPro
TyrLeuAspAspValArgGlnGlnAsnGlyLysIlePheProAspThrLeuAlaLysLeuSerGlyAspIleGluAlaHisLeuLysIleGlyLysValGlnLeuProGlyLeuGlnLeuAspAsp
MetGluThrTyrLeuHisAlaAspLysGlyHisIleAlaLeuSerArgPheLysSerGlyLeuTyrGlyGlyHisThrGluGlyGlyIleSerIleAlaAsnThrArgProAlaThrTyrArgLeu
GlnGlnAsnAlaSerAsnIleGlnIleGlnProLeuLeuGlnAspLeuPheGlyPheHisSerPheSerGlyAsnGlyAspAlaValIleAspLeuThrAlaGlyGlyGluThrArgLysGluLeu
IleArgSerLeuGlnGlySerLeuSerLeuAsnIleSerAsnGlyAlaTrpHisGlyIleAspMetAspAsnIleLeuLysAsnGlyIleSerGlyLysThrAlaAspAsnAlaAlaProSerThrPro
PheHisArgPheThrLeuAsnSerGluIleSerAspGlyIleSerArgHisIleAspThrGluLeuPheSerAspSerLeuTyrValThrSerAsnGlyTyrThrAsnLeuAspThrGlnGluLeu
SerGluAspValLeuIleArgAsnAlaValHisProLysAsnLysProIleProLeuLysIleThrGlyThrValAspLysProSerIleThrValAspTyrGlyArgLeuThrGlyGlyIleAsnSer
ArgLysGluLysGlnLysIleLeuGluAspThrLeuLeuGluGlnTrpGlnTrpLeuLysProLysGluPro-704

Hydrophilic Regions - Hopp-Woods (SEQ. ID. NO. 24312)

1-MetAspLeuLeuSerValPheHisLysTyrArgLeuLysTyrAlaValAlaValLeuThrIleLeuLeuLeuAlaAlaIleGlyLeuHisAlaSerValTyrArgIlePheThrProGluAsnIleArg
SerArgLeuGlnGlnSerIleAlaHisThrHisArgLysIleSerPheAspAlaAspIleGlnArgArgLeuLeuProArgProThrValIleLeuLysAsnLeuThrIleThrGluProGlyGlyAsp
ArgThrAlaValSerValGlnGluThrLysIleGlyLeuSerTrpLysAsnLeuTrpSerAspGlnIleGlnIleGluLysTrpValValSerSerAlaGluLeuAlaLeuThrArgAspGlyLysGly
ValTrpAsnIleGlnAspLeuIleAspSerGlnLysArgGlnAlaSerValAsnArgIleIleValGluAsnSerThrValArgLeuAsnPheLeuGlnGluGlnLeuIleLeuLysGluIleAsnLeu
AsnLeuGlnSerProAspSerSerGlyGlnProPheGluSerSerGlyIleLeuValTrpGlyLysLeuSerValProTrpLysSerArgGlyLeuPheLeuSerAspGlyIleGlyThrProLys
IleSerProPheHisPheGluAlaSerThrSerLeuAspGlyHisGlyIleThrIleSerThrThrGlySerProSerValArgPheAsnAlaGlyGlyAlaAspAlaAlaGlyLeuGlyLeuArgAla
AspThrSerPheArgAsnLeuHisLeuThrAlaGlnIleProThrLeuAlaLeuArgAsnAsnSerIleLysIleGluThrValAsnGlyAlaPheThrAlaGlyGlyGluTyrAlaGlnTrpAspGly
SerPheLysLeuAspLysAlaAsnLeuHisSerGlyIleAlaAsnIleGlyAsnAlaGluIleSerGlySerPheLysThrProArgHisGlnThrAsnPheSerLeuAsnSerProLeuValTrpThr
GluAsnLysGlyLeuAspAlaProArgLeuTyrValSerThrLeuGlnAspThrValAsnArgLeuProGlnProArgPheIleSerArgLeuAspGlySerLeuSerValProAsnLeuGlnAsn
TrpAsnAlaGluLeuAsnGlyThrPheAspArgGlnThrValAlaAlaLysPheArgTyrThrHisGluAspAlaProHisLeuGluAlaAlaValAlaLeuGlnLysLeuAsnLeuThrProTyr
LeuAspAspValArgGlnGlnAsnGlyLysIlePheProAspThrLeuAlaLysLeuSerGlyAspIleGluAlaHisLeuLysIleGlyLysValGlnLeuProGlyLeuGlnLeuAspAspMet
GluThrTyrLeuHisAlaAspLysGlyHisIleAlaLeuSerArgPheLysSerGlyLeuTyrGlyGlyHisThrGluGlyGlyIleSerIleAlaAsnThrArgProAlaThrTyrArgLeuGln
GlnAsnAlaSerAsnIleGlnIleGlnProLeuLeuGlnAspLeuPheGlyPheHisSerPheSerGlyAsnGlyAspAlaValIleAspLeuThrAlaGlyGlyGluThrArgLysGluLeuIleArg
SerLeuGlnGlySerLeuSerLeuAsnIleSerAsnGlyAlaTrpHisGlyIleAspMetAspAsnIleLeuLysAsnGlyIleSerGlyLysThrAlaAspAsnAlaAlaProSerThrProPheHis
ArgPheThrLeuAsnSerGluIleSerAspGlyIleSerArgHisIleAspThrGluLeuPheSerAspSerLeuTyrValThrSerAsnGlyTyrThrAsnLeuAspThrGlnGluLeuSerGluAsp
ValLeuIleArgAsnAlaValHisProLysAsnLysProIleProLeuLysIleThrGlyThrValAspLysProSerIleThrValAspTyrGlyArgLeuThrGlyGlyIleAsnSerArgLysGlu
LysGlnLysIleLeuGluAspThrLeuLeuGluGlnTrpGlnTrpLeuLysProLysGluPro-704 a772

AMPHI Regions - AMPHI

SEQ. ID. NO. 24313 1-MetPheGlyAlaValLeuArgIleAspAlaAspCysLeuGlnIleIleValAlaCysLysLeuPheGlnIleValAlaTyrGlyPheAlaAlaLeuValGlu
GlyGluPheHisGluPheGlyGluMetLeuGluIleValArgLeuAlaAspThrValPheHisArgAsnHisAlaAspAspGlyArgIleHisPheArgArg
GlyValGluArgPheGlyArgHisValAsnGlnHisPheHisIleGluGluIleLeuGlnHisHisAlaGlnAlaAlaValValValAlaPheArgArgGly
AsnHisThrIleAspHisPhePheLeuGlnHisLysValHisIleAspAspIleValArgHisLeuArgGlnLeuGluGlnLysArgArgGlyAsnValVal
GlyGlnValAlaAspAspPheLeuPheAlaCysAspAlaValGluIleLysLeuGlnTyrIleAlaPheValAsnHisGlnPheIleArgLysArgGlnArg
PheGlnThrAlaTyrAspValAlaValAspPheAspAsnValGlnAlaValGlnLeuPheArgGlnArgPheGlyAsnArgArgGlnThrArgThrAsp
PheAsnHisAspIleIleArgLeuArgAlaHisGlyValAspAsnIleAlaAspAsnProArgValLeuGlnLysIleLeuProGluThrLeuAlaGlyPhe
ValPhePheHisArgValSerPheSerValGluThrProProPheArgAlaValGluSerAspSerIleTrpGluGlyArgAsnSerPheGlnIleArgThr
AlaHisArgAlaValLeuTyrValSerSerCysValLeuLysHisLysCysValTyrSerIleArgLeuMetSerAlaLeu-298

Antigenic Index - Jameson-Wolf (SEQ. ID. NO. 24313)

1-MetPheGlyAlaValLeuArgIleAspAlaAspCysLeuGlnIleIleValAlaCysLysLeuPheGlnIleValAlaTyrGlyPheAlaAlaLeuValGluGlyGluPheHisGluPheGlyGlu
MetLeuGluIleValArgLeuAlaAspThrValPheHisArgAsnHisAlaAspAspGlyArgIleHisPheArgArgGlyValGluArgPheGlyArgHisValAsnGlnHisPheHisIleGlu
GluIleLeuGlnHisHisAlaGlnAlaAlaValValValAlaPheArgArgGlyAsnHisThrIleAspHisPhePheLeuGlnHisLysValHisIleAspAspIleValArgHisLeuArgGlnLeu

TABLE 1-continued

GluGlnLysArgArgGlyAsnValValGlyGlnValAlaAspAspPheLeuPheAlaCysAspAlaValGluIleLysLeuGlnTyrIleAlaPheValAsnHisGlnPheIleArgLysArgGln
ArgPheGlnThrAlaTyrAspValAlaValAspPheAspAsnValGlnAlaValGlnLeuPheArgGlnArgPheGlyAsnArgArgGlnThrArgThrAspPheAsnHisAspIleIleArg
LeuArgAlaHisGlyValAspAsnIleAlaAspAsnProArgValLeuGlnLysIleLeuProGluThrLeuAlaGlyPheValPhePheHisArgValSerPheSerValGluThrProProPhe
ArgAlaValGluSerAspSerIleTrpGluGlyArgAsnSerPheGlnIleArgThrAlaHisArgAlaValLeuTyrValSerSerCysValLeuLysHisLysCysValTyrSerIleArgLeu
MetSerAlaLeu-298

Hydrophilic Regions - Hopp-Woods
(SEQ. ID. NO. 24313)
1-MetPheGlyAlaValLeuArgIleAspAlaAspCysLeuGlnIleIleValAlaCysLysLeuPheGlnIleValAlaTyrGlyPheAlaAlaLeuValGluGlyGluPheHisGluPheGly
GluMetLeuGluIleValArgLeuAlaAspThrValPheHisArgAsnHisAlaAspAspGlyArgIleHisPheArgArgGlyValGluArgPheGlyArgHisValAsnGlnHisPheHisIle
GluGluIleLeuGlnHisHisAlaGlnAlaAlaValValValAlaPheArgArgGlyAsnHisThrIleAspHisPhePheLeuGlnHisLysValHisIleAspAspIleValArgHisLeuArg
GlnLeuGluGlnLysArgArgGlyAsnValValGlyGlnValAlaAspAspPheLeuPheAlaCysAspAlaValGluIleLysLeuGlnTyrIleAlaPheValAsnHisGlnPheIleArg
LysArgGlnArgPheGlnThrAlaTyrAspValAlaValAspPheAspAsnValGlnAlaValGlnLeuPheArgGlnArgPheGlyAsnArgArgGlnThrArgThrAspPheAsnHis
AspIleIleArgLeuArgAlaHisGlyValAspAsnIleAlaAspAsnProArgValLeuGlnLysIleLeuProGluThrLeuAlaGlyPheValPhePheHisArgValSerPheSerVal
GluThrProProPheArgAlaValGluSerAspSerIleTrpGluGlyArgAsnSerPheGlnIleArgThrAlaHisArgAlaValLeuTyrValSerSerCysValLeuLysHisLysCys
ValTyrSerIleArgLeuMetSerAlaLeu-298 a774

AMPHI Regions - AMPHI

SEQ. ID. NO. 24314 1-MetLysThrLysLeuProLeuPheIleIleTrpLeuSerValSerAlaAlaCysSerSerProValSerArgAsnIleGlnAspMetArgLeuGluProGlnAla
GluAlaGlySerSerAspAlaIleProTyrProValProThrLeuGlnAspArgLeuAspTyrLeuGluGlyThrLeuValArgLeuSerAsnGluValGluThr
LeuAsnGlyLysValLysAlaLeuGluHisAlaLysThrHisProSerSerArgAlaTyrValGlnLysLeuAspAspArgLysLeuLysGluHisTyrLeu
AsnThrGluGlyGlySerAlaSerAlaHisThrValGluThrAlaGlnAsnLeuTyrAsnGlnAlaLeuLysHisTyrLysSerGlyArgPheSerAlaAlaAla
SerLeuLeuLysGlyAlaAspGlyGlyAspGlyGlySerIleAlaGlnArgSerMetTyrLeuLeuLeuGlnSerArgAlaArgMetGlyAsnCysGluSer
ValIleGluIleGlyGlyArgTyrAlaAsnArgPheLysAspSerProThrAlaProGluAlaMetPheLysIleGlyGluCysGlnTyrArgLeuGlnGlnLys
AspIleAlaArgAlaThrTrpArgSerLeuIleGlnThrTyrProGlySerProAlaAlaLysArgAlaAlaAlaAlaValArgLysArg-238

Antigenic Index - Jameson-Wolf
(SEQ. ID. NO. 24314)
1-MetLysThrLysLeuProLeuPheIleIleTrpLeuSerValSerAlaAlaCysSerSerProValSerArgAsnIleGlnAspMetArgLeuGluProGlnAlaGluAlaGlySerSerAspAlaIle
ProTyrProValProThrLeuGlnAspArgLeuAspTyrLeuGluGlyThrLeuValArgLeuSerAsnGluValGluThrLeuAsnGlyLysValLysAlaLeuGluHisAlaLysThrHisPro
SerSerArgAlaTyrValGlnLysLeuAspAspArgLysLeuLysGluHisTyrLeuAsnThrGluGlyGlySerAlaSerAlaHisThrValGluThrAlaGlnAsnLeuTyrAsnGlnAlaLeu
LysHisTyrLysSerGlyArgPheSerAlaAlaAlaSerLeuLeuLysGlyAlaAspGlyGlyAspGlyGlySerIleAlaGlnArgSerMetTyrLeuLeuLeuGlnSerArgAlaArgMetGly
AsnCysGluSerValIleGluIleGlyGlyArgTyrAlaAsnArgPheLysAspSerProThrAlaProGluAlaMetPheLysIleGlyGluCysGlnTyrArgLeuGlnGlnLysAspIleAla
ArgAlaThrTrpArgSerLeuIleGlnThrTyrProGlySerProAlaAlaLysArgAlaAlaAlaAlaValArgLysArg-238

Hydrophilic Regions - Hopp-Woods
(SEQ. ID. NO. 24314)
1-MetLysThrLysLeuProLeuPheIleIleTrpLeuSerValSerAlaAlaCysSerSerProValSerArgAsnIleGlnAspMetArgLeuGluProGlnAlaGluAlaGlySerSerAspAlaIle
ProTyrProValProThrLeuGlnAspArgLeuAspTyrLeuGluGlyThrLeuValArgLeuSerAsnGluValGluThrLeuAsnGlyLysValLysAlaLeuGluHisAlaLysThrHisPro
SerSerArgAlaTyrValGlnLysLeuAspAspArgLysLeuLysGluHisTyrLeuAsnThrGluGlyGlySerAlaSerAlaHisThrValGluThrAlaGlnAsnLeuTyrAsnGlnAlaLeu
LysHisTyrLysSerGlyArgPheSerAlaAlaAlaSerLeuLeuLysGlyAlaAspGlyGlyAspGlyGlySerIleAlaGlnArgSerMetTyrLeuLeuLeuGlnSerArgAlaArgMetGly
AsnCysGluSerValIleGluIleGlyGlyArgTyrAlaAsnArgPheLysAspSerProThrAlaProGluAlaMetPheLysIleGlyGluCysGlnTyrArgLeuGlnGlnLysAspIleAla
ArgAlaThrTrpArgSerLeuIleGlnThrTyrProGlySerProAlaAlaLysArgAlaAlaAlaAlaValArgLysArg-238 a790

AMPHI Regions - AMPHI

SEQ. ID. NO. 24315 10-GluAlaAlaAlaGluVal-15
SEQ. ID. NO. 24316 44-GlyAsnGlnThrCysSerArgTyrSerAsn-53
SEQ. ID. NO. 24317 89-LysGlnAlaValThr-93
SEQ. ID. NO. 24318 103-ThrGlnAlaTyrAsnGluMetThrLysSerVal-113
SEQ. ID. NO. 24319 166-PheAlaArgThrGlyLysLeu-172
SEQ. ID. NO. 24320 174-GlySerPheAspLeuPheAlaSerVal-182
SEQ. ID. NO. 24321 253-ProSerGluAlaLeuAsp-258
SEQ. ID. NO. 24322 290-ThrAlaProAspValTrpThrVal-297
SEQ. ID. NO. 24323 320-PheLeuArgPheTrpGlnAlaThrArgGlyIle-330

Antigenic Index - Jameson-Wolf

SEQ. ID. NO. 24324 1-MetAlaArgArgSerLysThrPheGluGluAlaAlaAlaGluValGluGluArgPheGlyHisArgGlyIleLys-25
SEQ. ID. NO. 24325 30-GluGlyThrAlaLysProCysVal-37
SEQ. ID. NO. 24326 39-AsnCysProLysHisGlyAsnGlnThrCysSerArgTyrSer-52
SEQ. ID. NO. 24327 57-GlySerSerTrpGlyCysProSerCysGlyAsnGluGlnAlaAla-71
SEQ. ID. NO. 24328 77-ThrLeuArgLysAsnHisIle-83
SEQ. ID. NO. 24329 95-MetThrLysGlnGluArgIleThr-102
SEQ. ID. NO. 24330 123-AspValGlnGlyAspThrThrIle-130
SEQ. ID. NO. 24331 134-HisThrHisThrHisAsnHisSerAspAlaAspGlyLysAlaLeuSer-149
SEQ. ID. NO. 24332 152-LeuThrProArgProLeuLeuSerAspArgGlnAla-163
SEQ. ID. NO. 24333 167-AlaArgThrGlyLysLeuThrGly-174
SEQ. ID. NO. 24334 194-MetProAspThrSerMet-199
SEQ. ID. NO. 24335 201-ProValIleGluLysGlyAsp-207
SEQ. ID. NO. 24336 213-ProArgMetArgProAlaAspGluAspIleVal-223
SEQ. ID. NO. 24337 227-LeuSerAspLysArgLeuVal-233
SEQ. ID. NO. 24338 248-TyrGlnThrGlyArgProSerGluAlaLeuAspLeuProGluGly-262
SEQ. ID. NO. 24339 270-LeuGluSerLysAsnGlyLeuCysProProHisArgGlnGluGlyVal-285
SEQ. ID. NO. 24340 301-SerAlaSerLysThrSerCysThrArgProThrAlaAlaArgLysSerAla-317
SEQ. ID. NO. 24341 326-AlaThrArgGlyIleProLysThrArgSerTrpArgAsnProAsnAsnAlaCys-343

Hydrophilic Regions - Hopp-Woods

SEQ. ID. NO. 24342 1-MetAlaArgArgSerLysThrPheGluGluAlaAlaAlaGluValGluGluArgPheGlyHisArgGlyIleLys-25
SEQ. ID. NO. 24343 65-CysGlyAsnGluGlnAlaAla-71
SEQ. ID. NO. 24344 77-ThrLeuArgLysAsnHisIle-83
SEQ. ID. NO. 24345 96-ThrLysGlnGluArgIleThr-102
SEQ. ID. NO. 24346 139-AsnHisSerAspAlaAspGlyLysAlaLeuSer-149
SEQ. ID. NO. 24347 157-LeuLeuSerAspArgGlnAla-163
SEQ. ID. NO. 24348 168-ArgThrGlyLysLeu-172
SEQ. ID. NO. 24349 202-ValIleGluLysGlyAsp-207
SEQ. ID. NO. 24350 213-ProArgMetArgProAlaAspGluAspIleVal-223

TABLE 1-continued

| | |
|---|---|
| SEQ. ID. NO. 24351 | 227-LeuSerAspLysArgLeuVal-233 |
| SEQ. ID. NO. 24352 | 251-GlyArgProSerGluAlaLeuAspLeuProGlu-261 |
| SEQ. ID. NO. 24353 | 270-LeuGluSerLysAsnGlyLeu-276 |
| SEQ. ID. NO. 24354 | 280-HisArgGlnGluGlyVal-285 |
| SEQ. ID. NO. 24355 | 301-SerAlaSerLysThrSerCysThrArgProThrAlaAlaArgLysSerAla-317 |
| SEQ. ID. NO. 24356 | 328-ArgGlyIleProLysThrArgSerTrpArgAsn-338 |
| a900-2 | |
| AMPHI Regions - AMPHI | |
| SEQ. ID. NO. 24357 | 9-ValValAlaPheAlaArgPhe-15 |
| SEQ. ID. NO. 24358 | 36-ValGlyLysHisPheArgLysPheCysArgPheArg-47 |
| SEQ. ID. NO. 24359 | 62-ValGlyLeuLeuArgLeuAlaArgLeuPheHisIleGlyAspAspPheValAspArgPheLeuGlyPhePhe-85 |
| SEQ. ID. NO. 24360 | 120-GlnCysGluGluPheProGluAlaValValGluAla-131 |
| SEQ. ID. NO. 24361 | 198-HisGlnThrLeuGlyGlyAspAlaGly-206 |
| SEQ. ID. NO. 24362 | 210-ValGlnPheHisHisPheGly-216 |
| SEQ. ID. NO. 24363 | 233-GlyLysProSerGlyGlyAsnGlyLeuGlyGlyLeuValAsnHisLeuArgLeuValAla-252 |
| SEQ. ID. NO. 24364 | 268-IleArgValLeuArgArgAlaAspGlyGly-277 |
| SEQ. ID. NO. 24365 | 279-AspSerThrAspValValAlaGlnMet-287 |
| Antigenic Index - Jameson-Wolf | |
| SEQ. ID. NO. 24366 | 1-LeuArgArgValGlyGlyGln-7 |
| SEQ. ID. NO. 24367 | 20-ValAspPheArgArgGlnLys-26 |
| SEQ. ID. NO. 24368 | 38-LysHisPheArgLysPheCysArgPheArgArgArgGlyGluSer-52 |
| SEQ. ID. NO. 24369 | 56-PheLysGlnArgAla-60 |
| SEQ. ID. NO. 24370 | 74-GlyAspAspPheValAspArg-80 |
| SEQ. ID. NO. 24371 | 88-PheProLysArgAsnGlyValAla-95 |
| SEQ. ID. NO. 24372 | 105-GlnThrAsnGlnGlu-109 |
| SEQ. ID. NO. 24373 | 118-PheGlyGlnCysGluGluPhePro-125 |
| SEQ. ID. NO. 24374 | 155-GluHisGluAsnValGlySerHisGluAspArgValAla-167 |
| SEQ. ID. NO. 24375 | 201-LeuGlyGlyAspAlaGlyGlnAsnPro-209 |
| SEQ. ID. NO. 24376 | 229-ValGluSerAlaGlyLysProSerGlyGlyAsnGly-240 |
| SEQ. ID. NO. 24377 | 252-AlaPheAspAspThrValValIleGlyGluGluGluGluGlyPheGly-267 |
| SEQ. ID. NO. 24378 | 270-ValLeuArgArgAlaAspGlyGlyAlaAspSerThrAsp-282 |
| SEQ. ID. NO. 24379 | 285-AlaGlnMetArgAspAlaGlyGly-292 |
| SEQ. ID. NO. 24380 | 311-MetProSerGluArgGluLysAspAlaProIle-321 |
| SEQ. ID. NO. 24381 | 323-ProAspLeuProProThrSerSerArgGlnGlnThr-334 |
| Hydrophilic Regions - Hopp-Woods | |
| SEQ. ID. NO. 24382 | 1-LeuArgArgValGly-5 |
| SEQ. ID. NO. 24383 | 20-ValAspPheArgArgGlnLys-26 |
| SEQ. ID. NO. 24384 | 38-LysHisPheArgLysPheCysArgPheArgArgArgGlyGluSer-52 |
| SEQ. ID. NO. 24385 | 89-ProLysArgAsnGly-93 |
| SEQ. ID. NO. 24386 | 120-GlnCysGluGluPhePro-125 |
| SEQ. ID. NO. 24387 | 155-GluHisGluAsnValGlySerHisGluAspArgValAla-167 |
| SEQ. ID. NO. 24388 | 201-LeuGlyGlyAspAlaGlyGln-207 |
| SEQ. ID. NO. 24389 | 231-SerAlaGlyLysProSerGly-237 |
| SEQ. ID. NO. 24390 | 257-ValValIleGlyGluGluGluGluGlyPheGly-267 |
| SEQ. ID. NO. 24391 | 270-ValLeuArgArgAlaAspGlyGlyAlaAspSerThrAsp-282 |
| SEQ. ID. NO. 24392 | 285-AlaGlnMetArgAspAlaGly-291 |
| SEQ. ID. NO. 24393 | 311-MetProSerGluArgGluLysAspAlaProIle-321 |
| SEQ. ID. NO. 24394 | 326-ProProThrSerSerArgGlnGln-333 |
| a901 | |
| AMPHI Regions - AMPHI | |
| SEQ. ID. NO. 24395 | 20-GlyLeuPheThrValLeuGly-26 |
| SEQ. ID. NO. 24396 | 55-ValSerLeuThrGluIlePheSerLysSer-64 |
| SEQ. ID. NO. 24397 | 66-GluAlaPheAlaGluIleTyrAsp-73 |
| SEQ. ID. NO. 24398 | 84-AlaPheLeuAlaGlyMetGlyGlyIleAlaLeuIle-95 |
| SEQ. ID. NO. 24399 | 97-ArgLeuValProAsnProHisGluThrLeuAsp-107 |
| SEQ. ID. NO. 24400 | 124-ValGlyMetMetAlaAlaPhe-130 |
| SEQ. ID. NO. 24401 | 136-AsnPheProGluGlyLeuAlaThrPhePheAlaThrLeuGlu-149 |
| SEQ. ID. NO. 24402 | 164-HisAsnIleProGluGlyIleSer-171 |
| SEQ. ID. NO. 24403 | 190-CysLeuLeuSerGlyLeuAlaGluProLeuGlyAlaAla-202 |
| SEQ. ID. NO. 24404 | 217-PheGlySerValPheGlyValIleAlaGlyValMet-228 |
| SEQ. ID. NO. 24405 | 243-TyrSerAspGlyHisGlu-248 |
| Antigenic Index - Jameson-Wolf | |
| SEQ. ID. NO. 24406 | 1-MetProAspPheSerMet-6 |
| SEQ. ID. NO. 24407 | 33-SerLysThrProAsnProArgVal-40 |
| SEQ. ID. NO. 24408 | 61-PheSerLysSerSerGluAlaPhe-68 |
| SEQ. ID. NO. 24409 | 71-IleTyrAspLysAspHisAla-77 |
| SEQ. ID. NO. 24410 | 98-LeuValProAsnProHisGluThrLeuAspAlaGlnAspProSerPheGlnGluSerLysArgArgHisIleAla-122 |
| SEQ. ID. NO. 24411 | 136-AsnPheProGluGly-140 |
| SEQ. ID. NO. 24412 | 179-AlaThrArgSerArgLysLysThr-186 |
| SEQ. ID. NO. 24413 | 193-SerGlyLeuAlaGluProLeuGly-200 |
| SEQ. ID. NO. 24414 | 235-GluLeuLeuProAlaAlaLysArgTyrSerAspGlyHisGluThr-249 |
| Hydrophilic Regions - Hopp-Woods | |
| SEQ. ID. NO. 24415 | 61-PheSerLysSerSerGluAlaPhe-68 |
| SEQ. ID. NO. 24416 | 71-IleTyrAspLysAspHisAla-77 |

TABLE 1-continued

| | |
|---|---|
| SEQ. ID. NO. 24417 | 102-ProHisGluThrLeuAspAlaGlnAspProSerPheGlnGluSerLysArgArgHisIleAla-122 |
| SEQ. ID. NO. 24418 | 180-ThrArgSerArgLysLysThr-186 |
| SEQ. ID. NO. 24419 | 235-GluLeuLeuProAlaAlaLysArgTyrSerAspGlyHisGlu-248 |

a902

AMPHI Regions - AMPHI

| | |
|---|---|
| SEQ. ID. NO. 24420 | 1-LeuHisPheGlnArgIleIleLysCysSerGluGlyIleTrpAlaValGlyAlaArgProThrValGlyPhePheGlyLysSerPheLysIleThrCysLysHis ValValLeuArgArgArgThrValGlnAlaValAspPheThrThrCysLeuPheAlaValGlyHisPheValAspValProAlaTyrValPheAlaCysAsp AlaHisThrGlyGlyValAlaValLysArgValHisGlySerAspValValGlnAsnSerGlyGlyThrPheCy5GlnThrGlnGlyArgArgAsnThrVal PheGlyValMetPheGlnIleAlaGluGluProArgSerAlaLeuArgAlaAlaProTyrHisAsnAlaValCysGlyGlyLeuPheGluAspGlyLeuGly PheLeuArgArgGlyAsnValAlaValAspProAspArgAspValGlnThrAlaPheGlyPheGlyAsnGlnValValSerArgPheAlaPheValHis LeuArgAlaArgAlaSerValAspGlyLysGlyGlyAsnAlaAlaIlePheGlyAspPheGlyAspAspGlyGlnValLeuMetValValValProThrGln ThrGlyPheGluGlyAsnGlyTyrAlaArgArgPheAspHisArgLeuGlnAsnGlyGlyAsnGlnArgLeuValLeuHisGlnArgAlaThrGlyLeu AspIleAlaAspPhePheSerGlyThrAlaHisValAspValAspLysLeuArgProLysAlaAspValValThrArgGlyIleArgHisLeuLeuArgIle AlaSerGlyAsnLeuHisGlyAsnAsnAlaAlaPheIleGlyLysIleAlaAlaValGlnGlyPheSerSerIleSerGluArgArgValAlaGlyGlnHisPhe AlaHisArgProThrCysAlaLysIleSerAlaLysSerAlaGluArgPheValGlyAsnAlaArgHisArgArgLysCysAspGlyValValAspLysIle AlaAlaAspValHisAsnGlySerAlaPheGlnLysSerThrProLeuTyrIlePhe-359 |

Antigenic Index - Jameson-Wolf
(SEQ. ID. NO. 24420)
1-LeuHisPheGlnArgIleIleLysCysSerGluGlyIleTrpAlaValGlyAlaArgProThrValGlyPhePheGlyLysSerPheLysIleThrCysLysHisValValLeuArgArgArgThrVal GlnAlaValAspPheThrThrCysLeuPheAlaValGlyHisPheValAspValProAlaTyrValPheAlaCysAspAlaHisThrGlyGlyValAlaValLysArgValHisGlySerAspVal ValGlnAsnSerGlyGlyThrPheCysGlnThrGlnGlyArgArgAsnThrValPheGlyValMetPheGlnIleAlaGluGluProArgSerAlaLeuArgAlaAlaProTyrHisAsnAlaVal CysGlyGlyLeuPheGluAspGlyLeuGlyPheLeuArgArgGlyAsnValAlaValAspProAspArgAspValGlnThrAlaPheGlyPheGlyAsnGlnValValSerArgPheAlaPhe ValHisLeuArgAlaArgAlaSerValAspGlyLysGlyGlyAsnAlaAlaIlePheGlyAspPheGlyAspAspGlyGlnValLeuMetValValValProThrGlnThrGlyPheGluGlyAsn GlyTyrAlaArgArgPheAspHisArgLeuGlnAsnGlyGlyAsnGlnArgLeuValLeuHisGlnArgAlaThrGlyLeuAspIleAlaAspPhePheSerGlyThrAlaHisValAspValAsp LysLeuArgProLysAlaAspValValThrArgGlyIleArgHisLeuLeuArgIleAlaSerGlyAsnLeuHisGlyAsnAsnAlaAlaPheIleGlyLysIleAlaAlaValGlnGlyPheSerSer IleSerGluArgArgValAlaGlyGlnHisPheAlaHisArgProThrCysAlaLysIleSerAlaLysSerAlaGluArgPheValGlyAsnAlaArgHisArgArgLysCysAspGlyValVal AspLysIleAlaAlaAspValHisAsnGlySerAlaPheGlnLysSerThrProLeuTyrIlePhe-359

Hydrophilic Regions - Hopp-Woods
(SEQ. ID. NO. 24420)
1-LeuHisPheGlnArgIleIleLysCysSerGluGlyIleTrpAlaValGlyAlaArgProThrValGlyPhePheGlyLysSerPheLysIleThrCysLysHisValValLeuArgArgArgThrVal GlnAlaValAspPheThrThrCysLeuPheAlaValGlyHisPheValAspValProAlaTyrValPheAlaCysAspAlaHisThrGlyGlyValAlaValLysArgValHisGlySerAspVal ValGlnAsnSerGlyGlyThrPheCysGlnThrGlnGlyArgArgAsnThrValPheGlyValMetPheGlnIleAlaGluGluProArgSerAlaLeuArgAlaAlaProTyrHisAsnAlaVal CysGlyGlyLeuPheGluAspGlyLeuGlyPheLeuArgArgGlyAsnValAlaValAspProAspArgAspValGlnThrAlaPheGlyPheGlyAsnGlnValValSerArgPheAlaPhe ValHisLeuArgAlaArgAlaSerValAspGlyLysGlyGlyAsnAlaAlaIlePheGlyAspPheGlyAspAspGlyGlnValLeuMetValValValProThrGlnThrGlyPheGluGlyAsn GlyTyrAlaArgArgPheAspHisArgLeuGlnAsnGlyGlyAsnGlnArgLeuValLeuHisGlnArgAlaThrGlyLeuAspIleAlaAspPhePheSerGlyThrAlaHisValAspValAsp LysLeuArgProLysAlaAspValValThrArgGlyIleArgHisLeuLeuArgIleAlaSerGlyAsnLeuHisGlyAsnAsnAlaAlaPheIleGlyLysIleAlaAlaValGlnGlyPheSerSer IleSerGluArgArgValAlaGlyGlnHisPheAlaHisArgProThrCysAlaLysIleSerAlaLysSerAlaGluArgPheValGlyAsnAlaArgHisArgArgLysCysAspGlyValVal AspLysIleAlaAlaAspValHisAsnGlySerAlaPheGlnLysSerThrProLeuTyrIlePhe-359 a903-1

AMPHI Regions - AMPHI

| | |
|---|---|
| SEQ. ID. NO. 24421 | 1-MetLysPhePheProAlaProCysLeuLeuValIleLeuAlaValIleProLeuLysThrLeuAlaAlaAspGluAsnAspAlaGluLeuIleArgSerMet GlnArgGlnGlnHisIleAspAlaGluLeuLeuThrAspAlaAsnValArgPheGluGlnProLeuGluLysAsnAsnTyrValLeuSerGluAspGluThr ProCysThrArgValAsnTyrIleSerLeuAspAspLysThrAlaArgLysPheSerPheLeuProSerValLeuMetLysGluThrAlaPheLysThrGly MetCysLeuGlySerAsnAsnLeuSerArgLeuGlnLysAlaAlaGlnGlnIleLeuIleValArgGlyTyrLeuThrSerGlnAlaIleIleGlnProGlnAsn MetAspSerGlyIleLeuLysLeuArgValSerAlaGlyGluIleGlyAspIleArgTyrGluGluLysArgAspGlyLysSerAlaGluGlySerIleSerAla PheAsnAsnLysPheProLeuTyrArgAsnLysIleLeuAsnLeuArgAspValGluGlnGlyLeuGluAsnLeuArgArgLeuProSerValLysThrAsp IleGlnIleIleProSerGluGluGluGlyLysSerAspLeuGlnIleLysTrpGlnGlnAsnLysProIleArgPheSerIleGlyIleAspAspAlaGlyGlyLys ThrThrGlyLysTyrGlnGlyAsnValAlaLeuSerPheAspAsnProLeuGlyLeuSerAspLeuPheTyrValSerTyrGlyArgGlyLeuValHisLys ThrAspLeuThrAspAlaThrGlyThrGluThrGluSerGlySerArgSerTyrSerValHisTyrSerValProValLysLysTrpLeuPheSerPheAsnHis AsnGlyHisArgTyrHisGluAlaThrGluGlyTyrSerValAsnTyrAspTyrAsnGlyLysGlnTyrGlnSerSerLeuAlaAlaGluArgMetLeuTrp ArgAsnArgPheHisLysThrSerValGlyMetLysLeuTrpThrArgGlnThrTyrLysTyrIleAspAspAlaGluIleGluValGlnArgArgArgSer AlaGlyTrpGluAlaGluLeuArgHisArgAlaTyrLeuAsnArgTrpGlnLeuAspGlyLysLeuSerTyrLysArgGlyThrGlyMetArgGlnSerMet ProAlaProGluGluAsnGlyGlyGlyThrIleProGlyThrSerArgMetLysIleIleThrAlaGlyLeuAspAlaAlaAlaProPheMetLeuGlyLysGln GlnPhePheTyrAlaThrAlaIleGlnAlaGlnTrpAsnLysThrProLeuValAlaGlnAspLysLeuSerIleGlySerArgTyrThrValArgGlyPheAsp GlyGluGlnSerLeuPheGlyGluArgGlyPheTyrTrpGlnAsnThrLeuThrTrpTyrPheHisProAsnHisGlnPheTyrLeuGlyAlaAspTyrGly ArgValSerGlyGluSerAlaGlnTyrValSerGlyLysGlnLeuMetGlyAlaValValGlyPheArgGlyGlyHisLysValGlyGlyMetPheAlaTyr AspLeuPheAlaGlyLysProLeuHisLysProLysGlyPheGlnThrThrAsnThrValTyrGlyPheAsnLeuAsnTyrSerPhe-580 |

Antigenic Index - Jameson-Wolf
(SEQ. ID. NO. 24421)
1-MetLysPhePheProAlaProCysLeuLeuValIleLeuAlaValIleProLeuLysThrLeuAlaAlaAspGluAsnAspAlaGluLeuIleArgSerMetGlnArgGlnGlnHisIleAspAla GluLeuLeuThrAspAlaAsnValArgPheGluGlnProLeuGluLysAsnAsnTyrValLeuSerGluAspGluThrProCysThrArgValAsnTyrIleSerLeuAspAspLysThrAlaArg LysPheSerPheLeuProSerValLeuMetLysGluThrAlaPheLysThrGlyMetCysLeuGlySerAsnAsnLeuSerArgLeuGlnLysAlaAlaGlnGlnIleLeuIleValArgGlyTyr LeuThrSerGlnAlaIleIleGlnProGlnAsnMetAspSerGlyIleLeuLysLeuArgValSerAlaGlyGluIleGlyAspIleArgTyrGluGluLysArgAspGlyLysSerAlaGluGlySer IleSerAlaPheAsnAsnLysPheProLeuTyrArgAsnLysIleLeuAsnLeuArgAspValGluGlnGlyLeuGluAsnLeuArgArgLeuProSerValLysThrAspIleGlnIleIlePro SerGluGluGluGlyLysSerAspLeuGlnIleLysTrpGlnGlnAsnLysProIleArgPheSerIleGlyIleAspAspAlaGlyGlyLysThrThrGlyLysTyrGlnGlyAsnValAlaLeuSer PheAspAsnProLeuGlyLeuSerAspLeuPheTyrValSerTyrGlyArgGlyLeuValHisLysThrAspLeuThrAspAlaThrGlyThrGluThrGluSerGlySerArgSerTyrSerVal HisTyrSerValProValLysLysTrpLeuPheSerPheAsnHisAsnGlyHisArgTyrHisGluAlaThrGluGlyTyrSerValAsnTyrAspTyrAsnGlyLysGlnTyrGlnSerSerLeu AlaAlaGluArgMetLeuTrpArgAsnArgPheHisLysThrSerValGlyMetLysLeuTrpThrArgGlnThrTyrLysTyrIleAspAspAlaGluIleGluValGlnArgArgArgSerAla GlyTrpGluAlaGluLeuArgHisArgAlaTyrLeuAsnArgTrpGlnLeuAspGlyLysLeuSerTyrLysArgGlyThrGlyMetArgGlnSerMetProAlaProGluGluAsnGlyGly GlyThrIleProGlyThrSerArgMetLysIleIleThrAlaGlyLeuAspAlaAlaAlaProPheMetLeuGlyLysGlnGlnPhePheTyrAlaThrAlaIleGlnAlaGlnTrpAsnLysThrPro LeuValAlaGlnAspLysLeuSerIleGlySerArgTyrThrValArgGlyPheAspGlyGluGlnSerLeuPheGlyGluArgGlyPheTyrTrpGlnAsnThrLeuThrTrpTyrPheHisPro AsnHisGlnPheTyrLeuGlyAlaAspTyrGlyArgValSerGlyGluSerAlaGlnTyrValSerGlyLysGlnLeuMetGlyAlaValValGlyPheArgGlyGlyHisLysValGlyGlyMet PheAlaTyrAspLeuPheAlaGlyLysProLeuHisLysProLysGlyPheGlnThrThrAsnThrValTyrGlyPheAsnLeuAsnTyrSerPhe-580

Hydrophilic Regions - Hopp-Woods
(SEQ. ID. NO. 24421)
1-MetLysPhePheProAlaProCysLeuLeuValIleLeuAlaValIleProLeuLysThrLeuAlaAlaAspGluAsnAspAlaGluLeuIleArgSerMetGlnArgGlnGlnHisIleAspAla GluLeuLeuThrAspAlaAsnValArgPheGluGlnProLeuGluLysAsnAsnTyrValLeuSerGluAspGluThrProCysThrArgValAsnTyrIleSerLeuAspAspLysThrAlaArg LysPheSerPheLeuProSerValLeuMetLysGluThrAlaPheLysThrGlyMetCysLeuGlySerAsnAsnLeuSerArgLeuGlnLysAlaAlaGlnGlnIleLeuIleValArgGlyTyr LeuThrSerGlnAlaIleIleGlnProGlnAsnMetAspSerGlyIleLeuLysLeuArgValSerAlaGlyGluIleGlyAspIleArgTyrGluGluLysArgAspGlyLysSerAlaGluGlySer IleSerAlaPheAsnAsnLysPheProLeuTyrArgAsnLysIleLeuAsnLeuArgAspValGluGlnGlyLeuGluAsnLeuArgArgLeuProSerValLysThrAspIleGlnIleIleProSer TABLE 1-continued GluGluGluGlyLysSerAspLeuGlnIleLysTrpGlnGlnAsnLysProIleArgPheSerIleGlyIleAspAspAlaGlyGlyLysThrThrGlyLysTyrGlnGlyAsnValAlaLeuSerPhe AspAsnProLeuGlyLeuSerAspLeuPheTyrValSerTyrGlyArgGlyLeuValHisLysThrAspLeuThrAspAlaThrGlyThrGluThrGluSerGlySerArgSerTyrSerValHis TyrSerValProValLysLysTrpLeuPheSerPheAsnHisAsnGlyHisArgTyrHisGluAlaThrGluGlyTyrSerValAsnTyrAspTyrAsnGlyLysGlnTyrGlnSerSerLeuAla AlaGluArgMetLeuTrpArgAsnArgPheHisLysThrSerValGlyMetLysLeuTrpThrArgGlnThrTyrLysTyrIleAspAspAlaGluIleGluValGlnArgArgArgSerAlaGly TrpGluAlaGluLeuArgHisArgAlaTyrLeuAsnArgTrpGlnLeuAspGlyLysLeuSerTyrLysArgGlyThrGlyMetArgGlnSerMetProAlaProGluGluAsnGlyGlyGly ThrIleProGlyThrSerArgMetLysIleIleThrAlaGlyLeuAspAlaAlaAlaProPheMetLeuGlyLysGlnGlnPhePheTyrAlaThrAlaIleGlnAlaGlnTrpAsnLysThrProLeu ValAlaGlnAspLysLeuSerIleGlySerArgTyrThrValArgGlyPheAspGlyGluGlnSerLeuPheGlyGluArgGlyPheTyrTrpGlnAsnThrLeuThrTrpTyrPheHisProAsn HisGlnPheTyrLeuGlyAlaAspTyrGlyArgValSerGlyGluSerAlaGlnTyrValSerGlyLysGlnLeuMetGlyAlaValValGlyPheArgGlyGlyHisLysValGlyGlyMetPhe AlaTyrAspLeuPheAlaGlyLysProLeuHisLysProLysGlyPheGlnThrThrAsnThrValTyrGlyPheAsnLeuAsnTyrSerPhe-580 a904

AMPHI Regions - AMPHI

SEQ. ID. NO. 24422 1-MetMetGlnHisAsnArgPhePheAlaValGlyAlaGlyGlyAspAspGlyAspArgArgThrAlaAspPhePheAsnProPheGlnIleCysPheGlyIle GlyArgCysValValAlaPheHisAlaGluSerGlyPheAlaProThrGlyHisGlyPheValAsnArgLeuAlaGlyPheTyrArgIleArgAlaAlaArgGln AspValGlyPheAlaAlaValGlyGlnPheValAlaAspAlaAspIleAspGlyPheAsnAlaValHisTyrIleGluPheGlyAsnThrHisThrGlyAsnAla ValAspLeuAspGlyAlaPheGlnGlyGlyGlyIleLysProAlaAlaAlaAlaCysAlaSerGlyTyrArgThrGluPheValSerAlaPheCysGlnThrCys SerAspPheValGluGlnPheGlyArgGluArgAlaArgThrAspAlaArgGlyIleGlyPheAspAspAlaGlnAsnIleIleGlnHisLeuArgAlaTyrAla ArgAlaCysArgSerArgAlaGlyGluAlaValGlyArgSerAsnGluGlyValSerAlaValValAspValGlnGlnArgThrLeuArgAlaPheLysGln GlnPhePheAlaValPheValPhePheValGlnHisAlaGlyHisValGlyAsnHisArgArgAsnAlaArgArgAspPhePheAspAsnArgHisHisVal PheArgPheHisArgLeuGlyIleValGlnMetLeuGlnLeuAspValValIleSerLysAspGlyIleGlnPhePheThrGlnPhePheArgMetGlnGln IleGlyGlyAlaAsnGlyAlaAlaCysHisPheValPheValGlyArgAlaAspAlaAlaAlaGlyArgAlaAspPheAlaPheAlaAlaArgCysPheSer GlyLeuValGluArgAspValIleArgGlnAspGlnArgAlaGlyArgArgAspPheGlnThrAlaPheAspValPheHisAlaCysArgValGlnLeuVal AspPheAlaGlnGlnGlyPheGlyGlyAspAspAsnAlaArgThrAspGluAlaValGlnThrPheMetGlnAspAlaAlaArgAsnGlnAlaGlnAsn GlyPhePheAlaAlaAspAsnGlnGlyMetThrArgIleValAlaAlaLeuGluAlaHisHisAlaSerGlyPhePheArgGlnProValAsnAspPheThr PheThrLeuValAlaProLeuCysAlaAspTyrTyrAsnIlePheSerHisSerHisIleThrXxxArgTyr-435

Antigenic Index - Jameson-Wolf (SEQ. ID. NO. 24422)

1-MetMetGlnHisAsnArgPhePheAlaValGlyAlaGlyGlyAspAspGlyAspArgArgThrAlaAspPhePheAsnProPheGlnIleCysPheGlyIleGlyArgCysValValAlaPhe HisAlaGluSerGlyPheAlaProThrGlyHisGlyPheValAsnArgLeuAlaGlyPheTyrArgIleArgAlaAlaArgGlnAspValGlyPheAlaAlaValGlyGlnPheValAlaAspAla AspIleAspGlyPheAsnAlaValHisTyrIleGluPheGlyAsnThrHisThrGlyAsnAlaValAspLeuAspGlyAlaPheGlnGlyGlyGlyIleLysProAlaAlaAlaAlaCysAlaSer GlyTyrArgThrGluPheValSerAlaPheCysGlnThrCysSerAspPheValGluGlnPheGlyArgGluArgAlaArgThrAspAlaArgGlyIleGlyPheAspAspAlaGlnAsnIleIle GlnHisLeuArgAlaTyrAlaArgAlaCysArgSerArgAlaGlyGluAlaValGlyArgSerAsnGluGlyValSerAlaValValAspValGlnGlnArgThrLeuArgAlaPheLysGlnGln PhePheAlaValPheValPhePheValGlnHisAlaGlyHisValGlyAsnHisArgArgAsnAlaArgArgAspPhePheAspAsnArgHisHisValPheArgPheHisArgLeuGlyIleVal GlnMetLeuGlnLeuAspValValIleSerLysAspGlyIleGlnPhePheThrGlnPhePheArgMetGlnGlnIleGlyGlyAlaAsnGlyAlaAlaCysHisPheValPheValGlyArgAla AspAlaAlaAlaGlyArgAlaAspPheAlaPheAlaAlaArgCysPheSerGlyLeuValGluArgAspValIleArgGlnAspGlnArgAlaGlyArgArgAspPheGlnThrAlaPheAspVal PheHisAlaCysArgValGlnLeuValAspPheAlaGlnGlnGlyPheGlyGlyAspAspAsnAlaArgThrAspGluAlaValGlnThrPheMetGlnAspAlaAlaArgAsnGlnAlaGln AsnGlyPhePheAlaAlaAspAsnGlnGlyMetThrArgIleValAlaAlaLeuGluAlaHisHisAlaSerGlyPhePheArgGlnProValAsnAspPheThrPheThrLeuValAlaProLeu CysAlaAspTyrTyrAsnIlePheSerHisSerHisIleThrXxxArgTyr-435

Hydrophilic Regions - Hopp-Woods (SEQ. ID. NO. 24422)

1-MetMetGlnHisAsnArgPhePheAlaValGlyAlaGlyGlyAspAspGlyAspArgArgThrAlaAspPhePheAsnProPheGlnIleCysPheGlyIleGlyArgCysValValAlaPhe HisAlaGluSerGlyPheAlaProThrGlyHisGlyPheValAsnArgLeuAlaGlyPheTyrArgIleArgAlaAlaArgGlnAspValGlyPheAlaAlaValGlyGlnPheValAlaAspAla AspIleAspGlyPheAsnAlaValHisTyrIleGluPheGlyAsnThrHisThrGlyAsnAlaValAspLeuAspGlyAlaPheGlnGlyGlyGlyIleLysProAlaAlaAlaAlaCysAlaSer GlyTyrArgThrGluPheValSerAlaPheCysGlnThrCysSerAspPheValGluGlnPheGlyArgGluArgAlaArgThrAspAlaArgGlyIleGlyPheAspAspAlaGlnAsnIleIle GlnHisLeuArgAlaTyrAlaArgAlaCysArgSerArgAlaGlyGluAlaValGlyArgSerAsnGluGlyValSerAlaValValAspValGlnGlnArgThrLeuArgAlaPheLysGln GlnPhePheAlaValPheValPhePheValGlnHisAlaGlyHisValGlyAsnHisArgArgAsnAlaArgArgAspPhePheAspAsnArgHisHisValPheArgPheHisArgLeuGly IleValGlnMetLeuGlnLeuAspValValIleSerLysAspGlyIleGlnPhePheThrGlnPhePheArgMetGlnGlnIleGlyGlyAlaAsnGlyAlaAlaCysHisPheValPheValGly ArgAlaAspAlaAlaAlaGlyArgAlaAspPheAlaPheAlaAlaArgCysPheSerGlyLeuValGluArgAspValIleArgGlnAspGlnArgAlaGlyArgArgAspPheGlnThrAla PheAspValPheHisAlaCysArgValGlnLeuValAspPheAlaGlnGlnGlyPheGlyGlyAspAspAsnAlaArgThrAspGluAlaValGlnThrPheMetGlnAspAlaAlaArgAsn GlnAlaGlnAsnGlyPhePheAlaAlaAspAsnGlnGlyMetThrArgIleValAlaAlaLeuGluAlaHisHisAlaSerGlyPhePheArgGlnProValAsnAspPheThrPheThrLeuVal AlaProLeuCysAlaAspTyrTyrAsnIlePheSerHisSerHisIleThrXxxArgTyr-435 a907

AMPHI Regions - AMPHI

SEQ. ID. NO. 24423 1-MetLysLysProThrAspThrLeuProValAsnLeuGlnArgArgArgLeuLeuCysAlaAlaGlyAlaLeuLeuLeuSerProLeuAlaGlnAlaGlyAla GlnArgGluGluThrLeuAlaAspAspValAlaSerValMetArgSerSerValGlySerIleAsnProProArgLeuValPheAspAsnProLysGluGlyGlu ArgTrpLeuSerAlaMetSerAlaArgLeuAlaArgPheValProAspGluGluGluArgArgArgLeuLeuValAsnIleGlnTyrGluSerSerArgAlaGly LeuAspThrGlnIleValLeuGlyLeuIleGluValGluSerAlaPheArgGlnTyrAlaIleSerGlyValGlyAlaArgGlyLeuMetGlnValMetProPhe TrpLysAsnTyrIleGlyLysProAlaHisAsnLeuPheAspIleArgThrAsnLeuArgTyrGlyCysThrIleLeuArgHisTyrArgAsnLeuGluLys GlyAsnIleValArgAlaLeuAlaArgPheAsnGlySerLeuGlySerAsnLysTyrProAsnAlaValLeuGlyAlaTrpArgAsnArgTrpGlnTrpArg-207

Antigenic Index - Jameson-Wolf (SEQ. ID. NO. 24423)

1-MetLysLysProThrAspThrLeuProValAsnLeuGlnArgArgArgLeuLeuCysAlaAlaGlyAlaLeuLeuLeuSerProLeuAlaGlnAlaGlyAlaGlnArgGluGluThrLeuAla AspAspValAlaSerValMetArgSerSerValGlySerIleAsnProProArgLeuValPheAspAsnProLysGluGlyGluArgTrpLeuSerAlaMetSerAlaArgLeuAlaArgPheVal ProAspGluGluGluArgArgArgLeuLeuValAsnIleGlnTyrGluSerSerArgAlaGlyLeuAspThrGlnIleValLeuGlyLeuIleGluValGluSerAlaPheArgGlnTyrAlaIle SerGlyValGlyAlaArgGlyLeuMetGlnValMetProPheTrpLysAsnTyrIleGlyLysProAlaHisAsnLeuPheAspIleArgThrAsnLeuArgTyrGlyCysThrIleLeuArgHis TyrArgAsnLeuGluLysGlyAsnIleValArgAlaLeuAlaArgPheAsnGlySerLeuGlySerAsnLysTyrProAsnAlaValLeuGlyAlaTrpArgAsnArgTrpGlnTrpArg-207

Hydrophilic Regions - Hopp-Woods (SEQ. ID. NO. 24423)

1-MetLysLysProThrAspThrLeuProValAsnLeuGlnArgArgArgLeuLeuCysAlaAlaGlyAlaLeuLeuLeuSerProLeuAlaGlnAlaGlyAlaGlnArgGluGluThrLeuAla AspAspValAlaSerValMetArgSerSerValGlySerIleAsnProProArgLeuValPheAspAsnProLysGluGlyGluArgTrpLeuSerAlaMetSerAlaArgLeuAlaArgPheVal ProAspGluGluGluArgArgArgLeuLeuValAsnIleGlnTyrGluSerSerArgAlaGlyLeuAspThrGlnIleValLeuGlyLeuIleGluValGluSerAlaPheArgGlnTyrAlaIleSer GlyValGlyAlaArgGlyLeuMetGlnValMetProPheTrpLysAsnTyrIleGlyLysProAlaHisAsnLeuPheAspIleArgThrAsnLeuArgTyrGlyCysThrIleLeuArgHisTyr ArgAsnLeuGluLysGlyAsnIleValArgAlaLeuAlaArgPheAsnGlySerLeuGlySerAsnLysTyrProAsnAlaValLeuGlyAlaTrpArgAsnArgTrpGlnTrpArg-207 a908

AMPHI Regions - AMPHI

SEQ. ID. NO. 24424 1-MetArgLysSerArgLeuSerGlnTyrLysGlnAsnLysLeuIleGluLeuPheValAlaGlyValThrAlaArgThrAlaAlaGluLeuValGlyValAsn LysAsnThrAlaAlaTyrTyrPheHisArgLeuArgLeuLeuIleTyrGlnAsnSerProHisLeuGluMetPheAspGlyGluValGluAlaAspGluSer

TABLE 1-continued

TyrPheGlyGlyGlnArgLysGlyLysArgGlyArgGlyAlaAlaGlyLysValAlaValPheGlyLeuLeuLysArgAsnGlyLysValTyrThrValThr
ValProAsnThrGlnThrAlaThrLeuPheProIleIleArgGluGlnValLysProAspSerIleValTyrThrAspCysTyrArgSerTyrAspValLeuAsp
ValArgGluPheSerHisPheSerPheAlaGluThrSerPheSerTyrGlnSerGlnHisThrPheCysArgThrThrLysProTyr-166
Antigenic Index - Jameson-Wolf
(SEQ. ID. NO. 24424)
1-MetArgLysSerArgLeuSerGlnTyrLysGlnAsnLysLeuIleGluLeuPheValAlaGlyValThrAlaArgThrAlaAlaGluLeuValGlyValAsnLysAsnThrAlaAlaTyrTyrPhe
HisArgLeuArgLeuLeuIleTyrGlnAsnSerProHisLeuGluMetPheAspGlyGluValGluAlaAspGluSerTyrPheGlyGlyGlnArgLysGlyLysArgGlyArgGlyAlaAlaGly
LysValAlaValPheGlyLeuLeuLysArgAsnGlyLysValTyrThrValThrValProAsnThrGlnThrAlaThrLeuPheProIleIleArgGluGlnValLysProAspSerIleValTyrThr
AspCysTyrArgSerTyrAspValLeuAspValArgGluPheSerHisPheSerPheAlaGluThrSerPheSerTyrGlnSerGlnHisThrPheCysArgThrThrLysProTyr-166
Hydrophilic Regions - Hopp-Woods
(SEQ. ID. NO. 24424)
1-MetArgLysSerArgLeuSerGlnTyrLysGlnAsnLysLeuIleGluLeuPheValAlaGlyValThrAlaArgThrAlaAlaGluLeuValGlyValAsnLysAsnThrAlaAlaTyrTyrPhe
HisArgLeuArgLeuLeuIleTyrGlnAsnSerProHisLeuGluMetPheAspGlyGluValGluAlaAspGluSerTyrPheGlyGlyGlnArgLysGlyLysArgGlyArgGlyAlaAlaGly
LysValAlaValPheGlyLeuLeuLysArgAsnGlyLysValTyrThrValThrValProAsnThrGlnThrAlaThrLeuPheProIleIleArgGluGlnValLysProAspSerIleValTyrThr
AspCysTyrArgSerTyrAspValLeuAspValArgGluPheSerHisPheSerPheAlaGluThrSerPheSerTyrGlnSerGlnHisThrPheCysArgThrThrLysProTyr-166
a909
AMPHI Regions - AMPHI
SEQ. ID. NO. 24425 71-GlyAsnAsnAlaAspGlu-76
Antigenic Index - Jameson-Wolf
SEQ. ID. NO. 24426 22-ThrTyrGlnAspGlyAsnGlyLysThrAlaValArgGlnLysTyrProAlaGly-39
SEQ. ID. NO. 24427 45-GlnAspGlySerTyrSerLysAsnMetAsnTyrAsnGlnTyrArgProGluArgHisAla-64
SEQ. ID. NO. 24428 68-AsnGlnThrGlyAsnAsnAlaAspGluGluHisArgGlnHisTrpGlnLysProLysPheGlnAsnArg-90
Hydrophilic Regions - Hopp-Woods
SEQ. ID. NO. 24429 23-TyrGlnAspGlyAsnGlyLysThrAlaValArgGlnLysTyr-36
SEQ. ID. NO. 24430 58-TyrArgProGluArgHisAla-64
SEQ. ID. NO. 24431 72-AsnAsnAlaAspGluGluHisArgGlnHisTrpGln-83
SEQ. ID. NO. 24432 85-ProLysPheGlnAsnArg-90
a910
AMPHI Regions - AMPHI
SEQ. ID. NO. 24433 22-SerAlaGluArgGlnIle-27
SEQ. ID. NO. 24434 39-LysAlaValLysMetLeuGlu-45
SEQ. ID. NO. 24435 58-AspHisTrpGlyLysPro-63
SEQ. ID. NO. 24436 69-AlaTyrLysAspGlyArg-74
Antigenic Index - Jameson-Wolf
SEQ. ID. NO. 24437 19-AlaGlyAspSerAlaGluArgGlnIleTyr-28
SEQ. ID. NO. 24438 30-AspProTyrPheGluGlnAsnArgThrLysAlaValLysMetLeuGluGlnArgGlyTyrGln-50
SEQ. ID. NO. 24439 52-HisAspValAspAlaAspAspHisTrpGly-61
SEQ. ID. NO. 24440 68-GluAlaTyrLysAspGlyArgGluTyrAsp-77
SEQ. ID. NO. 24441 83-ProAspLeuLysIleIleLysGluGlnLeuAspArg-94
Hydrophilic Regions - Hopp-Woods
SEQ. ID. NO. 24442 21-AspSerAlaGluArgGlnIleTyr-28
SEQ. ID. NO. 24443 32-TyrPheGluGlnAsnArgThrLysAlaValLysMetLeuGluGlnArgGly-48
SEQ. ID. NO. 24444 52-HisAspValAspAlaAspAspHisTrpGly-61
SEQ. ID. NO. 24445 68-GluAlaTyrLysAspGlyArgGluTyrAsp-77
SEQ. ID. NO. 24446 86-LysIleIleLysGluGlnLeuAspArg-94
a911
AMPHI Regions - AMPHI
SEQ. ID. NO. 24447 6-LeuGluPheTrpValGlyLeuPhe-13
SEQ. ID. NO. 24448 43-ValTyrAlaAspPheGlyAspIleGly-51
SEQ. ID. NO. 24449 97-ValSerAlaGlnIle-101
SEQ. ID. NO. 24450 118-GlyAspThrGluAsnLeuAla-124
SEQ. ID. NO. 24451 140-AsnLeuIleGlyLysPheMetThrSerPhe-149
Antigenic Index - Jameson-Wolf
SEQ. ID. NO. 24452 1-MetLysLysAsnIle-5
SEQ. ID. NO. 24453 35-GlyGlySerAspLysThrTyr-41
SEQ. ID. NO. 24454 48-GlyAspIleGlyGlyLeuLysValAsnAlaProValLys-60
SEQ. ID. NO. 24455 74-LeuAspProLysSerTyrGlnAlaArgValArgLeuAspLeuAspGlyLysTyrGlnPheSerSerAspVal-97
SEQ. ID. NO. 24456 103-ThrSerGlyLeuLeuGly-108
SEQ. ID. NO. 24457 115-GlnGlnGlyGlyAspThrGluAsn-122
SEQ. ID. NO. 24458 149-PheAlaGluLysAsnAlaAspGlyGlyAsnAlaGluLysAlaAlaGlu-164
Hydrophilic Regions - Hopp-Woods
SEQ. ID. NO. 24459 1-MetLysLysAsnIle-5
SEQ. ID. NO. 24460 36-GlySerAspLysThr-40
SEQ. ID. NO. 24461 74-LeuAspProLysSerTyrGlnAlaArgValArgLeuAspLeuAspGly-89
SEQ. ID. NO. 24462 116-GlnGlyGlyAspThrGluAsn-122
SEQ. ID. NO. 24463 149-PheAlaGluLysAsnAlaAspGlyGlyAsnAlaGluLysAlaAlaGlu-164
a912
AMPHI Regions - AMPHI
SEQ. ID. NO. 24464 24-ProAlaAspAlaValAsnGlnIle-31
SEQ. ID. NO. 24465 38-ValLeuSerIleLeu-42
SEQ. ID. NO. 24466 62-PheAspPheGlnArgMetThrAlaLeuAlaValGlyAsnProTrpArgThrAlaSerAspAlaGlnLys-84
SEQ. ID. NO. 24467 89-LysGluPheGlnThrLeu-94
SEQ. ID. NO. 24468 169-TyrArgAsnGlnPheGlyGluIleIleLysAlaLys-180
Antigenic Index - Jameson-Wolf
SEQ. ID. NO. 24469 1-MetLysLysSerSer-5
SEQ. ID. NO. 24470 29-AsnGlnIleArgGlnAsnAlaThrGln-37
SEQ. ID. NO. 24471 42-LeuLysSerGlyAspAlaAsnThrAlaArgGlnLysAlaGluAla-56
SEQ. ID. NO. 24472 74-AsnProTrpArgThrAlaSerAspAlaGlnLysGlnAlaLeuAlaLysGluPhe-91
SEQ. ID. NO. 24473 104-LeuLysLeuLysAsnAlaAsnValAsnValLysAspAsnProIleValAsnLysGlyGlyLysGluIleIleVal-128
SEQ. ID. NO. 24474 130-AlaGluValGlyValProGlyGlnLysProValAsn-141

TABLE 1-continued

| | |
|---|---|
| SEQ. ID. NO. 24475 | 146-ThrTyrGlnSerGlyGlyLysTyrArgThr-155 |
| SEQ. ID. NO. 24476 | 169-TyrArgAsnGlnPhe-173 |
| SEQ. ID. NO. 24477 | 177-IleLysAlaLysGlyValAspGlyLeuIleAla-187 |
| SEQ. ID. NO. 24478 | 189-LeuLysAlaLysAsnGlySerLys-196 |
| Hydrophilic Regions - Hopp-Woods | |
| SEQ. ID. NO. 24479 | 1-MetLysLysSerSer-5 |
| SEQ. ID. NO. 24480 | 31-IleArgGlnAsnAla-35 |
| SEQ. ID. NO. 24481 | 43-LysSerGlyAspAlaAsnThrAlaArgGlnLysAlaGluAla-56 |
| SEQ. ID. NO. 24482 | 78-ThrAlaSerAspAlaGlnLysGlnAlaLeuAlaLysGluPhe-91 |
| SEQ. ID. NO. 24483 | 104-LeuLysLeuLysAsn-108 |
| SEQ. ID. NO. 24484 | 110-AsnValAsnValLysAspAsnProIleVal-119 |
| SEQ. ID. NO. 24485 | 121-LysGlyGlyLysGluIleIleVal-128 |
| SEQ. ID. NO. 24486 | 134-ValProGlyGlnLysProValAsn-141 |
| SEQ. ID. NO. 24487 | 177-IleLysAlaLysGlyValAsp-183 |
| SEQ. ID. NO. 24488 | 189-LeuLysAlaLysAsnGlySerLys-196 |
| a913 | |
| AMPHI Regions - AMPHI | |
| SEQ. ID. NO. 24489 | 22-GluThrArgProAlaAspProTyrGluGlyTyrAsnArg-34 |
| SEQ. ID. NO. 24490 | 53-ArgGlyTyrArgLysValAlaProLys-61 |
| SEQ. ID. NO. 24491 | 66-GlyValSerAsnPhePheAsnAsnLeuCysAspValValSer-79 |
| SEQ. ID. NO. 24492 | 107-LeuGlyGlyLeuIleAspIleAlaGlyAla-116 |
| SEQ. ID. NO. 24493 | 151-ValArgAspAlaLeuGlyThrGlyIleThrSerValTyrSer-164 |
| SEQ. ID. NO. 24494 | 193-AspLeuThrAspSerLeuAspGluAlaAla-202 |
| SEQ. ID. NO. 24495 | 238-LeuValGluSerAla-242 |
| SEQ. ID. NO. 24496 | 257-SerGluThrGlnAla-261 |
| Antigenic Index - Jameson-Wolf | |
| SEQ. ID. NO. 24497 | 21-AlaGluThrArgProAlaAspProTyrGluGlyTyrAsn-33 |
| SEQ. ID. NO. 24498 | 39-PheAsnAspGlnAlaAspArgTyr-46 |
| SEQ. ID. NO. 24499 | 51-AlaAlaArgGlyTyrArgLysValAlaProLysProValArgAla-65 |
| SEQ. ID. NO. 24500 | 81-GlySerAsnIleLeu-85 |
| SEQ. ID. NO. 24501 | 87-LeuAspIleLysArgAlaSerGluAspLeuVal-97 |
| SEQ. ID. NO. 24502 | 117-GlyGlyIleProAspAsnLysAsnThrLeuGlyAsp-128 |
| SEQ. ID. NO. 24503 | 132-SerTrpGlyTrpLysAsnSerAsn-139 |
| SEQ. ID. NO. 24504 | 149-SerThrValArgAspAlaLeu-155 |
| SEQ. ID. NO. 24505 | 163-TyrSerProLysAsnIle-168 |
| SEQ. ID. NO. 24506 | 172-ThrProValGlyArgTrpGly-178 |
| SEQ. ID. NO. 24507 | 185-ValSerThrArgGluGlyLeuLeuAspLeuThrAspSerLeuAspGluAlaAlaIleAspLysTyrSerTyrThrArgAspLeuTyrMet-214 |
| SEQ. ID. NO. 24508 | 216-ValArgAlaArgGlnThrGlyAlaThrProAlaGluGlyThrGluAspAsnIleAspIleAspGluLeuValGluSerAlaGluThrGlyAlaAla-247 |
| SEQ. ID. NO. 24509 | 250-AlaValGlnGluAspSerValSerGluThrGlnAlaGluAlaAlaGlyGluAlaGluThrGlnProGlyThrGlnProGlyThrGlnPro-279 |
| Hydrophilic Regions - Hopp-Woods | |
| SEQ. ID. NO. 24510 | 21-AlaGluThrArgProAlaAspProTyrGluGlyTyrAsn-33 |
| SEQ. ID. NO. 24511 | 40-AsnAspGlnAlaAsp-44 |
| SEQ. ID. NO. 24512 | 53-ArgGlyTyrArgLysValAlaProLysProValArg-64 |
| SEQ. ID. NO. 24513 | 87-LeuAspIleLysArgAlaSerGluAspLeuVal-97 |
| SEQ. ID. NO. 24514 | 118-GlyIleProAspAsnLysAsnThrLeu-126 |
| SEQ. ID. NO. 24515 | 150-ThrValArgAspAlaLeu-155 |
| SEQ. ID. NO. 24516 | 186-SerThrArgGluGlyLeuLeuAspLeuThrAspSerLeuAspGluAlaAlaIleAsp-204 |
| SEQ. ID. NO. 24517 | 216-ValArgAlaArgGlnThrGly-222 |
| SEQ. ID. NO. 24518 | 224-ThrProAlaGluGlyThrGluAspAsnIleAspIleAspGluLeuValGluSerAlaGluThrGlyAlaAla-247 |
| SEQ. ID. NO. 24519 | 250-AlaValGlnGluAspSerValSerGluThrGlnAlaGluAlaAlaGlyGluAlaGluThrGlnPro-271 |
| a914-2 | |
| AMPHI Regions - AMPHI | |
| SEQ. ID. NO. 24520 | 6-LeuGlyIleLeuThrAlaCysAlaAlaMet-15 |
| SEQ. ID. NO. 24521 | 17-AlaPheAlaAspArgIleGlyAspLeu-25 |
| SEQ. ID. NO. 24522 | 65-PheGlnLysThrPheGlu-70 |
| SEQ. ID. NO. 24523 | 81-GlnLysValArgGlnAlaCys-87 |
| Antigenic Index - Jameson-Wolf | |
| SEQ. ID. NO. 24524 | 18-PheAlaAspArgIleGlyAspLeuGluAlaArgLeuAlaGlnLeuGluHisArgValAlaVal-38 |
| SEQ. ID. NO. 24525 | 40-GluSerGlySerAsnThrValLys-47 |
| SEQ. ID. NO. 24526 | 50-LeuPheGlySerAsnSer-55 |
| SEQ. ID. NO. 24527 | 64-ProPheGlnLysThrPheGluAlaSerAspArgAsnGluGlyValAlaArgGlnLysValArgGlnAlaCysAsnArgGluThrSerAla-93 |
| SEQ. ID. NO. 24528 | 95-PheCysGluAspGluAlaIleArgCysArgLysPheAsp-107 |
| Hydrophilic Regions - Hopp-Woods | |
| SEQ. ID. NO. 24529 | 18-PheAlaAspArgIleGlyAspLeuGluAlaArgLeuAlaGlnLeuGluHisArgValAlaVal-38 |
| SEQ. ID. NO. 24530 | 67-LysThrPheGluAlaSerAspArgAsnGluGlyValAlaArgGlnLysValArgGlnAlaCysAsnArgGluThrSer-92 |
| SEQ. ID. NO. 24531 | 95-PheCysGluAspGluAlaIleArgCysArgLysPheAsp-107 |
| a915 | |
| AMPHI Regions - AMPHI | |
| SEQ. ID. NO. 24532 | 9-ValAlaValSerAlaLeuSerAlaCysArgGlnAla-20 |
| SEQ. ID. NO. 24533 | 31-IleSerAspArgSerVal-36 |
| SEQ. ID. NO. 24534 | 67-SerThrIleLysGlnMetPheGlyTyrThrLysLeuProGluGluProLysGlyIleArgValIleTyrValThrAspMetGlyAsnValThrAspTrpThr-100 |
| SEQ. ID. NO. 24535 | 139-GlnAlaGluLysPhe-143 |
| Antigenic Index - Jameson-Wolf | |
| SEQ. ID. NO. 24536 | 15-SerAlaCysArgGlnAlaGluGluGlyProProProLeuProArgGlnIleSerAspArgSerValGlyHis-38 |
| SEQ. ID. NO. 24537 | 43-AsnLeuThrGluHisAsnGlyProLysAla-52 |
| SEQ. ID. NO. 24538 | 57-AsnGlyLysProAspGlnProVal-64 |
| SEQ. ID. NO. 24539 | 75-TyrThrLysLeuProGluGluProLysGlyIle-85 |

TABLE 1-continued

| | |
|---|---|
| SEQ. ID. NO. 24540 | 97-ThrAspTrpThrAsnProAsnAlaAspThrGluTrpMetAspAlaLysLys-113 |
| SEQ. ID. NO. 24541 | 125-GlyMetGlyAlaGluAspAlaLeuProPheGlyAsnLysGluGlnAlaGluLysPheAlaLysAspLysGlyGlyLysValValGlyPheAspAspMetProAspThrTyr-161 |
| Hydrophilic Regions - Hopp-Woods | |
| SEQ. ID. NO. 24542 | 18-ArgGlnAlaGluGluGlyProProProLeu-27 |
| SEQ. ID. NO. 24543 | 30-GlnIleSerAspArgSerVal-36 |
| SEQ. ID. NO. 24544 | 46-GluHisAsnGlyProLys-51 |
| SEQ. ID. NO. 24545 | 58-GlyLysProAspGln-62 |
| SEQ. ID. NO. 24546 | 77-LysLeuProGluGluProLysGlyIle-85 |
| SEQ. ID. NO. 24547 | 103-AsnAlaAspThrGluTrpMetAspAlaLysLys-113 |
| SEQ. ID. NO. 24548 | 127-GlyAlaGluAspAlaLeu-132 |
| SEQ. ID. NO. 24549 | 135-GlyAsnLysGluGlnAlaGluLysPheAlaLysAspLysGlyGlyLys-150 |
| SEQ. ID. NO. 24550 | 155-AspAspMetProAsp-159 |
| a917 | |
| AMPHI Regions - AMPHI | |
| SEQ. ID. NO. 24551 | 6-ProLeuAlaValLeuThrAlaLeuLeuLeu-15 |
| SEQ. ID. NO. 24552 | 37-ValLeuLysIleTyrAsnTrpSerGluTyrValAspProGluThrValAlaAsp-54 |
| SEQ. ID. NO. 24553 | 99-IleLysAlaGlyAlaTyrGlnLysIleAspLysSerLeu-111 |
| SEQ. ID. NO. 24554 | 124-ArgLeuMetAspGlyValAspPro-131 |
| SEQ. ID. NO. 24555 | 152-ArgValLysLysAlaLeu-157 |
| SEQ. ID. NO. 24556 | 188-AspSerAlaAlaGlu-192 |
| SEQ. ID. NO. 24557 | 206-AsnSerSerAsnThrGluAspIleArgGluAlaThr-217 |
| SEQ. ID. NO. 24558 | 292-AlaLysAsnValAlaAsnAlaHisLysTyrIleAsnAspPheLeuAsp-307 |
| SEQ. ID. NO. 24559 | 325-LysProAlaArgGluLeuMetGluAsp-333 |
| Antigenic Index - Jameson-Wolf | |
| SEQ. ID. NO. 24560 | 18-CysGlyGlySerAspLysProProAlaGluLysProAlaProAlaGluAsnArgAsnVal-37 |
| SEQ. ID. NO. 24561 | 44-SerGluTyrValAspProGluThrValAlaAspPheGluLysLysAsnGlyIleLysValThr-64 |
| SEQ. ID. NO. 24562 | 68-TyrAspSerAspGluThrLeuGluSerLysValLeuThrGlyLysSerGlyTyrAsp-86 |
| SEQ. ID. NO. 24563 | 102-GlyAlaTyrGlnLysIleAspLysSerLeuIleProAsnTyrLysHisLeuAsnProGluMetMetArgLeuMetAspGlyValAspProGlyHisGluTyr-135 |
| SEQ. ID. NO. 24564 | 149-AsnThrGluArgValLysLysAlaLeuGlyThrAspLysLeuProAspAsnGln-166 |
| SEQ. ID. NO. 24565 | 171-PheAspProGluTyrThrSerLysLeuLysGlnCysGly-183 |
| SEQ. ID. NO. 24566 | 201-LeuGlyLysAsnProAsnSerSerAsnThrGluAspIleArgGluAlaThrAlaLeuLeuLysLysAsnArgProAsnIleLysArgPheThrSerSerGlyPheIle-236 |
| SEQ. ID. NO. 24567 | 238-AspLeuAlaArgGlyAspThr-244 |
| SEQ. ID. NO. 24568 | 255-AsnIleAlaLysArgArgAlaGluGluAlaGlyGlyLysGluLysIleArgValMetMetProLysGluGlyValGly-280 |
| SEQ. ID. NO. 24569 | 287-ValIleProLysAspAlaLysAsnValAlaAsn-297 |
| SEQ. ID. NO. 24570 | 305-PheLeuAspProGluValSerAlaLysAsnGlyAsn-316 |
| SEQ. ID. NO. 24571 | 320-TyrAlaProSerSerLysProAlaArgGluLeuMetGluAspGluPheLysAsnAspAsnThrIlePheProThrGluGluAspLeuLysAsn-350 |
| SEQ. ID. NO. 24572 | 368-GlnTrpGlnAspValLysAlaGlyLys-376 |
| Hydrophilic Regions - Hopp-Woods | |
| SEQ. ID. NO. 24573 | 19-GlyGlySerAspLysProProAlaGluLysProAlaProAlaGluAsnArgAsnVal-37 |
| SEQ. ID. NO. 24574 | 47-ValAspProGluThrValAlaAspPheGluLysLysAsnGlyIle-61 |
| SEQ. ID. NO. 24575 | 68-TyrAspSerAspGluThrLeuGluSerLysValLeuThr-80 |
| SEQ. ID. NO. 24576 | 105-GlnLysIleAspLysSerLeu-111 |
| SEQ. ID. NO. 24577 | 121-GluMetMetArgLeuMetAspGlyValAspProGlyHis-133 |
| SEQ. ID. NO. 24578 | 149-AsnThrGluArgValLysLysAlaLeuGlyThrAspLysLeuProAspAsnGln-166 |
| SEQ. ID. NO. 24579 | 174-GluTyrThrSerLysLeuLysGln-181 |
| SEQ. ID. NO. 24580 | 204-AsnProAsnSerSerAsnThrGluAspIleArgGluAlaThrAlaLeuLeuLysLysAsnArgProAsnIleLysArgPheThr-231 |
| SEQ. ID. NO. 24581 | 238-AspLeuAlaArgGlyAspThr-244 |
| SEQ. ID. NO. 24582 | 255-AsnIleAlaLysArgArgAlaGluGluAlaGlyGlyLysGluLysIleArgValMetMetProLysGluGly-278 |
| SEQ. ID. NO. 24583 | 290-LysAspAlaLysAsnValAlaAsn-297 |
| SEQ. ID. NO. 24584 | 305-PheLeuAspProGluValSerAlaLysAsn-314 |
| SEQ. ID. NO. 24585 | 322-ProSerSerLysProAlaArgGluLeuMetGluAspGluPheLysAsnAspAsn-339 |
| SEQ. ID. NO. 24586 | 343-ProThrGluGluAspLeuLysAsn-350 |
| SEQ. ID. NO. 24587 | 370-GlnAspValLysAlaGlyLys-376 |
| a919 | |
| AMPHI Regions - AMPHI | |
| SEQ. ID. NO. 24588 | 13-IleAlaAlaAlaIleLeu-18 |
| SEQ. ID. NO. 24589 | 24-LysSerIleGlnThrPheProGln-31 |
| SEQ. ID. NO. 24590 | 37-IleAsnGlyProAspArgProValGlyIleProAsp-48 |
| SEQ. ID. NO. 24591 | 76-AspPheAlaLysSerLeuGln-82 |
| SEQ. ID. NO. 24592 | 98-GlnAspValCysAlaGlnAlaPheGlnThrProVal-109 |
| SEQ. ID. NO. 24593 | 119-GluArgTyrPheThr-123 |
| SEQ. ID. NO. 24594 | 133-LeuAlaGlyThrValThrGlyTyrTyrGlu-142 |
| SEQ. ID. NO. 24595 | 161-GlyIleProAspAspPheIleSerValPro-170 |
| SEQ. ID. NO. 24596 | 176-ArgSerGlyLysAlaLeuValArgIleArgGln-186 |
| SEQ. ID. NO. 24597 | 191-SerGlyThrIleAspAsnThrGlyGlyThr-200 |
| SEQ. ID. NO. 24598 | 308-GlnGlyIleLysAlaTyrMetGlnGlnAsnProGlnArgLeuAlaGluValLeu-325 |
| SEQ. ID. NO. 24599 | 348-AlaLeuGlyThrProLeuMetGlyGluTyrAlaGlyAlaVal-361 |
| SEQ. ID. NO. 24600 | 382-ArgLysAlaLeuAsnArg-387 |
| Antigenic Index - Jameson-Wolf | |
| SEQ. ID. NO. 24601 | 21-CysGlnSerLysSerIleGlnThr-28 |
| SEQ. ID. NO. 24602 | 30-ProGlnProAspThr-34 |
| SEQ. ID. NO. 24603 | 36-ValIleAsnGlyProAspArgProValGlyIleProAspProAlaGlyThr-52 |
| SEQ. ID. NO. 24604 | 54-ValGlyGlyGlyGly-58 |
| SEQ. ID. NO. 24605 | 76-AspPheAlaLysSerLeuGln-82 |
| SEQ. ID. NO. 24606 | 87-GlyCysAlaAsnLeuLysAsnArgGlnGlyTrpGln-98 |
| SEQ. ID. NO. 24607 | 121-TyrPheThrProTrp-125 |
| SEQ. ID. NO. 24608 | 143-ProValLeuLysGlyAspAspArgArgThrAlaGln-154 |

TABLE 1-continued

| | |
|---|---|
| SEQ. ID. NO. 24609 | 162-IleProAspAspPheIle-167 |
| SEQ. ID. NO. 24610 | 173-AlaGlyLeuArgSerGlyLysAlaLeuValArgIleArgGlnThrGlyLysAsnSerGlyThrIleAspAsnThrGlyGlyThrHis-201 |
| SEQ. ID. NO. 24611 | 215-ThrAlaIleLysGlyArgPheGluGlySerArgPheLeuProTyrHisThrArgAsnGlnIleAsnGlyGlyAlaLeuAspGlyLysAlaPro-245 |
| SEQ. ID. NO. 24612 | 250-AlaGluAspProValGlu-255 |
| SEQ. ID. NO. 24613 | 262-GlnGlySerGlyArgLeuLysThrProSerGlyLysTyrIleArg-276 |
| SEQ. ID. NO. 24614 | 278-GlyTyrAlaAspLysAsnGluHisPro-286 |
| SEQ. ID. NO. 24615 | 293-TyrMetAlaAspLysGlyTyrLeuLysLeuGlyGln-304 |
| SEQ. ID. NO. 24616 | 316-GlnAsnProGlnArgLeuAlaGlu-323 |
| SEQ. ID. NO. 24617 | 326-GlyGlnAsnProSer-330 |
| SEQ. ID. NO. 24618 | 337-LeuThrGlySerSerAsnAspGlyProVal-346 |
| SEQ. ID. NO. 24619 | 359-GlyAlaValAspArgHisTyr-365 |
| SEQ. ID. NO. 24620 | 379-ProValThrArgLysAlaLeuAsn-386 |
| SEQ. ID. NO. 24621 | 393-AspThrGlySerAlaIleLysGlyAlaValArg-403 |
| SEQ. ID. NO. 24622 | 409-GlyTyrGlyAspGluAlaGlyGluLeuAlaGlyLysGlnLysThrThr-424 |
| SEQ. ID. NO. 24623 | 431-LeuProAsnGlyMetLysProGluTyrArgPro-441 |
| Hydrophilic Regions - Hopp-Woods | |
| SEQ. ID. NO. 24624 | 38-AsnGlyProAspArgProValGly-45 |
| SEQ. ID. NO. 24625 | 90-AsnLeuLysAsnArgGlnGlyTrp-97 |
| SEQ. ID. NO. 24626 | 144-ValLeuLysGlyAspAspArgArgThrAlaGln-154 |
| SEQ. ID. NO. 24627 | 175-LeuArgSerGlyLysAlaLeuValArgIleArgGlnThrGlyLysAsnSerGlyThrIleAspAsnThrGly-198 |
| SEQ. ID. NO. 24628 | 215-ThrAlaIleLysGlyArgPheGluGly-223 |
| SEQ. ID. NO. 24629 | 239-AlaLeuAspGlyLysAla-244 |
| SEQ. ID. NO. 24630 | 250-AlaGluAspProVal-254 |
| SEQ. ID. NO. 24631 | 265-GlyArgLeuLysThrProSer-271 |
| SEQ. ID. NO. 24632 | 279-TyrAlaAspLysAsnGluHis-285 |
| SEQ. ID. NO. 24633 | 317-AsnProGlnArgLeuAlaGlu-323 |
| SEQ. ID. NO. 24634 | 337-LeuThrGlySerSerAsnAspGlyPro-345 |
| SEQ. ID. NO. 24635 | 380-ValThrArgLysAlaLeuAsn-386 |
| SEQ. ID. NO. 24636 | 393-AspThrGlySerAlaIle-398 |
| SEQ. ID. NO. 24637 | 412-AspGluAlaGlyGluLeuAlaGlyLysGlnLysThr-423 |
| SEQ. ID. NO. 24638 | 434-GlyMetLysProGluTyrArgPro-441 |
| a919 | |
| AMPHI Regions - AMPHI | |
| SEQ. ID. NO. 24639 | 13-IleAlaAlaAlaIleLeu-18 |
| SEQ. ID. NO. 24640 | 24-LysSerIleGlnThrPheProGln-31 |
| SEQ. ID. NO. 24641 | 37-IleAsnGlyProAspArgProValGlyIleProAsp-48 |
| SEQ. ID. NO. 24642 | 76-AspPheAlaLysSerLeuGln-82 |
| SEQ. ID. NO. 24643 | 98-GlnAspValCysAlaGlnAlaPheGlnThrProVal-109 |
| SEQ. ID. NO. 24644 | 119-GluArgTyrPheThr-123 |
| SEQ. ID. NO. 24645 | 133-LeuAlaGlyThrValThrGlyTyrTyrGlu-142 |
| SEQ. ID. NO. 24646 | 161-GlyIleProAspAspPheIleSerValPro-170 |
| SEQ. ID. NO. 24647 | 176-ArgSerGlyLysAlaLeuValArgIleArgGln-186 |
| SEQ. ID. NO. 24648 | 191-SerGlyThrIleAspAsnThrGlyGlyThr-200 |
| SEQ. ID. NO. 24649 | 308-GlnGlyIleLysAlaTyrMetGlnGlnAsnProGlnArgLeuAlaGluValLeu-325 |
| SEQ. ID. NO. 24650 | 348-AlaLeuGlyThrProLeuMetGlyGluTyrAlaGlyAlaVal-361 |
| SEQ. ID. NO. 24651 | 382-ArgLysAlaLeuAsnArg-387 |
| Antigenic Index - Jameson-Wolf | |
| SEQ. ID. NO. 24652 | 21-CysGlnSerLysSerIleGlnThr-28 |
| SEQ. ID. NO. 24653 | 30-ProGlnProAspThr-34 |
| SEQ. ID. NO. 24654 | 36-ValIleAsnGlyProAspArgProValGlyIleProAspProAlaGlyThr-52 |
| SEQ. ID. NO. 24655 | 54-ValGlyGlyGlyGly-58 |
| SEQ. ID. NO. 24656 | 76-AspPheAlaLysSerLeuGln-82 |
| SEQ. ID. NO. 24657 | 87-GlyCysAlaAsnLeuLysAsnArgGlnGlyTrpGln-98 |
| SEQ. ID. NO. 24658 | 121-TyrPheThrProTrp-125 |
| SEQ. ID. NO. 24659 | 143-ProValLeuLysGlyAspAspArgArgThrAlaGln-154 |
| SEQ. ID. NO. 24660 | 162-IleProAspAspPheIle-167 |
| SEQ. ID. NO. 24661 | 173-AlaGlyLeuArgSerGlyLysAlaLeuValArgIleArgGlnThrGlyLysAsnSerGlyThrIleAspAsnThrGlyGlyThrHis-201 |
| SEQ. ID. NO. 24662 | 215-ThrAlaIleLysGlyArgPheGluGlySerArgPheLeuProTyrHisThrArgAsnGlnIleAsnGlyGlyAlaLeuAspGlyLysAlaPro-245 |
| SEQ. ID. NO. 24663 | 250-AlaGluAspProValGlu-255 |
| SEQ. ID. NO. 24664 | 262-GlnGlySerGlyArgLeuLysThrProSerGlyLysTyrIleArg-276 |
| SEQ. ID. NO. 24665 | 278-GlyTyrAlaAspLysAsnGluHisPro-286 |
| SEQ. ID. NO. 24666 | 293-TyrMetAlaAspLysGlyTyrLeuLysLeuGlyGln-304 |
| SEQ. ID. NO. 24667 | 316-GlnAsnProGlnArgLeuAlaGlu-323 |
| SEQ. ID. NO. 24668 | 326-GlyGlnAsnProSer-330 |
| SEQ. ID. NO. 24669 | 337-LeuThrGlySerSerAsnAspGlyProVal-346 |
| SEQ. ID. NO. 24670 | 359-GlyAlaValAspArgHisTyr-365 |
| SEQ. ID. NO. 24671 | 379-ProValThrArgLysAlaLeuAsn-386 |
| SEQ. ID. NO. 24672 | 393-AspThrGlySerAlaIleLysGlyAlaValArg-403 |
| SEQ. ID. NO. 24673 | 409-GlyTyrGlyAspGluAlaGlyGluLeuAlaGlyLysGlnLysThrThr-424 |
| SEQ. ID. NO. 24674 | 431-LeuProAsnGlyMetLysProGluTyrArgPro-441 |
| Hydrophilic Regions - Hopp-Woods | |
| SEQ. ID. NO. 24675 | 38-AsnGlyProAspArgProValGly-45 |
| SEQ. ID. NO. 24676 | 90-AsnLeuLysAsnArgGlnGlyTrp-97 |
| SEQ. ID. NO. 24677 | 144-ValLeuLysGlyAspAspArgArgThrAlaGln-154 |
| SEQ. ID. NO. 24678 | 175-LeuArgSerGlyLysAlaLeuValArgIleArgGlnThrGlyLysAsnSerGlyThrIleAspAsnThrGly-198 |
| SEQ. ID. NO. 24679 | 215-ThrAlaIleLysGlyArgPheGluGly-223 |
| SEQ. ID. NO. 24680 | 239-AlaLeuAspGlyLysAla-244 |
| SEQ. ID. NO. 24681 | 250-AlaGluAspProVal-254 |
| SEQ. ID. NO. 24682 | 265-GlyArgLeuLysThrProSer-271 |
| SEQ. ID. NO. 24683 | 279-TyrAlaAspLysAsnGluHis-285 |

TABLE 1-continued

| | |
|---|---|
| SEQ. ID. NO. 24684 | 317-AsnProGlnArgLeuAlaGlu-323 |
| SEQ. ID. NO. 24685 | 337-LeuThrGlySerSerAsnAspGlyPro-345 |
| SEQ. ID. NO. 24686 | 380-ValThrArgLysAlaLeuAsn-386 |
| SEQ. ID. NO. 24687 | 393-AspThrGlySerAlaIle-398 |
| SEQ. ID. NO. 24688 | 412-AspGluAlaGlyGluLeuAlaGlyLysGlnLysThr-423 |
| SEQ. ID. NO. 24689 | 434-GlyMetLysProGluTyrArgPro-441 |
| a920-2 | |
| AMPHI Regions - AMPHI | |
| SEQ. ID. NO. 24690 | 43-GlyGluPheProGluLeuGluProIleAla-52 |
| SEQ. ID. NO. 24691 | 118-IleLysGlnMetProAsp-123 |
| SEQ. ID. NO. 24692 | 135-LysAsnIleValAsnVal-140 |
| SEQ. ID. NO. 24693 | 163-LeuAspAsnProAlaAsn-168 |
| SEQ. ID. NO. 24694 | 190-ThrValThrAlaThrPheAspGlyPheAspThrSerAspArgSerLys-205 |
| SEQ. ID. NO. 24695 | 212-GlnAlaPheSerAspSerThr-218 |
| Antigenic Index - Jameson-Wolf | |
| SEQ. ID. NO. 24696 | 40-LeuGlyTyrGlyGlu-44 |
| SEQ. ID. NO. 24697 | 49-GluProIleAlaLysAspArgLeu-56 |
| SEQ. ID. NO. 24698 | 66-ValThrGluLysGlyLysGluAsnMetIle-75 |
| SEQ. ID. NO. 24699 | 82-TyrGlnTyrArgSerAsnArgProValLysAspGlySerTyr-95 |
| SEQ. ID. NO. 24700 | 104-ThrPheTrpSerLysAsnLysAlaGlyTrp-113 |
| SEQ. ID. NO. 24701 | 120-GlnMetProAspAlaSerTyrCysGluGlnThrArgMetPheGlyLysAsnIleValAsnValGlyHisGluSerAlaAspThr-147 |
| SEQ. ID. NO. 24702 | 152-LysProValGlyGlnAsnLeuGlu-159 |
| SEQ. ID. NO. 24703 | 162-ProLeuAspAsnProAla-167 |
| SEQ. ID. NO. 24704 | 173-GluArgPheLysVal-177 |
| SEQ. ID. NO. 24705 | 181-PheArgGlyGluProLeuProAsnAla-189 |
| SEQ. ID. NO. 24706 | 194-ThrPheAspGlyPheAspThrSerAspArgSerLysThrHisLysThrGluAla-211 |
| SEQ. ID. NO. 24707 | 213-AlaPheSerAspSerThrAspAspLysGlyGluValAsp-225 |
| SEQ. ID. NO. 24708 | 237-AsnValGluHisLysAlaAspPheProAspGlnSerValCysGlnLysGlnAlaAsnTyrSer-257 |
| Hydrophilic Regions - Hopp-Woods | |
| SEQ. ID. NO. 24709 | 49-GluProIleAlaLysAspArgLeu-56 |
| SEQ. ID. NO. 24710 | 66-ValThrGluLysGlyLysGluAsnMetIle-75 |
| SEQ. ID. NO. 24711 | 85-ArgSerAsnArgProValLysAspGlySer-94 |
| SEQ. ID. NO. 24712 | 107-SerLysAsnLysAlaGlyTrp-113 |
| SEQ. ID. NO. 24713 | 128-GluGlnThrArgMetPheGly-134 |
| SEQ. ID. NO. 24714 | 142-HisGluSerAlaAsp-146 |
| SEQ. ID. NO. 24715 | 173-GluArgPheLysVal-177 |
| SEQ. ID. NO. 24716 | 196-AspGlyPheAspThrSerAspArgSerLysThrHisLysThrGluAla-211 |
| SEQ. ID. NO. 24717 | 213-AlaPheSerAspSerThrAspAspLysGlyGluValAsp-225 |
| SEQ. ID. NO. 24718 | 237-AsnValGluHisLysAlaAspPheProAsp-246 |
| SEQ. ID. NO. 24719 | 248-SerValCysGlnLys-252 |
| a921 | |
| AMPHI Regions - AMPHI | |
| SEQ. ID. NO. 24720 | 10-IleValAlaValLeuSerGlyCysGlnSerIleTyrValProThrLeuThrGluIleProValAsn-31 |
| SEQ. ID. NO. 24721 | 33-IleAsnThrValLysThr-38 |
| SEQ. ID. NO. 24722 | 51-HisTrpThrAspValAlaLysIleSerAspGlu-61 |
| SEQ. ID. NO. 24723 | 72-GlyLysMetThrLysValGlnAlaAlaGlnTyrLeuAsnAsnPheArgLys-88 |
| SEQ. ID. NO. 24724 | 98-AspSerMetTyrGluIleTyrLeuArg-106 |
| SEQ. ID. NO. 24725 | 126-GlnAsnAlaLeuArgGlyTrpGlnGlnArg-135 |
| Antigenic Index - Jameson-Wolf | |
| SEQ. ID. NO. 24726 | 36-ValLysThrGluAlaProAlaLysGlyPheArg-46 |
| SEQ. ID. NO. 24727 | 56-AlaLysIleSerAspGluAlaThrArg-64 |
| SEQ. ID. NO. 24728 | 72-GlyLysMetThrLys-76 |
| SEQ. ID. NO. 24729 | 84-AsnAsnPheArgLysArgLeuValGlyArgAsnAlaValAspAspSerMet-100 |
| SEQ. ID. NO. 24730 | 108-AlaIleAspSerGlnArgGlyAlaIleAsnThrGluGlnSerLys-122 |
| SEQ. ID. NO. 24731 | 128-AlaLeuArgGlyTrpGlnGlnArgTrpLysAsnMetAspValLysProAsnAsnProAla-147 |
| Hydrophilic Regions - Hopp-Woods | |
| SEQ. ID. NO. 24732 | 36-ValLysThrGluAlaProAlaLysGlyPheArg-46 |
| SEQ. ID. NO. 24733 | 56-AlaLysIleSerAspGluAlaThrArg-64 |
| SEQ. ID. NO. 24734 | 86-PheArgLysArgLeuValGly-92 |
| SEQ. ID. NO. 24735 | 94-AsnAlaValAspAspSerMet-100 |
| SEQ. ID. NO. 24736 | 108-AlaIleAspSerGlnArgGlyAlaIleAsnThrGluGlnSerLys-122 |
| SEQ. ID. NO. 24737 | 136-TrpLysAsnMetAspValLysProAsnAsn-145 |
| a922 | |
| AMPHI Regions - AMPHI | |
| SEQ. ID. NO. 24738 | 16-LeuSerAlaCysThr-20 |
| SEQ. ID. NO. 24739 | 28-ArgAlaAsnGluAlaGlnAlaPro-35 |
| SEQ. ID. NO. 24740 | 72-ValArgArgPheValAspAsp-78 |
| SEQ. ID. NO. 24741 | 89-GluTrpGlnAspPhePheAspLys-96 |
| SEQ. ID. NO. 24742 | 104-ValLysIleMetHis-108 |
| SEQ. ID. NO. 24743 | 144-AspAspValAlaGln-148 |
| SEQ. ID. NO. 24744 | 172-GlySerPheArgValAlaAspAlaLeu-180 |
| SEQ. ID. NO. 24745 | 196-LysGluLeuValGluLeuLeuLysLeuAla-205 |
| SEQ. ID. NO. 24746 | 222-AlaMetGlyMetPro-226 |
| SEQ. ID. NO. 24747 | 245-HisArgAspIleTrpGlyAsnValGlyAspValAlaAlaSerIleAlaAsnTyrMetLysGlnHis-266 |
| SEQ. ID. NO. 24748 | 298-ArgThrValAlaAspLeuLysAlaTyr-306 |
| SEQ. ID. NO. 24749 | 335-TyrLeuGlyLeuAsnAsnPheTyrThr-343 |
| Antigenic Index - Jameson-Wolf | |
| SEQ. ID. NO. 24750 | 1-MetLysAsnArgLysIleLeu-7 |
| SEQ. ID. NO. 24751 | 22-MetGluAlaArgProProArgAlaAsnGluAlaGlnAlaProArgAlaAspGluMetLysLysGluSerArgProAlaPhe-48 |
| SEQ. ID. NO. 24752 | 61-ValSerAspSerGlyPhe-66 |

TABLE 1-continued

| | |
|---|---|
| SEQ. ID. NO. 24753 | 70-AlaAsnValArgArgPheValAspAspGluValGlyLysGlyAspPheSerArgAlaGluTrp-90 |
| SEQ. ID. NO. 24754 | 107-MetHisArgProSerThrSerArgPro-115 |
| SEQ. ID. NO. 24755 | 120-ArgThrGlyAsnSerGlyLysAlaLysPheArgGlyAlaArgArgPheTyrAlaGluAsnArgAlaLeuIle-143 |
| SEQ. ID. NO. 24756 | 145-AspValAlaGlnLysTyrGlyVal-152 |
| SEQ. ID. NO. 24757 | 163-IleGluThrAsnTyrGlyLysAsnThrGlySer-173 |
| SEQ. ID. NO. 24758 | 186-AspTyrProArgArgAlaGlyPhePhe-194 |
| SEQ. ID. NO. 24759 | 203-LysLeuAlaLysGluGluGlyGlyAsp-211 |
| SEQ. ID. NO. 24760 | 229-MetProSerSerTyrArgLysTrpAlaValAspTyrAspGlyAspGlyHisArgAspIle-248 |
| SEQ. ID. NO. 24761 | 266-HisGlyTrpArgThrGlyGlyLys-273 |
| SEQ. ID. NO. 24762 | 281-AlaProGlyAlaAsp-285 |
| SEQ. ID. NO. 24763 | 290-IleGlyGluLysThrAlaLeu-296 |
| SEQ. ID. NO. 24764 | 310-ProGlyGluGluLeuAlaAspAspGluLysAlaVal-321 |
| SEQ. ID. NO. 24765 | 326-GluThrAlaProGly-330 |
| SEQ. ID. NO. 24766 | 357-ValArgAspIleAlaAsnSerLeuGlyGlyProGlyLeu-369 |
| Hydrophilic Regions - Hopp-Woods | |
| SEQ. ID. NO. 24767 | 1-MetLysAsnArgLysIleLeu-7 |
| SEQ. ID. NO. 24768 | 22-MetGluAlaArgProProArgAlaAsnGluAlaGlnAlaProArgAlaAspGluMetLysLysGluSerArgProAlaPhe-48 |
| SEQ. ID. NO. 24769 | 70-AlaAsnValArgArgPheValAspAspGluValGlyLysGlyAspPheSerArgAlaGluTrp-90 |
| SEQ. ID. NO. 24770 | 122-GlyAsnSerGlyLysAlaLysPheArgGlyAlaArgArgPheTyrAlaGluAsnArgAlaLeuIle-143 |
| SEQ. ID. NO. 24771 | 166-AsnTyrGlyLysAsnThrGly-172 |
| SEQ. ID. NO. 24772 | 187-TyrProArgArgAlaGlyPhePhe-194 |
| SEQ. ID. NO. 24773 | 203-LysLeuAlaLysGluGluGlyGlyAsp-211 |
| SEQ. ID. NO. 24774 | 240-TyrAspGlyAspGlyHisArgAspIle-248 |
| SEQ. ID. NO. 24775 | 290-IleGlyGluLysThrAlaLeu-296 |
| SEQ. ID. NO. 24776 | 310-ProGlyGluGluLeuAlaAspAspGluLysAlaVal-321 |
| SEQ. ID. NO. 24777 | 357-ValArgAspIleAla-361 |
| a923-2 | |
| AMPHI Regions - AMPHI | |
| SEQ. ID. NO. 24778 | 9-LeuMetAlaCysAlaAlaPheLeu-16 |
| SEQ. ID. NO. 24779 | 26-LeuGlyAlaCysTyrAlaIleLeuSerLeuTyrAla-37 |
| SEQ. ID. NO. 24780 | 63-ProAlaLeuPheGlyGlyTrpAlaGly-71 |
| Antigenic Index - Jameson-Wolf | |
| SEQ. ID. NO. 24781 | 43-IleAspLysArgArgAlaValArgGlyLysArgArgIleProGluHisArgLeu-60 |
| SEQ. ID. NO. 24782 | 77-ArgIlePheArgHisLysThrAlaLysLysArgPhe-88 |
| Hydrophilic Regions - Hopp-Woods | |
| SEQ. ID. NO. 24783 | 43-IleAspLysArgArgAlaValArgGlyLysArgArgIleProGluHisArgLeu-60 |
| SEQ. ID. NO. 24784 | 77-ArgIlePheArgHisLysThrAlaLysLysArgPhe-88 |
| a925-1 | |
| AMPHI Regions - AMPHI | |
| SEQ. ID. NO. 24785 | 66-LysCysGlyGlnThrAlaGln-72 |
| SEQ. ID. NO. 24786 | 90-HisGlnAlaAlaIleGluGlnLeuLys-98 |
| SEQ. ID. NO. 24787 | 105-PheAspGluLeuGlu-109 |
| Antigenic Index - Jameson-Wolf | |
| SEQ. ID. NO. 24788 | 6-PheThrGlyLysGluGluSerMetLeuLeuSerGluLysAspGlyAla-21 |
| SEQ. ID. NO. 24789 | 25-AsnThrGlyIleGly-29 |
| SEQ. ID. NO. 24790 | 31-IleProIleLysLeuSerAspAspGlyLysGluLeuTyrValGluArgArgGlnTyrValLysThrAspAlaAlaMetLysAspLysIleIleAlaHisGlnLysLysCysGlyGlnThr-70 |
| SEQ. ID. NO. 24791 | 75-LeuAspAlaArgAsnAlaLeuProSerAsnGlnThrTyrGln-88 |
| SEQ. ID. NO. 24792 | 95-GluGlnLeuLysArgArgPheGluAlaGluPheAspGluLeuGluLysGluIleLysCysAsnGlyLysProThr-119 |
| Hydrophilic Regions - Hopp-Woods | |
| SEQ. ID. NO. 24793 | 7-ThrGlyLysGluGluSerMetLeuLeuSerGluLysAspGlyAla-21 |
| SEQ. ID. NO. 24794 | 31-IleProIleLysLeuSerAspAspGlyLysGluLeuTyrValGluArgArgGlnTyrValLysThrAspAlaAlaMetLysAspLysIleIleAlaHisGlnLysLysCysGlyGln-69 |
| SEQ. ID. NO. 24795 | 75-LeuAspAlaArgAsnAlaLeu-81 |
| SEQ. ID. NO. 24796 | 95-GluGlnLeuLysArgArgPheGluAlaGluPheAspGluLeuGluLysGluIleLysCysAsnGlyLys-117 |
| a926 | |
| AMPHI Regions - AMPHI | |
| SEQ. ID. NO. 24797 | 32-HisThrArgSerPhe-36 |
| SEQ. ID. NO. 24798 | 72-LeuGlySerThrLeuGlyGln-78 |
| SEQ. ID. NO. 24799 | 98-AlaGluSerAlaGluGluLeuSerArgGln-107 |
| SEQ. ID. NO. 24800 | 129-GlyAlaProTyrArgIleLeuProAspGlyIle-139 |
| SEQ. ID. NO. 24801 | 151-AlaAspSerGlyGlyGlnVal-157 |
| Antigenic Index - Jameson-Wolf | |
| SEQ. ID. NO. 24802 | 19-LeuProGlnAsnAsnGluAsnLeuTrpGlnProSerGluHisThrArgSerPheThrAlaGluGlyArgLeuAlaValLysAlaGluGlyLysGlySerTyrAla-53 |
| SEQ. ID. NO. 24803 | 70-ThrProLeuGlySer-74 |
| SEQ. ID. NO. 24804 | 79-LeuCysGlnAspArgAspGlyAlaLeu-87 |
| SEQ. ID. NO. 24805 | 89-ValAspGlyLysGlyAsnValTyr-96 |
| SEQ. ID. NO. 24806 | 99-GluSerAlaGluGluLeuSerArg-106 |
| SEQ. ID. NO. 24807 | 122-AlaAspGlyArgProValAlaGlyAlaPro-131 |
| SEQ. ID. NO. 24808 | 134-IleLeuProAspGlyIleLeu-140 |
| SEQ. ID. NO. 24809 | 148-GlyArgThrAlaAspSerGlyGlyGln-156 |
| SEQ. ID. NO. 24810 | 177-GlyMetProSerGluThrGluThrGlnGluGlnCysAla-189 |
| Hydrophilic Regions - Hopp-Woods | |
| SEQ. ID. NO. 24811 | 36-PheThrAlaGluGlyArgLeuAlaValLysAlaGluGlyLysGlySer-51 |
| SEQ. ID. NO. 24812 | 80-CysGlnAspArgAspGlyAlaLeu-87 |
| SEQ. ID. NO. 24813 | 89-ValAspGlyLysGly-93 |
| SEQ. ID. NO. 24814 | 99-GluSerAlaGluGluLeuSerArg-106 |
| SEQ. ID. NO. 24815 | 123-AspGlyArgProValAla-128 |

TABLE 1-continued

| | |
|---|---|
| SEQ. ID. NO. 24816 | 149-ArgThrAlaAspSerGlyGlyGln-156 |
| SEQ. ID. NO. 24817 | 180-SerGluThrGluThrGlnGluGlnCysAla-189 |
| a927 | |
| AMPHI Regions - AMPHI | |
| SEQ. ID. NO. 24818 | 13-LeuLeuSerAlaCysSer-18 |
| SEQ. ID. NO. 24819 | 48-SerTyrAspValAlaArgAspPheTyrLysGlu-58 |
| SEQ. ID. NO. 24820 | 120-LysGlyTrpGlnGlnAlaLeuPro-127 |
| SEQ. ID. NO. 24821 | 145-AsnProLysGlnIleArgAspTrpAsnAspLeuAlaLysAspGly-159 |
| SEQ. ID. NO. 24822 | 197-LysLeuValAlaSerIleLeu-203 |
| Antigenic Index - Jameson-Wolf | |
| SEQ. ID. NO. 24823 | 18-SerProAlaAlaAspSerAsnHisProSerGlyGlnAsnAlaProAlaAsnThrGluSerAspGlyLysAsnIleThr-43 |
| SEQ. ID. NO. 24824 | 48-SerTyrAspValAlaArgAspPheTyrLysGluTyrAsnPro-61 |
| SEQ. ID. NO. 24825 | 67-TyrGlnSerGluHisProGlyThrSer-75 |
| SEQ. ID. NO. 24826 | 80-GlnSerHisGlyGlySerSerLysGln-88 |
| SEQ. ID. NO. 24827 | 104-AsnGlnSerSerAspIleAspLeuLeuGluLysLysGlyLeuVal-118 |
| SEQ. ID. NO. 24828 | 126-LeuProAspHisAlaAlaProTyrThr-134 |
| SEQ. ID. NO. 24829 | 142-ArgLysAsnAsnProLysGlnIleArgAspTrpAsnAspLeuAlaLysAspGlyVal-160 |
| SEQ. ID. NO. 24830 | 166-AsnProLysThrSerGlyAsnGlyArg-174 |
| SEQ. ID. NO. 24831 | 185-LeuLysThrThrAsnGlyAsnGluGlnGluAlaGlnLys-197 |
| SEQ. ID. NO. 24832 | 203-LeuLysAsnThrProValPheGluAsnGlyGlyArgAlaProPrProProSerHisAsnAlaThrSer-225 |
| SEQ. ID. NO. 24833 | 230-SerLeuLeuLysThrLysProThrThrSerAlaLysAsn-242 |
| Hydrophilic Regions - Hopp-Woods | |
| SEQ. ID. NO. 24834 | 19-ProAlaAlaAspSerAsnHisProSer-27 |
| SEQ. ID. NO. 24835 | 33-AlaAsnThrGluSerAspGlyLysAsn-41 |
| SEQ. ID. NO. 24836 | 50-AspValAlaArgAspPheTyrLys-57 |
| SEQ. ID. NO. 24837 | 67-TyrGlnSerGluHisProGly-73 |
| SEQ. ID. NO. 24838 | 82-HisGlyGlySerSerLysGln-88 |
| SEQ. ID. NO. 24839 | 105-GlnSerSerAspIleAspLeuLeuGluLysLysGlyLeuVal-118 |
| SEQ. ID. NO. 24840 | 142-ArgLysAsnAsnProLysGlnIleArgAspTrpAsnAspLeuAlaLysAspGlyVal-160 |
| SEQ. ID. NO. 24841 | 167-ProLysThrSerGlyAsnGly-173 |
| SEQ. ID. NO. 24842 | 187-ThrThrAsnGlyAsnGluGlnGluAlaGlnLys-197 |
| SEQ. ID. NO. 24843 | 211-AsnGlyGlyArgAlaProPro-217 |
| SEQ. ID. NO. 24844 | 232-LeuLysThrLysProThrThrSerAlaLysAsn-242 |
| a929 | |
| AMPHI Regions - AMPHI | |
| SEQ. ID. NO. 24845 | 25-ValProAspGlyValLys-30 |
| SEQ. ID. NO. 24846 | 34-TrpThrLeuLeuAlaMetPheIleGlyValIleAlaAlaIleIle-48 |
| SEQ. ID. NO. 24847 | 76-GlyAlaAlaMetSerAspAlaLeuSerAlaPhe-86 |
| SEQ. ID. NO. 24848 | 155-HisProIleMetGlnSerIleAlaGlySerTyrGlySerAsnProAlaLys-171 |
| SEQ. ID. NO. 24849 | 180-TyrLeuAlaLeuVal-184 |
| SEQ. ID. NO. 24850 | 204-ProLeuIleValAsnLeuIleAlaGluAsnLeuGly-215 |
| SEQ. ID. NO. 24851 | 233-GlyValIleAlaPhePhe-238 |
| SEQ. ID. NO. 24852 | 265-ArgLeuArgGluMetGlyLysMetSer-273 |
| SEQ. ID. NO. 24853 | 280-AlaValIlePheGlyIle-285 |
| SEQ. ID. NO. 24854 | 355-LeuGlyLeuIleLysTrpPheSerGlyValLeuAlaGluSerValGlyGlyLeu-372 |
| SEQ. ID. NO. 24855 | 398-ThrAlaHisIleThrAlaMetPheGlyAlaPhePheAla-410 |
| SEQ. ID. NO. 24856 | 452-TyrThrThrMetGlyGluTrpTrp-459 |
| Antigenic Index - Jameson-Wolf | |
| SEQ. ID. NO. 24857 | 25-ValProAspGlyValLysProGln-32 |
| SEQ. ID. NO. 24858 | 71-ThrAlaAspLysProGlyAlaAlaMet-79 |
| SEQ. ID. NO. 24859 | 122-GlyArgLysThrLeuGlyIle-128 |
| SEQ. ID. NO. 24860 | 143-ThrProSerAsnThrAlaArgGlyGlyGly-152 |
| SEQ. ID. NO. 24861 | 163-GlySerTyrGlySerAsnProAlaLysGlyThrGluGlyLysMetGlyLys-179 |
| SEQ. ID. NO. 24862 | 187-HisSerAsnProIleSer-192 |
| SEQ. ID. NO. 24863 | 213-AsnLeuGlySerSerPhe-218 |
| SEQ. ID. NO. 24864 | 248-TyrProProGluIleLysGluThrProAsn-257 |
| SEQ. ID. NO. 24865 | 261-PheAlaLysAspArgLeuArgGluMetGlyLysMetSerAlaAspGluIle-277 |
| SEQ. ID. NO. 24866 | 328-AspValLeuLysGluLysSerAlaTrp-336 |
| Hydrophilic Regions - Hopp-Woods | |
| SEQ. ID. NO. 24867 | 71-ThrAlaAspLysProGlyAlaAlaMet-79 |
| SEQ. ID. NO. 24868 | 146-AsnThrAlaArgGly-150 |
| SEQ. ID. NO. 24869 | 168-AsnProAlaLysGlyThrGluGlyLysMetGlyLys-179 |
| SEQ. ID. NO. 24870 | 250-ProGluIleLysGluThrProAsn-257 |
| SEQ. ID. NO. 24871 | 261-PheAlaLysAspArgLeuArgGluMetGlyLysMetSerAlaAspGluIle-277 |
| SEQ. ID. NO. 24872 | 328-AspValLeuLysGluLysSerAlaTrp-336 |
| a931 | |
| AMPHI Regions - AMPHI | |
| SEQ. ID. NO. 24873 | 43-LysAlaProLysThrValAlaAsnPheValArgTyrAlaArgLys-57 |
| SEQ. ID. NO. 24874 | 67-ArgValIleGlyGly-71 |
| SEQ. ID. NO. 24875 | 81-GluAspLeuAlaGlnLysAlaSerAspLys-90 |
| SEQ. ID. NO. 24876 | 94-AsnGluSerGlyAsnGlyLeuLysAsnThrValGly-105 |
| SEQ. ID. NO. 24877 | 107-IleAlaMetAlaArgThrAlaAspProAsp-116 |
| SEQ. ID. NO. 24878 | 120-SerGlnPhePheIle-124 |
| SEQ. ID. NO. 24879 | 142-ThrValPheGlyArgValGluSerGlyMetAsnThrValSerLysIleAlaArgValLysThrAlaThrArgGlyPhe-167 |
| Antigenic Index - Jameson-Wolf | |
| SEQ. ID. NO. 24880 | 1-MetLysProLysPhe-5 |
| SEQ. ID. NO. 24881 | 30-ThrAspMetGlyAsn-34 |
| SEQ. ID. NO. 24882 | 38-ValLeuAspGluSerLysAlaProLysThr-47 |
| SEQ. ID. NO. 24883 | 53-ArgTyrAlaArgLysGlyPheTyrAspAsnThrIle-64 |
| SEQ. ID. NO. 24884 | 76-GlyGlyGlyLeuThrGluAspLeuAlaGlnLysAlaSerAspLysAlaValAlaAsnGluSerGlyAsnGlyLeuLysAsnThrVal-104 |

TABLE 1-continued

| | |
|---|---|
| SEQ. ID. NO. 24885 | 111-ArgThrAlaAspProAspSerAlaThr-119 |
| SEQ. ID. NO. 24886 | 127-ValAspAsnAspSerLeuAsnTyrLysAsnGlyGln-138 |
| SEQ. ID. NO. 24887 | 145-GlyArgValGluSerGlyMetAsnThrVal-154 |
| SEQ. ID. NO. 24888 | 156-LysIleAlaArgValLysThrAlaThrArgGlyPhe-167 |
| SEQ. ID. NO. 24889 | 176-ValLysIleArgArg-180 |
| Hydrophilic Regions - Hopp-Woods | |
| SEQ. ID. NO. 24890 | 1-MetLysProLysPhe-5 |
| SEQ. ID. NO. 24891 | 30-ThrAspMetGlyAsn-34 |
| SEQ. ID. NO. 24892 | 38-ValLeuAspGluSerLysAlaProLysThr-47 |
| SEQ. ID. NO. 24893 | 78-GlyLeuThrGluAspLeuAlaGlnLysAlaSerAspLysAlaValAlaAsnGluSerGlyAsnGlyLeu-100 |
| SEQ. ID. NO. 24894 | 111-ArgThrAlaAspProAspSerAlaThr-119 |
| SEQ. ID. NO. 24895 | 127-ValAspAsnAspSerLeuAsn-133 |
| SEQ. ID. NO. 24896 | 145-GlyArgValGluSerGlyMet-151 |
| SEQ. ID. NO. 24897 | 156-LysIleAlaArgValLysThrAlaThr-164 |
| SEQ. ID. NO. 24898 | 176-ValLysIleArgArg-180 |
| a933 | |
| AMPHI Regions - AMPHI | |
| SEQ. ID. NO. 24899 | 27-AsnIleProAlaLeuPheProLysHisProPheAspProPheGluAsnIleAsnAsnSerLysArg-48 |
| SEQ. ID. NO. 24900 | 63-GlyPheAlaGlnGlyLeu-68 |
| SEQ. ID. NO. 24901 | 78-GluLysProIleArgGlnTyrPheLysGluCysLeuAsnThrGly-92 |
| SEQ. ID. NO. 24902 | 95-SerAspAspThrCys-99 |
| SEQ. ID. NO. 24903 | 131-ValGlyAsnTyrIleGluTrpLeu-138 |
| SEQ. ID. NO. 24904 | 155-AspValAspProPheHisTyrIleGluVal-164 |
| SEQ. ID. NO. 24905 | 257-GluAsnProIleAspAspLeuLysSerLeuAspGlyHisGlnIleIleLysValAsn-275 |
| SEQ. ID. NO. 24906 | 304-GlyPhePheThrLys-308 |
| SEQ. ID. NO. 24907 | 351-TrpLeuArgValIleAspGlyHisSerAsn-360 |
| SEQ. ID. NO. 24908 | 426-AlaGlyIleTyrAlaThrTrpHis-433 |
| SEQ. ID. NO. 24909 | 447-TrpValGlnTyrGln-451 |
| SEQ. ID. NO. 24910 | 462-AlaThrGluArgPheThr-467 |
| SEQ. ID. NO. 24911 | 469-LysGlyIleThrAlaSer-474 |
| SEQ. ID. NO. 24912 | 478-GlyTyrAsnAlaLeuLeuAla-484 |
| SEQ. ID. NO. 24913 | 543-LeuTyrLysAsnIleAlaIleGlu-550 |
| SEQ. ID. NO. 24914 | 552-PheAlaAlaValAsn-556 |
| SEQ. ID. NO. 24915 | 601-PheAsnArgGlnThrGly-606 |
| Antigenic Index - Jameson-Wolf | |
| SEQ. ID. NO. 24916 | 1-LysLysLeuArgAspArgAsnSerGluTyrTrpLysGluGluThrTyrHisIleLysSerAsnAsnArgValTyrPro-26 |
| SEQ. ID. NO. 24917 | 33-ProLysHisProPheAspProPheGluAsnIleAsnAsnSerLysArgIleSerPheTyrAspLysGluTyrThrGluAspTyr-60 |
| SEQ. ID. NO. 24918 | 69-GlyValAlaLysArgAsnGlyGluThrGluLysProIleArg-82 |
| SEQ. ID. NO. 24919 | 88-CysLeuAsnThrGlyLysTyrSerAspAspThrCysLysSerGlnGlnSer-104 |
| SEQ. ID. NO. 24920 | 108-ValArgSerAspIle-112 |
| SEQ. ID. NO. 24921 | 117-ThrLysileLysAsnSerHisileAsnSerGluile-128 |
| SEQ. ID. NO. 24922 | 145-LeuSerSerSerGlnGluHisLeuTyrSerAspValAspProPheHis-160 |
| SEQ. ID. NO. 24923 | 163-GluValThrAspAsnSerHis-169 |
| SEQ. ID. NO. 24924 | 178-AspGluPheArgLeuGluAsnSerLeuTrpGluProArgTrpAspSerAspValGlyGluLeuLysThrThrAsnAlaAspileArgPheAsnThrLys SerGluSerLeuLeuValLysGluAspTyrAlaGlyGlyAlaArgPhe-226 |
| SEQ. ID. NO. 24925 | 231-GlyLeuLysAspLysValProGluThrPro-240 |
| SEQ. ID. NO. 24926 | 244-PheGluLysAsnIleThrGlyThrSer-252 |
| SEQ. ID. NO. 24927 | 255-IlePheGluAsnProileAspAspLeuLysSerLeuAspGlyHisGlnIleIle-272 |
| SEQ. ID. NO. 24928 | 274-ValAsnGlyThrAlaAspLysHisAlaPheArgLeuSerGlyLysHisGlnLysGly-292 |
| SEQ. ID. NO. 24929 | 298-LeuGlnGlnArgProGluGlyPhe-305 |
| SEQ. ID. NO. 24930 | 308-LysValGlnGluArgAspAspIleSer-316 |
| SEQ. ID. NO. 24931 | 332-ArgLeuAsnAspLysAsnSerAspIlePheAspArgThrLeuProArgLysGlyLeu-350 |
| SEQ. ID. NO. 24932 | 355-IleAspGlyHisSerAsnGlnTrpValGlnGlyLysThrAlaProValGluSerAsnArgLysGlyVal-377 |
| SEQ. ID. NO. 24933 | 387-GlnAsnGluSerAsnGlnLeu-393 |
| SEQ. ID. NO. 24934 | 399-SerGlyGlnAlaGluGlnArgSerThrPheArgAsnProAspThrAspAsnLeuThrThrGlyAsnValLysGlyPheGly-425 |
| SEQ. ID. NO. 24935 | 435-LeuGlnAspLysGlnThrGlyAlaTyrAlaAspSer-446 |
| SEQ. ID. NO. 24936 | 451-GlnArgPheArgHisArgileAsnThrGluAspAlaThrGluArgPheThrSerLysGlyIle-471 |
| SEQ. ID. NO. 24937 | 486-HisPheThrLysLysGlyAsnArgVal-494 |
| SEQ. ID. NO. 24938 | 509-ValAsnGlyLysPheSerAspSerGluAsnAla-519 |
| SEQ. ID. NO. 24939 | 524-LeuGlySerArgGlnLeuGlnSer-531 |
| SEQ. ID. NO. 24940 | 562-LysProPheGlyValGluMetAspGlyGluArgArgMetIleAsnAsnLysThrAlaIleGluSer-583 |
| SEQ. ID. NO. 24941 | 589-ValLysIleLysSer-593 |
| SEQ. ID. NO. 24942 | 600-ThrPheAsnArgGlnThrGlyLysHisHisGlnAlaLysGlnGly-614 |
| Hydrophilic Regions - Hopp-Woods | |
| SEQ. ID. NO. 24943 | 1-LysLysLeuArgAspArgAsnSerGluTyrTrpLysGluGluThrTyrHis-17 |
| SEQ. ID. NO. 24944 | 35-HisProPheAspPro-39 |
| SEQ. ID. NO. 24945 | 44-AsnAsnSerLysArgIleSerPheTyrAspLysGluTyrThrGlu-58 |
| SEQ. ID. NO. 24946 | 70-ValAlaLysArgAsnGlyGluThrGluLysProIle-81 |
| SEQ. ID. NO. 24947 | 93-LysTyrSerAspAspThrCysLysSerGlnGln-103 |
| SEQ. ID. NO. 24948 | 117-ThrLysIleLysAsn-121 |
| SEQ. ID. NO. 24949 | 152-LeuTyrSerAspValAsp-157 |
| SEQ. ID. NO. 24950 | 178-AspGluPheArgLeuGlu-183 |
| SEQ. ID. NO. 24951 | 189-ProArgTrpAspSerAspValGlyGluLeuLysThrThrAsnAlaAspIleArgPheAsnThrLysSerGluSerLeuLeuValLysGluAspTyrAla Gly-222 |
| SEQ. ID. NO. 24952 | 232-LeuLysAspLysValProGlu-238 |
| SEQ. ID. NO. 24953 | 246-LysAsnIleThrGly-250 |
| SEQ. ID. NO. 24954 | 258-AsnProIleAspAspLeuLysSerLeuAsp-267 |
| SEQ. ID. NO. 24955 | 276-GlyThrAlaAspLysHisAlaPhe-283 |
| SEQ. ID. NO. 24956 | 285-LeuSerGlyLysHisGlnLys-291 |
| SEQ. ID. NO. 24957 | 299-GlnGlnArgProGluGlyPhe-305 |

TABLE 1-continued

| | |
|---|---|
| SEQ. ID. NO. 24958 | 309-ValGlnGluArgAspAspIle-315 |
| SEQ. ID. NO. 24959 | 333-LeuAsnAspLysAsnSerAspIlePheAsp-342 |
| SEQ. ID. NO. 24960 | 366-LysThrAlaProValGluSerAsnArgLysGlyVal-377 |
| SEQ. ID. NO. 24961 | 388-AsnGluSerAsnGln-392 |
| SEQ. ID. NO. 24962 | 401-GlnAlaGluGlnArgSerThrPheArgAsnProAspThrAspAsnLeuThr-417 |
| SEQ. ID. NO. 24963 | 435-LeuGlnAspLysGlnThr-440 |
| SEQ. ID. NO. 24964 | 451-GlnArgPheArgHisArgIleAsnThrGluAspAlaThrGluArgPheThrSer-468 |
| SEQ. ID. NO. 24965 | 486-HisPheThrLysLysGlyAsnArg-493 |
| SEQ. ID. NO. 24966 | 512-LysPheSerAspSerGluAsnAla-519 |
| SEQ. ID. NO. 24967 | 527-ArgGlnLeuGlnSer-531 |
| SEQ. ID. NO. 24968 | 564-PheGlyValGluMetAspGlyGluArgArgMetIleAsn-576 |
| SEQ. ID. NO. 24969 | 589-ValLysIleLysSer-593 |
| SEQ. ID. NO. 24970 | 603-ArgGlnThrGlyLysHisHisGlnAlaLysGlnGly-614 |
| a935 | |
| AMPHI Regions - AMPHI | |
| SEQ. ID. NO. 24971 | 41-ValSerAspLysTrpAla-46 |
| SEQ. ID. NO. 24972 | 56-AlaProArgValVal-60 |
| SEQ. ID. NO. 24973 | 72-LeuGluHisSerLeuArgAsp-78 |
| SEQ. ID. NO. 24974 | 87-LeuIleAlaSerLeuAlaAspLeuTyrAlaLysLeu-98 |
| SEQ. ID. NO. 24975 | 111-AlaLeuLeuAlaLysLeuAlaGlyArgProAlaGluAlaValAlaArgTyrArgGlu-129 |
| SEQ. ID. NO. 24976 | 172-ProValLeuGluAsnValGlyArgPheArgLysLysAlaGlu-185 |
| SEQ. ID. NO. 24977 | 375-LysArgLeuGlyGluSerAlaThrValPheGlyGlyTrpGlnPheVal-390 |
| SEQ. ID. NO. 24978 | 415-AlaGlyTrpAlaGlnGluTrpArgGlnLeuGlyGlyLeu-427 |
| SEQ. ID. NO. 24979 | 435-TyrAlaArgArgAsnTyr-440 |
| Antigenic Index - Jameson-Wolf | |
| SEQ. ID. NO. 24980 | 27-AlaIleLeuAspAspLysAlaLeu-34 |
| SEQ. ID. NO. 24981 | 39-ArgSerValSerAspLysTrpAlaGluSerAspTrpLysValAspAsnAspAlaProArgValValAspGlyAspPhe-64 |
| SEQ. ID. NO. 24982 | 70-LysMetLeuGluHisSerLeuArgAspValLeuAsnGlyAsnGlnAlaAsp-86 |
| SEQ. ID. NO. 24983 | 97-LysLeuProAspTyrAspAla-103 |
| SEQ. ID. NO. 24984 | 108-ArgAlaArgAlaLeu-112 |
| SEQ. ID. NO. 24985 | 116-LeuAlaGlyArgProAlaGluAlaValAlaArgTyrArgGluLeuHisGlyGluAsnAlaAlaAspGluArgIleLeu-141 |
| SEQ. ID. NO. 24986 | 145-AlaAlaAlaGluPheAspAspPheArgLeuLysSerAlaGluArgHisPheAlaGluAlaGluLysLeuAspLeu-169 |
| SEQ. ID. NO. 24987 | 176-AsnValGlyArgPheArgLysLysAlaGluGlyLeuThrGly-189 |
| SEQ. ID. NO. 24988 | 192-PheSerGlyGlyIle-196 |
| SEQ. ID. NO. 24989 | 199-AlaValAsnArgAsnAlaAsnAsnAlaAla-208 |
| SEQ. ID. NO. 24990 | 210-GlnTyrCysArgGlnAsnGlyGlyArgGln-219 |
| SEQ. ID. NO. 24991 | 224-SerArgAlaGluArgAlaAla-230 |
| SEQ. ID. NO. 24992 | 236-IleGluAlaGluLysLeuThrAla-243 |
| SEQ. ID. NO. 24993 | 253-ArgSerAsnIleGlyGlyThrSerTyr-261 |
| SEQ. ID. NO. 24994 | 263-PheSerLysLysSerAlaTyrAspAspGlyPheGlyArg-275 |
| SEQ. ID. NO. 24995 | 279-GlyTrpGlnTyrLysAsnAlaArgGlnThr-288 |
| SEQ. ID. NO. 24996 | 300-SerGlySerAspGlyPheAspAlaLysThrLysArgValAsnAsnArgArgLeuProProTyr-320 |
| SEQ. ID. NO. 24997 | 332-HisThrTyrArgProAsnProGlyTrp-340 |
| SEQ. ID. NO. 24998 | 347-GluHisTyrArgGlnArgTyrArgGluGlnAspArgAlaGluTyrAsnAsnGlyArgGlnAspGlyPheTyr-370 |
| SEQ. ID. NO. 24999 | 373-SerAlaLysArgLeuGlyGlu-379 |
| SEQ. ID. NO. 25000 | 392-PheValProLysArgGluThrVal-399 |
| SEQ. ID. NO. 25001 | 406-AlaAlaTyrArgArgAsnGlyValTyrAlaGly-416 |
| SEQ. ID. NO. 25002 | 425-GlyGlyLeuAsnSerArgValSerAlaSerTyrAlaArgArgAsnTyrLysGly-442 |
| SEQ. ID. NO. 25003 | 448-ThrGluAlaGlnArgAsnArgGluTrpAsn-457 |
| SEQ. ID. NO. 25004 | 463-SerHisAspLysLeuSerTyrLysGly-471 |
| SEQ. ID. NO. 25005 | 480-PheGlyArgThrGluSerAsnValProTyrAlaLysArgArgAsnSerGlu-496 |
| SEQ. ID. NO. 25006 | 501-AlaAspTrpArgPhe-505 |
| Hydrophilic Regions - Hopp-Woods | |
| SEQ. ID. NO. 25007 | 27-AlaIleLeuAspAspLysAlaLeu-34 |
| SEQ. ID. NO. 25008 | 39-ArgSerValSerAspLysTrpAlaGluSerAspTrpLysValAspAsnAspAlaProArgValValAsp-61 |
| SEQ. ID. NO. 25009 | 70-LysMetLeuGluHisSerLeuArgAspValLeuAsn-81 |
| SEQ. ID. NO. 25010 | 108-ArgAlaArgAlaLeu-112 |
| SEQ. ID. NO. 25011 | 116-LeuAlaGlyArgProAlaGluAlaValAlaArgTyrArgGluLeuHisGly-132 |
| SEQ. ID. NO. 25012 | 134-AsnAlaAlaAspGluArgIleLeu-141 |
| SEQ. ID. NO. 25013 | 145-AlaAlaAlaGluPheAspAspPheArgLeuLysSerAlaGluArgHisPheAlaGluAlaGluLysLeuAspLeu-169 |
| SEQ. ID. NO. 25014 | 176-AsnValGlyArgPheArgLysLysAlaGluGly-186 |
| SEQ. ID. NO. 25015 | 200-ValAsnArgAsnAlaAsn-205 |
| SEQ. ID. NO. 25016 | 212-CysArgGlnAsnGlyGlyArgGln-219 |
| SEQ. ID. NO. 25017 | 224-SerArgAlaGluArgAlaAla-230 |
| SEQ. ID. NO. 25018 | 236-IleGluAlaGluLysLeuThrAla-243 |
| SEQ. ID. NO. 25019 | 265-LysLysSerAlaTyrAspAspGlyPheGly-274 |
| SEQ. ID. NO. 25020 | 283-LysAsnAlaArgGlnThr-288 |
| SEQ. ID. NO. 25021 | 303-AspGlyPheAspAlaLysThrLysArgValAsnAsnArgArgLeuPro-318 |
| SEQ. ID. NO. 25022 | 348-HisTyrArgGlnArgTyrArgGluGlnAspArgAlaGluTyrAsnAsnGlyArgGlnAsp-367 |
| SEQ. ID. NO. 25023 | 373-SerAlaLysArgLeuGlyGlu-379 |
| SEQ. ID. NO. 25024 | 393-ValProLysArgGluThrVal-399 |
| SEQ. ID. NO. 25025 | 407-AlaTyrArgArgAsnGly-412 |
| SEQ. ID. NO. 25026 | 435-TyrAlaArgArgAsnTyrLys-441 |
| SEQ. ID. NO. 25027 | 449-GluAlaGlnArgAsnArgGluTrp-456 |
| SEQ. ID. NO. 25028 | 463-SerHisAspLysLeuSerTyr-469 |

TABLE 1-continued

| | |
|---|---|
| SEQ. ID. NO. 25029 | 480-PheGlyArgThrGluSer-485 |
| SEQ. ID. NO. 25030 | 489-TyrAlaLysArgArgAsnSerGlu-496 |
| a936-1 | |
| AMPHI Regions - AMPHI | |
| SEQ. ID. NO. 25031 | 8-ValArgThrLeuThrAla-13 |
| SEQ. ID. NO. 25032 | 22-GlyCysValSerAlaVal-27 |
| SEQ. ID. NO. 25033 | 100-GlnPheValGlyGlnIle-105 |
| SEQ. ID. NO. 25034 | 112-AlaGluGlyValTyrAsnTyrIleThrValAlaSerLeuProArgThrAlaGlyAspIleAlaGlyAsp-134 |
| Antigenic Index - Jameson-Wolf | |
| SEQ. ID. NO. 25035 | 1-MetLysProLysProHisThrValArg-9 |
| SEQ. ID. NO. 25036 | 33-ValGlyAlaLysSerAlaValAspArgArgThrThrGlyAlaGlnThrAspAspAsnValMet-53 |
| SEQ. ID. NO. 25037 | 56-ArgIleGluThrThrAlaArgSerTyrLeuArgGlnAsnAsnGlnThrLysGlyTyr-74 |
| SEQ. ID. NO. 25038 | 94-AlaThrGluGlyGluLysGlnPhe-101 |
| SEQ. ID. NO. 25039 | 106-AlaArgSerGluGlnAlaAla-112 |
| SEQ. ID. NO. 25040 | 124-LeuProArgThrAlaGlyAspIleAlaGlyAspThrTrpAsnThrSerLysValArgAla-143 |
| SEQ. ID. NO. 25041 | 149-SerProAlaThrGlnAlaArgValLys-157 |
| SEQ. ID. NO. 25042 | 172-ThrProGluGluGlnAlaGlnIleThr-180 |
| Hydrophilic Regions - Hopp-Woods | |
| SEQ. ID. NO. 25043 | 1-MetLysProLysProHisThr-7 |
| SEQ. ID. NO. 25044 | 37-SerAlaValAspArgArgThrThrGlyAlaGlnThrAspAspAsnValMet-53 |
| SEQ. ID. NO. 25045 | 56-ArgIleGluThrThrAla-61 |
| SEQ. ID. NO. 25046 | 68-AsnAsnGlnThrLysGlyTyr-74 |
| SEQ. ID. NO. 25047 | 94-AlaThrGluGlyGluLysGlnPhe-101 |
| SEQ. ID. NO. 25048 | 106-AlaArgSerGluGlnAlaAla-112 |
| SEQ. ID. NO. 25049 | 125-ProArgThrAlaGly-129 |
| SEQ. ID. NO. 25050 | 152-ThrGlnAlaArgValLys-157 |
| SEQ. ID. NO. 25051 | 172-ThrProGluGluGlnAlaGlnIle-179 |
| a937 | |
| AMPHI Regions - AMPHI | |
| SEQ. ID. NO. 25052 | 6-LeuProAlaLeuProAlaIleLeuProLeuSerAla-17 |
| SEQ. ID. NO. 25053 | 232-LysGlnProAspArgLeuAsp-238 |
| Antigenic Index - Jameson-Wolf | |
| SEQ. ID. NO. 25054 | 27-AspIleMetThrAspLysGlyLysTrpLysLeuGluThr-39 |
| SEQ. ID. NO. 25055 | 44-LeuAsnSerGluAsnAsnArgAlaGluLeu-53 |
| SEQ. ID. NO. 25056 | 71-ThrGluIleGlnGluAsnGlySerAsnThr-80 |
| SEQ. ID. NO. 25057 | 95-GlyAsnThrAspIleTyrGlySerGlySer-104 |
| SEQ. ID. NO. 25058 | 108-HisGluGluArgLysLeuAspGlyAsnGlyLysThrArgAsnLysArgMetSerAsp-126 |
| SEQ. ID. NO. 25059 | 135-PheLeuLysAspAspLysAsnProAla-143 |
| SEQ. ID. NO. 25060 | 151-ThrValTyrGluLysSerArgAsnLysAlaSerSerGlyLysSer-165 |
| SEQ. ID. NO. 25061 | 187-TyrArgIleAsnGlySerLysThrLeuSerSerAsnThrLysTyrLysAlaGly-204 |
| SEQ. ID. NO. 25062 | 217-AlaAsnAspArgIleSerLeuThrGlyGly-226 |
| SEQ. ID. NO. 25063 | 231-GlyLysGlnProAspArgLeuAspGlyLysLysGluSerAlaArgAsnThrSerThr-249 |
| SEQ. ID. NO. 25064 | 273-ValSerGlyGlnSerSerSerGluLeuLysPhe-283 |
| Hydrophilic Regions - Hopp-Woods | |
| SEQ. ID. NO. 25065 | 27-AspIleMetThrAspLysGlyLysTrpLysLeu-37 |
| SEQ. ID. NO. 25066 | 47-GluAsnAsnArgAlaGluLeu-53 |
| SEQ. ID. NO. 25067 | 72-GluIleGlnGluAsnGlySerAsn-79 |
| SEQ. ID. NO. 25068 | 108-HisGluGluArgLysLeuAspGlyAsnGlyLysThrArgAsnLysArgMetSerAsp-126 |
| SEQ. ID. NO. 25069 | 135-PheLeuLysAspAspLysAsnPro-142 |
| SEQ. ID. NO. 25070 | 151-ThrValTyrGluLysSerArgAsnLysAlaSerSer-162 |
| SEQ. ID. NO. 25071 | 193-LysThrLeuSerSer-197 |
| SEQ. ID. NO. 25072 | 199-ThrLysTyrLysAla-203 |
| SEQ. ID. NO. 25073 | 217-AlaAsnAspArgIleSer-222 |
| SEQ. ID. NO. 25074 | 232-LysGlnProAspArgLeuAspGlyLysLysGluSerAlaArgAsn-246 |
| SEQ. ID. NO. 25075 | 277-SerSerSerGluLeuLysPhe-283 |
| a939 | |
| AMPHI Regions - AMPHI | |
| SEQ. ID. NO. 25076 | 32-AlaThrValCysAla-36 |
| SEQ. ID. NO. 25077 | 90-AspGlnAspIleLeu-94 |
| SEQ. ID. NO. 25078 | 121-LysIleTyrArgGly-125 |
| SEQ. ID. NO. 25079 | 135-CysMetSerCysHisGly-140 |
| SEQ. ID. NO. 25080 | 151-SerGluIleGlnAlaTyrProArgLeuGlyGly-161 |
| SEQ. ID. NO. 25081 | 169-GluGlnMetAsnAlaTyrLys-175 |
| SEQ. ID. NO. 25082 | 185-GluAspIleAlaAsnArgMetSer-192 |
| Antigenic Index - Jameson-Wolf | |
| SEQ. ID. NO. 25083 | 18-AlaSerProLysAlaAspValGluLysGlyLysGlnVal-30 |
| SEQ. ID. NO. 25084 | 40-AlaAlaAspGlyAsnSerGlyIle-47 |
| SEQ. ID. NO. 25085 | 66-IleGlyIleArgAspGlyLysArgThrHisGlySerAlaAlaVal-80 |
| SEQ. ID. NO. 25086 | 88-LeuSerAspGlnAspIle-93 |
| SEQ. ID. NO. 25087 | 102-LysGlnGlnProLysSerGlyGluAlaAsnProLysGluAsnProGluLeuGly-119 |
| SEQ. ID. NO. 25088 | 122-IleTyrArgGlyGlyLeuSerAspLysLysValPro-133 |
| SEQ. ID. NO. 25089 | 139-HisGlyProSerGlyAlaGlyMetProGlyGlyGlySerGluIleGlnAla-155 |
| SEQ. ID. NO. 25090 | 157-ProArgLeuGlyGlyGlnHisGln-164 |
| SEQ. ID. NO. 25091 | 172-AsnAlaTyrLysSerGlyGlnArgLysAsnThrIleMetGluAspIleAlaAsnArgMetSerGluGluAspLeuLysAla-198 |
| Hydrophilic Regions - Hopp-Woods | |
| SEQ. ID. NO. 25092 | 18-AlaSerProLysAlaAspValGluLysGlyLysGlnVal-30 |
| SEQ. ID. NO. 25093 | 40-AlaAlaAspGlyAsnSer-45 |
| SEQ. ID. NO. 25094 | 67-GlyIleArgAspGlyLysArgThrHisGly-76 |
| SEQ. ID. NO. 25095 | 89-SerAspGlnAspIle-93 |
| SEQ. ID. NO. 25096 | 103-GlnGlnProLysSerGlyGluAlaAsnProLysGluAsnProGluLeuGly-119 |

TABLE 1-continued

| | |
|---|---|
| SEQ. ID. NO. 25097 | 126-GlyLeuSerAspLysLysValPro-133 |
| SEQ. ID. NO. 25098 | 175-LysSerGlyGlnArgLysAsnThrIleMetGluAspIleAlaAsnArgMetSerGluGluAspLeuLysAla-198 |
| a950 | |
| AMPHI Regions - AMPHI | |
| SEQ. ID. NO. 25099 | 33-GlyValHisLysSerAlaHisGly-40 |
| SEQ. ID. NO. 25100 | 71-AlaThrValLysLysThrHisLysHisThrLysAla-82 |
| Antigenic Index - Jameson-Wolf | |
| SEQ. ID. NO. 25101 | 1-MetAsnLysAsnIle-5 |
| SEQ. ID. NO. 25102 | 23-AlaAlaAsnLysProAlaSerAsnAlaThrGlyValHisLysSerAlaHisGlySerCysGlyAlaSerLysSerAlaGluGlySerCysGlyAlaAlaGly SerLysAlaGlyGluGlyLysCysGlyGluGlyLysCysGlyAlaThrValLysLysThrHisLysHisThrLysAlaSerLysAlaLysAlaLysSerAlaGlu GlyLysCysGlyGluGlyLysCysGlySerLys-102 |
| Hydrophilic Regions - Hopp-Woods | |
| SEQ. ID. NO. 25103 | 23-AlaAlaAsnLysProAlaSer-29 |
| SEQ. ID. NO. 25104 | 33-GlyValHisLysSerAlaHis-39 |
| SEQ. ID. NO. 25105 | 43-GlyAlaSerLysSerAlaGluGlySerCys-52 |
| SEQ. ID. NO. 25106 | 55-AlaGlySerLysAlaGlyGluGlyLysCysGlyGluGlyLysCys-69 |
| SEQ. ID. NO. 25107 | 71-AlaThrValLysLysThrHisLysHisThrLysAlaSerLysAlaLysAlaLysSerAlaGluGlyLysCysGlyGluGlyLysCysGlySerLys-102 |
| a951 | |
| AMPHI Regions - AMPHI | |
| SEQ. ID. NO. 25108 | 7-ThrIleLeuSerValLeuAlaAla-14 |
| SEQ. ID. NO. 25109 | 28-AspAlaLysProProLysGluValGlyLysValPheArgLysGlnGlnArgTyr-45 |
| SEQ. ID. NO. 25110 | 60-ValGlyGluArgValAsn-65 |
| SEQ. ID. NO. 25111 | 125-TrpArgGlnIleGluProIleProGlyLys-134 |
| SEQ. ID. NO. 25112 | 153-HisLeuAspGlyLeuGluGluValLeuAla-162 |
| SEQ. ID. NO. 25113 | 187-AlaGlnLysAlaSerLysAlaValArgArg-196 |
| SEQ. ID. NO. 25114 | 202-GluHisLeuProGluAlaAla-208 |
| SEQ. ID. NO. 25115 | 226-GlyAlaLeuGlnArgLeuAlaLysLeu-234 |
| SEQ. ID. NO. 25116 | 252-LysTyrProGluIleLeuAspGlyPhePheGlu-262 |
| SEQ. ID. NO. 25117 | 276-MetGluIleMetAsnLeuValSerLeuHisArgLeuAspAspAla-290 |
| SEQ. ID. NO. 25118 | 323-ValIleAspGlyTyrAlaGluLys-330 |
| SEQ. ID. NO. 25119 | 360-ValArgGlnTrpLeuLys-365 |
| SEQ. ID. NO. 25120 | 393-AlaLeuArgGlnIleGlyArgValArgLysLeuProGluGlnGln-407 |
| SEQ. ID. NO. 25121 | 414-AspAsnLeuSerLysIle-419 |
| SEQ. ID. NO. 25122 | 421-MetPheAlaLeuSer-425 |
| SEQ. ID. NO. 25123 | 432-GluAlaLeuArgGlyLeuAspLysIleIleGluLys-443 |
| SEQ. ID. NO. 25124 | 475-SerAspLeuGluArgAlaPheArg-482 |
| SEQ. ID. NO. 25125 | 493-AsnLeuGlyTyrSer-497 |
| SEQ. ID. NO. 25126 | 501-AspSerLysArgLeu-505 |
| SEQ. ID. NO. 25127 | 561-HisLeuGlyGluVal-565 |
| SEQ. ID. NO. 25128 | 577-AspValTrpThrGlnAla-582 |
| SEQ. ID. NO. 25129 | 592-TrpArgGluThrLeu-596 |
| Antigenic Index - Jameson-Wolf | |
| SEQ. ID. NO. 25130 | 26-AlaAlaAspAlaLysProProLysGluValGlyLysValPheArgLysGlnGlnArgTyrSerGluGluGluIleLysAsnGluArgAlaArgLeu-57 |
| SEQ. ID. NO. 25131 | 59-AlaValGlyGluArgValAsn-65 |
| SEQ. ID. NO. 25132 | 75-ThrAlaLeuGlnLysGlyGlnAla-82 |
| SEQ. ID. NO. 25133 | 94-GluArgThrLysSerProGluValAlaGluArgAlaLeuGlu-107 |
| SEQ. ID. NO. 25134 | 124-LysTrpArgGlnIleGluProIleProGlyLysAlaGlnLysArgAlaGlyTrpLeuArgAsnValLeuArgGluArgGlyAsnGlnHisLeuAspGly LeuGluGluValLeuAlaGlnAlaAspGluGlyGlnAsnArgArg-171 |
| SEQ. ID. NO. 25135 | 181-ValGlnGlnAspGlyLeuAlaGlnLysAlaSerLysAlaValArgArgAlaAlaLeuArg-200 |
| SEQ. ID. NO. 25136 | 217-GlnGlyArgGluLysGluLysAlaIle-225 |
| SEQ. ID. NO. 25137 | 230-ArgLeuAlaLysLeuAspThrGluIleLeuPro-240 |
| SEQ. ID. NO. 25138 | 248-LeuThrAlaArgLysTyrProGluIleLeuAspGlyPhePheGluGlnThrAspThrGlnAsn-268 |
| SEQ. ID. NO. 25139 | 285-HisArgLeuAspAspAlaTyrAla-292 |
| SEQ. ID. NO. 25140 | 298-LeuGluArgAsnProAsnAlaAsp-305 |
| SEQ. ID. NO. 25141 | 315-AlaAsnArgLysGluGlyAlaSer-322 |
| SEQ. ID. NO. 25142 | 326-GlyTyrAlaGluLysAlaTyrGlyArgGlyThrGlyGluGlnArgGlyArgAla-343 |
| SEQ. ID. NO. 25143 | 352-AlaAspArgArgAspTyrThrLysValArgGlnTrpLeuLysLysValSerAlaPro-370 |
| SEQ. ID. NO. 25144 | 373-LeuPheAspLysGlyVal-378 |
| SEQ. ID. NO. 25145 | 385-ValGluLeuAspGlyGlyArgAlaAlaLeu-394 |
| SEQ. ID. NO. 25146 | 396-GlnIleGlyArgValArgLysLeuProGluGlnGlnGlyArgTyrPheThr-412 |
| SEQ. ID. NO. 25147 | 426-LysLeuProAspLysArgGluAlaLeuArgGlyLeuAspLysIleIleGluLysProProAlaGlySerAsnThrGluLeuGlnAla-454 |
| SEQ. ID. NO. 25148 | 466-ArgLeuGlyLysArgLysLysMetIleSerAspLeuGluArgAlaPheArgLeuAlaProAspAsn-487 |
| SEQ. ID. NO. 25149 | 499-LeuSerAspSerLysArgLeuAspGluGlyPhe-509 |
| SEQ. ID. NO. 25150 | 518-IleAsnProAspAspThrAlaValAsnAspSerIle-529 |
| SEQ. ID. NO. 25151 | 535-LeuLysGlyAspAlaGluSerAla-542 |
| SEQ. ID. NO. 25152 | 547-ArgTyrSerPheGluAsnAspProGluProGluVal-558 |
| SEQ. ID. NO. 25153 | 570-GlyGluArgAspGlnAla-575 |
| SEQ. ID. NO. 25154 | 584-HisLeuThrGlyAspLysLysIleTrpArgGluThrLeuLysArgHisGlyIleAlaLeuProGlnProSerArgLysProArgLys-612 |
| Hydrophilic Regions - Hopp-Woods | |
| SEQ. ID. NO. 25155 | 26-AlaAlaAspAlaLysProProLysGluValGlyLysValPheArgLysGlnGlnArgTyrSerGluGluGluIleLysAsnGluArgAlaArgLeu-57 |
| SEQ. ID. NO. 25156 | 59-AlaValGlyGluArgValAsn-65 |
| SEQ. ID. NO. 25157 | 75-ThrAlaLeuGlnLysGlyGlnAla-82 |
| SEQ. ID. NO. 25158 | 94-GluArgThrLysSerProGluValAlaGluArgAlaLeuGlu-107 |
| SEQ. ID. NO. 25159 | 131-IleProGlyLysAlaGlnLysArgAlaGlyTrp-141 |
| SEQ. ID. NO. 25160 | 145-ValLeuArgGluArgGlyAsnGlnHis-153 |
| SEQ. ID. NO. 25161 | 155-AspGlyLeuGluGluValLeuAlaGlnAlaAspGluGlyGlnAsnArgArg-171 |
| SEQ. ID. NO. 25162 | 185-GlyLeuAlaGlnLysAlaSerLysAlaValArgArgAlaAlaLeuArg-200 |
| SEQ. ID. NO. 25163 | 217-GlnGlyArgGluLysGluLysAlaIle-225 |
| SEQ. ID. NO. 25164 | 230-ArgLeuAlaLysLeuAspThrGluIle-238 |
| SEQ. ID. NO. 25165 | 248-LeuThrAlaArgLysTyrProGluIle-256 |

TABLE 1-continued

| | |
|---|---|
| SEQ. ID. NO. 25166 | 261-PheGluGlnThrAspThrGlnAsn-268 |
| SEQ. ID. NO. 25167 | 285-HisArgLeuAspAspAlaTyrAla-292 |
| SEQ. ID. NO. 25168 | 298-LeuGluArgAsnProAsn-303 |
| SEQ. ID. NO. 25169 | 315-AlaAsnArgLysGluGlyAlaSer-322 |
| SEQ. ID. NO. 25170 | 327-TyrAlaGluLysAlaTyrGly-333 |
| SEQ. ID. NO. 25171 | 335-GlyThrGlyGluGlnArgGlyArgAla-343 |
| SEQ. ID. NO. 25172 | 352-AlaAspArgArgAspTyrThrLys-359 |
| SEQ. ID. NO. 25173 | 385-ValGluLeuAspGlyGlyArgAlaAlaLeu-394 |
| SEQ. ID. NO. 25174 | 396-GlnIleGlyArgValArgLysLeuProGluGlnGlnGly-408 |
| SEQ. ID. NO. 25175 | 426-LysLeuProAspLysArgGluAlaLeuArgGlyLeuAspLysIleIleGluLysProProAla-446 |
| SEQ. ID. NO. 25176 | 448-SerAsnThrGluLeuGlnAla-454 |
| SEQ. ID. NO. 25177 | 466-ArgLeuGlyLysArgLysLysMetIleSerAspLeuGluArgAlaPheArgLeuAlaProAspAsn-487 |
| SEQ. ID. NO. 25178 | 500-SerAspSerLysArgLeuAspGlu-507 |
| SEQ. ID. NO. 25179 | 519-AsnProAspAspThrAlaVal-525 |
| SEQ. ID. NO. 25180 | 537-GlyAspAlaGluSer-541 |
| SEQ. ID. NO. 25181 | 550-PheGluAsnAspProGluProGluVal-558 |
| SEQ. ID. NO. 25182 | 570-GlyGluArgAspGlnAla-575 |
| SEQ. ID. NO. 25183 | 586-ThrGlyAspLysLysIleTrpArgGluThrLeuLysArgHisGly-600 |
| SEQ. ID. NO. 25184 | 605-GlnProSerArgLysProArgLys-612 |
| a952 | |
| AMPHI Regions - AMPHI | |
| SEQ. ID. NO. 25185 | 63-SerValAlaThrLeuLeuAsnAsnPheTyrGlyGln-74 |
| SEQ. ID. NO. 25186 | 81-ValLeuLysLysLeuAsp-86 |
| SEQ. ID. NO. 25187 | 94-PheGluAspMetArgArgIle-100 |
| SEQ. ID. NO. 25188 | 116-GluGlnLeuAlaGlnLeu-121 |
| SEQ. ID. NO. 25189 | 138-SerValLeuArgGlyIleAsp-144 |
| Antigenic Index - Jameson-Wolf | |
| SEQ. ID. NO. 25190 | 40-GlnSerTrpLysGluArgArgAspPheAsnIleValLysGlnAspLeuAspPheSerCys-59 |
| SEQ. ID. NO. 25191 | 70-AsnPheTyrGlyGlnThrLeuThrGluGluGluValLeuLysLysLeuAspLysGluGlnMetArgAlaSerPheGluAspMetArgArgIleMet Pro-102 |
| SEQ. ID. NO. 25192 | 104-LeuGlyPheGluAlaLysGlyTyr-111 |
| SEQ. ID. NO. 25193 | 129-LeuLysTyrArgLysAspAspHisPheSer-138 |
| SEQ. ID. NO. 25194 | 141-ArgGlyIleAspGlyAsnThr-147 |
| SEQ. ID. NO. 25195 | 169-TrpGlnThrArgGluGlyAsnLeuAla-177 |
| SEQ. ID. NO. 25196 | 184-ValProLysLysAlaGluThrIleSer-192 |
| SEQ. ID. NO. 25197 | 199-HisHisProLysArgGlnThrGlu-206 |
| SEQ. ID. NO. 25198 | 213-ArgGlnAlaArgAlaGlu-218 |
| Hydrophilic Regions - Hopp-Woods | |
| SEQ. ID. NO. 25199 | 41-SerTrpLysGluArgArgAspPheAsnIleValLysGlnAspLeuAspPhe-57 |
| SEQ. ID. NO. 25200 | 76-LeuThrGluGluGluValLeuLysLysLeuAspLysGluGlnMetArgAlaSerPheGluAspMetArgArgIleMetPro-102 |
| SEQ. ID. NO. 25201 | 104-LeuGlyPheGluAlaLysGly-110 |
| SEQ. ID. NO. 25202 | 130-LysTyrArgLysAspAspHisPheSer-138 |
| SEQ. ID. NO. 25203 | 169-TrpGlnThrArgGluGlyAsnLeu-176 |
| SEQ. ID. NO. 25204 | 184-ValProLysLysAlaGluThrIleSer-192 |
| SEQ. ID. NO. 25205 | 200-HisProLysArgGlnThrGlu-206 |
| SEQ. ID. NO. 25206 | 213-ArgGlnAlaArgAlaGlu-218 |
| a953 | |
| AMPHI Regions - AMPHI | |
| SEQ. ID. NO. 25207 | 39-AsnThrSerThrAsnValGlyGlyPheTyrGlyLeuThr-51 |
| SEQ. ID. NO. 25208 | 75-GlnSerGlySerGlnHisPheThrAspHisLeuLysSerAlaAspIlePheAspAlaAlaGln-95 |
| SEQ. ID. NO. 25209 | 151-GlyAspPheSerThrThr-156 |
| Antigenic Index - Jameson-Wolf | |
| SEQ. ID. NO. 25210 | 22-TyrLysValAspGluTyrHisAla-29 |
| SEQ. ID. NO. 25211 | 38-PheAsnThrSerThrAsnVal-44 |
| SEQ. ID. NO. 25212 | 54-ValGluPheAspGlnAlaLysArgAspGlyLysIleAspIle-67 |
| SEQ. ID. NO. 25213 | 83-AspHisLeuLysSer-87 |
| SEQ. ID. NO. 25214 | 95-GlnTyrProAspIleArgPheValSer-103 |
| SEQ. ID. NO. 25215 | 105-LysPheAsnPheAsnGlyLysLysLeuValSer-115 |
| SEQ. ID. NO. 25216 | 122-MetHisGlyLysThrAlaProValLysLeuLysAlaGluLys-135 |
| SEQ. ID. NO. 25217 | 137-AsnCysTyrGlnSerProMetLeuLys-145 |
| SEQ. ID. NO. 25218 | 147-GluValCysGlyGlyAsp-152 |
| SEQ. ID. NO. 25219 | 154-SerThrThrIleAspArgThrLysTrpGly-163 |
| SEQ. ID. NO. 25220 | 174-LysSerValArgIle-178 |
| SEQ. ID. NO. 25221 | 180-IleGlnIleGluAlaAlaLysGln-187 |
| Hydrophilic Regions - Hopp-Woods | |
| SEQ. ID. NO. 25222 | 22-TyrLysValAspGluTyrHisAla-29 |
| SEQ. ID. NO. 25223 | 54-ValGluPheAspGlnAlaLysArgAspGlyLysIleAspIle-67 |
| SEQ. ID. NO. 25224 | 83-AspHisLeuLysSer-87 |
| SEQ. ID. NO. 25225 | 108-PheAsnGlyLysLysLeuValSer-115 |
| SEQ. ID. NO. 25226 | 125-LysThrAlaProValLysLeuLysAlaGluLys-135 |
| SEQ. ID. NO. 25227 | 155-ThrThrIleAspArgThrLysTrp-162 |
| SEQ. ID. NO. 25228 | 174-LysSerValArgIle-178 |
| SEQ. ID. NO. 25229 | 180-IleGlnIleGluAlaAlaLysGln-187 |
| a957 | |
| AMPHI Regions - AMPHI | |
| SEQ. ID. NO. 25230 | 11-SerPhePheAlaLeuValPheAla-18 |
| SEQ. ID. NO. 25231 | 45-AlaPheValAlaLysLeuAlaArgLeuPheArgAsnAla-57 |
| SEQ. ID. NO. 25232 | 71-GluGluSerLeuAlaGlyAlaValAspAsp-80 |
| SEQ. ID. NO. 25233 | 195-GluAspValTyrGluHisCysLeuGlyCysTyrGlnMet-207 |
| SEQ. ID. NO. 25234 | 215-TyrArgAspValAlaAsnAspGlu-222 |

TABLE 1-continued

| | |
|---|---|
| SEQ. ID. NO. 25235 | 232-SerAsnArgIleAlaSer-237 |
| SEQ. ID. NO. 25236 | 246-GlnAsnMetArgGluLeuMetProArg-254 |
| SEQ. ID. NO. 25237 | 352-GluLysGluValSerArgTyrAlaGluAlaAlaAlaArg-364 |
| Antigenic Index - Jameson-Wolf | |
| SEQ. ID. NO. 25238 | 29-IleAsnProArgTrp-33 |
| SEQ. ID. NO. 25239 | 35-LeuSerAspThrAlaThrGluAsnProAsn-44 |
| SEQ. ID. NO. 25240 | 54-PheArgAsnAlaAspArgAla-60 |
| SEQ. ID. NO. 25241 | 64-ValLysGluSerMetArgThrGluGluSerLeu-74 |
| SEQ. ID. NO. 25242 | 77-AlaValAspAspGlyProLeuGlnSerGluLysAspTyr-89 |
| SEQ. ID. NO. 25243 | 95-ArgLeuSerArgLeuLysGluLysAlaLys-104 |
| SEQ. ID. NO. 25244 | 109-ThrGluGlnGluHisGlyGlu-115 |
| SEQ. ID. NO. 25245 | 122-TyrIleGlyGluGlyGly-127 |
| SEQ. ID. NO. 25246 | 133-LeuSerGlnArgSerProGluAlaPheVal-142 |
| SEQ. ID. NO. 25247 | 146-TyrLeuTyrArgAsnAspArgProPheSer-155 |
| SEQ. ID. NO. 25248 | 163-ValHisGlyGluAsnTyrGluThrThrGlyGluTyrArgVal-176 |
| SEQ. ID. NO. 25249 | 179-GlnProAspGlySerValPheAspAlaSerGlyArgGlyLysIleGlyGluAspValTyr-198 |
| SEQ. ID. NO. 25250 | 214-LysTyrArgAspValAlaAsnAspGluGlnLysValTrpAspPheArgGluGluSerAsnArgIleAlaSerAspSerArgAspSerValPhe-244 |
| SEQ. ID. NO. 25251 | 247-AsnMetArgGluLeuMetProArgGlyMetLysAlaAsnSer-260 |
| SEQ. ID. NO. 25252 | 265-TyrAspAlaAspGlyLeuProGln-272 |
| SEQ. ID. NO. 25253 | 277-SerPheAspAsnGlyLysLysArgGlnSerPheGluTyrTyrLeuLysAsnGlyAsn-295 |
| SEQ. ID. NO. 25254 | 306-LeuLysAlaAspGlyValThr-312 |
| SEQ. ID. NO. 25255 | 326-LeuAspGlyGlyArgIleValArgGluGluLysGlnGlyAspArgLeuProAspPhe-344 |
| SEQ. ID. NO. 25256 | 346-LeuAsnLeuGluAspLeuGluLysGluValSerArgTyrAlaGluAlaAlaAlaArgArgSerGlyGlyArgArgAspLeuSerHis-374 |
| Hydrophilic Regions - Hopp-Woods | |
| SEQ. ID. NO. 25257 | 38-ThrAlaThrGluAsnPro-43 |
| SEQ. ID. NO. 25258 | 54-PheArgAsnAlaAspArgAla-60 |
| SEQ. ID. NO. 25259 | 64-ValLysGluSerMetArgThrGluGluSerLeu-74 |
| SEQ. ID. NO. 25260 | 77-AlaValAspAspGlyProLeuGlnSerGluLysAspTyr-89 |
| SEQ. ID. NO. 25261 | 95-ArgLeuSerArgLeuLysGluLysAlaLys-104 |
| SEQ. ID. NO. 25262 | 109-ThrGluGlnGluHisGlyGlu-115 |
| SEQ. ID. NO. 25263 | 133-LeuSerGlnArgSerProGlu-139 |
| SEQ. ID. NO. 25264 | 148-TyrArgAsnAspArgProPhe-154 |
| SEQ. ID. NO. 25265 | 166-GluAsnTyrGluThrThrGlyGluTyr-174 |
| SEQ. ID. NO. 25266 | 187-AlaSerGlyArgGlyLysIleGlyGluAspValTyr-198 |
| SEQ. ID. NO. 25267 | 214-LysTyrArgAspValAlaAsnAspGluGlnLysValTrpAspPheArgGluGluSerAsnArgIleAlaSerAspSerArgAspSerVal-243 |
| SEQ. ID. NO. 25268 | 247-AsnMetArgGluLeuMetProArgGlyMetLys-257 |
| SEQ. ID. NO. 25269 | 265-TyrAspAlaAspGlyLeuPro-271 |
| SEQ. ID. NO. 25270 | 279-AspAsnGlyLysLysArgGlnSer-286 |
| SEQ. ID. NO. 25271 | 306-LeuLysAlaAspGlyValThr-312 |
| SEQ. ID. NO. 25272 | 328-GlyGlyArgIleValArgGluGluLysGlnGlyAspArgLeuPro-342 |
| SEQ. ID. NO. 25273 | 346-LeuAsnLeuGluAspLeuGluLysGluValSerArgTyrAlaGluAlaAlaAlaArgArgSerGlyGlyArgArgAspLeuSerHis-374 |
| a958 | |
| AMPHI Regions - AMPHI | |
| SEQ. ID. NO. 25274 | 39-GlyGlySerValArgSerValSerGluProIleGln-50 |
| SEQ. ID. NO. 25275 | 86-ProGluAspTyrThrArgIleValAlaAsp-95 |
| SEQ. ID. NO. 25276 | 127-TyrAspGlnSerGlyAsp-132 |
| SEQ. ID. NO. 25277 | 177-ArgArgLeuGlnSerValSerArgThrAlaGluMet-188 |
| SEQ. ID. NO. 25278 | 343-IleSerAspThrLeuGln-348 |
| SEQ. ID. NO. 25279 | 483-TyrTyrSerLeuAsnArgPhe-489 |
| SEQ. ID. NO. 25280 | 491-SerGlnGluAlaArgArgVal-497 |
| SEQ. ID. NO. 25281 | 500-ThrLeuProIleVal-504 |
| SEQ. ID. NO. 25282 | 541-GlnAsnAspLeuProAsnPheAsp-548 |
| SEQ. ID. NO. 25283 | 572-AsnThrAlaAsnSerLeuSerAlaAlaValGlnSer-583 |
| SEQ. ID. NO. 25284 | 693-AspLysLeuSerGln-697 |
| SEQ. ID. NO. 25285 | 723-LysLysProIleGlu-727 |
| SEQ. ID. NO. 25286 | 769-AspLeuSerSerValGlyArgAsnPro-777 |
| Antigenic Index -Jameson-Wolf | |
| SEQ. ID. NO. 25287 | 18-PheGlyThrHisCys-22 |
| SEQ. ID. NO. 25288 | 28-ValAlaAlaGluGluThrAspAsnProThrAlaGlyGlySerValArgSerValSerGluProIleGln-50 |
| SEQ. ID. NO. 25289 | 55-SerLeuGlySerThr-59 |
| SEQ. ID. NO. 25290 | 63-CysSerAsnGluSerGlySerProGluArgThrGluAlaAlaValGlnGlySerGlyGluAlaSerIleProGluAspTyrThrArgIleValAlaAspArg MetGluGlyGlnSerGlnValGlnValArgAlaGluGly-109 |
| SEQ. ID. NO. 25291 | 111-ValValValGluArgAsnArgThrThrLeuAsn-121 |
| SEQ. ID. NO. 25292 | 123-AspTrpAlaAspTyrAspGlnSerGlyAspThrValThrAlaGlyAspArgPheAlaLeuGlnGlnAspGlyThrLeuIleArgGlyGluThrLeu-154 |
| SEQ. ID. NO. 25293 | 158-LeuGluGlnGlnThrGlyGluAlaHisAsnValArgMetGluThrGluHisGlyGlyArgArgLeuGlnSerValSerArgThrAlaGluMetLeuGly GluGlyHisTyrLysLeuThrGluThrGlnPheAsnThrCysSerAlaGlyAspAlaGlyTrp-211 |
| SEQ. ID. NO. 25294 | 216-AlaSerValGluAlaAspArgGluLysGlyIleGly-227 |
| SEQ. ID. NO. 25295 | 249-PheProLeuAspGlyAsnArgLysSerGlyLeu-259 |
| SEQ. ID. NO. 25296 | 265-SerAlaGlySerAspGlyVal-271 |
| SEQ. ID. NO. 25297 | 292-GlyValIleGlyGluArgGlyAlaValPheAspGlyGlnValArgTyrLeuArgProAspTyrAlaGlyGlnSerAsp-317 |
| SEQ. ID. NO. 25298 | 321-LeuProHisAspLysLysSerGlyArgAsnAsnArgTyrGlnAla-335 |
| SEQ. ID. NO. 25299 | 337-TrpGlnHisArgHisAspIleSerAspThrLeu-347 |
| SEQ. ID. NO. 25300 | 352-AspPheAsnGlnValSerAspSerGlyTyrTyrArgAspPheTyrGlyAsnLysGluIleAlaGlyAsnValAsnLeuAsnArgArgValTrp-382 |
| SEQ. ID. NO. 25301 | 384-AspTyrGlyGlyArgAlaAlaGlyGlySerLeu-394 |
| SEQ. ID. NO. 25302 | 407-AlaAsnGlnSerGlyTyrLysAspLysProTyr-417 |
| SEQ. ID. NO. 25303 | 422-ArgLeuSerAlaAspTrpArgLysAsnThrGlyArgAla-434 |
| SEQ. ID. NO. 25304 | 444-ArgPheSerHisAspSerArgGlnAspGlySerArg-455 |
| SEQ. ID. NO. 25305 | 460-ProAspIleLysTrpAspPheSerAsnSerTrpGly-471 |
| SEQ. ID. NO. 25306 | 487-AsnArgPheGlySerGlnGluAlaArgArgValSerArg-499 |
| SEQ. ID. NO. 25307 | 507-AspSerGlyMetThrPheGluArgAsnThrArgMetPheGlyGlyGly-522 |

TABLE 1-continued

| | |
|---|---|
| SEQ. ID. NO. 25308 | 525-GlnThrLeuGluProArg-530 |
| SEQ. ID. NO. 25309 | 538-AlaLysSerGlnAsnAspLeuProAsnPheAspSerSerGluSerSerPheGly-555 |
| SEQ. ID. NO. 25310 | 560-PheArgGluAsnLeuTyrTyrGlyAsnAspArgIleAsnThrAlaAsnSer-576 |
| SEQ. ID. NO. 25311 | 581-ValGlnSerArgIleLeuAspGlyAlaThrGlyGluGluArgPheArgAlaGlyIleGlyGlnLysPheTyrPheLysAsnAspAlaValMetLeuAsp GlySerValGlyLysLysProArgSerArgSerAspTrp-626 |
| SEQ. ID. NO. 25312 | 631-SerSerGlyIleGlySerArgPheIleLeuAspSerSerIleHisTyrAsnGlnAsnAspLysArgAlaGluAsn-655 |
| SEQ. ID. NO. 25313 | 660-AlaSerTyrArgProAlaGlnGlyLysValLeuAsnAlaArgTyrLysTyrGlyArgAsnGluLysIleTyrLeuLysSerAspGlySerTyrPhe-691 |
| SEQ. ID. NO. 25314 | 693-AspLysLeuSerGln-697 |
| SEQ. ID. NO. 25315 | 718-TyrGlyPheGluAlaLysLysProIleGlu-727 |
| SEQ. ID. NO. 25316 | 732-AlaGluTyrLysSerSerCysGlyCysTrp-741 |
| SEQ. ID. NO. 25317 | 751-ValThrGlyGluAsnThrTyrLysAsn-759 |
| SEQ. ID. NO. 25318 | 766-GlnLeuLysAspLeuSerSerValGlyArgAsnProAlaAspArgMetAspVal-783 |
| Hydrophilic Regions - Hopp-Woods | |
| SEQ. ID. NO. 25319 | 28-ValAlaAlaGluGluThrAspAsnProThr-37 |
| SEQ. ID. NO. 25320 | 40-GlySerValArgSerValSerGluProIleGln-50 |
| SEQ. ID. NO. 25321 | 65-AsnGluSerGlySerProGluArgThrGluAlaAlaVal-77 |
| SEQ. ID. NO. 25322 | 79-GlySerGlyGluAlaSerIleProGluAspTyrThr-90 |
| SEQ. ID. NO. 25323 | 93-ValAlaAspArgMetGluGlyGlnSer-101 |
| SEQ. ID. NO. 25324 | 103-ValGlnValArgAlaGluGly-109 |
| SEQ. ID. NO. 25325 | 111-ValValValGluArgAsnArgThrThrLeu-120 |
| SEQ. ID. NO. 25326 | 125-AlaAspTyrAspGlnSerGlyAspThrValThrAlaGlyAspArgPheAlaLeu-142 |
| SEQ. ID. NO. 25327 | 147-ThrLeuIleArgGlyGluThr-153 |
| SEQ. ID. NO. 25328 | 160-GlnGlnThrGlyGluAlaHisAsnValArgMetGluThrGluHisGlyGlyArgArgLeuGlnSerValSerArgThrAlaGluMetLeuGly-190 |
| SEQ. ID. NO. 25329 | 192-GlyHisTyrLysLeuThrGlu-198 |
| SEQ. ID. NO. 25330 | 216-AlaSerValGluAlaAspArgGluLysGlyIleGly-227 |
| SEQ. ID. NO. 25331 | 250-ProLeuAspGlyAsnArgLysSerGly-258 |
| SEQ. ID. NO. 25332 | 266-AlaGlySerAspGlyVal-271 |
| SEQ. ID. NO. 25333 | 294-IleGlyGluArgGlyAlaVal-300 |
| SEQ. ID. NO. 25334 | 305-ValArgTyrLeuArg-309 |
| SEQ. ID. NO. 25335 | 323-HisAspLysLysSerGlyArgAsnAsnArgTyrGlnAla-335 |
| SEQ. ID. NO. 25336 | 337-TrpGlnHisArgHisAspIleSerAsp-345 |
| SEQ. ID. NO. 25337 | 410-SerGlyTyrLysAspLysProTyr-417 |
| SEQ. ID. NO. 25338 | 423-LeuSerAlaAspTrpArgLysAsnThrGlyArgAla-434 |
| SEQ. ID. NO. 25339 | 445-PheSerHisAspSerArgGlnAspGlySerArg-455 |
| SEQ. ID. NO. 25340 | 490-GlySerGlnGluAlaArgArgValSerArg-499 |
| SEQ. ID. NO. 25341 | 510-MetThrPheGluArgAsnThrArg-517 |
| SEQ. ID. NO. 25342 | 539-LysSerGlnAsnAsp-543 |
| SEQ. ID. NO. 25343 | 548-AspSerSerGluSer-552 |
| SEQ. ID. NO. 25344 | 569-AspArgIleAsnThr-573 |
| SEQ. ID. NO. 25345 | 589-AlaThrGlyGluGluArgPheArgAla-597 |
| SEQ. ID. NO. 25346 | 615-SerValGlyLysLysProArgSerArgSerAsp-625 |
| SEQ. ID. NO. 25347 | 648-GlnAsnAspLysArgAlaGluAsn-655 |
| SEQ. ID. NO. 25348 | 662-TyrArgProAlaGln-666 |
| SEQ. ID. NO. 25349 | 674-TyrLysTyrGlyArgAsnGluLysIleTyrLeuLysSerAspGly-688 |
| SEQ. ID. NO. 25350 | 720-PheGluAlaLysLysProIleGlu-727 |
| SEQ. ID. NO. 25351 | 732-AlaGluTyrLysSer-736 |
| SEQ. ID. NO. 25352 | 766-GlnLeuLysAspLeuSerSerValGlyArgAsnProAlaAspArgMetAspVal-783 |
| a959 | |
| AMPHI Regions - AMPHI | |
| SEQ. ID. NO. 25353 | 56-AlaAlaLeuAlaArgValGlyGly-63 |
| Antigenic Index - Jameson-Wolf | |
| SEQ. ID. NO. 25354 | 24-AlaHisHisAspGlyHisGlyAspAspAspHisGlyHis-36 |
| SEQ. ID. NO. 25355 | 40-GlnHisSerLysGlnAspLysIleIleSer-49 |
| SEQ. ID. NO. 25356 | 51-AlaGlnAlaGluLysAlaAlaLeu-58 |
| SEQ. ID. NO. 25357 | 60-ArgValGlyGlyLysIleThrAspIleAspLeuGluHisAspAsnGlyArgProHisTyrAspValGluIleValLysAsnGlyGlnGluTyr-90 |
| SEQ. ID. NO. 25358 | 94-ValAspAlaArgThrGlyArgValIleSerSerArgArgAspAsp-108 |
| Hydrophilic Regions - Hopp-Woods | |
| SEQ. ID. NO. 25359 | 27-AspGlyHisGlyAspAspAspHisGlyHis-36 |
| SEQ. ID. NO. 25360 | 40-GlnHisSerLysGlnAspLysIleIleSer-49 |
| SEQ. ID. NO. 25361 | 51-AlaGlnAlaGluLysAlaAlaLeu-58 |
| SEQ. ID. NO. 25362 | 61-ValGlyGlyLysIleThrAspIleAspLeuGluHisAspAsnGlyArgProHisTyr-79 |
| SEQ. ID. NO. 25363 | 82-GluIleValLysAsnGlyGlnGluTyr-90 |
| SEQ. ID. NO. 25364 | 94-ValAspAlaArgThrGlyArg-100 |
| SEQ. ID. NO. 25365 | 102-IleSerSerArgArgAspAsp-108 |
| a972 | |
| AMPHI Regions - AMPHI | |
| SEQ. ID. NO. 25366 | 15-SerSerGluArgMetSerGluValGluTyrPheSerHis-27 |
| SEQ. ID. NO. 25367 | 83-ArgLysLeuGluGluIleLeuGly-90 |
| SEQ. ID. NO. 25368 | 100-ArgGlyAsnLysPheTyrGluSerMetTyrArgLeu-111 |
| SEQ. ID. NO. 25369 | 154-LeuAspAspSerIleArg-159 |
| SEQ. ID. NO. 25370 | 226-PheValArgValTyrGluLysGly-233 |
| SEQ. ID. NO. 25371 | 275-IleCysArgLysPheLysAsnMetProValPro-285 |
| SEQ. ID. NO. 25372 | 308-AsnAlaValGlyLysLeuValAsnPhe-316 |
| SEQ. ID. NO. 25373 | 326-GluIleValGluSerLeuLysAla-333 |
| SEQ. ID. NO. 25374 | 336-GlyPheProLysGlyLeuGlu-342 |
| SEQ. ID. NO. 25375 | 348-LeuGluMetLeuArgAspGlyLeuLys-356 |
| SEQ. ID. NO. 25376 | 382-AsnSerAspLysPheAspArg-388 |
| Antigenic Index - Jameson-Wolf | |
| SEQ. ID. NO. 25377 | 1-LeuThrAsnArgGlyGlyAlaLysLeuLysThrAsnSerLysSerSerGluArgMetSerGlu-21 |
| SEQ. ID. NO. 25378 | 29-IleSerAspGlyLysGlyLysLeuLeuGluIleProGlnArgArgGlyLysGlnAspGlyVal-49 |

TABLE 1-continued

| | |
|---|---|
| SEQ. ID. NO. 25379 | 62-ThrLeuLeuLysValSerGly-68 |
| SEQ. ID. NO. 25380 | 83-ArgLysLeuGluGlu-87 |
| SEQ. ID. NO. 25381 | 93-IleThrArgLysCysLysSerArgGlyAsnLysPheTyrGlu-106 |
| SEQ. ID. NO. 25382 | 108-MetTyrArgLeuGlySerAspAspValAspTyrGly-119 |
| SEQ. ID. NO. 25383 | 122-HisPheGlyGlyGlnArgAsnThrVal-130 |
| SEQ. ID. NO. 25384 | 134-LeuLysGlyThrGlyCys-139 |
| SEQ. ID. NO. 25385 | 152-GlnPheLeuAspAspSerIleArgThrArgIleThrArg-164 |
| SEQ. ID. NO. 25386 | 172-PheAspGlyGluTyrThrProAspGlnAlaLeuLeuAspHisAspAsnGlyPhePheAspAsnSerAsnGlnArgProLysSerGluThrIleGly-203 |
| SEQ. ID. NO. 25387 | 205-AlaTrpArgAsnGluAspGlySerGlyLys-214 |
| SEQ. ID. NO. 25388 | 217-TyrValGlyArgLysLysAsnSerArgPhe-226 |
| SEQ. ID. NO. 25389 | 228-ArgValTyrGluLysGlyArgGlnLeuGlyAspLysGluSerLysTrpVal-244 |
| SEQ. ID. NO. 25390 | 251-AsnTyrGlyAspIleGluIle-257 |
| SEQ. ID. NO. 25391 | 263-IleAsnGlnGlySer-267 |
| SEQ. ID. NO. 25392 | 275-IleCysArgLysPheLysAsnMetProValProGluArgPheAspGlnArgLysLysThrLeu-295 |
| SEQ. ID. NO. 25393 | 321-GlyPheAspAsnSerGluIleValGluSerLeuLysAlaAspSerGlyPheProLysGlyLeuGluProGluLysTyrAla-347 |
| SEQ. ID. NO. 25394 | 350-MetLeuArgAspGlyLeuLys-356 |
| SEQ. ID. NO. 25395 | 361-HisGluGlnProAspIleAspLeuGluIleGluLeuAspGlu-374 |
| SEQ. ID. NO. 25396 | 380-PheLysAsnSerAspLysPheAspArgGluLysArgLeuPheSerProAspTyrAspValGluLysGluArgLysTyrGlnGluTyrLeu-409 |
| SEQ. ID. NO. 25397 | 417-ValAspTyrAspTyrPhe-422 |
| Hydrophilic Regions - Hopp-Woods | |
| SEQ. ID. NO. 25398 | 1-LeuThrAsnArgGlyGlyAlaLysLeuLysThrAsnSerLysSerSerGluArgMetSerGlu-21 |
| SEQ. ID. NO. 25399 | 30-SerAspGlyLysGlyLysLeuLeuGluIleProGlnArgArgGlyLysGlnAspGlyVal-49 |
| SEQ. ID. NO. 25400 | 83-ArgLysLeuGluGlu-87 |
| SEQ. ID. NO. 25401 | 93-IleThrArgLysCysLysSerArgGlyAsnLysPheTyr-105 |
| SEQ. ID. NO. 25402 | 111-LeuGlySerAspAspValAspTyrGly-119 |
| SEQ. ID. NO. 25403 | 134-LeuLysGlyThrGly-138 |
| SEQ. ID. NO. 25404 | 152-GlnPheLeuAspAspSerIleArgThrArgIleThrArg-164 |
| SEQ. ID. NO. 25405 | 181-AlaLeuLeuAspHisAspAsnGlyPhe-189 |
| SEQ. ID. NO. 25406 | 193-SerAsnGlnArgProLysSerGluThrIle-202 |
| SEQ. ID. NO. 25407 | 206-TrpArgAsnGluAspGlySerGly-213 |
| SEQ. ID. NO. 25408 | 219-GlyArgLysLysAsnSerArgPhe-226 |
| SEQ. ID. NO. 25409 | 228-ArgValTyrGluLysGlyArgGlnLeuGlyAspLysGluSerLysTrpVal-244 |
| SEQ. ID. NO. 25410 | 277-ArgLysPheLysAsn-281 |
| SEQ. ID. NO. 25411 | 283-ProValProGluArgPheAspGlnArgLysLysThrLeu-295 |
| SEQ. ID. NO. 25412 | 321-GlyPheAspAsnSerGluIleValGluSerLeuLysAlaAspSerGlyPhe-337 |
| SEQ. ID. NO. 25413 | 339-LysGlyLeuGluProGluLysTyrAla-347 |
| SEQ. ID. NO. 25414 | 350-MetLeuArgAspGlyLeuLys-356 |
| SEQ. ID. NO. 25415 | 362-GluGlnProAspIleAspLeuGluIleGluLeuAspGlu-374 |
| SEQ. ID. NO. 25416 | 381-LysAsnSerAspLysPheAspArgGluLysArgLeuPhe-393 |
| SEQ. ID. NO. 25417 | 396-AspTyrAspValGluLysGluArgLysTyrGlnGluTyrLeu-409 |
| a973 | |
| AMPHI Regions - AMPHI | |
| SEQ. ID. NO. 25418 | 12-GluArgLeuIleAlaArgLeuAlaArgGluProAspSerAla-25 |
| SEQ. ID. NO. 25419 | 44-AspThrLeuLeuArgLeuGluLysValLeuAspPhe-55 |
| SEQ. ID. NO. 25420 | 77-AspSerIleGluArgIleThrAlaTyr-85 |
| SEQ. ID. NO. 25421 | 112-AspLeuLeuLysTyrMet-117 |
| SEQ. ID. NO. 25422 | 143-AlaLeuLeuLysGluPheArgGluGln-151 |
| SEQ. ID. NO. 25423 | 171-PheGluAspIleIleGluGlnIleValGlyAspIleGluAsp-184 |
| SEQ. ID. NO. 25424 | 208-AlaThrGluIleGluAspIleAsnAlaPhe-217 |
| SEQ. ID. NO. 25425 | 235-IleGlnGluLeuGly-239 |
| Antigenic Index - Jameson-Wolf | |
| SEQ. ID. NO. 25426 | 1-MetAspGlyAlaGlnProLysThrAsnPhe-10 |
| SEQ. ID. NO. 25427 | 18-LeuAlaArgGluProAspSerAlaGluAsp-27 |
| SEQ. ID. NO. 25428 | 34-GlnAlaHisGluGlnGluValPheAspAlaAspThr-45 |
| SEQ. ID. NO. 25429 | 47-LeuArgLeuGluLysValLeuAsp-54 |
| SEQ. ID. NO. 25430 | 56-SerAspLeuGluValArgAspAlaMetIleThrArgSerArgMetAsnValLeuLysGluAsnAspSerIleGluArg-81 |
| SEQ. ID. NO. 25431 | 96-ValIleGlyGluAspLysAspGluVal-104 |
| SEQ. ID. NO. 25432 | 118-PheAsnProGluGlnPheHis-124 |
| SEQ. ID. NO. 25433 | 136-ProGluGlyLysSer-140 |
| SEQ. ID. NO. 25434 | 146-LysGluPheArgGluGlnArgAsnHis-154 |
| SEQ. ID. NO. 25435 | 159-IleAspGluTyrGlyGlyThrSerGly-167 |
| SEQ. ID. NO. 25436 | 178-IleValGlyAspIleGluAspGluPheAspGluAspGluSerAlaAspAsn-194 |
| SEQ. ID. NO. 25437 | 199-SerAlaGluArgTrpArg-204 |
| SEQ. ID. NO. 25438 | 209-ThrGluIleGluAsp-213 |
| SEQ. ID. NO. 25439 | 219-GlyThrGluTyrSerSerGluGluAlaAspThr-229 |
| SEQ. ID. NO. 25440 | 239-GlyHisLeuProValArgGlyGluLysValLeu-249 |
| SEQ. ID. NO. 25441 | 258-AlaArgAlaAspAsnArgArgLeuHis-266 |
| Hydrophilic Regions - Hopp-Woods | |
| SEQ. ID. NO. 25442 | 1-MetAspGlyAlaGlnProLys-7 |
| SEQ. ID. NO. 25443 | 18-LeuAlaArgGluProAspSerAlaGluAsp-27 |
| SEQ. ID. NO. 25444 | 34-GlnAlaHisGluGlnGluValPheAsp-42 |
| SEQ. ID. NO. 25445 | 47-LeuArgLeuGluLysValLeuAsp-54 |
| SEQ. ID. NO. 25446 | 56-SerAspLeuGluValArgAspAlaMetIleThrArgSerArgMetAsnValLeuLysGluAsnAspSerIleGluArg-81 |
| SEQ. ID. NO. 25447 | 96-ValIleGlyGluAspLysAspGluVal-104 |
| SEQ. ID. NO. 25448 | 136-ProGluGlyLysSer-140 |
| SEQ. ID. NO. 25449 | 146-LysGluPheArgGluGlnArgAsn-153 |
| SEQ. ID. NO. 25450 | 178-IleValGlyAspIleGluAspGluPheAspGluAspGluSerAlaAspAsn-194 |
| SEQ. ID. NO. 25451 | 199-SerAlaGluArgTrpArg-204 |
| SEQ. ID. NO. 25452 | 209-ThrGluIleGluAsp-213 |
| SEQ. ID. NO. 25453 | 222-TyrSerSerGluGluAlaAspThr-229 |

TABLE 1-continued

| | |
|---|---|
| SEQ. ID. NO. 25454 | 243-ValArgGlyGluLysValLeu-249 |
| SEQ. ID. NO. 25455 | 258-AlaArgAlaAspAsnArgArgLeuHis-266 |
| a981 | |
| AMPHI Regions - AMPHI | |
| SEQ. ID. NO. 25456 | 31-AlaAsnProAspLysValTyrArgValAlaSer-41 |
| SEQ. ID. NO. 25457 | 46-AlaProPheGluSerLeuAsp-52 |
| SEQ. ID. NO. 25458 | 66-AsnAlaMetAlaLys-70 |
| SEQ. ID. NO. 25459 | 132-LysIleSerSerSerGluAspLeuLysAsnMetAsnLysValGlyValVal-148 |
| SEQ. ID. NO. 25460 | 167-LysIleAlaArgPheGlu-172 |
| SEQ. ID. NO. 25461 | 181-LeuGluAsnGlyGlyLeuAspSerValVal-190 |
| SEQ. ID. NO. 25462 | 197-AlaAsnTyrValLysAsnAsnPro-204 |
| SEQ. ID. NO. 25463 | 207-GlyMetAspPheValThrLeuPro-214 |
| SEQ. ID. NO. 25464 | 233-ValLysMetLeuAsnAspAlaLeuLysLysValArgGluSerGlyGluTyr-249 |
| Antigenic Index - Jameson-Wolf | |
| SEQ. ID. NO. 25465 | 19-CysGlyGlyGlnGlyLysAspAlaAlaAla-28 |
| SEQ. ID. NO. 25466 | 31-AlaAsnProAspLysValTyrArg-38 |
| SEQ. ID. NO. 25467 | 49-GluSerLeuAspSerLysGlyAsnValGluGlyPheAsp-61 |
| SEQ. ID. NO. 25468 | 76-IleGluPheLysHisGlnProTrpAspSer-85 |
| SEQ. ID. NO. 25469 | 90-LeuAsnAsnGlyAspAlaAspVal-97 |
| SEQ. ID. NO. 25470 | 104-IleThrAspAspArgLysGlnSerMetAspPheSerAspProTyrPhe-119 |
| SEQ. ID. NO. 25471 | 127-ValProLysGlyLysLysIleSerSerSerGluAspLeuLysAsnMetAsnLys-144 |
| SEQ. ID. NO. 25472 | 160-LeuLeuGlyAsnAspAsnProLysIleAlaArg-170 |
| SEQ. ID. NO. 25473 | 179-LysGluLeuGluAsnGlyGlyLeuAspSerValValSerAspSerAla-194 |
| SEQ. ID. NO. 25474 | 201-LysAsnAsnProThrLysGlyMetAspPhe-210 |
| SEQ. ID. NO. 25475 | 214-ProAspPheThrThr-218 |
| SEQ. ID. NO. 25476 | 225-ValArgLysGlyAspGluAlaThrVal-233 |
| SEQ. ID. NO. 25477 | 235-MetLeuAsnAspAlaLeuLysLysValArgGluSerGlyGluTyrAspLysIleTyr-253 |
| SEQ. ID. NO. 25478 | 257-PheAlaLysGluAspGlyGlnAlaAlaLys-266 |
| Hydrophilic Regions - Hopp-Woods | |
| SEQ. ID. NO. 25479 | 21-GlyGlnGlyLysAspAlaAlaAla-28 |
| SEQ. ID. NO. 25480 | 31-AlaAsnProAspLysValTyrArg-38 |
| SEQ. ID. NO. 25481 | 49-GluSerLeuAspSerLysGlyAsnValGluGlyPheAsp-61 |
| SEQ. ID. NO. 25482 | 91-AsnAsnGlyAspAlaAspVal-97 |
| SEQ. ID. NO. 25483 | 104-IleThrAspAspArgLysGlnSerMetAspPheSer-115 |
| SEQ. ID. NO. 25484 | 128-ProLysGlyLysLysIleSerSerSerGluAspLeuLysAsnMetAsn-143 |
| SEQ. ID. NO. 25485 | 164-AspAsnProLysIleAlaArg-170 |
| SEQ. ID. NO. 25486 | 179-LysGluLeuGluAsnGlyGlyLeu-186 |
| SEQ. ID. NO. 25487 | 203-AsnProThrLysGlyMetAsp-209 |
| SEQ. ID. NO. 25488 | 225-ValArgLysGlyAspGluAlaThrVal-233 |
| SEQ. ID. NO. 25489 | 235-MetLeuAsnAspAlaLeuLysLysValArgGluSerGlyGluTyrAspLysIleTyr-253 |
| SEQ. ID. NO. 25490 | 257-PheAlaLysGluAspGlyGlnAlaAlaLys-266 |
| a982 | |
| AMPHI Regions - AMPHI | |
| SEQ. ID. NO. 25491 | 12-ValArgGlnLysMetValAsnGlyValAsnIleLeuAlaAsnAlaVal-27 |
| SEQ. ID. NO. 25492 | 71-AlaGlnMetValLysGluValAlaSerLysThr-81 |
| SEQ. ID. NO. 25493 | 100-ValAlaGluGlyMetLysTyr-106 |
| SEQ. ID. NO. 25494 | 115-AspLeuLysArgGlyIleAspLysAlaValAlaAlaLeuValGluGluLeuLysAsnIleAlaLysProCysAspThrSerLysGluIleAlaGlnValGly Ser-149 |
| SEQ. ID. NO. 25495 | 160-AlaIleIleAlaGluAlaMetGluLysValGly-170 |
| SEQ. ID. NO. 25496 | 185-AsnGluLeuAspValValGluGlyMet-193 |
| SEQ. ID. NO. 25497 | 209-GluLysGlnIleAlaGlyLeuAsp-216 |
| SEQ. ID. NO. 25498 | 227-IleSerAsnIleArgAspLeuLeuProValLeuGluGlnValAlaLysAla-243 |
| SEQ. ID. NO. 25499 | 265-AsnAsnIleArgGlyIleLeuLysThrValAla-275 |
| SEQ. ID. NO. 25500 | 313-ThrLeuAspAspLeuGlyGlnAlaLysArgIle-323 |
| SEQ. ID. NO. 25501 | 331-ThrIleIleAspGlyPheGlyAspAlaAla-340 |
| SEQ. ID. NO. 25502 | 367-GluArgValAlaLysLeuAlaGlyGlyVal-376 |
| SEQ. ID. NO. 25503 | 426-LeuGluAsnLeuHisThr-431 |
| SEQ. ID. NO. 25504 | 444-LeuArgAlaValGluSerProLeuArgGlnIleValAlaAsnAla-458 |
| SEQ. ID. NO. 25505 | 484-GluTyrGlyAspMetIleGluMet-491 |
| SEQ. ID. NO. 25506 | 500-ThrArgSerAlaLeu-504 |
| Antigenic Index - Jameson-Wolf | |
| SEQ. ID. NO. 25507 | 1-MetAlaAlaLysAspValGlnPhe-8 |
| SEQ. ID. NO. 25508 | 10-AsnGluValArgGlnLysMetValAsn-18 |
| SEQ. ID. NO. 25509 | 30-ThrLeuGlyProLysGlyArgAsnValValVal-40 |
| SEQ. ID. NO. 25510 | 43-AlaPheGlyGlyProHisIleThrLysAspGlyValThrValAlaLysGluIleGluLeuLysAspLysPheGluAsnMetGly-70 |
| SEQ. ID. NO. 25511 | 73-MetValLysGluValAlaSerLysThrAsnAspValAlaGlyAspGlyThrThr-90 |
| SEQ. ID. NO. 25512 | 112-AsnProThrAspLeuLysArgGlyIleAspLysAlaVal-124 |
| SEQ. ID. NO. 25513 | 129-GluGluLeuLysAsnIleAlaLysProCysAspThrSerLysGluIleAla-145 |
| SEQ. ID. NO. 25514 | 150-IleSerAlaAsnSerAspGluGlnVal-158 |
| SEQ. ID. NO. 25515 | 164-GluAlaMetGluLysValGlyLysGluGlyValIleThrValGluAspGlyLysSerLeuGluAsnGluLeuAspVal-189 |
| SEQ. ID. NO. 25516 | 193-MetGlnPheAspArgGlyTyr-199 |
| SEQ. ID. NO. 25517 | 207-AspAlaGluLysGlnIleAla-213 |
| SEQ. ID. NO. 25518 | 223-PheAspLysLysIleSerAsnIleArgAsp-232 |
| SEQ. ID. NO. 25519 | 239-GlnValAlaLysAlaSerArg-245 |
| SEQ. ID. NO. 25520 | 252-GluAspValGluGlyGluAla-258 |
| SEQ. ID. NO. 25521 | 266-AsnIleArgGlyIleLeu-271 |
| SEQ. ID. NO. 25522 | 278-AlaProGlyPheGlyAspArgArgLysAlaMetLeu-289 |
| SEQ. ID. NO. 25523 | 301-IleSerGluGluValGlyLeuSerLeuGluLysAlaThrLeuAspAspLeuGlyGlnAlaLysArgIleGluIleGlyLysGluAsnThrThr-331 |
| SEQ. ID. NO. 25524 | 334-AspGlyPheGlyAspAlaAlaGlnIleGluAlaArgValAlaGluIleArgGlnGlnIleGluThrAlaThrSerAspTyrAspLysGluLysLeuGlnGlu ArgValAlaLysLeuAlaGly-374 |

| | |
|---|---|
| SEQ. ID. NO. 25525 | 385-ThrGluValGluMetLysGluLysLysAspArgValGluAspAlaLeuHis-401 |
| SEQ. ID. NO. 25526 | 405-AlaAlaValGluGluGlyVal-411 |
| SEQ. ID. NO. 25527 | 421-ArgAlaArgAlaAlaLeu-426 |
| SEQ. ID. NO. 25528 | 429-LeuHisThrGlyAsnAlaAspGlnAspAlaGlyVal-440 |
| SEQ. ID. NO. 25529 | 446-AlaValGluSerProLeuArg-452 |
| SEQ. ID. NO. 25530 | 457-AsnAlaGlyGlyGluProSerVal-464 |
| SEQ. ID. NO. 25531 | 469-ValLeuGluGlyLysGlyAsnTyrGlyTyr-478 |
| SEQ. ID. NO. 25532 | 480-AlaGlySerGlyGluTyrGlyAspMetIleGlu-490 |
| SEQ. ID. NO. 25533 | 495-AspProAlaLysValThrArgSerAlaLeu-504 |
| SEQ. ID. NO. 25534 | 523-GluIleProGluAspLysProAlaMetProAspMetGlyGly-536 |
| Hydrophilic Regions - Hopp-Woods | |
| SEQ. ID. NO. 25535 | 1-MetAlaAlaLysAspValGlnPhe-8 |
| SEQ. ID. NO. 25536 | 10-AsnGluValArgGlnLysMet-16 |
| SEQ. ID. NO. 25537 | 33-ProLysGlyArgAsnValValVal-40 |
| SEQ. ID. NO. 25538 | 48-HisIleThrLysAspGlyValThrValAlaLysGluIleGluLeuLysAspLysPheGluAsn-68 |
| SEQ. ID. NO. 25539 | 73-MetValLysGluValAlaSerLysThrAsnAspValAlaGlyAspGlyThrThr-90 |
| SEQ. ID. NO. 25540 | 114-ThrAspLeuLysArgGlyIleAspLysAlaVal-124 |
| SEQ. ID. NO. 25541 | 129-GluGluLeuLysAsnIleAlaLysProCysAspThrSerLysGluIleAla-145 |
| SEQ. ID. NO. 25542 | 152-AlaAsnSerAspGluGlnVal-158 |
| SEQ. ID. NO. 25543 | 164-GluAlaMetGluLysValGlyLysGluGlyValIleThrValGluAspGlyLysSerLeuGluAsnGluLeuAspVal-189 |
| SEQ. ID. NO. 25544 | 207-AspAlaGluLysGlnIleAla-213 |
| SEQ. ID. NO. 25545 | 223-PheAspLysLysIleSerAsnIleArgAsp-232 |
| SEQ. ID. NO. 25546 | 239-GlnValAlaLysAlaSerArg-245 |
| SEQ. ID. NO. 25547 | 252-GluAspValGluGlyGluAla-258 |
| SEQ. ID. NO. 25548 | 280-GlyPheGlyAspArgArgLysAlaMetLeu-289 |
| SEQ. ID. NO. 25549 | 301-IleSerGluGluValGlyLeuSerLeuGluLysAlaThrLeuAspAspLeuGlyGlnAlaLysArgIleGluIleGlyLysGluAsnThrThr-331 |
| SEQ. ID. NO. 25550 | 340-AlaGlnIleGluAlaArgValAlaGluIleArgGlnGlnIleGluThrAlaThrSerAspTyrAspLysGluLysLeuGlnGluArgValAlaLys-371 |
| SEQ. ID. NO. 25551 | 385-ThrGluValGluMetLysGluLysLysAspArgValGluAspAlaLeuHis-401 |
| SEQ. ID. NO. 25552 | 405-AlaAlaValGluGluGlyVal-411 |
| SEQ. ID. NO. 25553 | 421-ArgAlaArgAlaAlaLeu-426 |
| SEQ. ID. NO. 25554 | 432-GlyAsnAlaAspGlnAspAla-438 |
| SEQ. ID. NO. 25555 | 446-AlaValGluSerProLeu-451 |
| SEQ. ID. NO. 25556 | 458-AlaGlyGlyGluPro-462 |
| SEQ. ID. NO. 25557 | 469-ValLeuGluGlyLysGly-474 |
| SEQ. ID. NO. 25558 | 481-GlySerGlyGluTyrGlyAsp-487 |
| SEQ. ID. NO. 25559 | 495-AspProAlaLysValThrArg-501 |
| SEQ. ID. NO. 25560 | 523-GluIleProGluAspLysProAlaMet-531 |
| a986 | |
| AMPHI Regions - AMPHI | |
| SEQ. ID. NO. 25561 | 6-GlnTyrLeuAlaLeuAla-11 |
| SEQ. ID. NO. 25562 | 18-LeuAlaGlyCysAspLysAlaGly-25 |
| SEQ. ID. NO. 25563 | 36-SerPheValGluArgIleLysHis-43 |
| SEQ. ID. NO. 25564 | 52-MetLeuLeuProAspPheValGlnLeuVal-61 |
| SEQ. ID. NO. 25565 | 97-AspProPheTyrGluPhePheLysArgLeuValProAsnMetProGluIleProGln-115 |
| SEQ. ID. NO. 25566 | 145-ThrGlyMetGlySerIle-150 |
| SEQ. ID. NO. 25567 | 162-AlaLysLeuIleGlySerAspVal-169 |
| SEQ. ID. NO. 25568 | 189-IleGlyAsnProLysAspLeuLysProGly-198 |
| SEQ. ID. NO. 25569 | 200-TrpValAlaAlaIleGly-205 |
| SEQ. ID. NO. 25570 | 287-AlaGluGlnLeuLysAsnThrGlyLysVal-296 |
| SEQ. ID. NO. 25571 | 393-AlaAlaGluHisIleGlyAlaSer-400 |
| SEQ. ID. NO. 25572 | 471-ArgLysAlaMetAspLysAla-477 |
| Antigenic Index - Jameson-Wolf | |
| SEQ. ID. NO. 25573 | 1-ValPheLysLysTyr-5 |
| SEQ. ID. NO. 25574 | 20-GlyCysAspLysAlaGly-25 |
| SEQ. ID. NO. 25575 | 29-GlyAlaAspLysLysGluAlaSerPheValGluArgIleLysHisThrLysAspAspGlySerVal-50 |
| SEQ. ID. NO. 25576 | 61-ValGlnSerGluGlyProAla-67 |
| SEQ. ID. NO. 25577 | 75-ProAlaProArgThrGlnAsnGlySerSerAsnAlaGluThrAspSerAspProLeuAlaAspSerAspProPhe-99 |
| SEQ. ID. NO. 25578 | 104-LysArgLeuValProAsnMetProGluIleProGlnGluGluAlaAspAspGlyGlyLeu-123 |
| SEQ. ID. NO. 25579 | 130-IleIleSerLysAspGlyTyr-136 |
| SEQ. ID. NO. 25580 | 154-LeuAsnAspLysArgGluTyrThr-161 |
| SEQ. ID. NO. 25581 | 165-IleGlySerAspValGlnSerAspValAla-174 |
| SEQ. ID. NO. 25582 | 179-AspAlaThrGluGluLeuPro-185 |
| SEQ. ID. NO. 25583 | 189-IleGlyAsnProLysAspLeuLysProGlyGlu-199 |
| SEQ. ID. NO. 25584 | 208-PheGlyPheAspAsnSerValThr-215 |
| SEQ. ID. NO. 25585 | 218-XxxValSerAlaLysGlyArgSerLeuProAsnGluSerTyr-231 |
| SEQ. ID. NO. 25586 | 242-AsnProGlyAsnSerGlyGlyPro-249 |
| SEQ. ID. NO. 25587 | 265-TyrSerArgSerGlyGly-270 |
| SEQ. ID. NO. 25588 | 288-GluGlnLeuLysAsnThrGlyLysValGlnArgGlyGlnLeu-301 |
| SEQ. ID. NO. 25589 | 316-PheGlyLeuAspLysAlaGlyGly-323 |
| SEQ. ID. NO. 25590 | 330-LeuProGlySerProAlaGluArgAlaGlyLeuArgAlaGlyAsp-344 |
| SEQ. ID. NO. 25591 | 349-LeuAspGlyGlyGluIleArgSerSerGlyAspLeu-360 |
| SEQ. ID. NO. 25592 | 368-ThrProGlyLysGluValSer-374 |
| SEQ. ID. NO. 25593 | 378-TrpArgLysGlyGluGluIleThrIle-386 |
| SEQ. ID. NO. 25594 | 397-IleGlyAlaSerSerLysThrAspGluAlaProTyrThrGluGlnGlnSerGlyThrPhe-416 |
| SEQ. ID. NO. 25595 | 427-ThrHisThrAspSerSerGlyGly-434 |

TABLE 1-continued

SEQ. ID. NO. 25596 440-ArgValSerAspAlaAlaGluArgAlaGlyLeuArgArgGlyAspGluIleLeu-457
SEQ. ID. NO. 25597 463-ProValAsnAspGluAlaGlyPheArgLysAlaMetAspLysAlaGlyLysAsnVal-481
SEQ. ID. NO. 25598 486-MetArgArgGlyAsnThr-491
Hydrophilic Regions - Hopp-Woods
SEQ. ID. NO. 25599 20-GlyCysAspLysAlaGly-25
SEQ. ID. NO. 25600 29-GlyAlaAspLysLysGluAlaSerPheValGluArgIleLysHisThrLysAspAspGlySer-49
SEQ. ID. NO. 25601 75-ProAlaProArgThrGlnAsnGlySerSerAsnAlaGluThrAspSerAspProLeuAlaAspSerAspPro-98
SEQ. ID. NO. 25602 111-ProGluIleProGlnGluGluAlaAspAspGlyGly-122
SEQ. ID. NO. 25603 131-IleSerLysAspGly-135
SEQ. ID. NO. 25604 154-LeuAsnAspLysArgGluTyrThr-161
SEQ. ID. NO. 25605 179-AspAlaThrGluGluLeuPro-185
SEQ. ID. NO. 25606 190-GlyAsnProLysAspLeuLysPro-197
SEQ. ID. NO. 25607 219-ValSerAlaLysGlyArgSerLeuPro-227
SEQ. ID. NO. 25608 288-GluGlnLeuLysAsnThrGlyLysValGlnArgGlyGln-300
SEQ. ID. NO. 25609 317-GlyLeuAspLysAlaGly-322
SEQ. ID. NO. 25610 333-SerProAlaGluArgAlaGlyLeuArgAlaGlyAsp-344
SEQ. ID. NO. 25611 350-AspGlyGlyGluIleArgSerSerGlyAsp-359
SEQ. ID. NO. 25612 368-ThrProGlyLysGluValSer-374
SEQ. ID. NO. 25613 379-ArgLysGlyGluGluIleThrIle-386
SEQ. ID. NO. 25614 397-IleGlyAlaSerSerLysThrAspGluAlaProTyrThrGluGlnGlnSer-413
SEQ. ID. NO. 25615 428-HisThrAspSerSerGly-433
SEQ. ID. NO. 25616 440-ArgValSerAspAlaAlaGluArgAlaGlyLeuArgArgGlyAspGluIleLeu-457
SEQ. ID. NO. 25617 463-ProValAsnAspGluAlaGlyPheArgLysAlaMetAspLysAlaGlyLys-479
a987
AMPHI Regions - AMPHI
SEQ. ID. NO. 25618 17-CysSerSerTrpLeu-21
SEQ. ID. NO. 25619 33-PheAsnThrSerLysProValArgLeuAspAsnIleLeuGlnIle-47
SEQ. ID. NO. 25620 65-ProHisGluAlaPhe-69
SEQ. ID. NO. 25621 144-AsnProPheValLeuArgLysTrpArgAlaLeuGlyTyrLeuThrAspPheProArgLeuAsnArg-165
SEQ. ID. NO. 25622 187-GlyAspGluTyrPheLysVal-193
SEQ. ID. NO. 25623 202-LeuAspIleLeuAlaThr-207
SEQ. ID. NO. 25624 211-ValGlyGluValSerHisAspPheAspArgTyrTrpAla-223
SEQ. ID. NO. 25625 230-AlaThrArgIleIleArgSerGly-237
SEQ. ID. NO. 25626 239-IleGlyLysGlyLeuGlnAla-245
SEQ. ID. NO. 25627 289-SerAspAspProAlaLysGlyLeuAspArg-298
SEQ. ID. NO. 25628 307-GlyArgLeuGlnAspAlaLeuLysGlnPro-316
SEQ. ID. NO. 25629 333-GlyThrAspAlaLeuAlaLysLeuValGlnAsp-343
SEQ. ID. NO. 25630 355-GlnAlaThrAspValAlaAla-361
SEQ. ID. NO. 25631 443-LysIleAlaGluGlnMetGluArgThrLeuAlaAspThr-455
SEQ. ID. NO. 25632 486-ProGluAlaLysLeuTrpLysArgIleAlaAlaLysIleLeuSerLeuLeuProIleGluSerLeu-507
Antigenic Index - Jameson-Wolf
SEQ. ID. NO. 25633 1-MetLysThrArgSer-5
SEQ. ID. NO. 25634 23-ProLeuGluGluArgThrGluSerArgHisPheAsnThrSerLysProValArgLeu-41
SEQ. ID. NO. 25635 49-HisThrProHisThrAsnGlyLeuSer-57
SEQ. ID. NO. 25636 77-GluSerAlaGluHisSerLeu-83
SEQ. ID. NO. 25637 90-TrpArgAsnAspIleSerGlyArgLeu-98
SEQ. ID. NO. 25638 107-AlaGluArgGlyValArg-112
SEQ. ID. NO. 25639 115-LeuLeuLeuAspAspAsnAsnThrArgGlyLeuAsp-126
SEQ. ID. NO. 25640 134-SerHisProAsnIleGluValArgLeu-142
SEQ. ID. NO. 25641 159-AspPheProArgLeuAsnArgArgMetHisAsnLysSerPheThrAlaAspAsnArgAla-178
SEQ. ID. NO. 25642 182-GlyGlyArgAsnIleGlyAspGluTyrPheLysValGlyGluAspThrVal-198
SEQ. ID. NO. 25643 214-ValSerHisAspPheAspArgTyrTrp-222
SEQ. ID. NO. 25644 225-HisSerAlaHisAsn-229
SEQ. ID. NO. 25645 232-ArgIleIleArgSerGlyAsnIleGlyLysGlyLeu-243
SEQ. ID. NO. 25646 247-GlyTyrAsnAspGluThrSerArg-254
SEQ. ID. NO. 25647 259-ArgTyrArgGluThrValGlu-265
SEQ. ID. NO. 25648 267-SerProLeuTyrGln-271
SEQ. ID. NO. 25649 273-IleGlnThrGlyArgIleAsp-279
SEQ. ID. NO. 25650 287-LeuIleSerAspAspProAlaLysGlyLeuAspArgAspArgArgLysProProIle-305
SEQ. ID. NO. 25651 308-ArgLeuGlnAspAlaLeuLysGlnProGluLysSer-319
SEQ. ID. NO. 25652 328-ValProThrLysSerGlyThrAspAlaLeu-337
SEQ. ID. NO. 25653 340-LeuValGlnAspGlyIleAsp-346
SEQ. ID. NO. 25654 367-ValLysTyrArgLysProLeuLeu-374
SEQ. ID. NO. 25655 391-AlaThrLysAspLysGlyLeuThrGlySerSer-401
SEQ. ID. NO. 25656 412-ValAspGlyLysArgIlePhe-418
SEQ. ID. NO. 25657 422-PheAsnLeuAspProArgSerAlaArgLeuAsnThr-433
SEQ. ID. NO. 25658 440-GluSerProLysIleAlaGluGlnMetGluArgThrLeuAlaAspThrSerProGluTyrAla-460
SEQ. ID. NO. 25659 463-ValThrLeuAspArgHisAsnArgLeuGlnTrpHisAspProAlaThrArgLysThrTyrProAsnGluProGluAlaLysLeuTrpLys-492
Hydrophilic Regions - Hopp-Woods
SEQ. ID. NO. 25660 1-MetLysThrArgSer-5
SEQ. ID. NO. 25661 24-LeuGluGluArgThrGluSerArgHisPheAsnThr-35
SEQ. ID. NO. 25662 37-LysProValArgLeu-41
SEQ. ID. NO. 25663 77-GluSerAlaGluHisSerLeu-83
SEQ. ID. NO. 25664 107-AlaGluArgGlyValArg-112
SEQ. ID. NO. 25665 115-LeuLeuLeuAspAspAsnAsnThrArgGlyLeuAsp-126
SEQ. ID. NO. 25666 161-ProArgLeuAsnArgArgMetHisAsn-169
SEQ. ID. NO. 25667 172-PheThrAlaAspAsnArgAla-178
SEQ. ID. NO. 25668 189-GluTyrPheLysValGlyGluAspThrVal-198
SEQ. ID. NO. 25669 214-ValSerHisAspPheAspArg-220
SEQ. ID. NO. 25670 248-TyrAsnAspGluThrSerArg-254

TABLE 1-continued

| | |
|---|---|
| SEQ. ID. NO. 25671 | 259-ArgTyrArgGluThrValGlu-265 |
| SEQ. ID. NO. 25672 | 274-GlnThrGlyArgIleAsp-279 |
| SEQ. ID. NO. 25673 | 287-LeuIleSerAspAspProAlaLysGlyLeuAspArgAspArgArgLysProProIle-305 |
| SEQ. ID. NO. 25674 | 308-ArgLeuGlnAspAlaLeuLysGlnProGluLysSer-319 |
| SEQ. ID. NO. 25675 | 331-LysSerGlyThrAspAlaLeu-337 |
| SEQ. ID. NO. 25676 | 340-LeuValGlnAspGlyIleAsp-346 |
| SEQ. ID. NO. 25677 | 367-ValLysTyrArgLysProLeuLeu-374 |
| SEQ. ID. NO. 25678 | 391-AlaThrLysAspLysGlyLeuThr-398 |
| SEQ. ID. NO. 25679 | 424-LeuAspProArgSerAlaArgLeuAsnThr-433 |
| SEQ. ID. NO. 25680 | 440-GluSerProLysIleAlaGluGlnMetGluArgThrLeuAlaAspThrSerPro-457 |
| SEQ. ID. NO. 25681 | 464-ThrLeuAspArgHisAsnArg-470 |
| SEQ. ID. NO. 25682 | 476-ProAlaThrArgLysThrTyrProAsnGluProGluAlaLysLeuTrpLys-492 |
| a988 | |
| AMPHI Regions - AMPHI | |
| SEQ. ID. NO. 25683 | 45-SerLysIleGluAlaLeu-50 |
| SEQ. ID. NO. 25684 | 66-ArgArgLeuLysAlaMet-71 |
| SEQ. ID. NO. 25685 | 125-GlnMetArgGlyIle-129 |
| SEQ. ID. NO. 25686 | 154-AspIleValGluArgAlaGlnSerLysVal-163 |
| SEQ. ID. NO. 25687 | 221-AlaLysIleIleGluValLeuGlyAspTyrAlaAsp-232 |
| SEQ. ID. NO. 25688 | 248-HisGlnPheSerGluAlaCysAlaLysAlaAlaLysLysIleProAspHisValArgLys-267 |
| SEQ. ID. NO. 25689 | 288-ThrAlaArgAspPheAspAsp-294 |
| SEQ. ID. NO. 25690 | 299-GluLysIleGlyArgAsnTyrArg-306 |
| SEQ. ID. NO. 25691 | 310-AlaIleAlaAspValSerHisTyrValArgProAspAsp-322 |
| SEQ. ID. NO. 25692 | 348-AsnLeuSerAsnGly-352 |
| SEQ. ID. NO. 25693 | 396-AsnGlnValTrpLysTrpLeuSer-403 |
| SEQ. ID. NO. 25694 | 405-GlyIleGluHisPro-409 |
| SEQ. ID. NO. 25695 | 411-LysThrGlnIleAspThrLeuTyrLysLeuPheLysIleLeuGlnLys-426 |
| SEQ. ID. NO. 25696 | 494-LeuGlyProThrProGluLysLeuAlaAlaLeu-504 |
| SEQ. ID. NO. 25697 | 524-LysAspTyrAlaAlaLeuAla-530 |
| SEQ. ID. NO. 25698 | 544-ValMetMetLeuArgSerMetGlnGlnAla-553 |
| SEQ. ID. NO. 25699 | 569-AlaTyrAlaHisPheThrSerProIleArgArgTyrProAspLeuThrValHisArgAlaIleLysAlaValLeu-593 |
| SEQ. ID. NO. 25700 | 619-AspAspAlaSerArgAspValGluAsnTrpLeuLys-630 |
| SEQ. ID. NO. 25701 | 646-IleSerGlyMetThrSerPheGlyIlePheValThrLeu-658 |
| SEQ. ID. NO. 25702 | 662-HisIleAspGlyLeuValHisIleSerAspLeuGlyGlu-674 |
| Antigenic Index - Jameson-Wolf | |
| SEQ. ID. NO. 25703 | 1-MetAsnLysAsnIleLys-6 |
| SEQ. ID. NO. 25704 | 8-LeuAsnLeuArgGluLysAspProPheLeuSerArgGluLysGlnArgTyrGluHisProLeuProSerArgGluTrpIle-34 |
| SEQ. ID. NO. 25705 | 37-LeuLeuGluArgLysGlyValProSerLysIleGluAlaLeuValArg-52 |
| SEQ. ID. NO. 25706 | 54-LeuSerIleLysGluGluGluTyrGluPhePheGluArgArgLeuLysAlaMetAlaArgAspGlyGln-76 |
| SEQ. ID. NO. 25707 | 79-IleAsnArgArgGlyAlaVal-85 |
| SEQ. ID. NO. 25708 | 87-AlaAlaAspLysLeuAspLeuValLysCysArgValLysAlaHisLysAspArgPheGlyPhe-107 |
| SEQ. ID. NO. 25709 | 111-LeuThrProAlaLysAspGlyAsp-118 |
| SEQ. ID. NO. 25710 | 124-ArgGlnMetArgGly-128 |
| SEQ. ID. NO. 25711 | 140-AlaGlyMetAspGlyArgGlyArgArgGluGlyThrVal-152 |
| SEQ. ID. NO. 25712 | 155-IleValGluArgAlaGlnSerLysValValGly-165 |
| SEQ. ID. NO. 25713 | 167-PheXxxMetAspArgGlyValAla-174 |
| SEQ. ID. NO. 25714 | 176-LeuGluProGluAspLysArgLeuAsnGln-185 |
| SEQ. ID. NO. 25715 | 189-LeuGluProAspGlyValAlaArgPheLysProGluSerGlyGln-203 |
| SEQ. ID. NO. 25716 | 210-GluValTyrProGluGlnAsnArgProAlaVal-220 |
| SEQ. ID. NO. 25717 | 227-LeuGlyAspTyrAlaAspSerGlyMetGluIle-237 |
| SEQ. ID. NO. 25718 | 239-IleAlaValArgLysHisHisLeu-246 |
| SEQ. ID. NO. 25719 | 253-AlaCysAlaLysAlaAlaLysLysIleProAspHisValArgLysSerAspLeuLysGlyArgValAspLeuArgAsp-278 |
| SEQ. ID. NO. 25720 | 283-ThrIleAspGlyGluThrAlaArgAspPheAspAsp-294 |
| SEQ. ID. NO. 25721 | 299-GluLysIleGlyArgAsnTyrArg-306 |
| SEQ. ID. NO. 25722 | 316-HisTyrValArgProAspAspAlaIleAspThrAspAlaGlnGluArgSerThrSerVal-335 |
| SEQ. ID. NO. 25723 | 337-PheProArgArgVal-341 |
| SEQ. ID. NO. 25724 | 345-LeuProGluAsnLeuSerAsnGly-352 |
| SEQ. ID. NO. 25725 | 374-AlaGlyAsnIleLysGluTyrArgPhe-382 |
| SEQ. ID. NO. 25726 | 402-LeuSerGlyGlyIleGluHisProPheLysThrGlnIle-414 |
| SEQ. ID. NO. 25727 | 424-LeuGlnLysLysArgPheGluArgGlyAlaValGluPheAspSerIleGlu-440 |
| SEQ. ID. NO. 25728 | 443-MetLeuPheAspAspAsnGlyLysIleGluLys-453 |
| SEQ. ID. NO. 25729 | 458-ValArgAsnAspAlaHisLysLeuIleGlu-467 |
| SEQ. ID. NO. 25730 | 482-LeuLysAsnLysHisThrAla-488 |
| SEQ. ID. NO. 25731 | 493-HisLeuGlyProThrProGluLysLeuAlaAlaLeuArgGluGlnLeu-508 |
| SEQ. ID. NO. 25732 | 516-GlyGlyGlyAspAsnProSerProLysAspTyrAla-527 |
| SEQ. ID. NO. 25733 | 532-GlnPheLysGlyArgProAspAlaGluLeu-541 |
| SEQ. ID. NO. 25734 | 556-GluProHisCysAspGlyHis-562 |
| SEQ. ID. NO. 25735 | 575-SerProIleArgArgTyrProAspLeuThrVal-585 |
| SEQ. ID. NO. 25736 | 597-ThrTyrThrProLysLysSerTrp-604 |
| SEQ. ID. NO. 25737 | 613-PheCysGluArgArgAlaAspAspAlaSerArgAspValGluAsn-627 |
| SEQ. ID. NO. 25738 | 633-TyrMetArgAspLysValGlyGluValPheGluGlyLysIleSerGly-648 |
| SEQ. ID. NO. 25739 | 670-SerAspLeuGlyGluAspTyrPheAsnPheArgPro-681 |
| SEQ. ID. NO. 25740 | 683-IleMetAlaIleGluGlyGluArgSerGlyIleArgPheAsnMetGlyAspArgValAlaValArgValAlaArgAlaAspLeuAspAspGlyLysIle-715 |
| SEQ. ID. NO. 25741 | 722-GlyGlySerGlyArgGlyArgLysValLysSerSerAlaSerAlaLysProAlaGlyThrAlaGlyLysGlyLysProLysThrAlaAlaGluLysLysThr AlaArgGlyGlyLysValArgGlyArgGlyAlaSerAlaAlaAlaGluSerArgLysLysAlaLysLysProValProIleLysValLysLysArgLysGlyLys Ser-791 |
| Hydrophilic Regions - Hopp-Woods | |
| SEQ. ID. NO. 25742 | 1-MetAsnLysAsnIleLys-6 |
| SEQ. ID. NO. 25743 | 8-LeuAsnLeuArgGluLysAspProPheLeuSerArgGluLysGlnArgTyrGluHis-26 |

TABLE 1-continued

| | |
|---|---|
| SEQ. ID. NO. 25744 | 37-LeuLeuGluArgLysGlyValProSerLysIleGluAlaLeuValArg-52 |
| SEQ. ID. NO. 25745 | 54-LeuSerIleLysGluGluGluTyrGluPhePheGluArgArgLeuLysAlaMetAlaArgAspGlyGln-76 |
| SEQ. ID. NO. 25746 | 79-IleAsnArgArgGlyAla-84 |
| SEQ. ID. NO. 25747 | 87-AlaAlaAspLysLeuAspLeuValLysCysArgValLysAlaHisLysAspArgPhe-105 |
| SEQ. ID. NO. 25748 | 113-ProAlaLysAspGlyAsp-118 |
| SEQ. ID. NO. 25749 | 140-AlaGlyMetAspGlyArgGlyArgArgGluGlyThrVal-152 |
| SEQ. ID. NO. 25750 | 155-IleValGluArgAlaGlnSerLysValValGly-165 |
| SEQ. ID. NO. 25751 | 167-PheXxxMetAspArgGlyValAla-174 |
| SEQ. ID. NO. 25752 | 176-LeuGluProGluAspLysArgLeuAsn-184 |
| SEQ. ID. NO. 25753 | 189-LeuGluProAspGlyValAlaArgPheLysProGluSerGly-202 |
| SEQ. ID. NO. 25754 | 210-GluValTyrProGluGlnAsnArgProAlaVal-220 |
| SEQ. ID. NO. 25755 | 230-TyrAlaAspSerGlyMetGluIle-237 |
| SEQ. ID. NO. 25756 | 239-IleAlaValArgLysHisHis-245 |
| SEQ. ID. NO. 25757 | 253-AlaCysAlaLysAlaAlaLysLysIleProAspHisValArgLysSerAspLeuLysGlyArgValAspLeuArgAsp-278 |
| SEQ. ID. NO. 25758 | 284-IleAspGlyGluThrAlaArgAspPheAspAsp-294 |
| SEQ. ID. NO. 25759 | 300-LysIleGlyArgAsnTyr-305 |
| SEQ. ID. NO. 25760 | 318-ValArgProAspAspAlaIleAspThrAspAlaGlnGluArgSerThr-333 |
| SEQ. ID. NO. 25761 | 376-AsnIleLysGluTyrArg-381 |
| SEQ. ID. NO. 25762 | 424-LeuGlnLysLysArgPheGluArgGlyAlaValGluPheAspSerIleGlu-440 |
| SEQ. ID. NO. 25763 | 443-MetLeuPheAspAspAsnGlyLysIleGluLys-453 |
| SEQ. ID. NO. 25764 | 458-ValArgAsnAspAlaHisLysLeuIleGlu-467 |
| SEQ. ID. NO. 25765 | 496-ProThrProGluLysLeuAlaAlaLeuArgGluGlnLeu-508 |
| SEQ. ID. NO. 25766 | 517-GlyGlyAspAsnProSerProLysAspTyrAla-527 |
| SEQ. ID. NO. 25767 | 533-PheLysGlyArgProAspAlaGluLeu-541 |
| SEQ. ID. NO. 25768 | 576-ProIleArgArgTyrProAsp-582 |
| SEQ. ID. NO. 25769 | 598-TyrThrProLysLysSerTrp-604 |
| SEQ. ID. NO. 25770 | 613-PheCysGluArgArgAlaAspAspAlaSerArgAspValGluAsn-627 |
| SEQ. ID. NO. 25771 | 633-TyrMetArgAspLysValGlyGluValPheGluGlyLysIle-646 |
| SEQ. ID. NO. 25772 | 683-IleMetAlaIleGluGlyGluArgSerGlyIle-693 |
| SEQ. ID. NO. 25773 | 696-AsnMetGlyAspArgValAlaValArgValAlaArgAlaAspLeuAspAspGlyLysIle-715 |
| SEQ. ID. NO. 25774 | 723-GlySerGlyArgGlyArgLysValLysSerSerAlaSerAlaLysProAlaGlyThrAlaGlyLysGlyLysProLysThrAlaAlaGluLysLysThrAla ArgGlyGlyLysValArgGlyArgGlyAlaSerAlaAlaAlaGluSerArgLysLysAlaLysLysProValProIleLysValLysLysArgLysGlyLysSer-791 |
| a989 | |
| AMPHI Regions - AMPHI | |
| SEQ. ID. NO. 25775 | 58-AlaGlyLeuThrLysLeu-63 |
| SEQ. ID. NO. 25776 | 85-SerAlaThrAspPhe-89 |
| SEQ. ID. NO. 25777 | 98-LysSerGlyLysIleThr-103 |
| SEQ. ID. NO. 25778 | 109-ProHisIleTyrGlyAla-114 |
| SEQ. ID. NO. 25779 | 183-GluLeuArgLysTyrAlaAspTrpGlyIleMetGluLysAlaLysAlaLeu-199 |
| SEQ. ID. NO. 25780 | 201-GluThrProProAsnProThrLysAla-209 |
| SEQ. ID. NO. 25781 | 299-SerValHisGlyMetTyrLysValSer-307 |
| SEQ. ID. NO. 25782 | 318-TrpThrArgHisSerArg-323 |
| SEQ. ID. NO. 25783 | 362-SerTyrGlnIleSerGluProLeu-369 |
| SEQ. ID. NO. 25784 | 448-PheLysAsnHisAlaAsp-453 |
| Antigenic Index - Jameson-Wolf | |
| SEQ. ID. NO. 25785 | 43-AlaAlaAlaGluAlaAlaAspAlaSer-51 |
| SEQ. ID. NO. 25786 | 57-ProAlaGlyLeuThrLysLeuAspSerSerGlnIleSer-69 |
| SEQ. ID. NO. 25787 | 81-TyrGluAlaAspSerAlaThrAspPheThr-90 |
| SEQ. ID. NO. 25788 | 94-ValGlnGlySerLysSerGlyLysIleThrLysThrThr-106 |
| SEQ. ID. NO. 25789 | 116-LysValAsnAspAsnLeuThr-122 |
| SEQ. ID. NO. 25790 | 132-GlySerAlaThrGluTyrGluLysAspSerValLeu-143 |
| SEQ. ID. NO. 25791 | 146-AsnIleAsnLysLeuGly-151 |
| SEQ. ID. NO. 25792 | 164-LysLeuAsnGluArgHisSerPheGly-172 |
| SEQ. ID. NO. 25793 | 180-ThrSerAlaGluLeuArgLysTyrAla-188 |
| SEQ. ID. NO. 25794 | 194-GluLysAlaLysAlaLeuLysGluThrProProAsnProThrLysAlaAlaGlnIleLysAlaAspGlyHisAlaAspValLysGlySerAspTrpGly-226 |
| SEQ. ID. NO. 25795 | 236-AspIleAsnAspArgAlaArgValGlyValAsnTyrArgSerLysValSerHisThrLeuLysGlyAspAlaGluTrpAlaAla-263 |
| SEQ. ID. NO. 25796 | 272-TrpAspAlaAsnLys-276 |
| SEQ. ID. NO. 25797 | 283-ThrProSerGluLysAlaArgValLysIleValThrProGluSer-297 |
| SEQ. ID. NO. 25798 | 304-TyrLysValSerAspLysAlaAspLeu-312 |
| SEQ. ID. NO. 25799 | 317-ThrTrpThrArgHisSerArgPheAspLysAlaGluLeuValPheGluLysGluLysThrIleValAsnGlyLysSerAspArgThrThrIle-347 |
| SEQ. ID. NO. 25800 | 349-ProAsnTrpArgAsnThrTyrLysValGlyPhe-359 |
| SEQ. ID. NO. 25801 | 361-GlySerTyrGlnIleSerGluLeuGln-370 |
| SEQ. ID. NO. 25802 | 375-IleAlaPheAspLysSerProValArgAsnAlaAspTyrArgMetAsnSerLeuProAspGlyAsn-396 |
| SEQ. ID. NO. 25803 | 407-HisIleGlyLysAsnHisVal-413 |
| SEQ. ID. NO. 25804 | 424-AsnAspThrSerTyrArgThrAlaLysAlaSerGlyAsnAspValAspSerLysGlyAlaSerSerAlaArgPheLysAsnHisAla-452 |
| Hydrophilic Regions - Hopp-Woods | |
| SEQ. ID. NO. 25805 | 43-AlaAlaAlaGluAlaAlaAsp-49 |
| SEQ. ID. NO. 25806 | 61-ThrLysLeuAspSerSerGln-67 |
| SEQ. ID. NO. 25807 | 81-TyrGluAlaAspSerAlaThr-87 |
| SEQ. ID. NO. 25808 | 95-GlnGlySerLysSerGlyLysIleThrLys-104 |
| SEQ. ID. NO. 25809 | 135-ThrGluTyrGluLysAspSerValLeu-143 |
| SEQ. ID. NO. 25810 | 164-LysLeuAsnGluArgHisSer-170 |
| SEQ. ID. NO. 25811 | 180-ThrSerAlaGluLeuArgLysTyrAla-188 |
| SEQ. ID. NO. 25812 | 194-GluLysAlaLysAlaLeuLysGluThrProProAsnProThrLysAlaAlaGlnIleLysAlaAspGlyHisAlaAspValLysGlySerAsp-224 |
| SEQ. ID. NO. 25813 | 237-IleAsnAspArgAlaArgVal-243 |
| SEQ. ID. NO. 25814 | 247-TyrArgSerLysVal-251 |
| SEQ. ID. NO. 25815 | 255-LeuLysGlyAspAlaGluTrpAlaAla-263 |
| SEQ. ID. NO. 25816 | 284-ProSerGluLysAlaArgValLysIleValThr-294 |

TABLE 1-continued

| | |
|---|---|
| SEQ. ID. NO. 25817 | 305-LysValSerAspLysAlaAspLeu-312 |
| SEQ. ID. NO. 25818 | 322-SerArgPheAspLysAlaGluLeuValPheGluLysGluLysThrIleVal-338 |
| SEQ. ID. NO. 25819 | 340-GlyLysSerAspArgThrThrIle-347 |
| SEQ. ID. NO. 25820 | 375-IleAlaPheAspLysSerProValArgAsnAlaAspTyrArgMet-389 |
| SEQ. ID. NO. 25821 | 391-SerLeuProAspGlyAsn-396 |
| SEQ. ID. NO. 25822 | 426-ThrSerTyrArgThrAlaLysAlaSerGlyAsnAspValAspSerLysGlyAlaSerSerAlaArgPheLysAsnHisAla-452 |
| a990 | |
| AMPHI Regions - AMPHI | |
| SEQ. ID. NO. 25823 | 76-IleThrAspThrTyrGlyAspAsnLeuLysAspAlaValLysLysGlnLeuGlnAspLeuTyrLys-97 |
| SEQ. ID. NO. 25824 | 131-AspLeuIleAsnLysLeuVal-137 |
| SEQ. ID. NO. 25825 | 151-ThrSerLeuAsnAsnIlePhe-157 |
| SEQ. ID. NO. 25826 | 195-AspIleHisMetLeu-199 |
| SEQ. ID. NO. 25827 | 260-ProGluAsnLeuLysThrLeuAspGly-268 |
| SEQ. ID. NO. 25828 | 293-TyrGluLeuLeuLeuLysGlnCys-300 |
| SEQ. ID. NO. 25829 | 419-SerTyrLeuHisGlyTyrGlyGlyGlyValTyrAlaAlaTrp-432 |
| SEQ. ID. NO. 25830 | 442-AlaTyrLeuAspGlyTrpLeuGlnTyr-450 |
| SEQ. ID. NO. 25831 | 472-ThrAlaSerValGluGlyGlyTyrAsnAlaLeu-482 |
| SEQ. ID. NO. 25832 | 550-GlnProPheAlaAlaPheAsnValLeuHisArg-560 |
| Antigenic Index - Jameson-Wolf | |
| SEQ. ID. NO. 25833 | 6-LeuGlySerAsnThrArgSerThrLysIleGlyAspAspAlaAspPheSerPheSerAspLysProLysProGlyThr-31 |
| SEQ. ID. NO. 25834 | 35-PheSerSerGlyLysThrAspGlnAsnSerSerGluTyrGlyTyrAspGluIleAsnIleGlnGlyLysAsnTyrAsnSerGlyIle-63 |
| SEQ. ID. NO. 25835 | 75-TyrIleThrAspThrTyrGlyAspAsnLeuLysAspAlaValLysLysGlnLeuGlnAspLeuTyrLysThrArgProGluAlaTrpGluGluAsnLys LysArgThrGluGluAlaTyr-114 |
| SEQ. ID. NO. 25836 | 123-SerIleLeuLysGlnLysAsnProAspLeuIle-133 |
| SEQ. ID. NO. 25837 | 145-HisSerAsnThrSerGlnThrSer-152 |
| SEQ. ID. NO. 25838 | 157-PheAsnLysLysLeuHisValLysIleGluAsnLysSerHisVal-171 |
| SEQ. ID. NO. 25839 | 179-ThrLysMetThrLeuLysAspSerLeuTrpGluProArgArgHisSerAspIleHisMet-198 |
| SEQ. ID. NO. 25840 | 200-GluThrSerAspAsnAlaArgIleArgLeuAsnThrLysAspGluLysLeuThrVal-218 |
| SEQ. ID. NO. 25841 | 222-TyrGlnGlyGlyAla-226 |
| SEQ. ID. NO. 25842 | 233-AspValArgGluSerAspLysProAlaLeuThrPheGluGluLysValSerGlyGlnSerGlyValValLeuGluArgArgProGluAsnLeuLysThr LeuAspGlyArgLysLeuIleAlaAlaGluLysAlaAspSerAsnSerPheAlaPheLysGlnAsnTyrArgGlnGlyLeu-292 |
| SEQ. ID. NO. 25843 | 298-LysGlnCysGluGlyGlyPhe-304 |
| SEQ. ID. NO. 25844 | 312-AlaIleProGluAlaGlu-317 |
| SEQ. ID. NO. 25845 | 335-ArgAlaAlaAspArgGlyAspAspValTyrAlaAlaAspProSerArgGlnLysLeu-353 |
| SEQ. ID. NO. 25846 | 358-IleGlyGlyArgSerHisGlnAsnIleArgGlyGlyAlaAlaAlaAspGlyArgArgLysGlyVal-379 |
| SEQ. ID. NO. 25847 | 385-ValPheValArgGlnAsnGluGlySerArgLeuAla-396 |
| SEQ. ID. NO. 25848 | 400-MetGlyGlyArgAlaGlyGln-406 |
| SEQ. ID. NO. 25849 | 408-AlaSerValAsnGlyLysGlyGlyAla-416 |
| SEQ. ID. NO. 25850 | 435-LeuArgAspLysGlnThrGlyAlaTyr-443 |
| SEQ. ID. NO. 25851 | 452-ArgPheLysHisArgIleAsnAspGluAsnArgAlaGluArgTyrLysThrLysGlyTrpThr-472 |
| SEQ. ID. NO. 25852 | 475-ValGluGlyGlyTyr-479 |
| SEQ. ID. NO. 25853 | 487-ValValGlyLysGlyAsnAsnValArg-495 |
| SEQ. ID. NO. 25854 | 510-AsnGlyGlyPheThrAspSerGluGlyThrAla-520 |
| SEQ. ID. NO. 25855 | 525-GlySerGlyGlnTrpGlnSerArgAlaGlyIleArgAlaLysThrArgPheAlaLeuArgAsnGlyValAsn-548 |
| SEQ. ID. NO. 25856 | 559-HisArgSerLysSerPheGlyValGluMetAspGlyGluLysGlnThrLeuAla-576 |
| SEQ. ID. NO. 25857 | 579-ThrAlaLeuGluGlyArgPheGlyIle-587 |
| SEQ. ID. NO. 25858 | 589-AlaGlyTrpLysGlyHisMet-595 |
| SEQ. ID. NO. 25859 | 600-GlyTyrGlyLysArgThrAspGlyAspLysGluAlaAlaLeu-613 |
| Hydrophilic Regions - Hopp-Woods | |
| SEQ. ID. NO. 25860 | 8-SerAsnThrArgSerThrLysIleGlyAspAspAlaAspPheSerPheSerAspLysProLysProGlyThr-31 |
| SEQ. ID. NO. 25861 | 38-GlyLysThrAspGlnAsnSerSer-45 |
| SEQ. ID. NO. 25862 | 79-ThrTyrGlyAspAsnLeuLysAspAlaValLysLysGlnLeuGlnAsp-94 |
| SEQ. ID. NO. 25863 | 96-TyrLysThrArgProGluAlaTrpGluGluAsnLysLysArgThrGluGluAlaTyr-114 |
| SEQ. ID. NO. 25864 | 123-SerIleLeuLysGlnLysAsnProAspLeuIle-133 |
| SEQ. ID. NO. 25865 | 161-LeuHisValLysIleGluAsnLysSerHisVal-171 |
| SEQ. ID. NO. 25866 | 179-ThrLysMetThrLeuLys-184 |
| SEQ. ID. NO. 25867 | 186-SerLeuTrpGluProArgArgHisSerAsp-195 |
| SEQ. ID. NO. 25868 | 200-GluThrSerAspAsnAlaArgIleArgLeuAsnThrLysAspGluLysLeuThrVal-218 |
| SEQ. ID. NO. 25869 | 233-AspValArgGluSerAspLysProAlaLeuThrPheGluGluLysValSerGly-250 |
| SEQ. ID. NO. 25870 | 255-ValLeuGluArgArgProGluAsnLeuLysThrLeuAspGlyArgLysLeuIleAlaAlaGluLysAlaAspSerAsn-280 |
| SEQ. ID. NO. 25871 | 312-AlaIleProGluAlaGlu-317 |
| SEQ. ID. NO. 25872 | 335-ArgAlaAlaAspArgGlyAspAspValTyrAla-345 |
| SEQ. ID. NO. 25873 | 347-AspProSerArgGln-351 |
| SEQ. ID. NO. 25874 | 361-ArgSerHisGlnAsnIleArgGly-368 |
| SEQ. ID. NO. 25875 | 370-AlaAlaAlaAspGlyArgArgLysGlyVal-379 |
| SEQ. ID. NO. 25876 | 385-ValPheValArgGlnAsnGluGlySerArg-394 |
| SEQ. ID. NO. 25877 | 410-ValAsnGlyLysGlyGlyAla-416 |
| SEQ. ID. NO. 25878 | 435-LeuArgAspLysGlnThr-440 |
| SEQ. ID. NO. 25879 | 452-ArgPheLysHisArgIleAsnAspGluAsnArgAlaGluArgTyrLysThr-468 |
| SEQ. ID. NO. 25880 | 487-ValValGlyLysGlyAsnAsn-493 |
| SEQ. ID. NO. 25881 | 513-PheThrAspSerGluGlyThr-519 |
| SEQ. ID. NO. 25882 | 533-AlaGlyIleArgAlaLysThrArgPheAlaLeu-543 |
| SEQ. ID. NO. 25883 | 559-HisArgSerLysSerPheGlyValGluMetAspGlyGluLysGlnThrLeuAla-576 |
| SEQ. ID. NO. 25884 | 579-ThrAlaLeuGluGly-583 |
| SEQ. ID. NO. 25885 | 600-GlyTyrGlyLysArgThrAspGlyAspLysGluAlaAlaLeu-613 |
| a990 | |
| AMPHI Regions - AMPHI | |
| SEQ. ID. NO. 25886 | 76-IleThrAspThrTyrGlyAspAsnLeuLysAspAlaValLysLysGlnLeuGlnAspLeuTyrLys-97 |
| SEQ. ID. NO. 25887 | 131-AspLeuIleAsnLysLeuVal-137 |
| SEQ. ID. NO. 25888 | 151-ThrSerLeuAsnAsnIlePhe-157 |

TABLE 1-continued

| | |
|---|---|
| SEQ. ID. NO. 25889 | 195-AspIleHisMetLeu-199 |
| SEQ. ID. NO. 25890 | 260-ProGluAsnLeuLysThrLeuAspGly-268 |
| SEQ. ID. NO. 25891 | 293-TyrGluLeuLeuLeuLysGlnCys-300 |
| SEQ. ID. NO. 25892 | 419-SerTyrLeuHisGlyTyrGlyGlyGlyValTyrAlaAlaTrp-432 |
| SEQ. ID. NO. 25893 | 442-AlaTyrLeuAspGlyTrpLeuGlnTyr-450 |
| SEQ. ID. NO. 25894 | 472-ThrAlaSerValGluGlyGlyTyrAsnAlaLeu-482 |
| SEQ. ID. NO. 25895 | 550-GlnProPheAlaAlaPheAsnValLeuHisArg-560 |
| Antigenic Index - Jameson-Wolf | |
| SEQ. ID. NO. 25896 | 6-LeuGlySerAsnThrArgSerThrLysIleGlyAspAspAlaAspPheSerPheSerAspLysProLysProGlyThr-31 |
| SEQ. ID. NO. 25897 | 35-PheSerSerGlyLysThrAspGlnAsnSerSerGluTyrGlyTyrAspGluIleAsnIleGlnGlyLysAsnTyrAsnSerGlyIle-63 |
| SEQ. ID. NO. 25898 | 75-TyrIleThrAspThrTyrGlyAspAsnLeuLysAspAlaValLysLysGlnLeuGlnAspLeuTyrLysThrArgProGluAlaTrpGluGluAsnLys LysArgThrGluGluAlaTyr-114 |
| SEQ. ID. NO. 25899 | 123-SerIleLeuLysGlnLysAsnProAspLeuIle-133 |
| SEQ. ID. NO. 25900 | 145-HisSerAsnThrSerGlnThrSer-152 |
| SEQ. ID. NO. 25901 | 157-PheAsnLysLysLeuHisValLysIleGluAsnLysSerHisVal-171 |
| SEQ. ID. NO. 25902 | 179-ThrLysMetThrLeuLysAspSerLeuTrpGluProArgArgHisSerAspIleHisMet-198 |
| SEQ. ID. NO. 25903 | 200-GluThrSerAspAsnAlaArgIleArgLeuAsnThrLysAspGluLysLeuThrVal-218 |
| SEQ. ID. NO. 25904 | 222-TyrGlnGlyGlyAla-226 |
| SEQ. ID. NO. 25905 | 233-AspValArgGluSerAspLysProAlaLeuThrPheGluGluLysValSerGlyGlnSerGlyValValLeuGluArgArgProGluAsnLeuLysThr LeuAspGlyArgLysLeuIleAlaAlaGluLysAlaAspSerAsnSerPheAlaPheLysGlnAsnTyrArgGlnGlyLeu-292 |
| SEQ. ID. NO. 25906 | 298-LysGlnCysGluGlyGlyPhe-304 |
| SEQ. ID. NO. 25907 | 312-AlaIleProGluAlaGlu-317 |
| SEQ. ID. NO. 25908 | 335-ArgAlaAlaAspArgGlyAspAspValTyrAlaAlaAspProSerArgGlnLysLeu-353 |
| SEQ. ID. NO. 25909 | 358-IleGlyGlyArgSerHisGlnAsnIleArgGlyGlyAlaAlaAlaAspGlyArgArgLysGlyVal-379 |
| SEQ. ID. NO. 25910 | 385-ValPheValArgGlnAsnGluGlySerArgLeuAla-396 |
| SEQ. ID. NO. 25911 | 400-MetGlyGlyArgAlaGlyGln-406 |
| SEQ. ID. NO. 25912 | 408-AlaSerValAsnGlyLysGlyGlyAla-416 |
| SEQ. ID. NO. 25913 | 435-LeuArgAspLysGlnThrGlyAlaTyr-443 |
| SEQ. ID. NO. 25914 | 452-ArgPheLysHisArgIleAsnAspGluAsnArgAlaGluArgTyrLysThrLysGlyTrpThr-472 |
| SEQ. ID. NO. 25915 | 475-ValGluGlyGlyTyr-479 |
| SEQ. ID. NO. 25916 | 487-ValValGlyLysGlyAsnAsnValArg-495 |
| SEQ. ID. NO. 25917 | 510-AsnGlyGlyPheThrAspSerGluGlyThrAla-520 |
| SEQ. ID. NO. 25918 | 525-GlySerGlyGlnTrpGlnSerArgAlaGlyIleArgAlaLysThrArgPheAlaLeuArgAsnGlyValAsn-548 |
| SEQ. ID. NO. 25919 | 559-HisArgSerLysSerPheGlyValGluMetAspGlyGluLysGlnThrLeuAla-576 |
| SEQ. ID. NO. 25920 | 579-ThrAlaLeuGluGlyArgPheGlyIle-587 |
| SEQ. ID. NO. 25921 | 589-AlaGlyTrpLysGlyHisMet-595 |
| SEQ. ID. NO. 25922 | 600-GlyTyrGlyLysArgThrAspGlyAspLysGluAlaAlaLeu-613 |
| Hydrophilic Regions - Hopp-Woods | |
| SEQ. ID. NO. 25923 | 8-SerAsnThrArgSerThrLysIleGlyAspAspAlaAspPheSerPheSerAspLysProLysProGlyThr-31 |
| SEQ. ID. NO. 25924 | 38-GlyLysThrAspGlnAsnSerSer-45 |
| SEQ. ID. NO. 25925 | 79-ThrTyrGlyAspAsnLeuLysAspAlaValLysLysGlnLeuGlnAsp-94 |
| SEQ. ID. NO. 25926 | 96-TyrLysThrArgProGluAlaTrpGluGluAsnLysLysArgThrGluGluAlaTyr-114 |
| SEQ. ID. NO. 25927 | 123-SerIleLeuLysGlnLysAsnProAspLeuIle-133 |
| SEQ. ID. NO. 25928 | 161-LeuHisValLysIleGluAsnLysSerHisVal-171 |
| SEQ. ID. NO. 25929 | 179-ThrLysMetThrLeuLys-184 |
| SEQ. ID. NO. 25930 | 186-SerLeuTrpGluProArgArgHisSerAsp-195 |
| SEQ. ID. NO. 25931 | 200-GluThrSerAspAsnAlaArgIleArgLeuAsnThrLysAspGluLysLeuThrVal-218 |
| SEQ. ID. NO. 25932 | 233-AspValArgGluSerAspLysProAlaLeuThrPheGluGluLysValSerGly-250 |
| SEQ. ID. NO. 25933 | 255-ValLeuGluArgArgProGluAsnLeuLysThrLeuAspGlyArgLysLeuIleAlaAlaGluLysAlaAspSerAsn-280 |
| SEQ. ID. NO. 25934 | 312-AlaIleProGluAlaGlu-317 |
| SEQ. ID. NO. 25935 | 335-ArgAlaAlaAspArgGlyAspAspValTyrAla-345 |
| SEQ. ID. NO. 25936 | 347-AspProSerArgGln-351 |
| SEQ. ID. NO. 25937 | 361-ArgSerHisGlnAsnIleArgGly-368 |
| SEQ. ID. NO. 25938 | 370-AlaAlaAlaAspGlyArgArgLysGlyVal-379 |
| SEQ. ID. NO. 25939 | 385-ValPheValArgGlnAsnGluGlySerArg-394 |
| SEQ. ID. NO. 25940 | 410-ValAsnGlyLysGlyGlyAla-416 |
| SEQ. ID. NO. 25941 | 435-LeuArgAspLysGlnThr-440 |
| SEQ. ID. NO. 25942 | 452-ArgPheLysHisArgIleAsnAspGluAsnArgAlaGluArgTyrLysThr-468 |
| SEQ. ID. NO. 25943 | 487-ValValGlyLysGlyAsnAsn-493 |
| SEQ. ID. NO. 25944 | 513-PheThrAspSerGluGlyThr-519 |
| SEQ. ID. NO. 25945 | 533-AlaGlyIleArgAlaLysThrArgPheAlaLeu-543 |
| SEQ. ID. NO. 25946 | 559-HisArgSerLysSerPheGlyValGluMetAspGlyGluLysGlnThrLeuAla-576 |
| SEQ. ID. NO. 25947 | 579-ThrAlaLeuGluGly-583 |
| SEQ. ID. NO. 25948 | 600-GlyTyrGlyLysArgThrAspGlyAspLysGluAlaAlaLeu-613 |
| a992 | |
| AMPHI Regions - AMPHI | |
| SEQ. ID. NO. 25949 | 6-ArgHisLeuLysAsnMetGlnIleLysLysIleMetLysTrp-19 |
| SEQ. ID. NO. 25950 | 24-LeuSerLeuLeuGlyAlaLeuGlyTyr-32 |
| SEQ. ID. NO. 25951 | 45-AlaValLeuAspValLeuGlyAlaAla-53 |
| SEQ. ID. NO. 25952 | 72-HisArgTyrThrGlyThrValSerLysValTyr-82 |
| SEQ. ID. NO. 25953 | 158-GlnValGlnAspGly-162 |
| SEQ. ID. NO. 25954 | 179-AspPheAlaAspTyr-183 |
| Antigenic Index - Jameson-Wolf | |
| SEQ. ID. NO. 25955 | 1-MetPheArgArgHisArgHisLeuLys-9 |
| SEQ. ID. NO. 25956 | 34-GlyTyrGlySerGluAlaValArg-41 |
| SEQ. ID. NO. 25957 | 52-AlaAlaGlyAspAlaGlySerAspAlaProAlaArgArgArgAlaSerAlaLysSerGlyHisArgTyrThr-75 |
| SEQ. ID. NO. 25958 | 79-SerLysValTyrAspGlyAspThr-86 |
| SEQ. ID. NO. 25959 | 90-IleAspGlyAspGlyAlaLysHisLysIle-99 |
| SEQ. ID. NO. 25960 | 105-AspAlaProGluMetLysGlnAlaTyrGlyThrArgSerArgAspAsnLeuArgAlaAlaAlaGluGlyArgLysValSer-131 |
| SEQ. ID. NO. 25961 | 134-ValPheAspThrAspArgTyrGlnArgGluValAla-145 |

TABLE 1-continued

| | |
|---|---|
| SEQ. ID. NO. 25962 | 148-SerValGlyLysThrAspLeuAsn-155 |
| SEQ. ID. NO. 25963 | 168-LysSerTyrAlaLysGluGlnGlnAspLysAlaAspPhe-180 |
| SEQ. ID. NO. 25964 | 187-GlnIleGlnAlaGluArgGluArgLysGlyLeuTrpLysAlaLysAsnProGlnAlaPro-206 |
| SEQ. ID. NO. 25965 | 208-AlaTyrArgArgAlaGlyArgSerGlyGlyGlyAsnLysAspTrpMetAsp-224 |
| Hydrophilic Regions - Hopp-Woods | |
| SEQ. ID. NO. 25966 | 1-MetPheArgArgHisArgHisLeuLys-9 |
| SEQ. ID. NO. 25967 | 54-GlyAspAlaGlySerAspAlaProAlaArgArgArgAlaSerAlaLysSerGlyHisArg-73 |
| SEQ. ID. NO. 25968 | 90-IleAspGlyAspGlyAlaLysHisLysIle-99 |
| SEQ. ID. NO. 25969 | 105-AspAlaProGluMetLysGln-111 |
| SEQ. ID. NO. 25970 | 113-TyrGlyThrArgSerArgAspAsnLeuArgAlaAlaAlaGluGlyArgLysValSer-131 |
| SEQ. ID. NO. 25971 | 134-ValPheAspThrAspArgTyrGlnArgGluValAla-145 |
| SEQ. ID. NO. 25972 | 148-SerValGlyLysThrAspLeu-154 |
| SEQ. ID. NO. 25973 | 169-SerTyrAlaLysGluGlnGlnAspLysAlaAspPhe-180 |
| SEQ. ID. NO. 25974 | 187-GlnIleGlnAlaGluArgGluArgLysGlyLeuTrpLysAlaLysAsnPro-203 |
| SEQ. ID. NO. 25975 | 211-ArgAlaGlyArgSerGlyGlyGlyAsnLysAspTrpMet-223 |
| a993 | |
| AMPHI Regions - AMPHI | |
| SEQ. ID. NO. 25976 | 6-SerSerPheGlnGlyProLeuAspLeuLeuLeu-16 |
| SEQ. ID. NO. 25977 | 35-ThrGluGlnTyrLeuHisTyrIleAlaGlnIle-45 |
| SEQ. ID. NO. 25978 | 105-GlyLeuAspAlaLeuProArgAla-112 |
| SEQ. ID. NO. 25979 | 136-IleThrAspLeuThrGlnAlaTrpLeuSer-145 |
| SEQ. ID. NO. 25980 | 152-HisThrArgSerHisGluValIle-159 |
| SEQ. ID. NO. 25981 | 169-MetThrAlaIleLeuArgArgLeuAsnLysHisGlyIleCysArgPheHisAspLeuPheAsnProGlu-191 |
| SEQ. ID. NO. 25982 | 199-ValAsnPheIleAlaLeuLeu-205 |
| Antigenic Index - Jameson-Wolf | |
| SEQ. ID. NO. 25983 | 7-SerPheGlnGlyProLeu-12 |
| SEQ. ID. NO. 25984 | 20-ArgLysGlnAsnIleAsp-25 |
| SEQ. ID. NO. 25985 | 70-LeuLeuLeuProArgThrGluThrValGluAspGluGluAlaAspProArgAlaGluLeuValArg-91 |
| SEQ. ID. NO. 25986 | 108-AlaLeuProArgAlaGlyArgAspPhe-116 |
| SEQ. ID. NO. 25987 | 148-SerArgAlaLysHisThrArgSerHisGluValIleLysGluThrIleSer-164 |
| SEQ. ID. NO. 25988 | 174-ArgArgLeuAsnLysHisGlyIle-181 |
| SEQ. ID. NO. 25989 | 188-PheAsnProGluGlnGly-193 |
| SEQ. ID. NO. 25990 | 207-LeuAlaLysGluGlyLeu-212 |
| SEQ. ID. NO. 25991 | 228-LeuAsnHisGluGlyAlaHisSerAspGlyIleSerGlyThrArgGlyGlyArgAspValPhe-248 |
| Hydrophilic Regions - Hopp-Woods | |
| SEQ. ID. NO. 25992 | 20-ArgLysGlnAsnIleAsp-25 |
| SEQ. ID. NO. 25993 | 70-LeuLeuLeuProArgThrGluThrValGluAspGluGluAlaAspProArgAlaGluLeuValArg-91 |
| SEQ. ID. NO. 25994 | 108-AlaLeuProArgAlaGlyArg-114 |
| SEQ. ID. NO. 25995 | 148-SerArgAlaLysHisThrArgSerHisGluValIleLysGluThrIleSer-164 |
| SEQ. ID. NO. 25996 | 174-ArgArgLeuAsnLys-178 |
| SEQ. ID. NO. 25997 | 207-LeuAlaLysGluGlyLeu-212 |
| SEQ. ID. NO. 25998 | 232-GlyAlaHisSerAspGlyIleSerGlyThrArgGlyGlyArgAspValPhe-248 |
| a996 | |
| AMPHI Regions - AMPHI | |
| SEQ. ID. NO. 25999 | 21-LysSerAlaArgThrHisAlaLysIlePro-30 |
| SEQ. ID. NO. 26000 | 50-ProGlyGluSerTyrProAlaGlnLeuGlnLysLeuThrGlyTrpAsn-65 |
| SEQ. ID. NO. 26001 | 75-ThrSerAlaGlnAlaLeuSerArgLeuProAla-85 |
| SEQ. ID. NO. 26002 | 104-LeuArgLysValProLysGlu-110 |
| SEQ. ID. NO. 26003 | 115-AsnIleAlaLysIleIleGluThrValGlnLys-125 |
| SEQ. ID. NO. 26004 | 140-LeuGlyAlaLeuPheGlyHisLeuSerAsp-149 |
| SEQ. ID. NO. 26005 | 167-GlyAlaTrpAlaGlu-171 |
| SEQ. ID. NO. 26006 | 186-AsnGlyLysGlyTyrArgLysPheAlaGluAspLeuAsnGlnPheLeuArgLysGlnGlyPhe-206 |
| Antigenic Index - Jameson-Wolf | |
| SEQ. ID. NO. 26007 | 1-MetAsnArgArgThrPhe-6 |
| SEQ. ID. NO. 26008 | 18-CysGlyArgLysSerAlaArgThrHisAlaLysIleProGluGlySerThr-34 |
| SEQ. ID. NO. 26009 | 46-TyrGlyAlaAsnProGlyGluSerTyrPro-55 |
| SEQ. ID. NO. 26010 | 69-GlyGlyValSerGlyAspThrSerAla-77 |
| SEQ. ID. NO. 26011 | 87-LeuAlaArgLysProLys-92 |
| SEQ. ID. NO. 26012 | 99-GlyGlyAsnAspPheLeuArgLysValProLysGluGlnThrArgAlaAsnIle-116 |
| SEQ. ID. NO. 26013 | 121-GluThrValGlnLysGluAsnIlePro-129 |
| SEQ. ID. NO. 26014 | 148-SerAspHisProLeuTyrGluAspLeuSerGluGluTyrGly-161 |
| SEQ. ID. NO. 26015 | 173-LeuGlyAspAsnAsnLeuLysSerAspGlnIleHisAlaAsnGlyLysGlyTyrArgLysPheAlaGluAspLeuAsnGlnPheLeuArgLysGln GlyPheArg-207 |
| Hydrophilic Regions - Hopp-Woods | |
| SEQ. ID. NO. 26016 | 18-CysGlyArgLysSerAlaArgThrHisAlaLysIleProGlu-31 |
| SEQ. ID. NO. 26017 | 49-AsnProGlyGluSerTyr-54 |
| SEQ. ID. NO. 26018 | 71-ValSerGlyAspThrSerAla-77 |
| SEQ. ID. NO. 26019 | 87-LeuAlaArgLysProLys-92 |
| SEQ. ID. NO. 26020 | 102-AspPheLeuArgLysValProLysGluGlnThrArgAlaAsnIle-116 |
| SEQ. ID. NO. 26021 | 121-GluThrValGlnLysGluAsnIle-128 |
| SEQ. ID. NO. 26022 | 154-GluAspLeuSerGluGluTyrGly-161 |
| SEQ. ID. NO. 26023 | 176-AsnAsnLeuLysSerAspGlnIleHisAlaAsn-186 |
| SEQ. ID. NO. 26024 | 188-LysGlyTyrArgLysPheAlaGluAspLeuAsnGlnPheLeuArg-202 |
| a997 | |
| AMPHI Regions - AMPHI | |
| SEQ. ID. NO. 26025 | 18-TrpAlaGlyLeuSerAlaAlaVal-25 |
| SEQ. ID. NO. 26026 | 70-TyrArgGlyValLeuArgLeuMetLysThrIleGlySerAsp-83 |
| SEQ. ID. NO. 26027 | 107-ProLeuProAlaProLeuHisIle-114 |
| SEQ. ID. NO. 26028 | 123-ArgValProSerAlaPheLysAlaLysLeuLeuAlaAspMetSerAspLeuGlnLysSerAlaArgLeuGly-146 |
| SEQ. ID. NO. 26029 | 164-AlaAlaValMetGlnPheTrpGlnProLeuValTrpGly-176 |

TABLE 1-continued

| | |
|---|---|
| SEQ. ID. NO. 26030 | 189-ValLeuCysAsnValLeuSerAsp-196 |
| SEQ. ID. NO. 26031 | 222-AlaLeuAlaGluLeuGlnArg-228 |
| SEQ. ID. NO. 26032 | 241-ArgLeuAsnThrLeuPro-246 |
| SEQ. ID. NO. 26033 | 275-GluGlyThrProGluHisValGlnThrAla-284 |
| SEQ. ID. NO. 26034 | 300-TyrAlaGluProValArgLeuProAlaProLeuThrGlyLeuAlaAspGly-316 |
| SEQ. ID. NO. 26035 | 354-AspLysValHisAlaAspLeuLysArgIleLeuProHisLeu-367 |
| SEQ. ID. NO. 26036 | 369-GluProGluAlaVal-373 |
| Antigenic Index - Jameson-Wolf | |
| SEQ. ID. NO. 26037 | 3-AsnThrProHisProArgProLysIle-11 |
| SEQ. ID. NO. 26038 | 37-GluAlaGlyArgGlnAlaGlyGlyArgAlaArgAla-48 |
| SEQ. ID. NO. 26039 | 50-AlaGlyAsnThrAspGlyPheGly-57 |
| SEQ. ID. NO. 26040 | 78-LysThrIleGlySerAspProHisAla-86 |
| SEQ. ID. NO. 26041 | 122-ArgArgValProSerAlaPheLys-129 |
| SEQ. ID. NO. 26042 | 132-LeuLeuAlaAspMetSerAspLeuGlnLysSerAlaArgLeuGlyGlnProAspThrThr-151 |
| SEQ. ID. NO. 26043 | 156-LeuLysGlnArgAsnValProArg-163 |
| SEQ. ID. NO. 26044 | 180-ThrProLeuGluThrAlaSer-186 |
| SEQ. ID. NO. 26045 | 197-GlyValLeuThrLysLysSerGlySerAspTyrLeuLeuProLysGlnAspLeu-214 |
| SEQ. ID. NO. 26046 | 225-GluLeuGlnArgLeuGlyAlaAspIleArgLeuGluThrArgIleCysArg-241 |
| SEQ. ID. NO. 26047 | 243-AsnThrLeuProAspGlyLysVal-250 |
| SEQ. ID. NO. 26048 | 273-LeuProGluGlyThrProGluHisVal-281 |
| SEQ. ID. NO. 26049 | 312-GlyLeuAlaAspGlyThr-317 |
| SEQ. ID. NO. 26050 | 323-CysArgGlyArgLeuGlyLeuProGluAsnGluVal-334 |
| SEQ. ID. NO. 26051 | 340-ValSerAspArgValGlyAla-346 |
| SEQ. ID. NO. 26052 | 356-ValHisAlaAspLeuLysArgIleLeu-364 |
| SEQ. ID. NO. 26053 | 367-LeuGlyGluProGluAlaValArgValIleThrGluLysArgAlaThrThrAlaAlaAspAlaProProProAspLeu-392 |
| SEQ. ID. NO. 26054 | 402-ProAlaGlyAspTyrLeuHisProAspTyrProAla-413 |
| Hydrophilic Regions - Hopp-Woods | |
| SEQ. ID. NO. 26055 | 5-ProHisProArgProLysIle-11 |
| SEQ. ID. NO. 26056 | 37-GluAlaGlyArgGlnAlaGlyGlyArgAlaArgAla-48 |
| SEQ. ID. NO. 26057 | 80-IleGlySerAspPro-84 |
| SEQ. ID. NO. 26058 | 122-ArgArgValProSer-126 |
| SEQ. ID. NO. 26059 | 132-LeuLeuAlaAspMetSerAspLeuGlnLysSerAlaArgLeuGlyGlnProAspThrThr-151 |
| SEQ. ID. NO. 26060 | 198-ValLeuThrLysLysSerGlySer-205 |
| SEQ. ID. NO. 26061 | 208-LeuLeuProLysGlnAspLeu-214 |
| SEQ. ID. NO. 26062 | 225-GluLeuGlnArgLeuGlyAlaAspIleArgLeuGluThrArgIleCysArg-241 |
| SEQ. ID. NO. 26063 | 246-ProAspGlyLysVal-250 |
| SEQ. ID. NO. 26064 | 276-GlyThrProGluHisVal-281 |
| SEQ. ID. NO. 26065 | 325-GlyArgLeuGlyLeuProGluAsnGluVal-334 |
| SEQ. ID. NO. 26066 | 340-ValSerAspArgValGly-345 |
| SEQ. ID. NO. 26067 | 356-ValHisAlaAspLeuLysArgIleLeu-364 |
| SEQ. ID. NO. 26068 | 368-GlyGluProGluAlaValArgValIleThrGluLysArgAlaThrThrAlaAlaAspAlaProProPro-390 |
| g001 | |
| AMPHI Regions - AMPHI | |
| SEQ. ID. NO. 26069 | 7-AlaAlaArgArgValSer-12 |
| SEQ. ID. NO. 26070 | 17-SerGlyArgAlaCys-21 |
| SEQ. ID. NO. 26071 | 67-AlaArgPhePheGlySerValCysAsnSerAla-77 |
| Antigenic Index - Jameson-Wolf | |
| SEQ. ID. NO. 26072 | 3-ProGlnGlyLysAlaAlaArgArgValSerAlaAsnGluValSerGlyArgAlaCysAla-22 |
| SEQ. ID. NO. 26073 | 31-ThrLeuProLysArgAspThrLeuAsnGlySerGlyThr-43 |
| SEQ. ID. NO. 26074 | 53-ProArgSerLeuArgSerLysSerThr-61 |
| SEQ. ID. NO. 26075 | 68-ArgPhePheGlySer-72 |
| SEQ. ID. NO. 26076 | 74-CysAsnSerAlaAlaArgArgSerSerCysProSerProLysIleGly-89 |
| SEQ. ID. NO. 26077 | 100-ValProSerGluAlaMetLeuArgLysSerSerGlyGluLysHisSerVal-116 |
| SEQ. ID. NO. 26078 | 119-AspCysProAlaSerSerGlyArgTrpAspAsnThrAla-131 |
| Hydrophilic Regions - Hopp-Woods | |
| SEQ. ID. NO. 26079 | 5-GlyLysAlaAlaArgArgValSerAlaAsnGluValSerGly-18 |
| SEQ. ID. NO. 26080 | 32-LeuProLysArgAspThrLeuAsn-39 |
| SEQ. ID. NO. 26081 | 54-ArgSerLeuArgSerLysSer-60 |
| SEQ. ID. NO. 26082 | 77-AlaAlaArgArgSerSerCysProSerProLys-87 |
| SEQ. ID. NO. 26083 | 104-AlaMetLeuArgLysSerSerGlyGluLysHisSerVal-116 |
| SEQ. ID. NO. 26084 | 125-GlyArgTrpAspAsn-129 |
| g003 | |
| AMPHI Regions - AMPHI | |
| SEQ. ID. NO. 26085 | 72-AsnGlnValValLeu-76 |
| SEQ. ID. NO. 26086 | 82-ValValGluValPheGlnArg-88 |
| SEQ. ID. NO. 26087 | 150-ValGlnAlaGluPheValGlyIleValGlyHisPheAspGlyLeuGlyMet-166 |
| SEQ. ID. NO. 26088 | 173-HisPhePheValArgValPheArg-180 |
| Antigenic Index - Jameson-Wolf | |
| SEQ. ID. NO. 26089 | 104-PheGluGlyGlyGlyAspAspGlyPhe-112 |
| SEQ. ID. NO. 26090 | 137-GlyArgIleAsnAspAlaGluIleIle-145 |
| SEQ. ID. NO. 26091 | 204-ProLysAlaAlaAlaGlyGluValAsnGly-213 |
| SEQ. ID. NO. 26092 | 215-ArgValHisAspCys-219 |
| Hydrophilic Regions - Hopp-Woods | |
| SEQ. ID. NO. 26093 | 106-GlyGlyGlyAspAspGlyPhe-112 |
| SEQ. ID. NO. 26094 | 137-GlyArgIleAsnAspAlaGluIleIle-145 |

TABLE 1-continued

SEQ. ID. NO. 26095 205-LysAlaAlaAlaGlyGluValAsnGly-213
SEQ. ID. NO. 26096 215-ArgValHisAspCys-219
g005
AMPHI Regions - AMPHI
SEQ. ID. NO. 26097 16-IleGlnSerMetTrpLysGlu-22
SEQ. ID. NO. 26098 32-LeuGluLeuLeuThrValPheGlyAlaIleAla-42
SEQ. ID. NO. 26099 62-LeuThrAspPheSerGluAsnTyr-69
SEQ. ID. NO. 26100 107-ArgLeuLysGluGlyGlyGluLysSerAlaGlu-117
SEQ. ID. NO. 26101 177-GlnLeuArgArgLeuArg-182
SEQ. ID. NO. 26102 213-AlaProPheAlaValIleGlySerValGlyValValAlaGluValProAsnIleHisArgLeuLeuLysLys-236
SEQ. ID. NO. 26103 249-PheLysArgThrVal-253
SEQ. ID. NO. 26104 274-ThrHisGlnLeuPheLysGln-280
SEQ. ID. NO. 26105 308-LeuAsnLeuIleAspGluIleSerThr-316
SEQ. ID. NO. 26106 320-LeuLeuLeuLysAlaPhe-325
Antigenic Index - Jameson-Wolf
SEQ. ID. NO. 26107 1-MetGlyMetAspAsn-5
SEQ. ID. NO. 26108 10-MetProGluGlnGluGluIleGlnSerMetTrp-20
SEQ. ID. NO. 26109 50-GlnSerLysLysGlnSerGluSerGlySer-59
SEQ. ID. NO. 26110 64-AspPheSerGluAsnTyrLysLysGlnArgGlnSerPhe-76
SEQ. ID. NO. 26111 82-SerGluGluGluThrLysHisGlnGluLysLysGluLysLysLysGluLysAlaGluAlaLysAlaGluLysLysArgLeuLysGluGlyGlyGluLys SerAlaGluThrGlnLysSerArg-122
SEQ. ID. NO. 26112 138-GluSerLeuArgHisGluIle-144
SEQ. ID. NO. 26113 151-AlaLysProGluAspGluValLeuLeu-159
SEQ. ID. NO. 26114 161-LeuGluSerProGlyGlyVal-167
SEQ. ID. NO. 26115 177-GlnLeuArgArgLeuArgGluArgAsnIle-186
SEQ. ID. NO. 26116 191-AlaValAspLysValAlaAla-197
SEQ. ID. NO. 26117 232-ArgLeuLeuLysLysHisAspIleAspVal-241
SEQ. ID. NO. 26118 247-GlyGluPheLysArgThr-252
SEQ. ID. NO. 26119 258-GluAsnThrGluLysGlyLysGlnLysPheArgGlnGluLeuGluGluThrHisGln-276
SEQ. ID. NO. 26120 281-PheValSerGluAsnArgProGlyLeuAspIleGluLysIleAlaThr-296
SEQ. ID. NO. 26121 312-AspGluIleSerThrSerAspAspLeuLeu-321
SEQ. ID. NO. 26122 325-PheGluAsnLysGlnValIle-331
SEQ. ID. NO. 26123 334-LysTyrGlnGluLysArgSerLeuIle-342
SEQ. ID. NO. 26124 351-AlaSerValGluLysLeuPhe-357
SEQ. ID. NO. 26125 361-ValAsnArgArgAlaAspVal-367
Hydrophilic Regions - Hopp-Woods
SEQ. ID. NO. 26126 10-MetProGluGlnGluGluIleGlnSerMetTrp-20
SEQ. ID. NO. 26127 50-GlnSerLysLysGlnSerGluSerGly-58
SEQ. ID. NO. 26128 64-AspPheSerGluAsnTyrLysLysGlnArgGlnSerPhe-76
SEQ. ID. NO. 26129 82-SerGluGluGluThrLysHisGlnGluLysLysGluLysLysLysGluLysAlaGluAlaLysAlaGluLysLysArgLeuLysGluGlyGlyGluLys SerAlaGluThrGlnLysSerArg-122
SEQ. ID. NO. 26130 138-GluSerLeuArgHisGluIle-144
SEQ. ID. NO. 26131 151-AlaLysProGluAspGluValLeuLeu-159
SEQ. ID. NO. 26132 161-LeuGluSerProGly-165
SEQ. ID. NO. 26133 177-GlnLeuArgArgLeuArgGluArgAsnIle-186
SEQ. ID. NO. 26134 191-AlaValAspLysValAlaAla-197
SEQ. ID. NO. 26135 232-ArgLeuLeuLysLysHisAspIleAspVal-241
SEQ. ID. NO. 26136 247-GlyGluPheLysArg-251
SEQ. ID. NO. 26137 258-GluAsnThrGluLysGlyLysGlnLysPheArgGlnGluLeuGluGluThrHisGln-276
SEQ. ID. NO. 26138 281-PheValSerGluAsnArgProGlyLeuAspIleGluLysIleAlaThr-296
SEQ. ID. NO. 26139 312-AspGluIleSerThrSerAspAspLeuLeu-321
SEQ. ID. NO. 26140 325-PheGluAsnLysGlnValIle-331
SEQ. ID. NO. 26141 334-LysTyrGlnGluLysArgSerLeuIle-342
SEQ. ID. NO. 26142 351-AlaSerValGluLysLeuPhe-357
SEQ. ID. NO. 26143 361-ValAsnArgArgAlaAspVal-367
g006-1
AMPHI Regions - AMPHI
SEQ. ID. NO. 26144 6-LysHisIleAlaLysThrHisArgLysArg-15
SEQ. ID. NO. 26145 19-ThrPheSerProValGlyLeuGluAsnLeuLeu-29
SEQ. ID. NO. 26146 48-ArgValTrpGlnAlaLeuLeuTyrAlaLeuValValPhe-60
SEQ. ID. NO. 26147 69-ArgArgIleAlaAspThrArgThrPheThrArgIleTyrThrGlu-83
SEQ. ID. NO. 26148 111-GluPheValSerPhePheGlu-117
SEQ. ID. NO. 26149 125-ThrSerValValSerIlePheGlyAlaCysIleMetLeuLeu-138
SEQ. ID. NO. 26150 195-HisTyrGlyLeuValSerArgLeu-202
SEQ. ID. NO. 26151 236-GlyTyrGlySerAlaGlyHisIleTyrSer-245
SEQ. ID. NO. 26152 257-LeuAspAspValProArgLeuValGluGlnTyrSerAsnLeuLysAspIle-273
Antigenic Index - Jameson-Wolf
SEQ. ID. NO. 26153 6-LysHisIleAlaLysThrHisArgLysArgLeu-16
SEQ. ID. NO. 26154 67-AlaAlaArgArgIleAlaAspThrArgThrPheThr-78
SEQ. ID. NO. 26155 90-LeuGluGlnArgGlnArgGlnValProHisSer-100
SEQ. ID. NO. 26156 173-LeuAsnAsnSerLeuGluArgAspAsnHisPheIleArgLysGlyAspGluArgGlnLeuTyr-193
SEQ. ID. NO. 26157 206-IleSerAsnArgGluAlaPhe-212
SEQ. ID. NO. 26158 256-SerLeuAspAspValProArgLeuValGluGlnTyrSerAsnLeuLysAspIleGlyGlnArgIleGluTrpSerGluArgAsnIleLysAlaGlyThr-288
Hydrophilic Regions - Hopp-Woods
SEQ. ID. NO. 26159 6-LysHisIleAlaLysThrHisArgLysArgLeu-16
SEQ. ID. NO. 26160 67-AlaAlaArgArgIleAlaAspThrArgThrPhe-77
SEQ. ID. NO. 26161 90-LeuGluGlnArgGlnArgGlnValPro-98
SEQ. ID. NO. 26162 175-AsnSerLeuGluArgAspAsnHisPheIleArgLysGlyAspGluArgGlnLeu-192
SEQ. ID. NO. 26163 206-IleSerAsnArgGluAla-211

TABLE 1-continued

SEQ. ID. NO. 26164 256-SerLeuAspAspValProArgLeuValGlu-265
SEQ. ID. NO. 26165 268-SerAsnLeuLysAspIleGlyGln-275
SEQ. ID. NO. 26166 277-IleGluTrpSerGluArgAsnIleLysAlaGlyThr-288
g007-1
AMPHI Regions - AMPHI
SEQ. ID. NO. 26167 71-HisSerMetValLysGlyIleAsn-78
SEQ. ID. NO. 26168 105-ValAlaThrTyrIleMetAsnAlaPheAspAsnGlyGlyGly-118
Antigenic Index - Jameson-Wolf
SEQ. ID. NO. 26169 1-MetAsnThrThrArgLeuProThr-8
SEQ. ID. NO. 26170 20-SerAlaAlaAspAsnSerIleMetThrLysGlyGlnLysValTyrGluSerAsnCys-38
SEQ. ID. NO. 26171 41-CysHisGlyLysLysGlyGluGlyArgGlyThrAlaPhePro-54
SEQ. ID. NO. 26172 56-LeuPheArgSerAspTyrIleMetAsnLysPro-66
SEQ. ID. NO. 26173 81-IleLysValAsnGlyLysThrTyrAsnGly-90
SEQ. ID. NO. 26174 98-SerAspAlaAspIle-102
SEQ. ID. NO. 26175 112-AlaPheAspAsnGlyGlyGlySerValThrGluLysAspValLysGlnAlaLysGlyLysLysAsn-133
Hydrophilic Regions - Hopp-Woods
SEQ. ID. NO. 26176 26-IleMetThrLysGlyGlnLysValTyrGlu-35
SEQ. ID. NO. 26177 42-HisGlyLysLysGlyGluGlyArgGly-50
SEQ. ID. NO. 26178 98-SerAspAlaAspIle-102
SEQ. ID. NO. 26179 119-SerValThrGluLysAspValLysGlnAlaLysGlyLysLyAsn-133
g008
AMPHI Regions - AMPHI
SEQ. ID. NO. 26180 15-LeuAspAsnProAlaGlnGlnIleArgGlyAlaLeuAspAlaLeuSer-30
SEQ. ID. NO. 26181 54-GlnProAspPheIleAsnAlaVal-61
SEQ. ID. NO. 26182 63-ThrValSerThrThr-67
SEQ. ID. NO. 26183 69-AspGlyIleAlaLeuLeuAlaGluLeuAsnArg-79
SEQ. ID. NO. 26184 90-PheArgAsnAlaPro-94
SEQ. ID. NO. 26185 129-ArgProLeuAlaGluIleLeuProAsp-137
SEQ. ID. NO. 26186 140-LeuGlyLysTyrGlyLysValValGluLeuSerLysArgLeuGly-154
Antigenic Index - Jameson-Wolf
SEQ. ID. NO. 26187 1-MetAsnAsnArgHis-5
SEQ. ID. NO. 26188 12-GlySerAsnLeuAspAsnProAlaGlnGlnIleArgGlyAlaLeu-26
SEQ. ID. NO. 26189 29-LeuSerSerHisProAspIleArgLeuGluGln-39
SEQ. ID. NO. 26190 49-ValGlyTyrAspAsnGlnPrAspPhe-57
SEQ. ID. NO. 26191 76-GluLeuAsnArgIleGluAlaAspPheGlyArgGluArgSerPheArgAsnAlaProArgThrLeuAspLeuAspIleIleAspPheAspGlyIleSerSer AspAspProArgLeuThrLeuProHisProArgAlaHisGluArgSerPheVal-127
SEQ. ID. NO. 26192 139-IleLeuGlyLysTyrGlyLysValValGluLeuSerLysArgLeuGlyAsnGlnGlyIle-158
SEQ. ID. NO. 26193 160-LeuLeuProAspArg-164
Hydrophilic Regions - Hopp-Woods
SEQ. ID. NO. 26194 14-AsnLeuAspAsnProAlaGlnGlnIle-22
SEQ. ID. NO. 26195 33-ProAspIleArgLeuGluGln-39
SEQ. ID. NO. 26196 76-GluLeuAsnArgIleGluAlaAspPheGlyArgGluArgSerPheArgAsnAlaProArgThrLeuAsp-98
SEQ. ID. NO. 26197 105-AspGlyIleSerSerAspAspProArgLeu-114
SEQ. ID. NO. 26198 120-ArgAlaHisGluArgSerPheVal-127
SEQ. ID. NO. 26199 147-ValGluLeuSerLysArgLeuGly-154
SEQ. ID. NO. 26200 160-LeuLeuProAspArg-164
g009
Antigenic Index - Jameson-Wolf
SEQ. ID. NO. 26201 6-ValAlaPheGluArgHisHisHisLysSerLysAlaGluGlnAsnThrHisArgArgAlaAspAlaGluIleAlaGlu-31
SEQ. ID. NO. 26202 37-AsnGlnHisThrGlnAlaArgAsnGlnSerVal-47
SEQ. ID. NO. 26203 57-PheSerAspLysVal-61
SEQ. ID. NO. 26204 77-AlaAspGlyGlyLysThrTrpGlnLysPro-86
Hydrophilic Regions - Hopp-Woods
SEQ. ID. NO. 26205 6-ValAlaPheGluArgHisHisHisLysSerLysAlaGluGlnAsnThrHisArgArgAlaAspAlaGluIleAlaGlu-31
SEQ. ID. NO. 26206 40-ThrGlnAlaArgAsnGlnSer-46
SEQ. ID. NO. 26207 78-AspGlyGlyLysThrTrpGln-84
g010-1
AMPHI Regions - AMPHI
SEQ. ID. NO. 26208 54-SerAlaSerLeuGly-58
SEQ. ID. NO. 26209 70-TyrAspThrValLysGly-75
SEQ. ID. NO. 26210 115-TyrGlnArgProPheGlyGlyHis-122
SEQ. ID. NO. 26211 125-GluHisGlyLysArgAlaVal-131
SEQ. ID. NO. 26212 146-LeuHisThrLeuTyrGln-151
SEQ. ID. NO. 26213 210-AlaSerSerThrAsn-214
SEQ. ID. NO. 26214 216-TyrMetAsnThrGlyAspGly-222
SEQ. ID. NO. 26215 275-ArgTyrAlaProThrValLys-281
SEQ. ID. NO. 26216 322-IleMetGluLysLeuProGlyIleArg-330
SEQ. ID. NO. 26217 338-GlyIleAspProIleLysAspProIlePro-347
SEQ. ID. NO. 26218 357-GlyGlyIleProThrAsnTyrHis-364
Antigenic Index - Jameson-Wolf
SEQ. ID. NO. 26219 15-GlyGlyGlyAlaGly-19
SEQ. ID. NO. 26220 26-LeuSerLysSerGlyLeu-31
SEQ. ID. NO. 26221 40-PheProThrArgSerHis-45
SEQ. ID. NO. 26222 59-AsnValGlnGluAspArgTrpAsp-66
SEQ. ID. NO. 26223 71-AspThrValLysGlySerAspTrpLeuGlyAspGlnAspAlaIle-85
SEQ. ID. NO. 26224 104-MetProPheAspArgValGluSerGlyLysIleTyrGlnArgProPheGly-120
SEQ. ID. NO. 26225 123-ThrAlaGluHisGlyLysArgAlaValGluArgAlaCysAlaValAlaAspArgThrGly-142
SEQ. ID. NO. 26226 152-GlnAsnValArgAlaAsnThr-158
SEQ. ID. NO. 26227 168-AspLeuIleArgAspGluAsnGlyAspVal-177
SEQ. ID. NO. 26228 183-MetGluMetGluThrGlyGlu-189

TABLE 1-continued

| | |
|---|---|
| SEQ. ID. NO. 26229 | 202-ThrGlyGlyGlyGlyArgIle-208 |
| SEQ. ID. NO. 26230 | 218-AsnThrGlyAspGly-222 |
| SEQ. ID. NO. 26231 | 231-IleProLeuGluAspMetGlu-237 |
| SEQ. ID. NO. 26232 | 255-GluGlyValArgGlyGluGlyGlyIle-263 |
| SEQ. ID. NO. 26233 | 266-AsnAlaAspGlyGluArgPheMetGlu-274 |
| SEQ. ID. NO. 26234 | 276-TyrAlaProThrValLysAspLeuAlaSerArgAspValValSer-290 |
| SEQ. ID. NO. 26235 | 297-IleTyrGluGlyArgGlyCysGlyLysAsnLysAspHisVal-310 |
| SEQ. ID. NO. 26236 | 315-AspHisIleGlyAlaGluLysIleMetGluLysLeuProGlyIleArgGluIleSer-333 |
| SEQ. ID. NO. 26237 | 338-GlyIleAspProIleLysAspProIle-346 |
| SEQ. ID. NO. 26238 | 368-ValValProGlnGlyAspGluTyrGluValProVal-379 |
| SEQ. ID. NO. 26239 | 395-GlyAlaAsnArgLeuGlyThrAsnSerLeu-404 |
| SEQ. ID. NO. 26240 | 411-ArgProThrProArg-415 |
| Hydrophilic Regions - Hopp-Woods | |
| SEQ. ID. NO. 26241 | 27-SerLysSerGlyLeu-31 |
| SEQ. ID. NO. 26242 | 59-AsnValGlnGluAspArgTrpAsp-66 |
| SEQ. ID. NO. 26243 | 71-AspThrValLysGly-75 |
| SEQ. ID. NO. 26244 | 77-AspTrpLeuGlyAspGlnAspAlaIle-85 |
| SEQ. ID. NO. 26245 | 105-ProPheAspArgValGluSerGlyLysIleTyr-115 |
| SEQ. ID. NO. 26246 | 123-ThrAlaGluHisGlyLysArgAlaValGluArgAlaCysAlaValAlaAspArgThrGly-142 |
| SEQ. ID. NO. 26247 | 168-AspLeuIleArgAspGluAsnGlyAsp-176 |
| SEQ. ID. NO. 26248 | 183-MetGluMetGluThrGlyGlu-189 |
| SEQ. ID. NO. 26249 | 231-IleProLeuGluAspMetGlu-237 |
| SEQ. ID. NO. 26250 | 255-GluGlyValArgGlyGluGly-261 |
| SEQ. ID. NO. 26251 | 267-AlaAspGlyGluArgPheMetGlu-274 |
| SEQ. ID. NO. 26252 | 276-TyrAlaProThrValLysAspLeuAlaSerArgAspValValSer-290 |
| SEQ. ID. NO. 26253 | 297-IleTyrGluGlyArgGlyCysGlyLysAsnLysAspHisVal-310 |
| SEQ. ID. NO. 26254 | 315-AspHisIleGlyAlaGluLysIleMetGluLysLeuProGlyIleArgGluIleSer-333 |
| SEQ. ID. NO. 26255 | 340-AspProIleLysAspProIle-346 |
| SEQ. ID. NO. 26256 | 371-GlnGlyAspGluTyrGluValProVal-379 |
| g011 | |
| AMPHI Regions - AMPHI | |
| SEQ. ID. NO. 26257 | 58-IleArgLeuIleAsnAlaAla-64 |
| SEQ. ID. NO. 26258 | 83-AlaIleLeuThrLys-87 |
| SEQ. ID. NO. 26259 | 116-AspValLeuHisArgTyrLeuProGlnMetLeuSerAlaGly-129 |
| SEQ. ID. NO. 26260 | 142-ThrGlyAlaAlaGlyMetAlaAspMetGlyLysValMet-154 |
| Antigenic Index - Jameson-Wolf | |
| SEQ. ID. NO. 26261 | 1-MetLysThrHisArgLysThrCysSer-9 |
| SEQ. ID. NO. 26262 | 17-ThrAlaSerLysProAlaValSerIleArgHisProSerGluAspIleMetSerLeuLysThrArgLeuThrGluAspMetLysThrAlaMetArgAlaLysAspGlnVal-53 |
| SEQ. ID. NO. 26263 | 66-LysGlnPheGluValAspGluArgThrGluAlaAspAspAlaLysIle-81 |
| SEQ. ID. NO. 26264 | 88-MetValLysGlnArgLysAspGlyAlaLysIleTyrThrGluAlaGlyArgGlnAspLeuAlaAspLysGluAsnAlaGluIle-115 |
| SEQ. ID. NO. 26265 | 127-SerAlaGlyGluIleArgThrAlaVal-135 |
| SEQ. ID. NO. 26266 | 159-ThrArgLeuAlaGlyLysAlaAspMetGlyGluValAsnLysIleLeu-174 |
| Hydrophilic Regions - Hopp-Woods | |
| SEQ. ID. NO. 26267 | 1-MetLysThrHisArgLysThrCys-8 |
| SEQ. ID. NO. 26268 | 27-HisProSerGluAspIleMetSerLeuLysThrArgLeuThrGluAspMetLysThrAlaMetArgAlaLysAspGlnVal-53 |
| SEQ. ID. NO. 26269 | 66-LysGlnPheGluValAspGluArgThrGluAlaAspAspAlaLysIle-81 |
| SEQ. ID. NO. 26270 | 88-MetValLysGlnArgLysAspGlyAlaLysIleTyrThrGluAlaGlyArgGlnAspLeuAlaAspLysGluAsnAlaGluIle-115 |
| SEQ. ID. NO. 26271 | 129-GlyGluIleArgThrAlaVal-135 |
| SEQ. ID. NO. 26272 | 159-ThrArgLeuAlaGlyLysAlaAspMetGlyGluValAsnLysIleLeu-174 |
| g012-1 | |
| AMPHI Regions - AMPHI | |
| SEQ. ID. NO. 26273 | 18-AspLysLeuLeuGluGlnLeuMetArgPheLeuGlnPheLeuProGluPheLeuPheAlaLeuPheArgIle-41 |
| SEQ. ID. NO. 26274 | 48-ArgAlaLeuLysPheAlaArgArg-55 |
| SEQ. ID. NO. 26275 | 89-AsnAsnPheIleArgHisThr-95 |
| SEQ. ID. NO. 26276 | 100-AlaAlaAlaCysArgAsp-105 |
| SEQ. ID. NO. 26277 | 133-HisAlaAlaArgThrPhe-138 |
| SEQ. ID. NO. 26278 | 160-GlnGlyPheTyrGlyVal-165 |
| SEQ. ID. NO. 26279 | 179-GlyPheLeuArgPheGlyArgPheLeuProAlaLeuLeuGlnThrLeu-194 |
| Antigenic Index - Jameson-Wolf | |
| SEQ. ID. NO. 26280 | 42-PheThrHisLysSerAsnArgAlaLeuLysPheAlaArgArgHisHis-57 |
| SEQ. ID. NO. 26281 | 72-ArgHisPheArgHisHisThrHisArgThrAspAspArgLysArgSerGlyAsnAsnPheIleArgHisThrArg-96 |
| SEQ. ID. NO. 26282 | 102-AlaCysArgAspLeuIleAspGlyAspGlyGlnArgAsn-114 |
| SEQ. ID. NO. 26283 | 119-GlnThrProLysLeuArgSerArgGln-127 |
| SEQ. ID. NO. 26284 | 137-ThrPheGlnSerGluGlnAsnLeu-144 |
| SEQ. ID. NO. 26285 | 147-ArgLeuGlyAsnGlnLysHisArgArgAsnLeuMetThrGln-160 |
| SEQ. ID. NO. 26286 | 173-IleGlnHisLysLysAlaGly-179 |
| Hydrophilic Regions - Hopp-Woods | |
| SEQ. ID. NO. 26287 | 45-LysSerAsnArgAlaLeuLysPheAlaArgArgHisHis-57 |
| SEQ. ID. NO. 26288 | 77-HisThrHisArgThrAspAspArgLysArgSerGly-88 |
| SEQ. ID. NO. 26289 | 102-AlaCysArgAspLeuIleAspGlyAspGlyGlnArg-113 |
| SEQ. ID. NO. 26290 | 121-ProLysLeuArgSerArgGln-127 |

TABLE 1-continued

| | |
|---|---|
| SEQ. ID. NO. 26291 | 149-GlyAsnGlnLysHisArgArgAsnLeu-157 |
| SEQ. ID. NO. 26292 | 173-IleGlnHisLysLysAlaGly-179 |
| g015 | |
| AMPHI Regions - AMPHI | |
| SEQ. ID. NO. 26293 | 36-LeuValGlyPheTrpLysAlaLeuProHis-45 |
| SEQ. ID. NO. 26294 | 107-MetCysCysIleAlaCys-112 |
| Antigenic Index - Jameson-Wolf | |
| SEQ. ID. NO. 26295 | 29-TrpLysAsnProGluLysProLeu-36 |
| SEQ. ID. NO. 26296 | 90-MetArgAlaArgProArgSerThrLys-98 |
| Hydrophilic Regions - Hopp-Woods | |
| SEQ. ID. NO. 26297 | 31-AsnProGluLysProLeu-36 |
| SEQ. ID. NO. 26298 | 90-MetArgAlaArgProArgSerThrLys-98 |
| g018-2 | |
| AMPHI Regions - AMPHI | |
| SEQ. ID. NO. 26299 | 6-IleGlnHisLeuArg-10 |
| SEQ. ID. NO. 26300 | 15-HisLeuMetArgProCysGlnGlnValSerGlnMetPheGly-28 |
| SEQ. ID. NO. 26301 | 152-ArgIleGlyAsnGlyTyr-157 |
| Antigenic Index - Jameson-Wolf | |
| SEQ. ID. NO. 26302 | 1-MetValGluArgHisIleGln-7 |
| SEQ. ID. NO. 26303 | 9-LeuArgAsnGlyHisLeu-14 |
| SEQ. ID. NO. 26304 | 27-PheGlyGlyArgAlaTyrAspPheArgAlaAspLysAlaAlaGly-41 |
| SEQ. ID. NO. 26305 | 67-TyrPheAlaAspAspLysPhe-73 |
| SEQ. ID. NO. 26306 | 78-LeuArgGlyAsnLeuArg-83 |
| SEQ. ID. NO. 26307 | 85-PheGlnThrAspLysAlaAspLeuArgThrGlyLysHisHisAlaAsnGly-101 |
| SEQ. ID. NO. 26308 | 108-AlaAspIleArgValAlaAla-114 |
| SEQ. ID. NO. 26309 | 136-ArgValAlaArgAsnLysAspMetArgAsnAlaGlyLeuHis-149 |
| SEQ. ID. NO. 26310 | 152-ArgIleGlyAsnGlyTyr-157 |
| SEQ. ID. NO. 26311 | 176-ArgThrAlaThrTyr-180 |
| SEQ. ID. NO. 26312 | 223-SerGluHisGlyPheArg-228 |
| Hydrophilic Regions - Hopp-Woods | |
| SEQ. ID. NO. 26313 | 1-MetValGluArgHisIleGln-7 |
| SEQ. ID. NO. 26314 | 30-ArgAlaTyrAspPheArgAlaAspLysAlaAla-40 |
| SEQ. ID. NO. 26315 | 67-TyrPheAlaAspAspLysPhe-73 |
| SEQ. ID. NO. 26316 | 85-PheGlnThrAspLysAlaAspLeuArgThrGlyLysHisHisAla-99 |
| SEQ. ID. NO. 26317 | 108-AlaAspIleArgValAlaAla-114 |
| SEQ. ID. NO. 26318 | 136-ArgValAlaArgAsnLysAspMetArgAsn-145 |
| g019-2 | |
| AMPHI Regions - AMPHI | |
| SEQ. ID. NO. 26319 | 33-ProAlaAspAsnIleGlu-38 |
| SEQ. ID. NO. 26320 | 55-GlyLysThrLeuAlaAspTyrGlyGlyTyrProSerAlaLeuAspAlaValLysGln-73 |
| SEQ. ID. NO. 26321 | 83-LeuGluAsnThrGlyAsp-88 |
| SEQ. ID. NO. 26322 | 90-AlaMetAlaGluAsnValArgLysGluTrpLeuLysSer-102 |
| SEQ. ID. NO. 26323 | 142-AlaAlaGluLeuValXxxAsnThrGlyLysLeuProSerGlyCysThrLysLeuLeuGluGlnAla-163 |
| SEQ. ID. NO. 26324 | 173-AspAlaTrpArgGlyValArgGlyLeu-181 |
| SEQ. ID. NO. 26325 | 195-AlaAlaLeuGlySerProPheAspGlyGlyThrGlnGly-207 |
| SEQ. ID. NO. 26326 | 215-AsnValIleGlyLysGluAlaArgLysSer-224 |
| SEQ. ID. NO. 26327 | 229-AlaLeuLeuSerGluMetGlu-235 |
| SEQ. ID. NO. 26328 | 259-AsnValProAlaAlaLeuAspTyrTyrGly-268 |
| SEQ. ID. NO. 26329 | 292-ArgArgTrpAspGluLeuAlaSerValIleSerHisMetProGluLysLeuGlnLys-310 |
| SEQ. ID. NO. 26330 | 329-GlnGluAlaGluLysLeuTyrLysGlnAla-338 |
| SEQ. ID. NO. 26331 | 451-ArgTyrIleSerPro-455 |
| SEQ. ID. NO. 26332 | 495-GlnGlyLeuMetGlnValMet-501 |
| SEQ. ID. NO. 26333 | 582-ArgAspTyrValLysLysValMet-589 |
| Antigenic Index - Jameson-Wolf | |
| SEQ. ID. NO. 26334 | 22-SerSerThrAsnThr-26 |
| SEQ. ID. NO. 26335 | 28-ProAlaGlyLysThrProAlaAspAsnIleGluThrAlaAspLeuSerAlaSerValProThrArgProAlaGluProGluGlyLysThrLeuAlaAspTyr GlyGlyTyrProSerAla-67 |
| SEQ. ID. NO. 26336 | 69-AspAlaValLysGlnAsnAsnAspAlaAla-78 |
| SEQ. ID. NO. 26337 | 84-GluAsnThrGlyAspSerAlaMet-91 |
| SEQ. ID. NO. 26338 | 93-GluAsnValArgLysGluTrpLeu-100 |
| SEQ. ID. NO. 26339 | 103-LeuGlyAlaArgArgGln-108 |
| SEQ. ID. NO. 26340 | 115-GluTyrAlaLysLeuLysProGluGlyGlyAlaGlnGluValGluCysTyrAlaAspSerSerArgAsnAspTyrThrArgAlaAlaGlu-144 |
| SEQ. ID. NO. 26341 | 147-XxxAsnThrGlyLysLeuProSerGlyCys-156 |
| SEQ. ID. NO. 26342 | 170-GlyGlyAsnAspAlaTrpArgGlyValArg-179 |
| SEQ. ID. NO. 26343 | 182-LeuAlaGlyArgProThrThrAspGlyArgAsn-192 |
| SEQ. ID. NO. 26344 | 199-SerProPheAspGlyGlyThrGlnGlySerArgGluTyr-211 |
| SEQ. ID. NO. 26345 | 217-IleGlyLysGluAlaArgLysSerProAsnAla-227 |
| SEQ. ID. NO. 26346 | 232-SerGluMetGluSerGlyLeuSerProGluGlnArgSer-244 |
| SEQ. ID. NO. 26347 | 254-GlnSerGlnSerLeu-258 |
| SEQ. ID. NO. 26348 | 266-TyrTyrGlyLysValAlaAspArgArgGlnLeuThrAspAspGlnIle-281 |
| SEQ. ID. NO. 26349 | 287-AlaAlaLeuArgAlaArgArgTrpAspGlu-296 |
| SEQ. ID. NO. 26350 | 304-MetProGluLysLeuGlnLysSerProThr-313 |
| SEQ. ID. NO. 26351 | 320-ArgSerArgAlaAlaThrGlyAsnThrGlnGluAlaGluLysLeuTyrLys-336 |
| SEQ. ID. NO. 26352 | 339-AlaAlaThrGlyArgAsn-344 |
| SEQ. ID. NO. 26353 | 350-AlaGlyGluGluLeuGlyArgLysIleAspThrArgAsnAsnValProAspAlaGlyLysAsnSerVal-372 |
| SEQ. ID. NO. 26354 | 374-ArgMetAlaGluAspGlyAlaIleLys-382 |
| SEQ. ID. NO. 26355 | 389-ArgAsnSerArgThrAlaGlyAspAlaLysMetArgArgGlnAlaGlnAla-405 |
| SEQ. ID. NO. 26356 | 409-PheAlaThrArgGlyPheAspGluAspLysLeuLeu-420 |
| SEQ. ID. NO. 26357 | 438-SerAlaGluArgThrAspArgLysLeuAsnTyr-448 |
| SEQ. ID. NO. 26358 | 454-SerProPheLysAspThrValIle-461 |

TABLE 1-continued

| | |
|---|---|
| SEQ. ID. NO. 26359 | 464-AlaGlnAsnValAsnValAspProAla-472 |
| SEQ. ID. NO. 26360 | 478-IleArgGlnGluSerArgPhe-484 |
| SEQ. ID. NO. 26361 | 488-AlaGlnSerArgValGlyAla-494 |
| SEQ. ID. NO. 26362 | 504-ThrAlaArgGluIleAlaGly-510 |
| SEQ. ID. NO. 26363 | 520-TyrThrAlaAspGlyAsnIleArgMetGly-529 |
| SEQ. ID. NO. 26364 | 535-AspThrLysArgArgLeuGlnAsnAsnGluIle-545 |
| SEQ. ID. NO. 26365 | 550-GlyTyrAsnAlaGlyProGlyArgAlaArgArgTrpGlnAlaAspThrProLeuGlu-568 |
| SEQ. ID. NO. 26366 | 579-SerGluThrArgAspTyrValLys-586 |
| SEQ. ID. NO. 26367 | 605-ProLeuLysGlnArgMetGlyThrValProAlaArg-616 |
| Hydrophilic Regions - Hopp-Woods | |
| SEQ. ID. NO. 26368 | 30-GlyLysThrProAlaAspAsnIleGluThrAlaAspLeu-42 |
| SEQ. ID. NO. 26369 | 46-ValProThrArgProAlaGluProGluGlyLysThrLeuAla-59 |
| SEQ. ID. NO. 26370 | 69-AspAlaValLysGlnAsnAsnAspAlaAla-78 |
| SEQ. ID. NO. 26371 | 85-AsnThrGlyAspSerAlaMet-91 |
| SEQ. ID. NO. 26372 | 93-GluAsnValArgLysGluTrpLeu-100 |
| SEQ. ID. NO. 26373 | 103-LeuGlyAlaArgArgGln-108 |
| SEQ. ID. NO. 26374 | 115-GluTyrAlaLysLeuLysProGluGlyGlyAlaGlnGluValGluCysTyrAlaAspSerSerArgAsnAspTyrThrArgAlaAlaGlu-144 |
| SEQ. ID. NO. 26375 | 150-GlyLysLeuProSerGlyCys-156 |
| SEQ. ID. NO. 26376 | 173-AspAlaTrpArgGly-177 |
| SEQ. ID. NO. 26377 | 186-ProThrThrAspGlyArgAsn-192 |
| SEQ. ID. NO. 26378 | 201-PheAspGlyGlyThrGlnGlySerArgGlu-210 |
| SEQ. ID. NO. 26379 | 217-IleGlyLysGluAlaArgLysSerProAsn-226 |
| SEQ. ID. NO. 26380 | 232-SerGluMetGluSerGlyLeuSerProGluGlnArgSer-244 |
| SEQ. ID. NO. 26381 | 270-ValAlaAspArgArgGlnLeuThrAspAspGlnIle-281 |
| SEQ. ID. NO. 26382 | 287-AlaAlaLeuArgAlaArgArgTrpAspGlu-296 |
| SEQ. ID. NO. 26383 | 304-MetProGluLysLeuGlnLys-310 |
| SEQ. ID. NO. 26384 | 320-ArgSerArgAlaAlaThr-325 |
| SEQ. ID. NO. 26385 | 327-AsnThrGlnGluAlaGluLysLeuTyrLys-336 |
| SEQ. ID. NO. 26386 | 350-AlaGlyGluGluLeuGlyArgLysIleAspThrArgAsnAsnValProAspAlaGlyLys-369 |
| SEQ. ID. NO. 26387 | 374-ArgMetAlaGluAspGlyAlaIleLys-382 |
| SEQ. ID. NO. 26388 | 389-ArgAsnSerArgThrAlaGlyAspAlaLysMetArgArgGlnAlaGlnAla-405 |
| SEQ. ID. NO. 26389 | 411-ThrArgGlyPheAspGluAspLysLeuLeu-420 |
| SEQ. ID. NO. 26390 | 438-SerAlaGluArgThrAspArgLysLeu-446 |
| SEQ. ID. NO. 26391 | 478-IleArgGlnGluSerArgPhe-484 |
| SEQ. ID. NO. 26392 | 504-ThrAlaArgGluIleAlaGly-510 |
| SEQ. ID. NO. 26393 | 535-AspThrLysArgArgLeuGlnAsn-542 |
| SEQ. ID. NO. 26394 | 554-GlyProGlyArgAlaArgArgTrpGlnAla-563 |
| SEQ. ID. NO. 26395 | 579-SerGluThrArgAspTyrValLys-586 |
| SEQ. ID. NO. 26396 | 606-LeuLysGlnArgMetGly-611 |
| g023 | |
| AMPHI Regions - AMPHI | |
| SEQ. ID. NO. 26397 | 43-GluTyrProAlaTrpGlnAlaPhePheSerGlnAlaTrpValLysValPheThrGlnValSerPheIleAlaValPheLeuHisAlaTrpValGly-74 |
| SEQ. ID. NO. 26398 | 77-AspLeuTrpMetAspTyrIleLys-84 |
| Antigenic Index - Jameson-Wolf | |
| SEQ. ID. NO. 26399 | 1-MetValGluArgLysLeuThr-7 |
| SEQ. ID. NO. 26400 | 40-LeuProLysGluTyrProAlaTrp-47 |
| Hydrophilic Regions - Hopp-Woods | |
| SEQ. ID. NO. 26401 | 1-MetValGluArgLysLeuThr-7 |
| g025 | |
| AMPHI Regions - AMPHI | |
| SEQ. ID. NO. 26402 | 9-AlaAlaCysThrAlaValAlaAlaLeuLeuGlyGlyCysAla-22 |
| SEQ. ID. NO. 26403 | 35-GlyMetGlnThrValSerSer-41 |
| SEQ. ID. NO. 26404 | 46-AsnProTyrGlyAlaThrProTyr-53 |
| SEQ. ID. NO. 26405 | 126-AspPheArgAlaTrpAsnGlyMetThrAsp-135 |
| SEQ. ID. NO. 26406 | 140-IleGlyGlnIleValLysVal-146 |
| SEQ. ID. NO. 26407 | 173-ValLysProAlaAla-177 |
| SEQ. ID. NO. 26408 | 181-ValGlnSerAlaProGlnPro-187 |
| SEQ. ID. NO. 26409 | 212-SerGlyThrArgSer-216 |
| SEQ. ID. NO. 26410 | 229-LysValValAlaAspPhe-234 |
| SEQ. ID. NO. 26411 | 265-GlyLeuArgGlyTyrGlyAsn-271 |
| Antigenic Index - Jameson-Wolf | |
| SEQ. ID. NO. 26412 | 22-AlaThrGlnGlnPro-26 |
| SEQ. ID. NO. 26413 | 108-ValArgGlyAspThr-112 |
| SEQ. ID. NO. 26414 | 115-AsnIleSerLysArgTyrHisIleSerGlnAspAspPheArgAla-129 |
| SEQ. ID. NO. 26415 | 131-AsnGlyMetThrAspAsnThrLeu-138 |
| SEQ. ID. NO. 26416 | 144-ValLysValLysProAlaGly-150 |
| SEQ. ID. NO. 26417 | 152-AlaAlaProLysThrAlaAlaValGluSerArgProAlaValPro-166 |
| SEQ. ID. NO. 26418 | 171-ThrProValLysProAlaAlaGlnProProValGlnSerAlaProGlnPro-187 |
| SEQ. ID. NO. 26419 | 190-ProAlaAlaGluAsnLysAlaValPro-198 |
| SEQ. ID. NO. 26420 | 202-ProAlaProGlnSerProAlaAlaSerProSerGlyThrArgSerValGly-218 |
| SEQ. ID. NO. 26421 | 224-ArgProThrGlnGlyLysValValAlaAspPheGlyGlyGlyAsnLysGlyValAsp-242 |
| SEQ. ID. NO. 26422 | 255-AlaAspGlyLysVal-259 |
| SEQ. ID. NO. 26423 | 264-SerGlyLeuArgGlyTyrGly-270 |
| SEQ. ID. NO. 26424 | 285-TyrGlyHisAsnGln-289 |
| SEQ. ID. NO. 26425 | 292-LeuValGlyGluGlyGlnGlnValLysArgGlyGlnGln-304 |
| SEQ. ID. NO. 26426 | 309-GlyAsnThrAspAlaSerArgThrGlnLeu-318 |
| SEQ. ID. NO. 26427 | 320-PheGluValArgGlnAsnGlyLysProValAsnProAsnSer-333 |
| Hydrophilic Regions - Hopp-Woods | |
| SEQ. ID. NO. 26428 | 108-ValArgGlyAspThr-112 |
| SEQ. ID. NO. 26429 | 120-TyrHisIleSerGlnAspAspPheArg-128 |

TABLE 1-continued

| | |
|---|---|
| SEQ. ID. NO. 26430 | 144-ValLysValLysPro-148 |
| SEQ. ID. NO. 26431 | 157-AlaAlaValGluSerArgProAla-164 |
| SEQ. ID. NO. 26432 | 171-ThrProValLysProAlaAla-177 |
| SEQ. ID. NO. 26433 | 190-ProAlaAlaGluAsnLysAlaValPro-198 |
| SEQ. ID. NO. 26434 | 212-SerGlyThrArgSer |
| SEQ. ID. NO. 26435 | 235-GlyGlyGlyAsnLysGlyValAsp-242 |
| SEQ. ID. NO. 26436 | 255-AlaAspGlyLysVal-259 |
| SEQ. ID. NO. 26437 | 295-GluGlyGlnGlnValLysArgGlyGln-303 |
| SEQ. ID. NO. 26438 | 311-ThrAspAlaSerArgThr-316 |
| SEQ. ID. NO. 26439 | 322-ValArgGlnAsnGlyLysProValAsn-330 |
| g032 | |
| AMPHI Regions - AMPHI | |
| SEQ. ID. NO. 26440 | 9-AlaValLeuArgArgProArgPheGlu-17 |
| SEQ. ID. NO. 26441 | 67-ProPheAlaGlyAsnValTyrProArgPheValGlnIle-79 |
| SEQ. ID. NO. 26442 | 114-ValHisGlyGlnIleGlnHisProValGlnProPheLeuArg-127 |
| SEQ. ID. NO. 26443 | 134-LeuGlyLeuLeuArgArgPheAspVal-142 |
| SEQ. ID. NO. 26444 | 174-GlnThrAlaLeuArg-178 |
| SEQ. ID. NO. 26445 | 204-LeuCysGlnGlnCysLysGlnPhePheGlnIleAla-215 |
| Antigenic Index - Jameson-Wolf | |
| SEQ. ID. NO. 26446 | 1-MetArgArgAsnVal-5 |
| SEQ. ID. NO. 26447 | 10-ValLeuArgArgProArgPhe-16 |
| SEQ. ID. NO. 26448 | 28-ArgAlaValProAlaGlyLysGlnGlyPhe-37 |
| SEQ. ID. NO. 26449 | 41-CysArgLeuThrGlnArg-46 |
| SEQ. ID. NO. 26450 | 58-GlyGlnArgAsnLeu-62 |
| SEQ. ID. NO. 26451 | 100-LeuGluGlnArgValValAlaHisArgGlnArgVal-111 |
| SEQ. ID. NO. 26452 | 138-ArgArgPheAspValGlyGlyArgValGlyAla-148 |
| SEQ. ID. NO. 26453 | 151-ProAlaPheAspGlnProGlyAla-158 |
| SEQ. ID. NO. 26454 | 160-LeuProProArgArgGlnLeuAlaArgGlnArgProThrVal-173 |
| SEQ. ID. NO. 26455 | 176-AlaLeuArgGlnProProGlnArgArgArgLysIleAlaProArgGlnValLeu-193 |
| SEQ. ID. NO. 26456 | 202-ArgHisLeuCysGlnGlnCysLys-209 |
| SEQ. ID. NO. 26457 | 216-ProValCysArgAsnArgValLeuArg-224 |
| SEQ. ID. NO. 26458 | 236-ValLysIleArgArgLysProValGlnAsnHisAsnArgProThrGlnIleSerLysAsnGln-256 |
| Hydrophilic Regions - Hopp-Woods | |
| SEQ. ID. NO. 26459 | 1-MetArgArgAsnVal-5 |
| SEQ. ID. NO. 26460 | 10-ValLeuArgArgProArgPhe-16 |
| SEQ. ID. NO. 26461 | 41-CysArgLeuThrGln-45 |
| SEQ. ID. NO. 26462 | 100-LeuGluGlnArgValValAlaHisArgGlnArgVal-111 |
| SEQ. ID. NO. 26463 | 138-ArgArgPheAspValGlyGly-144 |
| SEQ. ID. NO. 26464 | 161-ProProArgArgGlnLeuAlaArgGlnArgProThrVal-173 |
| SEQ. ID. NO. 26465 | 177-LeuArgGlnProProGlnArgArgArgLysIleAlaPro-189 |
| SEQ. ID. NO. 26466 | 218-CysArgAsnArgValLeu-223 |
| SEQ. ID. NO. 26467 | 236-ValLysIleArgArgLysProValGlnAsnHisAsnArgProThrGlnIleSerLysAsnGln-256 |
| g033-2 | |
| AMPHI Regions - AMPHI | |
| SEQ. ID. NO. 26468 | 6-GlnTyrGlyGlyLeuAlaGlyPheProLysArgCysGluSerGlu-20 |
| SEQ. ID. NO. 26469 | 64-GlyGlnAlaPheGluAlaLeuAsnCys-72 |
| SEQ. ID. NO. 26470 | 95-ValGlyAlaLeuProLysTyrLeuAlaSerAsnValValArgAspMetHisGlyLeuLeuSerThrVal-117 |
| SEQ. ID. NO. 26471 | 120-GlnThrGlyLysValLeuAspLysIleProGlyAlaMetGlu-133 |
| SEQ. ID. NO. 26472 | 142-IleLysThrLeuAlaGlu-147 |
| SEQ. ID. NO. 26473 | 157-SerLeu |
| SEQ. ID. NO. 26474 | PheGluAsnPhe-162 |
| SEQ. ID. NO. 26475 | 168-GlyProValAspGlyHisAsnValGluAsnLeuValAspValLeuLysAspLeuArgSerArg-188 |
| SEQ. ID. NO. 26476 | 207-AlaGluAsnAspPro-211 |
| SEQ. ID. NO. 26477 | 213-LysTyrHisAlaValAlaAsnLeuProLysGluGlyGlyAla-226 |
| SEQ. ID. NO. 26478 | 242-TyrThrGlnValPheGlyLys-248 |
| SEQ. ID. NO. 26479 | 280-PheProAspArgTyrPheAspVal-287 |
| SEQ. ID. NO. 26480 | 307-LysProValValAlaIleTyrSer-314 |
| SEQ. ID. NO. 26481 | 316-PheLeuGlnArgAlaTyrAspGlnLeu-324 |
| SEQ. ID. NO. 26482 | 363-CysValProAsnMet-367 |
| SEQ. ID. NO. 26483 | 390-AlaProAlaAlaValArgTyrProArgGlyThr-400 |
| SEQ. ID. NO. 26484 | 406-ValSerAspGlyMetGluThrValGlu-414 |
| SEQ. ID. NO. 26485 | 419-IleIleArgArgGlu-423 |
| SEQ. ID. NO. 26486 | 453-MetArgPheValLysProIleAspGluGlu-462 |
| SEQ. ID. NO. 26487 | 469-ArgSerHisAspArgIle-474 |
| SEQ. ID. NO. 26488 | 489-AlaValLeuGluValLeu-494 |
| SEQ. ID. NO. 26489 | 510-AspThrValThrGluHisGlyAspProLysLysLeuLeu-522 |
| Antigenic Index - Jameson-Wolf | |
| SEQ. ID. NO. 26490 | 11-AlaGlyPheProLysArgCysGluSerGluTyrAspAla-23 |
| SEQ. ID. NO. 26491 | 28-HisSerSerThrSerIle-33 |
| SEQ. ID. NO. 26492 | 41-AlaAlaAspLysLeuLeuGlyGlyAspArgArgSerVal-53 |
| SEQ. ID. NO. 26493 | 57-GlyAspGlyAlaMetThr-62 |
| SEQ. ID. NO. 26494 | 72-CysAlaGlyAspMetAspVal-78 |
| SEQ. ID. NO. 26495 | 85-AsnAspAsnGluMetSerIle-91 |
| SEQ. ID. NO. 26496 | 105-AsnValValArgAspMetHisGly-112 |
| SEQ. ID. NO. 26497 | 117-ValLysAlaGlnThrGlyLysValLeuAspLysIleProGly-130 |
| SEQ. ID. NO. 26498 | 134-PheAlaGlnLysValGluHisLysIleLysThrLeuAlaGluGluAlaGluHisAlaLysGln-154 |
| SEQ. ID. NO. 26499 | 166-TyrThrGlyProValAspGlyHisAsn-174 |
| SEQ. ID. NO. 26500 | 181-ValLeuLysAspLeuArgSerArgLysGlyProGln-192 |
| SEQ. ID. NO. 26501 | 197-IleThrLysLysGlyAsnGlyTyrLysLeuAlaGluAsnAspProValLys-213 |
| SEQ. ID. NO. 26502 | 219-AsnLeuProLysGluGlyGlyAlaGlnMetProSerGluLysGluProLysProAlaAlaLysProThrTyr-242 |

TABLE 1-continued

| | |
|---|---|
| SEQ. ID. NO. 26503 | 253-ArgAlaAlaAlaAspSerArgLeu-260 |
| SEQ. ID. NO. 26504 | 266-AlaMetArgGluGlySerGlyLeuValGluPheGluGlnArgPheProAspArgTyrPhe-285 |
| SEQ. ID. NO. 26505 | 345-ValGlyAlaAspGlyProThrHis-352 |
| SEQ. ID. NO. 26506 | 370-AlaAlaProSerAspGluAsnGluCysArg-379 |
| SEQ. ID. NO. 26507 | 395-ArgTyrProArgGlyThrGlyThrGlyAlaProValSerAspGlyMetGluThrValGluIleGlyLysGlyIleIleArgArgGluGlyGluLysThrAla-428 |
| SEQ. ID. NO. 26508 | 457-LysProIleAspGluGluLeuIle-464 |
| SEQ. ID. NO. 26509 | 467-LeuAlaArgSerHisAspArgIleValThrLeuGluGluAsnAlaGluGlnGlyGlyAlaGlyGly-488 |
| SEQ. ID. NO. 26510 | 511-ThrValThrGluHisGlyAspProLysLysLeuLeuAspAspLeuGlyLeu-527 |
| SEQ. ID. NO. 26511 | 530-GluAlaValGluArgArgValArgGluTrpLeuProAspArgAspAlaAlaAsn-547 |
| Hydrophilic Regions - Hopp-Woods | |
| SEQ. ID. NO. 26512 | 13-PheProLysArgCysGluSerGluTyrAsp-22 |
| SEQ. ID. NO. 26513 | 41-AlaAlaAspLysLeuLeuGlyGlyAspArgArgSerVal-53 |
| SEQ. ID. NO. 26514 | 74-GlyAspMetAspVal-78 |
| SEQ. ID. NO. 26515 | 85-AsnAspAsnGluMetSerIle-91 |
| SEQ. ID. NO. 26516 | 106-ValValArgAspMetHis-111 |
| SEQ. ID. NO. 26517 | 123-LysValLeuAspLysIleProGly-130 |
| SEQ. ID. NO. 26518 | 134-PheAlaGlnLysValGluHisLysIleLysThrLeuAlaGluGluAlaGluHisAlaLysGln-154 |
| SEQ. ID. NO. 26519 | 181-ValLeuLysAspLeuArgSerArgLysGlyPro-191 |
| SEQ. ID. NO. 26520 | 197-IleThrLysLysGlyAsnGly-203 |
| | 205-LysLeuAlaGluAsnAspProValLys-213 |
| SEQ. ID. NO. 26521 | 220-LeuProLysGluGlyGlyAla-226 |
| SEQ. ID. NO. 26522 | 228-MetProSerGluLysGluProLysProAlaAla-238 |
| SEQ. ID. NO. 26523 | 253-ArgAlaAlaAlaAspSerArgLeu-260 |
| SEQ. ID. NO. 26524 | 266-AlaMetArgGluGlySerGly-272 |
| SEQ. ID. NO. 26525 | 274-ValGluPheGluGlnArgPheProAspArgTyrPhe-285 |
| SEQ. ID. NO. 26526 | 372-ProSerAspGluAsnGluCys-378 |
| SEQ. ID. NO. 26527 | 405-ProValSerAspGlyMetGluThrValGluIleGlyLysGlyIleIleArgArgGluGlyGluLysThrAla-428 |
| SEQ. ID. NO. 26528 | 457-LysProIleAspGluGluLeuIle-464 |
| SEQ. ID. NO. 26529 | 467-LeuAlaArgSerHisAspArgIleValThrLeuGluGluAsnAlaGluGlnGlyGly-485 |
| SEQ. ID. NO. 26530 | 511-ThrValThrGluHisGlyAspProLysLysLeuLeuAsp-523 |
| SEQ. ID. NO. 26531 | 530-GluAlaValGluArgArgValArgGluTrpLeuProAspArgAspAlaAlaAsn-547 |
| g034 | |
| AMPHI Regions - AMPHI | |
| SEQ. ID. NO. 26532 | 35-LeuAspHisAlaAla-39 |
| SEQ. ID. NO. 26533 | 52-AsnLeuGluGlnMetArgAlaIleMetGluAlaAlaAspGln-65 |
| SEQ. ID. NO. 26534 | 94-AlaValGluGluPheProHisIlePro-102 |
| SEQ. ID. NO. 26535 | 152-ThrValValAsnPheSer-157 |
| SEQ. ID. NO. 26536 | 168-IleGlyValLeuGlyAsnLeuGluThrGly-177 |
| SEQ. ID. NO. 26537 | 197-LeuThrSerValGluAspAlaValArgPheValLysAspThrGly-211 |
| SEQ. ID. NO. 26538 | 226-TyrLysPheThrArgProProThrGly-234 |
| SEQ. ID. NO. 26539 | 236-ValLeuArgIleAspArgIleLysGluIleHisGlnAlaLeu-249 |
| SEQ. ID. NO. 26540 | 261-SerValProGlnGluTrpLeuLysValIleAsnGluTyrGlyGlyAsnIleGlyGluThrTyrGlyValProValGluGluIleValGluGlyIleLysHisGly-295 |
| SEQ. ID. NO. 26541 | 314-ArgArgTyrLeuAlaGluAsn-320 |
| SEQ. ID. NO. 26542 | 330-LeuGlyLysThrIleGluAlaMetLys-338 |
| Antigenic Index - Jameson-Wolf | |
| SEQ. ID. NO. 26543 | 20-LeuProLysGluThrGln-25 |
| SEQ. ID. NO. 26544 | 37-HisAlaAlaGluAsnSerTyrGly-44 |
| SEQ. ID. NO. 26545 | 54-GluGlnMetArgAlaIleMetGluAlaAlaAspGlnVal-66 |
| SEQ. ID. NO. 26546 | 75-SerAlaGlyAlaArgLysTyrAla-82 |
| SEQ. ID. NO. 26547 | 106-HisGlnAspHisGlyAlaSerProAspValCysGlnArgSerIle-120 |
| SEQ. ID. NO. 26548 | 132-SerLeuLeuGluAspGlyLysThrProSerSerTyrGluTyr-145 |
| SEQ. ID. NO. 26549 | 164-ValGluGlyGluIle-168 |
| SEQ. ID. NO. 26550 | 173-AsnLeuGluThrGlyGluAlaGlyGluGluAspGlyValGlyAla-187 |
| SEQ. ID. NO. 26551 | 191-LeuSerHisAspGln-195 |
| SEQ. ID. NO. 26552 | 199-SerValGluAspAlaValArgPheValLysAspThrGlyValAsp-213 |
| SEQ. ID. NO. 26553 | 221-ThrSerHisGlyAla-225 |
| SEQ. ID. NO. 26554 | 227-LysPheThrArgProProThrGlyAspValLeuArgIleAspArgIleLysGluIleHis-246 |
| SEQ. ID. NO. 26555 | 258-GlySerSerSerValPro-263 |
| SEQ. ID. NO. 26556 | 271-AsnGluTyrGlyGlyAsnIleGlyGlu-279 |
| SEQ. ID. NO. 26557 | 287-GluIleValGluGlyIleLysHisGlyValArgLysValAsnIleAspThrAspLeuArgLeuAlaSerThrGlyAlaVal-313 |
| SEQ. ID. NO. 26558 | 316-TyrLeuAlaGluAsnProSerAspPheAspProArgLysTyrLeuGlyLysThrIleGluAlaMetLys-338 |
| SEQ. ID. NO. 26559 | 350-CysGluGlyGlnAlaGlyLysIleLysProValSerLeuGluLysMetAlaSerArgTyrAlaLysGlyGluLeu-374 |
| Hydrophilic Regions - Hopp-Woods | |
| SEQ. ID. NO. 26560 | 54-GluGlnMetArgAlaIleMetGluAlaAlaAspGlnVal-66 |
| SEQ. ID. NO. 26561 | 76-AlaGlyAlaArgLysTyrAla-82 |
| SEQ. ID. NO. 26562 | 108-AspHisGlyAlaSerProAspValCysGln-117 |
| SEQ. ID. NO. 26563 | 132-SerLeuLeuGluAspGlyLysThrProSer-141 |
| SEQ. ID. NO. 26564 | 164-ValGluGlyGluIle-168 |
| SEQ. ID. NO. 26565 | 175-GluThrGlyGluAlaGlyGluGluAspGlyValGlyAla-187 |
| SEQ. ID. NO. 26566 | 199-SerValGluAspAlaValArgPheValLysAspThrGlyVal-212 |
| SEQ. ID. NO. 26567 | 235-AspValLeuArgIleAspArgIleLysGluIleHis-246 |
| SEQ. ID. NO. 26568 | 287-GluIleValGluGlyIleLysHisGlyValArgLysValAsnIleAspThrAspLeuArgLeu-307 |

TABLE 1-continued

| | |
|---|---|
| SEQ. ID. NO. 26569 | 320-AsnProSerAspPheAspProArgLysTyrLeu-330 |
| SEQ. ID. NO. 26570 | 333-ThrIleGluAlaMetLys-338 |
| SEQ. ID. NO. 26571 | 352-GlyGlnAlaGlyLysIleLysProValSerLeuGluLysMetAlaSerArgTyrAlaLysGlyGluLeu-374 |
| g036 | |
| AMPHI Regions - AMPHI | |
| SEQ. ID. NO. 26572 | 59-SerSerGlyArgPheCysGlnThrIleLysAlaAla-70 |
| SEQ. ID. NO. 26573 | 97-AlaAspGlyLeuGlnThrValSerSerAlaAla-107 |
| SEQ. ID. NO. 26574 | 142-AlaValArgArgValProArgGlnLeuArgAspSerArg-154 |
| SEQ. ID. NO. 26575 | 215-CysArgThrThrHisLysThrLeuArgProTyrAlaArgProGlnArgArg-231 |
| Antigenic Index - Jameson-Wolf | |
| SEQ. ID. NO. 26576 | 16-ProAlaArgThrSerSerSerArgArgCysValProSerGlyArgCys-31 |
| SEQ. ID. NO. 26577 | 35-TyrSerSerArgAlaAspAlaThrProArgArgArgHisSerGlyAlaVal-51 |
| SEQ. ID. NO. 26578 | 55-CysSerSerAspSerSerGlyArgPhe-63 |
| SEQ. ID. NO. 26579 | 74-SerPheSerAlaArgLysThrCysSerAspGlyGluThrSerAlaAspSerAsnTrpArg-93 |
| SEQ. ID. NO. 26580 | 109-AlaAlaGlnSerAspGlyGluAlaGlyArg-118 |
| SEQ. ID. NO. 26581 | 133-SerGlyArgPheCysCysGlyArgArgAlaValArgArgValProArgGlnLeuArgAspSerArgArgArgGlyArgAlaArgGluAsnArgArgArgSerAlaTyr-168 |
| SEQ. ID. NO. 26582 | 171-CysLeuArgArgAlaAspGlyPheProVal-180 |
| SEQ. ID. NO. 26583 | 182-ThrHisCysArgCysArgLeuLysArgArgThrProArgGlyGlyGlnCys-198 |
| SEQ. ID. NO. 26584 | 200-ProProTyrArgLeuAspAsnArgSerAsnGlyGlyGlySerAlaCysArgThrThrHisLysThrLeuArgProTyrAlaArgProGlnArgArgValCysSer-234 |
| SEQ. ID. NO. 26585 | 239-AlaAlaArgArgArgHisArgAlaTrpGlyCysArgLeuLysAlaCysArg-255 |
| SEQ. ID. NO. 26586 | 258-LeuProAsnLeuAlaProArgArgCysArgTyrAlaVal-270 |
| Hydrophilic Regions - Hopp-Woods | |
| SEQ. ID. NO. 26587 | 17-AlaArgThrSerSerSerArgArgCysValPro-27 |
| SEQ. ID. NO. 26588 | 37-SerArgAlaAspAlaThrProArgArgArgHisSerGly-49 |
| SEQ. ID. NO. 26589 | 55-CysSerSerAspSerSerGlyArg-62 |
| SEQ. ID. NO. 26590 | 76-SerAlaArgLysThrCysSerAspGlyGluThrSerAla-88 |
| SEQ. ID. NO. 26591 | 110-AlaGlnSerAspGlyGluAlaGlyArg-118 |
| SEQ. ID. NO. 26592 | 137-CysCysGlyArgArgAlaValArgArgValProArgGlnLeuArgAspSerArgArgArgGlyArgAlaArgGluAsnArgArgArgSerAlaTyr-168 |
| SEQ. ID. NO. 26593 | 171-CysLeuArgArgAlaAspGlyPhePro-179 |
| SEQ. ID. NO. 26594 | 182-ThrHisCysArgCysArgLeuLysArgArgThrProArgGlyGlyGln-197 |
| SEQ. ID. NO. 26595 | 202-TyrArgLeuAspAsnArgSerAsnGlyGly-211 |
| SEQ. ID. NO. 26596 | 213-SerAlaCysArgThrThrHisLysThrLeuArgProTyrAlaArgProGlnArgArgValCys-233 |
| SEQ. ID. NO. 26597 | 239-AlaAlaArgArgArgHisArgAlaTrp-247 |
| SEQ. ID. NO. 26598 | 251-LeuLysAlaCysArg-255 |
| SEQ. ID. NO. 26599 | 262-AlaProArgArgCysArgTyrAlaVal-270 |
| g038 | |
| AMPHI Regions - AMPHI | |
| SEQ. ID. NO. 26600 | 161-GlyLysLeuSerAlaValGlnGluValGluLys-171 |
| SEQ. ID. NO. 26601 | 178-AlaProIleAlaSerLeuAsn-184 |
| SEQ. ID. NO. 26602 | 195-GluPheGlyGlnPheLeuGluProValArgThrTyrArgArgGlnTyrGlyVal-212 |
| Antigenic Index - Jameson-Wolf | |
| SEQ. ID. NO. 26603 | 2-ThrAspPheArgGlnAspPhe-8 |
| SEQ. ID. NO. 26604 | 22-GluPheThrThrLysAlaGlyArgArgSerPro-32 |
| SEQ. ID. NO. 26605 | 38-GlyLeuPheAsnAspGlyAlaSer-45 |
| SEQ. ID. NO. 26606 | 58-IleGluSerGlyIleArg-63 |
| SEQ. ID. NO. 26607 | 85-LeuAlaGluLysGlyVal-90 |
| SEQ. ID. NO. 26608 | 96-TyrAsnArgLysGluAlaLysAspArgGlyGluGlyGlyVal-109 |
| SEQ. ID. NO. 26609 | 125-ValIleSerAlaGlyThrSerValArgGluSerIleLysLeuIleGluAlaGluGlyAlaThr-145 |
| SEQ. ID. NO. 26610 | 153-LeuAspArgMetGluLysGlyThrGlyLysLeuSerAla-165 |
| SEQ. ID. NO. 26611 | 167-GlnGluValGluLysGlnTyrGlyLeu-175 |
| SEQ. ID. NO. 26612 | 191-GlnAsnAsnProGluPheGlyGln-198 |
| SEQ. ID. NO. 26613 | 201-GluProValArgThrTyrArgArgGlnTyrGlyValGlu-213 |
| Hydrophilic Regions - Hopp-Woods | |
| SEQ. ID. NO. 26614 | 2-ThrAspPheArgGlnAspPhe-8 |
| SEQ. ID. NO. 26615 | 22-GluPheThrThrLysAlaGlyArgArgSer-31 |
| SEQ. ID. NO. 26616 | 85-LeuAlaGluLysGlyVal-90 |
| SEQ. ID. NO. 26617 | 96-TyrAsnArgLysGluAlaLysAspArgGlyGluGly-107 |
| SEQ. ID. NO. 26618 | 130-ThrSerValArgGluSerIleLysLeuIleGluAlaGluGlyAlaThr-145 |
| SEQ. ID. NO. 26619 | 153-LeuAspArgMetGluLysGlyThrGlyLys-162 |
| SEQ. ID. NO. 26620 | 167-GlnGluValGluLysGlnTyr-173 |
| SEQ. ID. NO. 26621 | 204-ArgThrTyrArgArgGlnTyrGly-211 |
| g040 | |
| AMPHI Regions - AMPHI | |
| SEQ. ID. NO. 26622 | 6-SerPheValAlaHisPhe-11 |
| SEQ. ID. NO. 26623 | 14-AlaAlaProTyrIleArgGlnMetArgGlyThr-24 |
| SEQ. ID. NO. 26624 | 38-GlyThrLeuAsnLysLeu-43 |
| SEQ. ID. NO. 26625 | 65-HisPheLeuAspArg-69 |
| SEQ. ID. NO. 26626 | 78-ProHisTyrCysArgGlyLeuArgValThrAspGluThr-90 |
| SEQ. ID. NO. 26627 | 95-AlaGlnGlnPheAlaGly-100 |
| SEQ. ID. NO. 26628 | 113-SerValSerGlyPheAlaArgAlaPro-121 |
| SEQ. ID. NO. 26629 | 136-MetGlyValIleAsp-140 |
| SEQ. ID. NO. 26630 | 146-TyrAlaGlyValIleArg-151 |
| SEQ. ID. NO. 26631 | 207-LeuSerAspGlyIleSerArgProAspGlyThrLeuAlaGlu-220 |
| SEQ. ID. NO. 26632 | 223-SerAlaGlnGluAlaGlnSerLeuAlaGluHisAla-234 |
| SEQ. ID. NO. 26633 | 244-SerAlaValAlaAlaLeuGluGly-251 |
| SEQ. ID. NO. 26634 | 277-IleGlyThrSerIle-281 |
| SEQ. ID. NO. 26635 | 289-IleArgGlnAlaHisSerGlyAspIleProHisIleAlaAlaLeuIleArgProLeuGlu-308 |

TABLE 1-continued

| | |
|---|---|
| SEQ. ID. NO. 26636 | 320-TyrLeuGluAsnHisIleSerGluPheSerIle-330 |
| SEQ. ID. NO. 26637 | 338-TyrGlyCysAlaAlaLeuLysThrPheAlaGluAlaAsp-350 |
| SEQ. ID. NO. 26638 | 371-ArgLeuLeuAlaHisIle-376 |
| SEQ. ID. NO. 26639 | 386-SerArgLeuPheAla-390 |
| Antigenic Index - Jameson-Wolf | |
| SEQ. ID. NO. 26640 | 2-AsnAlaProAspSer-6 |
| SEQ. ID. NO. 26641 | 11-PheArgGluAlaAlaProTyrIleArgGlnMetArgGlyThrThr-25 |
| SEQ. ID. NO. 26642 | 29-GlyIleAspGlyArgLeuLeuGluGlyGlyThr-39 |
| SEQ. ID. NO. 26643 | 74-GlnGlyArgThrProHisTyrCysArgGlyLeuArgValThrAspGluThrSerLeuGlyGln-94 |
| SEQ. ID. NO. 26644 | 101-ThrValArgSerArgPheGlu-107 |
| SEQ. ID. NO. 26645 | 119-ArgAlaProSerVal-123 |
| SEQ. ID. NO. 26646 | 134-ArgProMetGlyVal-138 |
| SEQ. ID. NO. 26647 | 140-AspGlyThrAspMetGluTyr-146 |
| SEQ. ID. NO. 26648 | 150-IleArgLysThrAspThrAlaAla-157 |
| SEQ. ID. NO. 26649 | 162-LeuAspAlaGlyAsn-166 |
| SEQ. ID. NO. 26650 | 173-LeuGlyHisSerTyrGlyGlyLysThrPheAsn-183 |
| SEQ. ID. NO. 26651 | 208-SerAspGlyIleSerArgProAspGlyThrLeuAla-219 |
| SEQ. ID. NO. 26652 | 222-LeuSerAlaGlnGluAlaGlnSerLeuAla-231 |
| SEQ. ID. NO. 26653 | 234-AlaAlaSerGluThrArgArgLeuIle-242 |
| SEQ. ID. NO. 26654 | 249-LeuGluGlyGlyVal-253 |
| SEQ. ID. NO. 26655 | 261-GlyAlaAlaAspGlySerLeuLeu-268 |
| SEQ. ID. NO. 26656 | 272-PheThrArgAsnGlyIleGlyThrSerIleAlaLysGluAla-285 |
| SEQ. ID. NO. 26657 | 290-ArgGlnAlaHisSerGlyAspIle-297 |
| SEQ. ID. NO. 26658 | 305-ArgProLeuGluGluGlnGly-311 |
| SEQ. ID. NO. 26659 | 315-HisArgSerArgGluTyrLeu-321 |
| SEQ. ID. NO. 26660 | 329-SerIleLeuGluHisAspGlyAspLeuTyr-338 |
| SEQ. ID. NO. 26661 | 345-ThrPheAlaGluAlaAspCysGlyGlu-353 |
| SEQ. ID. NO. 26662 | 361-ProGlnAlaGlnAspGlyGlyTyrGlyGluArgLeu-372 |
| SEQ. ID. NO. 26663 | 377-IleAspLysAlaArgGly-382 |
| SEQ. ID. NO. 26664 | 393-ThrAsnThrGlyGlu-397 |
| SEQ. ID. NO. 26665 | 402-ArgGlyPheGlnThrAlaSerGluAspGluLeuProGluThrArgArgLysAspTyrArgSerAsnGlyArgAsnProHisIleLeu-430 |
| Hydrophilic Regions - Hopp-Woods | |
| SEQ. ID. NO. 26666 | 11-PheArgGluAlaAlaPro-16 |
| SEQ. ID. NO. 26667 | 30-IleAspGlyArgLeuLeuGlu-36 |
| SEQ. ID. NO. 26668 | 84-LeuArgValThrAspGluThrSerLeu-92 |
| SEQ. ID. NO. 26669 | 102-ValArgSerArgPheGlu-107 |
| SEQ. ID. NO. 26670 | 140-AspGlyThrAspMetGluTyr-146 |
| SEQ. ID. NO. 26671 | 150-IleArgLysThrAspThrAlaAla-157 |
| SEQ. ID. NO. 26672 | 210-GlyIleSerArgProAspGlyThrLeu-218 |
| SEQ. ID. NO. 26673 | 222-LeuSerAlaGlnGluAlaGlnSerLeuAla-231 |
| SEQ. ID. NO. 26674 | 234-AlaAlaSerGluThrArgArgLeuIle-242 |
| SEQ. ID. NO. 26675 | 291-GlnAlaHisSerGlyAsp-296 |
| SEQ. ID. NO. 26676 | 305-ArgProLeuGluGluGlnGly-311 |
| SEQ. ID. NO. 26677 | 315-HisArgSerArgGluTyrLeu-321 |
| SEQ. ID. NO. 26678 | 332-GluHisAspGlyAspLeu-337 |
| SEQ. ID. NO. 26679 | 345-ThrPheAlaGluAlaAspCysGlyGlu-353 |
| SEQ. ID. NO. 26680 | 362-GlnAlaGlnAspGlyGlyTyrGlyGlu-370 |
| SEQ. ID. NO. 26681 | 377-IleAspLysAlaArgGly-382 |
| SEQ. ID. NO. 26682 | 402-ArgGlyPheGlnThrAlaSerGluAspGluLeuProGluThrArgArgLysAspTyrArgSerAsnGlyArgAsn-426 |
| g041-1 | |
| AMPHI Regions - AMPHI | |
| SEQ. ID. NO. 26683 | 6-AspProTyrArgHisPheGluAsnLeuAspSerAlaGluThr-19 |
| SEQ. ID. NO. 26684 | 45-AspGlyIleLeuAsnGlnMetGlnAsp-53 |
| SEQ. ID. NO. 26685 | 77-ProLysGlyValTyrArgMetCysThrAlaAla-87 |
| SEQ. ID. NO. 26686 | 102-ValAlaAspPheAspGluLeuLeu-109 |
| SEQ. ID. NO. 26687 | 117-GlyValSerHisLeuValGluGlnProAsn-126 |
| SEQ. ID. NO. 26688 | 218-MetValAsnAlaTrpArgTyrLeuAsp-226 |
| SEQ. ID. NO. 26689 | 232-IleAspLeuIleGluAlaSer-238 |
| SEQ. ID. NO. 26690 | 257-ProLeuAsnLeuProAsnAspCysAspValValGlyTyrLeu-270 |
| SEQ. ID. NO. 26691 | 317-GlnAlaLeuGluSerValGluThr-324 |
| SEQ. ID. NO. 26692 | 331-AlaSerLeuLeuGluAsnValGlnGlyArg-340 |
| SEQ. ID. NO. 26693 | 382-AspPheThrThrProLeu-387 |
| SEQ. ID. NO. 26694 | 451-GlyPheGlyIleProGluLeuProHisTyrLeuGlySerValGlyLys-466 |
| SEQ. ID. NO. 26695 | 493-AlaAlaGlnGlyIleSerLysHisLysSerValAspAspLeuLeuAlaValValArgAspLeuSerGluArg-516 |
| SEQ. ID. NO. 26696 | 519-SerSerProLysHis-523 |
| SEQ. ID. NO. 26697 | 541-ValArgGluProGlnSer-546 |
| SEQ. ID. NO. 26698 | 556-LeuThrAspMetIleArgTyr-562 |
| SEQ. ID. NO. 26699 | 571-TrpThrAspGluTyrGlyAsnProGlnLysTyrGluAlaCysLysArgArgLeuGly-589 |
| SEQ. ID. NO. 26700 | 591-LeuSerProTyrHisAsnLeuSerAspGlyIleAspTyrProPro-605 |
| SEQ. ID. NO. 26701 | 620-AlaHisAlaLeuLys-624 |
| SEQ. ID. NO. 26702 | 645-GlyHisThrGlyAsn-649 |
| SEQ. ID. NO. 26703 | 651-ThrGlnArgGluSer-655 |
| Antigenic Index - Jameson-Wolf | |
| SEQ. ID. NO. 26704 | 1-MetLysSerTyrProAspProTyrArgHisPheGluAsnLeuAspSerAlaGluThrGln-20 |
| SEQ. ID. NO. 26705 | 26-AlaAsnAlaGluThrArgAlaArgPheLeuAsnAsnAspLysAlaArgAlaLeuSerAspGlyIle-47 |
| SEQ. ID. NO. 26706 | 51-MetGlnAspThrArgGlnIleProPhe-59 |
| SEQ. ID. NO. 26707 | 61-GlnGluHisArgAlaArg-66 |
| SEQ. ID. NO. 26708 | 72-GlnAsnAlaGluTyrProLysGlyVal-80 |
| SEQ. ID. NO. 26709 | 89-TyrArgSerGlyTyrProGluTrp-96 |
| SEQ. ID. NO. 26710 | 104-AspPheAspGluLeuLeuGlyAspAspValTyr-114 |

TABLE 1-continued

| | |
|---|---|
| SEQ. ID. NO. 26711 | 123-GluGlnProAsnArg-127 |
| SEQ. ID. NO. 26712 | 132-LeuAsnLysSerGlyGlyAspThr-139 |
| SEQ. ID. NO. 26713 | 145-ValAspLeuGluAlaGlyGluLeuValGlu-154 |
| SEQ. ID. NO. 26714 | 161-AlaGlyLysAsnHisValSerTrpArgAspGluAsnSerVal-174 |
| SEQ. ID. NO. 26715 | 178-ProAlaTrpAspGluArgGlnLeuThrGluSerGlyTyrProArgGluValTrpLeuValGluArgGlyLysSerPheGluGluSerLeuPro-208 |
| SEQ. ID. NO. 26716 | 211-GlnIleAspLysGlyAla-216 |
| SEQ. ID. NO. 26717 | 223-ArgTyrLeuAspProGlnGlySerProIleAspLeuIleGluAlaSerAspGlyPheTyr-242 |
| SEQ. ID. NO. 26718 | 249-ValSerSerGluGlyGlyAlaLysProLeuAsnLeuProAsnAspCysAspVal-266 |
| SEQ. ID. NO. 26719 | 278-LeuArgLysAspTrpHisArgAlaAsnGlnSerTyrProSer-291 |
| SEQ. ID. NO. 26720 | 298-LysLeuAsnArgGlyGluLeuGly-305 |
| SEQ. ID. NO. 26721 | 313-ProAspGluThrGlnAla-318 |
| SEQ. ID. NO. 26722 | 320-GluSerValGluThrThrLys-326 |
| SEQ. ID. NO. 26723 | 337-ValGlnGlyArgLeuLysAla-343 |
| SEQ. ID. NO. 26724 | 345-ArgPheAlaAspSerLysTrpGlnGluAlaGluLeuProHisLeuProSerGly-362 |
| SEQ. ID. NO. 26725 | 365-GluMetThrAspGlnProTrpGlyGly-373 |
| SEQ. ID. NO. 26726 | 405-GlnProGlnGlnPheValSerAspGlyIleGluVal-416 |
| SEQ. ID. NO. 26727 | 422-ValSerSerAspGlyGluArgIle-429 |
| SEQ. ID. NO. 26728 | 435-GlyLysAsnAlaAlaProAspThr-442 |
| SEQ. ID. NO. 26729 | 479-AsnIleArgGlyGlyGlyGluPheGlyProArgTrpHis-491 |
| SEQ. ID. NO. 26730 | 496-GlyIleSerLysHisLysSerValAspAsp-505 |
| SEQ. ID. NO. 26731 | 511-ArgAspLeuSerGluArgGlyMetSerSerProLysHis-523 |
| SEQ. ID. NO. 26732 | 528-GlyGlySerAsnGly-532 |
| SEQ. ID. NO. 26733 | 540-PheValArgGluProGlnSerIleGlyAla-549 |
| SEQ. ID. NO. 26734 | 568-GlySerSerTrpThrAspGluTyrGlyAsnProGlnLysTyrGluAlaCysLysArgArgLeuGlyGluLeuSerProTyr-594 |
| SEQ. ID. NO. 26735 | 596-AsnLeuSerAspGlyIleAspTyrPro-604 |
| SEQ. ID. NO. 26736 | 610-ThrSerLeuSerAspAspArgValHis-618 |
| SEQ. ID. NO. 26737 | 627-AlaLysLeuArgGluThrSerProGlnSer-636 |
| SEQ. ID. NO. 26738 | 639-TyrSerProAspGlyGlyGlyHisThrGlyAsnGlyThrGlnArgGluSerAlaAspLysLeu-659 |
| Hydrophilic Regions - Hopp-Woods | |
| SEQ. ID. NO. 26739 | 3-SerTyrProAspProTyrArgHis-10 |
| SEQ. ID. NO. 26740 | 12-GluAsnLeuAspSerAlaGluThr-19 |
| SEQ. ID. NO. 26741 | 26-AlaAsnAlaGluThrArgAlaArgPheLeuAsnAsnAspLysAlaArgAlaLeuSer-44 |
| SEQ. ID. NO. 26742 | 51-MetGlnAspThrArgGln-56 |
| SEQ. ID. NO. 26743 | 61-GlnGluHisArgAlaArg-66 |
| SEQ. ID. NO. 26744 | 104-AspPheAspGluLeuLeuGly-110 |
| SEQ. ID. NO. 26745 | 134-LysSerGlyGlyAsp-138 |
| SEQ. ID. NO. 26746 | 145-ValAspLeuGluAlaGlyGluLeuValGlu-154 |
| SEQ. ID. NO. 26747 | 166-ValSerTrpArgAspGluAsnSer-173 |
| SEQ. ID. NO. 26748 | 180-TrpAspGluArgGlnLeuThr-186 |
| SEQ. ID. NO. 26749 | 198-GluArgGlyLysSerPheGluGluSerLeu-207 |
| SEQ. ID. NO. 26750 | 211-GlnIleAspLysGlyAla-216 |
| SEQ. ID. NO. 26751 | 233-AspLeuIleGluAlaSerAsp-239 |
| SEQ. ID. NO. 26752 | 250-SerSerGluGlyGlyAlaLys-256 |
| SEQ. ID. NO. 26753 | 278-LeuArgLysAspTrpHisArg-284 |
| SEQ. ID. NO. 26754 | 298-LysLeuAsnArgGlyGluLeuGly-305 |
| SEQ. ID. NO. 26755 | 313-ProAspGluThrGlnAla-318 |
| SEQ. ID. NO. 26756 | 320-GluSerValGluThrThrLys-326 |
| SEQ. ID. NO. 26757 | 337-ValGlnGlyArgLeuLysAla-343 |
| SEQ. ID. NO. 26758 | 347-AlaAspSerLysTrpGlnGluAlaGluLeu-356 |
| SEQ. ID. NO. 26759 | 412-AspGlyIleGluVal-416 |
| SEQ. ID. NO. 26760 | 424-SerAspGlyGluArg-428 |
| SEQ. ID. NO. 26761 | 436-LysAsnAlaAlaProAsp-441 |
| SEQ. ID. NO. 26762 | 481-ArgGlyGlyGlyGluPheGly-487 |
| SEQ. ID. NO. 26763 | 496-GlyIleSerLysHisLysSerValAspAsp-505 |
| SEQ. ID. NO. 26764 | 511-ArgAspLeuSerGluArgGlyMetSerSer-520 |
| SEQ. ID. NO. 26765 | 540-PheValArgGluProGlnSer-546 |
| SEQ. ID. NO. 26766 | 571-TrpThrAspGluTyrGlyAsn-577 |
| SEQ. ID. NO. 26767 | 579-GlnLysTyrGluAlaCysLysArgArgLeuGlyGlu-590 |
| SEQ. ID. NO. 26768 | 612-LeuSerAspAspArgValHis-618 |
| SEQ. ID. NO. 26769 | 627-AlaLysLeuArgGluThrSer-633 |
| SEQ. ID. NO. 26770 | 650-GlyThrGlnArgGluSerAlaAspLysLeu-659 |
| g042 | |
| AMPHI Regions - AMPHI | |
| SEQ. ID. NO. 26771 | 18-LeuSerAsnThrSerThr-23 |
| SEQ. ID. NO. 26772 | 33-AlaValArgSerMet-37 |
| SEQ. ID. NO. 26773 | 138-SerProLeuValArgIleLeuProLeuSer-147 |
| SEQ. ID. NO. 26774 | 151-SerMetValValAlaPhePheAlaAsn-159 |
| Antigenic Index - Jameson-Wolf | |
| SEQ. ID. NO. 26775 | 16-SerAlaLeuSerAsnThrSerThrAlaAlaGlyProSerCys-29 |
| SEQ. ID. NO. 26776 | 49-TyrSerLysGluThrGlyCysProCysProSerLeuArgLysAspSerSerThrGlyGlyArgProMetSerProCys-74 |
| SEQ. ID. NO. 26777 | 77-LeuAlaAsnArgAspCysValProLysAlaAspThr-88 |
| SEQ. ID. NO. 26778 | 93-ThrAspSerThrSerProArgProLeu-101 |
| SEQ. ID. NO. 26779 | 109-TrpAlaAsnSerAlaSer-114 |
| SEQ. ID. NO. 26780 | 120-SerAlaThrArgAlaSerLeuProLysIleArgAspArgVal-133 |
| SEQ. ID. NO. 26781 | 160-CysSerTyrAlaSerAlaProGlyPro-168 |
| SEQ. ID. NO. 26782 | 175-GlyLeuTrpArgCysArgAspSerGlnSerGlySerAsnSer-188 |
| SEQ. ID. NO. 26783 | 197-AsnAlaGlyCysLys-201 |
| Hydrophilic Regions - Hopp-Woods | |
| SEQ. ID. NO. 26784 | 49-TyrSerLysGluThrGlyCys-55 |
| SEQ. ID. NO. 26785 | 59-SerLeuArgLysAspSerSerThrGlyGlyArgProMet-71 |

TABLE 1-continued

SEQ. ID. NO. 26786 78-AlaAsnArgAspCysValProLysAlaAspThr-88
SEQ. ID. NO. 26787 94-AspSerThrSerProArg-99
SEQ. ID. NO. 26788 122-ThrArgAlaSerLeuProLysIleArgAspArgVal-133
SEQ. ID. NO. 26789 178-ArgCysArgAspSerGlnSerGly-185
g043-2
AMPHI Regions - AMPHI
SEQ. ID. NO. 26790 21-GluArgPheValGluProSerArg-28
SEQ. ID. NO. 26791 34-LysValHisArgGlyLeuAspGlyAlaAlaArgPheAspGluGlyGluArg-50
SEQ. ID. NO. 26792 59-AlaSerGlyAspGlyPhe-64
SEQ. ID. NO. 26793 81-AspAlaAlaGlyAspPheGlyAspGlyGlnArg-91
SEQ. ID. NO. 26794 98-GlnAsnIleGlyGlyPheValTyr-105
Antigenic Index - Jameson-Wolf
SEQ. ID. NO. 26795 1-MetProSerAlaPro-5
SEQ. ID. NO. 26796 12-ArgArgGlnLysSerValMetProProGluArgPheValGluProSerArg-28
SEQ. ID. NO. 26797 34-LysValHisArgGlyLeuAspGlyAlaAlaArgPheAspGluGlyGluArgValPhe-52
SEQ. ID. NO. 26798 56-AlaAlaGlnAlaSerGlyAspGlyPheAla-65
SEQ. ID. NO. 26799 79-GlnProAspAlaAlaGlyAspPheGlyAspGlyGlnArgAlaGlyGlu-94
SEQ. ID. NO. 26800 116-AlaGluGlyGluAla-120
Hydrophilic Regions - Hopp-Woods
SEQ. ID. NO. 26801 12-ArgArgGlnLysSerValMetProProGluArgPheValGluProSerArg-28
SEQ. ID. NO. 26802 34-LysValHisArgGlyLeuAspGlyAlaAlaArgPheAspGluGlyGluArgValPhe-52
SEQ. ID. NO. 26803 81-AspAlaAlaGlyAspPheGlyAspGlyGlnArgAlaGlyGlu-94
SEQ. ID. NO. 26804 116-AlaGluGlyGluAla-120
g046
AMPHI Regions - AMPHI
SEQ. ID. NO. 26805 6-ArgProThrSerSerPro-11
SEQ. ID. NO. 26806 46-ThrSerCysSerGlyLeuMetValSer-54
SEQ. ID. NO. 26807 64-PheSerLeuPheSerSer-69
SEQ. ID. NO. 26808 113-LysSerAlaSerSer-117
SEQ. ID. NO. 26809 143-SerCysAsnAlaPheSerSer-149
Antigenic Index - Jameson-Wolf
SEQ. ID. NO. 26810 6-ArgProThrSerSerProProArgArgAlaCys-16
SEQ. ID. NO. 26811 20-IleArgThrArgSerSerAlaLysArgLysThrCysAsnAlaProGlyGlnSerIleArgProAlaSerCysSer-44
SEQ. ID. NO. 26812 57-ProAsnMetGluArgLeuPro-63
SEQ. ID. NO. 26813 75-SerArgTyrSerLeuGluArgThrArgAlaMetArgProGlyMetLeuAsnArgSerAlaAla-95
SEQ. ID. NO. 26814 105-SerLeuArgGluSerAlaSerSerLysSerAlaSerSerAlaProAlaArgTyrAsnValLysGlyAspAlaProLeuPro-131
SEQ. ID. NO. 26815 133-ThrValTrpThrSerArgArgLeuProVal-142
SEQ. ID. NO. 26816 169-GluProThrCysProLeuProLys-176
Hydrophilic Regions - Hopp-Woods
SEQ. ID. NO. 26817 7-ProThrSerSerProProArgArgAlaCys-16
SEQ. ID. NO. 26818 20-IleArgThrArgSerSerAlaLysArgLysThrCysAsn-32
SEQ. ID. NO. 26819 36-GlnSerIleArgProAlaSer-42
SEQ. ID. NO. 26820 58-AsnMetGluArgLeuPro-63
SEQ. ID. NO. 26821 75-SerArgTyrSerLeuGluArgThrArgAlaMetArg-86
SEQ. ID. NO. 26822 105-SerLeuArgGluSerAlaSerSerLysSerAlaSer-116
SEQ. ID. NO. 26823 122-TyrAsnValLysGlyAspAlaProLeu-130
g047
AMPHI Regions - AMPHI
SEQ. ID. NO. 26824 17-IleAlaAspIleAlaGlnAspLeuProAspGlyAla-28
SEQ. ID. NO. 26825 62-AlaGluAsnIleGlyAlaVal-68
SEQ. ID. NO. 26826 89-AsnIleCysTyrArgLeuAlaLysGlnLeuGlu-99
SEQ. ID. NO. 26827 141-TyrIleAspGluIleAspValPhe-148
SEQ. ID. NO. 26828 161-SerAlaLeuLeuAla-165
SEQ. ID. NO. 26829 185-LeuLeuGluGlyAsn-189
SEQ. ID. NO. 26830 202-IleGlySerIleLeuAla-207
SEQ. ID. NO. 26831 247-SerGlyIleLysTrpProGluGlyCys-255
SEQ. ID. NO. 26832 257-IleAlaAlaValValArgAlaGlyThrGly-266
SEQ. ID. NO. 26833 293-IleLeuAsnGluLeuGluLysLeuIle-301
Antigenic Index - Jameson-Wolf
SEQ. ID. NO. 26834 5-GlnAlaArgArgGlyGlyLeuLeu-12
SEQ. ID. NO. 26835 20-IleAlaGlnAspLeuProAspGlyAlaAsp-29
SEQ. ID. NO. 26836 36-TyrArgAsnAsnArgLeu-41
SEQ. ID. NO. 26837 51-IleGluGlyAspGlu-55
SEQ. ID. NO. 26838 70-ProGluLeuArgProLysGluThrSerThrArgArgIleMet-83
SEQ. ID. NO. 26839 96-LysGlnLeuGluHis-100
SEQ. ID. NO. 26840 106-IleIleGluCysArgProArgArgAlaGluTrpIle-117
SEQ. ID. NO. 26841 119-GluAsnLeuAspAsnThrLeu-125
SEQ. ID. NO. 26842 130-SerAlaThrAspGluThrLeuLeuAspAsnGluTyrIleAspGluIleAsp-146
SEQ. ID. NO. 26843 152-ThrAsnAspAspGluSerAsnIle-159
SEQ. ID. NO. 26844 168-LeuGlyAlaLysArgVal-173
SEQ. ID. NO. 26845 178-AsnArgSerSerTyr-182
SEQ. ID. NO. 26846 186-LeuGluGlyAsnLysIle-191
SEQ. ID. NO. 26847 208-HisIleArgArgGlyAspIleVal-215
SEQ. ID. NO. 26848 219-ProIleArgArgGlyThrAlaGluAlaIleGlu-229
SEQ. ID. NO. 26849 232-AlaHisGlyAspLysLysThrSer-239
SEQ. ID. NO. 26850 242-IleGlyArgArgIleSerGlyIleLysTrpProGluGlyCysHis-256

TABLE 1-continued

| | |
|---|---|
| SEQ. ID. NO. 26851 | 262-ArgAlaGlyThrGlyGluThr-268 |
| SEQ. ID. NO. 26852 | 277-ValIleGlnAspGlyAspHis-283 |
| SEQ. ID. NO. 26853 | 288-ValSerArgArgArgIleLeuAsnGluLeuGluLys-299 |
| Hydrophilic Regions - Hopp-Woods | |
| SEQ. ID. NO. 26854 | 5-GlnAlaArgArgGlyGly-10 |
| SEQ. ID. NO. 26855 | 20-IleAlaGlnAspLeuProAspGlyAlaAsp-29 |
| SEQ. ID. NO. 26856 | 51-IleGluGlyAspGlu-55 |
| SEQ. ID. NO. 26857 | 70-ProGluLeuArgProLysGluThrSerThrArgArgIleMet-83 |
| SEQ. ID. NO. 26858 | 106-IleIleGluCysArgProArgArgAlaGluTrpIle-117 |
| SEQ. ID. NO. 26859 | 130-SerAlaThrAspGluThrLeuLeu-137 |
| SEQ. ID. NO. 26860 | 140-GluTyrIleAspGluIleAsp-146 |
| SEQ. ID. NO. 26861 | 152-ThrAsnAspAspGluSerAsnIle-159 |
| SEQ. ID. NO. 26862 | 168-LeuGlyAlaLysArgVal-173 |
| SEQ. ID. NO. 26863 | 186-LeuGluGlyAsnLysIle-191 |
| SEQ. ID. NO. 26864 | 209-IleArgArgGlyAspIle-214 |
| SEQ. ID. NO. 26865 | 219-ProIleArgArgGlyThrAlaGluAlaIleGlu-229 |
| SEQ. ID. NO. 26866 | 232-AlaHisGlyAspLysLysThrSer-239 |
| SEQ. ID. NO. 26867 | 242-IleGlyArgArgIleSer-247 |
| SEQ. ID. NO. 26868 | 277-ValIleGlnAspGlyAsp-282 |
| SEQ. ID. NO. 26869 | 289-SerArgArgArgIleLeuAsnGluLeuGluLys-299 |
| g049-2 | |
| AMPHI Regions - AMPHI | |
| SEQ. ID. NO. 26870 | 15-GlnHisLeuLeuGlu-19 |
| SEQ. ID. NO. 26871 | 34-AspHisAlaValAspGlyIleGlyGlnMet-43 |
| SEQ. ID. NO. 26872 | 50-GlnProPheGlyGln-54 |
| SEQ. ID. NO. 26873 | 61-GluHisPheAlaProValAspGlyPheArg-70 |
| SEQ. ID. NO. 26874 | 103-IleGlyValPheProAlaLeu-109 |
| SEQ. ID. NO. 26875 | 199-SerAspPheArgArg-203 |
| SEQ. ID. NO. 26876 | 217-AlaArgLeuThrGlnValPheGlnAlaPhePhe-227 |
| SEQ. ID. NO. 26877 | 241-ValLeuAsnLeuCysArgArgAla-248 |
| Antigenic Index - Jameson-Wolf | |
| SEQ. ID. NO. 26878 | 6-PheAspTyrArgThrArgLeu-12 |
| SEQ. ID. NO. 26879 | 21-IleSerLysGluArgHis-26 |
| SEQ. ID. NO. 26880 | 31-ArgArgThrAspHisAlaValAspGly-39 |
| SEQ. ID. NO. 26881 | 49-AspGlnProPheGly-53 |
| SEQ. ID. NO. 26882 | 64-AlaProValAspGlyPheArgValGlnAspIleAspLeuAspGlyHisGlnArgLeuPhe-83 |
| SEQ. ID. NO. 26883 | 90-PheArgAsnProValCysArgArgThrGlyPhe-100 |
| SEQ. ID. NO. 26884 | 122-GlyIleGluProAspSerProProArgPhe-131 |
| SEQ. ID. NO. 26885 | 135-PheArgAsnArgHisLeuGlnGlySerLeuArgVal-146 |
| SEQ. ID. NO. 26886 | 150-PheLeuLysAspAspHisArgValGly-158 |
| SEQ. ID. NO. 26887 | 199-SerAspPheArgArgPheGlyGlnArgHisIleGlyArgArgGlyIleHis-215 |
| SEQ. ID. NO. 26888 | 244-LeuCysArgArgAlaAsnProArgProLysArgSerLeu-256 |
| Hydrophilic Regions - Hopp-Woods | |
| SEQ. ID. NO. 26889 | 21-IleSerLysGluArgHis-26 |
| SEQ. ID. NO. 26890 | 31-ArgArgThrAspHisAlaVal-37 |
| SEQ. ID. NO. 26891 | 67-AspGlyPheArgValGlnAspIleAspLeuAspGlyHisGlnArgLeuPhe-83 |
| SEQ. ID. NO. 26892 | 93-ProValCysArgArgThrGlyPhe-100 |
| SEQ. ID. NO. 26893 | 124-GluProAspSerProProArg-130 |
| SEQ. ID. NO. 26894 | 150-PheLeuLysAspAspHisArgVal-157 |
| SEQ. ID. NO. 26895 | 200-AspPheArgArgPheGlyGln-206 |
| SEQ. ID. NO. 26896 | 208-HisIleGlyArgArgGlyIleHis-215 |
| SEQ. ID. NO. 26897 | 244-LeuCysArgArgAlaAsnProArgProLysArgSerLeu-256 |
| g050-1 | |
| AMPHI Regions - AMPHI | |
| SEQ. ID. NO. 26898 | 10-IleGlnSerIleCysAspAlaPheGlnPheIleSerTyrTyr-23 |
| SEQ. ID. NO. 26899 | 25-ProLysAspTyrIleAspAlaLeuTyrLysAlaTrpGlnLys-38 |
| SEQ. ID. NO. 26900 | 94-ValAsnGluGlyVal-98 |
| SEQ. ID. NO. 26901 | 163-AsnProSerAspAsnIleValAspTrpValLeuLys-174 |
| SEQ. ID. NO. 26902 | 177-ProThrMetGlyAla-181 |
| SEQ. ID. NO. 26903 | 235-LeuGluLeuPheGluLysValAsnAla-243 |
| SEQ. ID. NO. 26904 | 250-GlyLeuGlyGlyLeuThrThr-256 |
| SEQ. ID. NO. 26905 | 275-AlaMetIleProAsn-279 |
| SEQ. ID. NO. 26906 | 315-AsnGlyLysArgValAspValAsp-322 |
| SEQ. ID. NO. 26907 | 353-LysArgLeuValAsMetLeuAspLys-361 |
| SEQ. ID. NO. 26908 | 367-ValAspPheThrAsnArgLeu-373 |
| SEQ. ID. NO. 26909 | 379-ProValAspProValGlyAspGlu-386 |
| SEQ. ID. NO. 26910 | 396-AlaThrArgMetAspLysPheThrArgGlnMet-406 |
| SEQ. ID. NO. 26911 | 452-LysSerSerLysValLeuAlaPhe-459 |
| SEQ. ID. NO. 26912 | 490-AlaThrAlaProArgLysTrp-496 |
| Antigenic Index - Jameson-Wolf | |
| SEQ. ID. NO. 26913 | 4-IleLysGlnGluAspPheIle-10 |
| SEQ. ID. NO. 26914 | 23-TyrHisProLysAspTyrIleAspAlaLeu-32 |
| SEQ. ID. NO. 26915 | 36-TrpGlnLysGluGluAsnProAlaAlaLysAspAlaMet-48 |
| SEQ. ID. NO. 26916 | 55-SerArgMetCysAlaGluAsnAsnArgProIleCysGlnAspThrGly-70 |
| SEQ. ID. NO. 26917 | 88-MetSerValGluLysMetValAsnGluGlyValArgArgAlaTyrThrTrpGluGlyAsnThrLeuArgAlaSerVal-113 |
| SEQ. ID. NO. 26918 | 116-AspProAlaGlyLysArgGlnAsnThrLysAspAsnThr-128 |
| SEQ. ID. NO. 26919 | 138-ProGlyGlyLysValGluVal-144 |
| SEQ. ID. NO. 26920 | 148-AlaLysGlyGlyGlySerGluAsnLysSerLysLeu-159 |
| SEQ. ID. NO. 26921 | 163-AsnProSerAspAsnIle-168 |
| SEQ. ID. NO. 26922 | 192-GlyIleGlyGlyThrProGluLysAlaValLeuMetAlaLysGluSerLeu-208 |

TABLE 1-continued

| | |
|---|---|
| SEQ. ID. NO. 26923 | 213-AspIleGlnGluLeuGlnGluLysAlaAlaSerGlyAlaGluLeuSerThr-229 |
| SEQ. ID. NO. 26924 | 284-ArgHisValGluPheGluLeuAspGlySerGlyProValGluLeuThrProProArgValGluAspXxxProAspLeuThrTyrSerProAspAsnGly LysArgValAspValAspLysLeuThrLysGluGluValAlaSer |
| SEQ. ID. NO. 26925 | LysThrGlyAsp-336 |
| SEQ. ID. NO. 26926 | 345-LeuThrGlyArgAspAlaAlaHisLysArgLeu-355 |
| SEQ. ID. NO. 26927 | 359-LeuAspLysGlyGluGluLeuPro-366 |
| SEQ. ID. NO. 26928 | 379-ProValAspProValGlyAspGluValValGlyProAlaGlyProThrThrAlaThrArgMetAspLysPheThrArgGlnMetLeu-407 |
| SEQ. ID. NO. 26929 | 416-IleGlyLysSerGluArgGlyAlaAlaThr-425 |
| SEQ. ID. NO. 26930 | 428-AlaIleAlaAspAsnLysAla-434 |
| SEQ. ID. NO. 26931 | 450-AlaIleLysSerSerLys-455 |
| SEQ. ID. NO. 26932 | 470-PheGluValLysAspMetPro-476 |
| SEQ. ID. NO. 26933 | 481-ValAspSerLysGlyGluSerIle-488 |
| SEQ. ID. NO. 26934 | 492-AlaProArgLysTrpGlnAla-498 |
| Hydrophilic Regions - Hopp-Woods | |
| SEQ. ID. NO. 26935 | 4-IleLysGlnGluAspPheIle-10 |
| SEQ. ID. NO. 26936 | 36-TrpGlnLysGluGluAsnProAlaAlaLysAspAlaMet-48 |
| SEQ. ID. NO. 26937 | 57-MetCysAlaGluAsnAsnArgProIleCys-66 |
| SEQ. ID. NO. 26938 | 88-MetSerValGluLysMetValAsnGluGlyValArgArg-100 |
| SEQ. ID. NO. 26939 | 117-ProAlaGlyLysArgGlnAsnThrLysAspAsnThr-128 |
| SEQ. ID. NO. 26940 | 140-GlyLysValGluVal-144 |
| SEQ. ID. NO. 26941 | 148-AlaLysGlyGlyGlySerGluAsnLysSerLysLeu-159 |
| SEQ. ID. NO. 26942 | 195-GlyThrProGluLysAlaValLeuMetAlaLysGluSerLeu-208 |
| SEQ. ID. NO. 26943 | 213-AspIleGlnGluLeuGlnGluLysAlaAlaSer-223 |
| SEQ. ID. NO. 26944 | 225-AlaGluLeuSerThr-229 |
| SEQ. ID. NO. 26945 | 284-ArgHisValGluPheGluLeuAspGly-292 |
| SEQ. ID. NO. 26946 | 299-ThrProProArgValGluAspXxxProAsp-308 |
| SEQ. ID. NO. 26947 | 313-ProAspAsnGlyLysArgValAspValAspLysLeuThrLysGluGluValAlaSer-331 |
| SEQ. ID. NO. 26948 | 345-LeuThrGlyArgAspAlaAlaHisLysArgLeu-355 |
| SEQ. ID. NO. 26949 | 359-LeuAspLysGlyGluGluLeuPro-366 |
| SEQ. ID. NO. 26950 | 382-ProValGlyAspGluValVal-388 |
| SEQ. ID. NO. 26951 | 397-ThrArgMetAspLysPheThrArgGlnMetLeu-407 |
| SEQ. ID. NO. 26952 | 417-GlyLysSerGluArgGlyAlaAlaThr-425 |
| SEQ. ID. NO. 26953 | 428-AlaIleAlaAspAsnLysAla-434 |
| SEQ. ID. NO. 26954 | 450-AlaIleLysSerSerLys-455 |
| SEQ. ID. NO. 26955 | 470-PheGluValLysAspMetPro-476 |
| SEQ. ID. NO. 26956 | 481-ValAspSerLysGlyGluSerIle-488 |
| SEQ. ID. NO. 26957 | 492-AlaProArgLysTrpGlnAla-498 |
| g052 | |
| AMPHI Regions - AMPHI | |
| SEQ. ID. NO. 26958 | 12-AlaProCysPheLysGlyCysGluProThrGlyAsp-23 |
| SEQ. ID. NO. 26959 | 41-AlaLysAlaSerLysSerAlaThrSerProLysGlyLeuAspGlyValSerLys-58 |
| SEQ. ID. NO. 26960 | 67-ThrAlaAlaPheHisSerPheIleSer-75 |
| SEQ. ID. NO. 26961 | 84-MetProAsnLeuValThrMetLeu-91 |
| Antigenic Index - Jameson-Wolf | |
| SEQ. ID. NO. 26962 | 4-ValAlaGluGluThrGluIle-10 |
| SEQ. ID. NO. 26963 | 14-CysPheLysGlyCysGluProThrGlyAspSerArgLeuLeuSerThrThrLysSerAlaPro-34 |
| SEQ. ID. NO. 26964 | 37-CysAlaAsnSerAlaLysAlaSerLysSerAlaThrSerProLysGlyLeuAspGlyValSerLysAsnSerSer-61 |
| SEQ. ID. NO. 26965 | 75-SerValGlyAspThrArgLeuThrProMet-84 |
| SEQ. ID. NO. 26966 | 97-ValValProAsnArgLeuArgLeuGluThrThrTrpSerProAlaCysArgLysValLysAsnAlaAla-119 |
| Hydrophilic Regions - Hopp-Woods | |
| SEQ. ID. NO. 26967 | 4-ValAlaGluGluThrGluIle-10 |
| SEQ. ID. NO. 26968 | 16-LysGlyCysGluProThrGlyAspSerArgLeu-26 |
| SEQ. ID. NO. 26969 | 30-ThrLysSerAlaPro-34 |
| SEQ. ID. NO. 26970 | 39-AsnSerAlaLysAlaSerLysSerAlaThrSerProLysGlyLeuAspGlyValSerLysAsnSer-60 |
| SEQ. ID. NO. 26971 | 77-GlyAspThrArgLeu-81 |
| SEQ. ID. NO. 26972 | 100-AsnArgLeuArgLeu-104 |
| SEQ. ID. NO. 26973 | 111-AlaCysArgLysValLysAsnAlaAla-119 |
| g075-2 | |
| AMPHI Regions - AMPHI | |
| SEQ. ID. NO. 26974 | 15-LysSerAlaAlaLysThrProThrThrIleGlnProAlaSerIleProSer-31 |
| SEQ. ID. NO. 26975 | 65-AlaProTyrLeuArgGlnValLeu-72 |
| SEQ. ID. NO. 26976 | 80-PheLysLysCysLeuAla-85 |
| SEQ. ID. NO. 26977 | 92-PheArgArgProProAsn-97 |
| SEQ. ID. NO. 26978 | 114-ValAlaAspPhePheGlnThrCysValAsnArgPhePheGluValValGluIleIleGlyIleGly-135 |
| Antigenic Index - Jameson-Wolf | |
| SEQ. ID. NO. 26979 | 12-GluAsnThrLysSerAlaAlaLysThrProThr-22 |
| SEQ. ID. NO. 26980 | 25-GlnProAlaSerIlePro-30 |
| SEQ. ID. NO. 26981 | 52-AlaLysAlaSerGly-56 |
| SEQ. ID. NO. 26982 | 90-GluPhePheArgArgProProAsnIleArgLysSerValPheGlnLysSerGluTyrAspLys-110 |
| Hydrophilic Regions - Hopp-Woods | |
| SEQ. ID. NO. 26983 | 12-GluAsnThrLysSerAlaAlaLysThr-20 |
| SEQ. ID. NO. 26984 | 52-AlaLysAlaSerGly-56 |
| SEQ. ID. NO. 26985 | 90-GluPhePheArgArgProProAsnIleArgLysSerValPheGlnLysSerGluTyrAspLys-110 |
| g080-2 | |
| AMPHI Regions - AMPHI | |
| SEQ. ID. NO. 26986 | 6-GluAlaMetGluArgLeuThrArg-13 |
| SEQ. ID. NO. 26987 | 95-PheProAspThrValGlu-100 |
| SEQ. ID. NO. 26988 | 108-ProValAlaArgTrpGlyAspHis-115 |
| SEQ. ID. NO. 26989 | 144-SerAlaGluMetLeuArgArgTyrAspGluPheSerThrValLeu-158 |
| SEQ. ID. NO. 26990 | 195-LysArgLeuArgLeuPheThrGluAlaTrpGlnHis-206 |

TABLE 1-continued

Antigenic Index - Jameson-Wolf
SEQ. ID. NO. 26991 1-MetTrpAspAsnAlaGluAlaMetGluArgLeuThr-12
SEQ. ID. NO. 26992 33-AsnSerAsnHisLeuPro-38
SEQ. ID. NO. 26993 42-ValSerLeuLysGly-46
SEQ. ID. NO. 26994 50-TyrSerAspLysLysAlaLeu-56
SEQ. ID. NO. 26995 67-AsnIleLeuArgThrAspIleAsnGlyAlaGlnGluAlaTyrArg-81
SEQ. ID. NO. 26996 90-MetValArgArgArgPheProAspThrValGlu-100
SEQ. ID. NO. 26997 103-LeuThrGluArgLysProValAlaArgTrpGly-113
SEQ. ID. NO. 26998 116-AlaLeuValAspGlyGluGlyAsnValPhe-125
SEQ. ID. NO. 26999 127-AlaArgLeuAspArgProGlyMetPro-135
SEQ. ID. NO. 27000 138-ArgGlyAlaGluGlyThrSer-144
SEQ. ID. NO. 27001 146-GluMetLeuArgArgTyrAspGlu-153
SEQ. ID. NO. 27002 163-LeuGlyIleLysGlu-167
SEQ. ID. NO. 27003 180-LeuAspAsnGlyIle-184
SEQ. ID. NO. 27004 187-ArgLeuGlyArgGluAsnGluMetLysArgLeuArgLeu-199
SEQ. ID. NO. 27005 207-LeuLeuArgLysAsnLysAsnArgLeuSer-216
SEQ. ID. NO. 27006 220-MetArgTyrLysAspGlyPheSerVal-228
SEQ. ID. NO. 27007 230-HisAlaProAspGlyLeuProGluLysGluSerGluGlu-242
Hydrophilic Regions - Hopp-Woods
SEQ. ID. NO. 27008 3-AspAsnAlaGluAlaMetGluArgLeuThr-12
SEQ. ID. NO. 27009 50-TyrSerAspLysLysAlaLeu-56
SEQ. ID. NO. 27010 69-LeuArgThrAspIleAsnGlyAlaGlnGluAlaTyrArg-81
SEQ. ID. NO. 27011 90-MetValArgArgArgPheProAspThrVal-99
SEQ. ID. NO. 27012 103-LeuThrGluArgLysProValAlaArgTrpGly-113
SEQ. ID. NO. 27013 116-AlaLeuValAspGlyGluGlyAsnValPhe-125
SEQ. ID. NO. 27014 127-AlaArgLeuAspArgProGly-133
SEQ. ID. NO. 27015 138-ArgGlyAlaGluGlyThrSer-144
SEQ. ID. NO. 27016 146-GluMetLeuArgArgTyrAspGlu-153
SEQ. ID. NO. 27017 163-LeuGlyIleLysGlu-167
SEQ. ID. NO. 27018 187-ArgLeuGlyArgGluAsnGluMetLysArgLeuArgLeu-199
SEQ. ID. NO. 27019 208-LeuArgLysAsnLysAsnArgLeuSer-216
SEQ. ID. NO. 27020 220-MetArgTyrLysAspGlyPheSer-227
SEQ. ID. NO. 27021 230-HisAlaProAspGlyLeuProGluLysGluSerGluGlu-242
g081
AMPHI Regions - AMPHI
SEQ. ID. NO. 27022 22-LysProValSerArgIleValThrAspSerArgAspIleArg-35
SEQ. ID. NO. 27023 54-ValGlyGlyValLeuSer-59
SEQ. ID. NO. 27024 78-AlaLeuLysValAspAsp-83
SEQ. ID. NO. 27025 85-LeuAlaAlaLeuGlnThrLeuAlaLysAlaTrpArgAspAsn-98
SEQ. ID. NO. 27026 116-LysGluMetLeuAlaAlaValLeuArg-124
SEQ. ID. NO. 27027 130-AspAlaValSerAla-134
SEQ. ID. NO. 27028 165-MetAsnHisPheGlyGluLeuAlaValLeuThrGlnIleAlaLys-179
SEQ. ID. NO. 27029 186-AsnAsnAlaLeuArg-190
SEQ. ID. NO. 27030 198-AspGlyValGlyAspIleAlaLysAla-206
SEQ. ID. NO. 27031 303-LeuAsnAspValAlaGluGlyLeuGlnGlyPheSerAsn-315
SEQ. ID. NO. 27032 345-AlaAlaValAspValLeuAlaArgMetPro-354
SEQ. ID. NO. 27033 360-ValMetGlyAspMetGlyGluLeuGlyGlu-369
SEQ. ID. NO. 27034 399-ValGluAlaAlaGlu-403
Antigenic Index - Jameson-Wolf
SEQ. ID. NO. 27035 15-LeuProMetProSerGluAsnLysProValSer-25
SEQ. ID. NO. 27036 27-IleValThrAspSerArgAspIleArgGluGlyAsp-38
SEQ. ID. NO. 27037 44-AlaGlyGlyArgPheAspAla-50
SEQ. ID. NO. 27038 67-ValSerArgGluAspCysAla-73
SEQ. ID. NO. 27039 79-LeuLysValAspAspThrLeu-85
SEQ. ID. NO. 27040 94-AlaTrpArgAspAsnValAsnProPhe-102
SEQ. ID. NO. 27041 102-GlySerGlyGlyLysThrThrValLysGluMetLeu-119
SEQ. ID. NO. 27042 123-LeuArgArgArgPheGlyAspAspAlaVal-132
SEQ. ID. NO. 27043 138-AsnPheAsnAsnHisIle-143
SEQ. ID. NO. 27044 151-LysLeuAsnGluLysHisArg-157
SEQ. ID. NO. 27045 178-AlaLysProAspAla-182
SEQ. ID. NO. 27046 194-GlyCysGlyPheAspGlyValGlyAspIleAlaLysAlaLysSerGluIle-210
SEQ. ID. NO. 27047 223-ProGlnGluAspAlaAsn-228
SEQ. ID. NO. 27048 245-GlyValAspSerGlyAspValArgAlaGluAsnIleVal-257
SEQ. ID. NO. 27049 269-CysGlyAspGluArgThrAla-275
SEQ. ID. NO. 27050 280-ValProGlyArgHisAsnVal-286
SEQ. ID. NO. 27051 314-SerAsnIleLysGlyArgLeuAsnVal-322
SEQ. ID. NO. 27052 330-ThrLeuIleAspAspThrTyrAsnAlaAsnProAspSerMetLysAlaAlaVal-347
SEQ. ID. NO. 27053 363-AspMetGlyGluLeuGlyGluAspGluAlaAla-373
SEQ. ID. NO. 27054 381-AlaTyrAlaArgAspGlnGlyIle-388
SEQ. ID. NO. 27055 395-GlyAspAsnSerValGluAlaAlaGluLysPheGlyAla-407
SEQ. ID. NO. 27056 425-AspLeuProGluArgAlaThrVal-432
SEQ. ID. NO. 27057 434-ValLysGlySerArg-438
SEQ. ID. NO. 27058 443-GluGluValValGluAlaLeuGluAspLys-452
Hydrophilic Regions - Hopp-Woods
SEQ. ID. NO. 27059 17-MetProSerGluAsnLysProValSer-25
SEQ. ID. NO. 27060 27-IleValThrAspSerArgAspIleArgGluGlyAsp-38
SEQ. ID. NO. 27061 46-GlyArgPheAspAla-50
SEQ. ID. NO. 27062 67-ValSerArgGluAspCysAla-73
SEQ. ID. NO. 27063 79-LeuLysValAspAspThrLeu-85
SEQ. ID. NO. 27064 94-AlaTrpArgAspAsnVal-99

TABLE 1-continued

| | |
|---|---|
| SEQ. ID. NO. 27065 | 109-SerGlyGlyLysThrThrValLysGluMetLeu-119 |
| SEQ. ID. NO. 27066 | 123-LeuArgArgArgPheGlyAspAspAlaVal-132 |
| SEQ. ID. NO. 27067 | 151-LysLeuAsnGluLysHisArg-157 |
| SEQ. ID. NO. 27068 | 178-AlaLysProAspAla-182 |
| SEQ. ID. NO. 27069 | 199-GlyValGlyAspIleAlaLysAlaLysSerGluIle-210 |
| SEQ. ID. NO. 27070 | 223-ProGlnGluAspAlaAsn-228 |
| SEQ. ID. NO. 27071 | 247-AspSerGlyAspValArgAlaGluAsnIleVal-257 |
| SEQ. ID. NO. 27072 | 269-CysGlyAspGluArgThrAla-275 |
| SEQ. ID. NO. 27073 | 316-IleLysGlyArgLeuAsnVal-322 |
| SEQ. ID. NO. 27074 | 335-ThrTyrAsnAlaAsnProAspSerMetLysAlaAlaVal-347 |
| SEQ. ID. NO. 27075 | 363-AspMetGlyGluLeuGlyGluAspGluAlaAla-373 |
| SEQ. ID. NO. 27076 | 381-AlaTyrAlaArgAspGlnGlyIle-388 |
| SEQ. ID. NO. 27077 | 397-AsnSerValGluAlaAlaGluLysPheGlyAla-407 |
| SEQ. ID. NO. 27078 | 425-AspLeuProGluArgAlaThrVal-432 |
| SEQ. ID. NO. 27079 | 443-GluGluValValGluAlaLeuGluAspLys-452 |
| g084-2 | |
| AMPHI Regions - AMPHI | |
| SEQ. ID. NO. 27080 | 6-ArgIleLysAsnMetAspGlnThrLeuLysAsnThrLeuGly-19 |
| SEQ. ID. NO. 27081 | 21-CysAlaLeuLeuAla-25 |
| SEQ. ID. NO. 27082 | 48-AlaValGlyAlaLeuAla-53 |
| SEQ. ID. NO. 27083 | 65-PheProArgValSer-69 |
| SEQ. ID. NO. 27084 | 96-GlnIleValGlySerIleLeuGluSer-104 |
| SEQ. ID. NO. 27085 | 111-GluPheValGlyAsnLeuProGly-118 |
| Antigenic Index - Jameson-Wolf | |
| SEQ. ID. NO. 27086 | 1-MetLysGlnSerAlaArgIleLysAsnMetAspGlnThrLeuLysAsnThr-17 |
| SEQ. ID. NO. 27087 | 40-TyrGluTyrGlyTyrArgTyrSer-47 |
| SEQ. ID. NO. 27088 | 102-LeuGluSerAsnProAlaGluAlaArgGluPheValGly-114 |
| Hydrophilic Regions - Hopp-Woods | |
| SEQ. ID. NO. 27089 | 1-MetLysGlnSerAlaArgIleLysAsnMetAspGlnThrLeu-14 |
| SEQ. ID. NO. 27090 | 105-AsnProAlaGluAlaArgGluPheVal-113 |
| g085-2 | |
| AMPHI Regions - AMPHI | |
| SEQ. ID. NO. 27091 | 41-GluArgValAlaGlnIleGlyLysMetPheAspGlyLeu-53 |
| SEQ. ID. NO. 27092 | 60-LeuLysAspAlaLeuAspAsnGlyPheAsp-69 |
| SEQ. ID. NO. 27093 | 90-AsnGlyGlyArgValLeuGlyAspIleGluLeuLeuAlaAspIle-104 |
| SEQ. ID. NO. 27094 | 125-ThrSerLeuValGlyTyr-130 |
| SEQ. ID. NO. 27095 | 141-IleAlaGlyAsnIleGlyThr-147 |
| SEQ. ID. NO. 27096 | 174-GluAsnThrGluSerLeu-179 |
| SEQ. ID. NO. 27097 | 191-GluAspHisLeuAspArgTyrAspAspLeuLeuAspTyr-203 |
| SEQ. ID. NO. 27098 | 213-GlyAspGlyValGln-217 |
| SEQ. ID. NO. 27099 | 225-PheCysArgAlaMetLysArgAlaGlyArgGluVal-236 |
| SEQ. ID. NO. 27100 | 275-HisAsnAlaAlaAsnValMetAlaAlaValAlaLeuCysGluAla-289 |
| SEQ. ID. NO. 27101 | 300-HisValLysThrPheGlnGlyLeuProHisArgValGluLysIleGly-315 |
| SEQ. ID. NO. 27102 | 336-AlaAlaIleAlaGlyLeu-341 |
| SEQ. ID. NO. 27103 | 353-GlyLysGlyGlnAspPheThr-359 |
| SEQ. ID. NO. 27104 | 394-ThrAspCysValThrLeuGluGluAlaValGlnThr-405 |
| SEQ. ID. NO. 27105 | 424-SerPheAspMetPheLysGlyTyr-431 |
| Antigenic Index - Jameson-Wolf | |
| SEQ. ID. NO. 27106 | 4-GlnAsnLysLysIleLeu-9 |
| SEQ. ID. NO. 27107 | 23-TyrLeuArgLysAsnGlyAlaGluValAlaAlaTyrAspAlaGluLeuLysAlaGluArgValAlaGln-45 |
| SEQ. ID. NO. 27108 | 58-GlyArgLeuLysAspAlaLeuAspAsnGlyPhe-68 |
| SEQ. ID. NO. 27109 | 74-SerProGlyIleSerGluArgGlnProAspIleGluAlaPheLysGlnAsnGlyGlyArgValLeuGly-96 |
| SEQ. ID. NO. 27110 | 104-IleValAsnArgArgGlyAspLysVal-112 |
| SEQ. ID. NO. 27111 | 116-ThrGlySerAsnGlyLysThrThr-123 |
| SEQ. ID. NO. 27112 | 150-LeuGluAlaGluLeuGlnArgGluGlyLysLysAlaAsp-162 |
| SEQ. ID. NO. 27113 | 169-SerSerPheGlnLeuGluAsnThrGluSerLeuArgProThrAla-183 |
| SEQ. ID. NO. 27114 | 189-IleSerGluAspHisLeuAspArgTyrAspAspLeuLeu-201 |
| SEQ. ID. NO. 27115 | 204-AlaHisThrLysAlaGluIlePheArgGlyAspGlyVal-216 |
| SEQ. ID. NO. 27116 | 220-AsnAlaAspAspValPhe-225 |
| SEQ. ID. NO. 27117 | 228-AlaMetLysArgAlaGlyArgGluValLysArgPheSerLeuGluHisGluAla-245 |
| SEQ. ID. NO. 27118 | 251-ArgGlyThrGlyCysLeuLysGlnGlyAsnGluAspLeuIleSerThrGlnAspIlePro-270 |
| SEQ. ID. NO. 27119 | 291-GlyLeuProArgGluAlaLeu-297 |
| SEQ. ID. NO. 27120 | 307-LeuProHisArgValGluLysIleGlyGluLysAsnGly-319 |
| SEQ. ID. NO. 27121 | 322-PheIleAspAspSerLysGlyThrAsnVal-331 |
| SEQ. ID. NO. 27122 | 351-GlyMetGlyLysGlyGlnAspPheThrProLeuArgAspAlaLeuLysAspLysAlaLys-370 |
| SEQ. ID. NO. 27123 | 378-AspAlaProGlnIleArgArgAspLeuAspGlyCysGly-390 |
| SEQ. ID. NO. 27124 | 397-ValThrLeuGluGluAlaVal-403 |
| SEQ. ID. NO. 27125 | 431-TyrAlaHisArgSer-435 |
| Hydrophilic Regions - Hopp-Woods | |
| SEQ. ID. NO. 27126 | 4-GlnAsnLysLysIleLeu-9 |
| SEQ. ID. NO. 27127 | 25-ArgLysAsnGlyAlaGlu-30 |
| SEQ. ID. NO. 27128 | 32-AlaAlaTyrAspAlaGluLeuLysAlaGluArgValAlaGln-45 |
| SEQ. ID. NO. 27129 | 59-ArgLeuLysAspAlaLeuAspAsnGlyPhe-68 |
| SEQ. ID. NO. 27130 | 77-IleSerGluArgGlnProAspIleGluAlaPheLysGlnAsnGlyGly-92 |
| SEQ. ID. NO. 27131 | 104-IleValAsnArgArgGlyAspLysVal-112 |
| SEQ. ID. NO. 27132 | 118-SerAsnGlyLysThrThr-123 |
| SEQ. ID. NO. 27133 | 150-LeuGluAlaGluLeuGlnArgGluGlyLysLysAlaAsp-162 |
| SEQ. ID. NO. 27134 | 174-GluAsnThrGluSerLeuArgPro-181 |
| SEQ. ID. NO. 27135 | 189-IleSerGluAspHisLeuAspArgTyrAspAspLeuLeu-201 |
| SEQ. ID. NO. 27136 | 204-AlaHisThrLysAlaGluIlePheArgGlyAspGly-215 |

TABLE 1-continued

| | |
|---|---|
| SEQ. ID. NO. 27137 | 228-AlaMetLysArgAlaGlyArgGluValLysArgPheSerLeuGluHisGluAla-245 |
| SEQ. ID. NO. 27138 | 251-ArgGlyThrGlyCysLeuLysGlnGlyAsnGluAspLeuIleSer-265 |
| SEQ. ID. NO. 27139 | 291-GlyLeuProArgGluAlaLeu-297 |
| SEQ. ID. NO. 27140 | 309-HisArgValGluLysIleGlyGluLysAsnGly-319 |
| SEQ. ID. NO. 27141 | 324-AspAspSerLysGlyThrAsn-330 |
| SEQ. ID. NO. 27142 | 353-GlyLysGlyGlnAsp-357 |
| SEQ. ID. NO. 27143 | 359-ThrProLeuArgAspAlaLeuLysAspLysAlaLys-370 |
| SEQ. ID. NO. 27144 | 380-ProGlnIleArgArgAspLeuAspGly-388 |
| SEQ. ID. NO. 27145 | 397-ValThrLeuGluGluAlaVal-403 |
| SEQ. ID. NO. 27146 | 431-TyrAlaHisArgSer-435 |
| g086 | |
| AMPHI Regions - AMPHI | |
| SEQ. ID. NO. 27147 | 55-MetArgThrTrpArgArgLeuValPro-63 |
| SEQ. ID. NO. 27148 | 83-IleAsnGlyAlaThrArg-88 |
| SEQ. ID. NO. 27149 | 99-ProThrGluLeuPheLysLeuAlaVal-107 |
| SEQ. ID. NO. 27150 | 120-GluValLeuArgSerMetGluSerLeuGlyTrpGlnSerIleTrpArgGlyThrAlaAsn-139 |
| SEQ. ID. NO. 27151 | 155-GluMetTyrGlyArgPhe-160 |
| SEQ. ID. NO. 27152 | 185-SerPheValValIle-189 |
| SEQ. ID. NO. 27153 | 228-ArgValGlnArgValValAlaPheLeuAspProTrpLysAspProGln-243 |
| SEQ. ID. NO. 27154 | 293-GlyPhePheGlyMetCys-298 |
| SEQ. ID. NO. 27155 | 336-TrpIleGlyIleGlnSerPhe-342 |
| Antigenic Index - Jameson-Wolf | |
| SEQ. ID. NO. 27156 | 20-LeuAlaSerLysGluGlyGlyAsp-27 |
| SEQ. ID. NO. 27157 | 54-ArgMetArgThrTrpArgArg-60 |
| SEQ. ID. NO. 27158 | 79-AlaGlyArgGluIleAsnGlyAla-86 |
| SEQ. ID. NO. 27159 | 115-PheThrArgArgGluGluValLeuArgSerMetGlu-126 |
| SEQ. ID. NO. 27160 | 134-TrpArgGlyThrAla-138 |
| SEQ. ID. NO. 27161 | 144-AlaThrAsnProGlnAlaArgArgGluThrLeuGluMet-156 |
| SEQ. ID. NO. 27162 | 225-AlaProTyrArgVal-229 |
| SEQ. ID. NO. 27163 | 236-LeuAspProTrpLysAspProGlnGlyAla-245 |
| SEQ. ID. NO. 27164 | 265-GlyLeuGlyAlaSerLeuSerLysArgGlyPheLeu-276 |
| SEQ. ID. NO. 27165 | 313-SerIleGlyLysGlnSerArgAspLeuGly-322 |
| SEQ. ID. NO. 27166 | 352-LeuProThrLysGlyLeu-357 |
| SEQ. ID. NO. 27167 | 382-IleAspTyrGluAsnArgGlnLysMetArgGlyTyrArgValGlu-396 |
| Hydrophilic Regions - Hopp-Woods | |
| SEQ. ID. NO. 27168 | 21-AlaSerLysGluGlyGlyAsp-27 |
| SEQ. ID. NO. 27169 | 79-AlaGlyArgGluIleAsnGly-85 |
| SEQ. ID. NO. 27170 | 115-PheThrArgArgGluGluValLeuArgSerMetGlu-126 |
| SEQ. ID. NO. 27171 | 147-ProGlnAlaArgArgGluThrLeuGluMet-156 |
| SEQ. ID. NO. 27172 | 238-ProTrpLysAspProGlnGly-244 |
| SEQ. ID. NO. 27173 | 270-LeuSerLysArgGlyPheLeu-276 |
| SEQ. ID. NO. 27174 | 316-LysGlnSerArgAspLeu-321 |
| SEQ. ID. NO. 27175 | 382-IleAspTyrGluAsnArgGlnLysMetArgGlyTyrArgValGlu-396 |
| g087 | |
| AMPHI Regions - AMPHI | |
| SEQ. ID. NO. 27176 | 80-LysThrValArgGluAlaGlnArgIleIle-89 |
| SEQ. ID. NO. 27177 | 99-GlyPheGlyGlyPheValThrPheProGlyGlyLeuAlaAlaLysLeuLeu-115 |
| SEQ. ID. NO. 27178 | 129-GlyLeuSerAsnArgHisLeuSerArgTrpAlaLysArgValLeuTyrAlaPheProLys-148 |
| SEQ. ID. NO. 27179 | 157-ValGlyAsnProValArg-162 |
| SEQ. ID. NO. 27180 | 192-GlyAlaAspValLeuAsnLysThrVal-200 |
| SEQ. ID. NO. 27181 | 241-ValGluPheIleThrAspMetValSerAlaTyr-251 |
| SEQ. ID. NO. 27182 | 313-GluLysLeuAlaGluIleLeuGly-320 |
| SEQ. ID. NO. 27183 | 330-TrpAlaGluAsnAla-334 |
| Antigenic Index - Jameson-Wolf | |
| SEQ. ID. NO. 27184 | 25-AspSerLeuArgValArgGly-31 |
| SEQ. ID. NO. 27185 | 37-LeuGlySerLysAspSerMetGluGluArgIleValProGlnTyrGlyIle-53 |
| SEQ. ID. NO. 27186 | 61-LysGlyIleArgGlyAsnGlyIleLysArgLysLeu-72 |
| SEQ. ID. NO. 27187 | 80-LysThrValArgGluAlaGlnArgIleIleArgLysHisArgVal-94 |
| SEQ. ID. NO. 27188 | 130-LeuSerAsnArgHisLeuSerArgTrpAlaLys-140 |
| SEQ. ID. NO. 27189 | 150-PheSerHisGluGlyGlyLeu-156 |
| SEQ. ID. NO. 27190 | 159-AsnProValArgAlaAspIleSer-166 |
| SEQ. ID. NO. 27191 | 171-ProAlaGluArgPheGlnGlyArgGluGlyArgLeu-182 |
| SEQ. ID. NO. 27192 | 195-ValLeuAsnLysThrVal-200 |
| SEQ. ID. NO. 27193 | 207-LeuProGluGluValArgProGlnMetTyrHisGlnSerGlyArgAsnLysLeuGly-225 |
| SEQ. ID. NO. 27194 | 229-AlaAspTyrAspAla-233 |
| SEQ. ID. NO. 27195 | 235-GlyValLysAlaGluCys-240 |
| SEQ. ID. NO. 27196 | 249-SerAlaTyrArgAspAlaAsp-255 |
| SEQ. ID. NO. 27197 | 284-AlaValAspAspHisGlnThrAla-291 |
| SEQ. ID. NO. 27198 | 309-GlnLeuThrAlaGluLysLeuAlaGlu-317 |
| SEQ. ID. NO. 27199 | 321-SerLeuAsnArgGluLysCysLeuLys-329 |
| SEQ. ID. NO. 27200 | 332-GluAsnAlaArgThr-336 |
| SEQ. ID. NO. 27201 | 341-HisSerAlaAspAspValAlaGlu-348 |
| Hydrophilic Regions - Hopp-Woods | |
| SEQ. ID. NO. 27202 | 25-AspSerLeuArgValArgGly-31 |
| SEQ. ID. NO. 27203 | 39-SerLysAspSerMetGluGluArgIleVal-48 |
| SEQ. ID. NO. 27204 | 66-AsnGlyIleLysArgLysLeu-72 |
| SEQ. ID. NO. 27205 | 81-ThrValArgGluAlaGlnArgIleIleArgLysHisArgVal-94 |
| SEQ. ID. NO. 27206 | 134-HisLeuSerArgTrpAlaLys-140 |
| SEQ. ID. NO. 27207 | 161-ValArgAlaAspIle-165 |
| SEQ. ID. NO. 27208 | 171-ProAlaGluArgPheGlnGlyArgGluGlyArgLeu-182 |

TABLE 1-continued

| | |
|---|---|
| SEQ. ID. NO. 27209 | 207-LeuProGluGluValArgPro-213 |
| SEQ. ID. NO. 27210 | 219-SerGlyArgAsnLysLeu-224 |
| SEQ. ID. NO. 27211 | 235-GlyValLysAlaGluCys-240 |
| SEQ. ID. NO. 27212 | 249-SerAlaTyrArgAspAlaAsp-255 |
| SEQ. ID. NO. 27213 | 284-AlaValAspAspHisGlnThrAla-291 |
| SEQ. ID. NO. 27214 | 310-LeuThrAlaGluLysLeuAlaGlu-317 |
| SEQ. ID. NO. 27215 | 322-LeuAsnArgGluLysCysLeuLys-329 |
| SEQ. ID. NO. 27216 | 341-HisSerAlaAspAspValAlaGlu-348 |
| g088-2 | |
| AMPHI Regions - AMPHI | |
| SEQ. ID. NO. 27217 | 7-HisPheSerAsnTrpLeuThrGlyLeuAsnIlePheGlnTyrThrThr-22 |
| SEQ. ID. NO. 27218 | 24-ArgAlaValMetAlaAlaLeu-30 |
| SEQ. ID. NO. 27219 | 43-ThrIleArgArgLeuThrAlaLeuLysCysGlyGln-54 |
| SEQ. ID. NO. 27220 | 88-LeuTrpGlyAsnTrpAlaAsn-94 |
| SEQ. ID. NO. 27221 | 111-GlyPheTyrAspAspTrpArgLysValValTyr-121 |
| SEQ. ID. NO. 27222 | 140-AlaValIleAlaGlyLeuAlaLeu-147 |
| SEQ. ID. NO. 27223 | 175-GlyPheLeuValLeuSerTyrLeuThrIle-184 |
| SEQ. ID. NO. 27224 | 187-ThrSerAsnAlaValAsnLeuThrAspGlyLeuAspGlyLeuAlaAla-202 |
| SEQ. ID. NO. 27225 | 221-HisTyrGlnPheSerGlnTyrLeuGlnLeuProTyr-232 |
| SEQ. ID. NO. 27226 | 244-ThrAlaMetCysGlyAlaCysLeuGlyPhe-253 |
| Antigenic Index - Jameson-Wolf | |
| SEQ. ID. NO. 27227 | 48-ThrAlaLeuLysCysGlyGlnAlaValArgThrAspGlyProGln-62 |
| SEQ. ID. NO. 27228 | 66-ValLysAsnGlyThrProThrMet-73 |
| SEQ. ID. NO. 27229 | 114-AspAspTrpArgLysValValTyrLysAspProAsnGlyValSerAlaLysPhe-131 |
| SEQ. ID. NO. 27230 | 193-LeuThrAspGlyLeuAsp-198 |
| SEQ. ID. NO. 27231 | 312-LysLysThrLysLysArgIle-318 |
| SEQ. ID. NO. 27232 | 328-TyrGluGlnLysGlyTrpLysGluThrGlnVal-338 |
| Hydrophilic Regions - Hopp-Woods | |
| SEQ. ID. NO. 27233 | 56-ValArgThrAspGlyProGln-62 |
| SEQ. ID. NO. 27234 | 114-AspAspTrpArgLysValValTyrLysAspProAsnGlyVal-127 |
| SEQ. ID. NO. 27235 | 312-LysLysThrLysLysArgIle-318 |
| SEQ. ID. NO. 27236 | 331-LysGlyTrpLysGlu-335 |
| g089 | |
| AMPHI Regions - AMPHI | |
| SEQ. ID. NO. 27237 | 40-PheSerThrArgCysGlyLysProTrpLysValLeu-51 |
| SEQ. ID. NO. 27238 | 74-LeuAlaAlaLeuCysLysProCysSerGlyMetSerCys-86 |
| SEQ. ID. NO. 27239 | 119-ArgProAlaArgPhe-123 |
| Antigenic Index - Jameson-Wolf | |
| SEQ. ID. NO. 27240 | 1-MetProProLysIleThrLysSerGlyPhe-10 |
| SEQ. ID. NO. 27241 | 40-PheSerThrArgCysGlyLysProTrpLys-49 |
| SEQ. ID. NO. 27242 | 53-CysSerSerAsnAlaSerArgGlyLysProThrAlaSerHisLysAla-68 |
| SEQ. ID. NO. 27243 | 77-LeuCysLysProCysSerGlyMetSer-85 |
| SEQ. ID. NO. 27244 | 87-ValGluIleLysSerSerLeuProCysPheLysGlnProValProArgSerAsnGlnLysSerAlaSerCysSerLysGluAsnArgPheThrSerArgPro AlaArgPheMetAlaArgGlnAsnThrSerSerAlaPheLysThrCysThrProSerProArgLysIleSer-144 |
| Hydrophilic Regions - Hopp-Woods | |
| SEQ. ID. NO. 27245 | 43-ArgCysGlyLysPro-47 |
| SEQ. ID. NO. 27246 | 56-AsnAlaSerArgGlyLysProThrAlaSerHisLysAla-68 |
| SEQ. ID. NO. 27247 | 87-ValGluIleLysSer-91 |
| SEQ. ID. NO. 27248 | 99-ProValProArgSerAsnGlnLysSerAlaSerCysSerLysGluAsnArgPheThrSerArgProAlaArgPheMetAla-125 |
| SEQ. ID. NO. 27249 | 137-ThrProSerProArgLysIleSer-144 |
| g090-1 | |
| AMPHI Regions - AMPHI | |
| SEQ. ID. NO. 27250 | 10-SerGlnSerLeuLysArgPheAspLysHisPheArg-21 |
| SEQ. ID. NO. 27251 | 51-ArgLeuAsnArgLeuPhe-56 |
| SEQ. ID. NO. 27252 | 59-AspAlaValGlyGlnVal-64 |
| SEQ. ID. NO. 27253 | 129-PheAlaValValAspGlu-134 |
| SEQ. ID. NO. 27254 | 141-AlaAspPhePheHisThrValArgGlnAla-150 |
| SEQ. ID. NO. 27255 | 152-GluGlyPheAspValPheGlnGlnCysPheAla-162 |
| SEQ. ID. NO. 27256 | 164-GlnThrAspGlyLeuAlaGln-170 |
| SEQ. ID. NO. 27257 | 177-ValGlyGlyValValGlnThrLeuGlnArg-186 |
| SEQ. ID. NO. 27258 | 233-ValValArgIleGlnAsnLeuHisSerIle-242 |
| SEQ. ID. NO. 27259 | 253-ValValGluGlnIle-257 |
| SEQ. ID. NO. 27260 | 388-GluThrValValGlnArgIlePheGlnThrThr-398 |
| SEQ. ID. NO. 27261 | 404-ProValLysHisLeuThrAspLeuArg-412 |
| SEQ. ID. NO. 27262 | 425-AsnLeuArgAlaValPheAlaGlnIleGlyAsnHisGlyAsnThrArgAlaAlaLysSer-444 |
| Antigenic Index - Jameson-Wolf | |
| SEQ. ID. NO. 27263 | 8-ThrAlaSerGlnSerLeuLysArgPheAspLysHisPheArg-21 |
| SEQ. ID. NO. 27264 | 29-HisIleGluThrArgAlaGlyGlyAlaGluGlnAspAsnIleAla-43 |
| SEQ. ID. NO. 27265 | 51-ArgLeuAsnArgLeuPheGlnSerAspAlaVal-61 |
| SEQ. ID. NO. 27266 | 73-AlaAspLeuArgArgIleAspAlaAspGlnGluHis-84 |
| SEQ. ID. NO. 27267 | 94-AlaGlnGlyArgGluVal-99 |
| SEQ. ID. NO. 27268 | 107-GlnAsnHisGluGluArgValLeuGlnThrGlyAsnArgGlyGlyGlyArgAlaAspIleArg-127 |
| SEQ. ID. NO. 27269 | 149-GlnAlaLeuGluGlyPhe-154 |
| SEQ. ID. NO. 27270 | 161-PheAlaArgGlnThrAspGlyLeuAlaGlnSerHisGlySerHisAsnValGlyGly-179 |
| SEQ. ID. NO. 27271 | 183-ThrLeuGlnArgAspValLeuArgArgAsnGln-193 |
| SEQ. ID. NO. 27272 | 201-ThrAlaArgProAlaPheGlnPro-208 |
| SEQ. ID. NO. 27273 | 214-PheGlnGlyLysProPheHisPheThrProCysPro-225 |
| SEQ. ID. NO. 27274 | 268-ValHisHisArgArgArgSerArgAlaGln-277 |
| SEQ. ID. NO. 27275 | 285-GluAlaGlyLysLeuGln-290 |
| SEQ. ID. NO. 27276 | 305-LeuGlnAsnArgArgThrAspIleAlaArgAsnAspGlyIleGlnPro-320 |

TABLE 1-continued

| | |
|---|---|
| SEQ. ID. NO. 27277 | 322-LeuAspAlaGluIleAlaAspGlnAlaArgTyrArgGly-334 |
| SEQ. ID. NO. 27278 | 339-AlaGlyAsnArgAsnHis-344 |
| SEQ. ID. NO. 27279 | 353-ValArgGlnGlnPhe-357 |
| SEQ. ID. NO. 27280 | 369-GluArgLeuAspIle-373 |
| SEQ. ID. NO. 27281 | 379-AspAlaGlyThrGluArgGlnAsnIle-387 |
| SEQ. ID. NO. 27282 | 396-GlnThrThrArgValLysHisGlnProVal-405 |
| SEQ. ID. NO. 27283 | 407-HisLeuThrAspLeuArgHis-413 |
| SEQ. ID. NO. 27284 | 422-IleSerGlyAsnLeu-426 |
| SEQ. ID. NO. 27285 | 435-AsnHisGlyAsnThrArgAlaAlaLysSerGlyAspGluAspPhePhe-450 |
| Hydrophilic Regions - Hopp-Woods | |
| SEQ. ID. NO. 27286 | 9-AlaSerGlnSerLeuLysArgPheAspLysHisPheArg-21 |
| SEQ. ID. NO. 27287 | 29-HisIleGluThrArgAlaGlyGlyAlaGluGlnAspAsnIleAla-43 |
| SEQ. ID. NO. 27288 | 73-AlaAspLeuArgArgIleAspAlaAspGlnGluHis-84 |
| SEQ. ID. NO. 27289 | 94-AlaGlnGlyArgGluVal-99 |
| SEQ. ID. NO. 27290 | 107-GlnAsnHisGluGluArgValLeu-114 |
| SEQ. ID. NO. 27291 | 117-GlyAsnArgGlyGlyGlyArgAlaAspIleArg-127 |
| SEQ. ID. NO. 27292 | 163-ArgGlnThrAspGlyLeuAla-169 |
| SEQ. ID. NO. 27293 | 184-LeuGlnArgAspValLeuArgArgAsnGln-193 |
| SEQ. ID. NO. 27294 | 269-HisHisArgArgArgSerArgAla-276 |
| SEQ. ID. NO. 27295 | 285-GluAlaGlyLysLeuGln-290 |
| SEQ. ID. NO. 27296 | 306-GlnAsnArgArgThrAspIleAlaArgAsnAspGlyIle-318 |
| SEQ. ID. NO. 27297 | 322-LeuAspAlaGluIleAlaAspGlnAlaArgTyrArg-333 |
| SEQ. ID. NO. 27298 | 369-GluArgLeuAspIle-373 |
| SEQ. ID. NO. 27299 | 380-AlaGlyThrGluArgGlnAsnIle-387 |
| SEQ. ID. NO. 27300 | 398-ThrArgValLysHisGlnPro-404 |
| SEQ. ID. NO. 27301 | 409-ThrAspLeuArgHis-413 |
| SEQ. ID. NO. 27302 | 437-GlyAsnThrArgAlaAlaLysSerGlyAspGluAspPhePhe-450 |
| g091 | |
| AMPHI Regions - AMPHI | |
| SEQ. ID. NO. 27303 | 38-LysProLeuSerAspGlyIleAlaSerArgLeuIleThrArgLeu-52 |
| SEQ. ID. NO. 27304 | 61-ValLeuValSerValLeuThrSerLeuAlaLys-71 |
| Antigenic Index - Jameson-Wolf | |
| SEQ. ID. NO. 27305 | 5-ValProProSerProAlaThr-11 |
| SEQ. ID. NO. 27306 | 28-IleLeuGlyArgArgArgProProLeuProLysProLeuSerAspGlyIleAla-45 |
| SEQ. ID. NO. 27307 | 73-LeuLeuSerGluArgLysValLeu-80 |
| Hydrophilic Regions - Hopp-Woods | |
| SEQ. ID. NO. 27308 | 28-IleLeuGlyArgArgArgProProLeu-36 |
| SEQ. ID. NO. 27309 | 73-LeuLeuSerGluArgLysValLeu-80 |
| g092 | |
| AMPHI Regions - AMPHI | |
| SEQ. ID. NO. 27310 | 55-GlyMetSerGlyIleAlaGluValLeuHis-64 |
| SEQ. ID. NO. 27311 | 76-AlaArgAsnAlaAlaThrGluHisLeu-84 |
| SEQ. ID. NO. 27312 | 95-HisThrAlaGluHisValAsnGly-102 |
| SEQ. ID. NO. 27313 | 122-AlaLeuGluArgGln-126 |
| SEQ. ID. NO. 27314 | 137-AlaGluLeuMetArgPheArgAsp-144 |
| SEQ. ID. NO. 27315 | 209-LeuThrProIleMetSerValValThrAsnIleAsp-220 |
| SEQ. ID. NO. 27316 | 226-ThrTyrGlyHisSerValGluLysLeuHisGlnAlaPheIleAspPheIleHisArg-244 |
| SEQ. ID. NO. 27317 | 260-ValArgAlaIleLeuProLysValSerLysProTyr-271 |
| SEQ. ID. NO. 27318 | 273-ThrTyrGlyLeuAspAspThrAla-280 |
| SEQ. ID. NO. 27319 | 321-AsnValLeuAsnAlaLeuAlaAlaIle-329 |
| SEQ. ID. NO. 27320 | 339-ValGluAlaIleGlnLysGly-345 |
| SEQ. ID. NO. 27321 | 353-GlyArgArgPheGlnLysTyrGlyAspIleLys-363 |
| SEQ. ID. NO. 27322 | 407-ArgTyrThrArgThrArgAspLeuPheGluAspPheThrLysValLeuAsnThrValAspAlaLeu-428 |
| SEQ. ID. NO. 27323 | 449-LeuAlaArgAlaIleArgValLeuGlyLysLeu-459 |
| SEQ. ID. NO. 27324 | 464-CysGluAsnValAlaAspLeuProGlnMetLeuMetAsn-476 |
| Antigenic Index - Jameson-Wolf | |
| SEQ. ID. NO. 27325 | 17-AlaAsnGlyGlnThrPhe-22 |
| SEQ. ID. NO. 27326 | 25-ThrProLeuArgThrLysAsnGlnProGluArgAsnIleMetMetLysAsnArgVal-43 |
| SEQ. ID. NO. 27327 | 70-ValSerGlySerAspGlnAlaArgAsnAlaAla-80 |
| SEQ. ID. NO. 27328 | 111-AlaValLysLysGluAsnProGluVal-119 |
| SEQ. ID. NO. 27329 | 121-AlaAlaLeuGluArgGlnIle-127 |
| SEQ. ID. NO. 27330 | 140-MetArgPheArgAspGlyIle-146 |
| SEQ. ID. NO. 27331 | 150-GlyThrHisGlyLysThrThrThr-157 |
| SEQ. ID. NO. 27332 | 184-GlyThrAsnAlaArgLeuGlyLysGlyGluTyr-194 |
| SEQ. ID. NO. 27333 | 198-GluAlaAspGluSerAspAla-204 |
| SEQ. ID. NO. 27334 | 218-AsnIleAspGluAspHisMetAspThrTyrGly-228 |
| SEQ. ID. NO. 27335 | 230-SerValGluLysLeuHis-235 |
| SEQ. ID. NO. 27336 | 255-ValAspSerGluHisVal-260 |
| SEQ. ID. NO. 27337 | 263-IleLeuProLysValSerLysProTyrAla-272 |
| SEQ. ID. NO. 27338 | 275-GlyLeuAspAspThrAlaAsp-281 |
| SEQ. ID. NO. 27339 | 286-AspIleGluAsnValGlyAla-292 |
| SEQ. ID. NO. 27340 | 302-MetLysGlyHisGluGlnGlySerPhe-310 |
| SEQ. ID. NO. 27341 | 351-GlyValGlyArgArgPheGlnLysTyrGlyAspIleLysLeuProAsnGlyGly-368 |
| SEQ. ID. NO. 27342 | 374-AspAspTyrGlyHisHisPro-380 |
| SEQ. ID. NO. 27343 | 393-AlaTyrProGluLysArgLeu-399 |
| SEQ. ID. NO. 27344 | 404-GlnProHisArgTyrThrArgThrArgAspLeuPheGluAspPheThrLys-420 |
| SEQ. ID. NO. 27345 | 435-AlaAlaGlyGluGluProValAlaAlaAlaAspSerArgAlaLeuAlaArg-451 |
| SEQ. ID. NO. 27346 | 478-LeuGlnAspGlyAspVal-483 |
| SEQ. ID. NO. 27347 | 488-GlyAlaGlySerIleAsnArgValProSerAla-498 |

TABLE 1-continued

| | |
|---|---|
| Hydrophilic Regions - Hopp-Woods | |
| SEQ. ID. NO. 27348 | 26-ProLeuArgThrLysAsnGlnProGluArgAsnIleMetMetLysAsnArgVal-43 |
| SEQ. ID. NO. 27349 | 71-SerGlySerAspGlnAlaArgAsnAlaAla-80 |
| SEQ. ID. NO. 27350 | 111-AlaValLysLysGluAsnProGlu-118 |
| SEQ. ID. NO. 27351 | 121-AlaAlaLeuGluArgGlnIle-127 |
| SEQ. ID. NO. 27352 | 140-MetArgPheArgAsp-144 |
| SEQ. ID. NO. 27353 | 152-HisGlyLysThrThr-156 |
| SEQ. ID. NO. 27354 | 187-AlaArgLeuGlyLysGlyGlu-193 |
| SEQ. ID. NO. 27355 | 198-GluAlaAspGluSerAspAla-204 |
| SEQ. ID. NO. 27356 | 218-AsnIleAspGluAspHisMetAsp-225 |
| SEQ. ID. NO. 27357 | 230-SerValGluLysLeuHis-235 |
| SEQ. ID. NO. 27358 | 256-AspSerGluHisVal-260 |
| SEQ. ID. NO. 27359 | 275-GlyLeuAspAspThrAlaAsp-281 |
| SEQ. ID. NO. 27360 | 303-LysGlyHisGluGlnGlySer-309 |
| SEQ. ID. NO. 27361 | 351-GlyValGlyArgArgPheGlnLys-358 |
| SEQ. ID. NO. 27362 | 360-GlyAspIleLysLeu-364 |
| SEQ. ID. NO. 27363 | 393-AlaTyrProGluLysArgLeu-399 |
| SEQ. ID. NO. 27364 | 407-ArgTyrThrArgThrArgAspLeuPheGluAspPheThrLys-420 |
| SEQ. ID. NO. 27365 | 435-AlaAlaGlyGluGluProValAlaAlaAlaAspSerArgAlaLeuAlaArg-451 |
| SEQ. ID. NO. 27366 | 479-GlnAspGlyAspVal-483 |
| g093-2 | |
| AMPHI Regions - AMPHI | |
| SEQ. ID. NO. 27367 | 26-ThrAlaIleLeuAsn-30 |
| SEQ. ID. NO. 27368 | 59-ThrAlaPheAsnIleLeuHisGly-66 |
| SEQ. ID. NO. 27369 | 156-GlyArgLeuLysSerValTyrGluGluLeuLysHisLeu-168 |
| SEQ. ID. NO. 27370 | 196-IleHisIleIleProAlaThrGluPhe-204 |
| SEQ. ID. NO. 27371 | 254-PheLeuLysAspThr-258 |
| SEQ. ID. NO. 27372 | 267-IleAsnThrLeuProGlyMetThrGly-275 |
| Antigenic Index - Jameson-Wolf | |
| SEQ. ID. NO. 27373 | 12-GlyGlyPheSerSerGluArgGluIleSerLeuAspSerGlyThr-26 |
| SEQ. ID. NO. 27374 | 32-LeuLysSerLysGlyIleAsp-38 |
| SEQ. ID. NO. 27375 | 41-AlaPheAspProLysGluThrProLeuSerGluLeuLysGluArgGlyPhe-57 |
| SEQ. ID. NO. 27376 | 66-GlyThrTyrGlyGluAspGlyAlaVal-74 |
| SEQ. ID. NO. 27377 | 96-GlyMetAspLysTyrArgCys-102 |
| SEQ. ID. NO. 27378 | 121-AspAspThrAspPheAspAlaValGluGluLysLeuGly-133 |
| SEQ. ID. NO. 27379 | 140-ProAlaAlaGluGlySerSer-146 |
| SEQ. ID. NO. 27380 | 151-LysValLysGluLysGlyArgLeuLysSerValTyrGluGluLeuLysHisLeuGln-169 |
| SEQ. ID. NO. 27381 | 176-ArgPheIleGlyGlyGlyGluTyrSer-184 |
| SEQ. ID. NO. 27382 | 189-AsnGlyLysGlyLeuPro-194 |
| SEQ. ID. NO. 27383 | 203-GluPheTyrAspTyrGluAlaLysTyrAsnArgAspAspThrIleTyrGlnCysProSerGluAspLeuThrGluAlaGluGluSerLeuMetArg-234 |
| SEQ. ID. NO. 27384 | 245-GlyAlaGluGlyCysVal-250 |
| SEQ. ID. NO. 27385 | 253-AspPheLeuLysAspThrAspGly-260 |
| SEQ. ID. NO. 27386 | 269-ThrLeuProGlyMetThr-274 |
| SEQ. ID. NO. 27387 | 279-ValProLysSerAlaAla-284 |
| Hydrophilic Regions - Hopp-Woods | |
| SEQ. ID. NO. 27388 | 15-SerSerGluArgGluIleSerLeu-22 |
| SEQ. ID. NO. 27389 | 32-LeuLysSerLysGlyIleAsp-38 |
| SEQ. ID. NO. 27390 | 41-AlaPheAspProLysGluThrProLeuSerGluLeuLysGluArgGlyPhe-57 |
| SEQ. ID. NO. 27391 | 68-TyrGlyGluAspGlyAlaVal-74 |
| SEQ. ID. NO. 27392 | 96-GlyMetAspLysTyrArgCys-102 |
| SEQ. ID. NO. 27393 | 121-AspAspThrAspPheAspAlaValGluGluLysLeuGly-133 |
| SEQ. ID. NO. 27394 | 140-ProAlaAlaGluGlySerSer-146 |
| SEQ. ID. NO. 27395 | 151-LysValLysGluLysGlyArgLeuLysSerValTyrGluGluLeuLysHisLeuGln-169 |
| SEQ. ID. NO. 27396 | 205-TyrAspTyrGluAlaLysTyrAsnArgAspAspThrIle-217 |
| SEQ. ID. NO. 27397 | 221-ProSerGluAspLeuThrGluAlaGluGluSerLeuMetArg-234 |
| SEQ. ID. NO. 27398 | 253-AspPheLeuLysAspThrAspGly-260 |
| g094 | |
| AMPHI Regions - AMPHI | |
| SEQ. ID. NO. 27399 | 17-LeuProProIleThrLysValGlySer-25 |
| SEQ. ID. NO. 27400 | 64-ArgGlyIleThrGlyIleCysArg-71 |
| SEQ. ID. NO. 27401 | 80-PheSerPheLeuThrAlaVal-86 |
| Antigenic Index - Jameson-Wolf | |
| SEQ. ID. NO. 27402 | 4-ProLeuProLysArgAlaLeu-10 |
| SEQ. ID. NO. 27403 | 24-GlySerSerProAlaAlaProArgMetGluAla-34 |
| SEQ. ID. NO. 27404 | 50-MetProSerArgLysArgIleSer-57 |
| SEQ. ID. NO. 27405 | 60-SerIleLysAlaArgGly-65 |
| SEQ. ID. NO. 27406 | 70-CysArgSerAsnAlaAlaThrThrSer-78 |
| Hydrophilic Regions - Hopp-Woods | |
| SEQ. ID. NO. 27407 | 5-LeuProLysArgAlaLeu-10 |
| SEQ. ID. NO. 27408 | 28-AlaAlaProArgMetGluAla-34 |
| SEQ. ID. NO. 27409 | 51-ProSerArgLysArgIleSer-57 |
| SEQ. ID. NO. 27410 | 60-SerIleLysAlaArgGly-65 |
| g095-2 | |
| AMPHI Regions - AMPHI | |
| SEQ. ID. NO. 27411 | 7-GlyGlyCysIleSerAsnLeuPheArgGlnPheGlnGlnArgGlyGlyAsnAlaValAsp-26 |
| SEQ. ID. NO. 27412 | 38-IleLeuXxxAsnIleHisGlnHisLeuArgGlnValGlyAspValPheAlaVal-55 |
| SEQ. ID. NO. 27413 | 63-TyrAlaAspSerThr-67 |
| SEQ. ID. NO. 27414 | 86-PheGlyGlnTyrGlnArgIleAsnGlyIleGluTyrPheGlyLysValPheLysGlnIleAlaArg-107 |
| SEQ. ID. NO. 27415 | 131-LysGlyCysArgHisPheAspGlyValValSer-141 |
| SEQ. ID. NO. 27416 | 174-PheLeuAspArgPheAsnArgCysAlaAspPheGlnArgHisAlaAspGlyCysGlnCysValGlnHisVal-197 |

TABLE 1-continued

| | |
|---|---|
| SEQ. ID. NO. 27417 | 204-GlnHisAspPheLys-208 |
| SEQ. ID. NO. 27418 | 236-AspValGlyGlyIleValGlnThrValSerSerIle-247 |
| SEQ. ID. NO. 27419 | 274-ThrValAspGluIleAspLysArgLeuMetGlnPhePheAspAlaVal-289 |
| SEQ. ID. NO. 27420 | 370-AsnGlyAspAlaValThrGluAlaHis-378 |
| SEQ. ID. NO. 27421 | 417-ValAsnValPheCysGly-422 |
| SEQ. ID. NO. 27422 | 435-MetLeuGlySerGlyIleSerArgLeuIleArgThrGly-447 |
| SEQ. ID. NO. 27423 | 451-AlaGlnIleValGlnAspPheGlyAspThrAlaHisAla-463 |
| Antigenic Index - Jameson-Wolf | |
| SEQ. ID. NO. 27424 | 17-PheGlnGlnArgGlyGlyAsnAlaValAspAlaSerArgThrHisIle-32 |
| SEQ. ID. NO. 27425 | 62-GlnTyrAlaAspSerThrArgGlnGlyAlaGlyValGlyGlyGlyAsnArg-78 |
| SEQ. ID. NO. 27426 | 112-ValArgLeuGluGlyGluHisGlnThr-120 |
| SEQ. ID. NO. 27427 | 126-AlaAlaCysSerGlyLysGlyCysArgHisPheAspGly-138 |
| SEQ. ID. NO. 27428 | 163-AlaAlaAlaAspAlaPheLysAlaGluGlnAlaPhe-174 |
| SEQ. ID. NO. 27429 | 176-AspArgPheAsnArgCysAlaAspPheGlnArgHisAlaAspGlyCysGln-192 |
| SEQ. ID. NO. 27430 | 205-HisAspPheLysArg-209 |
| SEQ. ID. NO. 27431 | 253-GlyGlnAsnArgAlaAspVal-259 |
| SEQ. ID. NO. 27432 | 263-AsnThrGlnLysGlyPheAlaVal-270 |
| SEQ. ID. NO. 27433 | 273-HisThrValAspGluIleAspLysArgLeu-282 |
| SEQ. ID. NO. 27434 | 299-AspIleGlyAsnAspGlyHisAsnArgGlyGlnMetXxxGluArgGlyIle-315 |
| SEQ. ID. NO. 27435 | 339-PheAlaAlaAspAsnGluSerGlyValGluSerCysArgAlaGluAspGlyGlyGlyGlnAlaGlyGlyArg-362 |
| SEQ. ID. NO. 27436 | 364-PheAlaValArgThrGlyAsnGlyAspAlaValThr-375 |
| SEQ. ID. NO. 27437 | 384-GlnGlyAlaArgAsnAsnGlyAsnLeuProLeuGlnArgSerAspAsnPheGly-401 |
| SEQ. ID. NO. 27438 | 405-LeuAspGlyGlyArgGlyAsnAspAspIleArgThr-416 |
| SEQ. ID. NO. 27439 | 442-ArgLeuIleArgThrGlyAsnPheLys-450 |
| SEQ. ID. NO. 27440 | 455-GlnAspPheGlyAspThrAlaHisAlaAspAlaAlaAspThrAspLysMetAspVal-473 |
| Hydrophilic Regions - Hopp-Woods | |
| SEQ. ID. NO. 27441 | 17-PheGlnGlnArgGlyGlyAsnAlaValAspAlaSerArgThrHisIle-32 |
| SEQ. ID. NO. 27442 | 65-AspSerThrArgGlnGlyAla-71 |
| SEQ. ID. NO. 27443 | 112-ValArgLeuGluGlyGluHis-118 |
| SEQ. ID. NO. 27444 | 128-CysSerGlyLysGlyCysArgHisPheAsp-137 |
| SEQ. ID. NO. 27445 | 163-AlaAlaAlaAspAlaPheLysAlaGluGlnAlaPhe-174 |
| SEQ. ID. NO. 27446 | 182-AlaAspPheGlnArgHisAlaAspGly-190 |
| SEQ. ID. NO. 27447 | 205-HisAspPheLysArg-209 |
| SEQ. ID. NO. 27448 | 273-HisThrValAspGluIleAspLysArgLeu-282 |
| SEQ. ID. NO. 27449 | 300-IleGlyAsnAspGlyHisAsnArgGlyGlnMetXxxGluArgGlyIle-315 |
| SEQ. ID. NO. 27450 | 339-PheAlaAlaAspAsnGluSerGlyValGluSerCysArgAlaGluAspGlyGlyGly-357 |
| SEQ. ID. NO. 27451 | 368-ThrGlyAsnGlyAspAlaValThr-375 |
| SEQ. ID. NO. 27452 | 384-GlnGlyAlaArgAsnAsnGly-390 |
| SEQ. ID. NO. 27453 | 394-LeuGlnArgSerAspAsn-399 |
| SEQ. ID. NO. 27454 | 407-GlyGlyArgGlyAsnAspAspIleArgThr-416 |
| SEQ. ID. NO. 27455 | 461-AlaHisAlaAspAlaAlaAspThrAspLysMetAspVal-473 |
| g096-2 | |
| AMPHI Regions - AMPHI | |
| SEQ. ID. NO. 27456 | 19-GlyIlePheGluGluIleAspAlaHis-27 |
| SEQ. ID. NO. 27457 | 59-IleAsnGlyValValSerVal-65 |
| SEQ. ID. NO. 27458 | 112-GlnPhePheValAsnAlaPheGlnThrAlaPhePhePheAsp-125 |
| SEQ. ID. NO. 27459 | 161-GluLeuGlyAsnGlyXxx - 166 |
| SEQ. ID. NO. 27460 | 172-AsnGlnPheAlaAla-176 |
| SEQ. ID. NO. 27461 | 188-ThrAlaAlaGlyIleGlyAsnAlaGln-196 |
| SEQ. ID. NO. 27462 | 228-XxxArgArgPheLeu-232 |
| Antigenic Index - Jameson-Wolf | |
| SEQ. ID. NO. 27463 | 4-HisThrGlyGlnGly-8 |
| SEQ. ID. NO. 27464 | 22-GluGluIleAspAla-26 |
| SEQ. ID. NO. 27465 | 30-PheArgThrAspCys-34 |
| SEQ. ID. NO. 27466 | 74-LeuGlyCysGlyAspAspValTyrAla-82 |
| SEQ. ID. NO. 27467 | 88-ValGlnAspGlyAla-92 |
| SEQ. ID. NO. 27468 | 97-AlaAlaAspLysThrPheGlyAsn-104 |
| SEQ. ID. NO. 27469 | 133-AlaPheGlyArgArgLeuHisLysHisArgGlnThr-144 |
| SEQ. ID. NO. 27470 | 161-GluLeuGlyAsnGlyXxxSerGlnCysLeu-170 |
| SEQ. ID. NO. 27471 | 181-AlaAspGlyGlyGlyGlyAspThr-188 |
| SEQ. ID. NO. 27472 | 211-ThrValLysAspValGluCysArgLeuLysAla-221 |
| Hydrophilic Regions - Hopp-Woods | |
| SEQ. ID. NO. 27473 | 22-GluGluIleAspAla-26 |
| SEQ. ID. NO. 27474 | 75-GlyCysGlyAspAspValTyr-81 |
| SEQ. ID. NO. 27475 | 97-AlaAlaAspLysThrPheGly-103 |
| SEQ. ID. NO. 27476 | 133-AlaPheGlyArgArgLeuHisLysHisArgGln-143 |
| SEQ. ID. NO. 27477 | 182-AspGlyGlyGlyGlyAspThr-188 |
| SEQ. ID. NO. 27478 | 211-ThrValLysAspValGluCysArgLeuLysAla-221 |
| g097 | |
| AMPHI Regions - AMPHI | |
| SEQ. ID. NO. 27479 | 28-AlaGlyLeuThrThrPheLeuThrMetCysTyrIleVal-40 |
| SEQ. ID. NO. 27480 | 166-AlaThrLeuValGlyLeuGlyAspIleHisGlnProSerAlaLeuLeuAlaLeuPheGlyPheValMetValValValLeu-192 |
| SEQ. ID. NO. 27481 | 207-ThrIleThrValIleAlaSerLeuMetGlyLeuAsnGluPheHisGlyValValGlyGluValProGlyIle-230 |
| SEQ. ID. NO. 27482 | 242-LeuPheThrValSer-246 |
| SEQ. ID. NO. 27483 | 260-PheAspSerThrGlyThr-265 |
| SEQ. ID. NO. 27484 | 362-MetLeuArgSerAlaArgAspIle-369 |
| Antigenic Index - Jameson-Wolf | |
| SEQ. ID. NO. 27485 | 1-MetAspIleSerLysGlThrLeuLeu-9 |
| SEQ. ID. NO. 27486 | 16-LysAlaAsnGlyThrThrValArgThrGluLeu-26 |
| SEQ. ID. NO. 27487 | 125-LysValArgGluMetLeu-130 |

TABLE 1-continued

| | |
|---|---|
| SEQ. ID. NO. 27488 | 260-PheAspSerThrGly-264 |
| SEQ. ID. NO. 27489 | 277-ValAspGlyLysLeuProArgLeuLysArg-286 |
| SEQ. ID. NO. 27490 | 317-SerAlaGlyGlyArgThrGly-323 |
| SEQ. ID. NO. 27491 | 364-ArgSerAlaArgAspIleAspTrpAspAspMetThrGlu-376 |
| SEQ. ID. NO. 27492 | 410-LeuCysArgArgThrGlyAspValPro-418 |
| Hydrophilic Regions - Hopp-Woods | |
| SEQ. ID. NO. 27493 | 1-MetAspIleSerLys-5 |
| SEQ. ID. NO. 27494 | 17-AlaAsnGlyThrThrValArgThrGluLeu-26 |
| SEQ. ID. NO. 27495 | 125-LysValArgGluMetLeu-130 |
| SEQ. ID. NO. 27496 | 279-GlyLysLeuProArgLeuLysArg-286 |
| SEQ. ID. NO. 27497 | 318-AlaGlyGlyArgThr-322 |
| SEQ. ID. NO. 27498 | 364-ArgSerAlaArgAspIleAspTrpAspAspMetThrGlu-376 |
| SEQ. ID. NO. 27499 | 410-LeuCysArgArgThrGlyAsp-416 |
| g098 | |
| AMPHI Regions - AMPHI | |
| SEQ. ID. NO. 27500 | 33-AspGlnPheValGlyAspValAlaArg-41 |
| SEQ. ID. NO. 27501 | 62-ThrHisHisValHisArgMetGly-69 |
| Antigenic Index - Jameson-Wolf | |
| SEQ. ID. NO. 27502 | 25-GlnGlnAspAlaAlaGlnAlaGlyAspGlnPheVal-36 |
| SEQ. ID. NO. 27503 | 53-AsnAlaAlaGluHisGlyHisAlaGly-61 |
| SEQ. ID. NO. 27504 | 67-ArgMetGlyMetCysArg-72 |
| SEQ. ID. NO. 27505 | 79-AsnHisThrAspArgGlnAla-85 |
| Hydrophilic Regions - Hopp-Woods | |
| SEQ. ID. NO. 27506 | 26-GlnAspAlaAlaGlnAla-31 |
| SEQ. ID. NO. 27507 | 54-AlaAlaGluHisGlyHis-59 |
| SEQ. ID. NO. 27508 | 79-AsnHisThrAspArgGlnAla-85 |
| g099 | |
| AMPHI Regions - AMPHI | |
| SEQ. ID. NO. 27509 | 6-SerMetMetArgLeuProAspIleVal-14 |
| SEQ. ID. NO. 27510 | 47-AlaPheValGluPhePheGlyGluGly-55 |
| SEQ. ID. NO. 27511 | 102-LysLeuValGluThrTyrAlaLysThr-110 |
| SEQ. ID. NO. 27512 | 114-TrpAlaGlyGlyLeuLys-119 |
| SEQ. ID. NO. 27513 | 135-ThrArgAsnMetAlaGlyProSerAsn-143 |
| SEQ. ID. NO. 27514 | 154-AlaAlaLysGlyLeuAlaLysProTyrGluGluProSerAspGlyGln-169 |
| SEQ. ID. NO. 27515 | 178-AlaAlaIleThrSerCysThrAsnThrSerAsnProArgAsnVal-192 |
| SEQ. ID. NO. 27516 | 251-ThrCysAsnGlyMetSer-256 |
| SEQ. ID. NO. 27517 | 341-IleAspAlaIleValAlaGluTyr-348 |
| SEQ. ID. NO. 27518 | 350-LysProGlnGlnPheArgAspIle-357 |
| SEQ. ID. NO. 27519 | 371-ProSerProLeuTyrAspTrpArg-378 |
| SEQ. ID. NO. 27520 | 381-SerThrTyrIleArg-385 |
| SEQ. ID. NO. 27521 | 398-ArgThrLeuArgGlyMetArgProPro-406 |
| SEQ. ID. NO. 27522 | 443-AspPheAsnSerTyrAlaThr-449 |
| SEQ. ID. NO. 27523 | 468-PheAsnGluMetValArg-473 |
| SEQ. ID. NO. 27524 | 494-MetArgMetTrpGluAlaIleGluThrTyrMet-504 |
| SEQ. ID. NO. 27525 | 532-ArgLeuAlaGlyValGluAlaIle-539 |
| SEQ. ID. NO. 27526 | 541-AlaGluGlyPheGluArgIleHisArgThrAsn-551 |
| SEQ. ID. NO. 27527 | 575-GlyThrGluThrTyr-579 |
| Antigenic Index - Jameson-Wolf | |
| SEQ. ID. NO. 27528 | 18-LeuThrGlyLysArgGlnAla-24 |
| SEQ. ID. NO. 27529 | 38-PheLeuArgLysGluArgValVal-45 |
| SEQ. ID. NO. 27530 | 53-GlyGluGlyAlaArgSer-58 |
| SEQ. ID. NO. 27531 | 60-SerIleGlyAspArgAlaThr-66 |
| SEQ. ID. NO. 27532 | 70-MetThrProGluPhe-74 |
| SEQ. ID. NO. 27533 | 94-ThrGlyArgAspAspAlaGlnValLysLeu-103 |
| SEQ. ID. NO. 27534 | 133-SerValThrArgAsnMetAlaGlyProSerAsnProHis-145 |
| SEQ. ID. NO. 27535 | 157-GlyLeuAlaLysProTyrGluGluProSerAspGlyGlnMetProAspGly-173 |
| SEQ. ID. NO. 27536 | 183-CysThrAsnThrSerAsnProArgAsnVal-192 |
| SEQ. ID. NO. 27537 | 201-AsnAlaAsnArgLeuGlyLeuLysArgLysProTrpVal-213 |
| SEQ. ID. NO. 27538 | 216-SerPheAlaProGlySerLysValAla-224 |
| SEQ. ID. NO. 27539 | 235-ProGluMetGluLysLeu-240 |
| SEQ. ID. NO. 27540 | 251-ThrCysAsnGlyMetSerGlyAlaLeuAspProLysIleGlnGlnGluIleIleAspArgAspLeuTyr-273 |
| SEQ. ID. NO. 27541 | 279-SerGlyAsnArgAsnPheAspGlyArgIleHisProTyrAlaLys-293 |
| SEQ. ID. NO. 27542 | 312-IleArgPheAspIleGluAsnAspVal-320 |
| SEQ. ID. NO. 27543 | 322-GlyValAlaAspGlyArgGluIleArgLeuLysAspIleTrpProThrAspGluGluIleAsp-342 |
| SEQ. ID. NO. 27544 | 348-TyrValLysProGlnGlnPheArgAsp-356 |
| SEQ. ID. NO. 27545 | 361-MetSerAspThrGlyThrAlaGlnLysAlaProSerProLeuTyrAspTrpArgProMetSerThrTyrIleArgArgProProTyrTrp-390 |
| SEQ. ID. NO. 27546 | 394-LeuAlaGlyGluArgThrLeuArgGlyMetArgProProAlaIleLeuProAspAsnIleThrThrAspHisIleSerProSerAsn-422 |
| SEQ. ID. NO. 27547 | 438-GlyLeuProGluGluAspPheAsnSerTyrAlaThrHisArgGlyAspHisLeuThr-456 |
| SEQ. ID. NO. 27548 | 463-AlaAsnProLysLeuPhe-468 |
| SEQ. ID. NO. 27549 | 471-MetValArgAsnGluAspGlySerValArgGlnGlySerLeuAlaArgValGluProGluGlyGlnThr-493 |
| SEQ. ID. NO. 27550 | 503-TyrMetAsnArgLysGlnPro-509 |
| SEQ. ID. NO. 27551 | 516-AlaAspTyrGlyGlnGlySerSerArgAspTrpAlaAlaLysGlyValArg-532 |
| SEQ. ID. NO. 27552 | 542-GluGlyPheGluArgIleHisArgThrAsnLeu-552 |
| SEQ. ID. NO. 27553 | 562-PheLysProGlyThrAsnArgHisThrLeuGlnLeuAspGlyThrGluThrTyrAspValValGlyGluArgThrProArgCysGly-590 |
| SEQ. ID. NO. 27554 | 595-IleHisArgLysAsnGlyGluThrValGlu-604 |
| SEQ. ID. NO. 27555 | 607-ValThrCysArgProAspThrAlaGluGlu-616 |
| Hydrophilic Regions - Hopp-Woods | |
| SEQ. ID. NO. 27556 | 18-LeuThrGlyLysArgGlnAla-24 |
| SEQ. ID. NO. 27557 | 38-PheLeuArgLysGluArgValVal-45 |
| SEQ. ID. NO. 27558 | 53-GlyGluGlyAlaArg-57 |

TABLE 1-continued

| | |
|---|---|
| SEQ. ID. NO. 27559 | 60-SerIleGlyAspArgAlaThr-66 |
| SEQ. ID. NO. 27560 | 94-ThrGlyArgAspAspAlaGlnValLysLeu-103 |
| SEQ. ID. NO. 27561 | 157-GlyLeuAlaLysProTyrGluGluProSerAspGlyGlnMetPro-171 |
| SEQ. ID. NO. 27562 | 205-LeuGlyLeuLysArgLysProTrpVal-213 |
| SEQ. ID. NO. 27563 | 235-ProGluMetGluLysLeu-240 |
| SEQ. ID. NO. 27564 | 259-LeuAspProLysIleGlnGlnGluIleIleAspArgAspLeuTyr-273 |
| SEQ. ID. NO. 27565 | 282-ArgAsnPheAspGlyArgIle-288 |
| SEQ. ID. NO. 27566 | 312-IleArgPheAspIleGluAsnAspVal-320 |
| SEQ. ID. NO. 27567 | 324-AlaAspGlyArgGluIleArgLeuLysAsp-333 |
| SEQ. ID. NO. 27568 | 335-TrpProThrAspGluGluIleAsp-342 |
| SEQ. ID. NO. 27569 | 363-AspThrGlyThrAlaGlnLysAlaPro-371 |
| SEQ. ID. NO. 27570 | 394-LeuAlaGlyGluArgThrLeuArgGlyMetArg-404 |
| SEQ. ID. NO. 27571 | 438-GlyLeuProGluGluAspPheAsn-445 |
| SEQ. ID. NO. 27572 | 450-HisArgGlyAspHis-454 |
| SEQ. ID. NO. 27573 | 471-MetValArgAsnGluAspGlySerValArgGln-481 |
| SEQ. ID. NO. 27574 | 485-AlaArgValGluProGluGlyGlnThr-493 |
| SEQ. ID. NO. 27575 | 503-TyrMetAsnArgLysGlnPro-509 |
| SEQ. ID. NO. 27576 | 518-TyrGlyGlnGlySerSerArgAspTrpAlaAlaLysGlyValArg-532 |
| SEQ. ID. NO. 27577 | 542-GluGlyPheGluArgIleHisArg-549 |
| SEQ. ID. NO. 27578 | 564-ProGlyThrAsnArgHis-569 |
| SEQ. ID. NO. 27579 | 574-AspGlyThrGluThr-578 |
| SEQ. ID. NO. 27580 | 580-AspValValGlyGluArgThrProArg-588 |
| SEQ. ID. NO. 27581 | 596-HisArgLysAsnGlyGluThrValGlu-604 |
| SEQ. ID. NO. 27582 | 609-CysArgProAspThrAlaGluGlu-616 |
| g102 | |
| AMPHI Regions - AMPHI | |
| SEQ. ID. NO. 27583 | 26-ProAsnProThrAlaAsnLeuGlyAspGlyLeu-36 |
| SEQ. ID. NO. 27584 | 70-PheAspThrMetValLysAspLeuLeuGlyArgGlyTrpAsnIleIleAsnGlyIleAla-89 |
| SEQ. ID. NO. 27585 | 109-ThrAlaLysGlyIleGlySerAlaVal-117 |
| SEQ. ID. NO. 27586 | 128-LeuValPhePheGlyIleLeuAlaPheCys-137 |
| SEQ. ID. NO. 27587 | 144-LeuValAspArgPheThrGlyValLeu-152 |
| SEQ. ID. NO. 27588 | 155-GlyMetValLeuThr-159 |
| SEQ. ID. NO. 27589 | 207-AsnValSerSerLeuLeuLysTyrPheLys-216 |
| SEQ. ID. NO. 27590 | 221-LysValAlaLysSerIle-226 |
| SEQ. ID. NO. 27591 | 266-LeuAsnGluThrLeuSerLysPheAlaGlnThrGlyAspMetAspLysIleLeuSerLeuPheProTyr-288 |
| SEQ. ID. NO. 27592 | 300-LeuGlyLeuPheAspAsnIleAlaAspIlePheLysTrpAsnAsp-314 |
| SEQ. ID. NO. 27593 | 316-MetSerGlyArgGly-320 |
| SEQ. ID. NO. 27594 | 342-PhePheThrAlaIleGlyAla-348 |
| SEQ. ID. NO. 27595 | 374-GlyAlaGlyLysThrTyrLysVal-381 |
| Antigenic Index - Jameson-Wolf | |
| SEQ. ID. NO. 27596 | 1-MetSerAlaLysThrProSerLeu-8 |
| SEQ. ID. NO. 27597 | 26-ProAsnProThrAlaAsnLeuGlyAspGlyLeu-36 |
| SEQ. ID. NO. 27598 | 62-ThrHisAsnProArgGlyAlaSer-69 |
| SEQ. ID. NO. 27599 | 77-LeuLeuGlyArgGly-81 |
| SEQ. ID. NO. 27600 | 106-GlyAspLeuThrAla-110 |
| SEQ. ID. NO. 27601 | 169-AlaAspAlaLysPro-173 |
| SEQ. ID. NO. 27602 | 179-ThrGlnAlaProValGlyThr-185 |
| SEQ. ID. NO. 27603 | 214-TyrPheLysGlyAspAlaProLysValAla-223 |
| SEQ. ID. NO. 27604 | 246-SerAsnLeuProArgAsnGluPhe-253 |
| SEQ. ID. NO. 27605 | 258-AlaAlaGluArgGlnLeu-263 |
| SEQ. ID. NO. 27606 | 274-AlaGlnThrGlyAspMetAspLys-281 |
| SEQ. ID. NO. 27607 | 311-LysTrpAsnAspSerMetSerGlyArgGlyThrLys-322 |
| SEQ. ID. NO. 27608 | 369-SerProGlnLysIleGlyAlaGlyLysThrTyr-379 |
| Hydrophilic Regions - Hopp-Woods | |
| SEQ. ID. NO. 27609 | 1-MetSerAlaLysThr-5 |
| SEQ. ID. NO. 27610 | 62-ThrHisAsnProArgGlyAlaSer-69 |
| SEQ. ID. NO. 27611 | 169-AlaAspAlaLysPro-173 |
| SEQ. ID. NO. 27612 | 215-PheLysGlyAspAlaProLysValAla-223 |
| SEQ. ID. NO. 27613 | 247-AsnLeuProArgAsnGluPhe-253 |
| SEQ. ID. NO. 27614 | 258-AlaAlaGluArgGlnLeu-263 |
| SEQ. ID. NO. 27615 | 277-GlyAspMetAspLys-281 |
| SEQ. ID. NO. 27616 | 316-MetSerGlyArgGlyThrLys-322 |
| SEQ. ID. NO. 27617 | 371-GlnLysIleGlyAla-375 |
| g105 | |
| AMPHI Regions - AMPHI | |
| SEQ. ID. NO. 27618 | 11-TrpValGlyLeuGly-15 |
| SEQ. ID. NO. 27619 | 22-ValThrArgLeuLeuAsp-27 |
| SEQ. ID. NO. 27620 | 51-LysValTyrGlySerThrAlaGluLeuValArgAlaCys-63 |
| SEQ. ID. NO. 27621 | 74-AlaAlaValCysAspIleLeuAsnGlyValArgAspGlyLeu-87 |
| SEQ. ID. NO. 27622 | 97-ThrIleSerProThr-101 |
| SEQ. ID. NO. 27623 | 110-ValGluAlaAlaGlyGlyGlnPheAlaGluAlaProVal-122 |
| SEQ. ID. NO. 27624 | 143-AlaValLeuAsnProLeuGlnLysIlePheSer-153 |
| SEQ. ID. NO. 27625 | 162-PheGlyAspValGlyLysGlySer-169 |
| SEQ. ID. NO. 27626 | 176-AsnSerLeuLeuGlyIlePheGlyGluAlaTyr-186 |
| SEQ. ID. NO. 27627 | 203-IleValGluAlaIleGlyGlySerAla-211 |
| SEQ. ID. NO. 27628 | 249-LeuGluGlnAlaGlyAsnThrLeuProAlaValGlu-260 |
| SEQ. ID. NO. 27629 | 263-AlaAlaSerTyrArgLysAlaValGluAla-272 |
| Antigenic Index - Jameson-Wolf | |
| SEQ. ID. NO. 27630 | 25-LeuLeuAspGlyGlyIleGlu-31 |
| SEQ. ID. NO. 27631 | 34-ValTyrAsnArgSerProAspLysThrAlaProIleSerAlaLysGlyAlaLysValTyrGlySer-55 |

TABLE 1-continued

| | |
|---|---|
| SEQ. ID. NO. 27632 | 81-AsnGlyValArgAspGlyLeuAla-88 |
| SEQ. ID. NO. 27633 | 96-SerThrIleSerProThrGluAsnLeuAla-105 |
| SEQ. ID. NO. 27634 | 121-ProValSerGlySerValGlyProAlaThr-130 |
| SEQ. ID. NO. 27635 | 139-GlyGlySerGluAla-143 |
| SEQ. ID. NO. 27636 | 155-ValGlyLysLysThrPheHisPheGlyAspValGlyLysGlySerGly-170 |
| SEQ. ID. NO. 27637 | 196-PheGlyIleAspThrAspThrIleVal-204 |
| SEQ. ID. NO. 27638 | 210-SerAlaMetAspSerProMetPheGlnThrLysLysSerLeuTrpAlaAsnArgGluPheProPro-231 |
| SEQ. ID. NO. 27639 | 237-HisAlaSerLysAspLeuAsnLeuAlaValLysGluLeuGluGlnAlaGlyAsnThrLeuPro-257 |
| SEQ. ID. NO. 27640 | 264-AlaSerTyrArgLysAlaValGluAlaGlyTyrGlyGluGlnAspValSerGly-281 |
| Hydrophilic Regions - Hopp-Woods | |
| SEQ. ID. NO. 27641 | 25-LeuLeuAspGlyGlyIle-30 |
| SEQ. ID. NO. 27642 | 37-ArgSerProAspLysThrAlaProIleSerAlaLysGlyAlaLys-51 |
| SEQ. ID. NO. 27643 | 81-AsnGlyValArgAspGlyLeuAla-88 |
| SEQ. ID. NO. 27644 | 164-AspValGlyLysGlySerGly-170 |
| SEQ. ID. NO. 27645 | 196-PheGlyIleAspThrAspThrIle-203 |
| SEQ. ID. NO. 27646 | 218-GlnThrLysLysSerLeuTrpAla-225 |
| SEQ. ID. NO. 27647 | 237-HisAlaSerLysAspLeuAsnLeuAlaValLysGluLeuGluGlnAlaGly-253 |
| SEQ. ID. NO. 27648 | 265-SerTyrArgLysAlaValGlu-271 |
| SEQ. ID. NO. 27649 | 273-GlyTyrGlyGluGlnAspVal-279 |
| g109-2 | |
| AMPHI Regions - AMPHI | |
| SEQ. ID. NO. 27650 | 6-GlyThrTyrArgAspLeuHisArgProAlaSerGlu-17 |
| SEQ. ID. NO. 27651 | 53-LeuIleProAlaMetAlaGlyThrIleGly-62 |
| SEQ. ID. NO. 27652 | 143-GlyLeuLeuMetAla-147 |
| SEQ. ID. NO. 27653 | 154-IleMetAlaLysLeuThrSer-160 |
| SEQ. ID. NO. 27654 | 175-GlyThrThrGlyGlnValLysLysLeuPheSerTrpAlaGly-188 |
| SEQ. ID. NO. 27655 | 205-ValMetTyrAlaLeuLeuGluHisTrpLysLysArgTrpLeu-218 |
| SEQ. ID. NO. 27656 | 220-ValProLeuGlyCys-224 |
| SEQ. ID. NO. 27657 | 292-HisGlnValPheGlnLysIle-298 |
| SEQ. ID. NO. 27658 | 324-ValGlySerIleLeuGly-329 |
| SEQ. ID. NO. 27659 | 334-ThrSerSerTrpGlyThr-339 |
| SEQ. ID. NO. 27660 | 465-AlaValGlyMetLeuProGlyIleProProPheLeuGluGlnPheLysSerLeu-482 |
| Antigenic Index - Jameson-Wolf | |
| SEQ. ID. NO. 27661 | 1-MetGluLysHisAsnGlyThrTyrArgAspLeuHisArgProAlaSer-16 |
| SEQ. ID. NO. 27662 | 18-PheAlaThrArgAspGluTyrLeuGlu-26 |
| SEQ. ID. NO. 27663 | 32-MetGlnProLysArgTrpArgProAsnLeuProPheArgAspTyrArgPheGluTrp-50 |
| SEQ. ID. NO. 27664 | 76-LeuGlyLeuProAsp-80 |
| SEQ. ID. NO. 27665 | 107-ProGlyAlaAsnLeuProGlyThrHis-115 |
| SEQ. ID. NO. 27666 | 158-LeuThrSerAsnGlyVal-163 |
| SEQ. ID. NO. 27667 | 177-ThrGlyGlnValLysLys-182 |
| SEQ. ID. NO. 27668 | 243-AlaProGlyLeuProPro-248 |
| SEQ. ID. NO. 27669 | 254-TrpXxxGlyGluAsnSerGlyTrpHis-262 |
| SEQ. ID. NO. 27670 | 299-SerTyrProGluLysThrAspLysVal-307 |
| SEQ. ID. NO. 27671 | 310-AsnIleAspAspThrMetThr-316 |
| SEQ. ID. NO. 27672 | 350-ProIleProGlyGly-354 |
| SEQ. ID. NO. 27673 | 392-AlaGlyMetGluMetThrArgLysGlyLysThrThrGln-404 |
| SEQ. ID. NO. 27674 | 435-GlyCysLysGluArgSerAla-441 |
| Hydrophilic Regions - Hopp-Woods | |
| SEQ. ID. NO. 27675 | 1-MetGluLysHisAsnGlyThrTyrArgAspLeuHisArgProAlaSer-16 |
| SEQ. ID. NO. 27676 | 18-PheAlaThrArgAspGluTyrLeuGlu-26 |
| SEQ. ID. NO. 27677 | 35-LysArgTrpArgPro-39 |
| SEQ. ID. NO. 27678 | 44-ArgAspTyrArgPheGluTrp-50 |
| SEQ. ID. NO. 27679 | 178-GlyGlnValLysLys-182 |
| SEQ. ID. NO. 27680 | 299-SerTyrProGluLysThrAspLysVal-307 |
| SEQ. ID. NO. 27681 | 311-IleAspAspThrMetThr-316 |
| SEQ. ID. NO. 27682 | 392-AlaGlyMetGluMetThrArgLysGlyLysThrThrGln-404 |
| SEQ. ID. NO. 27683 | 435-GlyCysLysGluArgSerAla-441 |
| g111-2 | |
| AMPHI Regions - AMPHI | |
| SEQ. ID. NO. 27684 | 6-ArgLeuProAsnLeuIleArgAlaLeu-14 |
| SEQ. ID. NO. 27685 | 58-ProSerProAlaLysIleGlnLysArgIleAspAspAlaLeuLysGluValAsnArgGlnMetSer-79 |
| SEQ. ID. NO. 27686 | 90-PheAsnGlnHisThrAlaGly-96 |
| SEQ. ID. NO. 27687 | 128-GlyProLeuValAsnLeuTrp-134 |
| SEQ. ID. NO. 27688 | 151-IleLysGlnAlaAlaSerTyrThrGly-159 |
| SEQ. ID. NO. 27689 | 170-AspTyrAlaSerLeu-174 |
| SEQ. ID. NO. 27690 | 183-LeuAspLeuSerSerIleAlaLys-190 |
| SEQ. ID. NO. 27691 | 209-TyrLeuValGluIleGlyGly-215 |
| SEQ. ID. NO. 27692 | 314-GluThrGluAlaLeu-318 |
| SEQ. ID. NO. 27693 | 320-LeuAlaGluGlnGlu-324 |
| Antigenic Index - Jameson-Wolf | |
| SEQ. ID. NO. 27694 | 1-MetProSerGluThrArgLeuProAsnLeu-10 |
| SEQ. ID. NO. 27695 | 26-CysSerGluGlnThrAla-31 |
| SEQ. ID. NO. 27696 | 37-GlnGlyGluThrMetGly-42 |
| SEQ. ID. NO. 27697 | 49-TyrLeuSerAsnAsnArgAspLysLeuProSerProAlaLysIleGlnLysArgIleAspAspAlaLeuLysGluValAsnArgGlnMetSer-79 |
| SEQ. ID. NO. 27698 | 81-TyrGlnThrAspSerGluIleSerArgPheAsnGlnHisThrAlaGlyLysProLeuArgIleSerSerAspPhe-105 |
| SEQ. ID. NO. 27699 | 111-GluAlaValArgLeuAsnArg-117 |
| SEQ. ID. NO. 27700 | 135-GlyPheGlyProAspLysSerValThrArgGluProSerProGluGlnIleLysGln-153 |
| SEQ. ID. NO. 27701 | 164-IleLeuGlnGlnGlyLysAspTyrAlaSerLeuSerLysThrHisProLysAla-181 |
| SEQ. ID. NO. 27702 | 192-PheGlyValAspLysValAlaGlyGluLeuGluLysTyrGly-205 |
| SEQ. ID. NO. 27703 | 213-IleGlyGlyGluLeuHisGlyLysGlyLysAsnAlaHisGlyGluProTrpArgIleGlyIleGluGlnProAsn-237 |

TABLE 1-continued

| | |
|---|---|
| SEQ. ID. NO. 27704 | 250-LeuAsnAsnArgSerLeuAlaThrSerGlyAspTyrArg-262 |
| SEQ. ID. NO. 27705 | 264-PheHisValAspLysAsnGlyLysArgLeuSer-274 |
| SEQ. ID. NO. 27706 | 277-IleAsnProAsnAsnLysArgProIleSer-286 |
| SEQ. ID. NO. 27707 | 295-ValSerAspSerAlaMetThrAlaAspGlyLeuSer-306 |
| SEQ. ID. NO. 27708 | 314-GluThrGluAlaLeuArgLeuAlaGluGlnGluLys-325 |
| SEQ. ID. NO. 27709 | 332-ValArgAspLysAspGlyTyrArg-339 |
| SEQ. ID. NO. 27710 | 342-MetSerSerGluPhe-346 |
| Hydrophilic Regions - Hopp-Woods | |
| SEQ. ID. NO. 27711 | 1-MetProSerGluThrArgLeu-7 |
| SEQ. ID. NO. 27712 | 26-CysSerGluGlnThrAla-31 |
| SEQ. ID. NO. 27713 | 51-SerAsnAsnArgAspLysLeuProSer-59 |
| SEQ. ID. NO. 27714 | 61-AlaLysIleGlnLysArgIleAspAspAlaLeuLysGluValAsnArgGln-77 |
| SEQ. ID. NO. 27715 | 82-GlnThrAspSerGluIleSerArg-89 |
| SEQ. ID. NO. 27716 | 97-LysProLeuArgIleSerSer-103 |
| SEQ. ID. NO. 27717 | 111-GluAlaValArgLeuAsnArg-117 |
| SEQ. ID. NO. 27718 | 137-GlyProAspLysSerValThrArgGluProSerProGluGlnIleLysGln-153 |
| SEQ. ID. NO. 27719 | 167-GlnGlyLysAspTyrAlaSer-173 |
| SEQ. ID. NO. 27720 | 175-SerLysThrHisPro-179 |
| SEQ. ID. NO. 27721 | 192-PheGlyValAspLysValAlaGlyGluLeuGluLysTyrGly-205 |
| SEQ. ID. NO. 27722 | 217-LeuHisGlyLysGlyLysAsnAlaHis-225 |
| SEQ. ID. NO. 27723 | 267-AspLysAsnGlyLysArgLeuSer-274 |
| SEQ. ID. NO. 27724 | 279-ProAsnAsnLysArgProIle-285 |
| SEQ. ID. NO. 27725 | 314-GluThrGluAlaLeuArgLeuAlaGluGlnGluLys-325 |
| SEQ. ID. NO. 27726 | 332-ValArgAspLysAspGlyTyrArg-339 |
| g117-1 | |
| AMPHI Regions - AMPHI | |
| SEQ. ID. NO. 27727 | 6-ProIleGlnAspThrGlnSerAla-13 |
| SEQ. ID. NO. 27728 | 15-LeuGlnGluLeuArgGluTrpPheAspSerTyrCysAla-27 |
| SEQ. ID. NO. 27729 | 57-GlyGluProLeuProAspHis-63 |
| SEQ. ID. NO. 27730 | 69-GlnMetValAspGluLeuAspLeuLeu-77 |
| SEQ. ID. NO. 27731 | 79-AspAlaValAlaAlaThrLeuLeuAlaAspIleGlyArgTyr-92 |
| SEQ. ID. NO. 27732 | 104-CysAsnSerThrValAlaGluLeuValLysGlyValAspGluValGlnLysLeuThrHisPheAlaArgValAspSerLeu-130 |
| SEQ. ID. NO. 27733 | 145-LysMetLeuLeuAlaMet-150 |
| SEQ. ID. NO. 27734 | 170-PheLeuSerAsnAlaProAspSerProGluLys-180 |
| SEQ. ID. NO. 27735 | 216-GluProGluLysTyrArg-221 |
| SEQ. ID. NO. 27736 | 234-ArgLeuGluTyrIleGluAsnPheLeuAspIleLeuArg-246 |
| SEQ. ID. NO. 27737 | 260-GlyArgProLysHisIleTyrSerIleTyrLys-270 |
| SEQ. ID. NO. 27738 | 282-LeuPheAspIleArg-286 |
| SEQ. ID. NO. 27739 | 290-IleLeuValAspThrValProGluCysTyrThrThrLeuGlyIleValHisSerLeuTrpGlnProIleProGlyGluPheAspAspTyrIleAla-321 |
| SEQ. ID. NO. 27740 | 327-GlyTyrLysSerLeuHisThr-333 |
| SEQ. ID. NO. 27741 | 351-AspMetHisGlnPheAsnGluPheGlyValAla-361 |
| SEQ. ID. NO. 27742 | 385-GlnLeuLeuAspTrp-389 |
| SEQ. ID. NO. 27743 | 440-HisSerSerIleGlyAspArg-446 |
| SEQ. ID. NO. 27744 | 489-ValLysSerGlyLysAlaIleGlyLysIleArgAlaTyr-501 |
| SEQ. ID. NO. 27745 | 504-GlnGlnAsnAlaAsp-508 |
| SEQ. ID. NO. 27746 | 521-GlnLeuAlaLysLeu-525 |
| SEQ. ID. NO. 27747 | 532-GlnGluLeuAlaGlu-536 |
| SEQ. ID. NO. 27748 | 539-GlyTyrLysLysProGluAspLeuTyrThr-548 |
| SEQ. ID. NO. 27749 | 557-AsnArgAlaIleGlnLysAlaCysGlyThrLeuAsnGluProPro-571 |
| SEQ. ID. NO. 27750 | 585-LysIleLysLysGlyGly-590 |
| SEQ. ID. NO. 27751 | 603-MetThrThrLeuAlaLysCysCysLysProAlaProProAspAspIleAlaGly-620 |
| SEQ. ID. NO. 27752 | 637-SerPheArgHisLeuAlaGluHisAlaProGluLysValLeuAspAla-652 |
| SEQ. ID. NO. 27753 | 679-ArgAspValSerAspAla-684 |
| SEQ. ID. NO. 27754 | 714-GlnValAsnAspLeuProArgValLeuAlaGlyLeuGlyAspValLysGlyValLeuSerValThrArg-736 |
| Antigenic Index - Jameson-Wolf | |
| SEQ. ID. NO. 27755 | 5-SerProIleGlnAspThrGlnSerAlaThr-14 |
| SEQ. ID. NO. 27756 | 16-GlnGluLeuArgGluTrpPheAspSerTyrCysAlaAlaLeuProAspAsnAspLysAsnLeu-36 |
| SEQ. ID. NO. 27757 | 46-GluHisTyrProAla-50 |
| SEQ. ID. NO. 27758 | 52-AlaAlaThrProTyrGlyGluProLeuProAspHisPhe-64 |
| SEQ. ID. NO. 27759 | 70-MetValAspGluLeuAspLeuLeuPro-78 |
| SEQ. ID. NO. 27760 | 88-AspIleGlyArgTyrValProAspTrp-96 |
| SEQ. ID. NO. 27761 | 100-ValSerGluArgCysAsnSerThrVal-108 |
| SEQ. ID. NO. 27762 | 110-GluLeuValLysGlyValAspGluValGlnLys-120 |
| SEQ. ID. NO. 27763 | 125-AlaArgValAspSerLeuAlaThrProGluGluArgAlaGlnGlnAlaGluThrMetArg-144 |
| SEQ. ID. NO. 27764 | 162-AlaMetArgThrArgThr-167 |
| SEQ. ID. NO. 27765 | 173-AsnAlaProAspSerProGluLysArgAlaValAlaLysGluThrLeu-188 |
| SEQ. ID. NO. 27766 | 209-AspLeuGlyPheArgHisGlnGluProGluLysTyrArgGlu-222 |
| SEQ. ID. NO. 27767 | 227-LeuAspGluLysArgThrGluArgLeuGluTyr-237 |
| SEQ. ID. NO. 27768 | 245-LeuArgThrGluLeuLysLys-251 |
| SEQ. ID. NO. 27769 | 258-ValAlaGlyArgProLysHis-264 |
| SEQ. ID. NO. 27770 | 271-LysMetValLysLysLysLeuSerPhe-279 |
| SEQ. ID. NO. 27771 | 294-ThrValProGluCysTyr-299 |
| SEQ. ID. NO. 27772 | 311-ProIleProGlyGluPheAspAspTyrIleAlaAsnProLysGlyAsnGlyTyrLysSer-330 |
| SEQ. ID. NO. 27773 | 335-IleValGlyProGluGluLysGlyValGluValGlnIleArgThr-349 |
| SEQ. ID. NO. 27774 | 364-TrpArgTyrLysGluGlyGlyLysGlyAspSerAlaTyrGluGlnLys-379 |
| SEQ. ID. NO. 27775 | 387-LeuAspTrpArgGluAsnMetAlaGluSerGlyLysGluAspLeuAlaAla-403 |
| SEQ. ID. NO. 27776 | 418-ThrProHisGlyLys-422 |
| SEQ. ID. NO. 27777 | 440-HisSerSerIleGlyAspArgCysArgGlyAlaLysValGluGly-454 |
| SEQ. ID. NO. 27778 | 461-ThrProLeuGluAsnGlyGlnArgValGluIleIleThrAlaLysGluGlyHisProSerValAsn-482 |
| SEQ. ID. NO. 27779 | 487-GlyTrpValLysSerGlyLysAlaIleGlyLys-497 |

TABLE 1-continued

| | |
|---|---|
| SEQ. ID. NO. 27780 | 502-IleArgGlnGlnAsnAlaAspThrValArgGluGluGlyArgValGlnLeuAspLysGlnLeuAla-523 |
| SEQ. ID. NO. 27781 | 525-LeuThrProLysProAsnLeuGlnGluLeuAlaGlu-536 |
| SEQ. ID. NO. 27782 | 538-LeuGlyTyrLysLysProGluAspLeu-546 |
| SEQ. ID. NO. 27783 | 551-GlyGlnGlyGluIleSerAsnArgAlaIleGlnLysAlaCysGlyThrLeuAsnGluProProProVal-573 |
| SEQ. ID. NO. 27784 | 582-LysGlnSerLysIleLysLysGlyGlyLysThr-592 |
| SEQ. ID. NO. 27785 | 596-IleAspGlyGluAspGlyLeu-602 |
| SEQ. ID. NO. 27786 | 608-LysCysCysLysProAlaProProAspAspIleAla-619 |
| SEQ. ID. NO. 27787 | 622-ValThrArgGluArgGlyIleSerValHisArgLysThrCysProSerPhe-638 |
| SEQ. ID. NO. 27788 | 644-HisAlaProGluLysValLeuAsp-651 |
| SEQ. ID. NO. 27789 | 667-IleGluIleArgAlaGlnAspArgSerGlyLeuLeuArgAspValSerAspAlaLeuAlaArgHisLysLeu-690 |
| SEQ. ID. NO. 27790 | 696-GlnThrGlnSerArgAspLeuGluAlaSerMet-706 |
| SEQ. ID. NO. 27791 | 710-LeuGluValLysGlnValAsnAspLeuProArg-720 |
| SEQ. ID. NO. 27792 | 726-GlyAspValLysGly-730 |
| Hydrophilic Regions - Hopp-Woods | |
| SEQ. ID. NO. 27793 | 8-GlnAspThrGlnSer-12 |
| SEQ. ID. NO. 27794 | 16-GlnGluLeuArgGluTrpPhe-22 |
| SEQ. ID. NO. 27795 | 30-ProAspAsnAspLysAsnLeu-36 |
| SEQ. ID. NO. 27796 | 70-MetValAspGluLeuAspLeuLeuPro-78 |
| SEQ. ID. NO. 27797 | 100-ValSerGluArgCysAsnSerThr-107 |
| SEQ. ID. NO. 27798 | 110-GluLeuValLysGlyValAspGluValGlnLys-120 |
| SEQ. ID. NO. 27799 | 125-AlaArgValAspSer-129 |
| SEQ. ID. NO. 27800 | 131-AlaThrProGluGluArgAlaGlnGlnAlaGluThrMetArg-144 |
| SEQ. ID. NO. 27801 | 162-AlaMetArgThrArgThr-167 |
| SEQ. ID. NO. 27802 | 174-AlaProAspSerProGluLysArgAlaValAlaLysGluThrLeu-188 |
| SEQ. ID. NO. 27803 | 209-AspLeuGlyPheArgHisGlnGluProGluLysTyrArgGlu-222 |
| SEQ. ID. NO. 27804 | 227-LeuAspGluLysArgThrGluArgLeuGluTyr-237 |
| SEQ. ID. NO. 27805 | 245-LeuArgThrGluLeuLysLys-251 |
| SEQ. ID. NO. 27806 | 258-ValAlaGlyArgProLysHis-264 |
| SEQ. ID. NO. 27807 | 271-LysMetValLysLysLysLeuSerPhe-279 |
| SEQ. ID. NO. 27808 | 314-GlyGluPheAspAsp-318 |
| SEQ. ID. NO. 27809 | 323-ProLysGlyAsnGly-327 |
| SEQ. ID. NO. 27810 | 337-GlyProGluGluLysGlyValGluValGlnIleArgThr-349 |
| SEQ. ID. NO. 27811 | 365-ArgTyrLysGluGlyGlyLysGlyAspSerAlaTyrGluGln-378 |
| SEQ. ID. NO. 27812 | 387-LeuAspTrpArgGluAsnMetAlaGluSerGlyLysGluAspLeuAlaAla-403 |
| SEQ. ID. NO. 27813 | 443-IleGlyAspArgCysArgGlyAlaLysValGluGly-454 |
| SEQ. ID. NO. 27814 | 463-LeuGluAsnGlyGlnArgValGluIleIleThrAlaLysGluGlyHisPro-479 |
| SEQ. ID. NO. 27815 | 489-ValLysSerGlyLysAlaIleGlyLys-497 |
| SEQ. ID. NO. 27816 | 505-GlnAsnAlaAspThrValArgGluGluGlyArgValGlnLeuAspLysGlnLeuAla-523 |
| SEQ. ID. NO. 27817 | 538-LeuGlyTyrLysLysProGluAspLeu-546 |
| SEQ. ID. NO. 27818 | 553-GlyGluIleSerAsn-557 |
| SEQ. ID. NO. 27819 | 582-LysGlnSerLysIleLysLysGlyGlyLys-591 |
| SEQ. ID. NO. 27820 | 596-IleAspGlyGluAspGlyLeu-602 |
| SEQ. ID. NO. 27821 | 608-LysCysCysLysProAlaProProAspAspIle-618 |
| SEQ. ID. NO. 27822 | 622-ValThrArgGluArgGlyIleSerValHisArgLysThrCysPro-636 |
| SEQ. ID. NO. 27823 | 644-HisAlaProGluLysValLeu-650 |
| SEQ. ID. NO. 27824 | 667-IleGluIleArgAlaGlnAspArgSerGlyLeuLeuArgAspValSerAspAlaLeuAlaArgHisLysLeu-690 |
| SEQ. ID. NO. 27825 | 697-ThrGlnSerArgAspLeuGluAlaSerMet-706 |
| SEQ. ID. NO. 27826 | 710-LeuGluValLysGlnValAsnAspLeuProArg-720 |
| SEQ. ID. NO. 27827 | 726-GlyAspValLysGly-730 |
| g118 | |
| AMPHI Regions - AMPHI | |
| SEQ. ID. NO. 27828 | 24-GlyLysTrpTyrAsp-28 |
| SEQ. ID. NO. 27829 | 57-IleProArgAspIle-61 |
| SEQ. ID. NO. 27830 | 65-IleGlyThrIleIleAspPheLeuMetValProAsn-76 |
| SEQ. ID. NO. 27831 | 94-IleHisGluArgTyrGluArgPheThrThrMetLeuArg-106 |
| Antigenic Index - Jameson-Wolf | |
| SEQ. ID. NO. 27832 | 2-CysGluPheLysAspPheArgArgAsnIleProCys-13 |
| SEQ. ID. NO. 27833 | 15-GluGluTyrAspGluAsnSerPhe-22 |
| SEQ. ID. NO. 27834 | 24-GlyLysTrpTyrAspAspGlyValTrpAspAspGluGluTyrTrpLysLeuGluAsnAspLeuIleGluValArgArgLysTyrProTyrProMetAsp IleProArgAspIle-61 |
| SEQ. ID. NO. 27835 | 86-ProTrpLeuProAspSerValGlyIleHisGluArgTyrGluArg-100 |
| SEQ. ID. NO. 27836 | 109-PheThrGluLysAspIleVal-115 |
| SEQ. ID. NO. 27837 | 119-PheAspTyrTyrAsnLysLys-125 |
| Hydrophilic Regions - Hopp-Woods | |
| SEQ. ID. NO. 27838 | 2-CysGluPheLysAspPheArgArgAsnIleProCys-13 |
| SEQ. ID. NO. 27839 | 15-GluGluTyrAspGlu-19 |
| SEQ. ID. NO. 27840 | 30-GlyValTrpAspAspGluGluTyrTrpLysLeuGluAsnAspLeuIleGluValArgArgLysTyrProTyr-53 |
| SEQ. ID. NO. 27841 | 96-GluArgTyrGluArg-100 |
| SEQ. ID. NO. 27842 | 109-PheThrGluLysAspIleVal-115 |
| SEQ. ID. NO. 27843 | 121-TyrTyrAsnLysLys-125 |
| g120 | |
| AMPHI Regions - AMPHI | |
| SEQ. ID. NO. 27844 | 6-LysAsnIlePheSerAla-11 |
| SEQ. ID. NO. 27845 | 49-SerGlyAsnAlaTyrLysIleValSerThrIleLys-60 |
| SEQ. ID. NO. 27846 | 77-AsnThrLeuHisProAlaTyrTyrLysAspIleArgArg-89 |
| SEQ. ID. NO. 27847 | 142-IleThrAsnGlyLysLysLeuTyrSerValGlyGlyLeuAsnLysAlaGly-158 |
| SEQ. ID. NO. 27848 | 188-AlaProSerLeuAsnAsnIleProAla-196 |
| Antigenic Index - Jameson-Wolf | |
| SEQ. ID. NO. 27849 | 35-SerGlySerTyrGly-39 |
| SEQ. ID. NO. 27850 | 45-ThrPheGluArgSerGlyAsnAlaTyrLys-54 |

TABLE 1-continued

| | |
|---|---|
| SEQ. ID. NO. 27851 | 68-PheGluSerGlyGlyThrValVal-75 |
| SEQ. ID. NO. 27852 | 83-TyrTyrLysAspIleArgArgGlyLysLeuTyrAla-94 |
| SEQ. ID. NO. 27853 | 97-LysPheAlaAspGlySerValThrTyrGlyLysAlaGlyGluSerLysThrGluGlnSerProLysAla-119 |
| SEQ. ID. NO. 27854 | 131-AlaAsnAspAlaLysLeuProProGlyLeuLysIleThrAsnGlyLysLysLeuTyrSer-150 |
| SEQ. ID. NO. 27855 | 153-GlyLeuAsnLysAlaGlyThrGlyLysTyrSerIleGlyGlyValGluThrGluValValLysTyrArgValArgArgGlyAspAspThrVal-183 |
| SEQ. ID. NO. 27856 | 199-GlyTyrThrAspAspGlyLysThrTyr-207 |
| SEQ. ID. NO. 27857 | 218-GlyGlnAlaAlaLysPro-223 |
| Hydrophilic Regions - Hopp-Woods | |
| SEQ. ID. NO. 27858 | 45-ThrPheGluArgSerGlyAsn-51 |
| SEQ. ID. NO. 27859 | 85-LysAspIleArgArgGlyLysLeuTyrAla-94 |
| SEQ. ID. NO. 27860 | 107-LysAlaGlyGluSerLysThrGluGlnSerProLysAla-119 |
| SEQ. ID. NO. 27861 | 131-AlaAsnAspAlaLysLeu-136 |
| SEQ. ID. NO. 27862 | 143-ThrAsnGlyLysLysLeuTyr-149 |
| SEQ. ID. NO. 27863 | 155-AsnLysAlaGlyThrGly-160 |
| SEQ. ID. NO. 27864 | 167-ValGluThrGluValValLysTyrArgValArgArgGlyAspAspThr-182 |
| SEQ. ID. NO. 27865 | 200-TyrThrAspAspGlyLysThrTyr-207 |
| SEQ. ID. NO. 27866 | 219-GlnAlaAlaLysPro-223 |
| g121-1 | |
| AMPHI Regions - AMPHI | |
| SEQ. ID. NO. 27867 | 40-ProTyrProAspArgLeuArgArgLysLeu-49 |
| SEQ. ID. NO. 27868 | 68-GlnGluLeuSerArgLeuTyrAlaGlnThr-77 |
| SEQ. ID. NO. 27869 | 101-ThrValArgHisAlaPro-106 |
| SEQ. ID. NO. 27870 | 117-LeuProLeuLeuAlaGluLeuThrArgIlePheThrValGly-130 |
| SEQ. ID. NO. 27871 | 148-ProAlaPheHisGlu-152 |
| SEQ. ID. NO. 27872 | 167-IleGlyGlyIleAlaAsnIleSerVal-175 |
| SEQ. ID. NO. 27873 | 189-ProGlyAsnMetLeuMetAspAlaTrpThr-198 |
| SEQ. ID. NO. 27874 | 216-GlyAsnIleLeuProGlnLeuLeuGlyArgLeuLeuAlaHisPro-230 |
| SEQ. ID. NO. 27875 | 236-HisProLysSerThrGly-241 |
| SEQ. ID. NO. 27876 | 251-GluThrTyrLeuAsp-255 |
| SEQ. ID. NO. 27877 | 262-AspValLeuArgThrLeuSerArgPheThrAlaGlnThrValTrpAspAlaValSerHis-281 |
| SEQ. ID. NO. 27878 | 303-AlaAspLeuAlaGluCysPhe-309 |
| SEQ. ID. NO. 27879 | 341-IleAsnArgIleProGlySerPro-348 |
| Antigenic Index - Jameson-Wolf | |
| SEQ. ID. NO. 27880 | 13-ThrSerMetAspGlyAlaAsp-19 |
| SEQ. ID. NO. 27881 | 23-ValArgMetAspGlyGlyLysTrpLeuGly-32 |
| SEQ. ID. NO. 27882 | 40-ProTyrProAspArgLeuArgArgLysLeuLeuAspLeuGlnAspThrGlyThrAspGluLeuHisArgSerArgMetLeuSer-67 |
| SEQ. ID. NO. 27883 | 85-GlnAsnLeuAlaProCysAsp-91 |
| SEQ. ID. NO. 27884 | 97-CysHisGlyGlnThrValArgHisAlaProGluHisGlyTyrSer-111 |
| SEQ. ID. NO. 27885 | 128-ThrValGlyAspPheArgSerArgAspLeuAlaAlaGlyGlyGlnGly-143 |
| SEQ. ID. NO. 27886 | 154-LeuPheArgAspAspArgGluThrArgVal-163 |
| SEQ. ID. NO. 27887 | 186-AspThrGlyProGlyAsnMet-192 |
| SEQ. ID. NO. 27888 | 205-ProTyrAspLysAsnGlyAlaLysAlaAlaGlnGlyAsn-217 |
| SEQ. ID. NO. 27889 | 235-ProHisProLysSerThrGlyArgGlu-243 |
| SEQ. ID. NO. 27890 | 253-TyrLeuAspGlyGlyGluAsnArgTyrAspValLeuArgThrLeuSer-268 |
| SEQ. ID. NO. 27891 | 283-AlaAlaAspAlaArgGln-288 |
| SEQ. ID. NO. 27892 | 293-GlyGlyGlyIleArgAsnProValLeu-301 |
| SEQ. ID. NO. 27893 | 344-IleProGlySerProHisLysAlaThrGlyAlaSerLysProCysIle-359 |
| Hydrophilic Regions - Hopp-Woods | |
| SEQ. ID. NO. 27894 | 13-ThrSerMetAspGlyAlaAsp-19 |
| SEQ. ID. NO. 27895 | 41-TyrProAspArgLeuArgArgLysLeuLeuAspLeuGlnAspThrGlyThrAspGluLeuHisArgSerArgMetLeuSer-67 |
| SEQ. ID. NO. 27896 | 101-ThrValArgHisAlaPro-106 |
| SEQ. ID. NO. 27897 | 131-AspPheArgSerArgAspLeuAlaAla-139 |
| SEQ. ID. NO. 27898 | 154-LeuPheArgAspAspArgGluThrArgVal-163 |
| SEQ. ID. NO. 27899 | 206-TyrAspLysAsnGlyAlaLysAlaAlaGln-215 |
| SEQ. ID. NO. 27900 | 235-ProHisProLysSerThrGlyArgGlu-243 |
| SEQ. ID. NO. 27901 | 254-LeuAspGlyGlyGluAsnArgTyrAspVal-263 |
| SEQ. ID. NO. 27902 | 283-AlaAlaAspAlaArgGln-288 |
| SEQ. ID. NO. 27903 | 345-ProGlySerProHisLysAlaThrGlyAlaSerLys-356 |
| g122-1 | |
| AMPHI Regions - AMPHI | |
| SEQ. ID. NO. 27904 | 6-AsnIleHisLysThrPhe-11 |
| SEQ. ID. NO. 27905 | 42-ThrPheLeuArgCysLeuAsnAlaLeuGluMetProGlu-54 |
| SEQ. ID. NO. 27906 | 102-LeuGluAsnValMetGlu-107 |
| SEQ. ID. NO. 27907 | 126-LysLeuLeuGluLys-130 |
| SEQ. ID. NO. 27908 | 176-ProGluLeuValGlnAspValLeuAspAlaMetLysGluLeuAlaArgGluGly-193 |
| SEQ. ID. NO. 27909 | 227-ProLysGluLeuPheAspHisLeuLysHisGlu-237 |
| Antigenic Index - Jameson-Wolf | |
| SEQ. ID. NO. 27910 | 5-ArgAsnIleHisLysThrPheGlyGluAsnThrIle-16 |
| SEQ. ID. NO. 27911 | 20-IleAspLeuAspValGlyLysGlyGln-28 |
| SEQ. ID. NO. 27912 | 34-GlyProSerGlySerGlyLysThrThr-42 |
| SEQ. ID. NO. 27913 | 51-GluMetProGluAspGlyGlnIleGluPheAspAsnAlaArgProLeuArgIleAspPheSerLysLysThrSerLysHisAsp-78 |
| SEQ. ID. NO. 27914 | 81-AlaLeuArgArgLysSerGlyMet-88 |
| SEQ. ID. NO. 27915 | 96-PheProHisLysThrValLeu-102 |
| SEQ. ID. NO. 27916 | 114-GlyLysProAlaAlaGlnAlaArgGluGluAlaLeuLysLeuLeuGlu-129 |
| SEQ. ID. NO. 27917 | 131-ValGlyLeuGlyAspLysValAspLeuTyr-140 |
| SEQ. ID. NO. 27918 | 142-TyrGlnLeuSerGlyGlyGlnGlnGlnArgValGlyIle-154 |
| SEQ. ID. NO. 27919 | 168-AspGluProThrSerAlaLeuAspProGluLeuVal-179 |
| SEQ. ID. NO. 27920 | 182-ValLeuAspAlaMetLysGluLeuAlaArgGluGlyTrp-194 |
| SEQ. ID. NO. 27921 | 216-MetAspGlyGlyVal-220 |

TABLE 1-continued

| | |
|---|---|
| SEQ. ID. NO. 27922 | 222-ValGluGlnGlSerProLysGluLeuPheAsp-232 |
| SEQ. ID. NO. 27923 | 234-LeuLysHisGluArgThrArgArgPheLeu-243 |
| Hydrophilic Regions - Hopp-Woods | |
| SEQ. ID. NO. 27924 | 20-IleAspLeuAspValGlyLys-26 |
| SEQ. ID. NO. 27925 | 51-GluMetProGluAspGlyGlnIleGluPheAspAsnAlaArgProLeuArgIleAspPheSerLysLysThrSerLysHisAsp-78 |
| SEQ. ID. NO. 27926 | 81-AlaLeuArgArgLysSerGly-87 |
| SEQ. ID. NO. 27927 | 114-GlyLysProAlaAlaGlnAlaArgGluGluAlaLeuLysLeuLeuGlu-129 |
| SEQ. ID. NO. 27928 | 131-ValGlyLeuGlyAspLysValAsp-138 |
| SEQ. ID. NO. 27929 | 168-AspGluProThrSerAlaLeuAspProGluLeuVal-179 |
| SEQ. ID. NO. 27930 | 182-ValLeuAspAlaMetLysGluLeuAlaArg-191 |
| SEQ. ID. NO. 27931 | 224-GlnGlySerProLysGluLeuPheAsp-232 |
| SEQ. ID. NO. 27932 | 234-LeuLysHisGluArgThrArgArgPheLeu-243 |
| g126-1 | |
| AMPHI Regions - AMPHI | |
| SEQ. ID. NO. 27933 | 26-LeuLysGlnSerValArg-31 |
| SEQ. ID. NO. 27934 | 73-GlyCysGlnSerValGlnGluAla-80 |
| SEQ. ID. NO. 27935 | 112-PheGlnLeuValGluAla-117 |
| SEQ. ID. NO. 27936 | 143-LeuAspAlaGlyCysGln-148 |
| SEQ. ID. NO. 27937 | 150-LeuMetProTrpAlaAlaProIleGlyThrGlyLeuGlyAlaVal-164 |
| SEQ. ID. NO. 27938 | 213-SerGlyAspProValAsnMetAlaArgAlaPhe-223 |
| Antigenic Index - Jameson-Wolf | |
| SEQ. ID. NO. 27939 | 7-GluThrPheProSerArgLeu-13 |
| SEQ. ID. NO. 27940 | 24-GluIleLeuLysGlnSerValArgThrAlaArg-34 |
| SEQ. ID. NO. 27941 | 41-SerLeuArgArgThrGlyCysGlyGlyGluAlaHisGlyGlnGlyPhe-56 |
| SEQ. ID. NO. 27942 | 85-GlnMetAlaArgGluValPheGlu-92 |
| SEQ. ID. NO. 27943 | 99-GluLeuIleGlyAspAspAspThrLeuGln-108 |
| SEQ. ID. NO. 27944 | 121-LeuIleLysAspGlyPheLysValLeu-129 |
| SEQ. ID. NO. 27945 | 141-ArgLeuLeuAspAlaGlyCys-147 |
| SEQ. ID. NO. 27946 | 171-IleLeuArgGluArgLeuProAspThrProLeu-181 |
| SEQ. ID. NO. 27947 | 209-AlaValSerArgSerGlyAspProValAsn-218 |
| SEQ. ID. NO. 27948 | 228-GluSerGlyArgLeuAlaPhe-234 |
| SEQ. ID. NO. 27949 | 237-GlyProValGluAlaArghrLysAlaGlnAlaSerThrProThrVal-252 |
| Hydrophilic Regions - Hopp-Woods | |
| SEQ. ID. NO. 27950 | 24-GluIleLeuLysGlnSerValArgThrAlaArg-34 |
| SEQ. ID. NO. 27951 | 41-SerLeuArgArgThrGlyCysGlyGlyGluAlaHis-52 |
| SEQ. ID. NO. 27952 | 85-GlnMetAlaArgGluValPheGlu-92 |
| SEQ. ID. NO. 27953 | 100-LeuIleGlyAspAspAspThrLeuGln-108 |
| SEQ. ID. NO. 27954 | 171-IleLeuArgGluArgLeuProAsp-178 |
| SEQ. ID. NO. 27955 | 210-ValSerArgSerGlyAspPro-216 |
| SEQ. ID. NO. 27956 | 228-GluSerGlyArgLeuAlaPhe-234 |
| SEQ. ID. NO. 27957 | 237-GlyProValGluAlaArgThrLysAlaGlnAla-247 |
| g127 | |
| AMPHI Regions - AMPHI | |
| SEQ. ID. NO. 27958 | 6-MetLeuAsnThrTrpProAsp-12 |
| SEQ. ID. NO. 27959 | 22-GluSerValAlaAla-26 |
| SEQ. ID. NO. 27960 | 119-ValGlyAspTyrIleGluIle-125 |
| SEQ. ID. NO. 27961 | 135-IleAsnLeuLeuAsnThrLeuMet-142 |
| SEQ. ID. NO. 27962 | 147-ProAsnProLeuValGlyGlnLeuAla-155 |
| SEQ. ID. NO. 27963 | 206-LeuGluProLeuCysAlaPro-212 |
| SEQ. ID. NO. 27964 | 214-IleProAlaIleGlnArgTyrLeuGluAsnValGln-225 |
| SEQ. ID. NO. 27965 | 250-ArgIleIleValArgPheAlaSerProVal-259 |
| SEQ. ID. NO. 27966 | 268-AlaValMetAspGluPheLeuArgVal-276 |
| Antigenic Index - Jameson-Wolf | |
| SEQ. ID. NO. 27967 | 14-ValProIleArgAlaGluAlaAlaGlu-22 |
| SEQ. ID. NO. 27968 | 41-HisPheArgArgHisProAspPheGlyIleGluSerLysArgArgPheLeuVal-58 |
| SEQ. ID. NO. 27969 | 112-SerAlaThrGlnGlnTyrSerVal-119 |
| SEQ. ID. NO. 27970 | 126-AsnGlyLeuArgGlyArgValValAsp-134 |
| SEQ. ID. NO. 27971 | 169-HisProValArgArgAspAsnIleLeu-177 |
| SEQ. ID. NO. 27972 | 193-LeuAspSerAspGluAlaValCysArg-201 |
| SEQ. ID. NO. 27973 | 234-AlaAlaArgProArgValThrArgValProTyrAspAspLysAlaTyr-249 |
| SEQ. ID. NO. 27974 | 257-SerProValSerLysArgLeuGluIle-265 |
| SEQ. ID. NO. 27975 | 282-AsnHisProAlaGlySerGluThrLeu-290 |
| Hydrophilic Regions - Hopp-Woods | |
| SEQ. ID. NO. 27976 | 14-ValProIleArgAlaGluAlaAlaGlu-22 |
| SEQ. ID. NO. 27977 | 42-PheArgArgHisProAspPheGlyIleGluSerLysArgArgPheLeuVal-58 |
| SEQ. ID. NO. 27978 | 126-AsnGlyLeuArgGlyArgValVal-133 |
| SEQ. ID. NO. 27979 | 170-ProValArgArgAspAsnIleLeu-177 |
| SEQ. ID. NO. 27980 | 193-LeuAspSerAspGluAlaValCysArg-201 |
| SEQ. ID. NO. 27981 | 235-AlaArgProArgValThrArgValProTyrAspAspLysAlaTyr-249 |
| SEQ. ID. NO. 27982 | 259-ValSerLysArgLeuGluIle-265 |
| SEQ. ID. NO. 27983 | 285-AlaGlySerGluThrLeu-290 |
| g128-2 | |
| AMPHI Regions - AMPHI | |
| SEQ. ID. NO. 27984 | 43-AlaGlnThrHisThrGlyTrpAlaAsnThrValGluArgLeuThrGlyIleThrGluArgValGlyArgIleTrpGlyValValSerHisLeuAsnSerVal Val-77 |
| SEQ. ID. NO. 27985 | 85-ValTyrAsnGluLeuMetProGluIle-93 |
| SEQ. ID. NO. 27986 | 102-GlnAspIleGluLeuTyrAsnArgPheLysThrIleLysAsnSerProGlu-118 |
| SEQ. ID. NO. 27987 | 166-PheSerGlnAsnValLeuAspAlaThrAsp-175 |
| SEQ. ID. NO. 27988 | 189-GlyIleProGluAspAla-194 |
| SEQ. ID. NO. 27989 | 218-HisTyrLeuAlaVal-222 |

TABLE 1-continued

| | |
|---|---|
| SEQ. ID. NO. 27990 | 231-LeuArgGluGlnIleTyr-236 |
| SEQ. ID. NO. 27991 | 245-GluLeuSerAsnAspGlyLysPheAspAsnThrAlaAsnIleAspArgThrLeuGluAsnAlaLeuLysThrAlaLysLeuLeuGlyPheLysAsn TyrAlaGlu-279 |
| SEQ. ID. NO. 27992 | 286-MetAlaAspThrProGluGlnValLeuAsnPheLeuHisAspLeuAlaArgArgAla-304 |
| SEQ. ID. NO. 27993 | 313-AlaGluValLysAlaPhe-318 |
| SEQ. ID. NO. 27994 | 360-LysValLeuAlaGlyLeuPheAlaGlnIleLysLysLeuTyrGly-374 |
| SEQ. ID. NO. 27995 | 472-LeuHisHisLeuLeuThrGlnValAspGluLeu-482 |
| SEQ. ID. NO. 27996 | 496-GluLeuProSerGlnPhe-501 |
| SEQ. ID. NO. 27997 | 522-GlyGluProLeuProLysGluLeuPheAspLys-532 |
| SEQ. ID. NO. 27998 | 570-TrpGlnGlnValLeuAspSerVal-577 |
| SEQ. ID. NO. 27999 | 584-IleGlnProProGluTyrAsnArgPheAlaAsnSerPheGlyHisIlePheAlaGlyGly-603 |
| SEQ. ID. NO. 28000 | 610-SerTyrAlaTrpAlaGlu-615 |
| SEQ. ID. NO. 28001 | 623-AlaAlaPheGluGluSerAspAsp-630 |
| SEQ. ID. NO. 28002 | 636-LysArgPheTrpGlnGluIleLeuAla-644 |
| SEQ. ID. NO. 28003 | 651-AlaAlaGluSerPheLysAlaPheArg-659 |
| Antigenic Index - Jameson-Wolf | |
| SEQ. ID. NO. 28004 | 9-LeuGlyGluGluProArgPheAsnGlnIleLysThrGluAspIleLysProAlaVal-27 |
| SEQ. ID. NO. 28005 | 32-AlaGluAlaArgGly-36 |
| SEQ. ID. NO. 28006 | 43-AlaGlnThrHisThrGlyTrp-49 |
| SEQ. ID. NO. 28007 | 52-ThrValGluArgLeuThrGlyIleThrGluArgValGlyArgIleTrp-67 |
| SEQ. ID. NO. 28008 | 77-ValAspThrProGluLeu-82 |
| SEQ. ID. NO. 28009 | 100-IleGlyGlnAspIleGluLeuTyrAsnArgPheLysThrIleLysAsnSerProGluPhe-119 |
| SEQ. ID. NO. 28010 | 123-SerProAlaGlnLysThrLysLeuAspHisAspLeuArgAsp-136 |
| SEQ. ID. NO. 28011 | 140-SerGlyAlaGluLeuProProGluArgGlnAlaGluLeuAlaLysLeuGlnThrGluGlyAlaGlnLeu-162 |
| SEQ. ID. NO. 28012 | 165-LysPheSerGlnAsnVal-170 |
| SEQ. ID. NO. 28013 | 172-AspAlaThrAspAla-176 |
| SEQ. ID. NO. 28014 | 190-IleProGluAspAla-194 |
| SEQ. ID. NO. 28015 | 202-AlaGlnSerGluGlyLysThrGlyTyrLys-211 |
| SEQ. ID. NO. 28016 | 225-TyrAlaGlyAsnArgGluLeuArgGluGlnIle-235 |
| SEQ. ID. NO. 28017 | 242-ArgAlaSerGluLeuSerAsnAspGlyLysPheAspAsnThrAlaAsnIleAspArgThrLeuGluAsnAlaLeuLysThr-268 |
| SEQ. ID. NO. 28018 | 285-LysMetAlaAspThrProGluGln-292 |
| SEQ. ID. NO. 28019 | 300-LeuAlaArgArgAlaLysProTyrAlaGluLysAspLeuAlaGlu-314 |
| SEQ. ID. NO. 28020 | 316-LysAlaPheAlaArgGluHisLeuGlyLeuAlaAspProGlnProTrpAspLeu-333 |
| SEQ. ID. NO. 28021 | 335-TyrAlaGlyGluLysLeuArgGluAlaLysTyrAlaPheSerGluThrGluValLysLys-354 |
| SEQ. ID. NO. 28022 | 377-PheAlaGluLysThr-381 |
| SEQ. ID. NO. 28023 | 387-LysAspValArgTyrPheGluLeuGlnGlnAsnGlyLysThrIle-401 |
| SEQ. ID. NO. 28024 | 409-TyrAlaArgGluGlyLysArgGlyGlyAla-418 |
| SEQ. ID. NO. 28025 | 420-MetAsnAspTyrLysGlyArgArgArgPheAlaAspGlyThrLeu-434 |
| SEQ. ID. NO. 28026 | 447-ProProValGlyGlyLysGluAlaArgLeuSerHisAspGlu-460 |
| SEQ. ID. NO. 28027 | 478-GlnValAspGluLeuGlyVal-484 |
| SEQ. ID. NO. 28028 | 496-GluLeuProSerGln-500 |
| SEQ. ID. NO. 28029 | 516-SerAlaHisGluGluThrGlyGluProLeuPro-526 |
| SEQ. ID. NO. 28030 | 560-SerGluSerAspGluCysArgLeuLysAsn-569 |
| SEQ. ID. NO. 28031 | 575-AspSerValArgLysGluValAla-582 |
| SEQ. ID. NO. 28032 | 585-GlnProProGluTyrAsnArgPheAlaAsnSerPheGly-597 |
| SEQ. ID. NO. 28033 | 605-SerAlaGlyTyrTyrSerTyr-611 |
| SEQ. ID. NO. 28034 | 625-PheGluGluSerAspAspValAlaAlaThrGlyLysArgPheTrp-639 |
| SEQ. ID. NO. 28035 | 646-GlyGlySerArgSerAlaAlaGluSerPheLysAlaPheArgGlyArgGluProSerIle-665 |
| SEQ. ID. NO. 28036 | 669-LeuArgHisSerGlyPheAspAsnAlaAla-678 |
| Hydrophilic Regions - Hopp-Woods | |
| SEQ. ID. NO. 28037 | 9-LeuGlyGluGluProArgPheAsnGlnIleLysThrGluAspIleLysPro-25 |
| SEQ. ID. NO. 28038 | 32-AlaGluAlaArgGly-36 |
| SEQ. ID. NO. 28039 | 52-ThrValGluArgLeuThrGlyIleThrGluArgValGly-64 |
| SEQ. ID. NO. 28040 | 77-ValAspThrProGluLeu-82 |
| SEQ. ID. NO. 28041 | 100-IleGlyGlnAspIleGluLeu-106 |
| SEQ. ID. NO. 28042 | 111-LysThrIleLysAsnSerProGlu-118 |
| SEQ. ID. NO. 28043 | 124-ProAlaGlnLysThrLysLeuAspHisAspLeuArgAsp-136 |
| SEQ. ID. NO. 28044 | 143-GluLeuProProGluArgGlnAlaGluLeuAlaLysLeuGlnThrGluGlyAlaGlnLeu-162 |
| SEQ. ID. NO. 28045 | 190-IleProGluAspAla-194 |
| SEQ. ID. NO. 28046 | 202-AlaGlnSerGluGlyLysThrGlyTyr-210 |
| SEQ. ID. NO. 28047 | 227-GlyAsnArgGluLeuArgGluGlnIle-235 |
| SEQ. ID. NO. 28048 | 242-ArgAlaSerGluLeuSerAsnAspGlyLysPheAspAsn-254 |
| SEQ. ID. NO. 28049 | 256-AlaAsnIleAspArgThrLeuGluAsnAlaLeuLysThr-268 |
| SEQ. ID. NO. 28050 | 285-LysMetAlaAspThrProGlu-291 |
| SEQ. ID. NO. 28051 | 300-LeuAlaArgArgAlaLysProTyrAlaGluLysAspLeuAlaGlu-314 |
| SEQ. ID. NO. 28052 | 316-LysAlaPheAlaArgGluHisLeuGly-324 |
| SEQ. ID. NO. 28053 | 335-TyrAlaGlyGluLysLeuArgGluAlaLysTyrAlaPheSerGluThrGluValLysLys-354 |
| SEQ. ID. NO. 28054 | 377-PheAlaGluLysThr-381 |
| SEQ. ID. NO. 28055 | 387-LysAspValArgTyr-391 |
| SEQ. ID. NO. 28056 | 396-GlnAsnGlyLysThr-400 |
| SEQ. ID. NO. 28057 | 409-TyrAlaArgGluGlyLysArgGlyGly-417 |
| SEQ. ID. NO. 28058 | 423-TyrLysGlyArgArgArgPheAlaAsp-431 |
| SEQ. ID. NO. 28059 | 449-ValGlyGlyLysGluAlaArgLeuSerHisAspGlu-460 |
| SEQ. ID. NO. 28060 | 478-GlnValAspGluLeuGly-483 |
| SEQ. ID. NO. 28061 | 516-SerAlaHisGluGluThrGlyGluProLeuPro-526 |
| SEQ. ID. NO. 28062 | 560-SerGluSerAspGluCysArgLeuLysAsn-569 |
| SEQ. ID. NO. 28063 | 575-AspSerValArgLysGluValAla-582 |

TABLE 1-continued

| | |
|---|---|
| SEQ. ID. NO. 28064 | 625-PheGluGluSerAspAspValAlaAlaThrGly-635 |
| SEQ. ID. NO. 28065 | 647-GlySerArgSerAlaAlaGluSerPheLysAlaPheArgGlyArgGluProSerIle-665 |
| g130 | |
| AMPHI Regions - AMPHI | |
| SEQ. ID. NO. 28066 | 16-ThrLeuValSerGlyIle-21 |
| SEQ. ID. NO. 28067 | 36-GlySerGlySerPheGly-41 |
| SEQ. ID. NO. 28068 | 56-GlnProValGlyGlnLeu-61 |
| SEQ. ID. NO. 28069 | 91-AsnValProAsnAlaPro-96 |
| SEQ. ID. NO. 28070 | 110-GlnGlyPheAspThrLeuPheGlnHisAlaLeuAsnGlyPheAsnAlaMet-126 |
| SEQ. ID. NO. 28071 | 171-ThrAlaSerAlaPro-175 |
| SEQ. ID. NO. 28072 | 204-PheGluAlaThrCysGln-209 |
| SEQ. ID. NO. 28073 | 211-CysHisGlyGlySerIleProGlyIlePro-220 |
| SEQ. ID. NO. 28074 | 234-LysGlyLysGluThr-238 |
| SEQ. ID. NO. 28075 | 245-GluGlyPheAsnAlaMet-250 |
| Antigenic Index - Jameson-Wolf | |
| SEQ. ID. NO. 28076 | 1-MetLysGlnLeuArgAspAsnLysAlaGlnGlySer-12 |
| SEQ. ID. NO. 28077 | 35-AlaGlySerGlySerPheGlyAspValAspAlaThrThrGluAlaAlaThrGlnThrArgIleGlnProValGly-59 |
| SEQ. ID. NO. 28078 | 63-MetGlyAspGlyIleProValGlyGluArgGlnGlyGlu-75 |
| SEQ. ID. NO. 28079 | 87-AlaAlaAspSerAsnValProAsnAlaProLysLeuGluHisAsnGlyAspTrpAla-105 |
| SEQ. ID. NO. 28080 | 108-IleAlaGlnGlyPhe-112 |
| SEQ. ID. NO. 28081 | 126-MetProAlaLysGlyGlyAla-132 |
| SEQ. ID. NO. 28082 | 134-AspLeuThrAspGlnGluLeuLysArg-142 |
| SEQ. ID. NO. 28083 | 148-AlaAsnLysSerGlyGlySerPheProAsnProAspGluAlaAlaProAlaAspAsnAlaAlaSerGlyThrAlaSerAlaProAlaAspSerAlaAla ProAlaGluAlaLysAlaGluAspLysGlyAlaAla-192 |
| SEQ. ID. NO. 28084 | 197-GlyValAspGlyLysLysValPheGlu-205 |
| SEQ. ID. NO. 28085 | 221-GlyIleGlyLysLysAspAspTrpAlaProArgIleLysLysGlyLysGluThrLeuHis-240 |
| SEQ. ID. NO. 28086 | 251-ProAlaLysGlyGlyAsnAlaGlyLeuSerAspAspGluValLysAla-266 |
| SEQ. ID. NO. 28087 | 274-GlnSerGlyAlaLys-278 |
| Hydrophilic Regions - Hopp-Woods | |
| SEQ. ID. NO. 28088 | 1-MetLysGlnLeuArgAspAsnLysAlaGlnGly-11 |
| SEQ. ID. NO. 28089 | 41-GlyAspValAspAlaThrThrGluAlaAlaThr-51 |
| SEQ. ID. NO. 28090 | 68-ProValGlyGluArgGlnGlyGlu-75 |
| SEQ. ID. NO. 28091 | 87-AlaAlaAspSerAsnVal-92 |
| SEQ. ID. NO. 28092 | 96-ProLysLeuGluHisAsnGly-102 |
| SEQ. ID. NO. 28093 | 127-ProAlaLysGlyGlyAla-132 |
| SEQ. ID. NO. 28094 | 134-AspLeuThrAspGlnGluLeuLysArg-142 |
| SEQ. ID. NO. 28095 | 156-ProAsnProAspGluAlaAlaProAlaAspAsnAlaAla-168 |
| SEQ. ID. NO. 28096 | 174-AlaProAlaAspSerAlaAlaProAlaGluAlaLysAlaGluAspLysGlyAlaAla-192 |
| SEQ. ID. NO. 28097 | 198-ValAspGlyLysLysValPheGlu-205 |
| SEQ. ID. NO. 28098 | 222-IleGlyLysLysAspAspTrpAlaProArgIleLysLysGlyLysGluThrLeuHis-240 |
| SEQ. ID. NO. 28099 | 251-ProAlaLysGlyGlyAsn-256 |
| SEQ. ID. NO. 28100 | 258-GlyLeuSerAspAspGluValLysAla-266 |
| g132-2 | |
| AMPHI Regions - AMPHI | |
| SEQ. ID. NO. 28101 | 13-IleIleSerAlaLeuAlaVal-19 |
| SEQ. ID. NO. 28102 | 70-AlaThrCysMetAlaMetVal-76 |
| SEQ. ID. NO. 28103 | 92-IleArgGlnThrGlnGlnAlaProLysProValSerAsnThr-105 |
| Antigenic Index - Jameson-Wolf | |
| SEQ. ID. NO. 28104 | 26-GlnHisGlyLysGlyAlaAspAla-33 |
| SEQ. ID. NO. 28105 | 38-GlySerGlySerGlySerAla-44 |
| SEQ. ID. NO. 28106 | 81-HisThrThrLysHisGlyLeuAspPheSerAsnIleArgGlnThrGlnGlnAlaProLysProValSerAsnThrGluProSerAlaProValProGlnGln GlnLys-116 |
| Hydrophilic Regions - Hopp-Woods | |
| SEQ. ID. NO. 28107 | 28-GlyLysGlyAlaAspAla-33 |
| SEQ. ID. NO. 28108 | 93-ArgGlnThrGlnGlnAlaProLysProValSerAsnThrGluProSerAla-109 |
| g134 | |
| AMPHI Regions - AMPHI | |
| SEQ. ID. NO. 28109 | 39-IleGlnSerAlaGlyThrVal-45 |
| SEQ. ID. NO. 28110 | 47-GlyLysLysThrGly-51 |
| SEQ. ID. NO. 28111 | 56-SerAspTrpMetAspIleGluLysGlnArg-65 |
| SEQ. ID. NO. 28112 | 83-ValAsnLeuLeuAspThrProGlyHis-91 |
| SEQ. ID. NO. 28113 | 97-AspThrTyrArgValLeuThrAlaVal-105 |
| SEQ. ID. NO. 28114 | 114-AlaAlaLysGlyValGlu-119 |
| SEQ. ID. NO. 28115 | 123-IleLysLeuLeuAsnValCysArg-130 |
| SEQ. ID. NO. 28116 | 142-LysTyrAspArgGluVal-147 |
| SEQ. ID. NO. 28117 | 149-AspSerLeuGluLeuLeuAspGluValGluAspIleLeuGln-162 |
| SEQ. ID. NO. 28118 | 176-LysAsnPheLysGlyValTyrHisIleLeu-185 |
| SEQ. ID. NO. 28119 | 201-HisGluPheAspIleIleLysGlyIleAsnAsn-211 |
| SEQ. ID. NO. 28120 | 254-PheGlySerAlaIle-258 |
| SEQ. ID. NO. 28121 | 265-GluIleLeuAsnSerLeuIleAspTrpAlaPro-275 |
| SEQ. ID. NO. 28122 | 322-LysPheGluArgGlyMetLys-328 |
| SEQ. ID. NO. 28123 | 361-AspIleIleGlyIleProAsnHis-368 |
| SEQ. ID. NO. 28124 | 395-LeuPheArgSerValArgIleLys-402 |
| SEQ. ID. NO. 28125 | 404-ProLeuLysIleLysGln-409 |
| SEQ. ID. NO. 28126 | 411-GlnLysGlyLeuGlnGlnLeuGlyGlu-419 |
| SEQ. ID. NO. 28127 | 423-ValGlnValPheLysProMetSer-430 |
| SEQ. ID. NO. 28128 | 449-SerArgLeuAlaAsnGluTyr-455 |

TABLE 1-continued

| | |
|---|---|
| SEQ. ID. NO. 28129 | 481-AlaGluPheGluLysAlaAsn-487 |
| SEQ. ID. NO. 28130 | 515-ArgTrpProAspIle-519 |
| Antigenic Index - Jameson-Wolf | |
| SEQ. ID. NO. 28131 | 4-GluIleLeuAspGlnValArgArgArgArgThrPhe-15 |
| SEQ. ID. NO. 28132 | 19-SerHisProAspAlaGlyLysThrThrLeuThr-29 |
| SEQ. ID. NO. 28133 | 43-GlyThrValLysGlyLysLysThrGlyLysPheAlaThr-55 |
| SEQ. ID. NO. 28134 | 57-AspTrpMetAspIleGluLysGlnArgGly-66 |
| SEQ. ID. NO. 28135 | 76-PheAspTyrLysAspHisThrVal-83 |
| SEQ. ID. NO. 28136 | 85-LeuLeuAspThrProGlyHisGlnAspPheSerGluAspThrTyrArg-100 |
| SEQ. ID. NO. 28137 | 113-AspAlaAlaLysGlyValGlu-119 |
| SEQ. ID. NO. 28138 | 129-CysArgLeuArgAspThrPro-135 |
| SEQ. ID. NO. 28139 | 140-MetAsnLysTyrAspArgGluValArgAspSerLeuGluLeuLeuAspGluValGluAsp-159 |
| SEQ. ID. NO. 28140 | 173-GlyMetGlyLysAsnPheLys-179 |
| SEQ. ID. NO. 28141 | 194-AlaGlyGlyGluArgLeuProHis-201 |
| SEQ. ID. NO. 28142 | 207-LysGlyIleAsnAsnProGluLeuGluGlnArgPheProLeu-220 |
| SEQ. ID. NO. 28143 | 223-GlnGlnLeuArgAspGluIleGluLeu-231 |
| SEQ. ID. NO. 28144 | 235-AlaSerAsnGluPheAsnLeu-241 |
| SEQ. ID. NO. 28145 | 274-AlaProAlaProLysProArgAspAlaThrMet-284 |
| SEQ. ID. NO. 28146 | 286-MetValGlyProAspGluProLysPhe-294 |
| SEQ. ID. NO. 28147 | 302-GlnAlaAsnMetAspProLysHisArgAspArgIleAla-314 |
| SEQ. ID. NO. 28148 | 317-ArgValCysSerGlyLysPheGluArgGlyMetLysMetLysHisLeuArgIleAsnArgGluIleAla-339 |
| SEQ. ID. NO. 28149 | 348-SerHisAspArgGluLeuAlaGluGluAlaTyrAla-359 |
| SEQ. ID. NO. 28150 | 365-IleProAsnHisGly-369 |
| SEQ. ID. NO. 28151 | 373-IleGlyAspSerPheSerGluGlyGluGln-382 |
| SEQ. ID. NO. 28152 | 399-ValArgIleLysAsnProLeuLysIleLysGlnLeuGlnLysGlyLeuGlnGlnLeuGlyGluGluGlyAla-422 |
| SEQ. ID. NO. 28153 | 450-ArgLeuAlaAsnGluTyrGlyVal-457 |
| SEQ. ID. NO. 28154 | 459-AlaValPheAspSer-463 |
| SEQ. ID. NO. 28155 | 473-SerCysAspAspLysLysLysLeuAlaGluPheGluLysAlaAsnAla-488 |
| SEQ. ID. NO. 28156 | 503-AlaProAsnArgValAsnLeu-509 |
| SEQ. ID. NO. 28157 | 511-LeuThrGlnGluArgTrpProAspIleVal-520 |
| SEQ. ID. NO. 28158 | 523-GluThrArgGluHisSerVal-529 |
| Hydrophilic Regions - Hopp-Woods | |
| SEQ. ID. NO. 28159 | 4-GluIleLeuAspGlnValArgArgArgArgThr-14 |
| SEQ. ID. NO. 28160 | 21-ProAspAlaGlyLys-25 |
| SEQ. ID. NO. 28161 | 43-GlyThrValLysGlyLysLysThrGlyLys-52 |
| SEQ. ID. NO. 28162 | 59-MetAspIleGluLysGlnArgGly-66 |
| SEQ. ID. NO. 28163 | 77-AspTyrLysAspHisThr-82 |
| SEQ. ID. NO. 28164 | 92-GlnAspPheSerGluAspThrTyr-99 |
| SEQ. ID. NO. 28165 | 113-AspAlaAlaLysGlyValGlu-119 |
| SEQ. ID. NO. 28166 | 129-CysArgLeuArgAspThrPro-135 |
| SEQ. ID. NO. 28167 | 142-LysTyrAspArgGluValArgAspSerLeuGluLeuLeuAspGluValGluAsp-159 |
| SEQ. ID. NO. 28168 | 194-AlaGlyGlyGluArgLeuProHis-201 |
| SEQ. ID. NO. 28169 | 212-ProGluLeuGluGlnArgPheProLeu-220 |
| SEQ. ID. NO. 28170 | 223-GlnGlnLeuArgAspGluIleGluLeu-231 |
| SEQ. ID. NO. 28171 | 277-ProLysProArgAspAlaThrMet-284 |
| SEQ. ID. NO. 28172 | 287-ValGlyProAspGluProLysPhe-294 |
| SEQ. ID. NO. 28173 | 305-MetAspProLysHisArgAspArgIleAla-314 |
| SEQ. ID. NO. 28174 | 319-CysSerGlyLysPheGluArgGlyMetLysMetLysHisLeuArgIleAsnArgGluIleAla-339 |
| SEQ. ID. NO. 28175 | 348-SerHisAspArgGluLeuAlaGluGluAlaTyrAla-359 |
| SEQ. ID. NO. 28176 | 376-SerPheSerGluGlyGluGln-382 |
| SEQ. ID. NO. 28177 | 399-ValArgIleLysAsnProLeuLysIleLysGlnLeuGln-411 |
| SEQ. ID. NO. 28178 | 417-LeuGlyGluGluGlyAla-422 |
| SEQ. ID. NO. 28179 | 473-SerCysAspAspLysLysLysLeuAlaGluPheGluLysAlaAsnAla-488 |
| SEQ. ID. NO. 28180 | 512-ThrGlnGluArgTrpPro-517 |
| SEQ. ID. NO. 28181 | 523-GluThrArgGluHisSerVal-529 |
| g135-2 | |
| AMPHI Regions - AMPHI | |
| SEQ. ID. NO. 28182 | 29-ThrIleThrArgGlnLeuAlaAlaLeu-37 |
| SEQ. ID. NO. 28183 | 85-GluTyrThrAlaAsnLeu-90 |
| SEQ. ID. NO. 28184 | 169-AspIleAspGlyLeuTyrThr-175 |
| SEQ. ID. NO. 28185 | 185-ValArgLeuAspLysIleGluHis-192 |
| SEQ. ID. NO. 28186 | 212-GlyMetLeuThrLysIle-217 |
| SEQ. ID. NO. 28187 | 236-LeuLysProAspSerLeuAlaGluAlaAlaGlu-246 |
| SEQ. ID. NO. 28188 | 284-AlaGluHisAlaLeuSer-289 |
| SEQ. ID. NO. 28189 | 300-IleAlaGlyIleGluGly-305 |
| SEQ. ID. NO. 28190 | 308-SerArgMetAspThrValThrValTyr-316 |
| SEQ. ID. NO. 28191 | 318-LysAlaThrLysGlnPro-323 |
| Antigenic Index - Jameson-Wolf | |
| SEQ. ID. NO. 28192 | 1-MetLysTyrLysArgIleVal-7 |
| SEQ. ID. NO. 28193 | 14-SerIleThrArgSerAspGlySerLeuSerArgGlyLysIleGlnThrIle-30 |
| SEQ. ID. NO. 28194 | 60-GlyPheLysLysArgProValLysIleAlaAspLysGlnAlaSer-74 |
| SEQ. ID. NO. 28195 | 90-LeuSerSerAspGlyIle-95 |
| SEQ. ID. NO. 28196 | 105-AlaAspPheAlaAspLysArgArgTyrGlnAsnAlaGlyGly-118 |
| SEQ. ID. NO. 28197 | 124-LeuGlnArgArgAlaIle-129 |
| SEQ. ID. NO. 28198 | 132-IleAsnGluAsnAspThrValSerValGluGluLeuLysIleGlyAspAsnAspThrLeu-151 |
| SEQ. ID. NO. 28199 | 176-GlyAsnProAsnSerAsnProAspAlaValArgLeuAspLysIleGluHisIleAsn-194 |
| SEQ. ID. NO. 28200 | 202-GlyGlySerGlySerAlaAsnGlyThrGly-211 |
| SEQ. ID. NO. 28201 | 215-ThrLysIleLysAla-219 |
| SEQ. ID. NO. 28202 | 224-AlaGluSerGlyVal-228 |
| SEQ. ID. NO. 28203 | 233-CysSerSerLeuLysProAspSerLeuAlaGluAlaAlaGluHisGlnAlaAspGly-251 |

TABLE 1-continued

| | |
|---|---|
| SEQ. ID. NO. 28204 | 257-ArgAlaLysGlyLeuArgThrGlnLysGln-266 |
| SEQ. ID. NO. 28205 | 271-TyrSerGluSerArgGlySerValTyrValAspGluGlyAlaGluHisAlaLeuSerGluGlnGlyLysSerLeuLeu-296 |
| SEQ. ID. NO. 28206 | 305-GlyHisPheSerArgMetAspThr-312 |
| SEQ. ID. NO. 28207 | 317-SerLysAlaThrLysGlnProLeuGlyLysGlyArgVal-329 |
| SEQ. ID. NO. 28208 | 335-AlaAlaGluAspLeuLeuLysSerArgLysAlaLys-346 |
| SEQ. ID. NO. 28209 | 350-IleHisArgAspAspTrpIleSer-357 |
| Hydrophilic Regions - Hopp-Woods | |
| SEQ. ID. NO. 28210 | 1-MetLysTyrLysArgIleVal-7 |
| SEQ. ID. NO. 28211 | 14-SerIleThrArgSerAspGlySerLeuSerArgGlyLysIle-27 |
| SEQ. ID. NO. 28212 | 60-GlyPheLysLysArgProValLysIleAlaAspLysGlnAlaSer-74 |
| SEQ. ID. NO. 28213 | 105-AlaAspPheAlaAspLysArgArgTyrGlnAsn-115 |
| SEQ. ID. NO. 28214 | 124-LeuGlnArgArgAlaIle-129 |
| SEQ. ID. NO. 28215 | 133-AsnGluAsnAspThrValSerValGluGluLeuLysIleGlyAspAsnAspThrLeu-151 |
| SEQ. ID. NO. 28216 | 178-ProAsnSerAsnProAspAlaValArgLeuAspLysIleGluHisIleAsn-194 |
| SEQ. ID. NO. 28217 | 215-ThrLysIleLysAla-219 |
| SEQ. ID. NO. 28218 | 236-LeuLysProAspSerLeuAlaGluAlaAlaGluHisGlnAlaAsp-250 |
| SEQ. ID. NO. 28219 | 257-ArgAlaLysGlyLeuArgThrGlnLys-265 |
| SEQ. ID. NO. 28220 | 272-SerGluSerArgGly-276 |
| SEQ. ID. NO. 28221 | 278-ValTyrValAspGluGlyAlaGluHisAlaLeuSerGluGlnGlyLys-293 |
| SEQ. ID. NO. 28222 | 306-HisPheSerArgMetAspThr-312 |
| SEQ. ID. NO. 28223 | 318-LysAlaThrLysGlnProLeuGlyLysGlyArgVal-329 |
| SEQ. ID. NO. 28224 | 335-AlaAlaGluAspLeuLeuLysSerArgLysAlaLys-346 |
| SEQ. ID. NO. 28225 | 351-HisArgAspAspTrp-355 |
| g136 | |
| AMPHI Regions - AMPHI | |
| SEQ. ID. NO. 28226 | 61-AlaValAspValCysGlnArgValArgGlnPheGlyArgLysPheArgGlnLeuAlaPhe-80 |
| SEQ. ID. NO. 28227 | 100-HisHisGlyValLysGlnLeuPheLysArgPheIleIle-112 |
| SEQ. ID. NO. 28228 | 114-GlyPheLysProIleGlyArgHis-121 |
| SEQ. ID. NO. 28229 | 162-ArgHisCysGlnAsn-166 |
| SEQ. ID. NO. 28230 | 184-GlnHisPheGlyGlnPro-189 |
| SEQ. ID. NO. 28231 | 191-GluArgCysGlnPheVal-196 |
| Antigenic Index - Jameson-Wolf | |
| SEQ. ID. NO. 28232 | 1-MetGluIleArgPhe-5 |
| SEQ. ID. NO. 28233 | 52-ArgPheValAspAspArgLeuProVal-60 |
| SEQ. ID. NO. 28234 | 64-ValCysGlnArgValArgGlnPheGlyArgLysPheArg-76 |
| SEQ. ID. NO. 28235 | 83-LeuGlnAlaAspAsn-87 |
| SEQ. ID. NO. 28236 | 113-GlyGlyPheLysProIleGlyArgHisAsnValGln-124 |
| SEQ. ID. NO. 28237 | 153-IleArgHisArgGlyGlyCysPheHisArgHisCysGlnAsnGlnProPheAsp-170 |
| SEQ. ID. NO. 28238 | 173-ThrPheGlyGlyGlyLysLeuArg-180 |
| SEQ. ID. NO. 28239 | 185-HisPheGlyGlnProValGluArg-192 |
| SEQ. ID. NO. 28240 | 198-ProAlaGlnGlnArgArgHisLysThr-206 |
| Hydrophilic Regions - Hopp-Woods | |
| SEQ. ID. NO. 28241 | 1-MetGluIleArgPhe-5 |
| SEQ. ID. NO. 28242 | 52-ArgPheValAspAspArgLeuProVal-60 |
| SEQ. ID. NO. 28243 | 64-ValCysGlnArgValArgGlnPheGlyArgLysPheArg-76 |
| SEQ. ID. NO. 28244 | 199-AlaGlnGlnArgArgHisLysThr-206 |
| g137 | |
| AMPHI Regions - AMPHI | |
| SEQ. ID. NO. 28245 | 24-LeuSerTyrIleLeuGlyPhe-30 |
| SEQ. ID. NO. 28246 | 49-ThrLysGluSerLeu-53 |
| SEQ. ID. NO. 28247 | 55-AspPheLeuThrTrpGly-60 |
| SEQ. ID. NO. 28248 | 78-PheSerAspTyrLeuAlaHisProLeuAspIlePheLysValTrpGluGlyGly-95 |
| SEQ. ID. NO. 28249 | 101-GlyPheLeuGlyValValIle-107 |
| SEQ. ID. NO. 28250 | 120-PheLeuLysLeuMetAspThrValAlaProLeuValPro-132 |
| SEQ. ID. NO. 28251 | 139-ArgIleGlyAsnPheIle-144 |
| SEQ. ID. NO. 28252 | 149-TrpGlyArgIleThrAspIleAsnAlaPhe-158 |
| SEQ. ID. NO. 28253 | 178-ProLeuTrpAlaGluTrpLeuGlnGlnTyr-187 |
| SEQ. ID. NO. 28254 | 190-LeuProArgHisProSerGlnLeu-197 |
| SEQ. ID. NO. 28255 | 232-TyrGlyValPheArgPheIleAlaGluPheAlaArgGlnProAspAspTyrLeuGly-250 |
| Antigenic Index - Jameson-Wolf | |
| SEQ. ID. NO. 28256 | 36-LeuGlyArgArgArgIleAlaGln-43 |
| SEQ. ID. NO. 28257 | 48-PheThrLysGluSerLeuAspAsp-55 |
| SEQ. ID. NO. 28258 | 92-TrpGluGlyGlyMet-96 |
| SEQ. ID. NO. 28259 | 113-SerArgLysHisGlyIle-118 |
| SEQ. ID. NO. 28260 | 136-AlaSerGlyArgIle-140 |
| SEQ. ID. NO. 28261 | 166-AlaHisTyrGluAspAlaGluAlaAlaAla-175 |
| SEQ. ID. NO. 28262 | 191-ProArgHisProSerGlnLeu-197 |
| SEQ. ID. NO. 28263 | 215-SerLysLysProArgProThrGlyGln-223 |
| SEQ. ID. NO. 28264 | 241-PheAlaArgGlnProAspAspTyrLeu-249 |
| SEQ. ID. NO. 28265 | 277-PheGlyMetLysLysGlnHis-283 |
| Hydrophilic Regions - Hopp-Woods | |
| SEQ. ID. NO. 28266 | 37-GlyArgArgArgIleAla-42 |
| SEQ. ID. NO. 28267 | 48-PheThrLysGluSerLeuAsp-54 |
| SEQ. ID. NO. 28268 | 167-HisTyrGluAspAlaGluAlaAlaAla-175 |
| SEQ. ID. NO. 28269 | 216-LysLysProArgProThrGly-222 |

TABLE 1-continued

| | |
|---|---|
| SEQ. ID. NO. 28270 | 241-PheAlaArgGlnProAspAspTyr-248 |
| SEQ. ID. NO. 28271 | 278-GlyMetLysLysGlnHis-283 |
| g138 | |
| AMPHI Regions - AMPHI | |
| SEQ. ID. NO. 28272 | 21-ProTyrIleArgArgPheSerGlySer-29 |
| SEQ. ID. NO. 28273 | 74-AsnAlaMetLeuGluLysVal-80 |
| SEQ. ID. NO. 28274 | 85-GluPheValGlnGlyMet-90 |
| SEQ. ID. NO. 28275 | 109-ValAsnLysGluIleValSerMetIleAsnThrTyrGly-121 |
| SEQ. ID. NO. 28276 | 152-IleGlyGlnValGlyThrValGluSerIle-161 |
| SEQ. ID. NO. 28277 | 163-ThrGlyLeuValLysGlyLeu-169 |
| SEQ. ID. NO. 28278 | 199-GlyLysLeuAlaGluGluLeu-205 |
| SEQ. ID. NO. 28279 | 213-MetThrAsnIleAlaGlyValMetAspLysThrGlyAsnLeuLeuThrLysLeuThr-231 |
| SEQ. ID. NO. 28280 | 234-ArgIleAspGlyLeu-238 |
| SEQ. ID. NO. 28281 | 247-GlyMetLeuProLysIleAlaSerAlaValGluAlaAlaValAsn-261 |
| SEQ. ID. NO. 28282 | 276-AlaLeuLeuLeuGluIlePheThrAspAla-285 |
| Antigenic Index - Jameson-Wolf | |
| SEQ. ID. NO. 28283 | 9-AlaAlaAspLysAlaArgIleLeu-16 |
| SEQ. ID. NO. 28284 | 23-IleArgArgPheSerGlySer-29 |
| SEQ. ID. NO. 28285 | 35-TyrGlyGlyAsnAlaMetThr-41 |
| SEQ. ID. NO. 28286 | 43-ProAlaLeuLysGluGlyPheAla-50 |
| SEQ. ID. NO. 28287 | 68-GlyGlyGlyProGln-72 |
| SEQ. ID. NO. 28288 | 76-MetLeuGluLysValGlyLysLysGlyGluPhe-86 |
| SEQ. ID. NO. 28289 | 91-ArgValThrAspLysGluThrMetAsp-99 |
| SEQ. ID. NO. 28290 | 109-ValAsnLysGluIle-113 |
| SEQ. ID. NO. 28291 | 128-SerGlyArgAspAspHisPheIleLysAlaLysLysLeuLeuValAspThrProGluGlnAsnSerValAspIleGlyGln-154 |
| SEQ. ID. NO. 28292 | 159-GluSerIleAspThrGlyLeu-165 |
| SEQ. ID. NO. 28293 | 169-LeuIleGluArgGlyCysIle-175 |
| SEQ. ID. NO. 28294 | 182-GlyValGlyGluLysGlyGluAla-189 |
| SEQ. ID. NO. 28295 | 200-LysLeuAlaGluGluLeuAsnAlaGluLys-209 |
| SEQ. ID. NO. 28296 | 219-ValMetAspLysThrGlyAsnLeuLeuThrLysLeuThrProLysArgIleAspGlyLeuIleAla-240 |
| SEQ. ID. NO. 28297 | 259-AlaValAsnGlyValLys-264 |
| SEQ. ID. NO. 28298 | 269-IleAspGlyArgLeuProAsnAla-276 |
| SEQ. ID. NO. 28299 | 291-IleLeuGlyArgGlyGluAspAla-298 |
| Hydrophilic Regions - Hopp-Woods | |
| SEQ. ID. NO. 28300 | 9-AlaAlaAspLysAlaArgIleLeu-16 |
| SEQ. ID. NO. 28301 | 43-ProAlaLeuLysGluGlyPheAla-50 |
| SEQ. ID. NO. 28302 | 76-MetLeuGluLysValGlyLysLysGlyGluPhe-86 |
| SEQ. ID. NO. 28303 | 91-ArgValThrAspLysGluThrMetAsp-99 |
| SEQ. ID. NO. 28304 | 109-ValAsnLysGluIle-113 |
| SEQ. ID. NO. 28305 | 128-SerGlyArgAspAspHisPheIleLysAlaLysLysLeuLeuValAspThrProGluGlnAsnSerValAsp-151 |
| SEQ. ID. NO. 28306 | 183-ValGlyGluLysGlyGluAla-189 |
| SEQ. ID. NO. 28307 | 200-LysLeuAlaGluGluLeuAsnAlaGluLys-209 |
| SEQ. ID. NO. 28308 | 219-ValMetAspLysThrGly-224 |
| SEQ. ID. NO. 28309 | 230-LeuThrProLysArgIleAspGlyLeuIle-239 |
| SEQ. ID. NO. 28310 | 269-IleAspGlyArgLeu-273 |
| SEQ. ID. NO. 28311 | 293-GlyArgGlyGluAspAla-298 |
| g140 | |
| AMPHI Regions - AMPHI | |
| SEQ. ID. NO. 28312 | 10-TyrLeuAsnSerThr-14 |
| SEQ. ID. NO. 28313 | 32-PhePheLysAsnIleLysThr-38 |
| SEQ. ID. NO. 28314 | 45-SerLeuAspSerValGluLysThrAlaGly-54 |
| SEQ. ID. NO. 28315 | 68-AsnAlaAlaArgThrAlaSer-74 |
| SEQ. ID. NO. 28316 | 108-SerAlaThrProGluThrValGluThrAlaVal-118 |
| SEQ. ID. NO. 28317 | 137-AlaAlaAlaValGlnHisAlaAsnThrAlaAspGlyValArgIlePheAsnSerLeuAlaAlaThr-158 |
| SEQ. ID. NO. 28318 | 175-LeuLysAlaValSerAspGlyLeuAsp-183 |
| SEQ. ID. NO. 28319 | 189-LeuArgValIleAlaGln-194 |
| SEQ. ID. NO. 28320 | 266-IleGlyTyrLeuLysGlyLeuPheSerTyr-275 |
| SEQ. ID. NO. 28321 | 290-GluTyrAlaGluGlySer-295 |
| SEQ. ID. NO. 28322 | 303-LeuGlyAlaLeuGly-307 |
| SEQ. ID. NO. 28323 | 352-GlyThrLeuValGlyLeu-357 |
| SEQ. ID. NO. 28324 | 391-GlyGlyPheThrGlyAlaAla-397 |
| SEQ. ID. NO. 28325 | 425-AsnGlyTrpAsnGlyLeuAlaArg-432 |
| Antigenic Index - Jameson-Wolf | |
| SEQ. ID. NO. 28326 | 1-MetSerAlaArgGlyLysGlyAlaGly-9 |
| SEQ. ID. NO. 28327 | 12-AsnSerThrGlyArgHisVal-18 |
| SEQ. ID. NO. 28328 | 25-LysIleGlyGlnAspTyrSerPhe-32 |
| SEQ. ID. NO. 28329 | 34-LysAsnIleLysThrAspGlyGlyLeu-42 |
| SEQ. ID. NO. 28330 | 47-AspSerValGluLysThrAlaGlySerGluGlyAspThrProSer-61 |
| SEQ. ID. NO. 28331 | 63-TyrValArgArgGlyAsnAlaAlaArgThrAlaSer-74 |
| SEQ. ID. NO. 28332 | 86-HisAlaValGluGlnGlyGlySerAsnLeuGlu-96 |
| SEQ. ID. NO. 28333 | 102-LeuAspAlaSerGluSerSerAlaThrProGluThrValGlu-115 |
| SEQ. ID. NO. 28334 | 117-AlaValAlaAspArgThrAspMetProGlyIleArgLeuArgArgThrThrPhe-134 |
| SEQ. ID. NO. 28335 | 144-AsnThrAlaAspGlyValArg-150 |
| SEQ. ID. NO. 28336 | 160-TyrAlaAspSerAlaAlaAla-166 |
| SEQ. ID. NO. 28337 | 169-AspMetGlnGlyArgArgLeuLysAlaValSerAspGlyLeuAspHisAsnGlyThrGlyLeu-189 |
| SEQ. ID. NO. 28338 | 195-ThrGlnGlnAspGlyGlyThrTrpGluGlnGlyGlyValGluGlyLysMetArgGlySerThr-215 |
| SEQ. ID. NO. 28339 | 221-AlaAlaLysThrGlyGluAsnThrThr-229 |
| SEQ. ID. NO. 28340 | 236-IleGlyArgSerThrTrpSerGluAsnSerAlaAsnAlaLysThrAspSerIle-253 |
| SEQ. ID. NO. 28341 | 259-IleArgHisAspValGlyAsp-265 |
| SEQ. ID. NO. 28342 | 274-SerTyrGlyArgTyrLysAsnSerIleSerArgSerThrGlyAlaAspGluTyrAlaGlu-293 |

TABLE 1-continued

SEQ. ID. NO. 28343 315-AlaThrGlyAspLeuThrValGluGlyGlyLeuArgHisAspLeuLeuLys-331
SEQ. ID. NO. 28344 333-AspAlaPheAlaGluLysGlySerAlaLeuGlyTrpSerGlyAsnSerLeuThrGluGlyThr-353
SEQ. ID. NO. 28345 362-LeuSerGlnProLeuSerAspLysAlaVal-371
SEQ. ID. NO. 28346 376-AlaGlyValGluArgAspLeuAsnGlyArgAspTyrAla-388
SEQ. ID. NO. 28347 399-AlaThrGlyLysThrGlyAlaArgAsnMetProHisThrArgArgValAla-415
SEQ. ID. NO. 28348 421-ValGluPheGlyAsnGlyTrp-427
SEQ. ID. NO. 28349 434-SerTyrThrGlySerLysGlnTyrGlyAsnHisSerGly-446
Hydrophilic Regions - Hopp-Woods
SEQ. ID. NO. 28350 1-MetSerAlaArgGlyLysGly-7
SEQ. ID. NO. 28351 36-IleLysThrAspGly-40
SEQ. ID. NO. 28352 47-AspSerValGluLysThrAlaGlySerGluGlyAspThr-59
SEQ. ID. NO. 28353 63-TyrValArgArgGlyAsnAlaAlaArgThrAlaSer-74
SEQ. ID. NO. 28354 86-HisAlaValGluGlnGlyGlySerAsnLeu-95
SEQ. ID. NO. 28355 102-LeuAspAlaSerGluSerSerAlaThrProGluThrValGlu-115
SEQ. ID. NO. 28356 117-AlaValAlaAspArgThrAspMetProGlyIleArgLeuArgArgThrThrPhe-134
SEQ. ID. NO. 28357 144-AsnThrAlaAspGly-148
SEQ. ID. NO. 28358 169-AspMetGlnGlyArgArgLeuLysAlaValSerAspGlyLeuAspHisAsnGlyThr-187
SEQ. ID. NO. 28359 205-GlyGlyValGluGlyLysMetArgGlySerThr-215
SEQ. ID. NO. 28360 223-LysThrGlyGluAsnThrThr-229
SEQ. ID. NO. 28361 244-AsnSerAlaAsnAlaLysThrAspSer-252
SEQ. ID. NO. 28362 259-IleArgHisAspValGlyAsp-265
SEQ. ID. NO. 28363 277-ArgTyrLysAsnSerIleSerArgSerThrGlyAlaAspGluTyrAlaGlu-293
SEQ. ID. NO. 28364 323-GlyGlyLeuArgHisAspLeuLeuLys-331
SEQ. ID. NO. 28365 333-AspAlaPheAlaGluLysGlySer-340
SEQ. ID. NO. 28366 364-GlnProLeuSerAspLysAlaVal-371
SEQ. ID. NO. 28367 376-AlaGlyValGluArgAspLeuAsnGlyArgAspTyrAla-388
SEQ. ID. NO. 28368 399-AlaThrGlyLysThrGlyAlaArgAsnMetProHisThrArgArgValAla-415
g141
AMPHI Regions - AMPHI
SEQ. ID. NO. 28369 12-SerSerThrMetArgProIleGlyGluIle-21
SEQ. ID. NO. 28370 32-IleGluProTyrGly-36
SEQ. ID. NO. 28371 44-ProAlaGluAlaPheLysLeuPro-51
SEQ. ID. NO. 28372 80-AlaAspAlaLeuArgHisIle-86
SEQ. ID. NO. 28373 131-PheHisAlaIleGlyAla-136
SEQ. ID. NO. 28374 139-AsnLeuLeuAlaAlaMetLeuAspAsn-147
SEQ. ID. NO. 28375 174-GlnLeuArgAsnIleIleAspGlyMetGlyLysProValAspGlyValMetArgPro-192
SEQ. ID. NO. 28376 212-AspIleSerAspLeuLysGluArgPheGly-221
SEQ. ID. NO. 28377 244-AlaMetAlaAlaLeuLeuLysAspAlaIleLysProAsnLeu-257
SEQ. ID. NO. 28378 259-GlnThrIleGluGlyThrPro-265
SEQ. ID. NO. 28379 272-ProPheAlaAsnIleAlaHisGlyCysAsnSerValThrAlaThrArgLeuAlaLysHisLeuAlaAspTyrAla-296
SEQ. ID. NO. 28380 330-AlaThrValArgAla-334
SEQ. ID. NO. 28381 351-LeuGluAlaLeuAlaLysGlyLeuProAsnLeuLeuLysHisIleSerAsnLeuLysAsnValPheGly-373
SEQ. ID. NO. 28382 406-SerLeuThrGluValTrpGlyLys-413
SEQ. ID. NO. 28383 420-AspLeuAlaArgLysValValAsnAlaIleAspAsnGln-432
SEQ. ID. NO. 28384 473-IleAlaSerLeuGluLys-478
SEQ. ID. NO. 28385 502-LeuGlyCysProGluGly-507
SEQ. ID. NO. 28386 525-ValAlaLeuCysGlyAsnMetMetLysMetProGlyLeuProLysValProAlaAla-543
Antigenic Index - Jameson-Wolf
SEQ. ID. NO. 28387 3-PheLysThrAspAlaGluThrAlaGlnSerSerThrMetArgProIleGly-19
SEQ. ID. NO. 28388 27-LeuAsnValAspAsnIleGluProTyrGly-36
SEQ. ID. NO. 28389 38-TyrLysAlaLysIleAsnProAlaGluAlaPheLysLeuProGlnLysGlnGlyArg-56
SEQ. ID. NO. 28390 64-AsnProThrProAlaGlyGluGlyLysThrThr-74
SEQ. ID. NO. 28391 81-AspAlaLeuArgHisIleGlyLysAspSerValIleAlaLeuArgGluProSerLeuGlyPro-101
SEQ. ID. NO. 28392 105-ValLysGlyGlyAlaAlaGlyGlyGly-113
SEQ. ID. NO. 28393 151-GlnGlyAsnGluLeuAsnIleAspProLysArgValLeuTrp-164
SEQ. ID. NO. 28394 166-ArgValValAspMetAsnAspArgGlnLeuArgAsnIleIleAspGlyMetGlyLysProValAspGlyValMetArgProAspGlyPheAspIle-197
SEQ. ID. NO. 28395 211-LysAspIleSerAspLeuLysGluArgPheGly-221
SEQ. ID. NO. 28396 227-TyrAlaLysAspGlySerProValTyr-235
SEQ. ID. NO. 28397 237-LysAspLeuLysAla-241
SEQ. ID. NO. 28398 251-AspAlaIleLysProAsnLeu-257
SEQ. ID. NO. 28399 287-ArgLeuAlaLysHisLeuAla-293
SEQ. ID. NO. 28400 306-LeuGlyAlaGluLysPheCysAspIleLysCysArgLeuAlaGlyLeuLysProAspAla-325
SEQ. ID. NO. 28401 335-LeuLysTyrAsnGlyGlyValGluArgAlaAsnLeuGlyGluGluAsnLeuGluAlaLeuAla-355
SEQ. ID. NO. 28402 383-PheValSerAspSerAspAlaGluLeuAlaMetIleGluLysAlaCysAla-399
SEQ. ID. NO. 28403 411-TrpGlyLysGlyGlyAlaGlyGlyAlaAspLeuAlaArgLysValValAsn-427
SEQ. ID. NO. 28404 429-IleAspAsnGlnProAsnAsnPhe-436
SEQ. ID. NO. 28405 444-LeuGlyIleLysAspLysIleArgAlaIleAla-454
SEQ. ID. NO. 28406 458-TyrGlyAlaGluAspValAspPheSerAla-467
SEQ. ID. NO. 28407 474-AlaSerLeuGluLysLeuGlyLeuAspLysMetPro-485
SEQ. ID. NO. 28408 494-SerLeuSerAspAsnAlaLysLeu-501
SEQ. ID. NO. 28409 503-GlyCysProGluGlyPhe-508
SEQ. ID. NO. 28410 534-MetProGlyLeuPro-538
SEQ. ID. NO. 28411 541-ProAlaAlaGluLysIleAspValAspGluHisGly-552
Hydrophilic Regions - Hopp-Woods
SEQ. ID. NO. 28412 3-PheLysThrAspAlaGluThrAlaGln-11
SEQ. ID. NO. 28413 38-TyrLysAlaLysIleAsnPro-44
SEQ. ID. NO. 28414 46-GluAlaPheLysLeuProGlnLysGlnGlyArg-56
SEQ. ID. NO. 28415 67-ProAlaGlyGluGlyLysThr-73
SEQ. ID. NO. 28416 81-AspAlaLeuArgHisIleGlyLysAspSerValIleAlaLeuArgGluProSer-98

TABLE 1-continued

| | |
|---|---|
| SEQ. ID. NO. 28417 | 155-LeuAsnIleAspProLysArgValLeuTrp-164 |
| SEQ. ID. NO. 28418 | 166-ArgValValAspMetAsnAspArgGlnLeuArgAsnIleIle-179 |
| SEQ. ID. NO. 28419 | 181-GlyMetGlyLysProValAspGlyValMetArgProAspGlyPhe-195 |
| SEQ. ID. NO. 28420 | 211-LysAspIleSerAspLeuLysGluArgPheGly-221 |
| SEQ. ID. NO. 28421 | 228-AlaLysAspGlySer-232 |
| SEQ. ID. NO. 28422 | 237-LysAspLeuLysAla-241 |
| SEQ. ID. NO. 28423 | 287-ArgLeuAlaLysHisLeuAla-293 |
| SEQ. ID. NO. 28424 | 306-LeuGlyAlaGluLysPheCysAspIleLysCysArgLeuAlaGlyLeuLysProAspAla-325 |
| SEQ. ID. NO. 28425 | 339-GlyGlyValGluArgAlaAsnLeuGlyGluGluAsnLeuGluAlaLeuAla-355 |
| SEQ. ID. NO. 28426 | 383-PheValSerAspSerAspAlaGluLeuAlaMetIleGluLysAlaCysAla-399 |
| SEQ. ID. NO. 28427 | 420-AspLeuAlaArgLysValValAsn-427 |
| SEQ. ID. NO. 28428 | 444-LeuGlyIleLysAspLysIleArgAlaIleAla-454 |
| SEQ. ID. NO. 28429 | 458-TyrGlyAlaGluAspValAspPheSerAla-467 |
| SEQ. ID. NO. 28430 | 474-AlaSerLeuGluLysLeuGlyLeuAspLysMetPro-485 |
| SEQ. ID. NO. 28431 | 541-ProAlaAlaGluLysIleAspValAspGluHisGly-552 |
| g142 | |
| AMPHI Regions - AMPHI | |
| SEQ. ID. NO. 28432 | 26-ArgPheAlaAlaMetProAsnMetValGlyLys-36 |
| SEQ. ID. NO. 28433 | 44-GlyGlnProGlyLysMetPhe-50 |
| SEQ. ID. NO. 28434 | 100-AlaValThrProCysArg-105 |
| SEQ. ID. NO. 28435 | 107-ValCysArgAspAspMetAsn-113 |
| SEQ. ID. NO. 28436 | 118-GlyCysHisArgIleThrGluArgSerLeuLysSerPheLeuGlnIleArgHisPheSerProLeuAsnArg-141 |
| Antigenic Index - Jameson-Wolf | |
| SEQ. ID. NO. 28437 | 37-ProLeuPheGlyArgGlnAlaGlyGlnProGlyLysMet-49 |
| SEQ. ID. NO. 28438 | 60-HisIleAspAlaGluAlaAlaValPheArgGlnAspArgAsnAspSerArgThrPro-78 |
| SEQ. ID. NO. 28439 | 83-HisHisGlyArgArgLeuValGlyAsnArgArgAsnArgArgHisCysAsnAlaValThrProCysArgThrValCysArgAspAspMetAsnAla CysArgThrGlyCysHisArgIleThrGluArgSerLeuLys-128 |
| SEQ. ID. NO. 28440 | 137-SerProLeuAsnArgProLeuTyrLysAsnAlaAlaHisLysAlaSerProHis-154 |
| Hydrophilic Regions - Hopp-Woods | |
| SEQ. ID. NO. 28441 | 42-GlnAlaGlyGlnPro-46 |
| SEQ. ID. NO. 28442 | 60-HisIleAspAlaGluAlaAlaValPheArgGlnAspArgAsnAspSerArgThr-77 |
| SEQ. ID. NO. 28443 | 84-HisGlyArgArgLeuValGlyAsnArgArgAsnArgArgHisCys-98 |
| SEQ. ID. NO. 28444 | 106-ThrValCysArgAspAspMetAsnAlaCysArg-116 |
| SEQ. ID. NO. 28445 | 121-ArgIleThrGluArgSerLeuLys-128 |
| SEQ. ID. NO. 28446 | 147-AlaAlaHisLysAlaSerPro-153 |
| g144 | |
| AMPHI Regions - AMPHI | |
| SEQ. ID. NO. 28447 | 36-LeuGlyGlyIleValGlnGluPhe-43 |
| SEQ. ID. NO. 28448 | 45-ValLeuAlaAspGlyVal-50 |
| SEQ. ID. NO. 28449 | 58-PheAspAspAlaAlaSer-63 |
| SEQ. ID. NO. 28450 | 71-IleAsnLysGlnIleGlyArgValAlaGlyArg-81 |
| SEQ. ID. NO. 28451 | 144-TyrArgTyrLeuSerArgHis-150 |
| SEQ. ID. NO. 28452 | 170-GlyProAlaArgCysGlySerAlaTyrSerAlaGly-181 |
| SEQ. ID. NO. 28453 | 185-SerGlyArgCysArgLysThrAlaArgLeuAsnGlyPheArgArgProArgSer-202 |
| Antigenic Index - Jameson-Wolf | |
| SEQ. ID. NO. 28454 | 1-MetSerAspThrProAlaThrArgAspPheGlyLeuIleAspGlyArgAla-17 |
| SEQ. ID. NO. 28455 | 23-LeuSerAsnArgArgGlyThr-29 |
| SEQ. ID. NO. 28456 | 47-AlaAspGlyValArgGluAsnPro-54 |
| SEQ. ID. NO. 28457 | 57-SerPheAspAspAlaAlaSerTyrAlaAspAsnProPheGlnIleAsnLysGlnIleGly-76 |
| SEQ. ID. NO. 28458 | 78-ValAlaGlyArgIleArgGlyAlaAla-86 |
| SEQ. ID. NO. 28459 | 88-AspIleAsnGlyArgThrTyrArgValGluAlaAsnGluGlyArgAsnAlaLeuHisGlyGlySerHis-110 |
| SEQ. ID. NO. 28460 | 120-ValAlaAlaAspGlyArgArgLeuSerGlnArg-130 |
| SEQ. ID. NO. 28461 | 136-ProLeuGlyArgGlyArgProAlaTyr-144 |
| SEQ. ID. NO. 28462 | 146-TyrLeuSerArgHisArgAlaArgArgHisGlyValArgProAspAlaAlaHis-163 |
| SEQ. ID. NO. 28463 | 167-AlaGlyArgGlyProAlaArgCysGlySer-176 |
| SEQ. ID. NO. 28464 | 179-SerAlaGlyArgThrTyrSerGlyArgCysArgLysThrAlaArgLeuAsnGlyPheArgArgProArgSerIle-203 |
| Hydrophilic Regions - Hopp-Woods | |
| SEQ. ID. NO. 28465 | 1-MetSerAspThrProAlaThrArgAsp-9 |
| SEQ. ID. NO. 28466 | 24-SerAsnArgArgGlyThr-29 |
| SEQ. ID. NO. 28467 | 48-AspGlyValArgGluAsnPro-54 |
| SEQ. ID. NO. 28468 | 57-SerPheAspAspAlaAlaSer-63 |
| SEQ. ID. NO. 28469 | 78-ValAlaGlyArgIleArgGlyAlaAla-86 |
| SEQ. ID. NO. 28470 | 89-IleAsnGlyArgThrTyrArgValGluAlaAsnGluGlyArgAsnAlaLeu-105 |
| SEQ. ID. NO. 28471 | 121-AlaAlaAspGlyArgArgLeuSerGln-129 |
| SEQ. ID. NO. 28472 | 138-GlyArgGlyArgProAla-143 |
| SEQ. ID. NO. 28473 | 148-SerArgHisArgAlaArgArgHisGlyValArgProAspAla-161 |
| SEQ. ID. NO. 28474 | 168-GlyArgGlyProAlaArgCys-174 |
| SEQ. ID. NO. 28475 | 182-ArgThrTyrSerGlyArgCysArgLysThrAlaArg-193 |
| SEQ. ID. NO. 28476 | 195-AsnGlyPheArgArgProArgSerIle-203 |
| g146 | |
| AMPHI Regions - AMPHI | |
| SEQ. ID. NO. 28477 | 20-GlnTyrGlyLeuPheAspPheMetProCys-29 |
| SEQ. ID. NO. 28478 | 34-ProLeuAspAsnPheProThrVal-41 |
| SEQ. ID. NO. 28479 | 95-LeuArgAlaCysAlaValIle-101 |
| SEQ. ID. NO. 28480 | 140-AlaArgArgMetArg-144 |
| SEQ. ID. NO. 28481 | 158-ArgHisGlnArgGlyPheAlaArg-165 |

TABLE 1-continued

| | |
|---|---|
| Antigenic Index - Jameson-Wolf | |
| SEQ. ID. NO. 28482 | 13-IleAspHisAspLysValGluGln-20 |
| SEQ. ID. NO. 28483 | 29-CysLeuArgGlnProProLeuAspAsn-37 |
| SEQ. ID. NO. 28484 | 41-ValArgProAlaProPheGluAlaArgGlyLysHisValGluArgArgArgGlnAspLysAspThrAspSerPheArgGlnArgValAlaAsnLeuArgArgAlaLeu-76 |
| SEQ. ID. NO. 28485 | 86-AlaCysArgArgGlnArgIleHisAla-94 |
| SEQ. ID. NO. 28486 | 112-SerLeuLeuArgAspLysArgPhe-119 |
| SEQ. ID. NO. 28487 | 138-ArgArgAlaArgArgMetArgHisGlyAsnAla-148 |
| SEQ. ID. NO. 28488 | 155-GlnGlnProArgHisGlnArgGlyPheAla-164 |
| SEQ. ID. NO. 28489 | 166-AlaGlySerGlyArgAsnAspLysAspValAlaPheSerIle-179 |
| SEQ. ID. NO. 28490 | 193-ValSerGlnArgThr-197 |
| Hydrophilic Regions - Hopp-Woods | |
| SEQ. ID. NO. 28491 | 13-IleAspHisAspLysValGluGln-20 |
| SEQ. ID. NO. 28492 | 44-AlaProPheGluAlaArgGlyLysHisValGluArgArgArgGlnAspLysAspThrAspSerPheArgGlnArgValAlaAsnLeuArgArgAlaLeu-76 |
| SEQ. ID. NO. 28493 | 86-AlaCysArgArgGlnArgIleHisAla-94 |
| SEQ. ID. NO. 28494 | 112-SerLeuLeuArgAspLysArgPhe-119 |
| SEQ. ID. NO. 28495 | 138-ArgArgAlaArgArgMetArgHisGlyAsn-147 |
| SEQ. ID. NO. 28496 | 156-GlnProArgHisGlnArgGlyPheAla-164 |
| SEQ. ID. NO. 28497 | 167-GlySerGlyArgAsnAspLysAspValAla-176 |
| g148 | |
| AMPHI Regions - AMPHI | |
| SEQ. ID. NO. 28498 | 25-AlaAspLysIleArgLysIleGluAsnTrpPro-35 |
| SEQ. ID. NO. 28499 | 49-GlnSerAlaGluTyrPheArgLeuLeuValAspLeu-60 |
| SEQ. ID. NO. 28500 | 150-AlaGlyLeuGluLeuIleArgLysLeuGlyGlyGluIle-162 |
| SEQ. ID. NO. 28501 | 165-AlaAlaAlaIleLeuGluPheThrAspLeuGlnGlyGlyLysAsnIleArg-181 |
| Antigenic Index - Jameson-Wolf | |
| SEQ. ID. NO. 28502 | 4-LysThrSerAsnLeu-8 |
| SEQ. ID. NO. 28503 | 24-LeuAlaAspLysIleArgLysIleGluAsnTrpProGlnLysGly-38 |
| SEQ. ID. NO. 28504 | 66-MetAspGlnLysIleAspIle-72 |
| SEQ. ID. NO. 28505 | 76-LeuAspAlaArgGly-80 |
| SEQ. ID. NO. 28506 | 97-ProIleArgLysLysGlyLysLeuPro-105 |
| SEQ. ID. NO. 28507 | 117-TyrGlyGluAlaAlaVal-122 |
| SEQ. ID. NO. 28508 | 124-IleHisThrAspAlaValLysProGlySerArg-134 |
| SEQ. ID. NO. 28509 | 153-GluLeuIleArgLysLeuGlyGlyGluIleValGlu-164 |
| SEQ. ID. NO. 28510 | 172-ThrAspLeuGlnGlyGlyLysAsnIleArgAlaSerGlyAlaPro-186 |
| SEQ. ID. NO. 28511 | 192-GlnAsnGluGlyCysMetLysGly-199 |
| Hydrophilic Regions - Hopp-Woods | |
| SEQ. ID. NO. 28512 | 24-LeuAlaAspLysIleArgLysIleGluAsnTrpPro-35 |
| SEQ. ID. NO. 28513 | 66-MetAspGlnLysIleAspIle-72 |
| SEQ. ID. NO. 28514 | 97-ProIleArgLysLysGlyLysLeuPro-105 |
| SEQ. ID. NO. 28515 | 117-TyrGlyGluAlaAlaVal-122 |
| SEQ. ID. NO. 28516 | 124-IleHisThrAspAlaValLysProGlySer-133 |
| SEQ. ID. NO. 28517 | 153-GluLeuIleArgLysLeuGlyGlyGluIleValGlu-164 |
| SEQ. ID. NO. 28518 | 178-LysAsnIleArgAlaSerGly-184 |
| SEQ. ID. NO. 28519 | 195-GlyCysMetLysGly-199 |
| g149 | |
| AMPHI Regions - AMPHI | |
| SEQ. ID. NO. 28520 | 72-AsnLeuGlyAspAlaLeuAspGlyValProGlyIle-83 |
| SEQ. ID. NO. 28521 | 101-ThrGlyArgArgIleLysValLeuAsnHisHisGlyGluThrGlyAspMet-117 |
| SEQ. ID. NO. 28522 | 135-GlnValGluIleLeuArgGlyProValThr-144 |
| SEQ. ID. NO. 28523 | 152-ValAlaGlyLeuValAsp-157 |
| SEQ. ID. NO. 28524 | 164-ProGluLysMetProGluAsn-170 |
| SEQ. ID. NO. 28525 | 184-AsnLeuGluLysLeu-188 |
| SEQ. ID. NO. 28526 | 220-TyrArgAsnLeuLysArgLeuProAspSerHis-230 |
| SEQ. ID. NO. 28527 | 345-PheProGlyPheGlu-349 |
| SEQ. ID. NO. 28528 | 366-AlaGlyAspAlaValGluAsnPhePheAsnAsn-376 |
| SEQ. ID. NO. 28529 | 389-ProIleGlyArgLeuLys-394 |
| SEQ. ID. NO. 28530 | 411-AlaIleProGluThrVal-416 |
| SEQ. ID. NO. 28531 | 472-GlnProLeuProAspLeuGlyAla-479 |
| SEQ. ID. NO. 28532 | 565-ArgPheGlyAsnTyrIleTyrAlaGln-573 |
| SEQ. ID. NO. 28533 | 576-AsnAspGlyArgGlyProLysSerIleGluAsp-586 |
| SEQ. ID. NO. 28534 | 627-ArgGlyArgLeuLysAsnLeuProSer-635 |
| SEQ. ID. NO. 28535 | 672-LeuThrAspArgIle-676 |
| Antigenic Index - Jameson-Wolf | |
| SEQ. ID. NO. 28536 | 25-HisGluThrGluGln-29 |
| SEQ. ID. NO. 28537 | 40-GlyLysSerArgProArgAlaThrSerGly-49 |
| SEQ. ID. NO. 28538 | 55-ThrAlaSerAspLysIleIleSerGlyAspThrLeuArgGlnLysAla-70 |
| SEQ. ID. NO. 28539 | 97-IleArgGlyGlnThrGlyArgArgIleLysVal-107 |
| SEQ. ID. NO. 28540 | 109-AsnHisHisGlyGluThrGlyAspMetAlaAspPheSerProAspHis-124 |
| SEQ. ID. NO. 28541 | 137-GluIleLeuArgGlyPro-142 |
| SEQ. ID. NO. 28542 | 157-AspValAlaAspGlyLysIleProGluLysMetProGluAsnGlyValSerGlyGluAlaGlyLeu-178 |
| SEQ. ID. NO. 28543 | 180-LeuSerSerGlyAsnLeuGluLysLeuThrSer-190 |
| SEQ. ID. NO. 28544 | 207-GlyLeuTyrArgLysSerGlyAspTyrAlaValProArgTyrArgAsnLeuLysArgLeuProAspSerHisAlaAspSerGlnThrGly-236 |
| SEQ. ID. NO. 28545 | 244-GlyGluLysGlyPhe-248 |
| SEQ. ID. NO. 28546 | 252-AlaTyrSerAspArgArgAspArgTyrGlyLeuProAlaHisSerHisGluTyrAspAspCysHisAla-274 |
| SEQ. ID. NO. 28547 | 281-SerLeuIleAsnLysArgTyrLeu-288 |
| SEQ. ID. NO. 28548 | 295-LeuThrGluGluAspIleAspTyrAspAsnProGlyLeu-307 |
| SEQ. ID. NO. 28549 | 309-CysGlyPheHisAspGlyAspGlyAlaHis-318 |
| SEQ. ID. NO. 28550 | 320-HisThrHisAsnGlyLysProTrpIleAspLeuArgAsnLysArgTyrGluLeuArgAlaGluTrpLysGlnProPheProGly-347 |

TABLE 1-continued

| | |
|---|---|
| SEQ. ID. NO. 28551 | 354-HisLeuAsnArgAsnAspTyrHisHisAspGluLysAlaGlyAspAlaVal-370 |
| SEQ. ID. NO. 28552 | 374-PheAsnAsnLysThrHisAsnAlaArgIleGluLeuArgHisGlnProIleGlyArgLeuLysGlySerTrp-397 |
| SEQ. ID. NO. 28553 | 402-LeuGlyGlnLysSerSerAla-408 |
| SEQ. ID. NO. 28554 | 413-ProGluThrValGln-417 |
| SEQ. ID. NO. 28555 | 421-LeuIleAspAsnAsnValArg-427 |
| SEQ. ID. NO. 28556 | 437-AlaAsnTrpAspAsnPheThrLeuGluGlyGlyValArgValGluLysGlnLysAlaSerIleArgTyrAspLysAlaLeuIleAspArgGluAsnTyr TyrAsnGlnProLeuProAsp-476 |
| SEQ. ID. NO. 28557 | 506-SerHisGlnGluArgLeuProSerThrGlnGluLeuTyrAlaHisGly-521 |
| SEQ. ID. NO. 28558 | 531-ValGlyAsnLysHisLeuAsnLysGluArgSerAsnAsnIle-544 |
| SEQ. ID. NO. 28559 | 549-GlyTyrGluGlyAspArgTrpGln-556 |
| SEQ. ID. NO. 28560 | 562-TyrArgAsnArgPheGlyAsn-568 |
| SEQ. ID. NO. 28561 | 574-ThrLeuAsnAspGlyArgGlyProLysSerIleGluAspAspSerGluMetLysLeu-592 |
| SEQ. ID. NO. 28562 | 594-ArgTyrAsnGlnSerGlyAlaAspPheTyrGlyAlaGluGly-607 |
| SEQ. ID. NO. 28563 | 609-IleTyrPheLysProThrProArgTyrArgIle-619 |
| SEQ. ID. NO. 28564 | 621-ValSerGlyAspTyrValArgGlyArgLeuLysAsnLeuProSerLeuProGlyArgGluAspProTyrGlyLysArgProPhe-648 |
| SEQ. ID. NO. 28565 | 651-GlnAlaAspGlnAsnAlaProArgIleProAla-661 |
| SEQ. ID. NO. 28566 | 670-ThrSerLeuThrAspArgIleAspAlaAsnLeuAspTyr-682 |
| SEQ. ID. NO. 28567 | 689-AsnLysLeuAlaArgTyrGluThrArgThrProGlyHis-701 |
| SEQ. ID. NO. 28568 | 707-GlyAlaAsnTyrArgArgAsnThrArgTyrGlyGluTrp-719 |
| SEQ. ID. NO. 28569 | 725-AlaAspAsnLeuLeu-729 |
| SEQ. ID. NO. 28570 | 739-PheLeuSerAspThrProGlnMetGlyArgSerPheThrGlyGlyVal-754 |
| Hydrophilic Regions - Hopp-Woods | |
| SEQ. ID. NO. 28571 | 25-HisGluThrGluGln-29 |
| SEQ. ID. NO. 28572 | 40-GlyLysSerArgProArgAlaThr-47 |
| SEQ. ID. NO. 28573 | 55-ThrAlaSerAspLysIleIleSer-62 |
| SEQ. ID. NO. 28574 | 64-AspThrLeuArgGlnLysAla-70 |
| SEQ. ID. NO. 28575 | 100-GlnThrGlyArgArgIleLysVal-107 |
| SEQ. ID. NO. 28576 | 112-GlyGluThrGlyAspMetAlaAspPheSerPro-122 |
| SEQ. ID. NO. 28577 | 157-AspValAlaAspGlyLysIleProGluLysMetProGluAsnGlyValSerGly-174 |
| SEQ. ID. NO. 28578 | 181-SerSerGlyAsnLeuGluLysLeuThr-189 |
| SEQ. ID. NO. 28579 | 207-GlyLeuTyrArgLysSerGlyAsp-214 |
| SEQ. ID. NO. 28580 | 219-ArgTyrArgAsnLeuLysArgLeuProAspSerHisAlaAspSerGlnThr-235 |
| SEQ. ID. NO. 28581 | 253-TyrSerAspArgArgAspArgTyrGly-261 |
| SEQ. ID. NO. 28582 | 267-HisGluTyrAspAspCysHisAla-274 |
| SEQ. ID. NO. 28583 | 295-LeuThrGluGluAspIleAspTyrAspAsn-304 |
| SEQ. ID. NO. 28584 | 312-HisAspGlyAspGlyAlaHis-318 |
| SEQ. ID. NO. 28585 | 330-LeuArgAsnLysArgTyrGluLeuArgAlaGluTrp-341 |
| SEQ. ID. NO. 28586 | 354-HisLeuAsnArgAsnAspTyrHisHisAspGluLysAlaGlyAspAlaVal-370 |
| SEQ. ID. NO. 28587 | 377-LysThrHisAsnAlaArgIleGluLeuArgHis-387 |
| SEQ. ID. NO. 28588 | 391-GlyArgLeuLysGly-395 |
| SEQ. ID. NO. 28589 | 446-GlyGlyValArgValGluLysGlnLysAlaSerIleArgTyrAspLysAlaLeuIleAspArgGluAsnTyr-469 |
| SEQ. ID. NO. 28590 | 506-SerHisGlnGluArgLeuProSer-513 |
| SEQ. ID. NO. 28591 | 535-HisLeuAsnLysGluArgSerAsnAsn-543 |
| SEQ. ID. NO. 28592 | 550-TyrGluGlyAspArgTrp-555 |
| SEQ. ID. NO. 28593 | 562-TyrArgAsnArgPhe-566 |
| SEQ. ID. NO. 28594 | 575-LeuAsnAspGlyArgGlyProLysSerIleGluAspAspSerGluMetLysLeu-592 |
| SEQ. ID. NO. 28595 | 603-TyrGlyAlaGluGly-607 |
| SEQ. ID. NO. 28596 | 613-ProThrProArgTyrArgIle-619 |
| SEQ. ID. NO. 28597 | 624-AspTyrValArgGlyArgLeuLysAsn-632 |
| SEQ. ID. NO. 28598 | 637-ProGlyArgGluAspProTyrGlyLys-645 |
| SEQ. ID. NO. 28599 | 652-AlaAspGlnAsnAlaProArg-658 |
| SEQ. ID. NO. 28600 | 671-SerLeuThrAspArgIleAspAla-678 |
| SEQ. ID. NO. 28601 | 690-LysLeuAlaArgTyrGluThrArgThrProGly-700 |
| SEQ. ID. NO. 28602 | 709-AsnTyrArgArgAsnThrArgTyrGly-717 |
| g150 | |
| AMPHI Regions - AMPHI | |
| SEQ. ID. NO. 28603 | 60-GlyGluIleLeuAspLeuLeu-66 |
| SEQ. ID. NO. 28604 | 87-LeuLeuSerHisPheGlu-92 |
| SEQ. ID. NO. 28605 | 100-PheValLysGlyTyrAla-105 |
| SEQ. ID. NO. 28606 | 132-IleAlaGlyValLeuHisArgPheProAlaLysLeuThrAla-145 |
| SEQ. ID. NO. 28607 | 147-GlnPheAlaGlyLeuLeuArgProLeuAla-156 |
| SEQ. ID. NO. 28608 | 235-GlyValAlaProPheArg-240 |
| SEQ. ID. NO. 28609 | 272-ThrGluTrpGlnGlnPheAlaLys-279 |
| SEQ. ID. NO. 28610 | 304-IleArgGluGlnAla-308 |
| SEQ. ID. NO. 28611 | 327-AlaAlaLysMetAlaLysGluValGluAlaAlaLeuLeuAspValIleIleGly-344 |
| Antigenic Index - Jameson-Wolf | |
| SEQ. ID. NO. 28612 | 2-TerTyrCysLysAlaAspProPhePro-10 |
| SEQ. ID. NO. 28613 | 17-GlnLysIleThrAlaArgGlnSerAspLysAspValArgHisIleGluIleAspLeuSerGlySerAspLeu-40 |
| SEQ. ID. NO. 28614 | 43-LeuProGlyAspAla-47 |
| SEQ. ID. NO. 28615 | 52-PheAspAsnAspProAlaLeuVal-59 |
| SEQ. ID. NO. 28616 | 69-AsnProAlaThrGluIleGlnAlaGlyGlyLysThrLeu-81 |
| SEQ. ID. NO. 28617 | 93-LeuThrGlnAsnThrProAlaPhe-100 |
| SEQ. ID. NO. 28618 | 108-AlaAspAsnAspGluLeuAspArgIleAlaAla-118 |
| SEQ. ID. NO. 28619 | 163-SerSerSerGlnAlaGluAlaGlyAspGluValHis-174 |
| SEQ. ID. NO. 28620 | 181-ArgPheGluHisGluGlyArgAlaArgAlaGlyGlyAlaSerGlyPhePhe-197 |
| SEQ. ID. NO. 28621 | 199-AspArgLeuGluGluAspGlyThrVal-207 |
| SEQ. ID. NO. 28622 | 210-PheAlaGluArgAsnAspGlyPheArgLeuProGluAspSerArgLysPro-226 |
| SEQ. ID. NO. 28623 | 231-GlySerGlyThrGly-235 |
| SEQ. ID. NO. 28624 | 245-GlnArgAlaAlaGluAsnAlaGluGlyArgAsn-255 |
| SEQ. ID. NO. 28625 | 276-GlnPheAlaLysAspGlyPheLeuHisArgTyrAspPheAlaTrpSerArgAspGlnGluGluLysIleTyrVal-300 |

TABLE 1-continued

| | |
|---|---|
| SEQ. ID. NO. 28626 | 302-AspLysIleArgGluGlnAlaGlu-309 |
| SEQ. ID. NO. 28627 | 326-AspAlaAlaLysMetAlaLysGluValGlu-335 |
| SEQ. ID. NO. 28628 | 345-AlaGlyHisSerAspGluAspGlyAlaGluGlyTyr-356 |
| SEQ. ID. NO. 28629 | 359-MetLeuArgGluGluLysArgTyrGlnArgAspValTyr-371 |
| Hydrophilic Regions - Hopp-Woods | |
| SEQ. ID. NO. 28630 | 18-LysIleThrAlaArgGlnSerAspLysAspValArgHisIleGluIleAspLeuSerGly-37 |
| SEQ. ID. NO. 28631 | 72-ThrGluIleGlnAlaGlyGlyLys-79 |
| SEQ. ID. NO. 28632 | 108-AlaAspAsnAspGluLeuAspArgIleAlaAla-118 |
| SEQ. ID. NO. 28633 | 165-SerGlnAlaGluAlaGlyAspGluValHis-174 |
| SEQ. ID. NO. 28634 | 181-ArgPheGluHisGluGlyArgAlaArgAlaGlyGly-192 |
| SEQ. ID. NO. 28635 | 199-AspArgLeuGluGluAspGlyThrVal-207 |
| SEQ. ID. NO. 28636 | 210-PheAlaGluArgAsnAspGlyPheArgLeuProGluAspSerArgLysPro-226 |
| SEQ. ID. NO. 28637 | 246-ArgAlaAlaGluAsnAlaGluGlyArg-254 |
| SEQ. ID. NO. 28638 | 290-TrpSerArgAspGlnGluGluLysIleTyrVal-300 |
| SEQ. ID. NO. 28639 | 302-AspLysIleArgGluGlnAlaGlu-309 |
| SEQ. ID. NO. 28640 | 326-AspAlaAlaLysMetAlaLysGluValGlu-335 |
| SEQ. ID. NO. 28641 | 346-GlyHisSerAspGluAspGlyAlaGluGlyTyr-356 |
| SEQ. ID. NO. 28642 | 359-MetLeuArgGluGluLysArgTyrGlnArgAspValTyr-371 |
| g151 | |
| AMPHI Regions - AMPHI | |
| SEQ. ID. NO. 28643 | 6-AsnIleAlaIleIleAla-11 |
| SEQ. ID. NO. 28644 | 22-AspGlnLeuLeuArg-26 |
| SEQ. ID. NO. 28645 | 73-AspThrProGlyHis-77 |
| SEQ. ID. NO. 28646 | 81-GlyGlyGluValGluArgValLeuGlyMetValAspCysVal-94 |
| SEQ. ID. NO. 28647 | 128-LysIleAspLysPro-132 |
| SEQ. ID. NO. 28648 | 144-PheGluLeuPheAspAsnLeuGlyAlaThr-153 |
| SEQ. ID. NO. 28649 | 165-SerGlyLeuSerGlyPheAlaLysLeuGluGluThrAspGlu-178 |
| SEQ. ID. NO. 28650 | 182-MetArgProLeuPheAspThrIleLeuLysTyrThr-193 |
| SEQ. ID. NO. 28651 | 248-GlyArgIleAsnGlnLeuLeuGlyPheLysGlyLeuGluArgVal-262 |
| SEQ. ID. NO. 28652 | 273-ValIleIleSerGlyIleGlu-279 |
| SEQ. ID. NO. 28653 | 330-IleArgAspArgLeuGlnLysGluLeu-338 |
| SEQ. ID. NO. 28654 | 348-AspThrAlaAspAla-352 |
| SEQ. ID. NO. 28655 | 396-CysGluProTyrGluAsnLeuThrValAsp-405 |
| SEQ. ID. NO. 28656 | 457-LeuThrArgGlyValGly-462 |
| SEQ. ID. NO. 28657 | 464-MetSerHisValPheAsp-469 |
| SEQ. ID. NO. 28658 | 537-LysGlyLysLysLeuThrAsnIle-544 |
| SEQ. ID. NO. 28659 | 551-GluAlaValArgLeuThrThr-557 |
| Antigenic Index - Jameson-Wolf | |
| SEQ. ID. NO. 28660 | 1-MetLysGlnIleArg-5 |
| SEQ. ID. NO. 28661 | 13-ValAspHisGlyLysThrThrLeu-20 |
| SEQ. ID. NO. 28662 | 24-LeuLeuArgGlnSerGlyThrPheArgAlaAsnGlnGlnValAspGluArgValMetAspSerAsnAspLeuGluLysGluArgGlyIle-53 |
| SEQ. ID. NO. 28663 | 59-AsnThrAlaIleAspTyrGluGlyCysHis-68 |
| SEQ. ID. NO. 28664 | 72-ValAspThrProGlyHisAlaAspPheGlyGlyGluValGluArg-86 |
| SEQ. ID. NO. 28665 | 99-AspAlaGlnGluGlyProMetProGlnThrArgPheValThr-112 |
| SEQ. ID. NO. 28666 | 128-LysIleAspLysProSerAlaArgProSerTrp-138 |
| SEQ. ID. NO. 28667 | 151-GlyAlaThrAspGluGlnLeuAsp-158 |
| SEQ. ID. NO. 28668 | 171-AlaLysLeuGluGluThrAspGluSerSerAspMetArgProLeu-185 |
| SEQ. ID. NO. 28669 | 193-ThrProAlaProSerGlySerAlaAspGluProLeu-204 |
| SEQ. ID. NO. 28670 | 211-LeuAspTyrAspAsnTyrThrGly-218 |
| SEQ. ID. NO. 28671 | 226-LeuAsnGlyArgIleLysProGlyGln-234 |
| SEQ. ID. NO. 28672 | 241-HisGluGlnGlnIleAla-246 |
| SEQ. ID. NO. 28673 | 257-LysGlyLeuGluArgValProLeuGluGluAlaGluAlaGlyAsp-271 |
| SEQ. ID. NO. 28674 | 277-GlyIleGluAspIleGly-282 |
| SEQ. ID. NO. 28675 | 287-IleThrAspLysAspAsnProLysGlyLeuPro-297 |
| SEQ. ID. NO. 28676 | 300-SerValAspGluProThrLeu-306 |
| SEQ. ID. NO. 28677 | 314-ThrSerProLeuAlaGlyThrGluGlyLysPheValThrSerArgGlnIleArgAspArgLeuGlnLysGluLeuLeu-339 |
| SEQ. ID. NO. 28678 | 344-LeuArgValGluAspThrAlaAspAlaAspValPheArgValSerGlyArgGlyGluLeu-363 |
| SEQ. ID. NO. 28679 | 371-AsnMetArgArgGluGlyTyr-377 |
| SEQ. ID. NO. 28680 | 381-ValGlyLysProArgValValTyrArgAspIleAspGlyGlnLysCysGluProTyrGluAsnLeuThrValAspValProAspAspAsnGlnGlyAla ValMetGluGluLeuGlyArgArgArgGlyGluLeuThrAsnMetGluSerAspGlyAsnGlyArgThrArgLeuGluTyr-440 |
| SEQ. ID. NO. 28681 | 467-ValPheAspAspTyrAlaProValLysProAspMetProGlyArgHisAsnGly-484 |
| SEQ. ID. NO. 28682 | 489-GlnGluGlnGlyGlu-493 |
| SEQ. ID. NO. 28683 | 501-AsnLeuGluAspArgGlyArgMetPheValSerProAsnAspLysIleTyr-517 |
| SEQ. ID. NO. 28684 | 524-IleHisSerArgAspAsnAspLeu-531 |
| SEQ. ID. NO. 28685 | 535-ProLeuLysGlyLysLysLeuThrAsnIleArgAlaSerGlyThrAspGluAlaValArg-554 |
| SEQ. ID. NO. 28686 | 569-PheIleAspAspAspGluLeuValGlu-577 |
| SEQ. ID. NO. 28687 | 579-ThrProGlnSerIleArgLeuArgMet-587 |
| SEQ. ID. NO. 28688 | 591-SerGluLeuGluArgArgArgHisPheLysLysLeuAsp-603 |
| Hydrophilic Regions - Hopp-Woods | |
| SEQ. ID. NO. 28689 | 1-MetLysGlnIleArg-5 |
| SEQ. ID. NO. 28690 | 29-GlyThrPheArgAla-33 |
| SEQ. ID. NO. 28691 | 35-GlnGlnValAspGluArgValMetAspSerAsnAspLeuGluLysGluArgGlyIle-53 |
| SEQ. ID. NO. 28692 | 60-ThrAlaIleAspTyrGluGly-66 |
| SEQ. ID. NO. 28693 | 80-PheGlyGlyGluValGluArg-86 |
| SEQ. ID. NO. 28694 | 99-AspAlaGlnGluGlyProMetPro-106 |
| SEQ. ID. NO. 28695 | 128-LysIleAspLysProSerAla-134 |
| SEQ. ID. NO. 28696 | 151-GlyAlaThrAspGluGlnLeuAsp-158 |
| SEQ. ID. NO. 28697 | 171-AlaLysLeuGluGluThrAspGluSerSerAspMetArgProLeu-185 |
| SEQ. ID. NO. 28698 | 198-GlySerAlaAspGluProLeu-204 |
| SEQ. ID. NO. 28699 | 226-LeuAsnGlyArgIleLysPro-232 |

| | |
|---|---|
| SEQ. ID. NO. 28700 | 241-HisGluGlnGlnIleAla-246 |
| SEQ. ID. NO. 28701 | 258-GlyLeuGluArgValProLeuGluGluAlaGluAlaGlyAsp-271 |
| SEQ. ID. NO. 28702 | 277-GlyIleGluAspIleGly-282 |
| SEQ. ID. NO. 28703 | 287-IleThrAspLysAspAsnProLysGly-295 |
| SEQ. ID. NO. 28704 | 300-SerValAspGluProThrLeu-306 |
| SEQ. ID. NO. 28705 | 318-AlaGlyThrGluGlyLysPheValThr-326 |
| SEQ. ID. NO. 28706 | 328-ArgGlnIleArgAspArgLeuGlnLysGluLeuLeu-339 |
| SEQ. ID. NO. 28707 | 344-LeuArgValGluAspThrAlaAspAlaAspValPheArgValSerGlyArgGlyGluLeu-363 |
| SEQ. ID. NO. 28708 | 371-AsnMetArgArgGluGlyTyr-377 |
| SEQ. ID. NO. 28709 | 381-ValGlyLysProArgValValTyrArgAspIleAspGlyGlnLysCysGluProTyrGlu-400 |
| SEQ. ID. NO. 28710 | 405-AspValProAspAspAsnGlnGlyAlaValMetGluGluLeuGlyArgArgArgGlyGluLeuThrAsnMetGluSerAspGlyAsnGlyArgThrArgLeu-438 |
| SEQ. ID. NO. 28711 | 472-AlaProValLysProAspMetProGlyArgHis-482 |
| SEQ. ID. NO. 28712 | 489-GlnGluGlnGlyGlu-493 |
| SEQ. ID. NO. 28713 | 502-LeuGluAspArgGlyArgMet-508 |
| SEQ. ID. NO. 28714 | 512-ProAsnAspLysIleTyr-517 |
| SEQ. ID. NO. 28715 | 525-HisSerArgAspAsnAspLeu-531 |
| SEQ. ID. NO. 28716 | 536-LeuLysGlyLysLysLeuThrAsn-543 |
| SEQ. ID. NO. 28717 | 545-ArgAlaSerGlyThrAspGluAlaValArg-554 |
| SEQ. ID. NO. 28718 | 569-PheIleAspAspAspGluLeuValGlu-577 |
| SEQ. ID. NO. 28719 | 583-IleArgLeuArgMet-587 |
| SEQ. ID. NO. 28720 | 591-SerGluLeuGluArgArgArgHisPheLysLysLeuAsp-603 |
| g152 | |
| AMPHI Regions - AMPHI | |
| SEQ. ID. NO. 28721 | 10-PheProThrArgLeuPhe-15 |
| SEQ. ID. NO. 28722 | 66-ArgPheSerArgPheValArgGlyTrpAlaGlyIleArgGlyTyrLeuLysAsnGlyIleProGluHisIleGlnProGlyHisAsnProLeu-96 |
| SEQ. ID. NO. 28723 | 103-AlaLeuLeuAlaAla-107 |
| SEQ. ID. NO. 28724 | 130-LeuAsnHisLeuValSerGluHisThrGlySerLeu-141 |
| SEQ. ID. NO. 28725 | 150-PheLysLeuLeuAlaValPheSerAlaValHisIleAlaAlaValAlaAlaTyr-167 |
| SEQ. ID. NO. 28726 | 177-ArgProMetIleThr-181 |
| Antigenic Index - Jameson-Wolf | |
| SEQ. ID. NO. 28727 | 1-MetLysAsnLysThrLysValTrp-8 |
| SEQ. ID. NO. 28728 | 29-SerAlaLysAlaGlyGlyAsp-35 |
| SEQ. ID. NO. 28729 | 61-GlySerAspThrAlaArgPhe-67 |
| SEQ. ID. NO. 28730 | 79-GlyTyrLeuLysAsnGlyIleProGluHisIleGlnProGlyHisAsnProLeu-96 |
| SEQ. ID. NO. 28731 | 119-AlaAsnGluAsnThrPheSerThrAsnGlyTyr-129 |
| SEQ. ID. NO. 28732 | 137-HisThrGlySerLeuIleArg-143 |
| SEQ. ID. NO. 28733 | 169-IlePheLysLysLysAsnLeuVal-176 |
| SEQ. ID. NO. 28734 | 186-IleGluGlyLysThrSerIle-192 |
| Hydrophilic Regions - Hopp-Woods | |
| SEQ. ID. NO. 28735 | 1-MetLysAsnLysThrLysVal-7 |
| SEQ. ID. NO. 28736 | 63-AspThrAlaArgPhe-67 |
| SEQ. ID. NO. 28737 | 169-IlePheLysLysLysAsnLeuVal-176 |
| SEQ. ID. NO. 28738 | 186-IleGluGlyLysThrSerIle-192 |
| g153 | |
| AMPHI Regions - AMPHI | |
| SEQ. ID. NO. 28739 | 17-AlaAlaSerValLeuSerLeuProGluMetMetArgLeuMetValPhe-32 |
| SEQ. ID. NO. 28740 | 96-ThrLeuValAlaTyrIleLysLeuSerSerValAlaLys-108 |
| SEQ. ID. NO. 28741 | 130-ValSerValProGlnHisTrp-136 |
| SEQ. ID. NO. 28742 | 224-ThrIlePheSerGlyIleAlaTyr-231 |
| SEQ. ID. NO. 28743 | 274-AlaLysLysLeuSerHisLeuTyrArgIleThrGluAlaValGlyArgTrpSerMetIleAspIlePheValIle-298 |
| Antigenic Index - Jameson-Wolf | |
| SEQ. ID. NO. 28744 | 65-IleArgLysGlnAla-69 |
| SEQ. ID. NO. 28745 | 81-ValArgLeuArgGln-85 |
| SEQ. ID. NO. 28746 | 143-ArgLeuThrGlyAsnAsnAla-149 |
| SEQ. ID. NO. 28747 | 151-GlnThrAlaSerGluGlyLysThrCysCysSer-161 |
| SEQ. ID. NO. 28748 | 165-TyrPheArgAspSerAlaGluSerProCysGly-175 |
| SEQ. ID. NO. 28749 | 181-LeuTyrGlyGlyArgProLysSerLeuSer-190 |
| SEQ. ID. NO. 28750 | 215-SerAsnProAlaAlaThrGlu-221 |
| SEQ. ID. NO. 28751 | 234-AspGluGlyAspArgLeu-239 |
| SEQ. ID. NO. 28752 | 272-AlaGlyAlaLysLysLeu-277 |
| SEQ. ID. NO. 28753 | 339-LeuLeuTrpAspLysArgAlaSerAspGlyIleAla-350 |
| SEQ. ID. NO. 28754 | 352-AsnGluThrGluLysTyrAsp-358 |
| Hydrophilic Regions - Hopp-Woods | |
| SEQ. ID. NO. 28755 | 81-ValArgLeuArgGln-85 |
| SEQ. ID. NO. 28756 | 152-ThrAlaSerGluGlyLysThrCysCys-160 |
| SEQ. ID. NO. 28757 | 168-AspSerAlaGluSerPro-173 |
| SEQ. ID. NO. 28758 | 182-TyrGlyGlyArgProLysSerLeuSer-190 |
| SEQ. ID. NO. 28759 | 234-AspGluGlyAspArgLeu-239 |
| SEQ. ID. NO. 28760 | 273-GlyAlaLysLysLeu-277 |
| SEQ. ID. NO. 28761 | 339-LeuLeuTrpAspLysArgAlaSerAsp-347 |
| SEQ. ID. NO. 28762 | 352-AsnGluThrGluLysTyrAsp-358 |
| g154 | |
| AMPHI Regions - AMPHI | |
| SEQ. ID. NO. 28763 | 122-GlyValThrGlyLeuGlyThrLeuLeu-130 |
| SEQ. ID. NO. 28764 | 152-GlnAspIleProProValThr-158 |
| SEQ. ID. NO. 28765 | 262-ThrLysAsnSerLysAsnValLysSer-270 |
| SEQ. ID. NO. 28766 | 298-PheLysGlnSerVal-302 |
| SEQ. ID. NO. 28767 | 360-SerLysGluHisTrpLysGlnGlnPheGlnThrAlaLeuAsnLysGlyLeuThrAla-378 |
| SEQ. ID. NO. 28768 | 389-GlyLysMetIleGluLeuAsnAsp-396 |

TABLE 1-continued

| | |
|---|---|
| SEQ. ID. NO. 28769 | 429-LysLeuAlaAspLeuLeuAspLysPheAsnAsnLeuPro-441 |
| SEQ. ID. NO. 28770 | 446-ValAlaGluLeuAsnGly-451 |
| SEQ. ID. NO. 28771 | 467-LeuSerSerIleAspLysLeuValGlyAsnProGlnThrGlnAsnIleProAsnGluLeuAsnGlnThr-489 |
| SEQ. ID. NO. 28772 | 506-IleTyrGlyAspValGlnAsnThrLeuGlnSerLeuAspLysThrLeuLysAspValGlnProValIleAsnThrLeuLysGluLys-534 |
| Antigenic Index - Jameson-Wolf | |
| SEQ. ID. NO. 28773 | 1-MetThrAspAsnSerProProProAsnGlyHisAlaGlnAlaArgValArgLysAsnAsnThr-21 |
| SEQ. ID. NO. 28774 | 43-LysGluIleArgAsnArgGlyProVal-51 |
| SEQ. ID. NO. 28775 | 57-AspSerAlaGluGlyIleGluValAsnAsnThr-67 |
| SEQ. ID. NO. 28776 | 75-AspValGlyArgValThrArgIleLysLeuArgAspAspGlnLysGlyValGlu-92 |
| SEQ. ID. NO. 28777 | 100-AspValSerGlyLeuIleArgSerAspThrGln-110 |
| SEQ. ID. NO. 28778 | 114-ValLysProArgIleAspGlnSerGly-122 |
| SEQ. ID. NO. 28779 | 138-ThrProGlyLysSerGlyGluAlaLysAspValPheGln-150 |
| SEQ. ID. NO. 28780 | 169-LeuIleGlyLysAsnAspArgIleLeuAsn-178 |
| SEQ. ID. NO. 28781 | 196-AlaHisPheAspProSerAspGlnSer-204 |
| SEQ. ID. NO. 28782 | 212-GlnSerProAsnAspLysLeuIle-219 |
| SEQ. ID. NO. 28783 | 227-LeuGluSerGlyIleAsnIleGluThrThrGlySerGlyIleLysLeuAsnSer-244 |
| SEQ. ID. NO. 28784 | 256-SerPheAspSerProLysThrLysAsnSerLysAsnValLysSerGluAspSer-273 |
| SEQ. ID. NO. 28785 | 275-ThrLeuTyrAspSerArgSerGluIleAlaAsnLeuProAspAspArgSerLeu-292 |
| SEQ. ID. NO. 28786 | 300-GlnSerValArgGlyLeu-305 |
| SEQ. ID. NO. 28787 | 311-ValGluTyrLysGlyLeuAsnVal-318 |
| SEQ. ID. NO. 28788 | 325-ProTyrPheAspArgAsnAspSer-332 |
| SEQ. ID. NO. 28789 | 345-IleArgIleGluProSerArgLeuGluIleAsnAlaAspGluGlnSerLysGluHisTrpLysGlnGlnPhe-368 |
| SEQ. ID. NO. 28790 | 371-AlaLeuAsnLysGlyLeu-376 |
| SEQ. ID. NO. 28791 | 386-LeuThrGlyGlyLysMetIleGluLeuAsnAspGlnProSerAlaSerProLysLeuArgPro-406 |
| SEQ. ID. NO. 28792 | 416-IleAlaThrArgGlyGlyGlyLeuAspAspLeuGlnValLysLeu-430 |
| SEQ. ID. NO. 28793 | 432-AspLeuLeuAspLysPheAsnAsnLeuProLeuAspLysThrValAla-447 |
| SEQ. ID. NO. 28794 | 450-AsnGlySerLeuAlaGluLeuLysSerAlaLeuLysSerAlaAsn-464 |
| SEQ. ID. NO. 28795 | 469-SerIleAspLysLeuValGlyAsnProGlnThrGlnAsnIleProAsnGluLeuAsnGlnThrLeuLysGluLeuArgIle-495 |
| SEQ. ID. NO. 28796 | 500-ValSerProGlnSer-504 |
| SEQ. ID. NO. 28797 | 516-SerLeuAspLysThrLeuLysAspValGln-525 |
| SEQ. ID. NO. 28798 | 530-ThrLeuLysGluLysProAsnAla-537 |
| SEQ. ID. NO. 28799 | 541-AsnAsnSerSerLysAspProIleProLysGlySerArg-553 |
| Hydrophilic Regions - Hopp-Woods | |
| SEQ. ID. NO. 28800 | 1-MetThrAspAsnSerProProPro-8 |
| SEQ. ID. NO. 28801 | 12-AlaGlnAlaArgValArgLysAsnAsn-20 |
| SEQ. ID. NO. 28802 | 43-LysGluIleArgAsnArgGly-49 |
| SEQ. ID. NO. 28803 | 57-AspSerAlaGluGlyIleGlu-63 |
| SEQ. ID. NO. 28804 | 75-AspValGlyArgValThrArgIleLysLeuArgAspAspGlnLysGlyValGlu-92 |
| SEQ. ID. NO. 28805 | 105-IleArgSerAspThr-109 |
| SEQ. ID. NO. 28806 | 116-ProArgIleAspGln-120 |
| SEQ. ID. NO. 28807 | 140-GlyLysSerGlyGluAlaLysAspValPheGln-150 |
| SEQ. ID. NO. 28808 | 171-GlyLysAsnAspArgIleLeu-177 |
| SEQ. ID. NO. 28809 | 196-AlaHisPheAspProSerAspGln-203 |
| SEQ. ID. NO. 28810 | 214-ProAsnAspLysLeuIle-219 |
| SEQ. ID. NO. 28811 | 258-AspSerProLysThrLysAsnSerLysAsnValLysSerGluAspSer-273 |
| SEQ. ID. NO. 28812 | 278-AspSerArgSerGluIle-283 |
| SEQ. ID. NO. 28813 | 285-AsnLeuProAspAspArgSer-291 |
| SEQ. ID. NO. 28814 | 311-ValGluTyrLysGly-315 |
| SEQ. ID. NO. 28815 | 328-AspArgAsnAspSer-332 |
| SEQ. ID. NO. 28816 | 345-IleArgIleGluProSerArgLeuGluIleAsnAlaAspGluGlnSerLysGluHisTrpLys-365 |
| SEQ. ID. NO. 28817 | 390-LysMetIleGluLeuAsnAspGlnProSerAlaSerProLysLeuArgPro-406 |
| SEQ. ID. NO. 28818 | 419-ArgGlyGlyGlyLeuAspAspLeuGlnValLysLeu-430 |
| SEQ. ID. NO. 28819 | 432-AspLeuLeuAspLysPheAsn-438 |
| SEQ. ID. NO. 28820 | 441-ProLeuAspLysThrValAla-447 |
| SEQ. ID. NO. 28821 | 454-AlaGluLeuLysSerAlaLeuLysSerAlaAsn-464 |
| SEQ. ID. NO. 28822 | 469-SerIleAspLysLeuValGly-475 |
| SEQ. ID. NO. 28823 | 482-IleProAsnGluLeu-486 |
| SEQ. ID. NO. 28824 | 488-GlnThrLeuLysGluLeuArgIle-495 |
| SEQ. ID. NO. 28825 | 516-SerLeuAspLysThrLeuLysAspValGln-525 |
| SEQ. ID. NO. 28826 | 530-ThrLeuLysGluLysProAsn-536 |
| SEQ. ID. NO. 28827 | 543-SerSerLysAspProIleProLysGlySerArg-553 |
| g155 | |
| AMPHI Regions - AMPHI | |
| SEQ. ID. NO. 28828 | 28-LysLeuGlyPheGlu-32 |
| SEQ. ID. NO. 28829 | 42-AlaAlaSerLeuAsp-46 |
| SEQ. ID. NO. 28830 | 105-LeuArgAlaLysLysVal-110 |
| SEQ. ID. NO. 28831 | 118-ValProArgIleSerArgAlaGlnAlaLeuAspAlaLeuSerSerMetAlaAsnIleSerGlyTyrArgAlaValIleGluAlaAlaAsnAlaPheGlyArg PhePheThrGly-155 |
| SEQ. ID. NO. 28832 | 175-ValAlaGlyLeuAlaAlaIleGlyThrAlaAsnSerLeuGlyAlaValValArgAlaPhe-194 |
| SEQ. ID. NO. 28833 | 201-AlaGluGlnIleGluSerMetGlyGly-209 |
| SEQ. ID. NO. 28834 | 225-AspGlyTyrAlaLysValMet-231 |
| SEQ. ID. NO. 28835 | 262-LysProAlaProLysLeuIleThrLysGluMetValGluSerMetLys-277 |
| SEQ. ID. NO. 28836 | 294-LeuThrArgProGlyGlu-299 |
| SEQ. ID. NO. 28837 | 307-ValLysIleIleGlyTyrThrAspMetAlaAsnArgLeuAlaGlyGln-322 |
| SEQ. ID. NO. 28838 | 329-ThrAsnLeuValAsnLeuThrLysLeuLeuSer-339 |
| SEQ. ID. NO. 28839 | 403-LysLeuAlaProAlaAlaIle-409 |
| SEQ. ID. NO. 28840 | 427-AsnHisPheIleVal-431 |

TABLE 1-continued

| | |
|---|---|
| SEQ. ID. NO. 28841 | 450-LeuHisThrProLeuMetSerValThrAsnAlaIleSerGlyIleMet-465 |
| SEQ. ID. NO. 28842 | 468-GlyAlaLeuLeuGln-472 |
| SEQ. ID. NO. 28843 | 477-AsnGlyPheValSerLeuLeuSerPheValAla-487 |
| SEQ. ID. NO. 28844 | 493-IleAsnIlePheGlyGly-498 |
| Antigenic Index - Jameson-Wolf | |
| SEQ. ID. NO. 28845 | 4-GlyIleProArgGluSerLeuSerGlyGluThrArgVal-16 |
| SEQ. ID. NO. 28846 | 44-SerLeuAspAspAlaAla-49 |
| SEQ. ID. NO. 28847 | 72-ValAsnAlaProSerGluGlyGluLeuProLeuLeuLysGluGlyGln-87 |
| SEQ. ID. NO. 28848 | 94-TrpProArgGlnAsnGluAlaLeu-101 |
| SEQ. ID. NO. 28849 | 105-LeuArgAlaLysLysValAsn-111 |
| SEQ. ID. NO. 28850 | 117-MetValProArgIleSerArg-123 |
| SEQ. ID. NO. 28851 | 159-AlaAlaGlyLysValProProAla-166 |
| SEQ. ID. NO. 28852 | 194-PheAspThrArgLeuGluValAlaGluGlnIleGluSerMetGlyGlyLys-210 |
| SEQ. ID. NO. 28853 | 216-PheLeuGlnGluSerGlyGlySerGlyAspGlyTyrAla-228 |
| SEQ. ID. NO. 28854 | 242-LeuPheAlaGluGlnAlaLysGluValAsp-251 |
| SEQ. ID. NO. 28855 | 259-IleProGlyLysProAlaProLysLeuIleThr-269 |
| SEQ. ID. NO. 28856 | 271-GluMetValGluSerMetLysSerGlySer-280 |
| SEQ. ID. NO. 28857 | 289-GlyGlyAsnCysGluLeuThrArgProGlyGluLeuSerVal-302 |
| SEQ. ID. NO. 28858 | 319-LeuAlaGlyGlnSerSer-324 |
| SEQ. ID. NO. 28859 | 337-LeuLeuSerProAsnLysAspGlyGluIle-346 |
| SEQ. ID. NO. 28860 | 348-LeuAspPheGluAspValIle-354 |
| SEQ. ID. NO. 28861 | 359-ThrValThrArgAspGlyGluIleThrPhePro-369 |
| SEQ. ID. NO. 28862 | 376-SerAlaArgProGlnGlnThrProSerGluLysAlaAlaProAlaAlaLysProGluProLysPro-397 |
| Hydrophilic Regions - Hopp-Woods | |
| SEQ. ID. NO. 28863 | 4-GlyIleProArgGluSerLeuSerGlyGluThrArgVal-16 |
| SEQ. ID. NO. 28864 | 44-SerLeuAspAspAlaAla-49 |
| SEQ. ID. NO. 28865 | 74-AlaProSerGluGlyGluLeuProLeuLeuLysGluGlyGln-87 |
| SEQ. ID. NO. 28866 | 96-ArgGlnAsnGluAlaLeu-101 |
| SEQ. ID. NO. 28867 | 105-LeuArgAlaLysLysValAsn-111 |
| SEQ. ID. NO. 28868 | 117-MetValProArgIleSerArg-123 |
| SEQ. ID. NO. 28869 | 194-PheAspThrArgLeuGluValAlaGluGlnIleGluSerMetGly-208 |
| SEQ. ID. NO. 28870 | 220-SerGlyGlySerGlyAspGlyTyrAla-228 |
| SEQ. ID. NO. 28871 | 242-LeuPheAlaGluGlnAlaLysGluValAsp-251 |
| SEQ. ID. NO. 28872 | 260-ProGlyLysProAlaPro-265 |
| SEQ. ID. NO. 28873 | 271-GluMetValGluSerMetLysSer-278 |
| SEQ. ID. NO. 28874 | 290-GlyAsnCysGluLeuThrArgProGlyGlu-299 |
| SEQ. ID. NO. 28875 | 339-SerProAsnLysAspGlyGluIle-346 |
| SEQ. ID. NO. 28876 | 348-LeuAspPheGluAspValIle-354 |
| SEQ. ID. NO. 28877 | 359-ThrValThrArgAspGlyGluIle-366 |
| SEQ. ID. NO. 28878 | 377-AlaArgProGlnGlnThrProSerGluLysAlaAlaProAlaAlaLysProGluProLysPro-397 |
| g156 | |
| AMPHI Regions - AMPHI | |
| SEQ. ID. NO. 28879 | 56-AsnGlyPheGluAlaPheAlaProPhe-64 |
| SEQ. ID. NO. 28880 | 80-AlaThrValAsnThr-84 |
| Antigenic Index - Jameson-Wolf | |
| SEQ. ID. NO. 28881 | 21-TyrAlaLysLysAlaGlyGlyPheArgPheLysAspAsnHisAsnProArgGly-38 |
| SEQ. ID. NO. 28882 | 44-GlnGlyAlaAlaAla-48 |
| SEQ. ID. NO. 28883 | 51-HisAlaAlaGlnGlnAsnGlyPheGlu-59 |
| SEQ. ID. NO. 28884 | 73-AlaThrGlyAsnAlaGlyGln-79 |
| SEQ. ID. NO. 28885 | 103-AspLysAlaAlaLeu-107 |
| Hydrophilic Regions - Hopp-Woods | |
| SEQ. ID. NO. 28886 | 21-TyrAlaLysLysAlaGlyGlyPheArgPheLysAspAsnHisAsnPro-36 |
| SEQ. ID. NO. 28887 | 103-AspLysAlaAlaLeu-107 |
| g157 | |
| AMPHI Regions - AMPHI | |
| SEQ. ID. NO. 28888 | 21-GlyArgAspValArgAlaAla-27 |
| SEQ. ID. NO. 28889 | 29-AlaIleLysIleAsnArgLeuLeuLysArgTyrIleLysArgGly-43 |
| SEQ. ID. NO. 28890 | 57-ArgLeuGlyGlyPheValArgAlaAlaGln-66 |
| SEQ. ID. NO. 28891 | 137-LeuGlyGlnAlaGlyGly-142 |
| SEQ. ID. NO. 28892 | 167-GlnLeuValAspArgLeuProArgGluAla-176 |
| Antigenic Index - Jameson-Wolf | |
| SEQ. ID. NO. 28893 | 1-MetArgAsnGluGluLysArgAlaLeuArgArgGluLeuArgGlyArgArgSerGlnMetGlyArgAspValArgAla-26 |
| SEQ. ID. NO. 28894 | 34-ArgLeuLeuLysArgTyrIleLysArgGlyArgLysIle-46 |
| SEQ. ID. NO. 28895 | 51-ProMetGlyLysGluLeuArg-57 |
| SEQ. ID. NO. 28896 | 64-AlaAlaGlnLysArgGlyAlaLysLeu-72 |
| SEQ. ID. NO. 28897 | 77-IleGluProHisThrArgArgMetTrp-85 |
| SEQ. ID. NO. 28898 | 87-ThrProTyrProGluArgGlyMetGluArgGluArgLysArgGlyArgAlaLysLeu-105 |
| SEQ. ID. NO. 28899 | 110-PheAlaGlyArgLysIleArgVal-117 |
| SEQ. ID. NO. 28900 | 129-GlyIleAspArgGluGlyTyrArgLeuGlyGln-139 |
| SEQ. ID. NO. 28901 | 151-MetLysTyrArgLeuGlnAla-157 |
| SEQ. ID. NO. 28902 | 168-LeuValAspArgLeuProArgGluAlaHisAspLeuProLeu-181 |
| Hydrophilic Regions - Hopp-Woods | |
| SEQ. ID. NO. 28903 | 1-MetArgAsnGluGluLysArgAlaLeuArgArgGluLeuArgGlyArgArgSerGlnMetGlyArgAspValArgAla-26 |
| SEQ. ID. NO. 28904 | 34-ArgLeuLeuLysArgTyrIleLysArgGlyArgLysIle-46 |
| SEQ. ID. NO. 28905 | 64-AlaAlaGlnLysArgGlyAla-70 |
| SEQ. ID. NO. 28906 | 89-TyrProGluArgGlyMetGluArgGluArgLysArgGlyArgAlaLysLeu-105 |
| SEQ. ID. NO. 28907 | 111-AlaGlyArgLysIleArgVal-117 |
| SEQ. ID. NO. 28908 | 129-GlyIleAspArgGluGlyTyrArg-136 |

TABLE 1-continued

| | |
|---|---|
| SEQ. ID. NO. 28909 | 151-MetLysTyrArgLeuGlnAla-157 |
| SEQ. ID. NO. 28910 | 168-LeuValAspArgLeuProArgGluAlaHisAspLeuPro-180 |
| g158 | |
| AMPHI Regions - AMPHI | |
| SEQ. ID. NO. 28911 | 20-PheSerArgAlaAlaGluGlnLeuGlu-28 |
| SEQ. ID. NO. 28912 | 33-AlaValSerArgIleValLysArgLeuGlu-42 |
| SEQ. ID. NO. 28913 | 46-GlyValAsnLeuLeuAsnArgThrThrArgGlnLeuAsn-58 |
| SEQ. ID. NO. 28914 | 63-GlyAlaGlnTyrPheArgArgAlaGlnArgIleLeuGlnGlu-76 |
| SEQ. ID. NO. 28915 | 85-LeuAlaValHisGluValProGln-92 |
| SEQ. ID. NO. 28916 | 160-PheAspSerHisPheArgValValAlaSerPro-170 |
| SEQ. ID. NO. 28917 | 178-ThrProGlnSerAlaGluAspLeu-185 |
| SEQ. ID. NO. 28918 | 188-HisGlnCysLeuGlyPheThrGluProGlySerLeuAsnThrTrpAlaVal-204 |
| SEQ. ID. NO. 28919 | 287-AspPheLeuValLysGluLeuGlyLysAsnMetAsnArgThrAsnThr-302 |
| Antigenic Index - Jameson-Wolf | |
| SEQ. ID. NO. 28920 | 1-MetLysThrAsnSerGluGluLeu-8 |
| SEQ. ID. NO. 28921 | 16-GluSerGlySerPheSerArgAlaAlaGluGlnLeuGluMetAlaAsn-31 |
| SEQ. ID. NO. 28922 | 36-ArgIleValLysArgLeuGluGluLysLeuGly-46 |
| SEQ. ID. NO. 28923 | 49-LeuLeuAsnArgThrThrArgGlnLeuAsnLeuThrGluGluGlyAlaGlnTyrPheArgArgAlaGlnArgIleLeuGln-75 |
| SEQ. ID. NO. 28924 | 78-AlaAlaAlaGluThrGluMet-84 |
| SEQ. ID. NO. 28925 | 95-LeuArgValAspSer-99 |
| SEQ. ID. NO. 28926 | 114-LysPheAsnGluArgTyrProHisIleArg-123 |
| SEQ. ID. NO. 28927 | 136-IleGluArgLysValAspIle-142 |
| SEQ. ID. NO. 28928 | 144-LeuArgAlaGlyGluLeuAspAspSerGlyLeuArgAla-156 |
| SEQ. ID. NO. 28929 | 168-AlaSerProGluTyrLeuAla-174 |
| SEQ. ID. NO. 28930 | 176-HisGlyThrProGlnSerAlaGluAspLeuAla-186 |
| SEQ. ID. NO. 28931 | 192-GlyPheThrGluProGlySerLeuAsn-200 |
| SEQ. ID. NO. 28932 | 207-AlaGlnGlyAsnProTyrLysIle-214 |
| SEQ. ID. NO. 28933 | 216-ProHisPheThrAlaSerSerGlyGluIleLeu-226 |
| SEQ. ID. NO. 28934 | 229-LeuCysLeuSerSerCysGly-235 |
| SEQ. ID. NO. 28935 | 243-LeuValAspAsnAspIleThrGluGlyLysLeu-253 |
| SEQ. ID. NO. 28936 | 258-AlaGluGlnThrSerAsnLysThrHisProPhe-268 |
| SEQ. ID. NO. 28937 | 273-TyrSerAspLysAlaValAsnLeu-280 |
| SEQ. ID. NO. 28938 | 292-GluLeuGlyLysAsnMetAsnArgThrAsnThrLys-303 |
| Hydrophilic Regions - Hopp-Woods | |
| SEQ. ID. NO. 28939 | 1-MetLysThrAsnSerGluGluLeu-8 |
| SEQ. ID. NO. 28940 | 19-SerPheSerArgAlaAlaGluGlnLeuGluMet-29 |
| SEQ. ID. NO. 28941 | 36-ArgIleValLysArgLeuGluGluLysLeuGly-46 |
| SEQ. ID. NO. 28942 | 58-AsnLeuThrGluGluGlyAlaGlnTyrPheArgArgAlaGlnArgIleLeuGln-75 |
| SEQ. ID. NO. 28943 | 78-AlaAlaAlaGluThrGluMet-84 |
| SEQ. ID. NO. 28944 | 95-LeuArgValAspSer-99 |
| SEQ. ID. NO. 28945 | 114-LysPheAsnGluArgTyrPro-120 |
| SEQ. ID. NO. 28946 | 136-IleGluArgLysValAspIle-142 |
| SEQ. ID. NO. 28947 | 144-LeuArgAlaGlyGluLeuAspAspSerGlyLeuArgAla-156 |
| SEQ. ID. NO. 28948 | 180-GlnSerAlaGluAspLeuAla-186 |
| SEQ. ID. NO. 28949 | 246-AsnAspIleThrGluGlyLysLeu-253 |
| SEQ. ID. NO. 28950 | 260-GlnThrSerAsnLysThrHis-266 |
| SEQ. ID. NO. 28951 | 276-LysAlaValAsnLeu-280 |
| SEQ. ID. NO. 28952 | 292-GluLeuGlyLysAsnMetAsnArgThrAsnThrLys-303 |
| g160 | |
| AMPHI Regions - AMPHI | |
| SEQ. ID. NO. 28953 | 6-LysLeuValAspLeuAlaGlnLeuThrGly-15 |
| SEQ. ID. NO. 28954 | 27-TrpHisGluThrLeu-31 |
| SEQ. ID. NO. 28955 | 69-GlyLeuGlyHisVal-73 |
| SEQ. ID. NO. 28956 | 97-LysGlnCysGlyAsn-101 |
| SEQ. ID. NO. 28957 | 118-AlaAspLeuMetAsnGlyLeuProGluThr-127 |
| SEQ. ID. NO. 28958 | 154-GlyThrValSerValValAsnAlaLeuProSer-164 |
| SEQ. ID. NO. 28959 | 183-LeuSerGlyValLeuLysGlyTrpGlnAspLysArg-194 |
| SEQ. ID. NO. 28960 | 197-HisLeuIleGlnLysValIleAspLysProGlu-207 |
| SEQ. ID. NO. 28961 | 216-ValAlaAlaAlaAsn-220 |
| SEQ. ID. NO. 28962 | 226-LeuMetArgArgPheLysSer-232 |
| SEQ. ID. NO. 28963 | 239-HisAlaPheValAsnHisIleArg-246 |
| SEQ. ID. NO. 28964 | 276-PheGlyLysAlaPheLys-281 |
| Antigenic Index - Jameson-Wolf | |
| SEQ. ID. NO. 28965 | 2-AspIleLeuAspLysLeuValAsp-9 |
| SEQ. ID. NO. 28966 | 13-LeuThrGlySerAlaAspVal-19 |
| SEQ. ID. NO. 28967 | 30-ThrLeuGlnArgGluGlyLeu-36 |
| SEQ. ID. NO. 28968 | 49-IleAspGlyGluThrSerProArgProValGlyThrGlyAsp-62 |
| SEQ. ID. NO. 28969 | 74-LeuSerHisAspGlyLysTyrGlyGluSerLeuGlnProAspIleArgGlnAsnGlyThrPhe-94 |
| SEQ. ID. NO. 28970 | 98-GlnCysGlyAsnGlyLeu-103 |
| SEQ. ID. NO. 28971 | 112-PheArgTyrAspThrHisAla-118 |
| SEQ. ID. NO. 28972 | 120-LeuMetAsnGlyLeu-124 |
| SEQ. ID. NO. 28973 | 146-LeuGluSerGluLysProLeu-152 |
| SEQ. ID. NO. 28974 | 175-LeuGluGlnAspLysAspValGluLeu-183 |
| SEQ. ID. NO. 28975 | 189-GlyTrpGlnAspLysArgLeuGly-196 |
| SEQ. ID. NO. 28976 | 202-ValIleAspLysProGluAspGluTrpAsnIleAspLysMetVal-216 |
| SEQ. ID. NO. 28977 | 225-GlnLeuMetArgArgPheLysSerGlnVal-234 |
| SEQ. ID. NO. 28978 | 252-LeuLeuLeuLysLysThrProAspSerValLeu-262 |
| SEQ. ID. NO. 28979 | 271-GlnSerGluThrHisPhe-276 |
| SEQ. ID. NO. 28980 | 278-LysAlaPheLysArg-282 |
| SEQ. ID. NO. 28981 | 287-SerProGlyGlnTyrArgLysGluGlyGlyGlnLys-298 |

TABLE 1-continued

Hydrophilic Regions - Hopp-Woods
SEQ. ID. NO. 28982 2-AspIleLeuAspLysLeuValAsp-9
SEQ. ID. NO. 28983 30-ThrLeuGlnArgGluGlyLeu-36
SEQ. ID. NO. 28984 50-AspGlyGluThrSerProArgProValGly-59
SEQ. ID. NO. 28985 76-HisAspGlyLysTyrGlyGlu-82
SEQ. ID. NO. 28986 84-LeuGlnProAspIleArgGln-90
SEQ. ID. NO. 28987 146-LeuGluSerGluLysProLeu-152
SEQ. ID. NO. 28988 175-LeuGluGlnAspLysAspValGluLeu-183
SEQ. ID. NO. 28989 190-TrpGlnAspLysArgLeuGly-196
SEQ. ID. NO. 28990 202-ValIleAspLysProGluAspGluTrpAsnIle-212
SEQ. ID. NO. 28991 225-GlnLeuMetArgArgPheLysSer-232
SEQ. ID. NO. 28992 255-LysLysThrProAspSerValLeu-262
SEQ. ID. NO. 28993 278-LysAlaPheLysArg-282
SEQ. ID. NO. 28994 290-GlnTyrArgLysGluGlyGlyGlnLys-298
g163
AMPHI Regions - AMPHI
SEQ. ID. NO. 28995 60-SerGlyLeuGlyAsnIle-65
SEQ. ID. NO. 28996 67-LeuGlyArgAspGluAsp-72
SEQ. ID. NO. 28997 76-PheGlyPheLeuSerTrpLeuAlaMetLeuPhe-86
SEQ. ID. NO. 28998 100-AlaGluProLeuMetHisTyrPheSerAspIle-110
SEQ. ID. NO. 28999 170-IleSerGlyArgPheGlyAspAlaIleAspIleMetAlaLeuLeuAlaThrPhePheGlyIleIleThrThr-193
SEQ. ID. NO. 29000 227-MetSerLeuAlaValValSerAlaIleSerGlyValGlyLysGlyValLysValLeuSer-246
SEQ. ID. NO. 29001 272-AlaPheGlyAspAsnIleGlyAsnTyrLeuGlyAsnLeuValArg-286
SEQ. ID. NO. 29002 313-TrpCysSerTrpAlaProPheValGlyLeuPheIleAla-325
SEQ. ID. NO. 29003 346-LeuPheGlyValLeuTrpPhe-352
SEQ. ID. NO. 29004 367-AlaGlyGlyMetLeuGluLysMetThrSerSer-377
SEQ. ID. NO. 29005 380-ThrLeuLeuPheLysPhePheAsnTyrLeuProLeuProGluLeuThrSerIleValSerLeuLeu-401
SEQ. ID. NO. 29006 438-TrpGlyValLeuMetSerAla-444
SEQ. ID. NO. 29007 454-GlyLeuGlyAsnLeuGlnSerMetThrLeu-463
SEQ. ID. NO. 29008 510-ArgLeuValArgIleMetSer-516
SEQ. ID. NO. 29009 520-GluGlnAspIleLeuLysPheLeuLysHisThrAla-531
SEQ. ID. NO. 29010 535-MetHisGluLeuGlnArgGluLeu-542
SEQ. ID. NO. 29011 574-AspPheMetTyrGlyIle-579
SEQ. ID. NO. 29012 583-GlyGlnAspValSerAspGlnLeu-590
SEQ. ID. NO. 29013 630-AlaAspIleLeuLysAsnTyr-636
Antigenic Index - Jameson-Wolf
SEQ. ID. NO. 29014 29-AspArgAlaLysGlu-33
SEQ. ID. NO. 29015 65-IleArgLeuGlyArgAspGluAspValPro-74
SEQ. ID. NO. 29016 114-AlaProGluHisArgGlnGln-120
SEQ. ID. NO. 29017 166-LeuLysGluLysIleSerGlyArgPheGlyAspAlaIleAsp-179
SEQ. ID. NO. 29018 200-GlnLeuGlyAlaGlyLeu-205
SEQ. ID. NO. 29019 237-GlyValGlyLysGlyValLysVal-244
SEQ. ID. NO. 29020 293-AlaTyrGluArgGluHisLysProTrpPhe-302
SEQ. ID. NO. 29021 326-ArgIleSerLysGlyArgThrIleArg-334
SEQ. ID. NO. 29022 370-MetLeuGluLysMetThrSerSerProGlu-379
SEQ. ID. NO. 29023 409-ThrSerAlaAspSerGlyIle-415
SEQ. ID. NO. 29024 421-IleThrSerArgAspLysGlyLeuSerAlaProArgTrp-433
SEQ. ID. NO. 29025 451-ArgSerGlyGlyLeuGlyAsn-457
SEQ. ID. NO. 29026 484-LeuSerAlaAspLysLysTyrPheGluThrArgValAsnProThrSer-499
SEQ. ID. NO. 29027 503-ThrGlyGlyLysTrpLysGluArgLeuVal-512
SEQ. ID. NO. 29028 516-SerGlnThrGlnGluGlnAspIle-523
SEQ. ID. NO. 29029 537-GluLeuGlnArgGluLeuSerGluGluTyrGlyLeu-548
SEQ. ID. NO. 29030 550-ValArgValAspLysMetPheHisGlnAspGluProAla-562
SEQ. ID. NO. 29031 566-ValIleArgLysGluThrMetArg-573
SEQ. ID. NO. 29032 581-SerValGlyGlnAspValSerAspGlnLeuIleAsnAspGlyLysLeuProHisIleArgHisGlnThrThrTyrLysProTyr-608
SEQ. ID. NO. 29033 612-PheAspGlyArgValGlyTyr-618
SEQ. ID. NO. 29034 622-TyrMetAsnLysAspGluLeuIle-629
SEQ. ID. NO. 29035 632-IleLeuLysAsnTyrGlu-637
SEQ. ID. NO. 29036 654-GluGlnValGluLeuAlaGlu-660
Hydrophilic Regions - Hopp-Woods
SEQ. ID. NO. 29037 29-AspArgAlaLysGlu-33
SEQ. ID. NO. 29038 66-ArgLeuGlyArgAspGluAspValPro-74
SEQ. ID. NO. 29039 114-AlaProGluHisArgGlnGln-120
SEQ. ID. NO. 29040 166-LeuLysGluLysIleSerGlyArgPheGlyAsp-176
SEQ. ID. NO. 29041 238-ValGlyLysGlyValLysVal-244
SEQ. ID. NO. 29042 293-AlaTyrGluArgGluHisLysPro-300
SEQ. ID. NO. 29043 327-IleSerLysGlyArgThrIleArg-334
SEQ. ID. NO. 29044 370-MetLeuGluLysMetThrSerSerPro-378
SEQ. ID. NO. 29045 422-ThrSerArgAspLysGlyLeuSer-429
SEQ. ID. NO. 29046 484-LeuSerAlaAspLysLysTyrPheGlu-492
SEQ. ID. NO. 29047 506-LysTrpLysGluArgLeuVal-512
SEQ. ID. NO. 29048 516-SerGlnThrGlnGluGlnAspIle-523
SEQ. ID. NO. 29049 537-GluLeuGlnArgGluLeuSerGluGluTyrGlyLeu-548
SEQ. ID. NO. 29050 550-ValArgValAspLysMetPheHisGlnAspGluProAla-562
SEQ. ID. NO. 29051 566-ValIleArgLysGluThrMetArg-573
SEQ. ID. NO. 29052 581-SerValGlyGlnAspValSerAsp-588

TABLE 1-continued

SEQ. ID. NO. 29053 590-LeuIleAsnAspGlyLysLeuProHis-598
SEQ. ID. NO. 29054 622-TyrMetAsnLysAspGluLeuIle-629
SEQ. ID. NO. 29055 654-GluGlnValGluLeuAlaGlu-660
g164
AMPHI Regions - AMPHI
SEQ. ID. NO. 29056 12-TyrIleLeuAsnAspCys-17
SEQ. ID. NO. 29057 28-LeuSerLysGluLeuAlaGlyLeuLysAla-37
SEQ. ID. NO. 29058 62-PhePheGluAsnValArgArgPheProGlu-71
SEQ. ID. NO. 29059 75-LeuGlyArgGlnProArgIleAsnAspLeuAlaHis-86
SEQ. ID. NO. 29060 104-TyrAlaAsnLeuPheAlaAsnLeuAsnGlyIleGluArgIlePheLys-119
SEQ. ID. NO. 29061 179-ValProAlaIleTyrThr-184
SEQ. ID. NO. 29062 197-TrpPheAsnArgIle-201
SEQ. ID. NO. 29063 226-AlaLysLeuLeuGluGlyTyrGlyLeuSer-235
SEQ. ID. NO. 29064 277-GluValGlyGluLeuIle-282
SEQ. ID. NO. 29065 289-MetArgGlyTyrLeuAsn-294
SEQ. ID. NO. 29066 302-ThrIleValAsnGlyTrpLeuLys-309
SEQ. ID. NO. 29067 339-ValTyrProArgGluIleGluGluGlu-347
SEQ. ID. NO. 29068 349-HisLysLeuAspAlaValGluAlaAlaAla-358
SEQ. ID. NO. 29069 374-PheValGlnLeuLysGluGlyMet-381
SEQ. ID. NO. 29070 387-GluIleArgArgHisLeuArgThrVal-395
SEQ. ID. NO. 29071 399-PheLysIleProLysGln-404
SEQ. ID. NO. 29072 414-AsnAlaThrGlyLysValLeuLysArgValLeuLysGluGlnPheGluGlyAsn-431
Antigenic Index - Jameson-Wolf
SEQ. ID. NO. 29073 5-LeuLysAsnSerGlu-9
SEQ. ID. NO. 29074 15-AsnAspCysLysAla-19
SEQ. ID. NO. 29075 27-GlyLeuSerLysGluLeuAlaGly-34
SEQ. ID. NO. 29076 37-AlaGlnThrProValGlu-42
SEQ. ID. NO. 29077 45-IleTrpThrAspLysSerArgProAlaGlyGluThrAlaGluGly-59
SEQ. ID. NO. 29078 65-AsnValArgArgPheProGluLysProAspLeuGlyArgGlnProArgIleAsnAsp-83
SEQ. ID. NO. 29079 90-ThrSerGlyThrThrGlyHisProLysGlyAla-100
SEQ. ID. NO. 29080 112-AsnGlyIleGluArgIlePheLysIleSerLysArgAspArgPhe-126
SEQ. ID. NO. 29081 205-IleSerGlyGlyAlaProLeuAla-212
SEQ. ID. NO. 29082 219-PheLysAlaLysPheProArg-225
SEQ. ID. NO. 29083 230-GluGlyTyrGlyLeuSerGluAlaSer-238
SEQ. ID. NO. 29084 245-ThrProGluArgGlnLysAlaArgSerVal-254
SEQ. ID. NO. 29085 258-LeuProGlyLeuGluAlaLysAlaValAspGluGluLeuValGluValProArgGlyGluValGly-279
SEQ. ID. NO. 29086 282-IleValArgGlyGlySerValMet-289
SEQ. ID. NO. 29087 297-AlaAlaThrAspGluThrIle-303
SEQ. ID. NO. 29088 306-GlyTrpLeuLysThrGlyAsp-312
SEQ. ID. NO. 29089 315-ThrIleAspGluAspGly-320
SEQ. ID. NO. 29090 325-ValAspArgLysLysAspLeuIleIleSerLysGlyGlnAsnValTyrProArgGluIleGluGluGluIleHisLys-350
SEQ. ID. NO. 29091 361-GlyValLysAspArgTyrAlaAspGluGluIle-371
SEQ. ID. NO. 29092 377-LeuLysGluGlyMetAspLeuGlyGluAspGluIleArgArgHisLeu-392
SEQ. ID. NO. 29093 405-IleHisPheLysAspGlyLeuProArgAsnAlaThrGlyLysValLeuLysArgValLeuLysGluGlnPheGluGlyAsnLys-432
Hydrophilic Regions - Hopp-Woods
SEQ. ID. NO. 29094 27-GlyLeuSerLysGluLeuAlaGly-34
SEQ. ID. NO. 29095 48-AspLysSerArgProAlaGlyGluThrAlaGluGly-59
SEQ. ID. NO. 29096 65-AsnValArgArgPheProGluLysProAspLeuGlyArgGlnProArgIleAsnAsp-83
SEQ. ID. NO. 29097 113-GlyIleGluArgIlePheLysIleSerLysArgAspArgPhe-126
SEQ. ID. NO. 29098 219-PheLysAlaLysPheProArg-225
SEQ. ID. NO. 29099 245-ThrProGluArgGlnLysAlaArgSer-253
SEQ. ID. NO. 29100 261-LeuGluAlaLysAlaValAspGluGluLeuValGluValProArgGlyGluValGly-279
SEQ. ID. NO. 29101 297-AlaAlaThrAspGluThrIle-303
SEQ. ID. NO. 29102 315-ThrIleAspGluAspGly-320
SEQ. ID. NO. 29103 325-ValAspArgLysLysAspLeuIleIle-333
SEQ. ID. NO. 29104 340-TyrProArgGluIleGluGluGluIleHisLys-350
SEQ. ID. NO. 29105 361-GlyValLysAspArgTyrAlaAspGluGluIle-371
SEQ. ID. NO. 29106 377-LeuLysGluGlyMetAspLeuGlyGluAspGluIleArgArgHisLeu-392
SEQ. ID. NO. 29107 409-AspGlyLeuProArgAsnAlaThr-416
SEQ. ID. NO. 29108 418-LysValLeuLysArgValLeuLysGluGlnPheGluGlyAsnLys-432
g165-1
AMPHI Regions - AMPHI
SEQ. ID. NO. 29109 17-AlaThrLeuGlyValLeuLeuLysGluLeu-26
SEQ. ID. NO. 29110 33-ThrLeuIleGluArgLeuGluAsp-40
SEQ. ID. NO. 29111 73-IleAsnProAlaArgAlaLeuAsnIleAla-82
SEQ. ID. NO. 29112 90-GlnPheTrpAlaThr-94
SEQ. ID. NO. 29113 108-AsnAlaValProHis-112
SEQ. ID. NO. 29114 121-HisCysArgTyrLeuGlnLysArg-128
SEQ. ID. NO. 29115 130-AspValPheLysThrGlnLysLeuPheGluAsnMet-141
SEQ. ID. NO. 29116 182-ArgLeuThrArgGlnMetValLysTyrLeuGlnGly-193
SEQ. ID. NO. 29117 198-ThrGluPheAsnArgHisValGluAspIleLysArgGlu-210
SEQ. ID. NO. 29118 364-LysThrLysGluGlu-368
SEQ. ID. NO. 29119 371-AlaSerLeuLeuGluTyrTyrProArgGln-380
Antigenic Index - Jameson-Wolf
SEQ. ID. NO. 29120 1-MetAlaGluAlaThrAsp-6
SEQ. ID. NO. 29121 24-LysGluLeuGluProSerTrp-30
SEQ. ID. NO. 29122 36-GluArgLeuGluAspValAlaLeuGluSerSerAsnAlaTrpAsnAsnAlaGlyThrGly-55
SEQ. ID. NO. 29123 97-AlaGluGlyLysLeuGluAspAsnSer-105
SEQ. ID. NO. 29124 117-MetAsnGluAspHisCysArgTyrLeuGlnLysArgTyrAspValPheLysThrGlnLysLeuPheGlu-139
SEQ. ID. NO. 29125 141-MetGluPheSerThrAspArgAsnLysIleSerAsp-152

TABLE 1-continued

| | |
|---|---|
| SEQ. ID. NO. 29126 | 157-IleMetArgGlyArgAspGluAsnGlnPro-166 |
| SEQ. ID. NO. 29127 | 169-AlaAsnTyrSerAlaGluGlyThrAspValAspPheGlyArgLeuThrArgGlnMet-187 |
| SEQ. ID. NO. 29128 | 191-LeuGlnGlyLysGlyValLysThrGluPheAsnArgHisValGluAspIleLysArgGluSerAspGly-213 |
| SEQ. ID. NO. 29129 | 219-ThrAlaAspThrArgAsnProAspTrp-227 |
| SEQ. ID. NO. 29130 | 249-GlnLysSerGlyIleProGluGlyLysGlyTyrGlyGly-261 |
| SEQ. ID. NO. 29131 | 269-PheArgAsnSerAsnProGluThrAlaGluGlnHisAsn-281 |
| SEQ. ID. NO. 29132 | 300-LeuAspThrArgAsnValAspGlyLysArgHisLeu-311 |
| SEQ. ID. NO. 29133 | 322-AsnPheLeuLysGlnGlySerPheMet-330 |
| SEQ. ID. NO. 29134 | 361-GluLeuArgLysThrLysGluGluArgPhe-370 |
| SEQ. ID. NO. 29135 | 375-GluTyrTyrProArgGlnThrArgArg-383 |
| SEQ. ID. NO. 29136 | 395-IleXxxTyrAspSerLysLeuArgVal-403 |
| SEQ. ID. NO. 29137 | 410-ValProArgAspAlaArgSerArgIleLeuGluArgArgGlyAlaSerArg-426 |
| SEQ. ID. NO. 29138 | 430-IleSerAlaAspAspThrAlaProSer-438 |
| Hydrophilic Regions - Hopp-Woods | |
| SEQ. ID. NO. 29139 | 1-MetAlaGluAlaThrAsp-6 |
| SEQ. ID. NO. 29140 | 24-LysGluLeuGluPro-28 |
| SEQ. ID. NO. 29141 | 36-GluArgLeuGluAspValAlaLeuGluSer-45 |
| SEQ. ID. NO. 29142 | 97-AlaGluGlyLysLeuGluAspAsnSer-105 |
| SEQ. ID. NO. 29143 | 117-MetAsnGluAspHisCysArgTyrLeuGlnLysArgTyrAspVal-131 |
| SEQ. ID. NO. 29144 | 141-MetGluPheSerThrAspArgAsnLysIleSerAsp-152 |
| SEQ. ID. NO. 29145 | 158-MetArgGlyArgAspGluAsnGlnPro-166 |
| SEQ. ID. NO. 29146 | 172-SerAlaGluGlyThrAspValAspPhe-180 |
| SEQ. ID. NO. 29147 | 182-ArgLeuThrArgGlnMet-187 |
| SEQ. ID. NO. 29148 | 194-LysGlyValLysThrGluPheAsnArgHisValGluAspIleLysArgGluSerAspGly-213 |
| SEQ. ID. NO. 29149 | 219-ThrAlaAspThrArgAsnProAsp-226 |
| SEQ. ID. NO. 29150 | 252-GlyIleProGluGlyLysGly-258 |
| SEQ. ID. NO. 29151 | 272-SerAsnProGluThrAlaGluGlnHisAsn-281 |
| SEQ. ID. NO. 29152 | 300-LeuAspThrArgAsnValAspGlyLysArg-309 |
| SEQ. ID. NO. 29153 | 361-GluLeuArgLysThrLysGluGluArgPhe-370 |
| SEQ. ID. NO. 29154 | 378-ProArgGlnThrArgArg-383 |
| SEQ. ID. NO. 29155 | 397-TyrAspSerLysLeuArg-402 |
| SEQ. ID. NO. 29156 | 410-ValProArgAspAlaArgSerArgIleLeuGluArgArgGlyAlaSerArg-426 |
| SEQ. ID. NO. 29157 | 431-SerAlaAspAspThrAlaPro-437 |
| g204 | |
| AMPHI Regions - AMPHI | |
| SEQ. ID. NO. 29158 | 16-HisIleAlaSerValLeuHisGlyGly-24 |
| SEQ. ID. NO. 29159 | 45-GlnPheAlaAlaValPheGlyAspIleAlaHisGlnPheGly-58 |
| SEQ. ID. NO. 29160 | 89-ValValGlyMetLeuSerGlyGln-96 |
| SEQ. ID. NO. 29161 | 104-GlnAlaPheAsnArgIleThrAspLeuPhePhe-114 |
| SEQ. ID. NO. 29162 | 132-ArgArgIleValAspValPheAsp-139 |
| SEQ. ID. NO. 29163 | 144-PheArgArgAlaLeuCysArgIleLeuArgLeuPheArgArgIlePheGly-160 |
| SEQ. ID. NO. 29164 | 229-ArgAlaPheCysAla-233 |
| Antigenic Index - Jameson-Wolf | |
| SEQ. ID. NO. 29165 | 4-AlaGluIleLysArgProLeu-10 |
| SEQ. ID. NO. 29166 | 34-LeuGlnGlyGlyMetArgAsnGlnVal-42 |
| SEQ. ID. NO. 29167 | 55-HisGlnPheGlyLys-59 |
| SEQ. ID. NO. 29168 | 68-ArgProAlaArgArgArgValLeu-75 |
| SEQ. ID. NO. 29169 | 82-PheAlaAspAspGlyPheGln-88 |
| SEQ. ID. NO. 29170 | 93-LeuSerGlyGlnProAspGlyValLeu-101 |
| SEQ. ID. NO. 29171 | 125-SerGlnSerGlnThrGlyAsnArgArgIleValAsp-136 |
| SEQ. ID. NO. 29172 | 138-PheAspPheGluAsnArgPheArgArgAlaLeu-148 |
| SEQ. ID. NO. 29173 | 162-AlaAlaGlyGlyLysGlnGlnAla-169 |
| SEQ. ID. NO. 29174 | 172-GlnHisGlyLysArgTyrPhe-178 |
| SEQ. ID. NO. 29175 | 187-SerLysCysArgLeuLysCysArgLeuLysArgGlyArgArgArgPheGlyArgHisTrp-206 |
| SEQ. ID. NO. 29176 | 209-PheAsnGlyArgMetProThrAlaSerArgThrLeuSerAsnAsnSerArgAlaSerLeu-228 |
| Hydrophilic Regions - Hopp-Woods | |
| SEQ. ID. NO. 29177 | 4-AlaGluIleLysArgProLeu-10 |
| SEQ. ID. NO. 29178 | 68-ArgProAlaArgArgArgValLeu-75 |
| SEQ. ID. NO. 29179 | 83-AlaAspAspGlyPhe-87 |
| SEQ. ID. NO. 29180 | 128-GlnThrGlyAsnArgArgIleValAsp-136 |
| SEQ. ID. NO. 29181 | 138-PheAspPheGluAsnArgPheArgArgAlaLeu-148 |
| SEQ. ID. NO. 29182 | 165-GlyLysGlnGlnAla-169 |
| SEQ. ID. NO. 29183 | 172-GlnHisGlyLysArgTyrPhe-178 |
| SEQ. ID. NO. 29184 | 187-SerLysCysArgLeuLysCysArgLeuLysArgGlyArgArgArgPheGly-203 |
| SEQ. ID. NO. 29185 | 213-MetProThrAlaSerArgThrLeuSerAsnAsnSerArgAlaSerLeu-228 |
| g205-1 | |
| AMPHI Regions - AMPHI | |
| SEQ. ID. NO. 29186 | 6-PheAlaValLeuGlyGly-11 |
| SEQ. ID. NO. 29187 | 21-SerGluAsnThrAlaGluGlnProGlnAsnAlaAlaGlnSer-34 |
| SEQ. ID. NO. 29188 | 87-GlyLysHisProAsnAspLeuGluAlaValValGlyLys-99 |
| SEQ. ID. NO. 29189 | 119-HisThrLeuPheAlaLysLeuValGlyAsnIleAlaGluAspGlyGlyLys-135 |
| SEQ. ID. NO. 29190 | 147-GlnProTyrGlnAla-151 |
| Antigenic Index - Jameson-Wolf | |
| SEQ. ID. NO. 29191 | 18-CysGlyLysSerGluAsnThrAlaGluGlnProGlnAsnAlaAlaGlnSerAlaProLysProValPhe-40 |
| SEQ. ID. NO. 29192 | 56-GlyGlnSerSerGluGlyLysThrAsnAspGlyLysLysGlnIle-70 |
| SEQ. ID. NO. 29193 | 73-ProIleLysGlyLeuProGluGlnAsnAla-82 |
| SEQ. ID. NO. 29194 | 85-LeuThrGlyLysHisProAsnAspLeuGluAlaValVal-97 |
| SEQ. ID. NO. 29195 | 99-LysCysMetGluThrAspGlyLysAspAlaProSerGlyTrpAlaGluAsnGly-116 |
| SEQ. ID. NO. 29196 | 129-IleAlaGluAspGlyGlyLysLeuThr-137 |

TABLE 1-continued

| | |
|---|---|
| SEQ. ID. NO. 29197 | 149-TyrGlnAlaGlyLysSerGlyTyr-156 |
| SEQ. ID. NO. 29198 | 168-IleAspSerGluGlyAlaPhe-174 |
| Hydrophilic Regions - Hopp-Woods | |
| SEQ. ID. NO. 29199 | 19-GlyLysSerGluAsnThrAlaGluGlnProGln-29 |
| SEQ. ID. NO. 29200 | 57-GlnSerSerGluGlyLysThrAsnAspGlyLysLysGlnIle-70 |
| SEQ. ID. NO. 29201 | 85-LeuThrGlyLysHisProAsnAspLeuGluAlaValVal-97 |
| SEQ. ID. NO. 29202 | 99-LysCysMetGluThrAspGlyLysAspAlaPro-109 |
| SEQ. ID. NO. 29203 | 129-IleAlaGluAspGlyGlyLysLeu-136 |
| SEQ. ID. NO. 29204 | 150-GlnAlaGlyLysSerGly-155 |
| SEQ. ID. NO. 29205 | 168-IleAspSerGluGlyAlaPhe-174 |
| g206 | |
| AMPHI Regions - AMPHI | |
| SEQ. ID. NO. 29206 | 32-ProLysGlnThrValArgGlnIleGlnAlaVal-42 |
| SEQ. ID. NO. 29207 | 44-IleSerHisIleGlyArgThrGln-51 |
| SEQ. ID. NO. 29208 | 81-CysSerGlyMetIleGln-86 |
| SEQ. ID. NO. 29209 | 99-ArgThrAlaArgAspMet-104 |
| SEQ. ID. NO. 29210 | 150-SerGlyLysThrIleLysThrGlu-157 |
| Antigenic Index - Jameson-Wolf | |
| SEQ. ID. NO. 29211 | 2-PheSerProAspLysThrLeu-8 |
| SEQ. ID. NO. 29212 | 21-GlyThrThrSerGlyLysHisArgGlnProLysProLysGlnThrValArg-37 |
| SEQ. ID. NO. 29213 | 48-GlyArgThrGlnGlySerGlnGluLeu-56 |
| SEQ. ID. NO. 29214 | 66-ThrProTyrLysTrpGlyGlySerSerThr-75 |
| SEQ. ID. NO. 29215 | 96-LysLeuProArgThrAlaArgAspMetAlaAlaAlaSerArgLysIleProAspSerArgLeuLysAlaGly-119 |
| SEQ. ID. NO. 29216 | 126-ThrGlyGlyAlaHisArgTyrSer-133 |
| SEQ. ID. NO. 29217 | 146-HisAlaProGlySerGlyLysThrIleLysThrGluLysLeuSer-160 |
| Hydrophilic Regions - Hopp-Woods | |
| SEQ. ID. NO. 29218 | 23-ThrSerGlyLysHisArgGlnProLysProLysGlnThrVal-36 |
| SEQ. ID. NO. 29219 | 48-GlyArgThrGlnGlySerGln-54 |
| SEQ. ID. NO. 29220 | 96-LysLeuProArgThrAlaArgAspMetAlaAlaAlaSerArgLysIleProAspSerArgLeuLysAlaGly-119 |
| SEQ. ID. NO. 29221 | 149-GlySerGlyLysThrIleLysThrGluLysLeuSer-160 |
| g211 | |
| AMPHI Regions - AMPHI | |
| SEQ. ID. NO. 29222 | 18-ValGlyAsnGlyValAspLysPheGlyArgGlyAla-29 |
| SEQ. ID. NO. 29223 | 57-GlnPheGluArgAla-61 |
| SEQ. ID. NO. 29224 | 99-LysGlyPheAspGluIleAsnProAla-107 |
| SEQ. ID. NO. 29225 | 109-AlaLeuAlaGlnValIleGluLeu-116 |
| SEQ. ID. NO. 29226 | 153-AspGlyLysArgHisGlyLysLeuHis-161 |
| Antigenic Index - Jameson-Wolf | |
| SEQ. ID. NO. 29227 | 8-AsnGlnLeuGlyGlyArgAsnGlyAlaAlaVal-18 |
| SEQ. ID. NO. 29228 | 20-AsnGlyValAspLysPheGlyArgGlyAlaAspAsnGlnValGluPheLeuGlu-37 |
| SEQ. ID. NO. 29229 | 44-GlyAlaSerGlyArgAlaAla-50 |
| SEQ. ID. NO. 29230 | 73-GlyGluAspAspValVal-78 |
| SEQ. ID. NO. 29231 | 99-LysGlyPheAspGluIleAsnPro-106 |
| SEQ. ID. NO. 29232 | 140-CysProArgTyrHisProLysLeuHisAspGlyAsnGlnAspGlyLysArgHisGlyLysLeuHisAspGlyAlaTyr-165 |
| SEQ. ID. NO. 29233 | 169-GlnArgGlnSerAlaGly-174 |
| Hydrophilic Regions - Hopp-Woods | |
| SEQ. ID. NO. 29234 | 10-LeuGlyGlyArgAsnGlyAla-16 |
| SEQ. ID. NO. 29235 | 21-GlyValAspLysPheGlyArgGlyAlaAspAsnGlnValGluPheLeuGlu-37 |
| SEQ. ID. NO. 29236 | 73-GlyGluAspAspValVal-78 |
| SEQ. ID. NO. 29237 | 100-GlyPheAspGluIleAsn-105 |
| SEQ. ID. NO. 29238 | 143-TyrHisProLysLeuHisAspGlyAsnGlnAspGlyLysArgHisGlyLysLeuHisAsp-162 |
| g212 | |
| AMPHI Regions - AMPHI | |
| SEQ. ID. NO. 29239 | 6-TrpAspGlyIleProAspIleArgThr-14 |
| SEQ. ID. NO. 29240 | 16-AspGlnThrIleArgLysHisAlaHis-24 |
| SEQ. ID. NO. 29241 | 40-PheGlnThrAlaGln-44 |
| SEQ. ID. NO. 29242 | 63-CysLeuGlnPheAspSerIleAsnLeuIleGluHisIle-75 |
| SEQ. ID. NO. 29243 | 89-ThrArgArgLeuHisGluHis-95 |
| SEQ. ID. NO. 29244 | 142-AlaSerThrAlaHis-146 |
| SEQ. ID. NO. 29245 | 199-ArgLeuLeuGlyHis-203 |
| SEQ. ID. NO. 29246 | 238-HisAsnHisLeuTyrArgSerIleThrSerAlaGluAlaGluLysIle-253 |
| SEQ. ID. NO. 29247 | 262-TyrAlaGluProLeuCysGlyLeu-269 |
| SEQ. ID. NO. 29248 | 288-SerHisProLeuIleGluLeu-294 |
| SEQ. ID. NO. 29249 | 296-GluAsnThrThrLeu-300 |
| SEQ. ID. NO. 29250 | 397-TrpAsnGluAlaGluGluAla-403 |
| Antigenic Index - Jameson-Wolf | |
| SEQ. ID. NO. 29251 | 8-GlyIleProAspIleArgThrLeuAspGlnThrIleArgLysHisAlaHisProLeu-26 |
| SEQ. ID. NO. 29252 | 33-ProAspAsnGlnIleProAspPheGlnThrAlaGlnAspAlaSerAspSerGluCysArgLeuLysHisArgLeuAspGln-59 |
| SEQ. ID. NO. 29253 | 85-ProProSerArgThrArgArgLeuHisGlu-94 |
| SEQ. ID. NO. 29254 | 105-AlaIleProGlnThrGluSerLysSerAspLysProTrp-117 |
| SEQ. ID. NO. 29255 | 122-GlnThrSerGluArgLysLysProGluHis-131 |
| SEQ. ID. NO. 29256 | 158-LeuGluAlaArgLysAlaAlaGln-165 |
| SEQ. ID. NO. 29257 | 168-SerGlyAsnArgGlnGly-173 |
| SEQ. ID. NO. 29258 | 180-SerProHisAspThrGlyGlnThrGlu-188 |
| SEQ. ID. NO. 29259 | 193-GlyTyrGlyTyrThrLysArgLeuLeu-201 |
| SEQ. ID. NO. 29260 | 205-LeuProAspSerAspThrTrpGlyGlyAsn-214 |
| SEQ. ID. NO. 29261 | 220-AsnTyrSerArgThrGluGlnGlnArgAsnHisGluLeuGlyLeu-234 |
| SEQ. ID. NO. 29262 | 246-ThrSerAlaGluAlaGluLysIleAla-254 |
| SEQ. ID. NO. 29263 | 258-LeuAsnThrProTyrAlaGluProLeu-266 |
| SEQ. ID. NO. 29264 | 303-IleSerHisAspGlyGluLysTrpIle-311 |

TABLE 1-continued

| | |
|---|---|
| SEQ. ID. NO. 29265 | 328-ThrGlyAlaHisSerProCysLeuPro-336 |
| SEQ. ID. NO. 29266 | 346-ArgGlnIleArgGlyGlnThrGlyLeuThrProSerThrProPheSerGluGlnLeuArg-365 |
| SEQ. ID. NO. 29267 | 376-ProSerTrpHisGly-380 |
| SEQ. ID. NO. 29268 | 391-AsnSerSerAsnThrGlyTrpAsnGluAlaGluGluAlaSerAsnArgGlnAla-408 |
| Hydrophilic Regions - Hopp-Woods | |
| SEQ. ID. NO. 29269 | 10-ProAspIleArgThrLeuAspGlnThrIleArgLysHisAla-23 |
| SEQ. ID. NO. 29270 | 44-GlnAspAlaSerAspSerGluCysArgLeuLysHisArgLeuAspGln-59 |
| SEQ. ID. NO. 29271 | 87-SerArgThrArgArgLeuHisGlu-94 |
| SEQ. ID. NO. 29272 | 105-AlaIleProGlnThrGluSerLysSerAspLys-115 |
| SEQ. ID. NO. 29273 | 122-GlnThrSerGluArgLysLysProGluHis-131 |
| SEQ. ID. NO. 29274 | 158-LeuGluAlaArgLysAlaAlaGln-165 |
| SEQ. ID. NO. 29275 | 180-SerProHisAspThrGlyGln-186 |
| SEQ. ID. NO. 29276 | 206-ProAspSerAspThr-210 |
| SEQ. ID. NO. 29277 | 222-SerArgThrGluGlnGlnArgAsnHisGlu-231 |
| SEQ. ID. NO. 29278 | 246-ThrSerAlaGluAlaGluLysIleAla-254 |
| SEQ. ID. NO. 29279 | 304-SerHisAspGlyGluLysTrpIle-311 |
| SEQ. ID. NO. 29280 | 346-ArgGlnIleArgGly-350 |
| SEQ. ID. NO. 29281 | 398-AsnGluAlaGluGluAlaSerAsnArgGlnAla-408 |
| g214-1 | |
| Hydrophilic Regions - Hopp-Woods | |
| SEQ. ID. NO. 29282 | 10-ProAspIleArgThrLeuAspGlnThrIleArgLysHisAla-23 |
| SEQ. ID. NO. 29283 | 44-GlnAspAlaSerAspSerGluCysArgLeuLysHisArgLeuAspGln-59 |
| SEQ. ID. NO. 29284 | 87-SerArgThrArgArgLeuHisGlu-94 |
| SEQ. ID. NO. 29285 | 105-AlaIleProGlnThrGluSerLysSerAspLys-115 |
| SEQ. ID. NO. 29286 | 122-GlnThrSerGluArgLysLysProGluHis-131 |
| SEQ. ID. NO. 29287 | 158-LeuGluAlaArgLysAlaAlaGln-165 |
| SEQ. ID. NO. 29288 | 180-SerProHisAspThrGlyGln-186 |
| SEQ. ID. NO. 29289 | 206-ProAspSerAspThr-210 |
| SEQ. ID. NO. 29290 | 222-SerArgThrGluGlnGlnArgAsnHisGlu-231 |
| SEQ. ID. NO. 29291 | 246-ThrSerAlaGluAlaGluLysIleAla-254 |
| SEQ. ID. NO. 29292 | 304-SerHisAspGlyGluLysTrpIle-311 |
| SEQ. ID. NO. 29293 | 346-ArgGlnIleArgGly-350 |
| SEQ. ID. NO. 29294 | 398-AsnGluAlaGluGluAlaSerAsnArgGlnAla-408 |
| Antigenic Index - Jameson-Wolf | |
| SEQ. ID. NO. 29295 | 23-LeuGlnSerAspSerArgArgProIleGlnIleGluAlaAspGlnGlySerLeuAspGlnAlaAsnGlnSerThrThrPheSerGlyAsn-52 |
| SEQ. ID. NO. 29296 | 71-ArgGlyGlyLysGlyGlyGluSerValArgAlaGluGlySerProValArgPheSerGlnThrLeuAspGlyGlyLysGlyThrValArgGlyGlnAla AsnAsnVal-106 |
| SEQ. ID. NO. 29297 | 119-GlyAsnAlaLysValGlnArgGlyGlyAspValAlaGlu-131 |
| SEQ. ID. NO. 29298 | 138-AsnThrLysThrGluVal-143 |
| SEQ. ID. NO. 29299 | 148-GlySerThrLysSerGlyAlaLysSerAlaSerLysThrGlyArgVal-163 |
| SEQ. ID. NO. 29300 | 169-ProSerSerThrGlnLysThrGlu-176 |
| Hydrophilic Regions - Hopp-Woods | |
| SEQ. ID. NO. 29301 | 25-SerAspSerArgArgProIleGlnIleGluAlaAspGlnGlySerLeuAspGlnAlaAsn-44 |
| SEQ. ID. NO. 29302 | 71-ArgGlyGlyLysGlyGlyGluSerValArgAlaGluGlySerPro-85 |
| SEQ. ID. NO. 29303 | 92-LeuAspGlyGlyLysGlyThrValArgGlyGlnAla-103 |
| SEQ. ID. NO. 29304 | 121-AlaLysValGlnArgGlyGlyAspValAlaGlu-131 |
| SEQ. ID. NO. 29305 | 148-GlySerThrLysSerGlyAlaLysSerAlaSerLysThrGlyArg-162 |
| SEQ. ID. NO. 29306 | 171-SerThrGlnLysThrGlu-176 |
| g215 | |
| AMPHI Regions - AMPHI | |
| SEQ. ID. NO. 29307 | 21-SerLeuSerAlaTrpLeuGlyArgIle-29 |
| SEQ. ID. NO. 29308 | 67-SerAlaLysGlyAlaLysGlnPhe-74 |
| Antigenic Index - Jameson-Wolf | |
| SEQ. ID. NO. 29309 | 3-ValArgTrpArgTyrGly-8 |
| SEQ. ID. NO. 29310 | 28-ArgIleSerGluValGluIleGluGluValArgLeuAsnProAspGluProGlnTyrThrMetAspGlyLeuAspGlyArgArgPheAspGluGlnGly TyrLeuLys-63 |
| SEQ. ID. NO. 29311 | 65-HisLeuSerAlaLysGlyAlaLysGlnPheProGluAsnSerAspIleHisPheAspSerProHisLeu-87 |
| SEQ. ID. NO. 29312 | 99-ValGlySerAspGluAlaValTyrHisThrGluAsnLysGlnValLeuPhe-115 |
| SEQ. ID. NO. 29313 | 123-LysThrAlaAspGlyArgArgGlnAlaGlyLysValGluThrGluLysLeuHisValAspThrGluSerGlnTyrAlaGlnThrAspThrProVal-154 |
| SEQ. ID. NO. 29314 | 160-AlaSerHisGlyGlnAlaGlyGly-167 |
| SEQ. ID. NO. 29315 | 170-TyrAsnHisLysThrGly-175 |
| SEQ. ID. NO. 29316 | 179-PheSerSerLysValLys-184 |
| SEQ. ID. NO. 29317 | 187-IleTyrAspThrLysAspMet-193 |
| Hydrophilic Regions - Hopp-Woods | |
| SEQ. ID. NO. 29318 | 29-IleSerGluValGluIleGluGluValArgLeuAsnProAspGluProGlnTyr-46 |
| SEQ. ID. NO. 29319 | 49-AspGlyLeuAspGlyArgArgPheAspGlu-58 |
| SEQ. ID. NO. 29320 | 65-HisLeuSerAlaLysGlyAlaLysGlnPheProGluAsnSerAspIleHisPhe-82 |
| SEQ. ID. NO. 29321 | 99-ValGlySerAspGluAlaValTyr-106 |
| SEQ. ID. NO. 29322 | 108-ThrGluAsnLysGlnValLeu-114 |
| SEQ. ID. NO. 29323 | 123-LysThrAlaAspGlyArgArgGlnAlaGlyLysValGluThrGluLysLeuHisValAspThrGluSerGlnTyrAla-148 |
| SEQ. ID. NO. 29324 | 187-IleTyrAspThrLysAspMet-193 |
| g216-2 | |
| AMPHI Regions - AMPHI | |
| SEQ. ID. NO. 29325 | 19-AlaGluGlyLeuArgGluIleAlaAlaGluLeu-29 |
| SEQ. ID. NO. 29326 | 60-ArgLysMetAlaAla-64 |
| SEQ. ID. NO. 29327 | 165-LeuGlyAspAlaLeuAlaVal-171 |
| SEQ. ID. NO. 29328 | 201-ValAlaAspIleMetHis-206 |
| SEQ. ID. NO. 29329 | 251-GlyAspLeuArgArgLeuPheGlnGluCysAspAsnPheThrGlyLeuSerIle-268 |
| SEQ. ID. NO. 29330 | 272-MetHisThrHisProLysThrIleSerAla-281 |
| SEQ. ID. NO. 29331 | 290-LysValMetGlnAlaAsn-295 |

TABLE 1-continued

| | |
|---|---|
| Antigenic Index - Jameson-Wolf | |
| SEQ. ID. NO. 29332 | 1-MetAlaGluAsnGluLysTyrLeuAspTrpAlaArg-12 |
| SEQ. ID. NO. 29333 | 14-ValLeuHisThrGluAlaGluGlyLeuArgGluIleAlaAlaGluLeuAspGlu-31 |
| SEQ. ID. NO. 29334 | 43-CysLysGlyArgVal-47 |
| SEQ. ID. NO. 29335 | 51-GlyMetGlyLysSerGlyHisIleGlyArgLysMetAla-63 |
| SEQ. ID. NO. 29336 | 80-GluAlaAlaHisGlyAspLeu-86 |
| SEQ. ID. NO. 29337 | 90-ValAspAsnAspVal-94 |
| SEQ. ID. NO. 29338 | 99-SerAsnSerGlyGluSerAspGluIle-107 |
| SEQ. ID. NO. 29339 | 113-AlaLeuLysArgLysAspIle-119 |
| SEQ. ID. NO. 29340 | 125-ThrAlaArgProAspSerThrMetAlaArgHisAlaAsp-137 |
| SEQ. ID. NO. 29341 | 144-ValSerGlnGluAlaCysProLeu-151 |
| SEQ. ID. NO. 29342 | 177-ArgAlaPheThrProAspAspPheAla-185 |
| SEQ. ID. NO. 29343 | 190-AlaGlySerLeuGlyLys-195 |
| SEQ. ID. NO. 29344 | 203-AspIleMetHisLysGlyGlyGlyLeuProAla-213 |
| SEQ. ID. NO. 29345 | 227-MetSerGluLysGlyLeu-232 |
| SEQ. ID. NO. 29346 | 238-ThrAspGlyGlnGlyCysLeu-244 |
| SEQ. ID. NO. 29347 | 248-PheThrAspGlyAspLeuArgArgLeuPheGlnGluCysAspAsnPheThr-264 |
| SEQ. ID. NO. 29348 | 275-HisProLysThrIleSerAlaGluArgLeuAlaThrGluAlaLeuLys-290 |
| Hydrophilic Regions - Hopp-Woods | |
| SEQ. ID. NO. 29349 | 1-MetAlaGluAsnGluLysTyrLeuAspTrpAlaArg-12 |
| SEQ. ID. NO. 29350 | 14-ValLeuHisThrGluAlaGluGlyLeuArgGluIleAlaAlaGluLeuAspGlu-31 |
| SEQ. ID. NO. 29351 | 43-CysLysGlyArgVal-47 |
| SEQ. ID. NO. 29352 | 56-GlyHisIleGlyArgLysMetAla-63 |
| SEQ. ID. NO. 29353 | 100-AsnSerGlyGluSerAspGluIle-107 |
| SEQ. ID. NO. 29354 | 113-AlaLeuLysArgLysAspIle-119 |
| SEQ. ID. NO. 29355 | 126-AlaArgProAspSerThrMetAlaArgHisAlaAsp-137 |
| SEQ. ID. NO. 29356 | 144-ValSerGlnGluAla-148 |
| SEQ. ID. NO. 29357 | 177-ArgAlaPheThrProAspAsp-183 |
| SEQ. ID. NO. 29358 | 227-MetSerGluLysGlyLeu-232 |
| SEQ. ID. NO. 29359 | 251-GlyAspLeuArgArgLeuPheGlnGluCysAspAsn-262 |
| SEQ. ID. NO. 29360 | 277-LysThrIleSerAlaGluArgLeuAlaThrGluAlaLeuLys-290 |
| g218 | |
| AMPHI Regions - AMPHI | |
| SEQ. ID. NO. 29361 | 9-AlaLysValValAsnThrMet-15 |
| SEQ. ID. NO. 29362 | 23-HisThrMetAspGluIleHisGly-30 |
| SEQ. ID. NO. 29363 | 78-AlaArgSerTrpTrpArgAsnLeuHisGlyAlaPheGlyThrTrpValSerLeuIleLeu-97 |
| SEQ. ID. NO. 29364 | 111-TrpGlyGlyLysPheValGlnAlaTrpAsnGlnPhePro-123 |
| SEQ. ID. NO. 29365 | 176-ThrGluProAsnAsnIle-181 |
| SEQ. ID. NO. 29366 | 187-PheArgAlaGlyAsnArgPheGlnArgAlaLeuSerVal-199 |
| Antigenic Index - Jameson-Wolf | |
| SEQ. ID. NO. 29367 | 14-ThrMetProArgAsnGlnGlyTrp-21 |
| SEQ. ID. NO. 29368 | 26-AspGluIleHisGly-30 |
| SEQ. ID. NO. 29369 | 62-AlaLysGlnArgGlyIleLys-68 |
| SEQ. ID. NO. 29370 | 71-LeuLeuProProLysSerArgAlaArgSerTrpTrp-82 |
| SEQ. ID. NO. 29371 | 86-HisGlyAlaPheGly-90 |
| SEQ. ID. NO. 29372 | 123-ProAlaGlyLysTrpGlyValGluProAsnProVal-134 |
| SEQ. ID. NO. 29373 | 143-ValLeuAsnAspGlyLysValLysGlu-151 |
| SEQ. ID. NO. 29374 | 167-ThrValGlyGluAsnGlyIleAsnProThrGluProAsnAsnIleGlyAsnArgArgProPheArgAlaGlyAsnArgPheGlnArg-195 |
| SEQ. ID. NO. 29375 | 201-PheAlaGlnArgArgGlyArgGlyMetAspPhe-211 |
| Hydrophilic Regions - Hopp-Woods | |
| SEQ. ID. NO. 29376 | 26-AspGluIleHisGly-30 |
| SEQ. ID. NO. 29377 | 64-GlnArgGlyIleLys-68 |
| SEQ. ID. NO. 29378 | 74-ProLysSerArgAla-78 |
| SEQ. ID. NO. 29379 | 143-ValLeuAsnAspGlyLysValLysGlu-151 |
| SEQ. ID. NO. 29380 | 171-AsnGlyIleAsnProThrGluProAsnAsnIleGlyAsnArgArgProPheArgAlaGlyAsnArgPheGlnArg-195 |
| SEQ. ID. NO. 29381 | 201-PheAlaGlnArgArgGlyArgGlyMetAsp-210 |
| g225-1 | |
| AMPHI Regions - AMPHI | |
| SEQ. ID. NO. 29382 | 23-LeuAlaAspGluLeuThrAsn-29 |
| SEQ. ID. NO. 29383 | 37-IleLeuArgGlnPhe-41 |
| SEQ. ID. NO. 29384 | 92-AspLysLeuIleGlySerAlaMetArg-100 |
| SEQ. ID. NO. 29385 | 122-PheMetGlnHisIlePheLys-128 |
| SEQ. ID. NO. 29386 | 188-ThrGlyLysAsnIle-192 |
| Antigenic Index - Jameson-Wolf | |
| SEQ. ID. NO. 29387 | 22-AlaLeuAlaAspGluLeuThr-28 |
| SEQ. ID. NO. 29388 | 32-SerSerArgGluGlnIleLeu-38 |
| SEQ. ID. NO. 29389 | 41-PheAlaGluAspGluGlnProVal-48 |
| SEQ. ID. NO. 29390 | 50-ProValAsnArgAlaProAlaArgArgAlaGlyAsnAlaAspGluLeuIle-66 |
| SEQ. ID. NO. 29391 | 79-ArgValAsnArgAlaXxxAlaArgArgAlaGlyAsnAlaAspLysLeuIle-95 |
| SEQ. ID. NO. 29392 | 115-ThrGlyPheAspCysSerGly-121 |
| SEQ. ID. NO. 29393 | 135-LeuProArgThrSerAlaGluGlnAlaArgMet-145 |
| SEQ. ID. NO. 29394 | 147-AlaProValAlaArgSerGluLeuGlnProGlyAsp-158 |
| SEQ. ID. NO. 29395 | 165-LeuGlyGlySerArgIleSer-171 |
| SEQ. ID. NO. 29396 | 184-HisAlaProArgThrGlyLysAsnIleGlu-193 |
| SEQ. ID. NO. 29397 | 196-SerLeuSerHisLysTyrTrpSerGlyLys-205 |
| SEQ. ID. NO. 29398 | 210-ArgArgValLysLysAsnAspProSerArgPhe-220 |
| Hydrophilic Regions - Hopp-Woods | |
| SEQ. ID. NO. 29399 | 22-AlaLeuAlaAspGluLeuThr-28 |
| SEQ. ID. NO. 29400 | 32-SerSerArgGluGlnIleLeu-38 |
| SEQ. ID. NO. 29401 | 41-PheAlaGluAspGluGlnPro-47 |

TABLE 1-continued

SEQ. ID. NO. 29402 53-ArgAlaProAlaArgArgAlaGlyAsnAlaAspGluLeuIle-66
SEQ. ID. NO. 29403 79-ArgValAsnArgAlaXxxAlaArgArgAlaGlyAsnAlaAspLysLeuIle-95
SEQ. ID. NO. 29404 137-ArgThrSerAlaGluGlnAlaArgMet-145
SEQ. ID. NO. 29405 149-ValAlaArgSerGluLeuGlnPro-156
SEQ. ID. NO. 29406 187-ArgThrGlyLysAsnIleGlu-193
SEQ. ID. NO. 29407 210-ArgArgValLysLysAsnAspProSerArg-219
g226
AMPHI Regions - AMPHI
SEQ. ID. NO. 29408 44-LeuIleAlaTyrLeuLys-49
SEQ. ID. NO. 29409 98-GlnLeuAlaGlySerValThrGlyIleValThr-108
SEQ. ID. NO. 29410 142-ThrLeuTyrAlaArgValLeuProPro-150
SEQ. ID. NO. 29411 165-ThrLeuArgArgPhe-169
SEQ. ID. NO. 29412 174-LysLysLeuArgProPheLysProLeuLeuProVal-185
Antigenic Index - Jameson-Wolf
SEQ. ID. NO. 29413 3-GluIleLeuArgGlnProSer-9
SEQ. ID. NO. 29414 25-ValArgThrArgThrGlyAsnIle-32
SEQ. ID. NO. 29415 67-PheArgLeuLysPro-71
SEQ. ID. NO. 29416 81-TyrGlnAsnArgArgLysIle-87
SEQ. ID. NO. 29417 117-GlyProAspThrGlnPhe-122
SEQ. ID. NO. 29418 124-PheProProArgLeu-128
SEQ. ID. NO. 29419 155-ProProLeuLeuProArgLeuGlyProHisThrLeuArgArg-168
SEQ. ID. NO. 29420 171-IleLeuProLysLysLeuArgProPheLys-180
Hydrophilic Regions - Hopp-Woods
SEQ. ID. NO. 29421 25-ValArgThrArgThr-29
SEQ. ID. NO. 29422 82-GlnAsnArgArgLysIle-87
SEQ. ID. NO. 29423 173-ProLysLysLeuArgPro-178
g227
AMPHI Regions - AMPHI
SEQ. ID. NO. 29424 36-GlyValLeuPheAlaLeuLeuGlnAla-44
SEQ. ID. NO. 29425 51-TrpLeuGlnGlnLeuThrAspAlaLeu-59
SEQ. ID. NO. 29426 74-ValIleSerTyrLeuAspLeuIleAlaAspAspTrpPheSer-87
g230-1
AMPHI Regions - AMPHI
SEQ. ID. NO. 29427 6-GluLysTyrArgThr-10
SEQ. ID. NO. 29428 49-GluHisSerIleAsnAsn-54
SEQ. ID. NO. 29429 56-MetGlnAsnGluGln-60
SEQ. ID. NO. 29430 69-AspAlaValPheGlnSerLeuLeuGln-77
SEQ. ID. NO. 29431 81-LeuLysGlnGlyAlaLys-86
SEQ. ID. NO. 29432 96-GlnIleLysGlnMetIle-101
SEQ. ID. NO. 29433 115-SerHisAlaLeuLeuSer-120
SEQ. ID. NO. 29434 133-PheValGluGluIleArgAspGlnPhe-141
SEQ. ID. NO. 29435 144-GlnAsnLeuValSerLeu-149
SEQ. ID. NO. 29436 161-AlaGluGlnLeuIleArgLeuThrGlnValAsnArgThrIleArg-175
SEQ. ID. NO. 29437 184-PheIleAlaGlnVal-188
SEQ. ID. NO. 29438 194-AspLeuGlnLysPheTyrAsn-200
SEQ. ID. NO. 29439 234-GluValLysAsnAlaPheGluGluArgValAlaArgLeu-246
SEQ. ID. NO. 29440 272-ValAlaAspPheAsnLys-277
SEQ. ID. NO. 29441 284-AspAspAlaPheAsnHisProSerSerLeuAlaGluAla-296
SEQ. ID. NO. 29442 319-SerGlyMetProGluAsnLeuIleAsnAlaVal-329
SEQ. ID. NO. 29443 398-LeuAsnGlyGlyLys-402
SEQ. ID. NO. 29444 426-GluAlaTyrAlaGluLeu-431
SEQ. ID. NO. 29445 461-ThrProProGluAspIleAlaAla-468
SEQ. ID. NO. 29446 488-LeuLeuIleArgTyrPheAsn-494
Antigenic Index - Jameson-Wolf
SEQ. ID. NO. 29447 4-SerIleGluLysTyrArgThrProAla-12
SEQ. ID. NO. 29448 32-SerHisProGlyAlaAsp-37
SEQ. ID. NO. 29449 42-ValGlyAspGluLysIleSerGluHisSerIle-52
SEQ. ID. NO. 29450 56-MetGlnAsnGluGlnAlaAspGlyGlySerProTrpArg-68
SEQ. ID. NO. 29451 80-TyrLeuLysGlnGlyAla-85
SEQ. ID. NO. 29452 92-ValSerSerGluGlnIleLys-98
SEQ. ID. NO. 29453 101-IleValAspAspProAsnPheHisAspAlaAsnGlyLysPhe-114
SEQ. ID. NO. 29454 123-LeuSerGlnArgHisMetSerGluAspGlnPheValGluGluIleArgAsp-139
SEQ. ID. NO. 29455 169-GlnValAsnArgThrIleArgSerHisThrPheAsnProAspGluPhe-184
SEQ. ID. NO. 29456 189-LysAlaSerGluAlaAspLeu-195
SEQ. ID. NO. 29457 199-TyrAsnAlaAsnLysLysAspTyrLeu-207
SEQ. ID. NO. 29458 223-AspPheAlaAspLysGlnThrValSerGluThrGluValLysAsnAlaPheGluGluArgValAlaArg-245
SEQ. ID. NO. 29459 247-ProAlaHisGluAlaLysProSerPheGluGlnGluLysAlaAlaValGluAsnGluLeuLysMetLysLysAlaValAlaAspPheAsnLysAlaLys GluLysLeuGlyAspAspAlaPheAsnHisProSerSerLeuAlaGluAlaAlaLysAsnSerGlyLeuLysValGluThrGlnGluThrTrpLeuSerArg GlnAspAlaGlnMetSerGlyMetProGluAsn-324
SEQ. ID. NO. 29460 330-PheSerAspAspValLeuLysLysLysHisAsnSerGlu-342
SEQ. ID. NO. 29461 355-ArgAlaLysGluValArgGluGluLysAsnLeuLeu-366
SEQ. ID. NO. 29462 368-GluGluAlaLysAspAlaValArg-375
SEQ. ID. NO. 29463 377-AlaTyrIleArgThrGluAlaAlaLysLeuAlaGluAsnLysAlaLysGluValLeu-395
SEQ. ID. NO. 29464 399-AsnGlyGlyLysAlaValAsp-405
SEQ. ID. NO. 29465 417-GlnGlnAlaArgGlnSerMetProProGluAlaTyr-428
SEQ. ID. NO. 29466 432-LeuLysAlaLysProAlaAsnGlyLysProAla-442
SEQ. ID. NO. 29467 459-AlaValThrProProGluAspIleAla-467

TABLE 1-continued

SEQ. ID. NO. 29468 476-AlaLeuAlaGlnGlnGlnSerAlaAsnThrPhe-486
SEQ. ID. NO. 29469 493-PheAsnGlyLysIleLysGlnThrLysGlyAlaGlnSerValAspAsnGlyAspGlyGln-512
Hydrophilic Regions - Hopp-Woods
SEQ. ID. NO. 29470 6-GluLysTyrArgThr-10
SEQ. ID. NO. 29471 42-ValGlyAspGluLysIleSerGlu-49
SEQ. ID. NO. 29472 56-MetGlnAsnGluGlnAlaAspGly-63
SEQ. ID. NO. 29473 92-ValSerSerGluGlnIleLys-98
SEQ. ID. NO. 29474 101-IleValAspAspProAsnPhe-107
SEQ. ID. NO. 29475 110-AlaAsnGlyLysPhe-114
SEQ. ID. NO. 29476 126-ArgHisMetSerGluAspGlnPheValGluGluIleArgAsp-139
SEQ. ID. NO. 29477 189-LysAlaSerGluAlaAspLeu-195
SEQ. ID. NO. 29478 200-AsnAlaAsnLysLysAspTyrLeu-207
SEQ. ID. NO. 29479 223-AspPheAlaAspLysGlnThrValSerGluThrGluValLysAsnAlaPheGluGluArgValAlaArg-245
SEQ. ID. NO. 29480 247-ProAlaHisGluAlaLysProSerPheGluGlnGluLysAlaAlaValGluAsnGluLeuLysMetLysLysAlaValAlaAspPheAsnLysAlaLys GluLysLeuGlyAspAspAlaPheAsn-288
SEQ. ID. NO. 29481 292-SerLeuAlaGluAlaAlaLysAsnSerGlyLeuLysValGluThrGlnGlu-308
SEQ. ID. NO. 29482 310-TrpLeuSerArgGlnAspAlaGlnMet-318
SEQ. ID. NO. 29483 333-AspValLeuLysLysLysHisAsnSer-341
SEQ. ID. NO. 29484 355-ArgAlaLysGluValArgGluGluLysAsnLeuLeu-366
SEQ. ID. NO. 29485 368-GluGluAlaLysAspAlaValArg-375
SEQ. ID. NO. 29486 377-AlaTyrIleArgThrGluAlaAlaLysLeuAlaGluAsnLysAlaLysGluValLeu-395
SEQ. ID. NO. 29487 417-GlnGlnAlaArgGlnSerMetPro-424
SEQ. ID. NO. 29488 432-LeuLysAlaLysProAlaAsnGly-439
SEQ. ID. NO. 29489 461-ThrProProGluAspIleAla-467
SEQ. ID. NO. 29490 496-LysIleLysGlnThrLysGlyAlaGlnSerValAspAsnGlyAspGlyGln-512
g231-1
AMPHI Regions - AMPHI
SEQ. ID. NO. 29491 7-IleAsnArgProTyrGlnLysProAlaGluLeu-17
SEQ. ID. NO. 29492 98-ArgIlePheSerPheProGln-104
SEQ. ID. NO. 29493 169-TyrAsnGluPheArgThrLeuArgArg-177
SEQ. ID. NO. 29494 209-AlaValAspAspValLysGlyIleAlaVal-218
Antigenic Index - Jameson-Wolf
SEQ. ID. NO. 29495 1-MetSerLysArgLysSerIleAsnArgProTyrGlnLysProAlaGlu-16
SEQ. ID. NO. 29496 18-ProProLeuGlnAsnAsnProProPheTyrArgLysAsnArgArgLeuAsn-34
SEQ. ID. NO. 29497 39-AlaAspGlyGlyCysAlaSerProGlnLysCysArgAlaArgGlyPheGln-55
SEQ. ID. NO. 29498 90-ProAlaValArgProArgArgLeuArg-98
SEQ. ID. NO. 29499 135-MetProArgArgProVal-140
SEQ. ID. NO. 29500 167-HisThrTyrAsnGluPheArgThrLeuArgArgArgAlaGlnVal-181
SEQ. ID. NO. 29501 196-ValAspIleArgHisProAsn-202
SEQ. ID. NO. 29502 209-AlaValAspAspValLysGly-215
Hydrophilic Regions - Hopp-Woods
SEQ. ID. NO. 29503 1-MetSerLysArgLysSerIleAsn-8
SEQ. ID. NO. 29504 10-ProTyrGlnLysProAlaGlu-16
SEQ. ID. NO. 29505 26-PheTyrArgLysAsnArgArg-32
SEQ. ID. NO. 29506 45-SerProGlnLysCysArgAlaArgGly-53
SEQ. ID. NO. 29507 92-ValArgProArgArgLeuArg-98
SEQ. ID. NO. 29508 136-ProArgArgProVal-140
SEQ. ID. NO. 29509 173-ArgThrLeuArgArgArgAlaGlnVal-181
SEQ. ID. NO. 29510 196-ValAspIleArgHis-200
SEQ. ID. NO. 29511 209-AlaValAspAspValLysGly-215
g232
AMPHI Regions - AMPHI
SEQ. ID. NO. 29512 14-AlaIleLeuPheGly-18
SEQ. ID. NO. 29513 21-LeuGlyThrAlaVal-25
SEQ. ID. NO. 29514 68-ValArgGlyThrLysSerLeuLeuArgGluThrVal-79
SEQ. ID. NO. 29515 105-LeuProThrPheThrGln-110
SEQ. ID. NO. 29516 151-ValThrValGlyAlaLeuGlySerThrValCys-161
SEQ. ID. NO. 29517 173-ArgPheGluGlyLeuAsn-178
SEQ. ID. NO. 29518 194-AlaValMetThrLeuIleGlyPhePheGlyGlyPhePheSerValProLeuTyrThrTrpLeu-214
Antigenic Index - Jameson-Wolf
SEQ. ID. NO. 29519 54-ValProAlaLysAlaAlaAspThrGlnIle-63
SEQ. ID. NO. 29520 69-ArgGlyThrLysSerLeuLeuArgGluThrValArgHisAsnProVal-84
SEQ. ID. NO. 29521 112-HisLeuGlyGlyAsnAspAsnVal-119
SEQ. ID. NO. 29522 140-LysPheGlyArgGluArgLeu-146
SEQ. ID. NO. 29523 170-HisGlyHisArgPheGluGly-176
SEQ. ID. NO. 29524 217-AlaSerSerGluThrPheArgAlaArgAla-226
SEQ. ID. NO. 29525 274-IleLysArgGluArgArgPheLeu-281
SEQ. ID. NO. 29526 285-AlaIleArgLysLysPro-290
Hydrophilic Regions - Hopp-Woods
SEQ. ID. NO. 29527 55-ProAlaLysAlaAlaAspThrGlnIle-63
SEQ. ID. NO. 29528 69-ArgGlyThrLysSerLeuLeuArgGluThrValArg-80
SEQ. ID. NO. 29529 140-LysPheGlyArgGluArgLeu-146
SEQ. ID. NO. 29530 172-HisArgPheGluGly-176
SEQ. ID. NO. 29531 220-GluThrPheArgAlaArgAla-226
SEQ. ID. NO. 29532 274-IleLysArgGluArgArgPheLeu-281
SEQ. ID. NO. 29533 285-AlaIleArgLysLysPro-290
g233
AMPHI Regions - AMPHI
SEQ. ID. NO. 29534 36-GluHisValLeuGly-40
SEQ. ID. NO. 29535 61-PheAlaAspLysValGlnThr-67

TABLE 1-continued

| | |
|---|---|
| SEQ. ID. NO. 29536 | 71-GlnValArgValTrpLysAsn-77 |
| SEQ. ID. NO. 29537 | 88-AsnGlyValAlaLysLeuLeuGluThr-96 |
| SEQ. ID. NO. 29538 | 119-AlaLeuAlaArgLeuIleGluGlnAlaGlyAsnAla-130 |
| SEQ. ID. NO. 29539 | 138-ValProValAlaAspThrLeuLysArgAlaGluSer-149 |
| SEQ. ID. NO. 29540 | 182-GluAsnLeuGlyGlyIleThrAsp-189 |
| Antigenic Index - Jameson-Wolf | |
| SEQ. ID. NO. 29541 | 1-MetLysArgLysAsnIle-6 |
| SEQ. ID. NO. 29542 | 17-ArgPheGlyAlaAspLysProLysGlnTyrValGluIleGlySerLysThrValLeu-35 |
| SEQ. ID. NO. 29543 | 43-GluArgHisGluAlaValAsp-49 |
| SEQ. ID. NO. 29544 | 56-SerProGluAspThrPheAlaAspLysValGln-66 |
| SEQ. ID. NO. 29545 | 75-TrpLysAsnGlyGlyGlnThrArgAlaGluThrValArgAsnGlyVal-90 |
| SEQ. ID. NO. 29546 | 100-AlaGluThrAspAsn-104 |
| SEQ. ID. NO. 29547 | 109-AspAlaAlaArgCys-113 |
| SEQ. ID. NO. 29548 | 115-LeuProSerGluAlaLeu-120 |
| SEQ. ID. NO. 29549 | 123-LeuIleGluGlnAlaGlyAsnAlaAlaGluGlyGly-134 |
| SEQ. ID. NO. 29550 | 142-AspThrLeuLysArgAlaGluSerGlyGln-151 |
| SEQ. ID. NO. 29551 | 155-ThrValAspArgSerGlyLeu-161 |
| SEQ. ID. NO. 29552 | 183-AsnLeuGlyGlyIleThrAspGluAlaSerAlaValGluLysLeuGlyVal-199 |
| SEQ. ID. NO. 29553 | 206-GlyAspAlaArgAsnLeuLysLeuThrGlnProGlnAspAlaTyr-220 |
| Hydrophilic Regions - Hopp-Woods | |
| SEQ. ID. NO. 29554 | 1-MetLysArgLysAsnIle-6 |
| SEQ. ID. NO. 29555 | 18-PheGlyAlaAspLysProLysGlnTyrVal-27 |
| SEQ. ID. NO. 29556 | 43-GluArgHisGluAlaValAsp-49 |
| SEQ. ID. NO. 29557 | 56-SerProGluAspThrPheAlaAspLysValGln-66 |
| SEQ. ID. NO. 29558 | 79-GlyGlnThrArgAlaGluThrValArg-87 |
| SEQ. ID. NO. 29559 | 100-AlaGluThrAspAsn-104 |
| SEQ. ID. NO. 29560 | 127-AlaGlyAsnAlaAlaGlu-132 |
| SEQ. ID. NO. 29561 | 142-AspThrLeuLysArgAlaGluSerGlyGln-151 |
| SEQ. ID. NO. 29562 | 187-IleThrAspGluAlaSerAlaValGluLysLeuGlyVal-199 |
| SEQ. ID. NO. 29563 | 206-GlyAspAlaArgAsnLeuLys-212 |
| g234 | |
| AMPHI Regions - AMPHI | |
| SEQ. ID. NO. 29564 | 26-ArgSerLeuGluValAlaLysValAla-34 |
| SEQ. ID. NO. 29565 | 68-AspArgLeuGlySerGln-73 |
| SEQ. ID. NO. 29566 | 83-GlnGlnThrAsnArgPheAsnValLeuAsnArgThrAsn-95 |
| SEQ. ID. NO. 29567 | 121-GlyAspValThrGluPhe-126 |
| SEQ. ID. NO. 29568 | 205-GluAlaValAspAsnLeuValGlnAlaValAspAsn-216 |
| Antigenic Index - Jameson-Wolf | |
| SEQ. ID. NO. 29569 | 21-AlaThrGluSerSerArgSerLeuGluValAlaLys-32 |
| SEQ. ID. NO. 29570 | 51-ThrPheAspAsnArgSerSerPhe-58 |
| SEQ. ID. NO. 29571 | 62-IlePheSerAspSerGluAspArgLeuGlySerGlnAla-74 |
| SEQ. ID. NO. 29572 | 83-GlnGlnThrAsnArgPheAsnValLeuAsnArgThrAsn-95 |
| SEQ. ID. NO. 29573 | 99-LeuLysGlnGluSerGlyIleSerGlyLysAlaGlnAsnLeuLysGlyAlaAspTyr-117 |
| SEQ. ID. NO. 29574 | 121-GlyAspValThrGluPheGlyArgArgAspValGlyAsp-133 |
| SEQ. ID. NO. 29575 | 140-LeuGlyArgGlyLysSerGlnIle-147 |
| SEQ. ID. NO. 29576 | 169-GlnGlyAlaGlyGlu-173 |
| SEQ. ID. NO. 29577 | 175-AlaLeuSerAsnArgGluIle-181 |
| SEQ. ID. NO. 29578 | 185-GlyGlyThrSerGlyTyrAspAlaThrLeuAsnGlyLysValLeu-199 |
| SEQ. ID. NO. 29579 | 214-ValAspAsnGlyAlaTrpGlnSerAsnArg-223 |
| Hydrophilic Regions - Hopp-Woods | |
| SEQ. ID. NO. 29580 | 21-AlaThrGluSerSerArgSerLeuGluValAlaLys-32 |
| SEQ. ID. NO. 29581 | 52-PheAspAsnArgSerSerPhe-58 |
| SEQ. ID. NO. 29582 | 62-IlePheSerAspSerGluAspArgLeuGlySerGlnAla-74 |
| SEQ. ID. NO. 29583 | 99-LeuLysGlnGluSerGlyIleSerGlyLysAlaGlnAsnLeuLysGly-114 |
| SEQ. ID. NO. 29584 | 122-AspValThrGluPheGlyArgArgAspValGlyAsp-133 |
| SEQ. ID. NO. 29585 | 141-GlyArgGlyLysSer-145 |
| SEQ. ID. NO. 29586 | 176-LeuSerAsnArgGluIle-181 |
| g235 | |
| AMPHI Regions - AMPHI | |
| SEQ. ID. NO. 29587 | 8-LeuAlaAlaValLeuAlaLeu-14 |
| SEQ. ID. NO. 29588 | 18-GlnValArgLysAlaProAsp-24 |
| SEQ. ID. NO. 29589 | 88-AsnAlaAlaAspIle-92 |
| SEQ. ID. NO. 29590 | 95-ValArgProGluLysLeuHisGlnIlePhe-104 |
| SEQ. ID. NO. 29591 | 120-SerTyrGlnIleLeuAspSerValThrThr-129 |
| SEQ. ID. NO. 29592 | 165-GlyAlaLeuValGlyAlaValValAsnGlnIleAlaAsnSerLeuThr-180 |
| SEQ. ID. NO. 29593 | 187-SerLysThrAlaAlaTyrAsnLeuLeu-195 |
| Antigenic Index - Jameson-Wolf | |
| SEQ. ID. NO. 29594 | 17-CysGlnValArgLysAlaProAspLeuAspTyrThrSerPheLysGluSerLysProAla-36 |
| SEQ. ID. NO. 29595 | 43-ProLeuAsnGluSerProAspValAsnGlyThr-53 |
| SEQ. ID. NO. 29596 | 79-GluThrPheLysGluAsnGlyLeu-86 |
| SEQ. ID. NO. 29597 | 93-HisAlaValArgProGluLysLeu-100 |
| SEQ. ID. NO. 29598 | 131-SerAlaLysAlaArgLeuValAspSerArgAsnGlyLysGluLeuTrpSerGlySerAlaSerIleArgGluGlySerAsnAsnSerAsnSer-161 |
| SEQ. ID. NO. 29599 | 178-SerLeuThrAspArgGlyTyrGlnValSerLysThrAla-190 |
| SEQ. ID. NO. 29600 | 197-ProTyrSerArgAsnGlyIleLeuLysGlyProArgPheValGluGluGlnProLys-215 |
| Hydrophilic Regions - Hopp-Woods | |
| SEQ. ID. NO. 29601 | 18-GlnValArgLysAlaProAspLeuAsp-26 |
| SEQ. ID. NO. 29602 | 29-SerPheLysGluSerLysPro-35 |
| SEQ. ID. NO. 29603 | 44-LeuAsnGluSerProAspVal-50 |
| SEQ. ID. NO. 29604 | 79-GluThrPheLysGluAsnGlyLeu-86 |
| SEQ. ID. NO. 29605 | 93-HisAlaValArgProGluLysLeu-100 |

TABLE 1-continued

| | |
|---|---|
| SEQ. ID. NO. 29606 | 131-SerAlaLysAlaArgLeuValAspSerArgAsnGlyLysGluLeuTrp-146 |
| SEQ. ID. NO. 29607 | 150-AlaSerIleArgGluGlySerAsnAsnSer-159 |
| SEQ. ID. NO. 29608 | 179-LeuThrAspArgGlyTyrGln-185 |
| SEQ. ID. NO. 29609 | 207-ProArgPheValGluGluGlnProLys-215 |
| g236 | |
| AMPHI Regions - AMPHI | |
| SEQ. ID. NO. 29610 | 10-IleLeuArgThrAlaPhe-15 |
| SEQ. ID. NO. 29611 | 107-PheAlaArgPheAlaAspCysArgProPhe-116 |
| SEQ. ID. NO. 29612 | 146-AspAspValProArgPhePheAlaGlyGlu-155 |
| SEQ. ID. NO. 29613 | 168-ArgAspValValGlnGlyGlyLeu-175 |
| SEQ. ID. NO. 29614 | 213-GlyGluValGluGlyIleAlaArgIleValThrAlaCysGlnThrLeuLeuGlnProProArgGlnTyrGln-236 |
| SEQ. ID. NO. 29615 | 245-IleArgLeuLeuHisGlyIlePheAsnArgIleLysValAla-258 |
| SEQ. ID. NO. 29616 | 275-PheGlyAsnAlaPheGluAspPhe-282 |
| SEQ. ID. NO. 29617 | 316-ValAlaAspGlyPheArgHisPheAlaAla-325 |
| Antigenic Index - Jameson-Wolf | |
| SEQ. ID. NO. 29618 | 43-PheGlyGlyAsnGlyLysPheIleThr-51 |
| SEQ. ID. NO. 29619 | 58-ArgHisGlnGlnGlyLysAla-64 |
| SEQ. ID. NO. 29620 | 77-PhePheArgArgGlyAsnPheGlyPheArgLeuGlnGlyArgThrAspSerPhe-94 |
| SEQ. ID. NO. 29621 | 98-GlnArgLeuAspSerGlyGlyTyr-105 |
| SEQ. ID. NO. 29622 | 111-AlaAspCysArgProPhe-116 |
| SEQ. ID. NO. 29623 | 126-ValAspGlyArgGluLeuValProSerMetGluGluAspAla-139 |
| SEQ. ID. NO. 29624 | 145-AlaAspAspValPro-149 |
| SEQ. ID. NO. 29625 | 152-PheAlaGlyGluAlaGlnAsnArgCysAsnGlnGluAsnGlnAlaAlaArgAspValValGlnGlyGlyLeu-175 |
| SEQ. ID. NO. 29626 | 195-ValGluValGluArgAlaGlnValPheArgAlaGluArgAsnAsnValPhe-211 |
| SEQ. ID. NO. 29627 | 213-GlyGluValGluGlyIleAla-219 |
| SEQ. ID. NO. 29628 | 230-GlnProProArgGlnTyrGln-236 |
| SEQ. ID. NO. 29629 | 261-GlyLysGlnGluAlaGlnGly-267 |
| SEQ. ID. NO. 29630 | 292-IleGlyGlyCysArgProGlnAlaGlnAspValArgAla-304 |
| SEQ. ID. NO. 29631 | 310-PheLeuArgArgAspAspValAlaAspGly-319 |
| SEQ. ID. NO. 29632 | 341-CysAlaSerHisGly-345 |
| Hydrophilic Regions - Hopp-Woods | |
| SEQ. ID. NO. 29633 | 87-LeuGlnGlyArgThrAspSer-93 |
| SEQ. ID. NO. 29634 | 98-GlnArgLeuAspSer-102 |
| SEQ. ID. NO. 29635 | 127-AspGlyArgGluLeuValProSerMetGluGluAspAla-139 |
| SEQ. ID. NO. 29636 | 145-AlaAspAspValPro-149 |
| SEQ. ID. NO. 29637 | 156-AlaGlnAsnArgCysAsnGlnGluAsnGlnAlaAlaArgAspValVal-171 |
| SEQ. ID. NO. 29638 | 195-ValGluValGluArgAlaGlnValPheArgAlaGluArgAsnAsn-209 |
| SEQ. ID. NO. 29639 | 213-GlyGluValGluGlyIleAla-219 |
| SEQ. ID. NO. 29640 | 261-GlyLysGlnGluAlaGlnGly-267 |
| SEQ. ID. NO. 29641 | 295-CysArgProGlnAlaGlnAspValArgAla-304 |
| SEQ. ID. NO. 29642 | 310-PheLeuArgArgAspAspValAlaAspGly-319 |
| g238 | |
| AMPHI Regions - AMPHI | |
| SEQ. ID. NO. 29643 | 103-ValHisSerProPheAsp-108 |
| SEQ. ID. NO. 29644 | 115-ThrSerAspPheSerGlyGlyVal-122 |
| SEQ. ID. NO. 29645 | 129-TyrGlnLeuHisArgThrGlySer-136 |
| SEQ. ID. NO. 29646 | 140-ProAlaAspGlyTyrAspGlyProGlnGlyGlyGlyTyrProGluProGlnGlyAlaArgAspIleTyrSerTyr-164 |
| SEQ. ID. NO. 29647 | 221-AsnArgMetAspAspIleArgGlyIleValGlnGlyAlaValAsnProPheLeuThrGlyPheGlnGlyVal-244 |
| SEQ. ID. NO. 29648 | 246-IleGlyAlaIleThrAspSerAlaValSerProValThrAspThrAlaAlaGlnGlnThrLeuGlnGlyIleAsnAspLeuGlyAsn-274 |
| SEQ. ID. NO. 29649 | 298-IleAsnSerAlaArgGlnTrpAlaAspAla-307 |
| SEQ. ID. NO. 29650 | 342-AspTrpValLysAsn-346 |
| SEQ. ID. NO. 29651 | 351-LysProAlaAlaArgHisMetGlnThrVal-360 |
| SEQ. ID. NO. 29652 | 367-GlyAsnArgProProLysSerIleThrSer-376 |
| SEQ. ID. NO. 29653 | 383-AlaThrTyrProLysLeuValAsnGlnLeuAsnGluGlnAsnLeu-397 |
| SEQ. ID. NO. 29654 | 426-GluGluAlaAspArgLeuGlyLysIleTrpVal-436 |
| SEQ. ID. NO. 29655 | 454-ThrArgGlnTyrArg-458 |
| Antigenic Index - Jameson-Wolf | |
| SEQ. ID. NO. 29656 | 25-HisAlaAsnGlyLeuAspAlaArgLeuArgAspAspMetGlnAlaLysHisTyrGluProGlyGlyLys-47 |
| SEQ. ID. NO. 29657 | 53-AsnAlaArgGlySerValLysAsnArgVal-62 |
| SEQ. ID. NO. 29658 | 80-ThrHisGluArgThrGlyPheGluGly-88 |
| SEQ. ID. NO. 29659 | 96-PheSerGlyHisGlyHisGluVal-103 |
| SEQ. ID. NO. 29660 | 105-SerProPheAspAsnHisAspSerLysSerThrSerAspPheSerGlyGlyValAspGlyGly-125 |
| SEQ. ID. NO. 29661 | 131-LeuHisArgThrGlySerGluIleHisProAlaAspGlyTyrAspGlyProGlnGlyGlyGlyTyrProGluProGlnGlyAlaArgAspIleTyr-162 |
| SEQ. ID. NO. 29662 | 166-IleLysGlyThrSerThrLysThrLysIle-175 |
| SEQ. ID. NO. 29663 | 182-ProPheSerAspArgTrpLeuLysGluAsnAlaGlyAla-194 |
| SEQ. ID. NO. 29664 | 200-SerArgAlaAspGluAlaGly-206 |
| SEQ. ID. NO. 29665 | 210-TrpGluAsnAspProAspLysAsnTrpArgAlaAsnArgMetAspAspIleArgGlyIle-229 |
| SEQ. ID. NO. 29666 | 268-GlyIleAsnAspLeuGlyAsnLeuSerProGluAla-279 |
| SEQ. ID. NO. 29667 | 292-PheAlaValLysAspGlyIleAsnSerAlaArgGlnTrpAlaAspAlaHisProAsnIle-311 |
| SEQ. ID. NO. 29668 | 328-ValTrpArgGlyLysLysValGluLeuAsnProThrLysTrpAspTrpValLysAsnThrGlyTyrLysLysProAlaAlaArg-355 |
| SEQ. ID. NO. 29669 | 358-GlnThrValAspGlyGluMetAlaGlyGlyAsnArgProProLysSerIleThrSerGluGlyLysAlaAsn-381 |
| SEQ. ID. NO. 29670 | 391-GlnLeuAsnGluGlnAsnLeu-397 |
| SEQ. ID. NO. 29671 | 401-AlaAlaGlnAspProArgLeu-407 |
| SEQ. ID. NO. 29672 | 411-IleHisGluGlyLysLysAsnPhePro-419 |
| SEQ. ID. NO. 29673 | 423-AlaThrTyrGluGluAlaAspArgLeuGly-432 |
| SEQ. ID. NO. 29674 | 438-GluGlyAlaArgGlnThrSerGlyGlyGlyTrpLeuSerArgAspGlyThrArgGlnTyrArgProProThrGluLysLysSerGln-466 |
| SEQ. ID. NO. 29675 | 480-ThrIleAspSerAsnGluLysArgAsnLysIleLysAsnGly-493 |
| Hydrophilic Regions - Hopp-Woods | |
| SEQ. ID. NO. 29676 | 29-LeuAspAlaArgLeuArgAspAspMetGlnAlaLysHisTyrGluProGlyGly-46 |
| SEQ. ID. NO. 29677 | 54-AlaArgGlySerValLysAsnArgVal-62 |

TABLE 1-continued

| | |
|---|---|
| SEQ. ID. NO. 29678 | 80-ThrHisGluArgThrGlyPhe-86 |
| SEQ. ID. NO. 29679 | 107-PheAspAsnHisAspSerLysSerThrSerAspPhe-118 |
| SEQ. ID. NO. 29680 | 133-ArgThrGlySerGluIleHisPro-140 |
| SEQ. ID. NO. 29681 | 142-AspGlyTyrAspGlyProGln-148 |
| SEQ. ID. NO. 29682 | 151-GlyTyrProGluProGlnGlyAlaArgAsp-160 |
| SEQ. ID. NO. 29683 | 168-GlyThrSerThrLysThrLysIle-175 |
| SEQ. ID. NO. 29684 | 186-ArgTrpLeuLysGluAsnAlaGly-193 |
| SEQ. ID. NO. 29685 | 200-SerArgAlaAspGluAlaGly-206 |
| SEQ. ID. NO. 29686 | 212-AsnAspProAspLysAsnTrpArgAlaAsnArgMetAspAspIleArgGly-228 |
| SEQ. ID. NO. 29687 | 296-AspGlyIleAsnSer-300 |
| SEQ. ID. NO. 29688 | 329-TrpArgGlyLysLysValGluLeuAsnProThr-339 |
| SEQ. ID. NO. 29689 | 347-ThrGlyTyrLysLysProAlaAlaArg-355 |
| SEQ. ID. NO. 29690 | 360-ValAspGlyGluMetAlaGlyGlyAsnArgProProLysSerIleThrSerGluGlyLysAlaAsn-381 |
| SEQ. ID. NO. 29691 | 392-LeuAsnGluGlnAsnLeu-397 |
| SEQ. ID. NO. 29692 | 401-AlaAlaGlnAspProArgLeu-407 |
| SEQ. ID. NO. 29693 | 412-HisGluGlyLysLysAsnPhe-418 |
| SEQ. ID. NO. 29694 | 424-ThrTyrGluGluAlaAspArgLeuGly-432 |
| SEQ. ID. NO. 29695 | 438-GluGlyAlaArgGlnThrSer-444 |
| SEQ. ID. NO. 29696 | 449-LeuSerArgAspGlyThrArgGlnTyrArgProProThrGluLysLysSerGln-466 |
| SEQ. ID. NO. 29697 | 482-AspSerAsnGluLysArgAsnLysIleLysAsn-492 |
| g239 | |
| AMPHI Regions - AMPHI | |
| SEQ. ID. NO. 29698 | 49-PheArgLeuValGlnSerCys-55 |
| SEQ. ID. NO. 29699 | 72-AsnAlaHisArgLysGln-77 |
| SEQ. ID. NO. 29700 | 123-ProGlyPheAsnAlaLeuProThrIlePhe-132 |
| SEQ. ID. NO. 29701 | 154-GluTyrPheLeuThr-158 |
| SEQ. ID. NO. 29702 | 165-SerSerAsnGluTrp-169 |
| SEQ. ID. NO. 29703 | 221-PheCysAlaThrIleCysAlaSerLeuArg-230 |
| Antigenic Index - Jameson-Wolf | |
| SEQ. ID. NO. 29704 | 6-GlyIleAlaArgAsnArgArgMetGlu-14 |
| SEQ. ID. NO. 29705 | 19-CysArgArgProAspArgPheVal-26 |
| SEQ. ID. NO. 29706 | 28-ArgGlnThrArgLeuLeu-33 |
| SEQ. ID. NO. 29707 | 53-GlnSerCysGluValGluPro-59 |
| SEQ. ID. NO. 29708 | 66-HisAsnGlyLysSerGlyAsnAlaHisArgLysGlnGlnLysGluIleArg-82 |
| SEQ. ID. NO. 29709 | 84-ValHisCysArgSerAspVal-90 |
| SEQ. ID. NO. 29710 | 100-ProAlaValArgSerAlaThrArgLysThrAla-110 |
| SEQ. ID. NO. 29711 | 132-PheArgGlyGlySerGlyLysSerAlaSer-141 |
| SEQ. ID. NO. 29712 | 147-LeuGlyArgGlySerCysCysGluTyr-155 |
| SEQ. ID. NO. 29713 | 164-ArgSerSerAsnGluTrpLys-170 |
| SEQ. ID. NO. 29714 | 173-ThrAlaLysArgProProSerPheArgArgHisMetThrCysGlyAsnThrAlaProThrSerSerSerSerArgLeuIleLys-200 |
| SEQ. ID. NO. 29715 | 209-ValAlaGlySerCysProArgSerArgValArgThr-220 |
| SEQ. ID. NO. 29716 | 248-TrpArgLeuAsnArgSerSerPro-255 |
| Hydrophilic Regions - Hopp-Woods | |
| SEQ. ID. NO. 29717 | 6-GlyIleAlaArgAsnArgArgMetGlu-14 |
| SEQ. ID. NO. 29718 | 20-ArgArgProAspArgPheVal-26 |
| SEQ. ID. NO. 29719 | 67-AsnGlyLysSerGlyAsnAlaHisArgLysGlnGlnLysGluIleArg-82 |
| SEQ. ID. NO. 29720 | 102-ValArgSerAlaThrArgLysThrAla-110 |
| SEQ. ID. NO. 29721 | 135-GlySerGlyLysSerAlaSer-141 |
| SEQ. ID. NO. 29722 | 165-SerSerAsnGluTrpLys-170 |
| SEQ. ID. NO. 29723 | 173-ThrAlaLysArgProProSerPheArgArgHisMet-184 |
| SEQ. ID. NO. 29724 | 193-SerSerSerSerArgLeuIleLys-200 |
| SEQ. ID. NO. 29725 | 211-GlySerCysProArgSerArgValArgThr-220 |
| SEQ. ID. NO. 29726 | 251-AsnArgSerSerPro-255 |
| g240 | |
| AMPHI Regions - AMPHI | |
| SEQ. ID. NO. 29727 | 19-AlaAspValGlyArgPheLeuHis-26 |
| SEQ. ID. NO. 29728 | 64-IleGlnCysLeuArgAsnHis-70 |
| SEQ. ID. NO. 29729 | 88-AlaProLeuPheAla-92 |
| SEQ. ID. NO. 29730 | 108-GlnGlyGluAspPheProArgAlaGlyIleGlnAsnHis-120 |
| SEQ. ID. NO. 29731 | 164-ValGlnAlaValHisAsn-169 |
| SEQ. ID. NO. 29732 | 178-AsnPheArgAlaValPheAlaIle-185 |
| SEQ. ID. NO. 29733 | 189-PheLysArgLysPheGln-194 |
| Antigenic Index - Jameson-Wolf | |
| SEQ. ID. NO. 29734 | 10-AlaGluThrArgArgGlnPheAla-17 |
| SEQ. ID. NO. 29735 | 41-AlaHisGlyArgArgSerAspPheIleArg-50 |
| SEQ. ID. NO. 29736 | 68-ArgAsnHisGluArgPheAspCysArgThrArgPheAsp-80 |
| SEQ. ID. NO. 29737 | 102-ValGlyGlyArgIleGlyGlnGlyGluAspPheProArgAlaGlyIleGlnAsnHisHisArgSerGly-124 |
| SEQ. ID. NO. 29738 | 140-GlnGlyLeuAsnProLeuIleGluGlyLysAspAspVal-152 |
| SEQ. ID. NO. 29739 | 189-PheLysArgLysPhe-193 |
| SEQ. ID. NO. 29740 | 202-AsnIleGlyLysSerAspAspValCysLys-211 |
| Hydrophilic Regions - Hopp-Woods | |
| SEQ. ID. NO. 29741 | 10-AlaGluThrArgArgGlnPheAla-17 |
| SEQ. ID. NO. 29742 | 42-HisGlyArgArgSerAspPheIleArg-50 |
| SEQ. ID. NO. 29743 | 68-ArgAsnHisGluArgPheAspCysArgThrArgPheAsp-80 |
| SEQ. ID. NO. 29744 | 106-IleGlyGlnGlyGluAspPheProArg-114 |
| SEQ. ID. NO. 29745 | 146-IleGluGlyLysAspAspVal-152 |

TABLE 1-continued

| | |
|---|---|
| SEQ. ID. NO. 29746 | 189-PheLysArgLysPhe-193 |
| SEQ. ID. NO. 29747 | 204-GlyLysSerAspAspValCysLys-211 |
| g241-1 | |
| AMPHI Regions - AMPHI | |
| SEQ. ID. NO. 29748 | 6-ThrArgAlaAlaAsnProPro-12 |
| SEQ. ID. NO. 29749 | 35-ThrHisThrProHisGluProAlaSerSer-44 |
| SEQ. ID. NO. 29750 | 109-PheLeuIleGlyCysIleAlaHisAlaPheAsnArgSerPheLys-123 |
| SEQ. ID. NO. 29751 | 126-PheHisAlaCysGlnArgMetValAlaVal-135 |
| SEQ. ID. NO. 29752 | 195-HisPheAspArgIleAlaGlyIleLeuThrValln-206 |
| SEQ. ID. NO. 29753 | 228-GlyPheIleGlnLysLeuIleValGlyIleIleHis-239 |
| Antigenic Index - Jameson-Wolf | |
| SEQ. ID. NO. 29754 | 1-MetProThrArgProThrArgAlaAlaAsnProProThrPro-14 |
| SEQ. ID. NO. 29755 | 22-TyrCysProArgProProTyrArgProProSerValGlnThrHisThrProHisGluProAlaSerSerThrCysAlaAlaLysSerAlaAsnArgArgGlu AsnSerHisAsnAlaGlnPro-62 |
| SEQ. ID. NO. 29756 | 68-ProSerAsnLysMetProSerGluThrGluGlnThrLeuPheArgArgHisGlnIleProProSerCysArgGlnSer-93 |
| SEQ. ID. NO. 29757 | 119-AsnArgSerPheLysAla-124 |
| SEQ. ID. NO. 29758 | 147-ThrIleAspAspAsnIleAla-153 |
| SEQ. ID. NO. 29759 | 161-LysHisHisThrAspLeuAspPheAsnArgGluArgAlaArgIlePheAsnThrAspGlnLeu-181 |
| SEQ. ID. NO. 29760 | 188-ArgIleValGlyArgLysArgHisPheAspArg-198 |
| SEQ. ID. NO. 29761 | 209-PheHisGlnArgGluAsnAla-215 |
| SEQ. ID. NO. 29762 | 244-ArgAsnHisGlyIlePheCysAsnSerHis-253 |
| SEQ. ID. NO. 29763 | 255-CysProPheArgAsnSerArgLeuIle-263 |
| Hydrophilic Regions - Hopp-Woods | |
| SEQ. ID. NO. 29764 | 1-MetProThrArgProThrArgAlaAlaAsn-10 |
| SEQ. ID. NO. 29765 | 37-ThrProHisGluProAlaSer-43 |
| SEQ. ID. NO. 29766 | 46-CysAlaAlaLysSerAlaAsnArgArgGluAsnSerHis-58 |
| SEQ. ID. NO. 29767 | 70-AsnLysMetProSerGluThrGluGlnThrLeuPheArg-82 |
| SEQ. ID. NO. 29768 | 120-ArgSerPheLysAla-124 |
| SEQ. ID. NO. 29769 | 161-LysHisHisThrAspLeuAspPheAsnArgGluArgAlaArgIlePheAsn-177 |
| SEQ. ID. NO. 29770 | 188-ArgIleValGlyArgLysArgHisPheAspArg-198 |
| SEQ. ID. NO. 29771 | 209-PheHisGlnArgGluAsnAla-215 |
| g242 | |
| AMPHI Regions - AMPHI | |
| SEQ. ID. NO. 29772 | 25-ValAlaAlaGlnPheValAspPheValGluGln-35 |
| SEQ. ID. NO. 29773 | 46-HisIleLeuGlnAsn-50 |
| SEQ. ID. NO. 29774 | 100-AlaAspGlnThrGln-104 |
| SEQ. ID. NO. 29775 | 122-AsnProPhePheAspPhePheGlnAlaValVal-132 |
| SEQ. ID. NO. 29776 | 137-HisGlnSerGlyPheGlyAspValPhe-145 |
| SEQ. ID. NO. 29777 | 191-PheGlyHisThrArg-195 |
| SEQ. ID. NO. 29778 | 197-PheAspAlaCysLeu-201 |
| SEQ. ID. NO. 29779 | 262-HisProPheAlaAspPheGlyAsnLeuGlnAsnLeuLeuAlaLeu-276 |
| Antigenic Index - Jameson-Wolf | |
| SEQ. ID. NO. 29780 | 14-PheLysGlnArgAlaGlyGlyIleAla-22 |
| SEQ. ID. NO. 29781 | 33-ValGluGlnGluGlnArgValSer-40 |
| SEQ. ID. NO. 29782 | 54-HisArgAlaAspIleGlyThrAlaValProAla-64 |
| SEQ. ID. NO. 29783 | 73-AlaGlnGlyHisThrAspIlePheProProArgCysPheGlyAspGlyPheAlaGlnArgGlyPheAlaHisAlaArgArgAlaAspGlnThrGlnAsn ArgThrPhe-108 |
| SEQ. ID. NO. 29784 | 137-HisGlnSerGlyPhe-141 |
| SEQ. ID. NO. 29785 | 152-LeuProArgGlnSerGluGlnGlyVal-160 |
| SEQ. ID. NO. 29786 | 164-AlaTyrAspGlyGlyPheGlyArgHisArgArgHisHis-176 |
| SEQ. ID. NO. 29787 | 283-MetArgCysAspArgIleGly-289 |
| Hydrophilic Regions - Hopp-Woods | |
| SEQ. ID. NO. 29788 | 14-PheLysGlnArgAlaGlyGlyIle-21 |
| SEQ. ID. NO. 29789 | 33-ValGluGlnGluGlnArgVal-39 |
| SEQ. ID. NO. 29790 | 54-HisArgAlaAspIle-58 |
| SEQ. ID. NO. 29791 | 95-AlaHisAlaArgArgAlaAspGlnThrGlnAsnArgThrPhe-108 |
| SEQ. ID. NO. 29792 | 154-ArgGlnSerGluGlnGlyVal-160 |
| SEQ. ID. NO. 29793 | 168-GlyPheGlyArgHisArgArgHisHis-176 |
| SEQ. ID. NO. 29794 | 283-MetArgCysAspArgIleGly-289 |
| g243 | |
| AMPHI Regions - AMPHI | |
| SEQ. ID. NO. 29795 | 35-MetThrArgLeuAlaArgLysAlaValGlnArgLeuThrAlaSerHisIleGlnArgPheLeu-55 |
| SEQ. ID. NO. 29796 | 80-AspSerSerArgIleThrSerThrIle-88 |
| Antigenic Index - Jameson-Wolf | |
| SEQ. ID. NO. 29797 | 30-ProSerAsnAlaPro-34 |
| SEQ. ID. NO. 29798 | 37-ArgLeuAlaArgLysAlaValGln-44 |
| SEQ. ID. NO. 29799 | 55-LeuThrGluSerLysThrGlyAlaAsnArgSerSerSerSerCysLysPro-71 |
| SEQ. ID. NO. 29800 | 77-SerAlaSerAspSerSerArgIle-84 |
| SEQ. ID. NO. 29801 | 102-SerThrThrGlyAlaValThrLysSer-110 |
| Hydrophilic Regions - Hopp-Woods | |
| SEQ. ID. NO. 29802 | 37-ArgLeuAlaArgLysAlaValGln-44 |
| SEQ. ID. NO. 29803 | 55-LeuThrGluSerLysThrGlyAlaAsnArgSerSerSerSerCysLys-70 |
| SEQ. ID. NO. 29804 | 78-AlaSerAspSerSerArgIle-84 |
| g244-1 | |
| AMPHI Regions - AMPHI | |
| SEQ. ID. NO. 29805 | 13-IleAlaAlaLeuLeuArg-18 |
| SEQ. ID. NO. 29806 | 24-AsnAlaLeuGlnGluIleAsnGlnIleIleProGlnThr-36 |
| SEQ. ID. NO. 29807 | 76-ArgLeuHisArgLeu-80 |
| SEQ. ID. NO. 29808 | 98-LeuArgGlyIleLysArgLeuLeuGlnLeuIleGlnSerHisLeuHisThrHis-115 |
| SEQ. ID. NO. 29809 | 150-ArgIleGlyAsnPhe-154 |

TABLE 1-continued

| | |
|---|---|
| SEQ. ID. NO. 29810 | 206-CysLeuAspGlyPheHisArgLeuHis-214 |
| SEQ. ID. NO. 29811 | 217-AsnArgPhePheThr-221 |
| SEQ. ID. NO. 29812 | 249-IleArgThrPheSerArgAsnPheLysGln-258 |
| Antigenic Index - Jameson-Wolf | |
| SEQ. ID. NO. 29813 | 1-MetProProGluAlaArgProAlaGlySerAspGly-12 |
| SEQ. ID. NO. 29814 | 20-ValTyrThrGlnAsnAla-25 |
| SEQ. ID. NO. 29815 | 35-GlnThrProSerGly-39 |
| SEQ. ID. NO. 29816 | 43-CysHisArgAsnHisSerArgAlaGlnHis-52 |
| SEQ. ID. NO. 29817 | 81-MetAspIleArgIle-85 |
| SEQ. ID. NO. 29818 | 91-PheArgIleAspPheLeuAsp-97 |
| SEQ. ID. NO. 29819 | 99-ArgGlyIleLysArg-103 |
| SEQ. ID. NO. 29820 | 125-IleGlnLysArgHis-129 |
| SEQ. ID. NO. 29821 | 134-LeuAspArgGlnHisPheHisGlyLysLeuLeuSerGlyGluLeuValArg-150 |
| SEQ. ID. NO. 29822 | 178-PheGlnLeuGlyAsnProArgLeu-185 |
| SEQ. ID. NO. 29823 | 191-ArgLeuGlyGlySer-195 |
| SEQ. ID. NO. 29824 | 234-LeuLysThrAsnTrpLysSerLysSerGlyTyrTyrProSerLysIleArgThrPheSerArgAsnPheLysGlnArgGlnGluIleSerHisProProPro AsnThrLeuProGlnLysProTyrLysArg-277 |
| Hydrophilic Regions - Hopp-Woods | |
| SEQ. ID. NO. 29825 | 1-MetProProGluAlaArgProAlaGlySerAspGly-12 |
| SEQ. ID. NO. 29826 | 45-ArgAsnHisSerArgAlaGlnHis-52 |
| SEQ. ID. NO. 29827 | 81-MetAspIleArgIle-85 |
| SEQ. ID. NO. 29828 | 91-PheArgIleAspPheLeuAsp-97 |
| SEQ. ID. NO. 29829 | 99-ArgGlyIleLysArg-103 |
| SEQ. ID. NO. 29830 | 236-ThrAsnTrpLysSerLysSer-242 |
| SEQ. ID. NO. 29831 | 248-LysIleArgThrPheSerArgAsnPheLysGlnArgGlnGluIleSerHis-264 |
| SEQ. ID. NO. 29832 | 273-LysProTyrLysArg-277 |
| g246 | |
| AMPHI Regions - AMPHI | |
| SEQ. ID. NO. 29833 | 39-AlaValAsnIleAla-43 |
| SEQ. ID. NO. 29834 | 55-HisValValCysLysArgCysAlaGluValLeuValGluGlnPheAlaAspLeuPhePhe-74 |
| SEQ. ID. NO. 29835 | 83-AspMetGlyArgPhe-87 |
| SEQ. ID. NO. 29836 | 132-PheGlyCysAspAspValValAspAsnLeuAlaGlyPheGlyArgGlyPheArgPro-150 |
| Antigenic Index - Jameson-Wolf | |
| SEQ. ID. NO. 29837 | 1-MetTyrGlyArgAsnGlySerThrGln-9 |
| SEQ. ID. NO. 29838 | 17-AspGlnThrGlnArgAlaArgPheGlyAsnGlyGluVal-29 |
| SEQ. ID. NO. 29839 | 46-PheAlaGlyGluSerGlyGln-52 |
| SEQ. ID. NO. 29840 | 57-ValCysLysArgCysAla-62 |
| SEQ. ID. NO. 29841 | 78-AspCysGlyHisHisAspMetGlyArg-86 |
| SEQ. ID. NO. 29842 | 92-LeuAspAspLysLeuAla-97 |
| SEQ. ID. NO. 29843 | 133-GlyCysAspAspValValAsp-139 |
| SEQ. ID. NO. 29844 | 143-GlyPheGlyArgGlyPheArgProVal-151 |
| SEQ. ID. NO. 29845 | 165-LeuGlnGlnArgGly-169 |
| Hydrophilic Regions - Hopp-Woods | |
| SEQ. ID. NO. 29846 | 18-GlnThrGlnArgAlaArgPheGlyAsn-26 |
| SEQ. ID. NO. 29847 | 47-AlaGlyGluSerGly-51 |
| SEQ. ID. NO. 29848 | 57-ValCysLysArgCysAla-62 |
| SEQ. ID. NO. 29849 | 92-LeuAspAspLysLeuAla-97 |
| g247-1 | |
| AMPHI Regions - AMPHI | |
| SEQ. ID. NO. 29850 | 34-GlyPheIleGlnArgLeu-39 |
| SEQ. ID. NO. 29851 | 59-ValValSerSerCysSerLysIleAlaLysProGlyLysLysIleSerThrLeuGlnGlu-78 |
| SEQ. ID. NO. 29852 | 105-TyrAlaValGlyArgPheGlyAsn-112 |
| SEQ. ID. NO. 29853 | 164-ArgTyrThrAsnLysPheAspLysSerLys-173 |
| Antigenic Index - Jameson-Wolf | |
| SEQ. ID. NO. 29854 | 1-ProGlyAlaLysGlnGluAsnProLeuPheSerLeuLysArgSerGlyMetAspLysGlnLeu-21 |
| SEQ. ID. NO. 29855 | 26-GluSerIleAspIleLysTyr-32 |
| SEQ. ID. NO. 29856 | 48-IleAspAspLeuAspAlaSerAla-55 |
| SEQ. ID. NO. 29857 | 62-SerCysSerLysIleAlaLysProGlyLysLysIleSerThrLeuGlnGluAlaLysSer-81 |
| SEQ. ID. NO. 29858 | 85-IleThrAsnAspAspLysGlnAsnGlyAsnIleThrArgGlnLysHis-100 |
| SEQ. ID. NO. 29859 | 109-ArgPheGlyAsnAsnGluGluSerLeu-117 |
| SEQ. ID. NO. 29860 | 120-PheGlnLeuAspAspLysGlyLysTrpGlyAsn-130 |
| SEQ. ID. NO. 29861 | 136-LysLysValLysArgMetAspVal-143 |
| SEQ. ID. NO. 29862 | 149-SerGlyCysProGluAspGluAspAlaGlyLysGluGluLysPheArgTyrThrAsnLysPheAspLysSerLysAsnAlaValThr-177 |
| SEQ. ID. NO. 29863 | 193-IleAlaAlaSerSerAspAsnSer-200 |
| SEQ. ID. NO. 29864 | 210-IleArgGlyGlyAsnValCysAlaAsnArgThrLeu-221 |
| Hydrophilic Regions - Hopp-Woods | |
| SEQ. ID. NO. 29865 | 1-ProGlyAlaLysGlnGluAsn-7 |
| SEQ. ID. NO. 29866 | 11-SerLeuLysArgSerGlyMetAspLysGlnLeu-21 |
| SEQ. ID. NO. 29867 | 26-GluSerIleAspIleLys-31 |
| SEQ. ID. NO. 29868 | 48-IleAspAspLeuAspAlaSerAla-55 |
| SEQ. ID. NO. 29869 | 64-SerLysIleAlaLysProGlyLysLysIleSerThr-75 |
| SEQ. ID. NO. 29870 | 77-GlnGluAlaLysSer-81 |
| SEQ. ID. NO. 29871 | 86-ThrAsnAspAspLysGlnAsnGlyAsnIleThrArgGlnLysHis-100 |
| SEQ. ID. NO. 29872 | 111-GlyAsnAsnGluGluSerLeu-117 |
| SEQ. ID. NO. 29873 | 121-GlnLeuAspAspLysGlyLysTrpGly-129 |
| SEQ. ID. NO. 29874 | 136-LysLysValLysArgMetAspVal-143 |

TABLE 1-continued

| | |
|---|---|
| SEQ. ID. NO. 29875 | 151-CysProGluAspGluAspAlaGlyLysGluGluLysPheArgTyr-165 |
| SEQ. ID. NO. 29876 | 167-AsnLysPheAspLysSerLysAsnAlaVal-176 |
| SEQ. ID. NO. 29877 | 193-IleAlaAlaSerSerAspAsn-199 |
| g248-1 | |
| AMPHI Regions - AMPHI | |
| SEQ. ID. NO. 29878 | 87-SerGluAsnCysGluLysGlyLeu-94 |
| SEQ. ID. NO. 29879 | 109-GluAlaPheGlyAsn-113 |
| SEQ. ID. NO. 29880 | 122-ValGluAlaValLysArg-127 |
| SEQ. ID. NO. 29881 | 153-AlaAlaGlyValSerLysMetProArgTyrIleIleGlu-165 |
| SEQ. ID. NO. 29882 | 173-GlnAsnValTyrArgValThrAlaLysAlaTrpGlyLysAsn-186 |
| Antigenic Index - Jameson-Wolf | |
| SEQ. ID. NO. 29883 | 1-MetArgLysGlnAsnThrLeuThr-8 |
| SEQ. ID. NO. 29884 | 11-ProThrSerAspGlyGlnArgGlySer-19 |
| SEQ. ID. NO. 29885 | 40-GlnSerTyrAsnThrGluGlnArgIleSerAlaAsnGluSerAspArgLysLeuAla-58 |
| SEQ. ID. NO. 29886 | 64-AlaAlaLeuArgGluGlyGluPheGln-72 |
| SEQ. ID. NO. 29887 | 78-TyrAlaAlaAspSerLysValThrPheSerGluAsnCysGluLysGlyLeu-94 |
| SEQ. ID. NO. 29888 | 101-ArgThrAsnAsnAsnGlySerGluGluAlaPhe-111 |
| SEQ. ID. NO. 29889 | 118-GlyLysProAlaValGluAlaValLysArgSerCysProAlaLysSerGlyLysAsnSerThr-138 |
| SEQ. ID. NO. 29890 | 140-LeuCysIleAspAsnLysGlyMetGluTyrAsnLysGlyAlaAlaGlyValSerLysMetProArgTyrIle-163 |
| SEQ. ID. NO. 29891 | 168-GlyValLysAsnGlyGlnAsnVal-175 |
| SEQ. ID. NO. 29892 | 182-AlaTrpGlyLysAsnAlaAsnThr-189 |
| SEQ. ID. NO. 29893 | 197-ValGlyAsnAsnAspGluGln-203 |
| Hydrophilic Regions - Hopp-Woods | |
| SEQ. ID. NO. 29894 | 1-MetArgLysGlnAsnThr-6 |
| SEQ. ID. NO. 29895 | 11-ProThrSerAspGlyGlnArgGly-18 |
| SEQ. ID. NO. 29896 | 42-TyrAsnThrGluGlnArgIleSerAlaAsnGluSerAspArgLysLeuAla-58 |
| SEQ. ID. NO. 29897 | 64-AlaAlaLeuArgGluGlyGluPheGln-72 |
| SEQ. ID. NO. 29898 | 78-TyrAlaAlaAspSerLysValThrPhe-86 |
| SEQ. ID. NO. 29899 | 88-GluAsnCysGluLysGlyLeu-94 |
| SEQ. ID. NO. 29900 | 101-ArgThrAsnAsnAsnGlySerGluGluAlaPhe-111 |
| SEQ. ID. NO. 29901 | 120-ProAlaValGluAlaValLysArgSerCysProAlaLysSerGlyLysAsnSerThr-138 |
| SEQ. ID. NO. 29902 | 140-LeuCysIleAspAsnLysGlyMetGluTyrAsnLys-151 |
| SEQ. ID. NO. 29903 | 199-AsnAsnAspGluGln-203 |
| g249-1 | |
| AMPHI Regions - AMPHI | |
| SEQ. ID. NO. 29904 | 6-CysLeuArgLeuLys-10 |
| SEQ. ID. NO. 29905 | 15-GlyMetAlaLeuIleGluValLeuVal-23 |
| SEQ. ID. NO. 29906 | 42-ThrValAlaSerValArgGluAla-49 |
| SEQ. ID. NO. 29907 | 53-ThrIleValSerGlnIleThrGlnAsnLeuMetGluGlyMet-66 |
| SEQ. ID. NO. 29908 | 111-GluGlnLeuLysArgPheSerHisGluLeuLysAsnAlaLeu-124 |
| Antigenic Index - Jameson-Wolf | |
| SEQ. ID. NO. 29909 | 1-MetLysAsnAsnAspCysLeuArgLeuLysAsnProGlnSerGly-15 |
| SEQ. ID. NO. 29910 | 44-AlaSerValArgGluAlaGluThr-51 |
| SEQ. ID. NO. 29911 | 70-ProThrIleAspLeuAspSerAsnLysLysAsnTyr-81 |
| SEQ. ID. NO. 29912 | 85-MetGlyLysGlnThr-89 |
| SEQ. ID. NO. 29913 | 93-ValAspGlyGluPhe-97 |
| SEQ. ID. NO. 29914 | 99-LeuAspAlaGluLysSerLysAlaGlnLeuAlaGluGluGlnLeuLysArgPheSerHisGluLeuLysAsnAlaLeu-124 |
| SEQ. ID. NO. 29915 | 134-ValCysLysAspSerSerGlyAspAlaProThrLeuSerAspSerGlyAlaPheSerSerAsnCysAspAsnLysAlaAsnGlyAspThrLeu-164 |
| SEQ. ID. NO. 29916 | 172-AspSerAlaGlyAspSerAspIleSerArgThrAsnLeuGluValSerGlyAspAsn-190 |
| SEQ. ID. NO. 29917 | 197-AlaArgValGlyGlyArgGlu-203 |
| Hydrophilic Regions - Hopp-Woods | |
| SEQ. ID. NO. 29918 | 1-MetLysAsnAsnAspCysLeuArgLeuLysAsnProGln-13 |
| SEQ. ID. NO. 29919 | 44-AlaSerValArgGluAlaGluThr-51 |
| SEQ. ID. NO. 29920 | 72-IleAspLeuAspSerAsnLysLysAsnTyr-81 |
| SEQ. ID. NO. 29921 | 99-LeuAspAlaGluLysSerLysAlaGlnLeuAlaGluGluGlnLeuLysArgPheSerHisGluLeuLysAsnAlaLeu-124 |
| SEQ. ID. NO. 29922 | 134-ValCysLysAspSerSerGlyAspAlaProThrLeuSerAsp-147 |
| SEQ. ID. NO. 29923 | 154-AsnCysAspAsnLysAlaAsnGly-161 |
| SEQ. ID. NO. 29924 | 173-SerAlaGlyAspSerAspIleSerArgThrAsnLeu-184 |
| SEQ. ID. NO. 29925 | 199-ValGlyGlyArgGlu-203 |
| g250 | |
| AMPHI Regions - AMPHI | |
| SEQ. ID. NO. 29926 | 10-GluPheIleArgGlyIleLysGlu-17 |
| SEQ. ID. NO. 29927 | 54-PheAlaGlyGlySerGlu-59 |
| SEQ. ID. NO. 29928 | 61-AlaThrValAsnLeuTrpAlaGluPro-69 |
| Antigenic Index - Jameson-Wolf | |
| SEQ. ID. NO. 29929 | 3-HisThrAlaSerProArgAspGluPheIleArgGlyIleLysGluSerSerPro-20 |
| SEQ. ID. NO. 29930 | 34-MetGlnGlyGlyGlnLysGlyMetGlyArgLeu-44 |
| SEQ. ID. NO. 29931 | 54-PheAlaGlyGlySerGlu-59 |
| SEQ. ID. NO. 29932 | 83-AsnSerArgHisIleLeuMetGlyGlyGly-92 |
| SEQ. ID. NO. 29933 | 95-HisAlaHisGluArgAsnThrAlaGluLysSerArgAlaArg-108 |
| Hydrophilic Regions - Hopp-Woods | |
| SEQ. ID. NO. 29934 | 5-AlaSerProArgAspGluPheIleArgGlyIleLysGluSerSer-19 |
| SEQ. ID. NO. 29935 | 36-GlyGlyGlnLysGlyMetGlyArg-43 |
| SEQ. ID. NO. 29936 | 95-HisAlaHisGluArgAsnThrAlaGluLysSerArgAlaArg-108 |
| g251 | |
| AMPHI Regions - AMPHI | |
| SEQ. ID. NO. 29937 | 57-ValAlaAspPheGlyGlyIleGluGlyPhe-66 |
| SEQ. ID. NO. 29938 | 101-ArgThrValGlyGlyThrValArgLeuLeuLysMetIle-113 |
| SEQ. ID. NO. 29939 | 156-AlaArgThrValPheArgAlaHisLeuArg-165 |
| SEQ. ID. NO. 29940 | 179-AlaAlaArgValPheAlaValAla-186 |

TABLE 1-continued

| | |
|---|---|
| SEQ. ID. NO. 29941 | 200-LeuGlyGlnGluCysArg-205 |
| SEQ. ID. NO. 29942 | 207-ArgHisIleAlaArgValGluSerLeuLeuArgAlaPheGluTyrAla-222 |
| Antigenic Index - Jameson-Wolf | |
| SEQ. ID. NO. 29943 | 21-LeuArgGlyArgPheGlnArg-27 |
| SEQ. ID. NO. 29944 | 48-ValValThrGluValAspAla-54 |
| SEQ. ID. NO. 29945 | 90-ArgLeuValGlyThr-94 |
| SEQ. ID. NO. 29946 | 120-ProValValArgGluAlaGlyIle-127 |
| SEQ. ID. NO. 29947 | 153-ValLysHisAlaArgThrValPhe-160 |
| SEQ. ID. NO. 29948 | 196-IleLysAsnArgLeuGlyGlnGluCysArgAsnArgHisIleAlaArgValGluSerLeu-215 |
| SEQ. ID. NO. 29949 | 231-LysThrLysThrArgAlaGluGlnProArgProAla-242 |
| Hydrophilic Regions - Hopp-Woods | |
| SEQ. ID. NO. 29950 | 23-GlyArgPheGlnArg-27 |
| SEQ. ID. NO. 29951 | 48-ValValThrGluValAspAla-54 |
| SEQ. ID. NO. 29952 | 120-ProValValArgGluAlaGlyIle-127 |
| SEQ. ID. NO. 29953 | 153-ValLysHisAlaArgThrValPhe-160 |
| SEQ. ID. NO. 29954 | 198-AsnArgLeuGlyGlnGluCysArgAsnArgHisIleAlaArgValGluSerLeu-215 |
| SEQ. ID. NO. 29955 | 232-ThrLysThrArgAlaGluGlnProArg-240 |
| g254 | |
| AMPHI Regions - AMPHI | |
| SEQ. ID. NO. 29956 | 6-ArgPheAsnThrTyrSerHis-12 |
| SEQ. ID. NO. 29957 | 32-GlyHisGlyAspGlyTyrArg-38 |
| SEQ. ID. NO. 29958 | 66-LysLeuLysSerIleLeuLys-72 |
| SEQ. ID. NO. 29959 | 142-ValLeuAlaValMetLysSerLeuThrAlaSer-152 |
| Antigenic Index - Jameson-Wolf | |
| SEQ. ID. NO. 29960 | 5-GluArgPheAsnThrTyrSer-11 |
| SEQ. ID. NO. 29961 | 32-GlyHisGlyAspGlyTyrArg-38 |
| SEQ. ID. NO. 29962 | 65-GlyLysLeuLysSerIleLeuLysLysThrAspHis-76 |
| SEQ. ID. NO. 29963 | 94-SerLeuArgAsnGlyProGly-100 |
| SEQ. ID. NO. 29964 | 120-ThrIleGlyArgLysSerGluLysArgLeuLeu-130 |
| SEQ. ID. NO. 29965 | 177-AsnAspGluLysIleArgHisGlyHisGly-186 |
| Hydrophilic Regions - Hopp-Woods | |
| SEQ. ID. NO. 29966 | 65-GlyLysLeuLysSerIleLeuLysLysThrAspHis-76 |
| SEQ. ID. NO. 29967 | 120-ThrIleGlyArgLysSerGluLysArgLeuLeu-130 |
| SEQ. ID. NO. 29968 | 177-AsnAspGluLysIleArgHis-183 |
| g255 | |
| AMPHI Regions - AMPHI | |
| SEQ. ID. NO. 29969 | 23-ValLysThrCysAlaAspPheHisAlaPheAspGlyValAspAlaHisHisArg-40 |
| SEQ. ID. NO. 29970 | 71-GlyIleGlnGlyPheAlaHis-77 |
| Antigenic Index - Jameson-Wolf | |
| SEQ. ID. NO. 29971 | 33-AspGlyValAspAlaHisHisArgValGlyAspPheGlyIleGluAlaValGluAsnGlyPheAlaGlnThrAspGlyAspValGlyGly-62 |
| SEQ. ID. NO. 29972 | 67-PheArgAlaAspGlyIleGlnGly-74 |
| SEQ. ID. NO. 29973 | 91-ValGlyGlyLysLysArgIleLeu-98 |
| SEQ. ID. NO. 29974 | 115-GlyAsnValGlyGlyAspPheArgAla-123 |
| SEQ. ID. NO. 29975 | 130-PhePheGlyAsnGlySerGlyGlyAsnAlaGly-140 |
| SEQ. ID. NO. 29976 | 145-GlyGlyThrProAla-149 |
| SEQ. ID. NO. 29977 | 168-SerGlyAlaGluGlyGlyGlyAspVal-176 |
| Hydrophilic Regions - Hopp-Woods | |
| SEQ. ID. NO. 29978 | 33-AspGlyValAspAlaHisHisArgValGlyAspPheGly-45 |
| SEQ. ID. NO. 29979 | 56-ThrAspGlyAspValGlyGly-62 |
| SEQ. ID. NO. 29980 | 67-PheArgAlaAspGly-71 |
| SEQ. ID. NO. 29981 | 92-GlyGlyLysLysArgIleLeu-98 |
| SEQ. ID. NO. 29982 | 119-GlyAspPheArgAla-123 |
| SEQ. ID. NO. 29983 | 169-GlyAlaGluGlyGlyGly-174 |
| g256-1 | |
| AMPHI Regions - AMPHI | |
| SEQ. ID. NO. 29984 | 22-AlaLysPheLeuGlnHisPro-28 |
| SEQ. ID. NO. 29985 | 95-HisPheArgSerCysGlyGlyValAla-103 |
| SEQ. ID. NO. 29986 | 128-ArgTyrArgGluIleTyrAlaVal-135 |
| SEQ. ID. NO. 29987 | 143-AlaProAlaLysTyrLeuGlyGluGln-151 |
| SEQ. ID. NO. 29988 | 179-GlyIleThrArgLeuLeu-184 |
| SEQ. ID. NO. 29989 | 198-ArgSerLeuGlnGlyPheGlnThrAla-206 |
| SEQ. ID. NO. 29990 | 208-AlaAlaGlyCysLysThrLeuGlyGluPheAspAspArgPheThrAlaProLeuHisGly-227 |
| SEQ. ID. NO. 29991 | 234-TyrTyrArgGlnThrSerCysLysProLeuLeuLysHisValAla-248 |
| Antigenic Index - Jameson-Wolf | |
| SEQ. ID. NO. 29992 | 4-ThrProProAspThrProPhe-10 |
| SEQ. ID. NO. 29993 | 12-LeuArgAsnGlyAsnAlaAspThrIleAla-21 |
| SEQ. ID. NO. 29994 | 27-HisProAlaProAlaTyrArgArgGluMetLeuProAspSerThrGlyLysThrLysThrAlaTyr-48 |
| SEQ. ID. NO. 29995 | 51-SerAlaGlyGlyIleSerProAspAlaPro-60 |
| SEQ. ID. NO. 29996 | 68-LeuGluGlySerSerArgSerHisTyr-76 |
| SEQ. ID. NO. 29997 | 84-ValArgAsnArgGlyTrpHis-90 |
| SEQ. ID. NO. 29998 | 98-SerCysGlyGlyValAlaAsn-104 |
| SEQ. ID. NO. 29999 | 113-GlyAspThrAlaGlu-117 |
| SEQ. ID. NO. 30000 | 125-LeuThrAlaArgTyrArgGlu-131 |
| SEQ. ID. NO. 30001 | 140-GlyGlyAsnAlaProAlaLysTyrLeuGlyGluGlnGlyLysLysAlaLeuPro-157 |
| SEQ. ID. NO. 30002 | 167-ValAspAlaGluAlaAlaGlySerArgPheAspSerGlyIle-180 |
| SEQ. ID. NO. 30003 | 193-LeuIleProLysAlaArgSerLeuGln-201 |
| SEQ. ID. NO. 30004 | 213-ThrLeuGlyGluPheAspAspArgPheThr-222 |
| SEQ. ID. NO. 30005 | 228-PheAlaAspArgHisAspTyrTyrArgGlnThrSerCysLysProLeuLeu-244 |
| SEQ. ID. NO. 30006 | 259-AspProPheLeuProProGluAlaLeuProArgAlaAspGluAlaSerGlu-275 |
| SEQ. ID. NO. 30007 | 283-AlaHisGlyGlyHis-287 |

TABLE 1-continued

| | |
|---|---|
| SEQ. ID. NO. 30008 | 292-SerSerThrGlyGlyArgLeu-298 |
| SEQ. ID. NO. 30009 | 312-AspSerPheArgThrAsnArgArg-319 |
| Hydrophilic Regions - Hopp-Woods | |
| SEQ. ID. NO. 30010 | 31-AlaTyrArgArgGluMetLeuPro-38 |
| SEQ. ID. NO. 30011 | 40-SerThrGlyLysThrLysThr-46 |
| SEQ. ID. NO. 30012 | 69-GluGlySerSerArgSer-74 |
| SEQ. ID. NO. 30013 | 84-ValArgAsnArgGly-88 |
| SEQ. ID. NO. 30014 | 125-LeuThrAlaArgTyrArgGlu-131 |
| SEQ. ID. NO. 30015 | 147-TyrLeuGlyGluGlnGlyLysLysAlaLeuPro-157 |
| SEQ. ID. NO. 30016 | 167-ValAspAlaGluAlaAlaGlySerArgPheAspSerGlyIle-180 |
| SEQ. ID. NO. 30017 | 193-LeuIleProLysAlaArgSer-199 |
| SEQ. ID. NO. 30018 | 213-ThrLeuGlyGluPheAspAspArgPheThr-222 |
| SEQ. ID. NO. 30019 | 228-PheAlaAspArgHisAspTyrTyrArg-236 |
| SEQ. ID. NO. 30020 | 266-AlaLeuProArgAlaAspGluAlaSerGlu-275 |
| SEQ. ID. NO. 30021 | 314-PheArgThrAsnArgArg-319 |
| g257 | |
| AMPHI Regions - AMPHI | |
| SEQ. ID. NO. 30022 | 24-SerPheLeuProAsn-28 |
| SEQ. ID. NO. 30023 | 73-AspLeuValAsnLysValLeuAlaGluValAlaArgLeuGluLysMetPhe-89 |
| SEQ. ID. NO. 30024 | 109-SerProProAlaAspPheLeuGluLeuLeuSerLeuAlaAlaIlePheThr-125 |
| Antigenic Index - Jameson-Wolf | |
| SEQ. ID. NO. 30025 | 1-MetGlyArgHisPheGlyArgArgArgPheLeu-11 |
| SEQ. ID. NO. 30026 | 32-AlaGlyGlyGluLysArgAsnMetAspLysLysArgAspGluAsn-46 |
| SEQ. ID. NO. 30027 | 56-GlySerGlyAlaGlu-60 |
| SEQ. ID. NO. 30028 | 65-GlyValAspAspArgGlnAlaAla-72 |
| SEQ. ID. NO. 30029 | 83-AlaArgLeuGluLys-87 |
| SEQ. ID. NO. 30030 | 92-TyrArgGluAspSerLeuIleSerArgLeuAsnArgAspGlyTyrLeuThrSerProProAlaAspPhe-114 |
| Hydrophilic Regions - Hopp-Woods | |
| SEQ. ID. NO. 30031 | 4-HisPheGlyArgArgArgPheLeu-11 |
| SEQ. ID. NO. 30032 | 33-GlyGlyGluLysArgAsnMetAspLysLysArgAspGluAsn-46 |
| SEQ. ID. NO. 30033 | 65-GlyValAspAspArgGlnAlaAla-72 |
| SEQ. ID. NO. 30034 | 83-AlaArgLeuGluLys-87 |
| SEQ. ID. NO. 30035 | 92-TyrArgGluAspSerLeuIle-98 |
| SEQ. ID. NO. 30036 | 100-ArgLeuAsnArgAspGlyTyr-106 |
| g259-1 | |
| Antigenic Index - Jameson-Wolf | |
| SEQ. ID. NO. 30037 | 34-LysAlaTyrThrGluGluLeuProPro-42 |
| SEQ. ID. NO. 30038 | 62-ValArgSerLysAlaLysAlaGluLysPheTyrArgGluLysMetIleGln-78 |
| SEQ. ID. NO. 30039 | 93-LeuGluHisLysPro-97 |
| SEQ. ID. NO. 30040 | 105-LysAsnHisGlyLysGlyMetAlaGluGlnValArgPheLysAla-119 |
| SEQ. ID. NO. 30041 | 121-ValLeuProAspAspGluAspAlaArgThrIleAla-132 |
| SEQ. ID. NO. 30042 | 144-GlyThrAspAlaValAlaSerGlyGluThrTyrGlyArgVal-157 |
| Hydrophilic Regions - Hopp-Woods | |
| SEQ. ID. NO. 30043 | 35-AlaTyrThrGluGluLeuPro-41 |
| SEQ. ID. NO. 30044 | 62-ValArgSerLysAlaLysAlaGluLysPheTyrArgGluLysMetIleGln-78 |
| SEQ. ID. NO. 30045 | 93-LeuGluHisLysPro-97 |
| SEQ. ID. NO. 30046 | 106-AsnHisGlyLysGlyMetAlaGluGlnValArgPheLysAla-119 |
| SEQ. ID. NO. 30047 | 121-ValLeuProAspAspGluAspAlaArgThrIleAla-132 |
| g260 | |
| AMPHI Regions - AMPHI | |
| SEQ. ID. NO. 30048 | 12-ProPhePheSerLeuPheArgAlaLeuPheGlu-22 |
| SEQ. ID. NO. 30049 | 53-PheIleAspSerValGlyGlnIleThrAlaArgPhePheGlnAlaPhe-68 |
| SEQ. ID. NO. 30050 | 151-GlnTyrLeuAlaArgIleAsnGlnValGlyIleValAspLeuIleProValArg-168 |
| SEQ. ID. NO. 30051 | 177-ThrGlyCysThrGlyIleCysProLysTyrProThrGlyCysArgPro-192 |
| Antigenic Index - Jameson-Wolf | |
| SEQ. ID. NO. 30052 | 30-GlyAlaHisAspAlaAlaGlu-36 |
| SEQ. ID. NO. 30053 | 80-ProAlaPheArgAlaArgGluGlnAlaArgArgGlySerGly-93 |
| SEQ. ID. NO. 30054 | 97-GlyAsnAspLeuArgValLeuHisLysAspAlaValGluValAspIleAspGlyGlyAsnThrVal-118 |
| SEQ. ID. NO. 30055 | 126-ThrAspPheAspAspGlyAspAla-133 |
| SEQ. ID. NO. 30056 | 139-AlaGluAlaArgPhe-143 |
| SEQ. ID. NO. 30057 | 166-ProValArgAlaProGlnGlyGlyThrIle-175 |
| SEQ. ID. NO. 30058 | 183-CysProLysTyrProThrGlyCysArgProVal-193 |
| Hydrophilic Regions - Hopp-Woods | |
| SEQ. ID. NO. 30059 | 30-GlyAlaHisAspAlaAlaGlu-36 |
| SEQ. ID. NO. 30060 | 82-PheArgAlaArgGluGlnAlaArgArgGlySer-92 |
| SEQ. ID. NO. 30061 | 98-AsnAspLeuArgValLeuHisLysAspAlaValGluValAspIleAspGly-114 |
| SEQ. ID. NO. 30062 | 126-ThrAspPheAspAspGlyAspAla-133 |
| SEQ. ID. NO. 30063 | 139-AlaGluAlaArgPhe-143 |
| g261 | |
| AMPHI Regions - AMPHI | |
| SEQ. ID. NO. 30064 | 19-PheThrPheGlnThr-23 |
| SEQ. ID. NO. 30065 | 32-AspThrAlaArgAlaPheAlaAlaAla-40 |
| SEQ. ID. NO. 30066 | 50-GlyLeuPheAlaAspVal-55 |
| SEQ. ID. NO. 30067 | 138-ValHisLysGlyIleGlyAsnAlaValValGlyGlyPheAsp-151 |
| SEQ. ID. NO. 30068 | 164-GlyValValArgAsnLeu-169 |
| SEQ. ID. NO. 30069 | 203-GluGlyAspGlyLeuAspValPheAlaProVal-213 |
| SEQ. ID. NO. 30070 | 217-CysLeuAsnGlnAlaGlyGly-223 |
| Antigenic Index - Jameson-Wolf | |
| SEQ. ID. NO. 30071 | 13-AlaArgSerAspGly-17 |
| SEQ. ID. NO. 30072 | 23-ThrPheArgGlnProAla-28 |

TABLE 1-continued

| | |
|---|---|
| SEQ. ID. NO. 30073 | 40-AlaAlaAspAspThrLeu-45 |
| SEQ. ID. NO. 30074 | 62-ValArgGlnArgProArgLeuArgLeu-70 |
| SEQ. ID. NO. 30075 | 74-HisGlnArgArgValAspLeu-80 |
| SEQ. ID. NO. 30076 | 86-ArgGlnIleLysGlyAsnValHisGlyPheAspGluHisAla-99 |
| SEQ. ID. NO. 30077 | 111-AlaHisAlaArgAspAspValProAsp-119 |
| SEQ. ID. NO. 30078 | 122-ProPheGlyLysAsnGlyGlyValLysGlnGluLysArgValThrProVal-138 |
| SEQ. ID. NO. 30079 | 149-GlyPheAspGlyGlyGlyPheAspGlyGlyGly-159 |
| SEQ. ID. NO. 30080 | 183-GlnIleLeuArgAspProLeuCysAla-191 |
| SEQ. ID. NO. 30081 | 201-ValSerGluGlyAspGlyLeuAsp-208 |
| SEQ. ID. NO. 30082 | 219-AsnGlnAlaGlyGlyArgIleLeuThrAlaArgGluAspAspGlnGlyPhe-235 |
| Hydrophilic Regions - Hopp-Woods | |
| SEQ. ID. NO. 30083 | 13-AlaArgSerAspGly-17 |
| SEQ. ID. NO. 30084 | 40-AlaAlaAspAspThrLeu-45 |
| SEQ. ID. NO. 30085 | 62-ValArgGlnArgProArgLeuArgLeu-70 |
| SEQ. ID. NO. 30086 | 74-HisGlnArgArgValAspLeu-80 |
| SEQ. ID. NO. 30087 | 94-GlyPheAspGluHisAla-99 |
| SEQ. ID. NO. 30088 | 112-HisAlaArgAspAspValProAsp-119 |
| SEQ. ID. NO. 30089 | 127-GlyGlyValLysGlnGluLysArgValThrPro-137 |
| SEQ. ID. NO. 30090 | 202-SerGluGlyAspGlyLeu-207 |
| SEQ. ID. NO. 30091 | 226-LeuThrAlaArgGluAspAspGlnGly-234 |
| g263 | |
| AMPHI Regions - AMPHI | |
| SEQ. ID. NO. 30092 | 32-AsnLeuIleGlyValLeuAlaAsnAla-40 |
| SEQ. ID. NO. 30093 | 42-GluAlaLeuAlaPheTyrGlnGluValGlyLysLeuAsnAlaAlaAsnSerLeuThr-60 |
| SEQ. ID. NO. 30094 | 65-GluValIleArgIle-69 |
| SEQ. ID. NO. 30095 | 86-LysLeuAlaThrLeuLysLys-92 |
| SEQ. ID. NO. 30096 | 100-AsnAlaAlaArgAlaLeu-105 |
| SEQ. ID. NO. 30097 | 115-LeuGlyAlaLeuAlaAlaPheThrGln-123 |
| SEQ. ID. NO. 30098 | 137-LeuAsnAlaPheLeuGluAla-143 |
| SEQ. ID. NO. 30099 | 157-ValAlaLeuAlaThrLeuCysAsnTyrAlaAsnAsnLeuAla-170 |
| Antigenic Index - Jameson-Wolf | |
| SEQ. ID. NO. 30100 | 10-GluThrAlaProGluAlaAlaLysProArgValGluAlaValProLysAsnAsnGlyPhe-29 |
| SEQ. ID. NO. 30101 | 62-GlyGluValGluVal-66 |
| SEQ. ID. NO. 30102 | 73-ArgThrAsnGlnCysSer-78 |
| SEQ. ID. NO. 30103 | 97-GlnSerLeuAsnAla-101 |
| SEQ. ID. NO. 30104 | 108-GlyLysSerAspAspAlaLysLeu-115 |
| SEQ. ID. NO. 30105 | 126-MetAlaLysLysGlyAlaValSerAspAspGluLeu-137 |
| SEQ. ID. NO. 30106 | 144-GlyTyrAsnArgGlnGlnAla-150 |
| SEQ. ID. NO. 30107 | 172-ThrGluIleAsnProLysLeu-178 |
| Hydrophilic Regions - Hopp-Woods | |
| SEQ. ID. NO. 30108 | 11-ThrAlaProGluAlaAlaLysProArgValGluAlaValProLys-25 |
| SEQ. ID. NO. 30109 | 62-GlyGluValGluVal-66 |
| SEQ. ID. NO. 30110 | 97-GlnSerLeuAsnAla-101 |
| SEQ. ID. NO. 30111 | 108-GlyLysSerAspAspAlaLysLeu-115 |
| SEQ. ID. NO. 30112 | 126-MetAlaLysLysGlyAlaValSerAspAspGluLeu-137 |
| g264 | |
| AMPHI Regions - AMPHI | |
| SEQ. ID. NO. 30113 | 28-ValValLysProGluLys-33 |
| SEQ. ID. NO. 30114 | 40-ArgSerTyrLysValAlaGluPheThrGlnThrGly-51 |
| SEQ. ID. NO. 30115 | 85-IleProSerHisValArgVal-91 |
| SEQ. ID. NO. 30116 | 113-AsnArgIleIleAspValSer-119 |
| SEQ. ID. NO. 30117 | 172-LeuAsnGlnAlaAlaGlnAsnPhe-179 |
| Antigenic Index - Jameson-Wolf | |
| SEQ. ID. NO. 30118 | 27-AlaValValLysProGluLysLeuHisAlaSerAlaAsnArgSerTyrLys-43 |
| SEQ. ID. NO. 30119 | 48-ThrGlnThrGlyAsnAlaSerTrp-55 |
| SEQ. ID. NO. 30120 | 57-GlyGlyArgPheHisGlyArgLysThrSerGlyGlyAspArgTyrAsp-72 |
| SEQ. ID. NO. 30121 | 91-ValThrAsnThrLysAsnGlyLysSerVal-100 |
| SEQ. ID. NO. 30122 | 103-ArgValAsnAspArgGlyProPheHisGlyAsnArgIleIleAspValSerLysAlaAlaAla-123 |
| SEQ. ID. NO. 30123 | 142-ValProGlyGlnSerAlaProValAlaGluAsnLysAspIlePheIle-157 |
| SEQ. ID. NO. 30124 | 159-LeuLysSerPheGlyThrGluHisGluAla-168 |
| SEQ. ID. NO. 30125 | 181-AlaSerSerSerSerProAsnLeuSerValGluLysArgArgTyrGluTyr-197 |
| SEQ. ID. NO. 30126 | 205-AlaSerGlnGluArgAlaAlaGluAlaGluAlaGlnAla-217 |
| Hydrophilic Regions - Hopp-Woods | |
| SEQ. ID. NO. 30127 | 27-AlaValValLysProGluLysLeuHisAlaSerAlaAsnArgSerTyrLys-43 |
| SEQ. ID. NO. 30128 | 60-PheHisGlyArgLysThrSerGlyGlyAspArgTyrAsp-72 |
| SEQ. ID. NO. 30129 | 92-ThrAsnThrLysAsnGlyLys-98 |
| SEQ. ID. NO. 30130 | 104-ValAsnAspArgGlyProPheHis-111 |
| SEQ. ID. NO. 30131 | 114-ArgIleIleAspValSerLysAlaAlaAla-123 |
| SEQ. ID. NO. 30132 | 148-ProValAlaGluAsnLysAspIlePheIle-157 |
| SEQ. ID. NO. 30133 | 160-LysSerPheGlyThrGluHisGluAla-168 |
| SEQ. ID. NO. 30134 | 188-LeuSerValGluLysArgArgTyrGluTyr-197 |
| SEQ. ID. NO. 30135 | 205-AlaSerGlnGluArgAlaAlaGluAlaGluAlaGlnAla-217 |
| g266 | |
| Antigenic Index - Jameson-Wolf | |
| SEQ. ID. NO. 30136 | 2-GlnPheArgArgHisArgArgArgGlnCysProAsnArgLysProIle-17 |
| SEQ. ID. NO. 30137 | 47-AlaLeuLysArgLysHisPhe-53 |

TABLE 1-continued

SEQ. ID. NO. 30138 76-SerArgAlaGlyAla-80
SEQ. ID. NO. 30139 110-TrpHisThrArgAsnArgGlu-116
Hydrophilic Regions - Hopp-Woods
SEQ. ID. NO. 30140 2-GlnPheArgArgHisArgArgArgGlnCysProAsnArgLysProIle-17
SEQ. ID. NO. 30141 47-AlaLeuLysArgLysHisPhe-53
SEQ. ID. NO. 30142 76-SerArgAlaGlyAla-80
g268-1
AMPHI Regions - AMPHI
SEQ. ID. NO. 30143 42-GluIleLeuValLysLeuValArg-49
SEQ. ID. NO. 30144 57-ValLysThrPheAspAsp-62
SEQ. ID. NO. 30145 77-HisIleArgArgMetValGluArg-84
SEQ. ID. NO. 30146 92-ValArgThrThrGluLysThr-98
SEQ. ID. NO. 30147 129-IleGlyAsnSerHisLys-134
SEQ. ID. NO. 30148 136-ThrProAspPhePheGluProTyr-143
SEQ. ID. NO. 30149 169-PheAlaGluLeuSerGlnAlaHisAspIleIleHisProLeuSerGluLeuValSerMet-188
SEQ. ID. NO. 30150 191-IleLysGluProLeuAspLys-197
SEQ. ID. NO. 30151 215-AlaArgGluAlaGluGluAlaAla-222
SEQ. ID. NO. 30152 231-GlnGluAlaAlaArgValSerGluTrp-239
SEQ. ID. NO. 30153 249-GluPheGluGlnPheTrpLysGlyLeuProGlnThrValGlnAsn-263
SEQ. ID. NO. 30154 268-SerGlnLysThrTrpLysSerGlyMetAspLys-278
SEQ. ID. NO. 30155 289-GluThrProAsnGlyIleLys-295
Antigenic Index - Jameson-Wolf
SEQ. ID. NO. 30156 1-MetLysLysAsnLeu-5
SEQ. ID. NO. 30157 16-LeuSerGlyCysAspArgLeuGlyIleGlyAsnProPheSerGlyLysGluIleSerCysGlySerGluGluThrLysGluIleLeu-44
SEQ. ID. NO. 30158 47-LeuValArgAspAsnValGluGlyGluThrValLysThrPheAspAspAspAlaPheLysAspGlnAlaPhe-70
SEQ. ID. NO. 30159 77-HisIleArgArgMetValGlu-83
SEQ. ID. NO. 30160 85-LeuGlyIleThrValAspGluValArgThrThrGluLysThrAspThrSerSerLysLeuLysCysGluAlaAlaLeu-110
SEQ. ID. NO. 30161 112-LeuAspValProAspAspValVal-119
SEQ. ID. NO. 30162 127-GlnSerIleGlyAsnSerHisLysLysThrProAspPhePhe-140
SEQ. ID. NO. 30163 143-TyrTyrArgLysGluGlyAlaTyr-150
SEQ. ID. NO. 30164 158-SerValGlnProThrAspAspLysSerLysIle-168
SEQ. ID. NO. 30165 190-LeuIleLysGluProLeuAspLysAlaLysGlnArgAsnGluLysLeuGluAlaAlaGluAlaThrAlaGlnGluAlaArgGluAlaGluGluAlaAla Ala-223
SEQ. ID. NO. 30166 226-AlaLeuGlyArgGluGlnGluAlaAlaArgValSerGluTrpGluGluArgTyrLysLeuSerArgSerGluPhe-250
SEQ. ID. NO. 30167 261-ValGlnAsnLysLeuGlnAlaSerGlnLysThrTrpLysSerGlyMetAspLysIleCysAlaAsnAsnAlaLysAlaGluGlyGluThrProAsnGly IleLysValSerGluLeuAlaCysLysThrAlaGluThrGluAlaArgLeuGluGluLeuHisAsnArgLysLysAlaLeuIle-321
SEQ. ID. NO. 30168 323-GluMetValArgGluGluAspLysLysGluLeuProLysArgLeu-337
Hydrophilic Regions - Hopp-Woods
SEQ. ID. NO. 30169 1-MetLysLysAsnLeu-5
SEQ. ID. NO. 30170 18-GlyCysAspArgLeuGly-23
SEQ. ID. NO. 30171 28-PheSerGlyLysGluIleSerCysGlySerGluGluThrLysGluIleLeu-44
SEQ. ID. NO. 30172 47-LeuValArgAspAsnValGluGlyGluThrValLysThrPheAspAspAspAlaPheLysAspGlnAlaPhe-70
SEQ. ID. NO. 30173 77-HisIleArgArgMetValGlu-83
SEQ. ID. NO. 30174 85-LeuGlyIleThrValAspGluValArgThrThrGluLysThrAspThrSerSerLysLeuLysCysGluAlaAlaLeu-110
SEQ. ID. NO. 30175 112-LeuAspValProAspAspValVal-119
SEQ. ID. NO. 30176 131-AsnSerHisLysLysThrProAspPhe-139
SEQ. ID. NO. 30177 143-TyrTyrArgLysGluGly-148
SEQ. ID. NO. 30178 161-ProThrAspAspLysSerLysIle-168
SEQ. ID. NO. 30179 190-LeuIleLysGluProLeuAspLysAlaLysGlnArgAsnGluLysLeuGluAlaAlaGluAlaThrAlaGlnGluAlaArgGluAlaGluGluAlaAla Ala-223
SEQ. ID. NO. 30180 226-AlaLeuGlyArgGluGlnGluAlaAlaArgValSerGluTrpGluGluArgTyrLysLeuSerArgSerGluPhe-250
SEQ. ID. NO. 30181 270-LysThrTrpLysSerGlyMetAspLysIleCys-280
SEQ. ID. NO. 30182 283-AsnAlaLysAlaGluGlyGluThrProAsn-292
SEQ. ID. NO. 30183 294-IleLysValSerGluLeuAlaCysLysThrAlaGluThrGluAlaArgLeuGluGluLeuHisAsnArgLysLysAlaLeuIle-321
SEQ. ID. NO. 30184 323-GluMetValArgGluGluAspLysLysGluLeuProLysArgLeu-337
g269
AMPHI Regions - AMPHI
SEQ. ID. NO. 30185 36-LysProCysAlaSerLeuAspAlaSerSerAla-46
SEQ. ID. NO. 30186 54-TrpAspPheIleArgAsnThrAlaSerPro-63
SEQ. ID. NO. 30187 73-PheLysThrArgAlaLeuGlyArgPheSer-82
Antigenic Index - Jameson-Wolf
SEQ. ID. NO. 30188 28-TrpSerArgSerAlaPheSerCysLysProCysAla-39
SEQ. ID. NO. 30189 58-ArgAsnThrAlaSerProLysVal-65
SEQ. ID. NO. 30190 73-PheLysThrArgAlaLeuGlyArgPheSerAla-83
SEQ. ID. NO. 30191 90-LeuSerAsnArgGlyValLysLysProLeuSerPheLysSerProSerValGlnValAspThrSerAla-112
SEQ. ID. NO. 30192 117-SerLeuArgSerSer-121
Hydrophilic Regions - Hopp-Woods
SEQ. ID. NO. 30193 60-ThrAlaSerProLysVal-65
SEQ. ID. NO. 30194 73-PheLysThrArgAlaLeuGly-79
SEQ. ID. NO. 30195 93-ArgGlyValLysLysProLeuSer-100
g270
AMPHI Regions - AMPHI
SEQ. ID. NO. 30196 13-LeuLeuThrAlaPheAlaAlaPhe-20
SEQ. ID. NO. 30197 41-AspLeuThrGluGlyCys-46
SEQ. ID. NO. 30198 49-ProAspGlySerArg-53
Antigenic Index - Jameson-Wolf
SEQ. ID. NO. 30199 1-MetAsnLysAsnArgLysLeu-7
SEQ. ID. NO. 30200 41-AspLeuThrGluGlyCysThrLeuProAspGlySerArgValArgAlaAlaAlaValSerThrLysLysProPhe-65
SEQ. ID. NO. 30201 71-HisAlaProAlaGlyThrGlu-77
SEQ. ID. NO. 30202 86-LysAsnMetAspMetGlyPhe-92

TABLE 1-continued

| | |
|---|---|
| SEQ. ID. NO. 30203 | 95-TyrMetPheGluArgGlnProSerGlyThr-104 |
| SEQ. ID. NO. 30204 | 114-ValCysValGluGlyArgArgAspPheThrAla-124 |
| SEQ. ID. NO. 30205 | 128-IleGlySerArgThrPhe-133 |
| Hydrophilic Regions - Hopp-Woods | |
| SEQ. ID. NO. 30206 | 1-MetAsnLysAsnArgLysLeu-7 |
| SEQ. ID. NO. 30207 | 49-ProAspGlySerArgValArgAla-56 |
| SEQ. ID. NO. 30208 | 60-SerThrLysLysProPhe-65 |
| SEQ. ID. NO. 30209 | 73-ProAlaGlyThrGlu-77 |
| SEQ. ID. NO. 30210 | 96-MetPheGluArgGlnPro-101 |
| SEQ. ID. NO. 30211 | 116-ValGluGlyArgArgAspPheThrAla-124 |
| g271-2 | |
| AMPHI Regions - AMPHI | |
| SEQ. ID. NO. 30212 | 6-MetAlaArgIleTrp-10 |
| SEQ. ID. NO. 30213 | 20-SerProCysProAla-24 |
| SEQ. ID. NO. 30214 | 29-ProLysSerProAla-33 |
| Antigenic Index - Jameson-Wolf | |
| SEQ. ID. NO. 30215 | 2-PheSerSerArgMetAlaArg-8 |
| SEQ. ID. NO. 30216 | 25-LeuThrThrLysProLysSerProAlaLys-34 |
| SEQ. ID. NO. 30217 | 41-ArgSerAsnCysLeu-45 |
| SEQ. ID. NO. 30218 | 61-SerSerThrThrGlyAlaProThrSerArg-70 |
| SEQ. ID. NO. 30219 | 78-SerAlaSerIleAsnLysAspThrArgMetProAlaSerVal-91 |
| SEQ. ID. NO. 30220 | 102-CysCysAlaAsnThrSerLysProProSer-111 |
| Hydrophilic Regions - Hopp-Woods | |
| SEQ. ID. NO. 30221 | 27-ThrLysProLysSerProAlaLys-34 |
| SEQ. ID. NO. 30222 | 80-SerIleAsnLysAspThrArgMet-87 |
| SEQ. ID. NO. 30223 | 105-AsnThrSerLysProPro-110 |
| g272-2 | |
| AMPHI Regions - AMPHI | |
| SEQ. ID. NO. 30224 | 44-IleThrArgIleThrAspGlu-50 |
| SEQ. ID. NO. 30225 | 70-AlaGluGluPheSerSerThrAsn-77 |
| SEQ. ID. NO. 30226 | 106-PheArgAlaIleThrSer-111 |
| SEQ. ID. NO. 30227 | 165-IleIleThrIleGluAspProIleGlu-173 |
| SEQ. ID. NO. 30228 | 194-AsnTrpMetAlaAlaLeuLysAsnThrLeuArgGlnAla-206 |
| SEQ. ID. NO. 30229 | 244-AsnGlnAlaLeuAspArgIleIleAsn-252 |
| SEQ. ID. NO. 30230 | 307-GlyAsnIleHisGluIleLysGluValMetLys-317 |
| SEQ. ID. NO. 30231 | 328-AspGlnHisLeuTyrGln-333 |
| SEQ. ID. NO. 30232 | 343-GlnAspAlaLeuLysAsnAlaAspSer-351 |
| Antigenic Index - Jameson-Wolf | |
| SEQ. ID. NO. 30233 | 2-PheThrAspGluAsnMetThrAlaLysGluGluLeu-13 |
| SEQ. ID. NO. 30234 | 19-HisMetAsnLysAsnLysGlySerAsp-27 |
| SEQ. ID. NO. 30235 | 38-MetLysLeuAspGlyLysIleThrArgIleThrAspGluProLeuThrAlaGluLysCysMet-58 |
| SEQ. ID. NO. 30236 | 68-LysGlnAlaGluGluPheSerSerThrAsnGlu-78 |
| SEQ. ID. NO. 30237 | 85-LeuProAspThrSerArgPheArgVal-93 |
| SEQ. ID. NO. 30238 | 109-IleThrSerLysIleProLysPheGluSerLeuAsn-120 |
| SEQ. ID. NO. 30239 | 122-ProProAlaLeuLys-126 |
| SEQ. ID. NO. 30240 | 128-ValAlaLeuLysLysArgGly-134 |
| SEQ. ID. NO. 30241 | 142-ThrGlySerGlyLysSerThrSerLeu-150 |
| SEQ. ID. NO. 30242 | 154-IleAspTyrArgAsnGluAsnSerPheGly-163 |
| SEQ. ID. NO. 30243 | 168-IleGluAspProIle-172 |
| SEQ. ID. NO. 30244 | 176-HisGluHisLysAsnCys-181 |
| SEQ. ID. NO. 30245 | 184-ThrGlnArgGluValGlyValAspThrGluAsn-194 |
| SEQ. ID. NO. 30246 | 199-LeuLysAsnThrLeuArgGlnAlaProAsp-208 |
| SEQ. ID. NO. 30247 | 214-GluIleArgAspArgGluThrMet-221 |
| SEQ. ID. NO. 30248 | 241-AsnSerThrAsnGlnAlaLeuAspArg-249 |
| SEQ. ID. NO. 30249 | 254-PheProGluGluArgArgGluGlnLeuLeu-263 |
| SEQ. ID. NO. 30250 | 278-LeuValProArgAspGlyGlyLysGlyArgValAlaAla-290 |
| SEQ. ID. NO. 30251 | 310-HisGluIleLysGluValMetLysLysSerThr-320 |
| SEQ. ID. NO. 30252 | 336-GluLysGlyGluIleSerLeu-342 |
| SEQ. ID. NO. 30253 | 344-AspAlaLeuLysAsnAlaAspSerAlaHisAspLeu-355 |
| SEQ. ID. NO. 30254 | 361-LeuArgSerArgArgAlaGlnSerSerAspProAspLeuGluLeu-375 |
| Hydrophilic Regions - Hopp-Woods | |
| SEQ. ID. NO. 30255 | 2-PheThrAspGluAsnMetThrAlaLysGluGluLeu-13 |
| SEQ. ID. NO. 30256 | 20-MetAsnLysAsnLysGlySerAsp-27 |
| SEQ. ID. NO. 30257 | 38-MetLysLeuAspGlyLysIleThrArgIleThrAspGluProLeuThrAlaGluLysCysMet-58 |
| SEQ. ID. NO. 30258 | 68-LysGlnAlaGluGluPheSerSer-75 |
| SEQ. ID. NO. 30259 | 87-AspThrSerArgPheArgVal-93 |
| SEQ. ID. NO. 30260 | 112-LysIleProLysPheGluSer-118 |
| SEQ. ID. NO. 30261 | 128-ValAlaLeuLysLysArgGly-134 |
| SEQ. ID. NO. 30262 | 143-GlySerGlyLysSerThrSer-149 |
| SEQ. ID. NO. 30263 | 155-AspTyrArgAsnGluAsnSer-161 |
| SEQ. ID. NO. 30264 | 168-IleGluAspProIle-172 |
| SEQ. ID. NO. 30265 | 176-HisGluHisLysAsn-180 |
| SEQ. ID. NO. 30266 | 184-ThrGlnArgGluValGlyValAspThr-192 |
| SEQ. ID. NO. 30267 | 201-AsnThrLeuArgGlnAlaPro-207 |
| SEQ. ID. NO. 30268 | 214-GluIleArgAspArgGluThrMet-221 |
| SEQ. ID. NO. 30269 | 245-GlnAlaLeuAspArg-249 |
| SEQ. ID. NO. 30270 | 255-ProGluGluArgArgGluGlnLeuLeu-263 |
| SEQ. ID. NO. 30271 | 278-LeuValProArgAspGlyGlyLysGlyArgValAlaAla-290 |
| SEQ. ID. NO. 30272 | 310-HisGluIleLysGluValMetLysLysSerThr-320 |
| SEQ. ID. NO. 30273 | 336-GluLysGlyGluIleSerLeu-342 |

TABLE 1-continued

| | |
|---|---|
| SEQ. ID. NO. 30274 | 344-AspAlaLeuLysAsnAlaAspSerAlaHisAspLeu-355 |
| SEQ. ID. NO. 30275 | 361-LeuArgSerArgArgAlaGlnSerSerAspProAspLeuGluLeu-375 |
| g274 | |
| AMPHI Regions - AMPHI | |
| SEQ. ID. NO. 30276 | 31-TyrLysAspGlyLys-35 |
| SEQ. ID. NO. 30277 | 111-GluAlaValPheLys-115 |
| Antigenic Index - Jameson-Wolf | |
| SEQ. ID. NO. 30278 | 25-LeuValThrAspAspTyrTyrLysAspGlyLysHisIleAsp-38 |
| SEQ. ID. NO. 30279 | 40-GlnLeuHisArgAspGluGluAlaValArgArgHisIle-52 |
| SEQ. ID. NO. 30280 | 60-ProAspMetAsnAla-64 |
| SEQ. ID. NO. 30281 | 71-GlyGluPheAspGlyLysGlnPro-78 |
| SEQ. ID. NO. 30282 | 85-HisProThrArgLysAlaAspAspGlnThrVal-95 |
| SEQ. ID. NO. 30283 | 99-ProValGlySerAlaGlnAsnGlyArgAlaGluTyr-110 |
| SEQ. ID. NO. 30284 | 116-ThrLeuProProAlaAsnHis-122 |
| SEQ. ID. NO. 30285 | 126-ArgValGluAspAlaAlaGly-132 |
| SEQ. ID. NO. 30286 | 136-ValGluAsnLysTrpIleThrSerGlnGlyAsnAlaValAspLeuThrProMetAspLysLeuPheAsnAsnAlaGlySerLys-163 |
| Hydrophilic Regions - Hopp-Woods | |
| SEQ. ID. NO. 30287 | 29-AspTyrTyrLysAspGlyLysHisIleAsp-38 |
| SEQ. ID. NO. 30288 | 40-GlnLeuHisArgAspGluGluAlaValArgArgHisIle-52 |
| SEQ. ID. NO. 30289 | 72-GluPheAspGlyLysGln-77 |
| SEQ. ID. NO. 30290 | 86-ProThrArgLysAlaAspAspGlnThrVal-95 |
| SEQ. ID. NO. 30291 | 104-GlnAsnGlyArgAlaGluTyr-110 |
| SEQ. ID. NO. 30292 | 126-ArgValGluAspAlaAlaGly-132 |
| SEQ. ID. NO. 30293 | 151-ThrProMetAspLysLeuPhe-157 |
| g276 | |
| AMPHI Regions - AMPHI | |
| SEQ. ID. NO. 30294 | 19-ArgArgTrpAlaThrMetMet-25 |
| SEQ. ID. NO. 30295 | 60-SerPheLysMetAlaArg-65 |
| SEQ. ID. NO. 30296 | 80-ProPheAspProMetGlyTrp-86 |
| SEQ. ID. NO. 30297 | 115-GlyArgLeuTyrArgThrPheSerAsn-123 |
| SEQ. ID. NO. 30298 | 164-ThrLysArgGlyArgArgLeuThr-171 |
| SEQ. ID. NO. 30299 | 207-SerThrSerThrLeuArgLysLeuMetArgProSerThr-219 |
| Antigenic Index - Jameson-Wolf | |
| SEQ. ID. NO. 30300 | 9-MetMetArgSerAlaAspSerThrVal-17 |
| SEQ. ID. NO. 30301 | 29-PheSerIleArgArgSerSerAlaCysTrpThrArgArgSerAspSerLeuSer-46 |
| SEQ. ID. NO. 30302 | 52-SerSerAsnAsnAsnIle-57 |
| SEQ. ID. NO. 30303 | 67-MetAlaThrArgCysArgCysProProAspLysLeuLeuPro-80 |
| SEQ. ID. NO. 30304 | 82-AspProMetGlyTrp-86 |
| SEQ. ID. NO. 30305 | 88-SerProSerGlyAspAlaSerIleArg-96 |
| SEQ. ID. NO. 30306 | 103-TrpArgAlaAspArgThrSerAlaSerProAlaSerGlyArgLeuTyr-118 |
| SEQ. ID. NO. 30307 | 121-PheSerAsnArgValSerSerAsnArgAsnThrSerTrpGluThrArgAlaAsnTrpAlaArgArgGlnSerSerLeu-146 |
| SEQ. ID. NO. 30308 | 158-LeuProAlaAspGlySerThrLysArgGlyArgArgLeuThrThr-172 |
| SEQ. ID. NO. 30309 | 176-ProLeuProGluArgProThrArgAlaThrArgSerProCysLeu-190 |
| SEQ. ID. NO. 30310 | 194-LeuLysLeuSerArg-198 |
| SEQ. ID. NO. 30311 | 200-LeuMetProSerGluArgTyrSerThrSerThrLeuArgLysLeuMetArgProSerThrArgCysGlyAla-223 |
| SEQ. ID. NO. 30312 | 229-CysSerGlyGlyValSerArgAsnAlaHisThrProSerAlaAlaArgAsn-245 |
| Hydrophilic Regions - Hopp-Woods | |
| SEQ. ID. NO. 30313 | 29-PheSerIleArgArgSerSer-35 |
| SEQ. ID. NO. 30314 | 38-TrpThrArgArgSerAspSerLeu-45 |
| SEQ. ID. NO. 30315 | 67-MetAlaThrArgCysArgCysProProAspLys-77 |
| SEQ. ID. NO. 30316 | 90-SerGlyAspAlaSerIleArg-96 |
| SEQ. ID. NO. 30317 | 104-ArgAlaAspArgThrSerAla-110 |
| SEQ. ID. NO. 30318 | 124-ArgValSerSerAsnArgAsnThrSerTrpGluThr-135 |
| SEQ. ID. NO. 30319 | 137-AlaAsnTrpAlaArgArgGlnSerSer-145 |
| SEQ. ID. NO. 30320 | 161-AspGlySerThrLysArgGlyArgArgLeuThrThr-172 |
| SEQ. ID. NO. 30321 | 176-ProLeuProGluArgProThrArgAlaThrArg-186 |
| SEQ. ID. NO. 30322 | 194-LeuLysLeuSerArg-198 |
| SEQ. ID. NO. 30323 | 200-LeuMetProSerGluArgTyrSer-207 |
| SEQ. ID. NO. 30324 | 210-ThrLeuArgLysLeuMetArgProSerThrArgCys-221 |
| SEQ. ID. NO. 30325 | 232-GlyValSerArgAsnAlaHis-238 |
| g277-2 | |
| AMPHI Regions - AMPHI | |
| SEQ. ID. NO. 30326 | 39-GlyIleAlaValPheGluValValGlyArgLeuLeuAspPheValLeu-54 |
| SEQ. ID. NO. 30327 | 72-AsnGluValIleAspValPheHisAlaLeuGln-82 |
| SEQ. ID. NO. 30328 | 87-AlaPheAspAlaValGlyAsnPheAlaGluTyrGlyArgAlaIleAspThrAlaAspLeuLeuGluIleGlyLysLeuGlyTyrPheHis-116 |
| SEQ. ID. NO. 30329 | 180-AlaValGlyValValAlaValAla-187 |
| Antigenic Index - Jameson-Wolf | |
| SEQ. ID. NO. 30330 | 1-MetProArgPheGluAspGlnLeuValGlyArgXxxGlyLysAla-15 |
| SEQ. ID. NO. 30331 | 68-ArgPheCysProAsnGluVal-74 |
| SEQ. ID. NO. 30332 | 96-GluTyrGlyArgAlaIleAspThr-103 |
| SEQ. ID. NO. 30333 | 118-ValGluProAspPheProAlaGlnThrProArgThrGluGlyGly-132 |
| SEQ. ID. NO. 30334 | 138-PheAspLysAlaAspValVal-144 |
| SEQ. ID. NO. 30335 | 162-AspIleGlyGlyGlyGlyPheGluGlyAspLeu-172 |
| SEQ. ID. NO. 30336 | 196-LeuAspValGlyGlyLysProArgLeuGlyAlaGluArgAlaGlnAlaGlyGlyGlyMetGlyCysAlaGlyThrAspPheHis-223 |
| SEQ. ID. NO. 30337 | 226-GlyLeuAspAspGlyAla-231 |
| SEQ. ID. NO. 30338 | 237-GluGlyLeuGlnPheGluAspAspLeuLeuGluGlyLysHisGlyLeu-252 |
| Hydrophilic Regions - Hopp-Woods | |
| SEQ. ID. NO. 30339 | 2-ProArgPheGluAspGlnLeuVal-9 |
| SEQ. ID. NO. 30340 | 96-GluTyrGlyArgAlaIleAspThr-103 |
| SEQ. ID. NO. 30341 | 118-ValGluProAspPhe-122 |

TABLE 1-continued

| | |
|---|---|
| SEQ. ID. NO. 30342 | 126-ThrProArgThrGluGly-131 |
| SEQ. ID. NO. 30343 | 138-PheAspLysAlaAspValVal-144 |
| SEQ. ID. NO. 30344 | 167-GlyPheGluGlyAspLeu-172 |
| SEQ. ID. NO. 30345 | 198-ValGlyGlyLysProArgLeuGlyAlaGluArgAlaGlnAla-211 |
| SEQ. ID. NO. 30346 | 226-GlyLeuAspAspGlyAla-231 |
| SEQ. ID. NO. 30347 | 239-LeuGlnPheGluAspAspLeuLeuGluGlyLysHisGlyLeu-252 |
| g278-2 | |
| AMPHI Regions - AMPHI | |
| SEQ. ID. NO. 30348 | 20-IleGlyProLeuProSerIleGlyArg-28 |
| SEQ. ID. NO. 30349 | 42-ThrGlyThrSerLys-46 |
| SEQ. ID. NO. 30350 | 101-ArgThrIleProSerValThrGluIleThrValProArgValLeuThrSerAlaPhe-119 |
| SEQ. ID. NO. 30351 | 123-PheSerIleLeuAlaLeuIleArgSerLeuIleSer-134 |
| SEQ. ID. NO. 30352 | 157-LeuTyrArgGlnIleGlnAsnLeuIleThrHisPheAsnPheTyrAlaAla-173 |
| SEQ. ID. NO. 30353 | 189-GluThrLeuIleGlnHisLeuArgGlnLeuAlaAsp-200 |
| Antigenic Index - Jameson-Wolf | |
| SEQ. ID. NO. 30354 | 25-SerIleGlyArgProAsnAlaSerThrThrArgProThrAsnSerArgProThrGlyThrSerLysIleArgPro-49 |
| SEQ. ID. NO. 30355 | 63-SerProAsnThrThrAlaProThrGluSerArgSerArgPheIleAla-78 |
| SEQ. ID. NO. 30356 | 80-ProLysValLeuProGlyAsnSerSerIle-89 |
| SEQ. ID. NO. 30357 | 93-IleAlaSerAspLysProTrpMetArg-101 |
| SEQ. ID. NO. 30358 | 119-PheThrAspArgPheSer-124 |
| SEQ. ID. NO. 30359 | 146-ArgHisSerArgValGlnSerThr-153 |
| SEQ. ID. NO. 30360 | 178-PheAspPheAspArgAspPheGlnLeu-186 |
| SEQ. ID. NO. 30361 | 209-ThrValAsnAspGlyArgPheAspMetValGlu-219 |
| Hydrophilic Regions - Hopp-Woods | |
| SEQ. ID. NO. 30362 | 27-GlyArgProAsnAlaSerThrThrArgProThrAsnSerArgProThrGlyThrSerLysIleArgPro-49 |
| SEQ. ID. NO. 30363 | 68-AlaProThrGluSerArgSerArgPheIleAla-78 |
| SEQ. ID. NO. 30364 | 93-IleAlaSerAspLysProTrp-99 |
| SEQ. ID. NO. 30365 | 146-ArgHisSerArgValGln-151 |
| SEQ. ID. NO. 30366 | 178-PheAspPheAspArgAspPhe-184 |
| SEQ. ID. NO. 30367 | 211-AsnAspGlyArgPheAspMetValGlu-219 |
| g279 | |
| AMPHI Regions - AMPHI | |
| SEQ. ID. NO. 30368 | 6-GlyCysLeuIleSer-10 |
| SEQ. ID. NO. 30369 | 58-LeuProAlaIleThrThr-63 |
| Antigenic Index - Jameson-Wolf | |
| SEQ. ID. NO. 30370 | 28-GlnTrpGluGlyThrAspThrGlySerGlyArgAlaArgLeuAla-42 |
| SEQ. ID. NO. 30371 | 64-CysProGlyGluLeuLysLeuThr-71 |
| SEQ. ID. NO. 30372 | 74-ThrThrSerProCysAlaAspSer-81 |
| SEQ. ID. NO. 30373 | 88-CysSerSerSerLysProLysMet-95 |
| SEQ. ID. NO. 30374 | 102-ProCysGlyThrAlaAspCysIleSerSerAlaArgArgArgThrSerLeu-118 |
| SEQ. ID. NO. 30375 | 120-AlaSerAlaLysSerAsnAlaSer-127 |
| SEQ. ID. NO. 30376 | 148-ProProThrSerLys-152 |
| Hydrophilic Regions - Hopp-Woods | |
| SEQ. ID. NO. 30377 | 29-TrpGluGlyThrAspThrGlySerGlyArgAlaArgLeuAla-42 |
| SEQ. ID. NO. 30378 | 66-GlyGluLeuLysLeu-70 |
| SEQ. ID. NO. 30379 | 89-SerSerSerLysProLysMet-95 |
| SEQ. ID. NO. 30380 | 110-SerSerAlaArgArgArgThrSerLeu-118 |
| SEQ. ID. NO. 30381 | 120-AlaSerAlaLysSerAsnAla-126 |
| g280 | |
| AMPHI Regions - AMPHI | |
| SEQ. ID. NO. 30382 | 27-SerPheSerIleLeuGlyAspValAlaLys-36 |
| SEQ. ID. NO. 30383 | 64-AspIleLysLysIleArgSerAla-71 |
| SEQ. ID. NO. 30384 | 85-AspIleGlnArgAlaValLys-91 |
| SEQ. ID. NO. 30385 | 97-TyrAlaGluAlaThrLysGlyIleGlnProLeuLys-108 |
| SEQ. ID. NO. 30386 | 150-AspTyrAlaGlnAsnValAlaGluThrLeuIleLys-161 |
| SEQ. ID. NO. 30387 | 237-ValAlaAlaIleIleArgGlnIleLys-245 |
| SEQ. ID. NO. 30388 | 247-GluGlyIleLysAlaValPheThrGlu-255 |
| SEQ. ID. NO. 30389 | 258-LysAspThrArgMetValAspArgIleAlaLysGluThr-270 |
| SEQ. ID. NO. 30390 | 278-LeuTyrSerAspAlaLeuGlyAsnAlaProAlaAspThrTyrIle-292 |
| Antigenic Index - Jameson-Wolf | |
| SEQ. ID. NO. 30391 | 38-IleGlyGlyGluArgValAla-44 |
| SEQ. ID. NO. 30392 | 51-AlaAsnGlnAspThrHis-56 |
| SEQ. ID. NO. 30393 | 61-ThrSerGlyAspIleLysLysIleArgSerAlaLys-72 |
| SEQ. ID. NO. 30394 | 82-GluAlaAlaAspIleGlnArgAlaValLysGlnSerLysValSerTyrAlaGluAlaThrLysGlyIleGln-105 |
| SEQ. ID. NO. 30395 | 107-LeuLysAlaGluGluGluGlyGlyHisHisHisAspHisHisHisAspHisAspHisAspHisGluGlyHisHisHisAspHisGlyGluTyr AspProHisValTrpAsnAspProValLeu-147 |
| SEQ. ID. NO. 30396 | 158-ThrLeuIleLysAlaAspProGluGlyLysValTyrTyr-170 |
| SEQ. ID. NO. 30397 | 180-GlnLeuLysLysLeuHisSerAspAla-188 |
| SEQ. ID. NO. 30398 | 196-ProAlaAlaLysArgLysValLeuThr-204 |
| SEQ. ID. NO. 30399 | 212-MetGlyAsnArgTyr-216 |
| SEQ. ID. NO. 30400 | 224-GlnGlyValSerSerGluAlaGluProSerAlaLysGln-236 |
| SEQ. ID. NO. 30401 | 242-ArgGlnIleLysArgGluGlyIle-249 |
| SEQ. ID. NO. 30402 | 255-GluAsnIleLysAspThrArgMetValAspArgIleAlaLysGluThrGlyVal-272 |
| SEQ. ID. NO. 30403 | 274-ValSerGlyLysLeuTyrSer-280 |
| SEQ. ID. NO. 30404 | 286-AlaProAlaAspThr-290 |
| SEQ. ID. NO. 30405 | 295-TyrArgHisAsnVal-299 |
| Hydrophilic Regions - Hopp-Woods | |
| SEQ. ID. NO. 30406 | 38-IleGlyGlyGluArgValAla-44 |
| SEQ. ID. NO. 30407 | 63-GlyAspIleLysLysIleArgSerAlaLys-72 |
| SEQ. ID. NO. 30408 | 82-GluAlaAlaAspIleGlnArgAlaValLysGlnSerLys-94 |

TABLE 1-continued

| | |
|---|---|
| SEQ. ID. NO. 30409 | 99-GluAlaThrLysGly-103 |
| SEQ. ID. NO. 30410 | 107-LeuLysAlaGluGluGluGlyGlyHisHisHisAspHisHisHisAspHisAspHisAspHisGluGlyHisHisHisAspHisGlyGluTyrAsp-138 |
| SEQ. ID. NO. 30411 | 158-ThrLeuIleLysAlaAspProGluGly-166 |
| SEQ. ID. NO. 30412 | 180-GlnLeuLysLysLeuHisSerAspAla-188 |
| SEQ. ID. NO. 30413 | 196-ProAlaAlaLysArgLysValLeuThr-204 |
| SEQ. ID. NO. 30414 | 226-ValSerSerGluAlaGluProSerAlaLysGln-236 |
| SEQ. ID. NO. 30415 | 242-ArgGlnIleLysArgGluGlyIle-249 |
| SEQ. ID. NO. 30416 | 255-GluAsnIleLysAspThrArgMetValAspArgIleAlaLysGluThrGlyVal-272 |
| g281 | |
| AMPHI Regions - AMPHI | |
| SEQ. ID. NO. 30417 | 62-AlaAlaGlyMetLeuMetAlaLeuLeuAlaGlyLeuValSerArgPhe-77 |
| SEQ. ID. NO. 30418 | 126-LeuGlnLeuIleAlaAlaValSerGlyLeuThr-136 |
| SEQ. ID. NO. 30419 | 179-LeuValSerGlyPheGlnAlaLeuGlyIleLeu-189 |
| SEQ. ID. NO. 30420 | 216-SerValLeuIleAlaLeuPheCysGlyLeuIleGlyLeu-228 |
| Antigenic Index - Jameson-Wolf | |
| SEQ. ID. NO. 30421 | 25-ArgArgMetSerLeu-29 |
| SEQ. ID. NO. 30422 | 78-ThrThrLeuLysGluAspAlaAsn-85 |
| SEQ. ID. NO. 30423 | 102-SerLysAsnGlySerSerVal-108 |
| SEQ. ID. NO. 30424 | 158-LysSerValAsnGlyLysGlyGly-165 |
| SEQ. ID. NO. 30425 | 236-IleProSerGlyPro-240 |
| SEQ. ID. NO. 30426 | 256-LeuGlyLysGluGlyGlyIle-262 |
| SEQ. ID. NO. 30427 | 266-TrpPheLysAsnHisArgHisHisThrThr-275 |
| Hydrophilic Regions - Hopp-Woods | |
| SEQ. ID. NO. 30428 | 25-ArgArgMetSerLeu-29 |
| SEQ. ID. NO. 30429 | 78-ThrThrLeuLysGluAspAlaAsn-85 |
| SEQ. ID. NO. 30430 | 103-LysAsnGlySerSer-107 |
| SEQ. ID. NO. 30431 | 256-LeuGlyLysGluGlyGlyIle-262 |
| SEQ. ID. NO. 30432 | 270-HisArgHisHisThr-274 |
| g282 | |
| AMPHI Regions - AMPHI | |
| SEQ. ID. NO. 30433 | 10-LeuIleValAlaLeuLeuValLeuIleAsnProPheSerAlaLeu-24 |
| SEQ. ID. NO. 30434 | 50-ValPheAlaValIleAlaValPheAlaLeuIleGlyGlyAlaLeu-64 |
| SEQ. ID. NO. 30435 | 112-ArgProAlaArgAsn-116 |
| SEQ. ID. NO. 30436 | 176-ValSerArgLeuLeu-180 |
| SEQ. ID. NO. 30437 | 186-ThrIleLeuAsnArgIleMetGlyMet-194 |
| Antigenic Index - Jameson-Wolf | |
| SEQ. ID. NO. 30438 | 31-ThrAsnGlyHisSerThrLysGluArgArgLysValAlaArg-44 |
| SEQ. ID. NO. 30439 | 92-AsnGlyAsnAspAsnProAlaLysGlnAsnLeuGlyAlaGlnProGluThrGlyGlnAlaArgProAlaArgAsnAlaGly-118 |
| Hydrophilic Regions - Hopp-Woods | |
| SEQ. ID. NO. 30440 | 34-HisSerThrLysGluArgArgLysValAlaArg-44 |
| SEQ. ID. NO. 30441 | 92-AsnGlyAsnAspAsnProAlaLysGlnAsnLeu-102 |
| SEQ. ID. NO. 30442 | 104-AlaGlnProGluThrGlyGlnAlaArgProAlaArgAsn-116 |
| g283 | |
| AMPHI Regions - AMPHI | |
| SEQ. ID. NO. 30443 | 32-GlyGlyAsnSerTyrSerAspValProLysGlnLeuHis-44 |
| SEQ. ID. NO. 30444 | 48-SerGlnIleLeuAsnLeu-53 |
| Antigenic Index - Jameson-Wolf | |
| SEQ. ID. NO. 30445 | 28-TrpLysAspGlyGlyGlyAsnSerTyrSerAspValProLysGlnLeuHisProAspGlnSerGln-49 |
| SEQ. ID. NO. 30446 | 55-ThrLeuGlnThrLysProAlaValLysProLysProAlaValAspThrAsnAlaAspSerAlaLysGluAsnGluLysAspIleAlaGluLysAsnGly GlnLeuGluGluGluLysLysLysIleAlaGluThrGluArgGlnAsnLysGluGluAsnCysArgIleSerLysMetAsnLeu-115 |
| SEQ. ID. NO. 30447 | 119-GlyAsnSerAsnAlaLysAsnLysAspAspLeuIleArgLysTyrAsnAsnAlaValAsnLysTyrCysArg-142 |
| Hydrophilic Regions - Hopp-Woods | |
| SEQ. ID. NO. 30448 | 35-SerTyrSerAspValProLys-41 |
| SEQ. ID. NO. 30449 | 43-LeuHisProAspGlnSerGln-49 |
| SEQ. ID. NO. 30450 | 60-ProAlaValLysProLysProAlaValAspThrAsnAlaAspSerAlaLysGluAsnGluLysAspIleAlaGluLysAsnGlyGlnLeuGluGluGlu LysLysLysIleAlaGluThrGluArgGlnAsnLysGluGluAsnCysArgIleSerLysMetAsnLeu-115 |
| SEQ. ID. NO. 30451 | 121-SerAsnAlaLysAsnLysAspAspLeuIleArgLysTyrAsn-134 |
| g284-2 | |
| AMPHI Regions - AMPHI | |
| SEQ. ID. NO. 30452 | 43-GluAlaPheAlaGlyPhePheGluThrVal-52 |
| SEQ. ID. NO. 30453 | 61-ThrPheAlaAlaArgPhe-66 |
| SEQ. ID. NO. 30454 | 125-ValAspPheAspValPhe-130 |
| SEQ. ID. NO. 30455 | 154-ValValPheArgLeuPheArgGln-161 |
| SEQ. ID. NO. 30456 | 174-AsnThrAlaCysGlyAsnValGlyGly-182 |
| SEQ. ID. NO. 30457 | 186-PheAlaAlaAlaPhe-190 |
| SEQ. ID. NO. 30458 | 216-PheValGlnPheIleArgAspAspPheGlyHisArg-227 |
| SEQ. ID. NO. 30459 | 277-PheArgValPheGlyGlnPheAlaArgGlnPheAlaAspCysAlaVal-292 |
| SEQ. ID. NO. 30460 | 310-AspGlyPheAspValValAspLys-317 |
| SEQ. ID. NO. 30461 | 342-LeuHisGlnValArgGlnThrAlaArgSerGlyAspAsnGlnIleAspArgPheAlaGln-361 |
| SEQ. ID. NO. 30462 | 381-AlaHisIlePheGly-385 |
| SEQ. ID. NO. 30463 | 387-ArgGlnCysValPhe-391 |
| SEQ. ID. NO. 30464 | 408-ArgAlaPheAlaArgPhePheAlaAlaPheGlyGlnSerLeuGlnSer-423 |
| Antigenic Index - Jameson-Wolf | |
| SEQ. ID. NO. 30465 | 1-MetProSerGluThrArgAsnArgPhe-9 |
| SEQ. ID. NO. 30466 | 107-HisAlaPheAspGlyGlnPhe-113 |
| SEQ. ID. NO. 30467 | 132-HisPheGlyLysArgAsnArgAsnThrArgAla-142 |
| SEQ. ID. NO. 30468 | 147-GlyAlaProAspAlaVal-152 |
| SEQ. ID. NO. 30469 | 167-ValGlyAsnGlyArgTyrVal-173 |
| SEQ. ID. NO. 30470 | 178-GlyAsnValGlyGlyAsnGlnAsn-185 |
| SEQ. ID. NO. 30471 | 192-GlnIleArgGlnArgAlaVal-198 |

TABLE 1-continued

| | |
|---|---|
| SEQ. ID. NO. 30472 | 209-AlaValGlyGlyGlu-213 |
| SEQ. ID. NO. 30473 | 219-PheIleArgAspAspPheGlyHisArgPheGlyGlyArgGluAsnHisThr-235 |
| SEQ. ID. NO. 30474 | 292-ValProSerGlyGlyGluGlnXxxSer-300 |
| SEQ. ID. NO. 30475 | 303-ValGlyArgGlyGlyPheHisAspGlyPheAspValValAspLysAlaHis-319 |
| SEQ. ID. NO. 30476 | 346-ArgGlnThrAlaArgSerGlyAspAsnGlnIleAspArgPheAla-360 |
| SEQ. ID. NO. 30477 | 362-GlyAlaGlyLeuValAlaGluArgCysAlaAlaAspAspAlaAspGlyAlaGluPro-380 |
| SEQ. ID. NO. 30478 | 393-AspLeuArgArgGlnPheAlaGlyArgCysGlnHisGlnArgAlaArgAla-409 |
| SEQ. ID. NO. 30479 | 419-GlnSerLeuGlnSerArg-424 |
| Hydrophilic Regions - Hopp-Woods | |
| SEQ. ID. NO. 30480 | 1-MetProSerGluThrArgAsnArgPhe-9 |
| SEQ. ID. NO. 30481 | 134-GlyLysArgAsnArgAsnThrArgAla-142 |
| SEQ. ID. NO. 30482 | 193-IleArgGlnArgAlaVal-198 |
| SEQ. ID. NO. 30483 | 220-IleArgAspAspPheGlyHis-226 |
| SEQ. ID. NO. 30484 | 228-PheGlyGlyArgGluAsnHisThr-235 |
| SEQ. ID. NO. 30485 | 294-SerGlyGlyGluGlnXxx-299 |
| SEQ. ID. NO. 30486 | 313-AspValValAspLysAlaHis-319 |
| SEQ. ID. NO. 30487 | 346-ArgGlnThrAlaArgSerGlyAspAsnGlnIleAspArgPheAla-360 |
| SEQ. ID. NO. 30488 | 366-ValAlaGluArgCysAlaAlaAspAspAlaAspGlyAlaGlu-379 |
| SEQ. ID. NO. 30489 | 393-AspLeuArgArgGlnPheAla-399 |
| SEQ. ID. NO. 30490 | 402-CysGlnHisGlnArgAlaArgAla-409 |
| g285-1 | |
| AMPHI Regions - AMPHI | |
| SEQ. ID. NO. 30491 | 15-ValCysPheLeuGly-19 |
| SEQ. ID. NO. 30492 | 34-GlnIleProSerTrp-38 |
| SEQ. ID. NO. 30493 | 50-GlyThrLeuLeuAspGlyPheAsp-57 |
| SEQ. ID. NO. 30494 | 115-GlnGlyLeuProAspSerIleAspLeuPro-124 |
| SEQ. ID. NO. 30495 | 208-HisSerThrAlaArg-212 |
| SEQ. ID. NO. 30496 | 240-HisProPheAlaGluSerLeuAspLysThrLeuGluGluValLeu-254 |
| SEQ. ID. NO. 30497 | 266-ValProSerLeuPro-270 |
| SEQ. ID. NO. 30498 | 280-AlaIleProSerPheSerAsp-286 |
| SEQ. ID. NO. 30499 | 313-GlnValLeuGlyGly-317 |
| SEQ. ID. NO. 30500 | 592-IleGlyLysAlaAlaAspIle-598 |
| SEQ. ID. NO. 30501 | 671-GlyIleAsnArgGluLeuThrArgTrp-679 |
| SEQ. ID. NO. 30502 | 745-LeuHisIleAlaGluLeuHisAsnPhePheLysProProPhe-758 |
| SEQ. ID. NO. 30503 | 836-PheGlyGlyAsnMetAlaAsn-842 |
| SEQ. ID. NO. 30504 | 848-ArgIleThrAlaSerLeu-853 |
| SEQ. ID. NO. 30505 | 855-AspLeuGlyAlaLeu-859 |
| SEQ. ID. NO. 30506 | 868-GlnAsnIleThrGlySer-873 |
| SEQ. ID. NO. 30507 | 955-GlySerIleAlaAsp-959 |
| SEQ. ID. NO. 30508 | 1008-ThrAlaGluLeuSer-1012 |
| SEQ. ID. NO. 30509 | 1061-ValThrGlyMetIleLys-1066 |
| SEQ. ID. NO. 30510 | 1137-GlyAsnValArgGlyValGlyThrValArg-1146 |
| SEQ. ID. NO. 30511 | 1165-ThrValSerPheValGlyProLeuAsn-1173 |
| SEQ. ID. NO. 30512 | 1190-AlaGlyValGluIleLeuGlySerLeuAsn-1199 |
| SEQ. ID. NO. 30513 | 1244-LeuAlaGlyGlnIle-1248 |
| SEQ. ID. NO. 30514 | 1305-ValLysLeuIleTyrArgLeuThrArgAlaIleGlnAlaValAlaArgIleGlySer-1323 |
| SEQ. ID. NO. 30515 | 1335-ArgPheAspArgLeuPheGly-1341 |
| Antigenic Index - Jameson-Wolf | |
| SEQ. ID. NO. 30516 | 43-IleSerSerGlnAsnLeuLysGlyThrLeuLeuAspGlyPheAspGlyAspAsnTrpSerIleGluThrGluGlyAlaAspLeuLysIleSerArg-74 |
| SEQ. ID. NO. 30517 | 80-LysProSerGluLeuMetArgArgSerLeuHis-90 |
| SEQ. ID. NO. 30518 | 104-LysProThrProProLysGluGluArgProProGlnGlyLeuProAspSerIleAsp-122 |
| SEQ. ID. NO. 30519 | 130-AspArgPheGluThrGlyLysIleSerMetGlyLysThrPheAspLysGlnThrValTyr-149 |
| SEQ. ID. NO. 30520 | 157-TyrArgTyrAspArgLysGlyHisArgLeuAspLeuLysAlaAlaAspThrProTrpSerSerSerSerGlySerAla-182 |
| SEQ. ID. NO. 30521 | 185-GlyLeuLysLysProPheAla-191 |
| SEQ. ID. NO. 30522 | 198-ThrLysGlyGlyPheGluGlyGluThrIle-207 |
| SEQ. ID. NO. 30523 | 209-SerThrAlaArgLeuSerGlySerLeuLysAspValArgAla-222 |
| SEQ. ID. NO. 30524 | 224-LeuThrIleAspGlyGlyAsnIleArgLeuSerGlyLysSer-237 |
| SEQ. ID. NO. 30525 | 244-GluSerLeuAspLysThrLeuGlu-251 |
| SEQ. ID. NO. 30526 | 268-SerLeuProAspAla-272 |
| SEQ. ID. NO. 30527 | 292-GlySerLeuAspLeuGluAsnThrLys-300 |
| SEQ. ID. NO. 30528 | 302-GlyPheAlaAspArgAsnGlyIleProVal-311 |
| SEQ. ID. NO. 30529 | 320-IleArgGlnAspGlyThrVal-326 |
| SEQ. ID. NO. 30530 | 337-GlyArgGlyGlyIleArgLeuSerGlyLysIleAspThrGluLysAspIleLeu-354 |
| SEQ. ID. NO. 30531 | 362-SerValGlyAlaGluAspValLeu-369 |
| SEQ. ID. NO. 30532 | 372-AlaPheLysGlyArgLeuAspGlySerIle-381 |
| SEQ. ID. NO. 30533 | 386-ThrThrAlaSerProLysIle-392 |
| SEQ. ID. NO. 30534 | 397-GlyThrGlyThrAlaArgThrAspGlySerLeu-407 |
| SEQ. ID. NO. 30535 | 411-SerAspProAlaAsnGluGlnArgLysLeuVal-421 |
| SEQ. ID. NO. 30536 | 428-SerAlaGlyGluGlySerLeuThr-435 |
| SEQ. ID. NO. 30537 | 442-LeuPheLysAspArgLeuLeuLysLeuAspIleArgSerArgAlaPheAspProSerArgIleAspProGlnPheProAlaGlyAspIleAsnGly-473 |
| SEQ. ID. NO. 30538 | 480-GluLeuAlaLysGluLysPheThrGlyLys-489 |
| SEQ. ID. NO. 30539 | 508-IleValTyrGluSerArgHisLeuProArgAlaAlaVal-520 |
| SEQ. ID. NO. 30540 | 522-LeuArgLeuGlyArgAsnIleValLysThrAspGlyGlyPheGlyLysLysGlyAspArgLeuAsn-543 |
| SEQ. ID. NO. 30541 | 548-AlaProAspLeuSerArgPheGly-555 |
| SEQ. ID. NO. 30542 | 563-AsnValArgGlyHisLeuSerGlyAspLeuAspGlyGlyIleArgThrPheGluThrAspLeuSerGlyThrAlaArg-588 |
| SEQ. ID. NO. 30543 | 594-LysAlaAlaAspIleArgSer-600 |
| SEQ. ID. NO. 30544 | 605-LeuLysGlySerProGlyThrSerArgProMetArgAlaAspIleLysGlyGlyArgLeu-624 |
| SEQ. ID. NO. 30545 | 641-GluGlyThrGlyAla-645 |
| SEQ. ID. NO. 30546 | 647-HisArgIleArgThr-651 |
| SEQ. ID. NO. 30547 | 657-LeuAspGlyLysProPheLysLeuAspLeuAspAlaSerGlyGlyIleAsnArgGluLeuThrArgTrpLysGlySerIle-683 |

TABLE 1-continued

| | |
|---|---|
| SEQ. ID. NO. 30548 | 696-LeuGlnAsnArgMetThrLeu-702 |
| SEQ. ID. NO. 30549 | 729-SerTrpAspArgLysThrGlyIleSerAlaLysGlyGlyAlaArgGly-744 |
| SEQ. ID. NO. 30550 | 764-LeuAsnGlyAspTrp-768 |
| SEQ. ID. NO. 30551 | 774-HisAsnAlaArgGly-778 |
| SEQ. ID. NO. 30552 | 782-IleSerArgGlnSerGlyAspAlaValLeu-791 |
| SEQ. ID. NO. 30553 | 803-SerLeuLysThrArgPheGlnAsnAspArgIleGly-814 |
| SEQ. ID. NO. 30554 | 817-LeuAspGlyGlyAlaArgPheGlyArgIleAsnAla-828 |
| SEQ. ID. NO. 30555 | 844-ProLeuGlyGlyArgIleThr-850 |
| SEQ. ID. NO. 30556 | 880-IleGlyGlyArgValGlySerProSerVal-889 |
| SEQ. ID. NO. 30557 | 893-ValAsnGlySerSerAsnTyrGlyLysIleAsnGly-904 |
| SEQ. ID. NO. 30558 | 908-ValGlyGlnSerArgSerPheAspThrAlaProLeuGlyGlyArg-922 |
| SEQ. ID. NO. 30559 | 928-AlaAspAlaGluAlaPhe-933 |
| SEQ. ID. NO. 30560 | 941-GlnThrValLysGlySerLeu-947 |
| SEQ. ID. NO. 30561 | 956-SerIleAlaAspProHisLeuGlyGly-964 |
| SEQ. ID. NO. 30562 | 966-IleAsnGlyAspLysLeuTyrTyrArgAsnGlnThr-977 |
| SEQ. ID. NO. 30563 | 982-LeuAspAsnGlySerLeuArg-988 |
| SEQ. ID. NO. 30564 | 991-IleAlaGlyArgLysTrpVal-997 |
| SEQ. ID. NO. 30565 | 1001-LeuLysPheArgHisGluGlyThrAlaGluLeuSerGly-1013 |
| SEQ. ID. NO. 30566 | 1015-ValSerMetGluAsnSerValProAspValAspIle-1026 |
| SEQ. ID. NO. 30567 | 1031-AspLysTyrArgIleLeuSerArgProAsnArgArgLeuThr-1044 |
| SEQ. ID. NO. 30568 | 1047-GlyAsnThrArgLeuArgTyrSerProGlnLysGlyIle-1059 |
| SEQ. ID. NO. 30569 | 1065-IleLysThrAspGlnGlyLeuPheGlySerGlnLysSerSerMetProSerValGlyAspAspVal-1086 |
| SEQ. ID. NO. 30570 | 1091-GluValLysLysGluAlaAlaAla-1098 |
| SEQ. ID. NO. 30571 | 1109-AspLeuAsnAspGlyIleArgPhe-1116 |
| SEQ. ID. NO. 30572 | 1134-GlnProGlyGlyAsnValArgGlyValGly-1143 |
| SEQ. ID. NO. 30573 | 1146-ArgValIleLysGlyArgTyrLysAlaTyrGlyGlnAspLeuAspIleThrLysGlyThr-1165 |
| SEQ. ID. NO. 30574 | 1171-ProLeuAsnAspProAsnLeuAsnIleArgAlaGluArgArgLeuSerProValGly-1189 |
| SEQ. ID. NO. 30575 | 1197-SerLeuAsnSerProArgIle-1203 |
| SEQ. ID. NO. 30576 | 1207-AlaAsnGluProMetSerGluLysAspLysLeu-1217 |
| SEQ. ID. NO. 30577 | 1225-AlaGlySerGlySerSerGlyAspAsnAlaAla-1235 |
| SEQ. ID. NO. 30578 | 1246-GlyGlnIleAsnAspArgIleGlyLeu-1254 |
| SEQ. ID. NO. 30579 | 1256-AspAspLeuGlyPheThrSerLysArgSerArgAsnAlaGlnThrGlyGluLeuAsnProAlaGlu-1277 |
| SEQ. ID. NO. 30580 | 1283-GlyLysGlnLeuThrGlyLys-1289 |
| SEQ. ID. NO. 30581 | 1298-IleSerSerAlaGluGlnSerVal-1305 |
| SEQ. ID. NO. 30582 | 1321-IleGlySerArgSerSerGlyGlyGluLeu-1330 |
| SEQ. ID. NO. 30583 | 1335-ArgPheAspArgLeuPheGlySerAspLysLysAspSerAlaGlyAsnGlyLysGlyLys-1354 |
| Hydrophilic Regions - Hopp-Woods | |
| SEQ. ID. NO. 30584 | 56-PheAspGlyAspAsnTrpSerIleGluThrGluGlyAlaAspLeuLysIleSerArg-74 |
| SEQ. ID. NO. 30585 | 83-GluLeuMetArgArgSerLeuHis-90 |
| SEQ. ID. NO. 30586 | 105-ProThrProProLysGluGluArgProProGlnGlyLeu-117 |
| SEQ. ID. NO. 30587 | 130-AspArgPheGluThrGlyLys-136 |
| SEQ. ID. NO. 30588 | 141-LysThrPheAspLys-145 |
| SEQ. ID. NO. 30589 | 157-TyrArgTyrAspArgLysGlyHisArgLeuAspLeuLysAlaAlaAsp-172 |
| SEQ. ID. NO. 30590 | 200-GlyGlyPheGluGlyGluThrIle-207 |
| SEQ. ID. NO. 30591 | 215-GlySerLeuLysAspValArgAla-222 |
| SEQ. ID. NO. 30592 | 244-GluSerLeuAspLysThrLeuGlu-251 |
| SEQ. ID. NO. 30593 | 292-GlySerLeuAspLeuGluAsnThrLys-300 |
| SEQ. ID. NO. 30594 | 302-GlyPheAlaAspArgAsnGlyIlePro-310 |
| SEQ. ID. NO. 30595 | 320-IleArgGlnAspGly-324 |
| SEQ. ID. NO. 30596 | 343-LeuSerGlyLysIleAspThrGluLysAspIleLeu-354 |
| SEQ. ID. NO. 30597 | 364-GlyAlaGluAspValLeu-369 |
| SEQ. ID. NO. 30598 | 373-PheLysGlyArgLeuAspGly-379 |
| SEQ. ID. NO. 30599 | 400-ThrAlaArgThrAspGly-405 |
| SEQ. ID. NO. 30600 | 411-SerAspProAlaAsnGluGlnArgLysLeuVal-421 |
| SEQ. ID. NO. 30601 | 429-AlaGlyGluGlySerLeu-434 |
| SEQ. ID. NO. 30602 | 442-LeuPheLysAspArgLeuLeuLysLeuAspIleArgSerArgAlaPheAspProSerArgIleAspPro-464 |
| SEQ. ID. NO. 30603 | 480-GluLeuAlaLysGluLysPheThrGly-488 |
| SEQ. ID. NO. 30604 | 508-IleValTyrGluSerArgHisLeuPro-516 |
| SEQ. ID. NO. 30605 | 522-LeuArgLeuGlyArgAsnIleValLysThrAspGlyGlyPheGlyLysLysGlyAspArgLeuAsn-543 |
| SEQ. ID. NO. 30606 | 570-GlyAspLeuAspGlyGlyIleArgThrPheGluThrAspLeuSerGlyThrAla-587 |
| SEQ. ID. NO. 30607 | 594-LysAlaAlaAspIleArgSer-600 |
| SEQ. ID. NO. 30608 | 607-GlySerProGlyThrSerArgProMetArgAlaAspIleLysGlyGlyArg-623 |
| SEQ. ID. NO. 30609 | 647-HisArgIleArgThr-651 |
| SEQ. ID. NO. 30610 | 657-LeuAspGlyLysProPheLysLeuAspLeuAspAla-668 |
| SEQ. ID. NO. 30611 | 670-GlyGlyIleAsnArgGluLeuThrArgTrpLysGly-681 |
| SEQ. ID. NO. 30612 | 729-SerTrpAspArgLysThrGlyIleSerAlaLysGlyGlyAlaArg-743 |
| SEQ. ID. NO. 30613 | 783-SerArgGlnSerGly-787 |
| SEQ. ID. NO. 30614 | 806-ThrArgPheGlnAsnAspArgIle-813 |
| SEQ. ID. NO. 30615 | 819-GlyGlyAlaArgPheGlyArgIleAsnAla-828 |
| SEQ. ID. NO. 30616 | 928-AlaAspAlaGluAlaPhe-933 |
| SEQ. ID. NO. 30617 | 1001-LeuLysPheArgHisGluGlyThrAlaGluLeu-1011 |
| SEQ. ID. NO. 30618 | 1019-AsnSerValProAspValAspIle-1026 |
| SEQ. ID. NO. 30619 | 1031-AspLysTyrArgIleLeuSerArgProAsnArgArgLeuThr-1044 |
| SEQ. ID. NO. 30620 | 1049-ThrArgLeuArgTyrSerPro-1055 |
| SEQ. ID. NO. 30621 | 1065-IleLysThrAspGln-1069 |
| SEQ. ID. NO. 30622 | 1075-GlnLysSerSerMet-1079 |
| SEQ. ID. NO. 30623 | 1091-GluValLysLysGluAlaAlaAla-1098 |
| SEQ. ID. NO. 30624 | 1109-AspLeuAsnAspGlyIleArg-1115 |
| SEQ. ID. NO. 30625 | 1146-ArgValIleLysGlyArgTyrLysAlaTyrGlyGlnAspLeuAspIleThrLys-1163 |
| SEQ. ID. NO. 30626 | 1179-IleArgAlaGluArgArgLeuSer-1186 |

TABLE 1-continued

| | |
|---|---|
| SEQ. ID. NO. 30627 | 1209-GluProMetSerGluLysAspLysLeu-1217 |
| SEQ. ID. NO. 30628 | 1225-AlaGlySerGlySerSerGlyAspAsnAlaAla-1235 |
| SEQ. ID. NO. 30629 | 1248-IleAsnAspArgIleGlyLeu-1254 |
| SEQ. ID. NO. 30630 | 1259-GlyPheThrSerLysArgSerArgAsnAlaGlnThrGlyGluLeuAsnPro-1275 |
| SEQ. ID. NO. 30631 | 1300-SerAlaGluGlnSerVal-1305 |
| SEQ. ID. NO. 30632 | 1321-IleGlySerArgSerSerGlyGly-1328 |
| SEQ. ID. NO. 30633 | 1340-PheGlySerAspLysLysAspSerAlaGlyAsnGlyLysGlyLys-1354 |
| g286-2 | |
| AMPHI Regions - AMPHI | |
| SEQ. ID. NO. 30634 | 69-GluIleLysAspMetVal-74 |
| SEQ. ID. NO. 30635 | 102-ProAspAsnValLysThr-107 |
| SEQ. ID. NO. 30636 | 145-ValAlaIleLeuGlyAsp-150 |
| SEQ. ID. NO. 30637 | 157-LeuAlaGluTyrTyrArgAsnAlaLeuGluAsnTrpGlnGlnProValGlySer-174 |
| SEQ. ID. NO. 30638 | 199-LeuAlaLysLeuGlyAsn-204 |
| SEQ. ID. NO. 30639 | 238-ThrGlnArgTyrProGluGlnThrValSerGlyLeuAlaArgPheGlnProGlyThr-256 |
| SEQ. ID. NO. 30640 | 326-AspTyrTyrAsnLeuPheAsnLys-333 |
| SEQ. ID. NO. 30641 | 354-IleSerGlnProArg-358 |
| SEQ. ID. NO. 30642 | 375-ThrThrGlnAsnLeu-379 |
| SEQ. ID. NO. 30643 | 428-ThrAlaSerTrpLysArgGlnLeuLeu-436 |
| SEQ. ID. NO. 30644 | 455-ThrLeuGlyThrPheLeu-460 |
| SEQ. ID. NO. 30645 | 513-GlyAlaSerSerVal-517 |
| SEQ. ID. NO. 30646 | 555-LeuSerGlyAlaValPheHisAspMetGlyAspAlaAlaAlaAsn-569 |
| SEQ. ID. NO. 30647 | 584-ArgTrpPheSerProLeu-589 |
| Antigenic Index - Jameson-Wolf | |
| SEQ. ID. NO. 30648 | 1-MetHisAspThrArgThrMetMet-8 |
| SEQ. ID. NO. 30649 | 30-AlaAspLeuSerGluAsnLysAla-37 |
| SEQ. ID. NO. 30650 | 43-PheLysSerLysSerProAspThrGluSerValLysLeuLysProLysPheProVal-61 |
| SEQ. ID. NO. 30651 | 63-IleAspThrGlnAspSerGluIleLysAspMetValGluGluHisLeu-78 |
| SEQ. ID. NO. 30652 | 83-GlnGlnGlnGluGluValLeuAspLysGluGlnThr-94 |
| SEQ. ID. NO. 30653 | 97-LeuAlaGluGluAlaProAspAsnValLysThrMetLeuArgSerLysGlyTyrPheSerSerLysValSerLeuThrGluLysAspGlyAla-127 |
| SEQ. ID. NO. 30654 | 133-ThrProGlyProArgThrLysIle-140 |
| SEQ. ID. NO. 30655 | 151-IleLeuSerAspGlyAsnLeuAlaGluTyrTyrArgAsnAlaLeuGluAsnTrpGln-169 |
| SEQ. ID. NO. 30656 | 172-ValGlySerAspPheAspGlnAspSerTrpGluAsnSerLysThrSerVal-188 |
| SEQ. ID. NO. 30657 | 192-ValThrArgLysGlyTyrPro-198 |
| SEQ. ID. NO. 30658 | 201-LysLeuGlyAsnThrArgAlaAlaValAsnProAspThrAlaThrAla-216 |
| SEQ. ID. NO. 30659 | 223-AspSerGlyArgProIleAla-229 |
| SEQ. ID. NO. 30660 | 234-GluIleThrGlyThrGlnArgTyrProGluGlnThrVal-246 |
| SEQ. ID. NO. 30661 | 252-PheGlnProGlyThrProTyrAspLeu-260 |
| SEQ. ID. NO. 30662 | 270-LeuGluGlnAsnGlyHisTyrSerGly-278 |
| SEQ. ID. NO. 30663 | 283-AlaAspPheAspArgLeuGlnGlyAspArgValProVal-295 |
| SEQ. ID. NO. 30664 | 298-SerValThrGluValLysArgHisLysLeuGluThrGlyIleArgLeuAspSerGluTyrGlyLeuGlyGly-321 |
| SEQ. ID. NO. 30665 | 342-AspMetAspLysTyrGluThr-348 |
| SEQ. ID. NO. 30666 | 355-SerGlnProArgAsnTyrArgGlyAsnTyrTrp-365 |
| SEQ. ID. NO. 30667 | 368-AsnValSerTyrAsnArgSerThrThrGlnAsnLeuGluLysArgAlaPheSerGlyGly-387 |
| SEQ. ID. NO. 30668 | 391-ValArgAspArgAlaGlyIleAspAlaArgLeuGly-402 |
| SEQ. ID. NO. 30669 | 405-PheLeuAlaGluGlyArgLysIleProGlySerAspValAspLeuGlyAsnSerHis-423 |
| SEQ. ID. NO. 30670 | 430-SerTrpLysArgGlnLeu-435 |
| SEQ. ID. NO. 30671 | 441-HisProGluAsnGlyHisTyrLeuAspGlyLysIle-452 |
| SEQ. ID. NO. 30672 | 468-ThrSerAlaArgAlaGly-473 |
| SEQ. ID. NO. 30673 | 476-PheThrProGluAsnLysLysLeu-483 |
| SEQ. ID. NO. 30674 | 496-ValAlaArgAspAsnAlaAspValProSer-505 |
| SEQ. ID. NO. 30675 | 509-PheArgSerGlyGlyAlaSerSerValArgGlyTyrGluLeuAspSer-524 |
| SEQ. ID. NO. 30676 | 534-ValLeuProGluArgAlaLeu-540 |
| SEQ. ID. NO. 30677 | 562-AspMetGlyAspAla-566 |
| SEQ. ID. NO. 30678 | 568-AlaAsnPheLysArgMetLysLeuLysHisGlySerGlyLeu-581 |
| SEQ. ID. NO. 30679 | 598-TyrGlyHisSerAspLysLysIleArg-606 |
| Hydrophilic Regions - Hopp-Woods | |
| SEQ. ID. NO. 30680 | 1-MetHisAspThrArgThrMetMet-8 |
| SEQ. ID. NO. 30681 | 30-AlaAspLeuSerGluAsnLysAla-37 |
| SEQ. ID. NO. 30682 | 44-LysSerLysSerProAspThrGluSerValLysLeuLysProLysPheProVal-61 |
| SEQ. ID. NO. 30683 | 63-IleAspThrGlnAspSerGluIleLysAspMetValGluGluHisLeu-78 |
| SEQ. ID. NO. 30684 | 84-GlnGlnGluGluValLeuAspLysGluGlnThr-94 |
| SEQ. ID. NO. 30685 | 97-LeuAlaGluGluAlaProAspAsnValLysThrMetLeuArgSer-111 |
| SEQ. ID. NO. 30686 | 119-ValSerLeuThrGluLysAspGlyAla-127 |
| SEQ. ID. NO. 30687 | 134-ProGlyProArgThrLysIle-140 |
| SEQ. ID. NO. 30688 | 174-SerAspPheAspGlnAspSerTrpGluAsnSerLysThr-186 |
| SEQ. ID. NO. 30689 | 192-ValThrArgLysGlyTyrPro-198 |
| SEQ. ID. NO. 30690 | 206-ArgAlaAlaValAsnProAspThrAlaThr-215 |
| SEQ. ID. NO. 30691 | 239-GlnArgTyrProGlu-243 |
| SEQ. ID. NO. 30692 | 283-AlaAspPheAspArgLeuGlnGlyAspArgValProVal-295 |
| SEQ. ID. NO. 30693 | 298-SerValThrGluValLysArgHisLysLeuGluThrGlyIleArgLeuAspSerGluTyr-317 |
| SEQ. ID. NO. 30694 | 342-AspMetAspLysTyrGluThr-348 |
| SEQ. ID. NO. 30695 | 373-ArgSerThrThrGlnAsnLeuGluLysArgAlaPhe-384 |
| SEQ. ID. NO. 30696 | 392-ArgAspArgAlaGlyIleAspAlaArgLeuGly-402 |
| SEQ. ID. NO. 30697 | 405-PheLeuAlaGluGlyArgLysIleProGlySerAspValAspLeu-419 |
| SEQ. ID. NO. 30698 | 478-ProGluAsnLysLysLeu-483 |
| SEQ. ID. NO. 30699 | 496-ValAlaArgAspAsnAlaAspVal-503 |
| SEQ. ID. NO. 30700 | 518-ArgGlyTyrGluLeuAspSer-524 |
| SEQ. ID. NO. 30701 | 534-ValLeuProGluArgAlaLeu-540 |
| SEQ. ID. NO. 30702 | 562-AspMetGlyAspAla-566 |

TABLE 1-continued

| | |
|---|---|
| SEQ. ID. NO. 30703 | 568-AlaAsnPheLysArgMetLysLeuLysHis-577 |
| SEQ. ID. NO. 30704 | 600-HisSerAspLysLysIleArg-606 |
| g287 | |
| AMPHI Regions - AMPHI | |
| SEQ. ID. NO. 30705 | 32-AspThrProSerLysPro-37 |
| SEQ. ID. NO. 30706 | 111-MetProGlnAsnAlaAlaGluSerAlaAsnGlnThrGly-123 |
| SEQ. ID. NO. 30707 | 195-LeuSerAspGluGluLysIleLysArgTyrLysLys-206 |
| SEQ. ID. NO. 30708 | 351-LysSerValAspGlyIleIleAspSer-359 |
| SEQ. ID. NO. 30709 | 378-GlyPheLysGlyThrTrpThr-384 |
| SEQ. ID. NO. 30710 | 391-ValSerGlyArgPheTyr-396 |
| Antigenic Index - Jameson-Wolf | |
| SEQ. ID. NO. 30711 | 18-CysGlyGlyGlyGlyGlyGlySerProAspValLysSerAlaAspThrProSerLysProAla-38 |
| SEQ. ID. NO. 30712 | 50-ValLeuProLysGluLysLysAspGluGluAlaAlaGlyGlyAlaProGlnAlaAspThrGlnAspAlaThrAlaGlyGluGlySerGlnAsp-80 |
| SEQ. ID. NO. 30713 | 85-SerAlaGluAsnThrGlyAsnGlyGlyAlaAlaThrThrAspAsnProLysAsnGluAspAlaGlyAlaGlnAsnAspMetProGlnAsnAla AlaGluSerAlaAsnGlnThrGlyAsnAsnGlnProAlaGlySerSerAspSerAlaProAlaSerAsnProAlaProAlaAsnGlyGlySerAspPheGly ArgThrAsnValGly-154 |
| SEQ. ID. NO. 30714 | 160-AspGlyProSerGlnAsn-165 |
| SEQ. ID. NO. 30715 | 169-ThrHisCysLysGlyAspSerCysAsnGlyAspAsnLeuLeuAspGluGluAlaProSerLysSerGluPheGluLysLeuSerAspGluGluLys IleLysArgTyrLysLysAspGluGlnArgGluAsnPhe-213 |
| SEQ. ID. NO. 30716 | 217-ValAlaAspArgValLysLysAspGlyThrAsnLys-228 |
| SEQ. ID. NO. 30717 | 233-TyrThrAspLysProProThrArgSerAlaArgSerArgArgSerLeuPro-249 |
| SEQ. ID. NO. 30718 | 262-ThrLeuIleValAspGlyGluAla-269 |
| SEQ. ID. NO. 30719 | 281-AlaProGluGlyAsnTyrArgTyrLeu-289 |
| SEQ. ID. NO. 30720 | 292-GlyAlaGluLysLeuProGlyGlySerTyr-301 |
| SEQ. ID. NO. 30721 | 305-ValGlnGlyGluProAlaLysGlyGluMet-314 |
| SEQ. ID. NO. 30722 | 329-HisMetGluAsnGlyArgProTyrProSerGlyGlyArgPheAlaAla-344 |
| SEQ. ID. NO. 30723 | 346-ValAspPheGlySerLysSerValAspGlyIleIleAspSerGlyAspAspLeuHisMetGlyThrGlnLysPheLysAlaAlaIleAspGlyAsnGly PheLysGlyThrTrpThrGluAsnGlyGlyGlyAspValSerGly-393 |
| SEQ. ID. NO. 30724 | 395-PheTyrGlyProAlaGlyGluGluValAlaGlyLysTyrSerTyrArgProThrAspAlaGluLysGlyGlyPhe-419 |
| SEQ. ID. NO. 30725 | 423-AlaGlyLysLysAspArgAsp-429 |
| Hydrophilic Regions - Hopp-Woods | |
| SEQ. ID. NO. 30726 | 22-GlyGlyGlySerProAspValLysSerAlaAspThrProSerLysProAla-38 |
| SEQ. ID. NO. 30727 | 50-ValLeuProLysGluLysLysAspGluGluAlaAlaGly-62 |
| SEQ. ID. NO. 30728 | 65-ProGlnAlaAspThrGlnAspAlaThrAlaGlyGluGlySerGlnAsp-80 |
| SEQ. ID. NO. 30729 | 85-SerAlaGluAsnThrGly-90 |
| SEQ. ID. NO. 30730 | 95-AlaThrThrAspAsnProLysAsnGluAspAlaGlyAlaGlnAsnAspMetProGlnAsnAlaAlaGluSerAlaAsnGln-121 |
| SEQ. ID. NO. 30731 | 126-GlnProAlaGlySerSerAspSerAlaPro-135 |
| SEQ. ID. NO. 30732 | 144-GlyGlySerAspPheGlyArg-150 |
| SEQ. ID. NO. 30733 | 171-CysLysGlyAspSerCysAsnGly-178 |
| SEQ. ID. NO. 30734 | 180-AsnLeuLeuAspGluGluAlaProSerLysSerGluPheGluLysLeuSerAspGluGluLysIleLysArgTyrLysLysAspGluGlnArgGlu AsnPhe-213 |
| SEQ. ID. NO. 30735 | 217-ValAlaAspArgValLysLysAspGlyThrAsn-227 |
| SEQ. ID. NO. 30736 | 235-AspLysProProThrArgSerAlaArgSerArgArgSerLeuPro-249 |
| SEQ. ID. NO. 30737 | 263-LeuIleValAspGlyGluAla-269 |
| SEQ. ID. NO. 30738 | 292-GlyAlaGluLysLeuPro-297 |
| SEQ. ID. NO. 30739 | 305-ValGlnGlyGluProAlaLysGlyGluMet-314 |
| SEQ. ID. NO. 30740 | 331-GluAsnGlyArgProTyrProSer-338 |
| SEQ. ID. NO. 30741 | 346-ValAspPheGlySerLysSerValAspGlyIleIleAspSerGlyAspAspLeuHis-364 |
| SEQ. ID. NO. 30742 | 368-GlnLysPheLysAlaAlaIleAsp-375 |
| SEQ. ID. NO. 30743 | 387-GlyGlyGlyAspValSerGly-393 |
| SEQ. ID. NO. 30744 | 399-AlaGlyGluGluValAlaGly-405 |
| SEQ. ID. NO. 30745 | 407-TyrSerTyrArgProThrAspAlaGluLysGlyGly-418 |
| SEQ. ID. NO. 30746 | 423-AlaGlyLysLysAspArgAsp-429 |
| g288 | |
| AMPHI Regions - AMPHI | |
| SEQ. ID. NO. 30747 | 7-ValSerArgValLeu-11 |
| SEQ. ID. NO. 30748 | 54-IleValThrLysCysAla-59 |
| SEQ. ID. NO. 30749 | 61-ArgProTyrArgThrPheSerProLeuProVal-71 |
| SEQ. ID. NO. 30750 | 97-HisSerThrLeuArg-101 |
| SEQ. ID. NO. 30751 | 150-ThrLeuPheGlnAlaGlyPheAsp-157 |
| Antigenic Index - Jameson-Wolf | |
| SEQ. ID. NO. 30752 | 2-HisThrGlyGlnAla-6 |
| SEQ. ID. NO. 30753 | 28-AsnLeuProGluArgSerAlaGlySer-36 |
| SEQ. ID. NO. 30754 | 58-CysAlaValArgProTyrArgThrPheSerPro-68 |
| SEQ. ID. NO. 30755 | 72-LeuProLysGlnProSerAla-78 |
| SEQ. ID. NO. 30756 | 89-LeuProArgProAlaValAsnArgHisSerThrLeuArgSerProAspPheProProArgMet-109 |
| SEQ. ID. NO. 30757 | 113-IleArgGlyAspCysLeuPro-119 |
| SEQ. ID. NO. 30758 | 126-IleIleThrArgAsnAlaLysMetProSerGluThrValGlnValSerAspGlyIleGlnProLys-147 |
| SEQ. ID. NO. 30759 | 155-GlyPheAspGluAlaVal-160 |
| Hydrophilic Regions - Hopp-Woods | |
| SEQ. ID. NO. 30760 | 28-AsnLeuProGluArgSerAla-34 |
| SEQ. ID. NO. 30761 | 58-CysAlaValArgPro-62 |
| SEQ. ID. NO. 30762 | 98-SerThrLeuArgSerProAspPheProPro-107 |
| SEQ. ID. NO. 30763 | 113-IleArgGlyAspCys-117 |
| SEQ. ID. NO. 30764 | 126-IleIleThrArgAsnAlaLysMetProSerGluThrValGlnVal-140 |
| SEQ. ID. NO. 30765 | 155-GlyPheAspGluAlaVal-160 |
| g292-2 | |
| AMPHI Regions - AMPHI | |
| SEQ. ID. NO. 30766 | 7-LysIleLeuThrProPheThrValLeuProLeu-17 |
| SEQ. ID. NO. 30767 | 40-GlyLysSerValAla-44 |

TABLE 1-continued

| | |
|---|---|
| SEQ. ID. NO. 30768 | 62-ValLeuSerValSerGlu-67 |
| SEQ. ID. NO. 30769 | 69-ProValLysGlyIleTyrGlu-75 |
| SEQ. ID. NO. 30770 | 110-GluArgAlaAlaAspLeu-115 |
| SEQ. ID. NO. 30771 | 124-ProLeuAspLysAlaIleLysGluValArgGly-134 |
| SEQ. ID. NO. 30772 | 150-PheCysLysArgLeuGluHisGluPheGluLysMetThrAspValThr-165 |
| SEQ. ID. NO. 30773 | 195-LysAlaTrpThrAspTrpMetArg-202 |
| SEQ. ID. NO. 30774 | 212-IleCysAspAsnProVal-217 |
| Antigenic Index - Jameson-Wolf | |
| SEQ. ID. NO. 30775 | 1-MetLysThrLysLeu-5 |
| SEQ. ID. NO. 30776 | 23-ThrProValSerAsnAlaAsnAlaGluSerAlaValLysAlaGluSerAlaGlyLysSerVal-43 |
| SEQ. ID. NO. 30777 | 47-LeuLysAlaArgLeuGluLysThrTyrSerAlaGlnAspLeuLys-61 |
| SEQ. ID. NO. 30778 | 66-SerGluThrProValLysGlyIle-73 |
| SEQ. ID. NO. 30779 | 85-TyrThrAspAlaGluGlyGlyTyr-92 |
| SEQ. ID. NO. 30780 | 99-IleAsnIleAspThrArgLysAsnLeuThrGluGluArgAlaAlaAspLeuAsnLys-117 |
| SEQ. ID. NO. 30781 | 124-ProLeuAspLysAlaIleLysGluValArgGlyAsnGlyLysLeuLysVal-140 |
| SEQ. ID. NO. 30782 | 142-ValPheSerAspProAspCysProPhe-150 |
| SEQ. ID. NO. 30783 | 152-LysArgLeuGluHisGluPheGluLysMetThrAsp-163 |
| SEQ. ID. NO. 30784 | 177-HisProAspAlaAlaArgLysAla-184 |
| SEQ. ID. NO. 30785 | 189-CysGlnProAspArgAlaLysAla-196 |
| SEQ. ID. NO. 30786 | 200-TrpMetArgLysGlyLysPheProVal-208 |
| SEQ. ID. NO. 30787 | 210-GlySerIleCysAspAsnProValAlaGluThrThrSerLeuGlyGlu-225 |
| SEQ. ID. NO. 30788 | 238-ProAsnGlyArgThrGlnSerGlyTyrSerPro-248 |
| SEQ. ID. NO. 30789 | 250-ProGlnLeuGluGluIleIleArgLysAsnGlnGln-261 |
| Hydrophilic Regions - Hopp-Woods | |
| SEQ. ID. NO. 30790 | 1-MetLysThrLysLeu-5 |
| SEQ. ID. NO. 30791 | 28-AlaAsnAlaGluSerAlaValLysAlaGluSerAlaGlyLysSerVal-43 |
| SEQ. ID. NO. 30792 | 47-LeuLysAlaArgLeuGluLysThrTyrSer-56 |
| SEQ. ID. NO. 30793 | 99-IleAsnIleAspThrArgLysAsnLeuThrGluGluArgAlaAlaAspLeuAsnLys-117 |
| SEQ. ID. NO. 30794 | 124-ProLeuAspLysAlaIleLysGluValArgGlyAsnGlyLysLeuLys-139 |
| SEQ. ID. NO. 30795 | 144-SerAspProAspCysProPhe-150 |
| SEQ. ID. NO. 30796 | 152-LysArgLeuGluHisGluPheGluLysMetThrAsp-163 |
| SEQ. ID. NO. 30797 | 179-AspAlaAlaArgLysAla-184 |
| SEQ. ID. NO. 30798 | 190-GlnProAspArgAlaLysAla-196 |
| SEQ. ID. NO. 30799 | 200-TrpMetArgLysGlyLysPhe-206 |
| SEQ. ID. NO. 30800 | 240-GlyArgThrGlnSer-244 |
| SEQ. ID. NO. 30801 | 250-ProGlnLeuGluGluIleIleArgLysAsnGlnGln-261 |
| g294-2 | |
| AMPHI Regions - AMPHI | |
| SEQ. ID. NO. 30802 | 27-ArgPheProAlaAlaLeuArgArgTyrSer-36 |
| SEQ. ID. NO. 30803 | 45-LysProAlaGlyThr-49 |
| SEQ. ID. NO. 30804 | 51-TrpHisArgValArgArgPheLysSerAsnArgArgThrArgGlyValLysProLeu-69 |
| SEQ. ID. NO. 30805 | 85-AlaTrpThrAlaLeuSerHisAsnIleAlaGluArgAlaArgGluSerProArgArgCysGlyLysArgTyrAlaAspIleGlyGly-113 |
| SEQ. ID. NO. 30806 | 134-ValAlaHisIleIleHisLeuTyrCys-142 |
| SEQ. ID. NO. 30807 | 165-ValSerArgGluAlaArgArgGluVal-173 |
| SEQ. ID. NO. 30808 | 176-AlaMetSerTyrArg-180 |
| SEQ. ID. NO. 30809 | 212-PheAlaThrSerPheGly-217 |
| SEQ. ID. NO. 30810 | 227-AlaPheSerValLeuAlaHisPhe-234 |
| SEQ. ID. NO. 30811 | 247-ThrValGlyTrpSerLysTyrIleHisAlaVal-257 |
| Antigenic Index - Jameson-Wolf | |
| SEQ. ID. NO. 30812 | 20-AlaValArgThrSerSerAsnArgPhe-28 |
| SEQ. ID. NO. 30813 | 30-AlaAlaLeuArgArgTyrSerAlaPheArg-39 |
| SEQ. ID. NO. 30814 | 44-ProLysProAlaGlyThrProTrpHisArgValArgArgPheLysSerAsnArgArgThrArgGlyValLysProLeuLysLysProTyrLeu-74 |
| SEQ. ID. NO. 30815 | 76-ArgGlyAlaGluCysArgCysArgArgAla-85 |
| SEQ. ID. NO. 30816 | 93-IleAlaGluArgAlaArgGluSerProArgArgCysGlyLysArgTyrAlaAspIleGlyGlyAspSerAspThrIleArgIleArgValPheArgLeuGluHisArgMet-129 |
| SEQ. ID. NO. 30817 | 161-HisThrGlyArgValSerArgGluAlaArgArgGluValGluLysAlaMetSer-178 |
| SEQ. ID. NO. 30818 | 240-LysMetAlaArgSer-244 |
| Hydrophilic Regions - Hopp-Woods | |
| SEQ. ID. NO. 30819 | 20-AlaValArgThrSerSerAsnArg-27 |
| SEQ. ID. NO. 30820 | 30-AlaAlaLeuArgArg-34 |
| SEQ. ID. NO. 30821 | 52-HisArgValArgArgPheLysSerAsnArgArgThrArgGlyValLysProLeuLysLys-71 |
| SEQ. ID. NO. 30822 | 76-ArgGlyAlaGluCysArgCysArgArgAla-85 |
| SEQ. ID. NO. 30823 | 93-IleAlaGluArgAlaArgGluSerProArgArgCysGlyLysArgTyrAlaAspIleGlyGlyAspSerAspThrIleArg-119 |
| SEQ. ID. NO. 30824 | 121-ArgValPheArgLeuGluHisArgMet-129 |
| SEQ. ID. NO. 30825 | 164-ArgValSerArgGluAlaArgArgGluValGluLysAlaMetSer-178 |
| g295 | |
| AMPHI Regions - AMPHI | |
| SEQ. ID. NO. 30826 | 79-PheArgGlnProArg-83 |
| SEQ. ID. NO. 30827 | 111-ValGlnArgPhePheArgGlnPro-118 |
| SEQ. ID. NO. 30828 | 131-AlaPheLeuHisGlnIle-136 |
| SEQ. ID. NO. 30829 | 163-ValIleArgLysIleAlaAlaLeu-170 |
| SEQ. ID. NO. 30830 | 176-AsnLeuArgGlyPhePro-181 |
| SEQ. ID. NO. 30831 | 189-HisGlnGlnArgArgIleGlyLysThr-197 |
| SEQ. ID. NO. 30832 | 263-TyrIleIleLysProLeuGluHis-270 |
| Antigenic Index - Jameson-Wolf | |
| SEQ. ID. NO. 30833 | 4-MetAlaArgHisAspGlyGlnGlnGly-12 |
| SEQ. ID. NO. 30834 | 18-LeuProArgArgGlnGln-23 |
| SEQ. ID. NO. 30835 | 36-AlaAlaAlaHisGlyAsnArgProAlaSerAspAlaPhePheLysLeuProArgGlnArgPheHisVal-58 |
| SEQ. ID. NO. 30836 | 73-HisGlyCysArgAlaGlnPheArgGlnProArgArgIleArgLeuArgLeuArgGlnThrAlaArgGlnArgSerGlyCysGlyThrAspGlnAlaAlaAsp-106 |

TABLE 1-continued

| | |
|---|---|
| SEQ. ID. NO. 30837 | 115-PheArgGlnProArgIleArgGlnLysGlnArgHisThrArgSerProAla-131 |
| SEQ. ID. NO. 30838 | 137-GlyProAspPheGly-141 |
| SEQ. ID. NO. 30839 | 144-GlnAsnAlaGluHisArgAla-150 |
| SEQ. ID. NO. 30840 | 171-ArgIleGlyLysGlnAsnLeuArgGlyPheProSerArgArgGlyHisLeuArgHisGlnGlnArgArgIleGlyLysThrProProGlnLeuAla-202 |
| SEQ. ID. NO. 30841 | 207-GlyGlyThrArgPheSerAspArgAsnGlyValTyrProAsnArgAlaGlyAsnGlyIleArgMetArgLeuAlaGlu-232 |
| SEQ. ID. NO. 30842 | 239-ProValCysArgGlyThrSerGly-246 |
| SEQ. ID. NO. 30843 | 253-ProTyrProTyrArgArgLysGlnProGlnTyr-263 |
| SEQ. ID. NO. 30844 | 274-SerCysLysThrAsnAlaValArgThrValArgThrAlaPheArgGlnArgAsnGlnIleSer-294 |
| Hydrophilic Regions - Hopp-Woods | |
| SEQ. ID. NO. 30845 | 5-AlaArgHisAspGlyGlnGln-11 |
| SEQ. ID. NO. 30846 | 18-LeuProArgArgGlnGln-23 |
| SEQ. ID. NO. 30847 | 36-AlaAlaAlaHisGlyAsnArgProAlaSer-45 |
| SEQ. ID. NO. 30848 | 77-AlaGlnPheArgGlnProArgArgIleArgLeuArgLeuArgGlnThrAlaArgGlnArgSerGlyCysGlyThrAspGlnAlaAla-105 |
| SEQ. ID. NO. 30849 | 118-ProArgIleArgGlnLysGlnArgHisThrArg-128 |
| SEQ. ID. NO. 30850 | 146-AlaGluHisArgAla-150 |
| SEQ. ID. NO. 30851 | 171-ArgIleGlyLysGlnAsnLeu-177 |
| SEQ. ID. NO. 30852 | 180-PheProSerArgArgGlyHisLeuArgHisGlnGlnArgArgIleGlyLysThrProPro-199 |
| SEQ. ID. NO. 30853 | 210-ArgPheSerAspArgAsnGly-216 |
| SEQ. ID. NO. 30854 | 226-IleArgMetArgLeuAlaGlu-232 |
| SEQ. ID. NO. 30855 | 239-ProValCysArgGlyThr-244 |
| SEQ. ID. NO. 30856 | 255-ProTyrArgArgLysGlnPro-261 |
| SEQ. ID. NO. 30857 | 281-ArgThrValArgThrAlaPheArgGlnArgAsnGlnIle-293 |
| g297 | |
| AMPHI Regions - AMPHI | |
| SEQ. ID. NO. 30858 | 69-GlnProGlyAspSerLeuAlaAspValLeuAla-79 |
| SEQ. ID. NO. 30859 | 86-AspGluIleAlaArgIleThrGluLysTyr-95 |
| SEQ. ID. NO. 30860 | 157-LeuProThrLeuArg-161 |
| SEQ. ID. NO. 30861 | 199-LeuLysGluGlyAspAla-204 |
| SEQ. ID. NO. 30862 | 272-LeuValTyrThrArgIleSerSer-279 |
| SEQ. ID. NO. 30863 | 333-HisAlaAsnGlyValGluThrLeuTyrAlaHisLeuSerAlaPheSerGln-349 |
| Antigenic Index - Jameson-Wolf | |
| SEQ. ID. NO. 30864 | 8-AlaLysHisArgLysTyrAla-14 |
| SEQ. ID. NO. 30865 | 31-AlaSerThrGluGlyThrGluArgValArgProGlnArgValGluGlnLysLeuPro-49 |
| SEQ. ID. NO. 30866 | 52-SerTrpGlyGlyAsnGly-57 |
| SEQ. ID. NO. 30867 | 67-AlaValGlnProGlyAspSerLeuAla-75 |
| SEQ. ID. NO. 30868 | 78-LeuAlaArgSerGlyMetAlaArgAspGluIleAlaArgIleThrGluLysTyrGlyGlyGluAlaAspLeuArgHisLeuArgAlaAspGln SerVal-110 |
| SEQ. ID. NO. 30869 | 115-GlyGlyAspGlySerAlaArgGlu-122 |
| SEQ. ID. NO. 30870 | 127-ThrAspGluAspGlyGluArgAsnLeuValAlaLeuGluLysLysGlyGlyIleTrpArgArgSerAlaSerAspAlaAspMetLysVal-156 |
| SEQ. ID. NO. 30871 | 167-ThrSerAlaArgGlySerLeuAlaArgAlaGluValProValGluIleArgGluSerLeuSer-187 |
| SEQ. ID. NO. 30872 | 194-PheSerLeuAspGlyLeuLysGluGlyAspAlaVal-205 |
| SEQ. ID. NO. 30873 | 228-GluValValLysGlyGlyThrThr-235 |
| SEQ. ID. NO. 30874 | 240-TyrTyrArgSerAspLysGluGlyGlyGlyGlyGlyAsnTyrTyrAspGluAspGlyArgValLeuGlnGluLysGlyGlyPheAsn-268 |
| SEQ. ID. NO. 30875 | 276-ArgIleSerSerProPheGlyTyr-283 |
| SEQ. ID. NO. 30876 | 295-HisThrGlyIleAspTyrAla-301 |
| SEQ. ID. NO. 30877 | 303-ProGlnGlyThrProValArgAlaSerAlaAspGly-314 |
| SEQ. ID. NO. 30878 | 318-PheLysGlyArgLysGlyGlyTyrGly-326 |
| SEQ. ID. NO. 30879 | 333-HisAlaAsnGlyValGlu-338 |
| SEQ. ID. NO. 30880 | 350-AlaGlnGlyAsnValArgGlyGlyGlu-358 |
| SEQ. ID. NO. 30881 | 365-SerThrGlyArgSerThrGlyProHisLeu-374 |
| SEQ. ID. NO. 30882 | 376-TyrGluAlaArgIleAsnGlyGlnProValAsn-386 |
| SEQ. ID. NO. 30883 | 393-ProThrProGluLeuThrGlnAlaAspLysAlaAla-404 |
| SEQ. ID. NO. 30884 | 408-GlnLysGlnLysAlaAspAlaLeu-415 |
| SEQ. ID. NO. 30885 | 426-ValSerGlnSerAsp-430 |
| Hydrophilic Regions - Hopp-Woods | |
| SEQ. ID. NO. 30886 | 8-AlaLysHisArgLysTyrAla-14 |
| SEQ. ID. NO. 30887 | 33-ThrGluGlyThrGluArgValArgProGlnArgValGluGlnLysLeu-48 |
| SEQ. ID. NO. 30888 | 68-ValGlnProGlyAspSerLeuAla-75 |
| SEQ. ID. NO. 30889 | 82-GlyMetAlaArgAspGluIleAlaArgIleThrGluLysTyrGlyGlyGluAlaAspLeuArgHisLeuArgAlaAspGln-108 |
| SEQ. ID. NO. 30890 | 117-AspGlySerAlaArgGlu-122 |
| SEQ. ID. NO. 30891 | 127-ThrAspGluAspGlyGluArgAsnLeuValAlaLeuGluLysLysGlyGlyIleTrpArgArgSerAlaSerAspAlaAspMetLysVal-156 |
| SEQ. ID. NO. 30892 | 167-ThrSerAlaArgGlySerLeuAlaArgAlaGluValProValGluIleArgGluSerLeu-186 |
| SEQ. ID. NO. 30893 | 194-PheSerLeuAspGlyLeuLysGluGlyAspAlaVal-205 |
| SEQ. ID. NO. 30894 | 242-ArgSerAspLysGluGlyGlyGly-249 |
| SEQ. ID. NO. 30895 | 253-TyrTyrAspGluAspGlyArgValLeuGlnGluLysGlyGlyPhe-267 |
| SEQ. ID. NO. 30896 | 306-ThrProValArgAlaSerAla-312 |
| SEQ. ID. NO. 30897 | 319-LysGlyArgLysGlyGlyTyr-325 |
| SEQ. ID. NO. 30898 | 352-GlyAsnValArgGlyGlyGlu-358 |
| SEQ. ID. NO. 30899 | 366-ThrGlyArgSerThrGly-371 |
| SEQ. ID. NO. 30900 | 378-AlaArgIleAsnGly-382 |
| SEQ. ID. NO. 30901 | 396-GluLeuThrGlnAlaAspLysAlaAla-404 |
| SEQ. ID. NO. 30902 | 408-GlnLysGlnLysAlaAspAlaLeu-415 |
| g298 | |
| AMPHI Regions - AMPHI | |
| SEQ. ID. NO. 30903 | 6-SerLeuPheAlaSerIleLeuMetSerAlaLeuIleAla-18 |
| SEQ. ID. NO. 30904 | 26-IleAsnAlaTyrTrpGlnGln-32 |
| SEQ. ID. NO. 30905 | 42-ProLeuAlaAlaTyr-46 |
| SEQ. ID. NO. 30906 | 62-LeuSerAspGlyIleLysThrPhe-69 |
| SEQ. ID. NO. 30907 | 134-ValGlnLysSerLeuLys-139 |
| SEQ. ID. NO. 30908 | 148-AsnLeuSerLysGln-152 |

TABLE 1-continued

| | |
|---|---|
| SEQ. ID. NO. 30909 | 157-SerTyrProSerPhePheAspTrpProLysThrIleGluGluThrLeuLysLysHisProGlu-177 |
| SEQ. ID. NO. 30910 | 188-AsnAspProTrpAsp-192 |
| SEQ. ID. NO. 30911 | 208-AlaGlnGluTyrLeuLysArgValAspArgIleLeuGlu-220 |
| SEQ. ID. NO. 30912 | 246-MetArgTyrLeuAspLysLeuLeuSerGluHisLeu-257 |
| SEQ. ID. NO. 30913 | 276-ArgTyrThrAspSer-280 |
| SEQ. ID. NO. 30914 | 308-GluLysIleMetGluLys-313 |
| Antigenic Index - Jameson-Wolf | |
| SEQ. ID. NO. 30915 | 22-SerGlnAsnProIleAsnAlaTyr-29 |
| SEQ. ID. NO. 30916 | 34-TyrHisArgAsnSerProLeuGluPro-42 |
| SEQ. ID. NO. 30917 | 47-GlyTrpTrpArgSerGlyAlaAlaLeuGlnGlu-57 |
| SEQ. ID. NO. 30918 | 70-LeuSerGlyGluThrProProThrAlaGlnAspGlyGlySerAlaAspMetProProGluAlaAlaAlaSerGluAlaAlaProProAlaGlyGly ThrGluTrpLysGlnGlyThrGlu-109 |
| SEQ. ID. NO. 30919 | 111-AlaAlaValArgSerGlyAspLysValPhePhe-121 |
| SEQ. ID. NO. 30920 | 136-LysSerLeuLysGlnGlnTyrGlyIleGluSerAlaAsnLeuSerLysGlnSerThr-154 |
| SEQ. ID. NO. 30921 | 162-PheAspTrpProLysThrIleGluGluThrLeuLysLysHisProGlu-177 |
| SEQ. ID. NO. 30922 | 186-GlyProAsnAspProTrp-191 |
| SEQ. ID. NO. 30923 | 194-ProValGlyLysArgTyrLeu-200 |
| SEQ. ID. NO. 30924 | 203-AlaSerAspGluTrpAla-208 |
| SEQ. ID. NO. 30925 | 211-TyrLeuLysArgValAspArgIleLeuGlu-220 |
| SEQ. ID. NO. 30926 | 238-LysLysValLysLeuAspGlyGlnMetArgTyrLeuAsp-250 |
| SEQ. ID. NO. 30927 | 252-LeuLeuSerGluHisLeuLysGly-259 |
| SEQ. ID. NO. 30928 | 269-ThrLeuSerGlyGlyLysGlyArgTyrThrAspSerValAsnValAsnGlyLysProValArgTyrArgSerLysAspGlyIle-296 |
| SEQ. ID. NO. 30929 | 301-GluGlyGlnLysLeuLeuAla-307 |
| SEQ. ID. NO. 30930 | 318-ProSerThrGlnProSerSerThrGlnPro-327 |
| Hydrophilic Regions - Hopp-Woods | |
| SEQ. ID. NO. 30931 | 73-GluThrProProThrAlaGlnAspGlyGlySerAlaAspMetProProGluAlaAlaAlaSerGluAlaAlaPro-97 |
| SEQ. ID. NO. 30932 | 102-ThrGluTrpLysGlnGlyThrGlu-109 |
| SEQ. ID. NO. 30933 | 111-AlaAlaValArgSerGlyAsp-117 |
| SEQ. ID. NO. 30934 | 148-AsnLeuSerLysGlnSerThr-154 |
| SEQ. ID. NO. 30935 | 166-LysThrIleGluGluThrLeuLysLysHisProGlu-177 |
| SEQ. ID. NO. 30936 | 211-TyrLeuLysArgValAspArgIleLeuGlu-220 |
| SEQ. ID. NO. 30937 | 238-LysLysValLysLeuAspGlyGlnMetArgTyrLeuAsp-250 |
| SEQ. ID. NO. 30938 | 252-LeuLeuSerGluHisLeuLysGly-259 |
| SEQ. ID. NO. 30939 | 271-SerGlyGlyLysGlyArgTyrThrAsp-279 |
| SEQ. ID. NO. 30940 | 281-ValAsnValAsnGlyLysProValArgTyrArgSerLysAspGlyIle-296 |
| SEQ. ID. NO. 30941 | 301-GluGlyGlnLysLeuLeuAla-307 |
| SEQ. ID. NO. 30942 | 319-SerThrGlnProSerSerThrGlnPro-327 |
| g299 | |
| AMPHI Regions - AMPHI | |
| SEQ. ID. NO. 30943 | 1-MetAsnProLysHisPheIleAlaPheSerAlaLeuPheAlaAlaThrGlnAlaGluAlaLeuProValAlaSerValSerProAspThrValThrVal SerProSerAlaProTyrThrAspThrAsnGlyLeuLeuThrAspTyrGlyAsnAlaAlaAlaSerProTrpMetLysLysLeuArgSerValAlaGln GlySerGlyGluAlaPheArgIleLeuGlnIleGlyAspSerHisThrAlaGlyAspPhePheThrAspAlaLeuArgLysArgLeuGlnLysThrTrp GlyAspGlyGlyIleGlyTrpValTyrProAlaAsnValLysGlyGlnArgMetAlaAlaValArgHisSerGlyAsnTrpGlnSerPheThrSerArg AsnAsnThrGlyAspPheProLeuGlyGlyIleLeuAlaGlnThrGlySerGlyGlyGlyMetThrLeuThrAlaSerAspGlyLysThrGlyLysGln ArgValSerLeuPheAlaLysProLeuLeuAlaGluGlnThrLeuThrValAsnGlyAsnThrValSerAlaAsnGlyGlyGlyTrpGlnValLeuAsp ThrGlyAlaAlaLeuProLeuAlaIleGlnThrGluMetProTrpAspIleGlyPheIleAsnIleGluAsnProAlaGlyGlyIleThrValSerAlaMet GlyIleAsnGlyAlaGlnLeuThrGlnTrpSerLysTrpArgAlaAspArgMetAsnAspLeuAlaGlnThrGlyAlaAspLeuValIleLeuSerTyr GlyThrAsnGluAlaPheAsnAsnAsnIleAspIleAlaAspThrGluGlnLysTrpLeuAspThrValArgGlnIleArgAspSerLeuProAlaAla GlyIleLeuIleIleGlyAlaProGluSerLeuLysAsnThrLeuGlyValCysGlyThrArgProValLeuLeuThrGluValGlnGlnMetGlnArgArg ValAlaArgGlnGlyGlnThrMetPheTrpSerTrpGlnAsnAlaMetGlyGlyIleCysSerMetLysAsnTrpLeuAsnGlnGlyTrpAlaAlaLys AspGlyValHisPheSerAlaGlnGlyTyrArgArgAlaAlaGluMetLeuAlaAspSerLeuGluGluLeuValArgAlaAlaAlaIleArgGln-397 |

Antigenic Index - Jameson-Wolf
(SEQ. ID. NO. 30943)
1-MetAsnProLysHisPheIleAlaPheSerAlaLeuPheAlaAlaThrGlnAlaGluAlaLeuProValAlaSerValSerProAspThrValThrValSerProSerAlaProTyrThrAsp ThrAsnGlyLeuLeuThrAspTyrGlyAsnAlaAlaAlaSerProTrpMetLysLysLeuArgSerValAlaGlnGlySerGlyGluAlaPheArgIleLeuGlnIleGlyAspSerHisThr AlaGlyAspPhePheThrAspAlaLeuArgLysArgLeuGlnLysThrTrpGlyAspGlyGlyIleGlyTrpValTyrProAlaAsnValLysGlyGlnArgMetAlaAlaValArgHis SerGlyAsnTrpGlnSerPheThrSerArgAsnAsnThrGlyAspPheProLeuGlyGlyIleLeuAlaGlnThrGlySerGlyGlyGlyMetThrLeuThrAlaSerAspGlyLysThr GlyLysGlnArgValSerLeuPheAlaLysProLeuLeuAlaGluGlnThrLeuThrValAsnGlyAsnThrValSerAlaAsnGlyGlyGlyTrpGlnValLeuAspThrGlyAlaAla LeuProLeuAlaIleGlnThrGluMetProTrpAspIleGlyPheIleAsnIleGluAsnProAlaGlyGlyIleThrValSerAlaMetGlyIleAsnGlyAlaGlnLeuThrGlnTrpSerLys TrpArgAlaAspArgMetAsnAspLeuAlaGlnThrGlyAlaAspLeuValIleLeuSerTyrGlyThrAsnGluAlaPheAsnAsnAsnIleAspIleAlaAspThrGluGlnLysTrpLeu AspThrValArgGlnIleArgAspSerLeuProAlaAlaGlyIleLeuIleIleGlyAlaProGluSerLeuLysAsnThrLeuGlyValCysGlyThrArgProValLeuLeuThrGluValGln GlnMetGlnArgArgValAlaArgGlnGlyGlnThrMetPheTrpSerTrpGlnAsnAlaMetGlyGlyIleCysSerMetLysAsnTrpLeuAsnGlnGlyTrpAlaAlaLysAspGly ValHisPheSerAlaGlnGlyTyrArgArgAlaAlaGluMetLeuAlaAspSerLeuGluGluLeuValArgAlaAlaAlaIleArgGln-397

Hydrophilic Regions - Hopp-Woods
(SEQ. ID. NO. 30943)
1-MetAsnProLysHisPheIleAlaPheSerAlaLeuPheAlaAlaThrGlnAlaGluAlaLeuProValAlaSerValSerProAspThrValThrValSerProSerAlaProTyrThrAspThr AsnGlyLeuLeuThrAspTyrGlyAsnAlaAlaAlaSerProTrpMetLysLysLeuArgSerValAlaGlnGlySerGlyGluAlaPheArgIleLeuGlnIleGlyAspSerHisThrAlaGly AspPhePheThrAspAlaLeuArgLysArgLeuGlnLysThrTrpGlyAspGlyGlyIleGlyTrpValTyrProAlaAsnValLysGlyGlnArgMetAlaAlaValArgHisSerGlyAsn TrpGlnSerPheThrSerArgAsnAsnThrGlyAspPheProLeuGlyGlyIleLeuAlaGlnThrGlySerGlyGlyGlyMetThrLeuThrAlaSerAspGlyLysThrGlyLysGlnArg ValSerLeuPheAlaLysProLeuLeuAlaGluGlnThrLeuThrValAsnGlyAsnThrValSerAlaAsnGlyGlyGlyTrpGlnValLeuAspThrGlyAlaAlaLeuProLeuAlaIleGln ThrGluMetProTrpAspIleGlyPheIleAsnIleGluAsnProAlaGlyGlyIleThrValSerAlaMetGlyIleAsnGlyAlaGlnLeuThrGlnTrpSerLysTrpArgAlaAspArgMetAsn AspLeuAlaGlnThrGlyAlaAspLeuValIleLeuSerTyrGlyThrAsnGluAlaPheAsnAsnAsnIleAspIleAlaAspThrGluGlnLysTrpLeuAspThrValArgGlnIleArgAsp SerLeuProAlaAlaGlyIleLeuIleIleGlyAlaProGluSerLeuLysAsnThrLeuGlyValCysGlyThrArgProValLeuLeuThrGluValGlnGlnMetGlnArgArgValAlaArg GlnGlyGlnThrMetPheTrpSerTrpGlnAsnAlaMetGlyGlyIleCysSerMetLysAsnTrpLeuAsnGlnGlyTrpAlaAlaLysAspGlyValHisPheSerAlaGlnGlyTyrArg ArgAlaAlaGluMetLeuAlaAspSerLeuGluGluLeuValArgAlaAlaAlaIleArgGln-397

| | |
|---|---|
| g302 | |
| AMPHI Regions - AMPHI | |
| SEQ. ID. NO. 30944 | 20-SerGlyArgPheLeuArgThrValGluTrpLeuGlyAsnMetLeuProHisPro-37 |
| SEQ. ID. NO. 30945 | 81-ValValSerLeuLeuAspAlaAspGlyLeuIleLysIleLeuThrHisThrValLysAsnPheThrGlyPheAlaProLeuGlyThrValLeuVal SerLeu-114 |

TABLE 1-continued

| | |
|---|---|
| SEQ. ID. NO. 30946 | 127-SerAlaLeuMetArg-131 |
| SEQ. ID. NO. 30947 | 171-IlePheHisSerLeuGlyArgHisProLeuAlaGlyLeuAlaAlaAlaPheAlaGlyValSerGly-192 |
| SEQ. ID. NO. 30948 | 201-GlyThrIleAspProLeuLeuAlaGlyIleThrGlnGlnAla-214 |
| SEQ. ID. NO. 30949 | 240-IleAlaLeuIleGly-244 |
| SEQ. ID. NO. 30950 | 271-ArgHisSerAsnGluIle-276 |
| SEQ. ID. NO. 30951 | 294-LeuSerAlaLeuLeuAlaTrp-300 |
| SEQ. ID. NO. 30952 | 308-IleLeuArgHisProGluThr-314 |
| SEQ. ID. NO. 30953 | 341-TyrGlyArgIleThrArgSerLeuArgGly-350 |
| SEQ. ID. NO. 30954 | 352-ArgGluValValAsnAlaMetAlaGluSerMetSer-363 |
| SEQ. ID. NO. 30955 | 378-PheValAlaPhePheAsnTrpThrAsnIleGlyGlnTyrIle-391 |
| SEQ. ID. NO. 30956 | 448-AlaProGlnValIle-452 |
| SEQ. ID. NO. 30957 | 455-AlaTyrArgIleGlyAspSerValThrAsnIleIleThrProMetMetSerTyrPheGlyLeuIleMetAla-478 |
| SEQ. ID. NO. 30958 | 505-IleAlaTrpIleAlaLeuPheCysIle-513 |
| Antigenic Index - Jameson-Wolf | |
| SEQ. ID. NO. 30959 | 8-LysGluLysGlnMetSerGlnThrAspAlaArgArgSerGlyArgPheLeuArg-25 |
| SEQ. ID. NO. 30960 | 61-SerValProAspProArgProValGlyAlaLysGlyArgAlaAspAspGlyLeu-78 |
| SEQ. ID. NO. 30961 | 85-LeuAspAlaAspGlyLeu-90 |
| SEQ. ID. NO. 30962 | 119-IleAlaGluLysSerGly-124 |
| SEQ. ID. NO. 30963 | 134-LeuThrLysSerProArgLysLeuThr-142 |
| SEQ. ID. NO. 30964 | 152-LeuSerAsnThrAlaSerGlu-158 |
| SEQ. ID. NO. 30965 | 175-LeuGlyArgHisProLeu-180 |
| SEQ. ID. NO. 30966 | 250-LysIleValGluProGlnLeuGlyProTyrGlnSerAspLeuSerGlnGluGluLysAspIleArgHisSerAsnGluIleThrProLeuGluTyrLys-282 |
| SEQ. ID. NO. 30967 | 304-ProAlaAspGlyIleLeuArgHisProGluThrGlyLeu-316 |
| SEQ. ID. NO. 30968 | 343-ArgIleThrArgSerLeuArgGlyGluArgGluValVal-355 |
| SEQ. ID. NO. 30969 | 402-ValGlyLeuGlyGly-406 |
| SEQ. ID. NO. 30970 | 482-LysTyrLysLysAspAlaGlyVal-489 |
| Hydrophilic Regions - Hopp-Woods | |
| SEQ. ID. NO. 30971 | 8-LysGluLysGlnMetSerGlnThrAspAlaArgArgSerGlyArgPhe-23 |
| SEQ. ID. NO. 30972 | 63-ProAspProArgProValGlyAlaLysGlyArgAlaAspAspGlyLeu-78 |
| SEQ. ID. NO. 30973 | 85-LeuAspAlaAspGlyLeu-90 |
| SEQ. ID. NO. 30974 | 119-IleAlaGluLysSerGly-124 |
| SEQ. ID. NO. 30975 | 136-LysSerProArgLysLeu-141 |
| SEQ. ID. NO. 30976 | 263-LeuSerGlnGluGluLysAspIleArgHisSerAsnGlu-275 |
| SEQ. ID. NO. 30977 | 307-GlyIleLeuArgHisProGlu-313 |
| SEQ. ID. NO. 30978 | 344-IleThrArgSerLeuArgGlyGluArgGluValVal-355 |
| SEQ. ID. NO. 30979 | 482-LysTyrLysLysAspAlaGly-488 |
| g305 | |
| AMPHI Regions - AMPHI | |
| SEQ. ID. NO. 30980 | 10-LeuMetMetGlyLeuValGluGlyPheThrGluPheLeuPro-23 |
| SEQ. ID. NO. 30981 | 33-PheGlyAsnLeuIleGly-38 |
| SEQ. ID. NO. 30982 | 66-PheSerAsnValLeuHis-71 |
| SEQ. ID. NO. 30983 | 93-AlaAlaValMetGly-97 |
| SEQ. ID. NO. 30984 | 99-LeuPheAspLysGlnIleLysGluTyrLeuPhe-109 |
| SEQ. ID. NO. 30985 | 141-AspValAspAlaLeuArgProIleAspAla-150 |
| SEQ. ID. NO. 30986 | 155-ValAlaGlnValPheAla-160 |
| SEQ. ID. NO. 30987 | 202-AlaTyrAspValLeuLysHisTyrArgPhePheThrLeuHis-215 |
| SEQ. ID. NO. 30988 | 222-IleGlyPheIleAlaAlaPheValSer-230 |
| SEQ. ID. NO. 30989 | 235-ValLysAlaLeuLeuLys-240 |
| Antigenic Index - Jameson-Wolf | |
| SEQ. ID. NO. 30990 | 41-SerAsnHisLysValPhe-46 |
| SEQ. ID. NO. 30991 | 61-GluTyrArgGlnArgPheSerAsn-68 |
| SEQ. ID. NO. 30992 | 72-GlyValGlyLysAspArgLysAlaAsn-80 |
| SEQ. ID. NO. 30993 | 128-ValGluLysArgGlnSerArgAlaGluProLysIleAlaAsp-141 |
| SEQ. ID. NO. 30994 | 143-AspAlaLeuArgProIleAsp-149 |
| SEQ. ID. NO. 30995 | 163-ProGlyThrSerArgSerGlySerThr-171 |
| SEQ. ID. NO. 30996 | 180-IleGluArgLysThrAlaThr-186 |
| SEQ. ID. NO. 30997 | 241-PheValSerLysLysAsnTyr-247 |
| Hydrophilic Regions - Hopp-Woods | |
| SEQ. ID. NO. 30998 | 62-TyrArgGlnArgPhe-66 |
| SEQ. ID. NO. 30999 | 73-ValGlyLysAspArgLysAlaAsn-80 |
| SEQ. ID. NO. 31000 | 128-ValGluLysArgGlnSerArgAlaGluProLysIleAlaAsp-141 |
| SEQ. ID. NO. 31001 | 143-AspAlaLeuArgProIleAsp-149 |
| SEQ. ID. NO. 31002 | 165-ThrSerArgSerGlySer-170 |
| SEQ. ID. NO. 31003 | 180-IleGluArgLysThrAlaThr-186 |
| SEQ. ID. NO. 31004 | 242-ValSerLysLysAsn-246 |
| g308-1 | |
| AMPHI Regions - AMPHI | |
| SEQ. ID. NO. 31005 | 6-PheTyrArgIleLeuGlyValAlaAsp-14 |
| SEQ. ID. NO. 31006 | 27-ThrIleIleAlaGlyLeu-32 |
| SEQ. ID. NO. 31007 | 64-AlaLeuGluLeuLeuArgAlaGln-71 |
| SEQ. ID. NO. 31008 | 83-AlaGluMetAlaArgAlaSerGlu-90 |
| SEQ. ID. NO. 31009 | 101-LeuAlaAspPheValHisProIleGlyAsnIleGlyAlaCys-114 |
| SEQ. ID. NO. 31010 | 131-SerMetArgThrLeuAlaSerValAlaHisGlyPheGlyAsp-144 |
| SEQ. ID. NO. 31011 | 172-LeuAlaHisLeuAspAsnMetLysArgValThrGlu-183 |
| Antigenic Index - Jameson-Wolf | |
| SEQ. ID. NO. 31012 | 39-TrpGluArgArgMetMetVal-45 |
| SEQ. ID. NO. 31013 | 68-LeuArgAlaGlnAspValGluThr-75 |
| SEQ. ID. NO. 31014 | 80-SerLysGlyAlaGluMetAlaArgAlaSerGluThrAspTyrThrLysAspGluVal-98 |
| SEQ. ID. NO. 31015 | 118-GlyThrPheLysThrAspGlyMet-125 |
| SEQ. ID. NO. 31016 | 141-GlyPheGlyAspAsnLeuLeu-147 |

TABLE 1-continued

| | |
|---|---|
| SEQ. ID. NO. 31017 | 149-ArgAlaAlaAspValValLeuLysGluArgArgArgLeu-161 |
| SEQ. ID. NO. 31018 | 166-ArgGluThrProLeu-170 |
| SEQ. ID. NO. 31019 | 176-AspAsnMetLysArgValThrGluMetGly-185 |
| SEQ. ID. NO. 31020 | 195-MetTyrArgLysProGlnThrAlaAspAspIleVal-206 |
| SEQ. ID. NO. 31021 | 220-AspThrProAspLeuAlaGlu-226 |
| Hydrophilic Regions - Hopp-Woods | |
| SEQ. ID. NO. 31022 | 39-TrpGluArgArgMetMetVal-45 |
| SEQ. ID. NO. 31023 | 68-LeuArgAlaGlnAspValGluThr-75 |
| SEQ. ID. NO. 31024 | 81-LysGlyAlaGluMetAlaArgAlaSerGluThrAspTyrThrLysAspGluVal-98 |
| SEQ. ID. NO. 31025 | 120-PheLysThrAspGly-124 |
| SEQ. ID. NO. 31026 | 149-ArgAlaAlaAspValValLeuLysGluArgArgArgLeu-161 |
| SEQ. ID. NO. 31027 | 176-AspAsnMetLysArgValThrGlu-183 |
| SEQ. ID. NO. 31028 | 195-MetTyrArgLysProGlnThrAlaAspAspIleVal-206 |
| g311-1 | |
| AMPHI Regions - AMPHI | |
| SEQ. ID. NO. 31029 | 7-SerHisTrpArgValLeuAlaGluLeuAlaAspGlyLeuProGlnHisValSerGlnLeuAlaArg-28 |
| SEQ. ID. NO. 31030 | 37-LeuAsnGlyPheTrpGlnGlnMetProAlaHisIleArgGlyLeuLeuArg-53 |
| SEQ. ID. NO. 31031 | 55-HisAspGlyTyrTrpArgLeuValArgProLeuAlaValPheAspAlaGluGlyLeuArgAspLeuGly-77 |
| SEQ. ID. NO. 31032 | 124-ArgGlnGlyArgLysTrpSerHisArgLeu-133 |
| SEQ. ID. NO. 31033 | 155-LeuSerProValAlaAla-160 |
| SEQ. ID. NO. 31034 | 219-ValGluAsnAlaAlaSerValGlnSerLeuPheGln-230 |
| SEQ. ID. NO. 31035 | 245-GluThrLeuLeuAlaGluLeuGlyAlaValLeuGluGlnTyrAlaGluGlu-261 |
| SEQ. ID. NO. 31036 | 265-ProPheLeuAsnGlu-269 |
| SEQ. ID. NO. 31037 | 291-CysGluGlyThrVal-295 |
| SEQ. ID. NO. 31038 | 362-ThrValGlySerAlaProTyrArgAspLeuSerProLeu-374 |
| SEQ. ID. NO. 31039 | 426-TyrArgHisProGluGluHisGlySerAspArgTrpPheAsnAlaLeuGlySer-443 |
| SEQ. ID. NO. 31040 | 511-AlaValAlaSerGlyMetMetAspAlaValCysGly-522 |
| SEQ. ID. NO. 31041 | 550-AlaAlaLysValAlaGluAlaLeuProPro-559 |
| SEQ. ID. NO. 31042 | 576-HisGlyLeuLeuAsnLeu-581 |
| Antigenic Index - Jameson-Wolf | |
| SEQ. ID. NO. 31043 | 26-LeuAlaArgGluAlaAspMetLysProGlnGln-36 |
| SEQ. ID. NO. 31044 | 50-GlyLeuLeuArgGlnHisAspGlyTyr-58 |
| SEQ. ID. NO. 31045 | 71-GluGlyLeuArgAspLeuGlyGluArgSerGlyPheGlnThr-84 |
| SEQ. ID. NO. 31046 | 86-LeuLysHisGluCysAlaSerSerAsnAspGluIleLeuGlu-99 |
| SEQ. ID. NO. 31047 | 102-ArgIleAlaProAspLysAlaHisLys-110 |
| SEQ. ID. NO. 31048 | 116-HisLeuGlnSerLysGlyArgGlyArgGlnGlyArgLysTrpSerHisArgLeuGlyGlu-135 |
| SEQ. ID. NO. 31049 | 145-PheAspArgProGlnTyrGluLeuGlySer-154 |
| SEQ. ID. NO. 31050 | 162-AlaCysArgArgAlaLeuGly-168 |
| SEQ. ID. NO. 31051 | 174-ThrGlnIleLysTrpProAsn-180 |
| SEQ. ID. NO. 31052 | 182-LeuValValGlyArgAspLysLeuGly-190 |
| SEQ. ID. NO. 31053 | 196-ThrValArgAlaGlyGlyLysThrVal-204 |
| SEQ. ID. NO. 31054 | 215-LeuProLysGluValGluAsn-221 |
| SEQ. ID. NO. 31055 | 231-ThrAlaSerArgArgGlyAsnAlaAsp-239 |
| SEQ. ID. NO. 31056 | 257-GlnTyrAlaGluGluGlyPhe-263 |
| SEQ. ID. NO. 31057 | 269-GluTyrGluThrAlaAsnArgAspHisGlyLys-279 |
| SEQ. ID. NO. 31058 | 283-LeuLeuArgAspGlyGluThrValCysGluGlyThrValLysGlyValAspGlyArgGlyValLeu-304 |
| SEQ. ID. NO. 31059 | 307-GluThrAlaGluGlyGluGlnThrValValSerGlyGluIleSerLeuArgProAspAsnArgSerValSerValProLysArgProAspSerGluArg PheLeu-341 |
| SEQ. ID. NO. 31060 | 344-GluGlyGlyAsnSerArgLeuLys-351 |
| SEQ. ID. NO. 31061 | 364-GlySerAlaProTyrArgAspLeuSerProLeuGly-375 |
| SEQ. ID. NO. 31062 | 378-TrpAlaGluLysAlaAspGlyAsnValArgIle-388 |
| SEQ. ID. NO. 31063 | 394-CysGlyGluSerLysLysAlaGlnValLysGluGlnLeuAlaArgLysIleGlu-411 |
| SEQ. ID. NO. 31064 | 424-AsnHisTyrArgHisProGluGluHisGlySerAspArgTrp-437 |
| SEQ. ID. NO. 31065 | 440-AlaLeuGlySerArgArgPheSerArgAsnAla-450 |
| SEQ. ID. NO. 31066 | 464-AlaLeuThrAspAspGlyHisTyrLeuGly-473 |
| SEQ. ID. NO. 31067 | 483-MetLysGluSerLeuAla-488 |
| SEQ. ID. NO. 31068 | 492-AlaAsnLeuAsnArgProAlaGlyLysArgTyrPro-503 |
| SEQ. ID. NO. 31069 | 529-GlyArgLeuLysGluLysAsnGlyAlaGlyLysProVal-541 |
| SEQ. ID. NO. 31070 | 547-GlyGlyGlyAlaAlaLysValAlaGlu-555 |
| SEQ. ID. NO. 31071 | 565-AsnThrValArgValAlaAsp-571 |
| SEQ. ID. NO. 31072 | 584-AlaGluGlyGlyGluSerGluHisAla-592 |
| Hydrophilic Regions - Hopp-Woods | |
| SEQ. ID. NO. 31073 | 26-LeuAlaArgGluAlaAspMetLysProGlnGln-36 |
| SEQ. ID. NO. 31074 | 50-GlyLeuLeuArgGlnHis-55 |
| SEQ. ID. NO. 31075 | 71-GluGlyLeuArgAspLeuGlyGluArgSerGlyPhe-82 |
| SEQ. ID. NO. 31076 | 86-LeuLysHisGluCysAlaSerSerAsnAspGluIleLeuGlu-99 |
| SEQ. ID. NO. 31077 | 102-ArgIleAlaProAspLysAlaHisLys-110 |
| SEQ. ID. NO. 31078 | 118-GlnSerLysGlyArgGlyArgGlnGlyArgLysTrpSerHisArgLeuGlyGlu-135 |
| SEQ. ID. NO. 31079 | 162-AlaCysArgArgAlaLeu-167 |
| SEQ. ID. NO. 31080 | 183-ValValGlyArgAspLysLeuGly-190 |
| SEQ. ID. NO. 31081 | 196-ThrValArgAlaGlyGlyLys-202 |
| SEQ. ID. NO. 31082 | 217-LysGluValGluAsn-221 |
| SEQ. ID. NO. 31083 | 232-AlaSerArgArgGlyAsnAlaAsp-239 |
| SEQ. ID. NO. 31084 | 257-GlnTyrAlaGluGluGlyPhe-263 |
| SEQ. ID. NO. 31085 | 270-TyrGluThrAlaAsnArgAspHisGlyLys-279 |
| SEQ. ID. NO. 31086 | 285-ArgAspGlyGluThrValCys-291 |
| SEQ. ID. NO. 31087 | 293-GlyThrValLysGlyValAspGlyArgGly-302 |
| SEQ. ID. NO. 31088 | 307-GluThrAlaGluGlyGluGlnThrValVal-316 |
| SEQ. ID. NO. 31089 | 320-IleSerLeuArgProAspAsnArgSerValSerValProLysArgProAspSerGluArg-339 |
| SEQ. ID. NO. 31090 | 346-GlyAsnSerArgLeu-350 |

TABLE 1-continued

| | |
|---|---|
| SEQ. ID. NO. 31091 | 367-ProTyrArgAspLeuSer-372 |
| SEQ. ID. NO. 31092 | 378-TrpAlaGluLysAlaAspGlyAsnVal-386 |
| SEQ. ID. NO. 31093 | 395-GlyGluSerLysLysAlaGlnValLysGluGlnLeuAlaArgLysIleGlu-411 |
| SEQ. ID. NO. 31094 | 424-AsnHisTyrArgHisProGluGluHisGlySer-434 |
| SEQ. ID. NO. 31095 | 442-GlySerArgArgPheSerArg-448 |
| SEQ. ID. NO. 31096 | 464-AlaLeuThrAspAspGlyHis-470 |
| SEQ. ID. NO. 31097 | 483-MetLysGluSerLeuAla-488 |
| SEQ. ID. NO. 31098 | 493-AsnLeuAsnArgProAlaGlyLysArgTyrPro-503 |
| SEQ. ID. NO. 31099 | 529-GlyArgLeuLysGluLysAsnGlyAlaGlyLysProVal-541 |
| SEQ. ID. NO. 31100 | 549-GlyAlaAlaLysValAlaGlu-555 |
| SEQ. ID. NO. 31101 | 565-AsnThrValArgValAlaAsp-571 |
| SEQ. ID. NO. 31102 | 585-GluGlyGlyGluSerGluHisAla-592 |
| g312 | |
| AMPHI Regions - AMPHI | |
| SEQ. ID. NO. 31103 | 6-GlyGluIleLeuGluThrValLysMetValAlaAsp-17 |
| SEQ. ID. NO. 31104 | 44-GlnAsnIleTyrAsnLysIleThrThrValGlyLys-55 |
| SEQ. ID. NO. 31105 | 82-IleAlaGlnIleAlaAlaAlaThr-89 |
| SEQ. ID. NO. 31106 | 96-SerValAlaGlnThrLeuAspLysAlaAlaLys-106 |
| SEQ. ID. NO. 31107 | 109-GlyValSerPheIleGlyGlyPheSerAlaLeuValGln-121 |
| SEQ. ID. NO. 31108 | 133-ArgSerValProGluAlaMetLysThr-141 |
| SEQ. ID. NO. 31109 | 167-GlyGluThrIleLysArgThrAlaGluIle-176 |
| SEQ. ID. NO. 31110 | 182-GlyCysAlaLysIleValValPheCys-190 |
| SEQ. ID. NO. 31111 | 230-SerAspAlaValSerLeuThrGluValAlaGluValValLysLys-244 |
| SEQ. ID. NO. 31112 | 249-IleThrArgValGlyGluLeuIleGlyArgGluAlaSerLys-262 |
| SEQ. ID. NO. 31113 | 281-ValGlyAspSerValAlaArgIleLeuGluGluMetGly-293 |
| SEQ. ID. NO. 31114 | 309-LeuAsnAspAlaVal-313 |
| SEQ. ID. NO. 31115 | 322-SerAlaValGlyGlyLeuSerGly-329 |
| SEQ. ID. NO. 31116 | 349-LeuThrLeuAspLysLeuGluAlaMetThrAla-359 |
| SEQ. ID. NO. 31117 | 374-ThrProAlaHisThrIleSerGlyIleIle-383 |
| SEQ. ID. NO. 31118 | 409-ValGlyAspSerValGluPheGlyGlyLeuLeuGly-420 |
| Antigenic Index - Jameson-Wolf | |
| SEQ. ID. NO. 31119 | 4-GlnSerGlyGluIleLeuGlu-10 |
| SEQ. ID. NO. 31120 | 13-LysMetValAlaAspArgAsnPheAspVal-22 |
| SEQ. ID. NO. 31121 | 35-IleSerThrAspIleAspVal-41 |
| SEQ. ID. NO. 31122 | 52-ThrValGlyLysAspLeuValAla-59 |
| SEQ. ID. NO. 31123 | 64-LeuSerAlaLysTyr-68 |
| SEQ. ID. NO. 31124 | 89-ThrLysAlaAspSerTyrVal-95 |
| SEQ. ID. NO. 31125 | 100-ThrLeuAspLysAlaAlaLys-106 |
| SEQ. ID. NO. 31126 | 121-GlnLysGlyMetSerProSerAspGluValLeu-131 |
| SEQ. ID. NO. 31127 | 134-SerValProGluAlaMetLysThrThrAsp-143 |
| SEQ. ID. NO. 31128 | 152-GlySerThrArgAla-156 |
| SEQ. ID. NO. 31129 | 161-AspAlaValLysLeuAlaGlyGluThrIleLysArgThrAlaGluIleThrProGluGlyPheGly-182 |
| SEQ. ID. NO. 31130 | 192-AlaValGluAspAsnProPhe-198 |
| SEQ. ID. NO. 31131 | 204-HisGlySerGlyGluAlaAspAla-211 |
| SEQ. ID. NO. 31132 | 225-AlaAlaLeuGluAsnSerAspAla-232 |
| SEQ. ID. NO. 31133 | 237-GluValAlaGluValValLys-243 |
| SEQ. ID. NO. 31134 | 251-ArgValGlyGluLeuIleGlyArgGluAlaSerLys-262 |
| SEQ. ID. NO. 31135 | 280-AlaValGlyAspSerValAlaArgIleLeuGlu-290 |
| SEQ. ID. NO. 31136 | 311-AspAlaValLysLysGlyGlyMet-318 |
| SEQ. ID. NO. 31137 | 334-ValSerGluAspGluGlyMet-340 |
| SEQ. ID. NO. 31138 | 352-AspLysLeuGluAla-356 |
| SEQ. ID. NO. 31139 | 370-ValProGlyAspThrProAla-376 |
| SEQ. ID. NO. 31140 | 383-IleAlaAspGluAlaAla-388 |
| SEQ. ID. NO. 31141 | 392-IleAsnSerLysThrThrAla-398 |
| SEQ. ID. NO. 31142 | 405-ThrGlyLysThrValGlyAspSerValGlu-414 |
| SEQ. ID. NO. 31143 | 426-ProAlaLysGluGlySerCys-432 |
| SEQ. ID. NO. 31144 | 435-PheValAsnArgGlyGlyArgIle-442 |
| SEQ. ID. NO. 31145 | 447-GlnSerMetLysAsn-451 |
| Hydrophilic Regions - Hopp-Woods | |
| SEQ. ID. NO. 31146 | 13-LysMetValAlaAspArgAsnPheAspVal-22 |
| SEQ. ID. NO. 31147 | 35-IleSerThrAspIleAspVal-41 |
| SEQ. ID. NO. 31148 | 52-ThrValGlyLysAspLeuValAla-59 |
| SEQ. ID. NO. 31149 | 89-ThrLysAlaAspSer-93 |
| SEQ. ID. NO. 31150 | 100-ThrLeuAspLysAlaAlaLys-106 |
| SEQ. ID. NO. 31151 | 123-GlyMetSerProSerAspGluValLeu-131 |
| SEQ. ID. NO. 31152 | 134-SerValProGluAlaMetLysThrThrAsp-143 |
| SEQ. ID. NO. 31153 | 161-AspAlaValLysLeuAlaGlyGluThrIleLysArgThrAlaGluIleThrPro-178 |
| SEQ. ID. NO. 31154 | 192-AlaValGluAspAsnPro-197 |
| SEQ. ID. NO. 31155 | 207-GlyGluAlaAspAla-211 |
| SEQ. ID. NO. 31156 | 225-AlaAlaLeuGluAsnSerAspAla-232 |
| SEQ. ID. NO. 31157 | 237-GluValAlaGluValValLys-243 |
| SEQ. ID. NO. 31158 | 251-ArgValGlyGluLeuIleGlyArgGluAlaSerLys-262 |
| SEQ. ID. NO. 31159 | 284-SerValAlaArgIleLeuGlu-290 |
| SEQ. ID. NO. 31160 | 311-AspAlaValLysLysGlyGlyMet-318 |
| SEQ. ID. NO. 31161 | 334-ValSerGluAspGluGlyMet-340 |
| SEQ. ID. NO. 31162 | 352-AspLysLeuGluAla-356 |
| SEQ. ID. NO. 31163 | 383-IleAlaAspGluAlaAla-388 |
| SEQ. ID. NO. 31164 | 408-ThrValGlyAspSerValGlu-414 |

TABLE 1-continued

| | |
|---|---|
| SEQ. ID. NO. 31165 | 426-ProAlaLysGluGlySerCys-432 |
| SEQ. ID. NO. 31166 | 438-ArgGlyGlyArgIle-442 |
| SEQ. ID. NO. 31167 | 447-GlnSerMetLysAsn-451 |
| g313-2 | |
| AMPHI Regions - AMPHI | |
| SEQ. ID. NO. 31168 | 27-GlyMetAspAspProArgThrTyrGlySerGly-37 |
| SEQ. ID. NO. 31169 | 41-AlaThrAsnValLeu-45 |
| SEQ. ID. NO. 31170 | 60-AspAlaAlaLysGly-64 |
| SEQ. ID. NO. 31171 | 66-ValAlaValLeuLeuAlaArgValLeuGlnGluPro-77 |
| SEQ. ID. NO. 31172 | 88-ValAlaLeuAlaAlaLeuValGlyHisMetTrpPro-99 |
| SEQ. ID. NO. 31173 | 143-SerLeuAlaAlaLeuValAla-149 |
| Antigenic Index - Jameson-Wolf | |
| SEQ. ID. NO. 31174 | 26-TyrGlyMetAspAspProArgThrTyrGlySerGlyAsnProGlyAla-41 |
| SEQ. ID. NO. 31175 | 46-ArgSerGlyLysLysLysAlaAla-53 |
| SEQ. ID. NO. 31176 | 73-ValLeuGlnGluProLeuGlyLeuSerAspSerAla-84 |
| SEQ. ID. NO. 31177 | 104-PheLysGlyGlyLysGlyVal-110 |
| SEQ. ID. NO. 31178 | 180-ArgHisLysSerAsn-184 |
| SEQ. ID. NO. 31179 | 189-IleLysGlyLysGluSerLysIleGlyGluLysArg-200 |
| Hydrophilic Regions - Hopp-Woods | |
| SEQ. ID. NO. 31180 | 26-TyrGlyMetAspAspProArgThrTyrGly-35 |
| SEQ. ID. NO. 31181 | 46-ArgSerGlyLysLysLysAlaAla-53 |
| SEQ. ID. NO. 31182 | 105-LysGlyGlyLysGlyVal-110 |
| SEQ. ID. NO. 31183 | 189-IleLysGlyLysGluSerLysIleGlyGluLysArg-200 |
| g401 | |
| AMPHI Regions - AMPHI | |
| SEQ. ID. NO. 31184 | 46-ValLysProTyrAsnAlaLeu-52 |
| SEQ. ID. NO. 31185 | 65-CysTyrAsnCysHisSerGlnMetIleArgProPheArg-77 |
| SEQ. ID. NO. 31186 | 112-ValGlyGlyArgTyrSerAspGluTrpHisArgIle-123 |
| SEQ. ID. NO. 31187 | 157-MetLysAlaLeuArgLysValGlyThr-165 |
| SEQ. ID. NO. 31188 | 172-IleAlaLysAlaProGluAlaLeu-179 |
| Antigenic Index - Jameson-Wolf | |
| SEQ. ID. NO. 31189 | 5-GlnLeuAlaGluGluLysIle-11 |
| SEQ. ID. NO. 31190 | 38-AlaAlaThrGlnProAlaProGlyValLysProTyrAsn-50 |
| SEQ. ID. NO. 31191 | 55-AlaGlyArgAspIleTyrIleArgGluGlyCysTyrAsnCysHis-69 |
| SEQ. ID. NO. 31192 | 74-ArgProPheArgAlaGluThrGluArgTyrGlyHis-85 |
| SEQ. ID. NO. 31193 | 90-GlyGluSerValTyr-94 |
| SEQ. ID. NO. 31194 | 98-PheGlnTrpGlySerLysArgThrGlyProAspLeuAlaArgValGlyGlyArgTyrSerAspGluTrpHis-121 |
| SEQ. ID. NO. 31195 | 125-LeuLeuAsnProArgAspValValProGluSerAsnMetPro-138 |
| SEQ. ID. NO. 31196 | 146-AsnLysValAspValAspAla-152 |
| SEQ. ID. NO. 31197 | 158-LysAlaLeuArgLysValGlyThrProTyrSerAspGluGluIleAlaLysAlaProGlu-177 |
| SEQ. ID. NO. 31198 | 179-LeuAlaAsnLysSerGluLeuAspAla-187 |
| Hydrophilic Regions - Hopp-Woods | |
| SEQ. ID. NO. 31199 | 5-GlnLeuAlaGluGluLysIle-11 |
| SEQ. ID. NO. 31200 | 76-PheArgAlaGluThrGluArgTyrGly-84 |
| SEQ. ID. NO. 31201 | 101-GlySerLysArgThrGlyProAspLeuAlaArgValGlyGlyArgTyrSerAspGluTrpHis-121 |
| SEQ. ID. NO. 31202 | 127-AsnProArgAspValValPro-133 |
| SEQ. ID. NO. 31203 | 146-AsnLysValAspValAspAla-152 |
| SEQ. ID. NO. 31204 | 158-LysAlaLeuArgLysValGly-164 |
| SEQ. ID. NO. 31205 | 167-TyrSerAspGluGluIleAlaLysAlaProGlu-177 |
| SEQ. ID. NO. 31206 | 179-LeuAlaAsnLysSerGluLeuAspAla-187 |
| g402 | |
| AMPHI Regions - AMPHI | |
| SEQ. ID. NO. 31207 | 13-IleAsnMetLeuSerPheLeuThrGly-21 |
| SEQ. ID. NO. 31208 | 44-GlnAlaPheSerPheIle-49 |
| SEQ. ID. NO. 31209 | 85-AlaGlyIleAlaAspPhe-90 |
| SEQ. ID. NO. 31210 | 100-ThrGlyPheSerGlyPheValHis-107 |
| SEQ. ID. NO. 31211 | 117-AlaValValArgGlyLeu-122 |
| SEQ. ID. NO. 31212 | 136-LysSerGlyArgGln-140 |
| SEQ. ID. NO. 31213 | 146-PheAlaAsnValAlaGly-151 |
| SEQ. ID. NO. 31214 | 218-ValPheGlnAsnIleAlaGlyArgProAsp-227 |
| SEQ. ID. NO. 31215 | 261-AspIlePheAsnSerValAsnGlyIleGlu-270 |
| SEQ. ID. NO. 31216 | 279-LysSerGlyIleArg-283 |
| SEQ. ID. NO. 31217 | 294-SerTrpAlaArgValLeuSerAlaIleProGluMetGln-306 |
| SEQ. ID. NO. 31218 | 344-ArgLysTrpLeuArgArgHisPro-351 |
| SEQ. ID. NO. 31219 | 376-AlaGluPheLeuLysGlnValGlnSerHisLeu-386 |
| SEQ. ID. NO. 31220 | 398-HisSerProHisAlaPheAlaThrAlaValHisSerIlePro-411 |
| SEQ. ID. NO. 31221 | 437-GlnArgLeuSerArgLeu-442 |
| SEQ. ID. NO. 31222 | 460-AlaAlaGlnLysVal-464 |
| SEQ. ID. NO. 31223 | 466-SerArgMetLeuIleArgMet-472 |
| Antigenic Index - Jameson-Wolf | |
| SEQ. ID. NO. 31224 | 4-ValAsnThrLysProAsnThrSer-11 |
| SEQ. ID. NO. 31225 | 66-ArgIleCysArgSerArgPheValAsp-74 |
| SEQ. ID. NO. 31226 | 130-ValGlyThrAspGlyAsnLysSerGlyArgGlnValSer-142 |
| SEQ. ID. NO. 31227 | 223-AlaGlyArgProAspArgLeuIleGluAsnLysHisGly-235 |
| SEQ. ID. NO. 31228 | 240-TyrHisArgAspGlyAspLysValVal-248 |
| SEQ. ID. NO. 31229 | 264-AsnSerValAsnGlyIleGluArg-271 |
| SEQ. ID. NO. 31230 | 277-SerLeuLysSerGlyIleArgArg-284 |
| SEQ. ID. NO. 31231 | 321-IleAlaAspGluProGln-326 |
| SEQ. ID. NO. 31232 | 331-LeuGlnAspLysArgValGluIleValLeuAspAspGlyArgLysTrpLeuArgArgHisProAspGluLysPheAsp-356 |
| SEQ. ID. NO. 31233 | 385-HisLeuThrProAspGly-390 |

TABLE 1-continued

| | |
|---|---|
| SEQ. ID. NO. 31234 | 429-PheProAsnLysGluLeuLeuLysGlnArgLeuSer-440 |
| SEQ. ID. NO. 31235 | 444-TrpProGluSerGlyArgHisValPheAspSerSerThrVal-457 |
| SEQ. ID. NO. 31236 | 472-MetThrGluProSerAlaGly-478 |
| SEQ. ID. NO. 31237 | 481-ValIleThrAspAspAsnMet-487 |
| SEQ. ID. NO. 31238 | 489-ValGluTyrLysTyrGlyArgGlyIle-497 |
| Hydrophilic Regions - Hopp-Woods | |
| SEQ. ID. NO. 31239 | 4-ValAsnThrLysProAsn-9 |
| SEQ. ID. NO. 31240 | 131-GlyThrAspGlyAsnLysSerGlyArgGlnVal-141 |
| SEQ. ID. NO. 31241 | 223-AlaGlyArgProAspArgLeuIleGluAsnLysHis-234 |
| SEQ. ID. NO. 31242 | 241-HisArgAspGlyAspLysValVal-248 |
| SEQ. ID. NO. 31243 | 278-LeuLysSerGlyIleArg-283 |
| SEQ. ID. NO. 31244 | 321-IleAlaAspGluProGln-326 |
| SEQ. ID. NO. 31245 | 331-LeuGlnAspLysArgValGluIleValLeuAspAspGlyArgLysTrpLeuArgArgHisProAspGluLysPheAsp-356 |
| SEQ. ID. NO. 31246 | 430-ProAsnLysGluLeuLeuLysGlnArgLeuSer-440 |
| SEQ. ID. NO. 31247 | 446-GluSerGlyArgHisValPhe-452 |
| SEQ. ID. NO. 31248 | 472-MetThrGluProSerAlaGly-478 |
| SEQ. ID. NO. 31249 | 481-ValIleThrAspAspAsnMet-487 |
| g501 | |
| AMPHI Regions - AMPHI | |
| SEQ. ID. NO. 31250 | 63-ValGluValLeuGlnGluLeuPheArgGlnTyrArgValAlaArgGlnLeu-79 |
| SEQ. ID. NO. 31251 | 88-ValPheAlaAlaPheGlnAlaValPhePheGlnCysLeuAsnHisCysPheGly-105 |
| SEQ. ID. NO. 31252 | 127-AsnAlaPheGlnGly-131 |
| SEQ. ID. NO. 31253 | 139-ValPheGluAlaLeuGlyAsnIleThrArgArgThrThrGluAla-153 |
| SEQ. ID. NO. 31254 | 183-AspGlyPheThrArgIleAsnArgCysGlyLysArgCysHisAlaPheGlyAspPheIleAsp-203 |
| SEQ. ID. NO. 31255 | 253-AlaPheAlaGlyGlnIle-258 |
| SEQ. ID. NO. 31256 | 307-TyrGlyAsnPheLeuThrValPheGlnGluPheGlyArgIleAlaAlaAlaAsp-324 |
| SEQ. ID. NO. 31257 | 365-GlyAsnGlnTyrValAlaGlyPhe-372 |
| SEQ. ID. NO. 31258 | 492-GlyGluAsnHisPheAspValPheArgThr-501 |
| SEQ. ID. NO. 31259 | 513-PheGluArgGlyPheGluHisIleLysPheValArgValAspArgAlaLeuTyrAspValPheAlaGlnThr-536 |
| Antigenic Index - Jameson-Wolf | |
| SEQ. ID. NO. 31260 | 6-LeuThrAlaAspThrAspIle-12 |
| SEQ. ID. NO. 31261 | 19-GlyGlyAspGlyLysMetGlnHisHisPheAspGly-30 |
| SEQ. ID. NO. 31262 | 46-ValGluAlaGluGlyGln-51 |
| SEQ. ID. NO. 31263 | 56-ValArgAlaAspGlyGluAlaValGluVal-65 |
| SEQ. ID. NO. 31264 | 108-GlnSerAlaAspGluArgAsnHisAspPheAspValGlyGln-121 |
| SEQ. ID. NO. 31265 | 145-AsnIleThrArgArgThrThrGluAlaGlnHis-155 |
| SEQ. ID. NO. 31266 | 179-GlyHisThrAspAspGlyPheThrArgIleAsnArgCysGlyLysArgCysHisAla-197 |
| SEQ. ID. NO. 31267 | 202-IleAspValGluValAspArgGlyCysValThrGlyAspAlaAlaAspAsnPhe-219 |
| SEQ. ID. NO. 31268 | 231-GlnGlnGlyPheArgValAspAlaAspLeuAlaValAspAspLysPheHisThrArgGlnAlaAsp-252 |
| SEQ. ID. NO. 31269 | 258-IleGlyGluAlaGluCysGluPheGly-266 |
| SEQ. ID. NO. 31270 | 270-ValHisHisAspPheAspGlyCys-277 |
| SEQ. ID. NO. 31271 | 283-GlnGlyAspIleGly-287 |
| SEQ. ID. NO. 31272 | 295-GlyIleAspLysAlaGly-300 |
| SEQ. ID. NO. 31273 | 321-AlaAlaAlaAspAspGlyArgAsnThrGlnPheAlaArgAspAspGlyGlyValAla-339 |
| SEQ. ID. NO. 31274 | 345-ValGlyHisAspGlyGlySerThr-352 |
| SEQ. ID. NO. 31275 | 392-LeuThrAspGlyThr-396 |
| SEQ. ID. NO. 31276 | 398-PheAlaGlnAspGly-402 |
| SEQ. ID. NO. 31277 | 421-PheAspGlyPheGly-425 |
| SEQ. ID. NO. 31278 | 442-PheAspIleHisArg-446 |
| SEQ. ID. NO. 31279 | 453-AspGlyGlnArgVal-457 |
| SEQ. ID. NO. 31280 | 479-PheAspValGlyTyr-483 |
| SEQ. ID. NO. 31281 | 502-HisGlyLeuAlaGlnAspGlyGly-509 |
| SEQ. ID. NO. 31282 | 523-ValArgValAspArgAlaLeu-529 |
| SEQ. ID. NO. 31283 | 536-ThrValArgGlyGlyAsnLysAspAspLeuVal-546 |
| SEQ. ID. NO. 31284 | 552-ValGluGlyGluHisHisThr-558 |
| Hydrophilic Regions - Hopp-Woods | |
| SEQ. ID. NO. 31285 | 6-LeuThrAlaAspThr-10 |
| SEQ. ID. NO. 31286 | 19-GlyGlyAspGlyLysMet-24 |
| SEQ. ID. NO. 31287 | 46-ValGluAlaGluGlyGln-51 |
| SEQ. ID. NO. 31288 | 56-ValArgAlaAspGlyGluAlaValGluVal-65 |
| SEQ. ID. NO. 31289 | 108-GlnSerAlaAspGluArgAsnHisAspPheAspVal-119 |
| SEQ. ID. NO. 31290 | 146-IleThrArgArgThrThrGluAlaGlnHis-155 |
| SEQ. ID. NO. 31291 | 179-GlyHisThrAspAspGlyPheThrArgIleAsnArgCysGlyLysArgCysHisAla-197 |
| SEQ. ID. NO. 31292 | 202-IleAspValGluValAspArgGlyCysVal-211 |
| SEQ. ID. NO. 31293 | 214-AspAlaAlaAspAsnPhe-219 |
| SEQ. ID. NO. 31294 | 234-PheArgValAspAlaAspLeuAlaValAspAspLysPheHisThrArgGlnAlaAsp-252 |
| SEQ. ID. NO. 31295 | 258-IleGlyGluAlaGluCysGluPheGly-266 |
| SEQ. ID. NO. 31296 | 270-ValHisHisAspPhe-274 |
| SEQ. ID. NO. 31297 | 295-GlyIleAspLysAlaGly-300 |
| SEQ. ID. NO. 31298 | 321-AlaAlaAlaAspAspGlyArgAsnThrGlnPheAlaArgAspAspGlyGlyVal-338 |
| SEQ. ID. NO. 31299 | 345-ValGlyHisAspGly-349 |
| SEQ. ID. NO. 31300 | 523-ValArgValAspArgAlaLeu-529 |
| SEQ. ID. NO. 31301 | 537-ValArgGlyGlyAsnLysAspAspLeuVal-546 |
| SEQ. ID. NO. 31302 | 552-ValGluGlyGluHisHisThr-558 |
| g502-1 | |
| AMPHI Regions - AMPHI | |
| SEQ. ID. NO. 31303 | 6-AsnLeuPheGlnPheLeuAlaValCys-14 |
| SEQ. ID. NO. 31304 | 26-GlyAlaValAspAlaLeuLysGlnPheAsnAsnAspAlaAspGlyIleSerGlySerPheThrGln-47 |
| SEQ. ID. NO. 31305 | 98-GlnValThrLysSerSerGlnAsp-105 |
| SEQ. ID. NO. 31306 | 136-GlyIleAspTyrVal-140 |

TABLE 1-continued

Antigenic Index - Jameson-Wolf
SEQ. ID. NO. 31307 32-LysGlnPheAsnAsnAspAlaAspGlyIleSerGlySer-44
SEQ. ID. NO. 31308 48-ThrValGlnSerLysLysLysThrGlnThrAlaHisGlyThr-61
SEQ. ID. NO. 31309 98-GlnValThrLysSerSerGlnAspGlnAlaIleGlyGlySerPro-112
SEQ. ID. NO. 31310 116-LeuSerAsnLysThrAlaLeuGluSerSerTyrThrLeuLysGluAspGlySerSerAsnGly-136
SEQ. ID. NO. 31311 141-ArgAlaThrProLysArgAsnAsnAlaGly-150
SEQ. ID. NO. 31312 158-PheLysGlyGlyAsn-162
SEQ. ID. NO. 31313 167-GlnLeuLysAspSerPheGlyAsnGlnThr-176
SEQ. ID. NO. 31314 184-AsnThrAsnProGlnLeuSerArgGlyAlaPhe-194
SEQ. ID. NO. 31315 196-PheThrProProLysGlyValAspVal-204
Hydrophilic Regions - Hopp-Woods
SEQ. ID. NO. 31316 34-PheAsnAsnAspAlaAspGlyIle-41
SEQ. ID. NO. 31317 49-ValGlnSerLysLysLysThrGlnThr-57
SEQ. ID. NO. 31318 100-ThrLysSerSerGlnAspGlnAlaIle-108
SEQ. ID. NO. 31319 126-TyrThrLeuLysGluAspGlySerSerAsn-135
SEQ. ID. NO. 31320 141-ArgAlaThrProLysArgAsnAsnAla-149
SEQ. ID. NO. 31321 167-GlnLeuLysAspSerPheGly-173
g503-1
AMPHI Regions - AMPHI
SEQ. ID. NO. 31322 6-TyrArgGluAlaLys-10
SEQ. ID. NO. 31323 95-ThrSerSerThrSerAsnPheAlaArgAlaAlaGluMetArgSerPhe-110
Antigenic Index - Jameson-Wolf
SEQ. ID. NO. 31324 4-SerLeuTyrArgGluAlaLysThr-11
SEQ. ID. NO. 31325 32-ProAlaAsnAspAlaSerGlyArgSerSerAlaValAlaGluGluArgThrAlaThrGluMetSerAlaProSer-56
SEQ. ID. NO. 31326 69-SerAlaSerSerCysSerGlyLysGlyValSer-79
SEQ. ID. NO. 31327 87-LeuProThrArgAlaSerSerGluThrSerSerThrSerAsnPhe-101
SEQ. ID. NO. 31328 103-ArgAlaAlaGluMetArgSerPheArgProLeuCysAlaArgAsnAlaArg-119
Hydrophilic Regions - Hopp-Woods
SEQ. ID. NO. 31329 4-SerLeuTyrArgGluAlaLysThr-11
SEQ. ID. NO. 31330 35-AspAlaSerGlyArgSerSerAlaValAlaGluGluArgThrAlaThrGluMetSerAla-54
SEQ. ID. NO. 31331 73-CysSerGlyLysGlyValSer-79
SEQ. ID. NO. 31332 89-ThrArgAlaSerSerGluThrSerSer-97
SEQ. ID. NO. 31333 103-ArgAlaAlaGluMetArgSerPheArg-111
g505
AMPHI Regions - AMPHI
SEQ. ID. NO. 31334 20-LeuThrAlaLeuLeuLysCysLeuSerLeuLeuSerLeuSerCysLeu-35
SEQ. ID. NO. 31335 37-ThrLeuGlyAsnArg-41
SEQ. ID. NO. 31336 89-ProAlaPhePheLysLysProGluAspIleGluThrMetPheLysAlaValHisGlyTrpGluHisValGlnGlnAlaLeuAsp-116
SEQ. ID. NO. 31337 148-AlaMetTyrLysProProLysIleLysAlaIleAspLysIleMetGlnAlaGly-165
SEQ. ID. NO. 31338 178-IleGlnGlyValLysGlnIleIleLysAlaLeuArg-189
SEQ. ID. NO. 31339 209-GlyValTrpAlaAspPhePheGlyLysPro-218
Antigenic Index - Jameson-Wolf
SEQ. ID. NO. 31340 39-GlyAsnArgLeuGly-43
SEQ. ID. NO. 31341 50-LeuLysGluAspArgAlaArgIle-57
SEQ. ID. NO. 31342 64-AlaGlyLeuAsnProAspThrGlnThrVal-73
SEQ. ID. NO. 31343 79-GluThrAlaLysCysGlyLeu-85
SEQ. ID. NO. 31344 92-PheLysLysProGluAspIleGluThr-100
SEQ. ID. NO. 31345 114-AlaLeuAspLysGlyGluGlyLeu-121
SEQ. ID. NO. 31346 131-TyrAspLeuGlyGlyArgTyrIleSer-139
SEQ. ID. NO. 31347 151-LysProProLysIleLysAlaIleAspLysIleMetGln-163
SEQ. ID. NO. 31348 165-GlyArgValArgGlyLysGlyLysThrAlaProThrGly-177
SEQ. ID. NO. 31349 179-GlnGlyValLysGlnIleIleLys-186
SEQ. ID. NO. 31350 188-LeuArgAlaGlyGlu-192
SEQ. ID. NO. 31351 199-AspHisValProSerProGlnGluGlyGlyGlyVal-210
SEQ. ID. NO. 31352 241-CysGluArgLeuProAspGlyGlnGly-249
SEQ. ID. NO. 31353 257-ValGlnGlyGluLeuAsnGlyAsnLysAlaHisAsp-268
SEQ. ID. NO. 31354 273-AsnArgAsnThrGluTyrTrp-279
SEQ. ID. NO. 31355 292-AsnArgTyrLysThrPro-297
Hydrophilic Regions - Hopp-Woods
SEQ. ID. NO. 31356 50-LeuLysGluAspArgAlaArgIle-57
SEQ. ID. NO. 31357 65-GlyLeuAsnProAspThrGlnThr-72
SEQ. ID. NO. 31358 79-GluThrAlaLysCysGlyLeu-85
SEQ. ID. NO. 31359 92-PheLysLysProGluAspIleGluThr-100
SEQ. ID. NO. 31360 114-AlaLeuAspLysGlyGlu-119
SEQ. ID. NO. 31361 151-LysProProLysIleLysAlaIleAspLysIleMetGln-163
SEQ. ID. NO. 31362 165-GlyArgValArgGlyLysGlyLysThrAla-174
SEQ. ID. NO. 31363 188-LeuArgAlaGlyGlu-192
SEQ. ID. NO. 31364 201-ValProSerProGlnGluGly-207
SEQ. ID. NO. 31365 257-ValGlnGlyGluLeuAsnGlyAsnLysAlaHisAsp-268
g506
AMPHI Regions - AMPHI
SEQ. ID. NO. 31366 6-GluValGlyArgIleAlaHisGlyCysGlyGlyValVal-18
SEQ. ID. NO. 31367 25-ArgValValHisGlnValGluGlnGlyAlaArgLeuAla-37
SEQ. ID. NO. 31368 56-PheGlnArgArgPhe-60
SEQ. ID. NO. 31369 99-AlaThrArgThrIleAspGlyAsp-106
SEQ. ID. NO. 31370 123-GluGlnThrGlyLeuGln-128
SEQ. ID. NO. 31371 138-GlyAsnGluValAlaArgCys-144
SEQ. ID. NO. 31372 180-GlnValLysArgMetIleArgHisPhe-188
SEQ. ID. NO. 31373 199-ValHisArgProPheArgGluLeuAlaAlaLeuAspGlyPheValGlnVal-215
SEQ. ID. NO. 31374 224-GlyAspAspPheCysSerPhePheValGlyGlnValPheAsnProLeuLeu-240

TABLE 1-continued

| | |
|---|---|
| SEQ. ID. NO. 31375 | 249-LysThrPheAlaArgPheValPro-256 |
| SEQ. ID. NO. 31376 | 283-AsnLeuValGlnGlyPhe-288 |
| SEQ. ID. NO. 31377 | 313-PheValGlnValGlyGluPheAlaArgValAlaGlnGluGlu-326 |
| SEQ. ID. NO. 31378 | 372-GlyPhePheAlaAspPheAlaGluAsnPheGlyAlaGlyVal-385 |
| SEQ. ID. NO. 31379 | 408-PheGlyAspAspPheAlaHisGluValGlyGlu-418 |
| SEQ. ID. NO. 31380 | 465-CysSerPheSerGlnValGlyGlnMetGly-474 |
| Antigenic Index - Jameson-Wolf | |
| SEQ. ID. NO. 31381 | 12-HisGlyCysGlyGly-16 |
| SEQ. ID. NO. 31382 | 31-GluGlnGlyAlaArgLeuAla-37 |
| SEQ. ID. NO. 31383 | 54-ValAspPheGlnArgArgPheGlyGluVal-63 |
| SEQ. ID. NO. 31384 | 98-ArgAlaThrArgThrIleAspGlyAspLeuAlaGlu-109 |
| SEQ. ID. NO. 31385 | 131-IleArgAlaArgAlaAspThrGlyAsnGluValAlaArgCysGluGly-146 |
| SEQ. ID. NO. 31386 | 176-ProAsnPheGlyGlnValLysArgMetIle-185 |
| SEQ. ID. NO. 31387 | 195-HisAspLeuAspValHisArgProPheArgGlu-205 |
| SEQ. ID. NO. 31388 | 224-GlyAspAspPheCysSer-229 |
| SEQ. ID. NO. 31389 | 244-MetGluPheHisProLysThrPhe-251 |
| SEQ. ID. NO. 31390 | 259-ValGlyMetArgThrGluAla-265 |
| SEQ. ID. NO. 31391 | 279-HisHisAspGlyAsnLeu-284 |
| SEQ. ID. NO. 31392 | 288-PheGlyGlnGlnArgProGluValProVal-297 |
| SEQ. ID. NO. 31393 | 320-AlaArgValAlaGlnGluGluHisGlyArgValValAla-332 |
| SEQ. ID. NO. 31394 | 344-PheGlnArgLysThrAlaAspVal-351 |
| SEQ. ID. NO. 31395 | 362-CysHisGlyGlyGluThrGlyGlu-369 |
| SEQ. ID. NO. 31396 | 391-CysTyrGlyLysArgThrGluArgAlaArgThr-401 |
| SEQ. ID. NO. 31397 | 408-PheGlyAspAspPheAlaHisGluVal-416 |
| SEQ. ID. NO. 31398 | 428-GlnGlnGlyAlaAlaArgAlaGlyGlyGln-437 |
| SEQ. ID. NO. 31399 | 459-GlyGlySerHisArgSerCysSer-466 |
| SEQ. ID. NO. 31400 | 471-GlyGlnMetGlyGlyLysArgLeuThrValArgPheGlyGlyLysArgIleArgAsnArgPheLeuAspCysAsnLysPheLeuGlu-499 |
| SEQ. ID. NO. 31401 | 508-LysThrMetAspAlaIleIle-514 |
| SEQ. ID. NO. 31402 | 516-GlnAspPheArgTyr-520 |
| Hydrophilic Regions - Hopp-Woods | |
| SEQ. ID. NO. 31403 | 31-GluGlnGlyAlaArgLeuAla-37 |
| SEQ. ID. NO. 31404 | 54-ValAspPheGlnArgArgPheGlyGlu-62 |
| SEQ. ID. NO. 31405 | 98-ArgAlaThrArgThrIleAspGlyAspLeuAlaGlu-109 |
| SEQ. ID. NO. 31406 | 131-IleArgAlaArgAlaAspThrGlyAsnGluValAlaArgCysGluGly-146 |
| SEQ. ID. NO. 31407 | 180-GlnValLysArgMetIle-185 |
| SEQ. ID. NO. 31408 | 195-HisAspLeuAspVal-199 |
| SEQ. ID. NO. 31409 | 201-ArgProPheArgGlu-205 |
| SEQ. ID. NO. 31410 | 244-MetGluPheHisPro-248 |
| SEQ. ID. NO. 31411 | 259-ValGlyMetArgThrGluAla-265 |
| SEQ. ID. NO. 31412 | 289-GlyGlnGlnArgProGluVal-295 |
| SEQ. ID. NO. 31413 | 320-AlaArgValAlaGlnGluGluHisGlyArgValValAla-332 |
| SEQ. ID. NO. 31414 | 344-PheGlnArgLysThrAlaAspVal-351 |
| SEQ. ID. NO. 31415 | 364-GlyGlyGluThrGlyGlu-369 |
| SEQ. ID. NO. 31416 | 393-GlyLysArgThrGluArgAlaArgThr-401 |
| SEQ. ID. NO. 31417 | 412-PheAlaHisGluVal-416 |
| SEQ. ID. NO. 31418 | 429-GlnGlyAlaAlaArgAlaGlyGly-436 |
| SEQ. ID. NO. 31419 | 473-MetGlyGlyLysArgLeuThr-479 |
| SEQ. ID. NO. 31420 | 482-PheGlyGlyLysArgIleArgAsnArgPheLeuAsp-493 |
| SEQ. ID. NO. 31421 | 508-LysThrMetAspAlaIleIle-514 |
| SEQ. ID. NO. 31422 | 516-GlnAspPheArgTyr-520 |
| g513-2 | |
| AMPHI Regions - AMPHI | |
| SEQ. ID. NO. 31423 | 6-ThrGluTrpLeuHisGlyTrpValGlyAlaIleAsnAspProMetTrp-21 |
| SEQ. ID. NO. 31424 | 48-GlyArgSerIleLysGlu-53 |
| SEQ. ID. NO. 31425 | 66-GlyIleThrProPheGlnAlaPheValThrGlyLeuAla-78 |
| SEQ. ID. NO. 31426 | 119-SerSerLeuAlaGlnLeuPheLysValArgAsp-129 |
| SEQ. ID. NO. 31427 | 146-GlyLeuGlyGlnLysTrpLeuGlyVal-154 |
| SEQ. ID. NO. 31428 | 176-IleAlaAspThrVal-180 |
| SEQ. ID. NO. 31429 | 205-GlyGlyIleArgArgIleSerLysAlaAla-214 |
| SEQ. ID. NO. 31430 | 243-ValPheGlyGlnIlePheSer-249 |
| SEQ. ID. NO. 31431 | 259-GlyGlyLeuLeuGlyGlyLeuIle-266 |
| SEQ. ID. NO. 31432 | 288-AlaProAsnAlaAlaAlaAlaAla-295 |
| SEQ. ID. NO. 31433 | 303-GlnGlyMetIleGlnMetLeuGlyValPheValAsp-314 |
| SEQ. ID. NO. 31434 | 332-ProTyrGlyAspLeu-336 |
| SEQ. ID. NO. 31435 | 347-ValSerGlnValGlyGlnTrp-353 |
| SEQ. ID. NO. 31436 | 391-ThrAlaValPheArgMet-396 |
| SEQ. ID. NO. 31437 | 403-TyrPheGlyAlaValAla-408 |
| SEQ. ID. NO. 31438 | 423-IleMetAlaTrpIleAsnLeuValAlaIleLeuLeuLeuSer-436 |
| Antigenic Index - Jameson-Wolf | |
| SEQ. ID. NO. 31439 | 1-MetAsnGluAsnPhe-5 |
| SEQ. ID. NO. 31440 | 48-GlyArgSerIleLysGluMetLeuGlyGlyArgLysGlnGlyAspAspProHisGly-66 |
| SEQ. ID. NO. 31441 | 126-LysValArgAspCysAspAsnHisHisPheArgGlyGlyProAla-140 |
| SEQ. ID. NO. 31442 | 208-ArgArgIleSerLysAlaAlaGlu-215 |
| SEQ. ID. NO. 31443 | 273-GlyIleLysArgGlyLeuTyrSerAsnGluAlaGlyMetGlySerAlaProAsnAla-291 |
| SEQ. ID. NO. 31444 | 295-AlaGluValLysHisProValSer-302 |
| SEQ. ID. NO. 31445 | 331-GlnProTyrGlyAspLeuSerGly-338 |
| SEQ. ID. NO. 31446 | 375-AlaTyrAlaGluSerAsnVal-381 |
| SEQ. ID. NO. 31447 | 444-ArgAspTyrThrAlaLysLeuLysMetGlyLysAspProGluPheLysLeuSerGluHisProGlyLeuLysArgArgIleLysSerAspValTrp-475 |

TABLE 1-continued

| | |
|---|---|
| Hydrophilic Regions - Hopp-Woods | |
| SEQ. ID. NO. 31448 | 48-GlyArgSerIleLysGluMetLeuGlyGlyArgLysGlnGlyAspAspProHisGly-66 |
| SEQ. ID. NO. 31449 | 126-LysValArgAspCysAspAsnHisHis-134 |
| SEQ. ID. NO. 31450 | 208-ArgArgIleSerLysAlaAlaGlu-215 |
| SEQ. ID. NO. 31451 | 273-GlyIleLysArgGlyLeuTyr-279 |
| SEQ. ID. NO. 31452 | 295-AlaGluValLysHisProVal-301 |
| SEQ. ID. NO. 31453 | 450-LeuLysMetGlyLysAspProGluPheLysLeuSerGlu-462 |
| SEQ. ID. NO. 31454 | 464-ProGlyLeuLysArgArgIleLysSer-472 |
| g515-1 | |
| AMPHI Regions - AMPHI | |
| SEQ. ID. NO. 31455 | 8-ArgAlaAlaGlyValAlaArgGlyLeuHisSerGluPheAlaArg-22 |
| SEQ. ID. NO. 31456 | 59-AspValArgPhePheAlaGlnValGluGluIleGlyGlnAspPhePheAlaAspAla-77 |
| SEQ. ID. NO. 31457 | 90-AlaGlyGluCysAlaAspGluValSerAspGlnPro-101 |
| SEQ. ID. NO. 31458 | 122-GluSerAlaGlnSerAlaAlaGlyGlyGlyLeuThrAspGlyPheGly-137 |
| SEQ. ID. NO. 31459 | 176-CysGlyLysThrValGlyVal-182 |
| SEQ. ID. NO. 31460 | 192-LeuHisArgArgAla-196 |
| SEQ. ID. NO. 31461 | 233-ValAlaAspValLeuArg-238 |
| SEQ. ID. NO. 31462 | 251-PheGlyGlyValAlaGlyAspValGlyGlyGlyAlaAspGlyValAlaGlnGlyLeuPheGlyGluVal-273 |
| SEQ. ID. NO. 31463 | 306-HisAlaAspAlaLeuSerGluArgPheAla-315 |
| SEQ. ID. NO. 31464 | 334-AlaAlaGluValGluGluPheGlySerGlyValValGluGln-347 |
| Antigenic Index - Jameson-Wolf | |
| SEQ. ID. NO. 31465 | 24-ValThrAlaGluGluIleAlaPhe-31 |
| SEQ. ID. NO. 31466 | 38-HisGluAlaArgArgGlyGlyAsnThrPhe-47 |
| SEQ. ID. NO. 31467 | 51-IleAlaAlaAlaGluArgAlaGlyAsp-59 |
| SEQ. ID. NO. 31468 | 67-GluGluIleGlyGln-71 |
| SEQ. ID. NO. 31469 | 77-AlaValAspGlnGluThr-82 |
| SEQ. ID. NO. 31470 | 84-LeuAlaValGluArgAlaAlaGlyGluCysAlaAspGluValSerAspGlnProAlaArgAsnGlyGlyIleGluGluAspGlyValAlaAlaCysArg AspAlaAlaAlaAlaGluSerAlaGln-125 |
| SEQ. ID. NO. 31471 | 128-AlaGlyGlyGlyLeuThrAspGly-135 |
| SEQ. ID. NO. 31472 | 160-GlyGlyAsnAspAlaAlaGlyAsn-167 |
| SEQ. ID. NO. 31473 | 192-LeuHisArgArgAla-196 |
| SEQ. ID. NO. 31474 | 217-AlaAspGlyGlyPheArg-222 |
| SEQ. ID. NO. 31475 | 242-GlyValGlyLysSerGlyAla-248 |
| SEQ. ID. NO. 31476 | 257-AspValGlyGlyGlyAlaAspGlyVal-265 |
| SEQ. ID. NO. 31477 | 284-AspValAsnGlyAsnValGln-290 |
| SEQ. ID. NO. 31478 | 309-AlaLeuSerGluArgPheAla-315 |
| SEQ. ID. NO. 31479 | 318-GlyPheGlyGlyGlyArgAlaArgCys-326 |
| SEQ. ID. NO. 31480 | 328-CysGlnValGluArgAlaAlaAlaGluValGluGluPheGlySerGlyVal-344 |
| SEQ. ID. NO. 31481 | 347-GlnHisAsnAsnLeu-351 |
| Hydrophilic Regions - Hopp-Woods | |
| SEQ. ID. NO. 31482 | 24-ValThrAlaGluGluIleAlaPhe-31 |
| SEQ. ID. NO. 31483 | 38-HisGluAlaArgArgGlyGlyAsn-45 |
| SEQ. ID. NO. 31484 | 51-IleAlaAlaAlaGluArgAlaGlyAsp-59 |
| SEQ. ID. NO. 31485 | 77-AlaValAspGlnGluThr-82 |
| SEQ. ID. NO. 31486 | 84-LeuAlaValGluArgAlaAlaGlyGluCysAlaAspGluValSerAspGlnProAlaArgAsnGly GlyIleGluGluAspGlyValAlaAlaCysArgAspAlaAlaAlaAlaGluSerAlaGln-125 |
| SEQ. ID. NO. 31487 | 162-AsnAspAlaAlaGly-166 |
| SEQ. ID. NO. 31488 | 192-LeuHisArgArgAla-196 |
| SEQ. ID. NO. 31489 | 258-ValGlyGlyGlyAlaAspGlyVal-265 |
| SEQ. ID. NO. 31490 | 309-AlaLeuSerGluArgPheAla-315 |
| SEQ. ID. NO. 31491 | 322-GlyArgAlaArgCys-326 |
| SEQ. ID. NO. 31492 | 328-CysGlnValGluArgAlaAlaAlaGluValGluGluPheGly-341 |
| g519-1 | |
| AMPHI Regions - AMPHI | |
| SEQ. ID. NO. 31493 | 13-ValPheGlyPheLysSerPhe-19 |
| SEQ. ID. NO. 31494 | 29-ValValGluArgLeuGlyArgPheHisArgAlaLeuThrAlaGly-43 |
| SEQ. ID. NO. 31495 | 105-MetAlaIleThrGlnLeuAlaGlnThrThrLeuArgSerVal-118 |
| SEQ. ID. NO. 31496 | 139-ValSerAlaLeuAspGluAlaAla-146 |
| SEQ. ID. NO. 31497 | 165-GlnGluIleLeuArgAlaMetGln-172 |
| SEQ. ID. NO. 31498 | 192-LysIleGluGlnIle-196 |
| SEQ. ID. NO. 31499 | 221-SerAsnAlaGluLysIleAlaArgIleAsn-230 |
| SEQ. ID. NO. 31500 | 249-AlaIleArgGlnIleAlaAlaAla-256 |
| SEQ. ID. NO. 31501 | 273-GlnTyrValAlaAlaPheAsnAsnLeuAlaLys-283 |
| SEQ. ID. NO. 31502 | 292-AlaAsnValAlaAspIleGlySerLeuIleSerAlaGlyMetLysIleIleAspSerSerLysThrAla-314 |
| Antigenic Index - Jameson-Wolf | |
| SEQ. ID. NO. 31503 | 31-GluArgLeuGlyArgPheHisArg-38 |
| SEQ. ID. NO. 31504 | 58-HisSerLeuLysGluIleProLeuAspValProSerGln-70 |
| SEQ. ID. NO. 31505 | 72-CysIleThrArgAspAsnThrGlnLeuThrVal-82 |
| SEQ. ID. NO. 31506 | 91-ThrAspProLysLeuAlaSer-97 |
| SEQ. ID. NO. 31507 | 122-MetGluLeuAspLysThrPheGluGluArgAspGluIleAsn-135 |
| SEQ. ID. NO. 31508 | 141-AlaLeuAspGluAlaAlaGly-147 |
| SEQ. ID. NO. 31509 | 154-LeuArgTyrGluIleLysAspLeuValPro-163 |
| SEQ. ID. NO. 31510 | 175-IleThrAlaGluArgGluLysArgAlaArgIleAlaGluSerGluGlyArgLysIleGluGln-195 |
| SEQ. ID. NO. 31511 | 197-AsnLeuAlaSerGlyGlnArgGluAlaGluIleGlnGlnSerGluGlyGluAlaGlnAla-216 |
| SEQ. ID. NO. 31512 | 219-AsnAlaSerAsnAlaGluLysIleAlaArgIleAsnArgAlaLysGlyGluAlaGluSerLeuArgLeu-241 |
| SEQ. ID. NO. 31513 | 245-AlaAsnAlaGluAlaIleArg-251 |

TABLE 1-continued

| | |
|---|---|
| SEQ. ID. NO. 31514 | 258-GlnThrGlnGlyGlyAlaAspAlaValAsn-267 |
| SEQ. ID. NO. 31515 | 281-LeuAlaLysGluSerAsnThr-287 |
| SEQ. ID. NO. 31516 | 303-AlaGlyMetLysIleIleAspSerSerLysThrAlaLys-315 |
| Hydrophilic Regions - Hopp-Woods | |
| SEQ. ID. NO. 31517 | 31-GluArgLeuGlyArgPheHisArg-38 |
| SEQ. ID. NO. 31518 | 58-HisSerLeuLysGluIleProLeu-65 |
| SEQ. ID. NO. 31519 | 73-IleThrArgAspAsnThr-78 |
| SEQ. ID. NO. 31520 | 91-ThrAspProLysLeu-95 |
| SEQ. ID. NO. 31521 | 122-MetGluLeuAspLysThrPheGluGluArgAspGluIleAsn-135 |
| SEQ. ID. NO. 31522 | 141-AlaLeuAspGluAlaAla-146 |
| SEQ. ID. NO. 31523 | 154-LeuArgTyrGluIleLysAspLeuValPro-163 |
| SEQ. ID. NO. 31524 | 175-IleThrAlaGluArgGluLysArgAlaArgIleAlaGluSerGluGlyArgLysIleGluGln-195 |
| SEQ. ID. NO. 31525 | 200-SerGlyGlnArgGluAlaGluIleGlnGlnSerGluGlyGluAlaGlnAla-216 |
| SEQ. ID. NO. 31526 | 221-SerAsnAlaGluLysIleAlaArgIleAsnArgAlaLysGlyGluAlaGluSerLeuArgLeu-241 |
| SEQ. ID. NO. 31527 | 245-AlaAsnAlaGluAlaIleArg-251 |
| SEQ. ID. NO. 31528 | 281-LeuAlaLysGluSerAsn-286 |
| SEQ. ID. NO. 31529 | 306-LysIleIleAspSerSerLysThrAlaLys-315 |
| g520-1 | |
| AMPHI Regions - AMPHI | |
| SEQ. ID. NO. 31530 | 109-AspGlyGlnIleTrpArgAlaPheSerSerLeuLys-120 |
| Antigenic Index - Jameson-Wolf | |
| SEQ. ID. NO. 31531 | 20-LysProSerArgArgAlaLeu-26 |
| SEQ. ID. NO. 31532 | 47-AlaSerGlyLysIleSerLeuPro-54 |
| SEQ. ID. NO. 31533 | 84-ProProAsnAsnSerThrThrThrSerThrSerLeuArgAlaThrSerSerAsnGlySerLeuThrLysAlaAlaAsp-109 |
| SEQ. ID. NO. 31534 | 122-HisMetAlaGluIleArgIleSerArgProLysArgArgGluIleSerSerAlaLeuSerArgAsnThrAlaAlaAlaPro-148 |
| SEQ. ID. NO. 31535 | 150-ProThrValProLysProLysArgProMet-159 |
| SEQ. ID. NO. 31536 | 166-SerProCysLysProThrGluMet-173 |
| Hydrophilic Regions - Hopp-Woods | |
| SEQ. ID. NO. 31537 | 20-LysProSerArgArgAlaLeu-26 |
| SEQ. ID. NO. 31538 | 93-ThrSerLeuArgAlaThrSerSer-100 |
| SEQ. ID. NO. 31539 | 103-SerLeuThrLysAlaAlaAsp-109 |
| SEQ. ID. NO. 31540 | 122-HisMetAlaGluIleArgIleSerArgProLysArgArgGluIleSer-137 |
| SEQ. ID. NO. 31541 | 140-LeuSerArgAsnThrAla-145 |
| SEQ. ID. NO. 31542 | 151-ThrValProLysProLysArgProMet-159 |
| SEQ. ID. NO. 31543 | 168-CysLysProThrGluMet-173 |
| g521 | |
| AMPHI Regions - AMPHI | |
| SEQ. ID. NO. 31544 | 39-ThrLysProSerLysSerCys-45 |
| SEQ. ID. NO. 31545 | 50-LeuProProIleGly-54 |
| SEQ. ID. NO. 31546 | 86-ValLysThrValSerLysProAlaLysSer-95 |
| SEQ. ID. NO. 31547 | 126-AlaGlnLysMetLeu-130 |
| SEQ. ID. NO. 31548 | 132-GlnAlaArgLeuAlaLysGlyGlyAsn-140 |
| SEQ. ID. NO. 31549 | 146-IleAsnAlaLeuSerAsnValLeuAspArgGlnGlnAsnIle-159 |
| Antigenic Index - Jameson-Wolf | |
| SEQ. ID. NO. 31550 | 1-MetLysSerLysLeu-5 |
| SEQ. ID. NO. 31551 | 36-ValTyrThrThrLysProSerLysSerCysHisSerThrAspLeuProProIleGlyAsnTyrSerSerGluArgTyrIle-62 |
| SEQ. ID. NO. 31552 | 65-GlnThrProGluProAlaProSerProSerAsnGlyGlyGln-78 |
| SEQ. ID. NO. 31553 | 80-ValLysTyrLysAlaProVal-86 |
| SEQ. ID. NO. 31554 | 88-ThrValSerLysProAlaLysSerAsnThrProProGlnGlnAlaProValAsnAsnSerArgArgSerIleLeuGluAla GluLeuSerAsnGluArgLysAlaLeuThrGluAlaGlnLysMetLeuSer-131 |
| SEQ. ID. NO. 31555 | 134-ArgLeuAlaLysGlyGlyAsnIleAsnHisGlnLys-145 |
| SEQ. ID. NO. 31556 | 152-ValLeuAspArgGlnGlnAsn-158 |
| SEQ. ID. NO. 31557 | 162-LeuGlnArgGluLeuGlyArg-168 |
| Hydrophilic Regions - Hopp-Woods | |
| SEQ. ID. NO. 31558 | 1-MetLysSerLysLeu-5 |
| SEQ. ID. NO. 31559 | 40-LysProSerLysSerCysHis-46 |
| SEQ. ID. NO. 31560 | 57-SerSerGluArgTyrIle-62 |
| SEQ. ID. NO. 31561 | 66-ThrProGluProAlaProSerProSerAsnGly-76 |
| SEQ. ID. NO. 31562 | 80-ValLysTyrLysAlaProVal-86 |
| SEQ. ID. NO. 31563 | 88-ThrValSerLysProAlaLysSerAsnThrPro-98 |
| SEQ. ID. NO. 31564 | 105-AsnAsnSerArgArgSerIleLeuGluAlaGluLeuSerAsnGluArgLysAlaLeuThrGluAlaGlnLysMetLeuSer-131 |
| SEQ. ID. NO. 31565 | 152-ValLeuAspArgGlnGlnAsn-158 |
| SEQ. ID. NO. 31566 | 162-LeuGlnArgGluLeuGlyArg-168 |
| g522 | |
| AMPHI Regions - AMPHI | |
| SEQ. ID. NO. 31567 | 57-LysIleValGluSerCysMetLys-64 |
| SEQ. ID. NO. 31568 | 96-MetTrpGluGlnProLeuAspGlyLeuSerGluLysGlnIleSerSerPheGlyLysLeuGlyAlaGlnGluGlnLeuAspLeuLeuGlyGlyAla-127 |
| Antigenic Index - Jameson-Wolf | |
| SEQ. ID. NO. 31569 | 1-MetThrGluProLysHisGluThrProThrGluGluGlnValAlaAlaArgLysLysAlaLysAlaLysIleArgThr-26 |
| SEQ. ID. NO. 31570 | 48-AlaMetSerLysProGlnAlaLysGlnLysIleValGluSerCysMetLys-64 |
| SEQ. ID. NO. 31571 | 71-LysTrpGlnAsnAspLeuLysAlaArgGlyLeuAspAlaAspAsnThrArgLeu-88 |
| SEQ. ID. NO. 31572 | 103-GlyLeuSerGluLysGlnIleSerSerPheGlyLysLeuGlyAla-117 |
| SEQ. ID. NO. 31573 | 128-AsnAlaPheGluThrArgAspLysGlnCysValAlaAspLeuLysAlaAsp-144 |
| Hydrophilic Regions - Hopp-Woods | |
| SEQ. ID. NO. 31574 | 1-MetThrGluProLysHisGluThrProThrGluGluGlnValAlaAlaArgLysLysAlaLysAlaLysIleArgThr-26 |
| SEQ. ID. NO. 31575 | 48-AlaMetSerLysProGlnAlaLysGlnLysIleValGluSerCysMet-63 |

TABLE 1-continued

| | |
|---|---|
| SEQ. ID. NO. 31576 | 72-TrpGlnAsnAspLeuLysAlaArgGlyLeuAspAlaAspAsnThrArgLeu-88 |
| SEQ. ID. NO. 31577 | 103-GlyLeuSerGluLysGlnIle-109 |
| SEQ. ID. NO. 31578 | 130-PheGluThrArgAspLysGlnCysValAlaAspLeuLysAlaAsp-144 |
| g525-1 | |
| AMPHI Regions - AMPHI | |
| SEQ. ID. NO. 31579 | 59-GluPheAlaGluPheValAsnSerHisProGln-69 |
| SEQ. ID. NO. 31580 | 86-LysHisTrpMetLysAsnGly-92 |
| SEQ. ID. NO. 31581 | 125-ArgLeuProThrIleAspGluTrpGluPhe-134 |
| SEQ. ID. NO. 31582 | 154-ThrIleLeuAspTrpTyr-159 |
| SEQ. ID. NO. 31583 | 164-ArgLysGlyLeuHisAspValGly-171 |
| SEQ. ID. NO. 31584 | 178-TrpGlyValTyrAsp-182 |
| SEQ. ID. NO. 31585 | 188-TrpGluTrpThrGlu-192 |
| Antigenic Index - Jameson-Wolf | |
| SEQ. ID. NO. 31586 | 24-ValGlnIleGluGlyGlySerTyrArgProLeuTyrLeuLysLysAspThrGlyLeuIleLys-44 |
| SEQ. ID. NO. 31587 | 46-LysProPheLysLeuAspLysTyrProValThr-56 |
| SEQ. ID. NO. 31588 | 67-HisProGlnTrpGlnLysGlyArgIleGlySerLysGlnAlaGlu-81 |
| SEQ. ID. NO. 31589 | 88-TrpMetLysAsnGlySerArgSerTyrAlaProLysAlaGlyGluLeuLysGlnPro-106 |
| SEQ. ID. NO. 31590 | 122-GlnGlyLysArgLeuProThrIleAspGluTrpGlu-133 |
| SEQ. ID. NO. 31591 | 140-AlaThrGlnLysAsnGlySerAsnGluProGlyTyrAsnArgThr-154 |
| SEQ. ID. NO. 31592 | 159-TyrAlaAspGlyGlyArgLysGlyLeuHisAspValGlyLysAspArgProAsnTyr-177 |
| SEQ. ID. NO. 31593 | 190-TrpThrGluAspPheAsnSerSerLeuLeuSerSerGlyAsnAla-204 |
| SEQ. ID. NO. 31594 | 213-AlaSerValGlyAlaSerAspSerSerAsnTyr-223 |
| SEQ. ID. NO. 31595 | 234-SerLeuGlnSerLysTyr-239 |
| SEQ. ID. NO. 31596 | 245-GlyPheArgCysAlaSerArg-251 |
| Hydrophilic Regions - Hopp-Woods | |
| SEQ. ID. NO. 31597 | 35-TyrLeuLysLysAspThrGlyLeuIleLys-44 |
| SEQ. ID. NO. 31598 | 46-LysProPheLysLeuAspLysTyrPro-54 |
| SEQ. ID. NO. 31599 | 71-GlnLysGlyArgIleGlySerLysGlnAlaGlu-81 |
| SEQ. ID. NO. 31600 | 91-AsnGlySerArgSerTyrAla-97 |
| SEQ. ID. NO. 31601 | 99-LysAlaGlyGluLeuLysGln-105 |
| SEQ. ID. NO. 31602 | 122-GlnGlyLysArgLeuProThr-128 |
| SEQ. ID. NO. 31603 | 140-AlaThrGlnLysAsnGlySerAsnGluProGlyTyr-151 |
| SEQ. ID. NO. 31604 | 162-GlyGlyArgLysGlyLeuHisAspValGlyLysAspArgProAsn-176 |
| SEQ. ID. NO. 31605 | 216-GlyAlaSerAspSerSerAsn-222 |
| g527 | |
| AMPHI Regions - AMPHI | |
| SEQ. ID. NO. 31606 | 7-PhePheGlnProValGln-12 |
| SEQ. ID. NO. 31607 | 29-AspAlaAlaGluLeuValGluLeuPheAlaLeuPhePro-41 |
| SEQ. ID. NO. 31608 | 73-GlyLysGlyIleGluArgGlnValAspAsnIleAlaAspValTyrGlyPhe-89 |
| Antigenic Index - Jameson-Wolf | |
| SEQ. ID. NO. 31609 | 19-GlyArgSerAlaValGlyMetGlyGlySerAspAlaAlaGlu-32 |
| SEQ. ID. NO. 31610 | 52-GlnLysProArgLeuGlyCysArg-59 |
| SEQ. ID. NO. 31611 | 71-PheMetGlyLysGlyIleGluArgGlnValAspAsnIleAla-84 |
| SEQ. ID. NO. 31612 | 107-LeuLeuArgLysGlyThrGlyLeuGluLysThrCysArgProLysProPheValGlnProHisGlyGlyArg-130 |
| Hydrophilic Regions - Hopp-Woods | |
| SEQ. ID. NO. 31613 | 26-GlyGlySerAspAlaAlaGlu-32 |
| SEQ. ID. NO. 31614 | 53-LysProArgLeuGlyCys-58 |
| SEQ. ID. NO. 31615 | 71-PheMetGlyLysGlyIleGluArgGlnValAspAsnIleAla-84 |
| SEQ. ID. NO. 31616 | 107-LeuLeuArgLysGlyThrGlyLeuGluLysThrCysArgProLysPro-122 |
| g528 | |
| AMPHI Regions - AMPHI | |
| SEQ. ID. NO. 31617 | 23-ArgLeuAlaGlyTrpTyrGluCysSerSerLeuSerGlyTrpCysLysProArgLysProAlaAlaIle-45 |
| SEQ. ID. NO. 31618 | 69-AsnArgSerValArg-73 |
| SEQ. ID. NO. 31619 | 87-ArgLysIleGlyLysPhe-92 |
| SEQ. ID. NO. 31620 | 106-ProLeuValGluArgPheLys-112 |
| Antigenic Index - Jameson-Wolf | |
| SEQ. ID. NO. 31621 | 29-GluCysSerSerLeuSerGlyTrpCysLysProArgLysProAlaAla-44 |
| SEQ. ID. NO. 31622 | 49-AspIleGlyGlyGluSerProLeuSerLeuGluAspTyrGluIleProLeuSerAspGlyAsnArgSerValArgAlaAsnGluTyrGluSerAlaGln LysSerTyrPhe-85 |
| SEQ. ID. NO. 31623 | 88-LysIleGlyLysPheGluAlaCysGlyLeuAspTrpArgThrArgAspGlyLysProLeuValGluArgPheLysGlnGluGlyPheAspCysLeu GluLysGlnGlyLeuArgArgAsnGlyLeuSerGluArgValArgTrp-135 |
| Hydrophilic Regions - Hopp-Woods | |
| SEQ. ID. NO. 31624 | 37-CysLysProArgLysProAlaAla-44 |
| SEQ. ID. NO. 31625 | 54-SerProLeuSerLeuGluAspTyrGluIleProLeu-65 |
| SEQ. ID. NO. 31626 | 67-AspGlyAsnArgSerValArgAlaAsnGluTyrGluSerAlaGln-81 |
| SEQ. ID. NO. 31627 | 88-LysIleGlyLysPheGluAlaCys-95 |
| SEQ. ID. NO. 31628 | 99-TrpArgThrArgAspGlyLysProLeuValGluArgPheLysGlnGluGlyPheAspCysLeuGluLysGlnGlyLeu ArgArgAsnGlyLeuSerGluArgValArgTrp-135 |
| g531 | |
| AMPHI Regions - AMPHI | |
| SEQ. ID. NO. 31629 | 64-LeuAlaAspTyrMetAla-69 |
| SEQ. ID. NO. 31630 | 90-GlySerIleIleGlyIlePhePheSerLeuProGlyLeuIleLeuGly-105 |
| SEQ. ID. NO. 31631 | 108-IleGlyAlaAlaAlaGly-113 |
| SEQ. ID. NO. 31632 | 132-LeuLeuGlyLeuValVal-137 |

TABLE 1-continued

Antigenic Index - Jameson-Wolf
SEQ. ID. NO. 31633 77-ThrGlyAlaGlyLysLeuAlaVal-84
SEQ. ID. NO. 31634 114-GluLeuIleAspArgArgAsnMet-121
Hydrophilic Regions - Hopp-Woods
SEQ. ID. NO. 31635 114-GluLeuIleAspArgArgAsnMet-121
g532-2
AMPHI Regions - AMPHI
SEQ. ID. NO. 31636 6-LysLysGlnAlaAsp-10
SEQ. ID. NO. 31637 27-AlaLeuLeuSerAlaValThrHisLeuLeuAlaIlePheValProMetIleThr-44
SEQ. ID. NO. 31638 76-TyrLeuGlnValAsnArgPheGlySerVal-85
SEQ. ID. NO. 31639 122-SerThrLeuLeuGlyValSerPhe-129
SEQ. ID. NO. 31640 147-LysValIleThrProThrVal-153
SEQ. ID. NO. 31641 184-ThrPheGlySerMetGluAsnLeuGly-192
SEQ. ID. NO. 31642 206-CysMetLysAsnPro-210
SEQ. ID. NO. 31643 224-GlyTyrIleValAlaLeu-229
SEQ. ID. NO. 31644 236-PheSerAlaLeuGlnAsnLeuPro-243
SEQ. ID. NO. 31645 271-LeuGlyValPheGluAlaValGlyAspLeuThrAla-282
SEQ. ID. NO. 31646 297-ThrLysArgLeuArgGlyGlyVal-304
SEQ. ID. NO. 31647 307-AspGlyLeuValSerValIleAlaThrAlaLeuGly-318
SEQ. ID. NO. 31648 338-AlaSerArgHisValGlyLysTyr-345
SEQ. ID. NO. 31649 361-ArgAlaPheThrThrIleProSerProVal-370
Antigenic Index - Jameson-Wolf
SEQ. ID. NO. 31650 3-GluThrMetLysLysGlnAlaAspSerProAspLeu-14
SEQ. ID. NO. 31651 16-TyrGlyLeuGluAspArgProProPhe-24
SEQ. ID. NO. 31652 80-AsnArgPheGlySer-84
SEQ. ID. NO. 31653 94-XxxXxxXxxXxxSerSer-99
SEQ. ID. NO. 31654 108-AlaGlyMetLysGluGlyGlyLeuSerGluGlyAla-119
SEQ. ID. NO. 31655 177-PheGlyAlaLysAlaAspGlyThrPheGlySer-187
SEQ. ID. NO. 31656 207-MetLysAsnProLeuLeuArg-213
SEQ. ID. NO. 31657 286-ValSerAspGlnProIleGluGlyGluGluTyrThrLysArgLeuArgGlyGlyValLeu-305
SEQ. ID. NO. 31658 394-GlyIleArgArgArgGluAlaVal-401
SEQ. ID. NO. 31659 431-IleSerGlyGlyGly-435
SEQ. ID. NO. 31660 445-LeuProGluAspLysThrGluAlaAlaValLysPheAspThrAspHisLeuGluHis-463
Hydrophilic Regions - Hopp-Woods
SEQ. ID. NO. 31661 3-GluThrMetLysLysGlnAlaAspSerProAsp-13
SEQ. ID. NO. 31662 18-LeuGluAspArgProProPhe-24
SEQ. ID. NO. 31663 109-GlyMetLysGluGlyGlyLeuSer-116
SEQ. ID. NO. 31664 179-AlaLysAlaAspGly-183
SEQ. ID. NO. 31665 289-GlnProIleGluGlyGluGluTyrThrLysArgLeuArgGly-302
SEQ. ID. NO. 31666 394-GlyIleArgArgArgGluAlaVal-401
SEQ. ID. NO. 31667 445-LeuProGluAspLysThrGluAlaAlaValLysPheAspThrAspHisLeuGluHis-463
g537
AMPHI Regions - AMPHI
SEQ. ID. NO. 31668 38-GlnIleArgAspGlyGlyAspAlaLeuHisTyrLeuAsnArgIle-52
SEQ. ID. NO. 31669 86-HisGlyGluHisHis-90
SEQ. ID. NO. 31670 109-GlyTyrLeuTyrAsnGlyValHisGlu-117
SEQ. ID. NO. 31671 138-ArgGlnValAspAlaLeuMetSerAlaIleTyr-148
SEQ. ID. NO. 31672 180-AsnGlySerPheGluArg-185
SEQ. ID. NO. 31673 190-GlyArgArgGlnProGluAlaGlyArgLysTyrTyrArgAsnAlaCys-205
SEQ. ID. NO. 31674 281-ArgProValArgValLeuThrAlaGly-289
SEQ. ID. NO. 31675 315-TyrThrAlaValPheAspTyrValArgAsnGly-325
SEQ. ID. NO. 31676 374-ThrArgTyrThrTyr-378
Antigenic Index - Jameson-Wolf
SEQ. ID. NO. 31677 21-ThrGlnAsnGlnSerLeuProAlaGly-29
SEQ. ID. NO. 31678 32-ValTyrProSerAlaProGlnIleArgAspGlyGlyAspAla-45
SEQ. ID. NO. 31679 69-AsnSerAlaArgArgHisAlaArg-76
SEQ. ID. NO. 31680 80-LeuAsnProGluAspGlyHisGlyGluHisHisProAspAsnProHis-95
SEQ. ID. NO. 31681 99-GlnLysLeuThrGluArgThrArgLeu-107
SEQ. ID. NO. 31682 115-ValHisGluAsnIleSerThrGluGluGluAlaAlaGluSerSerAspSerAspIleArgThrGlnGlnArgGlnValAsp-141
SEQ. ID. NO. 31683 152-SerLeuLeuAspArgHisThrAspGluAlaGly-162
SEQ. ID. NO. 31684 165-PheValArgGluAsnGlyLysThr-172
SEQ. ID. NO. 31685 178-GlnGlyAsnGlySerPheGluArgAlaCysAlaLysGlyArgArgGlnProGluAlaGlyArgLysTyrTyrArgAsnAlaCysHisAsnGly-208
SEQ. ID. NO. 31686 238-TyrGlyGluArgProAspProValProGluTyrGluIleThrGlyAsnProAlaSer-256
SEQ. ID. NO. 31687 258-AspPheSerGluAlaAlaGly-264
SEQ. ID. NO. 31688 266-IleAlaMetLysSer-270
SEQ. ID. NO. 31689 274-TyrGlnGlyLysAsnGluIleArgPro-282
SEQ. ID. NO. 31690 287-ThrAlaGlyAsnAspProAsnGlyArgLeuThr-297
SEQ. ID. NO. 31691 321-TyrValArgAsnGlyArgHisAlaGln-329
SEQ. ID. NO. 31692 334-PheArgThrArgLysProAspTyrProTyr-343
SEQ. ID. NO. 31693 345-GluValAsnGlyGlyGluThrLeuAlaValArgLysGlyGluLys-359
SEQ. ID. NO. 31694 364-TrpArgGlyArgTrpCysLeu-370
SEQ. ID. NO. 31695 380-ArgGlnPheGlyAsnSer-385
SEQ. ID. NO. 31696 389-LeuArgHisGluAlaGlyGly-395
SEQ. ID. NO. 31697 402-GlyMetAlaGlySerArgIleArgLeuThrProGluAspSerProGluArgGly-419
Hydrophilic Regions - Hopp-Woods
SEQ. ID. NO. 31698 37-ProGlnIleArgAspGlyGlyAsp-44
SEQ. ID. NO. 31699 69-AsnSerAlaArgArgHisAlaArg-76
SEQ. ID. NO. 31700 81-AsnProGluAspGlyHisGlyGluHisHisProAsp-92
SEQ. ID. NO. 31701 100-LysLeuThrGluArgThrArgLeu-107
SEQ. ID. NO. 31702 119-IleSerThrGluGluGluAlaAlaGluSerSerAspSerAspIleArgThrGlnGlnArgGlnValAsp-141

TABLE 1-continued

| | |
|---|---|
| SEQ. ID. NO. 31703 | 152-SerLeuLeuAspArgHisThrAspGluAlaGly-162 |
| SEQ. ID. NO. 31704 | 165-PheValArgGluAsnGlyLys-171 |
| SEQ. ID. NO. 31705 | 181-GlySerPheGluArgAlaCysAlaLysGlyArgArgGlnProGluAlaGlyArgLysTyrTyrArg-202 |
| SEQ. ID. NO. 31706 | 240-GluArgProAspProValProGluTyrGluIle-250 |
| SEQ. ID. NO. 31707 | 258-AspPheSerGluAlaAlaGly-264 |
| SEQ. ID. NO. 31708 | 266-IleAlaMetLysSer-270 |
| SEQ. ID. NO. 31709 | 275-GlnGlyLysAsnGluIleArgPro-282 |
| SEQ. ID. NO. 31710 | 289-GlyAsnAspProAsnGlyArgLeuThr-297 |
| SEQ. ID. NO. 31711 | 323-ArgAsnGlyArgHisAlaGln-329 |
| SEQ. ID. NO. 31712 | 334-PheArgThrArgLysProAsp-340 |
| SEQ. ID. NO. 31713 | 352-LeuAlaValArgLysGlyGluLys-359 |
| SEQ. ID. NO. 31714 | 389-LeuArgHisGluAla-393 |
| SEQ. ID. NO. 31715 | 406-SerArgIleArgLeuThrProGluAspSerProGluArgGly-419 |
| g538 | |
| AMPHI Regions - AMPHI | |
| SEQ. ID. NO. 31716 | 41-ThrAlaLeuAlaGluAlaValGluLeuValLysAlaAlaGly-54 |
| SEQ. ID. NO. 31717 | 78-LysAlaAlaGluLeuSerGluAlaValAla-87 |
| SEQ. ID. NO. 31718 | 104-GlnGluArgAsnLeuGluLysIleLeuGlnCysArgValLeuAspArgVal-120 |
| SEQ. ID. NO. 31719 | 144-GlnLeuSerHisLeuAlaGlyArgLeuIleArgGlyTyrGlyHisLeuGln-160 |
| SEQ. ID. NO. 31720 | 187-IleAsnAlaLeuLysLysGlnLeuAla-195 |
| SEQ. ID. NO. 31721 | 211-GlyArgIleLysThrPheAlaLeuValGlyTyrThrAsn-223 |
| SEQ. ID. NO. 31722 | 230-PheAsnArgLeuThrLys-235 |
| SEQ. ID. NO. 31723 | 270-GlyPheValSerAspLeuProHisLysLeuIleSerAlaPheSerAlaThrLeuGlu-288 |
| SEQ. ID. NO. 31724 | 306-AsnSerGlyGlnGlnIleGluAspValGluAsnValLeuGlnGluIleHis-322 |
| SEQ. ID. NO. 31725 | 364-GluAsnThrGlyIleAspAlaLeuArgGluAlaIleAlaGluTyrCysAla-380 |
| Antigenic Index - Jameson-Wolf | |
| SEQ. ID. NO. 31726 | 1-SerGlyArgThrGlyArgAsnSerAlaThrGlnAlaGlnProGluArgVal-17 |
| SEQ. ID. NO. 31727 | 24-LeuAspLysAspAspThrGlySerAsnAlaAlaArg-35 |
| SEQ. ID. NO. 31728 | 47-ValGluLeuValLys-51 |
| SEQ. ID. NO. 31729 | 53-AlaGlyGlyAspSerValArgValGluThrAlaLysArgAspArgProHisThr-70 |
| SEQ. ID. NO. 31730 | 76-ThrGlyLysAlaAlaGluLeuSerGlu-84 |
| SEQ. ID. NO. 31731 | 99-GluLeuThrProThrGlnGluArgAsnLeuGluLys-110 |
| SEQ. ID. NO. 31732 | 128-AlaArgArgAlaArgThrGlnGluGlyArgLeuGlnVal-140 |
| SEQ. ID. NO. 31733 | 160-GlnSerGlnArgGlyGlyIleGlyMetLysGlyProGlyGluThrLysLeuGluThrAspArgArgLeuThrAla-184 |
| SEQ. ID. NO. 31734 | 188-AsnAlaLeuLysLysGlnLeuAlaAsnLeuLysLysGlnArgAlaLeuArgArgLysSerArgGluSerGlyArgIleLysThr-215 |
| SEQ. ID. NO. 31735 | 223-AsnValGlyLysSerSerLeu-229 |
| SEQ. ID. NO. 31736 | 232-ArgLeuThrLysSerGlyIleTyrAla-240 |
| SEQ. ID. NO. 31737 | 286-ThrLeuGluGluThrValGln-292 |
| SEQ. ID. NO. 31738 | 302-AlaAlaAlaArgAsnSerGlyGlnGlnIleGluAspValGluAsnValLeu-318 |
| SEQ. ID. NO. 31739 | 332-TyrAsnLysThrAspLeuLeuProSerGluGluGlnAsnThrGlyIle-347 |
| SEQ. ID. NO. 31740 | 364-GluAsnThrGlyIleAspAlaLeuArgGluAlaIle-375 |
| SEQ. ID. NO. 31741 | 380-AlaAlaAlaProAsnThrAspGluThrGluMetPro-391 |
| Hydrophilic Regions - Hopp-Woods | |
| SEQ. ID. NO. 31742 | 1-SerGlyArgThrGlyArgAsnSerAla-9 |
| SEQ. ID. NO. 31743 | 12-AlaGlnProGluArg-16 |
| SEQ. ID. NO. 31744 | 24-LeuAspLysAspAspThrGlySerAsnAlaAlaArg-35 |
| SEQ. ID. NO. 31745 | 47-ValGluLeuValLys-51 |
| SEQ. ID. NO. 31746 | 53-AlaGlyGlyAspSerValArgValGluThrAlaLysArgAspArgProHis-69 |
| SEQ. ID. NO. 31747 | 77-GlyLysAlaAlaGluLeuSerGlu-84 |
| SEQ. ID. NO. 31748 | 100-LeuThrProThrGlnGluArgAsnLeuGluLys-110 |
| SEQ. ID. NO. 31749 | 128-AlaArgArgAlaArgThrGlnGluGlyArgLeuGlnVal-140 |
| SEQ. ID. NO. 31750 | 160-GlnSerGlnArgGlyGlyIle-166 |
| SEQ. ID. NO. 31751 | 170-GlyProGlyGluThrLysLeuGluThrAspArgArgLeuThrAla-184 |
| SEQ. ID. NO. 31752 | 188-AsnAlaLeuLysLysGlnLeuAlaAsnLeuLysLysGlnArgAlaLeuArgArgLysSerArgGluSerGlyArgIleLys-214 |
| SEQ. ID. NO. 31753 | 286-ThrLeuGluGluThrValGln-292 |
| SEQ. ID. NO. 31754 | 302-AlaAlaAlaArgAsnSerGlyGlnGlnIleGluAspValGluAsnValLeu-318 |
| SEQ. ID. NO. 31755 | 336-AspLeuLeuProSerGluGluGlnAsn-344 |
| SEQ. ID. NO. 31756 | 369-AspAlaLeuArgGluAlaIle-375 |
| SEQ. ID. NO. 31757 | 383-ProAsnThrAspGluThrGluMetPro-391 |
| g538 | |
| AMPHI Regions - AMPHI | |
| SEQ. ID. NO. 31758 | 41-ThrAlaLeuAlaGluAlaValGluLeuValLysAlaAlaGly-54 |
| SEQ. ID. NO. 31759 | 78-LysAlaAlaGluLeuSerGluAlaValAla-87 |
| SEQ. ID. NO. 31760 | 104-GlnGluArgAsnLeuGluLysIleLeuGlnCysArgValLeuAspArgVal-120 |
| SEQ. ID. NO. 31761 | 144-GlnLeuSerHisLeuAlaGlyArgLeuIleArgGlyTyrGlyHisLeuGln-160 |
| SEQ. ID. NO. 31762 | 187-IleAsnAlaLeuLysLysGlnLeuAla-195 |
| SEQ. ID. NO. 31763 | 211-GlyArgIleLysThrPheAlaLeuValGlyTyrThrAsn-223 |
| SEQ. ID. NO. 31764 | 230-PheAsnArgLeuThrLys-235 |
| SEQ. ID. NO. 31765 | 270-GlyPheValSerAspLeuProHisLysLeuIleSerAlaPheSerAlaThrLeuGlu-288 |
| SEQ. ID. NO. 31766 | 306-AsnSerGlyGlnGlnIleGluAspValGluAsnValLeuGlnGluIleHis-322 |
| SEQ. ID. NO. 31767 | 364-GluAsnThrGlyIleAspAlaLeuArgGluAlaIleAlaGluTyrCysAla-380 |
| Antigenic Index - Jameson-Wolf | |
| SEQ. ID. NO. 31768 | 1-SerGlyArgThrGlyArgAsnSerAlaThrGlnAlaGlnProGluArgVal-17 |
| SEQ. ID. NO. 31769 | 24-LeuAspLysAspAspThrGlySerAsnAlaAlaArg-35 |
| SEQ. ID. NO. 31770 | 47-ValGluLeuValLys-51 |
| SEQ. ID. NO. 31771 | 53-AlaGlyGlyAspSerValArgValGluThrAlaLysArgAspArgProHisThr-70 |
| SEQ. ID. NO. 31772 | 76-ThrGlyLysAlaAlaGluLeuSerGlu-84 |
| SEQ. ID. NO. 31773 | 99-GluLeuThrProThrGlnGluArgAsnLeuGluLys-110 |
| SEQ. ID. NO. 31774 | 128-AlaArgArgAlaArgThrGlnGluGlyArgLeuGlnVal-140 |
| SEQ. ID. NO. 31775 | 160-GlnSerGlnArgGlyGlyIleGlyMetLysGlyProGlyGluThrLysLeuGluThrAspArgArgLeuThrAla-184 |

TABLE 1-continued

| | |
|---|---|
| SEQ. ID. NO. 31776 | 188-AsnAlaLeuLysLysGlnLeuAlaAsnLeuLysLysGlnArgAlaLeuArgArgLysSerArgGluSerGlyArgIleLysThr-215 |
| SEQ. ID. NO. 31777 | 223-AsnValGlyLysSerSerLeu-229 |
| SEQ. ID. NO. 31778 | 232-ArgLeuThrLysSerGlyIleTyrAla-240 |
| SEQ. ID. NO. 31779 | 286-ThrLeuGluGluThrValGln-292 |
| SEQ. ID. NO. 31780 | 302-AlaAlaAlaArgAsnSerGlyGlnGlnIleGluAspValGluAsnValLeu-318 |
| SEQ. ID. NO. 31781 | 332-TyrAsnLysThrAspLeuLeuProSerGluGluGlnAsnThrGlyIle-347 |
| SEQ. ID. NO. 31782 | 364-GluAsnThrGlyIleAspAlaLeuArgGluAlaIle-375 |
| SEQ. ID. NO. 31783 | 380-AlaAlaAlaProAsnThrAspGluThrGluMetPro-391 |
| Hydrophilic Regions - Hopp-Woods | |
| SEQ. ID. NO. 31784 | 1-SerGlyArgThrGlyArgAsnSerAla-9 |
| SEQ. ID. NO. 31785 | 12-AlaGlnProGluArg-16 |
| SEQ. ID. NO. 31786 | 24-LeuAspLysAspAspThrGlySerAsnAlaAlaArg-35 |
| SEQ. ID. NO. 31787 | 47-ValGluLeuValLys-51 |
| SEQ. ID. NO. 31788 | 53-AlaGlyGlyAspSerValArgValGluThrAlaLysArgAspArgProHis-69 |
| SEQ. ID. NO. 31789 | 77-GlyLysAlaAlaGluLeuSerGlu-84 |
| SEQ. ID. NO. 31790 | 100-LeuThrProThrGlnGluArgAsnLeuGluLys-110 |
| SEQ. ID. NO. 31791 | 128-AlaArgArgAlaArgThrGlnGluGlyArgLeuGlnVal-140 |
| SEQ. ID. NO. 31792 | 160-GlnSerGlnArgGlyGlyIle-166 |
| SEQ. ID. NO. 31793 | 170-GlyProGlyGluThrLysLeuGluThrAspArgArgLeuThrAla-184 |
| SEQ. ID. NO. 31794 | 188-AsnAlaLeuLysLysGlnLeuAlaAsnLeuLysLysGlnArgAlaLeuArgArgLysSerArgGluSerGlyArgIleLys-214 |
| SEQ. ID. NO. 31795 | 286-ThrLeuGluGluThrValGln-292 |
| SEQ. ID. NO. 31796 | 302-AlaAlaAlaArgAsnSerGlyGlnGlnIleGluAspValGluAsnValLeu-318 |
| SEQ. ID. NO. 31797 | 336-AspLeuLeuProSerGluGluGlnAsn-344 |
| SEQ. ID. NO. 31798 | 369-AspAlaLeuArgGluAlaIle-375 |
| SEQ. ID. NO. 31799 | 383-ProAsnThrAspGluThrGluMetPro-391 |
| g539 | |
| AMPHI Regions - AMPHI | |
| SEQ. ID. NO. 31800 | 18-ArgGlnArgGluHisHisArgLeuHisHisThr-28 |
| SEQ. ID. NO. 31801 | 44-LeuValGlyGlyPheAspPheLeuArgValIleGlyCysGlyGly-58 |
| SEQ. ID. NO. 31802 | 108-AlaGlyGlyAlaGlyAsnAlaAla-115 |
| SEQ. ID. NO. 31803 | 123-ArgAlaIleMetGlyPhe-128 |
| SEQ. ID. NO. 31804 | 142-AspLeuValGluAspPheLeu-148 |
| SEQ. ID. NO. 31805 | 172-AspAlaLeuCysAspCysLeuThr-179 |
| SEQ. ID. NO. 31806 | 197-GlnValPheGlyAsnValGln-203 |
| SEQ. ID. NO. 31807 | 220-PheGlyAlaAlaAlaGlnTyr-226 |
| SEQ. ID. NO. 31808 | 328-GlyArgSerLeuThrAsnPro-334 |
| SEQ. ID. NO. 31809 | 354-ValSerArgValAlaLysSerTrpSerPheAla-364 |
| SEQ. ID. NO. 31810 | 366-MetProAspLeuValSerArgLeu-373 |
| Antigenic Index - Jameson-Wolf | |
| SEQ. ID. NO. 31811 | 1-MetGluAspLeuGlnGluIleGly-8 |
| SEQ. ID. NO. 31812 | 15-LysValGlyArgGlnArgGluHisHisArg-24 |
| SEQ. ID. NO. 31813 | 26-HisHisThrGlnSerGlyAsnGlyLysAlaAspAsp-37 |
| SEQ. ID. NO. 31814 | 63-ProAspPheGlnGlnAsnValGlyGluAlaAsp-73 |
| SEQ. ID. NO. 31815 | 77-ValProAspAspAlaAlaAla-83 |
| SEQ. ID. NO. 31816 | 88-IleGluValAspAlaAspAspAlaValCys-97 |
| SEQ. ID. NO. 31817 | 102-LeuPheAspGlnProAspAlaGlyGlyAlaGlyAsnAlaAlaGluHis-117 |
| SEQ. ID. NO. 31818 | 169-GlyIleAspAspAlaLeuCys-175 |
| SEQ. ID. NO. 31819 | 229-MetAlaSerArgSerAlaSer-235 |
| SEQ. ID. NO. 31820 | 242-ThrGluMetArgThr-246 |
| SEQ. ID. NO. 31821 | 261-CysSerSerAspGlySerArgSer-268 |
| SEQ. ID. NO. 31822 | 304-ThrThrCysSerSerThrSer-310 |
| SEQ. ID. NO. 31823 | 313-ThrValSerSerLysValAlaGluLysAlaGluIle-324 |
| SEQ. ID. NO. 31824 | 326-LeuCysGlyArgSerLeuThrAsnProThrVal-336 |
| SEQ. ID. NO. 31825 | 348-TyrSerArgArgAlaValVal-354 |
| SEQ. ID. NO. 31826 | 356-ArgValAlaLysSer-360 |
| SEQ. ID. NO. 31827 | 369-LeuValSerArgLeuAsnArgLeuAspLeu-378 |
| Hydrophilic Regions - Hopp-Woods | |
| SEQ. ID. NO. 31828 | 1-MetGluAspLeuGlnGluIleGly-8 |
| SEQ. ID. NO. 31829 | 15-LysValGlyArgGlnArgGluHisHisArg-24 |
| SEQ. ID. NO. 31830 | 31-GlyAsnGlyLysAlaAspAsp-37 |
| SEQ. ID. NO. 31831 | 69-ValGlyGluAlaAsp-73 |
| SEQ. ID. NO. 31832 | 78-ProAspAspAlaAlaAla-83 |
| SEQ. ID. NO. 31833 | 88-IleGluValAspAlaAspAspAlaValCys-97 |
| SEQ. ID. NO. 31834 | 102-LeuPheAspGlnProAspAlaGlyGly-110 |
| SEQ. ID. NO. 31835 | 113-AsnAlaAlaGluHis-117 |
| SEQ. ID. NO. 31836 | 169-GlyIleAspAspAlaLeu-174 |
| SEQ. ID. NO. 31837 | 230-AlaSerArgSerAla-234 |
| SEQ. ID. NO. 31838 | 242-ThrGluMetArgThr-246 |
| SEQ. ID. NO. 31839 | 263-SerAspGlySerArg-267 |
| SEQ. ID. NO. 31840 | 317-LysValAlaGluLysAlaGluIle-324 |
| SEQ. ID. NO. 31841 | 348-TyrSerArgArgAlaValVal-354 |
| SEQ. ID. NO. 31842 | 369-LeuValSerArgLeuAsnArgLeuAspLeu-378 |
| g542 | |
| AMPHI Regions - AMPHI | |
| SEQ. ID. NO. 31843 | 6-ArgIleArgArgCysSerVal-12 |
| Antigenic Index - Jameson-Wolf | |
| SEQ. ID. NO. 31844 | 1-MetProLysTrpSerArgIleArgArgCysSerVal-12 |
| SEQ. ID. NO. 31845 | 29-ProProSerAsnAla-33 |
| SEQ. ID. NO. 31846 | 37-ValArgLeuLysSerSerAspGlyIleAlaSer-47 |
| SEQ. ID. NO. 31847 | 56-GlySerMetProSerGluThrValSerHisLysSerAspSerSerArgAsnThrSerAlaSerArgArgAsnValSerProLysCysProPheGly-87 |

TABLE 1-continued

| | |
|---|---|
| SEQ. ID. NO. 31848 | 90-CysArgGlnAspAlaAlaLysProArgArgPheGlyGlyLys-103 |
| SEQ. ID. NO. 31849 | 107-LeuThrGlySerArg-111 |
| Hydrophilic Regions - Hopp-Woods | |
| SEQ. ID. NO. 31850 | 5-SerArgIleArgArgCysSer-11 |
| SEQ. ID. NO. 31851 | 37-ValArgLeuLysSerSerAspGlyIleAla-46 |
| SEQ. ID. NO. 31852 | 58-MetProSerGluThrValSerHisLysSerAspSerSerArgAsnThrSerAlaSerArgArgAsnValSerPro-82 |
| SEQ. ID. NO. 31853 | 90-CysArgGlnAspAlaAlaLysProArgArgPheGlyGly-102 |
| g544-2 | |
| AMPHI Regions - AMPHI | |
| SEQ. ID. NO. 31854 | 55-PheTrpPheProSerCysProGlyCysValSerGluMetProLysValThrLysThrAlaAsnAspTyrLys-78 |
| SEQ. ID. NO. 31855 | 85-LeuAlaValAlaGlnProIleAspProIleGluSerValArgGlnTyrVal-101 |
| SEQ. ID. NO. 31856 | 116-LysAlaValGlyGlnAlaPhe-122 |
| Antigenic Index - Jameson-Wolf | |
| SEQ. ID. NO. 31857 | 1-MetLysLysIleLeu-5 |
| SEQ. ID. NO. 31858 | 22-IleProAspSerLysThrAlaPro-29 |
| SEQ. ID. NO. 31859 | 35-AspLeuHisGlyLysThrValSerAsnAlaAspLeuGlnGly-48 |
| SEQ. ID. NO. 31860 | 59-SerCysProGlyCys-63 |
| SEQ. ID. NO. 31861 | 66-GluMetProLysValThrLysThrAlaAsnAspTyrLysAsnLysAspPhe-82 |
| SEQ. ID. NO. 31862 | 90-ProIleAspProIleGluSerValArgGlnTyrValLysAspTyrGly-105 |
| SEQ. ID. NO. 31863 | 113-AspAlaAspLysAlaVal-118 |
| SEQ. ID. NO. 31864 | 133-IleGlyLysLysGlyGluIleLeu-140 |
| SEQ. ID. NO. 31865 | 144-ValGlyGluProAspPheGlyLysLeuTyrGlnGluIleAspThr-158 |
| Hydrophilic Regions - Hopp-Woods | |
| SEQ. ID. NO. 31866 | 1-MetLysLysIleLeu-5 |
| SEQ. ID. NO. 31867 | 23-ProAspSerLysThr-27 |
| SEQ. ID. NO. 31868 | 66-GluMetProLysValThrLysThrAlaAsnAspTyrLysAsnLysAspPhe-82 |
| SEQ. ID. NO. 31869 | 92-AspProIleGluSerValArgGlnTyrValLys-102 |
| SEQ. ID. NO. 31870 | 113-AspAlaAspLysAlaVal-118 |
| SEQ. ID. NO. 31871 | 133-IleGlyLysLysGlyGluIle-139 |
| g547 | |
| AMPHI Regions - AMPHI | |
| SEQ. ID. NO. 31872 | 7-PheAsnLysThrValAlaSerPheAlaGlnIleValGluThrPheAspVal-23 |
| SEQ. ID. NO. 31873 | 62-AsnArgSerPheLys-66 |
| SEQ. ID. NO. 31874 | 120-GluLeuLeuThrIleLeuValLys-127 |
| Antigenic Index - Jameson-Wolf | |
| SEQ. ID. NO. 31875 | 3-ValAspAsnGlyPheAsnLysThrVal-11 |
| SEQ. ID. NO. 31876 | 35-GlnMetLysGlnArgCysGly-41 |
| SEQ. ID. NO. 31877 | 56-CysGlyPheGluIleProAsnArgSerPheLysGlu-67 |
| SEQ. ID. NO. 31878 | 76-LeuSerGluArgPheArgThrAsnAlaGluValGluMet-88 |
| SEQ. ID. NO. 31879 | 128-AsnLeuSerProAsnGlyLysLysArgPhe-137 |
| Hydrophilic Regions - Hopp-Woods | |
| SEQ. ID. NO. 31880 | 36-MetLysGlnArgCys-40 |
| SEQ. ID. NO. 31881 | 60-IleProAsnArgSerPheLysGlu-67 |
| SEQ. ID. NO. 31882 | 76-LeuSerGluArgPheArgThrAsnAlaGluValGluMet-88 |
| SEQ. ID. NO. 31883 | 129-LeuSerProAsnGlyLysLysArgPhe-137 |
| g548 | |
| AMPHI Regions - AMPHI | |
| SEQ. ID. NO. 31884 | 7-SerPheLeuValLeuAlaAlaLeuAlaAlaCysLys-22 |
| SEQ. ID. NO. 31885 | 31-AlaAlaSerSerSer-35 |
| SEQ. ID. NO. 31886 | 41-AlaGluAsnAlaAlaLysPro-47 |
| SEQ. ID. NO. 31887 | 89-PheThrHisCysProAspValCysProThr-98 |
| SEQ. ID. NO. 31888 | 103-TyrSerAspThrLeuLysGlnLeuGlyGlyGln-113 |
| SEQ. ID. NO. 31889 | 132-GluIleIleGlyLysTyrAlaLys-139 |
| Antigenic Index - Jameson-Wolf | |
| SEQ. ID. NO. 31890 | 22-LysProGlnAspAsnSerAla-28 |
| SEQ. ID. NO. 31891 | 33-SerSerSerAlaSer-37 |
| SEQ. ID. NO. 31892 | 39-ProAlaAlaGluAsnAlaAlaLysProGlnThrArgGlyThrAspMetArgLysGluAspIleGlyGlyAspPheThrLeuThrAspGlyGluGly LysProPheSer-74 |
| SEQ. ID. NO. 31893 | 76-SerAspLeuLysGly-80 |
| SEQ. ID. NO. 31894 | 93-ProAspValCysPro-97 |
| SEQ. ID. NO. 31895 | 104-SerAspThrLeuLysGlnLeuGlyGlyGlnAlaLysAspValLys-118 |
| SEQ. ID. NO. 31896 | 124-IleAspProGluArgAspThrProGluIleIleGlyLysTyrAlaLysGlnPheAsnProAspPhe-145 |
| SEQ. ID. NO. 31897 | 150-AlaThrGlyGlyGln-154 |
| SEQ. ID. NO. 31898 | 169-LysIleAsnGlnLysAspAspSerGluAsnTyrLeu-180 |
| SEQ. ID. NO. 31899 | 189-LeuIleAspLysAsnGlyGlu-195 |
| SEQ. ID. NO. 31900 | 200-SerProTyrGlySerGluProGluThrIleAlaAlaAspVal-213 |
| Hydrophilic Regions - Hopp-Woods | |
| SEQ. ID. NO. 31901 | 22-LysProGlnAspAsnSerAla-28 |
| SEQ. ID. NO. 31902 | 39-ProAlaAlaGluAsnAlaAlaLysProGlnThrArgGlyThrAspMetArgLysGluAspIleGlyGly-61 |
| SEQ. ID. NO. 31903 | 64-ThrLeuThrAspGlyGluGlyLysPro-72 |
| SEQ. ID. NO. 31904 | 76-SerAspLeuLysGly-80 |
| SEQ. ID. NO. 31905 | 111-GlyGlyGlnAlaLysAspValLys-118 |
| SEQ. ID. NO. 31906 | 124-IleAspProGluArgAspThrProGluIleIle-134 |
| SEQ. ID. NO. 31907 | 170-IleAsnGlnLysAspAspSerGluAsnTyrLeu-180 |
| SEQ. ID. NO. 31908 | 191-AspLysAsnGlyGlu-195 |
| SEQ. ID. NO. 31909 | 203-GlySerGluProGluThrIleAlaAlaAspVal-213 |
| g553 | |
| AMPHI Regions - AMPHI | |
| SEQ. ID. NO. 31910 | 31-LeuAlaAlaValAlaGlyPheTyrGlyPheTyrThrAspLeu-44 |
| SEQ. ID. NO. 31911 | 59-AsnLeuAlaAspIleValArgPheAlaAspAsp-69 |

TABLE 1-continued

| | |
|---|---|
| SEQ. ID. NO. 31912 | 83-GluLeuGlySerLeu-87 |
| SEQ. ID. NO. 31913 | 99-HisPheValValLeu-103 |
| SEQ. ID. NO. 31914 | 162-GlyIleSerGlyLeuGlyArgThrLeuPhe-171 |
| SEQ. ID. NO. 31915 | 173-LeuLeuAlaLeuAlaAlaAlaMetGluValPheAlaPheLeu-186 |
| SEQ. ID. NO. 31916 | 232-HisAspIleTyrSerLeuProProPro-240 |
| Antigenic Index - Jameson-Wolf | |
| SEQ. ID. NO. 31917 | 11-LeuThrLysLysLeu-15 |
| SEQ. ID. NO. 31918 | 45-ArgAlaLeuArgSerLysTyr-51 |
| SEQ. ID. NO. 31919 | 55-LeuLysGlyGluAsnLeuAlaAsp-62 |
| SEQ. ID. NO. 31920 | 75-ArgAlaLeuArgLeuAspLeuAspGluLeuGlySer-86 |
| SEQ. ID. NO. 31921 | 106-ValSerSerAspGly-110 |
| SEQ. ID. NO. 31922 | 115-AspProAlaSerGlyArgArgLysValLysThrGluGluIleSerArgLysPheThr-133 |
| SEQ. ID. NO. 31923 | 140-TrpProAsnThrArgPheGluAlaGlyGluGluLysGlnGluIleArg-155 |
| SEQ. ID. NO. 31924 | 163-IleSerGlyLeuGly-167 |
| SEQ. ID. NO. 31925 | 192-LysIleGlyArgGlyGluSer-198 |
| SEQ. ID. NO. 31926 | 202-IleGlyArgSerGlyCysGlyLysSerThrLeu-212 |
| SEQ. ID. NO. 31927 | 216-LeuSerGlyAsnLeuProProGluSerGlyLysVal-227 |
| SEQ. ID. NO. 31928 | 245-PheGluCysAspGlyGlnGlyArgThr-253 |
| SEQ. ID. NO. 31929 | 258-GlyLeuAsnLeuAsnArg-263 |
| Hydrophilic Regions - Hopp-Woods | |
| SEQ. ID. NO. 31930 | 11-LeuThrLysLysLeu-15 |
| SEQ. ID. NO. 31931 | 45-ArgAlaLeuArgSer-49 |
| SEQ. ID. NO. 31932 | 55-LeuLysGlyGluAsnLeuAlaAsp-62 |
| SEQ. ID. NO. 31933 | 75-ArgAlaLeuArgLeuAspLeuAspGluLeuGlySer-86 |
| SEQ. ID. NO. 31934 | 106-ValSerSerAspGly-110 |
| SEQ. ID. NO. 31935 | 116-ProAlaSerGlyArgArgLysValLysThrGluGluIleSerArgLysPheThr-133 |
| SEQ. ID. NO. 31936 | 144-ArgPheGluAlaGlyGluGluLysGlnGluIleArg-155 |
| SEQ. ID. NO. 31937 | 192-LysIleGlyArgGlyGluSer-198 |
| SEQ. ID. NO. 31938 | 205-SerGlyCysGlyLys-209 |
| SEQ. ID. NO. 31939 | 220-LeuProProGluSerGlyLys-226 |
| SEQ. ID. NO. 31940 | 245-PheGluCysAspGlyGlnGly-251 |
| g554 | |
| AMPHI Regions - AMPHI | |
| SEQ. ID. NO. 31941 | 35-AlaProThrLeuGlnThrProGluThrLeu-44 |
| SEQ. ID. NO. 31942 | 71-AlaAlaLeuThrGlnLeuMet-77 |
| SEQ. ID. NO. 31943 | 110-ArgMetPheValArgProGlyAspThrVal-119 |
| SEQ. ID. NO. 31944 | 124-LeuLeuLysGlyMetIleAla-130 |
| SEQ. ID. NO. 31945 | 141-AlaAspArgLeuGlyAsnGlySerIleGluAsnPheValGlnGlnMetAsnLysGlu-159 |
| SEQ. ID. NO. 31946 | 193-GluAlaLeuMetArgAspPheProGluTyrTyrProLeuPheSer-207 |
| SEQ. ID. NO. 31947 | 280-ArgAlaLeuGlnAlaPheAspThrPro-288 |
| SEQ. ID. NO. 31948 | 296-ThrValAlaGlnIle-300 |
| SEQ. ID. NO. 31949 | 331-GluGlnIleLeuGluThrIleGlnProIleProAla-342 |
| Antigenic Index - Jameson-Wolf | |
| SEQ. ID. NO. 31950 | 24-SerProAlaProAsnArgProThr-31 |
| SEQ. ID. NO. 31951 | 37-ThrLeuGlnThrProGluThr-43 |
| SEQ. ID. NO. 31952 | 53-LeuGlnSerArgGlnThrLeuSerAlaLysAsnThrAsnThrProValGlu-69 |
| SEQ. ID. NO. 31953 | 84-LysAsnMetLysSerGlyAsnIleGlnSerGluGluAsnLeuLysIleProGlu-101 |
| SEQ. ID. NO. 31954 | 104-TrpAlaSerGluGlySerArgMetPheValArgProGlyAspThrValSerThrAspLysLeuLeu-125 |
| SEQ. ID. NO. 31955 | 142-AspArgLeuGlyAsnGlySerIleGluAsnPhe-152 |
| SEQ. ID. NO. 31956 | 156-MetAsnLysGluAlaArgArgLeuGlyMetLysAsnThrValPheLysAsnProThrGlyLeuGlyArgGluGlyGlnValSerThrAlaLysAsp LeuSerLeu-190 |
| SEQ. ID. NO. 31957 | 194-AlaLeuMetArgAspPheProGluTyrTyr-203 |
| SEQ. ID. NO. 31958 | 214-GluAsnIleGluGlnAsnAsnArgAsnIleLeu-224 |
| SEQ. ID. NO. 31959 | 226-TyrArgAspAsnAsnValAsnGlyLeuLysAlaGlyHisThrGluSerGlyGlyTyr-244 |
| SEQ. ID. NO. 31960 | 250-TyrSerGlyAsnGlyArgHis-256 |
| SEQ. ID. NO. 31961 | 262-LeuGlySerGluSerAlaGluThrArgAlaSerAspAsnSerLysLeuLeuAsn-279 |
| SEQ. ID. NO. 31962 | 286-AspThrProLysIleTyrProLysGlyLysThr-296 |
| SEQ. ID. NO. 31963 | 302-IleSerGlyGlySerLysLysThrValArg-311 |
| SEQ. ID. NO. 31964 | 323-ProHisLysGluAlaLysMetAlaGluGlnIleLeu-334 |
| SEQ. ID. NO. 31965 | 342-AlaProValLysLysGlyGlnIleLeuGlyLysIleLysIleArgGlnAsnGlyHisThrIleAlaGluLysGluIleValAla-369 |
| SEQ. ID. NO. 31966 | 371-GluAsnValGluLysArgSerArgTrpGlnArgLeu-382 |
| Hydrophilic Regions - Hopp-Woods | |
| SEQ. ID. NO. 31967 | 26-AlaProAsnArgProThr-31 |
| SEQ. ID. NO. 31968 | 57-GlnThrLeuSerAlaLysAsnThrAsnThrProValGlu-69 |
| SEQ. ID. NO. 31969 | 85-AsnMetLysSerGlyAsnIleGlnSerGluGluAsnLeuLysIleProGlu-101 |
| SEQ. ID. NO. 31970 | 107-GluGlySerArgMetPheValArgProGlyAspThrValSerThrAspLysLeuLeu-125 |
| SEQ. ID. NO. 31971 | 156-MetAsnLysGluAlaArgArgLeuGlyMet-165 |
| SEQ. ID. NO. 31972 | 174-ThrGlyLeuGlyArgGluGlyGlnValSerThrAlaLysAspLeuSerLeu-190 |
| SEQ. ID. NO. 31973 | 214-GluAsnIleGluGlnAsnAsnArg-221 |
| SEQ. ID. NO. 31974 | 227-ArgAspAsnAsnValAsn-232 |
| SEQ. ID. NO. 31975 | 237-GlyHisThrGluSerGly-242 |
| SEQ. ID. NO. 31976 | 264-SerGluSerAlaGluThrArgAlaSerAspAsnSerLysLeuLeuAsn-279 |
| SEQ. ID. NO. 31977 | 289-LysIleTyrProLysGlyLysThr-296 |
| SEQ. ID. NO. 31978 | 304-GlyGlySerLysLysThrValArg-311 |
| SEQ. ID. NO. 31979 | 323-ProHisLysGluAlaLysMetAlaGluGlnIleLeu-334 |
| SEQ. ID. NO. 31980 | 343-ProValLysLysGlyGlnIle-349 |
| SEQ. ID. NO. 31981 | 353-IleLysIleArgGlnAsnGly-359 |

TABLE 1-continued

| | |
|---|---|
| SEQ. ID. NO. 31982 | 362-IleAlaGluLysGluIleValAla-369 |
| SEQ. ID. NO. 31983 | 371-GluAsnValGluLysArgSerArgTrp-379 |
| g556 | |
| AMPHI Regions - AMPHI | |
| SEQ. ID. NO. 31984 | 61-IleGluArgLeuLys-65 |
| Antigenic Index - Jameson-Wolf | |
| SEQ. ID. NO. 31985 | 1-MetAspAsnLysThrLysLeuArgLeu-9 |
| SEQ. ID. NO. 31986 | 52-ThrSerArgArgGlnGlnArgGlnPheIleGluArgLeuLysLysPheAspIleAspProGluLysGlyArgIleAsnGluAlaAsnLeuArgArg MetTyrHisSerGlyGlyGlnHisGlnLysAspAla-95 |
| SEQ. ID. NO. 31987 | 102-SerGlnLysCysSerValAspGluAlaHisAlaMetPheLysLysArgProThrArgGlnGluIleAsn-124 |
| SEQ. ID. NO. 31988 | 127-AlaAlaLysGlnSerArgGlyGlnLysArgProHisArg-139 |
| Hydrophilic Regions - Hopp-Woods | |
| SEQ. ID. NO. 31989 | 1-MetAspAsnLysThrLysLeuArgLeu-9 |
| SEQ. ID. NO. 31990 | 53-SerArgArgGlnGlnArgGlnPheIleGluArgLeuLysLysPheAspIleAspProGluLysGlyArgIleAsnGluAlaAsnLeuArgArgMet Tyr-85 |
| SEQ. ID. NO. 31991 | 90-GlnHisGlnLysAspAla-95 |
| SEQ. ID. NO. 31992 | 105-CysSerValAspGluAlaHisAlaMetPheLysLysArgProThrArgGlnGluIleAsn-124 |
| SEQ. ID. NO. 31993 | 127-AlaAlaLysGlnSerArgGlyGlnLysArgProHisArg-139 |
| g557 | |
| AMPHI Regions - AMPHI | |
| SEQ. ID. NO. 31994 | 22-GlyAlaAspGlyIle-26 |
| SEQ. ID. NO. 31995 | 55-SerGlyArgValAspAspAlaAla-62 |
| SEQ. ID. NO. 31996 | 113-ThrValSerValArgArgIleLeuAspTyrAlaAsp-124 |
| SEQ. ID. NO. 31997 | 142-ArgGlnAspValAlaGluGlnIle-149 |
| Antigenic Index - Jameson-Wolf | |
| SEQ. ID. NO. 31998 | 20-LeuLysGlyAlaAspGlyIleSerProProLeuThrTyrArgSerTrpHisIleGluGlyGlyGlnAlaLeu-43 |
| SEQ. ID. NO. 31999 | 54-AlaSerGlyArgValAspAspAlaAlaGly-63 |
| SEQ. ID. NO. 32000 | 68-LeuArgIleAspSerValSerGlnAsnLysGluThrTyrThr-81 |
| SEQ. ID. NO. 32001 | 100-GlnValLeuLysArgGlyGluProValGlyLysProMet-112 |
| SEQ. ID. NO. 32002 | 118-ArgIleLeuAspTyrAlaAspAsnGluIleLeuGlyLysGlnGluGluGluGluThrLeu-137 |
| SEQ. ID. NO. 32003 | 141-MetArgGlnAspValAlaGluGlnIleValArg-151 |
| Hydrophilic Regions - Hopp-Woods | |
| SEQ. ID. NO. 32004 | 21-LysGlyAlaAspGlyIle-26 |
| SEQ. ID. NO. 32005 | 56-GlyArgValAspAspAlaAlaGly-63 |
| SEQ. ID. NO. 32006 | 68-LeuArgIleAspSerValSerGlnAsnLysGluThrTyrThr-81 |
| SEQ. ID. NO. 32007 | 100-GlnValLeuLysArgGlyGluProValGly-109 |
| SEQ. ID. NO. 32008 | 126-GluIleLeuGlyLysGlnGluGluGluGluThrLeu-137 |
| SEQ. ID. NO. 32009 | 141-MetArgGlnAspValAlaGluGlnIleValArg-151 |
| g560 | |
| AMPHI Regions - AMPHI | |
| SEQ. ID. NO. 32010 | 30-PheArgAspGlyAlaHisLysMetAlaArgValTrpValGly-43 |
| SEQ. ID. NO. 32011 | 167-ArgMetAlaLysMetPhe-172 |
| SEQ. ID. NO. 32012 | 192-PheLeuLysTyrProGlyGlu-198 |
| SEQ. ID. NO. 32013 | 216-GluLeuMetGluLysCysGluHisLeuIleGlu-226 |
| Antigenic Index - Jameson-Wolf | |
| SEQ. ID. NO. 32014 | 29-ProPheArgAspGlyAlaHisLysMet-37 |
| SEQ. ID. NO. 32015 | 63-GluHisIleProAspArgProSer-70 |
| SEQ. ID. NO. 32016 | 75-LysHisGlnSerGlyTrpGlu-81 |
| SEQ. ID. NO. 32017 | 95-ValAlaLysArgGluLeuPhe-101 |
| SEQ. ID. NO. 32018 | 116-IleGlyIleAspArgAsnAsnArgArgGluAlaAsnGluGlnLeuIle-131 |
| SEQ. ID. NO. 32019 | 134-GlyLeuAlaArgLysAsnGluGlyTyr-142 |
| SEQ. ID. NO. 32020 | 148-ProGluGlyThrArgLeuAlaProGlyLysArgGlyLysTyrLysLeuGlyGly-165 |
| SEQ. ID. NO. 32021 | 182-AsnSerGlyGluPheTrpProLysAsnSerPheLeuLysTyrProGlyGluIle-199 |
| SEQ. ID. NO. 32022 | 209-HisAlaSerGlySerGluAlaGluLeuMetGluLysCysGluHisLeuIle-225 |
| SEQ. ID. NO. 32023 | 242-MetProSerGluThr-246 |
| Hydrophilic Regions - Hopp-Woods | |
| SEQ. ID. NO. 32024 | 29-ProPheArgAspGlyAlaHisLysMet-37 |
| SEQ. ID. NO. 32025 | 64-HisIleProAspArgProSer-70 |
| SEQ. ID. NO. 32026 | 95-ValAlaLysArgGluLeuPhe-101 |
| SEQ. ID. NO. 32027 | 116-IleGlyIleAspArgAsnAsnArgArgGluAlaAsnGluGlnLeuIle-131 |
| SEQ. ID. NO. 32028 | 134-GlyLeuAlaArgLysAsnGlu-140 |
| SEQ. ID. NO. 32029 | 149-GluGlyThrArgLeuAlaProGlyLysArgGlyLysTyrLysLeuGlyGly-165 |
| SEQ. ID. NO. 32030 | 211-SerGlySerGluAlaGluLeuMetGluLysCysGluHisLeuIle-225 |
| SEQ. ID. NO. 32031 | 242-MetProSerGluThr-246 |
| g561-2 | |
| AMPHI Regions - AMPHI | |
| SEQ. ID. NO. 32032 | 6-ArgPheSerAspGly-10 |
| SEQ. ID. NO. 32033 | 22-GlyLeuTrpValGlyLeuAlaAla-29 |
| SEQ. ID. NO. 32034 | 46-AlaSerValIleGluGluAlaGlyAsn-54 |
| SEQ. ID. NO. 32035 | 74-GlnIleAspAsnGlnIleAlaGluPheGluLysSerLeuLysArgIleSerGlnSerAsp-93 |
| SEQ. ID. NO. 32036 | 128-AlaTyrArgArgProThrGlnIle-135 |
| SEQ. ID. NO. 32037 | 188-ValIleArgProLeuGlnAlaLeuArgGluGlyAlaGluArgIleGly-203 |
| SEQ. ID. NO. 32038 | 219-PheLysGlnValGlyArgCysPheAsnGln-228 |
| SEQ. ID. NO. 32039 | 237-TyrAspAspLeuGluGlyGln-243 |
| SEQ. ID. NO. 32040 | 247-GlnThrHisAsnLeuGluLysGln-254 |
| SEQ. ID. NO. 32041 | 263-ArgThrThrArgAspLeuHisGlnSerTyr-272 |
| SEQ. ID. NO. 32042 | 276-GlnAlaAlaGluGluPheLeuAsnHisIleLeuPro-287 |
| SEQ. ID. NO. 32043 | 358-GlnThrLeuIleArgGlnLeuGly-365 |
| SEQ. ID. NO. 32044 | 391-GlnGlyLeuHisAspSerIleAlaGlnAlaLeuThr-402 |
| SEQ. ID. NO. 32045 | 433-GlyValGlnGluCysTyrGluAspValArgGluLeu-444 |

TABLE 1-continued

| | |
|---|---|
| SEQ. ID. NO. 32046 | 455-LysGluPheProGluAlaValAlaAspLeuPheAlaArgPhe-468 |
| SEQ. ID. NO. 32047 | 503-LeuSerAsnIleArgLysHisAlaArg-511 |
| SEQ. ID. NO. 32048 | 539-ThrGluLysIleGlyGluProThr-546 |
| Antigenic Index - Jameson-Wolf | |
| SEQ. ID. NO. 32049 | 4-ProThrArgPheSerAspGlyIlePro-12 |
| SEQ. ID. NO. 32050 | 48-ValIleGluGluAlaGlyAsn-54 |
| SEQ. ID. NO. 32051 | 66-AlaGlyGluGlySerProArgAlaGlnIleAspAsnGlnIleAlaGluPheGluLysSerLeuLysArgIleSerGlnSerAspAlaIleHis-96 |
| SEQ. ID. NO. 32052 | 99-IleProSerAspAsnProLeuAla-106 |
| SEQ. ID. NO. 32053 | 124-ProProLeuGlnAlaTyrArgArgProThrGlnIleGluLeu-137 |
| SEQ. ID. NO. 32054 | 152-GluAsnAlaGlyGluLysAsnThrTrpTrp-161 |
| SEQ. ID. NO. 32055 | 193-GlnAlaLeuArgGluGlyAlaGluArgIleGlyGlnArgHisPheAspIleProValProGluAspGlyThrProGluPheLysGlnValGlyArg CysPheAsn-227 |
| SEQ. ID. NO. 32056 | 235-ThrLeuTyrAspAspLeuGluGlyGlnValAlaGluGlnThrHisAsnLeuGluLysGlnAsnArgAsnLeu-258 |
| SEQ. ID. NO. 32057 | 263-ArgThrThrArgAspLeuHisGlnSerTyrThrProArgGlnAlaAlaGluGluPhe-281 |
| SEQ. ID. NO. 32058 | 291-AlaGlnSerGlyAsn-295 |
| SEQ. ID. NO. 32059 | 297-CysLeuGluAsnGlySerAspThrAspIle-306 |
| SEQ. ID. NO. 32060 | 310-ThrAlaGluHisGlyLysLysProProLeuGluLysTyrHisAspGluThrPhe-327 |
| SEQ. ID. NO. 32061 | 331-TyrGlnAsnGluLysLeuGly-337 |
| SEQ. ID. NO. 32062 | 342-GlyPheSerAspGlyThrSerLeuThrGlyAspAspArgThrLeu-356 |
| SEQ. ID. NO. 32063 | 370-GlyAlaLysGlnGluGluGluLysArgLeu-379 |
| SEQ. ID. NO. 32064 | 383-LeuGlnGluArgAsnLeu-388 |
| SEQ. ID. NO. 32065 | 393-LeuHisAspSerIle-397 |
| SEQ. ID. NO. 32066 | 414-AlaPheAlaGluAsnLysArgGluGluAlaAlaGlu-425 |
| SEQ. ID. NO. 32067 | 433-GlyValGlnGluCysTyrGluAspValArgGlu-443 |
| SEQ. ID. NO. 32068 | 449-ArgThrLysIleSerAsnLysGluPheProGluAlaVal-461 |
| SEQ. ID. NO. 32069 | 480-TrpGluAsnGlySer-484 |
| SEQ. ID. NO. 32070 | 487-ProThrGlnAspGluGlnLeu-493 |
| SEQ. ID. NO. 32071 | 502-SerLeuSerAsnIleArgLysHisAlaArg-511 |
| SEQ. ID. NO. 32072 | 520-SerGluTyrGlyGlyArgPhe-526 |
| SEQ. ID. NO. 32073 | 530-IleGlnAspAsnGlyGlnGlyPheAspThrGluLysIleGlyGluProThrGlySerHis-549 |
| SEQ. ID. NO. 32074 | 555-MetGlnGluArgAlaLysArgIleArgAla-564 |
| SEQ. ID. NO. 32075 | 566-LeuGluIleArgSerGlnAlaGlnGlnGlyThr-576 |
| SEQ. ID. NO. 32076 | 581-ThrGlyAlaProLysGluSerLeuPro-589 |
| Hydrophilic Regions - Hopp-Woods | |
| SEQ. ID. NO. 32077 | 48-ValIleGluGluAlaGlyAsn-54 |
| SEQ. ID. NO. 32078 | 68-GluGlySerProArgAlaGlnIle-75 |
| SEQ. ID. NO. 32079 | 78-GlnIleAlaGluPheGluLysSerLeuLysArgIleSerGln-91 |
| SEQ. ID. NO. 32080 | 128-AlaTyrArgArgProThrGln-134 |
| SEQ. ID. NO. 32081 | 152-GluAsnAlaGlyGluLys-157 |
| SEQ. ID. NO. 32082 | 193-GlnAlaLeuArgGluGlyAlaGluArgIleGlyGlnArgHisPhe-207 |
| SEQ. ID. NO. 32083 | 210-ProValProGluAspGlyThrProGluPheLysGlnValGly-223 |
| SEQ. ID. NO. 32084 | 235-ThrLeuTyrAspAspLeuGluGlyGlnValAlaGluGlnThrHisAsnLeuGluLysGlnAsnArg-256 |
| SEQ. ID. NO. 32085 | 264-ThrThrArgAspLeuHis-269 |
| SEQ. ID. NO. 32086 | 276-GlnAlaAlaGluGluPhe-281 |
| SEQ. ID. NO. 32087 | 300-AsnGlySerAspThrAspIle-306 |
| SEQ. ID. NO. 32088 | 312-GluHisGlyLysLysProProLeuGluLysTyrHisAspGluThrPhe-327 |
| SEQ. ID. NO. 32089 | 331-TyrGlnAsnGluLysLeuGly-337 |
| SEQ. ID. NO. 32090 | 347-ThrSerLeuThrGlyAspAspArgThrLeu-356 |
| SEQ. ID. NO. 32091 | 370-GlyAlaLysGlnGluGluGluLysArgLeu-379 |
| SEQ. ID. NO. 32092 | 383-LeuGlnGluArgAsnLeu-388 |
| SEQ. ID. NO. 32093 | 414-AlaPheAlaGluAsnLysArgGluGluAlaAlaGlu-425 |
| SEQ. ID. NO. 32094 | 436-GluCysTyrGluAspValArgGlu-443 |
| SEQ. ID. NO. 32095 | 450-ThrLysIleSerAsnLysGluPheProGluAlaVal-461 |
| SEQ. ID. NO. 32096 | 488-ThrGlnAspGluGlnLeu-493 |
| SEQ. ID. NO. 32097 | 502-SerLeuSerAsnIleArgLysHisAlaArg-511 |
| SEQ. ID. NO. 32098 | 532-AspAsnGlyGlnGlyPheAspThrGluLysIleGlyGluProThrGly-547 |
| SEQ. ID. NO. 32099 | 555-MetGlnGluArgAlaLysArgIleArgAla-564 |
| SEQ. ID. NO. 32100 | 566-LeuGluIleArgSerGlnAlaGln-573 |
| SEQ. ID. NO. 32101 | 582-GlyAlaProLysGluSerLeuPro-589 |
| g562 | |
| AMPHI Regions - AMPHI | |
| SEQ. ID. NO. 32102 | 48-TrpSerLeuValSerAlaTrpMetValValIle-58 |
| SEQ. ID. NO. 32103 | 84-LeuGluThrThrValMetSerAlaValArgThrLeu-95 |
| SEQ. ID. NO. 32104 | 97-PheThrProTyrThrThrValAlaSerThrSer-107 |
| SEQ. ID. NO. 32105 | 116-ThrPhePheAlaProLeuSerArgTrp-124 |
| SEQ. ID. NO. 32106 | 133-AsnAlaProValHisSerMetThrLysSerThrProSerSerPheHis-148 |
| SEQ. ID. NO. 32107 | 184-ValSerAsnLeuValArgTrpAlaLeu-192 |
| Antigenic Index - Jameson-Wolf | |
| SEQ. ID. NO. 32108 | 9-PheAsnSerGlyLysThrLysPro-16 |
| SEQ. ID. NO. 32109 | 32-ProLeuArgAlaArgArgArgSerLeuTrpArg-42 |
| SEQ. ID. NO. 32110 | 72-AlaThrGlyGluArgGlnLeuVal-79 |
| SEQ. ID. NO. 32111 | 105-SerThrSerSerProProGlyAlaGluMet-114 |
| SEQ. ID. NO. 32112 | 139-MetThrLysSerThrProSerSerPheHisGlySerSerAla-152 |
| SEQ. ID. NO. 32113 | 154-LeuArgValGluLysLysGlyIleLeuSerProLeuThr-166 |
| SEQ. ID. NO. 32114 | 168-ArgLeuProProSerTrpAspThrSerAlaSerLysArgProCysThr-183 |
| Hydrophilic Regions - Hopp-Woods | |
| SEQ. ID. NO. 32115 | 11-SerGlyLysThrLysPro-16 |
| SEQ. ID. NO. 32116 | 33-LeuArgAlaArgArgArgSerLeuTrp-41 |
| SEQ. ID. NO. 32117 | 72-AlaThrGlyGluArgGlnLeuVal-79 |
| SEQ. ID. NO. 32118 | 110-ProGlyAlaGluMet-114 |

TABLE 1-continued

| | |
|---|---|
| SEQ. ID. NO. 32119 | 140-ThrLysSerThrPro-144 |
| SEQ. ID. NO. 32120 | 154-LeuArgValGluLysLysGlyIle-161 |
| SEQ. ID. NO. 32121 | 176-SerAlaSerLysArgProCysThr-183 |
| 563g | |
| AMPHI Regions - AMPHI | |
| SEQ. ID. NO. 32122 | 24-ThrLysArgGluGlyLysSerCys-31 |
| SEQ. ID. NO. 32123 | 115-AsnGlnTyrAlaGlnPhe-120 |
| SEQ. ID. NO. 32124 | 159-ValAsnGlnIleAsnSerSerHisProSerGlnLeuAsnGlyTyrIleGlu-175 |
| SEQ. ID. NO. 32125 | 292-AlaAlaAsnValGlnAspMetAsnAsnThrAla-302 |
| SEQ. ID. NO. 32126 | 332-IleGlnAsnThrGlyLysLeuLeuSerAlaGly-342 |
| SEQ. ID. NO. 32127 | 457-AspAsnAlaValGlnGly-462 |
| SEQ. ID. NO. 32128 | 495-GlnMetAsnAsnIleGlyThr-501 |
| SEQ. ID. NO. 32129 | 571-AlaGlnArgIleHisAsnAlaGly-578 |
| SEQ. ID. NO. 32130 | 594-LeuHisAsnThrAsnGlu-599 |
| SEQ. ID. NO. 32131 | 616-TyrGluAlaPheGlyArg-621 |
| SEQ. ID. NO. 32132 | 642-SerAspHisLeuArgThrProAspGlyValAlaHisGluAsnTrp-656 |
| SEQ. ID. NO. 32133 | 673-ThrAlaProAlaLysIle-678 |
| SEQ. ID. NO. 32134 | 729-GlyLysLeuHisAsnTyrTrpArg-736 |
| SEQ. ID. NO. 32135 | 756-GluGluIleThrArg-760 |
| SEQ. ID. NO. 32136 | 771-SerHisSerLysAlaLeu-776 |
| SEQ. ID. NO. 32137 | 809-ProAsnSerPheThrProLeuPro-816 |
| SEQ. ID. NO. 32138 | 861-LeuHisLysArgLeuGlyAspGlyTyr-869 |
| SEQ. ID. NO. 32139 | 877-GluGlnIleAlaGluLeuThrGlyHisArgArgLeuAspGlyTyrGlnAsn-893 |
| SEQ. ID. NO. 32140 | 899-LysAlaLeuMetAsp-903 |
| SEQ. ID. NO. 32141 | 1002-ThrLeuAspAsnIleGlyGly-1008 |
| SEQ. ID. NO. 32142 | 1019-AlaThrGlnAspIleAsnAsnIleGlyGlyIleLeu-1030 |
| SEQ. ID. NO. 32143 | 1051-LysSerSerGlnAsn-1055 |
| SEQ. ID. NO. 32144 | 1106-GlnAlaGlyArgAspIle-1111 |
| SEQ. ID. NO. 32145 | 1135-GlySerThrAsnGluValGlySerSer-1143 |
| SEQ. ID. NO. 32146 | 1191-ValAspAspAlaSerLysHisThrGlyArg-1200 |
| SEQ. ID. NO. 32147 | 1215-SerHisHisGluThr-1219 |
| SEQ. ID. NO. 32148 | 1254-GlnAlaGlyAsnHisVal-1259 |
| SEQ. ID. NO. 32149 | 1269-GlnSerGluThrTyrHisGln-1275 |
| SEQ. ID. NO. 32150 | 1326-TyrGluGlnThrGly-1330 |
| SEQ. ID. NO. 32151 | 1388-SerThrGlnSerSerLysGlnVal-1395 |
| SEQ. ID. NO. 32152 | 1416-TyrGlnThrGlyLysGlyAlaGlnAsnLeuAlaAsnGlyThrThrAsn-1431 |
| SEQ. ID. NO. 32153 | 1508-GluGlnSerAsnThrGluArgSerGln-1516 |
| SEQ. ID. NO. 32154 | 1542-GlyGlyAsnValGlyLysGlyTyr-1549 |
| SEQ. ID. NO. 32155 | 1692-SerAspIleGlnAsnTyrSerGln-1699 |
| SEQ. ID. NO. 32156 | 1718-LeuGlyGlnGlyAlaLys-1723 |
| SEQ. ID. NO. 32157 | 1761-IleAsnThrProLysAsnIle-1767 |
| SEQ. ID. NO. 32158 | 1796-ThrAspThrAlaGluArgHisSerGlySerLeuLysAsn-1808 |
| SEQ. ID. NO. 32159 | 1825-ValSerGlnAspPheSerLysAsnValGln-1834 |
| SEQ. ID. NO. 32160 | 1893-IleLeuAsnMetLeuAlaSerGlyLeuAlaGluProThr-1905 |
| SEQ. ID. NO. 32161 | 1925-GlyGlnHisPheLysAspLeuAlaGly-1933 |
| SEQ. ID. NO. 32162 | 1968-ProAlaGlyAlaLeu-1972 |
| SEQ. ID. NO. 32163 | 2006-SerAlaIleThrArgMetLeuGlyThrAla-2015 |
| SEQ. ID. NO. 32164 | 2032-PheGlnThrAlaSerAspPheAlaSerSerPheSerTyrProIleAsn-2047 |
| Antigenic Index - Jameson-Wolf | |
| SEQ. ID. NO. 32165 | 1-MetAsnLysThrLeu-5 |
| SEQ. ID. NO. 32166 | 9-IlePheAsnArgLysArgGlyAlaVal-17 |
| SEQ. ID. NO. 32167 | 22-GluThrThrLysArgGluGlyLysSerCysAlaAspSerGlySerGlySer-38 |
| SEQ. ID. NO. 32168 | 48-ProThrHisSerLys-52 |
| SEQ. ID. NO. 32169 | 78-IleIleThrAspLysAlaAlaProLysThrGlnGln-89 |
| SEQ. ID. NO. 32170 | 122-ValGlyAsnArgGlyAlaIleLeuAsnAsnSerArgSerAsnThrGlnThr-138 |
| SEQ. ID. NO. 32171 | 147-AsnProTrpLeuThrArgGlyGluAlaArgVal-157 |
| SEQ. ID. NO. 32172 | 162-IleAsnSerSerHisProSerGlnLeuAsnGly-172 |
| SEQ. ID. NO. 32173 | 174-IleGluValGlyGlyArgArgAlaGluVal-183 |
| SEQ. ID. NO. 32174 | 200-AsnAlaSerArgAlaThrLeu-206 |
| SEQ. ID. NO. 32175 | 208-ThrGlyGlnProGlnTyrGlnAlaGlyAspPheSerGlyPheLysIleArgGlnGlyAsnAla-228 |
| SEQ. ID. NO. 32176 | 234-GlyLeuAspAlaArgAspThrAspPhe-242 |
| SEQ. ID. NO. 32177 | 261-AlaGlyIleArgAsnGlnGlyGlnLeu-269 |
| SEQ. ID. NO. 32178 | 279-AspAlaAsnGlyArgLeuValAsn-286 |
| SEQ. ID. NO. 32179 | 296-GlnAspMetAsnAsnThrAlaGluHisLysValAsnIleArg-309 |
| SEQ. ID. NO. 32180 | 311-GlnAlaPheGluAsnSerGlyThrAlaVal-320 |
| SEQ. ID. NO. 32181 | 322-GlnGlnGlyThrGlnIleHis-328 |
| SEQ. ID. NO. 32182 | 330-GlnSerIleGlnAsnThrGlyLysLeu-338 |
| SEQ. ID. NO. 32183 | 340-SerAlaGlyThrGluAspLeuAlaVal-348 |
| SEQ. ID. NO. 32184 | 351-SerLeuAsnAsnGlnAsnGlyGluIleAlaThrAsn-362 |
| SEQ. ID. NO. 32185 | 366-IleIleHisAspGlyGlnGlnSer-373 |
| SEQ. ID. NO. 32186 | 379-AsnThrAsnGlyThrIleGlnSerGlyArgAspValAlaIle-392 |
| SEQ. ID. NO. 32187 | 395-LysSerLeuSerAsnAsnGlyThrLeuAlaAlaAspAsnLysLeuAspIleAlaLeu-413 |
| SEQ. ID. NO. 32188 | 415-AspAspPheTyrValGluArgLysIleValAlaGlyAsnGluLeu-429 |
| SEQ. ID. NO. 32189 | 431-LeuSerThrArgGlySerLeuLysAsnSerHisThr-442 |
| SEQ. ID. NO. 32190 | 444-GlnAlaGlyLysArgIleArgIleLysAlaAsnAsnLeuAspAsn-458 |
| SEQ. ID. NO. 32191 | 463-AsnIleGlnSerGlyGlyThrThrAspIleGlyThrGlnHisAsnLeuThrAsnArgGlyLeuIleAspGlyGlnGlnThrLysIleGln-492 |
| SEQ. ID. NO. 32192 | 513-AlaThrArgLeuAspAsnGlnAspGluAsnGlyThrGly-525 |
| SEQ. ID. NO. 32193 | 529-AlaAlaArgGluAsnLeu-534 |
| SEQ. ID. NO. 32194 | 540-GlnLeuAsnAsnArgGluAsnSerLeu-548 |
| SEQ. ID. NO. 32195 | 559-GlyAlaLeuAspThrAsnAspGlnAlaThrGlyLysAlaGlnArgIleHisAsnAlaGlyAla-579 |

TABLE 1-continued

| | |
|---|---|
| SEQ. ID. NO. 32196 | 583-AlaAlaGlyLysMetArgLeuGlyValGluLysLeuHisAsnThrAsnGluHisLeuLys-602 |
| SEQ. ID. NO. 32197 | 607-GluThrGlyArgGluArgIleValAsp-615 |
| SEQ. ID. NO. 32198 | 623-GluLeuLeuArgGluGlyThrGlnHis-631 |
| SEQ. ID. NO. 32199 | 638-TyrAsnAsnGluSerAspHisLeuArgThrProAspGlyValAlaHis-653 |
| SEQ. ID. NO. 32200 | 657-HisLysTyrAspTyrGluLysValThrGlnGluThrGlnVal-670 |
| SEQ. ID. NO. 32201 | 680-AlaGlySerAspLeuIleIleAspSerLysAlaValPheAsnSerAspSerArgIle-698 |
| SEQ. ID. NO. 32202 | 707-GlnThrGluLysAspGlyLeuHisAsnGluGlnThrPheGlyGluLysLysValPheSerGluAsnGlyLysLeuHisAsn-733 |
| SEQ. ID. NO. 32203 | 735-TrpArgAlaArgArgLysGlyHisAspGluThrGlyHisArgGluGlnAsnTyrThrLeuProGluGluIleThrArgAspIleSerLeu-764 |
| SEQ. ID. NO. 32204 | 770-GluSerHisSerLysAlaLeuSerArgHisAlaProSerGlnGlyThrGluLeuProGlnSerAsnArgAspAsnIleArgThrAlaLysSerAsnGlyIle-803 |
| SEQ. ID. NO. 32205 | 825-ProAlaAsnLysGlyTyrLeuValGluThrAspProArgPheAlaAsn-840 |
| SEQ. ID. NO. 32206 | 854-LeuLysLeuAspProAsnAsnLeuHisLysArgLeuGlyAspGlyTyrTyrGluGlnArgLeuIleAsn-876 |
| SEQ. ID. NO. 32207 | 883-ThrGlyHisArgArgLeuAspGlyTyrGlnAsnAspGluGluGlnPheLysAlaLeuMetAspAsnGlyAlaThrAlaAlaArgSerMetAsn-913 |
| SEQ. ID. NO. 32208 | 922-AlaGluGlnAlaAla-926 |
| SEQ. ID. NO. 32209 | 938-LysGluValLysLeuProAspGlyGlyThr-947 |
| SEQ. ID. NO. 32210 | 959-ValLysAsnGlyGlyIleAspGlyLysGly-968 |
| SEQ. ID. NO. 32211 | 982-GlySerLeuLysAsnSerGlyThrIleAlaGlyArgAsnAla-995 |
| SEQ. ID. NO. 32212 | 999-AsnThrAspThrLeuAspAsnIleGlyGly-1008 |
| SEQ. ID. NO. 32213 | 1010-IleHisAlaGlnLysSerAlaVal-1017 |
| SEQ. ID. NO. 32214 | 1040-AlaGlyAsnAsnIleAsnAsnGlnSerThrAlaLysSerSerGlnAsnAlaGlnGlySer-1059 |
| SEQ. ID. NO. 32215 | 1072-ThrGlyLysGluLysGlyVal-1078 |
| SEQ. ID. NO. 32216 | 1083-AlaGlyLysAspIleAsnIle-1089 |
| SEQ. ID. NO. 32217 | 1094-IleSerAsnGlnSerAspGlnGlyGlnThrArgLeuGlnAlaGlyArgAspIleAsnLeuAspThrValGlnThrGlyLysTyrGlnGluIleHisPheAspAlaAspAsnHisThrIleArgGlySerThrAsnGluValGlySerSerIleGlnThrLysGlyAspVal-1150 |
| SEQ. ID. NO. 32218 | 1155-GlyAsnAsnLeuAsnAlaLysAlaAlaGluValGlySerAlaLysGlyThr-1171 |
| SEQ. ID. NO. 32219 | 1175-TyrAlaLysAsnAspIleThrIle-1182 |
| SEQ. ID. NO. 32220 | 1190-GlnValAspAspAlaSerLysHisThrGlyArgSerGlyGlyGlyAsnLys-1206 |
| SEQ. ID. NO. 32221 | 1208-ValIleThrAspLysAlaGlnSerHisHisGluThrAlaGlnSerSerThrPheGluGlyLysGln-1229 |
| SEQ. ID. NO. 32222 | 1233-GlnAlaGlyAsnAspAlaAsn-1239 |
| SEQ. ID. NO. 32223 | 1245-ValIleSerAspAsnGlyThrArgIleGlnAla-1255 |
| SEQ. ID. NO. 32224 | 1262-GlyThrThrGlnThrGlnSerGlnSerGluThrTyrHisGlnThrGlnLysSerGlyLeu-1281 |
| SEQ. ID. NO. 32225 | 1291-GlySerLysThrAsnThrGlnGluAsnGlnSerGlnSerAsnGluHisThrGlySerThrValGlySerLeuLysGlyAspThrThrIle-1320 |
| SEQ. ID. NO. 32226 | 1324-LysHisTyrGluGlnThrGlySerAsnValSerSerProGluGlyAsnAsnLeu-1341 |
| SEQ. ID. NO. 32227 | 1354-AsnGlnLeuAsnSerLysThrThrGlnThrTyrGluGlnLysGlyLeu-1369 |
| SEQ. ID. NO. 32228 | 1379-ArgPheGlyThrThrSerAspCysArgSerThrGlnSerSerLysGlnValGlyGlnSerLysAsnAspArgValAsnAla-1405 |
| SEQ. ID. NO. 32229 | 1415-AlaTyrGlnThrGlyLysGlyAlaGlnAsnLeuAlaAsnGlyThrThrAsnAlaLys-1433 |
| SEQ. ID. NO. 32230 | 1441-TyrGlyGluGlnGlnAsnArgGlnThrThrGln-1451 |
| SEQ. ID. NO. 32231 | 1460-SerGlnIleGlnAlaGlyGlyLysThr-1468 |
| SEQ. ID. NO. 32232 | 1470-LeuTyrCysArgArgCysGlyGluGlnSerAsn-1480 |
| SEQ. ID. NO. 32233 | 1487-GlyValSerGlyArgAlaGlyThr-1494 |
| SEQ. ID. NO. 32234 | 1496-LeuIleAlaAspLysGlnIle-1502 |
| SEQ. ID. NO. 32235 | 1506-SerAlaGluGlnSerAsnThrGluArgSerGlnAsnLysSerAlaGlyTrpAsn-1523 |
| SEQ. ID. NO. 32236 | 1543-GlyAsnValGlyLysGlyTyrGlyTyrGlyAspSerValThrHisArgHisSerHisIleGlyAspLysGlySerGln-1568 |
| SEQ. ID. NO. 32237 | 1572-GlnSerGlyGlyAspThrIleIle-1579 |
| SEQ. ID. NO. 32238 | 1582-AlaGlnValArgGlyLysGlyValGlnValAsnAlaLysAsn-1595 |
| SEQ. ID. NO. 32239 | 1600-SerValGlnAspArgGluThrTyrGlnSerLysGlnGlnAsnAlaGlyAla-1616 |
| SEQ. ID. NO. 32240 | 1626-AlaSerGlyAspTyrSerGlnSerLysIleArgAlaAspHis-1639 |
| SEQ. ID. NO. 32241 | 1641-SerValThrGluGlnSerGlyIleTyrAlaGlyGluAspGlyTyrGln-1656 |
| SEQ. ID. NO. 32242 | 1660-GlyAsnHisThrGlyLeuLysGlyGlyIle-1669 |
| SEQ. ID. NO. 32243 | 1673-SerGlnSerAlaLysAspLysGlyLysAsnArgPheSerThrGlyThrLeuAlaGlySerAspIleGlnAsnTyrSerGlnTyrGluGlyLysSerPheGly-1706 |
| SEQ. ID. NO. 32244 | 1713-ValSerGlyLysThrLeuGlyGlnGlyAlaLysAsnLysProGlnAspLysHisLeu-1731 |
| SEQ. ID. NO. 32245 | 1734-IleAlaAspLysAsnGlyAlaSerSer-1742 |
| SEQ. ID. NO. 32246 | 1745-GlyTyrGlySerAspSerAspSerGlnSerSerIleThrLysSerGlyIleAsnThrProLysAsnIleGlnIleThrAspGluAlaAlaGln-1775 |
| SEQ. ID. NO. 32247 | 1778-LeuThrGlyLysIleAlaAlaGlnThrLysAlaAspIleAspThrAsnValThrThrAspThrAlaGluArgHisSerGlySerLeuLysAsnIlePheAspLysAspArgValGlnSerGluLeuAspLeuGlnArgThrValSerGlnAspPheSerLysAsnValGlnGlnThrAsnThrGluIle-1840 |
| SEQ. ID. NO. 32248 | 1842-GlnHisLeuAspLysLeuLysAlaAspLysGluAlaAlaGluThrAlaAla-1858 |
| SEQ. ID. NO. 32249 | 1863-AlaAsnGlyAspMetGluThrAlaLysArgLysAlaHisGluAlaGlnAspAlaAlaAlaLysAlaAspAsnTrpGlnGln-1889 |
| SEQ. ID. NO. 32250 | 1899-SerGlyLeuAlaGluProThrGlnSerGly-1908 |
| SEQ. ID. NO. 32251 | 1915-ThrAlaSerProAspValSer-1921 |
| SEQ. ID. NO. 32252 | 1927-HisPheLysAspLeuAlaGlyGlnAsnAlaAsnGlyLysLeuThrAlaSerGlnGluThr-1946 |
| SEQ. ID. NO. 32253 | 1963-XxxGlyAsnAsnAlaPro-1968 |
| SEQ. ID. NO. 32254 | 1973-GlyAlaGlyGlySerGluAlaAla-1980 |
| SEQ. ID. NO. 32255 | 1988-LeuTyrGlyLysGlyAspGlyGlySerLeuAsnAlaGluGluLysGluThrVal-2005 |
| SEQ. ID. NO. 32256 | 2017-GlyAlaAlaGluGlyAsnSerSerAlaAspAla-2027 |
| SEQ. ID. NO. 32257 | 2034-ThrAlaSerAspPheAlaSerSerPheSerTyr-2044 |
| Hydrophilic Regions - Hopp-Woods | |
| SEQ. ID. NO. 32258 | 10-PheAsnArgLysArgGlyAla-16 |
| SEQ. ID. NO. 32259 | 22-GluThrThrLysArgGluGlyLysSerCysAlaAspSerGlySer-36 |
| SEQ. ID. NO. 32260 | 78-IleIleThrAspLysAlaAlaProLysThrGlnGln-89 |
| SEQ. ID. NO. 32261 | 131-AsnSerArgSerAsnThr-136 |
| SEQ. ID. NO. 32262 | 153-GlyGluAlaArgVal-157 |
| SEQ. ID. NO. 32263 | 176-ValGlyGlyArgArgAlaGluVal-183 |
| SEQ. ID. NO. 32264 | 235-LeuAspAlaArgAspThrAspPhe-242 |
| SEQ. ID. NO. 32265 | 261-AlaGlyIleArgAsn-265 |
| SEQ. ID. NO. 32266 | 296-GlnAspMetAsnAsnThrAlaGluHisLysValAsnIle-308 |
| SEQ. ID. NO. 32267 | 311-GlnAlaPheGluAsnSerGly-317 |
| SEQ. ID. NO. 32268 | 342-GlyThrGluAspLeuAla-347 |
| SEQ. ID. NO. 32269 | 355-GlnAsnGlyGluIleAlaThr-361 |

TABLE 1-continued

| | |
|---|---|
| SEQ. ID. NO. 32270 | 385-GlnSerGlyArgAspValAlaIle-392 |
| SEQ. ID. NO. 32271 | 403-LeuAlaAlaAspAsnLysLeuAspIleAlaLeu-413 |
| SEQ. ID. NO. 32272 | 417-PheTyrValGluArgLysIleValAla-425 |
| SEQ. ID. NO. 32273 | 435-GlySerLeuLysAsn-439 |
| SEQ. ID. NO. 32274 | 444-GlnAlaGlyLysArgIleArgIleLysAlaAsnAsnLeu-456 |
| SEQ. ID. NO. 32275 | 468-GlyThrThrAspIleGlyThr-474 |
| SEQ. ID. NO. 32276 | 487-GlnGlnThrLysIleGln-492 |
| SEQ. ID. NO. 32277 | 514-ThrArgLeuAspAsnGlnAspGluAsnGlyThr-524 |
| SEQ. ID. NO. 32278 | 529-AlaAlaArgGluAsnLeu-534 |
| SEQ. ID. NO. 32279 | 540-GlnLeuAsnAsnArgGluAsnSer-547 |
| SEQ. ID. NO. 32280 | 561-LeuAspThrAsnAspGlnAlaThrGlyLysAlaGlnArgIleHis-575 |
| SEQ. ID. NO. 32281 | 583-AlaAlaGlyLysMetArgLeuGlyValGluLysLeuHisAsnThrAsnGluHisLeuLys-602 |
| SEQ. ID. NO. 32282 | 607-GluThrGlyArgGluArgIleValAsp-615 |
| SEQ. ID. NO. 32283 | 623-GluLeuLeuArgGluGlyThrGlnHis-631 |
| SEQ. ID. NO. 32284 | 640-AsnGluSerAspHisLeuArgThrProAspGlyValAla-652 |
| SEQ. ID. NO. 32285 | 659-TyrAspTyrGluLysValThrGln-666 |
| SEQ. ID. NO. 32286 | 684-LeuIleIleAspSerLysAla-690 |
| SEQ. ID. NO. 32287 | 694-SerAspSerArgIle-698 |
| SEQ. ID. NO. 32288 | 707-GlnThrGluLysAspGlyLeuHisAsn-715 |
| SEQ. ID. NO. 32289 | 717-GlnThrPheGlyGluLysLysValPheSerGluAsnGlyLys-730 |
| SEQ. ID. NO. 32290 | 736-ArgAlaArgArgLysGlyHisAspGluThrGlyHisArgGluGlnAsn-751 |
| SEQ. ID. NO. 32291 | 756-GluGluIleThrArgAspIleSer-763 |
| SEQ. ID. NO. 32292 | 771-SerHisSerLysAlaLeuSerArgHisAlaPro-781 |
| SEQ. ID. NO. 32293 | 783-GlnGlyThrGluLeuProGlnSerAsnArgAspAsnIleArgThrAlaLysSerAsnGly-802 |
| SEQ. ID. NO. 32294 | 830-TyrLeuValGluThrAspProArgPheAlaAsn-840 |
| SEQ. ID. NO. 32295 | 854-LeuLysLeuAspPro-858 |
| SEQ. ID. NO. 32296 | 860-AsnLeuHisLysArgLeuGly-866 |
| SEQ. ID. NO. 32297 | 883-ThrGlyHisArgArgLeuAspGlyTyrGlnAsnAspGluGluGlnPheLysAlaLeuMet-902 |
| SEQ. ID. NO. 32298 | 905-GlyAlaThrAlaAlaArg-910 |
| SEQ. ID. NO. 32299 | 922-AlaGluGlnAlaAla-926 |
| SEQ. ID. NO. 32300 | 938-LysGluValLysLeuProAspGlyGlyThr-947 |
| SEQ. ID. NO. 32301 | 959-ValLysAsnGlyGlyIleAspGlyLysGly-968 |
| SEQ. ID. NO. 32302 | 982-GlySerLeuLysAsn-986 |
| SEQ. ID. NO. 32303 | 1010-IleHisAlaGlnLysSerAlaVal-1017 |
| SEQ. ID. NO. 32304 | 1048-SerThrAlaLysSerSerGlnAsnAlaGlnGly-1058 |
| SEQ. ID. NO. 32305 | 1073-GlyLysGluLysGlyVal-1078 |
| SEQ. ID. NO. 32306 | 1083-AlaGlyLysAspIleAsn-1088 |
| SEQ. ID. NO. 32307 | 1096-AsnGlnSerAspGlnGlyGlnThrArgLeuGlnAlaGlyArgAspIleAsnLeu-1113 |
| SEQ. ID. NO. 32308 | 1125-HisPheAspAlaAspAsnHisThrIleArgGlySerThrAsnGluValGlySer-1142 |
| SEQ. ID. NO. 32309 | 1144-IleGlnThrLysGlyAspVal-1150 |
| SEQ. ID. NO. 32310 | 1158-LeuAsnAlaLysAlaAlaGluValGlySerAlaLysGly-1170 |
| SEQ. ID. NO. 32311 | 1176-AlaLysAsnAspIle-1180 |
| SEQ. ID. NO. 32312 | 1190-GlnValAspAspAlaSerLysHisThrGlyArgSerGlyGlyGly-1204 |
| SEQ. ID. NO. 32313 | 1208-ValIleThrAspLysAlaGlnSerHisHisGluThrAlaGln-1221 |
| SEQ. ID. NO. 32314 | 1223-SerThrPheGluGlyLysGln-1229 |
| SEQ. ID. NO. 32315 | 1249-AsnGlyThrArgIleGlnAla-1255 |
| SEQ. ID. NO. 32316 | 1267-GlnSerGlnSerGluThr-1272 |
| SEQ. ID. NO. 32317 | 1276-ThrGlnLysSerGlyLeu-1281 |
| SEQ. ID. NO. 32318 | 1292-SerLysThrAsnThrGlnGluAsnGlnSerGlnSerAsnGluHisThrGly-1308 |
| SEQ. ID. NO. 32319 | 1314-LeuLysGlyAspThr-1318 |
| SEQ. ID. NO. 32320 | 1324-LysHisTyrGluGlnThrGly-1330 |
| SEQ. ID. NO. 32321 | 1334-SerSerProGluGly-1338 |
| SEQ. ID. NO. 32322 | 1356-LeuAsnSerLysThrThrGln-1362 |
| SEQ. ID. NO. 32323 | 1364-TyrGluGlnLysGly-1368 |
| SEQ. ID. NO. 32324 | 1384-SerAspCysArgSerThrGlnSerSerLysGlnValGlyGlnSerLysAsnAspArgValAsn-1404 |
| SEQ. ID. NO. 32325 | 1417-GlnThrGlyLysGlyAlaGln-1423 |
| SEQ. ID. NO. 32326 | 1443-GluGlnGlnAsnArgGlnThrThr-1450 |
| SEQ. ID. NO. 32327 | 1474-ArgCysGlyGluGlnSerAsn-1480 |
| SEQ. ID. NO. 32328 | 1488-ValSerGlyArgAlaGly-1493 |
| SEQ. ID. NO. 32329 | 1497-IleAlaAspLysGlnIle-1502 |
| SEQ. ID. NO. 32330 | 1506-SerAlaGluGlnSerAsnThrGluArgSerGlnAsnLys-1518 |
| SEQ. ID. NO. 32331 | 1560-SerHisIleGlyAspLysGlySer-1567 |
| SEQ. ID. NO. 32332 | 1582-AlaGlnValArgGlyLysGlyVal-1589 |
| SEQ. ID. NO. 32333 | 1600-SerValGlnAspArgGluThrTyrGlnSerLysGlnGlnAsn-1613 |
| SEQ. ID. NO. 32334 | 1628-GlyAspTyrSerGlnSerLysIleArgAlaAspHis-1639 |
| SEQ. ID. NO. 32335 | 1650-AlaGlyGluAspGlyTyrGln-1656 |
| SEQ. ID. NO. 32336 | 1674-GlnSerAlaLysAspLysGlyLysAsnArgPheSer-1685 |
| SEQ. ID. NO. 32337 | 1700-TyrGluGlyLysSer-1704 |
| SEQ. ID. NO. 32338 | 1717-ThrLeuGlyGlnGlyAlaLysAsnLysProGlnAspLysHisLeu-1731 |
| SEQ. ID. NO. 32339 | 1734-IleAlaAspLysAsnGlyAla-1740 |
| SEQ. ID. NO. 32340 | 1748-SerAspSerAspSerGlnSerSerIleThr-1757 |
| SEQ. ID. NO. 32341 | 1768-GlnIleThrAspGluAlaAlaGln-1775 |
| SEQ. ID. NO. 32342 | 1786-ThrLysAlaAspIleAspThr-1792 |
| SEQ. ID. NO. 32343 | 1794-ValThrThrAspThrAlaGluArgHisSerGlySerLeu-1806 |
| SEQ. ID. NO. 32344 | 1808-AsnIlePheAspLysAspArgValGlnSerGluLeuAspLeuGlnArgThrValSer-1826 |
| SEQ. ID. NO. 32345 | 1836-ThrAsnThrGluIle-1840 |
| SEQ. ID. NO. 32346 | 1842-GlnHisLeuAspLysLeuLysAlaAspLysGluAlaAlaGluThrAlaAla-1858 |
| SEQ. ID. NO. 32347 | 1865-GlyAspMetGluThrAlaLysArgLysAlaHisGluAlaGlnAspAlaAlaAlaLysAlaAspAsn-1886 |
| SEQ. ID. NO. 32348 | 1901-LeuAlaGluProThrGln-1906 |
| SEQ. ID. NO. 32349 | 1927-HisPheLysAspLeuAlaGly-1933 |

TABLE 1-continued

| | |
|---|---|
| SEQ. ID. NO. 32350 | 1936-AlaAsnGlyLysLeuThrAlaSerGlnGluThr-1946 |
| SEQ. ID. NO. 32351 | 1975-GlyGlySerGluAlaAla-1980 |
| SEQ. ID. NO. 32352 | 1991-LysGlyAspGlyGlySerLeuAsnAlaGluGluLysGluThrVal-2005 |
| SEQ. ID. NO. 32353 | 2017-GlyAlaAlaGluGlyAsnSerSerAla-2025 |
| g565-2 | |
| AMPHI Regions - AMPHI | |
| SEQ. ID. NO. 32354 | 50-AlaThrCysThrArgAlaMetSerLysSer-59 |
| SEQ. ID. NO. 32355 | 66-SerSerTrpAlaArg-70 |
| SEQ. ID. NO. 32356 | 103-AspPheMetSerGlnLeuAspLeuThr-111 |
| SEQ. ID. NO. 32357 | 139-CysSerAsnSerGlyGluThrIleSerSerCysProAlaMetAlaSerIleThrLysProAsn-159 |
| SEQ. ID. NO. 32358 | 184-AlaAsnThrThrAsnAlaPheAsnThr-192 |
| Antigenic Index - Jameson-Wolf | |
| SEQ. ID. NO. 32359 | 1-MetAspSerThrLeuSerLysThrCys-9 |
| SEQ. ID. NO. 32360 | 23-PheAlaArgProArgProAlaAlaSerAsnThrSerLeu-35 |
| SEQ. ID. NO. 32361 | 37-PheAlaSerProAsnAspThrGlySer-45 |
| SEQ. ID. NO. 32362 | 55-AlaMetSerLysSerSerAlaLysTyrGly-64 |
| SEQ. ID. NO. 32363 | 67-SerTrpAlaArgThrArgProThrValCysProProLeuProLysProThrIle-84 |
| SEQ. ID. NO. 32364 | 86-ThrXxxSerAspLeu-90 |
| SEQ. ID. NO. 32365 | 97-MetLeuCysArgSerSerAspPheMetSer-106 |
| SEQ. ID. NO. 32366 | 109-AspLeuThrLysArgProThrSerAlaSerLeuProProLysArgLysGlyAlaIle-127 |
| SEQ. ID. NO. 32367 | 129-IleAspSerArgThrAlaAla-135 |
| SEQ. ID. NO. 32368 | 139-CysSerAsnSerGlyGluThrIleSer-147 |
| SEQ. ID. NO. 32369 | 155-IleThrLysProAsnSerProProCysAlaArgTyr-166 |
| SEQ. ID. NO. 32370 | 170-LeuArgLeuSerProThrGlu-176 |
| SEQ. ID. NO. 32371 | 194-SerIleAlaAsnSerIleAsnThrCysArgGlnProPro-206 |
| Hydrophilic Regions - Hopp-Woods | |
| SEQ. ID. NO. 32372 | 24-AlaArgProArgProAlaAla-30 |
| SEQ. ID. NO. 32373 | 39-SerProAsnAspThrGlySer-45 |
| SEQ. ID. NO. 32374 | 55-AlaMetSerLysSerSerAla-61 |
| SEQ. ID. NO. 32375 | 69-AlaArgThrArgPro-73 |
| SEQ. ID. NO. 32376 | 100-ArgSerSerAspPhe-104 |
| SEQ. ID. NO. 32377 | 109-AspLeuThrLysArgProThrSer-116 |
| SEQ. ID. NO. 32378 | 119-LeuProProLysArgLysGlyAlaIle-127 |
| SEQ. ID. NO. 32379 | 129-IleAspSerArgThr-133 |
| SEQ. ID. NO. 32380 | 141-AsnSerGlyGluThrIleSer-147 |
| SEQ. ID. NO. 32381 | 156-ThrLysProAsnSer-160 |
| g566 | |
| AMPHI Regions - AMPHI | |
| SEQ. ID. NO. 32382 | 52-GlyPheValGlyAspPheHisAlaPhe-60 |
| Antigenic Index - Jameson-Wolf | |
| SEQ. ID. NO. 32383 | 36-ProAsnCysGlyAlaAspGlyThrGlyGlyLysGlyHisAla-49 |
| SEQ. ID. NO. 32384 | 61-AlaValGlyGlyGluGluGlyGlyVal-69 |
| SEQ. ID. NO. 32385 | 77-AlaAspGlyGlyLysAlaAspGlyGlyArgIleAlaArg-89 |
| SEQ. ID. NO. 32386 | 105-AlaAlaGluArgAlaGlyAspAspPheAla-114 |
| Hydrophilic Regions - Hopp-Woods | |
| SEQ. ID. NO. 32387 | 39-GlyAlaAspGlyThrGlyGlyLysGlyHisAla-49 |
| SEQ. ID. NO. 32388 | 63-GlyGlyGluGluGlyGlyVal-69 |
| SEQ. ID. NO. 32389 | 78-AspGlyGlyLysAlaAspGlyGlyArgIleAlaArg-89 |
| SEQ. ID. NO. 32390 | 105-AlaAlaGluArgAlaGlyAspAspPheAla-114 |
| g567 | |
| AMPHI Regions - AMPHI | |
| SEQ. ID. NO. 32391 | 54-GluLeuValGlnGluIleAlaArgGluVal-63 |
| SEQ. ID. NO. 32392 | 68-AlaLeuLysAlaVal-72 |
| SEQ. ID. NO. 32393 | 110-TyrAlaLeuGluGlyIleSerAspLeuIleAlaThrValArgLysIleArgGln-127 |
| SEQ. ID. NO. 32394 | 136-ThrGlyIleValArg-140 |
| SEQ. ID. NO. 32395 | 151-AlaGluValSerGluGlnLeuArgSerHisPheGlyAspLeuLeu-165 |
| SEQ. ID. NO. 32396 | 170-IleProArgAsnIleArgLeuAla-177 |
| Antigenic Index - Jameson-Wolf | |
| SEQ. ID. NO. 32397 | 1-MetArgArgArgAlaAlaAlaSerThrArgArgValCysSerProAlaPhe-17 |
| SEQ. ID. NO. 32398 | 24-MetArgThrCysSerArgArgArgTyrAlaAlaLysArgAlaAspThr-39 |
| SEQ. ID. NO. 32399 | 51-AlaGluIleGluLeu-55 |
| SEQ. ID. NO. 32400 | 57-GlnGluIleAlaArgGluValArgLeuLysAsnAlaLeu-69 |
| SEQ. ID. NO. 32401 | 71-AlaValAlaGluAspTyrAsp-77 |
| SEQ. ID. NO. 32402 | 83-CysProProSerLeu-87 |
| SEQ. ID. NO. 32403 | 123-ArgLysIleArgGlnAlaValAsnProAspLeuAspIle-135 |
| SEQ. ID. NO. 32404 | 141-ThrMetTyrAspSerArgSerArgLeuValAlaGluValSerGluGlnLeuArgSerHisPheGlyAspLeu-164 |
| SEQ. ID. NO. 32405 | 169-AlaIleProArgAsnIleArgLeuAlaGluAlaProSerHisGly-183 |
| SEQ. ID. NO. 32406 | 191-AlaGlnAlaLysGlyAlaLys-197 |
| SEQ. ID. NO. 32407 | 204-AspGluLeuAlaAlaArgValSerGlyLys-213 |
| Hydrophilic Regions - Hopp-Woods | |
| SEQ. ID. NO. 32408 | 1-MetArgArgArgAlaAlaAlaSerThrArgArgValCys-13 |
| SEQ. ID. NO. 32409 | 26-ThrCysSerArgArgArgTyrAlaAlaLysArgAlaAspThr-39 |
| SEQ. ID. NO. 32410 | 51-AlaGluIleGluLeu-55 |
| SEQ. ID. NO. 32411 | 57-GlnGluIleAlaArgGluValArgLeuLysAsnAlaLeu-69 |
| SEQ. ID. NO. 32412 | 71-AlaValAlaGluAspTyrAsp-77 |
| SEQ. ID. NO. 32413 | 123-ArgLysIleArgGln-127 |
| SEQ. ID. NO. 32414 | 131-ProAspLeuAspIle-135 |
| SEQ. ID. NO. 32415 | 142-MetTyrAspSerArgSerArgLeuValAlaGluValSerGluGlnLeuArg-158 |
| SEQ. ID. NO. 32416 | 172-ArgAsnIleArgLeuAlaGlu-178 |
| SEQ. ID. NO. 32417 | 191-AlaGlnAlaLysGlyAlaLys-197 |

TABLE 1-continued

SEQ. ID. NO. 32418 204-AspGluLeuAlaAla-208
g568-2
AMPHI Regions - AMPHI
SEQ. ID. NO. 32419 32-AsnIlePheArgArgIle-37
SEQ. ID. NO. 32420 49-LysAlaCysLysAsn-53
SEQ. ID. NO. 32421 71-GluLysAlaAsnThrValArgTyr-78
SEQ. ID. NO. 32422 82-SerLeuAlaGlnCysPheThr-88
SEQ. ID. NO. 32423 112-ArgProLeuProSerIleIleThrAla-120
SEQ. ID. NO. 32424 154-ProXxxAspLeuAsn-158
SEQ. ID. NO. 32425 177-LeuValGlyGlnPheLeuAsnArgLeuPhe-186
SEQ. ID. NO. 32426 200-GluGluPhePheAspValValVal-207
SEQ. ID. NO. 32427 227-AspPheAsnGlnValPheAlaAlaPheLeu-236
SEQ. ID. NO. 32428 241-HisArgHisAlaAspGlnIleAlaAspSerCysArgValGlnSerGln-256
Antigenic Index - Jameson-Wolf
SEQ. ID. NO. 32429 12-LysAlaSerAlaSerSerIlePro-19
SEQ. ID. NO. 32430 21-ArgIleCysArgLeuLysArgSerArgLeuProAsnIlePhe-34
SEQ. ID. NO. 32431 39-PheSerCysArgArgArgThrCysPheCysLysAlaCysLysAsnSerProIleArgAsnGluThrSerSerSerGlyArgArgGlnPheSerVal GluLysAlaAsnThr-75
SEQ. ID. NO. 32432 91-SerAsnAlaSerLysProArgLeu-98
SEQ. ID. NO. 32433 102-IleArgGlyArgLysArgPhePheAla-110
SEQ. ID. NO. 32434 141-PheArgGlySerAlaPheLysCysArgLeuAsnAlaAlaProXxxAspLeuAsnArg-159
SEQ. ID. NO. 32435 166-GlySerGlnAsnLeu-170
SEQ. ID. NO. 32436 213-ValAlaAspArgAspAlaSer-219
SEQ. ID. NO. 32437 237-GlyGlnHisGlyHisArgHisAlaAspGlnIleAlaAspSerCysArgValGlnSerGln-256
Hydrophilic Regions - Hopp-Woods
SEQ. ID. NO. 32438 21-ArgIleCysArgLeuLysArgSerArgLeu-30
SEQ. ID. NO. 32439 41-CysArgArgArgThrCysPhe-47
SEQ. ID. NO. 32440 49-LysAlaCysLysAsnSerProIleArgAsnGluThrSerSerSerGlyArgArgGlnPheSerValGluLysAlaAsnThr-75
SEQ. ID. NO. 32441 93-AlaSerLysProArgLeu-98
SEQ. ID. NO. 32442 102-IleArgGlyArgLysArgPhePheAla-110
SEQ. ID. NO. 32443 144-SerAlaPheLysCysArgLeu-150
SEQ. ID. NO. 32444 152-AlaAlaProXxxAspLeuAsnArg-159
SEQ. ID. NO. 32445 213-ValAlaAspArgAspAlaSer-219
SEQ. ID. NO. 32446 239-HisGlyHisArgHisAlaAspGlnIleAlaAspSerCysArgVal-253
g569-2
AMPHI Regions - AMPHI
SEQ. ID. NO. 32447 29-AlaAlaPheCysGlyLeuIleAlaLeuThrAlaLeuTrpGluTyrAlaArgMetAlaGlyLeuCysLys-51
SEQ. ID. NO. 32448 86-PheTrpLeuAlaValMetPro-92
SEQ. ID. NO. 32449 161-IleAlaArgAlaIleSerProGlyLysSerTrpGluGlyAlaIle-175
SEQ. ID. NO. 32450 203-ThrValLeuIleGlyLeu-208
SEQ. ID. NO. 32451 210-LeuThrValValSerValCysGlyAspLeuLeuGluSerTrpLeuLys-225
Antigenic Index - Jameson-Wolf
SEQ. ID. NO. 32452 50-CysLysThrGluThrAsnHis-56
SEQ. ID. NO. 32453 98-LysTrpArgLeuAsnGlyGlyTrp-105
SEQ. ID. NO. 32454 124-SerLeuArgProHisProAspAspAlaLeu-133
SEQ. ID. NO. 32455 154-LysAlaLeuGlyLysHisLysIleAlaArg-163
SEQ. ID. NO. 32456 165-IleSerProGlyLysSerTrpGlu-172
SEQ. ID. NO. 32457 227-AlaAlaGlyIleLysAspSerSerAsnLeuLeuProGlyHis-240
SEQ. ID. NO. 32458 242-GlyValPheAspArgThrAspSer-249
Hydrophilic Regions - Hopp-Woods
SEQ. ID. NO. 32459 50-CysLysThrGluThr-54
SEQ. ID. NO. 32460 127-ProHisProAspAspAlaLeu-133
SEQ. ID. NO. 32461 155-AlaLeuGlyLysHisLysIleAlaArg-163
SEQ. ID. NO. 32462 227-AlaAlaGlyIleLysAspSerSerAsn-235
SEQ. ID. NO. 32463 243-ValPheAspArgThrAspSer-249
g570
AMPHI Regions - AMPHI
SEQ. ID. NO. 32464 6-ArgAlaPheAlaAlaAlaLeuIleGlyLeu-15
SEQ. ID. NO. 32465 22-HisAlaAspThrPheGlnLysIleGlyPheIleAsn-33
SEQ. ID. NO. 32466 43-GlnAlaArgAsnIleGlnLysThrLeuAspGly-53
SEQ. ID. NO. 32467 60-AspGluLeuGlnLysLeuGln-66
SEQ. ID. NO. 32468 81-LeuLysAspAlaLysLys-86
SEQ. ID. NO. 32469 91-GluLysTrpArgGlyLeuValGluAlaPheArg-101
SEQ. ID. NO. 32470 122-LeuGlnGlnAsnAlaAsnArgValIleValLysIle-133
Antigenic Index - Jameson-Wolf
SEQ. ID. NO. 32471 33-AsnThrGluArgIleTyrLeuGluSerLysGlnAlaArgAsnIleGlnLysThrLeuAspGlyGluPheSerAlaArgGlnAspGluLeuGlnLys LeuGlnArgGluGlyLeuAspLeuGluArgGlnLeuAlaGlyGlyLysLeuLysAspAlaLysLysAlaGlnAlaGluGluLysTrpArgGly-95
SEQ. ID. NO. 32472 99-AlaPheArgLysLysGlnAlaGlnPheGluGluAspTyrAsnLeuArgArgAsnGluGluPheAla-120
SEQ. ID. NO. 32473 123-GlnGlnAsnAlaAsnArgVal-129
SEQ. ID. NO. 32474 133-IleAlaLysGlnGluGlyTyrAspValIle-142
SEQ. ID. NO. 32475 150-AsnThrGlnTyrAspValThrAspSerValIleLysGluMetAsnAlaArg-166
Hydrophilic Regions - Hopp-Woods
SEQ. ID. NO. 32476 37-IleTyrLeuGluSerLysGlnAlaArgAsnIleGlnLysThrLeuAspGlyGluPheSerAlaArgGlnAspGluLeuGlnLysLeuGlnArgGlu GlyLeuAspLeuGluArgGlnLeuAla-77
SEQ. ID. NO. 32477 79-GlyLysLeuLysAspAlaLysLysAlaGlnAlaGluGluLysTrpArgGly-95
SEQ. ID. NO. 32478 99-AlaPheArgLysLysGlnAlaGlnPheGluGluAspTyrAsnLeuArgArgAsnGluGluPheAla-120

TABLE 1-continued

| | |
|---|---|
| SEQ. ID. NO. 32479 | 133-IleAlaLysGlnGluGlyTyr-139 |
| SEQ. ID. NO. 32480 | 154-AspValThrAspSerValIleLysGluMetAsnAlaArg-166 |
| g571 | |
| AMPHI Regions - AMPHI | |
| SEQ. ID. NO. 32481 | 10-ValValThrValPheGlyGlyGlyIleGlySerAlaVal-22 |
| SEQ. ID. NO. 32482 | 58-AlaAlaValAlaAspPhePheAlaVal-66 |
| SEQ. ID. NO. 32483 | 89-ValGluValPheLysGlu-94 |
| Antigenic Index - Jameson-Wolf | |
| SEQ. ID. NO. 32484 | 30-LysGlnAlaGlnAlaAspGly-36 |
| SEQ. ID. NO. 32485 | 40-PheArgThrGlyHisArgGluGluGlnLeuGlyGlyAspVal-53 |
| SEQ. ID. NO. 32486 | 72-ArgAlaGluArgAlaAla-77 |
| SEQ. ID. NO. 32487 | 91-ValPheLysGluGlyAspPhe-97 |
| SEQ. ID. NO. 32488 | 105-ArgAsnAlaAspPheAlaAlaGluHisGlnArgGluGlyPheAla-119 |
| Hydrophilic Regions - Hopp-Woods | |
| SEQ. ID. NO. 32489 | 30-LysGlnAlaGlnAlaAsp-35 |
| SEQ. ID. NO. 32490 | 42-ThrGlyHisArgGluGluGlnLeuGly-50 |
| SEQ. ID. NO. 32491 | 72-ArgAlaGluArgAlaAla-77 |
| SEQ. ID. NO. 32492 | 91-ValPheLysGluGlyAspPhe-97 |
| SEQ. ID. NO. 32493 | 105-ArgAsnAlaAspPheAlaAlaGluHisGlnArgGluGlyPheAla-119 |
| g572 | |
| AMPHI Regions - AMPHI | |
| SEQ. ID. NO. 32494 | 10-LeuProSerAlaLeuAla-15 |
| SEQ. ID. NO. 32495 | 61-GlnValLeuProArgAspTyrThrAspArgLeuAsn-72 |
| SEQ. ID. NO. 32496 | 94-SerThrPheAspSerIleThrPro-101 |
| SEQ. ID. NO. 32497 | 154-IleHisSerMetValArg-159 |
| SEQ. ID. NO. 32498 | 183-GlyLeuProGluArgIleAspSerGly-191 |
| SEQ. ID. NO. 32499 | 200-LeuSerAlaLeuThr-204 |
| Antigenic Index - Jameson-Wolf | |
| SEQ. ID. NO. 32500 | 18-GlnLysGlyLysThr-22 |
| SEQ. ID. NO. 32501 | 26-AlaAsnLysGluThrLeu-31 |
| SEQ. ID. NO. 32502 | 41-ThrAlaArgAlaAsnGly-46 |
| SEQ. ID. NO. 32503 | 51-ProValAspSerGluHis-56 |
| SEQ. ID. NO. 32504 | 63-LeuProArgAspTyrThrAspArgLeuAsnGluHisGlyIleAsp-77 |
| SEQ. ID. NO. 32505 | 97-AspSerIleThrProGluGlnAlaValLysHisProAsnTrpArgMetGlyArgLysIleSerValAspSer-120 |
| SEQ. ID. NO. 32506 | 122-ThrMetAlaAsnLysGlyLeuGluLeu-130 |
| SEQ. ID. NO. 32507 | 138-AsnCysProProAspLysLeuGluVal-146 |
| SEQ. ID. NO. 32508 | 158-ValArgTyrArgAspGlySerVal-165 |
| SEQ. ID. NO. 32509 | 170-GlyAsnProAspMetArgThr-176 |
| SEQ. ID. NO. 32510 | 184-LeuProGluArgIleAspSerGlyValGlyLysLeuAsp-196 |
| SEQ. ID. NO. 32511 | 205-PheGlnLysProAspPheGlyArg-212 |
| SEQ. ID. NO. 32512 | 224-AsnAlaGlyGlyAla-228 |
| Hydrophilic Regions - Hopp-Woods | |
| SEQ. ID. NO. 32513 | 27-AsnLysGluThrLeu-31 |
| SEQ. ID. NO. 32514 | 41-ThrAlaArgAlaAsnGly-46 |
| SEQ. ID. NO. 32515 | 52-ValAspSerGluHis-56 |
| SEQ. ID. NO. 32516 | 66-AspTyrThrAspArgLeuAsnGluHisGlyIle-76 |
| SEQ. ID. NO. 32517 | 111-ArgMetGlyArgLysIleSerVal-118 |
| SEQ. ID. NO. 32518 | 126-LysGlyLeuGluLeu-130 |
| SEQ. ID. NO. 32519 | 140-ProProAspLysLeuGlu-145 |
| SEQ. ID. NO. 32520 | 158-ValArgTyrArgAspGlySer-164 |
| SEQ. ID. NO. 32521 | 170-GlyAsnProAspMetArgThr-176 |
| SEQ. ID. NO. 32522 | 184-LeuProGluArgIleAspSerGlyValGlyLysLeuAsp-196 |
| SEQ. ID. NO. 32523 | 206-GlnLysProAspPheGly-211 |
| g574 | |
| AMPHI Regions - AMPHI | |
| SEQ. ID. NO. 32524 | 6-ProAsnSerLeuLysLys-11 |
| SEQ. ID. NO. 32525 | 47-LeuLysGlnAlaLysSerIleProSerGlyPheTyrLysSerLeuAspAlaLeuValAspArgAsnSerGlyArgAlaAlaArgGluLeuAlaGlu ValValAsp-81 |
| SEQ. ID. NO. 32526 | 94-GlyLysLeuTyrArgGln-99 |
| SEQ. ID. NO. 32527 | 113-MetLeuAspSerProAspThr-119 |
| SEQ. ID. NO. 32528 | 175-GluLysAlaValGlu-179 |
| SEQ. ID. NO. 32529 | 218-AsnValGlyLysAlaLeuGluAlaAsnLysLysCys-229 |
| SEQ. ID. NO. 32530 | 246-PheProAlaAlaValGluAlaTyrAlaAlaIleGlu-257 |
| SEQ. ID. NO. 32531 | 266-MetValGlyGluLysLeuTyrGluAlaTyrAla-276 |
| SEQ. ID. NO. 32532 | 281-ProGluGluGlyLeuAsnArgLeuThrGlyTyrMetGlnThrPheProGluLeuAspLeu-300 |
| SEQ. ID. NO. 32533 | 332-AsnGlyValTyrArg-336 |
| SEQ. ID. NO. 32534 | 357-ArgSerValIleGlyArgGlnLeuGlnArgSer-367 |
| Antigenic Index - Jameson-Wolf | |
| SEQ. ID. NO. 32535 | 7-AsnSerLeuLysLysAlaAspMetAspAsn-16 |
| SEQ. ID. NO. 32536 | 45-ThrValLeuLysGlnAlaLysSerIleProSerGlyPheTyrLysSerLeuAspAlaLeuValAspArgAsnSerGlyArgAlaAlaArgGluLeuAla GluValValAspGlyArgProGlnSerTyrAsp-88 |
| SEQ. ID. NO. 32537 | 96-LeuTyrArgGlnArgGlyGluAsnAspLysAlaileAsnileHisArgThrMetLeuAspSerProAspThrValGlyGluLysArgAlaArgVal-127 |
| SEQ. ID. NO. 32538 | 135-TyrGlnSerAlaGlyLeuValAspArgAlaGlu-145 |
| SEQ. ID. NO. 32539 | 151-LeuGlnAspGlyGluMetAlaArgGluAlaArgGln-162 |
| SEQ. ID. NO. 32540 | 168-TyrGlnGlnAspArgAspTrpGluLysAlaValGlu-179 |
| SEQ. ID. NO. 32541 | 185-SerHisAspGluGlnThrTyr-191 |
| SEQ. ID. NO. 32542 | 210-SerAsnPheAspAlaAlaArg-216 |
| SEQ. ID. NO. 32543 | 221-LysAlaLeuGluAlaAsnLysLysCysThrArg-231 |
| SEQ. ID. NO. 32544 | 238-AspileGluHisArgGlnGlyAsn-245 |
| SEQ. ID. NO. 32545 | 277-AlaGlnGlyLysProGluGluGlyLeuAsnArgLeuThrGlyTyr-291 |

TABLE 1-continued

| | |
|---|---|
| SEQ. ID. NO. 32546 | 309-LeuLeuLeuLysGlyGluLysGluAlaAla-318 |
| SEQ. ID. NO. 32547 | 323-GluLeuValArgArgLysProAspLeuAsnGly-333 |
| SEQ. ID. NO. 32548 | 341-LysLeuSerAspLeuAspProAlaTrpLysAlaAspAlaAspMetMetArg-357 |
| SEQ. ID. NO. 32549 | 368-ValMetTyrArgCysArgAsnCysHisPheLys-378 |
| SEQ. ID. NO. 32550 | 386-CysProAlaCysAsnLysTrpGlnThrPheThrProAsnLysileGluVal-402 |
| Hydrophilic Regions - Hopp-Woods | |
| SEQ. ID. NO. 32551 | 7-AsnSerLeuLysLysAlaAspMetAspAsn-16 |
| SEQ. ID. NO. 32552 | 45-ThrValLeuLysGlnAlaLysSerIle-53 |
| SEQ. ID. NO. 32553 | 62-AspAlaLeuValAspArgAsnSerGlyArgAlaAlaArgGluLeuAlaGluValValAspGlyArgProGlnSer-86 |
| SEQ. ID. NO. 32554 | 96-LeuTyrArgGlnArgGlyGluAsnAspLysAlaIleAsn-108 |
| SEQ. ID. NO. 32555 | 112-ThrMetLeuAspSerProAspThrValGlyGluLysArgAlaArgVal-127 |
| SEQ. ID. NO. 32556 | 140-LeuValAspArgAlaGlu-145 |
| SEQ. ID. NO. 32557 | 152-GlnAspGlyGluMetAlaArgGluAlaArgGln-162 |
| SEQ. ID. NO. 32558 | 169-GlnGlnAspArgAspTrpGluLysAlaValGlu-179 |
| SEQ. ID. NO. 32559 | 185-SerHisAspGluGlnThrTyr-191 |
| SEQ. ID. NO. 32560 | 211-AsnPheAspAlaAlaArg-216 |
| SEQ. ID. NO. 32561 | 221-LysAlaLeuGluAlaAsnLysLysCysThrArg-231 |
| SEQ. ID. NO. 32562 | 238-AspileGluHisArgGlnGlyAsn-245 |
| SEQ. ID. NO. 32563 | 279-GlyLysProGluGluGlyLeuAsn-286 |
| SEQ. ID. NO. 32564 | 309-LeuLeuLeuLysGlyGluLysGluAlaAla-318 |
| SEQ. ID. NO. 32565 | 323-GluLeuValArgArgLysProAspLeu-331 |
| SEQ. ID. NO. 32566 | 341-LysLeuSerAspLeuAspPro-347 |
| SEQ. ID. NO. 32567 | 349-TrpLysAlaAspAlaAspMetMetArg-357 |
| SEQ. ID. NO. 32568 | 368-ValMetTyrArgCysArgAsnCysHis-376 |
| SEQ. ID. NO. 32569 | 398-AsnLysileGluVal-402 |
| g575 | |
| AMPHI Regions - AMPHI | |
| SEQ. ID. NO. 32570 | 31-ProValArgGlnValArg-36 |
| SEQ. ID. NO. 32571 | 93-TrpArgSerValAlaGluAlaGlyValSer-102 |
| SEQ. ID. NO. 32572 | 104-ThrAlaGlyLeuGlySerGlyArgThrAlaGlyPheSerAlaPheAlaSerGlyAla-122 |
| SEQ. ID. NO. 32573 | 124-ThrPheAlaSerGlyPheSerThrGly-132 |
| SEQ. ID. NO. 32574 | 149-GlySerAspGlyMetAspAlaValSerAlaLeu-159 |
| Antigenic Index - Jameson-Wolf | |
| SEQ. ID. NO. 32575 | 3-CysLeuArgArgGlnAlaAlaArgCysThrAsnArgArgThrAspArgGlnThrVal-21 |
| SEQ. ID. NO. 32576 | 27-LeuArgGlnLysProValArgGlnValArgGlnArgValArgArg-41 |
| SEQ. ID. NO. 32577 | 49-GlnGlnValArgLysArgCysTyrArgPheArgArgSerAlaCysArgTrpGlnLysArgArgLeuLeuGlyGlyAlaAspSerAlaAlaVal-79 |
| SEQ. ID. NO. 32578 | 89-ThrGlyProGlyTrp-93 |
| SEQ. ID. NO. 32579 | 100-GlyValSerAspThrAlaGlyLeuGlySerGlyArgThrAla-113 |
| SEQ. ID. NO. 32580 | 129-PheSerThrGlyPheSerThr-135 |
| SEQ. ID. NO. 32581 | 147-LeuAspGlySerAspGlyMetAsp-154 |
| Hydrophilic Regions - Hopp-Woods | |
| SEQ. ID. NO. 32582 | 3-CysLeuArgArgGlnAlaAlaArgCysThrAsnArgArgThrAspArgGlnThrVal-21 |
| SEQ. ID. NO. 32583 | 27-LeuArgGlnLysProValArgGlnValArgGlnArgValArgArg-41 |
| SEQ. ID. NO. 32584 | 50-GlnValArgLysArgCysTyrArgPheArgArgSerAlaCysArgTrpGlnLysArgArgLeuLeuGly-72 |
| SEQ. ID. NO. 32585 | 74-AlaAspSerAlaAlaVal-79 |
| SEQ. ID. NO. 32586 | 148-AspGlySerAspGlyMetAsp-154 |
| g576-1 | |
| AMPHI Regions - AMPHI | |
| SEQ. ID. NO. 32587 | 31-AlaSerGluProAlaAlaAla-37 |
| SEQ. ID. NO. 32588 | 46-SerIleGlySerThr-50 |
| SEQ. ID. NO. 32589 | 63-GlyArgSerLeuLysGlnMetLys-70 |
| SEQ. ID. NO. 32590 | 82-ThrAspAlaMetGln-86 |
| SEQ. ID. NO. 32591 | 102-GlnGluValMetMetLysPheLeuGlnGluGlnGlnAlaLysAlaValGluLysHis-120 |
| SEQ. ID. NO. 32592 | 140-AlaLysAspGlyValLysThrThr-147 |
| SEQ. ID. NO. 32593 | 200-GlnValIleProGlyTrpThrGluGlyValArgLeuLeuLysGluGly-215 |
| Antigenic Index - Jameson-Wolf | |
| SEQ. ID. NO. 32594 | 20-AlaCysGlyLysLysGluAlaAlaPro-28 |
| SEQ. ID. NO. 32595 | 30-SerAlaSerGluProAlaAla-36 |
| SEQ. ID. NO. 32596 | 40-AlaGlnGlyAspThrSerSerIleGlySerThrMetGlnGln-53 |
| SEQ. ID. NO. 32597 | 61-AspIleGlyArgSerLeuLysGlnMetLysGluGlnGlyAlaGluIleAspLeu-78 |
| SEQ. ID. NO. 32598 | 89-TyrAspGlyLysGluIleLysMetThrGluGluGlnAlaGln-102 |
| SEQ. ID. NO. 32599 | 109-LeuGlnGluGlnGlnAlaLysAlaValGluLysHisLysAlaAspAlaLysAlaAsnLysGluLysGlyGluAlaPheLeuLysGluAsnAlaAla LysAspGlyValLysThrThrAlaSerGlyLeu-151 |
| SEQ. ID. NO. 32600 | 154-LysIleThrLysGlnGlyGluGlyLysGlnProThrLysAspAspIleVal-170 |
| SEQ. ID. NO. 32601 | 173-GluTyrGluGlyArgLeuIleAsp-180 |
| SEQ. ID. NO. 32602 | 183-ValPheAspSerSerLysAlaAsnGlyGlyPro-193 |
| SEQ. ID. NO. 32603 | 203-ProGlyTrpThrGlu-207 |
| SEQ. ID. NO. 32604 | 209-ValArgLeuLeuLysGluGlyGlyGlu-217 |
| SEQ. ID. NO. 32605 | 224-SerAsnLeuAlaTyrArgGluGlnGlyAlaGlyGluLysIleGlyPro-239 |
| SEQ. ID. NO. 32606 | 253-GlyAlaProGluAsnAlaProAlaLysGlnProAspGlnValAspIleLysLysValAsn-272 |
| Hydrophilic Regions - Hopp-Woods | |
| SEQ. ID. NO. 32607 | 21-CysGlyLysLysGluAlaAlaPro-28 |
| SEQ. ID. NO. 32608 | 30-SerAlaSerGluProAlaAla-36 |
| SEQ. ID. NO. 32609 | 40-AlaGlnGlyAspThrSerSer-46 |
| SEQ. ID. NO. 32610 | 61-AspIleGlyArgSerLeuLysGlnMetLysGluGlnGlyAlaGluIleAspLeu-78 |
| SEQ. ID. NO. 32611 | 89-TyrAspGlyLysGluIleLysMetThrGluGluGlnAlaGln-102 |
| SEQ. ID. NO. 32612 | 112-GlnGlnAlaLysAlaValGluLysHisLysAlaAspAlaLysAlaAsnLysGluLysGlyGluAlaPheLeuLysGluAsnAlaAlaLysAspGly ValLysThrThrAla-148 |
| SEQ. ID. NO. 32613 | 155-IleThrLysGlnGlyGluGlyLysGlnProThrLysAspAspIleVal-170 |
| SEQ. ID. NO. 32614 | 173-GluTyrGluGlyArgLeuIleAsp-180 |

TABLE 1-continued

| | |
|---|---|
| SEQ. ID. NO. 32615 | 185-AspSerSerLysAlaAsnGly-191 |
| SEQ. ID. NO. 32616 | 209-ValArgLeuLeuLysGluGlyGlyGlu-217 |
| SEQ. ID. NO. 32617 | 227-AlaTyrArgGluGlnGlyAlaGlyGluLysIleGlyPro-239 |
| SEQ. ID. NO. 32618 | 253-GlyAlaProGluAsnAlaProAlaLysGlnProAspGlnValAspIleLysLysValAsn-272 |
| g577 | |
| AMPHI Regions - AMPHI | |
| SEQ. ID. NO. 32619 | 8-GlyLysIleValGlyAsnArgIleLeuArgMetProSerGluHis-22 |
| SEQ. ID. NO. 32620 | 26-PheTyrProLysProCysLysSerPheLysLeuThr-37 |
| SEQ. ID. NO. 32621 | 62-ThrValIleLysIleIle-67 |
| SEQ. ID. NO. 32622 | 104-AlaPheValValGlyIle-109 |
| SEQ. ID. NO. 32623 | 112-GlyMetPheAlaLeuPheGlyArg-119 |
| Antigenic Index - Jameson-Wolf | |
| SEQ. ID. NO. 32624 | 1-MetGluArgSerGlyVal-6 |
| SEQ. ID. NO. 32625 | 14-ArgIleLeuArgMetProSerGluHis-22 |
| SEQ. ID. NO. 32626 | 28-ProLysProCysLysSerPheLysLeu-36 |
| SEQ. ID. NO. 32627 | 43-ValArgSerCysProCys-48 |
| SEQ. ID. NO. 32628 | 121-LeuSerLeuArgGlyGluAsnSerArgLeuArgAlaGluValLysLysSerAlaArgLeuSerGlyGlnLysLeuThrAla-147 |
| SEQ. ID. NO. 32629 | 152-AsnAlaAlaGluSerAlaLysGlnPro-160 |
| Hydrophilic Regions - Hopp-Woods | |
| SEQ. ID. NO. 32630 | 1-MetGluArgSerGlyVal-6 |
| SEQ. ID. NO. 32631 | 14-ArgIleLeuArgMetProSerGluHis-22 |
| SEQ. ID. NO. 32632 | 29-LysProCysLysSerPheLys-35 |
| SEQ. ID. NO. 32633 | 121-LeuSerLeuArgGlyGluAsnSerArgLeuArgAlaGluValLysLysSerAlaArgLeuSerGly-142 |
| SEQ. ID. NO. 32634 | 152-AsnAlaAlaGluSerAlaLysGlnPro-160 |
| g578 | |
| AMPHI Regions - AMPHI | |
| SEQ. ID. NO. 32635 | 10-PheAlaAspPhePheLysAspPheAlaProGlnPheGlyGlyPheGlnAsn-26 |
| SEQ. ID. NO. 32636 | 34-AspPhePheAlaAlaPheLeuGlyGlyLeuGluGlyHisValGlyAsp-49 |
| SEQ. ID. NO. 32637 | 58-PheHisGlyValValAlaPhe-64 |
| SEQ. ID. NO. 32638 | 71-AsnThrAspAlaAlaArgPhe-77 |
| Antigenic Index - Jameson-Wolf | |
| SEQ. ID. NO. 32639 | 13-PhePheLysAspPheAlaProGlnPheGlyGly-23 |
| SEQ. ID. NO. 32640 | 43-LeuGluGlyHisValGlyAspAlaAla-51 |
| SEQ. ID. NO. 32641 | 71-AsnThrAspAlaAlaArgPheAla-78 |
| SEQ. ID. NO. 32642 | 88-HisAsnGlnAsnIleGlnThrGlyAsnAspPheArgLeuGluArgGlyGlyValGly-106 |
| Hydrophilic Regions - Hopp-Woods | |
| SEQ. ID. NO. 32643 | 73-AspAlaAlaArgPheAla-78 |
| SEQ. ID. NO. 32644 | 96-AsnAspPheArgLeuGluArgGlyGlyVal-105 |
| g579 | |
| AMPHI Regions - AMPHI | |
| SEQ. ID. NO. 32645 | 6-PheAspPheLeuHisLeuIleSerValSerGlyTrpGlyHisLeuAlaGlu-22 |
| SEQ. ID. NO. 32646 | 49-ValAlaValMetArg-53 |
| SEQ. ID. NO. 32647 | 66-IleSerPheLeuCysAsn-71 |
| SEQ. ID. NO. 32648 | 115-LeuSerAsnPheAla-119 |
| SEQ. ID. NO. 32649 | 129-ProPheLysValGlyAspPheIleArgValGlyGlyPheGluGlyTyrValArgGluIleLys-149 |
| SEQ. ID. NO. 32650 | 206-LeuLysAlaAlaAlaGlu-211 |
| SEQ. ID. NO. 32651 | 258-GlnValValGluAsnLeuArg-264 |
| Antigenic Index - Jameson-Wolf | |
| SEQ. ID. NO. 32652 | 110-SerLeuLysAspGlnLeuSer-116 |
| SEQ. ID. NO. 32653 | 128-ArgProPheLysVal-132 |
| SEQ. ID. NO. 32654 | 136-IleArgValGlyGlyPheGluGlyTyrValArgGluIleLysMet-150 |
| SEQ. ID. NO. 32655 | 154-SerLeuArgThrThrAspAsnGluGluValValLeu-165 |
| SEQ. ID. NO. 32656 | 175-IleValAsnArgSerSerLeuProLeu-183 |
| SEQ. ID. NO. 32657 | 198-LeuLysValAlaLysGluAlaValLeu-206 |
| SEQ. ID. NO. 32658 | 216-ValGlnAsnGluGluArgGlnPro-223 |
| SEQ. ID. NO. 32659 | 231-GlyAspAsnAlaIle-235 |
| SEQ. ID. NO. 32660 | 244-AsnGluAlaAspArgTrpThrLeu-251 |
| SEQ. ID. NO. 32661 | 253-CysAspLeuAsnGluGlnValValGluAsnLeuArgLysValAsn-267 |
| SEQ. ID. NO. 32662 | 271-ProPheProGlnArgAspIleHis-278 |
| Hydrophilic Regions - Hopp-Woods | |
| SEQ. ID. NO. 32663 | 110-SerLeuLysAspGlnLeu-115 |
| SEQ. ID. NO. 32664 | 144-TyrValArgGluIleLysMet-150 |
| SEQ. ID. NO. 32665 | 155-LeuArgThrThrAspAsnGluGluValVal-164 |
| SEQ. ID. NO. 32666 | 198-LeuLysValAlaLysGluAlaValLeu-206 |
| SEQ. ID. NO. 32667 | 216-ValGlnAsnGluGluArgGlnPro-223 |
| SEQ. ID. NO. 32668 | 244-AsnGluAlaAspArgTrp-249 |
| SEQ. ID. NO. 32669 | 254-AspLeuAsnGluGlnValValGluAsnLeuArgLysValAsn-267 |
| SEQ. ID. NO. 32670 | 273-ProGlnArgAspIleHis-278 |
| g580 | |
| AMPHI Regions - AMPHI | |
| SEQ. ID. NO. 32671 | 47-ProValSerAlaSerLys-52 |
| SEQ. ID. NO. 32672 | 54-SerLeuValLysProLeuSerGlnProLeuAla-64 |
| Antigenic Index - Jameson-Wolf | |
| SEQ. ID. NO. 32673 | 1-MetAspSerProLysValGlyCysGly-9 |
| SEQ. ID. NO. 32674 | 48-ValSerAlaSerLys-52 |
| SEQ. ID. NO. 32675 | 66-AlaArgProGluAlaAlaHis-72 |
| SEQ. ID. NO. 32676 | 81-ArgProAspAlaLeuAlaAspAsnSerValSerProThrHisAlaThrSerGlyGluVal-100 |
| Hydrophilic Regions - Hopp-Woods | |
| SEQ. ID. NO. 32677 | 1-MetAspSerProLysVal-6 |
| SEQ. ID. NO. 32678 | 66-AlaArgProGluAlaAlaHis-72 |

TABLE 1-continued

SEQ. ID. NO. 32679 81-ArgProAspAlaLeuAla-86
SEQ. ID. NO. 32680 96-ThrSerGlyGluVal-100
g581
AMPHI Regions - AMPHI
SEQ. ID. NO. 32681 43-SerHisPheIleSerLeu-48
SEQ. ID. NO. 32682 56-ArgGluCysPheValGlyPhe-62
SEQ. ID. NO. 32683 76-AlaThrAlaPheGlyArgIleAsnGln-84
SEQ. ID. NO. 32684 90-GlnIleHisGlyPheLeuThrThrPheAlaGlyArgValAlaAsnProThrHisCysGlnSerGlnThr-112
Antigenic Index - Jameson-Wolf
SEQ. ID. NO. 32685 8-GlyGlnThrGlyIleGluGlnAsnThrPheCysArgArgGlyPheThrArgIleAspMetGlyGlyAsnThrAspVal-33
SEQ. ID. NO. 32686 35-ValGlnAlaAspArgGlyLeuThrSer-43
SEQ. ID. NO. 32687 49-SerLysLeuGluThrGluValArgGluCysPhe-59
SEQ. ID. NO. 32688 79-PheGlyArgIleAsnGln-84
SEQ. ID. NO. 32689 98-PheAlaGlyArgValAlaAsnProThrHisCysGlnSerGlnThrAla-113
Hydrophilic Regions - Hopp-Woods
SEQ. ID. NO. 32690 35-ValGlnAlaAspArgGlyLeu-41
SEQ. ID. NO. 32691 49-SerLysLeuGluThrGluValArgGlu-57
g582
AMPHI Regions - AMPHI
SEQ. ID. NO. 32692 27-ThrAspAsnValThrArgLeuAla-34
SEQ. ID. NO. 32693 65-ValArgSerSerLeu-69
SEQ. ID. NO. 32694 91-GlyGluThrAlaAspIleTyrThrProLeuSer-101
SEQ. ID. NO. 32695 139-SerSerProThrArg-143
SEQ. ID. NO. 32696 169-IleAlaGluAsnLeuPhe-174
SEQ. ID. NO. 32697 246-SerArgSerTrpAsnArgIleTyrAlaMet-255
SEQ. ID. NO. 32698 263-LeuThrValIleProArgValTrpValArgAlaPheAspGlnSer-277
SEQ. ID. NO. 32699 286-IleAlaAspTyrMetGlyTyr-292
SEQ. ID. NO. 32700 334-LeuLysGlyValValArgGlyPheHisGlyTyrGlyGlu-346
Antigenic Index - Jameson-Wolf
SEQ. ID. NO. 32701 26-LeuThrAspAsnValThr-31
SEQ. ID. NO. 32702 34-AlaCysTyrAspArg-38
SEQ. ID. NO. 32703 44-LeuProSerSerAlaGlyGlnGluGlyGlnGluSerLysAla-57
SEQ. ID. NO. 32704 63-GluThrValArgSerSerLeuAspLysGlyGluAla-74
SEQ. ID. NO. 32705 77-ValValGluLysGlyGlyAspAlaLeuProAlaAspSerAlaGlyGluThrAlaAsp-95
SEQ. ID. NO. 32706 105-AspLeuAspLysAsnAspLeuArgGly-113
SEQ. ID. NO. 32707 115-LeuGlyValArgGluHisAsnProMetTyr-124
SEQ. ID. NO. 32708 130-TyrAsnAsnSerProAsnTyrAlaProSerSerProThrArgGlyThrThrValGlnGluLysPheGlyGlnGlnLysArgAlaGluThrLys Leu-161
SEQ. ID. NO. 32709 165-PheLysSerLysIleAla-170
SEQ. ID. NO. 32710 173-LeuPheLysThrArgAla-178
SEQ. ID. NO. 32711 183-GlyTyrThrGlnArgSerAspTrpGlnIleTyrAsnGlnGlyArgLysSerAlaProPheArgAsnThrAspTyrLysPro-209
SEQ. ID. NO. 32712 216-ProValLysAlaAspLeuProPheGlyGlyArgLeuArgMet-229
SEQ. ID. NO. 32713 237-GlnSerAsnGlyGlnSerArgProGluSerArgSerTrpAsn-250
SEQ. ID. NO. 32714 273-AlaPheAspGlnSerGlyAspLysAsnAspAsnProAspIleAlaAsp-288
SEQ. ID. NO. 32715 291-GlyTyrGlyAspValLysLeuGlnTyrArgLeuAsnAspArgGlnAsnVal-307
SEQ. ID. NO. 32716 312-ArgTyrAsnProLysThrGlyTyr-319
SEQ. ID. NO. 32717 330-IleLysGlyLysLeuLysGlyValVal-338
SEQ. ID. NO. 32718 342-HisGlyTyrGlyGluSerLeuIleAspTyrAsnHisLysGlnAsnGly-357
SEQ. ID. NO. 32719 365-AsnAspTrpAspGlyIle-370
Hydrophilic Regions - Hopp-Woods
SEQ. ID. NO. 32720 48-AlaGlyGlnGluGlyGlnGluSerLysAla-57
SEQ. ID. NO. 32721 63-GluThrValArgSerSerLeuAspLysGlyGluAla-74
SEQ. ID. NO. 32722 79-GluLysGlyGlyAspAlaLeuPro-86
SEQ. ID. NO. 32723 88-AspSerAlaGlyGluThrAlaAsp-95
SEQ. ID. NO. 32724 105-AspLeuAspLysAsnAspLeuArgGly-113
SEQ. ID. NO. 32725 115-LeuGlyValArgGluHisAsn-121
SEQ. ID. NO. 32726 140-SerProThrArgGlyThrThrValGlnGluLysPheGlyGlnGlnLysArgAlaGluThrLysLeu-161
SEQ. ID. NO. 32727 165-PheLysSerLysIleAla-170
SEQ. ID. NO. 32728 173-LeuPheLysThrArgAla-178
SEQ. ID. NO. 32729 195-GlnGlyArgLysSerAlaProPheArgAsnThrAspTyrLysPro-209
SEQ. ID. NO. 32730 225-GlyArgLeuArgMet-229
SEQ. ID. NO. 32731 239-AsnGlyGlnSerArgProGluSerArgSerTrp-249
SEQ. ID. NO. 32732 274-PheAspGlnSerGlyAspLysAsnAspAsnProAspIleAlaAsp-288
SEQ. ID. NO. 32733 293-GlyAspValLysLeu-297
SEQ. ID. NO. 32734 299-TyrArgLeuAsnAspArgGlnAsn-306
SEQ. ID. NO. 32735 332-GlyLysLeuLysGlyValVal-338
SEQ. ID. NO. 32736 352-AsnHisLysGlnAsn-356
g583
AMPHI Regions - AMPHI
SEQ. ID. NO. 32737 11-HisLeuAlaPheCysAlaPheCysGlyIle-20
SEQ. ID. NO. 32738 28-ArgLeuHisAsnArgMetTyrAsnAlaAlaAlaAlaArg-40
SEQ. ID. NO. 32739 58-ValThrAspAlaGln-62
SEQ. ID. NO. 32740 66-SerLysAsnGlyAspLysGlnIle-73
SEQ. ID. NO. 32741 75-AspThrHisProGlnPro-80
SEQ. ID. NO. 32742 117-GlyTyrAlaGlyTyrCysAspGln-124
SEQ. ID. NO. 32743 141-AsnGlyGlyAsnHisThrAsp-147
SEQ. ID. NO. 32744 162-GlyTyrGlyGlnCysGlnAsnGlnGlyAla-171
Antigenic Index - Jameson-Wolf
SEQ. ID. NO. 32745 24-ThrAlaGlyAsnArgLeuHisAsnArgMetTyr-34
SEQ. ID. NO. 32746 41-GlyIleGlyArgGlyAsnGlySerGlnGlnGlnPheGlyLysSerGluThrValThrAspAlaGlnArgPheSerSerLysAsnGlyAspLysGln TABLE 1-continued

| | |
|---|---|
| | IleSerAspThrHisProGlnProCysPheGluGlnThrAlaArgAsnHisAsnCysAspGlyAsnGlnProAsnGlnArgIleGlyGluArgThrGln ArgIleAlaHisArgArgAlaArgPhe-114 |
| SEQ. ID. NO. 32747 | 117-GlyTyrAlaGlyTyrCysAspGlnProAspGlyAsnAsnArgGlnArgAlaGlnArgHisAsnLeuAlaAspAsnGlyGlyAsnHisThr AspLysHisSerGlnGlnArgProSerLeuArgLeuAspProValGlyTyrGlyGlnCysGlnAsnGlnGlyAlaGlnTyrCysGlyAsnGlyGlu GlyTyrArgPhe-182 |
| SEQ. ID. NO. 32748 | 190-AspLeuArgLysLysAspArgProGluLysSerGluLys-202 |
| Hydrophilic Regions - Hopp-Woods | |
| SEQ. ID. NO. 32749 | 27-AsnArgLeuHisAsn-31 |
| SEQ. ID. NO. 32750 | 41-GlyIleGlyArgGlyAsnGlySer-48 |
| SEQ. ID. NO. 32751 | 51-GlnPheGlyLysSerGluThrValThrAspAlaGlnArgPheSerSerLysAsnGlyAspLysGlnIleSerAspThrHisPro-78 |
| SEQ. ID. NO. 32752 | 84-GlnThrAlaArgAsnHisAsnCysAspGlyAsnGlnProAsnGlnArgIleGlyGluArgThrGlnArgIleAlaHisArgArgAlaArgPhe-114 |
| SEQ. ID. NO. 32753 | 123-AspGlnProAspGlyAsnAsnArgGlnArgAlaGlnArgHisAsnLeuAlaAspAsnGlyGlyAsnHisThrAspLysHisSerGlnGln ArgProSerLeuArgLeuAspPro-160 |
| SEQ. ID. NO. 32754 | 178-GluGlyTyrArgPhe-182 |
| SEQ. ID. NO. 32755 | 190-AspLeuArgLysLysAspArgProGluLysSerGluLys-202 |
| g584 | |
| AMPHI Regions - AMPHI | |
| SEQ. ID. NO. 32756 | 28-GluPheSerGluSerAlaGly-34 |
| SEQ. ID. NO. 32757 | 60-AlaGluPheValLysLysPheAsnAsnPheThrArgLys-72 |
| SEQ. ID. NO. 32758 | 116-PheAspAlaLeuAsnArgPheIleAlaAspVal-126 |
| SEQ. ID. NO. 32759 | 148-IleAspGlnValSerLysAsp-154 |
| SEQ. ID. NO. 32760 | 166-LeuAlaGlyValLeuGly-171 |
| Antigenic Index - Jameson-Wolf | |
| SEQ. ID. NO. 32761 | 37-ValAlaGlnAspThrMetSer-43 |
| SEQ. ID. NO. 32762 | 50-AlaGluGlyArgAspLysAsnAlaVal-58 |
| SEQ. ID. NO. 32763 | 61-GluPheValLysLysPheAsnAsnPheThrArgLysSerLysAsnGlySerPheLysThrGluLeuValSerArgSerAlaMetProArgTyrGln TyrThrAsnGlyArgArgIleGlnThrGlyTrpGluGluArgAlaGluPheLysAlaGluGlyArgAspPheAspAla-118 |
| SEQ. ID. NO. 32764 | 126-ValGlnThrAspAlaSerLeuGluAspThrAspPheSerValSerArgGluArgArgAsnGluValIleAspGlnValSerLysAspAlaVal Leu-157 |
| SEQ. ID. NO. 32765 | 159-PheLysAlaArgAlaGluLysLeuAla-167 |
| SEQ. ID. NO. 32766 | 189-IleAlaGlyAspGlyAlaValArgAlaLysMetLeuArg-201 |
| SEQ. ID. NO. 32767 | 210-AsnMetLysGlyThrAspSerAlaAlaProGlyValGluGluIleSer-225 |
| Hydrophilic Regions - Hopp-Woods | |
| SEQ. ID. NO. 32768 | 50-AlaGluGlyArgAspLysAsnAlaVal-58 |
| SEQ. ID. NO. 32769 | 67-AsnAsnPheThrArgLysSerLysAsnGlySerPheLysThrGluLeuValSer-84 |
| SEQ. ID. NO. 32770 | 95-AsnGlyArgArgIleGlnThrGlyTrpGluGluArgAlaGluPheLysAlaGluGlyArgAspPheAspAla-118 |
| SEQ. ID. NO. 32771 | 130-AlaSerLeuGluAspThrAspPheSerValSerArgGluArgArgAsnGluValIleAspGlnValSerLysAspAlaValLeu-157 |
| SEQ. ID. NO. 32772 | 159-PheLysAlaArgAlaGluLysLeuAla-167 |
| SEQ. ID. NO. 32773 | 193-GlyAlaValArgAlaLysMetLeuArg-201 |
| SEQ. ID. NO. 32774 | 210-AsnMetLysGlyThrAspSerAlaAlaProGlyValGluGluIleSer-225 |
| g585 | |
| AMPHI Regions - AMPHI | |
| SEQ. ID. NO. 32775 | 6-ArgIlePheAlaThrPheCysAlaValIleValCys-17 |
| SEQ. ID. NO. 32776 | 46-ThrThrLeuMetGlySerIleIleSer-54 |
| SEQ. ID. NO. 32777 | 65-ArgGluIleLeuThrGluTrpLys-72 |
| SEQ. ID. NO. 32778 | 93-AsnArgTyrIleAsp-97 |
| SEQ. ID. NO. 32779 | 136-AspAsnHisGlnAlaGlnArg-142 |
| SEQ. ID. NO. 32780 | 153-ProLeuAlaProIleTrp-158 |
| SEQ. ID. NO. 32781 | 178-LeuAlaGlyAsnIleAlaLysProIleArgIleLeuGlyAsnGlyMetAspArgValAlaGluArgGlu-200 |
| Antigenic Index - Jameson-Wolf | |
| SEQ. ID. NO. 32782 | 36-AsnGlnPheAsnGlnArgArgThrIleGlu-45 |
| SEQ. ID. NO. 32783 | 56-PheLysThrArgGlyAspAsnGlyAlaArgGluIleLeuThrGluTrpLysAsnSerProValSer-77 |
| SEQ. ID. NO. 32784 | 84-GlnGlyAspGluLysLysAspIleLeu-92 |
| SEQ. ID. NO. 32785 | 99-TyrThrIleGluArgAlaArgLeu-106 |
| SEQ. ID. NO. 32786 | 119-IleGluTyrAspArgPheGlyGlu-126 |
| SEQ. ID. NO. 32787 | 134-GlyTrpAspAsnHisGlnAlaGlnArgLeuProSerPro-146 |
| SEQ. ID. NO. 32788 | 189-LeuGlyAsnGlyMetAspArgValAlaGluArgGluLeuGluAspArgValCysGlnGlnValArgAspArgAspAspGluLeuAlaAsp-218 |
| SEQ. ID. NO. 32789 | 225-ThrMetValGluLysLeuGlu-231 |
| Hydrophilic Regions - Hopp-Woods | |
| SEQ. ID. NO. 32790 | 37-GlnPheAsnGlnArgArgThrIleGlu-45 |
| SEQ. ID. NO. 32791 | 56-PheLysThrArgGlyAspAsnGlyAlaArgGluIleLeuThr-69 |
| SEQ. ID. NO. 32792 | 84-GlnGlyAspGluLysLysAspIleLeu-92 |
| SEQ. ID. NO. 32793 | 100-ThrIleGluArgAlaArgLeu-106 |
| SEQ. ID. NO. 32794 | 119-IleGluTyrAspArgPheGlyGlu-126 |
| SEQ. ID. NO. 32795 | 139-GlnAlaGlnArgLeu-143 |
| SEQ. ID. NO. 32796 | 192-GlyMetAspArgValAlaGluArgGluLeuGluAspArgValCysGlnGlnValArgAspArgAspAspGluLeuAlaAsp-218 |
| SEQ. ID. NO. 32797 | 225-ThrMetValGluLysLeuGlu-231 |
| g586 | |
| AMPHI Regions - AMPHI | |
| SEQ. ID. NO. 32798 | 12-AspAsnPheLysTyrPheTrpLysThr-20 |
| SEQ. ID. NO. 32799 | 30-IleLeuAlaAlaLeuGly-35 |
| SEQ. ID. NO. 32800 | 56-ValLeuAlaAsnIleValGluLysAlaGlnAsnLysAlaPro-69 |
| SEQ. ID. NO. 32801 | 80-LeuGlnGlnSerTyrProHisSerIleSer-89 |
| SEQ. ID. NO. 32802 | 177-SerGlnGluAlaLeuLysAsnTyrGlyGlnAlaLeuGluLysMetProGlnAspSerValGlyArg-198 |
| Antigenic Index - Jameson-Wolf | |
| SEQ. ID. NO. 32803 | 4-HisLeuGluGluGlnGlnGluLeuAspAsn-13 |
| SEQ. ID. NO. 32804 | 43-GlnAsnArgAlaAlaSerGlnAsnGlnGluAla-53 |
| SEQ. ID. NO. 32805 | 60-IleValGluLysAlaGlnAsnLysAlaProGlnSerGluIleAsnAlaGluLeuSerLysLeuGlnGln-82 |
| SEQ. ID. NO. 32806 | 100-ThrGluPheAspAlaGlnArgTyrAspValAlaGluGly-112 |
| SEQ. ID. NO. 32807 | 118-LeuSerAsnGlnLysAspSerLeu-125 |

TABLE 1-continued

| | |
|---|---|
| SEQ. ID. NO. 32808 | 140-GlnGlnLysLysTyrAspAla-146 |
| SEQ. ID. NO. 32809 | 153-ThrProValGluAlaAspPhe-159 |
| SEQ. ID. NO. 32810 | 164-MetGluThrLysGlyAspVal-170 |
| SEQ. ID. NO. 32811 | 172-AlaAlaGlnGluLysSerGlnGluAlaLeuLysAsnTyrGlyGlnAlaLeuGluLysMetProGlnAspSerValGlyArgGluLeuLeu-201 |
| SEQ. ID. NO. 32812 | 204-LysLeuAspSerLeuLys-209 |
| Hydrophilic Regions - Hopp-Woods | |
| SEQ. ID. NO. 32813 | 4-HisLeuGluGluGlnGlnGluLeuAspAsn-13 |
| SEQ. ID. NO. 32814 | 45-ArgAlaAlaSerGlnAsnGlnGluAla-53 |
| SEQ. ID. NO. 32815 | 60-IleValGluLysAlaGlnAsnLysAlaProGlnSerGluIleAsnAlaGluLeuSerLysLeu-80 |
| SEQ. ID. NO. 32816 | 100-ThrGluPheAspAlaGlnArgTyrAspValAlaGluGly-112 |
| SEQ. ID. NO. 32817 | 120-AsnGlnLysAspSerLeu-125 |
| SEQ. ID. NO. 32818 | 140-GlnGlnLysLysTyrAspAla-146 |
| SEQ. ID. NO. 32819 | 153-ThrProValGluAlaAspPhe-159 |
| SEQ. ID. NO. 32820 | 164-MetGluThrLysGlyAspVal-170 |
| SEQ. ID. NO. 32821 | 172-AlaAlaGlnGluLysSerGlnGluAlaLeuLys-182 |
| SEQ. ID. NO. 32822 | 187-AlaLeuGluLysMetProGlnAspSerValGlyArgGluLeuLeu-201 |
| SEQ. ID. NO. 32823 | 204-LysLeuAspSerLeuLys-209 |
| g587 | |
| AMPHI Regions - AMPHI | |
| SEQ. ID. NO. 32824 | 6-LeuProAlaLeuProAlaIleLeuProLeuSerAla-17 |
| SEQ. ID. NO. 32825 | 122-LysArgMetSerAspIleSerAlaGlyIleSerHis-133 |
| Antigenic Index - Jameson-Wolf | |
| SEQ. ID. NO. 32826 | 27-AspIleMetThrAspLysGlyLysTrpLysLeuGluThr-39 |
| SEQ. ID. NO. 32827 | 45-AsnSerGluAsnSerArgAla-51 |
| SEQ. ID. NO. 32828 | 71-ThrGluIleGlnGluAsnGlySerAsnThr-80 |
| SEQ. ID. NO. 32829 | 95-GlyAsnThrAspIleTyrGlySerGlySer-104 |
| SEQ. ID. NO. 32830 | 108-HisGluGluArgLysLeuAspGlyAsnGlyLysThrArgAsnLysArgMetSerAspIle-127 |
| SEQ. ID. NO. 32831 | 135-PheLeuLysAspGlyLysAsnProAla-143 |
| SEQ. ID. NO. 32832 | 151-ThrValTyrGluLysSerArgAsnLysAlaSerLeuIleLysLysArgGlyLeuCys-169 |
| Hydrophilic Regions - Hopp-Woods | |
| SEQ. ID. NO. 32833 | 27-AspIleMetThrAspLysGlyLysTrpLysLeu-37 |
| SEQ. ID. NO. 32834 | 47-GluAsnSerArgAla-51 |
| SEQ. ID. NO. 32835 | 72-GluIleGlnGluAsnGlySerAsn-79 |
| SEQ. ID. NO. 32836 | 108-HisGluGluArgLysLeuAspGlyAsnGlyLysThrArgAsnLysArgMetSerAspIle-127 |
| SEQ. ID. NO. 32837 | 135-PheLeuLysAspGlyLysAsn-141 |
| SEQ. ID. NO. 32838 | 151-ThrValTyrGluLysSerArgAsnLysAlaSerLeuIleLysLysArgGlyLeu-168 |
| g588 | |
| AMPHI Regions - AMPHI | |
| SEQ. ID. NO. 32839 | 55-ArgGlyTyrThrGlySer-60 |
| Antigenic Index - Jameson-Wolf | |
| SEQ. ID. NO. 32840 | 24-SerProTyrGlnGluThrGlyCysThrTyrGluGlyGlyIleGlyLysAspGlyLeuProSerGlyLysGlyIleTrpArgCysArgAspGlyArgGly TyrThrGlySerPheLysAsnGlyLysPheAspGlyGlnGly-70 |
| SEQ. ID. NO. 32841 | 85-PheAsnSerAspSerThrLysPheArgAsn-94 |
| SEQ. ID. NO. 32842 | 105-LeuAlaHisGlyArgPheAlaAlaSerGlnAsnGlyGluThr-118 |
| SEQ. ID. NO. 32843 | 124-MetArgThrArgHisAsp-129 |
| Hydrophilic Regions - Hopp-Woods | |
| SEQ. ID. NO. 32844 | 36-GlyIleGlyLysAspGlyLeuProSer-44 |
| SEQ. ID. NO. 32845 | 49-TrpArgCysArgAspGlyArgGlyTyr-57 |
| SEQ. ID. NO. 32846 | 61-PheLysAsnGlyLysPheAspGly-68 |
| SEQ. ID. NO. 32847 | 85-PheAsnSerAspSerThrLysPheArgAsn-94 |
| SEQ. ID. NO. 32848 | 124-MetArgThrArgHisAsp-129 |
| g589 | |
| AMPHI Regions - AMPHI | |
| SEQ. ID. NO. 32849 | 18-AlaSerArgIleGluLysValLeu-25 |
| SEQ. ID. NO. 32850 | 54-ValAlaAspIleAlaLysIleIleGluLys-63 |
| SEQ. ID. NO. 32851 | 103-MetValGlyMetMet-107 |
| SEQ. ID. NO. 32852 | 127-ValLeuAlaSerIleValGlnLeuTrpLeuAla-137 |
| SEQ. ID. NO. 32853 | 155-MetAspValLeuValThrIle-161 |
| SEQ. ID. NO. 32854 | 198-PheValSerLeuGlyLysPheLeuGluHisArg-208 |
| SEQ. ID. NO. 32855 | 230-ValGlnArgAsnGlyGlu-235 |
| SEQ. ID. NO. 32856 | 245-GlnIleGlyAspLeuIleArg-251 |
| SEQ. ID. NO. 32857 | 315-LeuGlyAspMetMetAsnAlaLeuSerGluAlaGln-326 |
| SEQ. ID. NO. 32858 | 330-AlaProIleAlaArgValAlaAspLys-338 |
| SEQ. ID. NO. 32859 | 396-MetGlyLysAlaVal-400 |
| SEQ. ID. NO. 32860 | 471-IleValSerAlaAlaGln-476 |
| SEQ. ID. NO. 32861 | 482-IleProAlaAlaGln-486 |
| SEQ. ID. NO. 32862 | 502-GlyValGlyLeuValLys-507 |
| SEQ. ID. NO. 32863 | 539-LysProIleGlyAlaPheAlaLeuSerAspAlaLeuLys-551 |
| SEQ. ID. NO. 32864 | 553-AspThrAlaGluAlaIleGlyArgLeu-561 |
| SEQ. ID. NO. 32865 | 591-AlaPheGlyAsnMetSerProCysAspLysAlaAlaGluValGlnLysLeuLysAlaAla-610 |
| SEQ. ID. NO. 32866 | 617-ValGlyAspGlyIleAsnAspAlaPro-625 |
| SEQ. ID. NO. 32867 | 640-AlaAspValAlaGluHisThr-646 |
| SEQ. ID. NO. 32868 | 653-GlnHisSerValAsnGlnLeu-659 |
| SEQ. ID. NO. 32869 | 680-AlaPhePheTyrAsnIleLeu-686 |
| Antigenic Index - Jameson-Wolf | |
| SEQ. ID. NO. 32870 | 1-MetGlnGlnLysIleArgPhe-7 |
| SEQ. ID. NO. 32871 | 17-CysAlaSerArgIleGluLysValLeuAsnLysLysAspPheValGluSer-33 |
| SEQ. ID. NO. 32872 | 39-AlaSerGluGluAlaGlnValThrPheAspGlySerLysThrSerVal-54 |
| SEQ. ID. NO. 32873 | 59-LysIleIleGluLysThrGlyTyrGlyAlaLysGluLysThrGluAspThrLeuProGlnProGluAlaGluHis-83 |
| SEQ. ID. NO. 32874 | 114-ThrArgHisAspTrp-118 |

TABLE 1-continued

| | |
|---|---|
| SEQ. ID. NO. 32875 | 148-IleLysGlyGlyLeu-152 |
| SEQ. ID. NO. 32876 | 205-LeuGluHisArgThrLysLysSerSerLeuAsn-215 |
| SEQ. ID. NO. 32877 | 228-ValAsnValGlnArgAsnGlyGluTrpLysGlnLeuProIleAspGln-243 |
| SEQ. ID. NO. 32878 | 248-AspLeuIleArgThrAsnHisGlyGluArgIleAlaAla-260 |
| SEQ. ID. NO. 32879 | 262-GlyIleIleGluSerGlySerGlyTrpAlaAspGluSerHisLeuThrGlyGluSerAsnProGluGluLysLysAlaGlyGly-289 |
| SEQ. ID. NO. 32880 | 298-ThrGluGlySerVal-302 |
| SEQ. ID. NO. 32881 | 323-SerGluAlaGlnGlySerLysAlaProIle-332 |
| SEQ. ID. NO. 32882 | 334-ArgValAlaAspLysAlaAla-340 |
| SEQ. ID. NO. 32883 | 361-IleLysGlyAspTrp-365 |
| SEQ. ID. NO. 32884 | 396-MetGlyLysAlaValLys-401 |
| SEQ. ID. NO. 32885 | 409-AlaAlaAlaMetGluGluAlaAlaHis-417 |
| SEQ. ID. NO. 32886 | 422-ValLeuAspLysThrGlyThrLeuThrGluGlyArgProGlnVal-436 |
| SEQ. ID. NO. 32887 | 443-ProAspSerGlyPheAspGluAspAlaLeu-452 |
| SEQ. ID. NO. 32888 | 459-ValGluGlnAsnAla-463 |
| SEQ. ID. NO. 32889 | 498-AlaGluValGluGly-502 |
| SEQ. ID. NO. 32890 | 507-LysSerGlyLysAlaGluPheAla-514 |
| SEQ. ID. NO. 32891 | 520-LysPheSerAspGlyVal-525 |
| SEQ. ID. NO. 32892 | 535-SerValAsnGlyLysProIle-541 |
| SEQ. ID. NO. 32893 | 548-AspAlaLeuLysAlaAspThrAlaGluAlaIleGlyArgLeuLysLysHisAsnIle-566 |
| SEQ. ID. NO. 32894 | 572-SerGlyAspAsnGlnSerThrVal-579 |
| SEQ. ID. NO. 32895 | 596-SerProCysAspLysAlaAlaGluValGlnLysLeuLysAlaAlaGly-611 |
| SEQ. ID. NO. 32896 | 617-ValGlyAspGlyIleAsnAspAla-624 |
| SEQ. ID. NO. 32897 | 636-MetLysGlyGlyAlaAspValAlaGlu-644 |
| Hydrophilic Regions - Hopp-Woods | |
| SEQ. ID. NO. 32898 | 1-MetGlnGlnLysIleArgPhe-7 |
| SEQ. ID. NO. 32899 | 19-SerArgIleGluLysValLeuAsnLysLysAspPheValGlu-32 |
| SEQ. ID. NO. 32900 | 39-AlaSerGluGluAlaGlnVal-45 |
| SEQ. ID. NO. 32901 | 48-AspGlySerLysThrSerVal-54 |
| SEQ. ID. NO. 32902 | 64-ThrGlyTyrGlyAlaLysGluLysThrGluAspThrLeuProGlnProGluAlaGluHis-83 |
| SEQ. ID. NO. 32903 | 205-LeuGluHisArgThrLysLysSerSerLeu-214 |
| SEQ. ID. NO. 32904 | 229-AsnValGlnArgAsnGlyGluTrpLys-237 |
| SEQ. ID. NO. 32905 | 253-AsnHisGlyGluArgIleAlaAla-260 |
| SEQ. ID. NO. 32906 | 262-GlyIleIleGluSer-266 |
| SEQ. ID. NO. 32907 | 270-TrpAlaAspGluSerHisLeuThrGlyGluSerAsnProGluGluLysLysAlaGlyGly-289 |
| SEQ. ID. NO. 32908 | 323-SerGluAlaGlnGlySerLysAlaProIle-332 |
| SEQ. ID. NO. 32909 | 334-ArgValAlaAspLysAlaAla-340 |
| SEQ. ID. NO. 32910 | 409-AlaAlaAlaMetGluGluAlaAlaHis-417 |
| SEQ. ID. NO. 32911 | 422-ValLeuAspLysThrGlyThrLeuThrGluGlyArgProGln-435 |
| SEQ. ID. NO. 32912 | 445-SerGlyPheAspGluAspAlaLeu-452 |
| SEQ. ID. NO. 32913 | 459-ValGluGlnAsnAla-463 |
| SEQ. ID. NO. 32914 | 498-AlaGluValGluGly-502 |
| SEQ. ID. NO. 32915 | 507-LysSerGlyLysAlaGluPheAla-514 |
| SEQ. ID. NO. 32916 | 548-AspAlaLeuLysAlaAspThrAlaGluAlaIleGlyArgLeuLysLysHisAsnIle-566 |
| SEQ. ID. NO. 32917 | 573-GlyAspAsnGlnSer-577 |
| SEQ. ID. NO. 32918 | 596-SerProCysAspLysAlaAlaGluValGlnLysLeuLysAlaAlaGly-611 |
| SEQ. ID. NO. 32919 | 638-GlyGlyAlaAspValAlaGlu-644 |
| g590 | |
| AMPHI Regions - AMPHI | |
| SEQ. ID. NO. 32920 | 90-ValThrLeuValAsnHisIleThrHis-98 |
| SEQ. ID. NO. 32921 | 100-ProPheAlaGlyGlyPhe-105 |
| SEQ. ID. NO. 32922 | 123-LysValLeuGluArgPhePhe-129 |
| SEQ. ID. NO. 32923 | 132-GlnValProValSerLeu-137 |
| SEQ. ID. NO. 32924 | 177-TyrGlnLysGlyPheLysSerTyrArgAsnSer-187 |
| SEQ. ID. NO. 32925 | 213-GluThrSerAspGlyIleAsnProLeu-221 |
| SEQ. ID. NO. 32926 | 248-AsnGluLeuValAsnLeuVal-254 |
| SEQ. ID. NO. 32927 | 331-LysArgLysPheAla-335 |
| SEQ. ID. NO. 32928 | 420-LysMetLeuGluAsp-424 |
| SEQ. ID. NO. 32929 | 450-AspIleAsnGluThrLeuArgLeuMet-458 |
| SEQ. ID. NO. 32930 | 460-AspSerThrValGln-464 |
| Antigenic Index - Jameson-Wolf | |
| SEQ. ID. NO. 32931 | 1-MetLysLysProLeu-5 |
| SEQ. ID. NO. 32932 | 26-LysAlaGluGluSerLeuThrGlnGlnGlnLysIleLeuGlnLysThrGly-42 |
| SEQ. ID. NO. 32933 | 48-SerHisGlnTyrAspArgGlyTrpPheThrSerThrGluThrThrValIleArgLeuLysProGluLeu-70 |
| SEQ. ID. NO. 32934 | 75-GlnLysTyrLeuProAspAsnLeuLys-83 |
| SEQ. ID. NO. 32935 | 111-IleGluThrGluPheLysTyrAlaProGluThrGluLysValLeuGlu-126 |
| SEQ. ID. NO. 32936 | 128-PhePheGlyLysGlnVal-133 |
| SEQ. ID. NO. 32937 | 144-AsnGlySerGlyLysMetGluVal-151 |
| SEQ. ID. NO. 32938 | 157-AspTyrGluGluLeuSerGly-163 |
| SEQ. ID. NO. 32939 | 179-LysGlyPheLysSerTyrArgAsnSerTyrAspAlaProLeu-192 |
| SEQ. ID. NO. 32940 | 196-LysLeuAlaAspLysGlyAspAlaAlaPheGlu-206 |
| SEQ. ID. NO. 32941 | 208-AlaHisPheAspSerGluThrSerAspGlyIleAsn-219 |
| SEQ. ID. NO. 32942 | 233-PheSerLeuGluTrpLysGluGlyValAspTyr-243 |
| SEQ. ID. NO. 32943 | 264-AsnProAsnGlySerIleAlaProSerLysIleGluValGly-277 |
| SEQ. ID. NO. 32944 | 281-PheSerThrLysThrGlyGluSerGlyAla-290 |
| SEQ. ID. NO. 32945 | 292-IleAspSerGluGlyArgPheArgPhe-300 |
| SEQ. ID. NO. 32946 | 304-ValTyrGlyAspGluLysTyrGlyPro-312 |
| SEQ. ID. NO. 32947 | 329-ValLeuLysArgLysPheAla-335 |
| SEQ. ID. NO. 32948 | 338-SerAlaLysLysMetThrGluGluGlnIleArgAsnAspLeu-351 |
| SEQ. ID. NO. 32949 | 355-ValLysGlyAspAlaSerGly-361 |
| SEQ. ID. NO. 32950 | 378-LeuProGlnGlyLysIleAspValGlyGly-387 |

TABLE 1-continued

| | |
|---|---|
| SEQ. ID. NO. 32951 | 393-GlyMetLysLysGluAspLeuAsnGln-401 |
| SEQ. ID. NO. 32952 | 406-LeuLysLysThrGluAlaAsnIle-413 |
| SEQ. ID. NO. 32953 | 437-AsnAlaGluAspGluAlaGluAlaArgAlaSerIle-448 |
| SEQ. ID. NO. 32954 | 450-AspIleAsnGluThrLeu-455 |
| SEQ. ID. NO. 32955 | 466-MetAlaArgGluLysTyrLeu-472 |
| SEQ. ID. NO. 32956 | 485-LeuLysAsnAsnAlaLeuLysLeuAsnGlyLysThrLeuGlnAsnGluProAspProAspPheAspGluGlyAspMetVal SerGlyGlnProHis-516 |
| Hydrophilic Regions - Hopp-Woods | |
| SEQ. ID. NO. 32957 | 1-MetLysLysProLeu-5 |
| SEQ. ID. NO. 32958 | 26-LysAlaGluGluSerLeuThrGln-33 |
| SEQ. ID. NO. 32959 | 62-ThrValIleArgLeuLysProGluLeu-70 |
| SEQ. ID. NO. 32960 | 77-TyrLeuProAspAsnLeu-82 |
| SEQ. ID. NO. 32961 | 111-IleGluThrGluPheLysTyrAlaProGluThrGluLysValLeuGlu-126 |
| SEQ. ID. NO. 32962 | 147-GlyLysMetGluVal-151 |
| SEQ. ID. NO. 32963 | 157-AspTyrGluGluLeuSerGly-163 |
| SEQ. ID. NO. 32964 | 180-GlyPheLysSerTyrArgAsnSerTyr-188 |
| SEQ. ID. NO. 32965 | 196-LysLeuAlaAspLysGlyAspAlaAlaPheGlu-206 |
| SEQ. ID. NO. 32966 | 208-AlaHisPheAspSerGluThrSerAspGly-217 |
| SEQ. ID. NO. 32967 | 233-PheSerLeuGluTrpLysGluGlyValAspTyr-243 |
| SEQ. ID. NO. 32968 | 272-SerLysIleGluValGly-277 |
| SEQ. ID. NO. 32969 | 292-IleAspSerGluGlyArgPheArgPhe-300 |
| SEQ. ID. NO. 32970 | 304-ValTyrGlyAspGluLysTyrGlyPro-312 |
| SEQ. ID. NO. 32971 | 329-ValLeuLysArgLysPheAla-335 |
| SEQ. ID. NO. 32972 | 338-SerAlaLysLysMetThrGluGluGlnIleArgAsnAspLeu-351 |
| SEQ. ID. NO. 32973 | 355-ValLysGlyAspAla-359 |
| SEQ. ID. NO. 32974 | 381-GlyLysIleAspValGlyGly-387 |
| SEQ. ID. NO. 32975 | 393-GlyMetLysLysGluAspLeuAsn-400 |
| SEQ. ID. NO. 32976 | 406-LeuLysLysThrGluAlaAsnIle-413 |
| SEQ. ID. NO. 32977 | 437-AsnAlaGluAspGluAlaGluAlaArgAlaSerIle-448 |
| SEQ. ID. NO. 32978 | 450-AspIleAsnGluThrLeu-455 |
| SEQ. ID. NO. 32979 | 466-MetAlaArgGluLysTyrLeu-472 |
| SEQ. ID. NO. 32980 | 496-ThrLeuGlnAsnGluProAspProAspPheAspGluGlyAspMetValSer-512 |
| g591 | |
| AMPHI Regions - AMPHI | |
| SEQ. ID. NO. 32981 | 6-AlaPheIlePheAla-10 |
| SEQ. ID. NO. 32982 | 17-LeuHisGluPheGlyHisTyrIleValAla-26 |
| SEQ. ID. NO. 32983 | 61-LeuGlyGlyTyrValLysMetValAsp-69 |
| SEQ. ID. NO. 32984 | 143-GlyAspLysIleGlnSerValAsnGlyValSerValGln-155 |
| SEQ. ID. NO. 32985 | 181-SerGlyAlaGlnThrValArgThrIleAspAlaAlaGlyThrProGluAlaGlyLysIleAlaLys-202 |
| SEQ. ID. NO. 32986 | 218-AlaGlyGlyValGluLys-223 |
| SEQ. ID. NO. 32987 | 234-ProGlyAspArgLeu-238 |
| SEQ. ID. NO. 32988 | 245-ProIleAlaSerTrpGlnGluTrpAlaAsnLeuThrArg-257 |
| SEQ. ID. NO. 32989 | 304-AlaTrpAspAlaGlnIleArg-310 |
| SEQ. ID. NO. 32990 | 313-TyrArgProSerValValArgAlaPheGly-322 |
| SEQ. ID. NO. 32991 | 324-GlyTrpGluLysThrValSerHis-331 |
| SEQ. ID. NO. 32992 | 335-ThrLeuLysPhePheGlyLysLeuIle-343 |
| SEQ. ID. NO. 32993 | 351-HisIleSerGlyProLeuThrIleAla-359 |
| SEQ. ID. NO. 32994 | 373-TyrLeuGluPheLeuAlaLeu-379 |
| Antigenic Index - Jameson-Wolf | |
| SEQ. ID. NO. 32995 | 44-PhePheThrArgLysArgGlyAspThrGlu-53 |
| SEQ. ID. NO. 32996 | 68-ValAspThrArgGluGlyGluValSerGluAlaAspLeu-80 |
| SEQ. ID. NO. 32997 | 84-PheAspLysGlnHisProAlaLysArg-92 |
| SEQ. ID. NO. 32998 | 128-ThrValGluProAspThrValAla-135 |
| SEQ. ID. NO. 32999 | 139-GlyPheGlnSerGlyAspLysIleGlnSer-148 |
| SEQ. ID. NO. 33000 | 156-AspTrpSerSerAlaGlnThr-162 |
| SEQ. ID. NO. 33001 | 187-ArgThrIleAspAlaAlaGlyThrProGluAlaGlyLysIleAlaLysAsnGlnGly-205 |
| SEQ. ID. NO. 33002 | 219-GlyGlyValGluLysGlySerProAlaGluLysAlaGlyLeuLysProGlyAspArgLeuThrAlaAlaAspGlyLysProIle-246 |
| SEQ. ID. NO. 33003 | 254-AsnLeuThrArgGlnSerProGlyLysLysIle-264 |
| SEQ. ID. NO. 33004 | 268-TyrGluArgAlaGlyGlnThrHisThrAlaAspIleArgProAspThrValGluGlnProAspHisThrLeu-291 |
| SEQ. ID. NO. 33005 | 295-ValGlyLeuArgProGlnProAspArgAlaTrp-305 |
| SEQ. ID. NO. 33006 | 307-AlaGlnIleArgArgSerTyrArgProSerVal-317 |
| SEQ. ID. NO. 33007 | 327-LysThrValSerHisSer-332 |
| SEQ. ID. NO. 33008 | 343-IleSerGlyAsnAla-347 |
| SEQ. ID. NO. 33009 | 362-AlaGlyGlnSerAla-366 |
| SEQ. ID. NO. 33010 | 408-IleArgGlyLysProLeuGlyGluArgValGln-418 |
| Hydrophilic Regions - Hopp-Woods | |
| SEQ. ID. NO. 33011 | 44-PhePheThrArgLysArgGlyAspThr-52 |
| SEQ. ID. NO. 33012 | 68-ValAspThrArgGluGlyGluValSerGluAlaAspLeu-80 |
| SEQ. ID. NO. 33013 | 84-PheAspLysGlnHisProAlaLysArg-92 |
| SEQ. ID. NO. 33014 | 129-ValGluProAspThrValAla-135 |
| SEQ. ID. NO. 33015 | 139-GlyPheGlnSerGlyAspLysIleGlnSer-148 |
| SEQ. ID. NO. 33016 | 193-GlyThrProGluAlaGlyLysIleAlaLys-202 |
| SEQ. ID. NO. 33017 | 220-GlyValGluLysGlySerProAlaGluLysAlaGlyLeuLysProGlyAspArgLeuThrAlaAlaAspGlyLysPro-245 |
| SEQ. ID. NO. 33018 | 256-ThrArgGlnSerProGlyLysLysIle-264 |
| SEQ. ID. NO. 33019 | 268-TyrGluArgAlaGlyGln-273 |
| SEQ. ID. NO. 33020 | 277-AlaAspIleArgProAspThrValGluGlnProAsp-288 |
| SEQ. ID. NO. 33021 | 299-ProGlnProAspArgAlaTrp-305 |
| SEQ. ID. NO. 33022 | 308-GlnIleArgArgSerTyrArg-314 |

TABLE 1-continued

| | |
|---|---|
| SEQ. ID. NO. 33023 | 362-AlaGlyGlnSerAla-366 |
| SEQ. ID. NO. 33024 | 411-LysProLeuGlyGluArgValGln-418 |
| g592 | |
| AMPHI Regions - AMPHI | |
| SEQ. ID. NO. 33025 | 6-PheGlyGlnIlePheSer-11 |
| SEQ. ID. NO. 33026 | 21-GlyGlyLeuLeuGlyGlyLeuIle-28 |
| SEQ. ID. NO. 33027 | 50-AlaProAsnAlaAlaAlaAlaAla-57 |
| SEQ. ID. NO. 33028 | 65-GlnGlyMetIleGlnMetLeuGlyValPheValAsp-76 |
| SEQ. ID. NO. 33029 | 94-ProTyrGlyAspLeu-98 |
| SEQ. ID. NO. 33030 | 109-ValSerGlnValGlyGlnTrp-115 |
| SEQ. ID. NO. 33031 | 153-ThrAlaValPheArgMet-158 |
| SEQ. ID. NO. 33032 | 165-TyrPheGlyAlaValAla-170 |
| SEQ. ID. NO. 33033 | 185-IleMetAlaTrpIleAsnLeuValAlaIleLeuLeuLeuSer-198 |
| Antigenic Index - Jameson-Wolf | |
| SEQ. ID. NO. 33034 | 35-GlyIleLysArgGlyLeuTyrSerAsnGluAlaGlyMetGlySerAlaProAsnAla-53 |
| SEQ. ID. NO. 33035 | 57-AlaGluValLysHisProValSer-64 |
| SEQ. ID. NO. 33036 | 93-GlnProTyrGlyAspLeuSerGly-100 |
| SEQ. ID. NO. 33037 | 137-AlaTyrAlaGluSerAsnVal-143 |
| SEQ. ID. NO. 33038 | 206-ArgAspTyrThrAlaLysLeuLysMetGlyLysAspProGluPheLysLeuSerGluHisProGlyLeuLysArgArgIleLysSerAspValTrp-237 |
| Hydrophilic Regions - Hopp-Woods | |
| SEQ. ID. NO. 33039 | 35-GlyIleLysArgGlyLeuTyr-41 |
| SEQ. ID. NO. 33040 | 57-AlaGluValLysHisProVal-63 |
| SEQ. ID. NO. 33041 | 212-LeuLysMetGlyLysAspProGluPheLysLeuSerGlu-224 |
| SEQ. ID. NO. 33042 | 226-ProGlyLeuLysArgArgIleLysSer-234 |
| g593 | |
| AMPHI Regions - AMPHI | |
| SEQ. ID. NO. 33043 | 6-GlyLeuCysLysCysPheGlyGly-13 |
| SEQ. ID. NO. 33044 | 41-SerThrLeuLeuAsnMetIleAlaGlyIleValArg-52 |
| SEQ. ID. NO. 33045 | 87-HisMetSerAlaLeuGlu-92 |
| SEQ. ID. NO. 33046 | 113-LeuSerAlaLeuAlaGlu-118 |
| SEQ. ID. NO. 33047 | 125-AlaHisArgLysProGluLysLeuSerGlyGlyGlu-136 |
| SEQ. ID. NO. 33048 | 159-PheSerSerLeuAsp-163 |
| SEQ. ID. NO. 33049 | 165-HisLeuArgAspArgLeuArgArgMet-173 |
| SEQ. ID. NO. 33050 | 217-GluThrLeuIleGlnThrProAlaGlyValGlnValAlaArgLeuMetGlyLeu-234 |
| SEQ. ID. NO. 33051 | 259-LeuLeuSerLeuValArgLeuProAspSerLeuArg-270 |
| SEQ. ID. NO. 33052 | 290-HisThrAspGlyIle-294 |
| Antigenic Index - Jameson-Wolf | |
| SEQ. ID. NO. 33053 | 10-CysPheGlyGlyLysThrValAla-17 |
| SEQ. ID. NO. 33054 | 24-ValGlyArgGlyLysIle-29 |
| SEQ. ID. NO. 33055 | 33-LeuGlyArgSerGlyCysGlyLysSerThr-42 |
| SEQ. ID. NO. 33056 | 50-IleValArgProAspGlyGlyGluIleArgLeuAsnGlyGluAsnIleThr-66 |
| SEQ. ID. NO. 33057 | 69-ProProGluLysArgArgIle-75 |
| SEQ. ID. NO. 33058 | 99-LysMetGlnLysMetProLysAlaGluAlaGluArgLeuAla-112 |
| SEQ. ID. NO. 33059 | 119-ValGlyLeuGluAsnGluAlaHisArgLysProGluLysLeuSerGlyGlyGluLysGlnArgLeuAlaLeu-142 |
| SEQ. ID. NO. 33060 | 157-GluSerPheSerSerLeu-162 |
| SEQ. ID. NO. 33061 | 164-ThrHisLeuArgAspArgLeuArgArgMetThrAlaGluArgIleArgLysGlyGlyIle-183 |
| SEQ. ID. NO. 33062 | 190-HisSerProGluGluAlaCysThrAlaAlaAspGluIleAlaVal-204 |
| SEQ. ID. NO. 33063 | 206-HisGluGlyLysIleLeuGlnCysGlyThrProGluThrLeu-219 |
| SEQ. ID. NO. 33064 | 233-GlyLeuProAsnThrAspAspAspArgHisIleProGlnAsnAla-247 |
| SEQ. ID. NO. 33065 | 250-LeuAspAsnHisGlyThrGluCysArg-258 |
| SEQ. ID. NO. 33066 | 264-ArgLeuProAspSerLeuArgLeu-271 |
| SEQ. ID. NO. 33067 | 275-HisProGluHisGlyGlu-280 |
| SEQ. ID. NO. 33068 | 289-GlnHisThrAspGlyIleSerGlyAsnGly-298 |
| SEQ. ID. NO. 33069 | 300-ValArgIleArgValAspGluGlyArgIleValArgPheArg-313 |
| Hydrophilic Regions - Hopp-Woods | |
| SEQ. ID. NO. 33070 | 25-GlyArgGlyLysIle-29 |
| SEQ. ID. NO. 33071 | 36-SerGlyCysGlyLys-40 |
| SEQ. ID. NO. 33072 | 51-ValArgProAspGlyGlyGluIleArgLeuAsnGly-62 |
| SEQ. ID. NO. 33073 | 69-ProProGluLysArgArgIle-75 |
| SEQ. ID. NO. 33074 | 99-LysMetGlnLysMetProLysAlaGluAlaGluArgLeuAla-112 |
| SEQ. ID. NO. 33075 | 119-ValGlyLeuGluAsnGluAlaHisArgLysProGluLysLeuSerGlyGlyGluLysGlnArgLeuAlaLeu-142 |
| SEQ. ID. NO. 33076 | 164-ThrHisLeuArgAspArgLeuArgArgMetThrAlaGluArgIleArgLysGlyGly-182 |
| SEQ. ID. NO. 33077 | 191-SerProGluGluAlaCysThrAlaAlaAspGluIleAlaVal-204 |
| SEQ. ID. NO. 33078 | 206-HisGluGlyLysIle-210 |
| SEQ. ID. NO. 33079 | 236-AsnThrAspAspAspArgHisIlePro-244 |
| SEQ. ID. NO. 33080 | 253-HisGlyThrGluCysArg-258 |
| SEQ. ID. NO. 33081 | 264-ArgLeuProAspSerLeuArg-270 |
| SEQ. ID. NO. 33082 | 275-HisProGluHisGlyGlu-280 |
| SEQ. ID. NO. 33083 | 289-GlnHisThrAspGlyIleSer-295 |
| SEQ. ID. NO. 33084 | 300-ValArgIleArgValAspGluGlyArgIleValArgPheArg-313 |
| g594 | |
| AMPHI Regions - AMPHI | |
| SEQ. ID. NO. 33085 | 21-SerIleLeuArgLeu-25 |
| SEQ. ID. NO. 33086 | 108-AlaGlyArgLysCysGlnGluThrAlaAlaAla-118 |
| SEQ. ID. NO. 33087 | 138-AlaIleLysHisCysAsnPheThr-145 |
| Antigenic Index - Jameson-Wolf | |
| SEQ. ID. NO. 33088 | 1-MetGlyAlaAspThrAspGlyAspLysAspValArgLeuAsnArgThr-16 |
| SEQ. ID. NO. 33089 | 51-ValGluHisProAsnArgPhe-57 |
| SEQ. ID. NO. 33090 | 75-HisLeuAspGlySerThrGlyGly-82 |
| SEQ. ID. NO. 33091 | 86-PheArgArgGluLysThrGlyHisLysArgArgCysHisThrGlnCys-101 |

TABLE 1-continued

| | |
|---|---|
| SEQ. ID. NO. 33092 | 103-HisSerAlaArgAlaAlaGlyArgLysCysGlnGluThr-115 |
| SEQ. ID. NO. 33093 | 137-ArgAlaIleLysHisCysAsn-143 |
| Hydrophilic Regions - Hopp-Woods | |
| SEQ. ID. NO. 33094 | 1-MetGlyAlaAspThrAspGlyAspLysAspValArgLeuAsnArg-15 |
| SEQ. ID. NO. 33095 | 86-PheArgArgGluLysThrGlyHisLysArgArgCysHis-98 |
| SEQ. ID. NO. 33096 | 105-AlaArgAlaAlaGlyArgLysCysGlnGluThr-115 |
| g595 | |
| AMPHI Regions - AMPHI | |
| SEQ. ID. NO. 33097 | 20-CysGlnProProGluAla-25 |
| SEQ. ID. NO. 33098 | 98-GlyLeuSerAspLysMetAsnArg-105 |
| SEQ. ID. NO. 33099 | 140-AlaAspLeuGluLysLeuProGlnProLeuAlaAspTyrLys-153 |
| SEQ. ID. NO. 33100 | 157-GlnGlyGluValLys-161 |
| SEQ. ID. NO. 33101 | 170-PheThrGluAlaValLysAlaGlyAspIleGluLysAlaLys-183 |
| SEQ. ID. NO. 33102 | 196-IleGluProIleAlaGluLeuPheSerGluLeuAspProValIleAspAlaCysGluAspAspPheLysAspGly-220 |
| SEQ. ID. NO. 33103 | 224-AlaGlyPheThrGlyPheHisArg-231 |
| SEQ. ID. NO. 33104 | 247-GluThrAlaAlaLysLeuMetThrAspValGluAlaLeuGlnLysGluIleAsp-264 |
| SEQ. ID. NO. 33105 | 274-ValGlyGlyAlaSerGluLeuIleGlu-282 |
| SEQ. ID. NO. 33106 | 311-SerLysLysIleValAspLeuPheArgProLeu-321 |
| SEQ. ID. NO. 33107 | 337-PheLysGlnValAsnGluIleLeuAlaLys-346 |
| SEQ. ID. NO. 33108 | 351-AspGlyPheGluThrTyrAspLysLeuSerGluAlaAsp-363 |
| SEQ. ID. NO. 33109 | 369-AlaProIleAsnAlaLeuAlaGluAspLeuAlaGlnLeuArgGlyIleLeuGlyLeu-387 |
| Antigenic Index - Jameson-Wolf | |
| SEQ. ID. NO. 33110 | 1-MetArgLysPheAsn-5 |
| SEQ. ID. NO. 33111 | 21-GlnProProGluAlaGluLysAlaAlaPro-30 |
| SEQ. ID. NO. 33112 | 32-AlaSerGlyGluThrGlnSerAlaAsnGluGlyGlySer-44 |
| SEQ. ID. NO. 33113 | 50-AsnAspAsnAlaCysGluProMetAsnLeu-59 |
| SEQ. ID. NO. 33114 | 70-IleLysAsnAsnSerGlyArgLysLeuGluTrpGluIle-82 |
| SEQ. ID. NO. 33115 | 87-MetValValAspGluArgGluAsnIleAla-96 |
| SEQ. ID. NO. 33116 | 98-GlyLeuSerAspLysMetAsnArgAsnLeuLeuProGlyGluTyrGluMet-114 |
| SEQ. ID. NO. 33117 | 120-ThrAsnProArgGlyLysLeuValVal-128 |
| SEQ. ID. NO. 33118 | 130-AspSerGlyPheLysAspThrAlaAsnGluAlaAspLeuGluLysLeuPro-146 |
| SEQ. ID. NO. 33119 | 158-GlyGluValLysGluLeuAlaAlaLysThrLysThrPheThrGluAlaValLysAlaGlyAspIleGluLysAlaLysSer-184 |
| SEQ. ID. NO. 33120 | 191-ValHisTyrGluArgIleGluProIle-199 |
| SEQ. ID. NO. 33121 | 204-SerGluLeuAspProValIleAspAlaCysGluAspAspPheLysAspGlyAlaLysAspAlaGly-225 |
| SEQ. ID. NO. 33122 | 238-ValGluLysAspValSerGlyValLysGluThrAlaAla-250 |
| SEQ. ID. NO. 33123 | 252-LeuMetThrAspValGluAlaLeuGlnLysGluIleAsp-264 |
| SEQ. ID. NO. 33124 | 269-ProProGlyLysValValGlyGlyAla-277 |
| SEQ. ID. NO. 33125 | 279-GluLeuIleGluGluAlaAlaGlySerLysIleSerGlyGluGluAspArgTyrSerHisThrAspLeuSerAspPheGlnAlaAsnAla AspGlySerLysLysIleValAsp-316 |
| SEQ. ID. NO. 33126 | 322-IleGluAlaLysAsnLysAlaLeuLeuGluLysThrAspThrAsnPheLysGlnValAsn-341 |
| SEQ. ID. NO. 33127 | 345-AlaLysTyrArgThrLysAspGlyPheGluThrTyrAspLysLeuSerGluAlaAspArgLysAlaLeu-367 |
| SEQ. ID. NO. 33128 | 374-LeuAlaGluAspLeuAlaGln-380 |
| Hydrophilic Regions- Hopp-Woods | |
| SEQ. ID. NO. 33129 | 1-MetArgLysPheAsn-5 |
| SEQ. ID. NO. 33130 | 21-GlnProProGluAlaGluLysAlaAlaPro-30 |
| SEQ. ID. NO. 33131 | 32-AlaSerGlyGluThrGlnSerAlaAsnGluGlyGlySer-44 |
| SEQ. ID. NO. 33132 | 72-AsnAsnSerGlyArgLysLeuGluTrpGluIle-82 |
| SEQ. ID. NO. 33133 | 87-MetValValAspGluArgGluAsnIle-95 |
| SEQ. ID. NO. 33134 | 99-LeuSerAspLysMetAsnArg-105 |
| SEQ. ID. NO. 33135 | 110-GlyGluTyrGluMet-114 |
| SEQ. ID. NO. 33136 | 122-ProArgGlyLysLeuValVal-128 |
| SEQ. ID. NO. 33137 | 131-SerGlyPheLysAspThrAlaAsnGluAlaAspLeuGluLysLeuPro-146 |
| SEQ. ID. NO. 33138 | 158-GlyGluValLysGluLeuAlaAlaLysThrLysThrPheThrGluAlaValLysAlaGlyAspIleGluLysAlaLysSer-184 |
| SEQ. ID. NO. 33139 | 191-ValHisTyrGluArgIleGluProIle-199 |
| SEQ. ID. NO. 33140 | 204-SerGluLeuAspProValIleAspAlaCysGluAspAspPheLysAspGlyAlaLysAspAlaGly-225 |
| SEQ. ID. NO. 33141 | 238-ValGluLysAspValSerGlyValLysGluThrAlaAla-250 |
| SEQ. ID. NO. 33142 | 252-LeuMetThrAspValGluAlaLeuGlnLysGluIleAsp-264 |
| SEQ. ID. NO. 33143 | 279-GluLeuIleGluGluAlaAlaGlySerLysIleSerGlyGluGluAspArgTyrSerHis-298 |
| SEQ. ID. NO. 33144 | 308-AlaAspGlySerLysLysIleValAsp-316 |
| SEQ. ID. NO. 33145 | 322-IleGluAlaLysAsnLysAlaLeuLeuGluLysThrAspThrAsnPhe-337 |
| SEQ. ID. NO. 33146 | 347-TyrArgThrLysAspGlyPheGluThrTyrAspLysLeuSerGluAlaAspArgLysAlaLeu-367 |
| SEQ. ID. NO. 33147 | 374-LeuAlaGluAspLeuAlaGln-380 |
| g596-2 | |
| AMPHI Regions - AMPHI | |
| SEQ. ID. NO. 33148 | 9-MetLeuArgValSerLysValVal-16 |
| SEQ. ID. NO. 33149 | 50-LeuArgIleMetAlaGlyValAspLys-58 |
| SEQ. ID. NO. 33150 | 87-ValArgGluGluValGluSerGlyLeuGlyGluValAlaAlaAlaGlnLysArgLeuGluGluValTyrAlaGluTyr-112 |
| SEQ. ID. NO. 33151 | 192-ProThrAsnHisLeuAsp-197 |
| SEQ. ID. NO. 33152 | 202-GluTrpLeuGluGlnPheLeuValArgPheProGly-213 |
| SEQ. ID. NO. 33153 | 296-ArgPheGluGluMetSerAsnTyr-303 |
| SEQ. ID. NO. 33154 | 322-LeuGlyAsnGluValIleGluPheValAsnValSerLysSerPhe-336 |
| SEQ. ID. NO. 33155 | 366-SerThrLeuPheLysMet-371 |
| SEQ. ID. NO. 33156 | 409-AspAsnIleAlaGlu-413 |
| SEQ. ID. NO. 33157 | 440-AspGlnSerLysIleAlaArgGlnLeuSerGly-450 |
| SEQ. ID. NO. 33158 | 483-LeuArgAlaLeuGluAspAlaLeuLeuGluPheAla-494 |
| Antigenic Index - Jameson-Wolf | |
| SEQ. ID. NO. 33159 | 16-ValProProGlnLysThrIleIleLysAspIleSer-27 |
| SEQ. ID. NO. 33160 | 41-LeuAsnGlyThrGlyLysSerThrVal-49 |
| SEQ. ID. NO. 33161 | 54-AlaGlyValAspLysGluPheGluGlyGluAla-64 |
| SEQ. ID. NO. 33162 | 75-LeuProGlnGluProGluLeuAspProGluLysThrValArgGluGluValGluSerGlyLeu-95 |

TABLE 1-continued

| | |
|---|---|
| SEQ. ID. NO. 33163 | 99-AlaAlaAlaGlnLysArgLeuGluGluValTyr-109 |
| SEQ. ID. NO. 33164 | 112-TyrAlaAsnProAspAlaAspPheAspAlaLeuAlaGluGluGlnGlyArgLeuGlu-130 |
| SEQ. ID. NO. 33165 | 136-GlySerSerThrGlyGlyGlyAlaGluHisGluLeuGluIleAlaAlaAspAlaLeuArgLeuProAspTrpAspAlaLysIle-163 |
| SEQ. ID. NO. 33166 | 165-AsnLeuSerGlyGlyGluLysArgArgValAla-175 |
| SEQ. ID. NO. 33167 | 181-LeuSerLysProAspMet-186 |
| SEQ. ID. NO. 33168 | 190-AspGluProThrAsnHisLeuAspAlaGluSer-200 |
| SEQ. ID. NO. 33169 | 219-ThrHisAspArgTyrPhe-224 |
| SEQ. ID. NO. 33170 | 233-LeuGluLeuAspArgGlyHisGlyIle-241 |
| SEQ. ID. NO. 33171 | 243-TrpLysGlyAsnTyrSerSer-249 |
| SEQ. ID. NO. 33172 | 251-LeuGluGlnLysGluLysArgLeuGluAsnGluAlaLysSerGluAlaAlaArgValLysAlaMetLysGlnGluLeuGluTrpValArgGlnAsn AlaLysGlyArgGlnAlaLysProLysAlaArgLeuAlaArgPheGluGluMetSerAsnTyrGluTyrGlnLysArgAsnGluThrGlnGlu-313 |
| SEQ. ID. NO. 33173 | 319-AlaGluArgLeuGlyAsnGluVal-326 |
| SEQ. ID. NO. 33174 | 333-SerLysSerPheGlyAspLysValLeu-341 |
| SEQ. ID. NO. 33175 | 360-ProAsnGlyAlaGlyLysSerThrLeu-368 |
| SEQ. ID. NO. 33176 | 373-AlaGlyLysGluGlnProAspSerGlyGluValLysIle-385 |
| SEQ. ID. NO. 33177 | 395-AspGlnSerArgGluGlyLeuGlnAsnAspLysThrValPhe-408 |
| SEQ. ID. NO. 33178 | 411-IleAlaGluGlyArgAspIleLeu-418 |
| SEQ. ID. NO. 33179 | 425-IleProAlaArgGlnTyrLeuGlyArgPheAsnPheLysGlySerAspGlnSerLysIleAlaArgGlnLeuSerGlyGlyGluArgGlyArgLeu HisLeu-458 |
| SEQ. ID. NO. 33180 | 471-LeuAspGluProSerAsnAspLeuAspValGluThrLeuArgAlaLeuGlu-487 |
| SEQ. ID. NO. 33181 | 501-SerHisAspArgTrpPhe-506 |
| SEQ. ID. NO. 33182 | 516-AlaCysGluGlyAspSerLysTrp-523 |
| SEQ. ID. NO. 33183 | 527-AspGlyAsnTyrGlnGluTyrGluAlaAspLysLysArgArgLeuGlyLysGluGlyAlaLysProLysArgIleLysTyrLysProValThrArg-558 |
| Hydrophilic Regions - Hopp-Woods | |
| SEQ. ID. NO. 33184 | 54-AlaGlyValAspLysGluPheGluGlyGluAla-64 |
| SEQ. ID. NO. 33185 | 77-GlnGluProGluLeuAspProGluLysThrValArgGluGluValGluSerGlyLeu-95 |
| SEQ. ID. NO. 33186 | 99-AlaAlaAlaGlnLysArgLeuGluGluValTyr-109 |
| SEQ. ID. NO. 33187 | 113-AlaAsnProAspAlaAspPheAspAlaLeuAlaGluGluGlnGlyArgLeuGlu-130 |
| SEQ. ID. NO. 33188 | 141-GlyGlyAlaGluHisGluLeuGluIleAlaAlaAspAlaLeuArg-155 |
| SEQ. ID. NO. 33189 | 157-ProAspTrpAspAlaLysIle-163 |
| SEQ. ID. NO. 33190 | 167-SerGlyGlyGluLysArgArgValAla-175 |
| SEQ. ID. NO. 33191 | 181-LeuSerLysProAsp-185 |
| SEQ. ID. NO. 33192 | 190-AspGluProThrAsnHisLeuAspAlaGluSer-200 |
| SEQ. ID. NO. 33193 | 233-LeuGluLeuAspArgGlyHis-239 |
| SEQ. ID. NO. 33194 | 251-LeuGluGlnLysGluLysArgLeuGluAsnGluAlaLysSerGluAlaAlaArgValLysAlaMetLysGlnGluLeuGluTrp-278 |
| SEQ. ID. NO. 33195 | 280-ArgGlnAsnAlaLysGlyArgGlnAlaLysProLysAlaArgLeuAlaArgPheGluGluMetSerAsn-302 |
| SEQ. ID. NO. 33196 | 304-GluTyrGlnLysArgAsnGluThrGln-312 |
| SEQ. ID. NO. 33197 | 319-AlaGluArgLeuGlyAsnGluVal-326 |
| SEQ. ID. NO. 33198 | 373-AlaGlyLysGluGlnProAspSerGlyGluValLysIle-385 |
| SEQ. ID. NO. 33199 | 395-AspGlnSerArgGluGlyLeuGlnAsnAspLysThrValPhe-408 |
| SEQ. ID. NO. 33200 | 411-IleAlaGluGlyArgAspIleLeu-418 |
| SEQ. ID. NO. 33201 | 435-AsnPheLysGlySerAspGlnSerLysIleAlaArg-446 |
| SEQ. ID. NO. 33202 | 448-LeuSerGlyGlyGluArgGlyArgLeuHisLeu-458 |
| SEQ. ID. NO. 33203 | 472-AspGluProSerAsnAspLeuAspValGluThrLeuArgAlaLeuGlu-487 |
| SEQ. ID. NO. 33204 | 517-CysGluGlyAspSer-521 |
| SEQ. ID. NO. 33205 | 529-AsnTyrGlnGluTyrGluAlaAspLysLysArgArgLeuGlyLysGluGlyAlaLysProLysArgIleLysTyr-553 |
| g597 | |
| AMPHI Regions - AMPHI | |
| SEQ. ID. NO. 33206 | 6-SerAsnSerLeuLysGlnLeuGlnGlu-14 |
| SEQ. ID. NO. 33207 | 45-TrpAspLysPheGlnLysLeu-51 |
| SEQ. ID. NO. 33208 | 68-GlnIleSerArgPheValSerGly-75 |
| SEQ. ID. NO. 33209 | 101-LeuArgTyrThrArgTyrValAsnAla-109 |
| SEQ. ID. NO. 33210 | 111-AsnArgGluValValLysAspLeuGluLysGlnGln-122 |
| SEQ. ID. NO. 33211 | 132-IleAsnAsnGluLeuAlaArgLeuLysLys-141 |
| SEQ. ID. NO. 33212 | 144-AlaAsnValGlnSerLeu-149 |
| SEQ. ID. NO. 33213 | 157-AspAlaAlaGluGlnThrGlu-163 |
| SEQ. ID. NO. 33214 | 170-LysIleSerLysAspAlaArg-176 |
| SEQ. ID. NO. 33215 | 189-AsnLysLeuLeuSer-193 |
| SEQ. ID. NO. 33216 | 253-ProSerValMetGlyIleGlySerAlaAspGlyPheSerArgMetGlnGlyArgLeuLysLysProValAspGlyValProThrGly-281 |
| SEQ. ID. NO. 33217 | 302-ProAlaThrValGluSerIleAla-309 |
| SEQ. ID. NO. 33218 | 314-SerTyrAlaAspGluLeuAspGlyTyrGlyLysVal-325 |
| SEQ. ID. NO. 33219 | 336-SerIleTyrAlaGlyLeuSerGluIleSerAlaGlyLys-348 |
| Antigenic Index - Jameson-Wolf | |
| SEQ. ID. NO. 33220 | 7-AsnSerLeuLysGlnLeuGlnGluGluArgIleArgGlnGluArgIleArgGlnGluArgIleArgGlnAlaArgGlyAsnLeu-34 |
| SEQ. ID. NO. 33221 | 36-SerValAsnArgLysGlnArgGluAlaTrpAspLysPheGlnLysLeuAsnThrGluLeuAsnArgLeuLysThrGluValAlaAla-64 |
| SEQ. ID. NO. 33222 | 74-SerGlyAsnTyrLysAsnSerArgProAsnAla-84 |
| SEQ. ID. NO. 33223 | 91-AsnAlaGluProGlyGlnLysAsnArgPhe-100 |
| SEQ. ID. NO. 33224 | 107-ValAsnAlaSerAsnArgGluValValLysAspLeuGluLysGlnGlnLys-123 |
| SEQ. ID. NO. 33225 | 128-GlnGluGlnLysIleAsnAsnGluLeuAlaArgLeuLysLysIleGln-143 |
| SEQ. ID. NO. 33226 | 149-LeuLeuLysLysGlnGlyValThrAspAlaAlaGluGlnThrGluSerArgArgGlnAsnAlaLysIleSerLysAspAlaArgLysLeuLeuGlu GlnLysGlyAsnGluGlnGlnLeu-188 |
| SEQ. ID. NO. 33227 | 191-LeuLeuSerAsnLeuGluLysLysLysAlaGluHisArgIleGlnAspAlaGluAlaLysArgLysLeuAlaGluAlaLysLeuAlaAlaAlaGlu LysAlaArgLysGluAlaAlaGlnGlnLysAlaGluAlaArgArgAlaGluMetSerAsnLeuThrAlaGluAspArgAsnIleGlnAlaProSer-254 |
| SEQ. ID. NO. 33228 | 259-GlySerAlaAspGlyPheSerArgMetGlnGlyArgLeuLysLysProValAspGlyValProThr-280 |
| SEQ. ID. NO. 33229 | 284-GlyGlnAsnArgSerGlyGlyAspVal-292 |
| SEQ. ID. NO. 33230 | 314-SerTyrAlaAspGluLeuAspGlyTyrGly-323 |
| SEQ. ID. NO. 33231 | 329-AspHisGlyGluAsnTyr-334 |
| SEQ. ID. NO. 33232 | 343-GluIleSerAlaGlyLysGlyTyrThr-351 |
| SEQ. ID. NO. 33233 | 354-AlaGlySerLysIleGlyThrSerGlySerLeuProAspGlyGluGluGlyLeu-371 |
| SEQ. ID. NO. 33234 | 375-IleArgTyrArgGlyGlnValLeuAsnProSerGlyTrp-387 |

TABLE 1-continued

| | |
|---|---|
| Hydrophilic Regions - Hopp-Woods | |
| SEQ. ID. NO. 33235 | 7-AsnSerLeuLysGlnLeuGlnGluGluArgIleArgGlnGluArgIleArgGlnGluArgIleArgGlnAlaArgGlyAsn-33 |
| SEQ. ID. NO. 33236 | 37-ValAsnArgLysGlnArgGluAlaTrpAspLysPheGlnLysLeuAsnThrGluLeuAsnArgLeuLysThrGluValAlaAla-64 |
| SEQ. ID. NO. 33237 | 77-TyrLysAsnSerArgProAsn-83 |
| SEQ. ID. NO. 33238 | 91-AsnAlaGluProGlyGlnLysAsnArgPhe-100 |
| SEQ. ID. NO. 33239 | 110-SerAsnArgGluValValLysAspLeuGluLysGlnGlnLys-123 |
| SEQ. ID. NO. 33240 | 128-GlnGluGlnLysIleAsnAsnGluLeuAlaArgLeuLysLysIleGln-143 |
| SEQ. ID. NO. 33241 | 149-LeuLeuLysLysGlnGlyValThrAspAlaAlaGluGlnThrGluSerArgArgGlnAsnAlaLysIleSerLysAspAlaArgLysLeuLeuGlu GlnLysGlyAsnGluGlnGlnLeu-188 |
| SEQ. ID. NO. 33242 | 193-SerAsnLeuGluLysLysLysAlaGluHisArgIleGlnAspAlaGluAlaLysArgLysLeuAlaGluAlaLysLeuAlaAlaAlaGluLysAla ArgLysGluAlaAlaGlnGlnLysAlaGluAlaArgArgAlaGluMet-240 |
| SEQ. ID. NO. 33243 | 244-ThrAlaGluAspArgAsnIleGln-251 |
| SEQ. ID. NO. 33244 | 267-MetGlnGlyArgLeuLysLysProValAsp-276 |
| SEQ. ID. NO. 33245 | 286-AsnArgSerGlyGlyAspVal-292 |
| SEQ. ID. NO. 33246 | 315-TyrAlaAspGluLeuAspGlyTyrGly-323 |
| SEQ. ID. NO. 33247 | 356-SerLysIleGlyThr-360 |
| SEQ. ID. NO. 33248 | 363-SerLeuProAspGlyGluGluGlyLeu-371 |
| g601 | |
| AMPHI Regions - AMPHI | |
| SEQ. ID. NO. 33249 | 7-LeuValAspGluIleAspValProAsnIleGlyArg-18 |
| SEQ. ID. NO. 33250 | 26-AlaGlyIleProThrValPhe-32 |
| SEQ. ID. NO. 33251 | 42-GlyLysGluLeuGlnAspAspIleAsnAsnAspAlaAlaAlaLeuGluLysPheGluThrIleArgAlaTyrGlyAlaLeu-68 |
| SEQ. ID. NO. 33252 | 70-MetGlyLeuIleSerAspValSerGlu-78 |
| SEQ. ID. NO. 33253 | 100-SerSerGlyLysThrValAsn-106 |
| SEQ. ID. NO. 33254 | 137-AlaValLeuGlyThrLeuValAsnLeuAlaAla-147 |
| SEQ. ID. NO. 33255 | 167-GlyAlaAlaAlaGlu-171 |
| Antigenic Index - Jameson-Wolf | |
| SEQ. ID. NO. 33256 | 3-ProThrGlyAsnLeuValAspGluIleAspValProAsnIleGlyArgLeuLys-20 |
| SEQ. ID. NO. 33257 | 39-GlyTyrThrGlyLysGluLeuGlnAspAspIleAsnAsnAspAlaAlaAlaLeuGluLysPheGluThr-61 |
| SEQ. ID. NO. 33258 | 75-AspValSerGluAlaAlaAlaArgAlaArgThrProLysProAlaPhe-90 |
| SEQ. ID. NO. 33259 | 97-TyrThrAlaSerSerGlyLysThrValAsn-106 |
| SEQ. ID. NO. 33260 | 108-AlaAspIleAspLeuProVal-114 |
| SEQ. ID. NO. 33261 | 147-AlaGlyGlyGlyThrArgLysGluValArgPheGlyHisProSerGlyThrLeuArg-165 |
| SEQ. ID. NO. 33262 | 170-AlaGluCysGlnAspGlyGln-176 |
| SEQ. ID. NO. 33263 | 183-ValMetSerArgSerAlaArgValIle-191 |
| SEQ. ID. NO. 33264 | 196-ValArgValProAspAspCysPhe-203 |
| Hydrophilic Regions - Hopp-Woods | |
| SEQ. ID. NO. 33265 | 7-LeuValAspGluIleAspVal-13 |
| SEQ. ID. NO. 33266 | 40-TyrThrGlyLysGluLeuGlnAspAspIleAsnAsnAspAlaAlaAlaLeuGluLysPheGluThr-61 |
| SEQ. ID. NO. 33267 | 75-AspValSerGluAlaAlaAlaArgAlaArgThrProLys-87 |
| SEQ. ID. NO. 33268 | 99-AlaSerSerGlyLysThrValAsn-106 |
| SEQ. ID. NO. 33269 | 108-AlaAspIleAspLeuProVal-114 |
| SEQ. ID. NO. 33270 | 149-GlyGlyThrArgLysGluValArgPhe-157 |
| SEQ. ID. NO. 33271 | 170-AlaGluCysGlnAsp-174 |
| SEQ. ID. NO. 33272 | 186-ArgSerAlaArgValIle-191 |
| SEQ. ID. NO. 33273 | 198-ValProAspAspCysPhe-203 |
| g602 | |
| AMPHI Regions - AMPHI | |
| SEQ. ID. NO. 33274 | 54-ArgGlnValAlaGlnIle-59 |
| SEQ. ID. NO. 33275 | 61-AlaGlyLeuHisValCysAsnGlyVal-69 |
| Antigenic Index - Jameson-Wolf | |
| SEQ. ID. NO. 33276 | 5-GlnCysAspLysAlaArgHisMetArgPro-14 |
| SEQ. ID. NO. 33277 | 17-LeuGlyGlyGlnIleAsnArgHisArgGlnAlaSerAsnArgGlyLeuCys-33 |
| SEQ. ID. NO. 33278 | 35-PheGlyGlyPheGlnGlyAsnArgGluAlaGln-45 |
| SEQ. ID. NO. 33279 | 51-LeuIleAspArgGlnVal-56 |
| SEQ. ID. NO. 33280 | 88-GlyArgGlnMetProSerGluLysThrLeu-97 |
| SEQ. ID. NO. 33281 | 103-GlnMetArgAspTyr-107 |
| Hydrophilic Regions - Hopp-Woods | |
| SEQ. ID. NO. 33282 | 5-GlnCysAspLysAlaArgHisMet-12 |
| SEQ. ID. NO. 33283 | 21-IleAsnArgHisArgGlnAlaSerAsnArgGly-31 |
| SEQ. ID. NO. 33284 | 39-GlnGlyAsnArgGluAlaGln-45 |
| SEQ. ID. NO. 33285 | 51-LeuIleAspArgGlnVal-56 |
| SEQ. ID. NO. 33286 | 91-MetProSerGluLysThrLeu-97 |
| g603 | |
| AMPHI Regions - AMPHI | |
| SEQ. ID. NO. 33287 | 119-MetLeuLeuAsnGluLeuGluLys-126 |
| SEQ. ID. NO. 33288 | 131-AspArgIleLysAlaIleGlyArgArgIleAlaHisGlyGlyGluLysTyr-147 |
| SEQ. ID. NO. 33289 | 157-ValLeuAspGluLeuLysAlaCysIlePro-166 |
| SEQ. ID. NO. 33290 | 171-HisAsnProAlaAsnIleSerGlyIleLeuAla-181 |
| SEQ. ID. NO. 33291 | 185-HisPheProGlyLeuProAsnValGly-193 |
| SEQ. ID. NO. 33292 | 198-SerPheHisGlnThrMetPro-204 |
| SEQ. ID. NO. 33293 | 211-AlaValProArgGluLeu-216 |
| SEQ. ID. NO. 33294 | 238-GluAlaAlaArgIleLeuGlyLysProLeuGluAspIleArgMetIleIleAlaHis-256 |
| SEQ. ID. NO. 33295 | 259-AsnGlyAlaSerIleThrAlaValLysAsnGlyLysSerVal-272 |
| SEQ. ID. NO. 33296 | 279-ThrProIleGluGly-283 |
| SEQ. ID. NO. 33297 | 298-TyrSerTyrProThr-302 |
| SEQ. ID. NO. 33298 | 323-ProGlyIleSerGluLeuProAsnAspCysArgThr-334 |
| SEQ. ID. NO. 33299 | 356-ArgLeuAlaLysTyrIleAlaSerMetAla-365 |
| SEQ. ID. NO. 33300 | 392-ValSerTyrLeuAsp-396 |

TABLE 1-continued

| | |
|---|---|
| Antigenic Index - Jameson-Wolf | |
| SEQ. ID. NO. 33301 | 1-MetAspSerArgLeuArgGlyAsnAspAlaArgLysTyrGly-14 |
| SEQ. ID. NO. 33302 | 17-PheAlaGlnArgGlyArgLeuLysHisThrProProAsnAlaHisProPheSerAspGlyProAlaProLysLysGlnProGlnThrThrArgArg AsnIleMetSer-52 |
| SEQ. ID. NO. 33303 | 64-SerSerLeuLysGlyAlaValIleAspArgLysSerGlySer-77 |
| SEQ. ID. NO. 33304 | 83-LeuGlyGluArgLeuThrThrProGluAla-92 |
| SEQ. ID. NO. 33305 | 95-ThrPheAsnLysAspGlyAsnLysArgGlnValProLeuSerGlyArgAsnCysHis-113 |
| SEQ. ID. NO. 33306 | 123-GluLeuGluLysHisGlyLeuHisAspArgIleLysAlaIleGlyArgArgIleAlaHisGlyGlyGluLysTyrHisGlu-149 |
| SEQ. ID. NO. 33307 | 151-ValLeuIleAspGlnAspValLeuAspGluLeuLysAla-163 |
| SEQ. ID. NO. 33308 | 202-ThrMetProGluArgAlaTyr-208 |
| SEQ. ID. NO. 33309 | 214-ArgGluLeuArgLysLysTyrAlaPheArgArgTyrGlyPheHisGlyThrGlyMet-232 |
| SEQ. ID. NO. 33310 | 238-GluAlaAlaArgIleLeuGlyLysProLeuGluAspIleArg-251 |
| SEQ. ID. NO. 33311 | 257-LeuGlyAsnGlyAla-261 |
| SEQ. ID. NO. 33312 | 264-ThrAlaValLysAsnGlyLysSerValAspThrGlyMet-276 |
| SEQ. ID. NO. 33313 | 288-ThrArgCysGlyAspThrAspProGlyVal-297 |
| SEQ. ID. NO. 33314 | 310-AlaGlnValAspGluMetLeuAsnGluLysSerGlyPheProGlyIleSerGluLeuProAsnAspCysArgThrLeuGluIleAlaAlaAsp GluGlyArgGluGlyAlaArgLeu-348 |
| SEQ. ID. NO. 33315 | 379-GlyIleGlyGluAsnSerArgAsnIleArgAlaLysThr-391 |
| SEQ. ID. NO. 33316 | 402-IleAspThrLysAlaAsnMetGluLysArgTyrGlyAsnSerGlyIle-417 |
| SEQ. ID. NO. 33317 | 419-SerProThrAspSerSerPro-425 |
| SEQ. ID. NO. 33318 | 431-ProThrAsnGluGluLeu-436 |
| Hydrophilic Regions - Hopp-Woods | |
| SEQ. ID. NO. 33319 | 1-MetAspSerArgLeuArgGlyAsnAspAlaArgLysTyrGly-14 |
| SEQ. ID. NO. 33320 | 17-PheAlaGlnArgGlyArgLeuLysHisThrPro-27 |
| SEQ. ID. NO. 33321 | 34-SerAspGlyProAlaProLysLysGlnProGlnThrThrArgArgAsnIleMet-51 |
| SEQ. ID. NO. 33322 | 69-AlaValIleAspArgLysSerGly-76 |
| SEQ. ID. NO. 33323 | 83-LeuGlyGluArgLeuThrThr-89 |
| SEQ. ID. NO. 33324 | 96-PheAsnLysAspGlyAsnLysArgGlnValProLeuSerGlyArgAsnCysHis-113 |
| SEQ. ID. NO. 33325 | 123-GluLeuGluLysHisGlyLeuHisAspArgIleLysAlaIleGlyArgArgIleAlaHisGlyGlyGluLysTyrHisGlu-149 |
| SEQ. ID. NO. 33326 | 156-AspValLeuAspGluLeuLysAla-163 |
| SEQ. ID. NO. 33327 | 203-MetProGluArgAlaTyr-208 |
| SEQ. ID. NO. 33328 | 214-ArgGluLeuArgLysLysTyrAlaPhe-222 |
| SEQ. ID. NO. 33329 | 238-GluAlaAlaArgIleLeuGlyLysProLeuGluAspIleArg-251 |
| SEQ. ID. NO. 33330 | 267-LysAsnGlyLysSerValAspThr-274 |
| SEQ. ID. NO. 33331 | 289-ArgCysGlyAspThrAspPro-295 |
| SEQ. ID. NO. 33332 | 310-AlaGlnValAspGluMetLeuAsnGluLysSerGly-321 |
| SEQ. ID. NO. 33333 | 328-LeuProAsnAspCysArgThrLeuGluIleAlaAlaAspGluGlyArgGluGlyAlaArgLeu-348 |
| SEQ. ID. NO. 33334 | 380-IleGlyGluAsnSerArgAsnIleArgAlaLysThr-391 |
| SEQ. ID. NO. 33335 | 402-IleAspThrLysAlaAsnMetGluLysArgTyrGly-413 |
| SEQ. ID. NO. 33336 | 432-ThrAsnGluGluLeu-436 |
| g604 | |
| AMPHI Regions - AMPHI | |
| SEQ. ID. NO. 33337 | 35-SerValValGlnPheAla-40 |
| SEQ. ID. NO. 33338 | 49-IleAspValGlyGlyValTyrGly-56 |
| SEQ. ID. NO. 33339 | 98-AspGlyPheLysPhePheGln-104 |
| SEQ. ID. NO. 33340 | 111-AspValValLeuGlnLeuPheAlaArgValAlaGlnValGlyGlyValGlnGluAsn-129 |
| SEQ. ID. NO. 33341 | 146-ArgHisIleAsnPheValAspGlnIleAlaGlyTrpGlu-158 |
| Antigenic Index - Jameson-Wolf | |
| SEQ. ID. NO. 33342 | 10-SerAlaAlaCysGlyLysValAspGlnArgThrGluHisGlyGlyGlyAspGlyAspArgGlyAspAlaHis-33 |
| SEQ. ID. NO. 33343 | 44-GlyAlaTyrArgGlnIleAspVal-51 |
| SEQ. ID. NO. 33344 | 65-GlyGlyGlyArgAspGluGlyGlyPheArgArgAlaArgAlaGlyGlyGlyPhe-82 |
| SEQ. ID. NO. 33345 | 95-IleCysAlaAspGly-99 |
| SEQ. ID. NO. 33346 | 101-LysPhePheGlnArgGlyGlyIle-108 |
| SEQ. ID. NO. 33347 | 125-GlyValGlnGluAsnGlyArgAsnAlaArgValAspGluArgGlyPheGln-141 |
| Hydrophilic Regions - Hopp-Woods | |
| SEQ. ID. NO. 33348 | 14-GlyLysValAspGlnArgThrGluHisGlyGlyGlyAspGlyAspArgGlyAspAlaHis-33 |
| SEQ. ID. NO. 33349 | 66-GlyGlyArgAspGluGlyGlyPheArgArgAlaArgAla-78 |
| SEQ. ID. NO. 33350 | 125-GlyValGlnGluAsnGlyArgAsnAlaArgValAspGluArgGlyPhe-140 |
| g605 | |
| AMPHI Regions - AMPHI | |
| SEQ. ID. NO. 33351 | 13-ArgGlnIleTrpLysIleAlaAsp-20 |
| SEQ. ID. NO. 33352 | 38-ThrLeuPheTyrArgPheIleSerGluAsnPheThrAspTyrMetGln-53 |
| SEQ. ID. NO. 33353 | 107-LysLeuLysGluIlePheThrAlaIle-115 |
| SEQ. ID. NO. 33354 | 126-GlnGlyIleLysGlyLeuPheAspAspPheAsp-136 |
| SEQ. ID. NO. 33355 | 141-ArgLeuGlySerThr-145 |
| SEQ. ID. NO. 33356 | 155-AlaValLeuLysGlyValAlaGluLeu-163 |
| SEQ. ID. NO. 33357 | 178-AspAlaTyrGluTyrLeuIleSerAsn-186 |
| SEQ. ID. NO. 33358 | 188-AlaAlaAsnAlaGlyLys-193 |
| SEQ. ID. NO. 33359 | 204-ValSerLysLeuIleAlaArg-210 |
| SEQ. ID. NO. 33360 | 217-GluLysValAsnLysIleTyrAspPro-225 |
| SEQ. ID. NO. 33361 | 240-PheAspGluHisIle-244 |
| SEQ. ID. NO. 33362 | 291-AspSerLysProPheAspAlaValValSerAsn-301 |
| SEQ. ID. NO. 33363 | 341-HisAlaLeuAsnTyr-345 |
| SEQ. ID. NO. 33364 | 355-ValSerPheProGly-359 |
| SEQ. ID. NO. 33365 | 433-GluHisIleAlaGluIleValLysLeuPheAla-443 |
| SEQ. ID. NO. 33366 | 452-AlaGlnAsnAlaAlaGlnGlnThr-459 |
| SEQ. ID. NO. 33367 | 478-ThrArgGluValIleAspIle-484 |
| SEQ. ID. NO. 33368 | 489-AlaGluIleSerGluThrValAlaLysIleGluArgLeuArgArgGluIleAspGluValIleAlaGluIleGlu-513 |

TABLE 1-continued

| | |
|---|---|
| Antigenic Index - Jameson-Wolf | |
| SEQ. ID. NO. 33369 | 5-MetGlnGlnArgAlaGlnLeu-11 |
| SEQ. ID. NO. 33370 | 18-IleAlaAspGluValArgGlyAlaValAspGlyTrpAsp-30 |
| SEQ. ID. NO. 33371 | 44-IleSerGluAsnPheThrAspTyrMetGlnAlaGlyAspSerSerIleAsp-60 |
| SEQ. ID. NO. 33372 | 63-AlaMetProAspSer-67 |
| SEQ. ID. NO. 33373 | 71-ProGluIleLysAspAspAlaValLysVal-80 |
| SEQ. ID. NO. 33374 | 98-AlaHisGlnAsnGluGluLeuAsnThrLysLeuLysGlu-110 |
| SEQ. ID. NO. 33375 | 116-GluSerSerAlaSerGlyTyrProSerGluGlnGlyIleLysGlyLeuPheAspAspPheAspThrThrSerSerArgLeu-142 |
| SEQ. ID. NO. 33376 | 146-ValAlaAspLysAsnLysArgLeu-153 |
| SEQ. ID. NO. 33377 | 164-AspPheGlyAsnPheGluAspHisArgIle-173 |
| SEQ. ID. NO. 33378 | 190-AsnAlaGlyLysSerGlyGlyGluPhePheThr-200 |
| SEQ. ID. NO. 33379 | 215-GlyGlnGluLysValAsnLysIleTyrAspProAlaCysGlySerGlySer-231 |
| SEQ. ID. NO. 33380 | 235-GlnAlaLysLysGlnPheAsp-241 |
| SEQ. ID. NO. 33381 | 253-GluIleAsnHisThrThrTyrAsn-260 |
| SEQ. ID. NO. 33382 | 280-LeuGlyAspThrLeuThrAsnProLysLeuLysAspSerLysProPheAspAla-297 |
| SEQ. ID. NO. 33383 | 309-IleGlySerAspAspProThrLeuIleAsnAspAspArgPheAlaPro-324 |
| SEQ. ID. NO. 33384 | 330-ProLysSerLysAlaAsp-335 |
| SEQ. ID. NO. 33385 | 345-TyrLeuSerGlyArgGlyArgAlaAla-353 |
| SEQ. ID. NO. 33386 | 362-TyrArgGlyGlyAlaGluGlnLysIleArg-371 |
| SEQ. ID. NO. 33387 | 403-LeuSerLysHisLysAspAsnThrAsp-411 |
| SEQ. ID. NO. 33388 | 419-GlyPhePheLysLysGluThrAsnAsnAsnValLeuThrGluGluHisIle-435 |
| SEQ. ID. NO. 33389 | 442-PheAlaAspLysAlaAspVal-448 |
| SEQ. ID. NO. 33390 | 458-GlnThrValLysAspAsnGlyTyr-465 |
| SEQ. ID. NO. 33391 | 473-ValGluAlaGluAspThrArgGluValIleAsp-483 |
| SEQ. ID. NO. 33392 | 490-GluIleSerGluThrValAlaLysIleGluArgLeuArgArgGluIleAspGluValIleAlaGluIleGluThr-514 |
| Hydrophilic Regions - Hopp-Woods | |
| SEQ. ID. NO. 33393 | 18-IleAlaAspGluValArgGlyAlaValAsp-27 |
| SEQ. ID. NO. 33394 | 55-GlyAspSerSerIle-59 |
| SEQ. ID. NO. 33395 | 71-ProGluIleLysAspAspAlaValLysVal-80 |
| SEQ. ID. NO. 33396 | 98-AlaHisGlnAsnGluGluLeuAsnThrLysLeuLysGlu-110 |
| SEQ. ID. NO. 33397 | 131-LeuPheAspAspPheAspThrThrSerSerArgLeu-142 |
| SEQ. ID. NO. 33398 | 146-ValAlaAspLysAsnLysArgLeu-153 |
| SEQ. ID. NO. 33399 | 167-AsnPheGluAspHisArgIle-173 |
| SEQ. ID. NO. 33400 | 191-AlaGlyLysSerGlyGly-196 |
| SEQ. ID. NO. 33401 | 215-GlyGlnGluLysValAsnLysIleTyrAsp-224 |
| SEQ. ID. NO. 33402 | 235-GlnAlaLysLysGlnPheAsp-241 |
| SEQ. ID. NO. 33403 | 287-ProLysLeuLysAspSerLysProPhe-295 |
| SEQ. ID. NO. 33404 | 310-GlySerAspAspProThrLeuIleAsnAspAspArgPheAla-323 |
| SEQ. ID. NO. 33405 | 330-ProLysSerLysAlaAsp-335 |
| SEQ. ID. NO. 33406 | 348-GlyArgGlyArgAla-352 |
| SEQ. ID. NO. 33407 | 364-GlyGlyAlaGluGlnLysIleArg-371 |
| SEQ. ID. NO. 33408 | 404-SerLysHisLysAspAsnThrAsp-411 |
| SEQ. ID. NO. 33409 | 419-GlyPhePheLysLysGluThrAsn-426 |
| SEQ. ID. NO. 33410 | 430-LeuThrGluGluHisIle-435 |
| SEQ. ID. NO. 33411 | 442-PheAlaAspLysAlaAspVal-448 |
| SEQ. ID. NO. 33412 | 458-GlnThrValLysAspAsnGly-464 |
| SEQ. ID. NO. 33413 | 473-ValGluAlaGluAspThrArgGluValIleAsp-483 |
| SEQ. ID. NO. 33414 | 490-GluIleSerGluThrValAlaLysIleGluArgLeuArgArgGluIleAspGluValIleAlaGluIleGluThr-514 |
| g606 | |
| AMPHI Regions - AMPHI | |
| SEQ. ID. NO. 33415 | 72-LeuLeuAspHisMetThrArgAspGlu-80 |
| SEQ. ID. NO. 33416 | 90-AlaHisValGlyAsnGlyAsp-96 |
| SEQ. ID. NO. 33417 | 100-LeuThrLeuIleGlnGlyValValAsnThrPhe-110 |
| SEQ. ID. NO. 33418 | 116-ArgIleIleAlaAsn-120 |
| SEQ. ID. NO. 33419 | 139-SerMetValPheGlnIleLeuPheGlyPheLeuAlaSerLeuIleVal-154 |
| SEQ. ID. NO. 33420 | 171-LysLeuValGlyAlaProLysMetIleSerAlaLeuGlnArg-184 |
| SEQ. ID. NO. 33421 | 191-AspLeuProGluGluMetAsnAla-198 |
| Antigenic Index - Jameson-Wolf | |
| SEQ. ID. NO. 33422 | 13-GluValIleAspThrProArgThrGluGluGluAla-24 |
| SEQ. ID. NO. 33423 | 31-GluAlaGlnAlaArgGlnTrpAsnLeuLysThrProGlu-43 |
| SEQ. ID. NO. 33424 | 48-HisSerProGluProAsnAla-54 |
| SEQ. ID. NO. 33425 | 57-ThrGlyAlaSerArgAsnSerSer-64 |
| SEQ. ID. NO. 33426 | 75-HisMetThrArgAspGluValGluAla-83 |
| SEQ. ID. NO. 33427 | 92-ValGlyAsnGlyAsp-96 |
| SEQ. ID. NO. 33428 | 122-IleAlaArgAsnAsnAspGlySerGlnSerGlnGlyThr-134 |
| SEQ. ID. NO. 33429 | 159-ArgGlnArgGluTyrArgAlaAspAlaGlyAla-169 |
| SEQ. ID. NO. 33430 | 182-LeuGlnArgLeuLysGlyAsnProValAspLeuProGluGluMetAsn-197 |
| SEQ. ID. NO. 33431 | 203-GlyAspThrArgAspSerLeuLeuSerThrHisProSerLeuAspAsnArgIleAlaArgLeuLysSer-225 |
| Hydrophilic Regions - Hopp-Woods | |
| SEQ. ID. NO. 33432 | 13-GluValIleAspThrProArgThrGluGluGluAla-24 |
| SEQ. ID. NO. 33433 | 59-AlaSerArgAsnSer-63 |
| SEQ. ID. NO. 33434 | 75-HisMetThrArgAspGluValGluAla-83 |
| SEQ. ID. NO. 33435 | 124-ArgAsnAsnAspGlySerGlnSer-131 |
| SEQ. ID. NO. 33436 | 159-ArgGlnArgGluTyrArgAlaAspAlaGlyAla-169 |
| SEQ. ID. NO. 33437 | 183-GlnArgLeuLysGlyAsnPro-189 |
| SEQ. ID. NO. 33438 | 191-AspLeuProGluGluMetAsn-197 |

TABLE 1-continued

| | |
|---|---|
| SEQ. ID. NO. 33439 | 203-GlyAspThrArgAspSerLeu-209 |
| SEQ. ID. NO. 33440 | 214-ProSerLeuAspAsnArgIleAlaArgLeuLysSer-225 |
| g607 | |
| AMPHI Regions - AMPHI | |
| SEQ. ID. NO. 33441 | 15-LysGluIleArgLeuLeuThrAlaLeuAlaLeu-25 |
| SEQ. ID. NO. 33442 | 70-PheMetGlyIleMetAlaAlaLeuAsnProMetIleAlaGln-83 |
| SEQ. ID. NO. 33443 | 90-ThrGlyGluAlaGlyGlu-95 |
| SEQ. ID. NO. 33444 | 104-GlyLeuIleLeuGlyIlePheGlyMetIleLeuMetTrpAlaAlaIleThrProPheArgAsnTrpLeuThrLeuSerAspTyrValGluGlyThrMet-136 |
| SEQ. ID. NO. 33445 | 151-MetValHisArgAlaLeuHisAlaTyrAlaSerSer-162 |
| SEQ. ID. NO. 33446 | 226-PhePheArgProPheGly-231 |
| SEQ. ID. NO. 33447 | 244-PheLysGlnIleTrpLysIleGlyAla-252 |
| SEQ. ID. NO. 33448 | 320-AlaArgTyrIleSerGlyValSerLeu-328 |
| SEQ. ID. NO. 33449 | 337-IleThrValLeuSerLeuVal-343 |
| SEQ. ID. NO. 33450 | 348-ProLeuAlaSerMetTyr-353 |
| SEQ. ID. NO. 33451 | 373-PheGlnProAlaAspPheThrGlnCysIleAlaSerTyrAla-386 |
| SEQ. ID. NO. 33452 | 424-TyrGlyPheTrpThrAlaLeuIleAla-432 |
| Antigenic Index - Jameson-Wolf | |
| SEQ. ID. NO. 33453 | 4-AspLeuAspArgPheSer-9 |
| SEQ. ID. NO. 33454 | 47-GlyAlaGlyLysGluAspLeuAla-54 |
| SEQ. ID. NO. 33455 | 86-GlyAlaGlyLysThrGlyGluAlaGlyGluThrGlyArgGln-99 |
| SEQ. ID. NO. 33456 | 121-ProPheArgAsnTrp-125 |
| SEQ. ID. NO. 33457 | 128-LeuSerAspTyrValGluGlyThr-135 |
| SEQ. ID. NO. 33458 | 160-AlaSerSerLeuAsnArgProArgLeu-168 |
| SEQ. ID. NO. 33459 | 222-AlaLysGluLysPhePheArg-228 |
| SEQ. ID. NO. 33460 | 234-AlaLysPheGlyLysProAspTrp-241 |
| SEQ. ID. NO. 33461 | 311-SerLeuGlyArgArgGluPheSerArgAlaArgTyrIleSer-324 |
| SEQ. ID. NO. 33462 | 348-ProLeuAlaSerMetTyrAsnAspAspProAla-358 |
| SEQ. ID. NO. 33463 | 388-ArgGlyTyrLysValThrLys-394 |
| SEQ. ID. NO. 33464 | 452-LeuValLysSerHisLysAlaVal-459 |
| Hydrophilic Regions - Hopp-Woods | |
| SEQ. ID. NO. 33465 | 47-GlyAlaGlyLysGluAspLeuAla-54 |
| SEQ. ID. NO. 33466 | 89-LysThrGlyGluAlaGlyGluThrGlyArg-98 |
| SEQ. ID. NO. 33467 | 163-LeuAsnArgProArg-167 |
| SEQ. ID. NO. 33468 | 222-AlaLysGluLysPhePhe-227 |
| SEQ. ID. NO. 33469 | 312-LeuGlyArgArgGluPheSerArg-319 |
| SEQ. ID. NO. 33470 | 353-TyrAsnAspAspProAla-358 |
| SEQ. ID. NO. 33471 | 390-TyrLysValThrLys-394 |
| SEQ. ID. NO. 33472 | 452-LeuValLysSerHisLysAlaVal-459 |
| g608 | |
| AMPHI Regions - AMPHI | |
| SEQ. ID. NO. 33473 | 66-AlaIleArgLysIleLeuGln-72 |
| SEQ. ID. NO. 33474 | 93-ValLeuSerLeuLeu-97 |
| SEQ. ID. NO. 33475 | 103-ArgAlaSerAspGluLeuAlaArgIlePheGlyThr-114 |
| SEQ. ID. NO. 33476 | 124-AspIleGlyHisGlyIleLysGlnIleGlyArgAsnIleAlaGluGlnIleGlyGlyPheSerArgGluProGluSerAlaAsnThrGlyAsnGluAlaLeuAlaAspCysLeuAspGluIleSerArgLeuArgAspGlyValGluArgLeuAsnGluArgLeuAspArgLeu-181 |
| Antigenic Index - Jameson-Wolf | |
| SEQ. ID. NO. 33477 | 13-LeuGlnSerProAspSerArgSerGluLeuThr-23 |
| SEQ. ID. NO. 33478 | 39-LeuAlaGlyArgIleThrGluAspGlyLeuLeuSerAlaGlyAsnGlyPheAlaAspThrGluIleThrPheArgAsnSerAlaIleArgLysIleLeuGlnGlyGlyGluProGlyAlaGlyAspIleArgLeuGluGly-85 |
| SEQ. ID. NO. 33479 | 98-GlySerLeuArgSerArgAlaSerAspGluLeuAla-109 |
| SEQ. ID. NO. 33480 | 116-AlaGlyIleGlySerArgAlaThrAspIle-125 |
| SEQ. ID. NO. 33481 | 130-LysGlnIleGlyArgAsnIleAla-137 |
| SEQ. ID. NO. 33482 | 140-IleGlyGlyPheSerArgGluProGluSerAlaAsnThrGlyAsnGluAlaLeuAlaAspCysLeuAspGluIleSerArgLeuArgAspGlyValGluArgLeuAsnGluArgLeuAspArgLeuGluArgAspIleTrp-186 |
| Hydrophilic Regions - Hopp-Woods | |
| SEQ. ID. NO. 33483 | 15-SerProAspSerArgSerGluLeu-22 |
| SEQ. ID. NO. 33484 | 39-LeuAlaGlyArgIleThrGluAspGlyLeu-48 |
| SEQ. ID. NO. 33485 | 56-AlaAspThrGluIleThrPhe-62 |
| SEQ. ID. NO. 33486 | 65-SerAlaIleArgLysIleLeuGln-72 |
| SEQ. ID. NO. 33487 | 74-GlyGluProGlyAlaGlyAspIleArgLeuGluGly-85 |
| SEQ. ID. NO. 33488 | 100-LeuArgSerArgAlaSerAspGluLeuAla-109 |
| SEQ. ID. NO. 33489 | 118-IleGlySerArgAlaThrAsp-124 |
| SEQ. ID. NO. 33490 | 143-PheSerArgGluProGluSerAlaAsnThrGlyAsnGluAlaLeuAlaAspCysLeuAspGluIleSerArgLeuArgAspGlyValGluArgLeuAsnGluArgLeuAspArgLeuGluArgAspIleTrp-186 |
| g609 | |
| AMPHI Regions - AMPHI | |
| SEQ. ID. NO. 33491 | 15-ThrLeuAspAlaPheVal-20 |
| SEQ. ID. NO. 33492 | 30-HisHisIlePheHisGluPheArgValPheValGlyLeuPhe-43 |
| SEQ. ID. NO. 33493 | 52-PheGluGlnAlaValGlu-57 |
| SEQ. ID. NO. 33494 | 67-IleAspAsnPheLeu-71 |
| SEQ. ID. NO. 33495 | 114-ValAlaValCysProVal-119 |
| Antigenic Index - Jameson-Wolf | |
| SEQ. ID. NO. 33496 | 10-AlaLeuAspAspGluThrLeu-16 |
| SEQ. ID. NO. 33497 | 20-ValGlyAsnGlnArgSerSerAspIleAla-29 |
| SEQ. ID. NO. 33498 | 71-LeuAspThrAspPheGlyIleGlySerGlnAlaAspGlyAsnValArg-86 |
| SEQ. ID. NO. 33499 | 99-GlyThrArgAlaLysArgGlyTyrGlyAsnHisAspLeu-111 |
| SEQ. ID. NO. 33500 | 124-ArgGluAlaAspIle-128 |

TABLE 1-continued

| | |
|---|---|
| Hydrophilic Regions - Hopp-Woods | |
| SEQ. ID. NO. 33501 | 10-AlaLeuAspAspGluThrLeu-16 |
| SEQ. ID. NO. 33502 | 23-GlnArgSerSerAspIle-28 |
| SEQ. ID. NO. 33503 | 79-SerGlnAlaAspGlyAsnVal-85 |
| SEQ. ID. NO. 33504 | 100-ThrArgAlaLysArgGlyTyrGly-107 |
| SEQ. ID. NO. 33505 | 124-ArgGluAlaAspIle-128 |
| g610 | |
| AMPHI Regions - AMPHI | |
| SEQ. ID. NO. 33506 | 6-MetGlnPheProTyrArg-11 |
| SEQ. ID. NO. 33507 | 18-MetArgArgMetArgArg-23 |
| SEQ. ID. NO. 33508 | 97-ThrGlyArgAlaGlnGluAlaTyr-104 |
| SEQ. ID. NO. 33509 | 111-ProSerThrValArgAlaLeuArgGluArg-120 |
| SEQ. ID. NO. 33510 | 187-IleArgGluAlaLeuGlu-192 |
| SEQ. ID. NO. 33511 | 208-TyrAlaSerAlaPheTyrGlyProPheArgAsp-218 |
| SEQ. ID. NO. 33512 | 223-SerGlyAsnLeuGlyLysAlaAsp-230 |
| SEQ. ID. NO. 33513 | 268-LeuAspValValArgArgValLysAspGlu-277 |
| SEQ. ID. NO. 33514 | 296-AlaAlaValAlaAsn-300 |
| Antigenic Index - Jameson-Wolf | |
| SEQ. ID. NO. 33515 | 11-ArgAsnValProAlaSerArgMetArgArgMetArgArgAspAspPheSerArgArgLeuMetArg-32 |
| SEQ. ID. NO. 33516 | 34-HisMetLeuThrAlaAspAsp-40 |
| SEQ. ID. NO. 33517 | 50-GlyAlaAlaArgGluGluAspValProSerMetProGlyValLysArgGlnSerLeuAsp-69 |
| SEQ. ID. NO. 33518 | 75-AlaGluGluAlaValLys-80 |
| SEQ. ID. NO. 33519 | 93-ThrAlaAsnLysThrGlyArgAlaGlnGluAlaTyrAsnProGluGlyLeuVal-110 |
| SEQ. ID. NO. 33520 | 115-ArgAlaLeuArgGluArgPhePro-122 |
| SEQ. ID. NO. 33521 | 139-GlyGlnAspGlyLeuThrAspGluAsnGlyTyrValMetAsnAspGluThrVal-156 |
| SEQ. ID. NO. 33522 | 175-AlaProSerAspMetMetAspGlyArgIleGlyAlaIleArgGluAlaLeuGluAspAlaGlyHis-196 |
| SEQ. ID. NO. 33523 | 215-ProPheArgAspAlaValGlySerSerGlyAsnLeuGlyLysAlaAspLysLysThrTyrGlnMetAspProAlaAsnThrAspGluAlaLeu His-246 |
| SEQ. ID. NO. 33524 | 250-LeuAspIleGlnGluGlyAlaAsp-257 |
| SEQ. ID. NO. 33525 | 270-ValValArgArgValLysAspGluPheGlyVal-280 |
| SEQ. ID. NO. 33526 | 302-TrpLeuAspGlyGlyLysValVal-309 |
| SEQ. ID. NO. 33527 | 317-LysArgAlaGlyAlaAspGly-323 |
| SEQ. ID. NO. 33528 | 331-GluAlaAlaLysMetLeuLysArg-338 |
| Hydrophilic Regions - Hopp-Woods | |
| SEQ. ID. NO. 33529 | 14-ProAlaSerArgMetArgArgMetArgArgAspAspPheSerArgArgLeuMetArg-32 |
| SEQ. ID. NO. 33530 | 34-HisMetLeuThrAla-38 |
| SEQ. ID. NO. 33531 | 50-GlyAlaAlaArgGluGluAspValProSer-59 |
| SEQ. ID. NO. 33532 | 61-ProGlyValLysArgGlnSerLeuAsp-69 |
| SEQ. ID. NO. 33533 | 75-AlaGluGluAlaValLys-80 |
| SEQ. ID. NO. 33534 | 95-AsnLysThrGlyArgAlaGlnGluAlaTyrAsn-105 |
| SEQ. ID. NO. 33535 | 115-ArgAlaLeuArgGluArgPhePro-122 |
| SEQ. ID. NO. 33536 | 141-AspGlyLeuThrAspGluAsnGly-148 |
| SEQ. ID. NO. 33537 | 151-MetAsnAspGluThrVal-156 |
| SEQ. ID. NO. 33538 | 178-AspMetMetAspGlyArgIleGlyAlaIleArgGluAlaLeuGluAspAlaGly-195 |
| SEQ. ID. NO. 33539 | 216-PheArgAspAlaValGly-221 |
| SEQ. ID. NO. 33540 | 225-AsnLeuGlyLysAlaAspLysLysThrTyrGln-235 |
| SEQ. ID. NO. 33541 | 238-ProAlaAsnThrAspGluAlaLeuHis-246 |
| SEQ. ID. NO. 33542 | 250-LeuAspIleGlnGluGlyAlaAsp-257 |
| SEQ. ID. NO. 33543 | 270-ValValArgArgValLysAspGluPheGly-279 |
| SEQ. ID. NO. 33544 | 317-LysArgAlaGlyAla-321 |
| SEQ. ID. NO. 33545 | 331-GluAlaAlaLysMetLeuLysArg-338 |
| g611 | |
| AMPHI Regions - AMPHI | |
| SEQ. ID. NO. 33546 | 15-CysArgLeuPheGlyLysLeuSerLeu-23 |
| SEQ. ID. NO. 33547 | 26-ArgLeuLeuProGlyLeuCysArgGly-34 |
| SEQ. ID. NO. 33548 | 48-ArgSerValArgArgValIle-54 |
| SEQ. ID. NO. 33549 | 63-GlnValValAlaVal-67 |
| SEQ. ID. NO. 33550 | 104-ValPheIleGluAspPheVal-110 |
| SEQ. ID. NO. 33551 | 130-GlyPheLeuGlyAsnValLeuArgThr-138 |
| Antigenic Index - Jameson-Wolf | |
| SEQ. ID. NO. 33552 | 1-MetProSerGluAsnGlyMetGlyLysArgGlnLeuAla-13 |
| SEQ. ID. NO. 33553 | 29-ProGlyLeuCysArgGlyGlyValCysArgGlyArgCys-41 |
| SEQ. ID. NO. 33554 | 45-PheProSerArgSerValArgArgValIlePheArgArgValArgIle-60 |
| SEQ. ID. NO. 33555 | 119-AsnProAlaAspPheArgVal-125 |
| SEQ. ID. NO. 33556 | 142-AlaProGlnGluAsp-146 |
| Hydrophilic Regions - Hopp-Woods | |
| SEQ. ID. NO. 33557 | 1-MetProSerGluAsnGlyMetGlyLysArgGlnLeuAla-13 |
| SEQ. ID. NO. 33558 | 35-GlyValCysArgGlyArgCys-41 |
| SEQ. ID. NO. 33559 | 53-ValIlePheArgArgValArgIle-60 |
| SEQ. ID. NO. 33560 | 121-AlaAspPheArgVal-125 |
| g612 | |
| AMPHI Regions - AMPHI | |
| SEQ. ID. NO. 33561 | 6-AsnIleAlaLysLysLeuAlaGlyVal-14 |
| SEQ. ID. NO. 33562 | 57-LysAlaValGluLysCysAlaGluAsnValLeu-67 |
| SEQ. ID. NO. 33563 | 80-ValGlyAspPheProAsn-85 |
| Antigenic Index - Jameson-Wolf | |
| SEQ. ID. NO. 33564 | 7-IleAlaLysLysLeuAlaGlyValAsp-15 |
| SEQ. ID. NO. 33565 | 17-IleAlaPheAspPheAspGly-23 |
| SEQ. ID. NO. 33566 | 27-AspPheGlyArgAspAspAlaValArgHisSerGlyVal-39 |
| SEQ. ID. NO. 33567 | 57-LysAlaValGluLysCysAlaGlu-64 |

TABLE 1-continued

SEQ. ID. NO. 33568 98-HisHisArgAsnProTyrIleLysLeuAsnLysSerLysSerProAspIlePheArg-116
SEQ. ID. NO. 33569 119-PheTyrGlyHisSerAsn-124
Hydrophilic Regions - Hopp-Woods
SEQ. ID. NO. 33570 7-IleAlaLysLysLeuAlaGlyValAsp-15
SEQ. ID. NO. 33571 28-PheGlyArgAspAspAlaValArg-35
SEQ. ID. NO. 33572 57-LysAlaValGluLysCysAlaGlu-64
SEQ. ID. NO. 33573 105-LysLeuAsnLysSerLysSerProAspIlePhe-115
g613
AMPHI Regions - AMPHI
SEQ. ID. NO. 33574 95-MetProArgMetArgSerProSerSerLeuMetSerProAla-108
SEQ. ID. NO. 33575 140-SerSerValMetArgProAla-146
SEQ. ID. NO. 33576 166-GluArgLeuSerGlyLeuCysArgIle-174
SEQ. ID. NO. 33577 184-AspIlePheSerAspTrpGly-190
Antigenic Index - Jameson-Wolf
SEQ. ID. NO. 33578 1-MetSerArgSerSerLeuSerArgArgSerLeuArgArgSerThrProSerArg-18
SEQ. ID. NO. 33579 23-SerSerArgGlnSerAlaArgAla-30
SEQ. ID. NO. 33580 36-AlaAspSerGlySerArgGluAsnProProIleCysSer-48
SEQ. ID. NO. 33581 73-ProLysIleArgAlaAsnSerSerAspAlaArgGluArgArgLeuProSerArgAspSerThrAla-94
SEQ. ID. NO. 33582 96-ProArgMetArgSerProSerSerLeu-104
SEQ. ID. NO. 33583 107-ProAlaProGlySerProPro-113
SEQ. ID. NO. 33584 130-AlaLysProPheProAlaGluSerLysProSerSerValMetArgProAlaSer-147
SEQ. ID. NO. 33585 159-ProAlaLysGluValSerSerGluArgLeuSerGlyLeuCysArgIleArgArg-176
SEQ. ID. NO. 33586 178-MetMetGlyArgArgAlaAspIlePheSerAspTrpGlyGlyGluCys-193
Hydrophilic Regions - Hopp-Woods
SEQ. ID. NO. 33587 1-MetSerArgSerSerLeuSerArgArgSerLeuArgArgSerThrProSer-17
SEQ. ID. NO. 33588 24-SerArgGlnSerAlaArgAla-30
SEQ. ID. NO. 33589 38-SerGlySerArgGluAsnProPro-45
SEQ. ID. NO. 33590 73-ProLysIleArgAlaAsnSerSerAspAlaArgGluArgArgLeuProSerArgAspSerThrAla-94
SEQ. ID. NO. 33591 96-ProArgMetArgSerProSer-102
SEQ. ID. NO. 33592 133-PheProAlaGluSerLysProSerSerValMetArg-144
SEQ. ID. NO. 33593 159-ProAlaLysGluValSerSerGluArgLeuSerGly-170
SEQ. ID. NO. 33594 172-CysArgIleArgArg-176
SEQ. ID. NO. 33595 178-MetMetGlyArgArgAlaAspIle-185
g614
AMPHI Regions - AMPHI
SEQ. ID. NO. 33596 20-SerGlnPheIleArgGlnValAsnAsnGly-29
SEQ. ID. NO. 33597 65-AsnLeuIleGlnThrLeuLeuAsn-72
SEQ. ID. NO. 33598 90-AlaLeuPheTyrSerLeuLeuProValLeu-99
SEQ. ID. NO. 33599 144-ValAlaGlyCysAspGluAlaLysGluGluValGlnGluIleValAspTyrLeuLysAlaProAsnArgTyrGlnSerLeu-170
SEQ. ID. NO. 33600 210-AspPheValGluMetPheVal-216
SEQ. ID. NO. 33601 222-ArgValArgAspMetPheGluGln-229
SEQ. ID. NO. 33602 242-GluIleAspAlaValGlyArg-248
SEQ. ID. NO. 33603 295-ProAlaLeuGlnArgProGlyArgPheAsp-304
SEQ. ID. NO. 33604 333-SerValAspLeuLeuSerLeuAla-340
SEQ. ID. NO. 33605 349-AlaAspLeuAlaLysLeuVal-355
Antigenic Index - Jameson-Wolf
SEQ. ID. NO. 33606 7-LeuAspGlyLysLysGluAspAsnGlyGlnIleGlu-18
SEQ. ID. NO. 33607 25-GlnValAsnAsnGlyGluValSerGly-33
SEQ. ID. NO. 33608 45-LeuIleLysGlyGluArgThrAspLysSerThrPhe-56
SEQ. ID. NO. 33609 59-AsnAlaProLeuAspAspAsnLeu-66
SEQ. ID. NO. 33610 70-LeuLeuAsnLysAsnValArgValLysValThrProGluGluLysProSerAla-87
SEQ. ID. NO. 33611 112-GlnAlaGlyGlyGlyGlyLysGlyGly-120
SEQ. ID. NO. 33612 123-SerPheGlyLysSerArgAlaArgLeuLeuAspLysAspAlaAsnLys-138
SEQ. ID. NO. 33613 145-AlaGlyCysAspGluAlaLysGluGluValGlnGlu-156
SEQ. ID. NO. 33614 161-LeuLysAlaProAsnArgTyrGlnSerLeuGlyGlyArgValProArgGly-177
SEQ. ID. NO. 33615 182-GlySerProGlyThrGlyLysThrLeuLeu-191
SEQ. ID. NO. 33616 207-SerGlySerAspPhe-211
SEQ. ID. NO. 33617 219-GlyAlaSerArgValArgAspMetPheGluGlnAlaLysLysAsnAla-234
SEQ. ID. NO. 33618 241-AspGluIleAspAlaValGlyArgGlnArgGlyAlaGlyLeuGlyGlyGlyAsnAspGluArgGluGlnThrLeu-265
SEQ. ID. NO. 33619 272-MetAspGlyPheGluSerAsnGln-279
SEQ. ID. NO. 33620 287-ThrAsnArgProAspValLeuAspProAlaLeuGlnArgProGlyArgPheAspArg-305
SEQ. ID. NO. 33621 311-LeuProAspIleArgGlyArgGluGlnXxx-320
SEQ. ID. NO. 33622 323-ValHisSerLysLysValProLeuAspGluSerValAsp-335
SEQ. ID. NO. 33623 341-ArgGlyThrProGlyPheSerGly-348
SEQ. ID. NO. 33624 362-AlaGlyArgArgAsnLysValLysValAspGlnSerAspLeuLysThrProLysThrLysSer-382
Hydrophilic Regions - Hopp-Woods
SEQ. ID. NO. 33625 7-LeuAspGlyLysLysGluAspAsnGlyGln-16
SEQ. ID. NO. 33626 26-ValAsnAsnGlyGluValSer-32
SEQ. ID. NO. 33627 46-IleLysGlyGluArgThrAspLysSerThr-55
SEQ. ID. NO. 33628 61-ProLeuAspAspAsnLeu-66
SEQ. ID. NO. 33629 73-LysAsnValArgValLysValThrProGluGluLysProSerAla-87
SEQ. ID. NO. 33630 115-GlyGlyGlyLysGlyGly-120
SEQ. ID. NO. 33631 125-GlyLysSerArgAlaArgLeuLeuAspLysAspAlaAsnLys-138
SEQ. ID. NO. 33632 145-AlaGlyCysAspGluAlaLysGluGluValGlnGlu-156
SEQ. ID. NO. 33633 162-LysAlaProAsnArg-166
SEQ. ID. NO. 33634 171-GlyGlyArgValProArg-176
SEQ. ID. NO. 33635 221-SerArgValArgAspMetPheGluGlnAlaLysLysAsnAla-234
SEQ. ID. NO. 33636 241-AspGluIleAspAlaValGlyArgGlnArgGlyAlaGly-253
SEQ. ID. NO. 33637 256-GlyGlyAsnAspGluArgGluGlnThr-264
SEQ. ID. NO. 33638 273-AspGlyPheGluSer-277

TABLE 1-continued

| | |
|---|---|
| SEQ. ID. NO. 33639 | 287-ThrAsnArgProAspValLeuAsp-294 |
| SEQ. ID. NO. 33640 | 296-AlaLeuGlnArgProGlyArgPheAspArg-305 |
| SEQ. ID. NO. 33641 | 312-ProAspIleArgGlyArgGluGlnXxx-320 |
| SEQ. ID. NO. 33642 | 324-HisSerLysLysValProLeuAspGluSerValAsp-335 |
| SEQ. ID. NO. 33643 | 362-AlaGlyArgArgAsnLysValLysValAspGlnSerAspLeuLysThrProLysThrLys-381 |
| g616 | |
| AMPHI Regions - AMPHI | |
| SEQ. ID. NO. 33644 | 6-LysMetValValGlyLeu-11 |
| SEQ. ID. NO. 33645 | 13-AsnProGlyLysGluTyrGlu-19 |
| SEQ. ID. NO. 33646 | 48-PheGlyGluValAlaArgAla-54 |
| SEQ. ID. NO. 33647 | 77-ValAlaAlaLeuAlaGlnPheTyrLys-85 |
| SEQ. ID. NO. 33648 | 115-GlyHisAsnGlyLeuLysAspIle-122 |
| SEQ. ID. NO. 33649 | 152-LeuAsnLysProSerAla-157 |
| SEQ. ID. NO. 33650 | 177-HisHisPheArgGlnMetGlyArg-184 |
| SEQ. ID. NO. 33651 | 203-ThrAlaPheSerArgPheProTyr-210 |
| SEQ. ID. NO. 33652 | 267-AlaProValGlnAsnLeuProAsnValAla-276 |
| SEQ. ID. NO. 33653 | 299-GlyGlyIleTyrSerLeuLeuPhe-306 |
| SEQ. ID. NO. 33654 | 319-PheAspLysAlaAla-323 |
| SEQ. ID. NO. 33655 | 363-GluCysAlaGlnAlaTrp-368 |
| SEQ. ID. NO. 33656 | 374-ThrGlySerLeuGlyAspValLeuAlaAspLeuThr-385 |
| Antigenic Index - Jameson-Wolf | |
| SEQ. ID. NO. 33657 | 11-LeuGlyAsnProGlyLysGluTyrGluGlnThrArgHisAsnAlaGlyPhe-27 |
| SEQ. ID. NO. 33658 | 39-AlaSerPheLysGluGluLysLysPhePhe-48 |
| SEQ. ID. NO. 33659 | 55-AlaLeuProAspGly-59 |
| SEQ. ID. NO. 33660 | 70-MetAsnArgSerGlyGlnAla-76 |
| SEQ. ID. NO. 33661 | 86-IleLysProGluGlu-90 |
| SEQ. ID. NO. 33662 | 96-AspGluLeuAspIleProCysGlyArgIleLysPhe-107 |
| SEQ. ID. NO. 33663 | 109-LeuGlyGlyGlyAsnGlyGlyHisAsnGlyLeuLysAspIleGlnAla-124 |
| SEQ. ID. NO. 33664 | 138-IleGlyHisProGlyAspArgAsnLeu-146 |
| SEQ. ID. NO. 33665 | 152-LeuAsnLysProSerAlaGluAlaProProAlaAsnArgArgCysArgArgGlnIleProAlaGlyArgThrArgHisHisPheArgGlnMetGlyArgGlyAsnAlaLeu-188 |
| SEQ. ID. NO. 33666 | 197-ArgLeuLysProPheGlnThrAla-204 |
| SEQ. ID. NO. 33667 | 209-ProTyrProAsnSerHisGluArgThrGlnAla-219 |
| SEQ. ID. NO. 33668 | 221-TyrProAsnGlyIleHisProArgHisArgArgAsnProArgPheProAla-237 |
| SEQ. ID. NO. 33669 | 239-ArgMetGlnHisArgArgSerThrValArgArgArgSerGlyThrMetAlaArgHisThrCysArgThrArgArgGlnIle-265 |
| SEQ. ID. NO. 33670 | 275-ValAlaGlyArgGlyGlyGlyMetLysLeuProArgAsnArgPhe-289 |
| SEQ. ID. NO. 33671 | 308-AlaAlaAspThrAlaProProPro-315 |
| SEQ. ID. NO. 33672 | 317-ProHisPheAspLysAlaAla-323 |
| SEQ. ID. NO. 33673 | 338-AlaPheLysThrGlyLysLeuProIlePro-347 |
| SEQ. ID. NO. 33674 | 371-AlaThrArgThrGlySerLeuGly-378 |
| SEQ. ID. NO. 33675 | 394-AlaArgSerAlaCysArgProAsp-401 |
| Hydrophilic Regions - Hopp-Woods | |
| SEQ. ID. NO. 33676 | 13-AsnProGlyLysGluTyrGluGlnThrArgHis-23 |
| SEQ. ID. NO. 33677 | 39-AlaSerPheLysGluGluLysLysPhePhe-48 |
| SEQ. ID. NO. 33678 | 86-IleLysProGluGlu-90 |
| SEQ. ID. NO. 33679 | 96-AspGluLeuAspIleProCysGlyArgIleLysPhe-107 |
| SEQ. ID. NO. 33680 | 117-AsnGlyLeuLysAspIleGlnAla-124 |
| SEQ. ID. NO. 33681 | 140-HisProGlyAspArgAsnLeu-146 |
| SEQ. ID. NO. 33682 | 155-ProSerAlaGluAlaProProAlaAsnArgArgCysArgArgGlnIleProAlaGlyArgThrArgHisHisPhe-179 |
| SEQ. ID. NO. 33683 | 212-AsnSerHisGluArgThrGln-218 |
| SEQ. ID. NO. 33684 | 225-IleHisProArgHisArgArgAsnProArg-234 |
| SEQ. ID. NO. 33685 | 240-MetGlnHisArgArgSerThrValArgArgArgSerGlyThrMet-254 |
| SEQ. ID. NO. 33686 | 257-HisThrCysArgThrArgArgGlnIle-265 |
| SEQ. ID. NO. 33687 | 276-AlaGlyArgGlyGlyGly-281 |
| SEQ. ID. NO. 33688 | 283-LysLeuProArgAsnArgPhe-289 |
| SEQ. ID. NO. 33689 | 308-AlaAlaAspThrAla-312 |
| SEQ. ID. NO. 33690 | 318-HisPheAspLysAlaAla-323 |
| SEQ. ID. NO. 33691 | 338-AlaPheLysThrGlyLys-343 |
| SEQ. ID. NO. 33692 | 396-SerAlaCysArgProAsp-401 |
| g619 | |
| AMPHI Regions - AMPHI | |
| SEQ. ID. NO. 33693 | 50-LysLeuAlaAlaLeuLeu-55 |
| SEQ. ID. NO. 33694 | 66-GlnLeuPheGlnThrLeuThrAsn-73 |
| SEQ. ID. NO. 33695 | 146-GlyValIlePheGlyIleLeuPheArgSerLeuSerSerLeuLeuSerArg-162 |
| SEQ. ID. NO. 33696 | 165-AspProGluGluPhe-169 |
| SEQ. ID. NO. 33697 | 175-AsnMetPheAlaGlyPheAsn-181 |
| SEQ. ID. NO. 33698 | 246-AlaValValGlyProValSerPhePheGlyLeuLeuAlaAlaSerLeuAlaAsnHisPheSer-266 |
| SEQ. ID. NO. 33699 | 303-LeuSerValValValGluPhe-309 |
| Antigenic Index - Jameson-Wolf | |
| SEQ. ID. NO. 33700 | 1-MetProSerGluLysAsnIle-7 |
| SEQ. ID. NO. 33701 | 12-GlySerSerArgProLeuArg-18 |
| SEQ. ID. NO. 33702 | 35-AsnValLysGlyAspTrpAsp-41 |
| SEQ. ID. NO. 33703 | 132-IleArgGlnGlyGlyArgAspLeuPro-140 |
| SEQ. ID. NO. 33704 | 163-MetIleAspProGluGluPheThr-170 |
| SEQ. ID. NO. 33705 | 182-ThrValArgSerGluLeu-187 |
| SEQ. ID. NO. 33706 | 205-GluArgTyrArgSerAspValHisLeuLeuGlyArgAspGlnAlaVal-220 |
| SEQ. ID. NO. 33707 | 265-PheSerProSerValArgHisSerVal-273 |
| Hydrophilic Regions - Hopp-Woods | |
| SEQ. ID. NO. 33708 | 1-MetProSerGluLysAsnIle-7 |
| SEQ. ID. NO. 33709 | 13-SerSerArgProLeu-17 |

TABLE 1-continued

| | |
|---|---|
| SEQ. ID. NO. 33710 | 134-GlnGlyGlyArgAspLeuPro-140 |
| SEQ. ID. NO. 33711 | 163-MetIleAspProGluGluPheThr-170 |
| SEQ. ID. NO. 33712 | 183-ValArgSerGluLeu-187 |
| SEQ. ID. NO. 33713 | 205-GluArgTyrArgSerAspVal-211 |
| SEQ. ID. NO. 33714 | 213-LeuLeuGlyArgAspGlnAla-219 |
| SEQ. ID. NO. 33715 | 269-ValArgHisSerVal-273 |
| g620 | |
| AMPHI Regions - AMPHI | |
| SEQ. ID. NO. 33716 | 8-IleValAlaValPheAlaLeuSerAla-16 |
| SEQ. ID. NO. 33717 | 31-IleSerAspArgSerVal-36 |
| SEQ. ID. NO. 33718 | 69-ValLysGlnMetPheGlyTyrThrLysLeuProGluGluProLysGlyIleArgValIleTyrValThrAspMetGlyAsnValThrAspTrpThr-100 |
| SEQ. ID. NO. 33719 | 139-GlnAlaGluLysPhe-143 |
| Antigenic Index - Jameson-Wolf | |
| SEQ. ID. NO. 33720 | 16-AlaCysArgGlnAlaGluGluAlaProProProLeuProArgGlnIleSerAspArgSerValGlyHisTyrCysSerMetAsnLeuThrGluHisAsn GlyProLysAla-52 |
| SEQ. ID. NO. 33721 | 56-LeuAsnGlyLysProAspGlnProVal-64 |
| SEQ. ID. NO. 33722 | 75-TyrThrLysLeuProGluGluProLysGlyIle-85 |
| SEQ. ID. NO. 33723 | 92-AspMetGlyAsnValThrAspTrpThrAsnProAsnAlaAspThrGluTrpIleAspAlaLysLys-113 |
| SEQ. ID. NO. 33724 | 125-GlyMetGlyAlaGluAspAlaLeuProPheGlyAsnLysGluGlnAlaGluLysPheAlaLysAspLysGlyGlyLysValValGly-153 |
| SEQ. ID. NO. 33725 | 155-AspAspMetProAsp-159 |
| Hydrophilic Regions - Hopp-Woods | |
| SEQ. ID. NO. 33726 | 18-ArgGlnAlaGluGluAlaProProProLeu-27 |
| SEQ. ID. NO. 33727 | 30-GlnIleSerAspArgSerVal-36 |
| SEQ. ID. NO. 33728 | 46-GluHisAsnGlyProLys-51 |
| SEQ. ID. NO. 33729 | 58-GlyLysProAspGln-62 |
| SEQ. ID. NO. 33730 | 77-LysLeuProGluGluProLysGlyIle-85 |
| SEQ. ID. NO. 33731 | 103-AsnAlaAspThrGluTrpIleAspAlaLysLys-113 |
| SEQ. ID. NO. 33732 | 127-GlyAlaGluAspAlaLeu-132 |
| SEQ. ID. NO. 33733 | 135-GlyAsnLysGluGlnAlaGluLysPheAlaLysAspLysGlyGlyLys-150 |
| SEQ. ID. NO. 33734 | 155-AspAspMetProAsp-159 |
| g622 | |
| AMPHI Regions - AMPHI | |
| SEQ. ID. NO. 33735 | 28-LeuProGluAlaValArgAsnLeuAlaArg-37 |
| SEQ. ID. NO. 33736 | 62-GluGluIleIleArgTrpLeuAlaAsp-70 |
| SEQ. ID. NO. 33737 | 112-IleLeuGlyGlnIleLysAspAlaValArgAlaAlaGlnGlu-125 |
| SEQ. ID. NO. 33738 | 132-LysLeuAsnAlaLeuPheGlnLys-139 |
| SEQ. ID. NO. 33739 | 142-SerValAlaLysGluVal-147 |
| SEQ. ID. NO. 33740 | 169-GluGlnIlePheProAspIleGlyAsp-177 |
| SEQ. ID. NO. 33741 | 187-GluMetIleGluLeuValAla-193 |
| SEQ. ID. NO. 33742 | 214-AlaGlnGluLeuCysAspLys-220 |
| SEQ. ID. NO. 33743 | 232-AspLeuProAlaIleLeuHis-238 |
| SEQ. ID. NO. 33744 | 288-AspLeuAsnAspAla-292 |
| SEQ. ID. NO. 33745 | 297-ValAspAspMetValAsnIleValGlnSerGly-307 |
| SEQ. ID. NO. 33746 | 324-GluLysValAlaGluPheValArgGlnGln-333 |
| SEQ. ID. NO. 33747 | 345-LeuArgAspGluGlyGluLys-351 |
| SEQ. ID. NO. 33748 | 354-LysGlnValLeuGluAsnAlaMetLysGlnLeuAlaLys-366 |
| SEQ. ID. NO. 33749 | 372-GluValLeuGluArgLeuSerValGlnLeuThr-382 |
| SEQ. ID. NO. 33750 | 384-LysLeuLeuHisSerProThrGlnThrLeuAsnLysAlaGlyGlu-398 |
| Antigenic Index - Jameson-Wolf | |
| SEQ. ID. NO. 33751 | 16-SerIleArgGluLysLeuAla-22 |
| SEQ. ID. NO. 33752 | 30-GluAlaValArgAsnLeuAlaArgSerAsnAlaAla-41 |
| SEQ. ID. NO. 33753 | 49-ThrCysAsnArgThrGlu-54 |
| SEQ. ID. NO. 33754 | 57-CysValGlyAspSerGluGluIleIle-65 |
| SEQ. ID. NO. 33755 | 75-ProIleGluGluIleArgProTyr-82 |
| SEQ. ID. NO. 33756 | 87-AspMetGlnGluThrValArgHis-94 |
| SEQ. ID. NO. 33757 | 115-GlnIleLysAspAlaValArgAlaAlaGlnGluGlnGluSerMetGlyAla-131 |
| SEQ. ID. NO. 33758 | 142-SerValAlaLysGluValArgThrAspThrAlaValGlyGluAsnSerVal-158 |
| SEQ. ID. NO. 33759 | 174-AspIleGlyAspLeuAsn-179 |
| SEQ. ID. NO. 33760 | 199-LysAsnProArgLeu-203 |
| SEQ. ID. NO. 33761 | 210-ThrLeuAlaArgAlaGlnGluLeuCysAspLysLeuGlyValAsnAlaGlu-226 |
| SEQ. ID. NO. 33762 | 257-GlyMetValGluArgAlaLeuLysGlnArgGlnSer-268 |
| SEQ. ID. NO. 33763 | 277-AlaValProArgAspIleGluAlaGluValGlyAspLeuAsnAsp-291 |
| SEQ. ID. NO. 33764 | 305-GlnSerGlyLysGluAlaArgGlnLysAlaAlaAlaAla-317 |
| SEQ. ID. NO. 33765 | 321-LeuValSerGluLysValAlaGluPheValArgGlnGlnGlnGlyArgGlnSerVal-339 |
| SEQ. ID. NO. 33766 | 343-LysAlaLeuArgAspGluGlyGluLysAlaArgLysGlnValLeu-357 |
| SEQ. ID. NO. 33767 | 368-AlaThrAlaGluGluValLeuGlu-375 |
| SEQ. ID. NO. 33768 | 381-LeuThrAsnLysLeuLeuHisSerProThrGlnThrLeuAsnLysAlaGlyGluGluAspLysAspLeuVal-404 |
| Hydrophilic Regions - Hopp-Woods | |
| SEQ. ID. NO. 33769 | 16-SerIleArgGluLysLeuAla-22 |
| SEQ. ID. NO. 33770 | 30-GluAlaValArgAsnLeuAlaArgSerAsnAlaAla-41 |
| SEQ. ID. NO. 33771 | 59-GlyAspSerGluGluIleIle-65 |
| SEQ. ID. NO. 33772 | 75-ProIleGluGluIleArg-80 |
| SEQ. ID. NO. 33773 | 87-AspMetGlnGluThrValArgHis-94 |
| SEQ. ID. NO. 33774 | 115-GlnIleLysAspAlaValArgAlaAlaGlnGluGlnGluSerMetGly-130 |
| SEQ. ID. NO. 33775 | 142-SerValAlaLysGluValArgThrAspThrAlaValGly-154 |
| SEQ. ID. NO. 33776 | 210-ThrLeuAlaArgAlaGlnGluLeuCysAsp-219 |
| SEQ. ID. NO. 33777 | 257-GlyMetValGluArgAlaLeuLysGlnArgGlnSer-268 |
| SEQ. ID. NO. 33778 | 277-AlaValProArgAspIleGluAlaGluValGlyAspLeuAsn-290 |
| SEQ. ID. NO. 33779 | 305-GlnSerGlyLysGluAlaArgGlnLysAlaAlaAlaAla-317 |
| SEQ. ID. NO. 33780 | 321-LeuValSerGluLysValAlaGluPheValArg-331 |

TABLE 1-continued

| | |
|---|---|
| SEQ. ID. NO. 33781 | 333-GlnGlnGlyArgGlnSer-338 |
| SEQ. ID. NO. 33782 | 343-LysAlaLeuArgAspGluGlyGluLysAlaArgLysGlnValLeu-357 |
| SEQ. ID. NO. 33783 | 368-AlaThrAlaGluGluValLeuGlu-375 |
| SEQ. ID. NO. 33784 | 392-ThrLeuAsnLysAlaGlyGluGluAspLysAspLeuVal-404 |
| g624 | |
| AMPHI Regions - AMPHI | |
| SEQ. ID. NO. 33785 | 17-GlyIleIleGlyIlePheLeuPro-24 |
| SEQ. ID. NO. 33786 | 45-ArgPheHisArgTrpLeuHis-51 |
| SEQ. ID. NO. 33787 | 58-ProMetValHisAsn-62 |
| SEQ. ID. NO. 33788 | 102-SerSerValPheCys-106 |
| Antigenic Index - Jameson-Wolf | |
| SEQ. ID. NO. 33789 | 41-LysAlaSerProArgPheHisArgTrp-49 |
| SEQ. ID. NO. 33790 | 51-HisArgHisArgTyrPheGlyProMet-59 |
| SEQ. ID. NO. 33791 | 63-TrpGluGlnAsnGlyAlaValProArgLysAlaLys-74 |
| SEQ. ID. NO. 33792 | 114-TrpHisArgProGluSer-119 |
| Hydrophilic Regions - Hopp-Woods | |
| SEQ. ID. NO. 33793 | 67-GlyAlaValProArgLysAlaLys-74 |
| SEQ. ID. NO. 33794 | 115-HisArgProGluSer-119 |
| g625 | |
| AMPHI Regions - AMPHI | |
| SEQ. ID. NO. 33795 | 14-ThrArgArgValArgSerTrpLeuAla-22 |
| SEQ. ID. NO. 33796 | 24-SerSerGlyArgIleIleSerIleAlaAla-33 |
| SEQ. ID. NO. 33797 | 64-LysMetProProGluMetValTyrArgAla-73 |
| SEQ. ID. NO. 33798 | 78-MetLysGlyIleTyrSer-83 |
| Antigenic Index - Jameson-Wolf | |
| SEQ. ID. NO. 33799 | 5-ArgLysMetLysLysMetThrMetCysThrArgArgValArg-18 |
| SEQ. ID. NO. 33800 | 57-ProPheLysSerProGlnThrLysMetProPro-67 |
| SEQ. ID. NO. 33801 | 73-AlaSerSerSerArgMetLysGly-80 |
| SEQ. ID. NO. 33802 | 96-AspAlaProLysThrLysLeuAsnGlyMetArgLysSerAsnValGln-111 |
| Hydrophilic Regions - Hopp-Woods | |
| SEQ. ID. NO. 33803 | 5-ArgLysMetLysLysMetThrMetCysThrArgArgValArg-18 |
| SEQ. ID. NO. 33804 | 60-SerProGlnThrLysMetProPro-67 |
| SEQ. ID. NO. 33805 | 74-SerSerSerArgMetLysGly-80 |
| SEQ. ID. NO. 33806 | 96-AspAlaProLysThrLysLeuAsnGlyMetArgLysSerAsnValGln-111 |
| g627 | |
| AMPHI Regions - AMPHI | |
| SEQ. ID. NO. 33807 | 21-LeuGlnAsnLeuVal-25 |
| SEQ. ID. NO. 33808 | 56-IleAlaGluValGlyLysLeuPheLeuGlyIlePheIleThrIlePheProValLeuSerIleLeuLysAlaGlyGluAlaGlyAlaLeuGlyGlyValVal SerLeuValHisAspThrAlaGlyHisPro-99 |
| SEQ. ID. NO. 33809 | 109-GlyIleLeuSerAlaPheLeuAspAsnAla-118 |
| SEQ. ID. NO. 33810 | 153-PheMetGlyAlaLeuThrTyrIleGlyAsnAlaProAsnPheMetValLys-169 |
| SEQ. ID. NO. 33811 | 180-ProThrPhePheArgTyr-185 |
| Antigenic Index - Jameson-Wolf | |
| SEQ. ID. NO. 33812 | 3-GlyLeuTrpLysProGluHisProGlyPhe-12 |
| SEQ. ID. NO. 33813 | 41-ThrProLysGlnValArgAlaGlyAsnGluPheAsnPhe-53 |
| SEQ. ID. NO. 33814 | 94-AspThrAlaGlyHis-98 |
| SEQ. ID. NO. 33815 | 128-AlaGlyGlyAspAla-132 |
| SEQ. ID. NO. 33816 | 170-AlaIleAlaGluGlnArgGlyValPro-178 |
| Hydrophilic Regions - Hopp-Woods | |
| SEQ. ID. NO. 33817 | 5-TrpLysProGluHisProGly-11 |
| SEQ. ID. NO. 33818 | 43-LysGlnValArgAlaGlyAsn-49 |
| SEQ. ID. NO. 33819 | 170-AlaIleAlaGluGlnArgGlyVal-177 |
| g628 | |
| AMPHI Regions - AMPHI | |
| SEQ. ID. NO. 33820 | 10-CysGlyProProAsnSerCysValSerIleLeuAlaAlaPhe-23 |
| SEQ. ID. NO. 33821 | 25-AspGlyThrSerAlaProAlaAla-32 |
| SEQ. ID. NO. 33822 | 34-HisThrTrpIleLeuArgSer-40 |
| Antigenic Index - Jameson-Wolf | |
| SEQ. ID. NO. 33823 | 6-LysProAlaGlyCysGlyProProAsnSer-15 |
| SEQ. ID. NO. 33824 | 23-PheSerAspGlyThrSerAla-29 |
| SEQ. ID. NO. 33825 | 40-SerValArgArgLeuAsnThrAsnArgProArgLeuLysSerSerAla-55 |
| SEQ. ID. NO. 33826 | 77-MetAlaAsnGlySerAlaSerThr-84 |
| SEQ. ID. NO. 33827 | 91-GlyArgValArgSerAlaValHisLysProAspIleArgLeuArgArg-106 |
| SEQ. ID. NO. 33828 | 115-SerAlaSerGlyThr-119 |
| Hydrophilic Regions - Hopp-Woods | |
| SEQ. ID. NO. 33829 | 40-SerValArgArgLeuAsnThrAsnArgProArgLeuLysSerSerAla-55 |
| SEQ. ID. NO. 33830 | 91-GlyArgValArgSerAlaValHisLysProAspIleArgLeuArgArg-106 |
| g629 | |
| AMPHI Regions - AMPHI | |
| SEQ. ID. NO. 33831 | 32-ArgTrpSerAspValPheSer-38 |
| SEQ. ID. NO. 33832 | 48-IleSerArgLeuProArgThrPhe-55 |
| SEQ. ID. NO. 33833 | 116-ValAlaAlaLeuIleGlyMetLeu-123 |
| SEQ. ID. NO. 33834 | 145-XxxIlePheGlyGlyValValGluAlaValAlaThrPhe-157 |
| SEQ. ID. NO. 33835 | 164-MetLeuGlnMetLeuGlyValTrpGlnGlnGlyAsp-175 |
| SEQ. ID. NO. 33836 | 206-IleLeuGlyLeuGlyGlu-211 |
| SEQ. ID. NO. 33837 | 253-ValProAsnIleValSerArgLeuMetGlyAspArgLeuArgGlnSer-268 |
| SEQ. ID. NO. 33838 | 285-IleIleGlyArgMet-289 |
| SEQ. ID. NO. 33839 | 300-ThrValPheGlyValLeu-305 |

TABLE 1-continued

Antigenic Index - Jameson-Wolf
SEQ. ID. NO. 33840 38-SerLeuSerAspSerGln-43
SEQ. ID. NO. 33841 50-ArgLeuProArgThr-54
SEQ. ID. NO. 33842 77-AsnArgPheValGluProSerMetAlaGlyAlaGlyGln-89
SEQ. ID. NO. 33843 130-ArgArgLeuProProThrAla-136
SEQ. ID. NO. 33844 260-LeuMetGlyAspArgLeuArgGlnSer-268
Hydrophilic Regions - Hopp-Woods
SEQ. ID. NO. 33845 260-LeuMetGlyAspArgLeuArgGln-267
g630
AMPHI Regions - AMPHI
SEQ. ID. NO. 33846 30-ProAspLeuLeuGlnGln-35
SEQ. ID. NO. 33847 81-GlyGlyPheTrpGluValLeuPheAla-89
SEQ. ID. NO. 33848 135-PheGlyGlyThrGlyLysAsnPhe-142
SEQ. ID. NO. 33849 169-AlaValAspGlyTyrSerGlyAlaThrAlaLeuAlaGlnTrp-182
SEQ. ID. NO. 33850 187-AlaAspGlyLeuLysAsnAlaVal-194
SEQ. ID. NO. 33851 203-AspAlaPheIleGlyLysLeuProGlySerIleGlyGluValSer-217
SEQ. ID. NO. 33852 230-PheAlaArgIleAlaSerTrpArgIleIleAlaGlyValMet-243
SEQ. ID. NO. 33853 247-IleAlaMetSerSerLeuIleAsnPhe-255
Antigenic Index - Jameson-Wolf
SEQ. ID. NO. 33854 37-IleAlaHisAspGlyAsnTyr-43
SEQ. ID. NO. 33855 53-MetSerProGluAla-57
SEQ. ID. NO. 33856 90-SerValArgLysHisGluIleAsnGlu-98
SEQ. ID. NO. 33857 133-GluValPheGlyGlyThrGlyLysAsnPheMet-143
SEQ. ID. NO. 33858 157-TyrProAlaAsnLeuSerGlyAspAla-165
SEQ. ID. NO. 33859 186-GlyAlaAspGlyLeuLys-191
SEQ. ID. NO. 33860 209-LeuProGlySerIleGly-214
SEQ. ID. NO. 33861 257-GlySerAspThrLysAla-262
SEQ. ID. NO. 33862 271-GlyThrTrpTrpLysAspAspTyrHisSerLeu-281
Hydrophilic Regions - Hopp-Woods
SEQ. ID. NO. 33863 90-SerValArgLysHisGluIleAsn-97
SEQ. ID. NO. 33864 258-SerAspThrLysAla-262
g638
AMPHI Regions - AMPHI
SEQ. ID. NO. 33865 17-LeuAlaArgPheValAspAsnIle-24
SEQ. ID. NO. 33866 30-IleValAspIleValGlu-35
SEQ. ID. NO. 33867 46-AspIleValGluHisPheGluProPheGlyLys-56
SEQ. ID. NO. 33868 108-ProPheGlyAsnValValAlaAsp-115
SEQ. ID. NO. 33869 118-ArgAlaGlyArgValPro-123
SEQ. ID. NO. 33870 148-ArgIleGlyArgThrMetLysValTyrAlaGluArgIleIle-161
SEQ. ID. NO. 33871 198-GluArgTyrValArgArgValTyrGly-206
SEQ. ID. NO. 33872 212-LeuValProPheAspGlyCysGlyThrValGlyArg-223
SEQ. ID. NO. 33873 242-SerGlnPheAspArgIleAlaArgProGlyAlaGlyLysAsnPheGlyLysValValLeuArgGlyAsnVal-265
SEQ. ID. NO. 33874 304-TrpProAsnLysIleLysHisHis-311
Antigenic Index - Jameson-Wolf
SEQ. ID. NO. 33875 13-GlyLysAsnAlaLeu-17
SEQ. ID. NO. 33876 43-AlaAspGlyAspIle-47
SEQ. ID. NO. 33877 52-GluProPheGlyLys-56
SEQ. ID. NO. 33878 81-ValAspGlyGluThrGlnVal-87
SEQ. ID. NO. 33879 99-AlaGlyIleGlyLysAsnAlaVal-106
SEQ. ID. NO. 33880 113-ValAlaAspAspLeuArgAlaGlyArgValProAsnGlyAsn-126
SEQ. ID. NO. 33881 148-ArgIleGlyArgThrMet-153
SEQ. ID. NO. 33882 169-GlnGlyAlaArgGlyGlyPhe-175
SEQ. ID. NO. 33883 188-HisThrGlyThrGlyAsnGlyGlnValAlaGluArgTyrValArg-202
SEQ. ID. NO. 33884 216-AspGlyCysGlyThrValGlyArgProPheAsnArgAsnArgPheValAsp-232
SEQ. ID. NO. 33885 240-AlaGlySerGlnPheAspArgIleAlaArgProGlyAlaGlyLysAsnPheGly-257
SEQ. ID. NO. 33886 260-ValLeuArgGlyAsnValAspAspGlyCysArgCysArgLeuLysAsnAlaAlaGlyGlyLysTyrGlnHis-283
SEQ. ID. NO. 33887 285-LeuGlnProTyrThrGluArgGlyCys-293
SEQ. ID. NO. 33888 304-TrpProAsnLysIleLysHisHisSerAsn-313
SEQ. ID. NO. 33889 319-AlaLysProProGluThrValArg-326
Hydrophilic Regions - Hopp-Woods
SEQ. ID. NO. 33890 43-AlaAspGlyAspIle-47
SEQ. ID. NO. 33891 81-ValAspGlyGluThrGlnVal-87
SEQ. ID. NO. 33892 113-ValAlaAspAspLeuArgAlaGlyArgValProAsn-124
SEQ. ID. NO. 33893 148-ArgIleGlyArgThrMet-153
SEQ. ID. NO. 33894 195-GlnValAlaGluArgTyrValArg-202
SEQ. ID. NO. 33895 243-GlnPheAspArgIleAlaArgProGlyAlaGlyLysAsnPheGly-257
SEQ. ID. NO. 33896 263-GlyAsnValAspAspGlyCysArgCysArgLeuLysAsnAlaAla-277
SEQ. ID. NO. 33897 288-TyrThrGluArgGlyCys-293
SEQ. ID. NO. 33898 320-LysProProGluThrValArg-326
g639-1
AMPHI Regions - AMPHI
SEQ. ID. NO. 33899 95-TyrLysAsnAsnArg-99
SEQ. ID. NO. 33900 137-LeuLysValPheAspAsnIle-143
SEQ. ID. NO. 33901 156-ValAsnTyrSerAspIleHisAspAsnIleIleAsnLysAla-169
SEQ. ID. NO. 33902 268-AlaProValSerArg-272
SEQ. ID. NO. 33903 289-GlnPheProAlaValLeuProGly-296
Antigenic Index - Jameson-Wolf
SEQ. ID. NO. 33904 25-AsnIlePheAspAsnSerPhe-31
SEQ. ID. NO. 33905 41-AlaMetValArgGluAsnLysIleValGly-50
SEQ. ID. NO. 33906 52-AlaThrLeuArgValAsnGluArgGlyAsnGly-62

TABLE 1-continued

| | |
|---|---|
| SEQ. ID. NO. 33907 | 75-GlyAsnAspIleSerLysGlyArgAspGlyIlePheSerAsnThrSerThrHisAsnThrTyrLysAsnAsnArgPheSerAsp-102 |
| SEQ. ID. NO. 33908 | 111-TyrThrAsnAspSerGluValSerGly-119 |
| SEQ. ID. NO. 33909 | 135-GluArgLeuLysVal-139 |
| SEQ. ID. NO. 33910 | 145-ValGlySerArgAspGlyIle-151 |
| SEQ. ID. NO. 33911 | 159-SerAspIleHisAspAsnIleIleAsnLysAlaGlyLys-171 |
| SEQ. ID. NO. 33912 | 178-AlaAsnTyrAspLysLeuSerAlaAsnHis-187 |
| SEQ. ID. NO. 33913 | 202-GluGlyThrSerLeuHisAspAsnSer-210 |
| SEQ. ID. NO. 33914 | 212-IleAsnAsnGlySerGlnValLysTyrValSer-222 |
| SEQ. ID. NO. 33915 | 227-AspTrpSerGluGlyGlyHisGlyAsnTyrTrpSerAspAsnSerProPhe-243 |
| SEQ. ID. NO. 33916 | 245-LeuAsnGlyAspGlyPheGlyAspSerAlaTyrArgProAspGlyIleIle-261 |
| SEQ. ID. NO. 33917 | 296-GlyGlyValValAspSerLysProLeuMetLysProTyrAlaProLysIleGlnThr-314 |
| SEQ. ID. NO. 33918 | 317-GlnAlaMetLysAspGluLeuLeuLysGluAlaGluThrArgGlnSerGluArgGlyArgAlaGluAsnGlySerLeuAsn-343 |
| Hydrophilic Regions - Hopp-Woods | |
| SEQ. ID. NO. 33919 | 41-AlaMetValArgGluAsnLysIleValGly-50 |
| SEQ. ID. NO. 33920 | 52-AlaThrLeuArgValAsnGluArgGlyAsn-61 |
| SEQ. ID. NO. 33921 | 77-AspIleSerLysGlyArgAspGlyIle-85 |
| SEQ. ID. NO. 33922 | 95-TyrLysAsnAsnArgPheSerAsp-102 |
| SEQ. ID. NO. 33923 | 113-AsnAspSerGluValSerGly-119 |
| SEQ. ID. NO. 33924 | 135-GluArgLeuLysVal-139 |
| SEQ. ID. NO. 33925 | 146-GlySerArgAspGlyIle-151 |
| SEQ. ID. NO. 33926 | 179-AsnTyrAspLysLeuSer-184 |
| SEQ. ID. NO. 33927 | 253-SerAlaTyrArgProAspGlyIleIle-261 |
| SEQ. ID. NO. 33928 | 298-ValValAspSerLysProLeuMet-305 |
| SEQ. ID. NO. 33929 | 317-GlnAlaMetLysAspGluLeuLeuLysGluAlaGluThrArgGlnSerGluArgGlyArgAlaGluAsnGlySer-341 |
| g640 | |
| AMPHI Regions - AMPHI | |
| SEQ. ID. NO. 33930 | 6-SerIleLeuLysSerIleGly-12 |
| SEQ. ID. NO. 33931 | 22-SerIleArgArgMetSer-27 |
| SEQ. ID. NO. 33932 | 47-LeuProAlaTyrAlaGluArgLeuProAspPheLeuAlaLysIleGlnPro-63 |
| SEQ. ID. NO. 33933 | 72-ArgTyrGlyLysPro-76 |
| SEQ. ID. NO. 33934 | 109-SerLysProIleAspThrLeuMetAla-117 |
| SEQ. ID. NO. 33935 | 127-AlaLysLeuValAspHisHis-133 |
| SEQ. ID. NO. 33936 | 145-ArgValAspLysPheIleAsp-151 |
| SEQ. ID. NO. 33937 | 155-GlyLeuAsnPheIleLysAsnProProThr-164 |
| SEQ. ID. NO. 33938 | 187-IleGlnArgSerTyrLysValIle-194 |
| SEQ. ID. NO. 33939 | 209-AlaSerAlaSerAsp-213 |
| SEQ. ID. NO. 33940 | 224-ArgProArgArgMetAlaAsnProAsp-232 |
| SEQ. ID. NO. 33941 | 255-LeuAspGlnIleAsnLysLeuPheGluLysGly-265 |
| SEQ. ID. NO. 33942 | 267-LysAlaGlyValAlaAspHisAlaGluGlnGly-277 |
| SEQ. ID. NO. 33943 | 281-AspThrPheIleAspLeuTyrVal-288 |
| SEQ. ID. NO. 33944 | 346-MetIleGlnGlyGluAsnSerPhe-353 |
| SEQ. ID. NO. 33945 | 359-GlnHisGluArgValValGluLeuSerAlaAlaAspAlaProArg-373 |
| Antigenic Index - Jameson-Wolf | |
| SEQ. ID. NO. 33946 | 24-ArgArgMetSerAlaPheArgAlaArgIle-33 |
| SEQ. ID. NO. 33947 | 50-TyrAlaGluArgLeuProAspPhe-57 |
| SEQ. ID. NO. 33948 | 59-AlaLysIleGlnProSerGluIlePheProGlyAlaAspArgTyrGlyLysProGluGlyLysProMetVal-82 |
| SEQ. ID. NO. 33949 | 84-ArgValTyrLysGlyAspGluGlnLeu-92 |
| SEQ. ID. NO. 33950 | 101-AlaValAsnThrArgGlyTyrSerSerLysProIleAsp-113 |
| SEQ. ID. NO. 33951 | 128-LysLeuValAspHisHisGlu-134 |
| SEQ. ID. NO. 33952 | 142-ProGlnSerArgValAspLysPheIleAsp-151 |
| SEQ. ID. NO. 33953 | 159-IleLysAsnProProThrProSerValAlaProGlyAsp-171 |
| SEQ. ID. NO. 33954 | 184-AsnAspSerIleGlnArgSerTyrLys-192 |
| SEQ. ID. NO. 33955 | 196-AsnGlnTyrArgLeuGlySerAspLysAlaLeuGln-207 |
| SEQ. ID. NO. 33956 | 209-AlaSerAlaSerAspValArgGluAlaAlaProAlaSerGluThrArgProArgArgMetAlaAsnProAspLysGlnAspIle-236 |
| SEQ. ID. NO. 33957 | 241-GluLeuLeuLysGlnLysAla-247 |
| SEQ. ID. NO. 33958 | 257-GlnIleAsnLysLeuPheGluLysGlyGlyLysAlaGlyVal-270 |
| SEQ. ID. NO. 33959 | 272-AspHisAlaGluGlnGlyAspProAspAspThrPheIle-284 |
| SEQ. ID. NO. 33960 | 294-ProSerIleGlyLysSerLeuLeuGlyGluAspGlyTrp-306 |
| SEQ. ID. NO. 33961 | 309-LeuGlnLysArgLeuLysProGlyGln-317 |
| SEQ. ID. NO. 33962 | 322-ValAlaGlyGluGlyArgTyrSerTrpLysGlySerGlyTyrValArg-337 |
| SEQ. ID. NO. 33963 | 342-AspArgIleGluMetIleGlnGlyGluAsnSerPheArgPheThrAspAlaGlnHisGluArgValValGlu-365 |
| SEQ. ID. NO. 33964 | 367-SerAlaAlaAspAlaProArgPheLysGlu-376 |
| SEQ. ID. NO. 33965 | 382-IleProGluGlyValAla-387 |
| SEQ. ID. NO. 33966 | 389-AspGlyAlaGluProTrpArg-395 |
| Hydrophilic Regions - Hopp-Woods | |
| SEQ. ID. NO. 33967 | 24-ArgArgMetSerAlaPheArgAlaArgIle-33 |
| SEQ. ID. NO. 33968 | 50-TyrAlaGluArgLeuPro-55 |
| SEQ. ID. NO. 33969 | 68-ProGlyAlaAspArgTyrGlyLysProGluGlyLysProMetVal-82 |
| SEQ. ID. NO. 33970 | 85-ValTyrLysGlyAspGluGlnLeu-92 |
| SEQ. ID. NO. 33971 | 128-LysLeuValAspHisHisGlu-134 |
| SEQ. ID. NO. 33972 | 143-GlnSerArgValAspLysPheIleAsp-151 |
| SEQ. ID. NO. 33973 | 186-SerIleGlnArgSerTyrLys-192 |
| SEQ. ID. NO. 33974 | 200-LeuGlySerAspLysAlaLeuGln-207 |
| SEQ. ID. NO. 33975 | 210-SerAlaSerAspValArgGluAlaAlaProAlaSerGluThrArgProArgArgMetAlaAsnProAspLysGlnAsp-235 |
| SEQ. ID. NO. 33976 | 241-GluLeuLeuLysGlnLysAla-247 |
| SEQ. ID. NO. 33977 | 257-GlnIleAsnLysLeuPheGluLysGlyGlyLysAlaGlyVal-270 |
| SEQ. ID. NO. 33978 | 272-AspHisAlaGluGlnGlyAspProAspAspThrPhe-283 |
| SEQ. ID. NO. 33979 | 309-LeuGlnLysArgLeuLysProGlyGln-317 |
| SEQ. ID. NO. 33980 | 324-GlyGluGlyArgTyrSerTrp-330 |
| SEQ. ID. NO. 33981 | 342-AspArgIleGluMetIleGlnGly-349 |

TABLE 1-continued

| | |
|---|---|
| SEQ. ID. NO. 33982 | 351-AsnSerPheArgPheThrAspAlaGlnHisGluArgValValGlu-365 |
| SEQ. ID. NO. 33983 | 367-SerAlaAlaAspAlaProArgPheLysGlu-376 |
| g642 | |
| AMPHI Regions - AMPHI | |
| SEQ. ID. NO. 33984 | 22-LysSerAlaCysArg-26 |
| SEQ. ID. NO. 33985 | 28-IleCysProLeuSerAlaIleSerAlaVal-37 |
| SEQ. ID. NO. 33986 | 63-SerGlyAspAspPhe-67 |
| SEQ. ID. NO. 33987 | 139-IleLysHisIleValArgAlaPhe-146 |
| SEQ. ID. NO. 33988 | 157-AspIleAlaGlyTrpValSerAlaPheLysThrLeuArgAlaGlnGluPheLeuGlnHisLeuArgGlyGlyVal-181 |
| SEQ. ID. NO. 33989 | 184-PheArgGlyGluGly-188 |
| SEQ. ID. NO. 33990 | 190-AspAspValArgLeu-194 |
| SEQ. ID. NO. 33991 | 209-AlaAspValAlaValLysAspPheGlyAsnLeuMetAlaAlaLeuAsp-224 |
| SEQ. ID. NO. 33992 | 241-ValGlnValValLysAspValPheHisAsnAlaValArgHisAlaAspGlnLeuGln-259 |
| SEQ. ID. NO. 33993 | 293-ValAspGlyValThrAspGlyAla-300 |
| SEQ. ID. NO. 33994 | 319-GlnValAspAspPheGlyGluPheAlaValPhe-329 |
| SEQ. ID. NO. 33995 | 348-PheArgGlyValAspVal-353 |
| SEQ. ID. NO. 33996 | 403-GluLeuLeuGlnArg-407 |
| SEQ. ID. NO. 33997 | 410-HisGlnArgAlaPheAspAlaGlyThr-418 |
| Antigenic Index - Jameson-Wolf | |
| SEQ. ID. NO. 33998 | 1-MetArgTyrProPro-5 |
| SEQ. ID. NO. 33999 | 16-CysLeuLeuArgArgProLysSerAlaCysArgArgIleCysPro-30 |
| SEQ. ID. NO. 34000 | 45-ValGlnGlnGluGlyCysGly-51 |
| SEQ. ID. NO. 34001 | 58-TyrGluAspLysLysSerGlyAspAspPheAlaAspGluAspPheLeu-73 |
| SEQ. ID. NO. 34002 | 75-GlyAlaGlyValGly-79 |
| SEQ. ID. NO. 34003 | 98-GlyAsnGlyGlyLysAlaAspIle-105 |
| SEQ. ID. NO. 34004 | 126-PheGlyGlyGlyAlaAspGluLeu-133 |
| SEQ. ID. NO. 34005 | 146-PheLysAsnArgGluGlyAlaAspIleAspGlyAspIle-158 |
| SEQ. ID. NO. 34006 | 166-LysThrLeuArgAla-170 |
| SEQ. ID. NO. 34007 | 184-PheArgGlyGluGlyPheAspAspValArgLeu-194 |
| SEQ. ID. NO. 34008 | 198-MetGlyAspGlyArgAspGlyArgAsnGlyMet-208 |
| SEQ. ID. NO. 34009 | 230-IleAspGluSerAspIleValAla-237 |
| SEQ. ID. NO. 34010 | 253-ArgHisAlaAspGlnLeuGlnAlaAlaAlaAspLysAspValLeuGluArgAlaGlnThrGlySerValAlaProGlyGlu-279 |
| SEQ. ID. NO. 34011 | 281-HisHisGlyGlyCysArg-286 |
| SEQ. ID. NO. 34012 | 288-PheGlyIleAspAlaValAspGlyValThrAspGly-299 |
| SEQ. ID. NO. 34013 | 313-CysPheGlyAspGluGlnGlnValAspAspPheGly-324 |
| SEQ. ID. NO. 34014 | 332-PheGlyGlyAsnGluGluGluValAla-340 |
| SEQ. ID. NO. 34015 | 369-CysAsnArgArgAlaGlyGlyPhe-376 |
| SEQ. ID. NO. 34016 | 412-ArgAlaPheAspAlaGlyThrGlnArgAsnGly-422 |
| SEQ. ID. NO. 34017 | 425-ValMetProArgAsnPro-430 |
| Hydrophilic Regions - Hopp-Woods | |
| SEQ. ID. NO. 34018 | 16-CysLeuLeuArgArgProLysSerAlaCysArgArgIleCys-29 |
| SEQ. ID. NO. 34019 | 58-TyrGluAspLysLysSerGlyAspAspPheAlaAspGluAspPheLeu-73 |
| SEQ. ID. NO. 34020 | 99-AsnGlyGlyLysAlaAspIle-105 |
| SEQ. ID. NO. 34021 | 129-GlyAlaAspGluLeu-133 |
| SEQ. ID. NO. 34022 | 146-PheLysAsnArgGluGlyAlaAspIleAspGlyAspIle-158 |
| SEQ. ID. NO. 34023 | 166-LysThrLeuArgAla-170 |
| SEQ. ID. NO. 34024 | 187-GluGlyPheAspAspValArgLeu-194 |
| SEQ. ID. NO. 34025 | 199-GlyAspGlyArgAspGlyArgAsnGlyMet-208 |
| SEQ. ID. NO. 34026 | 230-IleAspGluSerAspIleValAla-237 |
| SEQ. ID. NO. 34027 | 253-ArgHisAlaAspGlnLeuGlnAlaAlaAlaAspLysAspValLeuGluArgAlaGlnThr-272 |
| SEQ. ID. NO. 34028 | 292-AlaValAspGlyValThrAspGly-299 |
| SEQ. ID. NO. 34029 | 313-CysPheGlyAspGluGlnGlnValAspAspPheGly-324 |
| SEQ. ID. NO. 34030 | 334-GlyAsnGluGluGluValAla-340 |
| SEQ. ID. NO. 34031 | 369-CysAsnArgArgAlaGly-374 |
| SEQ. ID. NO. 34032 | 417-GlyThrGlnArgAsnGly-422 |
| g644 | |
| AMPHI Regions - AMPHI | |
| SEQ. ID. NO. 34033 | 26-GlyArgArgPheAspArgPro-32 |
| SEQ. ID. NO. 34034 | 55-MetAspThrAlaAlaPheLeuLysHisIleGluSerAlaPheProArgIlePheSerAspGlyIleAspLeuMetArgTyrLeu-82 |
| SEQ. ID. NO. 34035 | 111-GlnPheGluIleGlnGluValLeuArgIleAlaGly-122 |
| SEQ. ID. NO. 34036 | 141-GlnProLeuGlnGluPheGlyGly-148 |
| SEQ. ID. NO. 34037 | 181-ArgGluMetGlnSerCysTyrGluTyr-189 |
| SEQ. ID. NO. 34038 | 202-TyrTrpGlnGlyAsn-206 |
| SEQ. ID. NO. 34039 | 224-LeuAlaLysValIleAspLeuLeu-231 |
| SEQ. ID. NO. 34040 | 267-ValMetLysLeuSerArg-272 |
| SEQ. ID. NO. 34041 | 278-LeuArgAlaPheGlnAsn-283 |
| SEQ. ID. NO. 34042 | 295-MetThrHisGlyIleMetGluTyrIleLeuAspAsnLeuAsnArgTyrValArgAsn-313 |
| SEQ. ID. NO. 34043 | 333-GluIleLeuTyrArgTyrValCysHis-341 |
| SEQ. ID. NO. 34044 | 343-ValSerProValAlaProValAlaHis-351 |
| SEQ. ID. NO. 34045 | 356-AlaAsnIleValLysThrLeuAla-363 |
| SEQ. ID. NO. 34046 | 372-GlnMetLeuGlnLys-376 |
| SEQ. ID. NO. 34047 | 399-PheThrIlePheGluGlyProAsn-406 |
| SEQ. ID. NO. 34048 | 408-MetLeuTyrAlaGluIleTyrAspGlnPheValArgAla-420 |
| SEQ. ID. NO. 34049 | 456-LeuProGluAspIleArgSerPhe-463 |
| SEQ. ID. NO. 34050 | 481-GlyLysIleIleAlaArgLeu-487 |
| Antigenic Index - Jameson-Wolf | |
| SEQ. ID. NO. 34051 | 1-MetProSerGluArgProAlaAspCysCys-10 |
| SEQ. ID. NO. 34052 | 22-ThrLeuAsnCysGlyArgArgPheAspArgProProIleAsnGlyAsnArgGlnArgLysProMetIleHisThrGluProSer AlaGlnProSerThrMetAsp-56 |

TABLE 1-continued

| | |
|---|---|
| SEQ. ID. NO. 34053 | 70-ArgIlePheSerAspGlyIleAspLeu-78 |
| SEQ. ID. NO. 34054 | 82-LeuProGluAspLysTrpLeu-88 |
| SEQ. ID. NO. 34055 | 100-LeuAspLysLysHisGlyGlyArgLysGlySerGln-111 |
| SEQ. ID. NO. 34056 | 160-PheLysGlyGluSerArgArgLeuGlyValThrGluProGluThrSerGly-176 |
| SEQ. ID. NO. 34057 | 178-AlaIleAlaArgGluMetGlnSerCysTyrGluTyrThrAspGluGlnThr-194 |
| SEQ. ID. NO. 34058 | 202-TyrTrpGlnGlyAsnSerGlnSerAspPhe-211 |
| SEQ. ID. NO. 34059 | 216-AlaLysGluArgLysAsnGlyLysLeuAlaLys-226 |
| SEQ. ID. NO. 34060 | 235-LysThrTyrIleArg-239 |
| SEQ. ID. NO. 34061 | 241-GluThrLeuAlaSerGluGlyLeuArg-249 |
| SEQ. ID. NO. 34062 | 254-AlaValAsnArgIleAspAlaGluMet-262 |
| SEQ. ID. NO. 34063 | 269-LysLeuSerArgGlyAspAlaAlaGly-277 |
| SEQ. ID. NO. 34064 | 306-AsnLeuAsnArgTyrValArgAsnAspIleArgPheValAspTyrGluArgArgGluIleGlnArgArgHisGlnVal-331 |
| SEQ. ID. NO. 34065 | 381-LysGlyPheGluArgGlyHisProAlaGly-390 |
| SEQ. ID. NO. 34066 | 403-GluGlyProAsnAspMetLeu-409 |
| SEQ. ID. NO. 34067 | 420-AlaThrAlaGluGluLysGluAlaGlyIleLysLeuAspLysAsnGlnThr-436 |
| SEQ. ID. NO. 34068 | 441-ValGlnThrAspValArg-446 |
| SEQ. ID. NO. 34069 | 449-AlaValAlaArgAspTyrAlaLeu-456 |
| SEQ. ID. NO. 34070 | 458-GluAspIleArgSerPheLeu-464 |
| SEQ. ID. NO. 34071 | 492-GlnGluGluHisGluAspThrThr-499 |
| SEQ. ID. NO. 34072 | 505-AspIleArgLysAspIleLeuAspCysArgTyrCysGly-517 |
| Hydrophilic Regions - Hopp-Woods | |
| SEQ. ID. NO. 34073 | 1-MetProSerGluArgProAlaAsp-8 |
| SEQ. ID. NO. 34074 | 25-CysGlyArgArgPheAspArgProProIleAsnGlyAsnArgGlnArgLysProMetIle-44 |
| SEQ. ID. NO. 34075 | 72-PheSerAspGlyIleAsp-77 |
| SEQ. ID. NO. 34076 | 82-LeuProGluAspLysTrpLeu-88 |
| SEQ. ID. NO. 34077 | 100-LeuAspLysLysHisGlyGlyArgLysGlySerGln-111 |
| SEQ. ID. NO. 34078 | 160-PheLysGlyGluSerArgArgLeuGlyValThrGluProGluThrSerGly-176 |
| SEQ. ID. NO. 34079 | 178-AlaIleAlaArgGluMetGlnSer-185 |
| SEQ. ID. NO. 34080 | 188-GluTyrThrAspGluGlnThr-194 |
| SEQ. ID. NO. 34081 | 216-AlaLysGluArgLysAsnGlyLysLeuAlaLys-226 |
| SEQ. ID. NO. 34082 | 254-AlaValAsnArgIleAspAlaGluMet-262 |
| SEQ. ID. NO. 34083 | 269-LysLeuSerArgGlyAspAlaAlaGly-277 |
| SEQ. ID. NO. 34084 | 306-AsnLeuAsnArgTyrValArgAsnAspIleArgPheValAspTyrGluArgArgGluIleGlnArgArgHisGlnVal-331 |
| SEQ. ID. NO. 34085 | 381-LysGlyPheGluArgGlyHisPro-388 |
| SEQ. ID. NO. 34086 | 420-AlaThrAlaGluGluLysGluAlaGlyIleLysLeuAspLysAsnGlnThr-436 |
| SEQ. ID. NO. 34087 | 441-ValGlnThrAspValArg-446 |
| SEQ. ID. NO. 34088 | 458-GluAspIleArgSerPheLeu-464 |
| SEQ. ID. NO. 34089 | 492-GlnGluGluHisGluAspThrThr-499 |
| SEQ. ID. NO. 34090 | 505-AspIleArgLysAspIleLeuAsp-512 |
| g645 | |
| AMPHI Regions - AMPHI | |
| SEQ. ID. NO. 34091 | 87-ArgThrLeuProSerLeuAsnGlyLeuThrLys-97 |
| SEQ. ID. NO. 34092 | 149-ArgThrProLysArgCysSerSerSerIle-158 |
| SEQ. ID. NO. 34093 | 162-ProLysPheLeuAsnPheMetSerSerCysThrAsnLeuCys-175 |
| SEQ. ID. NO. 34094 | 211-SerAlaLysArgSer-215 |
| SEQ. ID. NO. 34095 | 250-SerValLeuProLysProThrSerProHisThrSerArg-262 |
| Antigenic Index - Jameson-Wolf | |
| SEQ. ID. NO. 34096 | 24-AsnLeuCysCysLysLysSerArgMetThrCysSerSerSerArgSerArgSerCysProCys-44 |
| SEQ. ID. NO. 34097 | 47-ProIleArgAlaSerGlySerArgValSerSerArgSerArgIle-61 |
| SEQ. ID. NO. 34098 | 68-SerLeuCysArgLysAsnThrCysProProArgLeuSerSerArgAsnThrAlaSerArgThrLeuProSer-91 |
| SEQ. ID. NO. 34099 | 99-PheThrAlaArgArgArgLeuGly-106 |
| SEQ. ID. NO. 34100 | 110-IleSerGluLysSerArgArgProSerSerAlaMetLeuArg-123 |
| SEQ. ID. NO. 34101 | 137-ThrLeuAlaArgArgArgLeuSerCysSerPheCysArgThrProLysArgCysSerSer-156 |
| SEQ. ID. NO. 34102 | 158-IleIleAsnLysProLysPheLeuAsn-166 |
| SEQ. ID. NO. 34103 | 168-MetSerSerCysThrAsn-173 |
| SEQ. ID. NO. 34104 | 199-LeuLysArgGluArgLeuAla-205 |
| SEQ. ID. NO. 34105 | 208-ThrGlyLysSerAlaLysArgSerAlaLys-217 |
| SEQ. ID. NO. 34106 | 222-CysSerThrArgSerValValGlyAla-230 |
| SEQ. ID. NO. 34107 | 243-AsnAlaAlaArgArgAlaThr-249 |
| SEQ. ID. NO. 34108 | 251-ValLeuProLysProThrSerProHisThrSerArg-262 |
| Hydrophilic Regions - Hopp-Woods | |
| SEQ. ID. NO. 34109 | 26-CysCysLysLysSerArgMetThrCysSerSerSerArgSerArgSerCysPro-43 |
| SEQ. ID. NO. 34110 | 48-IleArgAlaSerGlySerArgValSerSerArgSerArgIle-61 |
| SEQ. ID. NO. 34111 | 69-LeuCysArgLysAsnThrCysProProArgLeuSerSerArgAsnThrAlaSerArgThr-88 |
| SEQ. ID. NO. 34112 | 99-PheThrAlaArgArgArgLeuGly-106 |
| SEQ. ID. NO. 34113 | 110-IleSerGluLysSerArgArgProSer-118 |
| SEQ. ID. NO. 34114 | 137-ThrLeuAlaArgArgArgLeuSer-144 |
| SEQ. ID. NO. 34115 | 149-ArgThrProLysArgCysSer-155 |
| SEQ. ID. NO. 34116 | 158-IleIleAsnLysProLys-163 |
| SEQ. ID. NO. 34117 | 199-LeuLysArgGluArgLeuAla-205 |
| SEQ. ID. NO. 34118 | 210-LysSerAlaLysArgSerAlaLys-217 |
| SEQ. ID. NO. 34119 | 243-AsnAlaAlaArgArgAlaThr-249 |
| g647 | |
| AMPHI Regions - AMPHI | |
| SEQ. ID. NO. 34120 | 38-GlyLysValCysArgCysPheGluGlnVal-47 |
| SEQ. ID. NO. 34121 | 69-ThrValPheArgGlnIleValGlyValVal-78 |
| Antigenic Index - Jameson-Wolf | |
| SEQ. ID. NO. 34122 | 26-GlyLeuValLysGluArgAlaArg-33 |
| SEQ. ID. NO. 34123 | 39-LysValCysArgCysPhe-44 |

TABLE 1-continued

| | |
|---|---|
| SEQ. ID. NO. 34124 | 54-GlyThrValGlyGlnThrGluArgGlyThr-63 |
| SEQ. ID. NO. 34125 | 78-ValAspAspThrAspAlaGluArgThrAlaValHisSerArgGlyThrArgGlyPhe-96 |
| Hydrophilic Regions - Hopp-Woods | |
| SEQ. ID. NO. 34126 | 26-GlyLeuValLysGluArgAlaArg-33 |
| SEQ. ID. NO. 34127 | 40-ValCysArgCysPhe-44 |
| SEQ. ID. NO. 34128 | 56-ValGlyGlnThrGluArgGlyThr-63 |
| SEQ. ID. NO. 34129 | 78-ValAspAspThrAspAlaGluArgThrAlaValHisSerArgGlyThrArgGly-95 |
| g648 | |
| AMPHI Regions - AMPHI | |
| SEQ. ID. NO. 34130 | 7-ArgIleGluArgAlaValArg-13 |
| SEQ. ID. NO. 34131 | 15-AlaValIleAspValLeuAsn-21 |
| SEQ. ID. NO. 34132 | 94-AlaValAspLeuHisAlaIleIleLysLeuAlaAspThr-106 |
| SEQ. ID. NO. 34133 | 127-GlnGlyValGluGlnGly-132 |
| SEQ. ID. NO. 34134 | 148-ArgLeuLysHisLeuLysGluGlyAsnAla-157 |
| SEQ. ID. NO. 34135 | 182-AlaArgAlaLeuGlyAsnValPheHis-190 |
| SEQ. ID. NO. 34136 | 194-GlySerGlyIleAspGlyIleGlnThrIleValAlaPheAsnGlnHisThr-210 |
| Antigenic Index - Jameson-Wolf | |
| SEQ. ID. NO. 34137 | 1-MetAsnArgArgAsnAlaArgIleGluArgAlaValArg-13 |
| SEQ. ID. NO. 34138 | 24-AlaProGlyProGly-28 |
| SEQ. ID. NO. 34139 | 30-LeuLeuHisGlnArgGlyLysGlnValGlySerArgAsnAspThrLeuAla-46 |
| SEQ. ID. NO. 34140 | 65-GlyLysLysArgPheValGlnProArgAsnLeuValGlyArgLysGlnArgAsn-82 |
| SEQ. ID. NO. 34141 | 123-PheAsnMetProGlnGlyValGluGlnGlyCysArg-134 |
| SEQ. ID. NO. 34142 | 141-LeuArgThrArgPheAspArgArgLeuLysHisLeuLysGluGlyAsnAla-157 |
| SEQ. ID. NO. 34143 | 170-ValGlnProAlaAspThrSerGlyIleAspAlaAspAlaArgAla-184 |
| SEQ. ID. NO. 34144 | 191-AsnArgAlaGlySerGlyIleAspGly-199 |
| Hydrophilic Regions - Hopp-Woods | |
| SEQ. ID. NO. 34145 | 1-MetAsnArgArgAsnAlaArgIleGluArgAlaValArg-13 |
| SEQ. ID. NO. 34146 | 33-GlnArgGlyLysGlnValGlySerArgAsnAspThr-44 |
| SEQ. ID. NO. 34147 | 65-GlyLysLysArgPheValGln-71 |
| SEQ. ID. NO. 34148 | 74-AsnLeuValGlyArgLysGlnArgAsn-82 |
| SEQ. ID. NO. 34149 | 127-GlnGlyValGluGlnGlyCysArg-134 |
| SEQ. ID. NO. 34150 | 141-LeuArgThrArgPheAspArgArgLeuLysHisLeuLysGluGlyAsnAla-157 |
| SEQ. ID. NO. 34151 | 172-ProAlaAspThrSerGlyIleAspAlaAspAlaArgAla-184 |
| g649 | |
| AMPHI Regions - AMPHI | |
| SEQ. ID. NO. 34152 | 6-LeuSerAlaIleLeuGlyLeuVal-13 |
| SEQ. ID. NO. 34153 | 24-ProAlaHisArgHisThrLysHisIleSerLysAla-35 |
| SEQ. ID. NO. 34154 | 57-SerGlnGlyAsnVal-61 |
| SEQ. ID. NO. 34155 | 63-GluLeuArgGluAsnLys-68 |
| SEQ. ID. NO. 34156 | 71-ArgLysAlaPheArgThrLeuPro-78 |
| Antigenic Index - Jameson-Wolf | |
| SEQ. ID. NO. 34157 | 20-GlyThrSerGluProAlaHisArgHisThrLysHisIleSerLysAlaAsnLys-37 |
| SEQ. ID. NO. 34158 | 40-LeuHisProGluCysArgLysTyrLeuGluArgArgAlaAla-53 |
| SEQ. ID. NO. 34159 | 56-ArgSerGlnGlyAsnValGlnGluLeuArgGluAsnLysLysAlaArgLysAlaPheArg-75 |
| SEQ. ID. NO. 34160 | 80-AlaGluGlnLysIleGlnCys-86 |
| SEQ. ID. NO. 34161 | 92-AlaPheAspAspPheAspGlyGlyArgPheArgArg-103 |
| Hydrophilic Regions - Hopp-Woods | |
| SEQ. ID. NO. 34162 | 20-GlyThrSerGluProAlaHisArgHisThrLysHisIleSerLysAlaAsnLys-37 |
| SEQ. ID. NO. 34163 | 42-ProGluCysArgLysTyrLeuGluArgArgAlaAla-53 |
| SEQ. ID. NO. 34164 | 59-GlyAsnValGlnGluLeuArgGluAsnLysLysAlaArgLysAlaPheArg-75 |
| SEQ. ID. NO. 34165 | 80-AlaGluGlnLysIleGlnCys-86 |
| SEQ. ID. NO. 34166 | 92-AlaPheAspAspPheAspGlyGlyArgPheArgArg-103 |
| g650 | |
| AMPHI Regions - AMPHI | |
| SEQ. ID. NO. 34167 | 15-SerValCysProGly-19 |
| SEQ. ID. NO. 34168 | 57-LeuTrpAspGluLeuArgGlnGly-64 |
| SEQ. ID. NO. 34169 | 72-ProGluLeuValArgArgHisGlu-79 |
| SEQ. ID. NO. 34170 | 89-PheAspArgValValAsn-94 |
| SEQ. ID. NO. 34171 | 137-SerGlyLeuTrpGln-141 |
| SEQ. ID. NO. 34172 | 173-AsnTyrLeuGlnTyrLeuTyrGlyLeuPheGlyAspTrpPro-186 |
| SEQ. ID. NO. 34173 | 198-AsnValGlyArgAlaValAsnArgAlaArg-207 |
| SEQ. ID. NO. 34174 | 218-LeuArgMetProAsnGluThr-224 |
| SEQ. ID. NO. 34175 | 260-ValGluProGlyArgProLeu-266 |
| SEQ. ID. NO. 34176 | 269-GluAlaIleAlaArgLeuAlaGlyIleThrGlnSer-280 |
| SEQ. ID. NO. 34177 | 314-SerAsnTyrLeuAsnAlaAlaProAsp-322 |
| SEQ. ID. NO. 34178 | 341-IleSerThrAlaThrGlyMet-347 |
| SEQ. ID. NO. 34179 | 349-IleAlaAspIleLysArgLeuAsnAsnLeu-358 |
| SEQ. ID. NO. 34180 | 433-ValArgThrGlyThrArgSer-439 |
| Antigenic Index - Jameson-Wolf | |
| SEQ. ID. NO. 34181 | 1-MetSerLysLeuLys-5 |
| SEQ. ID. NO. 34182 | 24-GlnAsnThrSerSerHis-29 |
| SEQ. ID. NO. 34183 | 38-LeuAsnSerSerIleLeuAspLeuProProThrLysGlnTyrPhe-52 |
| SEQ. ID. NO. 34184 | 54-SerGlySerLeuTrpAspGluLeuArgGlnGlyPheArgMetGlyGluValAsnProGluLeuValArgArgHisGluSerLysPheIleAla-84 |
| SEQ. ID. NO. 34185 | 87-SerTyrPheAspArgValValAsnArgSerArgPro-98 |
| SEQ. ID. NO. 34186 | 105-AsnGluValLysLysArgAsnMetProAla-114 |
| SEQ. ID. NO. 34187 | 128-ThrLysAlaLysSerHisValGlyAlaSerGly-138 |
| SEQ. ID. NO. 34188 | 145-AlaThrGlyArgHisTyrGlyLeuGluLysThrProValTyrAspGlyArgHisAspVal-164 |
| SEQ. ID. NO. 34189 | 192-TyrAsnTrpGlyGluGlyAsnValGlyArgAlaValAsnArgAlaArgAspGlnGlyLeuGluProThrTyrGluAsnLeuArgMetProAsn GluThrArgAsnTyrVal-228 |

TABLE 1-continued

| | |
|---|---|
| SEQ. ID. NO. 34190 | 247-AsnIleSerAspIleAspAsnLysProTyr-256 |
| SEQ. ID. NO. 34191 | 259-AlaValGluProGlyArgProLeuAspAsnGluAlaIleAla-272 |
| SEQ. ID. NO. 34192 | 294-PheIleProLysAsnLysArgLysLeu-302 |
| SEQ. ID. NO. 34193 | 318-AsnAlaAlaProAspSer-323 |
| SEQ. ID. NO. 34194 | 332-ProAlaAlaLysThrSerLeuSerAspIleSerThr-343 |
| SEQ. ID. NO. 34195 | 350-AlaAspIleLysArgLeuAsnAsnLeuAsnGly-360 |
| SEQ. ID. NO. 34196 | 370-LeuValAlaLysAsnGlyLysThrLeu-378 |
| SEQ. ID. NO. 34197 | 388-IleAspIleAspAsnThrProAspThrTyrArgSerAsnMetProAla-403 |
| SEQ. ID. NO. 34198 | 431-GluThrValArgThrGlyThrArgSerProCysProHisTyrArgThrArgProCysAspSerArgSerAlaThrSerAsnArgLysThrAspCys HisAla-464 |
| Hydrophilic Regions - Hopp-Woods | |
| SEQ. ID. NO. 34199 | 1-MetSerLysLeuLys-5 |
| SEQ. ID. NO. 34200 | 59-AspGluLeuArgGlnGlyPheArgMetGlyGluValAsnProGluLeuValArgArgHisGluSerLysPheIleAla-84 |
| SEQ. ID. NO. 34201 | 92-ValValAsnArgSerArgPro-98 |
| SEQ. ID. NO. 34202 | 105-AsnGluValLysLysArgAsnMetProAla-114 |
| SEQ. ID. NO. 34203 | 128-ThrLysAlaLysSerHisVal-134 |
| SEQ. ID. NO. 34204 | 150-TyrGlyLeuGluLysThrProValTyrAspGlyArgHisAspVal-164 |
| SEQ. ID. NO. 34205 | 202-AlaValAsnArgAlaArgAspGlnGlyLeu-211 |
| SEQ. ID. NO. 34206 | 213-ProThrTyrGluAsnLeuArgMetProAsnGluThrArgAsnTyrVal-228 |
| SEQ. ID. NO. 34207 | 249-SerAspIleAspAsn-253 |
| SEQ. ID. NO. 34208 | 261-GluProGlyArgProLeuAspAsnGluAlaIleAla-272 |
| SEQ. ID. NO. 34209 | 296-ProLysAsnLysArgLysLeu-302 |
| SEQ. ID. NO. 34210 | 334-AlaLysThrSerLeu-338 |
| SEQ. ID. NO. 34211 | 350-AlaAspIleLysArgLeuAsn-356 |
| SEQ. ID. NO. 34212 | 373-LysAsnGlyLysThr-377 |
| SEQ. ID. NO. 34213 | 389-AspIleAspAsnThrProAspThrTyrArg-398 |
| SEQ. ID. NO. 34214 | 431-GluThrValArgThrGlyThrArgSerPro-440 |
| SEQ. ID. NO. 34215 | 444-TyrArgThrArgProCysAspSerArgSerAlaThrSerAsnArgLysThrAspCys-462 |
| g652-1 | |
| AMPHI Regions - AMPHI | |
| SEQ. ID. NO. 34216 | 6-AspIlePheAlaArg-10 |
| SEQ. ID. NO. 34217 | 52-ArgAspGlyAspLys-56 |
| SEQ. ID. NO. 34218 | 62-LysGlyValLeuLysAlaValGluHisValAsnAsnGlnIleAlaGlnAla-78 |
| SEQ. ID. NO. 34219 | 130-LeuTyrArgTyrLeuGlyGlyAlaGlyPro-139 |
| SEQ. ID. NO. 34220 | 149-ValIleAsnGlyGly-153 |
| SEQ. ID. NO. 34221 | 173-LysSerPheArgGluAlaLeuArgCys-181 |
| SEQ. ID. NO. 34222 | 184-GluIlePheHisAlaLeuLysLys-191 |
| SEQ. ID. NO. 34223 | 266-AlaGluPheAlaGluTyrLeuGluGlyLeuValAsn-277 |
| SEQ. ID. NO. 34224 | 299-LeuThrGluLysLeu-303 |
| SEQ. ID. NO. 34225 | 323-AlaGluGlyIleGluLysGlyVal-330 |
| SEQ. ID. NO. 34226 | 338-ValAsnGlnIleGlyThrLeuSerGluThrLeuLysAlaValAspLeuAlaLysCysAsnArgTyrAlaSer-361 |
| SEQ. ID. NO. 34227 | 377-AspLeuAlaValAla-381 |
| SEQ. ID. NO. 34228 | 391-SerLeuSerArgSerAspArgMetAlaLysTyrAsnGlnLeuLeuArgIleGluGlu-409 |
| Antigenic Index - Jameson-Wolf | |
| SEQ. ID. NO. 34229 | 11-GluIleLeuAspSerArgGlyAsnProThrValGlu-22 |
| SEQ. ID. NO. 34230 | 36-AlaValProSerGlyAlaSerThrGlyGlnLysGluAlaLeuGluLeuArgAspGlyAspLysSerArgTyrSerGlyLysGlyValLeuLys AlaValGluHisValAsn-72 |
| SEQ. ID. NO. 34231 | 83-AspAlaAsnGluGlnSerTyr-89 |
| SEQ. ID. NO. 34232 | 97-LeuAspGlyThrGluAsnLysGlyAsnLeuGly-107 |
| SEQ. ID. NO. 34233 | 121-AlaAlaAlaGluAspSerGlyLeuPro-129 |
| SEQ. ID. NO. 34234 | 135-GlyGlyAlaGlyProMet-140 |
| SEQ. ID. NO. 34235 | 151-AsnGlyGlyGluHisAlaAsnAsnSer-159 |
| SEQ. ID. NO. 34236 | 173-LysSerPheArgGluAlaLeuArgCysGlyAla-183 |
| SEQ. ID. NO. 34237 | 190-LysLysLeuCysAspSerLysGlyPheProThrThrValGlyAspGluGlyGlyPhe-208 |
| SEQ. ID. NO. 34238 | 211-AsnLeuAsnSerHisLysGluAlaLeu-219 |
| SEQ. ID. NO. 34239 | 243-CysAlaSerSerGluPheTyrLysAspGlyLysTyrHisLeuGluAlaGluGlyArgSerTyrThrAsn-265 |
| SEQ. ID. NO. 34240 | 283-SerIleGluAspGlyMetAspGluAsnAspTrpGluGly-295 |
| SEQ. ID. NO. 34241 | 299-LeuThrGluLysLeuGlyLysLysValGlnLeuValGlyAspAspLeu-314 |
| SEQ. ID. NO. 34242 | 318-AsnProLysIleLeuAlaGluGlyIleGluLysGlyVal-330 |
| SEQ. ID. NO. 34243 | 352-AspLeuAlaLysCysAsnArgTyr-359 |
| SEQ. ID. NO. 34244 | 363-MetSerHisArgSerGlyGluThrGluAspSerThrIle-375 |
| SEQ. ID. NO. 34245 | 388-LysThrGlySerLeuSerArgSerAspArgMetAlaLys-400 |
| SEQ. ID. NO. 34246 | 405-LeuArgIleGluGluGluLeuAlaGlu-413 |
| Hydrophilic Regions - Hopp-Woods | |
| SEQ. ID. NO. 34247 | 11-GluIleLeuAspSerArgGlyAsnProThrValGlu-22 |
| SEQ. ID. NO. 34248 | 43-ThrGlyGlnLysGluAlaLeuGluLeuArgAspGlyAspLysSerArgTyrSerGly-61 |
| SEQ. ID. NO. 34249 | 63-GlyValLeuLysAlaValGlu-69 |
| SEQ. ID. NO. 34250 | 97-LeuAspGlyThrGluAsnLysGlyAsnLeu-106 |
| SEQ. ID. NO. 34251 | 121-AlaAlaAlaGluAspSerGly-127 |
| SEQ. ID. NO. 34252 | 153-GlyGluHisAlaAsn-157 |
| SEQ. ID. NO. 34253 | 173-LysSerPheArgGluAlaLeuArgCysGlyAla-183 |
| SEQ. ID. NO. 34254 | 190-LysLysLeuCysAspSerLysGly-197 |
| SEQ. ID. NO. 34255 | 202-ValGlyAspGluGlyGlyPhe-208 |
| SEQ. ID. NO. 34256 | 213-AsnSerHisLysGluAlaLeu-219 |
| SEQ. ID. NO. 34257 | 247-GluPheTyrLysAspGlyLysTyrHisLeuGluAlaGluGlyArgSerTyrThr-264 |
| SEQ. ID. NO. 34258 | 283-SerIleGluAspGlyMetAspGluAsnAspTrpGluGly-295 |
| SEQ. ID. NO. 34259 | 299-LeuThrGluLysLeuGlyLysLysValGlnLeuValGly-311 |
| SEQ. ID. NO. 34260 | 321-IleLeuAlaGluGlyIleGluLysGlyVal-330 |
| SEQ. ID. NO. 34261 | 352-AspLeuAlaLysCysAsnArg-358 |
| SEQ. ID. NO. 34262 | 364-SerHisArgSerGlyGluThrGluAspSerThrIle-375 |

TABLE 1-continued

SEQ. ID. NO. 34263 391-SerLeuSerArgSerAspArgMetAlaLys-400
SEQ. ID. NO. 34264 405-LeuArgIleGluGluGluLeuAlaGlu-413
g653
AMPHI Regions - AMPHI
SEQ. ID. NO. 34265 60-ThrMetArgLysProArgLeuThr-67
SEQ. ID. NO. 34266 75-AlaLeuIlePheThrCysPheAla-82
SEQ. ID. NO. 34267 96-ThrAlaLeuAlaAlaIleThrCysIle-104
SEQ. ID. NO. 34268 111-LeuGlyLysMetGluGluPheSer-118
Antigenic Index - Jameson-Wolf
SEQ. ID. NO. 34269 4-GluProMetArgMetProGlu-10
SEQ. ID. NO. 34270 14-GlyPheSerGlySer-18
SEQ. ID. NO. 34271 45-GlyCysArgSerThrArgLysThr-52
SEQ. ID. NO. 34272 56-ValArgProGluThrMetArgLysProArgLeuThrAsnSerSerAla-71
SEQ. ID. NO. 34273 86-AsnSerGlyCysAsnAla-91
SEQ. ID. NO. 34274 103-CysIleAsnGlyProProCysArgLeuGlyLysMetGluGlu-116
SEQ. ID. NO. 34275 125-SerArgHisLysIleThrProProArgGlyProArgArgVal-138
SEQ. ID. NO. 34276 145-ThrLysSerGlnAsnGlyThrGly-152
SEQ. ID. NO. 34277 156-SerProProAlaThrSerProAla-163
Hydrophilic Regions - Hopp-Woods
SEQ. ID. NO. 34278 4-GluProMetArgMetProGlu-10
SEQ. ID. NO. 34279 47-ArgSerThrArgLysThr-52
SEQ. ID. NO. 34280 57-ArgProGluThrMetArgLysProArgLeuThrAsn-68
SEQ. ID. NO. 34281 107-ProProCysArgLeuGlyLysMetGluGlu-116
SEQ. ID. NO. 34282 126-ArgHisLysIleThrProProArgGlyProArg-136
g656
AMPHI Regions - AMPHI
SEQ. ID. NO. 34283 6-GlySerIleSerSerMetIleSerIleAlaArgThrPheGlyAlaProGlu-22
SEQ. ID. NO. 34284 42-LysGlnProSerThr-46
SEQ. ID. NO. 34285 92-LeuAlaSerLeuAsnLysSerCys-99
Antigenic Index - Jameson-Wolf
SEQ. ID. NO. 34286 4-PheSerGlySerIle-8
SEQ. ID. NO. 34287 19-GlyAlaProGluSerValProAlaGlyLysValAlaAla-31
SEQ. ID. NO. 34288 40-SerPheLysGlnProSerThrLeuGlu-48
SEQ. ID. NO. 34289 74-ArgProThrSerLeuArgProLysSerIle-83
SEQ. ID. NO. 34290 94-SerLeuAsnLysSerCysSerLeuAlaArgSerSerAlaGlyValLeuProArgArgArgValProAla-116
SEQ. ID. NO. 34291 120-ThrMetThrSerSerArgSerArgArgThrArgIleSerGlyGluGluProThrMetTrpLysSerProLysSer-144
Hydrophilic Regions - Hopp-Woods
SEQ. ID. NO. 34292 76-ThrSerLeuArgProLysSer-82
SEQ. ID. NO. 34293 99-CysSerLeuAlaArgSerSer-105
SEQ. ID. NO. 34294 109-LeuProArgArgArgValProAla-116
SEQ. ID. NO. 34295 121-MetThrSerSerArgSerArgArgThrArgIleSerGlyGluGluProThrMet-138
SEQ. ID. NO. 34296 140-LysSerProLysSer-144
g657
AMPHI Regions - AMPHI
SEQ. ID. NO. 34297 20-LeuGlyArgMetPheAla-25
SEQ. ID. NO. 34298 65-AspGluLeuAlaLysCysAlaAla-72
SEQ. ID. NO. 34299 83-AspAlaMetArgSerLeuAlaLysHisThrAsn-93
SEQ. ID. NO. 34300 128-CysLysAlaGluAspIleThrGluAlaSer-137
SEQ. ID. NO. 34301 139-GlnPheLeuProGlyIleLeuLysThr-147
SEQ. ID. NO. 34302 161-LysThrLeuAspGluLeuLysAlaAla-169
SEQ. ID. NO. 34303 178-CysValLeuGluLysMetValAsp-185
SEQ. ID. NO. 34304 205-PheAspProAlaGluAsnIle-211
SEQ. ID. NO. 34305 232-GlnGlnAlaArgGlnThrAlaGlnArgLeuAlaAspGluLeuAspTyrValGlyValLeu-251
Antigenic Index - Jameson-Wolf
SEQ. ID. NO. 34306 37-ValLeuAspProAspProAsnAlaPro-45
SEQ. ID. NO. 34307 57-ProPheAspAspArgAlaAlaLeuAspGluLeuAlaLys-69
SEQ. ID. NO. 34308 75-ThrGluPheGluAsnValAsnAlaAspAlaMetArgSerLeuAlaLysHisThrAsnValSerProSerGlyAspCysVal-101
SEQ. ID. NO. 34309 104-AlaGlnAsnArgIleGlnGluLysAlaTrpIle-114
SEQ. ID. NO. 34310 128-CysLysAlaGluAspIleThrGluAla-136
SEQ. ID. NO. 34311 150-LeuGlyTyrAspGlyLysGlyGlnIleArgValLysThrLeuAspGluLeuLysAlaAlaPhe-170
SEQ. ID. NO. 34312 182-LysMetValAspLeuArgGlyGluIle-190
SEQ. ID. NO. 34313 196-ArgLeuAsnAspGluAsnValGln-203
SEQ. ID. NO. 34314 205-PheAspProAlaGluAsnIleHisGluAsnGly-215
SEQ. ID. NO. 34315 230-ValGlnGlnGlnAlaArgGlnThrAlaGlnArgLeuAlaAspGluLeuAsp-246
SEQ. ID. NO. 34316 268-GluThrAlaProArgThrHisAsnSerGlyHisHis-279
SEQ. ID. NO. 34317 288-GlnPheGlnGlnGln-292
SEQ. ID. NO. 34318 300-ProProAlaAspThrLysLeuLeuSer-308
SEQ. ID. NO. 34319 319-ValTrpGlnGluAspGlyGlyGluProAspTrp-329
SEQ. ID. NO. 34320 332-LeuGlnSerArgProAsnAla-338
SEQ. ID. NO. 34321 344-GlyLysLysThrAlaGlnLysGlyArgLysMetGly-355
SEQ. ID. NO. 34322 361-ThrThrAspSerAspThrAlaPheGlnGluAlaLysLysLeuHis-375
Hydrophilic Regions - Hopp-Woods
SEQ. ID. NO. 34323 37-ValLeuAspProAspProAsnAlaPro-45
SEQ. ID. NO. 34324 57-ProPheAspAspArgAlaAlaLeuAspGluLeuAlaLys-69
SEQ. ID. NO. 34325 75-ThrGluPheGluAsnValAsn-81
SEQ. ID. NO. 34326 83-AspAlaMetArgSerLeuAlaLys-90
SEQ. ID. NO. 34327 128-CysLysAlaGluAspIleThrGluAla-136
SEQ. ID. NO. 34328 152-TyrAspGlyLysGlyGlnIleArgValLysThrLeuAspGluLeuLysAlaAlaPhe-170
SEQ. ID. NO. 34329 182-LysMetValAspLeuArgGlyGluIle-190
SEQ. ID. NO. 34330 196-ArgLeuAsnAspGluAsnValGln-203

TABLE 1-continued

| | |
|---|---|
| SEQ. ID. NO. 34331 | 206-AspProAlaGluAsnIleHis-212 |
| SEQ. ID. NO. 34332 | 230-ValGlnGlnGlnAlaArgGlnThrAlaGlnArgLeuAlaAspGluLeuAsp-246 |
| SEQ. ID. NO. 34333 | 269-ThrAlaProArgThrHisAsn-275 |
| SEQ. ID. NO. 34334 | 301-ProAlaAspThrLysLeu-306 |
| SEQ. ID. NO. 34335 | 320-TrpGlnGluAspGlyGlyGluProAsp-328 |
| SEQ. ID. NO. 34336 | 344-GlyLysLysThrAlaGlnLysGlyArgLysMetGly-355 |
| SEQ. ID. NO. 34337 | 362-ThrAspSerAspThrAlaPheGlnGluAlaLysLysLeuHis-375 |
| g658 | |
| AMPHI Regions - AMPHI | |
| SEQ. ID. NO. 34338 | 28-ArgGlnTyrAlaAspIleIleGlnPheValArgGlnAlaLeuArgArgLeuProArgLeuLeuLeu-49 |
| SEQ. ID. NO. 34339 | 68-ValAspValPheGlyGlyValGluGly-76 |
| SEQ. ID. NO. 34340 | 93-AlaGlnValHisHisPhePheGlnAsnAlaIleHisAla-105 |
| SEQ. ID. NO. 34341 | 139-GlnLysLeuArgAlaCysPheSerAsnValPheGly-150 |
| SEQ. ID. NO. 34342 | 155-LeuIleArgArgGlyLeuGln-161 |
| Antigenic Index - Jameson-Wolf | |
| SEQ. ID. NO. 34343 | 6-ValArgAlaArgGlyGlyPheIleAsp-14 |
| SEQ. ID. NO. 34344 | 21-AlaAspAsnLysHisPhe-26 |
| SEQ. ID. NO. 34345 | 40-AlaLeuArgArgLeuPro-45 |
| SEQ. ID. NO. 34346 | 53-ThrGlnProArgGlyAspAspGlyIleSerGlnAspAlaVal-66 |
| SEQ. ID. NO. 34347 | 86-TyrAspHisGlyAsn-90 |
| SEQ. ID. NO. 34348 | 107-ValPheGlyLysArgGlyPheGluPhe-115 |
| SEQ. ID. NO. 34349 | 130-GlnArgSerArgPheGlnAspAlaGlyGlnLysLeuArgAla-143 |
| SEQ. ID. NO. 34350 | 154-ArgLeuIleArgArgGlyLeuGln-161 |
| SEQ. ID. NO. 34351 | 193-ArgAlaHisArgValGly-198 |
| SEQ. ID. NO. 34352 | 202-PheLysPheGlyArgAsnArgArgAla-210 |
| SEQ. ID. NO. 34353 | 216-GlnArgGlyProValValLysArgArgAlaGln-226 |
| SEQ. ID. NO. 34354 | 230-GlyLysPheArgArgArgArgIleArgValGlyIleGluAsnGly-244 |
| SEQ. ID. NO. 34355 | 251-PheSerGlyAsnGlyLysHisSerAla-259 |
| Hydrophilic Regions - Hopp-Woods | |
| SEQ. ID. NO. 34356 | 6-ValArgAlaArgGlyGlyPheIle-13 |
| SEQ. ID. NO. 34357 | 21-AlaAspAsnLysHisPhe-26 |
| SEQ. ID. NO. 34358 | 40-AlaLeuArgArgLeuPro-45 |
| SEQ. ID. NO. 34359 | 53-ThrGlnProArgGlyAspAspGlyIleSer-62 |
| SEQ. ID. NO. 34360 | 130-GlnArgSerArgPheGlnAspAlaGlyGlnLysLeuArgAla-143 |
| SEQ. ID. NO. 34361 | 154-ArgLeuIleArgArgGlyLeu-160 |
| SEQ. ID. NO. 34362 | 193-ArgAlaHisArgValGly-198 |
| SEQ. ID. NO. 34363 | 205-GlyArgAsnArgArgAla-210 |
| SEQ. ID. NO. 34364 | 210-ProValValLysArgArgAlaGln-226 |
| SEQ. ID. NO. 34365 | 230-GlyLysPheArgArgArgArgIleArgValGlyIle-241 |
| SEQ. ID. NO. 34366 | 253-GlyAsnGlyLysHisSerAla-259 |
| g661 | |
| AMPHI Regions - AMPHI | |
| SEQ. ID. NO. 34367 | 19-GlyIleAlaAspLysProPheArgArgLeuCysArgAlaPheGlyAla-34 |
| SEQ. ID. NO. 34368 | 48-LeuArgAsnThrGlyLysThrLeu-55 |
| SEQ. ID. NO. 34369 | 76-ProGluGlnMetAlaAsp-81 |
| SEQ. ID. NO. 34370 | 122-AlaAlaIleLeuGluAlaValValLys-130 |
| SEQ. ID. NO. 34371 | 152-ProAlaValAlaLysIleAlaGlu-159 |
| SEQ. ID. NO. 34372 | 222-HisAspArgAlaArg-226 |
| SEQ. ID. NO. 34373 | 237-PheGluAlaLeuCysArg-242 |
| SEQ. ID. NO. 34374 | 246-PheThrAlaCysLeuGluPhe-252 |
| Antigenic Index - Jameson-Wolf | |
| SEQ. ID. NO. 34375 | 20-IleAlaAspLysProPheArgArgLeuCysArg-30 |
| SEQ. ID. NO. 34376 | 45-AspProThrLeuArgAsnThrGlyLysThrLeuHisArgSerAspPheAlaAspGluGlyGly-65 |
| SEQ. ID. NO. 34377 | 72-AlaGlySerAspProGluGlnMetAlaAspAlaAlaArg-84 |
| SEQ. ID. NO. 34378 | 97-AsnMetGlyCysProAlaLysLysValCys-106 |
| SEQ. ID. NO. 34379 | 115-MetGlnAspGluProLeu-120 |
| SEQ. ID. NO. 34380 | 143-GlyTrpHisAspAspAspGlnAsnLeu-151 |
| SEQ. ID. NO. 34381 | 156-LysIleAlaGluAspCysGly-162 |
| SEQ. ID. NO. 34382 | 169-ProArgAlaArgAla-173 |
| SEQ. ID. NO. 34383 | 175-AlaAsnValGlnArgArgGlyAlaLeuArgThrHisArgArgAspGlnLysProSerGluHisProGlyLeuGlyGlnArgArgHisHisPhe AlaAlaLysSerArgArgArgProGlnThrAsnArgArgArgArgHisHisAspArgAlaArgArgAlaArgGln-230 |
| SEQ. ID. NO. 34384 | 241-CysArgThrArgArgPhe-246 |
| SEQ. ID. NO. 34385 | 253-GlyArgMetGlnSerArgHisPheGluProHisProArgHisAlaArg-268 |
| SEQ. ID. NO. 34386 | 271-TrpXxxAspArgArgCysAlaHisArgThrGlnThrHisArgLeuValHisArgArgAsnAlaArgArgArgThrGlyAlaAla-298 |
| Hydrophilic Regions - Hopp-Woods | |
| SEQ. ID. NO. 34387 | 20-IleAlaAspLysProPheArgArgLeuCysArg-30 |
| SEQ. ID. NO. 34388 | 46-ProThrLeuArgAsnThrGlyLysThrLeuHisArgSerAspPheAlaAspGluGlyGly-65 |
| SEQ. ID. NO. 34389 | 73-GlySerAspProGluGlnMetAlaAspAlaAlaArg-84 |
| SEQ. ID. NO. 34390 | 100-CysProAlaLysLysValCys-106 |
| SEQ. ID. NO. 34391 | 115-MetGlnAspGluProLeu-120 |
| SEQ. ID. NO. 34392 | 144-TrpHisAspAspAspGlnAsn-150 |
| SEQ. ID. NO. 34393 | 156-LysIleAlaGluAspCysGly-162 |
| SEQ. ID. NO. 34394 | 169-ProArgAlaArgAla-173 |
| SEQ. ID. NO. 34395 | 175-AlaAsnValGlnArgArgGlyAlaLeuArgThrHisArgArgAspGlnLysProSerGluHisProGlyLeuGlyGlnArgArgHisHis Phe-205 |
| SEQ. ID. NO. 34396 | 207-AlaLysSerArgArgArgProGlnThrAsnArgArgArgArgHisHisAspArgAlaArgArgAlaArgGln-230 |
| SEQ. ID. NO. 34397 | 241-CysArgThrArgArgPhe-246 |
| SEQ. ID. NO. 34398 | 253-GlyArgMetGlnSerArgHisPheGluProHisProArgHisAla-267 |

TABLE 1-continued

| | |
|---|---|
| SEQ. ID. NO. 34399 | 271-TrpXxxAspArgArgCysAlaHisArgThrGlnThr-282 |
| SEQ. ID. NO. 34400 | 285-LeuValHisArgArgAsnAlaArgArgArgThrGlyAla-297 |
| g663 | |
| AMPHI Regions - AMPHI | |
| SEQ. ID. NO. 34401 | 19-ProPheAlaLeuLeuHisLysIleAlaGlyLeuIleGlySerLeuAlaTyr-35 |
| SEQ. ID. NO. 34402 | 66-LysGlnHisPheLysHisMetAlaLysLeu-75 |
| SEQ. ID. NO. 34403 | 86-SerAlaLysCysLeuLysSerLeuValArg-95 |
| SEQ. ID. NO. 34404 | 168-GluGlyLeuArgAlaLeuValLysGlnPheArgLys-179 |
| SEQ. ID. NO. 34405 | 209-ThrIleThrGlyLeuSerArgIleAlaAlaLeuAlaAsn-221 |
| SEQ. ID. NO. 34406 | 243-ProAlaTrpLysSer-247 |
| SEQ. ID. NO. 34407 | 258-GlnArgMetAsnArgPheIleGluGluArgValArgGluHis-271 |
| Antigenic Index - Jameson-Wolf | |
| SEQ. ID. NO. 34408 | 38-ValLysProArgArgArgIleGlyGlu-46 |
| SEQ. ID. NO. 34409 | 54-ProGluTrpAspGluGluLysArgLysThrValLeu-65 |
| SEQ. ID. NO. 34410 | 87-AlaLysCysLeuLysSer-92 |
| SEQ. ID. NO. 34411 | 94-ValArgTyrArgAsnLysHisTyrLeuAsp-103 |
| SEQ. ID. NO. 34412 | 105-AlaLeuAlaAlaGlyGluLys-111 |
| SEQ. ID. NO. 34413 | 139-TyrSerHisGlnLysAsnLysIleLeuAsp-148 |
| SEQ. ID. NO. 34414 | 150-GlnIleLeuLysGlyArgAsnArgTyr-158 |
| SEQ. ID. NO. 34415 | 166-ArgThrGluGlyLeuArgAlaLeu-173 |
| SEQ. ID. NO. 34416 | 175-LysGlnPheArgLysSerSerAla-182 |
| SEQ. ID. NO. 34417 | 188-ProAspGlnAspPheGlyArgAsnAsnSer-197 |
| SEQ. ID. NO. 34418 | 229-ProValArgGluAlaAspAsnThrVal-237 |
| SEQ. ID. NO. 34419 | 243-ProAlaTrpLysSerPheProSerGluAspAlaGlnAlaAspAlaGlnArgMetAsnArgPheIleGluGluArgValArgGluHisPro Glu-273 |
| SEQ. ID. NO. 34420 | 280-LysArgPheLysThrArgProGluGlySerProAspPheTyr-293 |
| Hydrophilic Regions - Hopp-Woods | |
| SEQ. ID. NO. 34421 | 39-LysProArgArgArgIleGlyGlu-46 |
| SEQ. ID. NO. 34422 | 54-ProGluTrpAspGluGluLysArgLysThrValLeu-65 |
| SEQ. ID. NO. 34423 | 88-LysCysLeuLysSer-92 |
| SEQ. ID. NO. 34424 | 94-ValArgTyrArgAsn-98 |
| SEQ. ID. NO. 34425 | 105-AlaLeuAlaAlaGlyGluLys-111 |
| SEQ. ID. NO. 34426 | 142-GlnLysAsnLysIleLeuAsp-148 |
| SEQ. ID. NO. 34427 | 150-GlnIleLeuLysGlyArgAsnArgTyr-158 |
| SEQ. ID. NO. 34428 | 166-ArgThrGluGlyLeuArgAlaLeu-173 |
| SEQ. ID. NO. 34429 | 176-GlnPheArgLysSerSer-181 |
| SEQ. ID. NO. 34430 | 190-GlnAspPheGlyArg-194 |
| SEQ. ID. NO. 34431 | 229-ProValArgGluAlaAspAsn-235 |
| SEQ. ID. NO. 34432 | 248-PheProSerGluAspAlaGlnAlaAspAlaGlnArgMetAsnArgPheIleGluGluArgValArgGluHisProGlu-273 |
| SEQ. ID. NO. 34433 | 280-LysArgPheLysThrArgProGluGlySerPro-290 |
| g664 | |
| AMPHI Regions - AMPHI | |
| SEQ. ID. NO. 34434 | 28-AlaHisArgMetGly-32 |
| SEQ. ID. NO. 34435 | 47-AlaAspValLeuAspAlaAlaHisGlyAlaAlaGly-58 |
| SEQ. ID. NO. 34436 | 90-ProValValGluIle-94 |
| SEQ. ID. NO. 34437 | 158-LeuHisArgValPheSerThrIleProArg-167 |
| Antigenic Index - Jameson-Wolf | |
| SEQ. ID. NO. 34438 | 26-AspGlyAlaHisArgMetGlyGlyArgAla-35 |
| SEQ. ID. NO. 34439 | 73-PheLeuGlnArgLysLeuGluPro-80 |
| SEQ. ID. NO. 34440 | 113-AlaValGlyGluAspGluLeuGlyVal-121 |
| SEQ. ID. NO. 34441 | 138-TyrGlyAspAspHisGluAsn-144 |
| SEQ. ID. NO. 34442 | 163-SerThrIleProArgGlnSerArgProTrp-172 |
| SEQ. ID. NO. 34443 | 175-ProLeuArgTrpCysLysThrArgPhe-183 |
| Hydrophilic Regions - Hopp-Woods | |
| SEQ. ID. NO. 34444 | 27-GlyAlaHisArgMetGlyGly-33 |
| SEQ. ID. NO. 34445 | 74-LeuGlnArgLysLeuGluPro-80 |
| SEQ. ID. NO. 34446 | 113-AlaValGlyGluAspGluLeuGlyVal-121 |
| SEQ. ID. NO. 34447 | 138-TyrGlyAspAspHisGluAsn-144 |
| SEQ. ID. NO. 34448 | 166-ProArgGlnSerArg-170 |
| g665-1 | |
| AMPHI Regions - AMPHI | |
| SEQ. ID. NO. 34449 | 6-ArgTyrLeuLysAspTyrGln-12 |
| SEQ. ID. NO. 34450 | 115-GlnCysGluProGluGlyPheArgLysIleThr-125 |
| SEQ. ID. NO. 34451 | 132-AspValMetSerLysPheThrThrThr-140 |
| SEQ. ID. NO. 34452 | 167-ArgHisTrpValLysTrpGluAspProPhe-176 |
| SEQ. ID. NO. 34453 | 225-SerLeuLysAsnAlaMetLys-231 |
| SEQ. ID. NO. 34454 | 286-GlyIleGluSerValVal-291 |
| SEQ. ID. NO. 34455 | 294-GluTyrPheHisAsnTrpThr-300 |
| SEQ. ID. NO. 34456 | 307-ArgAspTrpPheGlnLeuSerLeu-314 |
| SEQ. ID. NO. 34457 | 329-AspArgAlaGlyArgAlaValArgArgIleGluAsnIleArgLeuLeuArgGln-346 |
| SEQ. ID. NO. 34458 | 358-HisProValArgProValSerTyrGluGluMetAsnAsnPheTyrThr-373 |
| SEQ. ID. NO. 34459 | 380-GlyAlaGluValValArgMetTyrHisThrLeu-390 |
| SEQ. ID. NO. 34460 | 396-PheGlnLysGlyMetLys-401 |
| SEQ. ID. NO. 34461 | 517-GluGlyValThrGluAlaValValProSerLeuLeuArgGlyPheSerAlaProVal-535 |
| SEQ. ID. NO. 34462 | 559-CysTrpGluAlaAla-563 |
| SEQ. ID. NO. 34463 | 575-LeuAlaAlaLeuSerAspGlyIle-582 |
| SEQ. ID. NO. 34464 | 589-LysLeuLeuAlaAlaValGlu-595 |
| SEQ. ID. NO. 34465 | 603-LeuAspAsnAlaPheLysAlaLeu-610 |
| SEQ. ID. NO. 34466 | 622-AspGlyThrGluAsnIleAspProLeu-630 |
| SEQ. ID. NO. 34467 | 642-ThrLeuAlaValArg-646 |

TABLE 1-continued

| | |
|---|---|
| SEQ. ID. NO. 34468 | 648-LeuProLysTrpHisGluLeuAspArg-656 |
| SEQ. ID. NO. 34469 | 674-AspTrpArgThrLeuArgAsnValCysArgAla-684 |
| SEQ. ID. NO. 34470 | 696-ThrValAlaGluLysTyrGlyGluMetAlaGlnAsnMet-708 |
| SEQ. ID. NO. 34471 | 712-TrpGlyIleLeuSer-716 |
| SEQ. ID. NO. 34472 | 730-LeuAlaGlnPheAlaAspLysPheSer-738 |
| SEQ. ID. NO. 34473 | 758-AspThrLeuGlnGlnValGlnThrAla-766 |
| SEQ. ID. NO. 34474 | 782-SerLeuIleGlySerPheSerArgAsnVal-791 |
| SEQ. ID. NO. 34475 | 822-ArgLeuValGlnAlaPheAsnLeuCysAsnLysLeu-833 |
| Antigenic Index - Jameson-Wolf | |
| SEQ. ID. NO. 34476 | 1-MetSerLysThrValArgTyrLeuLysAspTyrGlnThrProAla-15 |
| SEQ. ID. NO. 34477 | 32-ThrValValLysSerArgLeuThrValGluProGlnArgAlaGlyGlu-47 |
| SEQ. ID. NO. 34478 | 49-LeuValLeuAspGlySerAla-55 |
| SEQ. ID. NO. 34479 | 79-AlaAspValProSerGluArgPheThrVal-88 |
| SEQ. ID. NO. 34480 | 90-ValGluThrGluIleLeuProAlaGluAsnLysSerLeu-102 |
| SEQ. ID. NO. 34481 | 115-GlnCysGluProGluGlyPheArgLys-123 |
| SEQ. ID. NO. 34482 | 128-IleAspArgProAspValMetSer-135 |
| SEQ. ID. NO. 34483 | 142-ValAlaAspLysLysArgTyrPro-149 |
| SEQ. ID. NO. 34484 | 153-SerAsnGlyAsnLysIleAspGlyGlyGluPheSerAspGlyArgHisTrpValLysTrpGluAspProPheAlaLysProSer-180 |
| SEQ. ID. NO. 34485 | 191-AlaValThrGluAspArgPheThrThrMetSerGlyArgAsnValLysIle-207 |
| SEQ. ID. NO. 34486 | 211-ThrThrGluAlaAspLysProLysVal-219 |
| SEQ. ID. NO. 34487 | 230-MetLysTrpAspGluThrArgPhe-237 |
| SEQ. ID. NO. 34488 | 255-AsnMetGlyAlaMetGluAsnLysGlyLeu-264 |
| SEQ. ID. NO. 34489 | 275-AspSerArgThrAlaThrAspThrAspPheGluGlyIleGlu-288 |
| SEQ. ID. NO. 34490 | 295-TyrPheHisAsnTrpThrGlyAsnArgValThrCysArgAspTrp-309 |
| SEQ. ID. NO. 34491 | 313-SerLeuLysGluGly-317 |
| SEQ. ID. NO. 34492 | 322-ArgAspGlnGluPheSerGlyAspArgAlaGlyArgAlaValArgArgIleGluAsn-340 |
| SEQ. ID. NO. 34493 | 342-ArgLeuLeuArgGlnAsnGlnPheProGluAspAlaGlyProThrAlaHisProValArgProValSerTyrGluGluMetAsn-369 |
| SEQ. ID. NO. 34494 | 376-ValTyrGluLysGlyAlaGluVal-383 |
| SEQ. ID. NO. 34495 | 394-GluGlyPheGlnLysGlyMet-400 |
| SEQ. ID. NO. 34496 | 404-PheGlnArgHisAspGlyGlnAlaValThrCysAspAspPheArgAlaAlaMet-421 |
| SEQ. ID. NO. 34497 | 437-SerGlnAlaGlyThrPro-442 |
| SEQ. ID. NO. 34498 | 444-LeuGluAlaGluGlyArgLeuLysAsnAsnVal-454 |
| SEQ. ID. NO. 34499 | 459-IleLysGlnThrValProProThrProAspMetAlaAspLysGlnPro-474 |
| SEQ. ID. NO. 34500 | 483-LeuLeuAsnArgAsnGlyGluAlaVal-491 |
| SEQ. ID. NO. 34501 | 494-AspTyrGlnGlyLysArgAlaThrGlu-502 |
| SEQ. ID. NO. 34502 | 508-ThrGluAlaGluGln-512 |
| SEQ. ID. NO. 34503 | 538-AsnTyrProTyrSerAspAspAspLeu-546 |
| SEQ. ID. NO. 34504 | 552-HisAspSerAspAla-556 |
| SEQ. ID. NO. 34505 | 578-LeuSerAspGlyIleGlyLeuProLysHisGluLysLeu-590 |
| SEQ. ID. NO. 34506 | 594-ValGluLysValIleSerAspAspLeuLeu-603 |
| SEQ. ID. NO. 34507 | 614-ValProSerGluAlaGluLeuTrpAspGlyThrGluAsnIleAspProLeuArg-631 |
| SEQ. ID. NO. 34508 | 633-HisGlnAlaArgGluAlaLeu-639 |
| SEQ. ID. NO. 34509 | 652-HisGluLeuAspArgGlnAlaAlaLysGlnGluAsnGlnSerTyrGluTyrSerProGluThrAlaAsp-674 |
| SEQ. ID. NO. 34510 | 676-ArgThrLeuArgAsnValCys-682 |
| SEQ. ID. NO. 34511 | 689-AlaAspProAlaHis-693 |
| SEQ. ID. NO. 34512 | 696-ThrValAlaGluLysTyrGlyGlu-703 |
| SEQ. ID. NO. 34513 | 718-ValAsnGlyAsnGluSerAspThrArgAsnCys-728 |
| SEQ. ID. NO. 34514 | 733-PheAlaAspLysPheSerAspAspAlaLeuVal-743 |
| SEQ. ID. NO. 34515 | 752-GlySerSerArgArgSerAspThrLeuGln-761 |
| SEQ. ID. NO. 34516 | 768-GlnHisProLysPheSerLeuGluAsnProAsnLysAlaArgSer-782 |
| SEQ. ID. NO. 34517 | 785-GlySerPheSerArgAsnValPro-792 |
| SEQ. ID. NO. 34518 | 796-AlaGlnAspGlySerGlyTyrArgPheIleAla-806 |
| SEQ. ID. NO. 34519 | 808-LysValIleGluIleAspArgPheAsnProGlnVal-819 |
| SEQ. ID. NO. 34520 | 831-AsnLysLeuGluProHisArgLysAsnLeuValLysGlnGluLeuGlnCys-847 |
| SEQ. ID. NO. 34521 | 849-ArgAlaGlnGluGlyLeuSerLysAspValGlyGluIleVal-862 |
| Hydrophilic Regions - Hopp-Woods | |
| SEQ. ID. NO. 34522 | 1-MetSerLysThrValArgTyrLeuLys-9 |
| SEQ. ID. NO. 34523 | 32-ThrValValLysSerArgLeuThrValGluProGlnArgAlaGlyGlu-47 |
| SEQ. ID. NO. 34524 | 81-ValProSerGluArgPheThrVal-88 |
| SEQ. ID. NO. 34525 | 90-ValGluThrGluIleLeuProAlaGluAsnLysSer-101 |
| SEQ. ID. NO. 34526 | 116-CysGluProGluGlyPheArg-122 |
| SEQ. ID. NO. 34527 | 129-AspArgProAspValMetSer-135 |
| SEQ. ID. NO. 34528 | 142-ValAlaAspLysLysArgTyr-148 |
| SEQ. ID. NO. 34529 | 154-AsnGlyAsnLysIleAspGlyGlyGluPheSerAsp-165 |
| SEQ. ID. NO. 34530 | 170-ValLysTrpGluAspProPheAla-177 |
| SEQ. ID. NO. 34531 | 191-AlaValThrGluAspArgPheThr-198 |
| SEQ. ID. NO. 34532 | 201-SerGlyArgAsnValLys-206 |
| SEQ. ID. NO. 34533 | 213-GluAlaAspLysProLysVal-219 |
| SEQ. ID. NO. 34534 | 230-MetLysTrpAspGluThrArgPhe-237 |
| SEQ. ID. NO. 34535 | 258-AlaMetGluAsnLysGly-263 |
| SEQ. ID. NO. 34536 | 275-AspSerArgThrAlaThrAspThrAspPheGluGlyIleGlu-288 |
| SEQ. ID. NO. 34537 | 313-SerLeuLysGluGly-317 |
| SEQ. ID. NO. 34538 | 322-ArgAspGlnGluPheSerGlyAspArgAlaGlyArgAlaValArgArgIleGluAsn-340 |
| SEQ. ID. NO. 34539 | 348-GlnPheProGluAspAlaGlyPro-355 |
| SEQ. ID. NO. 34540 | 363-ValSerTyrGluGluMetAsn-369 |
| SEQ. ID. NO. 34541 | 376-ValTyrGluLysGlyAlaGluVal-383 |
| SEQ. ID. NO. 34542 | 394-GluGlyPheGlnLysGlyMet-400 |
| SEQ. ID. NO. 34543 | 406-ArgHisAspGlyGln-410 |
| SEQ. ID. NO. 34544 | 413-ThrCysAspAspPheArgAlaAlaMet-421 |
| SEQ. ID. NO. 34545 | 444-LeuGluAlaGluGlyArgLeuLysAsnAsnVal-454 |

TABLE 1-continued

| | |
|---|---|
| SEQ. ID. NO. 34546 | 467-ProAspMetAlaAspLysGlnPro-474 |
| SEQ. ID. NO. 34547 | 495-TyrGlnGlyLysArgAlaThrGlu-502 |
| SEQ. ID. NO. 34548 | 508-ThrGluAlaGluGln-512 |
| SEQ. ID. NO. 34549 | 541-TyrSerAspAspAspLeu-546 |
| SEQ. ID. NO. 34550 | 552-HisAspSerAspAla-556 |
| SEQ. ID. NO. 34551 | 585-ProLysHisGluLysLeu-590 |
| SEQ. ID. NO. 34552 | 594-ValGluLysValIleSer-599 |
| SEQ. ID. NO. 34553 | 616-SerGluAlaGluLeu-620 |
| SEQ. ID. NO. 34554 | 622-AspGlyThrGluAsnIleAspPro-629 |
| SEQ. ID. NO. 34555 | 633-HisGlnAlaArgGluAlaLeu-639 |
| SEQ. ID. NO. 34556 | 652-HisGluLeuAspArgGlnAlaAlaLysGlnGluAsnGlnSer-665 |
| SEQ. ID. NO. 34557 | 668-TyrSerProGluThrAlaAsp-674 |
| SEQ. ID. NO. 34558 | 689-AlaAspProAlaHis-693 |
| SEQ. ID. NO. 34559 | 696-ThrValAlaGluLysTyrGlyGlu-703 |
| SEQ. ID. NO. 34560 | 719-AsnGlyAsnGluSerAspThrArgAsn-727 |
| SEQ. ID. NO. 34561 | 733-PheAlaAspLysPheSerAspAspAlaLeuVal-743 |
| SEQ. ID. NO. 34562 | 753-SerSerArgArgSerAspThrLeu-760 |
| SEQ. ID. NO. 34563 | 776-AsnProAsnLysAlaArgSer-782 |
| SEQ. ID. NO. 34564 | 797-GlnAspGlySerGly-801 |
| SEQ. ID. NO. 34565 | 808-LysValIleGluIleAspArgPheAsn-816 |
| SEQ. ID. NO. 34566 | 831-AsnLysLeuGluProHisArgLysAsnLeuValLysGlnGluLeuGlnCys-847 |
| SEQ. ID. NO. 34567 | 849-ArgAlaGlnGluGlyLeuSerLysAspValGlyGluIleVal-862 |
| g666 | |
| AMPHI Regions - AMPHI | |
| SEQ. ID. NO. 34568 | 24-AlaLeuIleMetSerMetVal-30 |
| SEQ. ID. NO. 34569 | 57-HisThrProGluHisValThrGly-64 |
| SEQ. ID. NO. 34570 | 89-GlyTyrAspIleLeuLysGlnGlyGlySer-98 |
| SEQ. ID. NO. 34571 | 162-LeuLysPheMetGluAlaValVal-169 |
| Antigenic Index - Jameson-Wolf | |
| SEQ. ID. NO. 34572 | 6-TyrGlnSerAsnSerGlyGluGlyValLeu-15 |
| SEQ. ID. NO. 34573 | 40-AsnGlnGlyLysValAsnThr-46 |
| SEQ. ID. NO. 34574 | 55-AspAlaHisThrProGluHis-61 |
| SEQ. ID. NO. 34575 | 63-ThrGlyLeuThrGluGlnLysGln-70 |
| SEQ. ID. NO. 34576 | 80-SerAlaAsnProLeuAla-85 |
| SEQ. ID. NO. 34577 | 92-IleLeuLysGlnGlyGlySerAlaAla-100 |
| SEQ. ID. NO. 34578 | 114-GluProGlnSerSerGlyLeuGlyGly-122 |
| SEQ. ID. NO. 34579 | 130-AspAsnThrAlaLysThr-135 |
| SEQ. ID. NO. 34580 | 137-ThrThrPheAspGlyArgGluThrAlaPro-146 |
| SEQ. ID. NO. 34581 | 154-PheLeuAspLysAspGlyXxxProLeuLys-163 |
| Hydrophilic Regions - Hopp-Woods | |
| SEQ. ID. NO. 34582 | 40-AsnGlnGlyLysValAsnThr-46 |
| SEQ. ID. NO. 34583 | 66-ThrGluGlnLysGln-70 |
| SEQ. ID. NO. 34584 | 96-GlyGlySerAlaAla-100 |
| SEQ. ID. NO. 34585 | 139-PheAspGlyArgGluThrAlaPro-146 |
| SEQ. ID. NO. 34586 | 154-PheLeuAspLysAspGlyXxxPro-161 |
| g667 | |
| AMPHI Regions - AMPHI | |
| SEQ. ID. NO. 34587 | 46-PheAlaIleIleAlaAsp-51 |
| SEQ. ID. NO. 34588 | 56-AlaArgValGluArgPheProHisPheAlaAla-66 |
| SEQ. ID. NO. 34589 | 71-LeuAlaArgLysAlaAlaGlnPhe-78 |
| SEQ. ID. NO. 34590 | 115-IleAlaAlaValAlaGluIle-121 |
| SEQ. ID. NO. 34591 | 153-AlaAspGlnLeuArgArgMetPhePheAsnGlnPheGluLysLeuGlyAsnHisAsp-171 |
| SEQ. ID. NO. 34592 | 202-GluValValLeuHisLysIleAlaAlaGlyLeu-212 |
| Antigenic Index - Jameson-Wolf | |
| SEQ. ID. NO. 34593 | 7-LeuGlyGlyGluIleValSerAspProCysAspPhe-18 |
| SEQ. ID. NO. 34594 | 25-ValGluSerAlaAlaAspGlnThrGluThrGln-35 |
| SEQ. ID. NO. 34595 | 56-AlaArgValGluArg-60 |
| SEQ. ID. NO. 34596 | 71-LeuAlaArgLysAlaAlaGln-77 |
| SEQ. ID. NO. 34597 | 84-ArgHisIleArgProArgLeuValLysArgGluGlnIle-96 |
| SEQ. ID. NO. 34598 | 152-ProAlaAspGlnLeuArg-157 |
| SEQ. ID. NO. 34599 | 165-GluLysLeuGlyAsnHisAspPhe-172 |
| SEQ. ID. NO. 34600 | 192-HisThrAlaGlyAsnArgHisAsnLeu-200 |
| SEQ. ID. NO. 34601 | 225-ValIleArgGlnGlyArgArgGlnValIleGlnArgThrAspThrLeu-240 |
| SEQ. ID. NO. 34602 | 248-IleGluSerGlnAsnArgIleHisGlySerThrLeuHisSerLysThrAspLeu-265 |
| Hydrophilic Regions - Hopp-Woods | |
| SEQ. ID. NO. 34603 | 11-IleValSerAspProCysAsp-17 |
| SEQ. ID. NO. 34604 | 25-ValGluSerAlaAlaAspGlnThrGluThrGln-35 |
| SEQ. ID. NO. 34605 | 56-AlaArgValGluArg-60 |
| SEQ. ID. NO. 34606 | 71-LeuAlaArgLysAlaAlaGln-77 |
| SEQ. ID. NO. 34607 | 84-ArgHisIleArgProArgLeuValLysArgGluGlnIle-96 |
| SEQ. ID. NO. 34608 | 165-GluLysLeuGlyAsn-169 |
| SEQ. ID. NO. 34609 | 227-ArgGlnGlyArgArgGlnValIleGlnArgThrAspThr-239 |
| SEQ. ID. NO. 34610 | 250-SerGlnAsnArgIleHis-255 |
| SEQ. ID. NO. 34611 | 259-LeuHisSerLysThrAspLeu-265 |
| g669 | |
| AMPHI Regions - AMPHI | |
| SEQ. ID. NO. 34612 | 24-LysLeuHisArgAlaPhe-29 |
| SEQ. ID. NO. 34613 | 59-GlnIlePheArgHisValGlnSer-66 |
| SEQ. ID. NO. 34614 | 79-LysProProAsnThrAla-84 |

TABLE 1-continued

| | |
|---|---|
| Antigenic Index - Jameson-Wolf | |
| SEQ. ID. NO. 34615 | 1-MetArgArgIleValLysLysHisGlnProValAsnAla-13 |
| SEQ. ID. NO. 34616 | 33-GlyArgLysArgProHisHisHisAspArgSerLeuArgArgGlnHisGlyIleGluGlyMetGlyPhe-55 |
| SEQ. ID. NO. 34617 | 64-ValGlnSerSerAsnArgGlnSerGlyArgGlnProValCysThrLysProProAsnThrAlaSer-85 |
| SEQ. ID. NO. 34618 | 100-AlaAspIleLysArgIleLeu-106 |
| Hydrophilic Regions - Hopp-Woods | |
| SEQ. ID. NO. 34619 | 1-MetArgArgIleValLysLysHisGlnPro-10 |
| SEQ. ID. NO. 34620 | 33-GlyArgLysArgProHisHisHisAspArgSerLeuArgArgGlnHisGly-49 |
| SEQ. ID. NO. 34621 | 65-GlnSerSerAsnArgGlnSerGlyArgGlnProValCysThrLysProProAsn-82 |
| SEQ. ID. NO. 34622 | 100-AlaAspIleLysArgIleLeu-106 |
| g670 | |
| AMPHI Regions - AMPHI | |
| SEQ. ID. NO. 34623 | 10-ArgSerCysPheGly-14 |
| SEQ. ID. NO. 34624 | 16-ValLysAsnAlaSerGlyValSer-23 |
| SEQ. ID. NO. 34625 | 34-IleThrArgSerAla-38 |
| SEQ. ID. NO. 34626 | 126-PheSerAlaCysSerAlaPheCysProLeu-135 |
| Antigenic Index - Jameson-Wolf | |
| SEQ. ID. NO. 34627 | 4-CysArgAsnCysLeuAlaArgSerCys-12 |
| SEQ. ID. NO. 34628 | 18-AsnAlaSerGlyValSerSerSerArgIleCysProLeuSer-31 |
| SEQ. ID. NO. 34629 | 33-LysIleThrArgSerAlaThrSerArgAlaAsnProIle-45 |
| SEQ. ID. NO. 34630 | 65-AsnThrSerProThrIleSerGlySerSerAlaGluValGlySerSerAsnSerIleThrArgGlySerIleAlaSerProArgAlaIleAla-95 |
| SEQ. ID. NO. 34631 | 100-TrpProProGluSerTrpGluGlyLysAla-109 |
| SEQ. ID. NO. 34632 | 114-AlaSerProThrArgSerLysSerSer-122 |
| SEQ. ID. NO. 34633 | 128-AlaCysSerAlaPhe-132 |
| SEQ. ID. NO. 34634 | 146-AsnThrValArgCysGly-151 |
| Hydrophilic Regions - Hopp-Woods | |
| SEQ. ID. NO. 34635 | 33-LysIleThrArgSerAlaThrSerArgAlaAsn-43 |
| SEQ. ID. NO. 34636 | 73-SerSerAlaGluValGlySer-79 |
| SEQ. ID. NO. 34637 | 116-ProThrArgSerLysSer-121 |
| g671 | |
| AMPHI Regions - AMPHI | |
| SEQ. ID. NO. 34638 | 11-PheAsnAlaProAsn-15 |
| SEQ. ID. NO. 34639 | 72-LysGlyAlaAlaLys-76 |
| SEQ. ID. NO. 34640 | 119-ArgLeuPheIleArgTyr-124 |
| Antigenic Index - Jameson-Wolf | |
| SEQ. ID. NO. 34641 | 9-ThrProPheAsnAlaProAsnThrProProLysMetArgLeuAlaLysProArgProThrAlaGluThrAlaProValSerSerGluArg-38 |
| SEQ. ID. NO. 34642 | 45-GlnAlaMetThrAsnArgGluMetAsnAspArgAlaAsnAlaAsnArgArgGlyTrpAsnGluAlaLysAlaArgSerAlaLysGlyAla Ala-75 |
| SEQ. ID. NO. 34643 | 77-SerLeuAlaLysLysLysGluThrThr-85 |
| SEQ. ID. NO. 34644 | 110-AlaGluAlaArgArgSerAlaMet-117 |
| Hydrophilic Regions - Hopp-Woods | |
| SEQ. ID. NO. 34645 | 16-ThrProProLysMetArgLeuAlaLysProArgProThrAlaGlu-30 |
| SEQ. ID. NO. 34646 | 32-AlaProValSerSerGluArg-38 |
| SEQ. ID. NO. 34647 | 47-MetThrAsnArgGluMetAsnAspArgAlaAsnAlaAsnArgArgGlyTrpAsnGluAlaLysAlaArgSerAlaLysGlyAlaAla-75 |
| SEQ. ID. NO. 34648 | 77-SerLeuAlaLysLysLysGluThrThr-85 |
| SEQ. ID. NO. 34649 | 110-AlaGluAlaArgArgSerAlaMet-117 |
| g672 | |
| AMPHI Regions - AMPHI | |
| SEQ. ID. NO. 34650 | 38-ArgAlaIleAspIleIleLysAlaGlnLys-47 |
| SEQ. ID. NO. 34651 | 50-AlaAlaLeuProProPheValSerValVal-59 |
| SEQ. ID. NO. 34652 | 67-AlaGlnAsnIleArgArgIleLeuAlaGluValPro-78 |
| SEQ. ID. NO. 34653 | 91-AlaPheCysArgGlnPheAspArgProTyr-100 |
| SEQ. ID. NO. 34654 | 105-ArgValGlnThrAlaSerAspIle-112 |
| SEQ. ID. NO. 34655 | 115-AlaAlaThrArgPheProAsn-121 |
| SEQ. ID. NO. 34656 | 131-HisProSerGluTyrGly-136 |
| SEQ. ID. NO. 34657 | 163-ProGluAsnValGlyGluAlaValArg-171 |
| SEQ. ID. NO. 34658 | 173-ThrGlyAlaGluAla-177 |
| Antigenic Index - Jameson-Wolf | |
| SEQ. ID. NO. 34659 | 1-MetArgLysIleArgThrLysIleCysGlyIleThrThrProGluAspAlaLeu-18 |
| SEQ. ID. NO. 34660 | 34-ProGlnSerProArgAlaIleAspIleIleLysAlaGlnLys-47 |
| SEQ. ID. NO. 34661 | 65-GluSerAlaGlnAsnIleArgArgIleLeuAla-75 |
| SEQ. ID. NO. 34662 | 84-PheHisGlyAspGluAspAspAlaPhe-92 |
| SEQ. ID. NO. 34663 | 95-GlnPheAspArgProTyrIle-101 |
| SEQ. ID. NO. 34664 | 107-GlnThrAlaSerAspIleArgAsnAlaAla-116 |
| SEQ. ID. NO. 34665 | 130-TyrHisProSerGluTyrGlyGlyThrGlyHisArgPheAsp-143 |
| SEQ. ID. NO. 34666 | 149-GluTyrSerGlyLysPro-154 |
| SEQ. ID. NO. 34667 | 159-GlyGlyLeuThrProGluAsnValGlyGluAlaValArg-171 |
| SEQ. ID. NO. 34668 | 176-GluAlaValAspValSerGlyGlyValGluAlaSerLysGlyLysLysAspProAlaLys-195 |
| SEQ. ID. NO. 34669 | 202-ThrAlaAsnArgLeuSerArg-208 |
| Hydrophilic Regions - Hopp-Woods | |
| SEQ. ID. NO. 34670 | 1-MetArgLysIleArgThrLysIle-8 |
| SEQ. ID. NO. 34671 | 13-ThrProGluAspAlaLeu-18 |
| SEQ. ID. NO. 34672 | 36-SerProArgAlaIleAsp-41 |
| SEQ. ID. NO. 34673 | 43-IleLysAlaGlnLys-47 |
| SEQ. ID. NO. 34674 | 66-SerAlaGlnAsnIleArgArgIleLeuAla-75 |
| SEQ. ID. NO. 34675 | 85-HisGlyAspGluAspAspAlaPhe-92 |
| SEQ. ID. NO. 34676 | 110-SerAspIleArgAsnAlaAla-116 |
| SEQ. ID. NO. 34677 | 165-AsnValGlyGluAlaValArg-171 |

TABLE 1-continued

SEQ. ID. NO. 34678 184-ValGluAlaSerLysGlyLysLysAspProAlaLys-195
SEQ. ID. NO. 34679 204-AsnArgLeuSerArg-208
g673
AMPHI Regions - AMPHI
SEQ. ID. NO. 34680 84-LeuAsnAspArgLeuAsnGlnAsnValThrGluAlaLeuGlyGlyValAspVal-101
SEQ. ID. NO. 34681 110-ArgLeuThrAspAla-114
SEQ. ID. NO. 34682 117-ValValLeuLysGlnLeuProLys-124
SEQ. ID. NO. 34683 172-ArgIleAlaAsnLeuLeuGluLeuLeuLysProTyrLeu-184
SEQ. ID. NO. 34684 212-LysLeuPheArgTyrLeuGlyGluGlu-220
SEQ. ID. NO. 34685 232-PheGluGluGlyAspGly-237
SEQ. ID. NO. 34686 261-GlyGluArgLeuLysLysIleSerThr-269
SEQ. ID. NO. 34687 286-LysValTrpValLysValLys-292
Antigenic Index - Jameson-Wolf
SEQ. ID. NO. 34688 7-LeuAlaGlyGluArgAlaAlaGlyGlyTyrArg-17
SEQ. ID. NO. 34689 24-ValGlyArgProAsnValGlyLysSerThr-33
SEQ. ID. NO. 34690 44-SerIleThrSerLysLysAlaGlnThrThrArgAsnArgValThr-58
SEQ. ID. NO. 34691 61-TyrThrAspAspThrAla-66
SEQ. ID. NO. 34692 73-ThrProGlyPheGlnThrAspHisArgAsnAlaLeuAsnAspArgLeuAsnGlnAsnValThrGlu-94
SEQ. ID. NO. 34693 109-MetArgLeuThrAspAlaAspArgValVal-118
SEQ. ID. NO. 34694 121-GlnLeuProLysHisThr-126
SEQ. ID. NO. 34695 134-LysIleAspLysAspLysAlaLysAspArgTyrAla-145
SEQ. ID. NO. 34696 153-ValArgAlaGluPhe-157
SEQ. ID. NO. 34697 180-LeuLysProTyrLeuProGluSerVal-188
SEQ. ID. NO. 34698 190-MetTyrProGluAspMetValThrAspLysSerAlaArg-202
SEQ. ID. NO. 34699 208-IleValArgGluLysLeuPhe-214
SEQ. ID. NO. 34700 217-LeuGlyGluGluLeuPro-222
SEQ. ID. NO. 34701 227-ValGluValGluGlnPheGluGluGlyAspGlyLeuAsn-239
SEQ. ID. NO. 34702 247-ValAspLysGluSerGlnLys-253
SEQ. ID. NO. 34703 258-GlyLysGlyGlyGluArgLeuLysLysIleSerThrGluAlaArgLeuAspMetGluLysLeuPheAspAsnLysVal-283
SEQ. ID. NO. 34704 291-ValLysSerGlyTrpAlaAspAspIleArgPheLeuArg-303
Hydrophilic Regions - Hopp-Woods
SEQ. ID. NO. 34705 7-LeuAlaGlyGluArgAlaAlaGly-14
SEQ. ID. NO. 34706 45-IleThrSerLysLysAlaGlnThrThrArgAsnArgVal-57
SEQ. ID. NO. 34707 61-TyrThrAspAspThrAla-66
SEQ. ID. NO. 34708 78-ThrAspHisArgAsnAlaLeuAsnAspArgLeuAsn-89
SEQ. ID. NO. 34709 109-MetArgLeuThrAspAlaAspArgValVal-118
SEQ. ID. NO. 34710 134-LysIleAspLysAspLysAlaLysAspArgTyrAla-145
SEQ. ID. NO. 34711 153-ValArgAlaGluPhe-157
SEQ. ID. NO. 34712 194-AspMetValThrAspLysSerAlaArg-202
SEQ. ID. NO. 34713 208-IleValArgGluLysLeuPhe-214
SEQ. ID. NO. 34714 217-LeuGlyGluGluLeuPro-222
SEQ. ID. NO. 34715 227-ValGluValGluGlnPheGluGluGlyAspGlyLeuAsn-239
SEQ. ID. NO. 34716 247-ValAspLysGluSerGlnLys-253
SEQ. ID. NO. 34717 259-LysGlyGlyGluArgLeuLysLysIleSerThrGluAlaArgLeuAspMetGluLysLeuPheAsp-280
SEQ. ID. NO. 34718 293-SerGlyTrpAlaAspAspIleArgPheLeuArg-303
g674
AMPHI Regions - AMPHI
SEQ. ID. NO. 34719 16-ValTyrGlnSerLeuIle-21
SEQ. ID. NO. 34720 24-ThrAlaAlaProGluIleAlaLysAsnIleArgGluMetSerAspPheAlaLysAlaAspGluGluLeu-46
SEQ. ID. NO. 34721 58-AlaAlaAspTyrIleGlnLysIleArg-66
SEQ. ID. NO. 34722 86-ThrAlaCysHisGluLeuSerAlaMetProGluThr-97
SEQ. ID. NO. 34723 107-IleGluValThrLysThrPheGlyGlyThrAspGlyHisLysPheValAsnGlyIleLeuAspLysLeuAla-130
Antigenic Index - Jameson-Wolf
SEQ. ID. NO. 34724 1-MetLysThrAlaArgArgArgSerArgGluLeuAla-12
SEQ. ID. NO. 34725 28-GluIleAlaLysAsnIleArgGluMetSerAspPheAlaLysAlaAspGluGluLeuPhe-47
SEQ. ID. NO. 34726 54-ThrGlnThrAsnAla-58
SEQ. ID. NO. 34727 61-TyrIleGlnLysIleArgProLeuLeuAspArgAspGluLysAspLeuAsnProIleGluArg-81
SEQ. ID. NO. 34728 93-AlaMetProGluThrProTyr-99
SEQ. ID. NO. 34729 105-GluAlaIleGluValThrLysThrPheGlyGlyThrAspGlyHisLysPhe-121
SEQ. ID. NO. 34730 129-LeuAlaAlaGlnIleArgProAspGluProLysArgArg-141
Hydrophilic Regions - Hopp-Woods
SEQ. ID. NO. 34731 1-MetLysThrAlaArgArgArgSerArgGluLeuAla-12
SEQ. ID. NO. 34732 28-GluIleAlaLysAsnIleArgGluMetSerAspPheAlaLysAlaAspGluGluLeuPhe-47
SEQ. ID. NO. 34733 63-GlnLysIleArgProLeuLeuAspArgAspGluLysAspLeuAsnProIleGluArg-81
SEQ. ID. NO. 34734 105-GluAlaIleGluVal-109
SEQ. ID. NO. 34735 133-IleArgProAspGluProLysArgArg-141
g675
AMPHI Regions - AMPHI
SEQ. ID. NO. 34736 21-ArgPheThrAsnGluIleGlySerGlnMetLeuLysValCysCysArgThrLeuGlnGluLeuGly-42
SEQ. ID. NO. 34737 74-AlaLeuIleAlaIle-78
SEQ. ID. NO. 34738 123-GlnAlaIleGluArgIleGlyGluLysAlaSerAsp-134
SEQ. ID. NO. 34739 141-GluCysAlaAsnLeuValAsnLeuLeuLeuGlu-151
Antigenic Index - Jameson-Wolf
SEQ. ID. NO. 34740 6-ProAsnLeuAspGlyLysHisLeuArg-14
SEQ. ID. NO. 34741 42-GlyValAlaAspGluAsnIle-48
SEQ. ID. NO. 34742 68-SerSerGluLysPheAsp-73
SEQ. ID. NO. 34743 82-IleArgGlyGluThrTyr-87
SEQ. ID. NO. 34744 93-AlaAsnGluSerGlyAlaGlyIle-100
SEQ. ID. NO. 34745 118-ThrGluAsnAspAlaGlnAlaIleGluArgIleGlyGluLysAlaSerAspAlaAlaLysValAlaVal-140
SEQ. ID. NO. 34746 152-GluGlnPheGluAspGluGlu-158

TABLE 1-continued

Hydrophilic Regions - Hopp-Woods
SEQ. ID. NO. 34747 8-LeuAspGlyLysHisLeuArg-14
SEQ. ID. NO. 34748 42-GlyValAlaAspGluAsnIle-48
SEQ. ID. NO. 34749 68-SerSerGluLysPheAsp-73
SEQ. ID. NO. 34750 82-IleArgGlyGluThrTyr-87
SEQ. ID. NO. 34751 95-GluSerGlyAlaGly-99
SEQ. ID. NO. 34752 118-ThrGluAsnAspAlaGlnAlaIleGluArgIleGlyGluLysAlaSerAspAlaAlaLysValAlaVal-140
SEQ. ID. NO. 34753 152-GluGlnPheGluAspGluGlu-158
g677
AMPHI Regions - AMPHI
SEQ. ID. NO. 34754 19-ThrValArgLeuCysArgPheArgArg-27
SEQ. ID. NO. 34755 45-LeuThrAlaPheArgArgValGlnAsnHisPheValAlaPheAlaArgPheAsnGlnAlaThrArgGlnArgArg-69
SEQ. ID. NO. 34756 79-IleAspPheIleAspAlaAsp-85
SEQ. ID. NO. 34757 87-PheAspGlyLeuLeuAla-92
SEQ. ID. NO. 34758 155-CysArgProValAspAspLeuAspAsp-163
SEQ. ID. NO. 34759 166-AlaPhePheIleAspGlnLeuIleLysLeuValPheGlnCys-179
Antigenic Index - Jameson-Wolf
SEQ. ID. NO. 34760 23-CysArgPheArgArgHisSerArgSerValAsp-33
SEQ. ID. NO. 34761 35-AspValPheAspArgLysAspPheAsnPhe-44
SEQ. ID. NO. 34762 63-GlnAlaThrArgGlnArgArgAsnProArgAsnPheVal-75
SEQ. ID. NO. 34763 82-IleAspAlaAspAspPheAspGly-89
SEQ. ID. NO. 34764 97-GlnGlnThrAspGlyArgAlaGluLys-105
SEQ. ID. NO. 34765 115-GlyIleAspAspAspGlySerLeu-122
SEQ. ID. NO. 34766 125-PheGlyGlnGluThrAspAlaAlaVal-133
SEQ. ID. NO. 34767 156-ArgProValAspAspLeuAspAspPheGly-165
SEQ. ID. NO. 34768 181-ProSerGlyGlyArgAsn-186
Hydrophilic Regions - Hopp-Woods
SEQ. ID. NO. 34769 23-CysArgPheArgArgHisSerArgSerValAsp-33
SEQ. ID. NO. 34770 35-AspValPheAspArgLysAspPhe-42
SEQ. ID. NO. 34771 63-GlnAlaThrArgGlnArgArgAsnProArg-72
SEQ. ID. NO. 34772 82-IleAspAlaAspAspPheAsp-88
SEQ. ID. NO. 34773 97-GlnGlnThrAspGlyArgAlaGluLys-105
SEQ. ID. NO. 34774 115-GlyIleAspAspAspGlySer-121
SEQ. ID. NO. 34775 126-GlyGlnGluThrAspAlaAlaVal-133
SEQ. ID. NO. 34776 156-ArgProValAspAspLeuAspAsp-163
g678
AMPHI Regions - AMPHI
SEQ. ID. NO. 34777 24-MetArgGlyValIle-28
SEQ. ID. NO. 34778 47-PheAlaAlaProPhe-51
SEQ. ID. NO. 34779 80-IleGlnLysMetLeuArgSerLeuLeuThrGlyAla-91
SEQ. ID. NO. 34780 102-ArgIleLeuGlyGlyValPheGlyAlaLeu-111
SEQ. ID. NO. 34781 130-ProAspThrGluGlu-134
Antigenic Index - Jameson-Wolf
SEQ. ID. NO. 34782 125-SerLysThrAspLeuProAspThrGluGluTrpGlnGlnSerTyr-139
SEQ. ID. NO. 34783 153-AsnHisThrAspAsnAlaProGluSerLeuAspAspAsp-165
Hydrophilic Regions - Hopp-Woods
SEQ. ID. NO. 34784 125-SerLysThrAspLeuProAspThrGluGluTrpGln-136
SEQ. ID. NO. 34785 155-ThrAspAsnAlaProGluSerLeuAspAspAsp-165
g681
AMPHI Regions - AMPHI
SEQ. ID. NO. 34786 12-PheSerGluGluAlaLysPheIleSerAlaMet-22
SEQ. ID. NO. 34787 110-CysAlaValPheGlyLysLeuProArg-118
SEQ. ID. NO. 34788 123-LeuGlyLysGlnCysGly-128
SEQ. ID. NO. 34789 137-ValGlyGluAlaAspAspAla-143
SEQ. ID. NO. 34790 146-ValGlyValValGlyValPheVal-153
SEQ. ID. NO. 34791 202-LysCysValHisCysGlyAsnThr-209
SEQ. ID. NO. 34792 212-GlyGlyLysLeuAlaAspPheThrThrIleProAla-223
SEQ. ID. NO. 34793 235-CysAlaProPheAlaAlaLeuArgCysPheCysIlePheGlyValTrpLysArgIleArgAlaValPheCysGlyArg-260
Antigenic Index - Jameson-Wolf
SEQ. ID. NO. 34794 11-AsnPheSerGluGluAlaLysPhe-18
SEQ. ID. NO. 34795 39-AlaThrProAsnSerTrpArgValArgGlnGln-49
SEQ. ID. NO. 34796 59-LeuValLysArgAlaCys-64
SEQ. ID. NO. 34797 67-ProMetArgArgCysLeuProSerArgLeu-76
SEQ. ID. NO. 34798 91-SerGluCysArgLeuLys-96
SEQ. ID. NO. 34799 122-GlyLeuGlyLysGlnCysGlyGlyPhe-130
SEQ. ID. NO. 34800 134-PheGlyAspValGlyGluAlaAspAspAlaGluVal-145
SEQ. ID. NO. 34801 157-AlaAlaGluGluThrPro-162
SEQ. ID. NO. 34802 173-AlaValLysGluAlaAspGly-179
SEQ. ID. NO. 34803 185-AspGlyValGlyGlyAspAlaAlaValGluCysArgGlyLysCysLeuCys-201
SEQ. ID. NO. 34804 209-ThrLeuGlyGlyGlyLysLeuAlaAsp-217
SEQ. ID. NO. 34805 224-LeuSerAlaAspGlyGlyGly-230
SEQ. ID. NO. 34806 257-PheCysGlyArgArg-261
Hydrophilic Regions - Hopp-Woods
SEQ. ID. NO. 34807 11-AsnPheSerGluGluAlaLysPhe-18
SEQ. ID. NO. 34808 44-TrpArgValArgGln-48
SEQ. ID. NO. 34809 59-LeuValLysArgAlaCys-64
SEQ. ID. NO. 34810 67-ProMetArgArgCysLeuPro-73
SEQ. ID. NO. 34811 91-SerGluCysArgLeuLys-96
SEQ. ID. NO. 34812 136-AspValGlyGluAlaAspAspAlaGluVal-145
SEQ. ID. NO. 34813 157-AlaAlaGluGluThrPro-162

TABLE 1-continued

| | |
|---|---|
| SEQ. ID. NO. 34814 | 173-AlaValLysGluAlaAspGly-179 |
| SEQ. ID. NO. 34815 | 191-AlaAlaValGluCysArgGlyLysCysLeu-200 |
| SEQ. ID. NO. 34816 | 257-PheCysGlyArgArg-261 |
| g682 | |
| AMPHI Regions - AMPHI | |
| SEQ. ID. NO. 34817 | 33-ArgLeuArgLysCysGlyArgIleLeuSerGlyIleCysGluProPhe-48 |
| SEQ. ID. NO. 34818 | 75-IleLysMetProSerGluPro-81 |
| SEQ. ID. NO. 34819 | 91-AlaGlyPheIleArgPhePro-97 |
| Antigenic Index - Jameson-Wolf | |
| SEQ. ID. NO. 34820 | 9-ProTyrGlyGluArgArgLysAsnTrpAsp-18 |
| SEQ. ID. NO. 34821 | 29-LeuSerProThrArgLeuArgLysCysGlyArg-39 |
| SEQ. ID. NO. 34822 | 70-CysValAsnAspGluIleLysMetProSerGluProAspTrp-83 |
| SEQ. ID. NO. 34823 | 95-ArgPheProThrAspArgProIleLeu-103 |
| SEQ. ID. NO. 34824 | 112-IleSerProArgThrGlyPheArgTyrProThrArgSerLeuProLysSerLysLysAlaTyrGly-133 |
| Hydrophilic Regions - Hopp-Woods | |
| SEQ. ID. NO. 34825 | 11-GlyGluArgArgLysAsnTrpAsp-18 |
| SEQ. ID. NO. 34826 | 30-SerProThrArgLeuArgLysCysGlyArg-39 |
| SEQ. ID. NO. 34827 | 72-AsnAspGluIleLysMetProSerGluProAspTrp-83 |
| SEQ. ID. NO. 34828 | 97-ProThrAspArgProIleLeu-103 |
| SEQ. ID. NO. 34829 | 124-SerLeuProLysSerLysLysAlaTyrGly-133 |
| g683 | |
| AMPHI Regions - AMPHI | |
| SEQ. ID. NO. 34830 | 26-ThrProAspLysSerAlaArgTrpGluAsnIleGlyThrIleSerAsn-41 |
| SEQ. ID. NO. 34831 | 75-ArgPheAlaAsnThrPro-80 |
| SEQ. ID. NO. 34832 | 101-SerSerLeuGlnLeuPhe-106 |
| SEQ. ID. NO. 34833 | 124-ArgProMetSerIleLeuSerGly-131 |
| Antigenic Index - Jameson-Wolf | |
| SEQ. ID. NO. 34834 | 24-CysSerThrProAspLysSerAlaArgTrpGluAsn-35 |
| SEQ. ID. NO. 34835 | 37-GlyThrIleSerAsnGly-42 |
| SEQ. ID. NO. 34836 | 48-IleAsnLysAspSerValArgLysAsnGlyAsn-58 |
| SEQ. ID. NO. 34837 | 63-GlnAspLysLysValValThrAsnLeuLysGlnGluArgPheAlaAsnThrProAlaTyr-82 |
| SEQ. ID. NO. 34838 | 93-CysAsnAsnLysThrTyrArgLeu-100 |
| SEQ. ID. NO. 34839 | 106-PheAspThrLysAsnThrGluIleSerThrGlnAsnTyrThrAlaSerSerLeuArgPro-125 |
| SEQ. ID. NO. 34840 | 131-GlyThrLeuThrGluLysGlnTyrGlu-139 |
| SEQ. ID. NO. 34841 | 141-ValCysGlyLysLysLeu-146 |
| Hydrophilic Regions - Hopp-Woods | |
| SEQ. ID. NO. 34842 | 25-SerThrProAspLysSerAlaArgTrpGluAsn-35 |
| SEQ. ID. NO. 34843 | 48-IleAsnLysAspSerValArgLysAsnGly-57 |
| SEQ. ID. NO. 34844 | 63-GlnAspLysLysValValThr-69 |
| SEQ. ID. NO. 34845 | 71-LeuLysGlnGluArgPheAla-77 |
| SEQ. ID. NO. 34846 | 107-AspThrLysAsnThrGluIleSer-114 |
| SEQ. ID. NO. 34847 | 133-LeuThrGluLysGlnTyrGlu-139 |
| SEQ. ID. NO. 34848 | 141-ValCysGlyLysLysLeu-146 |
| g684 | |
| AMPHI Regions - AMPHI | |
| SEQ. ID. NO. 34849 | 13-AlaAlaCysGlyThrValGln-19 |
| SEQ. ID. NO. 34850 | 47-LeuAlaGluProLeu-51 |
| SEQ. ID. NO. 34851 | 73-TrpAlaAspThrLeuAspAspMetLeuGluAlaAlaLeuSerAsnAlaPheAsnArgLeuAspSerThrArg-96 |
| SEQ. ID. NO. 34852 | 110-TrpThrValTyrIleAspAlaPheGlnGlySerTyr-121 |
| SEQ. ID. NO. 34853 | 154-AlaMetThrAlaAlaLeuGluGlnGlyLeuLysGlnAlaAlaGlnGlnMetVal-171 |
| Antigenic Index - Jameson-Wolf | |
| SEQ. ID. NO. 34854 | 26-LeuProAspSerArgTyrIleArgProAlaThrGlnGlyGlyGluThrAlaValGluValArgLeuAlaGluProLeuLysArgGlyGlyLeu-56 |
| SEQ. ID. NO. 34855 | 60-ThrAspProTyrArgIleAsnThrAlaGln-69 |
| SEQ. ID. NO. 34856 | 76-ThrLeuAspAspMetLeuGlu-82 |
| SEQ. ID. NO. 34857 | 90-AsnArgLeuAspSerThrArgThrPhe-98 |
| SEQ. ID. NO. 34858 | 101-AlaSerArgSerGlySerThrAspLys-109 |
| SEQ. ID. NO. 34859 | 117-PheGlnGlySerTyrThrGlyLysThrLeu-126 |
| SEQ. ID. NO. 34860 | 133-LeuProAspGlyThrAsnArgProPheHisIleGluThrGluGlnGlnGlyAspGlyTyrAla-153 |
| SEQ. ID. NO. 34861 | 161-GlnGlyLeuLysGlnAlaAla-167 |
| Hydrophilic Regions - Hopp-Woods | |
| SEQ. ID. NO. 34862 | 27-ProAspSerArgTyrIleArg-33 |
| SEQ. ID. NO. 34863 | 35-AlaThrGlnGlyGlyGluThrAlaValGluValArgLeuAlaGluProLeuLysArgGlyGly-55 |
| SEQ. ID. NO. 34864 | 76-ThrLeuAspAspMetLeuGlu-82 |
| SEQ. ID. NO. 34865 | 90-AsnArgLeuAspSerThrArg-96 |
| SEQ. ID. NO. 34866 | 102-SerArgSerGlySerThrAspLys-109 |
| SEQ. ID. NO. 34867 | 141-PheHisIleGluThrGluGlnGlnGlyAsp-150 |
| SEQ. ID. NO. 34868 | 161-GlnGlyLeuLysGlnAlaAla-167 |
| g685 | |
| AMPHI Regions - AMPHI | |
| SEQ. ID. NO. 34869 | 7-AsnPheAlaPheCysGlyValVal-14 |
| SEQ. ID. NO. 34870 | 44-CysAlaValLeuPro-48 |
| SEQ. ID. NO. 34871 | 61-ValSerAlaAlaSerGln-66 |
| SEQ. ID. NO. 34872 | 98-TrpAlaAlaLeuAspThrLeuThrGluPro-107 |
| SEQ. ID. NO. 34873 | 141-CysGluSerLeuHisArgHis-147 |
| SEQ. ID. NO. 34874 | 158-GlyAlaGluAlaTyrGluGlnLeuAlaLysAsn-168 |
| SEQ. ID. NO. 34875 | 186-GluLysGlnMetGluThrLeuSerArgIlePheGly-197 |
| SEQ. ID. NO. 34876 | 300-AlaValGluValLeu-304 |
| SEQ. ID. NO. 34877 | 340-AlaAlaGluGlnLeuLysAlaAla-347 |

TABLE 1-continued

| | |
|---|---|
| Antigenic Index - Jameson-Wolf | |
| SEQ. ID. NO. 34878 | 20-LeuAsnAsnLysHisSerTyrSerTyrAlaLysGluProHisThrValLysProArgPhe-39 |
| SEQ. ID. NO. 34879 | 51-CysSerProGluProAlaAlaGluLysThrValSer-62 |
| SEQ. ID. NO. 34880 | 78-ProThrAlaArgGlyAspAlaValValProLysAsnProGluArgValAla-94 |
| SEQ. ID. NO. 34881 | 103-ThrLeuThrGluProGlyVal-109 |
| SEQ. ID. NO. 34882 | 126-AlaPheAspLysAlaAla-131 |
| SEQ. ID. NO. 34883 | 137-PheGluProAspCysGluSerLeuHisArgHisAsnPro-149 |
| SEQ. ID. NO. 34884 | 155-GlyGlyProGlyAlaGluAlaTyrGluGlnLeuAlaLysAsnAlaThr-170 |
| SEQ. ID. NO. 34885 | 174-LeuThrValAspAsnGlyAsnIleArgThrSerGlyGluLysGlnMetGluThrLeu-192 |
| SEQ. ID. NO. 34886 | 195-IlePheGlyLysGluAlaArgValAlaGlu-204 |
| SEQ. ID. NO. 34887 | 213-PheAlaGlnLysArgGluAlaAlaLysGlyLysGlyArgGlyLeu-227 |
| SEQ. ID. NO. 34888 | 231-ValThrGlyAsnLysValSerAlaPheGlyThrGlnSerArgLeu-245 |
| SEQ. ID. NO. 34889 | 251-GlyAspIleGlyLeuProProValAspGluSerLeuArgAsnGluGlyHisGlyGln-269 |
| SEQ. ID. NO. 34890 | 275-TyrIleLysGluLysAsnProGlyTrp-283 |
| SEQ. ID. NO. 34891 | 289-ArgThrAlaAlaIleGlyGlnGluGlyProAla-299 |
| SEQ. ID. NO. 34892 | 313-AsnAlaTrpLysArgLysGln-319 |
| SEQ. ID. NO. 34893 | 342-GluGlnLeuLysAlaAlaPheGluLysAlaGluProValAla-355 |
| Hydrophilic Regions - Hopp-Woods | |
| SEQ. ID. NO. 34894 | 28-TyrAlaLysGluProHisThrValLys-36 |
| SEQ. ID. NO. 34895 | 51-CysSerProGluProAlaAlaGluLysThrValSer-62 |
| SEQ. ID. NO. 34896 | 79-ThrAlaArgGlyAspAlaValVal-86 |
| SEQ. ID. NO. 34897 | 88-LysAsnProGluArgValAla-94 |
| SEQ. ID. NO. 34898 | 126-AlaPheAspLysAlaAla-131 |
| SEQ. ID. NO. 34899 | 137-PheGluProAspCysGluSerLeuHisArgHis-147 |
| SEQ. ID. NO. 34900 | 160-GluAlaTyrGluGlnLeuAlaLys-167 |
| SEQ. ID. NO. 34901 | 179-GlyAsnIleArgThrSerGlyGluLysGlnMetGluThrLeu-192 |
| SEQ. ID. NO. 34902 | 195-IlePheGlyLysGluAlaArgValAlaGlu-204 |
| SEQ. ID. NO. 34903 | 213-PheAlaGlnLysArgGluAlaAlaLysGlyLysGlyArgGly-226 |
| SEQ. ID. NO. 34904 | 257-ProValAspGluSerLeuArgAsnGluGlyHisGly-268 |
| SEQ. ID. NO. 34905 | 275-TyrIleLysGluLysAsnPro-281 |
| SEQ. ID. NO. 34906 | 294-GlyGlnGluGlyProAla-299 |
| SEQ. ID. NO. 34907 | 314-AlaTrpLysArgLysGln-319 |
| SEQ. ID. NO. 34908 | 342-GluGlnLeuLysAlaAlaPheGluLysAlaGluProValAla-355 |
| g686 | |
| AMPHI Regions - AMPHI | |
| SEQ. ID. NO. 34909 | 10-AspValPheAspAspIleCysSerAlaValGluGlyPheGlyGlyIleAlaArgSerValGlnLeu-31 |
| SEQ. ID. NO. 34910 | 50-SerAlaGlyIleValGluThrValGlyLysProLeu-61 |
| SEQ. ID. NO. 34911 | 70-ValGluAlaAspIle-74 |
| SEQ. ID. NO. 34912 | 86-IleProArgAlaPheGlySerGlyIleAlaAlaAlaLeu-98 |
| Antigenic Index - Jameson-Wolf | |
| SEQ. ID. NO. 34913 | 1-TerTerAsnPheSerCysArgAlaAspAspValPheAsp-13 |
| SEQ. ID. NO. 34914 | 46-LeuArgGlnHisSerAlaGlyIle-53 |
| SEQ. ID. NO. 34915 | 56-ThrValGlyLysProLeuSerGlyAla-64 |
| SEQ. ID. NO. 34916 | 70-ValGluAlaAspIle-74 |
| SEQ. ID. NO. 34917 | 115-AspAlaValLysAlaGluSerValAsnGlyThrThrGly-127 |
| Hydrophilic Regions - Hopp-Woods | |
| SEQ. ID. NO. 34918 | 6-CysArgAlaAspAspValPheAsp-13 |
| SEQ. ID. NO. 34919 | 70-ValGluAlaAspIle-74 |
| SEQ. ID. NO. 34920 | 115-AspAlaValLysAlaGluSerValAsn-123 |
| g687 | |
| AMPHI Regions - AMPHI | |
| SEQ. ID. NO. 34921 | 13-AlaAlaLeuPheAlaLeu-18 |
| SEQ. ID. NO. 34922 | 66-LysValGluValLeuGluPhePheGlyTyrPheCysPro-78 |
| SEQ. ID. NO. 34923 | 80-CysAlaArgLeuGluPro-85 |
| SEQ. ID. NO. 34924 | 87-LeuSerLysHisAlaLysSerPhe-94 |
| SEQ. ID. NO. 34925 | 114-LeuAlaArgLeuAlaAlaAla-120 |
| SEQ. ID. NO. 34926 | 137-PheAspAlaMetVal-141 |
| SEQ. ID. NO. 34927 | 150-ProGluValLeuLysLysTrpLeu-157 |
| SEQ. ID. NO. 34928 | 174-SerProGluSerGln-178 |
| SEQ. ID. NO. 34929 | 182-GlyLysMetGlnGluLeuThrGluThrPhe-191 |
| Antigenic Index - Jameson-Wolf | |
| SEQ. ID. NO. 34930 | 1-MetLysSerArgHis-5 |
| SEQ. ID. NO. 34931 | 21-CysAspSerLysValGlnThrSerValProAlaAspSerAlaPro-35 |
| SEQ. ID. NO. 34932 | 45-GlyLeuValGluGlyGlnAsnTyr-52 |
| SEQ. ID. NO. 34933 | 58-ProIleProGlnGlnGlnAlaGlyLysValGluVal-69 |
| SEQ. ID. NO. 34934 | 77-CysProHisCysAlaArgLeuGluProValLeu-87 |
| SEQ. ID. NO. 34935 | 89-LysHisAlaLysSerPheLysAspAspMetTyrLeu-100 |
| SEQ. ID. NO. 34936 | 124-AlaAlaAlaGluSerLysAspValAlaAsn-133 |
| SEQ. ID. NO. 34937 | 143-GlnLysIleLysLeuGlnGluProGluValLeuLys-154 |
| SEQ. ID. NO. 34938 | 161-ThrAlaPheAspGlyLysLysVal-168 |
| SEQ. ID. NO. 34939 | 173-GluSerProGluSerGlnAlaArgAlaGlyLysMetGlnGluLeuThrGlu-189 |
| SEQ. ID. NO. 34940 | 191-PheGlnIleAspGlyThrPro-197 |
| SEQ. ID. NO. 34941 | 201-ValGlyGlyLysTyrLysValGluPheAlaAsp-211 |
| SEQ. ID. NO. 34942 | 213-GluSerGlyMetAsnThr-218 |
| SEQ. ID. NO. 34943 | 222-LeuAlaAspLysValArgGluGluGlnLysAlaAlaGln-234 |
| Hydrophilic Regions - Hopp-Woods | |
| SEQ. ID. NO. 34944 | 1-MetLysSerArgHis-5 |
| SEQ. ID. NO. 34945 | 21-CysAspSerLysValGlnThr-27 |
| SEQ. ID. NO. 34946 | 29-ValProAlaAspSerAlaPro-35 |
| SEQ. ID. NO. 34947 | 63-GlnAlaGlyLysValGluVal-69 |

TABLE 1-continued

| | |
|---|---|
| SEQ. ID. NO. 34948 | 81-AlaArgLeuGluProValLeu-87 |
| SEQ. ID. NO. 34949 | 89-LysHisAlaLysSerPheLysAspAspMetTyrLeu-100 |
| SEQ. ID. NO. 34950 | 124-AlaAlaAlaGluSerLysAspValAla-132 |
| SEQ. ID. NO. 34951 | 143-GlnLysIleLysLeuGlnGluProGluValLeuLys-154 |
| SEQ. ID. NO. 34952 | 161-ThrAlaPheAspGlyLysLysVal-168 |
| SEQ. ID. NO. 34953 | 173-GluSerProGluSerGlnAlaArgAlaGlyLysMetGlnGluLeuThrGlu-189 |
| SEQ. ID. NO. 34954 | 203-GlyLysTyrLysValGluPheAlaAsp-211 |
| SEQ. ID. NO. 34955 | 222-LeuAlaAspLysValArgGluGluGlnLysAlaAlaGln-234 |
| g688 | |
| AMPHI Regions - AMPHI | |
| SEQ. ID. NO. 34956 | 22-LeuSerAlaLeuPheSerLeu-28 |
| SEQ. ID. NO. 34957 | 119-GlyAspAlaLeuGlnAsnAlaAla-126 |
| Antigenic Index - Jameson-Wolf | |
| SEQ. ID. NO. 34958 | 5-SerArgPheAlaGlnLysGlySerProValAsnLys-16 |
| SEQ. ID. NO. 34959 | 31-CysSerValGluArg-35 |
| SEQ. ID. NO. 34960 | 46-IleIleGlnGlyAsnGluLeuGluProArgAla-56 |
| SEQ. ID. NO. 34961 | 61-ArgProGlyMetThrLysAspGln-68 |
| SEQ. ID. NO. 34962 | 81-AlaPheHisThrAspArgTrpAspTyr-89 |
| SEQ. ID. NO. 34963 | 91-PheAsnThrSerArgAsnGlyIleIleLysGluArgSerAsnLeu-105 |
| SEQ. ID. NO. 34964 | 115-ValArgThrGluGlyAspAlaLeuGlnAsnAlaAlaGluAlaLeuArgAlaLysGlnAsnAlaAspLysGln-138 |
| Hydrophilic Regions - Hopp-Woods | |
| SEQ. ID. NO. 34965 | 7-PheAlaGlnLysGlySerProVal-14 |
| SEQ. ID. NO. 34966 | 50-AsnGluLeuGluProArgAla-56 |
| SEQ. ID. NO. 34967 | 63-GlyMetThrLysAspGln-68 |
| SEQ. ID. NO. 34968 | 97-GlyIleIleLysGluArgSerAsn-104 |
| SEQ. ID. NO. 34969 | 115-ValArgThrGluGlyAspAlaLeuGlnAsnAlaAlaGluAlaLeuArgAlaLysGlnAsnAlaAspLysGln-138 |
| g689 | |
| AMPHI Regions - AMPHI | |
| SEQ. ID. NO. 34970 | 16-ValLeuMetAlaValLeuValAlaLeu-24 |
| SEQ. ID. NO. 34971 | 33-LeuProAlaIleProGluMetAlaGln-41 |
| SEQ. ID. NO. 34972 | 49-ArgIleGluSerLeu-53 |
| SEQ. ID. NO. 34973 | 62-PheGlyGlnValAlaGlyGly-68 |
| SEQ. ID. NO. 34974 | 73-IleLysGlyArgLys-77 |
| SEQ. ID. NO. 34975 | 103-LeuLeuAsnLeuArgAlaValGlnAlaPhe-112 |
| SEQ. ID. NO. 34976 | 138-PheAlaLeuIleGlyIleIleLeu-145 |
| SEQ. ID. NO. 34977 | 152-AlaProMetValGlyAlaLeuLeuGlnGlyLeuGlyGlyTrpArgAlaIlePheVal-170 |
| SEQ. ID. NO. 34978 | 177-ProValLeuProGlyLeuValGlnTyrPhe-186 |
| SEQ. ID. NO. 34979 | 195-LysIleGlyArgAspVal-200 |
| SEQ. ID. NO. 34980 | 207-ArgPheLysArgValLeu-212 |
| SEQ. ID. NO. 34981 | 227-SerPheGlySerMetPheAla-233 |
| SEQ. ID. NO. 34982 | 288-GlyIleValValGln-292 |
| SEQ. ID. NO. 34983 | 347-AlaAsnAlaValSerGlyValPheArgSerLeuIle-358 |
| Antigenic Index - Jameson-Wolf | |
| SEQ. ID. NO. 34984 | 1-TerTerSerProProLeuProProMetSerGlyLys-12 |
| SEQ. ID. NO. 34985 | 46-AspIleHisArgIleGluSer-52 |
| SEQ. ID. NO. 34986 | 71-SerAspIleLysGlyArgLysProVal-79 |
| SEQ. ID. NO. 34987 | 98-SerSerThrGluGln-102 |
| SEQ. ID. NO. 34988 | 124-MetValArgAspTyrTyrSerGlyArgLysAlaAla-135 |
| SEQ. ID. NO. 34989 | 189-AsnProAlaValGlyGlyLysIleGlyArgAspVal-200 |
| SEQ. ID. NO. 34990 | 207-ArgPheLysArgValLeuLysThrArgAla-216 |
| SEQ. ID. NO. 34991 | 275-LeuLysThrGlyAlaHisProGlnSer-283 |
| SEQ. ID. NO. 34992 | 340-PheLysGluGluGlyGlySerAla-347 |
| SEQ. ID. NO. 34993 | 390-LysAlaTrpLysGluAsnGluLysLysArgIleLeu-401 |
| Hydrophilic Regions - Hopp-Woods | |
| SEQ. ID. NO. 34994 | 46-AspIleHisArgIleGluSer-52 |
| SEQ. ID. NO. 34995 | 71-SerAspIleLysGlyArgLysProVal-79 |
| SEQ. ID. NO. 34996 | 128-TyrTyrSerGlyArgLysAlaAla-135 |
| SEQ. ID. NO. 34997 | 195-LysIleGlyArgAspVal-200 |
| SEQ. ID. NO. 34998 | 207-ArgPheLysArgValLeuLysThrArgAla-216 |
| SEQ. ID. NO. 34999 | 340-PheLysGluGluGlyGlySer-346 |
| SEQ. ID. NO. 35000 | 390-LysAlaTrpLysGluAsnGluLysLysArgIleLeu-401 |
| g690 | |
| AMPHI Regions - AMPHI | |
| SEQ. ID. NO. 35001 | 38-SerSerAlaSerSer-42 |
| SEQ. ID. NO. 35002 | 54-SerAlaProAspAsnValLysGlnAla-62 |
| SEQ. ID. NO. 35003 | 73-HisProAlaAlaGlyIleGlyAspLeuIleGlnGlnIleAlaGluHisIle-89 |
| SEQ. ID. NO. 35004 | 112-GlyTyrAspAsnIleGlnArgLeu-119 |
| SEQ. ID. NO. 35005 | 146-ThrArgThrIleSerArgGlnAlaGlnAspAla-156 |
| SEQ. ID. NO. 35006 | 185-ProLysArgAlaArgTyrPhe-191 |
| SEQ. ID. NO. 35007 | 209-GlyAsnPheGlnTyrIleGlyGlnLeuProGlyTyrLeuLysMetHisGlyGluMet-227 |
| Antigenic Index - Jameson-Wolf | |
| SEQ. ID. NO. 35008 | 1-MetLysAsnLysThrSerSerLeu-8 |
| SEQ. ID. NO. 35009 | 20-ArgSerProSerLysGluAspLysThrLysGluAsnGlyAla-33 |
| SEQ. ID. NO. 35010 | 37-SerSerSerAlaSerSerAlaSerSerGlnThrAspLeuGlnPro-51 |
| SEQ. ID. NO. 35011 | 54-SerAlaProAspAsnValLysGlnAlaGluSerAlaProLeuAsnCysThrGly-71 |
| SEQ. ID. NO. 35012 | 86-AlaGluHisIleAspSerAspCys-93 |
| SEQ. ID. NO. 35013 | 100-AsnGluLeuGluThrArgPhe-106 |
| SEQ. ID. NO. 35014 | 108-LeuProGlyGlyGlyTyrAspAsnIleGln-117 |
| SEQ. ID. NO. 35015 | 122-ProAspIleArgProGluAspProAspTyrHisGln-133 |
| SEQ. ID. NO. 35016 | 140-GluAspLeuArgTyrGlyThrArgThrIleSerArgGlnAlaGln-154 |

TABLE 1-continued

| | |
|---|---|
| SEQ. ID. NO. 35017 | 156-AlaIleMetGluGlnGluArgArgLeuArgGluAlaThr-168 |
| SEQ. ID. NO. 35018 | 173-GlnGlySerGlnLysThrArgGlyGlnGlyGluGluProLysArgAlaArgTyr-190 |
| SEQ. ID. NO. 35019 | 199-TyrLeuAsnArgHisAsnAsnGlyLeuGlyGlyAsn-210 |
| SEQ. ID. NO. 35020 | 223-MetHisGlyGluMetLeuGluAsnGlnSerLeu-233 |
| SEQ. ID. NO. 35021 | 235-ArgLeuSerAsnArgGluArgAsnProAspLysProPheLeu-248 |
| SEQ. ID. NO. 35022 | 251-HisPheAspGluAsnGlyLysIleThr-259 |
| SEQ. ID. NO. 35023 | 263-ValTyrGluLysAsnIle-268 |
| Hydrophilic Regions - Hopp-Woods | |
| SEQ. ID. NO. 35024 | 1-MetLysAsnLysThrSer-6 |
| SEQ. ID. NO. 35025 | 20-ArgSerProSerLysGluAspLysThrLysGluAsnGlyAla-33 |
| SEQ. ID. NO. 35026 | 39-SerAlaSerSerAlaSerSerGlnThrAspLeu-49 |
| SEQ. ID. NO. 35027 | 54-SerAlaProAspAsnValLysGlnAlaGluSerAlaPro-66 |
| SEQ. ID. NO. 35028 | 87-GluHisIleAspSer-91 |
| SEQ. ID. NO. 35029 | 100-AsnGluLeuGluThr-104 |
| SEQ. ID. NO. 35030 | 124-IleArgProGluAspProAspTyrHisGln-133 |
| SEQ. ID. NO. 35031 | 140-GluAspLeuArgTyrGlyThr-146 |
| SEQ. ID. NO. 35032 | 148-ThrIleSerArgGlnAlaGln-154 |
| SEQ. ID. NO. 35033 | 156-AlaIleMetGluGlnGluArgArgLeuArgGluAlaThr-168 |
| SEQ. ID. NO. 35034 | 174-GlySerGlnLysThrArgGlyGlnGlyGluGluProLysArgAlaArgTyr-190 |
| SEQ. ID. NO. 35035 | 223-MetHisGlyGluMetLeuGlu-229 |
| SEQ. ID. NO. 35036 | 236-LeuSerAsnArgGluArgAsnProAspLysProPhe-247 |
| SEQ. ID. NO. 35037 | 251-HisPheAspGluAsnGlyLysIleThr-259 |
| g691 | |
| AMPHI Regions - AMPHI | |
| SEQ. ID. NO. 35038 | 11-LysProAlaAlaSer-15 |
| SEQ. ID. NO. 35039 | 55-HisAsnGluLeuArgLysIleArgAla-63 |
| SEQ. ID. NO. 35040 | 101-AlaArgAspTyrVal-105 |
| Antigenic Index - Jameson-Wolf | |
| SEQ. ID. NO. 35041 | 7-CysArgPheAlaLys-11 |
| SEQ. ID. NO. 35042 | 35-ProProAsnAspPheGlnProAsnCysAspIleArgArgLeuGlyLeuThrGlnGlyGlnHisAsnGluLeuArgLysIleArgAla-63 |
| SEQ. ID. NO. 35043 | 67-MetAlaGlyAspArgAlaArgLeuLysValMetHis-78 |
| SEQ. ID. NO. 35044 | 80-GluHisSerArgArgArgSerVal-87 |
| SEQ. ID. NO. 35045 | 91-IleSerSerAspValPheAsnArgAsnGluAlaArgAspTyrValGluSerArgTyrHisSerSerMet-113 |
| SEQ. ID. NO. 35046 | 115-PheAlaValAspGluLeuGluIle-122 |
| SEQ. ID. NO. 35047 | 131-ThrProGlnGlnGlnGln-136 |
| SEQ. ID. NO. 35048 | 140-SerSerCysLeuLys-144 |
| Hydrophilic Regions - Hopp-Woods | |
| SEQ. ID. NO. 35049 | 43-CysAspIleArgArgLeuGly-49 |
| SEQ. ID. NO. 35050 | 54-GlnHisAsnGluLeuArgLysIleArgAla-63 |
| SEQ. ID. NO. 35051 | 67-MetAlaGlyAspArgAlaArgLeuLysValMetHis-78 |
| SEQ. ID. NO. 35052 | 80-GluHisSerArgArgArgSerVal-87 |
| SEQ. ID. NO. 35053 | 95-ValPheAsnArgAsnGluAlaArgAspTyrValGlu-106 |
| SEQ. ID. NO. 35054 | 115-PheAlaValAspGluLeuGluIle-122 |
| g692 | |
| AMPHI Regions - AMPHI | |
| SEQ. ID. NO. 35055 | 9-SerGluSerIleArgArgIleTrpArgAsnGlyArgGlu-21 |
| SEQ. ID. NO. 35056 | 58-PheValAlaLeuGluAla-63 |
| SEQ. ID. NO. 35057 | 77-LeuGlyTyrValPheLysProLeuAlaValPheVal-88 |
| SEQ. ID. NO. 35058 | 106-GlnGlyPheGlyGlnLeuHis-112 |
| SEQ. ID. NO. 35059 | 143-PheAspValPheGlnValPheArgAsp-151 |
| SEQ. ID. NO. 35060 | 179-CysGluValGlyArgValValGlyArgGlyTyrGlyAlaAlaValPheAspPhePheGlnArgPheGlnPhe-202 |
| SEQ. ID. NO. 35061 | 205-IleGlnSerGlnArgArgGlyArgHisLeuGluGlyPheGlyAsp-219 |
| SEQ. ID. NO. 35062 | 254-ValGlyLysPheAspGlnPheAspGlyVal-263 |
| SEQ. ID. NO. 35063 | 275-PheAspHisIleAlaGluVal-281 |
| SEQ. ID. NO. 35064 | 302-GlyGlyArgGlyCys-306 |
| Antigenic Index - Jameson-Wolf | |
| SEQ. ID. NO. 35065 | 4-ThrArgCysArgCysSerGluSerIleArgArgIleTrpArgAsnGlyArgGluTrpArgIleLysGlyGlnLysCysArgLeuAsnThrAsp AlaValGln-37 |
| SEQ. ID. NO. 35066 | 89-GlyGlyPheAspGlyArgProValAspIleGlyLysAlaArgLeuLeuGlu-105 |
| SEQ. ID. NO. 35067 | 120-AlaValAspAspGlyLysIle-126 |
| SEQ. ID. NO. 35068 | 136-CysGlyPheLysLeuAspAspPheAspVal-145 |
| SEQ. ID. NO. 35069 | 150-ArgAspValGlyPheGlyCysGlyGlnArgIle-160 |
| SEQ. ID. NO. 35070 | 177-GlyAlaCysGluValGlyArgValValGlyArgGlyTyr-189 |
| SEQ. ID. NO. 35071 | 204-ArgIleGlnSerGlnArgArgGlyArgHisLeuGluGlyPheGlyAsp-219 |
| SEQ. ID. NO. 35072 | 236-GluAspValAspVal-240 |
| SEQ. ID. NO. 35073 | 256-LysPheAspGlnPheAspGlyVal-263 |
| SEQ. ID. NO. 35074 | 282-AlaHisGlyArgAlaGluAspAspPhePhePhe-292 |
| SEQ. ID. NO. 35075 | 296-ValIleGlyArgArgGlyGlyGlyArgGlyCysGlyArg-308 |
| SEQ. ID. NO. 35076 | 316-GlyCysGluAspGluArgGluCysGlyGlyGlyLysGlyPheGluGlu-331 |
| Hydrophilic Regions - Hopp-Woods | |
| SEQ. ID. NO. 35077 | 4-ThrArgCysArgCysSerGluSerIleArgArgIleTrpArgAsnGlyArgGluTrpArgIleLysGlyGlnLysCysArgLeuAsnThr-33 |
| SEQ. ID. NO. 35078 | 91-PheAspGlyArgProValAspIleGlyLysAlaArgLeuLeuGlu-105 |
| SEQ. ID. NO. 35079 | 120-AlaValAspAspGlyLysIle-126 |
| SEQ. ID. NO. 35080 | 139-LysLeuAspAspPheAsp-144 |
| SEQ. ID. NO. 35081 | 179-CysGluValGlyArgValValGly-186 |
| SEQ. ID. NO. 35082 | 206-GlnSerGlnArgArgGlyArgHisLeuGluGlyPheGly-218 |
| SEQ. ID. NO. 35083 | 236-GluAspValAspVal-240 |
| SEQ. ID. NO. 35084 | 282-AlaHisGlyArgAlaGluAspAspPhePhePhe-292 |
| SEQ. ID. NO. 35085 | 296-ValIleGlyArgArgGlyGlyGlyArgGlyCysGly-307 |

TABLE 1-continued

SEQ. ID. NO. 35086 316-GlyCysGluAspGluArgGluCysGlyGly-325
SEQ. ID. NO. 35087 327-LysGlyPheGluGlu-331
g694
AMPHI Regions - AMPHI
SEQ. ID. NO. 35088 13-LeuThrProAlaSerThr-18
SEQ. ID. NO. 35089 69-ArgGlyArgAlaCysArg-74
SEQ. ID. NO. 35090 88-GlnValGlyArgValVal-93
SEQ. ID. NO. 35091 103-CysArgHisPheAlaGln-108
SEQ. ID. NO. 35092 110-ValAlaValGlyArgIleGly-116
SEQ. ID. NO. 35093 139-ArgArgIleAlaAspValPheLeuVal-147
SEQ. ID. NO. 35094 149-IleAlaAspIleGlyGlu-154
SEQ. ID. NO. 35095 171-ArgGlyLeuAlaAspIleGlyGluPheValGlyValSerAsp-184
SEQ. ID. NO. 35096 194-PheAspGlnLysHisPheAlaArgCys-202
SEQ. ID. NO. 35097 238-HisGlnArgAlaSerArgIleLys-245
SEQ. ID. NO. 35098 270-ArgAlaArgArgHisPheArgGlnValPheAsp-280
SEQ. ID. NO. 35099 298-AspPheValAlaHisIle-303
SEQ. ID. NO. 35100 327-AlaAlaArgIleGlyLysAspAsp-334
Antigenic Index - Jameson-Wolf
SEQ. ID. NO. 35101 34-GlyGlnAspGluHisAspAla-40
SEQ. ID. NO. 35102 45-ProProPheAlaHisGlyPhe-51
SEQ. ID. NO. 35103 53-ProProSerAlaTyrGlyCysGln-60
SEQ. ID. NO. 35104 63-ProHisGlnHisPheGlyArgGlyArgAlaCysArgTyr-75
SEQ. ID. NO. 35105 82-PheLysProArgAla-86
SEQ. ID. NO. 35106 97-ArgIleAspSerAlaArgCysArgHis-105
SEQ. ID. NO. 35107 113-GlyArgIleGlyArgThrAspHisAsnHisAsp-123
SEQ. ID. NO. 35108 130-LeuPheAspGlyGlyLeuProValGlyArgArgIleAla-142
SEQ. ID. NO. 35109 150-AlaAspIleGlyGluThrArgValGlnArgGlyAspAsp-162
SEQ. ID. NO. 35110 167-IleAspArgGluArgGlyLeuAlaAsp-175
SEQ. ID. NO. 35111 189-HisIleSerAspArgPheAspGlnLysHisPheAla-200
SEQ. ID. NO. 35112 202-CysLysLeuProHisArgAlaPheAsp-210
SEQ. ID. NO. 35113 214-ProLeuMetProAspHisAspAspPheThr-223
SEQ. ID. NO. 35114 237-ArgHisGlnArgAlaSerArgIleLysTyrProGluThrAlaLeu-251
SEQ. ID. NO. 35115 265-ArgIleAsnGlnCysArgAlaArgArgHisPhe-275
SEQ. ID. NO. 35116 278-ValPheAspLysHisArg-283
SEQ. ID. NO. 35117 303-IleAsnArgArgAlaGluPhe-309
SEQ. ID. NO. 35118 313-ThrPheAspAsnThrAspCysProIleHisThrGlyAlaGluAlaAlaArgIleGlyLysAspAspGlyPheSer-337
SEQ. ID. NO. 35119 344-ProCysSerAspGly-348
SEQ. ID. NO. 35120 356-LeuCysAspGlyArgTyrCysGlnAlaProProThrProHisArgArgArg-372
Hydrophilic Regions - Hopp-Woods
SEQ. ID. NO. 35121 34-GlyGlnAspGluHisAspAla-40
SEQ. ID. NO. 35122 68-GlyArgGlyArgAlaCysArg-74
SEQ. ID. NO. 35123 82-PheLysProArgAla-86
SEQ. ID. NO. 35124 97-ArgIleAspSerAlaArgCysArgHis-105
SEQ. ID. NO. 35125 114-ArgIleGlyArgThrAspHisAsnHis-122
SEQ. ID. NO. 35126 137-ValGlyArgArgIleAla-142
SEQ. ID. NO. 35127 150-AlaAspIleGlyGluThrArgValGlnArgGlyAspAsp-162
SEQ. ID. NO. 35128 167-IleAspArgGluArgGlyLeuAlaAsp-175
SEQ. ID. NO. 35129 189-HisIleSerAspArgPheAspGlnLysHisPheAla-200
SEQ. ID. NO. 35130 202-CysLysLeuProHisArgAlaPhe-209
SEQ. ID. NO. 35131 217-ProAspHisAspAsp-221
SEQ. ID. NO. 35132 237-ArgHisGlnArgAlaSerArgIleLysTyrProGluThrAlaLeu-251
SEQ. ID. NO. 35133 267-AsnGlnCysArgAlaArgArgHisPhe-275
SEQ. ID. NO. 35134 278-ValPheAspLysHisArg-283
SEQ. ID. NO. 35135 303-IleAsnArgArgAlaGluPhe-309
SEQ. ID. NO. 35136 314-PheAspAsnThrAsp-318
SEQ. ID. NO. 35137 325-AlaGluAlaAlaArgIleGlyLysAspAspGlyPheSer-337
SEQ. ID. NO. 35138 367-ThrProHisArgArgArg-372
g695
AMPHI Regions - AMPHI
SEQ. ID. NO. 35139 34-GlnAsnSerGlnArg-38
SEQ. ID. NO. 35140 41-SerLysProAlaGluArgTyrAlaAspCysProHis-52
SEQ. ID. NO. 35141 83-AlaSerCysAlaSerValLeu-89
SEQ. ID. NO. 35142 128-ValArgLeuSerAsnGluVal-134
SEQ. ID. NO. 35143 157-ValGlnLysLeuAsp-161
SEQ. ID. NO. 35144 182-ValGluThrAlaGlnAsnLeuTyrAsnGlnAlaLeuLysHisTyrGlnAsnGly-199
SEQ. ID. NO. 35145 237-CysGluSerValIleGluIle-243
SEQ. ID. NO. 35146 247-TyrAlaAsnArgPheLysAspSer-254
SEQ. ID. NO. 35147 277-AlaArgAlaThrTrpArgSerLeuIleGlnThrTyrProGly-290
Antigenic Index - Jameson-Wolf
SEQ. ID. NO. 35148 1-LeuProGlnThrArgProAlaArgArgHisHisArgHisArgGlnTyrPheValGluArgLysGlyAspAlaArgSerGlyPhe-28
SEQ. ID. NO. 35149 32-GlnCysGlnAsnSerGlnArgPheGlnSerLysProAlaGluArgTyrAlaAspCysProHisHisProAlaArgArgArgArgPheAspPro AlaSerGluLysIleMetLysThrLys-71
SEQ. ID. NO. 35150 90-ProValProGluGlySerArgThrGluMetProThrGlnGluAsnAlaSerAspGlyIleProTyr-111
SEQ. ID. NO. 35151 116-LeuGlnAspArgLeuAspTyrLeuGlu-124
SEQ. ID. NO. 35152 126-LysIleValArgLeuSerAsnGluValGluMetLeuAsnGlyLysValLysAlaLeuGluHisThrLysIleHisProSerGlyArgThrTyr ValGlnLysLeuAspAspArgLysLeuLysGlu-167
SEQ. ID. NO. 35153 169-TyrLeuAsnThrGluGlyGlySerAla-177
SEQ. ID. NO. 35154 192-AlaLeuLysHisTyrGlnAsnGlyArg-200
SEQ. ID. NO. 35155 208-LeuLysGlyAlaAspGlyGlyAspGlyGlySerIleAlaGln-221
SEQ. ID. NO. 35156 229-GlnSerArgAlaArgMetGlyAsnCys-237

TABLE 1-continued

| | |
|---|---|
| SEQ. ID. NO. 35157 | 243-IleGlyGlyArgTyrAlaAsnArgPheLysAspSerProThrAla-257 |
| SEQ. ID. NO. 35158 | 265-GlyGluCysGlnTyr-269 |
| SEQ. ID. NO. 35159 | 271-LeuGlnGlnLysAspIleAla-277 |
| SEQ. ID. NO. 35160 | 288-TyrProGlySerProAlaAlaLysArgAlaAlaAlaAlaValArgLysArg-304 |
| Hydrophilic Regions - Hopp-Woods | |
| SEQ. ID. NO. 35161 | 2-ProGlnThrArgProAlaArgArgHisHisArgHisArg-14 |
| SEQ. ID. NO. 35162 | 17-PheValGluArgLysGlyAspAlaArgSer-26 |
| SEQ. ID. NO. 35163 | 35-AsnSerGlnArgPheGlnSerLysProAlaGluArgTyrAlaAsp-49 |
| SEQ. ID. NO. 35164 | 51-ProHisHisProAlaArgArgArgArgPheAspProAlaSerGluLysIleMetLysThrLys-71 |
| SEQ. ID. NO. 35165 | 92-ProGluGlySerArgThrGluMetProThrGlnGluAsnAlaSerAsp-107 |
| SEQ. ID. NO. 35166 | 116-LeuGlnAspArgLeuAspTyrLeuGlu-124 |
| SEQ. ID. NO. 35167 | 126-LysIleValArgLeuSerAsnGluValGluMetLeuAsnGlyLysValLysAlaLeuGluHisThrLysIleHisProSerGly-153 |
| SEQ. ID. NO. 35168 | 156-TyrValGlnLysLeuAspAspArgLysLeuLysGlu-167 |
| SEQ. ID. NO. 35169 | 209-LysGlyAlaAspGlyGlyAspGlyGlySerIleAlaGln-221 |
| SEQ. ID. NO. 35170 | 230-SerArgAlaArgMetGlyAsn-236 |
| SEQ. ID. NO. 35171 | 247-TyrAlaAsnArgPheLysAspSerProThrAla-257 |
| SEQ. ID. NO. 35172 | 265-GlyGluCysGlnTyr-269 |
| SEQ. ID. NO. 35173 | 271-LeuGlnGlnLysAspIleAla-277 |
| SEQ. ID. NO. 35174 | 292-ProAlaAlaLysArgAlaAlaAlaAlaValArgLysArg-304 |
| g700 | |
| AMPHI Regions - AMPHI | |
| SEQ. ID. NO. 35175 | 6-ThrLeuPheSerValLeuValProMetPheAlaGlyPhePheIleArgValProLys-24 |
| SEQ. ID. NO. 35176 | 51-ArgValGluAspLeuGlySerArg-58 |
| SEQ. ID. NO. 35177 | 80-AlaLeuAlaValLeuGlyLysLeu-87 |
| SEQ. ID. NO. 35178 | 189-GlyValSerTrpThrLysGlyLeu-196 |
| SEQ. ID. NO. 35179 | 204-TrpTyrSerLeuSerGlyLeuVal-211 |
| SEQ. ID. NO. 35180 | 216-TyrGlyAlaValTrp-220 |
| SEQ. ID. NO. 35181 | 228-AspLeuAlaArgGluLeu-233 |
| SEQ. ID. NO. 35182 | 268-GlyAlaGlyGlyLeu-272 |
| Antigenic Index - Jameson-Wolf | |
| SEQ. ID. NO. 35183 | 21-ArgValProLysProTyrLeuProAlaSerAspLysVal-33 |
| SEQ. ID. NO. 35184 | 50-SerArgValGluAspLeuGlySerArgLeuGlyAsp-61 |
| SEQ. ID. NO. 35185 | 88-SerProTrpArgIleGlyGlyLysGlyLysGlyVal-99 |
| SEQ. ID. NO. 35186 | 103-ValSerGlySerValArg-108 |
| SEQ. ID. NO. 35187 | 118-ValSerGlyLysLeuMet-123 |
| SEQ. ID. NO. 35188 | 128-MetProSerGluAsnAlaGlyMet-135 |
| SEQ. ID. NO. 35189 | 149-LeuLysSerSerGlyValSerLeu-156 |
| SEQ. ID. NO. 35190 | 160-LeuLeuAsnArgArgGlyIleArgLeu-168 |
| SEQ. ID. NO. 35191 | 245-ArgPheProAspAla-249 |
| SEQ. ID. NO. 35192 | 268-GlyAlaGlyGlyLeu-272 |
| Hydrophilic Regions - Hopp-Woods | |
| SEQ. ID. NO. 35193 | 29-AlaSerAspLysVal-33 |
| SEQ. ID. NO. 35194 | 50-SerArgValGluAspLeuGlySerArgLeuGlyAsp-61 |
| SEQ. ID. NO. 35195 | 92-IleGlyGlyLysGlyLysGlyVal-99 |
| SEQ. ID. NO. 35196 | 149-LeuLysSerSerGlyValSer-155 |
| SEQ. ID. NO. 35197 | 160-LeuLeuAsnArgArgGlyIleArg-167 |
| g701 | |
| AMPHI Regions - AMPHI | |
| SEQ. ID. NO. 35198 | 6-PheGlnValAlaGly-10 |
| SEQ. ID. NO. 35199 | 30-CysLeuGluThrSer-34 |
| SEQ. ID. NO. 35200 | 45-ProAsnSerPheAlaGlyPheLysArgPheSerSerIle-57 |
| SEQ. ID. NO. 35201 | 79-GlyProAlaProAlaMet-84 |
| SEQ. ID. NO. 35202 | 111-ArgAlaIleSerSerLeu-116 |
| Antigenic Index - Jameson-Wolf | |
| SEQ. ID. NO. 35203 | 17-AlaGlnSerThrProSerSerProThrMet-26 |
| SEQ. ID. NO. 35204 | 29-ThrCysLeuGluThrSerProGluAlaGly-38 |
| SEQ. ID. NO. 35205 | 52-LysArgPheSerSer-56 |
| SEQ. ID. NO. 35206 | 72-AsnLysAlaAspIleProThrGlyProAla-81 |
| SEQ. ID. NO. 35207 | 104-GlyLysAlaSerLeuAsnSerArgAla-112 |
| SEQ. ID. NO. 35208 | 119-SerCysGlyGlyThrArgLeu-125 |
| Hydrophilic Regions - Hopp-Woods | |
| SEQ. ID. NO. 35209 | 72-AsnLysAlaAspIleProThr-78 |
| g702 | |
| AMPHI Regions - AMPHI | |
| SEQ. ID. NO. 35210 | 51-CysSerGlyLeuValThrValProAla-59 |
| SEQ. ID. NO. 35211 | 74-AlaSerSerProThrGlyValArgLysValIle-84 |
| Antigenic Index - Jameson-Wolf | |
| SEQ. ID. NO. 35212 | 1-MetProCysSerLysAlaSerTrp-8 |
| SEQ. ID. NO. 35213 | 10-SerProGlyValAla-14 |
| SEQ. ID. NO. 35214 | 27-AlaLeuAlaArgAspSerCysLysProGlyLeu-37 |
| SEQ. ID. NO. 35215 | 41-ThrAlaProAlaSerSer-46 |
| SEQ. ID. NO. 35216 | 69-AlaIleArgArgMetAlaSerSerProThrGlyValArgLysValIleSer-85 |
| SEQ. ID. NO. 35217 | 88-GlyMetProProSerThrArgAlaArgAspLysSerThrAla-101 |
| SEQ. ID. NO. 35218 | 118-ArgIleSerArgGlyValSer-124 |
| Hydrophilic Regions - Hopp-Woods | |
| SEQ. ID. NO. 35219 | 27-AlaLeuAlaArgAspSerCysLys-34 |
| SEQ. ID. NO. 35220 | 69-AlaIleArgArgMetAlaSer-75 |
| SEQ. ID. NO. 35221 | 78-ThrGlyValArgLysValIleSer-85 |

TABLE 1-continued

| | |
|---|---|
| SEQ. ID. NO. 35222 | 91-ProSerThrArgAlaArgAspLysSerThrAla-101 |
| SEQ. ID. NO. 35223 | 118-ArgIleSerArgGlyValSer-124 |
| g703 | |
| AMPHI Regions - AMPHI | |
| SEQ. ID. NO. 35224 | 21-GlnThrLeuAlaThrValAsnGly-28 |
| SEQ. ID. NO. 35225 | 64-GluValValAsnThrValValAlaGlnGlu-73 |
| SEQ. ID. NO. 35226 | 79-LeuAspArgSerAlaGlu-84 |
| SEQ. ID. NO. 35227 | 136-GlnGluValLysAlaValTyrAspAsnIleSerGlyPheTyrLysGly-151 |
| SEQ. ID. NO. 35228 | 181-PheAspAlaValLeu-185 |
| SEQ. ID. NO. 35229 | 204-ValProLeuLysAspLeuGluGlnGlyValProProLeuTyrGlnAlaIleLysAspLeuLysLys-225 |
| SEQ. ID. NO. 35230 | 252-ValProSerPheAsp-256 |
| SEQ. ID. NO. 35231 | 270-ArgIleAspArgAlaValCys-276 |
| Antigenic Index - Jameson-Wolf | |
| SEQ. ID. NO. 35232 | 1-MetLysAlaLysIle-5 |
| SEQ. ID. NO. 35233 | 26-ValAsnGlyGlnLysIleAspSerSerVal-35 |
| SEQ. ID. NO. 35234 | 43-PheArgAlaGluAsnSerArgAlaGluAspThrProGlnLeuArg-57 |
| SEQ. ID. NO. 35235 | 72-GlnGluValLysArgLeuLysLeuAspArgSerAlaGluPheLysAspAlaLeuAlaLysLeuArgAlaGluAlaLysLysSerGlyAsp AspLysLysProSerPheLysThr-109 |
| SEQ. ID. NO. 35236 | 129-LysThrGlnProValSerGluGlnGluValLysAlaValTyr-142 |
| SEQ. ID. NO. 35237 | 144-AsnIleSerGlyPheTyrLysGlyThrGlnGluValGlnLeu-157 |
| SEQ. ID. NO. 35238 | 160-IleLeuThrAspLysGluGluAsnAlaLysLysAlaValAlaAspLeuLysAlaLysLysGlyPhe-181 |
| SEQ. ID. NO. 35239 | 188-TyrSerLeuAsnAspArgThrLysArgThrGlyAlaProAspGlyTyrValPro-205 |
| SEQ. ID. NO. 35240 | 207-LysAspLeuGluGlnGlyValProPro-215 |
| SEQ. ID. NO. 35241 | 221-LysAspLeuLysLysGlyGluPheThrAlaThrProLeuLysAsnGlyAspPhe-238 |
| SEQ. ID. NO. 35242 | 243-TyrValAsnAspSerArgGluValLysValProSerPheAspGluMetLysGly-260 |
| SEQ. ID. NO. 35243 | 266-LeuGlnAlaGluArgIleAspArgAlaVal-275 |
| SEQ. ID. NO. 35244 | 282-AlaAsnIleLysProAlaLys-288 |
| Hydrophilic Regions - Hopp-Woods | |
| SEQ. ID. NO. 35245 | 1-MetLysAlaLysIle-5 |
| SEQ. ID. NO. 35246 | 29-GlnLysIleAspSerSerVal-35 |
| SEQ. ID. NO. 35247 | 43-PheArgAlaGluAsnSerArgAlaGluAspThrProGlnLeuArg-57 |
| SEQ. ID. NO. 35248 | 72-GlnGluValLysArgLeuLysLeuAspArgSerAlaGluPheLysAspAlaLeuAlaLysLeuArgAlaGluAlaLysLysSerGlyAsp AspLysLysProSerPhe-107 |
| SEQ. ID. NO. 35249 | 131-GlnProValSerGluGlnGluValLysAlaValTyr-142 |
| SEQ. ID. NO. 35250 | 160-IleLeuThrAspLysGluGluAsnAlaLysLysAlaValAlaAspLeuLysAlaLysLysGlyPhe-181 |
| SEQ. ID. NO. 35251 | 189-SerLeuAsnAspArgThrLysArgThrGlyAla-199 |
| SEQ. ID. NO. 35252 | 207-LysAspLeuGluGln-211 |
| SEQ. ID. NO. 35253 | 221-LysAspLeuLysLysGlyGluPhe-228 |
| SEQ. ID. NO. 35254 | 245-AsnAspSerArgGluValLysValProSerPheAspGluMetLysGly-260 |
| SEQ. ID. NO. 35255 | 266-LeuGlnAlaGluArgIleAspArgAlaVal-275 |
| SEQ. ID. NO. 35256 | 282-AlaAsnIleLysProAlaLys-288 |
| g704 | |
| AMPHI Regions - AMPHI | |
| SEQ. ID. NO. 35257 | 36-AlaValAlaGlnSerIleIleAspSerGlyLeuGly-47 |
| SEQ. ID. NO. 35258 | 65-GlnGluIleLeuAspGlnIleArgLeuTyrAspLeuProGluValGlnSerAspPheValGluThrHis-87 |
| SEQ. ID. NO. 35259 | 184-LeuGlyMetMetGln-188 |
| SEQ. ID. NO. 35260 | 208-LeuGlnIleLeuHisTrpGlyGlyPheLeuMetValLeuPro-221 |
| SEQ. ID. NO. 35261 | 232-GlnGlyAlaLeuArgAspLeuLys-239 |
| SEQ. ID. NO. 35262 | 252-AlaIleIleMetThrPheIleAlaGlyIleTyrSer-263 |
| SEQ. ID. NO. 35263 | 289-PheMetGluHisIleAlaArg-295 |
| SEQ. ID. NO. 35264 | 298-AlaGlyAspAlaAlaGluArgLeuValLysLeuIleProAlaPheCysHisArgMetProGlyTyrProAlaValGlnAsp-324 |
| SEQ. ID. NO. 35265 | 326-ArgGluSerAlaValVal-331 |
| SEQ. ID. NO. 35266 | 400-GlyGlyThrArgLeuSerHisIleValArgLeuLeuAspArgAlaLeuAla-416 |
| SEQ. ID. NO. 35267 | 423-GluLeuAlaGluGlnTyr-428 |
| SEQ. ID. NO. 35268 | 499-AlaIleGluThrLeuSerGln-505 |
| SEQ. ID. NO. 35269 | 527-IleGluLeuLeuGlySerMet-533 |
| SEQ. ID. NO. 35270 | 574-GlnArgLeuAsnArgIleGlyGluGlyValGly-584 |
| SEQ. ID. NO. 35271 | 639-LeuLysAspSerAlaAlaGluAlaValArgGlnLeuAla-651 |
| SEQ. ID. NO. 35272 | 670-GluThrAlaArgAlaLeuGlyIle-677 |
| SEQ. ID. NO. 35273 | 691-GluTyrValGluAlaLeuGlnLysGlu-699 |
| SEQ. ID. NO. 35274 | 744-AspLeuArgThrValAlaHisLeuLeuAsp-753 |
| SEQ. ID. NO. 35275 | 780-AlaValLeuGlyTyrValGlnProTrpIleAlaAla-791 |
| SEQ. ID. NO. 35276 | 799-LeuAlaValLeuGly-803 |
| Antigenic Index - Jameson-Wolf | |
| SEQ. ID. NO. 35277 | 1-MetLysLysThrCys-5 |
| SEQ. ID. NO. 35278 | 9-GlyLeuAspValProGluAsn-15 |
| SEQ. ID. NO. 35279 | 20-ValArgTyrGluGlyGluAspArgGluThrCysCysValGly-33 |
| SEQ. ID. NO. 35280 | 42-IleAspSerGlyLeuGlySerTyrTyrLysArgArgThrAlaAspAlaLysLysThrGluLeuProProGlnGluIleLeuAsp-69 |
| SEQ. ID. NO. 35281 | 77-ProGluValGlnSerAspPheValGluThrHisAsnGlyThrHis-91 |
| SEQ. ID. NO. 35282 | 112-GlnLeuLeuArgThrAspGlyIleVal-120 |
| SEQ. ID. NO. 35283 | 124-LeuAsnTyrSerThrHisArgCys-131 |
| SEQ. ID. NO. 35284 | 133-ValValTrpAspAspGlyLysIleArgLeu-142 |
| SEQ. ID. NO. 35285 | 149-IleArgGlnThrGlyTyr-154 |
| SEQ. ID. NO. 35286 | 158-ProTyrAspAlaGlnLysIleGluAlaAlaAsnGlnLysGluArgLysGlnTyr-175 |
| SEQ. ID. NO. 35287 | 199-TyrGlyGlyAspIleGluProAspPhe-207 |
| SEQ. ID. NO. 35288 | 234-AlaLeuArgAspLeuLysAsnArgArgAlaGlyMetAspThrPro-248 |
| SEQ. ID. NO. 35289 | 293-IleAlaArgArgLysAlaGlyAspAlaAlaGluArgLeuVal-306 |
| SEQ. ID. NO. 35290 | 315-ArgMetProGlyTyr-319 |
| SEQ. ID. NO. 35291 | 323-GlnAspValArgGluSerAlaVal-330 |
| SEQ. ID. NO. 35292 | 342-LysProGlyGluThrIleProValAspGlyThrVal-353 |

TABLE 1-continued

| | |
|---|---|
| SEQ. ID. NO. 35293 | 355-GluGlyAsnSerAlaValAsnGluSer-363 |
| SEQ. ID. NO. 35294 | 365-LeuThrGlyGluSer-369 |
| SEQ. ID. NO. 35295 | 374-LysMetProSerGluLysValThrAla-382 |
| SEQ. ID. NO. 35296 | 393-IleArgThrAspArgThrGlyGlyGlyThrArg-403 |
| SEQ. ID. NO. 35297 | 414-AlaLeuAlaGlnLysProArgThrAlaGluLeuAlaGlu-426 |
| SEQ. ID. NO. 35298 | 486-ThrLeuAlaArgGluGlyIle-492 |
| SEQ. ID. NO. 35299 | 495-GlyGlyLysGlnAlaIle-500 |
| SEQ. ID. NO. 35300 | 510-IlePheAspLysThrGlyThrLeuThrGlnGlyAsnProAlaValArgArgIleGluLeu-529 |
| SEQ. ID. NO. 35301 | 544-SerLeuGluGlnGlnSerGluHisProLeu-553 |
| SEQ. ID. NO. 35302 | 561-ArgIleSerGlyGlySerValPro-568 |
| SEQ. ID. NO. 35303 | 571-GlnValGlyGlnArgLeuAsnArgIleGlyGluGlyVal-583 |
| SEQ. ID. NO. 35304 | 589-ValAsnGlyGluThr-593 |
| SEQ. ID. NO. 35305 | 605-AlaGluIleSerGlyLysGluProGlnThrGluGlyGlyGlySer-619 |
| SEQ. ID. NO. 35306 | 635-LeuGlnAspProLeuLysAspSerAlaAlaGluAlaValArg-648 |
| SEQ. ID. NO. 35307 | 650-LeuAlaGlyLysAsnLeu-655 |
| SEQ. ID. NO. 35308 | 659-IleLeuSerGlyAspArgGluGluAlaValAlaGluThrAlaArg-673 |
| SEQ. ID. NO. 35309 | 684-AlaMetProGluAspLysLeuGluTyr-692 |
| SEQ. ID. NO. 35310 | 694-GluAlaLeuGlnLysGluGlyLysLys-702 |
| SEQ. ID. NO. 35311 | 707-GlyAspGlyIleAsnAspAla-713 |
| SEQ. ID. NO. 35312 | 727-GlyGlyThrAspIleAlaArgAspGlyAlaAsp-737 |
| SEQ. ID. NO. 35313 | 743-GluAspLeuArgThr-747 |
| SEQ. ID. NO. 35314 | 753-AspGlnAlaArgArgThrArgHisIleIle-762 |
| SEQ. ID. NO. 35315 | 807-ArgLeuHisLysArgGlyGluMetProSerGluGln-818 |
| Hydrophilic Regions - Hopp-Woods | |
| SEQ. ID. NO. 35316 | 1-MetLysLysThrCys-5 |
| SEQ. ID. NO. 35317 | 22-TyrGluGlyGluAspArgGluThrCys-30 |
| SEQ. ID. NO. 35318 | 50-TyrLysArgArgThrAlaAspAlaLysLysThrGluLeuProPro-64 |
| SEQ. ID. NO. 35319 | 77-ProGluValGlnSerAspPheValGlu-85 |
| SEQ. ID. NO. 35320 | 87-HisAsnGlyThrHis-91 |
| SEQ. ID. NO. 35321 | 112-GlnLeuLeuArgThrAspGlyIleVal-120 |
| SEQ. ID. NO. 35322 | 133-ValValTrpAspAspGlyLysIleArgLeu-142 |
| SEQ. ID. NO. 35323 | 160-AspAlaGlnLysIleGluAlaAlaAsnGlnLysGluArgLysGlnTyr-175 |
| SEQ. ID. NO. 35324 | 201-GlyAspIleGluProAspPhe-207 |
| SEQ. ID. NO. 35325 | 234-AlaLeuArgAspLeuLysAsnArgArgAlaGlyMet-245 |
| SEQ. ID. NO. 35326 | 293-IleAlaArgArgLysAlaGlyAspAlaAlaGluArgLeuVal-306 |
| SEQ. ID. NO. 35327 | 323-GlnAspValArgGluSerAlaVal-330 |
| SEQ. ID. NO. 35328 | 375-MetProSerGluLysValThr-381 |
| SEQ. ID. NO. 35329 | 393-IleArgThrAspArgThrGlyGlyGlyThrArg-403 |
| SEQ. ID. NO. 35330 | 414-AlaLeuAlaGlnLysProArgThrAlaGluLeuAlaGlu-426 |
| SEQ. ID. NO. 35331 | 486-ThrLeuAlaArgGluGlyIle-492 |
| SEQ. ID. NO. 35332 | 522-ProAlaValArgArgIleGluLeu-529 |
| SEQ. ID. NO. 35333 | 545-LeuGluGlnGlnSerGluHisProLeu-553 |
| SEQ. ID. NO. 35334 | 574-GlnArgLeuAsnArgIleGlyGlu-581 |
| SEQ. ID. NO. 35335 | 607-IleSerGlyLysGluProGlnThrGluGlyGlyGly-618 |
| SEQ. ID. NO. 35336 | 637-AspProLeuLysAspSerAlaAlaGluAlaValArg-648 |
| SEQ. ID. NO. 35337 | 661-SerGlyAspArgGluGluAlaValAlaGluThrAlaArg-673 |
| SEQ. ID. NO. 35338 | 684-AlaMetProGluAspLysLeuGluTyr-692 |
| SEQ. ID. NO. 35339 | 694-GluAlaLeuGlnLysGluGlyLysLys-702 |
| SEQ. ID. NO. 35340 | 730-AspIleAlaArgAspGlyAlaAsp-737 |
| SEQ. ID. NO. 35341 | 743-GluAspLeuArgThr-747 |
| SEQ. ID. NO. 35342 | 753-AspGlnAlaArgArgThrArgHisIleIle-762 |
| SEQ. ID. NO. 35343 | 807-ArgLeuHisLysArgGlyGluMetProSerGluGln-818 |
| g705 | |
| AMPHI Regions - AMPHI | |
| SEQ. ID. NO. 35344 | 67-LysCysLeuLeuLysLeu-72 |
| SEQ. ID. NO. 35345 | 104-AsnProIleProAla-108 |
| SEQ. ID. NO. 35346 | 147-TyrMetGlnThrPheArgArgIleValAlaProGln-158 |
| SEQ. ID. NO. 35347 | 169-AsnGluPheIleGlyLeuPheLysAsn-177 |
| SEQ. ID. NO. 35348 | 183-ValValThrValThrGluLeuPheArgValAlaGln-194 |
| SEQ. ID. NO. 35349 | 196-ThrAlaAsnArgThr-200 |
| Antigenic Index - Jameson-Wolf | |
| SEQ. ID. NO. 35350 | 13-ThrGluThrArgAlaAspMet-19 |
| SEQ. ID. NO. 35351 | 132-ValProLysGlyGlnTrpGlu-138 |
| SEQ. ID. NO. 35352 | 165-ProProLeuSerAsnGlu-170 |
| SEQ. ID. NO. 35353 | 193-AlaGlnGluThrAlaAsnArgThrTyrAsp-202 |
| SEQ. ID. NO. 35354 | 226-AlaArgLeuGluLysArgPheAspArgTyrValAla-237 |
| Hydrophilic Regions - Hopp-Woods | |
| SEQ. ID. NO. 35355 | 13-ThrGluThrArgAlaAspMet-19 |
| SEQ. ID. NO. 35356 | 193-AlaGlnGluThrAlaAsnArgThr-200 |
| SEQ. ID. NO. 35357 | 226-AlaArgLeuGluLysArgPheAspArgTyrValAla-237 |
| g706 | |
| AMPHI Regions - AMPHI | |
| SEQ. ID. NO. 35358 | 11-GlyArgTrpLeuAsnSerTyr-17 |
| SEQ. ID. NO. 35359 | 24-ArgLeuIleHisAlaValArg-30 |
| SEQ. ID. NO. 35360 | 39-ThrAlaLeuAlaArgLeuLeuHis-46 |
| SEQ. ID. NO. 35361 | 70-IleTyrSerAsnAlaValGluArgMetLeuGlyThrValIleGly-84 |
| SEQ. ID. NO. 35362 | 111-ThrAlaSerAlaLeuAlaGlyTrpAlaAla-120 |
| SEQ. ID. NO. 35363 | 153-ArgAlaMetAsnValLeu-158 |
| SEQ. ID. NO. 35364 | 183-LeuAlaAspAsnLeuAlaAspCysSerLysMetIleAlaGluIleSerAsnGlyArg-201 |

TABLE 1-continued

| | |
|---|---|
| SEQ. ID. NO. 35365 | 241-SerMetMetGluAlaMetGlnHisAlaHisArgLysIleVal-254 |
| SEQ. ID. NO. 35366 | 318-AlaLeuAlaGluHisLeuHis-324 |
| Antigenic Index - Jameson-Wolf | |
| SEQ. ID. NO. 35367 | 1-MetAsnSerSerGlnArgLysArgLeuSerGlyArgTrpLeuAsnSerTyrGluArgTyrArgHisArgArgLeu-25 |
| SEQ. ID. NO. 35368 | 30-ArgLeuGlyGlyThr-34 |
| SEQ. ID. NO. 35369 | 71-TyrSerAsnAlaValGluArgMetLeu-79 |
| SEQ. ID. NO. 35370 | 97-HisTyrPheHisGlyAsnLeu-103 |
| SEQ. ID. NO. 35371 | 122-GlyLysAsnGlyTyrVal-127 |
| SEQ. ID. NO. 35372 | 140-GlyAspAsnGlySerGluTrpLeuAsp-148 |
| SEQ. ID. NO. 35373 | 186-AsnLeuAlaAspCysSerLysMetIleAlaGluIleSerAsnGlyArgArgMetThrArgGluArgLeuGluGlnAsnMetValLysMetArg GlnIleAsn-219 |
| SEQ. ID. NO. 35374 | 221-ArgMetValLysSerArgSerHisLeuAlaAlaThrSerGlyGluSerArgIleSerProSerMet-242 |
| SEQ. ID. NO. 35375 | 249-AlaHisArgLysIleValAsn-255 |
| SEQ. ID. NO. 35376 | 266-LysLeuGlnSerProLysLeuAsnGlySerGluIleArgLeuLeuAsp-281 |
| SEQ. ID. NO. 35377 | 289-ThrAspLeuGlnGln-293 |
| SEQ. ID. NO. 35378 | 300-GlyArgHisAlaArgArgIleArgIleAspThrAlaIleAsnProGluLeuGluAlaLeuAla-320 |
| SEQ. ID. NO. 35379 | 334-SerThrAsnMetArgGlnGluIle-341 |
| SEQ. ID. NO. 35380 | 349-GlnArgThrArgArgLysTrpLeuAspAlaHisGluArgGlnHisLeu-364 |
| SEQ. ID. NO. 35381 | 367-SerLeuLeuGluThrArgGluHisGly-375 |
| Hydrophilic Regions - Hopp-Woods | |
| SEQ. ID. NO. 35382 | 3-SerSerGlnArgLysArgLeuSer-10 |
| SEQ. ID. NO. 35383 | 17-TyrGluArgTyrArgHisArgArgLeu-25 |
| SEQ. ID. NO. 35384 | 74-AlaValGluArgMetLeu-79 |
| SEQ. ID. NO. 35385 | 142-AsnGlySerGluTrpLeu-147 |
| SEQ. ID. NO. 35386 | 186-AsnLeuAlaAspCysSerLysMetIleAla-195 |
| SEQ. ID. NO. 35387 | 198-SerAsnGlyArgArgMetThrArgGluArgLeuGluGlnAsnMetValLysMetArgGlnIleAsn-219 |
| SEQ. ID. NO. 35388 | 221-ArgMetValLysSerArgSerHis-228 |
| SEQ. ID. NO. 35389 | 232-ThrSerGlyGluSerArgIleSer-239 |
| SEQ. ID. NO. 35390 | 249-AlaHisArgLysIleValAsn-255 |
| SEQ. ID. NO. 35391 | 266-LysLeuGlnSerProLysLeuAsnGlySerGluIleArgLeuLeuAsp-281 |
| SEQ. ID. NO. 35392 | 301-ArgHisAlaArgArgIleArgIle-308 |
| SEQ. ID. NO. 35393 | 314-ProGluLeuGluAlaLeuAla-320 |
| SEQ. ID. NO. 35394 | 336-AsnMetArgGlnGluIle-341 |
| SEQ. ID. NO. 35395 | 349-GlnArgThrArgArgLysTrpLeuAspAlaHisGluArgGlnHisLeu-364 |
| SEQ. ID. NO. 35396 | 367-SerLeuLeuGluThrArgGluHisGly-375 |
| g707 | |
| AMPHI Regions - AMPHI | |
| SEQ. ID. NO. 35397 | 36-GlyIleGluLysMetAlaThrGln-43 |
| SEQ. ID. NO. 35398 | 91-HisAlaGlyAspIleAsnGlnIleMetSerLeu-101 |
| SEQ. ID. NO. 35399 | 116-IleLeuAlaAlaPro-120 |
| SEQ. ID. NO. 35400 | 134-ProGlyTyrLeuArgSerIleArgIle-142 |
| SEQ. ID. NO. 35401 | 168-AspLeuLeuAsnLeuArgAsp-174 |
| SEQ. ID. NO. 35402 | 182-LeuLysCysLeuPro-186 |
| SEQ. ID. NO. 35403 | 208-ValGlnTrpArgArgLeuLeuPro-215 |
| SEQ. ID. NO. 35404 | 248-SerAspMetPheTyr-252 |
| SEQ. ID. NO. 35405 | 256-GlyArgSerIleGlyGly-261 |
| SEQ. ID. NO. 35406 | 301-ArgTyrHisGlnAlaValSerGlyLeuSerGluValTyrAsp-314 |
| SEQ. ID. NO. 35407 | 368-TrpLeuAlaGluLeuSerHis-374 |
| SEQ. ID. NO. 35408 | 393-ThrGlyMetLysAspAlaLeuArgAlaProGluGluAlaPheGlyGluGly-409 |
| SEQ. ID. NO. 35409 | 440-HisAlaGlnTrpAsnLys-445 |
| SEQ. ID. NO. 35410 | 542-LeuLysLysProGluTyrPhe-548 |
| Antigenic Index - Jameson-Wolf | |
| SEQ. ID. NO. 35411 | 1-GluAlaValSerGlnGlnGlnAspIleLeuGlnArgGlnArgGluLysGlnLeuArgGluGlnMetGlnProGluGlnAspValArgLeuAsp GlyThrAspThrGlyIleGluLysMetAla-41 |
| SEQ. ID. NO. 35412 | 44-ValGlyGlyAlaAsnSerAspGluAlaSerProCys-55 |
| SEQ. ID. NO. 35413 | 62-GluLeuValGlyGluGluAlaAlaLys-70 |
| SEQ. ID. NO. 35414 | 120-ProGlnAspLeuAsnSerGlyLysLeu-128 |
| SEQ. ID. NO. 35415 | 140-IleArgIleAspArgSerAsnAspAspGlnThrHis-151 |
| SEQ. ID. NO. 35416 | 160-AsnLysPheProThrArgSerAsnAspLeuLeuAsn-171 |
| SEQ. ID. NO. 35417 | 173-ArgAspLeuGluGlnGlyLeuGluAsn-181 |
| SEQ. ID. NO. 35418 | 188-AlaGluAlaAspLeu-192 |
| SEQ. ID. NO. 35419 | 196-ProValGluArgGluProAsnGlnSerAsp-205 |
| SEQ. ID. NO. 35420 | 221-GlyMetAspAsnSerGlySerGluAlaThrGlyLysTyrGlnGly-235 |
| SEQ. ID. NO. 35421 | 241-AlaAspAsnProPheGlyLeu-247 |
| SEQ. ID. NO. 35422 | 255-TyrGlyArgSerIleGlyGlyThrProAspGluGluAsnPheAspGlyHisArgLysGluGlyGlySerAsn-278 |
| SEQ. ID. NO. 35423 | 297-HisAsnGlyTyrArg-301 |
| SEQ. ID. NO. 35424 | 311-GluValTyrAspTyrAsnGlyLysSerTyrAsnThrAspPheGlyPhe-326 |
| SEQ. ID. NO. 35425 | 330-LeuTyrArgAspAlaLysArgLysThrTyrLeu-340 |
| SEQ. ID. NO. 35426 | 345-TrpThrArgGluThrLysSerTyrIleAspAspAlaGluLeuThrValGlnArgArgLysThrThr-366 |
| SEQ. ID. NO. 35427 | 372-LeuSerHisLysGlyTyrIleGlyArgSerThrAlaAspPheLysLeuLysTyrLysHisGlyThrGlyMetLysAspAlaLeuArgAlaPro GluGluAlaPheGlyGluGlyThrSerArg-412 |
| SEQ. ID. NO. 35428 | 419-SerAlaAspValAsnThrPro-425 |
| SEQ. ID. NO. 35429 | 442-GlnTrpAsnLysThrProLeuThrSerGlnAspLysLeuAla-455 |
| SEQ. ID. NO. 35430 | 460-HisThrValArgGlyPheAspGlyGluMetSerLeuProAlaGluArgGlyTrpTyrTrpArgAsnAspLeuSerTrpGlnPheLysProGly His-491 |
| SEQ. ID. NO. 35431 | 503-SerGlyGlnSerAlaLys-508 |
| SEQ. ID. NO. 35432 | 540-ArgAlaLeuLysLysProGluTyrPheGlnThrLysLysTrpValThr-555 |
| Hydrophilic Regions - Hopp-Woods | |
| SEQ. ID. NO. 35433 | 1-GluAlaValSerGlnGlnGlnAspIleLeuGlnArgGlnArgGluLysGlnLeuArgGluGlnMetGlnProGluGlnAspValArgLeuAsp GlyThrAspThrGlyIleGluLysMetAla-41 |

TABLE 1-continued

| | |
|---|---|
| SEQ. ID. NO. 35434 | 47-AlaAsnSerAspGluAlaSer-53 |
| SEQ. ID. NO. 35435 | 62-GluLeuValGlyGluGluAlaAlaLys-70 |
| SEQ. ID. NO. 35436 | 121-GlnAspLeuAsnSerGlyLys-127 |
| SEQ. ID. NO. 35437 | 140-IleArgIleAspArgSerAsnAspAspGlnThrHis-151 |
| SEQ. ID. NO. 35438 | 162-PheProThrArgSerAsnAsp-168 |
| SEQ. ID. NO. 35439 | 173-ArgAspLeuGluGlnGlyLeuGluAsn-181 |
| SEQ. ID. NO. 35440 | 188-AlaGluAlaAspLeu-192 |
| SEQ. ID. NO. 35441 | 196-ProValGluArgGluProAsnGlnSer-204 |
| SEQ. ID. NO. 35442 | 222-MetAspAsnSerGlySerGluAlaThrGlyLysTyr-233 |
| SEQ. ID. NO. 35443 | 259-IleGlyGlyThrProAspGluGluAsnPheAspGlyHisArgLysGluGlyGlySer-277 |
| SEQ. ID. NO. 35444 | 313-TyrAspTyrAsnGly-317 |
| SEQ. ID. NO. 35445 | 330-LeuTyrArgAspAlaLysArgLysThrTyrLeu-340 |
| SEQ. ID. NO. 35446 | 345-TrpThrArgGluThrLysSerTyrIleAspAspAlaGluLeuThrValGlnArgArgLysThrThr-366 |
| SEQ. ID. NO. 35447 | 381-SerThrAlaAspPheLysLeuLysTyrLysHis-391 |
| SEQ. ID. NO. 35448 | 393-ThrGlyMetLysAspAlaLeuArgAlaProGluGluAlaPheGly-407 |
| SEQ. ID. NO. 35449 | 447-ProLeuThrSerGlnAspLysLeuAla-455 |
| SEQ. ID. NO. 35450 | 463-ArgGlyPheAspGlyGluMet-469 |
| SEQ. ID. NO. 35451 | 540-ArgAlaLeuLysLysProGluTyrPheGln-549 |
| g708 | |
| AMPHI Regions - AMPHI | |
| SEQ. ID. NO. 35452 | 26-ProSerArgAlaGluLysAlaAsnGlnValSerAsnIle-38 |
| SEQ. ID. NO. 35453 | 56-ThrAlaSerIleGluAspAlaLeuLysSerAsnPro-67 |
| SEQ. ID. NO. 35454 | 79-IleTyrGlnTyrLeuLys-84 |
| SEQ. ID. NO. 35455 | 89-AlaGlnGluSerPhe-93 |
| SEQ. ID. NO. 35456 | 119-AsnArgProAlaGluSerMetAla-126 |
| SEQ. ID. NO. 35457 | 128-PheAspLysAlaLeu-132 |
| SEQ. ID. NO. 35458 | 142-IleAlaAsnLeuAsnLys-147 |
| SEQ. ID. NO. 35459 | 176-ProAlaPheLysGluLeuAlaArg-183 |
| SEQ. ID. NO. 35460 | 221-LysAlaLeuGlyAsnValGlnAla-228 |
| Antigenic Index - Jameson-Wolf | |
| SEQ. ID. NO. 35461 | 2-ProPheLysProSerLysArgIleSer-10 |
| SEQ. ID. NO. 35462 | 19-AlaCysSerThrSerTyrArgProSerArgAlaGluLysAlaAsnGln-34 |
| SEQ. ID. NO. 35463 | 46-TyrMetArgGlyGlnAspTyrArgGlnAlaThrAlaSerIleGluAspAlaLeuLysSerAsnProLysAsnGluLeu-71 |
| SEQ. ID. NO. 35464 | 84-LysValAsnAspLysAlaGlnGluSerPheArg-94 |
| SEQ. ID. NO. 35465 | 97-LeuSerIleLysProAspSerAlaGluIleAsnAsnAsnTyrGlyTrp-112 |
| SEQ. ID. NO. 35466 | 115-CysGlyArgLeuAsnArgProAlaGlu-123 |
| SEQ. ID. NO. 35467 | 131-AlaLeuAlaAspProThrTyrProThr-139 |
| SEQ. ID. NO. 35468 | 145-LeuAsnLysGlyIleCysSerAlaLysGlnGlyGln-156 |
| SEQ. ID. NO. 35469 | 176-ProAlaPheLysGluLeuAlaArgThrLysMet-186 |
| SEQ. ID. NO. 35470 | 191-LeuGlyAspAlaAspTyrTyrPheLysLysTyrGlnSerArgValGluValLeuGlnAlaAspAspLeu-213 |
| SEQ. ID. NO. 35471 | 240-PheProTyrSerGluGluLeuGln-247 |
| Hydrophilic Regions - Hopp-Woods | |
| SEQ. ID. NO. 35472 | 4-LysProSerLysArgIle-9 |
| SEQ. ID. NO. 35473 | 24-TyrArgProSerArgAlaGluLysAlaAsnGln-34 |
| SEQ. ID. NO. 35474 | 46-TyrMetArgGlyGlnAspTyrArgGln-54 |
| SEQ. ID. NO. 35475 | 56-ThrAlaSerIleGluAspAlaLeuLysSerAsnProLysAsnGlu-70 |
| SEQ. ID. NO. 35476 | 84-LysValAsnAspLysAlaGlnGluSerPheArg-94 |
| SEQ. ID. NO. 35477 | 99-IleLysProAspSerAlaGluIle-106 |
| SEQ. ID. NO. 35478 | 117-ArgLeuAsnArgProAlaGlu-123 |
| SEQ. ID. NO. 35479 | 149-IleCysSerAlaLysGlnGly-155 |
| SEQ. ID. NO. 35480 | 177-AlaPheLysGluLeuAlaArgThrLysMet-186 |
| SEQ. ID. NO. 35481 | 201-TyrGlnSerArgValGluValLeuGlnAlaAspAspLeu-213 |
| g709 | |
| AMPHI Regions - AMPHI | |
| SEQ. ID. NO. 35482 | 6-SerLeuLeuAspMetProArgGlyGlu-14 |
| SEQ. ID. NO. 35483 | 18-ValValValAlaLeuIleAlaAlaMetGly-27 |
| SEQ. ID. NO. 35484 | 37-ProHisMetSerIleIleAlaAlaIleValValLeu-48 |
| SEQ. ID. NO. 35485 | 54-AlaArgGlyLeuLysTyr-59 |
| SEQ. ID. NO. 35486 | 67-IleGlyAlaLeuAsnGlnGlyMet-74 |
| SEQ. ID. NO. 35487 | 115-SerAlaPheAlaLeuCysSerVal-122 |
| SEQ. ID. NO. 35488 | 130-SerLeuThrAlaCysAla-135 |
| SEQ. ID. NO. 35489 | 171-ProLeuSerAspThr-175 |
| SEQ. ID. NO. 35490 | 185-IleAspLeuPheGluHisIleLysAsnMetMetTyrThrThr-198 |
| SEQ. ID. NO. 35491 | 221-LeuAsnSerValGluSerPheArg-228 |
| SEQ. ID. NO. 35492 | 245-PheAlaLeuLeuValValLeu-251 |
| SEQ. ID. NO. 35493 | 261-AlaMetLeuPheThrValIleAlaAlaValAlaValThrTyr-274 |
| SEQ. ID. NO. 35494 | 278-ThrProAspLeuArgGlnLeuGlyAlaTrpPhe-288 |
| SEQ. ID. NO. 35495 | 298-AlaPheLysAspIleAlaLysLeuIleSerArgGlyGly-310 |
| SEQ. ID. NO. 35496 | 334-LeuGlyValIleProSerLeuLeuGluAlaValArgThrPheLeuThr-349 |
| SEQ. ID. NO. 35497 | 382-ThrPheLysProVal-386 |
| SEQ. ID. NO. 35498 | 396-AsnLeuSerArgThrLeuGluAspAlaGlyThrValIleAsnProLeuValProTrpSerValCysGlyValPheIleSerHis-423 |
| Antigenic Index - Jameson-Wolf | |
| SEQ. ID. NO. 35499 | 8-LeuAspMetProArgGlyGluAla-15 |
| SEQ. ID. NO. 35500 | 55-ArgGlyLeuLysTyrAsnAspMetGln-63 |
| SEQ. ID. NO. 35501 | 165-PheGlyAspLysMetSerProLeuSerAspThrThrGly-177 |
| SEQ. ID. NO. 35502 | 222-AsnSerValGluSerPheArgSerGlnLeuGlu-232 |
| SEQ. ID. NO. 35503 | 277-SerThrProAspLeuArgGln-283 |
| SEQ. ID. NO. 35504 | 290-GlyGlyTyrLysLeuGluGlyGluAlaPheLysAspIleAlaLysLeuIleSerArgGlyGlyLeuGlu-312 |
| SEQ. ID. NO. 35505 | 349-ThrAsnAlaGlyArgAlaThr-355 |

TABLE 1-continued

| | |
|---|---|
| SEQ. ID. NO. 35506 | 378-LeuSerGlyGluThrPheLysProValTyrAspLysLeuGly-391 |
| SEQ. ID. NO. 35507 | 396-AsnLeuSerArgThrLeuGluAspAlaGlyThr-406 |
| Hydrophilic Regions - Hopp-Woods | |
| SEQ. ID. NO. 35508 | 8-LeuAspMetProArgGlyGluAla-15 |
| SEQ. ID. NO. 35509 | 57-LeuLysTyrAsnAsp-61 |
| SEQ. ID. NO. 35510 | 167-AspLysMetSerProLeuSerAsp-174 |
| SEQ. ID. NO. 35511 | 225-GluSerPheArgSerGlnLeuGlu-232 |
| SEQ. ID. NO. 35512 | 279-ProAspLeuArgGln-283 |
| SEQ. ID. NO. 35513 | 293-LysLeuGluGlyGluAlaPheLysAspIleAlaLysLeuIleSer-307 |
| SEQ. ID. NO. 35514 | 399-ArgThrLeuGluAspAlaGly-405 |
| g716 | |
| AMPHI Regions - AMPHI | |
| SEQ. ID. NO. 35515 | 33-GlyValGlnLysSerAlaGlnGly-40 |
| SEQ. ID. NO. 35516 | 81-AlaThrValLysLysAlaHisLysHisThrLysAla-92 |
| Antigenic Index - Jameson-Wolf | |
| SEQ. ID. NO. 35517 | 1-MetAsnLysAsnIle-5 |
| SEQ. ID. NO. 35518 | 26-LysProAlaSerAsnAlaThrGlyValGlnLysSerAlaGlnGlySerCysGlyAlaSerLysSerAlaGluGlySerCysGlyAlaSerLys SerAlaGluGlySerCysGly-63 |
| SEQ. ID. NO. 35519 | 65-AlaAlaSerLysAlaGlyGluGlyLysCysGlyGluGlyLysCysGlyAlaThrValLysLysAlaHisLysHisThrLysAlaSerLysAla LysAlaLysSerAlaGluGlyLysCysGlyGluGlyLysCysGlySerLys-112 |
| Hydrophilic Regions - Hopp-Woods | |
| SEQ. ID. NO. 35520 | 33-GlyValGlnLysSerAlaGln-39 |
| SEQ. ID. NO. 35521 | 43-GlyAlaSerLysSerAlaGluGlySerCysGlyAlaSerLysSerAlaGluGlySerCys-62 |
| SEQ. ID. NO. 35522 | 65-AlaAlaSerLysAlaGlyGluGlyLysCysGlyGluGlyLysCys-79 |
| SEQ. ID. NO. 35523 | 81-AlaThrValLysLysAlaHisLysHisThrLysAlaSerLysAlaLysAlaLysSerAlaGluGlyLysCysGlyGluGlyLysCysGlySer Lys-112 |
| g717 | |
| AMPHI Regions - AMPHI | |
| SEQ. ID. NO. 35524 | 87-AlaAlaIleAlaAla-91 |
| SEQ. ID. NO. 35525 | 174-ThrAlaValTyrAlaLeuAlaAsn-181 |
| SEQ. ID. NO. 35526 | 209-LeuHisArgGlyLeu-213 |
| SEQ. ID. NO. 35527 | 223-SerLeuAlaTyrTrp-227 |
| SEQ. ID. NO. 35528 | 241-AlaGlyLeuGluGlnLeuGly-247 |
| SEQ. ID. NO. 35529 | 263-GlnSerIlePheSerThrValTrpThrProTyrIlePheArgAlaIleGluGlu-280 |
| SEQ. ID. NO. 35530 | 305-ThrGlyIlePheSerProLeuAlaSer-313 |
| SEQ. ID. NO. 35531 | 347-LeuAsnValValArgLysThr-353 |
| SEQ. ID. NO. 35532 | 358-LeuAlaThrLeuGlyAlaLeuAla-365 |
| SEQ. ID. NO. 35533 | 401-SerSerCysArgLeuTrpGlnProLeuLysArgLeu-412 |
| SEQ. ID. NO. 35534 | 430-CysPheGlyThrPro-434 |
| SEQ. ID. NO. 35535 | 442-GlyValTrpAlaAlaTyrLeuAlaGly-450 |
| SEQ. ID. NO. 35536 | 457-LysAsnLeuHisLysLeuPheHisTyr-465 |
| Antigenic Index - Jameson-Wolf | |
| SEQ. ID. NO. 35537 | 1-MetAspThrLysGlu-5 |
| SEQ. ID. NO. 35538 | 32-ProAlaAspAspIleGlyArg-38 |
| SEQ. ID. NO. 35539 | 69-AlaAspLysAspThrLeu-74 |
| SEQ. ID. NO. 35540 | 95-SerArgProSerLeuProSerGluIle-103 |
| SEQ. ID. NO. 35541 | 135-MetGluGlyArgAla-139 |
| SEQ. ID. NO. 35542 | 192-AsnArgCysArgLeuLysAlaValArgArgAlaProPheSer-205 |
| SEQ. ID. NO. 35543 | 231-SerAlaAspArgLeuPheLeu-237 |
| SEQ. ID. NO. 35544 | 277-AlaIleGluGluAsnAlaThrProAlaArgLeu-287 |
| SEQ. ID. NO. 35545 | 289-AlaThrAlaGluSer-293 |
| SEQ. ID. NO. 35546 | 317-ProGluAsnTyrAla-321 |
| SEQ. ID. NO. 35547 | 349-ValValArgLysThrArgProIleAla-357 |
| SEQ. ID. NO. 35548 | 376-ProSerGlyGlyThrArgGlyAla-383 |
| SEQ. ID. NO. 35549 | 398-LysThrGluSerSerCysArgLeu-405 |
| SEQ. ID. NO. 35550 | 453-LeuArgHisArgLysAsnLeu-459 |
| Hydrophilic Regions - Hopp-Woods | |
| SEQ. ID. NO. 35551 | 1-MetAspThrLysGlu-5 |
| SEQ. ID. NO. 35552 | 69-AlaAspLysAspThrLeu-74 |
| SEQ. ID. NO. 35553 | 135-MetGluGlyArgAla-139 |
| SEQ. ID. NO. 35554 | 192-AsnArgCysArgLeuLysAlaValArgArgAlaPro-203 |
| SEQ. ID. NO. 35555 | 277-AlaIleGluGluAsnAlaThrProAlaArgLeu-287 |
| SEQ. ID. NO. 35556 | 289-AlaThrAlaGluSer-293 |
| SEQ. ID. NO. 35557 | 349-ValValArgLysThrArgPro-355 |
| SEQ. ID. NO. 35558 | 378-GlyGlyThrArgGly-382 |
| SEQ. ID. NO. 35559 | 399-ThrGluSerSerCys-403 |
| SEQ. ID. NO. 35560 | 453-LeuArgHisArgLysAsnLeu-459 |
| g728 | |
| AMPHI Regions - AMPHI | |
| SEQ. ID. NO. 35561 | 11-SerPhePheAlaLeuValPheAla-18 |
| SEQ. ID. NO. 35562 | 39-AlaThrGluValProGluAsnPro-46 |
| SEQ. ID. NO. 35563 | 48-AlaPheValAlaLysLeuAlaArgLeuPheArgAsnAla-60 |
| SEQ. ID. NO. 35564 | 74-GluGluSerLeuAlaGlyAlaValAspAsp-83 |
| SEQ. ID. NO. 35565 | 167-HisGlyGluAsnTyrGluThr-173 |
| SEQ. ID. NO. 35566 | 198-GluAspValTyrGluHisCysLeuGlyCysTyrGlnMet-210 |
| SEQ. ID. NO. 35567 | 218-TyrArgAspValAlaAsn-223 |
| SEQ. ID. NO. 35568 | 235-SerAsnArgIleAlaSer-240 |
| SEQ. ID. NO. 35569 | 251-MetArgGluLeuMetProArg-257 |
| SEQ. ID. NO. 35570 | 355-GluLysGluValSerArgTyrAlaGluAlaAlaAlaArg-367 |

TABLE 1-continued

Antigenic Index - Jameson-Wolf
SEQ. ID. NO. 35571 29-IleAsnProArgTrp-33
SEQ. ID. NO. 35572 35-LeuSerAspThrAlaThrGluValProGluAsnProAsnAla-48
SEQ. ID. NO. 35573 57-PheArgAsnAlaAspArgAla-63
SEQ. ID. NO. 35574 67-ValLysGluSerMetArgThrGluGluSerLeu-77
SEQ. ID. NO. 35575 80-AlaValAspAspGlyProLeuGlnSerGluLysAspTyr-92
SEQ. ID. NO. 35576 98-ArgLeuSerArgLeuLysGluLysAlaLys-107
SEQ. ID. NO. 35577 112-ThrGluGlnGluHisGlyGlu-118
SEQ. ID. NO. 35578 125-TyrIleGlyGluGlyGly-130
SEQ. ID. NO. 35579 136-LeuSerGlnArgSerProGluAlaPheVal-145
SEQ. ID. NO. 35580 149-TyrLeuTyrArgAsnAspArgProPheSer-158
SEQ. ID. NO. 35581 166-AlaHisGlyGluAsnTyrGluThrThrGlyGluTyrArgVal-179
SEQ. ID. NO. 35582 182-GlnProAspGlySerVal-187
SEQ. ID. NO. 35583 190-AlaAlaGlyArgGlyLysIleGlyGluAspValTyr-201
SEQ. ID. NO. 35584 217-LysTyrArgAspValAlaAsnAspGluGlnLysValTrpAspPheArgGluGluSerAsnArgIleAlaSerAspSerArgAspTyrVal-246
SEQ. ID. NO. 35585 250-AsnMetArgGluLeuMetProArgGlyMetLysAlaAsnSer-263
SEQ. ID. NO. 35586 267-GlyTyrAspAlaAspGlyLeuProGlnLys-276
SEQ. ID. NO. 35587 280-SerPheAspAsnGlyLysLysArgGlnSerPheGluTyrTyrLeuLysAsnGlyAsn-298
SEQ. ID. NO. 35588 309-LeuLysAlaAspGlyValThr-315
SEQ. ID. NO. 35589 329-LeuAspGlyGlyArgIleIleArgGluGluLysGlnGlyAspArgLeuProAspPhe-347
SEQ. ID. NO. 35590 349-LeuAsnLeuGluAspLeuGluLysGluValSerArgTyrAlaGluAlaAlaAlaArgArgSerGlyGlyArgArgGlyLeuSerHis-377
Hydrophilic Regions - Hopp-Woods
SEQ. ID. NO. 35591 38-ThrAlaThrGluValProGluAsnPro-46
SEQ. ID. NO. 35592 57-PheArgAsnAlaAspArgAla-63
SEQ. ID. NO. 35593 67-ValLysGluSerMetArgThrGluGluSerLeu-77
SEQ. ID. NO. 35594 80-AlaValAspAspGlyProLeuGlnSerGluLysAspTyr-92
SEQ. ID. NO. 35595 98-ArgLeuSerArgLeuLysGluLysAlaLys-107
SEQ. ID. NO. 35596 112-ThrGluGlnGluHisGlyGlu-118
SEQ. ID. NO. 35597 136-LeuSerGlnArgSerProGlu-142
SEQ. ID. NO. 35598 151-TyrArgAsnAspArgProPhe-157
SEQ. ID. NO. 35599 169-GluAsnTyrGluThrThrGlyGluTyr-177
SEQ. ID. NO. 35600 190-AlaAlaGlyArgGlyLysIleGlyGluAspValTyr-201
SEQ. ID. NO. 35601 217LysTyrArgAspValAlaAsnAspGluGlnLysValTrpAspPheArgGluGluSerAsnArgIleAlaSerAspSerArgAsp-244
SEQ. ID. NO. 35602 250-AsnMetArgGluLeuMetProArgGlyMetLys-260
SEQ. ID. NO. 35603 268-TyrAspAlaAspGlyLeuPro-274
SEQ. ID. NO. 35604 282-AspAsnGlyLysLysArgGlnSer-289
SEQ. ID. NO. 35605 309-LeuLysAlaAspGlyValThr-315
SEQ. ID. NO. 35606 331-GlyGlyArgIleIleArgGluGluLysGlnGlyAspArgLeuPro-345
SEQ. ID. NO. 35607 349-LeuAsnLeuGluAspLeuGluLysGluValSerArgTyrAlaGluAlaAlaAlaArgArgSerGlyGlyArgArgGlyLeuSer-376
g729
AMPHI Regions - AMPHI
SEQ. ID. NO. 35608 21-CysThrMetIleProGlnTyr-27
SEQ. ID. NO. 35609 55-HisAspTyrPheAla-59
SEQ. ID. NO. 35610 61-ProArgLeuGlnLysLeuIleAspIle-69
SEQ. ID. NO. 35611 149-GlnGlyTyrPheAla-153
SEQ. ID. NO. 35612 242-LeuAlaThrLeuIleAsn-247
SEQ. ID. NO. 35613 250-IleProGluAspLeuProAla-256
SEQ. ID. NO. 35614 268-LysLeuProAlaGlyLeu-273
SEQ. ID. NO. 35615 321-GluLeuGlyGlyLeuPheLysSerGly-329
SEQ. ID. NO. 35616 371-ValGlnSerAlaPheGlnAspValAlaAsnAla-381
SEQ. ID. NO. 35617 388-LeuAspLysAlaTyrAspAlaLeuSerLysGlnSerArg-400
SEQ. ID. NO. 35618 419-GlyAlaLeuAspLeuLeuAspAlaGlu-427
SEQ. ID. NO. 35619 442-LeuThrArgAlaGluAsnLeuAlaAspLeuTyrLysAlaLeuAspGlyGlyLeu-459
Antigenic Index - Jameson-Wolf
SEQ. ID. NO. 35620 25-ProGlnTyrGluGlnProLysValGluVal-34
SEQ. ID. NO. 35621 36-GluThrPheGlnAsnAspThrSerValSerSer-46
SEQ. ID. NO. 35622 53-GlyTrpHisAspTyrPheAlaAspProArgLeuGlnLys-65
SEQ. ID. NO. 35623 70-AlaLeuGluArgAsnThrSerLeuArgThr-79
SEQ. ID. NO. 35624 85-GluIleTyrArgLysGlnTyrMetIleGluArgAsnAsnLeuLeuPro-100
SEQ. ID. NO. 35625 106-AlaAsnGlySerArgGlnGlySerLeuSerGlyGlyAsnValSerSerSerTyrAsn-124
SEQ. ID. NO. 35626 138-GlyArgValArgSerAsnSerGluAlaAla-147
SEQ. ID. NO. 35627 156-AlaAsnArgAspAlaAla-161
SEQ. ID. NO. 35628 173-TyrPheAsnGluArgTyrAlaGluLysAlaMet-183
SEQ. ID. NO. 35629 188-ArgValLeuLysThrArgGluGluThrTyrLysLeuSerGluLeuArgTyr-204
SEQ. ID. NO. 35630 215-ArgGlnGlnGluAlaLeuIleGluSerAlaLysAlaAspTyr-228
SEQ. ID. NO. 35631 232-AlaArgSerArgGluGlnAlaArgAsn-240
SEQ. ID. NO. 35632 247-AsnArgProIleProGluAspLeuProAla-256
SEQ. ID. NO. 35633 277-ValLeuLeuAspArgProAspIleArgAlaAlaGluHisAlaLeuLysGlnAlaAsnAla-296
SEQ. ID. NO. 35634 310-ArgLeuThrGlySerValGlyThrGlySer-319
SEQ. ID. NO. 35635 326-PheLysSerGlyThr-330
SEQ. ID. NO. 35636 347-GlyThrAsnLysAlaAsnLeuAspValAlaLysLeuArgGlnGln-361
SEQ. ID. NO. 35637 383-AlaAlaArgGluGlnLeuAspLysAlaTyrAspAlaLeuSerLysGlnSerArgAlaSerLysGluAlaLeuArg-407
SEQ. ID. NO. 35638 411-LeuArgTyrLysHisGlyValSer-418
SEQ. ID. NO. 35639 424-LeuAspAlaGluArgIleSerTyrSerAlaGluGly-435
SEQ. ID. NO. 35640 442-LeuThrArgAlaGluAsnLeu-448
SEQ. ID. NO. 35641 455-LeuAspGlyGlyLeuLysArgAspThrGlnThrGlyLys-467
Hydrophilic Regions - Hopp-Woods
SEQ. ID. NO. 35642 28-GluGlnProLysValGluVal-34
SEQ. ID. NO. 35643 42-ThrSerValSerSer-46
SEQ. ID. NO. 35644 61-ProArgLeuGlnLys-65

TABLE 1-continued

| | |
|---|---|
| SEQ. ID. NO. 35645 | 70-AlaLeuGluArgAsnThrSerLeu-77 |
| SEQ. ID. NO. 35646 | 91-TyrMetIleGluArgAsnAsn-97 |
| SEQ. ID. NO. 35647 | 107-AsnGlySerArgGlnGlySer-113 |
| SEQ. ID. NO. 35648 | 138-GlyArgValArgSerAsnSerGluAlaAla-147 |
| SEQ. ID. NO. 35649 | 156-AlaAsnArgAspAlaAla-161 |
| SEQ. ID. NO. 35650 | 177-ArgTyrAlaGluLysAlaMet-183 |
| SEQ. ID. NO. 35651 | 188-ArgValLeuLysThrArgGluGluThrTyrLys-198 |
| SEQ. ID. NO. 35652 | 200-SerGluLeuArgTyr-204 |
| SEQ. ID. NO. 35653 | 215-ArgGlnGlnGluAlaLeuIleGluSerAlaLysAlaAspTyr-228 |
| SEQ. ID. NO. 35654 | 232-AlaArgSerArgGluGlnAlaArgAsn-240 |
| SEQ. ID. NO. 35655 | 249-ProIleProGluAspLeuPro-255 |
| SEQ. ID. NO. 35656 | 277-ValLeuLeuAspArgProAspIleArgAlaAlaGluHisAlaLeuLysGlnAlaAsn-295 |
| SEQ. ID. NO. 35657 | 350-LysAlaAsnLeuAspValAlaLysLeuArgGln-360 |
| SEQ. ID. NO. 35658 | 383-AlaAlaArgGluGlnLeuAspLysAlaTyrAspAlaLeuSerLysGlnSerArgAlaSerLysGluAlaLeuArg-407 |
| SEQ. ID. NO. 35659 | 424-LeuAspAlaGluArgIleSerTyr-431 |
| SEQ. ID. NO. 35660 | 442-LeuThrArgAlaGluAsnLeu-448 |
| SEQ. ID. NO. 35661 | 455-LeuAspGlyGlyLeuLysArgAspThrGlnThrGlyLys-467 |
| g730 | |
| AMPHI Regions - AMPHI | |
| SEQ. ID. NO. 35662 | 6-ArgLeuThrAsnLeuLeuAlaAlaCysAla-15 |
| SEQ. ID. NO. 35663 | 26-LeuAlaAlaAspLeu-30 |
| SEQ. ID. NO. 35664 | 67-LysIleAsnValIleGlnAspTyrThrHisGln-77 |
| SEQ. ID. NO. 35665 | 111-AsnHisAlaAlaAsp-115 |
| SEQ. ID. NO. 35666 | 141-HisProAlaAspAlaTyrAspGlyProLysGlyGlyAsnTyrProLysProThr-158 |
| SEQ. ID. NO. 35667 | 187-GlnArgIlePheAspAsnTyrAsnAsnLeuGlySerAsnPheSerAspArgAlaAspGlu-206 |
| SEQ. ID. NO. 35668 | 214-HisAsnAlaLysLeu-218 |
| SEQ. ID. NO. 35669 | 220-ArgTrpGlyAsnSerMetGluPheValAsnGlyValAla-232 |
| SEQ. ID. NO. 35670 | 234-GlyAlaLeuAsnProPheIleSer-241 |
| SEQ. ID. NO. 35671 | 262-AlaAlaMetArgAsnIleAla-268 |
| SEQ. ID. NO. 35672 | 277-AlaAlaIleGlyGlyLeuGlySerAla-285 |
| SEQ. ID. NO. 35673 | 288-PheGluLysAsnThrArgGluAlaValAspArgTrpIleGlnGlu-302 |
| SEQ. ID. NO. 35674 | 305-AsnAlaAlaGluThrValGluAlaLeuValAsnValLeuProPheAlaLysValLysAsnLeuThrLysAlaAlaLysPro-331 |
| SEQ. ID. NO. 35675 | 353-LeuValLysThrAlaAspGlyTyrLysAlaIleAlaHisIleGlnAla-368 |
| SEQ. ID. NO. 35676 | 390-ArgTyrGlyAsnProTyr-395 |
| SEQ. ID. NO. 35677 | 403-ValSerAspGlyIle-407 |
| SEQ. ID. NO. 35678 | 434-LysAlaGlySerArgLeuLeuSerGluSer-443 |
| SEQ. ID. NO. 35679 | 458-ProLeuLysAlaTyr-462 |
| SEQ. ID. NO. 35680 | 510-AspSerHisArgSerValGlyAspSerAsnArgValValArgGluGlyLys-526 |
| SEQ. ID. NO. 35681 | 553-GlnValThrGlnPheLys-558 |
| Antigenic Index - Jameson-Wolf | |
| SEQ. ID. NO. 35682 | 2-LysProLeuArgArgLeuThr-8 |
| SEQ. ID. NO. 35683 | 35-PheIleThrAspAsnThrGlnArgGlnHisTyrGluProGlyGlyLys-50 |
| SEQ. ID. NO. 35684 | 55-GlyAspProArgGlySerValSerAspArgThrGlyLysIleAsnVal-70 |
| SEQ. ID. NO. 35685 | 99-SerGlyHisGlyHisGluGluHisAlaProPheAsp-110 |
| SEQ. ID. NO. 35686 | 112-HisAlaAlaAspSerAlaSerGluGluLysGlyAsnValAspAspGlyPhe-128 |
| SEQ. ID. NO. 35687 | 133-LeuAsnTrpGluGlyHisGluHisHisProAlaAspAlaTyrAspGlyProLysGlyGlyAsnTyrProLysProThrGlyAlaArgAspGlu TyrThrTyrHisVal-168 |
| SEQ. ID. NO. 35688 | 170-GlyThrAlaArgSerIleLysLeuAsnProThrAspThrArgSerIleArgGlnArgIle-189 |
| SEQ. ID. NO. 35689 | 191-AspAsnTyrAsnAsnLeuGlySerAsnPheSerAspArgAlaAspGluAlaAsnArgLysMetPheGluHisAsnAlaLysLeuAspArg TrpGlyAsnSer-224 |
| SEQ. ID. NO. 35690 | 257-TyrAlaIleAspLysAlaAlaMet-264 |
| SEQ. ID. NO. 35691 | 271-ProAlaGluGlyLysPhe-276 |
| SEQ. ID. NO. 35692 | 287-GlyPheGluLysAsnThrArgGluAlaValAsp-297 |
| SEQ. ID. NO. 35693 | 299-TrpIleGlnGluAsnProAsnAlaAlaGluThrValGlu-311 |
| SEQ. ID. NO. 35694 | 323-LysAsnLeuThrLysAlaAlaLysProGlyLysAlaAlaValSerGlyAspPheSerLysSerTyr-344 |
| SEQ. ID. NO. 35695 | 355-LysThrAlaAspGlyTyrLys-361 |
| SEQ. ID. NO. 35696 | 367-GlnAlaGlyAspArgValLeuSerLysAspGluAlaSerGlyGluThrGlyTyrLysProValThrAlaArgTyrGlyAsnProTyrGln Glu-397 |
| SEQ. ID. NO. 35697 | 403-ValSerAspGlyIleGlyAsnSer-410 |
| SEQ. ID. NO. 35698 | 422-TyrSerAspGlyLysTrpIleLysAlaGluAspLeuLysAlaGlySerArgLeuLeuSerGluSerGlyLysThrGlnThr-448 |
| SEQ. ID. NO. 35699 | 453-ValValLysProLysProLeuLys-460 |
| SEQ. ID. NO. 35700 | 474-ValLysGlyAsnGlnAlaGluThrGlu-482 |
| SEQ. ID. NO. 35701 | 487-HisAsnAspCysProProLysProLysProThrAsnHisAlaGlnGlnArgLysGluGluAlaLysAsnAspSerHisArgSerValGlyAsp SerAsnArgValValArgGluGlyLysGlnTyrLeuAspSerAspThrGlyAsn-535 |
| SEQ. ID. NO. 35702 | 538-TyrValLysGlyAspLysVal-544 |
| SEQ. ID. NO. 35703 | 547-LeuThrProAspGlyArgGlnValThrGlnPheLysAsnSerLysAlaAsnThrSerLysArgValLysAsnGlyLysTrpThrProLys-576 |
| Hydrophilic Regions - Hopp-Woods | |
| SEQ. ID. NO. 35704 | 2-LysProLeuArgArgLeuThr-8 |
| SEQ. ID. NO. 35705 | 39-AsnThrGlnArgGlnHisTyrGluProGlyGly-49 |
| SEQ. ID. NO. 35706 | 55-GlyAspProArgGlySerValSerAspArgThrGlyLys-67 |
| SEQ. ID. NO. 35707 | 102-GlyHisGluGluHisAlaPro-108 |
| SEQ. ID. NO. 35708 | 112-HisAlaAlaAspSerAlaSerGluGluLysGlyAsnValAspAspGly-127 |
| SEQ. ID. NO. 35709 | 135-TrpGluGlyHisGluHisHisPro-142 |
| SEQ. ID. NO. 35710 | 144-AspAlaTyrAspGlyProLysGlyGlyAsnTyrProLys-156 |
| SEQ. ID. NO. 35711 | 158-ThrGlyAlaArgAspGluTyr-164 |
| SEQ. ID. NO. 35712 | 170-GlyThrAlaArgSerIleLys-176 |
| SEQ. ID. NO. 35713 | 178-AsnProThrAspThrArgSerIleArgGlnArgIle-189 |
| SEQ. ID. NO. 35714 | 200-PheSerAspArgAlaAspGluAlaAsnArgLysMetPheGluHisAsnAlaLysLeuAspArgTrpGlyAsn-223 |
| SEQ. ID. NO. 35715 | 257-TyrAlaIleAspLysAlaAlaMet-264 |
| SEQ. ID. NO. 35716 | 271-ProAlaGluGlyLysPhe-276 |

TABLE 1-continued

| | |
|---|---|
| SEQ. ID. NO. 35717 | 287-GlyPheGluLysAsnThrArgGluAlaValAsp-297 |
| SEQ. ID. NO. 35718 | 303-AsnProAsnAlaAlaGluThrValGlu-311 |
| SEQ. ID. NO. 35719 | 323-LysAsnLeuThrLysAlaAlaLysProGlyLysAlaAlaVal-336 |
| SEQ. ID. NO. 35720 | 355-LysThrAlaAspGlyTyrLys-361 |
| SEQ. ID. NO. 35721 | 368-AlaGlyAspArgValLeuSerLysAspGluAlaSerGlyGluThrGlyTyr-384 |
| SEQ. ID. NO. 35722 | 403-ValSerAspGlyIleGly-408 |
| SEQ. ID. NO. 35723 | 426-LysTrpIleLysAlaGluAspLeuLysAlaGlySer-437 |
| SEQ. ID. NO. 35724 | 439-LeuLeuSerGluSerGlyLysThrGlnThr-448 |
| SEQ. ID. NO. 35725 | 453-ValValLysProLysProLeuLys-460 |
| SEQ. ID. NO. 35726 | 477-AsnGlnAlaGluThrGlu-482 |
| SEQ. ID. NO. 35727 | 489-AspCysProProLysProLysProThrAsn-498 |
| SEQ. ID. NO. 35728 | 500-AlaGlnGlnArgLysGluGluAlaLysAsnAspSerHisArgSerValGlyAspSerAsnArgValValArgGluGlyLysGlnTyrLeuAsp SerAspThrGly-534 |
| SEQ. ID. NO. 35729 | 539-ValLysGlyAspLys-543 |
| SEQ. ID. NO. 35730 | 549-ProAspGlyArgGln-553 |
| SEQ. ID. NO. 35731 | 558-LysAsnSerLysAlaAsnThrSerLysArgValLysAsnGlyLysTrpThrPro-575 |
| g731 | |
| AMPHI Regions - AMPHI | |
| SEQ. ID. NO. 35732 | 17-AlaCysAlaValProGluAlaTyrAspGlyGly-27 |
| SEQ. ID. NO. 35733 | 40-GlyProAspAspPheArgAlaPheSerCys-49 |
| Antigenic Index - Jameson-Wolf | |
| SEQ. ID. NO. 35734 | 22-GluAlaTyrAspGlyGlyGlyArgGlyTyr-31 |
| SEQ. ID. NO. 35735 | 33-ProProValGlnAsnGlnAlaGlyProAspAspPheArgAla-46 |
| SEQ. ID. NO. 35736 | 48-SerCysGluAsnGlyLeu-53 |
| SEQ. ID. NO. 35737 | 55-ValArgValArgAsnLeuAspGlyGlyLysIleAlaLeuArgLeuAspGlyArgArgAlaValLeuSerSerAspValAlaAlaSerGlyGlu ArgTyrThrAla-89 |
| SEQ. ID. NO. 35738 | 92-GlyLeuPheGlyAsnGlyThrGluTrpHisGlnLysGlyGlyGluAla-107 |
| SEQ. ID. NO. 35739 | 113-AspAlaTyrGlyAsnSerValGluThrSerCysArgAlaArg-126 |
| Hydrophilic Regions - Hopp-Woods | |
| SEQ. ID. NO. 35740 | 22-GluAlaTyrAspGlyGlyGly-28 |
| SEQ. ID. NO. 35741 | 39-AlaGlyProAspAspPheArg-45 |
| SEQ. ID. NO. 35742 | 55-ValArgValArgAsnLeuAspGlyGlyLysIleAlaLeuArgLeuAspGlyArgArgAlaValLeu-76 |
| SEQ. ID. NO. 35743 | 80-ValAlaAlaSerGlyGluArgTyrThrAla-89 |
| SEQ. ID. NO. 35744 | 100-TrpHisGlnLysGlyGlyGlu-106 |
| SEQ. ID. NO. 35745 | 119-ValGluThrSerCysArgAlaArg-126 |
| g732 | |
| AMPHI Regions - AMPHI | |
| SEQ. ID. NO. 35746 | 14-LeuGlyAlaIleSer-18 |
| SEQ. ID. NO. 35747 | 43-ValGlnSerIleArgThrMetAlaGluValTyrGly-54 |
| SEQ. ID. NO. 35748 | 66-AspAlaAspLeuPheGluGlyAlaMetLysGlyMetVal-78 |
| SEQ. ID. NO. 35749 | 95-GluIleLysGluSerThrSerGly-102 |
| SEQ. ID. NO. 35750 | 115-AspGlyPheValLysValValSerProIleGluAsp-126 |
| SEQ. ID. NO. 35751 | 155-GluAlaValLysLysMet-160 |
| SEQ. ID. NO. 35752 | 183-ValAsnLeuThrArg-187 |
| SEQ. ID. NO. 35753 | 214-GluArgThrValGluSerValAsnThrAlaAlaLys-225 |
| SEQ. ID. NO. 35754 | 283-LysAlaValProGluAspTyrValTyr-291 |
| SEQ. ID. NO. 35755 | 293-MetGlyGlyAspProLeuAlaGlyIleProAlaGluLeu-305 |
| SEQ. ID. NO. 35756 | 322-SerGluIleValAlaGly-327 |
| SEQ. ID. NO. 35757 | 400-LeuValGlyHisIleGlyAsn-406 |
| SEQ. ID. NO. 35758 | 446-ArgArgIleProAsnProAlaLysAsp-454 |
| SEQ. ID. NO. 35759 | 459-LysAlaLeuAspLeuValLysSerProGluGlnTrpGlnLysSerLeu-474 |
| Antigenic Index - Jameson-Wolf | |
| SEQ. ID. NO. 35760 | 30-AlaAlaGluLysAspGlyArgAspAsnGluVal-40 |
| SEQ. ID. NO. 35761 | 59-AsnTyrTyrHisAspLysProAspAlaAspLeuPhe-70 |
| SEQ. ID. NO. 35762 | 82-AspProHisSerGluTyrMetAspLysLysGlyTyrAlaGluIleLysGluSerThrSerGlyGluPheGlyGly-106 |
| SEQ. ID. NO. 35763 | 111-IleGlyGlnGluAspGlyPhe-117 |
| SEQ. ID. NO. 35764 | 122-SerProIleGluAspThrProAlaGluArgAlaGluValLysSerGlyAspPhe-139 |
| SEQ. ID. NO. 35765 | 144-AspAsnValSerThrArgGlyMetThr-152 |
| SEQ. ID. NO. 35766 | 155-GluAlaValLysLysMetArgGlyLysProGlyThrLysIle-168 |
| SEQ. ID. NO. 35767 | 172-LeuSerArgLysAsnAlaAspLysProIle-181 |
| SEQ. ID. NO. 35768 | 199-LeuIleGluProAspTyrGlyTyr-206 |
| SEQ. ID. NO. 35769 | 211-GlnPheGlnGluArgThrValGlu-218 |
| SEQ. ID. NO. 35770 | 221-AsnThrAlaAlaLysGluLeuValLysGluAsnLysGlyLysProLeuLys-237 |
| SEQ. ID. NO. 35771 | 242-AspLeuArgAspAspProGlyGlyLeu-250 |
| SEQ. ID. NO. 35772 | 269-ValSerThrLysGlyArgAspGlyLysAspGlyMetVal-281 |
| SEQ. ID. NO. 35773 | 284-AlaValProGluAspTyr-289 |
| SEQ. ID. NO. 35774 | 293-MetGlyGlyAspPro-297 |
| SEQ. ID. NO. 35775 | 303-AlaGluLeuLysThr-307 |
| SEQ. ID. NO. 35776 | 316-SerGlySerAlaSerAla-321 |
| SEQ. ID. NO. 35777 | 330-GlnAspHisLysArgAlaVal-336 |
| SEQ. ID. NO. 35778 | 340-ThrGlnSerPheGlyLysGlySerVal-348 |
| SEQ. ID. NO. 35779 | 354-LeuSerAsnGlySer-358 |
| SEQ. ID. NO. 35780 | 368-TyrThrProAsnAspArgSerIleGln-376 |
| SEQ. ID. NO. 35781 | 384-ValGluValLysAspLysGluArgThrPheGluSerArgGluAlaAspLeu-400 |
| SEQ. ID. NO. 35782 | 405-GlyAsnProLeuGlyGlyGluAspValAsnSerGlu-416 |

TABLE 1-continued

| | |
|---|---|
| SEQ. ID. NO. 35783 | 421-ProLeuGluLysAspAlaAspLysProAlaAlaLysGluLysGlyLysLysLysLysAspGluAspLeuSerSerArgArgIleProAsnPro AlaLysAspAspGlnLeuArgLysAlaLeuAspLeuValLysSerProGluGlnTrpGlnLys-472 |
| SEQ. ID. NO. 35784 | 477-AlaAlaLysLysProValSerAsnLysAspLysLysAspLysLys-491 |
| Hydrophilic Regions - Hopp-Woods | |
| SEQ. ID. NO. 35785 | 30-AlaAlaGluLysAspGlyArgAspAsnGluVal-40 |
| SEQ. ID. NO. 35786 | 60-TyrTyrHisAspLysProAspAlaAspLeuPhe-70 |
| SEQ. ID. NO. 35787 | 82-AspProHisSerGluTyrMetAspLysLysGlyTyrAlaGluIleLysGluSerThrSerGlyGlu-103 |
| SEQ. ID. NO. 35788 | 111-IleGlyGlnGluAspGlyPhe-117 |
| SEQ. ID. NO. 35789 | 122-SerProIleGluAspThrProAlaGluArgAlaGluValLysSerGlyAspPhe-139 |
| SEQ. ID. NO. 35790 | 144-AspAsnValSerThr-148 |
| SEQ. ID. NO. 35791 | 155-GluAlaValLysLysMetArgGlyLysProGlyThr-166 |
| SEQ. ID. NO. 35792 | 172-LeuSerArgLysAsnAlaAspLysProIle-181 |
| SEQ. ID. NO. 35793 | 211-GlnPheGlnGluArgThrValGlu-218 |
| SEQ. ID. NO. 35794 | 221-AsnThrAlaAlaLysGluLeuValLysGluAsnLysGlyLysProLeuLys-237 |
| SEQ. ID. NO. 35795 | 242-AspLeuArgAspAspProGly-248 |
| SEQ. ID. NO. 35796 | 271-ThrLysGlyArgAspGlyLysAspGlyMetVal-281 |
| SEQ. ID. NO. 35797 | 303-AlaGluLeuLysThr-307 |
| SEQ. ID. NO. 35798 | 330-GlnAspHisLysArgAlaVal-336 |
| SEQ. ID. NO. 35799 | 370-ProAsnAspArgSerIleGln-376 |
| SEQ. ID. NO. 35800 | 384-ValGluValLysAspLysGluArgThrPheGluSerArgGluAlaAspLeu-400 |
| SEQ. ID. NO. 35801 | 408-LeuGlyGlyGluAspValAsnSer-415 |
| SEQ. ID. NO. 35802 | 421-ProLeuGluLysAspAlaAspLysProAlaAlaLysGluLysGlyLysLysLysLysAspGluAspLeuSerSerArgArgIleProAsnPro AlaLysAspAspGlnLeuArgLysAlaLeuAspLeuValLysSerProGluGlnTrpGln-471 |
| SEQ. ID. NO. 35803 | 477-AlaAlaLysLysProValSerAsnLysAspLysLysAspLysLys-491 |
| g733 | |
| AMPHI Regions - AMPHI | |
| SEQ. ID. NO. 35804 | 6-ThrLeuGlyArgLeuSer-11 |
| SEQ. ID. NO. 35805 | 16-ValLeuAlaLeuThrAla-21 |
| SEQ. ID. NO. 35806 | 33-TyrGlyGlyTyrProAspThrValTyrGluGly-43 |
| SEQ. ID. NO. 35807 | 53-LysGlnThrGluLysMetGluLysTyrPheAlaGluAlaAlaAsn-67 |
| SEQ. ID. NO. 35808 | 92-GlyAlaPheArgGlnPheGluGlu-99 |
| Antigenic Index - Jameson-Wolf | |
| SEQ. ID. NO. 35809 | 2-MetAsnProLysThrLeuGly-8 |
| SEQ. ID. NO. 35810 | 23-AlaGlyGlyGlyHisLys-28 |
| SEQ. ID. NO. 35811 | 32-TyrTyrGlyGlyTyrProAspThrValTyrGluGlyLeuLysAsnAspAspThrSerLeuGlyLysGlnThrGluLysMetGluLysTyrPhe-62 |
| SEQ. ID. NO. 35812 | 65-AlaAlaAsnLysLysMetAsnAlaAlaProGlyAla-76 |
| SEQ. ID. NO. 35813 | 84-LeuSerArgSerGlyAspLysGluGlyAlaPheArgGlnPheGluGluGluLysArgLeuPheProGlu-106 |
| SEQ. ID. NO. 35814 | 115-MetLysThrGlyLysGlyGlyLysArg-123 |
| Hydrophilic Regions - Hopp-Woods | |
| SEQ. ID. NO. 35815 | 40-ValTyrGluGlyLeuLysAsnAspAspThrSerLeuGlyLysGlnThrGluLysMetGluLysTyrPhe-62 |
| SEQ. ID. NO. 35816 | 65-AlaAlaAsnLysLysMetAsnAla-72 |
| SEQ. ID. NO. 35817 | 86-ArgSerGlyAspLysGluGlyAlaPheArgGlnPheGluGluGluLysArgLeuPhePro-105 |
| SEQ. ID. NO. 35818 | 115-MetLysThrGlyLysGlyGlyLysArg-123 |
| g734 | |
| AMPHI Regions - AMPHI | |
| SEQ. ID. NO. 35819 | 26-TyrLeuAlaValTrpGlnAsnProGlnAspAlaAsnAspValLeuGlnVal-42 |
| SEQ. ID. NO. 35820 | 53-GluAlaPheAlaGluLeuGluAlaPheCysLys-63 |
| SEQ. ID. NO. 35821 | 77-ThrGlyCysArgSerValValSer-84 |
| SEQ. ID. NO. 35822 | 92-LeuAlaTyrProLysAlaLeuGlyAlaMetArg-102 |
| SEQ. ID. NO. 35823 | 113-ArgPheThrSerVal-117 |
| SEQ. ID. NO. 35824 | 121-AlaLeuAsnGlnCysIleLysLys-128 |
| Antigenic Index - Jameson-Wolf | |
| SEQ. ID. NO. 35825 | 31-GlnAsnProGlnAspAlaAsnAspValLeuGln-41 |
| SEQ. ID. NO. 35826 | 43-LysThrThrLysGluAspSerAlaLysSerGluAlaPheAlaGlu-57 |
| SEQ. ID. NO. 35827 | 60-AlaPheCysLysGlyGlnAspThr-67 |
| SEQ. ID. NO. 35828 | 71-IleAlaGluAspGluProThrGlyCysArgSer-81 |
| SEQ. ID. NO. 35829 | 101-MetArgValGluAsn-105 |
| SEQ. ID. NO. 35830 | 111-SerProArgPheThrSer-116 |
| SEQ. ID. NO. 35831 | 125-CysIleLysLysTyrGlyAlaGlnGly-133 |
| SEQ. ID. NO. 35832 | 145-SerSerTyrTyrGly-149 |
| Hydrophilic Regions - Hopp-Woods | |
| SEQ. ID. NO. 35833 | 34-GlnAspAlaAsnAsp-38 |
| SEQ. ID. NO. 35834 | 43-LysThrThrLysGluAspSerAlaLysSerGluAlaPheAlaGlu-57 |
| SEQ. ID. NO. 35835 | 60-AlaPheCysLysGlyGlnAspThr-67 |
| SEQ. ID. NO. 35836 | 71-IleAlaGluAspGluProThrGlyCys-79 |
| SEQ. ID. NO. 35837 | 101-MetArgValGluAsn-105 |
| SEQ. ID. NO. 35838 | 125-CysIleLysLysTyrGlyAla-131 |
| g736 | |
| AMPHI Regions - AMPHI | |
| SEQ. ID. NO. 35839 | 13-GlyLeuIleGlnSerPheGlySer-20 |
| SEQ. ID. NO. 35840 | 50-GlyValLeuSerVal-54 |
| SEQ. ID. NO. 35841 | 61-GlyLeuPheValGly-65 |
| SEQ. ID. NO. 35842 | 70-LeuGlnGlyTyrThrGlnLeuSerLysPheLysSerAlaAspIle-84 |
| SEQ. ID. NO. 35843 | 93-LeuLeuArgGluLeuGlyProVal-100 |
| SEQ. ID. NO. 35844 | 120-LeuMetLysThrThrGlyGlnLeuGluAlaMetAsnValMet-133 |
| SEQ. ID. NO. 35845 | 135-ValAsnProValAlaArgValVal-142 |
| SEQ. ID. NO. 35846 | 144-ProArgPheTrpAlaGlyValPheSerMetPro-154 |

TABLE 1-continued

| | |
|---|---|
| SEQ. ID. NO. 35847 | 156-LeuAlaSerIlePheAsnValAlaGlyIlePheGlyAla-168 |
| SEQ. ID. NO. 35848 | 196-AspValIleAsnGlyLeu-201 |
| SEQ. ID. NO. 35849 | 230-LeuArgAlaSerThrArgThr-236 |
| Antigenic Index - Jameson-Wolf | |
| SEQ. ID. NO. 35850 | 30-AlaLysSerGlyThrAlaPheAlaArgProArgLeuSerVal-43 |
| SEQ. ID. NO. 35851 | 77-SerLysPheLysSer-81 |
| SEQ. ID. NO. 35852 | 93-LeuLeuArgGluLeuGly-98 |
| SEQ. ID. NO. 35853 | 109-SerAlaGlyGlyAlaMetThrSer-116 |
| SEQ. ID. NO. 35854 | 186-GlnMetGlnAsnAsn-190 |
| SEQ. ID. NO. 35855 | 224-ProThrSerGluGlyIleLeuArgAlaSerThr-234 |
| Hydrophilic Regions - Hopp-Woods | |
| SEQ. ID. NO. 35856 | 37-AlaArgProArgLeuSerVal-43 |
| SEQ. ID. NO. 35857 | 77-SerLysPheLysSer-81 |
| SEQ. ID. NO. 35858 | 93-LeuLeuArgGluLeuGly-98 |
| g737 | |
| AMPHI Regions - AMPHI | |
| SEQ. ID. NO. 35859 | 56-AlaAlaTrpAlaArgValGlyGly-63 |
| Antigenic Index - Jameson-Wolf | |
| SEQ. ID. NO. 35860 | 24-AlaHisHisAspGlyHisGlyAspAspAspHisGlyHis-36 |
| SEQ. ID. NO. 35861 | 38-AlaHisGlnHisGlyLysGlnAspLysIleIleSer-49 |
| SEQ. ID. NO. 35862 | 51-AlaGlnAlaGluLysAlaAla-57 |
| SEQ. ID. NO. 35863 | 60-ArgValGlyGlyLysIleThrAspIleAspLeuGluHisAspAspGlyArgProHisTyrAspValGluIleValLysAsnGlyGlnGluTyr-90 |
| SEQ. ID. NO. 35864 | 94-ValAspAlaArgThrGlyArgValIleSerSerArgArgAspAsp-108 |
| Hydrophilic Regions - Hopp-Woods | |
| SEQ. ID. NO. 35865 | 27-AspGlyHisGlyAspAspAspHisGlyHis-36 |
| SEQ. ID. NO. 35866 | 40-GlnHisGlyLysGlnAspLysIleIleSer-49 |
| SEQ. ID. NO. 35867 | 51-AlaGlnAlaGluLysAlaAla-57 |
| SEQ. ID. NO. 35868 | 61-ValGlyGlyLysIleThrAspIleAspLeuGluHisAspAspGlyArgProHisTyr-79 |
| SEQ. ID. NO. 35869 | 82-GluIleValLysAsnGlyGlnGluTyr-90 |
| SEQ. ID. NO. 35870 | 94-ValAspAlaArgThrGlyArg-100 |
| SEQ. ID. NO. 35871 | 102-IleSerSerArgArgAspAsp-108 |
| g738 | |
| AMPHI Regions - AMPHI | |
| SEQ. ID. NO. 35872 | 91-LeuMetAsnLeuIleTyrProGlyMetAsnAspIleAla-103 |
| SEQ. ID. NO. 35873 | 139-IleGlySerLeuLeuGlnSerCysIle-147 |
| SEQ. ID. NO. 35874 | 201-LysIleProAlaAlaLeu-206 |
| SEQ. ID. NO. 35875 | 228-ThrTyrIleAlaAlaIleAlaLeuIle-236 |
| SEQ. ID. NO. 35876 | 271-AlaIleLeuGluThrPheThrGlyIle-279 |
| SEQ. ID. NO. 35877 | 285-ValGluArgValAlaAsnGlyGlyPheThrAspLeuProArgGlnSer-300 |
| SEQ. ID. NO. 35878 | 304-LysAlaLeuAlaAlaPheGlnSer-311 |
| SEQ. ID. NO. 35879 | 316-GlyHisGlyTrpAsnSerPheAla-323 |
| SEQ. ID. NO. 35880 | 338-AspAsnPheLeuSerThrLeuPheThr-346 |
| SEQ. ID. NO. 35881 | 353-LeuGlnLeuLeuAlaGlu-358 |
| SEQ. ID. NO. 35882 | 371-LeuLeuThrGlyIleAlaGlyLeuLeuLysArg-381 |
| SEQ. ID. NO. 35883 | 398-MetCysHisSerMetLeu-403 |
| SEQ. ID. NO. 35884 | 461-ArgLeuValAsnSerPheSerPro-468 |
| SEQ. ID. NO. 35885 | 472-AspSerAlaLysThrLeuAsnArgLys-480 |
| SEQ. ID. NO. 35886 | 482-AsnGluLeuArgTyrIleSer-488 |
| SEQ. ID. NO. 35887 | 507-LeuProGluTyrProGluThr-513 |
| SEQ. ID. NO. 35888 | 549-AlaLysGlnTrpMetArgAlaThr-556 |
| SEQ. ID. NO. 35889 | 567-TyrAlaAspGluIleArgLysLeuProVal-576 |
| SEQ. ID. NO. 35890 | 579-ProLeuLeuProGluLeuLeuLysAspCysLysAlaPheAlaAlaAlaPro-595 |
| Antigenic Index - Jameson-Wolf | |
| SEQ. ID. NO. 35891 | 5-ThrThrValSerGlyAlaArgProAlaAla-14 |
| SEQ. ID. NO. 35892 | 37-ArgLeuLysProSerProAspPheTyr-45 |
| SEQ. ID. NO. 35893 | 62-AlaGlyLysLysLeuPheAsp-68 |
| SEQ. ID. NO. 35894 | 124-TyrGlyGlnGluArgIle-129 |
| SEQ. ID. NO. 35895 | 167-HisArgGlyGlnGly-171 |
| SEQ. ID. NO. 35896 | 176-IleGlyGlnArgAsnAsnLeuGly-183 |
| SEQ. ID. NO. 35897 | 196-LeuAsnGlyGlnArgLysIlePro-203 |
| SEQ. ID. NO. 35898 | 242-PheArgSerAspLysSerAsnArgArgThrMet-252 |
| SEQ. ID. NO. 35899 | 283-ThrAlaValGluArgValAlaAsnGlyGlyPheThrAspLeuProArgGlnSerGluTrpAsn-303 |
| SEQ. ID. NO. 35900 | 316-GlyHisGlyTrpAsnSerPheAla-323 |
| SEQ. ID. NO. 35901 | 335-ThrIleHisAspAsnPhe-340 |
| SEQ. ID. NO. 35902 | 378-LeuLeuLysArgSerLeuThrProAlaSer-387 |
| SEQ. ID. NO. 35903 | 424-ProAlaGluAlaSerAspGlyIleAlaPheLysLysAlaAla-437 |
| SEQ. ID. NO. 35904 | 467-SerProAlaAlaAspAspSerAlaLysThrLeuAsnArgLysIleAsnGlu-483 |
| SEQ. ID. NO. 35905 | 508-ProGluTyrProGluThrGlnThrTrpAlaGlu-518 |
| SEQ. ID. NO. 35906 | 525-LeuLysTyrArgProTyrSerAla-532 |
| SEQ. ID. NO. 35907 | 542-ArgGlnGlyLysValAlaGluAlaLysGlnTrpMet-553 |
| SEQ. ID. NO. 35908 | 555-AlaThrGlnSerTyr-559 |
| SEQ. ID. NO. 35909 | 566-ArgTyrAlaAspGluIleArgLys-573 |
| SEQ. ID. NO. 35910 | 584-LeuLeuLysAspCysLysAla-590 |
| SEQ. ID. NO. 35911 | 595-ProGlyHisProGluThrLysProCysLys-604 |
| Hydrophilic Regions - Hopp-Woods | |
| SEQ. ID. NO. 35912 | 5-ThrThrValSerGlyAlaArgProAlaAla-14 |
| SEQ. ID. NO. 35913 | 38-LeuLysProSerPro-42 |
| SEQ. ID. NO. 35914 | 62-AlaGlyLysLysLeuPheAsp-68 |
| SEQ. ID. NO. 35915 | 125-GlyGlnGluArgIle-129 |
| SEQ. ID. NO. 35916 | 177-GlyGlnArgAsnAsn-181 |

TABLE 1-continued

| | |
|---|---|
| SEQ. ID. NO. 35917 | 198-GlyGlnArgLysIlePro-203 |
| SEQ. ID. NO. 35918 | 243-ArgSerAspLysSerAsnArgArgThrMet-252 |
| SEQ. ID. NO. 35919 | 283-ThrAlaValGluArgValAla-289 |
| SEQ. ID. NO. 35920 | 295-AspLeuProArgGlnSerGluTrpAsn-303 |
| SEQ. ID. NO. 35921 | 378-LeuLeuLysArgSerLeuThr-384 |
| SEQ. ID. NO. 35922 | 425-AlaGluAlaSerAsp-429 |
| SEQ. ID. NO. 35923 | 431-IleAlaPheLysLysAlaAla-437 |
| SEQ. ID. NO. 35924 | 468-ProAlaAlaAspAspSerAlaLysThrLeuAsnArgLysIleAsnGlu-483 |
| SEQ. ID. NO. 35925 | 542-ArgGlnGlyLysValAlaGluAlaLysGlnTrpMet-553 |
| SEQ. ID. NO. 35926 | 566-ArgTyrAlaAspGluIleArgLys-573 |
| SEQ. ID. NO. 35927 | 584-LeuLeuLysAspCysLysAla-590 |
| SEQ. ID. NO. 35928 | 596-GlyHisProGluThrLysProCysLys-604 |
| g739 | |
| AMPHI Regions - AMPHI | |
| SEQ. ID. NO. 35929 | 6-AsnLysProPheArgLeu-11 |
| SEQ. ID. NO. 35930 | 53-HisThrAspSerPro-57 |
| SEQ. ID. NO. 35931 | 88-GlnProAspGlyThrGlu-93 |
| SEQ. ID. NO. 35932 | 116-AspAlaAlaArgAlaAlaAspSerLeuThrGlyThr-127 |
| SEQ. ID. NO. 35933 | 131-AlaGluAsnThrLeu-135 |
| Antigenic Index - Jameson-Wolf | |
| SEQ. ID. NO. 35934 | 1-MetAlaLysLysProAsnLysProPheArgLeuThrPro-13 |
| SEQ. ID. NO. 35935 | 39-PheAsnProAsnGlyAspLysThrLeuGlnThrGluProGlnHisThrAspSerProArgGluThrGluPhe-62 |
| SEQ. ID. NO. 35936 | 64-LeuProAsnGlyAlaValGlyGlnAspAlaAlaGlnProGluHisHisHis-80 |
| SEQ. ID. NO. 35937 | 82-AlaSerSerGluProAlaGlnProAspGlyThrGluGluSerGlySerGlyLeuProSerProAlaAlaProLysLys AsnArgValLysProArgProSerAspAlaAlaArgAlaAlaAspSerLeuThrGlyThrGlyThrGlnAlaGluAsnThrLeuLysGluThrPro Val-140 |
| SEQ. ID. NO. 35938 | 142-ProThrAsnAlaProHisProGluProArgLysGluThrProGluLysGlnAlaGlnProLysGluThrProLysGluLysGluThrProLysGlu AsnHisThrLysProAspThrProLysAsnThrProAlaLysProHisLysGluIleLeu-193 |
| Hydrophilic Regions - Hopp-Woods | |
| SEQ. ID. NO. 35939 | 1-MetAlaLysLysProAsnLysProPheArgLeu-11 |
| SEQ. ID. NO. 35940 | 41-ProAsnGlyAspLysThrLeuGlnThrGluProGlnHisThrAspSerProArgGluThrGlu-61 |
| SEQ. ID. NO. 35941 | 69-ValGlyGlnAspAlaAlaGlnProGluHisHisHis-80 |
| SEQ. ID. NO. 35942 | 82-AlaSerSerGluProAlaGlnProAspGlyThrGluGluSerGlySer-97 |
| SEQ. ID. NO. 35943 | 103-AlaAlaProLysLysAsnArgValLysProArgProSerAspAlaAlaArgAlaAlaAspSerLeuThr-125 |
| SEQ. ID. NO. 35944 | 129-ThrGlnAlaGluAsnThrLeuLysGluThrPro-139 |
| SEQ. ID. NO. 35945 | 146-ProHisProGluProArgLysGluThrProGluLysGlnAlaGlnProLysGluThrProLysGluLysGluThrProLysGluAsnHisThrLys ProAspThrProLysAsnThrProAlaLysProHisLysGluIleLeu-193 |
| g740 | |
| AMPHI Regions - AMPHI | |
| SEQ. ID. NO. 35946 | 6-LeuValArgTrpLeuAlaVal-12 |
| SEQ. ID. NO. 35947 | 57-IleLysHisHisLeu-61 |
| Antigenic Index - Jameson-Wolf | |
| SEQ. ID. NO. 35948 | 25-AlaAsnProProGluAspLysProGln-33 |
| SEQ. ID. NO. 35949 | 57-IleLysHisHisLeu-61 |
| SEQ. ID. NO. 35950 | 63-GlnGlyPheAspLeuLysArgGlnThr-71 |
| Hydrophilic Regions - Hopp-Woods | |
| SEQ. ID. NO. 35951 | 27-ProProGluAspLysProGln-33 |
| SEQ. ID. NO. 35952 | 57-IleLysHisHisLeu-61 |
| SEQ. ID. NO. 35953 | 63-GlnGlyPheAspLeuLysArgGlnThr-71 |
| g741 | |
| AMPHI Regions - AMPHI | |
| SEQ. ID. NO. 35954 | 35-GlyThrGlyLeuAlaAspAlaLeuThrAla-44 |
| SEQ. ID. NO. 35955 | 74-GlyAlaGluLysThrPheLysAlaGly-82 |
| SEQ. ID. NO. 35956 | 138-LysIleAsnAsnProAspLysIleAspSerLeuIle-149 |
| SEQ. ID. NO. 35957 | 164-ThrAlaPheAsnGlnLeuProAsp-171 |
| SEQ. ID. NO. 35958 | 205-IleGluHisLeuLys-209 |
| Antigenic Index - Jameson-Wolf | |
| SEQ. ID. NO. 35959 | 1-ValAsnArgThrThrPhe-6 |
| SEQ. ID. NO. 35960 | 12-ThrAlaGlyProAspSerAspArgLeuGlnGlnArgArgGlyGlyGlyGlyGlyVal-30 |
| SEQ. ID. NO. 35961 | 46-LeuAspHisLysAspLysGlyLeuLys-54 |
| SEQ. ID. NO. 35962 | 61-SerIleProGlnAsnGly-66 |
| SEQ. ID. NO. 35963 | 73-GlnGlyAlaGluLysThrPheLysAlaGlyGlyLysAspAsnSerLeuAsnThrGlyLysLeuLysAsnAspLysIleSerArg-100 |
| SEQ. ID. NO. 35964 | 107-IleGluValAspGlyGln-112 |
| SEQ. ID. NO. 35965 | 123-IleTyrLysGlnAspHisSerAla-130 |
| SEQ. ID. NO. 35966 | 135-ArgIleGluLysIleAsnAsnProAspLysIleAspSer-147 |
| SEQ. ID. NO. 35967 | 149-IleAsnGlnArgSer-153 |
| SEQ. ID. NO. 35968 | 157-SerAspLeuGlyGlyGluHisThr-164 |
| SEQ. ID. NO. 35969 | 168-GlnLeuProAspGlyLysAlaGluTyrHisGly-178 |
| SEQ. ID. NO. 35970 | 180-AlaPheSerSerAspAspAlaAspGlyLysLeu-190 |
| SEQ. ID. NO. 35971 | 196-PheAlaAlaLysGlnGlyHisGlyLysIleGluHisLeuLysThrProGluGlnAsnVal-215 |
| SEQ. ID. NO. 35972 | 218-AlaSerAlaGluLeuLysAlaAspGluLysSerHis-229 |
| SEQ. ID. NO. 35973 | 234-GlyAspThrArgTyrGlyGlyGluGluLysGlyThrTyrArg-247 |
| SEQ. ID. NO. 35974 | 251-PheGlyAspArgAlaGlnGluIleAlaGly-260 |
| SEQ. ID. NO. 35975 | 265-LysIleGlyGluLysValHisGlu-272 |
| SEQ. ID. NO. 35976 | 274-GlyIleAlaAspLysGln-279 |
| Hydrophilic Regions - Hopp-Woods | |
| SEQ. ID. NO. 35977 | 13-AlaGlyProAspSerAspArgLeuGlnGlnArgArgGlyGlyGly-27 |
| SEQ. ID. NO. 35978 | 46-LeuAspHisLysAspLysGlyLeuLys-54 |
| SEQ. ID. NO. 35979 | 73-GlnGlyAlaGluLysThrPheLysAlaGlyGlyLysAspAsnSerLeuAsn-89 |
| SEQ. ID. NO. 35980 | 91-GlyLysLeuLysAsnAspLysIleSerArg-100 |

TABLE 1-continued

| | |
|---|---|
| SEQ. ID. NO. 35981 | 107-IleGluValAspGly-111 |
| SEQ. ID. NO. 35982 | 135-ArgIleGluLysIleAsnAsnProAspLysIleAspSer-147 |
| SEQ. ID. NO. 35983 | 170-ProAspGlyLysAlaGluTyrHisGly-178 |
| SEQ. ID. NO. 35984 | 180-AlaPheSerSerAspAspAlaAspGlyLysLeu-190 |
| SEQ. ID. NO. 35985 | 200-GlnGlyHisGlyLysIleGluHisLeuLysThrProGluGlnAsnVal-215 |
| SEQ. ID. NO. 35986 | 218-AlaSerAlaGluLeuLysAlaAspGluLysSerHis-229 |
| SEQ. ID. NO. 35987 | 236-ThrArgTyrGlyGlyGluGluLysGlyThrTyr-246 |
| SEQ. ID. NO. 35988 | 252-GlyAspArgAlaGlnGluIleAlaGly-260 |
| SEQ. ID. NO. 35989 | 265-LysIleGlyGluLysValHisGlu-272 |
| SEQ. ID. NO. 35990 | 274-GlyIleAlaAspLysGln-279 |
| g746 | |
| AMPHI Regions - AMPHI | |
| SEQ. ID. NO. 35991 | 83-ThrAlaAlaAspLysProGlnAsp-90 |
| SEQ. ID. NO. 35992 | 105-SerGluProGluAsn-109 |
| SEQ. ID. NO. 35993 | 126-IleLysGlyLeuGluGluSerGluLysLeuGlnGlnAlaGlu-139 |
| SEQ. ID. NO. 35994 | 154-GluLysValSerAlaThr-159 |
| SEQ. ID. NO. 35995 | 164-AspThrValAlaValGlu-169 |
| SEQ. ID. NO. 35996 | 171-ProLysArgThrAlaGluPro-177 |
| SEQ. ID. NO. 35997 | 181-LysAlaGluArgThr-185 |
| SEQ. ID. NO. 35998 | 195-ThrLysThrAlaGluLysValAlaAspLysProLys-206 |
| SEQ. ID. NO. 35999 | 221-SerAlaValLysGluAlaLysLysAlaAspLysAlaGluGly-234 |
| SEQ. ID. NO. 36000 | 249-GluThrAlaGlnLysThrAspLysAlaAspLysThrLysThrAlaGluLysGluLysSerGlyLysAla-271 |
| SEQ. ID. NO. 36001 | 301-SerThrIleThrGluIleMetThr-308 |
| SEQ. ID. NO. 36002 | 321-TyrLysAsnAlaArgAspAlaGluArgAspLeu-331 |
| Antigenic Index - Jameson-Wolf | |
| SEQ. ID. NO. 36003 | 1-MetSerGluAsnLysGlnAsnGlu-8 |
| SEQ. ID. NO. 36004 | 14-GluGlnLeuLysArgArgAsnArgArgArgLeuValThr-26 |
| SEQ. ID. NO. 36005 | 42-LeuSerSerAspProAlaAspSerAsnProAlaProGlnAlaGlyGluThrGlyAlaThrGluSerGlnThrAlaAsnThrAlaGln-70 |
| SEQ. ID. NO. 36006 | 76-SerAlaAlaGluAsnGlyGluThrAlaAlaAspLysProGlnAspLeuAlaGlyGluAspLysProSerAlaAlaAspSerGluIleSerGlu ProGluAsnVal-110 |
| SEQ. ID. NO. 36007 | 118-AsnAspArgLeuGluAspSerAsnIleLysGlyLeuGluGluSerGluLysLeuGlnGlnAlaGluThrAlaLysThrGluProLysGlnAla LysGlnArgAlaAlaGluLysValSerAlaThrAlaAspSerThrAspThrValAlaValGluLysProLysArgThrAlaGluProLysProGln LysAlaGluArgThrAlaGluAlaLysProLysAlaLysGluThrLysThrAlaGluLysValAlaAspLysProLysThrAlaAlaGluLysThr LysProAspThrAlaLysSerAspSerAlaValLysGluAlaLysLysAlaAspLysAlaGluGlyLysLysThrAlaGluLysAspArgSerAsp GlyLysLysHisGluThrAlaGlnLysThrAspLysAlaAspLysThrLysThrAlaGluLysGluLysSerGlyLysAlaGlyLysLysAlaAla-276 |
| SEQ. ID. NO. 36008 | 280-GlyTyrAlaGluLysGluArgAlaLeuSerLeuGlnArgLysMetLysAlaAlaGlyIle-299 |
| SEQ. ID. NO. 36009 | 306-IleMetThrAspAsnGlyLysValTyrArgValLysSerSerAsnTyrLysAsnAlaArgAspAlaGluArgAspLeuAsnLysLeuArgVal-336 |
| Hydrophilic Regions - Hopp-Woods | |
| SEQ. ID. NO. 36010 | 1-MetSerGluAsnLysGlnAsnGlu-8 |
| SEQ. ID. NO. 36011 | 14-GluGlnLeuLysArgArgAsnArgArgArgLeuVal-25 |
| SEQ. ID. NO. 36012 | 42-LeuSerSerAspProAlaAspSerAsnPro-51 |
| SEQ. ID. NO. 36013 | 54-GlnAlaGlyGluThrGlyAlaThrGluSerGlnThr-65 |
| SEQ. ID. NO. 36014 | 76-SerAlaAlaGluAsnGlyGluThrAlaAlaAspLysProGlnAspLeuAlaGlyGluAspLysProSerAlaAlaAspSerGluIleSerGluPro GluAsnVal-110 |
| SEQ. ID. NO. 36015 | 119-AspArgLeuGluAspSerAsnIleLysGlyLeuGluGluSerGluLysLeuGlnGlnAlaGluThrAlaLysThrGluProLysGlnAlaLys GlnArgAlaAlaGluLysValSerAlaThrAlaAspSerThrAsp-164 |
| SEQ. ID. NO. 36016 | 166-ValAlaValGluLysProLysArgThrAlaGluProLysProGlnLysAlaGluArgThrAlaGluAlaLysProLysAlaLysGluThrLys ThrAlaGluLysValAlaAspLysProLysThrAlaAlaGluLysThrLysProAspThrAlaLysSerAspSerAlaValLysGluAlaLysLys AlaAspLysAlaGluGlyLysLysThrAlaGluLysAspArgSerAspGlyLysLysHisGluThrAlaGlnLysThrAspLysAlaAspLysThr LysThrAlaGluLysGluLysSerGlyLysAlaGlyLysLysAlaAla-276 |
| SEQ. ID. NO. 36017 | 281-TyrAlaGluLysGluArgAlaLeuSerLeuGlnArgLysMetLysAlaAlaGlyIle-299 |
| SEQ. ID. NO. 36018 | 306-IleMetThrAspAsnGlyLysValTyrArgValLysSerSerAsnTyrLysAsnAlaArgAspAlaGluArgAspLeuAsnLysLeuArg Val-336 |
| g748 | |
| AMPHI Regions - AMPHI | |
| SEQ. ID. NO. 36019 | 22-GlyAlaIleGlyAlaIleGlyGly-29 |
| SEQ. ID. NO. 36020 | 37-GlyGluThrAlaGluArgThrAlaGluSerGlnHis-48 |
| SEQ. ID. NO. 36021 | 82-SerAlaLysGlnLeuGluAsnLeuPheArgThrLeu-93 |
| SEQ. ID. NO. 36022 | 155-LeuGlnGluMetArgAspPheProAsnAspLysLeuGlnLysSerTrp-170 |
| SEQ. ID. NO. 36023 | 188-GlnThrAlaLeuArgAspIleIleLysHisThr-198 |
| SEQ. ID. NO. 36024 | 250-GlyValAlaAlaAsnSer-255 |
| SEQ. ID. NO. 36025 | 257-AspGluProGluTrp-261 |
| SEQ. ID. NO. 36026 | 268-GlnAlaValArgLeuIleArgArgPheValGluPheTrpAspArg-282 |
| SEQ. ID. NO. 36027 | 310-GlnProAspPheAlaLysAspProGlu-318 |
| SEQ. ID. NO. 36028 | 330-LeuAlaAsnProArgAspProGlu-337 |
| SEQ. ID. NO. 36029 | 390-LeuGluGluTyrIleSerProPhe-397 |
| Antigenic Index - Jameson-Wolf | |
| SEQ. ID. NO. 36030 | 1-MetSerGlnAsnGlnProAlaGlnProThrLysArgAsnLeuPhe-15 |
| SEQ. ID. NO. 36031 | 30-TyrPheGlyGlyLysLysGlnGlyGluThrAlaGluArgThrAlaGluSerGlnHisSerProGlnAla-52 |
| SEQ. ID. NO. 36032 | 80-AlaGlnSerAlaLysGlnLeuGluAsn-88 |
| SEQ. ID. NO. 36033 | 101-ThrGlnGlyGlyGluTyrGlnAspGlyAspAspLysLeuProSerAlaGlySerGly-119 |
| SEQ. ID. NO. 36034 | 125-PheAsnProAspGlyLeuThr-131 |
| SEQ. ID. NO. 36035 | 139-SerLeuPheAspGlyArgPheGlyLeuLysAspLysLysThrValHis-154 |
| SEQ. ID. NO. 36036 | 156-GlnGluMetArgAspPheProAsnAspLysLeuGlnLysSerTrpCysAspGlyAspLeuSer-176 |
| SEQ. ID. NO. 36037 | 183-ThrProGluThrCys-187 |
| SEQ. ID. NO. 36038 | 208-IleAspGlyTrpGlnProLysSerGluProGlyAlaMetAla-221 |
| SEQ. ID. NO. 36039 | 226-LeuGlyPheArgAspGlyThrGlyAsnProLysValSerAspProLysThrAlaAspGlu-245 |
| SEQ. ID. NO. 36040 | 255-SerLeuAspGluProGluTrpAlaLysAsnGlySerTyrGlnAla-269 |
| SEQ. ID. NO. 36041 | 271-ArgLeuIleArgArgPhe-276 |

TABLE 1-continued

| | |
|---|---|
| SEQ. ID. NO. 36042 | 279-PheTrpAspArgThrProLeuGlnGluGlnThrAspIlePheGlyArgArgLysTyrSerGlyAlaProMetAspGlyLysLysGluAlaAspGln ProAspPheAlaLysAspProGluGlyAspIleThrProLysAspSerHisMetArgLeuAlaAsnProArgAspProGluPheLeuLys-340 |
| SEQ. ID. NO. 36043 | 348-AlaTyrSerTyrSerArgGlyProAlaSerSerGlyGlnLeu-361 |
| SEQ. ID. NO. 36044 | 385-LeuAsnGlyGluProLeuGluGluTyr-393 |
| SEQ. ID. NO. 36045 | 407-GlyValGlyLysGlyGlyPhe-413 |
| Hydrophilic Regions - Hopp-Woods | |
| SEQ. ID. NO. 36046 | 8-GlnProThrLysArgAsnLeuPhe-15 |
| SEQ. ID. NO. 36047 | 32-GlyGlyLysLysGlnGlyGluThrAlaGluArgThrAlaGluSerGlnHis-48 |
| SEQ. ID. NO. 36048 | 80-AlaGlnSerAlaLysGlnLeuGluAsn-88 |
| SEQ. ID. NO. 36049 | 104-GlyGluTyrGlnAspGlyAspAspLysLeuProSer-115 |
| SEQ. ID. NO. 36050 | 145-PheGlyLeuLysAspLysLysThrValHis-154 |
| SEQ. ID. NO. 36051 | 156-GlnGluMetArgAspPheProAsnAspLysLeuGlnLysSerTrpCysAspGlyAspLeu-175 |
| SEQ. ID. NO. 36052 | 211-TrpGlnProLysSerGluProGlyAlaMetAla-221 |
| SEQ. ID. NO. 36053 | 229-ArgAspGlyThrGlyAsnProLysValSerAspProLysThrAlaAsp-244 |
| SEQ. ID. NO. 36054 | 255-SerLeuAspGluProGluTrpAlaLys-263 |
| SEQ. ID. NO. 36055 | 271-ArgLeuIleArgArgPhe-276 |
| SEQ. ID. NO. 36056 | 283-ThrProLeuGlnGluGlnThrAspIlePheGlyArgArgLysTyrSer-298 |
| SEQ. ID. NO. 36057 | 301-ProMetAspGlyLysLysGluAlaAspGlnProAspPheAlaLysAspProGluGlyAspIleThrProLyAspSerHisMet-328s |
| SEQ. ID. NO. 36058 | 331-AlaAsnProArgAspProGluPheLeuLys-340 |
| SEQ. ID. NO. 36059 | 353-ArgGlyProAlaSer-357 |
| SEQ. ID. NO. 36060 | 388-GluProLeuGluGluTyr-393 |
| g749 | |
| AMPHI Regions - AMPHI | |
| SEQ. ID. NO. 36061 | 1-MetArgLysPheAsnLeuThrAlaLeuSerValMetLeuAlaLeuGlyLeuThrAlaCysGlnProProGluAlaGluLysAlaAlaProAla AlaSerGlyGluThrGlnSerAlaAsnGluGlyGlySerValGlyIleAlaValAsnAspAsnAlaCysGluProMetAsnLeuThrValProSer GlyGlnValValPheAsnIleLysAsnAsnSerGlyArgLysLeuGluTrpGluIleLeuLysGlyValMetValValAspGluArgGluAsnIle AlaProGlyLeuSerAspLysMetThrValThrLeuLeuProGlyGluTyrGluMetThrCysGlyLeuLeuThrAsnProArgGlyLysLeuVal ValAlaAspSerGlyPheLysAspThrAlaAsnGluAlaAspLeuGluLysLeuProGlnProLeuAlaAspTyrLysAlaTyrValGlnGly GluValLysGluLeuAlaAlaLysThrLysThrPheThrGluAlaValLysAlaGlyAspIleGluLysAlaLysSerLeuPheAlaAlaThrArgVal HisTyrGluArgIleGluProIleAlaGluLeuPheSerGluLeuAspProValIleAspAlaCysGluAspAspPheLysAspGlyAlaLysAspAla GlyPheThrGlyPheHisArgIleGluHisAlaLeuTrpValGluLysAspValSerGlyValLysGluThrAlaAlaLysLeuMetThrAspValGlu AlaLeuGlnLysGluIleAspAlaLeuAlaPheProProGlyLysValValGlyGlyAlaSerGluLeuIleGluGluAlaAlaGlySerLysIleSerGly GluGluAspArgTyrSerHisThrAspLeuSerAspPheGlnAlaAsnAlaAspGlySerLysLysIleValAspLeuPheArgProLeuIleGlu AlaLysAsnLysAlaLeuLeuGluLysThrAspThrAsnPheLysGlnValAsnGluIleLeuAlaLysTyrArgThrLysAspGlyPheGluThrTyr AspLysLeuSerGluAlaAspArgLysAlaLeuGlnAlaProIleAsnAlaLeuAlaGluAspLeuAlaGlnLeuArgGlyIleLeuGlyLeuLys-388 |

Antigenic Index - Jameson-Wolf
(SEQ. ID. NO. 36061)
1-MetArgLysPheAsnLeuThrAlaLeuSerValMetLeuAlaLeuGlyLeuThrAlaCysGlnProProGluAlaGluLysAlaAlaProAlaAlaSerGlyGluThrGlnSerAlaAsn GluGlyGlySerValGlyIleAlaValAsnAspAsnAlaCysGluProMetAsnLeuThrValProSerGlyGlnValValPheAsnIleLysAsnAsnSerGlyArgLysLeuGluTrp GluIleLeuLysGlyValMetValValAspGluArgGluAsnIleAlaProGlyLeuSerAspLysMetThrValThrLeuLeuProGlyGluTyrGluMetThrCysGlyLeuLeuThr AsnProArgGlyLysLeuValValAlaAspSerGlyPheLysAspThrAlaAsnGluAlaAspLeuGluLysLeuProGlnProLeuAlaAspTyrLysAlaTyrValGlnGlyGluVal LysGluLeuAlaAlaLysThrLysThrPheThrGluAlaValLysAlaGlyAspIleGluLysAlaLysSerLeuPheAlaAlaThrArgValHisTyrGluArgIleGluProIleAlaGlu LeuPheSerGluLeuAspProValIleAspAlaCysGluAspAspPheLysAspGlyAlaLysAspAlaGlyPheThrGlyPheHisArgIleGluHisAlaLeuTrpValGluLysAsp ValSerGlyValLysGluThrAlaAlaLysLeuMetThrAspValGluAlaLeuGlnLysGluIleAspAlaLeuAlaPheProProGlyLysValValGlyGlyAlaSerGluLeuIle GluGluAlaAlaGlySerLysIleSerGlyGluGluAspArgTyrSerHisThrAspLeuSerAspPheGlnAlaAsnAlaAspGlySerLysLysIleValAspLeuPheArgProLeu IleGluAlaLysAsnLysAlaLeuLeuGluLysThrAspThrAsnPheLysGlnValAsnGluIleLeuAlaLysTyrArgThrLysAspGlyPheGluThrTyrAspLysLeuSerGlu AlaAspArgLysAlaLeuGlnAlaProIleAsnAlaLeuAlaGluAspLeuAlaGlnLeuArgGlyIleLeuGlyLeuLys-388

Hydrophilic Regions - Hopp-Woods
(SEQ. ID. NO. 36061)
1-MetArgLysPheAsnLeuThrAlaLeuSerValMetLeuAlaLeuGlyLeuThrAlaCysGlnProProGluAlaGluLysAlaAlaProAlaAlaSerGlyGluThrGlnSerAla AsnGluGlyGlySerValGlyIleAlaValAsnAspAsnAlaCysGluProMetAsnLeuThrValProSerGlyGlnValValPheAsnIleLysAsnAsnSerGlyArgLysLeu GluTrpGluIleLeuLysGlyValMetValValAspGluArgGluAsnIleAlaProGlyLeuSerAspLysMetThrValThrLeuLeuProGlyGluTyrGluMetThrCysGly LeuLeuThrAsnProArgGlyLysLeuValValAlaAspSerGlyPheLysAspThrAlaAsnGluAlaAspLeuGluLysLeuProGlnProLeuAlaAspTyrLysAlaTyr ValGlnGlyGluValLysGluLeuAlaAlaLysThrLysThrPheThrGluAlaValLysAlaGlyAspIleGluLysAlaLysSerLeuPheAlaAlaThrArgValHisTyrGlu ArgIleGluProIleAlaGluLeuPheSerGluLeuAspProValIleAspAlaCysGluAspAspPheLysAspGlyAlaLysAspAlaGlyPheThrGlyPheHisArgIleGlu HisAlaLeuTrpValGluLysAspValSerGlyValLysGluThrAlaAlaLysLeuMetThrAspValGluAlaLeuGlnLysGluIleAspAlaLeuAlaPheProProGlyLys ValValGlyGlyAlaSerGluLeuIleGluGluAlaAlaGlySerLysIleSerGlyGluGluAspArgTyrSerHisThrAspLeuSerAspPheGlnAlaAsnAlaAspGlySerLys LysIleValAspLeuPheArgProLeuIleGluAlaLysAsnLysAlaLeuLeuGluLysThrAspThrAsnPheLysGlnValAsnGluIleLeuAlaLysTyrArgThrLysAsp GlyPheGluThrTyrAspLysLeuSerGluAlaAspArgLysAlaLeuGlnAlaProIleAsnAlaLeuAlaGluAspLeuAlaGlnLeuArgGlyIleLeuGlyLeuLys-388

| | |
|---|---|
| g750 | |
| AMPHI Regions - AMPHI | |
| SEQ. ID. NO. 36062 | 1-ValLysProArgPheTyrTrpAlaAlaCysAlaValLeuProAlaAlaCysSerProGluProAlaAlaGluLysThrVal SerAlaAlaSerGlnAlaAlaSerThrProValAlaThrLeuThrValProThrAlaArgGlyAspAlaValValProLysAsnProGluArgValAlaVal TyrAspTrpAlaAlaLeuAspThrLeuThrGluProGlyValAsnValGlyAlaThrThrAlaProValArgValAspTyrLeuGlnProAlaPheAsp LysAlaAlaThrValGlyThrLeuPheGluProAspCysGluSerLeuHisArgHisAsnProGlnPheValIleThrGlyGlyProGlyAlaGluAlaTyr GluGlnLeuAlaLysAsnAlaThrThrIleAspLeuThrValAspAsnGlyAsnIleArgThrSerGlyGluLysGlnMetGluThrLeuSerArgIlePhe GlyLysGluAlaArgValAlaGluLeuAsnAlaGlnIleAspAlaLeuPheAlaGlnLysArgGluAlaAlaLysGlyLysGlyArgGlyLeuValLeu SerValThrGlyAsnLysValSerAlaPheGlyThrGlnSerArgLeuAlaSerTrpIleHisGlyAspIleGlyLeuProProValAspGluSerLeuArg AsnGluGlyHisGlyGlnProValSerPheGluTyrIleLysGluLysAsnProGlyTrpIlePheIleIleAspArgThrAlaAlaIleGlyGlnGluGlyPro AlaAlaValGluValLeuAspAsnAlaLeuValCysGlyThrAsnAlaTrpLysArgLysGlnIleIleValMetProAlaAlaAsnTyrIleValAlaGly GlyAlaArgGlnLeuIleGlnAlaAlaGluGlnLeuLysAlaAlaPheGluLysAlaGluProValAlaAlaGln-323 |

Antigenic Index - Jameson-Wolf
(SEQ. ID. NO. 36062)
1-ValLysProArgPheTyrTrpAlaAlaCysAlaValLeuProAlaAlaCysSerProGluProAlaAlaGluLysThrValSerAlaAlaSerGlnAlaAlaSerThrProValAlaThrLeu ThrValProThrAlaArgGlyAspAlaValValProLysAsnProGluArgValAlaValTyrAspTrpAlaAlaLeuAspThrLeuThrGluProGlyValAsnValGlyAlaThrThr AlaProValArgValAspTyrLeuGlnProAlaPheAspLysAlaAlaThrValGlyThrLeuPheGluProAspCysGluSerLeuHisArgHisAsnProGlnPheValIleThrGly GlyProGlyAlaGluAlaTyrGluGlnLeuAlaLysAsnAlaThrThrIleAspLeuThrValAspAsnGlyAsnIleArgThrSerGlyGluLysGlnMetGluThrLeuSerArgIle PheGlyLysGluAlaArgValAlaGluLeuAsnAlaGlnIleAspAlaLeuPheAlaGlnLysArgGluAlaAlaLysGlyLysGlyArgGlyLeuValLeuSerValThrGlyAsnLys ValSerAlaPheGlyThrGlnSerArgLeuAlaSerTrpIleHisGlyAspIleGlyLeuProProValAspGluSerLeuArgAsnGluGlyHisGlyGlnProValSerPheGluTyrIle LysGluLysAsnProGlyTrpIlePheIleIleAspArgThrAlaAlaIleGlyGlnGluGlyProAlaAlaValGluValLeuAspAsnAlaLeuValCysGlyThrAsnAlaTrpLysArg TABLE 1-continued LysGlnIleIleValMetProAlaAlaAsnTyrIleValAlaGlyGlyAlaArgGlnLeuIleGlnAlaAlaGluGlnLeuLysAlaAlaPheGluLysAlaGluProValAlaAlaGln-323
Hydrophilic Regions - Hopp-Woods
(SEQ. ID. NO. 36062)
1-ValLysProArgPheTyrTrpAlaAlaCysAlaValLeuProAlaAlaCysSerProGluProAlaAlaGluLysThrValSerAlaAlaSerGlnAlaAlaSerThrProValAlaThr
LeuThrValProThrAlaArgGlyAspAlaValValProLysAsnProGluArgValAlaValTyrAspTrpAlaAlaLeuAspThrLeuThrGluProGlyValAsnValGlyAla
ThrThrAlaProValArgValAspTyrLeuGlnProAlaPheAspLysAlaAlaThrValGlyThrLeuPheGluProAspCysGluSerLeuHisArgHisAsnProGlnPheVal
IleThrGlyGlyProGlyAlaGluAlaTyrGluGlnLeuAlaLysAsnAlaThrThrIleAspLeuThrValAspAsnGlyAsnIleArgThrSerGlyGluLysGlnMetGluThr
LeuSerArgIlePheGlyLysGluAlaArgValAlaGluLeuAsnAlaGlnIleAspAlaLeuPheAlaGlnLysArgGluAlaAlaLysGlyLysGlyArgGlyLeuValLeuSer
ValThrGlyAsnLysValSerAlaPheGlyThrGlnSerArgLeuAlaSerTrpIleHisGlyAspIleGlyLeuProProValAspGluSerLeuArgAsnGluGlyHisGlyGln
ProValSerPheGluTyrIleLysGluLysAsnProGlyTrpIlePheIleIleAspArgThrAlaAlaIleGlyGlnGluGlyProAlaAlaValGluValLeuAspAsnAlaLeuVal
CysGlyThrAsnAlaTrpLysArgLysGlnIleIleValMetProAlaAlaAsnTyrIleValAlaGlyGlyAlaArgGlnLeuIleGlnAlaAlaGluGlnLeuLysAlaAlaPhe
GluLysAlaGluProValAlaAlaGln-323
g760
AMPHI Regions - AMPHI
SEQ. ID. NO. 36063 1-AsnAsnArgAsnThrArgTyrAlaAlaLeuGlyLysArgValMetGluGlyValGluThrGluIleSerGlyAlaIleThrProLysTrpGln
IleHisAlaGlyTyrSerTyrLeuHisSerGlnIleLysThrAlaAlaAsnProArgAspAspGlyIlePheLeuLeuValProLysHisSerAla
AsnLeuTrpThrThrTyrGlnValThrProGlyLeuThrValGlyGlyGlyValAsnAlaMetSerGlyIleThrSerSerAlaGlyMetHisAla
GlyGlyTyrAlaThrPheAspAlaMetAlaAlaTyrArgPheThrProLysLeuLysLeuGlnIleAsnAlaAspAsnIlePheAsnArgHis
TyrTyrAlaArgValGlyGlyThrAsnThrPheAsnIleProGlySerGluArgSerLeuThrAlaAsnLeuArgTyrSerPhe-154
Antigenic Index - Jameson-Wolf
(SEQ. ID. NO. 36063)
1-AsnAsnArgAsnThrArgTyrAlaAlaLeuGlyLysArgValMetGluGlyValGluThrGluIleSerGlyAlaIleThrProLysTrpGlnIleHisAlaGlyTyrSerTyrLeuHis
SerGlnIleLysThrAlaAlaAsnProArgAspAspGlyIlePheLeuLeuValProLysHisSerAlaAsnLeuTrpThrThrTyrGlnValThrProGlyLeuThrValGlyGlyGly
ValAsnAlaMetSerGlyIleThrSerSerAlaGlyMetHisAlaGlyGlyTyrAlaThrPheAspAlaMetAlaAlaTyrArgPheThrProLysLeuLysLeuGlnIleAsnAla
AspAsnIlePheAsnArgHisTyrTyrAlaArgValGlyGlyThrAsnThrPheAsnIleProGlySerGluArgSerLeuThrAlaAsnLeuArgTyrSerPhe-154
Hydrophilic Regions - Hopp-Woods
(SEQ. ID. NO. 36063)
1-AsnAsnArgAsnThrArgTyrAlaAlaLeuGlyLysArgValMetGluGlyValGluThrGluIleSerGlyAlaIleThrProLysTrpGlnIleHisAlaGlyTyrSerTyrLeu
HisSerGlnIleLysThrAlaAlaAsnProArgAspAspGlyIlePheLeuLeuValProLysHisSerAlaAsnLeuTrpThrThrTyrGlnValThrProGlyLeuThrValGly
GlyGlyValAsnAlaMetSerGlyIleThrSerSerAlaGlyMetHisAlaGlyGlyTyrAlaThrPheAspAlaMetAlaAlaTyrArgPheThrProLysLeuLysLeuGlnIleAsn
AlaAspAsnIlePheAsnArgHisTyrTyrAlaArgValGlyGlyThrAsnThrPheAsnIleProGlySerGluArgSerLeuThrAlaAsnLeuArgTyrSerPhe-154
g767
AMPHI Regions - AMPHI
SEQ. ID. NO. 36064 41-GlyLysIleGluValLeuGluPhePheGlyTyrPheCysVal-54
SEQ. ID. NO. 36065 89-GlyLeuAlaArgMetAlaAlaAlaValLys-98
SEQ. ID. NO. 36066 140-LysLysLeuMetArgAlaTyrAspSerProGlu-150
SEQ. ID. NO. 36067 160-LysLeuThrGluGlnTyr-165
SEQ. ID. NO. 36068 187-PheAspGlyGlyValHisThrIleLysGluLeuValAla-199
Antigenic Index - Jameson-Wolf
SEQ. ID. NO. 36069 23-ThrGluGlyGluAspTyrLeuVal-30
SEQ. ID. NO. 36070 32-AspLysProIleProGlnGluGlnProGlyLysIleGluVal-45
SEQ. ID. NO. 36071 66-LeuGlyLysAlaLeuProSerAspThrTyrLeuArg-77
SEQ. ID. NO. 36072 99-LeuSerGlyLeuLysTyrGlnAla-106
SEQ. ID. NO. 36073 115-TyrGluGlnLysIleArgLeuGluAsnArgAlaValAla-127
SEQ. ID. NO. 36074 132-LeuSerGlnLysGlyPheAspGlyLysLysLeuMetArgAlaTyrAspSerProGluAla-151
SEQ. ID. NO. 36075 157-LysMetGlnLysLeuThrGluGlnTyrGlyIleAspSerThrPro-171
SEQ. ID. NO. 36076 175-ValGlyGlyLysTyrArgVal-181
SEQ. ID. NO. 36077 183-PheAsnAsnGlyPheAspGlyGly-190
SEQ. ID. NO. 36078 197-LeuValAlaLysValArgGluGluArgLysArgGlnThrProAlaValGlnLys-214
Hydrophilic Regions - Hopp-Woods
SEQ. ID. NO. 36079 23-ThrGluGlyGluAsp-27
SEQ. ID. NO. 36080 33-LysProIleProGlnGluGlnProGlyLysIleGluVal-45
SEQ. ID. NO. 36081 115-TyrGluGlnLysIleArgLeuGluAsnArgAlaValAla-127
SEQ. ID. NO. 36082 135-LysGlyPheAspGlyLysLysLeuMetArgAlaTyrAspSerProGluAla-151
SEQ. ID. NO. 36083 157-LysMetGlnLysLeuThrGlu-163
SEQ. ID. NO. 36084 197-LeuValAlaLysValArgGluGluArgLysArgGlnThrProAlaValGlnLys-214
g768
AMPHI Regions - AMPHI
SEQ. ID. NO. 36085 1-MetAsnIleLysGlnLeuIleThrAlaAlaLeuIleAlaSerAlaAlaPheAlaThrGlnAlaAlaProGlnLysProValSerAlaAlaGlnThr
AlaGlnHisSerAlaValTrpIleAspValArgSerGluGlnGluPheSerGluGlyHisLeuHisAsnAlaValAsnIleProValAspGlnIle
ValArgArgIleTyrGluAlaAlaProAspLysAspThrProValAsnLeuTyrCysArgSerGlyArgArgAlaGluAlaAlaLeuGlnGlu
LeuLysLysAlaGlyTyrThrAsnValAlaAsnHisGlyGlyTyrGluAspLeuLeuLysLysGlyMetLys-119
Antigenic Index - Jameson-Wolf
(SEQ. ID. NO. 36085)
1-MetAsnIleLysGlnLeuIleThrAlaAlaLeuIleAlaSerAlaAlaPheAlaThrGlnAlaAlaProGlnLysProValSerAlaAlaGlnThrAlaGlnHisSerAlaValTrpIle
AspValArgSerGluGlnGluPheSerGluGlyHisLeuHisAsnAlaValAsnIleProValAspGlnIleValArgArgIleTyrGluAlaAlaProAspLysAspThrProValAsn
LeuTyrCysArgSerGlyArgArgAlaGluAlaAlaLeuGlnGluLeuLysLysAlaGlyTyrThrAsnValAlaAsnHisGlyGlyTyrGluAspLeuLeuLysLysGlyMetLys-119
Hydrophilic Regions - Hopp-Woods
(SEQ. ID. NO. 36085)
1-MetAsnIleLysGlnLeuIleThrAlaAlaLeuIleAlaSerAlaAlaPheAlaThrGlnAlaAlaProGlnLysProValSerAlaAlaGlnThrAlaGlnHisSerAlaValTrpIle
AspValArgSerGluGlnGluPheSerGluGlyHisLeuHisAsnAlaValAsnIleProValAspGlnIleValArgArgIleTyrGluAlaAlaProAspLysAspThrProValAsn
LeuTyrCysArgSerGlyArgArgAlaGluAlaAlaLeuGlnGluLeuLysLysAlaGlyTyrThrAsnValAlaAsnHisGlyGlyTyrGluAspLeuLeuLysLysGlyMetLys-119
g769
AMPHI Regions - AMPHI
SEQ. ID. NO. 36086 1-LeuIleMetValIlePheTyrPheTyrPheCysGlyLysThrPheMetProAlaArgAsnArgTrpMetLeuLeuProLeuLeuAlaSerAla
AlaTyrAlaGluGluThrProCysGluProAspLeuArgSerArgProGluPheArgLeuHisGluAlaGluValLysProIleAspArgGluLys
ValProGlyGlnValArgGluLysGlyLysValLeuGlnValAspGlyGluThrLeuLeuLysAsnProGluLeuLeuSerArgAlaMetTyr
SerAlaValValSerAsnAsnIleAlaGlyIleArgValIleLeuProIleTyrLeuGlnGlnAlaArgGlnAspLysMetLeuAlaLeuTyrAla
GlnGlyIleLeuAlaGlnAlaGluGlyArgValLysGluAlaValSerHisTyrArgGluLeuIleAlaAlaGlnProAspAlaProAlaValArg
MetArgLeuAlaAlaAlaLeuPheGluAspArgGlnAsnGluAlaAlaAlaAspGlnPheAspArgLeuLysThrGluAspLeuProPro TABLE 1-continued GlnLeuMetGluGlnValGluLeuTyrArgLysAlaLeuArgGluArgAspAlaTrpLysValAsnGlyGlyPheSerValThrArgGluHis
AsnIleAsnGlnAlaProLysGlnGlnGlnTyrGlyAsnTrpThrPheProLysGlnValAspGlyThrAlaValAsnTyrArgPheGlyAla
GluLysLysTrpSerLeuLysAsnGlyTrpTyrThrThrAlaGlyGlyAspValSerGlyArgValTyrProGlyAsnLysLysPheAsnAsp
MetThrAlaGlyValSerGlyGlyIleGlyPheAlaAspArgArgLysAspValGlyLeuAlaValPheHisGluArgArgThrTyrGly
AsnAspAlaTyrSerTyrAlaAsnGlyAlaArgLeuTyrPheAsnArgTrpGlnThrProArgTrpGlnThrLeuSerSerAlaGluTrp
GlyArgLeuLysAsnThrArgArgAlaArgSerAspAsnThrHisLeuGlnIleSerAsnSerLeuValPheTyrArgAsnAlaArgGln
TyrTrpThrGlyGlyLeuAspPheTyrArgGluArgAsnProAlaAspArgGlyAspAsnPheAsnArgTyrGlyLeuArgPheAla
TrpGlyGlnGluTrpGlyGlySerGlyLeuSerSerLeuPheArgLeuGlyValAlaLysArgHisTyrGluLysProGlyPhePheSerSer
PheLysGlyGluArgArgArgAspLysGluSerAspThrSerLeuSerLeuTrpHisArgAlaLeuHisPheLysGlyIleThrProArgLeu
ThrLeuSerHisArgGluThrTrpSerAsnAspValPheAsnGluTyrGluLysAsnArgAlaPheValGluPheAsnLysThrPhe-491

Antigenic Index - Jameson-Wolf
(SEQ. ID. NO. 36086)
1-LeuIleMetValIlePheTyrPheTyrPheCysGlyLysThrPheMetProAlaArgAsnArgTrpMetLeuLeuProLeuLeuAlaSerAlaAlaTyrAlaGluGluThrProCys
GluProAspLeuArgSerArgProGluPheArgLeuHisGluAlaGluValLysProIleAspArgGluLysValProGlyGlnValArgGluLysGlyLysValLeuGlnValAsp
GlyGluThrLeuLeuLysAsnProGluLeuLeuSerArgAlaMetTyrSerAlaValValSerAsnAsnIleAlaGlyIleArgValIleLeuProIleTyrLeuGlnGlnAlaArg
GlnAspLysMetLeuAlaLeuTyrAlaGlnGlyIleLeuAlaGlnAlaGluGlyArgValLysGluAlaValSerHisTyrArgGluLeuIleAlaAlaGlnProAspAlaProAla
ValArgMetArgLeuAlaAlaAlaLeuPheGluAspArgGlnAsnGluAlaAlaAlaAspGlnPheAspArgLeuLysThrGluAspLeuProProGlnLeuMetGluGln
ValGluLeuTyrArgLysAlaLeuArgGluArgAspAlaTrpLysValAsnGlyGlyPheSerValThrArgGluHisAsnIleAsnGlnAlaProLysGlnGlnGlnTyrGly
AsnTrpThrPheProLysGlnValAspGlyThrAlaValAsnTyrArgPheGlyAlaGluLysLysTrpSerLeuLysAsnGlyTrpTyrThrThrAlaGlyGlyAspValSer
GlyArgValTyrProGlyAsnLysLysPheAsnAspMetThrAlaGlyValSerGlyGlyIleGlyPheAlaAspArgArgLysAspValGlyLeuAlaValPheHisGluArg
ArgThrTyrGlyAsnAspAlaTyrSerTyrAlaAsnGlyAlaArgLeuTyrPheAsnArgTrpGlnThrProArgTrpGlnThrLeuSerSerAlaGluTrpGlyArgLeuLys
AsnThrArgArgAlaArgSerAspAsnThrHisLeuGlnIleSerAsnSerLeuValPheTyrArgAsnAlaArgGlnTyrTrpThrGlyGlyLeuAspPheTyrArgGluArg
AsnProAlaAspArgGlyAspAsnPheAsnArgTyrGlyLeuArgPheAlaTrpGlyGlnGluTrpGlyGlySerGlyLeuSerSerLeuPheArgLeuGlyValAlaLys
ArgHisTyrGluLysProGlyPhePheSerSerPheLysGlyGluArgArgArgAspLysGluSerAspThrSerLeuSerLeuTrpHisArgAlaLeuHisPheLysGlyIle
ThrProArgLeuThrLeuSerHisArgGluThrTrpSerAsnAspValPheAsnGluTyrGluLysAsnArgAlaPheValGluPheAsnLysThrPhe-491

Hydrophilic Regions - Hopp-Woods
(SEQ. ID. NO. 36086)
1-LeuIleMetValIlePheTyrPheTyrPheCysGlyLysThrPheMetProAlaArgAsnArgTrpMetLeuLeuProLeuLeuAlaSerAlaAlaTyrAlaGluGluThrPro
CysGluProAspLeuArgSerArgProGluPheArgLeuHisGluAlaGluValLysProIleAspArgGluLysValProGlyGlnValArgGluLysGlyLysValLeuGln
ValAspGlyGluThrLeuLeuLysAsnProGluLeuLeuSerArgAlaMetTyrSerAlaValValSerAsnAsnIleAlaGlyIleArgValIleLeuProIleTyrLeuGlnGln
AlaArgGlnAspLysMetLeuAlaLeuTyrAlaGlnGlyIleLeuAlaGlnAlaGluGlyArgValLysGluAlaValSerHisTyrArgGluLeuIleAlaAlaGlnProAspAla
ProAlaValArgMetArgLeuAlaAlaAlaLeuPheGluAspArgGlnAsnGluAlaAlaAlaAspGlnPheAspArgLeuLysThrGluAspLeuProProGlnLeuMetGlu
GlnValGluLeuTyrArgLysAlaLeuArgGluArgAspAlaTrpLysValAsnGlyGlyPheSerValThrArgGluHisAsnIleAsnGlnAlaProLysGlnGlnGlnTyr
GlyAsnTrpThrPheProLysGlnValAspGlyThrAlaValAsnTyrArgPheGlyAlaGluLysLysTrpSerLeuLysAsnGlyTrpTyrThrThrAlaGlyGlyAspVal
SerGlyArgValTyrProGlyAsnLysLysPheAsnAspMetThrAlaGlyValSerGlyGlyIleGlyPheAlaAspArgArgLysAspValGlyLeuAlaValPheHisGlu
ArgArgThrTyrGlyAsnAspAlaTyrSerTyrAlaAsnGlyAlaArgLeuTyrPheAsnArgTrpGlnThrProArgTrpGlnThrLeuSerSerAlaGluTrpGlyArgLeu
LysAsnThrArgArgAlaArgSerAspAsnThrHisLeuGlnIleSerAsnSerLeuValPheTyrArgAsnAlaArgGlnTyrTrpThrGlyGlyLeuAspPheTyrArgGlu
ArgAsnProAlaAspArgGlyAspAsnPheAsnArgTyrGlyLeuArgPheAlaTrpGlyGlnGluTrpGlyGlySerGlyLeuSerSerLeuPheArgLeuGlyValAlaLys
ArgHisTyrGluLysProGlyPhePheSerSerPheLysGlyGluArgArgArgAspLysGluSerAspThrSerLeuSerLeuTrpHisArgAlaLeuHisPheLysGlyIle
ThrProArgLeuThrLeuSerHisArgGluThrTrpSerAsnAspValPheAsnGluTyrGluLysAsnArgAlaPheValGluPheAsnLysThrPhe-491 g770
AMPHI Regions - AMPHI
SEQ. ID. NO. 36087 1-MetAsnArgLeuLeuLeuLeuSerAlaAlaValLeuProThrAlaCysGlySerGlyGluThrAspLysIleGlyArgAlaSerThrVal
PheAsnMetLeuGlyLysAsnAspArgIleGluValGluGlyPheAspAspProAspValGlnGlyValAlaCysTyrIleSerTyrAlaLys
LysGlyGlyLeuLysGluMetValAsnLeuGluGluAspAlaSerAspAlaSerValSerCysValGlnThrAlaSerSerIleSerPheAsp
GluThrAlaValArgLysProLysGluValPheLysArgGlyThrGlyPheAlaPheLysSerArgGlnIleValArgTyrTyrAspProLys
ArgLysAlaPheAlaTyrLeuValTyrSerAspLysIleValGlnGlySerProLysAsnSerLeuSerAlaValSerCysPheGlySerGly
IleProGlnThrAspGlyValGlnAlaAspThrSerGlyLysLeuLeuAlaGlyAlaCysIleIleSerAsnProIleLysAsnProAspLysArg-186

Antigenic Index - Jameson-Wolf
(SEQ. ID. NO. 36087)
1-MetAsnArgLeuLeuLeuLeuSerAlaAlaValLeuProThrAlaCysGlySerGlyGluThrAspLysIleGlyArgAlaSerThrValPheAsnMetLeuGlyLysAsn
AspArgIleGluValGluGlyPheAspAspProAspValGlnGlyValAlaCysTyrIleSerTyrAlaLysLysGlyGlyLeuLysGluMetValAsnLeuGluGluAsp
AlaSerAspAlaSerValSerCysValGlnThrAlaSerSerIleSerPheAspGluThrAlaValArgLysProLysGluValPheLysArgGlyThrGlyPheAlaPheLys
SerArgGlnIleValArgTyrTyrAspProLysArgLysAlaPheAlaTyrLeuValTyrSerAspLysIleValGlnGlySerProLysAsnSerLeuSerAlaValSerCys
PheGlySerGlyIleProGlnThrAspGlyValGlnAlaAspThrSerGlyLysLeuLeuAlaGlyAlaCysIleIleSerAsnProIleLysAsnProAspLysArg-186

Hydrophilic Regions - Hopp-Woods
(SEQ. ID. NO. 36087)
1-MetAsnArgLeuLeuLeuLeuSerAlaAlaValLeuProThrAlaCysGlySerGlyGluThrAspLysIleGlyArgAlaSerThrValPheAsnMetLeuGlyLys
AsnAspArgIleGluValGluGlyPheAspAspProAspValGlnGlyValAlaCysTyrIleSerTyrAlaLysLysGlyGlyLeuLysGluMetValAsnLeuGluGlu
AspAlaSerAspAlaSerValSerCysValGlnThrAlaSerSerIleSerPheAspGluThrAlaValArgLysProLysGluValPheLysArgGlyThrGlyPheAlaPhe
LysSerArgGlnIleValArgTyrTyrAspProLysArgLysAlaPheAlaTyrLeuValTyrSerAspLysIleValGlnGlySerProLysAsnSerLeuSerAlaValSer
CysPheGlySerGlyIleProGlnThrAspGlyValGlnAlaAspThrSerGlyLysLeuLeuAlaGlyAlaCysIleIleSerAsnProIleLysAsnProAspLysArg-186 g771
AMPHI Regions - AMPHI
SEQ. ID. NO. 36088 49-SerIleAlaHisThr-53
SEQ. ID. NO. 36089 133-IleGlnAspLeuPheAspGlyAla-140
SEQ. ID. NO. 36090 312-GlyIleAlaAsnIleGlyAsn-318
SEQ. ID. NO. 36091 358-LeuGlnAspThrValAspArgLeuPro-366
SEQ. ID. NO. 36092 369-ArgPheIleSerArgLeuAspGlySer-377
SEQ. ID. NO. 36093 391-AsnGlyThrPheAsp-395
SEQ. ID. NO. 36094 427-TyrLeuAspGluPheArg-432
SEQ. ID. NO. 36095 437-LysIlePheProAspIleLeuGlyArgLeuSerGly-448
SEQ. ID. NO. 36096 523-LeuGlnAspLeuPheGlyPheHis-530
SEQ. ID. NO. 36097 581-GlyLeuSerGlyLys-585
SEQ. ID. NO. 36098 601-IleSerAspGlyIleSerArgHisIleAspThr-611

Antigenic Index - Jameson-Wolf
SEQ. ID. NO. 36099 37-PheThrProGluAsnIleArgSerArgLeuGlnGln-48
SEQ. ID. NO. 36100 52-HisThrHisArgLysIleSerPhe-59
SEQ. ID. NO. 36101 61-AlaAspIleArgArgArgLeuLeuProArgProThrVal-73
SEQ. ID. NO. 36102 79-ThrIleThrGluProAspGlyGlyArg-87

TABLE 1-continued

| | |
|---|---|
| SEQ. ID. NO. 36103 | 90-ValSerValLysGluThrLysIle-97 |
| SEQ. ID. NO. 36104 | 104-LeuTrpSerAspArgIleGlnVal-111 |
| SEQ. ID. NO. 36105 | 122-AlaLeuThrArgAspArgAsnGlyAlaTrp-131 |
| SEQ. ID. NO. 36106 | 135-AspLeuPheAspGlyAlaLysHisSerAlaSerValAsn-147 |
| SEQ. ID. NO. 36107 | 150-IleValGluAsnSerThrValArg-157 |
| SEQ. ID. NO. 36108 | 174-LeuGlnSerProAspSerSerGlyGlnGlnPheGluSerSerGly-188 |
| SEQ. ID. NO. 36109 | 197-ValProTrpLysSerArgGlyLeuPhe-205 |
| SEQ. ID. NO. 36110 | 208-AspGlyIleGlyThrProGluIleSerPro-217 |
| SEQ. ID. NO. 36111 | 222-AlaSerThrSerLeuAspGlyHisGly-230 |
| SEQ. ID. NO. 36112 | 235-ThrThrGlySerProSerValArgPheAsnAlaGlyGlyAlaAsp-249 |
| SEQ. ID. NO. 36113 | 255-LeuArgAlaAspThrSerPhe-261 |
| SEQ. ID. NO. 36114 | 275-LeuLysAsnAsnSerIleLysThrGlyThrVal-285 |
| SEQ. ID. NO. 36115 | 291-AlaGlyGlyGluTyrAlaArgTrpAspGlySerPheLysLeuAspLysAlaAsnLeu-309 |
| SEQ. ID. NO. 36116 | 317-GlyAsnAlaGluIleSerGlySerPheLysThrProArgLeuGln-331 |
| SEQ. ID. NO. 36117 | 342-TrpSerArgAspAsnGlyLeuAspAlaProArg-352 |
| SEQ. ID. NO. 36118 | 360-AspThrValAspArgLeuProGlnProArgPheIleSerArgLeuAspGlySerLeu-378 |
| SEQ. ID. NO. 36119 | 389-GluLeuAsnGlyThrPheAspArgGlnProVal-399 |
| SEQ. ID. NO. 36120 | 404-LysTyrThrArgGluGlyAlaProHisLeu-413 |
| SEQ. ID. NO. 36121 | 429-AspGluPheArgGlnGlnAsnGlyLysIle-438 |
| SEQ. ID. NO. 36122 | 443-LeuGlyArgLeuSerGlyAsnValGluAla-452 |
| SEQ. ID. NO. 36123 | 464-LeuGlnLeuAspAspMetGlu-470 |
| SEQ. ID. NO. 36124 | 473-LeuHisAlaAspLysAspHisIleAla-481 |
| SEQ. ID. NO. 36125 | 483-SerArgPheLysSerGlyLeuTyrGlyGlyHisThrGluGlyGlyIle-498 |
| SEQ. ID. NO. 36126 | 502-AsnThrArgProAlaThrTyrArgLeuGlnGlnAsnAlaSerAsn-516 |
| SEQ. ID. NO. 36127 | 531-SerPheSerGlyAsnGlyAspAlaVal-539 |
| SEQ. ID. NO. 36128 | 543-ThrAlaSerGlyGluAsnArgLysGlnLeuIleArgSerLeuGlnGlySerLeu-560 |
| SEQ. ID. NO. 36129 | 564-IleSerAsnGlyAla-568 |
| SEQ. ID. NO. 36130 | 573-AspMetAspSerIleLeuLysAsnGlyLeuSerGlyLysIleSerGly-588 |
| SEQ. ID. NO. 36131 | 597-LeuAsnSerGluIleSerAspGlyIleSerArgHisIleAsp-610 |
| SEQ. ID. NO. 36132 | 623-AsnGlyTyrThrAsnLeuAspThrGlnGluLeuSerGlu-635 |
| SEQ. ID. NO. 36133 | 642-AlaValHisProLysAsnLysProIlePro-651 |
| SEQ. ID. NO. 36134 | 656-GlyThrValAspLysProSerIleThrValAspTyrGlyArgLeuThrGlyGlyIleAsnSerArgLysGluLysGlnLysIleLeuGlu-685 |
| SEQ. ID. NO. 36135 | 695-LeuLysProLysGluPro-700 |
| Hydrophilic Regions - Hopp-Woods | |
| SEQ. ID. NO. 36136 | 40-GluAsnIleArgSerArgLeuGln-47 |
| SEQ. ID. NO. 36137 | 53-ThrHisArgLysIleSerPhe-59 |
| SEQ. ID. NO. 36138 | 61-AlaAspIleArgArgArgLeuLeuPro-69 |
| SEQ. ID. NO. 36139 | 81-ThrGluProAspGlyGlyArg-87 |
| SEQ. ID. NO. 36140 | 90-ValSerValLysGluThrLysIle-97 |
| SEQ. ID. NO. 36141 | 122-AlaLeuThrArgAspArgAsnGly-129 |
| SEQ. ID. NO. 36142 | 135-AspLeuPheAspGlyAlaLysHisSerAlaSer-145 |
| SEQ. ID. NO. 36143 | 175-GlnSerProAspSerSerGlyGlnGlnPheGlu-185 |
| SEQ. ID. NO. 36144 | 255-LeuArgAlaAspThrSerPhe-261 |
| SEQ. ID. NO. 36145 | 302-PheLysLeuAspLysAlaAsnLeu-309 |
| SEQ. ID. NO. 36146 | 325-PheLysThrProArgLeu-330 |
| SEQ. ID. NO. 36147 | 344-ArgAspAsnGlyLeuAspAlaProArg-352 |
| SEQ. ID. NO. 36148 | 360-AspThrValAspArgLeuProGln-367 |
| SEQ. ID. NO. 36149 | 370-PheIleSerArgLeuAspGly-376 |
| SEQ. ID. NO. 36150 | 392-GlyThrPheAspArgGlnProVal-399 |
| SEQ. ID. NO. 36151 | 404-LysTyrThrArgGluGlyAlaPro-411 |
| SEQ. ID. NO. 36152 | 429-AspGluPheArgGlnGlnAsn-435 |
| SEQ. ID. NO. 36153 | 465-GlnLeuAspAspMetGlu-470 |
| SEQ. ID. NO. 36154 | 473-LeuHisAlaAspLysAspHisIleAla-481 |
| SEQ. ID. NO. 36155 | 544-AlaSerGlyGluAsnArgLysGlnLeuIle-553 |
| SEQ. ID. NO. 36156 | 600-GluIleSerAspGlyIleSerArgHisIleAsp-610 |
| SEQ. ID. NO. 36157 | 629-AspThrGlnGluLeuSerGlu-635 |
| SEQ. ID. NO. 36158 | 643-ValHisProLysAsnLysProIlePro-651 |
| SEQ. ID. NO. 36159 | 656-GlyThrValAspLysProSerIle-663 |
| SEQ. ID. NO. 36160 | 674-IleAsnSerArgLysGluLysGlnLysIleLeuGlu-685 |
| SEQ. ID. NO. 36161 | 696-LysProLysGluPro-700 |
| g772 | |
| AMPHI Regions - AMPHI | |
| SEQ. ID. NO. 36162 | 1-ValPheGlyThrValLeuArgThrAspAlaAspCysLeuGlnIleIleValValGlyLysPhePheGlnValValAlaTyrGlyPheAlaAla LeuAlaGluGlyGluPheHisGlnPheGlyGluMetIleGluIleValArgLeuAlaAspThrValPheHisArgAsnHisAlaHisHisCysGly IleAspPheArgArgGlyIleGluArgPheGlyArgHisValAsnGlnGlnLeuHisIleGluLysIleLeuGlnHisHisThrGlnAlaThrVal ValValAlaPheArgArgGlyAsnHisAlaLeuAspHisPhePheLeuGlnHisLysValHisIleGlyAspIleValArgHisLeuArgGln PheGluGlnLysArgArgGlyAspValIleArgGlnValAlaAspAspPheLeuPheAlaAspAlaValGluIleLysLeuGlnHisValAla PheValAsnHisGlnPheIleArgLysArgGlnArgPheGlnThrAlaTyrAspValAlaValAspPheAspAsnValGlnAlaValGlnLeu PheArgGlnArgPheGlyAsnCysArgGlnThrArgAlaAspPheAsnHisAspIleIleArgLeuArgAlaHisGlyValAspAsnIleAla AspAsnProArgValLeuGlnLysIleLeuProGluThrLeuAlaGlyPheValPhePheHisArgValSerSerSerValGluThrProPro PheArgAlaAlaGlySerAspSerValTrpAlaGlyArgAsnProPheGlnIleArgThrThrHisArgAlaValLeuTyrValSerSer CysValLeuGluHisLysCysValTyrSerIleArgLeuMetSerAlaLeu-297 |

Antigenic Index - Jameson-Wolf
(SEQ. ID. NO. 36162)
1-ValPheGlyThrValLeuArgThrAspAlaAspCysLeuGlnIleIleValValGlyLysPhePheGlnValValAlaTyrGlyPheAlaAlaLeuAlaGluGlyGluPheHisGln PheGlyGluMetIleGluIleValArgLeuAlaAspThrValPheHisArgAsnHisAlaHisHisCysGlyIleAspPheArgArgGlyIleGluArgPheGlyArgHisValAsnGln GlnLeuHisIleGluLysIleLeuGlnHisHisThrGlnAlaThrValValValAlaPheArgArgGlyAsnHisAlaLeuAspHisPhePheLeuGlnHisLysValHisIleGlyAsp IleValArgHisLeuArgGlnPheGluGlnLysArgArgGlyAspValIleArgGlnValAlaAspAspPheLeuPheAlaAspAlaValGluIleLysLeuGlnHisValAlaPhe ValAsnHisGlnPheIleArgLysArgGlnArgPheGlnThrAlaTyrAspValAlaValAspPheAspAsnValGlnAlaValGlnLeuPheArgGlnArgPheGlyAsnCys ArgGlnThrArgAlaAspPheAsnHisAspIleIleArgLeuArgAlaHisGlyValAspAsnIleAlaAspAsnProArgValLeuGlnLysIleLeuProGluThrLeuAlaGly TABLE 1-continued PheValPhePheHisArgValSerSerSerValGluThrProProPheArgAlaAlaGlySerAspSerValTrpAlaGlyArgAsnProPheGlnIleArgThrThrHisArg AlaValLeuTyrValSerSerCysValLeuGluHisLysCysValTyrSerIleArgLeuMetSerAlaLeu-297

Hydrophilic Regions - Hopp-Woods (SEQ. ID. NO. 36162)

1-ValPheGlyThrValLeuArgThrAspAlaAspCysLeuGlnIleIleValValGlyLysPhePheGlnValValAlaTyrGlyPheAlaAlaLeuAlaGluGlyGluPheHis GlnPheGlyGluMetIleGluIleValArgLeuAlaAspThrValPheHisArgAsnHisAlaHisHisCysGlyIleAspPheArgArgGlyIleGluArgPheGlyArgHis ValAsnGlnGlnLeuHisIleGluLysIleLeuGlnHisHisThrGlnAlaThrValValValAlaPheArgArgGlyAsnHisAlaLeuAspHisPhePheLeuGlnHisLys ValHisIleGlyAspIleValArgHisLeuArgGlnPheGluGlnLysArgArgGlyAspValIleArgGlnValAlaAspAspPheLeuPheAlaAspAlaValGluIleLys LeuGlnHisValAlaPheValAsnHisGlnPheIleArgLysArgGlnArgPheGlnThrAlaTyrAspValAlaValAspPheAspAsnValGlnAlaValGlnLeuPheArg GlnArgPheGlyAsnCysArgGlnThrArgAlaAspPheAsnHisAspIleIleArgLeuArgAlaHisGlyValAspAsnIleAlaAspAsnProArgValLeuGlnLysIle LeuProGluThrLeuAlaGlyPheValPhePheHisArgValSerSerSerValGluThrProProPheArgAlaAlaGlySerAspSerValTrpAlaGlyArgAsnProPhe GlnIleArgThrThrHisArgAlaValLeuTyrValSerSerCysValLeuGluHisLysCysValTyrSerIleArgLeuMetSerAlaLeu-297 g774

AMPHI Regions - AMPHI

| | |
|---|---|
| SEQ. ID. NO. 36163 | 16-AlaSerCysAlaSerValLeu-22 |
| SEQ. ID. NO. 36164 | 61-ValArgLeuSerAsnGluVal-67 |
| SEQ. ID. NO. 36165 | 90-ValGlnLysLeuAsp-94 |
| SEQ. ID. NO. 36166 | 115-ValGluThrAlaGlnAsnLeuTyrAsnGlnAlaLeuLysHisTyrGlnAsnGly-132 |
| SEQ. ID. NO. 36167 | 170-CysGluSerValIleGluIle-176 |
| SEQ. ID. NO. 36168 | 180-TyrAlaAsnArgPheLysAspSer-187 |
| SEQ. ID. NO. 36169 | 210-AlaArgAlaThrTrpArgSerLeuIleGlnThrTyrProGly-223 |

Antigenic Index - Jameson-Wolf

| | |
|---|---|
| SEQ. ID. NO. 36170 | 23-ProValProGluGlySerArgThrGluMetProThrGlnGluAsnAlaSerAspGlyIlePro-43 |
| SEQ. ID. NO. 36171 | 49-LeuGlnAspArgLeuAspTyrLeuGlu-57 |
| SEQ. ID. NO. 36172 | 59-LysIleValArgLeuSerAsnGluValGluMetLeuAsnGlyLysValLysAlaLeuGluHisThrLysIleHisProSerGlyArgThrTyrVal GlnLysLeuAspAspArgLysLeuLysGlu-100 |
| SEQ. ID. NO. 36173 | 102-TyrLeuAsnThrGluGlyGlySerAla-110 |
| SEQ. ID. NO. 36174 | 125-AlaLeuLysHisTyrGlnAsnGlyArgPhe-134 |
| SEQ. ID. NO. 36175 | 142-LysGlyAlaAspGlyGlyAspGlyGlySerIleAlaGln-154 |
| SEQ. ID. NO. 36176 | 162-GlnSerArgAlaArgMetGlyAsnCys-170 |
| SEQ. ID. NO. 36177 | 176-IleGlyGlyArgTyrAlaAsnArgPheLysAspSerProThrAla-190 |
| SEQ. ID. NO. 36178 | 198-GlyGluCysGlnTyr-202 |
| SEQ. ID. NO. 36179 | 204-LeuGlnGlnLysAspIleAla-210 |
| SEQ. ID. NO. 36180 | 221-TyrProGlySerProAlaAlaLysArgAlaAlaAlaAlaValArgLysArg-237 |

Hydrophilic Regions - Hopp-Woods

| | |
|---|---|
| SEQ. ID. NO. 36181 | 25-ProGluGlySerArgThrGluMetProThrGlnGluAsnAlaSerAsp-40 |
| SEQ. ID. NO. 36182 | 49-LeuGlnAspArgLeuAspTyrLeuGlu-57 |
| SEQ. ID. NO. 36183 | 59-LysIleValArgLeuSerAsnGluValGluMetLeuAsnGlyLysValLysAlaLeuGluHisThrLysIleHisProSerGly-86 |
| SEQ. ID. NO. 36184 | 89-TyrValGlnLysLeuAspAspArgLysLeuLysGlu-100 |
| SEQ. ID. NO. 36185 | 142-LysGlyAlaAspGlyGlyAspGlyGlySerIleAlaGln-154 |
| SEQ. ID. NO. 36186 | 163-SerArgAlaArgMetGlyAsn-169 |
| SEQ. ID. NO. 36187 | 180-TyrAlaAsnArgPheLysAspSerProThrAla-190 |
| SEQ. ID. NO. 36188 | 198-GlyGluCysGlnTyr-202 |
| SEQ. ID. NO. 36189 | 204-LeuGlnGlnLysAspIleAla-210 |
| SEQ. ID. NO. 36190 | 225-ProAlaAlaLysArgAlaAlaAlaAlaValArgLysArg-237 |

g900-2

AMPHI Regions - AMPHI

| | |
|---|---|
| SEQ. ID. NO. 36191 | 6-LeuGluAsnGlyThrHisSer-12 |
| SEQ. ID. NO. 36192 | 19-GluArgThrTyrProGluProCysHisGluCysLysTerTerLeuArgArgIle-36 |
| SEQ. ID. NO. 36193 | 43-AlaPheAlaGlnPheCys-48 |
| SEQ. ID. NO. 36194 | 68-ValGlyLysHisLeuArgLysPheArgArgPheArgArgArgGly-82 |
| SEQ. ID. NO. 36195 | 94-ValGlyLeuPheArgLeuAlaArgLeuPheHisValGlyAsnAspPheValAspArgPheLeuGlyPhePhe-117 |
| SEQ. ID. NO. 36196 | 130-PheGlyHisPheAlaSer-135 |
| SEQ. ID. NO. 36197 | 153-GlyGluGluPheLeuGluThrValValGluAlaAlaGlyAsnValAlaArgHisPheAspValLeuAspLeu-176 |
| SEQ. ID. NO. 36198 | 193-SerHisGlnAsnArgIle-198 |
| SEQ. ID. NO. 36199 | 230-HisGlnThrLeuGlyGlyAspAlaGly-238 |
| SEQ. ID. NO. 36200 | 242-ValGlnLeuHisHisPheGly-248 |
| SEQ. ID. NO. 36201 | 265-GlyLysProSerGlyGlyAsnGlyLeuGlyGlyLeuValAsn-278 |
| SEQ. ID. NO. 36202 | 311-AspGlyAlaAspValValAlaGlnMet-319 |

Antigenic Index - Jameson-Wolf

| | |
|---|---|
| SEQ. ID. NO. 36203 | 1-GlyTerProGluProLeuGluAsnGlyThrHisSerGluProThrGluMetAsxGluArgThrTyrProGluProCysHisGluCysLysTer TerLeuArgArgIleArgGlyGlnCys-40 |
| SEQ. ID. NO. 36204 | 50-PheGlyValAspPheArgArgArgLysPhePhe-60 |
| SEQ. ID. NO. 36205 | 70-LysHisLeuArgLysPheArgArgPheArgArgArgGlyGluGlyPheIle-86 |
| SEQ. ID. NO. 36206 | 88-PheLysGlnArgAla-92 |
| SEQ. ID. NO. 36207 | 105-ValGlyAsnAspPheValAsp-111 |
| SEQ. ID. NO. 36208 | 120-PheProLysArgAsnGlyIleAla-127 |
| SEQ. ID. NO. 36209 | 135-SerValGlnThrAspGlnGluPhe-142 |
| SEQ. ID. NO. 36210 | 150-PheGlyGlnGlyGluGluPheLeu-157 |
| SEQ. ID. NO. 36211 | 163-AlaAlaGlyAsnVal-167 |
| SEQ. ID. NO. 36212 | 177-ValAlaProAspGlyAspPheValGly-185 |
| SEQ. ID. NO. 36213 | 189-GlnAsnValGlySerHisGlnAsnArgIleThrGluGlnThrHisPhe-204 |
| SEQ. ID. NO. 36214 | 233-LeuGlyGlyAspAlaGlyGlnAsnPro-241 |
| SEQ. ID. NO. 36215 | 261-ValGluSerAlaGlyLysProSerGlyGlyAsnGly-272 |
| SEQ. ID. NO. 36216 | 289-ValValIleGlyGluGluGluGluGlyPhe-298 |
| SEQ. ID. NO. 36217 | 302-ValLeuArgArgAlaAspGlyGlyAlaAspGlyAlaAsp-314 |
| SEQ. ID. NO. 36218 | 319-MetArgGlyAlaGlyGlyGlyTyrAlaGly-328 |
| SEQ. ID. NO. 36219 | 343-MetProSerGluArgGluLysMetArgArg-352 |
| SEQ. ID. NO. 36220 | 361-ProAlaAspAsnArg-365 |

TABLE 1-continued

Hydrophilic Regions - Hopp-Woods
SEQ. ID. NO. 36221 1-GlyTerProGluProLeuGluAsnGlyThrHisSerGluProThrGluMetAsxGluArgThrTyrPro-23
SEQ. ID. NO. 36222 25-ProCysHisGluCysLysTerTerLeuArgArgIleArgGly-38
SEQ. ID. NO. 36223 53-AspPheArgArgArgLysPhePhe-60
SEQ. ID. NO. 36224 70-LysHisLeuArgLysPheArgArgPheArgArgArgGlyGluGly-84
SEQ. ID. NO. 36225 121-ProLysArgAsnGly-125
SEQ. ID. NO. 36226 137-GlnThrAspGlnGluPhe-142
SEQ. ID. NO. 36227 152-GlnGlyGluGluPheLeu-157
SEQ. ID. NO. 36228 177-ValAlaProAspGlyAspPheValGly-185
SEQ. ID. NO. 36229 194-HisGlnAsnArgIleThrGlu-200
SEQ. ID. NO. 36230 233-LeuGlyGlyAspAlaGlyGln-239
SEQ. ID. NO. 36231 263-SerAlaGlyLysProSerGly-269
SEQ. ID. NO. 36232 289-ValValIleGlyGluGluGluGluGlyPhe-298
SEQ. ID. NO. 36233 302-ValLeuArgArgAlaAspGlyGlyAlaAspGlyAlaAsp-314
SEQ. ID. NO. 36234 343-MetProSerGluArgGluLysMetArgArg-352
g902
AMPHI Regions - AMPHI
SEQ. ID. NO. 36235 56-AlaValGlyHisPheAlaAspValProAla-65
SEQ. ID. NO. 36236 77-LeuThrIleLysArgValHisGly-84
SEQ. ID. NO. 36237 128-AspAlaValGlyGlyGly-133
SEQ. ID. NO. 36238 190-PheGlyAspPheGlyAsp-195
SEQ. ID. NO. 36239 216-AlaArgArgLeuAsp-220
SEQ. ID. NO. 36240 241-AspValAlaHisPheLeuGlyGlyAla-249
SEQ. ID. NO. 36241 266-ArgArgIleArgHisLeuPheGlyVal-274
SEQ. ID. NO. 36242 288-GlyLysIleThrAlaValGlnGlyPheSer-297
SEQ. ID. NO. 36243 318-ArgProThrGluAlaAlaGluGlyPhe-326
SEQ. ID. NO. 36244 334-ArgLysCysAspGlyValValAspLysIleThrAlaAspVal-347
Antigenic Index - Jameson-Wolf
SEQ. ID. NO. 36245 1-MetProSerGluProGluArgArgHisGlyAsnThrAla-13
SEQ. ID. NO. 36246 26-PheSerGlyLysProPheLysIleThrGly-35
SEQ. ID. NO. 36247 38-ValValLeuArgArgArgIleValGln-46
SEQ. ID. NO. 36248 72-AlaHisThrAspGlyLeuThrIleLysArgValHisGly-84
SEQ. ID. NO. 36249 89-GlnAsnGlyGlySer-93
SEQ. ID. NO. 36250 97-GlnThrGlnGlyArgArgXxxAsn-104
SEQ. ID. NO. 36251 113-IleAlaGluLysProArgProAlaLeu-121
SEQ. ID. NO. 36252 134-LeuPheGluAspGlyGlyGlyPheLeuArgArgSerAspValAlaValAspProGlyArgAspValGln-156
SEQ. ID. NO. 36253 175-ArgAlaArgAlaProValAsnGlyLysGlyGlyAsn-186
SEQ. ID. NO. 36254 192-AspPheGlyAspGlyGlyGln-198
SEQ. ID. NO. 36255 210-PheGluGlyAsnGlyTyrAlaArgArgLeuAspHisArgLeuGlnAsnGlyGlyAsnGlnArgLeu-231
SEQ. ID. NO. 36256 252-IleAspValAspAspLeuArgProGluSerAspValValThrArgArgIleArg-269
SEQ. ID. NO. 36257 277-GlyAsnLeuHisGlyAsnAspAla-284
SEQ. ID. NO. 36258 296-PheSerGlyIleProGluArgArgIleAla-305
SEQ. ID. NO. 36259 310-AlaHisArgProThrCysAlaLysArgProThrGluAlaAlaGlu-324
SEQ. ID. NO. 36260 330-AlaArgHisArgArgLysCysAspGlyValValAspLysIleThrAla-345
SEQ. ID. NO. 36261 347-ValHisAsnGlyProAlaPheGlnLysSerAla-357
Hydrophilic Regions - Hopp-Woods
SEQ. ID. NO. 36262 1-MetProSerGluProGluArgArgHisGlyAsn-11
SEQ. ID. NO. 36263 29-LysProPheLysIleThrGly-35
SEQ. ID. NO. 36264 38-ValValLeuArgArgArgIleValGln-46
SEQ. ID. NO. 36265 77-LeuThrIleLysArgValHisGly-84
SEQ. ID. NO. 36266 99-GlnGlyArgArgXxxAsn-104
SEQ. ID. NO. 36267 113-IleAlaGluLysProArgProAlaLeu-121
SEQ. ID. NO. 36268 134-LeuPheGluAspGlyGlyGlyPheLeuArgArgSerAspValAlaValAspProGlyArgAspValGln-156
SEQ. ID. NO. 36269 175-ArgAlaArgAlaProValAsnGlyLysGlyGlyAsn-186
SEQ. ID. NO. 36270 214-GlyTyrAlaArgArgLeuAspHisArgLeuGlnAsn-225
SEQ. ID. NO. 36271 252-IleAspValAspAspLeuArgProGluSerAspValValThrArgArgIleArg-269
SEQ. ID. NO. 36272 299-IleProGluArgArgIleAla-305
SEQ. ID. NO. 36273 313-ProThrCysAlaLysArgProThrGluAlaAlaGlu-324
SEQ. ID. NO. 36274 330-AlaArgHisArgArgLysCysAspGlyValValAspLysIleThrAla-345
g904
AMPHI Regions - AMPHI
SEQ. ID. NO. 36275 1-MetMetGlnHisAsnArgPhePheAlaValGlyAlaGlyGlyAspAspGlyAspArgArgAlaAlaAspPhePheAsnProPhe
GlnIleCysPheGlyIleGlyArgGlnCysValValAlaPheHisAlaAspSerArgPheAlaProAlaGlyHisGlyPheValAsnArg
PheAlaGlyPheHisArgIleArgThrAlaArgGlnAspValGlyPheAlaAlaAlaTrpGlnPheValAlaAspAlaAspIleAspGly
PheAsnAlaValHisTyrIleGluPheGlyAsnAlaHisThrGlyAsnAlaValAspLeuAspGlyAlaPheGlnGlyGlyGlyIleLys
ProAlaAlaAlaAlaArgAlaAlaGlyTyrArgThrGluPheValSerAlaLeuArgGlnThrCysAlaTyrPheValGluGlnPheGly
ArgGluArgAlaArgThrAspAlaArgGlyIleGlyPheAspAspAlaGlnAsnIleIleGlnHisLeuArgThrTyrAlaArgAlaCys
ArgSerArgAlaGlyGluThrValGlyArgGlyAsnGluGlyValSerAlaValValAspValGlnGlnArgThrLeuArgAlaPheLys
GlnGlnPhePheAlaValPheValPhePheValGlnHisAlaGlyHisValGlyAsnHisArgArgAsnAlaArgArgAspPhePheAsp
AsnArgHisHisValPheArgPheAsnArgSerGlyValMetGlnValLeuGluLeuAspValValIleGlyLysAspGlyIleGlnPhe
PheThrGlnPhePheArgMetGlnGlnIleGlyGlyAlaAsnGlyAlaAlaCysHisPheValPheValGlyArgAlaAspAlaAlaAla
GlyArgAlaAspPheAlaPheAlaAlaArgCysPheAlaGlyLeuValGluArgAspValValArgGlnAspGlnArgAlaGlyArg
ArgAspPheGlnThrAlaPheAspValPheHisAlaCysArgValGlnLeuValAspPheAlaGlnGlnGlyPheGlyGlyAsnAsp
AsnAlaArgThrAspGluAlaIleGlnSerPheValGlnAspThrAlaArgAsnGlnAlaGlnAsnGlyPhePheAlaAlaAspAspGln
GlyMetAlaArgIleValAlaAlaLeuGluAlaHisAspAlaAlaGlyPhePheArgGlnProValAsnAspPheThrPheThrLeuVal
AlaProLeuCysAlaAspTyrTyrAsnIlePheSerHisSerHisIleThrTyrArgTyr-436
Antigenic Index - Jameson-Wolf
(SEQ. ID. NO. 36275)
1-MetMetGlnHisAsnArgPhePheAlaValGlyAlaGlyGlyAspAspGlyAspArgArgAlaAlaAspPhePheAsnProPheGlnIleCysPheGlyIleGlyArgGln
CysValValAlaPheHisAlaAspSerArgPheAlaProAlaGlyHisGlyPheValAsnArgPheAlaGlyPheHisArgIleArgThrAlaArgGlnAspValGlyPheAla TABLE 1-continued AlaAlaTrpGlnPheValAlaAspAlaAspIleAspGlyPheAsnAlaValHisTyrIleGluPheGlyAsnAlaHisThrGlyAsnAlaValAspLeuAspGlyAlaPheGln
GlyGlyGlyIleLysProAlaAlaAlaAlaArgAlaAlaGlyTyrArgThrGluPheValSerAlaLeuArgGlnThrCysAlaTyrPheValGluGlnPheGlyArgGluArg
AlaArgThrAspAlaArgGlyIleGlyPheAspAspAlaGlnAsnIleIleGlnHisLeuArgThrTyrAlaArgAlaCysArgSerArgAlaGlyGluThrValGlyArgGly
AsnGluGlyValSerAlaValValAspValGlnGlnArgThrLeuArgAlaPheLysGlnGlnPhePheAlaValPheValPhePheValGlnHisAlaGlyHisValGlyAsn
HisArgArgAsnAlaArgArgAspPhePheAspAsnArgHisHisValPheArgPheAsnArgSerGlyValMetGlnValLeuGluLeuAspValValIleGlyLysAsp
GlyIleGlnPhePheThrGlnPhePheArgMetGlnGlnIleGlyGlyAlaAsnGlyAlaAlaCysHisPheValPheValGlyArgAlaAspAlaAlaAlaGlyArgAlaAsp
PheAlaPheAlaAlaArgCysPheAlaGlyLeuValGluArgAspValValArgGlnAspGlnArgAlaGlyArgArgAspPheGlnThrAlaPheAspValPheHisAla
CysArgValGlnLeuValAspPheAlaGlnGlnGlyPheGlyGlyAsnAspAsnAlaArgThrAspGluAlaIleGlnSerPheValGlnAspThrAlaArgAsnGlnAla
GlnAsnGlyPhePheAlaAlaAspAspGlnGlyMetAlaArgIleValAlaAlaLeuGluAlaHisAspAlaAlaGlyPhePheArgGlnProValAsnAspPheThrPheThr
LeuValAlaProLeuCysAlaAspTyrTyrAsnIlePheSerHisSerHisIleThrTyrArgTyr-436

Hydrophilic Regions - Hopp-Woods (SEQ. ID. NO. 36275)

1-MetMetGlnHisAsnArgPhePheAlaValGlyAlaGlyGlyAspAspGlyAspArgArgAlaAlaAspPhePheAsnProPheGlnIleCysPheGlyIleGlyArgGln
CysValValAlaPheHisAlaAspSerArgPheAlaProAlaGlyHisGlyPheValAsnArgPheAlaGlyPheHisArgIleArgThrAlaArgGlnAspValGlyPheAla
AlaAlaTrpGlnPheValAlaAspAlaAspIleAspGlyPheAsnAlaValHisTyrIleGluPheGlyAsnAlaHisThrGlyAsnAlaValAspLeuAspGlyAlaPheGln
GlyGlyGlyIleLysProAlaAlaAlaAlaArgAlaAlaGlyTyrArgThrGluPheValSerAlaLeuArgGlnThrCysAlaTyrPheValGluGlnPheGlyArgGluArg
AlaArgThrAspAlaArgGlyIleGlyPheAspAspAlaGlnAsnIleIleGlnHisLeuArgThrTyrAlaArgAlaCysArgSerArgAlaGlyGluThrValGlyArgGly
AsnGluGlyValSerAlaValValAspValGlnGlnArgThrLeuArgAlaPheLysGlnGlnPhePheAlaValPheValPhePheValGlnHisAlaGlyHisValGlyAsn
HisArgArgAsnAlaArgArgAspPhePheAspAsnArgHisHisValPheArgPheAsnArgSerGlyValMetGlnValLeuGluLeuAspValValIleGlyLysAspGly
IleGlnPhePheThrGlnPhePheArgMetGlnGlnIleGlyGlyAlaAsnGlyAlaAlaCysHisPheValPheValGlyArgAlaAspAlaAlaAlaGlyArgAlaAspPhe
AlaPheAlaAlaArgCysPheAlaGlyLeuValGluArgAspValValArgGlnAspGlnArgAlaGlyArgArgAspPheGlnThrAlaPheAspValPheHisAlaCys
ArgValGlnLeuValAspPheAlaGlnGlnGlyPheGlyGlyAsnAspAsnAlaArgThrAspGluAlaIleGlnSerPheValGlnAspThrAlaArgAsnGlnAlaGlnAsn
GlyPhePheAlaAlaAspAspGlnGlyMetAlaArgIleValAlaAlaLeuGluAlaHisAspAlaAlaGlyPhePheArgGlnProValAsnAspPheThrPheThrLeuVal
AlaProLeuCysAlaAspTyrTyrAsnIlePheSerHisSerHisIleThrTyrArgTyr-436 g907-2

AMPHI Regions - AMPHI

| | |
|---|---|
| SEQ. ID. NO. 36276 | 6-LeuGluAsnGlyThrHisSer-12 |
| SEQ. ID. NO. 36277 | 19-GluArgThrTyrProGluProCysHisGluCysLysTerTerMetLysLysProThrAspThrLeuPro-41 |
| SEQ. ID. NO. 36278 | 74-AspAspValAlaSerValMetArgSer-82 |
| SEQ. ID. NO. 36279 | 98-LysGluGlyGluArgTrpLeuSerAlaMetSer-108 |
| SEQ. ID. NO. 36280 | 110-ArgLeuAlaArgPheValPro-116 |
| SEQ. ID. NO. 36281 | 161-GlyAlaArgGlyLeu-165 |
| SEQ. ID. NO. 36282 | 174-AsnTyrIleGlyLysProAlaHis-181 |
| SEQ. ID. NO. 36283 | 197-LeuArgHisTyrArgAsnLeuGluLysGlyAspIleValArgAlaLeuAlaArgPheAsnGly-217 |

Antigenic Index - Jameson-Wolf

| | |
|---|---|
| SEQ. ID. NO. 36284 | 1-GlyTerProGluProLeuGluAsnGlyThrHisSerGluProThrGluMetAsxGluArgThrTyrProGluProCysHisGluCysLysTer TerMetLysLysProThrAspThrLeuPro-41 |
| SEQ. ID. NO. 36285 | 44-LeuGlnArgArgArgLeuLeu-50 |
| SEQ. ID. NO. 36286 | 65-GlyAlaGlnArgGluGluThrLeuAlaAspAspValAlaSer-78 |
| SEQ. ID. NO. 36287 | 83-SerValGlySerValAsnProProArgLeuValPheAspAsnProLysGluGlyGluArgTrp-103 |
| SEQ. ID. NO. 36288 | 113-ArgPheValProAspGluGlyGluArgArgArgLeu-124 |
| SEQ. ID. NO. 36289 | 129-GlnTyrGluSerSerArgAlaGlyLeu-137 |
| SEQ. ID. NO. 36290 | 147-GluValGluSerAlaPhe-152 |
| SEQ. ID. NO. 36291 | 174-AsnTyrIleGlyLysProAlaHisAsn-182 |
| SEQ. ID. NO. 36292 | 187-ArgThrAsnLeuArgTyrGly-193 |
| SEQ. ID. NO. 36293 | 200-TyrArgAsnLeuGluLysGlyAspIleVal-209 |
| SEQ. ID. NO. 36294 | 216-AsnGlySerLeuGlySerAsnLysTyrProAsnAla-227 |
| SEQ. ID. NO. 36295 | 232-TrpArgAsnArgTrpGlnTrp-238 |

Hydrophilic Regions - Hopp-Woods

| | |
|---|---|
| SEQ. ID. NO. 36296 | 1-GlyTerProGluProLeuGluAsnGlyThrHisSerGluProThrGluMetAsxGluArgThrTyrPro-23 |
| SEQ. ID. NO. 36297 | 25-ProCysHisGluCysLysTerTerMetLysLysProThrAsp-38 |
| SEQ. ID. NO. 36298 | 44-LeuGlnArgArgArgLeuLeu-50 |
| SEQ. ID. NO. 36299 | 65-GlyAlaGlnArgGluGluThrLeuAlaAspAspValAlaSer-78 |
| SEQ. ID. NO. 36300 | 92-LeuValPheAspAsnProLysGluGlyGluArgTrp-103 |
| SEQ. ID. NO. 36301 | 115-ValProAspGluGlyGluArgArgArgLeu-124 |
| SEQ. ID. NO. 36302 | 131-GluSerSerArgAlaGlyLeu-137 |
| SEQ. ID. NO. 36303 | 147-GluValGluSerAlaPhe-152 |
| SEQ. ID. NO. 36304 | 201-ArgAsnLeuGluLysGlyAspIleVal-209 |

g908

AMPHI Regions - AMPHI

| | |
|---|---|
| SEQ. ID. NO. 36305 | 24-ThrAlaAlaGluLeu-28 |
| SEQ. ID. NO. 36306 | 125-ThrAspCysTyrArgSerTyrAspValLeuAspValSerGluPheSerHisPheSer-143 |

Antigenic Index - Jameson-Wolf

| | |
|---|---|
| SEQ. ID. NO. 36307 | 1-LysSerArgLeuSerArgTyrLysGlnAsnLysLeu-12 |
| SEQ. ID. NO. 36308 | 30-GlyIleAsnLysAsnThrAla-36 |
| SEQ. ID. NO. 36309 | 49-GlnAsnGlyProHis-53 |
| SEQ. ID. NO. 36310 | 57-PheAspGlyGluValGluAlaAspGluSerTyrPheGlyGlyGlnArgLysGlyLysArgGlyArgGlyAlaAlaGlyLys-83 |
| SEQ. ID. NO. 36311 | 89-LeuLeuLysArgAsnGlyLysVal-96 |
| SEQ. ID. NO. 36312 | 113-IleArgGluGlnValLysProAspSerIleVal-123 |
| SEQ. ID. NO. 36313 | 125-ThrAspCysTyrArgSerTyrAsp-132 |
| SEQ. ID. NO. 36314 | 159-ArgThrThrLysProTyr-164 |

Hydrophilic Regions - Hopp-Woods

| | |
|---|---|
| SEQ. ID. NO. 36315 | 1-LysSerArgLeuSerArgTyrLysGlnAsnLys-11 |
| SEQ. ID. NO. 36316 | 57-PheAspGlyGluValGluAlaAspGluSerTyr-67 |

TABLE 1-continued

| | |
|---|---|
| SEQ. ID. NO. 36317 | 70-GlyGlnArgLysGlyLysArgGlyArgGlyAlaAlaGly-82 |
| SEQ. ID. NO. 36318 | 90-LeuLysArgAsnGlyLys-95 |
| SEQ. ID. NO. 36319 | 113-IleArgGluGlnValLysProAspSer-121 |
| g909 | |
| AMPHI Regions - AMPHI | |
| SEQ. ID. NO. 36320 | 24-GlnAspGlySerGly-28 |
| Antigenic Index - Jameson-Wolf | |
| SEQ. ID. NO. 36321 | 22-ThrTyrGlnAspGlySerGlyLysThrAlaValArgAlaLysCysSerThrGlyThrPro-41 |
| SEQ. ID. NO. 36322 | 45-GlnAspGlyArgGlySerLysLysValAspCysAspGluTyrGlyGlyGluArgArgAlaValLeuArgAsnGlnLysArgGlyLysPro AlaThrArgArgAlaAlaThr-81 |
| SEQ. ID. NO. 36323 | 83-GlyLysProSerPheArgAlaArgAspGlyGlyGlyArgValAsnArgAlaGluThrGlyGluGlyLyArgSerAlaArg-109s |
| Hydrophilic Regions - Hopp-Woods | |
| SEQ. ID. NO. 36324 | 23-TyrGlnAspGlySerGlyLysThrAlaValArgAlaLysCysSerThr-38 |
| SEQ. ID. NO. 36325 | 46-AspGlyArgGlySerLysLysValAspCysAspGluTyrGlyGlyGluArgArgAlaValLeuArgAsnGlnLysArgGlyLysProAla ThrArgArgAlaAlaThr-81 |
| SEQ. ID. NO. 36326 | 85-ProSerPheArgAlaArgAspGlyGlyGlyArgValAsnArgAlaGluThrGlyGluGlyLysArgSerAlaArg-109 |
| g910 | |
| AMPHI Regions - AMPHI | |
| SEQ. ID. NO. 36327 | 22-SerAlaGluArgGlnIle-27 |
| SEQ. ID. NO. 36328 | 39-LysAlaValLysMetLeuGlu-45 |
| SEQ. ID. NO. 36329 | 69-AlaTyrLysAspGlyArg-74 |
| Antigenic Index - Jameson-Wolf | |
| SEQ. ID. NO. 36330 | 19-AlaGlyAspSerAlaGluArgGlnIleTyrGlyAspProHisPheGluGlnAsnArgThrLysAlaValLysMetLeuGluGlnArgGlyTyr Gln-50 |
| SEQ. ID. NO. 36331 | 53-AspValAspAlaAspAspTyrTrpGlyLysProValLeuGlu-66 |
| SEQ. ID. NO. 36332 | 68-GluAlaTyrLysAspGlyArgGluTyrAsp-77 |
| SEQ. ID. NO. 36333 | 83-ProAspLeuLysIleIleLysGluGlnLeuAspArg-94 |
| Hydrophilic Regions - Hopp-Woods | |
| SEQ. ID. NO. 36334 | 21-AspSerAlaGluArgGlnIleTyr-28 |
| SEQ. ID. NO. 36335 | 31-ProHisPheGluGlnAsnArgThrLysAlaValLysMetLeuGluGlnArgGly-48 |
| SEQ. ID. NO. 36336 | 53-AspValAspAlaAspAspTyrTrp-60 |
| SEQ. ID. NO. 36337 | 68-GluAlaTyrLysAspGlyArgGluTyrAsp-77 |
| SEQ. ID. NO. 36338 | 86-LysIleIleLysGluGlnLeuAspArg-94 |
| g911 | |
| AMPHI Regions - AMPHI | |
| SEQ. ID. NO. 36339 | 6-LeuGluPheTrpValGlyLeuPhe-13 |
| SEQ. ID. NO. 36340 | 43-ValTyrAlaAspPheGlyAspIleGly-51 |
| SEQ. ID. NO. 36341 | 97-ValSerAlaGlnIle-101 |
| SEQ. ID. NO. 36342 | 118-GlyAspThrGluAsnLeuAla-124 |
| SEQ. ID. NO. 36343 | 140-AsnLeuIleGlyLysPheMetThrSerPhe-149 |
| Antigenic Index - Jameson-Wolf | |
| SEQ. ID. NO. 36344 | 1-MetLysLysAsnIle-5 |
| SEQ. ID. NO. 36345 | 35-GlyGlySerAspLysThrTyr-41 |
| SEQ. ID. NO. 36346 | 48-GlyAspIleGlyGlyLeuLysValAsnAlaProValLys-60 |
| SEQ. ID. NO. 36347 | 74-LeuAspProLysSerTyrGlnAlaArgValArgLeuAspLeuAspGlyLysTyrGlnPheSerSerAspVal-97 |
| SEQ. ID. NO. 36348 | 103-ThrSerGlyLeuLeuGly-108 |
| SEQ. ID. NO. 36349 | 115-GlnGlnGlyGlyAspThrGluAsn-122 |
| SEQ. ID. NO. 36350 | 149-PheAlaGluLysAsnAlaGluGlyGlyAsnAlaGluLysAlaAlaGlu-164 |
| Hydrophilic Regions - Hopp-Woods | |
| SEQ. ID. NO. 36351 | 1-MetLysLysAsnIle-5 |
| SEQ. ID. NO. 36352 | 36-GlySerAspLysThr-40 |
| SEQ. ID. NO. 36353 | 74-LeuAspProLysSerTyrGlnAlaArgValArgLeuAspLeuAspGly-89 |
| SEQ. ID. NO. 36354 | 116-GlnGlyGlyAspThrGluAsn-122 |
| SEQ. ID. NO. 36355 | 149-PheAlaGluLysAsnAlaGluGlyGlyAsnAlaGluLysAlaAlaGlu-164 |
| g912 | |
| AMPHI Regions - AMPHI | |
| SEQ. ID. NO. 36356 | 23-SerProAlaAspAlaValGlyGlnIle-31 |
| SEQ. ID. NO. 36357 | 63-AspPheGlnArgMetThrAlaLeuAlaValGlyAsnProTrpArgThrAlaSerAspAlaGlnLys-84 |
| SEQ. ID. NO. 36358 | 89-LysGluPheGlnThrLeu-94 |
| SEQ. ID. NO. 36359 | 169-TyrArgAsnGlnPheGlyGluIleIleLysAlaLysGlyIleAspGlyLeuIleAla-187 |
| Antigenic Index - Jameson-Wolf | |
| SEQ. ID. NO. 36360 | 1-ValLysLysSerSer-5 |
| SEQ. ID. NO. 36361 | 23-SerProAlaAspAla-27 |
| SEQ. ID. NO. 36362 | 31-IleArgGlnAsnAlaThrGln-37 |
| SEQ. ID. NO. 36363 | 42-LeuLysSerGlyAspAlaAlaSerAlaArgProLysAlaGluAla-56 |
| SEQ. ID. NO. 36364 | 74-AsnProTrpArgThrAlaSerAspAlaGlnLysGlnAlaLeuAlaLysGluPhe-91 |
| SEQ. ID. NO. 36365 | 104-LeuLysPheLysAsn-108 |
| SEQ. ID. NO. 36366 | 112-AsnValLysAspAsnProIleValAsnLysGlyGlyLysGluIleValVal-128 |
| SEQ. ID. NO. 36367 | 134-IleProGlyGlnLysProValAsnMet-142 |
| SEQ. ID. NO. 36368 | 146-ThrTyrGlnSerGlyGlyLysTyrArgThr-155 |
| SEQ. ID. NO. 36369 | 169-TyrArgAsnGlnPhe-173 |
| SEQ. ID. NO. 36370 | 177-IleLysAlaLysGlyIleAsp-183 |
| SEQ. ID. NO. 36371 | 189-LeuLysAlaLysAsnGlyGlyLys-196 |
| Hydrophilic Regions - Hopp-Woods | |
| SEQ. ID. NO. 36372 | 1-ValLysLysSerSer-5 |
| SEQ. ID. NO. 36373 | 31-IleArgGlnAsnAla-35 |
| SEQ. ID. NO. 36374 | 43-LysSerGlyAspAlaAlaSerAlaArgProLysAlaGluAla-56 |
| SEQ. ID. NO. 36375 | 78-ThrAlaSerAspAlaGlnLysGlnAlaLeuAlaLysGluPhe-91 |
| SEQ. ID. NO. 36376 | 104-LeuLysPheLysAsn-108 |
| SEQ. ID. NO. 36377 | 112-AsnValLysAspAsnProIleVal-119 |

TABLE 1-continued

| | |
|---|---|
| SEQ. ID. NO. 36378 | 121-LysGlyGlyLysGluIleValVal-128 |
| SEQ. ID. NO. 36379 | 177-IleLysAlaLysGlyIleAsp-183 |
| SEQ. ID. NO. 36380 | 189-LeuLysAlaLysAsnGlyGlyLys-196 |
| g913 | |
| AMPHI Regions - AMPHI | |
| SEQ. ID. NO. 36381 | 22-GluThrArgProAlaAspProTyrGluGlyTyrAsnArgAlaValSerLysPheAsnAspGlnAla-43 |
| SEQ. ID. NO. 36382 | 53-ArgGlyTyrArgLysValThrProLys-61 |
| SEQ. ID. NO. 36383 | 66-GlyValSerAsnPhePheAsnAsnLeuArgAspValValSer-79 |
| SEQ. ID. NO. 36384 | 107-LeuGlyGlyLeuIleAspIleAlaGly-115 |
| SEQ. ID. NO. 36385 | 151-ValArgAspAlaLeuGlyThrGlyIleThrSerValTyr-163 |
| SEQ. ID. NO. 36386 | 193-AspLeuThrAspSerLeuAspGluAlaAla-202 |
| SEQ. ID. NO. 36387 | 240-LeuValGluSerAla-244 |
| SEQ. ID. NO. 36388 | 259-SerGluThrGlnAla-263 |
| Antigenic Index - Jameson-Wolf | |
| SEQ. ID. NO. 36389 | 1-MetLysLysThrAla-5 |
| SEQ. ID. NO. 36390 | 21-AlaGluThrArgProAlaAspProTyrGluGlyTyrAsnArgAlaValSerLysPheAsnAspGlnAlaAspArgTyr-46 |
| SEQ. ID. NO. 36391 | 51-AlaAlaArgGlyTyrArgLysValThrProLysProValArgAla-65 |
| SEQ. ID. NO. 36392 | 87-LeuAspIleLysArgAlaSerGluAspLeuVal-97 |
| SEQ. ID. NO. 36393 | 117-GlyGlyValProAspAsnLysAsnThrLeuGlyAsp-128 |
| SEQ. ID. NO. 36394 | 132-SerTrpGlyTrpLysAsnSerAsn-139 |
| SEQ. ID. NO. 36395 | 149-SerThrValArgAspAlaLeu-155 |
| SEQ. ID. NO. 36396 | 163-TyrProProLysAsn-167 |
| SEQ. ID. NO. 36397 | 173-ProAlaGlyArgTrpGly-178 |
| SEQ. ID. NO. 36398 | 186-SerThrArgGluGlyLeuLeuAspLeuThrAspSerLeuAspGluAlaAlaIleAspLysTyrSerTyrThrArgAspLeuTyrMet-214 |
| SEQ. ID. NO. 36399 | 216-ValArgAlaArgGlnThrGlyAlaThrProAlaGluGlyThrGluAspAsnIleAspIleAspIleAspGluLeuValGluSerAlaGluThrGly AlaAla-249 |
| SEQ. ID. NO. 36400 | 252-AlaValHisGluAspSerValSerGluThrGlnAlaGluAlaAlaGlyGluAlaGluThrGlnProGlyThrGlnPro-277 |
| Hydrophilic Regions - Hopp-Woods | |
| SEQ. ID. NO. 36401 | 1-MetLysLysThrAla-5 |
| SEQ. ID. NO. 36402 | 21-AlaGluThrArgProAlaAspProTyrGluGlyTyrAsn-33 |
| SEQ. ID. NO. 36403 | 35-AlaValSerLysPheAsnAspGlnAlaAsp-44 |
| SEQ. ID. NO. 36404 | 53-ArgGlyTyrArgLysValThrProLysProValArg-64 |
| SEQ. ID. NO. 36405 | 87-LeuAspIleLysArgAlaSerGluAspLeuVal-97 |
| SEQ. ID. NO. 36406 | 118-GlyValProAspAsnLysAsnThrLeu-126 |
| SEQ. ID. NO. 36407 | 150-ThrValArgAspAlaLeu-155 |
| SEQ. ID. NO. 36408 | 186-SerThrArgGluGlyLeuLeuAspLeuThrAspSerLeuAspGluAlaAlaIleAsp-204 |
| SEQ. ID. NO. 36409 | 216-ValArgAlaArgGlnThrGly-222 |
| SEQ. ID. NO. 36410 | 224-ThrProAlaGluGlyThrGluAspAsnIleAspIleAspIleAspGluLeuValGluSerAlaGluThrGlyAlaAla-249 |
| SEQ. ID. NO. 36411 | 252-AlaValHisGluAspSerValSerGluThrGlnAlaGluAlaAlaGlyGluAlaGluThrGlnPro-273 |
| g914-2 | |
| AMPHI Regions - AMPHI | |
| SEQ. ID. NO. 36412 | 6-LeuGlyIleLeuThrAlaCysAlaAlaMet-15 |
| SEQ. ID. NO. 36413 | 17-AlaPheAlaAspArgIleSerAspLeu-25 |
| SEQ. ID. NO. 36414 | 65-PheGlnLysThrPheGlu-70 |
| SEQ. ID. NO. 36415 | 81-GlnLysValArgGlnAlaCys-87 |
| Antigenic Index - Jameson-Wolf | |
| SEQ. ID. NO. 36416 | 18-PheAlaAspArgIleSerAspLeuGluAlaArgLeuAlaGlnLeuGluHisArgValAlaValLeuGluSerGlyGlyAsnThrValLys-47 |
| SEQ. ID. NO. 36417 | 50-LeuPheGlySerAsnSer-55 |
| SEQ. ID. NO. 36418 | 64-ProPheGlnLysThrPheGluAlaSerAspArgAsnGluGlyValAlaArgGlnLysValArgGlnAlaCysAsnArgGluThrSerAla-93 |
| SEQ. ID. NO. 36419 | 96-CysGlyAspGluAlaIleArgCysArgLysPheAsp-107 |
| Hydrophilic Regions - Hopp-Woods | |
| SEQ. ID. NO. 36420 | 18-PheAlaAspArgIleSerAspLeuGluAlaArgLeuAlaGlnLeuGluHisArgValAlaVal-38 |
| SEQ. ID. NO. 36421 | 67-LysThrPheGluAlaSerAspArgAsnGluGlyValAlaArgGlnLysValArgGlnAlaCysAsnArgGluThrSer-92 |
| SEQ. ID. NO. 36422 | 96-CysGlyAspGluAlaIleArgCysArgLysPheAsp-107 |
| g915 | |
| AMPHI Regions - AMPHI | |
| SEQ. ID. NO. 36423 | 8-IleValAlaValPheAlaLeuSerAla-16 |
| SEQ. ID. NO. 36424 | 31-IleSerAspArgSerVal-36 |
| SEQ. ID. NO. 36425 | 69-ValLysGlnMetPheGlyTyrThrLysLeuProGluGluProLysGlyIleArgValIleTyrValThrAspMetGlyAsnValThrAspTrp Thr-100 |
| SEQ. ID. NO. 36426 | 139-GlnAlaGluLysPhe-143 |
| Antigenic Index - Jameson-Wolf | |
| SEQ. ID. NO. 36427 | 16-AlaCysArgGlnAlaGluGluAlaProProProLeuProArgGlnIleSerAspArgSerValGlyHisTyrCysSerMetAsnLeuThrGlu HisAsnGlyProLysAla-52 |
| SEQ. ID. NO. 36428 | 56-LeuAsnGlyLysProAspGlnProVal-64 |
| SEQ. ID. NO. 36429 | 75-TyrThrLysLeuProGluGluProLysGlyIle-85 |
| SEQ. ID. NO. 36430 | 92-AspMetGlyAsnValThrAspTrpThrAsnProAsnAlaAspThrGluTrpIleAspAlaLysLys-113 |
| SEQ. ID. NO. 36431 | 125-GlyMetGlyAlaGluAspAlaLeuProPheGlyAsnLysGluGlnAlaGluLysPheAlaLysAspLysGlyGlyLysValValGly-153 |
| SEQ. ID. NO. 36432 | 155-AspAspMetProAsp-159 |
| Hydrophilic Regions - Hopp-Woods | |
| SEQ. ID. NO. 36433 | 18-ArgGlnAlaGluGluAlaProProProLeu-27 |
| SEQ. ID. NO. 36434 | 30-GlnIleSerAspArgSerVal-36 |
| SEQ. ID. NO. 36435 | 46-GluHisAsnGlyProLys-51 |
| SEQ. ID. NO. 36436 | 58-GlyLysProAspGln-62 |
| SEQ. ID. NO. 36437 | 77-LysLeuProGluGluProLysGlyIle-85 |
| SEQ. ID. NO. 36438 | 103-AsnAlaAspThrGluTrpIleAspAlaLysLys-113 |

TABLE 1-continued

| | |
|---|---|
| SEQ. ID. NO. 36439 | 127-GlyAlaGluAspAlaLeu-132 |
| SEQ. ID. NO. 36440 | 135-GlyAsnLysGluGlnAlaGluLysPheAlaLysAspLysGlyGlyLys-150 |
| SEQ. ID. NO. 36441 | 155-AspAspMetProAsp-159 |
| g917 | |
| AMPHI Regions - AMPHI | |
| SEQ. ID. NO. 36442 | 6-ProLeuAlaValLeuThrAlaLeuLeuLeu-15 |
| SEQ. ID. NO. 36443 | 35-GlnAsnValLeuLysIleTyrAsnTrpSerGluTyrValAspProGluThrValAlaAsp-54 |
| SEQ. ID. NO. 36444 | 99-IleLysAlaGlyAlaTyrGlnLysIleAspLysSer-110 |
| SEQ. ID. NO. 36445 | 124-ArgLeuMetAspGlyValAsp-130 |
| SEQ. ID. NO. 36446 | 152-ArgValLysLysAlaLeu-157 |
| SEQ. ID. NO. 36447 | 188-AspSerAlaAlaGlu-192 |
| SEQ. ID. NO. 36448 | 206-AsnSerSerAsnThrGluAspIleArgGluAlaThr-217 |
| SEQ. ID. NO. 36449 | 292-AlaLysAsnValAlaAsnAlaHisLysTyrIleAsnAspPheLeuAsp-307 |
| SEQ. ID. NO. 36450 | 325-LysProAlaArgAspLeuMetGluAsp-333 |
| Antigenic Index - Jameson-Wolf | |
| SEQ. ID. NO. 36451 | 18-CysGlyGlySerAspLysProProAlaGluLysProAlaProAlaGluAsnGlnAsnVal-37 |
| SEQ. ID. NO. 36452 | 44-SerGluTyrValAspProGluThrValAlaAspPheGluLysLysAsnGlyIleLysValThr-64 |
| SEQ. ID. NO. 36453 | 68-TyrAspSerAspGluThrLeuGluSerLysValLeuThrGlyLysSerGlyTyrAsp-86 |
| SEQ. ID. NO. 36454 | 102-GlyAlaTyrGlnLysIleAspLysSerMetIleProAsnTyrLysHisLeuAsnProGluMetMetArgLeuMetAspGlyValAspProAsp HisGluTyr-135 |
| SEQ. ID. NO. 36455 | 149-AsnThrGluArgValLysLysAlaLeuGlyThrAspLysLeuProAspAsnGln-166 |
| SEQ. ID. NO. 36456 | 171-PheAsnProGluTyr-175 |
| SEQ. ID. NO. 36457 | 179-LeuLysGlnCysGly-183 |
| SEQ. ID. NO. 36458 | 201-LeuGlyLysAsnProAsnSerSerAsnThrGluAspIleArgGluAlaThrAlaLeuLeuLysLysAsnArgProAsnIleLysArgPheThr SerSerGlyPheIle-236 |
| SEQ. ID. NO. 36459 | 238-AspLeuAlaArgGlyAspThr-244 |
| SEQ. ID. NO. 36460 | 255-AsnIleAlaLysArgArgAlaGluGluAlaGlyGlyLysGluLysIleArgValMetMetProLysGluGlyValGly-280 |
| SEQ. ID. NO. 36461 | 287-ValIleProLysAspAlaLysAsnValAlaAsn-297 |
| SEQ. ID. NO. 36462 | 305-PheLeuAspProGluValSerAlaLysAsnGlyAsn-316 |
| SEQ. ID. NO. 36463 | 320-TyrAlaProSerSerLysProAlaArgAspLeuMetGluAspGluPheLysAsnAspAsnThrIlePheProSerGlyGluAspLeuLys Asn-350 |
| SEQ. ID. NO. 36464 | 368-GlnTrpGlnAspValLysAlaGlyLys-376 |
| Hydrophilic Regions - Hopp-Woods | |
| SEQ. ID. NO. 36465 | 19-GlyGlySerAspLysProProAlaGluLysProAlaProAlaGluAsn-34 |
| SEQ. ID. NO. 36466 | 47-ValAspProGluThrValAlaAspPheGluLysLysAsnGlyIle-61 |
| SEQ. ID. NO. 36467 | 68-TyrAspSerAspGluThrLeuGluSerLysValLeuThr-80 |
| SEQ. ID. NO. 36468 | 105-GlnLysIleAspLysSerMet-111 |
| SEQ. ID. NO. 36469 | 121-GluMetMetArgLeuMetAspGlyValAspProAspHisGluTyr-135 |
| SEQ. ID. NO. 36470 | 149-AsnThrGluArgValLysLysAlaLeuGlyThrAspLysLeuProAspAsnGln-166 |
| SEQ. ID. NO. 36471 | 204-AsnProAsnSerSerAsnThrGluAspIleArgGluAlaThrAlaLeuLeuLysLysAsnArgProAsnIleLysArgPheThr-231 |
| SEQ. ID. NO. 36472 | 238-AspLeuAlaArgGlyAspThr-244 |
| SEQ. ID. NO. 36473 | 255-AsnIleAlaLysArgArgAlaGluGluAlaGlyGlyLysGluLysIleArgValMetMetProLysGluGly-278 |
| SEQ. ID. NO. 36474 | 290-LysAspAlaLysAsnValAlaAsn-297 |
| SEQ. ID. NO. 36475 | 305-PheLeuAspProGluValSerAlaLysAsn-314 |
| SEQ. ID. NO. 36476 | 322-ProSerSerLysProAlaArgAspLeuMetGluAspGluPheLysAsnAspAsn-339 |
| SEQ. ID. NO. 36477 | 344-SerGlyGluAspLeuLysAsn-350 |
| SEQ. ID. NO. 36478 | 370-GlnAspValLysAlaGlyLys-376 |
| g919 | |
| AMPHI Regions - AMPHI | |
| SEQ. ID. NO. 36479 | 8-SerAlaLeuTyrGlyIleAlaAlaAlaIleLeu-18 |
| SEQ. ID. NO. 36480 | 24-ArgSerIleGlnThrPheProGln-31 |
| SEQ. ID. NO. 36481 | 37-IleAsnGlyProAspArgProAlaGlyIleProAspProAlaGly-51 |
| SEQ. ID. NO. 36482 | 76-AspPheAlaLysSerLeuGln-82 |
| SEQ. ID. NO. 36483 | 98-GlnAspValCysAlaGlnAlaPheGlnThrProVal-109 |
| SEQ. ID. NO. 36484 | 118-PheGluArgTyrPheThr-123 |
| SEQ. ID. NO. 36485 | 133-LeuAlaGlyThrValThrGlyTyrTyrGlu-142 |
| SEQ. ID. NO. 36486 | 161-GlyIleProAspAspPheIleSerValPro-170 |
| SEQ. ID. NO. 36487 | 176-ArgGlyGlyLysAsnLeuValArgIleArgGln-186 |
| SEQ. ID. NO. 36488 | 191-SerGlyThrIleAspAsnAlaGlyGlyThr-200 |
| SEQ. ID. NO. 36489 | 308-GlnGlyIleLysAlaTyrMetArgGlnAsnProGlnArgLeuAlaGluValLeu-325 |
| SEQ. ID. NO. 36490 | 348-AlaLeuGlyThrProLeuMetGlyGluTyrAlaGlyAlaIle-361 |
| SEQ. ID. NO. 36491 | 382-ArgLysAlaLeuAsnArg-387 |
| Antigenic Index - Jameson-Wolf | |
| SEQ. ID. NO. 36492 | 1-MetLysLysHisLeuLeu-6 |
| SEQ. ID. NO. 36493 | 21-CysGlnSerArgSerIleGln-27 |
| SEQ. ID. NO. 36494 | 30-ProGlnProAspThr-34 |
| SEQ. ID. NO. 36495 | 36-ValIleAsnGlyProAspArgProAlaGlyIleProAspProAlaGly-51 |
| SEQ. ID. NO. 36496 | 76-AspPheAlaLysSerLeuGln-82 |
| SEQ. ID. NO. 36497 | 87-GlyCysAlaAsnLeuLysAsnArgGlnGlyTrpGln-98 |
| SEQ. ID. NO. 36498 | 113-GlnAlaLysArgPhePhe-118 |
| SEQ. ID. NO. 36499 | 121-TyrPheThrProTrp-125 |
| SEQ. ID. NO. 36500 | 143-ProValLeuLysGlyAspGlyArgArgThrGluArgAlaArg-156 |
| SEQ. ID. NO. 36501 | 161-GlyIleProAspAspPheIle-167 |
| SEQ. ID. NO. 36502 | 173-AlaGlyLeuArgGlyGlyLysAsnLeuValArgIleArgGlnThrGlyLysAsnSerGlyThrIleAspAsnAlaGlyGlyThrHis-201 |
| SEQ. ID. NO. 36503 | 215-ThrAlaIleLysGlyArgPheGluGlySerArgPheLeuProTyrHisThrArgAsnGlnIleAsnGlyGlyAlaLeuAspGlyLysAla Pro-245 |
| SEQ. ID. NO. 36504 | 250-AlaGluAspProValGlu-255 |
| SEQ. ID. NO. 36505 | 262-GlnGlySerGlyArgLeuLysThrProSerGlyLysTyrIleArg-276 |
| SEQ. ID. NO. 36506 | 278-GlyTyrAlaAspLysAsnGluHisPro-286 |
| SEQ. ID. NO. 36507 | 293-TyrMetAlaAspLysGlyTyrLeuLysLeuGlyGln-304 |

TABLE 1-continued

SEQ. ID. NO. 36508 312-AlaTyrMetArgGlnAsnProGlnArgLeuAlaGlu-323
SEQ. ID. NO. 36509 326-GlyGlnAsnProSer-330
SEQ. ID. NO. 36510 337-LeuAlaGlySerGlyAsnGluGlyProVal-346
SEQ. ID. NO. 36511 359-GlyAlaIleAspArgHisTyr-365
SEQ. ID. NO. 36512 379-ProValThrArgLysAlaLeuAsn-386
SEQ. ID. NO. 36513 393-AspThrGlySerAlaIleLysGlyAlaValArg-403
SEQ. ID. NO. 36514 409-GlyTyrGlyAspGluAlaGlyGluLeuAlaGlyLysGlnLysThrThr-424
SEQ. ID. NO. 36515 431-LeuProAsnGlyMetLysProGluTyrArgPro-441
Hydrophilic Regions - Hopp-Woods
SEQ. ID. NO. 36516 1-MetLysLysHisLeuLeu-6
SEQ. ID. NO. 36517 38-AsnGlyProAspArgProAlaGlyIleProAspProAlaGly-51
SEQ. ID. NO. 36518 90-AsnLeuLysAsnArgGlnGlyTrp-97
SEQ. ID. NO. 36519 144-ValLeuLysGlyAspGlyArgArgThrGluArgAlaArg-156
SEQ. ID. NO. 36520 175-LeuArgGlyGlyLysAsnLeuValArgIleArgGlnThrGlyLysAsnSerGlyThrIleAspAsnAlaGly-198
SEQ. ID. NO. 36521 215-ThrAlaIleLysGlyArgPheGluGly-223
SEQ. ID. NO. 36522 239-AlaLeuAspGlyLysAla-244
SEQ. ID. NO. 36523 250-AlaGluAspProVal-254
SEQ. ID. NO. 36524 265-GlyArgLeuLysThrProSer-271
SEQ. ID. NO. 36525 279-TyrAlaAspLysAsnGluHis-285
SEQ. ID. NO. 36526 317-AsnProGlnArgLeuAlaGlu-323
SEQ. ID. NO. 36527 337-LeuAlaGlySerGlyAsnGluGlyPro-345
SEQ. ID. NO. 36528 380-ValThrArgLysAlaLeuAsn-386
SEQ. ID. NO. 36529 393-AspThrGlySerAlaIle-398
SEQ. ID. NO. 36530 412-AspGluAlaGlyGluLeuAlaGlyLysGlnLysThr-423
SEQ. ID. NO. 36531 434-GlyMetLysProGluTyrArgPro-441
g920-2
AMPHI Regions - AMPHI
SEQ. ID. NO. 36532 43-GlyGluPheProGluLeuGluProIleAla-52
SEQ. ID. NO. 36533 117-GlyIleLysGluMetProAsp-123
SEQ. ID. NO. 36534 135-LysAsnIleValAsnVal-140
SEQ. ID. NO. 36535 163-LeuAspAsnProAlaAsn-168
SEQ. ID. NO. 36536 190-ThrValThrAlaThrPheAspGlyPheAspThrSerAspArgSerLys-205
SEQ. ID. NO. 36537 212-GlnAlaPheSerAspSerThr-218
Antigenic Index - Jameson-Wolf
SEQ. ID. NO. 36538 40-LeuGlyTyrGlyGluPheProGlu-47
SEQ. ID. NO. 36539 49-GluProIleAlaLysAspArgLeu-56
SEQ. ID. NO. 36540 66-ValThrGluLysGlyLysGluAsnMetIle-75
SEQ. ID. NO. 36541 77-ArgGlyThrTyrAsnTyrGlnTyrArgSerAsnArgProValLysAspGlySerTyr-95
SEQ. ID. NO. 36542 104-ThrPheTrpSerLysAsnLysAlaGlyTrp-113
SEQ. ID. NO. 36543 116-AlaGlyIleLysGluMetProAspAlaSerTyrCysGluGlnThrArgMetPheGlyLysAsnIleValAsnValGlyHisGluSerAla
AspThr-147
SEQ. ID. NO. 36544 152-LysProValGlyGlnAsnLeuGlu-159
SEQ. ID. NO. 36545 162-ProLeuAspAsnProAla-167
SEQ. ID. NO. 36546 173-GluArgPheLysVal-177
SEQ. ID. NO. 36547 181-PheArgGlyGluProLeuProAsnAla-189
SEQ. ID. NO. 36548 194-ThrPheAspGlyPheAspThrSerAspArgSerLysThrHisLysThrGluAla-211
SEQ. ID. NO. 36549 213-AlaPheSerAspSerThrAspAspLysGlyGluValAsp-225
SEQ. ID. NO. 36550 237-AsnValGluHisLysThrAspPheProAspGlnSerValCysGlnLysGlnAlaAsnTyrSer-257
Hydrophilic Regions - Hopp-Woods
SEQ. ID. NO. 36551 49-GluProIleAlaLysAspArgLeu-56
SEQ. ID. NO. 36552 66-ValThrGluLysGlyLysGluAsnMetIle-75
SEQ. ID. NO. 36553 85-ArgSerAsnArgProValLysAspGlySer-94
SEQ. ID. NO. 36554 107-SerLysAsnLysAlaGlyTrp-113
SEQ. ID. NO. 36555 116-AlaGlyIleLysGluMetProAsp-123
SEQ. ID. NO. 36556 128-GluGlnThrArgMetPheGly-134
SEQ. ID. NO. 36557 142-HisGluSerAlaAsp-146
SEQ. ID. NO. 36558 173-GluArgPheLysVal-177
SEQ. ID. NO. 36559 196-AspGlyPheAspThrSerAspArgSerLysThrHisLysThrGluAla-211
SEQ. ID. NO. 36560 213-AlaPheSerAspSerThrAspAspLysGlyGluValAsp-225
SEQ. ID. NO. 36561 237-AsnValGluHisLysThrAspPheProAsp-246
SEQ. ID. NO. 36562 248-SerValCysGlnLys-252
g921
AMPHI Regions - AMPHI
SEQ. ID. NO. 36563 12-AlaValLeuSerGlyCysGlnSerIleTyrValProThrLeuThrGluIleProValAsn-31
SEQ. ID. NO. 36564 33-IleAsnThrValLysThr-38
SEQ. ID. NO. 36565 51-HisTrpAlaAspValAlaLysIleSerAspGlu-61
SEQ. ID. NO. 36566 72-GlyLysMetThrLysValGlnAlaAlaGlnTyrLeuAsnAsnPheArgLys-88
SEQ. ID. NO. 36567 98-AspSerMetTyrGluIleTyrLeuArg-106
SEQ. ID. NO. 36568 126-GluAsnAlaLeuArgGlyTrpGlnGlnArgTrp-136
Antigenic Index - Jameson-Wolf
SEQ. ID. NO. 36569 36-ValLysThrGluAlaProAlaLysGlyPheArg-46
SEQ. ID. NO. 36570 56-AlaLysIleSerAspGluAlaThrArg-64
SEQ. ID. NO. 36571 72-GlyLysMetThrLys-76
SEQ. ID. NO. 36572 84-AsnAsnPheArgLysArgLeuValGlyArgAsnAlaValAspAspSerMet-100
SEQ. ID. NO. 36573 107-SerAlaValAspSerGlnArgGlyGluIleAsnThrGluGlnSerLysLeuTyr-124
SEQ. ID. NO. 36574 128-AlaLeuArgGlyTrpGlnGlnArgTrpLysAsnMetAspAlaLysProAspAsnProAla-147
Hydrophilic Regions - Hopp-Woods
SEQ. ID. NO. 36575 36-ValLysThrGluAlaProAlaLysGlyPheArg-46
SEQ. ID. NO. 36576 56-AlaLysIleSerAspGluAlaThrArg-64
SEQ. ID. NO. 36577 86-PheArgLysArgLeuValGly-92

TABLE 1-continued

| | |
|---|---|
| SEQ. ID. NO. 36578 | 94-AsnAlaValAspAspSerMet-100 |
| SEQ. ID. NO. 36579 | 107-SerAlaValAspSerGlnArgGlyGluIleAsnThrGluGlnSerLysLeuTyr-124 |
| SEQ. ID. NO. 36580 | 136-TrpLysAsnMetAspAlaLysProAspAsn-145 |
| g922 | |
| AMPHI Regions - AMPHI | |
| SEQ. ID. NO. 36581 | 16-LeuSerAlaCysThrAla-21 |
| SEQ. ID. NO. 36582 | 28-ArgAlaAsnGluAlaGlnAlaPro-35 |
| SEQ. ID. NO. 36583 | 66-ValArgArgPheValAspAsp-72 |
| SEQ. ID. NO. 36584 | 82-AlaGluTrpGlnAspPhePheAspLys-90 |
| SEQ. ID. NO. 36585 | 98-ValLysIleMetHis-102 |
| SEQ. ID. NO. 36586 | 138-AspAspValAlaGln-142 |
| SEQ. ID. NO. 36587 | 166-GlySerPheArgValAlaAspAlaLeu-174 |
| SEQ. ID. NO. 36588 | 190-LysGluLeuValGluLeuLeuLysLeuAla-199 |
| SEQ. ID. NO. 36589 | 216-AlaMetGlyMetPro-220 |
| SEQ. ID. NO. 36590 | 239-HisArgAspIleTrpGlyAsnValGlyAspValAlaAlaSerValAlaAsnTyrMetLysGlnHis-260 |
| SEQ. ID. NO. 36591 | 292-ArgThrValAlaAspLeuLysAlaTyr-300 |
| SEQ. ID. NO. 36592 | 329-TyrLeuGlyLeuAsnAsnPheTyrThr-337 |
| Antigenic Index - Jameson-Wolf | |
| SEQ. ID. NO. 36593 | 1-MetGluLysArgLysIleLeu-7 |
| SEQ. ID. NO. 36594 | 22-MetGluAlaArgThrProArgAlaAsnGluAlaGlnAlaProArgAlaAspGluMetLysLysGluSerArgProAlaPhe-48 |
| SEQ. ID. NO. 36595 | 55-ValSerAspSerGlyPhe-60 |
| SEQ. ID. NO. 36596 | 64-AlaAsnValArgArgPheValAspAspGluValGlyLysGlyAspPheSerGln-81 |
| SEQ. ID. NO. 36597 | 101-MetHisArgProSerThrSerArgPro-109 |
| SEQ. ID. NO. 36598 | 114-ArgThrGlyAsnSerGlyArgAlaLysPheHisGly-125 |
| SEQ. ID. NO. 36599 | 127-ArgArgPheTyrAlaGluAsnArgAlaValIleAspAspValAlaGlnLysTyrGlyVal-146 |
| SEQ. ID. NO. 36600 | 157-IleGluThrAsnTyrGlyLysAsnThrGlySer-167 |
| SEQ. ID. NO. 36601 | 180-AspTyrProArgArgAlaGlyPhePhe-188 |
| SEQ. ID. NO. 36602 | 197-LysLeuAlaLysGluGluGlyGlyAsp-205 |
| SEQ. ID. NO. 36603 | 223-MetProSerSerTyrArgLysTrpAlaValAspTyrAspGlyAspGlyHisArgAspIle-242 |
| SEQ. ID. NO. 36604 | 260-HisGlyTrpArgThrGlyGlyLysMet-268 |
| SEQ. ID. NO. 36605 | 275-AlaProGlyAlaAsp-279 |
| SEQ. ID. NO. 36606 | 284-IleGlyGluLysThrAlaLeu-290 |
| SEQ. ID. NO. 36607 | 304-ProGlyGluThrLeuAlaAspAspGluLysAlaVal-315 |
| SEQ. ID. NO. 36608 | 320-GluThrAlaProGly-324 |
| SEQ. ID. NO. 36609 | 351-ValArgAspIleAlaAsnSerLeuGlyGlyProGlyLeu-363 |
| Hydrophilic Regions - Hopp-Woods | |
| SEQ. ID. NO. 36610 | 1-MetGluLysArgLysIleLeu-7 |
| SEQ. ID. NO. 36611 | 22-MetGluAlaArgThrProArgAlaAsnGluAlaGlnAlaProArgAlaAspGluMetLysLysGluSerArgProAlaPhe-48 |
| SEQ. ID. NO. 36612 | 64-AlaAsnValArgArgPheValAspAspGluValGlyLysGlyAspPheSerGln-81 |
| SEQ. ID. NO. 36613 | 116-GlyAsnSerGlyArgAlaLysPheHisGly-125 |
| SEQ. ID. NO. 36614 | 127-ArgArgPheTyrAlaGluAsnArgAlaValIleAspAspValAlaGln-142 |
| SEQ. ID. NO. 36615 | 160-AsnTyrGlyLysAsnThrGly-166 |
| SEQ. ID. NO. 36616 | 181-TyrProArgArgAlaGlyPhePhe-188 |
| SEQ. ID. NO. 36617 | 197-LysLeuAlaLysGluGluGlyGlyAsp-205 |
| SEQ. ID. NO. 36618 | 234-TyrAspGlyAspGlyHisArgAspIle-242 |
| SEQ. ID. NO. 36619 | 284-IleGlyGluLysThrAlaLeu-290 |
| SEQ. ID. NO. 36620 | 307-ThrLeuAlaAspAspGluLysAlaVal-315 |
| SEQ. ID. NO. 36621 | 351-ValArgAspIleAla-355 |
| g923-2 | |
| AMPHI Regions - AMPHI | |
| SEQ. ID. NO. 36622 | 9-ProMetAlaCysAlaAlaPheLeu-16 |
| SEQ. ID. NO. 36623 | 26-LeuGlyAlaCysTyrAlaIleLeuSerLeuTyrAla-37 |
| SEQ. ID. NO. 36624 | 63-ProAlaLeuPheGlyGlyTrpThrGly-71 |
| Antigenic Index - Jameson-Wolf | |
| SEQ. ID. NO. 36625 | 43-IleAspLysArgArgAlaValArgGlyLysArgArgIleProGluHisArgLeu-60 |
| SEQ. ID. NO. 36626 | 77-ArgMetPheArgHisLysThrAlaLysLysArgPhe-88 |
| Hydrophilic Regions - Hopp-Woods | |
| SEQ. ID. NO. 36627 | 43-IleAspLysArgArgAlaValArgGlyLysArgArgIleProGluHisArgLeu-60 |
| SEQ. ID. NO. 36628 | 77-ArgMetPheArgHisLysThrAlaLysLysArgPhe-88 |
| g925-1 | |
| AMPHI Regions - AMPHI | |
| SEQ. ID. NO. 36629 | 115-LysCysGlyGlnThrAlaGln-121 |
| SEQ. ID. NO. 36630 | 154-PheAspGluLeuGlu-158 |
| Antigenic Index - Jameson-Wolf | |
| SEQ. ID. NO. 36631 | 16-GlyCysGlyLysAspAlaGlyGlyTyrGluGlyTyrTrpArgGluLysSerAspLysLysGluGly ValIleAlaValLysLysLysGlyAsnTyrPhe-48 |
| SEQ. ID. NO. 36632 | 56-ThrGlyLysGluGluSerLeuLeuLeuSerGluLysAspGlyAla-70 |
| SEQ. ID. NO. 36633 | 74-AsnThrGlyIleGly-78 |
| SEQ. ID. NO. 36634 | 80-IleProIleLysLeuSerAspAspGlyLysGluLeuTyrValGluArgArgArgTyrValLysThrAspAlaAlaMetLysAspLysIleIle AlaHisGlnLysLysCysGlyGlnThr-119 |
| SEQ. ID. NO. 36635 | 124-LeuAspAlaArgAsnAlaLeuProSerAsnGlnThrTyrGlnGlnArgGlnAlaAla-142 |
| SEQ. ID. NO. 36636 | 144-GluGlnLeuLysArgArgPheGluAlaGluPheAspGluLeuGluLysGluIleLysCysAsnGlyLysProThr-168 |
| Hydrophilic Regions - Hopp-Woods | |
| SEQ. ID. NO. 36637 | 17-CysGlyLysAspAlaGlyGly-23 |
| SEQ. ID. NO. 36638 | 27-TyrTrpArgGluLysSerAspLysLysGluGlyValIleAlaValLysLysLysGly-45 |
| SEQ. ID. NO. 36639 | 56-ThrGlyLysGluGluSerLeuLeuLeuSerGluLysAspGlyAla-70 |
| SEQ. ID. NO. 36640 | 80-IleProIleLysLeuSerAspAspGlyLysGluLeuTyrValGluArgArgArgTyrValLysThrAspAlaAlaMetLysAspLysIleIle AlaHisGlnLysLysCysGlyGln-118 |

TABLE 1-continued

| | |
|---|---|
| SEQ. ID. NO. 36641 | 124-LeuAspAlaArgAsnAlaLeu-130 |
| SEQ. ID. NO. 36642 | 136-TyrGlnGlnArgGlnAlaAla-142 |
| SEQ. ID. NO. 36643 | 144-GluGlnLeuLysArgArgPheGluAlaGluPheAspGluLeuGluLysGluIleLysCysAsnGlyLys-166 |
| g926 | |
| AMPHI Regions - AMPHI | |
| SEQ. ID. NO. 36644 | 29-ProSerGluHisIleSerSerPhe-36 |
| SEQ. ID. NO. 36645 | 72-LeuGlySerThrLeuGlyGln-78 |
| SEQ. ID. NO. 36646 | 98-AlaGluGlyThrGluAspLeuSerArgGln-107 |
| Antigenic Index - Jameson-Wolf | |
| SEQ. ID. NO. 36647 | 19-LeuProGlnAsnAsnGluAsnLeuTrpGlnProSerGluHisIleSer-34 |
| SEQ. ID. NO. 36648 | 37-AlaAlaGluGlyArgLeuAlaValLysAlaGluGlyLysGlySerTyrAla-53 |
| SEQ. ID. NO. 36649 | 70-ThrProLeuGlySer-74 |
| SEQ. ID. NO. 36650 | 79-LeuCysGlnAspArgAspGlyAlaLeu-87 |
| SEQ. ID. NO. 36651 | 89-ValAspGlyLysGlyAsnValTyr-96 |
| SEQ. ID. NO. 36652 | 98-AlaGluGlyThrGluAspLeuSerArgGln-107 |
| SEQ. ID. NO. 36653 | 123-GluGlyArgArgValAlaGlyAlaProTyrArgIleArgSerAspGlyIleLeu-140 |
| SEQ. ID. NO. 36654 | 143-TyrGlyTrpThrIleGlyGlnAsnCysArgGlnTrpGly-155 |
| SEQ. ID. NO. 36655 | 157-SerProAsnValAlaThrGlu-163 |
| Hydrophilic Regions - Hopp-Woods | |
| SEQ. ID. NO. 36656 | 37-AlaAlaGluGlyArgLeuAlaValLysAlaGluGlyLysGlySer-51 |
| SEQ. ID. NO. 36657 | 80-CysGlnAspArgAspGlyAlaLeu-87 |
| SEQ. ID. NO. 36658 | 89-ValAspGlyLysGly-93 |
| SEQ. ID. NO. 36659 | 99-GluGlyThrGluAspLeuSerArg-106 |
| SEQ. ID. NO. 36660 | 123-GluGlyArgArgValAla-128 |
| SEQ. ID. NO. 36661 | 132-TyrArgIleArgSerAspGlyIleLeu-140 |
| g927 | |
| AMPHI Regions - AMPHI | |
| SEQ. ID. NO. 36662 | 13-LeuLeuThrAlaCys-17 |
| SEQ. ID. NO. 36663 | 48-SerTyrAspValThrArgTyrPheTyrLysGlu-58 |
| SEQ. ID. NO. 36664 | 120-LysGlyTrpGlnGlnAlaLeuPro-127 |
| SEQ. ID. NO. 36665 | 145-AsnProLysGlnIleArgAspTrpAsnAspLeuAlaLysAspGly-159 |
| SEQ. ID. NO. 36666 | 195-LysLeuValAlaSerIleLeu-201 |
| Antigenic Index - Jameson-Wolf | |
| SEQ. ID. NO. 36667 | 17-CysSerProAlaAlaAspSerAsnHisProSerGlyGlnAsnAlaProAlaAsnThrGluSerAspGlyLysAsnIle-42 |
| SEQ. ID. NO. 36668 | 65-GlyThrTyrGlnSerGluHisProGlyThrSer-75 |
| SEQ. ID. NO. 36669 | 81-SerHisGlyGlyPheSer-86 |
| SEQ. ID. NO. 36670 | 104-AsnGlnSerSerAspIleAspLeuLeuGluLysXxxGlyLeuVal-118 |
| SEQ. ID. NO. 36671 | 126-LeuProAspHisAlaAlaProTyrThr-134 |
| SEQ. ID. NO. 36672 | 142-ArgLysAsnAsnProLysGlnIleArgAspTrpAsnAspLeuAlaLysAspGlyVal-160 |
| SEQ. ID. NO. 36673 | 165-AlaLysThrSerGlyAsnGlyArg-172 |
| SEQ. ID. NO. 36674 | 183-LeuLysAlaAsnAsnGlyAsnGluGlnGluAlaGlnLys-195 |
| SEQ. ID. NO. 36675 | 201-LeuLysAsnThrProValPheGluAsnGlyGlyArgXxxProProProProProSerHisAsnAlaThrSer-224 |
| SEQ. ID. NO. 36676 | 229-SerLeuLeuLysThrLysProThrThrSerAlaLysAsn-241 |
| Hydrophilic Regions - Hopp-Woods | |
| SEQ. ID. NO. 36677 | 19-ProAlaAlaAspSerAsnHisProSer-27 |
| SEQ. ID. NO. 36678 | 33-AlaAsnThrGluSerAspGlyLysAsn-41 |
| SEQ. ID. NO. 36679 | 68-GlnSerGluHisProGly-73 |
| SEQ. ID. NO. 36680 | 105-GlnSerSerAspIleAspLeuLeuGluLysXxxGlyLeuVal-118 |
| SEQ. ID. NO. 36681 | 142-ArgLysAsnAsnProLysGlnIleArgAspTrpAsnAspLeuAlaLysAspGlyVal-160 |
| SEQ. ID. NO. 36682 | 167-ThrSerGlyAsnGly-171 |
| SEQ. ID. NO. 36683 | 185-AlaAsnAsnGlyAsnGluGlnGluAlaGlnLys-195 |
| SEQ. ID. NO. 36684 | 209-AsnGlyGlyArgXxxProProPro-216 |
| SEQ. ID. NO. 36685 | 231-LeuLysThrLysProThrThrSerAlaLysAsn-241 |
| g929 | |
| AMPHI Regions - AMPHI | |
| SEQ. ID. NO. 36686 | 25-ValProAspGlyValLys-30 |
| SEQ. ID. NO. 36687 | 34-TrpThrLeuLeuAlaMetPheValGlyValIleAlaAlaIleIleGly-49 |
| SEQ. ID. NO. 36688 | 53-ProLeuGlyAlaLeuSer-58 |
| SEQ. ID. NO. 36689 | 76-GlyAlaAlaMetSerAspAlaLeuSerAlaPhe-86 |
| SEQ. ID. NO. 36690 | 155-HisProIleMetGlnSerIleAlaGlySerTyrGlySerAsnProAlaLys-171 |
| SEQ. ID. NO. 36691 | 180-TyrLeuAlaLeuVal-184 |
| SEQ. ID. NO. 36692 | 187-HisSerAsnProIle-191 |
| SEQ. ID. NO. 36693 | 204-ProLeuIleValAsnLeuIleAlaGluAsnLeuGly-215 |
| SEQ. ID. NO. 36694 | 233-GlyValIleAlaPhePhe-238 |
| SEQ. ID. NO. 36695 | 265-ArgLeuSerGluMetGlyLys-271 |
| SEQ. ID. NO. 36696 | 280-AlaValIlePheGlyIle-285 |
| SEQ. ID. NO. 36697 | 355-LeuGlyLeuIleLysTrpPheSerGlyValLeuAlaGluSerValGlyGlyLeu-372 |
| SEQ. ID. NO. 36698 | 398-ThrAlaHisIleThrAlaMetPheGlyAlaPheLeuAla-410 |
| SEQ. ID. NO. 36699 | 452-TyrThrThrMetGlyGluTrpTrp-459 |
| SEQ. ID. NO. 36700 | 469-AsnPheLeuIlePheSerValIleGlySerIleTrpTrpLysValLeuGlyTyr-486 |
| Antigenic Index - Jameson-Wolf | |
| SEQ. ID. NO. 36701 | 25-ValProAspGlyValLysProGln-32 |
| SEQ. ID. NO. 36702 | 71-ThrAlaAspLysProGlyAlaAlaMet-79 |
| SEQ. ID. NO. 36703 | 122-GlyArgLysThrLeuGlyIle-128 |
| SEQ. ID. NO. 36704 | 143-ThrProSerAsnThrAlaArgGlyGlyGly-152 |
| SEQ. ID. NO. 36705 | 163-GlySerTyrGlySerAsnProAlaLysGlyThrGluGlyLysMetGlyLys-179 |
| SEQ. ID. NO. 36706 | 187-HisSerAsnProIleSer-192 |
| SEQ. ID. NO. 36707 | 213-AsnLeuGlySerSerPhe-218 |
| SEQ. ID. NO. 36708 | 248-TyrProProGluIleLysGluThrProAsn-257 |

TABLE 1-continued

| | |
|---|---|
| SEQ. ID. NO. 36709 | 261-PheAlaLysAspArgLeuSerGluMetGlyLysMetSerAlaAspGluIle-277 |
| SEQ. ID. NO. 36710 | 328-AspValLeuLysGluLysSerAlaTrp-336 |
| Hydrophilic Regions - Hopp-Woods | |
| SEQ. ID. NO. 36711 | 71-ThrAlaAspLysProGlyAlaAlaMet-79 |
| SEQ. ID. NO. 36712 | 146-AsnThrAlaArgGly-150 |
| SEQ. ID. NO. 36713 | 168-AsnProAlaLysGlyThrGluGlyLysMetGlyLys-179 |
| SEQ. ID. NO. 36714 | 250-ProGluIleLysGluThrProAsn-257 |
| SEQ. ID. NO. 36715 | 261-PheAlaLysAspArgLeuSerGluMetGlyLysMetSerAlaAspGluIle-277 |
| SEQ. ID. NO. 36716 | 328-AspValLeuLysGluLysSerAlaTrp-336 |
| g930-1 | |
| AMPHI Regions - AMPHI | |
| SEQ. ID. NO. 36717 | 6-AlaGlyAspIleAsnGlnIleMetSerLeu-15 |
| SEQ. ID. NO. 36718 | 30-IleLeuAlaAlaPro-34 |
| SEQ. ID. NO. 36719 | 48-ProGlyTyrLeuArgSerIleArgIle-56 |
| SEQ. ID. NO. 36720 | 82-AspLeuLeuAsnLeuArgAsp-88 |
| SEQ. ID. NO. 36721 | 96-LeuLysCysLeuPro-100 |
| SEQ. ID. NO. 36722 | 163-SerAspMetPheTyr-167 |
| SEQ. ID. NO. 36723 | 171-GlyArgSerIleGlyGly-176 |
| SEQ. ID. NO. 36724 | 216-ArgTyrHisGlnAlaValSerGlyLeuSerGluValTyrAsp-229 |
| SEQ. ID. NO. 36725 | 283-TrpLeuAlaGluLeuSerHis-289 |
| SEQ. ID. NO. 36726 | 308-ThrGlyMetLysAspAlaLeuArgAlaProGluGluAlaPheGlyGluGly-324 |
| SEQ. ID. NO. 36727 | 355-HisAlaGlnTrpAsnLys-360 |
| SEQ. ID. NO. 36728 | 457-LeuLysLysProGluTyrPhe-463 |
| Antigenic Index - Jameson-Wolf | |
| SEQ. ID. NO. 36729 | 1-GlyLysCysLeuHisAlaGlyAsp-8 |
| SEQ. ID. NO. 36730 | 34-ProGlnAspLeuAsnSerGlyLysLeu-42 |
| SEQ. ID. NO. 36731 | 54-IleArgIleAspArgSerAsnAspAspGlnThrHisAlaGlyArgIleAla-70 |
| SEQ. ID. NO. 36732 | 74-AsnLysPheProThrArgSerAsnAspLeuLeuAsn-85 |
| SEQ. ID. NO. 36733 | 87-ArgAspLeuGluGlnGlyLeuGluAsn-95 |
| SEQ. ID. NO. 36734 | 102-AlaGluAlaAspLeu-106 |
| SEQ. ID. NO. 36735 | 110-ProValGluArgGluProAsnGlnSerAsp-119 |
| SEQ. ID. NO. 36736 | 136-GlyMetAspAsnSerGlySerGluAlaThrGlyLysTyrGlnGly-150 |
| SEQ. ID. NO. 36737 | 156-AlaAspAsnProPheGlyLeu-162 |
| SEQ. ID. NO. 36738 | 170-TyrGlyArgSerIleGlyGlyThrProAspGluGluAsnPheAspGlyHisArgLysGluGlyGlySerAsn-193 |
| SEQ. ID. NO. 36739 | 212-HisAsnGlyTyrArg-216 |
| SEQ. ID. NO. 36740 | 226-GluValTyrAspTyrAsnGlyLysSerTyrAsnThrAspPheGlyPhe-241 |
| SEQ. ID. NO. 36741 | 245-LeuTyrArgAspAlaLysArgLysThrTyrLeu-255 |
| SEQ. ID. NO. 36742 | 260-TrpThrArgGluThrLysSerTyrIleAspAspAlaGluLeuThrValGlnArgArgLysThrThr-281 |
| SEQ. ID. NO. 36743 | 287-LeuSerHisLysGlyTyrIleGlyArgSerThrAlaAspPheLysLeuLysTyrLysHisGlyThrGlyMetLysAspAlaLeuArgAlaPro GluGluAlaPheGlyGluGlyThrSerArg-327 |
| SEQ. ID. NO. 36744 | 334-SerAlaAspValAsnThrPro-340 |
| SEQ. ID. NO. 36745 | 357-GlnTrpAsnLysThrProLeuThrSerGlnAspLysLeuAla-370 |
| SEQ. ID. NO. 36746 | 375-HisThrValArgGlyPheAspGlyGluMetSerLeuProAlaGluArgGlyTrpTyrTrpArgAsnAspLeuSerTrpGlnPheLysProGly His-406 |
| SEQ. ID. NO. 36747 | 418-SerGlyGlnSerAlaLys-423 |
| SEQ. ID. NO. 36748 | 455-ArgAlaLeuLysLysProGluTyrPheGlnThrLysLysTrpValThr-470 |
| Hydrophilic Regions - Hopp-Woods | |
| SEQ. ID. NO. 36749 | 35-GlnAspLeuAsnSerGlyLys-41 |
| SEQ. ID. NO. 36750 | 54-IleArgIleAspArgSerAsnAspAspGlnThrHisAla-66 |
| SEQ. ID. NO. 36751 | 76-PheProThrArgSerAsnAsp-82 |
| SEQ. ID. NO. 36752 | 87-ArgAspLeuGluGlnGlyLeuGluAsn-95 |
| SEQ. ID. NO. 36753 | 102-AlaGluAlaAspLeu-106 |
| SEQ. ID. NO. 36754 | 110-ProValGluArgGluProAsnGlnSer-118 |
| SEQ. ID. NO. 36755 | 137-MetAspAsnSerGlySerGluAlaThrGlyLysTyr-148 |
| SEQ. ID. NO. 36756 | 174-IleGlyGlyThrProAspGluGluAsnPheAspGlyHisArgLysGluGlyGlySer-192 |
| SEQ. ID. NO. 36757 | 228-TyrAspTyrAsnGly-232 |
| SEQ. ID. NO. 36758 | 245-LeuTyrArgAspAlaLysArgLysThrTyrLeu-255 |
| SEQ. ID. NO. 36759 | 260-TrpThrArgGluThrLysSerTyrIleAspAspAlaGluLeuThrValGlnArgArgLysThrThr-281 |
| SEQ. ID. NO. 36760 | 296-SerThrAlaAspPheLysLeuLysTyrLysHis-306 |
| SEQ. ID. NO. 36761 | 308-ThrGlyMetLysAspAlaLeuArgAlaProGluGluAlaPheGly-322 |
| SEQ. ID. NO. 36762 | 362-ProLeuThrSerGlnAspLysLeuAla-370 |
| SEQ. ID. NO. 36763 | 378-ArgGlyPheAspGlyGluMet-384 |
| SEQ. ID. NO. 36764 | 455-ArgAlaLeuLysLysProGluTyrPheGln-464 |
| g931 | |
| AMPHI Regions - AMPHI | |
| SEQ. ID. NO. 36765 | 43-LysAlaSerLysThrValAlaAsnPheValArgTyrAlaArgLys-57 |
| SEQ. ID. NO. 36766 | 67-ArgValIleGlyGly-71 |
| SEQ. ID. NO. 36767 | 81-GluAspLeuValGlnLysAlaThrAspLysAla-91 |
| SEQ. ID. NO. 36768 | 93-AlaAsnGluSerGlyAsnGlyLeuLysAsnThrValGly-105 |
| SEQ. ID. NO. 36769 | 142-ThrValPheGlyArgValGluSerGlyMetAspThrValSerLysIleAlaArgValLysThrAlaThrArgGlyPhe-167 |
| Antigenic Index - Jameson-Wolf | |
| SEQ. ID. NO. 36770 | 1-MetLysProLysPhe-5 |
| SEQ. ID. NO. 36771 | 30-ThrAspMetGlyAsn-34 |
| SEQ. ID. NO. 36772 | 38-ValLeuAspGluSerLysAlaSerLysThr-47 |
| SEQ. ID. NO. 36773 | 54-TyrAlaArgLysGlyPheTyrAspAsn-62 |
| SEQ. ID. NO. 36774 | 75-GlnGlyAspGlyLeuThrGluAspLeuValGlnLysAlaThrAspLysAlaValAlaAsnGluSerGlyAsnGlyLeuLysAsnThrVal-104 |
| SEQ. ID. NO. 36775 | 113-AlaAlaProAspSerAla-118 |
| SEQ. ID. NO. 36776 | 127-AlaAspAsnGlySerLeuAspTyrLysAsnGlyGlnTyrGly-140 |
| SEQ. ID. NO. 36777 | 145-GlyArgValGluSerGlyMetAspThrValSerLysIleAlaArgValLysThrAlaThrArgGlyPhe-167 |
| SEQ. ID. NO. 36778 | 176-ValLysIleArgArg-180 |

TABLE 1-continued

| | |
|---|---|
| Hydrophilic Regions - Hopp-Woods | |
| SEQ. ID. NO. 36779 | 1-MetLysProLysPhe-5 |
| SEQ. ID. NO. 36780 | 30-ThrAspMetGlyAsn-34 |
| SEQ. ID. NO. 36781 | 38-ValLeuAspGluSerLysAlaSerLysThr-47 |
| SEQ. ID. NO. 36782 | 78-GlyLeuThrGluAspLeuValGlnLysAlaThrAspLysAlaValAlaAsnGluSerGlyAsnGlyLeu-100 |
| SEQ. ID. NO. 36783 | 113-AlaAlaProAspSerAla-118 |
| SEQ. ID. NO. 36784 | 130-GlySerLeuAspTyrLysAsn-136 |
| SEQ. ID. NO. 36785 | 145-GlyArgValGluSerGlyMetAspThrValSerLysIleAlaArgValLysThrAlaThr-164 |
| SEQ. ID. NO. 36786 | 176-ValLysIleArgArg-180 |
| g933 | |
| AMPHI Regions - AMPHI | |
| SEQ. ID. NO. 36787 | 26-ProAsnIleProAlaLeuPheProLysHisProPheAspProPheGluAsnIleAsnAsnSerLysLys-48 |
| SEQ. ID. NO. 36788 | 63-GlyPheAlaArgGly-67 |
| SEQ. ID. NO. 36789 | 78-GluLysProLeuArgGlnTyrPheLysAspCysValAsnThr-91 |
| SEQ. ID. NO. 36790 | 101-IleSerSerPheGlyAsn-106 |
| SEQ. ID. NO. 36791 | 135-ValGlyAsnTyrIleGluTrpLeu-142 |
| SEQ. ID. NO. 36792 | 145-ThrLeuAsnLysLeuThrGlyTrpGlnGluHisLeuTyrAlaGlyLeuAspProPheHisTyrIleGluVal-168 |
| SEQ. ID. NO. 36793 | 264-AlaLeuAspAsnLeuLysHisLeuAspGlyHisGlnIleValLysValAsn-280 |
| SEQ. ID. NO. 36794 | 309-GlyPhePheThrLys-313 |
| SEQ. ID. NO. 36795 | 356-TrpLeuArgValIleAspGlyHisSerAsn-365 |
| SEQ. ID. NO. 36796 | 374-ProValGluGlyTyrArgLysGly-381 |
| SEQ. ID. NO. 36797 | 431-AlaGlyValTyrAlaThrTrpHis-438 |
| SEQ. ID. NO. 36798 | 447-AlaTyrValAspSerTrpMetGlnTyrGln-456 |
| SEQ. ID. NO. 36799 | 474-LysGlyIleThrAlaSer-479 |
| SEQ. ID. NO. 36800 | 483-GlyTyrAsnAlaLeuLeuAla-489 |
| SEQ. ID. NO. 36801 | 555-GlnProPheValAlaVal-560 |
| SEQ. ID. NO. 36802 | 606-PheAsnArgGlnThrSer-611 |
| Antigenic Index - Jameson-Wolf | |
| SEQ. ID. NO. 36803 | 1-LysLysLeuArgAspArgAsnSerGluTyrTrpLysGluGluThrTyrHisIleLysSerAsnGlyArgThrTyrPro-26 |
| SEQ. ID. NO. 36804 | 33-ProLysHisProPheAspProPheGluAsnIleAsnAsnSerLysLysIleSerPheTyrAspLysGluTyrThrGluAspTyr-60 |
| SEQ. ID. NO. 36805 | 68-PheGlyValGluLysArgAsnGlyGluGluGluLysProLeuArg-82 |
| SEQ. ID. NO. 36806 | 88-CysValAsnThrGluAsnSerAsnAsnAspAsnCysLysIleSerSer-103 |
| SEQ. ID. NO. 36807 | 112-IleLysSerAspIle-116 |
| SEQ. ID. NO. 36808 | 122-GlnIleLysAsnSerHisIleAsnSerGluIle-132 |
| SEQ. ID. NO. 36809 | 144-ProThrLeuAsnLysLeuThrGlyTrpGlnGlu-154 |
| SEQ. ID. NO. 36810 | 167-GluValThrAspAsnSerHis-173 |
| SEQ. ID. NO. 36811 | 189-SerLeuTrpLysProArgTrpAsnSerAsnIle-199 |
| SEQ. ID. NO. 36812 | 205-LysAsnAlaGluIleArgPheAsnThrLysAsnGluSerLeuLeuValLysGluAspTyrAlaGlyGlyAlaArgPhe-230 |
| SEQ. ID. NO. 36813 | 234-TyrAspLeuLysAspLysValProGlu-242 |
| SEQ. ID. NO. 36814 | 248-PheGluLysAsnIleThrGlyThrSer-256 |
| SEQ. ID. NO. 36815 | 263-LysAlaLeuAspAsnLeuLysHisLeuAspGlyHisGlnIleValLysValAsnAspThrAlaAspLysAspAlaPheArgLeuSerSer LysTyrArgLys-296 |
| SEQ. ID. NO. 36816 | 303-LeuGlnGlnArgProGluGlyPhe-310 |
| SEQ. ID. NO. 36817 | 313-LysValGlnGluArgAspAspIle-320 |
| SEQ. ID. NO. 36818 | 337-ArgLeuAsnAspLysAsnSerAspIlePheAspArgThrLeuProArgLysGlyLeu-355 |
| SEQ. ID. NO. 36819 | 360-IleAspGlyHisSerAsnGlnTrpValGlnGlyLysThrAlaProValGluGlyTyrArgLysGlyVal-382 |
| SEQ. ID. NO. 36820 | 392-GlnAsnGluSerAsnGlnLeu-398 |
| SEQ. ID. NO. 36821 | 403-MetGlyGlyGlnAlaGluGlnArgSerThrPheArgAsnProAspThrAspAsnLeuThr-422 |
| SEQ. ID. NO. 36822 | 424-GlyAsnValLysGly-428 |
| SEQ. ID. NO. 36823 | 440-LeuGlnAspLysGlnThrGlyAlaTyr-448 |
| SEQ. ID. NO. 36824 | 456-GlnArgPheArgHisArgIleAsnThrGluTyrAlaThrGluArgPheThrSerLysGlyIle-476 |
| SEQ. ID. NO. 36825 | 491-HisPheThrLysLysGlyAsnSerLeu-499 |
| SEQ. ID. NO. 36826 | 514-ValAsnGlyLysPheSerAspSerGluAsnAla-524 |
| SEQ. ID. NO. 36827 | 529-LeuGlySerArgGlnLeuGlnSerArgValGlyVal-540 |
| SEQ. ID. NO. 36828 | 567-LysProPheGlyValGluIleAspGlyAspArgArgValIleAsnAsnLysThrValIleGluThr-588 |
| SEQ. ID. NO. 36829 | 594-AlaLysIleLysSer-598 |
| SEQ. ID. NO. 36830 | 605-SerPheAsnArgGlnThrSerLysHisHisHisAlaLys-617 |
| Hydrophilic Regions - Hopp-Woods | |
| SEQ. ID. NO. 36831 | 1-LysLysLeuArgAspArgAsnSerGluTyrTrpLysGluGluThrTyrHis-17 |
| SEQ. ID. NO. 36832 | 20-SerAsnGlyArgThr-24 |
| SEQ. ID. NO. 36833 | 35-HisProPheAspPro-39 |
| SEQ. ID. NO. 36834 | 44-AsnAsnSerLysLysIleSerPheTyrAspLysGluTyrThrGlu-58 |
| SEQ. ID. NO. 36835 | 68-PheGlyValGluLysArgAsnGlyGluGluGluLysProLeu-81 |
| SEQ. ID. NO. 36836 | 88-CysValAsnThrGluAsnSerAsnAsnAspAsnCysLys-100 |
| SEQ. ID. NO. 36837 | 205-LysAsnAlaGluIleArgPheAsnThrLysAsnGluSerLeuLeuValLysGluAspTyrAlaGly-226 |
| SEQ. ID. NO. 36838 | 234-TyrAspLeuLysAspLysValProGlu-242 |
| SEQ. ID. NO. 36839 | 250-LysAsnIleThrGly-254 |
| SEQ. ID. NO. 36840 | 263-LysAlaLeuAspAsnLeuLysHisLeuAsp-272 |
| SEQ. ID. NO. 36841 | 278-LysValAsnAspThrAlaAspLysAspAlaPheArgLeuSerSerLysTyrArgLys-296 |
| SEQ. ID. NO. 36842 | 304-GlnGlnArgProGluGlyPhe-310 |
| SEQ. ID. NO. 36843 | 314-ValGlnGluArgAspAspIle-320 |
| SEQ. ID. NO. 36844 | 338-LeuAsnAspLysAsnSerAspIlePheAsp-347 |
| SEQ. ID. NO. 36845 | 376-GluGlyTyrArgLysGlyVal-382 |
| SEQ. ID. NO. 36846 | 393-AsnGluSerAsnGln-397 |
| SEQ. ID. NO. 36847 | 406-GlnAlaGluGlnArgSerThrPheArgAsnProAspThrAspAsnLeuThr-422 |
| SEQ. ID. NO. 36848 | 440-LeuGlnAspLysGlnThr-445 |
| SEQ. ID. NO. 36849 | 456-GlnArgPheArgHisArgIleAsnThr-464 |
| SEQ. ID. NO. 36850 | 491-HisPheThrLysLysGlyAsnSer-498 |
| SEQ. ID. NO. 36851 | 517-LysPheSerAspSerGluAsnAla-524 |
| SEQ. ID. NO. 36852 | 532-ArgGlnLeuGlnSer-536 |

TABLE 1-continued

| | |
|---|---|
| SEQ. ID. NO. 36853 | 569-PheGlyValGluIleAspGlyAspArgArgValIleAsn-581 |
| SEQ. ID. NO. 36854 | 594-AlaLysIleLysSer-598 |
| SEQ. ID. NO. 36855 | 606-PheAsnArgGlnThrSerLysHisHisHisAlaLys-617 |
| g933 | |
| AMPHI Regions - AMPHI | |
| SEQ. ID. NO. 36856 | 26-ProAsnIleProAlaLeuPheProLysHisProPheAspProPheGluAsnIleAsnAsnSerLysLys-48 |
| SEQ. ID. NO. 36857 | 63-GlyPheAlaArgGly-67 |
| SEQ. ID. NO. 36858 | 78-GluLysProLeuArgGlnTyrPheLysAspCysValAsnThr-91 |
| SEQ. ID. NO. 36859 | 101-IleSerSerPheGlyAsn-106 |
| SEQ. ID. NO. 36860 | 135-ValGlyAsnTyrIleGluTrpLeu-142 |
| SEQ. ID. NO. 36861 | 145-ThrLeuAsnLysLeuThrGlyTrpGlnGluHisLeuTyrAlaGlyLeuAspProPheHisTyrIleGluVal-168 |
| SEQ. ID. NO. 36862 | 264-AlaLeuAspAsnLeuLysHisLeuAspGlyHisGlnIleValLysValAsn-280 |
| SEQ. ID. NO. 36863 | 309-GlyPhePheThrLys-313 |
| SEQ. ID. NO. 36864 | 356-TrpLeuArgValIleAspGlyHisSerAsn-365 |
| SEQ. ID. NO. 36865 | 374-ProValGluGlyTyrArgLysGly-381 |
| SEQ. ID. NO. 36866 | 431-AlaGlyValTyrAlaThrTrpHis-438 |
| SEQ. ID. NO. 36867 | 447-AlaTyrValAspSerTrpMetGlnTyrGln-456 |
| SEQ. ID. NO. 36868 | 474-LysGlyIleThrAlaSer-479 |
| SEQ. ID. NO. 36869 | 483-GlyTyrAsnAlaLeuLeuAla-489 |
| SEQ. ID. NO. 36870 | 555-GlnProPheValAlaVal-560 |
| SEQ. ID. NO. 36871 | 606-PheAsnArgGlnThrSer-611 |
| Antigenic Index - Jameson-Wolf | |
| SEQ. ID. NO. 36872 | 1-LysLysLeuArgAspArgAsnSerGluTyrTrpLysGluGluThrTyrHisIleLysSerAsnGlyArgThrTyrPro-26 |
| SEQ. ID. NO. 36873 | 33-ProLysHisProPheAspProPheGluAsnIleAsnAsnSerLysLysIleSerPheTyrAspLysGluTyrThrGluAspTyr-60 |
| SEQ. ID. NO. 36874 | 68-PheGlyValGluLysArgAsnGlyGluGluGluLysProLeuArg-82 |
| SEQ. ID. NO. 36875 | 88-CysValAsnThrGluAsnSerAsnAsnAspAsnCysLysIleSerSer-103 |
| SEQ. ID. NO. 36876 | 112-IleLysSerAspIle-116 |
| SEQ. ID. NO. 36877 | 122-GlnIleLysAsnSerHisIleAsnSerGluIle-132 |
| SEQ. ID. NO. 36878 | 144-ProThrLeuAsnLysLeuThrGlyTrpGlnGlu-154 |
| SEQ. ID. NO. 36879 | 167-GluValThrAspAsnSerHis-173 |
| SEQ. ID. NO. 36880 | 189-SerLeuTrpLysProArgTrpAsnSerAsnIle-199 |
| SEQ. ID. NO. 36881 | 205-LysAsnAlaGluIleArgPheAsnThrLysAsnGluSerLeuLeuValLysGluAspTyrAlaGlyGlyAlaArgPhe-230 |
| SEQ. ID. NO. 36882 | 234-TyrAspLeuLysAspLysValProGlu-242 |
| SEQ. ID. NO. 36883 | 248-PheGluLysAsnIleThrGlyThrSer-256 |
| SEQ. ID. NO. 36884 | 263-LysAlaLeuAspAsnLeuLysHisLeuAspGlyHisGlnIleValLysValAsnAspThrAlaAspLysAspAlaPheArgLeuSer SerLysTyrArgLys-296 |
| SEQ. ID. NO. 36885 | 303-LeuGlnGlnArgProGluGlyPhe-310 |
| SEQ. ID. NO. 36886 | 313-LysValGlnGluArgAspAspIle-320 |
| SEQ. ID. NO. 36887 | 337-ArgLeuAsnAspLysAsnSerAspIlePheAspArgThrLeuProArgLysGlyLeu-355 |
| SEQ. ID. NO. 36888 | 360-IleAspGlyHisSerAsnGlnTrpValGlnGlyLysThrAlaProValGluGlyTyrArgLysGlyVal-382 |
| SEQ. ID. NO. 36889 | 392-GlnAsnGluSerAsnGlnLeu-398 |
| SEQ. ID. NO. 36890 | 403-MetGlyGlyGlnAlaGluGlnArgSerThrPheArgAsnProAspThrAspAsnLeuThr-422 |
| SEQ. ID. NO. 36891 | 424-GlyAsnValLysGly-428 |
| SEQ. ID. NO. 36892 | 440-LeuGlnAspLysGlnThrGlyAlaTyr-448 |
| SEQ. ID. NO. 36893 | 456-GlnArgPheArgHisArgIleAsnThrGluTyrAlaThrGluArgPheThrSerLysGlyIle-476 |
| SEQ. ID. NO. 36894 | 491-HisPheThrLysLysGlyAsnSerLeu-499 |
| SEQ. ID. NO. 36895 | 514-ValAsnGlyLysPheSerAspSerGluAsnAla-524 |
| SEQ. ID. NO. 36896 | 529-LeuGlySerArgGlnLeuGlnSerArgValGlyVal-540 |
| SEQ. ID. NO. 36897 | 567-LysProPheGlyValGluIleAspGlyAspArgArgValIleAsnAsnLysThrValIleGluThr-588 |
| SEQ. ID. NO. 36898 | 594-AlaLysIleLysSer-598 |
| SEQ. ID. NO. 36899 | 605-SerPheAsnArgGlnThrSerLysHisHisHisAlaLys-617 |
| Hydrophilic Regions - Hopp-Woods | |
| SEQ. ID. NO. 36900 | 1-LysLysLeuArgAspArgAsnSerGluTyrTrpLysGluGluThrTyrHis-17 |
| SEQ. ID. NO. 36901 | 20-SerAsnGlyArgThr-24 |
| SEQ. ID. NO. 36902 | 35-HisProPheAspPro-39 |
| SEQ. ID. NO. 36903 | 44-AsnAsnSerLysLysIleSerPheTyrAspLysGluTyrThrGlu-58 |
| SEQ. ID. NO. 36904 | 68-PheGlyValGluLysArgAsnGlyGluGluGluLysProLeu-81 |
| SEQ. ID. NO. 36905 | 88-CysValAsnThrGluAsnSerAsnAsnAspAsnCysLys-100 |
| SEQ. ID. NO. 36906 | 205-LysAsnAlaGluIleArgPheAsnThrLysAsnGluSerLeuLeuValLysGluAspTyrAlaGly-226 |
| SEQ. ID. NO. 36907 | 234-TyrAspLeuLysAspLysValProGlu-242 |
| SEQ. ID. NO. 36908 | 250-LysAsnIleThrGly-254 |
| SEQ. ID. NO. 36909 | 263-LysAlaLeuAspAsnLeuLysHisLeuAsp-272 |
| SEQ. ID. NO. 36910 | 278-LysValAsnAspThrAlaAspLysAspAlaPheArgLeuSerSerLysTyrArgLys-296 |
| SEQ. ID. NO. 36911 | 304-GlnGlnArgProGluGlyPhe-310 |
| SEQ. ID. NO. 36912 | 314-ValGlnGluArgAspAspIle-320 |
| SEQ. ID. NO. 36913 | 338-LeuAsnAspLysAsnSerAspIlePheAsp-347 |
| SEQ. ID. NO. 36914 | 376-GluGlyTyrArgLysGlyVal-382 |
| SEQ. ID. NO. 36915 | 393-AsnGluSerAsnGln-397 |
| SEQ. ID. NO. 36916 | 406-GlnAlaGluGlnArgSerThrPheArgAsnProAspThrAspAsnLeuThr-422 |
| SEQ. ID. NO. 36917 | 440-LeuGlnAspLysGlnThr-445 |
| SEQ. ID. NO. 36918 | 456-GlnArgPheArgHisArgIleAsnThr-464 |
| SEQ. ID. NO. 36919 | 491-HisPheThrLysLysGlyAsnSer-498 |
| SEQ. ID. NO. 36920 | 517-LysPheSerAspSerGluAsnAla-524 |
| SEQ. ID. NO. 36921 | 532-ArgGlnLeuGlnSer-536 |

SEQ. ID. NO. 36922 569-PheGlyValGluIleAspGlyAspArgArgValIleAsn-581
SEQ. ID. NO. 36923 594-AlaLysIleLysSer-598
SEQ. ID. NO. 36924 606-PheAsnArgGlnThrSerLysHisHisHisAlaLys-617
g936-1
AMPHI Regions - AMPHI
SEQ. ID. NO. 36925 10-ThrLeuIleAlaAla-14
SEQ. ID. NO. 36926 19-AlaLeuGlyGlyCysPheSerAlaVal-27
SEQ. ID. NO. 36927 100-GlnPheValGlyGlnIle-105
SEQ. ID. NO. 36928 112-AlaGluGlyValTyrAsnTyrIleThrValAlaSerLeuProArgThrAlaGlyAspIleAlaGlyAsp-134
Antigenic Index - Jameson-Wolf
SEQ. ID. NO. 36929 1-MetLysProLysProHisThrVal-8
SEQ. ID. NO. 36930 37-SerValIleAspArgArgThrThrGlyAlaGlnThrAspAspAsnValMet-53
SEQ. ID. NO. 36931 56-ArgIleGluThrThrAlaArgSerTyrLeuArgGlnAsnAsnGlnThrLysGlyTyr-74
SEQ. ID. NO. 36932 94-AlaThrGluGlyGluLysGlnPhe-101
SEQ. ID. NO. 36933 106-AlaArgSerGluGlnAlaAla-112
SEQ. ID. NO. 36934 124-LeuProArgThrAlaGlyAspIleAlaGlyAspThrTrpAsnThrSerLysValArgAla-143
SEQ. ID. NO. 36935 149-SerProAlaThrGlnAlaArgValLys-157
SEQ. ID. NO. 36936 172-ThrProGluGluGlnAlaGlnIleThr-180
Hydrophilic Regions - Hopp-Woods
SEQ. ID. NO. 36937 1-MetLysProLysProHisThr-7
SEQ. ID. NO. 36938 37-SerValIleAspArgArgThrThrGlyAlaGlnThrAspAspAsnValMet-53
SEQ. ID. NO. 36939 56-ArgIleGluThrThrAla-61
SEQ. ID. NO. 36940 68-AsnAsnGlnThrLysGlyTyr-74
SEQ. ID. NO. 36941 94-AlaThrGluGlyGluLysGlnPhe-101
SEQ. ID. NO. 36942 106-AlaArgSerGluGlnAlaAla-112
SEQ. ID. NO. 36943 125-ProArgThrAlaGly-129
SEQ. ID. NO. 36944 152-ThrGlnAlaArgValLys-157
SEQ. ID. NO. 36945 172-ThrProGluGluGlnAlaGlnIle-179
g937
AMPHI Regions - AMPHI
SEQ. ID. NO. 36946 121-LysArgMetSerAspIleSerAlaGlyIleSerHis-132
SEQ. ID. NO. 36947 231-LysGlnProAspArgIleAsp-237
Antigenic Index - Jameson-Wolf
SEQ. ID. NO. 36948 18-ThrAspLeuProLeuAsnIle-24
SEQ. ID. NO. 36949 26-AspIleMetThrAspLysGlyLysTrpLysLeuGluThr-38
SEQ. ID. NO. 36950 43-LeuAsnSerGluAsnSerArgAlaAlaLeu-52
SEQ. ID. NO. 36951 69-ProThrGluIleGlnGluAsnGlySerAsnThrAsp-80
SEQ. ID. NO. 36952 94-GlyAsnThrAspIleTyrGlySerGlySer-103
SEQ. ID. NO. 36953 107-HisGluGluArgLysLeuAspGlyAsnGlyLysThrArgAsnLysArgMetSerAspIle-126
SEQ. ID. NO. 36954 134-PheLeuLysAspGlyLysAsnProAla-142
SEQ. ID. NO. 36955 150-ThrValTyrGluLysSerArgAsnLysAlaSerSerGlyLys-163
SEQ. ID. NO. 36956 186-TyrArgIleAsnGlySerLysThrLeuSerAspAspValLysTyrLysAlaGly-203
SEQ. ID. NO. 36957 216-AlaAsnAspArgIleSerLeuThrGlyGly-225
SEQ. ID. NO. 36958 230-GlyLysGlnProAspArgIleAspGlyLysLysGluSerAlaArgAsnThrSerThr-248
SEQ. ID. NO. 36959 272-ValSerGlyGlnSerSerSerGluLeuLysLeu-282
Hydrophilic Regions - Hopp-Woods
SEQ. ID. NO. 36960 26-AspIleMetThrAspLysGlyLysTrpLysLeu-36
SEQ. ID. NO. 36961 46-GluAsnSerArgAlaAlaLeu-52
SEQ. ID. NO. 36962 71-GluIleGlnGluAsnGlySerAsnThr-79
SEQ. ID. NO. 36963 107-HisGluGluArgLysLeuAspGlyAsnGlyLysThrArgAsnLysArgMetSerAspIle-126
SEQ. ID. NO. 36964 134-PheLeuLysAspGlyLysAsn-140
SEQ. ID. NO. 36965 150-ThrValTyrGluLysSerArgAsnLysAlaSerSerGly-162
SEQ. ID. NO. 36966 192-LysThrLeuSerAspAspValLysTyrLysAla-202
SEQ. ID. NO. 36967 216-AlaAsnAspArgIleSer-221
SEQ. ID. NO. 36968 231-LysGlnProAspArgIleAspGlyLysLysGluSerAlaArgAsn-245
SEQ. ID. NO. 36969 276-SerSerSerGluLeuLysLeu-282
g950
AMPHI Regions - AMPHI
SEQ. ID. NO. 36970 33-GlyValGlnLysSerAlaGlnGly-40
SEQ. ID. NO. 36971 81-AlaThrValLysLysAlaHisLysHisThrLysAla-92
Antigenic Index - Jameson-Wolf
SEQ. ID. NO. 36972 1-MetAsnLysAsnIle-5
SEQ. ID. NO. 36973 26-LysProAlaSerAsnAlaThrGlyValGlnLysSerAlaGlnGlySerCysGlyAlaSerLysSerAlaGluGlySerCysGlyAlaSerLysSer AlaGluGlySerCysGly-63
SEQ. ID. NO. 36974 65-AlaAlaSerLysAlaGlyGluGlyLysCysGlyGluGlyLysCysGlyAlaThrValLysLysAlaHisLysHisThrLysAlaSerLysAlaLys AlaLysSerAlaGluGlyLysCysGlyGluGlyLysCysGlySerLys-112
Hydrophilic Regions - Hopp-Woods
SEQ. ID. NO. 36975 33-GlyValGlnLysSerAlaGln-39
SEQ. ID. NO. 36976 43-GlyAlaSerLysSerAlaGluGlySerCysGlyAlaSerLysSerAlaGluGlySerCys-62
SEQ. ID. NO. 36977 65-AlaAlaSerLysAlaGlyGluGlyLysCysGlyGluGlyLysCys-79
SEQ. ID. NO. 36978 81-AlaThrValLysLysAlaHisLysHisThrLysAlaSerLysAlaLysAlaLysSerAlaGluGlyLysCysGlyGluGlyLysCysGlySer Lys-112
g951
AMPHI Regions - AMPHI
SEQ. ID. NO. 36979 9-ThrIleLeuSerValLeuAlaAla-16
SEQ. ID. NO. 36980 32-GluLeuProLysGluValGlyLysValLeuArgLysHisArgArgTyr-47
SEQ. ID. NO. 36981 62-ValGlyGluArgValAsnArgValPhe-70
SEQ. ID. NO. 36982 127-TrpArgGlnIleGluProIleProGlyGlu-136
SEQ. ID. NO. 36983 145-ArgAsnValLeuArgGluGlyGlyAsnGlnHisLeuAspGlyLeuGluGluValLeuAla-164
SEQ. ID. NO. 36984 189-AlaGlnLysAlaSerLysAlaValArgArg-198

TABLE 1-continued

| | |
|---|---|
| SEQ. ID. NO. 36985 | 204-GluHisLeuProGluAlaAla-210 |
| SEQ. ID. NO. 36986 | 227-IleGluAlaLeuGlnArgLeuAlaLysLeu-236 |
| SEQ. ID. NO. 36987 | 254-LysTyrProGluIleLeuAspGlyPhePheGlu-264 |
| SEQ. ID. NO. 36988 | 278-MetGluIleMetAsnLeuValSerLeuArgLysProAspAspAla-292 |
| SEQ. ID. NO. 36989 | 325-ValIleAspGlyTyrAlaGluLys-332 |
| SEQ. ID. NO. 36990 | 362-ValArgGlnTrpLeuLys-367 |
| SEQ. ID. NO. 36991 | 395-AlaLeuArgGlnIleGlyArgValArgLysLeuProGluGlnGln-409 |
| SEQ. ID. NO. 36992 | 416-AspAsnLeuSerLysIle-421 |
| SEQ. ID. NO. 36993 | 423-MetLeuAlaLeuSer-427 |
| SEQ. ID. NO. 36994 | 441-AsnIleIleAlaLysLeuSerAlaAlaGlySerThrGluProLeuAlaGlu-457 |
| SEQ. ID. NO. 36995 | 474-LysMetIleAlaAspLeuGluThr-481 |
| SEQ. ID. NO. 36996 | 495-AsnLeuGlyTyrSer-499 |
| SEQ. ID. NO. 36997 | 503-AspSerLysArgLeu-507 |
| SEQ. ID. NO. 36998 | 563-HisLeuGlyGluVal-567 |
| SEQ. ID. NO. 36999 | 579-AspValTrpThrGlnAla-584 |
| SEQ. ID. NO. 37000 | 592-LysIleTrpArgGluThrLeuLys-599 |
| Antigenic Index - Jameson-Wolf | |
| SEQ. ID. NO. 37001 | 29-AlaAspValGluLeuProLysGluValGlyLysValLeuArgLysHisArgArgTyrSerGluGluGluIleLysAsnGluArgAlaArgLeu-59 |
| SEQ. ID. NO. 37002 | 61-AlaValGlyGluArgValAsnArg-68 |
| SEQ. ID. NO. 37003 | 77-ThrAlaLeuGlnLysGlyGlnAla-84 |
| SEQ. ID. NO. 37004 | 96-GluArgThrLysSerProGluValAlaGluArgAlaLeuGlu-109 |
| SEQ. ID. NO. 37005 | 126-LysTrpArgGlnIleGluProIleProGlyGluAlaGlnLysArgAlaGlyTrp-143 |
| SEQ. ID. NO. 37006 | 147-ValLeuArgGluGlyGlyAsnGlnHisLeuAspGlyLeuGluGluValLeuAlaGlnSerAspAspValGlnLysArgArgIle-174 |
| SEQ. ID. NO. 37007 | 187-GlyValAlaGlnLysAlaSerLysAlaValArgArgAlaAlaLeuLys-202 |
| SEQ. ID. NO. 37008 | 219-GlnGlyArgGluLysGluLysAlaIleGluAlaLeuGlnArgLeuAlaLysLeuAspThrGluIleLeuPro-242 |
| SEQ. ID. NO. 37009 | 250-LeuThrAlaArgLysTyrProGluIleLeuAspGlyPhePheGluGlnThrAspThrGlnAsn-270 |
| SEQ. ID. NO. 37010 | 285-SerLeuArgLysProAspAspAlaTyrAla-294 |
| SEQ. ID. NO. 37011 | 301-GluHisAsnProAsnAlaAsn-307 |
| SEQ. ID. NO. 37012 | 317-AlaAsnArgLysGluGlyAlaSer-324 |
| SEQ. ID. NO. 37013 | 326-IleAspGlyTyrAlaGluLysAlaTyrGlyArgGlyThrGlyGluGlnArgGlyArgAla-345 |
| SEQ. ID. NO. 37014 | 354-AlaAspArgArgAspTyrAlaLys-361 |
| SEQ. ID. NO. 37015 | 364-GlnTrpLeuLysLysValSerAlaPro-372 |
| SEQ. ID. NO. 37016 | 375-LeuPheAspLysGlyVal-380 |
| SEQ. ID. NO. 37017 | 387-AlaGluLeuAspGlyGlyArgAlaAlaLeu-396 |
| SEQ. ID. NO. 37018 | 398-GlnIleGlyArgValArgLysLeuProGluGlnGlnGlyArgTyrPheThr-414 |
| SEQ. ID. NO. 37019 | 428-LysLeuProAspLysArgGluAlaLeu-436 |
| SEQ. ID. NO. 37020 | 447-SerAlaAlaGlySerThrGluProLeuAla-456 |
| SEQ. ID. NO. 37021 | 467-GluGlnPheGlyLysArgGlyLysMetIleAlaAspLeuGluThr-481 |
| SEQ. ID. NO. 37022 | 485-LeuThrProAspAsn-489 |
| SEQ. ID. NO. 37023 | 501-LeuSerAspSerLysArgLeuAspGluGlyPhe-511 |
| SEQ. ID. NO. 37024 | 519-GlnIleAsnProAspAspThrAlaValAsnAspSerIle-531 |
| SEQ. ID. NO. 37025 | 537-LeuLysGlyAspAlaGluSerAla-544 |
| SEQ. ID. NO. 37026 | 549-ArgTyrSerPheGluAsnAspProGluProGluVal-560 |
| SEQ. ID. NO. 37027 | 572-GlyGluArgAspGlnAla-577 |
| SEQ. ID. NO. 37028 | 585-AlaHisLeuArgGlyAspLysLysIleTrpArgGluThrLeuLysArgTyrGly-602 |
| SEQ. ID. NO. 37029 | 604-AlaLeuProGluProSerArgLysProArgLys-614 |
| Hydrophilic Regions - Hopp-Woods | |
| SEQ. ID. NO. 37030 | 29-AlaAspValGluLeuProLysGluValGlyLysValLeuArgLysHisArgArgTyrSerGluGluGluIleLysAsnGluArgAlaArgLeu-59 |
| SEQ. ID. NO. 37031 | 61-AlaValGlyGluArgValAsnArg-68 |
| SEQ. ID. NO. 37032 | 77-ThrAlaLeuGlnLysGlyGlnAla-84 |
| SEQ. ID. NO. 37033 | 96-GluArgThrLysSerProGluValAlaGluArgAlaLeuGlu-109 |
| SEQ. ID. NO. 37034 | 133-IleProGlyGluAlaGlnLysArgAlaGlyTrp-143 |
| SEQ. ID. NO. 37035 | 147-ValLeuArgGluGlyGlyAsnGlnHis-155 |
| SEQ. ID. NO. 37036 | 157-AspGlyLeuGluGluValLeuAlaGlnSerAspAspValGlnLysArgArgIle-174 |
| SEQ. ID. NO. 37037 | 188-ValAlaGlnLysAlaSerLysAlaValArgArgAlaAlaLeuLys-202 |
| SEQ. ID. NO. 37038 | 219-GlnGlyArgGluLysGluLysAlaIleGluAlaLeuGlnArgLeuAlaLysLeuAspThrGluIle-240 |
| SEQ. ID. NO. 37039 | 250-LeuThrAlaArgLysTyrProGluIle-258 |
| SEQ. ID. NO. 37040 | 263-PheGluGlnThrAspThrGlnAsn-270 |
| SEQ. ID. NO. 37041 | 285-SerLeuArgLysProAspAspAlaTyrAla-294 |
| SEQ. ID. NO. 37042 | 317-AlaAsnArgLysGluGlyAlaSer-324 |
| SEQ. ID. NO. 37043 | 329-TyrAlaGluLysAlaTyrGly-335 |
| SEQ. ID. NO. 37044 | 337-GlyThrGlyGluGlnArgGlyArgAla-345 |
| SEQ. ID. NO. 37045 | 354-AlaAspArgArgAspTyrAlaLys-361 |
| SEQ. ID. NO. 37046 | 387-AlaGluLeuAspGlyGlyArgAlaAlaLeu-396 |
| SEQ. ID. NO. 37047 | 398-GlnIleGlyArgValArgLysLeuProGluGlnGlnGly-410 |
| SEQ. ID. NO. 37048 | 428-LysLeuProAspLysArgGluAlaLeu-436 |
| SEQ. ID. NO. 37049 | 450-GlySerThrGluProLeuAla-456 |
| SEQ. ID. NO. 37050 | 469-PheGlyLysArgGlyLysMetIleAlaAspLeuGluThr-481 |
| SEQ. ID. NO. 37051 | 485-LeuThrProAspAsn-489 |
| SEQ. ID. NO. 37052 | 502-SerAspSerLysArgLeuAspGlu-509 |
| SEQ. ID. NO. 37053 | 521-AsnProAspAspThrAlaVal-527 |
| SEQ. ID. NO. 37054 | 539-GlyAspAlaGluSer-543 |
| SEQ. ID. NO. 37055 | 552-PheGluAsnAspProGluProGluVal-560 |
| SEQ. ID. NO. 37056 | 572-GlyGluArgAspGlnAla-577 |
| SEQ. ID. NO. 37057 | 587-LeuArgGlyAspLysLysIleTrpArgGluThrLeuLys-599 |
| SEQ. ID. NO. 37058 | 607-GluProSerArgLysProArgLys-614 |
| g952 | |
| AMPHI Regions - AMPHI | |
| SEQ. ID. NO. 37059 | 47-SerValAlaThrLeuLeuAsn-53 |
| SEQ. ID. NO. 37060 | 66-LeuGluLysLeuGlyLysGluGlnMetArgAla-76 |

TABLE 1-continued

| | |
|---|---|
| SEQ. ID. NO. 37061 | 78-PheGluAspMetArgArgIle-84 |
| SEQ. ID. NO. 37062 | 100-GluGlnLeuAlaGlnLeu-105 |
| SEQ. ID. NO. 37063 | 122-SerValLeuArgGlyVal-127 |
| SEQ. ID. NO. 37064 | 147-AlaGlnPheLeuGluAla-152 |
| Antigenic Index - Jameson-Wolf | |
| SEQ. ID. NO. 37065 | 24-GlnSerTrpLysAlaArgArgAspPheAsnIleValLysGlnAspLeuAspPheSerCys-43 |
| SEQ. ID. NO. 37066 | 59-LysLeuThrGluGluGluValLeuGluLysLeuGlyLysGluGlnMetArgAlaSerPheGluAspMetArgArgIleMetPro-86 |
| SEQ. ID. NO. 37067 | 88-LeuGlyPheGluAlaLysGlyTyr-95 |
| SEQ. ID. NO. 37068 | 113-LeuLysTyrArgLysAspAspHisPheSer-122 |
| SEQ. ID. NO. 37069 | 125-ArgGlyValAspGlyAsnThr-131 |
| SEQ. ID. NO. 37070 | 135-AlaAspProSerProGlyHis-141 |
| SEQ. ID. NO. 37071 | 153-TrpGlnThrArgGluGlyAsnLeuAlaGly-162 |
| SEQ. ID. NO. 37072 | 168-ValProLysLysAlaGluAlaIleSer-176 |
| SEQ. ID. NO. 37073 | 183-HisHisProLysArgGlnThrGlu-190 |
| Hydrophilic Regions - Hopp-Woods | |
| SEQ. ID. NO. 37074 | 25-SerTrpLysAlaArgArgAspPheAsnIleValLysGlnAspLeuAspPhe-41 |
| SEQ. ID. NO. 37075 | 59-LysLeuThrGluGluGluValLeuGluLysLeuGlyLysGluGlnMetArgAlaSerPheGluAspMetArgArgIleMetPro-86 |
| SEQ. ID. NO. 37076 | 88-LeuGlyPheGluAlaLysGly-94 |
| SEQ. ID. NO. 37077 | 114-LysTyrArgLysAspAspHisPheSer-122 |
| SEQ. ID. NO. 37078 | 153-TrpGlnThrArgGluGlyAsnLeu-160 |
| SEQ. ID. NO. 37079 | 168-ValProLysLysAlaGluAlaIleSer-176 |
| SEQ. ID. NO. 37080 | 184-HisProLysArgGlnThrGlu-190 |
| g953 | |
| AMPHI Regions - AMPHI | |
| SEQ. ID. NO. 37081 | 38-AsnThrSerThrAsnValGlyGlyPheTyrGlyLeuThr-50 |
| SEQ. ID. NO. 37082 | 79-ProPheThrGlyHis-83 |
| SEQ. ID. NO. 37083 | 85-LysSerAlaAspIlePheAspAlaAlaGln-94 |
| SEQ. ID. NO. 37084 | 150-GlyAspPheSerThrThr-155 |
| Antigenic Index - Jameson-Wolf | |
| SEQ. ID. NO. 37085 | 21-TyrLysValAspGluTyrHisAla-28 |
| SEQ. ID. NO. 37086 | 37-PheAsnThrSerThrAsnVal-43 |
| SEQ. ID. NO. 37087 | 53-ValGluPheAspGlnAlaLysArgAspGlyLysIleAspIle-66 |
| SEQ. ID. NO. 37088 | 74-GlnSerGlySerGlnPro-79 |
| SEQ. ID. NO. 37089 | 94-GlnTyrProAspIleArgPheValSer-102 |
| SEQ. ID. NO. 37090 | 104-LysPheAsnPheAsnGlyLysLysLeuValSer-114 |
| SEQ. ID. NO. 37091 | 121-MetArgGlyLysThrAlaProValLysLeuLysAlaGluLys-134 |
| SEQ. ID. NO. 37092 | 136-AsnCysTyrGlnSerProMetAlaGluThrGluValCysGlyGlyAspPheSerThrThrIleAspArgThrLysTrpGlyValAsp-164 |
| SEQ. ID. NO. 37093 | 170-GlyMetThrLysAsnValArgIle-177 |
| SEQ. ID. NO. 37094 | 179-IleGlnIleGluAlaAlaLysGln-186 |
| Hydrophilic Regions - Hopp-Woods | |
| SEQ. ID. NO. 37095 | 21-TyrLysValAspGluTyrHisAla-28 |
| SEQ. ID. NO. 37096 | 53-ValGluPheAspGlnAlaLysArgAspGlyLysIleAspIle-66 |
| SEQ. ID. NO. 37097 | 107-PheAsnGlyLysLysLeuValSer-114 |
| SEQ. ID. NO. 37098 | 121-MetArgGlyLysThrAlaProValLysLeuLysAlaGluLys-134 |
| SEQ. ID. NO. 37099 | 142-MetAlaGluThrGluValCysGly-149 |
| SEQ. ID. NO. 37100 | 154-ThrThrIleAspArgThrLysTrp-161 |
| SEQ. ID. NO. 37101 | 173-LysAsnValArgIle-177 |
| SEQ. ID. NO. 37102 | 179-IleGlnIleGluAlaAlaLysGln-186 |
| g957-2 | |
| AMPHI Regions - AMPHI | |
| SEQ. ID. NO. 37103 | 11-SerPhePheAlaLeuValPheAla-18 |
| SEQ. ID. NO. 37104 | 39-AlaThrGluValProGluAsnPro-46 |
| SEQ. ID. NO. 37105 | 48-AlaPheValAlaLysLeuAlaArgLeuPheArgAsnAla-60 |
| SEQ. ID. NO. 37106 | 74-GluGluSerLeuAlaGlyAlaValAspAsp-83 |
| SEQ. ID. NO. 37107 | 167-HisGlyGluAsnTyrGluThr-173 |
| SEQ. ID. NO. 37108 | 198-GluAspValTyrGluHisCysLeuGlyCysTyrGlnMet-210 |
| SEQ. ID. NO. 37109 | 218-TyrArgAspValAlaAsn-223 |
| SEQ. ID. NO. 37110 | 235-SerAsnArgIleAlaSer-240 |
| SEQ. ID. NO. 37111 | 251-MetArgGluLeuMetProArg-257 |
| SEQ. ID. NO. 37112 | 355-GluLysGluValSerArgTyrAlaGluAlaAlaAlaArg-367 |
| Antigenic Index - Jameson-Wolf | |
| SEQ. ID. NO. 37113 | 29-IleAsnProArgTrp-33 |
| SEQ. ID. NO. 37114 | 35-LeuSerAspThrAlaThrGluValProGluAsnProAsnAla-48 |
| SEQ. ID. NO. 37115 | 57-PheArgAsnAlaAspArgAla-63 |
| SEQ. ID. NO. 37116 | 67-ValLysGluSerMetArgThrGluGluSerLeu-77 |
| SEQ. ID. NO. 37117 | 80-AlaValAspAspGlyProLeuGlnSerGluLysAspTyr-92 |
| SEQ. ID. NO. 37118 | 98-ArgLeuSerArgLeuLysGluLysAlaLys-107 |
| SEQ. ID. NO. 37119 | 112-ThrGluGlnGluHisGlyGlu-118 |
| SEQ. ID. NO. 37120 | 125-TyrIleGlyGluGlyGly-130 |
| SEQ. ID. NO. 37121 | 136-LeuSerGlnArgSerProGluAlaPheVal-145 |
| SEQ. ID. NO. 37122 | 149-TyrLeuTyrArgAsnAspArgProPheSer-158 |
| SEQ. ID. NO. 37123 | 166-AlaHisGlyGluAsnTyrGluThrThrGlyGluTyrArgVal-179 |
| SEQ. ID. NO. 37124 | 182-GlnProAspGlySerVal-187 |
| SEQ. ID. NO. 37125 | 190-AlaAlaGlyArgGlyLysIleGlyGluAspValTyr-201 |
| SEQ. ID. NO. 37126 | 217-LysTyrArgAspValAlaAsnAspGluGlnLysValTrpAspPheArgGluGluSerAsnArgIleAlaSerAspSerArgAspTyrVal-246 |
| SEQ. ID. NO. 37127 | 250-AsnMetArgGluLeuMetProArgGlyMetLysAlaAsnSer-263 |
| SEQ. ID. NO. 37128 | 267-GlyTyrAspAlaAspGlyLeuProGlnLys-276 |
| SEQ. ID. NO. 37129 | 280-SerPheAspAsnGlyLysLysArgGlnSerPheGluTyrTyrLeuLysAsnGlyAsn-298 |
| SEQ. ID. NO. 37130 | 309-LeuLysAlaAspGlyValThr-315 |

TABLE 1-continued

| | |
|---|---|
| SEQ. ID. NO. 37131 | 329-LeuAspGlyGlyArgIleIleArgGluGluLysGlnGlyAspArgLeuProAspPhe-347 |
| SEQ. ID. NO. 37132 | 349-LeuAsnLeuGluAspLeuGluLysGluValSerArgTyrAlaGluAlaAlaAlaArgArgSerGlyGlyArgArgGlyLeuSerHis-377 |
| Hydrophilic Regions - Hopp-Woods | |
| SEQ. ID. NO. 37133 | 38-ThrAlaThrGluValProGluAsnPro-46 |
| SEQ. ID. NO. 37134 | 57-PheArgAsnAlaAspArgAla-63 |
| SEQ. ID. NO. 37135 | 67-ValLysGluSerMetArgThrGluGluSerLeu-77 |
| SEQ. ID. NO. 37136 | 80-AlaValAspAspGlyProLeuGlnSerGluLysAspTyr-92 |
| SEQ. ID. NO. 37137 | 98-ArgLeuSerArgLeuLysGluLysAlaLys-107 |
| SEQ. ID. NO. 37138 | 112-ThrGluGlnGluHisGlyGlu-118 |
| SEQ. ID. NO. 37139 | 136-LeuSerGlnArgSerProGlu-142 |
| SEQ. ID. NO. 37140 | 151-TyrArgAsnAspArgProPhe-157 |
| SEQ. ID. NO. 37141 | 169-GluAsnTyrGluThrThrGlyGluTyr-177 |
| SEQ. ID. NO. 37142 | 190-AlaAlaGlyArgGlyLysIleGlyGluAspValTyr-201 |
| SEQ. ID. NO. 37143 | 217-LysTyrArgAspValAlaAsnAspGluGlnLysValTrpAspPheArgGluGluSerAsnArgIleAlaSerAspSerArgAsp-244 |
| SEQ. ID. NO. 37144 | 250-AsnMetArgGluLeuMetProArgGlyMetLys-260 |
| SEQ. ID. NO. 37145 | 268-TyrAspAlaAspGlyLeuPro-274 |
| SEQ. ID. NO. 37146 | 282-AspAsnGlyLysLysArgGlnSer-289 |
| SEQ. ID. NO. 37147 | 309-LeuLysAlaAspGlyValThr-315 |
| SEQ. ID. NO. 37148 | 331-GlyGlyArgIleIleArgGluGluLysGlnGlyAspArgLeuPro-345 |
| SEQ. ID. NO. 37149 | 349-LeuAsnLeuGluAspLeuGluLysGluValSerArgTyrAlaGluAlaAlaAlaArgArgSerGlyGlyArgArgGlyLeuSer-376 |
| g958 | |
| AMPHI Regions - AMPHI | |
| SEQ. ID. NO. 37150 | 39-GlyGlyAlaGlnGlyAlaSerGluSerAlaGln-49 |
| SEQ. ID. NO. 37151 | 85-ProGluAspTyrThrArgIleValAlaAsp-94 |
| SEQ. ID. NO. 37152 | 175-GlyArgArgLeuGlnSerValSerArgThrAlaGluMetLeuGly-189 |
| SEQ. ID. NO. 37153 | 342-IleSerAspThrLeuGln-347 |
| SEQ. ID. NO. 37154 | 400-GlnLysTyrGlnThrLeuAlaAsn-407 |
| SEQ. ID. NO. 37155 | 426-TrpHisLysAsnAlaGly-431 |
| SEQ. ID. NO. 37156 | 489-GlyGlyLysAlaSerArgSerValGlyArgValLeuProValVal-503 |
| SEQ. ID. NO. 37157 | 526-IleGluProArgLeu-530 |
| SEQ. ID. NO. 37158 | 540-GlnAsnAspLeuProAsnPheAsp-547 |
| SEQ. ID. NO. 37159 | 571-AsnAlaAlaAsnSerLeuSerThrAlaValGlnSer-582<br>615-ValGlyLysAsnPro-619 |
| SEQ. ID. NO. 37160 | 692-AspLysLeuSerGln-696 |
| SEQ. ID. NO. 37161 | 722-LysLysProIleGlu-726<br>768-AspLeuSerSerValGlyArgAsnPro-776 |
| Antigenic Index - Jameson-Wolf | |
| SEQ. ID. NO. 37162 | 19-GlyThrHisCysAla-23 |
| SEQ. ID. NO. 37163 | 27-ValAlaAlaGluGluAlaAspGlyArgValAlaGluGlyGlyAlaGlnGlyAlaSerGluSerAlaGlnAlaSer-51 |
| SEQ. ID. NO. 37164 | 62-CysSerAsnGluSerGlySerProGluArgThrGluAlaAlaValGlnGlySerGlyGluAlaSerValProGluAspTyrThrArgIleVal AlaAspArgMetGluGlyGlnSerLysValLysValArgAlaGluGly-108 |
| SEQ. ID. NO. 37165 | 110-ValIleIleGluArgAspGlyAlaValLeu-119 |
| SEQ. ID. NO. 37166 | 122-AspTrpAlaAspTyrAspGlnSerGlyAsp-131 |
| SEQ. ID. NO. 37167 | 134-ThrValGlyAspArgPheAlaLeuGlnGlnAspGlyThrLeuIleArgGlyGluThrLeu-153 |
| SEQ. ID. NO. 37168 | 157-LeuAspGlnGlnThrGlyGluAlaHisAsnValArgMetGluThrGluGlnGlyGlyArgArgLeuGlnSerValSerArgThrAlaGlu MetLeuGlyGluGlyArgTyrLysLeuThrGluThrGlnPheAsnThrCysSerAlaGlyAspAlaGlyTrp-210 |
| SEQ. ID. NO. 37169 | 215-AlaSerValGluAlaAspArgGlyLysGlyIleGly-226 |
| SEQ. ID. NO. 37170 | 248-PheProLeuAspGlyAsnArgLysSerGlyLeu-258 |
| SEQ. ID. NO. 37171 | 264-SerAlaGlySerAspGlyVal-270 |
| SEQ. ID. NO. 37172 | 291-GlyIleIleGlyGluArgGlyAlaThrPheAspGlyGlnIleArgTyrLeuArgProAspTyrSerGlyGlnThrAsp-316 |
| SEQ. ID. NO. 37173 | 320-LeuProHisAspLysLysSerGlyArgAsnAsnArgTyrGlnAla-334 |
| SEQ. ID. NO. 37174 | 336-TrpGlnHisArgHisAspIleSerAspThrLeu-346 |
| SEQ. ID. NO. 37175 | 351-AspPheAsnGlnValSerAspSerGlyTyrTyrArgAspPheTyrGlyGlyGluGluIleAlaGlyAsnValAsnLeuAsnArgArgValTrp-381 |
| SEQ. ID. NO. 37176 | 383-AspTyrGlyGlyArgAlaAlaGlyGlySerLeuAsn-394 |
| SEQ. ID. NO. 37177 | 400-GlnLysTyrGlnThr-404 |
| SEQ. ID. NO. 37178 | 406-AlaAsnGlnSerGlyTyrLysAspGluProTyr-416 |
| SEQ. ID. NO. 37179 | 420-ProArgLeuSerAlaAspTrpHisLysAsnAlaGlyArgAlaGlnIle-435 |
| SEQ. ID. NO. 37180 | 443-ArgPheSerHisAspGlyArgGlnAspGlySerArg-454 |
| SEQ. ID. NO. 37181 | 465-PheSerAsnSerTrpGly-470 |
| SEQ. ID. NO. 37182 | 473-ArgProLysLeuGlyLeu-478 |
| SEQ. ID. NO. 37183 | 487-SerPheGlyGlyLysAlaSerArgSerValGlyArg-498 |
| SEQ. ID. NO. 37184 | 506-AspGlyGlyThrThrPheGluArgAsnThrArgLeuPheGlyGlyGly-521 |
| SEQ. ID. NO. 37185 | 537-AlaLysSerGlnAsnAspLeuProAsnPheAspSerSerGluSerSerPheGly-554 |
| SEQ. ID. NO. 37186 | 559-PheArgGluAsnLeuTyrTyrGlyAsnAspArgIleAsnAla-572 |
| SEQ. ID. NO. 37187 | 583-ArgIleLeuAspGlyAlaThrGlyGluGluArgPheArgAlaGlyIleGlyGlnLysPheTyrPheLysAspAspAlaValMetLeuAspGly SerValGlyLysAsnProArgSerArgSerAspTrp-625 |
| SEQ. ID. NO. 37188 | 630-SerGlyGlyIleGlyGly-635 |
| SEQ. ID. NO. 37189 | 641-SerSerIleHisTyrAsnGlnAsnAspLysArgAlaGluHis-654 |
| SEQ. ID. NO. 37190 | 659-AlaGlyTyrArgProAlaProGlyLysValLeuAsnAlaArgTyrLysTyrGlyArgAsnGluLysIle-681 |
| SEQ. ID. NO. 37191 | 692-AspLysLeuSerGln-696 |
| SEQ. ID. NO. 37192 | 717-TyrGlyPheGluAlaLysLysProIleGlu-726 |
| SEQ. ID. NO. 37193 | 731-AlaGluTyrLysSerSerCysGlyCysTrp-740 |
| SEQ. ID. NO. 37194 | 750-ValThrGlyGluAsnThrTyrLysAsn-758 |
| SEQ. ID. NO. 37195 | 765-GlnLeuLysAspLeuSerSerValGlyArgAsnProAlaGlyArgMetAspVal-782 |
| SEQ. ID. NO. 37196 | 792-SerLeuSerAlaGlyArgAsnLysArgPro-801 |
| Hydrophilic Regions - Hopp-Woods | |
| SEQ. ID. NO. 37197 | 27-ValAlaAlaGluGluAlaAspGlyArgValAlaGluGlyGlyAla-41 |
| SEQ. ID. NO. 37198 | 43-GlyAlaSerGluSerAlaGlnAlaSer-51 |
| SEQ. ID. NO. 37199 | 64-AsnGluSerGlySerProGluArgThrGluAlaAlaVal-76 |
| SEQ. ID. NO. 37200 | 78-GlySerGlyGluAlaSerValProGluAspTyrThr-89 |

TABLE 1-continued

| | |
|---|---|
| SEQ. ID. NO. 37201 | 92-ValAlaAspArgMetGluGlyGlnSerLysValLysValArgAlaGluGly-108 |
| SEQ. ID. NO. 37202 | 110-ValIleIleGluArgAspGlyAla-117 |
| SEQ. ID. NO. 37203 | 124-AlaAspTyrAspGlnSerGlyAsp-131 |
| SEQ. ID. NO. 37204 | 146-ThrLeuIleArgGlyGluThr-152 |
| SEQ. ID. NO. 37205 | 159-GlnGlnThrGlyGluAlaHisAsnValArgMetGluThrGluGlnGlyGlyArgArgLeuGlnSerValSerArgThrAlaGluMetLeu GlyGluGlyArgTyrLysLeuThrGlu-197 |
| SEQ. ID. NO. 37206 | 215-AlaSerValGluAlaAspArgGlyLysGly-224 |
| SEQ. ID. NO. 37207 | 249-ProLeuAspGlyAsnArgLysSerGly-257 |
| SEQ. ID. NO. 37208 | 265-AlaGlySerAspGlyVal-270 |
| SEQ. ID. NO. 37209 | 293-IleGlyGluArgGlyAlaThr-299 |
| SEQ. ID. NO. 37210 | 304-IleArgTyrLeuArg-308 |
| SEQ. ID. NO. 37211 | 322-HisAspLysLysSerGlyArgAsnAsnArgTyrGlnAla-334 |
| SEQ. ID. NO. 37212 | 336-TrpGlnHisArgHisAspIleSerAsp-344 |
| SEQ. ID. NO. 37213 | 409-SerGlyTyrLysAspGluProTyr-416 |
| SEQ. ID. NO. 37214 | 422-LeuSerAlaAspTrpHisLysAsnAlaGlyArgAla-433 |
| SEQ. ID. NO. 37215 | 444-PheSerHisAspGlyArgGlnAspGlySerArg-454 |
| SEQ. ID. NO. 37216 | 488-PheGlyGlyLysAlaSerArgSerValGly-497 |
| SEQ. ID. NO. 37217 | 509-ThrThrPheGluArgAsnThrArg-516 |
| SEQ. ID. NO. 37218 | 538-LysSerGlnAsnAsp-542 |
| SEQ. ID. NO. 37219 | 547-AspSerSerGluSer-551 |
| SEQ. ID. NO. 37220 | 568-AspArgIleAsnAla-572 |
| SEQ. ID. NO. 37221 | 588-AlaThrGlyGluGluArgPheArgAla-596 |
| SEQ. ID. NO. 37222 | 603-TyrPheLysAspAspAlaValMet-610 |
| SEQ. ID. NO. 37223 | 614-SerValGlyLysAsnProArgSerArgSerAsp-624 |
| SEQ. ID. NO. 37224 | 647-GlnAsnAspLysArgAlaGluHis-654 |
| SEQ. ID. NO. 37225 | 673-TyrLysTyrGlyArgAsnGluLysIle-681 |
| SEQ. ID. NO. 37226 | 719-PheGluAlaLysLysProIleGlu-726 |
| SEQ. ID. NO. 37227 | 731-AlaGluTyrLysSer-735 |
| SEQ. ID. NO. 37228 | 765-GlnLeuLysAspLeuSerSerValGlyArgAsnProAlaGlyArgMetAspVal-782 |
| SEQ. ID. NO. 37229 | 794-SerAlaGlyArgAsnLysArgPro-801 |
| g959 | |
| AMPHI Regions - AMPHI | |
| SEQ. ID. NO. 37230 | 56-AlaAlaTrpAlaArgValGlyGly-63 |
| Antigenic Index - Jameson-Wolf | |
| SEQ. ID. NO. 37231 | 24-AlaHisHisAspGlyHisGlyAspAspAspHisGlyHis-36 |
| SEQ. ID. NO. 37232 | 38-AlaHisGlnHisGlyLysGlnAspLysIleIleSer-49 |
| SEQ. ID. NO. 37233 | 51-AlaGlnAlaGluLysAlaAla-57 |
| SEQ. ID. NO. 37234 | 60-ArgValGlyGlyLysIleThrAspIleAspLeuGluHisAspAspGlyArgProHisTyrAspValGluIleValLysAsnGlyGlnGluTyr-90 |
| SEQ. ID. NO. 37235 | 94-ValAspAlaArgThrGlyArgValIleSerSerArgArgAspAsp-108 |
| Hydrophilic Regions - Hopp-Woods | |
| SEQ. ID. NO. 37236 | 27-AspGlyHisGlyAspAspAspHisGlyHis-36 |
| SEQ. ID. NO. 37237 | 40-GlnHisGlyLysGlnAspLysIleIleSer-49 |
| SEQ. ID. NO. 37238 | 51-AlaGlnAlaGluLysAlaAla-57 |
| SEQ. ID. NO. 37239 | 61-ValGlyGlyLysIleThrAspIleAspLeuGluHisAspAspGlyArgProHisTyr-79 |
| SEQ. ID. NO. 37240 | 82-GluIleValLysAsnGlyGlnGluTyr-90 |
| SEQ. ID. NO. 37241 | 94-ValAspAlaArgThrGlyArg-100 |
| SEQ. ID. NO. 37242 | 102-IleSerSerArgArgAspAsp-108 |
| g973 | |
| AMPHI Regions - AMPHI | |
| SEQ. ID. NO. 37243 | 12-GluArgLeuIleAlaArgLeuAlaArgGluProAspSerAlaGluAspValLeuAsnLeuLeuArgGlnAla-35 |
| SEQ. ID. NO. 37244 | 44-AspThrLeuThrArgLeuGluLysValLeuAspPhe-55 |
| SEQ. ID. NO. 37245 | 77-AspSerIleGluArgIleThrAlaTyr-85 |
| SEQ. ID. NO. 37246 | 112-AspLeuLeuLysTyrMet-117 |
| SEQ. ID. NO. 37247 | 143-AlaLeuLeuLysGluPheArgGluGln-151 |
| SEQ. ID. NO. 37248 | 171-PheGluAspIleIleGluGlnIleValGlyAspIleGluAsp-184 |
| SEQ. ID. NO. 37249 | 190-GluSerAlaAspAspIleHisSerVal-198 |
| SEQ. ID. NO. 37250 | 208-AlaThrGluIleGluAspIleAsnAlaPhe-217 |
| SEQ. ID. NO. 37251 | 235-IleGlnGluLeuGly-239 |
| Antigenic Index - Jameson-Wolf | |
| SEQ. ID. NO. 37252 | 1-MetAspGlyAlaGlnProLysThrAsnPhe-10 |
| SEQ. ID. NO. 37253 | 18-LeuAlaArgGluProAspSerAlaGluAspVal-28 |
| SEQ. ID. NO. 37254 | 34-GlnAlaHisGluGlnGluValPheAspAlaAspThrLeuThrArgLeuGluLysValLeuAsp-54 |
| SEQ. ID. NO. 37255 | 56-AlaGluLeuGluValArgAspAlaMetIleThrArgSerArgMetAsnValLeuLysGluAsnAspSerIleGluArg-81 |
| SEQ. ID. NO. 37256 | 96-ValIleGlyGluAspLysAspGluVal-104 |
| SEQ. ID. NO. 37257 | 118-PheAsnProGluGlnPheHis-124 |
| SEQ. ID. NO. 37258 | 136-ProGluGlyLysSer-140 |
| SEQ. ID. NO. 37259 | 146-LysGluPheArgGluGlnArgAsnHis-154 |
| SEQ. ID. NO. 37260 | 159-IleAspGluTyrGlyGlyThrSerGly-167 |
| SEQ. ID. NO. 37261 | 178-IleValGlyAspIleGluAspGluPheAspGluAspGluSerAlaAspAspIleHis-196 |
| SEQ. ID. NO. 37262 | 199-SerAlaGluArgTrpArg-204 |
| SEQ. ID. NO. 37263 | 209-ThrGluIleGluAsp-213 |
| SEQ. ID. NO. 37264 | 219-GlyThrGluTyrGlySerGluGluAlaAspThr-229 |
| SEQ. ID. NO. 37265 | 239-GlyHisLeuProValArgGlyGluLysValLeu-249 |
| SEQ. ID. NO. 37266 | 258-AlaArgAlaAspAsnArgArgLeuHis-266 |
| Hydrophilic Regions - Hopp-Woods | |
| SEQ. ID. NO. 37267 | 1-MetAspGlyAlaGlnProLys-7 |
| SEQ. ID. NO. 37268 | 18-LeuAlaArgGluProAspSerAlaGluAspVal-28 |
| SEQ. ID. NO. 37269 | 34-GlnAlaHisGluGlnGluValPheAsp-42 |
| SEQ. ID. NO. 37270 | 44-AspThrLeuThrArgLeuGluLysValLeuAsp-54 |
| SEQ. ID. NO. 37271 | 56-AlaGluLeuGluValArgAspAlaMetIleThrArgSerArgMetAsnValLeuLysGluAsnAspSerIleGluArg-81 |

TABLE 1-continued

| | |
|---|---|
| SEQ. ID. NO. 37272 | 96-ValIleGlyGluAspLysAspGluVal-104 |
| SEQ. ID. NO. 37273 | 136-ProGluGlyLysSer-140 |
| SEQ. ID. NO. 37274 | 146-LysGluPheArgGluGlnArgAsn-153 |
| SEQ. ID. NO. 37275 | 178-IleValGlyAspIleGluAspGluPheAspGluAspGluSerAlaAspAspIleHis-196 |
| SEQ. ID. NO. 37276 | 199-SerAlaGluArgTrpArg-204 |
| SEQ. ID. NO. 37277 | 209-ThrGluIleGluAsp-213 |
| SEQ. ID. NO. 37278 | 222-TyrGlySerGluGluAlaAspThr-229 |
| SEQ. ID. NO. 37279 | 243-ValArgGlyGluLysValLeu-249 |
| SEQ. ID. NO. 37280 | 258-AlaArgAlaAspAsnArgArgLeuHis-266 |
| g981 | |
| AMPHI Regions - AMPHI | |
| SEQ. ID. NO. 37281 | 32-AsnProGlyLysValTyrArgValAlaSer-41 |
| SEQ. ID. NO. 37282 | 46-AlaProPheGluSerLeuAsp-52 |
| SEQ. ID. NO. 37283 | 66-AsnAlaMetAlaLys-70 |
| SEQ. ID. NO. 37284 | 132-LysValSerSerSerGluAspLeuLysLysMetAsnLysValGly-146 |
| SEQ. ID. NO. 37285 | 167-LysIleAlaArgPheGlu-172 |
| SEQ. ID. NO. 37286 | 181-LeuGluAsnGlyGlyLeuAspSerValVal-190 |
| SEQ. ID. NO. 37287 | 197-AlaAsnTyrValLysAsnAsnPro-204 |
| SEQ. ID. NO. 37288 | 207-GlyMetAspPheValThrLeuPro-214 |
| SEQ. ID. NO. 37289 | 233-ValLysMetLeuAsnAspAlaLeuGluLysValArgGluSerGlyGluTyr-249 |
| Antigenic Index - Jameson-Wolf | |
| SEQ. ID. NO. 37290 | 19-CysGlyGlyGlnGlyLysAspAlaAlaAla-28 |
| SEQ. ID. NO. 37291 | 30-AlaAlaAsnProGlyLysValTyrArg-38 |
| SEQ. ID. NO. 37292 | 49-GluSerLeuAspSerLysGlyAsnValGluGlyPheAsp-61 |
| SEQ. ID. NO. 37293 | 76-IleGluPheLysHisGlnProTrpAspSer-85 |
| SEQ. ID. NO. 37294 | 90-LeuAsnAsnGlyAspAlaAspVal-97 |
| SEQ. ID. NO. 37295 | 104-IleThrAspAspArgLysGlnSerMetAspPheSerAspProTyrPhe-119 |
| SEQ. ID. NO. 37296 | 127-ValProLysGlyLysLysValSerSerSerGluAspLeuLysLysMetAsnLysValGly-146 |
| SEQ. ID. NO. 37297 | 149-ThrGlyHisThrGlyAspPheSerVal-157 |
| SEQ. ID. NO. 37298 | 159-LysLeuLeuGlyAsnAspAsnProLysIleAlaArg-170 |
| SEQ. ID. NO. 37299 | 179-LysGluLeuGluAsnGlyGlyLeuAspSerValValSerAspSerAla-194 |
| SEQ. ID. NO. 37300 | 201-LysAsnAsnProAlaLysGlyMetAspPhe-210 |
| SEQ. ID. NO. 37301 | 214-ProAspPheThrThr-218 |
| SEQ. ID. NO. 37302 | 225-ValArgLysGlyAspGluAlaThrVal-233 |
| SEQ. ID. NO. 37303 | 235-MetLeuAsnAspAlaLeuGluLysValArgGluSerGlyGluTyrAspLysIleTyr-253 |
| SEQ. ID. NO. 37304 | 257-PheAlaLysGluGlyGlyGlnAlaAlaLys-266 |
| Hydrophilic Regions - Hopp-Woods | |
| SEQ. ID. NO. 37305 | 21-GlyGlnGlyLysAspAlaAlaAla-28 |
| SEQ. ID. NO. 37306 | 49-GluSerLeuAspSerLysGlyAsnValGluGlyPheAsp-61 |
| SEQ. ID. NO. 37307 | 91-AsnAsnGlyAspAlaAspVal-97 |
| SEQ. ID. NO. 37308 | 104-IleThrAspAspArgLysGlnSerMetAspPheSer-115 |
| SEQ. ID. NO. 37309 | 128-ProLysGlyLysLysValSerSerSerGluAspLeuLysLysMetAsnLys-144 |
| SEQ. ID. NO. 37310 | 164-AspAsnProLysIleAlaArg-170 |
| SEQ. ID. NO. 37311 | 179-LysGluLeuGluAsnGlyGlyLeu-186 |
| SEQ. ID. NO. 37312 | 203-AsnProAlaLysGlyMetAsp-209 |
| SEQ. ID. NO. 37313 | 225-ValArgLysGlyAspGluAlaThrVal-233 |
| SEQ. ID. NO. 37314 | 235-MetLeuAsnAspAlaLeuGluLysValArgGluSerGlyGluTyrAspLysIleTyr-253 |
| SEQ. ID. NO. 37315 | 257-PheAlaLysGluGlyGlyGlnAlaAlaLys-266 |
| g982 | |
| AMPHI Regions - AMPHI | |
| SEQ. ID. NO. 37316 | 10-ArgPheLeuGlnLysMetValAsnGlyValAsnIleLeuProAlaAlaAspTrp-27 |
| SEQ. ID. NO. 37317 | 70-AlaGlnMetValLysGluValAlaSerLysThr-80 |
| SEQ. ID. NO. 37318 | 99-ValAlaGluGlyMetLysTyr-105 |
| SEQ. ID. NO. 37319 | 114-AspLeuLysArgGlyIleAspLysAlaValAlaAlaLeuValGluGluLeuLysAsnIleAlaLysProCysAspThrSerLysGluIleAla GlnValGlySer-148 |
| SEQ. ID. NO. 37320 | 159-AlaIleIleAlaGluAlaMetGluLysValGly-169 |
| SEQ. ID. NO. 37321 | 184-AsnGluLeuAspValValGluGlyMet-192 |
| SEQ. ID. NO. 37322 | 208-GluLysGlnIleAlaGlyLeuAsp-215 |
| SEQ. ID. NO. 37323 | 226-IleSerAsnIleArgAspLeuLeuProValLeuGluGlnValAlaLysAla-242 |
| SEQ. ID. NO. 37324 | 264-AsnAsnIleArgGlyIleLeuLysThrValAla-274 |
| SEQ. ID. NO. 37325 | 312-ThrLeuAspAspLeuGlyGlnThrLysArg-321 |
| SEQ. ID. NO. 37326 | 330-ThrValIleAspGlyPheGlyAspAlaAla-339 |
| SEQ. ID. NO. 37327 | 366-GluArgValAlaLysLeuAlaGlyGlyVal-375 |
| SEQ. ID. NO. 37328 | 425-LeuGluAsnLeuHisThr-430 |
| SEQ. ID. NO. 37329 | 443-LeuArgAlaValGluSerProLeuArgGlnIleValAlaAsnAla-457 |
| SEQ. ID. NO. 37330 | 483-GluTyrGlyAspMetIleGlyMet-490 |
| SEQ. ID. NO. 37331 | 499-ThrArgSerAlaLeu-503 |
| Antigenic Index - Jameson-Wolf | |
| SEQ. ID. NO. 37332 | 1-AlaSerGlnAsnLeuArgPheAspAsnArgPheLeu-12 |
| SEQ. ID. NO. 37333 | 31-GlyAlaLysGlyArgAsnValValVal-39 |
| SEQ. ID. NO. 37334 | 42-AlaPheGlyGlyProHisIleThrLysAspGlyValThrValAlaLysGluIleGluLeuLysAspLysPheGluAsnMetGly-69 |
| SEQ. ID. NO. 37335 | 72-MetValLysGluValAlaSerLysThrAsnAspValAlaGlyAspGlyThrThr-89 |
| SEQ. ID. NO. 37336 | 111-AsnProThrAspLeuLysArgGlyIleAspLysAlaVal-123 |
| SEQ. ID. NO. 37337 | 128-GluGluLeuLysAsnIleAlaLysProCysAspThrSerLysGluIleAla-144 |
| SEQ. ID. NO. 37338 | 149-IleSerAlaAsnSerAspGluGlnVal-157 |
| SEQ. ID. NO. 37339 | 163-GluAlaMetGluLysValGlyLysGluGlyValIleThrValGluAspGlyLysSerLeuGluAsnGluLeuAspVal-188 |
| SEQ. ID. NO. 37340 | 192-MetGlnPheAspArgGlyTyr-198 |
| SEQ. ID. NO. 37341 | 206-AspAlaGluLysGlnIleAla-212 |
| SEQ. ID. NO. 37342 | 222-PheAspLysLysIleSerAsnIleArgAsp-231 |
| SEQ. ID. NO. 37343 | 238-GlnValAlaLysAlaSerArg-244 |

TABLE 1-continued

| | |
|---|---|
| SEQ. ID. NO. 37344 | 251-GluAspValGluGlyGluAla-257 |
| SEQ. ID. NO. 37345 | 265-AsnIleArgGlyIleLeu-270 |
| SEQ. ID. NO. 37346 | 277-AlaProGlyPheGlyAspArgArgLysAlaMetLeu-288 |
| SEQ. ID. NO. 37347 | 300-IleSerGluGluValGlyLeuSerLeuGluLysAlaThrLeuAspAspLeuGlyGlnThrLysArgIleGluIleGlyGluGluAsnThrThr-330 |
| SEQ. ID. NO. 37348 | 333-AspGlyPheGlyAspAlaAlaGlnIleGluAlaArgValAlaGluIleArgGlnGlnIleGluThrAlaThrSerAspTyrAspLysGluLysLeu GlnGluArgValAlaLysLeuAlaGly-373 |
| SEQ. ID. NO. 37349 | 384-ThrGluValGluMetLysGluLysLysAspArgValGluAspAlaLeuHis-400 |
| SEQ. ID. NO. 37350 | 404-AlaAlaValGluGluGlyVal-410 |
| SEQ. ID. NO. 37351 | 420-ArgAlaArgAlaAlaLeu-425 |
| SEQ. ID. NO. 37352 | 428-LeuHisThrGlyAsnAlaAspGlnAspAlaGlyVal-439 |
| SEQ. ID. NO. 37353 | 445-AlaValGluSerProLeuArg-451 |
| SEQ. ID. NO. 37354 | 456-AsnAlaGlyGlyGluProSerVal-463 |
| SEQ. ID. NO. 37355 | 468-ValLeuGluGlyLysGlyAsnTyrGlyTyr-477 |
| SEQ. ID. NO. 37356 | 479-AlaGlySerGlyGluTyrGlyAsp-486 |
| SEQ. ID. NO. 37357 | 494-AspProAlaLysValThrArgSerAlaLeu-503 |
| SEQ. ID. NO. 37358 | 522-GluIleProGluGluLysProAlaValProAspMetGlyGly-535 |
| Hydrophilic Regions - Hopp-Woods | |
| SEQ. ID. NO. 37359 | 5-LeuArgPheAspAsn-9 |
| SEQ. ID. NO. 37360 | 32-AlaLysGlyArgAsnValValVal-39 |
| SEQ. ID. NO. 37361 | 47-HisIleThrLysAspGlyValThrValAlaLysGluIleGluLeuLysAspLysPheGluAsn-67 |
| SEQ. ID. NO. 37362 | 72-MetValLysGluValAlaSerLysThrAsnAspValAlaGlyAspGlyThrThr-89 |
| SEQ. ID. NO. 37363 | 113-ThrAspLeuLysArgGlyIleAspLysAlaVal-123 |
| SEQ. ID. NO. 37364 | 128-GluGluLeuLysAsnIleAlaLysProCysAspThrSerLysGluIleAla-144 |
| SEQ. ID. NO. 37365 | 151-AlaAsnSerAspGluGlnVal-157 |
| SEQ. ID. NO. 37366 | 163-GluAlaMetGluLysValGlyLysGluGlyValIleThrValGluAspGlyLysSerLeuGluAsnGluLeuAspVal-188 |
| SEQ. ID. NO. 37367 | 206-AspAlaGluLysGlnIleAla-212 |
| SEQ. ID. NO. 37368 | 222-PheAspLysLysIleSerAsnIleArgAsp-231 |
| SEQ. ID. NO. 37369 | 238-GlnValAlaLysAlaSerArg-244 |
| SEQ. ID. NO. 37370 | 251-GluAspValGluGlyGluAla-257 |
| SEQ. ID. NO. 37371 | 279-GlyPheGlyAspArgArgLysAlaMetLeu-288 |
| SEQ. ID. NO. 37372 | 300-IleSerGluGluValGlyLeuSerLeuGluLysAlaThrLeuAspAspLeuGlyGlnThrLysArgIleGluIleGlyGluGluAsnThrThr-330 |
| SEQ. ID. NO. 37373 | 339-AlaGlnIleGluAlaArgValAlaGluIleArgGlnGlnIleGluThrAlaThrSerAspTyrAspLysGluLysLeuGlnGluArgValAla Lys-370 |
| SEQ. ID. NO. 37374 | 384-ThrGluValGluMetLysGluLysLysAspArgValGluAspAlaLeuHis-400 |
| SEQ. ID. NO. 37375 | 404-AlaAlaValGluGluGlyVal-410 |
| SEQ. ID. NO. 37376 | 420-ArgAlaArgAlaAlaLeu-425 |
| SEQ. ID. NO. 37377 | 431-GlyAsnAlaAspGlnAspAla-437 |
| SEQ. ID. NO. 37378 | 445-AlaValGluSerProLeu-450 |
| SEQ. ID. NO. 37379 | 457-AlaGlyGlyGluPro-461 |
| SEQ. ID. NO. 37380 | 468-ValLeuGluGlyLysGly-473 |
| SEQ. ID. NO. 37381 | 480-GlySerGlyGluTyrGlyAsp-486 |
| SEQ. ID. NO. 37382 | 494-AspProAlaLysValThrArg-500 |
| SEQ. ID. NO. 37383 | 522-GluIleProGluGluLysProAlaVal-530 |
| g986 | |
| AMPHI Regions - AMPHI | |
| SEQ. ID. NO. 37384 | 6-GlnTyrPheAlaLeuAlaAlaLeuCysAlaAlaLeuLeuAla-19 |
| SEQ. ID. NO. 37385 | 21-CysGluLysAlaGly-25 |
| SEQ. ID. NO. 37386 | 36-SerPheValGluArgIleGluHis-43 |
| SEQ. ID. NO. 37387 | 55-ProAspPheAlaGlnLeuValGln-62 |
| SEQ. ID. NO. 37388 | 97-AspProPheTyrGluPhePheLysArgLeuValProAsnMetProGluIleProGln-115 |
| SEQ. ID. NO. 37389 | 145-AlaGlyMetGlySerIle-150 |
| SEQ. ID. NO. 37390 | 162-AlaLysLeuIleGlySerAspVal-169 |
| SEQ. ID. NO. 37391 | 189-IleGlyAsnProLysAsnLeuLysProGly-198 |
| SEQ. ID. NO. 37392 | 200-TrpValAlaAlaIleGly-205 |
| SEQ. ID. NO. 37393 | 287-AlaGluGlnLeuLysAsnThrGlyLysVal-296 |
| SEQ. ID. NO. 37394 | 393-AlaAlaGluHisThrGly-398 |
| SEQ. ID. NO. 37395 | 471-ArgLysAlaMetAspLysAla-477 |
| Antigenic Index - Jameson-Wolf | |
| SEQ. ID. NO. 37396 | 20-GlyCysGluLysAlaGlySer-26 |
| SEQ. ID. NO. 37397 | 29-GlyAlaAspLysLysGluAlaSerPheValGluArgIleGluHisThrLysAspAspGlySerVal-50 |
| SEQ. ID. NO. 37398 | 61-ValGlnSerGluGlyProAla-67 |
| SEQ. ID. NO. 37399 | 75-ProAlaProArgThrGlnAsnGlySerGlyAsnAlaGluThrAspSerAspProLeuAlaAspSerAspProPhe-99 |
| SEQ. ID. NO. 37400 | 104-LysArgLeuValProAsnMetProGluIleProGlnGluGluAlaAspAspGlyGlyLeu-123 |
| SEQ. ID. NO. 37401 | 154-LeuAsnAspLysArgGluTyrThr-161 |
| SEQ. ID. NO. 37402 | 165-IleGlySerAspValGlnSerAspValAla-174 |
| SEQ. ID. NO. 37403 | 179-AspAlaThrGluGluLeuPro-185 |
| SEQ. ID. NO. 37404 | 189-IleGlyAsnProLysAsnLeuLysProGlyGlu-199 |
| SEQ. ID. NO. 37405 | 208-PheGlyPheAspAsnSerVal-214 |
| SEQ. ID. NO. 37406 | 219-ValSerAlaLysGlyArgSerLeuProAsnGluSerTyr-231 |
| SEQ. ID. NO. 37407 | 242-AsnProGlyAsnSerGlyGlyPro-249 |
| SEQ. ID. NO. 37408 | 265-TyrSerArgSerGlyGly-270 |
| SEQ. ID. NO. 37409 | 288-GluGlnLeuLysAsnThrGlyLysValGlnArgGlyGlnLeu-301 |
| SEQ. ID. NO. 37410 | 316-PheGlyLeuAspLysAlaSerGly-323 |
| SEQ. ID. NO. 37411 | 330-LeuProGlySerProAlaGluArgAlaGlyLeuGlnAlaGlyAsp-344 |
| SEQ. ID. NO. 37412 | 349-LeuAspGlyGlyGluIleArgSerSerGlyAspLeu-360 |
| SEQ. ID. NO. 37413 | 368-ThrProGlyLysGluValSer-374 |
| SEQ. ID. NO. 37414 | 378-TrpArgLysGlyGluGluIleThrIle-386 |
| SEQ. ID. NO. 37415 | 394-AlaGluHisThrGlyAlaSerSerLysThrAspGluAlaProTyrThrGluGlnGlnSerGlyThrPhe-416 |
| SEQ. ID. NO. 37416 | 427-ThrHisThrAspSerSerGlyLysHis-435 |
| SEQ. ID. NO. 37417 | 440-ArgValSerAspAlaAlaGluArgAlaGlyLeuArgArgGlyAspGluIleLeu-457 |

TABLE 1-continued

| | |
|---|---|
| SEQ. ID. NO. 37418 | 463-ProValAsnAspGluAlaGlyPheArgLysAlaMetAspLysAlaGlyLysAsnVal-481 |
| SEQ. ID. NO. 37419 | 486-MetArgArgGlyAsnThr-491 |
| Hydrophilic Regions - Hopp-Woods | |
| SEQ. ID. NO. 37420 | 20-GlyCysGluLysAlaGly-25 |
| SEQ. ID. NO. 37421 | 29-GlyAlaAspLysLysGluAlaSerPheValGluArgIleGluHisThrLysAspAspGlySer-49 |
| SEQ. ID. NO. 37422 | 75-ProAlaProArgThrGlnAsnGlySerGlyAsnAlaGluThrAspSerAspProLeuAlaAspSerAspPro-98 |
| SEQ. ID. NO. 37423 | 111-ProGluIleProGlnGluGluAlaAspAspGlyGly-122 |
| SEQ. ID. NO. 37424 | 154-LeuAsnAspLysArgGluTyrThr-161 |
| SEQ. ID. NO. 37425 | 179-AspAlaThrGluGluLeuPro-185 |
| SEQ. ID. NO. 37426 | 193-LysAsnLeuLysPro-197 |
| SEQ. ID. NO. 37427 | 221-AlaLysGlyArgSerLeuPro-227 |
| SEQ. ID. NO. 37428 | 288-GluGlnLeuLysAsnThrGlyLysValGlnArgGlyGln-300 |
| SEQ. ID. NO. 37429 | 317-GlyLeuAspLysAlaSer-322 |
| SEQ. ID. NO. 37430 | 333-SerProAlaGluArgAlaGlyLeuGln-341 |
| SEQ. ID. NO. 37431 | 350-AspGlyGlyGluIleArgSerSerGlyAsp-359 |
| SEQ. ID. NO. 37432 | 368-ThrProGlyLysGluValSer-374 |
| SEQ. ID. NO. 37433 | 379-ArgLysGlyGluGluIleThrIle-386 |
| SEQ. ID. NO. 37434 | 394-AlaGluHisThrGlyAlaSerSerLysThrAspGluAlaProTyrThrGluGlnGlnSer-413 |
| SEQ. ID. NO. 37435 | 428-HisThrAspSerSerGly-433 |
| SEQ. ID. NO. 37436 | 440-ArgValSerAspAlaAlaGluArgAlaGlyLeuArgArgGlyAspGluIleLeu-457 |
| SEQ. ID. NO. 37437 | 463-ProValAsnAspGluAlaGlyPheArgLysAlaMetAspLysAlaGlyLys-479 |
| g987 | |
| AMPHI Regions - AMPHI | |
| SEQ. ID. NO. 37438 | 17-CysSerSerTrpLeu-21 |
| SEQ. ID. NO. 37439 | 65-ProHisGluAlaPhe-69 |
| SEQ. ID. NO. 37440 | 121-AsnThrArgGly-124 |
| SEQ. ID. NO. 37441 | 135-HisProAsnIleValArgLeuPheAsnProPheValLeuArgLysTrpArgAlaLeuGlyTyrLeuThrAspPheProArgLeuAsnArg-164 |
| SEQ. ID. NO. 37442 | 186-GlyAspGluTyrPheLysVal-192 |
| SEQ. ID. NO. 37443 | 201-LeuAspIleLeuAlaThr-206 |
| SEQ. ID. NO. 37444 | 210-ValGlyGluValSerHisAspPheAspArgTyrTrpAla-222 |
| SEQ. ID. NO. 37445 | 229-AlaThrArgIleIleArgSerGly-236 |
| SEQ. ID. NO. 37446 | 238-IleGlyLysGlyLeuGlnAla-244 |
| SEQ. ID. NO. 37447 | 288-SerAspSerProAlaLysGlyLeuAspArg-297 |
| SEQ. ID. NO. 37448 | 306-GlyArgLeuGlnAspAlaLeuLysGlnPro-315 |
| SEQ. ID. NO. 37449 | 332-GlyThrAspAlaLeuAlaLysLeuValGlnAsp-342 |
| SEQ. ID. NO. 37450 | 354-GlnAlaThrAspValAlaAla-360 |
| SEQ. ID. NO. 37451 | 442-LysIleAlaGluGlnMetGluArgThrLeuAlaAspThrThrPro-456 |
| SEQ. ID. NO. 37452 | 485-ProGluAlaLysLeuTrpLysArgIleAlaAlaLysIleLeuSerLeuLeuProIleGluGlyLeu-506 |
| Antigenic Index - Jameson-Wolf | |
| SEQ. ID. NO. 37453 | 1-MetLysThrArgSer-5 |
| SEQ. ID. NO. 37454 | 23-ProLeuGluGluArgThrGluSerArgHisPheAsnThrSerLysProValLeu-40 |
| SEQ. ID. NO. 37455 | 49-HisThrProHisAsnAsnGlyLeuSer-57 |
| SEQ. ID. NO. 37456 | 77-GluSerAlaGluHisSerLeu-83 |
| SEQ. ID. NO. 37457 | 90-TrpArgAsnAspIleSerGlyArgLeu-98 |
| SEQ. ID. NO. 37458 | 107-AlaGluArgGlyValArg-112 |
| SEQ. ID. NO. 37459 | 115-LeuLeuLeuAspAspAsnAsnThrArgGlyLeuAsp-126 |
| SEQ. ID. NO. 37460 | 134-SerHisProAsnIle-138 |
| SEQ. ID. NO. 37461 | 158-AspPheProArgLeuAsnArgArgMetHisAsnLysSerPheThrAlaAspAsnArgAla-177 |
| SEQ. ID. NO. 37462 | 181-GlyGlyArgAsnIleGlyAspGluTyrPheLysValGlyGluAspThrVal-197 |
| SEQ. ID. NO. 37463 | 213-ValSerHisAspPheAspArgTyrTrp-221 |
| SEQ. ID. NO. 37464 | 224-HisSerAlaHisAsn-228 |
| SEQ. ID. NO. 37465 | 231-ArgIleIleArgSerGlyAsnIleGlyLysGlyLeu-242 |
| SEQ. ID. NO. 37466 | 246-GlyTyrAsnAspGluThrSerArg-253 |
| SEQ. ID. NO. 37467 | 258-ArgTyrArgGluThrValGlu-264 |
| SEQ. ID. NO. 37468 | 266-SerProLeuTyrGln-270 |
| SEQ. ID. NO. 37469 | 272-IleGlnThrGlyArgIleAsp-278 |
| SEQ. ID. NO. 37470 | 286-LeuIleSerAspSerProAlaLysGlyLeuAspArgAspArgArgLysProProIle-304 |
| SEQ. ID. NO. 37471 | 307-ArgLeuGlnAspAlaLeuLysGlnProGluLysSer-318 |
| SEQ. ID. NO. 37472 | 327-ValProThrLysSerGlyThrAspAlaLeu-336 |
| SEQ. ID. NO. 37473 | 339-LeuValGlnAspGlyIleAsp-345 |
| SEQ. ID. NO. 37474 | 366-ValLysTyrArgLysProLeuLeu-373 |
| SEQ. ID. NO. 37475 | 390-AlaThrLysAspLysGlyLeuThrGlySerSerVal-401 |
| SEQ. ID. NO. 37476 | 411-ValAspGlyLysArgIlePhe-417 |
| SEQ. ID. NO. 37477 | 421-PheAsnLeuAspProArgSerAlaArgLeuAsnThr-432 |
| SEQ. ID. NO. 37478 | 439-GluSerProLysIleAlaGluGlnMetGluArgThrLeuAlaAspThrThrProGluTyrAlaTyr-460 |
| SEQ. ID. NO. 37479 | 462-ValThrLeuAspLysHisAsnArgLeuGlnTrpHisAspProAlaThrArgLysThrTyrProAsnGluProGluAlaLysLeuTrpLys-491 |
| Hydrophilic Regions - Hopp-Woods | |
| SEQ. ID. NO. 37480 | 1-MetLysThrArgSer-5 |
| SEQ. ID. NO. 37481 | 24-LeuGluGluArgThrGluSerArgHisPheAsnThr-35 |
| SEQ. ID. NO. 37482 | 77-GluSerAlaGluHisSerLeu-83 |
| SEQ. ID. NO. 37483 | 107-AlaGluArgGlyValArg-112 |
| SEQ. ID. NO. 37484 | 115-LeuLeuLeuAspAspAsnAsnThrArgGlyLeuAsp-126 |
| SEQ. ID. NO. 37485 | 160-ProArgLeuAsnArgArgMetHisAsn-168 |
| SEQ. ID. NO. 37486 | 171-PheThrAlaAspAsnArgAla-177 |
| SEQ. ID. NO. 37487 | 188-GluTyrPheLysValGlyGluAspThrVal-197 |
| SEQ. ID. NO. 37488 | 213-ValSerHisAspPheAspArg-219 |
| SEQ. ID. NO. 37489 | 247-TyrAsnAspGluThrSerArg-253 |
| SEQ. ID. NO. 37490 | 258-ArgTyrArgGluThrValGlu-264 |
| SEQ. ID. NO. 37491 | 273-GlnThrGlyArgIleAsp-278 |
| SEQ. ID. NO. 37492 | 290-SerProAlaLysGlyLeuAspArgAspArgArgLysProProIle-304 |

TABLE 1-continued

| | |
|---|---|
| SEQ. ID. NO. 37493 | 307-ArgLeuGlnAspAlaLeuLysGlnProGluLysSer-318 |
| SEQ. ID. NO. 37494 | 330-LysSerGlyThrAspAlaLeu-336 |
| SEQ. ID. NO. 37495 | 339-LeuValGlnAspGlyIleAsp-345 |
| SEQ. ID. NO. 37496 | 366-ValLysTyrArgLysProLeuLeu-373 |
| SEQ. ID. NO. 37497 | 390-AlaThrLysAspLysGlyLeuThr-397 |
| SEQ. ID. NO. 37498 | 423-LeuAspProArgSerAlaArgLeuAsnThr-432 |
| SEQ. ID. NO. 37499 | 439-GluSerProLysIleAlaGluGlnMetGluArgThrLeuAla-452 |
| SEQ. ID. NO. 37500 | 463-ThrLeuAspLysHisAsnArg-469 |
| SEQ. ID. NO. 37501 | 475-ProAlaThrArgLysThrTyrProAsnGluProGluAlaLysLeuTrpLys-491 |
| g988 | |
| AMPHI Regions - AMPHI | |
| SEQ. ID. NO. 37502 | 45-SerLysIleGluSerLeuAlaArg-52 |
| SEQ. ID. NO. 37503 | 125-GlnMetArgGlyVal-129 |
| SEQ. ID. NO. 37504 | 154-AspIleValGluArgAlaGlnSerLysVal-163 |
| SEQ. ID. NO. 37505 | 221-AlaLysIleIleGluValLeuGlyAspTyrAlaAsp-232 |
| SEQ. ID. NO. 37506 | 248-HisArgPheSerGluAlaCysAlaLysSerAlaLysLysIleProAspHisValArgLys-267 |
| SEQ. ID. NO. 37507 | 288-ThrAlaArgAspPheAspAsp-294 |
| SEQ. ID. NO. 37508 | 299-GluLysValGlyArgAsnTyr-305 |
| SEQ. ID. NO. 37509 | 310-AlaIleAlaAspValSerHisTyrValArgProAspAsp-322 |
| SEQ. ID. NO. 37510 | 348-AsnLeuSerAsnGly-352 |
| SEQ. ID. NO. 37511 | 396-AsnGlnValTrpLysTrpLeuSerAspGlyIleGlyAsnProHisLys-411 |
| SEQ. ID. NO. 37512 | 413-GlnIleAspThrLeuTyrLysLeuPheLysIleLeuGlnLys-426 |
| SEQ. ID. NO. 37513 | 494-LeuGlyProThrProGluLysLeuAlaThrLeu-504 |
| SEQ. ID. NO. 37514 | 524-LysAspTyrAlaAlaLeuAlaGluGlnPheLys-534 |
| SEQ. ID. NO. 37515 | 544-ValMetMetLeuArgSerMetGlnGlnAla-553 |
| SEQ. ID. NO. 37516 | 555-TyrGluProHisCys-559 |
| SEQ. ID. NO. 37517 | 569-AlaTyrAlaHisPheThrSerProIleArgArgTyrProAspLeuThrValHisArgAlaIleLysAlaVal-592 |
| SEQ. ID. NO. 37518 | 618-AlaAspAspAlaGlyArgAspValGluAsnTrpLeuLys-630 |
| SEQ. ID. NO. 37519 | 641-IlePheGluGlyLysIleSerArgGly-649 |
| SEQ. ID. NO. 37520 | 653-PheGlyIlePheValThrLeu-659 |
| SEQ. ID. NO. 37521 | 667-LeuValHisIleSerAspLeuGlyGlu-675 |
| Antigenic Index - Jameson-Wolf | |
| SEQ. ID. NO. 37522 | 1-MetAsnLysAsnIleLys-6 |
| SEQ. ID. NO. 37523 | 8-LeuAsnLeuArgGluLysAspProPheLeuSerArgGluLysGlnArgTyrGluHisProLeuProSerArgGluTrpIle-34 |
| SEQ. ID. NO. 37524 | 37-LeuLeuGluArgLysGlyValProSerLysIleGluSerLeuAlaArgGluLeuSerIleThrGluAspGluTyrValPhePheGluArgArg LeuLysAlaMetAlaArgAspGlyGln-76 |
| SEQ. ID. NO. 37525 | 79-IleAsnArgArgGlyAlaVal-85 |
| SEQ. ID. NO. 37526 | 87-AlaAlaAspLysLeuAspLeuValLysCysArgValGluAlaHisLysAspGlyPhe-105 |
| SEQ. ID. NO. 37527 | 113-ProMetAspGluGlyAsp-118 |
| SEQ. ID. NO. 37528 | 124-ArgGlnMetArgGlyValMetHisGlyAspThrValThr-136 |
| SEQ. ID. NO. 37529 | 138-ArgProAlaGlyMetAspArgArgGlyArgArgGluGlyThrPhe-152 |
| SEQ. ID. NO. 37530 | 154-AspIleValGluArgAlaGlnSerLysValVal-164 |
| SEQ. ID. NO. 37531 | 168-TyrMetAspArgGlyValAla-174 |
| SEQ. ID. NO. 37532 | 176-LeuGluProGluAspLysArgLeuAsnGlnSerIle-187 |
| SEQ. ID. NO. 37533 | 189-LeuGluProAspGlyValAlaArgPheLysProGluSerGlyGln-203 |
| SEQ. ID. NO. 37534 | 210-GluValTyrProGluGlnAsnArgProAlaVal-220 |
| SEQ. ID. NO. 37535 | 227-LeuGlyAspTyrAlaAspSerGlyMetGluIle-237 |
| SEQ. ID. NO. 37536 | 239-IleAlaValArgLysHisHisLeuProHisArgPheSerGluAlaCysAlaLysSerAlaLysLysIleProAspHisValArgLysSerAspLeu LysGlyArgValAspLeuCys-277 |
| SEQ. ID. NO. 37537 | 283-ThrIleAspGlyGluThrAlaArgAspPheAspAsp-294 |
| SEQ. ID. NO. 37538 | 299-GluLysValGlyArgAsnTyrArg-306 |
| SEQ. ID. NO. 37539 | 316-HisTyrValArgProAspAspAlaIleAspAlaAspAlaGlnGluArgSerThrSerValTyrPheProArgArgMetIleProMetLeuPro GluAsnLeuSerAsnGlyIleCysSerLeuAsnProAspValGluArgLeu-363 |
| SEQ. ID. NO. 37540 | 374-AlaGlyAsnIleLysGluTyrArgPhe-382 |
| SEQ. ID. NO. 37541 | 393-LeuThrTyrAsnGln-397 |
| SEQ. ID. NO. 37542 | 402-LeuSerAspGlyIleGlyAsnProHisLysAlaGlnIle-414 |
| SEQ. ID. NO. 37543 | 424-LeuGlnLysLysArgLeuAlaArgGlyAlaValGluPheGluSerValGlu-440 |
| SEQ. ID. NO. 37544 | 443-MetIlePheAspAspAsnGlyLysIleGluLys-453 |
| SEQ. ID. NO. 37545 | 458-ValArgAsnAspAlaHisLysLeuIleGlu-467 |
| SEQ. ID. NO. 37546 | 482-LeuLysAsnLysHisThrAla-488 |
| SEQ. ID. NO. 37547 | 493-HisLeuGlyProThrProGluLysLeuAlaThrLeuArgGluGlnLeu-508 |
| SEQ. ID. NO. 37548 | 516-GlyGlyGlyAspAsnProSerProLysAspTyrAlaAla-528 |
| SEQ. ID. NO. 37549 | 531-GluGlnPheLysGlyArgProAspAlaGluLeu-541 |
| SEQ. ID. NO. 37550 | 555-TyrGluProHisCysGluGlyHis-562 |
| SEQ. ID. NO. 37551 | 575-SerProIleArgArgTyrProAspLeuThrVal-585 |
| SEQ. ID. NO. 37552 | 592-ValLeuAsnArgLysThrTyrThrProAsnLysSerTrp-604 |
| SEQ. ID. NO. 37553 | 613-PheCysGluArgArgAlaAspAspAlaGlyArgAspValGluAsn-627 |
| SEQ. ID. NO. 37554 | 633-TyrMetArgAspLysValGlyGluIlePheGluGlyLysIleSerArgGlyValAla-651 |
| SEQ. ID. NO. 37555 | 671-SerAspLeuGlyGluAspTyrPheAsnPheArgPro-682 |
| SEQ. ID. NO. 37556 | 684-IleMetAlaIleGluGlyGluArgSerGlyIleArgPheAsnMetGlyAspArgValAlaValArgValAlaArgAlaAspLeuAspAsp GlyLysIle-716 |
| SEQ. ID. NO. 37557 | 724-GluSerGlyArgArgArgLysValLysLeu-733 |
| SEQ. ID. NO. 37558 | 735-AlaSerAlaLysProAlaGlyAlaAlaGlyLysGlyLysSerLysThrThrAlaGluLysLysThrAlaArgCysGlyLysValArgGly ArgGlyValProAla-769 |
| SEQ. ID. NO. 37559 | 771-AlaGluSerGlyLysLysAlaLysLysProValProIleLysValLysLysArgLysGlyLysSer-792 |
| Hydrophilic Regions - Hopp-Woods | |
| SEQ. ID. NO. 37560 | 1-MetAsnLysAsnIleLys-6 |
| SEQ. ID. NO. 37561 | 8-LeuAsnLeuArgGluLysAspProPheLeuSerArgGluLysGlnArgTyrGluHis-26 |
| SEQ. ID. NO. 37562 | 37-LeuLeuGluArgLysGlyValProSerLysIleGluSerLeuAlaArgGluLeuSerIleThrGluAspGluTyrValPhePheGluArgArgLeu LysAlaMetAlaArgAspGlyGln-76 |

TABLE 1-continued

| | |
|---|---|
| SEQ. ID. NO. 37563 | 79-IleAsnArgArgGlyAla-84 |
| SEQ. ID. NO. 37564 | 87-AlaAlaAspLysLeuAspLeuValLysCysArgValGluAlaHisLysAspGlyPhe-105 |
| SEQ. ID. NO. 37565 | 113-ProMetAspGluGlyAsp-118 |
| SEQ. ID. NO. 37566 | 140-AlaGlyMetAspArgArgGlyArgArgGluGlyThr-151 |
| SEQ. ID. NO. 37567 | 155-IleValGluArgAlaGlnSerLysValVal-164 |
| SEQ. ID. NO. 37568 | 176-LeuGluProGluAspLysArgLeuAsn-184 |
| SEQ. ID. NO. 37569 | 189-LeuGluProAspGlyValAlaArgPheLysProGluSerGly-202 |
| SEQ. ID. NO. 37570 | 210-GluValTyrProGluGlnAsnArgProAlaVal-220 |
| SEQ. ID. NO. 37571 | 230-TyrAlaAspSerGlyMetGluIle-237 |
| SEQ. ID. NO. 37572 | 239-IleAlaValArgLysHisHisLeu-246 |
| SEQ. ID. NO. 37573 | 249-ArgPheSerGluAlaCysAlaLysSerAlaLysLysIleProAspHisValArgLysSerAspLeuLysGlyArgValAspLeu-276 |
| SEQ. ID. NO. 37574 | 284-IleAspGlyGluThrAlaArgAspPheAspAsp-294 |
| SEQ. ID. NO. 37575 | 299-GluLysValGlyArgAsnTyr-305 |
| SEQ. ID. NO. 37576 | 318-ValArgProAspAspAlaIleAspAlaAspAlaGlnGluArgSerThr-333 |
| SEQ. ID. NO. 37577 | 358-ProAspValGluArg-362 |
| SEQ. ID. NO. 37578 | 376-AsnIleLysGluTyrArg-381 |
| SEQ. ID. NO. 37579 | 406-IleGlyAsnProHisLysAlaGlnIle-414 |
| SEQ. ID. NO. 37580 | 424-LeuGlnLysLysArgLeuAlaArgGlyAlaValGluPheGluSerValGlu-440 |
| SEQ. ID. NO. 37581 | 443-MetIlePheAspAspAsnGlyLysIleGluLys-453 |
| SEQ. ID. NO. 37582 | 458-ValArgAsnAspAlaHisLysLeuIleGlu-467 |
| SEQ. ID. NO. 37583 | 496-ProThrProGluLysLeuAlaThrLeuArgGluGlnLeu-508 |
| SEQ. ID. NO. 37584 | 517-GlyGlyAspAsnProSerProLysAspTyrAlaAla-528 |
| SEQ. ID. NO. 37585 | 531-GluGlnPheLysGlyArgProAspAlaGluLeu-541 |
| SEQ. ID. NO. 37586 | 576-ProIleArgArgTyrProAsp-582 |
| SEQ. ID. NO. 37587 | 592-ValLeuAsnArgLysThrTyrThrPro-600 |
| SEQ. ID. NO. 37588 | 613-PheCysGluArgArgAlaAspAspAlaGlyArgAspValGluAsn-627 |
| SEQ. ID. NO. 37589 | 633-TyrMetArgAspLysValGlyGluIlePheGluGlyLysIleSerArg-648 |
| SEQ. ID. NO. 37590 | 684-IleMetAlaIleGluGlyGluArgSerGlyIle-694 |
| SEQ. ID. NO. 37591 | 697-AsnMetGlyAspArgValAlaValArgValAlaArgAlaAspLeuAspAspGlyLysIle-716 |
| SEQ. ID. NO. 37592 | 724-GluSerGlyArgArgArgLysValLysLeu-733 |
| SEQ. ID. NO. 37593 | 735-AlaSerAlaLysProAlaGlyAlaAlaGlyLysGlyLysSerLysThrThrAlaGluLysLysThrAlaArgCysGlyLysValArgGlyArg Gly-766 |
| SEQ. ID. NO. 37594 | 771-AlaGluSerGlyLysLysAlaLysLysProValProIleLysValLysLysArgLysGlyLysSer-792 |
| g989 | |
| AMPHI Regions - AMPHI | |
| SEQ. ID. NO. 37595 | 36-AlaGlnSerThrAlaAsnAlaAla-43 |
| SEQ. ID. NO. 37596 | 53-AlaGlyLeuThrLysLeu-58 |
| SEQ. ID. NO. 37597 | 80-SerAlaThrAspPhe-84 |
| SEQ. ID. NO. 37598 | 104-ProHisIleTyrGlyAla-109 |
| SEQ. ID. NO. 37599 | 178-GluLeuArgLysTyrAlaAspGlyIle-186 |
| SEQ. ID. NO. 37600 | 195-AlaThrProSerAsnProThr-201 |
| SEQ. ID. NO. 37601 | 287-ValThrProGluSer-291 |
| SEQ. ID. NO. 37602 | 293-SerValHisGlyMetTyrLysValSer-301 |
| SEQ. ID. NO. 37603 | 312-TrpThrArgHisSerArg-317 |
| SEQ. ID. NO. 37604 | 357-SerTyrGlnIleSerGluPro-363 |
| SEQ. ID. NO. 37605 | 439-SerCysAlaArgPheLysAsnHisAlaAsp-448 |
| Antigenic Index - Jameson-Wolf | |
| SEQ. ID. NO. 37606 | 41-AsnAlaAlaAspAlaSer-46 |
| SEQ. ID. NO. 37607 | 52-ProAlaGlyLeuThrLysLeuAspSerSerGlnIle-63 |
| SEQ. ID. NO. 37608 | 76-TyrGluAlaAspSerAlaThrAspPheThr-85 |
| SEQ. ID. NO. 37609 | 89-ValGlnGlySerLysAsnGlyLysIleThrLysThrThr-101 |
| SEQ. ID. NO. 37610 | 111-LysValAsnAspAsnLeuThr-117 |
| SEQ. ID. NO. 37611 | 127-GlySerAlaThrGluTyrGluLysAspSerValLeu-138 |
| SEQ. ID. NO. 37612 | 141-AsnIleAsnLysLeuGly-146 |
| SEQ. ID. NO. 37613 | 159-LysLeuAsnGluArgHisSerPheGly-167 |
| SEQ. ID. NO. 37614 | 174-HisAsnSerAlaGluLeuArgLysTyrAlaAspGlyIleProLysLysAlaGln-191 |
| SEQ. ID. NO. 37615 | 196-ThrProSerAsnPro-200 |
| SEQ. ID. NO. 37616 | 206-IleLysAlaAspGlyHisAlaAspValLysGlySerAspTrpGly-220 |
| SEQ. ID. NO. 37617 | 230-AspIleAsnAspArgAlaArgValGlyValAsnTyrArgSerLysValSerHisThrLeuLysGlyAspAlaGluTrpAlaAla-257 |
| SEQ. ID. NO. 37618 | 259-GlyAlaAlaAlaLysGlnGlnTrpAsnAspAsnMet-270 |
| SEQ. ID. NO. 37619 | 278-AlaAsnGluLysAlaSerVal-284 |
| SEQ. ID. NO. 37620 | 287-ValThrProGluSer-291 |
| SEQ. ID. NO. 37621 | 298-TyrLysValSerAspLysAlaAspLeu-306 |
| SEQ. ID. NO. 37622 | 313-ThrArgHisSerArgPheAsnLys-320 |
| SEQ. ID. NO. 37623 | 323-LeuPhePheGluLysGluLysAsnIleAlaAsnGlyLysLysSerAspArgThrThrIleThrProAsnTrpArgAsnThrTyrLys-351 |
| SEQ. ID. NO. 37624 | 353-GlyLeuGlyGlySerTyrGlnIleSerGlu-362 |
| SEQ. ID. NO. 37625 | 372-PheAspLysProProValArgAsnAlaAspTyrArgMetAsnSerLeuProAspGlyAsnArg-392 |
| SEQ. ID. NO. 37626 | 402-HisIleGlyLysAsnHisVal-408 |
| SEQ. ID. NO. 37627 | 419-AsnAspThrSerTyrArgThrAlaLysAlaSerGlyAsnAspValAspSerLysGlyAlaSerCysAlaArgPheLysAsnHisAla-447 |
| Hydrophilic Regions - Hopp-Woods | |
| SEQ. ID. NO. 37628 | 56-ThrLysLeuAspSerSerGln-62 |
| SEQ. ID. NO. 37629 | 76-TyrGluAlaAspSerAlaThr-82 |
| SEQ. ID. NO. 37630 | 90-GlnGlySerLysAsnGlyLysIleThrLys-99 |
| SEQ. ID. NO. 37631 | 130-ThrGluTyrGluLysAspSerValLeu-138 |
| SEQ. ID. NO. 37632 | 159-LysLeuAsnGluArgHisSer-165 |
| SEQ. ID. NO. 37633 | 175-AsnSerAlaGluLeuArgLysTyrAlaAspGlyIleProLysLysAlaGln-191 |
| SEQ. ID. NO. 37634 | 206-IleLysAlaAspGlyHisAlaAspValLysGlySerAsp-218 |
| SEQ. ID. NO. 37635 | 231-IleAsnAspArgAlaArgVal-237 |
| SEQ. ID. NO. 37636 | 241-TyrArgSerLysVal-245 |
| SEQ. ID. NO. 37637 | 249-LeuLysGlyAspAlaGluTrpAlaAla-257 |

TABLE 1-continued

SEQ. ID. NO. 37638 278-AlaAsnGluLysAlaSerVal-284
SEQ. ID. NO. 37639 299-LysValSerAspLysAlaAspLeu-306
SEQ. ID. NO. 37640 316-SerArgPheAsnLys-320
SEQ. ID. NO. 37641 323-LeuPhePheGluLysGluLysAsnIleAlaAsnGlyLysLysSerAspArgThrThrIle-342
SEQ. ID. NO. 37642 372-PheAspLysProProValArgAsnAlaAspTyrArgMet-384
SEQ. ID. NO. 37643 386-SerLeuProAspGlyAsn-391
SEQ. ID. NO. 37644 421-ThrSerTyrArgThrAlaLysAlaSerGlyAsnAspValAspSerLysGlyAlaSer-439
SEQ. ID. NO. 37645 441-AlaArgPheLysAsnHisAla-447
g992
AMPHI Regions - AMPHI
SEQ. ID. NO. 37646 6-ArgHisLeuLysAsnMetGlnIleLysLysIleMetLysTrp-19
SEQ. ID. NO. 37647 24-LeuSerLeuLeuGlyAlaLeuGlyTyr-32
SEQ. ID. NO. 37648 45-AlaValLeuAspValLeuGlyThr-52
SEQ. ID. NO. 37649 72-HisSerTyrThrGlyThrValSerLysValTyr-82
SEQ. ID. NO. 37650 140-TyrGlnArgGluValAlaGlnVal-147
SEQ. ID. NO. 37651 158-GlnValGlnAspGly-162
SEQ. ID. NO. 37652 179-AspPheAlaAspTyr-183
Antigenic Index - Jameson-Wolf
SEQ. ID. NO. 37653 1-MetPheArgArgHisArgHisLeuLys-9
SEQ. ID. NO. 37654 33-ThrGlyTyrAspSerGluAlaValArg-41
SEQ. ID. NO. 37655 51-GlyThrAlaGlyAspValGlyPhe-58
SEQ. ID. NO. 37656 60-AlaProValArgArgArgAlaSerAlaLysSerGlyHisSerTyr-74
SEQ. ID. NO. 37657 79-SerLysValTyrAspGlyAspThr-86
SEQ. ID. NO. 37658 90-IleAspGlyAspGlyAlaLysHisLysIle-99
SEQ. ID. NO. 37659 105-AspAlaProGluMetLysGlnAlaTyrGlyThrArgSerArgAspAsnLeuArgAlaAlaAlaGluGlyArgLysValSer-131
SEQ. ID. NO. 37660 134-ValPheGluThrAspArgTyrGlnArgGluValAla-145
SEQ. ID. NO. 37661 148-SerAlaGlyLysThrAspLeu-154
SEQ. ID. NO. 37662 168-LysSerTyrAlaLysGluGlnGlnAspLysAlaAspPhe-180
SEQ. ID. NO. 37663 187-GlnIleGlnAlaGluArgGluArgLysGlyLeuTrpLysAlaLysAsnProGlnAlaPro-206
SEQ. ID. NO. 37664 208-AlaTyrArgArgAlaGlyArgSerGlyGlyGlyAsnLysAspTrpMetAspSerValGlyGlu-228
Hydrophilic Regions - Hopp-Woods
SEQ. ID. NO. 37665 1-MetPheArgArgHisArgHisLeuLys-9
SEQ. ID. NO. 37666 35-TyrAspSerGluAlaValArg-41
SEQ. ID. NO. 37667 60-AlaProValArgArgArgAlaSerAlaLysSerGlyHis-72
SEQ. ID. NO. 37668 80-LysValTyrAspGlyAspThr-86
SEQ. ID. NO. 37669 90-IleAspGlyAspGlyAlaLysHisLysIle-99
SEQ. ID. NO. 37670 105-AspAlaProGluMetLysGln-111
SEQ. ID. NO. 37671 113-TyrGlyThrArgSerArgAspAsnLeuArgAlaAlaAlaGluGlyArgLysValSer-131
SEQ. ID. NO. 37672 134-ValPheGluThrAspArgTyrGlnArgGluValAla-145
SEQ. ID. NO. 37673 148-SerAlaGlyLysThrAspLeu-154
SEQ. ID. NO. 37674 169-SerTyrAlaLysGluGlnGlnAspLysAlaAspPhe-180
SEQ. ID. NO. 37675 187-GlnIleGlnAlaGluArgGluArgLysGlyLeuTrpLysAlaLysAsnPro-203
SEQ. ID. NO. 37676 211-ArgAlaGlyArgSerGlyGlyGlyAsnLysAspTrpMetAspSerVal-226
g993
AMPHI Regions - AMPHI
SEQ. ID. NO. 37677 6-GlySerPheGlnGlyProLeuAspLeuLeuLeu-16
SEQ. ID. NO. 37678 35-ThrGlyGlnTyrLeuHisTyrIleAlaGlnMet-45
SEQ. ID. NO. 37679 105-GlyLeuAspAlaLeuProArgAla-112
SEQ. ID. NO. 37680 133-GluValTyrIleAlaAspLeuMetGlnAlaTrpLeuGly-145
SEQ. ID. NO. 37681 152-HisThrArgSerHisGluValIle-159
SEQ. ID. NO. 37682 169-MetThrAlaIleLeuArgArgLeuAsnGluHisGlyIleCysArgPheHisAlaLeuPheAsn-189
SEQ. ID. NO. 37683 198-IleValAsnPheIleAlaLeuLeu-205
Antigenic Index - Jameson-Wolf
SEQ. ID. NO. 37684 7-SerPheGlnGlyProLeu-12
SEQ. ID. NO. 37685 20-ArgLysGlnAsnIleAsp-25
SEQ. ID. NO. 37686 70-LeuLeuLeuProArgThrGluAlaValGluAspGluGluAlaAspProArgAlaGluLeuValArg-91
SEQ. ID. NO. 37687 108-AlaLeuProArgAlaGlyArgAspPhe-116
SEQ. ID. NO. 37688 125-IleAlaAlaGluThrLysLeuPro-132
SEQ. ID. NO. 37689 148-SerArgAlaLysHisThrArgSerHisGluValIleGln-160
SEQ. ID. NO. 37690 174-ArgArgLeuAsnGluHisGlyIle-181
SEQ. ID. NO. 37691 189-AsnProGluGlnGly-193
SEQ. ID. NO. 37692 207-LeuAlaLysGluGlyLeu-212
SEQ. ID. NO. 37693 216-ValGlnGluAspGlyPheGlyGluIleArgIle-226
SEQ. ID. NO. 37694 228-LeuAsnHisGluGlyAlaHisSerAspGlyIlePheGlyThrArgGlyGlyArgAspValPhe-248
Hydrophilic Regions - Hopp-Woods
SEQ. ID. NO. 37695 20-ArgLysGlnAsnIleAsp-25
SEQ. ID. NO. 37696 70-LeuLeuLeuProArgThrGluAlaValGluAspGluGluAlaAspProArgAlaGluLeuValArg-91
SEQ. ID. NO. 37697 108-AlaLeuProArgAlaGlyArg-114
SEQ. ID. NO. 37698 125-IleAlaAlaGluThrLysLeuPro-132
SEQ. ID. NO. 37699 148-SerArgAlaLysHisThrArgSerHisGluValIleGln-160
SEQ. ID. NO. 37700 174-ArgArgLeuAsnGlu-178
SEQ. ID. NO. 37701 207-LeuAlaLysGluGlyLeu-212
SEQ. ID. NO. 37702 216-ValGlnGluAspGlyPheGly-222
SEQ. ID. NO. 37703 242-ArgGlyGlyArgAspValPhe-248
g996
AMPHI Regions - AMPHI
SEQ. ID. NO. 37704 21-LysSerAlaArgThrHisAlaLysIlePro-30
SEQ. ID. NO. 37705 50-ProGlyGluSerTyrProAlaGlnLeuGlnLysLeuThrGlyTrpAsn-65
SEQ. ID. NO. 37706 75-ThrSerAlaGlnAlaLeuSerArgLeuProAla-85
SEQ. ID. NO. 37707 104-LeuArgLysValProGluGlu-110

TABLE 1-continued

| | |
|---|---|
| SEQ. ID. NO. 37708 | 115-AsnIleAlaLysIleIleGluThrValGlnLys-125 |
| SEQ. ID. NO. 37709 | 140-LeuGlyAlaLeuPheGlyHisLeuSerAsp-149 |
| SEQ. ID. NO. 37710 | 167-GlyAlaTrpAlaGlu-171 |
| SEQ. ID. NO. 37711 | 186-AsnGlyLysGlyTyrArgLysPheAlaGluAsnLeuAsnGlnPheLeuArgLysHisGlyPhe-206 |
| Antigenic Index - Jameson-Wolf | |
| SEQ. ID. NO. 37712 | 1-MetAsnArgArgThrPhe-6 |
| SEQ. ID. NO. 37713 | 18-CysGlyArgLysSerAlaArgThrHisAlaLysIleProGluGlySerThr-34 |
| SEQ. ID. NO. 37714 | 46-TyrGlyAlaAsnProGlyGluSerTyrPro-55 |
| SEQ. ID. NO. 37715 | 69-GlyGlyValSerGlyAspThrSerAla-77 |
| SEQ. ID. NO. 37716 | 87-LeuAlaArgLysProLys-92 |
| SEQ. ID. NO. 37717 | 99-GlyGlyAsnAspPheLeuArgLysValProGluGluGlnThrArgAlaAsnIle-116 |
| SEQ. ID. NO. 37718 | 121-GluThrValGlnLysGluAsnIle-128 |
| SEQ. ID. NO. 37719 | 148-SerAspHisProLeuTyrGluAspLeuSerGluGluTyrGly-161 |
| SEQ. ID. NO. 37720 | 174-GlyAsnAsnAsnLeuLysSerAspGlnIleHisAlaAsnGlyLysGlyTyrArgLysPheAlaGluAsnLeuAsnGlnPheLeuArgLys HisGlyPheArg-207 |
| Hydrophilic Regions - Hopp-Woods | |
| SEQ. ID. NO. 37721 | 18-CysGlyArgLysSerAlaArgThrHisAlaLysIleProGlu-31 |
| SEQ. ID. NO. 37722 | 49-AsnProGlyGluSerTyr-54 |
| SEQ. ID. NO. 37723 | 71-ValSerGlyAspThrSerAla-77 |
| SEQ. ID. NO. 37724 | 87-LeuAlaArgLysProLys-92 |
| SEQ. ID. NO. 37725 | 102-AspPheLeuArgLysValProGluGluGlnThrArgAlaAsnIle-116 |
| SEQ. ID. NO. 37726 | 121-GluThrValGlnLysGluAsnIle-128 |
| SEQ. ID. NO. 37727 | 154-GluAspLeuSerGluGluTyrGly-161 |
| SEQ. ID. NO. 37728 | 177-AsnLeuLysSerAspGlnIleHisAlaAsn-186 |
| SEQ. ID. NO. 37729 | 188-LysGlyTyrArgLysPheAlaGlu-195 |
| g997 | |
| AMPHI Regions - AMPHI | |
| SEQ. ID. NO. 37730 | 18-TrpAlaGlyLeuSerAlaAlaVal-25 |
| SEQ. ID. NO. 37731 | 70-TyrArgGlyValLeuArgLeuMetLysThrIleGly-81 |
| SEQ. ID. NO. 37732 | 107-ProLeuProAlaProLeuHisIle-114 |
| SEQ. ID. NO. 37733 | 123-ArgValProSerAlaPheLysAlaLysLeuLeuAlaAspMetSerAspLeuGlnLysSerAlaArgLeuGly-146 |
| SEQ. ID. NO. 37734 | 164-AlaAlaValMetGlnPheTrpGlnProLeuValTrpGly-176 |
| SEQ. ID. NO. 37735 | 189-ValLeuCysAsnValLeuSerAsp-196 |
| SEQ. ID. NO. 37736 | 222-AlaLeuAlaGluLeuGlnArg-228 |
| SEQ. ID. NO. 37737 | 241-ArgLeuAsnThrLeuPro-246 |
| SEQ. ID. NO. 37738 | 275-GluGlyThrProGluHisValGlnThrAla-284 |
| SEQ. ID. NO. 37739 | 300-TyrAlaGluProValArgLeuProAlaProLeuThrGlyIleAlaAspGly-316 |
| Antigenic Index - Jameson-Wolf | |
| SEQ. ID. NO. 37740 | 3-AsnThrProHisProArgProLysIle-11 |
| SEQ. ID. NO. 37741 | 37-GluAlaGlyArgGlnAlaGlyGlyArgAlaArgThrLeuAlaGlyAsnThrAspGlyPheGly-57 |
| SEQ. ID. NO. 37742 | 78-LysThrIleGlySerAspProArgAlaAla-87 |
| SEQ. ID. NO. 37743 | 122-ArgArgValProSerAlaPheLys-129 |
| SEQ. ID. NO. 37744 | 132-LeuLeuAlaAspMetSerAspLeuGlnLysSerAlaArgLeuGlyGlnProAspThrThr-151 |
| SEQ. ID. NO. 37745 | 156-LeuLysGlnArgAsnValProArg-163 |
| SEQ. ID. NO. 37746 | 180-ThrProLeuGluThrAlaSer-186 |
| SEQ. ID. NO. 37747 | 197-GlyValLeuThrLysLysSerGlySerAspTyrLeuLeuProLysGlnAspLeu-214 |
| SEQ. ID. NO. 37748 | 225-GluLeuGlnArgLeuGlyAlaAspIleArgLeuGluThrArgValCysArg-241 |
| SEQ. ID. NO. 37749 | 243-AsnThrLeuProAspGlyLysVal-250 |
| SEQ. ID. NO. 37750 | 273-LeuProGluGlyThrProGluHisVal-281 |
| SEQ. ID. NO. 37751 | 324-ProGlyGlnAlaProAspCysProGlnAsnGluValSer-336 |
| SEQ. ID. NO. 37752 | 341-ValSerAspArgValGlyAlaPheAlaAsnArgTerTerTerTer-355 |
| Hydrophilic Regions - Hopp-Woods | |
| SEQ. ID. NO. 37753 | 5-ProHisProArgProLysIle-11 |
| SEQ. ID. NO. 37754 | 37-GluAlaGlyArgGlnAlaGlyGlyArgAlaArgThrLeuAlaGlyAsn-52 |
| SEQ. ID. NO. 37755 | 80-IleGlySerAspProArgAlaAla-87 |
| SEQ. ID. NO. 37756 | 122-ArgArgValProSer-126 |
| SEQ. ID. NO. 37757 | 132-LeuLeuAlaAspMetSerAspLeuGlnLysSerAlaArgLeuGlyGlnProAspThrThr-151 |
| SEQ. ID. NO. 37758 | 198-ValLeuThrLysLysSerGlySer-205 |
| SEQ. ID. NO. 37759 | 208-LeuLeuProLysGlnAspLeu-214 |
| SEQ. ID. NO. 37760 | 225-GluLeuGlnArgLeuGlyAlaAspIleArgLeuGluThrArgValCysArg-241 |
| SEQ. ID. NO. 37761 | 246-ProAspGlyLysVal-250 |
| SEQ. ID. NO. 37762 | 276-GlyThrProGluHisVal-281 |
| SEQ. ID. NO. 37763 | 326-GlnAlaProAspCysProGlnAsnGluVal-335 |
| SEQ. ID. NO. 37764 | 341-ValSerAspArgValGly-346 |

It will be understood that the invention is described above by way of example only and modifications may be made whilst remaining within the scope and spirit of the invention.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09067987B2). An electronic copy of the "Sequence Listing" will also be available from the USPTO upon request and payment of the fee set forth in 37 CFR 1.19(b)(3).

---

What is claimed is:

1. A composition comprising an isolated polypeptide comprising the amino acid sequence of SEQ ID NO: 24057 and an immunostimulatory effective amount of aluminum phosphate adjuvant.

2. The composition of claim 1, wherein the polypeptide does not comprise the full length protein sequence of SEQ ID NO: 41371.

3. The composition of claim 1, wherein the amino acid sequence of SEQ ID NO: 24057 is an antigenic fragment of SEQ ID NO: 41371.

4. The composition of claim 3, wherein the polypeptide does not comprise the full length protein sequence of SEQ ID NO: 41371.

5. The composition of claim 1, further comprising a pharmaceutically acceptable carrier.

6. The composition of claim 2, further comprising a pharmaceutically acceptable carrier.

7. The composition of claim 3, further comprising a pharmaceutically acceptable carrier.

8. The composition of claim 4, further comprising a pharmaceutically acceptable carrier.

9. A composition comprising a purified polypeptide comprising the amino acid sequence of SEQ ID NO: 24057 and an immunostimulatory effective amount of aluminum phosphate adjuvant.

10. The composition of claim 9, wherein the polypeptide does not comprise the full length protein sequence of SEQ ID NO: 41371.

11. The composition of claim 9, wherein the amino acid sequence of SEQ ID NO: 24057 is an antigenic fragment of SEQ ID NO: 41371.

12. The composition of claim 11, wherein the polypeptide does not comprise the full length protein sequence of SEQ ID NO: 41371.

13. The composition of claim 9, further comprising a pharmaceutically acceptable carrier.

14. The composition of claim 10, further comprising a pharmaceutically acceptable carrier.

15. The composition of claim 11, further comprising a pharmaceutically acceptable carrier.

16. The composition of claim 12, further comprising a pharmaceutically acceptable carrier.

* * * * *